(12) United States Patent
ter Haar et al.

(10) Patent No.: US 7,666,647 B2
(45) Date of Patent: Feb. 23, 2010

(54) INHIBITORS OF GSK-3 AND CRYSTAL STRUCTURES OF GSK-3β PROTEIN AND PROTEIN COMPLEXES

(75) Inventors: Ernst ter Haar, Roslindale, MA (US); Lovorka Swenson, Belmont, MA (US); Jeremy Green, Burlngton, MA (US); Michael J. Arnost, North Andover, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/079,917

(22) Filed: Mar. 28, 2008

(65) Prior Publication Data

US 2008/0262205 A1 Oct. 23, 2008

Related U.S. Application Data

(62) Division of application No. 10/135,255, filed on Apr. 29, 2002, now Pat. No. 7,390,808.

(60) Provisional application No. 60/361,899, filed on Feb. 27, 2002, provisional application No. 60/297,094, filed on Jun. 8, 2001, provisional application No. 60/287,366, filed on Apr. 30, 2001.

(51) Int. Cl.
| | |
|---|---|
| *C12N 9/00* | (2006.01) |
| *C12N 9/10* | (2006.01) |
| *C12N 9/12* | (2006.01) |
| *C12P 21/04* | (2006.01) |
| *C07K 14/00* | (2006.01) |
| *A61K 38/17* | (2006.01) |
| *A61K 38/45* | (2006.01) |

(52) U.S. Cl. .................. 435/194; 435/183; 435/193; 435/69.1; 530/350

(58) Field of Classification Search .................. None
See application file for complete search history.

(56) References Cited

U.S. PATENT DOCUMENTS

| | | | |
|---|---|---|---|
| 4,886,646 | A | 12/1989 | Carter et al. |
| 5,096,676 | A | 3/1992 | McPherson et al. |
| 5,130,105 | A | 7/1992 | Carter et al. |
| 5,221,410 | A | 6/1993 | Kushner et al. |
| 5,353,236 | A | 10/1994 | Subbiah |
| 5,400,741 | A | 3/1995 | DeTitta et al. |
| 6,162,613 | A | 12/2000 | Su et al. |
| 6,387,641 | B1 | 5/2002 | Bellon et al. |

FOREIGN PATENT DOCUMENTS

| | | |
|---|---|---|
| WO | WO 92/14211 | 8/1992 |
| WO | WO 93/02209 | 2/1993 |
| WO | WO 94/25860 | 11/1994 |
| WO | WO 98/35048 | 8/1998 |
| WO | WO 99/65897 | 12/1999 |
| WO | WO 00/12497 | 3/2000 |
| WO | WO 00/38675 | 7/2000 |
| WO | WO 02/24694 | 3/2002 |
| WO | WO 02/24893 | 3/2002 |

OTHER PUBLICATIONS

Giege et al., Crystallogenesis of Biological Macromolecules: Facts and Perspectives. Acta Cryst., 1994, D50: 339-350.*
Branden et al., "Introduction to Protein Structure Second Edition", Garland Publishing Inc., New York, 1999.*
Drenth et al. "Principles of X-ray Crystallography," Springer, New York, 1995.*
Kierzek et al. (2001), Biophys Chem 91:1-20.*
Wiencek (Ann Rev Biomed Eng, 1999, 1:505-534).*
Adams, "Kinetic and Catalytic Mechanisms of Protein Kinases," *Chem. Rev.*, 101:2271-2290 (2001).
Aoki et al., "Expression, Purification and Crystallization of Human Tau-protein Kinase I/Glycogen Synthase Kinase-3β," *Acta Crystallographica Section D*, D56:1464-1465 (2000).
Balbes et al., "A Perspective of Modern Methods in Computer-Aided Drug Design," in *"Reviews in Computational Chemistry,"* K.B. Lipkowitz and D.B. Boyd, Eds., VCH Publishers, New York, 5:337-379 (1994).
Bartlett et al., "CAVEAT: A Program to Facilitate the Structure-Derived Design of Biologically Active Molecules," in *"Molecular Recognition in Chemical and Biological Problems,"* S.M. Roberts, Ed., Royal Society of Chemistry, Special Publication No. 78:182-196 (1989).
Bax et al., "The Structure of Phosphorylated GSK-3β Complexed with a Peptide, FRATtide, that Inhibits β-Cantenin Phosphorylation," *Structure*, 9:1143-1152 (2001).
Bellon et al., "The Structure of Phosphorylated P38γ is Monomeric and Reveals a Conserved Activation-Loop Conformation," *Structure*, 7:1057-1065 (1999).

(Continued)

*Primary Examiner*—David J Steadman
*Assistant Examiner*—Jae W Lee
(74) *Attorney, Agent, or Firm*—Ropes & Gray LLP; James F. Haley, Jr.; Raymond M. Doss

(57) ABSTRACT

The present invention relates to inhibitors of GSK-3 and methods for producing these inhibitors. The invention also provides pharmaceutical compositions comprising the inhibitors and methods of utilizing those compositions in the treatment and prevention of various disorders, such as diabetes and Alzheimer's disease. In addition, the invention relates to molecules or molecular complexes which comprise binding pockets of GSK-3β or its homologues. The invention relates to a computer comprising a data storage medium encoded with the structure coordinates of such binding pockets. The invention also relates to methods of using the structure coordinates to solve the structure of homologous proteins or protein complexes. The invention relates to methods of using the structure coordinates to screen for and design compounds that bind to GSK-3β protein or homologues thereof. The invention also relates to crystallizable compositions and crystals comprising GSK-3β protein or GSK-3β protein complexes.

3 Claims, 619 Drawing Sheets

OTHER PUBLICATIONS

Böhm, "The Computer Program LUDI: A New Method for the De Novo Design of Enzyme Inhibitors," *J. Comp. Aid. Molec. Design*, 6:61-78 (1992).
Bossemeyer et al., "Phosphotransferase and Substrate Binding Mechanishm of the cAMP-Dependent Protein Kinase Catalytic Subunit from Porcine Heart as Deduced from the 2.0 Å Structure of the Complex with $Mn^{2+}$ Adenylyl Imidodiphosphate and Inhibitor Peptide PKI(5-24)," *The EMBO Journal*, 12:849-859 (1993).
Boulton et al., "ERKs: A Family of Protein-Serine/Threonine Kinases that are Activated and Tyrosine Phosphorylated in Response to Insulin and NGF," *Cell*, 65:663-675 (1991).
Brown et al., "Crystallography in the Study of Protein-DNA Interactions," *Methods in Molecular Biology*, 56:293-318 (1996).
Brown et al., "The Structural Basis for Specificity of Substrate and Recruitment Peptides for Cyclin-Dependent Kinases," *Nature Cell Biol.*, 1:438-443 (1999).
Brownlees et al., "Tau Phosphorylation in Transgenic Mice Expressing Glycogen Synthase Kinase-3β Transgenes," *NeuroReport*, 8:3251-3255 (1997).
Bryan, "Protein Engineering," *Biotech Adv.*, 5:221-234 (1987).
Campbell et al., "Diffraction, in Biological Spectroscopy," *The Benjamin/Cummings Publishing Company, Inc.*, Menlo Park, CA, pp. 299-326 (1984).
Canagarajah et al., "Activation Mechanism of the MAP Kinase ERK2 by Dual Phosphorylation," *Cell*, 90:859-869 (1997).
Coghlan et al., "Selective Small Molecule Inhibitors of Glycogen Synthase Kinase-3 Modulate Glycogen Metabolism and Gene Transcription," *Chemistry & Biology*, 7:793-803 (2000).
Cohen et al., "Molecular Modeling Software and Methods for Medicinal Chemistry," *J. Med. Chem.*, 33:883-894 (1990).
Cohen, "Dissection of the Protein Phosphorylation Cascades Involved in Insulin and Growth Factor Action," *Biochem. Soc. Trans.*, 21:555-567 (1993).
Collaborative Computational Project, No. 4, "The CCP4 Suite: Programs for Protein Crystallography," *Acta Cryst.*, D50:760-763 (1994).
Cross et al., "The Inhibition of Glycogen Synthase Kinase-3 by Insulin or Insulin-Like Growth Factor 1 in the Rat Skeletal Muscle Cell Line L6 is Blocked by Wortmannin, but not by Rapamycin: Evidence that Wortmannin Blocks Activation of the Mitogen-Activated Protein Kinase Pathway in L6 Cells between Ras and Raf," *Biochem. J.*, 303:21-26 (1994).
Dajani et al., "Crystal Structure of Glycogen Synthase Kinase 3β: Structure Basis for Phosphate-Primed Substrate Specificity and Autoinhibition," *Cell*, 105:721-732 (2001).
Deeb et al., "Studies on Polyazaindenes Synthesis of Several New Condensed Pyridazine Derivatives," *Collect. Czech. Chem. Commun.*, 55:2795-2799 (1990).
Ding et al., "Differential Regulation of Glycogen Synthase Kinase 3β by Insulin and Wnt Signaling," *J. Biol. Chem.*, 275:32475-32481 (2000).
Eisen et al., "HOOK: A Program for Finding Novel Molecular Architectures that Satisfy the Chemical and Steric Requirements of a Macromolecule Binding Site," *Proteins Struct. Funct. Genet.*, 19:199-221 (1994).
Fang et al., "Phosphorylation and Inactivation of Glycogen Synthase Kinase 3 by Protein Kinase A," *Proc. Natl. Acad. Sci. USA*, 97:11960-11965 (2000).
Fox et al. "A Single Amino Acid Substitution Makes ERK2 Susceptible to Pyridinyl Imidazole Inhibitors of p38 MAP Kinase," *Protein Sci.*, 7:2249-2255 (1998).
Gerstein et al., "Average Core Structures and Variability Measures for Protein Families: Application to the Immunoglobulins," *J. Mol. Biol.*, 251:161-175 (1995).
Gillet et al., "SPROUT: A Program for Structure Generation," *J. Comp. Aid. Molec. Design*, 7:127-153 (1993).
Goldsmith et al., "Protein Kinases," *Current Opinion in Structural Biology*, 4:833-840 (1994).
Goodford, "A Computational Procedure for Determining Energetically Favorable Binding Sites on Biologically Important Macromolecules," *J. Med. Chem.*, 28:849-857 (1985).
Goodsell et al., "Automated Docking of Substrates to Proteins by Simulated Annealing," *Proteins Struct. Funct. Genet.*, 8:195-202 (1990).
Guida, "Software for Structure-Based Drug Design," *Curr. Opin. Struct. Biology*, 4:777-781 (1994).
Haar et al., "Structure of GSK3β Reveals a Primed Phosphorylation Mechanism," *Nature Structural Biology*, 8(7):593-596 (2001).
Hanks et al., "Protein Kinase Catalytic Domain Sequence Database: Identification of Conserved Features of Primary Structure and Classification of Family Members," *Methods in Enzymology*, 200:38-62 (1991).
Hanks et al., "The Eukaryotic Protein Kinase Superfamily: Kinase (Catalytic) Domain Structure and Classification," *FASEB J.*, 9:576-596 (1995).
Hanks et al., "The Protein Kinase Family: Conserved Features and Deduced Phylogeny of the Catalytic Domains," *Science*, 241:42-52 (1988).
Haq et al., "Glycogen Synthase Kinase-3β Is a Negative Regulator of Cardiomyocyte Hypertrophy," *J. Cell Biol.*, 151:117-129 (2000).
Hoeflich et al., "Requirement for Glycogen Synthase Kinase-3β in Cell Survival and NF-κB Activation," *Nature*, 406:86-90 (2000).
Ikeda et al., "Axin, a Negative Regulator of the Wnt Signaling Pathway, Forms a Complex with GSK-3β and β-Catenin and Promotes GSK-3β-Dependent Phosphorylation of β-Catenin," *EMBO J.*, 17:1371-1384 (1998).
Iyoda et al., "Synthesis of Riccardin B by Nickel-Catalyzed Intramolecular Cyclization," *Tetrahedron Letters*, 26:4777-4780 (1985).
Johnson et al., "Active and Inactive Protein Kinases: Structural Basis for Regulation," *Cell*, 85:149-158 (1996).
Kajihara et al., "Protein Modeling Using a Chimera Reference Protein Derived From Exons," *Protein Eng'g*, 6:615-620 (1993).
Kim et al., "GSK3, a Master Switch Regulating Cell-Fate Specification and Tumorigenesis," *Current Opinion in Genetics & Development*, 10:508-514 (2000).
Klein et al., "A Molecular Mechanism for the Effect of Lithium on Development," *Proc. Natl. Acad. Sci. USA*, 93:8455-8459 (1996).
Knighton et al., "Crystal Structure of the Catalytic Subunit of Cyclic Adenosine Monophosphate-Dependent Protein Kinase," *Science*, 253:407-413 (1991).
Knighton et al., "Structure of Peptide Inhibitor Bound to the Catalytic Subunit of Cyclic Adenosine Monophosphate-Dependent Protein Kinase," *Science*, 253:414-420 (1991).
Kuntz et al., "A Geometric Approach to Macromolecule-Ligand Interactions," *J. Mol. Biol.*, 161:269-288 (1982).
Kuret et al., "Multisite Phosphorylation of Glycogen Synthase from Rabbit Skeletal Muscle: Identification of the Sites Phosphorylated by Casein Kinase-I," *Eur. J. Biochem.*, 151:39-48 (1985).
Lauri et al., "CAVEAT: A Program to Facilitate the Design of Organic Molecules," *J. Comp. Aid. Molec. Design*, 8:51-66 (1994).
Lawrie et al., "Protein Kinase Inhibition by Staurosporine Revealed in Details of the Molecular Interaction with CDK2," *Nature Struct. Biol.*, 4:796-801 (1997).
Lee et al., "A Protein Kinase Involved in the Regulation of Inflammatory Cytokine Biosynthesis," *Nature*, 372:739-746 (1994).
Lovell et al., "The Penultimate Rotamer Library," *Proteins Struct. Funct. Genet.*, 40:389-408 (2000).
Lovestone et al., "Alzheimer's Disease-Like Phosphorylation of the Microtubule-Associated Protein Tau by Glycogen Synthase Kinase-3 in Transfected Mammalian Cells," *Current Biology*, 4:1077-1086 (1994).
Madhusudan et al, "cAMP-Dependent Protein Kinase: Crystallographic Insights Into Substrate Recognition and Phosphotransfer," *Protein Sci.*, 3:176-187 (1994).
Martin, "3D Database Searching in Drug Design," *J. Med. Chem.*, 35:2145-2154 (1992).
Martinez et al., "First Non-ATP Competitive Glycogen Synthase Kinase 3β (GSK-3β) Inhibitors: Thiadiazolidinones (TDZD) as Potential Drugs for the Treatment of Alzheimer's Disease," *J. Med. Chem.*, 45:1292-1299 (2002).
Massillon et al., "Identification of the Glycogenic Compound 5-iodotubercidin as a General Protein Kinase Inhibitor," *Biochem. J.*, 299:123-128 (1994).

Meng et al., "Automated Docking with Grid-Based Energy Evaluation," *Journal of Computational Chemistry*, 13:505-524 (1992).

Miranker et al., "Functionality Maps of Binding Sites: A Multiple Copy Simultaneous Search Method," *Proteins Struct. Funct. Genet.*, 11:29-34 (1991).

Navia et al., "Use of Structural Information in Drug Design," *Current Opinion Structural Biology*, 2:202-210 (1992).

Nishibata et al., "Automatic Creation of Drug Candidate Structures Based on Receptor Structure. Starting Point for Artificial Lead Generation." *Tetrahedron*, 47:8985-8990 (1991).

Pav et al., "Microtube Batch Protein Crystallization: Applications to Human Immunodeficiency Virus Type 2 (HIV-2) Protease and Human Renin," *Proteins Struct. Funct. Genet.*, 20:98-102 (1994).

Pei et al., "Distribution of Active Glycogen Synthase Kinase 3β (GSK-3β) in Brains Staged for Alzheimer Disease Neurofibrillary Changes," *Journal of Neuropathology and Experimental Neurology*, 58:1010-1019 (1999).

Ross et al., "Glycogen Synthase Kinase 3 Is an Insulin-Regulated C/EBPα Kinase," *Mol. Cell. Biol.*, 19:8433-8441 (1999).

Russell et al., "Rational Modification of Enzyme Catalysis by Engineering Surface Charge," *Nature*, 328:496-500 (1987).

Russo et al., "Structural Basis of Cyclin-Dependent Kinase Activation by Phosphorylation," *Nature Struct. Biol.*, 3:696-700 (1996).

Said et al., "Some Reactions with 3-Chloro-4-Cyano-5,6-Diphenyl Pyridazinone," *Asian Journal of Chemistry*, 1:376-383 (1989).

Salic et al., "Control of β-Catenin Stability: Reconstitution of the Cytoplasmic Steps of the Wnt Pathway in *Xenopus* Egg Extracts," *Mol. Cell*, 5:523-532 (2000).

Sato et al., "Facile synthesis of Benzyl Ketones by the Reductive Coupling of Benzyl Bromide and Acyl Chlorides in the Presence of a Palladium Catalyst and Zinc Powder," *Chemistry Letters*, 1135-1138 (1981).

Schulze-Gahmen et al., "Multiple Modes of Ligand Recognition: Crystal Structures of Cyclin-Dependent Protein Kinase 2 in Complex With ATP and Two Inhibitors, Olomoucine and Isopentenyladenine," *Proteins Struct. Funct. Genet.*, 22:378-391 (1995).

Shalaby, "Reactions of Ethyl Monohaloacetate and Hydrazine Hydrate with 4-Cyano and 4-Carbethoxypyryridazin-3(2H)-ones and their 3-Mercapto Derivatives. Syntheses of Furo, Thieno and Pyrazolo Pyridazines," *Journal f. prakt. Chemie*, 332:104-108 (1990).

Shilcrat et al., "Synthesis, X-Ray Crystal Structure Determination and Antiinflammatory Activity of the Regioisomers: 5-Phenyl-6-(4-pyridyl)-2,3-dihydroimidazo[2,1-*b*]thiazole and 6-Phenyl-5-(4-pyridyl)-2,3-dihydroimidazo[2,1-*b*]thiazole. A Structural Reassignment," *J. Heterocyclic Chem.*, 28:1181-1187 (1991).

Singh et al., "Structure-Based Design of a Potent, Selective, and Irreversible Inhibitor of the Catalytic Domain of the erbB Receptor Subfamily of Protein Tyrosine Kinases," *J. Med. Chem.*, 40:1130-1135 (1997).

Smith et al., "Comparison of Biosequences," *Advances in Applied Mathematics*, 2:482-489 (1981).

Summers et al., "The Role of Glycogen Synthase Kinase 3β in Insulin-Stimulated Glucose Metabolism," *J. Biol. Chem.*, 274:17934-17940 (1999).

Takashima et al., "Tau Protein Kinase I is Essential for Amyloid β-Protein-Induced Neurotoxicity," *Proc. Natl. Acad. Sci. USA*, 90:7789-7793 (1993).

Taylor et al., "Three Protein Kinase Structures Define a Common Motif," *Structure*, 2:345-355 (1994).

Thomas et al., "A GSK3-Binding Peptide from FRAT1 Selectively Inhibits the GSK3-Catalysed Phosphorylation of Axin and β-catenin," *FEBS Letters*, 458:247-251 (1999).

Waltzer et al., "The Control of β-Catenin and TCF During Embryonic Development and Cancer," *Cancer and Metastasis Reviews*, 18:231-246 (1999).

Wilson et al., "Crystal Structure of p38 Mitogen-activated Protein Kinase," *J. Biol. Chem.*, 271:27696-27700 (1996).

Wilson et al., "The Structural Basis for the Specificity of Pyridinylimidazole Inhibitors of p38 MAP Kinase," *Chem. & Biol.*, 4:423-431 (1997).

Woodgett et al., "Multisite Phosphorylation of Glycogen Synthase—Molecular Basis for the Substrate Specificity of Glycogen Synthase Kinase-3 and Casein Kinase-II (Glycogen Synthase Kinase-5),"*Biochimica et Biophysica Acta*, 788:339-347 (1984).

Woodgett, "Molecular Cloning and Expression of Glycogen Synthse Kinase-3/Factor A," *EMBO J.*, 9:2431-2438 (1990).

Xie et al., "Crystal *Structure* of JNK3: A Kinase Implicated in Neuronal Apoptosis," *Structure*, 6:983-991 (1998).

Yost et al., "GBP, an Inhibitor of GSK-3, Is Implicated in *Xenopus* Development and Oncogenesis," *Cell*, 93:1031-1041 (1998).

Zhang et al., "Activity of the MAP Kinase ERK2 is Controlled by a Flexible Surface Loop," *Structure*, 3:299-307 (1995).

Zhang et al., "Atomic Structure of the MAP Kinase ERK2 at 2.3 Å Resolution," *Nature*, 367:704-711 (1994).

Zhang et al., "Destabilization of β-Catenin by Mutations in Presenilin-1 Potentiates Neuronal Apoptosis," *Nature*, 395:698-702 (1998).

Zheng et al., "2.2 Å Refined Crystal Structure of the Catalytic Subunit of cAMP-Dependent Protein Kinase Complexed with MnATP and a Peptide Inhibitor," *Acta Cryst.*, D49:362-365 (1993).

Zhu et al., "The Direct Formation of Functionalized Alkyl(aryl)zinc Halides by Oxidative Addition of Highly Reactive Zinc with Organic Halides and Their Reactions with Acid Chlorides, α,β-Unsaturated Ketones, and Allylic, Aryl, and Vinyl Halides," *J. Org. Chem.*, 56:1445-1453 (1991).

\* cited by examiner

FIG. 1-1

|  |  | Atom Type | Resid | # | X | Y | Z | OCC | B |  |
|---|---|---|---|---|---|---|---|---|---|---|
| ATOM | 1 | N | SER A | 25 | 49.761 | 12.124 | 57.404 | 1.00 | 73.06 | N |
| ATOM | 2 | CA | SER A | 25 | 49.843 | 13.283 | 58.345 | 1.00 | 73.06 | C |
| ATOM | 3 | C | SER A | 25 | 50.651 | 14.389 | 57.666 | 1.00 | 73.06 | C |
| ATOM | 4 | O | SER A | 25 | 50.845 | 14.354 | 56.450 | 0.00 | 73.06 | O |
| ATOM | 5 | CB | SER A | 25 | 50.535 | 12.861 | 59.654 | 1.00 | 74.21 | C |
| ATOM | 6 | OG | SER A | 25 | 51.881 | 12.446 | 59.431 | 1.00 | 74.21 | O |
| ATOM | 7 | N | MET A | 26 | 51.124 | 15.366 | 58.439 | 1.00 | 60.23 | N |
| ATOM | 8 | CA | MET A | 26 | 51.921 | 16.424 | 57.824 | 1.00 | 60.23 | C |
| ATOM | 9 | C | MET A | 26 | 53.407 | 16.337 | 58.174 | 1.00 | 60.23 | C |
| ATOM | 10 | O | MET A | 26 | 53.781 | 16.042 | 59.315 | 1.00 | 60.23 | O |
| ATOM | 11 | CB | MET A | 26 | 51.352 | 17.824 | 58.147 | 1.00 | 70.25 | C |
| ATOM | 12 | CG | MET A | 26 | 51.419 | 18.290 | 59.592 | 1.00 | 70.25 | C |
| ATOM | 13 | SD | MET A | 26 | 50.344 | 19.765 | 59.811 | 1.00 | 70.25 | S |
| ATOM | 14 | CE | MET A | 26 | 48.782 | 18.955 | 60.093 | 1.00 | 70.25 | C |
| ATOM | 15 | N | LYS A | 27 | 54.235 | 16.565 | 57.153 | 1.00 | 56.51 | N |
| ATOM | 16 | CA | LYS A | 27 | 55.692 | 16.533 | 57.262 | 1.00 | 56.51 | C |
| ATOM | 17 | C | LYS A | 27 | 56.201 | 17.936 | 56.941 | 1.00 | 56.51 | C |
| ATOM | 18 | O | LYS A | 27 | 55.820 | 18.521 | 55.923 | 1.00 | 56.51 | O |
| ATOM | 19 | CB | LYS A | 27 | 56.269 | 15.513 | 56.273 | 1.00 | 46.92 | C |
| ATOM | 20 | CG | LYS A | 27 | 55.663 | 14.129 | 56.427 | 1.00 | 46.92 | C |
| ATOM | 21 | CD | LYS A | 27 | 56.373 | 13.074 | 55.597 | 0.00 | 46.92 | C |
| ATOM | 22 | CE | LYS A | 27 | 57.742 | 12.749 | 56.167 | 0.00 | 46.92 | C |
| ATOM | 23 | NZ | LYS A | 27 | 58.347 | 11.567 | 55.494 | 1.00 | 46.92 | N |
| ATOM | 24 | N | VAL A | 28 | 57.071 | 18.464 | 57.802 | 1.00 | 77.30 | N |
| ATOM | 25 | CA | VAL A | 28 | 57.594 | 19.824 | 57.645 | 1.00 | 77.30 | C |
| ATOM | 26 | C | VAL A | 28 | 59.109 | 19.917 | 57.462 | 1.00 | 77.30 | C |
| ATOM | 27 | O | VAL A | 28 | 59.849 | 19.965 | 58.445 | 1.00 | 77.30 | O |
| ATOM | 28 | CB | VAL A | 28 | 57.187 | 20.691 | 58.879 | 1.00 | 74.69 | C |
| ATOM | 29 | CG1 | VAL A | 28 | 57.571 | 19.979 | 60.170 | 0.00 | 74.69 | C |
| ATOM | 30 | CG2 | VAL A | 28 | 57.853 | 22.057 | 58.812 | 1.00 | 74.69 | C |
| ATOM | 31 | N | SER A | 29 | 59.562 | 19.953 | 56.206 | 1.00 | 60.45 | N |
| ATOM | 32 | CA | SER A | 29 | 60.987 | 20.058 | 55.915 | 1.00 | 60.45 | C |
| ATOM | 33 | C | SER A | 29 | 61.401 | 21.504 | 55.656 | 1.00 | 60.45 | C |
| ATOM | 34 | O | SER A | 29 | 60.549 | 22.390 | 55.583 | 1.00 | 60.45 | O |
| ATOM | 35 | N | ARG A | 30 | 62.705 | 21.753 | 55.522 | 1.00 | 100.00 | N |
| ATOM | 36 | CA | ARG A | 30 | 63.210 | 23.109 | 55.275 | 1.00 | 100.00 | C |
| ATOM | 37 | C | ARG A | 30 | 64.306 | 23.124 | 54.204 | 1.00 | 100.00 | C |
| ATOM | 38 | O | ARG A | 30 | 65.501 | 23.089 | 54.517 | 1.00 | 100.00 | O |
| ATOM | 39 | CB | ARG A | 30 | 63.741 | 23.734 | 56.582 | 1.00 | 93.57 | C |
| ATOM | 40 | CG | ARG A | 30 | 62.723 | 23.680 | 57.736 | 1.00 | 93.57 | C |
| ATOM | 41 | CD | ARG A | 30 | 62.760 | 24.920 | 58.641 | 1.00 | 93.57 | C |
| ATOM | 42 | NE | ARG A | 30 | 63.946 | 24.972 | 59.497 | 1.00 | 93.57 | N |
| ATOM | 43 | CZ | ARG A | 30 | 64.233 | 24.092 | 60.456 | 1.00 | 93.57 | C |
| ATOM | 44 | NH1 | ARG A | 30 | 63.420 | 23.072 | 60.697 | 0.00 | 93.57 | N |
| ATOM | 45 | NH2 | ARG A | 30 | 65.344 | 24.241 | 61.179 | 1.00 | 93.57 | N |
| ATOM | 46 | N | ASP A | 31 | 63.889 | 23.163 | 52.941 | 1.00 | 64.77 | N |
| ATOM | 47 | CA | ASP A | 31 | 64.842 | 23.183 | 51.853 | 0.00 | 64.77 | C |
| ATOM | 48 | C | ASP A | 31 | 64.524 | 24.323 | 50.914 | 1.00 | 64.77 | C |
| ATOM | 49 | O | ASP A | 31 | 63.517 | 25.024 | 51.097 | 1.00 | 64.77 | O |
| ATOM | 50 | N | LYS A | 32 | 65.380 | 24.508 | 49.907 | 1.00 | 94.72 | N |
| ATOM | 51 | CA | LYS A | 32 | 65.171 | 25.571 | 48.937 | 1.00 | 94.72 | C |
| ATOM | 52 | C | LYS A | 32 | 65.379 | 26.960 | 49.533 | 1.00 | 94.72 | C |
| ATOM | 53 | O | LYS A | 32 | 64.425 | 27.754 | 49.653 | 1.00 | 94.72 | O |
| ATOM | 54 | N | ASP A | 33 | 66.627 | 27.251 | 49.914 | 1.00 | 100.00 | N |
| ATOM | 55 | CA | ASP A | 33 | 66.961 | 28.548 | 50.491 | 1.00 | 100.00 | C |
| ATOM | 56 | C | ASP A | 33 | 66.187 | 28.957 | 51.741 | 1.00 | 100.00 | C |
| ATOM | 57 | O | ASP A | 33 | 65.140 | 29.613 | 51.650 | 1.00 | 100.00 | O |
| ATOM | 58 | N | GLY A | 34 | 66.705 | 28.575 | 52.907 | 1.00 | 55.02 | N |
| ATOM | 59 | CA | GLY A | 34 | 66.079 | 28.920 | 54.172 | 0.00 | 55.02 | C |
| ATOM | 60 | C | GLY A | 34 | 64.595 | 29.238 | 54.137 | 0.00 | 55.02 | C |

FIG. 1-2

| | | | | | | | | | |
|---|---|---|---|---|---|---|---|---|---|
| ATOM | 61 | O | GLY A | 34 | 64.195 | 30.402 | 54.124 | 0.00 55.02 | O |
| ATOM | 62 | N | SER A | 35 | 63.780 | 28.191 | 54.122 | 1.00 67.60 | N |
| ATOM | 63 | CA | SER A | 35 | 62.336 | 28.345 | 54.107 | 1.00 67.60 | C |
| ATOM | 64 | C | SER A | 35 | 61.644 | 27.095 | 54.652 | 1.00 67.60 | C |
| ATOM | 65 | O | SER A | 35 | 61.932 | 25.974 | 54.207 | 1.00 67.60 | O |
| ATOM | 66 | N | LYS A | 36 | 60.739 | 27.272 | 55.616 | 1.00 65.29 | N |
| ATOM | 67 | CA | LYS A | 36 | 60.010 | 26.138 | 56.199 | 1.00 65.29 | C |
| ATOM | 68 | C | LYS A | 36 | 58.952 | 25.617 | 55.247 | 1.00 65.29 | C |
| ATOM | 69 | O | LYS A | 36 | 58.126 | 26.383 | 54.745 | 1.00 65.29 | O |
| ATOM | 70 | CB | LYS A | 36 | 59.320 | 26.545 | 57.496 | 1.00 48.96 | C |
| ATOM | 71 | CG | LYS A | 36 | 58.431 | 25.464 | 58.105 | 1.00 48.96 | C |
| ATOM | 72 | CD | LYS A | 36 | 57.820 | 25.955 | 59.427 | 1.00 48.96 | C |
| ATOM | 73 | CE | LYS A | 36 | 57.028 | 24.873 | 60.134 | 1.00 48.96 | C |
| ATOM | 74 | NZ | LYS A | 36 | 56.438 | 25.361 | 61.412 | 0.00 48.96 | N |
| ATOM | 75 | N | VAL A | 37 | 58.968 | 24.309 | 55.010 | 1.00 60.62 | N |
| ATOM | 76 | CA | VAL A | 37 | 57.992 | 23.691 | 54.119 | 1.00 60.62 | C |
| ATOM | 77 | C | VAL A | 37 | 57.112 | 22.687 | 54.830 | 1.00 60.62 | C |
| ATOM | 78 | O | VAL A | 37 | 57.591 | 21.779 | 55.508 | 0.00 60.62 | O |
| ATOM | 79 | CB | VAL A | 37 | 58.668 | 22.974 | 52.944 | 1.00 46.81 | C |
| ATOM | 80 | CG1 | VAL A | 37 | 57.627 | 22.175 | 52.153 | 1.00 46.81 | C |
| ATOM | 81 | CG2 | VAL A | 37 | 59.352 | 23.994 | 52.044 | 1.00 46.81 | C |
| ATOM | 82 | N | THR A | 38 | 55.809 | 22.869 | 54.661 | 1.00 44.94 | N |
| ATOM | 83 | CA | THR A | 38 | 54.836 | 21.972 | 55.254 | 1.00 44.94 | C |
| ATOM | 84 | C | THR A | 38 | 54.233 | 21.142 | 54.129 | 1.00 44.94 | C |
| ATOM | 85 | O | THR A | 38 | 53.713 | 21.677 | 53.138 | 1.00 44.94 | O |
| ATOM | 86 | CB | THR A | 38 | 53.712 | 22.740 | 55.987 | 1.00 45.12 | C |
| ATOM | 87 | OG1 | THR A | 38 | 54.290 | 23.633 | 56.952 | 1.00 45.12 | O |
| ATOM | 88 | CG2 | THR A | 38 | 52.783 | 21.752 | 56.701 | 1.00 45.12 | C |
| ATOM | 89 | N | THR A | 39 | 54.343 | 19.827 | 54.278 | 1.00 39.35 | N |
| ATOM | 90 | CA | THR A | 39 | 53.818 | 18.901 | 53.300 | 1.00 39.35 | C |
| ATOM | 91 | C | THR A | 39 | 52.789 | 18.053 | 54.003 | 1.00 39.35 | C |
| ATOM | 92 | O | THR A | 39 | 52.973 | 17.646 | 55.149 | 1.00 39.35 | O |
| ATOM | 93 | CB | THR A | 39 | 54.914 | 17.998 | 52.738 | 1.00 43.54 | C |
| ATOM | 94 | OG1 | THR A | 39 | 55.894 | 18.803 | 52.063 | 1.00 43.54 | O |
| ATOM | 95 | CG2 | THR A | 39 | 54.315 | 16.996 | 51.755 | 1.00 43.54 | C |
| ATOM | 96 | N | VAL A | 40 | 51.692 | 17.795 | 53.316 | 1.00 39.28 | N |
| ATOM | 97 | CA | VAL A | 40 | 50.620 | 17.013 | 53.895 | 1.00 39.28 | C |
| ATOM | 98 | C | VAL A | 40 | 49.848 | 16.368 | 52.766 | 1.00 39.28 | C |
| ATOM | 99 | O | VAL A | 40 | 49.945 | 16.782 | 51.609 | 1.00 39.28 | O |
| ATOM | 100 | CB | VAL A | 40 | 49.647 | 17.914 | 54.710 | 1.00 35.69 | C |
| ATOM | 101 | CG1 | VAL A | 40 | 48.947 | 18.905 | 53.785 | 1.00 35.69 | C |
| ATOM | 102 | CG2 | VAL A | 40 | 48.622 | 17.055 | 55.432 | 0.00 35.69 | C |
| ATOM | 103 | N | VAL A | 41 | 49.077 | 15.351 | 53.106 | 1.00 37.75 | N |
| ATOM | 104 | CA | VAL A | 41 | 48.280 | 14.668 | 52.115 | 1.00 37.75 | C |
| ATOM | 105 | C | VAL A | 41 | 46.846 | 15.066 | 52.375 | 1.00 37.75 | C |
| ATOM | 106 | O | VAL A | 41 | 46.294 | 14.711 | 53.407 | 1.00 37.75 | O |
| ATOM | 107 | CB | VAL A | 41 | 48.429 | 13.149 | 52.257 | 1.00 35.15 | C |
| ATOM | 108 | CG1 | VAL A | 41 | 47.543 | 12.434 | 51.244 | 1.00 35.15 | C |
| ATOM | 109 | CG2 | VAL A | 41 | 49.894 | 12.767 | 52.075 | 1.00 35.15 | C |
| ATOM | 110 | N | ALA A | 42 | 46.246 | 15.812 | 51.453 | 1.00 35.42 | N |
| ATOM | 111 | CA | ALA A | 42 | 44.862 | 16.244 | 51.634 | 1.00 35.42 | C |
| ATOM | 112 | C | ALA A | 42 | 43.924 | 15.684 | 50.578 | 1.00 35.42 | C |
| ATOM | 113 | O | ALA A | 42 | 44.341 | 14.941 | 49.689 | 1.00 35.42 | O |
| ATOM | 114 | CB | ALA A | 42 | 44.782 | 17.757 | 51.634 | 1.00 58.29 | C |
| ATOM | 115 | N | THR A | 43 | 42.655 | 16.070 | 50.689 | 1.00 42.71 | N |
| ATOM | 116 | CA | THR A | 43 | 41.590 | 15.635 | 49.786 | 1.00 42.71 | C |
| ATOM | 117 | C | THR A | 43 | 41.051 | 16.801 | 48.950 | 1.00 42.71 | C |
| ATOM | 118 | O | THR A | 43 | 40.747 | 17.869 | 49.491 | 1.00 42.71 | O |
| ATOM | 119 | CB | THR A | 43 | 40.392 | 15.060 | 50.589 | 1.00 41.19 | C |
| ATOM | 120 | OG1 | THR A | 43 | 40.870 | 14.157 | 51.590 | 1.00 41.19 | O |
| ATOM | 121 | CG2 | THR A | 43 | 39.423 | 14.322 | 49.672 | 1.00 41.19 | C |

FIG. 1-3

| | | | | | | | | | | |
|---|---|---|---|---|---|---|---|---|---|---|
| ATOM | 122 | N   | PRO | A | 44 | 40.899 | 16.603 | 47.628 | 1.00 40.41 | N |
| ATOM | 123 | CA  | PRO | A | 44 | 40.385 | 17.640 | 46.729 | 1.00 40.41 | C |
| ATOM | 124 | C   | PRO | A | 44 | 39.113 | 18.213 | 47.319 | 1.00 40.41 | C |
| ATOM | 125 | O   | PRO | A | 44 | 38.334 | 17.477 | 47.925 | 1.00 40.41 | O |
| ATOM | 126 | CB  | PRO | A | 44 | 40.090 | 16.872 | 45.445 | 1.00 39.12 | C |
| ATOM | 127 | CG  | PRO | A | 44 | 41.122 | 15.825 | 45.437 | 1.00 39.12 | C |
| ATOM | 128 | CD  | PRO | A | 44 | 41.125 | 15.351 | 46.888 | 1.00 39.12 | C |
| ATOM | 129 | N   | GLY | A | 45 | 38.897 | 19.515 | 47.157 | 1.00 31.93 | N |
| ATOM | 130 | CA  | GLY | A | 45 | 37.687 | 20.113 | 47.687 | 1.00 31.93 | C |
| ATOM | 131 | C   | GLY | A | 45 | 36.476 | 19.506 | 47.011 | 1.00 31.93 | C |
| ATOM | 132 | O   | GLY | A | 45 | 35.509 | 19.121 | 47.660 | 1.00 31.93 | O |
| ATOM | 133 | N   | GLN | A | 46 | 36.541 | 19.422 | 45.689 | 1.00 46.73 | N |
| ATOM | 134 | CA  | GLN | A | 46 | 35.468 | 18.853 | 44.885 | 1.00 46.73 | C |
| ATOM | 135 | C   | GLN | A | 46 | 36.067 | 17.703 | 44.082 | 1.00 46.73 | C |
| ATOM | 136 | O   | GLN | A | 46 | 37.292 | 17.621 | 43.919 | 1.00 46.73 | O |
| ATOM | 137 | CB  | GLN | A | 46 | 34.901 | 19.910 | 43.950 | 1.00 47.06 | C |
| ATOM | 138 | N   | GLY | A | 47 | 35.216 | 16.813 | 43.579 | 1.00 65.73 | N |
| ATOM | 139 | CA  | GLY | A | 47 | 35.722 | 15.684 | 42.809 | 1.00 65.73 | C |
| ATOM | 140 | C   | GLY | A | 47 | 35.779 | 14.418 | 43.650 | 1.00 65.73 | C |
| ATOM | 141 | O   | GLY | A | 47 | 35.366 | 14.430 | 44.817 | 1.00 65.73 | O |
| ATOM | 142 | N   | PRO | A | 48 | 36.288 | 13.305 | 43.095 | 1.00 49.54 | N |
| ATOM | 143 | CA  | PRO | A | 48 | 36.386 | 12.029 | 43.820 | 1.00 49.54 | C |
| ATOM | 144 | C   | PRO | A | 48 | 37.581 | 12.049 | 44.781 | 1.00 49.54 | C |
| ATOM | 145 | O   | PRO | A | 48 | 38.625 | 12.627 | 44.467 | 1.00 49.54 | O |
| ATOM | 146 | CB  | PRO | A | 48 | 36.578 | 11.002 | 42.698 | 1.00 58.10 | C |
| ATOM | 147 | CG  | PRO | A | 48 | 36.272 | 11.782 | 41.404 | 1.00 58.10 | C |
| ATOM | 148 | CD  | PRO | A | 48 | 36.772 | 13.149 | 41.717 | 1.00 58.10 | C |
| ATOM | 149 | N   | ASP | A | 49 | 37.428 | 11.419 | 45.940 | 1.00 61.37 | N |
| ATOM | 150 | CA  | ASP | A | 49 | 38.497 | 11.388 | 46.936 | 1.00 61.37 | C |
| ATOM | 151 | C   | ASP | A | 49 | 39.746 | 10.738 | 46.347 | 1.00 61.37 | C |
| ATOM | 152 | O   | ASP | A | 49 | 39.815 |  9.510 | 46.243 | 1.00 61.37 | O |
| ATOM | 153 | CB  | ASP | A | 49 | 38.063 | 10.591 | 48.179 | 1.00 57.83 | C |
| ATOM | 154 | CG  | ASP | A | 49 | 38.999 | 10.804 | 49.371 | 1.00 57.83 | C |
| ATOM | 155 | OD1 | ASP | A | 49 | 40.235 | 10.962 | 49.172 | 1.00 57.83 | O |
| ATOM | 156 | OD2 | ASP | A | 49 | 38.486 | 10.803 | 50.513 | 1.00 57.83 | O |
| ATOM | 157 | N   | ARG | A | 50 | 40.721 | 11.563 | 45.970 | 1.00 44.76 | N |
| ATOM | 158 | CA  | ARG | A | 50 | 41.976 | 11.091 | 45.394 | 1.00 44.76 | C |
| ATOM | 159 | C   | ARG | A | 50 | 43.095 | 11.965 | 45.954 | 1.00 44.76 | C |
| ATOM | 160 | O   | ARG | A | 50 | 43.581 | 12.890 | 45.291 | 1.00 44.76 | O |
| ATOM | 161 | CB  | ARG | A | 50 | 41.927 | 11.184 | 43.868 | 1.00 49.13 | C |
| ATOM | 162 | CG  | ARG | A | 50 | 40.824 | 10.341 | 43.264 | 1.00 49.13 | C |
| ATOM | 163 | CD  | ARG | A | 50 | 41.134 |  8.852 | 43.346 | 1.00 49.13 | C |
| ATOM | 164 | NE  | ARG | A | 50 | 42.017 |  8.452 | 42.253 | 1.00 49.13 | N |
| ATOM | 165 | CZ  | ARG | A | 50 | 42.534 |  7.235 | 42.102 | 1.00 49.13 | C |
| ATOM | 166 | NH1 | ARG | A | 50 | 42.261 |  6.278 | 42.978 | 0.00 49.13 | N |
| ATOM | 167 | NH2 | ARG | A | 50 | 43.318 |  6.976 | 41.063 | 1.00 49.13 | N |
| ATOM | 168 | N   | PRO | A | 51 | 43.530 | 11.655 | 47.186 | 1.00 32.41 | N |
| ATOM | 169 | CA  | PRO | A | 51 | 44.577 | 12.346 | 47.939 | 1.00 32.41 | C |
| ATOM | 170 | C   | PRO | A | 51 | 45.713 | 12.895 | 47.100 | 1.00 32.41 | C |
| ATOM | 171 | O   | PRO | A | 51 | 45.946 | 12.434 | 45.990 | 1.00 32.41 | O |
| ATOM | 172 | CB  | PRO | A | 51 | 45.040 | 11.281 | 48.933 | 1.00 34.03 | C |
| ATOM | 173 | CG  | PRO | A | 51 | 44.677 |  9.986 | 48.262 | 1.00 34.03 | C |
| ATOM | 174 | CD  | PRO | A | 51 | 43.326 | 10.302 | 47.732 | 1.00 34.03 | C |
| ATOM | 175 | N   | GLN | A | 52 | 46.401 | 13.904 | 47.632 | 1.00 44.27 | N |
| ATOM | 176 | CA  | GLN | A | 52 | 47.541 | 14.509 | 46.946 | 1.00 44.27 | C |
| ATOM | 177 | C   | GLN | A | 52 | 48.532 | 15.144 | 47.915 | 1.00 44.27 | C |
| ATOM | 178 | O   | GLN | A | 52 | 48.202 | 15.421 | 49.077 | 1.00 44.27 | O |
| ATOM | 179 | CB  | GLN | A | 52 | 47.076 | 15.564 | 45.958 | 0.00 68.01 | C |
| ATOM | 180 | CG  | GLN | A | 52 | 45.589 | 15.689 | 45.884 | 0.00 68.01 | C |
| ATOM | 181 | CD  | GLN | A | 52 | 45.145 | 16.042 | 44.505 | 1.00 68.01 | C |
| ATOM | 182 | OE1 | GLN | A | 52 | 45.422 | 17.145 | 44.014 | 1.00 68.01 | O |
| ATOM | 183 | NE2 | GLN | A | 52 | 44.464 | 15.104 | 43.846 | 1.00 68.01 | N |

FIG. 1-4

| ATOM | 184 | N | GLU | A | 53 | 49.753 | 15.349 | 47.428 | 1.00 | 37.18 | N |
|---|---|---|---|---|---|---|---|---|---|---|---|
| ATOM | 185 | CA | GLU | A | 53 | 50.809 | 15.972 | 48.211 | 1.00 | 37.18 | C |
| ATOM | 186 | C | GLU | A | 53 | 50.690 | 17.475 | 48.033 | 1.00 | 37.18 | C |
| ATOM | 187 | O | GLU | A | 53 | 50.883 | 17.987 | 46.932 | 1.00 | 37.18 | O |
| ATOM | 188 | CB | GLU | A | 53 | 52.187 | 15.540 | 47.716 | 1.00 | 47.66 | C |
| ATOM | 189 | CG | GLU | A | 53 | 52.569 | 14.112 | 48.019 | 1.00 | 47.66 | C |
| ATOM | 190 | CD | GLU | A | 53 | 53.813 | 14.034 | 48.875 | 1.00 | 47.66 | C |
| ATOM | 191 | OE1 | GLU | A | 53 | 54.795 | 14.750 | 48.556 | 1.00 | 47.66 | O |
| ATOM | 192 | OE2 | GLU | A | 53 | 53.805 | 13.256 | 49.856 | 1.00 | 47.66 | O |
| ATOM | 193 | N | VAL | A | 54 | 50.374 | 18.180 | 49.112 | 1.00 | 39.29 | N |
| ATOM | 194 | CA | VAL | A | 54 | 50.259 | 19.621 | 49.037 | 1.00 | 39.29 | C |
| ATOM | 195 | C | VAL | A | 54 | 51.333 | 20.241 | 49.910 | 1.00 | 39.29 | C |
| ATOM | 196 | O | VAL | A | 54 | 51.416 | 19.967 | 51.107 | 1.00 | 39.29 | O |
| ATOM | 197 | CB | VAL | A | 54 | 48.863 | 20.083 | 49.473 | 1.00 | 31.58 | C |
| ATOM | 198 | CG1 | VAL | A | 54 | 48.758 | 21.599 | 49.382 | 1.00 | 31.58 | C |
| ATOM | 199 | CG2 | VAL | A | 54 | 47.817 | 19.435 | 48.578 | 1.00 | 31.58 | C |
| ATOM | 200 | N | SER | A | 55 | 52.173 | 21.065 | 49.295 | 1.00 | 42.34 | N |
| ATOM | 201 | CA | SER | A | 55 | 53.259 | 21.708 | 50.020 | 1.00 | 42.34 | C |
| ATOM | 202 | C | SER | A | 55 | 53.152 | 23.226 | 49.958 | 1.00 | 42.34 | C |
| ATOM | 203 | O | SER | A | 55 | 53.131 | 23.829 | 48.878 | 1.00 | 42.34 | O |
| ATOM | 204 | CB | SER | A | 55 | 54.603 | 21.292 | 49.435 | 1.00 | 48.76 | C |
| ATOM | 205 | OG | SER | A | 55 | 54.845 | 21.999 | 48.229 | 1.00 | 48.76 | O |
| ATOM | 206 | N | TYR | A | 56 | 53.110 | 23.846 | 51.127 | 1.00 | 56.49 | N |
| ATOM | 207 | CA | TYR | A | 56 | 53.002 | 25.290 | 51.189 | 1.00 | 56.49 | C |
| ATOM | 208 | C | TYR | A | 56 | 54.009 | 25.847 | 52.149 | 1.00 | 56.49 | C |
| ATOM | 209 | O | TYR | A | 56 | 54.557 | 25.121 | 52.976 | 1.00 | 56.49 | O |
| ATOM | 210 | CB | TYR | A | 56 | 51.612 | 25.691 | 51.652 | 1.00 | 34.56 | C |
| ATOM | 211 | CG | TYR | A | 56 | 51.278 | 25.232 | 53.053 | 1.00 | 34.56 | C |
| ATOM | 212 | CD1 | TYR | A | 56 | 51.574 | 26.019 | 54.164 | 1.00 | 34.56 | C |
| ATOM | 213 | CD2 | TYR | A | 56 | 50.594 | 24.038 | 53.257 | 1.00 | 34.56 | C |
| ATOM | 214 | CE1 | TYR | A | 56 | 51.173 | 25.634 | 55.444 | 1.00 | 34.56 | C |
| ATOM | 215 | CE2 | TYR | A | 56 | 50.198 | 23.644 | 54.523 | 1.00 | 34.56 | C |
| ATOM | 216 | CZ | TYR | A | 56 | 50.484 | 24.448 | 55.612 | 1.00 | 34.56 | C |
| ATOM | 217 | OH | TYR | A | 56 | 50.032 | 24.068 | 56.858 | 1.00 | 34.56 | O |
| ATOM | 218 | N | THR | A | 57 | 54.239 | 27.147 | 52.047 | 1.00 | 50.93 | N |
| ATOM | 219 | CA | THR | A | 57 | 55.182 | 27.802 | 52.923 | 1.00 | 50.93 | C |
| ATOM | 220 | C | THR | A | 57 | 54.670 | 29.187 | 53.287 | 1.00 | 50.93 | C |
| ATOM | 221 | O | THR | A | 57 | 53.611 | 29.606 | 52.811 | 1.00 | 50.93 | O |
| ATOM | 222 | CB | THR | A | 57 | 56.536 | 27.929 | 52.243 | 1.00 | 66.35 | C |
| ATOM | 223 | OG1 | THR | A | 57 | 57.426 | 28.632 | 53.113 | 1.00 | 66.35 | O |
| ATOM | 224 | CG2 | THR | A | 57 | 56.408 | 28.684 | 50.934 | 0.00 | 66.35 | C |
| ATOM | 225 | N | ASP | A | 58 | 55.423 | 29.888 | 54.133 | 1.00 | 59.63 | N |
| ATOM | 226 | CA | ASP | A | 58 | 55.063 | 31.237 | 54.560 | 1.00 | 59.63 | C |
| ATOM | 227 | C | ASP | A | 58 | 53.720 | 31.256 | 55.299 | 1.00 | 59.63 | C |
| ATOM | 228 | O | ASP | A | 58 | 52.869 | 32.118 | 55.031 | 1.00 | 59.63 | O |
| ATOM | 229 | CB | ASP | A | 58 | 54.980 | 32.180 | 53.344 | 1.00 | 61.93 | C |
| ATOM | 230 | CG | ASP | A | 58 | 56.237 | 32.150 | 52.485 | 1.00 | 61.93 | C |
| ATOM | 231 | OD1 | ASP | A | 58 | 57.277 | 31.664 | 52.987 | 1.00 | 61.93 | O |
| ATOM | 232 | OD2 | ASP | A | 58 | 56.190 | 32.625 | 51.319 | 1.00 | 61.93 | O |
| ATOM | 233 | N | THR | A | 59 | 53.518 | 30.320 | 56.222 | 1.00 | 48.28 | N |
| ATOM | 234 | CA | THR | A | 59 | 52.257 | 30.288 | 56.955 | 1.00 | 48.28 | C |
| ATOM | 235 | C | THR | A | 59 | 52.272 | 31.364 | 58.024 | 1.00 | 48.28 | C |
| ATOM | 236 | O | THR | A | 59 | 53.131 | 31.352 | 58.906 | 1.00 | 48.28 | O |
| ATOM | 237 | CB | THR | A | 59 | 52.004 | 28.919 | 57.644 | 1.00 | 63.84 | C |
| ATOM | 238 | OG1 | THR | A | 59 | 52.862 | 28.789 | 58.787 | 1.00 | 63.84 | O |
| ATOM | 239 | CG2 | THR | A | 59 | 52.280 | 27.775 | 56.680 | 1.00 | 63.84 | C |
| ATOM | 240 | N | LYS | A | 60 | 51.323 | 32.295 | 57.928 | 1.00 | 61.08 | N |
| ATOM | 241 | CA | LYS | A | 60 | 51.191 | 33.403 | 58.884 | 1.00 | 61.08 | C |
| ATOM | 242 | C | LYS | A | 60 | 49.749 | 33.499 | 59.376 | 1.00 | 61.08 | C |
| ATOM | 243 | O | LYS | A | 60 | 48.818 | 33.584 | 58.569 | 1.00 | 61.08 | O |
| ATOM | 244 | CB | LYS | A | 60 | 51.616 | 34.739 | 58.249 | 1.00 | 57.34 | C |
| ATOM | 245 | CG | LYS | A | 60 | 51.353 | 34.847 | 56.759 | 1.00 | 57.34 | C |

FIG. 1-5

```
ATOM    246  CD   LYS A  60      51.449  36.292  56.249  1.00 57.34           C
ATOM    247  CE   LYS A  60      52.858  36.868  56.356  1.00 57.34           C
ATOM    248  NZ   LYS A  60      53.897  36.075  55.626  1.00 57.34           N
ATOM    249  N    VAL A  61      49.588  33.492  60.701  1.00 65.10           N
ATOM    250  CA   VAL A  61      48.289  33.536  61.377  1.00 65.10           C
ATOM    251  C    VAL A  61      47.505  34.808  61.113  1.00 65.10           C
ATOM    252  O    VAL A  61      47.152  35.526  62.047  1.00 65.10           O
ATOM    253  CB   VAL A  61      48.455  33.391  62.919  1.00 40.01           C
ATOM    254  CG1  VAL A  61      47.101  33.164  63.578  0.00 40.01           C
ATOM    255  CG2  VAL A  61      49.407  32.249  63.238  0.00 40.01           C
ATOM    256  N    ILE A  62      47.207  35.073  59.846  1.00100.00           N
ATOM    257  CA   ILE A  62      46.467  36.277  59.455  1.00100.00           C
ATOM    258  C    ILE A  62      45.156  36.519  60.196  1.00100.00           C
ATOM    259  O    ILE A  62      44.836  37.668  60.531  1.00100.00           O
ATOM    260  CB   ILE A  62      46.099  36.274  57.956  1.00 50.02           C
ATOM    261  CG1  ILE A  62      45.123  35.123  57.678  1.00 50.02           C
ATOM    262  CG2  ILE A  62      47.362  36.214  57.105  1.00 50.02           C
ATOM    263  CD1  ILE A  62      44.528  35.137  56.283  1.00 50.02           C
ATOM    264  N    GLY A  63      44.386  35.457  60.427  1.00 44.28           N
ATOM    265  CA   GLY A  63      43.111  35.635  61.087  1.00 44.28           C
ATOM    266  C    GLY A  63      42.932  34.729  62.272  1.00 44.28           C
ATOM    267  O    GLY A  63      43.567  33.674  62.384  1.00 44.28           O
ATOM    268  N    ASN A  64      42.052  35.156  63.163  1.00 62.35           N
ATOM    269  CA   ASN A  64      41.742  34.426  64.384  1.00 62.35           C
ATOM    270  C    ASN A  64      40.240  34.409  64.673  1.00 62.35           C
ATOM    271  O    ASN A  64      39.780  34.764  65.750  1.00 62.35           O
ATOM    272  CB   ASN A  64      42.484  35.099  65.540  1.00 83.43           C
ATOM    273  CG   ASN A  64      42.465  34.196  66.747  1.00 83.43           C
ATOM    274  OD1  ASN A  64      41.449  34.028  67.415  1.00 83.43           O
ATOM    275  ND2  ASN A  64      43.645  33.630  67.054  0.00 83.43           N
ATOM    276  N    GLY A  65      39.455  34.023  63.653  1.00 85.88           N
ATOM    277  CA   GLY A  65      38.018  33.917  63.883  1.00 85.88           C
ATOM    278  C    GLY A  65      37.748  33.418  65.305  1.00 85.88           C
ATOM    279  O    GLY A  65      38.578  33.522  66.198  1.00 85.88           O
ATOM    280  N    SER A  66      36.527  32.884  65.514  1.00 83.87           N
ATOM    281  CA   SER A  66      36.196  32.388  66.845  1.00 83.87           C
ATOM    282  C    SER A  66      36.304  30.866  66.942  1.00 83.87           C
ATOM    283  O    SER A  66      36.889  30.311  67.865  1.00 83.87           O
ATOM    284  CB   SER A  66      34.781  32.841  67.208  1.00 65.14           C
ATOM    285  OG   SER A  66      34.043  33.090  66.010  1.00 65.14           O
ATOM    286  N    PHE A  67      35.683  30.179  65.963  1.00 87.07           N
ATOM    287  CA   PHE A  67      35.646  28.718  66.018  1.00 87.07           C
ATOM    288  C    PHE A  67      37.039  28.094  65.947  1.00 87.07           C
ATOM    289  O    PHE A  67      37.275  26.976  66.391  1.00 87.07           O
ATOM    290  CB   PHE A  67      34.791  28.204  64.858  1.00 77.20           C
ATOM    291  CG   PHE A  67      33.373  28.655  65.042  1.00 77.20           C
ATOM    292  CD1  PHE A  67      33.037  29.966  64.738  1.00 77.20           C
ATOM    293  CD2  PHE A  67      32.443  27.805  65.618  1.00 77.20           C
ATOM    294  CE1  PHE A  67      31.760  30.431  65.016  0.00 77.20           C
ATOM    295  CE2  PHE A  67      31.162  28.282  65.897  1.00 77.20           C
ATOM    296  CZ   PHE A  67      30.817  29.594  65.597  1.00 77.20           C
ATOM    297  N    GLY A  68      37.973  28.836  65.331  1.00 62.91           N
ATOM    298  CA   GLY A  68      39.311  28.276  65.181  1.00 62.91           C
ATOM    299  C    GLY A  68      40.320  29.337  64.736  1.00 62.91           C
ATOM    300  O    GLY A  68      40.232  30.510  65.075  1.00 62.91           O
ATOM    301  N    VAL A  69      41.335  28.875  63.983  1.00 53.87           N
ATOM    302  CA   VAL A  69      42.347  29.803  63.495  1.00 53.87           C
ATOM    303  C    VAL A  69      42.351  29.872  61.967  1.00 53.87           C
ATOM    304  O    VAL A  69      42.098  28.900  61.268  1.00 53.87           O
ATOM    305  CB   VAL A  69      43.710  29.329  63.999  1.00 67.84           C
ATOM    306  CG1  VAL A  69      44.227  30.280  65.077  0.00 67.84           C
ATOM    307  CG2  VAL A  69      43.591  27.932  64.578  1.00 67.84           C
```

FIG. 1-6

```
ATOM    308  N    VAL A  70      42.610  31.089  61.456  1.00 54.39           N
ATOM    309  CA   VAL A  70      42.671  31.266  60.011  1.00 54.39           C
ATOM    310  C    VAL A  70      44.100  31.567  59.551  1.00 54.39           C
ATOM    311  O    VAL A  70      44.699  32.576  59.899  1.00 54.39           O
ATOM    312  CB   VAL A  70      41.745  32.424  59.634  1.00 28.35           C
ATOM    313  CG1  VAL A  70      41.969  32.815  58.174  1.00 28.35           C
ATOM    314  CG2  VAL A  70      40.297  32.015  59.826  0.00 28.35           C
ATOM    315  N    TYR A  71      44.661  30.622  58.773  1.00 54.24           N
ATOM    316  CA   TYR A  71      46.038  30.785  58.321  1.00 54.24           C
ATOM    317  C    TYR A  71      46.112  31.192  56.847  1.00 54.24           C
ATOM    318  O    TYR A  71      45.257  30.869  56.033  1.00 54.24           O
ATOM    319  CB   TYR A  71      46.765  29.456  58.521  1.00 56.39           C
ATOM    320  CG   TYR A  71      46.872  29.146  59.971  1.00 56.39           C
ATOM    321  CD1  TYR A  71      45.925  28.324  60.574  1.00 56.39           C
ATOM    322  CD2  TYR A  71      47.969  29.593  60.709  1.00 56.39           C
ATOM    323  CE1  TYR A  71      46.079  27.938  61.897  1.00 56.39           C
ATOM    324  CE2  TYR A  71      48.123  29.207  62.033  1.00 56.39           C
ATOM    325  CZ   TYR A  71      47.187  28.379  62.624  1.00 56.39           C
ATOM    326  OH   TYR A  71      47.363  27.944  63.923  1.00 56.39           O
ATOM    327  N    GLN A  72      47.169  31.961  56.523  1.00 40.81           N
ATOM    328  CA   GLN A  72      47.368  32.365  55.136  1.00 40.81           C
ATOM    329  C    GLN A  72      48.642  31.748  54.552  1.00 40.81           C
ATOM    330  O    GLN A  72      49.706  31.764  55.158  1.00 40.81           O
ATOM    331  CB   GLN A  72      47.460  33.891  55.091  1.00 71.49           C
ATOM    332  CG   GLN A  72      47.226  34.453  53.687  0.00 71.49           C
ATOM    333  CD   GLN A  72      48.554  34.639  52.992  1.00 71.49           C
ATOM    334  OE1  GLN A  72      49.409  33.770  52.951  1.00 71.49           O
ATOM    335  NE2  GLN A  72      48.699  35.846  52.409  1.00 71.49           N
ATOM    336  N    ALA A  73      48.711  31.077  53.405  1.00 48.24           N
ATOM    337  CA   ALA A  73      49.960  30.453  52.989  1.00 48.24           C
ATOM    338  C    ALA A  73      50.239  30.505  51.493  1.00 48.24           C
ATOM    339  O    ALA A  73      49.409  30.945  50.688  1.00 48.24           O
ATOM    340  CB   ALA A  73      50.006  29.006  53.472  1.00 31.25           C
ATOM    341  N    LYS A  74      51.428  30.034  51.131  1.00 51.92           N
ATOM    342  CA   LYS A  74      51.883  30.029  49.751  1.00 51.92           C
ATOM    343  C    LYS A  74      52.137  28.589  49.294  1.00 51.92           C
ATOM    344  O    LYS A  74      52.856  27.839  49.962  1.00 51.92           O
ATOM    345  CB   LYS A  74      53.175  30.858  49.653  1.00 49.31           C
ATOM    346  CG   LYS A  74      53.682  31.081  48.233  1.00 49.31           C
ATOM    347  CD   LYS A  74      54.790  32.136  48.168  1.00 49.31           C
ATOM    348  CE   LYS A  74      55.300  32.298  46.743  0.00 49.31           C
ATOM    349  NZ   LYS A  74      55.857  31.026  46.202  0.00 49.31           N
ATOM    350  N    LEU A  75      51.535  28.198  48.172  1.00 52.53           N
ATOM    351  CA   LEU A  75      51.732  26.851  47.649  1.00 52.53           C
ATOM    352  C    LEU A  75      53.084  26.845  46.934  1.00 52.53           C
ATOM    353  O    LEU A  75      53.322  27.649  46.022  1.00 52.53           O
ATOM    354  CB   LEU A  75      50.612  26.480  46.674  1.00 33.25           C
ATOM    355  CG   LEU A  75      49.186  26.317  47.227  1.00 33.25           C
ATOM    356  CD1  LEU A  75      48.275  25.795  46.118  1.00 33.25           C
ATOM    357  CD2  LEU A  75      49.175  25.362  48.406  1.00 33.25           C
ATOM    358  N    CYS A  76      53.967  25.945  47.362  1.00 54.76           N
ATOM    359  CA   CYS A  76      55.308  25.843  46.799  1.00 54.76           C
ATOM    360  C    CYS A  76      55.424  25.778  45.289  1.00 54.76           C
ATOM    361  O    CYS A  76      56.356  26.346  44.712  1.00 54.76           O
ATOM    362  CB   CYS A  76      56.016  24.635  47.368  1.00 54.02           C
ATOM    363  SG   CYS A  76      56.149  24.736  49.116  1.00 54.02           S
ATOM    364  N    ASP A  77      54.500  25.081  44.641  1.00 52.22           N
ATOM    365  CA   ASP A  77      54.577  24.951  43.200  1.00 52.22           C
ATOM    366  C    ASP A  77      53.997  26.139  42.424  1.00 52.22           C
ATOM    367  O    ASP A  77      54.756  26.939  41.860  1.00 52.22           O
ATOM    368  CB   ASP A  77      53.931  23.627  42.797  1.00 81.37           C
ATOM    369  CG   ASP A  77      54.744  22.412  43.293  1.00 81.37           C
```

FIG. 1-7

| ATOM | 370 | OD1 | ASP | A | 77 | 55.813 | 22.630 | 43.931 | 1.00 | 81.37 | O |
|---|---|---|---|---|---|---|---|---|---|---|---|
| ATOM | 371 | OD2 | ASP | A | 77 | 54.323 | 21.245 | 43.045 | 1.00 | 81.37 | O |
| ATOM | 372 | N | SER | A | 78 | 52.669 | 26.263 | 42.397 | 1.00 | 65.45 | N |
| ATOM | 373 | CA | SER | A | 78 | 52.013 | 27.373 | 41.693 | 1.00 | 65.45 | C |
| ATOM | 374 | C | SER | A | 78 | 52.378 | 28.736 | 42.305 | 1.00 | 65.45 | C |
| ATOM | 375 | O | SER | A | 78 | 52.338 | 29.770 | 41.633 | 1.00 | 65.45 | O |
| ATOM | 376 | CB | SER | A | 78 | 50.491 | 27.216 | 41.759 | 1.00 | 60.65 | C |
| ATOM | 377 | OG | SER | A | 78 | 50.021 | 27.564 | 43.056 | 1.00 | 60.65 | O |
| ATOM | 378 | N | GLY | A | 79 | 52.726 | 28.738 | 43.586 | 1.00 | 63.24 | N |
| ATOM | 379 | CA | GLY | A | 79 | 53.054 | 29.993 | 44.237 | 1.00 | 63.24 | C |
| ATOM | 380 | C | GLY | A | 79 | 51.776 | 30.710 | 44.655 | 1.00 | 63.24 | C |
| ATOM | 381 | O | GLY | A | 79 | 51.825 | 31.794 | 45.250 | 1.00 | 63.24 | O |
| ATOM | 382 | N | GLU | A | 80 | 50.624 | 30.107 | 44.350 | 1.00 | 59.92 | N |
| ATOM | 383 | CA | GLU | A | 80 | 49.333 | 30.703 | 44.706 | 1.00 | 59.92 | C |
| ATOM | 384 | C | GLU | A | 80 | 49.184 | 30.881 | 46.208 | 1.00 | 59.92 | C |
| ATOM | 385 | O | GLU | A | 80 | 49.721 | 30.101 | 46.995 | 1.00 | 59.92 | O |
| ATOM | 386 | CB | GLU | A | 80 | 48.188 | 29.833 | 44.200 | 1.00 | 74.64 | C |
| ATOM | 387 | CG | GLU | A | 80 | 48.007 | 29.855 | 42.703 | 1.00 | 74.64 | C |
| ATOM | 388 | CD | GLU | A | 80 | 47.013 | 28.820 | 42.260 | 1.00 | 74.64 | C |
| ATOM | 389 | OE1 | GLU | A | 80 | 47.311 | 27.607 | 42.398 | 1.00 | 74.64 | O |
| ATOM | 390 | OE2 | GLU | A | 80 | 45.923 | 29.220 | 41.789 | 1.00 | 74.64 | O |
| ATOM | 391 | N | LEU | A | 81 | 48.456 | 31.913 | 46.609 | 1.00 | 43.62 | N |
| ATOM | 392 | CA | LEU | A | 81 | 48.247 | 32.168 | 48.023 | 1.00 | 43.62 | C |
| ATOM | 393 | C | LEU | A | 81 | 46.940 | 31.545 | 48.458 | 1.00 | 43.62 | C |
| ATOM | 394 | O | LEU | A | 81 | 45.888 | 31.822 | 47.893 | 1.00 | 43.62 | O |
| ATOM | 395 | CB | LEU | A | 81 | 48.234 | 33.673 | 48.291 | 1.00 | 60.15 | C |
| ATOM | 396 | CG | LEU | A | 81 | 49.631 | 34.295 | 48.325 | 1.00 | 60.15 | C |
| ATOM | 397 | CD1 | LEU | A | 81 | 49.555 | 35.818 | 48.466 | 1.00 | 60.15 | C |
| ATOM | 398 | CD2 | LEU | A | 81 | 50.388 | 33.674 | 49.507 | 1.00 | 60.15 | C |
| ATOM | 399 | N | VAL | A | 82 | 47.007 | 30.685 | 49.456 | 1.00 | 32.15 | N |
| ATOM | 400 | CA | VAL | A | 82 | 45.812 | 30.031 | 49.940 | 1.00 | 32.15 | C |
| ATOM | 401 | C | VAL | A | 82 | 45.549 | 30.482 | 51.355 | 1.00 | 32.15 | C |
| ATOM | 402 | O | VAL | A | 82 | 46.362 | 31.183 | 51.948 | 1.00 | 32.15 | O |
| ATOM | 403 | CB | VAL | A | 82 | 45.966 | 28.489 | 49.920 | 1.00 | 25.28 | C |
| ATOM | 404 | CG1 | VAL | A | 82 | 45.867 | 27.974 | 48.489 | 1.00 | 25.28 | C |
| ATOM | 405 | CG2 | VAL | A | 82 | 47.303 | 28.094 | 50.533 | 1.00 | 25.28 | C |
| ATOM | 406 | N | ALA | A | 83 | 44.401 | 30.080 | 51.881 | 1.00 | 36.55 | N |
| ATOM | 407 | CA | ALA | A | 83 | 44.011 | 30.413 | 53.238 | 1.00 | 36.55 | C |
| ATOM | 408 | C | ALA | A | 83 | 43.668 | 29.103 | 53.904 | 1.00 | 36.55 | C |
| ATOM | 409 | O | ALA | A | 83 | 43.085 | 28.211 | 53.284 | 1.00 | 36.55 | O |
| ATOM | 410 | CB | ALA | A | 83 | 42.798 | 31.320 | 53.228 | 1.00 | 40.81 | C |
| ATOM | 411 | N | ILE | A | 84 | 44.019 | 28.973 | 55.170 | 1.00 | 42.30 | N |
| ATOM | 412 | CA | ILE | A | 84 | 43.734 | 27.736 | 55.858 | 1.00 | 42.30 | C |
| ATOM | 413 | C | ILE | A | 84 | 42.967 | 28.008 | 57.132 | 1.00 | 42.30 | C |
| ATOM | 414 | O | ILE | A | 84 | 43.491 | 28.607 | 58.073 | 1.00 | 42.30 | O |
| ATOM | 415 | CB | ILE | A | 84 | 45.046 | 26.990 | 56.166 | 1.00 | 28.52 | C |
| ATOM | 416 | CG1 | ILE | A | 84 | 45.822 | 26.789 | 54.853 | 1.00 | 28.52 | C |
| ATOM | 417 | CG2 | ILE | A | 84 | 44.747 | 25.665 | 56.860 | 1.00 | 28.52 | C |
| ATOM | 418 | CD1 | ILE | A | 84 | 47.146 | 26.082 | 54.999 | 1.00 | 28.52 | C |
| ATOM | 419 | N | LYS | A | 85 | 41.713 | 27.589 | 57.158 | 1.00 | 34.53 | N |
| ATOM | 420 | CA | LYS | A | 85 | 40.910 | 27.801 | 58.343 | 1.00 | 34.53 | C |
| ATOM | 421 | C | LYS | A | 85 | 40.972 | 26.534 | 59.182 | 1.00 | 34.53 | C |
| ATOM | 422 | O | LYS | A | 85 | 40.342 | 25.530 | 58.844 | 1.00 | 34.53 | O |
| ATOM | 423 | CB | LYS | A | 85 | 39.446 | 28.097 | 57.974 | 1.00 | 53.69 | C |
| ATOM | 424 | CG | LYS | A | 85 | 38.555 | 28.240 | 59.205 | 1.00 | 53.69 | C |
| ATOM | 425 | CD | LYS | A | 85 | 37.058 | 28.157 | 58.908 | 1.00 | 53.69 | C |
| ATOM | 426 | CE | LYS | A | 85 | 36.519 | 29.379 | 58.154 | 1.00 | 53.69 | C |
| ATOM | 427 | NZ | LYS | A | 85 | 35.021 | 29.335 | 58.021 | 1.00 | 53.69 | N |
| ATOM | 428 | N | LYS | A | 86 | 41.742 | 26.564 | 60.264 | 1.00 | 44.17 | N |
| ATOM | 429 | CA | LYS | A | 86 | 41.822 | 25.391 | 61.122 | 1.00 | 44.17 | C |
| ATOM | 430 | C | LYS | A | 86 | 40.811 | 25.537 | 62.239 | 1.00 | 44.17 | C |
| ATOM | 431 | O | LYS | A | 86 | 40.958 | 26.415 | 63.091 | 1.00 | 44.17 | O |

FIG. 1-8

| | | | | | | | | | | |
|---|---|---|---|---|---|---|---|---|---|---|
| ATOM | 432 | CB  | LYS | A | 86 | 43.221 | 25.236 | 61.722 | 1.00 43.95 | C |
| ATOM | 433 | CG  | LYS | A | 86 | 43.349 | 24.035 | 62.648 | 0.00 43.95 | C |
| ATOM | 434 | CD  | LYS | A | 86 | 44.716 | 23.374 | 62.544 | 0.00 43.95 | C |
| ATOM | 435 | CE  | LYS | A | 86 | 45.843 | 24.296 | 62.978 | 0.00 43.95 | C |
| ATOM | 436 | NZ  | LYS | A | 86 | 47.169 | 23.621 | 62.840 | 1.00 43.95 | N |
| ATOM | 437 | N   | VAL | A | 87 | 39.776 | 24.698 | 62.225 | 1.00 48.58 | N |
| ATOM | 438 | CA  | VAL | A | 87 | 38.755 | 24.735 | 63.269 | 1.00 48.58 | C |
| ATOM | 439 | C   | VAL | A | 87 | 38.853 | 23.404 | 64.014 | 1.00 48.58 | C |
| ATOM | 440 | O   | VAL | A | 87 | 39.323 | 22.408 | 63.450 | 1.00 48.58 | O |
| ATOM | 441 | CB  | VAL | A | 87 | 37.335 | 24.893 | 62.689 | 1.00 34.61 | C |
| ATOM | 442 | CG1 | VAL | A | 87 | 36.881 | 23.588 | 62.077 | 1.00 34.61 | C |
| ATOM | 443 | CG2 | VAL | A | 87 | 36.374 | 25.331 | 63.781 | 0.00 34.61 | C |
| ATOM | 444 | N   | LEU | A | 88 | 38.406 | 23.392 | 65.272 | 1.00 79.34 | N |
| ATOM | 445 | CA  | LEU | A | 88 | 38.484 | 22.196 | 66.119 | 1.00 79.34 | C |
| ATOM | 446 | C   | LEU | A | 88 | 37.542 | 21.069 | 65.692 | 1.00 79.34 | C |
| ATOM | 447 | O   | LEU | A | 88 | 36.480 | 20.871 | 66.284 | 1.00 79.34 | O |
| ATOM | 448 | CB  | LEU | A | 88 | 38.216 | 22.578 | 67.582 | 1.00 59.72 | C |
| ATOM | 449 | CG  | LEU | A | 88 | 38.780 | 21.662 | 68.674 | 1.00 59.72 | C |
| ATOM | 450 | CD1 | LEU | A | 88 | 38.094 | 20.304 | 68.667 | 0.00 59.72 | C |
| ATOM | 451 | CD2 | LEU | A | 88 | 40.285 | 21.517 | 68.446 | 1.00 59.72 | C |
| ATOM | 452 | N   | GLN | A | 89 | 37.944 | 20.323 | 64.666 | 1.00 72.41 | N |
| ATOM | 453 | CA  | GLN | A | 89 | 37.137 | 19.216 | 64.169 | 1.00 72.41 | C |
| ATOM | 454 | C   | GLN | A | 89 | 36.832 | 18.254 | 65.306 | 1.00 72.41 | C |
| ATOM | 455 | O   | GLN | A | 89 | 37.666 | 18.033 | 66.194 | 1.00 72.41 | O |
| ATOM | 456 | CB  | GLN | A | 89 | 37.873 | 18.485 | 63.063 | 0.00 35.69 | C |
| ATOM | 457 | N   | ASP | A | 90 | 35.630 | 17.687 | 65.269 | 1.00 90.18 | N |
| ATOM | 458 | CA  | ASP | A | 90 | 35.181 | 16.732 | 66.281 | 1.00 90.18 | C |
| ATOM | 459 | C   | ASP | A | 90 | 34.732 | 15.443 | 65.593 | 1.00 90.18 | C |
| ATOM | 460 | O   | ASP | A | 90 | 34.280 | 15.470 | 64.449 | 0.00 90.18 | O |
| ATOM | 461 | CB  | ASP | A | 90 | 34.010 | 17.330 | 67.078 | 1.00 57.39 | C |
| ATOM | 462 | N   | LYS | A | 91 | 34.859 | 14.317 | 66.290 | 1.00 91.89 | N |
| ATOM | 463 | CA  | LYS | A | 91 | 34.419 | 13.040 | 65.721 | 1.00 91.89 | C |
| ATOM | 464 | C   | LYS | A | 91 | 32.926 | 12.808 | 66.058 | 1.00 91.89 | C |
| ATOM | 465 | O   | LYS | A | 91 | 32.292 | 11.894 | 65.514 | 1.00 91.89 | O |
| ATOM | 466 | CB  | LYS | A | 91 | 35.271 | 11.894 | 66.270 | 1.00 68.26 | C |
| ATOM | 467 | N   | ARG | A | 92 | 32.374 | 13.646 | 66.940 | 1.00 72.03 | N |
| ATOM | 468 | CA  | ARG | A | 92 | 30.972 | 13.530 | 67.347 | 1.00 72.03 | C |
| ATOM | 469 | C   | ARG | A | 92 | 29.995 | 13.660 | 66.172 | 1.00 72.03 | C |
| ATOM | 470 | O   | ARG | A | 92 | 28.799 | 13.360 | 66.325 | 1.00 72.03 | O |
| ATOM | 471 | CB  | ARG | A | 92 | 30.642 | 14.592 | 68.420 | 1.00 56.05 | C |
| ATOM | 472 | N   | PHE | A | 93 | 30.490 | 14.116 | 65.013 | 1.00 67.00 | N |
| ATOM | 473 | CA  | PHE | A | 93 | 29.636 | 14.277 | 63.817 | 1.00 67.00 | C |
| ATOM | 474 | C   | PHE | A | 93 | 30.360 | 14.863 | 62.589 | 1.00 67.00 | C |
| ATOM | 475 | O   | PHE | A | 93 | 31.562 | 15.149 | 62.627 | 1.00 67.00 | O |
| ATOM | 476 | CB  | PHE | A | 93 | 28.420 | 15.141 | 64.157 | 0.00 35.69 | C |
| ATOM | 477 | N   | LYS | A | 94 | 29.624 | 15.031 | 61.494 | 1.00 51.48 | N |
| ATOM | 478 | CA  | LYS | A | 94 | 30.203 | 15.594 | 60.273 | 1.00 51.48 | C |
| ATOM | 479 | C   | LYS | A | 94 | 30.321 | 17.118 | 60.429 | 1.00 51.48 | C |
| ATOM | 480 | O   | LYS | A | 94 | 29.620 | 17.738 | 61.250 | 1.00 51.48 | O |
| ATOM | 481 | CB  | LYS | A | 94 | 29.331 | 15.253 | 59.071 | 0.00 35.69 | C |
| ATOM | 482 | N   | ASN | A | 95 | 31.218 | 17.717 | 59.655 | 1.00 34.95 | N |
| ATOM | 483 | CA  | ASN | A | 95 | 31.401 | 19.160 | 59.717 | 1.00 34.95 | C |
| ATOM | 484 | C   | ASN | A | 95 | 30.562 | 19.796 | 58.608 | 1.00 34.95 | C |
| ATOM | 485 | O   | ASN | A | 95 | 30.909 | 19.742 | 57.432 | 1.00 34.95 | O |
| ATOM | 486 | CB  | ASN | A | 95 | 32.880 | 19.523 | 59.555 | 1.00 44.43 | C |
| ATOM | 487 | CG  | ASN | A | 95 | 33.152 | 20.968 | 59.890 | 1.00 44.43 | C |
| ATOM | 488 | OD1 | ASN | A | 95 | 32.707 | 21.867 | 59.176 | 1.00 44.43 | O |
| ATOM | 489 | ND2 | ASN | A | 95 | 33.870 | 21.207 | 60.993 | 1.00 44.43 | N |
| ATOM | 490 | N   | ARG | A | 96 | 29.438 | 20.379 | 59.008 | 1.00 34.56 | N |
| ATOM | 491 | CA  | ARG | A | 96 | 28.504 | 21.016 | 58.090 | 1.00 34.56 | C |
| ATOM | 492 | C   | ARG | A | 96 | 29.121 | 21.976 | 57.078 | 1.00 34.56 | C |
| ATOM | 493 | O   | ARG | A | 96 | 28.735 | 21.963 | 55.912 | 1.00 34.56 | O |

FIG. 1-9

| | | | | | | | | | |
|---|---|---|---|---|---|---|---|---|---|
| ATOM | 494 | CB | ARG A | 96 | 27.424 | 21.745 | 58.882 | 1.00 40.73 | C |
| ATOM | 495 | CG | ARG A | 96 | 26.445 | 22.485 | 58.012 | 1.00 40.73 | C |
| ATOM | 496 | CD | ARG A | 96 | 25.496 | 23.294 | 58.854 | 1.00 40.73 | C |
| ATOM | 497 | NE | ARG A | 96 | 24.681 | 22.440 | 59.702 | 1.00 40.73 | N |
| ATOM | 498 | CZ | ARG A | 96 | 23.859 | 22.893 | 60.641 | 1.00 40.73 | C |
| ATOM | 499 | NH1 | ARG A | 96 | 23.752 | 24.201 | 60.854 | 1.00 40.73 | N |
| ATOM | 500 | NH2 | ARG A | 96 | 23.135 | 22.039 | 61.355 | 1.00 40.73 | N |
| ATOM | 501 | N | GLU A | 97 | 30.058 | 22.815 | 57.512 | 1.00 27.76 | N |
| ATOM | 502 | CA | GLU A | 97 | 30.686 | 23.751 | 56.591 | 1.00 27.76 | C |
| ATOM | 503 | C | GLU A | 97 | 31.401 | 22.947 | 55.519 | 1.00 27.76 | C |
| ATOM | 504 | O | GLU A | 97 | 31.151 | 23.130 | 54.330 | 1.00 27.76 | O |
| ATOM | 505 | CB | GLU A | 97 | 31.666 | 24.684 | 57.324 | 1.00 34.86 | C |
| ATOM | 506 | CG | GLU A | 97 | 32.493 | 25.561 | 56.381 | 1.00 34.86 | C |
| ATOM | 507 | CD | GLU A | 97 | 33.175 | 26.742 | 57.065 | 1.00 34.86 | C |
| ATOM | 508 | OE1 | GLU A | 97 | 33.379 | 26.690 | 58.299 | 1.00 34.86 | O |
| ATOM | 509 | OE2 | GLU A | 97 | 33.524 | 27.719 | 56.353 | 1.00 34.86 | O |
| ATOM | 510 | N | LEU A | 98 | 32.278 | 22.045 | 55.947 | 1.00 29.35 | N |
| ATOM | 511 | CA | LEU A | 98 | 33.000 | 21.187 | 55.022 | 1.00 29.35 | C |
| ATOM | 512 | C | LEU A | 98 | 32.024 | 20.498 | 54.079 | 1.00 29.35 | C |
| ATOM | 513 | O | LEU A | 98 | 32.208 | 20.488 | 52.867 | 1.00 29.35 | O |
| ATOM | 514 | CB | LEU A | 98 | 33.768 | 20.113 | 55.779 | 1.00 27.06 | C |
| ATOM | 515 | CG | LEU A | 98 | 34.273 | 18.972 | 54.888 | 1.00 27.06 | C |
| ATOM | 516 | CD1 | LEU A | 98 | 35.236 | 19.512 | 53.843 | 1.00 27.06 | C |
| ATOM | 517 | CD2 | LEU A | 98 | 34.950 | 17.927 | 55.743 | 1.00 27.06 | C |
| ATOM | 518 | N | GLN A | 99 | 30.981 | 19.911 | 54.635 | 1.00 35.85 | N |
| ATOM | 519 | CA | GLN A | 99 | 30.027 | 19.227 | 53.795 | 1.00 35.85 | C |
| ATOM | 520 | C | GLN A | 99 | 29.423 | 20.174 | 52.760 | 1.00 35.85 | C |
| ATOM | 521 | O | GLN A | 99 | 29.413 | 19.870 | 51.560 | 1.00 35.85 | O |
| ATOM | 522 | CB | GLN A | 99 | 28.935 | 18.554 | 54.649 | 1.00 48.31 | C |
| ATOM | 523 | CG | GLN A | 99 | 29.467 | 17.459 | 55.595 | 0.00 48.31 | C |
| ATOM | 524 | CD | GLN A | 99 | 30.595 | 16.603 | 54.997 | 1.00 48.31 | C |
| ATOM | 525 | OE1 | GLN A | 99 | 30.452 | 16.003 | 53.926 | 1.00 48.31 | O |
| ATOM | 526 | NE2 | GLN A | 99 | 31.722 | 16.544 | 55.700 | 1.00 48.31 | N |
| ATOM | 527 | N | ILE A | 100 | 28.945 | 21.331 | 53.210 | 1.00 37.51 | N |
| ATOM | 528 | CA | ILE A | 100 | 28.337 | 22.289 | 52.293 | 1.00 37.51 | C |
| ATOM | 529 | C | ILE A | 100 | 29.301 | 22.772 | 51.214 | 1.00 37.51 | C |
| ATOM | 530 | O | ILE A | 100 | 28.977 | 22.779 | 50.021 | 1.00 37.51 | O |
| ATOM | 531 | CB | ILE A | 100 | 27.786 | 23.487 | 53.060 | 1.00 24.76 | C |
| ATOM | 532 | CG1 | ILE A | 100 | 26.602 | 23.025 | 53.909 | 1.00 24.76 | C |
| ATOM | 533 | CG2 | ILE A | 100 | 27.384 | 24.602 | 52.094 | 1.00 24.76 | C |
| ATOM | 534 | CD1 | ILE A | 100 | 26.069 | 24.076 | 54.806 | 1.00 24.76 | C |
| ATOM | 535 | N | MET A | 101 | 30.493 | 23.169 | 51.624 | 1.00 34.60 | N |
| ATOM | 536 | CA | MET A | 101 | 31.452 | 23.646 | 50.657 | 1.00 34.60 | C |
| ATOM | 537 | C | MET A | 101 | 31.939 | 22.556 | 49.733 | 1.00 34.60 | C |
| ATOM | 538 | O | MET A | 101 | 32.421 | 22.831 | 48.637 | 1.00 34.60 | O |
| ATOM | 539 | CB | MET A | 101 | 32.623 | 24.289 | 51.372 | 1.00 44.27 | C |
| ATOM | 540 | CG | MET A | 101 | 32.278 | 25.669 | 51.904 | 1.00 44.27 | C |
| ATOM | 541 | SD | MET A | 101 | 33.586 | 26.784 | 51.454 | 1.00 44.27 | S |
| ATOM | 542 | CE | MET A | 101 | 34.778 | 26.342 | 52.697 | 1.00 44.27 | C |
| ATOM | 543 | N | ARG A | 102 | 31.806 | 21.315 | 50.176 | 1.00 44.54 | N |
| ATOM | 544 | CA | ARG A | 102 | 32.248 | 20.181 | 49.384 | 1.00 44.54 | C |
| ATOM | 545 | C | ARG A | 102 | 31.359 | 20.058 | 48.137 | 1.00 44.54 | C |
| ATOM | 546 | O | ARG A | 102 | 31.740 | 19.415 | 47.154 | 1.00 44.54 | O |
| ATOM | 547 | CB | ARG A | 102 | 32.164 | 18.911 | 50.236 | 1.00 47.18 | C |
| ATOM | 548 | CG | ARG A | 102 | 32.971 | 17.725 | 49.747 | 1.00 47.18 | C |
| ATOM | 549 | CD | ARG A | 102 | 34.103 | 17.414 | 50.708 | 1.00 47.18 | C |
| ATOM | 550 | NE | ARG A | 102 | 34.693 | 16.092 | 50.479 | 1.00 47.18 | N |
| ATOM | 551 | CZ | ARG A | 102 | 34.083 | 14.933 | 50.737 | 1.00 47.18 | C |
| ATOM | 552 | NH1 | ARG A | 102 | 32.850 | 14.915 | 51.241 | 1.00 47.18 | N |
| ATOM | 553 | NH2 | ARG A | 102 | 34.706 | 13.789 | 50.488 | 0.00 47.18 | N |
| ATOM | 554 | N | LYS A | 103 | 30.187 | 20.687 | 48.164 | 1.00 25.86 | N |
| ATOM | 555 | CA | LYS A | 103 | 29.288 | 20.597 | 47.025 | 1.00 25.86 | C |

FIG. 1-10

| | | | | | | | | | |
|---|---|---|---|---|---|---|---|---|---|
| ATOM | 556 | C | LYS | A | 103 | 29.047 | 21.891 | 46.269 | 1.00 25.86 | C |
| ATOM | 557 | O | LYS | A | 103 | 28.101 | 21.999 | 45.504 | 1.00 25.86 | O |
| ATOM | 558 | CB | LYS | A | 103 | 27.935 | 19.999 | 47.447 | 1.00 42.64 | C |
| ATOM | 559 | CG | LYS | A | 103 | 27.255 | 20.630 | 48.647 | 1.00 42.64 | C |
| ATOM | 560 | CD | LYS | A | 103 | 25.724 | 20.455 | 48.594 | 1.00 42.64 | C |
| ATOM | 561 | CE | LYS | A | 103 | 25.233 | 19.015 | 48.773 | 1.00 42.64 | C |
| ATOM | 562 | NZ | LYS | A | 103 | 25.461 | 18.448 | 50.150 | 1.00 42.64 | N |
| ATOM | 563 | N | LEU | A | 104 | 29.911 | 22.872 | 46.455 | 1.00 37.96 | N |
| ATOM | 564 | CA | LEU | A | 104 | 29.724 | 24.136 | 45.765 | 1.00 37.96 | C |
| ATOM | 565 | C | LEU | A | 104 | 30.795 | 24.393 | 44.722 | 1.00 37.96 | C |
| ATOM | 566 | O | LEU | A | 104 | 31.987 | 24.275 | 44.990 | 1.00 37.96 | O |
| ATOM | 567 | CB | LEU | A | 104 | 29.688 | 25.284 | 46.775 | 1.00 37.19 | C |
| ATOM | 568 | CG | LEU | A | 104 | 28.326 | 25.673 | 47.370 | 1.00 37.19 | C |
| ATOM | 569 | CD1 | LEU | A | 104 | 27.526 | 24.451 | 47.771 | 1.00 37.19 | C |
| ATOM | 570 | CD2 | LEU | A | 104 | 28.566 | 26.583 | 48.565 | 1.00 37.19 | C |
| ATOM | 571 | N | ASP | A | 105 | 30.354 | 24.713 | 43.513 | 1.00 35.85 | N |
| ATOM | 572 | CA | ASP | A | 105 | 31.274 | 25.017 | 42.434 | 1.00 35.85 | C |
| ATOM | 573 | C | ASP | A | 105 | 30.652 | 26.168 | 41.667 | 1.00 35.85 | C |
| ATOM | 574 | O | ASP | A | 105 | 29.788 | 25.960 | 40.810 | 1.00 35.85 | O |
| ATOM | 575 | CB | ASP | A | 105 | 31.470 | 23.811 | 41.521 | 0.00 46.91 | C |
| ATOM | 576 | CG | ASP | A | 105 | 32.491 | 24.073 | 40.443 | 1.00 46.91 | C |
| ATOM | 577 | OD1 | ASP | A | 105 | 33.552 | 24.660 | 40.761 | 1.00 46.91 | O |
| ATOM | 578 | OD2 | ASP | A | 105 | 32.238 | 23.696 | 39.278 | 1.00 46.91 | O |
| ATOM | 579 | N | HIS | A | 106 | 31.076 | 27.387 | 42.007 | 1.00 22.60 | N |
| ATOM | 580 | CA | HIS | A | 106 | 30.546 | 28.583 | 41.371 | 1.00 22.60 | C |
| ATOM | 581 | C | HIS | A | 106 | 31.606 | 29.665 | 41.329 | 1.00 22.60 | C |
| ATOM | 582 | O | HIS | A | 106 | 32.392 | 29.810 | 42.252 | 1.00 22.60 | O |
| ATOM | 583 | CB | HIS | A | 106 | 29.308 | 29.065 | 42.120 | 1.00 24.71 | C |
| ATOM | 584 | CG | HIS | A | 106 | 28.550 | 30.135 | 41.403 | 1.00 24.71 | C |
| ATOM | 585 | ND1 | HIS | A | 106 | 28.996 | 31.435 | 41.318 | 1.00 24.71 | N |
| ATOM | 586 | CD2 | HIS | A | 106 | 27.373 | 30.096 | 40.732 | 1.00 24.71 | C |
| ATOM | 587 | CE1 | HIS | A | 106 | 28.125 | 32.153 | 40.629 | 1.00 24.71 | C |
| ATOM | 588 | NE2 | HIS | A | 106 | 27.132 | 31.363 | 40.262 | 1.00 24.71 | N |
| ATOM | 589 | N | CYS | A | 107 | 31.620 | 30.424 | 40.241 | 1.00 38.47 | N |
| ATOM | 590 | CA | CYS | A | 107 | 32.616 | 31.468 | 40.052 | 1.00 38.47 | C |
| ATOM | 591 | C | CYS | A | 107 | 32.495 | 32.617 | 41.029 | 1.00 38.47 | C |
| ATOM | 592 | O | CYS | A | 107 | 33.287 | 33.543 | 40.986 | 1.00 38.47 | O |
| ATOM | 593 | CB | CYS | A | 107 | 32.562 | 32.007 | 38.616 | 1.00 37.90 | C |
| ATOM | 594 | SG | CYS | A | 107 | 31.007 | 32.828 | 38.143 | 1.00 37.90 | S |
| ATOM | 595 | N | ASN | A | 108 | 31.525 | 32.554 | 41.928 | 1.00 34.41 | N |
| ATOM | 596 | CA | ASN | A | 108 | 31.345 | 33.632 | 42.887 | 1.00 34.41 | C |
| ATOM | 597 | C | ASN | A | 108 | 31.354 | 33.178 | 44.338 | 1.00 34.41 | C |
| ATOM | 598 | O | ASN | A | 108 | 30.897 | 33.888 | 45.231 | 1.00 34.41 | O |
| ATOM | 599 | CB | ASN | A | 108 | 30.056 | 34.386 | 42.558 | 1.00 26.75 | C |
| ATOM | 600 | CG | ASN | A | 108 | 30.225 | 35.321 | 41.371 | 1.00 26.75 | C |
| ATOM | 601 | OD1 | ASN | A | 108 | 29.311 | 35.526 | 40.569 | 1.00 26.75 | O |
| ATOM | 602 | ND2 | ASN | A | 108 | 31.402 | 35.902 | 41.265 | 1.00 26.75 | N |
| ATOM | 603 | N | ILE | A | 109 | 31.880 | 31.985 | 44.574 | 1.00 26.40 | N |
| ATOM | 604 | CA | ILE | A | 109 | 31.970 | 31.463 | 45.929 | 1.00 26.40 | C |
| ATOM | 605 | C | ILE | A | 109 | 33.422 | 31.034 | 46.123 | 1.00 26.40 | C |
| ATOM | 606 | O | ILE | A | 109 | 34.013 | 30.445 | 45.217 | 1.00 26.40 | O |
| ATOM | 607 | CB | ILE | A | 109 | 31.049 | 30.245 | 46.116 | 1.00 20.95 | C |
| ATOM | 608 | CG1 | ILE | A | 109 | 29.592 | 30.648 | 45.890 | 1.00 20.95 | C |
| ATOM | 609 | CG2 | ILE | A | 109 | 31.243 | 29.660 | 47.496 | 1.00 20.95 | C |
| ATOM | 610 | CD1 | ILE | A | 109 | 28.635 | 29.474 | 45.843 | 0.00 20.95 | C |
| ATOM | 611 | N | VAL | A | 110 | 34.014 | 31.343 | 47.271 | 1.00 21.56 | N |
| ATOM | 612 | CA | VAL | A | 110 | 35.392 | 30.928 | 47.494 | 1.00 21.56 | C |
| ATOM | 613 | C | VAL | A | 110 | 35.488 | 29.447 | 47.184 | 1.00 21.56 | C |
| ATOM | 614 | O | VAL | A | 110 | 34.571 | 28.682 | 47.450 | 1.00 21.56 | O |
| ATOM | 615 | CB | VAL | A | 110 | 35.860 | 31.150 | 48.951 | 1.00 28.38 | C |
| ATOM | 616 | CG1 | VAL | A | 110 | 36.336 | 32.556 | 49.129 | 1.00 28.38 | C |
| ATOM | 617 | CG2 | VAL | A | 110 | 34.725 | 30.847 | 49.914 | 1.00 28.38 | C |

FIG. 1-11

```
ATOM    618  N    ARG A 111      36.619  29.061  46.620  1.00 26.01       N
ATOM    619  CA   ARG A 111      36.882  27.689  46.233  1.00 26.01       C
ATOM    620  C    ARG A 111      37.595  26.926  47.356  1.00 26.01       C
ATOM    621  O    ARG A 111      38.528  27.438  47.987  1.00 26.01       O
ATOM    622  CB   ARG A 111      37.753  27.709  44.968  1.00 74.46       C
ATOM    623  CG   ARG A 111      37.449  26.661  43.902  1.00 74.46       C
ATOM    624  CD   ARG A 111      38.176  27.020  42.592  1.00 74.46       C
ATOM    625  NE   ARG A 111      39.614  27.206  42.804  1.00 74.46       N
ATOM    626  CZ   ARG A 111      40.294  28.326  42.525  1.00 74.46       C
ATOM    627  NH1  ARG A 111      39.663  29.385  42.010  1.00 74.46       N
ATOM    628  NH2  ARG A 111      41.608  28.392  42.758  1.00 74.46       N
ATOM    629  N    LEU A 112      37.131  25.708  47.615  1.00 28.45       N
ATOM    630  CA   LEU A 112      37.757  24.857  48.619  1.00 28.45       C
ATOM    631  C    LEU A 112      38.804  24.020  47.874  1.00 28.45       C
ATOM    632  O    LEU A 112      38.483  22.965  47.337  1.00 28.45       O
ATOM    633  CB   LEU A 112      36.735  23.916  49.267  1.00 23.28       C
ATOM    634  CG   LEU A 112      37.352  22.977  50.319  1.00 23.28       C
ATOM    635  CD1  LEU A 112      37.639  23.768  51.586  1.00 23.28       C
ATOM    636  CD2  LEU A 112      36.425  21.797  50.624  1.00 23.28       C
ATOM    637  N    ARG A 113      40.047  24.484  47.826  1.00 26.78       N
ATOM    638  CA   ARG A 113      41.078  23.734  47.118  1.00 26.78       C
ATOM    639  C    ARG A 113      41.241  22.325  47.701  1.00 26.78       C
ATOM    640  O    ARG A 113      41.126  21.327  46.992  1.00 26.78       O
ATOM    641  CB   ARG A 113      42.424  24.466  47.194  1.00 66.27       C
ATOM    642  CG   ARG A 113      42.325  25.990  47.160  1.00 66.27       C
ATOM    643  CD   ARG A 113      41.871  26.498  45.816  1.00 66.27       C
ATOM    644  NE   ARG A 113      42.985  26.718  44.895  1.00 66.27       N
ATOM    645  CZ   ARG A 113      43.812  27.764  44.951  1.00 66.27       C
ATOM    646  NH1  ARG A 113      43.646  28.686  45.893  1.00 66.27       N
ATOM    647  NH2  ARG A 113      44.794  27.900  44.055  1.00 66.27       N
ATOM    648  N    TYR A 114      41.496  22.247  49.003  1.00 41.01       N
ATOM    649  CA   TYR A 114      41.707  20.966  49.657  1.00 41.01       C
ATOM    650  C    TYR A 114      41.279  21.086  51.099  1.00 41.01       C
ATOM    651  O    TYR A 114      40.965  22.170  51.578  1.00 41.01       O
ATOM    652  CB   TYR A 114      43.202  20.609  49.677  1.00 35.34       C
ATOM    653  CG   TYR A 114      43.946  20.748  48.366  1.00 35.34       C
ATOM    654  CD1  TYR A 114      43.812  19.797  47.365  1.00 35.34       C
ATOM    655  CD2  TYR A 114      44.794  21.829  48.134  1.00 35.34       C
ATOM    656  CE1  TYR A 114      44.501  19.918  46.161  1.00 35.34       C
ATOM    657  CE2  TYR A 114      45.484  21.960  46.933  1.00 35.34       C
ATOM    658  CZ   TYR A 114      45.331  20.998  45.954  1.00 35.34       C
ATOM    659  OH   TYR A 114      45.995  21.115  44.757  1.00 35.34       O
ATOM    660  N    PHE A 115      41.303  19.956  51.790  1.00 39.24       N
ATOM    661  CA   PHE A 115      41.006  19.913  53.207  1.00 39.24       C
ATOM    662  C    PHE A 115      41.721  18.696  53.810  1.00 39.24       C
ATOM    663  O    PHE A 115      41.898  17.679  53.144  1.00 39.24       O
ATOM    664  CB   PHE A 115      39.499  19.860  53.436  1.00 31.61       C
ATOM    665  CG   PHE A 115      38.864  18.580  53.022  1.00 31.61       C
ATOM    666  CD1  PHE A 115      38.748  17.529  53.922  1.00 31.61       C
ATOM    667  CD2  PHE A 115      38.305  18.448  51.751  1.00 31.61       C
ATOM    668  CE1  PHE A 115      38.072  16.368  53.568  1.00 31.61       C
ATOM    669  CE2  PHE A 115      37.623  17.287  51.383  1.00 31.61       C
ATOM    670  CZ   PHE A 115      37.504  16.249  52.294  1.00 31.61       C
ATOM    671  N    PHE A 116      42.166  18.818  55.056  1.00 46.90       N
ATOM    672  CA   PHE A 116      42.862  17.723  55.724  1.00 46.90       C
ATOM    673  C    PHE A 116      42.779  17.895  57.232  1.00 46.90       C
ATOM    674  O    PHE A 116      42.307  18.926  57.723  1.00 46.90       O
ATOM    675  CB   PHE A 116      44.322  17.681  55.282  1.00 27.87       C
ATOM    676  CG   PHE A 116      45.112  18.890  55.687  1.00 27.87       C
ATOM    677  CD1  PHE A 116      45.650  18.991  56.960  1.00 27.87       C
ATOM    678  CD2  PHE A 116      45.319  19.938  54.789  1.00 27.87       C
ATOM    679  CE1  PHE A 116      46.382  20.123  57.337  1.00 27.87       C
```

FIG. 1-12

```
ATOM    680  CE2 PHE A 116      46.050  21.072  55.159  1.00 27.87           C
ATOM    681  CZ  PHE A 116      46.581  21.162  56.434  1.00 27.87           C
ATOM    682  N   TYR A 117      43.253  16.888  57.961  1.00 64.42           N
ATOM    683  CA  TYR A 117      43.221  16.908  59.421  1.00 64.42           C
ATOM    684  C   TYR A 117      44.594  17.059  60.126  1.00 64.42           C
ATOM    685  O   TYR A 117      45.635  16.612  59.613  1.00 64.42           O
ATOM    686  CB  TYR A 117      42.489  15.652  59.895  1.00 44.40           C
ATOM    687  CG  TYR A 117      41.058  15.583  59.375  1.00 44.40           C
ATOM    688  CD1 TYR A 117      40.078  16.473  59.838  1.00 44.40           C
ATOM    689  CD2 TYR A 117      40.686  14.648  58.404  1.00 44.40           C
ATOM    690  CE1 TYR A 117      38.766  16.428  59.350  1.00 44.40           C
ATOM    691  CE2 TYR A 117      39.381  14.597  57.911  1.00 44.40           C
ATOM    692  CZ  TYR A 117      38.428  15.486  58.388  1.00 44.40           C
ATOM    693  OH  TYR A 117      37.128  15.419  57.920  1.00 44.40           O
ATOM    694  N   SER A 118      44.577  17.722  61.292  1.00 83.11           N
ATOM    695  CA  SER A 118      45.773  17.972  62.124  1.00 83.11           C
ATOM    696  C   SER A 118      45.413  17.716  63.583  1.00 83.11           C
ATOM    697  O   SER A 118      44.267  17.959  63.999  1.00 83.11           O
ATOM    698  CB  SER A 118      46.235  19.430  62.022  1.00 70.63           C
ATOM    699  OG  SER A 118      46.412  19.833  60.677  1.00 70.63           O
ATOM    700  N   SER A 119      46.395  17.260  64.361  1.00 68.91           N
ATOM    701  CA  SER A 119      46.180  16.967  65.779  1.00 68.91           C
ATOM    702  C   SER A 119      46.199  18.227  66.648  1.00 68.91           C
ATOM    703  O   SER A 119      46.474  19.326  66.162  1.00 68.91           O
ATOM    704  CB  SER A 119      47.248  15.987  66.269  1.00 69.37           C
ATOM    705  OG  SER A 119      47.158  14.759  65.562  1.00 69.37           O
ATOM    706  N   TYR A 127      42.467  20.925  64.527  1.00 61.36           N
ATOM    707  CA  TYR A 127      41.976  19.596  64.149  1.00 61.36           C
ATOM    708  C   TYR A 127      41.643  19.495  62.642  1.00 61.36           C
ATOM    709  O   TYR A 127      42.286  18.728  61.919  1.00 61.36           O
ATOM    710  CB  TYR A 127      40.746  19.214  65.007  1.00 37.80           C
ATOM    711  N   LEU A 128      40.638  20.241  62.172  1.00 53.88           N
ATOM    712  CA  LEU A 128      40.281  20.224  60.742  1.00 53.88           C
ATOM    713  C   LEU A 128      40.810  21.467  60.042  1.00 53.88           C
ATOM    714  O   LEU A 128      40.764  22.578  60.595  1.00 53.88           O
ATOM    715  CB  LEU A 128      38.766  20.163  60.520  1.00 37.71           C
ATOM    716  CG  LEU A 128      38.395  20.424  59.051  1.00 37.71           C
ATOM    717  CD1 LEU A 128      39.234  19.529  58.154  1.00 37.71           C
ATOM    718  CD2 LEU A 128      36.913  20.177  58.815  1.00 37.71           C
ATOM    719  N   ASN A 129      41.285  21.278  58.815  1.00 50.03           N
ATOM    720  CA  ASN A 129      41.849  22.374  58.043  1.00 50.03           C
ATOM    721  C   ASN A 129      41.112  22.576  56.730  1.00 50.03           C
ATOM    722  O   ASN A 129      40.812  21.605  56.037  1.00 50.03           O
ATOM    723  CB  ASN A 129      43.324  22.087  57.754  1.00 36.05           C
ATOM    724  CG  ASN A 129      44.147  21.895  59.029  1.00 36.05           C
ATOM    725  OD1 ASN A 129      44.813  22.818  59.504  1.00 36.05           O
ATOM    726  ND2 ASN A 129      44.094  20.688  59.591  1.00 36.05           N
ATOM    727  N   LEU A 130      40.816  23.833  56.391  1.00 48.89           N
ATOM    728  CA  LEU A 130      40.156  24.142  55.126  1.00 48.89           C
ATOM    729  C   LEU A 130      41.036  25.048  54.254  1.00 48.89           C
ATOM    730  O   LEU A 130      41.168  26.246  54.516  1.00 48.89           O
ATOM    731  CB  LEU A 130      38.817  24.826  55.357  1.00 34.06           C
ATOM    732  CG  LEU A 130      37.698  24.044  56.035  1.00 34.06           C
ATOM    733  CD1 LEU A 130      36.403  24.790  55.780  1.00 34.06           C
ATOM    734  CD2 LEU A 130      37.589  22.639  55.483  1.00 34.06           C
ATOM    735  N   VAL A 131      41.643  24.475  53.222  1.00 33.05           N
ATOM    736  CA  VAL A 131      42.490  25.249  52.331  1.00 33.05           C
ATOM    737  C   VAL A 131      41.584  25.914  51.304  1.00 33.05           C
ATOM    738  O   VAL A 131      41.027  25.238  50.435  1.00 33.05           O
ATOM    739  CB  VAL A 131      43.494  24.344  51.612  1.00 25.51           C
ATOM    740  CG1 VAL A 131      44.532  25.182  50.913  1.00 25.51           C
ATOM    741  CG2 VAL A 131      44.147  23.413  52.607  1.00 25.51           C
```

FIG. 1-13

| | | | | | | | | | |
|---|---|---|---|---|---|---|---|---|---|
| ATOM | 742 | N | LEU | A | 132 | 41.444 | 27.237 | 51.409 | 1.00 37.71 N |
| ATOM | 743 | CA | LEU | A | 132 | 40.580 | 28.020 | 50.515 | 1.00 37.71 C |
| ATOM | 744 | C | LEU | A | 132 | 41.344 | 29.014 | 49.659 | 1.00 37.71 C |
| ATOM | 745 | O | LEU | A | 132 | 42.514 | 29.292 | 49.928 | 1.00 37.71 O |
| ATOM | 746 | CB | LEU | A | 132 | 39.573 | 28.793 | 51.348 | 1.00 23.63 C |
| ATOM | 747 | CG | LEU | A | 132 | 38.726 | 27.947 | 52.286 | 1.00 23.63 C |
| ATOM | 748 | CD1 | LEU | A | 132 | 38.515 | 28.697 | 53.579 | 1.00 23.63 C |
| ATOM | 749 | CD2 | LEU | A | 132 | 37.412 | 27.613 | 51.614 | 1.00 23.63 C |
| ATOM | 750 | N | ASP | A | 133 | 40.688 | 29.546 | 48.625 | 1.00 40.09 N |
| ATOM | 751 | CA | ASP | A | 133 | 41.332 | 30.550 | 47.780 | 1.00 40.09 C |
| ATOM | 752 | C | ASP | A | 133 | 41.609 | 31.722 | 48.713 | 1.00 40.09 C |
| ATOM | 753 | O | ASP | A | 133 | 40.865 | 31.951 | 49.670 | 1.00 40.09 O |
| ATOM | 754 | CB | ASP | A | 133 | 40.403 | 31.071 | 46.674 | 1.00 52.78 C |
| ATOM | 755 | CG | ASP | A | 133 | 40.311 | 30.141 | 45.466 | 1.00 52.78 C |
| ATOM | 756 | OD1 | ASP | A | 133 | 41.310 | 29.447 | 45.156 | 1.00 52.78 O |
| ATOM | 757 | OD2 | ASP | A | 133 | 39.235 | 30.137 | 44.808 | 1.00 52.78 O |
| ATOM | 758 | N | TYR | A | 134 | 42.672 | 32.467 | 48.447 | 1.00 51.56 N |
| ATOM | 759 | CA | TYR | A | 134 | 42.970 | 33.623 | 49.279 | 1.00 51.56 C |
| ATOM | 760 | C | TYR | A | 134 | 42.667 | 34.884 | 48.504 | 1.00 51.56 C |
| ATOM | 761 | O | TYR | A | 134 | 43.071 | 35.021 | 47.350 | 1.00 51.56 O |
| ATOM | 762 | CB | TYR | A | 134 | 44.426 | 33.656 | 49.670 | 1.00 64.72 C |
| ATOM | 763 | CG | TYR | A | 134 | 44.760 | 34.885 | 50.461 | 1.00 64.72 C |
| ATOM | 764 | CD1 | TYR | A | 134 | 44.292 | 35.040 | 51.766 | 1.00 64.72 C |
| ATOM | 765 | CD2 | TYR | A | 134 | 45.574 | 35.884 | 49.920 | 1.00 64.72 C |
| ATOM | 766 | CE1 | TYR | A | 134 | 44.633 | 36.157 | 52.526 | 1.00 64.72 C |
| ATOM | 767 | CE2 | TYR | A | 134 | 45.923 | 37.004 | 50.665 | 1.00 64.72 C |
| ATOM | 768 | CZ | TYR | A | 134 | 45.454 | 37.133 | 51.970 | 1.00 64.72 C |
| ATOM | 769 | OH | TYR | A | 134 | 45.835 | 38.228 | 52.721 | 1.00 64.72 O |
| ATOM | 770 | N | VAL | A | 135 | 41.961 | 35.807 | 49.139 | 1.00 34.95 N |
| ATOM | 771 | CA | VAL | A | 135 | 41.602 | 37.059 | 48.492 | 1.00 34.95 C |
| ATOM | 772 | C | VAL | A | 135 | 41.826 | 38.179 | 49.505 | 1.00 34.95 C |
| ATOM | 773 | O | VAL | A | 135 | 41.124 | 38.293 | 50.511 | 1.00 34.95 O |
| ATOM | 774 | CB | VAL | A | 135 | 40.147 | 37.012 | 48.026 | 1.00 27.14 C |
| ATOM | 775 | CG1 | VAL | A | 135 | 39.836 | 38.199 | 47.135 | 1.00 27.14 C |
| ATOM | 776 | CG2 | VAL | A | 135 | 39.900 | 35.705 | 47.296 | 1.00 27.14 C |
| ATOM | 777 | N | PRO | A | 136 | 42.811 | 39.035 | 49.227 | 1.00 55.48 N |
| ATOM | 778 | CA | PRO | A | 136 | 43.225 | 40.170 | 50.051 | 1.00 55.48 C |
| ATOM | 779 | C | PRO | A | 136 | 42.168 | 41.217 | 50.396 | 1.00 55.48 C |
| ATOM | 780 | O | PRO | A | 136 | 41.998 | 41.572 | 51.567 | 1.00 55.48 O |
| ATOM | 781 | CB | PRO | A | 136 | 44.374 | 40.757 | 49.244 | 1.00 53.53 C |
| ATOM | 782 | CG | PRO | A | 136 | 43.874 | 40.604 | 47.848 | 1.00 53.53 C |
| ATOM | 783 | CD | PRO | A | 136 | 43.341 | 39.177 | 47.856 | 1.00 53.53 C |
| ATOM | 784 | N | GLU | A | 137 | 41.453 | 41.709 | 49.393 | 1.00 27.12 N |
| ATOM | 785 | CA | GLU | A | 137 | 40.466 | 42.749 | 49.639 | 1.00 27.12 C |
| ATOM | 786 | C | GLU | A | 137 | 39.053 | 42.221 | 49.879 | 1.00 27.12 C |
| ATOM | 787 | O | GLU | A | 137 | 38.720 | 41.120 | 49.477 | 1.00 27.12 O |
| ATOM | 788 | CB | GLU | A | 137 | 40.490 | 43.740 | 48.471 | 1.00 54.17 C |
| ATOM | 789 | CG | GLU | A | 137 | 40.158 | 45.159 | 48.865 | 1.00 54.17 C |
| ATOM | 790 | CD | GLU | A | 137 | 41.004 | 45.651 | 50.032 | 1.00 54.17 C |
| ATOM | 791 | OE1 | GLU | A | 137 | 42.107 | 46.212 | 49.812 | 1.00 54.17 O |
| ATOM | 792 | OE2 | GLU | A | 137 | 40.565 | 45.460 | 51.186 | 1.00 54.17 O |
| ATOM | 793 | N | THR | A | 138 | 38.234 | 43.020 | 50.553 | 1.00 24.91 N |
| ATOM | 794 | CA | THR | A | 138 | 36.852 | 42.664 | 50.860 | 1.00 24.91 C |
| ATOM | 795 | C | THR | A | 138 | 35.984 | 43.887 | 50.619 | 1.00 24.91 C |
| ATOM | 796 | O | THR | A | 138 | 36.472 | 45.004 | 50.614 | 1.00 24.91 O |
| ATOM | 797 | CB | THR | A | 138 | 36.680 | 42.259 | 52.330 | 1.00 31.52 C |
| ATOM | 798 | OG1 | THR | A | 138 | 36.902 | 43.400 | 53.169 | 1.00 31.52 O |
| ATOM | 799 | CG2 | THR | A | 138 | 37.663 | 41.168 | 52.699 | 1.00 31.52 C |
| ATOM | 800 | N | VAL | A | 139 | 34.691 | 43.685 | 50.424 | 1.00 27.42 N |
| ATOM | 801 | CA | VAL | A | 139 | 33.813 | 44.812 | 50.186 | 1.00 27.42 C |
| ATOM | 802 | C | VAL | A | 139 | 33.867 | 45.755 | 51.373 | 1.00 27.42 C |
| ATOM | 803 | O | VAL | A | 139 | 33.842 | 46.969 | 51.219 | 1.00 27.42 O |

FIG. 1-14

```
ATOM    804  CB   VAL A 139      32.367  44.351  49.949  1.00 26.39           C
ATOM    805  CG1  VAL A 139      31.405  45.536  50.103  1.00 26.39           C
ATOM    806  CG2  VAL A 139      32.248  43.748  48.548  1.00 26.39           C
ATOM    807  N    TYR A 140      33.953  45.179  52.560  1.00 28.15           N
ATOM    808  CA   TYR A 140      34.024  45.952  53.775  1.00 28.15           C
ATOM    809  C    TYR A 140      35.190  46.941  53.684  1.00 28.15           C
ATOM    810  O    TYR A 140      34.999  48.153  53.763  1.00 28.15           O
ATOM    811  CB   TYR A 140      34.222  45.015  54.963  1.00 29.23           C
ATOM    812  CG   TYR A 140      34.441  45.736  56.267  1.00 29.23           C
ATOM    813  CD1  TYR A 140      33.378  46.326  56.949  1.00 29.23           C
ATOM    814  CD2  TYR A 140      35.718  45.860  56.803  1.00 29.23           C
ATOM    815  CE1  TYR A 140      33.584  47.030  58.133  1.00 29.23           C
ATOM    816  CE2  TYR A 140      35.937  46.557  57.980  1.00 29.23           C
ATOM    817  CZ   TYR A 140      34.870  47.140  58.641  1.00 29.23           C
ATOM    818  OH   TYR A 140      35.096  47.852  59.792  1.00 29.23           O
ATOM    819  N    ARG A 141      36.399  46.420  53.509  1.00 29.92           N
ATOM    820  CA   ARG A 141      37.571  47.273  53.414  1.00 29.92           C
ATOM    821  C    ARG A 141      37.448  48.355  52.349  1.00 29.92           C
ATOM    822  O    ARG A 141      37.799  49.504  52.582  1.00 29.92           O
ATOM    823  CB   ARG A 141      38.809  46.430  53.152  1.00 61.43           C
ATOM    824  CG   ARG A 141      39.293  45.649  54.372  1.00 61.43           C
ATOM    825  CD   ARG A 141      40.677  45.065  54.119  1.00 61.43           C
ATOM    826  NE   ARG A 141      41.506  46.012  53.372  1.00 61.43           N
ATOM    827  CZ   ARG A 141      42.714  45.731  52.899  1.00 61.43           C
ATOM    828  NH1  ARG A 141      43.243  44.527  53.109  1.00 61.43           N
ATOM    829  NH2  ARG A 141      43.374  46.637  52.179  1.00 61.43           N
ATOM    830  N    VAL A 142      36.950  47.995  51.175  1.00 36.65           N
ATOM    831  CA   VAL A 142      36.799  48.980  50.117  1.00 36.65           C
ATOM    832  C    VAL A 142      35.778  50.036  50.521  1.00 36.65           C
ATOM    833  O    VAL A 142      36.065  51.228  50.480  1.00 36.65           O
ATOM    834  CB   VAL A 142      36.356  48.327  48.796  1.00 25.48           C
ATOM    835  CG1  VAL A 142      36.110  49.380  47.754  1.00 25.48           C
ATOM    836  CG2  VAL A 142      37.416  47.370  48.314  1.00 25.48           C
ATOM    837  N    ALA A 143      34.591  49.609  50.931  1.00 26.42           N
ATOM    838  CA   ALA A 143      33.563  50.570  51.320  1.00 26.42           C
ATOM    839  C    ALA A 143      34.039  51.495  52.431  1.00 26.42           C
ATOM    840  O    ALA A 143      33.655  52.657  52.470  1.00 26.42           O
ATOM    841  CB   ALA A 143      32.284  49.842  51.756  1.00 31.94           C
ATOM    842  N    ARG A 144      34.876  50.969  53.319  1.00 30.25           N
ATOM    843  CA   ARG A 144      35.403  51.724  54.456  1.00 30.25           C
ATOM    844  C    ARG A 144      36.392  52.783  53.983  1.00 30.25           C
ATOM    845  O    ARG A 144      36.352  53.925  54.433  1.00 30.25           O
ATOM    846  CB   ARG A 144      36.091  50.768  55.440  1.00 46.52           C
ATOM    847  CG   ARG A 144      36.504  51.391  56.758  1.00 46.52           C
ATOM    848  CD   ARG A 144      37.357  50.429  57.593  1.00 46.52           C
ATOM    849  NE   ARG A 144      37.502  50.867  58.978  0.00 46.52           N
ATOM    850  CZ   ARG A 144      36.493  50.966  59.838  0.00 46.52           C
ATOM    851  NH1  ARG A 144      35.261  50.659  59.454  0.00 46.52           N
ATOM    852  NH2  ARG A 144      36.712  51.368  61.082  0.00 46.52           N
ATOM    853  N    HIS A 145      37.278  52.387  53.075  1.00 35.85           N
ATOM    854  CA   HIS A 145      38.276  53.283  52.508  1.00 35.85           C
ATOM    855  C    HIS A 145      37.592  54.547  51.972  1.00 35.85           C
ATOM    856  O    HIS A 145      37.940  55.670  52.351  1.00 35.85           O
ATOM    857  CB   HIS A 145      39.003  52.573  51.369  1.00 46.47           C
ATOM    858  CG   HIS A 145      40.063  53.399  50.714  1.00 46.47           C
ATOM    859  ND1  HIS A 145      41.407  53.205  50.954  1.00 46.47           N
ATOM    860  CD2  HIS A 145      39.981  54.421  49.828  1.00 46.47           C
ATOM    861  CE1  HIS A 145      42.107  54.071  50.238  1.00 46.47           C
ATOM    862  NE2  HIS A 145      41.268  54.821  49.546  1.00 46.47           N
ATOM    863  N    TYR A 146      36.612  54.354  51.093  1.00 35.25           N
ATOM    864  CA   TYR A 146      35.884  55.466  50.502  1.00 35.25           C
ATOM    865  C    TYR A 146      35.126  56.252  51.539  1.00 35.25           C
```

FIG. 1-15

```
ATOM    866  O    TYR A 146      35.114  57.483  51.512  1.00 35.25           O
ATOM    867  CB   TYR A 146      34.902  54.968  49.437  1.00 26.45           C
ATOM    868  CG   TYR A 146      35.576  54.507  48.172  1.00 26.45           C
ATOM    869  CD1  TYR A 146      36.298  53.322  48.142  1.00 26.45           C
ATOM    870  CD2  TYR A 146      35.559  55.302  47.022  1.00 26.45           C
ATOM    871  CE1  TYR A 146      36.989  52.937  47.007  1.00 26.45           C
ATOM    872  CE2  TYR A 146      36.248  54.929  45.879  1.00 26.45           C
ATOM    873  CZ   TYR A 146      36.967  53.745  45.877  1.00 26.45           C
ATOM    874  OH   TYR A 146      37.682  53.381  44.753  1.00 26.45           O
ATOM    875  N    SER A 147      34.503  55.543  52.468  1.00 38.55           N
ATOM    876  CA   SER A 147      33.714  56.205  53.491  1.00 38.55           C
ATOM    877  C    SER A 147      34.547  57.133  54.363  1.00 38.55           C
ATOM    878  O    SER A 147      34.071  58.191  54.786  1.00 38.55           O
ATOM    879  CB   SER A 147      33.006  55.173  54.367  1.00 46.88           C
ATOM    880  OG   SER A 147      31.981  55.793  55.126  1.00 46.88           O
ATOM    881  N    ARG A 148      35.787  56.736  54.631  1.00 44.27           N
ATOM    882  CA   ARG A 148      36.666  57.544  55.453  1.00 44.27           C
ATOM    883  C    ARG A 148      37.076  58.789  54.673  1.00 44.27           C
ATOM    884  O    ARG A 148      37.144  59.886  55.233  1.00 44.27           O
ATOM    885  CB   ARG A 148      37.913  56.750  55.849  1.00 40.43           C
ATOM    886  CG   ARG A 148      37.665  55.525  56.728  1.00 40.43           C
ATOM    887  CD   ARG A 148      36.858  55.872  57.962  1.00 40.43           C
ATOM    888  NE   ARG A 148      36.949  54.835  58.984  0.00 40.43           N
ATOM    889  CZ   ARG A 148      38.075  54.498  59.604  0.00 40.43           C
ATOM    890  NH1  ARG A 148      39.210  55.116  59.306  0.00 40.43           N
ATOM    891  NH2  ARG A 148      38.067  53.547  60.526  0.00 40.43           N
ATOM    892  N    ALA A 149      37.341  58.618  53.381  1.00 38.37           N
ATOM    893  CA   ALA A 149      37.752  59.729  52.530  1.00 38.37           C
ATOM    894  C    ALA A 149      36.546  60.558  52.092  1.00 38.37           C
ATOM    895  O    ALA A 149      36.610  61.293  51.104  1.00 38.37           O
ATOM    896  CB   ALA A 149      38.507  59.199  51.299  1.00 20.40           C
ATOM    897  N    LYS A 150      35.443  60.440  52.825  1.00 54.55           N
ATOM    898  CA   LYS A 150      34.233  61.183  52.487  1.00 54.55           C
ATOM    899  C    LYS A 150      33.969  61.123  50.977  1.00 54.55           C
ATOM    900  O    LYS A 150      33.400  62.049  50.384  1.00 54.55           O
ATOM    901  CB   LYS A 150      34.352  62.643  52.948  1.00 59.91           C
ATOM    902  CG   LYS A 150      34.441  62.820  54.464  1.00 59.91           C
ATOM    903  CD   LYS A 150      34.362  64.295  54.853  0.00 59.91           C
ATOM    904  CE   LYS A 150      33.016  64.902  54.479  1.00 59.91           C
ATOM    905  NZ   LYS A 150      32.906  66.353  54.862  1.00 59.91           N
ATOM    906  N    GLN A 151      34.399  60.028  50.359  1.00 44.44           N
ATOM    907  CA   GLN A 151      34.182  59.827  48.930  1.00 44.44           C
ATOM    908  C    GLN A 151      33.140  58.722  48.763  1.00 44.44           C
ATOM    909  O    GLN A 151      32.525  58.267  49.745  1.00 44.44           O
ATOM    910  CB   GLN A 151      35.486  59.416  48.254  1.00 51.73           C
ATOM    911  CG   GLN A 151      36.625  60.380  48.515  1.00 51.73           C
ATOM    912  CD   GLN A 151      37.972  59.838  48.063  1.00 51.73           C
ATOM    913  OE1  GLN A 151      39.001  60.500  48.210  1.00 51.73           O
ATOM    914  NE2  GLN A 151      37.973  58.627  47.509  1.00 51.73           N
ATOM    915  N    THR A 152      32.917  58.302  47.524  1.00 51.39           N
ATOM    916  CA   THR A 152      31.959  57.231  47.287  1.00 51.39           C
ATOM    917  C    THR A 152      32.396  56.366  46.136  1.00 51.39           C
ATOM    918  O    THR A 152      33.016  56.830  45.167  1.00 51.39           O
ATOM    919  CB   THR A 152      30.537  57.748  46.996  1.00 72.10           C
ATOM    920  OG1  THR A 152      29.597  56.749  47.405  1.00 72.10           O
ATOM    921  CG2  THR A 152      30.340  58.016  45.511  0.00 72.10           C
ATOM    922  N    LEU A 153      32.065  55.092  46.259  1.00 40.52           N
ATOM    923  CA   LEU A 153      32.414  54.110  45.255  1.00 40.52           C
ATOM    924  C    LEU A 153      31.584  54.303  43.985  1.00 40.52           C
ATOM    925  O    LEU A 153      30.374  54.516  44.050  1.00 40.52           O
ATOM    926  CB   LEU A 153      32.164  52.717  45.825  1.00 33.52           C
ATOM    927  CG   LEU A 153      32.729  51.570  45.003  1.00 33.52           C
```

FIG. 1-16

```
ATOM    928  CD1 LEU A 153      34.246  51.536  45.166  1.00 33.52           C
ATOM    929  CD2 LEU A 153      32.091  50.270  45.455  1.00 33.52           C
ATOM    930  N   PRO A 154      32.234  54.271  42.816  1.00 28.10           N
ATOM    931  CA  PRO A 154      31.528  54.428  41.544  1.00 28.10           C
ATOM    932  C   PRO A 154      30.486  53.315  41.418  1.00 28.10           C
ATOM    933  O   PRO A 154      30.808  52.139  41.565  1.00 28.10           O
ATOM    934  CB  PRO A 154      32.640  54.281  40.517  1.00 34.70           C
ATOM    935  CG  PRO A 154      33.802  54.894  41.217  1.00 34.70           C
ATOM    936  CD  PRO A 154      33.690  54.357  42.622  1.00 34.70           C
ATOM    937  N   VAL A 155      29.246  53.711  41.152  1.00 35.03           N
ATOM    938  CA  VAL A 155      28.123  52.801  41.013  1.00 35.03           C
ATOM    939  C   VAL A 155      28.469  51.573  40.186  1.00 35.03           C
ATOM    940  O   VAL A 155      27.975  50.482  40.460  1.00 35.03           O
ATOM    941  CB  VAL A 155      26.908  53.515  40.376  1.00 22.64           C
ATOM    942  CG1 VAL A 155      26.464  54.670  41.258  0.00 22.64           C
ATOM    943  CG2 VAL A 155      27.268  54.018  38.986  0.00 22.64           C
ATOM    944  N   ILE A 156      29.316  51.739  39.177  1.00 27.63           N
ATOM    945  CA  ILE A 156      29.687  50.602  38.349  1.00 27.63           C
ATOM    946  C   ILE A 156      30.146  49.446  39.244  1.00 27.63           C
ATOM    947  O   ILE A 156      29.787  48.293  39.002  1.00 27.63           O
ATOM    948  CB  ILE A 156      30.803  50.980  37.353  1.00 24.51           C
ATOM    949  CG1 ILE A 156      31.297  49.743  36.600  1.00 24.51           C
ATOM    950  CG2 ILE A 156      31.940  51.625  38.089  1.00 24.51           C
ATOM    951  CD1 ILE A 156      30.333  49.197  35.573  1.00 24.51           C
ATOM    952  N   TYR A 157      30.931  49.748  40.277  1.00 23.27           N
ATOM    953  CA  TYR A 157      31.398  48.706  41.188  1.00 23.27           C
ATOM    954  C   TYR A 157      30.239  48.215  42.024  1.00 23.27           C
ATOM    955  O   TYR A 157      30.139  47.035  42.321  1.00 23.27           O
ATOM    956  CB  TYR A 157      32.495  49.223  42.129  1.00 37.48           C
ATOM    957  CG  TYR A 157      33.819  49.461  41.453  1.00 37.48           C
ATOM    958  CD1 TYR A 157      34.418  50.722  41.469  1.00 37.48           C
ATOM    959  CD2 TYR A 157      34.452  48.437  40.746  1.00 37.48           C
ATOM    960  CE1 TYR A 157      35.609  50.955  40.786  1.00 37.48           C
ATOM    961  CE2 TYR A 157      35.630  48.660  40.061  1.00 37.48           C
ATOM    962  CZ  TYR A 157      36.203  49.917  40.086  1.00 37.48           C
ATOM    963  OH  TYR A 157      37.373  50.127  39.405  1.00 37.48           O
ATOM    964  N   VAL A 158      29.367  49.134  42.410  1.00 25.33           N
ATOM    965  CA  VAL A 158      28.224  48.776  43.223  1.00 25.33           C
ATOM    966  C   VAL A 158      27.443  47.711  42.464  1.00 25.33           C
ATOM    967  O   VAL A 158      27.139  46.645  42.999  1.00 25.33           O
ATOM    968  CB  VAL A 158      27.339  50.026  43.506  1.00 23.12           C
ATOM    969  CG1 VAL A 158      26.188  49.671  44.453  1.00 23.12           C
ATOM    970  CG2 VAL A 158      28.189  51.125  44.117  1.00 23.12           C
ATOM    971  N   LYS A 159      27.152  48.007  41.201  1.00 26.41           N
ATOM    972  CA  LYS A 159      26.416  47.106  40.330  1.00 26.41           C
ATOM    973  C   LYS A 159      27.164  45.796  40.177  1.00 26.41           C
ATOM    974  O   LYS A 159      26.597  44.725  40.358  1.00 26.41           O
ATOM    975  CB  LYS A 159      26.217  47.755  38.962  1.00 30.79           C
ATOM    976  CG  LYS A 159      25.480  49.092  39.010  1.00 30.79           C
ATOM    977  CD  LYS A 159      25.282  49.655  37.617  1.00 30.79           C
ATOM    978  CE  LYS A 159      24.500  50.953  37.622  1.00 30.79           C
ATOM    979  NZ  LYS A 159      24.241  51.420  36.226  1.00 30.79           N
ATOM    980  N   LEU A 160      28.442  45.886  39.843  1.00 28.98           N
ATOM    981  CA  LEU A 160      29.267  44.700  39.682  1.00 28.98           C
ATOM    982  C   LEU A 160      29.241  43.802  40.903  1.00 28.98           C
ATOM    983  O   LEU A 160      28.957  42.613  40.802  1.00 28.98           O
ATOM    984  CB  LEU A 160      30.718  45.090  39.398  1.00 27.95           C
ATOM    985  CG  LEU A 160      31.101  45.332  37.941  1.00 27.95           C
ATOM    986  CD1 LEU A 160      32.508  45.865  37.869  1.00 27.95           C
ATOM    987  CD2 LEU A 160      30.988  44.032  37.160  1.00 27.95           C
ATOM    988  N   TYR A 161      29.544  44.373  42.061  1.00 30.87           N
ATOM    989  CA  TYR A 161      29.591  43.597  43.289  1.00 30.87           C
```

FIG. 1-17

```
ATOM    990  C   TYR A 161      28.241  43.008  43.680  1.00 30.87           C
ATOM    991  O   TYR A 161      28.121  41.794  43.895  1.00 30.87           O
ATOM    992  CB  TYR A 161      30.120  44.447  44.452  1.00 30.35           C
ATOM    993  CG  TYR A 161      31.512  45.025  44.293  1.00 30.35           C
ATOM    994  CD1 TYR A 161      32.444  44.456  43.432  1.00 30.35           C
ATOM    995  CD2 TYR A 161      31.905  46.138  45.047  1.00 30.35           C
ATOM    996  CE1 TYR A 161      33.730  44.977  43.329  1.00 30.35           C
ATOM    997  CE2 TYR A 161      33.194  46.664  44.954  1.00 30.35           C
ATOM    998  CZ  TYR A 161      34.097  46.080  44.096  1.00 30.35           C
ATOM    999  OH  TYR A 161      35.373  46.588  44.021  1.00 30.35           O
ATOM   1000  N   MET A 162      27.227  43.861  43.784  1.00 23.41           N
ATOM   1001  CA  MET A 162      25.906  43.394  44.171  1.00 23.41           C
ATOM   1002  C   MET A 162      25.369  42.295  43.257  1.00 23.41           C
ATOM   1003  O   MET A 162      24.759  41.335  43.733  1.00 23.41           O
ATOM   1004  CB  MET A 162      24.915  44.564  44.227  1.00 22.26           C
ATOM   1005  CG  MET A 162      25.111  45.500  45.418  1.00 22.26           C
ATOM   1006  SD  MET A 162      25.381  44.652  46.986  1.00 22.26           S
ATOM   1007  CE  MET A 162      23.973  43.619  47.107  1.00 22.26           C
ATOM   1008  N   TYR A 163      25.598  42.447  41.951  1.00 21.29           N
ATOM   1009  CA  TYR A 163      25.156  41.480  40.957  1.00 21.29           C
ATOM   1010  C   TYR A 163      25.762  40.114  41.252  1.00 21.29           C
ATOM   1011  O   TYR A 163      25.065  39.099  41.360  1.00 21.29           O
ATOM   1012  CB  TYR A 163      25.599  41.922  39.569  1.00 27.46           C
ATOM   1013  CG  TYR A 163      25.196  40.971  38.463  1.00 27.46           C
ATOM   1014  CD1 TYR A 163      23.945  41.065  37.860  1.00 27.46           C
ATOM   1015  CD2 TYR A 163      26.066  39.978  38.025  1.00 27.46           C
ATOM   1016  CE1 TYR A 163      23.570  40.192  36.843  1.00 27.46           C
ATOM   1017  CE2 TYR A 163      25.706  39.106  37.021  1.00 27.46           C
ATOM   1018  CZ  TYR A 163      24.460  39.216  36.423  1.00 27.46           C
ATOM   1019  OH  TYR A 163      24.120  38.373  35.380  1.00 27.46           O
ATOM   1020  N   GLN A 164      27.078  40.098  41.377  1.00 23.12           N
ATOM   1021  CA  GLN A 164      27.768  38.864  41.648  1.00 23.12           C
ATOM   1022  C   GLN A 164      27.300  38.214  42.951  1.00 23.12           C
ATOM   1023  O   GLN A 164      27.198  36.991  43.029  1.00 23.12           O
ATOM   1024  CB  GLN A 164      29.276  39.116  41.641  1.00 30.11           C
ATOM   1025  CG  GLN A 164      29.763  39.698  40.313  1.00 30.11           C
ATOM   1026  CD  GLN A 164      31.266  39.831  40.232  1.00 30.11           C
ATOM   1027  OE1 GLN A 164      31.973  38.841  40.085  1.00 30.11           O
ATOM   1028  NE2 GLN A 164      31.765  41.058  40.334  1.00 30.11           N
ATOM   1029  N   LEU A 165      26.999  39.017  43.969  1.00 24.85           N
ATOM   1030  CA  LEU A 165      26.528  38.450  45.225  1.00 24.85           C
ATOM   1031  C   LEU A 165      25.153  37.818  45.006  1.00 24.85           C
ATOM   1032  O   LEU A 165      24.876  36.713  45.472  1.00 24.85           O
ATOM   1033  CB  LEU A 165      26.455  39.527  46.309  1.00 19.06           C
ATOM   1034  CG  LEU A 165      25.716  39.235  47.625  1.00 19.06           C
ATOM   1035  CD1 LEU A 165      26.302  38.018  48.340  1.00 19.06           C
ATOM   1036  CD2 LEU A 165      25.789  40.460  48.508  1.00 19.06           C
ATOM   1037  N   PHE A 166      24.289  38.507  44.275  1.00 26.70           N
ATOM   1038  CA  PHE A 166      22.968  37.959  44.036  1.00 26.70           C
ATOM   1039  C   PHE A 166      23.044  36.654  43.268  1.00 26.70           C
ATOM   1040  O   PHE A 166      22.239  35.745  43.469  1.00 26.70           O
ATOM   1041  CB  PHE A 166      22.094  38.970  43.303  1.00 15.81           C
ATOM   1042  CG  PHE A 166      21.510  40.001  44.204  1.00 15.81           C
ATOM   1043  CD1 PHE A 166      20.795  39.619  45.332  1.00 15.81           C
ATOM   1044  CD2 PHE A 166      21.688  41.352  43.951  1.00 15.81           C
ATOM   1045  CE1 PHE A 166      20.268  40.566  46.199  1.00 15.81           C
ATOM   1046  CE2 PHE A 166      21.163  42.302  44.812  1.00 15.81           C
ATOM   1047  CZ  PHE A 166      20.452  41.903  45.940  1.00 15.81           C
ATOM   1048  N   ARG A 167      24.029  36.558  42.393  1.00 36.56           N
ATOM   1049  CA  ARG A 167      24.196  35.352  41.618  1.00 36.56           C
ATOM   1050  C   ARG A 167      24.684  34.240  42.539  1.00 36.56           C
ATOM   1051  O   ARG A 167      24.209  33.109  42.473  1.00 36.56           O
```

FIG. 1-18

```
ATOM   1052  CB   ARG A 167      25.193  35.593  40.496  1.00 35.25           C
ATOM   1053  CG   ARG A 167      25.194  34.513  39.452  1.00 35.25           C
ATOM   1054  CD   ARG A 167      26.048  34.929  38.290  1.00 35.25           C
ATOM   1055  NE   ARG A 167      26.250  33.830  37.367  1.00 35.25           N
ATOM   1056  CZ   ARG A 167      27.311  33.725  36.585  1.00 35.25           C
ATOM   1057  NH1  ARG A 167      28.251  34.662  36.635  1.00 35.25           N
ATOM   1058  NH2  ARG A 167      27.430  32.696  35.753  1.00 35.25           N
ATOM   1059  N    SER A 168      25.623  34.560  43.418  1.00 31.54           N
ATOM   1060  CA   SER A 168      26.121  33.542  44.325  1.00 31.54           C
ATOM   1061  C    SER A 168      24.994  33.039  45.224  1.00 31.54           C
ATOM   1062  O    SER A 168      24.991  31.885  45.632  1.00 31.54           O
ATOM   1063  CB   SER A 168      27.266  34.091  45.175  1.00 22.91           C
ATOM   1064  OG   SER A 168      26.815  35.085  46.062  1.00 22.91           O
ATOM   1065  N    LEU A 169      24.027  33.903  45.508  1.00 25.05           N
ATOM   1066  CA   LEU A 169      22.928  33.537  46.379  1.00 25.05           C
ATOM   1067  C    LEU A 169      21.940  32.660  45.667  1.00 25.05           C
ATOM   1068  O    LEU A 169      21.365  31.759  46.264  1.00 25.05           O
ATOM   1069  CB   LEU A 169      22.228  34.786  46.910  1.00 26.63           C
ATOM   1070  CG   LEU A 169      22.394  35.175  48.390  1.00 26.63           C
ATOM   1071  CD1  LEU A 169      23.849  35.228  48.786  1.00 26.63           C
ATOM   1072  CD2  LEU A 169      21.726  36.531  48.614  1.00 26.63           C
ATOM   1073  N    ALA A 170      21.742  32.917  44.381  1.00 29.29           N
ATOM   1074  CA   ALA A 170      20.808  32.122  43.601  1.00 29.29           C
ATOM   1075  C    ALA A 170      21.369  30.708  43.482  1.00 29.29           C
ATOM   1076  O    ALA A 170      20.644  29.726  43.475  1.00 29.29           O
ATOM   1077  CB   ALA A 170      20.625  32.740  42.230  1.00  8.31           C
ATOM   1078  N    TYR A 171      22.684  30.614  43.421  1.00 28.63           N
ATOM   1079  CA   TYR A 171      23.320  29.328  43.282  1.00 28.63           C
ATOM   1080  C    TYR A 171      23.184  28.449  44.511  1.00 28.63           C
ATOM   1081  O    TYR A 171      22.729  27.318  44.410  1.00 28.63           O
ATOM   1082  CB   TYR A 171      24.789  29.517  42.941  1.00 35.01           C
ATOM   1083  CG   TYR A 171      25.518  28.219  42.790  1.00 35.01           C
ATOM   1084  CD1  TYR A 171      25.255  27.366  41.721  1.00 35.01           C
ATOM   1085  CD2  TYR A 171      26.473  27.835  43.716  1.00 35.01           C
ATOM   1086  CE1  TYR A 171      25.934  26.164  41.577  1.00 35.01           C
ATOM   1087  CE2  TYR A 171      27.160  26.633  43.585  1.00 35.01           C
ATOM   1088  CZ   TYR A 171      26.889  25.802  42.512  1.00 35.01           C
ATOM   1089  OH   TYR A 171      27.601  24.627  42.370  1.00 35.01           O
ATOM   1090  N    ILE A 172      23.587  28.954  45.670  1.00 23.62           N
ATOM   1091  CA   ILE A 172      23.492  28.170  46.891  1.00 23.62           C
ATOM   1092  C    ILE A 172      22.041  27.962  47.309  1.00 23.62           C
ATOM   1093  O    ILE A 172      21.702  26.948  47.906  1.00 23.62           O
ATOM   1094  CB   ILE A 172      24.263  28.822  48.051  1.00 20.34           C
ATOM   1095  CG1  ILE A 172      23.753  30.238  48.287  1.00 20.34           C
ATOM   1096  CG2  ILE A 172      25.750  28.809  47.755  1.00 20.34           C
ATOM   1097  CD1  ILE A 172      24.191  30.792  49.601  1.00 20.34           C
ATOM   1098  N    HIS A 173      21.185  28.924  46.995  1.00 26.99           N
ATOM   1099  CA   HIS A 173      19.779  28.796  47.338  1.00 26.99           C
ATOM   1100  C    HIS A 173      19.170  27.654  46.532  1.00 26.99           C
ATOM   1101  O    HIS A 173      18.306  26.917  47.022  1.00 26.99           O
ATOM   1102  CB   HIS A 173      19.021  30.103  47.054  1.00 22.05           C
ATOM   1103  CG   HIS A 173      19.186  31.149  48.120  1.00 22.05           C
ATOM   1104  ND1  HIS A 173      18.495  32.340  48.104  1.00 22.05           N
ATOM   1105  CD2  HIS A 173      19.989  31.201  49.207  1.00 22.05           C
ATOM   1106  CE1  HIS A 173      18.870  33.081  49.130  1.00 22.05           C
ATOM   1107  NE2  HIS A 173      19.776  32.415  49.815  1.00 22.05           N
ATOM   1108  N    SER A 174      19.635  27.499  45.297  1.00 35.53           N
ATOM   1109  CA   SER A 174      19.128  26.451  44.428  1.00 35.53           C
ATOM   1110  C    SER A 174      19.321  25.091  45.082  1.00 35.53           C
ATOM   1111  O    SER A 174      18.616  24.149  44.748  1.00 35.53           O
ATOM   1112  CB   SER A 174      19.818  26.495  43.059  1.00 34.86           C
ATOM   1113  OG   SER A 174      21.175  26.113  43.151  1.00 34.86           O
```

FIG. 1-19

| | | | | | | | | | | |
|---|---|---|---|---|---|---|---|---|---|---|
| ATOM | 1114 | N | PHE | A | 175 | 20.275 | 24.991 | 46.004 | 1.00 28.76 | N |
| ATOM | 1115 | CA | PHE | A | 175 | 20.525 | 23.749 | 46.724 | 1.00 28.76 | C |
| ATOM | 1116 | C | PHE | A | 175 | 19.823 | 23.820 | 48.067 | 1.00 28.76 | C |
| ATOM | 1117 | O | PHE | A | 175 | 20.035 | 22.970 | 48.934 | 1.00 28.76 | O |
| ATOM | 1118 | CB | PHE | A | 175 | 22.016 | 23.543 | 46.980 | 1.00 47.49 | C |
| ATOM | 1119 | CG | PHE | A | 175 | 22.815 | 23.237 | 45.749 | 1.00 47.49 | C |
| ATOM | 1120 | CD1 | PHE | A | 175 | 22.334 | 22.357 | 44.792 | 1.00 47.49 | C |
| ATOM | 1121 | CD2 | PHE | A | 175 | 24.070 | 23.799 | 45.567 | 1.00 47.49 | C |
| ATOM | 1122 | CE1 | PHE | A | 175 | 23.089 | 22.041 | 43.665 | 1.00 47.49 | C |
| ATOM | 1123 | CE2 | PHE | A | 175 | 24.838 | 23.493 | 44.445 | 1.00 47.49 | C |
| ATOM | 1124 | CZ | PHE | A | 175 | 24.348 | 22.610 | 43.488 | 1.00 47.49 | C |
| ATOM | 1125 | N | GLY | A | 176 | 18.997 | 24.849 | 48.240 | 1.00 30.85 | N |
| ATOM | 1126 | CA | GLY | A | 176 | 18.283 | 25.042 | 49.491 | 1.00 30.85 | C |
| ATOM | 1127 | C | GLY | A | 176 | 19.168 | 25.516 | 50.636 | 1.00 30.85 | C |
| ATOM | 1128 | O | GLY | A | 176 | 18.747 | 25.511 | 51.788 | 1.00 30.85 | O |
| ATOM | 1129 | N | ILE | A | 177 | 20.393 | 25.926 | 50.320 | 1.00 26.68 | N |
| ATOM | 1130 | CA | ILE | A | 177 | 21.331 | 26.394 | 51.333 | 1.00 26.68 | C |
| ATOM | 1131 | C | ILE | A | 177 | 21.291 | 27.905 | 51.564 | 1.00 26.68 | C |
| ATOM | 1132 | O | ILE | A | 177 | 21.374 | 28.690 | 50.631 | 1.00 26.68 | O |
| ATOM | 1133 | CB | ILE | A | 177 | 22.770 | 25.997 | 50.980 | 1.00 30.66 | C |
| ATOM | 1134 | CG1 | ILE | A | 177 | 22.870 | 24.480 | 50.893 | 1.00 30.66 | C |
| ATOM | 1135 | CG2 | ILE | A | 177 | 23.733 | 26.511 | 52.044 | 1.00 30.66 | C |
| ATOM | 1136 | CD1 | ILE | A | 177 | 24.173 | 24.010 | 50.333 | 1.00 30.66 | C |
| ATOM | 1137 | N | CYS | A | 178 | 21.178 | 28.292 | 52.830 | 1.00 23.27 | N |
| ATOM | 1138 | CA | CYS | A | 178 | 21.106 | 29.688 | 53.233 | 1.00 23.27 | C |
| ATOM | 1139 | C | CYS | A | 178 | 22.415 | 30.049 | 53.907 | 1.00 23.27 | C |
| ATOM | 1140 | O | CYS | A | 178 | 22.857 | 29.354 | 54.811 | 1.00 23.27 | O |
| ATOM | 1141 | CB | CYS | A | 178 | 19.943 | 29.859 | 54.198 | 1.00 24.81 | C |
| ATOM | 1142 | SG | CYS | A | 178 | 19.595 | 31.517 | 54.719 | 1.00 24.81 | S |
| ATOM | 1143 | N | HIS | A | 179 | 23.036 | 31.134 | 53.462 | 1.00 22.31 | N |
| ATOM | 1144 | CA | HIS | A | 179 | 24.314 | 31.543 | 54.023 | 1.00 22.31 | C |
| ATOM | 1145 | C | HIS | A | 179 | 24.145 | 31.959 | 55.478 | 1.00 22.31 | C |
| ATOM | 1146 | O | HIS | A | 179 | 24.888 | 31.510 | 56.343 | 1.00 22.31 | O |
| ATOM | 1147 | CB | HIS | A | 179 | 24.914 | 32.683 | 53.184 | 1.00 20.53 | C |
| ATOM | 1148 | CG | HIS | A | 179 | 26.342 | 32.992 | 53.511 | 1.00 20.53 | C |
| ATOM | 1149 | ND1 | HIS | A | 179 | 26.714 | 33.698 | 54.637 | 1.00 20.53 | N |
| ATOM | 1150 | CD2 | HIS | A | 179 | 27.489 | 32.662 | 52.879 | 1.00 20.53 | C |
| ATOM | 1151 | CE1 | HIS | A | 179 | 28.029 | 33.787 | 54.683 | 1.00 20.53 | C |
| ATOM | 1152 | NE2 | HIS | A | 179 | 28.525 | 33.166 | 53.628 | 1.00 20.53 | N |
| ATOM | 1153 | N | ARG | A | 180 | 23.159 | 32.815 | 55.732 | 1.00 34.54 | N |
| ATOM | 1154 | CA | ARG | A | 180 | 22.849 | 33.292 | 57.075 | 1.00 34.54 | C |
| ATOM | 1155 | C | ARG | A | 180 | 23.777 | 34.346 | 57.671 | 1.00 34.54 | C |
| ATOM | 1156 | O | ARG | A | 180 | 23.511 | 34.853 | 58.761 | 1.00 34.54 | O |
| ATOM | 1157 | CB | ARG | A | 180 | 22.798 | 32.129 | 58.039 | 1.00 18.15 | C |
| ATOM | 1158 | CG | ARG | A | 180 | 21.666 | 31.199 | 57.856 | 1.00 18.15 | C |
| ATOM | 1159 | CD | ARG | A | 180 | 22.049 | 29.996 | 58.616 | 1.00 18.15 | C |
| ATOM | 1160 | NE | ARG | A | 180 | 21.007 | 29.512 | 59.487 | 1.00 18.15 | N |
| ATOM | 1161 | CZ | ARG | A | 180 | 21.237 | 28.665 | 60.472 | 1.00 18.15 | C |
| ATOM | 1162 | NH1 | ARG | A | 180 | 22.466 | 28.240 | 60.690 | 1.00 18.15 | N |
| ATOM | 1163 | NH2 | ARG | A | 180 | 20.241 | 28.235 | 61.218 | 1.00 18.15 | N |
| ATOM | 1164 | N | ASP | A | 181 | 24.866 | 34.669 | 56.991 | 1.00 23.17 | N |
| ATOM | 1165 | CA | ASP | A | 181 | 25.770 | 35.676 | 57.525 | 1.00 23.17 | C |
| ATOM | 1166 | C | ASP | A | 181 | 26.338 | 36.569 | 56.409 | 1.00 23.17 | C |
| ATOM | 1167 | O | ASP | A | 181 | 27.544 | 36.811 | 56.317 | 1.00 23.17 | O |
| ATOM | 1168 | CB | ASP | A | 181 | 26.885 | 34.987 | 58.326 | 1.00 30.39 | C |
| ATOM | 1169 | CG | ASP | A | 181 | 27.696 | 35.960 | 59.165 | 1.00 30.39 | C |
| ATOM | 1170 | OD1 | ASP | A | 181 | 27.178 | 37.058 | 59.464 | 1.00 30.39 | O |
| ATOM | 1171 | OD2 | ASP | A | 181 | 28.845 | 35.620 | 59.540 | 1.00 30.39 | O |
| ATOM | 1172 | N | ILE | A | 182 | 25.445 | 37.060 | 55.566 | 1.00 12.70 | N |
| ATOM | 1173 | CA | ILE | A | 182 | 25.854 | 37.913 | 54.481 | 1.00 12.70 | C |
| ATOM | 1174 | C | ILE | A | 182 | 26.198 | 39.282 | 55.049 | 1.00 12.70 | C |
| ATOM | 1175 | O | ILE | A | 182 | 25.362 | 39.959 | 55.639 | 1.00 12.70 | O |

FIG. 1-20

| | | | | | | | | | |
|---|---|---|---|---|---|---|---|---|---|
| ATOM | 1176 | CB | ILE | A | 182 | 24.733 | 38.035 | 53.417 | 1.00 18.50 | C |
| ATOM | 1177 | CG1 | ILE | A | 182 | 24.390 | 36.648 | 52.867 | 1.00 18.50 | C |
| ATOM | 1178 | CG2 | ILE | A | 182 | 25.154 | 38.975 | 52.297 | 1.00 18.50 | C |
| ATOM | 1179 | CD1 | ILE | A | 182 | 25.543 | 35.928 | 52.216 | 1.00 18.50 | C |
| ATOM | 1180 | N | LYS | A | 183 | 27.450 | 39.669 | 54.887 | 1.00 22.40 | N |
| ATOM | 1181 | CA | LYS | A | 183 | 27.912 | 40.947 | 55.372 | 1.00 22.40 | C |
| ATOM | 1182 | C | LYS | A | 183 | 29.123 | 41.353 | 54.558 | 1.00 22.40 | C |
| ATOM | 1183 | O | LYS | A | 183 | 29.874 | 40.506 | 54.073 | 1.00 22.40 | O |
| ATOM | 1184 | CB | LYS | A | 183 | 28.284 | 40.868 | 56.852 | 1.00 28.78 | C |
| ATOM | 1185 | CG | LYS | A | 183 | 29.327 | 39.814 | 57.188 | 1.00 28.78 | C |
| ATOM | 1186 | CD | LYS | A | 183 | 29.784 | 39.987 | 58.614 | 1.00 28.78 | C |
| ATOM | 1187 | CE | LYS | A | 183 | 30.439 | 38.737 | 59.150 | 1.00 28.78 | C |
| ATOM | 1188 | NZ | LYS | A | 183 | 30.875 | 38.884 | 60.564 | 0.00 28.78 | N |
| ATOM | 1189 | N | PRO | A | 184 | 29.340 | 42.662 | 54.420 | 1.00 25.56 | N |
| ATOM | 1190 | CA | PRO | A | 184 | 30.454 | 43.232 | 53.664 | 1.00 25.56 | C |
| ATOM | 1191 | C | PRO | A | 184 | 31.780 | 42.508 | 53.819 | 1.00 25.56 | C |
| ATOM | 1192 | O | PRO | A | 184 | 32.515 | 42.372 | 52.848 | 1.00 25.56 | O |
| ATOM | 1193 | CB | PRO | A | 184 | 30.509 | 44.667 | 54.173 | 1.00 20.25 | C |
| ATOM | 1194 | CG | PRO | A | 184 | 29.075 | 44.965 | 54.462 | 1.00 20.25 | C |
| ATOM | 1195 | CD | PRO | A | 184 | 28.617 | 43.710 | 55.158 | 1.00 20.25 | C |
| ATOM | 1196 | N | GLN | A | 185 | 32.077 | 42.041 | 55.031 | 1.00 23.26 | N |
| ATOM | 1197 | CA | GLN | A | 185 | 33.335 | 41.341 | 55.304 | 1.00 23.26 | C |
| ATOM | 1198 | C | GLN | A | 185 | 33.437 | 39.961 | 54.693 | 1.00 23.26 | C |
| ATOM | 1199 | O | GLN | A | 185 | 34.536 | 39.465 | 54.484 | 1.00 23.26 | O |
| ATOM | 1200 | CB | GLN | A | 185 | 33.586 | 41.205 | 56.807 | 1.00 41.92 | C |
| ATOM | 1201 | CG | GLN | A | 185 | 33.616 | 42.510 | 57.564 | 1.00 41.92 | C |
| ATOM | 1202 | CD | GLN | A | 185 | 32.273 | 42.847 | 58.164 | 1.00 41.92 | C |
| ATOM | 1203 | OE1 | GLN | A | 185 | 31.253 | 42.905 | 57.464 | 1.00 41.92 | O |
| ATOM | 1204 | NE2 | GLN | A | 185 | 32.258 | 43.064 | 59.477 | 1.00 41.92 | N |
| ATOM | 1205 | N | ASN | A | 186 | 32.295 | 39.338 | 54.422 | 1.00 19.39 | N |
| ATOM | 1206 | CA | ASN | A | 186 | 32.293 | 38.011 | 53.829 | 1.00 19.39 | C |
| ATOM | 1207 | C | ASN | A | 186 | 32.199 | 38.070 | 52.320 | 1.00 19.39 | C |
| ATOM | 1208 | O | ASN | A | 186 | 31.858 | 37.088 | 51.668 | 1.00 19.39 | O |
| ATOM | 1209 | CB | ASN | A | 186 | 31.158 | 37.164 | 54.390 | 1.00 23.19 | C |
| ATOM | 1210 | CG | ASN | A | 186 | 31.369 | 36.812 | 55.841 | 1.00 23.19 | C |
| ATOM | 1211 | OD1 | ASN | A | 186 | 32.500 | 36.606 | 56.273 | 1.00 23.19 | O |
| ATOM | 1212 | ND2 | ASN | A | 186 | 30.282 | 36.731 | 56.599 | 1.00 23.19 | N |
| ATOM | 1213 | N | LEU | A | 187 | 32.505 | 39.238 | 51.777 | 1.00 16.46 | N |
| ATOM | 1214 | CA | LEU | A | 187 | 32.499 | 39.433 | 50.345 | 1.00 16.46 | C |
| ATOM | 1215 | C | LEU | A | 187 | 33.925 | 39.728 | 49.903 | 1.00 16.46 | C |
| ATOM | 1216 | O | LEU | A | 187 | 34.386 | 40.861 | 49.964 | 1.00 16.46 | O |
| ATOM | 1217 | CB | LEU | A | 187 | 31.578 | 40.590 | 49.966 | 1.00 21.42 | C |
| ATOM | 1218 | CG | LEU | A | 187 | 30.114 | 40.438 | 50.384 | 1.00 21.42 | C |
| ATOM | 1219 | CD1 | LEU | A | 187 | 29.348 | 41.638 | 49.928 | 1.00 21.42 | C |
| ATOM | 1220 | CD2 | LEU | A | 187 | 29.514 | 39.164 | 49.801 | 1.00 21.42 | C |
| ATOM | 1221 | N | LEU | A | 188 | 34.633 | 38.691 | 49.478 | 1.00 26.45 | N |
| ATOM | 1222 | CA | LEU | A | 188 | 36.004 | 38.848 | 49.028 | 1.00 26.45 | C |
| ATOM | 1223 | C | LEU | A | 188 | 35.994 | 39.337 | 47.594 | 1.00 26.45 | C |
| ATOM | 1224 | O | LEU | A | 188 | 35.086 | 39.026 | 46.818 | 1.00 26.45 | O |
| ATOM | 1225 | CB | LEU | A | 188 | 36.745 | 37.515 | 49.088 | 1.00 28.74 | C |
| ATOM | 1226 | CG | LEU | A | 188 | 36.637 | 36.664 | 50.352 | 1.00 28.74 | C |
| ATOM | 1227 | CD1 | LEU | A | 188 | 37.412 | 35.392 | 50.137 | 1.00 28.74 | C |
| ATOM | 1228 | CD2 | LEU | A | 188 | 37.173 | 37.406 | 51.560 | 1.00 28.74 | C |
| ATOM | 1229 | N | LEU | A | 189 | 37.006 | 40.107 | 47.230 | 1.00 31.93 | N |
| ATOM | 1230 | CA | LEU | A | 189 | 37.075 | 40.596 | 45.873 | 1.00 31.93 | C |
| ATOM | 1231 | C | LEU | A | 189 | 38.495 | 40.884 | 45.400 | 1.00 31.93 | C |
| ATOM | 1232 | O | LEU | A | 189 | 39.360 | 41.292 | 46.169 | 1.00 31.93 | O |
| ATOM | 1233 | CB | LEU | A | 189 | 36.168 | 41.824 | 45.716 | 1.00 28.57 | C |
| ATOM | 1234 | CG | LEU | A | 189 | 36.507 | 43.170 | 46.340 | 1.00 28.57 | C |
| ATOM | 1235 | CD1 | LEU | A | 189 | 35.261 | 44.016 | 46.315 | 1.00 28.57 | C |
| ATOM | 1236 | CD2 | LEU | A | 189 | 36.994 | 43.010 | 47.751 | 0.00 28.57 | C |
| ATOM | 1237 | N | ASP | A | 190 | 38.718 | 40.606 | 44.121 | 1.00 38.76 | N |

FIG. 1-21

```
ATOM   1238  CA   ASP A 190      39.991  40.812  43.451  1.00 38.76           C
ATOM   1239  C    ASP A 190      39.926  42.256  42.991  1.00 38.76           C
ATOM   1240  O    ASP A 190      39.009  42.629  42.270  1.00 38.76           O
ATOM   1241  CB   ASP A 190      40.082  39.881  42.245  1.00 48.51           C
ATOM   1242  CG   ASP A 190      41.351  40.069  41.456  1.00 48.51           C
ATOM   1243  OD1  ASP A 190      41.693  41.248  41.171  1.00 48.51           O
ATOM   1244  OD2  ASP A 190      41.991  39.042  41.116  1.00 48.51           O
ATOM   1245  N    PRO A 191      40.897  43.088  43.396  1.00 50.51           N
ATOM   1246  CA   PRO A 191      40.897  44.501  43.005  1.00 50.51           C
ATOM   1247  C    PRO A 191      40.987  44.813  41.513  1.00 50.51           C
ATOM   1248  O    PRO A 191      40.411  45.806  41.045  1.00 50.51           O
ATOM   1249  CB   PRO A 191      42.060  45.080  43.803  1.00 49.44           C
ATOM   1250  CG   PRO A 191      42.989  43.914  43.959  1.00 49.44           C
ATOM   1251  CD   PRO A 191      42.057  42.772  44.253  1.00 49.44           C
ATOM   1252  N    ASP A 192      41.681  43.976  40.753  1.00 42.25           N
ATOM   1253  CA   ASP A 192      41.802  44.245  39.327  1.00 42.25           C
ATOM   1254  C    ASP A 192      40.721  43.625  38.468  1.00 42.25           C
ATOM   1255  O    ASP A 192      40.156  44.297  37.612  1.00 42.25           O
ATOM   1256  CB   ASP A 192      43.175  43.814  38.841  1.00 49.21           C
ATOM   1257  CG   ASP A 192      44.270  44.582  39.523  1.00 49.21           C
ATOM   1258  OD1  ASP A 192      44.255  45.826  39.412  1.00 49.21           O
ATOM   1259  OD2  ASP A 192      45.126  43.957  40.182  1.00 49.21           O
ATOM   1260  N    THR A 193      40.426  42.350  38.684  1.00 29.33           N
ATOM   1261  CA   THR A 193      39.397  41.688  37.899  1.00 29.33           C
ATOM   1262  C    THR A 193      37.991  42.148  38.290  1.00 29.33           C
ATOM   1263  O    THR A 193      37.080  42.157  37.464  1.00 29.33           O
ATOM   1264  CB   THR A 193      39.495  40.166  38.063  1.00 34.77           C
ATOM   1265  OG1  THR A 193      39.388  39.823  39.450  1.00 34.77           O
ATOM   1266  CG2  THR A 193      40.823  39.671  37.532  1.00 34.77           C
ATOM   1267  N    ALA A 194      37.830  42.532  39.553  1.00 23.90           N
ATOM   1268  CA   ALA A 194      36.550  42.986  40.087  1.00 23.90           C
ATOM   1269  C    ALA A 194      35.613  41.818  40.375  1.00 23.90           C
ATOM   1270  O    ALA A 194      34.409  42.010  40.529  1.00 23.90           O
ATOM   1271  CB   ALA A 194      35.873  43.964  39.118  1.00  9.74           C
ATOM   1272  N    VAL A 195      36.148  40.604  40.439  1.00 29.57           N
ATOM   1273  CA   VAL A 195      35.279  39.473  40.713  1.00 29.57           C
ATOM   1274  C    VAL A 195      35.125  39.322  42.213  1.00 29.57           C
ATOM   1275  O    VAL A 195      36.091  39.427  42.973  1.00 29.57           O
ATOM   1276  CB   VAL A 195      35.783  38.129  40.049  1.00 32.11           C
ATOM   1277  CG1  VAL A 195      36.886  38.418  39.064  1.00 32.11           C
ATOM   1278  CG2  VAL A 195      36.198  37.107  41.103  1.00 32.11           C
ATOM   1279  N    LEU A 196      33.887  39.095  42.630  1.00 27.44           N
ATOM   1280  CA   LEU A 196      33.576  38.954  44.032  1.00 27.44           C
ATOM   1281  C    LEU A 196      33.298  37.496  44.345  1.00 27.44           C
ATOM   1282  O    LEU A 196      32.859  36.743  43.484  1.00 27.44           O
ATOM   1283  CB   LEU A 196      32.375  39.843  44.368  1.00 15.60           C
ATOM   1284  CG   LEU A 196      31.772  39.758  45.762  1.00 15.60           C
ATOM   1285  CD1  LEU A 196      31.063  41.042  46.092  1.00 15.60           C
ATOM   1286  CD2  LEU A 196      30.829  38.582  45.820  1.00 15.60           C
ATOM   1287  N    LYS A 197      33.586  37.098  45.575  1.00 23.44           N
ATOM   1288  CA   LYS A 197      33.353  35.730  45.990  1.00 23.44           C
ATOM   1289  C    LYS A 197      32.820  35.680  47.399  1.00 23.44           C
ATOM   1290  O    LYS A 197      33.408  36.253  48.310  1.00 23.44           O
ATOM   1291  CB   LYS A 197      34.641  34.922  45.888  1.00 30.76           C
ATOM   1292  CG   LYS A 197      35.011  34.626  44.472  1.00 30.76           C
ATOM   1293  CD   LYS A 197      36.302  33.890  44.382  1.00 30.76           C
ATOM   1294  CE   LYS A 197      36.624  33.624  42.930  1.00 30.76           C
ATOM   1295  NZ   LYS A 197      37.910  32.895  42.780  1.00 30.76           N
ATOM   1296  N    LEU A 198      31.695  35.002  47.584  1.00 25.20           N
ATOM   1297  CA   LEU A 198      31.133  34.912  48.916  1.00 25.20           C
ATOM   1298  C    LEU A 198      31.959  33.914  49.695  1.00 25.20           C
ATOM   1299  O    LEU A 198      32.332  32.872  49.179  1.00 25.20           O
```

FIG. 1-22

| | | | | | | | | | |
|---|---|---|---|---|---|---|---|---|---|
| ATOM | 1300 | CB | LEU | A | 198 | 29.685 | 34.455 | 48.883 | 1.00 24.11 | C |
| ATOM | 1301 | CG | LEU | A | 198 | 28.877 | 34.984 | 50.062 | 1.00 24.11 | C |
| ATOM | 1302 | CD1 | LEU | A | 198 | 27.541 | 34.314 | 50.020 | 1.00 24.11 | C |
| ATOM | 1303 | CD2 | LEU | A | 198 | 29.551 | 34.722 | 51.391 | 0.00 24.11 | C |
| ATOM | 1304 | N | CYS | A | 199 | 32.259 | 34.237 | 50.940 | 1.00 21.99 | N |
| ATOM | 1305 | CA | CYS | A | 199 | 33.044 | 33.334 | 51.744 | 1.00 21.99 | C |
| ATOM | 1306 | C | CYS | A | 199 | 32.413 | 33.097 | 53.097 | 1.00 21.99 | C |
| ATOM | 1307 | O | CYS | A | 199 | 31.312 | 33.560 | 53.378 | 1.00 21.99 | O |
| ATOM | 1308 | CB | CYS | A | 199 | 34.451 | 33.890 | 51.934 | 1.00 29.06 | C |
| ATOM | 1309 | SG | CYS | A | 199 | 34.512 | 35.423 | 52.831 | 1.00 29.06 | S |
| ATOM | 1310 | N | ASP | A | 200 | 33.131 | 32.344 | 53.919 | 1.00 24.47 | N |
| ATOM | 1311 | CA | ASP | A | 200 | 32.719 | 32.024 | 55.274 | 1.00 24.47 | C |
| ATOM | 1312 | C | ASP | A | 200 | 31.352 | 31.376 | 55.428 | 1.00 24.47 | C |
| ATOM | 1313 | O | ASP | A | 200 | 30.389 | 32.028 | 55.813 | 1.00 24.47 | O |
| ATOM | 1314 | CB | ASP | A | 200 | 32.782 | 33.281 | 56.117 | 1.00 45.70 | C |
| ATOM | 1315 | CG | ASP | A | 200 | 32.661 | 32.984 | 57.569 | 1.00 45.70 | C |
| ATOM | 1316 | OD1 | ASP | A | 200 | 33.267 | 31.971 | 58.004 | 1.00 45.70 | O |
| ATOM | 1317 | OD2 | ASP | A | 200 | 31.968 | 33.759 | 58.270 | 1.00 45.70 | O |
| ATOM | 1318 | N | PHE | A | 201 | 31.285 | 30.082 | 55.146 | 1.00 23.81 | N |
| ATOM | 1319 | CA | PHE | A | 201 | 30.038 | 29.346 | 55.244 | 1.00 23.81 | C |
| ATOM | 1320 | C | PHE | A | 201 | 29.875 | 28.656 | 56.579 | 1.00 23.81 | C |
| ATOM | 1321 | O | PHE | A | 201 | 29.098 | 27.731 | 56.720 | 1.00 23.81 | O |
| ATOM | 1322 | CB | PHE | A | 201 | 29.951 | 28.331 | 54.112 | 1.00 17.81 | C |
| ATOM | 1323 | CG | PHE | A | 201 | 29.820 | 28.962 | 52.766 | 1.00 17.81 | C |
| ATOM | 1324 | CD1 | PHE | A | 201 | 30.888 | 29.655 | 52.209 | 1.00 17.81 | C |
| ATOM | 1325 | CD2 | PHE | A | 201 | 28.609 | 28.929 | 52.086 | 1.00 17.81 | C |
| ATOM | 1326 | CE1 | PHE | A | 201 | 30.746 | 30.313 | 50.989 | 1.00 17.81 | C |
| ATOM | 1327 | CE2 | PHE | A | 201 | 28.458 | 29.580 | 50.873 | 1.00 17.81 | C |
| ATOM | 1328 | CZ | PHE | A | 201 | 29.522 | 30.277 | 50.320 | 1.00 17.81 | C |
| ATOM | 1329 | N | GLY | A | 202 | 30.604 | 29.142 | 57.567 | 1.00 20.45 | N |
| ATOM | 1330 | CA | GLY | A | 202 | 30.540 | 28.563 | 58.889 | 1.00 20.45 | C |
| ATOM | 1331 | C | GLY | A | 202 | 29.183 | 28.704 | 59.538 | 1.00 20.45 | C |
| ATOM | 1332 | O | GLY | A | 202 | 28.952 | 28.139 | 60.604 | 1.00 20.45 | O |
| ATOM | 1333 | N | SER | A | 203 | 28.280 | 29.444 | 58.907 | 1.00 28.53 | N |
| ATOM | 1334 | CA | SER | A | 203 | 26.944 | 29.627 | 59.474 | 1.00 28.53 | C |
| ATOM | 1335 | C | SER | A | 203 | 25.884 | 29.102 | 58.515 | 1.00 28.53 | C |
| ATOM | 1336 | O | SER | A | 203 | 24.692 | 29.142 | 58.810 | 1.00 28.53 | O |
| ATOM | 1337 | CB | SER | A | 203 | 26.690 | 31.114 | 59.776 | 1.00 27.90 | C |
| ATOM | 1338 | OG | SER | A | 203 | 27.546 | 31.584 | 60.800 | 1.00 27.90 | O |
| ATOM | 1339 | N | ALA | A | 204 | 26.341 | 28.601 | 57.371 | 1.00 22.96 | N |
| ATOM | 1340 | CA | ALA | A | 204 | 25.462 | 28.086 | 56.337 | 1.00 22.96 | C |
| ATOM | 1341 | C | ALA | A | 204 | 24.753 | 26.827 | 56.773 | 1.00 22.96 | C |
| ATOM | 1342 | O | ALA | A | 204 | 25.292 | 26.003 | 57.520 | 1.00 22.96 | O |
| ATOM | 1343 | CB | ALA | A | 204 | 26.255 | 27.824 | 55.072 | 1.00 20.62 | C |
| ATOM | 1344 | N | LYS | A | 205 | 23.533 | 26.674 | 56.292 | 1.00 33.91 | N |
| ATOM | 1345 | CA | LYS | A | 205 | 22.737 | 25.517 | 56.628 | 1.00 33.91 | C |
| ATOM | 1346 | C | LYS | A | 205 | 21.677 | 25.306 | 55.566 | 1.00 33.91 | C |
| ATOM | 1347 | O | LYS | A | 205 | 21.088 | 26.255 | 55.060 | 1.00 33.91 | O |
| ATOM | 1348 | CB | LYS | A | 205 | 22.039 | 25.735 | 57.965 | 1.00 32.05 | C |
| ATOM | 1349 | CG | LYS | A | 205 | 21.308 | 24.510 | 58.466 | 1.00 32.05 | C |
| ATOM | 1350 | CD | LYS | A | 205 | 20.141 | 24.864 | 59.375 | 1.00 32.05 | C |
| ATOM | 1351 | CE | LYS | A | 205 | 19.483 | 23.602 | 59.955 | 1.00 32.05 | C |
| ATOM | 1352 | NZ | LYS | A | 205 | 18.258 | 23.874 | 60.780 | 1.00 32.05 | N |
| ATOM | 1353 | N | GLN | A | 206 | 21.429 | 24.057 | 55.212 | 1.00 36.97 | N |
| ATOM | 1354 | CA | GLN | A | 206 | 20.378 | 23.813 | 54.254 | 1.00 36.97 | C |
| ATOM | 1355 | C | GLN | A | 206 | 19.094 | 23.860 | 55.061 | 1.00 36.97 | C |
| ATOM | 1356 | O | GLN | A | 206 | 18.964 | 23.134 | 56.036 | 1.00 36.97 | O |
| ATOM | 1357 | CB | GLN | A | 206 | 20.525 | 22.448 | 53.618 | 1.00 58.75 | C |
| ATOM | 1358 | CG | GLN | A | 206 | 19.285 | 22.091 | 52.831 | 1.00 58.75 | C |
| ATOM | 1359 | CD | GLN | A | 206 | 19.457 | 20.860 | 51.976 | 1.00 58.75 | C |
| ATOM | 1360 | OE1 | GLN | A | 206 | 18.467 | 20.295 | 51.484 | 1.00 58.75 | O |
| ATOM | 1361 | NE2 | GLN | A | 206 | 20.719 | 20.434 | 51.779 | 1.00 58.75 | N |

FIG. 1-23

```
ATOM   1362  N    LEU A 207      18.158  24.719  54.659  1.00 40.39           N
ATOM   1363  CA   LEU A 207      16.887  24.876  55.361  1.00 40.39           C
ATOM   1364  C    LEU A 207      15.795  23.974  54.801  1.00 40.39           C
ATOM   1365  O    LEU A 207      15.569  23.924  53.585  1.00 40.39           O
ATOM   1366  CB   LEU A 207      16.408  26.323  55.273  1.00 21.32           C
ATOM   1367  CG   LEU A 207      17.335  27.473  55.684  1.00 21.32           C
ATOM   1368  CD1  LEU A 207      16.665  28.788  55.319  1.00 21.32           C
ATOM   1369  CD2  LEU A 207      17.652  27.420  57.172  1.00 21.32           C
ATOM   1370  N    VAL A 208      15.109  23.268  55.691  1.00 39.57           N
ATOM   1371  CA   VAL A 208      14.032  22.382  55.276  1.00 39.57           C
ATOM   1372  C    VAL A 208      12.716  22.826  55.879  1.00 39.57           C
ATOM   1373  O    VAL A 208      12.600  22.933  57.103  1.00 39.57           O
ATOM   1374  CB   VAL A 208      14.284  20.961  55.733  1.00 29.39           C
ATOM   1375  CG1  VAL A 208      13.162  20.075  55.254  1.00 29.39           C
ATOM   1376  CG2  VAL A 208      15.627  20.495  55.226  1.00 29.39           C
ATOM   1377  N    ARG A 209      11.721  23.077  55.029  1.00 40.70           N
ATOM   1378  CA   ARG A 209      10.412  23.505  55.520  1.00 40.70           C
ATOM   1379  C    ARG A 209      10.003  22.538  56.618  1.00 40.70           C
ATOM   1380  O    ARG A 209      10.265  21.333  56.533  1.00 40.70           O
ATOM   1381  CB   ARG A 209       9.368  23.483  54.398  1.00 85.10           C
ATOM   1382  CG   ARG A 209       8.128  24.315  54.682  0.00 85.10           C
ATOM   1383  CD   ARG A 209       7.075  24.073  53.620  0.00 85.10           C
ATOM   1384  NE   ARG A 209       7.679  23.980  52.296  1.00 85.10           N
ATOM   1385  CZ   ARG A 209       7.016  23.643  51.187  1.00 85.10           C
ATOM   1386  NH1  ARG A 209       5.709  23.369  51.240  1.00 85.10           N
ATOM   1387  NH2  ARG A 209       7.666  23.558  50.021  1.00 85.10           N
ATOM   1388  N    GLY A 210       9.367  23.072  57.650  1.00 41.81           N
ATOM   1389  CA   GLY A 210       8.960  22.243  58.764  1.00 41.81           C
ATOM   1390  C    GLY A 210      10.007  22.300  59.858  1.00 41.81           C
ATOM   1391  O    GLY A 210       9.668  22.477  61.024  1.00 41.81           O
ATOM   1392  N    GLU A 211      11.279  22.160  59.488  1.00 54.48           N
ATOM   1393  CA   GLU A 211      12.385  22.194  60.457  1.00 54.48           C
ATOM   1394  C    GLU A 211      12.723  23.618  60.931  1.00 54.48           C
ATOM   1395  O    GLU A 211      12.869  24.535  60.122  1.00 54.48           O
ATOM   1396  CB   GLU A 211      13.649  21.548  59.859  1.00 81.01           C
ATOM   1397  CG   GLU A 211      13.657  20.017  59.844  1.00 81.01           C
ATOM   1398  CD   GLU A 211      14.987  19.435  59.329  1.00 81.01           C
ATOM   1399  OE1  GLU A 211      15.254  18.217  59.556  1.00 81.01           O
ATOM   1400  OE2  GLU A 211      15.764  20.201  58.696  1.00 81.01           O
ATOM   1401  N    PRO A 212      12.859  23.808  62.258  1.00 40.07           N
ATOM   1402  CA   PRO A 212      13.176  25.089  62.912  1.00 40.07           C
ATOM   1403  C    PRO A 212      14.669  25.427  62.905  1.00 40.07           C
ATOM   1404  O    PRO A 212      15.507  24.527  62.878  1.00 40.07           O
ATOM   1405  CB   PRO A 212      12.657  24.869  64.325  1.00 38.64           C
ATOM   1406  CG   PRO A 212      13.068  23.416  64.564  1.00 38.64           C
ATOM   1407  CD   PRO A 212      12.631  22.750  63.266  1.00 38.64           C
ATOM   1408  N    ASN A 213      14.999  26.716  62.964  1.00 28.50           N
ATOM   1409  CA   ASN A 213      16.403  27.132  62.953  1.00 28.50           C
ATOM   1410  C    ASN A 213      16.722  28.250  63.941  1.00 28.50           C
ATOM   1411  O    ASN A 213      15.885  29.120  64.182  1.00 28.50           O
ATOM   1412  CB   ASN A 213      16.771  27.582  61.551  1.00 27.76           C
ATOM   1413  CG   ASN A 213      16.288  26.628  60.502  1.00 27.76           C
ATOM   1414  OD1  ASN A 213      16.830  25.535  60.346  1.00 27.76           O
ATOM   1415  ND2  ASN A 213      15.244  27.027  59.779  1.00 27.76           N
ATOM   1416  N    VAL A 214      17.930  28.240  64.504  1.00 20.19           N
ATOM   1417  CA   VAL A 214      18.294  29.282  65.463  1.00 20.19           C
ATOM   1418  C    VAL A 214      18.167  30.634  64.835  1.00 20.19           C
ATOM   1419  O    VAL A 214      18.460  30.816  63.660  1.00 20.19           O
ATOM   1420  CB   VAL A 214      19.730  29.190  65.961  1.00 10.57           C
ATOM   1421  CG1  VAL A 214      19.873  27.959  66.868  1.00 10.57           C
ATOM   1422  CG2  VAL A 214      20.724  29.302  64.746  1.00 10.57           C
ATOM   1423  N    SER A 215      17.758  31.599  65.636  1.00 27.64           N
```

FIG. 1-24

```
ATOM   1424  CA  SER A 215      17.486  32.908  65.054  1.00 27.64           C
ATOM   1425  C   SER A 215      18.557  33.923  65.452  1.00 27.64           C
ATOM   1426  O   SER A 215      18.393  35.131  65.345  1.00 27.64           O
ATOM   1427  CB  SER A 215      16.109  33.377  65.532  1.00 34.41           C
ATOM   1428  OG  SER A 215      16.138  33.573  66.945  1.00 34.41           O
ATOM   1429  N   TYR A 216      19.674  33.381  65.967  1.00 27.22           N
ATOM   1430  CA  TYR A 216      20.797  34.231  66.337  1.00 27.22           C
ATOM   1431  C   TYR A 216      22.058  33.838  65.563  1.00 27.22           C
ATOM   1432  O   TYR A 216      23.053  33.390  66.115  1.00 27.22           O
ATOM   1433  CB  TYR A 216      21.038  34.067  67.838  1.00 34.54           C
ATOM   1434  CG  TYR A 216      21.243  32.629  68.161  1.00 34.54           C
ATOM   1435  CD1 TYR A 216      22.340  31.949  67.638  1.00 34.54           C
ATOM   1436  CD2 TYR A 216      20.340  31.951  68.980  1.00 34.54           C
ATOM   1437  CE1 TYR A 216      22.534  30.607  67.931  1.00 34.54           C
ATOM   1438  CE2 TYR A 216      20.533  30.609  69.273  1.00 34.54           C
ATOM   1439  CZ  TYR A 216      21.625  29.938  68.753  1.00 34.54           C
ATOM   1440  OH  TYR A 216      21.848  28.613  69.075  1.00 34.54           O
ATOM   1441  N   ILE A 217      21.975  33.983  64.228  1.00 41.65           N
ATOM   1442  CA  ILE A 217      23.089  33.559  63.390  1.00 41.65           C
ATOM   1443  C   ILE A 217      23.558  34.676  62.455  1.00 41.65           C
ATOM   1444  O   ILE A 217      24.606  34.605  61.828  1.00 41.65           O
ATOM   1445  CB  ILE A 217      22.626  32.356  62.568  1.00 29.43           C
ATOM   1446  CG1 ILE A 217      21.099  32.257  62.593  1.00 29.43           C
ATOM   1447  CG2 ILE A 217      23.192  31.058  63.171  1.00 29.43           C
ATOM   1448  CD1 ILE A 217      20.440  33.159  61.549  1.00 29.43           C
ATOM   1449  N   CYS A 218      22.717  35.721  62.343  1.00 31.34           N
ATOM   1450  CA  CYS A 218      23.042  36.804  61.423  1.00 31.34           C
ATOM   1451  C   CYS A 218      23.754  37.961  62.125  1.00 31.34           C
ATOM   1452  O   CYS A 218      23.629  38.180  63.324  1.00 31.34           O
ATOM   1453  CB  CYS A 218      21.744  37.298  60.784  1.00 31.69           C
ATOM   1454  SG  CYS A 218      22.030  38.092  59.187  1.00 31.69           S
ATOM   1455  N   SER A 219      24.559  38.692  61.331  1.00 23.25           N
ATOM   1456  CA  SER A 219      25.203  39.900  61.831  1.00 23.25           C
ATOM   1457  C   SER A 219      24.177  40.929  62.312  1.00 23.25           C
ATOM   1458  O   SER A 219      22.992  40.859  62.011  1.00 23.25           O
ATOM   1459  CB  SER A 219      26.049  40.492  60.703  1.00 11.21           C
ATOM   1460  OG  SER A 219      27.304  39.815  60.653  0.00 11.21           O
ATOM   1461  N   ARG A 220      24.667  41.887  63.120  1.00 28.67           N
ATOM   1462  CA  ARG A 220      23.767  42.891  63.679  1.00 28.67           C
ATOM   1463  C   ARG A 220      23.107  43.748  62.593  1.00 28.67           C
ATOM   1464  O   ARG A 220      21.920  43.645  62.316  1.00 28.67           O
ATOM   1465  CB  ARG A 220      24.565  43.773  64.640  0.00 67.76           C
ATOM   1466  CG  ARG A 220      24.656  43.163  66.039  0.00 67.76           C
ATOM   1467  CD  ARG A 220      25.838  43.724  66.839  0.00 67.76           C
ATOM   1468  NE  ARG A 220      25.543  45.078  67.317  1.00 67.76           N
ATOM   1469  CZ  ARG A 220      26.088  46.105  66.637  1.00 67.76           C
ATOM   1470  NH1 ARG A 220      26.846  45.872  65.579  0.00 67.76           N
ATOM   1471  NH2 ARG A 220      25.860  47.359  67.039  1.00 67.76           N
ATOM   1472  N   TYR A 221      23.914  44.647  61.997  1.00 20.20           N
ATOM   1473  CA  TYR A 221      23.368  45.518  60.960  1.00 20.20           C
ATOM   1474  C   TYR A 221      22.770  44.711  59.803  1.00 20.20           C
ATOM   1475  O   TYR A 221      22.145  45.246  58.897  1.00 20.20           O
ATOM   1476  CB  TYR A 221      24.492  46.420  60.445  1.00 47.15           C
ATOM   1477  CG  TYR A 221      25.111  47.157  61.578  1.00 47.15           C
ATOM   1478  CD1 TYR A 221      24.347  47.484  62.695  1.00 47.15           C
ATOM   1479  CD2 TYR A 221      26.462  47.503  61.541  1.00 47.15           C
ATOM   1480  CE1 TYR A 221      24.929  48.145  63.768  1.00 47.15           C
ATOM   1481  CE2 TYR A 221      27.043  48.163  62.613  1.00 47.15           C
ATOM   1482  CZ  TYR A 221      26.284  48.481  63.725  1.00 47.15           C
ATOM   1483  OH  TYR A 221      26.870  49.083  64.822  1.00 47.15           O
ATOM   1484  N   TYR A 222      22.817  43.375  59.655  1.00 23.68           N
ATOM   1485  CA  TYR A 222      22.209  42.776  58.469  1.00 23.68           C
```

FIG. 1-25

```
ATOM   1486  C    TYR A 222      21.126  41.754  58.822  1.00 23.68           C
ATOM   1487  O    TYR A 222      20.614  41.035  57.973  1.00 23.68           O
ATOM   1488  CB   TYR A 222      23.315  42.110  57.649  1.00 22.29           C
ATOM   1489  CG   TYR A 222      24.478  43.031  57.538  1.00 22.29           C
ATOM   1490  CD1  TYR A 222      25.552  42.900  58.415  1.00 22.29           C
ATOM   1491  CD2  TYR A 222      24.455  44.091  56.631  1.00 22.29           C
ATOM   1492  CE1  TYR A 222      26.586  43.825  58.395  1.00 22.29           C
ATOM   1493  CE2  TYR A 222      25.487  45.017  56.612  1.00 22.29           C
ATOM   1494  CZ   TYR A 222      26.546  44.889  57.492  1.00 22.29           C
ATOM   1495  OH   TYR A 222      27.571  45.815  57.488  1.00 22.29           O
ATOM   1496  N    ARG A 223      20.715  41.632  60.077  1.00 28.31           N
ATOM   1497  CA   ARG A 223      19.701  40.658  60.443  1.00 28.31           C
ATOM   1498  C    ARG A 223      18.345  41.086  59.935  1.00 28.31           C
ATOM   1499  O    ARG A 223      17.962  42.247  60.048  1.00 28.31           O
ATOM   1500  CB   ARG A 223      19.627  40.500  61.953  1.00 36.69           C
ATOM   1501  CG   ARG A 223      20.971  40.587  62.639  1.00 36.69           C
ATOM   1502  CD   ARG A 223      20.837  40.282  64.119  1.00 36.69           C
ATOM   1503  NE   ARG A 223      20.397  38.899  64.298  1.00 36.69           N
ATOM   1504  CZ   ARG A 223      19.459  38.514  65.155  1.00 36.69           C
ATOM   1505  NH1  ARG A 223      18.856  39.405  65.924  1.00 36.69           N
ATOM   1506  NH2  ARG A 223      19.112  37.244  65.221  1.00 36.69           N
ATOM   1507  N    ALA A 224      17.626  40.137  59.359  1.00 24.40           N
ATOM   1508  CA   ALA A 224      16.295  40.398  58.859  1.00 24.40           C
ATOM   1509  C    ALA A 224      15.353  40.555  60.056  1.00 24.40           C
ATOM   1510  O    ALA A 224      15.523  39.906  61.091  1.00 24.40           O
ATOM   1511  CB   ALA A 224      15.845  39.244  57.980  1.00 16.64           C
ATOM   1512  N    PRO A 225      14.347  41.424  59.928  1.00 28.21           N
ATOM   1513  CA   PRO A 225      13.382  41.656  61.005  1.00 28.21           C
ATOM   1514  C    PRO A 225      12.925  40.389  61.726  1.00 28.21           C
ATOM   1515  O    PRO A 225      12.790  40.377  62.949  1.00 28.21           O
ATOM   1516  CB   PRO A 225      12.234  42.373  60.292  1.00 27.42           C
ATOM   1517  CG   PRO A 225      12.502  42.144  58.800  1.00 27.42           C
ATOM   1518  CD   PRO A 225      13.978  42.181  58.724  1.00 27.42           C
ATOM   1519  N    GLU A 226      12.692  39.325  60.962  1.00 36.44           N
ATOM   1520  CA   GLU A 226      12.262  38.043  61.517  1.00 36.44           C
ATOM   1521  C    GLU A 226      13.296  37.519  62.514  1.00 36.44           C
ATOM   1522  O    GLU A 226      12.961  37.053  63.608  1.00 36.44           O
ATOM   1523  CB   GLU A 226      12.103  37.012  60.408  1.00 33.70           C
ATOM   1524  CG   GLU A 226      11.499  37.565  59.156  1.00 33.70           C
ATOM   1525  CD   GLU A 226      12.524  37.794  58.075  1.00 33.70           C
ATOM   1526  OE1  GLU A 226      12.969  36.799  57.448  1.00 33.70           O
ATOM   1527  OE2  GLU A 226      12.883  38.971  57.865  1.00 33.70           O
ATOM   1528  N    LEU A 227      14.561  37.571  62.123  1.00 28.87           N
ATOM   1529  CA   LEU A 227      15.597  37.115  63.014  1.00 28.87           C
ATOM   1530  C    LEU A 227      15.503  37.948  64.291  1.00 28.87           C
ATOM   1531  O    LEU A 227      15.635  37.423  65.385  1.00 28.87           O
ATOM   1532  CB   LEU A 227      16.961  37.278  62.339  1.00 20.76           C
ATOM   1533  CG   LEU A 227      17.100  36.496  61.027  1.00 20.76           C
ATOM   1534  CD1  LEU A 227      18.488  36.720  60.459  1.00 20.76           C
ATOM   1535  CD2  LEU A 227      16.841  35.009  61.259  1.00 20.76           C
ATOM   1536  N    ILE A 228      15.244  39.244  64.136  1.00 25.06           N
ATOM   1537  CA   ILE A 228      15.138  40.168  65.259  1.00 25.06           C
ATOM   1538  C    ILE A 228      13.943  39.810  66.118  1.00 25.06           C
ATOM   1539  O    ILE A 228      13.978  39.924  67.336  1.00 25.06           O
ATOM   1540  CB   ILE A 228      14.978  41.619  64.770  1.00 24.30           C
ATOM   1541  CG1  ILE A 228      16.204  42.027  63.945  1.00 24.30           C
ATOM   1542  CG2  ILE A 228      14.785  42.548  65.960  1.00 24.30           C
ATOM   1543  CD1  ILE A 228      16.122  43.415  63.307  1.00 24.30           C
ATOM   1544  N    PHE A 229      12.875  39.390  65.466  1.00 20.97           N
ATOM   1545  CA   PHE A 229      11.680  38.985  66.171  1.00 20.97           C
ATOM   1546  C    PHE A 229      11.830  37.548  66.670  1.00 20.97           C
ATOM   1547  O    PHE A 229      10.879  36.968  67.166  1.00 20.97           O
```

FIG. 1-26

```
ATOM   1548  CB   PHE A 229      10.456  39.087  65.259  1.00 31.34           C
ATOM   1549  CG   PHE A 229       9.930  40.480  65.104  1.00 31.34           C
ATOM   1550  CD1  PHE A 229       9.581  41.227  66.219  1.00 31.34           C
ATOM   1551  CD2  PHE A 229       9.770  41.046  63.840  1.00 31.34           C
ATOM   1552  CE1  PHE A 229       9.081  42.524  66.083  1.00 31.34           C
ATOM   1553  CE2  PHE A 229       9.272  42.341  63.694  1.00 31.34           C
ATOM   1554  CZ   PHE A 229       8.928  43.081  64.816  1.00 31.34           C
ATOM   1555  N    GLY A 230      13.020  36.978  66.529  1.00 25.31           N
ATOM   1556  CA   GLY A 230      13.251  35.621  66.999  1.00 25.31           C
ATOM   1557  C    GLY A 230      12.540  34.473  66.277  1.00 25.31           C
ATOM   1558  O    GLY A 230      12.422  33.379  66.835  1.00 25.31           O
ATOM   1559  N    ALA A 231      12.069  34.703  65.051  1.00 21.06           N
ATOM   1560  CA   ALA A 231      11.406  33.657  64.275  1.00 21.06           C
ATOM   1561  C    ALA A 231      12.369  32.492  64.085  1.00 21.06           C
ATOM   1562  O    ALA A 231      13.576  32.698  63.997  1.00 21.06           O
ATOM   1563  CB   ALA A 231      10.976  34.202  62.915  1.00 14.27           C
ATOM   1564  N    THR A 232      11.843  31.272  64.033  1.00 25.78           N
ATOM   1565  CA   THR A 232      12.701  30.106  63.849  1.00 25.78           C
ATOM   1566  C    THR A 232      12.293  29.338  62.605  1.00 25.78           C
ATOM   1567  O    THR A 232      12.861  28.290  62.290  1.00 25.78           O
ATOM   1568  CB   THR A 232      12.645  29.150  65.054  1.00 38.77           C
ATOM   1569  OG1  THR A 232      11.361  28.521  65.115  1.00 38.77           O
ATOM   1570  CG2  THR A 232      12.890  29.910  66.337  1.00 38.77           C
ATOM   1571  N    ASP A 233      11.308  29.881  61.900  1.00 29.45           N
ATOM   1572  CA   ASP A 233      10.795  29.289  60.670  1.00 29.45           C
ATOM   1573  C    ASP A 233      11.153  30.180  59.476  1.00 29.45           C
ATOM   1574  O    ASP A 233      10.468  30.161  58.454  1.00 29.45           O
ATOM   1575  CB   ASP A 233       9.273  29.161  60.760  1.00 35.57           C
ATOM   1576  CG   ASP A 233       8.592  30.509  60.852  1.00 35.57           C
ATOM   1577  OD1  ASP A 233       9.239  31.464  61.316  1.00 35.57           O
ATOM   1578  OD2  ASP A 233       7.415  30.622  60.475  1.00 35.57           O
ATOM   1579  N    TYR A 234      12.213  30.969  59.610  1.00 23.50           N
ATOM   1580  CA   TYR A 234      12.622  31.848  58.524  1.00 23.50           C
ATOM   1581  C    TYR A 234      13.056  31.070  57.285  1.00 23.50           C
ATOM   1582  O    TYR A 234      13.426  29.896  57.361  1.00 23.50           O
ATOM   1583  CB   TYR A 234      13.738  32.791  58.987  1.00 16.93           C
ATOM   1584  CG   TYR A 234      14.973  32.120  59.545  1.00 16.93           C
ATOM   1585  CD1  TYR A 234      15.953  31.609  58.704  1.00 16.93           C
ATOM   1586  CD2  TYR A 234      15.170  32.017  60.916  1.00 16.93           C
ATOM   1587  CE1  TYR A 234      17.092  31.016  59.214  1.00 16.93           C
ATOM   1588  CE2  TYR A 234      16.307  31.423  61.434  1.00 16.93           C
ATOM   1589  CZ   TYR A 234      17.261  30.924  60.581  1.00 16.93           C
ATOM   1590  OH   TYR A 234      18.364  30.299  61.097  1.00 16.93           O
ATOM   1591  N    THR A 235      12.990  31.734  56.139  1.00 28.45           N
ATOM   1592  CA   THR A 235      13.360  31.128  54.873  1.00 28.45           C
ATOM   1593  C    THR A 235      14.672  31.711  54.432  1.00 28.45           C
ATOM   1594  O    THR A 235      15.094  32.748  54.937  1.00 28.45           O
ATOM   1595  CB   THR A 235      12.335  31.441  53.800  1.00 25.35           C
ATOM   1596  OG1  THR A 235      12.297  32.856  53.584  1.00 25.35           O
ATOM   1597  CG2  THR A 235      10.969  30.983  54.234  1.00 25.35           C
ATOM   1598  N    SER A 236      15.313  31.062  53.471  1.00 27.63           N
ATOM   1599  CA   SER A 236      16.593  31.554  52.991  1.00 27.63           C
ATOM   1600  C    SER A 236      16.502  32.981  52.447  1.00 27.63           C
ATOM   1601  O    SER A 236      17.507  33.550  52.052  1.00 27.63           O
ATOM   1602  CB   SER A 236      17.159  30.625  51.920  1.00 18.08           C
ATOM   1603  OG   SER A 236      16.497  30.813  50.696  1.00 18.08           O
ATOM   1604  N    SER A 237      15.315  33.575  52.435  1.00 27.48           N
ATOM   1605  CA   SER A 237      15.233  34.925  51.918  1.00 27.48           C
ATOM   1606  C    SER A 237      15.835  35.942  52.879  1.00 27.48           C
ATOM   1607  O    SER A 237      15.849  37.139  52.588  1.00 27.48           O
ATOM   1608  CB   SER A 237      13.795  35.314  51.560  1.00 24.33           C
ATOM   1609  OG   SER A 237      13.001  35.535  52.702  1.00 24.33           O
```

FIG. 1-27

```
ATOM   1610  N    ILE A 238      16.331  35.481  54.025  1.00 29.83           N
ATOM   1611  CA   ILE A 238      16.966  36.407  54.956  1.00 29.83           C
ATOM   1612  C    ILE A 238      18.305  36.855  54.347  1.00 29.83           C
ATOM   1613  O    ILE A 238      18.841  37.895  54.706  1.00 29.83           O
ATOM   1614  CB   ILE A 238      17.233  35.776  56.343  1.00 23.63           C
ATOM   1615  CG1  ILE A 238      18.061  34.508  56.198  1.00 23.63           C
ATOM   1616  CG2  ILE A 238      15.936  35.494  57.044  1.00 23.63           C
ATOM   1617  CD1  ILE A 238      18.605  34.016  57.513  1.00 23.63           C
ATOM   1618  N    ASP A 239      18.838  36.054  53.428  1.00 27.51           N
ATOM   1619  CA   ASP A 239      20.077  36.381  52.743  1.00 27.51           C
ATOM   1620  C    ASP A 239      19.827  37.573  51.833  1.00 27.51           C
ATOM   1621  O    ASP A 239      20.704  38.409  51.627  1.00 27.51           O
ATOM   1622  CB   ASP A 239      20.563  35.209  51.898  1.00 21.27           C
ATOM   1623  CG   ASP A 239      21.273  34.163  52.713  1.00 21.27           C
ATOM   1624  OD1  ASP A 239      21.701  34.480  53.840  1.00 21.27           O
ATOM   1625  OD2  ASP A 239      21.421  33.027  52.218  1.00 21.27           O
ATOM   1626  N    VAL A 240      18.620  37.654  51.293  1.00 23.41           N
ATOM   1627  CA   VAL A 240      18.275  38.756  50.406  1.00 23.41           C
ATOM   1628  C    VAL A 240      18.175  40.088  51.158  1.00 23.41           C
ATOM   1629  O    VAL A 240      18.592  41.127  50.653  1.00 23.41           O
ATOM   1630  CB   VAL A 240      16.961  38.454  49.669  1.00 19.10           C
ATOM   1631  CG1  VAL A 240      16.540  39.637  48.821  1.00 19.10           C
ATOM   1632  CG2  VAL A 240      17.149  37.224  48.803  1.00 19.10           C
ATOM   1633  N    TRP A 241      17.629  40.041  52.372  1.00 22.76           N
ATOM   1634  CA   TRP A 241      17.485  41.224  53.202  1.00 22.76           C
ATOM   1635  C    TRP A 241      18.878  41.777  53.473  1.00 22.76           C
ATOM   1636  O    TRP A 241      19.139  42.964  53.295  1.00 22.76           O
ATOM   1637  CB   TRP A 241      16.777  40.862  54.521  1.00 20.47           C
ATOM   1638  CG   TRP A 241      16.707  42.011  55.513  1.00 20.47           C
ATOM   1639  CD1  TRP A 241      17.689  42.406  56.369  1.00 20.47           C
ATOM   1640  CD2  TRP A 241      15.647  42.967  55.656  1.00 20.47           C
ATOM   1641  NE1  TRP A 241      17.320  43.542  57.025  1.00 20.47           N
ATOM   1642  CE2  TRP A 241      16.072  43.912  56.613  1.00 20.47           C
ATOM   1643  CE3  TRP A 241      14.385  43.118  55.066  1.00 20.47           C
ATOM   1644  CZ2  TRP A 241      15.276  45.005  56.998  1.00 20.47           C
ATOM   1645  CZ3  TRP A 241      13.593  44.206  55.447  1.00 20.47           C
ATOM   1646  CH2  TRP A 241      14.044  45.132  56.406  1.00 20.47           C
ATOM   1647  N    SER A 242      19.767  40.892  53.897  1.00 23.50           N
ATOM   1648  CA   SER A 242      21.140  41.257  54.188  1.00 23.50           C
ATOM   1649  C    SER A 242      21.789  41.915  52.989  1.00 23.50           C
ATOM   1650  O    SER A 242      22.464  42.931  53.125  1.00 23.50           O
ATOM   1651  CB   SER A 242      21.951  40.020  54.559  1.00 29.39           C
ATOM   1652  OG   SER A 242      21.385  39.370  55.673  1.00 29.39           O
ATOM   1653  N    ALA A 243      21.589  41.311  51.819  1.00 26.63           N
ATOM   1654  CA   ALA A 243      22.159  41.813  50.586  1.00 26.63           C
ATOM   1655  C    ALA A 243      21.642  43.218  50.348  1.00 26.63           C
ATOM   1656  O    ALA A 243      22.400  44.111  49.976  1.00 26.63           O
ATOM   1657  CB   ALA A 243      21.785  40.905  49.436  1.00 21.53           C
ATOM   1658  N    GLY A 244      20.347  43.413  50.564  1.00 28.52           N
ATOM   1659  CA   GLY A 244      19.781  44.732  50.389  1.00 28.52           C
ATOM   1660  C    GLY A 244      20.447  45.715  51.338  1.00 28.52           C
ATOM   1661  O    GLY A 244      20.545  46.900  51.045  1.00 28.52           O
ATOM   1662  N    CYS A 245      20.907  45.216  52.481  1.00 29.37           N
ATOM   1663  CA   CYS A 245      21.577  46.046  53.474  1.00 29.37           C
ATOM   1664  C    CYS A 245      22.977  46.407  53.020  1.00 29.37           C
ATOM   1665  O    CYS A 245      23.465  47.503  53.287  1.00 29.37           O
ATOM   1666  CB   CYS A 245      21.637  45.324  54.823  1.00 20.33           C
ATOM   1667  SG   CYS A 245      20.102  45.379  55.736  1.00 20.33           S
ATOM   1668  N    VAL A 246      23.629  45.473  52.342  1.00 21.92           N
ATOM   1669  CA   VAL A 246      24.964  45.714  51.824  1.00 21.92           C
ATOM   1670  C    VAL A 246      24.867  46.794  50.751  1.00 21.92           C
ATOM   1671  O    VAL A 246      25.639  47.743  50.744  1.00 21.92           O
```

FIG. 1-28

```
ATOM   1672  CB   VAL A 246      25.551  44.433  51.210  1.00 25.13           C
ATOM   1673  CG1  VAL A 246      26.869  44.736  50.514  1.00 25.13           C
ATOM   1674  CG2  VAL A 246      25.746  43.400  52.299  1.00 25.13           C
ATOM   1675  N    LEU A 247      23.886  46.635  49.868  1.00 20.11           N
ATOM   1676  CA   LEU A 247      23.630  47.555  48.771  1.00 20.11           C
ATOM   1677  C    LEU A 247      23.345  48.955  49.281  1.00 20.11           C
ATOM   1678  O    LEU A 247      23.983  49.923  48.876  1.00 20.11           O
ATOM   1679  CB   LEU A 247      22.447  47.052  47.956  1.00 25.29           C
ATOM   1680  CG   LEU A 247      21.822  48.030  46.965  1.00 25.29           C
ATOM   1681  CD1  LEU A 247      22.832  48.486  45.909  1.00 25.29           C
ATOM   1682  CD2  LEU A 247      20.633  47.344  46.323  1.00 25.29           C
ATOM   1683  N    ALA A 248      22.368  49.048  50.170  1.00 27.36           N
ATOM   1684  CA   ALA A 248      22.000  50.314  50.768  1.00 27.36           C
ATOM   1685  C    ALA A 248      23.207  50.944  51.464  1.00 27.36           C
ATOM   1686  O    ALA A 248      23.389  52.155  51.419  1.00 27.36           O
ATOM   1687  CB   ALA A 248      20.891  50.099  51.763  1.00 10.48           C
ATOM   1688  N    GLU A 249      24.031  50.124  52.108  1.00 21.02           N
ATOM   1689  CA   GLU A 249      25.198  50.643  52.794  1.00 21.02           C
ATOM   1690  C    GLU A 249      26.215  51.205  51.810  1.00 21.02           C
ATOM   1691  O    GLU A 249      26.838  52.229  52.070  1.00 21.02           O
ATOM   1692  CB   GLU A 249      25.839  49.547  53.642  1.00 24.29           C
ATOM   1693  CG   GLU A 249      26.943  50.043  54.549  1.00 24.29           C
ATOM   1694  CD   GLU A 249      27.495  48.952  55.424  1.00 24.29           C
ATOM   1695  OE1  GLU A 249      26.685  48.153  55.928  1.00 24.29           O
ATOM   1696  OE2  GLU A 249      28.727  48.905  55.623  1.00 24.29           O
ATOM   1697  N    LEU A 250      26.387  50.524  50.682  1.00 28.26           N
ATOM   1698  CA   LEU A 250      27.319  50.960  49.653  1.00 28.26           C
ATOM   1699  C    LEU A 250      26.929  52.326  49.104  1.00 28.26           C
ATOM   1700  O    LEU A 250      27.781  53.156  48.814  1.00 28.26           O
ATOM   1701  CB   LEU A 250      27.350  49.951  48.515  1.00 19.31           C
ATOM   1702  CG   LEU A 250      27.995  48.599  48.812  1.00 19.31           C
ATOM   1703  CD1  LEU A 250      28.001  47.749  47.563  1.00 19.31           C
ATOM   1704  CD2  LEU A 250      29.401  48.816  49.316  1.00 19.31           C
ATOM   1705  N    LEU A 251      25.629  52.552  48.972  1.00 28.98           N
ATOM   1706  CA   LEU A 251      25.111  53.802  48.459  1.00 28.98           C
ATOM   1707  C    LEU A 251      25.101  54.914  49.490  1.00 28.98           C
ATOM   1708  O    LEU A 251      25.218  56.077  49.135  1.00 28.98           O
ATOM   1709  CB   LEU A 251      23.687  53.604  47.951  1.00 14.16           C
ATOM   1710  CG   LEU A 251      23.474  52.537  46.882  1.00 14.16           C
ATOM   1711  CD1  LEU A 251      21.991  52.316  46.676  1.00 14.16           C
ATOM   1712  CD2  LEU A 251      24.160  52.942  45.601  1.00 14.16           C
ATOM   1713  N    LEU A 252      24.967  54.562  50.763  1.00 28.99           N
ATOM   1714  CA   LEU A 252      24.895  55.546  51.838  1.00 28.99           C
ATOM   1715  C    LEU A 252      26.224  55.896  52.503  1.00 28.99           C
ATOM   1716  O    LEU A 252      26.389  56.994  53.021  1.00 28.99           O
ATOM   1717  CB   LEU A 252      23.908  55.060  52.902  1.00 27.47           C
ATOM   1718  CG   LEU A 252      22.882  56.045  53.473  1.00 27.47           C
ATOM   1719  CD1  LEU A 252      22.028  56.611  52.353  0.00 27.47           C
ATOM   1720  CD2  LEU A 252      22.018  55.338  54.504  0.00 27.47           C
ATOM   1721  N    GLY A 253      27.178  54.978  52.499  1.00 27.31           N
ATOM   1722  CA   GLY A 253      28.456  55.263  53.131  1.00 27.31           C
ATOM   1723  C    GLY A 253      28.508  54.802  54.580  1.00 27.31           C
ATOM   1724  O    GLY A 253      29.527  54.940  55.256  1.00 27.31           O
ATOM   1725  N    GLN A 254      27.398  54.247  55.048  1.00 27.88           N
ATOM   1726  CA   GLN A 254      27.274  53.749  56.412  1.00 27.88           C
ATOM   1727  C    GLN A 254      26.091  52.786  56.422  1.00 27.88           C
ATOM   1728  O    GLN A 254      25.270  52.813  55.508  1.00 27.88           O
ATOM   1729  CB   GLN A 254      26.994  54.908  57.368  1.00 51.39           C
ATOM   1730  CG   GLN A 254      25.709  55.657  57.030  1.00 51.39           C
ATOM   1731  CD   GLN A 254      25.455  56.873  57.918  1.00 51.39           C
ATOM   1732  OE1  GLN A 254      25.280  56.756  59.141  1.00 51.39           O
ATOM   1733  NE2  GLN A 254      25.429  58.051  57.301  1.00 51.39           N
```

FIG. 1-29

| ATOM | 1734 | N   | PRO A 255 | 26.001 | 51.912 | 57.441 | 1.00 | 33.15 | N |
| ATOM | 1735 | CA  | PRO A 255 | 24.898 | 50.956 | 57.540 | 1.00 | 33.15 | C |
| ATOM | 1736 | C   | PRO A 255 | 23.584 | 51.709 | 57.538 | 1.00 | 33.15 | C |
| ATOM | 1737 | O   | PRO A 255 | 23.525 | 52.849 | 57.985 | 1.00 | 33.15 | O |
| ATOM | 1738 | CB  | PRO A 255 | 25.152 | 50.277 | 58.877 | 1.00 | 21.02 | C |
| ATOM | 1739 | CG  | PRO A 255 | 26.631 | 50.260 | 58.956 | 1.00 | 21.02 | C |
| ATOM | 1740 | CD  | PRO A 255 | 27.011 | 51.643 | 58.480 | 1.00 | 21.02 | C |
| ATOM | 1741 | N   | ILE A 256 | 22.530 | 51.075 | 57.042 | 1.00 | 29.77 | N |
| ATOM | 1742 | CA  | ILE A 256 | 21.228 | 51.707 | 56.995 | 1.00 | 29.77 | C |
| ATOM | 1743 | C   | ILE A 256 | 20.360 | 51.396 | 58.220 | 1.00 | 29.77 | C |
| ATOM | 1744 | O   | ILE A 256 | 19.510 | 52.196 | 58.590 | 1.00 | 29.77 | O |
| ATOM | 1745 | CB  | ILE A 256 | 20.486 | 51.309 | 55.704 | 1.00 | 22.31 | C |
| ATOM | 1746 | CG1 | ILE A 256 | 19.158 | 52.052 | 55.620 | 1.00 | 22.31 | C |
| ATOM | 1747 | CG2 | ILE A 256 | 20.266 | 49.816 | 55.662 | 1.00 | 22.31 | C |
| ATOM | 1748 | CD1 | ILE A 256 | 18.564 | 52.075 | 54.233 | 1.00 | 22.31 | C |
| ATOM | 1749 | N   | PHE A 257 | 20.579 | 50.250 | 58.859 | 1.00 | 26.75 | N |
| ATOM | 1750 | CA  | PHE A 257 | 19.793 | 49.873 | 60.034 | 1.00 | 26.75 | C |
| ATOM | 1751 | C   | PHE A 257 | 20.684 | 49.530 | 61.218 | 1.00 | 26.75 | C |
| ATOM | 1752 | O   | PHE A 257 | 20.745 | 48.385 | 61.656 | 1.00 | 26.75 | O |
| ATOM | 1753 | CB  | PHE A 257 | 18.902 | 48.669 | 59.726 | 1.00 | 28.25 | C |
| ATOM | 1754 | CG  | PHE A 257 | 18.025 | 48.854 | 58.536 | 1.00 | 28.25 | C |
| ATOM | 1755 | CD1 | PHE A 257 | 17.262 | 50.005 | 58.392 | 1.00 | 28.25 | C |
| ATOM | 1756 | CD2 | PHE A 257 | 17.950 | 47.882 | 57.557 | 1.00 | 28.25 | C |
| ATOM | 1757 | CE1 | PHE A 257 | 16.436 | 50.185 | 57.289 | 1.00 | 28.25 | C |
| ATOM | 1758 | CE2 | PHE A 257 | 17.126 | 48.056 | 56.450 | 1.00 | 28.25 | C |
| ATOM | 1759 | CZ  | PHE A 257 | 16.370 | 49.208 | 56.317 | 1.00 | 28.25 | C |
| ATOM | 1760 | N   | PRO A 258 | 21.398 | 50.517 | 61.754 | 1.00 | 31.14 | N |
| ATOM | 1761 | CA  | PRO A 258 | 22.250 | 50.184 | 62.888 | 1.00 | 31.14 | C |
| ATOM | 1762 | C   | PRO A 258 | 21.453 | 50.205 | 64.185 | 1.00 | 31.14 | C |
| ATOM | 1763 | O   | PRO A 258 | 20.242 | 50.445 | 64.181 | 1.00 | 31.14 | O |
| ATOM | 1764 | CB  | PRO A 258 | 23.313 | 51.259 | 62.829 | 1.00 | 19.46 | C |
| ATOM | 1765 | CG  | PRO A 258 | 22.535 | 52.441 | 62.399 | 1.00 | 19.46 | C |
| ATOM | 1766 | CD  | PRO A 258 | 21.604 | 51.911 | 61.327 | 1.00 | 19.46 | C |
| ATOM | 1767 | N   | GLY A 259 | 22.140 | 49.942 | 65.289 | 1.00 | 29.28 | N |
| ATOM | 1768 | CA  | GLY A 259 | 21.489 | 49.926 | 66.580 | 1.00 | 29.28 | C |
| ATOM | 1769 | C   | GLY A 259 | 22.201 | 48.973 | 67.510 | 1.00 | 29.28 | C |
| ATOM | 1770 | O   | GLY A 259 | 22.611 | 47.892 | 67.093 | 1.00 | 29.28 | O |
| ATOM | 1771 | N   | ASP A 260 | 22.374 | 49.373 | 68.764 | 1.00 | 36.38 | N |
| ATOM | 1772 | CA  | ASP A 260 | 23.038 | 48.521 | 69.739 | 1.00 | 36.38 | C |
| ATOM | 1773 | C   | ASP A 260 | 22.120 | 47.370 | 70.134 | 1.00 | 36.38 | C |
| ATOM | 1774 | O   | ASP A 260 | 22.592 | 46.315 | 70.545 | 1.00 | 36.38 | O |
| ATOM | 1775 | CB  | ASP A 260 | 23.420 | 49.323 | 70.987 | 1.00 | 47.71 | C |
| ATOM | 1776 | CG  | ASP A 260 | 24.776 | 50.008 | 70.855 | 1.00 | 47.71 | C |
| ATOM | 1777 | OD1 | ASP A 260 | 25.300 | 50.097 | 69.716 | 1.00 | 47.71 | O |
| ATOM | 1778 | OD2 | ASP A 260 | 25.310 | 50.463 | 71.896 | 1.00 | 47.71 | O |
| ATOM | 1779 | N   | SER A 261 | 20.812 | 47.577 | 70.006 | 1.00 | 17.64 | N |
| ATOM | 1780 | CA  | SER A 261 | 19.852 | 46.550 | 70.357 | 1.00 | 17.64 | C |
| ATOM | 1781 | C   | SER A 261 | 18.826 | 46.331 | 69.253 | 1.00 | 17.64 | C |
| ATOM | 1782 | O   | SER A 261 | 18.721 | 47.114 | 68.324 | 1.00 | 17.64 | O |
| ATOM | 1783 | CB  | SER A 261 | 19.120 | 46.935 | 71.638 | 1.00 | 27.99 | C |
| ATOM | 1784 | OG  | SER A 261 | 18.171 | 47.965 | 71.386 | 1.00 | 27.99 | O |
| ATOM | 1785 | N   | GLY A 262 | 18.062 | 45.255 | 69.375 | 1.00 | 31.16 | N |
| ATOM | 1786 | CA  | GLY A 262 | 17.038 | 44.975 | 68.398 | 1.00 | 31.16 | C |
| ATOM | 1787 | C   | GLY A 262 | 16.107 | 46.163 | 68.362 | 1.00 | 31.16 | C |
| ATOM | 1788 | O   | GLY A 262 | 15.875 | 46.750 | 67.310 | 1.00 | 31.16 | O |
| ATOM | 1789 | N   | VAL A 263 | 15.580 | 46.538 | 69.517 | 1.00 | 25.51 | N |
| ATOM | 1790 | CA  | VAL A 263 | 14.674 | 47.672 | 69.581 | 1.00 | 25.51 | C |
| ATOM | 1791 | C   | VAL A 263 | 15.180 | 48.841 | 68.742 | 1.00 | 25.51 | C |
| ATOM | 1792 | O   | VAL A 263 | 14.433 | 49.408 | 67.954 | 1.00 | 25.51 | O |
| ATOM | 1793 | CB  | VAL A 263 | 14.456 | 48.141 | 71.046 | 1.00 | 26.72 | C |
| ATOM | 1794 | CG1 | VAL A 263 | 13.550 | 49.377 | 71.078 | 1.00 | 26.72 | C |
| ATOM | 1795 | CG2 | VAL A 263 | 13.830 | 47.020 | 71.852 | 1.00 | 26.72 | C |

FIG. 1-30

| ATOM | 1796 | N | ASP A 264 | 16.446 | 49.195 | 68.902 | 1.00 | 23.62 | N |
|---|---|---|---|---|---|---|---|---|---|
| ATOM | 1797 | CA | ASP A 264 | 16.992 | 50.297 | 68.132 | 1.00 | 23.62 | C |
| ATOM | 1798 | C | ASP A 264 | 16.962 | 50.012 | 66.641 | 1.00 | 23.62 | C |
| ATOM | 1799 | O | ASP A 264 | 16.538 | 50.855 | 65.848 | 1.00 | 23.62 | O |
| ATOM | 1800 | CB | ASP A 264 | 18.421 | 50.594 | 68.566 | 1.00 | 36.57 | C |
| ATOM | 1801 | CG | ASP A 264 | 18.488 | 51.166 | 69.958 | 1.00 | 36.57 | C |
| ATOM | 1802 | OD1 | ASP A 264 | 17.525 | 51.854 | 70.338 | 1.00 | 36.57 | O |
| ATOM | 1803 | OD2 | ASP A 264 | 19.493 | 50.945 | 70.663 | 1.00 | 36.57 | O |
| ATOM | 1804 | N | GLN A 265 | 17.423 | 48.817 | 66.272 | 1.00 | 27.66 | N |
| ATOM | 1805 | CA | GLN A 265 | 17.458 | 48.370 | 64.883 | 1.00 | 27.66 | C |
| ATOM | 1806 | C | GLN A 265 | 16.065 | 48.472 | 64.264 | 1.00 | 27.66 | C |
| ATOM | 1807 | O | GLN A 265 | 15.900 | 48.988 | 63.158 | 1.00 | 27.66 | O |
| ATOM | 1808 | CB | GLN A 265 | 17.952 | 46.925 | 64.817 | 1.00 | 38.02 | C |
| ATOM | 1809 | CG | GLN A 265 | 19.470 | 46.759 | 64.893 | 1.00 | 38.02 | C |
| ATOM | 1810 | CD | GLN A 265 | 19.888 | 45.365 | 65.365 | 1.00 | 38.02 | C |
| ATOM | 1811 | OE1 | GLN A 265 | 19.269 | 44.376 | 65.006 | 1.00 | 38.02 | C |
| ATOM | 1812 | NE2 | GLN A 265 | 20.940 | 45.292 | 66.170 | 1.00 | 38.02 | N |
| ATOM | 1813 | N | LEU A 266 | 15.059 | 47.985 | 64.977 | 1.00 | 29.79 | N |
| ATOM | 1814 | CA | LEU A 266 | 13.712 | 48.065 | 64.455 | 1.00 | 29.79 | C |
| ATOM | 1815 | C | LEU A 266 | 13.312 | 49.514 | 64.227 | 1.00 | 29.79 | C |
| ATOM | 1816 | O | LEU A 266 | 12.702 | 49.829 | 63.208 | 1.00 | 29.79 | O |
| ATOM | 1817 | CB | LEU A 266 | 12.724 | 47.381 | 65.395 | 1.00 | 30.81 | C |
| ATOM | 1818 | CG | LEU A 266 | 12.338 | 45.984 | 64.932 | 1.00 | 30.81 | C |
| ATOM | 1819 | CD1 | LEU A 266 | 13.576 | 45.190 | 64.729 | 1.00 | 30.81 | C |
| ATOM | 1820 | CD2 | LEU A 266 | 11.448 | 45.316 | 65.944 | 1.00 | 30.81 | C |
| ATOM | 1821 | N | VAL A 267 | 13.660 | 50.396 | 65.160 | 1.00 | 27.95 | N |
| ATOM | 1822 | CA | VAL A 267 | 13.329 | 51.808 | 65.010 | 1.00 | 27.95 | C |
| ATOM | 1823 | C | VAL A 267 | 13.797 | 52.295 | 63.645 | 1.00 | 27.95 | C |
| ATOM | 1824 | O | VAL A 267 | 13.018 | 52.815 | 62.844 | 1.00 | 27.95 | O |
| ATOM | 1825 | CB | VAL A 267 | 14.010 | 52.675 | 66.092 | 1.00 | 35.03 | C |
| ATOM | 1826 | CG1 | VAL A 267 | 13.841 | 54.158 | 65.769 | 1.00 | 35.03 | C |
| ATOM | 1827 | CG2 | VAL A 267 | 13.412 | 52.369 | 67.441 | 1.00 | 35.03 | C |
| ATOM | 1828 | N | GLU A 268 | 15.080 | 52.119 | 63.384 | 1.00 | 40.12 | N |
| ATOM | 1829 | CA | GLU A 268 | 15.627 | 52.537 | 62.111 | 1.00 | 40.12 | C |
| ATOM | 1830 | C | GLU A 268 | 14.919 | 51.849 | 60.935 | 1.00 | 40.12 | C |
| ATOM | 1831 | O | GLU A 268 | 14.607 | 52.488 | 59.934 | 1.00 | 40.12 | O |
| ATOM | 1832 | CB | GLU A 268 | 17.137 | 52.281 | 62.080 | 1.00 | 48.16 | C |
| ATOM | 1833 | CG | GLU A 268 | 17.923 | 53.207 | 63.003 | 1.00 | 48.16 | C |
| ATOM | 1834 | CD | GLU A 268 | 17.444 | 54.649 | 62.911 | 1.00 | 48.16 | C |
| ATOM | 1835 | OE1 | GLU A 268 | 17.356 | 55.192 | 61.785 | 1.00 | 48.16 | O |
| ATOM | 1836 | OE2 | GLU A 268 | 17.146 | 55.239 | 63.971 | 1.00 | 48.16 | O |
| ATOM | 1837 | N | ILE A 269 | 14.645 | 50.556 | 61.055 | 1.00 | 28.21 | N |
| ATOM | 1838 | CA | ILE A 269 | 13.952 | 49.861 | 59.978 | 1.00 | 28.21 | C |
| ATOM | 1839 | C | ILE A 269 | 12.587 | 50.511 | 59.712 | 1.00 | 28.21 | C |
| ATOM | 1840 | O | ILE A 269 | 12.221 | 50.790 | 58.566 | 1.00 | 28.21 | O |
| ATOM | 1841 | CB | ILE A 269 | 13.771 | 48.374 | 60.321 | 1.00 | 12.18 | C |
| ATOM | 1842 | CG1 | ILE A 269 | 15.142 | 47.703 | 60.345 | 1.00 | 12.18 | C |
| ATOM | 1843 | CG2 | ILE A 269 | 12.855 | 47.704 | 59.321 | 1.00 | 12.18 | C |
| ATOM | 1844 | CD1 | ILE A 269 | 15.101 | 46.204 | 60.519 | 1.00 | 12.18 | C |
| ATOM | 1845 | N | ILE A 270 | 11.852 | 50.769 | 60.785 | 1.00 | 38.75 | N |
| ATOM | 1846 | CA | ILE A 270 | 10.542 | 51.378 | 60.678 | 1.00 | 38.75 | C |
| ATOM | 1847 | C | ILE A 270 | 10.626 | 52.806 | 60.131 | 1.00 | 38.75 | C |
| ATOM | 1848 | O | ILE A 270 | 9.827 | 53.197 | 59.269 | 1.00 | 38.75 | O |
| ATOM | 1849 | CB | ILE A 270 | 9.833 | 51.367 | 62.054 | 1.00 | 36.77 | C |
| ATOM | 1850 | CG1 | ILE A 270 | 9.534 | 49.916 | 62.456 | 1.00 | 36.77 | C |
| ATOM | 1851 | CG2 | ILE A 270 | 8.532 | 52.163 | 61.990 | 1.00 | 36.77 | C |
| ATOM | 1852 | CD1 | ILE A 270 | 9.003 | 49.744 | 63.857 | 1.00 | 36.77 | C |
| ATOM | 1853 | N | LYS A 271 | 11.590 | 53.583 | 60.614 | 1.00 | 38.41 | N |
| ATOM | 1854 | CA | LYS A 271 | 11.738 | 54.954 | 60.139 | 1.00 | 38.41 | C |
| ATOM | 1855 | C | LYS A 271 | 11.741 | 55.018 | 58.614 | 1.00 | 38.41 | C |
| ATOM | 1856 | O | LYS A 271 | 11.315 | 56.011 | 58.027 | 1.00 | 38.41 | O |
| ATOM | 1857 | CB | LYS A 271 | 13.036 | 55.585 | 60.663 | 1.00 | 37.99 | C |

FIG. 1-31

```
ATOM   1858  CG  LYS A 271      12.988  56.118  62.083  1.00 37.99           C
ATOM   1859  CD  LYS A 271      14.318  56.785  62.467  1.00 37.99           C
ATOM   1860  CE  LYS A 271      14.241  57.404  63.853  0.00 37.99           C
ATOM   1861  NZ  LYS A 271      15.513  58.075  64.233  0.00 37.99           N
ATOM   1862  N   VAL A 272      12.215  53.969  57.956  1.00 54.30           N
ATOM   1863  CA  VAL A 272      12.262  54.007  56.500  1.00 54.30           C
ATOM   1864  C   VAL A 272      11.197  53.184  55.791  1.00 54.30           C
ATOM   1865  O   VAL A 272      10.608  53.642  54.799  1.00 54.30           O
ATOM   1866  CB  VAL A 272      13.637  53.580  55.975  1.00 55.29           C
ATOM   1867  CG1 VAL A 272      14.577  54.756  56.003  1.00 55.29           C
ATOM   1868  CG2 VAL A 272      14.201  52.476  56.844  1.00 55.29           C
ATOM   1869  N   LEU A 273      10.943  51.977  56.282  1.00 40.87           N
ATOM   1870  CA  LEU A 273       9.934  51.144  55.652  1.00 40.87           C
ATOM   1871  C   LEU A 273       8.524  51.541  56.069  1.00 40.87           C
ATOM   1872  O   LEU A 273       7.560  51.300  55.343  1.00 40.87           O
ATOM   1873  CB  LEU A 273      10.164  49.675  55.999  1.00 29.67           C
ATOM   1874  CG  LEU A 273      11.261  48.951  55.234  1.00 29.67           C
ATOM   1875  CD1 LEU A 273      11.190  47.491  55.599  1.00 29.67           C
ATOM   1876  CD2 LEU A 273      11.070  49.124  53.740  0.00 29.67           C
ATOM   1877  N   GLY A 274       8.400  52.153  57.239  1.00 52.25           N
ATOM   1878  CA  GLY A 274       7.077  52.520  57.717  1.00 52.25           C
ATOM   1879  C   GLY A 274       6.592  51.464  58.688  1.00 52.25           C
ATOM   1880  O   GLY A 274       7.061  50.323  58.645  1.00 52.25           O
ATOM   1881  N   THR A 275       5.675  51.828  59.572  1.00 47.53           N
ATOM   1882  CA  THR A 275       5.168  50.911  60.588  1.00 47.53           C
ATOM   1883  C   THR A 275       4.584  49.619  59.977  1.00 47.53           C
ATOM   1884  O   THR A 275       3.838  49.634  59.008  1.00 47.53           O
ATOM   1885  CB  THR A 275       4.042  51.644  61.436  1.00 64.24           C
ATOM   1886  OG1 THR A 275       4.675  52.510  62.399  1.00 64.24           O
ATOM   1887  CG2 THR A 275       3.100  50.629  62.113  1.00 64.24           C
ATOM   1888  N   PRO A 276       4.898  48.466  60.546  1.00 59.25           N
ATOM   1889  CA  PRO A 276       4.299  47.287  59.918  1.00 59.25           C
ATOM   1890  C   PRO A 276       2.834  47.036  60.244  1.00 59.25           C
ATOM   1891  O   PRO A 276       2.378  47.188  61.388  1.00 59.25           O
ATOM   1892  CB  PRO A 276       5.185  46.162  60.376  1.00 56.82           C
ATOM   1893  CG  PRO A 276       6.005  46.787  61.522  1.00 56.82           C
ATOM   1894  CD  PRO A 276       5.536  48.132  61.810  1.00 56.82           C
ATOM   1895  N   THR A 277       2.144  46.581  59.217  1.00 63.97           N
ATOM   1896  CA  THR A 277       0.756  46.257  59.382  1.00 63.97           C
ATOM   1897  C   THR A 277       0.681  44.943  60.114  1.00 63.97           C
ATOM   1898  O   THR A 277       1.732  44.280  60.229  1.00 63.97           O
ATOM   1899  CB  THR A 277       0.085  46.093  58.007  1.00 62.34           C
ATOM   1900  OG1 THR A 277       0.705  44.991  57.306  1.00 62.34           O
ATOM   1901  CG2 THR A 277       0.217  47.369  57.215  1.00 62.34           C
ATOM   1902  N   ARG A 278      -0.500  44.588  60.608  1.00 59.83           N
ATOM   1903  CA  ARG A 278      -0.700  43.352  61.298  1.00 59.83           C
ATOM   1904  C   ARG A 278      -0.339  42.143  60.461  1.00 59.83           C
ATOM   1905  O   ARG A 278       0.131  41.174  60.993  1.00 59.83           O
ATOM   1906  CB  ARG A 278      -2.189  43.217  61.914  0.00 35.69           C
ATOM   1907  N   GLU A 279      -0.676  42.199  59.175  1.00 67.05           N
ATOM   1908  CA  GLU A 279      -0.378  41.084  58.287  1.00 67.05           C
ATOM   1909  C   GLU A 279       1.155  41.017  58.180  1.00 67.05           C
ATOM   1910  O   GLU A 279       1.793  39.983  58.525  1.00 67.05           O
ATOM   1911  CB  GLU A 279      -1.059  41.264  56.897  1.00100.00           C
ATOM   1912  CG  GLU A 279      -2.546  40.928  56.958  1.00100.00           C
ATOM   1913  CD  GLU A 279      -2.837  39.631  57.745  1.00100.00           C
ATOM   1914  OE1 GLU A 279      -2.052  38.631  57.620  1.00100.00           O
ATOM   1915  OE2 GLU A 279      -3.869  39.608  58.492  1.00100.00           O
ATOM   1916  N   GLN A 280       1.753  42.135  57.756  1.00 69.01           N
ATOM   1917  CA  GLN A 280       3.201  42.194  57.609  1.00 69.01           C
ATOM   1918  C   GLN A 280       3.899  41.514  58.779  1.00 69.01           C
ATOM   1919  O   GLN A 280       4.871  40.768  58.593  1.00 69.01           O
```

FIG. 1-32

```
ATOM   1920  CB   GLN A 280       3.678  43.655  57.480  1.00 63.74           C
ATOM   1921  CG   GLN A 280       3.420  44.297  56.110  1.00 63.74           C
ATOM   1922  CD   GLN A 280       3.982  45.697  56.020  1.00 63.74           C
ATOM   1923  OE1  GLN A 280       3.886  46.360  54.980  1.00 63.74           O
ATOM   1924  NE2  GLN A 280       4.580  46.162  57.116  1.00 63.74           N
ATOM   1925  N    ILE A 281       3.389  41.739  59.985  1.00 74.60           N
ATOM   1926  CA   ILE A 281       4.005  41.129  61.147  1.00 74.60           C
ATOM   1927  C    ILE A 281       3.804  39.629  61.167  1.00 74.60           C
ATOM   1928  O    ILE A 281       4.768  38.869  61.285  1.00 74.60           O
ATOM   1929  CB   ILE A 281       3.435  41.706  62.415  1.00 72.22           C
ATOM   1930  CG1  ILE A 281       3.623  43.233  62.388  1.00 72.22           C
ATOM   1931  CG2  ILE A 281       4.116  41.046  63.612  1.00 72.22           C
ATOM   1932  CD1  ILE A 281       2.664  44.027  63.287  1.00 72.22           C
ATOM   1933  N    ARG A 282       2.546  39.209  61.042  1.00 63.19           N
ATOM   1934  CA   ARG A 282       2.224  37.794  61.048  1.00 63.19           C
ATOM   1935  C    ARG A 282       3.187  37.043  60.158  1.00 63.19           C
ATOM   1936  O    ARG A 282       3.652  35.969  60.519  1.00 63.19           O
ATOM   1937  CB   ARG A 282       0.797  37.575  60.568  1.00 58.92           C
ATOM   1938  N    GLU A 283       3.496  37.622  59.000  1.00 98.45           N
ATOM   1939  CA   GLU A 283       4.402  36.978  58.047  1.00 98.45           C
ATOM   1940  C    GLU A 283       5.842  36.999  58.559  1.00 98.45           C
ATOM   1941  O    GLU A 283       6.670  36.180  58.141  1.00 98.45           O
ATOM   1942  CB   GLU A 283       4.290  37.658  56.686  0.00 85.00           C
ATOM   1943  CG   GLU A 283       2.860  37.639  56.157  0.00 85.00           C
ATOM   1944  CD   GLU A 283       2.653  38.684  55.130  1.00 85.00           C
ATOM   1945  OE1  GLU A 283       3.448  39.655  55.176  1.00 85.00           O
ATOM   1946  OE2  GLU A 283       1.715  38.584  54.285  1.00 85.00           O
ATOM   1947  N    MET A 284       6.123  37.911  59.490  1.00 73.55           N
ATOM   1948  CA   MET A 284       7.462  38.002  60.062  1.00 73.55           C
ATOM   1949  C    MET A 284       7.711  36.894  61.057  1.00 73.55           C
ATOM   1950  O    MET A 284       8.391  35.917  60.739  1.00 73.55           O
ATOM   1951  CB   MET A 284       7.695  39.355  60.732  1.00 75.43           C
ATOM   1952  CG   MET A 284       8.283  40.366  59.780  1.00 75.43           C
ATOM   1953  SD   MET A 284       8.408  41.862  60.689  1.00 75.43           S
ATOM   1954  CE   MET A 284       9.078  42.774  59.560  1.00 75.43           C
ATOM   1955  N    ASN A 285       7.166  37.026  62.256  1.00 68.20           N
ATOM   1956  CA   ASN A 285       7.402  35.974  63.222  1.00 68.20           C
ATOM   1957  C    ASN A 285       7.076  36.410  64.626  1.00 68.20           C
ATOM   1958  O    ASN A 285       5.998  36.061  65.108  1.00 68.20           O
ATOM   1959  N    TRP A 301      12.071  56.413  51.578  1.00 61.19           N
ATOM   1960  CA   TRP A 301      13.023  55.807  50.655  1.00 61.19           C
ATOM   1961  C    TRP A 301      13.648  56.851  49.727  1.00 61.19           C
ATOM   1962  O    TRP A 301      14.833  56.831  49.420  1.00 61.19           O
ATOM   1963  CB   TRP A 301      12.280  54.756  49.829  1.00 42.80           C
ATOM   1964  CG   TRP A 301      12.497  53.409  50.404  1.00 42.80           C
ATOM   1965  CD1  TRP A 301      11.516  52.421  50.641  1.00 42.80           C
ATOM   1966  CD2  TRP A 301      13.759  52.850  50.841  1.00 42.80           C
ATOM   1967  NE1  TRP A 301      12.037  51.290  51.185  1.00 42.80           N
ATOM   1968  CE2  TRP A 301      13.493  51.545  51.324  1.00 42.80           C
ATOM   1969  CE3  TRP A 301      15.063  53.336  50.864  1.00 42.80           C
ATOM   1970  CZ2  TRP A 301      14.526  50.768  51.820  1.00 42.80           C
ATOM   1971  CZ3  TRP A 301      16.097  52.558  51.359  1.00 42.80           C
ATOM   1972  CH2  TRP A 301      15.824  51.265  51.841  1.00 42.80           C
ATOM   1973  N    THR A 302      12.789  57.767  49.246  1.00 54.08           N
ATOM   1974  CA   THR A 302      13.268  58.791  48.326  1.00 54.08           C
ATOM   1975  C    THR A 302      14.139  59.832  49.035  1.00 54.08           C
ATOM   1976  O    THR A 302      14.910  60.562  48.427  1.00 54.08           O
ATOM   1977  CB   THR A 302      12.051  59.463  47.690  1.00 72.44           C
ATOM   1978  OG1  THR A 302      11.102  59.772  48.713  1.00 72.44           O
ATOM   1979  CG2  THR A 302      11.397  58.512  46.683  0.00 72.44           C
ATOM   1980  N    LYS A 303      13.965  59.912  50.369  1.00 42.66           N
ATOM   1981  CA   LYS A 303      14.756  60.879  51.120  1.00 42.66           C
```

FIG. 1-33

```
ATOM   1982  C    LYS A 303      15.760  60.185  52.043  1.00 42.66           C
ATOM   1983  O    LYS A 303      16.146  60.688  53.090  1.00 42.66           O
ATOM   1984  CB   LYS A 303      13.799  61.742  51.944  1.00 60.61           C
ATOM   1985  N    VAL A 304      16.154  58.964  51.636  1.00 57.27           N
ATOM   1986  CA   VAL A 304      17.096  58.204  52.448  1.00 57.27           C
ATOM   1987  C    VAL A 304      18.520  58.288  51.893  1.00 57.27           C
ATOM   1988  O    VAL A 304      19.483  58.552  52.601  1.00 57.27           O
ATOM   1989  CB   VAL A 304      16.633  56.747  52.473  1.00 33.85           C
ATOM   1990  CG1  VAL A 304      17.801  55.836  52.848  1.00 33.85           C
ATOM   1991  CG2  VAL A 304      15.518  56.575  53.488  1.00 33.85           C
ATOM   1992  N    PHE A 305      18.638  58.012  50.580  1.00 37.26           N
ATOM   1993  CA   PHE A 305      19.955  58.026  49.954  1.00 37.26           C
ATOM   1994  C    PHE A 305      20.357  59.433  49.507  1.00 37.26           C
ATOM   1995  O    PHE A 305      19.536  60.323  49.325  1.00 37.26           O
ATOM   1996  CB   PHE A 305      19.918  57.090  48.746  1.00 37.35           C
ATOM   1997  CG   PHE A 305      19.730  55.675  49.207  1.00 37.35           C
ATOM   1998  CD1  PHE A 305      18.450  55.136  49.263  1.00 37.35           C
ATOM   1999  CD2  PHE A 305      20.826  54.918  49.585  1.00 37.35           C
ATOM   2000  CE1  PHE A 305      18.271  53.832  49.702  1.00 37.35           C
ATOM   2001  CE2  PHE A 305      20.639  53.610  50.025  1.00 37.35           C
ATOM   2002  CZ   PHE A 305      19.363  53.064  50.085  1.00 37.35           C
ATOM   2003  N    ARG A 306      21.682  59.628  49.370  1.00 31.29           N
ATOM   2004  CA   ARG A 306      22.172  60.920  48.910  1.00 31.29           C
ATOM   2005  C    ARG A 306      21.530  61.313  47.577  1.00 31.29           C
ATOM   2006  O    ARG A 306      21.054  60.485  46.811  1.00 31.29           O
ATOM   2007  CB   ARG A 306      23.690  60.825  48.752  1.00 61.41           C
ATOM   2008  CG   ARG A 306      24.143  61.070  47.313  1.00 61.41           C
ATOM   2009  CD   ARG A 306      25.026  59.931  46.787  1.00 61.41           C
ATOM   2010  NE   ARG A 306      26.116  60.464  45.965  1.00 61.41           N
ATOM   2011  CZ   ARG A 306      27.118  59.624  45.644  1.00 61.41           C
ATOM   2012  NH1  ARG A 306      27.091  58.368  46.057  1.00 61.41           N
ATOM   2013  NH2  ARG A 306      28.150  60.073  44.927  1.00 61.41           N
ATOM   2014  N    PRO A 307      21.492  62.637  47.333  1.00 53.14           N
ATOM   2015  CA   PRO A 307      20.901  63.176  46.116  1.00 53.14           C
ATOM   2016  C    PRO A 307      21.664  62.732  44.866  1.00 53.14           C
ATOM   2017  O    PRO A 307      22.816  62.322  44.913  1.00 53.14           O
ATOM   2018  CB   PRO A 307      20.920  64.701  46.223  1.00 64.42           C
ATOM   2019  CG   PRO A 307      21.315  65.072  47.651  1.00 64.42           C
ATOM   2020  CD   PRO A 307      21.990  63.717  48.167  1.00 64.42           C
ATOM   2021  N    ARG A 308      20.957  62.786  43.720  1.00 40.68           N
ATOM   2022  CA   ARG A 308      21.597  62.439  42.455  1.00 40.68           C
ATOM   2023  C    ARG A 308      21.934  60.949  42.375  1.00 40.68           C
ATOM   2024  O    ARG A 308      22.704  60.498  41.537  1.00 40.68           O
ATOM   2025  CB   ARG A 308      22.876  63.267  42.324  0.00 35.69           C
ATOM   2026  N    THR A 309      21.354  60.178  43.313  1.00 34.01           N
ATOM   2027  CA   THR A 309      21.635  58.747  43.336  1.00 34.01           C
ATOM   2028  C    THR A 309      20.659  57.963  42.458  1.00 34.01           C
ATOM   2029  O    THR A 309      19.452  58.162  42.493  1.00 34.01           O
ATOM   2030  CB   THR A 309      21.545  58.259  44.782  1.00 33.02           C
ATOM   2031  OG1  THR A 309      21.821  56.858  44.817  1.00 33.02           O
ATOM   2032  CG2  THR A 309      20.135  58.499  45.330  1.00 33.02           C
ATOM   2033  N    PRO A 310      21.105  57.128  41.510  1.00 38.98           N
ATOM   2034  CA   PRO A 310      20.190  56.439  40.630  1.00 38.98           C
ATOM   2035  C    PRO A 310      18.969  55.967  41.411  1.00 38.98           C
ATOM   2036  O    PRO A 310      19.056  55.394  42.489  1.00 38.98           O
ATOM   2037  CB   PRO A 310      20.935  55.246  40.037  1.00 20.74           C
ATOM   2038  CG   PRO A 310      22.409  55.341  40.440  1.00 20.74           C
ATOM   2039  CD   PRO A 310      22.467  56.749  41.203  1.00 20.74           C
ATOM   2040  N    PRO A 311      17.875  56.267  40.684  1.00 39.47           N
ATOM   2041  CA   PRO A 311      16.543  55.842  41.090  1.00 39.47           C
ATOM   2042  C    PRO A 311      16.341  54.340  40.867  1.00 39.47           C
ATOM   2043  O    PRO A 311      15.580  53.675  41.558  1.00 39.47           O
```

FIG. 1-34

```
ATOM   2044  CB   PRO A 311      15.532  56.637  40.260  1.00 36.28           C
ATOM   2045  CG   PRO A 311      16.301  57.586  39.338  1.00 36.28           C
ATOM   2046  CD   PRO A 311      17.796  57.027  39.451  1.00 36.28           C
ATOM   2047  N    GLU A 312      17.085  53.665  40.003  1.00 32.81           N
ATOM   2048  CA   GLU A 312      16.999  52.214  39.903  1.00 32.81           C
ATOM   2049  C    GLU A 312      17.545  51.536  41.155  1.00 32.81           C
ATOM   2050  O    GLU A 312      17.016  50.512  41.600  1.00 32.81           O
ATOM   2051  CB   GLU A 312      17.773  51.710  38.688  1.00 59.36           C
ATOM   2052  CG   GLU A 312      17.230  52.203  37.372  1.00 59.36           C
ATOM   2053  CD   GLU A 312      17.179  53.722  37.294  1.00 59.36           C
ATOM   2054  OE1  GLU A 312      18.077  54.395  37.878  1.00 59.36           O
ATOM   2055  OE2  GLU A 312      16.242  54.237  36.632  1.00 59.36           O
ATOM   2056  N    ALA A 313      18.600  52.116  41.719  1.00 27.51           N
ATOM   2057  CA   ALA A 313      19.225  51.564  42.910  1.00 27.51           C
ATOM   2058  C    ALA A 313      18.299  51.666  44.101  1.00 27.51           C
ATOM   2059  O    ALA A 313      18.207  50.751  44.923  1.00 27.51           O
ATOM   2060  CB   ALA A 313      20.522  52.296  43.204  1.00 47.57           C
ATOM   2061  N    ILE A 314      17.621  52.800  44.191  1.00 31.65           N
ATOM   2062  CA   ILE A 314      16.701  53.043  45.279  1.00 31.65           C
ATOM   2063  C    ILE A 314      15.500  52.115  45.126  1.00 31.65           C
ATOM   2064  O    ILE A 314      14.946  51.639  46.111  1.00 31.65           O
ATOM   2065  CB   ILE A 314      16.237  54.504  45.281  1.00 32.54           C
ATOM   2066  CG1  ILE A 314      17.447  55.439  45.291  0.00 32.54           C
ATOM   2067  CG2  ILE A 314      15.371  54.758  46.507  1.00 32.54           C
ATOM   2068  CD1  ILE A 314      17.088  56.908  45.242  0.00 32.54           C
ATOM   2069  N    ALA A 315      15.108  51.850  43.884  1.00 30.21           N
ATOM   2070  CA   ALA A 315      13.975  50.969  43.626  1.00 30.21           C
ATOM   2071  C    ALA A 315      14.271  49.552  44.102  1.00 30.21           C
ATOM   2072  O    ALA A 315      13.484  48.973  44.840  1.00 30.21           O
ATOM   2073  CB   ALA A 315      13.646  50.963  42.143  1.00 24.26           C
ATOM   2074  N    LEU A 316      15.406  49.002  43.667  1.00 29.43           N
ATOM   2075  CA   LEU A 316      15.836  47.652  44.037  1.00 29.43           C
ATOM   2076  C    LEU A 316      15.888  47.500  45.556  1.00 29.43           C
ATOM   2077  O    LEU A 316      15.361  46.533  46.110  1.00 29.43           O
ATOM   2078  CB   LEU A 316      17.218  47.342  43.433  1.00 23.31           C
ATOM   2079  CG   LEU A 316      17.832  45.970  43.756  1.00 23.31           C
ATOM   2080  CD1  LEU A 316      17.018  44.852  43.137  1.00 23.31           C
ATOM   2081  CD2  LEU A 316      19.256  45.914  43.247  1.00 23.31           C
ATOM   2082  N    CYS A 317      16.518  48.456  46.229  1.00 29.07           N
ATOM   2083  CA   CYS A 317      16.601  48.396  47.683  1.00 29.07           C
ATOM   2084  C    CYS A 317      15.230  48.137  48.287  1.00 29.07           C
ATOM   2085  O    CYS A 317      15.075  47.264  49.132  1.00 29.07           O
ATOM   2086  CB   CYS A 317      17.147  49.703  48.260  1.00 36.87           C
ATOM   2087  SG   CYS A 317      18.896  49.960  48.001  1.00 36.87           S
ATOM   2088  N    SER A 318      14.243  48.903  47.837  1.00 31.67           N
ATOM   2089  CA   SER A 318      12.884  48.792  48.332  1.00 31.67           C
ATOM   2090  C    SER A 318      12.255  47.433  48.065  1.00 31.67           C
ATOM   2091  O    SER A 318      11.400  46.985  48.833  1.00 31.67           O
ATOM   2092  CB   SER A 318      12.014  49.878  47.709  1.00 44.38           C
ATOM   2093  OG   SER A 318      11.875  49.661  46.310  1.00 44.38           O
ATOM   2094  N    ARG A 319      12.658  46.779  46.979  1.00 31.95           N
ATOM   2095  CA   ARG A 319      12.103  45.467  46.653  1.00 31.95           C
ATOM   2096  C    ARG A 319      12.905  44.356  47.320  1.00 31.95           C
ATOM   2097  O    ARG A 319      12.592  43.180  47.159  1.00 31.95           O
ATOM   2098  CB   ARG A 319      12.079  45.248  45.140  1.00 39.24           C
ATOM   2099  CG   ARG A 319      11.378  46.352  44.355  1.00 39.24           C
ATOM   2100  CD   ARG A 319       9.861  46.361  44.522  1.00 39.24           C
ATOM   2101  NE   ARG A 319       9.240  45.174  43.940  1.00 39.24           N
ATOM   2102  CZ   ARG A 319       9.037  44.032  44.594  1.00 39.24           C
ATOM   2103  NH1  ARG A 319       9.395  43.912  45.869  1.00 39.24           N
ATOM   2104  NH2  ARG A 319       8.496  42.995  43.967  1.00 39.24           N
ATOM   2105  N    LEU A 320      13.944  44.730  48.061  1.00 31.81           N
```

FIG. 1-35

```
ATOM   2106  CA   LEU A 320      14.756  43.749  48.767  1.00 31.81           C
ATOM   2107  C    LEU A 320      14.476  43.811  50.264  1.00 31.81           C
ATOM   2108  O    LEU A 320      14.458  42.788  50.947  1.00 31.81           O
ATOM   2109  CB   LEU A 320      16.240  44.005  48.529  1.00 25.62           C
ATOM   2110  CG   LEU A 320      16.820  43.750  47.137  1.00 25.62           C
ATOM   2111  CD1  LEU A 320      18.204  44.341  47.072  1.00 25.62           C
ATOM   2112  CD2  LEU A 320      16.871  42.270  46.846  1.00 25.62           C
ATOM   2113  N    LEU A 321      14.249  45.018  50.768  1.00 29.10           N
ATOM   2114  CA   LEU A 321      14.014  45.217  52.195  1.00 29.10           C
ATOM   2115  C    LEU A 321      12.521  45.330  52.511  1.00 29.10           C
ATOM   2116  O    LEU A 321      11.984  46.402  52.763  1.00 29.10           O
ATOM   2117  CB   LEU A 321      14.735  46.496  52.625  1.00 21.28           C
ATOM   2118  CG   LEU A 321      16.250  46.410  52.432  1.00 21.28           C
ATOM   2119  CD1  LEU A 321      16.970  47.680  52.889  1.00 21.28           C
ATOM   2120  CD2  LEU A 321      16.883  45.255  53.208  1.00 21.28           C
ATOM   2121  N    GLU A 322      11.838  44.173  52.455  1.00 39.08           N
ATOM   2122  CA   GLU A 322      10.405  44.172  52.723  1.00 39.08           C
ATOM   2123  C    GLU A 322      10.063  43.364  53.975  1.00 39.08           C
ATOM   2124  O    GLU A 322      10.642  42.324  54.262  1.00 39.08           O
ATOM   2125  CB   GLU A 322       9.696  43.570  51.510  1.00 55.55           C
ATOM   2126  CG   GLU A 322      10.113  44.238  50.199  1.00 55.55           C
ATOM   2127  CD   GLU A 322       8.938  45.000  49.630  1.00 55.55           C
ATOM   2128  OE1  GLU A 322       8.070  45.396  50.395  1.00 55.55           O
ATOM   2129  OE2  GLU A 322       8.896  45.185  48.415  1.00 55.55           O
ATOM   2130  N    TYR A 323       9.110  43.902  54.758  1.00 30.49           N
ATOM   2131  CA   TYR A 323       8.663  43.184  55.945  1.00 30.49           C
ATOM   2132  C    TYR A 323       8.285  41.741  55.607  1.00 30.49           C
ATOM   2133  O    TYR A 323       8.700  40.786  56.251  1.00 30.49           O
ATOM   2134  CB   TYR A 323       7.450  43.918  56.517  1.00 33.61           C
ATOM   2135  CG   TYR A 323       7.899  45.110  57.284  1.00 33.61           C
ATOM   2136  CD1  TYR A 323       7.251  46.330  57.113  1.00 33.61           C
ATOM   2137  CD2  TYR A 323       8.964  45.014  58.180  1.00 33.61           C
ATOM   2138  CE1  TYR A 323       7.662  47.444  57.829  1.00 33.61           C
ATOM   2139  CE2  TYR A 323       9.375  46.128  58.897  1.00 33.61           C
ATOM   2140  CZ   TYR A 323       8.729  47.338  58.723  1.00 33.61           C
ATOM   2141  OH   TYR A 323       9.119  48.448  59.448  1.00 33.61           O
ATOM   2142  N    THR A 324       7.429  41.608  54.576  1.00 27.56           N
ATOM   2143  CA   THR A 324       7.040  40.276  54.133  1.00 27.56           C
ATOM   2144  C    THR A 324       8.206  39.558  53.453  1.00 27.56           C
ATOM   2145  O    THR A 324       8.640  39.913  52.365  1.00 27.56           O
ATOM   2146  CB   THR A 324       5.878  40.423  53.150  1.00 33.13           C
ATOM   2147  OG1  THR A 324       4.840  41.191  53.762  1.00 33.13           O
ATOM   2148  CG2  THR A 324       5.322  39.043  52.785  1.00 33.13           C
ATOM   2149  N    PRO A 325       8.718  38.515  54.106  1.00 37.10           N
ATOM   2150  CA   PRO A 325       9.844  37.756  53.566  1.00 37.10           C
ATOM   2151  C    PRO A 325       9.556  37.224  52.172  1.00 37.10           C
ATOM   2152  O    PRO A 325      10.434  37.166  51.310  1.00 37.10           O
ATOM   2153  CB   PRO A 325      10.021  36.634  54.591  1.00 24.40           C
ATOM   2154  CG   PRO A 325       9.476  37.230  55.853  1.00 24.40           C
ATOM   2155  CD   PRO A 325       8.241  37.916  55.359  1.00 24.40           C
ATOM   2156  N    THR A 326       8.305  36.864  51.947  1.00 32.23           N
ATOM   2157  CA   THR A 326       7.910  36.293  50.676  1.00 32.23           C
ATOM   2158  C    THR A 326       7.697  37.318  49.554  1.00 32.23           C
ATOM   2159  O    THR A 326       7.446  36.952  48.405  1.00 32.23           O
ATOM   2160  CB   THR A 326       6.655  35.417  50.895  1.00 36.85           C
ATOM   2161  OG1  THR A 326       6.513  34.513  49.804  1.00 36.85           O
ATOM   2162  CG2  THR A 326       5.418  36.263  51.034  1.00 36.85           C
ATOM   2163  N    ALA A 327       7.836  38.598  49.889  1.00 32.40           N
ATOM   2164  CA   ALA A 327       7.660  39.676  48.919  1.00 32.40           C
ATOM   2165  C    ALA A 327       8.993  40.184  48.374  1.00 32.40           C
ATOM   2166  O    ALA A 327       9.036  40.934  47.392  1.00 32.40           O
ATOM   2167  CB   ALA A 327       6.896  40.826  49.552  1.00 22.71           C
```

FIG. 1-36

```
ATOM   2168  N    ARG A 328      10.081  39.781  49.018  1.00 29.48           N
ATOM   2169  CA   ARG A 328      11.403  40.195  48.586  1.00 29.48           C
ATOM   2170  C    ARG A 328      11.739  39.497  47.268  1.00 29.48           C
ATOM   2171  O    ARG A 328      11.318  38.366  47.020  1.00 29.48           O
ATOM   2172  CB   ARG A 328      12.439  39.842  49.657  1.00 24.82           C
ATOM   2173  CG   ARG A 328      12.228  40.558  50.979  1.00 24.82           C
ATOM   2174  CD   ARG A 328      12.873  39.823  52.139  1.00 24.82           C
ATOM   2175  NE   ARG A 328      12.317  40.282  53.413  1.00 24.82           N
ATOM   2176  CZ   ARG A 328      12.558  39.724  54.598  1.00 24.82           C
ATOM   2177  NH1  ARG A 328      13.349  38.671  54.699  1.00 24.82           N
ATOM   2178  NH2  ARG A 328      12.000  40.222  55.687  1.00 24.82           N
ATOM   2179  N    LEU A 329      12.472  40.196  46.411  1.00 24.91           N
ATOM   2180  CA   LEU A 329      12.879  39.646  45.132  1.00 24.91           C
ATOM   2181  C    LEU A 329      13.737  38.443  45.415  1.00 24.91           C
ATOM   2182  O    LEU A 329      14.281  38.299  46.507  1.00 24.91           O
ATOM   2183  CB   LEU A 329      13.704  40.667  44.354  1.00 35.89           C
ATOM   2184  CG   LEU A 329      12.990  41.653  43.431  1.00 35.89           C
ATOM   2185  CD1  LEU A 329      11.593  41.992  43.947  1.00 35.89           C
ATOM   2186  CD2  LEU A 329      13.863  42.900  43.308  1.00 35.89           C
ATOM   2187  N    THR A 330      13.854  37.575  44.427  1.00 27.02           N
ATOM   2188  CA   THR A 330      14.686  36.405  44.581  1.00 27.02           C
ATOM   2189  C    THR A 330      16.005  36.805  43.964  1.00 27.02           C
ATOM   2190  O    THR A 330      16.066  37.733  43.163  1.00 27.02           O
ATOM   2191  CB   THR A 330      14.141  35.218  43.814  1.00 37.14           C
ATOM   2192  OG1  THR A 330      14.347  35.429  42.411  1.00 37.14           O
ATOM   2193  CG2  THR A 330      12.658  35.054  44.101  1.00 37.14           C
ATOM   2194  N    PRO A 331      17.086  36.121  44.338  1.00 26.91           N
ATOM   2195  CA   PRO A 331      18.396  36.453  43.783  1.00 26.91           C
ATOM   2196  C    PRO A 331      18.392  36.654  42.268  1.00 26.91           C
ATOM   2197  O    PRO A 331      18.976  37.617  41.764  1.00 26.91           O
ATOM   2198  CB   PRO A 331      19.256  35.277  44.229  1.00 24.45           C
ATOM   2199  CG   PRO A 331      18.683  34.975  45.582  1.00 24.45           C
ATOM   2200  CD   PRO A 331      17.189  35.048  45.340  1.00 24.45           C
ATOM   2201  N    LEU A 332      17.729  35.758  41.541  1.00 33.38           N
ATOM   2202  CA   LEU A 332      17.682  35.885  40.092  1.00 33.38           C
ATOM   2203  C    LEU A 332      16.915  37.123  39.688  1.00 33.38           C
ATOM   2204  O    LEU A 332      17.292  37.790  38.735  1.00 33.38           O
ATOM   2205  CB   LEU A 332      17.050  34.658  39.442  1.00 38.61           C
ATOM   2206  CG   LEU A 332      17.919  33.426  39.163  1.00 38.61           C
ATOM   2207  CD1  LEU A 332      17.076  32.396  38.439  1.00 38.61           C
ATOM   2208  CD2  LEU A 332      19.103  33.792  38.305  1.00 38.61           C
ATOM   2209  N    GLU A 333      15.842  37.435  40.408  1.00 36.97           N
ATOM   2210  CA   GLU A 333      15.057  38.627  40.093  1.00 36.97           C
ATOM   2211  C    GLU A 333      15.873  39.882  40.406  1.00 36.97           C
ATOM   2212  O    GLU A 333      15.729  40.920  39.755  1.00 36.97           O
ATOM   2213  CB   GLU A 333      13.738  38.631  40.880  1.00 39.30           C
ATOM   2214  CG   GLU A 333      12.857  37.429  40.567  1.00 39.30           C
ATOM   2215  CD   GLU A 333      11.646  37.303  41.486  1.00 39.30           C
ATOM   2216  OE1  GLU A 333      11.776  37.603  42.691  1.00 39.30           O
ATOM   2217  OE2  GLU A 333      10.567  36.880  41.010  1.00 39.30           O
ATOM   2218  N    ALA A 334      16.745  39.780  41.397  1.00 32.12           N
ATOM   2219  CA   ALA A 334      17.582  40.908  41.762  1.00 32.12           C
ATOM   2220  C    ALA A 334      18.535  41.136  40.608  1.00 32.12           C
ATOM   2221  O    ALA A 334      18.742  42.260  40.190  1.00 32.12           O
ATOM   2222  CB   ALA A 334      18.347  40.604  43.040  1.00 22.68           C
ATOM   2223  N    CYS A 335      19.092  40.055  40.080  1.00 31.34           N
ATOM   2224  CA   CYS A 335      20.026  40.129  38.958  1.00 31.34           C
ATOM   2225  C    CYS A 335      19.455  40.746  37.695  1.00 31.34           C
ATOM   2226  O    CYS A 335      20.172  41.406  36.943  1.00 31.34           O
ATOM   2227  CB   CYS A 335      20.530  38.739  38.590  1.00 28.29           C
ATOM   2228  SG   CYS A 335      21.696  38.049  39.729  1.00 28.29           S
ATOM   2229  N    ALA A 336      18.172  40.506  37.452  1.00 25.38           N
```

FIG. 1-37

| | | | | | | | | | |
|---|---|---|---|---|---|---|---|---|---|
| ATOM | 2230 | CA | ALA | A | 336 | 17.507 | 41.009 | 36.257 | 1.00 25.38 | C |
| ATOM | 2231 | C | ALA | A | 336 | 16.890 | 42.385 | 36.449 | 1.00 25.38 | C |
| ATOM | 2232 | O | ALA | A | 336 | 16.183 | 42.884 | 35.572 | 1.00 25.38 | O |
| ATOM | 2233 | CB | ALA | A | 336 | 16.443 | 40.020 | 35.816 | 1.00 20.49 | C |
| ATOM | 2234 | N | HIS | A | 337 | 17.150 | 42.990 | 37.600 | 1.00 25.00 | N |
| ATOM | 2235 | CA | HIS | A | 337 | 16.610 | 44.307 | 37.881 | 1.00 25.00 | C |
| ATOM | 2236 | C | HIS | A | 337 | 17.274 | 45.325 | 36.960 | 1.00 25.00 | C |
| ATOM | 2237 | O | HIS | A | 337 | 18.437 | 45.164 | 36.583 | 1.00 25.00 | O |
| ATOM | 2238 | CB | HIS | A | 337 | 16.847 | 44.691 | 39.345 | 1.00 25.76 | C |
| ATOM | 2239 | CG | HIS | A | 337 | 16.185 | 45.975 | 39.738 | 1.00 25.76 | C |
| ATOM | 2240 | ND1 | HIS | A | 337 | 14.927 | 46.022 | 40.296 | 1.00 25.76 | N |
| ATOM | 2241 | CD2 | HIS | A | 337 | 16.579 | 47.260 | 39.593 | 1.00 25.76 | C |
| ATOM | 2242 | CE1 | HIS | A | 337 | 14.575 | 47.281 | 40.478 | 1.00 25.76 | C |
| ATOM | 2243 | NE2 | HIS | A | 337 | 15.559 | 48.054 | 40.059 | 1.00 25.76 | N |
| ATOM | 2244 | N | SER | A | 338 | 16.535 | 46.369 | 36.598 | 1.00 33.10 | N |
| ATOM | 2245 | CA | SER | A | 338 | 17.068 | 47.392 | 35.705 | 1.00 33.10 | C |
| ATOM | 2246 | C | SER | A | 338 | 18.389 | 47.987 | 36.196 | 1.00 33.10 | C |
| ATOM | 2247 | O | SER | A | 338 | 19.247 | 48.336 | 35.386 | 1.00 33.10 | O |
| ATOM | 2248 | CB | SER | A | 338 | 16.030 | 48.498 | 35.477 | 1.00 46.43 | C |
| ATOM | 2249 | OG | SER | A | 338 | 15.598 | 49.057 | 36.705 | 1.00 46.43 | O |
| ATOM | 2250 | N | PHE | A | 339 | 18.553 | 48.086 | 37.512 | 1.00 25.39 | N |
| ATOM | 2251 | CA | PHE | A | 339 | 19.783 | 48.612 | 38.108 | 1.00 25.39 | C |
| ATOM | 2252 | C | PHE | A | 339 | 21.048 | 47.945 | 37.557 | 1.00 25.39 | C |
| ATOM | 2253 | O | PHE | A | 339 | 22.129 | 48.526 | 37.588 | 1.00 25.39 | O |
| ATOM | 2254 | CB | PHE | A | 339 | 19.757 | 48.434 | 39.634 | 1.00 25.22 | C |
| ATOM | 2255 | CG | PHE | A | 339 | 20.991 | 48.941 | 40.327 | 1.00 25.22 | C |
| ATOM | 2256 | CD1 | PHE | A | 339 | 21.347 | 50.284 | 40.248 | 1.00 25.22 | C |
| ATOM | 2257 | CD2 | PHE | A | 339 | 21.814 | 48.069 | 41.032 | 1.00 25.22 | C |
| ATOM | 2258 | CE1 | PHE | A | 339 | 22.499 | 50.755 | 40.854 | 1.00 25.22 | C |
| ATOM | 2259 | CE2 | PHE | A | 339 | 22.974 | 48.529 | 41.647 | 1.00 25.22 | C |
| ATOM | 2260 | CZ | PHE | A | 339 | 23.316 | 49.881 | 41.555 | 1.00 25.22 | C |
| ATOM | 2261 | N | PHE | A | 340 | 20.913 | 46.726 | 37.053 | 1.00 26.97 | N |
| ATOM | 2262 | CA | PHE | A | 340 | 22.056 | 46.016 | 36.512 | 1.00 26.97 | C |
| ATOM | 2263 | C | PHE | A | 340 | 22.082 | 46.031 | 34.994 | 1.00 26.97 | C |
| ATOM | 2264 | O | PHE | A | 340 | 22.797 | 45.241 | 34.374 | 1.00 26.97 | O |
| ATOM | 2265 | CB | PHE | A | 340 | 22.056 | 44.577 | 37.010 | 1.00 20.05 | C |
| ATOM | 2266 | CG | PHE | A | 340 | 22.178 | 44.461 | 38.494 | 1.00 20.05 | C |
| ATOM | 2267 | CD1 | PHE | A | 340 | 23.372 | 44.777 | 39.132 | 1.00 20.05 | C |
| ATOM | 2268 | CD2 | PHE | A | 340 | 21.094 | 44.058 | 39.265 | 1.00 20.05 | C |
| ATOM | 2269 | CE1 | PHE | A | 340 | 23.485 | 44.691 | 40.511 | 1.00 20.05 | C |
| ATOM | 2270 | CE2 | PHE | A | 340 | 21.197 | 43.969 | 40.645 | 1.00 20.05 | C |
| ATOM | 2271 | CZ | PHE | A | 340 | 22.394 | 44.285 | 41.270 | 1.00 20.05 | C |
| ATOM | 2272 | N | ASP | A | 341 | 21.312 | 46.930 | 34.384 | 1.00 31.18 | N |
| ATOM | 2273 | CA | ASP | A | 341 | 21.283 | 46.986 | 32.929 | 1.00 31.18 | C |
| ATOM | 2274 | C | ASP | A | 341 | 22.637 | 47.374 | 32.335 | 1.00 31.18 | C |
| ATOM | 2275 | O | ASP | A | 341 | 23.035 | 46.834 | 31.314 | 1.00 31.18 | O |
| ATOM | 2276 | CB | ASP | A | 341 | 20.173 | 47.933 | 32.437 | 1.00 36.78 | C |
| ATOM | 2277 | CG | ASP | A | 341 | 18.795 | 47.262 | 32.425 | 1.00 36.78 | C |
| ATOM | 2278 | OD1 | ASP | A | 341 | 18.759 | 46.014 | 32.490 | 1.00 36.78 | O |
| ATOM | 2279 | OD2 | ASP | A | 341 | 17.752 | 47.961 | 32.335 | 1.00 36.78 | O |
| ATOM | 2280 | N | GLU | A | 342 | 23.354 | 48.293 | 32.973 | 1.00 28.84 | N |
| ATOM | 2281 | CA | GLU | A | 342 | 24.663 | 48.704 | 32.463 | 1.00 28.84 | C |
| ATOM | 2282 | C | GLU | A | 342 | 25.551 | 47.462 | 32.293 | 1.00 28.84 | C |
| ATOM | 2283 | O | GLU | A | 342 | 26.273 | 47.336 | 31.312 | 1.00 28.84 | O |
| ATOM | 2284 | CB | GLU | A | 342 | 25.339 | 49.697 | 33.438 | 1.00 37.21 | C |
| ATOM | 2285 | CG | GLU | A | 342 | 26.453 | 50.556 | 32.831 | 1.00 37.21 | C |
| ATOM | 2286 | CD | GLU | A | 342 | 27.265 | 51.353 | 33.868 | 1.00 37.21 | C |
| ATOM | 2287 | OE1 | GLU | A | 342 | 26.684 | 51.856 | 34.854 | 1.00 37.21 | O |
| ATOM | 2288 | OE2 | GLU | A | 342 | 28.498 | 51.496 | 33.692 | 1.00 37.21 | O |
| ATOM | 2289 | N | LEU | A | 343 | 25.492 | 46.545 | 33.255 | 1.00 34.22 | N |
| ATOM | 2290 | CA | LEU | A | 343 | 26.311 | 45.347 | 33.202 | 1.00 34.22 | C |
| ATOM | 2291 | C | LEU | A | 343 | 25.972 | 44.534 | 31.966 | 1.00 34.22 | C |

FIG. 1-38

```
ATOM   2292  O   LEU A 343      26.816  43.815  31.428  1.00 34.22           O
ATOM   2293  CB  LEU A 343      26.091  44.499  34.456  1.00 33.33           C
ATOM   2294  CG  LEU A 343      26.357  45.196  35.790  1.00 33.33           C
ATOM   2295  CD1 LEU A 343      26.132  44.227  36.942  1.00 33.33           C
ATOM   2296  CD2 LEU A 343      27.783  45.727  35.806  1.00 33.33           C
ATOM   2297  N   ARG A 344      24.730  44.646  31.518  1.00 38.25           N
ATOM   2298  CA  ARG A 344      24.304  43.908  30.350  1.00 38.25           C
ATOM   2299  C   ARG A 344      24.775  44.565  29.056  1.00 38.25           C
ATOM   2300  O   ARG A 344      24.904  43.893  28.027  1.00 38.25           O
ATOM   2301  CB  ARG A 344      22.784  43.721  30.363  1.00 30.47           C
ATOM   2302  CG  ARG A 344      22.348  42.457  31.114  1.00 30.47           C
ATOM   2303  CD  ARG A 344      20.839  42.242  31.113  1.00 30.47           C
ATOM   2304  NE  ARG A 344      20.145  43.139  32.032  1.00 30.47           N
ATOM   2305  CZ  ARG A 344      20.171  43.027  33.356  1.00 30.47           C
ATOM   2306  NH1 ARG A 344      20.858  42.051  33.935  1.00 30.47           N
ATOM   2307  NH2 ARG A 344      19.497  43.889  34.103  1.00 30.47           N
ATOM   2308  N   ASP A 345      25.057  45.866  29.109  1.00 36.28           N
ATOM   2309  CA  ASP A 345      25.540  46.589  27.936  1.00 36.28           C
ATOM   2310  C   ASP A 345      26.738  45.860  27.328  1.00 36.28           C
ATOM   2311  O   ASP A 345      27.570  45.303  28.038  1.00 36.28           O
ATOM   2312  CB  ASP A 345      25.968  48.001  28.322  1.00 54.81           C
ATOM   2313  CG  ASP A 345      26.315  48.869  27.109  1.00 54.81           C
ATOM   2314  OD1 ASP A 345      27.238  48.503  26.331  1.00 54.81           O
ATOM   2315  OD2 ASP A 345      25.658  49.927  26.946  1.00 54.81           O
ATOM   2316  N   PRO A 346      26.836  45.844  25.997  1.00 36.28           N
ATOM   2317  CA  PRO A 346      27.975  45.154  25.392  1.00 36.28           C
ATOM   2318  C   PRO A 346      29.270  45.958  25.436  1.00 36.28           C
ATOM   2319  O   PRO A 346      30.351  45.376  25.403  1.00 36.28           O
ATOM   2320  CB  PRO A 346      27.502  44.910  23.967  1.00 29.59           C
ATOM   2321  CG  PRO A 346      26.639  46.105  23.706  1.00 29.59           C
ATOM   2322  CD  PRO A 346      25.834  46.205  24.979  1.00 29.59           C
ATOM   2323  N   ASN A 347      29.166  47.285  25.519  1.00 50.30           N
ATOM   2324  CA  ASN A 347      30.358  48.140  25.535  1.00 50.30           C
ATOM   2325  C   ASN A 347      30.938  48.462  26.918  1.00 50.30           C
ATOM   2326  O   ASN A 347      31.947  49.171  27.024  1.00 50.30           O
ATOM   2327  CB  ASN A 347      30.074  49.459  24.807  0.00 52.63           C
ATOM   2328  CG  ASN A 347      29.667  49.256  23.360  1.00 52.63           C
ATOM   2329  OD1 ASN A 347      28.632  49.764  22.925  1.00 52.63           O
ATOM   2330  ND2 ASN A 347      30.478  48.514  22.604  1.00 52.63           N
ATOM   2331  N   VAL A 348      30.330  47.928  27.974  1.00 43.46           N
ATOM   2332  CA  VAL A 348      30.793  48.218  29.324  1.00 43.46           C
ATOM   2333  C   VAL A 348      32.133  47.586  29.694  1.00 43.46           C
ATOM   2334  O   VAL A 348      32.438  46.454  29.325  1.00 43.46           O
ATOM   2335  CB  VAL A 348      29.728  47.790  30.382  1.00 52.14           C
ATOM   2336  CG1 VAL A 348      29.686  46.256  30.508  1.00 52.14           C
ATOM   2337  CG2 VAL A 348      30.030  48.452  31.731  1.00 52.14           C
ATOM   2338  N   LYS A 349      32.929  48.343  30.434  1.00 40.96           N
ATOM   2339  CA  LYS A 349      34.225  47.876  30.897  1.00 40.96           C
ATOM   2340  C   LYS A 349      34.479  48.496  32.270  1.00 40.96           C
ATOM   2341  O   LYS A 349      33.711  49.339  32.731  1.00 40.96           O
ATOM   2342  CB  LYS A 349      35.314  48.284  29.905  1.00 49.14           C
ATOM   2343  CG  LYS A 349      34.986  47.877  28.461  1.00 49.14           C
ATOM   2344  CD  LYS A 349      36.244  47.631  27.632  1.00 49.14           C
ATOM   2345  CE  LYS A 349      37.016  46.420  28.149  1.00 49.14           C
ATOM   2346  NZ  LYS A 349      38.397  46.300  27.585  1.00 49.14           N
ATOM   2347  N   LEU A 350      35.538  48.071  32.938  1.00 38.10           N
ATOM   2348  CA  LEU A 350      35.843  48.624  34.245  1.00 38.10           C
ATOM   2349  C   LEU A 350      36.566  49.929  34.006  1.00 38.10           C
ATOM   2350  O   LEU A 350      37.191  50.097  32.962  1.00 38.10           O
ATOM   2351  CB  LEU A 350      36.736  47.662  35.011  1.00 30.19           C
ATOM   2352  CG  LEU A 350      36.202  46.227  35.043  1.00 30.19           C
ATOM   2353  CD1 LEU A 350      37.156  45.354  35.830  1.00 30.19           C
```

FIG. 1-39

```
ATOM   2354  CD2 LEU A 350      34.816  46.199  35.651  1.00 30.19           C
ATOM   2355  N   PRO A 351      36.498  50.872  34.962  1.00 48.81           N
ATOM   2356  CA  PRO A 351      37.180  52.168  34.795  1.00 48.81           C
ATOM   2357  C   PRO A 351      38.595  51.859  34.362  1.00 48.81           C
ATOM   2358  O   PRO A 351      39.256  52.621  33.668  1.00 48.81           O
ATOM   2359  CB  PRO A 351      37.137  52.755  36.197  1.00 41.63           C
ATOM   2360  CG  PRO A 351      37.230  51.547  37.045  1.00 41.63           C
ATOM   2361  CD  PRO A 351      36.233  50.616  36.385  1.00 41.63           C
ATOM   2362  N   ASN A 352      39.006  50.683  34.800  1.00 44.98           N
ATOM   2363  CA  ASN A 352      40.288  50.068  34.557  1.00 44.98           C
ATOM   2364  C   ASN A 352      40.641  49.972  33.066  1.00 44.98           C
ATOM   2365  O   ASN A 352      41.800  50.140  32.672  1.00 44.98           O
ATOM   2366  CB  ASN A 352      40.209  48.663  35.143  1.00 62.78           C
ATOM   2367  CG  ASN A 352      41.538  48.063  35.350  1.00 62.78           C
ATOM   2368  OD1 ASN A 352      42.539  48.590  34.857  1.00 62.78           O
ATOM   2369  ND2 ASN A 352      41.584  46.950  36.081  1.00 62.78           N
ATOM   2370  N   GLY A 353      39.634  49.682  32.244  1.00 41.80           N
ATOM   2371  CA  GLY A 353      39.852  49.522  30.820  1.00 41.80           C
ATOM   2372  C   GLY A 353      39.692  48.043  30.522  1.00 41.80           C
ATOM   2373  O   GLY A 353      39.389  47.649  29.395  1.00 41.80           O
ATOM   2374  N   ARG A 354      39.899  47.214  31.545  1.00 33.12           N
ATOM   2375  CA  ARG A 354      39.756  45.762  31.404  1.00 33.12           C
ATOM   2376  C   ARG A 354      38.282  45.402  31.267  1.00 33.12           C
ATOM   2377  O   ARG A 354      37.395  46.218  31.517  1.00 33.12           O
ATOM   2378  CB  ARG A 354      40.341  45.040  32.626  1.00 60.57           C
ATOM   2379  CG  ARG A 354      41.776  45.437  32.924  1.00 60.57           C
ATOM   2380  CD  ARG A 354      42.350  44.793  34.188  1.00 60.57           C
ATOM   2381  NE  ARG A 354      42.624  43.364  34.035  1.00 60.57           N
ATOM   2382  CZ  ARG A 354      43.483  42.684  34.800  1.00 60.57           C
ATOM   2383  NH1 ARG A 354      44.155  43.303  35.773  1.00 60.57           N
ATOM   2384  NH2 ARG A 354      43.675  41.383  34.595  1.00 60.57           N
ATOM   2385  N   ASP A 355      38.023  44.170  30.868  1.00 31.58           N
ATOM   2386  CA  ASP A 355      36.656  43.717  30.705  1.00 31.58           C
ATOM   2387  C   ASP A 355      36.064  43.308  32.045  1.00 31.58           C
ATOM   2388  O   ASP A 355      36.794  43.062  33.017  1.00 31.58           O
ATOM   2389  CB  ASP A 355      36.617  42.534  29.740  1.00 57.55           C
ATOM   2390  CG  ASP A 355      35.948  42.882  28.422  1.00 57.55           C
ATOM   2391  OD1 ASP A 355      34.694  42.805  28.340  1.00 57.55           O
ATOM   2392  OD2 ASP A 355      36.678  43.247  27.471  1.00 57.55           O
ATOM   2393  N   THR A 356      34.738  43.245  32.096  1.00 22.57           N
ATOM   2394  CA  THR A 356      34.065  42.845  33.314  1.00 22.57           C
ATOM   2395  C   THR A 356      34.219  41.331  33.447  1.00 22.57           C
ATOM   2396  O   THR A 356      34.465  40.623  32.474  1.00 22.57           O
ATOM   2397  CB  THR A 356      32.552  43.200  33.297  1.00 29.12           C
ATOM   2398  OG1 THR A 356      31.849  42.315  32.422  1.00 29.12           O
ATOM   2399  CG2 THR A 356      32.339  44.614  32.832  1.00 29.12           C
ATOM   2400  N   PRO A 357      34.099  40.816  34.667  1.00 31.50           N
ATOM   2401  CA  PRO A 357      34.240  39.368  34.800  1.00 31.50           C
ATOM   2402  C   PRO A 357      33.018  38.707  34.175  1.00 31.50           C
ATOM   2403  O   PRO A 357      32.069  39.389  33.790  1.00 31.50           O
ATOM   2404  CB  PRO A 357      34.326  39.177  36.315  1.00 41.97           C
ATOM   2405  CG  PRO A 357      33.464  40.297  36.849  1.00 41.97           C
ATOM   2406  CD  PRO A 357      33.852  41.467  35.969  1.00 41.97           C
ATOM   2407  N   ALA A 358      33.039  37.388  34.050  1.00 29.10           N
ATOM   2408  CA  ALA A 358      31.902  36.694  33.478  1.00 29.10           C
ATOM   2409  C   ALA A 358      30.695  37.026  34.338  1.00 29.10           C
ATOM   2410  O   ALA A 358      30.790  37.031  35.560  1.00 29.10           O
ATOM   2411  CB  ALA A 358      32.148  35.191  33.478  0.00 35.69           C
ATOM   2412  N   LEU A 359      29.570  37.322  33.700  1.00 28.58           N
ATOM   2413  CA  LEU A 359      28.351  37.641  34.427  1.00 28.58           C
ATOM   2414  C   LEU A 359      27.150  36.921  33.847  1.00 28.58           C
ATOM   2415  O   LEU A 359      26.087  36.863  34.472  1.00 28.58           O
```

FIG. 1-40

```
ATOM   2416  CB   LEU A 359      28.078  39.138  34.378  1.00 30.76           C
ATOM   2417  CG   LEU A 359      29.200  40.053  34.854  1.00 30.76           C
ATOM   2418  CD1  LEU A 359      28.704  41.499  34.831  1.00 30.76           C
ATOM   2419  CD2  LEU A 359      29.641  39.647  36.254  1.00 30.76           C
ATOM   2420  N    PHE A 360      27.327  36.364  32.652  1.00 37.37           N
ATOM   2421  CA   PHE A 360      26.248  35.673  31.957  1.00 37.37           C
ATOM   2422  C    PHE A 360      26.391  34.152  31.756  1.00 37.37           C
ATOM   2423  O    PHE A 360      25.471  33.506  31.266  1.00 37.37           O
ATOM   2424  CB   PHE A 360      26.056  36.344  30.610  1.00 30.39           C
ATOM   2425  CG   PHE A 360      26.165  37.831  30.666  1.00 30.39           C
ATOM   2426  CD1  PHE A 360      25.249  38.581  31.391  1.00 30.39           C
ATOM   2427  CD2  PHE A 360      27.182  38.488  29.987  1.00 30.39           C
ATOM   2428  CE1  PHE A 360      25.344  39.970  31.436  1.00 30.39           C
ATOM   2429  CE2  PHE A 360      27.283  39.873  30.026  1.00 30.39           C
ATOM   2430  CZ   PHE A 360      26.359  40.615  30.755  1.00 30.39           C
ATOM   2431  N    ASN A 361      27.528  33.579  32.129  1.00 33.59           N
ATOM   2432  CA   ASN A 361      27.725  32.148  31.956  1.00 33.59           C
ATOM   2433  C    ASN A 361      26.911  31.335  32.973  1.00 33.59           C
ATOM   2434  O    ASN A 361      27.448  30.530  33.760  1.00 33.59           O
ATOM   2435  CB   ASN A 361      29.218  31.822  32.051  1.00 42.55           C
ATOM   2436  CG   ASN A 361      29.825  32.288  33.340  1.00 42.55           C
ATOM   2437  OD1  ASN A 361      29.370  33.277  33.932  1.00 42.55           O
ATOM   2438  ND2  ASN A 361      30.872  31.592  33.790  1.00 42.55           N
ATOM   2439  N    PHE A 362      25.598  31.548  32.926  1.00 48.99           N
ATOM   2440  CA   PHE A 362      24.652  30.880  33.809  1.00 48.99           C
ATOM   2441  C    PHE A 362      24.545  29.378  33.587  1.00 48.99           C
ATOM   2442  O    PHE A 362      24.934  28.871  32.534  1.00 48.99           O
ATOM   2443  CB   PHE A 362      23.275  31.510  33.627  1.00 38.42           C
ATOM   2444  CG   PHE A 362      23.124  32.840  34.320  1.00 38.42           C
ATOM   2445  CD1  PHE A 362      23.062  32.911  35.712  1.00 38.42           C
ATOM   2446  CD2  PHE A 362      23.048  34.023  33.586  1.00 38.42           C
ATOM   2447  CE1  PHE A 362      22.929  34.135  36.353  1.00 38.42           C
ATOM   2448  CE2  PHE A 362      22.914  35.254  34.228  1.00 38.42           C
ATOM   2449  CZ   PHE A 362      22.854  35.305  35.610  1.00 38.42           C
ATOM   2450  N    THR A 363      24.014  28.667  34.580  1.00 41.08           N
ATOM   2451  CA   THR A 363      23.826  27.222  34.457  1.00 41.08           C
ATOM   2452  C    THR A 363      22.365  26.848  34.677  1.00 41.08           C
ATOM   2453  O    THR A 363      21.565  27.677  35.122  1.00 41.08           O
ATOM   2454  CB   THR A 363      24.676  26.448  35.469  1.00 37.00           C
ATOM   2455  OG1  THR A 363      24.205  26.704  36.802  1.00 37.00           O
ATOM   2456  CG2  THR A 363      26.133  26.856  35.336  1.00 37.00           C
ATOM   2457  N    THR A 364      22.011  25.611  34.349  1.00 41.13           N
ATOM   2458  CA   THR A 364      20.634  25.151  34.541  1.00 41.13           C
ATOM   2459  C    THR A 364      20.395  25.201  36.037  1.00 41.13           C
ATOM   2460  O    THR A 364      19.319  25.585  36.504  1.00 41.13           O
ATOM   2461  CB   THR A 364      20.436  23.698  34.061  1.00 37.94           C
ATOM   2462  OG1  THR A 364      21.219  22.813  34.872  0.00 37.94           O
ATOM   2463  CG2  THR A 364      20.857  23.564  32.610  1.00 37.94           C
ATOM   2464  N    GLN A 365      21.431  24.812  36.773  1.00 41.29           N
ATOM   2465  CA   GLN A 365      21.406  24.812  38.227  1.00 41.29           C
ATOM   2466  C    GLN A 365      21.041  26.215  38.698  1.00 41.29           C
ATOM   2467  O    GLN A 365      20.152  26.393  39.543  1.00 41.29           O
ATOM   2468  CB   GLN A 365      22.787  24.435  38.768  1.00 48.42           C
ATOM   2469  CG   GLN A 365      22.851  24.277  40.267  1.00 48.42           C
ATOM   2470  CD   GLN A 365      21.817  23.292  40.769  1.00 48.42           C
ATOM   2471  OE1  GLN A 365      21.587  22.264  40.135  1.00 48.42           O
ATOM   2472  NE2  GLN A 365      21.191  23.589  41.914  1.00 48.42           N
ATOM   2473  N    GLU A 366      21.720  27.211  38.132  1.00 37.78           N
ATOM   2474  CA   GLU A 366      21.490  28.593  38.502  1.00 37.78           C
ATOM   2475  C    GLU A 366      20.132  29.124  38.134  1.00 37.78           C
ATOM   2476  O    GLU A 366      19.481  29.747  38.964  1.00 37.78           O
ATOM   2477  CB   GLU A 366      22.533  29.514  37.871  1.00 50.83           C
```

FIG. 1-41

```
ATOM   2478  CG  GLU A 366      23.944  29.277  38.349  1.00 50.83           C
ATOM   2479  CD  GLU A 366      24.889  30.390  37.943  1.00 50.83           C
ATOM   2480  OE1 GLU A 366      24.662  31.536  38.399  1.00 50.83           O
ATOM   2481  OE2 GLU A 366      25.851  30.108  37.181  1.00 50.83           O
ATOM   2482  N   LEU A 367      19.701  28.890  36.901  1.00 30.92           N
ATOM   2483  CA  LEU A 367      18.425  29.422  36.429  1.00 30.92           C
ATOM   2484  C   LEU A 367      17.180  28.620  36.806  1.00 30.92           C
ATOM   2485  O   LEU A 367      16.055  29.021  36.471  1.00 30.92           O
ATOM   2486  CB  LEU A 367      18.482  29.558  34.916  1.00 29.00           C
ATOM   2487  CG  LEU A 367      19.753  30.228  34.410  1.00 29.00           C
ATOM   2488  CD1 LEU A 367      20.084  29.713  33.030  1.00 29.00           C
ATOM   2489  CD2 LEU A 367      19.572  31.736  34.410  1.00 29.00           C
ATOM   2490  N   SER A 368      17.382  27.495  37.494  1.00 46.84           N
ATOM   2491  CA  SER A 368      16.277  26.618  37.882  1.00 46.84           C
ATOM   2492  C   SER A 368      15.114  27.301  38.600  1.00 46.84           C
ATOM   2493  O   SER A 368      13.958  26.980  38.332  1.00 46.84           O
ATOM   2494  CB  SER A 368      16.785  25.463  38.746  1.00 35.11           C
ATOM   2495  OG  SER A 368      17.241  25.906  40.016  1.00 35.11           O
ATOM   2496  N   SER A 369      15.400  28.237  39.503  1.00 37.04           N
ATOM   2497  CA  SER A 369      14.324  28.911  40.230  1.00 37.04           C
ATOM   2498  C   SER A 369      13.305  29.542  39.273  1.00 37.04           C
ATOM   2499  O   SER A 369      12.125  29.621  39.596  1.00 37.04           O
ATOM   2500  CB  SER A 369      14.895  29.980  41.174  1.00 33.53           C
ATOM   2501  OG  SER A 369      14.796  31.295  40.642  1.00 33.53           O
ATOM   2502  N   ASN A 370      13.767  29.974  38.097  1.00 46.91           N
ATOM   2503  CA  ASN A 370      12.908  30.607  37.096  1.00 46.91           C
ATOM   2504  C   ASN A 370      13.632  30.703  35.740  1.00 46.91           C
ATOM   2505  O   ASN A 370      14.044  31.785  35.310  1.00 46.91           O
ATOM   2506  CB  ASN A 370      12.505  32.009  37.570  1.00 40.14           C
ATOM   2507  CG  ASN A 370      11.582  32.725  36.590  1.00 40.14           C
ATOM   2508  OD1 ASN A 370      11.781  32.663  35.376  1.00 40.14           O
ATOM   2509  ND2 ASN A 370      10.577  33.425  37.115  1.00 40.14           N
ATOM   2510  N   PRO A 371      13.793  29.564  35.051  1.00 42.70           N
ATOM   2511  CA  PRO A 371      14.462  29.499  33.751  1.00 42.70           C
ATOM   2512  C   PRO A 371      14.163  30.659  32.802  1.00 42.70           C
ATOM   2513  O   PRO A 371      15.077  31.288  32.262  1.00 42.70           O
ATOM   2514  CB  PRO A 371      13.984  28.167  33.207  1.00 33.77           C
ATOM   2515  CG  PRO A 371      13.967  27.313  34.449  1.00 33.77           C
ATOM   2516  CD  PRO A 371      13.304  28.232  35.458  1.00 33.77           C
ATOM   2517  N   PRO A 372      12.881  30.956  32.577  1.00 37.15           N
ATOM   2518  CA  PRO A 372      12.516  32.054  31.677  1.00 37.15           C
ATOM   2519  C   PRO A 372      13.143  33.401  31.966  1.00 37.15           C
ATOM   2520  O   PRO A 372      13.033  34.326  31.152  1.00 37.15           O
ATOM   2521  CB  PRO A 372      10.987  32.097  31.758  1.00 41.47           C
ATOM   2522  CG  PRO A 372      10.644  31.271  32.973  1.00 41.47           C
ATOM   2523  CD  PRO A 372      11.691  30.201  32.987  1.00 41.47           C
ATOM   2524  N   LEU A 373      13.796  33.534  33.114  1.00 34.30           N
ATOM   2525  CA  LEU A 373      14.418  34.812  33.424  1.00 34.30           C
ATOM   2526  C   LEU A 373      15.681  34.998  32.606  1.00 34.30           C
ATOM   2527  O   LEU A 373      16.243  36.092  32.542  1.00 34.30           O
ATOM   2528  CB  LEU A 373      14.722  34.930  34.915  1.00 28.60           C
ATOM   2529  CG  LEU A 373      13.548  35.427  35.774  1.00 28.60           C
ATOM   2530  CD1 LEU A 373      14.027  35.644  37.203  0.00 28.60           C
ATOM   2531  CD2 LEU A 373      12.981  36.716  35.189  1.00 28.60           C
ATOM   2532  N   ALA A 374      16.108  33.922  31.961  1.00 40.00           N
ATOM   2533  CA  ALA A 374      17.301  33.953  31.130  1.00 40.00           C
ATOM   2534  C   ALA A 374      17.129  34.903  29.926  1.00 40.00           C
ATOM   2535  O   ALA A 374      18.109  35.392  29.360  1.00 40.00           O
ATOM   2536  CB  ALA A 374      17.609  32.553  30.653  1.00 28.45           C
ATOM   2537  N   THR A 375      15.881  35.162  29.541  1.00 40.27           N
ATOM   2538  CA  THR A 375      15.599  36.041  28.418  1.00 40.27           C
ATOM   2539  C   THR A 375      15.987  37.467  28.775  1.00 40.27           C
```

FIG. 1-42

```
ATOM   2540  O    THR A 375      16.067  38.333  27.913  1.00 40.27           O
ATOM   2541  CB   THR A 375      14.102  35.991  28.016  1.00 31.59           C
ATOM   2542  OG1  THR A 375      13.293  36.541  29.063  1.00 31.59           O
ATOM   2543  CG2  THR A 375      13.680  34.560  27.766  1.00 31.59           C
ATOM   2544  N    ILE A 376      16.213  37.720  30.055  1.00 45.14           N
ATOM   2545  CA   ILE A 376      16.640  39.042  30.474  1.00 45.14           C
ATOM   2546  C    ILE A 376      18.079  38.886  30.942  1.00 45.14           C
ATOM   2547  O    ILE A 376      18.956  39.665  30.559  1.00 45.14           O
ATOM   2548  CB   ILE A 376      15.804  39.599  31.644  1.00 36.61           C
ATOM   2549  CG1  ILE A 376      14.328  39.701  31.250  1.00 36.61           C
ATOM   2550  CG2  ILE A 376      16.334  40.972  32.027  1.00 36.61           C
ATOM   2551  CD1  ILE A 376      13.426  40.236  32.341  0.00 36.61           C
ATOM   2552  N    LEU A 377      18.312  37.850  31.745  1.00 32.88           N
ATOM   2553  CA   LEU A 377      19.633  37.566  32.302  1.00 32.88           C
ATOM   2554  C    LEU A 377      20.760  37.410  31.292  1.00 32.88           C
ATOM   2555  O    LEU A 377      21.856  37.920  31.517  1.00 32.88           O
ATOM   2556  CB   LEU A 377      19.577  36.318  33.180  1.00 40.08           C
ATOM   2557  CG   LEU A 377      18.758  36.407  34.472  1.00 40.08           C
ATOM   2558  CD1  LEU A 377      18.716  35.029  35.117  1.00 40.08           C
ATOM   2559  CD2  LEU A 377      19.373  37.446  35.415  1.00 40.08           C
ATOM   2560  N    ILE A 378      20.511  36.690  30.197  1.00 43.30           N
ATOM   2561  CA   ILE A 378      21.531  36.508  29.163  1.00 43.30           C
ATOM   2562  C    ILE A 378      21.261  37.478  28.011  1.00 43.30           C
ATOM   2563  O    ILE A 378      20.361  37.274  27.199  1.00 43.30           O
ATOM   2564  CB   ILE A 378      21.555  35.061  28.639  1.00 30.57           C
ATOM   2565  CG1  ILE A 378      21.857  34.103  29.796  1.00 30.57           C
ATOM   2566  CG2  ILE A 378      22.610  34.925  27.569  1.00 30.57           C
ATOM   2567  CD1  ILE A 378      22.140  32.662  29.388  1.00 30.57           C
ATOM   2568  N    PRO A 379      22.060  38.548  27.919  1.00 39.61           N
ATOM   2569  CA   PRO A 379      21.909  39.564  26.877  1.00 39.61           C
ATOM   2570  C    PRO A 379      22.275  39.095  25.471  1.00 39.61           C
ATOM   2571  O    PRO A 379      23.170  38.270  25.281  1.00 39.61           O
ATOM   2572  CB   PRO A 379      22.805  40.683  27.377  1.00 32.34           C
ATOM   2573  CG   PRO A 379      23.952  39.922  27.948  1.00 32.34           C
ATOM   2574  CD   PRO A 379      23.292  38.776  28.696  1.00 32.34           C
ATOM   2575  N    PRO A 380      21.582  39.638  24.463  1.00 34.90           N
ATOM   2576  CA   PRO A 380      21.752  39.345  23.040  1.00 34.90           C
ATOM   2577  C    PRO A 380      23.182  39.093  22.593  1.00 34.90           C
ATOM   2578  O    PRO A 380      23.491  38.000  22.121  1.00 34.90           O
ATOM   2579  CB   PRO A 380      21.151  40.570  22.369  1.00 43.65           C
ATOM   2580  CG   PRO A 380      20.005  40.891  23.271  1.00 43.65           C
ATOM   2581  CD   PRO A 380      20.600  40.722  24.658  1.00 43.65           C
ATOM   2582  N    HIS A 381      24.058  40.089  22.730  1.00 31.94           N
ATOM   2583  CA   HIS A 381      25.432  39.891  22.286  1.00 31.94           C
ATOM   2584  C    HIS A 381      26.027  38.613  22.864  1.00 31.94           C
ATOM   2585  O    HIS A 381      26.861  37.967  22.230  1.00 31.94           O
ATOM   2586  CB   HIS A 381      26.314  41.117  22.589  1.00 42.72           C
ATOM   2587  CG   HIS A 381      26.465  41.446  24.040  1.00 42.72           C
ATOM   2588  ND1  HIS A 381      27.485  40.925  24.825  1.00 42.72           N
ATOM   2589  CD2  HIS A 381      25.798  42.311  24.838  1.00 42.72           C
ATOM   2590  CE1  HIS A 381      27.435  41.464  26.024  1.00 42.72           C
ATOM   2591  NE2  HIS A 381      26.418  42.316  26.065  1.00 42.72           N
ATOM   2592  N    ALA A 382      25.564  38.221  24.046  1.00 47.93           N
ATOM   2593  CA   ALA A 382      26.056  37.001  24.679  1.00 47.93           C
ATOM   2594  C    ALA A 382      25.575  35.746  23.931  1.00 47.93           C
ATOM   2595  O    ALA A 382      26.067  34.634  24.173  1.00 47.93           O
ATOM   2596  CB   ALA A 382      25.605  36.950  26.126  1.00 51.96           C
ATOM   2597  N    ARG A 383      24.630  35.932  23.012  1.00 65.05           N
ATOM   2598  CA   ARG A 383      24.079  34.828  22.235  1.00 65.05           C
ATOM   2599  C    ARG A 383      24.639  34.795  20.810  1.00 65.05           C
ATOM   2600  O    ARG A 383      23.971  34.342  19.872  1.00 65.05           O
ATOM   2601  CB   ARG A 383      22.543  34.932  22.202  1.00 55.86           C
```

FIG. 1-43

```
ATOM   2602  CG   ARG A 383      21.860  34.470  23.487  1.00 55.86           C
ATOM   2603  CD   ARG A 383      20.930  35.515  24.090  1.00 55.86           C
ATOM   2604  NE   ARG A 383      19.519  35.334  23.742  1.00 55.86           N
ATOM   2605  CZ   ARG A 383      18.523  35.994  24.336  1.00 55.86           C
ATOM   2606  NH1  ARG A 383      18.779  36.871  25.302  1.00 55.86           N
ATOM   2607  NH2  ARG A 383      17.266  35.784  23.967  1.00 55.86           N
ATOM   2608  N    ILE A 384      25.872  35.262  20.654  1.00 66.55           N
ATOM   2609  CA   ILE A 384      26.513  35.294  19.346  1.00 66.55           C
ATOM   2610  C    ILE A 384      27.751  34.391  19.360  1.00 66.55           C
ATOM   2611  O    ILE A 384      28.407  34.334  20.435  1.00 66.55           O
ATOM   2612  CB   ILE A 384      26.918  36.742  19.009  1.00 45.60           C
ATOM   2613  CG1  ILE A 384      25.666  37.629  19.027  1.00 45.60           C
ATOM   2614  CG2  ILE A 384      27.619  36.793  17.670  1.00 45.60           C
ATOM   2615  CD1  ILE A 384      25.953  39.127  19.005  1.00 45.60           C
TER    2616       ILE A 384
ATOM   2617  N    VAL B  37      14.552  82.083  77.018  1.00 56.12           N
ATOM   2618  CA   VAL B  37      13.942  81.747  78.345  1.00 56.12           C
ATOM   2619  C    VAL B  37      12.523  81.177  78.206  1.00 56.12           C
ATOM   2620  O    VAL B  37      11.555  81.926  78.150  1.00 56.12           O
ATOM   2621  CB   VAL B  37      13.875  82.990  79.253  1.00 52.00           C
ATOM   2622  CG1  VAL B  37      13.231  82.624  80.581  1.00 52.00           C
ATOM   2623  CG2  VAL B  37      15.271  83.548  79.479  0.00 52.00           C
ATOM   2624  N    THR B  38      12.408  79.851  78.170  1.00 50.61           N
ATOM   2625  CA   THR B  38      11.114  79.171  78.020  1.00 50.61           C
ATOM   2626  C    THR B  38      10.316  78.942  79.309  1.00 50.61           C
ATOM   2627  O    THR B  38      10.876  78.558  80.346  1.00 50.61           O
ATOM   2628  CB   THR B  38      11.308  77.796  77.351  1.00 36.91           C
ATOM   2629  OG1  THR B  38      11.830  77.984  76.031  1.00 36.91           O
ATOM   2630  CG2  THR B  38       9.993  77.039  77.270  1.00 36.91           C
ATOM   2631  N    THR B  39       9.005  79.170  79.233  1.00 35.81           N
ATOM   2632  CA   THR B  39       8.109  78.962  80.375  1.00 35.81           C
ATOM   2633  C    THR B  39       7.008  77.971  80.011  1.00 35.81           C
ATOM   2634  O    THR B  39       6.230  78.201  79.085  1.00 35.81           O
ATOM   2635  CB   THR B  39       7.439  80.276  80.841  1.00 39.66           C
ATOM   2636  OG1  THR B  39       8.434  81.167  81.359  1.00 39.66           O
ATOM   2637  CG2  THR B  39       6.414  79.998  81.935  1.00 39.66           C
ATOM   2638  N    VAL B  40       6.947  76.865  80.740  1.00 41.05           N
ATOM   2639  CA   VAL B  40       5.938  75.852  80.474  1.00 41.05           C
ATOM   2640  C    VAL B  40       5.248  75.539  81.794  1.00 41.05           C
ATOM   2641  O    VAL B  40       5.676  76.006  82.851  1.00 41.05           O
ATOM   2642  CB   VAL B  40       6.588  74.551  79.913  1.00 19.78           C
ATOM   2643  CG1  VAL B  40       7.415  73.880  80.985  1.00 19.78           C
ATOM   2644  CG2  VAL B  40       5.516  73.604  79.399  0.00 19.78           C
ATOM   2645  N    VAL B  41       4.168  74.773  81.740  1.00 31.97           N
ATOM   2646  CA   VAL B  41       3.477  74.387  82.957  1.00 31.97           C
ATOM   2647  C    VAL B  41       3.739  72.883  83.078  1.00 31.97           C
ATOM   2648  O    VAL B  41       3.239  72.082  82.291  1.00 31.97           O
ATOM   2649  CB   VAL B  41       1.966  74.715  82.863  1.00 24.67           C
ATOM   2650  CG1  VAL B  41       1.356  74.043  81.647  0.00 24.67           C
ATOM   2651  CG2  VAL B  41       1.265  74.293  84.138  1.00 24.67           C
ATOM   2652  N    ALA B  42       4.549  72.496  84.052  1.00 33.95           N
ATOM   2653  CA   ALA B  42       4.891  71.092  84.191  1.00 33.95           C
ATOM   2654  C    ALA B  42       4.369  70.395  85.434  1.00 33.95           C
ATOM   2655  O    ALA B  42       4.246  70.990  86.501  1.00 33.95           O
ATOM   2656  CB   ALA B  42       6.410  70.927  84.101  1.00 51.36           C
ATOM   2657  N    THR B  43       4.083  69.109  85.279  1.00 37.68           N
ATOM   2658  CA   THR B  43       3.576  68.290  86.364  1.00 37.68           C
ATOM   2659  C    THR B  43       4.746  67.575  87.025  1.00 37.68           C
ATOM   2660  O    THR B  43       5.542  66.921  86.356  1.00 37.68           O
ATOM   2661  CB   THR B  43       2.596  67.238  85.832  1.00 34.53           C
ATOM   2662  OG1  THR B  43       1.518  67.892  85.161  1.00 34.53           O
ATOM   2663  CG2  THR B  43       2.041  66.397  86.965  1.00 34.53           C
```

FIG. 1-44

| ATOM | 2664 | N | PRO | B | 44 | 4.877 | 67.709 | 88.348 | 1.00 | 34.56 | N |
|---|---|---|---|---|---|---|---|---|---|---|---|
| ATOM | 2665 | CA | PRO | B | 44 | 5.963 | 67.062 | 89.092 | 1.00 | 34.56 | C |
| ATOM | 2666 | C | PRO | B | 44 | 5.900 | 65.529 | 89.007 | 1.00 | 34.56 | C |
| ATOM | 2667 | O | PRO | B | 44 | 4.817 | 64.937 | 89.023 | 1.00 | 34.56 | O |
| ATOM | 2668 | CB | PRO | B | 44 | 5.752 | 67.575 | 90.514 | 1.00 | 26.17 | C |
| ATOM | 2669 | CG | PRO | B | 44 | 5.167 | 68.935 | 90.285 | 1.00 | 26.17 | C |
| ATOM | 2670 | CD | PRO | B | 44 | 4.165 | 68.684 | 89.193 | 1.00 | 26.17 | C |
| ATOM | 2671 | N | GLY | B | 45 | 7.064 | 64.893 | 88.923 | 1.00 | 35.52 | N |
| ATOM | 2672 | CA | GLY | B | 45 | 7.116 | 63.445 | 88.828 | 1.00 | 35.52 | C |
| ATOM | 2673 | C | GLY | B | 45 | 6.416 | 62.752 | 89.975 | 1.00 | 35.52 | C |
| ATOM | 2674 | O | GLY | B | 45 | 5.636 | 61.825 | 89.756 | 1.00 | 35.52 | O |
| ATOM | 2675 | N | GLN | B | 46 | 6.696 | 63.211 | 91.195 | 1.00 | 53.35 | N |
| ATOM | 2676 | CA | GLN | B | 46 | 6.111 | 62.650 | 92.412 | 1.00 | 53.35 | C |
| ATOM | 2677 | C | GLN | B | 46 | 4.783 | 63.330 | 92.734 | 1.00 | 53.35 | C |
| ATOM | 2678 | O | GLN | B | 46 | 4.261 | 64.109 | 91.920 | 1.00 | 53.35 | O |
| ATOM | 2679 | CB | GLN | B | 46 | 7.081 | 62.815 | 93.577 | 0.00 | 35.69 | C |
| ATOM | 2680 | N | GLY | B | 47 | 4.245 | 63.027 | 93.915 | 1.00 | 56.57 | N |
| ATOM | 2681 | CA | GLY | B | 47 | 2.983 | 63.600 | 94.355 | 0.00 | 56.57 | C |
| ATOM | 2682 | C | GLY | B | 47 | 1.859 | 63.454 | 93.348 | 1.00 | 56.57 | C |
| ATOM | 2683 | O | GLY | B | 47 | 2.074 | 62.931 | 92.252 | 1.00 | 56.57 | O |
| ATOM | 2684 | N | PRO | B | 48 | 0.633 | 63.894 | 93.686 | 1.00 | 57.40 | N |
| ATOM | 2685 | CA | PRO | B | 48 | -0.478 | 63.775 | 92.731 | 1.00 | 57.40 | C |
| ATOM | 2686 | C | PRO | B | 48 | -0.367 | 64.882 | 91.676 | 1.00 | 57.40 | C |
| ATOM | 2687 | O | PRO | B | 48 | 0.295 | 65.891 | 91.914 | 1.00 | 57.40 | O |
| ATOM | 2688 | CB | PRO | B | 48 | -1.701 | 63.932 | 93.621 | 1.00 | 31.51 | C |
| ATOM | 2689 | CG | PRO | B | 48 | -1.226 | 64.924 | 94.638 | 0.00 | 31.51 | C |
| ATOM | 2690 | CD | PRO | B | 48 | 0.160 | 64.413 | 94.981 | 0.00 | 31.51 | C |
| ATOM | 2691 | N | ASP | B | 49 | -1.008 | 64.708 | 90.523 | 1.00 | 47.39 | N |
| ATOM | 2692 | CA | ASP | B | 49 | -0.925 | 65.724 | 89.476 | 1.00 | 47.39 | C |
| ATOM | 2693 | C | ASP | B | 49 | -1.165 | 67.154 | 89.974 | 1.00 | 47.39 | C |
| ATOM | 2694 | O | ASP | B | 49 | -2.290 | 67.652 | 89.945 | 1.00 | 47.39 | O |
| ATOM | 2695 | CB | ASP | B | 49 | -1.892 | 65.410 | 88.324 | 1.00 | 55.67 | C |
| ATOM | 2696 | CG | ASP | B | 49 | -1.395 | 64.281 | 87.433 | 1.00 | 55.67 | C |
| ATOM | 2697 | OD1 | ASP | B | 49 | -1.916 | 64.117 | 86.304 | 1.00 | 55.67 | O |
| ATOM | 2698 | OD2 | ASP | B | 49 | -0.485 | 63.543 | 87.870 | 1.00 | 55.67 | O |
| ATOM | 2699 | N | ARG | B | 50 | -0.083 | 67.814 | 90.392 | 1.00 | 45.98 | N |
| ATOM | 2700 | CA | ARG | B | 50 | -0.121 | 69.183 | 90.922 | 1.00 | 45.98 | C |
| ATOM | 2701 | C | ARG | B | 50 | 0.768 | 70.097 | 90.059 | 1.00 | 45.98 | C |
| ATOM | 2702 | O | ARG | B | 50 | 1.798 | 70.583 | 90.527 | 1.00 | 45.98 | O |
| ATOM | 2703 | CB | ARG | B | 50 | 0.421 | 69.164 | 92.351 | 1.00 | 70.01 | C |
| ATOM | 2704 | CG | ARG | B | 50 | -0.140 | 70.225 | 93.277 | 1.00 | 70.01 | C |
| ATOM | 2705 | CD | ARG | B | 50 | -1.448 | 69.768 | 93.921 | 1.00 | 70.01 | C |
| ATOM | 2706 | NE | ARG | B | 50 | -2.530 | 69.633 | 92.944 | 1.00 | 70.01 | N |
| ATOM | 2707 | CZ | ARG | B | 50 | -3.815 | 69.491 | 93.275 | 1.00 | 70.01 | C |
| ATOM | 2708 | NH1 | ARG | B | 50 | -4.166 | 69.460 | 94.553 | 0.00 | 70.01 | N |
| ATOM | 2709 | NH2 | ARG | B | 50 | -4.754 | 69.394 | 92.332 | 1.00 | 70.01 | N |
| ATOM | 2710 | N | PRO | B | 51 | 0.381 | 70.337 | 88.793 | 1.00 | 33.39 | N |
| ATOM | 2711 | CA | PRO | B | 51 | 1.114 | 71.179 | 87.835 | 1.00 | 33.39 | C |
| ATOM | 2712 | C | PRO | B | 51 | 1.512 | 72.548 | 88.361 | 1.00 | 33.39 | C |
| ATOM | 2713 | O | PRO | B | 51 | 0.789 | 73.146 | 89.137 | 1.00 | 33.39 | O |
| ATOM | 2714 | CB | PRO | B | 51 | 0.141 | 71.302 | 86.668 | 1.00 | 25.10 | C |
| ATOM | 2715 | CG | PRO | B | 51 | -0.589 | 70.024 | 86.704 | 1.00 | 25.10 | C |
| ATOM | 2716 | CD | PRO | B | 51 | -0.849 | 69.812 | 88.180 | 1.00 | 25.10 | C |
| ATOM | 2717 | N | GLN | B | 52 | 2.661 | 73.051 | 87.933 | 1.00 | 31.52 | N |
| ATOM | 2718 | CA | GLN | B | 52 | 3.112 | 74.372 | 88.357 | 1.00 | 31.52 | C |
| ATOM | 2719 | C | GLN | B | 52 | 3.814 | 75.029 | 87.193 | 1.00 | 31.52 | C |
| ATOM | 2720 | O | GLN | B | 52 | 4.183 | 74.362 | 86.232 | 1.00 | 31.52 | O |
| ATOM | 2721 | CB | GLN | B | 52 | 4.053 | 74.283 | 89.571 | 1.00 | 48.92 | C |
| ATOM | 2722 | CG | GLN | B | 52 | 5.087 | 73.175 | 89.484 | 1.00 | 48.92 | C |
| ATOM | 2723 | CD | GLN | B | 52 | 5.887 | 72.998 | 90.774 | 1.00 | 48.92 | C |
| ATOM | 2724 | OE1 | GLN | B | 52 | 6.846 | 73.734 | 91.037 | 1.00 | 48.92 | O |
| ATOM | 2725 | NE2 | GLN | B | 52 | 5.489 | 72.024 | 91.585 | 0.00 | 48.92 | N |

FIG. 1-45

```
ATOM   2726  N    GLU B  53       3.966  76.344  87.247  1.00 38.95           N
ATOM   2727  CA   GLU B  53       4.650  77.036  86.166  1.00 38.95           C
ATOM   2728  C    GLU B  53       6.156  76.838  86.382  1.00 38.95           C
ATOM   2729  O    GLU B  53       6.670  76.993  87.497  1.00 38.95           O
ATOM   2730  CB   GLU B  53       4.252  78.528  86.146  1.00 73.86           C
ATOM   2731  CG   GLU B  53       2.766  78.743  85.768  1.00 73.86           C
ATOM   2732  CD   GLU B  53       2.200  80.131  86.133  1.00 73.86           C
ATOM   2733  OE1  GLU B  53       2.446  80.609  87.275  1.00 73.86           O
ATOM   2734  OE2  GLU B  53       1.490  80.730  85.280  1.00 73.86           O
ATOM   2735  N    VAL B  54       6.838  76.446  85.306  1.00 31.78           N
ATOM   2736  CA   VAL B  54       8.270  76.185  85.330  1.00 31.78           C
ATOM   2737  C    VAL B  54       8.977  76.902  84.175  1.00 31.78           C
ATOM   2738  O    VAL B  54       8.542  76.824  83.021  1.00 31.78           O
ATOM   2739  CB   VAL B  54       8.546  74.665  85.226  1.00 20.11           C
ATOM   2740  CG1  VAL B  54      10.032  74.391  85.393  1.00 20.11           C
ATOM   2741  CG2  VAL B  54       7.760  73.917  86.279  1.00 20.11           C
ATOM   2742  N    SER B  55      10.068  77.600  84.494  1.00 37.42           N
ATOM   2743  CA   SER B  55      10.845  78.333  83.488  1.00 37.42           C
ATOM   2744  C    SER B  55      12.308  77.887  83.422  1.00 37.42           C
ATOM   2745  O    SER B  55      12.982  77.753  84.446  1.00 37.42           O
ATOM   2746  CB   SER B  55      10.780  79.837  83.771  1.00 49.54           C
ATOM   2747  OG   SER B  55       9.465  80.335  83.562  1.00 49.54           O
ATOM   2748  N    TYR B  56      12.793  77.661  82.207  1.00 44.46           N
ATOM   2749  CA   TYR B  56      14.173  77.231  82.003  1.00 44.46           C
ATOM   2750  C    TYR B  56      14.799  77.949  80.806  1.00 44.46           C
ATOM   2751  O    TYR B  56      14.088  78.480  79.928  1.00 44.46           O
ATOM   2752  CB   TYR B  56      14.229  75.718  81.775  1.00 34.06           C
ATOM   2753  CG   TYR B  56      13.523  75.218  80.520  1.00 34.06           C
ATOM   2754  CD1  TYR B  56      14.085  75.390  79.248  1.00 34.06           C
ATOM   2755  CD2  TYR B  56      12.305  74.532  80.607  1.00 34.06           C
ATOM   2756  CE1  TYR B  56      13.453  74.881  78.093  1.00 34.06           C
ATOM   2757  CE2  TYR B  56      11.668  74.022  79.457  1.00 34.06           C
ATOM   2758  CZ   TYR B  56      12.250  74.203  78.210  1.00 34.06           C
ATOM   2759  OH   TYR B  56      11.618  73.706  77.093  1.00 34.06           O
ATOM   2760  N    THR B  57      16.131  77.958  80.757  1.00 63.55           N
ATOM   2761  CA   THR B  57      16.817  78.613  79.651  1.00 63.55           C
ATOM   2762  C    THR B  57      18.191  77.993  79.370  1.00 63.55           C
ATOM   2763  O    THR B  57      18.516  76.924  79.908  1.00 63.55           O
ATOM   2764  CB   THR B  57      16.951  80.123  79.932  1.00 44.35           C
ATOM   2765  OG1  THR B  57      17.145  80.830  78.696  1.00 44.35           O
ATOM   2766  CG2  THR B  57      18.103  80.376  80.907  1.00 44.35           C
ATOM   2767  N    ASP B  58      18.987  78.665  78.532  1.00 61.81           N
ATOM   2768  CA   ASP B  58      20.319  78.181  78.148  1.00 61.81           C
ATOM   2769  C    ASP B  58      20.138  76.761  77.639  1.00 61.81           C
ATOM   2770  O    ASP B  58      20.860  75.844  78.030  1.00 61.81           O
ATOM   2771  CB   ASP B  58      21.278  78.189  79.350  1.00 60.47           C
ATOM   2772  CG   ASP B  58      21.455  79.579  79.950  1.00 60.47           C
ATOM   2773  OD1  ASP B  58      21.159  80.580  79.253  1.00 60.47           O
ATOM   2774  OD2  ASP B  58      21.901  79.677  81.115  1.00 60.47           O
ATOM   2775  N    THR B  59      19.171  76.602  76.747  1.00 46.38           N
ATOM   2776  CA   THR B  59      18.807  75.302  76.203  1.00 46.38           C
ATOM   2777  C    THR B  59      19.540  74.828  74.959  1.00 46.38           C
ATOM   2778  O    THR B  59      19.313  75.356  73.861  1.00 46.38           O
ATOM   2779  CB   THR B  59      17.294  75.288  75.918  1.00 44.29           C
ATOM   2780  OG1  THR B  59      16.596  75.512  77.152  1.00 44.29           O
ATOM   2781  CG2  THR B  59      16.857  73.972  75.285  1.00 44.29           C
ATOM   2782  N    LYS B  60      20.390  73.813  75.135  1.00 56.43           N
ATOM   2783  CA   LYS B  60      21.138  73.257  74.013  1.00 56.43           C
ATOM   2784  C    LYS B  60      20.959  71.741  73.912  1.00 56.43           C
ATOM   2785  O    LYS B  60      20.663  71.050  74.879  1.00 56.43           O
ATOM   2786  CB   LYS B  60      22.617  73.590  74.215  1.00 46.68           C
ATOM   2787  CG   LYS B  60      23.273  72.691  75.265  1.00 46.68           C
```

FIG. 1-46

```
ATOM   2788  CD   LYS B  60      24.747  73.037  75.489  0.00 46.68           C
ATOM   2789  CE   LYS B  60      24.937  74.410  76.140  0.00 46.68           C
ATOM   2790  NZ   LYS B  60      24.177  74.474  77.388  0.00 46.68           N
ATOM   2791  N    VAL B  61      21.111  71.232  72.675  1.00 52.10           N
ATOM   2792  CA   VAL B  61      20.994  69.794  72.467  1.00 52.10           C
ATOM   2793  C    VAL B  61      22.231  69.053  72.981  1.00 52.10           C
ATOM   2794  O    VAL B  61      23.360  69.511  72.869  1.00 52.10           O
ATOM   2795  CB   VAL B  61      20.825  69.545  70.968  1.00 33.83           C
ATOM   2796  CG1  VAL B  61      20.703  68.047  70.698  1.00 33.83           C
ATOM   2797  CG2  VAL B  61      19.579  70.248  70.463  1.00 33.83           C
ATOM   2798  N    ILE B  62      21.980  67.883  73.599  1.00 46.31           N
ATOM   2799  CA   ILE B  62      23.088  67.106  74.140  1.00 46.31           C
ATOM   2800  C    ILE B  62      23.037  65.646  73.683  1.00 46.31           C
ATOM   2801  O    ILE B  62      23.389  64.722  74.404  1.00 46.31           O
ATOM   2802  CB   ILE B  62      23.025  67.181  75.667  1.00 46.04           C
ATOM   2803  CG1  ILE B  62      21.730  66.542  76.177  1.00 46.04           C
ATOM   2804  CG2  ILE B  62      23.032  68.653  76.116  1.00 46.04           C
ATOM   2805  CD1  ILE B  62      21.747  66.327  77.692  1.00 46.04           C
ATOM   2806  N    GLY B  63      22.538  65.450  72.448  1.00 47.10           N
ATOM   2807  CA   GLY B  63      22.471  64.097  71.909  1.00 47.10           C
ATOM   2808  C    GLY B  63      21.111  63.808  71.270  1.00 47.10           C
ATOM   2809  O    GLY B  63      20.113  64.471  71.523  1.00 47.10           O
ATOM   2810  N    ASN B  64      21.106  62.800  70.378  1.00 62.66           N
ATOM   2811  CA   ASN B  64      19.862  62.434  69.712  1.00 62.66           C
ATOM   2812  C    ASN B  64      19.632  60.922  69.742  1.00 62.66           C
ATOM   2813  O    ASN B  64      20.358  60.137  69.146  1.00 62.66           O
ATOM   2814  CB   ASN B  64      19.935  62.920  68.264  1.00 87.20           C
ATOM   2815  CG   ASN B  64      19.849  64.424  68.235  1.00 87.20           C
ATOM   2816  OD1  ASN B  64      18.885  65.010  67.752  1.00 87.20           O
ATOM   2817  ND2  ASN B  64      20.900  65.061  68.779  1.00 87.20           N
ATOM   2818  N    GLY B  65      18.600  60.517  70.504  1.00 91.55           N
ATOM   2819  CA   GLY B  65      18.291  59.096  70.600  1.00 91.55           C
ATOM   2820  C    GLY B  65      17.528  58.602  69.368  1.00 91.55           C
ATOM   2821  O    GLY B  65      17.514  59.224  68.314  0.00 91.55           O
ATOM   2822  N    SER B  66      16.909  57.416  69.520  1.00 76.40           N
ATOM   2823  CA   SER B  66      16.146  56.855  68.412  1.00 76.40           C
ATOM   2824  C    SER B  66      14.673  57.262  68.483  1.00 76.40           C
ATOM   2825  O    SER B  66      13.973  57.362  67.484  1.00 76.40           O
ATOM   2826  CB   SER B  66      16.270  55.332  68.471  1.00 42.15           C
ATOM   2827  OG   SER B  66      17.555  54.984  68.986  1.00 42.15           O
ATOM   2828  N    PHE B  67      14.197  57.460  69.726  1.00 43.17           N
ATOM   2829  CA   PHE B  67      12.803  57.847  69.910  1.00 43.17           C
ATOM   2830  C    PHE B  67      12.625  59.365  69.834  1.00 43.17           C
ATOM   2831  O    PHE B  67      11.657  59.886  69.296  1.00 43.17           O
ATOM   2832  CB   PHE B  67      12.343  57.337  71.276  1.00 20.00           C
ATOM   2833  CG   PHE B  67      12.326  55.837  71.278  1.00 20.00           C
ATOM   2834  CD1  PHE B  67      13.432  55.138  71.745  1.00 20.00           C
ATOM   2835  CD2  PHE B  67      11.214  55.156  70.809  1.00 20.00           C
ATOM   2836  CE1  PHE B  67      13.421  53.750  71.742  1.00 20.00           C
ATOM   2837  CE2  PHE B  67      11.211  53.764  70.810  1.00 20.00           C
ATOM   2838  CZ   PHE B  67      12.312  53.057  71.276  1.00 20.00           C
ATOM   2839  N    GLY B  68      13.590  60.081  70.440  1.00 50.61           N
ATOM   2840  CA   GLY B  68      13.525  61.537  70.425  1.00 50.61           C
ATOM   2841  C    GLY B  68      14.874  62.162  70.786  1.00 50.61           C
ATOM   2842  O    GLY B  68      15.882  61.489  70.958  1.00 50.61           O
ATOM   2843  N    VAL B  69      14.880  63.506  70.857  1.00 42.75           N
ATOM   2844  CA   VAL B  69      16.116  64.201  71.197  1.00 42.75           C
ATOM   2845  C    VAL B  69      16.193  64.516  72.692  1.00 42.75           C
ATOM   2846  O    VAL B  69      15.211  64.473  73.422  1.00 42.75           O
ATOM   2847  CB   VAL B  69      16.174  65.497  70.388  1.00 36.53           C
ATOM   2848  CG1  VAL B  69      17.277  66.402  70.934  1.00 36.53           C
ATOM   2849  CG2  VAL B  69      16.458  65.187  68.930  0.00 36.53           C
```

FIG. 1-47

| | | | | | | | | | | |
|---|---|---|---|---|---|---|---|---|---|---|
| ATOM | 2850 | N | VAL | B | 70 | 17.426 | 64.800 | 73.150 | 1.00 37.08 | N |
| ATOM | 2851 | CA | VAL | B | 70 | 17.615 | 65.114 | 74.560 | 1.00 37.08 | C |
| ATOM | 2852 | C | VAL | B | 70 | 18.339 | 66.449 | 74.747 | 1.00 37.08 | C |
| ATOM | 2853 | O | VAL | B | 70 | 19.486 | 66.631 | 74.362 | 1.00 37.08 | O |
| ATOM | 2854 | CB | VAL | B | 70 | 18.430 | 63.987 | 75.195 | 1.00 29.90 | C |
| ATOM | 2855 | CG1 | VAL | B | 70 | 18.765 | 64.338 | 76.643 | 1.00 29.90 | C |
| ATOM | 2856 | CG2 | VAL | B | 70 | 17.638 | 62.693 | 75.164 | 1.00 29.90 | C |
| ATOM | 2857 | N | TYR | B | 71 | 17.605 | 67.418 | 75.326 | 1.00 36.25 | N |
| ATOM | 2858 | CA | TYR | B | 71 | 18.199 | 68.729 | 75.555 | 1.00 36.25 | C |
| ATOM | 2859 | C | TYR | B | 71 | 18.782 | 68.845 | 76.965 | 1.00 36.25 | C |
| ATOM | 2860 | O | TYR | B | 71 | 18.431 | 68.103 | 77.874 | 1.00 36.25 | O |
| ATOM | 2861 | CB | TYR | B | 71 | 17.113 | 69.787 | 75.351 | 1.00 47.16 | C |
| ATOM | 2862 | CG | TYR | B | 71 | 16.428 | 69.563 | 74.049 | 1.00 47.16 | C |
| ATOM | 2863 | CD1 | TYR | B | 71 | 15.421 | 68.609 | 73.950 | 1.00 47.16 | C |
| ATOM | 2864 | CD2 | TYR | B | 71 | 16.783 | 70.313 | 72.927 | 1.00 47.16 | C |
| ATOM | 2865 | CE1 | TYR | B | 71 | 14.770 | 68.404 | 72.742 | 1.00 47.16 | C |
| ATOM | 2866 | CE2 | TYR | B | 71 | 16.133 | 70.108 | 71.718 | 1.00 47.16 | C |
| ATOM | 2867 | CZ | TYR | B | 71 | 15.130 | 69.160 | 71.624 | 1.00 47.16 | C |
| ATOM | 2868 | OH | TYR | B | 71 | 14.462 | 68.967 | 70.431 | 1.00 47.16 | O |
| ATOM | 2869 | N | GLN | B | 72 | 19.607 | 69.842 | 77.260 | 1.00 45.35 | N |
| ATOM | 2870 | CA | GLN | B | 72 | 20.009 | 70.092 | 78.634 | 1.00 45.35 | C |
| ATOM | 2871 | C | GLN | B | 72 | 19.556 | 71.524 | 78.937 | 1.00 45.35 | C |
| ATOM | 2872 | O | GLN | B | 72 | 19.410 | 72.340 | 78.020 | 1.00 45.35 | O |
| ATOM | 2873 | CB | GLN | B | 72 | 21.515 | 69.956 | 78.797 | 1.00 46.73 | C |
| ATOM | 2874 | CG | GLN | B | 72 | 22.239 | 71.264 | 78.969 | 1.00 46.73 | C |
| ATOM | 2875 | CD | GLN | B | 72 | 23.283 | 71.198 | 80.065 | 1.00 46.73 | C |
| ATOM | 2876 | OE1 | GLN | B | 72 | 24.143 | 72.074 | 80.161 | 1.00 46.73 | O |
| ATOM | 2877 | NE2 | GLN | B | 72 | 23.213 | 70.158 | 80.904 | 1.00 46.73 | N |
| ATOM | 2878 | N | ALA | B | 73 | 19.317 | 71.846 | 80.202 | 1.00 28.13 | N |
| ATOM | 2879 | CA | ALA | B | 73 | 18.861 | 73.186 | 80.499 | 1.00 28.13 | C |
| ATOM | 2880 | C | ALA | B | 73 | 19.069 | 73.593 | 81.933 | 1.00 28.13 | C |
| ATOM | 2881 | O | ALA | B | 73 | 19.506 | 72.799 | 82.776 | 1.00 28.13 | O |
| ATOM | 2882 | CB | ALA | B | 73 | 17.405 | 73.328 | 80.129 | 1.00 26.55 | C |
| ATOM | 2883 | N | LYS | B | 74 | 18.727 | 74.849 | 82.198 | 1.00 42.42 | N |
| ATOM | 2884 | CA | LYS | B | 74 | 18.898 | 75.434 | 83.515 | 1.00 42.42 | C |
| ATOM | 2885 | C | LYS | B | 74 | 17.608 | 76.043 | 84.058 | 1.00 42.42 | C |
| ATOM | 2886 | O | LYS | B | 74 | 17.096 | 77.025 | 83.511 | 1.00 42.42 | O |
| ATOM | 2887 | CB | LYS | B | 74 | 19.980 | 76.518 | 83.446 | 1.00 65.58 | C |
| ATOM | 2888 | CG | LYS | B | 74 | 20.341 | 77.120 | 84.788 | 1.00 65.58 | C |
| ATOM | 2889 | CD | LYS | B | 74 | 20.980 | 78.494 | 84.610 | 1.00 65.58 | C |
| ATOM | 2890 | CE | LYS | B | 74 | 21.459 | 79.062 | 85.953 | 1.00 65.58 | C |
| ATOM | 2891 | NZ | LYS | B | 74 | 21.878 | 80.496 | 85.840 | 1.00 65.58 | N |
| ATOM | 2892 | N | LEU | B | 75 | 17.088 | 75.457 | 85.133 | 1.00 44.40 | N |
| ATOM | 2893 | CA | LEU | B | 75 | 15.878 | 75.976 | 85.758 | 1.00 44.40 | C |
| ATOM | 2894 | C | LEU | B | 75 | 16.185 | 77.439 | 86.074 | 1.00 44.40 | C |
| ATOM | 2895 | O | LEU | B | 75 | 17.188 | 77.741 | 86.727 | 1.00 44.40 | O |
| ATOM | 2896 | CB | LEU | B | 75 | 15.563 | 75.216 | 87.057 | 1.00 30.55 | C |
| ATOM | 2897 | CG | LEU | B | 75 | 15.393 | 73.684 | 87.016 | 1.00 30.55 | C |
| ATOM | 2898 | CD1 | LEU | B | 75 | 14.893 | 73.192 | 88.366 | 0.00 30.55 | C |
| ATOM | 2899 | CD2 | LEU | B | 75 | 14.428 | 73.293 | 85.904 | 1.00 30.55 | C |
| ATOM | 2900 | N | CYS | B | 76 | 15.345 | 78.354 | 85.610 | 1.00 49.50 | N |
| ATOM | 2901 | CA | CYS | B | 76 | 15.613 | 79.756 | 85.876 | 1.00 49.50 | C |
| ATOM | 2902 | C | CYS | B | 76 | 15.795 | 80.076 | 87.359 | 1.00 49.50 | C |
| ATOM | 2903 | O | CYS | B | 76 | 16.826 | 80.632 | 87.735 | 1.00 49.50 | O |
| ATOM | 2904 | CB | CYS | B | 76 | 14.540 | 80.640 | 85.243 | 1.00 37.27 | C |
| ATOM | 2905 | SG | CYS | B | 76 | 14.594 | 80.599 | 83.398 | 1.00 37.27 | S |
| ATOM | 2906 | N | ASP | B | 77 | 14.852 | 79.724 | 88.226 | 1.00 50.48 | N |
| ATOM | 2907 | CA | ASP | B | 77 | 15.083 | 80.066 | 89.629 | 1.00 50.48 | C |
| ATOM | 2908 | C | ASP | B | 77 | 16.235 | 79.301 | 90.278 | 1.00 50.48 | C |
| ATOM | 2909 | O | ASP | B | 77 | 17.333 | 79.832 | 90.404 | 1.00 50.48 | O |
| ATOM | 2910 | CB | ASP | B | 77 | 13.808 | 79.924 | 90.487 | 1.00 89.67 | C |
| ATOM | 2911 | CG | ASP | B | 77 | 13.106 | 78.584 | 90.311 | 1.00 89.67 | C |

FIG. 1-48

| | | | | | | | | | |
|---|---|---|---|---|---|---|---|---|---|
| ATOM | 2912 | OD1 | ASP | B | 77 | 13.735 | 77.614 | 89.803 | 1.00 89.67 | O |
| ATOM | 2913 | OD2 | ASP | B | 77 | 11.913 | 78.504 | 90.703 | 1.00 89.67 | O |
| ATOM | 2914 | N | SER | B | 78 | 16.002 | 78.061 | 90.690 | 1.00 48.72 | N |
| ATOM | 2915 | CA | SER | B | 78 | 17.057 | 77.280 | 91.333 | 1.00 48.72 | C |
| ATOM | 2916 | C | SER | B | 78 | 18.365 | 77.318 | 90.547 | 1.00 48.72 | C |
| ATOM | 2917 | O | SER | B | 78 | 19.433 | 77.094 | 91.102 | 1.00 48.72 | O |
| ATOM | 2918 | CB | SER | B | 78 | 16.615 | 75.818 | 91.513 | 1.00 60.46 | C |
| ATOM | 2919 | OG | SER | B | 78 | 16.594 | 75.116 | 90.277 | 1.00 60.46 | O |
| ATOM | 2920 | N | GLY | B | 79 | 18.281 | 77.592 | 89.252 | 1.00 53.55 | N |
| ATOM | 2921 | CA | GLY | B | 79 | 19.490 | 77.637 | 88.452 | 1.00 53.55 | C |
| ATOM | 2922 | C | GLY | B | 79 | 20.117 | 76.267 | 88.238 | 1.00 53.55 | C |
| ATOM | 2923 | O | GLY | B | 79 | 21.197 | 76.156 | 87.654 | 1.00 53.55 | O |
| ATOM | 2924 | N | GLU | B | 80 | 19.447 | 75.214 | 88.696 | 1.00 51.07 | N |
| ATOM | 2925 | CA | GLU | B | 80 | 19.975 | 73.860 | 88.534 | 1.00 51.07 | C |
| ATOM | 2926 | C | GLU | B | 80 | 19.954 | 73.386 | 87.081 | 1.00 51.07 | C |
| ATOM | 2927 | O | GLU | B | 80 | 19.295 | 73.982 | 86.219 | 1.00 51.07 | O |
| ATOM | 2928 | CB | GLU | B | 80 | 19.177 | 72.886 | 89.387 | 1.00 57.03 | C |
| ATOM | 2929 | CG | GLU | B | 80 | 19.187 | 73.210 | 90.857 | 1.00 57.03 | C |
| ATOM | 2930 | CD | GLU | B | 80 | 18.311 | 72.259 | 91.650 | 1.00 57.03 | C |
| ATOM | 2931 | OE1 | GLU | B | 80 | 18.490 | 71.026 | 91.496 | 1.00 57.03 | O |
| ATOM | 2932 | OE2 | GLU | B | 80 | 17.448 | 72.741 | 92.424 | 1.00 57.03 | O |
| ATOM | 2933 | N | LEU | B | 81 | 20.685 | 72.310 | 86.815 | 1.00 36.12 | N |
| ATOM | 2934 | CA | LEU | B | 81 | 20.746 | 71.758 | 85.475 | 1.00 36.12 | C |
| ATOM | 2935 | C | LEU | B | 81 | 19.886 | 70.514 | 85.404 | 1.00 36.12 | C |
| ATOM | 2936 | O | LEU | B | 81 | 19.949 | 69.631 | 86.265 | 1.00 36.12 | O |
| ATOM | 2937 | CB | LEU | B | 81 | 22.188 | 71.426 | 85.094 | 1.00 49.98 | C |
| ATOM | 2938 | CG | LEU | B | 81 | 23.133 | 72.634 | 85.029 | 1.00 49.98 | C |
| ATOM | 2939 | CD1 | LEU | B | 81 | 24.560 | 72.157 | 84.770 | 1.00 49.98 | C |
| ATOM | 2940 | CD2 | LEU | B | 81 | 22.681 | 73.587 | 83.923 | 1.00 49.98 | C |
| ATOM | 2941 | N | VAL | B | 82 | 19.071 | 70.461 | 84.363 | 1.00 36.66 | N |
| ATOM | 2942 | CA | VAL | B | 82 | 18.168 | 69.351 | 84.157 | 1.00 36.66 | C |
| ATOM | 2943 | C | VAL | B | 82 | 18.322 | 68.927 | 82.718 | 1.00 36.66 | C |
| ATOM | 2944 | O | VAL | B | 82 | 18.778 | 69.712 | 81.882 | 1.00 36.66 | O |
| ATOM | 2945 | CB | VAL | B | 82 | 16.695 | 69.783 | 84.391 | 1.00 30.54 | C |
| ATOM | 2946 | CG1 | VAL | B | 82 | 16.537 | 70.327 | 85.788 | 1.00 30.54 | C |
| ATOM | 2947 | CG2 | VAL | B | 82 | 16.281 | 70.847 | 83.364 | 1.00 30.54 | C |
| ATOM | 2948 | N | ALA | B | 83 | 17.936 | 67.689 | 82.439 | 1.00 27.82 | N |
| ATOM | 2949 | CA | ALA | B | 83 | 17.998 | 67.142 | 81.098 | 1.00 27.82 | C |
| ATOM | 2950 | C | ALA | B | 83 | 16.566 | 66.993 | 80.629 | 1.00 27.82 | C |
| ATOM | 2951 | O | ALA | B | 83 | 15.691 | 66.620 | 81.412 | 1.00 27.82 | O |
| ATOM | 2952 | CB | ALA | B | 83 | 18.672 | 65.792 | 81.129 | 1.00 31.27 | C |
| ATOM | 2953 | N | ILE | B | 84 | 16.309 | 67.297 | 79.362 | 1.00 35.11 | N |
| ATOM | 2954 | CA | ILE | B | 84 | 14.956 | 67.157 | 78.853 | 1.00 35.11 | C |
| ATOM | 2955 | C | ILE | B | 84 | 14.922 | 66.132 | 77.742 | 1.00 35.11 | C |
| ATOM | 2956 | O | ILE | B | 84 | 15.550 | 66.311 | 76.711 | 1.00 35.11 | O |
| ATOM | 2957 | CB | ILE | B | 84 | 14.388 | 68.482 | 78.318 | 1.00 31.83 | C |
| ATOM | 2958 | CG1 | ILE | B | 84 | 14.429 | 69.555 | 79.403 | 1.00 31.83 | C |
| ATOM | 2959 | CG2 | ILE | B | 84 | 12.940 | 68.282 | 77.902 | 1.00 31.83 | C |
| ATOM | 2960 | CD1 | ILE | B | 84 | 13.780 | 70.870 | 78.988 | 1.00 31.83 | C |
| ATOM | 2961 | N | LYS | B | 85 | 14.194 | 65.050 | 77.969 | 1.00 41.14 | N |
| ATOM | 2962 | CA | LYS | B | 85 | 14.065 | 63.990 | 76.990 | 1.00 41.14 | C |
| ATOM | 2963 | C | LYS | B | 85 | 12.688 | 64.137 | 76.372 | 1.00 41.14 | C |
| ATOM | 2964 | O | LYS | B | 85 | 11.681 | 63.850 | 77.015 | 1.00 41.14 | O |
| ATOM | 2965 | CB | LYS | B | 85 | 14.188 | 62.630 | 77.672 | 1.00 32.95 | C |
| ATOM | 2966 | CG | LYS | B | 85 | 14.010 | 61.453 | 76.737 | 1.00 32.95 | C |
| ATOM | 2967 | CD | LYS | B | 85 | 14.173 | 60.119 | 77.454 | 1.00 32.95 | C |
| ATOM | 2968 | CE | LYS | B | 85 | 14.088 | 58.975 | 76.459 | 1.00 32.95 | C |
| ATOM | 2969 | NZ | LYS | B | 85 | 14.169 | 57.645 | 77.115 | 1.00 32.95 | N |
| ATOM | 2970 | N | LYS | B | 86 | 12.660 | 64.578 | 75.121 | 1.00 36.80 | N |
| ATOM | 2971 | CA | LYS | B | 86 | 11.430 | 64.804 | 74.374 | 1.00 36.80 | C |
| ATOM | 2972 | C | LYS | B | 86 | 11.157 | 63.669 | 73.400 | 1.00 36.80 | C |
| ATOM | 2973 | O | LYS | B | 86 | 11.937 | 63.453 | 72.488 | 1.00 36.80 | O |

FIG. 1-49

```
ATOM   2974  CB   LYS B  86      11.587  66.116  73.606  1.00  26.01           C
ATOM   2975  CG   LYS B  86      10.462  66.516  72.697  1.00  26.01           C
ATOM   2976  CD   LYS B  86      10.774  67.890  72.133  1.00  26.01           C
ATOM   2977  CE   LYS B  86       9.646  68.431  71.261  1.00  26.01           C
ATOM   2978  NZ   LYS B  86       9.983  69.765  70.687  0.00  26.01           N
ATOM   2979  N    VAL B  87      10.061  62.944  73.577  1.00  28.90           N
ATOM   2980  CA   VAL B  87       9.747  61.852  72.660  1.00  28.90           C
ATOM   2981  C    VAL B  87       8.361  62.065  72.053  1.00  28.90           C
ATOM   2982  O    VAL B  87       7.528  62.748  72.630  1.00  28.90           O
ATOM   2983  CB   VAL B  87       9.772  60.494  73.377  1.00  34.71           C
ATOM   2984  CG1  VAL B  87      10.979  60.419  74.298  1.00  34.71           C
ATOM   2985  CG2  VAL B  87       8.496  60.287  74.146  1.00  34.71           C
ATOM   2986  N    LEU B  88       8.109  61.489  70.884  1.00  46.68           N
ATOM   2987  CA   LEU B  88       6.815  61.659  70.244  1.00  46.68           C
ATOM   2988  C    LEU B  88       5.822  60.776  70.970  1.00  46.68           C
ATOM   2989  O    LEU B  88       6.039  59.576  71.105  1.00  46.68           O
ATOM   2990  CB   LEU B  88       6.905  61.265  68.777  1.00  48.05           C
ATOM   2991  CG   LEU B  88       5.891  61.882  67.808  1.00  48.05           C
ATOM   2992  CD1  LEU B  88       6.239  61.414  66.415  1.00  48.05           C
ATOM   2993  CD2  LEU B  88       4.473  61.472  68.169  0.00  48.05           C
ATOM   2994  N    GLN B  89       4.720  61.355  71.429  1.00  48.15           N
ATOM   2995  CA   GLN B  89       3.754  60.571  72.185  1.00  48.15           C
ATOM   2996  C    GLN B  89       2.343  60.623  71.632  1.00  48.15           C
ATOM   2997  O    GLN B  89       1.812  61.703  71.374  1.00  48.15           O
ATOM   2998  CB   GLN B  89       3.759  61.041  73.643  0.00  59.22           C
ATOM   2999  CG   GLN B  89       2.735  60.368  74.534  1.00  59.22           C
ATOM   3000  CD   GLN B  89       2.763  58.847  74.416  1.00  59.22           C
ATOM   3001  OE1  GLN B  89       3.734  58.265  73.921  1.00  59.22           O
ATOM   3002  NE2  GLN B  89       1.696  58.196  74.882  1.00  59.22           N
ATOM   3003  N    ASP B  90       1.736  59.452  71.452  1.00  61.58           N
ATOM   3004  CA   ASP B  90       0.367  59.379  70.946  1.00  61.58           C
ATOM   3005  C    ASP B  90      -0.660  59.553  72.072  1.00  61.58           C
ATOM   3006  O    ASP B  90      -0.778  58.696  72.970  1.00  61.58           O
ATOM   3007  CB   ASP B  90       0.114  58.049  70.242  1.00  58.64           C
ATOM   3008  CG   ASP B  90      -1.346  57.892  69.812  1.00  58.64           C
ATOM   3009  OD1  ASP B  90      -2.219  57.757  70.704  1.00  58.64           O
ATOM   3010  OD2  ASP B  90      -1.622  57.915  68.585  1.00  58.64           O
ATOM   3011  N    LYS B  91      -1.401  60.663  72.003  1.00  58.28           N
ATOM   3012  CA   LYS B  91      -2.428  61.012  72.987  1.00  58.28           C
ATOM   3013  C    LYS B  91      -3.242  59.802  73.441  1.00  58.28           C
ATOM   3014  O    LYS B  91      -3.607  59.708  74.625  1.00  58.28           O
ATOM   3015  CB   LYS B  91      -3.355  62.077  72.414  0.00  35.69           C
ATOM   3016  N    ARG B  92      -3.520  58.885  72.509  1.00  52.70           N
ATOM   3017  CA   ARG B  92      -4.287  57.680  72.821  1.00  52.70           C
ATOM   3018  C    ARG B  92      -3.540  56.753  73.799  1.00  52.70           C
ATOM   3019  O    ARG B  92      -3.967  56.589  74.945  1.00  52.70           O
ATOM   3020  CB   ARG B  92      -4.638  56.926  71.540  0.00  35.69           C
ATOM   3021  N    PHE B  93      -2.433  56.149  73.354  1.00  72.05           N
ATOM   3022  CA   PHE B  93      -1.647  55.243  74.205  1.00  72.05           C
ATOM   3023  C    PHE B  93      -1.095  55.968  75.446  1.00  72.05           C
ATOM   3024  O    PHE B  93      -0.996  57.209  75.461  1.00  72.05           O
ATOM   3025  CB   PHE B  93      -0.501  54.643  73.402  0.00  35.69           C
ATOM   3026  N    LYS B  94      -0.761  55.200  76.487  1.00  45.43           N
ATOM   3027  CA   LYS B  94      -0.200  55.765  77.715  1.00  45.43           C
ATOM   3028  C    LYS B  94       1.288  55.431  77.688  1.00  45.43           C
ATOM   3029  O    LYS B  94       1.656  54.272  77.491  1.00  45.43           O
ATOM   3030  CB   LYS B  94      -0.845  55.128  78.948  1.00  48.79           C
ATOM   3031  CG   LYS B  94      -1.028  56.084  80.125  1.00  48.79           C
ATOM   3032  CD   LYS B  94      -2.079  57.136  79.804  0.00  48.79           C
ATOM   3033  CE   LYS B  94      -2.347  58.045  80.991  0.00  48.79           C
ATOM   3034  NZ   LYS B  94      -3.393  59.058  80.676  0.00  48.79           N
ATOM   3035  N    ASN B  95       2.138  56.436  77.891  1.00  32.06           N
```

FIG. 1-50

| | | | | | | | | | |
|---|---|---|---|---|---|---|---|---|---|
| ATOM | 3036 | CA | ASN | B | 95 | 3.588 | 56.240 | 77.848 | 1.00 32.06 | C |
| ATOM | 3037 | C | ASN | B | 95 | 4.174 | 55.443 | 78.998 | 1.00 32.06 | C |
| ATOM | 3038 | O | ASN | B | 95 | 4.227 | 55.911 | 80.135 | 1.00 32.06 | O |
| ATOM | 3039 | CB | ASN | B | 95 | 4.301 | 57.581 | 77.771 | 1.00 26.97 | C |
| ATOM | 3040 | CG | ASN | B | 95 | 5.794 | 57.426 | 77.668 | 1.00 26.97 | C |
| ATOM | 3041 | OD1 | ASN | B | 95 | 6.446 | 56.944 | 78.589 | 1.00 26.97 | O |
| ATOM | 3042 | ND2 | ASN | B | 95 | 6.346 | 57.828 | 76.536 | 1.00 26.97 | N |
| ATOM | 3043 | N | ARG | B | 96 | 4.662 | 54.248 | 78.685 | 1.00 30.08 | N |
| ATOM | 3044 | CA | ARG | B | 96 | 5.224 | 53.375 | 79.696 | 1.00 30.08 | C |
| ATOM | 3045 | C | ARG | B | 96 | 6.360 | 53.971 | 80.511 | 1.00 30.08 | C |
| ATOM | 3046 | O | ARG | B | 96 | 6.392 | 53.827 | 81.740 | 1.00 30.08 | O |
| ATOM | 3047 | CB | ARG | B | 96 | 5.689 | 52.073 | 79.060 | 1.00 46.35 | C |
| ATOM | 3048 | CG | ARG | B | 96 | 5.092 | 50.883 | 79.749 | 1.00 46.35 | C |
| ATOM | 3049 | CD | ARG | B | 96 | 6.126 | 49.873 | 80.138 | 1.00 46.35 | C |
| ATOM | 3050 | NE | ARG | B | 96 | 6.598 | 49.087 | 79.001 | 1.00 46.35 | N |
| ATOM | 3051 | CZ | ARG | B | 96 | 5.826 | 48.302 | 78.252 | 1.00 46.35 | C |
| ATOM | 3052 | NH1 | ARG | B | 96 | 4.526 | 48.204 | 78.506 | 1.00 46.35 | N |
| ATOM | 3053 | NH2 | ARG | B | 96 | 6.361 | 47.576 | 77.275 | 1.00 46.35 | N |
| ATOM | 3054 | N | GLU | B | 97 | 7.290 | 54.634 | 79.833 | 1.00 20.49 | N |
| ATOM | 3055 | CA | GLU | B | 97 | 8.427 | 55.230 | 80.507 | 1.00 20.49 | C |
| ATOM | 3056 | C | GLU | B | 97 | 7.955 | 56.234 | 81.547 | 1.00 20.49 | C |
| ATOM | 3057 | O | GLU | B | 97 | 8.364 | 56.173 | 82.698 | 1.00 20.49 | O |
| ATOM | 3058 | CB | GLU | B | 97 | 9.361 | 55.895 | 79.488 | 1.00 29.56 | C |
| ATOM | 3059 | CG | GLU | B | 97 | 10.623 | 56.510 | 80.082 | 1.00 29.56 | C |
| ATOM | 3060 | CD | GLU | B | 97 | 11.613 | 56.970 | 79.026 | 1.00 29.56 | C |
| ATOM | 3061 | OE1 | GLU | B | 97 | 12.707 | 57.439 | 79.389 | 1.00 29.56 | O |
| ATOM | 3062 | OE2 | GLU | B | 97 | 11.303 | 56.865 | 77.829 | 1.00 29.56 | O |
| ATOM | 3063 | N | LEU | B | 98 | 7.087 | 57.153 | 81.154 | 1.00 20.95 | N |
| ATOM | 3064 | CA | LEU | B | 98 | 6.583 | 58.129 | 82.109 | 1.00 20.95 | C |
| ATOM | 3065 | C | LEU | B | 98 | 5.951 | 57.376 | 83.266 | 1.00 20.95 | C |
| ATOM | 3066 | O | LEU | B | 98 | 6.198 | 57.661 | 84.432 | 1.00 20.95 | O |
| ATOM | 3067 | CB | LEU | B | 98 | 5.520 | 59.021 | 81.459 | 1.00 22.17 | C |
| ATOM | 3068 | CG | LEU | B | 98 | 4.680 | 59.879 | 82.410 | 1.00 22.17 | C |
| ATOM | 3069 | CD1 | LEU | B | 98 | 5.549 | 60.878 | 83.141 | 1.00 22.17 | C |
| ATOM | 3070 | CD2 | LEU | B | 98 | 3.629 | 60.590 | 81.624 | 1.00 22.17 | C |
| ATOM | 3071 | N | GLN | B | 99 | 5.126 | 56.405 | 82.909 | 1.00 28.37 | N |
| ATOM | 3072 | CA | GLN | B | 99 | 4.422 | 55.592 | 83.871 | 1.00 28.37 | C |
| ATOM | 3073 | C | GLN | B | 99 | 5.297 | 55.076 | 85.007 | 1.00 28.37 | C |
| ATOM | 3074 | O | GLN | B | 99 | 4.988 | 55.308 | 86.174 | 1.00 28.37 | O |
| ATOM | 3075 | CB | GLN | B | 99 | 3.744 | 54.413 | 83.151 | 1.00 81.31 | C |
| ATOM | 3076 | CG | GLN | B | 99 | 2.963 | 53.459 | 84.077 | 1.00 81.31 | C |
| ATOM | 3077 | CD | GLN | B | 99 | 2.314 | 52.283 | 83.339 | 1.00 81.31 | C |
| ATOM | 3078 | OE1 | GLN | B | 99 | 1.505 | 51.546 | 83.918 | 1.00 81.31 | O |
| ATOM | 3079 | NE2 | GLN | B | 99 | 2.670 | 52.097 | 82.069 | 1.00 81.31 | N |
| ATOM | 3080 | N | ILE | B | 100 | 6.389 | 54.383 | 84.683 | 1.00 33.97 | N |
| ATOM | 3081 | CA | ILE | B | 100 | 7.226 | 53.832 | 85.752 | 1.00 33.97 | C |
| ATOM | 3082 | C | ILE | B | 100 | 8.135 | 54.860 | 86.428 | 1.00 33.97 | C |
| ATOM | 3083 | O | ILE | B | 100 | 8.454 | 54.719 | 87.597 | 1.00 33.97 | O |
| ATOM | 3084 | CB | ILE | B | 100 | 8.079 | 52.591 | 85.279 | 1.00 30.63 | C |
| ATOM | 3085 | CG1 | ILE | B | 100 | 7.531 | 51.265 | 84.745 | 1.00 30.63 | C |
| ATOM | 3086 | CG2 | ILE | B | 100 | 8.970 | 52.276 | 86.495 | 1.00 30.63 | C |
| ATOM | 3087 | CD1 | ILE | B | 100 | 8.319 | 50.146 | 84.062 | 1.00 30.63 | C |
| ATOM | 3088 | N | MET | B | 101 | 8.548 | 55.895 | 85.706 | 1.00 30.86 | N |
| ATOM | 3089 | CA | MET | B | 101 | 9.402 | 56.931 | 86.295 | 1.00 30.86 | C |
| ATOM | 3090 | C | MET | B | 101 | 8.659 | 57.539 | 87.482 | 1.00 30.86 | C |
| ATOM | 3091 | O | MET | B | 101 | 9.196 | 57.679 | 88.581 | 1.00 30.86 | O |
| ATOM | 3092 | CB | MET | B | 101 | 9.691 | 58.039 | 85.273 | 1.00 50.72 | C |
| ATOM | 3093 | CG | MET | B | 101 | 10.661 | 57.676 | 84.151 | 1.00 50.72 | C |
| ATOM | 3094 | SD | MET | B | 101 | 12.380 | 58.030 | 84.563 | 1.00 50.72 | S |
| ATOM | 3095 | CE | MET | B | 101 | 12.699 | 56.669 | 85.726 | 1.00 50.72 | C |
| ATOM | 3096 | N | ARG | B | 102 | 7.409 | 57.897 | 87.225 | 1.00 36.65 | N |
| ATOM | 3097 | CA | ARG | B | 102 | 6.518 | 58.505 | 88.202 | 1.00 36.65 | C |

FIG. 1-51

| | | | | | | | | | | |
|---|---|---|---|---|---|---|---|---|---|---|
| ATOM | 3098 | C | ARG | B | 102 | 6.444 | 57.845 | 89.579 | 1.00 36.65 | C |
| ATOM | 3099 | O | ARG | B | 102 | 6.241 | 58.534 | 90.586 | 1.00 36.65 | O |
| ATOM | 3100 | CB | ARG | B | 102 | 5.119 | 58.575 | 87.598 | 1.00 36.45 | C |
| ATOM | 3101 | CG | ARG | B | 102 | 4.998 | 59.626 | 86.541 | 1.00 36.45 | C |
| ATOM | 3102 | CD | ARG | B | 102 | 4.463 | 60.872 | 87.148 | 1.00 36.45 | C |
| ATOM | 3103 | NE | ARG | B | 102 | 3.049 | 60.960 | 86.853 | 1.00 36.45 | N |
| ATOM | 3104 | CZ | ARG | B | 102 | 2.211 | 61.795 | 87.451 | 1.00 36.45 | C |
| ATOM | 3105 | NH1 | ARG | B | 102 | 2.653 | 62.621 | 88.400 | 1.00 36.45 | N |
| ATOM | 3106 | NH2 | ARG | B | 102 | 0.936 | 61.813 | 87.080 | 1.00 36.45 | N |
| ATOM | 3107 | N | LYS | B | 103 | 6.600 | 56.523 | 89.619 | 1.00 27.44 | N |
| ATOM | 3108 | CA | LYS | B | 103 | 6.527 | 55.789 | 90.872 | 1.00 27.44 | C |
| ATOM | 3109 | C | LYS | B | 103 | 7.895 | 55.353 | 91.399 | 1.00 27.44 | C |
| ATOM | 3110 | O | LYS | B | 103 | 7.997 | 54.433 | 92.213 | 1.00 27.44 | O |
| ATOM | 3111 | CB | LYS | B | 103 | 5.623 | 54.561 | 90.700 | 1.00 46.06 | C |
| ATOM | 3112 | CG | LYS | B | 103 | 6.336 | 53.326 | 90.201 | 1.00 46.06 | C |
| ATOM | 3113 | CD | LYS | B | 103 | 5.435 | 52.108 | 90.221 | 1.00 46.06 | C |
| ATOM | 3114 | CE | LYS | B | 103 | 4.335 | 52.221 | 89.177 | 1.00 46.06 | C |
| ATOM | 3115 | NZ | LYS | B | 103 | 3.732 | 50.878 | 88.899 | 1.00 46.06 | N |
| ATOM | 3116 | N | LEU | B | 104 | 8.946 | 56.020 | 90.945 | 1.00 26.13 | N |
| ATOM | 3117 | CA | LEU | B | 104 | 10.290 | 55.675 | 91.364 | 1.00 26.13 | C |
| ATOM | 3118 | C | LEU | B | 104 | 10.907 | 56.751 | 92.218 | 1.00 26.13 | C |
| ATOM | 3119 | O | LEU | B | 104 | 10.772 | 57.932 | 91.939 | 1.00 26.13 | O |
| ATOM | 3120 | CB | LEU | B | 104 | 11.158 | 55.422 | 90.137 | 1.00 27.85 | C |
| ATOM | 3121 | CG | LEU | B | 104 | 11.366 | 53.955 | 89.770 | 1.00 27.85 | C |
| ATOM | 3122 | CD1 | LEU | B | 104 | 10.087 | 53.136 | 89.991 | 1.00 27.85 | C |
| ATOM | 3123 | CD2 | LEU | B | 104 | 11.849 | 53.890 | 88.335 | 1.00 27.85 | C |
| ATOM | 3124 | N | ASP | B | 105 | 11.588 | 56.344 | 93.274 | 1.00 26.38 | N |
| ATOM | 3125 | CA | ASP | B | 105 | 12.217 | 57.308 | 94.151 | 1.00 26.38 | C |
| ATOM | 3126 | C | ASP | B | 105 | 13.330 | 56.642 | 94.941 | 1.00 26.38 | C |
| ATOM | 3127 | O | ASP | B | 105 | 13.104 | 56.090 | 96.010 | 1.00 26.38 | O |
| ATOM | 3128 | CB | ASP | B | 105 | 11.173 | 57.900 | 95.082 | 1.00 48.94 | C |
| ATOM | 3129 | CG | ASP | B | 105 | 11.750 | 58.928 | 96.004 | 1.00 48.94 | C |
| ATOM | 3130 | OD1 | ASP | B | 105 | 12.593 | 59.720 | 95.528 | 1.00 48.94 | O |
| ATOM | 3131 | OD2 | ASP | B | 105 | 11.359 | 58.945 | 97.194 | 1.00 48.94 | O |
| ATOM | 3132 | N | HIS | B | 106 | 14.536 | 56.702 | 94.385 | 1.00 21.83 | N |
| ATOM | 3133 | CA | HIS | B | 106 | 15.719 | 56.097 | 94.978 | 1.00 21.83 | C |
| ATOM | 3134 | C | HIS | B | 106 | 16.930 | 56.981 | 94.695 | 1.00 21.83 | C |
| ATOM | 3135 | O | HIS | B | 106 | 17.095 | 57.479 | 93.591 | 1.00 21.83 | O |
| ATOM | 3136 | CB | HIS | B | 106 | 15.910 | 54.708 | 94.376 | 1.00 30.89 | C |
| ATOM | 3137 | CG | HIS | B | 106 | 16.905 | 53.863 | 95.103 | 1.00 30.89 | C |
| ATOM | 3138 | ND1 | HIS | B | 106 | 18.264 | 53.967 | 94.894 | 1.00 30.89 | N |
| ATOM | 3139 | CD2 | HIS | B | 106 | 16.738 | 52.892 | 96.029 | 1.00 30.89 | C |
| ATOM | 3140 | CE1 | HIS | B | 106 | 18.889 | 53.091 | 95.660 | 1.00 30.89 | C |
| ATOM | 3141 | NE2 | HIS | B | 106 | 17.987 | 52.425 | 96.358 | 1.00 30.89 | N |
| ATOM | 3142 | N | CYS | B | 107 | 17.774 | 57.181 | 95.694 | 1.00 21.99 | N |
| ATOM | 3143 | CA | CYS | B | 107 | 18.940 | 58.036 | 95.537 | 1.00 21.99 | C |
| ATOM | 3144 | C | CYS | B | 107 | 19.835 | 57.623 | 94.386 | 1.00 21.99 | C |
| ATOM | 3145 | O | CYS | B | 107 | 20.590 | 58.440 | 93.861 | 1.00 21.99 | O |
| ATOM | 3146 | CB | CYS | B | 107 | 19.751 | 58.045 | 96.824 | 1.00 28.50 | C |
| ATOM | 3147 | SG | CYS | B | 107 | 20.348 | 56.432 | 97.301 | 1.00 28.50 | S |
| ATOM | 3148 | N | ASN | B | 108 | 19.739 | 56.356 | 93.993 | 1.00 24.69 | N |
| ATOM | 3149 | CA | ASN | B | 108 | 20.547 | 55.824 | 92.911 | 1.00 24.69 | C |
| ATOM | 3150 | C | ASN | B | 108 | 19.831 | 55.690 | 91.583 | 1.00 24.69 | C |
| ATOM | 3151 | O | ASN | B | 108 | 20.191 | 54.855 | 90.765 | 1.00 24.69 | O |
| ATOM | 3152 | CB | ASN | B | 108 | 21.116 | 54.469 | 93.309 | 1.00 25.83 | C |
| ATOM | 3153 | CG | ASN | B | 108 | 22.234 | 54.585 | 94.308 | 1.00 25.83 | C |
| ATOM | 3154 | OD1 | ASN | B | 108 | 22.343 | 53.775 | 95.223 | 1.00 25.83 | O |
| ATOM | 3155 | ND2 | ASN | B | 108 | 23.082 | 55.584 | 94.132 | 1.00 25.83 | N |
| ATOM | 3156 | N | ILE | B | 109 | 18.805 | 56.496 | 91.371 | 1.00 18.34 | N |
| ATOM | 3157 | CA | ILE | B | 109 | 18.084 | 56.467 | 90.110 | 1.00 18.34 | C |
| ATOM | 3158 | C | ILE | B | 109 | 17.802 | 57.902 | 89.718 | 1.00 18.34 | C |
| ATOM | 3159 | O | ILE | B | 109 | 17.457 | 58.712 | 90.573 | 1.00 18.34 | O |

FIG. 1-52

```
ATOM   3160  CB   ILE B 109      16.772  55.677  90.220  1.00 15.88           C
ATOM   3161  CG1  ILE B 109      17.100  54.224  90.540  1.00 15.88           C
ATOM   3162  CG2  ILE B 109      15.991  55.766  88.917  1.00 15.88           C
ATOM   3163  CD1  ILE B 109      15.910  53.321  90.644  1.00 15.88           C
ATOM   3164  N    VAL B 110      17.977  58.220  88.438  1.00 20.08           N
ATOM   3165  CA   VAL B 110      17.743  59.580  87.967  1.00 20.08           C
ATOM   3166  C    VAL B 110      16.286  59.966  88.211  1.00 20.08           C
ATOM   3167  O    VAL B 110      15.372  59.246  87.853  1.00 20.08           O
ATOM   3168  CB   VAL B 110      18.112  59.742  86.453  1.00 24.07           C
ATOM   3169  CG1  VAL B 110      17.350  58.744  85.612  1.00 24.07           C
ATOM   3170  CG2  VAL B 110      17.807  61.155  85.979  1.00 24.07           C
ATOM   3171  N    ARG B 111      16.093  61.115  88.834  1.00 26.42           N
ATOM   3172  CA   ARG B 111      14.775  61.604  89.157  1.00 26.42           C
ATOM   3173  C    ARG B 111      14.046  62.356  88.048  1.00 26.42           C
ATOM   3174  O    ARG B 111      14.624  63.185  87.349  1.00 26.42           O
ATOM   3175  CB   ARG B 111      14.864  62.501  90.395  1.00 68.98           C
ATOM   3176  CG   ARG B 111      13.553  63.185  90.760  1.00 68.98           C
ATOM   3177  CD   ARG B 111      13.666  64.005  92.035  1.00 68.98           C
ATOM   3178  NE   ARG B 111      14.680  65.047  91.911  1.00 68.98           N
ATOM   3179  CZ   ARG B 111      15.002  65.897  92.883  1.00 68.98           C
ATOM   3180  NH1  ARG B 111      14.387  65.835  94.056  0.00 68.98           N
ATOM   3181  NH2  ARG B 111      15.947  66.812  92.680  1.00 68.98           N
ATOM   3182  N    LEU B 112      12.766  62.050  87.889  1.00 24.53           N
ATOM   3183  CA   LEU B 112      11.948  62.750  86.920  1.00 24.53           C
ATOM   3184  C    LEU B 112      11.497  63.976  87.708  1.00 24.53           C
ATOM   3185  O    LEU B 112      10.731  63.847  88.659  1.00 24.53           O
ATOM   3186  CB   LEU B 112      10.737  61.907  86.534  1.00 24.78           C
ATOM   3187  CG   LEU B 112       9.638  62.629  85.747  1.00 24.78           C
ATOM   3188  CD1  LEU B 112      10.146  63.010  84.373  1.00 24.78           C
ATOM   3189  CD2  LEU B 112       8.406  61.725  85.631  1.00 24.78           C
ATOM   3190  N    ARG B 113      11.990  65.156  87.354  1.00 27.71           N
ATOM   3191  CA   ARG B 113      11.594  66.364  88.079  1.00 27.71           C
ATOM   3192  C    ARG B 113      10.203  66.821  87.622  1.00 27.71           C
ATOM   3193  O    ARG B 113       9.351  67.169  88.430  1.00 27.71           O
ATOM   3194  CB   ARG B 113      12.589  67.499  87.824  1.00 55.49           C
ATOM   3195  CG   ARG B 113      14.038  67.077  87.765  1.00 55.49           C
ATOM   3196  CD   ARG B 113      14.657  66.937  89.142  1.00 55.49           C
ATOM   3197  NE   ARG B 113      15.688  67.948  89.388  1.00 55.49           N
ATOM   3198  CZ   ARG B 113      15.442  69.234  89.626  1.00 55.49           C
ATOM   3199  NH1  ARG B 113      14.191  69.683  89.651  1.00 55.49           N
ATOM   3200  NH2  ARG B 113      16.449  70.069  89.857  1.00 55.49           N
ATOM   3201  N    TYR B 114       9.995  66.824  86.310  1.00 41.56           N
ATOM   3202  CA   TYR B 114       8.730  67.243  85.731  1.00 41.56           C
ATOM   3203  C    TYR B 114       8.515  66.511  84.423  1.00 41.56           C
ATOM   3204  O    TYR B 114       9.331  65.701  84.015  1.00 41.56           O
ATOM   3205  CB   TYR B 114       8.753  68.747  85.436  1.00 37.17           C
ATOM   3206  CG   TYR B 114       8.980  69.612  86.641  1.00 37.17           C
ATOM   3207  CD1  TYR B 114       7.989  69.765  87.601  1.00 37.17           C
ATOM   3208  CD2  TYR B 114      10.208  70.240  86.851  1.00 37.17           C
ATOM   3209  CE1  TYR B 114       8.210  70.518  88.743  1.00 37.17           C
ATOM   3210  CE2  TYR B 114      10.441  70.990  87.993  1.00 37.17           C
ATOM   3211  CZ   TYR B 114       9.436  71.122  88.933  1.00 37.17           C
ATOM   3212  OH   TYR B 114       9.657  71.845  90.079  1.00 37.17           O
ATOM   3213  N    PHE B 115       7.395  66.807  83.784  1.00 30.06           N
ATOM   3214  CA   PHE B 115       7.062  66.264  82.482  1.00 30.06           C
ATOM   3215  C    PHE B 115       5.959  67.157  81.965  1.00 30.06           C
ATOM   3216  O    PHE B 115       5.232  67.767  82.742  1.00 30.06           O
ATOM   3217  CB   PHE B 115       6.643  64.781  82.548  1.00 30.07           C
ATOM   3218  CG   PHE B 115       5.346  64.516  83.254  1.00 30.07           C
ATOM   3219  CD1  PHE B 115       4.167  64.372  82.539  1.00 30.07           C
ATOM   3220  CD2  PHE B 115       5.314  64.329  84.627  1.00 30.07           C
ATOM   3221  CE1  PHE B 115       2.977  64.039  83.180  1.00 30.07           C
```

FIG. 1-53

| ATOM | 3222 | CE2 | PHE | B | 115 | 4.124 | 63.995 | 85.277 | 1.00 | 30.07 | C |
|---|---|---|---|---|---|---|---|---|---|---|---|
| ATOM | 3223 | CZ | PHE | B | 115 | 2.958 | 63.849 | 84.550 | 1.00 | 30.07 | C |
| ATOM | 3224 | N | PHE | B | 116 | 5.877 | 67.281 | 80.652 | 1.00 | 31.41 | N |
| ATOM | 3225 | CA | PHE | B | 116 | 4.869 | 68.124 | 80.045 | 1.00 | 31.41 | C |
| ATOM | 3226 | C | PHE | B | 116 | 4.780 | 67.808 | 78.568 | 1.00 | 31.41 | C |
| ATOM | 3227 | O | PHE | B | 116 | 5.650 | 67.134 | 78.031 | 1.00 | 31.41 | O |
| ATOM | 3228 | CB | PHE | B | 116 | 5.213 | 69.605 | 80.282 | 1.00 | 24.12 | C |
| ATOM | 3229 | CG | PHE | B | 116 | 6.529 | 70.058 | 79.687 | 1.00 | 24.12 | C |
| ATOM | 3230 | CD1 | PHE | B | 116 | 6.649 | 70.308 | 78.328 | 1.00 | 24.12 | C |
| ATOM | 3231 | CD2 | PHE | B | 116 | 7.632 | 70.288 | 80.501 | 1.00 | 24.12 | C |
| ATOM | 3232 | CE1 | PHE | B | 116 | 7.854 | 70.783 | 77.786 | 1.00 | 24.12 | C |
| ATOM | 3233 | CE2 | PHE | B | 116 | 8.837 | 70.762 | 79.972 | 1.00 | 24.12 | C |
| ATOM | 3234 | CZ | PHE | B | 116 | 8.946 | 71.011 | 78.612 | 1.00 | 24.12 | C |
| ATOM | 3235 | N | TYR | B | 117 | 3.721 | 68.267 | 77.913 | 1.00 | 37.66 | N |
| ATOM | 3236 | CA | TYR | B | 117 | 3.570 | 68.012 | 76.485 | 1.00 | 37.66 | C |
| ATOM | 3237 | C | TYR | B | 117 | 3.758 | 69.295 | 75.690 | 1.00 | 37.66 | C |
| ATOM | 3238 | O | TYR | B | 117 | 3.533 | 70.389 | 76.205 | 1.00 | 37.66 | O |
| ATOM | 3239 | CB | TYR | B | 117 | 2.200 | 67.402 | 76.184 | 1.00 | 27.23 | C |
| ATOM | 3240 | CG | TYR | B | 117 | 1.917 | 66.165 | 76.994 | 1.00 | 27.23 | C |
| ATOM | 3241 | CD1 | TYR | B | 117 | 1.417 | 66.257 | 78.286 | 1.00 | 27.23 | C |
| ATOM | 3242 | CD2 | TYR | B | 117 | 2.196 | 64.900 | 76.489 | 1.00 | 27.23 | C |
| ATOM | 3243 | CE1 | TYR | B | 117 | 1.204 | 65.131 | 79.055 | 1.00 | 27.23 | C |
| ATOM | 3244 | CE2 | TYR | B | 117 | 1.987 | 63.760 | 77.258 | 1.00 | 27.23 | C |
| ATOM | 3245 | CZ | TYR | B | 117 | 1.494 | 63.888 | 78.539 | 1.00 | 27.23 | C |
| ATOM | 3246 | OH | TYR | B | 117 | 1.326 | 62.775 | 79.323 | 1.00 | 27.23 | O |
| ATOM | 3247 | N | SER | B | 118 | 4.187 | 69.149 | 74.438 | 1.00 | 46.94 | N |
| ATOM | 3248 | CA | SER | B | 118 | 4.414 | 70.287 | 73.550 | 1.00 | 46.94 | C |
| ATOM | 3249 | C | SER | B | 118 | 4.074 | 69.910 | 72.099 | 1.00 | 46.94 | C |
| ATOM | 3250 | O | SER | B | 118 | 4.019 | 68.723 | 71.747 | 1.00 | 46.94 | O |
| ATOM | 3251 | CB | SER | B | 118 | 5.869 | 70.729 | 73.640 | 1.00 | 56.00 | C |
| ATOM | 3252 | OG | SER | B | 118 | 6.714 | 69.722 | 73.110 | 1.00 | 56.00 | O |
| ATOM | 3253 | N | SER | B | 119 | 3.858 | 70.928 | 71.266 | 1.00 | 78.48 | N |
| ATOM | 3254 | CA | SER | B | 119 | 3.492 | 70.733 | 69.860 | 1.00 | 78.48 | C |
| ATOM | 3255 | C | SER | B | 119 | 4.583 | 70.157 | 68.969 | 1.00 | 78.48 | C |
| ATOM | 3256 | O | SER | B | 119 | 5.676 | 70.740 | 68.817 | 1.00 | 78.48 | O |
| ATOM | 3257 | CB | SER | B | 119 | 2.993 | 72.045 | 69.243 | 1.00 | 47.32 | C |
| ATOM | 3258 | OG | SER | B | 119 | 1.600 | 72.185 | 69.455 | 1.00 | 47.32 | O |
| ATOM | 3259 | N | GLY | B | 120 | 4.264 | 69.009 | 68.369 | 1.00 | 100.00 | N |
| ATOM | 3260 | CA | GLY | B | 120 | 5.217 | 68.356 | 67.479 | 1.00 | 100.00 | C |
| ATOM | 3261 | C | GLY | B | 120 | 5.431 | 69.166 | 66.200 | 1.00 | 100.00 | C |
| ATOM | 3262 | O | GLY | B | 120 | 4.695 | 70.089 | 65.880 | 1.00 | 100.00 | O |
| ATOM | 3263 | N | GLU | B | 121 | 6.508 | 68.813 | 65.475 | 1.00 | 91.82 | N |
| ATOM | 3264 | CA | GLU | B | 121 | 6.806 | 69.526 | 64.239 | 1.00 | 91.82 | C |
| ATOM | 3265 | C | GLU | B | 121 | 5.623 | 69.482 | 63.270 | 1.00 | 91.82 | C |
| ATOM | 3266 | O | GLU | B | 121 | 5.507 | 70.268 | 62.338 | 1.00 | 91.82 | O |
| ATOM | 3267 | CB | GLU | B | 121 | 8.033 | 68.876 | 63.596 | 1.00 | 31.03 | C |
| ATOM | 3268 | N | LYS | B | 122 | 4.744 | 68.491 | 63.496 | 1.00 | 74.25 | N |
| ATOM | 3269 | CA | LYS | B | 122 | 3.597 | 68.330 | 62.613 | 1.00 | 74.25 | C |
| ATOM | 3270 | C | LYS | B | 122 | 2.317 | 68.854 | 63.264 | 1.00 | 74.25 | C |
| ATOM | 3271 | O | LYS | B | 122 | 2.327 | 69.478 | 64.316 | 1.00 | 74.25 | O |
| ATOM | 3272 | CB | LYS | B | 122 | 3.447 | 66.843 | 62.292 | 0.00 | 35.69 | C |
| ATOM | 3273 | N | LYS | B | 123 | 1.188 | 68.617 | 62.574 | 1.00 | 83.38 | N |
| ATOM | 3274 | CA | LYS | B | 123 | -0.083 | 69.095 | 63.102 | 1.00 | 83.38 | C |
| ATOM | 3275 | C | LYS | B | 123 | -0.652 | 68.139 | 64.154 | 1.00 | 83.38 | C |
| ATOM | 3276 | O | LYS | B | 123 | -0.767 | 68.466 | 65.328 | 1.00 | 83.38 | O |
| ATOM | 3277 | CB | LYS | B | 123 | -1.062 | 69.232 | 61.935 | 1.00 | 56.49 | C |
| ATOM | 3278 | N | ASP | B | 124 | -1.057 | 66.885 | 63.954 | 1.00 | 86.23 | N |
| ATOM | 3279 | CA | ASP | B | 124 | -1.570 | 66.054 | 65.047 | 1.00 | 86.23 | C |
| ATOM | 3280 | C | ASP | B | 124 | -0.474 | 65.322 | 65.849 | 1.00 | 86.23 | C |
| ATOM | 3281 | O | ASP | B | 124 | -0.759 | 64.317 | 66.500 | 0.00 | 86.23 | O |
| ATOM | 3282 | CB | ASP | B | 124 | -2.568 | 65.045 | 64.495 | 0.00 | 35.69 | C |
| ATOM | 3283 | N | GLU | B | 125 | 0.773 | 65.812 | 65.801 | 1.00 | 71.69 | N |

FIG. 1-54

| | | | | | | | | | |
|---|---|---|---|---|---|---|---|---|---|
| ATOM | 3284 | CA | GLU | B | 125 | 1.853 | 65.158 | 66.558 | 1.00 71.69 | C |
| ATOM | 3285 | C | GLU | B | 125 | 2.221 | 65.936 | 67.813 | 1.00 71.69 | C |
| ATOM | 3286 | O | GLU | B | 125 | 2.446 | 67.147 | 67.768 | 1.00 71.69 | O |
| ATOM | 3287 | CB | GLU | B | 125 | 3.113 | 64.929 | 65.697 | 1.00 71.11 | C |
| ATOM | 3288 | CG | GLU | B | 125 | 3.815 | 66.178 | 65.168 | 1.00 71.11 | C |
| ATOM | 3289 | CD | GLU | B | 125 | 5.144 | 65.846 | 64.459 | 1.00 71.11 | C |
| ATOM | 3290 | OE1 | GLU | B | 125 | 5.177 | 64.913 | 63.601 | 1.00 71.11 | O |
| ATOM | 3291 | OE2 | GLU | B | 125 | 6.161 | 66.525 | 64.760 | 1.00 71.11 | O |
| ATOM | 3292 | N | VAL | B | 126 | 2.266 | 65.234 | 68.938 | 1.00 34.98 | N |
| ATOM | 3293 | CA | VAL | B | 126 | 2.604 | 65.884 | 70.186 | 1.00 34.98 | C |
| ATOM | 3294 | C | VAL | B | 126 | 3.668 | 65.082 | 70.916 | 1.00 34.98 | C |
| ATOM | 3295 | O | VAL | B | 126 | 3.723 | 63.846 | 70.828 | 1.00 34.98 | O |
| ATOM | 3296 | CB | VAL | B | 126 | 1.345 | 66.060 | 71.091 | 1.00 35.27 | C |
| ATOM | 3297 | CG1 | VAL | B | 126 | 0.146 | 66.450 | 70.228 | 1.00 35.27 | C |
| ATOM | 3298 | CG2 | VAL | B | 126 | 1.049 | 64.788 | 71.361 | 1.00 35.27 | C |
| ATOM | 3299 | N | TYR | B | 127 | 4.517 | 65.796 | 71.641 | 1.00 37.11 | N |
| ATOM | 3300 | CA | TYR | B | 127 | 5.581 | 65.152 | 72.371 | 1.00 37.11 | C |
| ATOM | 3301 | C | TYR | B | 127 | 5.386 | 65.159 | 73.866 | 1.00 37.11 | C |
| ATOM | 3302 | O | TYR | B | 127 | 4.664 | 65.983 | 74.415 | 1.00 37.11 | O |
| ATOM | 3303 | CB | TYR | B | 127 | 6.900 | 65.834 | 72.075 | 1.00 69.17 | C |
| ATOM | 3304 | CG | TYR | B | 127 | 7.322 | 65.772 | 70.642 | 1.00 69.17 | C |
| ATOM | 3305 | CD1 | TYR | B | 127 | 7.277 | 66.907 | 69.841 | 1.00 69.17 | C |
| ATOM | 3306 | CD2 | TYR | B | 127 | 7.820 | 64.590 | 70.095 | 1.00 69.17 | C |
| ATOM | 3307 | CE1 | TYR | B | 127 | 7.730 | 66.878 | 68.530 | 1.00 69.17 | C |
| ATOM | 3308 | CE2 | TYR | B | 127 | 8.273 | 64.540 | 68.778 | 1.00 69.17 | C |
| ATOM | 3309 | CZ | TYR | B | 127 | 8.227 | 65.696 | 67.998 | 1.00 69.17 | C |
| ATOM | 3310 | OH | TYR | B | 127 | 8.678 | 65.686 | 66.690 | 1.00 69.17 | O |
| ATOM | 3311 | N | LEU | B | 128 | 6.063 | 64.221 | 74.514 | 1.00 35.76 | N |
| ATOM | 3312 | CA | LEU | B | 128 | 6.055 | 64.089 | 75.958 | 1.00 35.76 | C |
| ATOM | 3313 | C | LEU | B | 128 | 7.447 | 64.560 | 76.341 | 1.00 35.76 | C |
| ATOM | 3314 | O | LEU | B | 128 | 8.435 | 64.095 | 75.783 | 1.00 35.76 | O |
| ATOM | 3315 | CB | LEU | B | 128 | 5.861 | 62.630 | 76.360 | 1.00 23.71 | C |
| ATOM | 3316 | CG | LEU | B | 128 | 6.155 | 62.311 | 77.823 | 1.00 23.71 | C |
| ATOM | 3317 | CD1 | LEU | B | 128 | 5.191 | 63.066 | 78.730 | 1.00 23.71 | C |
| ATOM | 3318 | CD2 | LEU | B | 128 | 6.040 | 60.812 | 78.040 | 1.00 23.71 | C |
| ATOM | 3319 | N | ASN | B | 129 | 7.524 | 65.498 | 77.270 | 1.00 26.19 | N |
| ATOM | 3320 | CA | ASN | B | 129 | 8.807 | 66.034 | 77.698 | 1.00 26.19 | C |
| ATOM | 3321 | C | ASN | B | 129 | 9.159 | 65.533 | 79.080 | 1.00 26.19 | C |
| ATOM | 3322 | O | ASN | B | 129 | 8.418 | 65.752 | 80.031 | 1.00 26.19 | O |
| ATOM | 3323 | CB | ASN | B | 129 | 8.756 | 67.563 | 77.702 | 1.00 38.77 | C |
| ATOM | 3324 | CG | ASN | B | 129 | 8.549 | 68.144 | 76.313 | 1.00 38.77 | C |
| ATOM | 3325 | OD1 | ASN | B | 129 | 9.482 | 68.657 | 75.697 | 1.00 38.77 | O |
| ATOM | 3326 | ND2 | ASN | B | 129 | 7.324 | 68.059 | 75.811 | 1.00 38.77 | N |
| ATOM | 3327 | N | LEU | B | 130 | 10.290 | 64.851 | 79.189 | 1.00 33.93 | N |
| ATOM | 3328 | CA | LEU | B | 130 | 10.736 | 64.333 | 80.475 | 1.00 33.93 | C |
| ATOM | 3329 | C | LEU | B | 130 | 11.864 | 65.194 | 81.021 | 1.00 33.93 | C |
| ATOM | 3330 | O | LEU | B | 130 | 12.980 | 65.175 | 80.500 | 1.00 33.93 | O |
| ATOM | 3331 | CB | LEU | B | 130 | 11.203 | 62.878 | 80.336 | 1.00 30.88 | C |
| ATOM | 3332 | CG | LEU | B | 130 | 10.092 | 61.821 | 80.356 | 1.00 30.88 | C |
| ATOM | 3333 | CD1 | LEU | B | 130 | 9.086 | 62.143 | 79.288 | 1.00 30.88 | C |
| ATOM | 3334 | CD2 | LEU | B | 130 | 10.661 | 60.431 | 80.146 | 1.00 30.88 | C |
| ATOM | 3335 | N | VAL | B | 131 | 11.556 | 65.969 | 82.056 | 1.00 34.92 | N |
| ATOM | 3336 | CA | VAL | B | 131 | 12.541 | 66.833 | 82.686 | 1.00 34.92 | C |
| ATOM | 3337 | C | VAL | B | 131 | 13.202 | 66.033 | 83.783 | 1.00 34.92 | C |
| ATOM | 3338 | O | VAL | B | 131 | 12.641 | 65.866 | 84.865 | 1.00 34.92 | O |
| ATOM | 3339 | CB | VAL | B | 131 | 11.895 | 68.067 | 83.309 | 1.00 27.17 | C |
| ATOM | 3340 | CG1 | VAL | B | 131 | 12.909 | 68.802 | 84.166 | 1.00 27.17 | C |
| ATOM | 3341 | CG2 | VAL | B | 131 | 11.374 | 68.974 | 82.217 | 1.00 27.17 | C |
| ATOM | 3342 | N | LEU | B | 132 | 14.399 | 65.540 | 83.492 | 1.00 31.94 | N |
| ATOM | 3343 | CA | LEU | B | 132 | 15.149 | 64.731 | 84.435 | 1.00 31.94 | C |
| ATOM | 3344 | C | LEU | B | 132 | 16.348 | 65.456 | 84.988 | 1.00 31.94 | C |
| ATOM | 3345 | O | LEU | B | 132 | 16.743 | 66.495 | 84.485 | 1.00 31.94 | O |

FIG. 1-55

```
ATOM   3346  CB   LEU B 132      15.638  63.476  83.739  1.00 26.39           C
ATOM   3347  CG   LEU B 132      14.522  62.679  83.087  1.00 26.39           C
ATOM   3348  CD1  LEU B 132      15.005  62.182  81.741  1.00 26.39           C
ATOM   3349  CD2  LEU B 132      14.087  61.547  83.999  1.00 26.39           C
ATOM   3350  N    ASP B 133      16.925  64.900  86.041  1.00 31.67           N
ATOM   3351  CA   ASP B 133      18.128  65.470  86.617  1.00 31.67           C
ATOM   3352  C    ASP B 133      19.228  65.315  85.576  1.00 31.67           C
ATOM   3353  O    ASP B 133      19.218  64.374  84.782  1.00 31.67           O
ATOM   3354  CB   ASP B 133      18.518  64.707  87.873  1.00 40.71           C
ATOM   3355  CG   ASP B 133      17.855  65.255  89.102  1.00 40.71           C
ATOM   3356  OD1  ASP B 133      17.718  64.495  90.072  1.00 40.71           O
ATOM   3357  OD2  ASP B 133      17.483  66.448  89.106  1.00 40.71           O
ATOM   3358  N    TYR B 134      20.172  66.242  85.559  1.00 35.47           N
ATOM   3359  CA   TYR B 134      21.268  66.141  84.613  1.00 35.47           C
ATOM   3360  C    TYR B 134      22.488  65.568  85.323  1.00 35.47           C
ATOM   3361  O    TYR B 134      22.778  65.907  86.471  1.00 35.47           O
ATOM   3362  CB   TYR B 134      21.613  67.506  84.037  1.00 64.33           C
ATOM   3363  CG   TYR B 134      22.881  67.492  83.211  1.00 64.33           C
ATOM   3364  CD1  TYR B 134      22.903  66.946  81.929  1.00 64.33           C
ATOM   3365  CD2  TYR B 134      24.065  68.010  83.727  1.00 64.33           C
ATOM   3366  CE1  TYR B 134      24.069  66.919  81.190  1.00 64.33           C
ATOM   3367  CE2  TYR B 134      25.232  67.986  82.999  1.00 64.33           C
ATOM   3368  CZ   TYR B 134      25.231  67.440  81.735  1.00 64.33           C
ATOM   3369  OH   TYR B 134      26.422  67.399  81.044  1.00 64.33           O
ATOM   3370  N    VAL B 135      23.192  64.675  84.650  1.00 30.56           N
ATOM   3371  CA   VAL B 135      24.370  64.089  85.243  1.00 30.56           C
ATOM   3372  C    VAL B 135      25.398  63.981  84.141  1.00 30.56           C
ATOM   3373  O    VAL B 135      25.229  63.241  83.170  1.00 30.56           O
ATOM   3374  CB   VAL B 135      24.056  62.738  85.852  1.00 22.63           C
ATOM   3375  CG1  VAL B 135      25.287  62.169  86.517  1.00 22.63           C
ATOM   3376  CG2  VAL B 135      22.943  62.902  86.862  1.00 22.63           C
ATOM   3377  N    PRO B 136      26.492  64.734  84.289  1.00 35.98           N
ATOM   3378  CA   PRO B 136      27.631  64.832  83.368  1.00 35.98           C
ATOM   3379  C    PRO B 136      28.259  63.512  82.899  1.00 35.98           C
ATOM   3380  O    PRO B 136      28.084  63.107  81.750  1.00 35.98           O
ATOM   3381  CB   PRO B 136      28.610  65.700  84.145  1.00 40.90           C
ATOM   3382  CG   PRO B 136      28.342  65.271  85.585  1.00 40.90           C
ATOM   3383  CD   PRO B 136      26.847  65.256  85.626  1.00 40.90           C
ATOM   3384  N    GLU B 137      28.984  62.837  83.781  1.00 28.75           N
ATOM   3385  CA   GLU B 137      29.637  61.594  83.396  1.00 28.75           C
ATOM   3386  C    GLU B 137      28.745  60.355  83.351  1.00 28.75           C
ATOM   3387  O    GLU B 137      27.585  60.375  83.757  1.00 28.75           O
ATOM   3388  CB   GLU B 137      30.807  61.301  84.334  1.00 50.44           C
ATOM   3389  CG   GLU B 137      31.938  62.303  84.315  0.00 50.44           C
ATOM   3390  CD   GLU B 137      32.535  62.479  82.939  1.00 50.44           C
ATOM   3391  OE1  GLU B 137      32.658  61.478  82.197  1.00 50.44           O
ATOM   3392  OE2  GLU B 137      32.897  63.624  82.599  1.00 50.44           O
ATOM   3393  N    THR B 138      29.324  59.277  82.840  1.00 27.67           N
ATOM   3394  CA   THR B 138      28.665  57.981  82.754  1.00 27.67           C
ATOM   3395  C    THR B 138      29.761  56.954  82.974  1.00 27.67           C
ATOM   3396  O    THR B 138      30.930  57.240  82.757  1.00 27.67           O
ATOM   3397  CB   THR B 138      28.037  57.714  81.367  1.00 24.07           C
ATOM   3398  OG1  THR B 138      29.067  57.644  80.383  1.00 24.07           O
ATOM   3399  CG2  THR B 138      27.059  58.803  80.995  1.00 24.07           C
ATOM   3400  N    VAL B 139      29.389  55.768  83.427  1.00 24.31           N
ATOM   3401  CA   VAL B 139      30.368  54.723  83.636  1.00 24.31           C
ATOM   3402  C    VAL B 139      31.078  54.456  82.320  1.00 24.31           C
ATOM   3403  O    VAL B 139      32.248  54.100  82.310  1.00 24.31           O
ATOM   3404  CB   VAL B 139      29.701  53.423  84.137  1.00 25.24           C
ATOM   3405  CG1  VAL B 139      30.678  52.246  84.046  1.00 25.24           C
ATOM   3406  CG2  VAL B 139      29.257  53.614  85.560  1.00 25.24           C
ATOM   3407  N    TYR B 140      30.364  54.640  81.214  1.00 26.09           N
```

FIG. 1-56

| ATOM | 3408 | CA | TYR B 140 | 30.928 | 54.424 | 79.889 | 1.00 26.09 | C |
| --- | --- | --- | --- | --- | --- | --- | --- | --- |
| ATOM | 3409 | C | TYR B 140 | 32.098 | 55.377 | 79.610 | 1.00 26.09 | C |
| ATOM | 3410 | O | TYR B 140 | 33.233 | 54.933 | 79.424 | 1.00 26.09 | O |
| ATOM | 3411 | CB | TYR B 140 | 29.867 | 54.624 | 78.811 | 1.00 42.32 | C |
| ATOM | 3412 | CG | TYR B 140 | 30.452 | 54.552 | 77.424 | 1.00 42.32 | C |
| ATOM | 3413 | CD1 | TYR B 140 | 30.799 | 53.325 | 76.860 | 1.00 42.32 | C |
| ATOM | 3414 | CD2 | TYR B 140 | 30.732 | 55.713 | 76.702 | 1.00 42.32 | C |
| ATOM | 3415 | CE1 | TYR B 140 | 31.410 | 53.248 | 75.617 | 1.00 42.32 | C |
| ATOM | 3416 | CE2 | TYR B 140 | 31.348 | 55.648 | 75.458 | 1.00 42.32 | C |
| ATOM | 3417 | CZ | TYR B 140 | 31.684 | 54.406 | 74.920 | 1.00 42.32 | C |
| ATOM | 3418 | OH | TYR B 140 | 32.297 | 54.311 | 73.686 | 1.00 42.32 | O |
| ATOM | 3419 | N | ARG B 141 | 31.816 | 56.682 | 79.564 | 1.00 33.10 | N |
| ATOM | 3420 | CA | ARG B 141 | 32.849 | 57.680 | 79.312 | 1.00 33.10 | C |
| ATOM | 3421 | C | ARG B 141 | 34.049 | 57.465 | 80.220 | 1.00 33.10 | C |
| ATOM | 3422 | O | ARG B 141 | 35.197 | 57.567 | 79.782 | 1.00 33.10 | O |
| ATOM | 3423 | CB | ARG B 141 | 32.329 | 59.100 | 79.546 | 1.00 64.61 | C |
| ATOM | 3424 | CG | ARG B 141 | 31.473 | 59.684 | 78.441 | 1.00 64.61 | C |
| ATOM | 3425 | CD | ARG B 141 | 31.388 | 61.205 | 78.609 | 1.00 64.61 | C |
| ATOM | 3426 | NE | ARG B 141 | 32.711 | 61.828 | 78.451 | 1.00 64.61 | N |
| ATOM | 3427 | CZ | ARG B 141 | 33.190 | 62.808 | 79.221 | 1.00 64.61 | C |
| ATOM | 3428 | NH1 | ARG B 141 | 32.457 | 63.296 | 80.218 | 1.00 64.61 | N |
| ATOM | 3429 | NH2 | ARG B 141 | 34.413 | 63.288 | 79.000 | 1.00 64.61 | N |
| ATOM | 3430 | N | VAL B 142 | 33.780 | 57.178 | 81.487 | 1.00 26.47 | N |
| ATOM | 3431 | CA | VAL B 142 | 34.849 | 56.979 | 82.446 | 1.00 26.47 | C |
| ATOM | 3432 | C | VAL B 142 | 35.674 | 55.763 | 82.130 | 1.00 26.47 | C |
| ATOM | 3433 | O | VAL B 142 | 36.879 | 55.859 | 81.961 | 1.00 26.47 | O |
| ATOM | 3434 | CB | VAL B 142 | 34.297 | 56.870 | 83.861 | 1.00 22.73 | C |
| ATOM | 3435 | CG1 | VAL B 142 | 35.361 | 56.356 | 84.811 | 1.00 22.73 | C |
| ATOM | 3436 | CG2 | VAL B 142 | 33.810 | 58.237 | 84.299 | 1.00 22.73 | C |
| ATOM | 3437 | N | ALA B 143 | 35.025 | 54.615 | 82.037 | 1.00 31.01 | N |
| ATOM | 3438 | CA | ALA B 143 | 35.735 | 53.383 | 81.724 | 1.00 31.01 | C |
| ATOM | 3439 | C | ALA B 143 | 36.558 | 53.527 | 80.443 | 1.00 31.01 | C |
| ATOM | 3440 | O | ALA B 143 | 37.628 | 52.933 | 80.319 | 1.00 31.01 | O |
| ATOM | 3441 | CB | ALA B 143 | 34.746 | 52.238 | 81.577 | 1.00 38.81 | C |
| ATOM | 3442 | N | ARG B 144 | 36.057 | 54.317 | 79.497 | 1.00 38.23 | N |
| ATOM | 3443 | CA | ARG B 144 | 36.745 | 54.513 | 78.229 | 1.00 38.23 | C |
| ATOM | 3444 | C | ARG B 144 | 38.046 | 55.270 | 78.416 | 1.00 38.23 | C |
| ATOM | 3445 | O | ARG B 144 | 39.026 | 55.003 | 77.724 | 1.00 38.23 | O |
| ATOM | 3446 | CB | ARG B 144 | 35.858 | 55.266 | 77.244 | 1.00 59.20 | C |
| ATOM | 3447 | CG | ARG B 144 | 36.376 | 55.247 | 75.821 | 1.00 59.20 | C |
| ATOM | 3448 | CD | ARG B 144 | 35.399 | 55.922 | 74.870 | 1.00 59.20 | C |
| ATOM | 3449 | NE | ARG B 144 | 35.901 | 55.933 | 73.500 | 1.00 59.20 | N |
| ATOM | 3450 | CZ | ARG B 144 | 35.200 | 56.351 | 72.444 | 1.00 59.20 | C |
| ATOM | 3451 | NH1 | ARG B 144 | 33.948 | 56.797 | 72.596 | 1.00 59.20 | N |
| ATOM | 3452 | NH2 | ARG B 144 | 35.748 | 56.330 | 71.230 | 1.00 59.20 | N |
| ATOM | 3453 | N | HIS B 145 | 38.067 | 56.210 | 79.351 | 1.00 38.97 | N |
| ATOM | 3454 | CA | HIS B 145 | 39.282 | 56.959 | 79.586 | 1.00 38.97 | C |
| ATOM | 3455 | C | HIS B 145 | 40.371 | 56.083 | 80.187 | 1.00 38.97 | C |
| ATOM | 3456 | O | HIS B 145 | 41.476 | 56.024 | 79.656 | 1.00 38.97 | O |
| ATOM | 3457 | CB | HIS B 145 | 39.005 | 58.163 | 80.486 | 1.00 93.08 | C |
| ATOM | 3458 | CG | HIS B 145 | 38.368 | 59.309 | 79.763 | 1.00 93.08 | C |
| ATOM | 3459 | ND1 | HIS B 145 | 37.378 | 60.091 | 80.327 | 1.00 93.08 | N |
| ATOM | 3460 | CD2 | HIS B 145 | 38.562 | 59.789 | 78.514 | 1.00 93.08 | C |
| ATOM | 3461 | CE1 | HIS B 145 | 36.987 | 61.000 | 79.450 | 1.00 93.08 | C |
| ATOM | 3462 | NE2 | HIS B 145 | 37.688 | 60.840 | 78.342 | 1.00 93.08 | N |
| ATOM | 3463 | N | TYR B 146 | 40.077 | 55.394 | 81.279 | 1.00 29.76 | N |
| ATOM | 3464 | CA | TYR B 146 | 41.094 | 54.555 | 81.877 | 1.00 29.76 | C |
| ATOM | 3465 | C | TYR B 146 | 41.565 | 53.547 | 80.849 | 1.00 29.76 | C |
| ATOM | 3466 | O | TYR B 146 | 42.743 | 53.185 | 80.798 | 1.00 29.76 | O |
| ATOM | 3467 | CB | TYR B 146 | 40.547 | 53.836 | 83.108 | 1.00 30.48 | C |
| ATOM | 3468 | CG | TYR B 146 | 40.420 | 54.737 | 84.309 | 1.00 30.48 | C |
| ATOM | 3469 | CD1 | TYR B 146 | 39.383 | 55.660 | 84.404 | 1.00 30.48 | C |

FIG. 1-57

| ATOM | 3470 | CD2 | TYR | B | 146 | 41.371 | 54.706 | 85.328 | 1.00 | 30.48 | C |
| ATOM | 3471 | CE1 | TYR | B | 146 | 39.296 | 56.526 | 85.479 | 1.00 | 30.48 | C |
| ATOM | 3472 | CE2 | TYR | B | 146 | 41.292 | 55.572 | 86.408 | 1.00 | 30.48 | C |
| ATOM | 3473 | CZ | TYR | B | 146 | 40.252 | 56.477 | 86.473 | 1.00 | 30.48 | C |
| ATOM | 3474 | OH | TYR | B | 146 | 40.151 | 57.330 | 87.536 | 1.00 | 30.48 | O |
| ATOM | 3475 | N | SER | B | 147 | 40.635 | 53.117 | 80.008 | 1.00 | 35.64 | N |
| ATOM | 3476 | CA | SER | B | 147 | 40.938 | 52.135 | 78.990 | 1.00 | 35.64 | C |
| ATOM | 3477 | C | SER | B | 147 | 41.828 | 52.738 | 77.915 | 1.00 | 35.64 | C |
| ATOM | 3478 | O | SER | B | 147 | 42.930 | 52.256 | 77.651 | 1.00 | 35.64 | O |
| ATOM | 3479 | CB | SER | B | 147 | 39.640 | 51.625 | 78.378 | 1.00 | 47.74 | C |
| ATOM | 3480 | OG | SER | B | 147 | 39.859 | 50.415 | 77.678 | 1.00 | 47.74 | O |
| ATOM | 3481 | N | ARG | B | 148 | 41.342 | 53.802 | 77.293 | 1.00 | 49.06 | N |
| ATOM | 3482 | CA | ARG | B | 148 | 42.079 | 54.490 | 76.236 | 1.00 | 49.06 | C |
| ATOM | 3483 | C | ARG | B | 148 | 43.491 | 54.825 | 76.720 | 1.00 | 49.06 | C |
| ATOM | 3484 | O | ARG | B | 148 | 44.417 | 54.937 | 75.925 | 1.00 | 49.06 | O |
| ATOM | 3485 | CB | ARG | B | 148 | 41.338 | 55.778 | 75.861 | 1.00 | 58.59 | C |
| ATOM | 3486 | CG | ARG | B | 148 | 40.945 | 55.933 | 74.398 | 1.00 | 58.59 | C |
| ATOM | 3487 | CD | ARG | B | 148 | 41.941 | 56.839 | 73.676 | 0.00 | 58.59 | C |
| ATOM | 3488 | NE | ARG | B | 148 | 41.391 | 57.434 | 72.460 | 1.00 | 58.59 | N |
| ATOM | 3489 | CZ | ARG | B | 148 | 41.945 | 58.464 | 71.819 | 1.00 | 58.59 | C |
| ATOM | 3490 | NH1 | ARG | B | 148 | 43.071 | 59.023 | 72.271 | 1.00 | 58.59 | N |
| ATOM | 3491 | NH2 | ARG | B | 148 | 41.365 | 58.949 | 70.726 | 1.00 | 58.59 | N |
| ATOM | 3492 | N | ALA | B | 149 | 43.652 | 54.987 | 78.028 | 1.00 | 28.91 | N |
| ATOM | 3493 | CA | ALA | B | 149 | 44.958 | 55.312 | 78.600 | 1.00 | 28.91 | C |
| ATOM | 3494 | C | ALA | B | 149 | 45.665 | 54.067 | 79.175 | 1.00 | 28.91 | C |
| ATOM | 3495 | O | ALA | B | 149 | 46.592 | 54.170 | 79.980 | 1.00 | 28.91 | O |
| ATOM | 3496 | CB | ALA | B | 149 | 44.790 | 56.369 | 79.681 | 1.00 | 22.19 | C |
| ATOM | 3497 | N | LYS | B | 150 | 45.219 | 52.894 | 78.741 | 1.00 | 44.90 | N |
| ATOM | 3498 | CA | LYS | B | 150 | 45.775 | 51.631 | 79.210 | 1.00 | 44.90 | C |
| ATOM | 3499 | C | LYS | B | 150 | 46.014 | 51.669 | 80.714 | 1.00 | 44.90 | C |
| ATOM | 3500 | O | LYS | B | 150 | 47.122 | 51.437 | 81.185 | 1.00 | 44.90 | O |
| ATOM | 3501 | CB | LYS | B | 150 | 47.071 | 51.321 | 78.478 | 1.00 | 50.99 | C |
| ATOM | 3502 | N | GLN | B | 151 | 44.968 | 51.992 | 81.460 | 1.00 | 40.59 | N |
| ATOM | 3503 | CA | GLN | B | 151 | 45.037 | 52.041 | 82.912 | 1.00 | 40.59 | C |
| ATOM | 3504 | C | GLN | B | 151 | 43.744 | 51.424 | 83.443 | 1.00 | 40.59 | C |
| ATOM | 3505 | O | GLN | B | 151 | 42.708 | 51.427 | 82.763 | 1.00 | 40.59 | O |
| ATOM | 3506 | CB | GLN | B | 151 | 45.188 | 53.483 | 83.414 | 1.00 | 25.05 | C |
| ATOM | 3507 | CG | GLN | B | 151 | 46.526 | 54.112 | 83.094 | 0.00 | 25.05 | C |
| ATOM | 3508 | CD | GLN | B | 151 | 46.679 | 55.475 | 83.728 | 1.00 | 25.05 | C |
| ATOM | 3509 | OE1 | GLN | B | 151 | 46.615 | 55.616 | 84.948 | 0.00 | 25.05 | O |
| ATOM | 3510 | NE2 | GLN | B | 151 | 46.884 | 56.493 | 82.899 | 0.00 | 25.05 | N |
| ATOM | 3511 | N | THR | B | 152 | 43.808 | 50.890 | 84.658 | 1.00 | 54.76 | N |
| ATOM | 3512 | CA | THR | B | 152 | 42.652 | 50.246 | 85.267 | 1.00 | 54.76 | C |
| ATOM | 3513 | C | THR | B | 152 | 41.882 | 51.155 | 86.220 | 1.00 | 54.76 | C |
| ATOM | 3514 | O | THR | B | 152 | 42.475 | 51.883 | 87.009 | 1.00 | 54.76 | O |
| ATOM | 3515 | CB | THR | B | 152 | 43.085 | 48.981 | 86.053 | 1.00 | 65.66 | C |
| ATOM | 3516 | OG1 | THR | B | 152 | 42.402 | 48.953 | 87.317 | 1.00 | 65.66 | O |
| ATOM | 3517 | CG2 | THR | B | 152 | 44.620 | 48.972 | 86.279 | 1.00 | 65.66 | C |
| ATOM | 3518 | N | LEU | B | 153 | 40.561 | 51.119 | 86.147 | 1.00 | 34.37 | N |
| ATOM | 3519 | CA | LEU | B | 153 | 39.768 | 51.922 | 87.058 | 1.00 | 34.37 | C |
| ATOM | 3520 | C | LEU | B | 153 | 39.990 | 51.351 | 88.471 | 1.00 | 34.37 | C |
| ATOM | 3521 | O | LEU | B | 153 | 39.784 | 50.162 | 88.704 | 1.00 | 34.37 | O |
| ATOM | 3522 | CB | LEU | B | 153 | 38.290 | 51.831 | 86.684 | 1.00 | 26.23 | C |
| ATOM | 3523 | CG | LEU | B | 153 | 37.313 | 52.522 | 87.646 | 1.00 | 26.23 | C |
| ATOM | 3524 | CD1 | LEU | B | 153 | 37.367 | 54.022 | 87.459 | 1.00 | 26.23 | C |
| ATOM | 3525 | CD2 | LEU | B | 153 | 35.903 | 52.005 | 87.397 | 1.00 | 26.23 | C |
| ATOM | 3526 | N | PRO | B | 154 | 40.422 | 52.188 | 89.427 | 1.00 | 27.76 | N |
| ATOM | 3527 | CA | PRO | B | 154 | 40.655 | 51.719 | 90.801 | 1.00 | 27.76 | C |
| ATOM | 3528 | C | PRO | B | 154 | 39.451 | 50.948 | 91.340 | 1.00 | 27.76 | C |
| ATOM | 3529 | O | PRO | B | 154 | 38.328 | 51.424 | 91.253 | 1.00 | 27.76 | O |
| ATOM | 3530 | CB | PRO | B | 154 | 40.904 | 53.012 | 91.561 | 1.00 | 28.15 | C |
| ATOM | 3531 | CG | PRO | B | 154 | 41.580 | 53.865 | 90.533 | 1.00 | 28.15 | C |

FIG. 1-58

```
ATOM   3532  CD   PRO B 154      40.747  53.618  89.296  1.00 28.15           C
ATOM   3533  N    VAL B 155      39.686  49.767  91.908  1.00 29.65           N
ATOM   3534  CA   VAL B 155      38.592  48.941  92.422  1.00 29.65           C
ATOM   3535  C    VAL B 155      37.692  49.635  93.444  1.00 29.65           C
ATOM   3536  O    VAL B 155      36.622  49.141  93.778  1.00 29.65           O
ATOM   3537  CB   VAL B 155      39.114  47.597  93.040  1.00 35.58           C
ATOM   3538  CG1  VAL B 155      40.230  47.036  92.186  1.00 35.58           C
ATOM   3539  CG2  VAL B 155      39.579  47.794  94.471  1.00 35.58           C
ATOM   3540  N    ILE B 156      38.114  50.781  93.949  1.00 23.25           N
ATOM   3541  CA   ILE B 156      37.285  51.459  94.924  1.00 23.25           C
ATOM   3542  C    ILE B 156      36.057  51.982  94.189  1.00 23.25           C
ATOM   3543  O    ILE B 156      34.948  51.947  94.718  1.00 23.25           O
ATOM   3544  CB   ILE B 156      38.069  52.604  95.641  1.00 22.07           C
ATOM   3545  CG1  ILE B 156      37.215  53.214  96.749  1.00 22.07           C
ATOM   3546  CG2  ILE B 156      38.496  53.654  94.652  1.00 22.07           C
ATOM   3547  CD1  ILE B 156      37.044  52.330  97.950  1.00 22.07           C
ATOM   3548  N    TYR B 157      36.258  52.437  92.956  1.00 25.85           N
ATOM   3549  CA   TYR B 157      35.162  52.954  92.136  1.00 25.85           C
ATOM   3550  C    TYR B 157      34.320  51.817  91.593  1.00 25.85           C
ATOM   3551  O    TYR B 157      33.103  51.932  91.472  1.00 25.85           O
ATOM   3552  CB   TYR B 157      35.701  53.774  90.972  1.00 35.67           C
ATOM   3553  CG   TYR B 157      36.420  55.017  91.416  1.00 35.67           C
ATOM   3554  CD1  TYR B 157      35.786  55.960  92.227  1.00 35.67           C
ATOM   3555  CD2  TYR B 157      37.737  55.259  91.027  1.00 35.67           C
ATOM   3556  CE1  TYR B 157      36.450  57.114  92.638  1.00 35.67           C
ATOM   3557  CE2  TYR B 157      38.409  56.410  91.429  1.00 35.67           C
ATOM   3558  CZ   TYR B 157      37.763  57.331  92.232  1.00 35.67           C
ATOM   3559  OH   TYR B 157      38.430  58.468  92.617  1.00 35.67           O
ATOM   3560  N    VAL B 158      34.990  50.726  91.250  1.00 27.71           N
ATOM   3561  CA   VAL B 158      34.309  49.552  90.747  1.00 27.71           C
ATOM   3562  C    VAL B 158      33.366  49.086  91.853  1.00 27.71           C
ATOM   3563  O    VAL B 158      32.209  48.772  91.587  1.00 27.71           O
ATOM   3564  CB   VAL B 158      35.313  48.443  90.399  1.00 22.20           C
ATOM   3565  CG1  VAL B 158      34.598  47.253  89.789  1.00 22.20           C
ATOM   3566  CG2  VAL B 158      36.349  48.982  89.455  1.00 22.20           C
ATOM   3567  N    LYS B 159      33.857  49.061  93.091  1.00 26.79           N
ATOM   3568  CA   LYS B 159      33.034  48.666  94.235  1.00 26.79           C
ATOM   3569  C    LYS B 159      31.851  49.633  94.412  1.00 26.79           C
ATOM   3570  O    LYS B 159      30.701  49.221  94.549  1.00 26.79           O
ATOM   3571  CB   LYS B 159      33.855  48.693  95.525  1.00 27.27           C
ATOM   3572  CG   LYS B 159      34.990  47.699  95.606  1.00 27.27           C
ATOM   3573  CD   LYS B 159      35.776  47.902  96.893  1.00 27.27           C
ATOM   3574  CE   LYS B 159      36.910  46.911  97.023  1.00 27.27           C
ATOM   3575  NZ   LYS B 159      36.435  45.519  96.912  1.00 27.27           N
ATOM   3576  N    LEU B 160      32.162  50.925  94.413  1.00 30.06           N
ATOM   3577  CA   LEU B 160      31.175  51.978  94.590  1.00 30.06           C
ATOM   3578  C    LEU B 160      30.112  52.009  93.508  1.00 30.06           C
ATOM   3579  O    LEU B 160      28.921  52.104  93.796  1.00 30.06           O
ATOM   3580  CB   LEU B 160      31.876  53.335  94.638  1.00 32.79           C
ATOM   3581  CG   LEU B 160      31.337  54.303  95.684  1.00 32.79           C
ATOM   3582  CD1  LEU B 160      31.496  53.698  97.063  1.00 32.79           C
ATOM   3583  CD2  LEU B 160      32.084  55.618  95.599  0.00 32.79           C
ATOM   3584  N    TYR B 161      30.542  51.941  92.256  1.00 21.41           N
ATOM   3585  CA   TYR B 161      29.609  51.969  91.145  1.00 21.41           C
ATOM   3586  C    TYR B 161      28.720  50.726  91.082  1.00 21.41           C
ATOM   3587  O    TYR B 161      27.514  50.830  90.887  1.00 21.41           O
ATOM   3588  CB   TYR B 161      30.379  52.131  89.841  1.00 29.26           C
ATOM   3589  CG   TYR B 161      31.181  53.410  89.748  1.00 29.26           C
ATOM   3590  CD1  TYR B 161      31.170  54.344  90.784  1.00 29.26           C
ATOM   3591  CD2  TYR B 161      31.893  53.719  88.589  1.00 29.26           C
ATOM   3592  CE1  TYR B 161      31.840  55.559  90.667  1.00 29.26           C
ATOM   3593  CE2  TYR B 161      32.566  54.927  88.455  1.00 29.26           C
```

FIG. 1-59

```
ATOM   3594  CZ   TYR B 161      32.531  55.847  89.493  1.00 29.26           C
ATOM   3595  OH   TYR B 161      33.136  57.073  89.336  1.00 29.26           O
ATOM   3596  N    MET B 162      29.310  49.548  91.256  1.00 24.74           N
ATOM   3597  CA   MET B 162      28.533  48.313  91.206  1.00 24.74           C
ATOM   3598  C    MET B 162      27.537  48.190  92.347  1.00 24.74           C
ATOM   3599  O    MET B 162      26.437  47.667  92.180  1.00 24.74           O
ATOM   3600  CB   MET B 162      29.455  47.093  91.204  1.00 22.38           C
ATOM   3601  CG   MET B 162      30.317  46.965  89.954  1.00 22.38           C
ATOM   3602  SD   MET B 162      29.387  47.058  88.413  1.00 22.38           S
ATOM   3603  CE   MET B 162      28.237  45.713  88.638  1.00 22.38           C
ATOM   3604  N    TYR B 163      27.929  48.676  93.512  1.00 26.83           N
ATOM   3605  CA   TYR B 163      27.071  48.622  94.686  1.00 26.83           C
ATOM   3606  C    TYR B 163      25.801  49.444  94.468  1.00 26.83           C
ATOM   3607  O    TYR B 163      24.705  48.988  94.775  1.00 26.83           O
ATOM   3608  CB   TYR B 163      27.835  49.144  95.911  1.00 21.69           C
ATOM   3609  CG   TYR B 163      27.015  49.204  97.176  1.00 21.69           C
ATOM   3610  CD1  TYR B 163      26.822  48.065  97.961  1.00 21.69           C
ATOM   3611  CD2  TYR B 163      26.420  50.398  97.581  1.00 21.69           C
ATOM   3612  CE1  TYR B 163      26.062  48.120  99.109  1.00 21.69           C
ATOM   3613  CE2  TYR B 163      25.654  50.459  98.726  1.00 21.69           C
ATOM   3614  CZ   TYR B 163      25.481  49.318  99.486  1.00 21.69           C
ATOM   3615  OH   TYR B 163      24.731  49.374 100.633  1.00 21.69           O
ATOM   3616  N    GLN B 164      25.968  50.655  93.937  1.00 28.12           N
ATOM   3617  CA   GLN B 164      24.852  51.557  93.677  1.00 28.12           C
ATOM   3618  C    GLN B 164      23.958  51.051  92.534  1.00 28.12           C
ATOM   3619  O    GLN B 164      22.751  51.302  92.510  1.00 28.12           O
ATOM   3620  CB   GLN B 164      25.392  52.964  93.386  1.00 24.38           C
ATOM   3621  CG   GLN B 164      26.209  53.544  94.547  1.00 24.38           C
ATOM   3622  CD   GLN B 164      26.797  54.908  94.247  1.00 24.38           C
ATOM   3623  OE1  GLN B 164      26.083  55.907  94.165  1.00 24.38           O
ATOM   3624  NE2  GLN B 164      28.109  54.956  94.073  1.00 24.38           N
ATOM   3625  N    LEU B 165      24.549  50.328  91.588  1.00 34.87           N
ATOM   3626  CA   LEU B 165      23.778  49.779  90.489  1.00 34.87           C
ATOM   3627  C    LEU B 165      22.925  48.679  91.085  1.00 34.87           C
ATOM   3628  O    LEU B 165      21.728  48.648  90.864  1.00 34.87           O
ATOM   3629  CB   LEU B 165      24.682  49.171  89.418  1.00 12.92           C
ATOM   3630  CG   LEU B 165      24.102  48.943  88.016  1.00 12.92           C
ATOM   3631  CD1  LEU B 165      24.787  47.754  87.426  1.00 12.92           C
ATOM   3632  CD2  LEU B 165      22.617  48.721  88.038  1.00 12.92           C
ATOM   3633  N    PHE B 166      23.547  47.776  91.836  1.00 24.28           N
ATOM   3634  CA   PHE B 166      22.813  46.681  92.452  1.00 24.28           C
ATOM   3635  C    PHE B 166      21.706  47.181  93.373  1.00 24.28           C
ATOM   3636  O    PHE B 166      20.681  46.517  93.539  1.00 24.28           O
ATOM   3637  CB   PHE B 166      23.759  45.754  93.226  1.00 22.27           C
ATOM   3638  CG   PHE B 166      24.545  44.821  92.351  1.00 22.27           C
ATOM   3639  CD1  PHE B 166      23.905  44.025  91.399  1.00 22.27           C
ATOM   3640  CD2  PHE B 166      25.921  44.741  92.462  1.00 22.27           C
ATOM   3641  CE1  PHE B 166      24.633  43.170  90.571  1.00 22.27           C
ATOM   3642  CE2  PHE B 166      26.650  43.887  91.639  1.00 22.27           C
ATOM   3643  CZ   PHE B 166      26.006  43.105  90.694  1.00 22.27           C
ATOM   3644  N    ARG B 167      21.914  48.348  93.974  1.00 27.11           N
ATOM   3645  CA   ARG B 167      20.915  48.935  94.856  1.00 27.11           C
ATOM   3646  C    ARG B 167      19.756  49.370  93.991  1.00 27.11           C
ATOM   3647  O    ARG B 167      18.624  49.001  94.238  1.00 27.11           O
ATOM   3648  CB   ARG B 167      21.478  50.147  95.600  1.00 28.07           C
ATOM   3649  CG   ARG B 167      22.148  49.821  96.922  1.00 28.07           C
ATOM   3650  CD   ARG B 167      21.328  50.358  98.067  1.00 28.07           C
ATOM   3651  NE   ARG B 167      21.631  51.755  98.350  1.00 28.07           N
ATOM   3652  CZ   ARG B 167      20.879  52.543  99.109  1.00 28.07           C
ATOM   3653  NH1  ARG B 167      19.769  52.077  99.657  1.00 28.07           N
ATOM   3654  NH2  ARG B 167      21.251  53.790  99.334  1.00 28.07           N
ATOM   3655  N    SER B 168      20.040  50.148  92.960  1.00 27.02           N
```

FIG. 1-60

| ATOM | 3656 | CA | SER | B | 168 | 18.986 | 50.605 | 92.080 | 1.00 | 27.02 | C |
|---|---|---|---|---|---|---|---|---|---|---|---|
| ATOM | 3657 | C | SER | B | 168 | 18.205 | 49.411 | 91.559 | 1.00 | 27.02 | C |
| ATOM | 3658 | O | SER | B | 168 | 16.997 | 49.468 | 91.410 | 1.00 | 27.02 | O |
| ATOM | 3659 | CB | SER | B | 168 | 19.576 | 51.399 | 90.911 | 1.00 | 22.20 | C |
| ATOM | 3660 | OG | SER | B | 168 | 20.303 | 50.565 | 90.031 | 1.00 | 22.20 | O |
| ATOM | 3661 | N | LEU | B | 169 | 18.905 | 48.322 | 91.297 | 1.00 | 21.22 | N |
| ATOM | 3662 | CA | LEU | B | 169 | 18.277 | 47.118 | 90.778 | 1.00 | 21.22 | C |
| ATOM | 3663 | C | LEU | B | 169 | 17.384 | 46.401 | 91.782 | 1.00 | 21.22 | C |
| ATOM | 3664 | O | LEU | B | 169 | 16.311 | 45.929 | 91.428 | 1.00 | 21.22 | O |
| ATOM | 3665 | CB | LEU | B | 169 | 19.351 | 46.173 | 90.235 | 1.00 | 15.10 | C |
| ATOM | 3666 | CG | LEU | B | 169 | 19.509 | 46.105 | 88.707 | 1.00 | 15.10 | C |
| ATOM | 3667 | CD1 | LEU | B | 169 | 19.167 | 47.413 | 88.024 | 1.00 | 15.10 | C |
| ATOM | 3668 | CD2 | LEU | B | 169 | 20.918 | 45.683 | 88.413 | 1.00 | 15.10 | C |
| ATOM | 3669 | N | ALA | B | 170 | 17.826 | 46.323 | 93.033 | 1.00 | 28.26 | N |
| ATOM | 3670 | CA | ALA | B | 170 | 17.038 | 45.688 | 94.091 | 1.00 | 28.26 | C |
| ATOM | 3671 | C | ALA | B | 170 | 15.771 | 46.520 | 94.246 | 1.00 | 28.26 | C |
| ATOM | 3672 | O | ALA | B | 170 | 14.670 | 46.003 | 94.456 | 1.00 | 28.26 | O |
| ATOM | 3673 | CB | ALA | B | 170 | 17.824 | 45.672 | 95.398 | 1.00 | 16.51 | C |
| ATOM | 3674 | N | TYR | B | 171 | 15.945 | 47.824 | 94.116 | 1.00 | 22.86 | N |
| ATOM | 3675 | CA | TYR | B | 171 | 14.842 | 48.743 | 94.210 | 1.00 | 22.86 | C |
| ATOM | 3676 | C | TYR | B | 171 | 13.790 | 48.449 | 93.154 | 1.00 | 22.86 | C |
| ATOM | 3677 | O | TYR | B | 171 | 12.745 | 47.903 | 93.461 | 1.00 | 22.86 | O |
| ATOM | 3678 | CB | TYR | B | 171 | 15.321 | 50.173 | 94.042 | 1.00 | 18.75 | C |
| ATOM | 3679 | CG | TYR | B | 171 | 14.200 | 51.148 | 94.194 | 1.00 | 18.75 | C |
| ATOM | 3680 | CD1 | TYR | B | 171 | 13.580 | 51.319 | 95.421 | 1.00 | 18.75 | C |
| ATOM | 3681 | CD2 | TYR | B | 171 | 13.718 | 51.871 | 93.105 | 1.00 | 18.75 | C |
| ATOM | 3682 | CE1 | TYR | B | 171 | 12.516 | 52.178 | 95.569 | 1.00 | 18.75 | C |
| ATOM | 3683 | CE2 | TYR | B | 171 | 12.646 | 52.739 | 93.243 | 1.00 | 18.75 | C |
| ATOM | 3684 | CZ | TYR | B | 171 | 12.052 | 52.882 | 94.486 | 1.00 | 18.75 | C |
| ATOM | 3685 | OH | TYR | B | 171 | 10.995 | 53.731 | 94.658 | 1.00 | 18.75 | O |
| ATOM | 3686 | N | ILE | B | 172 | 14.061 | 48.793 | 91.904 | 1.00 | 28.69 | N |
| ATOM | 3687 | CA | ILE | B | 172 | 13.075 | 48.566 | 90.861 | 1.00 | 28.69 | C |
| ATOM | 3688 | C | ILE | B | 172 | 12.568 | 47.126 | 90.801 | 1.00 | 28.69 | C |
| ATOM | 3689 | O | ILE | B | 172 | 11.412 | 46.894 | 90.485 | 1.00 | 28.69 | O |
| ATOM | 3690 | CB | ILE | B | 172 | 13.595 | 48.997 | 89.456 | 1.00 | 14.84 | C |
| ATOM | 3691 | CG1 | ILE | B | 172 | 14.803 | 48.148 | 89.045 | 1.00 | 14.84 | C |
| ATOM | 3692 | CG2 | ILE | B | 172 | 13.919 | 50.485 | 89.461 | 1.00 | 14.84 | C |
| ATOM | 3693 | CD1 | ILE | B | 172 | 15.027 | 48.099 | 87.559 | 1.00 | 14.84 | C |
| ATOM | 3694 | N | HIS | B | 173 | 13.403 | 46.149 | 91.112 | 1.00 | 27.82 | N |
| ATOM | 3695 | CA | HIS | B | 173 | 12.903 | 44.789 | 91.065 | 1.00 | 27.82 | C |
| ATOM | 3696 | C | HIS | B | 173 | 11.809 | 44.525 | 92.105 | 1.00 | 27.82 | C |
| ATOM | 3697 | O | HIS | B | 173 | 10.848 | 43.793 | 91.836 | 1.00 | 27.82 | O |
| ATOM | 3698 | CB | HIS | B | 173 | 14.037 | 43.783 | 91.217 | 1.00 | 17.84 | C |
| ATOM | 3699 | CG | HIS | B | 173 | 14.879 | 43.653 | 89.990 | 1.00 | 17.84 | C |
| ATOM | 3700 | ND1 | HIS | B | 173 | 15.771 | 42.623 | 89.804 | 1.00 | 17.84 | N |
| ATOM | 3701 | CD2 | HIS | B | 173 | 15.003 | 44.457 | 88.908 | 1.00 | 17.84 | C |
| ATOM | 3702 | CE1 | HIS | B | 173 | 16.413 | 42.800 | 88.665 | 1.00 | 17.84 | C |
| ATOM | 3703 | NE2 | HIS | B | 173 | 15.966 | 43.907 | 88.102 | 1.00 | 17.84 | N |
| ATOM | 3704 | N | SER | B | 174 | 11.939 | 45.129 | 93.281 | 1.00 | 29.40 | N |
| ATOM | 3705 | CA | SER | B | 174 | 10.944 | 44.930 | 94.315 | 1.00 | 29.40 | C |
| ATOM | 3706 | C | SER | B | 174 | 9.554 | 45.291 | 93.799 | 1.00 | 29.40 | C |
| ATOM | 3707 | O | SER | B | 174 | 8.560 | 44.851 | 94.361 | 1.00 | 29.40 | O |
| ATOM | 3708 | CB | SER | B | 174 | 11.281 | 45.760 | 95.549 | 1.00 | 29.34 | C |
| ATOM | 3709 | OG | SER | B | 174 | 10.922 | 47.113 | 95.369 | 1.00 | 29.34 | O |
| ATOM | 3710 | N | PHE | B | 175 | 9.472 | 46.077 | 92.731 | 1.00 | 30.15 | N |
| ATOM | 3711 | CA | PHE | B | 175 | 8.168 | 46.439 | 92.176 | 1.00 | 30.15 | C |
| ATOM | 3712 | C | PHE | B | 175 | 7.823 | 45.578 | 90.974 | 1.00 | 30.15 | C |
| ATOM | 3713 | O | PHE | B | 175 | 6.802 | 45.804 | 90.317 | 1.00 | 30.15 | O |
| ATOM | 3714 | CB | PHE | B | 175 | 8.134 | 47.895 | 91.724 | 1.00 | 53.96 | C |
| ATOM | 3715 | CG | PHE | B | 175 | 8.375 | 48.866 | 92.816 | 1.00 | 53.96 | C |
| ATOM | 3716 | CD1 | PHE | B | 175 | 9.662 | 49.116 | 93.260 | 1.00 | 53.96 | C |
| ATOM | 3717 | CD2 | PHE | B | 175 | 7.306 | 49.502 | 93.440 | 1.00 | 53.96 | C |

FIG. 1-61

```
ATOM   3718  CE1 PHE B 175       9.888  49.990  94.320  1.00 53.96           C
ATOM   3719  CE2 PHE B 175       7.510  50.376  94.500  1.00 53.96           C
ATOM   3720  CZ  PHE B 175       8.807  50.622  94.945  1.00 53.96           C
ATOM   3721  N   GLY B 176       8.684  44.608  90.675  1.00 31.38           N
ATOM   3722  CA  GLY B 176       8.449  43.746  89.534  1.00 31.38           C
ATOM   3723  C   GLY B 176       8.853  44.396  88.222  1.00 31.38           C
ATOM   3724  O   GLY B 176       8.416  43.972  87.155  1.00 31.38           O
ATOM   3725  N   ILE B 177       9.688  45.426  88.303  1.00 38.54           N
ATOM   3726  CA  ILE B 177      10.161  46.138  87.123  1.00 38.54           C
ATOM   3727  C   ILE B 177      11.560  45.683  86.686  1.00 38.54           C
ATOM   3728  O   ILE B 177      12.450  45.482  87.512  1.00 38.54           O
ATOM   3729  CB  ILE B 177      10.212  47.655  87.381  1.00 27.99           C
ATOM   3730  CG1 ILE B 177       8.805  48.179  87.678  1.00 27.99           C
ATOM   3731  CG2 ILE B 177      10.819  48.365  86.185  1.00 27.99           C
ATOM   3732  CD1 ILE B 177       8.761  49.658  88.047  1.00 27.99           C
ATOM   3733  N   CYS B 178      11.750  45.514  85.385  1.00 26.93           N
ATOM   3734  CA  CYS B 178      13.045  45.115  84.870  1.00 26.93           C
ATOM   3735  C   CYS B 178      13.464  46.220  83.916  1.00 26.93           C
ATOM   3736  O   CYS B 178      12.712  46.583  83.023  1.00 26.93           O
ATOM   3737  CB  CYS B 178      12.936  43.779  84.132  1.00 26.16           C
ATOM   3738  SG  CYS B 178      14.492  43.108  83.516  1.00 26.16           S
ATOM   3739  N   HIS B 179      14.658  46.763  84.119  1.00 20.61           N
ATOM   3740  CA  HIS B 179      15.167  47.835  83.275  1.00 20.61           C
ATOM   3741  C   HIS B 179      15.328  47.360  81.828  1.00 20.61           C
ATOM   3742  O   HIS B 179      14.998  48.076  80.895  1.00 20.61           O
ATOM   3743  CB  HIS B 179      16.505  48.334  83.845  1.00 18.60           C
ATOM   3744  CG  HIS B 179      17.093  49.493  83.104  1.00 18.60           C
ATOM   3745  ND1 HIS B 179      17.723  49.358  81.886  1.00 18.60           N
ATOM   3746  CD2 HIS B 179      17.136  50.812  83.407  1.00 18.60           C
ATOM   3747  CE1 HIS B 179      18.128  50.544  81.471  1.00 18.60           C
ATOM   3748  NE2 HIS B 179      17.784  51.443  82.376  1.00 18.60           N
ATOM   3749  N   ARG B 180      15.835  46.140  81.676  1.00 26.80           N
ATOM   3750  CA  ARG B 180      16.063  45.500  80.378  1.00 26.80           C
ATOM   3751  C   ARG B 180      17.120  46.105  79.447  1.00 26.80           C
ATOM   3752  O   ARG B 180      17.208  45.710  78.288  1.00 26.80           O
ATOM   3753  CB  ARG B 180      14.759  45.413  79.602  1.00 22.91           C
ATOM   3754  CG  ARG B 180      13.746  44.443  80.141  1.00 22.91           C
ATOM   3755  CD  ARG B 180      12.416  44.906  79.668  1.00 22.91           C
ATOM   3756  NE  ARG B 180      11.722  43.922  78.868  1.00 22.91           N
ATOM   3757  CZ  ARG B 180      10.768  44.224  77.999  1.00 22.91           C
ATOM   3758  NH1 ARG B 180      10.403  45.485  77.808  1.00 22.91           N
ATOM   3759  NH2 ARG B 180      10.159  43.255  77.339  1.00 22.91           N
ATOM   3760  N   ASP B 181      17.911  47.055  79.934  1.00 22.02           N
ATOM   3761  CA  ASP B 181      18.939  47.666  79.103  1.00 22.02           C
ATOM   3762  C   ASP B 181      20.011  48.256  80.021  1.00 22.02           C
ATOM   3763  O   ASP B 181      20.261  49.455  80.038  1.00 22.02           O
ATOM   3764  CB  ASP B 181      18.316  48.732  78.194  1.00 28.37           C
ATOM   3765  CG  ASP B 181      19.271  49.206  77.106  1.00 28.37           C
ATOM   3766  OD1 ASP B 181      19.981  48.352  76.522  1.00 28.37           O
ATOM   3767  OD2 ASP B 181      19.300  50.427  76.835  1.00 28.37           O
ATOM   3768  N   ILE B 182      20.662  47.324  80.738  1.00 24.27           N
ATOM   3769  CA  ILE B 182      21.658  47.779  81.688  1.00 24.27           C
ATOM   3770  C   ILE B 182      22.981  47.701  80.939  1.00 24.27           C
ATOM   3771  O   ILE B 182      23.420  46.628  80.542  1.00 24.27           O
ATOM   3772  CB  ILE B 182      21.766  46.828  82.914  1.00 11.90           C
ATOM   3773  CG1 ILE B 182      20.465  46.898  83.727  1.00 11.90           C
ATOM   3774  CG2 ILE B 182      22.995  47.152  83.750  1.00 11.90           C
ATOM   3775  CD1 ILE B 182      20.183  48.232  84.344  1.00 11.90           C
ATOM   3776  N   LYS B 183      23.582  48.858  80.720  1.00 25.61           N
ATOM   3777  CA  LYS B 183      24.840  48.953  80.017  1.00 25.61           C
ATOM   3778  C   LYS B 183      25.529  50.185  80.599  1.00 25.61           C
ATOM   3779  O   LYS B 183      24.864  51.071  81.133  1.00 25.61           O
```

FIG. 1-62

```
ATOM   3780  CB  LYS B 183      24.587  49.097  78.521  1.00 26.84           C
ATOM   3781  CG  LYS B 183      23.655  50.227  78.160  1.00 26.84           C
ATOM   3782  CD  LYS B 183      23.386  50.212  76.676  1.00 26.84           C
ATOM   3783  CE  LYS B 183      22.511  51.361  76.259  1.00 26.84           C
ATOM   3784  NZ  LYS B 183      22.311  51.388  74.793  1.00 26.84           N
ATOM   3785  N   PRO B 184      26.864  50.262  80.493  1.00 24.98           N
ATOM   3786  CA  PRO B 184      27.637  51.390  81.028  1.00 24.98           C
ATOM   3787  C   PRO B 184      27.109  52.772  80.686  1.00 24.98           C
ATOM   3788  O   PRO B 184      27.178  53.689  81.499  1.00 24.98           O
ATOM   3789  CB  PRO B 184      29.033  51.144  80.469  1.00 26.91           C
ATOM   3790  CG  PRO B 184      29.075  49.638  80.323  1.00 26.91           C
ATOM   3791  CD  PRO B 184      27.731  49.346  79.732  1.00 26.91           C
ATOM   3792  N   GLN B 185      26.580  52.906  79.478  1.00 25.81           N
ATOM   3793  CA  GLN B 185      26.048  54.171  78.985  1.00 25.81           C
ATOM   3794  C   GLN B 185      24.842  54.664  79.776  1.00 25.81           C
ATOM   3795  O   GLN B 185      24.535  55.855  79.783  1.00 25.81           O
ATOM   3796  CB  GLN B 185      25.661  54.035  77.504  1.00 36.37           C
ATOM   3797  CG  GLN B 185      26.826  53.687  76.573  1.00 36.37           C
ATOM   3798  CD  GLN B 185      27.430  52.332  76.885  1.00 36.37           C
ATOM   3799  OE1 GLN B 185      26.987  51.315  76.374  1.00 36.37           O
ATOM   3800  NE2 GLN B 185      28.434  52.316  77.748  0.00 36.37           N
ATOM   3801  N   ASN B 186      24.154  53.739  80.437  1.00 30.97           N
ATOM   3802  CA  ASN B 186      22.984  54.092  81.223  1.00 30.97           C
ATOM   3803  C   ASN B 186      23.307  54.276  82.685  1.00 30.97           C
ATOM   3804  O   ASN B 186      22.403  54.435  83.500  1.00 30.97           O
ATOM   3805  CB  ASN B 186      21.888  53.046  81.078  1.00 18.75           C
ATOM   3806  CG  ASN B 186      21.236  53.078  79.732  1.00 18.75           C
ATOM   3807  OD1 ASN B 186      21.075  54.132  79.138  1.00 18.75           O
ATOM   3808  ND2 ASN B 186      20.838  51.921  79.246  1.00 18.75           N
ATOM   3809  N   LEU B 187      24.589  54.243  83.024  1.00 21.44           N
ATOM   3810  CA  LEU B 187      24.998  54.463  84.404  1.00 21.44           C
ATOM   3811  C   LEU B 187      25.540  55.899  84.601  1.00 21.44           C
ATOM   3812  O   LEU B 187      26.734  56.163  84.424  1.00 21.44           O
ATOM   3813  CB  LEU B 187      26.043  53.419  84.797  1.00 26.67           C
ATOM   3814  CG  LEU B 187      25.584  52.033  85.281  1.00 26.67           C
ATOM   3815  CD1 LEU B 187      24.105  51.819  85.046  1.00 26.67           C
ATOM   3816  CD2 LEU B 187      26.386  50.967  84.581  1.00 26.67           C
ATOM   3817  N   LEU B 188      24.656  56.835  84.943  1.00 23.69           N
ATOM   3818  CA  LEU B 188      25.087  58.218  85.153  1.00 23.69           C
ATOM   3819  C   LEU B 188      25.867  58.343  86.453  1.00 23.69           C
ATOM   3820  O   LEU B 188      25.525  57.704  87.441  1.00 23.69           O
ATOM   3821  CB  LEU B 188      23.889  59.159  85.228  1.00 27.99           C
ATOM   3822  CG  LEU B 188      22.887  59.177  84.077  1.00 27.99           C
ATOM   3823  CD1 LEU B 188      21.903  60.288  84.317  1.00 27.99           C
ATOM   3824  CD2 LEU B 188      23.581  59.387  82.766  1.00 27.99           C
ATOM   3825  N   LEU B 189      26.914  59.163  86.456  1.00 25.95           N
ATOM   3826  CA  LEU B 189      27.693  59.346  87.670  1.00 25.95           C
ATOM   3827  C   LEU B 189      28.250  60.745  87.866  1.00 25.95           C
ATOM   3828  O   LEU B 189      28.472  61.479  86.913  1.00 25.95           O
ATOM   3829  CB  LEU B 189      28.821  58.313  87.741  1.00 37.67           C
ATOM   3830  CG  LEU B 189      29.947  58.308  86.715  1.00 37.67           C
ATOM   3831  CD1 LEU B 189      30.933  59.435  86.993  0.00 37.67           C
ATOM   3832  CD2 LEU B 189      30.658  56.958  86.805  1.00 37.67           C
ATOM   3833  N   ASP B 190      28.444  61.111  89.127  1.00 32.61           N
ATOM   3834  CA  ASP B 190      28.983  62.410  89.482  1.00 32.61           C
ATOM   3835  C   ASP B 190      30.426  62.172  89.897  1.00 32.61           C
ATOM   3836  O   ASP B 190      30.685  61.519  90.908  1.00 32.61           O
ATOM   3837  CB  ASP B 190      28.205  63.015  90.646  1.00 39.95           C
ATOM   3838  CG  ASP B 190      28.748  64.369  91.063  1.00 39.95           C
ATOM   3839  OD1 ASP B 190      29.982  64.491  91.251  1.00 39.95           O
ATOM   3840  OD2 ASP B 190      27.940  65.309  91.211  1.00 39.95           O
ATOM   3841  N   PRO B 191      31.386  62.719  89.133  1.00 50.68           N
```

FIG. 1-63

```
ATOM   3842  CA  PRO B 191      32.805  62.542  89.437  1.00 50.68           C
ATOM   3843  C   PRO B 191      33.152  62.863  90.876  1.00 50.68           C
ATOM   3844  O   PRO B 191      33.746  62.029  91.574  1.00 50.68           O
ATOM   3845  CB  PRO B 191      33.491  63.479  88.448  0.00 60.50           C
ATOM   3846  CG  PRO B 191      32.532  64.582  88.337  1.00 60.50           C
ATOM   3847  CD  PRO B 191      31.211  63.833  88.184  1.00 60.50           C
ATOM   3848  N   ASP B 192      32.757  64.056  91.322  1.00 41.81           N
ATOM   3849  CA  ASP B 192      33.054  64.518  92.676  1.00 41.81           C
ATOM   3850  C   ASP B 192      32.441  63.700  93.822  1.00 41.81           C
ATOM   3851  O   ASP B 192      33.104  63.423  94.819  1.00 41.81           O
ATOM   3852  CB  ASP B 192      32.623  65.983  92.852  1.00 58.23           C
ATOM   3853  CG  ASP B 192      33.083  66.895  91.702  1.00 58.23           C
ATOM   3854  OD1 ASP B 192      34.262  66.788  91.253  1.00 58.23           O
ATOM   3855  OD2 ASP B 192      32.249  67.742  91.267  1.00 58.23           O
ATOM   3856  N   THR B 193      31.181  63.314  93.703  1.00 27.29           N
ATOM   3857  CA  THR B 193      30.561  62.580  94.794  1.00 27.29           C
ATOM   3858  C   THR B 193      30.584  61.063  94.634  1.00 27.29           C
ATOM   3859  O   THR B 193      30.344  60.336  95.585  1.00 27.29           O
ATOM   3860  CB  THR B 193      29.123  63.069  94.994  1.00 28.38           C
ATOM   3861  OG1 THR B 193      28.315  62.652  93.890  1.00 28.38           O
ATOM   3862  CG2 THR B 193      29.102  64.584  95.052  1.00 28.38           C
ATOM   3863  N   ALA B 194      30.889  60.585  93.434  1.00 24.90           N
ATOM   3864  CA  ALA B 194      30.932  59.146  93.179  1.00 24.90           C
ATOM   3865  C   ALA B 194      29.542  58.511  93.285  1.00 24.90           C
ATOM   3866  O   ALA B 194      29.405  57.316  93.535  1.00 24.90           O
ATOM   3867  CB  ALA B 194      31.897  58.468  94.148  1.00 15.13           C
ATOM   3868  N   VAL B 195      28.516  59.330  93.087  1.00 23.36           N
ATOM   3869  CA  VAL B 195      27.135  58.880  93.147  1.00 23.36           C
ATOM   3870  C   VAL B 195      26.725  58.335  91.790  1.00 23.36           C
ATOM   3871  O   VAL B 195      26.898  58.993  90.773  1.00 23.36           O
ATOM   3872  CB  VAL B 195      26.203  60.053  93.536  1.00 15.16           C
ATOM   3873  CG1 VAL B 195      24.752  59.695  93.304  1.00 15.16           C
ATOM   3874  CG2 VAL B 195      26.421  60.403  94.980  1.00 15.16           C
ATOM   3875  N   LEU B 196      26.194  57.124  91.768  1.00 19.41           N
ATOM   3876  CA  LEU B 196      25.764  56.552  90.510  1.00 19.41           C
ATOM   3877  C   LEU B 196      24.253  56.633  90.422  1.00 19.41           C
ATOM   3878  O   LEU B 196      23.566  56.597  91.433  1.00 19.41           O
ATOM   3879  CB  LEU B 196      26.223  55.094  90.391  1.00 19.09           C
ATOM   3880  CG  LEU B 196      25.774  54.309  89.151  1.00 19.09           C
ATOM   3881  CD1 LEU B 196      26.694  53.126  88.926  1.00 19.09           C
ATOM   3882  CD2 LEU B 196      24.328  53.855  89.320  1.00 19.09           C
ATOM   3883  N   LYS B 197      23.745  56.759  89.206  1.00 25.21           N
ATOM   3884  CA  LYS B 197      22.311  56.829  88.978  1.00 25.21           C
ATOM   3885  C   LYS B 197      21.907  56.062  87.738  1.00 25.21           C
ATOM   3886  O   LYS B 197      22.498  56.238  86.677  1.00 25.21           O
ATOM   3887  CB  LYS B 197      21.859  58.281  88.850  1.00 21.67           C
ATOM   3888  CG  LYS B 197      21.609  58.937  90.172  1.00 21.67           C
ATOM   3889  CD  LYS B 197      21.334  60.399  90.008  1.00 21.67           C
ATOM   3890  CE  LYS B 197      20.902  61.012  91.327  1.00 21.67           C
ATOM   3891  NZ  LYS B 197      21.876  60.720  92.392  1.00 21.67           N
ATOM   3892  N   LEU B 198      20.916  55.189  87.883  1.00 24.72           N
ATOM   3893  CA  LEU B 198      20.425  54.418  86.753  1.00 24.72           C
ATOM   3894  C   LEU B 198      19.507  55.338  85.954  1.00 24.72           C
ATOM   3895  O   LEU B 198      18.703  56.068  86.530  1.00 24.72           O
ATOM   3896  CB  LEU B 198      19.659  53.187  87.240  1.00 13.35           C
ATOM   3897  CG  LEU B 198      19.010  52.280  86.194  1.00 13.35           C
ATOM   3898  CD1 LEU B 198      20.025  51.791  85.212  1.00 13.35           C
ATOM   3899  CD2 LEU B 198      18.363  51.113  86.871  1.00 13.35           C
ATOM   3900  N   CYS B 199      19.651  55.325  84.632  1.00 22.21           N
ATOM   3901  CA  CYS B 199      18.823  56.160  83.768  1.00 22.21           C
ATOM   3902  C   CYS B 199      18.315  55.392  82.542  1.00 22.21           C
ATOM   3903  O   CYS B 199      18.629  54.225  82.357  1.00 22.21           O
```

FIG. 1-64

```
ATOM   3904  CB   CYS B 199      19.604  57.397  83.308  1.00 28.99           C
ATOM   3905  SG   CYS B 199      20.866  57.074  82.054  1.00 28.99           S
ATOM   3906  N    ASP B 200      17.524  56.070  81.719  1.00 23.92           N
ATOM   3907  CA   ASP B 200      16.956  55.484  80.515  1.00 23.92           C
ATOM   3908  C    ASP B 200      16.026  54.289  80.752  1.00 23.92           C
ATOM   3909  O    ASP B 200      16.443  53.131  80.646  1.00 23.92           O
ATOM   3910  CB   ASP B 200      18.057  55.053  79.563  1.00 34.92           C
ATOM   3911  CG   ASP B 200      17.512  54.618  78.231  1.00 34.92           C
ATOM   3912  OD1  ASP B 200      16.270  54.557  78.095  1.00 34.92           O
ATOM   3913  OD2  ASP B 200      18.319  54.339  77.317  1.00 34.92           O
ATOM   3914  N    PHE B 201      14.759  54.564  81.045  1.00 29.97           N
ATOM   3915  CA   PHE B 201      13.805  53.495  81.281  1.00 29.97           C
ATOM   3916  C    PHE B 201      12.904  53.211  80.069  1.00 29.97           C
ATOM   3917  O    PHE B 201      11.803  52.680  80.203  1.00 29.97           O
ATOM   3918  CB   PHE B 201      12.971  53.824  82.524  1.00 21.34           C
ATOM   3919  CG   PHE B 201      13.738  53.713  83.806  1.00 21.34           C
ATOM   3920  CD1  PHE B 201      14.659  54.683  84.166  1.00 21.34           C
ATOM   3921  CD2  PHE B 201      13.596  52.595  84.618  1.00 21.34           C
ATOM   3922  CE1  PHE B 201      15.437  54.536  85.318  1.00 21.34           C
ATOM   3923  CE2  PHE B 201      14.363  52.438  85.765  1.00 21.34           C
ATOM   3924  CZ   PHE B 201      15.288  53.411  86.116  1.00 21.34           C
ATOM   3925  N    GLY B 202      13.388  53.549  78.882  1.00 21.68           N
ATOM   3926  CA   GLY B 202      12.601  53.324  77.685  1.00 21.68           C
ATOM   3927  C    GLY B 202      12.315  51.869  77.356  1.00 21.68           C
ATOM   3928  O    GLY B 202      11.433  51.575  76.552  1.00 21.68           O
ATOM   3929  N    SER B 203      13.048  50.954  77.975  1.00 32.70           N
ATOM   3930  CA   SER B 203      12.856  49.534  77.715  1.00 32.70           C
ATOM   3931  C    SER B 203      12.335  48.806  78.921  1.00 32.70           C
ATOM   3932  O    SER B 203      12.117  47.608  78.855  1.00 32.70           O
ATOM   3933  CB   SER B 203      14.171  48.881  77.311  1.00 29.51           C
ATOM   3934  OG   SER B 203      14.771  49.595  76.259  1.00 29.51           O
ATOM   3935  N    ALA B 204      12.156  49.528  80.020  1.00 20.67           N
ATOM   3936  CA   ALA B 204      11.687  48.942  81.262  1.00 20.67           C
ATOM   3937  C    ALA B 204      10.236  48.489  81.209  1.00 20.67           C
ATOM   3938  O    ALA B 204       9.406  49.062  80.496  1.00 20.67           O
ATOM   3939  CB   ALA B 204      11.882  49.932  82.405  1.00 28.67           C
ATOM   3940  N    LYS B 205       9.933  47.465  81.993  1.00 24.34           N
ATOM   3941  CA   LYS B 205       8.590  46.930  82.035  1.00 24.34           C
ATOM   3942  C    LYS B 205       8.311  46.105  83.293  1.00 24.34           C
ATOM   3943  O    LYS B 205       9.210  45.511  83.879  1.00 24.34           O
ATOM   3944  CB   LYS B 205       8.359  46.057  80.809  1.00 33.91           C
ATOM   3945  CG   LYS B 205       6.923  45.660  80.675  1.00 33.91           C
ATOM   3946  CD   LYS B 205       6.705  44.576  79.642  1.00 33.91           C
ATOM   3947  CE   LYS B 205       5.210  44.354  79.383  1.00 33.91           C
ATOM   3948  NZ   LYS B 205       4.954  43.138  78.564  1.00 33.91           N
ATOM   3949  N    GLN B 206       7.056  46.083  83.715  1.00 31.27           N
ATOM   3950  CA   GLN B 206       6.670  45.280  84.862  1.00 31.27           C
ATOM   3951  C    GLN B 206       6.597  43.871  84.292  1.00 31.27           C
ATOM   3952  O    GLN B 206       5.893  43.642  83.317  1.00 31.27           O
ATOM   3953  CB   GLN B 206       5.300  45.705  85.366  1.00 53.66           C
ATOM   3954  CG   GLN B 206       5.180  47.198  85.627  1.00 53.66           C
ATOM   3955  CD   GLN B 206       4.520  47.475  86.971  1.00 53.66           C
ATOM   3956  OE1  GLN B 206       4.259  48.638  87.338  1.00 53.66           O
ATOM   3957  NE2  GLN B 206       4.247  46.395  87.721  1.00 53.66           N
ATOM   3958  N    LEU B 207       7.331  42.934  84.876  1.00 33.98           N
ATOM   3959  CA   LEU B 207       7.336  41.569  84.361  1.00 33.98           C
ATOM   3960  C    LEU B 207       6.400  40.639  85.101  1.00 33.98           C
ATOM   3961  O    LEU B 207       6.827  39.908  85.997  1.00 33.98           O
ATOM   3962  CB   LEU B 207       8.743  40.969  84.418  1.00 29.59           C
ATOM   3963  CG   LEU B 207       9.856  41.433  83.481  1.00 29.59           C
ATOM   3964  CD1  LEU B 207      11.024  40.470  83.647  1.00 29.59           C
ATOM   3965  CD2  LEU B 207       9.385  41.450  82.026  1.00 29.59           C
```

FIG. 1-65

| | | | | | | | | | | |
|---|---|---|---|---|---|---|---|---|---|---|
| ATOM | 3966 | N | VAL | B | 208 | 5.132 | 40.648 | 84.715 | 1.00 44.62 | N |
| ATOM | 3967 | CA | VAL | B | 208 | 4.133 | 39.791 | 85.350 | 1.00 44.62 | C |
| ATOM | 3968 | C | VAL | B | 208 | 4.300 | 38.335 | 84.900 | 1.00 44.62 | C |
| ATOM | 3969 | O | VAL | B | 208 | 4.349 | 38.054 | 83.705 | 1.00 44.62 | O |
| ATOM | 3970 | CB | VAL | B | 208 | 2.720 | 40.267 | 84.988 | 1.00 41.62 | C |
| ATOM | 3971 | CG1 | VAL | B | 208 | 1.710 | 39.724 | 85.987 | 0.00 41.62 | C |
| ATOM | 3972 | CG2 | VAL | B | 208 | 2.696 | 41.794 | 84.939 | 1.00 41.62 | C |
| ATOM | 3973 | N | ARG | B | 209 | 4.389 | 37.410 | 85.853 | 1.00 45.27 | N |
| ATOM | 3974 | CA | ARG | B | 209 | 4.549 | 35.987 | 85.520 | 1.00 45.27 | C |
| ATOM | 3975 | C | ARG | B | 209 | 3.458 | 35.489 | 84.550 | 1.00 45.27 | C |
| ATOM | 3976 | O | ARG | B | 209 | 2.294 | 35.902 | 84.622 | 1.00 45.27 | O |
| ATOM | 3977 | CB | ARG | B | 209 | 4.541 | 35.142 | 86.804 | 1.00 34.94 | C |
| ATOM | 3978 | N | GLY | B | 210 | 3.839 | 34.607 | 83.634 | 1.00 39.40 | N |
| ATOM | 3979 | CA | GLY | B | 210 | 2.874 | 34.097 | 82.682 | 1.00 39.40 | C |
| ATOM | 3980 | C | GLY | B | 210 | 2.739 | 34.939 | 81.428 | 1.00 39.40 | C |
| ATOM | 3981 | O | GLY | B | 210 | 2.256 | 34.451 | 80.402 | 1.00 39.40 | O |
| ATOM | 3982 | N | GLU | B | 211 | 3.147 | 36.203 | 81.495 | 1.00 48.68 | N |
| ATOM | 3983 | CA | GLU | B | 211 | 3.066 | 37.074 | 80.323 | 1.00 48.68 | C |
| ATOM | 3984 | C | GLU | B | 211 | 4.365 | 37.073 | 79.534 | 1.00 48.68 | C |
| ATOM | 3985 | O | GLU | B | 211 | 5.446 | 37.193 | 80.097 | 1.00 48.68 | O |
| ATOM | 3986 | CB | GLU | B | 211 | 2.728 | 38.495 | 80.728 | 1.00 61.36 | C |
| ATOM | 3987 | CG | GLU | B | 211 | 1.302 | 38.658 | 81.185 | 1.00 61.36 | C |
| ATOM | 3988 | CD | GLU | B | 211 | 1.004 | 40.078 | 81.629 | 1.00 61.36 | C |
| ATOM | 3989 | OE1 | GLU | B | 211 | -0.121 | 40.323 | 82.132 | 1.00 61.36 | O |
| ATOM | 3990 | OE2 | GLU | B | 211 | 1.901 | 40.946 | 81.470 | 1.00 61.36 | O |
| ATOM | 3991 | N | PRO | B | 212 | 4.271 | 36.924 | 78.211 | 1.00 42.30 | N |
| ATOM | 3992 | CA | PRO | B | 212 | 5.459 | 36.909 | 77.364 | 1.00 42.30 | C |
| ATOM | 3993 | C | PRO | B | 212 | 6.042 | 38.299 | 77.164 | 1.00 42.30 | C |
| ATOM | 3994 | O | PRO | B | 212 | 5.309 | 39.295 | 77.171 | 1.00 42.30 | O |
| ATOM | 3995 | CB | PRO | B | 212 | 4.940 | 36.297 | 76.063 | 1.00 48.75 | C |
| ATOM | 3996 | CG | PRO | B | 212 | 3.553 | 36.807 | 76.004 | 1.00 48.75 | C |
| ATOM | 3997 | CD | PRO | B | 212 | 3.063 | 36.625 | 77.420 | 1.00 48.75 | C |
| ATOM | 3998 | N | ASN | B | 213 | 7.362 | 38.358 | 77.002 | 1.00 29.63 | N |
| ATOM | 3999 | CA | ASN | B | 213 | 8.043 | 39.621 | 76.780 | 1.00 29.63 | C |
| ATOM | 4000 | C | ASN | B | 213 | 8.996 | 39.474 | 75.601 | 1.00 29.63 | C |
| ATOM | 4001 | O | ASN | B | 213 | 9.568 | 38.405 | 75.387 | 1.00 29.63 | O |
| ATOM | 4002 | CB | ASN | B | 213 | 8.790 | 40.032 | 78.041 | 1.00 23.53 | C |
| ATOM | 4003 | CG | ASN | B | 213 | 7.869 | 40.178 | 79.229 | 1.00 23.53 | C |
| ATOM | 4004 | OD1 | ASN | B | 213 | 7.045 | 41.096 | 79.288 | 1.00 23.53 | O |
| ATOM | 4005 | ND2 | ASN | B | 213 | 7.991 | 39.256 | 80.180 | 1.00 23.53 | N |
| ATOM | 4006 | N | VAL | B | 214 | 9.141 | 40.543 | 74.826 | 1.00 26.81 | N |
| ATOM | 4007 | CA | VAL | B | 214 | 10.079 | 40.505 | 73.707 | 1.00 26.81 | C |
| ATOM | 4008 | C | VAL | B | 214 | 11.504 | 40.191 | 74.176 | 1.00 26.81 | C |
| ATOM | 4009 | O | VAL | B | 214 | 11.892 | 40.452 | 75.307 | 1.00 26.81 | O |
| ATOM | 4010 | CB | VAL | B | 214 | 10.043 | 41.860 | 72.999 | 1.00 21.30 | C |
| ATOM | 4011 | CG1 | VAL | B | 214 | 8.640 | 42.126 | 72.456 | 1.00 21.30 | C |
| ATOM | 4012 | CG2 | VAL | B | 214 | 10.422 | 42.965 | 73.969 | 1.00 21.30 | C |
| ATOM | 4013 | N | SER | B | 215 | 12.283 | 39.571 | 73.268 | 1.00 28.62 | N |
| ATOM | 4014 | CA | SER | B | 215 | 13.621 | 39.099 | 73.612 | 1.00 28.62 | C |
| ATOM | 4015 | C | SER | B | 215 | 14.704 | 40.039 | 73.079 | 1.00 28.62 | C |
| ATOM | 4016 | O | SER | B | 215 | 15.822 | 40.103 | 73.576 | 1.00 28.62 | O |
| ATOM | 4017 | CB | SER | B | 215 | 13.805 | 37.705 | 73.015 | 1.00 30.12 | C |
| ATOM | 4018 | OG | SER | B | 215 | 13.657 | 37.776 | 71.597 | 1.00 30.12 | O |
| ATOM | 4019 | N | TYR | B | 216 | 14.348 | 40.751 | 71.995 | 1.00 29.71 | N |
| ATOM | 4020 | CA | TYR | B | 216 | 15.281 | 41.710 | 71.414 | 1.00 29.71 | C |
| ATOM | 4021 | C | TYR | B | 216 | 15.185 | 43.066 | 72.113 | 1.00 29.71 | C |
| ATOM | 4022 | O | TYR | B | 216 | 14.718 | 44.053 | 71.561 | 1.00 29.71 | O |
| ATOM | 4023 | CB | TYR | B | 216 | 14.921 | 41.871 | 69.936 | 1.00 34.42 | C |
| ATOM | 4024 | CG | TYR | B | 216 | 13.545 | 42.430 | 69.821 | 1.00 34.42 | C |
| ATOM | 4025 | CD1 | TYR | B | 216 | 13.324 | 43.781 | 70.074 | 1.00 34.42 | C |
| ATOM | 4026 | CD2 | TYR | B | 216 | 12.462 | 41.592 | 69.554 | 1.00 34.42 | C |
| ATOM | 4027 | CE1 | TYR | B | 216 | 12.033 | 44.290 | 70.070 | 1.00 34.42 | C |

FIG. 1-66

```
ATOM   4028  CE2 TYR B 216      11.170  42.100  69.550  1.00 34.42           C
ATOM   4029  CZ  TYR B 216      10.955  43.442  69.808  1.00 34.42           C
ATOM   4030  OH  TYR B 216       9.675  43.961  69.782  1.00 34.42           O
ATOM   4031  N   ILE B 217      15.613  43.086  73.389  1.00 44.24           N
ATOM   4032  CA  ILE B 217      15.470  44.310  74.169  1.00 44.24           C
ATOM   4033  C   ILE B 217      16.809  44.801  74.728  1.00 44.24           C
ATOM   4034  O   ILE B 217      17.135  45.980  74.702  1.00 44.24           O
ATOM   4035  CB  ILE B 217      14.486  44.034  75.307  1.00 22.42           C
ATOM   4036  CG1 ILE B 217      14.199  45.321  76.084  1.00 22.42           C
ATOM   4037  CG2 ILE B 217      15.093  43.012  76.287  1.00 22.42           C
ATOM   4038  CD1 ILE B 217      13.249  46.254  75.333  1.00 22.42           C
ATOM   4039  N   CYS B 218      17.582  43.850  75.284  1.00 30.97           N
ATOM   4040  CA  CYS B 218      18.877  44.218  75.846  1.00 30.97           C
ATOM   4041  C   CYS B 218      19.884  44.577  74.752  1.00 30.97           C
ATOM   4042  O   CYS B 218      19.589  44.574  73.565  1.00 30.97           O
ATOM   4043  CB  CYS B 218      19.398  43.038  76.668  1.00 33.67           C
ATOM   4044  SG  CYS B 218      20.588  43.554  77.927  1.00 33.67           S
ATOM   4045  N   SER B 219      21.102  44.935  75.197  1.00 27.56           N
ATOM   4046  CA  SER B 219      22.140  45.291  74.238  1.00 27.56           C
ATOM   4047  C   SER B 219      23.031  44.094  73.903  1.00 27.56           C
ATOM   4048  O   SER B 219      22.896  43.004  74.444  1.00 27.56           O
ATOM   4049  CB  SER B 219      22.981  46.415  74.844  1.00 30.92           C
ATOM   4050  OG  SER B 219      22.585  47.660  74.267  1.00 30.92           O
ATOM   4051  N   ARG B 220      23.943  44.318  72.940  1.00 31.13           N
ATOM   4052  CA  ARG B 220      24.848  43.247  72.541  1.00 31.13           C
ATOM   4053  C   ARG B 220      25.697  42.509  73.579  1.00 31.13           C
ATOM   4054  O   ARG B 220      25.429  41.371  73.943  1.00 31.13           O
ATOM   4055  CB  ARG B 220      25.850  43.821  71.538  1.00 26.70           C
ATOM   4056  N   TYR B 221      26.700  43.258  74.067  1.00 28.91           N
ATOM   4057  CA  TYR B 221      27.606  42.635  75.012  1.00 28.91           C
ATOM   4058  C   TYR B 221      26.809  42.484  76.315  1.00 28.91           C
ATOM   4059  O   TYR B 221      27.156  41.750  77.232  1.00 28.91           O
ATOM   4060  CB  TYR B 221      28.799  43.593  75.285  1.00 45.58           C
ATOM   4061  CG  TYR B 221      29.362  44.052  73.988  1.00 45.58           C
ATOM   4062  CD1 TYR B 221      29.333  43.210  72.880  1.00 45.58           C
ATOM   4063  CD2 TYR B 221      29.926  45.323  73.876  1.00 45.58           C
ATOM   4064  CE1 TYR B 221      29.856  43.637  71.668  1.00 45.58           C
ATOM   4065  CE2 TYR B 221      30.449  45.749  72.664  1.00 45.58           C
ATOM   4066  CZ  TYR B 221      30.410  44.914  71.563  1.00 45.58           C
ATOM   4067  OH  TYR B 221      30.865  45.357  70.336  1.00 45.58           O
ATOM   4068  N   TYR B 222      25.637  43.083  76.591  1.00 28.02           N
ATOM   4069  CA  TYR B 222      25.017  42.855  77.895  1.00 28.02           C
ATOM   4070  C   TYR B 222      23.809  41.917  77.812  1.00 28.02           C
ATOM   4071  O   TYR B 222      23.160  41.608  78.803  1.00 28.02           O
ATOM   4072  CB  TYR B 222      24.599  44.209  78.465  1.00 23.72           C
ATOM   4073  CG  TYR B 222      25.717  45.179  78.311  1.00 23.72           C
ATOM   4074  CD1 TYR B 222      25.784  45.982  77.176  1.00 23.72           C
ATOM   4075  CD2 TYR B 222      26.757  45.209  79.240  1.00 23.72           C
ATOM   4076  CE1 TYR B 222      26.887  46.794  76.961  1.00 23.72           C
ATOM   4077  CE2 TYR B 222      27.861  46.021  79.025  1.00 23.72           C
ATOM   4078  CZ  TYR B 222      27.930  46.808  77.889  1.00 23.72           C
ATOM   4079  OH  TYR B 222      29.030  47.610  77.659  1.00 23.72           O
ATOM   4080  N   ARG B 223      23.377  41.376  76.660  1.00 24.53           N
ATOM   4081  CA  ARG B 223      22.227  40.481  76.678  1.00 24.53           C
ATOM   4082  C   ARG B 223      22.550  39.164  77.391  1.00 24.53           C
ATOM   4083  O   ARG B 223      23.540  38.502  77.107  1.00 24.53           O
ATOM   4084  CB  ARG B 223      21.814  40.212  75.231  1.00 26.99           C
ATOM   4085  CG  ARG B 223      21.984  41.446  74.343  1.00 26.99           C
ATOM   4086  CD  ARG B 223      21.564  41.177  72.894  1.00 26.99           C
ATOM   4087  NE  ARG B 223      20.208  40.623  72.844  1.00 26.99           N
ATOM   4088  CZ  ARG B 223      19.995  39.593  72.005  1.00 26.99           C
ATOM   4089  NH1 ARG B 223      20.985  39.123  71.266  1.00 26.99           N
```

FIG. 1-67

```
ATOM   4090  NH2 ARG B 223      18.783  39.034  71.940  1.00 26.99           N
ATOM   4091  N   ALA B 224      21.619  38.783  78.255  1.00 17.47           N
ATOM   4092  CA  ALA B 224      21.740  37.528  78.954  1.00 17.47           C
ATOM   4093  C   ALA B 224      21.665  36.408  77.954  1.00 17.47           C
ATOM   4094  O   ALA B 224      21.072  36.535  76.891  1.00 17.47           O
ATOM   4095  CB  ALA B 224      20.643  37.383  79.979  1.00 11.85           C
ATOM   4096  N   PRO B 225      22.284  35.285  78.281  1.00 28.48           N
ATOM   4097  CA  PRO B 225      22.224  34.188  77.338  1.00 28.48           C
ATOM   4098  C   PRO B 225      20.783  33.821  76.883  1.00 28.48           C
ATOM   4099  O   PRO B 225      20.528  33.760  75.683  1.00 28.48           O
ATOM   4100  CB  PRO B 225      23.014  33.105  78.080  1.00 23.08           C
ATOM   4101  CG  PRO B 225      22.796  33.413  79.479  1.00 23.08           C
ATOM   4102  CD  PRO B 225      23.028  34.885  79.481  1.00 23.08           C
ATOM   4103  N   GLU B 226      19.840  33.624  77.802  1.00 30.52           N
ATOM   4104  CA  GLU B 226      18.461  33.294  77.408  1.00 30.52           C
ATOM   4105  C   GLU B 226      17.892  34.283  76.380  1.00 30.52           C
ATOM   4106  O   GLU B 226      17.102  33.899  75.523  1.00 30.52           O
ATOM   4107  CB  GLU B 226      17.533  33.249  78.624  1.00 32.28           C
ATOM   4108  CG  GLU B 226      17.508  34.535  79.428  1.00 32.28           C
ATOM   4109  CD  GLU B 226      18.283  34.415  80.716  1.00 32.28           C
ATOM   4110  OE1 GLU B 226      19.417  33.905  80.680  1.00 32.28           O
ATOM   4111  OE2 GLU B 226      17.765  34.833  81.769  1.00 32.28           O
ATOM   4112  N   LEU B 227      18.268  35.556  76.468  1.00 23.55           N
ATOM   4113  CA  LEU B 227      17.787  36.531  75.489  1.00 23.55           C
ATOM   4114  C   LEU B 227      18.331  36.190  74.096  1.00 23.55           C
ATOM   4115  O   LEU B 227      17.621  36.292  73.095  1.00 23.55           O
ATOM   4116  CB  LEU B 227      18.220  37.949  75.860  1.00 25.52           C
ATOM   4117  CG  LEU B 227      17.671  38.519  77.164  1.00 25.52           C
ATOM   4118  CD1 LEU B 227      18.146  39.960  77.310  1.00 25.52           C
ATOM   4119  CD2 LEU B 227      16.154  38.452  77.170  1.00 25.52           C
ATOM   4120  N   ILE B 228      19.595  35.789  74.036  1.00 23.90           N
ATOM   4121  CA  ILE B 228      20.189  35.431  72.767  1.00 23.90           C
ATOM   4122  C   ILE B 228      19.395  34.253  72.203  1.00 23.90           C
ATOM   4123  O   ILE B 228      19.049  34.232  71.028  1.00 23.90           O
ATOM   4124  CB  ILE B 228      21.676  35.055  72.937  1.00 17.80           C
ATOM   4125  CG1 ILE B 228      22.445  36.244  73.536  1.00 17.80           C
ATOM   4126  CG2 ILE B 228      22.262  34.678  71.598  1.00 17.80           C
ATOM   4127  CD1 ILE B 228      23.931  35.991  73.773  1.00 17.80           C
ATOM   4128  N   PHE B 229      19.087  33.283  73.054  1.00 40.04           N
ATOM   4129  CA  PHE B 229      18.324  32.126  72.615  1.00 40.04           C
ATOM   4130  C   PHE B 229      16.868  32.439  72.304  1.00 40.04           C
ATOM   4131  O   PHE B 229      16.080  31.527  72.073  1.00 40.04           O
ATOM   4132  CB  PHE B 229      18.370  31.004  73.650  1.00 26.10           C
ATOM   4133  CG  PHE B 229      19.666  30.255  73.676  1.00 26.10           C
ATOM   4134  CD1 PHE B 229      20.157  29.623  72.532  1.00 26.10           C
ATOM   4135  CD2 PHE B 229      20.393  30.166  74.845  1.00 26.10           C
ATOM   4136  CE1 PHE B 229      21.352  28.915  72.559  1.00 26.10           C
ATOM   4137  CE2 PHE B 229      21.593  29.457  74.884  1.00 26.10           C
ATOM   4138  CZ  PHE B 229      22.075  28.837  73.754  1.00 26.10           C
ATOM   4139  N   GLY B 230      16.493  33.712  72.311  1.00 35.01           N
ATOM   4140  CA  GLY B 230      15.123  34.065  71.972  1.00 35.01           C
ATOM   4141  C   GLY B 230      13.999  33.814  72.965  1.00 35.01           C
ATOM   4142  O   GLY B 230      12.833  33.915  72.595  1.00 35.01           O
ATOM   4143  N   ALA B 231      14.327  33.495  74.212  1.00 26.93           N
ATOM   4144  CA  ALA B 231      13.311  33.265  75.235  1.00 26.93           C
ATOM   4145  C   ALA B 231      12.386  34.471  75.355  1.00 26.93           C
ATOM   4146  O   ALA B 231      12.765  35.589  75.021  1.00 26.93           O
ATOM   4147  CB  ALA B 231      13.974  32.991  76.578  1.00  7.70           C
ATOM   4148  N   THR B 232      11.176  34.248  75.848  1.00 31.17           N
ATOM   4149  CA  THR B 232      10.208  35.327  75.998  1.00 31.17           C
ATOM   4150  C   THR B 232       9.579  35.279  77.385  1.00 31.17           C
ATOM   4151  O   THR B 232       8.714  36.095  77.733  1.00 31.17           O
```

FIG. 1-68

| | | | | | | | | | | |
|---|---|---|---|---|---|---|---|---|---|---|
| ATOM | 4152 | CB | THR | B | 232 | 9.112 | 35.196 | 74.948 | 1.00 36.16 | C |
| ATOM | 4153 | OG1 | THR | B | 232 | 8.775 | 33.809 | 74.811 | 1.00 36.16 | O |
| ATOM | 4154 | CG2 | THR | B | 232 | 9.581 | 35.740 | 73.603 | 1.00 36.16 | C |
| ATOM | 4155 | N | ASP | B | 233 | 10.034 | 34.312 | 78.172 | 1.00 28.99 | N |
| ATOM | 4156 | CA | ASP | B | 233 | 9.544 | 34.114 | 79.522 | 1.00 28.99 | C |
| ATOM | 4157 | C | ASP | B | 233 | 10.674 | 34.393 | 80.506 | 1.00 28.99 | C |
| ATOM | 4158 | O | ASP | B | 233 | 10.757 | 33.763 | 81.564 | 1.00 28.99 | O |
| ATOM | 4159 | CB | ASP | B | 233 | 9.064 | 32.677 | 79.678 | 1.00 34.28 | C |
| ATOM | 4160 | CG | ASP | B | 233 | 10.192 | 31.684 | 79.618 | 1.00 34.28 | C |
| ATOM | 4161 | OD1 | ASP | B | 233 | 11.262 | 32.011 | 79.053 | 1.00 34.28 | O |
| ATOM | 4162 | OD2 | ASP | B | 233 | 10.006 | 30.564 | 80.131 | 1.00 34.28 | O |
| ATOM | 4163 | N | TYR | B | 234 | 11.541 | 35.336 | 80.149 | 1.00 31.44 | N |
| ATOM | 4164 | CA | TYR | B | 234 | 12.668 | 35.693 | 80.996 | 1.00 31.44 | C |
| ATOM | 4165 | C | TYR | B | 234 | 12.240 | 36.504 | 82.211 | 1.00 31.44 | C |
| ATOM | 4166 | O | TYR | B | 234 | 11.190 | 37.135 | 82.206 | 1.00 31.44 | O |
| ATOM | 4167 | CB | TYR | B | 234 | 13.695 | 36.480 | 80.197 | 1.00 22.01 | C |
| ATOM | 4168 | CG | TYR | B | 234 | 13.144 | 37.722 | 79.545 | 1.00 22.01 | C |
| ATOM | 4169 | CD1 | TYR | B | 234 | 12.596 | 37.678 | 78.264 | 1.00 22.01 | C |
| ATOM | 4170 | CD2 | TYR | B | 234 | 13.212 | 38.956 | 80.184 | 1.00 22.01 | C |
| ATOM | 4171 | CE1 | TYR | B | 234 | 12.146 | 38.827 | 77.637 | 1.00 22.01 | C |
| ATOM | 4172 | CE2 | TYR | B | 234 | 12.757 | 40.112 | 79.559 | 1.00 22.01 | C |
| ATOM | 4173 | CZ | TYR | B | 234 | 12.228 | 40.036 | 78.288 | 1.00 22.01 | C |
| ATOM | 4174 | OH | TYR | B | 234 | 11.754 | 41.164 | 77.671 | 1.00 22.01 | O |
| ATOM | 4175 | N | THR | B | 235 | 13.065 | 36.486 | 83.252 | 1.00 26.32 | N |
| ATOM | 4176 | CA | THR | B | 235 | 12.774 | 37.211 | 84.482 | 1.00 26.32 | C |
| ATOM | 4177 | C | THR | B | 235 | 13.649 | 38.428 | 84.646 | 1.00 26.32 | C |
| ATOM | 4178 | O | THR | B | 235 | 14.346 | 38.840 | 83.729 | 1.00 26.32 | O |
| ATOM | 4179 | CB | THR | B | 235 | 12.981 | 36.339 | 85.722 | 1.00 18.24 | C |
| ATOM | 4180 | OG1 | THR | B | 235 | 14.364 | 35.999 | 85.849 | 1.00 18.24 | O |
| ATOM | 4181 | CG2 | THR | B | 235 | 12.158 | 35.081 | 85.617 | 1.00 18.24 | C |
| ATOM | 4182 | N | SER | B | 236 | 13.614 | 38.998 | 85.837 | 1.00 31.43 | N |
| ATOM | 4183 | CA | SER | B | 236 | 14.402 | 40.175 | 86.112 | 1.00 31.43 | C |
| ATOM | 4184 | C | SER | B | 236 | 15.882 | 39.909 | 86.198 | 1.00 31.43 | C |
| ATOM | 4185 | O | SER | B | 236 | 16.676 | 40.822 | 86.017 | 1.00 31.43 | O |
| ATOM | 4186 | CB | SER | B | 236 | 13.924 | 40.818 | 87.397 | 1.00 49.49 | C |
| ATOM | 4187 | OG | SER | B | 236 | 12.705 | 41.485 | 87.147 | 1.00 49.49 | O |
| ATOM | 4188 | N | SER | B | 237 | 16.256 | 38.664 | 86.478 | 1.00 30.23 | N |
| ATOM | 4189 | CA | SER | B | 237 | 17.650 | 38.274 | 86.631 | 1.00 30.23 | C |
| ATOM | 4190 | C | SER | B | 237 | 18.473 | 38.685 | 85.409 | 1.00 30.23 | C |
| ATOM | 4191 | O | SER | B | 237 | 19.696 | 38.643 | 85.400 | 1.00 30.23 | O |
| ATOM | 4192 | CB | SER | B | 237 | 17.703 | 36.757 | 86.813 | 1.00 31.67 | C |
| ATOM | 4193 | OG | SER | B | 237 | 16.897 | 36.134 | 85.813 | 1.00 31.67 | O |
| ATOM | 4194 | N | ILE | B | 238 | 17.750 | 39.055 | 84.335 | 1.00 19.62 | N |
| ATOM | 4195 | CA | ILE | B | 238 | 18.435 | 39.494 | 83.126 | 1.00 19.62 | C |
| ATOM | 4196 | C | ILE | B | 238 | 19.168 | 40.819 | 83.347 | 1.00 19.62 | C |
| ATOM | 4197 | O | ILE | B | 238 | 20.184 | 41.117 | 82.732 | 1.00 19.62 | O |
| ATOM | 4198 | CB | ILE | B | 238 | 17.396 | 39.636 | 82.013 | 1.00 27.89 | C |
| ATOM | 4199 | CG1 | ILE | B | 238 | 16.362 | 40.703 | 82.379 | 1.00 27.89 | C |
| ATOM | 4200 | CG2 | ILE | B | 238 | 16.651 | 38.301 | 81.826 | 1.00 27.89 | C |
| ATOM | 4201 | CD1 | ILE | B | 238 | 15.546 | 41.157 | 81.169 | 0.00 27.89 | C |
| ATOM | 4202 | N | ASP | B | 239 | 18.589 | 41.646 | 84.238 | 1.00 28.07 | N |
| ATOM | 4203 | CA | ASP | B | 239 | 19.275 | 42.870 | 84.633 | 1.00 28.07 | C |
| ATOM | 4204 | C | ASP | B | 239 | 20.539 | 42.545 | 85.430 | 1.00 28.07 | C |
| ATOM | 4205 | O | ASP | B | 239 | 21.525 | 43.271 | 85.427 | 1.00 28.07 | O |
| ATOM | 4206 | CB | ASP | B | 239 | 18.318 | 43.689 | 85.501 | 1.00 24.72 | C |
| ATOM | 4207 | CG | ASP | B | 239 | 17.384 | 44.489 | 84.607 | 1.00 24.72 | C |
| ATOM | 4208 | OD1 | ASP | B | 239 | 17.682 | 44.598 | 83.418 | 1.00 24.72 | O |
| ATOM | 4209 | OD2 | ASP | B | 239 | 16.379 | 44.988 | 85.102 | 1.00 24.72 | O |
| ATOM | 4210 | N | VAL | B | 240 | 20.463 | 41.417 | 86.164 | 1.00 19.83 | N |
| ATOM | 4211 | CA | VAL | B | 240 | 21.604 | 40.983 | 86.959 | 1.00 19.83 | C |
| ATOM | 4212 | C | VAL | B | 240 | 22.764 | 40.533 | 86.069 | 1.00 19.83 | C |
| ATOM | 4213 | O | VAL | B | 240 | 23.911 | 40.928 | 86.237 | 1.00 19.83 | O |

FIG. 1-69

```
ATOM   4214  CB   VAL B 240      21.149  39.821  87.844  1.00 18.12      C
ATOM   4215  CG1  VAL B 240      22.353  39.195  88.543  1.00 18.12      C
ATOM   4216  CG2  VAL B 240      20.166  40.314  88.888  1.00 18.12      C
ATOM   4217  N    TRP B 241      22.437  39.638  85.119  1.00 21.79      N
ATOM   4218  CA   TRP B 241      23.458  39.179  84.187  1.00 21.79      C
ATOM   4219  C    TRP B 241      24.140  40.359  83.494  1.00 21.79      C
ATOM   4220  O    TRP B 241      25.346  40.391  83.291  1.00 21.79      O
ATOM   4221  CB   TRP B 241      22.786  38.281  83.147  1.00 24.64      C
ATOM   4222  CG   TRP B 241      23.715  38.010  82.026  1.00 24.64      C
ATOM   4223  CD1  TRP B 241      23.990  38.859  80.931  1.00 24.64      C
ATOM   4224  CD2  TRP B 241      24.504  36.812  81.827  1.00 24.64      C
ATOM   4225  NE1  TRP B 241      24.878  38.313  80.059  1.00 24.64      N
ATOM   4226  CE2  TRP B 241      25.228  36.984  80.620  1.00 24.64      C
ATOM   4227  CE3  TRP B 241      24.662  35.637  82.556  1.00 24.64      C
ATOM   4228  CZ2  TRP B 241      26.082  35.986  80.177  1.00 24.64      C
ATOM   4229  CZ3  TRP B 241      25.515  34.639  82.113  1.00 24.64      C
ATOM   4230  CH2  TRP B 241      26.229  34.817  80.914  1.00 24.64      C
ATOM   4231  N    SER B 242      23.306  41.334  83.087  1.00 16.88      N
ATOM   4232  CA   SER B 242      23.850  42.531  82.456  1.00 16.88      C
ATOM   4233  C    SER B 242      24.794  43.276  83.400  1.00 16.88      C
ATOM   4234  O    SER B 242      25.876  43.708  83.025  1.00 16.88      O
ATOM   4235  CB   SER B 242      22.681  43.440  82.074  1.00 18.23      C
ATOM   4236  OG   SER B 242      22.036  42.918  80.912  1.00 18.23      O
ATOM   4237  N    ALA B 243      24.363  43.386  84.652  1.00 29.48      N
ATOM   4238  CA   ALA B 243      25.178  44.022  85.677  1.00 29.48      C
ATOM   4239  C    ALA B 243      26.497  43.267  85.783  1.00 29.48      C
ATOM   4240  O    ALA B 243      27.556  43.875  85.901  1.00 29.48      O
ATOM   4241  CB   ALA B 243      24.462  44.010  86.997  1.00 12.02      C
ATOM   4242  N    GLY B 244      26.435  41.941  85.733  1.00 26.93      N
ATOM   4243  CA   GLY B 244      27.651  41.155  85.798  1.00 26.93      C
ATOM   4244  C    GLY B 244      28.591  41.487  84.651  1.00 26.93      C
ATOM   4245  O    GLY B 244      29.805  41.495  84.822  1.00 26.93      O
ATOM   4246  N    CYS B 245      28.041  41.755  83.475  1.00 22.38      N
ATOM   4247  CA   CYS B 245      28.865  42.104  82.320  1.00 22.38      C
ATOM   4248  C    CYS B 245      29.507  43.478  82.495  1.00 22.38      C
ATOM   4249  O    CYS B 245      30.571  43.745  81.955  1.00 22.38      O
ATOM   4250  CB   CYS B 245      28.035  42.098  81.029  1.00 29.42      C
ATOM   4251  SG   CYS B 245      27.454  40.481  80.496  1.00 29.42      S
ATOM   4252  N    VAL B 246      28.850  44.360  83.238  1.00 21.80      N
ATOM   4253  CA   VAL B 246      29.410  45.677  83.460  1.00 21.80      C
ATOM   4254  C    VAL B 246      30.540  45.576  84.469  1.00 21.80      C
ATOM   4255  O    VAL B 246      31.546  46.257  84.329  1.00 21.80      O
ATOM   4256  CB   VAL B 246      28.363  46.666  83.969  1.00 17.88      C
ATOM   4257  CG1  VAL B 246      29.040  47.982  84.338  1.00 17.88      C
ATOM   4258  CG2  VAL B 246      27.305  46.888  82.904  1.00 17.88      C
ATOM   4259  N    LEU B 247      30.376  44.723  85.480  1.00 25.71      N
ATOM   4260  CA   LEU B 247      31.412  44.524  86.491  1.00 25.71      C
ATOM   4261  C    LEU B 247      32.645  43.925  85.832  1.00 25.71      C
ATOM   4262  O    LEU B 247      33.760  44.382  86.042  1.00 25.71      O
ATOM   4263  CB   LEU B 247      30.919  43.588  87.598  1.00 19.87      C
ATOM   4264  CG   LEU B 247      31.979  42.855  88.428  1.00 19.87      C
ATOM   4265  CD1  LEU B 247      32.758  43.811  89.310  1.00 19.87      C
ATOM   4266  CD2  LEU B 247      31.294  41.808  89.259  1.00 19.87      C
ATOM   4267  N    ALA B 248      32.438  42.890  85.033  1.00 32.57      N
ATOM   4268  CA   ALA B 248      33.543  42.253  84.350  1.00 32.57      C
ATOM   4269  C    ALA B 248      34.275  43.276  83.477  1.00 32.57      C
ATOM   4270  O    ALA B 248      35.502  43.409  83.558  1.00 32.57      O
ATOM   4271  CB   ALA B 248      33.031  41.102  83.506  1.00 22.47      C
ATOM   4272  N    GLU B 249      33.525  44.010  82.656  1.00 30.07      N
ATOM   4273  CA   GLU B 249      34.115  45.015  81.773  1.00 30.07      C
ATOM   4274  C    GLU B 249      34.978  46.014  82.542  1.00 30.07      C
ATOM   4275  O    GLU B 249      36.026  46.436  82.045  1.00 30.07      O
```

FIG. 1-70

```
ATOM   4276  CB   GLU B 249      33.020  45.766  80.995  1.00 23.84           C
ATOM   4277  CG   GLU B 249      33.542  46.725  79.924  1.00 23.84           C
ATOM   4278  CD   GLU B 249      32.492  47.106  78.877  1.00 23.84           C
ATOM   4279  OE1  GLU B 249      31.435  46.441  78.798  1.00 23.84           O
ATOM   4280  OE2  GLU B 249      32.732  48.064  78.115  1.00 23.84           O
ATOM   4281  N    LEU B 250      34.546  46.393  83.747  1.00 27.10           N
ATOM   4282  CA   LEU B 250      35.314  47.345  84.539  1.00 27.10           C
ATOM   4283  C    LEU B 250      36.603  46.720  85.010  1.00 27.10           C
ATOM   4284  O    LEU B 250      37.619  47.393  85.130  1.00 27.10           O
ATOM   4285  CB   LEU B 250      34.521  47.836  85.743  1.00 20.94           C
ATOM   4286  CG   LEU B 250      33.316  48.691  85.377  1.00 20.94           C
ATOM   4287  CD1  LEU B 250      32.576  49.088  86.638  1.00 20.94           C
ATOM   4288  CD2  LEU B 250      33.783  49.908  84.576  1.00 20.94           C
ATOM   4289  N    LEU B 251      36.563  45.424  85.272  1.00 33.59           N
ATOM   4290  CA   LEU B 251      37.750  44.735  85.712  1.00 33.59           C
ATOM   4291  C    LEU B 251      38.720  44.504  84.537  1.00 33.59           C
ATOM   4292  O    LEU B 251      39.932  44.647  84.685  1.00 33.59           O
ATOM   4293  CB   LEU B 251      37.364  43.405  86.350  1.00 20.83           C
ATOM   4294  CG   LEU B 251      36.515  43.441  87.618  1.00 20.83           C
ATOM   4295  CD1  LEU B 251      36.190  42.019  88.020  1.00 20.83           C
ATOM   4296  CD2  LEU B 251      37.253  44.145  88.745  1.00 20.83           C
ATOM   4297  N    LEU B 252      38.182  44.188  83.363  1.00 29.76           N
ATOM   4298  CA   LEU B 252      39.003  43.900  82.189  1.00 29.76           C
ATOM   4299  C    LEU B 252      39.405  45.066  81.298  1.00 29.76           C
ATOM   4300  O    LEU B 252      40.381  44.964  80.556  1.00 29.76           O
ATOM   4301  CB   LEU B 252      38.290  42.872  81.311  1.00 41.19           C
ATOM   4302  CG   LEU B 252      38.095  41.469  81.874  1.00 41.19           C
ATOM   4303  CD1  LEU B 252      36.941  40.803  81.149  1.00 41.19           C
ATOM   4304  CD2  LEU B 252      39.391  40.673  81.743  1.00 41.19           C
ATOM   4305  N    GLY B 253      38.649  46.155  81.328  1.00 21.90           N
ATOM   4306  CA   GLY B 253      38.982  47.272  80.470  1.00 21.90           C
ATOM   4307  C    GLY B 253      38.396  47.086  79.082  1.00 21.90           C
ATOM   4308  O    GLY B 253      38.745  47.811  78.149  1.00 21.90           O
ATOM   4309  N    GLN B 254      37.513  46.101  78.935  1.00 27.16           N
ATOM   4310  CA   GLN B 254      36.855  45.840  77.659  1.00 27.16           C
ATOM   4311  C    GLN B 254      35.671  44.897  77.845  1.00 27.16           C
ATOM   4312  O    GLN B 254      35.587  44.171  78.827  1.00 27.16           O
ATOM   4313  CB   GLN B 254      37.847  45.270  76.635  1.00 44.50           C
ATOM   4314  CG   GLN B 254      38.381  43.891  76.948  1.00 44.50           C
ATOM   4315  CD   GLN B 254      39.390  43.417  75.920  1.00 44.50           C
ATOM   4316  OE1  GLN B 254      39.790  42.257  75.918  1.00 44.50           O
ATOM   4317  NE2  GLN B 254      39.808  44.318  75.038  1.00 44.50           N
ATOM   4318  N    PRO B 255      34.727  44.905  76.901  1.00 40.09           N
ATOM   4319  CA   PRO B 255      33.574  44.017  77.052  1.00 40.09           C
ATOM   4320  C    PRO B 255      34.052  42.591  77.256  1.00 40.09           C
ATOM   4321  O    PRO B 255      35.067  42.206  76.692  1.00 40.09           O
ATOM   4322  CB   PRO B 255      32.840  44.186  75.724  1.00 24.34           C
ATOM   4323  CG   PRO B 255      33.211  45.554  75.302  1.00 24.34           C
ATOM   4324  CD   PRO B 255      34.678  45.604  75.611  1.00 24.34           C
ATOM   4325  N    ILE B 256      33.343  41.802  78.050  1.00 32.18           N
ATOM   4326  CA   ILE B 256      33.771  40.425  78.244  1.00 32.18           C
ATOM   4327  C    ILE B 256      33.139  39.458  77.244  1.00 32.18           C
ATOM   4328  O    ILE B 256      33.733  38.443  76.918  1.00 32.18           O
ATOM   4329  CB   ILE B 256      33.476  39.922  79.678  1.00 27.08           C
ATOM   4330  CG1  ILE B 256      33.865  38.445  79.793  1.00 27.08           C
ATOM   4331  CG2  ILE B 256      32.017  40.124  80.011  1.00 27.08           C
ATOM   4332  CD1  ILE B 256      33.659  37.832  81.170  1.00 27.08           C
ATOM   4333  N    PHE B 257      31.946  39.771  76.750  1.00 27.33           N
ATOM   4334  CA   PHE B 257      31.257  38.891  75.800  1.00 27.33           C
ATOM   4335  C    PHE B 257      30.880  39.592  74.504  1.00 27.33           C
ATOM   4336  O    PHE B 257      29.701  39.733  74.197  1.00 27.33           O
ATOM   4337  CB   PHE B 257      29.974  38.322  76.418  1.00 25.37           C
```

FIG. 1-71

| ATOM | 4338 | CG  | PHE | B | 257 | 30.198 | 37.503 | 77.639 | 1.00 | 25.37 | C |
| --- | --- | --- | --- | --- | --- | --- | --- | --- | --- | --- | --- |
| ATOM | 4339 | CD1 | PHE | B | 257 | 31.077 | 36.430 | 77.620 | 1.00 | 25.37 | C |
| ATOM | 4340 | CD2 | PHE | B | 257 | 29.508 | 37.780 | 78.806 | 1.00 | 25.37 | C |
| ATOM | 4341 | CE1 | PHE | B | 257 | 31.262 | 35.629 | 78.755 | 1.00 | 25.37 | C |
| ATOM | 4342 | CE2 | PHE | B | 257 | 29.681 | 36.992 | 79.949 | 1.00 | 25.37 | C |
| ATOM | 4343 | CZ  | PHE | B | 257 | 30.562 | 35.913 | 79.921 | 1.00 | 25.37 | C |
| ATOM | 4344 | N   | PRO | B | 258 | 31.874 | 40.039 | 73.726 | 1.00 | 27.82 | N |
| ATOM | 4345 | CA  | PRO | B | 258 | 31.596 | 40.723 | 72.464 | 1.00 | 27.82 | C |
| ATOM | 4346 | C   | PRO | B | 258 | 31.270 | 39.739 | 71.348 | 1.00 | 27.82 | C |
| ATOM | 4347 | O   | PRO | B | 258 | 31.434 | 38.517 | 71.502 | 1.00 | 27.82 | O |
| ATOM | 4348 | CB  | PRO | B | 258 | 32.888 | 41.465 | 72.199 | 1.00 | 18.96 | C |
| ATOM | 4349 | CG  | PRO | B | 258 | 33.892 | 40.478 | 72.646 | 1.00 | 18.96 | C |
| ATOM | 4350 | CD  | PRO | B | 258 | 33.326 | 40.006 | 73.977 | 1.00 | 18.96 | C |
| ATOM | 4351 | N   | GLY | B | 259 | 30.820 | 40.291 | 70.226 | 1.00 | 32.91 | N |
| ATOM | 4352 | CA  | GLY | B | 259 | 30.470 | 39.494 | 69.065 | 1.00 | 32.91 | C |
| ATOM | 4353 | C   | GLY | B | 259 | 29.362 | 40.156 | 68.273 | 1.00 | 32.91 | C |
| ATOM | 4354 | O   | GLY | B | 259 | 28.355 | 40.555 | 68.843 | 1.00 | 32.91 | O |
| ATOM | 4355 | N   | ASP | B | 260 | 29.530 | 40.285 | 66.963 | 1.00 | 29.78 | N |
| ATOM | 4356 | CA  | ASP | B | 260 | 28.498 | 40.916 | 66.152 | 1.00 | 29.78 | C |
| ATOM | 4357 | C   | ASP | B | 260 | 27.260 | 40.038 | 65.948 | 1.00 | 29.78 | C |
| ATOM | 4358 | O   | ASP | B | 260 | 26.215 | 40.527 | 65.523 | 1.00 | 29.78 | O |
| ATOM | 4359 | CB  | ASP | B | 260 | 29.066 | 41.337 | 64.797 | 1.00 | 55.97 | C |
| ATOM | 4360 | CG  | ASP | B | 260 | 30.193 | 42.338 | 64.931 | 1.00 | 55.97 | C |
| ATOM | 4361 | OD1 | ASP | B | 260 | 30.044 | 43.308 | 65.714 | 1.00 | 55.97 | O |
| ATOM | 4362 | OD2 | ASP | B | 260 | 31.230 | 42.161 | 64.247 | 1.00 | 55.97 | O |
| ATOM | 4363 | N   | SER | B | 261 | 27.386 | 38.747 | 66.243 | 1.00 | 27.61 | N |
| ATOM | 4364 | CA  | SER | B | 261 | 26.267 | 37.823 | 66.108 | 1.00 | 27.61 | C |
| ATOM | 4365 | C   | SER | B | 261 | 26.016 | 37.098 | 67.437 | 1.00 | 27.61 | C |
| ATOM | 4366 | O   | SER | B | 261 | 26.881 | 37.072 | 68.311 | 1.00 | 27.61 | O |
| ATOM | 4367 | CB  | SER | B | 261 | 26.557 | 36.790 | 65.023 | 1.00 | 21.12 | C |
| ATOM | 4368 | OG  | SER | B | 261 | 27.431 | 35.784 | 65.504 | 1.00 | 21.12 | O |
| ATOM | 4369 | N   | GLY | B | 262 | 24.829 | 36.519 | 67.585 | 1.00 | 31.64 | N |
| ATOM | 4370 | CA  | GLY | B | 262 | 24.525 | 35.784 | 68.798 | 1.00 | 31.64 | C |
| ATOM | 4371 | C   | GLY | B | 262 | 25.488 | 34.624 | 68.950 | 1.00 | 31.64 | C |
| ATOM | 4372 | O   | GLY | B | 262 | 25.879 | 34.265 | 70.060 | 1.00 | 31.64 | O |
| ATOM | 4373 | N   | VAL | B | 263 | 25.878 | 34.035 | 67.823 | 1.00 | 31.86 | N |
| ATOM | 4374 | CA  | VAL | B | 263 | 26.809 | 32.913 | 67.819 | 1.00 | 31.86 | C |
| ATOM | 4375 | C   | VAL | B | 263 | 28.136 | 33.311 | 68.443 | 1.00 | 31.86 | C |
| ATOM | 4376 | O   | VAL | B | 263 | 28.612 | 32.669 | 69.380 | 1.00 | 31.86 | O |
| ATOM | 4377 | CB  | VAL | B | 263 | 27.089 | 32.414 | 66.389 | 1.00 | 43.99 | C |
| ATOM | 4378 | CG1 | VAL | B | 263 | 28.138 | 31.299 | 66.419 | 1.00 | 43.99 | C |
| ATOM | 4379 | CG2 | VAL | B | 263 | 25.826 | 31.904 | 65.773 | 1.00 | 43.99 | C |
| ATOM | 4380 | N   | ASP | B | 264 | 28.742 | 34.360 | 67.905 | 1.00 | 33.92 | N |
| ATOM | 4381 | CA  | ASP | B | 264 | 30.011 | 34.816 | 68.441 | 1.00 | 33.92 | C |
| ATOM | 4382 | C   | ASP | B | 264 | 29.872 | 35.056 | 69.940 | 1.00 | 33.92 | C |
| ATOM | 4383 | O   | ASP | B | 264 | 30.636 | 34.511 | 70.742 | 1.00 | 33.92 | O |
| ATOM | 4384 | CB  | ASP | B | 264 | 30.458 | 36.100 | 67.747 | 1.00 | 58.74 | C |
| ATOM | 4385 | CG  | ASP | B | 264 | 30.641 | 35.923 | 66.251 | 1.00 | 58.74 | C |
| ATOM | 4386 | OD1 | ASP | B | 264 | 31.049 | 34.827 | 65.815 | 1.00 | 58.74 | O |
| ATOM | 4387 | OD2 | ASP | B | 264 | 30.393 | 36.892 | 65.506 | 1.00 | 58.74 | O |
| ATOM | 4388 | N   | GLN | B | 265 | 28.887 | 35.866 | 70.309 | 1.00 | 28.36 | N |
| ATOM | 4389 | CA  | GLN | B | 265 | 28.634 | 36.166 | 71.707 | 1.00 | 28.36 | C |
| ATOM | 4390 | C   | GLN | B | 265 | 28.504 | 34.876 | 72.486 | 1.00 | 28.36 | C |
| ATOM | 4391 | O   | GLN | B | 265 | 29.003 | 34.764 | 73.593 | 1.00 | 28.36 | O |
| ATOM | 4392 | CB  | GLN | B | 265 | 27.358 | 36.989 | 71.857 | 1.00 | 26.30 | C |
| ATOM | 4393 | CG  | GLN | B | 265 | 27.451 | 38.354 | 71.233 | 1.00 | 26.30 | C |
| ATOM | 4394 | CD  | GLN | B | 265 | 26.205 | 39.162 | 71.438 | 1.00 | 26.30 | C |
| ATOM | 4395 | OE1 | GLN | B | 265 | 25.103 | 38.706 | 71.141 | 1.00 | 26.30 | O |
| ATOM | 4396 | NE2 | GLN | B | 265 | 26.364 | 40.377 | 71.949 | 0.00 | 26.30 | N |
| ATOM | 4397 | N   | LEU | B | 266 | 27.840 | 33.898 | 71.894 | 1.00 | 28.75 | N |
| ATOM | 4398 | CA  | LEU | B | 266 | 27.657 | 32.613 | 72.543 | 1.00 | 28.75 | C |
| ATOM | 4399 | C   | LEU | B | 266 | 28.976 | 31.858 | 72.719 | 1.00 | 28.75 | C |

FIG. 1-72

```
ATOM   4400  O   LEU B 266      29.234  31.308  73.781  1.00 28.75           O
ATOM   4401  CB  LEU B 266      26.662  31.774  71.744  1.00 28.63           C
ATOM   4402  CG  LEU B 266      25.330  31.442  72.413  1.00 28.63           C
ATOM   4403  CD1 LEU B 266      24.818  32.618  73.192  1.00 28.63           C
ATOM   4404  CD2 LEU B 266      24.329  31.035  71.353  1.00 28.63           C
ATOM   4405  N   VAL B 267      29.823  31.824  71.695  1.00 38.65           N
ATOM   4406  CA  VAL B 267      31.091  31.110  71.853  1.00 38.65           C
ATOM   4407  C   VAL B 267      31.938  31.841  72.886  1.00 38.65           C
ATOM   4408  O   VAL B 267      32.723  31.226  73.603  1.00 38.65           O
ATOM   4409  CB  VAL B 267      31.891  30.980  70.513  1.00 39.88           C
ATOM   4410  CG1 VAL B 267      31.035  30.323  69.480  1.00 39.88           C
ATOM   4411  CG2 VAL B 267      32.355  32.324  70.014  1.00 39.88           C
ATOM   4412  N   GLU B 268      31.762  33.156  72.963  1.00 36.51           N
ATOM   4413  CA  GLU B 268      32.499  33.958  73.922  1.00 36.51           C
ATOM   4414  C   GLU B 268      32.032  33.598  75.335  1.00 36.51           C
ATOM   4415  O   GLU B 268      32.842  33.465  76.250  1.00 36.51           O
ATOM   4416  CB  GLU B 268      32.268  35.450  73.643  1.00 54.53           C
ATOM   4417  CG  GLU B 268      33.548  36.277  73.557  1.00 54.53           C
ATOM   4418  CD  GLU B 268      34.549  35.674  72.592  1.00 54.53           C
ATOM   4419  OE1 GLU B 268      34.132  35.359  71.456  1.00 54.53           O
ATOM   4420  OE2 GLU B 268      35.738  35.512  72.957  1.00 54.53           O
ATOM   4421  N   ILE B 269      30.724  33.431  75.507  1.00 36.11           N
ATOM   4422  CA  ILE B 269      30.169  33.076  76.807  1.00 36.11           C
ATOM   4423  C   ILE B 269      30.553  31.657  77.202  1.00 36.11           C
ATOM   4424  O   ILE B 269      30.924  31.393  78.353  1.00 36.11           O
ATOM   4425  CB  ILE B 269      28.638  33.169  76.811  1.00 18.31           C
ATOM   4426  CG1 ILE B 269      28.204  34.625  76.758  1.00 18.31           C
ATOM   4427  CG2 ILE B 269      28.081  32.524  78.060  1.00 18.31           C
ATOM   4428  CD1 ILE B 269      26.728  34.796  76.506  1.00 18.31           C
ATOM   4429  N   ILE B 270      30.447  30.744  76.244  1.00 33.52           N
ATOM   4430  CA  ILE B 270      30.780  29.354  76.483  1.00 33.52           C
ATOM   4431  C   ILE B 270      32.253  29.247  76.834  1.00 33.52           C
ATOM   4432  O   ILE B 270      32.630  28.466  77.702  1.00 33.52           O
ATOM   4433  CB  ILE B 270      30.484  28.486  75.244  1.00 28.24           C
ATOM   4434  CG1 ILE B 270      28.987  28.549  74.915  1.00 28.24           C
ATOM   4435  CG2 ILE B 270      30.925  27.048  75.503  1.00 28.24           C
ATOM   4436  CD1 ILE B 270      28.593  27.813  73.666  1.00 28.24           C
ATOM   4437  N   LYS B 271      33.083  30.041  76.171  1.00 38.26           N
ATOM   4438  CA  LYS B 271      34.509  30.010  76.456  1.00 38.26           C
ATOM   4439  C   LYS B 271      34.784  30.135  77.957  1.00 38.26           C
ATOM   4440  O   LYS B 271      35.520  29.324  78.535  1.00 38.26           O
ATOM   4441  CB  LYS B 271      35.245  31.129  75.707  1.00 53.65           C
ATOM   4442  CG  LYS B 271      35.912  30.693  74.408  1.00 53.65           C
ATOM   4443  CD  LYS B 271      36.435  31.900  73.617  1.00 53.65           C
ATOM   4444  CE  LYS B 271      37.134  31.464  72.321  1.00 53.65           C
ATOM   4445  NZ  LYS B 271      37.221  32.531  71.253  1.00 53.65           N
ATOM   4446  N   VAL B 272      34.194  31.131  78.607  1.00 44.83           N
ATOM   4447  CA  VAL B 272      34.464  31.271  80.026  1.00 44.83           C
ATOM   4448  C   VAL B 272      33.527  30.498  80.939  1.00 44.83           C
ATOM   4449  O   VAL B 272      33.924  30.143  82.039  1.00 44.83           O
ATOM   4450  CB  VAL B 272      34.538  32.765  80.453  1.00 28.34           C
ATOM   4451  CG1 VAL B 272      34.172  33.656  79.276  1.00 28.34           C
ATOM   4452  CG2 VAL B 272      33.662  33.023  81.678  1.00 28.34           C
ATOM   4453  N   LEU B 273      32.303  30.208  80.514  1.00 41.39           N
ATOM   4454  CA  LEU B 273      31.414  29.450  81.400  1.00 41.39           C
ATOM   4455  C   LEU B 273      31.427  27.955  81.083  1.00 41.39           C
ATOM   4456  O   LEU B 273      30.767  27.164  81.746  1.00 41.39           O
ATOM   4457  CB  LEU B 273      29.967  29.947  81.306  1.00 34.53           C
ATOM   4458  CG  LEU B 273      29.619  31.415  81.542  1.00 34.53           C
ATOM   4459  CD1 LEU B 273      28.145  31.488  81.883  1.00 34.53           C
ATOM   4460  CD2 LEU B 273      30.436  32.007  82.671  1.00 34.53           C
ATOM   4461  N   GLY B 274      32.185  27.554  80.075  1.00 42.38           N
```

FIG. 1-73

```
ATOM   4462  CA  GLY B 274      32.188  26.147  79.724  1.00 42.38           C
ATOM   4463  C   GLY B 274      30.885  25.899  78.981  1.00 42.38           C
ATOM   4464  O   GLY B 274      30.004  26.753  79.011  1.00 42.38           O
ATOM   4465  N   THR B 275      30.751  24.764  78.296  1.00 39.88           N
ATOM   4466  CA  THR B 275      29.528  24.479  77.537  1.00 39.88           C
ATOM   4467  C   THR B 275      28.324  24.418  78.497  1.00 39.88           C
ATOM   4468  O   THR B 275      28.463  24.185  79.677  1.00 39.88           O
ATOM   4469  CB  THR B 275      29.571  23.103  76.792  1.00 66.35           C
ATOM   4470  OG1 THR B 275      30.918  22.733  76.458  1.00 66.35           O
ATOM   4471  CG2 THR B 275      28.741  23.178  75.512  1.00 66.35           C
ATOM   4472  N   PRO B 276      27.117  24.620  77.983  1.00 61.18           N
ATOM   4473  CA  PRO B 276      25.963  24.559  78.890  1.00 61.18           C
ATOM   4474  C   PRO B 276      25.533  23.112  78.966  1.00 61.18           C
ATOM   4475  O   PRO B 276      25.862  22.338  78.071  1.00 61.18           O
ATOM   4476  CB  PRO B 276      24.909  25.410  78.205  1.00 58.97           C
ATOM   4477  CG  PRO B 276      25.574  25.950  76.991  1.00 58.97           C
ATOM   4478  CD  PRO B 276      26.751  25.148  76.667  1.00 58.97           C
ATOM   4479  N   THR B 277      24.820  22.756  80.030  1.00 61.20           N
ATOM   4480  CA  THR B 277      24.340  21.410  80.262  1.00 61.20           C
ATOM   4481  C   THR B 277      22.928  21.439  79.766  1.00 61.20           C
ATOM   4482  O   THR B 277      22.373  22.520  79.559  1.00 61.20           O
ATOM   4483  CB  THR B 277      24.294  21.099  81.740  1.00 67.39           C
ATOM   4484  OG1 THR B 277      23.608  19.868  81.950  1.00 67.39           O
ATOM   4485  CG2 THR B 277      23.554  22.149  82.456  0.00 67.39           C
ATOM   4486  N   ARG B 278      22.340  20.263  79.590  1.00 59.77           N
ATOM   4487  CA  ARG B 278      20.988  20.191  79.053  1.00 59.77           C
ATOM   4488  C   ARG B 278      20.048  20.894  80.006  1.00 59.77           C
ATOM   4489  O   ARG B 278      19.128  21.607  79.619  1.00 59.77           O
ATOM   4490  CB  ARG B 278      20.579  18.722  78.865  1.00 80.99           C
ATOM   4491  N   GLU B 279      20.280  20.720  81.281  0.00 74.44           N
ATOM   4492  CA  GLU B 279      19.394  21.370  82.194  1.00 74.44           C
ATOM   4493  C   GLU B 279      19.417  22.906  82.055  1.00 74.44           C
ATOM   4494  O   GLU B 279      18.381  23.576  82.213  1.00 74.44           O
ATOM   4495  CB  GLU B 279      19.770  20.956  83.616  1.00100.00           C
ATOM   4496  CG  GLU B 279      18.855  21.511  84.709  1.00100.00           C
ATOM   4497  CD  GLU B 279      19.242  20.978  86.092  1.00100.00           C
ATOM   4498  OE1 GLU B 279      18.578  21.359  87.112  1.00100.00           O
ATOM   4499  OE2 GLU B 279      20.222  20.166  86.169  1.00100.00           O
ATOM   4500  N   GLN B 280      20.597  23.451  81.762  1.00 49.40           N
ATOM   4501  CA  GLN B 280      20.767  24.886  81.689  1.00 49.40           C
ATOM   4502  C   GLN B 280      20.126  25.436  80.448  1.00 49.40           C
ATOM   4503  O   GLN B 280      19.741  26.602  80.394  0.00 49.40           O
ATOM   4504  CB  GLN B 280      22.245  25.240  81.736  1.00 52.20           C
ATOM   4505  CG  GLN B 280      22.919  24.978  83.083  1.00 52.20           C
ATOM   4506  CD  GLN B 280      24.418  25.173  82.983  1.00 52.20           C
ATOM   4507  OE1 GLN B 280      25.154  25.010  83.952  1.00 52.20           O
ATOM   4508  NE2 GLN B 280      24.879  25.536  81.791  1.00 52.20           N
ATOM   4509  N   ILE B 281      19.995  24.569  79.455  1.00 75.99           N
ATOM   4510  CA  ILE B 281      19.383  24.970  78.211  1.00 75.99           C
ATOM   4511  C   ILE B 281      17.863  25.073  78.359  1.00 75.99           C
ATOM   4512  O   ILE B 281      17.278  26.075  77.926  1.00 75.99           O
ATOM   4513  CB  ILE B 281      19.740  23.994  77.077  0.00 79.77           C
ATOM   4514  CG1 ILE B 281      19.001  24.353  75.802  1.00 79.77           C
ATOM   4515  CG2 ILE B 281      19.320  22.628  77.425  1.00 79.77           C
ATOM   4516  CD1 ILE B 281      19.305  23.354  74.681  1.00 79.77           C
ATOM   4517  N   ARG B 282      17.216  24.071  78.972  1.00 75.81           N
ATOM   4518  CA  ARG B 282      15.753  24.119  79.111  1.00 75.81           C
ATOM   4519  C   ARG B 282      15.419  25.333  79.945  1.00 75.81           C
ATOM   4520  O   ARG B 282      14.409  26.018  79.758  1.00 75.81           O
ATOM   4521  CB  ARG B 282      15.204  22.820  79.803  1.00 70.19           C
ATOM   4522  N   GLU B 283      16.327  25.621  80.846  1.00 65.28           N
ATOM   4523  CA  GLU B 283      16.118  26.712  81.735  1.00 65.28           C
```

FIG. 1-74

```
ATOM   4524  C    GLU B 283      16.499  28.038  81.093  1.00 65.28           C
ATOM   4525  O    GLU B 283      16.196  29.121  81.608  1.00 65.28           O
ATOM   4526  CB   GLU B 283      16.957  26.457  82.935  1.00100.00           C
ATOM   4527  CG   GLU B 283      16.909  27.617  83.791  1.00100.00           C
ATOM   4528  CD   GLU B 283      17.816  27.474  84.974  1.00100.00           C
ATOM   4529  OE1  GLU B 283      17.846  28.420  85.822  1.00100.00           O
ATOM   4530  OE2  GLU B 283      18.512  26.416  85.080  1.00100.00           O
ATOM   4531  N    MET B 284      17.138  27.918  79.937  1.00100.00           N
ATOM   4532  CA   MET B 284      17.596  29.044  79.174  1.00100.00           C
ATOM   4533  C    MET B 284      16.739  29.353  77.925  1.00100.00           C
ATOM   4534  O    MET B 284      16.206  30.470  77.799  1.00100.00           O
ATOM   4535  CB   MET B 284      19.013  28.762  78.783  0.00 72.50           C
ATOM   4536  CG   MET B 284      19.646  29.896  78.189  1.00 72.50           C
ATOM   4537  SD   MET B 284      21.389  29.541  78.241  1.00 72.50           S
ATOM   4538  CE   MET B 284      21.842  31.052  77.167  1.00 72.50           C
ATOM   4539  N    ASN B 285      16.601  28.397  77.005  1.00 87.37           N
ATOM   4540  CA   ASN B 285      15.819  28.618  75.787  1.00 87.37           C
ATOM   4541  C    ASN B 285      14.346  28.250  75.967  1.00 87.37           C
ATOM   4542  O    ASN B 285      14.012  27.369  76.775  1.00 87.37           O
ATOM   4543  CB   ASN B 285      16.429  27.804  74.639  1.00 72.72           C
ATOM   4544  N    PHE B 291      20.827  23.254  69.045  1.00 66.65           N
ATOM   4545  CA   PHE B 291      22.007  23.681  69.787  1.00 66.65           C
ATOM   4546  C    PHE B 291      23.179  22.717  69.586  1.00 66.65           C
ATOM   4547  O    PHE B 291      23.154  21.563  69.994  1.00 66.65           O
ATOM   4548  CB   PHE B 291      21.640  23.751  71.270  1.00 50.75           C
ATOM   4549  CG   PHE B 291      22.851  24.114  72.076  1.00 50.75           C
ATOM   4550  CD1  PHE B 291      23.267  25.439  72.133  1.00 50.75           C
ATOM   4551  CD2  PHE B 291      23.557  23.130  72.748  0.00 50.75           C
ATOM   4552  CE1  PHE B 291      24.395  25.776  72.867  1.00 50.75           C
ATOM   4553  CE2  PHE B 291      24.688  23.476  73.482  0.00 50.75           C
ATOM   4554  CZ   PHE B 291      25.111  24.798  73.545  1.00 50.75           C
ATOM   4555  N    LYS B 292      24.217  23.219  68.892  1.00 91.46           N
ATOM   4556  CA   LYS B 292      25.388  22.386  68.644  1.00 91.46           C
ATOM   4557  C    LYS B 292      26.633  23.233  68.369  1.00 91.46           C
ATOM   4558  O    LYS B 292      27.082  23.389  67.241  1.00 91.46           O
ATOM   4559  CB   LYS B 292      25.091  21.491  67.441  1.00 56.32           C
ATOM   4560  N    PHE B 293      27.171  23.823  69.453  1.00 98.94           N
ATOM   4561  CA   PHE B 293      28.358  24.656  69.303  1.00 98.94           C
ATOM   4562  C    PHE B 293      29.643  23.845  69.485  1.00 98.94           C
ATOM   4563  O    PHE B 293      30.391  23.600  68.548  1.00 98.94           O
ATOM   4564  CB   PHE B 293      28.294  25.770  70.349  1.00 52.03           C
ATOM   4565  CG   PHE B 293      27.212  26.744  69.987  1.00 52.03           C
ATOM   4566  CD1  PHE B 293      25.881  26.349  70.055  1.00 52.03           C
ATOM   4567  CD2  PHE B 293      27.542  28.026  69.580  1.00 52.03           C
ATOM   4568  CE1  PHE B 293      24.878  27.245  69.712  0.00 52.03           C
ATOM   4569  CE2  PHE B 293      26.529  28.919  69.238  1.00 52.03           C
ATOM   4570  CZ   PHE B 293      25.197  28.533  69.303  0.00 52.03           C
ATOM   4571  N    PRO B 294      29.901  23.463  70.749  1.00 96.91           N
ATOM   4572  CA   PRO B 294      31.101  22.686  71.036  1.00 96.91           C
ATOM   4573  C    PRO B 294      30.970  21.912  72.350  1.00 96.91           C
ATOM   4574  O    PRO B 294      31.094  22.458  73.438  1.00 96.91           O
ATOM   4575  N    GLN B 295      30.676  20.606  72.204  1.00 72.54           N
ATOM   4576  CA   GLN B 295      30.534  19.764  73.385  1.00 72.54           C
ATOM   4577  C    GLN B 295      31.679  19.984  74.376  1.00 72.54           C
ATOM   4578  O    GLN B 295      31.713  19.419  75.461  1.00 72.54           O
ATOM   4579  N    ILE B 296      32.732  20.771  74.154  1.00 83.25           N
ATOM   4580  CA   ILE B 296      33.771  20.911  75.161  1.00 83.25           C
ATOM   4581  C    ILE B 296      34.046  22.373  75.497  1.00 83.25           C
ATOM   4582  O    ILE B 296      33.124  23.192  75.645  1.00 83.25           O
ATOM   4583  N    LYS B 297      35.323  22.714  75.628  1.00100.00           N
ATOM   4584  CA   LYS B 297      35.776  24.074  75.881  1.00100.00           C
ATOM   4585  C    LYS B 297      35.342  24.559  77.265  1.00100.00           C
```

FIG. 1-75

| ATOM | 4586 | O | LYS | B | 297 | 34.427 | 25.356 | 77.421 | 1.00 | 100.00 | O |
|---|---|---|---|---|---|---|---|---|---|---|---|
| ATOM | 4587 | CB | LYS | B | 297 | 35.185 | 24.981 | 74.801 | 1.00 | 46.14 | C |
| ATOM | 4588 | N | ALA | B | 298 | 36.009 | 24.012 | 78.299 | 1.00 | 100.00 | N |
| ATOM | 4589 | CA | ALA | B | 298 | 35.710 | 24.455 | 79.655 | 1.00 | 100.00 | C |
| ATOM | 4590 | C | ALA | B | 298 | 36.015 | 25.946 | 79.825 | 1.00 | 100.00 | C |
| ATOM | 4591 | O | ALA | B | 298 | 36.598 | 26.595 | 78.967 | 1.00 | 100.00 | O |
| ATOM | 4592 | CB | ALA | B | 298 | 36.557 | 23.632 | 80.626 | 1.00 | 63.79 | C |
| ATOM | 4593 | N | HIS | B | 299 | 35.561 | 26.502 | 80.964 | 1.00 | 82.91 | N |
| ATOM | 4594 | CA | HIS | B | 299 | 35.772 | 27.926 | 81.186 | 1.00 | 82.91 | C |
| ATOM | 4595 | C | HIS | B | 299 | 36.526 | 28.201 | 82.489 | 1.00 | 82.91 | C |
| ATOM | 4596 | O | HIS | B | 299 | 36.146 | 27.770 | 83.571 | 1.00 | 82.91 | O |
| ATOM | 4597 | N | PRO | B | 300 | 37.664 | 28.907 | 82.350 | 1.00 | 100.00 | N |
| ATOM | 4598 | CA | PRO | B | 300 | 38.436 | 29.352 | 83.494 | 1.00 | 100.00 | C |
| ATOM | 4599 | C | PRO | B | 300 | 37.888 | 30.671 | 84.041 | 1.00 | 100.00 | C |
| ATOM | 4600 | O | PRO | B | 300 | 37.218 | 31.433 | 83.357 | 1.00 | 100.00 | O |
| ATOM | 4601 | CB | PRO | B | 300 | 39.870 | 29.552 | 83.011 | 1.00 | 82.31 | C |
| ATOM | 4602 | CG | PRO | B | 300 | 39.851 | 29.659 | 81.484 | 1.00 | 82.31 | C |
| ATOM | 4603 | CD | PRO | B | 300 | 38.324 | 29.323 | 81.125 | 1.00 | 82.31 | C |
| ATOM | 4604 | N | TRP | B | 301 | 38.160 | 30.914 | 85.335 | 1.00 | 95.69 | N |
| ATOM | 4605 | CA | TRP | B | 301 | 37.677 | 32.149 | 85.941 | 1.00 | 95.69 | C |
| ATOM | 4606 | C | TRP | B | 301 | 38.829 | 33.028 | 86.429 | 1.00 | 95.69 | C |
| ATOM | 4607 | O | TRP | B | 301 | 38.988 | 34.178 | 86.044 | 1.00 | 95.69 | O |
| ATOM | 4608 | CB | TRP | B | 301 | 36.772 | 31.782 | 87.118 | 1.00 | 45.45 | C |
| ATOM | 4609 | CG | TRP | B | 301 | 35.352 | 31.991 | 86.756 | 1.00 | 45.45 | C |
| ATOM | 4610 | CD1 | TRP | B | 301 | 34.281 | 31.100 | 86.991 | 1.00 | 45.45 | C |
| ATOM | 4611 | CD2 | TRP | B | 301 | 34.795 | 33.122 | 86.040 | 1.00 | 45.45 | C |
| ATOM | 4612 | NE1 | TRP | B | 301 | 33.105 | 31.554 | 86.487 | 1.00 | 45.45 | N |
| ATOM | 4613 | CE2 | TRP | B | 301 | 33.413 | 32.863 | 85.862 | 1.00 | 45.45 | C |
| ATOM | 4614 | CE3 | TRP | B | 301 | 35.341 | 34.298 | 85.534 | 1.00 | 45.45 | C |
| ATOM | 4615 | CZ2 | TRP | B | 301 | 32.622 | 33.771 | 85.178 | 1.00 | 45.45 | C |
| ATOM | 4616 | CZ3 | TRP | B | 301 | 34.549 | 35.205 | 84.849 | 1.00 | 45.45 | C |
| ATOM | 4617 | CH2 | TRP | B | 301 | 33.181 | 34.937 | 84.668 | 1.00 | 45.45 | C |
| ATOM | 4618 | N | THR | B | 302 | 39.628 | 32.453 | 87.343 | 1.00 | 65.12 | N |
| ATOM | 4619 | CA | THR | B | 302 | 40.725 | 33.217 | 87.921 | 1.00 | 65.12 | C |
| ATOM | 4620 | C | THR | B | 302 | 41.698 | 33.709 | 86.847 | 1.00 | 65.12 | C |
| ATOM | 4621 | O | THR | B | 302 | 42.475 | 34.631 | 87.051 | 1.00 | 65.12 | O |
| ATOM | 4622 | CB | THR | B | 302 | 41.448 | 32.311 | 88.917 | 1.00 | 68.67 | C |
| ATOM | 4623 | OG1 | THR | B | 302 | 40.515 | 31.885 | 89.913 | 1.00 | 68.67 | O |
| ATOM | 4624 | CG2 | THR | B | 302 | 42.585 | 33.076 | 89.600 | 1.00 | 68.67 | C |
| ATOM | 4625 | N | LYS | B | 303 | 41.603 | 33.065 | 85.680 | 1.00 | 67.32 | N |
| ATOM | 4626 | CA | LYS | B | 303 | 42.473 | 33.398 | 84.555 | 1.00 | 67.32 | C |
| ATOM | 4627 | C | LYS | B | 303 | 41.890 | 34.337 | 83.500 | 1.00 | 67.32 | C |
| ATOM | 4628 | O | LYS | B | 303 | 42.567 | 34.689 | 82.530 | 1.00 | 67.32 | O |
| ATOM | 4629 | CB | LYS | B | 303 | 42.972 | 32.108 | 83.903 | 1.00 | 63.31 | C |
| ATOM | 4630 | CG | LYS | B | 303 | 43.843 | 31.267 | 84.859 | 1.00 | 63.31 | C |
| ATOM | 4631 | CD | LYS | B | 303 | 44.373 | 30.011 | 84.190 | 0.00 | 63.31 | C |
| ATOM | 4632 | CE | LYS | B | 303 | 45.238 | 29.210 | 85.152 | 0.00 | 63.31 | C |
| ATOM | 4633 | NZ | LYS | B | 303 | 45.742 | 27.946 | 84.547 | 0.00 | 63.31 | N |
| ATOM | 4634 | N | VAL | B | 304 | 40.645 | 34.755 | 83.696 | 1.00 | 48.89 | N |
| ATOM | 4635 | CA | VAL | B | 304 | 40.009 | 35.671 | 82.765 | 1.00 | 48.89 | C |
| ATOM | 4636 | C | VAL | B | 304 | 40.552 | 37.086 | 83.002 | 1.00 | 48.89 | C |
| ATOM | 4637 | O | VAL | B | 304 | 40.678 | 37.874 | 82.065 | 1.00 | 48.89 | O |
| ATOM | 4638 | CB | VAL | B | 304 | 38.474 | 35.714 | 82.979 | 1.00 | 35.95 | C |
| ATOM | 4639 | CG1 | VAL | B | 304 | 37.831 | 36.609 | 81.934 | 0.00 | 35.95 | C |
| ATOM | 4640 | CG2 | VAL | B | 304 | 37.887 | 34.318 | 82.926 | 1.00 | 35.95 | C |
| ATOM | 4641 | N | PHE | B | 305 | 40.892 | 37.391 | 84.255 | 1.00 | 43.83 | N |
| ATOM | 4642 | CA | PHE | B | 305 | 41.367 | 38.726 | 84.634 | 1.00 | 43.83 | C |
| ATOM | 4643 | C | PHE | B | 305 | 42.864 | 38.877 | 84.911 | 1.00 | 43.83 | C |
| ATOM | 4644 | O | PHE | B | 305 | 43.594 | 37.898 | 84.940 | 1.00 | 43.83 | O |
| ATOM | 4645 | CB | PHE | B | 305 | 40.594 | 39.176 | 85.864 | 1.00 | 32.65 | C |
| ATOM | 4646 | CG | PHE | B | 305 | 39.112 | 39.002 | 85.734 | 1.00 | 32.65 | C |
| ATOM | 4647 | CD1 | PHE | B | 305 | 38.348 | 39.937 | 85.060 | 1.00 | 32.65 | C |

FIG. 1-76

```
ATOM   4648  CD2 PHE B 305      38.484  37.884  86.261  1.00 32.65           C
ATOM   4649  CE1 PHE B 305      36.988  39.765  84.921  1.00 32.65           C
ATOM   4650  CE2 PHE B 305      37.117  37.707  86.122  1.00 32.65           C
ATOM   4651  CZ  PHE B 305      36.371  38.645  85.449  1.00 32.65           C
ATOM   4652  N   ARG B 306      43.311  40.119  85.113  1.00 44.90           N
ATOM   4653  CA  ARG B 306      44.719  40.404  85.405  1.00 44.90           C
ATOM   4654  C   ARG B 306      45.061  39.663  86.690  1.00 44.90           C
ATOM   4655  O   ARG B 306      44.194  39.443  87.537  1.00 44.90           O
ATOM   4656  CB  ARG B 306      44.933  41.903  85.587  1.00 23.70           C
ATOM   4657  N   PRO B 307      46.334  39.274  86.862  1.00 56.05           N
ATOM   4658  CA  PRO B 307      46.732  38.542  88.080  1.00 56.05           C
ATOM   4659  C   PRO B 307      46.495  39.330  89.371  1.00 56.05           C
ATOM   4660  O   PRO B 307      46.385  38.749  90.455  1.00 56.05           O
ATOM   4661  CB  PRO B 307      48.219  38.247  87.845  1.00 73.61           C
ATOM   4662  CG  PRO B 307      48.380  38.348  86.318  1.00 73.61           C
ATOM   4663  CD  PRO B 307      47.497  39.529  85.990  1.00 73.61           C
ATOM   4664  N   ARG B 308      46.415  40.653  89.251  1.00 45.08           N
ATOM   4665  CA  ARG B 308      46.178  41.504  90.416  1.00 45.08           C
ATOM   4666  C   ARG B 308      44.723  41.680  90.864  1.00 45.08           C
ATOM   4667  O   ARG B 308      44.454  42.225  91.936  1.00 45.08           O
ATOM   4668  CB  ARG B 308      46.482  42.956  90.063  0.00 35.69           C
ATOM   4669  N   THR B 309      43.792  41.362  89.986  1.00 47.61           N
ATOM   4670  CA  THR B 309      42.351  41.277  90.259  1.00 47.61           C
ATOM   4671  C   THR B 309      41.907  40.592  91.547  1.00 47.61           C
ATOM   4672  O   THR B 309      42.059  39.387  91.709  1.00 47.61           O
ATOM   4673  CB  THR B 309      41.626  40.590  89.116  1.00 35.64           C
ATOM   4674  OG1 THR B 309      42.081  41.136  87.877  1.00 35.64           O
ATOM   4675  CG2 THR B 309      40.142  40.823  89.236  1.00 35.64           C
ATOM   4676  N   PRO B 310      41.323  41.364  92.471  1.00 44.91           N
ATOM   4677  CA  PRO B 310      40.840  40.868  93.761  1.00 44.91           C
ATOM   4678  C   PRO B 310      39.954  39.646  93.597  1.00 44.91           C
ATOM   4679  O   PRO B 310      38.952  39.693  92.884  1.00 44.91           O
ATOM   4680  CB  PRO B 310      40.064  42.052  94.308  1.00 31.40           C
ATOM   4681  CG  PRO B 310      40.810  43.216  93.764  1.00 31.40           C
ATOM   4682  CD  PRO B 310      41.055  42.807  92.335  1.00 31.40           C
ATOM   4683  N   PRO B 311      40.304  38.534  94.264  1.00 45.87           N
ATOM   4684  CA  PRO B 311      39.508  37.308  94.167  1.00 45.87           C
ATOM   4685  C   PRO B 311      38.003  37.493  94.358  1.00 45.87           C
ATOM   4686  O   PRO B 311      37.223  37.148  93.473  1.00 45.87           O
ATOM   4687  CB  PRO B 311      40.130  36.404  95.234  1.00 36.21           C
ATOM   4688  CG  PRO B 311      40.725  37.364  96.205  1.00 36.21           C
ATOM   4689  CD  PRO B 311      41.352  38.381  95.285  1.00 36.21           C
ATOM   4690  N   GLU B 312      37.578  38.033  95.493  1.00 41.29           N
ATOM   4691  CA  GLU B 312      36.142  38.187  95.692  1.00 41.29           C
ATOM   4692  C   GLU B 312      35.477  39.038  94.602  1.00 41.29           C
ATOM   4693  O   GLU B 312      34.262  38.974  94.408  1.00 41.29           O
ATOM   4694  CB  GLU B 312      35.817  38.715  97.103  1.00 70.73           C
ATOM   4695  CG  GLU B 312      36.611  39.903  97.573  1.00 70.73           C
ATOM   4696  CD  GLU B 312      38.084  39.596  97.653  1.00 70.73           C
ATOM   4697  OE1 GLU B 312      38.793  39.856  96.647  1.00 70.73           O
ATOM   4698  OE2 GLU B 312      38.522  39.079  98.711  1.00 70.73           O
ATOM   4699  N   ALA B 313      36.268  39.825  93.882  1.00 36.56           N
ATOM   4700  CA  ALA B 313      35.714  40.612  92.789  1.00 36.56           C
ATOM   4701  C   ALA B 313      35.435  39.590  91.694  1.00 36.56           C
ATOM   4702  O   ALA B 313      34.479  39.710  90.936  1.00 36.56           O
ATOM   4703  CB  ALA B 313      36.723  41.637  92.302  1.00 44.46           C
ATOM   4704  N   ILE B 314      36.292  38.578  91.624  1.00 33.59           N
ATOM   4705  CA  ILE B 314      36.146  37.513  90.649  1.00 33.59           C
ATOM   4706  C   ILE B 314      35.054  36.531  91.068  1.00 33.59           C
ATOM   4707  O   ILE B 314      34.269  36.076  90.234  1.00 33.59           O
ATOM   4708  CB  ILE B 314      37.471  36.758  90.472  1.00 40.76           C
ATOM   4709  CG1 ILE B 314      38.474  37.684  89.781  1.00 40.76           C
```

FIG. 1-77

```
ATOM   4710  CG2 ILE B 314      37.254  35.460  89.697  1.00 40.76           C
ATOM   4711  CD1 ILE B 314      39.771  37.015  89.370  1.00 40.76           C
ATOM   4712  N   ALA B 315      35.002  36.205  92.357  1.00 35.68           N
ATOM   4713  CA  ALA B 315      33.996  35.283  92.865  1.00 35.68           C
ATOM   4714  C   ALA B 315      32.615  35.820  92.547  1.00 35.68           C
ATOM   4715  O   ALA B 315      31.750  35.094  92.049  1.00 35.68           O
ATOM   4716  CB  ALA B 315      34.145  35.131  94.345  1.00 29.50           C
ATOM   4717  N   LEU B 316      32.418  37.103  92.841  1.00 42.05           N
ATOM   4718  CA  LEU B 316      31.149  37.780  92.608  1.00 42.05           C
ATOM   4719  C   LEU B 316      30.718  37.686  91.151  1.00 42.05           C
ATOM   4720  O   LEU B 316      29.540  37.509  90.860  1.00 42.05           O
ATOM   4721  CB  LEU B 316      31.254  39.248  93.034  1.00 30.04           C
ATOM   4722  CG  LEU B 316      30.075  40.155  92.684  1.00 30.04           C
ATOM   4723  CD1 LEU B 316      28.821  39.677  93.384  1.00 30.04           C
ATOM   4724  CD2 LEU B 316      30.405  41.573  93.084  1.00 30.04           C
ATOM   4725  N   CYS B 317      31.663  37.807  90.229  1.00 48.54           N
ATOM   4726  CA  CYS B 317      31.316  37.702  88.816  1.00 48.54           C
ATOM   4727  C   CYS B 317      30.669  36.367  88.464  1.00 48.54           C
ATOM   4728  O   CYS B 317      29.641  36.324  87.776  1.00 48.54           O
ATOM   4729  CB  CYS B 317      32.552  37.868  87.947  1.00 54.56           C
ATOM   4730  SG  CYS B 317      32.625  39.460  87.158  1.00 54.56           S
ATOM   4731  N   SER B 318      31.275  35.278  88.928  1.00 34.00           N
ATOM   4732  CA  SER B 318      30.761  33.956  88.632  1.00 34.00           C
ATOM   4733  C   SER B 318      29.398  33.695  89.254  1.00 34.00           C
ATOM   4734  O   SER B 318      28.716  32.734  88.871  1.00 34.00           O
ATOM   4735  CB  SER B 318      31.739  32.901  89.114  1.00 51.64           C
ATOM   4736  OG  SER B 318      31.894  32.999  90.514  1.00 51.64           O
ATOM   4737  N   ARG B 319      28.999  34.523  90.218  1.00 30.97           N
ATOM   4738  CA  ARG B 319      27.698  34.332  90.841  1.00 30.97           C
ATOM   4739  C   ARG B 319      26.650  35.192  90.160  1.00 30.97           C
ATOM   4740  O   ARG B 319      25.461  35.158  90.509  1.00 30.97           O
ATOM   4741  CB  ARG B 319      27.748  34.640  92.334  1.00 36.64           C
ATOM   4742  CG  ARG B 319      28.523  33.620  93.147  1.00 36.64           C
ATOM   4743  CD  ARG B 319      28.176  32.183  92.747  1.00 36.64           C
ATOM   4744  NE  ARG B 319      26.740  31.947  92.594  1.00 36.64           N
ATOM   4745  CZ  ARG B 319      25.860  31.946  93.590  1.00 36.64           C
ATOM   4746  NH1 ARG B 319      26.254  32.172  94.836  1.00 36.64           N
ATOM   4747  NH2 ARG B 319      24.578  31.707  93.335  1.00 36.64           N
ATOM   4748  N   LEU B 320      27.110  35.968  89.182  1.00 33.21           N
ATOM   4749  CA  LEU B 320      26.234  36.823  88.386  1.00 33.21           C
ATOM   4750  C   LEU B 320      26.120  36.179  86.993  1.00 33.21           C
ATOM   4751  O   LEU B 320      25.026  35.820  86.543  1.00 33.21           O
ATOM   4752  CB  LEU B 320      26.821  38.241  88.275  1.00 28.69           C
ATOM   4753  CG  LEU B 320      26.952  38.986  89.612  1.00 28.69           C
ATOM   4754  CD1 LEU B 320      27.668  40.317  89.446  1.00 28.69           C
ATOM   4755  CD2 LEU B 320      25.569  39.212  90.180  1.00 28.69           C
ATOM   4756  N   LEU B 321      27.267  36.008  86.334  1.00 29.93           N
ATOM   4757  CA  LEU B 321      27.310  35.424  85.005  1.00 29.93           C
ATOM   4758  C   LEU B 321      27.126  33.910  85.111  1.00 29.93           C
ATOM   4759  O   LEU B 321      28.070  33.124  85.004  1.00 29.93           O
ATOM   4760  CB  LEU B 321      28.629  35.821  84.340  1.00 27.53           C
ATOM   4761  CG  LEU B 321      28.716  37.358  84.294  1.00 27.53           C
ATOM   4762  CD1 LEU B 321      29.968  37.828  83.591  1.00 27.53           C
ATOM   4763  CD2 LEU B 321      27.488  37.900  83.586  1.00 27.53           C
ATOM   4764  N   GLU B 322      25.870  33.526  85.314  1.00 33.10           N
ATOM   4765  CA  GLU B 322      25.467  32.144  85.504  1.00 33.10           C
ATOM   4766  C   GLU B 322      24.362  31.775  84.545  1.00 33.10           C
ATOM   4767  O   GLU B 322      23.367  32.489  84.456  1.00 33.10           O
ATOM   4768  CB  GLU B 322      24.929  31.983  86.913  1.00 49.43           C
ATOM   4769  CG  GLU B 322      25.064  30.611  87.481  1.00 49.43           C
ATOM   4770  CD  GLU B 322      26.169  30.549  88.492  1.00 49.43           C
ATOM   4771  OE1 GLU B 322      26.012  31.176  89.567  1.00 49.43           O
```

FIG. 1-78

| | | | | | | | | | |
|---|---|---|---|---|---|---|---|---|---|
| ATOM | 4772 | OE2 | GLU B 322 | 27.194 | 29.890 | 88.210 | 1.00 | 49.43 | O |
| ATOM | 4773 | N | TYR B 323 | 24.514 | 30.653 | 83.849 | 1.00 | 32.76 | N |
| ATOM | 4774 | CA | TYR B 323 | 23.506 | 30.198 | 82.897 | 1.00 | 32.76 | C |
| ATOM | 4775 | C | TYR B 323 | 22.083 | 30.186 | 83.454 | 1.00 | 32.76 | C |
| ATOM | 4776 | O | TYR B 323 | 21.196 | 30.836 | 82.928 | 1.00 | 32.76 | O |
| ATOM | 4777 | CB | TYR B 323 | 23.859 | 28.795 | 82.395 | 1.00 | 34.11 | C |
| ATOM | 4778 | CG | TYR B 323 | 24.926 | 28.776 | 81.330 | 1.00 | 34.11 | C |
| ATOM | 4779 | CD1 | TYR B 323 | 24.779 | 29.514 | 80.162 | 1.00 | 34.11 | C |
| ATOM | 4780 | CD2 | TYR B 323 | 26.083 | 28.017 | 81.487 | 1.00 | 34.11 | C |
| ATOM | 4781 | CE1 | TYR B 323 | 25.766 | 29.495 | 79.179 | 1.00 | 34.11 | C |
| ATOM | 4782 | CE2 | TYR B 323 | 27.077 | 27.989 | 80.506 | 1.00 | 34.11 | C |
| ATOM | 4783 | CZ | TYR B 323 | 26.911 | 28.728 | 79.363 | 1.00 | 34.11 | C |
| ATOM | 4784 | OH | TYR B 323 | 27.897 | 28.706 | 78.417 | 1.00 | 34.11 | O |
| ATOM | 4785 | N | THR B 324 | 21.887 | 29.430 | 84.521 | 1.00 | 28.09 | N |
| ATOM | 4786 | CA | THR B 324 | 20.607 | 29.266 | 85.204 | 1.00 | 28.09 | C |
| ATOM | 4787 | C | THR B 324 | 20.200 | 30.584 | 85.847 | 1.00 | 28.09 | C |
| ATOM | 4788 | O | THR B 324 | 20.772 | 30.975 | 86.850 | 1.00 | 28.09 | O |
| ATOM | 4789 | CB | THR B 324 | 20.800 | 28.120 | 86.240 | 1.00 | 39.41 | C |
| ATOM | 4790 | OG1 | THR B 324 | 20.698 | 26.874 | 85.543 | 1.00 | 39.41 | O |
| ATOM | 4791 | CG2 | THR B 324 | 19.828 | 28.199 | 87.455 | 1.00 | 39.41 | C |
| ATOM | 4792 | N | PRO B 325 | 19.230 | 31.310 | 85.254 | 1.00 | 38.29 | N |
| ATOM | 4793 | CA | PRO B 325 | 18.811 | 32.592 | 85.843 | 1.00 | 38.29 | C |
| ATOM | 4794 | C | PRO B 325 | 18.619 | 32.508 | 87.352 | 1.00 | 38.29 | C |
| ATOM | 4795 | O | PRO B 325 | 19.221 | 33.265 | 88.131 | 1.00 | 38.29 | O |
| ATOM | 4796 | CB | PRO B 325 | 17.504 | 32.904 | 85.111 | 1.00 | 33.50 | C |
| ATOM | 4797 | CG | PRO B 325 | 17.756 | 32.345 | 83.741 | 1.00 | 33.50 | C |
| ATOM | 4798 | CD | PRO B 325 | 18.442 | 31.009 | 84.043 | 1.00 | 33.50 | C |
| ATOM | 4799 | N | THR B 326 | 17.779 | 31.565 | 87.756 | 1.00 | 37.45 | N |
| ATOM | 4800 | CA | THR B 326 | 17.493 | 31.366 | 89.167 | 1.00 | 37.45 | C |
| ATOM | 4801 | C | THR B 326 | 18.735 | 31.103 | 89.999 | 1.00 | 37.45 | C |
| ATOM | 4802 | O | THR B 326 | 18.666 | 31.113 | 91.221 | 1.00 | 37.45 | O |
| ATOM | 4803 | CB | THR B 326 | 16.520 | 30.202 | 89.375 | 1.00 | 32.11 | C |
| ATOM | 4804 | OG1 | THR B 326 | 16.986 | 29.061 | 88.650 | 1.00 | 32.11 | O |
| ATOM | 4805 | CG2 | THR B 326 | 15.131 | 30.576 | 88.889 | 1.00 | 32.11 | C |
| ATOM | 4806 | N | ALA B 327 | 19.870 | 30.867 | 89.357 | 1.00 | 27.18 | N |
| ATOM | 4807 | CA | ALA B 327 | 21.079 | 30.606 | 90.119 | 1.00 | 27.18 | C |
| ATOM | 4808 | C | ALA B 327 | 21.866 | 31.887 | 90.319 | 1.00 | 27.18 | C |
| ATOM | 4809 | O | ALA B 327 | 22.786 | 31.949 | 91.131 | 1.00 | 27.18 | O |
| ATOM | 4810 | CB | ALA B 327 | 21.928 | 29.582 | 89.413 | 1.00 | 13.76 | C |
| ATOM | 4811 | N | ARG B 328 | 21.502 | 32.916 | 89.568 | 1.00 | 31.26 | N |
| ATOM | 4812 | CA | ARG B 328 | 22.193 | 34.192 | 89.660 | 1.00 | 31.26 | C |
| ATOM | 4813 | C | ARG B 328 | 21.819 | 34.903 | 90.939 | 1.00 | 31.26 | C |
| ATOM | 4814 | O | ARG B 328 | 20.665 | 34.882 | 91.343 | 1.00 | 31.26 | O |
| ATOM | 4815 | CB | ARG B 328 | 21.815 | 35.073 | 88.480 | 1.00 | 27.28 | C |
| ATOM | 4816 | CG | ARG B 328 | 22.131 | 34.458 | 87.153 | 1.00 | 27.28 | C |
| ATOM | 4817 | CD | ARG B 328 | 21.522 | 35.230 | 85.997 | 1.00 | 27.28 | C |
| ATOM | 4818 | NE | ARG B 328 | 21.710 | 34.480 | 84.763 | 1.00 | 27.28 | N |
| ATOM | 4819 | CZ | ARG B 328 | 20.940 | 34.584 | 83.691 | 1.00 | 27.28 | C |
| ATOM | 4820 | NH1 | ARG B 328 | 19.910 | 35.419 | 83.674 | 1.00 | 27.28 | N |
| ATOM | 4821 | NH2 | ARG B 328 | 21.202 | 33.830 | 82.640 | 1.00 | 27.28 | N |
| ATOM | 4822 | N | LEU B 329 | 22.798 | 35.528 | 91.580 | 1.00 | 27.49 | N |
| ATOM | 4823 | CA | LEU B 329 | 22.535 | 36.285 | 92.796 | 1.00 | 27.49 | C |
| ATOM | 4824 | C | LEU B 329 | 21.405 | 37.287 | 92.542 | 1.00 | 27.49 | C |
| ATOM | 4825 | O | LEU B 329 | 21.132 | 37.665 | 91.407 | 1.00 | 27.49 | O |
| ATOM | 4826 | CB | LEU B 329 | 23.790 | 37.046 | 93.211 | 1.00 | 20.62 | C |
| ATOM | 4827 | CG | LEU B 329 | 24.734 | 36.415 | 94.230 | 1.00 | 20.62 | C |
| ATOM | 4828 | CD1 | LEU B 329 | 24.805 | 34.914 | 94.029 | 1.00 | 20.62 | C |
| ATOM | 4829 | CD2 | LEU B 329 | 26.101 | 37.061 | 94.096 | 1.00 | 20.62 | C |
| ATOM | 4830 | N | THR B 330 | 20.726 | 37.697 | 93.601 | 1.00 | 30.40 | N |
| ATOM | 4831 | CA | THR B 330 | 19.672 | 38.689 | 93.462 | 1.00 | 30.40 | C |
| ATOM | 4832 | C | THR B 330 | 20.386 | 40.012 | 93.727 | 1.00 | 30.40 | C |
| ATOM | 4833 | O | THR B 330 | 21.402 | 40.042 | 94.407 | 1.00 | 30.40 | O |

FIG. 1-79

| ATOM | 4834 | CB | THR | B | 330 | 18.553 | 38.472 | 94.492 | 1.00 | 29.69 | C |
|---|---|---|---|---|---|---|---|---|---|---|---|
| ATOM | 4835 | OG1 | THR | B | 330 | 19.054 | 38.746 | 95.801 | 1.00 | 29.69 | O |
| ATOM | 4836 | CG2 | THR | B | 330 | 18.049 | 37.039 | 94.434 | 0.00 | 29.69 | C |
| ATOM | 4837 | N | PRO | B | 331 | 19.883 | 41.115 | 93.175 | 1.00 | 22.73 | N |
| ATOM | 4838 | CA | PRO | B | 331 | 20.533 | 42.406 | 93.393 | 1.00 | 22.73 | C |
| ATOM | 4839 | C | PRO | B | 331 | 20.918 | 42.659 | 94.848 | 1.00 | 22.73 | C |
| ATOM | 4840 | O | PRO | B | 331 | 22.038 | 43.087 | 95.148 | 1.00 | 22.73 | O |
| ATOM | 4841 | CB | PRO | B | 331 | 19.494 | 43.392 | 92.892 | 1.00 | 23.90 | C |
| ATOM | 4842 | CG | PRO | B | 331 | 18.882 | 42.654 | 91.771 | 1.00 | 23.90 | C |
| ATOM | 4843 | CD | PRO | B | 331 | 18.677 | 41.270 | 92.350 | 1.00 | 23.90 | C |
| ATOM | 4844 | N | LEU | B | 332 | 19.985 | 42.370 | 95.751 | 1.00 | 37.71 | N |
| ATOM | 4845 | CA | LEU | B | 332 | 20.204 | 42.591 | 97.174 | 1.00 | 37.71 | C |
| ATOM | 4846 | C | LEU | B | 332 | 21.293 | 41.690 | 97.718 | 1.00 | 37.71 | C |
| ATOM | 4847 | O | LEU | B | 332 | 22.073 | 42.109 | 98.574 | 1.00 | 37.71 | O |
| ATOM | 4848 | CB | LEU | B | 332 | 18.911 | 42.360 | 97.953 | 1.00 | 28.88 | C |
| ATOM | 4849 | CG | LEU | B | 332 | 18.872 | 43.032 | 99.324 | 1.00 | 28.88 | C |
| ATOM | 4850 | CD1 | LEU | B | 332 | 18.844 | 44.524 | 99.135 | 1.00 | 28.88 | C |
| ATOM | 4851 | CD2 | LEU | B | 332 | 17.647 | 42.598 | 100.097 | 1.00 | 28.88 | C |
| ATOM | 4852 | N | GLU | B | 333 | 21.340 | 40.452 | 97.232 | 1.00 | 29.59 | N |
| ATOM | 4853 | CA | GLU | B | 333 | 22.359 | 39.512 | 97.682 | 1.00 | 29.59 | C |
| ATOM | 4854 | C | GLU | B | 333 | 23.692 | 40.014 | 97.190 | 1.00 | 29.59 | C |
| ATOM | 4855 | O | GLU | B | 333 | 24.692 | 39.908 | 97.879 | 1.00 | 29.59 | O |
| ATOM | 4856 | CB | GLU | B | 333 | 22.110 | 38.108 | 97.131 | 1.00 | 45.27 | C |
| ATOM | 4857 | CG | GLU | B | 333 | 20.891 | 37.404 | 97.706 | 1.00 | 45.27 | C |
| ATOM | 4858 | CD | GLU | B | 333 | 20.557 | 36.131 | 96.943 | 1.00 | 45.27 | C |
| ATOM | 4859 | OE1 | GLU | B | 333 | 20.941 | 36.048 | 95.752 | 1.00 | 45.27 | O |
| ATOM | 4860 | OE2 | GLU | B | 333 | 19.901 | 35.222 | 97.512 | 1.00 | 45.27 | O |
| ATOM | 4861 | N | ALA | B | 334 | 23.698 | 40.571 | 95.990 | 1.00 | 30.95 | N |
| ATOM | 4862 | CA | ALA | B | 334 | 24.915 | 41.106 | 95.414 | 1.00 | 30.95 | C |
| ATOM | 4863 | C | ALA | B | 334 | 25.469 | 42.237 | 96.293 | 1.00 | 30.95 | C |
| ATOM | 4864 | O | ALA | B | 334 | 26.674 | 42.319 | 96.535 | 1.00 | 30.95 | O |
| ATOM | 4865 | CB | ALA | B | 334 | 24.632 | 41.610 | 94.000 | 1.00 | 48.94 | C |
| ATOM | 4866 | N | CYS | B | 335 | 24.587 | 43.103 | 96.772 | 1.00 | 29.48 | N |
| ATOM | 4867 | CA | CYS | B | 335 | 25.008 | 44.201 | 97.626 | 1.00 | 29.48 | C |
| ATOM | 4868 | C | CYS | B | 335 | 25.680 | 43.692 | 98.899 | 1.00 | 29.48 | C |
| ATOM | 4869 | O | CYS | B | 335 | 26.563 | 44.349 | 99.449 | 1.00 | 29.48 | O |
| ATOM | 4870 | CB | CYS | B | 335 | 23.809 | 45.067 | 98.005 | 1.00 | 30.52 | C |
| ATOM | 4871 | SG | CYS | B | 335 | 23.177 | 46.115 | 96.668 | 1.00 | 30.52 | S |
| ATOM | 4872 | N | ALA | B | 336 | 25.278 | 42.513 | 99.356 | 1.00 | 28.04 | N |
| ATOM | 4873 | CA | ALA | B | 336 | 25.826 | 41.953 | 100.576 | 1.00 | 28.04 | C |
| ATOM | 4874 | C | ALA | B | 336 | 27.040 | 41.064 | 100.375 | 1.00 | 28.04 | C |
| ATOM | 4875 | O | ALA | B | 336 | 27.432 | 40.334 | 101.285 | 1.00 | 28.04 | O |
| ATOM | 4876 | CB | ALA | B | 336 | 24.746 | 41.184 | 101.314 | 1.00 | 27.36 | C |
| ATOM | 4877 | N | HIS | B | 337 | 27.641 | 41.133 | 99.196 | 1.00 | 28.78 | N |
| ATOM | 4878 | CA | HIS | B | 337 | 28.813 | 40.322 | 98.870 | 1.00 | 28.78 | C |
| ATOM | 4879 | C | HIS | B | 337 | 30.114 | 40.906 | 99.455 | 1.00 | 28.78 | C |
| ATOM | 4880 | O | HIS | B | 337 | 30.266 | 42.121 | 99.595 | 1.00 | 28.78 | O |
| ATOM | 4881 | CB | HIS | B | 337 | 28.899 | 40.192 | 97.348 | 1.00 | 32.11 | C |
| ATOM | 4882 | CG | HIS | B | 337 | 29.796 | 39.093 | 96.871 | 1.00 | 32.11 | C |
| ATOM | 4883 | ND1 | HIS | B | 337 | 31.166 | 39.234 | 96.781 | 1.00 | 32.11 | N |
| ATOM | 4884 | CD2 | HIS | B | 337 | 29.514 | 37.848 | 96.431 | 1.00 | 32.11 | C |
| ATOM | 4885 | CE1 | HIS | B | 337 | 31.686 | 38.121 | 96.303 | 1.00 | 32.11 | C |
| ATOM | 4886 | NE2 | HIS | B | 337 | 30.707 | 37.261 | 96.081 | 1.00 | 32.11 | N |
| ATOM | 4887 | N | SER | B | 338 | 31.049 | 40.030 | 99.802 | 1.00 | 34.64 | N |
| ATOM | 4888 | CA | SER | B | 338 | 32.325 | 40.448 | 100.383 | 1.00 | 34.64 | C |
| ATOM | 4889 | C | SER | B | 338 | 33.040 | 41.528 | 99.585 | 1.00 | 34.64 | C |
| ATOM | 4890 | O | SER | B | 338 | 33.648 | 42.441 | 100.144 | 1.00 | 34.64 | O |
| ATOM | 4891 | CB | SER | B | 338 | 33.248 | 39.248 | 100.505 | 1.00 | 44.51 | C |
| ATOM | 4892 | OG | SER | B | 338 | 32.578 | 38.205 | 101.179 | 1.00 | 44.51 | O |
| ATOM | 4893 | N | PHE | B | 339 | 32.975 | 41.410 | 98.267 | 1.00 | 32.14 | N |
| ATOM | 4894 | CA | PHE | B | 339 | 33.630 | 42.368 | 97.403 | 1.00 | 32.14 | C |
| ATOM | 4895 | C | PHE | B | 339 | 33.272 | 43.805 | 97.768 | 1.00 | 32.14 | C |

FIG. 1-80

```
ATOM   4896  O    PHE B 339      34.001  44.733  97.436  1.00 32.14           O
ATOM   4897  CB   PHE B 339      33.262  42.078  95.948  1.00 36.64           C
ATOM   4898  CG   PHE B 339      33.869  43.037  94.973  1.00 36.64           C
ATOM   4899  CD1  PHE B 339      35.251  43.240  94.943  1.00 36.64           C
ATOM   4900  CD2  PHE B 339      33.063  43.785  94.120  1.00 36.64           C
ATOM   4901  CE1  PHE B 339      35.819  44.185  94.084  1.00 36.64           C
ATOM   4902  CE2  PHE B 339      33.623  44.730  93.258  1.00 36.64           C
ATOM   4903  CZ   PHE B 339      35.003  44.929  93.242  1.00 36.64           C
ATOM   4904  N    PHE B 340      32.162  43.990  98.472  1.00 31.47           N
ATOM   4905  CA   PHE B 340      31.731  45.329  98.843  1.00 31.47           C
ATOM   4906  C    PHE B 340      31.962  45.655 100.318  1.00 31.47           C
ATOM   4907  O    PHE B 340      31.581  46.727 100.790  1.00 31.47           O
ATOM   4908  CB   PHE B 340      30.253  45.507  98.488  1.00 26.64           C
ATOM   4909  CG   PHE B 340      29.964  45.430  97.001  1.00 26.64           C
ATOM   4910  CD1  PHE B 340      30.567  46.319  96.111  1.00 26.64           C
ATOM   4911  CD2  PHE B 340      29.084  44.479  96.492  1.00 26.64           C
ATOM   4912  CE1  PHE B 340      30.297  46.258  94.754  1.00 26.64           C
ATOM   4913  CE2  PHE B 340      28.813  44.419  95.129  1.00 26.64           C
ATOM   4914  CZ   PHE B 340      29.418  45.306  94.266  1.00 26.64           C
ATOM   4915  N    ASP B 341      32.606  44.737 101.034  1.00 32.86           N
ATOM   4916  CA   ASP B 341      32.881  44.920 102.455  1.00 32.86           C
ATOM   4917  C    ASP B 341      33.642  46.211 102.736  1.00 32.86           C
ATOM   4918  O    ASP B 341      33.342  46.914 103.697  1.00 32.86           O
ATOM   4919  CB   ASP B 341      33.675  43.733 103.017  1.00 37.27           C
ATOM   4920  CG   ASP B 341      32.860  42.449 103.078  1.00 37.27           C
ATOM   4921  OD1  ASP B 341      31.631  42.494 102.863  1.00 37.27           O
ATOM   4922  OD2  ASP B 341      33.448  41.387 103.354  1.00 37.27           O
ATOM   4923  N    GLU B 342      34.627  46.530 101.913  1.00 26.18           N
ATOM   4924  CA   GLU B 342      35.378  47.752 102.130  1.00 26.18           C
ATOM   4925  C    GLU B 342      34.472  48.972 102.191  1.00 26.18           C
ATOM   4926  O    GLU B 342      34.774  49.953 102.868  1.00 26.18           O
ATOM   4927  CB   GLU B 342      36.405  47.953 101.024  1.00 50.98           C
ATOM   4928  CG   GLU B 342      36.912  49.371 100.949  1.00 50.98           C
ATOM   4929  CD   GLU B 342      38.091  49.527 100.013  1.00 50.98           C
ATOM   4930  OE1  GLU B 342      38.063  48.924  98.917  1.00 50.98           O
ATOM   4931  OE2  GLU B 342      39.044  50.264 100.371  1.00 50.98           O
ATOM   4932  N    LEU B 343      33.358  48.927 101.475  1.00 34.06           N
ATOM   4933  CA   LEU B 343      32.474  50.070 101.485  1.00 34.06           C
ATOM   4934  C    LEU B 343      31.814  50.187 102.838  1.00 34.06           C
ATOM   4935  O    LEU B 343      31.289  51.240 103.192  1.00 34.06           O
ATOM   4936  CB   LEU B 343      31.414  49.933 100.404  1.00 24.96           C
ATOM   4937  CG   LEU B 343      31.901  49.837  98.966  1.00 24.96           C
ATOM   4938  CD1  LEU B 343      30.687  49.878  98.062  1.00 24.96           C
ATOM   4939  CD2  LEU B 343      32.850  50.977  98.638  1.00 24.96           C
ATOM   4940  N    ARG B 344      31.842  49.104 103.604  1.00 39.71           N
ATOM   4941  CA   ARG B 344      31.225  49.120 104.920  1.00 39.71           C
ATOM   4942  C    ARG B 344      32.187  49.511 106.043  1.00 39.71           C
ATOM   4943  O    ARG B 344      31.788  49.624 107.213  1.00 39.71           O
ATOM   4944  CB   ARG B 344      30.571  47.764 105.206  1.00 27.83           C
ATOM   4945  CG   ARG B 344      29.214  47.610 104.535  1.00 27.83           C
ATOM   4946  CD   ARG B 344      28.552  46.304 104.894  1.00 27.83           C
ATOM   4947  NE   ARG B 344      29.096  45.169 104.150  1.00 27.83           N
ATOM   4948  CZ   ARG B 344      28.827  44.909 102.874  1.00 27.83           C
ATOM   4949  NH1  ARG B 344      28.017  45.701 102.186  1.00 27.83           N
ATOM   4950  NH2  ARG B 344      29.358  43.850 102.287  1.00 27.83           N
ATOM   4951  N    ASP B 345      33.449  49.726 105.679  1.00 40.61           N
ATOM   4952  CA   ASP B 345      34.462  50.118 106.642  1.00 40.61           C
ATOM   4953  C    ASP B 345      34.264  51.577 107.004  1.00 40.61           C
ATOM   4954  O    ASP B 345      34.430  52.453 106.153  1.00 40.61           O
ATOM   4955  CB   ASP B 345      35.862  49.966 106.056  1.00 75.95           C
ATOM   4956  CG   ASP B 345      36.951  50.326 107.063  1.00 75.95           C
ATOM   4957  OD1  ASP B 345      37.513  49.393 107.685  1.00 75.95           O
```

FIG. 1-81

```
ATOM   4958  OD2 ASP B 345      37.226  51.539 107.248  1.00 75.95           O
ATOM   4959  N   PRO B 346      33.925  51.864 108.273  1.00 38.56           N
ATOM   4960  CA  PRO B 346      33.709  53.245 108.732  1.00 38.56           C
ATOM   4961  C   PRO B 346      34.832  54.219 108.355  1.00 38.56           C
ATOM   4962  O   PRO B 346      34.630  55.433 108.333  1.00 38.56           O
ATOM   4963  CB  PRO B 346      33.534  53.090 110.244  1.00 38.64           C
ATOM   4964  CG  PRO B 346      34.215  51.760 110.561  1.00 38.64           C
ATOM   4965  CD  PRO B 346      33.818  50.911 109.390  1.00 38.64           C
ATOM   4966  N   ASN B 347      36.007  53.687 108.036  1.00 46.79           N
ATOM   4967  CA  ASN B 347      37.134  54.529 107.647  1.00 46.79           C
ATOM   4968  C   ASN B 347      37.246  54.724 106.137  1.00 46.79           C
ATOM   4969  O   ASN B 347      38.087  55.494 105.683  1.00 46.79           O
ATOM   4970  CB  ASN B 347      38.451  53.925 108.137  1.00 61.20           C
ATOM   4971  CG  ASN B 347      38.593  53.963 109.649  1.00 61.20           C
ATOM   4972  OD1 ASN B 347      38.934  52.953 110.270  1.00 61.20           O
ATOM   4973  ND2 ASN B 347      38.346  55.135 110.251  1.00 61.20           N
ATOM   4974  N   VAL B 348      36.428  54.030 105.349  1.00 41.91           N
ATOM   4975  CA  VAL B 348      36.543  54.181 103.903  1.00 41.91           C
ATOM   4976  C   VAL B 348      36.306  55.630 103.548  1.00 41.91           C
ATOM   4977  O   VAL B 348      35.518  56.314 104.194  1.00 41.91           O
ATOM   4978  CB  VAL B 348      35.557  53.271 103.122  1.00 64.67           C
ATOM   4979  CG1 VAL B 348      34.114  53.726 103.325  1.00 64.67           C
ATOM   4980  CG2 VAL B 348      35.290  53.271 101.656  1.00 64.67           C
ATOM   4981  N   LYS B 349      37.005  56.091 102.524  1.00 28.60           N
ATOM   4982  CA  LYS B 349      36.925  57.476 102.083  1.00 28.60           C
ATOM   4983  C   LYS B 349      37.144  57.452 100.573  1.00 28.60           C
ATOM   4984  O   LYS B 349      37.487  56.403 100.013  1.00 28.60           O
ATOM   4985  CB  LYS B 349      38.055  58.268 102.758  1.00 44.54           C
ATOM   4986  CG  LYS B 349      37.668  59.588 103.429  1.00 44.54           C
ATOM   4987  CD  LYS B 349      36.807  59.365 104.642  1.00 44.54           C
ATOM   4988  CE  LYS B 349      36.492  60.677 105.339  1.00 44.54           C
ATOM   4989  NZ  LYS B 349      35.555  60.486 106.503  1.00 44.54           N
ATOM   4990  N   LEU B 350      36.947  58.582  99.901  1.00 36.18           N
ATOM   4991  CA  LEU B 350      37.182  58.618  98.449  1.00 36.18           C
ATOM   4992  C   LEU B 350      38.595  59.111  98.182  1.00 36.18           C
ATOM   4993  O   LEU B 350      39.129  59.889  98.958  1.00 36.18           O
ATOM   4994  CB  LEU B 350      36.194  59.553  97.750  1.00 17.38           C
ATOM   4995  CG  LEU B 350      34.728  59.116  97.829  1.00 17.38           C
ATOM   4996  CD1 LEU B 350      33.837  60.106  97.099  1.00 17.38           C
ATOM   4997  CD2 LEU B 350      34.576  57.735  97.223  1.00 17.38           C
ATOM   4998  N   PRO B 351      39.235  58.647  97.099  1.00 39.56           N
ATOM   4999  CA  PRO B 351      40.597  59.115  96.807  1.00 39.56           C
ATOM   5000  C   PRO B 351      40.536  60.636  96.726  1.00 39.56           C
ATOM   5001  O   PRO B 351      41.532  61.349  96.749  1.00 39.56           O
ATOM   5002  CB  PRO B 351      40.909  58.456  95.464  1.00 37.60           C
ATOM   5003  CG  PRO B 351      39.558  58.185  94.880  1.00 37.60           C
ATOM   5004  CD  PRO B 351      38.760  57.727  96.057  1.00 37.60           C
ATOM   5005  N   ASN B 352      39.306  61.098  96.652  1.00 35.58           N
ATOM   5006  CA  ASN B 352      38.936  62.496  96.588  1.00 35.58           C
ATOM   5007  C   ASN B 352      39.244  63.163  97.934  1.00 35.58           C
ATOM   5008  O   ASN B 352      39.546  64.354  98.023  1.00 35.58           O
ATOM   5009  CB  ASN B 352      37.433  62.533  96.340  1.00 47.59           C
ATOM   5010  CG  ASN B 352      36.962  63.848  95.871  1.00 47.59           C
ATOM   5011  OD1 ASN B 352      35.765  64.091  95.821  1.00 47.59           O
ATOM   5012  ND2 ASN B 352      37.893  64.720  95.504  1.00 47.59           N
ATOM   5013  N   GLY B 353      39.135  62.371  98.989  1.00 33.34           N
ATOM   5014  CA  GLY B 353      39.371  62.879 100.318  1.00 33.34           C
ATOM   5015  C   GLY B 353      38.032  63.055 100.996  1.00 33.34           C
ATOM   5016  O   GLY B 353      37.930  63.006 102.221  1.00 33.34           O
ATOM   5017  N   ARG B 354      36.996  63.252 100.192  1.00 30.07           N
ATOM   5018  CA  ARG B 354      35.676  63.443 100.751  1.00 30.07           C
ATOM   5019  C   ARG B 354      34.939  62.131 101.015  1.00 30.07           C
```

FIG. 1-82

```
ATOM   5020  O    ARG B 354      35.330  61.077 100.537  1.00 30.07           O
ATOM   5021  CB   ARG B 354      34.846  64.377  99.853  1.00 49.54           C
ATOM   5022  CG   ARG B 354      34.388  63.798  98.538  1.00 49.54           C
ATOM   5023  CD   ARG B 354      33.411  64.742  97.847  1.00 49.54           C
ATOM   5024  NE   ARG B 354      34.067  65.898  97.239  1.00 49.54           N
ATOM   5025  CZ   ARG B 354      33.420  66.860  96.580  1.00 49.54           C
ATOM   5026  NH1  ARG B 354      32.092  66.809  96.449  1.00 49.54           N
ATOM   5027  NH2  ARG B 354      34.099  67.864  96.035  1.00 49.54           N
ATOM   5028  N    ASP B 355      33.879  62.213 101.809  1.00 49.23           N
ATOM   5029  CA   ASP B 355      33.065  61.056 102.176  1.00 49.23           C
ATOM   5030  C    ASP B 355      32.365  60.300 101.057  1.00 49.23           C
ATOM   5031  O    ASP B 355      31.963  60.890 100.041  1.00 49.23           O
ATOM   5032  CB   ASP B 355      31.984  61.472 103.161  1.00 56.92           C
ATOM   5033  CG   ASP B 355      32.476  61.513 104.572  1.00 56.92           C
ATOM   5034  OD1  ASP B 355      31.641  61.735 105.475  1.00 56.92           O
ATOM   5035  OD2  ASP B 355      33.694  61.323 104.783  1.00 56.92           O
ATOM   5036  N    THR B 356      32.198  58.993 101.276  1.00 26.81           N
ATOM   5037  CA   THR B 356      31.490  58.151 100.326  1.00 26.81           C
ATOM   5038  C    THR B 356      30.038  58.613 100.351  1.00 26.81           C
ATOM   5039  O    THR B 356      29.563  59.173 101.345  1.00 26.81           O
ATOM   5040  CB   THR B 356      31.516  56.657 100.716  1.00 34.33           C
ATOM   5041  OG1  THR B 356      31.109  56.518 102.076  1.00 34.33           O
ATOM   5042  CG2  THR B 356      32.901  56.064 100.537  1.00 34.33           C
ATOM   5043  N    PRO B 357      29.313  58.391  99.252  1.00 29.88           N
ATOM   5044  CA   PRO B 357      27.917  58.813  99.219  1.00 29.88           C
ATOM   5045  C    PRO B 357      27.040  57.896 100.062  1.00 29.88           C
ATOM   5046  O    PRO B 357      27.538  56.970 100.716  1.00 29.88           O
ATOM   5047  CB   PRO B 357      27.588  58.736  97.739  1.00 26.18           C
ATOM   5048  CG   PRO B 357      28.363  57.520  97.317  1.00 26.18           C
ATOM   5049  CD   PRO B 357      29.703  57.761  97.977  1.00 26.18           C
ATOM   5050  N    ALA B 358      25.738  58.180 100.046  1.00 21.54           N
ATOM   5051  CA   ALA B 358      24.739  57.390 100.758  1.00 21.54           C
ATOM   5052  C    ALA B 358      24.842  55.973 100.243  1.00 21.54           C
ATOM   5053  O    ALA B 358      24.737  55.724  99.044  1.00 21.54           O
ATOM   5054  CB   ALA B 358      23.354  57.931 100.490  1.00 14.47           C
ATOM   5055  N    LEU B 359      25.043  55.041 101.154  1.00 24.66           N
ATOM   5056  CA   LEU B 359      25.196  53.659 100.779  1.00 24.66           C
ATOM   5057  C    LEU B 359      24.280  52.758 101.583  1.00 24.66           C
ATOM   5058  O    LEU B 359      23.837  51.718 101.102  1.00 24.66           O
ATOM   5059  CB   LEU B 359      26.652  53.256 101.019  1.00 26.46           C
ATOM   5060  CG   LEU B 359      27.612  53.079  99.843  1.00 26.46           C
ATOM   5061  CD1  LEU B 359      27.368  54.115  98.774  1.00 26.46           C
ATOM   5062  CD2  LEU B 359      29.036  53.150 100.365  1.00 26.46           C
ATOM   5063  N    PHE B 360      23.977  53.185 102.803  1.00 28.43           N
ATOM   5064  CA   PHE B 360      23.195  52.376 103.720  1.00 28.43           C
ATOM   5065  C    PHE B 360      21.784  52.820 104.085  1.00 28.43           C
ATOM   5066  O    PHE B 360      21.155  52.225 104.959  1.00 28.43           O
ATOM   5067  CB   PHE B 360      24.021  52.192 104.994  1.00 28.12           C
ATOM   5068  CG   PHE B 360      25.465  51.928 104.728  1.00 28.12           C
ATOM   5069  CD1  PHE B 360      25.880  50.706 104.213  1.00 28.12           C
ATOM   5070  CD2  PHE B 360      26.415  52.919 104.964  1.00 28.12           C
ATOM   5071  CE1  PHE B 360      27.218  50.479 103.916  1.00 28.12           C
ATOM   5072  CE2  PHE B 360      27.752  52.706 104.673  1.00 28.12           C
ATOM   5073  CZ   PHE B 360      28.161  51.478 104.153  1.00 28.12           C
ATOM   5074  N    ASN B 361      21.265  53.845 103.428  1.00 25.80           N
ATOM   5075  CA   ASN B 361      19.919  54.294 103.750  1.00 25.80           C
ATOM   5076  C    ASN B 361      18.838  53.423 103.102  1.00 25.80           C
ATOM   5077  O    ASN B 361      18.014  53.907 102.347  1.00 25.80           O
ATOM   5078  CB   ASN B 361      19.754  55.749 103.329  1.00 26.59           C
ATOM   5079  CG   ASN B 361      20.045  55.957 101.879  1.00 26.59           C
ATOM   5080  OD1  ASN B 361      20.901  55.285 101.308  1.00 26.59           O
ATOM   5081  ND2  ASN B 361      19.339  56.892 101.264  1.00 26.59           N
```

FIG. 1-83

```
ATOM   5082  N    PHE B 362      18.847  52.136 103.417  1.00 24.90           N
ATOM   5083  CA   PHE B 362      17.879  51.199 102.879  1.00 24.90           C
ATOM   5084  C    PHE B 362      16.496  51.424 103.445  1.00 24.90           C
ATOM   5085  O    PHE B 362      16.357  51.817 104.601  1.00 24.90           O
ATOM   5086  CB   PHE B 362      18.300  49.781 103.231  1.00 31.54           C
ATOM   5087  CG   PHE B 362      19.409  49.252 102.398  1.00 31.54           C
ATOM   5088  CD1  PHE B 362      19.150  48.670 101.170  1.00 31.54           C
ATOM   5089  CD2  PHE B 362      20.715  49.294 102.856  1.00 31.54           C
ATOM   5090  CE1  PHE B 362      20.178  48.128 100.409  1.00 31.54           C
ATOM   5091  CE2  PHE B 362      21.758  48.755 102.100  1.00 31.54           C
ATOM   5092  CZ   PHE B 362      21.483  48.169 100.875  1.00 31.54           C
ATOM   5093  N    THR B 363      15.474  51.170 102.633  1.00 39.25           N
ATOM   5094  CA   THR B 363      14.080  51.285 103.085  1.00 39.25           C
ATOM   5095  C    THR B 363      13.514  49.868 103.089  1.00 39.25           C
ATOM   5096  O    THR B 363      14.111  48.950 102.510  1.00 39.25           O
ATOM   5097  CB   THR B 363      13.184  52.137 102.146  1.00 19.80           C
ATOM   5098  OG1  THR B 363      13.108  51.516 100.857  1.00 19.80           O
ATOM   5099  CG2  THR B 363      13.709  53.540 102.025  1.00 19.80           C
ATOM   5100  N    THR B 364      12.364  49.690 103.736  1.00 32.91           N
ATOM   5101  CA   THR B 364      11.729  48.379 103.811  1.00 32.91           C
ATOM   5102  C    THR B 364      11.472  47.855 102.401  1.00 32.91           C
ATOM   5103  O    THR B 364      11.810  46.723 102.081  1.00 32.91           O
ATOM   5104  CB   THR B 364      10.385  48.447 104.552  1.00 34.16           C
ATOM   5105  OG1  THR B 364      10.515  49.282 105.705  1.00 34.16           O
ATOM   5106  CG2  THR B 364       9.962  47.073 105.001  1.00 34.16           C
ATOM   5107  N    GLN B 365      10.877  48.689 101.561  1.00 28.22           N
ATOM   5108  CA   GLN B 365      10.584  48.288 100.204  1.00 28.22           C
ATOM   5109  C    GLN B 365      11.825  47.743  99.513  1.00 28.22           C
ATOM   5110  O    GLN B 365      11.779  46.738  98.806  1.00 28.22           O
ATOM   5111  CB   GLN B 365      10.039  49.478  99.414  1.00 40.21           C
ATOM   5112  CG   GLN B 365       9.985  49.244  97.917  1.00 40.21           C
ATOM   5113  CD   GLN B 365       9.154  48.032  97.541  1.00 40.21           C
ATOM   5114  OE1  GLN B 365       8.027  48.167  97.092  1.00 40.21           O
ATOM   5115  NE2  GLN B 365       9.708  46.845  97.730  0.00 40.21           N
ATOM   5116  N    GLU B 366      12.949  48.407  99.729  1.00 36.17           N
ATOM   5117  CA   GLU B 366      14.186  48.002  99.089  1.00 36.17           C
ATOM   5118  C    GLU B 366      14.749  46.708  99.637  1.00 36.17           C
ATOM   5119  O    GLU B 366      15.452  45.982  98.930  1.00 36.17           O
ATOM   5120  CB   GLU B 366      15.200  49.133  99.227  1.00 39.37           C
ATOM   5121  CG   GLU B 366      16.539  48.858  98.589  1.00 39.37           C
ATOM   5122  CD   GLU B 366      17.368  50.110  98.518  1.00 39.37           C
ATOM   5123  OE1  GLU B 366      17.099  51.014  99.345  1.00 39.37           O
ATOM   5124  OE2  GLU B 366      18.271  50.185  97.654  1.00 39.37           O
ATOM   5125  N    LEU B 367      14.430  46.421 100.897  1.00 31.88           N
ATOM   5126  CA   LEU B 367      14.909  45.213 101.568  1.00 31.88           C
ATOM   5127  C    LEU B 367      13.912  44.074 101.504  1.00 31.88           C
ATOM   5128  O    LEU B 367      14.239  42.934 101.835  1.00 31.88           O
ATOM   5129  CB   LEU B 367      15.175  45.509 103.036  1.00 41.02           C
ATOM   5130  CG   LEU B 367      16.157  46.626 103.361  1.00 41.02           C
ATOM   5131  CD1  LEU B 367      15.908  47.131 104.785  1.00 41.02           C
ATOM   5132  CD2  LEU B 367      17.573  46.108 103.186  1.00 41.02           C
ATOM   5133  N    SER B 368      12.694  44.395 101.087  1.00 37.83           N
ATOM   5134  CA   SER B 368      11.615  43.423 101.018  1.00 37.83           C
ATOM   5135  C    SER B 368      11.963  42.072 100.406  1.00 37.83           C
ATOM   5136  O    SER B 368      11.341  41.069 100.743  1.00 37.83           O
ATOM   5137  CB   SER B 368      10.417  44.031 100.295  1.00 55.37           C
ATOM   5138  OG   SER B 368      10.784  44.520  99.016  1.00 55.37           O
ATOM   5139  N    SER B 369      12.949  42.030  99.517  1.00 38.48           N
ATOM   5140  CA   SER B 369      13.333  40.759  98.909  1.00 38.48           C
ATOM   5141  C    SER B 369      13.920  39.803  99.934  1.00 38.48           C
ATOM   5142  O    SER B 369      13.703  38.612  99.845  1.00 38.48           O
ATOM   5143  CB   SER B 369      14.335  40.976  97.770  1.00 42.54           C
```

FIG. 1-84

```
ATOM   5144  OG  SER B 369      15.371  41.878   98.128  1.00 42.54        O
ATOM   5145  N   ASN B 370      14.654  40.325  100.907  1.00 25.59        N
ATOM   5146  CA  ASN B 370      15.260  39.486  101.934  1.00 25.59        C
ATOM   5147  C   ASN B 370      15.723  40.333  103.126  1.00 25.59        C
ATOM   5148  O   ASN B 370      16.901  40.665  103.260  1.00 25.59        O
ATOM   5149  CB  ASN B 370      16.426  38.710  101.328  1.00 36.57        C
ATOM   5150  CG  ASN B 370      17.109  37.794  102.323  1.00 36.57        C
ATOM   5151  OD1 ASN B 370      17.918  36.951  101.940  1.00 36.57        O
ATOM   5152  ND2 ASN B 370      16.802  37.957  103.600  1.00 36.57        N
ATOM   5153  N   PRO B 371      14.781  40.681  104.018  1.00 38.05        N
ATOM   5154  CA  PRO B 371      15.011  41.494  105.223  1.00 38.05        C
ATOM   5155  C   PRO B 371      16.213  41.088  106.080  1.00 38.05        C
ATOM   5156  O   PRO B 371      16.988  41.938  106.515  1.00 38.05        O
ATOM   5157  CB  PRO B 371      13.687  41.370  105.976  1.00 25.90        C
ATOM   5158  CG  PRO B 371      12.691  41.261  104.865  1.00 25.90        C
ATOM   5159  CD  PRO B 371      13.362  40.279  103.926  1.00 25.90        C
ATOM   5160  N   PRO B 372      16.373  39.786  106.350  1.00 37.48        N
ATOM   5161  CA  PRO B 372      17.512  39.362  107.165  1.00 37.48        C
ATOM   5162  C   PRO B 372      18.813  40.066  106.790  1.00 37.48        C
ATOM   5163  O   PRO B 372      19.637  40.353  107.655  1.00 37.48        O
ATOM   5164  CB  PRO B 372      17.561  37.861  106.916  1.00 28.16        C
ATOM   5165  CG  PRO B 372      16.107  37.510  106.847  1.00 28.16        C
ATOM   5166  CD  PRO B 372      15.508  38.637  106.015  1.00 28.16        C
ATOM   5167  N   LEU B 373      18.983  40.353  105.502  1.00 34.53        N
ATOM   5168  CA  LEU B 373      20.185  41.014  104.993  1.00 34.53        C
ATOM   5169  C   LEU B 373      20.564  42.320  105.678  1.00 34.53        C
ATOM   5170  O   LEU B 373      21.746  42.646  105.759  1.00 34.53        O
ATOM   5171  CB  LEU B 373      20.039  41.262  103.491  1.00 37.09        C
ATOM   5172  CG  LEU B 373      20.376  40.102  102.545  1.00 37.09        C
ATOM   5173  CD1 LEU B 373      19.965  38.797  103.191  1.00 37.09        C
ATOM   5174  CD2 LEU B 373      19.686  40.290  101.186  1.00 37.09        C
ATOM   5175  N   ALA B 374      19.573  43.061  106.171  1.00 31.16        N
ATOM   5176  CA  ALA B 374      19.822  44.346  106.828  1.00 31.16        C
ATOM   5177  C   ALA B 374      21.016  44.270  107.749  1.00 31.16        C
ATOM   5178  O   ALA B 374      21.763  45.235  107.899  1.00 31.16        O
ATOM   5179  CB  ALA B 374      18.593  44.798  107.611  1.00 26.64        C
ATOM   5180  N   THR B 375      21.201  43.105  108.353  1.00 37.11        N
ATOM   5181  CA  THR B 375      22.305  42.889  109.278  1.00 37.11        C
ATOM   5182  C   THR B 375      23.662  43.066  108.650  1.00 37.11        C
ATOM   5183  O   THR B 375      24.616  43.399  109.339  1.00 37.11        O
ATOM   5184  CB  THR B 375      22.228  41.505  109.896  1.00 34.79        C
ATOM   5185  OG1 THR B 375      21.188  41.505  110.877  1.00 34.79        O
ATOM   5186  CG2 THR B 375      23.552  41.123  110.549  1.00 34.79        C
ATOM   5187  N   ILE B 376      23.756  42.827  107.348  1.00 41.34        N
ATOM   5188  CA  ILE B 376      25.025  43.001  106.663  1.00 41.34        C
ATOM   5189  C   ILE B 376      24.978  44.320  105.908  1.00 41.34        C
ATOM   5190  O   ILE B 376      25.906  45.116  105.978  1.00 41.34        O
ATOM   5191  CB  ILE B 376      25.305  41.868  105.671  1.00 31.14        C
ATOM   5192  CG1 ILE B 376      25.202  40.521  106.374  1.00 31.14        C
ATOM   5193  CG2 ILE B 376      26.698  42.021  105.113  1.00 31.14        C
ATOM   5194  CD1 ILE B 376      25.472  39.332  105.465  1.00 31.14        C
ATOM   5195  N   LEU B 377      23.882  44.542  105.195  1.00 27.23        N
ATOM   5196  CA  LEU B 377      23.687  45.764  104.430  1.00 27.23        C
ATOM   5197  C   LEU B 377      23.908  47.025  105.268  1.00 27.23        C
ATOM   5198  O   LEU B 377      24.431  48.024  104.774  1.00 27.23        O
ATOM   5199  CB  LEU B 377      22.274  45.768  103.839  1.00 32.98        C
ATOM   5200  CG  LEU B 377      22.142  45.157  102.442  1.00 32.98        C
ATOM   5201  CD1 LEU B 377      23.117  44.008  102.269  1.00 32.98        C
ATOM   5202  CD2 LEU B 377      20.699  44.714  102.206  1.00 32.98        C
ATOM   5203  N   ILE B 378      23.512  46.970  106.534  1.00 33.35        N
ATOM   5204  CA  ILE B 378      23.660  48.106  107.427  1.00 33.35        C
ATOM   5205  C   ILE B 378      24.732  47.826  108.477  1.00 33.35        C
```

FIG. 1-85

| | | | | | | | | | | |
|---|---|---|---|---|---|---|---|---|---|---|
| ATOM | 5206 | O | ILE | B | 378 | 24.494 | 47.127 | 109.447 | 1.00 33.35 | O |
| ATOM | 5207 | CB | ILE | B | 378 | 22.321 | 48.427 | 108.090 | 1.00 39.29 | C |
| ATOM | 5208 | CG1 | ILE | B | 378 | 21.334 | 48.876 | 107.012 | 1.00 39.29 | C |
| ATOM | 5209 | CG2 | ILE | B | 378 | 22.497 | 49.505 | 109.130 | 1.00 39.29 | C |
| ATOM | 5210 | CD1 | ILE | B | 378 | 19.913 | 49.057 | 107.493 | 1.00 39.29 | C |
| ATOM | 5211 | N | PRO | B | 379 | 25.933 | 48.394 | 108.290 | 1.00 45.99 | N |
| ATOM | 5212 | CA | PRO | B | 379 | 27.063 | 48.209 | 109.199 | 1.00 45.99 | C |
| ATOM | 5213 | C | PRO | B | 379 | 26.803 | 48.864 | 110.545 | 1.00 45.99 | C |
| ATOM | 5214 | O | PRO | B | 379 | 26.045 | 49.833 | 110.636 | 1.00 45.99 | O |
| ATOM | 5215 | CB | PRO | B | 379 | 28.202 | 48.870 | 108.448 | 1.00 44.90 | C |
| ATOM | 5216 | CG | PRO | B | 379 | 27.507 | 50.080 | 107.882 | 1.00 44.90 | C |
| ATOM | 5217 | CD | PRO | B | 379 | 26.211 | 49.490 | 107.341 | 1.00 44.90 | C |
| ATOM | 5218 | N | PRO | B | 380 | 27.451 | 48.348 | 111.602 | 1.00 54.40 | N |
| ATOM | 5219 | CA | PRO | B | 380 | 27.346 | 48.816 | 112.987 | 1.00 54.40 | C |
| ATOM | 5220 | C | PRO | B | 380 | 27.403 | 50.333 | 113.166 | 1.00 54.40 | C |
| ATOM | 5221 | O | PRO | B | 380 | 26.720 | 50.875 | 114.035 | 1.00 54.40 | O |
| ATOM | 5222 | CB | PRO | B | 380 | 28.511 | 48.109 | 113.679 | 1.00 51.12 | C |
| ATOM | 5223 | CG | PRO | B | 380 | 28.643 | 46.836 | 112.910 | 1.00 51.12 | C |
| ATOM | 5224 | CD | PRO | B | 380 | 28.491 | 47.307 | 111.484 | 1.00 51.12 | C |
| ATOM | 5225 | N | HIS | B | 381 | 28.203 | 51.028 | 112.364 | 1.00 39.13 | N |
| ATOM | 5226 | CA | HIS | B | 381 | 28.278 | 52.477 | 112.525 | 1.00 39.13 | C |
| ATOM | 5227 | C | HIS | B | 381 | 27.184 | 53.206 | 111.738 | 1.00 39.13 | C |
| ATOM | 5228 | O | HIS | B | 381 | 26.837 | 54.330 | 112.069 | 1.00 39.13 | O |
| ATOM | 5229 | CB | HIS | B | 381 | 29.656 | 52.978 | 112.100 | 1.00 45.13 | C |
| ATOM | 5230 | CG | HIS | B | 381 | 29.992 | 52.648 | 110.684 | 1.00 45.13 | C |
| ATOM | 5231 | ND1 | HIS | B | 381 | 29.624 | 53.451 | 109.624 | 1.00 45.13 | N |
| ATOM | 5232 | CD2 | HIS | B | 381 | 30.605 | 51.568 | 110.143 | 1.00 45.13 | C |
| ATOM | 5233 | CE1 | HIS | B | 381 | 29.998 | 52.883 | 108.491 | 1.00 45.13 | C |
| ATOM | 5234 | NE2 | HIS | B | 381 | 30.596 | 51.738 | 108.780 | 1.00 45.13 | N |
| ATOM | 5235 | N | ALA | B | 382 | 26.643 | 52.572 | 110.700 | 1.00 53.09 | N |
| ATOM | 5236 | CA | ALA | B | 382 | 25.598 | 53.204 | 109.891 | 1.00 53.09 | C |
| ATOM | 5237 | C | ALA | B | 382 | 24.438 | 53.694 | 110.753 | 1.00 53.09 | C |
| ATOM | 5238 | O | ALA | B | 382 | 24.217 | 53.183 | 111.859 | 1.00 53.09 | O |
| ATOM | 5239 | CB | ALA | B | 382 | 25.085 | 52.230 | 108.851 | 0.00 35.69 | C |
| TER | 5240 | | ALA | B | 382 | | | | | |
| HETATM | 5241 | P | PO4 | | 101 | 6.674 | 44.717 | 75.601 | 1.00100.00 | P |
| HETATM | 5242 | O1 | PO4 | | 101 | 5.864 | 45.844 | 75.197 | 1.00100.00 | O |
| HETATM | 5243 | O2 | PO4 | | 101 | 6.533 | 44.553 | 77.054 | 1.00100.00 | O |
| HETATM | 5244 | O3 | PO4 | | 101 | 8.069 | 45.007 | 75.230 | 1.00100.00 | O |
| HETATM | 5245 | O4 | PO4 | | 101 | 6.207 | 43.462 | 74.899 | 1.00100.00 | O |
| HETATM | 5246 | P | PO4 | | 102 | 20.855 | 25.652 | 63.621 | 1.00 84.35 | P |
| HETATM | 5247 | O1 | PO4 | | 102 | 20.939 | 26.503 | 64.776 | 1.00 84.35 | O |
| HETATM | 5248 | O2 | PO4 | | 102 | 20.692 | 24.267 | 64.090 | 1.00 84.35 | O |
| HETATM | 5249 | O3 | PO4 | | 102 | 22.103 | 25.807 | 62.865 | 1.00 84.35 | O |
| HETATM | 5250 | O4 | PO4 | | 102 | 19.672 | 26.051 | 62.776 | 1.00 84.35 | O |
| HETATM | 5251 | P | PO4 | | 103 | 14.872 | 32.932 | 47.919 | 1.00 66.00 | P |
| HETATM | 5252 | O1 | PO4 | | 103 | 14.128 | 34.220 | 47.710 | 1.00 66.00 | O |
| HETATM | 5253 | O2 | PO4 | | 103 | 14.605 | 32.419 | 49.305 | 1.00 66.00 | O |
| HETATM | 5254 | O3 | PO4 | | 103 | 16.325 | 33.159 | 47.739 | 1.00 66.00 | O |
| HETATM | 5255 | O4 | PO4 | | 103 | 14.413 | 31.927 | 46.921 | 1.00 66.00 | O |
| HETATM | 5256 | P | PO4 | | 104 | 15.879 | 39.372 | 90.825 | 1.00 70.83 | P |
| HETATM | 5257 | O1 | PO4 | | 104 | 14.867 | 40.478 | 90.860 | 1.00 70.83 | O |
| HETATM | 5258 | O2 | PO4 | | 104 | 16.157 | 38.910 | 92.226 | 1.00 70.83 | O |
| HETATM | 5259 | O3 | PO4 | | 104 | 17.150 | 39.862 | 90.202 | 1.00 70.83 | O |
| HETATM | 5260 | O4 | PO4 | | 104 | 15.337 | 38.231 | 90.020 | 1.00 70.83 | O |
| HETATM | 5261 | O | HOH | | 1 | 9.191 | 37.329 | 44.636 | 1.00 49.67 | O |
| HETATM | 5262 | O | HOH | | 2 | 15.038 | 50.827 | 80.223 | 1.00 21.84 | O |
| HETATM | 5263 | O | HOH | | 3 | 19.402 | 41.863 | 66.281 | 1.00 28.26 | O |
| HETATM | 5264 | O | HOH | | 4 | 20.267 | 40.502 | 79.708 | 1.00 24.44 | O |
| HETATM | 5265 | O | HOH | | 5 | 26.076 | 47.256 | 102.637 | 1.00 22.06 | O |
| HETATM | 5266 | O | HOH | | 6 | 19.478 | 44.435 | 81.151 | 1.00 26.60 | O |
| HETATM | 5267 | O | HOH | | 7 | 12.462 | 34.455 | 55.823 | 1.00 27.03 | O |

FIG. 1-86

```
HETATM 5268  O   HOH    8     27.998  31.207  56.576  1.00 32.82           O
HETATM 5269  O   HOH    9     19.068  37.507  89.791  1.00 28.09           O
HETATM 5270  O   HOH   10     22.489  36.839  55.671  1.00 18.10           O
HETATM 5271  O   HOH   11     23.639  53.938  97.457  1.00 23.00           O
HETATM 5272  O   HOH   12     22.210  39.688  33.394  1.00 29.50           O
HETATM 5273  O   HOH   13      9.251  51.644  79.293  1.00 27.54           O
HETATM 5274  O   HOH   14     14.011  28.741  52.236  1.00 20.48           O
HETATM 5275  O   HOH   15     22.113  48.057  58.719  1.00 17.07           O
HETATM 5276  O   HOH   16     17.953  60.685  92.504  1.00 29.75           O
HETATM 5277  O   HOH   17      5.362  47.793  82.405  1.00 37.81           O
HETATM 5278  O   HOH   18     31.088  43.222  79.519  1.00 29.72           O
HETATM 5279  O   HOH   19     15.632  35.357  83.246  1.00 25.61           O
HETATM 5280  O   HOH   20     12.181  36.442  48.562  1.00 33.87           O
HETATM 5281  O   HOH   21     24.906  60.578  98.815  1.00 29.46           O
HETATM 5282  O   HOH   22     30.348  41.575  77.756  1.00 14.18           O
HETATM 5283  O   HOH   23      2.239  50.498  79.907  1.00 28.29           O
HETATM 5284  O   HOH   24     23.104  58.041  78.414  1.00 40.94           O
HETATM 5285  O   HOH   25     18.905  45.022  58.992  1.00 38.17           O
HETATM 5286  O   HOH   26     29.225  36.586  38.097  1.00 30.20           O
HETATM 5287  O   HOH   27     19.258  38.337  57.570  1.00 28.48           O
HETATM 5288  O   HOH   28     15.467  33.678  87.085  1.00 32.59           O
HETATM 5289  O   HOH   29     17.338  41.559  95.186  1.00 24.45           O
HETATM 5290  O   HOH   30     26.087  39.010  77.232  1.00 27.43           O
HETATM 5291  O   HOH   31     15.962  30.757  67.920  1.00 41.75           O
HETATM 5292  O   HOH   32     10.967  48.375  50.863  1.00 35.33           O
HETATM 5293  O   HOH   33      6.505  43.542  52.898  1.00 41.84           O
HETATM 5294  O   HOH   34     13.752  46.755  37.095  1.00 26.83           O
HETATM 5295  O   HOH   35     16.682  33.443  42.693  1.00 38.86           O
HETATM 5296  O   HOH   36     14.262  55.977  75.096  1.00 32.77           O
HETATM 5297  O   HOH   37     16.537  51.554  77.202  1.00 26.04           O
HETATM 5298  O   HOH   38      7.552  54.446  76.907  1.00 33.82           O
HETATM 5299  O   HOH   39     28.049  29.694  63.259  1.00 40.22           O
HETATM 5300  O   HOH   40     11.611  50.753  74.054  1.00 44.65           O
HETATM 5301  O   HOH   41      4.009  49.944  84.253  1.00 44.06           O
HETATM 5302  O   HOH   42      7.836  46.108  53.542  1.00 29.68           O
HETATM 5303  O   HOH   43     27.869  25.677  57.946  1.00 14.67           O
HETATM 5304  O   HOH   44     29.546  33.027  59.435  1.00 24.04           O
HETATM 5305  O   HOH   45     30.800  35.677  62.119  1.00 46.57           O
HETATM 5306  O   HOH   46     18.389  30.071  43.481  1.00 31.90           O
CONECT 5241 5242 5243 5244 5245
CONECT 5242 5241
CONECT 5243 5241
CONECT 5244 5241
CONECT 5245 5241
CONECT 5246 5247 5248 5249 5250
CONECT 5247 5246
CONECT 5248 5246
CONECT 5249 5246
CONECT 5250 5246
CONECT 5251 5252 5253 5254 5255
CONECT 5252 5251
CONECT 5253 5251
CONECT 5254 5251
CONECT 5255 5251
CONECT 5256 5257 5258 5259 5260
CONECT 5257 5256
CONECT 5258 5256
CONECT 5259 5256
CONECT 5260 5256
MASTER        486    0    4   32   25    0    0    6 5304    2   20   66
END
```

FIG. 2-1

|      | Atom Type | Resid | # | X | Y | Z | OCC | B | |
|------|-----------|-------|---|---|---|---|-----|---|---|
| ATOM | 1  | CB  | VAL A | 37 | 24.016 | -4.419 | 22.952 | 1.00 | 43.19 | C |
| ATOM | 2  | CG1 | VAL A | 37 | 22.659 | -4.307 | 23.637 | 1.00 | 44.26 | C |
| ATOM | 3  | CG2 | VAL A | 37 | 24.253 | -5.845 | 22.488 | 1.00 | 44.65 | C |
| ATOM | 4  | C   | VAL A | 37 | 23.549 | -2.093 | 22.205 | 1.00 | 42.31 | C |
| ATOM | 5  | O   | VAL A | 37 | 24.169 | -1.420 | 23.025 | 1.00 | 42.51 | O |
| ATOM | 6  | N   | VAL A | 37 | 25.445 | -3.418 | 21.159 | 1.00 | 41.74 | N |
| ATOM | 7  | CA  | VAL A | 37 | 24.075 | -3.462 | 21.752 | 1.00 | 43.02 | C |
| ATOM | 8  | N   | THR A | 38 | 22.397 | -1.703 | 21.660 | 1.00 | 41.95 | N |
| ATOM | 9  | CA  | THR A | 38 | 21.752 | -0.435 | 21.987 | 1.00 | 41.33 | C |
| ATOM | 10 | CB  | THR A | 38 | 21.345 | 0.338  | 20.712 | 1.00 | 41.73 | C |
| ATOM | 11 | OG1 | THR A | 38 | 22.484 | 0.484  | 19.856 | 1.00 | 42.64 | O |
| ATOM | 12 | CG2 | THR A | 38 | 20.803 | 1.723  | 21.065 | 1.00 | 40.94 | C |
| ATOM | 13 | C   | THR A | 38 | 20.491 | -0.697 | 22.805 | 1.00 | 41.33 | C |
| ATOM | 14 | O   | THR A | 38 | 19.782 | -1.679 | 22.567 | 1.00 | 40.90 | O |
| ATOM | 15 | N   | THR A | 39 | 20.233 | 0.177  | 23.777 | 1.00 | 41.08 | N |
| ATOM | 16 | CA  | THR A | 39 | 19.054 | 0.066  | 24.638 | 1.00 | 40.35 | C |
| ATOM | 17 | CB  | THR A | 39 | 19.431 | -0.374 | 26.073 | 1.00 | 39.40 | C |
| ATOM | 18 | OG1 | THR A | 39 | 20.097 | -1.641 | 26.019 | 1.00 | 40.85 | O |
| ATOM | 19 | CG2 | THR A | 39 | 18.180 | -0.508 | 26.937 | 1.00 | 38.74 | C |
| ATOM | 20 | C   | THR A | 39 | 18.352 | 1.416  | 24.702 | 1.00 | 39.57 | C |
| ATOM | 21 | O   | THR A | 39 | 18.970 | 2.435  | 25.001 | 1.00 | 39.59 | O |
| ATOM | 22 | N   | VAL A | 40 | 17.054 | 1.414  | 24.415 | 1.00 | 37.93 | N |
| ATOM | 23 | CA  | VAL A | 40 | 16.268 | 2.638  | 24.429 | 1.00 | 35.62 | C |
| ATOM | 24 | CB  | VAL A | 40 | 15.966 | 3.105  | 23.001 | 1.00 | 34.89 | C |
| ATOM | 25 | CG1 | VAL A | 40 | 17.258 | 3.334  | 22.242 | 1.00 | 32.75 | C |
| ATOM | 26 | CG2 | VAL A | 40 | 15.121 | 2.074  | 22.298 | 1.00 | 32.80 | C |
| ATOM | 27 | C   | VAL A | 40 | 14.947 | 2.409  | 25.137 | 1.00 | 36.24 | C |
| ATOM | 28 | O   | VAL A | 40 | 14.466 | 1.284  | 25.217 | 1.00 | 36.19 | O |
| ATOM | 29 | N   | VAL A | 41 | 14.368 | 3.478  | 25.665 | 1.00 | 37.26 | N |
| ATOM | 30 | CA  | VAL A | 41 | 13.083 | 3.386  | 26.343 | 1.00 | 38.78 | C |
| ATOM | 31 | CB  | VAL A | 41 | 13.001 | 4.400  | 27.500 | 1.00 | 38.94 | C |
| ATOM | 32 | CG1 | VAL A | 41 | 11.586 | 4.453  | 28.059 | 1.00 | 38.55 | C |
| ATOM | 33 | CG2 | VAL A | 41 | 13.991 | 4.010  | 28.583 | 1.00 | 37.26 | C |
| ATOM | 34 | C   | VAL A | 41 | 12.027 | 3.711  | 25.292 | 1.00 | 39.46 | C |
| ATOM | 35 | O   | VAL A | 41 | 11.784 | 4.881  | 24.981 | 1.00 | 41.11 | O |
| ATOM | 36 | N   | ALA A | 42 | 11.401 | 2.672  | 24.750 | 1.00 | 38.75 | N |
| ATOM | 37 | CA  | ALA A | 42 | 10.408 | 2.846  | 23.701 | 1.00 | 39.04 | C |
| ATOM | 38 | CB  | ALA A | 42 | 10.834 | 2.064  | 22.471 | 1.00 | 38.10 | C |
| ATOM | 39 | C   | ALA A | 42 | 8.987  | 2.466  | 24.073 | 1.00 | 38.81 | C |
| ATOM | 40 | O   | ALA A | 42 | 8.752  | 1.510  | 24.811 | 1.00 | 39.19 | O |
| ATOM | 41 | N   | THR A | 43 | 8.037  | 3.214  | 23.530 | 1.00 | 39.96 | N |
| ATOM | 42 | CA  | THR A | 43 | 6.624  | 2.968  | 23.784 | 1.00 | 40.47 | C |
| ATOM | 43 | CB  | THR A | 43 | 5.824  | 4.274  | 23.738 | 1.00 | 40.09 | C |
| ATOM | 44 | OG1 | THR A | 43 | 6.518  | 5.294  | 24.468 | 1.00 | 41.86 | O |
| ATOM | 45 | CG2 | THR A | 43 | 4.455  | 4.071  | 24.343 | 1.00 | 39.07 | C |
| ATOM | 46 | C   | THR A | 43 | 6.078  | 2.042  | 22.701 | 1.00 | 41.20 | C |
| ATOM | 47 | O   | THR A | 43 | 6.498  | 2.115  | 21.543 | 1.00 | 40.45 | O |
| ATOM | 48 | N   | PRO A | 44 | 5.141  | 1.152  | 23.066 | 1.00 | 43.26 | N |
| ATOM | 49 | CD  | PRO A | 44 | 4.712  | 0.788  | 24.425 | 1.00 | 43.22 | C |
| ATOM | 50 | CA  | PRO A | 44 | 4.557  | 0.230  | 22.086 | 1.00 | 45.12 | C |
| ATOM | 51 | CB  | PRO A | 44 | 3.634  | -0.639 | 22.938 | 1.00 | 45.12 | C |
| ATOM | 52 | CG  | PRO A | 44 | 4.345  | -0.673 | 24.248 | 1.00 | 44.31 | C |
| ATOM | 53 | C   | PRO A | 44 | 3.798  | 1.045  | 21.048 | 1.00 | 46.03 | C |
| ATOM | 54 | O   | PRO A | 44 | 3.005  | 1.921  | 21.402 | 1.00 | 46.81 | O |
| ATOM | 55 | N   | GLY A | 45 | 4.057  | 0.764  | 19.774 | 1.00 | 47.95 | N |
| ATOM | 56 | CA  | GLY A | 45 | 3.416  | 1.501  | 18.699 | 1.00 | 49.62 | C |
| ATOM | 57 | C   | GLY A | 45 | 1.914  | 1.395  | 18.783 | 1.00 | 50.81 | C |
| ATOM | 58 | O   | GLY A | 45 | 1.188  | 2.363  | 18.564 | 1.00 | 50.00 | O |
| ATOM | 59 | N   | ALA A | 46 | 1.449  | 0.202  | 19.122 | 1.00 | 52.89 | N |
| ATOM | 60 | CA  | ALA A | 46 | 0.023  | -0.062 | 19.241 | 1.00 | 55.18 | C |

FIG. 2-2

| | | | | | | | | | | |
|---|---|---|---|---|---|---|---|---|---|---|
| ATOM | 61 | CB | ALA | A | 46 | -0.430 | -0.964 | 18.097 | 1.00 54.45 | C |
| ATOM | 62 | C | ALA | A | 46 | -0.267 | -0.724 | 20.583 | 1.00 56.42 | C |
| ATOM | 63 | O | ALA | A | 46 | -0.236 | -1.947 | 20.701 | 1.00 56.72 | O |
| ATOM | 64 | N | GLY | A | 47 | -0.545 | 0.091 | 21.595 | 1.00 57.09 | N |
| ATOM | 65 | CA | GLY | A | 47 | -0.840 | -0.462 | 22.904 | 1.00 58.03 | C |
| ATOM | 66 | C | GLY | A | 47 | -0.903 | 0.572 | 24.011 | 1.00 58.65 | C |
| ATOM | 67 | O | GLY | A | 47 | -1.004 | 1.772 | 23.732 | 1.00 58.46 | O |
| ATOM | 68 | N | PRO | A | 48 | -0.845 | 0.132 | 25.282 | 1.00 58.66 | N |
| ATOM | 69 | CD | PRO | A | 48 | -0.565 | -1.244 | 25.717 | 1.00 58.47 | C |
| ATOM | 70 | CA | PRO | A | 48 | -0.897 | 1.035 | 26.434 | 1.00 58.14 | C |
| ATOM | 71 | CB | PRO | A | 48 | -0.817 | 0.093 | 27.635 | 1.00 58.39 | C |
| ATOM | 72 | CG | PRO | A | 48 | -1.197 | -1.258 | 27.072 | 1.00 58.39 | C |
| ATOM | 73 | C | PRO | A | 48 | 0.301 | 1.958 | 26.358 | 1.00 58.04 | C |
| ATOM | 74 | O | PRO | A | 48 | 1.448 | 1.510 | 26.297 | 1.00 57.19 | O |
| ATOM | 75 | N | ASP | A | 49 | 0.026 | 3.253 | 26.382 | 1.00 58.39 | N |
| ATOM | 76 | CA | ASP | A | 49 | 1.074 | 4.246 | 26.276 | 1.00 59.11 | C |
| ATOM | 77 | CB | ASP | A | 49 | 0.502 | 5.542 | 25.704 | 1.00 61.42 | C |
| ATOM | 78 | CG | ASP | A | 49 | 1.493 | 6.677 | 25.759 | 1.00 64.51 | C |
| ATOM | 79 | OD1 | ASP | A | 49 | 2.664 | 6.455 | 25.355 | 1.00 67.45 | O |
| ATOM | 80 | OD2 | ASP | A | 49 | 1.111 | 7.788 | 26.204 | 1.00 65.29 | O |
| ATOM | 81 | C | ASP | A | 49 | 1.916 | 4.570 | 27.503 | 1.00 59.32 | C |
| ATOM | 82 | O | ASP | A | 49 | 1.760 | 5.626 | 28.122 | 1.00 60.47 | O |
| ATOM | 83 | N | ARG | A | 50 | 2.806 | 3.642 | 27.840 | 1.00 58.19 | N |
| ATOM | 84 | CA | ARG | A | 50 | 3.785 | 3.777 | 28.925 | 1.00 56.50 | C |
| ATOM | 85 | CB | ARG | A | 50 | 3.172 | 3.457 | 30.301 | 1.00 58.21 | C |
| ATOM | 86 | CG | ARG | A | 50 | 2.470 | 4.704 | 30.911 | 1.00 59.04 | C |
| ATOM | 87 | CD | ARG | A | 50 | 2.757 | 4.961 | 32.411 | 1.00 60.18 | C |
| ATOM | 88 | NE | ARG | A | 50 | 4.183 | 5.146 | 32.751 | 1.00 61.04 | N |
| ATOM | 89 | CZ | ARG | A | 50 | 4.962 | 6.152 | 32.338 | 1.00 60.36 | C |
| ATOM | 90 | NH1 | ARG | A | 50 | 4.477 | 7.100 | 31.547 | 1.00 60.40 | N |
| ATOM | 91 | NH2 | ARG | A | 50 | 6.229 | 6.216 | 32.734 | 1.00 58.09 | N |
| ATOM | 92 | C | ARG | A | 50 | 4.904 | 2.819 | 28.491 | 1.00 53.95 | C |
| ATOM | 93 | O | ARG | A | 50 | 4.696 | 1.613 | 28.352 | 1.00 52.54 | O |
| ATOM | 94 | N | PRO | A | 51 | 6.110 | 3.369 | 28.262 | 1.00 51.26 | N |
| ATOM | 95 | CD | PRO | A | 51 | 6.468 | 4.710 | 28.764 | 1.00 50.65 | C |
| ATOM | 96 | CA | PRO | A | 51 | 7.292 | 2.638 | 27.806 | 1.00 49.89 | C |
| ATOM | 97 | CB | PRO | A | 51 | 8.264 | 3.756 | 27.433 | 1.00 50.03 | C |
| ATOM | 98 | CG | PRO | A | 51 | 7.916 | 4.871 | 28.358 | 1.00 50.81 | C |
| ATOM | 99 | C | PRO | A | 51 | 7.964 | 1.500 | 28.569 | 1.00 49.60 | C |
| ATOM | 100 | O | PRO | A | 51 | 7.664 | 1.201 | 29.726 | 1.00 49.72 | O |
| ATOM | 101 | N | GLN | A | 52 | 8.874 | 0.848 | 27.853 | 1.00 48.69 | N |
| ATOM | 102 | CA | GLN | A | 52 | 9.636 | -0.281 | 28.351 | 1.00 47.79 | C |
| ATOM | 103 | CB | GLN | A | 52 | 8.882 | -1.579 | 28.072 | 1.00 49.27 | C |
| ATOM | 104 | CG | GLN | A | 52 | 8.088 | -1.572 | 26.776 | 1.00 50.74 | C |
| ATOM | 105 | CD | GLN | A | 52 | 7.511 | -2.955 | 26.412 | 1.00 52.97 | C |
| ATOM | 106 | OE1 | GLN | A | 52 | 8.241 | -3.854 | 25.944 | 1.00 52.17 | O |
| ATOM | 107 | NE2 | GLN | A | 52 | 6.198 | -3.131 | 26.630 | 1.00 52.02 | N |
| ATOM | 108 | C | GLN | A | 52 | 10.969 | -0.301 | 27.636 | 1.00 47.05 | C |
| ATOM | 109 | O | GLN | A | 52 | 11.086 | 0.185 | 26.508 | 1.00 47.80 | O |
| ATOM | 110 | N | GLU | A | 53 | 11.975 | -0.854 | 28.295 | 1.00 45.97 | N |
| ATOM | 111 | CA | GLU | A | 53 | 13.293 | -0.933 | 27.703 | 1.00 44.69 | C |
| ATOM | 112 | CB | GLU | A | 53 | 14.332 | -1.342 | 28.752 | 1.00 44.89 | C |
| ATOM | 113 | CG | GLU | A | 53 | 14.540 | -0.320 | 29.866 | 1.00 44.27 | C |
| ATOM | 114 | CD | GLU | A | 53 | 15.637 | -0.729 | 30.831 | 1.00 46.36 | C |
| ATOM | 115 | OE1 | GLU | A | 53 | 16.186 | -1.842 | 30.661 | 1.00 47.13 | O |
| ATOM | 116 | OE2 | GLU | A | 53 | 15.957 | 0.056 | 31.751 | 1.00 45.62 | O |
| ATOM | 117 | C | GLU | A | 53 | 13.288 | -1.935 | 26.557 | 1.00 43.22 | C |
| ATOM | 118 | O | GLU | A | 53 | 12.710 | -3.022 | 26.653 | 1.00 41.83 | O |
| ATOM | 119 | N | VAL | A | 54 | 13.930 | -1.540 | 25.465 | 1.00 41.47 | N |
| ATOM | 120 | CA | VAL | A | 54 | 14.043 | -2.364 | 24.277 | 1.00 39.43 | C |
| ATOM | 121 | CB | VAL | A | 54 | 13.152 | -1.841 | 23.144 | 1.00 39.77 | C |
| ATOM | 122 | CG1 | VAL | A | 54 | 13.370 | -2.687 | 21.897 | 1.00 41.24 | C |
| ATOM | 123 | CG2 | VAL | A | 54 | 11.688 | -1.874 | 23.569 | 1.00 37.88 | C |
| ATOM | 124 | C | VAL | A | 54 | 15.482 | -2.328 | 23.805 | 1.00 39.63 | C |
| ATOM | 125 | O | VAL | A | 54 | 16.071 | -1.255 | 23.650 | 1.00 38.18 | O |
| ATOM | 126 | N | SER | A | 55 | 16.055 | -3.502 | 23.584 | 1.00 40.09 | N |
| ATOM | 127 | CA | SER | A | 55 | 17.433 | -3.579 | 23.114 | 1.00 41.88 | C |

FIG. 2-3

```
ATOM    128  CB   SER A  55      18.289   -4.376   24.103  1.00 43.92           C
ATOM    129  OG   SER A  55      18.633   -3.572   25.228  1.00 45.09           O
ATOM    130  C    SER A  55      17.521   -4.200   21.728  1.00 42.20           C
ATOM    131  O    SER A  55      16.822   -5.167   21.418  1.00 42.29           O
ATOM    132  N    TYR A  56      18.373   -3.621   20.891  1.00 42.22           N
ATOM    133  CA   TYR A  56      18.570   -4.103   19.529  1.00 42.61           C
ATOM    134  CB   TYR A  56      17.702   -3.311   18.542  1.00 38.89           C
ATOM    135  CG   TYR A  56      17.952   -1.814   18.479  1.00 37.57           C
ATOM    136  CD1  TYR A  56      19.053   -1.289   17.803  1.00 35.43           C
ATOM    137  CE1  TYR A  56      19.250    0.094   17.709  1.00 33.77           C
ATOM    138  CD2  TYR A  56      17.057   -0.921   19.063  1.00 36.63           C
ATOM    139  CE2  TYR A  56      17.246    0.455   18.975  1.00 35.41           C
ATOM    140  CZ   TYR A  56      18.340    0.957   18.298  1.00 34.92           C
ATOM    141  OH   TYR A  56      18.513    2.323   18.218  1.00 35.27           O
ATOM    142  C    TYR A  56      20.043   -4.017   19.130  1.00 44.84           C
ATOM    143  O    TYR A  56      20.828   -3.290   19.743  1.00 43.64           O
ATOM    144  N    THR A  57      20.414   -4.766   18.094  1.00 46.94           N
ATOM    145  CA   THR A  57      21.791   -4.777   17.645  1.00 48.44           C
ATOM    146  CB   THR A  57      22.598   -5.818   18.472  1.00 48.71           C
ATOM    147  OG1  THR A  57      24.003   -5.549   18.353  1.00 49.45           O
ATOM    148  CG2  THR A  57      22.299   -7.230   17.997  1.00 47.90           C
ATOM    149  C    THR A  57      21.912   -5.047   16.139  1.00 49.15           C
ATOM    150  O    THR A  57      20.913   -5.276   15.459  1.00 48.21           O
ATOM    151  N    ASP A  58      23.143   -5.006   15.630  1.00 50.30           N
ATOM    152  CA   ASP A  58      23.428   -5.216   14.206  1.00 50.52           C
ATOM    153  CB   ASP A  58      22.885   -6.556   13.702  1.00 51.58           C
ATOM    154  CG   ASP A  58      23.402   -7.724   14.486  1.00 52.74           C
ATOM    155  OD1  ASP A  58      24.606   -7.713   14.831  1.00 53.02           O
ATOM    156  OD2  ASP A  58      22.601   -8.654   14.739  1.00 53.89           O
ATOM    157  C    ASP A  58      22.777   -4.126   13.380  1.00 49.86           C
ATOM    158  O    ASP A  58      22.185   -4.405   12.335  1.00 50.15           O
ATOM    159  N    THR A  59      22.895   -2.886   13.828  1.00 49.03           N
ATOM    160  CA   THR A  59      22.268   -1.795   13.102  1.00 49.25           C
ATOM    161  CB   THR A  59      21.988   -0.596   14.032  1.00 48.94           C
ATOM    162  OG1  THR A  59      23.218    0.065   14.342  1.00 51.68           O
ATOM    163  CG2  THR A  59      21.338   -1.067   15.314  1.00 46.70           C
ATOM    164  C    THR A  59      23.078   -1.319   11.898  1.00 49.58           C
ATOM    165  O    THR A  59      24.299   -1.171   11.973  1.00 49.07           O
ATOM    166  N    LYS A  60      22.377   -1.112   10.782  1.00 50.21           N
ATOM    167  CA   LYS A  60      22.981   -0.636    9.532  1.00 50.79           C
ATOM    168  CB   LYS A  60      23.523   -1.803    8.680  1.00 50.80           C
ATOM    169  CG   LYS A  60      22.543   -2.921    8.350  1.00 51.38           C
ATOM    170  CD   LYS A  60      23.121   -3.822    7.269  1.00 52.69           C
ATOM    171  CE   LYS A  60      22.214   -4.999    6.932  1.00 53.62           C
ATOM    172  NZ   LYS A  60      22.596   -5.626    5.624  1.00 54.42           N
ATOM    173  C    LYS A  60      21.991    0.179    8.700  1.00 50.41           C
ATOM    174  O    LYS A  60      20.780   -0.069    8.719  1.00 50.71           O
ATOM    175  N    VAL A  61      22.526    1.162    7.978  1.00 50.13           N
ATOM    176  CA   VAL A  61      21.718    2.036    7.133  1.00 48.87           C
ATOM    177  CB   VAL A  61      22.541    3.249    6.618  1.00 48.82           C
ATOM    178  CG1  VAL A  61      21.660    4.179    5.793  1.00 49.02           C
ATOM    179  CG2  VAL A  61      23.146    3.993    7.785  1.00 46.99           C
ATOM    180  C    VAL A  61      21.207    1.230    5.944  1.00 48.28           C
ATOM    181  O    VAL A  61      21.927    0.394    5.394  1.00 48.15           O
ATOM    182  N    ILE A  62      19.955    1.480    5.566  1.00 46.53           N
ATOM    183  CA   ILE A  62      19.320    0.777    4.458  1.00 44.95           C
ATOM    184  CB   ILE A  62      18.562   -0.476    4.935  1.00 42.88           C
ATOM    185  CG2  ILE A  62      19.475   -1.356    5.772  1.00 40.60           C
ATOM    186  CG1  ILE A  62      17.321   -0.053    5.735  1.00 41.66           C
ATOM    187  CD1  ILE A  62      16.373   -1.193    6.074  1.00 40.59           C
ATOM    188  C    ILE A  62      18.285    1.663    3.783  1.00 46.21           C
ATOM    189  O    ILE A  62      17.472    1.173    2.998  1.00 47.15           O
ATOM    190  N    GLY A  63      18.295    2.957    4.091  1.00 46.66           N
ATOM    191  CA   GLY A  63      17.310    3.839    3.492  1.00 47.12           C
ATOM    192  C    GLY A  63      17.495    5.316    3.774  1.00 48.09           C
ATOM    193  O    GLY A  63      17.704    5.713    4.917  1.00 48.32           O
ATOM    194  N    ASN A  64      17.420    6.114    2.711  1.00 49.81           N
```

FIG. 2-4

| | | | | | | | | | |
|---|---|---|---|---|---|---|---|---|---|
| ATOM | 195 | CA | ASN A | 64 | 17.558 | 7.563 | 2.767 | 1.00 49.75 | C |
| ATOM | 196 | CB | ASN A | 64 | 18.393 | 8.064 | 1.590 | 1.00 51.28 | C |
| ATOM | 197 | CG | ASN A | 64 | 19.795 | 8.459 | 1.997 | 1.00 55.47 | C |
| ATOM | 198 | OD1 | ASN A | 64 | 19.992 | 9.173 | 2.986 | 1.00 57.55 | O |
| ATOM | 199 | ND2 | ASN A | 64 | 20.780 | 8.022 | 1.226 | 1.00 57.75 | N |
| ATOM | 200 | C | ASN A | 64 | 16.169 | 8.187 | 2.660 | 1.00 48.93 | C |
| ATOM | 201 | O | ASN A | 64 | 15.168 | 7.486 | 2.493 | 1.00 48.93 | O |
| ATOM | 202 | N | GLY A | 65 | 16.112 | 9.511 | 2.740 | 1.00 46.50 | N |
| ATOM | 203 | CA | GLY A | 65 | 14.838 | 10.188 | 2.637 | 1.00 45.21 | C |
| ATOM | 204 | C | GLY A | 65 | 14.956 | 11.638 | 3.033 | 1.00 44.89 | C |
| ATOM | 205 | O | GLY A | 65 | 15.966 | 12.045 | 3.593 | 1.00 45.46 | O |
| ATOM | 206 | N | SER A | 66 | 13.935 | 12.426 | 2.740 | 1.00 44.47 | N |
| ATOM | 207 | CA | SER A | 66 | 13.965 | 13.834 | 3.096 | 1.00 44.39 | C |
| ATOM | 208 | CB | SER A | 66 | 12.835 | 14.569 | 2.371 | 1.00 45.45 | C |
| ATOM | 209 | OG | SER A | 66 | 11.570 | 13.979 | 2.656 | 1.00 46.75 | O |
| ATOM | 210 | C | SER A | 66 | 13.798 | 13.963 | 4.607 | 1.00 43.29 | C |
| ATOM | 211 | O | SER A | 66 | 14.246 | 14.931 | 5.212 | 1.00 42.73 | O |
| ATOM | 212 | N | PHE A | 67 | 13.151 | 12.959 | 5.191 | 1.00 42.55 | N |
| ATOM | 213 | CA | PHE A | 67 | 12.857 | 12.877 | 6.621 | 1.00 41.63 | C |
| ATOM | 214 | CB | PHE A | 67 | 11.764 | 11.841 | 6.830 | 1.00 40.91 | C |
| ATOM | 215 | CG | PHE A | 67 | 12.159 | 10.471 | 6.351 | 1.00 41.06 | C |
| ATOM | 216 | CD1 | PHE A | 67 | 12.966 | 9.649 | 7.130 | 1.00 39.66 | C |
| ATOM | 217 | CD2 | PHE A | 67 | 11.783 | 10.028 | 5.085 | 1.00 40.62 | C |
| ATOM | 218 | CE1 | PHE A | 67 | 13.398 | 8.412 | 6.655 | 1.00 40.51 | C |
| ATOM | 219 | CE2 | PHE A | 67 | 12.212 | 8.791 | 4.605 | 1.00 40.37 | C |
| ATOM | 220 | CZ | PHE A | 67 | 13.019 | 7.983 | 5.390 | 1.00 39.43 | C |
| ATOM | 221 | C | PHE A | 67 | 14.062 | 12.471 | 7.472 | 1.00 42.06 | C |
| ATOM | 222 | O | PHE A | 67 | 14.130 | 12.791 | 8.662 | 1.00 42.38 | O |
| ATOM | 223 | N | GLY A | 68 | 14.990 | 11.730 | 6.870 | 1.00 41.39 | N |
| ATOM | 224 | CA | GLY A | 68 | 16.159 | 11.282 | 7.606 | 1.00 39.65 | C |
| ATOM | 225 | C | GLY A | 68 | 16.808 | 10.000 | 7.118 | 1.00 38.74 | C |
| ATOM | 226 | O | GLY A | 68 | 17.240 | 9.920 | 5.966 | 1.00 39.48 | O |
| ATOM | 227 | N | VAL A | 69 | 16.867 | 8.995 | 7.994 | 1.00 37.02 | N |
| ATOM | 228 | CA | VAL A | 69 | 17.506 | 7.717 | 7.685 | 1.00 35.17 | C |
| ATOM | 229 | CB | VAL A | 69 | 18.922 | 7.659 | 8.331 | 1.00 35.03 | C |
| ATOM | 230 | CG1 | VAL A | 69 | 19.599 | 6.343 | 8.013 | 1.00 33.33 | C |
| ATOM | 231 | CG2 | VAL A | 69 | 19.770 | 8.830 | 7.845 | 1.00 36.13 | C |
| ATOM | 232 | C | VAL A | 69 | 16.718 | 6.501 | 8.171 | 1.00 35.82 | C |
| ATOM | 233 | O | VAL A | 69 | 15.963 | 6.579 | 9.139 | 1.00 36.04 | O |
| ATOM | 234 | N | VAL A | 70 | 16.896 | 5.376 | 7.490 | 1.00 35.99 | N |
| ATOM | 235 | CA | VAL A | 70 | 16.239 | 4.141 | 7.880 | 1.00 35.59 | C |
| ATOM | 236 | CB | VAL A | 70 | 15.321 | 3.591 | 6.771 | 1.00 33.87 | C |
| ATOM | 237 | CG1 | VAL A | 70 | 14.659 | 2.292 | 7.235 | 1.00 31.70 | C |
| ATOM | 238 | CG2 | VAL A | 70 | 14.270 | 4.620 | 6.412 | 1.00 32.14 | C |
| ATOM | 239 | C | VAL A | 70 | 17.329 | 3.109 | 8.157 | 1.00 37.71 | C |
| ATOM | 240 | O | VAL A | 70 | 18.235 | 2.897 | 7.342 | 1.00 37.21 | O |
| ATOM | 241 | N | TYR A | 71 | 17.242 | 2.467 | 9.316 | 1.00 39.12 | N |
| ATOM | 242 | CA | TYR A | 71 | 18.218 | 1.458 | 9.694 | 1.00 38.71 | C |
| ATOM | 243 | CB | TYR A | 71 | 18.818 | 1.752 | 11.072 | 1.00 39.21 | C |
| ATOM | 244 | CG | TYR A | 71 | 19.557 | 3.054 | 11.211 | 1.00 39.73 | C |
| ATOM | 245 | CD1 | TYR A | 71 | 18.874 | 4.255 | 11.349 | 1.00 39.93 | C |
| ATOM | 246 | CE1 | TYR A | 71 | 19.565 | 5.454 | 11.497 | 1.00 41.91 | C |
| ATOM | 247 | CD2 | TYR A | 71 | 20.954 | 3.081 | 11.221 | 1.00 40.60 | C |
| ATOM | 248 | CE2 | TYR A | 71 | 21.655 | 4.273 | 11.366 | 1.00 40.20 | C |
| ATOM | 249 | CZ | TYR A | 71 | 20.957 | 5.453 | 11.502 | 1.00 41.06 | C |
| ATOM | 250 | OH | TYR A | 71 | 21.647 | 6.638 | 11.625 | 1.00 42.45 | O |
| ATOM | 251 | C | TYR A | 71 | 17.561 | 0.108 | 9.789 | 1.00 38.72 | C |
| ATOM | 252 | O | TYR A | 71 | 16.335 | -0.014 | 9.829 | 1.00 37.34 | O |
| ATOM | 253 | N | GLN A | 72 | 18.399 | -0.914 | 9.816 | 1.00 38.30 | N |
| ATOM | 254 | CA | GLN A | 72 | 17.913 | -2.260 | 9.997 | 1.00 39.34 | C |
| ATOM | 255 | CB | GLN A | 72 | 18.406 | -3.203 | 8.916 | 1.00 40.14 | C |
| ATOM | 256 | CG | GLN A | 72 | 18.005 | -4.631 | 9.210 | 1.00 41.78 | C |
| ATOM | 257 | CD | GLN A | 72 | 18.656 | -5.625 | 8.276 | 1.00 43.42 | C |
| ATOM | 258 | OE1 | GLN A | 72 | 19.081 | -6.700 | 8.699 | 1.00 44.23 | O |
| ATOM | 259 | NE2 | GLN A | 72 | 18.738 | -5.274 | 6.995 | 1.00 43.61 | N |
| ATOM | 260 | C | GLN A | 72 | 18.536 | -2.650 | 11.318 | 1.00 38.98 | C |
| ATOM | 261 | O | GLN A | 72 | 19.657 | -2.251 | 11.623 | 1.00 39.05 | O |

FIG. 2-5

```
ATOM    262  N   ALA A  73      17.809  -3.414  12.111  1.00 39.51           N
ATOM    263  CA  ALA A  73      18.325  -3.826  13.395  1.00 40.86           C
ATOM    264  CB  ALA A  73      18.041  -2.757  14.442  1.00 40.82           C
ATOM    265  C   ALA A  73      17.694  -5.135  13.791  1.00 41.65           C
ATOM    266  O   ALA A  73      16.735  -5.594  13.167  1.00 41.06           O
ATOM    267  N   LYS A  74      18.251  -5.718  14.843  1.00 43.89           N
ATOM    268  CA  LYS A  74      17.820  -7.003  15.373  1.00 45.18           C
ATOM    269  CB  LYS A  74      18.937  -8.015  15.113  1.00 46.06           C
ATOM    270  CG  LYS A  74      18.795  -9.401  15.700  1.00 47.06           C
ATOM    271  CD  LYS A  74      19.924 -10.219  15.106  1.00 48.93           C
ATOM    272  CE  LYS A  74      19.934 -11.663  15.547  1.00 50.02           C
ATOM    273  NZ  LYS A  74      20.929 -12.402  14.698  1.00 50.02           N
ATOM    274  C   LYS A  74      17.524  -6.885  16.866  1.00 45.62           C
ATOM    275  O   LYS A  74      18.411  -6.594  17.666  1.00 44.56           O
ATOM    276  N   LEU A  75      16.259  -7.109  17.217  1.00 46.26           N
ATOM    277  CA  LEU A  75      15.798  -7.050  18.592  1.00 45.73           C
ATOM    278  CB  LEU A  75      14.268  -7.134  18.630  1.00 44.80           C
ATOM    279  CG  LEU A  75      13.459  -6.088  17.852  1.00 43.46           C
ATOM    280  CD1 LEU A  75      11.971  -6.367  18.012  1.00 40.85           C
ATOM    281  CD2 LEU A  75      13.792  -4.697  18.365  1.00 43.72           C
ATOM    282  C   LEU A  75      16.402  -8.206  19.384  1.00 46.73           C
ATOM    283  O   LEU A  75      16.172  -9.378  19.062  1.00 46.50           O
ATOM    284  N   CYS A  76      17.180  -7.865  20.413  1.00 48.60           N
ATOM    285  CA  CYS A  76      17.839  -8.850  21.282  1.00 49.46           C
ATOM    286  CB  CYS A  76      18.601  -8.137  22.406  1.00 48.19           C
ATOM    287  SG  CYS A  76      20.047  -7.191  21.891  1.00 47.35           S
ATOM    288  C   CYS A  76      16.826  -9.798  21.909  1.00 50.36           C
ATOM    289  O   CYS A  76      17.177 -10.865  22.403  1.00 50.28           O
ATOM    290  N   ASP A  77      15.568  -9.390  21.887  1.00 52.38           N
ATOM    291  CA  ASP A  77      14.493 -10.160  22.475  1.00 54.20           C
ATOM    292  CB  ASP A  77      13.256  -9.265  22.643  1.00 56.30           C
ATOM    293  CG  ASP A  77      13.514  -7.787  22.257  1.00 59.05           C
ATOM    294  OD1 ASP A  77      12.515  -7.018  22.177  1.00 59.16           O
ATOM    295  OD2 ASP A  77      14.693  -7.378  22.047  1.00 59.58           O
ATOM    296  C   ASP A  77      14.123 -11.418  21.680  1.00 54.77           C
ATOM    297  O   ASP A  77      14.385 -12.539  22.120  1.00 55.18           O
ATOM    298  N   SER A  78      13.519 -11.222  20.509  1.00 54.50           N
ATOM    299  CA  SER A  78      13.073 -12.322  19.650  1.00 53.92           C
ATOM    300  CB  SER A  78      11.707 -11.981  19.041  1.00 54.31           C
ATOM    301  OG  SER A  78      11.733 -10.685  18.452  1.00 53.66           O
ATOM    302  C   SER A  78      14.044 -12.629  18.518  1.00 53.98           C
ATOM    303  O   SER A  78      13.815 -13.541  17.717  1.00 53.75           O
ATOM    304  N   GLY A  79      15.134 -11.873  18.453  1.00 53.79           N
ATOM    305  CA  GLY A  79      16.090 -12.086  17.381  1.00 52.28           C
ATOM    306  C   GLY A  79      15.516 -11.458  16.122  1.00 51.80           C
ATOM    307  O   GLY A  79      16.258 -11.110  15.200  1.00 51.68           O
ATOM    308  N   GLU A  80      14.193 -11.294  16.102  1.00 51.28           N
ATOM    309  CA  GLU A  80      13.473 -10.711  14.962  1.00 51.47           C
ATOM    310  CB  GLU A  80      12.036 -10.338  15.348  1.00 53.87           C
ATOM    311  CG  GLU A  80      11.110 -11.496  15.692  1.00 57.17           C
ATOM    312  CD  GLU A  80       9.736 -11.017  16.134  1.00 60.23           C
ATOM    313  OE1 GLU A  80       9.645 -10.324  17.180  1.00 61.81           O
ATOM    314  OE2 GLU A  80       8.739 -11.329  15.435  1.00 62.38           O
ATOM    315  C   GLU A  80      14.132  -9.470  14.392  1.00 49.48           C
ATOM    316  O   GLU A  80      14.758  -8.691  15.113  1.00 49.02           O
ATOM    317  N   LEU A  81      13.977  -9.295  13.087  1.00 47.91           N
ATOM    318  CA  LEU A  81      14.539  -8.140  12.417  1.00 46.40           C
ATOM    319  CB  LEU A  81      15.008  -8.503  11.005  1.00 47.51           C
ATOM    320  CG  LEU A  81      16.424  -9.074  10.869  1.00 48.03           C
ATOM    321  CD1 LEU A  81      16.833  -9.084   9.400  1.00 47.42           C
ATOM    322  CD2 LEU A  81      17.396  -8.195  11.668  1.00 48.37           C
ATOM    323  C   LEU A  81      13.503  -7.038  12.344  1.00 44.26           C
ATOM    324  O   LEU A  81      12.301  -7.293  12.258  1.00 43.78           O
ATOM    325  N   VAL A  82      13.976  -5.803  12.387  1.00 41.44           N
ATOM    326  CA  VAL A  82      13.077  -4.675  12.329  1.00 39.19           C
ATOM    327  CB  VAL A  82      12.676  -4.184  13.736  1.00 39.01           C
ATOM    328  CG1 VAL A  82      12.039  -5.310  14.519  1.00 37.51           C
```

FIG. 2-6

```
ATOM    329  CG2 VAL A  82      13.892  -3.621  14.453  1.00 37.99           C
ATOM    330  C   VAL A  82      13.743  -3.525  11.616  1.00 38.15           C
ATOM    331  O   VAL A  82      14.961  -3.489  11.468  1.00 38.17           O
ATOM    332  N   ALA A  83      12.922  -2.587  11.169  1.00 36.63           N
ATOM    333  CA  ALA A  83      13.414  -1.408  10.496  1.00 36.15           C
ATOM    334  CB  ALA A  83      12.620  -1.161   9.224  1.00 35.39           C
ATOM    335  C   ALA A  83      13.218  -0.261  11.477  1.00 35.25           C
ATOM    336  O   ALA A  83      12.294  -0.274  12.296  1.00 33.66           O
ATOM    337  N   ILE A  84      14.104   0.719  11.416  1.00 35.22           N
ATOM    338  CA  ILE A  84      13.988   1.862  12.294  1.00 36.94           C
ATOM    339  CB  ILE A  84      15.117   1.879  13.356  1.00 37.47           C
ATOM    340  CG2 ILE A  84      14.991   3.112  14.236  1.00 36.46           C
ATOM    341  CG1 ILE A  84      15.027   0.625  14.224  1.00 38.48           C
ATOM    342  CD1 ILE A  84      16.003   0.608  15.372  1.00 40.91           C
ATOM    343  C   ILE A  84      14.050   3.132  11.464  1.00 37.44           C
ATOM    344  O   ILE A  84      15.109   3.505  10.949  1.00 37.84           O
ATOM    345  N   LYS A  85      12.910   3.790  11.321  1.00 38.11           N
ATOM    346  CA  LYS A  85      12.862   5.014  10.547  1.00 39.27           C
ATOM    347  CB  LYS A  85      11.475   5.189   9.922  1.00 39.58           C
ATOM    348  CG  LYS A  85      11.380   6.282   8.863  1.00 37.71           C
ATOM    349  CD  LYS A  85       9.962   6.310   8.309  1.00 39.18           C
ATOM    350  CE  LYS A  85       9.762   7.333   7.207  1.00 38.99           C
ATOM    351  NZ  LYS A  85       8.348   7.312   6.736  1.00 40.98           N
ATOM    352  C   LYS A  85      13.178   6.166  11.486  1.00 40.01           C
ATOM    353  O   LYS A  85      12.410   6.463  12.404  1.00 40.49           O
ATOM    354  N   LYS A  86      14.336   6.780  11.269  1.00 41.82           N
ATOM    355  CA  LYS A  86      14.787   7.908  12.077  1.00 43.19           C
ATOM    356  CB  LYS A  86      16.313   7.906  12.170  1.00 45.09           C
ATOM    357  CG  LYS A  86      16.903   8.896  13.150  1.00 46.50           C
ATOM    358  CD  LYS A  86      18.425   8.803  13.137  1.00 49.98           C
ATOM    359  CE  LYS A  86      19.041   9.701  14.202  1.00 52.69           C
ATOM    360  NZ  LYS A  86      20.520   9.553  14.302  1.00 55.15           N
ATOM    361  C   LYS A  86      14.299   9.173  11.382  1.00 43.64           C
ATOM    362  O   LYS A  86      14.594   9.399  10.208  1.00 42.94           O
ATOM    363  N   VAL A  87      13.547   9.987  12.115  1.00 44.58           N
ATOM    364  CA  VAL A  87      12.978  11.210  11.577  1.00 45.62           C
ATOM    365  CB  VAL A  87      11.455  11.086  11.435  1.00 44.58           C
ATOM    366  CG1 VAL A  87      10.831  12.473  11.333  1.00 44.53           C
ATOM    367  CG2 VAL A  87      11.112  10.258  10.209  1.00 42.75           C
ATOM    368  C   VAL A  87      13.236  12.427  12.426  1.00 47.67           C
ATOM    369  O   VAL A  87      13.141  12.371  13.641  1.00 48.67           O
ATOM    370  N   LEU A  88      13.536  13.539  11.781  1.00 51.08           N
ATOM    371  CA  LEU A  88      13.763  14.764  12.511  1.00 54.83           C
ATOM    372  CB  LEU A  88      14.631  15.716  11.691  1.00 55.85           C
ATOM    373  CG  LEU A  88      15.248  16.843  12.519  1.00 57.59           C
ATOM    374  CD1 LEU A  88      16.176  16.223  13.567  1.00 57.59           C
ATOM    375  CD2 LEU A  88      16.032  17.807  11.627  1.00 57.03           C
ATOM    376  C   LEU A  88      12.409  15.408  12.767  1.00 57.25           C
ATOM    377  O   LEU A  88      11.727  15.820  11.835  1.00 57.35           O
ATOM    378  N   GLN A  89      12.003  15.477  14.027  1.00 60.00           N
ATOM    379  CA  GLN A  89      10.745  16.114  14.358  1.00 62.66           C
ATOM    380  CB  GLN A  89       9.770  15.145  15.016  1.00 63.73           C
ATOM    381  CG  GLN A  89       8.440  15.820  15.319  1.00 66.30           C
ATOM    382  CD  GLN A  89       7.559  15.871  14.088  1.00 67.08           C
ATOM    383  OE1 GLN A  89       8.047  15.914  12.945  1.00 69.15           O
ATOM    384  NE2 GLN A  89       6.255  15.878  14.307  1.00 67.86           N
ATOM    385  C   GLN A  89      11.074  17.211  15.326  1.00 63.95           C
ATOM    386  O   GLN A  89      11.746  16.978  16.335  1.00 64.56           O
ATOM    387  N   ASP A  90      10.635  18.421  15.019  1.00 65.34           N
ATOM    388  CA  ASP A  90      10.924  19.478  15.947  1.00 67.13           C
ATOM    389  CB  ASP A  90      10.849  20.838  15.254  1.00 67.57           C
ATOM    390  CG  ASP A  90       9.476  21.443  15.314  1.00 68.81           C
ATOM    391  OD1 ASP A  90       8.505  20.739  14.980  1.00 70.11           O
ATOM    392  OD2 ASP A  90       9.353  22.625  15.708  1.00 69.97           O
ATOM    393  C   ASP A  90       9.802  19.275  16.959  1.00 67.57           C
ATOM    394  O   ASP A  90       8.633  19.137  16.576  1.00 67.91           O
ATOM    395  N   ALA A  91      10.150  19.181  18.238  1.00 67.48           N
```

FIG. 2-7

```
ATOM    396  CA   ALA A  91       9.138  18.985  19.277  1.00 66.84           C
ATOM    397  CB   ALA A  91       9.812  18.812  20.641  1.00 65.38           C
ATOM    398  C    ALA A  91       8.214  20.205  19.295  1.00 66.58           C
ATOM    399  O    ALA A  91       8.586  21.268  18.804  1.00 66.30           O
ATOM    400  N    ALA A  92       7.014  20.037  19.844  1.00 66.05           N
ATOM    401  CA   ALA A  92       6.031  21.118  19.944  1.00 66.10           C
ATOM    402  CB   ALA A  92       6.730  22.484  20.125  1.00 66.90           C
ATOM    403  C    ALA A  92       5.054  21.174  18.758  1.00 64.95           C
ATOM    404  O    ALA A  92       4.156  22.032  18.706  1.00 65.71           O
ATOM    405  N    ALA A  93       5.241  20.267  17.805  1.00 63.11           N
ATOM    406  CA   ALA A  93       4.356  20.147  16.648  1.00 59.88           C
ATOM    407  CB   ALA A  93       5.014  20.676  15.394  1.00 58.42           C
ATOM    408  C    ALA A  93       4.256  18.625  16.601  1.00 58.06           C
ATOM    409  O    ALA A  93       5.288  17.941  16.562  1.00 58.04           O
ATOM    410  N    ALA A  94       3.036  18.087  16.652  1.00 54.47           N
ATOM    411  CA   ALA A  94       2.846  16.634  16.621  1.00 51.21           C
ATOM    412  CB   ALA A  94       1.403  16.288  16.959  1.00 51.62           C
ATOM    413  C    ALA A  94       3.227  16.026  15.275  1.00 48.97           C
ATOM    414  O    ALA A  94       3.123  16.682  14.234  1.00 47.54           O
ATOM    415  N    ASN A  95       3.687  14.776  15.310  1.00 46.82           N
ATOM    416  CA   ASN A  95       4.096  14.061  14.097  1.00 43.68           C
ATOM    417  CB   ASN A  95       5.253  13.104  14.386  1.00 43.32           C
ATOM    418  CG   ASN A  95       5.868  12.526  13.112  1.00 42.96           C
ATOM    419  OD1  ASN A  95       5.323  11.606  12.497  1.00 41.10           O
ATOM    420  ND2  ASN A  95       7.011  13.077  12.710  1.00 42.91           N
ATOM    421  C    ASN A  95       2.928  13.280  13.537  1.00 41.82           C
ATOM    422  O    ASN A  95       2.434  12.328  14.152  1.00 42.01           O
ATOM    423  N    ARG A  96       2.489  13.703  12.361  1.00 40.01           N
ATOM    424  CA   ARG A  96       1.365  13.083  11.689  1.00 39.58           C
ATOM    425  CB   ARG A  96       1.106  13.798  10.359  1.00 39.21           C
ATOM    426  CG   ARG A  96      -0.227  13.447   9.719  1.00 40.20           C
ATOM    427  CD   ARG A  96      -0.411  14.157   8.385  1.00 41.13           C
ATOM    428  NE   ARG A  96      -0.731  15.577   8.510  1.00 43.81           N
ATOM    429  CZ   ARG A  96      -0.562  16.461   7.530  1.00 44.56           C
ATOM    430  NH1  ARG A  96      -0.072  16.070   6.361  1.00 45.91           N
ATOM    431  NH2  ARG A  96      -0.882  17.735   7.712  1.00 45.06           N
ATOM    432  C    ARG A  96       1.597  11.589  11.451  1.00 38.18           C
ATOM    433  O    ARG A  96       0.761  10.756  11.806  1.00 37.82           O
ATOM    434  N    GLU A  97       2.741  11.249  10.867  1.00 36.83           N
ATOM    435  CA   GLU A  97       3.037   9.854  10.582  1.00 35.83           C
ATOM    436  CB   GLU A  97       4.446   9.699  10.017  1.00 35.55           C
ATOM    437  CG   GLU A  97       4.857   8.249   9.853  1.00 34.07           C
ATOM    438  CD   GLU A  97       6.009   8.075   8.899  1.00 33.84           C
ATOM    439  OE1  GLU A  97       6.630   9.088   8.524  1.00 32.46           O
ATOM    440  OE2  GLU A  97       6.289   6.925   8.519  1.00 33.29           O
ATOM    441  C    GLU A  97       2.882   8.973  11.809  1.00 36.15           C
ATOM    442  O    GLU A  97       2.304   7.886  11.737  1.00 36.21           O
ATOM    443  N    LEU A  98       3.394   9.435  12.942  1.00 36.98           N
ATOM    444  CA   LEU A  98       3.282   8.641  14.150  1.00 37.65           C
ATOM    445  CB   LEU A  98       4.145   9.227  15.273  1.00 37.12           C
ATOM    446  CG   LEU A  98       3.973   8.539  16.636  1.00 35.69           C
ATOM    447  CD1  LEU A  98       4.224   7.043  16.519  1.00 37.16           C
ATOM    448  CD2  LEU A  98       4.914   9.168  17.630  1.00 36.61           C
ATOM    449  C    LEU A  98       1.834   8.490  14.623  1.00 37.78           C
ATOM    450  O    LEU A  98       1.458   7.409  15.070  1.00 36.47           O
ATOM    451  N    GLN A  99       1.022   9.545  14.521  1.00 40.08           N
ATOM    452  CA   GLN A  99      -0.380   9.451  14.968  1.00 42.48           C
ATOM    453  CB   GLN A  99      -1.151  10.758  14.825  1.00 44.54           C
ATOM    454  CG   GLN A  99      -0.498  12.059  15.182  1.00 47.68           C
ATOM    455  CD   GLN A  99      -1.398  13.188  14.692  1.00 51.85           C
ATOM    456  OE1  GLN A  99      -0.994  14.358  14.608  1.00 53.12           O
ATOM    457  NE2  GLN A  99      -2.652  12.831  14.373  1.00 52.83           N
ATOM    458  C    GLN A  99      -1.176   8.455  14.141  1.00 41.10           C
ATOM    459  O    GLN A  99      -2.016   7.725  14.667  1.00 41.16           O
ATOM    460  N    ILE A 100      -0.948   8.475  12.832  1.00 40.13           N
ATOM    461  CA   ILE A 100      -1.668   7.586  11.927  1.00 39.49           C
ATOM    462  CB   ILE A 100      -1.428   7.976  10.448  1.00 38.95           C
```

FIG. 2-8

| | | | | | | | | | |
|---|---|---|---|---|---|---|---|---|---|
| ATOM | 463 | CG2 | ILE | A | 100 | -2.033 | 6.931 | 9.527 | 1.00 38.51 | C |
| ATOM | 464 | CG1 | ILE | A | 100 | -2.045 | 9.342 | 10.164 | 1.00 37.83 | C |
| ATOM | 465 | CD1 | ILE | A | 100 | -1.838 | 9.817 | 8.750 | 1.00 38.82 | C |
| ATOM | 466 | C | ILE | A | 100 | -1.244 | 6.145 | 12.131 | 1.00 39.77 | C |
| ATOM | 467 | O | ILE | A | 100 | -2.072 | 5.236 | 12.177 | 1.00 39.61 | O |
| ATOM | 468 | N | MET | A | 101 | 0.059 | 5.947 | 12.265 | 1.00 40.38 | N |
| ATOM | 469 | CA | MET | A | 101 | 0.615 | 4.623 | 12.447 | 1.00 41.48 | C |
| ATOM | 470 | CB | MET | A | 101 | 2.131 | 4.719 | 12.482 | 1.00 42.91 | C |
| ATOM | 471 | CG | MET | A | 101 | 2.838 | 3.429 | 12.149 | 1.00 45.77 | C |
| ATOM | 472 | SD | MET | A | 101 | 3.125 | 3.300 | 10.375 | 1.00 46.26 | S |
| ATOM | 473 | CE | MET | A | 101 | 4.341 | 4.600 | 10.189 | 1.00 46.40 | C |
| ATOM | 474 | C | MET | A | 101 | 0.122 | 4.009 | 13.745 | 1.00 43.04 | C |
| ATOM | 475 | O | MET | A | 101 | -0.222 | 2.824 | 13.813 | 1.00 43.67 | O |
| ATOM | 476 | N | ARG | A | 102 | 0.093 | 4.836 | 14.779 | 1.00 44.61 | N |
| ATOM | 477 | CA | ARG | A | 102 | -0.316 | 4.421 | 16.115 | 1.00 45.35 | C |
| ATOM | 478 | CB | ARG | A | 102 | -0.175 | 5.612 | 17.063 | 1.00 46.40 | C |
| ATOM | 479 | CG | ARG | A | 102 | 0.146 | 5.254 | 18.488 | 1.00 48.90 | C |
| ATOM | 480 | CD | ARG | A | 102 | 1.483 | 5.849 | 18.906 | 1.00 50.71 | C |
| ATOM | 481 | NE | ARG | A | 102 | 1.761 | 5.545 | 20.307 | 1.00 52.49 | N |
| ATOM | 482 | CZ | ARG | A | 102 | 1.105 | 6.081 | 21.333 | 1.00 51.86 | C |
| ATOM | 483 | NH1 | ARG | A | 102 | 0.135 | 6.958 | 21.116 | 1.00 51.78 | N |
| ATOM | 484 | NH2 | ARG | A | 102 | 1.409 | 5.725 | 22.579 | 1.00 53.32 | N |
| ATOM | 485 | C | ARG | A | 102 | -1.728 | 3.829 | 16.215 | 1.00 45.65 | C |
| ATOM | 486 | O | ARG | A | 102 | -2.008 | 3.076 | 17.142 | 1.00 45.89 | O |
| ATOM | 487 | N | LYS | A | 103 | -2.621 | 4.154 | 15.283 | 1.00 46.19 | N |
| ATOM | 488 | CA | LYS | A | 103 | -3.971 | 3.594 | 15.360 | 1.00 46.14 | C |
| ATOM | 489 | CB | LYS | A | 103 | -5.023 | 4.703 | 15.262 | 1.00 46.77 | C |
| ATOM | 490 | CG | LYS | A | 103 | -5.418 | 5.079 | 13.845 | 1.00 47.77 | C |
| ATOM | 491 | CD | LYS | A | 103 | -6.403 | 6.245 | 13.828 | 1.00 48.79 | C |
| ATOM | 492 | CE | LYS | A | 103 | -5.748 | 7.522 | 14.322 | 1.00 48.62 | C |
| ATOM | 493 | NZ | LYS | A | 103 | -6.671 | 8.686 | 14.242 | 1.00 50.95 | N |
| ATOM | 494 | C | LYS | A | 103 | -4.259 | 2.526 | 14.308 | 1.00 46.13 | C |
| ATOM | 495 | O | LYS | A | 103 | -5.414 | 2.171 | 14.083 | 1.00 45.94 | O |
| ATOM | 496 | N | LEU | A | 104 | -3.211 | 2.010 | 13.665 | 1.00 44.91 | N |
| ATOM | 497 | CA | LEU | A | 104 | -3.379 | 0.982 | 12.631 | 1.00 43.39 | C |
| ATOM | 498 | CB | LEU | A | 104 | -2.616 | 1.387 | 11.364 | 1.00 41.62 | C |
| ATOM | 499 | CG | LEU | A | 104 | -3.397 | 2.001 | 10.188 | 1.00 40.62 | C |
| ATOM | 500 | CD1 | LEU | A | 104 | -4.469 | 2.954 | 10.674 | 1.00 38.09 | C |
| ATOM | 501 | CD2 | LEU | A | 104 | -2.417 | 2.698 | 9.255 | 1.00 39.06 | C |
| ATOM | 502 | C | LEU | A | 104 | -2.930 | -0.411 | 13.069 | 1.00 43.15 | C |
| ATOM | 503 | O | LEU | A | 104 | -1.864 | -0.576 | 13.656 | 1.00 43.20 | O |
| ATOM | 504 | N | ASP | A | 105 | -3.758 | -1.411 | 12.794 | 1.00 44.02 | N |
| ATOM | 505 | CA | ASP | A | 105 | -3.432 | -2.793 | 13.126 | 1.00 45.24 | C |
| ATOM | 506 | CB | ASP | A | 105 | -3.852 | -3.150 | 14.544 | 1.00 48.61 | C |
| ATOM | 507 | CG | ASP | A | 105 | -3.317 | -4.504 | 14.980 | 1.00 52.72 | C |
| ATOM | 508 | OD1 | ASP | A | 105 | -3.478 | -5.487 | 14.224 | 1.00 55.75 | O |
| ATOM | 509 | OD2 | ASP | A | 105 | -2.741 | -4.591 | 16.083 | 1.00 54.91 | O |
| ATOM | 510 | C | ASP | A | 105 | -4.176 | -3.672 | 12.143 | 1.00 45.11 | C |
| ATOM | 511 | O | ASP | A | 105 | -5.370 | -3.941 | 12.305 | 1.00 45.44 | O |
| ATOM | 512 | N | HIS | A | 106 | -3.450 | -4.122 | 11.124 | 1.00 45.21 | N |
| ATOM | 513 | CA | HIS | A | 106 | -4.020 | -4.945 | 10.072 | 1.00 43.84 | C |
| ATOM | 514 | CB | HIS | A | 106 | -4.617 | -4.021 | 9.006 | 1.00 43.75 | C |
| ATOM | 515 | CG | HIS | A | 106 | -5.464 | -4.724 | 7.996 | 1.00 43.80 | C |
| ATOM | 516 | CD2 | HIS | A | 106 | -6.808 | -4.862 | 7.904 | 1.00 43.94 | C |
| ATOM | 517 | ND1 | HIS | A | 106 | -4.934 | -5.397 | 6.917 | 1.00 42.56 | N |
| ATOM | 518 | CE1 | HIS | A | 106 | -5.915 | -5.919 | 6.204 | 1.00 43.83 | C |
| ATOM | 519 | NE2 | HIS | A | 106 | -7.064 | -5.609 | 6.783 | 1.00 43.92 | N |
| ATOM | 520 | C | HIS | A | 106 | -2.938 | -5.836 | 9.465 | 1.00 43.18 | C |
| ATOM | 521 | O | HIS | A | 106 | -1.797 | -5.406 | 9.275 | 1.00 42.37 | O |
| ATOM | 522 | N | CYS | A | 107 | -3.310 | -7.078 | 9.164 | 1.00 42.66 | N |
| ATOM | 523 | CA | CYS | A | 107 | -2.399 | -8.069 | 8.587 | 1.00 42.04 | C |
| ATOM | 524 | CB | CYS | A | 107 | -3.177 | -9.354 | 8.257 | 1.00 44.28 | C |
| ATOM | 525 | SG | CYS | A | 107 | -4.710 | -9.082 | 7.244 | 1.00 48.11 | S |
| ATOM | 526 | C | CYS | A | 107 | -1.669 | -7.585 | 7.335 | 1.00 40.91 | C |
| ATOM | 527 | O | CYS | A | 107 | -0.618 | -8.117 | 6.983 | 1.00 40.27 | O |
| ATOM | 528 | N | ASN | A | 108 | -2.220 | -6.578 | 6.662 | 1.00 39.70 | N |
| ATOM | 529 | CA | ASN | A | 108 | -1.602 | -6.078 | 5.442 | 1.00 38.42 | C |

FIG. 2-9

| | | | | | | | | | |
|---|---|---|---|---|---|---|---|---|---|
| ATOM | 530 | CB | ASN | A | 108 | -2.634 | -6.042 | 4.324 | 1.00 38.08 | C |
| ATOM | 531 | CG | ASN | A | 108 | -3.083 | -7.428 | 3.912 | 1.00 38.44 | C |
| ATOM | 532 | OD1 | ASN | A | 108 | -4.282 | -7.716 | 3.856 | 1.00 39.21 | O |
| ATOM | 533 | ND2 | ASN | A | 108 | -2.120 | -8.298 | 3.624 | 1.00 35.56 | N |
| ATOM | 534 | C | ASN | A | 108 | -0.937 | -4.718 | 5.551 | 1.00 37.92 | C |
| ATOM | 535 | O | ASN | A | 108 | -0.855 | -3.984 | 4.568 | 1.00 38.00 | O |
| ATOM | 536 | N | ILE | A | 109 | -0.459 | -4.370 | 6.738 | 1.00 36.74 | N |
| ATOM | 537 | CA | ILE | A | 109 | 0.213 | -3.093 | 6.918 | 1.00 36.63 | C |
| ATOM | 538 | CB | ILE | A | 109 | -0.762 | -2.042 | 7.497 | 1.00 36.53 | C |
| ATOM | 539 | CG2 | ILE | A | 109 | -0.020 | -0.752 | 7.812 | 1.00 35.59 | C |
| ATOM | 540 | CG1 | ILE | A | 109 | -1.897 | -1.792 | 6.502 | 1.00 36.89 | C |
| ATOM | 541 | CD1 | ILE | A | 109 | -2.969 | -0.831 | 7.002 | 1.00 37.41 | C |
| ATOM | 542 | C | ILE | A | 109 | 1.390 | -3.286 | 7.862 | 1.00 36.44 | C |
| ATOM | 543 | O | ILE | A | 109 | 1.233 | -3.899 | 8.915 | 1.00 35.59 | O |
| ATOM | 544 | N | VAL | A | 110 | 2.567 | -2.789 | 7.483 | 1.00 37.78 | N |
| ATOM | 545 | CA | VAL | A | 110 | 3.727 | -2.933 | 8.358 | 1.00 40.13 | C |
| ATOM | 546 | CB | VAL | A | 110 | 4.957 | -2.096 | 7.895 | 1.00 40.17 | C |
| ATOM | 547 | CG1 | VAL | A | 110 | 5.335 | -2.460 | 6.470 | 1.00 42.25 | C |
| ATOM | 548 | CG2 | VAL | A | 110 | 4.663 | -0.615 | 8.016 | 1.00 41.20 | C |
| ATOM | 549 | C | VAL | A | 110 | 3.284 | -2.433 | 9.724 | 1.00 40.83 | C |
| ATOM | 550 | O | VAL | A | 110 | 2.620 | -1.404 | 9.831 | 1.00 40.96 | O |
| ATOM | 551 | N | ARG | A | 111 | 3.639 | -3.174 | 10.763 | 1.00 42.04 | N |
| ATOM | 552 | CA | ARG | A | 111 | 3.257 | -2.816 | 12.118 | 1.00 43.52 | C |
| ATOM | 553 | CB | ARG | A | 111 | 3.159 | -4.089 | 12.970 | 1.00 46.80 | C |
| ATOM | 554 | CG | ARG | A | 111 | 2.838 | -3.909 | 14.461 | 1.00 50.77 | C |
| ATOM | 555 | CD | ARG | A | 111 | 2.808 | -5.289 | 15.153 | 1.00 53.34 | C |
| ATOM | 556 | NE | ARG | A | 111 | 4.067 | -6.008 | 14.927 | 1.00 58.42 | N |
| ATOM | 557 | CZ | ARG | A | 111 | 4.170 | -7.293 | 14.574 | 1.00 60.50 | C |
| ATOM | 558 | NH1 | ARG | A | 111 | 3.076 | -8.029 | 14.401 | 1.00 61.08 | N |
| ATOM | 559 | NH2 | ARG | A | 111 | 5.372 | -7.838 | 14.388 | 1.00 60.00 | N |
| ATOM | 560 | C | ARG | A | 111 | 4.258 | -1.855 | 12.738 | 1.00 43.27 | C |
| ATOM | 561 | O | ARG | A | 111 | 5.449 | -1.890 | 12.424 | 1.00 42.94 | O |
| ATOM | 562 | N | LEU | A | 112 | 3.757 | -0.976 | 13.598 | 1.00 42.56 | N |
| ATOM | 563 | CA | LEU | A | 112 | 4.618 | -0.045 | 14.308 | 1.00 41.70 | C |
| ATOM | 564 | CB | LEU | A | 112 | 3.968 | 1.331 | 14.441 | 1.00 40.53 | C |
| ATOM | 565 | CG | LEU | A | 112 | 4.706 | 2.317 | 15.354 | 1.00 40.29 | C |
| ATOM | 566 | CD1 | LEU | A | 112 | 6.133 | 2.543 | 14.848 | 1.00 40.08 | C |
| ATOM | 567 | CD2 | LEU | A | 112 | 3.945 | 3.635 | 15.404 | 1.00 40.33 | C |
| ATOM | 568 | C | LEU | A | 112 | 4.775 | -0.691 | 15.678 | 1.00 41.18 | C |
| ATOM | 569 | O | LEU | A | 112 | 3.899 | -0.576 | 16.529 | 1.00 41.05 | O |
| ATOM | 570 | N | ARG | A | 113 | 5.889 | -1.397 | 15.859 | 1.00 41.09 | N |
| ATOM | 571 | CA | ARG | A | 113 | 6.193 | -2.099 | 17.100 | 1.00 40.66 | C |
| ATOM | 572 | CB | ARG | A | 113 | 7.470 | -2.923 | 16.940 | 1.00 43.33 | C |
| ATOM | 573 | CG | ARG | A | 113 | 7.596 | -3.697 | 15.632 | 1.00 46.76 | C |
| ATOM | 574 | CD | ARG | A | 113 | 6.600 | -4.837 | 15.550 | 1.00 50.95 | C |
| ATOM | 575 | NE | ARG | A | 113 | 7.108 | -6.094 | 16.123 | 1.00 55.59 | N |
| ATOM | 576 | CZ | ARG | A | 113 | 8.001 | -6.884 | 15.526 | 1.00 56.09 | C |
| ATOM | 577 | NH1 | ARG | A | 113 | 8.494 | -6.554 | 14.338 | 1.00 54.89 | N |
| ATOM | 578 | NH2 | ARG | A | 113 | 8.388 | -8.007 | 16.116 | 1.00 56.12 | N |
| ATOM | 579 | C | ARG | A | 113 | 6.389 | -1.123 | 18.247 | 1.00 39.27 | C |
| ATOM | 580 | O | ARG | A | 113 | 5.754 | -1.249 | 19.289 | 1.00 40.32 | O |
| ATOM | 581 | N | TYR | A | 114 | 7.288 | -0.164 | 18.057 | 1.00 37.25 | N |
| ATOM | 582 | CA | TYR | A | 114 | 7.582 | 0.825 | 19.084 | 1.00 36.78 | C |
| ATOM | 583 | CB | TYR | A | 114 | 8.762 | 0.388 | 19.953 | 1.00 37.87 | C |
| ATOM | 584 | CG | TYR | A | 114 | 8.709 | -1.024 | 20.464 | 1.00 38.86 | C |
| ATOM | 585 | CD1 | TYR | A | 114 | 7.874 | -1.372 | 21.521 | 1.00 39.64 | C |
| ATOM | 586 | CE1 | TYR | A | 114 | 7.841 | -2.668 | 22.012 | 1.00 40.22 | C |
| ATOM | 587 | CD2 | TYR | A | 114 | 9.514 | -2.013 | 19.906 | 1.00 39.46 | C |
| ATOM | 588 | CE2 | TYR | A | 114 | 9.489 | -3.315 | 20.389 | 1.00 40.55 | C |
| ATOM | 589 | CZ | TYR | A | 114 | 8.648 | -3.630 | 21.446 | 1.00 40.97 | C |
| ATOM | 590 | OH | TYR | A | 114 | 8.620 | -4.910 | 21.941 | 1.00 43.30 | O |
| ATOM | 591 | C | TYR | A | 114 | 7.999 | 2.118 | 18.429 | 1.00 36.81 | C |
| ATOM | 592 | O | TYR | A | 114 | 8.172 | 2.185 | 17.213 | 1.00 37.21 | O |
| ATOM | 593 | N | PHE | A | 115 | 8.173 | 3.140 | 19.258 | 1.00 35.84 | N |
| ATOM | 594 | CA | PHE | A | 115 | 8.645 | 4.433 | 18.804 | 1.00 35.06 | C |
| ATOM | 595 | CB | PHE | A | 115 | 7.496 | 5.317 | 18.309 | 1.00 35.39 | C |
| ATOM | 596 | CG | PHE | A | 115 | 6.625 | 5.879 | 19.388 | 1.00 34.94 | C |

FIG. 2-10

| ATOM | 597 | CD1 | PHE | A | 115 | 6.877 | 7.141 | 19.920 | 1.00 | 34.27 | C |
|---|---|---|---|---|---|---|---|---|---|---|---|
| ATOM | 598 | CD2 | PHE | A | 115 | 5.511 | 5.174 | 19.828 | 1.00 | 34.50 | C |
| ATOM | 599 | CE1 | PHE | A | 115 | 6.026 | 7.698 | 20.872 | 1.00 | 33.97 | C |
| ATOM | 600 | CE2 | PHE | A | 115 | 4.653 | 5.717 | 20.777 | 1.00 | 34.01 | C |
| ATOM | 601 | CZ | PHE | A | 115 | 4.909 | 6.983 | 21.301 | 1.00 | 34.04 | C |
| ATOM | 602 | C | PHE | A | 115 | 9.358 | 5.034 | 19.991 | 1.00 | 34.84 | C |
| ATOM | 603 | O | PHE | A | 115 | 8.973 | 4.799 | 21.132 | 1.00 | 35.55 | O |
| ATOM | 604 | N | PHE | A | 116 | 10.422 | 5.778 | 19.735 | 1.00 | 34.85 | N |
| ATOM | 605 | CA | PHE | A | 116 | 11.169 | 6.346 | 20.832 | 1.00 | 34.58 | C |
| ATOM | 606 | CB | PHE | A | 116 | 12.074 | 5.278 | 21.429 | 1.00 | 32.94 | C |
| ATOM | 607 | CG | PHE | A | 116 | 13.153 | 4.805 | 20.492 | 1.00 | 32.76 | C |
| ATOM | 608 | CD1 | PHE | A | 116 | 14.345 | 5.509 | 20.365 | 1.00 | 31.49 | C |
| ATOM | 609 | CD2 | PHE | A | 116 | 12.987 | 3.647 | 19.744 | 1.00 | 31.17 | C |
| ATOM | 610 | CE1 | PHE | A | 116 | 15.354 | 5.064 | 19.511 | 1.00 | 30.35 | C |
| ATOM | 611 | CE2 | PHE | A | 116 | 13.994 | 3.201 | 18.891 | 1.00 | 29.60 | C |
| ATOM | 612 | CZ | PHE | A | 116 | 15.176 | 3.910 | 18.776 | 1.00 | 28.32 | C |
| ATOM | 613 | C | PHE | A | 116 | 12.002 | 7.510 | 20.347 | 1.00 | 36.20 | C |
| ATOM | 614 | O | PHE | A | 116 | 12.433 | 7.535 | 19.198 | 1.00 | 37.30 | O |
| ATOM | 615 | N | TYR | A | 117 | 12.250 | 8.463 | 21.237 | 1.00 | 36.02 | N |
| ATOM | 616 | CA | TYR | A | 117 | 13.024 | 9.641 | 20.894 | 1.00 | 36.94 | C |
| ATOM | 617 | CB | TYR | A | 117 | 12.421 | 10.850 | 21.606 | 1.00 | 37.41 | C |
| ATOM | 618 | CG | TYR | A | 117 | 10.950 | 10.989 | 21.321 | 1.00 | 38.65 | C |
| ATOM | 619 | CD1 | TYR | A | 117 | 10.495 | 11.803 | 20.285 | 1.00 | 39.49 | C |
| ATOM | 620 | CE1 | TYR | A | 117 | 9.150 | 11.837 | 19.931 | 1.00 | 40.05 | C |
| ATOM | 621 | CD2 | TYR | A | 117 | 10.021 | 10.215 | 22.008 | 1.00 | 37.91 | C |
| ATOM | 622 | CE2 | TYR | A | 117 | 8.680 | 10.234 | 21.666 | 1.00 | 39.76 | C |
| ATOM | 623 | CZ | TYR | A | 117 | 8.250 | 11.045 | 20.624 | 1.00 | 41.49 | C |
| ATOM | 624 | OH | TYR | A | 117 | 6.922 | 11.035 | 20.256 | 1.00 | 44.67 | O |
| ATOM | 625 | C | TYR | A | 117 | 14.491 | 9.475 | 21.260 | 1.00 | 38.18 | C |
| ATOM | 626 | O | TYR | A | 117 | 14.833 | 8.755 | 22.200 | 1.00 | 38.23 | O |
| ATOM | 627 | N | SER | A | 118 | 15.356 | 10.145 | 20.506 | 1.00 | 40.00 | N |
| ATOM | 628 | CA | SER | A | 118 | 16.794 | 10.081 | 20.729 | 1.00 | 42.18 | C |
| ATOM | 629 | CB | SER | A | 118 | 17.402 | 8.975 | 19.862 | 1.00 | 42.36 | C |
| ATOM | 630 | OG | SER | A | 118 | 17.286 | 9.294 | 18.483 | 1.00 | 40.42 | O |
| ATOM | 631 | C | SER | A | 118 | 17.438 | 11.423 | 20.384 | 1.00 | 44.18 | C |
| ATOM | 632 | O | SER | A | 118 | 16.832 | 12.243 | 19.688 | 1.00 | 43.20 | O |
| ATOM | 633 | N | SER | A | 119 | 18.659 | 11.649 | 20.870 | 1.00 | 47.49 | N |
| ATOM | 634 | CA | SER | A | 119 | 19.378 | 12.900 | 20.588 | 1.00 | 49.81 | C |
| ATOM | 635 | CB | SER | A | 119 | 20.067 | 13.428 | 21.853 | 1.00 | 50.48 | C |
| ATOM | 636 | OG | SER | A | 119 | 19.132 | 13.978 | 22.777 | 1.00 | 50.85 | O |
| ATOM | 637 | C | SER | A | 119 | 20.423 | 12.708 | 19.491 | 1.00 | 50.28 | C |
| ATOM | 638 | O | SER | A | 119 | 20.453 | 13.459 | 18.510 | 1.00 | 51.12 | O |
| ATOM | 639 | N | ALA | A | 125 | 19.254 | 17.623 | 19.061 | 1.00 | 63.10 | N |
| ATOM | 640 | CA | ALA | A | 125 | 17.879 | 17.981 | 18.681 | 1.00 | 62.43 | C |
| ATOM | 641 | CB | ALA | A | 125 | 17.825 | 18.351 | 17.199 | 1.00 | 61.56 | C |
| ATOM | 642 | C | ALA | A | 125 | 17.044 | 16.737 | 18.952 | 1.00 | 61.66 | C |
| ATOM | 643 | O | ALA | A | 125 | 17.556 | 15.773 | 19.527 | 1.00 | 62.56 | O |
| ATOM | 644 | N | ALA | A | 126 | 15.775 | 16.734 | 18.562 | 1.00 | 59.77 | N |
| ATOM | 645 | CA | ALA | A | 126 | 14.961 | 15.543 | 18.814 | 1.00 | 58.10 | C |
| ATOM | 646 | CB | ALA | A | 126 | 13.700 | 15.915 | 19.589 | 1.00 | 57.48 | C |
| ATOM | 647 | C | ALA | A | 126 | 14.591 | 14.776 | 17.553 | 1.00 | 56.22 | C |
| ATOM | 648 | O | ALA | A | 126 | 14.018 | 15.322 | 16.609 | 1.00 | 56.30 | O |
| ATOM | 649 | N | TYR | A | 127 | 14.951 | 13.501 | 17.538 | 1.00 | 53.41 | N |
| ATOM | 650 | CA | TYR | A | 127 | 14.624 | 12.650 | 16.413 | 1.00 | 52.14 | C |
| ATOM | 651 | CB | TYR | A | 127 | 15.860 | 11.902 | 15.888 | 1.00 | 54.85 | C |
| ATOM | 652 | CG | TYR | A | 127 | 16.961 | 12.811 | 15.386 | 1.00 | 58.96 | C |
| ATOM | 653 | CD1 | TYR | A | 127 | 17.493 | 13.811 | 16.213 | 1.00 | 61.45 | C |
| ATOM | 654 | CE1 | TYR | A | 127 | 18.520 | 14.645 | 15.773 | 1.00 | 62.79 | C |
| ATOM | 655 | CD2 | TYR | A | 127 | 17.486 | 12.666 | 14.100 | 1.00 | 60.32 | C |
| ATOM | 656 | CE2 | TYR | A | 127 | 18.516 | 13.489 | 13.644 | 1.00 | 62.10 | C |
| ATOM | 657 | CZ | TYR | A | 127 | 19.029 | 14.479 | 14.489 | 1.00 | 64.13 | C |
| ATOM | 658 | OH | TYR | A | 127 | 20.056 | 15.308 | 14.052 | 1.00 | 65.95 | O |
| ATOM | 659 | C | TYR | A | 127 | 13.592 | 11.665 | 16.926 | 1.00 | 49.42 | C |
| ATOM | 660 | O | TYR | A | 127 | 13.612 | 11.274 | 18.099 | 1.00 | 47.74 | O |
| ATOM | 661 | N | LEU | A | 128 | 12.657 | 11.312 | 16.052 | 1.00 | 46.30 | N |
| ATOM | 662 | CA | LEU | A | 128 | 11.614 | 10.365 | 16.386 | 1.00 | 43.43 | C |
| ATOM | 663 | CB | LEU | A | 128 | 10.266 | 10.831 | 15.855 | 1.00 | 43.53 | C |

FIG. 2-11

```
ATOM    664  CG   LEU A 128       9.203    9.731   15.868  1.00 44.46           C
ATOM    665  CD1  LEU A 128       8.900    9.318   17.308  1.00 44.75           C
ATOM    666  CD2  LEU A 128       7.945   10.240   15.172  1.00 44.80           C
ATOM    667  C    LEU A 128      12.008    9.088   15.691  1.00 41.86           C
ATOM    668  O    LEU A 128      12.319    9.098   14.501  1.00 42.35           O
ATOM    669  N    ASN A 129      11.998    7.987   16.428  1.00 40.06           N
ATOM    670  CA   ASN A 129      12.367    6.705   15.855  1.00 37.56           C
ATOM    671  CB   ASN A 129      13.469    6.052   16.694  1.00 36.76           C
ATOM    672  CG   ASN A 129      14.727    6.889   16.750  1.00 36.24           C
ATOM    673  OD1  ASN A 129      15.621    6.744   15.924  1.00 34.39           O
ATOM    674  ND2  ASN A 129      14.792    7.786   17.723  1.00 36.12           N
ATOM    675  C    ASN A 129      11.162    5.799   15.803  1.00 36.77           C
ATOM    676  O    ASN A 129      10.439    5.667   16.785  1.00 36.75           O
ATOM    677  N    LEU A 130      10.945    5.187   14.647  1.00 36.70           N
ATOM    678  CA   LEU A 130       9.839    4.260   14.474  1.00 35.85           C
ATOM    679  CB   LEU A 130       9.005    4.649   13.253  1.00 35.92           C
ATOM    680  CG   LEU A 130       8.254    5.969   13.375  1.00 35.86           C
ATOM    681  CD1  LEU A 130       7.733    6.384   12.023  1.00 35.53           C
ATOM    682  CD2  LEU A 130       7.121    5.821   14.386  1.00 36.59           C
ATOM    683  C    LEU A 130      10.419    2.873   14.269  1.00 35.05           C
ATOM    684  O    LEU A 130      11.231    2.660   13.362  1.00 35.24           O
ATOM    685  N    VAL A 131      10.025    1.936   15.123  1.00 32.91           N
ATOM    686  CA   VAL A 131      10.503    0.565   15.005  1.00 32.56           C
ATOM    687  CB   VAL A 131      10.709   -0.081   16.364  1.00 32.06           C
ATOM    688  CG1  VAL A 131      11.301   -1.465   16.178  1.00 32.00           C
ATOM    689  CG2  VAL A 131      11.628    0.790   17.206  1.00 32.32           C
ATOM    690  C    VAL A 131       9.434   -0.181   14.247  1.00 32.82           C
ATOM    691  O    VAL A 131       8.343   -0.404   14.756  1.00 33.20           O
ATOM    692  N    LEU A 132       9.758   -0.583   13.027  1.00 32.81           N
ATOM    693  CA   LEU A 132       8.779   -1.236   12.180  1.00 34.13           C
ATOM    694  CB   LEU A 132       8.534   -0.349   10.966  1.00 34.16           C
ATOM    695  CG   LEU A 132       8.162    1.088   11.327  1.00 35.13           C
ATOM    696  CD1  LEU A 132       8.575    2.043   10.225  1.00 32.26           C
ATOM    697  CD2  LEU A 132       6.689    1.146   11.596  1.00 33.83           C
ATOM    698  C    LEU A 132       9.117   -2.633   11.701  1.00 35.71           C
ATOM    699  O    LEU A 132      10.258   -3.073   11.775  1.00 37.31           O
ATOM    700  N    ASP A 133       8.095   -3.329   11.215  1.00 36.85           N
ATOM    701  CA   ASP A 133       8.250   -4.666   10.660  1.00 38.12           C
ATOM    702  CB   ASP A 133       6.953   -5.115    9.973  1.00 40.49           C
ATOM    703  CG   ASP A 133       5.927   -5.692   10.930  1.00 44.60           C
ATOM    704  OD1  ASP A 133       4.709   -5.579   10.605  1.00 44.70           O
ATOM    705  OD2  ASP A 133       6.325   -6.277   11.977  1.00 45.47           O
ATOM    706  C    ASP A 133       9.320   -4.522    9.578  1.00 38.99           C
ATOM    707  O    ASP A 133       9.327   -3.535    8.846  1.00 38.10           O
ATOM    708  N    TYR A 134      10.207   -5.504    9.469  1.00 39.30           N
ATOM    709  CA   TYR A 134      11.234   -5.467    8.443  1.00 39.33           C
ATOM    710  CB   TYR A 134      12.612   -5.773    9.021  1.00 39.76           C
ATOM    711  CG   TYR A 134      13.680   -5.815    7.951  1.00 39.51           C
ATOM    712  CD1  TYR A 134      14.180   -4.639    7.404  1.00 40.92           C
ATOM    713  CE1  TYR A 134      15.116   -4.656    6.381  1.00 40.43           C
ATOM    714  CD2  TYR A 134      14.149   -7.027    7.443  1.00 39.02           C
ATOM    715  CE2  TYR A 134      15.094   -7.055    6.409  1.00 39.00           C
ATOM    716  CZ   TYR A 134      15.567   -5.857    5.891  1.00 39.88           C
ATOM    717  OH   TYR A 134      16.494   -5.842    4.880  1.00 41.55           O
ATOM    718  C    TYR A 134      10.932   -6.492    7.352  1.00 40.69           C
ATOM    719  O    TYR A 134      11.207   -7.682    7.512  1.00 42.07           O
ATOM    720  N    VAL A 135      10.362   -6.031    6.247  1.00 40.64           N
ATOM    721  CA   VAL A 135      10.038   -6.914    5.140  1.00 40.59           C
ATOM    722  CB   VAL A 135       8.546   -6.802    4.788  1.00 39.31           C
ATOM    723  CG1  VAL A 135       8.150   -7.878    3.804  1.00 36.24           C
ATOM    724  CG2  VAL A 135       7.720   -6.927    6.064  1.00 37.10           C
ATOM    725  C    VAL A 135      10.940   -6.474    3.985  1.00 42.91           C
ATOM    726  O    VAL A 135      10.805   -5.373    3.448  1.00 43.66           O
ATOM    727  N    PRO A 136      11.879   -7.351    3.594  1.00 44.14           N
ATOM    728  CD   PRO A 136      11.793   -8.774    3.994  1.00 44.36           C
ATOM    729  CA   PRO A 136      12.880   -7.174    2.536  1.00 44.14           C
ATOM    730  CB   PRO A 136      13.702   -8.452    2.645  1.00 44.33           C
```

FIG. 2-12

| | | | | | | | | | | |
|---|---|---|---|---|---|---|---|---|---|---|
| ATOM | 731 | CG | PRO | A | 136 | 12.652 | -9.468 | 2.960 | 1.00 44.28 | C |
| ATOM | 732 | C | PRO | A | 136 | 12.392 | -6.916 | 1.107 | 1.00 43.77 | C |
| ATOM | 733 | O | PRO | A | 136 | 12.746 | -5.906 | 0.500 | 1.00 43.24 | O |
| ATOM | 734 | N | GLU | A | 137 | 11.595 | -7.837 | 0.573 | 1.00 42.36 | N |
| ATOM | 735 | CA | GLU | A | 137 | 11.083 | -7.724 | -0.787 | 1.00 40.10 | C |
| ATOM | 736 | CB | GLU | A | 137 | 10.617 | -9.091 | -1.286 | 1.00 41.23 | C |
| ATOM | 737 | CG | GLU | A | 137 | 11.721 | -9.902 | -1.914 | 1.00 44.55 | C |
| ATOM | 738 | CD | GLU | A | 137 | 12.230 | -9.264 | -3.193 | 1.00 45.70 | C |
| ATOM | 739 | OE1 | GLU | A | 137 | 12.578 | -8.061 | -3.182 | 1.00 46.35 | O |
| ATOM | 740 | OE2 | GLU | A | 137 | 12.279 | -9.967 | -4.213 | 1.00 47.63 | O |
| ATOM | 741 | C | GLU | A | 137 | 9.959 | -6.725 | -0.990 | 1.00 37.83 | C |
| ATOM | 742 | O | GLU | A | 137 | 9.156 | -6.472 | -0.090 | 1.00 37.20 | O |
| ATOM | 743 | N | THR | A | 138 | 9.908 | -6.180 | -2.200 | 1.00 35.00 | N |
| ATOM | 744 | CA | THR | A | 138 | 8.896 | -5.209 | -2.590 | 1.00 33.85 | C |
| ATOM | 745 | CB | THR | A | 138 | 9.494 | -3.797 | -2.746 | 1.00 33.62 | C |
| ATOM | 746 | OG1 | THR | A | 138 | 10.460 | -3.799 | -3.805 | 1.00 33.42 | O |
| ATOM | 747 | CG2 | THR | A | 138 | 10.160 | -3.357 | -1.457 | 1.00 31.39 | C |
| ATOM | 748 | C | THR | A | 138 | 8.334 | -5.644 | -3.937 | 1.00 33.82 | C |
| ATOM | 749 | O | THR | A | 138 | 8.970 | -6.402 | -4.666 | 1.00 33.21 | O |
| ATOM | 750 | N | VAL | A | 139 | 7.137 | -5.180 | -4.265 | 1.00 32.62 | N |
| ATOM | 751 | CA | VAL | A | 139 | 6.545 | -5.548 | -5.531 | 1.00 31.68 | C |
| ATOM | 752 | CB | VAL | A | 139 | 5.083 | -5.051 | -5.620 | 1.00 32.08 | C |
| ATOM | 753 | CG1 | VAL | A | 139 | 4.530 | -5.227 | -7.025 | 1.00 30.55 | C |
| ATOM | 754 | CG2 | VAL | A | 139 | 4.228 | -5.828 | -4.629 | 1.00 29.37 | C |
| ATOM | 755 | C | VAL | A | 139 | 7.393 | -4.945 | -6.641 | 1.00 33.82 | C |
| ATOM | 756 | O | VAL | A | 139 | 7.528 | -5.534 | -7.709 | 1.00 35.61 | O |
| ATOM | 757 | N | TYR | A | 140 | 7.991 | -3.784 | -6.384 | 1.00 34.34 | N |
| ATOM | 758 | CA | TYR | A | 140 | 8.832 | -3.133 | -7.387 | 1.00 34.89 | C |
| ATOM | 759 | CB | TYR | A | 140 | 9.368 | -1.795 | -6.876 | 1.00 33.04 | C |
| ATOM | 760 | CG | TYR | A | 140 | 10.414 | -1.200 | -7.792 | 1.00 32.64 | C |
| ATOM | 761 | CD1 | TYR | A | 140 | 10.056 | -0.549 | -8.970 | 1.00 33.66 | C |
| ATOM | 762 | CE1 | TYR | A | 140 | 11.026 | -0.049 | -9.841 | 1.00 33.97 | C |
| ATOM | 763 | CD2 | TYR | A | 140 | 11.768 | -1.336 | -7.505 | 1.00 32.31 | C |
| ATOM | 764 | CE2 | TYR | A | 140 | 12.744 | -0.843 | -8.365 | 1.00 32.84 | C |
| ATOM | 765 | CZ | TYR | A | 140 | 12.370 | -0.202 | -9.529 | 1.00 34.48 | C |
| ATOM | 766 | OH | TYR | A | 140 | 13.338 | 0.285 | -10.376 | 1.00 35.84 | O |
| ATOM | 767 | C | TYR | A | 140 | 10.016 | -4.000 | -7.834 | 1.00 36.41 | C |
| ATOM | 768 | O | TYR | A | 140 | 10.317 | -4.066 | -9.019 | 1.00 38.19 | O |
| ATOM | 769 | N | ARG | A | 141 | 10.688 | -4.646 | -6.889 | 1.00 36.70 | N |
| ATOM | 770 | CA | ARG | A | 141 | 11.827 | -5.488 | -7.215 | 1.00 38.19 | C |
| ATOM | 771 | CB | ARG | A | 141 | 12.595 | -5.856 | -5.948 | 1.00 39.78 | C |
| ATOM | 772 | CG | ARG | A | 141 | 13.393 | -4.712 | -5.355 | 1.00 44.37 | C |
| ATOM | 773 | CD | ARG | A | 141 | 13.381 | -4.761 | -3.835 | 1.00 47.97 | C |
| ATOM | 774 | NE | ARG | A | 141 | 14.655 | -4.313 | -3.283 | 1.00 52.29 | N |
| ATOM | 775 | CZ | ARG | A | 141 | 15.777 | -5.028 | -3.321 | 1.00 54.55 | C |
| ATOM | 776 | NH1 | ARG | A | 141 | 15.776 | -6.232 | -3.886 | 1.00 55.12 | N |
| ATOM | 777 | NH2 | ARG | A | 141 | 16.896 | -4.540 | -2.796 | 1.00 56.07 | N |
| ATOM | 778 | C | ARG | A | 141 | 11.394 | -6.757 | -7.934 | 1.00 38.50 | C |
| ATOM | 779 | O | ARG | A | 141 | 12.091 | -7.244 | -8.823 | 1.00 37.55 | O |
| ATOM | 780 | N | VAL | A | 142 | 10.245 | -7.297 | -7.548 | 1.00 37.99 | N |
| ATOM | 781 | CA | VAL | A | 142 | 9.738 | -8.500 | -8.179 | 1.00 36.91 | C |
| ATOM | 782 | CB | VAL | A | 142 | 8.535 | -9.073 | -7.400 | 1.00 37.14 | C |
| ATOM | 783 | CG1 | VAL | A | 142 | 7.815 | -10.128 | -8.219 | 1.00 37.75 | C |
| ATOM | 784 | CG2 | VAL | A | 142 | 9.028 | -9.686 | -6.099 | 1.00 36.91 | C |
| ATOM | 785 | C | VAL | A | 142 | 9.347 | -8.210 | -9.621 | 1.00 37.87 | C |
| ATOM | 786 | O | VAL | A | 142 | 9.754 | -8.930 | -10.533 | 1.00 39.44 | O |
| ATOM | 787 | N | ALA | A | 143 | 8.575 | -7.151 | -9.838 | 1.00 37.04 | N |
| ATOM | 788 | CA | ALA | A | 143 | 8.164 | -6.795 | -11.190 | 1.00 37.69 | C |
| ATOM | 789 | CB | ALA | A | 143 | 7.289 | -5.559 | -11.161 | 1.00 36.63 | C |
| ATOM | 790 | C | ALA | A | 143 | 9.401 | -6.544 | -12.041 | 1.00 38.72 | C |
| ATOM | 791 | O | ALA | A | 143 | 9.479 | -6.981 | -13.188 | 1.00 39.93 | O |
| ATOM | 792 | N | ARG | A | 144 | 10.372 | -5.851 | -11.457 | 1.00 40.46 | N |
| ATOM | 793 | CA | ARG | A | 144 | 11.623 | -5.522 | -12.129 | 1.00 41.87 | C |
| ATOM | 794 | CB | ARG | A | 144 | 12.489 | -4.682 | -11.179 | 1.00 43.17 | C |
| ATOM | 795 | CG | ARG | A | 144 | 13.383 | -3.638 | -11.845 | 1.00 43.11 | C |
| ATOM | 796 | CD | ARG | A | 144 | 14.845 | -4.003 | -11.694 | 1.00 44.28 | C |
| ATOM | 797 | NE | ARG | A | 144 | 15.239 | -4.189 | -10.295 | 1.00 46.64 | N |

FIG. 2-13

| ATOM | 798 | CZ | ARG A 144 | 15.623 | -3.207 | -9.478 | 1.00 | 47.53 | C |
| --- | --- | --- | --- | --- | --- | --- | --- | --- | --- |
| ATOM | 799 | NH1 | ARG A 144 | 15.677 | -1.953 | -9.910 | 1.00 | 48.31 | N |
| ATOM | 800 | NH2 | ARG A 144 | 15.952 | -3.480 | -8.226 | 1.00 | 46.85 | N |
| ATOM | 801 | C | ARG A 144 | 12.351 | -6.801 | -12.575 | 1.00 | 42.38 | C |
| ATOM | 802 | O | ARG A 144 | 12.798 | -6.891 | -13.715 | 1.00 | 42.09 | O |
| ATOM | 803 | N | HIS A 145 | 12.449 | -7.785 | -11.680 | 1.00 | 43.86 | N |
| ATOM | 804 | CA | HIS A 145 | 13.100 | -9.065 | -11.975 | 1.00 | 45.92 | C |
| ATOM | 805 | CB | HIS A 145 | 13.083 | -9.949 | -10.710 | 1.00 | 49.72 | C |
| ATOM | 806 | CG | HIS A 145 | 13.675 | -11.321 | -10.887 | 1.00 | 55.23 | C |
| ATOM | 807 | CD2 | HIS A 145 | 14.173 | -11.958 | -11.980 | 1.00 | 57.20 | C |
| ATOM | 808 | ND1 | HIS A 145 | 13.769 | -12.225 | -9.845 | 1.00 | 56.56 | N |
| ATOM | 809 | CE1 | HIS A 145 | 14.294 | -13.357 | -10.288 | 1.00 | 56.99 | C |
| ATOM | 810 | NE2 | HIS A 145 | 14.547 | -13.222 | -11.580 | 1.00 | 57.40 | N |
| ATOM | 811 | C | HIS A 145 | 12.413 | -9.769 | -13.158 | 1.00 | 45.51 | C |
| ATOM | 812 | O | HIS A 145 | 13.090 | -10.219 | -14.075 | 1.00 | 46.01 | O |
| ATOM | 813 | N | TYR A 146 | 11.080 | -9.859 | -13.153 | 1.00 | 45.04 | N |
| ATOM | 814 | CA | TYR A 146 | 10.369 | -10.508 | -14.253 | 1.00 | 43.09 | C |
| ATOM | 815 | CB | TYR A 146 | 8.876 | -10.644 | -13.964 | 1.00 | 41.22 | C |
| ATOM | 816 | CG | TYR A 146 | 8.528 | -11.792 | -13.066 | 1.00 | 41.40 | C |
| ATOM | 817 | CD1 | TYR A 146 | 8.739 | -11.704 | -11.701 | 1.00 | 41.17 | C |
| ATOM | 818 | CE1 | TYR A 146 | 8.477 | -12.773 | -10.867 | 1.00 | 42.77 | C |
| ATOM | 819 | CD2 | TYR A 146 | 8.037 | -12.992 | -13.587 | 1.00 | 40.38 | C |
| ATOM | 820 | CE2 | TYR A 146 | 7.770 | -14.079 | -12.751 | 1.00 | 41.66 | C |
| ATOM | 821 | CZ | TYR A 146 | 7.998 | -13.955 | -11.391 | 1.00 | 41.86 | C |
| ATOM | 822 | OH | TYR A 146 | 7.754 | -15.002 | -10.535 | 1.00 | 42.64 | O |
| ATOM | 823 | C | TYR A 146 | 10.512 | -9.743 | -15.535 | 1.00 | 44.00 | C |
| ATOM | 824 | O | TYR A 146 | 10.647 | -10.328 | -16.609 | 1.00 | 46.60 | O |
| ATOM | 825 | N | SER A 147 | 10.462 | -8.427 | -15.424 | 1.00 | 45.12 | N |
| ATOM | 826 | CA | SER A 147 | 10.549 | -7.548 | -16.583 | 1.00 | 46.45 | C |
| ATOM | 827 | CB | SER A 147 | 10.155 | -6.131 | -16.162 | 1.00 | 46.80 | C |
| ATOM | 828 | OG | SER A 147 | 10.261 | -5.235 | -17.247 | 1.00 | 48.70 | O |
| ATOM | 829 | C | SER A 147 | 11.916 | -7.537 | -17.264 | 1.00 | 47.98 | C |
| ATOM | 830 | O | SER A 147 | 12.000 | -7.576 | -18.489 | 1.00 | 47.18 | O |
| ATOM | 831 | N | ARG A 148 | 12.990 | -7.474 | -16.480 | 1.00 | 49.60 | N |
| ATOM | 832 | CA | ARG A 148 | 14.321 | -7.471 | -17.073 | 1.00 | 51.35 | C |
| ATOM | 833 | CB | ARG A 148 | 15.397 | -7.350 | -16.001 | 1.00 | 51.34 | C |
| ATOM | 834 | CG | ARG A 148 | 15.718 | -5.944 | -15.511 | 1.00 | 54.79 | C |
| ATOM | 835 | CD | ARG A 148 | 16.519 | -6.121 | -14.234 | 1.00 | 55.82 | C |
| ATOM | 836 | NE | ARG A 148 | 17.042 | -4.906 | -13.615 | 1.00 | 57.73 | N |
| ATOM | 837 | CZ | ARG A 148 | 17.548 | -4.891 | -12.382 | 1.00 | 58.91 | C |
| ATOM | 838 | NH1 | ARG A 148 | 17.574 | -6.017 | -11.672 | 1.00 | 59.55 | N |
| ATOM | 839 | NH2 | ARG A 148 | 18.046 | -3.771 | -11.870 | 1.00 | 59.17 | N |
| ATOM | 840 | C | ARG A 148 | 14.538 | -8.775 | -17.840 | 1.00 | 52.45 | C |
| ATOM | 841 | O | ARG A 148 | 15.307 | -8.821 | -18.803 | 1.00 | 53.17 | O |
| ATOM | 842 | N | ALA A 149 | 13.869 | -9.837 | -17.407 | 1.00 | 52.30 | N |
| ATOM | 843 | CA | ALA A 149 | 14.009 | -11.132 | -18.065 | 1.00 | 53.57 | C |
| ATOM | 844 | CB | ALA A 149 | 13.957 | -12.254 | -17.033 | 1.00 | 53.24 | C |
| ATOM | 845 | C | ALA A 149 | 12.923 | -11.338 | -19.108 | 1.00 | 54.81 | C |
| ATOM | 846 | O | ALA A 149 | 12.572 | -12.471 | -19.450 | 1.00 | 55.17 | O |
| ATOM | 847 | N | LYS A 150 | 12.383 | -10.234 | -19.603 | 1.00 | 56.15 | N |
| ATOM | 848 | CA | LYS A 150 | 11.339 | -10.288 | -20.615 | 1.00 | 56.52 | C |
| ATOM | 849 | CB | LYS A 150 | 11.956 | -10.554 | -21.987 | 1.00 | 58.63 | C |
| ATOM | 850 | CG | LYS A 150 | 11.581 | -9.508 | -23.029 | 1.00 | 60.61 | C |
| ATOM | 851 | CD | LYS A 150 | 11.921 | -8.104 | -22.566 | 1.00 | 61.80 | C |
| ATOM | 852 | CE | LYS A 150 | 13.396 | -7.789 | -22.767 | 1.00 | 62.72 | C |
| ATOM | 853 | NZ | LYS A 150 | 13.705 | -7.383 | -24.186 | 1.00 | 63.65 | N |
| ATOM | 854 | C | LYS A 150 | 10.290 | -11.345 | -20.317 | 1.00 | 55.71 | C |
| ATOM | 855 | O | LYS A 150 | 9.898 | -12.111 | -21.196 | 1.00 | 55.79 | O |
| ATOM | 856 | N | GLN A 151 | 9.842 | -11.392 | -19.071 | 1.00 | 54.47 | N |
| ATOM | 857 | CA | GLN A 151 | 8.814 | -12.346 | -18.702 | 1.00 | 53.41 | C |
| ATOM | 858 | CB | GLN A 151 | 9.392 | -13.457 | -17.836 | 1.00 | 55.06 | C |
| ATOM | 859 | CG | GLN A 151 | 8.441 | -14.618 | -17.692 | 1.00 | 57.19 | C |
| ATOM | 860 | CD | GLN A 151 | 9.165 | -15.924 | -17.738 | 1.00 | 57.66 | C |
| ATOM | 861 | OE1 | GLN A 151 | 10.098 | -16.143 | -16.969 | 1.00 | 58.63 | O |
| ATOM | 862 | NE2 | GLN A 151 | 8.750 | -16.807 | -18.642 | 1.00 | 58.04 | N |
| ATOM | 863 | C | GLN A 151 | 7.707 | -11.612 | -17.957 | 1.00 | 52.09 | C |
| ATOM | 864 | O | GLN A 151 | 7.891 | -10.479 | -17.512 | 1.00 | 51.62 | O |

FIG. 2-14

```
ATOM    865  N    THR A 152       6.563  -12.265  -17.816  1.00 50.08           N
ATOM    866  CA   THR A 152       5.406  -11.662  -17.175  1.00 48.35           C
ATOM    867  CB   THR A 152       4.219  -11.661  -18.163  1.00 49.29           C
ATOM    868  OG1  THR A 152       2.988  -11.465  -17.459  1.00 49.63           O
ATOM    869  CG2  THR A 152       4.164  -12.988  -18.923  1.00 50.42           C
ATOM    870  C    THR A 152       4.974  -12.336  -15.876  1.00 47.20           C
ATOM    871  O    THR A 152       4.699  -13.538  -15.844  1.00 49.03           O
ATOM    872  N    LEU A 153       4.897  -11.557  -14.803  1.00 43.79           N
ATOM    873  CA   LEU A 153       4.491  -12.089  -13.505  1.00 40.79           C
ATOM    874  CB   LEU A 153       4.426  -10.953  -12.481  1.00 39.28           C
ATOM    875  CG   LEU A 153       3.955  -11.281  -11.065  1.00 37.97           C
ATOM    876  CD1  LEU A 153       5.126  -11.714  -10.209  1.00 35.65           C
ATOM    877  CD2  LEU A 153       3.295  -10.042  -10.475  1.00 36.79           C
ATOM    878  C    LEU A 153       3.131  -12.801  -13.579  1.00 40.44           C
ATOM    879  O    LEU A 153       2.136  -12.216  -14.016  1.00 39.43           O
ATOM    880  N    PRO A 154       3.083  -14.088  -13.177  1.00 40.10           N
ATOM    881  CD   PRO A 154       4.253  -14.919  -12.823  1.00 40.15           C
ATOM    882  CA   PRO A 154       1.857  -14.900  -13.177  1.00 39.95           C
ATOM    883  CB   PRO A 154       2.268  -16.112  -12.351  1.00 40.03           C
ATOM    884  CG   PRO A 154       3.680  -16.318  -12.801  1.00 39.69           C
ATOM    885  C    PRO A 154       0.699  -14.130  -12.536  1.00 39.54           C
ATOM    886  O    PRO A 154       0.869  -13.538  -11.471  1.00 39.54           O
ATOM    887  N    VAL A 155      -0.473  -14.143  -13.170  1.00 40.18           N
ATOM    888  CA   VAL A 155      -1.616  -13.405  -12.640  1.00 40.64           C
ATOM    889  CB   VAL A 155      -2.874  -13.520  -13.558  1.00 39.61           C
ATOM    890  CG1  VAL A 155      -2.569  -12.962  -14.932  1.00 39.26           C
ATOM    891  CG2  VAL A 155      -3.332  -14.960  -13.655  1.00 39.85           C
ATOM    892  C    VAL A 155      -2.002  -13.799  -11.224  1.00 40.79           C
ATOM    893  O    VAL A 155      -2.563  -12.985  -10.489  1.00 42.48           O
ATOM    894  N    ILE A 156      -1.704  -15.029  -10.819  1.00 41.26           N
ATOM    895  CA   ILE A 156      -2.064  -15.442   -9.466  1.00 40.77           C
ATOM    896  CB   ILE A 156      -1.734  -16.942   -9.204  1.00 40.59           C
ATOM    897  CG2  ILE A 156      -0.230  -17.166   -9.205  1.00 40.53           C
ATOM    898  CG1  ILE A 156      -2.321  -17.378   -7.854  1.00 40.30           C
ATOM    899  CD1  ILE A 156      -3.831  -17.193   -7.742  1.00 39.16           C
ATOM    900  C    ILE A 156      -1.344  -14.561   -8.442  1.00 40.36           C
ATOM    901  O    ILE A 156      -1.898  -14.252   -7.391  1.00 40.94           O
ATOM    902  N    TYR A 157      -0.112  -14.155   -8.748  1.00 39.96           N
ATOM    903  CA   TYR A 157       0.630  -13.284   -7.843  1.00 39.99           C
ATOM    904  CB   TYR A 157       2.099  -13.210   -8.253  1.00 40.21           C
ATOM    905  CG   TYR A 157       2.863  -14.467   -7.916  1.00 41.76           C
ATOM    906  CD1  TYR A 157       3.727  -15.047   -8.836  1.00 43.16           C
ATOM    907  CE1  TYR A 157       4.443  -16.200   -8.528  1.00 44.08           C
ATOM    908  CD2  TYR A 157       2.731  -15.068   -6.675  1.00 42.41           C
ATOM    909  CE2  TYR A 157       3.440  -16.220   -6.355  1.00 44.14           C
ATOM    910  CZ   TYR A 157       4.300  -16.779   -7.288  1.00 45.27           C
ATOM    911  OH   TYR A 157       5.032  -17.906   -6.975  1.00 45.31           O
ATOM    912  C    TYR A 157      -0.019  -11.910   -7.919  1.00 39.78           C
ATOM    913  O    TYR A 157      -0.217  -11.244   -6.901  1.00 38.90           O
ATOM    914  N    VAL A 158      -0.364  -11.509   -9.142  1.00 39.02           N
ATOM    915  CA   VAL A 158      -1.021  -10.237   -9.387  1.00 37.59           C
ATOM    916  CB   VAL A 158      -1.334  -10.041  -10.892  1.00 38.19           C
ATOM    917  CG1  VAL A 158      -2.198   -8.805  -11.087  1.00 38.00           C
ATOM    918  CG2  VAL A 158      -0.030   -9.892  -11.687  1.00 37.77           C
ATOM    919  C    VAL A 158      -2.324  -10.185   -8.602  1.00 37.34           C
ATOM    920  O    VAL A 158      -2.610   -9.189   -7.936  1.00 37.82           O
ATOM    921  N    LYS A 159      -3.115  -11.253   -8.672  1.00 36.92           N
ATOM    922  CA   LYS A 159      -4.389  -11.287   -7.946  1.00 38.52           C
ATOM    923  CB   LYS A 159      -5.161  -12.575   -8.241  1.00 38.55           C
ATOM    924  CG   LYS A 159      -5.674  -12.700   -9.656  1.00 39.52           C
ATOM    925  CD   LYS A 159      -6.507  -13.950   -9.778  1.00 40.89           C
ATOM    926  CE   LYS A 159      -6.755  -14.328  -11.224  1.00 42.11           C
ATOM    927  NZ   LYS A 159      -7.636  -15.530  -11.284  1.00 42.40           N
ATOM    928  C    LYS A 159      -4.175  -11.189   -6.443  1.00 39.01           C
ATOM    929  O    LYS A 159      -4.871  -10.447   -5.745  1.00 39.04           O
ATOM    930  N    LEU A 160      -3.216  -11.970   -5.953  1.00 39.57           N
ATOM    931  CA   LEU A 160      -2.875  -12.009   -4.539  1.00 38.26           C
```

FIG. 2-15

| | | | | | | | | | |
|---|---|---|---|---|---|---|---|---|---|
| ATOM | 932 | CB | LEU A 160 | -1.781 | -13.049 | -4.307 | 1.00 | 38.48 | C |
| ATOM | 933 | CG | LEU A 160 | -2.221 | -14.515 | -4.371 | 1.00 | 39.58 | C |
| ATOM | 934 | CD1 | LEU A 160 | -1.031 | -15.404 | -4.707 | 1.00 | 36.72 | C |
| ATOM | 935 | CD2 | LEU A 160 | -2.841 | -14.904 | -3.027 | 1.00 | 38.57 | C |
| ATOM | 936 | C | LEU A 160 | -2.403 | -10.660 | -4.024 | 1.00 | 38.36 | C |
| ATOM | 937 | O | LEU A 160 | -2.917 | -10.153 | -3.030 | 1.00 | 38.45 | O |
| ATOM | 938 | N | TYR A 161 | -1.418 | -10.084 | -4.706 | 1.00 | 36.84 | N |
| ATOM | 939 | CA | TYR A 161 | -0.867 | -8.807 | -4.301 | 1.00 | 36.33 | C |
| ATOM | 940 | CB | TYR A 161 | 0.321 | -8.430 | -5.186 | 1.00 | 37.60 | C |
| ATOM | 941 | CG | TYR A 161 | 1.469 | -9.401 | -5.091 | 1.00 | 38.66 | C |
| ATOM | 942 | CD1 | TYR A 161 | 1.665 | -10.159 | -3.943 | 1.00 | 38.60 | C |
| ATOM | 943 | CE1 | TYR A 161 | 2.721 | -11.055 | -3.843 | 1.00 | 40.15 | C |
| ATOM | 944 | CD2 | TYR A 161 | 2.363 | -9.558 | -6.141 | 1.00 | 38.78 | C |
| ATOM | 945 | CE2 | TYR A 161 | 3.426 | -10.451 | -6.050 | 1.00 | 39.26 | C |
| ATOM | 946 | CZ | TYR A 161 | 3.599 | -11.194 | -4.901 | 1.00 | 40.58 | C |
| ATOM | 947 | OH | TYR A 161 | 4.652 | -12.081 | -4.801 | 1.00 | 43.96 | O |
| ATOM | 948 | C | TYR A 161 | -1.894 | -7.701 | -4.341 | 1.00 | 36.29 | C |
| ATOM | 949 | O | TYR A 161 | -2.052 | -6.955 | -3.372 | 1.00 | 35.64 | O |
| ATOM | 950 | N | MET A 162 | -2.596 | -7.585 | -5.460 | 1.00 | 36.04 | N |
| ATOM | 951 | CA | MET A 162 | -3.602 | -6.537 | -5.591 | 1.00 | 35.73 | C |
| ATOM | 952 | CB | MET A 162 | -4.180 | -6.523 | -7.000 | 1.00 | 34.65 | C |
| ATOM | 953 | CG | MET A 162 | -3.168 | -6.145 | -8.054 | 1.00 | 35.72 | C |
| ATOM | 954 | SD | MET A 162 | -2.395 | -4.539 | -7.720 | 1.00 | 35.74 | S |
| ATOM | 955 | CE | MET A 162 | -3.815 | -3.518 | -7.620 | 1.00 | 35.44 | C |
| ATOM | 956 | C | MET A 162 | -4.719 | -6.698 | -4.575 | 1.00 | 35.95 | C |
| ATOM | 957 | O | MET A 162 | -5.186 | -5.714 | -3.999 | 1.00 | 36.87 | O |
| ATOM | 958 | N | TYR A 163 | -5.143 | -7.936 | -4.342 | 1.00 | 34.81 | N |
| ATOM | 959 | CA | TYR A 163 | -6.214 | -8.172 | -3.392 | 1.00 | 35.01 | C |
| ATOM | 960 | CB | TYR A 163 | -6.569 | -9.650 | -3.313 | 1.00 | 35.57 | C |
| ATOM | 961 | CG | TYR A 163 | -7.614 | -9.940 | -2.260 | 1.00 | 35.19 | C |
| ATOM | 962 | CD1 | TYR A 163 | -8.964 | -9.689 | -2.508 | 1.00 | 34.90 | C |
| ATOM | 963 | CE1 | TYR A 163 | -9.933 | -9.943 | -1.542 | 1.00 | 34.20 | C |
| ATOM | 964 | CD2 | TYR A 163 | -7.254 | -10.449 | -1.018 | 1.00 | 33.71 | C |
| ATOM | 965 | CE2 | TYR A 163 | -8.210 | -10.706 | -0.044 | 1.00 | 35.07 | C |
| ATOM | 966 | CZ | TYR A 163 | -9.548 | -10.453 | -0.313 | 1.00 | 35.35 | C |
| ATOM | 967 | OH | TYR A 163 | -10.503 | -10.720 | 0.643 | 1.00 | 37.60 | O |
| ATOM | 968 | C | TYR A 163 | -5.825 | -7.709 | -2.009 | 1.00 | 35.47 | C |
| ATOM | 969 | O | TYR A 163 | -6.654 | -7.171 | -1.270 | 1.00 | 36.06 | O |
| ATOM | 970 | N | GLN A 164 | -4.564 | -7.936 | -1.651 | 1.00 | 35.10 | N |
| ATOM | 971 | CA | GLN A 164 | -4.071 | -7.556 | -0.335 | 1.00 | 33.06 | C |
| ATOM | 972 | CB | GLN A 164 | -2.760 | -8.288 | -0.033 | 1.00 | 33.04 | C |
| ATOM | 973 | CG | GLN A 164 | -2.923 | -9.792 | 0.107 | 1.00 | 33.49 | C |
| ATOM | 974 | CD | GLN A 164 | -1.660 | -10.473 | 0.612 | 1.00 | 36.15 | C |
| ATOM | 975 | OE1 | GLN A 164 | -1.313 | -10.382 | 1.797 | 1.00 | 35.65 | O |
| ATOM | 976 | NE2 | GLN A 164 | -0.959 | -11.153 | -0.290 | 1.00 | 34.16 | N |
| ATOM | 977 | C | GLN A 164 | -3.897 | -6.051 | -0.205 | 1.00 | 31.59 | C |
| ATOM | 978 | O | GLN A 164 | -4.192 | -5.483 | 0.843 | 1.00 | 31.84 | O |
| ATOM | 979 | N | LEU A 165 | -3.428 | -5.400 | -1.265 | 1.00 | 30.09 | N |
| ATOM | 980 | CA | LEU A 165 | -3.261 | -3.954 | -1.220 | 1.00 | 28.36 | C |
| ATOM | 981 | CB | LEU A 165 | -2.587 | -3.435 | -2.489 | 1.00 | 26.50 | C |
| ATOM | 982 | CG | LEU A 165 | -2.793 | -1.956 | -2.832 | 1.00 | 24.60 | C |
| ATOM | 983 | CD1 | LEU A 165 | -2.306 | -1.049 | -1.718 | 1.00 | 23.95 | C |
| ATOM | 984 | CD2 | LEU A 165 | -2.075 | -1.660 | -4.122 | 1.00 | 22.60 | C |
| ATOM | 985 | C | LEU A 165 | -4.624 | -3.299 | -1.068 | 1.00 | 28.89 | C |
| ATOM | 986 | O | LEU A 165 | -4.813 | -2.428 | -0.217 | 1.00 | 29.03 | O |
| ATOM | 987 | N | PHE A 166 | -5.573 | -3.722 | -1.896 | 1.00 | 29.25 | N |
| ATOM | 988 | CA | PHE A 166 | -6.919 | -3.156 | -1.842 | 1.00 | 30.67 | C |
| ATOM | 989 | CB | PHE A 166 | -7.833 | -3.824 | -2.882 | 1.00 | 28.68 | C |
| ATOM | 990 | CG | PHE A 166 | -7.738 | -3.201 | -4.251 | 1.00 | 27.88 | C |
| ATOM | 991 | CD1 | PHE A 166 | -7.968 | -1.833 | -4.417 | 1.00 | 26.07 | C |
| ATOM | 992 | CD2 | PHE A 166 | -7.413 | -3.962 | -5.366 | 1.00 | 24.46 | C |
| ATOM | 993 | CE1 | PHE A 166 | -7.875 | -1.235 | -5.667 | 1.00 | 24.30 | C |
| ATOM | 994 | CE2 | PHE A 166 | -7.318 | -3.367 | -6.623 | 1.00 | 25.24 | C |
| ATOM | 995 | CZ | PHE A 166 | -7.551 | -1.998 | -6.772 | 1.00 | 25.96 | C |
| ATOM | 996 | C | PHE A 166 | -7.531 | -3.260 | -0.447 | 1.00 | 31.68 | C |
| ATOM | 997 | O | PHE A 166 | -8.172 | -2.327 | 0.033 | 1.00 | 31.65 | O |
| ATOM | 998 | N | ARG A 167 | -7.314 | -4.390 | 0.209 | 1.00 | 32.35 | N |

FIG. 2-16

| | | | | | | | | | |
|---|---|---|---|---|---|---|---|---|---|
| ATOM | 999 | CA | ARG | A | 167 | -7.855 | -4.587 | 1.534 | 1.00 33.04 | C |
| ATOM | 1000 | CB | ARG | A | 167 | -7.590 | -6.015 | 1.982 | 1.00 32.14 | C |
| ATOM | 1001 | CG | ARG | A | 167 | -8.605 | -6.515 | 2.960 | 1.00 32.68 | C |
| ATOM | 1002 | CD | ARG | A | 167 | -8.212 | -7.850 | 3.505 | 1.00 33.09 | C |
| ATOM | 1003 | NE | ARG | A | 167 | -8.841 | -8.058 | 4.795 | 1.00 34.29 | N |
| ATOM | 1004 | CZ | ARG | A | 167 | -8.467 | -8.988 | 5.661 | 1.00 35.47 | C |
| ATOM | 1005 | NH1 | ARG | A | 167 | -7.464 | -9.802 | 5.365 | 1.00 35.82 | N |
| ATOM | 1006 | NH2 | ARG | A | 167 | -9.086 | -9.091 | 6.830 | 1.00 36.15 | N |
| ATOM | 1007 | C | ARG | A | 167 | -7.263 | -3.596 | 2.542 | 1.00 34.56 | C |
| ATOM | 1008 | O | ARG | A | 167 | -7.981 | -3.056 | 3.384 | 1.00 35.05 | O |
| ATOM | 1009 | N | SER | A | 168 | -5.956 | -3.356 | 2.449 | 1.00 35.08 | N |
| ATOM | 1010 | CA | SER | A | 168 | -5.281 | -2.432 | 3.359 | 1.00 35.46 | C |
| ATOM | 1011 | CB | SER | A | 168 | -3.759 | -2.470 | 3.152 | 1.00 35.97 | C |
| ATOM | 1012 | OG | SER | A | 168 | -3.338 | -1.604 | 2.109 | 1.00 36.24 | O |
| ATOM | 1013 | C | SER | A | 168 | -5.783 | -1.008 | 3.135 | 1.00 35.40 | C |
| ATOM | 1014 | O | SER | A | 168 | -5.849 | -0.201 | 4.065 | 1.00 36.62 | O |
| ATOM | 1015 | N | LEU | A | 169 | -6.126 | -0.703 | 1.892 | 1.00 34.23 | N |
| ATOM | 1016 | CA | LEU | A | 169 | -6.625 | 0.612 | 1.551 | 1.00 33.47 | C |
| ATOM | 1017 | CB | LEU | A | 169 | -6.577 | 0.812 | 0.027 | 1.00 31.68 | C |
| ATOM | 1018 | CG | LEU | A | 169 | -5.500 | 1.760 | -0.542 | 1.00 32.15 | C |
| ATOM | 1019 | CD1 | LEU | A | 169 | -4.281 | 1.852 | 0.367 | 1.00 33.68 | C |
| ATOM | 1020 | CD2 | LEU | A | 169 | -5.095 | 1.286 | -1.921 | 1.00 31.87 | C |
| ATOM | 1021 | C | LEU | A | 169 | -8.048 | 0.749 | 2.106 | 1.00 34.50 | C |
| ATOM | 1022 | O | LEU | A | 169 | -8.445 | 1.820 | 2.579 | 1.00 34.76 | O |
| ATOM | 1023 | N | ALA | A | 170 | -8.811 | -0.341 | 2.077 | 1.00 33.93 | N |
| ATOM | 1024 | CA | ALA | A | 170 | -10.167 | -0.308 | 2.617 | 1.00 33.77 | C |
| ATOM | 1025 | CB | ALA | A | 170 | -10.852 | -1.653 | 2.421 | 1.00 30.92 | C |
| ATOM | 1026 | C | ALA | A | 170 | -10.046 | 0.010 | 4.106 | 1.00 34.57 | C |
| ATOM | 1027 | O | ALA | A | 170 | -10.681 | 0.932 | 4.623 | 1.00 35.14 | O |
| ATOM | 1028 | N | TYR | A | 171 | -9.197 | -0.752 | 4.781 | 1.00 36.13 | N |
| ATOM | 1029 | CA | TYR | A | 171 | -8.966 | -0.569 | 6.201 | 1.00 38.49 | C |
| ATOM | 1030 | CB | TYR | A | 171 | -7.918 | -1.563 | 6.684 | 1.00 41.53 | C |
| ATOM | 1031 | CG | TYR | A | 171 | -7.462 | -1.335 | 8.101 | 1.00 43.54 | C |
| ATOM | 1032 | CD1 | TYR | A | 171 | -8.219 | -1.790 | 9.177 | 1.00 44.28 | C |
| ATOM | 1033 | CE1 | TYR | A | 171 | -7.811 | -1.572 | 10.485 | 1.00 44.52 | C |
| ATOM | 1034 | CD2 | TYR | A | 171 | -6.279 | -0.655 | 8.362 | 1.00 43.86 | C |
| ATOM | 1035 | CE2 | TYR | A | 171 | -5.859 | -0.428 | 9.663 | 1.00 46.80 | C |
| ATOM | 1036 | CZ | TYR | A | 171 | -6.634 | -0.893 | 10.724 | 1.00 47.02 | C |
| ATOM | 1037 | OH | TYR | A | 171 | -6.228 | -0.663 | 12.020 | 1.00 48.43 | O |
| ATOM | 1038 | C | TYR | A | 171 | -8.524 | 0.852 | 6.575 | 1.00 39.02 | C |
| ATOM | 1039 | O | TYR | A | 171 | -9.050 | 1.433 | 7.515 | 1.00 38.61 | O |
| ATOM | 1040 | N | ILE | A | 172 | -7.556 | 1.417 | 5.863 | 1.00 38.84 | N |
| ATOM | 1041 | CA | ILE | A | 172 | -7.128 | 2.755 | 6.214 | 1.00 40.00 | C |
| ATOM | 1042 | CB | ILE | A | 172 | -5.771 | 3.122 | 5.589 | 1.00 40.89 | C |
| ATOM | 1043 | CG2 | ILE | A | 172 | -4.647 | 2.459 | 6.377 | 1.00 40.72 | C |
| ATOM | 1044 | CG1 | ILE | A | 172 | -5.750 | 2.734 | 4.115 | 1.00 41.88 | C |
| ATOM | 1045 | CD1 | ILE | A | 172 | -4.494 | 3.189 | 3.381 | 1.00 42.41 | C |
| ATOM | 1046 | C | ILE | A | 172 | -8.144 | 3.820 | 5.834 | 1.00 41.46 | C |
| ATOM | 1047 | O | ILE | A | 172 | -8.306 | 4.813 | 6.548 | 1.00 42.27 | O |
| ATOM | 1048 | N | HIS | A | 173 | -8.843 | 3.632 | 4.720 | 1.00 40.38 | N |
| ATOM | 1049 | CA | HIS | A | 173 | -9.835 | 4.623 | 4.312 | 1.00 38.35 | C |
| ATOM | 1050 | CB | HIS | A | 173 | -10.325 | 4.321 | 2.900 | 1.00 37.13 | C |
| ATOM | 1051 | CG | HIS | A | 173 | -9.312 | 4.648 | 1.853 | 1.00 36.44 | C |
| ATOM | 1052 | CD2 | HIS | A | 173 | -8.088 | 5.219 | 1.953 | 1.00 36.35 | C |
| ATOM | 1053 | ND1 | HIS | A | 173 | -9.500 | 4.382 | 0.516 | 1.00 36.91 | N |
| ATOM | 1054 | CE1 | HIS | A | 173 | -8.436 | 4.771 | -0.162 | 1.00 35.34 | C |
| ATOM | 1055 | NE2 | HIS | A | 173 | -7.566 | 5.282 | 0.688 | 1.00 36.10 | N |
| ATOM | 1056 | C | HIS | A | 173 | -10.985 | 4.696 | 5.294 | 1.00 38.25 | C |
| ATOM | 1057 | O | HIS | A | 173 | -11.587 | 5.752 | 5.468 | 1.00 38.49 | O |
| ATOM | 1058 | N | SER | A | 174 | -11.249 | 3.583 | 5.971 | 1.00 39.57 | N |
| ATOM | 1059 | CA | SER | A | 174 | -12.322 | 3.508 | 6.955 | 1.00 40.52 | C |
| ATOM | 1060 | CB | SER | A | 174 | -12.407 | 2.088 | 7.504 | 1.00 40.03 | C |
| ATOM | 1061 | OG | SER | A | 174 | -11.320 | 1.838 | 8.371 | 1.00 41.62 | O |
| ATOM | 1062 | C | SER | A | 174 | -12.109 | 4.502 | 8.104 | 1.00 41.07 | C |
| ATOM | 1063 | O | SER | A | 174 | -13.027 | 4.764 | 8.889 | 1.00 41.29 | O |
| ATOM | 1064 | N | PHE | A | 175 | -10.895 | 5.047 | 8.193 | 1.00 41.98 | N |
| ATOM | 1065 | CA | PHE | A | 175 | -10.540 | 6.019 | 9.229 | 1.00 42.87 | C |

FIG. 2-17

| | | | | | | | | | |
|---|---|---|---|---|---|---|---|---|---|
| ATOM | 1066 | CB | PHE A 175 | -9.215 | 5.629 | 9.901 | 1.00 | 45.52 | C |
| ATOM | 1067 | CG | PHE A 175 | -9.294 | 4.375 | 10.724 | 1.00 | 48.85 | C |
| ATOM | 1068 | CD1 | PHE A 175 | -8.154 | 3.622 | 10.980 | 1.00 | 48.54 | C |
| ATOM | 1069 | CD2 | PHE A 175 | -10.518 | 3.939 | 11.234 | 1.00 | 50.19 | C |
| ATOM | 1070 | CE1 | PHE A 175 | -8.230 | 2.446 | 11.726 | 1.00 | 50.79 | C |
| ATOM | 1071 | CE2 | PHE A 175 | -10.603 | 2.762 | 11.984 | 1.00 | 50.53 | C |
| ATOM | 1072 | CZ | PHE A 175 | -9.458 | 2.015 | 12.230 | 1.00 | 49.97 | C |
| ATOM | 1073 | C | PHE A 175 | -10.403 | 7.424 | 8.649 | 1.00 | 42.24 | C |
| ATOM | 1074 | O | PHE A 175 | -10.155 | 8.385 | 9.378 | 1.00 | 43.53 | O |
| ATOM | 1075 | N | GLY A 176 | -10.564 | 7.541 | 7.336 | 1.00 | 40.87 | N |
| ATOM | 1076 | CA | GLY A 176 | -10.443 | 8.839 | 6.702 | 1.00 | 40.36 | C |
| ATOM | 1077 | C | GLY A 176 | -9.012 | 9.116 | 6.279 | 1.00 | 40.14 | C |
| ATOM | 1078 | O | GLY A 176 | -8.689 | 10.176 | 5.736 | 1.00 | 41.67 | O |
| ATOM | 1079 | N | ILE A 177 | -8.147 | 8.147 | 6.541 | 1.00 | 38.13 | N |
| ATOM | 1080 | CA | ILE A 177 | -6.743 | 8.258 | 6.213 | 1.00 | 36.79 | C |
| ATOM | 1081 | CB | ILE A 177 | -5.903 | 7.317 | 7.080 | 1.00 | 38.17 | C |
| ATOM | 1082 | CG2 | ILE A 177 | -4.426 | 7.637 | 6.908 | 1.00 | 36.28 | C |
| ATOM | 1083 | CG1 | ILE A 177 | -6.323 | 7.448 | 8.539 | 1.00 | 37.63 | C |
| ATOM | 1084 | CD1 | ILE A 177 | -5.932 | 6.270 | 9.376 | 1.00 | 40.81 | C |
| ATOM | 1085 | C | ILE A 177 | -6.485 | 7.888 | 4.764 | 1.00 | 36.12 | C |
| ATOM | 1086 | O | ILE A 177 | -6.917 | 6.834 | 4.291 | 1.00 | 35.90 | O |
| ATOM | 1087 | N | CYS A 178 | -5.772 | 8.766 | 4.067 | 1.00 | 34.06 | N |
| ATOM | 1088 | CA | CYS A 178 | -5.415 | 8.547 | 2.676 | 1.00 | 33.14 | C |
| ATOM | 1089 | CB | CYS A 178 | -5.850 | 9.735 | 1.818 | 1.00 | 33.28 | C |
| ATOM | 1090 | SG | CYS A 178 | -5.555 | 9.533 | 0.052 | 1.00 | 34.81 | S |
| ATOM | 1091 | C | CYS A 178 | -3.900 | 8.404 | 2.634 | 1.00 | 33.71 | C |
| ATOM | 1092 | O | CYS A 178 | -3.182 | 9.234 | 3.187 | 1.00 | 34.76 | O |
| ATOM | 1093 | N | HIS A 179 | -3.421 | 7.348 | 1.982 | 1.00 | 32.52 | N |
| ATOM | 1094 | CA | HIS A 179 | -1.993 | 7.078 | 1.890 | 1.00 | 30.59 | C |
| ATOM | 1095 | CB | HIS A 179 | -1.780 | 5.674 | 1.336 | 1.00 | 29.91 | C |
| ATOM | 1096 | CG | HIS A 179 | -0.361 | 5.209 | 1.402 | 1.00 | 30.41 | C |
| ATOM | 1097 | CD2 | HIS A 179 | 0.246 | 4.312 | 2.216 | 1.00 | 32.11 | C |
| ATOM | 1098 | ND1 | HIS A 179 | 0.617 | 5.678 | 0.553 | 1.00 | 29.56 | N |
| ATOM | 1099 | CE1 | HIS A 179 | 1.763 | 5.086 | 0.839 | 1.00 | 31.83 | C |
| ATOM | 1100 | NE2 | HIS A 179 | 1.565 | 4.253 | 1.842 | 1.00 | 31.05 | N |
| ATOM | 1101 | C | HIS A 179 | -1.223 | 8.096 | 1.055 | 1.00 | 30.96 | C |
| ATOM | 1102 | O | HIS A 179 | -0.090 | 8.460 | 1.387 | 1.00 | 31.84 | O |
| ATOM | 1103 | N | ARG A 180 | -1.838 | 8.547 | -0.030 | 1.00 | 30.32 | N |
| ATOM | 1104 | CA | ARG A 180 | -1.234 | 9.530 | -0.920 | 1.00 | 29.78 | C |
| ATOM | 1105 | CB | ARG A 180 | -1.144 | 10.876 | -0.211 | 1.00 | 30.61 | C |
| ATOM | 1106 | CG | ARG A 180 | -2.477 | 11.364 | 0.289 | 1.00 | 29.27 | C |
| ATOM | 1107 | CD | ARG A 180 | -2.277 | 12.395 | 1.356 | 1.00 | 31.78 | C |
| ATOM | 1108 | NE | ARG A 180 | -2.002 | 13.716 | 0.827 | 1.00 | 32.13 | N |
| ATOM | 1109 | CZ | ARG A 180 | -1.451 | 14.685 | 1.546 | 1.00 | 33.48 | C |
| ATOM | 1110 | NH1 | ARG A 180 | -1.114 | 14.457 | 2.805 | 1.00 | 33.76 | N |
| ATOM | 1111 | NH2 | ARG A 180 | -1.259 | 15.886 | 1.020 | 1.00 | 36.08 | N |
| ATOM | 1112 | C | ARG A 180 | 0.138 | 9.157 | -1.487 | 1.00 | 29.82 | C |
| ATOM | 1113 | O | ARG A 180 | 0.825 | 10.013 | -2.049 | 1.00 | 29.25 | O |
| ATOM | 1114 | N | ASP A 181 | 0.547 | 7.899 | -1.333 | 1.00 | 30.10 | N |
| ATOM | 1115 | CA | ASP A 181 | 1.825 | 7.467 | -1.893 | 1.00 | 30.86 | C |
| ATOM | 1116 | CB | ASP A 181 | 2.980 | 7.781 | -0.950 | 1.00 | 32.43 | C |
| ATOM | 1117 | CG | ASP A 181 | 4.330 | 7.704 | -1.651 | 1.00 | 33.40 | C |
| ATOM | 1118 | OD1 | ASP A 181 | 4.357 | 7.782 | -2.895 | 1.00 | 32.61 | O |
| ATOM | 1119 | OD2 | ASP A 181 | 5.363 | 7.571 | -0.962 | 1.00 | 37.08 | O |
| ATOM | 1120 | C | ASP A 181 | 1.870 | 5.990 | -2.298 | 1.00 | 31.36 | C |
| ATOM | 1121 | O | ASP A 181 | 2.886 | 5.311 | -2.127 | 1.00 | 29.91 | O |
| ATOM | 1122 | N | ILE A 182 | 0.749 | 5.508 | -2.843 | 1.00 | 31.31 | N |
| ATOM | 1123 | CA | ILE A 182 | 0.634 | 4.133 | -3.304 | 1.00 | 29.91 | C |
| ATOM | 1124 | CB | ILE A 182 | -0.824 | 3.771 | -3.658 | 1.00 | 27.35 | C |
| ATOM | 1125 | CG2 | ILE A 182 | -0.895 | 2.371 | -4.265 | 1.00 | 24.41 | C |
| ATOM | 1126 | CG1 | ILE A 182 | -1.684 | 3.843 | -2.396 | 1.00 | 25.83 | C |
| ATOM | 1127 | CD1 | ILE A 182 | -1.154 | 3.003 | -1.250 | 1.00 | 25.80 | C |
| ATOM | 1128 | C | ILE A 182 | 1.513 | 3.942 | -4.531 | 1.00 | 30.16 | C |
| ATOM | 1129 | O | ILE A 182 | 1.366 | 4.640 | -5.536 | 1.00 | 28.99 | O |
| ATOM | 1130 | N | LYS A 183 | 2.448 | 3.003 | -4.412 | 1.00 | 30.02 | N |
| ATOM | 1131 | CA | LYS A 183 | 3.379 | 2.669 | -5.481 | 1.00 | 30.49 | C |
| ATOM | 1132 | CB | LYS A 183 | 4.407 | 3.792 | -5.658 | 1.00 | 31.00 | C |

FIG. 2-18

```
ATOM   1133  CG   LYS A 183       5.290   4.034  -4.452  1.00 32.97           C
ATOM   1134  CD   LYS A 183       6.320   5.100  -4.758  1.00 35.22           C
ATOM   1135  CE   LYS A 183       7.151   5.419  -3.535  1.00 37.22           C
ATOM   1136  NZ   LYS A 183       8.231   6.387  -3.845  1.00 40.88           N
ATOM   1137  C    LYS A 183       4.093   1.342  -5.165  1.00 30.08           C
ATOM   1138  O    LYS A 183       4.263   0.984  -4.004  1.00 30.49           O
ATOM   1139  N    PRO A 184       4.520   0.606  -6.203  1.00 29.30           N
ATOM   1140  CD   PRO A 184       4.498   1.070  -7.605  1.00 28.98           C
ATOM   1141  CA   PRO A 184       5.216  -0.683  -6.094  1.00 28.43           C
ATOM   1142  CB   PRO A 184       5.752  -0.904  -7.507  1.00 30.01           C
ATOM   1143  CG   PRO A 184       4.738  -0.200  -8.366  1.00 30.25           C
ATOM   1144  C    PRO A 184       6.329  -0.741  -5.055  1.00 28.20           C
ATOM   1145  O    PRO A 184       6.492  -1.756  -4.388  1.00 27.25           O
ATOM   1146  N    GLN A 185       7.090   0.343  -4.923  1.00 29.81           N
ATOM   1147  CA   GLN A 185       8.199   0.390  -3.970  1.00 30.32           C
ATOM   1148  CB   GLN A 185       9.078   1.625  -4.213  1.00 31.28           C
ATOM   1149  CG   GLN A 185       9.704   1.702  -5.602  1.00 33.65           C
ATOM   1150  CD   GLN A 185       8.789   2.361  -6.622  1.00 35.78           C
ATOM   1151  OE1  GLN A 185       7.570   2.199  -6.586  1.00 33.89           O
ATOM   1152  NE2  GLN A 185       9.382   3.101  -7.547  1.00 39.22           N
ATOM   1153  C    GLN A 185       7.743   0.379  -2.516  1.00 29.59           C
ATOM   1154  O    GLN A 185       8.540   0.110  -1.616  1.00 30.45           O
ATOM   1155  N    ASN A 186       6.467   0.677  -2.284  1.00 28.94           N
ATOM   1156  CA   ASN A 186       5.933   0.693  -0.931  1.00 27.85           C
ATOM   1157  CB   ASN A 186       5.156   1.984  -0.660  1.00 26.33           C
ATOM   1158  CG   ASN A 186       6.051   3.208  -0.630  1.00 26.71           C
ATOM   1159  OD1  ASN A 186       7.194   3.153  -0.179  1.00 27.50           O
ATOM   1160  ND2  ASN A 186       5.526   4.325  -1.101  1.00 27.38           N
ATOM   1161  C    ASN A 186       5.048  -0.508  -0.661  1.00 29.00           C
ATOM   1162  O    ASN A 186       4.243  -0.492   0.264  1.00 28.54           O
ATOM   1163  N    LEU A 187       5.195  -1.553  -1.467  1.00 29.41           N
ATOM   1164  CA   LEU A 187       4.412  -2.765  -1.266  1.00 31.28           C
ATOM   1165  CB   LEU A 187       3.627  -3.126  -2.535  1.00 30.32           C
ATOM   1166  CG   LEU A 187       2.549  -2.146  -3.032  1.00 28.96           C
ATOM   1167  CD1  LEU A 187       1.990  -2.691  -4.331  1.00 29.97           C
ATOM   1168  CD2  LEU A 187       1.438  -1.953  -2.012  1.00 27.12           C
ATOM   1169  C    LEU A 187       5.394  -3.876  -0.901  1.00 32.57           C
ATOM   1170  O    LEU A 187       6.041  -4.463  -1.767  1.00 30.34           O
ATOM   1171  N    LEU A 188       5.512  -4.137   0.395  1.00 35.35           N
ATOM   1172  CA   LEU A 188       6.418  -5.159   0.893  1.00 39.19           C
ATOM   1173  CB   LEU A 188       6.879  -4.801   2.302  1.00 38.57           C
ATOM   1174  CG   LEU A 188       7.217  -3.330   2.522  1.00 38.90           C
ATOM   1175  CD1  LEU A 188       7.441  -3.111   3.990  1.00 40.18           C
ATOM   1176  CD2  LEU A 188       8.432  -2.923   1.700  1.00 37.71           C
ATOM   1177  C    LEU A 188       5.707  -6.500   0.924  1.00 41.46           C
ATOM   1178  O    LEU A 188       4.533  -6.582   1.290  1.00 42.51           O
ATOM   1179  N    LEU A 189       6.427  -7.553   0.559  1.00 42.65           N
ATOM   1180  CA   LEU A 189       5.847  -8.881   0.534  1.00 46.06           C
ATOM   1181  CB   LEU A 189       5.352  -9.220  -0.882  1.00 47.01           C
ATOM   1182  CG   LEU A 189       5.895  -8.343  -2.008  1.00 47.19           C
ATOM   1183  CD1  LEU A 189       7.394  -8.166  -1.811  1.00 49.46           C
ATOM   1184  CD2  LEU A 189       5.606  -8.966  -3.368  1.00 47.00           C
ATOM   1185  C    LEU A 189       6.847  -9.921   0.973  1.00 46.63           C
ATOM   1186  O    LEU A 189       8.045  -9.778   0.759  1.00 46.97           O
ATOM   1187  N    ASP A 190       6.342 -10.955   1.625  1.00 47.41           N
ATOM   1188  CA   ASP A 190       7.180 -12.050   2.061  1.00 49.42           C
ATOM   1189  CB   ASP A 190       6.652 -12.653   3.361  1.00 50.80           C
ATOM   1190  CG   ASP A 190       7.528 -13.785   3.872  1.00 51.73           C
ATOM   1191  OD1  ASP A 190       7.718 -14.768   3.112  1.00 51.87           O
ATOM   1192  OD2  ASP A 190       8.016 -13.689   5.022  1.00 52.74           O
ATOM   1193  C    ASP A 190       7.092 -13.067   0.937  1.00 49.47           C
ATOM   1194  O    ASP A 190       6.017 -13.583   0.641  1.00 49.03           O
ATOM   1195  N    PRO A 191       8.223 -13.348   0.283  1.00 49.70           N
ATOM   1196  CD   PRO A 191       9.580 -12.943   0.691  1.00 50.64           C
ATOM   1197  CA   PRO A 191       8.279 -14.304  -0.827  1.00 50.28           C
ATOM   1198  CB   PRO A 191       9.762 -14.319  -1.191  1.00 50.88           C
ATOM   1199  CG   PRO A 191      10.427 -14.076   0.138  1.00 51.55           C
```

FIG. 2-19

| ATOM | 1200 | C   | PRO A 191 |  7.727 | -15.709 | -0.596 | 1.00 | 49.47 | C |
| ATOM | 1201 | O   | PRO A 191 |  7.123 | -16.276 | -1.501 | 1.00 | 50.39 | O |
| ATOM | 1202 | N   | ASP A 192 |  7.927 | -16.285 |  0.585 | 1.00 | 47.75 | N |
| ATOM | 1203 | CA  | ASP A 192 |  7.420 | -17.633 |  0.812 | 1.00 | 46.07 | C |
| ATOM | 1204 | CB  | ASP A 192 |  8.217 | -18.357 |  1.906 | 1.00 | 47.02 | C |
| ATOM | 1205 | CG  | ASP A 192 |  9.733 | -18.187 |  1.760 | 1.00 | 48.63 | C |
| ATOM | 1206 | OD1 | ASP A 192 | 10.272 | -18.169 |  0.632 | 1.00 | 48.08 | O |
| ATOM | 1207 | OD2 | ASP A 192 | 10.403 | -18.088 |  2.803 | 1.00 | 51.80 | O |
| ATOM | 1208 | C   | ASP A 192 |  5.944 | -17.664 |  1.178 | 1.00 | 45.05 | C |
| ATOM | 1209 | O   | ASP A 192 |  5.231 | -18.576 |  0.767 | 1.00 | 46.63 | O |
| ATOM | 1210 | N   | THR A 193 |  5.473 | -16.675 |  1.936 | 1.00 | 42.71 | N |
| ATOM | 1211 | CA  | THR A 193 |  4.066 | -16.643 |  2.348 | 1.00 | 40.59 | C |
| ATOM | 1212 | CB  | THR A 193 |  3.898 | -16.060 |  3.775 | 1.00 | 40.05 | C |
| ATOM | 1213 | OG1 | THR A 193 |  4.573 | -14.800 |  3.870 | 1.00 | 39.50 | O |
| ATOM | 1214 | CG2 | THR A 193 |  4.461 | -17.019 |  4.813 | 1.00 | 39.24 | C |
| ATOM | 1215 | C   | THR A 193 |  3.165 | -15.860 |  1.400 | 1.00 | 39.44 | C |
| ATOM | 1216 | O   | THR A 193 |  1.954 | -16.079 |  1.356 | 1.00 | 38.60 | O |
| ATOM | 1217 | N   | ALA A 194 |  3.766 | -14.950 |  0.645 | 1.00 | 39.08 | N |
| ATOM | 1218 | CA  | ALA A 194 |  3.037 | -14.132 | -0.319 | 1.00 | 39.27 | C |
| ATOM | 1219 | CB  | ALA A 194 |  2.192 | -15.021 | -1.246 | 1.00 | 38.72 | C |
| ATOM | 1220 | C   | ALA A 194 |  2.154 | -13.054 |  0.307 | 1.00 | 39.21 | C |
| ATOM | 1221 | O   | ALA A 194 |  1.244 | -12.537 | -0.353 | 1.00 | 39.50 | O |
| ATOM | 1222 | N   | VAL A 195 |  2.400 | -12.704 |  1.567 | 1.00 | 37.15 | N |
| ATOM | 1223 | CA  | VAL A 195 |  1.586 | -11.661 |  2.170 | 1.00 | 35.67 | C |
| ATOM | 1224 | CB  | VAL A 195 |  1.460 | -11.815 |  3.713 | 1.00 | 37.17 | C |
| ATOM | 1225 | CG1 | VAL A 195 |  1.691 | -13.260 |  4.115 | 1.00 | 34.84 | C |
| ATOM | 1226 | CG2 | VAL A 195 |  2.401 | -10.869 |  4.429 | 1.00 | 38.47 | C |
| ATOM | 1227 | C   | VAL A 195 |  2.224 | -10.325 |  1.829 | 1.00 | 33.78 | C |
| ATOM | 1228 | O   | VAL A 195 |  3.444 | -10.200 |  1.777 | 1.00 | 34.23 | O |
| ATOM | 1229 | N   | LEU A 196 |  1.396 |  -9.334 |  1.563 | 1.00 | 32.46 | N |
| ATOM | 1230 | CA  | LEU A 196 |  1.894 |  -8.019 |  1.224 | 1.00 | 31.84 | C |
| ATOM | 1231 | CB  | LEU A 196 |  1.233 |  -7.560 | -0.084 | 1.00 | 29.72 | C |
| ATOM | 1232 | CG  | LEU A 196 |  1.246 |  -6.099 | -0.526 | 1.00 | 27.20 | C |
| ATOM | 1233 | CD1 | LEU A 196 |  1.141 |  -6.028 | -2.036 | 1.00 | 25.69 | C |
| ATOM | 1234 | CD2 | LEU A 196 |  0.122 |  -5.352 |  0.156 | 1.00 | 22.70 | C |
| ATOM | 1235 | C   | LEU A 196 |  1.564 |  -7.073 |  2.375 | 1.00 | 31.74 | C |
| ATOM | 1236 | O   | LEU A 196 |  0.689 |  -7.363 |  3.198 | 1.00 | 31.83 | O |
| ATOM | 1237 | N   | LYS A 197 |  2.274 |  -5.952 |  2.442 | 1.00 | 31.33 | N |
| ATOM | 1238 | CA  | LYS A 197 |  2.029 |  -4.953 |  3.479 | 1.00 | 30.54 | C |
| ATOM | 1239 | CB  | LYS A 197 |  2.944 |  -5.156 |  4.690 | 1.00 | 32.33 | C |
| ATOM | 1240 | CG  | LYS A 197 |  2.759 |  -6.481 |  5.394 | 1.00 | 34.61 | C |
| ATOM | 1241 | CD  | LYS A 197 |  3.623 |  -6.564 |  6.623 | 1.00 | 36.09 | C |
| ATOM | 1242 | CE  | LYS A 197 |  3.636 |  -7.981 |  7.153 | 1.00 | 36.80 | C |
| ATOM | 1243 | NZ  | LYS A 197 |  2.248 |  -8.494 |  7.318 | 1.00 | 39.55 | N |
| ATOM | 1244 | C   | LYS A 197 |  2.281 |  -3.580 |  2.907 | 1.00 | 29.61 | C |
| ATOM | 1245 | O   | LYS A 197 |  3.298 |  -3.345 |  2.266 | 1.00 | 28.04 | O |
| ATOM | 1246 | N   | LEU A 198 |  1.331 |  -2.680 |  3.130 | 1.00 | 29.95 | N |
| ATOM | 1247 | CA  | LEU A 198 |  1.447 |  -1.314 |  2.669 | 1.00 | 28.79 | C |
| ATOM | 1248 | CB  | LEU A 198 |  0.102 |  -0.607 |  2.777 | 1.00 | 29.35 | C |
| ATOM | 1249 | CG  | LEU A 198 | -0.307 |   0.357 |  1.657 | 1.00 | 32.43 | C |
| ATOM | 1250 | CD1 | LEU A 198 | -1.344 |   1.334 |  2.209 | 1.00 | 33.14 | C |
| ATOM | 1251 | CD2 | LEU A 198 |  0.890 |   1.110 |  1.109 | 1.00 | 31.16 | C |
| ATOM | 1252 | C   | LEU A 198 |  2.415 |  -0.699 |  3.658 | 1.00 | 29.38 | C |
| ATOM | 1253 | O   | LEU A 198 |  2.327 |  -0.978 |  4.855 | 1.00 | 30.81 | O |
| ATOM | 1254 | N   | CYS A 199 |  3.343 |   0.119 |  3.183 | 1.00 | 28.99 | N |
| ATOM | 1255 | CA  | CYS A 199 |  4.291 |   0.737 |  4.094 | 1.00 | 30.94 | C |
| ATOM | 1256 | CB  | CYS A 199 |  5.630 |  -0.011 |  4.075 | 1.00 | 29.54 | C |
| ATOM | 1257 | SG  | CYS A 199 |  6.739 |   0.416 |  2.692 | 1.00 | 31.32 | S |
| ATOM | 1258 | C   | CYS A 199 |  4.509 |   2.205 |  3.751 | 1.00 | 31.60 | C |
| ATOM | 1259 | O   | CYS A 199 |  3.936 |   2.723 |  2.793 | 1.00 | 31.06 | O |
| ATOM | 1260 | N   | ASP A 200 |  5.338 |   2.866 |  4.554 | 1.00 | 31.25 | N |
| ATOM | 1261 | CA  | ASP A 200 |  5.661 |   4.275 |  4.377 | 1.00 | 31.41 | C |
| ATOM | 1262 | CB  | ASP A 200 |  6.411 |   4.499 |  3.070 | 1.00 | 33.09 | C |
| ATOM | 1263 | CG  | ASP A 200 |  6.859 |   5.935 |  2.904 | 1.00 | 36.04 | C |
| ATOM | 1264 | OD1 | ASP A 200 |  6.678 |   6.723 |  3.853 | 1.00 | 38.27 | O |
| ATOM | 1265 | OD2 | ASP A 200 |  7.401 |   6.280 |  1.834 | 1.00 | 37.07 | O |
| ATOM | 1266 | C   | ASP A 200 |  4.459 |   5.211 |  4.421 | 1.00 | 32.08 | C |

FIG. 2-20

| | | | | | | | | | |
|---|---|---|---|---|---|---|---|---|---|
| ATOM | 1267 | O | ASP | A | 200 | 3.914 | 5.588 | 3.387 | 1.00 31.49 | O |
| ATOM | 1268 | N | PHE | A | 201 | 4.057 | 5.596 | 5.626 | 1.00 31.39 | N |
| ATOM | 1269 | CA | PHE | A | 201 | 2.935 | 6.495 | 5.773 | 1.00 30.98 | C |
| ATOM | 1270 | CB | PHE | A | 201 | 2.064 | 6.057 | 6.960 | 1.00 30.27 | C |
| ATOM | 1271 | CG | PHE | A | 201 | 1.219 | 4.835 | 6.676 | 1.00 29.20 | C |
| ATOM | 1272 | CD1 | PHE | A | 201 | 1.776 | 3.555 | 6.690 | 1.00 27.75 | C |
| ATOM | 1273 | CD2 | PHE | A | 201 | -0.130 | 4.975 | 6.341 | 1.00 27.95 | C |
| ATOM | 1274 | CE1 | PHE | A | 201 | 1.003 | 2.436 | 6.370 | 1.00 28.51 | C |
| ATOM | 1275 | CE2 | PHE | A | 201 | -0.910 | 3.862 | 6.020 | 1.00 28.95 | C |
| ATOM | 1276 | CZ | PHE | A | 201 | -0.344 | 2.588 | 6.032 | 1.00 29.19 | C |
| ATOM | 1277 | C | PHE | A | 201 | 3.396 | 7.950 | 5.925 | 1.00 31.63 | C |
| ATOM | 1278 | O | PHE | A | 201 | 2.707 | 8.767 | 6.536 | 1.00 32.82 | O |
| ATOM | 1279 | N | GLY | A | 202 | 4.555 | 8.267 | 5.346 | 1.00 30.70 | N |
| ATOM | 1280 | CA | GLY | A | 202 | 5.099 | 9.612 | 5.427 | 1.00 31.27 | C |
| ATOM | 1281 | C | GLY | A | 202 | 4.385 | 10.681 | 4.601 | 1.00 31.92 | C |
| ATOM | 1282 | O | GLY | A | 202 | 4.742 | 11.856 | 4.672 | 1.00 33.10 | O |
| ATOM | 1283 | N | SER | A | 203 | 3.386 | 10.283 | 3.815 | 1.00 31.33 | N |
| ATOM | 1284 | CA | SER | A | 203 | 2.620 | 11.211 | 2.991 | 1.00 29.57 | C |
| ATOM | 1285 | CB | SER | A | 203 | 2.828 | 10.934 | 1.495 | 1.00 31.64 | C |
| ATOM | 1286 | OG | SER | A | 203 | 4.186 | 10.711 | 1.180 | 1.00 32.99 | O |
| ATOM | 1287 | C | SER | A | 203 | 1.145 | 11.001 | 3.306 | 1.00 29.70 | C |
| ATOM | 1288 | O | SER | A | 203 | 0.278 | 11.572 | 2.654 | 1.00 30.28 | O |
| ATOM | 1289 | N | ALA | A | 204 | 0.868 | 10.158 | 4.292 | 1.00 28.35 | N |
| ATOM | 1290 | CA | ALA | A | 204 | -0.500 | 9.856 | 4.680 | 1.00 28.96 | C |
| ATOM | 1291 | CB | ALA | A | 204 | -0.525 | 8.605 | 5.545 | 1.00 29.32 | C |
| ATOM | 1292 | C | ALA | A | 204 | -1.138 | 11.028 | 5.421 | 1.00 30.34 | C |
| ATOM | 1293 | O | ALA | A | 204 | -0.452 | 11.810 | 6.083 | 1.00 30.28 | O |
| ATOM | 1294 | N | LYS | A | 205 | -2.455 | 11.147 | 5.306 | 1.00 30.56 | N |
| ATOM | 1295 | CA | LYS | A | 205 | -3.171 | 12.235 | 5.946 | 1.00 30.49 | C |
| ATOM | 1296 | CB | LYS | A | 205 | -2.979 | 13.530 | 5.149 | 1.00 29.02 | C |
| ATOM | 1297 | CG | LYS | A | 205 | -3.653 | 14.767 | 5.755 | 1.00 26.54 | C |
| ATOM | 1298 | CD | LYS | A | 205 | -3.414 | 15.996 | 4.890 | 1.00 25.13 | C |
| ATOM | 1299 | CE | LYS | A | 205 | -4.076 | 17.232 | 5.469 | 1.00 26.48 | C |
| ATOM | 1300 | NZ | LYS | A | 205 | -3.820 | 18.457 | 4.653 | 1.00 26.84 | N |
| ATOM | 1301 | C | LYS | A | 205 | -4.651 | 11.930 | 6.058 | 1.00 32.84 | C |
| ATOM | 1302 | O | LYS | A | 205 | -5.228 | 11.260 | 5.193 | 1.00 32.93 | O |
| ATOM | 1303 | N | GLN | A | 206 | -5.264 | 12.410 | 7.134 | 1.00 36.09 | N |
| ATOM | 1304 | CA | GLN | A | 206 | -6.692 | 12.205 | 7.332 | 1.00 39.32 | C |
| ATOM | 1305 | CB | GLN | A | 206 | -7.034 | 12.178 | 8.830 | 1.00 40.76 | C |
| ATOM | 1306 | CG | GLN | A | 206 | -7.007 | 10.769 | 9.441 | 1.00 45.19 | C |
| ATOM | 1307 | CD | GLN | A | 206 | -6.290 | 10.714 | 10.809 | 1.00 48.38 | C |
| ATOM | 1308 | OE1 | GLN | A | 206 | -5.289 | 11.423 | 11.032 | 1.00 49.50 | O |
| ATOM | 1309 | NE2 | GLN | A | 206 | -6.790 | 9.865 | 11.717 | 1.00 45.12 | N |
| ATOM | 1310 | C | GLN | A | 206 | -7.341 | 13.391 | 6.628 | 1.00 39.67 | C |
| ATOM | 1311 | O | GLN | A | 206 | -7.221 | 14.531 | 7.070 | 1.00 38.53 | O |
| ATOM | 1312 | N | LEU | A | 207 | -7.987 | 13.117 | 5.500 | 1.00 41.38 | N |
| ATOM | 1313 | CA | LEU | A | 207 | -8.634 | 14.163 | 4.728 | 1.00 41.27 | C |
| ATOM | 1314 | CB | LEU | A | 207 | -8.969 | 13.651 | 3.328 | 1.00 38.51 | C |
| ATOM | 1315 | CG | LEU | A | 207 | -7.796 | 13.081 | 2.535 | 1.00 37.32 | C |
| ATOM | 1316 | CD1 | LEU | A | 207 | -8.319 | 12.485 | 1.260 | 1.00 36.55 | C |
| ATOM | 1317 | CD2 | LEU | A | 207 | -6.755 | 14.164 | 2.260 | 1.00 35.85 | C |
| ATOM | 1318 | C | LEU | A | 207 | -9.900 | 14.614 | 5.424 | 1.00 42.67 | C |
| ATOM | 1319 | O | LEU | A | 207 | -10.733 | 13.798 | 5.811 | 1.00 42.22 | O |
| ATOM | 1320 | N | VAL | A | 208 | -10.024 | 15.923 | 5.595 | 1.00 44.97 | N |
| ATOM | 1321 | CA | VAL | A | 208 | -11.194 | 16.506 | 6.221 | 1.00 47.55 | C |
| ATOM | 1322 | CB | VAL | A | 208 | -10.811 | 17.428 | 7.398 | 1.00 47.97 | C |
| ATOM | 1323 | CG1 | VAL | A | 208 | -12.050 | 18.092 | 7.965 | 1.00 47.25 | C |
| ATOM | 1324 | CG2 | VAL | A | 208 | -10.112 | 16.631 | 8.480 | 1.00 46.97 | C |
| ATOM | 1325 | C | VAL | A | 208 | -11.881 | 17.324 | 5.148 | 1.00 48.95 | C |
| ATOM | 1326 | O | VAL | A | 208 | -11.287 | 18.244 | 4.578 | 1.00 48.54 | O |
| ATOM | 1327 | N | ARG | A | 209 | -13.127 | 16.974 | 4.849 | 1.00 50.85 | N |
| ATOM | 1328 | CA | ARG | A | 209 | -13.867 | 17.707 | 3.829 | 1.00 53.21 | C |
| ATOM | 1329 | CB | ARG | A | 209 | -15.308 | 17.195 | 3.745 | 1.00 55.70 | C |
| ATOM | 1330 | CG | ARG | A | 209 | -15.978 | 17.447 | 2.393 | 1.00 60.52 | C |
| ATOM | 1331 | CD | ARG | A | 209 | -17.421 | 16.942 | 2.405 | 1.00 64.17 | C |
| ATOM | 1332 | NE | ARG | A | 209 | -17.512 | 15.580 | 2.942 | 1.00 66.64 | N |
| ATOM | 1333 | CZ | ARG | A | 209 | -18.654 | 14.943 | 3.182 | 1.00 68.12 | C |

FIG. 2-21

```
ATOM   1334  NH1 ARG A 209     -19.822  15.540   2.933  1.00 67.43           N
ATOM   1335  NH2 ARG A 209     -18.618  13.713   3.686  1.00 68.56           N
ATOM   1336  C   ARG A 209     -13.848  19.181   4.236  1.00 52.77           C
ATOM   1337  O   ARG A 209     -14.137  19.520   5.389  1.00 52.99           O
ATOM   1338  N   GLY A 210     -13.482  20.046   3.299  1.00 51.67           N
ATOM   1339  CA  GLY A 210     -13.432  21.463   3.590  1.00 51.36           C
ATOM   1340  C   GLY A 210     -12.022  21.988   3.716  1.00 51.86           C
ATOM   1341  O   GLY A 210     -11.728  23.112   3.304  1.00 51.69           O
ATOM   1342  N   GLU A 211     -11.145  21.178   4.304  1.00 51.49           N
ATOM   1343  CA  GLU A 211      -9.736  21.551   4.473  1.00 50.79           C
ATOM   1344  CB  GLU A 211      -9.126  20.852   5.684  1.00 52.25           C
ATOM   1345  CG  GLU A 211      -9.897  20.956   6.965  1.00 53.69           C
ATOM   1346  CD  GLU A 211      -9.335  20.015   8.013  1.00 53.73           C
ATOM   1347  OE1 GLU A 211      -9.723  20.155   9.196  1.00 53.01           O
ATOM   1348  OE2 GLU A 211      -8.515  19.139   7.635  1.00 53.06           O
ATOM   1349  C   GLU A 211      -8.937  21.133   3.251  1.00 49.36           C
ATOM   1350  O   GLU A 211      -8.912  19.956   2.885  1.00 50.93           O
ATOM   1351  N   PRO A 212      -8.240  22.079   2.625  1.00 47.67           N
ATOM   1352  CD  PRO A 212      -8.079  23.494   3.005  1.00 47.60           C
ATOM   1353  CA  PRO A 212      -7.445  21.754   1.433  1.00 45.29           C
ATOM   1354  CB  PRO A 212      -7.090  23.123   0.877  1.00 45.83           C
ATOM   1355  CG  PRO A 212      -6.914  23.934   2.121  1.00 46.23           C
ATOM   1356  C   PRO A 212      -6.204  20.926   1.707  1.00 42.30           C
ATOM   1357  O   PRO A 212      -5.651  20.946   2.801  1.00 41.90           O
ATOM   1358  N   ASN A 213      -5.777  20.191   0.697  1.00 40.09           N
ATOM   1359  CA  ASN A 213      -4.601  19.353   0.804  1.00 37.64           C
ATOM   1360  CB  ASN A 213      -5.012  17.884   0.822  1.00 36.75           C
ATOM   1361  CG  ASN A 213      -6.071  17.601   1.846  1.00 36.14           C
ATOM   1362  OD1 ASN A 213      -5.866  17.793   3.043  1.00 39.69           O
ATOM   1363  ND2 ASN A 213      -7.223  17.160   1.385  1.00 38.08           N
ATOM   1364  C   ASN A 213      -3.826  19.699  -0.452  1.00 35.89           C
ATOM   1365  O   ASN A 213      -4.404  20.187  -1.420  1.00 35.54           O
ATOM   1366  N   VAL A 214      -2.526  19.456  -0.431  1.00 34.82           N
ATOM   1367  CA  VAL A 214      -1.691  19.798  -1.555  1.00 35.55           C
ATOM   1368  CB  VAL A 214      -0.222  19.985  -1.077  1.00 35.97           C
ATOM   1369  CG1 VAL A 214       0.205  18.817  -0.204  1.00 37.11           C
ATOM   1370  CG2 VAL A 214       0.711  20.137  -2.265  1.00 38.67           C
ATOM   1371  C   VAL A 214      -1.804  18.816  -2.725  1.00 36.65           C
ATOM   1372  O   VAL A 214      -1.860  17.587  -2.541  1.00 35.11           O
ATOM   1373  N   SER A 215      -1.842  19.381  -3.934  1.00 36.48           N
ATOM   1374  CA  SER A 215      -1.995  18.602  -5.160  1.00 35.74           C
ATOM   1375  CB  SER A 215      -2.608  19.480  -6.256  1.00 35.28           C
ATOM   1376  OG  SER A 215      -1.806  20.610  -6.511  1.00 38.00           O
ATOM   1377  C   SER A 215      -0.762  17.896  -5.708  1.00 34.72           C
ATOM   1378  O   SER A 215      -0.872  16.791  -6.234  1.00 35.28           O
ATOM   1379  N   PTY A 216       0.404  18.516  -5.612  1.00 34.35           N
ATOM   1380  CA  PTY A 216       1.609  17.879  -6.126  1.00 33.64           C
ATOM   1381  C   PTY A 216       2.071  16.784  -5.174  1.00 35.17           C
ATOM   1382  O   PTY A 216       3.065  16.930  -4.461  1.00 35.61           O
ATOM   1383  CB  PTY A 216       2.721  18.916  -6.303  1.00 33.07           C
ATOM   1384  CG  PTY A 216       3.798  18.303  -7.148  1.00 34.38           C
ATOM   1385  CD1 PTY A 216       3.651  18.180  -8.598  1.00 33.03           C
ATOM   1386  CD2 PTY A 216       4.984  17.704  -6.489  1.00 33.58           C
ATOM   1387  CE1 PTY A 216       4.660  17.474  -9.378  1.00 35.41           C
ATOM   1388  CE2 PTY A 216       5.995  16.998  -7.245  1.00 33.57           C
ATOM   1389  CZ  PTY A 216       5.835  16.887  -8.691  1.00 35.46           C
ATOM   1390  OH  PTY A 216       6.916  16.588  -9.378  1.00 37.08           O
ATOM   1391  P   PTY A 216       7.184  15.289  -9.958  1.00 38.30           P
ATOM   1392  OP1 PTY A 216       8.419  15.912 -10.430  1.00 41.12           O
ATOM   1393  OP2 PTY A 216       6.262  14.911 -11.109  1.00 38.93           O
ATOM   1394  OP3 PTY A 216       7.461  14.199  -9.070  1.00 37.29           O
ATOM   1395  N   ILE A 217       1.346  15.678  -5.144  1.00 36.32           N
ATOM   1396  CA  ILE A 217       1.737  14.612  -4.254  1.00 36.20           C
ATOM   1397  CB  ILE A 217       0.905  14.663  -2.962  1.00 37.58           C
ATOM   1398  CG2 ILE A 217      -0.513  14.153  -3.226  1.00 35.83           C
ATOM   1399  CG1 ILE A 217       1.658  13.897  -1.869  1.00 38.35           C
ATOM   1400  CD1 ILE A 217       1.172  14.139  -0.480  1.00 37.35           C
```

FIG. 2-22

| | | | | | | | | | |
|---|---|---|---|---|---|---|---|---|---|
| ATOM | 1401 | C | ILE | A | 217 | 1.609 | 13.266 | -4.959 | 1.00 36.52 | C |
| ATOM | 1402 | O | ILE | A | 217 | 1.121 | 13.201 | -6.084 | 1.00 36.17 | O |
| ATOM | 1403 | N | CYS | A | 218 | 2.060 | 12.201 | -4.300 | 1.00 36.04 | N |
| ATOM | 1404 | CA | CYS | A | 218 | 2.056 | 10.847 | -4.867 | 1.00 36.09 | C |
| ATOM | 1405 | CB | CYS | A | 218 | 0.771 | 10.517 | -5.626 | 1.00 38.39 | C |
| ATOM | 1406 | SG | CYS | A | 218 | -0.736 | 10.597 | -4.721 | 1.00 44.31 | S |
| ATOM | 1407 | C | CYS | A | 218 | 3.173 | 10.839 | -5.883 | 1.00 34.47 | C |
| ATOM | 1408 | O | CYS | A | 218 | 3.583 | 11.898 | -6.364 | 1.00 32.18 | O |
| ATOM | 1409 | N | SER | A | 219 | 3.652 | 9.646 | -6.213 | 1.00 34.26 | N |
| ATOM | 1410 | CA | SER | A | 219 | 4.710 | 9.490 | -7.198 | 1.00 33.32 | C |
| ATOM | 1411 | CB | SER | A | 219 | 5.285 | 8.077 | -7.090 | 1.00 33.65 | C |
| ATOM | 1412 | OG | SER | A | 219 | 6.552 | 8.014 | -7.697 | 1.00 32.28 | O |
| ATOM | 1413 | C | SER | A | 219 | 4.092 | 9.730 | -8.584 | 1.00 32.66 | C |
| ATOM | 1414 | O | SER | A | 219 | 3.022 | 9.216 | -8.882 | 1.00 33.33 | O |
| ATOM | 1415 | N | ARG | A | 220 | 4.785 | 10.488 | -9.427 | 1.00 32.85 | N |
| ATOM | 1416 | CA | ARG | A | 220 | 4.311 | 10.825 | -10.774 | 1.00 32.72 | C |
| ATOM | 1417 | CB | ARG | A | 220 | 5.473 | 11.273 | -11.654 | 1.00 31.77 | C |
| ATOM | 1418 | CG | ARG | A | 220 | 5.008 | 11.859 | -12.972 | 1.00 33.84 | C |
| ATOM | 1419 | CD | ARG | A | 220 | 5.951 | 12.947 | -13.411 | 1.00 33.91 | C |
| ATOM | 1420 | NE | ARG | A | 220 | 7.168 | 12.409 | -14.002 | 1.00 36.23 | N |
| ATOM | 1421 | CZ | ARG | A | 220 | 8.380 | 12.909 | -13.794 | 1.00 36.27 | C |
| ATOM | 1422 | NH1 | ARG | A | 220 | 8.537 | 13.959 | -12.994 | 1.00 33.49 | N |
| ATOM | 1423 | NH2 | ARG | A | 220 | 9.426 | 12.369 | -14.410 | 1.00 37.73 | N |
| ATOM | 1424 | C | ARG | A | 220 | 3.523 | 9.772 | -11.545 | 1.00 33.43 | C |
| ATOM | 1425 | O | ARG | A | 220 | 2.375 | 9.997 | -11.915 | 1.00 34.27 | O |
| ATOM | 1426 | N | TYR | A | 221 | 4.149 | 8.635 | -11.816 | 1.00 32.62 | N |
| ATOM | 1427 | CA | TYR | A | 221 | 3.492 | 7.580 | -12.569 | 1.00 32.82 | C |
| ATOM | 1428 | CB | TYR | A | 221 | 4.415 | 6.375 | -12.694 | 1.00 32.44 | C |
| ATOM | 1429 | CG | TYR | A | 221 | 5.713 | 6.644 | -13.416 | 1.00 32.65 | C |
| ATOM | 1430 | CD1 | TYR | A | 221 | 5.884 | 7.781 | -14.206 | 1.00 32.74 | C |
| ATOM | 1431 | CE1 | TYR | A | 221 | 7.070 | 7.997 | -14.893 | 1.00 32.70 | C |
| ATOM | 1432 | CD2 | TYR | A | 221 | 6.764 | 5.739 | -13.336 | 1.00 33.10 | C |
| ATOM | 1433 | CE2 | TYR | A | 221 | 7.948 | 5.946 | -14.019 | 1.00 31.97 | C |
| ATOM | 1434 | CZ | TYR | A | 221 | 8.098 | 7.068 | -14.795 | 1.00 32.65 | C |
| ATOM | 1435 | OH | TYR | A | 221 | 9.275 | 7.259 | -15.476 | 1.00 31.38 | O |
| ATOM | 1436 | C | TYR | A | 221 | 2.158 | 7.122 | -12.002 | 1.00 33.10 | C |
| ATOM | 1437 | O | TYR | A | 221 | 1.285 | 6.682 | -12.751 | 1.00 33.73 | O |
| ATOM | 1438 | N | TYR | A | 222 | 1.999 | 7.217 | -10.686 | 1.00 32.68 | N |
| ATOM | 1439 | CA | TYR | A | 222 | 0.764 | 6.777 | -10.035 | 1.00 30.81 | C |
| ATOM | 1440 | CB | TYR | A | 222 | 1.092 | 5.804 | -8.899 | 1.00 30.81 | C |
| ATOM | 1441 | CG | TYR | A | 222 | 2.253 | 4.896 | -9.228 | 1.00 33.17 | C |
| ATOM | 1442 | CD1 | TYR | A | 222 | 3.568 | 5.306 | -8.990 | 1.00 33.10 | C |
| ATOM | 1443 | CE1 | TYR | A | 222 | 4.646 | 4.533 | -9.402 | 1.00 32.97 | C |
| ATOM | 1444 | CD2 | TYR | A | 222 | 2.052 | 3.671 | -9.880 | 1.00 33.41 | C |
| ATOM | 1445 | CE2 | TYR | A | 222 | 3.128 | 2.889 | -10.297 | 1.00 32.92 | C |
| ATOM | 1446 | CZ | TYR | A | 222 | 4.421 | 3.329 | -10.061 | 1.00 32.99 | C |
| ATOM | 1447 | OH | TYR | A | 222 | 5.488 | 2.593 | -10.516 | 1.00 33.31 | O |
| ATOM | 1448 | C | TYR | A | 222 | -0.071 | 7.935 | -9.502 | 1.00 30.86 | C |
| ATOM | 1449 | O | TYR | A | 222 | -1.028 | 7.726 | -8.759 | 1.00 31.13 | O |
| ATOM | 1450 | N | ARG | A | 223 | 0.290 | 9.153 | -9.890 | 1.00 28.09 | N |
| ATOM | 1451 | CA | ARG | A | 223 | -0.429 | 10.332 | -9.450 | 1.00 27.49 | C |
| ATOM | 1452 | CB | ARG | A | 223 | 0.412 | 11.583 | -9.709 | 1.00 26.71 | C |
| ATOM | 1453 | CG | ARG | A | 223 | -0.328 | 12.876 | -9.460 | 1.00 26.66 | C |
| ATOM | 1454 | CD | ARG | A | 223 | 0.579 | 13.918 | -8.842 | 1.00 28.37 | C |
| ATOM | 1455 | NE | ARG | A | 223 | 1.670 | 14.281 | -9.727 | 1.00 29.06 | N |
| ATOM | 1456 | CZ | ARG | A | 223 | 2.958 | 14.084 | -9.464 | 1.00 29.40 | C |
| ATOM | 1457 | NH1 | ARG | A | 223 | 3.337 | 13.521 | -8.325 | 1.00 24.46 | N |
| ATOM | 1458 | NH2 | ARG | A | 223 | 3.872 | 14.458 | -10.353 | 1.00 30.55 | N |
| ATOM | 1459 | C | ARG | A | 223 | -1.781 | 10.465 | -10.137 | 1.00 27.70 | C |
| ATOM | 1460 | O | ARG | A | 223 | -1.866 | 10.475 | -11.366 | 1.00 27.33 | O |
| ATOM | 1461 | N | ALA | A | 224 | -2.833 | 10.568 | -9.334 | 1.00 27.20 | N |
| ATOM | 1462 | CA | ALA | A | 224 | -4.188 | 10.705 | -9.849 | 1.00 28.88 | C |
| ATOM | 1463 | CB | ALA | A | 224 | -5.189 | 10.786 | -8.693 | 1.00 29.07 | C |
| ATOM | 1464 | C | ALA | A | 224 | -4.289 | 11.948 | -10.716 | 1.00 29.31 | C |
| ATOM | 1465 | O | ALA | A | 224 | -3.602 | 12.942 | -10.485 | 1.00 29.85 | O |
| ATOM | 1466 | N | PRO | A | 225 | -5.156 | 11.908 | -11.730 | 1.00 29.19 | N |
| ATOM | 1467 | CD | PRO | A | 225 | -5.948 | 10.751 | -12.167 | 1.00 29.59 | C |

FIG. 2-23

```
ATOM   1468  CA   PRO A 225      -5.336  13.042 -12.629  1.00 28.85           C
ATOM   1469  CB   PRO A 225      -6.205  12.462 -13.742  1.00 28.09           C
ATOM   1470  CG   PRO A 225      -6.987  11.396 -13.041  1.00 29.69           C
ATOM   1471  C    PRO A 225      -5.924  14.309 -11.985  1.00 29.34           C
ATOM   1472  O    PRO A 225      -5.609  15.418 -12.423  1.00 28.61           O
ATOM   1473  N    GLU A 226      -6.762  14.168 -10.957  1.00 29.89           N
ATOM   1474  CA   GLU A 226      -7.320  15.359 -10.313  1.00 30.87           C
ATOM   1475  CB   GLU A 226      -8.273  15.022  -9.166  1.00 29.98           C
ATOM   1476  CG   GLU A 226      -9.172  13.855  -9.408  1.00 30.89           C
ATOM   1477  CD   GLU A 226      -8.517  12.558  -9.037  1.00 28.21           C
ATOM   1478  OE1  GLU A 226      -8.678  12.119  -7.881  1.00 25.77           O
ATOM   1479  OE2  GLU A 226      -7.828  11.993  -9.906  1.00 30.27           O
ATOM   1480  C    GLU A 226      -6.158  16.128  -9.723  1.00 31.55           C
ATOM   1481  O    GLU A 226      -6.189  17.352  -9.650  1.00 32.79           O
ATOM   1482  N    LEU A 227      -5.138  15.398  -9.286  1.00 30.40           N
ATOM   1483  CA   LEU A 227      -3.966  16.018  -8.700  1.00 29.20           C
ATOM   1484  CB   LEU A 227      -3.058  14.941  -8.088  1.00 29.09           C
ATOM   1485  CG   LEU A 227      -3.696  14.026  -7.026  1.00 28.07           C
ATOM   1486  CD1  LEU A 227      -2.794  12.833  -6.771  1.00 26.83           C
ATOM   1487  CD2  LEU A 227      -3.961  14.798  -5.739  1.00 24.21           C
ATOM   1488  C    LEU A 227      -3.217  16.832  -9.755  1.00 28.59           C
ATOM   1489  O    LEU A 227      -2.917  18.002  -9.529  1.00 29.37           O
ATOM   1490  N    ILE A 228      -2.934  16.231 -10.907  1.00 28.71           N
ATOM   1491  CA   ILE A 228      -2.227  16.930 -11.971  1.00 31.09           C
ATOM   1492  CB   ILE A 228      -2.076  16.051 -13.219  1.00 31.80           C
ATOM   1493  CG2  ILE A 228      -1.140  16.718 -14.215  1.00 30.05           C
ATOM   1494  CG1  ILE A 228      -1.535  14.683 -12.829  1.00 31.58           C
ATOM   1495  CD1  ILE A 228      -1.560  13.693 -13.953  1.00 30.62           C
ATOM   1496  C    ILE A 228      -2.970  18.198 -12.386  1.00 33.62           C
ATOM   1497  O    ILE A 228      -2.356  19.154 -12.848  1.00 34.57           O
ATOM   1498  N    PHE A 229      -4.294  18.178 -12.244  1.00 35.44           N
ATOM   1499  CA   PHE A 229      -5.145  19.311 -12.579  1.00 36.08           C
ATOM   1500  CB   PHE A 229      -6.587  18.854 -12.815  1.00 36.13           C
ATOM   1501  CG   PHE A 229      -6.929  18.628 -14.253  1.00 35.19           C
ATOM   1502  CD1  PHE A 229      -6.958  19.689 -15.152  1.00 34.89           C
ATOM   1503  CD2  PHE A 229      -7.234  17.351 -14.709  1.00 36.13           C
ATOM   1504  CE1  PHE A 229      -7.285  19.485 -16.490  1.00 35.15           C
ATOM   1505  CE2  PHE A 229      -7.563  17.130 -16.042  1.00 36.07           C
ATOM   1506  CZ   PHE A 229      -7.588  18.202 -16.937  1.00 35.85           C
ATOM   1507  C    PHE A 229      -5.144  20.341 -11.455  1.00 36.93           C
ATOM   1508  O    PHE A 229      -5.903  21.305 -11.499  1.00 38.07           O
ATOM   1509  N    GLY A 230      -4.327  20.115 -10.432  1.00 37.43           N
ATOM   1510  CA   GLY A 230      -4.244  21.059  -9.332  1.00 36.98           C
ATOM   1511  C    GLY A 230      -5.334  20.991  -8.282  1.00 36.57           C
ATOM   1512  O    GLY A 230      -5.435  21.895  -7.456  1.00 37.78           O
ATOM   1513  N    ALA A 231      -6.148  19.942  -8.303  1.00 36.26           N
ATOM   1514  CA   ALA A 231      -7.217  19.805  -7.317  1.00 36.84           C
ATOM   1515  CB   ALA A 231      -7.976  18.521  -7.552  1.00 36.49           C
ATOM   1516  C    ALA A 231      -6.660  19.831  -5.896  1.00 37.80           C
ATOM   1517  O    ALA A 231      -5.516  19.439  -5.655  1.00 38.08           O
ATOM   1518  N    THR A 232      -7.477  20.276  -4.953  1.00 37.67           N
ATOM   1519  CA   THR A 232      -7.042  20.369  -3.573  1.00 37.91           C
ATOM   1520  CB   THR A 232      -6.740  21.824  -3.221  1.00 39.27           C
ATOM   1521  OG1  THR A 232      -7.961  22.575  -3.223  1.00 41.40           O
ATOM   1522  CG2  THR A 232      -5.805  22.432  -4.258  1.00 37.93           C
ATOM   1523  C    THR A 232      -8.110  19.835  -2.629  1.00 38.08           C
ATOM   1524  O    THR A 232      -7.904  19.767  -1.420  1.00 38.20           O
ATOM   1525  N    ASP A 233      -9.242  19.440  -3.198  1.00 38.43           N
ATOM   1526  CA   ASP A 233     -10.361  18.914  -2.435  1.00 39.63           C
ATOM   1527  CB   ASP A 233     -11.623  19.707  -2.755  1.00 44.02           C
ATOM   1528  CG   ASP A 233     -12.109  19.467  -4.179  1.00 48.53           C
ATOM   1529  OD1  ASP A 233     -11.268  19.558  -5.113  1.00 48.12           O
ATOM   1530  OD2  ASP A 233     -13.330  19.192  -4.363  1.00 51.15           O
ATOM   1531  C    ASP A 233     -10.604  17.458  -2.800  1.00 38.98           C
ATOM   1532  O    ASP A 233     -11.743  16.986  -2.781  1.00 39.94           O
ATOM   1533  N    TYR A 234      -9.539  16.753  -3.154  1.00 36.83           N
ATOM   1534  CA   TYR A 234      -9.659  15.359  -3.535  1.00 34.90           C
```

FIG. 2-24

```
ATOM   1535  CB   TYR A 234      -8.401  14.918  -4.269  1.00 33.46           C
ATOM   1536  CG   TYR A 234      -7.131  15.230  -3.527  1.00 34.22           C
ATOM   1537  CD1  TYR A 234      -6.635  14.366  -2.553  1.00 33.48           C
ATOM   1538  CE1  TYR A 234      -5.442  14.639  -1.892  1.00 32.96           C
ATOM   1539  CD2  TYR A 234      -6.406  16.381  -3.812  1.00 33.43           C
ATOM   1540  CE2  TYR A 234      -5.214  16.658  -3.153  1.00 33.15           C
ATOM   1541  CZ   TYR A 234      -4.740  15.780  -2.196  1.00 32.32           C
ATOM   1542  OH   TYR A 234      -3.555  16.039  -1.558  1.00 34.66           O
ATOM   1543  C    TYR A 234      -9.932  14.455  -2.345  1.00 34.38           C
ATOM   1544  O    TYR A 234      -9.855  14.878  -1.190  1.00 34.76           O
ATOM   1545  N    THR A 235     -10.270  13.208  -2.638  1.00 34.10           N
ATOM   1546  CA   THR A 235     -10.582  12.236  -1.605  1.00 33.35           C
ATOM   1547  CB   THR A 235     -11.968  11.644  -1.820  1.00 32.30           C
ATOM   1548  OG1  THR A 235     -11.951  10.809  -2.984  1.00 34.55           O
ATOM   1549  CG2  THR A 235     -12.977  12.745  -2.029  1.00 33.19           C
ATOM   1550  C    THR A 235      -9.580  11.095  -1.620  1.00 34.18           C
ATOM   1551  O    THR A 235      -8.613  11.106  -2.382  1.00 35.09           O
ATOM   1552  N    SER A 236      -9.820  10.096  -0.785  1.00 34.50           N
ATOM   1553  CA   SER A 236      -8.923   8.967  -0.728  1.00 35.41           C
ATOM   1554  CB   SER A 236      -9.240   8.088   0.485  1.00 34.74           C
ATOM   1555  OG   SER A 236     -10.525   7.510   0.381  1.00 36.36           O
ATOM   1556  C    SER A 236      -8.983   8.143  -2.010  1.00 35.82           C
ATOM   1557  O    SER A 236      -8.175   7.231  -2.204  1.00 37.93           O
ATOM   1558  N    SER A 237      -9.920   8.453  -2.897  1.00 34.63           N
ATOM   1559  CA   SER A 237     -10.005   7.695  -4.135  1.00 33.15           C
ATOM   1560  CB   SER A 237     -11.242   8.098  -4.947  1.00 30.09           C
ATOM   1561  OG   SER A 237     -11.279   9.488  -5.198  1.00 32.37           O
ATOM   1562  C    SER A 237      -8.734   7.871  -4.973  1.00 32.42           C
ATOM   1563  O    SER A 237      -8.534   7.155  -5.953  1.00 33.57           O
ATOM   1564  N    ILE A 238      -7.867   8.808  -4.593  1.00 30.30           N
ATOM   1565  CA   ILE A 238      -6.634   8.975  -5.352  1.00 29.30           C
ATOM   1566  CB   ILE A 238      -5.803  10.201  -4.909  1.00 29.96           C
ATOM   1567  CG2  ILE A 238      -6.504  11.492  -5.317  1.00 28.31           C
ATOM   1568  CG1  ILE A 238      -5.524  10.122  -3.406  1.00 30.00           C
ATOM   1569  CD1  ILE A 238      -4.461  11.087  -2.924  1.00 27.91           C
ATOM   1570  C    ILE A 238      -5.764   7.736  -5.156  1.00 28.55           C
ATOM   1571  O    ILE A 238      -4.912   7.437  -5.988  1.00 28.29           O
ATOM   1572  N    ASP A 239      -5.972   7.018  -4.056  1.00 27.56           N
ATOM   1573  CA   ASP A 239      -5.185   5.819  -3.814  1.00 30.24           C
ATOM   1574  CB   ASP A 239      -5.313   5.358  -2.366  1.00 29.73           C
ATOM   1575  CG   ASP A 239      -4.576   6.262  -1.405  1.00 29.42           C
ATOM   1576  OD1  ASP A 239      -3.569   6.872  -1.813  1.00 32.29           O
ATOM   1577  OD2  ASP A 239      -4.985   6.357  -0.239  1.00 29.85           O
ATOM   1578  C    ASP A 239      -5.630   4.703  -4.743  1.00 32.16           C
ATOM   1579  O    ASP A 239      -4.828   3.887  -5.204  1.00 32.18           O
ATOM   1580  N    VAL A 240      -6.928   4.689  -5.025  1.00 32.10           N
ATOM   1581  CA   VAL A 240      -7.530   3.702  -5.900  1.00 29.22           C
ATOM   1582  CB   VAL A 240      -9.049   3.840  -5.838  1.00 29.31           C
ATOM   1583  CG1  VAL A 240      -9.714   2.890  -6.812  1.00 28.78           C
ATOM   1584  CG2  VAL A 240      -9.505   3.574  -4.417  1.00 24.31           C
ATOM   1585  C    VAL A 240      -7.010   3.864  -7.328  1.00 29.49           C
ATOM   1586  O    VAL A 240      -6.792   2.876  -8.035  1.00 29.15           O
ATOM   1587  N    TRP A 241      -6.794   5.111  -7.740  1.00 28.83           N
ATOM   1588  CA   TRP A 241      -6.255   5.392  -9.066  1.00 29.70           C
ATOM   1589  CB   TRP A 241      -6.187   6.910  -9.326  1.00 29.95           C
ATOM   1590  CG   TRP A 241      -5.404   7.279 -10.569  1.00 30.53           C
ATOM   1591  CD2  TRP A 241      -5.917   7.413 -11.902  1.00 30.79           C
ATOM   1592  CE2  TRP A 241      -4.817   7.674 -12.750  1.00 31.11           C
ATOM   1593  CE3  TRP A 241      -7.200   7.335 -12.465  1.00 30.63           C
ATOM   1594  CD1  TRP A 241      -4.050   7.467 -10.664  1.00 30.81           C
ATOM   1595  NE1  TRP A 241      -3.691   7.702 -11.968  1.00 28.67           N
ATOM   1596  CZ2  TRP A 241      -4.962   7.855 -14.135  1.00 32.68           C
ATOM   1597  CZ3  TRP A 241      -7.338   7.515 -13.841  1.00 31.79           C
ATOM   1598  CH2  TRP A 241      -6.226   7.771 -14.657  1.00 31.34           C
ATOM   1599  C    TRP A 241      -4.858   4.798  -9.093  1.00 28.63           C
ATOM   1600  O    TRP A 241      -4.496   4.073 -10.009  1.00 28.93           O
ATOM   1601  N    SER A 242      -4.086   5.108  -8.060  1.00 30.26           N
```

FIG. 2-25

```
ATOM   1602  CA  SER A 242      -2.723   4.612  -7.931  1.00 29.53           C
ATOM   1603  CB  SER A 242      -2.135   5.091  -6.604  1.00 29.07           C
ATOM   1604  OG  SER A 242      -1.989   6.495  -6.589  1.00 26.99           O
ATOM   1605  C   SER A 242      -2.680   3.090  -8.004  1.00 29.28           C
ATOM   1606  O   SER A 242      -1.873   2.526  -8.730  1.00 29.28           O
ATOM   1607  N   ALA A 243      -3.560   2.442  -7.244  1.00 28.76           N
ATOM   1608  CA  ALA A 243      -3.644   0.991  -7.215  1.00 28.73           C
ATOM   1609  CB  ALA A 243      -4.748   0.552  -6.280  1.00 26.17           C
ATOM   1610  C   ALA A 243      -3.889   0.437  -8.619  1.00 31.37           C
ATOM   1611  O   ALA A 243      -3.348  -0.604  -8.995  1.00 31.71           O
ATOM   1612  N   GLY A 244      -4.715   1.137  -9.389  1.00 31.91           N
ATOM   1613  CA  GLY A 244      -5.001   0.712 -10.741  1.00 30.85           C
ATOM   1614  C   GLY A 244      -3.767   0.851 -11.610  1.00 31.88           C
ATOM   1615  O   GLY A 244      -3.570   0.076 -12.546  1.00 32.54           O
ATOM   1616  N   CYS A 245      -2.937   1.845 -11.305  1.00 31.34           N
ATOM   1617  CA  CYS A 245      -1.699   2.077 -12.049  1.00 29.68           C
ATOM   1618  CB  CYS A 245      -1.071   3.418 -11.654  1.00 28.66           C
ATOM   1619  SG  CYS A 245      -1.815   4.867 -12.464  1.00 30.27           S
ATOM   1620  C   CYS A 245      -0.702   0.967 -11.784  1.00 28.31           C
ATOM   1621  O   CYS A 245       0.132   0.661 -12.627  1.00 26.33           O
ATOM   1622  N   VAL A 246      -0.789   0.381 -10.594  1.00 28.73           N
ATOM   1623  CA  VAL A 246       0.101  -0.704 -10.218  1.00 29.47           C
ATOM   1624  CB  VAL A 246       0.109  -0.908  -8.691  1.00 29.19           C
ATOM   1625  CG1 VAL A 246       0.893  -2.155  -8.335  1.00 29.34           C
ATOM   1626  CG2 VAL A 246       0.725   0.307  -8.009  1.00 27.43           C
ATOM   1627  C   VAL A 246      -0.363  -1.987 -10.895  1.00 30.33           C
ATOM   1628  O   VAL A 246       0.447  -2.758 -11.389  1.00 31.56           O
ATOM   1629  N   LEU A 247      -1.672  -2.213 -10.896  1.00 30.42           N
ATOM   1630  CA  LEU A 247      -2.239  -3.386 -11.529  1.00 29.71           C
ATOM   1631  CB  LEU A 247      -3.750  -3.419 -11.322  1.00 29.66           C
ATOM   1632  CG  LEU A 247      -4.561  -4.362 -12.216  1.00 30.75           C
ATOM   1633  CD1 LEU A 247      -3.981  -5.773 -12.169  1.00 30.55           C
ATOM   1634  CD2 LEU A 247      -6.013  -4.359 -11.771  1.00 27.51           C
ATOM   1635  C   LEU A 247      -1.922  -3.364 -13.016  1.00 29.42           C
ATOM   1636  O   LEU A 247      -1.367  -4.316 -13.551  1.00 31.75           O
ATOM   1637  N   ALA A 248      -2.271  -2.279 -13.689  1.00 29.22           N
ATOM   1638  CA  ALA A 248      -1.998  -2.187 -15.111  1.00 29.20           C
ATOM   1639  CB  ALA A 248      -2.372  -0.805 -15.643  1.00 25.61           C
ATOM   1640  C   ALA A 248      -0.518  -2.455 -15.326  1.00 30.52           C
ATOM   1641  O   ALA A 248      -0.134  -3.158 -16.255  1.00 31.60           O
ATOM   1642  N   GLU A 249       0.310  -1.901 -14.445  1.00 30.69           N
ATOM   1643  CA  GLU A 249       1.750  -2.063 -14.548  1.00 30.64           C
ATOM   1644  CB  GLU A 249       2.455  -1.232 -13.484  1.00 31.98           C
ATOM   1645  CG  GLU A 249       3.936  -1.148 -13.734  1.00 35.05           C
ATOM   1646  CD  GLU A 249       4.658  -0.219 -12.786  1.00 35.48           C
ATOM   1647  OE1 GLU A 249       4.225   0.948 -12.641  1.00 34.88           O
ATOM   1648  OE2 GLU A 249       5.668  -0.659 -12.198  1.00 36.93           O
ATOM   1649  C   GLU A 249       2.206  -3.512 -14.432  1.00 30.27           C
ATOM   1650  O   GLU A 249       3.159  -3.921 -15.093  1.00 30.74           O
ATOM   1651  N   LEU A 250       1.533  -4.283 -13.588  1.00 28.94           N
ATOM   1652  CA  LEU A 250       1.884  -5.681 -13.396  1.00 29.45           C
ATOM   1653  CB  LEU A 250       1.271  -6.192 -12.090  1.00 27.15           C
ATOM   1654  CG  LEU A 250       1.919  -5.629 -10.829  1.00 26.38           C
ATOM   1655  CD1 LEU A 250       1.151  -6.100  -9.617  1.00 25.77           C
ATOM   1656  CD2 LEU A 250       3.378  -6.063 -10.758  1.00 26.26           C
ATOM   1657  C   LEU A 250       1.448  -6.556 -14.572  1.00 30.45           C
ATOM   1658  O   LEU A 250       2.033  -7.604 -14.816  1.00 30.84           O
ATOM   1659  N   LEU A 251       0.421  -6.116 -15.294  1.00 32.27           N
ATOM   1660  CA  LEU A 251      -0.078  -6.847 -16.448  1.00 32.19           C
ATOM   1661  CB  LEU A 251      -1.529  -6.471 -16.721  1.00 31.64           C
ATOM   1662  CG  LEU A 251      -2.518  -6.738 -15.589  1.00 33.66           C
ATOM   1663  CD1 LEU A 251      -3.828  -6.001 -15.859  1.00 32.14           C
ATOM   1664  CD2 LEU A 251      -2.744  -8.234 -15.454  1.00 31.78           C
ATOM   1665  C   LEU A 251       0.750  -6.519 -17.684  1.00 33.32           C
ATOM   1666  O   LEU A 251       0.865  -7.333 -18.595  1.00 35.41           O
ATOM   1667  N   LEU A 252       1.328  -5.322 -17.703  1.00 33.80           N
ATOM   1668  CA  LEU A 252       2.120  -4.843 -18.827  1.00 34.10           C
```

FIG. 2-26

```
ATOM   1669  CB   LEU A 252      1.853   -3.359  -19.047  1.00 36.43           C
ATOM   1670  CG   LEU A 252      0.685   -2.923  -19.916  1.00 39.28           C
ATOM   1671  CD1  LEU A 252     -0.591   -3.587  -19.461  1.00 41.69           C
ATOM   1672  CD2  LEU A 252      0.563   -1.424  -19.825  1.00 41.05           C
ATOM   1673  C    LEU A 252      3.626   -5.025  -18.762  1.00 35.39           C
ATOM   1674  O    LEU A 252      4.286   -5.069  -19.801  1.00 36.16           O
ATOM   1675  N    GLY A 253      4.185   -5.102  -17.562  1.00 35.55           N
ATOM   1676  CA   GLY A 253      5.626   -5.242  -17.451  1.00 36.41           C
ATOM   1677  C    GLY A 253      6.313   -3.888  -17.457  1.00 37.89           C
ATOM   1678  O    GLY A 253      7.534   -3.804  -17.573  1.00 38.45           O
ATOM   1679  N    GLN A 254      5.523   -2.825  -17.344  1.00 38.37           N
ATOM   1680  CA   GLN A 254      6.049   -1.465  -17.309  1.00 39.87           C
ATOM   1681  CB   GLN A 254      6.568   -1.062  -18.691  1.00 41.81           C
ATOM   1682  CG   GLN A 254      5.528   -1.130  -19.787  1.00 45.30           C
ATOM   1683  CD   GLN A 254      6.094   -0.737  -21.140  1.00 46.34           C
ATOM   1684  OE1  GLN A 254      6.627    0.360  -21.309  1.00 47.62           O
ATOM   1685  NE2  GLN A 254      5.979   -1.634  -22.111  1.00 47.21           N
ATOM   1686  C    GLN A 254      4.937   -0.519  -16.864  1.00 39.08           C
ATOM   1687  O    GLN A 254      3.756   -0.864  -16.934  1.00 39.61           O
ATOM   1688  N    PRO A 255      5.295    0.686  -16.396  1.00 38.40           N
ATOM   1689  CD   PRO A 255      6.649    1.208  -16.154  1.00 37.56           C
ATOM   1690  CA   PRO A 255      4.278    1.646  -15.947  1.00 37.98           C
ATOM   1691  CB   PRO A 255      5.112    2.803  -15.392  1.00 37.50           C
ATOM   1692  CG   PRO A 255      6.410    2.150  -14.998  1.00 38.11           C
ATOM   1693  C    PRO A 255      3.344    2.091  -17.074  1.00 37.43           C
ATOM   1694  O    PRO A 255      3.802    2.533  -18.128  1.00 38.55           O
ATOM   1695  N    ILE A 256      2.039    1.988  -16.842  1.00 36.18           N
ATOM   1696  CA   ILE A 256      1.051    2.362  -17.851  1.00 35.52           C
ATOM   1697  CB   ILE A 256     -0.405    2.062  -17.351  1.00 36.82           C
ATOM   1698  CG2  ILE A 256     -0.733    2.871  -16.092  1.00 36.99           C
ATOM   1699  CG1  ILE A 256     -1.416    2.375  -18.454  1.00 35.40           C
ATOM   1700  CD1  ILE A 256     -1.263    1.510  -19.655  1.00 35.08           C
ATOM   1701  C    ILE A 256      1.156    3.824  -18.304  1.00 36.13           C
ATOM   1702  O    ILE A 256      1.025    4.127  -19.489  1.00 35.31           O
ATOM   1703  N    PHE A 257      1.407    4.732  -17.370  1.00 35.20           N
ATOM   1704  CA   PHE A 257      1.518    6.147  -17.711  1.00 34.85           C
ATOM   1705  CB   PHE A 257      0.415    6.935  -17.004  1.00 33.47           C
ATOM   1706  CG   PHE A 257     -0.962    6.363  -17.183  1.00 32.88           C
ATOM   1707  CD1  PHE A 257     -1.468    6.094  -18.454  1.00 33.61           C
ATOM   1708  CD2  PHE A 257     -1.776    6.136  -16.078  1.00 32.85           C
ATOM   1709  CE1  PHE A 257     -2.767    5.608  -18.625  1.00 33.37           C
ATOM   1710  CE2  PHE A 257     -3.075    5.652  -16.232  1.00 33.48           C
ATOM   1711  CZ   PHE A 257     -3.576    5.386  -17.513  1.00 32.27           C
ATOM   1712  C    PHE A 257      2.895    6.694  -17.297  1.00 35.50           C
ATOM   1713  O    PHE A 257      3.039    7.318  -16.243  1.00 36.23           O
ATOM   1714  N    PRO A 258      3.923    6.469  -18.126  1.00 34.60           N
ATOM   1715  CD   PRO A 258      3.931    5.598  -19.320  1.00 35.11           C
ATOM   1716  CA   PRO A 258      5.275    6.942  -17.819  1.00 33.94           C
ATOM   1717  CB   PRO A 258      6.150    5.942  -18.570  1.00 34.28           C
ATOM   1718  CG   PRO A 258      5.364    5.741  -19.831  1.00 34.54           C
ATOM   1719  C    PRO A 258      5.548    8.384  -18.244  1.00 34.44           C
ATOM   1720  O    PRO A 258      6.310    8.620  -19.179  1.00 35.20           O
ATOM   1721  N    GLY A 259      4.938    9.343  -17.557  1.00 35.84           N
ATOM   1722  CA   GLY A 259      5.150   10.737  -17.900  1.00 37.50           C
ATOM   1723  C    GLY A 259      6.544   11.224  -17.549  1.00 38.70           C
ATOM   1724  O    GLY A 259      7.129   10.785  -16.557  1.00 40.91           O
ATOM   1725  N    ASP A 260      7.094   12.138  -18.341  1.00 38.35           N
ATOM   1726  CA   ASP A 260      8.439   12.629  -18.051  1.00 38.77           C
ATOM   1727  CB   ASP A 260      9.254   12.783  -19.339  1.00 38.24           C
ATOM   1728  CG   ASP A 260      8.814   13.966  -20.173  1.00 39.15           C
ATOM   1729  OD1  ASP A 260      7.989   14.761  -19.681  1.00 40.79           O
ATOM   1730  OD2  ASP A 260      9.300   14.110  -21.318  1.00 38.47           O
ATOM   1731  C    ASP A 260      8.392   13.956  -17.307  1.00 38.87           C
ATOM   1732  O    ASP A 260      9.346   14.730  -17.332  1.00 39.23           O
ATOM   1733  N    SER A 261      7.269   14.219  -16.651  1.00 38.30           N
ATOM   1734  CA   SER A 261      7.089   15.456  -15.887  1.00 37.63           C
ATOM   1735  CB   SER A 261      7.314   16.686  -16.776  1.00 37.36           C
```

FIG. 2-27

```
ATOM   1736  OG   SER A 261       6.101  17.395 -16.984  1.00 38.61           O
ATOM   1737  C    SER A 261       5.681  15.497 -15.306  1.00 36.57           C
ATOM   1738  O    SER A 261       4.803  14.749 -15.734  1.00 35.60           O
ATOM   1739  N    GLY A 262       5.486  16.376 -14.328  1.00 36.31           N
ATOM   1740  CA   GLY A 262       4.201  16.507 -13.670  1.00 35.60           C
ATOM   1741  C    GLY A 262       3.057  16.752 -14.624  1.00 35.74           C
ATOM   1742  O    GLY A 262       1.963  16.220 -14.439  1.00 35.42           O
ATOM   1743  N    VAL A 263       3.321  17.559 -15.647  1.00 37.13           N
ATOM   1744  CA   VAL A 263       2.329  17.905 -16.662  1.00 37.49           C
ATOM   1745  CB   VAL A 263       2.637  19.305 -17.247  1.00 37.26           C
ATOM   1746  CG1  VAL A 263       1.677  19.633 -18.379  1.00 35.65           C
ATOM   1747  CG2  VAL A 263       2.540  20.348 -16.140  1.00 36.95           C
ATOM   1748  C    VAL A 263       2.219  16.876 -17.806  1.00 37.73           C
ATOM   1749  O    VAL A 263       1.121  16.604 -18.291  1.00 37.49           O
ATOM   1750  N    ASP A 264       3.350  16.312 -18.237  1.00 38.22           N
ATOM   1751  CA   ASP A 264       3.350  15.314 -19.315  1.00 37.72           C
ATOM   1752  CB   ASP A 264       4.791  14.912 -19.687  1.00 38.54           C
ATOM   1753  CG   ASP A 264       4.866  13.974 -20.910  1.00 40.71           C
ATOM   1754  OD1  ASP A 264       5.629  12.978 -20.854  1.00 39.65           O
ATOM   1755  OD2  ASP A 264       4.188  14.237 -21.930  1.00 40.32           O
ATOM   1756  C    ASP A 264       2.578  14.089 -18.830  1.00 37.96           C
ATOM   1757  O    ASP A 264       1.984  13.362 -19.629  1.00 38.23           O
ATOM   1758  N    GLN A 265       2.591  13.866 -17.516  1.00 36.44           N
ATOM   1759  CA   GLN A 265       1.886  12.736 -16.928  1.00 35.92           C
ATOM   1760  CB   GLN A 265       1.884  12.839 -15.402  1.00 34.28           C
ATOM   1761  CG   GLN A 265       1.224  11.665 -14.681  1.00 31.51           C
ATOM   1762  CD   GLN A 265       1.858  10.329 -15.022  1.00 30.33           C
ATOM   1763  OE1  GLN A 265       3.017  10.270 -15.422  1.00 29.39           O
ATOM   1764  NE2  GLN A 265       1.104   9.251 -14.852  1.00 27.96           N
ATOM   1765  C    GLN A 265       0.452  12.715 -17.432  1.00 36.53           C
ATOM   1766  O    GLN A 265      -0.083  11.660 -17.765  1.00 38.09           O
ATOM   1767  N    LEU A 266      -0.172  13.884 -17.488  1.00 36.46           N
ATOM   1768  CA   LEU A 266      -1.541  13.973 -17.962  1.00 36.71           C
ATOM   1769  CB   LEU A 266      -2.056  15.407 -17.814  1.00 37.12           C
ATOM   1770  CG   LEU A 266      -3.538  15.664 -18.119  1.00 37.80           C
ATOM   1771  CD1  LEU A 266      -4.408  14.812 -17.208  1.00 37.31           C
ATOM   1772  CD2  LEU A 266      -3.848  17.144 -17.933  1.00 36.02           C
ATOM   1773  C    LEU A 266      -1.580  13.545 -19.426  1.00 36.95           C
ATOM   1774  O    LEU A 266      -2.421  12.736 -19.832  1.00 37.49           O
ATOM   1775  N    VAL A 267      -0.656  14.086 -20.211  1.00 35.66           N
ATOM   1776  CA   VAL A 267      -0.585  13.765 -21.623  1.00 35.47           C
ATOM   1777  CB   VAL A 267       0.640  14.415 -22.262  1.00 33.70           C
ATOM   1778  CG1  VAL A 267       0.717  14.045 -23.732  1.00 33.15           C
ATOM   1779  CG2  VAL A 267       0.563  15.911 -22.082  1.00 32.27           C
ATOM   1780  C    VAL A 267      -0.537  12.254 -21.851  1.00 37.34           C
ATOM   1781  O    VAL A 267      -1.236  11.718 -22.718  1.00 38.55           O
ATOM   1782  N    GLU A 268       0.281  11.564 -21.065  1.00 37.07           N
ATOM   1783  CA   GLU A 268       0.402  10.120 -21.180  1.00 37.46           C
ATOM   1784  CB   GLU A 268       1.543   9.633 -20.287  1.00 37.36           C
ATOM   1785  CG   GLU A 268       2.924   9.971 -20.829  1.00 36.52           C
ATOM   1786  CD   GLU A 268       3.279   9.133 -22.038  1.00 35.99           C
ATOM   1787  OE1  GLU A 268       3.205   7.898 -21.925  1.00 36.05           O
ATOM   1788  OE2  GLU A 268       3.626   9.699 -23.091  1.00 36.19           O
ATOM   1789  C    GLU A 268      -0.907   9.413 -20.809  1.00 37.04           C
ATOM   1790  O    GLU A 268      -1.305   8.449 -21.459  1.00 38.09           O
ATOM   1791  N    ILE A 269      -1.569   9.910 -19.770  1.00 37.52           N
ATOM   1792  CA   ILE A 269      -2.834   9.356 -19.296  1.00 37.73           C
ATOM   1793  CB   ILE A 269      -3.309  10.096 -18.007  1.00 36.56           C
ATOM   1794  CG2  ILE A 269      -4.828  10.031 -17.882  1.00 34.04           C
ATOM   1795  CG1  ILE A 269      -2.607   9.503 -16.778  1.00 36.18           C
ATOM   1796  CD1  ILE A 269      -2.814  10.290 -15.489  1.00 34.76           C
ATOM   1797  C    ILE A 269      -3.896   9.513 -20.377  1.00 38.54           C
ATOM   1798  O    ILE A 269      -4.722   8.622 -20.602  1.00 38.60           O
ATOM   1799  N    ILE A 270      -3.849  10.660 -21.044  1.00 38.32           N
ATOM   1800  CA   ILE A 270      -4.781  11.001 -22.104  1.00 39.17           C
ATOM   1801  CB   ILE A 270      -4.641  12.513 -22.445  1.00 39.97           C
ATOM   1802  CG2  ILE A 270      -5.331  12.835 -23.755  1.00 38.20           C
```

FIG. 2-28

```
ATOM   1803  CG1 ILE A 270      -5.208  13.348 -21.278  1.00 39.82           C
ATOM   1804  CD1 ILE A 270      -4.963  14.850 -21.385  1.00 38.73           C
ATOM   1805  C   ILE A 270      -4.585  10.125 -23.349  1.00 39.59           C
ATOM   1806  O   ILE A 270      -5.536   9.848 -24.082  1.00 38.97           O
ATOM   1807  N   LYS A 271      -3.357   9.663 -23.570  1.00 40.90           N
ATOM   1808  CA  LYS A 271      -3.068   8.813 -24.721  1.00 40.64           C
ATOM   1809  CB  LYS A 271      -1.568   8.512 -24.787  1.00 40.13           C
ATOM   1810  CG  LYS A 271      -0.748   9.757 -25.090  1.00 42.58           C
ATOM   1811  CD  LYS A 271       0.737   9.554 -24.909  1.00 42.52           C
ATOM   1812  CE  LYS A 271       1.337   8.732 -26.016  1.00 44.52           C
ATOM   1813  NZ  LYS A 271       2.826   8.762 -25.924  1.00 46.88           N
ATOM   1814  C   LYS A 271      -3.896   7.524 -24.722  1.00 40.51           C
ATOM   1815  O   LYS A 271      -4.163   6.968 -25.787  1.00 41.45           O
ATOM   1816  N   VAL A 272      -4.309   7.045 -23.549  1.00 38.88           N
ATOM   1817  CA  VAL A 272      -5.135   5.842 -23.523  1.00 37.64           C
ATOM   1818  CB  VAL A 272      -4.547   4.697 -22.608  1.00 36.00           C
ATOM   1819  CG1 VAL A 272      -3.132   5.021 -22.181  1.00 34.52           C
ATOM   1820  CG2 VAL A 272      -5.456   4.435 -21.431  1.00 34.80           C
ATOM   1821  C   VAL A 272      -6.586   6.138 -23.125  1.00 38.01           C
ATOM   1822  O   VAL A 272      -7.507   5.673 -23.796  1.00 40.13           O
ATOM   1823  N   LEU A 273      -6.807   6.904 -22.059  1.00 37.99           N
ATOM   1824  CA  LEU A 273      -8.179   7.217 -21.655  1.00 38.16           C
ATOM   1825  CB  LEU A 273      -8.240   7.773 -20.224  1.00 38.70           C
ATOM   1826  CG  LEU A 273      -7.757   6.955 -19.018  1.00 38.44           C
ATOM   1827  CD1 LEU A 273      -8.285   7.589 -17.741  1.00 35.39           C
ATOM   1828  CD2 LEU A 273      -8.238   5.519 -19.124  1.00 37.96           C
ATOM   1829  C   LEU A 273      -8.769   8.255 -22.602  1.00 38.31           C
ATOM   1830  O   LEU A 273      -9.983   8.459 -22.644  1.00 38.49           O
ATOM   1831  N   GLY A 274      -7.901   8.908 -23.365  1.00 38.28           N
ATOM   1832  CA  GLY A 274      -8.360   9.927 -24.289  1.00 39.28           C
ATOM   1833  C   GLY A 274      -8.656  11.203 -23.528  1.00 40.29           C
ATOM   1834  O   GLY A 274      -8.540  11.234 -22.304  1.00 40.45           O
ATOM   1835  N   THR A 275      -9.038  12.256 -24.244  1.00 40.13           N
ATOM   1836  CA  THR A 275      -9.343  13.533 -23.616  1.00 39.40           C
ATOM   1837  CB  THR A 275      -9.613  14.613 -24.667  1.00 38.37           C
ATOM   1838  OG1 THR A 275      -8.432  14.824 -25.445  1.00 38.15           O
ATOM   1839  CG2 THR A 275     -10.003  15.920 -23.999  1.00 40.01           C
ATOM   1840  C   THR A 275     -10.534  13.460 -22.669  1.00 39.43           C
ATOM   1841  O   THR A 275     -11.481  12.706 -22.896  1.00 40.48           O
ATOM   1842  N   PRO A 276     -10.478  14.224 -21.567  1.00 39.15           N
ATOM   1843  CD  PRO A 276      -9.292  14.916 -21.028  1.00 36.87           C
ATOM   1844  CA  PRO A 276     -11.571  14.236 -20.593  1.00 39.18           C
ATOM   1845  CB  PRO A 276     -10.936  14.876 -19.356  1.00 38.59           C
ATOM   1846  CG  PRO A 276      -9.462  14.719 -19.564  1.00 37.40           C
ATOM   1847  C   PRO A 276     -12.730  15.083 -21.113  1.00 40.09           C
ATOM   1848  O   PRO A 276     -12.521  16.085 -21.812  1.00 40.48           O
ATOM   1849  N   THR A 277     -13.951  14.682 -20.782  1.00 40.81           N
ATOM   1850  CA  THR A 277     -15.129  15.434 -21.193  1.00 40.34           C
ATOM   1851  CB  THR A 277     -16.422  14.621 -20.978  1.00 39.83           C
ATOM   1852  OG1 THR A 277     -16.635  14.400 -19.576  1.00 39.79           O
ATOM   1853  CG2 THR A 277     -16.318  13.272 -21.677  1.00 39.70           C
ATOM   1854  C   THR A 277     -15.151  16.641 -20.277  1.00 41.16           C
ATOM   1855  O   THR A 277     -14.802  16.533 -19.107  1.00 41.62           O
ATOM   1856  N   ARG A 278     -15.539  17.791 -20.808  1.00 42.24           N
ATOM   1857  CA  ARG A 278     -15.580  19.001 -20.004  1.00 42.08           C
ATOM   1858  CB  ARG A 278     -16.412  20.063 -20.704  1.00 43.22           C
ATOM   1859  CG  ARG A 278     -16.829  21.205 -19.784  1.00 45.59           C
ATOM   1860  CD  ARG A 278     -18.085  21.873 -20.331  1.00 46.66           C
ATOM   1861  NE  ARG A 278     -17.938  22.214 -21.753  1.00 43.99           N
ATOM   1862  CZ  ARG A 278     -18.950  22.366 -22.602  1.00 42.69           C
ATOM   1863  NH1 ARG A 278     -20.209  22.211 -22.203  1.00 40.99           N
ATOM   1864  NH2 ARG A 278     -18.694  22.675 -23.856  1.00 44.00           N
ATOM   1865  C   ARG A 278     -16.176  18.711 -18.632  1.00 42.22           C
ATOM   1866  O   ARG A 278     -15.802  19.333 -17.632  1.00 41.88           O
ATOM   1867  N   GLU A 279     -17.109  17.765 -18.585  1.00 42.32           N
ATOM   1868  CA  GLU A 279     -17.746  17.398 -17.323  1.00 42.46           C
ATOM   1869  CB  GLU A 279     -18.976  16.523 -17.577  1.00 42.65           C
```

FIG. 2-29

```
ATOM   1870  CG   GLU A 279     -20.223  17.338 -17.880  1.00 44.20           C
ATOM   1871  CD   GLU A 279     -20.191  17.984 -19.251  1.00 44.08           C
ATOM   1872  OE1  GLU A 279     -20.630  19.149 -19.366  1.00 45.25           O
ATOM   1873  OE2  GLU A 279     -19.740  17.318 -20.208  1.00 43.79           O
ATOM   1874  C    GLU A 279     -16.777  16.679 -16.390  1.00 42.89           C
ATOM   1875  O    GLU A 279     -16.721  16.964 -15.183  1.00 42.65           O
ATOM   1876  N    GLN A 280     -16.017  15.742 -16.950  1.00 41.71           N
ATOM   1877  CA   GLN A 280     -15.035  15.002 -16.166  1.00 41.80           C
ATOM   1878  CB   GLN A 280     -14.256  14.021 -17.063  1.00 42.03           C
ATOM   1879  CG   GLN A 280     -14.986  12.704 -17.349  1.00 41.17           C
ATOM   1880  CD   GLN A 280     -14.402  11.958 -18.542  1.00 42.14           C
ATOM   1881  OE1  GLN A 280     -14.647  10.762 -18.734  1.00 43.58           O
ATOM   1882  NE2  GLN A 280     -13.633  12.666 -19.359  1.00 41.52           N
ATOM   1883  C    GLN A 280     -14.079  16.004 -15.504  1.00 42.21           C
ATOM   1884  O    GLN A 280     -13.876  15.986 -14.279  1.00 42.26           O
ATOM   1885  N    ILE A 281     -13.505  16.885 -16.319  1.00 41.36           N
ATOM   1886  CA   ILE A 281     -12.582  17.908 -15.832  1.00 40.13           C
ATOM   1887  CB   ILE A 281     -12.253  18.926 -16.943  1.00 36.59           C
ATOM   1888  CG2  ILE A 281     -11.573  20.135 -16.354  1.00 36.78           C
ATOM   1889  CG1  ILE A 281     -11.368  18.276 -18.003  1.00 34.62           C
ATOM   1890  CD1  ILE A 281     -11.129  19.152 -19.205  1.00 31.10           C
ATOM   1891  C    ILE A 281     -13.135  18.660 -14.621  1.00 41.45           C
ATOM   1892  O    ILE A 281     -12.388  19.023 -13.710  1.00 41.98           O
ATOM   1893  N    ALA A 282     -14.445  18.884 -14.607  1.00 43.17           N
ATOM   1894  CA   ALA A 282     -15.071  19.600 -13.503  1.00 44.25           C
ATOM   1895  CB   ALA A 282     -16.462  20.074 -13.908  1.00 43.41           C
ATOM   1896  C    ALA A 282     -15.140  18.772 -12.221  1.00 44.67           C
ATOM   1897  O    ALA A 282     -14.983  19.311 -11.124  1.00 45.75           O
ATOM   1898  N    GLU A 283     -15.363  17.466 -12.351  1.00 45.28           N
ATOM   1899  CA   GLU A 283     -15.451  16.591 -11.174  1.00 46.37           C
ATOM   1900  CB   GLU A 283     -16.095  15.249 -11.556  1.00 45.36           C
ATOM   1901  CG   GLU A 283     -17.534  15.386 -12.051  1.00 45.14           C
ATOM   1902  CD   GLU A 283     -17.877  14.415 -13.181  1.00 43.43           C
ATOM   1903  OE1  GLU A 283     -16.988  14.110 -14.002  1.00 42.39           O
ATOM   1904  OE2  GLU A 283     -19.040  13.976 -13.260  1.00 42.18           O
ATOM   1905  C    GLU A 283     -14.084  16.354 -10.518  1.00 47.49           C
ATOM   1906  O    GLU A 283     -14.011  15.926  -9.362  1.00 46.50           O
ATOM   1907  N    MET A 284     -13.014  16.640 -11.263  1.00 49.33           N
ATOM   1908  CA   MET A 284     -11.643  16.477 -10.786  1.00 50.75           C
ATOM   1909  CB   MET A 284     -10.692  16.260 -11.968  1.00 51.56           C
ATOM   1910  CG   MET A 284     -11.121  15.182 -12.960  1.00 50.19           C
ATOM   1911  SD   MET A 284      -9.897  14.944 -14.293  1.00 48.52           S
ATOM   1912  CE   MET A 284      -9.278  13.411 -13.820  1.00 46.37           C
ATOM   1913  C    MET A 284     -11.177  17.704 -10.015  1.00 51.97           C
ATOM   1914  O    MET A 284     -10.594  17.589  -8.939  1.00 51.56           O
ATOM   1915  N    ASN A 285     -11.431  18.873 -10.595  1.00 54.46           N
ATOM   1916  CA   ASN A 285     -11.048  20.155 -10.015  1.00 57.00           C
ATOM   1917  CB   ASN A 285      -9.565  20.420 -10.266  1.00 57.60           C
ATOM   1918  CG   ASN A 285      -9.153  21.819  -9.868  1.00 57.50           C
ATOM   1919  OD1  ASN A 285      -9.503  22.290  -8.789  1.00 57.91           O
ATOM   1920  ND2  ASN A 285      -8.398  22.490 -10.733  1.00 58.00           N
ATOM   1921  C    ASN A 285     -11.876  21.213 -10.721  1.00 58.46           C
ATOM   1922  O    ASN A 285     -11.482  21.723 -11.775  1.00 58.76           O
ATOM   1923  N    PRO A 286     -13.037  21.563 -10.150  1.00 60.34           N
ATOM   1924  CD   PRO A 286     -13.515  21.173  -8.814  1.00 60.68           C
ATOM   1925  CA   PRO A 286     -13.914  22.570 -10.764  1.00 62.52           C
ATOM   1926  CB   PRO A 286     -14.913  22.916  -9.647  1.00 61.75           C
ATOM   1927  CG   PRO A 286     -14.277  22.389  -8.390  1.00 61.21           C
ATOM   1928  C    PRO A 286     -13.224  23.799 -11.361  1.00 64.16           C
ATOM   1929  O    PRO A 286     -13.334  24.060 -12.561  1.00 64.96           O
ATOM   1930  N    ASN A 287     -12.509  24.536 -10.519  1.00 64.92           N
ATOM   1931  CA   ASN A 287     -11.788  25.751 -10.907  1.00 65.00           C
ATOM   1932  CB   ASN A 287     -10.999  26.256  -9.702  1.00 65.58           C
ATOM   1933  CG   ASN A 287     -11.896  26.611  -8.535  1.00 66.70           C
ATOM   1934  OD1  ASN A 287     -12.616  27.610  -8.587  1.00 67.12           O
ATOM   1935  ND2  ASN A 287     -11.870  25.788  -7.477  1.00 66.16           N
ATOM   1936  C    ASN A 287     -10.858  25.616 -12.106  1.00 65.25           C
```

FIG. 2-30

```
ATOM   1937  O    ASN A 287     -11.212   25.013  -13.121  1.00 65.40           O
ATOM   1938  N    ALA A 294      -6.951   19.797  -26.820  1.00 58.74           N
ATOM   1939  CA   ALA A 294      -6.306   18.818  -27.690  1.00 59.85           C
ATOM   1940  CB   ALA A 294      -4.889   18.526  -27.195  1.00 59.11           C
ATOM   1941  C    ALA A 294      -7.133   17.542  -27.682  1.00 60.39           C
ATOM   1942  O    ALA A 294      -7.041   16.738  -26.748  1.00 60.91           O
ATOM   1943  N    ALA A 295      -7.930   17.342  -28.725  1.00 60.05           N
ATOM   1944  CA   ALA A 295      -8.790   16.164  -28.788  1.00 60.52           C
ATOM   1945  CB   ALA A 295     -10.035   16.491  -29.606  1.00 60.07           C
ATOM   1946  C    ALA A 295      -8.158   14.864  -29.293  1.00 60.27           C
ATOM   1947  O    ALA A 295      -7.881   14.711  -30.484  1.00 60.00           O
ATOM   1948  N    ALA A 296      -7.937   13.935  -28.364  1.00 59.99           N
ATOM   1949  CA   ALA A 296      -7.368   12.614  -28.660  1.00 59.12           C
ATOM   1950  CB   ALA A 296      -6.144   12.336  -27.764  1.00 58.66           C
ATOM   1951  C    ALA A 296      -8.478   11.566  -28.420  1.00 58.35           C
ATOM   1952  O    ALA A 296      -9.288   11.691  -27.497  1.00 56.79           O
ATOM   1953  N    ALA A 297      -8.474   10.527  -29.252  1.00 57.71           N
ATOM   1954  CA   ALA A 297      -9.481    9.465  -29.269  1.00 56.86           C
ATOM   1955  CB   ALA A 297      -9.152    8.526  -30.397  1.00 56.58           C
ATOM   1956  C    ALA A 297      -9.913    8.624  -28.065  1.00 56.40           C
ATOM   1957  O    ALA A 297     -11.097    8.628  -27.720  1.00 57.31           O
ATOM   1958  N    ALA A 298      -8.987    7.869  -27.479  1.00 55.04           N
ATOM   1959  CA   ALA A 298      -9.261    6.962  -26.357  1.00 55.07           C
ATOM   1960  CB   ALA A 298     -10.693    7.095  -25.861  1.00 54.15           C
ATOM   1961  C    ALA A 298      -9.045    5.579  -26.935  1.00 55.65           C
ATOM   1962  O    ALA A 298      -9.915    5.027  -27.611  1.00 55.58           O
ATOM   1963  N    HIS A 299      -7.859    5.041  -26.693  1.00 56.14           N
ATOM   1964  CA   HIS A 299      -7.483    3.726  -27.181  1.00 56.37           C
ATOM   1965  CB   HIS A 299      -6.024    3.480  -26.810  1.00 57.10           C
ATOM   1966  CG   HIS A 299      -5.356    2.421  -27.620  1.00 58.88           C
ATOM   1967  CD2  HIS A 299      -4.836    2.446  -28.873  1.00 58.97           C
ATOM   1968  ND1  HIS A 299      -5.083    1.160  -27.123  1.00 59.09           N
ATOM   1969  CE1  HIS A 299      -4.421    0.464  -28.025  1.00 59.40           C
ATOM   1970  NE2  HIS A 299      -4.257    1.223  -29.102  1.00 59.62           N
ATOM   1971  C    HIS A 299      -8.397    2.753  -26.445  1.00 56.28           C
ATOM   1972  O    HIS A 299      -8.802    3.023  -25.318  1.00 56.07           O
ATOM   1973  N    PRO A 300      -8.791    1.642  -27.083  1.00 56.54           N
ATOM   1974  CD   PRO A 300      -8.835    1.298  -28.514  1.00 56.29           C
ATOM   1975  CA   PRO A 300      -9.662    0.754  -26.302  1.00 55.90           C
ATOM   1976  CB   PRO A 300     -10.464    0.005  -27.372  1.00 56.00           C
ATOM   1977  CG   PRO A 300      -9.524   -0.067  -28.497  1.00 56.78           C
ATOM   1978  C    PRO A 300      -8.833   -0.161  -25.415  1.00 55.04           C
ATOM   1979  O    PRO A 300      -7.791   -0.658  -25.816  1.00 54.34           O
ATOM   1980  N    TRP A 301      -9.317   -0.369  -24.197  1.00 55.55           N
ATOM   1981  CA   TRP A 301      -8.649   -1.186  -23.193  1.00 54.35           C
ATOM   1982  CB   TRP A 301      -9.612   -1.464  -22.048  1.00 53.10           C
ATOM   1983  CG   TRP A 301      -9.817   -0.262  -21.215  1.00 53.08           C
ATOM   1984  CD2  TRP A 301      -8.841    0.347  -20.363  1.00 53.35           C
ATOM   1985  CE2  TRP A 301      -9.448    1.488  -19.789  1.00 53.53           C
ATOM   1986  CE3  TRP A 301      -7.517    0.039  -20.031  1.00 52.99           C
ATOM   1987  CD1  TRP A 301     -10.938    0.503  -21.131  1.00 53.76           C
ATOM   1988  NE1  TRP A 301     -10.724    1.563  -20.271  1.00 54.34           N
ATOM   1989  CZ2  TRP A 301      -8.765    2.319  -18.897  1.00 53.27           C
ATOM   1990  CZ3  TRP A 301      -6.840    0.865  -19.145  1.00 52.02           C
ATOM   1991  CH2  TRP A 301      -7.465    1.992  -18.587  1.00 52.23           C
ATOM   1992  C    TRP A 301      -8.024   -2.484  -23.661  1.00 55.61           C
ATOM   1993  O    TRP A 301      -6.807   -2.668  -23.556  1.00 56.30           O
ATOM   1994  N    THR A 302      -8.848   -3.396  -24.158  1.00 55.98           N
ATOM   1995  CA   THR A 302      -8.357   -4.690  -24.636  1.00 55.78           C
ATOM   1996  CB   THR A 302      -9.431   -5.400  -25.463  1.00 56.35           C
ATOM   1997  OG1  THR A 302      -9.720   -4.615  -26.632  1.00 56.40           O
ATOM   1998  CG2  THR A 302     -10.702   -5.573  -24.649  1.00 55.35           C
ATOM   1999  C    THR A 302      -7.111   -4.538  -25.510  1.00 54.98           C
ATOM   2000  O    THR A 302      -6.204   -5.370  -25.465  1.00 54.78           O
ATOM   2001  N    ALA A 303      -7.067   -3.467  -26.297  1.00 53.87           N
ATOM   2002  CA   ALA A 303      -5.927   -3.219  -27.177  1.00 53.50           C
ATOM   2003  CB   ALA A 303      -6.330   -2.230  -28.277  1.00 53.73           C
```

FIG. 2-31

```
ATOM   2004  C    ALA A 303      -4.687  -2.708 -26.438  1.00 53.07           C
ATOM   2005  O    ALA A 303      -3.573  -2.786 -26.954  1.00 52.45           O
ATOM   2006  N    VAL A 304      -4.889  -2.182 -25.233  1.00 52.82           N
ATOM   2007  CA   VAL A 304      -3.799  -1.653 -24.417  1.00 51.75           C
ATOM   2008  CB   VAL A 304      -4.335  -0.685 -23.332  1.00 51.51           C
ATOM   2009  CG1  VAL A 304      -3.235  -0.336 -22.336  1.00 50.47           C
ATOM   2010  CG2  VAL A 304      -4.869   0.575 -23.991  1.00 51.94           C
ATOM   2011  C    VAL A 304      -2.999  -2.749 -23.735  1.00 52.13           C
ATOM   2012  O    VAL A 304      -1.770  -2.686 -23.673  1.00 51.62           O
ATOM   2013  N    PHE A 305      -3.695  -3.749 -23.212  1.00 52.84           N
ATOM   2014  CA   PHE A 305      -3.024  -4.847 -22.535  1.00 54.26           C
ATOM   2015  CB   PHE A 305      -3.991  -5.491 -21.547  1.00 53.32           C
ATOM   2016  CG   PHE A 305      -4.415  -4.542 -20.464  1.00 53.64           C
ATOM   2017  CD1  PHE A 305      -3.547  -4.236 -19.423  1.00 52.52           C
ATOM   2018  CD2  PHE A 305      -5.615  -3.848 -20.555  1.00 52.90           C
ATOM   2019  CE1  PHE A 305      -3.855  -3.248 -18.491  1.00 51.69           C
ATOM   2020  CE2  PHE A 305      -5.937  -2.857 -19.628  1.00 52.96           C
ATOM   2021  CZ   PHE A 305      -5.054  -2.551 -18.591  1.00 51.62           C
ATOM   2022  C    PHE A 305      -2.466  -5.835 -23.543  1.00 56.01           C
ATOM   2023  O    PHE A 305      -2.757  -5.745 -24.736  1.00 56.75           O
ATOM   2024  N    ARG A 306      -1.646  -6.768 -23.083  1.00 57.62           N
ATOM   2025  CA   ARG A 306      -1.041  -7.708 -24.008  1.00 58.81           C
ATOM   2026  CB   ARG A 306       0.166  -8.339 -23.323  1.00 60.98           C
ATOM   2027  CG   ARG A 306       1.068  -7.200 -22.794  1.00 63.97           C
ATOM   2028  CD   ARG A 306       2.446  -7.645 -22.341  1.00 65.88           C
ATOM   2029  NE   ARG A 306       2.354  -8.708 -21.353  1.00 68.68           N
ATOM   2030  CZ   ARG A 306       2.897  -9.910 -21.505  1.00 70.64           C
ATOM   2031  NH1  ARG A 306       3.574 -10.188 -22.613  1.00 71.49           N
ATOM   2032  NH2  ARG A 306       2.751 -10.832 -20.555  1.00 70.53           N
ATOM   2033  C    ARG A 306      -2.070  -8.714 -24.501  1.00 58.04           C
ATOM   2034  O    ARG A 306      -3.124  -8.875 -23.884  1.00 57.71           O
ATOM   2035  N    PRO A 307      -1.792  -9.390 -25.629  1.00 57.71           N
ATOM   2036  CD   PRO A 307      -0.512  -9.466 -26.354  1.00 57.23           C
ATOM   2037  CA   PRO A 307      -2.753 -10.364 -26.162  1.00 56.71           C
ATOM   2038  CB   PRO A 307      -1.933 -11.163 -27.185  1.00 57.14           C
ATOM   2039  CG   PRO A 307      -0.509 -10.905 -26.797  1.00 57.60           C
ATOM   2040  C    PRO A 307      -3.506 -11.252 -25.185  1.00 55.99           C
ATOM   2041  O    PRO A 307      -4.735 -11.214 -25.143  1.00 56.05           O
ATOM   2042  N    ALA A 308      -2.814 -12.061 -24.399  1.00 55.18           N
ATOM   2043  CA   ALA A 308      -3.548 -12.939 -23.488  1.00 54.89           C
ATOM   2044  CB   ALA A 308      -2.860 -14.301 -23.417  1.00 55.13           C
ATOM   2045  C    ALA A 308      -3.814 -12.405 -22.077  1.00 54.03           C
ATOM   2046  O    ALA A 308      -3.862 -13.176 -21.111  1.00 53.36           O
ATOM   2047  N    THR A 309      -3.985 -11.089 -21.959  1.00 52.55           N
ATOM   2048  CA   THR A 309      -4.289 -10.485 -20.666  1.00 51.25           C
ATOM   2049  CB   THR A 309      -4.184  -8.937 -20.702  1.00 50.42           C
ATOM   2050  OG1  THR A 309      -2.826  -8.552 -20.949  1.00 49.95           O
ATOM   2051  CG2  THR A 309      -4.629  -8.339 -19.369  1.00 49.29           C
ATOM   2052  C    THR A 309      -5.734 -10.885 -20.385  1.00 51.40           C
ATOM   2053  O    THR A 309      -6.616 -10.650 -21.205  1.00 51.92           O
ATOM   2054  N    PRO A 310      -5.995 -11.505 -19.226  1.00 51.26           N
ATOM   2055  CD   PRO A 310      -5.074 -11.705 -18.094  1.00 50.93           C
ATOM   2056  CA   PRO A 310      -7.354 -11.937 -18.867  1.00 51.11           C
ATOM   2057  CB   PRO A 310      -7.177 -12.541 -17.480  1.00 50.39           C
ATOM   2058  CG   PRO A 310      -5.707 -12.884 -17.411  1.00 50.33           C
ATOM   2059  C    PRO A 310      -8.385 -10.815 -18.839  1.00 52.32           C
ATOM   2060  O    PRO A 310      -8.104  -9.705 -18.395  1.00 53.05           O
ATOM   2061  N    PRO A 311      -9.611 -11.106 -19.290  1.00 53.08           N
ATOM   2062  CD   PRO A 311     -10.015 -12.447 -19.755  1.00 53.44           C
ATOM   2063  CA   PRO A 311     -10.744 -10.173 -19.351  1.00 51.57           C
ATOM   2064  CB   PRO A 311     -11.907 -11.081 -19.749  1.00 52.03           C
ATOM   2065  CG   PRO A 311     -11.229 -12.133 -20.593  1.00 52.27           C
ATOM   2066  C    PRO A 311     -11.028  -9.416 -18.048  1.00 50.52           C
ATOM   2067  O    PRO A 311     -11.085  -8.186 -18.040  1.00 50.57           O
ATOM   2068  N    GLU A 312     -11.205 -10.149 -16.956  1.00 49.38           N
ATOM   2069  CA   GLU A 312     -11.509  -9.540 -15.661  1.00 49.57           C
ATOM   2070  CB   GLU A 312     -11.887 -10.616 -14.636  1.00 52.21           C
```

FIG. 2-32

```
ATOM   2071  CG   GLU A 312     -12.981  -11.558  -15.123  1.00 57.17           C
ATOM   2072  CD   GLU A 312     -12.454  -12.631  -16.085  1.00 61.67           C
ATOM   2073  OE1  GLU A 312     -11.430  -12.381  -16.777  1.00 63.35           O
ATOM   2074  OE2  GLU A 312     -13.066  -13.730  -16.159  1.00 63.31           O
ATOM   2075  C    GLU A 312     -10.364   -8.688  -15.114  1.00 48.19           C
ATOM   2076  O    GLU A 312     -10.579   -7.823  -14.268  1.00 47.92           O
ATOM   2077  N    ALA A 313      -9.146   -8.937  -15.584  1.00 46.49           N
ATOM   2078  CA   ALA A 313      -8.011   -8.146  -15.140  1.00 44.59           C
ATOM   2079  CB   ALA A 313      -6.703   -8.771  -15.616  1.00 44.73           C
ATOM   2080  C    ALA A 313      -8.214   -6.785  -15.790  1.00 44.14           C
ATOM   2081  O    ALA A 313      -8.220   -5.745  -15.130  1.00 43.86           O
ATOM   2082  N    ILE A 314      -8.413   -6.824  -17.104  1.00 43.08           N
ATOM   2083  CA   ILE A 314      -8.639   -5.639  -17.915  1.00 41.18           C
ATOM   2084  CB   ILE A 314      -8.752   -6.033  -19.411  1.00 40.41           C
ATOM   2085  CG2  ILE A 314      -9.155   -4.825  -20.248  1.00 41.33           C
ATOM   2086  CG1  ILE A 314      -7.418   -6.605  -19.895  1.00 39.50           C
ATOM   2087  CD1  ILE A 314      -7.412   -7.048  -21.341  1.00 34.08           C
ATOM   2088  C    ILE A 314      -9.901   -4.890  -17.478  1.00 41.34           C
ATOM   2089  O    ILE A 314      -9.949   -3.656  -17.518  1.00 41.19           O
ATOM   2090  N    ALA A 315     -10.916   -5.633  -17.050  1.00 40.30           N
ATOM   2091  CA   ALA A 315     -12.179   -5.038  -16.610  1.00 40.52           C
ATOM   2092  CB   ALA A 315     -13.226   -6.132  -16.411  1.00 40.57           C
ATOM   2093  C    ALA A 315     -12.033   -4.227  -15.325  1.00 40.71           C
ATOM   2094  O    ALA A 315     -12.426   -3.059  -15.264  1.00 40.44           O
ATOM   2095  N    LEU A 316     -11.490   -4.870  -14.296  1.00 40.91           N
ATOM   2096  CA   LEU A 316     -11.267   -4.230  -13.006  1.00 40.40           C
ATOM   2097  CB   LEU A 316     -10.508   -5.179  -12.072  1.00 39.91           C
ATOM   2098  CG   LEU A 316      -9.871   -4.584  -10.812  1.00 40.64           C
ATOM   2099  CD1  LEU A 316     -10.929   -3.868   -9.991  1.00 40.79           C
ATOM   2100  CD2  LEU A 316      -9.211   -5.684   -9.998  1.00 40.73           C
ATOM   2101  C    LEU A 316     -10.438   -2.977  -13.232  1.00 40.91           C
ATOM   2102  O    LEU A 316     -10.707   -1.922  -12.663  1.00 41.61           O
ATOM   2103  N    CYS A 317      -9.436   -3.109  -14.085  1.00 40.52           N
ATOM   2104  CA   CYS A 317      -8.546   -2.012  -14.384  1.00 41.58           C
ATOM   2105  CB   CYS A 317      -7.559   -2.435  -15.469  1.00 42.08           C
ATOM   2106  SG   CYS A 317      -5.915   -1.700  -15.303  1.00 45.21           S
ATOM   2107  C    CYS A 317      -9.307   -0.765  -14.815  1.00 42.53           C
ATOM   2108  O    CYS A 317      -9.105    0.319  -14.263  1.00 44.86           O
ATOM   2109  N    SER A 318     -10.198   -0.911  -15.786  1.00 41.97           N
ATOM   2110  CA   SER A 318     -10.967    0.226  -16.280  1.00 40.62           C
ATOM   2111  CB   SER A 318     -11.725   -0.175  -17.547  1.00 40.24           C
ATOM   2112  OG   SER A 318     -12.477   -1.353  -17.324  1.00 41.90           O
ATOM   2113  C    SER A 318     -11.938    0.821  -15.259  1.00 38.87           C
ATOM   2114  O    SER A 318     -12.429    1.939  -15.437  1.00 38.94           O
ATOM   2115  N    ARG A 319     -12.219    0.090  -14.190  1.00 38.10           N
ATOM   2116  CA   ARG A 319     -13.133    0.597  -13.169  1.00 37.95           C
ATOM   2117  CB   ARG A 319     -13.939   -0.554  -12.581  1.00 37.76           C
ATOM   2118  CG   ARG A 319     -14.718   -1.345  -13.612  1.00 41.11           C
ATOM   2119  CD   ARG A 319     -15.900   -0.558  -14.161  1.00 41.66           C
ATOM   2120  NE   ARG A 319     -16.856   -0.246  -13.111  1.00 41.80           N
ATOM   2121  CZ   ARG A 319     -16.939    0.930  -12.502  1.00 42.44           C
ATOM   2122  NH1  ARG A 319     -16.122    1.916  -12.854  1.00 41.07           N
ATOM   2123  NH2  ARG A 319     -17.823    1.103  -11.523  1.00 41.39           N
ATOM   2124  C    ARG A 319     -12.360    1.320  -12.067  1.00 37.01           C
ATOM   2125  O    ARG A 319     -12.942    1.827  -11.105  1.00 36.80           O
ATOM   2126  N    LEU A 320     -11.038    1.343  -12.224  1.00 37.21           N
ATOM   2127  CA   LEU A 320     -10.131    2.001  -11.291  1.00 34.58           C
ATOM   2128  CB   LEU A 320      -8.967    1.067  -10.928  1.00 33.08           C
ATOM   2129  CG   LEU A 320      -9.314   -0.234  -10.196  1.00 34.21           C
ATOM   2130  CD1  LEU A 320      -8.065   -1.085   -9.999  1.00 34.95           C
ATOM   2131  CD2  LEU A 320      -9.957    0.091   -8.866  1.00 34.39           C
ATOM   2132  C    LEU A 320      -9.597    3.253  -11.982  1.00 34.10           C
ATOM   2133  O    LEU A 320      -9.746    4.365  -11.480  1.00 33.59           O
ATOM   2134  N    LEU A 321      -8.989    3.069  -13.149  1.00 33.80           N
ATOM   2135  CA   LEU A 321      -8.441    4.196  -13.884  1.00 34.35           C
ATOM   2136  CB   LEU A 321      -7.388    3.712  -14.878  1.00 34.26           C
ATOM   2137  CG   LEU A 321      -6.230    2.977  -14.200  1.00 32.44           C
```

FIG. 2-33

```
ATOM   2138  CD1 LEU A 321      -5.262   2.484 -15.246  1.00 31.74           C
ATOM   2139  CD2 LEU A 321      -5.555   3.883 -13.196  1.00 30.88           C
ATOM   2140  C   LEU A 321      -9.525   4.999 -14.593  1.00 35.49           C
ATOM   2141  O   LEU A 321      -9.579   5.059 -15.823  1.00 36.36           O
ATOM   2142  N   GLU A 322     -10.404   5.599 -13.797  1.00 35.43           N
ATOM   2143  CA  GLU A 322     -11.473   6.432 -14.319  1.00 36.14           C
ATOM   2144  CB  GLU A 322     -12.804   6.112 -13.636  1.00 36.81           C
ATOM   2145  CG  GLU A 322     -13.327   4.708 -13.914  1.00 41.71           C
ATOM   2146  CD  GLU A 322     -14.649   4.716 -14.678  1.00 42.90           C
ATOM   2147  OE1 GLU A 322     -14.679   5.179 -15.842  1.00 41.53           O
ATOM   2148  OE2 GLU A 322     -15.660   4.266 -14.101  1.00 44.84           O
ATOM   2149  C   GLU A 322     -11.077   7.863 -14.012  1.00 35.88           C
ATOM   2150  O   GLU A 322     -10.357   8.110 -13.045  1.00 36.70           O
ATOM   2151  N   TYR A 323     -11.529   8.802 -14.838  1.00 35.44           N
ATOM   2152  CA  TYR A 323     -11.222  10.208 -14.622  1.00 34.36           C
ATOM   2153  CB  TYR A 323     -11.557  11.034 -15.860  1.00 33.74           C
ATOM   2154  CG  TYR A 323     -10.465  11.092 -16.898  1.00 35.03           C
ATOM   2155  CD1 TYR A 323      -9.187  11.554 -16.573  1.00 35.17           C
ATOM   2156  CE1 TYR A 323      -8.187  11.656 -17.538  1.00 34.69           C
ATOM   2157  CD2 TYR A 323     -10.716  10.731 -18.218  1.00 34.50           C
ATOM   2158  CE2 TYR A 323      -9.724  10.831 -19.187  1.00 35.40           C
ATOM   2159  CZ  TYR A 323      -8.466  11.296 -18.842  1.00 34.82           C
ATOM   2160  OH  TYR A 323      -7.502  11.413 -19.809  1.00 36.67           O
ATOM   2161  C   TYR A 323     -12.033  10.727 -13.453  1.00 35.44           C
ATOM   2162  O   TYR A 323     -11.517  11.434 -12.593  1.00 37.24           O
ATOM   2163  N   THR A 324     -13.313  10.384 -13.431  1.00 35.04           N
ATOM   2164  CA  THR A 324     -14.188  10.825 -12.363  1.00 35.30           C
ATOM   2165  CB  THR A 324     -15.650  10.595 -12.748  1.00 36.60           C
ATOM   2166  OG1 THR A 324     -15.829  10.944 -14.126  1.00 36.29           O
ATOM   2167  CG2 THR A 324     -16.566  11.463 -11.903  1.00 34.56           C
ATOM   2168  C   THR A 324     -13.854  10.052 -11.090  1.00 35.87           C
ATOM   2169  O   THR A 324     -14.071   8.843 -11.014  1.00 35.99           O
ATOM   2170  N   PRO A 325     -13.312  10.747 -10.076  1.00 35.91           N
ATOM   2171  CD  PRO A 325     -13.154  12.210 -10.061  1.00 36.06           C
ATOM   2172  CA  PRO A 325     -12.920  10.176  -8.783  1.00 33.31           C
ATOM   2173  CB  PRO A 325     -12.671  11.411  -7.926  1.00 34.28           C
ATOM   2174  CG  PRO A 325     -12.181  12.409  -8.927  1.00 33.53           C
ATOM   2175  C   PRO A 325     -14.016   9.300  -8.213  1.00 33.32           C
ATOM   2176  O   PRO A 325     -13.763   8.202  -7.714  1.00 32.36           O
ATOM   2177  N   THR A 326     -15.238   9.808  -8.305  1.00 33.06           N
ATOM   2178  CA  THR A 326     -16.431   9.131  -7.810  1.00 31.97           C
ATOM   2179  CB  THR A 326     -17.616  10.095  -7.832  1.00 30.63           C
ATOM   2180  OG1 THR A 326     -17.725  10.679  -9.140  1.00 30.27           O
ATOM   2181  CG2 THR A 326     -17.424  11.196  -6.808  1.00 27.12           C
ATOM   2182  C   THR A 326     -16.821   7.884  -8.597  1.00 33.27           C
ATOM   2183  O   THR A 326     -17.593   7.058  -8.112  1.00 34.16           O
ATOM   2184  N   ALA A 327     -16.290   7.757  -9.810  1.00 34.25           N
ATOM   2185  CA  ALA A 327     -16.588   6.625 -10.689  1.00 34.86           C
ATOM   2186  CB  ALA A 327     -16.352   7.039 -12.135  1.00 36.14           C
ATOM   2187  C   ALA A 327     -15.774   5.374 -10.374  1.00 35.20           C
ATOM   2188  O   ALA A 327     -16.166   4.264 -10.729  1.00 34.98           O
ATOM   2189  N   ARG A 328     -14.641   5.566  -9.706  1.00 36.24           N
ATOM   2190  CA  ARG A 328     -13.750   4.468  -9.351  1.00 34.75           C
ATOM   2191  CB  ARG A 328     -12.403   5.030  -8.916  1.00 35.19           C
ATOM   2192  CG  ARG A 328     -11.799   5.957  -9.934  1.00 34.46           C
ATOM   2193  CD  ARG A 328     -10.585   6.672  -9.397  1.00 35.45           C
ATOM   2194  NE  ARG A 328     -10.222   7.765 -10.295  1.00 36.45           N
ATOM   2195  CZ  ARG A 328      -9.600   8.873  -9.913  1.00 34.14           C
ATOM   2196  NH1 ARG A 328      -9.258   9.048  -8.645  1.00 33.71           N
ATOM   2197  NH2 ARG A 328      -9.349   9.818 -10.798  1.00 34.66           N
ATOM   2198  C   ARG A 328     -14.304   3.591  -8.243  1.00 34.27           C
ATOM   2199  O   ARG A 328     -14.983   4.075  -7.341  1.00 34.24           O
ATOM   2200  N   LEU A 329     -14.004   2.298  -8.311  1.00 33.24           N
ATOM   2201  CA  LEU A 329     -14.451   1.348  -7.294  1.00 34.74           C
ATOM   2202  CB  LEU A 329     -14.062  -0.087  -7.685  1.00 34.43           C
ATOM   2203  CG  LEU A 329     -14.801  -0.864  -8.776  1.00 33.73           C
ATOM   2204  CD1 LEU A 329     -15.221   0.079  -9.884  1.00 35.78           C
```

FIG. 2-34

```
ATOM   2205  CD2 LEU A 329     -13.899  -1.973  -9.298  1.00 31.29           C
ATOM   2206  C   LEU A 329     -13.799   1.676  -5.952  1.00 36.33           C
ATOM   2207  O   LEU A 329     -12.713   2.253  -5.908  1.00 37.77           O
ATOM   2208  N   THR A 330     -14.458   1.311  -4.858  1.00 36.40           N
ATOM   2209  CA  THR A 330     -13.891   1.547  -3.535  1.00 37.29           C
ATOM   2210  CB  THR A 330     -14.984   1.659  -2.446  1.00 35.55           C
ATOM   2211  OG1 THR A 330     -15.569   0.375  -2.215  1.00 34.01           O
ATOM   2212  CG2 THR A 330     -16.068   2.635  -2.877  1.00 34.17           C
ATOM   2213  C   THR A 330     -13.007   0.336  -3.236  1.00 39.23           C
ATOM   2214  O   THR A 330     -13.153  -0.721  -3.867  1.00 39.22           O
ATOM   2215  N   PRO A 331     -12.068   0.476  -2.289  1.00 40.50           N
ATOM   2216  CD  PRO A 331     -11.696   1.695  -1.543  1.00 40.75           C
ATOM   2217  CA  PRO A 331     -11.186  -0.645  -1.950  1.00 41.18           C
ATOM   2218  CB  PRO A 331     -10.453  -0.130  -0.713  1.00 42.21           C
ATOM   2219  CG  PRO A 331     -10.328   1.347  -1.005  1.00 41.19           C
ATOM   2220  C   PRO A 331     -11.953  -1.960  -1.702  1.00 41.93           C
ATOM   2221  O   PRO A 331     -11.566  -3.011  -2.213  1.00 41.11           O
ATOM   2222  N   LEU A 332     -13.038  -1.896  -0.928  1.00 42.86           N
ATOM   2223  CA  LEU A 332     -13.844  -3.085  -0.648  1.00 43.53           C
ATOM   2224  CB  LEU A 332     -14.972  -2.772   0.337  1.00 43.49           C
ATOM   2225  CG  LEU A 332     -14.828  -3.201   1.795  1.00 44.92           C
ATOM   2226  CD1 LEU A 332     -16.215  -3.213   2.429  1.00 45.51           C
ATOM   2227  CD2 LEU A 332     -14.207  -4.600   1.884  1.00 45.53           C
ATOM   2228  C   LEU A 332     -14.462  -3.651  -1.925  1.00 44.53           C
ATOM   2229  O   LEU A 332     -14.463  -4.864  -2.144  1.00 44.34           O
ATOM   2230  N   GLU A 333     -15.002  -2.760  -2.753  1.00 44.91           N
ATOM   2231  CA  GLU A 333     -15.625  -3.140  -4.017  1.00 45.16           C
ATOM   2232  CB  GLU A 333     -16.166  -1.888  -4.726  1.00 46.68           C
ATOM   2233  CG  GLU A 333     -17.658  -1.631  -4.503  1.00 47.09           C
ATOM   2234  CD  GLU A 333     -18.062  -0.178  -4.729  1.00 47.55           C
ATOM   2235  OE1 GLU A 333     -17.739   0.387  -5.803  1.00 47.72           O
ATOM   2236  OE2 GLU A 333     -18.716   0.392  -3.823  1.00 48.41           O
ATOM   2237  C   GLU A 333     -14.619  -3.858  -4.914  1.00 45.21           C
ATOM   2238  O   GLU A 333     -14.940  -4.870  -5.537  1.00 45.13           O
ATOM   2239  N   ALA A 334     -13.397  -3.328  -4.964  1.00 44.79           N
ATOM   2240  CA  ALA A 334     -12.332  -3.914  -5.772  1.00 42.83           C
ATOM   2241  CB  ALA A 334     -11.096  -3.030  -5.725  1.00 42.34           C
ATOM   2242  C   ALA A 334     -12.002  -5.317  -5.270  1.00 41.74           C
ATOM   2243  O   ALA A 334     -11.697  -6.219  -6.060  1.00 41.06           O
ATOM   2244  N   CYS A 335     -12.068  -5.494  -3.956  1.00 40.92           N
ATOM   2245  CA  CYS A 335     -11.801  -6.791  -3.345  1.00 40.45           C
ATOM   2246  CB  CYS A 335     -11.776  -6.668  -1.821  1.00 39.90           C
ATOM   2247  SG  CYS A 335     -10.192  -6.194  -1.127  1.00 36.85           S
ATOM   2248  C   CYS A 335     -12.895  -7.774  -3.740  1.00 40.71           C
ATOM   2249  O   CYS A 335     -12.657  -8.972  -3.863  1.00 40.80           O
ATOM   2250  N   ALA A 336     -14.097  -7.254  -3.951  1.00 40.33           N
ATOM   2251  CA  ALA A 336     -15.208  -8.107  -4.325  1.00 40.56           C
ATOM   2252  CB  ALA A 336     -16.527  -7.465  -3.907  1.00 39.78           C
ATOM   2253  C   ALA A 336     -15.227  -8.428  -5.817  1.00 40.89           C
ATOM   2254  O   ALA A 336     -15.979  -9.299  -6.240  1.00 41.91           O
ATOM   2255  N   HIS A 337     -14.399  -7.753  -6.608  1.00 41.19           N
ATOM   2256  CA  HIS A 337     -14.377  -7.995  -8.052  1.00 41.37           C
ATOM   2257  CB  HIS A 337     -13.260  -7.193  -8.719  1.00 39.59           C
ATOM   2258  CG  HIS A 337     -13.371  -7.135 -10.210  1.00 38.19           C
ATOM   2259  CD2 HIS A 337     -12.984  -8.011 -11.167  1.00 37.50           C
ATOM   2260  ND1 HIS A 337     -13.967  -6.084 -10.874  1.00 37.55           N
ATOM   2261  CE1 HIS A 337     -13.939  -6.313 -12.174  1.00 36.86           C
ATOM   2262  NE2 HIS A 337     -13.347  -7.476 -12.377  1.00 37.70           N
ATOM   2263  C   HIS A 337     -14.214  -9.475  -8.416  1.00 42.44           C
ATOM   2264  O   HIS A 337     -13.699 -10.268  -7.627  1.00 44.49           O
ATOM   2265  N   SER A 338     -14.643  -9.838  -9.621  1.00 42.60           N
ATOM   2266  CA  SER A 338     -14.567 -11.227 -10.073  1.00 43.77           C
ATOM   2267  CB  SER A 338     -15.483 -11.447 -11.287  1.00 42.93           C
ATOM   2268  OG  SER A 338     -14.959 -10.851 -12.460  1.00 43.12           O
ATOM   2269  C   SER A 338     -13.148 -11.700 -10.413  1.00 44.30           C
ATOM   2270  O   SER A 338     -12.863 -12.900 -10.399  1.00 44.38           O
ATOM   2271  N   PHE A 339     -12.268 -10.750 -10.721  1.00 43.61           N
```

FIG. 2-35

| ATOM | 2272 | CA | PHE A 339 | -10.875 | -11.031 | -11.066 | 1.00 | 42.40 | C |
| ATOM | 2273 | CB | PHE A 339 | -10.162 | -9.716 | -11.386 | 1.00 | 42.49 | C |
| ATOM | 2274 | CG | PHE A 339 | -8.664 | -9.811 | -11.400 | 1.00 | 42.23 | C |
| ATOM | 2275 | CD1 | PHE A 339 | -8.002 | -10.561 | -12.364 | 1.00 | 42.19 | C |
| ATOM | 2276 | CD2 | PHE A 339 | -7.912 | -9.089 | -10.485 | 1.00 | 41.69 | C |
| ATOM | 2277 | CE1 | PHE A 339 | -6.608 | -10.577 | -12.420 | 1.00 | 41.90 | C |
| ATOM | 2278 | CE2 | PHE A 339 | -6.523 | -9.101 | -10.534 | 1.00 | 41.64 | C |
| ATOM | 2279 | CZ | PHE A 339 | -5.868 | -9.844 | -11.503 | 1.00 | 41.39 | C |
| ATOM | 2280 | C | PHE A 339 | -10.180 | -11.730 | -9.903 | 1.00 | 42.42 | C |
| ATOM | 2281 | O | PHE A 339 | -9.215 | -12.477 | -10.085 | 1.00 | 40.98 | O |
| ATOM | 2282 | N | PHE A 340 | -10.692 | -11.476 | -8.703 | 1.00 | 42.23 | N |
| ATOM | 2283 | CA | PHE A 340 | -10.132 | -12.060 | -7.499 | 1.00 | 43.07 | C |
| ATOM | 2284 | CB | PHE A 340 | -10.164 | -11.040 | -6.345 | 1.00 | 41.82 | C |
| ATOM | 2285 | CG | PHE A 340 | -9.279 | -9.836 | -6.563 | 1.00 | 41.55 | C |
| ATOM | 2286 | CD1 | PHE A 340 | -7.931 | -9.994 | -6.856 | 1.00 | 40.41 | C |
| ATOM | 2287 | CD2 | PHE A 340 | -9.793 | -8.545 | -6.489 | 1.00 | 40.87 | C |
| ATOM | 2288 | CE1 | PHE A 340 | -7.110 | -8.895 | -7.061 | 1.00 | 38.46 | C |
| ATOM | 2289 | CE2 | PHE A 340 | -8.967 | -7.443 | -6.694 | 1.00 | 38.08 | C |
| ATOM | 2290 | CZ | PHE A 340 | -7.627 | -7.622 | -6.986 | 1.00 | 36.36 | C |
| ATOM | 2291 | C | PHE A 340 | -10.874 | -13.330 | -7.089 | 1.00 | 44.31 | C |
| ATOM | 2292 | O | PHE A 340 | -10.574 | -13.911 | -6.041 | 1.00 | 44.70 | O |
| ATOM | 2293 | N | ASP A 341 | -11.836 | -13.764 | -7.904 | 1.00 | 45.42 | N |
| ATOM | 2294 | CA | ASP A 341 | -12.610 | -14.969 | -7.585 | 1.00 | 46.41 | C |
| ATOM | 2295 | CB | ASP A 341 | -13.536 | -15.362 | -8.748 | 1.00 | 47.54 | C |
| ATOM | 2296 | CG | ASP A 341 | -14.823 | -14.563 | -8.765 | 1.00 | 49.20 | C |
| ATOM | 2297 | OD1 | ASP A 341 | -15.304 | -14.179 | -7.676 | 1.00 | 51.33 | O |
| ATOM | 2298 | OD2 | ASP A 341 | -15.367 | -14.325 | -9.865 | 1.00 | 51.01 | O |
| ATOM | 2299 | C | ASP A 341 | -11.721 | -16.153 | -7.225 | 1.00 | 45.81 | C |
| ATOM | 2300 | O | ASP A 341 | -11.887 | -16.755 | -6.167 | 1.00 | 45.25 | O |
| ATOM | 2301 | N | GLU A 342 | -10.795 | -16.497 | -8.115 | 1.00 | 45.67 | N |
| ATOM | 2302 | CA | GLU A 342 | -9.890 | -17.603 | -7.856 | 1.00 | 46.57 | C |
| ATOM | 2303 | CB | GLU A 342 | -8.648 | -17.487 | -8.746 | 1.00 | 46.51 | C |
| ATOM | 2304 | CG | GLU A 342 | -7.534 | -18.468 | -8.411 | 1.00 | 46.98 | C |
| ATOM | 2305 | CD | GLU A 342 | -6.546 | -18.656 | -9.550 | 1.00 | 48.92 | C |
| ATOM | 2306 | OE1 | GLU A 342 | -6.267 | -17.682 | -10.290 | 1.00 | 48.66 | O |
| ATOM | 2307 | OE2 | GLU A 342 | -6.028 | -19.785 | -9.700 | 1.00 | 50.70 | O |
| ATOM | 2308 | C | GLU A 342 | -9.490 | -17.646 | -6.383 | 1.00 | 47.49 | C |
| ATOM | 2309 | O | GLU A 342 | -9.655 | -18.668 | -5.720 | 1.00 | 49.39 | O |
| ATOM | 2310 | N | LEU A 343 | -8.994 | -16.528 | -5.864 | 1.00 | 48.46 | N |
| ATOM | 2311 | CA | LEU A 343 | -8.567 | -16.438 | -4.467 | 1.00 | 48.57 | C |
| ATOM | 2312 | CB | LEU A 343 | -8.136 | -15.014 | -4.140 | 1.00 | 48.69 | C |
| ATOM | 2313 | CG | LEU A 343 | -7.012 | -14.414 | -4.981 | 1.00 | 48.83 | C |
| ATOM | 2314 | CD1 | LEU A 343 | -6.831 | -12.950 | -4.578 | 1.00 | 49.38 | C |
| ATOM | 2315 | CD2 | LEU A 343 | -5.731 | -15.196 | -4.764 | 1.00 | 47.64 | C |
| ATOM | 2316 | C | LEU A 343 | -9.657 | -16.839 | -3.490 | 1.00 | 48.25 | C |
| ATOM | 2317 | O | LEU A 343 | -9.381 | -17.164 | -2.333 | 1.00 | 47.85 | O |
| ATOM | 2318 | N | ARG A 344 | -10.898 | -16.799 | -3.954 | 1.00 | 48.94 | N |
| ATOM | 2319 | CA | ARG A 344 | -12.033 | -17.144 | -3.110 | 1.00 | 49.59 | C |
| ATOM | 2320 | CB | ARG A 344 | -13.235 | -16.259 | -3.461 | 1.00 | 48.33 | C |
| ATOM | 2321 | CG | ARG A 344 | -13.368 | -15.008 | -2.594 | 1.00 | 45.72 | C |
| ATOM | 2322 | CD | ARG A 344 | -14.537 | -14.175 | -3.056 | 1.00 | 43.72 | C |
| ATOM | 2323 | NE | ARG A 344 | -14.332 | -13.731 | -4.432 | 1.00 | 44.21 | N |
| ATOM | 2324 | CZ | ARG A 344 | -13.747 | -12.586 | -4.765 | 1.00 | 43.16 | C |
| ATOM | 2325 | NH1 | ARG A 344 | -13.319 | -11.763 | -3.815 | 1.00 | 42.10 | N |
| ATOM | 2326 | NH2 | ARG A 344 | -13.570 | -12.277 | -6.044 | 1.00 | 42.04 | N |
| ATOM | 2327 | C | ARG A 344 | -12.415 | -18.617 | -3.195 | 1.00 | 50.83 | C |
| ATOM | 2328 | O | ARG A 344 | -13.345 | -19.068 | -2.525 | 1.00 | 50.94 | O |
| ATOM | 2329 | N | ASP A 345 | -11.693 | -19.361 | -4.024 | 1.00 | 53.45 | N |
| ATOM | 2330 | CA | ASP A 345 | -11.916 | -20.795 | -4.184 | 1.00 | 56.52 | C |
| ATOM | 2331 | CB | ASP A 345 | -11.264 | -21.278 | -5.486 | 1.00 | 57.97 | C |
| ATOM | 2332 | CG | ASP A 345 | -11.282 | -22.797 | -5.645 | 1.00 | 59.58 | C |
| ATOM | 2333 | OD1 | ASP A 345 | -11.441 | -23.523 | -4.634 | 1.00 | 60.61 | O |
| ATOM | 2334 | OD2 | ASP A 345 | -11.108 | -23.265 | -6.798 | 1.00 | 59.79 | O |
| ATOM | 2335 | C | ASP A 345 | -11.244 | -21.470 | -2.992 | 1.00 | 58.37 | C |
| ATOM | 2336 | O | ASP A 345 | -10.114 | -21.109 | -2.626 | 1.00 | 59.06 | O |
| ATOM | 2337 | N | PRO A 346 | -11.930 | -22.449 | -2.366 | 1.00 | 59.44 | N |
| ATOM | 2338 | CD | PRO A 346 | -13.305 | -22.876 | -2.685 | 1.00 | 59.42 | C |

FIG. 2-36

```
ATOM   2339  CA  PRO A 346     -11.415 -23.193  -1.206  1.00 59.00           C
ATOM   2340  CB  PRO A 346     -12.604 -24.045  -0.787  1.00 59.06           C
ATOM   2341  CG  PRO A 346     -13.336 -24.248  -2.083  1.00 59.24           C
ATOM   2342  C   PRO A 346     -10.183 -24.046  -1.515  1.00 58.71           C
ATOM   2343  O   PRO A 346      -9.396 -24.363  -0.619  1.00 58.61           O
ATOM   2344  N   ASN A 347     -10.015 -24.423  -2.776  1.00 57.78           N
ATOM   2345  CA  ASN A 347      -8.864 -25.235  -3.147  1.00 58.46           C
ATOM   2346  CB  ASN A 347      -9.162 -26.054  -4.409  1.00 59.09           C
ATOM   2347  CG  ASN A 347      -9.784 -27.415  -4.093  1.00 60.89           C
ATOM   2348  OD1 ASN A 347     -10.141 -28.168  -5.006  1.00 62.15           O
ATOM   2349  ND2 ASN A 347      -9.908 -27.739  -2.804  1.00 59.76           N
ATOM   2350  C   ASN A 347      -7.581 -24.443  -3.353  1.00 57.60           C
ATOM   2351  O   ASN A 347      -6.528 -24.803  -2.814  1.00 58.54           O
ATOM   2352  N   VAL A 348      -7.675 -23.363  -4.121  1.00 56.54           N
ATOM   2353  CA  VAL A 348      -6.516 -22.525  -4.439  1.00 55.19           C
ATOM   2354  CB  VAL A 348      -6.912 -21.032  -4.565  1.00 54.53           C
ATOM   2355  CG1 VAL A 348      -7.302 -20.471  -3.197  1.00 53.40           C
ATOM   2356  CG2 VAL A 348      -5.738 -20.244  -5.142  1.00 52.92           C
ATOM   2357  C   VAL A 348      -5.343 -22.609  -3.459  1.00 54.19           C
ATOM   2358  O   VAL A 348      -5.527 -22.635  -2.239  1.00 53.99           O
ATOM   2359  N   LYS A 349      -4.138 -22.643  -4.009  1.00 52.88           N
ATOM   2360  CA  LYS A 349      -2.930 -22.680  -3.199  1.00 53.18           C
ATOM   2361  CB  LYS A 349      -2.434 -24.121  -3.004  1.00 53.59           C
ATOM   2362  CG  LYS A 349      -3.410 -24.960  -2.178  1.00 54.30           C
ATOM   2363  CD  LYS A 349      -2.740 -26.072  -1.390  1.00 55.00           C
ATOM   2364  CE  LYS A 349      -3.766 -26.717  -0.487  1.00 55.69           C
ATOM   2365  NZ  LYS A 349      -4.607 -25.643   0.145  1.00 56.42           N
ATOM   2366  C   LYS A 349      -1.908 -21.842  -3.934  1.00 52.37           C
ATOM   2367  O   LYS A 349      -2.186 -21.369  -5.034  1.00 52.46           O
ATOM   2368  N   LEU A 350      -0.749 -21.620  -3.328  1.00 51.87           N
ATOM   2369  CA  LEU A 350       0.274 -20.822  -3.987  1.00 52.34           C
ATOM   2370  CB  LEU A 350       1.186 -20.156  -2.953  1.00 52.15           C
ATOM   2371  CG  LEU A 350       0.565 -19.282  -1.851  1.00 52.10           C
ATOM   2372  CD1 LEU A 350       1.682 -18.533  -1.103  1.00 50.74           C
ATOM   2373  CD2 LEU A 350      -0.406 -18.287  -2.470  1.00 50.83           C
ATOM   2374  C   LEU A 350       1.108 -21.726  -4.877  1.00 52.64           C
ATOM   2375  O   LEU A 350       1.177 -22.935  -4.654  1.00 52.72           O
ATOM   2376  N   PRO A 351       1.738 -21.159  -5.915  1.00 53.29           N
ATOM   2377  CD  PRO A 351       1.750 -19.758  -6.365  1.00 52.61           C
ATOM   2378  CA  PRO A 351       2.564 -21.999  -6.789  1.00 54.12           C
ATOM   2379  CB  PRO A 351       3.074 -21.014  -7.842  1.00 53.24           C
ATOM   2380  CG  PRO A 351       3.030 -19.701  -7.148  1.00 52.07           C
ATOM   2381  C   PRO A 351       3.678 -22.557  -5.915  1.00 55.37           C
ATOM   2382  O   PRO A 351       4.518 -23.356  -6.341  1.00 56.11           O
ATOM   2383  N   ASN A 352       3.649 -22.109  -4.666  1.00 56.49           N
ATOM   2384  CA  ASN A 352       4.603 -22.502  -3.640  1.00 57.08           C
ATOM   2385  CB  ASN A 352       4.561 -21.469  -2.511  1.00 58.52           C
ATOM   2386  CG  ASN A 352       5.877 -21.357  -1.782  1.00 60.70           C
ATOM   2387  OD1 ASN A 352       6.086 -20.441  -0.980  1.00 61.10           O
ATOM   2388  ND2 ASN A 352       6.780 -22.297  -2.053  1.00 62.96           N
ATOM   2389  C   ASN A 352       4.203 -23.873  -3.103  1.00 56.23           C
ATOM   2390  O   ASN A 352       4.960 -24.524  -2.379  1.00 55.40           O
ATOM   2391  N   GLY A 353       2.998 -24.293  -3.478  1.00 55.22           N
ATOM   2392  CA  GLY A 353       2.469 -25.565  -3.029  1.00 54.41           C
ATOM   2393  C   GLY A 353       1.819 -25.363  -1.678  1.00 53.98           C
ATOM   2394  O   GLY A 353       1.046 -26.200  -1.206  1.00 53.52           O
ATOM   2395  N   ARG A 354       2.135 -24.220  -1.069  1.00 54.46           N
ATOM   2396  CA  ARG A 354       1.629 -23.835   0.250  1.00 53.63           C
ATOM   2397  CB  ARG A 354       2.629 -22.881   0.917  1.00 55.58           C
ATOM   2398  CG  ARG A 354       4.062 -23.423   0.967  1.00 59.33           C
ATOM   2399  CD  ARG A 354       5.099 -22.365   1.406  1.00 60.91           C
ATOM   2400  NE  ARG A 354       4.649 -21.593   2.570  1.00 62.44           N
ATOM   2401  CZ  ARG A 354       5.445 -21.140   3.535  1.00 62.67           C
ATOM   2402  NH1 ARG A 354       6.754 -21.381   3.494  1.00 62.47           N
ATOM   2403  NH2 ARG A 354       4.923 -20.443   4.541  1.00 62.38           N
ATOM   2404  C   ARG A 354       0.263 -23.156   0.162  1.00 52.09           C
ATOM   2405  O   ARG A 354      -0.245 -22.883  -0.928  1.00 51.18           O
```

FIG. 2-37

```
ATOM   2406  N    ASP A 355      -0.331 -22.893   1.318  1.00 50.84           N
ATOM   2407  CA   ASP A 355      -1.624 -22.235   1.352  1.00 50.82           C
ATOM   2408  CB   ASP A 355      -2.381 -22.583   2.631  1.00 52.70           C
ATOM   2409  CG   ASP A 355      -2.837 -24.023   2.655  1.00 54.54           C
ATOM   2410  OD1  ASP A 355      -1.988 -24.909   2.900  1.00 56.10           O
ATOM   2411  OD2  ASP A 355      -4.042 -24.271   2.411  1.00 56.26           O
ATOM   2412  C    ASP A 355      -1.479 -20.728   1.243  1.00 49.55           C
ATOM   2413  O    ASP A 355      -0.440 -20.157   1.585  1.00 48.02           O
ATOM   2414  N    THR A 356      -2.539 -20.097   0.754  1.00 48.58           N
ATOM   2415  CA   THR A 356      -2.564 -18.659   0.576  1.00 47.47           C
ATOM   2416  CB   THR A 356      -3.719 -18.215  -0.349  1.00 47.25           C
ATOM   2417  OG1  THR A 356      -4.976 -18.467   0.293  1.00 45.03           O
ATOM   2418  CG2  THR A 356      -3.672 -18.980  -1.666  1.00 46.56           C
ATOM   2419  C    THR A 356      -2.780 -18.014   1.918  1.00 47.60           C
ATOM   2420  O    THR A 356      -3.443 -18.569   2.789  1.00 46.86           O
ATOM   2421  N    PRO A 357      -2.218 -16.821   2.111  1.00 49.03           N
ATOM   2422  CD   PRO A 357      -1.441 -15.987   1.179  1.00 49.37           C
ATOM   2423  CA   PRO A 357      -2.411 -16.150   3.399  1.00 49.41           C
ATOM   2424  CB   PRO A 357      -1.671 -14.819   3.215  1.00 48.92           C
ATOM   2425  CG   PRO A 357      -1.691 -14.596   1.723  1.00 48.93           C
ATOM   2426  C    PRO A 357      -3.908 -15.974   3.645  1.00 50.30           C
ATOM   2427  O    PRO A 357      -4.703 -15.989  -2.702  1.00 50.49           O
ATOM   2428  N    ALA A 358      -4.298 -15.844   4.909  1.00 51.62           N
ATOM   2429  CA   ALA A 358      -5.706 -15.658   5.250  1.00 52.20           C
ATOM   2430  CB   ALA A 358      -5.867 -15.489   6.740  1.00 52.42           C
ATOM   2431  C    ALA A 358      -6.178 -14.409   4.531  1.00 52.79           C
ATOM   2432  O    ALA A 358      -5.658 -13.320   4.756  1.00 53.42           O
ATOM   2433  N    LEU A 359      -7.170 -14.572   3.665  1.00 52.66           N
ATOM   2434  CA   LEU A 359      -7.685 -13.458   2.890  1.00 51.24           C
ATOM   2435  CB   LEU A 359      -7.547 -13.796   1.413  1.00 50.57           C
ATOM   2436  CG   LEU A 359      -6.092 -14.061   1.057  1.00 51.11           C
ATOM   2437  CD1  LEU A 359      -5.981 -14.749  -0.305  1.00 51.48           C
ATOM   2438  CD2  LEU A 359      -5.343 -12.732   1.083  1.00 49.61           C
ATOM   2439  C    LEU A 359      -9.139 -13.162   3.208  1.00 51.43           C
ATOM   2440  O    LEU A 359      -9.751 -12.301   2.570  1.00 50.32           O
ATOM   2441  N    PHE A 360      -9.674 -13.851   4.217  1.00 50.84           N
ATOM   2442  CA   PHE A 360     -11.082 -13.712   4.570  1.00 50.76           C
ATOM   2443  CB   PHE A 360     -11.777 -15.045   4.289  1.00 50.34           C
ATOM   2444  CG   PHE A 360     -11.444 -15.610   2.945  1.00 50.85           C
ATOM   2445  CD1  PHE A 360     -11.719 -14.882   1.793  1.00 50.38           C
ATOM   2446  CD2  PHE A 360     -10.821 -16.851   2.825  1.00 51.14           C
ATOM   2447  CE1  PHE A 360     -11.384 -15.378   0.538  1.00 50.42           C
ATOM   2448  CE2  PHE A 360     -10.481 -17.354   1.570  1.00 50.65           C
ATOM   2449  CZ   PHE A 360     -10.763 -16.614   0.425  1.00 50.63           C
ATOM   2450  C    PHE A 360     -11.449 -13.229   5.966  1.00 50.59           C
ATOM   2451  O    PHE A 360     -12.628 -12.987   6.239  1.00 50.18           O
ATOM   2452  N    ASN A 361     -10.460 -13.071   6.840  1.00 50.45           N
ATOM   2453  CA   ASN A 361     -10.729 -12.626   8.207  1.00 50.61           C
ATOM   2454  CB   ASN A 361      -9.578 -13.042   9.142  1.00 49.90           C
ATOM   2455  CG   ASN A 361      -8.240 -12.440   8.752  1.00 50.50           C
ATOM   2456  OD1  ASN A 361      -7.924 -12.292   7.567  1.00 50.00           O
ATOM   2457  ND2  ASN A 361      -7.430 -12.112   9.756  1.00 50.48           N
ATOM   2458  C    ASN A 361     -10.996 -11.129   8.302  1.00 50.96           C
ATOM   2459  O    ASN A 361     -10.162 -10.356   8.775  1.00 52.45           O
ATOM   2460  N    PHE A 362     -12.184 -10.737   7.857  1.00 51.21           N
ATOM   2461  CA   PHE A 362     -12.606  -9.346   7.876  1.00 50.59           C
ATOM   2462  CB   PHE A 362     -13.675  -9.122   6.810  1.00 47.78           C
ATOM   2463  CG   PHE A 362     -13.130  -9.049   5.421  1.00 44.70           C
ATOM   2464  CD1  PHE A 362     -12.676  -7.838   4.907  1.00 42.85           C
ATOM   2465  CD2  PHE A 362     -13.040 -10.191   4.633  1.00 43.06           C
ATOM   2466  CE1  PHE A 362     -12.143  -7.767   3.630  1.00 41.42           C
ATOM   2467  CE2  PHE A 362     -12.508 -10.127   3.354  1.00 42.51           C
ATOM   2468  CZ   PHE A 362     -12.057  -8.913   2.848  1.00 40.79           C
ATOM   2469  C    PHE A 362     -13.162  -8.944   9.230  1.00 51.70           C
ATOM   2470  O    PHE A 362     -13.708  -9.773   9.955  1.00 52.49           O
ATOM   2471  N    THR A 363     -13.015  -7.665   9.561  1.00 52.86           N
ATOM   2472  CA   THR A 363     -13.513  -7.111  10.812  1.00 54.37           C
```

FIG. 2-38

```
ATOM   2473  CB  THR A 363     -12.428  -6.309  11.523  1.00 54.67           C
ATOM   2474  OG1 THR A 363     -11.932  -5.299  10.632  1.00 55.22           O
ATOM   2475  CG2 THR A 363     -11.288  -7.214  11.953  1.00 53.48           C
ATOM   2476  C   THR A 363     -14.630  -6.142  10.441  1.00 56.47           C
ATOM   2477  O   THR A 363     -14.671  -5.647   9.308  1.00 57.48           O
ATOM   2478  N   THR A 364     -15.528  -5.859  11.383  1.00 57.25           N
ATOM   2479  CA  THR A 364     -16.636  -4.943  11.115  1.00 57.85           C
ATOM   2480  CB  THR A 364     -17.498  -4.674  12.382  1.00 58.49           C
ATOM   2481  OG1 THR A 364     -16.833  -3.728  13.235  1.00 59.58           O
ATOM   2482  CG2 THR A 364     -17.736  -5.971  13.152  1.00 57.89           C
ATOM   2483  C   THR A 364     -16.117  -3.607  10.581  1.00 57.62           C
ATOM   2484  O   THR A 364     -16.735  -2.989   9.711  1.00 58.28           O
ATOM   2485  N   GLN A 365     -14.970  -3.170  11.093  1.00 56.58           N
ATOM   2486  CA  GLN A 365     -14.370  -1.921  10.641  1.00 55.26           C
ATOM   2487  CB  GLN A 365     -13.097  -1.634  11.444  1.00 56.54           C
ATOM   2488  CG  GLN A 365     -12.304  -0.409  10.984  1.00 58.74           C
ATOM   2489  CD  GLN A 365     -12.975   0.905  11.339  1.00 59.20           C
ATOM   2490  OE1 GLN A 365     -13.389   1.108  12.480  1.00 60.19           O
ATOM   2491  NE2 GLN A 365     -13.064   1.811  10.374  1.00 58.78           N
ATOM   2492  C   GLN A 365     -14.040  -2.010   9.144  1.00 54.58           C
ATOM   2493  O   GLN A 365     -14.421  -1.136   8.364  1.00 54.08           O
ATOM   2494  N   GLU A 366     -13.336  -3.067   8.748  1.00 54.01           N
ATOM   2495  CA  GLU A 366     -12.962  -3.255   7.344  1.00 53.44           C
ATOM   2496  CB  GLU A 366     -12.259  -4.600   7.133  1.00 53.01           C
ATOM   2497  CG  GLU A 366     -10.984  -4.816   7.928  1.00 52.95           C
ATOM   2498  CD  GLU A 366     -10.214  -6.037   7.453  1.00 52.66           C
ATOM   2499  OE1 GLU A 366      -9.703  -6.009   6.312  1.00 50.19           O
ATOM   2500  OE2 GLU A 366     -10.122  -7.024   8.221  1.00 53.80           O
ATOM   2501  C   GLU A 366     -14.190  -3.230   6.448  1.00 53.60           C
ATOM   2502  O   GLU A 366     -14.209  -2.579   5.398  1.00 53.96           O
ATOM   2503  N   LEU A 367     -15.214  -3.963   6.865  1.00 53.38           N
ATOM   2504  CA  LEU A 367     -16.451  -4.059   6.100  1.00 53.62           C
ATOM   2505  CB  LEU A 367     -17.166  -5.368   6.471  1.00 52.99           C
ATOM   2506  CG  LEU A 367     -16.446  -6.644   6.008  1.00 52.59           C
ATOM   2507  CD1 LEU A 367     -17.078  -7.883   6.617  1.00 51.21           C
ATOM   2508  CD2 LEU A 367     -16.492  -6.712   4.491  1.00 52.13           C
ATOM   2509  C   LEU A 367     -17.386  -2.860   6.305  1.00 53.60           C
ATOM   2510  O   LEU A 367     -18.321  -2.649   5.528  1.00 53.51           O
ATOM   2511  N   SER A 368     -17.101  -2.062   7.331  1.00 53.33           N
ATOM   2512  CA  SER A 368     -17.919  -0.903   7.676  1.00 52.85           C
ATOM   2513  CB  SER A 368     -17.119   0.077   8.557  1.00 52.99           C
ATOM   2514  OG  SER A 368     -16.008   0.642   7.873  1.00 53.02           O
ATOM   2515  C   SER A 368     -18.573  -0.132   6.524  1.00 52.89           C
ATOM   2516  O   SER A 368     -19.766   0.177   6.588  1.00 53.19           O
ATOM   2517  N   SER A 369     -17.823   0.162   5.467  1.00 52.95           N
ATOM   2518  CA  SER A 369     -18.375   0.937   4.347  1.00 52.47           C
ATOM   2519  CB  SER A 369     -17.262   1.366   3.390  1.00 51.91           C
ATOM   2520  OG  SER A 369     -16.787   0.242   2.664  1.00 52.87           O
ATOM   2521  C   SER A 369     -19.459   0.253   3.524  1.00 51.90           C
ATOM   2522  O   SER A 369     -20.246   0.925   2.855  1.00 51.56           O
ATOM   2523  N   ASN A 370     -19.501  -1.076   3.552  1.00 52.16           N
ATOM   2524  CA  ASN A 370     -20.496  -1.800   2.759  1.00 52.03           C
ATOM   2525  CB  ASN A 370     -20.066  -1.813   1.295  1.00 51.11           C
ATOM   2526  CG  ASN A 370     -21.174  -2.263   0.368  1.00 50.56           C
ATOM   2527  OD1 ASN A 370     -22.125  -2.923   0.791  1.00 49.80           O
ATOM   2528  ND2 ASN A 370     -21.052  -1.918  -0.911  1.00 50.20           N
ATOM   2529  C   ASN A 370     -20.670  -3.234   3.249  1.00 52.70           C
ATOM   2530  O   ASN A 370     -20.342  -4.194   2.541  1.00 53.06           O
ATOM   2531  N   PRO A 371     -21.212  -3.400   4.464  1.00 53.16           N
ATOM   2532  CD  PRO A 371     -21.704  -2.298   5.314  1.00 52.77           C
ATOM   2533  CA  PRO A 371     -21.451  -4.700   5.104  1.00 53.91           C
ATOM   2534  CB  PRO A 371     -22.478  -4.355   6.176  1.00 54.19           C
ATOM   2535  CG  PRO A 371     -22.003  -3.001   6.620  1.00 53.91           C
ATOM   2536  C   PRO A 371     -21.892  -5.873   4.205  1.00 54.75           C
ATOM   2537  O   PRO A 371     -21.268  -6.939   4.210  1.00 54.39           O
ATOM   2538  N   PRO A 372     -22.965  -5.692   3.417  1.00 55.63           N
ATOM   2539  CD  PRO A 372     -23.717  -4.453   3.145  1.00 55.86           C
```

FIG. 2-39

```
ATOM   2540  CA   PRO A 372     -23.426   -6.781    2.550  1.00 55.46           C
ATOM   2541  CB   PRO A 372     -24.550   -6.130    1.743  1.00 55.55           C
ATOM   2542  CG   PRO A 372     -24.174   -4.682    1.727  1.00 56.17           C
ATOM   2543  C    PRO A 372     -22.360   -7.426    1.664  1.00 55.95           C
ATOM   2544  O    PRO A 372     -22.501   -8.582    1.252  1.00 56.38           O
ATOM   2545  N    LEU A 373     -21.294   -6.693    1.363  1.00 55.17           N
ATOM   2546  CA   LEU A 373     -20.230   -7.243    0.523  1.00 54.68           C
ATOM   2547  CB   LEU A 373     -19.148   -6.195    0.285  1.00 54.03           C
ATOM   2548  CG   LEU A 373     -19.512   -5.266   -0.871  1.00 53.60           C
ATOM   2549  CD1  LEU A 373     -18.587   -4.047   -0.899  1.00 53.35           C
ATOM   2550  CD2  LEU A 373     -19.411   -6.060   -2.160  1.00 52.65           C
ATOM   2551  C    LEU A 373     -19.618   -8.478    1.156  1.00 54.91           C
ATOM   2552  O    LEU A 373     -18.864   -9.214    0.513  1.00 54.84           O
ATOM   2553  N    ALA A 374     -19.962   -8.703    2.419  1.00 55.50           N
ATOM   2554  CA   ALA A 374     -19.453   -9.842    3.172  1.00 56.71           C
ATOM   2555  CB   ALA A 374     -19.910   -9.745    4.611  1.00 55.32           C
ATOM   2556  C    ALA A 374     -19.885  -11.174    2.580  1.00 57.62           C
ATOM   2557  O    ALA A 374     -19.199  -12.186    2.733  1.00 58.36           O
ATOM   2558  N    THR A 375     -21.035  -11.177    1.917  1.00 59.03           N
ATOM   2559  CA   THR A 375     -21.536  -12.400    1.310  1.00 60.08           C
ATOM   2560  CB   THR A 375     -22.986  -12.228    0.822  1.00 61.26           C
ATOM   2561  OG1  THR A 375     -23.039  -11.181   -0.159  1.00 63.23           O
ATOM   2562  CG2  THR A 375     -23.904  -11.872    1.992  1.00 60.95           C
ATOM   2563  C    THR A 375     -20.657  -12.801    0.133  1.00 59.42           C
ATOM   2564  O    THR A 375     -20.618  -13.972   -0.245  1.00 59.35           O
ATOM   2565  N    ILE A 376     -19.950  -11.829   -0.443  1.00 59.10           N
ATOM   2566  CA   ILE A 376     -19.065  -12.118   -1.571  1.00 58.87           C
ATOM   2567  CB   ILE A 376     -19.066  -11.004   -2.630  1.00 58.90           C
ATOM   2568  CG2  ILE A 376     -18.577  -11.580   -3.964  1.00 59.59           C
ATOM   2569  CG1  ILE A 376     -20.467  -10.410   -2.795  1.00 58.91           C
ATOM   2570  CD1  ILE A 376     -20.495   -9.205   -3.732  1.00 57.97           C
ATOM   2571  C    ILE A 376     -17.621  -12.261   -1.121  1.00 58.37           C
ATOM   2572  O    ILE A 376     -16.918  -13.188   -1.544  1.00 58.72           O
ATOM   2573  N    LEU A 377     -17.189  -11.347   -0.261  1.00 57.31           N
ATOM   2574  CA   LEU A 377     -15.816  -11.328    0.241  1.00 55.73           C
ATOM   2575  CB   LEU A 377     -15.561  -10.021    0.990  1.00 53.43           C
ATOM   2576  CG   LEU A 377     -15.851   -8.750    0.194  1.00 51.99           C
ATOM   2577  CD1  LEU A 377     -15.803   -7.562    1.123  1.00 53.19           C
ATOM   2578  CD2  LEU A 377     -14.854   -8.603   -0.933  1.00 50.62           C
ATOM   2579  C    LEU A 377     -15.483  -12.503    1.145  1.00 55.73           C
ATOM   2580  O    LEU A 377     -14.343  -12.977    1.162  1.00 55.48           O
ATOM   2581  N    ILE A 378     -16.474  -12.956    1.906  1.00 56.09           N
ATOM   2582  CA   ILE A 378     -16.289  -14.080    2.814  1.00 56.91           C
ATOM   2583  CB   ILE A 378     -16.880  -13.797    4.212  1.00 55.69           C
ATOM   2584  CG2  ILE A 378     -16.492  -14.923    5.169  1.00 55.43           C
ATOM   2585  CG1  ILE A 378     -16.358  -12.467    4.749  1.00 54.61           C
ATOM   2586  CD1  ILE A 378     -16.812  -12.162    6.163  1.00 54.48           C
ATOM   2587  C    ILE A 378     -17.011  -15.276    2.215  1.00 58.44           C
ATOM   2588  O    ILE A 378     -18.211  -15.468    2.444  1.00 58.49           O
ATOM   2589  N    PRO A 379     -16.287  -16.103    1.445  1.00 59.68           N
ATOM   2590  CD   PRO A 379     -14.817  -16.157    1.322  1.00 59.74           C
ATOM   2591  CA   PRO A 379     -16.906  -17.274    0.821  1.00 60.91           C
ATOM   2592  CB   PRO A 379     -15.763  -17.873    0.011  1.00 60.81           C
ATOM   2593  CG   PRO A 379     -14.580  -17.587    0.889  1.00 60.55           C
ATOM   2594  C    PRO A 379     -17.460  -18.238    1.852  1.00 62.30           C
ATOM   2595  O    PRO A 379     -17.127  -18.165    3.035  1.00 63.05           O
ATOM   2596  N    PRO A 380     -18.329  -19.149    1.417  1.00 63.51           N
ATOM   2597  CD   PRO A 380     -18.894  -19.214    0.058  1.00 64.61           C
ATOM   2598  CA   PRO A 380     -18.951  -20.147    2.289  1.00 64.32           C
ATOM   2599  CB   PRO A 380     -19.811  -20.957    1.318  1.00 65.00           C
ATOM   2600  CG   PRO A 380     -20.206  -19.940    0.298  1.00 65.00           C
ATOM   2601  C    PRO A 380     -17.934  -21.028    3.017  1.00 64.27           C
ATOM   2602  O    PRO A 380     -17.966  -21.146    4.242  1.00 63.29           O
ATOM   2603  N    HIS A 381     -17.027  -21.621    2.252  1.00 65.26           N
ATOM   2604  CA   HIS A 381     -16.015  -22.509    2.816  1.00 66.98           C
ATOM   2605  CB   HIS A 381     -15.143  -23.070    1.701  1.00 67.65           C
ATOM   2606  CG   HIS A 381     -14.133  -22.098    1.188  1.00 69.29           C
```

FIG. 2-40

```
ATOM   2607  CD2 HIS A 381     -14.127 -21.319   0.079  1.00 70.04           C
ATOM   2608  ND1 HIS A 381     -12.954 -21.832   1.854  1.00 69.56           N
ATOM   2609  CE1 HIS A 381     -12.264 -20.931   1.174  1.00 70.10           C
ATOM   2610  NE2 HIS A 381     -12.951 -20.603   0.094  1.00 70.09           N
ATOM   2611  C   HIS A 381     -15.127 -21.813   3.843  1.00 68.17           C
ATOM   2612  O   HIS A 381     -14.208 -22.422   4.394  1.00 67.88           O
ATOM   2613  N   ALA A 382     -15.393 -20.528   4.084  1.00 70.08           N
ATOM   2614  CA  ALA A 382     -14.631 -19.744   5.057  1.00 71.17           C
ATOM   2615  CB  ALA A 382     -14.318 -18.373   4.491  1.00 70.98           C
ATOM   2616  C   ALA A 382     -15.428 -19.618   6.349  1.00 72.43           C
ATOM   2617  O   ALA A 382     -14.911 -19.885   7.434  1.00 73.01           O
ATOM   2618  N   ARG A 383     -16.691 -19.214   6.228  1.00 73.90           N
ATOM   2619  CA  ARG A 383     -17.571 -19.082   7.388  1.00 74.74           C
ATOM   2620  CB  ARG A 383     -18.968 -18.602   6.970  1.00 74.73           C
ATOM   2621  CG  ARG A 383     -19.019 -17.178   6.450  1.00 75.00           C
ATOM   2622  CD  ARG A 383     -19.417 -17.126   4.980  1.00 75.80           C
ATOM   2623  NE  ARG A 383     -20.757 -17.673   4.746  1.00 76.47           N
ATOM   2624  CZ  ARG A 383     -21.480 -17.447   3.650  1.00 76.89           C
ATOM   2625  NH1 ARG A 383     -20.998 -16.680   2.678  1.00 77.31           N
ATOM   2626  NH2 ARG A 383     -22.687 -17.989   3.529  1.00 77.31           N
ATOM   2627  C   ARG A 383     -17.696 -20.430   8.075  1.00 75.86           C
ATOM   2628  O   ARG A 383     -17.685 -20.461   9.334  1.00 76.70           O
ATOM   2629  OXT ARG A 383     -17.825 -21.433   7.334  1.00 76.46           O
TER    2630      ARG A 383
ATOM   2631  CB  VAL B  37     -20.058  29.474  41.282  1.00 50.23           C
ATOM   2632  CG1 VAL B  37     -19.164  30.434  42.065  1.00 51.03           C
ATOM   2633  CG2 VAL B  37     -19.539  29.356  39.846  1.00 50.70           C
ATOM   2634  C   VAL B  37     -20.007  28.289  43.475  1.00 49.38           C
ATOM   2635  O   VAL B  37     -20.999  28.679  44.082  1.00 49.30           O
ATOM   2636  N   VAL B  37     -21.220  27.264  41.530  1.00 49.26           N
ATOM   2637  CA  VAL B  37     -20.054  28.084  41.961  1.00 49.59           C
ATOM   2638  N   THR B  38     -18.852  28.012  44.080  1.00 48.95           N
ATOM   2639  CA  THR B  38     -18.669  28.187  45.522  1.00 47.55           C
ATOM   2640  CB  THR B  38     -18.120  26.908  46.209  1.00 48.42           C
ATOM   2641  OG1 THR B  38     -18.993  25.801  45.956  1.00 50.13           O
ATOM   2642  CG2 THR B  38     -18.014  27.122  47.718  1.00 46.95           C
ATOM   2643  C   THR B  38     -17.652  29.302  45.755  1.00 46.11           C
ATOM   2644  O   THR B  38     -16.672  29.422  45.016  1.00 44.42           O
ATOM   2645  N   THR B  39     -17.902  30.123  46.773  1.00 44.03           N
ATOM   2646  CA  THR B  39     -16.994  31.218  47.120  1.00 42.02           C
ATOM   2647  CB  THR B  39     -17.583  32.610  46.761  1.00 41.11           C
ATOM   2648  OG1 THR B  39     -17.682  32.741  45.339  1.00 39.79           O
ATOM   2649  CG2 THR B  39     -16.674  33.718  47.294  1.00 40.13           C
ATOM   2650  C   THR B  39     -16.679  31.190  48.609  1.00 40.98           C
ATOM   2651  O   THR B  39     -17.575  31.194  49.452  1.00 41.19           O
ATOM   2652  N   VAL B  40     -15.394  31.159  48.925  1.00 39.56           N
ATOM   2653  CA  VAL B  40     -14.963  31.132  50.309  1.00 37.76           C
ATOM   2654  CB  VAL B  40     -14.394  29.753  50.679  1.00 37.56           C
ATOM   2655  CG1 VAL B  40     -15.456  28.689  50.477  1.00 36.32           C
ATOM   2656  CG2 VAL B  40     -13.168  29.451  49.838  1.00 34.19           C
ATOM   2657  C   VAL B  40     -13.883  32.174  50.505  1.00 37.38           C
ATOM   2658  O   VAL B  40     -13.223  32.588  49.553  1.00 37.63           O
ATOM   2659  N   VAL B  41     -13.721  32.618  51.738  1.00 36.86           N
ATOM   2660  CA  VAL B  41     -12.694  33.599  52.047  1.00 38.31           C
ATOM   2661  CB  VAL B  41     -13.173  34.565  53.166  1.00 38.32           C
ATOM   2662  CG1 VAL B  41     -12.048  35.518  53.568  1.00 36.48           C
ATOM   2663  CG2 VAL B  41     -14.380  35.353  52.676  1.00 36.89           C
ATOM   2664  C   VAL B  41     -11.530  32.744  52.533  1.00 38.42           C
ATOM   2665  O   VAL B  41     -11.577  32.201  53.635  1.00 39.50           O
ATOM   2666  N   ALA B  42     -10.504  32.595  51.704  1.00 38.73           N
ATOM   2667  CA  ALA B  42      -9.367  31.758  52.066  1.00 40.59           C
ATOM   2668  CB  ALA B  42      -9.336  30.531  51.164  1.00 41.05           C
ATOM   2669  C   ALA B  42      -8.016  32.459  52.024  1.00 40.82           C
ATOM   2670  O   ALA B  42      -7.743  33.256  51.124  1.00 41.64           O
ATOM   2671  N   THR B  43      -7.163  32.135  52.995  1.00 40.99           N
ATOM   2672  CA  THR B  43      -5.822  32.718  53.086  1.00 41.48           C
ATOM   2673  CB  THR B  43      -5.305  32.702  54.528  1.00 41.89           C
```

FIG. 2-41

| ATOM | 2674 | OG1 | THR | B | 43 | -6.371 | 33.019 | 55.432 | 1.00 | 43.62 | O |
| --- | --- | --- | --- | --- | --- | --- | --- | --- | --- | --- | --- |
| ATOM | 2675 | CG2 | THR | B | 43 | -4.190 | 33.715 | 54.694 | 1.00 | 41.53 | C |
| ATOM | 2676 | C | THR | B | 43 | -4.838 | 31.910 | 52.244 | 1.00 | 42.26 | C |
| ATOM | 2677 | O | THR | B | 43 | -4.904 | 30.684 | 52.228 | 1.00 | 42.77 | O |
| ATOM | 2678 | N | PRO | B | 44 | -3.904 | 32.581 | 51.545 | 1.00 | 44.24 | N |
| ATOM | 2679 | CD | PRO | B | 44 | -3.765 | 34.035 | 51.378 | 1.00 | 43.55 | C |
| ATOM | 2680 | CA | PRO | B | 44 | -2.921 | 31.872 | 50.714 | 1.00 | 46.62 | C |
| ATOM | 2681 | CB | PRO | B | 44 | -2.147 | 33.006 | 50.039 | 1.00 | 45.72 | C |
| ATOM | 2682 | CG | PRO | B | 44 | -3.142 | 34.132 | 50.006 | 1.00 | 44.37 | C |
| ATOM | 2683 | C | PRO | B | 44 | -2.007 | 30.981 | 51.557 | 1.00 | 48.92 | C |
| ATOM | 2684 | O | PRO | B | 44 | -1.560 | 31.384 | 52.631 | 1.00 | 50.13 | O |
| ATOM | 2685 | N | GLY | B | 45 | -1.733 | 29.775 | 51.065 | 1.00 | 51.64 | N |
| ATOM | 2686 | CA | GLY | B | 45 | -0.887 | 28.848 | 51.797 | 1.00 | 55.52 | C |
| ATOM | 2687 | C | GLY | B | 45 | 0.452 | 29.452 | 52.151 | 1.00 | 58.29 | C |
| ATOM | 2688 | O | GLY | B | 45 | 0.861 | 29.454 | 53.314 | 1.00 | 57.94 | O |
| ATOM | 2689 | N | ASP | B | 46 | 1.144 | 29.961 | 51.142 | 1.00 | 61.47 | N |
| ATOM | 2690 | CA | ASP | B | 46 | 2.441 | 30.586 | 51.354 | 1.00 | 65.35 | C |
| ATOM | 2691 | CB | ASP | B | 46 | 3.532 | 29.834 | 50.576 | 1.00 | 67.14 | C |
| ATOM | 2692 | CG | ASP | B | 46 | 4.937 | 30.301 | 50.932 | 1.00 | 69.84 | C |
| ATOM | 2693 | OD1 | ASP | B | 46 | 5.887 | 29.939 | 50.194 | 1.00 | 70.82 | O |
| ATOM | 2694 | OD2 | ASP | B | 46 | 5.096 | 31.023 | 51.951 | 1.00 | 70.56 | O |
| ATOM | 2695 | C | ASP | B | 46 | 2.352 | 32.034 | 50.880 | 1.00 | 66.66 | C |
| ATOM | 2696 | O | ASP | B | 46 | 2.016 | 32.312 | 49.726 | 1.00 | 66.32 | O |
| ATOM | 2697 | N | GLY | B | 47 | 2.651 | 32.950 | 51.793 | 1.00 | 67.33 | N |
| ATOM | 2698 | CA | GLY | B | 47 | 2.609 | 34.360 | 51.469 | 1.00 | 67.70 | C |
| ATOM | 2699 | C | GLY | B | 47 | 2.164 | 35.194 | 52.650 | 1.00 | 68.35 | C |
| ATOM | 2700 | O | GLY | B | 47 | 2.301 | 34.765 | 53.804 | 1.00 | 69.52 | O |
| ATOM | 2701 | N | PRO | B | 48 | 1.629 | 36.402 | 52.393 | 1.00 | 67.98 | N |
| ATOM | 2702 | CD | PRO | B | 48 | 1.455 | 37.021 | 51.064 | 1.00 | 67.52 | C |
| ATOM | 2703 | CA | PRO | B | 48 | 1.162 | 37.298 | 53.450 | 1.00 | 66.30 | C |
| ATOM | 2704 | CB | PRO | B | 48 | 1.149 | 38.651 | 52.757 | 1.00 | 66.93 | C |
| ATOM | 2705 | CG | PRO | B | 48 | 0.672 | 38.289 | 51.388 | 1.00 | 67.24 | C |
| ATOM | 2706 | C | PRO | B | 48 | -0.221 | 36.847 | 53.888 | 1.00 | 65.17 | C |
| ATOM | 2707 | O | PRO | B | 48 | -1.131 | 36.721 | 53.069 | 1.00 | 64.50 | O |
| ATOM | 2708 | N | ASP | B | 49 | -0.362 | 36.577 | 55.179 | 1.00 | 64.17 | N |
| ATOM | 2709 | CA | ASP | B | 49 | -1.633 | 36.137 | 55.759 | 1.00 | 63.41 | C |
| ATOM | 2710 | CB | ASP | B | 49 | -1.449 | 35.939 | 57.269 | 1.00 | 64.50 | C |
| ATOM | 2711 | CG | ASP | B | 49 | -2.715 | 35.485 | 57.965 | 1.00 | 65.97 | C |
| ATOM | 2712 | OD1 | ASP | B | 49 | -3.726 | 36.224 | 57.894 | 1.00 | 66.87 | O |
| ATOM | 2713 | OD2 | ASP | B | 49 | -2.697 | 34.394 | 58.594 | 1.00 | 66.31 | O |
| ATOM | 2714 | C | ASP | B | 49 | -2.701 | 37.192 | 55.477 | 1.00 | 62.55 | C |
| ATOM | 2715 | O | ASP | B | 49 | -3.013 | 38.018 | 56.326 | 1.00 | 63.42 | O |
| ATOM | 2716 | N | ARG | B | 50 | -3.272 | 37.146 | 54.277 | 1.00 | 61.63 | N |
| ATOM | 2717 | CA | ARG | B | 50 | -4.278 | 38.124 | 53.855 | 1.00 | 59.75 | C |
| ATOM | 2718 | CB | ARG | B | 50 | -3.595 | 39.121 | 52.920 | 1.00 | 60.95 | C |
| ATOM | 2719 | CG | ARG | B | 50 | -4.148 | 40.531 | 52.938 | 1.00 | 64.27 | C |
| ATOM | 2720 | CD | ARG | B | 50 | -4.762 | 40.954 | 51.601 | 1.00 | 65.68 | C |
| ATOM | 2721 | NE | ARG | B | 50 | -3.909 | 40.711 | 50.439 | 1.00 | 67.78 | N |
| ATOM | 2722 | CZ | ARG | B | 50 | -3.797 | 39.536 | 49.815 | 1.00 | 70.13 | C |
| ATOM | 2723 | NH1 | ARG | B | 50 | -4.481 | 38.485 | 50.246 | 1.00 | 69.94 | N |
| ATOM | 2724 | NH2 | ARG | B | 50 | -3.029 | 39.420 | 48.732 | 1.00 | 70.44 | N |
| ATOM | 2725 | C | ARG | B | 50 | -5.435 | 37.418 | 53.136 | 1.00 | 57.59 | C |
| ATOM | 2726 | O | ARG | B | 50 | -5.366 | 37.185 | 51.928 | 1.00 | 57.78 | O |
| ATOM | 2727 | N | PRO | B | 51 | -6.522 | 37.090 | 53.864 | 1.00 | 54.47 | N |
| ATOM | 2728 | CD | PRO | B | 51 | -6.851 | 37.484 | 55.244 | 1.00 | 53.24 | C |
| ATOM | 2729 | CA | PRO | B | 51 | -7.654 | 36.403 | 53.232 | 1.00 | 52.05 | C |
| ATOM | 2730 | CB | PRO | B | 51 | -8.640 | 36.225 | 54.380 | 1.00 | 51.39 | C |
| ATOM | 2731 | CG | PRO | B | 51 | -8.360 | 37.411 | 55.239 | 1.00 | 52.69 | C |
| ATOM | 2732 | C | PRO | B | 51 | -8.269 | 37.121 | 52.034 | 1.00 | 50.97 | C |
| ATOM | 2733 | O | PRO | B | 51 | -8.447 | 38.340 | 52.035 | 1.00 | 51.40 | O |
| ATOM | 2734 | N | GLN | B | 52 | -8.574 | 36.341 | 51.000 | 1.00 | 49.50 | N |
| ATOM | 2735 | CA | GLN | B | 52 | -9.178 | 36.852 | 49.781 | 1.00 | 47.21 | C |
| ATOM | 2736 | CB | GLN | B | 52 | -8.121 | 37.039 | 48.688 | 1.00 | 47.79 | C |
| ATOM | 2737 | CG | GLN | B | 52 | -6.961 | 36.065 | 48.739 | 1.00 | 49.25 | C |
| ATOM | 2738 | CD | GLN | B | 52 | -5.873 | 36.399 | 47.720 | 1.00 | 51.16 | C |
| ATOM | 2739 | OE1 | GLN | B | 52 | -6.057 | 36.221 | 46.510 | 1.00 | 50.86 | O |
| ATOM | 2740 | NE2 | GLN | B | 52 | -4.735 | 36.892 | 48.206 | 1.00 | 51.80 | N |

FIG. 2-42

```
ATOM   2741  C    GLN B  52     -10.240  35.894  49.314  1.00  46.22           C
ATOM   2742  O    GLN B  52     -10.154  34.689  49.561  1.00  46.33           O
ATOM   2743  N    GLU B  53     -11.260  36.437  48.667  1.00  45.98           N
ATOM   2744  CA   GLU B  53     -12.343  35.620  48.152  1.00  45.32           C
ATOM   2745  CB   GLU B  53     -13.448  36.504  47.558  1.00  45.45           C
ATOM   2746  CG   GLU B  53     -14.385  37.108  48.599  1.00  46.12           C
ATOM   2747  CD   GLU B  53     -15.479  37.960  47.989  1.00  47.39           C
ATOM   2748  OE1  GLU B  53     -15.741  37.812  46.774  1.00  48.63           O
ATOM   2749  OE2  GLU B  53     -16.088  38.766  48.726  1.00  46.63           O
ATOM   2750  C    GLU B  53     -11.766  34.711  47.085  1.00  44.63           C
ATOM   2751  O    GLU B  53     -10.939  35.126  46.280  1.00  43.68           O
ATOM   2752  N    VAL B  54     -12.194  33.459  47.104  1.00  43.86           N
ATOM   2753  CA   VAL B  54     -11.738  32.483  46.135  1.00  43.57           C
ATOM   2754  CB   VAL B  54     -10.728  31.510  46.760  1.00  44.48           C
ATOM   2755  CG1  VAL B  54     -10.445  30.371  45.797  1.00  45.81           C
ATOM   2756  CG2  VAL B  54      -9.443  32.245  47.115  1.00  43.58           C
ATOM   2757  C    VAL B  54     -12.944  31.693  45.649  1.00  44.32           C
ATOM   2758  O    VAL B  54     -13.739  31.196  46.451  1.00  43.53           O
ATOM   2759  N    SER B  55     -13.079  31.578  44.333  1.00  44.27           N
ATOM   2760  CA   SER B  55     -14.199  30.842  43.766  1.00  46.06           C
ATOM   2761  CB   SER B  55     -15.023  31.754  42.848  1.00  47.05           C
ATOM   2762  OG   SER B  55     -15.829  32.639  43.615  1.00  48.48           O
ATOM   2763  C    SER B  55     -13.786  29.588  43.005  1.00  46.10           C
ATOM   2764  O    SER B  55     -12.786  29.573  42.282  1.00  45.36           O
ATOM   2765  N    TYR B  56     -14.567  28.529  43.184  1.00  45.29           N
ATOM   2766  CA   TYR B  56     -14.314  27.260  42.520  1.00  45.49           C
ATOM   2767  CB   TYR B  56     -13.357  26.387  43.351  1.00  42.92           C
ATOM   2768  CG   TYR B  56     -13.875  25.962  44.714  1.00  39.85           C
ATOM   2769  CD1  TYR B  56     -14.824  24.947  44.846  1.00  37.77           C
ATOM   2770  CE1  TYR B  56     -15.295  24.555  46.102  1.00  36.53           C
ATOM   2771  CD2  TYR B  56     -13.397  26.570  45.877  1.00  39.44           C
ATOM   2772  CE2  TYR B  56     -13.857  26.190  47.131  1.00  38.51           C
ATOM   2773  CZ   TYR B  56     -14.801  25.176  47.239  1.00  38.47           C
ATOM   2774  OH   TYR B  56     -15.253  24.813  48.491  1.00  38.46           O
ATOM   2775  C    TYR B  56     -15.619  26.521  42.294  1.00  47.69           C
ATOM   2776  O    TYR B  56     -16.589  26.700  43.031  1.00  47.56           O
ATOM   2777  N    THR B  57     -15.636  25.686  41.262  1.00  49.56           N
ATOM   2778  CA   THR B  57     -16.821  24.904  40.931  1.00  50.95           C
ATOM   2779  CB   THR B  57     -17.699  25.652  39.899  1.00  51.11           C
ATOM   2780  OG1  THR B  57     -18.944  24.963  39.743  1.00  50.33           O
ATOM   2781  CG2  THR B  57     -16.990  25.747  38.553  1.00  51.34           C
ATOM   2782  C    THR B  57     -16.361  23.565  40.370  1.00  50.82           C
ATOM   2783  O    THR B  57     -15.173  23.379  40.131  1.00  51.70           O
ATOM   2784  N    ASP B  58     -17.295  22.640  40.169  1.00  51.07           N
ATOM   2785  CA   ASP B  58     -16.966  21.312  39.638  1.00  51.33           C
ATOM   2786  CB   ASP B  58     -15.870  21.394  38.563  1.00  52.10           C
ATOM   2787  CG   ASP B  58     -16.361  21.979  37.250  1.00  53.40           C
ATOM   2788  OD1  ASP B  58     -17.157  22.943  37.282  1.00  55.47           O
ATOM   2789  OD2  ASP B  58     -15.932  21.485  36.180  1.00  51.96           O
ATOM   2790  C    ASP B  58     -16.445  20.401  40.750  1.00  51.06           C
ATOM   2791  O    ASP B  58     -15.560  19.576  40.510  1.00  51.98           O
ATOM   2792  N    THR B  59     -16.983  20.527  41.956  1.00  49.48           N
ATOM   2793  CA   THR B  59     -16.480  19.710  43.050  1.00  48.62           C
ATOM   2794  CB   THR B  59     -16.592  20.456  44.394  1.00  47.90           C
ATOM   2795  OG1  THR B  59     -17.932  20.368  44.883  1.00  49.33           O
ATOM   2796  CG2  THR B  59     -16.215  21.910  44.211  1.00  47.03           C
ATOM   2797  C    THR B  59     -17.094  18.317  43.198  1.00  48.27           C
ATOM   2798  O    THR B  59     -18.307  18.134  43.100  1.00  48.06           O
ATOM   2799  N    LYS B  60     -16.218  17.340  43.436  1.00  47.86           N
ATOM   2800  CA   LYS B  60     -16.596  15.943  43.619  1.00  47.44           C
ATOM   2801  CB   LYS B  60     -16.632  15.206  42.274  1.00  46.79           C
ATOM   2802  CG   LYS B  60     -15.548  15.618  41.302  1.00  46.62           C
ATOM   2803  CD   LYS B  60     -15.066  14.453  40.461  1.00  48.50           C
ATOM   2804  CE   LYS B  60     -14.537  14.925  39.105  1.00  50.96           C
ATOM   2805  NZ   LYS B  60     -13.581  16.082  39.201  1.00  51.97           N
ATOM   2806  C    LYS B  60     -15.604  15.252  44.544  1.00  47.20           C
ATOM   2807  O    LYS B  60     -14.411  15.572  44.547  1.00  47.86           O
```

FIG. 2-43

| ATOM | 2808 | N | VAL | B | 61 | -16.112 | 14.307 | 45.331 | 1.00 | 46.75 | N |
| --- | --- | --- | --- | --- | --- | --- | --- | --- | --- | --- | --- |
| ATOM | 2809 | CA | VAL | B | 61 | -15.301 | 13.543 | 46.270 | 1.00 | 45.23 | C |
| ATOM | 2810 | CB | VAL | B | 61 | -16.191 | 12.632 | 47.154 | 1.00 | 45.73 | C |
| ATOM | 2811 | CG1 | VAL | B | 61 | -15.330 | 11.623 | 47.917 | 1.00 | 43.58 | C |
| ATOM | 2812 | CG2 | VAL | B | 61 | -17.002 | 13.485 | 48.125 | 1.00 | 44.24 | C |
| ATOM | 2813 | C | VAL | B | 61 | -14.280 | 12.674 | 45.544 | 1.00 | 44.88 | C |
| ATOM | 2814 | O | VAL | B | 61 | -14.542 | 12.184 | 44.445 | 1.00 | 44.98 | O |
| ATOM | 2815 | N | ILE | B | 62 | -13.115 | 12.500 | 46.165 | 1.00 | 44.60 | N |
| ATOM | 2816 | CA | ILE | B | 62 | -12.041 | 11.679 | 45.610 | 1.00 | 43.97 | C |
| ATOM | 2817 | CB | ILE | B | 62 | -11.157 | 12.460 | 44.608 | 1.00 | 43.87 | C |
| ATOM | 2818 | CG2 | ILE | B | 62 | -12.006 | 13.030 | 43.483 | 1.00 | 42.75 | C |
| ATOM | 2819 | CG1 | ILE | B | 62 | -10.397 | 13.570 | 45.341 | 1.00 | 42.94 | C |
| ATOM | 2820 | CD1 | ILE | B | 62 | -9.227 | 14.121 | 44.552 | 1.00 | 41.53 | C |
| ATOM | 2821 | C | ILE | B | 62 | -11.114 | 11.178 | 46.719 | 1.00 | 43.91 | C |
| ATOM | 2822 | O | ILE | B | 62 | -10.076 | 10.581 | 46.434 | 1.00 | 43.11 | O |
| ATOM | 2823 | N | GLY | B | 63 | -11.484 | 11.409 | 47.978 | 1.00 | 43.69 | N |
| ATOM | 2824 | CA | GLY | B | 63 | -10.622 | 10.987 | 49.069 | 1.00 | 43.23 | C |
| ATOM | 2825 | C | GLY | B | 63 | -11.270 | 10.847 | 50.429 | 1.00 | 43.79 | C |
| ATOM | 2826 | O | GLY | B | 63 | -12.010 | 11.724 | 50.875 | 1.00 | 45.34 | O |
| ATOM | 2827 | N | ASN | B | 64 | -10.967 | 9.732 | 51.086 | 1.00 | 44.46 | N |
| ATOM | 2828 | CA | ASN | B | 64 | -11.482 | 9.401 | 52.407 | 1.00 | 43.82 | C |
| ATOM | 2829 | CB | ASN | B | 64 | -12.171 | 8.041 | 52.368 | 1.00 | 44.05 | C |
| ATOM | 2830 | CG | ASN | B | 64 | -13.621 | 8.118 | 52.734 | 1.00 | 46.12 | C |
| ATOM | 2831 | OD1 | ASN | B | 64 | -13.972 | 8.466 | 53.861 | 1.00 | 49.14 | O |
| ATOM | 2832 | ND2 | ASN | B | 64 | -14.485 | 7.786 | 51.790 | 1.00 | 48.46 | N |
| ATOM | 2833 | C | ASN | B | 64 | -10.293 | 9.313 | 53.363 | 1.00 | 44.10 | C |
| ATOM | 2834 | O | ASN | B | 64 | -9.134 | 9.247 | 52.944 | 1.00 | 43.02 | O |
| ATOM | 2835 | N | GLY | B | 65 | -10.587 | 9.277 | 54.652 | 1.00 | 43.26 | N |
| ATOM | 2836 | CA | GLY | B | 65 | -9.527 | 9.184 | 55.623 | 1.00 | 43.49 | C |
| ATOM | 2837 | C | GLY | B | 65 | -10.105 | 9.427 | 56.989 | 1.00 | 43.87 | C |
| ATOM | 2838 | O | GLY | B | 65 | -11.224 | 9.930 | 57.118 | 1.00 | 43.48 | O |
| ATOM | 2839 | N | SER | B | 66 | -9.350 | 9.061 | 58.013 | 1.00 | 45.12 | N |
| ATOM | 2840 | CA | SER | B | 66 | -9.809 | 9.260 | 59.380 | 1.00 | 46.67 | C |
| ATOM | 2841 | CB | SER | B | 66 | -8.745 | 8.751 | 60.349 | 1.00 | 47.44 | C |
| ATOM | 2842 | OG | SER | B | 66 | -7.446 | 9.107 | 59.892 | 1.00 | 53.51 | O |
| ATOM | 2843 | C | SER | B | 66 | -10.061 | 10.749 | 59.594 | 1.00 | 46.21 | C |
| ATOM | 2844 | O | SER | B | 66 | -10.865 | 11.142 | 60.435 | 1.00 | 46.25 | O |
| ATOM | 2845 | N | PHE | B | 67 | -9.377 | 11.563 | 58.797 | 1.00 | 45.88 | N |
| ATOM | 2846 | CA | PHE | B | 67 | -9.470 | 13.018 | 58.873 | 1.00 | 44.95 | C |
| ATOM | 2847 | CB | PHE | B | 67 | -8.207 | 13.624 | 58.278 | 1.00 | 44.32 | C |
| ATOM | 2848 | CG | PHE | B | 67 | -7.967 | 13.220 | 56.849 | 1.00 | 45.83 | C |
| ATOM | 2849 | CD1 | PHE | B | 67 | -8.642 | 13.852 | 55.805 | 1.00 | 44.35 | C |
| ATOM | 2850 | CD2 | PHE | B | 67 | -7.077 | 12.193 | 56.547 | 1.00 | 45.04 | C |
| ATOM | 2851 | CE1 | PHE | B | 67 | -8.430 | 13.468 | 54.490 | 1.00 | 43.46 | C |
| ATOM | 2852 | CE2 | PHE | B | 67 | -6.862 | 11.807 | 55.237 | 1.00 | 44.06 | C |
| ATOM | 2853 | CZ | PHE | B | 67 | -7.539 | 12.446 | 54.202 | 1.00 | 43.03 | C |
| ATOM | 2854 | C | PHE | B | 67 | -10.684 | 13.619 | 58.169 | 1.00 | 44.77 | C |
| ATOM | 2855 | O | PHE | B | 67 | -11.173 | 14.675 | 58.563 | 1.00 | 44.63 | O |
| ATOM | 2856 | N | GLY | B | 68 | -11.149 | 12.968 | 57.107 | 1.00 | 42.87 | N |
| ATOM | 2857 | CA | GLY | B | 68 | -12.293 | 13.499 | 56.401 | 1.00 | 41.22 | C |
| ATOM | 2858 | C | GLY | B | 68 | -12.415 | 13.129 | 54.940 | 1.00 | 41.15 | C |
| ATOM | 2859 | O | GLY | B | 68 | -12.229 | 11.970 | 54.562 | 1.00 | 42.58 | O |
| ATOM | 2860 | N | VAL | B | 69 | -12.721 | 14.128 | 54.113 | 1.00 | 39.68 | N |
| ATOM | 2861 | CA | VAL | B | 69 | -12.914 | 13.924 | 52.683 | 1.00 | 38.02 | C |
| ATOM | 2862 | CB | VAL | B | 69 | -14.375 | 14.250 | 52.286 | 1.00 | 36.66 | C |
| ATOM | 2863 | CG1 | VAL | B | 69 | -14.641 | 13.827 | 50.855 | 1.00 | 36.14 | C |
| ATOM | 2864 | CG2 | VAL | B | 69 | -15.336 | 13.577 | 53.246 | 1.00 | 35.31 | C |
| ATOM | 2865 | C | VAL | B | 69 | -11.990 | 14.792 | 51.832 | 1.00 | 38.53 | C |
| ATOM | 2866 | O | VAL | B | 69 | -11.512 | 15.836 | 52.272 | 1.00 | 39.44 | O |
| ATOM | 2867 | N | VAL | B | 70 | -11.741 | 14.350 | 50.606 | 1.00 | 37.68 | N |
| ATOM | 2868 | CA | VAL | B | 70 | -10.903 | 15.103 | 49.693 | 1.00 | 36.79 | C |
| ATOM | 2869 | CB | VAL | B | 70 | -9.593 | 14.366 | 49.372 | 1.00 | 34.88 | C |
| ATOM | 2870 | CG1 | VAL | B | 70 | -8.711 | 15.241 | 48.498 | 1.00 | 32.77 | C |
| ATOM | 2871 | CG2 | VAL | B | 70 | -8.870 | 14.010 | 50.658 | 1.00 | 33.95 | C |
| ATOM | 2872 | C | VAL | B | 70 | -11.694 | 15.307 | 48.410 | 1.00 | 38.20 | C |
| ATOM | 2873 | O | VAL | B | 70 | -12.169 | 14.353 | 47.800 | 1.00 | 38.29 | O |
| ATOM | 2874 | N | TYR | B | 71 | -11.847 | 16.564 | 48.018 | 1.00 | 38.75 | N |

FIG. 2-44

| | | | | | | | | | |
|---|---|---|---|---|---|---|---|---|---|
| ATOM | 2875 | CA | TYR | B | 71 | -12.590 | 16.895 | 46.824 | 1.00 38.87 | C |
| ATOM | 2876 | CB | TYR | B | 71 | -13.589 | 18.018 | 47.111 | 1.00 38.36 | C |
| ATOM | 2877 | CG | TYR | B | 71 | -14.539 | 17.768 | 48.258 | 1.00 39.09 | C |
| ATOM | 2878 | CD1 | TYR | B | 71 | -14.139 | 17.939 | 49.583 | 1.00 38.97 | C |
| ATOM | 2879 | CE1 | TYR | B | 71 | -15.043 | 17.747 | 50.631 | 1.00 40.15 | C |
| ATOM | 2880 | CD2 | TYR | B | 71 | -15.859 | 17.389 | 48.013 | 1.00 39.02 | C |
| ATOM | 2881 | CE2 | TYR | B | 71 | -16.762 | 17.194 | 49.050 | 1.00 38.97 | C |
| ATOM | 2882 | CZ | TYR | B | 71 | -16.354 | 17.375 | 50.350 | 1.00 39.63 | C |
| ATOM | 2883 | OH | TYR | B | 71 | -17.268 | 17.198 | 51.361 | 1.00 41.24 | O |
| ATOM | 2884 | C | TYR | B | 71 | -11.670 | 17.374 | 45.732 | 1.00 39.88 | C |
| ATOM | 2885 | O | TYR | B | 71 | -10.519 | 17.750 | 45.979 | 1.00 41.11 | O |
| ATOM | 2886 | N | GLN | B | 72 | -12.184 | 17.349 | 44.508 | 1.00 40.35 | N |
| ATOM | 2887 | CA | GLN | B | 72 | -11.438 | 17.868 | 43.376 | 1.00 39.38 | C |
| ATOM | 2888 | CB | GLN | B | 72 | -11.380 | 16.888 | 42.220 | 1.00 39.76 | C |
| ATOM | 2889 | CG | GLN | B | 72 | -10.357 | 17.316 | 41.191 | 1.00 41.46 | C |
| ATOM | 2890 | CD | GLN | B | 72 | -10.578 | 16.677 | 39.844 | 1.00 42.85 | C |
| ATOM | 2891 | OE1 | GLN | B | 72 | -11.083 | 17.310 | 38.915 | 1.00 44.23 | O |
| ATOM | 2892 | NE2 | GLN | B | 72 | -10.216 | 15.412 | 39.732 | 1.00 44.09 | N |
| ATOM | 2893 | C | GLN | B | 72 | -12.299 | 19.042 | 42.981 | 1.00 39.45 | C |
| ATOM | 2894 | O | GLN | B | 72 | -13.493 | 19.042 | 43.243 | 1.00 39.27 | O |
| ATOM | 2895 | N | ALA | B | 73 | -11.705 | 20.050 | 42.368 | 1.00 39.98 | N |
| ATOM | 2896 | CA | ALA | B | 73 | -12.469 | 21.215 | 41.968 | 1.00 40.33 | C |
| ATOM | 2897 | CB | ALA | B | 73 | -12.958 | 21.960 | 43.195 | 1.00 40.29 | C |
| ATOM | 2898 | C | ALA | B | 73 | -11.541 | 22.083 | 41.167 | 1.00 41.43 | C |
| ATOM | 2899 | O | ALA | B | 73 | -10.331 | 21.876 | 41.187 | 1.00 40.43 | O |
| ATOM | 2900 | N | LYS | B | 74 | -12.105 | 23.029 | 40.430 | 1.00 44.34 | N |
| ATOM | 2901 | CA | LYS | B | 74 | -11.278 | 23.926 | 39.657 | 1.00 47.70 | C |
| ATOM | 2902 | CB | LYS | B | 74 | -11.421 | 23.678 | 38.153 | 1.00 49.63 | C |
| ATOM | 2903 | CG | LYS | B | 74 | -12.686 | 24.217 | 37.552 | 1.00 51.69 | C |
| ATOM | 2904 | CD | LYS | B | 74 | -12.606 | 24.248 | 36.038 | 1.00 53.82 | C |
| ATOM | 2905 | CE | LYS | B | 74 | -13.858 | 24.902 | 35.467 | 1.00 54.74 | C |
| ATOM | 2906 | NZ | LYS | B | 74 | -13.855 | 24.912 | 33.982 | 1.00 54.31 | N |
| ATOM | 2907 | C | LYS | B | 74 | -11.665 | 25.350 | 39.994 | 1.00 48.33 | C |
| ATOM | 2908 | O | LYS | B | 74 | -12.836 | 25.675 | 40.203 | 1.00 47.67 | O |
| ATOM | 2909 | N | LEU | B | 75 | -10.641 | 26.188 | 40.046 | 1.00 48.67 | N |
| ATOM | 2910 | CA | LEU | B | 75 | -10.778 | 27.591 | 40.369 | 1.00 48.54 | C |
| ATOM | 2911 | CB | LEU | B | 75 | -9.395 | 28.138 | 40.727 | 1.00 47.55 | C |
| ATOM | 2912 | CG | LEU | B | 75 | -8.770 | 27.296 | 41.847 | 1.00 44.76 | C |
| ATOM | 2913 | CD1 | LEU | B | 75 | -7.380 | 27.787 | 42.152 | 1.00 41.96 | C |
| ATOM | 2914 | CD2 | LEU | B | 75 | -9.657 | 27.354 | 43.092 | 1.00 43.26 | C |
| ATOM | 2915 | C | LEU | B | 75 | -11.402 | 28.360 | 39.211 | 1.00 48.85 | C |
| ATOM | 2916 | O | LEU | B | 75 | -10.970 | 28.242 | 38.062 | 1.00 49.76 | O |
| ATOM | 2917 | N | CYS | B | 76 | -12.427 | 29.144 | 39.532 | 1.00 50.86 | N |
| ATOM | 2918 | CA | CYS | B | 76 | -13.180 | 29.936 | 38.557 | 1.00 52.09 | C |
| ATOM | 2919 | CB | CYS | B | 76 | -14.298 | 30.694 | 39.259 | 1.00 50.15 | C |
| ATOM | 2920 | SG | CYS | B | 76 | -15.589 | 29.688 | 39.954 | 1.00 52.24 | S |
| ATOM | 2921 | C | CYS | B | 76 | -12.398 | 30.947 | 37.749 | 1.00 53.39 | C |
| ATOM | 2922 | O | CYS | B | 76 | -12.883 | 31.421 | 36.720 | 1.00 54.12 | O |
| ATOM | 2923 | N | ASP | B | 77 | -11.207 | 31.308 | 38.210 | 1.00 55.22 | N |
| ATOM | 2924 | CA | ASP | B | 77 | -10.426 | 32.316 | 37.499 | 1.00 57.62 | C |
| ATOM | 2925 | CB | ASP | B | 77 | -9.848 | 33.321 | 38.503 | 1.00 60.54 | C |
| ATOM | 2926 | CG | ASP | B | 77 | -10.831 | 34.435 | 38.845 | 1.00 63.71 | C |
| ATOM | 2927 | OD1 | ASP | B | 77 | -12.011 | 34.135 | 39.170 | 1.00 65.05 | O |
| ATOM | 2928 | OD2 | ASP | B | 77 | -10.420 | 35.615 | 38.789 | 1.00 65.20 | O |
| ATOM | 2929 | C | ASP | B | 77 | -9.315 | 31.793 | 36.610 | 1.00 57.30 | C |
| ATOM | 2930 | O | ASP | B | 77 | -8.874 | 32.491 | 35.700 | 1.00 57.68 | O |
| ATOM | 2931 | N | SER | B | 78 | -8.856 | 30.574 | 36.858 | 1.00 56.60 | N |
| ATOM | 2932 | CA | SER | B | 78 | -7.767 | 30.030 | 36.052 | 1.00 56.10 | C |
| ATOM | 2933 | CB | SER | B | 78 | -6.525 | 29.882 | 36.923 | 1.00 55.91 | C |
| ATOM | 2934 | OG | SER | B | 78 | -6.805 | 29.016 | 38.013 | 1.00 56.26 | O |
| ATOM | 2935 | C | SER | B | 78 | -8.104 | 28.687 | 35.428 | 1.00 55.86 | C |
| ATOM | 2936 | O | SER | B | 78 | -7.325 | 28.149 | 34.644 | 1.00 55.79 | O |
| ATOM | 2937 | N | GLY | B | 79 | -9.270 | 28.151 | 35.773 | 1.00 55.09 | N |
| ATOM | 2938 | CA | GLY | B | 79 | -9.639 | 26.859 | 35.247 | 1.00 53.76 | C |
| ATOM | 2939 | C | GLY | B | 79 | -8.816 | 25.799 | 35.958 | 1.00 53.47 | C |
| ATOM | 2940 | O | GLY | B | 79 | -9.251 | 24.655 | 36.052 | 1.00 53.94 | O |
| ATOM | 2941 | N | GLU | B | 80 | -7.638 | 26.180 | 36.469 | 1.00 51.97 | N |

FIG. 2-45

```
ATOM   2942  CA  GLU B  80      -6.748  25.245  37.170  1.00 50.73           C
ATOM   2943  CB  GLU B  80      -5.699  25.985  38.000  1.00 52.58           C
ATOM   2944  CG  GLU B  80      -4.510  26.528  37.245  1.00 55.08           C
ATOM   2945  CD  GLU B  80      -3.476  27.128  38.194  1.00 56.59           C
ATOM   2946  OE1 GLU B  80      -3.843  28.047  38.969  1.00 57.59           O
ATOM   2947  OE2 GLU B  80      -2.305  26.681  38.173  1.00 57.10           O
ATOM   2948  C   GLU B  80      -7.491  24.306  38.096  1.00 48.79           C
ATOM   2949  O   GLU B  80      -8.460  24.694  38.752  1.00 48.42           O
ATOM   2950  N   LEU B  81      -7.015  23.070  38.161  1.00 46.99           N
ATOM   2951  CA  LEU B  81      -7.638  22.075  39.018  1.00 45.55           C
ATOM   2952  CB  LEU B  81      -7.570  20.689  38.381  1.00 45.62           C
ATOM   2953  CG  LEU B  81      -8.562  20.359  37.258  1.00 44.54           C
ATOM   2954  CD1 LEU B  81      -8.432  18.884  36.903  1.00 43.77           C
ATOM   2955  CD2 LEU B  81      -9.991  20.661  37.729  1.00 44.87           C
ATOM   2956  C   LEU B  81      -6.974  22.045  40.381  1.00 44.27           C
ATOM   2957  O   LEU B  81      -5.785  22.331  40.525  1.00 44.60           O
ATOM   2958  N   VAL B  82      -7.758  21.699  41.389  1.00 41.89           N
ATOM   2959  CA  VAL B  82      -7.251  21.654  42.743  1.00 38.96           C
ATOM   2960  CB  VAL B  82      -7.553  22.963  43.489  1.00 38.12           C
ATOM   2961  CG1 VAL B  82      -6.736  24.092  42.896  1.00 38.49           C
ATOM   2962  CG2 VAL B  82      -9.042  23.278  43.407  1.00 38.48           C
ATOM   2963  C   VAL B  82      -7.848  20.523  43.539  1.00 38.56           C
ATOM   2964  O   VAL B  82      -8.869  19.952  43.170  1.00 39.17           O
ATOM   2965  N   ALA B  83      -7.183  20.200  44.639  1.00 38.11           N
ATOM   2966  CA  ALA B  83      -7.646  19.170  45.545  1.00 37.12           C
ATOM   2967  CB  ALA B  83      -6.531  18.146  45.795  1.00 37.03           C
ATOM   2968  C   ALA B  83      -7.966  19.938  46.823  1.00 36.50           C
ATOM   2969  O   ALA B  83      -7.258  20.881  47.180  1.00 34.62           O
ATOM   2970  N   ILE B  84      -9.045  19.565  47.495  1.00 35.39           N
ATOM   2971  CA  ILE B  84      -9.396  20.233  48.737  1.00 34.75           C
ATOM   2972  CB  ILE B  84     -10.708  21.058  48.618  1.00 32.42           C
ATOM   2973  CG2 ILE B  84     -11.076  21.648  49.969  1.00 29.80           C
ATOM   2974  CG1 ILE B  84     -10.523  22.192  47.602  1.00 34.66           C
ATOM   2975  CD1 ILE B  84     -11.794  22.988  47.298  1.00 31.49           C
ATOM   2976  C   ILE B  84      -9.547  19.205  49.846  1.00 36.02           C
ATOM   2977  O   ILE B  84     -10.464  18.380  49.835  1.00 37.54           O
ATOM   2978  N   LYS B  85      -8.637  19.255  50.806  1.00 35.23           N
ATOM   2979  CA  LYS B  85      -8.686  18.330  51.912  1.00 36.77           C
ATOM   2980  CB  LYS B  85      -7.262  17.968  52.345  1.00 35.14           C
ATOM   2981  CG  LYS B  85      -7.163  16.801  53.307  1.00 33.34           C
ATOM   2982  CD  LYS B  85      -5.704  16.486  53.593  1.00 33.75           C
ATOM   2983  CE  LYS B  85      -5.559  15.433  54.678  1.00 34.55           C
ATOM   2984  NZ  LYS B  85      -4.132  15.167  55.019  1.00 34.26           N
ATOM   2985  C   LYS B  85      -9.470  18.983  53.049  1.00 38.81           C
ATOM   2986  O   LYS B  85      -9.009  19.943  53.670  1.00 39.60           O
ATOM   2987  N   LYS B  86     -10.669  18.462  53.290  1.00 40.54           N
ATOM   2988  CA  LYS B  86     -11.564  18.962  54.332  1.00 42.43           C
ATOM   2989  CB  LYS B  86     -13.019  18.780  53.864  1.00 42.61           C
ATOM   2990  CG  LYS B  86     -14.120  19.377  54.732  1.00 42.34           C
ATOM   2991  CD  LYS B  86     -15.275  19.838  53.841  1.00 44.74           C
ATOM   2992  CE  LYS B  86     -16.602  19.997  54.589  1.00 46.03           C
ATOM   2993  NZ  LYS B  86     -17.223  18.679  54.965  1.00 45.79           N
ATOM   2994  C   LYS B  86     -11.286  18.175  55.611  1.00 43.43           C
ATOM   2995  O   LYS B  86     -11.407  16.950  55.630  1.00 43.99           O
ATOM   2996  N   VAL B  87     -10.899  18.882  56.669  1.00 44.25           N
ATOM   2997  CA  VAL B  87     -10.572  18.249  57.939  1.00 45.28           C
ATOM   2998  CB  VAL B  87      -9.066  18.392  58.260  1.00 43.79           C
ATOM   2999  CG1 VAL B  87      -8.819  18.099  59.730  1.00 43.28           C
ATOM   3000  CG2 VAL B  87      -8.247  17.445  57.395  1.00 41.59           C
ATOM   3001  C   VAL B  87     -11.329  18.816  59.121  1.00 47.69           C
ATOM   3002  O   VAL B  87     -11.551  20.026  59.205  1.00 48.30           O
ATOM   3003  N   LEU B  88     -11.720  17.943  60.045  1.00 50.77           N
ATOM   3004  CA  LEU B  88     -12.416  18.398  61.240  1.00 53.86           C
ATOM   3005  CB  LEU B  88     -13.175  17.246  61.904  1.00 53.84           C
ATOM   3006  CG  LEU B  88     -14.273  17.705  62.875  1.00 54.46           C
ATOM   3007  CD1 LEU B  88     -15.442  18.249  62.056  1.00 53.72           C
ATOM   3008  CD2 LEU B  88     -14.745  16.552  63.752  1.00 54.38           C
```

FIG. 2-46

```
ATOM   3009  C    LEU  B   88     -11.339   18.921   62.194   1.00  55.56           C
ATOM   3010  O    LEU  B   88     -10.530   18.149   62.708   1.00  57.09           O
ATOM   3011  N    GLN  B   89     -11.318   20.229   62.414   1.00  57.40           N
ATOM   3012  CA   GLN  B   89     -10.331   20.826   63.301   1.00  59.19           C
ATOM   3013  CB   GLN  B   89      -9.638   21.999   62.600   1.00  59.78           C
ATOM   3014  CG   GLN  B   89      -8.637   22.763   63.459   1.00  61.00           C
ATOM   3015  CD   GLN  B   89      -7.602   21.866   64.124   1.00  61.30           C
ATOM   3016  OE1  GLN  B   89      -7.633   20.638   63.973   1.00  61.24           O
ATOM   3017  NE2  GLN  B   89      -6.674   22.482   64.867   1.00  60.92           N
ATOM   3018  C    GLN  B   89     -10.987   21.310   64.581   1.00  60.34           C
ATOM   3019  O    GLN  B   89     -11.951   22.072   64.545   1.00  60.15           O
ATOM   3020  N    ASP  B   90     -10.460   20.848   65.711   1.00  61.90           N
ATOM   3021  CA   ASP  B   90     -10.961   21.244   67.022   1.00  63.13           C
ATOM   3022  CB   ASP  B   90     -10.554   20.201   68.065   1.00  64.02           C
ATOM   3023  CG   ASP  B   90     -11.003   20.567   69.462   1.00  65.37           C
ATOM   3024  OD1  ASP  B   90     -10.951   19.677   70.346   1.00  66.22           O
ATOM   3025  OD2  ASP  B   90     -11.392   21.744   69.674   1.00  65.16           O
ATOM   3026  C    ASP  B   90     -10.350   22.602   67.354   1.00  63.40           C
ATOM   3027  O    ASP  B   90      -9.138   22.707   67.553   1.00  63.63           O
ATOM   3028  N    LYS  B   91     -11.178   23.640   67.444   1.00  63.19           N
ATOM   3029  CA   LYS  B   91     -10.642   24.979   67.706   1.00  63.49           C
ATOM   3030  CB   LYS  B   91     -11.776   26.001   67.839   1.00  63.39           C
ATOM   3031  CG   LYS  B   91     -11.828   26.988   66.674   1.00  64.27           C
ATOM   3032  CD   LYS  B   91     -10.503   27.736   66.497   1.00  64.97           C
ATOM   3033  CE   LYS  B   91     -10.062   27.804   65.022   1.00  65.05           C
ATOM   3034  NZ   LYS  B   91      -8.705   28.444   64.859   1.00  64.20           N
ATOM   3035  C    LYS  B   91      -9.665   25.140   68.875   1.00  63.12           C
ATOM   3036  O    LYS  B   91      -8.912   26.119   68.918   1.00  62.78           O
ATOM   3037  N    ALA  B   92      -9.667   24.188   69.804   1.00  63.18           N
ATOM   3038  CA   ALA  B   92      -8.762   24.234   70.958   1.00  63.35           C
ATOM   3039  CB   ALA  B   92      -8.968   22.994   71.839   1.00  63.66           C
ATOM   3040  C    ALA  B   92      -7.307   24.300   70.491   1.00  62.78           C
ATOM   3041  O    ALA  B   92      -6.646   25.339   70.614   1.00  62.35           O
ATOM   3042  N    ALA  B   93      -6.828   23.183   69.947   1.00  61.67           N
ATOM   3043  CA   ALA  B   93      -5.461   23.083   69.451   1.00  59.93           C
ATOM   3044  CB   ALA  B   93      -4.954   21.658   69.638   1.00  60.59           C
ATOM   3045  C    ALA  B   93      -5.333   23.491   67.983   1.00  58.12           C
ATOM   3046  O    ALA  B   93      -6.258   23.318   67.194   1.00  57.53           O
ATOM   3047  N    ALA  B   94      -4.179   24.048   67.630   1.00  55.49           N
ATOM   3048  CA   ALA  B   94      -3.911   24.453   66.255   1.00  52.93           C
ATOM   3049  CB   ALA  B   94      -2.625   25.225   66.192   1.00  53.29           C
ATOM   3050  C    ALA  B   94      -3.744   23.160   65.458   1.00  50.81           C
ATOM   3051  O    ALA  B   94      -3.658   22.085   66.047   1.00  50.27           O
ATOM   3052  N    ASN  B   95      -3.713   23.259   64.130   1.00  47.18           N
ATOM   3053  CA   ASN  B   95      -3.579   22.080   63.258   1.00  42.60           C
ATOM   3054  CB   ASN  B   95      -4.493   22.230   62.027   1.00  43.87           C
ATOM   3055  CG   ASN  B   95      -4.434   21.025   61.084   1.00  44.45           C
ATOM   3056  OD1  ASN  B   95      -3.455   20.831   60.348   1.00  44.76           O
ATOM   3057  ND2  ASN  B   95      -5.489   20.211   61.102   1.00  42.43           N
ATOM   3058  C    ASN  B   95      -2.136   21.880   62.815   1.00  40.16           C
ATOM   3059  O    ASN  B   95      -1.516   22.772   62.233   1.00  39.22           O
ATOM   3060  N    ARG  B   96      -1.602   20.700   63.097   1.00  38.07           N
ATOM   3061  CA   ARG  B   96      -0.229   20.397   62.745   1.00  36.92           C
ATOM   3062  CB   ARG  B   96       0.192   19.058   63.362   1.00  35.33           C
ATOM   3063  CG   ARG  B   96       1.690   18.803   63.328   1.00  35.91           C
ATOM   3064  CD   ARG  B   96       2.067   17.485   63.998   1.00  38.77           C
ATOM   3065  NE   ARG  B   96       1.967   17.520   65.461   1.00  42.95           N
ATOM   3066  CZ   ARG  B   96       2.095   16.449   66.243   1.00  43.09           C
ATOM   3067  NH1  ARG  B   96       2.325   15.254   65.708   1.00  44.67           N
ATOM   3068  NH2  ARG  B   96       1.994   16.566   67.556   1.00  43.40           N
ATOM   3069  C    ARG  B   96      -0.010   20.375   61.235   1.00  37.33           C
ATOM   3070  O    ARG  B   96       0.939   20.980   60.734   1.00  37.27           O
ATOM   3071  N    GLU  B   97      -0.891   19.700   60.501   1.00  37.25           N
ATOM   3072  CA   GLU  B   97      -0.725   19.614   59.051   1.00  36.97           C
ATOM   3073  CB   GLU  B   97      -1.871   18.820   58.410   1.00  38.32           C
ATOM   3074  CG   GLU  B   97      -1.472   18.164   57.095   1.00  37.20           C
ATOM   3075  CD   GLU  B   97      -2.607   17.405   56.432   1.00  36.58           C
```

FIG. 2-47

| ATOM | 3076 | OE1 | GLU | B | 97 | -3.401 | 16.757 | 57.143 | 1.00 | 36.86 | O |
|---|---|---|---|---|---|---|---|---|---|---|---|
| ATOM | 3077 | OE2 | GLU | B | 97 | -2.694 | 17.440 | 55.196 | 1.00 | 35.29 | O |
| ATOM | 3078 | C | GLU | B | 97 | -0.631 | 20.996 | 58.410 | 1.00 | 37.12 | C |
| ATOM | 3079 | O | GLU | B | 97 | 0.221 | 21.239 | 57.551 | 1.00 | 36.62 | O |
| ATOM | 3080 | N | LEU | B | 98 | -1.496 | 21.912 | 58.829 | 1.00 | 36.34 | N |
| ATOM | 3081 | CA | LEU | B | 98 | -1.458 | 23.254 | 58.264 | 1.00 | 35.61 | C |
| ATOM | 3082 | CB | LEU | B | 98 | -2.681 | 24.059 | 58.715 | 1.00 | 34.28 | C |
| ATOM | 3083 | CG | LEU | B | 98 | -2.704 | 25.547 | 58.366 | 1.00 | 31.69 | C |
| ATOM | 3084 | CD1 | LEU | B | 98 | -2.394 | 25.759 | 56.898 | 1.00 | 32.64 | C |
| ATOM | 3085 | CD2 | LEU | B | 98 | -4.055 | 26.109 | 58.732 | 1.00 | 31.27 | C |
| ATOM | 3086 | C | LEU | B | 98 | -0.164 | 24.003 | 58.618 | 1.00 | 35.99 | C |
| ATOM | 3087 | O | LEU | B | 98 | 0.460 | 24.614 | 57.748 | 1.00 | 33.10 | O |
| ATOM | 3088 | N | GLN | B | 99 | 0.244 | 23.946 | 59.885 | 1.00 | 38.08 | N |
| ATOM | 3089 | CA | GLN | B | 99 | 1.462 | 24.633 | 60.319 | 1.00 | 39.87 | C |
| ATOM | 3090 | CB | GLN | B | 99 | 1.751 | 24.335 | 61.796 | 1.00 | 43.70 | C |
| ATOM | 3091 | CG | GLN | B | 99 | 0.748 | 24.918 | 62.769 | 1.00 | 48.80 | C |
| ATOM | 3092 | CD | GLN | B | 99 | 1.080 | 24.573 | 64.218 | 1.00 | 53.01 | C |
| ATOM | 3093 | OE1 | GLN | B | 99 | 0.287 | 24.849 | 65.130 | 1.00 | 57.14 | O |
| ATOM | 3094 | NE2 | GLN | B | 99 | 2.255 | 23.965 | 64.438 | 1.00 | 53.18 | N |
| ATOM | 3095 | C | GLN | B | 99 | 2.681 | 24.252 | 59.485 | 1.00 | 37.91 | C |
| ATOM | 3096 | O | GLN | B | 99 | 3.404 | 25.121 | 59.006 | 1.00 | 36.20 | O |
| ATOM | 3097 | N | ILE | B | 100 | 2.897 | 22.947 | 59.323 | 1.00 | 37.69 | N |
| ATOM | 3098 | CA | ILE | B | 100 | 4.028 | 22.422 | 58.546 | 1.00 | 37.00 | C |
| ATOM | 3099 | CB | ILE | B | 100 | 4.103 | 20.884 | 58.650 | 1.00 | 35.39 | C |
| ATOM | 3100 | CG2 | ILE | B | 100 | 5.003 | 20.330 | 57.548 | 1.00 | 34.95 | C |
| ATOM | 3101 | CG1 | ILE | B | 100 | 4.588 | 20.483 | 60.039 | 1.00 | 33.32 | C |
| ATOM | 3102 | CD1 | ILE | B | 100 | 4.389 | 19.023 | 60.353 | 1.00 | 33.04 | C |
| ATOM | 3103 | C | ILE | B | 100 | 3.918 | 22.793 | 57.072 | 1.00 | 38.03 | C |
| ATOM | 3104 | O | ILE | B | 100 | 4.892 | 23.193 | 56.436 | 1.00 | 38.57 | O |
| ATOM | 3105 | N | MET | B | 101 | 2.711 | 22.643 | 56.548 | 1.00 | 39.15 | N |
| ATOM | 3106 | CA | MET | B | 101 | 2.420 | 22.939 | 55.172 | 1.00 | 40.12 | C |
| ATOM | 3107 | CB | MET | B | 101 | 0.972 | 22.600 | 54.880 | 1.00 | 39.96 | C |
| ATOM | 3108 | CG | MET | B | 101 | 0.779 | 22.268 | 53.415 | 1.00 | 42.10 | C |
| ATOM | 3109 | SD | MET | B | 101 | 0.827 | 20.510 | 53.065 | 1.00 | 41.87 | S |
| ATOM | 3110 | CE | MET | B | 101 | 1.333 | 20.571 | 51.343 | 1.00 | 38.27 | C |
| ATOM | 3111 | C | MET | B | 101 | 2.663 | 24.410 | 54.860 | 1.00 | 41.37 | C |
| ATOM | 3112 | O | MET | B | 101 | 3.301 | 24.767 | 53.864 | 1.00 | 41.19 | O |
| ATOM | 3113 | N | ARG | B | 102 | 2.147 | 25.262 | 55.734 | 1.00 | 43.11 | N |
| ATOM | 3114 | CA | ARG | B | 102 | 2.247 | 26.710 | 55.588 | 1.00 | 44.59 | C |
| ATOM | 3115 | CB | ARG | B | 102 | 1.541 | 27.381 | 56.771 | 1.00 | 45.19 | C |
| ATOM | 3116 | CG | ARG | B | 102 | 1.205 | 28.841 | 56.569 | 1.00 | 45.92 | C |
| ATOM | 3117 | CD | ARG | B | 102 | -0.220 | 29.047 | 56.070 | 1.00 | 45.29 | C |
| ATOM | 3118 | NE | ARG | B | 102 | -0.529 | 30.477 | 55.983 | 1.00 | 45.40 | N |
| ATOM | 3119 | CZ | ARG | B | 102 | -0.823 | 31.248 | 57.029 | 1.00 | 45.04 | C |
| ATOM | 3120 | NH1 | ARG | B | 102 | -0.863 | 30.728 | 58.248 | 1.00 | 44.39 | N |
| ATOM | 3121 | NH2 | ARG | B | 102 | -1.047 | 32.546 | 56.858 | 1.00 | 46.00 | N |
| ATOM | 3122 | C | ARG | B | 102 | 3.665 | 27.266 | 55.455 | 1.00 | 45.16 | C |
| ATOM | 3123 | O | ARG | B | 102 | 3.832 | 28.418 | 55.062 | 1.00 | 46.97 | O |
| ATOM | 3124 | N | LYS | B | 103 | 4.683 | 26.464 | 55.762 | 1.00 | 45.64 | N |
| ATOM | 3125 | CA | LYS | B | 103 | 6.061 | 26.941 | 55.668 | 1.00 | 45.33 | C |
| ATOM | 3126 | CB | LYS | B | 103 | 6.742 | 26.830 | 57.038 | 1.00 | 46.10 | C |
| ATOM | 3127 | CG | LYS | B | 103 | 7.629 | 25.601 | 57.206 | 1.00 | 48.60 | C |
| ATOM | 3128 | CD | LYS | B | 103 | 8.363 | 25.599 | 58.544 | 1.00 | 52.23 | C |
| ATOM | 3129 | CE | LYS | B | 103 | 7.405 | 25.307 | 59.697 | 1.00 | 53.96 | C |
| ATOM | 3130 | NZ | LYS | B | 103 | 8.121 | 25.223 | 61.011 | 1.00 | 56.75 | N |
| ATOM | 3131 | C | LYS | B | 103 | 6.913 | 26.215 | 54.626 | 1.00 | 46.15 | C |
| ATOM | 3132 | O | LYS | B | 103 | 8.134 | 26.395 | 54.586 | 1.00 | 46.19 | O |
| ATOM | 3133 | N | LEU | B | 104 | 6.290 | 25.403 | 53.776 | 1.00 | 45.89 | N |
| ATOM | 3134 | CA | LEU | B | 104 | 7.053 | 24.662 | 52.771 | 1.00 | 44.29 | C |
| ATOM | 3135 | CB | LEU | B | 104 | 6.618 | 23.189 | 52.795 | 1.00 | 41.94 | C |
| ATOM | 3136 | CG | LEU | B | 104 | 7.563 | 22.193 | 53.502 | 1.00 | 41.58 | C |
| ATOM | 3137 | CD1 | LEU | B | 104 | 8.219 | 22.818 | 54.710 | 1.00 | 38.31 | C |
| ATOM | 3138 | CD2 | LEU | B | 104 | 6.786 | 20.941 | 53.893 | 1.00 | 40.75 | C |
| ATOM | 3139 | C | LEU | B | 104 | 6.963 | 25.235 | 51.356 | 1.00 | 43.39 | C |
| ATOM | 3140 | O | LEU | B | 104 | 5.934 | 25.782 | 50.962 | 1.00 | 44.25 | O |
| ATOM | 3141 | N | ASP | B | 105 | 8.054 | 25.144 | 50.604 | 1.00 | 43.33 | N |
| ATOM | 3142 | CA | ASP | B | 105 | 8.063 | 25.642 | 49.229 | 1.00 | 44.67 | C |

FIG. 2-48

| ATOM | 3143 | CB | ASP | B | 105 | 8.279 | 27.150 | 49.174 | 1.00 | 47.13 | C |
| ATOM | 3144 | CG | ASP | B | 105 | 7.988 | 27.727 | 47.793 | 1.00 | 50.33 | C |
| ATOM | 3145 | OD1 | ASP | B | 105 | 8.518 | 27.206 | 46.788 | 1.00 | 53.15 | O |
| ATOM | 3146 | OD2 | ASP | B | 105 | 7.223 | 28.705 | 47.705 | 1.00 | 52.00 | O |
| ATOM | 3147 | C | ASP | B | 105 | 9.164 | 24.969 | 48.434 | 1.00 | 44.17 | C |
| ATOM | 3148 | O | ASP | B | 105 | 10.320 | 25.407 | 48.453 | 1.00 | 44.09 | O |
| ATOM | 3149 | N | HIS | B | 106 | 8.791 | 23.906 | 47.728 | 1.00 | 44.61 | N |
| ATOM | 3150 | CA | HIS | B | 106 | 9.737 | 23.136 | 46.936 | 1.00 | 42.90 | C |
| ATOM | 3151 | CB | HIS | B | 106 | 10.294 | 21.978 | 47.775 | 1.00 | 41.54 | C |
| ATOM | 3152 | CG | HIS | B | 106 | 11.618 | 21.478 | 47.302 | 1.00 | 40.94 | C |
| ATOM | 3153 | CD2 | HIS | B | 106 | 12.881 | 21.766 | 47.716 | 1.00 | 41.41 | C |
| ATOM | 3154 | ND1 | HIS | B | 106 | 11.762 | 20.612 | 46.241 | 1.00 | 39.52 | N |
| ATOM | 3155 | CE1 | HIS | B | 106 | 13.042 | 20.388 | 46.018 | 1.00 | 40.71 | C |
| ATOM | 3156 | NE2 | HIS | B | 106 | 13.743 | 21.082 | 46.905 | 1.00 | 41.38 | N |
| ATOM | 3157 | C | HIS | B | 106 | 9.064 | 22.602 | 45.675 | 1.00 | 41.59 | C |
| ATOM | 3158 | O | HIS | B | 106 | 7.875 | 22.266 | 45.679 | 1.00 | 40.46 | O |
| ATOM | 3159 | N | CYS | B | 107 | 9.840 | 22.549 | 44.599 | 1.00 | 40.97 | N |
| ATOM | 3160 | CA | CYS | B | 107 | 9.375 | 22.066 | 43.306 | 1.00 | 40.66 | C |
| ATOM | 3161 | CB | CYS | B | 107 | 10.493 | 22.240 | 42.270 | 1.00 | 43.15 | C |
| ATOM | 3162 | SG | CYS | B | 107 | 12.146 | 21.626 | 42.842 | 1.00 | 48.31 | S |
| ATOM | 3163 | C | CYS | B | 107 | 8.956 | 20.596 | 43.385 | 1.00 | 39.11 | C |
| ATOM | 3164 | O | CYS | B | 107 | 8.330 | 20.075 | 42.470 | 1.00 | 39.55 | O |
| ATOM | 3165 | N | ASN | B | 108 | 9.294 | 19.934 | 44.486 | 1.00 | 37.88 | N |
| ATOM | 3166 | CA | ASN | B | 108 | 8.956 | 18.536 | 44.647 | 1.00 | 35.58 | C |
| ATOM | 3167 | CB | ASN | B | 108 | 10.231 | 17.735 | 44.855 | 1.00 | 34.17 | C |
| ATOM | 3168 | CG | ASN | B | 108 | 11.156 | 17.801 | 43.655 | 1.00 | 34.54 | C |
| ATOM | 3169 | OD1 | ASN | B | 108 | 12.215 | 18.425 | 43.703 | 1.00 | 34.20 | O |
| ATOM | 3170 | ND2 | ASN | B | 108 | 10.752 | 17.159 | 42.564 | 1.00 | 34.72 | N |
| ATOM | 3171 | C | ASN | B | 108 | 7.971 | 18.268 | 45.776 | 1.00 | 35.13 | C |
| ATOM | 3172 | O | ASN | B | 108 | 7.986 | 17.199 | 46.390 | 1.00 | 34.61 | O |
| ATOM | 3173 | N | ILE | B | 109 | 7.110 | 19.243 | 46.043 | 1.00 | 35.13 | N |
| ATOM | 3174 | CA | ILE | B | 109 | 6.105 | 19.109 | 47.086 | 1.00 | 35.34 | C |
| ATOM | 3175 | CB | ILE | B | 109 | 6.591 | 19.723 | 48.415 | 1.00 | 35.54 | C |
| ATOM | 3176 | CG2 | ILE | B | 109 | 5.410 | 20.093 | 49.296 | 1.00 | 33.08 | C |
| ATOM | 3177 | CG1 | ILE | B | 109 | 7.524 | 18.739 | 49.113 | 1.00 | 35.14 | C |
| ATOM | 3178 | CD1 | ILE | B | 109 | 8.462 | 19.392 | 50.086 | 1.00 | 36.44 | C |
| ATOM | 3179 | C | ILE | B | 109 | 4.831 | 19.801 | 46.658 | 1.00 | 35.43 | C |
| ATOM | 3180 | O | ILE | B | 109 | 4.870 | 20.913 | 46.135 | 1.00 | 35.50 | O |
| ATOM | 3181 | N | VAL | B | 110 | 3.708 | 19.126 | 46.876 | 1.00 | 37.08 | N |
| ATOM | 3182 | CA | VAL | B | 110 | 2.417 | 19.684 | 46.521 | 1.00 | 38.98 | C |
| ATOM | 3183 | CB | VAL | B | 110 | 1.247 | 18.798 | 46.993 | 1.00 | 38.29 | C |
| ATOM | 3184 | CG1 | VAL | B | 110 | 1.420 | 17.404 | 46.460 | 1.00 | 40.91 | C |
| ATOM | 3185 | CG2 | VAL | B | 110 | 1.159 | 18.786 | 48.509 | 1.00 | 38.21 | C |
| ATOM | 3186 | C | VAL | B | 110 | 2.322 | 21.020 | 47.221 | 1.00 | 40.05 | C |
| ATOM | 3187 | O | VAL | B | 110 | 2.592 | 21.113 | 48.408 | 1.00 | 39.51 | O |
| ATOM | 3188 | N | ARG | B | 111 | 1.945 | 22.058 | 46.488 | 1.00 | 42.12 | N |
| ATOM | 3189 | CA | ARG | B | 111 | 1.837 | 23.371 | 47.085 | 1.00 | 43.47 | C |
| ATOM | 3190 | CB | ARG | B | 111 | 2.069 | 24.457 | 46.033 | 1.00 | 46.54 | C |
| ATOM | 3191 | CG | ARG | B | 111 | 1.674 | 25.878 | 46.487 | 1.00 | 51.35 | C |
| ATOM | 3192 | CD | ARG | B | 111 | 2.168 | 26.971 | 45.527 | 1.00 | 53.80 | C |
| ATOM | 3193 | NE | ARG | B | 111 | 1.390 | 27.111 | 44.291 | 1.00 | 57.13 | N |
| ATOM | 3194 | CZ | ARG | B | 111 | 1.316 | 26.199 | 43.319 | 1.00 | 58.85 | C |
| ATOM | 3195 | NH1 | ARG | B | 111 | 1.966 | 25.049 | 43.426 | 1.00 | 59.57 | N |
| ATOM | 3196 | NH2 | ARG | B | 111 | 0.629 | 26.456 | 42.209 | 1.00 | 58.41 | N |
| ATOM | 3197 | C | ARG | B | 111 | 0.489 | 23.592 | 47.748 | 1.00 | 43.87 | C |
| ATOM | 3198 | O | ARG | B | 111 | -0.541 | 23.091 | 47.285 | 1.00 | 44.39 | O |
| ATOM | 3199 | N | LEU | B | 112 | 0.517 | 24.347 | 48.843 | 1.00 | 43.67 | N |
| ATOM | 3200 | CA | LEU | B | 112 | -0.682 | 24.710 | 49.585 | 1.00 | 42.89 | C |
| ATOM | 3201 | CB | LEU | B | 112 | -0.390 | 24.774 | 51.082 | 1.00 | 41.71 | C |
| ATOM | 3202 | CG | LEU | B | 112 | -1.539 | 25.262 | 51.965 | 1.00 | 41.98 | C |
| ATOM | 3203 | CD1 | LEU | B | 112 | -2.812 | 24.491 | 51.637 | 1.00 | 43.04 | C |
| ATOM | 3204 | CD2 | LEU | B | 112 | -1.173 | 25.074 | 53.431 | 1.00 | 42.15 | C |
| ATOM | 3205 | C | LEU | B | 112 | -1.101 | 26.087 | 49.073 | 1.00 | 42.88 | C |
| ATOM | 3206 | O | LEU | B | 112 | -0.584 | 27.111 | 49.513 | 1.00 | 41.81 | O |
| ATOM | 3207 | N | ARG | B | 113 | -2.035 | 26.086 | 48.125 | 1.00 | 43.18 | N |
| ATOM | 3208 | CA | ARG | B | 113 | -2.549 | 27.303 | 47.502 | 1.00 | 42.90 | C |
| ATOM | 3209 | CB | ARG | B | 113 | -3.532 | 26.935 | 46.385 | 1.00 | 44.79 | C |

FIG. 2-49

| ATOM | 3210 | CG | ARG | B | 113 | -3.059 | 25.793 | 45.490 | 1.00 | 47.54 | C |
| --- | --- | --- | --- | --- | --- | --- | --- | --- | --- | --- | --- |
| ATOM | 3211 | CD | ARG | B | 113 | -1.942 | 26.228 | 44.553 | 1.00 | 52.27 | C |
| ATOM | 3212 | NE | ARG | B | 113 | -2.482 | 26.771 | 43.309 | 1.00 | 56.65 | N |
| ATOM | 3213 | CZ | ARG | B | 113 | -2.976 | 26.024 | 42.322 | 1.00 | 57.78 | C |
| ATOM | 3214 | NH1 | ARG | B | 113 | -2.982 | 24.699 | 42.434 | 1.00 | 58.02 | N |
| ATOM | 3215 | NH2 | ARG | B | 113 | -3.494 | 26.600 | 41.238 | 1.00 | 57.87 | N |
| ATOM | 3216 | C | ARG | B | 113 | -3.250 | 28.210 | 48.505 | 1.00 | 42.32 | C |
| ATOM | 3217 | O | ARG | B | 113 | -2.973 | 29.407 | 48.577 | 1.00 | 43.39 | O |
| ATOM | 3218 | N | TYR | B | 114 | -4.172 | 27.631 | 49.266 | 1.00 | 40.81 | N |
| ATOM | 3219 | CA | TYR | B | 114 | -4.935 | 28.375 | 50.260 | 1.00 | 39.74 | C |
| ATOM | 3220 | CB | TYR | B | 114 | -6.197 | 28.974 | 49.645 | 1.00 | 40.42 | C |
| ATOM | 3221 | CG | TYR | B | 114 | -5.995 | 29.775 | 48.388 | 1.00 | 42.55 | C |
| ATOM | 3222 | CD1 | TYR | B | 114 | -5.669 | 31.127 | 48.446 | 1.00 | 43.72 | C |
| ATOM | 3223 | CE1 | TYR | B | 114 | -5.504 | 31.878 | 47.292 | 1.00 | 44.87 | C |
| ATOM | 3224 | CD2 | TYR | B | 114 | -6.148 | 29.187 | 47.136 | 1.00 | 43.40 | C |
| ATOM | 3225 | CE2 | TYR | B | 114 | -5.983 | 29.926 | 45.972 | 1.00 | 45.29 | C |
| ATOM | 3226 | CZ | TYR | B | 114 | -5.661 | 31.272 | 46.060 | 1.00 | 46.39 | C |
| ATOM | 3227 | OH | TYR | B | 114 | -5.496 | 32.015 | 44.913 | 1.00 | 48.58 | O |
| ATOM | 3228 | C | TYR | B | 114 | -5.390 | 27.420 | 51.339 | 1.00 | 39.52 | C |
| ATOM | 3229 | O | TYR | B | 114 | -5.044 | 26.242 | 51.335 | 1.00 | 40.51 | O |
| ATOM | 3230 | N | PHE | B | 115 | -6.181 | 27.950 | 52.260 | 1.00 | 39.30 | N |
| ATOM | 3231 | CA | PHE | B | 115 | -6.771 | 27.167 | 53.331 | 1.00 | 38.26 | C |
| ATOM | 3232 | CB | PHE | B | 115 | -5.730 | 26.801 | 54.406 | 1.00 | 40.05 | C |
| ATOM | 3233 | CG | PHE | B | 115 | -5.209 | 27.967 | 55.198 | 1.00 | 39.50 | C |
| ATOM | 3234 | CD1 | PHE | B | 115 | -5.888 | 28.424 | 56.323 | 1.00 | 39.70 | C |
| ATOM | 3235 | CD2 | PHE | B | 115 | -4.019 | 28.584 | 54.838 | 1.00 | 39.08 | C |
| ATOM | 3236 | CE1 | PHE | B | 115 | -5.384 | 29.481 | 57.081 | 1.00 | 39.39 | C |
| ATOM | 3237 | CE2 | PHE | B | 115 | -3.509 | 29.641 | 55.590 | 1.00 | 39.14 | C |
| ATOM | 3238 | CZ | PHE | B | 115 | -4.193 | 30.088 | 56.713 | 1.00 | 38.04 | C |
| ATOM | 3239 | C | PHE | B | 115 | -7.879 | 28.052 | 53.866 | 1.00 | 37.46 | C |
| ATOM | 3240 | O | PHE | B | 115 | -7.723 | 29.271 | 53.931 | 1.00 | 37.40 | O |
| ATOM | 3241 | N | PHE | B | 116 | -9.014 | 27.453 | 54.200 | 1.00 | 36.15 | N |
| ATOM | 3242 | CA | PHE | B | 116 | -10.135 | 28.232 | 54.692 | 1.00 | 37.19 | C |
| ATOM | 3243 | CB | PHE | B | 116 | -10.958 | 28.753 | 53.510 | 1.00 | 38.42 | C |
| ATOM | 3244 | CG | PHE | B | 116 | -11.681 | 27.675 | 52.746 | 1.00 | 39.24 | C |
| ATOM | 3245 | CD1 | PHE | B | 116 | -12.910 | 27.197 | 53.185 | 1.00 | 39.04 | C |
| ATOM | 3246 | CD2 | PHE | B | 116 | -11.140 | 27.143 | 51.584 | 1.00 | 38.65 | C |
| ATOM | 3247 | CE1 | PHE | B | 116 | -13.593 | 26.208 | 52.477 | 1.00 | 37.60 | C |
| ATOM | 3248 | CE2 | PHE | B | 116 | -11.817 | 26.152 | 50.871 | 1.00 | 38.25 | C |
| ATOM | 3249 | CZ | PHE | B | 116 | -13.047 | 25.687 | 51.321 | 1.00 | 36.97 | C |
| ATOM | 3250 | C | PHE | B | 116 | -11.005 | 27.398 | 55.612 | 1.00 | 37.28 | C |
| ATOM | 3251 | O | PHE | B | 116 | -10.945 | 26.180 | 55.571 | 1.00 | 38.10 | O |
| ATOM | 3252 | N | TYR | B | 117 | -11.810 | 28.053 | 56.441 | 1.00 | 37.38 | N |
| ATOM | 3253 | CA | TYR | B | 117 | -12.678 | 27.343 | 57.364 | 1.00 | 37.66 | C |
| ATOM | 3254 | CB | TYR | B | 117 | -12.628 | 28.027 | 58.736 | 1.00 | 38.14 | C |
| ATOM | 3255 | CG | TYR | B | 117 | -11.230 | 28.000 | 59.325 | 1.00 | 39.17 | C |
| ATOM | 3256 | CD1 | TYR | B | 117 | -10.779 | 26.909 | 60.067 | 1.00 | 39.03 | C |
| ATOM | 3257 | CE1 | TYR | B | 117 | -9.444 | 26.817 | 60.475 | 1.00 | 39.31 | C |
| ATOM | 3258 | CD2 | TYR | B | 117 | -10.312 | 29.000 | 59.021 | 1.00 | 38.92 | C |
| ATOM | 3259 | CE2 | TYR | B | 117 | -8.981 | 28.912 | 59.421 | 1.00 | 38.56 | C |
| ATOM | 3260 | CZ | TYR | B | 117 | -8.554 | 27.821 | 60.139 | 1.00 | 39.71 | C |
| ATOM | 3261 | OH | TYR | B | 117 | -7.224 | 27.708 | 60.475 | 1.00 | 40.62 | O |
| ATOM | 3262 | C | TYR | B | 117 | -14.104 | 27.274 | 56.824 | 1.00 | 38.78 | C |
| ATOM | 3263 | O | TYR | B | 117 | -14.526 | 28.116 | 56.024 | 1.00 | 38.40 | O |
| ATOM | 3264 | N | SER | B | 118 | -14.839 | 26.254 | 57.251 | 1.00 | 39.65 | N |
| ATOM | 3265 | CA | SER | B | 118 | -16.205 | 26.069 | 56.802 | 1.00 | 41.25 | C |
| ATOM | 3266 | CB | SER | B | 118 | -16.223 | 25.273 | 55.499 | 1.00 | 41.61 | C |
| ATOM | 3267 | OG | SER | B | 118 | -15.949 | 23.907 | 55.744 | 1.00 | 39.92 | O |
| ATOM | 3268 | C | SER | B | 118 | -16.965 | 25.309 | 57.872 | 1.00 | 42.59 | C |
| ATOM | 3269 | O | SER | B | 118 | -16.355 | 24.723 | 58.761 | 1.00 | 42.89 | O |
| ATOM | 3270 | N | SER | B | 119 | -18.295 | 25.319 | 57.781 | 1.00 | 45.03 | N |
| ATOM | 3271 | CA | SER | B | 119 | -19.148 | 24.633 | 58.750 | 1.00 | 46.39 | C |
| ATOM | 3272 | CB | SER | B | 119 | -20.377 | 25.491 | 59.056 | 1.00 | 47.38 | C |
| ATOM | 3273 | OG | SER | B | 119 | -20.024 | 26.685 | 59.748 | 1.00 | 46.67 | O |
| ATOM | 3274 | C | SER | B | 119 | -19.598 | 23.262 | 58.248 | 1.00 | 47.23 | C |
| ATOM | 3275 | O | SER | B | 119 | -19.799 | 22.333 | 59.037 | 1.00 | 47.46 | O |
| ATOM | 3276 | N | ALA | B | 125 | -17.985 | 20.959 | 64.031 | 1.00 | 56.01 | N |

FIG. 2-50

```
ATOM   3277  CA   ALA B 125     -18.160  22.391  64.258  1.00 56.69           C
ATOM   3278  CB   ALA B 125     -17.540  22.794  65.611  1.00 57.13           C
ATOM   3279  C    ALA B 125     -17.503  23.166  63.135  1.00 56.42           C
ATOM   3280  O    ALA B 125     -18.168  23.598  62.190  1.00 57.33           O
ATOM   3281  N    ALA B 126     -16.187  23.332  63.251  1.00 54.73           N
ATOM   3282  CA   ALA B 126     -15.395  24.042  62.250  1.00 52.37           C
ATOM   3283  CB   ALA B 126     -14.532  25.111  62.926  1.00 51.59           C
ATOM   3284  C    ALA B 126     -14.517  23.039  61.523  1.00 50.57           C
ATOM   3285  O    ALA B 126     -13.972  22.125  62.132  1.00 50.34           O
ATOM   3286  N    TYR B 127     -14.408  23.189  60.213  1.00 48.39           N
ATOM   3287  CA   TYR B 127     -13.568  22.295  59.432  1.00 46.81           C
ATOM   3288  CB   TYR B 127     -14.319  21.666  58.258  1.00 48.72           C
ATOM   3289  CG   TYR B 127     -15.254  20.536  58.590  1.00 50.22           C
ATOM   3290  CD1  TYR B 127     -16.439  20.764  59.269  1.00 51.31           C
ATOM   3291  CE1  TYR B 127     -17.339  19.731  59.497  1.00 52.97           C
ATOM   3292  CD2  TYR B 127     -14.985  19.245  58.145  1.00 52.34           C
ATOM   3293  CE2  TYR B 127     -15.872  18.207  58.366  1.00 53.22           C
ATOM   3294  CZ   TYR B 127     -17.052  18.455  59.032  1.00 53.26           C
ATOM   3295  OH   TYR B 127     -17.946  17.424  59.216  1.00 54.20           O
ATOM   3296  C    TYR B 127     -12.468  23.135  58.840  1.00 44.92           C
ATOM   3297  O    TYR B 127     -12.653  24.323  58.582  1.00 43.77           O
ATOM   3298  N    LEU B 128     -11.319  22.511  58.627  1.00 42.47           N
ATOM   3299  CA   LEU B 128     -10.206  23.200  58.010  1.00 39.82           C
ATOM   3300  CB   LEU B 128      -8.881  22.834  58.668  1.00 37.96           C
ATOM   3301  CG   LEU B 128      -7.707  23.437  57.901  1.00 38.87           C
ATOM   3302  CD1  LEU B 128      -7.644  24.942  58.118  1.00 37.81           C
ATOM   3303  CD2  LEU B 128      -6.427  22.775  58.332  1.00 39.69           C
ATOM   3304  C    LEU B 128     -10.203  22.704  56.586  1.00 38.78           C
ATOM   3305  O    LEU B 128     -10.403  21.515  56.338  1.00 38.43           O
ATOM   3306  N    ASN B 129      -9.982  23.607  55.646  1.00 36.97           N
ATOM   3307  CA   ASN B 129      -9.963  23.216  54.253  1.00 35.86           C
ATOM   3308  CB   ASN B 129     -11.095  23.923  53.504  1.00 35.29           C
ATOM   3309  CG   ASN B 129     -12.468  23.465  53.965  1.00 35.77           C
ATOM   3310  OD1  ASN B 129     -13.011  22.493  53.454  1.00 38.56           O
ATOM   3311  ND2  ASN B 129     -13.025  24.154  54.948  1.00 36.42           N
ATOM   3312  C    ASN B 129      -8.611  23.589  53.690  1.00 35.65           C
ATOM   3313  O    ASN B 129      -8.185  24.738  53.784  1.00 37.49           O
ATOM   3314  N    LEU B 130      -7.919  22.602  53.139  1.00 35.50           N
ATOM   3315  CA   LEU B 130      -6.612  22.822  52.554  1.00 35.02           C
ATOM   3316  CB   LEU B 130      -5.635  21.751  53.044  1.00 35.28           C
ATOM   3317  CG   LEU B 130      -5.266  21.808  54.530  1.00 35.77           C
ATOM   3318  CD1  LEU B 130      -4.610  20.511  54.986  1.00 34.79           C
ATOM   3319  CD2  LEU B 130      -4.341  22.993  54.746  1.00 37.88           C
ATOM   3320  C    LEU B 130      -6.780  22.718  51.051  1.00 35.11           C
ATOM   3321  O    LEU B 130      -7.239  21.691  50.555  1.00 36.42           O
ATOM   3322  N    VAL B 131      -6.444  23.782  50.329  1.00 34.66           N
ATOM   3323  CA   VAL B 131      -6.547  23.763  48.874  1.00 36.20           C
ATOM   3324  CB   VAL B 131      -6.987  25.123  48.310  1.00 37.42           C
ATOM   3325  CG1  VAL B 131      -7.187  25.020  46.802  1.00 37.00           C
ATOM   3326  CG2  VAL B 131      -8.284  25.566  48.984  1.00 37.32           C
ATOM   3327  C    VAL B 131      -5.157  23.423  48.365  1.00 37.41           C
ATOM   3328  O    VAL B 131      -4.206  24.162  48.613  1.00 39.47           O
ATOM   3329  N    LEU B 132      -5.041  22.312  47.641  1.00 37.70           N
ATOM   3330  CA   LEU B 132      -3.744  21.846  47.166  1.00 36.92           C
ATOM   3331  CB   LEU B 132      -3.373  20.583  47.931  1.00 35.83           C
ATOM   3332  CG   LEU B 132      -3.358  20.720  49.446  1.00 35.10           C
ATOM   3333  CD1  LEU B 132      -3.955  19.480  50.072  1.00 34.42           C
ATOM   3334  CD2  LEU B 132      -1.949  20.964  49.916  1.00 31.89           C
ATOM   3335  C    LEU B 132      -3.658  21.535  45.687  1.00 38.35           C
ATOM   3336  O    LEU B 132      -4.669  21.304  45.031  1.00 39.20           O
ATOM   3337  N    ASP B 133      -2.431  21.515  45.174  1.00 39.75           N
ATOM   3338  CA   ASP B 133      -2.180  21.189  43.774  1.00 41.83           C
ATOM   3339  CB   ASP B 133      -0.682  20.958  43.524  1.00 44.76           C
ATOM   3340  CG   ASP B 133       0.113  22.240  43.353  1.00 47.88           C
ATOM   3341  OD1  ASP B 133       1.342  22.197  43.668  1.00 47.86           O
ATOM   3342  OD2  ASP B 133      -0.468  23.256  42.888  1.00 46.54           O
ATOM   3343  C    ASP B 133      -2.880  19.860  43.529  1.00 43.11           C
```

FIG. 2-51

```
ATOM   3344  O    ASP B 133      -2.796  18.943  44.355  1.00 42.47           O
ATOM   3345  N    TYR B 134      -3.548  19.740  42.391  1.00 43.69           N
ATOM   3346  CA   TYR B 134      -4.209  18.492  42.063  1.00 42.89           C
ATOM   3347  CB   TYR B 134      -5.596  18.733  41.476  1.00 43.93           C
ATOM   3348  CG   TYR B 134      -6.266  17.455  41.051  1.00 43.85           C
ATOM   3349  CD1  TYR B 134      -6.792  16.579  41.997  1.00 44.88           C
ATOM   3350  CE1  TYR B 134      -7.373  15.381  41.617  1.00 45.46           C
ATOM   3351  CD2  TYR B 134      -6.335  17.101  39.709  1.00 43.13           C
ATOM   3352  CE2  TYR B 134      -6.913  15.904  39.314  1.00 44.38           C
ATOM   3353  CZ   TYR B 134      -7.432  15.046  40.273  1.00 45.66           C
ATOM   3354  OH   TYR B 134      -8.022  13.853  39.893  1.00 46.16           O
ATOM   3355  C    TYR B 134      -3.376  17.749  41.041  1.00 42.19           C
ATOM   3356  O    TYR B 134      -3.388  18.092  39.866  1.00 43.08           O
ATOM   3357  N    VAL B 135      -2.648  16.733  41.482  1.00 41.87           N
ATOM   3358  CA   VAL B 135      -1.829  15.957  40.563  1.00 41.04           C
ATOM   3359  CB   VAL B 135      -0.374  15.880  41.050  1.00 39.57           C
ATOM   3360  CG1  VAL B 135       0.486  15.214  40.002  1.00 37.45           C
ATOM   3361  CG2  VAL B 135       0.140  17.276  41.372  1.00 36.92           C
ATOM   3362  C    VAL B 135      -2.462  14.573  40.517  1.00 42.83           C
ATOM   3363  O    VAL B 135      -2.492  13.857  41.518  1.00 44.49           O
ATOM   3364  N    PRO B 136      -2.984  14.179  39.345  1.00 44.08           N
ATOM   3365  CD   PRO B 136      -2.917  14.926  38.074  1.00 45.07           C
ATOM   3366  CA   PRO B 136      -3.641  12.882  39.147  1.00 43.50           C
ATOM   3367  CB   PRO B 136      -4.142  12.968  37.707  1.00 43.50           C
ATOM   3368  CG   PRO B 136      -3.128  13.834  37.045  1.00 43.63           C
ATOM   3369  C    PRO B 136      -2.858  11.601  39.398  1.00 41.58           C
ATOM   3370  O    PRO B 136      -3.195  10.815  40.283  1.00 41.23           O
ATOM   3371  N    GLU B 137      -1.816  11.393  38.614  1.00 39.26           N
ATOM   3372  CA   GLU B 137      -1.041  10.178  38.728  1.00 37.78           C
ATOM   3373  CB   GLU B 137      -0.183  10.015  37.469  1.00 37.87           C
ATOM   3374  CG   GLU B 137      -0.432   8.695  36.737  1.00 41.82           C
ATOM   3375  CD   GLU B 137      -1.820   8.147  37.006  1.00 44.15           C
ATOM   3376  OE1  GLU B 137      -2.809   8.780  36.578  1.00 44.69           O
ATOM   3377  OE2  GLU B 137      -1.929   7.089  37.659  1.00 47.43           O
ATOM   3378  C    GLU B 137      -0.188  10.053  39.987  1.00 36.39           C
ATOM   3379  O    GLU B 137       0.261  11.049  40.562  1.00 35.94           O
ATOM   3380  N    THR B 138       0.025   8.807  40.405  1.00 33.49           N
ATOM   3381  CA   THR B 138       0.838   8.504  41.575  1.00 33.11           C
ATOM   3382  CB   THR B 138      -0.003   7.994  42.765  1.00 32.27           C
ATOM   3383  OG1  THR B 138      -0.511   6.689  42.466  1.00 33.46           O
ATOM   3384  CG2  THR B 138      -1.162   8.929  43.047  1.00 30.50           C
ATOM   3385  C    THR B 138       1.811   7.397  41.206  1.00 33.45           C
ATOM   3386  O    THR B 138       1.517   6.559  40.351  1.00 34.33           O
ATOM   3387  N    VAL B 139       2.975   7.398  41.840  1.00 32.99           N
ATOM   3388  CA   VAL B 139       3.969   6.374  41.584  1.00 30.90           C
ATOM   3389  CB   VAL B 139       5.192   6.556  42.520  1.00 30.72           C
ATOM   3390  CG1  VAL B 139       6.129   5.364  42.423  1.00 30.13           C
ATOM   3391  CG2  VAL B 139       5.924   7.835  42.166  1.00 27.08           C
ATOM   3392  C    VAL B 139       3.317   5.011  41.834  1.00 32.68           C
ATOM   3393  O    VAL B 139       3.678   4.016  41.206  1.00 33.95           O
ATOM   3394  N    TYR B 140       2.346   4.966  42.743  1.00 32.74           N
ATOM   3395  CA   TYR B 140       1.661   3.713  43.047  1.00 33.80           C
ATOM   3396  CB   TYR B 140       0.679   3.877  44.210  1.00 35.18           C
ATOM   3397  CG   TYR B 140      -0.167   2.634  44.402  1.00 35.87           C
ATOM   3398  CD1  TYR B 140       0.385   1.464  44.924  1.00 36.43           C
ATOM   3399  CE1  TYR B 140      -0.365   0.290  45.012  1.00 38.08           C
ATOM   3400  CD2  TYR B 140      -1.493   2.600  43.979  1.00 36.84           C
ATOM   3401  CE2  TYR B 140      -2.250   1.432  44.061  1.00 38.13           C
ATOM   3402  CZ   TYR B 140      -1.680   0.283  44.576  1.00 38.13           C
ATOM   3403  OH   TYR B 140      -2.419  -0.872  44.648  1.00 40.21           O
ATOM   3404  C    TYR B 140       0.887   3.136  41.863  1.00 34.52           C
ATOM   3405  O    TYR B 140       0.911   1.933  41.625  1.00 32.82           O
ATOM   3406  N    ARG B 141       0.176   4.001  41.150  1.00 34.70           N
ATOM   3407  CA   ARG B 141      -0.601   3.589  40.000  1.00 35.96           C
ATOM   3408  CB   ARG B 141      -1.497   4.736  39.540  1.00 40.39           C
ATOM   3409  CG   ARG B 141      -2.657   5.031  40.476  1.00 46.02           C
ATOM   3410  CD   ARG B 141      -2.966   6.525  40.541  1.00 49.60           C
```

FIG. 2-52

```
ATOM   3411  NE   ARG B 141      -4.316   6.764  41.040  1.00 53.63           N
ATOM   3412  CZ   ARG B 141      -5.404   6.755  40.276  1.00 54.94           C
ATOM   3413  NH1  ARG B 141      -5.294   6.526  38.971  1.00 55.30           N
ATOM   3414  NH2  ARG B 141      -6.600   6.956  40.822  1.00 55.89           N
ATOM   3415  C    ARG B 141       0.328   3.176  38.873  1.00 35.01           C
ATOM   3416  O    ARG B 141       0.095   2.167  38.217  1.00 33.61           O
ATOM   3417  N    VAL B 142       1.384   3.947  38.652  1.00 34.19           N
ATOM   3418  CA   VAL B 142       2.311   3.610  37.589  1.00 33.82           C
ATOM   3419  CB   VAL B 142       3.369   4.704  37.366  1.00 32.08           C
ATOM   3420  CG1  VAL B 142       4.421   4.218  36.391  1.00 32.29           C
ATOM   3421  CG2  VAL B 142       2.710   5.955  36.822  1.00 31.53           C
ATOM   3422  C    VAL B 142       3.009   2.304  37.903  1.00 35.17           C
ATOM   3423  O    VAL B 142       3.136   1.449  37.035  1.00 36.96           O
ATOM   3424  N    ALA B 143       3.456   2.137  39.141  1.00 34.60           N
ATOM   3425  CA   ALA B 143       4.133   0.905  39.512  1.00 34.60           C
ATOM   3426  CB   ALA B 143       4.619   0.984  40.938  1.00 34.72           C
ATOM   3427  C    ALA B 143       3.170  -0.263  39.345  1.00 34.26           C
ATOM   3428  O    ALA B 143       3.558  -1.340  38.896  1.00 34.68           O
ATOM   3429  N    ARG B 144       1.913  -0.036  39.698  1.00 35.61           N
ATOM   3430  CA   ARG B 144       0.884  -1.060  39.590  1.00 38.20           C
ATOM   3431  CB   ARG B 144      -0.414  -0.555  40.228  1.00 39.15           C
ATOM   3432  CG   ARG B 144      -1.336  -1.658  40.713  1.00 40.25           C
ATOM   3433  CD   ARG B 144      -2.634  -1.669  39.940  1.00 42.20           C
ATOM   3434  NE   ARG B 144      -3.407  -0.452  40.159  1.00 45.07           N
ATOM   3435  CZ   ARG B 144      -4.183  -0.232  41.216  1.00 46.54           C
ATOM   3436  NH1  ARG B 144      -4.303  -1.154  42.169  1.00 47.11           N
ATOM   3437  NH2  ARG B 144      -4.832   0.921  41.325  1.00 47.37           N
ATOM   3438  C    ARG B 144       0.646  -1.437  38.125  1.00 39.31           C
ATOM   3439  O    ARG B 144       0.571  -2.617  37.789  1.00 39.03           O
ATOM   3440  N    HIS B 145       0.534  -0.421  37.267  1.00 41.76           N
ATOM   3441  CA   HIS B 145       0.314  -0.596  35.828  1.00 43.21           C
ATOM   3442  CB   HIS B 145       0.273   0.780  35.143  1.00 45.91           C
ATOM   3443  CG   HIS B 145       0.124   0.730  33.651  1.00 51.22           C
ATOM   3444  CD2  HIS B 145       0.280  -0.283  32.761  1.00 52.90           C
ATOM   3445  ND1  HIS B 145      -0.197   1.846  32.902  1.00 53.04           N
ATOM   3446  CE1  HIS B 145      -0.233   1.523  31.619  1.00 52.48           C
ATOM   3447  NE2  HIS B 145       0.053   0.236  31.507  1.00 52.27           N
ATOM   3448  C    HIS B 145       1.405  -1.473  35.218  1.00 43.01           C
ATOM   3449  O    HIS B 145       1.096  -2.476  34.584  1.00 43.47           O
ATOM   3450  N    TYR B 146       2.673  -1.106  35.410  1.00 42.90           N
ATOM   3451  CA   TYR B 146       3.782  -1.892  34.874  1.00 41.49           C
ATOM   3452  CB   TYR B 146       5.133  -1.263  35.192  1.00 38.50           C
ATOM   3453  CG   TYR B 146       5.517  -0.160  34.262  1.00 37.79           C
ATOM   3454  CD1  TYR B 146       4.901   1.081  34.351  1.00 37.16           C
ATOM   3455  CE1  TYR B 146       5.215   2.097  33.476  1.00 37.56           C
ATOM   3456  CD2  TYR B 146       6.473  -0.361  33.257  1.00 36.64           C
ATOM   3457  CE2  TYR B 146       6.796   0.661  32.368  1.00 37.21           C
ATOM   3458  CZ   TYR B 146       6.156   1.887  32.487  1.00 36.81           C
ATOM   3459  OH   TYR B 146       6.428   2.925  31.634  1.00 38.59           O
ATOM   3460  C    TYR B 146       3.813  -3.280  35.438  1.00 43.03           C
ATOM   3461  O    TYR B 146       4.306  -4.203  34.799  1.00 45.83           O
ATOM   3462  N    SER B 147       3.300  -3.434  36.646  1.00 43.41           N
ATOM   3463  CA   SER B 147       3.334  -4.728  37.299  1.00 45.15           C
ATOM   3464  CB   SER B 147       3.300  -4.544  38.810  1.00 45.39           C
ATOM   3465  OG   SER B 147       3.080  -5.794  39.440  1.00 48.40           O
ATOM   3466  C    SER B 147       2.252  -5.718  36.895  1.00 46.19           C
ATOM   3467  O    SER B 147       2.529  -6.909  36.743  1.00 45.63           O
ATOM   3468  N    ARG B 148       1.018  -5.250  36.746  1.00 47.31           N
ATOM   3469  CA   ARG B 148      -0.050  -6.160  36.355  1.00 49.70           C
ATOM   3470  CB   ARG B 148      -1.376  -5.404  36.217  1.00 50.73           C
ATOM   3471  CG   ARG B 148      -2.024  -5.050  37.545  1.00 52.52           C
ATOM   3472  CD   ARG B 148      -3.238  -4.165  37.332  1.00 53.64           C
ATOM   3473  NE   ARG B 148      -4.100  -4.124  38.512  1.00 55.34           N
ATOM   3474  CZ   ARG B 148      -4.964  -3.144  38.776  1.00 55.69           C
ATOM   3475  NH1  ARG B 148      -5.077  -2.111  37.950  1.00 54.98           N
ATOM   3476  NH2  ARG B 148      -5.735  -3.208  39.858  1.00 55.91           N
ATOM   3477  C    ARG B 148       0.309  -6.842  35.030  1.00 50.61           C
```

FIG. 2-53

| | | | | | | | | | | |
|---|---|---|---|---|---|---|---|---|---|---|
| ATOM | 3478 | O | ARG | B | 148 | -0.008 | -8.013 | 34.812 | 1.00 50.85 | O |
| ATOM | 3479 | N | ALA | B | 149 | 0.989 | -6.106 | 34.156 | 1.00 50.88 | N |
| ATOM | 3480 | CA | ALA | B | 149 | 1.391 | -6.642 | 32.858 | 1.00 51.66 | C |
| ATOM | 3481 | CB | ALA | B | 149 | 1.221 | -5.581 | 31.778 | 1.00 50.52 | C |
| ATOM | 3482 | C | ALA | B | 149 | 2.832 | -7.153 | 32.868 | 1.00 51.87 | C |
| ATOM | 3483 | O | ALA | B | 149 | 3.562 | -7.006 | 31.885 | 1.00 51.22 | O |
| ATOM | 3484 | N | LYS | B | 150 | 3.227 | -7.752 | 33.991 | 1.00 52.85 | N |
| ATOM | 3485 | CA | LYS | B | 150 | 4.562 | -8.315 | 34.150 | 1.00 53.30 | C |
| ATOM | 3486 | CB | LYS | B | 150 | 4.575 | -9.757 | 33.649 | 1.00 55.11 | C |
| ATOM | 3487 | CG | LYS | B | 150 | 4.662 | -10.783 | 34.764 | 1.00 58.20 | C |
| ATOM | 3488 | CD | LYS | B | 150 | 3.308 | -11.113 | 35.394 | 1.00 59.36 | C |
| ATOM | 3489 | CE | LYS | B | 150 | 2.703 | -12.387 | 34.763 | 1.00 60.61 | C |
| ATOM | 3490 | NZ | LYS | B | 150 | 1.622 | -13.015 | 35.598 | 1.00 59.70 | N |
| ATOM | 3491 | C | LYS | B | 150 | 5.684 | -7.537 | 33.464 | 1.00 53.40 | C |
| ATOM | 3492 | O | LYS | B | 150 | 6.507 | -8.114 | 32.761 | 1.00 53.30 | O |
| ATOM | 3493 | N | GLN | B | 151 | 5.715 | -6.225 | 33.660 | 1.00 53.27 | N |
| ATOM | 3494 | CA | GLN | B | 151 | 6.758 | -5.404 | 33.061 | 1.00 51.45 | C |
| ATOM | 3495 | CB | GLN | B | 151 | 6.142 | -4.338 | 32.163 | 1.00 51.15 | C |
| ATOM | 3496 | CG | GLN | B | 151 | 7.151 | -3.604 | 31.291 | 1.00 53.32 | C |
| ATOM | 3497 | CD | GLN | B | 151 | 7.375 | -4.292 | 29.961 | 1.00 54.22 | C |
| ATOM | 3498 | OE1 | GLN | B | 151 | 6.431 | -4.805 | 29.361 | 1.00 56.36 | O |
| ATOM | 3499 | NE2 | GLN | B | 151 | 8.618 | -4.290 | 29.481 | 1.00 53.71 | N |
| ATOM | 3500 | C | GLN | B | 151 | 7.537 | -4.735 | 34.192 | 1.00 50.09 | C |
| ATOM | 3501 | O | GLN | B | 151 | 7.055 | -4.625 | 35.321 | 1.00 48.80 | O |
| ATOM | 3502 | N | THR | B | 152 | 8.739 | -4.279 | 33.876 | 1.00 48.11 | N |
| ATOM | 3503 | CA | THR | B | 152 | 9.599 | -3.633 | 34.856 | 1.00 46.20 | C |
| ATOM | 3504 | CB | THR | B | 152 | 10.943 | -4.381 | 34.957 | 1.00 46.58 | C |
| ATOM | 3505 | OG1 | THR | B | 152 | 11.969 | -3.477 | 35.374 | 1.00 47.47 | O |
| ATOM | 3506 | CG2 | THR | B | 152 | 11.315 | -4.991 | 33.610 | 1.00 48.20 | C |
| ATOM | 3507 | C | THR | B | 152 | 9.849 | -2.182 | 34.478 | 1.00 43.72 | C |
| ATOM | 3508 | O | THR | B | 152 | 10.485 | -1.896 | 33.466 | 1.00 44.29 | O |
| ATOM | 3509 | N | LEU | B | 153 | 9.334 | -1.271 | 35.291 | 1.00 40.95 | N |
| ATOM | 3510 | CA | LEU | B | 153 | 9.494 | 0.157 | 35.043 | 1.00 38.98 | C |
| ATOM | 3511 | CB | LEU | B | 153 | 9.124 | 0.936 | 36.300 | 1.00 38.19 | C |
| ATOM | 3512 | CG | LEU | B | 153 | 9.118 | 2.457 | 36.207 | 1.00 38.36 | C |
| ATOM | 3513 | CD1 | LEU | B | 153 | 7.841 | 2.930 | 35.547 | 1.00 35.98 | C |
| ATOM | 3514 | CD2 | LEU | B | 153 | 9.246 | 3.032 | 37.610 | 1.00 37.72 | C |
| ATOM | 3515 | C | LEU | B | 153 | 10.923 | 0.516 | 34.617 | 1.00 38.31 | C |
| ATOM | 3516 | O | LEU | B | 153 | 11.889 | 0.174 | 35.302 | 1.00 36.72 | O |
| ATOM | 3517 | N | PRO | B | 154 | 11.074 | 1.205 | 33.469 | 1.00 38.07 | N |
| ATOM | 3518 | CD | PRO | B | 154 | 10.025 | 1.603 | 32.511 | 1.00 38.38 | C |
| ATOM | 3519 | CA | PRO | B | 154 | 12.398 | 1.599 | 32.981 | 1.00 36.87 | C |
| ATOM | 3520 | CB | PRO | B | 154 | 12.067 | 2.547 | 31.840 | 1.00 36.50 | C |
| ATOM | 3521 | CG | PRO | B | 154 | 10.829 | 1.927 | 31.271 | 1.00 37.69 | C |
| ATOM | 3522 | C | PRO | B | 154 | 13.203 | 2.278 | 34.087 | 1.00 36.80 | C |
| ATOM | 3523 | O | PRO | B | 154 | 12.681 | 3.123 | 34.817 | 1.00 36.69 | O |
| ATOM | 3524 | N | VAL | B | 155 | 14.475 | 1.907 | 34.197 | 1.00 36.28 | N |
| ATOM | 3525 | CA | VAL | B | 155 | 15.360 | 2.452 | 35.216 | 1.00 35.66 | C |
| ATOM | 3526 | CB | VAL | B | 155 | 16.754 | 1.783 | 35.135 | 1.00 34.61 | C |
| ATOM | 3527 | CG1 | VAL | B | 155 | 17.645 | 2.262 | 36.270 | 1.00 33.77 | C |
| ATOM | 3528 | CG2 | VAL | B | 155 | 16.596 | 0.279 | 35.195 | 1.00 35.70 | C |
| ATOM | 3529 | C | VAL | B | 155 | 15.516 | 3.974 | 35.190 | 1.00 36.24 | C |
| ATOM | 3530 | O | VAL | B | 155 | 15.866 | 4.574 | 36.204 | 1.00 37.26 | O |
| ATOM | 3531 | N | ILE | B | 156 | 15.254 | 4.612 | 34.052 | 1.00 36.67 | N |
| ATOM | 3532 | CA | ILE | B | 156 | 15.376 | 6.068 | 33.982 | 1.00 35.85 | C |
| ATOM | 3533 | CB | ILE | B | 156 | 15.345 | 6.590 | 32.509 | 1.00 36.47 | C |
| ATOM | 3534 | CG2 | ILE | B | 156 | 14.037 | 6.211 | 31.836 | 1.00 37.16 | C |
| ATOM | 3535 | CG1 | ILE | B | 156 | 15.477 | 8.121 | 32.481 | 1.00 35.95 | C |
| ATOM | 3536 | CD1 | ILE | B | 156 | 16.752 | 8.657 | 33.121 | 1.00 36.69 | C |
| ATOM | 3537 | C | ILE | B | 156 | 14.250 | 6.721 | 34.779 | 1.00 35.42 | C |
| ATOM | 3538 | O | ILE | B | 156 | 14.435 | 7.783 | 35.366 | 1.00 35.96 | O |
| ATOM | 3539 | N | TYR | B | 157 | 13.083 | 6.084 | 34.799 | 1.00 35.03 | N |
| ATOM | 3540 | CA | TYR | B | 157 | 11.954 | 6.619 | 35.549 | 1.00 35.54 | C |
| ATOM | 3541 | CB | TYR | B | 157 | 10.662 | 5.890 | 35.147 | 1.00 35.92 | C |
| ATOM | 3542 | CG | TYR | B | 157 | 10.145 | 6.292 | 33.773 | 1.00 37.07 | C |
| ATOM | 3543 | CD1 | TYR | B | 157 | 9.938 | 5.341 | 32.768 | 1.00 37.20 | C |
| ATOM | 3544 | CE1 | TYR | B | 157 | 9.469 | 5.715 | 31.499 | 1.00 38.64 | C |

FIG. 2-54

```
ATOM   3545  CD2 TYR B 157      9.865   7.629  33.478  1.00 38.47           C
ATOM   3546  CE2 TYR B 157      9.397   8.014  32.217  1.00 39.09           C
ATOM   3547  CZ  TYR B 157      9.199   7.057  31.232  1.00 39.97           C
ATOM   3548  OH  TYR B 157      8.737   7.444  29.987  1.00 39.12           O
ATOM   3549  C   TYR B 157     12.264   6.438  37.041  1.00 35.59           C
ATOM   3550  O   TYR B 157     11.992   7.316  37.868  1.00 33.02           O
ATOM   3551  N   VAL B 158     12.866   5.294  37.358  1.00 34.67           N
ATOM   3552  CA  VAL B 158     13.262   4.969  38.717  1.00 33.02           C
ATOM   3553  CB  VAL B 158     13.905   3.562  38.782  1.00 33.52           C
ATOM   3554  CG1 VAL B 158     14.267   3.204  40.217  1.00 32.36           C
ATOM   3555  CG2 VAL B 158     12.935   2.533  38.216  1.00 31.12           C
ATOM   3556  C   VAL B 158     14.264   6.013  39.223  1.00 32.88           C
ATOM   3557  O   VAL B 158     14.106   6.563  40.315  1.00 32.44           O
ATOM   3558  N   LYS B 159     15.287   6.304  38.426  1.00 30.90           N
ATOM   3559  CA  LYS B 159     16.272   7.295  38.836  1.00 30.81           C
ATOM   3560  CB  LYS B 159     17.377   7.432  37.790  1.00 30.12           C
ATOM   3561  CG  LYS B 159     18.137   6.157  37.529  1.00 29.89           C
ATOM   3562  CD  LYS B 159     19.210   6.392  36.495  1.00 31.10           C
ATOM   3563  CE  LYS B 159     19.796   5.084  35.996  1.00 30.42           C
ATOM   3564  NZ  LYS B 159     20.955   5.351  35.097  1.00 32.73           N
ATOM   3565  C   LYS B 159     15.608   8.647  39.059  1.00 32.10           C
ATOM   3566  O   LYS B 159     15.834   9.309  40.075  1.00 32.70           O
ATOM   3567  N   LEU B 160     14.785   9.058  38.104  1.00 33.25           N
ATOM   3568  CA  LEU B 160     14.083  10.330  38.197  1.00 33.73           C
ATOM   3569  CB  LEU B 160     13.228  10.549  36.953  1.00 34.21           C
ATOM   3570  CG  LEU B 160     13.968  10.975  35.686  1.00 34.33           C
ATOM   3571  CD1 LEU B 160     13.087  10.711  34.491  1.00 32.68           C
ATOM   3572  CD2 LEU B 160     14.364  12.445  35.786  1.00 33.82           C
ATOM   3573  C   LEU B 160     13.194  10.446  39.424  1.00 34.27           C
ATOM   3574  O   LEU B 160     13.262  11.433  40.150  1.00 33.76           O
ATOM   3575  N   TYR B 161     12.354   9.445  39.656  1.00 34.76           N
ATOM   3576  CA  TYR B 161     11.450   9.503  40.798  1.00 34.86           C
ATOM   3577  CB  TYR B 161     10.484   8.317  40.790  1.00 36.64           C
ATOM   3578  CG  TYR B 161      9.583   8.259  39.578  1.00 37.45           C
ATOM   3579  CD1 TYR B 161      9.345   9.386  38.803  1.00 36.68           C
ATOM   3580  CE1 TYR B 161      8.529   9.320  37.678  1.00 39.24           C
ATOM   3581  CD2 TYR B 161      8.978   7.065  39.203  1.00 39.55           C
ATOM   3582  CE2 TYR B 161      8.158   6.988  38.084  1.00 40.00           C
ATOM   3583  CZ  TYR B 161      7.938   8.114  37.326  1.00 40.28           C
ATOM   3584  OH  TYR B 161      7.126   8.031  36.217  1.00 42.16           O
ATOM   3585  C   TYR B 161     12.163   9.567  42.136  1.00 33.69           C
ATOM   3586  O   TYR B 161     11.913  10.475  42.926  1.00 32.29           O
ATOM   3587  N   MET B 162     13.045   8.607  42.391  1.00 33.73           N
ATOM   3588  CA  MET B 162     13.783   8.566  43.651  1.00 32.75           C
ATOM   3589  CB  MET B 162     14.720   7.360  43.679  1.00 32.53           C
ATOM   3590  CG  MET B 162     14.005   6.016  43.636  1.00 32.77           C
ATOM   3591  SD  MET B 162     12.722   5.848  44.888  1.00 32.78           S
ATOM   3592  CE  MET B 162     13.656   6.164  46.405  1.00 33.30           C
ATOM   3593  C   MET B 162     14.587   9.838  43.888  1.00 32.46           C
ATOM   3594  O   MET B 162     14.595  10.371  44.995  1.00 32.49           O
ATOM   3595  N   TYR B 163     15.262  10.320  42.852  1.00 31.48           N
ATOM   3596  CA  TYR B 163     16.051  11.526  42.990  1.00 32.59           C
ATOM   3597  CB  TYR B 163     16.670  11.925  41.657  1.00 33.34           C
ATOM   3598  CG  TYR B 163     17.474  13.203  41.735  1.00 33.33           C
ATOM   3599  CD1 TYR B 163     18.783  13.198  42.204  1.00 33.88           C
ATOM   3600  CE1 TYR B 163     19.528  14.371  42.271  1.00 33.10           C
ATOM   3601  CD2 TYR B 163     16.925  14.417  41.338  1.00 32.86           C
ATOM   3602  CE2 TYR B 163     17.663  15.599  41.403  1.00 32.61           C
ATOM   3603  CZ  TYR B 163     18.964  15.565  41.867  1.00 33.32           C
ATOM   3604  OH  TYR B 163     19.715  16.717  41.904  1.00 34.28           O
ATOM   3605  C   TYR B 163     15.199  12.680  43.498  1.00 33.27           C
ATOM   3606  O   TYR B 163     15.590  13.383  44.429  1.00 34.99           O
ATOM   3607  N   GLN B 164     14.036  12.873  42.882  1.00 31.89           N
ATOM   3608  CA  GLN B 164     13.140  13.955  43.267  1.00 29.74           C
ATOM   3609  CB  GLN B 164     12.022  14.111  42.233  1.00 31.18           C
ATOM   3610  CG  GLN B 164     12.515  14.575  40.863  1.00 31.83           C
ATOM   3611  CD  GLN B 164     11.387  14.708  39.856  1.00 32.03           C
```

FIG. 2-55

```
ATOM   3612  OE1 GLN B 164      10.653  15.700  39.845  1.00 30.71           O
ATOM   3613  NE2 GLN B 164      11.236  13.696  39.011  1.00 31.09           N
ATOM   3614  C   GLN B 164      12.546  13.742  44.654  1.00 29.43           C
ATOM   3615  O   GLN B 164      12.275  14.703  45.367  1.00 28.30           O
ATOM   3616  N   LEU B 165      12.334  12.485  45.030  1.00 28.64           N
ATOM   3617  CA  LEU B 165      11.806  12.187  46.343  1.00 28.80           C
ATOM   3618  CB  LEU B 165      11.396  10.719  46.452  1.00 28.87           C
ATOM   3619  CG  LEU B 165      11.195  10.196  47.881  1.00 28.04           C
ATOM   3620  CD1 LEU B 165      10.170  11.039  48.606  1.00 28.39           C
ATOM   3621  CD2 LEU B 165      10.782   8.746  47.846  1.00 27.05           C
ATOM   3622  C   LEU B 165      12.901  12.484  47.354  1.00 30.91           C
ATOM   3623  O   LEU B 165      12.645  13.069  48.411  1.00 32.32           O
ATOM   3624  N   PHE B 166      14.129  12.086  47.034  1.00 30.42           N
ATOM   3625  CA  PHE B 166      15.240  12.332  47.953  1.00 31.30           C
ATOM   3626  CB  PHE B 166      16.533  11.671  47.458  1.00 29.03           C
ATOM   3627  CG  PHE B 166      16.650  10.225  47.834  1.00 27.18           C
ATOM   3628  CD1 PHE B 166      16.505   9.829  49.160  1.00 27.63           C
ATOM   3629  CD2 PHE B 166      16.882   9.254  46.877  1.00 24.81           C
ATOM   3630  CE1 PHE B 166      16.585   8.482  49.520  1.00 26.81           C
ATOM   3631  CE2 PHE B 166      16.963   7.905  47.232  1.00 24.96           C
ATOM   3632  CZ  PHE B 166      16.813   7.522  48.556  1.00 24.59           C
ATOM   3633  C   PHE B 166      15.463  13.820  48.150  1.00 32.85           C
ATOM   3634  O   PHE B 166      15.793  14.270  49.244  1.00 34.75           O
ATOM   3635  N   ARG B 167      15.265  14.593  47.093  1.00 32.26           N
ATOM   3636  CA  ARG B 167      15.466  16.018  47.204  1.00 32.11           C
ATOM   3637  CB  ARG B 167      15.463  16.657  45.817  1.00 31.46           C
ATOM   3638  CG  ARG B 167      16.012  18.060  45.806  1.00 31.22           C
ATOM   3639  CD  ARG B 167      16.077  18.601  44.411  1.00 30.49           C
ATOM   3640  NE  ARG B 167      16.132  20.056  44.444  1.00 33.30           N
ATOM   3641  CZ  ARG B 167      15.835  20.838  43.412  1.00 33.85           C
ATOM   3642  NH1 ARG B 167      15.465  20.306  42.253  1.00 31.87           N
ATOM   3643  NH2 ARG B 167      15.890  22.154  43.545  1.00 34.98           N
ATOM   3644  C   ARG B 167      14.413  16.668  48.104  1.00 32.77           C
ATOM   3645  O   ARG B 167      14.738  17.534  48.910  1.00 33.89           O
ATOM   3646  N   SER B 168      13.158  16.247  47.979  1.00 32.58           N
ATOM   3647  CA  SER B 168      12.098  16.817  48.798  1.00 31.53           C
ATOM   3648  CB  SER B 168      10.728  16.281  48.374  1.00 31.16           C
ATOM   3649  OG  SER B 168      10.506  14.970  48.859  1.00 30.18           O
ATOM   3650  C   SER B 168      12.331  16.486  50.269  1.00 32.20           C
ATOM   3651  O   SER B 168      12.120  17.323  51.149  1.00 33.15           O
ATOM   3652  N   LEU B 169      12.756  15.257  50.535  1.00 31.86           N
ATOM   3653  CA  LEU B 169      13.015  14.826  51.900  1.00 31.88           C
ATOM   3654  CB  LEU B 169      13.359  13.327  51.915  1.00 29.46           C
ATOM   3655  CG  LEU B 169      12.327  12.321  52.477  1.00 30.65           C
ATOM   3656  CD1 LEU B 169      10.892  12.845  52.417  1.00 30.11           C
ATOM   3657  CD2 LEU B 169      12.452  11.023  51.709  1.00 28.38           C
ATOM   3658  C   LEU B 169      14.140  15.684  52.494  1.00 33.03           C
ATOM   3659  O   LEU B 169      14.041  16.156  53.627  1.00 32.58           O
ATOM   3660  N   ALA B 170      15.197  15.908  51.714  1.00 33.59           N
ATOM   3661  CA  ALA B 170      16.310  16.744  52.151  1.00 34.04           C
ATOM   3662  CB  ALA B 170      17.285  16.966  51.001  1.00 31.39           C
ATOM   3663  C   ALA B 170      15.743  18.086  52.615  1.00 35.30           C
ATOM   3664  O   ALA B 170      16.097  18.606  53.678  1.00 36.71           O
ATOM   3665  N   TYR B 171      14.847  18.627  51.802  1.00 35.32           N
ATOM   3666  CA  TYR B 171      14.204  19.901  52.079  1.00 36.13           C
ATOM   3667  CB  TYR B 171      13.263  20.263  50.939  1.00 36.25           C
ATOM   3668  CG  TYR B 171      12.577  21.581  51.148  1.00 35.40           C
ATOM   3669  CD1 TYR B 171      13.247  22.769  50.914  1.00 35.09           C
ATOM   3670  CE1 TYR B 171      12.634  23.988  51.119  1.00 35.47           C
ATOM   3671  CD2 TYR B 171      11.265  21.640  51.599  1.00 36.09           C
ATOM   3672  CE2 TYR B 171      10.639  22.860  51.811  1.00 36.98           C
ATOM   3673  CZ  TYR B 171      11.333  24.032  51.564  1.00 36.06           C
ATOM   3674  OH  TYR B 171      10.732  25.259  51.749  1.00 39.95           O
ATOM   3675  C   TYR B 171      13.417  19.951  53.384  1.00 36.12           C
ATOM   3676  O   TYR B 171      13.633  20.844  54.198  1.00 36.51           O
ATOM   3677  N   ILE B 172      12.487  19.020  53.574  1.00 36.53           N
ATOM   3678  CA  ILE B 172      11.697  19.020  54.797  1.00 38.33           C
```

FIG. 2-56

| ATOM | 3679 | CB | ILE | B | 172 | 10.492 | 18.048 | 54.727 | 1.00 | 39.03 | C |
| ATOM | 3680 | CG2 | ILE | B | 172 | 9.426 | 18.601 | 53.795 | 1.00 | 38.78 | C |
| ATOM | 3681 | CG1 | ILE | B | 172 | 10.971 | 16.659 | 54.301 | 1.00 | 39.94 | C |
| ATOM | 3682 | CD1 | ILE | B | 172 | 9.951 | 15.574 | 54.539 | 1.00 | 41.21 | C |
| ATOM | 3683 | C | ILE | B | 172 | 12.544 | 18.637 | 56.000 | 1.00 | 39.11 | C |
| ATOM | 3684 | O | ILE | B | 172 | 12.275 | 19.077 | 57.119 | 1.00 | 40.33 | O |
| ATOM | 3685 | N | HIS | B | 173 | 13.560 | 17.809 | 55.774 | 1.00 | 39.03 | N |
| ATOM | 3686 | CA | HIS | B | 173 | 14.436 | 17.372 | 56.862 | 1.00 | 39.65 | C |
| ATOM | 3687 | CB | HIS | B | 173 | 15.287 | 16.186 | 56.416 | 1.00 | 37.64 | C |
| ATOM | 3688 | CG | HIS | B | 173 | 14.546 | 14.888 | 56.399 | 1.00 | 36.36 | C |
| ATOM | 3689 | CD2 | HIS | B | 173 | 13.256 | 14.583 | 56.695 | 1.00 | 35.02 | C |
| ATOM | 3690 | ND1 | HIS | B | 173 | 15.111 | 13.713 | 55.949 | 1.00 | 35.25 | N |
| ATOM | 3691 | CE1 | HIS | B | 173 | 14.211 | 12.756 | 55.957 | 1.00 | 35.10 | C |
| ATOM | 3692 | NE2 | HIS | B | 173 | 13.069 | 13.259 | 56.407 | 1.00 | 33.61 | N |
| ATOM | 3693 | C | HIS | B | 173 | 15.341 | 18.452 | 57.443 | 1.00 | 40.41 | C |
| ATOM | 3694 | O | HIS | B | 173 | 15.743 | 18.371 | 58.607 | 1.00 | 41.41 | O |
| ATOM | 3695 | N | SER | B | 174 | 15.652 | 19.466 | 56.643 | 1.00 | 41.02 | N |
| ATOM | 3696 | CA | SER | B | 174 | 16.517 | 20.551 | 57.095 | 1.00 | 41.62 | C |
| ATOM | 3697 | CB | SER | B | 174 | 17.091 | 21.296 | 55.902 | 1.00 | 41.30 | C |
| ATOM | 3698 | OG | SER | B | 174 | 16.079 | 22.035 | 55.256 | 1.00 | 42.27 | O |
| ATOM | 3699 | C | SER | B | 174 | 15.746 | 21.527 | 57.978 | 1.00 | 42.45 | C |
| ATOM | 3700 | O | SER | B | 174 | 16.332 | 22.435 | 58.567 | 1.00 | 42.40 | O |
| ATOM | 3701 | N | PHE | B | 175 | 14.430 | 21.341 | 58.045 | 1.00 | 43.64 | N |
| ATOM | 3702 | CA | PHE | B | 175 | 13.562 | 22.163 | 58.877 | 1.00 | 43.15 | C |
| ATOM | 3703 | CB | PHE | B | 175 | 12.214 | 22.400 | 58.202 | 1.00 | 46.80 | C |
| ATOM | 3704 | CG | PHE | B | 175 | 12.247 | 23.418 | 57.111 | 1.00 | 49.71 | C |
| ATOM | 3705 | CD1 | PHE | B | 175 | 13.153 | 23.318 | 56.065 | 1.00 | 51.75 | C |
| ATOM | 3706 | CD2 | PHE | B | 175 | 11.357 | 24.480 | 57.125 | 1.00 | 50.88 | C |
| ATOM | 3707 | CE1 | PHE | B | 175 | 13.171 | 24.269 | 55.047 | 1.00 | 52.67 | C |
| ATOM | 3708 | CE2 | PHE | B | 175 | 11.366 | 25.435 | 56.115 | 1.00 | 52.18 | C |
| ATOM | 3709 | CZ | PHE | B | 175 | 12.275 | 25.330 | 55.074 | 1.00 | 52.94 | C |
| ATOM | 3710 | C | PHE | B | 175 | 13.313 | 21.350 | 60.128 | 1.00 | 41.87 | C |
| ATOM | 3711 | O | PHE | B | 175 | 12.674 | 21.812 | 61.070 | 1.00 | 41.68 | O |
| ATOM | 3712 | N | GLY | B | 176 | 13.800 | 20.116 | 60.108 | 1.00 | 40.76 | N |
| ATOM | 3713 | CA | GLY | B | 176 | 13.621 | 19.227 | 61.237 | 1.00 | 41.42 | C |
| ATOM | 3714 | C | GLY | B | 176 | 12.311 | 18.494 | 61.093 | 1.00 | 41.51 | C |
| ATOM | 3715 | O | GLY | B | 176 | 11.857 | 17.808 | 62.007 | 1.00 | 41.99 | O |
| ATOM | 3716 | N | ILE | B | 177 | 11.700 | 18.646 | 59.922 | 1.00 | 41.25 | N |
| ATOM | 3717 | CA | ILE | B | 177 | 10.425 | 18.013 | 59.628 | 1.00 | 39.90 | C |
| ATOM | 3718 | CB | ILE | B | 177 | 9.579 | 18.905 | 58.711 | 1.00 | 39.84 | C |
| ATOM | 3719 | CG2 | ILE | B | 177 | 8.162 | 18.348 | 58.612 | 1.00 | 40.39 | C |
| ATOM | 3720 | CG1 | ILE | B | 177 | 9.527 | 20.319 | 59.289 | 1.00 | 40.90 | C |
| ATOM | 3721 | CD1 | ILE | B | 177 | 8.933 | 21.349 | 58.362 | 1.00 | 42.63 | C |
| ATOM | 3722 | C | ILE | B | 177 | 10.589 | 16.632 | 58.979 | 1.00 | 39.41 | C |
| ATOM | 3723 | O | ILE | B | 177 | 11.270 | 16.474 | 57.961 | 1.00 | 39.60 | O |
| ATOM | 3724 | N | CYS | B | 178 | 9.960 | 15.641 | 59.601 | 1.00 | 36.80 | N |
| ATOM | 3725 | CA | CYS | B | 178 | 9.976 | 14.270 | 59.139 | 1.00 | 35.33 | C |
| ATOM | 3726 | CB | CYS | B | 178 | 10.218 | 13.332 | 60.314 | 1.00 | 36.22 | C |
| ATOM | 3727 | SG | CYS | B | 178 | 10.433 | 11.585 | 59.854 | 1.00 | 36.39 | S |
| ATOM | 3728 | C | CYS | B | 178 | 8.593 | 14.017 | 58.559 | 1.00 | 35.61 | C |
| ATOM | 3729 | O | CYS | B | 178 | 7.604 | 14.534 | 59.077 | 1.00 | 35.16 | O |
| ATOM | 3730 | N | HIS | B | 179 | 8.524 | 13.236 | 57.483 | 1.00 | 34.49 | N |
| ATOM | 3731 | CA | HIS | B | 179 | 7.261 | 12.947 | 56.833 | 1.00 | 31.99 | C |
| ATOM | 3732 | CB | HIS | B | 179 | 7.504 | 12.561 | 55.374 | 1.00 | 33.02 | C |
| ATOM | 3733 | CG | HIS | B | 179 | 6.252 | 12.479 | 54.560 | 1.00 | 32.98 | C |
| ATOM | 3734 | CD2 | HIS | B | 179 | 5.721 | 13.338 | 53.651 | 1.00 | 32.90 | C |
| ATOM | 3735 | ND1 | HIS | B | 179 | 5.345 | 11.449 | 54.676 | 1.00 | 31.68 | N |
| ATOM | 3736 | CE1 | HIS | B | 179 | 4.317 | 11.672 | 53.883 | 1.00 | 33.57 | C |
| ATOM | 3737 | NE2 | HIS | B | 179 | 4.523 | 12.818 | 53.248 | 1.00 | 31.45 | N |
| ATOM | 3738 | C | HIS | B | 179 | 6.493 | 11.845 | 57.545 | 1.00 | 32.46 | C |
| ATOM | 3739 | O | HIS | B | 179 | 5.269 | 11.921 | 57.695 | 1.00 | 31.78 | O |
| ATOM | 3740 | N | ARG | B | 180 | 7.212 | 10.814 | 57.972 | 1.00 | 30.89 | N |
| ATOM | 3741 | CA | ARG | B | 180 | 6.604 | 9.701 | 58.680 | 1.00 | 29.48 | C |
| ATOM | 3742 | CB | ARG | B | 180 | 5.988 | 10.201 | 59.992 | 1.00 | 30.49 | C |
| ATOM | 3743 | CG | ARG | B | 180 | 7.030 | 10.734 | 60.963 | 1.00 | 29.61 | C |
| ATOM | 3744 | CD | ARG | B | 180 | 6.405 | 11.604 | 62.011 | 1.00 | 27.55 | C |
| ATOM | 3745 | NE | ARG | B | 180 | 5.596 | 10.848 | 62.946 | 1.00 | 27.80 | N |

FIG. 2-57

| | | | | | | | | | |
|---|---|---|---|---|---|---|---|---|---|
| ATOM | 3746 | CZ | ARG | B | 180 | 4.621 | 11.375 | 63.681 | 1.00 28.01 | C |
| ATOM | 3747 | NH1 | ARG | B | 180 | 4.319 | 12.658 | 63.592 | 1.00 28.61 | N |
| ATOM | 3748 | NH2 | ARG | B | 180 | 3.947 | 10.620 | 64.525 | 1.00 30.23 | N |
| ATOM | 3749 | C | ARG | B | 180 | 5.565 | 8.920 | 57.879 | 1.00 29.33 | C |
| ATOM | 3750 | O | ARG | B | 180 | 4.861 | 8.087 | 58.442 | 1.00 29.49 | O |
| ATOM | 3751 | N | ASP | B | 181 | 5.442 | 9.185 | 56.583 | 1.00 29.79 | N |
| ATOM | 3752 | CA | ASP | B | 181 | 4.493 | 8.423 | 55.777 | 1.00 30.21 | C |
| ATOM | 3753 | CB | ASP | B | 181 | 3.071 | 8.954 | 55.929 | 1.00 28.26 | C |
| ATOM | 3754 | CG | ASP | B | 181 | 2.035 | 7.950 | 55.467 | 1.00 28.93 | C |
| ATOM | 3755 | OD1 | ASP | B | 181 | 2.314 | 6.735 | 55.541 | 1.00 28.26 | O |
| ATOM | 3756 | OD2 | ASP | B | 181 | 0.939 | 8.373 | 55.045 | 1.00 32.30 | O |
| ATOM | 3757 | C | ASP | B | 181 | 4.858 | 8.350 | 54.302 | 1.00 31.15 | C |
| ATOM | 3758 | O | ASP | B | 181 | 4.001 | 8.446 | 53.426 | 1.00 31.78 | O |
| ATOM | 3759 | N | ILE | B | 182 | 6.147 | 8.179 | 54.039 | 1.00 30.64 | N |
| ATOM | 3760 | CA | ILE | B | 182 | 6.625 | 8.072 | 52.680 | 1.00 31.03 | C |
| ATOM | 3761 | CB | ILE | B | 182 | 8.164 | 8.187 | 52.611 | 1.00 30.45 | C |
| ATOM | 3762 | CG2 | ILE | B | 182 | 8.658 | 7.883 | 51.201 | 1.00 28.18 | C |
| ATOM | 3763 | CG1 | ILE | B | 182 | 8.596 | 9.590 | 53.041 | 1.00 29.20 | C |
| ATOM | 3764 | CD1 | ILE | B | 182 | 8.025 | 10.695 | 52.180 | 1.00 28.72 | C |
| ATOM | 3765 | C | ILE | B | 182 | 6.197 | 6.714 | 52.147 | 1.00 32.08 | C |
| ATOM | 3766 | O | ILE | B | 182 | 6.524 | 5.673 | 52.725 | 1.00 31.82 | O |
| ATOM | 3767 | N | LYS | B | 183 | 5.429 | 6.747 | 51.062 | 1.00 30.93 | N |
| ATOM | 3768 | CA | LYS | B | 183 | 4.940 | 5.548 | 50.400 | 1.00 31.27 | C |
| ATOM | 3769 | CB | LYS | B | 183 | 3.754 | 4.951 | 51.163 | 1.00 29.78 | C |
| ATOM | 3770 | CG | LYS | B | 183 | 2.534 | 5.838 | 51.256 | 1.00 29.88 | C |
| ATOM | 3771 | CD | LYS | B | 183 | 1.445 | 5.144 | 52.029 | 1.00 29.06 | C |
| ATOM | 3772 | CE | LYS | B | 183 | 0.225 | 6.009 | 52.110 | 1.00 31.67 | C |
| ATOM | 3773 | NZ | LYS | B | 183 | -0.731 | 5.514 | 53.137 | 1.00 35.93 | N |
| ATOM | 3774 | C | LYS | B | 183 | 4.538 | 5.902 | 48.963 | 1.00 30.40 | C |
| ATOM | 3775 | O | LYS | B | 183 | 4.238 | 7.054 | 48.662 | 1.00 30.55 | O |
| ATOM | 3776 | N | PRO | B | 184 | 4.538 | 4.909 | 48.060 | 1.00 29.60 | N |
| ATOM | 3777 | CD | PRO | B | 184 | 4.812 | 3.490 | 48.369 | 1.00 28.82 | C |
| ATOM | 3778 | CA | PRO | B | 184 | 4.187 | 5.074 | 46.642 | 1.00 28.25 | C |
| ATOM | 3779 | CB | PRO | B | 184 | 4.044 | 3.631 | 46.156 | 1.00 28.44 | C |
| ATOM | 3780 | CG | PRO | B | 184 | 5.050 | 2.906 | 46.992 | 1.00 29.10 | C |
| ATOM | 3781 | C | PRO | B | 184 | 2.930 | 5.902 | 46.382 | 1.00 27.02 | C |
| ATOM | 3782 | O | PRO | B | 184 | 2.888 | 6.697 | 45.441 | 1.00 23.54 | O |
| ATOM | 3783 | N | GLN | B | 185 | 1.918 | 5.711 | 47.224 | 1.00 26.72 | N |
| ATOM | 3784 | CA | GLN | B | 185 | 0.656 | 6.428 | 47.090 | 1.00 27.61 | C |
| ATOM | 3785 | CB | GLN | B | 185 | -0.411 | 5.811 | 47.995 | 1.00 29.13 | C |
| ATOM | 3786 | CG | GLN | B | 185 | -0.701 | 4.353 | 47.689 | 1.00 31.35 | C |
| ATOM | 3787 | CD | GLN | B | 185 | 0.282 | 3.401 | 48.347 | 1.00 32.80 | C |
| ATOM | 3788 | OE1 | GLN | B | 185 | 1.403 | 3.774 | 48.692 | 1.00 31.24 | O |
| ATOM | 3789 | NE2 | GLN | B | 185 | -0.135 | 2.152 | 48.512 | 1.00 34.56 | N |
| ATOM | 3790 | C | GLN | B | 185 | 0.757 | 7.919 | 47.385 | 1.00 27.65 | C |
| ATOM | 3791 | O | GLN | B | 185 | -0.129 | 8.684 | 47.005 | 1.00 26.87 | O |
| ATOM | 3792 | N | ASN | B | 186 | 1.824 | 8.335 | 48.062 | 1.00 27.92 | N |
| ATOM | 3793 | CA | ASN | B | 186 | 1.996 | 9.746 | 48.390 | 1.00 28.48 | C |
| ATOM | 3794 | CB | ASN | B | 186 | 2.373 | 9.930 | 49.863 | 1.00 27.69 | C |
| ATOM | 3795 | CG | ASN | B | 186 | 1.228 | 9.616 | 50.798 | 1.00 27.82 | C |
| ATOM | 3796 | OD1 | ASN | B | 186 | 0.064 | 9.805 | 50.456 | 1.00 30.70 | O |
| ATOM | 3797 | ND2 | ASN | B | 186 | 1.553 | 9.144 | 51.993 | 1.00 30.30 | N |
| ATOM | 3798 | C | ASN | B | 186 | 3.027 | 10.427 | 47.514 | 1.00 29.09 | C |
| ATOM | 3799 | O | ASN | B | 186 | 3.583 | 11.455 | 47.885 | 1.00 28.79 | O |
| ATOM | 3800 | N | LEU | B | 187 | 3.280 | 9.850 | 46.347 | 1.00 29.56 | N |
| ATOM | 3801 | CA | LEU | B | 187 | 4.237 | 10.424 | 45.412 | 1.00 29.68 | C |
| ATOM | 3802 | CB | LEU | B | 187 | 5.368 | 9.424 | 45.138 | 1.00 27.87 | C |
| ATOM | 3803 | CG | LEU | B | 187 | 6.267 | 9.026 | 46.328 | 1.00 26.19 | C |
| ATOM | 3804 | CD1 | LEU | B | 187 | 7.176 | 7.865 | 45.944 | 1.00 24.99 | C |
| ATOM | 3805 | CD2 | LEU | B | 187 | 7.095 | 10.216 | 46.770 | 1.00 27.71 | C |
| ATOM | 3806 | C | LEU | B | 187 | 3.458 | 10.753 | 44.130 | 1.00 31.86 | C |
| ATOM | 3807 | O | LEU | B | 187 | 3.298 | 9.903 | 43.256 | 1.00 31.50 | O |
| ATOM | 3808 | N | LEU | B | 188 | 2.951 | 11.982 | 44.040 | 1.00 34.21 | N |
| ATOM | 3809 | CA | LEU | B | 188 | 2.182 | 12.414 | 42.875 | 1.00 37.20 | C |
| ATOM | 3810 | CB | LEU | B | 188 | 1.334 | 13.644 | 43.216 | 1.00 35.34 | C |
| ATOM | 3811 | CG | LEU | B | 188 | 0.551 | 13.646 | 44.528 | 1.00 37.23 | C |
| ATOM | 3812 | CD1 | LEU | B | 188 | -0.253 | 14.932 | 44.638 | 1.00 36.26 | C |

FIG. 2-58

| | | | | | | | | | | |
|---|---|---|---|---|---|---|---|---|---|---|
| ATOM | 3813 | CD2 | LEU | B | 188 | -0.364 | 12.434 | 44.599 | 1.00 36.48 | C |
| ATOM | 3814 | C | LEU | B | 188 | 3.118 | 12.775 | 41.728 | 1.00 39.25 | C |
| ATOM | 3815 | O | LEU | B | 188 | 4.215 | 13.283 | 41.958 | 1.00 40.41 | O |
| ATOM | 3816 | N | LEU | B | 189 | 2.697 | 12.520 | 40.492 | 1.00 41.45 | N |
| ATOM | 3817 | CA | LEU | B | 189 | 3.540 | 12.876 | 39.359 | 1.00 44.22 | C |
| ATOM | 3818 | CB | LEU | B | 189 | 4.540 | 11.751 | 39.050 | 1.00 44.60 | C |
| ATOM | 3819 | CG | LEU | B | 189 | 4.156 | 10.278 | 39.214 | 1.00 45.54 | C |
| ATOM | 3820 | CD1 | LEU | B | 189 | 3.133 | 9.901 | 38.162 | 1.00 46.77 | C |
| ATOM | 3821 | CD2 | LEU | B | 189 | 5.394 | 9.395 | 39.067 | 1.00 44.61 | C |
| ATOM | 3822 | C | LEU | B | 189 | 2.795 | 13.286 | 38.095 | 1.00 43.44 | C |
| ATOM | 3823 | O | LEU | B | 189 | 1.656 | 12.897 | 37.867 | 1.00 42.56 | O |
| ATOM | 3824 | N | ASP | B | 190 | 3.463 | 14.114 | 37.305 | 1.00 44.57 | N |
| ATOM | 3825 | CA | ASP | B | 190 | 2.948 | 14.621 | 36.047 | 1.00 46.24 | C |
| ATOM | 3826 | CB | ASP | B | 190 | 3.429 | 16.059 | 35.864 | 1.00 47.10 | C |
| ATOM | 3827 | CG | ASP | B | 190 | 2.801 | 16.747 | 34.670 | 1.00 46.91 | C |
| ATOM | 3828 | OD1 | ASP | B | 190 | 2.792 | 16.149 | 33.578 | 1.00 48.39 | O |
| ATOM | 3829 | OD2 | ASP | B | 190 | 2.335 | 17.892 | 34.818 | 1.00 47.31 | O |
| ATOM | 3830 | C | ASP | B | 190 | 3.551 | 13.713 | 34.975 | 1.00 47.43 | C |
| ATOM | 3831 | O | ASP | B | 190 | 4.740 | 13.817 | 34.654 | 1.00 47.41 | O |
| ATOM | 3832 | N | PRO | B | 191 | 2.736 | 12.810 | 34.409 | 1.00 48.54 | N |
| ATOM | 3833 | CD | PRO | B | 191 | 1.267 | 12.790 | 34.537 | 1.00 48.45 | C |
| ATOM | 3834 | CA | PRO | B | 191 | 3.173 | 11.867 | 33.374 | 1.00 48.88 | C |
| ATOM | 3835 | CB | PRO | B | 191 | 1.864 | 11.204 | 32.945 | 1.00 49.67 | C |
| ATOM | 3836 | CG | PRO | B | 191 | 0.847 | 12.284 | 33.184 | 1.00 49.16 | C |
| ATOM | 3837 | C | PRO | B | 191 | 3.950 | 12.435 | 32.183 | 1.00 48.53 | C |
| ATOM | 3838 | O | PRO | B | 191 | 4.760 | 11.722 | 31.592 | 1.00 49.39 | O |
| ATOM | 3839 | N | ASP | B | 192 | 3.710 | 13.696 | 31.822 | 1.00 47.29 | N |
| ATOM | 3840 | CA | ASP | B | 192 | 4.412 | 14.297 | 30.683 | 1.00 46.53 | C |
| ATOM | 3841 | CB | ASP | B | 192 | 3.517 | 15.306 | 29.947 | 1.00 48.12 | C |
| ATOM | 3842 | CG | ASP | B | 192 | 2.150 | 14.739 | 29.589 | 1.00 49.86 | C |
| ATOM | 3843 | OD1 | ASP | B | 192 | 2.063 | 13.584 | 29.121 | 1.00 50.76 | O |
| ATOM | 3844 | OD2 | ASP | B | 192 | 1.153 | 15.467 | 29.767 | 1.00 50.88 | O |
| ATOM | 3845 | C | ASP | B | 192 | 5.711 | 15.002 | 31.062 | 1.00 44.86 | C |
| ATOM | 3846 | O | ASP | B | 192 | 6.666 | 15.004 | 30.288 | 1.00 44.66 | O |
| ATOM | 3847 | N | THR | B | 193 | 5.750 | 15.607 | 32.244 | 1.00 42.90 | N |
| ATOM | 3848 | CA | THR | B | 193 | 6.951 | 16.315 | 32.683 | 1.00 41.22 | C |
| ATOM | 3849 | CB | THR | B | 193 | 6.594 | 17.618 | 33.397 | 1.00 41.63 | C |
| ATOM | 3850 | OG1 | THR | B | 193 | 5.570 | 17.356 | 34.361 | 1.00 42.11 | O |
| ATOM | 3851 | CG2 | THR | B | 193 | 6.103 | 18.659 | 32.406 | 1.00 41.00 | C |
| ATOM | 3852 | C | THR | B | 193 | 7.808 | 15.477 | 33.617 | 1.00 39.24 | C |
| ATOM | 3853 | O | THR | B | 193 | 8.991 | 15.760 | 33.808 | 1.00 37.94 | O |
| ATOM | 3854 | N | ALA | B | 194 | 7.196 | 14.444 | 34.185 | 1.00 38.24 | N |
| ATOM | 3855 | CA | ALA | B | 194 | 7.868 | 13.538 | 35.107 | 1.00 37.80 | C |
| ATOM | 3856 | CB | ALA | B | 194 | 9.075 | 12.905 | 34.431 | 1.00 36.54 | C |
| ATOM | 3857 | C | ALA | B | 194 | 8.286 | 14.186 | 36.434 | 1.00 37.46 | C |
| ATOM | 3858 | O | ALA | B | 194 | 9.117 | 13.637 | 37.150 | 1.00 36.81 | O |
| ATOM | 3859 | N | VAL | B | 195 | 7.721 | 15.344 | 36.770 | 1.00 36.68 | N |
| ATOM | 3860 | CA | VAL | B | 195 | 8.076 | 15.957 | 38.037 | 1.00 36.34 | C |
| ATOM | 3861 | CB | VAL | B | 195 | 7.763 | 17.479 | 38.091 | 1.00 37.21 | C |
| ATOM | 3862 | CG1 | VAL | B | 195 | 8.381 | 18.179 | 36.893 | 1.00 36.00 | C |
| ATOM | 3863 | CG2 | VAL | B | 195 | 6.268 | 17.715 | 38.135 | 1.00 40.50 | C |
| ATOM | 3864 | C | VAL | B | 195 | 7.271 | 15.229 | 39.103 | 1.00 35.96 | C |
| ATOM | 3865 | O | VAL | B | 195 | 6.102 | 14.896 | 38.900 | 1.00 35.58 | O |
| ATOM | 3866 | N | LEU | B | 196 | 7.916 | 14.956 | 40.229 | 1.00 34.80 | N |
| ATOM | 3867 | CA | LEU | B | 196 | 7.266 | 14.262 | 41.324 | 1.00 32.52 | C |
| ATOM | 3868 | CB | LEU | B | 196 | 8.158 | 13.107 | 41.793 | 1.00 32.64 | C |
| ATOM | 3869 | CG | LEU | B | 196 | 7.768 | 12.207 | 42.968 | 1.00 31.29 | C |
| ATOM | 3870 | CD1 | LEU | B | 196 | 8.274 | 10.804 | 42.691 | 1.00 30.16 | C |
| ATOM | 3871 | CD2 | LEU | B | 196 | 8.345 | 12.755 | 44.266 | 1.00 29.95 | C |
| ATOM | 3872 | C | LEU | B | 196 | 7.020 | 15.256 | 42.450 | 1.00 31.95 | C |
| ATOM | 3873 | O | LEU | B | 196 | 7.729 | 16.254 | 42.564 | 1.00 31.04 | O |
| ATOM | 3874 | N | LYS | B | 197 | 5.998 | 14.992 | 43.258 | 1.00 31.41 | N |
| ATOM | 3875 | CA | LYS | B | 197 | 5.653 | 15.851 | 44.389 | 1.00 31.14 | C |
| ATOM | 3876 | CB | LYS | B | 197 | 4.484 | 16.790 | 44.062 | 1.00 33.36 | C |
| ATOM | 3877 | CG | LYS | B | 197 | 4.801 | 17.856 | 43.044 | 1.00 35.77 | C |
| ATOM | 3878 | CD | LYS | B | 197 | 3.544 | 18.546 | 42.594 | 1.00 38.96 | C |
| ATOM | 3879 | CE | LYS | B | 197 | 3.827 | 19.414 | 41.384 | 1.00 40.59 | C |

FIG. 2-59

| | | | | | | | | | | |
|---|---|---|---|---|---|---|---|---|---|---|
| ATOM | 3880 | NZ | LYS | B | 197 | 5.012 | 20.281 | 41.659 | 1.00 42.20 | N |
| ATOM | 3881 | C | LYS | B | 197 | 5.263 | 15.003 | 45.583 | 1.00 30.43 | C |
| ATOM | 3882 | O | LYS | B | 197 | 4.428 | 14.106 | 45.475 | 1.00 29.19 | O |
| ATOM | 3883 | N | LEU | B | 198 | 5.890 | 15.290 | 46.720 | 1.00 30.73 | N |
| ATOM | 3884 | CA | LEU | B | 198 | 5.608 | 14.587 | 47.956 | 1.00 28.51 | C |
| ATOM | 3885 | CB | LEU | B | 198 | 6.695 | 14.879 | 48.989 | 1.00 29.45 | C |
| ATOM | 3886 | CG | LEU | B | 198 | 7.156 | 13.733 | 49.894 | 1.00 30.75 | C |
| ATOM | 3887 | CD1 | LEU | B | 198 | 7.822 | 14.304 | 51.140 | 1.00 29.31 | C |
| ATOM | 3888 | CD2 | LEU | B | 198 | 5.990 | 12.861 | 50.277 | 1.00 30.67 | C |
| ATOM | 3889 | C | LEU | B | 198 | 4.294 | 15.202 | 48.410 | 1.00 28.41 | C |
| ATOM | 3890 | O | LEU | B | 198 | 4.111 | 16.414 | 48.304 | 1.00 28.79 | O |
| ATOM | 3891 | N | CYS | B | 199 | 3.375 | 14.379 | 48.888 | 1.00 26.89 | N |
| ATOM | 3892 | CA | CYS | B | 199 | 2.101 | 14.895 | 49.340 | 1.00 27.75 | C |
| ATOM | 3893 | CB | CYS | B | 199 | 1.029 | 14.728 | 48.252 | 1.00 27.11 | C |
| ATOM | 3894 | SG | CYS | B | 199 | 0.185 | 13.100 | 48.234 | 1.00 29.08 | S |
| ATOM | 3895 | C | CYS | B | 199 | 1.650 | 14.183 | 50.614 | 1.00 27.32 | C |
| ATOM | 3896 | O | CYS | B | 199 | 2.217 | 13.164 | 51.013 | 1.00 25.49 | O |
| ATOM | 3897 | N | ASP | B | 200 | 0.617 | 14.736 | 51.240 | 1.00 28.66 | N |
| ATOM | 3898 | CA | ASP | B | 200 | 0.053 | 14.180 | 52.456 | 1.00 30.67 | C |
| ATOM | 3899 | CB | ASP | B | 200 | -0.319 | 12.716 | 52.250 | 1.00 29.76 | C |
| ATOM | 3900 | CG | ASP | B | 200 | -1.186 | 12.191 | 53.365 | 1.00 32.01 | C |
| ATOM | 3901 | OD1 | ASP | B | 200 | -1.390 | 12.913 | 54.359 | 1.00 31.56 | O |
| ATOM | 3902 | OD2 | ASP | B | 200 | -1.671 | 11.055 | 53.251 | 1.00 35.06 | O |
| ATOM | 3903 | C | ASP | B | 200 | 0.948 | 14.302 | 53.681 | 1.00 32.10 | C |
| ATOM | 3904 | O | ASP | B | 200 | 1.580 | 13.336 | 54.112 | 1.00 34.06 | O |
| ATOM | 3905 | N | PHE | B | 201 | 1.001 | 15.500 | 54.241 | 1.00 31.07 | N |
| ATOM | 3906 | CA | PHE | B | 201 | 1.800 | 15.725 | 55.424 | 1.00 30.86 | C |
| ATOM | 3907 | CB | PHE | B | 201 | 2.443 | 17.118 | 55.371 | 1.00 29.48 | C |
| ATOM | 3908 | CG | PHE | B | 201 | 3.571 | 17.229 | 54.386 | 1.00 29.07 | C |
| ATOM | 3909 | CD1 | PHE | B | 201 | 3.324 | 17.308 | 53.022 | 1.00 29.36 | C |
| ATOM | 3910 | CD2 | PHE | B | 201 | 4.889 | 17.230 | 54.825 | 1.00 27.33 | C |
| ATOM | 3911 | CE1 | PHE | B | 201 | 4.380 | 17.384 | 52.112 | 1.00 30.37 | C |
| ATOM | 3912 | CE2 | PHE | B | 201 | 5.949 | 17.309 | 53.922 | 1.00 27.65 | C |
| ATOM | 3913 | CZ | PHE | B | 201 | 5.696 | 17.385 | 52.567 | 1.00 27.74 | C |
| ATOM | 3914 | C | PHE | B | 201 | 0.949 | 15.562 | 56.683 | 1.00 31.26 | C |
| ATOM | 3915 | O | PHE | B | 201 | 1.213 | 16.203 | 57.690 | 1.00 33.07 | O |
| ATOM | 3916 | N | GLY | B | 202 | -0.060 | 14.693 | 56.620 | 1.00 31.71 | N |
| ATOM | 3917 | CA | GLY | B | 202 | -0.931 | 14.466 | 57.759 | 1.00 30.89 | C |
| ATOM | 3918 | C | GLY | B | 202 | -0.370 | 13.555 | 58.847 | 1.00 32.02 | C |
| ATOM | 3919 | O | GLY | B | 202 | -1.099 | 13.151 | 59.751 | 1.00 32.57 | O |
| ATOM | 3920 | N | SER | B | 203 | 0.916 | 13.221 | 58.758 | 1.00 31.89 | N |
| ATOM | 3921 | CA | SER | B | 203 | 1.592 | 12.373 | 59.740 | 1.00 30.99 | C |
| ATOM | 3922 | CB | SER | B | 203 | 1.842 | 10.962 | 59.191 | 1.00 30.73 | C |
| ATOM | 3923 | OG | SER | B | 203 | 0.650 | 10.265 | 58.942 | 1.00 31.46 | O |
| ATOM | 3924 | C | SER | B | 203 | 2.946 | 13.004 | 60.028 | 1.00 31.07 | C |
| ATOM | 3925 | O | SER | B | 203 | 3.721 | 12.494 | 60.828 | 1.00 32.54 | O |
| ATOM | 3926 | N | ALA | B | 204 | 3.231 | 14.100 | 59.339 | 1.00 30.75 | N |
| ATOM | 3927 | CA | ALA | B | 204 | 4.490 | 14.803 | 59.490 | 1.00 31.61 | C |
| ATOM | 3928 | CB | ALA | B | 204 | 4.641 | 15.821 | 58.379 | 1.00 31.56 | C |
| ATOM | 3929 | C | ALA | B | 204 | 4.568 | 15.494 | 60.842 | 1.00 33.59 | C |
| ATOM | 3930 | O | ALA | B | 204 | 3.553 | 15.912 | 61.401 | 1.00 33.43 | O |
| ATOM | 3931 | N | LYS | B | 205 | 5.779 | 15.613 | 61.362 | 1.00 35.62 | N |
| ATOM | 3932 | CA | LYS | B | 205 | 5.989 | 16.254 | 62.645 | 1.00 35.89 | C |
| ATOM | 3933 | CB | LYS | B | 205 | 5.730 | 15.262 | 63.778 | 1.00 33.37 | C |
| ATOM | 3934 | CG | LYS | B | 205 | 5.946 | 15.831 | 65.178 | 1.00 31.25 | C |
| ATOM | 3935 | CD | LYS | B | 205 | 5.902 | 14.722 | 66.220 | 1.00 30.83 | C |
| ATOM | 3936 | CE | LYS | B | 205 | 5.847 | 15.273 | 67.632 | 1.00 30.18 | C |
| ATOM | 3937 | NZ | LYS | B | 205 | 5.747 | 14.182 | 68.633 | 1.00 28.26 | N |
| ATOM | 3938 | C | LYS | B | 205 | 7.418 | 16.746 | 62.735 | 1.00 38.14 | C |
| ATOM | 3939 | O | LYS | B | 205 | 8.326 | 16.184 | 62.115 | 1.00 37.77 | O |
| ATOM | 3940 | N | GLN | B | 206 | 7.618 | 17.799 | 63.515 | 1.00 40.88 | N |
| ATOM | 3941 | CA | GLN | B | 206 | 8.956 | 18.329 | 63.706 | 1.00 43.44 | C |
| ATOM | 3942 | CB | GLN | B | 206 | 8.901 | 19.824 | 63.986 | 1.00 46.32 | C |
| ATOM | 3943 | CG | GLN | B | 206 | 10.248 | 20.505 | 63.956 | 1.00 50.97 | C |
| ATOM | 3944 | CD | GLN | B | 206 | 10.130 | 21.929 | 63.433 | 1.00 55.45 | C |
| ATOM | 3945 | OE1 | GLN | B | 206 | 11.046 | 22.754 | 63.601 | 1.00 57.25 | O |
| ATOM | 3946 | NE2 | GLN | B | 206 | 8.990 | 22.230 | 62.786 | 1.00 56.48 | N |

FIG. 2-60

| ATOM | 3947 | C | GLN | B | 206 | 9.486 | 17.575 | 64.915 | 1.00 | 43.47 | C |
| --- | --- | --- | --- | --- | --- | --- | --- | --- | --- | --- | --- |
| ATOM | 3948 | O | GLN | B | 206 | 8.892 | 17.614 | 65.984 | 1.00 | 43.08 | O |
| ATOM | 3949 | N | LEU | B | 207 | 10.584 | 16.862 | 64.737 | 1.00 | 44.37 | N |
| ATOM | 3950 | CA | LEU | B | 207 | 11.138 | 16.094 | 65.831 | 1.00 | 45.94 | C |
| ATOM | 3951 | CB | LEU | B | 207 | 11.855 | 14.856 | 65.275 | 1.00 | 44.42 | C |
| ATOM | 3952 | CG | LEU | B | 207 | 11.052 | 13.938 | 64.342 | 1.00 | 42.83 | C |
| ATOM | 3953 | CD1 | LEU | B | 207 | 11.980 | 12.921 | 63.722 | 1.00 | 42.12 | C |
| ATOM | 3954 | CD2 | LEU | B | 207 | 9.912 | 13.256 | 65.092 | 1.00 | 40.96 | C |
| ATOM | 3955 | C | LEU | B | 207 | 12.091 | 16.917 | 66.693 | 1.00 | 47.75 | C |
| ATOM | 3956 | O | LEU | B | 207 | 13.025 | 17.544 | 66.191 | 1.00 | 47.70 | O |
| ATOM | 3957 | N | VAL | B | 208 | 11.828 | 16.915 | 67.995 | 1.00 | 50.18 | N |
| ATOM | 3958 | CA | VAL | B | 208 | 12.645 | 17.612 | 68.979 | 1.00 | 51.62 | C |
| ATOM | 3959 | CB | VAL | B | 208 | 11.781 | 18.525 | 69.873 | 1.00 | 52.47 | C |
| ATOM | 3960 | CG1 | VAL | B | 208 | 12.463 | 18.739 | 71.227 | 1.00 | 52.68 | C |
| ATOM | 3961 | CG2 | VAL | B | 208 | 11.557 | 19.862 | 69.186 | 1.00 | 53.81 | C |
| ATOM | 3962 | C | VAL | B | 208 | 13.235 | 16.518 | 69.846 | 1.00 | 52.83 | C |
| ATOM | 3963 | O | VAL | B | 208 | 12.497 | 15.856 | 70.583 | 1.00 | 53.03 | O |
| ATOM | 3964 | N | ARG | B | 209 | 14.549 | 16.314 | 69.778 | 1.00 | 54.45 | N |
| ATOM | 3965 | CA | ARG | B | 209 | 15.150 | 15.262 | 70.597 | 1.00 | 56.56 | C |
| ATOM | 3966 | CB | ARG | B | 209 | 16.667 | 15.222 | 70.447 | 1.00 | 57.51 | C |
| ATOM | 3967 | CG | ARG | B | 209 | 17.211 | 13.843 | 70.805 | 1.00 | 61.77 | C |
| ATOM | 3968 | CD | ARG | B | 209 | 18.630 | 13.911 | 71.366 | 1.00 | 64.55 | C |
| ATOM | 3969 | NE | ARG | B | 209 | 19.447 | 14.882 | 70.639 | 1.00 | 67.32 | N |
| ATOM | 3970 | CZ | ARG | B | 209 | 20.633 | 15.321 | 71.048 | 1.00 | 68.56 | C |
| ATOM | 3971 | NH1 | ARG | B | 209 | 21.155 | 14.872 | 72.192 | 1.00 | 67.51 | N |
| ATOM | 3972 | NH2 | ARG | B | 209 | 21.283 | 16.220 | 70.310 | 1.00 | 67.94 | N |
| ATOM | 3973 | C | ARG | B | 209 | 14.786 | 15.473 | 72.065 | 1.00 | 56.64 | C |
| ATOM | 3974 | O | ARG | B | 209 | 14.847 | 16.590 | 72.579 | 1.00 | 56.87 | O |
| ATOM | 3975 | N | GLY | B | 210 | 14.410 | 14.394 | 72.735 | 1.00 | 56.29 | N |
| ATOM | 3976 | CA | GLY | B | 210 | 14.024 | 14.506 | 74.126 | 1.00 | 57.27 | C |
| ATOM | 3977 | C | GLY | B | 210 | 12.532 | 14.293 | 74.262 | 1.00 | 57.69 | C |
| ATOM | 3978 | O | GLY | B | 210 | 12.069 | 13.605 | 75.172 | 1.00 | 58.07 | O |
| ATOM | 3979 | N | GLU | B | 211 | 11.772 | 14.892 | 73.352 | 1.00 | 57.51 | N |
| ATOM | 3980 | CA | GLU | B | 211 | 10.321 | 14.742 | 73.351 | 1.00 | 56.80 | C |
| ATOM | 3981 | CB | GLU | B | 211 | 9.704 | 15.980 | 72.697 | 1.00 | 57.65 | C |
| ATOM | 3982 | CG | GLU | B | 211 | 10.096 | 17.255 | 73.466 | 1.00 | 59.89 | C |
| ATOM | 3983 | CD | GLU | B | 211 | 9.611 | 18.558 | 72.836 | 1.00 | 61.38 | C |
| ATOM | 3984 | OE1 | GLU | B | 211 | 9.663 | 19.595 | 73.545 | 1.00 | 61.54 | O |
| ATOM | 3985 | OE2 | GLU | B | 211 | 9.197 | 18.552 | 71.650 | 1.00 | 61.07 | O |
| ATOM | 3986 | C | GLU | B | 211 | 10.098 | 13.468 | 72.542 | 1.00 | 55.75 | C |
| ATOM | 3987 | O | GLU | B | 211 | 10.618 | 13.337 | 71.435 | 1.00 | 56.49 | O |
| ATOM | 3988 | N | PRO | B | 212 | 9.358 | 12.496 | 73.096 | 1.00 | 54.66 | N |
| ATOM | 3989 | CD | PRO | B | 212 | 8.617 | 12.573 | 74.368 | 1.00 | 54.69 | C |
| ATOM | 3990 | CA | PRO | B | 212 | 9.085 | 11.218 | 72.425 | 1.00 | 53.22 | C |
| ATOM | 3991 | CB | PRO | B | 212 | 8.648 | 10.327 | 73.572 | 1.00 | 53.29 | C |
| ATOM | 3992 | CG | PRO | B | 212 | 7.798 | 11.274 | 74.361 | 1.00 | 53.72 | C |
| ATOM | 3993 | C | PRO | B | 212 | 8.034 | 11.290 | 71.341 | 1.00 | 51.00 | C |
| ATOM | 3994 | O | PRO | B | 212 | 7.274 | 12.257 | 71.267 | 1.00 | 51.44 | O |
| ATOM | 3995 | N | ASN | B | 213 | 7.999 | 10.248 | 70.515 | 1.00 | 47.75 | N |
| ATOM | 3996 | CA | ASN | B | 213 | 7.055 | 10.150 | 69.404 | 1.00 | 45.76 | C |
| ATOM | 3997 | CB | ASN | B | 213 | 7.755 | 10.409 | 68.081 | 1.00 | 43.67 | C |
| ATOM | 3998 | CG | ASN | B | 213 | 8.505 | 11.695 | 68.076 | 1.00 | 43.25 | C |
| ATOM | 3999 | OD1 | ASN | B | 213 | 7.912 | 12.771 | 68.080 | 1.00 | 45.10 | O |
| ATOM | 4000 | ND2 | ASN | B | 213 | 9.825 | 11.604 | 68.087 | 1.00 | 42.12 | N |
| ATOM | 4001 | C | ASN | B | 213 | 6.471 | 8.765 | 69.345 | 1.00 | 44.92 | C |
| ATOM | 4002 | O | ASN | B | 213 | 7.056 | 7.814 | 69.854 | 1.00 | 46.19 | O |
| ATOM | 4003 | N | VAL | B | 214 | 5.319 | 8.654 | 68.702 | 1.00 | 42.84 | N |
| ATOM | 4004 | CA | VAL | B | 214 | 4.652 | 7.374 | 68.538 | 1.00 | 42.31 | C |
| ATOM | 4005 | CB | VAL | B | 214 | 3.251 | 7.574 | 67.929 | 1.00 | 43.26 | C |
| ATOM | 4006 | CG1 | VAL | B | 214 | 2.251 | 7.833 | 69.025 | 1.00 | 41.87 | C |
| ATOM | 4007 | CG2 | VAL | B | 214 | 3.269 | 8.763 | 66.972 | 1.00 | 44.83 | C |
| ATOM | 4008 | C | VAL | B | 214 | 5.497 | 6.491 | 67.616 | 1.00 | 41.81 | C |
| ATOM | 4009 | O | VAL | B | 214 | 6.090 | 6.972 | 66.647 | 1.00 | 40.12 | O |
| ATOM | 4010 | N | SER | B | 215 | 5.561 | 5.201 | 67.926 | 1.00 | 40.29 | N |
| ATOM | 4011 | CA | SER | B | 215 | 6.357 | 4.281 | 67.123 | 1.00 | 40.07 | C |
| ATOM | 4012 | CB | SER | B | 215 | 7.029 | 3.242 | 68.030 | 1.00 | 39.62 | C |
| ATOM | 4013 | OG | SER | B | 215 | 6.058 | 2.522 | 68.760 | 1.00 | 41.37 | O |

FIG. 2-61

| | | | | | | | | | | |
|---|---|---|---|---|---|---|---|---|---|---|
| ATOM | 4014 | C | SER | B | 215 | 5.527 | 3.585 | 66.044 | 1.00 38.34 | C |
| ATOM | 4015 | O | SER | B | 215 | 6.045 | 3.244 | 64.976 | 1.00 38.04 | O |
| ATOM | 4016 | N | PTY | B | 216 | 4.248 | 3.367 | 66.331 | 1.00 36.80 | N |
| ATOM | 4017 | CA | PTY | B | 216 | 3.364 | 2.737 | 65.363 | 1.00 34.29 | C |
| ATOM | 4018 | C | PTY | B | 216 | 2.896 | 3.769 | 64.343 | 1.00 34.49 | C |
| ATOM | 4019 | O | PTY | B | 216 | 1.773 | 4.263 | 64.434 | 1.00 34.25 | O |
| ATOM | 4020 | CB | PTY | B | 216 | 2.153 | 2.132 | 66.065 | 1.00 33.76 | C |
| ATOM | 4021 | CG | PTY | B | 216 | 1.432 | 1.188 | 65.105 | 1.00 34.44 | C |
| ATOM | 4022 | CD1 | PTY | B | 216 | 1.904 | -0.208 | 64.957 | 1.00 32.17 | C |
| ATOM | 4023 | CD2 | PTY | B | 216 | 0.278 | 1.635 | 64.268 | 1.00 33.51 | C |
| ATOM | 4024 | CE1 | PTY | B | 216 | 1.242 | -1.120 | 64.003 | 1.00 32.64 | C |
| ATOM | 4025 | CE2 | PTY | B | 216 | -0.365 | 0.711 | 63.321 | 1.00 32.60 | C |
| ATOM | 4026 | CZ | PTY | B | 216 | 0.106 | -0.665 | 63.182 | 1.00 33.14 | C |
| ATOM | 4027 | OH | PTY | B | 216 | -0.635 | -1.552 | 62.446 | 1.00 34.51 | O |
| ATOM | 4028 | P | PTY | B | 216 | -0.397 | -1.776 | 61.004 | 1.00 35.66 | P |
| ATOM | 4029 | OP1 | PTY | B | 216 | 0.678 | -2.725 | 60.967 | 1.00 34.26 | O |
| ATOM | 4030 | OP2 | PTY | B | 216 | -0.012 | -0.504 | 60.335 | 1.00 33.28 | O |
| ATOM | 4031 | OP3 | PTY | B | 216 | -1.700 | -2.313 | 60.485 | 1.00 35.06 | O |
| ATOM | 4032 | N | ILE | B | 217 | 3.772 | 4.121 | 63.408 | 1.00 33.84 | N |
| ATOM | 4033 | CA | ILE | B | 217 | 3.436 | 5.080 | 62.373 | 1.00 34.08 | C |
| ATOM | 4034 | CB | ILE | B | 217 | 3.941 | 6.507 | 62.679 | 1.00 36.01 | C |
| ATOM | 4035 | CG2 | ILE | B | 217 | 3.155 | 7.110 | 63.814 | 1.00 38.40 | C |
| ATOM | 4036 | CG1 | ILE | B | 217 | 5.445 | 6.488 | 62.945 | 1.00 36.25 | C |
| ATOM | 4037 | CD1 | ILE | B | 217 | 6.076 | 7.837 | 62.691 | 1.00 39.01 | C |
| ATOM | 4038 | C | ILE | B | 217 | 4.108 | 4.613 | 61.112 | 1.00 33.69 | C |
| ATOM | 4039 | O | ILE | B | 217 | 4.896 | 3.673 | 61.148 | 1.00 32.89 | O |
| ATOM | 4040 | N | CYS | B | 218 | 3.807 | 5.293 | 60.012 | 1.00 33.21 | N |
| ATOM | 4041 | CA | CYS | B | 218 | 4.346 | 4.961 | 58.698 | 1.00 33.77 | C |
| ATOM | 4042 | CB | CYS | B | 218 | 5.797 | 4.500 | 58.773 | 1.00 35.62 | C |
| ATOM | 4043 | SG | CYS | B | 218 | 7.005 | 5.774 | 58.807 | 1.00 42.50 | S |
| ATOM | 4044 | C | CYS | B | 218 | 3.534 | 3.790 | 58.194 | 1.00 31.98 | C |
| ATOM | 4045 | O | CYS | B | 218 | 2.967 | 3.028 | 58.975 | 1.00 30.07 | O |
| ATOM | 4046 | N | SER | B | 219 | 3.486 | 3.646 | 56.882 | 1.00 32.10 | N |
| ATOM | 4047 | CA | SER | B | 219 | 2.767 | 2.544 | 56.295 | 1.00 30.84 | C |
| ATOM | 4048 | CB | SER | B | 219 | 2.454 | 2.852 | 54.842 | 1.00 32.94 | C |
| ATOM | 4049 | OG | SER | B | 219 | 1.141 | 2.413 | 54.570 | 1.00 36.19 | O |
| ATOM | 4050 | C | SER | B | 219 | 3.606 | 1.276 | 56.449 | 1.00 30.10 | C |
| ATOM | 4051 | O | SER | B | 219 | 4.739 | 1.201 | 55.981 | 1.00 29.54 | O |
| ATOM | 4052 | N | ARG | B | 220 | 3.021 | 0.290 | 57.116 | 1.00 29.39 | N |
| ATOM | 4053 | CA | ARG | B | 220 | 3.668 | -0.974 | 57.428 | 1.00 30.78 | C |
| ATOM | 4054 | CB | ARG | B | 220 | 2.605 | -2.041 | 57.662 | 1.00 29.25 | C |
| ATOM | 4055 | CG | ARG | B | 220 | 3.165 | -3.333 | 58.205 | 1.00 30.56 | C |
| ATOM | 4056 | CD | ARG | B | 220 | 2.041 | -4.091 | 58.838 | 1.00 32.08 | C |
| ATOM | 4057 | NE | ARG | B | 220 | 1.402 | -4.971 | 57.879 | 1.00 36.51 | N |
| ATOM | 4058 | CZ | ARG | B | 220 | 0.121 | -5.310 | 57.925 | 1.00 38.74 | C |
| ATOM | 4059 | NH1 | ARG | B | 220 | -0.650 | -4.825 | 58.892 | 1.00 35.31 | N |
| ATOM | 4060 | NH2 | ARG | B | 220 | -0.381 | -6.132 | 57.007 | 1.00 38.50 | N |
| ATOM | 4061 | C | ARG | B | 220 | 4.759 | -1.547 | 56.520 | 1.00 31.16 | C |
| ATOM | 4062 | O | ARG | B | 220 | 5.810 | -1.953 | 57.013 | 1.00 32.43 | O |
| ATOM | 4063 | N | TYR | B | 221 | 4.507 | -1.625 | 55.220 | 1.00 30.94 | N |
| ATOM | 4064 | CA | TYR | B | 221 | 5.489 | -2.176 | 54.294 | 1.00 31.21 | C |
| ATOM | 4065 | CB | TYR | B | 221 | 4.894 | -2.287 | 52.892 | 1.00 31.30 | C |
| ATOM | 4066 | CG | TYR | B | 221 | 3.798 | -3.300 | 52.759 | 1.00 32.81 | C |
| ATOM | 4067 | CD1 | TYR | B | 221 | 3.537 | -4.222 | 53.775 | 1.00 33.25 | C |
| ATOM | 4068 | CE1 | TYR | B | 221 | 2.539 | -5.177 | 53.633 | 1.00 33.93 | C |
| ATOM | 4069 | CD2 | TYR | B | 221 | 3.031 | -3.359 | 51.600 | 1.00 32.77 | C |
| ATOM | 4070 | CE2 | TYR | B | 221 | 2.030 | -4.306 | 51.446 | 1.00 31.85 | C |
| ATOM | 4071 | CZ | TYR | B | 221 | 1.787 | -5.215 | 52.461 | 1.00 33.44 | C |
| ATOM | 4072 | OH | TYR | B | 221 | 0.802 | -6.168 | 52.310 | 1.00 32.26 | O |
| ATOM | 4073 | C | TYR | B | 221 | 6.711 | -1.285 | 54.242 | 1.00 30.17 | C |
| ATOM | 4074 | O | TYR | B | 221 | 7.825 | -1.758 | 54.039 | 1.00 29.88 | O |
| ATOM | 4075 | N | TYR | B | 222 | 6.476 | 0.010 | 54.421 | 1.00 30.99 | N |
| ATOM | 4076 | CA | TYR | B | 222 | 7.526 | 1.017 | 54.388 | 1.00 30.72 | C |
| ATOM | 4077 | CB | TYR | B | 222 | 7.092 | 2.181 | 53.501 | 1.00 29.73 | C |
| ATOM | 4078 | CG | TYR | B | 222 | 6.343 | 1.724 | 52.276 | 1.00 32.49 | C |
| ATOM | 4079 | CD1 | TYR | B | 222 | 4.953 | 1.635 | 52.283 | 1.00 30.02 | C |
| ATOM | 4080 | CE1 | TYR | B | 222 | 4.266 | 1.115 | 51.200 | 1.00 29.96 | C |

FIG. 2-62

```
ATOM   4081  CD2 TYR B 222       7.026   1.292  51.134  1.00 31.93           C
ATOM   4082  CE2 TYR B 222       6.339   0.768  50.042  1.00 32.44           C
ATOM   4083  CZ  TYR B 222       4.961   0.683  50.084  1.00 31.78           C
ATOM   4084  OH  TYR B 222       4.275   0.142  49.026  1.00 31.99           O
ATOM   4085  C   TYR B 222       7.820   1.531  55.795  1.00 31.12           C
ATOM   4086  O   TYR B 222       8.221   2.682  55.969  1.00 34.04           O
ATOM   4087  N   ARG B 223       7.608   0.683  56.796  1.00 27.89           N
ATOM   4088  CA  ARG B 223       7.861   1.059  58.180  1.00 27.26           C
ATOM   4089  CB  ARG B 223       6.802   0.437  59.091  1.00 27.10           C
ATOM   4090  CG  ARG B 223       7.104   0.583  60.561  1.00 26.22           C
ATOM   4091  CD  ARG B 223       5.835   0.790  61.352  1.00 26.23           C
ATOM   4092  NE  ARG B 223       4.946  -0.354  61.278  1.00 27.01           N
ATOM   4093  CZ  ARG B 223       3.642  -0.274  61.050  1.00 26.15           C
ATOM   4094  NH1 ARG B 223       3.064   0.902  60.864  1.00 25.42           N
ATOM   4095  NH2 ARG B 223       2.908  -1.377  61.024  1.00 27.16           N
ATOM   4096  C   ARG B 223       9.256   0.631  58.634  1.00 27.29           C
ATOM   4097  O   ARG B 223       9.621  -0.542  58.522  1.00 25.29           O
ATOM   4098  N   ALA B 224      10.027   1.591  59.141  1.00 27.18           N
ATOM   4099  CA  ALA B 224      11.387   1.335  59.618  1.00 28.16           C
ATOM   4100  CB  ALA B 224      12.056   2.643  60.022  1.00 27.85           C
ATOM   4101  C   ALA B 224      11.416   0.353  60.786  1.00 27.71           C
ATOM   4102  O   ALA B 224      10.514   0.332  61.621  1.00 27.48           O
ATOM   4103  N   PRO B 225      12.469  -0.471  60.860  1.00 28.97           N
ATOM   4104  CD  PRO B 225      13.621  -0.531  59.939  1.00 28.90           C
ATOM   4105  CA  PRO B 225      12.596  -1.458  61.935  1.00 30.04           C
ATOM   4106  CB  PRO B 225      13.837  -2.258  61.523  1.00 29.92           C
ATOM   4107  CG  PRO B 225      14.654  -1.266  60.759  1.00 28.82           C
ATOM   4108  C   PRO B 225      12.664  -0.909  63.376  1.00 31.07           C
ATOM   4109  O   PRO B 225      12.178  -1.562  64.303  1.00 30.75           O
ATOM   4110  N   GLU B 226      13.255   0.273  63.574  1.00 30.99           N
ATOM   4111  CA  GLU B 226      13.335   0.851  64.922  1.00 31.54           C
ATOM   4112  CB  GLU B 226      14.009   2.232  64.925  1.00 32.26           C
ATOM   4113  CG  GLU B 226      15.221   2.368  64.045  1.00 33.82           C
ATOM   4114  CD  GLU B 226      14.879   2.909  62.675  1.00 32.31           C
ATOM   4115  OE1 GLU B 226      14.882   4.145  62.488  1.00 29.55           O
ATOM   4116  OE2 GLU B 226      14.601   2.086  61.792  1.00 34.51           O
ATOM   4117  C   GLU B 226      11.920   1.034  65.439  1.00 31.49           C
ATOM   4118  O   GLU B 226      11.640   0.792  66.607  1.00 32.04           O
ATOM   4119  N   LEU B 227      11.038   1.473  64.545  1.00 31.55           N
ATOM   4120  CA  LEU B 227       9.641   1.709  64.871  1.00 30.89           C
ATOM   4121  CB  LEU B 227       8.920   2.286  63.648  1.00 31.74           C
ATOM   4122  CG  LEU B 227       9.420   3.638  63.108  1.00 30.96           C
ATOM   4123  CD1 LEU B 227       8.954   3.825  61.680  1.00 29.33           C
ATOM   4124  CD2 LEU B 227       8.943   4.774  63.997  1.00 28.75           C
ATOM   4125  C   LEU B 227       8.956   0.429  65.329  1.00 31.00           C
ATOM   4126  O   LEU B 227       8.266   0.427  66.348  1.00 30.14           O
ATOM   4127  N   ILE B 228       9.144  -0.656  64.578  1.00 31.59           N
ATOM   4128  CA  ILE B 228       8.551  -1.942  64.930  1.00 32.83           C
ATOM   4129  CB  ILE B 228       8.929  -3.051  63.924  1.00 33.65           C
ATOM   4130  CG2 ILE B 228       8.229  -4.356  64.306  1.00 31.43           C
ATOM   4131  CG1 ILE B 228       8.536  -2.639  62.503  1.00 33.49           C
ATOM   4132  CD1 ILE B 228       8.927  -3.665  61.441  1.00 30.63           C
ATOM   4133  C   ILE B 228       9.055  -2.372  66.311  1.00 34.16           C
ATOM   4134  O   ILE B 228       8.349  -3.057  67.049  1.00 32.59           O
ATOM   4135  N   PHE B 229      10.285  -1.972  66.631  1.00 35.47           N
ATOM   4136  CA  PHE B 229      10.910  -2.280  67.909  1.00 37.12           C
ATOM   4137  CB  PHE B 229      12.431  -2.091  67.831  1.00 36.90           C
ATOM   4138  CG  PHE B 229      13.185  -3.362  67.563  1.00 38.62           C
ATOM   4139  CD1 PHE B 229      13.196  -4.394  68.501  1.00 39.41           C
ATOM   4140  CD2 PHE B 229      13.862  -3.545  66.363  1.00 38.51           C
ATOM   4141  CE1 PHE B 229      13.869  -5.593  68.243  1.00 39.18           C
ATOM   4142  CE2 PHE B 229      14.537  -4.738  66.094  1.00 39.26           C
ATOM   4143  CZ  PHE B 229      14.540  -5.764  67.036  1.00 39.69           C
ATOM   4144  C   PHE B 229      10.346  -1.405  69.024  1.00 37.36           C
ATOM   4145  O   PHE B 229      10.722  -1.565  70.179  1.00 38.19           O
ATOM   4146  N   GLY B 230       9.452  -0.484  68.680  1.00 38.33           N
ATOM   4147  CA  GLY B 230       8.855   0.364  69.694  1.00 39.06           C
```

FIG. 2-63

| | | | | | | | | | |
|---|---|---|---|---|---|---|---|---|---|
| ATOM | 4148 | C | GLY | B | 230 | 9.626 | 1.626 | 70.033 | 1.00 39.63 | C |
| ATOM | 4149 | O | GLY | B | 230 | 9.239 | 2.379 | 70.940 | 1.00 40.52 | O |
| ATOM | 4150 | N | ALA | B | 231 | 10.721 | 1.851 | 69.316 | 1.00 39.66 | N |
| ATOM | 4151 | CA | ALA | B | 231 | 11.546 | 3.034 | 69.525 | 1.00 40.39 | C |
| ATOM | 4152 | CB | ALA | B | 231 | 12.555 | 3.165 | 68.401 | 1.00 40.02 | C |
| ATOM | 4153 | C | ALA | B | 231 | 10.647 | 4.261 | 69.567 | 1.00 40.99 | C |
| ATOM | 4154 | O | ALA | B | 231 | 9.604 | 4.292 | 68.911 | 1.00 42.65 | O |
| ATOM | 4155 | N | THR | B | 232 | 11.035 | 5.264 | 70.347 | 1.00 42.39 | N |
| ATOM | 4156 | CA | THR | B | 232 | 10.244 | 6.482 | 70.450 | 1.00 43.03 | C |
| ATOM | 4157 | CB | THR | B | 232 | 9.483 | 6.538 | 71.786 | 1.00 44.88 | C |
| ATOM | 4158 | OG1 | THR | B | 232 | 10.419 | 6.592 | 72.870 | 1.00 47.38 | O |
| ATOM | 4159 | CG2 | THR | B | 232 | 8.620 | 5.294 | 71.950 | 1.00 45.78 | C |
| ATOM | 4160 | C | THR | B | 232 | 11.143 | 7.699 | 70.327 | 1.00 42.76 | C |
| ATOM | 4161 | O | THR | B | 232 | 10.676 | 8.829 | 70.375 | 1.00 41.78 | O |
| ATOM | 4162 | N | ASP | B | 233 | 12.436 | 7.454 | 70.143 | 1.00 44.19 | N |
| ATOM | 4163 | CA | ASP | B | 233 | 13.418 | 8.521 | 69.999 | 1.00 46.25 | C |
| ATOM | 4164 | CB | ASP | B | 233 | 14.556 | 8.333 | 71.003 | 1.00 51.25 | C |
| ATOM | 4165 | CG | ASP | B | 233 | 15.487 | 7.195 | 70.611 | 1.00 55.99 | C |
| ATOM | 4166 | OD1 | ASP | B | 233 | 15.002 | 6.030 | 70.557 | 1.00 58.63 | O |
| ATOM | 4167 | OD2 | ASP | B | 233 | 16.693 | 7.467 | 70.352 | 1.00 57.09 | O |
| ATOM | 4168 | C | ASP | B | 233 | 14.013 | 8.489 | 68.594 | 1.00 44.84 | C |
| ATOM | 4169 | O | ASP | B | 233 | 15.169 | 8.876 | 68.389 | 1.00 46.39 | O |
| ATOM | 4170 | N | TYR | B | 234 | 13.243 | 8.015 | 67.625 | 1.00 41.70 | N |
| ATOM | 4171 | CA | TYR | B | 234 | 13.747 | 7.933 | 66.257 | 1.00 37.50 | C |
| ATOM | 4172 | CB | TYR | B | 234 | 12.806 | 7.089 | 65.408 | 1.00 33.16 | C |
| ATOM | 4173 | CG | TYR | B | 234 | 11.392 | 7.600 | 65.387 | 1.00 30.63 | C |
| ATOM | 4174 | CD1 | TYR | B | 234 | 11.010 | 8.626 | 64.528 | 1.00 29.14 | C |
| ATOM | 4175 | CE1 | TYR | B | 234 | 9.694 | 9.073 | 64.486 | 1.00 27.73 | C |
| ATOM | 4176 | CD2 | TYR | B | 234 | 10.421 | 7.041 | 66.210 | 1.00 30.51 | C |
| ATOM | 4177 | CE2 | TYR | B | 234 | 9.109 | 7.484 | 66.173 | 1.00 29.26 | C |
| ATOM | 4178 | CZ | TYR | B | 234 | 8.756 | 8.496 | 65.309 | 1.00 28.16 | C |
| ATOM | 4179 | OH | TYR | B | 234 | 7.456 | 8.923 | 65.265 | 1.00 31.73 | O |
| ATOM | 4180 | C | TYR | B | 234 | 13.956 | 9.307 | 65.627 | 1.00 37.03 | C |
| ATOM | 4181 | O | TYR | B | 234 | 13.481 | 10.325 | 66.136 | 1.00 37.24 | O |
| ATOM | 4182 | N | THR | B | 235 | 14.686 | 9.325 | 64.519 | 1.00 35.56 | N |
| ATOM | 4183 | CA | THR | B | 235 | 14.997 | 10.553 | 63.804 | 1.00 34.47 | C |
| ATOM | 4184 | CB | THR | B | 235 | 16.484 | 10.688 | 63.598 | 1.00 34.02 | C |
| ATOM | 4185 | OG1 | THR | B | 235 | 16.895 | 9.771 | 62.580 | 1.00 32.65 | O |
| ATOM | 4186 | CG2 | THR | B | 235 | 17.227 | 10.344 | 64.881 | 1.00 33.68 | C |
| ATOM | 4187 | C | THR | B | 235 | 14.346 | 10.520 | 62.430 | 1.00 35.50 | C |
| ATOM | 4188 | O | THR | B | 235 | 13.641 | 9.566 | 62.088 | 1.00 36.88 | O |
| ATOM | 4189 | N | SER | B | 236 | 14.588 | 11.556 | 61.638 | 1.00 34.58 | N |
| ATOM | 4190 | CA | SER | B | 236 | 14.011 | 11.624 | 60.307 | 1.00 33.61 | C |
| ATOM | 4191 | CB | SER | B | 236 | 14.221 | 13.013 | 59.698 | 1.00 32.56 | C |
| ATOM | 4192 | OG | SER | B | 236 | 15.584 | 13.233 | 59.387 | 1.00 35.02 | O |
| ATOM | 4193 | C | SER | B | 236 | 14.601 | 10.561 | 59.380 | 1.00 32.94 | C |
| ATOM | 4194 | O | SER | B | 236 | 14.220 | 10.469 | 58.213 | 1.00 33.83 | O |
| ATOM | 4195 | N | SER | B | 237 | 15.518 | 9.748 | 59.889 | 1.00 31.60 | N |
| ATOM | 4196 | CA | SER | B | 237 | 16.105 | 8.726 | 59.048 | 1.00 30.21 | C |
| ATOM | 4197 | CB | SER | B | 237 | 17.356 | 8.122 | 59.709 | 1.00 28.10 | C |
| ATOM | 4198 | OG | SER | B | 237 | 17.042 | 7.246 | 60.777 | 1.00 29.05 | O |
| ATOM | 4199 | C | SER | B | 237 | 15.072 | 7.644 | 58.734 | 1.00 28.86 | C |
| ATOM | 4200 | O | SER | B | 237 | 15.276 | 6.835 | 57.835 | 1.00 29.69 | O |
| ATOM | 4201 | N | ILE | B | 238 | 13.964 | 7.624 | 59.466 | 1.00 28.19 | N |
| ATOM | 4202 | CA | ILE | B | 238 | 12.928 | 6.634 | 59.179 | 1.00 29.12 | C |
| ATOM | 4203 | CB | ILE | B | 238 | 11.713 | 6.708 | 60.152 | 1.00 30.75 | C |
| ATOM | 4204 | CG2 | ILE | B | 238 | 12.100 | 6.167 | 61.520 | 1.00 28.07 | C |
| ATOM | 4205 | CG1 | ILE | B | 238 | 11.167 | 8.141 | 60.184 | 1.00 29.50 | C |
| ATOM | 4206 | CD1 | ILE | B | 238 | 9.836 | 8.288 | 60.864 | 1.00 30.19 | C |
| ATOM | 4207 | C | ILE | B | 238 | 12.388 | 6.887 | 57.768 | 1.00 28.36 | C |
| ATOM | 4208 | O | ILE | B | 238 | 11.972 | 5.960 | 57.086 | 1.00 26.43 | O |
| ATOM | 4209 | N | ASP | B | 239 | 12.379 | 8.146 | 57.343 | 1.00 26.12 | N |
| ATOM | 4210 | CA | ASP | B | 239 | 11.893 | 8.472 | 56.011 | 1.00 27.52 | C |
| ATOM | 4211 | CB | ASP | B | 239 | 11.824 | 9.980 | 55.800 | 1.00 27.26 | C |
| ATOM | 4212 | CG | ASP | B | 239 | 10.602 | 10.595 | 56.415 | 1.00 28.46 | C |
| ATOM | 4213 | OD1 | ASP | B | 239 | 9.680 | 9.837 | 56.784 | 1.00 28.42 | O |
| ATOM | 4214 | OD2 | ASP | B | 239 | 10.558 | 11.838 | 56.517 | 1.00 29.33 | O |

FIG. 2-64

```
ATOM   4215  C    ASP B 239      12.790    7.896   54.942  1.00 28.52           C
ATOM   4216  O    ASP B 239      12.329    7.492   53.880  1.00 30.37           O
ATOM   4217  N    VAL B 240      14.085    7.882   55.231  1.00 28.91           N
ATOM   4218  CA   VAL B 240      15.088    7.381   54.310  1.00 27.22           C
ATOM   4219  CB   VAL B 240      16.485    7.745   54.810  1.00 26.01           C
ATOM   4220  CG1  VAL B 240      17.540    7.006   54.017  1.00 24.48           C
ATOM   4221  CG2  VAL B 240      16.680    9.248   54.701  1.00 21.50           C
ATOM   4222  C    VAL B 240      14.947    5.879   54.155  1.00 29.86           C
ATOM   4223  O    VAL B 240      15.126    5.336   53.062  1.00 30.67           O
ATOM   4224  N    TRP B 241      14.622    5.202   55.251  1.00 30.12           N
ATOM   4225  CA   TRP B 241      14.416    3.765   55.195  1.00 29.94           C
ATOM   4226  CB   TRP B 241      14.130    3.197   56.592  1.00 27.23           C
ATOM   4227  CG   TRP B 241      13.508    1.835   56.570  1.00 26.46           C
ATOM   4228  CD2  TRP B 241      14.183    0.575   56.673  1.00 26.86           C
ATOM   4229  CE2  TRP B 241      13.205   -0.436   56.531  1.00 27.04           C
ATOM   4230  CE3  TRP B 241      15.517    0.200   56.867  1.00 26.80           C
ATOM   4231  CD1  TRP B 241      12.188    1.542   56.381  1.00 26.67           C
ATOM   4232  NE1  TRP B 241      11.997    0.183   56.357  1.00 25.76           N
ATOM   4233  CZ2  TRP B 241      13.522   -1.800   56.577  1.00 28.09           C
ATOM   4234  CZ3  TRP B 241      15.832   -1.158   56.913  1.00 27.80           C
ATOM   4235  CH2  TRP B 241      14.836   -2.139   56.767  1.00 29.73           C
ATOM   4236  C    TRP B 241      13.216    3.579   54.276  1.00 30.72           C
ATOM   4237  O    TRP B 241      13.259    2.778   53.344  1.00 32.37           O
ATOM   4238  N    SER B 242      12.153    4.333   54.546  1.00 31.26           N
ATOM   4239  CA   SER B 242      10.927    4.282   53.743  1.00 31.82           C
ATOM   4240  CB   SER B 242       9.926    5.349   54.218  1.00 29.82           C
ATOM   4241  OG   SER B 242       9.252    4.951   55.393  1.00 29.37           O
ATOM   4242  C    SER B 242      11.227    4.514   52.269  1.00 30.85           C
ATOM   4243  O    SER B 242      10.618    3.900   51.407  1.00 29.65           O
ATOM   4244  N    ALA B 243      12.170    5.410   52.001  1.00 30.38           N
ATOM   4245  CA   ALA B 243      12.551    5.731   50.642  1.00 32.17           C
ATOM   4246  CB   ALA B 243      13.520    6.909   50.630  1.00 31.00           C
ATOM   4247  C    ALA B 243      13.181    4.513   49.967  1.00 34.25           C
ATOM   4248  O    ALA B 243      12.740    4.097   48.901  1.00 35.96           O
ATOM   4249  N    GLY B 244      14.210    3.942   50.587  1.00 34.43           N
ATOM   4250  CA   GLY B 244      14.851    2.780   50.008  1.00 34.19           C
ATOM   4251  C    GLY B 244      13.849    1.652   49.815  1.00 34.12           C
ATOM   4252  O    GLY B 244      14.058    0.749   48.999  1.00 35.39           O
ATOM   4253  N    CYS B 245      12.759    1.706   50.579  1.00 32.43           N
ATOM   4254  CA   CYS B 245      11.683    0.709   50.509  1.00 30.90           C
ATOM   4255  CB   CYS B 245      10.721    0.868   51.684  1.00 28.81           C
ATOM   4256  SG   CYS B 245      10.899   -0.391   52.974  1.00 29.95           S
ATOM   4257  C    CYS B 245      10.890    0.877   49.228  1.00 30.62           C
ATOM   4258  O    CYS B 245      10.463   -0.094   48.606  1.00 29.41           O
ATOM   4259  N    VAL B 246      10.679    2.129   48.854  1.00 28.70           N
ATOM   4260  CA   VAL B 246       9.959    2.440   47.643  1.00 27.85           C
ATOM   4261  CB   VAL B 246       9.516    3.919   47.641  1.00 27.42           C
ATOM   4262  CG1  VAL B 246       9.583    4.491   46.239  1.00 26.85           C
ATOM   4263  CG2  VAL B 246       8.102    4.032   48.203  1.00 26.60           C
ATOM   4264  C    VAL B 246      10.853    2.146   46.436  1.00 28.50           C
ATOM   4265  O    VAL B 246      10.365    1.711   45.402  1.00 28.72           O
ATOM   4266  N    LEU B 247      12.159    2.369   46.580  1.00 28.10           N
ATOM   4267  CA   LEU B 247      13.112    2.113   45.500  1.00 27.73           C
ATOM   4268  CB   LEU B 247      14.503    2.652   45.854  1.00 28.38           C
ATOM   4269  CG   LEU B 247      15.699    2.142   45.022  1.00 29.15           C
ATOM   4270  CD1  LEU B 247      15.650    2.692   43.602  1.00 29.85           C
ATOM   4271  CD2  LEU B 247      17.004    2.541   45.691  1.00 29.28           C
ATOM   4272  C    LEU B 247      13.220    0.627   45.220  1.00 27.53           C
ATOM   4273  O    LEU B 247      13.171    0.203   44.073  1.00 28.99           O
ATOM   4274  N    ALA B 248      13.380   -0.163   46.275  1.00 29.23           N
ATOM   4275  CA   ALA B 248      13.495   -1.602   46.127  1.00 29.02           C
ATOM   4276  CB   ALA B 248      13.647   -2.260   47.482  1.00 25.95           C
ATOM   4277  C    ALA B 248      12.236   -2.091   45.440  1.00 29.91           C
ATOM   4278  O    ALA B 248      12.287   -2.946   44.559  1.00 30.95           O
ATOM   4279  N    GLU B 249      11.101   -1.529   45.842  1.00 29.57           N
ATOM   4280  CA   GLU B 249       9.829   -1.918   45.262  1.00 29.48           C
ATOM   4281  CB   GLU B 249       8.675   -1.137   45.891  1.00 28.81           C
```

FIG. 2-65

```
ATOM   4282  CG   GLU B 249       7.326  -1.787  45.630  1.00 30.29           C
ATOM   4283  CD   GLU B 249       6.199  -1.226  46.474  1.00 30.72           C
ATOM   4284  OE1  GLU B 249       6.350  -1.162  47.714  1.00 31.32           O
ATOM   4285  OE2  GLU B 249       5.155  -0.855  45.897  1.00 29.71           O
ATOM   4286  C    GLU B 249       9.830  -1.701  43.757  1.00 29.75           C
ATOM   4287  O    GLU B 249       9.460  -2.590  43.002  1.00 32.58           O
ATOM   4288  N    LEU B 250      10.246  -0.521  43.323  1.00 28.78           N
ATOM   4289  CA   LEU B 250      10.279  -0.213  41.911  1.00 28.45           C
ATOM   4290  CB   LEU B 250      10.681   1.244  41.713  1.00 26.40           C
ATOM   4291  CG   LEU B 250       9.701   2.235  42.341  1.00 25.28           C
ATOM   4292  CD1  LEU B 250      10.372   3.587  42.432  1.00 24.43           C
ATOM   4293  CD2  LEU B 250       8.407   2.306  41.545  1.00 21.07           C
ATOM   4294  C    LEU B 250      11.201  -1.134  41.121  1.00 30.26           C
ATOM   4295  O    LEU B 250      10.901  -1.471  39.987  1.00 31.99           O
ATOM   4296  N    LEU B 251      12.317  -1.545  41.712  1.00 31.71           N
ATOM   4297  CA   LEU B 251      13.246  -2.430  41.033  1.00 31.06           C
ATOM   4298  CB   LEU B 251      14.587  -2.436  41.746  1.00 30.98           C
ATOM   4299  CG   LEU B 251      15.357  -1.128  41.769  1.00 31.94           C
ATOM   4300  CD1  LEU B 251      16.659  -1.348  42.534  1.00 31.93           C
ATOM   4301  CD2  LEU B 251      15.634  -0.656  40.347  1.00 29.86           C
ATOM   4302  C    LEU B 251      12.738  -3.855  40.984  1.00 32.10           C
ATOM   4303  O    LEU B 251      13.126  -4.627  40.114  1.00 32.89           O
ATOM   4304  N    LEU B 252      11.869  -4.189  41.927  1.00 34.05           N
ATOM   4305  CA   LEU B 252      11.323  -5.528  42.080  1.00 34.81           C
ATOM   4306  CB   LEU B 252      11.289  -5.867  43.556  1.00 36.83           C
ATOM   4307  CG   LEU B 252      12.094  -7.063  44.031  1.00 39.61           C
ATOM   4308  CD1  LEU B 252      13.564  -6.874  43.717  1.00 40.43           C
ATOM   4309  CD2  LEU B 252      11.881  -7.200  45.522  1.00 41.89           C
ATOM   4310  C    LEU B 252       9.943  -5.798  41.514  1.00 35.60           C
ATOM   4311  O    LEU B 252       9.612  -6.947  41.233  1.00 35.71           O
ATOM   4312  N    GLY B 253       9.126  -4.764  41.373  1.00 35.88           N
ATOM   4313  CA   GLY B 253       7.787  -4.972  40.852  1.00 37.04           C
ATOM   4314  C    GLY B 253       6.785  -5.351  41.929  1.00 38.34           C
ATOM   4315  O    GLY B 253       5.651  -5.719  41.624  1.00 38.40           O
ATOM   4316  N    GLN B 254       7.210  -5.263  43.189  1.00 38.64           N
ATOM   4317  CA   GLN B 254       6.367  -5.575  44.342  1.00 38.56           C
ATOM   4318  CB   GLN B 254       6.124  -7.082  44.423  1.00 39.55           C
ATOM   4319  CG   GLN B 254       7.396  -7.889  44.296  1.00 43.80           C
ATOM   4320  CD   GLN B 254       7.193  -9.348  44.607  1.00 44.44           C
ATOM   4321  OE1  GLN B 254       6.648  -9.700  45.647  1.00 47.29           O
ATOM   4322  NE2  GLN B 254       7.637 -10.211  43.707  1.00 46.95           N
ATOM   4323  C    GLN B 254       7.103  -5.101  45.595  1.00 38.17           C
ATOM   4324  O    GLN B 254       8.318  -4.894  45.562  1.00 37.78           O
ATOM   4325  N    PRO B 255       6.379  -4.916  46.714  1.00 37.93           N
ATOM   4326  CD   PRO B 255       4.921  -5.036  46.858  1.00 38.27           C
ATOM   4327  CA   PRO B 255       6.978  -4.464  47.975  1.00 36.84           C
ATOM   4328  CB   PRO B 255       5.791  -4.439  48.932  1.00 36.35           C
ATOM   4329  CG   PRO B 255       4.646  -4.129  48.032  1.00 37.60           C
ATOM   4330  C    PRO B 255       8.068  -5.416  48.446  1.00 36.52           C
ATOM   4331  O    PRO B 255       7.877  -6.629  48.450  1.00 37.94           O
ATOM   4332  N    ILE B 256       9.209  -4.870  48.848  1.00 35.04           N
ATOM   4333  CA   ILE B 256      10.302  -5.712  49.303  1.00 33.06           C
ATOM   4334  CB   ILE B 256      11.604  -4.878  49.467  1.00 33.97           C
ATOM   4335  CG2  ILE B 256      11.372  -3.712  50.418  1.00 35.68           C
ATOM   4336  CG1  ILE B 256      12.753  -5.770  49.940  1.00 32.44           C
ATOM   4337  CD1  ILE B 256      13.254  -6.719  48.906  1.00 32.33           C
ATOM   4338  C    ILE B 256       9.940  -6.443  50.603  1.00 32.44           C
ATOM   4339  O    ILE B 256      10.270  -7.617  50.768  1.00 33.52           O
ATOM   4340  N    PHE B 257       9.242  -5.774  51.513  1.00 30.39           N
ATOM   4341  CA   PHE B 257       8.868  -6.416  52.769  1.00 30.50           C
ATOM   4342  CB   PHE B 257       9.537  -5.702  53.941  1.00 28.63           C
ATOM   4343  CG   PHE B 257      11.005  -5.449  53.751  1.00 28.50           C
ATOM   4344  CD1  PHE B 257      11.896  -6.498  53.571  1.00 28.36           C
ATOM   4345  CD2  PHE B 257      11.503  -4.154  53.797  1.00 28.24           C
ATOM   4346  CE1  PHE B 257      13.268  -6.253  53.446  1.00 29.17           C
ATOM   4347  CE2  PHE B 257      12.870  -3.904  53.673  1.00 28.84           C
ATOM   4348  CZ   PHE B 257      13.754  -4.953  53.498  1.00 25.61           C
```

FIG. 2-66

```
ATOM   4349  C    PHE B 257       7.347  -6.414  52.973  1.00 30.75           C
ATOM   4350  O    PHE B 257       6.799  -5.504  53.590  1.00 30.52           O
ATOM   4351  N    PRO B 258       6.648  -7.443  52.459  1.00 31.74           N
ATOM   4352  CD   PRO B 258       7.165  -8.452  51.515  1.00 31.47           C
ATOM   4353  CA   PRO B 258       5.188  -7.554  52.581  1.00 32.79           C
ATOM   4354  CB   PRO B 258       4.816  -8.337  51.329  1.00 31.09           C
ATOM   4355  CG   PRO B 258       5.937  -9.308  51.235  1.00 31.24           C
ATOM   4356  C    PRO B 258       4.663  -8.219  53.860  1.00 33.85           C
ATOM   4357  O    PRO B 258       4.059  -9.293  53.802  1.00 33.08           O
ATOM   4358  N    GLY B 259       4.877  -7.565  55.002  1.00 35.35           N
ATOM   4359  CA   GLY B 259       4.433  -8.106  56.278  1.00 36.28           C
ATOM   4360  C    GLY B 259       2.928  -8.129  56.441  1.00 38.29           C
ATOM   4361  O    GLY B 259       2.237  -7.203  56.018  1.00 38.83           O
ATOM   4362  N    ASP B 260       2.400  -9.184  57.058  1.00 38.84           N
ATOM   4363  CA   ASP B 260       0.954  -9.263  57.232  1.00 38.78           C
ATOM   4364  CB   ASP B 260       0.446 -10.705  57.065  1.00 39.54           C
ATOM   4365  CG   ASP B 260       0.855 -11.620  58.205  1.00 42.26           C
ATOM   4366  OD1  ASP B 260       1.015 -11.127  59.350  1.00 43.47           O
ATOM   4367  OD2  ASP B 260       0.993 -12.849  57.955  1.00 41.95           O
ATOM   4368  C    ASP B 260       0.495  -8.684  58.564  1.00 38.04           C
ATOM   4369  O    ASP B 260      -0.647  -8.886  58.984  1.00 38.02           O
ATOM   4370  N    SER B 261       1.397  -7.965  59.225  1.00 36.68           N
ATOM   4371  CA   SER B 261       1.096  -7.326  60.507  1.00 35.64           C
ATOM   4372  CB   SER B 261       0.731  -8.370  61.572  1.00 35.11           C
ATOM   4373  OG   SER B 261       1.872  -9.012  62.100  1.00 34.85           O
ATOM   4374  C    SER B 261       2.290  -6.502  60.978  1.00 34.79           C
ATOM   4375  O    SER B 261       3.391  -6.630  60.442  1.00 35.37           O
ATOM   4376  N    GLY B 262       2.064  -5.659  61.979  1.00 32.94           N
ATOM   4377  CA   GLY B 262       3.121  -4.813  62.492  1.00 31.29           C
ATOM   4378  C    GLY B 262       4.349  -5.574  62.932  1.00 31.51           C
ATOM   4379  O    GLY B 262       5.470  -5.094  62.763  1.00 31.68           O
ATOM   4380  N    VAL B 263       4.145  -6.764  63.489  1.00 33.18           N
ATOM   4381  CA   VAL B 263       5.251  -7.589  63.974  1.00 34.60           C
ATOM   4382  CB   VAL B 263       4.819  -8.436  65.191  1.00 34.75           C
ATOM   4383  CG1  VAL B 263       5.973  -9.309  65.661  1.00 31.59           C
ATOM   4384  CG2  VAL B 263       4.357  -7.519  66.306  1.00 34.33           C
ATOM   4385  C    VAL B 263       5.834  -8.515  62.911  1.00 35.59           C
ATOM   4386  O    VAL B 263       7.028  -8.820  62.934  1.00 35.75           O
ATOM   4387  N    ASP B 264       4.996  -8.979  61.990  1.00 36.31           N
ATOM   4388  CA   ASP B 264       5.484  -9.852  60.927  1.00 37.35           C
ATOM   4389  CB   ASP B 264       4.308 -10.479  60.162  1.00 40.71           C
ATOM   4390  CG   ASP B 264       4.746 -11.262  58.923  1.00 43.93           C
ATOM   4391  OD1  ASP B 264       4.003 -11.214  57.912  1.00 43.70           O
ATOM   4392  OD2  ASP B 264       5.812 -11.926  58.957  1.00 44.93           O
ATOM   4393  C    ASP B 264       6.322  -8.976  59.995  1.00 37.38           C
ATOM   4394  O    ASP B 264       7.211  -9.467  59.304  1.00 37.71           O
ATOM   4395  N    GLN B 265       6.040  -7.672  59.985  1.00 36.30           N
ATOM   4396  CA   GLN B 265       6.788  -6.763  59.129  1.00 36.87           C
ATOM   4397  CB   GLN B 265       6.325  -5.321  59.317  1.00 35.74           C
ATOM   4398  CG   GLN B 265       6.986  -4.323  58.362  1.00 34.59           C
ATOM   4399  CD   GLN B 265       6.818  -4.701  56.898  1.00 33.30           C
ATOM   4400  OE1  GLN B 265       5.810  -5.284  56.512  1.00 33.42           O
ATOM   4401  NE2  GLN B 265       7.799  -4.351  56.078  1.00 31.34           N
ATOM   4402  C    GLN B 265       8.280  -6.860  59.421  1.00 37.56           C
ATOM   4403  O    GLN B 265       9.098  -6.751  58.515  1.00 39.37           O
ATOM   4404  N    LEU B 266       8.633  -7.064  60.684  1.00 37.85           N
ATOM   4405  CA   LEU B 266      10.030  -7.185  61.049  1.00 37.82           C
ATOM   4406  CB   LEU B 266      10.189  -7.096  62.564  1.00 36.90           C
ATOM   4407  CG   LEU B 266      11.574  -7.275  63.206  1.00 36.01           C
ATOM   4408  CD1  LEU B 266      12.600  -6.333  62.582  1.00 34.17           C
ATOM   4409  CD2  LEU B 266      11.448  -7.005  64.706  1.00 33.21           C
ATOM   4410  C    LEU B 266      10.544  -8.526  60.547  1.00 38.97           C
ATOM   4411  O    LEU B 266      11.684  -8.638  60.088  1.00 38.75           O
ATOM   4412  N    VAL B 267       9.696  -9.544  60.621  1.00 38.99           N
ATOM   4413  CA   VAL B 267      10.092 -10.867  60.168  1.00 39.24           C
ATOM   4414  CB   VAL B 267       8.969 -11.895  60.389  1.00 38.98           C
ATOM   4415  CG1  VAL B 267       9.363 -13.233  59.783  1.00 37.96           C
```

FIG. 2-67

| ATOM | 4416 | CG2 | VAL | B | 267 | 8.700 | -12.041 | 61.870 | 1.00 | 37.90 | C |
|---|---|---|---|---|---|---|---|---|---|---|---|
| ATOM | 4417 | C | VAL | B | 267 | 10.455 | -10.834 | 58.692 | 1.00 | 40.20 | C |
| ATOM | 4418 | O | VAL | B | 267 | 11.443 | -11.439 | 58.280 | 1.00 | 42.35 | O |
| ATOM | 4419 | N | GLU | B | 268 | 9.658 | -10.124 | 57.899 | 1.00 | 39.06 | N |
| ATOM | 4420 | CA | GLU | B | 268 | 9.905 | -10.015 | 56.465 | 1.00 | 37.12 | C |
| ATOM | 4421 | CB | GLU | B | 268 | 8.748 | -9.281 | 55.782 | 1.00 | 37.01 | C |
| ATOM | 4422 | CG | GLU | B | 268 | 7.480 | -10.109 | 55.638 | 1.00 | 36.42 | C |
| ATOM | 4423 | CD | GLU | B | 268 | 7.714 | -11.408 | 54.882 | 1.00 | 35.76 | C |
| ATOM | 4424 | OE1 | GLU | B | 268 | 8.248 | -11.363 | 53.756 | 1.00 | 35.58 | O |
| ATOM | 4425 | OE2 | GLU | B | 268 | 7.363 | -12.478 | 55.416 | 1.00 | 36.79 | O |
| ATOM | 4426 | C | GLU | B | 268 | 11.213 | -9.285 | 56.186 | 1.00 | 36.41 | C |
| ATOM | 4427 | O | GLU | B | 268 | 11.907 | -9.591 | 55.215 | 1.00 | 37.46 | O |
| ATOM | 4428 | N | ILE | B | 269 | 11.534 | -8.318 | 57.041 | 1.00 | 36.06 | N |
| ATOM | 4429 | CA | ILE | B | 269 | 12.753 | -7.535 | 56.917 | 1.00 | 35.67 | C |
| ATOM | 4430 | CB | ILE | B | 269 | 12.751 | -6.344 | 57.903 | 1.00 | 34.51 | C |
| ATOM | 4431 | CG2 | ILE | B | 269 | 14.186 | -5.911 | 58.210 | 1.00 | 31.65 | C |
| ATOM | 4432 | CG1 | ILE | B | 269 | 11.905 | -5.199 | 57.332 | 1.00 | 31.59 | C |
| ATOM | 4433 | CD1 | ILE | B | 269 | 11.661 | -4.053 | 58.309 | 1.00 | 29.91 | C |
| ATOM | 4434 | C | ILE | B | 269 | 13.952 | -8.419 | 57.219 | 1.00 | 37.16 | C |
| ATOM | 4435 | O | ILE | B | 269 | 14.960 | -8.392 | 56.511 | 1.00 | 38.00 | O |
| ATOM | 4436 | N | ILE | B | 270 | 13.829 | -9.212 | 58.274 | 1.00 | 38.37 | N |
| ATOM | 4437 | CA | ILE | B | 270 | 14.904 | -10.097 | 58.682 | 1.00 | 39.35 | C |
| ATOM | 4438 | CB | ILE | B | 270 | 14.569 | -10.747 | 60.044 | 1.00 | 38.58 | C |
| ATOM | 4439 | CG2 | ILE | B | 270 | 15.466 | -11.946 | 60.307 | 1.00 | 37.61 | C |
| ATOM | 4440 | CG1 | ILE | B | 270 | 14.735 | -9.699 | 61.147 | 1.00 | 38.57 | C |
| ATOM | 4441 | CD1 | ILE | B | 270 | 14.379 | -10.194 | 62.532 | 1.00 | 37.78 | C |
| ATOM | 4442 | C | ILE | B | 270 | 15.222 | -11.160 | 57.633 | 1.00 | 39.60 | C |
| ATOM | 4443 | O | ILE | B | 270 | 16.363 | -11.614 | 57.532 | 1.00 | 38.90 | O |
| ATOM | 4444 | N | LYS | B | 271 | 14.224 | -11.528 | 56.833 | 1.00 | 41.23 | N |
| ATOM | 4445 | CA | LYS | B | 271 | 14.406 | -12.542 | 55.792 | 1.00 | 41.71 | C |
| ATOM | 4446 | CB | LYS | B | 271 | 13.056 | -12.962 | 55.220 | 1.00 | 40.18 | C |
| ATOM | 4447 | CG | LYS | B | 271 | 12.168 | -13.665 | 56.214 | 1.00 | 41.93 | C |
| ATOM | 4448 | CD | LYS | B | 271 | 10.745 | -13.811 | 55.706 | 1.00 | 44.01 | C |
| ATOM | 4449 | CE | LYS | B | 271 | 10.658 | -14.698 | 54.478 | 1.00 | 44.53 | C |
| ATOM | 4450 | NZ | LYS | B | 271 | 9.271 | -15.222 | 54.306 | 1.00 | 46.31 | N |
| ATOM | 4451 | C | LYS | B | 271 | 15.328 | -12.129 | 54.639 | 1.00 | 43.18 | C |
| ATOM | 4452 | O | LYS | B | 271 | 15.571 | -12.925 | 53.732 | 1.00 | 44.62 | O |
| ATOM | 4453 | N | VAL | B | 272 | 15.819 | -10.889 | 54.646 | 1.00 | 42.89 | N |
| ATOM | 4454 | CA | VAL | B | 272 | 16.747 | -10.447 | 53.602 | 1.00 | 42.21 | C |
| ATOM | 4455 | CB | VAL | B | 272 | 16.084 | -9.507 | 52.506 | 1.00 | 41.99 | C |
| ATOM | 4456 | CG1 | VAL | B | 272 | 14.635 | -9.894 | 52.269 | 1.00 | 40.07 | C |
| ATOM | 4457 | CG2 | VAL | B | 272 | 16.217 | -8.049 | 52.890 | 1.00 | 44.10 | C |
| ATOM | 4458 | C | VAL | B | 272 | 17.918 | -9.729 | 54.271 | 1.00 | 42.05 | C |
| ATOM | 4459 | O | VAL | B | 272 | 19.078 | -10.009 | 53.966 | 1.00 | 42.38 | O |
| ATOM | 4460 | N | LEU | B | 273 | 17.632 | -8.824 | 55.200 | 1.00 | 42.49 | N |
| ATOM | 4461 | CA | LEU | B | 273 | 18.718 | -8.137 | 55.885 | 1.00 | 42.99 | C |
| ATOM | 4462 | CB | LEU | B | 273 | 18.226 | -6.879 | 56.607 | 1.00 | 42.95 | C |
| ATOM | 4463 | CG | LEU | B | 273 | 17.565 | -5.744 | 55.805 | 1.00 | 45.84 | C |
| ATOM | 4464 | CD1 | LEU | B | 273 | 17.753 | -4.430 | 56.561 | 1.00 | 44.28 | C |
| ATOM | 4465 | CD2 | LEU | B | 273 | 18.168 | -5.634 | 54.413 | 1.00 | 45.00 | C |
| ATOM | 4466 | C | LEU | B | 273 | 19.338 | -9.084 | 56.901 | 1.00 | 43.27 | C |
| ATOM | 4467 | O | LEU | B | 273 | 20.408 | -8.819 | 57.455 | 1.00 | 43.66 | O |
| ATOM | 4468 | N | GLY | B | 274 | 18.660 | -10.202 | 57.137 | 1.00 | 43.07 | N |
| ATOM | 4469 | CA | GLY | B | 274 | 19.149 | -11.167 | 58.101 | 1.00 | 43.10 | C |
| ATOM | 4470 | C | GLY | B | 274 | 18.848 | -10.669 | 59.500 | 1.00 | 43.54 | C |
| ATOM | 4471 | O | GLY | B | 274 | 18.243 | -9.608 | 59.667 | 1.00 | 43.64 | O |
| ATOM | 4472 | N | THR | B | 275 | 19.265 | -11.419 | 60.512 | 1.00 | 43.14 | N |
| ATOM | 4473 | CA | THR | B | 275 | 19.011 | -11.017 | 61.894 | 1.00 | 43.02 | C |
| ATOM | 4474 | CB | THR | B | 275 | 19.240 | -12.202 | 62.854 | 1.00 | 42.45 | C |
| ATOM | 4475 | OG1 | THR | B | 275 | 18.443 | -13.316 | 62.427 | 1.00 | 42.01 | O |
| ATOM | 4476 | CG2 | THR | B | 275 | 18.832 | -11.830 | 64.269 | 1.00 | 41.81 | C |
| ATOM | 4477 | C | THR | B | 275 | 19.858 | -9.823 | 62.349 | 1.00 | 43.36 | C |
| ATOM | 4478 | O | THR | B | 275 | 21.009 | -9.672 | 61.940 | 1.00 | 44.09 | O |
| ATOM | 4479 | N | PRO | B | 276 | 19.275 | -8.937 | 63.174 | 1.00 | 42.95 | N |
| ATOM | 4480 | CD | PRO | B | 276 | 17.838 | -8.877 | 63.494 | 1.00 | 42.51 | C |
| ATOM | 4481 | CA | PRO | B | 276 | 19.972 | -7.753 | 63.694 | 1.00 | 43.57 | C |
| ATOM | 4482 | CB | PRO | B | 276 | 18.845 | -6.920 | 64.314 | 1.00 | 42.41 | C |

FIG. 2-68

```
ATOM   4483  CG  PRO B 276      17.604  -7.405  63.635  1.00 42.64           C
ATOM   4484  C   PRO B 276      20.991  -8.164  64.765  1.00 44.49           C
ATOM   4485  O   PRO B 276      20.715  -9.053  65.579  1.00 43.18           O
ATOM   4486  N   THR B 277      22.158  -7.524  64.775  1.00 45.69           N
ATOM   4487  CA  THR B 277      23.174  -7.834  65.779  1.00 46.99           C
ATOM   4488  CB  THR B 277      24.591  -7.338  65.366  1.00 47.11           C
ATOM   4489  OG1 THR B 277      24.655  -5.906  65.449  1.00 47.54           O
ATOM   4490  CG2 THR B 277      24.920  -7.775  63.945  1.00 45.63           C
ATOM   4491  C   THR B 277      22.759  -7.109  67.047  1.00 48.96           C
ATOM   4492  O   THR B 277      21.942  -6.181  67.000  1.00 49.62           O
ATOM   4493  N   ALA B 278      23.307  -7.530  68.184  1.00 51.14           N
ATOM   4494  CA  ALA B 278      22.963  -6.897  69.460  1.00 50.99           C
ATOM   4495  CB  ALA B 278      23.839  -7.450  70.573  1.00 51.45           C
ATOM   4496  C   ALA B 278      23.110  -5.380  69.378  1.00 51.54           C
ATOM   4497  O   ALA B 278      22.213  -4.644  69.801  1.00 51.77           O
ATOM   4498  N   GLU B 279      24.229  -4.907  68.831  1.00 51.10           N
ATOM   4499  CA  GLU B 279      24.431  -3.467  68.721  1.00 52.97           C
ATOM   4500  CB  GLU B 279      25.773  -3.143  68.057  1.00 55.36           C
ATOM   4501  CG  GLU B 279      26.938  -3.120  69.028  1.00 60.01           C
ATOM   4502  CD  GLU B 279      27.107  -4.447  69.759  1.00 62.59           C
ATOM   4503  OE1 GLU B 279      26.777  -4.509  70.975  1.00 62.56           O
ATOM   4504  OE2 GLU B 279      27.562  -5.424  69.103  1.00 63.86           O
ATOM   4505  C   GLU B 279      23.307  -2.847  67.910  1.00 52.44           C
ATOM   4506  O   GLU B 279      22.613  -1.941  68.378  1.00 53.02           O
ATOM   4507  N   GLN B 280      23.141  -3.343  66.688  1.00 51.42           N
ATOM   4508  CA  GLN B 280      22.102  -2.864  65.784  1.00 49.69           C
ATOM   4509  CB  GLN B 280      21.933  -3.860  64.624  1.00 47.51           C
ATOM   4510  CG  GLN B 280      23.040  -3.763  63.568  1.00 44.50           C
ATOM   4511  CD  GLN B 280      22.983  -4.876  62.525  1.00 43.82           C
ATOM   4512  OE1 GLN B 280      23.562  -4.762  61.438  1.00 43.36           O
ATOM   4513  NE2 GLN B 280      22.297  -5.964  62.857  1.00 43.18           N
ATOM   4514  C   GLN B 280      20.782  -2.667  66.538  1.00 49.13           C
ATOM   4515  O   GLN B 280      20.215  -1.571  66.547  1.00 49.26           O
ATOM   4516  N   ILE B 281      20.311  -3.719  67.193  1.00 48.91           N
ATOM   4517  CA  ILE B 281      19.065  -3.643  67.947  1.00 50.32           C
ATOM   4518  CB  ILE B 281      18.721  -5.007  68.583  1.00 50.42           C
ATOM   4519  CG2 ILE B 281      17.572  -4.850  69.582  1.00 51.06           C
ATOM   4520  CG1 ILE B 281      18.346  -6.007  67.486  1.00 50.50           C
ATOM   4521  CD1 ILE B 281      17.835  -7.339  68.011  1.00 50.46           C
ATOM   4522  C   ILE B 281      19.100  -2.577  69.049  1.00 50.33           C
ATOM   4523  O   ILE B 281      18.055  -2.154  69.564  1.00 49.90           O
ATOM   4524  N   ALA B 282      20.306  -2.143  69.411  1.00 51.24           N
ATOM   4525  CA  ALA B 282      20.467  -1.128  70.451  1.00 50.98           C
ATOM   4526  CB  ALA B 282      21.827  -1.303  71.163  1.00 50.49           C
ATOM   4527  C   ALA B 282      20.323   0.304  69.916  1.00 49.85           C
ATOM   4528  O   ALA B 282      19.588   1.110  70.492  1.00 48.67           O
ATOM   4529  N   GLU B 283      21.018   0.627  68.828  1.00 49.29           N
ATOM   4530  CA  GLU B 283      20.911   1.975  68.264  1.00 50.15           C
ATOM   4531  CB  GLU B 283      21.961   2.188  67.169  1.00 50.42           C
ATOM   4532  CG  GLU B 283      23.312   2.615  67.728  1.00 51.06           C
ATOM   4533  CD  GLU B 283      24.477   2.193  66.858  1.00 52.41           C
ATOM   4534  OE1 GLU B 283      24.518   1.005  66.456  1.00 53.66           O
ATOM   4535  OE2 GLU B 283      25.360   3.038  66.587  1.00 53.71           O
ATOM   4536  C   GLU B 283      19.506   2.264  67.726  1.00 49.69           C
ATOM   4537  O   GLU B 283      19.169   3.409  67.424  1.00 49.12           O
ATOM   4538  N   MET B 284      18.693   1.215  67.635  1.00 48.79           N
ATOM   4539  CA  MET B 284      17.319   1.313  67.169  1.00 48.68           C
ATOM   4540  CB  MET B 284      16.871  -0.035  66.580  1.00 49.16           C
ATOM   4541  CG  MET B 284      17.498  -0.378  65.205  1.00 48.69           C
ATOM   4542  SD  MET B 284      17.077  -2.038  64.558  1.00 46.94           S
ATOM   4543  CE  MET B 284      15.416  -1.757  64.196  1.00 46.72           C
ATOM   4544  C   MET B 284      16.378   1.729  68.303  1.00 49.44           C
ATOM   4545  O   MET B 284      15.287   2.237  68.060  1.00 49.97           O
ATOM   4546  N   GLY B 285      16.806   1.522  69.546  1.00 50.00           N
ATOM   4547  CA  GLY B 285      15.983   1.894  70.683  1.00 49.92           C
ATOM   4548  C   GLY B 285      15.287   0.696  71.283  1.00 50.55           C
ATOM   4549  O   GLY B 285      15.940  -0.281  71.659  1.00 52.02           O
```

FIG. 2-69

```
ATOM   4550  N    ALA B 296      17.042  -15.838  59.123  1.00 45.19           N
ATOM   4551  CA   ALA B 296      18.117  -15.636  60.084  1.00 44.73           C
ATOM   4552  CB   ALA B 296      18.371  -16.929  60.868  1.00 43.55           C
ATOM   4553  C    ALA B 296      19.402  -15.145  59.400  1.00 45.18           C
ATOM   4554  O    ALA B 296      19.900  -14.070  59.731  1.00 45.00           O
ATOM   4555  N    ALA B 297      19.934  -15.914  58.451  1.00 45.65           N
ATOM   4556  CA   ALA B 297      21.157  -15.517  57.741  1.00 46.41           C
ATOM   4557  CB   ALA B 297      21.892  -16.748  57.216  1.00 44.43           C
ATOM   4558  C    ALA B 297      20.857  -14.559  56.583  1.00 47.67           C
ATOM   4559  O    ALA B 297      20.034  -14.861  55.716  1.00 47.66           O
ATOM   4560  N    ALA B 298      21.532  -13.408  56.568  1.00 47.41           N
ATOM   4561  CA   ALA B 298      21.330  -12.408  55.518  1.00 47.14           C
ATOM   4562  CB   ALA B 298      22.351  -11.284  55.652  1.00 45.92           C
ATOM   4563  C    ALA B 298      21.410  -13.014  54.125  1.00 48.10           C
ATOM   4564  O    ALA B 298      22.292  -13.824  53.832  1.00 48.15           O
ATOM   4565  N    HIS B 299      20.478  -12.611  53.266  1.00 49.91           N
ATOM   4566  CA   HIS B 299      20.405  -13.096  51.887  1.00 50.60           C
ATOM   4567  CB   HIS B 299      18.935  -13.306  51.524  1.00 51.52           C
ATOM   4568  CG   HIS B 299      18.718  -13.952  50.192  1.00 53.69           C
ATOM   4569  CD2  HIS B 299      18.912  -15.229  49.776  1.00 54.03           C
ATOM   4570  ND1  HIS B 299      18.191  -13.271  49.119  1.00 54.72           N
ATOM   4571  CE1  HIS B 299      18.062  -14.101  48.092  1.00 54.52           C
ATOM   4572  NE2  HIS B 299      18.491  -15.291  48.466  1.00 54.69           N
ATOM   4573  C    HIS B 299      21.042  -12.009  51.015  1.00 49.97           C
ATOM   4574  O    HIS B 299      20.543  -10.888  50.948  1.00 50.38           O
ATOM   4575  N    PRO B 300      22.153  -12.320  50.329  1.00 50.60           N
ATOM   4576  CD   PRO B 300      23.010  -13.517  50.359  1.00 50.71           C
ATOM   4577  CA   PRO B 300      22.764  -11.266  49.508  1.00 50.11           C
ATOM   4578  CB   PRO B 300      23.983  -11.961  48.874  1.00 49.45           C
ATOM   4579  CG   PRO B 300      23.706  -13.424  49.032  1.00 49.67           C
ATOM   4580  C    PRO B 300      21.914  -10.502  48.490  1.00 49.14           C
ATOM   4581  O    PRO B 300      21.192  -11.074  47.674  1.00 47.85           O
ATOM   4582  N    TRP B 301      22.043   -9.183  48.589  1.00 49.54           N
ATOM   4583  CA   TRP B 301      21.382   -8.182  47.755  1.00 50.01           C
ATOM   4584  CB   TRP B 301      22.119   -6.857  47.923  1.00 49.64           C
ATOM   4585  CG   TRP B 301      21.702   -6.178  49.140  1.00 50.57           C
ATOM   4586  CD2  TRP B 301      20.352   -5.906  49.513  1.00 49.99           C
ATOM   4587  CE2  TRP B 301      20.398   -5.266  50.772  1.00 50.25           C
ATOM   4588  CE3  TRP B 301      19.125   -6.123  48.896  1.00 49.73           C
ATOM   4589  CD1  TRP B 301      22.489   -5.721  50.153  1.00 51.99           C
ATOM   4590  NE1  TRP B 301      21.702   -5.172  51.146  1.00 50.95           N
ATOM   4591  CZ2  TRP B 301      19.230   -4.866  51.433  1.00 50.05           C
ATOM   4592  CZ3  TRP B 301      17.975   -5.725  49.550  1.00 50.96           C
ATOM   4593  CH2  TRP B 301      18.033   -5.092  50.806  1.00 50.30           C
ATOM   4594  C    TRP B 301      21.293   -8.503  46.283  1.00 49.96           C
ATOM   4595  O    TRP B 301      20.209   -8.564  45.697  1.00 50.17           O
ATOM   4596  N    THR B 302      22.464   -8.646  45.688  1.00 50.52           N
ATOM   4597  CA   THR B 302      22.588   -8.962  44.283  1.00 50.77           C
ATOM   4598  CB   THR B 302      24.033   -9.377  43.974  1.00 50.09           C
ATOM   4599  OG1  THR B 302      24.318  -10.621  44.627  1.00 49.14           O
ATOM   4600  CG2  THR B 302      25.006   -8.317  44.509  1.00 49.69           C
ATOM   4601  C    THR B 302      21.625  -10.092  43.928  1.00 50.73           C
ATOM   4602  O    THR B 302      21.038  -10.094  42.848  1.00 51.54           O
ATOM   4603  N    ALA B 303      21.448  -11.040  44.845  1.00 49.53           N
ATOM   4604  CA   ALA B 303      20.543  -12.165  44.604  1.00 48.46           C
ATOM   4605  CB   ALA B 303      21.005  -13.394  45.404  1.00 48.36           C
ATOM   4606  C    ALA B 303      19.078  -11.852  44.926  1.00 47.96           C
ATOM   4607  O    ALA B 303      18.190  -12.653  44.636  1.00 46.95           O
ATOM   4608  N    VAL B 304      18.829  -10.694  45.532  1.00 48.86           N
ATOM   4609  CA   VAL B 304      17.468  -10.274  45.875  1.00 48.23           C
ATOM   4610  CB   VAL B 304      17.469   -9.292  47.076  1.00 48.41           C
ATOM   4611  CG1  VAL B 304      16.070   -8.736  47.301  1.00 48.99           C
ATOM   4612  CG2  VAL B 304      17.951  -10.004  48.331  1.00 48.36           C
ATOM   4613  C    VAL B 304      16.793   -9.585  44.680  1.00 48.76           C
ATOM   4614  O    VAL B 304      15.588   -9.714  44.478  1.00 47.36           O
ATOM   4615  N    PHE B 305      17.589   -8.866  43.888  1.00 49.84           N
ATOM   4616  CA   PHE B 305      17.082   -8.139  42.726  1.00 51.00           C
```

FIG. 2-70

```
ATOM   4617  CB   PHE B 305      17.799  -6.794  42.614  1.00 49.06           C
ATOM   4618  CG   PHE B 305      17.486  -5.858  43.744  1.00 48.64           C
ATOM   4619  CD1  PHE B 305      16.232  -5.280  43.850  1.00 47.03           C
ATOM   4620  CD2  PHE B 305      18.427  -5.589  44.730  1.00 48.67           C
ATOM   4621  CE1  PHE B 305      15.912  -4.449  44.922  1.00 46.99           C
ATOM   4622  CE2  PHE B 305      18.116  -4.757  45.807  1.00 48.23           C
ATOM   4623  CZ   PHE B 305      16.855  -4.186  45.903  1.00 46.07           C
ATOM   4624  C    PHE B 305      17.203  -8.910  41.410  1.00 52.78           C
ATOM   4625  O    PHE B 305      18.137  -9.686  41.218  1.00 52.33           O
ATOM   4626  N    ARG B 306      16.253  -8.686  40.502  1.00 53.82           N
ATOM   4627  CA   ARG B 306      16.265  -9.373  39.223  1.00 54.61           C
ATOM   4628  CB   ARG B 306      15.257  -8.746  38.254  1.00 56.38           C
ATOM   4629  CG   ARG B 306      15.751  -7.484  37.577  1.00 58.31           C
ATOM   4630  CD   ARG B 306      14.892  -7.113  36.386  1.00 59.87           C
ATOM   4631  NE   ARG B 306      15.530  -6.095  35.551  1.00 61.60           N
ATOM   4632  CZ   ARG B 306      15.824  -4.861  35.951  1.00 62.04           C
ATOM   4633  NH1  ARG B 306      15.539  -4.478  37.195  1.00 61.82           N
ATOM   4634  NH2  ARG B 306      16.396  -4.014  35.098  1.00 59.97           N
ATOM   4635  C    ARG B 306      17.663  -9.308  38.614  1.00 54.76           C
ATOM   4636  O    ARG B 306      18.366  -8.306  38.747  1.00 53.75           O
ATOM   4637  N    PRO B 307      18.074 -10.388  37.933  1.00 55.26           N
ATOM   4638  CD   PRO B 307      17.220 -11.576  37.738  1.00 55.29           C
ATOM   4639  CA   PRO B 307      19.368 -10.565  37.263  1.00 55.20           C
ATOM   4640  CB   PRO B 307      19.061 -11.632  36.225  1.00 54.82           C
ATOM   4641  CG   PRO B 307      18.140 -12.527  36.978  1.00 55.78           C
ATOM   4642  C    PRO B 307      19.989  -9.318  36.643  1.00 54.87           C
ATOM   4643  O    PRO B 307      21.143  -8.988  36.918  1.00 54.95           O
ATOM   4644  N    ALA B 308      19.230  -8.626  35.803  1.00 54.62           N
ATOM   4645  CA   ALA B 308      19.750  -7.429  35.135  1.00 54.66           C
ATOM   4646  CB   ALA B 308      19.219  -7.369  33.693  1.00 55.31           C
ATOM   4647  C    ALA B 308      19.478  -6.096  35.855  1.00 53.91           C
ATOM   4648  O    ALA B 308      19.154  -5.092  35.219  1.00 53.49           O
ATOM   4649  N    THR B 309      19.615  -6.094  37.181  1.00 51.56           N
ATOM   4650  CA   THR B 309      19.413  -4.888  37.978  1.00 48.04           C
ATOM   4651  CB   THR B 309      18.927  -5.244  39.407  1.00 47.78           C
ATOM   4652  OG1  THR B 309      17.656  -5.902  39.335  1.00 45.97           O
ATOM   4653  CG2  THR B 309      18.793  -3.988  40.265  1.00 47.29           C
ATOM   4654  C    THR B 309      20.745  -4.132  38.060  1.00 47.31           C
ATOM   4655  O    THR B 309      21.764  -4.709  38.421  1.00 47.54           O
ATOM   4656  N    PRO B 310      20.752  -2.833  37.715  1.00 45.72           N
ATOM   4657  CD   PRO B 310      19.589  -2.031  37.298  1.00 45.14           C
ATOM   4658  CA   PRO B 310      21.971  -2.009  37.754  1.00 44.82           C
ATOM   4659  CB   PRO B 310      21.463  -0.615  37.383  1.00 44.51           C
ATOM   4660  CG   PRO B 310      20.245  -0.906  36.537  1.00 44.84           C
ATOM   4661  C    PRO B 310      22.682  -2.008  39.117  1.00 44.80           C
ATOM   4662  O    PRO B 310      22.111  -1.602  40.130  1.00 44.44           O
ATOM   4663  N    PRO B 311      23.953  -2.439  39.146  1.00 44.41           N
ATOM   4664  CD   PRO B 311      24.765  -2.734  37.949  1.00 44.42           C
ATOM   4665  CA   PRO B 311      24.774  -2.504  40.362  1.00 42.07           C
ATOM   4666  CB   PRO B 311      26.194  -2.591  39.807  1.00 43.64           C
ATOM   4667  CG   PRO B 311      26.001  -3.366  38.542  1.00 43.57           C
ATOM   4668  C    PRO B 311      24.594  -1.306  41.288  1.00 39.53           C
ATOM   4669  O    PRO B 311      24.484  -1.462  42.500  1.00 38.56           O
ATOM   4670  N    GLU B 312      24.566  -0.116  40.701  1.00 37.92           N
ATOM   4671  CA   GLU B 312      24.403   1.120  41.456  1.00 37.67           C
ATOM   4672  CB   GLU B 312      24.644   2.340  40.555  1.00 39.24           C
ATOM   4673  CG   GLU B 312      26.012   2.385  39.881  1.00 41.99           C
ATOM   4674  CD   GLU B 312      26.114   1.463  38.666  1.00 46.16           C
ATOM   4675  OE1  GLU B 312      25.177   0.661  38.424  1.00 48.46           O
ATOM   4676  OE2  GLU B 312      27.138   1.532  37.939  1.00 46.18           O
ATOM   4677  C    GLU B 312      23.024   1.239  42.115  1.00 37.21           C
ATOM   4678  O    GLU B 312      22.872   1.925  43.115  1.00 38.03           O
ATOM   4679  N    ALA B 313      22.013   0.594  41.554  1.00 36.15           N
ATOM   4680  CA   ALA B 313      20.697   0.664  42.159  1.00 36.28           C
ATOM   4681  CB   ALA B 313      19.632   0.101  41.213  1.00 36.45           C
ATOM   4682  C    ALA B 313      20.779  -0.182  43.415  1.00 36.87           C
ATOM   4683  O    ALA B 313      20.308   0.207  44.483  1.00 37.47           O
```

FIG. 2-71

```
ATOM   4684  N   ILE B 314      21.394  -1.350  43.273  1.00 37.72           N
ATOM   4685  CA  ILE B 314      21.557  -2.293  44.366  1.00 37.26           C
ATOM   4686  CB  ILE B 314      22.153  -3.630  43.842  1.00 38.25           C
ATOM   4687  CG2 ILE B 314      22.409  -4.583  45.001  1.00 36.53           C
ATOM   4688  CG1 ILE B 314      21.197  -4.261  42.820  1.00 38.03           C
ATOM   4689  CD1 ILE B 314      21.662  -5.589  42.245  1.00 34.78           C
ATOM   4690  C   ILE B 314      22.451  -1.738  45.474  1.00 36.65           C
ATOM   4691  O   ILE B 314      22.208  -2.003  46.641  1.00 37.87           O
ATOM   4692  N   ALA B 315      23.478  -0.976  45.112  1.00 36.09           N
ATOM   4693  CA  ALA B 315      24.393  -0.401  46.099  1.00 35.89           C
ATOM   4694  CB  ALA B 315      25.636   0.149  45.408  1.00 34.82           C
ATOM   4695  C   ALA B 315      23.727   0.702  46.908  1.00 36.99           C
ATOM   4696  O   ALA B 315      23.934   0.824  48.119  1.00 37.15           O
ATOM   4697  N   LEU B 316      22.942   1.525  46.223  1.00 37.29           N
ATOM   4698  CA  LEU B 316      22.226   2.621  46.872  1.00 36.95           C
ATOM   4699  CB  LEU B 316      21.559   3.520  45.828  1.00 34.01           C
ATOM   4700  CG  LEU B 316      20.396   4.401  46.258  1.00 33.70           C
ATOM   4701  CD1 LEU B 316      20.842   5.432  47.279  1.00 33.38           C
ATOM   4702  CD2 LEU B 316      19.827   5.071  45.025  1.00 33.57           C
ATOM   4703  C   LEU B 316      21.160   2.035  47.774  1.00 37.75           C
ATOM   4704  O   LEU B 316      20.928   2.513  48.884  1.00 39.86           O
ATOM   4705  N   CYS B 317      20.519   0.985  47.289  1.00 37.10           N
ATOM   4706  CA  CYS B 317      19.462   0.364  48.046  1.00 37.87           C
ATOM   4707  CB  CYS B 317      18.816  -0.747  47.218  1.00 38.36           C
ATOM   4708  SG  CYS B 317      17.252  -1.311  47.892  1.00 41.58           S
ATOM   4709  C   CYS B 317      19.982  -0.180  49.374  1.00 37.43           C
ATOM   4710  O   CYS B 317      19.336  -0.032  50.415  1.00 36.59           O
ATOM   4711  N   SER B 318      21.159  -0.792  49.338  1.00 37.34           N
ATOM   4712  CA  SER B 318      21.771  -1.366  50.537  1.00 37.44           C
ATOM   4713  CB  SER B 318      23.037  -2.135  50.155  1.00 36.92           C
ATOM   4714  OG  SER B 318      23.969  -1.270  49.524  1.00 39.22           O
ATOM   4715  C   SER B 318      22.131  -0.325  51.596  1.00 36.74           C
ATOM   4716  O   SER B 318      22.078  -0.605  52.795  1.00 37.91           O
ATOM   4717  N   ARG B 319      22.510   0.869  51.155  1.00 37.32           N
ATOM   4718  CA  ARG B 319      22.902   1.934  52.074  1.00 37.62           C
ATOM   4719  CB  ARG B 319      23.926   2.820  51.385  1.00 37.78           C
ATOM   4720  CG  ARG B 319      25.184   2.054  51.057  1.00 40.92           C
ATOM   4721  CD  ARG B 319      25.988   1.791  52.318  1.00 41.76           C
ATOM   4722  NE  ARG B 319      26.687   3.011  52.704  1.00 44.22           N
ATOM   4723  CZ  ARG B 319      26.362   3.764  53.745  1.00 45.42           C
ATOM   4724  NH1 ARG B 319      25.342   3.415  54.523  1.00 45.95           N
ATOM   4725  NH2 ARG B 319      27.047   4.875  53.994  1.00 46.01           N
ATOM   4726  C   ARG B 319      21.726   2.759  52.583  1.00 37.47           C
ATOM   4727  O   ARG B 319      21.902   3.773  53.266  1.00 37.59           O
ATOM   4728  N   LEU B 320      20.525   2.308  52.234  1.00 37.20           N
ATOM   4729  CA  LEU B 320      19.289   2.946  52.650  1.00 34.71           C
ATOM   4730  CB  LEU B 320      18.361   3.136  51.451  1.00 32.73           C
ATOM   4731  CG  LEU B 320      18.733   4.202  50.426  1.00 31.98           C
ATOM   4732  CD1 LEU B 320      17.740   4.189  49.274  1.00 34.01           C
ATOM   4733  CD2 LEU B 320      18.742   5.552  51.097  1.00 30.80           C
ATOM   4734  C   LEU B 320      18.651   1.999  53.648  1.00 34.80           C
ATOM   4735  O   LEU B 320      18.341   2.382  54.770  1.00 34.77           O
ATOM   4736  N   LEU B 321      18.488   0.747  53.236  1.00 36.24           N
ATOM   4737  CA  LEU B 321      17.876  -0.262  54.084  1.00 37.30           C
ATOM   4738  CB  LEU B 321      17.224  -1.324  53.203  1.00 36.85           C
ATOM   4739  CG  LEU B 321      16.095  -0.743  52.342  1.00 35.95           C
ATOM   4740  CD1 LEU B 321      15.703  -1.729  51.266  1.00 33.90           C
ATOM   4741  CD2 LEU B 321      14.910  -0.380  53.227  1.00 35.84           C
ATOM   4742  C   LEU B 321      18.843  -0.904  55.079  1.00 37.60           C
ATOM   4743  O   LEU B 321      19.188  -2.086  54.973  1.00 38.39           O
ATOM   4744  N   GLU B 322      19.270  -0.095  56.043  1.00 37.64           N
ATOM   4745  CA  GLU B 322      20.176  -0.511  57.108  1.00 37.43           C
ATOM   4746  CB  GLU B 322      21.380   0.434  57.180  1.00 37.42           C
ATOM   4747  CG  GLU B 322      22.226   0.470  55.913  1.00 41.05           C
ATOM   4748  CD  GLU B 322      23.680   0.041  56.141  1.00 41.72           C
ATOM   4749  OE1 GLU B 322      23.907  -0.938  56.886  1.00 41.02           O
ATOM   4750  OE2 GLU B 322      24.585   0.679  55.551  1.00 42.64           O
```

FIG. 2-72

```
ATOM   4751  C    GLU B 322      19.409   -0.453   58.433  1.00 37.21           C
ATOM   4752  O    GLU B 322      18.501    0.361   58.585  1.00 36.92           O
ATOM   4753  N    TYR B 323      19.762   -1.313   59.383  1.00 36.95           N
ATOM   4754  CA   TYR B 323      19.088   -1.305   60.675  1.00 36.84           C
ATOM   4755  CB   TYR B 323      19.450   -2.545   61.486  1.00 37.12           C
ATOM   4756  CG   TYR B 323      18.756   -3.814   61.044  1.00 37.80           C
ATOM   4757  CD1  TYR B 323      17.389   -3.993   61.248  1.00 36.24           C
ATOM   4758  CE1  TYR B 323      16.760   -5.178   60.888  1.00 35.95           C
ATOM   4759  CD2  TYR B 323      19.478   -4.856   60.459  1.00 38.66           C
ATOM   4760  CE2  TYR B 323      18.856   -6.044   60.095  1.00 38.54           C
ATOM   4761  CZ   TYR B 323      17.500   -6.200   60.317  1.00 37.50           C
ATOM   4762  OH   TYR B 323      16.894   -7.391   60.000  1.00 38.92           O
ATOM   4763  C    TYR B 323      19.506   -0.058   61.436  1.00 37.41           C
ATOM   4764  O    TYR B 323      18.662    0.724   61.857  1.00 39.99           O
ATOM   4765  N    THR B 324      20.811    0.128   61.608  1.00 36.07           N
ATOM   4766  CA   THR B 324      21.324    1.290   62.319  1.00 35.37           C
ATOM   4767  CB   THR B 324      22.876    1.280   62.344  1.00 36.26           C
ATOM   4768  OG1  THR B 324      23.334    0.053   62.924  1.00 36.07           O
ATOM   4769  CG2  THR B 324      23.422    2.440   63.168  1.00 33.19           C
ATOM   4770  C    THR B 324      20.804    2.533   61.598  1.00 34.77           C
ATOM   4771  O    THR B 324      21.268    2.882   60.512  1.00 34.72           O
ATOM   4772  N    PRO B 325      19.821    3.216   62.201  1.00 34.56           N
ATOM   4773  CD   PRO B 325      19.376    2.970   63.582  1.00 33.99           C
ATOM   4774  CA   PRO B 325      19.190    4.426   61.665  1.00 35.23           C
ATOM   4775  CB   PRO B 325      18.422    4.971   62.863  1.00 34.29           C
ATOM   4776  CG   PRO B 325      18.095    3.739   63.643  1.00 33.13           C
ATOM   4777  C    PRO B 325      20.236    5.411   61.188  1.00 36.04           C
ATOM   4778  O    PRO B 325      20.079    6.107   60.181  1.00 36.72           O
ATOM   4779  N    THR B 326      21.319    5.437   61.944  1.00 36.83           N
ATOM   4780  CA   THR B 326      22.447    6.317   61.731  1.00 35.69           C
ATOM   4781  CB   THR B 326      23.216    6.407   63.057  1.00 36.56           C
ATOM   4782  OG1  THR B 326      23.624    7.757   63.282  1.00 37.49           O
ATOM   4783  CG2  THR B 326      24.423    5.467   63.045  1.00 36.84           C
ATOM   4784  C    THR B 326      23.372    5.871   60.595  1.00 34.60           C
ATOM   4785  O    THR B 326      24.179    6.655   60.102  1.00 34.65           O
ATOM   4786  N    ALA B 327      23.253    4.612   60.191  1.00 34.51           N
ATOM   4787  CA   ALA B 327      24.080    4.065   59.124  1.00 33.73           C
ATOM   4788  CB   ALA B 327      24.127    2.551   59.236  1.00 31.42           C
ATOM   4789  C    ALA B 327      23.532    4.474   57.759  1.00 34.57           C
ATOM   4790  O    ALA B 327      24.259    4.513   56.775  1.00 35.05           O
ATOM   4791  N    ARG B 328      22.240    4.788   57.714  1.00 35.23           N
ATOM   4792  CA   ARG B 328      21.569    5.182   56.483  1.00 34.72           C
ATOM   4793  CB   ARG B 328      20.070    5.303   56.750  1.00 34.75           C
ATOM   4794  CG   ARG B 328      19.427    3.968   57.079  1.00 34.73           C
ATOM   4795  CD   ARG B 328      18.018    4.115   57.593  1.00 34.25           C
ATOM   4796  NE   ARG B 328      17.648    2.934   58.360  1.00 34.20           N
ATOM   4797  CZ   ARG B 328      16.771    2.931   59.357  1.00 34.76           C
ATOM   4798  NH1  ARG B 328      16.159    4.050   59.716  1.00 32.91           N
ATOM   4799  NH2  ARG B 328      16.518    1.807   60.013  1.00 36.40           N
ATOM   4800  C    ARG B 328      22.090    6.483   55.882  1.00 35.36           C
ATOM   4801  O    ARG B 328      22.586    7.354   56.600  1.00 35.81           O
ATOM   4802  N    LEU B 329      21.974    6.607   54.561  1.00 35.47           N
ATOM   4803  CA   LEU B 329      22.415    7.809   53.854  1.00 36.18           C
ATOM   4804  CB   LEU B 329      22.453    7.562   52.336  1.00 36.99           C
ATOM   4805  CG   LEU B 329      23.622    6.796   51.700  1.00 37.01           C
ATOM   4806  CD1  LEU B 329      23.952    5.596   52.554  1.00 40.01           C
ATOM   4807  CD2  LEU B 329      23.274    6.374   50.279  1.00 36.22           C
ATOM   4808  C    LEU B 329      21.445    8.950   54.139  1.00 36.53           C
ATOM   4809  O    LEU B 329      20.303    8.709   54.527  1.00 36.91           O
ATOM   4810  N    THR B 330      21.896   10.189   53.960  1.00 36.21           N
ATOM   4811  CA   THR B 330      21.014   11.329   54.174  1.00 36.64           C
ATOM   4812  CB   THR B 330      21.767   12.579   54.688  1.00 37.55           C
ATOM   4813  OG1  THR B 330      22.595   13.111   53.646  1.00 37.86           O
ATOM   4814  CG2  THR B 330      22.636   12.217   55.882  1.00 36.95           C
ATOM   4815  C    THR B 330      20.420   11.643   52.808  1.00 36.88           C
ATOM   4816  O    THR B 330      21.067   11.429   51.782  1.00 36.59           O
ATOM   4817  N    PRO B 331      19.175   12.139   52.773  1.00 36.07           N
```

FIG. 2-73

| | | | | | | | | | |
|---|---|---|---|---|---|---|---|---|---|
| ATOM | 4818 | CD | PRO | B | 331 | 18.276 | 12.466 | 53.895 | 1.00 35.13 | C |
| ATOM | 4819 | CA | PRO | B | 331 | 18.553 | 12.459 | 51.487 | 1.00 35.48 | C |
| ATOM | 4820 | CB | PRO | B | 331 | 17.369 | 13.323 | 51.893 | 1.00 35.83 | C |
| ATOM | 4821 | CG | PRO | B | 331 | 16.956 | 12.700 | 53.198 | 1.00 35.13 | C |
| ATOM | 4822 | C | PRO | B | 331 | 19.501 | 13.151 | 50.499 | 1.00 36.11 | C |
| ATOM | 4823 | O | PRO | B | 331 | 19.531 | 12.798 | 49.319 | 1.00 36.87 | O |
| ATOM | 4824 | N | LEU | B | 332 | 20.285 | 14.116 | 50.969 | 1.00 36.05 | N |
| ATOM | 4825 | CA | LEU | B | 332 | 21.219 | 14.820 | 50.086 | 1.00 36.74 | C |
| ATOM | 4826 | CB | LEU | B | 332 | 21.865 | 16.018 | 50.794 | 1.00 37.18 | C |
| ATOM | 4827 | CG | LEU | B | 332 | 21.527 | 17.434 | 50.326 | 1.00 38.13 | C |
| ATOM | 4828 | CD1 | LEU | B | 332 | 22.632 | 18.364 | 50.806 | 1.00 40.15 | C |
| ATOM | 4829 | CD2 | LEU | B | 332 | 21.429 | 17.502 | 48.801 | 1.00 39.36 | C |
| ATOM | 4830 | C | LEU | B | 332 | 22.327 | 13.904 | 49.594 | 1.00 36.91 | C |
| ATOM | 4831 | O | LEU | B | 332 | 22.828 | 14.080 | 48.483 | 1.00 38.23 | O |
| ATOM | 4832 | N | GLU | B | 333 | 22.716 | 12.941 | 50.428 | 1.00 36.87 | N |
| ATOM | 4833 | CA | GLU | B | 333 | 23.780 | 11.996 | 50.083 | 1.00 37.90 | C |
| ATOM | 4834 | CB | GLU | B | 333 | 24.234 | 11.224 | 51.339 | 1.00 40.10 | C |
| ATOM | 4835 | CG | GLU | B | 333 | 25.448 | 11.843 | 52.046 | 1.00 41.42 | C |
| ATOM | 4836 | CD | GLU | B | 333 | 25.519 | 11.539 | 53.544 | 1.00 43.91 | C |
| ATOM | 4837 | OE1 | GLU | B | 333 | 25.433 | 10.354 | 53.942 | 1.00 44.02 | O |
| ATOM | 4838 | OE2 | GLU | B | 333 | 25.677 | 12.499 | 54.333 | 1.00 46.05 | O |
| ATOM | 4839 | C | GLU | B | 333 | 23.291 | 11.034 | 49.006 | 1.00 36.60 | C |
| ATOM | 4840 | O | GLU | B | 333 | 24.037 | 10.682 | 48.088 | 1.00 35.40 | O |
| ATOM | 4841 | N | ALA | B | 334 | 22.024 | 10.639 | 49.123 | 1.00 36.58 | N |
| ATOM | 4842 | CA | ALA | B | 334 | 21.383 | 9.734 | 48.179 | 1.00 35.74 | C |
| ATOM | 4843 | CB | ALA | B | 334 | 20.000 | 9.354 | 48.681 | 1.00 34.27 | C |
| ATOM | 4844 | C | ALA | B | 334 | 21.285 | 10.387 | 46.800 | 1.00 35.80 | C |
| ATOM | 4845 | O | ALA | B | 334 | 21.450 | 9.718 | 45.775 | 1.00 36.08 | O |
| ATOM | 4846 | N | CYS | B | 335 | 21.028 | 11.693 | 46.779 | 1.00 36.16 | N |
| ATOM | 4847 | CA | CYS | B | 335 | 20.936 | 12.436 | 45.517 | 1.00 36.42 | C |
| ATOM | 4848 | CB | CYS | B | 335 | 20.543 | 13.899 | 45.764 | 1.00 34.14 | C |
| ATOM | 4849 | SG | CYS | B | 335 | 18.840 | 14.195 | 46.235 | 1.00 33.25 | S |
| ATOM | 4850 | C | CYS | B | 335 | 22.283 | 12.416 | 44.794 | 1.00 37.41 | C |
| ATOM | 4851 | O | CYS | B | 335 | 22.342 | 12.388 | 43.561 | 1.00 37.21 | O |
| ATOM | 4852 | N | ALA | B | 336 | 23.362 | 12.436 | 45.574 | 1.00 37.62 | N |
| ATOM | 4853 | CA | ALA | B | 336 | 24.710 | 12.426 | 45.020 | 1.00 38.83 | C |
| ATOM | 4854 | CB | ALA | B | 336 | 25.686 | 13.061 | 46.006 | 1.00 40.30 | C |
| ATOM | 4855 | C | ALA | B | 336 | 25.190 | 11.024 | 44.663 | 1.00 39.16 | C |
| ATOM | 4856 | O | ALA | B | 336 | 26.320 | 10.848 | 44.201 | 1.00 39.54 | O |
| ATOM | 4857 | N | HIS | B | 337 | 24.339 | 10.024 | 44.866 | 1.00 39.01 | N |
| ATOM | 4858 | CA | HIS | B | 337 | 24.734 | 8.659 | 44.559 | 1.00 38.87 | C |
| ATOM | 4859 | CB | HIS | B | 337 | 23.696 | 7.664 | 45.074 | 1.00 37.22 | C |
| ATOM | 4860 | CG | HIS | B | 337 | 24.153 | 6.238 | 45.013 | 1.00 35.47 | C |
| ATOM | 4861 | CD2 | HIS | B | 337 | 24.312 | 5.398 | 43.962 | 1.00 34.39 | C |
| ATOM | 4862 | ND1 | HIS | B | 337 | 24.522 | 5.521 | 46.131 | 1.00 34.35 | N |
| ATOM | 4863 | CE1 | HIS | B | 337 | 24.884 | 4.303 | 45.772 | 1.00 34.21 | C |
| ATOM | 4864 | NE2 | HIS | B | 337 | 24.765 | 4.204 | 44.462 | 1.00 32.96 | N |
| ATOM | 4865 | C | HIS | B | 337 | 24.928 | 8.470 | 43.060 | 1.00 39.98 | C |
| ATOM | 4866 | O | HIS | B | 337 | 24.222 | 9.068 | 42.242 | 1.00 39.72 | O |
| ATOM | 4867 | N | SER | B | 338 | 25.888 | 7.621 | 42.705 | 1.00 41.82 | N |
| ATOM | 4868 | CA | SER | B | 338 | 26.204 | 7.356 | 41.305 | 1.00 42.40 | C |
| ATOM | 4869 | CB | SER | B | 338 | 27.385 | 6.393 | 41.219 | 1.00 41.59 | C |
| ATOM | 4870 | OG | SER | B | 338 | 27.017 | 5.113 | 41.682 | 1.00 43.45 | O |
| ATOM | 4871 | C | SER | B | 338 | 25.027 | 6.822 | 40.482 | 1.00 42.55 | C |
| ATOM | 4872 | O | SER | B | 338 | 24.976 | 7.033 | 39.269 | 1.00 43.90 | O |
| ATOM | 4873 | N | PHE | B | 339 | 24.089 | 6.138 | 41.138 | 1.00 40.97 | N |
| ATOM | 4874 | CA | PHE | B | 339 | 22.903 | 5.585 | 40.473 | 1.00 40.37 | C |
| ATOM | 4875 | CB | PHE | B | 339 | 21.975 | 4.946 | 41.520 | 1.00 39.92 | C |
| ATOM | 4876 | CG | PHE | B | 339 | 20.615 | 4.546 | 40.994 | 1.00 39.67 | C |
| ATOM | 4877 | CD1 | PHE | B | 339 | 20.479 | 3.574 | 40.007 | 1.00 40.30 | C |
| ATOM | 4878 | CD2 | PHE | B | 339 | 19.463 | 5.106 | 41.531 | 1.00 38.62 | C |
| ATOM | 4879 | CE1 | PHE | B | 339 | 19.210 | 3.164 | 39.571 | 1.00 39.54 | C |
| ATOM | 4880 | CE2 | PHE | B | 339 | 18.197 | 4.701 | 41.099 | 1.00 38.53 | C |
| ATOM | 4881 | CZ | PHE | B | 339 | 18.072 | 3.729 | 40.120 | 1.00 38.16 | C |
| ATOM | 4882 | C | PHE | B | 339 | 22.164 | 6.694 | 39.718 | 1.00 40.53 | C |
| ATOM | 4883 | O | PHE | B | 339 | 21.476 | 6.442 | 38.730 | 1.00 40.51 | O |
| ATOM | 4884 | N | PHE | B | 340 | 22.332 | 7.927 | 40.182 | 1.00 39.40 | N |

FIG. 2-74

```
ATOM   4885  CA  PHE B 340      21.676    9.062   39.556  1.00 39.22           C
ATOM   4886  CB  PHE B 340      21.120   10.005   40.615  1.00 36.79           C
ATOM   4887  CG  PHE B 340      20.215    9.344   41.607  1.00 37.42           C
ATOM   4888  CD1 PHE B 340      18.955    8.889   41.234  1.00 35.22           C
ATOM   4889  CD2 PHE B 340      20.607    9.211   42.933  1.00 34.42           C
ATOM   4890  CE1 PHE B 340      18.101    8.320   42.167  1.00 33.89           C
ATOM   4891  CE2 PHE B 340      19.757    8.643   43.867  1.00 33.59           C
ATOM   4892  CZ  PHE B 340      18.500    8.199   43.485  1.00 33.67           C
ATOM   4893  C   PHE B 340      22.627    9.851   38.675  1.00 40.51           C
ATOM   4894  O   PHE B 340      22.278   10.942   38.217  1.00 41.24           O
ATOM   4895  N   ASP B 341      23.829    9.327   38.454  1.00 40.71           N
ATOM   4896  CA  ASP B 341      24.801   10.037   37.623  1.00 41.22           C
ATOM   4897  CB  ASP B 341      26.090    9.217   37.466  1.00 41.05           C
ATOM   4898  CG  ASP B 341      27.038    9.422   38.626  1.00 41.38           C
ATOM   4899  OD1 ASP B 341      26.597   10.032   39.623  1.00 42.79           O
ATOM   4900  OD2 ASP B 341      28.207    8.988   38.557  1.00 41.29           O
ATOM   4901  C   ASP B 341      24.222   10.382   36.264  1.00 40.58           C
ATOM   4902  O   ASP B 341      24.408   11.491   35.775  1.00 40.43           O
ATOM   4903  N   GLU B 342      23.510    9.437   35.662  1.00 39.55           N
ATOM   4904  CA  GLU B 342      22.905    9.689   34.372  1.00 39.89           C
ATOM   4905  CB  GLU B 342      21.958    8.549   34.000  1.00 40.92           C
ATOM   4906  CG  GLU B 342      21.087    8.860   32.797  1.00 43.50           C
ATOM   4907  CD  GLU B 342      20.377    7.642   32.249  1.00 44.87           C
ATOM   4908  OE1 GLU B 342      19.942    6.789   33.051  1.00 43.81           O
ATOM   4909  OE2 GLU B 342      20.242    7.551   31.010  1.00 46.04           O
ATOM   4910  C   GLU B 342      22.150   11.019   34.353  1.00 40.36           C
ATOM   4911  O   GLU B 342      22.393   11.852   33.491  1.00 41.39           O
ATOM   4912  N   LEU B 343      21.249   11.220   35.315  1.00 40.76           N
ATOM   4913  CA  LEU B 343      20.455   12.443   35.397  1.00 40.90           C
ATOM   4914  CB  LEU B 343      19.607   12.453   36.672  1.00 41.21           C
ATOM   4915  CG  LEU B 343      18.634   11.304   36.976  1.00 41.48           C
ATOM   4916  CD1 LEU B 343      17.864   11.655   38.251  1.00 40.01           C
ATOM   4917  CD2 LEU B 343      17.671   11.085   35.825  1.00 40.93           C
ATOM   4918  C   LEU B 343      21.302   13.711   35.369  1.00 41.60           C
ATOM   4919  O   LEU B 343      20.814   14.780   34.999  1.00 41.55           O
ATOM   4920  N   ARG B 344      22.561   13.597   35.775  1.00 41.94           N
ATOM   4921  CA  ARG B 344      23.457   14.748   35.788  1.00 43.15           C
ATOM   4922  CB  ARG B 344      24.526   14.575   36.871  1.00 42.30           C
ATOM   4923  CG  ARG B 344      24.154   15.150   38.227  1.00 40.16           C
ATOM   4924  CD  ARG B 344      25.240   14.849   39.245  1.00 41.13           C
ATOM   4925  NE  ARG B 344      25.245   13.439   39.615  1.00 41.90           N
ATOM   4926  CZ  ARG B 344      24.523   12.923   40.607  1.00 41.06           C
ATOM   4927  NH1 ARG B 344      23.740   13.705   41.337  1.00 40.52           N
ATOM   4928  NH2 ARG B 344      24.572   11.623   40.862  1.00 39.84           N
ATOM   4929  C   ARG B 344      24.126   14.973   34.429  1.00 44.75           C
ATOM   4930  O   ARG B 344      24.791   15.983   34.207  1.00 44.00           O
ATOM   4931  N   ASP B 345      23.947   14.024   33.522  1.00 47.04           N
ATOM   4932  CA  ASP B 345      24.511   14.116   32.175  1.00 49.83           C
ATOM   4933  CB  ASP B 345      24.227   12.811   31.431  1.00 50.85           C
ATOM   4934  CG  ASP B 345      24.646   12.855   29.983  1.00 53.06           C
ATOM   4935  OD1 ASP B 345      24.626   13.955   29.386  1.00 53.68           O
ATOM   4936  OD2 ASP B 345      24.979   11.777   29.435  1.00 52.87           O
ATOM   4937  C   ASP B 345      23.856   15.286   31.435  1.00 51.22           C
ATOM   4938  O   ASP B 345      22.632   15.429   31.469  1.00 52.66           O
ATOM   4939  N   PRO B 346      24.650   16.125   30.742  1.00 51.90           N
ATOM   4940  CD  PRO B 346      26.117   16.109   30.605  1.00 52.14           C
ATOM   4941  CA  PRO B 346      24.079   17.268   30.010  1.00 51.28           C
ATOM   4942  CB  PRO B 346      25.315   18.040   29.562  1.00 51.59           C
ATOM   4943  CG  PRO B 346      26.323   16.959   29.366  1.00 51.35           C
ATOM   4944  C   PRO B 346      23.166   16.918   28.826  1.00 50.51           C
ATOM   4945  O   PRO B 346      22.410   17.764   28.344  1.00 50.70           O
ATOM   4946  N   ASN B 347      23.240   15.673   28.373  1.00 49.50           N
ATOM   4947  CA  ASN B 347      22.448   15.199   27.252  1.00 49.09           C
ATOM   4948  CB  ASN B 347      23.260   14.181   26.457  1.00 49.88           C
ATOM   4949  CG  ASN B 347      24.478   14.801   25.804  1.00 52.95           C
ATOM   4950  OD1 ASN B 347      25.376   14.091   25.334  1.00 54.73           O
ATOM   4951  ND2 ASN B 347      24.520   16.134   25.767  1.00 52.55           N
```

FIG. 2-75

```
ATOM   4952  C    ASN B 347      21.122  14.573  27.655  1.00 48.70      C
ATOM   4953  O    ASN B 347      20.109  14.766  26.979  1.00 49.24      O
ATOM   4954  N    VAL B 348      21.126  13.815  28.746  1.00 47.73      N
ATOM   4955  CA   VAL B 348      19.920  13.134  29.198  1.00 47.05      C
ATOM   4956  CB   VAL B 348      19.995  12.788  30.707  1.00 46.33      C
ATOM   4957  CG1  VAL B 348      19.728  14.033  31.559  1.00 45.82      C
ATOM   4958  CG2  VAL B 348      19.001  11.690  31.024  1.00 45.53      C
ATOM   4959  C    VAL B 348      18.630  13.904  28.938  1.00 46.71      C
ATOM   4960  O    VAL B 348      18.513  15.090  29.246  1.00 46.05      O
ATOM   4961  N    LYS B 349      17.663  13.199  28.373  1.00 46.22      N
ATOM   4962  CA   LYS B 349      16.358  13.763  28.077  1.00 46.75      C
ATOM   4963  CB   LYS B 349      16.235  14.064  26.573  1.00 48.36      C
ATOM   4964  CG   LYS B 349      17.157  15.201  26.107  1.00 50.15      C
ATOM   4965  CD   LYS B 349      16.904  15.618  24.669  1.00 53.19      C
ATOM   4966  CE   LYS B 349      18.011  16.536  24.165  1.00 55.34      C
ATOM   4967  NZ   LYS B 349      17.921  16.789  22.686  1.00 57.76      N
ATOM   4968  C    LYS B 349      15.343  12.717  28.524  1.00 45.87      C
ATOM   4969  O    LYS B 349      15.732  11.620  28.913  1.00 45.55      O
ATOM   4970  N    LEU B 350      14.056  13.047  28.513  1.00 45.02      N
ATOM   4971  CA   LEU B 350      13.047  12.072  28.928  1.00 44.48      C
ATOM   4972  CB   LEU B 350      11.761  12.780  29.355  1.00 44.13      C
ATOM   4973  CG   LEU B 350      11.812  13.792  30.500  1.00 43.03      C
ATOM   4974  CD1  LEU B 350      10.396  14.270  30.826  1.00 40.95      C
ATOM   4975  CD2  LEU B 350      12.440  13.144  31.711  1.00 41.69      C
ATOM   4976  C    LEU B 350      12.736  11.148  27.758  1.00 44.78      C
ATOM   4977  O    LEU B 350      12.892  11.532  26.605  1.00 44.38      O
ATOM   4978  N    PRO B 351      12.277   9.920  28.037  1.00 45.94      N
ATOM   4979  CD   PRO B 351      11.866   9.405  29.348  1.00 46.03      C
ATOM   4980  CA   PRO B 351      11.944   8.963  26.973  1.00 47.24      C
ATOM   4981  CB   PRO B 351      11.440   7.736  27.738  1.00 46.25      C
ATOM   4982  CG   PRO B 351      11.968   7.922  29.131  1.00 46.63      C
ATOM   4983  C    PRO B 351      10.822   9.600  26.160  1.00 48.43      C
ATOM   4984  O    PRO B 351      10.284   9.024  25.209  1.00 49.72      O
ATOM   4985  N    ASN B 352      10.488  10.809  26.585  1.00 49.77      N
ATOM   4986  CA   ASN B 352       9.445  11.640  26.020  1.00 50.32      C
ATOM   4987  CB   ASN B 352       8.982  12.612  27.100  1.00 52.86      C
ATOM   4988  CG   ASN B 352       7.499  12.761  27.123  1.00 54.76      C
ATOM   4989  OD1  ASN B 352       6.945  13.423  27.996  1.00 55.29      O
ATOM   4990  ND2  ASN B 352       6.830  12.134  26.154  1.00 56.70      N
ATOM   4991  C    ASN B 352       9.970  12.439  24.850  1.00 50.02      C
ATOM   4992  O    ASN B 352       9.211  12.894  24.001  1.00 50.19      O
ATOM   4993  N    GLY B 353      11.284  12.623  24.838  1.00 50.08      N
ATOM   4994  CA   GLY B 353      11.918  13.402  23.801  1.00 50.66      C
ATOM   4995  C    GLY B 353      12.108  14.762  24.427  1.00 52.00      C
ATOM   4996  O    GLY B 353      12.881  15.586  23.950  1.00 52.16      O
ATOM   4997  N    ARG B 354      11.388  14.982  25.526  1.00 52.86      N
ATOM   4998  CA   ARG B 354      11.429  16.239  26.269  1.00 53.01      C
ATOM   4999  CB   ARG B 354      10.096  16.444  26.994  1.00 55.00      C
ATOM   5000  CG   ARG B 354       8.891  16.145  26.121  1.00 58.09      C
ATOM   5001  CD   ARG B 354       7.577  16.373  26.860  1.00 60.19      C
ATOM   5002  NE   ARG B 354       7.542  17.689  27.494  1.00 61.04      N
ATOM   5003  CZ   ARG B 354       6.430  18.319  27.853  1.00 61.30      C
ATOM   5004  NH1  ARG B 354       5.243  17.750  27.634  1.00 60.22      N
ATOM   5005  NH2  ARG B 354       6.515  19.519  28.433  1.00 61.61      N
ATOM   5006  C    ARG B 354      12.568  16.291  27.279  1.00 51.85      C
ATOM   5007  O    ARG B 354      13.195  15.275  27.589  1.00 51.69      O
ATOM   5008  N    ASP B 355      12.843  17.486  27.787  1.00 50.43      N
ATOM   5009  CA   ASP B 355      13.905  17.637  28.765  1.00 49.96      C
ATOM   5010  CB   ASP B 355      14.481  19.060  28.733  1.00 52.37      C
ATOM   5011  CG   ASP B 355      15.147  19.394  27.401  1.00 54.01      C
ATOM   5012  OD1  ASP B 355      14.432  19.833  26.471  1.00 55.24      O
ATOM   5013  OD2  ASP B 355      16.384  19.206  27.278  1.00 54.62      O
ATOM   5014  C    ASP B 355      13.409  17.300  30.167  1.00 48.12      C
ATOM   5015  O    ASP B 355      12.230  17.451  30.480  1.00 47.13      O
ATOM   5016  N    THR B 356      14.328  16.821  30.996  1.00 46.82      N
ATOM   5017  CA   THR B 356      14.030  16.450  32.370  1.00 44.76      C
ATOM   5018  CB   THR B 356      15.221  15.721  33.011  1.00 44.89      C
```

FIG. 2-76

```
ATOM   5019  OG1 THR B 356      16.393  16.544  32.912  1.00 42.21           O
ATOM   5020  CG2 THR B 356      15.480  14.398  32.310  1.00 42.61           C
ATOM   5021  C   THR B 356      13.769  17.695  33.192  1.00 44.45           C
ATOM   5022  O   THR B 356      14.313  18.764  32.909  1.00 44.63           O
ATOM   5023  N   PRO B 357      12.936  17.579  34.231  1.00 44.07           N
ATOM   5024  CD  PRO B 357      12.184  16.410  34.716  1.00 43.73           C
ATOM   5025  CA  PRO B 357      12.673  18.761  35.051  1.00 43.81           C
ATOM   5026  CB  PRO B 357      11.680  18.249  36.097  1.00 43.77           C
ATOM   5027  CG  PRO B 357      11.949  16.771  36.163  1.00 43.70           C
ATOM   5028  C   PRO B 357      13.981  19.272  35.663  1.00 44.79           C
ATOM   5029  O   PRO B 357      15.008  18.584  35.614  1.00 45.26           O
ATOM   5030  N   ALA B 358      13.951  20.485  36.213  1.00 45.25           N
ATOM   5031  CA  ALA B 358      15.134  21.078  36.832  1.00 45.32           C
ATOM   5032  CB  ALA B 358      14.832  22.480  37.298  1.00 45.31           C
ATOM   5033  C   ALA B 358      15.490  20.202  38.015  1.00 45.89           C
ATOM   5034  O   ALA B 358      14.666  20.004  38.904  1.00 47.78           O
ATOM   5035  N   LEU B 359      16.709  19.676  38.031  1.00 45.58           N
ATOM   5036  CA  LEU B 359      17.135  18.784  39.107  1.00 45.00           C
ATOM   5037  CB  LEU B 359      17.566  17.446  38.509  1.00 43.37           C
ATOM   5038  CG  LEU B 359      16.538  16.823  37.582  1.00 42.44           C
ATOM   5039  CD1 LEU B 359      17.065  15.521  36.991  1.00 41.68           C
ATOM   5040  CD2 LEU B 359      15.259  16.602  38.387  1.00 43.15           C
ATOM   5041  C   LEU B 359      18.301  19.374  39.866  1.00 45.47           C
ATOM   5042  O   LEU B 359      18.688  18.870  40.915  1.00 45.98           O
ATOM   5043  N   PHE B 360      18.840  20.465  39.333  1.00 45.87           N
ATOM   5044  CA  PHE B 360      20.022  21.108  39.900  1.00 44.98           C
ATOM   5045  CB  PHE B 360      21.071  21.179  38.802  1.00 44.49           C
ATOM   5046  CG  PHE B 360      21.155  19.925  38.002  1.00 44.93           C
ATOM   5047  CD1 PHE B 360      21.432  18.715  38.634  1.00 45.00           C
ATOM   5048  CD2 PHE B 360      20.920  19.932  36.634  1.00 44.43           C
ATOM   5049  CE1 PHE B 360      21.477  17.530  37.916  1.00 45.19           C
ATOM   5050  CE2 PHE B 360      20.963  18.748  35.911  1.00 45.79           C
ATOM   5051  CZ  PHE B 360      21.240  17.543  36.554  1.00 45.01           C
ATOM   5052  C   PHE B 360      19.876  22.473  40.548  1.00 44.28           C
ATOM   5053  O   PHE B 360      20.856  23.012  41.070  1.00 44.06           O
ATOM   5054  N   ASN B 361      18.671  23.032  40.529  1.00 44.57           N
ATOM   5055  CA  ASN B 361      18.450  24.351  41.118  1.00 44.97           C
ATOM   5056  CB  ASN B 361      17.222  25.006  40.483  1.00 44.24           C
ATOM   5057  CG  ASN B 361      15.948  24.237  40.753  1.00 43.92           C
ATOM   5058  OD1 ASN B 361      15.928  23.003  40.724  1.00 44.06           O
ATOM   5059  ND2 ASN B 361      14.873  24.962  41.012  1.00 43.89           N
ATOM   5060  C   ASN B 361      18.281  24.271  42.621  1.00 45.51           C
ATOM   5061  O   ASN B 361      17.215  24.587  43.150  1.00 46.73           O
ATOM   5062  N   PHE B 362      19.338  23.838  43.305  1.00 45.84           N
ATOM   5063  CA  PHE B 362      19.335  23.716  44.761  1.00 46.06           C
ATOM   5064  CB  PHE B 362      20.550  22.917  45.224  1.00 43.65           C
ATOM   5065  CG  PHE B 362      20.472  21.461  44.901  1.00 42.66           C
ATOM   5066  CD1 PHE B 362      19.766  20.592  45.728  1.00 42.40           C
ATOM   5067  CD2 PHE B 362      21.075  20.955  43.756  1.00 41.35           C
ATOM   5068  CE1 PHE B 362      19.668  19.242  45.415  1.00 42.39           C
ATOM   5069  CE2 PHE B 362      20.980  19.605  43.434  1.00 40.77           C
ATOM   5070  CZ  PHE B 362      20.275  18.745  44.263  1.00 41.01           C
ATOM   5071  C   PHE B 362      19.372  25.084  45.427  1.00 47.31           C
ATOM   5072  O   PHE B 362      19.681  26.086  44.790  1.00 48.21           O
ATOM   5073  N   THR B 363      19.054  25.117  46.713  1.00 49.13           N
ATOM   5074  CA  THR B 363      19.086  26.347  47.483  1.00 51.04           C
ATOM   5075  CB  THR B 363      17.693  26.704  48.049  1.00 50.93           C
ATOM   5076  OG1 THR B 363      17.197  25.614  48.834  1.00 52.12           O
ATOM   5077  CG2 THR B 363      16.722  26.997  46.914  1.00 51.15           C
ATOM   5078  C   THR B 363      20.054  26.095  48.637  1.00 53.49           C
ATOM   5079  O   THR B 363      20.429  24.948  48.908  1.00 53.98           O
ATOM   5080  N   THR B 364      20.473  27.158  49.315  1.00 54.85           N
ATOM   5081  CA  THR B 364      21.400  27.015  50.430  1.00 55.54           C
ATOM   5082  CB  THR B 364      21.858  28.382  50.945  1.00 56.65           C
ATOM   5083  OG1 THR B 364      20.746  29.070  51.531  1.00 58.82           O
ATOM   5084  CG2 THR B 364      22.416  29.217  49.800  1.00 57.10           C
ATOM   5085  C   THR B 364      20.713  26.254  51.555  1.00 55.72           C
```

FIG. 2-77

```
ATOM   5086  O   THR B 364      21.362  25.601  52.382  1.00 55.80           O
ATOM   5087  N   GLN B 365      19.384  26.317  51.556  1.00 55.24           N
ATOM   5088  CA  GLN B 365      18.567  25.640  52.558  1.00 54.12           C
ATOM   5089  CB  GLN B 365      17.138  26.179  52.516  1.00 54.90           C
ATOM   5090  CG  GLN B 365      16.169  25.494  53.469  1.00 56.65           C
ATOM   5091  CD  GLN B 365      16.669  25.490  54.896  1.00 57.41           C
ATOM   5092  OE1 GLN B 365      17.587  26.238  55.243  1.00 59.70           O
ATOM   5093  NE2 GLN B 365      16.061  24.658  55.738  1.00 56.07           N
ATOM   5094  C   GLN B 365      18.545  24.126  52.372  1.00 53.86           C
ATOM   5095  O   GLN B 365      18.421  23.388  53.349  1.00 54.08           O
ATOM   5096  N   GLU B 366      18.649  23.658  51.129  1.00 53.51           N
ATOM   5097  CA  GLU B 366      18.653  22.211  50.885  1.00 53.13           C
ATOM   5098  CB  GLU B 366      18.170  21.857  49.488  1.00 52.88           C
ATOM   5099  CG  GLU B 366      16.923  22.527  49.018  1.00 52.75           C
ATOM   5100  CD  GLU B 366      16.689  22.239  47.554  1.00 51.60           C
ATOM   5101  OE1 GLU B 366      16.451  21.064  47.203  1.00 50.57           O
ATOM   5102  OE2 GLU B 366      16.764  23.183  46.753  1.00 52.39           O
ATOM   5103  C   GLU B 366      20.065  21.668  50.998  1.00 52.96           C
ATOM   5104  O   GLU B 366      20.279  20.590  51.547  1.00 53.21           O
ATOM   5105  N   LEU B 367      21.023  22.407  50.445  1.00 52.32           N
ATOM   5106  CA  LEU B 367      22.410  21.972  50.490  1.00 52.83           C
ATOM   5107  CB  LEU B 367      23.250  22.797  49.503  1.00 51.78           C
ATOM   5108  CG  LEU B 367      23.008  22.342  48.044  1.00 51.53           C
ATOM   5109  CD1 LEU B 367      23.558  23.343  47.034  1.00 49.76           C
ATOM   5110  CD2 LEU B 367      23.657  20.981  47.850  1.00 50.27           C
ATOM   5111  C   LEU B 367      22.926  22.080  51.927  1.00 53.44           C
ATOM   5112  O   LEU B 367      23.918  21.459  52.306  1.00 53.22           O
ATOM   5113  N   SER B 368      22.188  22.844  52.729  1.00 54.21           N
ATOM   5114  CA  SER B 368      22.466  23.081  54.141  1.00 53.18           C
ATOM   5115  CB  SER B 368      21.141  23.432  54.834  1.00 54.06           C
ATOM   5116  OG  SER B 368      21.146  23.099  56.216  1.00 56.49           O
ATOM   5117  C   SER B 368      23.169  21.925  54.876  1.00 52.75           C
ATOM   5118  O   SER B 368      24.342  22.032  55.243  1.00 53.42           O
ATOM   5119  N   SER B 369      22.460  20.821  55.081  1.00 51.87           N
ATOM   5120  CA  SER B 369      23.014  19.660  55.787  1.00 50.27           C
ATOM   5121  CB  SER B 369      22.140  18.425  55.553  1.00 49.77           C
ATOM   5122  OG  SER B 369      22.610  17.690  54.419  1.00 49.98           O
ATOM   5123  C   SER B 369      24.443  19.261  55.414  1.00 49.44           C
ATOM   5124  O   SER B 369      25.112  18.570  56.196  1.00 49.84           O
ATOM   5125  N   ASN B 370      24.921  19.679  54.245  1.00 48.78           N
ATOM   5126  CA  ASN B 370      26.249  19.241  53.798  1.00 48.50           C
ATOM   5127  CB  ASN B 370      26.162  17.733  53.560  1.00 48.31           C
ATOM   5128  CG  ASN B 370      27.488  17.102  53.234  1.00 49.87           C
ATOM   5129  OD1 ASN B 370      28.406  17.760  52.750  1.00 50.16           O
ATOM   5130  ND2 ASN B 370      27.588  15.797  53.475  1.00 50.62           N
ATOM   5131  C   ASN B 370      26.664  19.956  52.494  1.00 47.98           C
ATOM   5132  O   ASN B 370      26.928  19.313  51.474  1.00 47.76           O
ATOM   5133  N   PRO B 371      26.759  21.294  52.525  1.00 47.47           N
ATOM   5134  CD  PRO B 371      26.829  22.074  53.774  1.00 46.61           C
ATOM   5135  CA  PRO B 371      27.127  22.131  51.373  1.00 47.84           C
ATOM   5136  CB  PRO B 371      27.636  23.409  52.029  1.00 47.25           C
ATOM   5137  CG  PRO B 371      26.788  23.480  53.267  1.00 46.45           C
ATOM   5138  C   PRO B 371      28.118  21.594  50.325  1.00 49.23           C
ATOM   5139  O   PRO B 371      27.843  21.628  49.124  1.00 49.10           O
ATOM   5140  N   PRO B 372      29.285  21.093  50.757  1.00 50.90           N
ATOM   5141  CD  PRO B 372      29.718  20.821  52.140  1.00 51.43           C
ATOM   5142  CA  PRO B 372      30.273  20.580  49.803  1.00 51.19           C
ATOM   5143  CB  PRO B 372      31.160  19.694  50.668  1.00 49.99           C
ATOM   5144  CG  PRO B 372      31.178  20.432  51.949  1.00 51.02           C
ATOM   5145  C   PRO B 372      29.667  19.818  48.634  1.00 52.40           C
ATOM   5146  O   PRO B 372      29.969  20.099  47.471  1.00 53.46           O
ATOM   5147  N   LEU B 373      28.793  18.867  48.939  1.00 51.98           N
ATOM   5148  CA  LEU B 373      28.177  18.048  47.892  1.00 52.28           C
ATOM   5149  CB  LEU B 373      27.079  17.164  48.484  1.00 51.80           C
ATOM   5150  CG  LEU B 373      27.578  16.028  49.379  1.00 51.59           C
ATOM   5151  CD1 LEU B 373      26.378  15.245  49.878  1.00 52.02           C
ATOM   5152  CD2 LEU B 373      28.529  15.122  48.615  1.00 50.53           C
```

FIG. 2-78

```
ATOM   5153  C    LEU B 373      27.634  18.794  46.673  1.00 52.48           C
ATOM   5154  O    LEU B 373      27.250  18.169  45.680  1.00 53.07           O
ATOM   5155  N    ALA B 374      27.609  20.123  46.737  1.00 52.06           N
ATOM   5156  CA   ALA B 374      27.138  20.917  45.612  1.00 51.75           C
ATOM   5157  CB   ALA B 374      27.090  22.392  45.988  1.00 50.24           C
ATOM   5158  C    ALA B 374      28.055  20.713  44.416  1.00 52.19           C
ATOM   5159  O    ALA B 374      27.646  20.918  43.276  1.00 53.14           O
ATOM   5160  N    THR B 375      29.294  20.302  44.666  1.00 52.86           N
ATOM   5161  CA   THR B 375      30.230  20.088  43.564  1.00 53.37           C
ATOM   5162  CB   THR B 375      31.702  19.982  44.059  1.00 53.97           C
ATOM   5163  OG1  THR B 375      31.778  19.104  45.194  1.00 55.14           O
ATOM   5164  CG2  THR B 375      32.238  21.356  44.438  1.00 53.35           C
ATOM   5165  C    THR B 375      29.871  18.835  42.780  1.00 52.71           C
ATOM   5166  O    THR B 375      30.336  18.648  41.660  1.00 52.13           O
ATOM   5167  N    ILE B 376      29.042  17.982  43.381  1.00 52.68           N
ATOM   5168  CA   ILE B 376      28.594  16.750  42.730  1.00 52.62           C
ATOM   5169  CB   ILE B 376      28.569  15.548  43.699  1.00 53.20           C
ATOM   5170  CG2  ILE B 376      27.994  14.326  42.977  1.00 53.26           C
ATOM   5171  CG1  ILE B 376      29.969  15.240  44.224  1.00 52.88           C
ATOM   5172  CD1  ILE B 376      29.990  14.139  45.281  1.00 52.91           C
ATOM   5173  C    ILE B 376      27.165  16.907  42.208  1.00 51.87           C
ATOM   5174  O    ILE B 376      26.852  16.465  41.106  1.00 52.55           O
ATOM   5175  N    LEU B 377      26.306  17.520  43.018  1.00 50.96           N
ATOM   5176  CA   LEU B 377      24.901  17.720  42.664  1.00 50.30           C
ATOM   5177  CB   LEU B 377      24.114  18.160  43.899  1.00 49.01           C
ATOM   5178  CG   LEU B 377      24.080  17.171  45.070  1.00 48.18           C
ATOM   5179  CD1  LEU B 377      23.476  17.852  46.290  1.00 47.40           C
ATOM   5180  CD2  LEU B 377      23.287  15.936  44.690  1.00 47.10           C
ATOM   5181  C    LEU B 377      24.687  18.725  41.538  1.00 50.17           C
ATOM   5182  O    LEU B 377      23.982  18.434  40.577  1.00 49.31           O
ATOM   5183  N    ILE B 378      25.273  19.912  41.670  1.00 51.32           N
ATOM   5184  CA   ILE B 378      25.145  20.941  40.642  1.00 52.46           C
ATOM   5185  CB   ILE B 378      25.262  22.363  41.243  1.00 51.17           C
ATOM   5186  CG2  ILE B 378      24.793  23.400  40.232  1.00 51.31           C
ATOM   5187  CG1  ILE B 378      24.387  22.486  42.485  1.00 51.24           C
ATOM   5188  CD1  ILE B 378      24.605  23.772  43.259  1.00 51.32           C
ATOM   5189  C    ILE B 378      26.287  20.725  39.651  1.00 53.97           C
ATOM   5190  O    ILE B 378      27.381  21.245  39.838  1.00 54.82           O
ATOM   5191  N    PRO B 379      26.045  19.953  38.581  1.00 55.70           N
ATOM   5192  CD   PRO B 379      24.734  19.497  38.080  1.00 55.96           C
ATOM   5193  CA   PRO B 379      27.093  19.696  37.593  1.00 57.08           C
ATOM   5194  CB   PRO B 379      26.417  18.731  36.632  1.00 57.15           C
ATOM   5195  CG   PRO B 379      25.011  19.237  36.614  1.00 56.37           C
ATOM   5196  C    PRO B 379      27.565  20.978  36.908  1.00 59.33           C
ATOM   5197  O    PRO B 379      26.938  22.037  37.041  1.00 59.58           O
ATOM   5198  N    PRO B 380      28.677  20.900  36.158  1.00 61.17           N
ATOM   5199  CD   PRO B 380      29.528  19.707  35.992  1.00 61.80           C
ATOM   5200  CA   PRO B 380      29.253  22.051  35.441  1.00 62.31           C
ATOM   5201  CB   PRO B 380      30.445  21.439  34.700  1.00 62.07           C
ATOM   5202  CG   PRO B 380      30.862  20.321  35.604  1.00 62.45           C
ATOM   5203  C    PRO B 380      28.264  22.707  34.480  1.00 62.86           C
ATOM   5204  O    PRO B 380      27.927  23.884  34.626  1.00 62.45           O
ATOM   5205  N    HIS B 381      27.802  21.932  33.502  1.00 63.51           N
ATOM   5206  CA   HIS B 381      26.856  22.423  32.506  1.00 64.68           C
ATOM   5207  CB   HIS B 381      26.447  21.288  31.564  1.00 65.82           C
ATOM   5208  CG   HIS B 381      25.448  20.347  32.161  1.00 66.65           C
ATOM   5209  CD2  HIS B 381      25.566  19.060  32.567  1.00 66.94           C
ATOM   5210  ND1  HIS B 381      24.153  20.726  32.453  1.00 66.51           N
ATOM   5211  CE1  HIS B 381      23.518  19.713  33.015  1.00 66.98           C
ATOM   5212  NE2  HIS B 381      24.351  18.689  33.097  1.00 67.44           N
ATOM   5213  C    HIS B 381      25.600  23.001  33.150  1.00 65.89           C
ATOM   5214  O    HIS B 381      24.680  23.428  32.452  1.00 65.88           O
ATOM   5215  N    ALA B 382      25.548  22.993  34.479  1.00 67.50           N
ATOM   5216  CA   ALA B 382      24.396  23.533  35.193  1.00 68.57           C
ATOM   5217  CB   ALA B 382      23.837  22.487  36.156  1.00 67.99           C
ATOM   5218  C    ALA B 382      24.760  24.815  35.946  1.00 69.73           C
ATOM   5219  O    ALA B 382      23.889  25.635  36.237  1.00 70.17           O
```

FIG. 2-79

```
ATOM   5220  N    ARG B 383     26.041  24.985  36.273  1.00 71.28           N
ATOM   5221  CA   ARG B 383     26.484  26.191  36.978  1.00 72.20           C
ATOM   5222  CB   ARG B 383     27.968  26.091  37.377  1.00 71.94           C
ATOM   5223  CG   ARG B 383     28.265  25.174  38.550  1.00 71.48           C
ATOM   5224  CD   ARG B 383     28.698  23.787  38.098  1.00 71.61           C
ATOM   5225  NE   ARG B 383     30.137  23.594  38.276  1.00 72.36           N
ATOM   5226  CZ   ARG B 383     30.684  22.790  39.188  1.00 72.86           C
ATOM   5227  NH1  ARG B 383     29.914  22.092  40.012  1.00 72.83           N
ATOM   5228  NH2  ARG B 383     32.008  22.692  39.285  1.00 73.15           N
ATOM   5229  C    ARG B 383     26.301  27.408  36.085  1.00 73.05           C
ATOM   5230  O    ARG B 383     25.474  28.285  36.427  1.00 73.47           O
ATOM   5231  OXT  ARG B 383     27.005  27.460  35.050  1.00 73.90           O
TER    5232       ARG B 383
ATOM   5233  O    HOH W   1     -1.266   8.542 -13.084  1.00 14.72           O
ATOM   5234  O    HOH W   2     -2.998   9.432  -6.812  1.00 15.65           O
ATOM   5235  O    HOH W   3      9.785  -1.916  56.208  1.00 19.78           O
ATOM   5236  O    HOH W   4      8.933   9.805  29.446  1.00 24.72           O
ATOM   5237  O    HOH W   5      1.827  -0.751  54.225  1.00 21.82           O
ATOM   5238  O    HOH W   6    -10.281  12.225  -5.503  1.00 26.73           O
ATOM   5239  O    HOH W   7     -9.904  21.576  -5.887  1.00 31.82           O
ATOM   5240  O    HOH W   8      3.618  11.961  67.656  1.00 32.99           O
ATOM   5241  O    HOH W   9      6.850   7.948 -10.496  1.00 26.54           O
ATOM   5242  O    HOH W  10      1.475  16.642 -11.459  1.00 30.73           O
ATOM   5243  O    HOH W  11     -9.038  32.369  55.850  1.00 36.07           O
ATOM   5244  O    HOH W  12      5.386  -2.421  63.540  1.00 45.57           O
ATOM   5245  O    HOH W  13     -3.401  13.202   9.117  1.00 39.47           O
ATOM   5246  O    HOH W  14     -5.902  -8.009   9.752  1.00 31.40           O
ATOM   5247  O    HOH W  15      2.459   7.676   2.942  1.00 24.28           O
ATOM   5248  O    HOH W  16      1.212 -10.287 -15.241  1.00 25.00           O
ATOM   5249  O    HOH W  17     22.684  16.165  41.069  1.00 44.25           O
ATOM   5250  O    HOH W  18     14.185  18.047  41.501  1.00 35.23           O
ATOM   5251  O    HOH W  19    -12.340  30.469  55.509  1.00 48.41           O
ATOM   5252  O    HOH W  20     15.295   3.090  31.834  1.00 39.30           O
ATOM   5253  O    HOH W  21     -7.619  16.792   4.653  1.00 49.13           O
ATOM   5254  O    HOH W  22      1.509  -0.311  48.741  1.00 37.76           O
ATOM   5255  O    HOH W  23     -0.729 -16.958 -12.544  1.00 50.10           O
ATOM   5256  O    HOH W  24    -14.842   6.544  -6.115  1.00 26.75           O
ATOM   5257  O    HOH W  25      3.589  11.159  -1.679  1.00 49.96           O
ATOM   5258  O    HOH W  26      8.607   7.447  55.916  1.00 37.34           O
ATOM   5259  O    HOH W  27     -5.490 -10.158   3.059  1.00 35.71           O
ATOM   5260  O    HOH W  28      1.923   4.482 -14.833  1.00 22.25           O
ATOM   5261  O    HOH W  29     19.763  15.158  53.621  1.00 41.36           O
ATOM   5262  O    HOH W  30    -14.137  -3.358  13.898  1.00 52.64           O
ATOM   5263  O    HOH W  31     17.776  28.660  51.568  1.00 37.35           O
ATOM   5264  O    HOH W  32      9.817   4.643  58.639  1.00 18.67           O
ATOM   5265  O    HOH W  33      8.837   6.465  24.658  1.00 38.39           O
ATOM   5266  O    HOH W  34      4.942  -3.799  20.145  1.00 38.77           O
ATOM   5267  O    HOH W  35     12.047  -2.552   4.756  1.00 25.11           O
ATOM   5268  O    HOH W  36      9.465   4.048   5.637  1.00 31.42           O
ATOM   5269  O    HOH W  37     12.428  -1.209  -3.858  1.00 30.72           O
ATOM   5270  O    HOH W  38      7.410 -14.265  -6.580  1.00 43.24           O
ATOM   5271  O    HOH W  39      9.313   5.019  -0.505  1.00 47.49           O
ATOM   5272  O    HOH W  40      8.620  13.251   8.315  1.00 43.76           O
ATOM   5273  O    HOH W  41      8.786   9.151   3.874  1.00 37.23           O
ATOM   5274  O    HOH W  42     -1.331  18.415   2.847  1.00 30.70           O
ATOM   5275  O    HOH W  43      6.336  14.830  -3.593  1.00 28.35           O
ATOM   5276  O    HOH W  44      1.876   2.309 -13.627  1.00 26.10           O
ATOM   5277  O    HOH W  45     -3.191  21.138 -16.692  1.00 40.52           O
ATOM   5278  O    HOH W  46    -15.049  17.703  -5.989  1.00 49.15           O
ATOM   5279  O    HOH W  47      7.775  -2.356 -13.990  1.00 38.74           O
ATOM   5280  O    HOH W  48      3.494   3.720 -22.134  1.00 37.42           O
ATOM   5281  O    HOH W  49     12.528  17.436 -19.899  1.00 41.37           O
ATOM   5282  O    HOH W  50      7.521  18.039 -13.046  1.00 45.90           O
ATOM   5283  O    HOH W  51      4.285  16.633 -23.145  1.00 44.71           O
ATOM   5284  O    HOH W  52    -10.845   3.884 -22.045  1.00 38.68           O
ATOM   5285  O    HOH W  53    -13.228   7.970 -20.498  1.00 36.86           O
ATOM   5286  O    HOH W  54    -12.353  18.434 -23.038  1.00 39.41           O
```

FIG. 2-80

| | | | | | | | | | |
|---|---|---|---|---|---|---|---|---|---|
| ATOM | 5287 | O | HOH W | 55 | -19.736 | 12.560 | -15.750 | 1.00 40.32 | O |
| ATOM | 5288 | O | HOH W | 56 | -18.614 | 7.306 | -5.565 | 1.00 29.06 | O |
| ATOM | 5289 | O | HOH W | 57 | -18.866 | 3.114 | -6.902 | 1.00 29.87 | O |
| ATOM | 5290 | O | HOH W | 58 | 4.548 | -19.094 | -4.472 | 1.00 30.15 | O |
| ATOM | 5291 | O | HOH W | 59 | -1.562 | 31.086 | 46.525 | 1.00 35.60 | O |
| ATOM | 5292 | O | HOH W | 60 | -16.129 | 21.933 | 50.459 | 1.00 35.02 | O |
| ATOM | 5293 | O | HOH W | 61 | -17.916 | 25.194 | 51.475 | 1.00 48.13 | O |
| ATOM | 5294 | O | HOH W | 62 | -16.095 | 15.055 | 36.400 | 1.00 44.80 | O |
| ATOM | 5295 | O | HOH W | 63 | -4.710 | 22.147 | 36.647 | 1.00 42.49 | O |
| ATOM | 5296 | O | HOH W | 64 | -4.377 | 14.277 | 43.981 | 1.00 22.95 | O |
| ATOM | 5297 | O | HOH W | 65 | -0.564 | 13.610 | 37.656 | 1.00 59.25 | O |
| ATOM | 5298 | O | HOH W | 66 | 17.908 | 13.912 | 56.928 | 1.00 37.58 | O |
| ATOM | 5299 | O | HOH W | 67 | -0.786 | 17.340 | 53.673 | 1.00 48.99 | O |
| ATOM | 5300 | O | HOH W | 68 | 6.846 | 16.376 | 70.823 | 1.00 47.26 | O |
| ATOM | 5301 | O | HOH W | 69 | 6.328 | 15.810 | 76.044 | 1.00 54.44 | O |
| ATOM | 5302 | O | HOH W | 70 | 0.718 | 5.223 | 68.861 | 1.00 42.42 | O |
| ATOM | 5303 | O | HOH W | 71 | 4.796 | 8.735 | 72.668 | 1.00 42.23 | O |
| ATOM | 5304 | O | HOH W | 72 | -0.679 | 4.187 | 61.277 | 1.00 39.55 | O |
| ATOM | 5305 | O | HOH W | 73 | 15.671 | 6.652 | 62.858 | 1.00 25.65 | O |
| ATOM | 5306 | O | HOH W | 74 | 8.704 | -1.527 | 49.188 | 1.00 23.45 | O |
| ATOM | 5307 | O | HOH W | 75 | 26.656 | -5.532 | 62.975 | 1.00 38.36 | O |
| ATOM | 5308 | O | HOH W | 76 | 26.316 | 8.554 | 56.662 | 1.00 33.50 | O |
| ATOM | 5309 | O | HOH W | 77 | 28.841 | 6.565 | 52.139 | 1.00 53.34 | O |
| ATOM | 5310 | O | HOH W | 78 | 21.438 | 8.185 | 58.552 | 1.00 32.74 | O |
| ATOM | 5311 | O | HOH W | 79 | 21.306 | 17.170 | 32.847 | 1.00 41.33 | O |
| ATOM | 5312 | O | HOH W | 80 | 5.009 | 19.405 | 35.953 | 1.00 38.17 | O |
| ATOM | 5313 | O | HOH W | 81 | -18.006 | 10.433 | -20.033 | 1.00 44.97 | O |
| ATOM | 5314 | O | HOH W | 82 | -16.672 | 17.338 | -24.015 | 1.00 44.37 | O |
| ATOM | 5315 | O | HOH W | 83 | -13.487 | 10.522 | -22.044 | 1.00 44.93 | O |
| TER | 5316 | | HOH W | 83 | | | | | |
| END | | | | | | | | | |

FIG. 3-1

|  | | Atom Type | Resid | # | X | Y | Z | OCC | B | | |
|---|---|---|---|---|---|---|---|---|---|---|---|
| ATOM | 1 | CB | VAL A | 37 | 23.813 | -4.451 | 22.235 | 1.00 | 53.77 | A | C |
| ATOM | 2 | CG1 | VAL A | 37 | 22.591 | -4.098 | 23.069 | 1.00 | 53.77 | A | C |
| ATOM | 3 | CG2 | VAL A | 37 | 23.675 | -5.901 | 21.733 | 1.00 | 53.77 | A | C |
| ATOM | 4 | C | VAL A | 37 | 23.455 | -2.090 | 21.514 | 1.00 | 51.96 | A | C |
| ATOM | 5 | O | VAL A | 37 | 24.096 | -1.462 | 22.344 | 1.00 | 51.96 | A | O |
| ATOM | 6 | N | VAL A | 37 | 25.303 | -3.477 | 20.430 | 1.00 | 51.96 | A | N |
| ATOM | 7 | CA | VAL A | 37 | 23.929 | -3.466 | 21.034 | 1.00 | 51.96 | A | C |
| ATOM | 8 | N | THR A | 38 | 22.317 | -1.640 | 20.987 | 1.00 | 55.35 | A | N |
| ATOM | 9 | CA | THR A | 38 | 21.736 | -0.353 | 21.363 | 1.00 | 55.35 | A | C |
| ATOM | 10 | CB | THR A | 38 | 21.245 | 0.429 | 20.138 | 1.00 | 57.52 | A | C |
| ATOM | 11 | OG1 | THR A | 38 | 22.313 | 0.564 | 19.196 | 1.00 | 57.52 | A | O |
| ATOM | 12 | CG2 | THR A | 38 | 20.768 | 1.807 | 20.545 | 1.00 | 57.52 | A | C |
| ATOM | 13 | C | THR A | 38 | 20.531 | -0.597 | 22.261 | 1.00 | 55.35 | A | C |
| ATOM | 14 | O | THR A | 38 | 19.774 | -1.546 | 22.039 | 1.00 | 55.35 | A | O |
| ATOM | 15 | N | THR A | 39 | 20.370 | 0.251 | 23.278 | 1.00 | 61.66 | A | N |
| ATOM | 16 | CA | THR A | 39 | 19.249 | 0.154 | 24.217 | 1.00 | 61.66 | A | C |
| ATOM | 17 | CB | THR A | 39 | 19.716 | -0.268 | 25.635 | 1.00 | 40.02 | A | C |
| ATOM | 18 | OG1 | THR A | 39 | 20.110 | -1.642 | 25.609 | 1.00 | 40.02 | A | O |
| ATOM | 19 | CG2 | THR A | 39 | 18.594 | -0.092 | 26.664 | 1.00 | 40.02 | A | C |
| ATOM | 20 | C | THR A | 39 | 18.537 | 1.501 | 24.310 | 1.00 | 61.66 | A | C |
| ATOM | 21 | O | THR A | 39 | 19.149 | 2.527 | 24.634 | 1.00 | 61.66 | A | O |
| ATOM | 22 | N | VAL A | 40 | 17.241 | 1.491 | 24.020 | 1.00 | 30.79 | A | N |
| ATOM | 23 | CA | VAL A | 40 | 16.456 | 2.709 | 24.061 | 1.00 | 30.79 | A | C |
| ATOM | 24 | CB | VAL A | 40 | 16.066 | 3.140 | 22.641 | 1.00 | 33.45 | A | C |
| ATOM | 25 | CG1 | VAL A | 40 | 17.317 | 3.436 | 21.825 | 1.00 | 33.45 | A | C |
| ATOM | 26 | CG2 | VAL A | 40 | 15.238 | 2.035 | 21.977 | 1.00 | 33.45 | A | C |
| ATOM | 27 | C | VAL A | 40 | 15.191 | 2.492 | 24.858 | 1.00 | 30.79 | A | C |
| ATOM | 28 | O | VAL A | 40 | 14.769 | 1.354 | 25.072 | 1.00 | 30.79 | A | O |
| ATOM | 29 | N | VAL A | 41 | 14.593 | 3.579 | 25.319 | 1.00 | 45.23 | A | N |
| ATOM | 30 | CA | VAL A | 41 | 13.339 | 3.465 | 26.054 | 1.00 | 45.23 | A | C |
| ATOM | 31 | CB | VAL A | 41 | 13.293 | 4.389 | 27.301 | 1.00 | 34.90 | A | C |
| ATOM | 32 | CG1 | VAL A | 41 | 11.905 | 4.357 | 27.932 | 1.00 | 34.90 | A | C |
| ATOM | 33 | CG2 | VAL A | 41 | 14.328 | 3.929 | 28.312 | 1.00 | 34.90 | A | C |
| ATOM | 34 | C | VAL A | 41 | 12.283 | 3.871 | 25.040 | 1.00 | 45.23 | A | C |
| ATOM | 35 | O | VAL A | 41 | 12.155 | 5.047 | 24.682 | 1.00 | 45.23 | A | O |
| ATOM | 36 | N | ALA A | 42 | 11.549 | 2.872 | 24.563 | 1.00 | 33.07 | A | N |
| ATOM | 37 | CA | ALA A | 42 | 10.535 | 3.093 | 23.560 | 1.00 | 33.07 | A | C |
| ATOM | 38 | CB | ALA A | 42 | 10.866 | 2.283 | 22.320 | 1.00 | 33.89 | A | C |
| ATOM | 39 | C | ALA A | 42 | 9.115 | 2.796 | 23.986 | 1.00 | 33.07 | A | C |
| ATOM | 40 | O | ALA A | 42 | 8.825 | 1.750 | 24.560 | 1.00 | 33.07 | A | O |
| ATOM | 41 | N | THR A | 43 | 8.236 | 3.746 | 23.685 | 1.00 | 38.30 | A | N |
| ATOM | 42 | CA | THR A | 43 | 6.810 | 3.622 | 23.947 | 1.00 | 38.30 | A | C |
| ATOM | 43 | CB | THR A | 43 | 6.093 | 4.979 | 23.753 | 1.00 | 56.48 | A | C |
| ATOM | 44 | OG1 | THR A | 43 | 6.918 | 6.043 | 24.248 | 1.00 | 56.48 | A | O |
| ATOM | 45 | CG2 | THR A | 43 | 4.756 | 4.985 | 24.489 | 1.00 | 56.48 | A | C |
| ATOM | 46 | C | THR A | 43 | 6.312 | 2.648 | 22.857 | 1.00 | 38.30 | A | C |
| ATOM | 47 | O | THR A | 43 | 6.750 | 2.711 | 21.702 | 1.00 | 38.30 | A | O |
| ATOM | 48 | N | PRO A | 44 | 5.404 | 1.731 | 23.209 | 1.00 | 49.45 | A | N |
| ATOM | 49 | CD | PRO A | 44 | 4.949 | 1.359 | 24.556 | 1.00 | 43.65 | A | C |
| ATOM | 50 | CA | PRO A | 44 | 4.902 | 0.782 | 22.214 | 1.00 | 49.45 | A | C |
| ATOM | 51 | CB | PRO A | 44 | 4.121 | -0.223 | 23.056 | 1.00 | 43.65 | A | C |
| ATOM | 52 | CG | PRO A | 44 | 4.784 | -0.134 | 24.411 | 1.00 | 43.65 | A | C |
| ATOM | 53 | C | PRO A | 44 | 4.024 | 1.498 | 21.193 | 1.00 | 49.45 | A | C |
| ATOM | 54 | O | PRO A | 44 | 3.408 | 2.522 | 21.511 | 1.00 | 49.45 | A | O |
| ATOM | 55 | N | GLY A | 45 | 3.971 | 0.966 | 19.972 | 1.00 | 54.69 | A | N |
| ATOM | 56 | CA | GLY A | 45 | 3.187 | 1.593 | 18.922 | 1.00 | 54.69 | A | C |
| ATOM | 57 | C | GLY A | 45 | 1.721 | 1.730 | 19.257 | 1.00 | 54.69 | A | C |
| ATOM | 58 | O | GLY A | 45 | 1.233 | 2.808 | 19.602 | 1.00 | 54.69 | A | O |
| ATOM | 59 | N | ALA A | 46 | 1.011 | 0.618 | 19.146 | 1.00 | 84.98 | A | N |
| ATOM | 60 | CA | ALA A | 46 | -0.413 | 0.592 | 19.437 | 1.00 | 84.98 | A | C |

FIG. 3-2

| | | | | | | | | | | | |
|---|---|---|---|---|---|---|---|---|---|---|---|
| ATOM | 61 | CB | ALA | A | 46 | -1.147 | -0.287 | 18.389 | 1.00 | 54.67 | A | C |
| ATOM | 62 | C | ALA | A | 46 | -0.566 | 0.007 | 20.843 | 1.00 | 84.98 | A | C |
| ATOM | 63 | O | ALA | A | 46 | -0.404 | -1.208 | 21.038 | 1.00 | 84.98 | A | O |
| ATOM | 64 | N | GLY | A | 47 | -0.859 | 0.862 | 21.822 | 1.00 | 58.86 | A | N |
| ATOM | 65 | CA | GLY | A | 47 | -1.008 | 0.354 | 23.172 | 1.00 | 58.86 | A | C |
| ATOM | 66 | C | GLY | A | 47 | -1.054 | 1.422 | 24.238 | 1.00 | 58.86 | A | C |
| ATOM | 67 | O | GLY | A | 47 | -1.374 | 2.573 | 23.945 | 1.00 | 58.86 | A | O |
| ATOM | 68 | N | PRO | A | 48 | -0.721 | 1.072 | 25.494 | 1.00 | 56.57 | A | N |
| ATOM | 69 | CD | PRO | A | 48 | 0.007 | -0.134 | 25.922 | 1.00 | 57.85 | A | C |
| ATOM | 70 | CA | PRO | A | 48 | -0.747 | 2.055 | 26.580 | 1.00 | 56.57 | A | C |
| ATOM | 71 | CB | PRO | A | 48 | -0.753 | 1.186 | 27.843 | 1.00 | 57.85 | A | C |
| ATOM | 72 | CG | PRO | A | 48 | -0.488 | -0.287 | 27.335 | 1.00 | 57.85 | A | C |
| ATOM | 73 | C | PRO | A | 48 | 0.518 | 2.895 | 26.457 | 1.00 | 56.57 | A | C |
| ATOM | 74 | O | PRO | A | 48 | 1.627 | 2.354 | 26.425 | 1.00 | 56.57 | A | O |
| ATOM | 75 | N | ASP | A | 49 | 0.340 | 4.209 | 26.356 | 1.00 | 51.99 | A | N |
| ATOM | 76 | CA | ASP | A | 49 | 1.454 | 5.141 | 26.210 | 1.00 | 51.99 | A | C |
| ATOM | 77 | CB | ASP | A | 49 | 0.917 | 6.575 | 26.071 | 1.00 | 70.33 | A | C |
| ATOM | 78 | CG | ASP | A | 49 | 2.004 | 7.573 | 25.689 | 1.00 | 70.33 | A | C |
| ATOM | 79 | OD1 | ASP | A | 49 | 3.160 | 7.357 | 26.120 | 1.00 | 70.33 | A | O |
| ATOM | 80 | OD2 | ASP | A | 49 | 1.713 | 8.569 | 24.975 | 1.00 | 70.33 | A | O |
| ATOM | 81 | C | ASP | A | 49 | 2.364 | 5.041 | 27.436 | 1.00 | 51.99 | A | C |
| ATOM | 82 | O | ASP | A | 49 | 2.348 | 5.922 | 28.298 | 1.00 | 51.99 | A | O |
| ATOM | 83 | N | ARG | A | 50 | 3.164 | 3.978 | 27.504 | 1.00 | 49.79 | A | N |
| ATOM | 84 | CA | ARG | A | 50 | 4.044 | 3.766 | 28.647 | 1.00 | 49.79 | A | C |
| ATOM | 85 | CB | ARG | A | 50 | 3.235 | 3.104 | 29.758 | 1.00 | 99.34 | A | C |
| ATOM | 86 | CG | ARG | A | 50 | 3.745 | 3.441 | 31.139 | 1.00 | 99.34 | A | C |
| ATOM | 87 | CD | ARG | A | 50 | 2.806 | 2.942 | 32.215 | 1.00 | 99.34 | A | C |
| ATOM | 88 | NE | ARG | A | 50 | 2.360 | 1.545 | 32.047 | 1.00 | 99.34 | A | N |
| ATOM | 89 | CZ | ARG | A | 50 | 3.083 | 0.535 | 31.546 | 1.00 | 99.34 | A | C |
| ATOM | 90 | NH1 | ARG | A | 50 | 4.330 | 0.733 | 31.121 | 1.00 | 99.34 | A | N |
| ATOM | 91 | NH2 | ARG | A | 50 | 2.562 | -0.695 | 31.501 | 1.00 | 99.34 | A | N |
| ATOM | 92 | C | ARG | A | 50 | 5.282 | 2.927 | 28.292 | 1.00 | 49.79 | A | C |
| ATOM | 93 | O | ARG | A | 50 | 5.240 | 1.695 | 28.308 | 1.00 | 49.79 | A | O |
| ATOM | 94 | N | PRO | A | 51 | 6.412 | 3.603 | 28.013 | 1.00 | 40.28 | A | N |
| ATOM | 95 | CD | PRO | A | 51 | 6.505 | 5.037 | 28.334 | 1.00 | 39.13 | A | C |
| ATOM | 96 | CA | PRO | A | 51 | 7.732 | 3.097 | 27.627 | 1.00 | 40.28 | A | C |
| ATOM | 97 | CB | PRO | A | 51 | 8.563 | 4.376 | 27.518 | 1.00 | 39.13 | A | C |
| ATOM | 98 | CG | PRO | A | 51 | 7.985 | 5.228 | 28.552 | 1.00 | 39.13 | A | C |
| ATOM | 99 | C | PRO | A | 51 | 8.448 | 2.011 | 28.427 | 1.00 | 40.28 | A | C |
| ATOM | 100 | O | PRO | A | 51 | 8.333 | 1.909 | 29.643 | 1.00 | 40.28 | A | O |
| ATOM | 101 | N | GLN | A | 52 | 9.207 | 1.208 | 27.695 | 1.00 | 50.11 | A | N |
| ATOM | 102 | CA | GLN | A | 52 | 9.997 | 0.116 | 28.238 | 1.00 | 50.11 | A | C |
| ATOM | 103 | CB | GLN | A | 52 | 9.237 | -1.195 | 28.137 | 1.00 | 66.13 | A | C |
| ATOM | 104 | CG | GLN | A | 52 | 8.518 | -1.380 | 26.827 | 1.00 | 66.13 | A | C |
| ATOM | 105 | CD | GLN | A | 52 | 7.529 | -2.527 | 26.882 | 1.00 | 66.13 | A | C |
| ATOM | 106 | OE1 | GLN | A | 52 | 7.846 | -3.654 | 26.482 | 1.00 | 66.13 | A | O |
| ATOM | 107 | NE2 | GLN | A | 52 | 6.322 | -2.252 | 27.400 | 1.00 | 66.13 | A | N |
| ATOM | 108 | C | GLN | A | 52 | 11.298 | 0.008 | 27.467 | 1.00 | 50.11 | A | C |
| ATOM | 109 | O | GLN | A | 52 | 11.438 | 0.561 | 26.381 | 1.00 | 50.11 | A | O |
| ATOM | 110 | N | GLU | A | 53 | 12.258 | -0.706 | 28.036 | 1.00 | 56.03 | A | N |
| ATOM | 111 | CA | GLU | A | 53 | 13.557 | -0.849 | 27.392 | 1.00 | 56.03 | A | C |
| ATOM | 112 | CB | GLU | A | 53 | 14.611 | -1.306 | 28.400 | 1.00 | 60.29 | A | C |
| ATOM | 113 | CG | GLU | A | 53 | 15.066 | -0.214 | 29.335 | 1.00 | 60.29 | A | C |
| ATOM | 114 | CD | GLU | A | 53 | 15.896 | -0.757 | 30.479 | 1.00 | 60.29 | A | C |
| ATOM | 115 | OE1 | GLU | A | 53 | 16.797 | -1.594 | 30.214 | 1.00 | 60.29 | A | O |
| ATOM | 116 | OE2 | GLU | A | 53 | 15.652 | -0.340 | 31.637 | 1.00 | 60.29 | A | O |
| ATOM | 117 | C | GLU | A | 53 | 13.518 | -1.799 | 26.221 | 1.00 | 56.03 | A | C |
| ATOM | 118 | O | GLU | A | 53 | 12.870 | -2.850 | 26.272 | 1.00 | 56.03 | A | O |
| ATOM | 119 | N | VAL | A | 54 | 14.223 | -1.404 | 25.165 | 1.00 | 47.60 | A | N |
| ATOM | 120 | CA | VAL | A | 54 | 14.299 | -2.173 | 23.934 | 1.00 | 47.60 | A | C |
| ATOM | 121 | CB | VAL | A | 54 | 13.402 | -1.551 | 22.838 | 1.00 | 45.63 | A | C |
| ATOM | 122 | CG1 | VAL | A | 54 | 13.542 | -2.341 | 21.545 | 1.00 | 45.63 | A | C |
| ATOM | 123 | CG2 | VAL | A | 54 | 11.951 | -1.515 | 23.300 | 1.00 | 45.63 | A | C |
| ATOM | 124 | C | VAL | A | 54 | 15.730 | -2.167 | 23.429 | 1.00 | 47.60 | A | C |
| ATOM | 125 | O | VAL | A | 54 | 16.339 | -1.105 | 23.291 | 1.00 | 47.60 | A | O |
| ATOM | 126 | N | SER | A | 55 | 16.270 | -3.351 | 23.170 | 1.00 | 48.87 | A | N |
| ATOM | 127 | CA | SER | A | 55 | 17.628 | -3.463 | 22.644 | 1.00 | 48.87 | A | C |

FIG. 3-3

| ATOM | 128 | CB  | SER | A | 55 | 18.508 | -4.291 | 23.586 | 1.00 | 49.03 | A | C |
| ---- | --- | --- | --- | - | -- | ------ | ------ | ------ | ---- | ----- | - | - |
| ATOM | 129 | OG  | SER | A | 55 | 18.790 | -3.566 | 24.773 | 1.00 | 49.03 | A | O |
| ATOM | 130 | C   | SER | A | 55 | 17.634 | -4.073 | 21.231 | 1.00 | 48.87 | A | C |
| ATOM | 131 | O   | SER | A | 55 | 16.894 | -5.020 | 20.924 | 1.00 | 48.87 | A | O |
| ATOM | 132 | N   | TYR | A | 56 | 18.457 | -3.503 | 20.364 | 1.00 | 45.37 | A | N |
| ATOM | 133 | CA  | TYR | A | 56 | 18.555 | -3.983 | 19.002 | 1.00 | 45.37 | A | C |
| ATOM | 134 | CB  | TYR | A | 56 | 17.635 | -3.181 | 18.070 | 1.00 | 30.24 | A | C |
| ATOM | 135 | CG  | TYR | A | 56 | 17.914 | -1.689 | 18.014 | 1.00 | 30.24 | A | C |
| ATOM | 136 | CD1 | TYR | A | 56 | 19.054 | -1.188 | 17.387 | 1.00 | 30.24 | A | C |
| ATOM | 137 | CE1 | TYR | A | 56 | 19.290 |  0.182 | 17.317 | 1.00 | 30.24 | A | C |
| ATOM | 138 | CD2 | TYR | A | 56 | 17.018 | -0.778 | 18.572 | 1.00 | 30.24 | A | C |
| ATOM | 139 | CE2 | TYR | A | 56 | 17.241 |  0.584 | 18.507 | 1.00 | 30.24 | A | C |
| ATOM | 140 | CZ  | TYR | A | 56 | 18.374 |  1.060 | 17.879 | 1.00 | 30.24 | A | C |
| ATOM | 141 | OH  | TYR | A | 56 | 18.574 |  2.420 | 17.804 | 1.00 | 30.24 | A | O |
| ATOM | 142 | C   | TYR | A | 56 | 19.993 | -3.857 | 18.552 | 1.00 | 45.37 | A | C |
| ATOM | 143 | O   | TYR | A | 56 | 20.772 | -3.087 | 19.122 | 1.00 | 45.37 | A | O |
| ATOM | 144 | N   | THR | A | 57 | 20.342 | -4.614 | 17.520 | 1.00 | 71.48 | A | N |
| ATOM | 145 | CA  | THR | A | 57 | 21.697 | -4.580 | 17.013 | 1.00 | 71.48 | A | C |
| ATOM | 146 | CB  | THR | A | 57 | 22.544 | -5.636 | 17.736 | 1.00 | 59.52 | A | C |
| ATOM | 147 | OG1 | THR | A | 57 | 23.926 | -5.468 | 17.386 | 1.00 | 59.52 | A | O |
| ATOM | 148 | CG2 | THR | A | 57 | 22.058 | -7.039 | 17.362 | 1.00 | 59.52 | A | C |
| ATOM | 149 | C   | THR | A | 57 | 21.738 | -4.827 | 15.500 | 1.00 | 71.48 | A | C |
| ATOM | 150 | O   | THR | A | 57 | 20.697 | -4.864 | 14.833 | 1.00 | 71.48 | A | O |
| ATOM | 151 | N   | ASP | A | 58 | 22.948 | -4.991 | 14.971 | 1.00 | 59.74 | A | N |
| ATOM | 152 | CA  | ASP | A | 58 | 23.143 | -5.240 | 13.552 | 1.00 | 59.74 | A | C |
| ATOM | 153 | CB  | ASP | A | 58 | 22.515 | -6.579 | 13.119 | 1.00 | 64.42 | A | C |
| ATOM | 154 | CG  | ASP | A | 58 | 23.052 | -7.771 | 13.899 | 1.00 | 64.42 | A | C |
| ATOM | 155 | OD1 | ASP | A | 58 | 24.100 | -7.624 | 14.563 | 1.00 | 64.42 | A | O |
| ATOM | 156 | OD2 | ASP | A | 58 | 22.433 | -8.862 | 13.839 | 1.00 | 64.42 | A | O |
| ATOM | 157 | C   | ASP | A | 58 | 22.466 | -4.136 | 12.785 | 1.00 | 59.74 | A | C |
| ATOM | 158 | O   | ASP | A | 58 | 21.906 | -4.386 | 11.723 | 1.00 | 59.74 | A | O |
| ATOM | 159 | N   | THR | A | 59 | 22.504 | -2.915 | 13.304 | 1.00 | 39.80 | A | N |
| ATOM | 160 | CA  | THR | A | 59 | 21.839 | -1.829 | 12.591 | 1.00 | 39.80 | A | C |
| ATOM | 161 | CB  | THR | A | 59 | 21.575 | -0.616 | 13.518 | 1.00 | 45.95 | A | C |
| ATOM | 162 | OG1 | THR | A | 59 | 22.740 |  0.209 | 13.581 | 1.00 | 45.95 | A | O |
| ATOM | 163 | CG2 | THR | A | 59 | 21.230 | -1.081 | 14.916 | 1.00 | 45.95 | A | C |
| ATOM | 164 | C   | THR | A | 59 | 22.602 | -1.349 | 11.353 | 1.00 | 39.80 | A | C |
| ATOM | 165 | O   | THR | A | 59 | 23.801 | -1.080 | 11.414 | 1.00 | 39.80 | A | O |
| ATOM | 166 | N   | LYS | A | 60 | 21.899 | -1.256 | 10.225 | 1.00 | 81.88 | A | N |
| ATOM | 167 | CA  | LYS | A | 60 | 22.506 | -0.785 |  8.974 | 1.00 | 81.88 | A | C |
| ATOM | 168 | CB  | LYS | A | 60 | 22.985 | -1.961 |  8.111 | 1.00 | 55.16 | A | C |
| ATOM | 169 | CG  | LYS | A | 60 | 21.894 | -2.902 |  7.652 | 1.00 | 55.16 | A | C |
| ATOM | 170 | CD  | LYS | A | 60 | 22.423 | -3.810 |  6.549 | 1.00 | 55.16 | A | C |
| ATOM | 171 | CE  | LYS | A | 60 | 21.421 | -4.914 |  6.195 | 1.00 | 55.16 | A | C |
| ATOM | 172 | NZ  | LYS | A | 60 | 21.979 | -5.917 |  5.236 | 1.00 | 55.16 | A | N |
| ATOM | 173 | C   | LYS | A | 60 | 21.533 |  0.079 |  8.165 | 1.00 | 81.88 | A | C |
| ATOM | 174 | O   | LYS | A | 60 | 20.327 | -0.179 |  8.154 | 1.00 | 81.88 | A | O |
| ATOM | 175 | N   | VAL | A | 61 | 22.068 |  1.098 |  7.490 | 1.00 | 55.81 | A | N |
| ATOM | 176 | CA  | VAL | A | 61 | 21.264 |  2.025 |  6.696 | 1.00 | 55.81 | A | C |
| ATOM | 177 | CB  | VAL | A | 61 | 22.100 |  3.236 |  6.233 | 1.00 | 31.54 | A | C |
| ATOM | 178 | CG1 | VAL | A | 61 | 21.248 |  4.141 |  5.364 | 1.00 | 31.54 | A | C |
| ATOM | 179 | CG2 | VAL | A | 61 | 22.612 |  4.008 |  7.434 | 1.00 | 31.54 | A | C |
| ATOM | 180 | C   | VAL | A | 61 | 20.642 |  1.372 |  5.468 | 1.00 | 55.81 | A | C |
| ATOM | 181 | O   | VAL | A | 61 | 21.311 |  0.628 |  4.750 | 1.00 | 55.81 | A | O |
| ATOM | 182 | N   | ILE | A | 62 | 19.363 |  1.662 |  5.222 | 1.00 | 48.02 | A | N |
| ATOM | 183 | CA  | ILE | A | 62 | 18.665 |  1.083 |  4.076 | 1.00 | 48.02 | A | C |
| ATOM | 184 | CB  | ILE | A | 62 | 17.844 | -0.163 |  4.491 | 1.00 | 41.15 | A | C |
| ATOM | 185 | CG2 | ILE | A | 62 | 18.723 | -1.117 |  5.307 | 1.00 | 41.15 | A | C |
| ATOM | 186 | CG1 | ILE | A | 62 | 16.617 |  0.250 |  5.309 | 1.00 | 41.15 | A | C |
| ATOM | 187 | CD1 | ILE | A | 62 | 15.624 | -0.893 |  5.513 | 1.00 | 41.15 | A | C |
| ATOM | 188 | C   | ILE | A | 62 | 17.729 |  2.037 |  3.345 | 1.00 | 48.02 | A | C |
| ATOM | 189 | O   | ILE | A | 62 | 16.959 |  1.607 |  2.479 | 1.00 | 48.02 | A | O |
| ATOM | 190 | N   | GLY | A | 63 | 17.787 |  3.323 |  3.686 | 1.00 | 46.28 | A | N |
| ATOM | 191 | CA  | GLY | A | 63 | 16.912 |  4.274 |  3.022 | 1.00 | 46.28 | A | C |
| ATOM | 192 | C   | GLY | A | 63 | 17.119 |  5.724 |  3.395 | 1.00 | 46.28 | A | C |
| ATOM | 193 | O   | GLY | A | 63 | 17.358 |  6.025 |  4.553 | 1.00 | 46.28 | A | O |
| ATOM | 194 | N   | ASN | A | 64 | 17.021 |  6.610 |  2.401 | 1.00 | 50.58 | A | N |

FIG. 3-4

| | | | | | | | | | | | |
|---|---|---|---|---|---|---|---|---|---|---|---|
| ATOM | 195 | CA | ASN | A | 64 | 17.170 | 8.055 | 2.574 | 1.00 | 50.58 | A C |
| ATOM | 196 | CB | ASN | A | 64 | 17.945 | 8.660 | 1.408 | 1.00 | 82.07 | A C |
| ATOM | 197 | CG | ASN | A | 64 | 19.432 | 8.430 | 1.515 | 1.00 | 82.07 | A C |
| ATOM | 198 | OD1 | ASN | A | 64 | 20.155 | 9.189 | 2.176 | 1.00 | 82.07 | A O |
| ATOM | 199 | ND2 | ASN | A | 64 | 19.906 | 7.366 | 0.874 | 1.00 | 82.07 | A N |
| ATOM | 200 | C | ASN | A | 64 | 15.788 | 8.678 | 2.586 | 1.00 | 50.58 | A C |
| ATOM | 201 | O | ASN | A | 64 | 14.821 | 8.046 | 2.987 | 1.00 | 50.58 | A O |
| ATOM | 202 | N | GLY | A | 65 | 15.692 | 9.917 | 2.120 | 1.00 | 50.05 | A N |
| ATOM | 203 | CA | GLY | A | 65 | 14.409 | 10.587 | 2.088 | 1.00 | 50.05 | A C |
| ATOM | 204 | C | GLY | A | 65 | 14.553 | 11.968 | 2.675 | 1.00 | 50.05 | A C |
| ATOM | 205 | O | GLY | A | 65 | 15.526 | 12.239 | 3.380 | 1.00 | 50.05 | A O |
| ATOM | 206 | N | SER | A | 66 | 13.592 | 12.841 | 2.379 | 1.00 | 63.41 | A N |
| ATOM | 207 | CA | SER | A | 66 | 13.610 | 14.212 | 2.887 | 1.00 | 63.41 | A C |
| ATOM | 208 | CB | SER | A | 66 | 12.590 | 15.066 | 2.137 | 1.00 | 68.29 | A C |
| ATOM | 209 | OG | SER | A | 66 | 11.293 | 14.504 | 2.262 | 1.00 | 68.29 | A O |
| ATOM | 210 | C | SER | A | 66 | 13.278 | 14.221 | 4.378 | 1.00 | 63.41 | A C |
| ATOM | 211 | O | SER | A | 66 | 13.473 | 15.232 | 5.067 | 1.00 | 63.41 | A O |
| ATOM | 212 | N | PHE | A | 67 | 12.781 | 13.082 | 4.857 | 1.00 | 54.08 | A N |
| ATOM | 213 | CA | PHE | A | 67 | 12.402 | 12.911 | 6.251 | 1.00 | 54.08 | A C |
| ATOM | 214 | CB | PHE | A | 67 | 11.374 | 11.796 | 6.357 | 1.00 | 59.07 | A C |
| ATOM | 215 | CG | PHE | A | 67 | 11.863 | 10.475 | 5.834 | 1.00 | 59.07 | A C |
| ATOM | 216 | CD1 | PHE | A | 67 | 12.750 | 9.697 | 6.580 | 1.00 | 59.07 | A C |
| ATOM | 217 | CD2 | PHE | A | 67 | 11.425 | 10.001 | 4.603 | 1.00 | 59.07 | A C |
| ATOM | 218 | CE1 | PHE | A | 67 | 13.189 | 8.464 | 6.108 | 1.00 | 59.07 | A C |
| ATOM | 219 | CE2 | PHE | A | 67 | 11.859 | 8.767 | 4.121 | 1.00 | 59.07 | A C |
| ATOM | 220 | CZ | PHE | A | 67 | 12.741 | 7.995 | 4.876 | 1.00 | 59.07 | A C |
| ATOM | 221 | C | PHE | A | 67 | 13.601 | 12.563 | 7.116 | 1.00 | 54.08 | A C |
| ATOM | 222 | O | PHE | A | 67 | 13.657 | 12.935 | 8.289 | 1.00 | 54.08 | A O |
| ATOM | 223 | N | GLY | A | 68 | 14.551 | 11.835 | 6.536 | 1.00 | 43.94 | A N |
| ATOM | 224 | CA | GLY | A | 68 | 15.734 | 11.449 | 7.277 | 1.00 | 43.94 | A C |
| ATOM | 225 | C | GLY | A | 68 | 16.303 | 10.170 | 6.720 | 1.00 | 43.94 | A C |
| ATOM | 226 | O | GLY | A | 68 | 16.368 | 10.011 | 5.510 | 1.00 | 43.94 | A O |
| ATOM | 227 | N | VAL | A | 69 | 16.699 | 9.259 | 7.606 | 1.00 | 44.41 | A N |
| ATOM | 228 | CA | VAL | A | 69 | 17.274 | 7.979 | 7.221 | 1.00 | 44.41 | A C |
| ATOM | 229 | CB | VAL | A | 69 | 18.686 | 7.822 | 7.795 | 1.00 | 28.34 | A C |
| ATOM | 230 | CG1 | VAL | A | 69 | 19.317 | 6.538 | 7.305 | 1.00 | 28.34 | A C |
| ATOM | 231 | CG2 | VAL | A | 69 | 19.527 | 9.008 | 7.405 | 1.00 | 28.34 | A C |
| ATOM | 232 | C | VAL | A | 69 | 16.428 | 6.836 | 7.751 | 1.00 | 44.41 | A C |
| ATOM | 233 | O | VAL | A | 69 | 15.555 | 7.040 | 8.589 | 1.00 | 44.41 | A O |
| ATOM | 234 | N | VAL | A | 70 | 16.692 | 5.633 | 7.257 | 1.00 | 47.70 | A N |
| ATOM | 235 | CA | VAL | A | 70 | 15.979 | 4.451 | 7.699 | 1.00 | 47.70 | A C |
| ATOM | 236 | CB | VAL | A | 70 | 14.928 | 3.994 | 6.684 | 1.00 | 47.40 | A C |
| ATOM | 237 | CG1 | VAL | A | 70 | 14.027 | 2.935 | 7.311 | 1.00 | 47.40 | A C |
| ATOM | 238 | CG2 | VAL | A | 70 | 14.121 | 5.164 | 6.216 | 1.00 | 47.40 | A C |
| ATOM | 239 | C | VAL | A | 70 | 16.992 | 3.326 | 7.840 | 1.00 | 47.70 | A C |
| ATOM | 240 | O | VAL | A | 70 | 17.624 | 2.920 | 6.864 | 1.00 | 47.70 | A O |
| ATOM | 241 | N | TYR | A | 71 | 17.151 | 2.821 | 9.055 | 1.00 | 43.93 | A N |
| ATOM | 242 | CA | TYR | A | 71 | 18.078 | 1.734 | 9.279 | 1.00 | 43.93 | A C |
| ATOM | 243 | CB | TYR | A | 71 | 18.864 | 1.937 | 10.581 | 1.00 | 45.54 | A C |
| ATOM | 244 | CG | TYR | A | 71 | 19.453 | 3.311 | 10.790 | 1.00 | 45.54 | A C |
| ATOM | 245 | CD1 | TYR | A | 71 | 18.640 | 4.400 | 11.095 | 1.00 | 45.54 | A C |
| ATOM | 246 | CE1 | TYR | A | 71 | 19.183 | 5.666 | 11.314 | 1.00 | 45.54 | A C |
| ATOM | 247 | CD2 | TYR | A | 71 | 20.828 | 3.521 | 10.706 | 1.00 | 45.54 | A C |
| ATOM | 248 | CE2 | TYR | A | 71 | 21.383 | 4.784 | 10.920 | 1.00 | 45.54 | A C |
| ATOM | 249 | CZ | TYR | A | 71 | 20.554 | 5.850 | 11.225 | 1.00 | 45.54 | A C |
| ATOM | 250 | OH | TYR | A | 71 | 21.094 | 7.099 | 11.444 | 1.00 | 45.54 | A O |
| ATOM | 251 | C | TYR | A | 71 | 17.275 | 0.450 | 9.412 | 1.00 | 43.93 | A C |
| ATOM | 252 | O | TYR | A | 71 | 16.038 | 0.465 | 9.458 | 1.00 | 43.93 | A O |
| ATOM | 253 | N | GLN | A | 72 | 17.991 | -0.668 | 9.457 | 1.00 | 42.24 | A N |
| ATOM | 254 | CA | GLN | A | 72 | 17.369 | -1.961 | 9.667 | 1.00 | 42.24 | A C |
| ATOM | 255 | CB | GLN | A | 72 | 17.721 | -2.944 | 8.572 | 1.00 | 58.43 | A C |
| ATOM | 256 | CG | GLN | A | 72 | 17.162 | -4.302 | 8.862 | 1.00 | 58.43 | A C |
| ATOM | 257 | CD | GLN | A | 72 | 17.820 | -5.379 | 8.052 | 1.00 | 58.43 | A C |
| ATOM | 258 | OE1 | GLN | A | 72 | 19.021 | -5.658 | 8.213 | 1.00 | 58.43 | A O |
| ATOM | 259 | NE2 | GLN | A | 72 | 17.043 | -6.000 | 7.168 | 1.00 | 58.43 | A N |
| ATOM | 260 | C | GLN | A | 72 | 18.043 | -2.402 | 10.949 | 1.00 | 42.24 | A C |
| ATOM | 261 | O | GLN | A | 72 | 19.130 | -1.908 | 11.273 | 1.00 | 42.24 | A O |

FIG. 3-5

```
ATOM    262  N    ALA A  73      17.420  -3.312  11.686  1.00 36.61      A  N
ATOM    263  CA   ALA A  73      18.020  -3.769  12.928  1.00 36.61      A  C
ATOM    264  CB   ALA A  73      17.929  -2.683  13.992  1.00 30.91      A  C
ATOM    265  C    ALA A  73      17.376  -5.043  13.425  1.00 36.61      A  C
ATOM    266  O    ALA A  73      16.339  -5.486  12.920  1.00 36.61      A  O
ATOM    267  N    LYS A  74      18.002  -5.624  14.438  1.00 50.49      A  N
ATOM    268  CA   LYS A  74      17.537  -6.873  15.007  1.00 50.49      A  C
ATOM    269  CB   LYS A  74      18.591  -7.947  14.736  1.00 55.00      A  C
ATOM    270  CG   LYS A  74      18.233  -9.346  15.173  1.00 55.00      A  C
ATOM    271  CD   LYS A  74      19.425 -10.252  14.909  1.00 55.00      A  C
ATOM    272  CE   LYS A  74      19.309 -11.600  15.600  1.00 55.00      A  C
ATOM    273  NZ   LYS A  74      20.526 -12.425  15.289  1.00 55.00      A  N
ATOM    274  C    LYS A  74      17.283  -6.721  16.504  1.00 50.49      A  C
ATOM    275  O    LYS A  74      18.165  -6.307  17.257  1.00 50.49      A  O
ATOM    276  N    LEU A  75      16.060  -7.044  16.919  1.00 49.83      A  N
ATOM    277  CA   LEU A  75      15.674  -6.960  18.316  1.00 49.83      A  C
ATOM    278  CB   LEU A  75      14.156  -7.114  18.456  1.00 22.75      A  C
ATOM    279  CG   LEU A  75      13.229  -6.103  17.771  1.00 22.75      A  C
ATOM    280  CD1  LEU A  75      11.832  -6.260  18.312  1.00 22.75      A  C
ATOM    281  CD2  LEU A  75      13.687  -4.701  18.035  1.00 22.75      A  C
ATOM    282  C    LEU A  75      16.389  -8.068  19.088  1.00 49.83      A  C
ATOM    283  O    LEU A  75      16.350  -9.242  18.694  1.00 49.83      A  O
ATOM    284  N    CYS A  76      17.035  -7.699  20.195  1.00 57.70      A  N
ATOM    285  CA   CYS A  76      17.765  -8.672  20.996  1.00 57.70      A  C
ATOM    286  CB   CYS A  76      18.679  -7.966  21.991  1.00 50.69      A  C
ATOM    287  SG   CYS A  76      20.358  -7.727  21.361  1.00 50.69      A  S
ATOM    288  C    CYS A  76      16.883  -9.658  21.731  1.00 57.70      A  C
ATOM    289  O    CYS A  76      17.391 -10.512  22.437  1.00 57.70      A  O
ATOM    290  N    ASP A  77      15.571  -9.570  21.559  1.00 51.44      A  N
ATOM    291  CA   ASP A  77      14.674 -10.489  22.253  1.00 51.44      A  C
ATOM    292  CB   ASP A  77      13.394  -9.777  22.683  1.00100.00      A  C
ATOM    293  CG   ASP A  77      13.654  -8.403  23.266  1.00100.00      A  C
ATOM    294  OD1  ASP A  77      13.992  -7.459  22.481  1.00100.00      A  O
ATOM    295  OD2  ASP A  77      13.523  -8.281  24.516  1.00100.00      A  O
ATOM    296  C    ASP A  77      14.278 -11.652  21.368  1.00 51.44      A  C
ATOM    297  O    ASP A  77      14.570 -12.817  21.654  1.00 51.44      A  O
ATOM    298  N    SER A  78      13.589 -11.315  20.288  1.00 64.80      A  N
ATOM    299  CA   SER A  78      13.108 -12.308  19.341  1.00 64.80      A  C
ATOM    300  CB   SER A  78      11.684 -11.954  18.921  1.00 73.13      A  C
ATOM    301  OG   SER A  78      11.616 -10.579  18.559  1.00 73.13      A  O
ATOM    302  C    SER A  78      13.995 -12.369  18.110  1.00 64.80      A  C
ATOM    303  O    SER A  78      13.754 -13.169  17.205  1.00 64.80      A  O
ATOM    304  N    GLY A  79      15.023 -11.529  18.072  1.00 48.97      A  N
ATOM    305  CA   GLY A  79      15.885 -11.527  16.907  1.00 48.97      A  C
ATOM    306  C    GLY A  79      15.093 -10.944  15.748  1.00 48.97      A  C
ATOM    307  O    GLY A  79      15.653 -10.620  14.701  1.00 48.97      A  O
ATOM    308  N    GLU A  80      13.783 -10.801  15.948  1.00 48.54      A  N
ATOM    309  CA   GLU A  80      12.891 -10.250  14.931  1.00 48.54      A  C
ATOM    310  CB   GLU A  80      11.541  -9.875  15.547  1.00 66.68      A  C
ATOM    311  CG   GLU A  80      10.555 -11.023  15.670  1.00 66.68      A  C
ATOM    312  CD   GLU A  80       9.247 -10.596  16.336  1.00 66.68      A  C
ATOM    313  OE1  GLU A  80       9.205 -10.533  17.593  1.00 66.68      A  O
ATOM    314  OE2  GLU A  80       8.264 -10.307  15.600  1.00 66.68      A  O
ATOM    315  C    GLU A  80      13.492  -9.024  14.268  1.00 48.54      A  C
ATOM    316  O    GLU A  80      14.014  -8.133  14.939  1.00 48.54      A  O
ATOM    317  N    LEU A  81      13.413  -8.980  12.946  1.00 39.32      A  N
ATOM    318  CA   LEU A  81      13.960  -7.860  12.213  1.00 39.32      A  C
ATOM    319  CB   LEU A  81      14.284  -8.284  10.782  1.00 68.38      A  C
ATOM    320  CG   LEU A  81      15.458  -9.254  10.643  1.00 68.38      A  C
ATOM    321  CD1  LEU A  81      15.701  -9.562   9.181  1.00 68.38      A  C
ATOM    322  CD2  LEU A  81      16.707  -8.628  11.266  1.00 68.38      A  C
ATOM    323  C    LEU A  81      13.002  -6.676  12.208  1.00 39.32      A  C
ATOM    324  O    LEU A  81      11.778  -6.844  12.276  1.00 39.32      A  O
ATOM    325  N    VAL A  82      13.570  -5.475  12.126  1.00 46.15      A  N
ATOM    326  CA   VAL A  82      12.779  -4.251  12.121  1.00 46.15      A  C
ATOM    327  CB   VAL A  82      12.606  -3.665  13.563  1.00 37.97      A  C
ATOM    328  CG1  VAL A  82      11.904  -4.659  14.450  1.00 37.97      A  C
```

FIG. 3-6

| | | | | | | | | | | |
|---|---|---|---|---|---|---|---|---|---|---|
| ATOM | 329 | CG2 | VAL A | 82 | 13.962 | -3.289 | 14.151 | 1.00 37.97 | A | C |
| ATOM | 330 | C | VAL A | 82 | 13.421 | -3.163 | 11.273 | 1.00 46.15 | A | C |
| ATOM | 331 | O | VAL A | 82 | 14.566 | -3.279 | 10.839 | 1.00 46.15 | A | O |
| ATOM | 332 | N | ALA A | 83 | 12.668 | -2.095 | 11.052 | 1.00 59.23 | A | N |
| ATOM | 333 | CA | ALA A | 83 | 13.163 | -0.953 | 10.297 | 1.00 59.23 | A | C |
| ATOM | 334 | CB | ALA A | 83 | 12.385 | -0.797 | 8.987 | 1.00 60.41 | A | C |
| ATOM | 335 | C | ALA A | 83 | 12.938 | 0.261 | 11.196 | 1.00 59.23 | A | C |
| ATOM | 336 | O | ALA A | 83 | 11.849 | 0.437 | 11.754 | 1.00 59.23 | A | O |
| ATOM | 337 | N | ILE A | 84 | 13.962 | 1.086 | 11.359 | 1.00 37.09 | A | N |
| ATOM | 338 | CA | ILE A | 84 | 13.806 | 2.259 | 12.192 | 1.00 37.09 | A | C |
| ATOM | 339 | CB | ILE A | 84 | 14.890 | 2.293 | 13.301 | 1.00 26.02 | A | C |
| ATOM | 340 | CG2 | ILE A | 84 | 14.624 | 3.440 | 14.262 | 1.00 26.02 | A | C |
| ATOM | 341 | CG1 | ILE A | 84 | 14.861 | 0.970 | 14.074 | 1.00 26.02 | A | C |
| ATOM | 342 | CD1 | ILE A | 84 | 15.907 | 0.844 | 15.146 | 1.00 26.02 | A | C |
| ATOM | 343 | C | ILE A | 84 | 13.850 | 3.520 | 11.334 | 1.00 37.09 | A | C |
| ATOM | 344 | O | ILE A | 84 | 14.874 | 3.862 | 10.746 | 1.00 37.09 | A | O |
| ATOM | 345 | N | LYS A | 85 | 12.715 | 4.198 | 11.246 | 1.00 43.25 | A | N |
| ATOM | 346 | CA | LYS A | 85 | 12.631 | 5.414 | 10.460 | 1.00 43.25 | A | C |
| ATOM | 347 | CB | LYS A | 85 | 11.213 | 5.569 | 9.901 | 1.00 41.87 | A | C |
| ATOM | 348 | CG | LYS A | 85 | 11.057 | 6.643 | 8.840 | 1.00 41.87 | A | C |
| ATOM | 349 | CD | LYS A | 85 | 9.611 | 6.742 | 8.355 | 1.00 41.87 | A | C |
| ATOM | 350 | CE | LYS A | 85 | 9.402 | 8.005 | 7.516 | 1.00 41.87 | A | C |
| ATOM | 351 | NZ | LYS A | 85 | 8.047 | 8.085 | 6.913 | 1.00 41.87 | A | N |
| ATOM | 352 | C | LYS A | 85 | 13.006 | 6.599 | 11.347 | 1.00 43.25 | A | C |
| ATOM | 353 | O | LYS A | 85 | 12.244 | 6.998 | 12.229 | 1.00 43.25 | A | O |
| ATOM | 354 | N | LYS A | 86 | 14.197 | 7.144 | 11.127 | 1.00 48.44 | A | N |
| ATOM | 355 | CA | LYS A | 86 | 14.664 | 8.276 | 11.917 | 1.00 48.44 | A | C |
| ATOM | 356 | CB | LYS A | 86 | 16.198 | 8.257 | 12.040 | 1.00 58.22 | A | C |
| ATOM | 357 | CG | LYS A | 86 | 16.708 | 9.041 | 13.245 | 1.00 58.22 | A | C |
| ATOM | 358 | CD | LYS A | 86 | 18.102 | 9.640 | 13.041 | 1.00 58.22 | A | C |
| ATOM | 359 | CE | LYS A | 86 | 19.236 | 8.633 | 13.220 | 1.00 58.22 | A | C |
| ATOM | 360 | NZ | LYS A | 86 | 19.352 | 8.108 | 14.621 | 1.00 58.22 | A | N |
| ATOM | 361 | C | LYS A | 86 | 14.210 | 9.555 | 11.230 | 1.00 48.44 | A | C |
| ATOM | 362 | O | LYS A | 86 | 14.478 | 9.757 | 10.053 | 1.00 48.44 | A | O |
| ATOM | 363 | N | VAL A | 87 | 13.526 | 10.419 | 11.968 | 1.00 38.31 | A | N |
| ATOM | 364 | CA | VAL A | 87 | 13.018 | 11.663 | 11.411 | 1.00 38.31 | A | C |
| ATOM | 365 | CB | VAL A | 87 | 11.486 | 11.611 | 11.244 | 1.00 39.20 | A | C |
| ATOM | 366 | CG1 | VAL A | 87 | 10.965 | 12.976 | 10.871 | 1.00 39.20 | A | C |
| ATOM | 367 | CG2 | VAL A | 87 | 11.105 | 10.587 | 10.188 | 1.00 39.20 | A | C |
| ATOM | 368 | C | VAL A | 87 | 13.323 | 12.853 | 12.291 | 1.00 38.31 | A | C |
| ATOM | 369 | O | VAL A | 87 | 13.133 | 12.790 | 13.506 | 1.00 38.31 | A | O |
| ATOM | 370 | N | LEU A | 88 | 13.783 | 13.943 | 11.682 | 1.00 51.97 | A | N |
| ATOM | 371 | CA | LEU A | 88 | 14.064 | 15.167 | 12.433 | 1.00 51.97 | A | C |
| ATOM | 372 | CB | LEU A | 88 | 14.820 | 16.176 | 11.556 | 1.00 62.22 | A | C |
| ATOM | 373 | CG | LEU A | 88 | 15.413 | 17.502 | 12.089 | 1.00 62.22 | A | C |
| ATOM | 374 | CD1 | LEU A | 88 | 14.348 | 18.335 | 12.799 | 1.00 62.22 | A | C |
| ATOM | 375 | CD2 | LEU A | 88 | 16.584 | 17.192 | 13.027 | 1.00 62.22 | A | C |
| ATOM | 376 | C | LEU A | 88 | 12.684 | 15.726 | 12.786 | 1.00 51.97 | A | C |
| ATOM | 377 | O | LEU A | 88 | 11.963 | 16.197 | 11.905 | 1.00 51.97 | A | O |
| ATOM | 378 | N | GLN A | 89 | 12.297 | 15.644 | 14.057 | 1.00 59.91 | A | N |
| ATOM | 379 | CA | GLN A | 89 | 10.998 | 16.163 | 14.460 | 1.00 59.91 | A | C |
| ATOM | 380 | CB | GLN A | 89 | 10.192 | 15.124 | 15.235 | 1.00 59.62 | A | C |
| ATOM | 381 | CG | GLN A | 89 | 8.803 | 15.623 | 15.617 | 1.00 59.62 | A | C |
| ATOM | 382 | CD | GLN A | 89 | 8.006 | 16.156 | 14.418 | 1.00 59.62 | A | C |
| ATOM | 383 | OE1 | GLN A | 89 | 8.500 | 16.168 | 13.280 | 1.00 59.62 | A | O |
| ATOM | 384 | NE2 | GLN A | 89 | 6.765 | 16.599 | 14.673 | 1.00 59.62 | A | N |
| ATOM | 385 | C | GLN A | 89 | 11.145 | 17.427 | 15.293 | 1.00 59.91 | A | C |
| ATOM | 386 | O | GLN A | 89 | 11.997 | 17.517 | 16.181 | 1.00 59.91 | A | O |
| ATOM | 387 | N | ASP A | 90 | 10.289 | 18.397 | 14.996 | 1.00 68.30 | A | N |
| ATOM | 388 | CA | ASP A | 90 | 10.323 | 19.681 | 15.656 | 1.00 68.30 | A | C |
| ATOM | 389 | CB | ASP A | 90 | 9.867 | 20.756 | 14.681 | 1.00 96.51 | A | C |
| ATOM | 390 | CG | ASP A | 90 | 9.698 | 22.112 | 15.334 | 1.00 96.51 | A | C |
| ATOM | 391 | OD1 | ASP A | 90 | 9.552 | 23.092 | 14.559 | 1.00 96.51 | A | O |
| ATOM | 392 | OD2 | ASP A | 90 | 9.699 | 22.202 | 16.593 | 1.00 96.51 | A | O |
| ATOM | 393 | C | ASP A | 90 | 9.530 | 19.787 | 16.930 | 1.00 68.30 | A | C |
| ATOM | 394 | O | ASP A | 90 | 8.321 | 20.057 | 16.911 | 1.00 68.30 | A | O |
| ATOM | 395 | N | ALA A | 91 | 10.255 | 19.637 | 18.036 | 1.00100.00 | A | N |

FIG. 3-7

| | | | | | | | | | | |
|---|---|---|---|---|---|---|---|---|---|---|
| ATOM | 396 | CA | ALA | A | 91 | 9.666 | 19.757 | 19.357 | 1.00 100.00 | A C |
| ATOM | 397 | CB | ALA | A | 91 | 10.752 | 19.663 | 20.455 | 1.00 47.73 | A C |
| ATOM | 398 | C | ALA | A | 91 | 8.970 | 21.123 | 19.394 | 1.00 100.00 | A C |
| ATOM | 399 | O | ALA | A | 91 | 9.600 | 22.188 | 19.375 | 1.00 100.00 | A O |
| ATOM | 400 | N | ALA | A | 92 | 7.651 | 21.040 | 19.377 | 1.00 89.18 | A N |
| ATOM | 401 | CA | ALA | A | 92 | 6.701 | 22.148 | 19.439 | 1.00 89.18 | A C |
| ATOM | 402 | CB | ALA | A | 92 | 7.219 | 23.404 | 18.712 | 1.00 79.74 | A C |
| ATOM | 403 | C | ALA | A | 92 | 5.421 | 21.623 | 18.773 | 1.00 89.18 | A C |
| ATOM | 404 | O | ALA | A | 92 | 4.303 | 21.840 | 19.277 | 1.00 89.18 | A O |
| ATOM | 405 | N | ALA | A | 93 | 5.600 | 20.921 | 17.649 | 1.00 79.38 | A N |
| ATOM | 406 | CA | ALA | A | 93 | 4.487 | 20.338 | 16.903 | 1.00 79.38 | A C |
| ATOM | 407 | CB | ALA | A | 93 | 4.510 | 20.839 | 15.462 | 1.00 39.68 | A C |
| ATOM | 408 | C | ALA | A | 93 | 4.525 | 18.795 | 16.935 | 1.00 79.38 | A C |
| ATOM | 409 | O | ALA | A | 93 | 5.596 | 18.172 | 16.864 | 1.00 79.38 | A O |
| ATOM | 410 | N | ALA | A | 94 | 3.343 | 18.190 | 17.060 | 1.00 63.78 | A N |
| ATOM | 411 | CA | ALA | A | 94 | 3.220 | 16.739 | 17.081 | 1.00 63.78 | A C |
| ATOM | 412 | CB | ALA | A | 94 | 1.816 | 16.337 | 17.546 | 1.00 33.55 | A C |
| ATOM | 413 | C | ALA | A | 94 | 3.480 | 16.229 | 15.660 | 1.00 63.78 | A C |
| ATOM | 414 | O | ALA | A | 94 | 3.178 | 16.918 | 14.670 | 1.00 63.78 | A O |
| ATOM | 415 | N | ASN | A | 95 | 4.049 | 15.028 | 15.568 | 1.00 38.53 | A N |
| ATOM | 416 | CA | ASN | A | 95 | 4.366 | 14.389 | 14.287 | 1.00 38.53 | A C |
| ATOM | 417 | CB | ASN | A | 95 | 5.459 | 13.347 | 14.518 | 1.00 43.12 | A C |
| ATOM | 418 | CG | ASN | A | 95 | 6.004 | 12.777 | 13.238 | 1.00 43.12 | A C |
| ATOM | 419 | OD1 | ASN | A | 95 | 5.428 | 11.859 | 12.664 | 1.00 43.12 | A O |
| ATOM | 420 | ND2 | ASN | A | 95 | 7.122 | 13.324 | 12.774 | 1.00 43.12 | A N |
| ATOM | 421 | C | ASN | A | 95 | 3.121 | 13.744 | 13.657 | 1.00 38.53 | A C |
| ATOM | 422 | O | ASN | A | 95 | 2.494 | 12.860 | 14.242 | 1.00 38.53 | A O |
| ATOM | 423 | N | ARG | A | 96 | 2.771 | 14.189 | 12.455 | 1.00 47.01 | A N |
| ATOM | 424 | CA | ARG | A | 96 | 1.587 | 13.674 | 11.776 | 1.00 47.01 | A C |
| ATOM | 425 | CB | ARG | A | 96 | 1.330 | 14.468 | 10.493 | 1.00 62.26 | A C |
| ATOM | 426 | CG | ARG | A | 96 | -0.052 | 14.237 | 9.903 | 1.00 62.26 | A C |
| ATOM | 427 | CD | ARG | A | 96 | -0.215 | 14.934 | 8.552 | 1.00 62.26 | A C |
| ATOM | 428 | NE | ARG | A | 96 | -0.631 | 16.335 | 8.641 | 1.00 62.26 | A N |
| ATOM | 429 | CZ | ARG | A | 96 | -0.691 | 17.152 | 7.588 | 1.00 62.26 | A C |
| ATOM | 430 | NH1 | ARG | A | 96 | -0.358 | 16.712 | 6.375 | 1.00 62.26 | A N |
| ATOM | 431 | NH2 | ARG | A | 96 | -1.085 | 18.406 | 7.731 | 1.00 62.26 | A N |
| ATOM | 432 | C | ARG | A | 96 | 1.644 | 12.176 | 11.466 | 1.00 47.01 | A C |
| ATOM | 433 | O | ARG | A | 96 | 0.660 | 11.468 | 11.665 | 1.00 47.01 | A O |
| ATOM | 434 | N | GLU | A | 97 | 2.787 | 11.687 | 10.992 | 1.00 40.91 | A N |
| ATOM | 435 | CA | GLU | A | 97 | 2.917 | 10.268 | 10.676 | 1.00 40.91 | A C |
| ATOM | 436 | CB | GLU | A | 97 | 4.296 | 9.972 | 10.085 | 1.00 30.74 | A C |
| ATOM | 437 | CG | GLU | A | 97 | 4.437 | 8.551 | 9.555 | 1.00 30.74 | A C |
| ATOM | 438 | CD | GLU | A | 97 | 5.731 | 8.334 | 8.801 | 1.00 30.74 | A C |
| ATOM | 439 | OE1 | GLU | A | 97 | 6.404 | 9.337 | 8.495 | 1.00 30.74 | A O |
| ATOM | 440 | OE2 | GLU | A | 97 | 6.067 | 7.171 | 8.500 | 1.00 30.74 | A O |
| ATOM | 441 | C | GLU | A | 97 | 2.697 | 9.411 | 11.923 | 1.00 40.91 | A C |
| ATOM | 442 | O | GLU | A | 97 | 1.977 | 8.407 | 11.885 | 1.00 40.91 | A O |
| ATOM | 443 | N | LEU | A | 98 | 3.311 | 9.814 | 13.032 | 1.00 42.28 | A N |
| ATOM | 444 | CA | LEU | A | 98 | 3.180 | 9.074 | 14.277 | 1.00 42.28 | A C |
| ATOM | 445 | CB | LEU | A | 98 | 4.052 | 9.701 | 15.358 | 1.00 33.53 | A C |
| ATOM | 446 | CG | LEU | A | 98 | 3.922 | 9.067 | 16.743 | 1.00 33.53 | A C |
| ATOM | 447 | CD1 | LEU | A | 98 | 3.995 | 7.544 | 16.622 | 1.00 33.53 | A C |
| ATOM | 448 | CD2 | LEU | A | 98 | 5.025 | 9.609 | 17.650 | 1.00 33.53 | A C |
| ATOM | 449 | C | LEU | A | 98 | 1.742 | 8.990 | 14.768 | 1.00 42.28 | A C |
| ATOM | 450 | O | LEU | A | 98 | 1.297 | 7.935 | 15.220 | 1.00 42.28 | A O |
| ATOM | 451 | N | GLN | A | 99 | 1.010 | 10.094 | 14.680 | 1.00 42.69 | A N |
| ATOM | 452 | CA | GLN | A | 99 | -0.377 | 10.102 | 15.127 | 1.00 42.69 | A C |
| ATOM | 453 | CB | GLN | A | 99 | -0.953 | 11.517 | 15.075 | 1.00 100.00 | A C |
| ATOM | 454 | CG | GLN | A | 99 | -0.538 | 12.407 | 16.243 | 1.00 100.00 | A C |
| ATOM | 455 | CD | GLN | A | 99 | -1.117 | 13.827 | 16.128 | 1.00 100.00 | A C |
| ATOM | 456 | OE1 | GLN | A | 99 | -0.928 | 14.672 | 17.033 | 1.00 100.00 | A O |
| ATOM | 457 | NE2 | GLN | A | 99 | -1.822 | 14.101 | 15.012 | 1.00 100.00 | A N |
| ATOM | 458 | C | GLN | A | 99 | -1.246 | 9.165 | 14.304 | 1.00 42.69 | A C |
| ATOM | 459 | O | GLN | A | 99 | -2.084 | 8.455 | 14.857 | 1.00 42.69 | A O |
| ATOM | 460 | N | ILE | A | 100 | -1.052 | 9.159 | 12.987 | 1.00 38.43 | A N |
| ATOM | 461 | CA | ILE | A | 100 | -1.832 | 8.282 | 12.124 | 1.00 38.43 | A C |
| ATOM | 462 | CB | ILE | A | 100 | -1.593 | 8.599 | 10.631 | 1.00 38.07 | A C |

FIG. 3-8

```
ATOM    463  CG2 ILE A 100      -2.265    7.546    9.760  1.00 38.07           A    C
ATOM    464  CG1 ILE A 100      -2.167    9.979   10.301  1.00 38.07           A    C
ATOM    465  CD1 ILE A 100      -1.916   10.445    8.877  1.00 38.07           A    C
ATOM    466  C   ILE A 100      -1.430    6.839   12.396  1.00 38.43           A    C
ATOM    467  O   ILE A 100      -2.249    6.000   12.781  1.00 38.43           A    O
ATOM    468  N   MET A 101      -0.143    6.579   12.208  1.00 48.46           A    N
ATOM    469  CA  MET A 101       0.443    5.264   12.401  1.00 48.46           A    C
ATOM    470  CB  MET A 101       1.957    5.406   12.470  1.00 72.51           A    C
ATOM    471  CG  MET A 101       2.695    4.126   12.208  1.00 72.51           A    C
ATOM    472  SD  MET A 101       2.476    3.640   10.478  1.00 72.51           A    S
ATOM    473  CE  MET A 101       4.033    4.350    9.712  1.00 72.51           A    C
ATOM    474  C   MET A 101      -0.049    4.605   13.675  1.00 48.46           A    C
ATOM    475  O   MET A 101      -0.508    3.460   13.668  1.00 48.46           A    O
ATOM    476  N   ARG A 102       0.056    5.354   14.769  1.00 55.26           A    N
ATOM    477  CA  ARG A 102      -0.315    4.917   16.112  1.00 55.26           A    C
ATOM    478  CB  ARG A 102      -0.035    6.073   17.081  1.00 63.42           A    C
ATOM    479  CG  ARG A 102       0.037    5.709   18.559  1.00 63.42           A    C
ATOM    480  CD  ARG A 102       1.479    5.571   19.049  1.00 63.42           A    C
ATOM    481  NE  ARG A 102       1.547    5.496   20.508  1.00 63.42           A    N
ATOM    482  CZ  ARG A 102       1.397    6.545   21.309  1.00 63.42           A    C
ATOM    483  NH1 ARG A 102       1.180    7.744   20.787  1.00 63.42           A    N
ATOM    484  NH2 ARG A 102       1.451    6.395   22.626  1.00 63.42           A    N
ATOM    485  C   ARG A 102      -1.754    4.409   16.309  1.00 55.26           A    C
ATOM    486  O   ARG A 102      -2.015    3.671   17.255  1.00 55.26           A    O
ATOM    487  N   LYS A 103      -2.688    4.785   15.434  1.00 51.59           A    N
ATOM    488  CA  LYS A 103      -4.078    4.345   15.605  1.00 51.59           A    C
ATOM    489  CB  LYS A 103      -5.032    5.550   15.582  1.00 61.81           A    C
ATOM    490  CG  LYS A 103      -5.334    6.098   14.194  1.00 61.81           A    C
ATOM    491  CD  LYS A 103      -6.380    7.209   14.220  1.00 61.81           A    C
ATOM    492  CE  LYS A 103      -5.815    8.506   14.781  1.00 61.81           A    C
ATOM    493  NZ  LYS A 103      -6.654    9.689   14.405  1.00 61.81           A    N
ATOM    494  C   LYS A 103      -4.543    3.325   14.575  1.00 51.59           A    C
ATOM    495  O   LYS A 103      -5.745    3.083   14.430  1.00 51.59           A    O
ATOM    496  N   LEU A 104      -3.591    2.730   13.867  1.00 43.94           A    N
ATOM    497  CA  LEU A 104      -3.899    1.732   12.848  1.00 43.94           A    C
ATOM    498  CB  LEU A 104      -3.190    2.095   11.543  1.00 40.73           A    C
ATOM    499  CG  LEU A 104      -3.911    2.930   10.484  1.00 40.73           A    C
ATOM    500  CD1 LEU A 104      -4.723    4.044   11.103  1.00 40.73           A    C
ATOM    501  CD2 LEU A 104      -2.867    3.474    9.536  1.00 40.73           A    C
ATOM    502  C   LEU A 104      -3.479    0.327   13.275  1.00 43.94           A    C
ATOM    503  O   LEU A 104      -2.417    0.142   13.863  1.00 43.94           A    O
ATOM    504  N   ASP A 105      -4.322   -0.655   12.988  1.00 35.34           A    N
ATOM    505  CA  ASP A 105      -4.012   -2.029   13.311  1.00 35.34           A    C
ATOM    506  CB  ASP A 105      -4.532   -2.419   14.695  1.00 52.66           A    C
ATOM    507  CG  ASP A 105      -4.064   -3.814   15.116  1.00 52.66           A    C
ATOM    508  OD1 ASP A 105      -3.361   -4.481   14.310  1.00 52.66           A    O
ATOM    509  OD2 ASP A 105      -4.396   -4.243   16.247  1.00 52.66           A    O
ATOM    510  C   ASP A 105      -4.650   -2.919   12.258  1.00 35.34           A    C
ATOM    511  O   ASP A 105      -5.771   -3.432   12.422  1.00 35.34           A    O
ATOM    512  N   HIS A 106      -3.954   -3.075   11.145  1.00 66.25           A    N
ATOM    513  CA  HIS A 106      -4.446   -3.930   10.082  1.00 66.25           A    C
ATOM    514  CB  HIS A 106      -4.983   -3.060    8.933  1.00 59.60           A    C
ATOM    515  CG  HIS A 106      -5.963   -3.751    8.057  1.00 59.60           A    C
ATOM    516  CD2 HIS A 106      -7.309   -3.637    7.940  1.00 59.60           A    C
ATOM    517  ND1 HIS A 106      -5.561   -4.678    7.129  1.00 59.60           A    N
ATOM    518  CE1 HIS A 106      -6.620   -5.109    6.465  1.00 59.60           A    C
ATOM    519  NE2 HIS A 106      -7.691   -4.495    6.937  1.00 59.60           A    N
ATOM    520  C   HIS A 106      -3.263   -4.750    9.622  1.00 66.25           A    C
ATOM    521  O   HIS A 106      -2.149   -4.273    9.524  1.00 66.25           A    O
ATOM    522  N   CYS A 107      -3.586   -6.021    9.323  1.00 41.53           A    N
ATOM    523  CA  CYS A 107      -2.597   -7.014    8.872  1.00 41.53           A    C
ATOM    524  CB  CYS A 107      -2.931   -8.627    9.072  1.00 83.38           A    C
ATOM    525  SG  CYS A 107      -2.691   -8.995   10.899  1.00 83.38           A    S
ATOM    526  C   CYS A 107      -2.088   -6.676    7.538  1.00 41.53           A    C
ATOM    527  O   CYS A 107      -1.202   -7.263    7.076  1.00 41.53           A    O
ATOM    528  N   ASN A 108      -2.599   -5.602    6.960  1.00 47.72           A    N
ATOM    529  CA  ASN A 108      -2.137   -5.202    5.630  1.00 47.72           A    C
```

FIG. 3-9

```
ATOM    530  CB   ASN A 108     -3.295   -5.205    4.581  1.00 46.00      A  C
ATOM    531  CG   ASN A 108     -3.663   -6.616    4.121  1.00 46.00      A  C
ATOM    532  OD1  ASN A 108     -4.809   -7.058    4.250  1.00 46.00      A  O
ATOM    533  ND2  ASN A 108     -2.667   -7.345    3.619  1.00 46.00      A  N
ATOM    534  C    ASN A 108     -1.426   -3.894    5.656  1.00 47.72      A  C
ATOM    535  O    ASN A 108     -1.186   -3.268    4.630  1.00 47.72      A  O
ATOM    536  N    ILE A 109     -1.035   -3.541    6.866  1.00 34.69      A  N
ATOM    537  CA   ILE A 109     -0.294   -2.325    7.098  1.00 34.69      A  C
ATOM    538  CB   ILE A 109     -1.193   -1.245    7.755  1.00 39.96      A  C
ATOM    539  CG2  ILE A 109     -0.393    0.008    8.082  1.00 39.96      A  C
ATOM    540  CG1  ILE A 109     -2.321   -0.877    6.805  1.00 39.96      A  C
ATOM    541  CD1  ILE A 109     -3.240    0.198    7.337  1.00 39.96      A  C
ATOM    542  C    ILE A 109      0.907   -2.613    7.994  1.00 34.69      A  C
ATOM    543  O    ILE A 109      0.771   -3.363    8.956  1.00 34.69      A  O
ATOM    544  N    VAL A 110      2.077   -2.040    7.686  1.00 33.72      A  N
ATOM    545  CA   VAL A 110      3.240   -2.283    8.542  1.00 33.72      A  C
ATOM    546  CB   VAL A 110      4.482   -1.447    8.181  1.00 40.92      A  C
ATOM    547  CG1  VAL A 110      4.971   -1.804    6.818  1.00 40.92      A  C
ATOM    548  CG2  VAL A 110      4.164    0.024    8.270  1.00 40.92      A  C
ATOM    549  C    VAL A 110      2.847   -1.881    9.940  1.00 33.72      A  C
ATOM    550  O    VAL A 110      2.199   -0.861   10.139  1.00 33.72      A  O
ATOM    551  N    ARG A 111      3.230   -2.690   10.910  1.00 39.88      A  N
ATOM    552  CA   ARG A 111      2.909   -2.386   12.287  1.00 39.88      A  C
ATOM    553  CB   ARG A 111      2.830   -3.661   13.063  1.00 71.21      A  C
ATOM    554  CG   ARG A 111      2.484   -3.507   14.470  1.00 71.21      A  C
ATOM    555  CD   ARG A 111      2.683   -4.805   14.701  1.00 71.21      A  C
ATOM    556  NE   ARG A 111      2.487   -5.205   15.981  1.00 71.21      A  N
ATOM    557  CZ   ARG A 111      2.856   -6.362   16.460  1.00 71.21      A  C
ATOM    558  NH1  ARG A 111      2.514   -6.514   17.713  1.00 71.21      A  N
ATOM    559  NH2  ARG A 111      3.540   -7.288   15.748  1.00 71.21      A  N
ATOM    560  C    ARG A 111      3.995   -1.504   12.872  1.00 39.88      A  C
ATOM    561  O    ARG A 111      5.171   -1.607   12.497  1.00 39.88      A  O
ATOM    562  N    LEU A 112      3.591   -0.606   13.761  1.00 45.04      A  N
ATOM    563  CA   LEU A 112      4.534    0.281   14.420  1.00 45.04      A  C
ATOM    564  CB   LEU A 112      3.934    1.678   14.596  1.00 30.01      A  C
ATOM    565  CG   LEU A 112      4.728    2.665   15.453  1.00 30.01      A  C
ATOM    566  CD1  LEU A 112      5.918    3.202   14.666  1.00 30.01      A  C
ATOM    567  CD2  LEU A 112      3.826    3.804   15.885  1.00 30.01      A  C
ATOM    568  C    LEU A 112      4.717   -0.380   15.773  1.00 45.04      A  C
ATOM    569  O    LEU A 112      3.867   -0.237   16.646  1.00 45.04      A  O
ATOM    570  N    ARG A 113      5.812   -1.124   15.931  1.00 46.44      A  N
ATOM    571  CA   ARG A 113      6.116   -1.832   17.177  1.00 46.44      A  C
ATOM    572  CB   ARG A 113      7.362   -2.704   16.996  1.00 65.74      A  C
ATOM    573  CG   ARG A 113      7.298   -3.660   15.814  1.00 65.74      A  C
ATOM    574  CD   ARG A 113      6.277   -4.772   16.049  1.00 65.74      A  C
ATOM    575  NE   ARG A 113      6.838   -5.906   16.784  1.00 65.74      A  N
ATOM    576  CZ   ARG A 113      7.749   -6.743   16.283  1.00 65.74      A  C
ATOM    577  NH1  ARG A 113      8.206   -6.574   15.038  1.00 65.74      A  N
ATOM    578  NH2  ARG A 113      8.199   -7.755   17.021  1.00 65.74      A  N
ATOM    579  C    ARG A 113      6.339   -0.862   18.336  1.00 46.44      A  C
ATOM    580  O    ARG A 113      5.774   -1.035   19.414  1.00 46.44      A  O
ATOM    581  N    TYR A 114      7.166    0.152   18.100  1.00 37.76      A  N
ATOM    582  CA   TYR A 114      7.480    1.155   19.109  1.00 37.76      A  C
ATOM    583  CB   TYR A 114      8.698    0.741   19.961  1.00 42.56      A  C
ATOM    584  CG   TYR A 114      8.700   -0.677   20.470  1.00 42.56      A  C
ATOM    585  CD1  TYR A 114      7.858   -1.067   21.508  1.00 42.56      A  C
ATOM    586  CE1  TYR A 114      7.820   -2.391   21.941  1.00 42.56      A  C
ATOM    587  CD2  TYR A 114      9.510   -1.644   19.879  1.00 42.56      A  C
ATOM    588  CE2  TYR A 114      9.476   -2.968   20.303  1.00 42.56      A  C
ATOM    589  CZ   TYR A 114      8.628   -3.337   21.330  1.00 42.56      A  C
ATOM    590  OH   TYR A 114      8.562   -4.651   21.727  1.00 42.56      A  O
ATOM    591  C    TYR A 114      7.879    2.430   18.395  1.00 37.76      A  C
ATOM    592  O    TYR A 114      7.934    2.492   17.167  1.00 37.76      A  O
ATOM    593  N    PHE A 115      8.168    3.447   19.190  1.00 41.62      A  N
ATOM    594  CA   PHE A 115      8.655    4.705   18.673  1.00 41.62      A  C
ATOM    595  CB   PHE A 115      7.510    5.596   18.170  1.00 39.31      A  C
ATOM    596  CG   PHE A 115      6.664    6.201   19.246  1.00 39.31      A  C
```

FIG. 3-10

| ATOM | 597 | CD1 | PHE A 115 | 6.982 | 7.443 | 19.783 | 1.00 | 39.31 | A | C |
|------|-----|-----|-----------|-------|-------|--------|------|-------|---|---|
| ATOM | 598 | CD2 | PHE A 115 | 5.511 | 5.563 | 19.674 | 1.00 | 39.31 | A | C |
| ATOM | 599 | CE1 | PHE A 115 | 6.160 | 8.042 | 20.727 | 1.00 | 39.31 | A | C |
| ATOM | 600 | CE2 | PHE A 115 | 4.680 | 6.153 | 20.619 | 1.00 | 39.31 | A | C |
| ATOM | 601 | CZ | PHE A 115 | 5.004 | 7.393 | 21.143 | 1.00 | 39.31 | A | C |
| ATOM | 602 | C | PHE A 115 | 9.417 | 5.309 | 19.842 | 1.00 | 41.62 | A | C |
| ATOM | 603 | O | PHE A 115 | 9.045 | 5.127 | 21.002 | 1.00 | 41.62 | A | O |
| ATOM | 604 | N | PHE A 116 | 10.521 | 5.976 | 19.543 | 1.00 | 47.22 | A | N |
| ATOM | 605 | CA | PHE A 116 | 11.328 | 6.563 | 20.589 | 1.00 | 47.22 | A | C |
| ATOM | 606 | CB | PHE A 116 | 12.311 | 5.511 | 21.129 | 1.00 | 48.62 | A | C |
| ATOM | 607 | CG | PHE A 116 | 13.402 | 5.116 | 20.164 | 1.00 | 48.62 | A | C |
| ATOM | 608 | CD1 | PHE A 116 | 14.551 | 5.896 | 20.026 | 1.00 | 48.62 | A | C |
| ATOM | 609 | CD2 | PHE A 116 | 13.305 | 3.938 | 19.427 | 1.00 | 48.62 | A | C |
| ATOM | 610 | CE1 | PHE A 116 | 15.588 | 5.505 | 19.174 | 1.00 | 48.62 | A | C |
| ATOM | 611 | CE2 | PHE A 116 | 14.342 | 3.537 | 18.565 | 1.00 | 48.62 | A | C |
| ATOM | 612 | CZ | PHE A 116 | 15.483 | 4.321 | 18.441 | 1.00 | 48.62 | A | C |
| ATOM | 613 | C | PHE A 116 | 12.055 | 7.784 | 20.055 | 1.00 | 47.22 | A | C |
| ATOM | 614 | O | PHE A 116 | 12.110 | 7.997 | 18.848 | 1.00 | 47.22 | A | O |
| ATOM | 615 | N | TYR A 117 | 12.594 | 8.591 | 20.958 | 1.00 | 55.46 | A | N |
| ATOM | 616 | CA | TYR A 117 | 13.307 | 9.801 | 20.579 | 1.00 | 55.46 | A | C |
| ATOM | 617 | CB | TYR A 117 | 12.759 | 10.976 | 21.379 | 1.00 | 50.26 | A | C |
| ATOM | 618 | CG | TYR A 117 | 11.298 | 11.178 | 21.101 | 1.00 | 50.26 | A | C |
| ATOM | 619 | CD1 | TYR A 117 | 10.877 | 11.931 | 20.003 | 1.00 | 50.26 | A | C |
| ATOM | 620 | CE1 | TYR A 117 | 9.532 | 12.036 | 19.673 | 1.00 | 50.26 | A | C |
| ATOM | 621 | CD2 | TYR A 117 | 10.330 | 10.535 | 21.871 | 1.00 | 50.26 | A | C |
| ATOM | 622 | CE2 | TYR A 117 | 8.982 | 10.629 | 21.549 | 1.00 | 50.26 | A | C |
| ATOM | 623 | CZ | TYR A 117 | 8.590 | 11.381 | 20.446 | 1.00 | 50.26 | A | C |
| ATOM | 624 | OH | TYR A 117 | 7.256 | 11.460 | 20.117 | 1.00 | 50.26 | A | O |
| ATOM | 625 | C | TYR A 117 | 14.809 | 9.654 | 20.790 | 1.00 | 55.46 | A | C |
| ATOM | 626 | O | TYR A 117 | 15.268 | 8.706 | 21.435 | 1.00 | 55.46 | A | O |
| ATOM | 627 | N | SER A 118 | 15.577 | 10.593 | 20.247 | 1.00 | 47.23 | A | N |
| ATOM | 628 | CA | SER A 118 | 17.016 | 10.521 | 20.376 | 1.00 | 47.23 | A | C |
| ATOM | 629 | CB | SER A 118 | 17.528 | 9.333 | 19.563 | 1.00 | 44.24 | A | C |
| ATOM | 630 | OG | SER A 118 | 16.956 | 9.339 | 18.268 | 1.00 | 44.24 | A | O |
| ATOM | 631 | C | SER A 118 | 17.728 | 11.799 | 19.943 | 1.00 | 47.23 | A | C |
| ATOM | 632 | O | SER A 118 | 17.106 | 12.746 | 19.439 | 1.00 | 47.23 | A | O |
| ATOM | 633 | N | SER A 119 | 19.045 | 11.810 | 20.142 | 1.00 | 80.15 | A | N |
| ATOM | 634 | CA | SER A 119 | 19.869 | 12.960 | 19.797 | 1.00 | 80.15 | A | C |
| ATOM | 635 | CB | SER A 119 | 20.786 | 13.314 | 20.972 | 1.00 | 65.16 | A | C |
| ATOM | 636 | OG | SER A 119 | 20.023 | 13.692 | 22.113 | 1.00 | 65.16 | A | O |
| ATOM | 637 | C | SER A 119 | 20.700 | 12.685 | 18.552 | 1.00 | 80.15 | A | C |
| ATOM | 638 | O | SER A 119 | 20.668 | 13.464 | 17.597 | 1.00 | 80.15 | A | O |
| ATOM | 639 | N | ALA A 125 | 18.556 | 19.312 | 18.875 | 1.00 | 100.00 | A | N |
| ATOM | 640 | CA | ALA A 125 | 17.422 | 18.810 | 18.085 | 1.00 | 100.00 | A | C |
| ATOM | 641 | CB | ALA A 125 | 17.781 | 18.803 | 16.579 | 1.00 | 55.28 | A | C |
| ATOM | 642 | C | ALA A 125 | 16.994 | 17.400 | 18.538 | 1.00 | 100.00 | A | C |
| ATOM | 643 | O | ALA A 125 | 17.803 | 16.628 | 19.090 | 1.00 | 100.00 | A | O |
| ATOM | 644 | N | ALA A 126 | 15.725 | 17.064 | 18.310 | 1.00 | 67.09 | A | N |
| ATOM | 645 | CA | ALA A 126 | 15.204 | 15.758 | 18.705 | 1.00 | 67.09 | A | C |
| ATOM | 646 | CB | ALA A 126 | 14.117 | 15.934 | 19.773 | 1.00 | 30.53 | A | C |
| ATOM | 647 | C | ALA A 126 | 14.650 | 14.999 | 17.498 | 1.00 | 67.09 | A | C |
| ATOM | 648 | O | ALA A 126 | 13.778 | 15.501 | 16.797 | 1.00 | 67.09 | A | O |
| ATOM | 649 | N | TYR A 127 | 15.165 | 13.795 | 17.258 | 1.00 | 60.33 | A | N |
| ATOM | 650 | CA | TYR A 127 | 14.707 | 12.966 | 16.141 | 1.00 | 60.33 | A | C |
| ATOM | 651 | CB | TYR A 127 | 15.864 | 12.182 | 15.516 | 1.00 | 75.69 | A | C |
| ATOM | 652 | CG | TYR A 127 | 17.031 | 13.009 | 15.034 | 1.00 | 75.69 | A | C |
| ATOM | 653 | CD1 | TYR A 127 | 17.815 | 13.733 | 15.934 | 1.00 | 75.69 | A | C |
| ATOM | 654 | CE1 | TYR A 127 | 18.930 | 14.465 | 15.503 | 1.00 | 75.69 | A | C |
| ATOM | 655 | CD2 | TYR A 127 | 17.381 | 13.036 | 13.677 | 1.00 | 75.69 | A | C |
| ATOM | 656 | CE2 | TYR A 127 | 18.491 | 13.761 | 13.230 | 1.00 | 75.69 | A | C |
| ATOM | 657 | CZ | TYR A 127 | 19.265 | 14.474 | 14.149 | 1.00 | 75.69 | A | C |
| ATOM | 658 | OH | TYR A 127 | 20.380 | 15.184 | 13.728 | 1.00 | 75.69 | A | O |
| ATOM | 659 | C | TYR A 127 | 13.683 | 11.946 | 16.626 | 1.00 | 60.33 | A | C |
| ATOM | 660 | O | TYR A 127 | 13.832 | 11.376 | 17.706 | 1.00 | 60.33 | A | O |
| ATOM | 661 | N | LEU A 128 | 12.651 | 11.711 | 15.824 | 1.00 | 60.13 | A | N |
| ATOM | 662 | CA | LEU A 128 | 11.627 | 10.728 | 16.172 | 1.00 | 60.13 | A | C |
| ATOM | 663 | CB | LEU A 128 | 10.270 | 11.160 | 15.620 | 1.00 | 48.37 | A | C |

FIG. 3-11

```
ATOM    664  CG   LEU A 128       9.144   10.139   15.730  1.00 48.37      A    C
ATOM    665  CD1  LEU A 128       8.869    9.841   17.192  1.00 48.37      A    C
ATOM    666  CD2  LEU A 128       7.905   10.679   15.040  1.00 48.37      A    C
ATOM    667  C    LEU A 128      12.049    9.412   15.535  1.00 60.13      A    C
ATOM    668  O    LEU A 128      12.610    9.406   14.438  1.00 60.13      A    O
ATOM    669  N    ASN A 129      11.784    8.297   16.201  1.00 40.24      A    N
ATOM    670  CA   ASN A 129      12.184    7.014   15.642  1.00 40.24      A    C
ATOM    671  CB   ASN A 129      13.313    6.412   16.477  1.00 41.77      A    C
ATOM    672  CG   ASN A 129      14.578    7.258   16.442  1.00 41.77      A    C
ATOM    673  OD1  ASN A 129      15.482    7.011   15.647  1.00 41.77      A    O
ATOM    674  ND2  ASN A 129      14.637    8.272   17.299  1.00 41.77      A    N
ATOM    675  C    ASN A 129      11.022    6.051   15.574  1.00 40.24      A    C
ATOM    676  O    ASN A 129      10.458    5.664   16.594  1.00 40.24      A    O
ATOM    677  N    LEU A 130      10.660    5.672   14.356  1.00 41.54      A    N
ATOM    678  CA   LEU A 130       9.566    4.742   14.151  1.00 41.54      A    C
ATOM    679  CB   LEU A 130       8.745    5.165   12.928  1.00 43.12      A    C
ATOM    680  CG   LEU A 130       8.118    6.554   13.072  1.00 43.12      A    C
ATOM    681  CD1  LEU A 130       7.619    7.053   11.740  1.00 43.12      A    C
ATOM    682  CD2  LEU A 130       6.993    6.489   14.091  1.00 43.12      A    C
ATOM    683  C    LEU A 130      10.157    3.358   13.943  1.00 41.54      A    C
ATOM    684  O    LEU A 130      10.921    3.144   13.010  1.00 41.54      A    O
ATOM    685  N    VAL A 131       9.822    2.429   14.830  1.00 41.93      A    N
ATOM    686  CA   VAL A 131      10.318    1.062   14.729  1.00 41.93      A    C
ATOM    687  CB   VAL A 131      10.590    0.454   16.098  1.00 41.42      A    C
ATOM    688  CG1  VAL A 131      11.290   -0.878   15.920  1.00 41.42      A    C
ATOM    689  CG2  VAL A 131      11.400    1.422   16.956  1.00 41.42      A    C
ATOM    690  C    VAL A 131       9.220    0.252   14.097  1.00 41.93      A    C
ATOM    691  O    VAL A 131       8.219   -0.030   14.749  1.00 41.93      A    O
ATOM    692  N    LEU A 132       9.420   -0.141   12.842  1.00 38.60      A    N
ATOM    693  CA   LEU A 132       8.413   -0.888   12.095  1.00 38.60      A    C
ATOM    694  CB   LEU A 132       8.106   -0.139   10.811  1.00 29.05      A    C
ATOM    695  CG   LEU A 132       7.907    1.342   11.085  1.00 29.05      A    C
ATOM    696  CD1  LEU A 132       8.363    2.161    9.900  1.00 29.05      A    C
ATOM    697  CD2  LEU A 132       6.453    1.580   11.440  1.00 29.05      A    C
ATOM    698  C    LEU A 132       8.818   -2.302   11.741  1.00 38.60      A    C
ATOM    699  O    LEU A 132      10.009   -2.606   11.641  1.00 38.60      A    O
ATOM    700  N    ASP A 133       7.817   -3.162   11.551  1.00 44.86      A    N
ATOM    701  CA   ASP A 133       8.057   -4.545   11.154  1.00 44.86      A    C
ATOM    702  CB   ASP A 133       6.751   -5.253   10.798  1.00 99.49      A    C
ATOM    703  CG   ASP A 133       5.908   -5.579   12.012  1.00 99.49      A    C
ATOM    704  OD1  ASP A 133       4.693   -5.842   11.823  1.00 99.49      A    O
ATOM    705  OD2  ASP A 133       6.451   -5.584   13.150  1.00 99.49      A    O
ATOM    706  C    ASP A 133       8.908   -4.483    9.902  1.00 44.86      A    C
ATOM    707  O    ASP A 133       8.776   -3.566    9.092  1.00 44.86      A    O
ATOM    708  N    TYR A 134       9.789   -5.454    9.741  1.00 48.67      A    N
ATOM    709  CA   TYR A 134      10.622   -5.475    8.563  1.00 48.67      A    C
ATOM    710  CB   TYR A 134      12.027   -5.962    8.890  1.00 47.26      A    C
ATOM    711  CG   TYR A 134      12.946   -5.883    7.700  1.00 47.26      A    C
ATOM    712  CD1  TYR A 134      13.378   -4.647    7.218  1.00 47.26      A    C
ATOM    713  CE1  TYR A 134      14.183   -4.550    6.092  1.00 47.26      A    C
ATOM    714  CD2  TYR A 134      13.345   -7.033    7.020  1.00 47.26      A    C
ATOM    715  CE2  TYR A 134      14.151   -6.951    5.883  1.00 47.26      A    C
ATOM    716  CZ   TYR A 134      14.564   -5.705    5.427  1.00 47.26      A    C
ATOM    717  OH   TYR A 134      15.352   -5.608    4.304  1.00 47.26      A    O
ATOM    718  C    TYR A 134      10.006   -6.428    7.561  1.00 48.67      A    C
ATOM    719  O    TYR A 134       9.533   -7.500    7.931  1.00 48.67      A    O
ATOM    720  N    VAL A 135       9.984   -6.020    6.300  1.00 41.66      A    N
ATOM    721  CA   VAL A 135       9.479   -6.867    5.242  1.00 41.66      A    C
ATOM    722  CB   VAL A 135       8.079   -6.471    4.816  1.00 41.85      A    C
ATOM    723  CG1  VAL A 135       7.482   -7.573    3.984  1.00 41.85      A    C
ATOM    724  CG2  VAL A 135       7.223   -6.224    6.036  1.00 41.85      A    C
ATOM    725  C    VAL A 135      10.486   -6.597    4.141  1.00 41.66      A    C
ATOM    726  O    VAL A 135      10.705   -5.442    3.760  1.00 41.66      A    O
ATOM    727  N    PRO A 136      11.135   -7.663    3.633  1.00 55.48      A    N
ATOM    728  CD   PRO A 136      10.891   -9.056    4.067  1.00 54.70      A    C
ATOM    729  CA   PRO A 136      12.159   -7.617    2.582  1.00 55.48      A    C
ATOM    730  CB   PRO A 136      12.811   -8.991    2.695  1.00 54.70      A    C
```

FIG. 3-12

| | | | | | | | | | | |
|---|---|---|---|---|---|---|---|---|---|---|
| ATOM | 731 | CG | PRO A 136 | 11.625 | -9.872 | 3.017 | 1.00 | 54.70 | A | C |
| ATOM | 732 | C | PRO A 136 | 11.740 | -7.296 | 1.153 | 1.00 | 55.48 | A | C |
| ATOM | 733 | O | PRO A 136 | 12.399 | -6.516 | 0.467 | 1.00 | 55.48 | A | O |
| ATOM | 734 | N | GLU A 137 | 10.658 | -7.895 | 0.685 | 1.00 | 50.56 | A | N |
| ATOM | 735 | CA | GLU A 137 | 10.244 | -7.628 | -0.682 | 1.00 | 50.56 | A | C |
| ATOM | 736 | CB | GLU A 137 | 9.635 | -8.885 | -1.314 | 1.00 | 85.53 | A | C |
| ATOM | 737 | CG | GLU A 137 | 10.645 | -9.828 | -1.937 | 1.00 | 85.53 | A | C |
| ATOM | 738 | CD | GLU A 137 | 11.481 | -9.163 | -3.021 | 1.00 | 85.53 | A | C |
| ATOM | 739 | OE1 | GLU A 137 | 12.425 | -8.401 | -2.669 | 1.00 | 85.53 | A | O |
| ATOM | 740 | OE2 | GLU A 137 | 11.183 | -9.402 | -4.222 | 1.00 | 85.53 | A | O |
| ATOM | 741 | C | GLU A 137 | 9.262 | -6.479 | -0.836 | 1.00 | 50.56 | A | C |
| ATOM | 742 | O | GLU A 137 | 8.618 | -6.052 | 0.123 | 1.00 | 50.56 | A | O |
| ATOM | 743 | N | THR A 138 | 9.170 | -5.980 | -2.063 | 1.00 | 59.25 | A | N |
| ATOM | 744 | CA | THR A 138 | 8.237 | -4.916 | -2.398 | 1.00 | 59.25 | A | C |
| ATOM | 745 | CB | THR A 138 | 8.920 | -3.541 | -2.450 | 1.00 | 32.28 | A | C |
| ATOM | 746 | OG1 | THR A 138 | 9.829 | -3.501 | -3.555 | 1.00 | 32.28 | A | O |
| ATOM | 747 | CG2 | THR A 138 | 9.646 | -3.266 | -1.135 | 1.00 | 32.28 | A | C |
| ATOM | 748 | C | THR A 138 | 7.719 | -5.282 | -3.788 | 1.00 | 59.25 | A | C |
| ATOM | 749 | O | THR A 138 | 8.437 | -5.938 | -4.549 | 1.00 | 59.25 | A | O |
| ATOM | 750 | N | VAL A 139 | 6.477 | -4.900 | -4.102 | 1.00 | 34.89 | A | N |
| ATOM | 751 | CA | VAL A 139 | 5.881 | -5.185 | -5.402 | 1.00 | 34.89 | A | C |
| ATOM | 752 | CB | VAL A 139 | 4.454 | -4.559 | -5.514 | 1.00 | 29.64 | A | C |
| ATOM | 753 | CG1 | VAL A 139 | 3.922 | -4.669 | -6.945 | 1.00 | 29.64 | A | C |
| ATOM | 754 | CG2 | VAL A 139 | 3.509 | -5.261 | -4.567 | 1.00 | 29.64 | A | C |
| ATOM | 755 | C | VAL A 139 | 6.781 | -4.612 | -6.492 | 1.00 | 34.89 | A | C |
| ATOM | 756 | O | VAL A 139 | 6.911 | -5.192 | -7.568 | 1.00 | 34.89 | A | O |
| ATOM | 757 | N | TYR A 140 | 7.414 | -3.477 | -6.204 | 1.00 | 34.71 | A | N |
| ATOM | 758 | CA | TYR A 140 | 8.292 | -2.842 | -7.179 | 1.00 | 34.71 | A | C |
| ATOM | 759 | CB | TYR A 140 | 8.967 | -1.595 | -6.612 | 1.00 | 53.72 | A | C |
| ATOM | 760 | CG | TYR A 140 | 9.901 | -0.963 | -7.617 | 1.00 | 53.72 | A | C |
| ATOM | 761 | CD1 | TYR A 140 | 9.395 | -0.352 | -8.758 | 1.00 | 53.72 | A | C |
| ATOM | 762 | CE1 | TYR A 140 | 10.231 | 0.133 | -9.750 | 1.00 | 53.72 | A | C |
| ATOM | 763 | CD2 | TYR A 140 | 11.286 | -1.068 | -7.485 | 1.00 | 53.72 | A | C |
| ATOM | 764 | CE2 | TYR A 140 | 12.138 | -0.583 | -8.478 | 1.00 | 53.72 | A | C |
| ATOM | 765 | CZ | TYR A 140 | 11.595 | 0.013 | -9.612 | 1.00 | 53.72 | A | C |
| ATOM | 766 | OH | TYR A 140 | 12.401 | 0.473 | -10.631 | 1.00 | 53.72 | A | O |
| ATOM | 767 | C | TYR A 140 | 9.369 | -3.799 | -7.620 | 1.00 | 34.71 | A | C |
| ATOM | 768 | O | TYR A 140 | 9.569 | -4.012 | -8.808 | 1.00 | 34.71 | A | O |
| ATOM | 769 | N | ARG A 141 | 10.073 | -4.359 | -6.648 | 1.00 | 41.48 | A | N |
| ATOM | 770 | CA | ARG A 141 | 11.130 | -5.263 | -6.911 | 1.00 | 41.48 | A | C |
| ATOM | 771 | CB | ARG A 141 | 11.756 | -5.763 | -5.592 | 1.00 | 78.39 | A | C |
| ATOM | 772 | CG | ARG A 141 | 12.793 | -4.790 | -5.053 | 1.00 | 78.39 | A | C |
| ATOM | 773 | CD | ARG A 141 | 12.988 | -4.922 | -3.546 | 1.00 | 78.39 | A | C |
| ATOM | 774 | NE | ARG A 141 | 14.323 | -4.455 | -3.198 | 1.00 | 78.39 | A | N |
| ATOM | 775 | CZ | ARG A 141 | 15.404 | -5.230 | -3.228 | 1.00 | 78.39 | A | C |
| ATOM | 776 | NH1 | ARG A 141 | 15.294 | -6.516 | -3.572 | 1.00 | 78.39 | A | N |
| ATOM | 777 | NH2 | ARG A 141 | 16.597 | -4.711 | -2.962 | 1.00 | 78.39 | A | N |
| ATOM | 778 | C | ARG A 141 | 10.599 | -6.526 | -7.667 | 1.00 | 41.48 | A | C |
| ATOM | 779 | O | ARG A 141 | 11.172 | -6.931 | -8.676 | 1.00 | 41.48 | A | O |
| ATOM | 780 | N | VAL A 142 | 9.509 | -7.108 | -7.179 | 1.00 | 46.78 | A | N |
| ATOM | 781 | CA | VAL A 142 | 8.921 | -8.262 | -7.849 | 1.00 | 46.78 | A | C |
| ATOM | 782 | CB | VAL A 142 | 7.691 | -8.809 | -7.077 | 1.00 | 35.74 | A | C |
| ATOM | 783 | CG1 | VAL A 142 | 6.912 | -9.777 | -7.936 | 1.00 | 35.74 | A | C |
| ATOM | 784 | CG2 | VAL A 142 | 8.147 | -9.508 | -5.815 | 1.00 | 35.74 | A | C |
| ATOM | 785 | C | VAL A 142 | 8.484 | -7.885 | -9.264 | 1.00 | 46.78 | A | C |
| ATOM | 786 | O | VAL A 142 | 8.750 | -8.620 | -10.217 | 1.00 | 46.78 | A | O |
| ATOM | 787 | N | ALA A 143 | 7.823 | -6.738 | -9.401 | 1.00 | 33.50 | A | N |
| ATOM | 788 | CA | ALA A 143 | 7.346 | -6.303 | -10.702 | 1.00 | 33.50 | A | C |
| ATOM | 789 | CB | ALA A 143 | 6.599 | -4.996 | -10.565 | 1.00 | 37.56 | A | C |
| ATOM | 790 | C | ALA A 143 | 8.502 | -6.149 | -11.669 | 1.00 | 33.50 | A | C |
| ATOM | 791 | O | ALA A 143 | 8.431 | -6.604 | -12.813 | 1.00 | 33.50 | A | O |
| ATOM | 792 | N | ARG A 144 | 9.566 | -5.509 | -11.189 | 1.00 | 39.59 | A | N |
| ATOM | 793 | CA | ARG A 144 | 10.768 | -5.258 | -11.977 | 1.00 | 39.59 | A | C |
| ATOM | 794 | CB | ARG A 144 | 11.788 | -4.493 | -11.125 | 1.00 | 61.16 | A | C |
| ATOM | 795 | CG | ARG A 144 | 12.835 | -3.699 | -11.906 | 1.00 | 61.16 | A | C |
| ATOM | 796 | CD | ARG A 144 | 14.262 | -4.120 | -11.548 | 1.00 | 61.16 | A | C |
| ATOM | 797 | NE | ARG A 144 | 14.709 | -3.711 | -10.208 | 1.00 | 61.16 | A | N |

FIG. 3-13

```
ATOM    798  CZ   ARG A 144      15.038   -2.460   -9.850  1.00 61.16      A  C
ATOM    799  NH1  ARG A 144      14.978   -1.460  -10.736  1.00 61.16      A  N
ATOM    800  NH2  ARG A 144      15.422   -2.201   -8.593  1.00 61.16      A  N
ATOM    801  C    ARG A 144      11.365   -6.578  -12.443  1.00 39.59      A  C
ATOM    802  O    ARG A 144      11.707   -6.748  -13.614  1.00 39.59      A  O
ATOM    803  N    HIS A 145      11.464   -7.519  -11.510  1.00 55.72      A  N
ATOM    804  CA   HIS A 145      12.029   -8.837  -11.778  1.00 55.72      A  C
ATOM    805  CB   HIS A 145      12.012   -9.665  -10.490  1.00 95.48      A  C
ATOM    806  CG   HIS A 145      12.852  -10.906  -10.547  1.00 95.48      A  C
ATOM    807  CD2  HIS A 145      13.446  -11.538  -11.590  1.00 95.48      A  C
ATOM    808  ND1  HIS A 145      13.081  -11.699   -9.437  1.00 95.48      A  N
ATOM    809  CE1  HIS A 145      13.773  -12.767   -9.798  1.00 95.48      A  C
ATOM    810  NE2  HIS A 145      14.005  -12.695  -11.099  1.00 95.48      A  N
ATOM    811  C    HIS A 145      11.346   -9.585  -12.937  1.00 55.72      A  C
ATOM    812  O    HIS A 145      12.040  -10.149  -13.785  1.00 55.72      A  O
ATOM    813  N    TYR A 146      10.013   -9.601  -12.999  1.00 42.32      A  N
ATOM    814  CA   TYR A 146       9.359  -10.275  -14.122  1.00 42.32      A  C
ATOM    815  CB   TYR A 146       7.865  -10.482  -13.886  1.00 40.96      A  C
ATOM    816  CG   TYR A 146       7.516  -11.533  -12.870  1.00 40.96      A  C
ATOM    817  CD1  TYR A 146       7.715  -11.302  -11.513  1.00 40.96      A  C
ATOM    818  CE1  TYR A 146       7.420  -12.273  -10.566  1.00 40.96      A  C
ATOM    819  CD2  TYR A 146       7.004  -12.771  -13.260  1.00 40.96      A  C
ATOM    820  CE2  TYR A 146       6.702  -13.753  -12.314  1.00 40.96      A  C
ATOM    821  CZ   TYR A 146       6.920  -13.496  -10.966  1.00 40.96      A  C
ATOM    822  OH   TYR A 146       6.696  -14.456  -10.001  1.00 40.96      A  O
ATOM    823  C    TYR A 146       9.526   -9.408  -15.360  1.00 42.32      A  C
ATOM    824  O    TYR A 146       9.679   -9.903  -16.475  1.00 42.32      A  O
ATOM    825  N    SER A 147       9.507   -8.099  -15.151  1.00 43.19      A  N
ATOM    826  CA   SER A 147       9.628   -7.146  -16.247  1.00 43.19      A  C
ATOM    827  CB   SER A 147       9.360   -5.738  -15.728  1.00 50.78      A  C
ATOM    828  OG   SER A 147       9.376   -4.809  -16.789  1.00 50.78      A  O
ATOM    829  C    SER A 147      10.965   -7.180  -16.991  1.00 43.19      A  C
ATOM    830  O    SER A 147      10.996   -7.097  -18.220  1.00 43.19      A  O
ATOM    831  N    ARG A 148      12.069   -7.292  -16.257  1.00 51.06      A  N
ATOM    832  CA   ARG A 148      13.380   -7.344  -16.897  1.00 51.06      A  C
ATOM    833  CB   ARG A 148      14.497   -7.243  -15.866  1.00 85.14      A  C
ATOM    834  CG   ARG A 148      14.869   -5.836  -15.464  1.00 85.14      A  C
ATOM    835  CD   ARG A 148      15.915   -5.920  -14.373  1.00 85.14      A  C
ATOM    836  NE   ARG A 148      16.284   -4.615  -13.839  1.00 85.14      A  N
ATOM    837  CZ   ARG A 148      16.873   -4.451  -12.658  1.00 85.14      A  C
ATOM    838  NH1  ARG A 148      17.146   -5.521  -11.903  1.00 85.14      A  N
ATOM    839  NH2  ARG A 148      17.180   -3.224  -12.230  1.00 85.14      A  N
ATOM    840  C    ARG A 148      13.569   -8.638  -17.671  1.00 51.06      A  C
ATOM    841  O    ARG A 148      14.307   -8.676  -18.655  1.00 51.06      A  O
ATOM    842  N    ALA A 149      12.915   -9.699  -17.210  1.00 62.19      A  N
ATOM    843  CA   ALA A 149      13.022  -10.999  -17.863  1.00 62.19      A  C
ATOM    844  CB   ALA A 149      12.847  -12.136  -16.838  1.00 32.38      A  C
ATOM    845  C    ALA A 149      11.967  -11.114  -18.945  1.00 62.19      A  C
ATOM    846  O    ALA A 149      11.568  -12.222  -19.310  1.00 62.19      A  O
ATOM    847  N    LYS A 150      11.501   -9.971  -19.442  1.00 59.65      A  N
ATOM    848  CA   LYS A 150      10.490   -9.958  -20.493  1.00 59.65      A  C
ATOM    849  CB   LYS A 150      11.161  -10.289  -21.832  1.00 78.22      A  C
ATOM    850  CG   LYS A 150      10.562   -9.568  -23.034  1.00 78.22      A  C
ATOM    851  CD   LYS A 150      11.065   -8.113  -23.180  1.00 78.22      A  C
ATOM    852  CE   LYS A 150      12.516   -8.055  -23.676  1.00 78.22      A  C
ATOM    853  NZ   LYS A 150      12.893   -6.718  -24.247  1.00 78.22      A  N
ATOM    854  C    LYS A 150       9.408  -11.003  -20.161  1.00 59.65      A  C
ATOM    855  O    LYS A 150       9.060  -11.831  -20.994  1.00 59.65      A  O
ATOM    856  N    GLN A 151       8.882  -10.950  -18.938  1.00 71.57      A  N
ATOM    857  CA   GLN A 151       7.871  -11.907  -18.457  1.00 71.57      A  C
ATOM    858  CB   GLN A 151       8.567  -12.892  -17.502  1.00 78.09      A  C
ATOM    859  CG   GLN A 151       7.714  -14.020  -16.956  1.00 78.09      A  C
ATOM    860  CD   GLN A 151       7.953  -15.323  -17.698  1.00 78.09      A  C
ATOM    861  OE1  GLN A 151       9.090  -15.802  -17.790  1.00 78.09      A  O
ATOM    862  NE2  GLN A 151       6.882  -15.907  -18.235  1.00 78.09      A  N
ATOM    863  C    GLN A 151       6.705  -11.192  -17.726  1.00 71.57      A  C
ATOM    864  O    GLN A 151       6.893  -10.124  -17.133  1.00 71.57      A  O
```

FIG. 3-14

```
ATOM    865  N    THR A 152       5.507  -11.772  -17.756  1.00 64.30      A    N
ATOM    866  CA   THR A 152       4.373  -11.135  -17.087  1.00 64.30      A    C
ATOM    867  CB   THR A 152       3.086  -11.154  -17.980  1.00 53.56      A    C
ATOM    868  OG1  THR A 152       2.052  -11.913  -17.333  1.00 53.56      A    O
ATOM    869  CG2  THR A 152       3.383  -11.769  -19.354  1.00 53.56      A    C
ATOM    870  C    THR A 152       4.048  -11.801  -15.751  1.00 64.30      A    C
ATOM    871  O    THR A 152       4.017  -13.029  -15.660  1.00 64.30      A    O
ATOM    872  N    LEU A 153       3.810  -10.997  -14.713  1.00 35.15      A    N
ATOM    873  CA   LEU A 153       3.464  -11.528  -13.395  1.00 35.15      A    C
ATOM    874  CB   LEU A 153       3.316  -10.384  -12.392  1.00 38.44      A    C
ATOM    875  CG   LEU A 153       2.885  -10.753  -10.960  1.00 38.44      A    C
ATOM    876  CD1  LEU A 153       4.079  -11.295  -10.193  1.00 38.44      A    C
ATOM    877  CD2  LEU A 153       2.314   -9.535  -10.247  1.00 38.44      A    C
ATOM    878  C    LEU A 153       2.145  -12.305  -13.450  1.00 35.15      A    C
ATOM    879  O    LEU A 153       1.148  -11.809  -13.953  1.00 35.15      A    O
ATOM    880  N    PRO A 154       2.125  -13.536  -12.930  1.00 37.31      A    N
ATOM    881  CD   PRO A 154       3.249  -14.323  -12.390  1.00 29.59      A    C
ATOM    882  CA   PRO A 154       0.887  -14.325  -12.949  1.00 37.31      A    C
ATOM    883  CB   PRO A 154       1.276  -15.573  -12.156  1.00 29.59      A    C
ATOM    884  CG   PRO A 154       2.728  -15.732  -12.476  1.00 29.59      A    C
ATOM    885  C    PRO A 154      -0.303  -13.574  -12.318  1.00 37.31      A    C
ATOM    886  O    PRO A 154      -0.179  -13.015  -11.225  1.00 37.31      A    O
ATOM    887  N    VAL A 155      -1.456  -13.579  -12.989  1.00 49.63      A    N
ATOM    888  CA   VAL A 155      -2.638  -12.881  -12.475  1.00 49.63      A    C
ATOM    889  CB   VAL A 155      -3.831  -12.903  -13.475  1.00 32.71      A    C
ATOM    890  CG1  VAL A 155      -3.450  -12.203  -14.751  1.00 32.71      A    C
ATOM    891  CG2  VAL A 155      -4.254  -14.321  -13.759  1.00 32.71      A    C
ATOM    892  C    VAL A 155      -3.146  -13.384  -11.129  1.00 49.63      A    C
ATOM    893  O    VAL A 155      -4.083  -12.814  -10.580  1.00 49.63      A    O
ATOM    894  N    ILE A 156      -2.561  -14.448  -10.587  1.00 41.28      A    N
ATOM    895  CA   ILE A 156      -3.018  -14.911   -9.279  1.00 41.28      A    C
ATOM    896  CB   ILE A 156      -2.663  -16.406   -9.002  1.00 33.71      A    C
ATOM    897  CG2  ILE A 156      -1.171  -16.620   -9.039  1.00 33.71      A    C
ATOM    898  CG1  ILE A 156      -3.201  -16.824   -7.629  1.00 33.71      A    C
ATOM    899  CD1  ILE A 156      -4.706  -16.759   -7.518  1.00 33.71      A    C
ATOM    900  C    ILE A 156      -2.332  -14.021   -8.258  1.00 41.28      A    C
ATOM    901  O    ILE A 156      -2.868  -13.755   -7.190  1.00 41.28      A    O
ATOM    902  N    TYR A 157      -1.137  -13.553   -8.594  1.00 40.46      A    N
ATOM    903  CA   TYR A 157      -0.419  -12.665   -7.692  1.00 40.46      A    C
ATOM    904  CB   TYR A 157       1.069  -12.649   -8.037  1.00 49.51      A    C
ATOM    905  CG   TYR A 157       1.797  -13.887   -7.577  1.00 49.51      A    C
ATOM    906  CD1  TYR A 157       2.613  -14.603   -8.444  1.00 49.51      A    C
ATOM    907  CE1  TYR A 157       3.272  -15.754   -8.029  1.00 49.51      A    C
ATOM    908  CD2  TYR A 157       1.657  -14.350   -6.279  1.00 49.51      A    C
ATOM    909  CE2  TYR A 157       2.308  -15.499   -5.851  1.00 49.51      A    C
ATOM    910  CZ   TYR A 157       3.116  -16.199   -6.732  1.00 49.51      A    C
ATOM    911  OH   TYR A 157       3.767  -17.343   -6.319  1.00 49.51      A    O
ATOM    912  C    TYR A 157      -1.015  -11.266   -7.825  1.00 40.46      A    C
ATOM    913  O    TYR A 157      -1.081  -10.505   -6.859  1.00 40.46      A    O
ATOM    914  N    VAL A 158      -1.467  -10.948   -9.035  1.00 42.41      A    N
ATOM    915  CA   VAL A 158      -2.067   -9.661   -9.302  1.00 42.41      A    C
ATOM    916  CB   VAL A 158      -2.373   -9.497  -10.791  1.00 32.15      A    C
ATOM    917  CG1  VAL A 158      -2.986   -8.129  -11.039  1.00 32.15      A    C
ATOM    918  CG2  VAL A 158      -1.100   -9.649  -11.603  1.00 32.15      A    C
ATOM    919  C    VAL A 158      -3.353   -9.550   -8.501  1.00 42.41      A    C
ATOM    920  O    VAL A 158      -3.668   -8.493   -7.951  1.00 42.41      A    O
ATOM    921  N    LYS A 159      -4.095  -10.643   -8.421  1.00 37.13      A    N
ATOM    922  CA   LYS A 159      -5.333  -10.624   -7.668  1.00 37.13      A    C
ATOM    923  CB   LYS A 159      -6.124  -11.900   -7.917  1.00 38.32      A    C
ATOM    924  CG   LYS A 159      -6.633  -12.044   -9.323  1.00 38.32      A    C
ATOM    925  CD   LYS A 159      -7.265  -13.396   -9.505  1.00 38.32      A    C
ATOM    926  CE   LYS A 159      -7.783  -13.591  -10.915  1.00 38.32      A    C
ATOM    927  NZ   LYS A 159      -8.612  -14.825  -10.988  1.00 38.32      A    N
ATOM    928  C    LYS A 159      -5.038  -10.495   -6.187  1.00 37.13      A    C
ATOM    929  O    LYS A 159      -5.659   -9.700   -5.483  1.00 37.13      A    O
ATOM    930  N    LEU A 160      -4.081  -11.286   -5.720  1.00 51.24      A    N
ATOM    931  CA   LEU A 160      -3.691  -11.283   -4.316  1.00 51.24      A    C
```

FIG. 3-15

```
ATOM    932  CB   LEU A 160      -2.615 -12.333  -4.069  1.00 56.41      A    C
ATOM    933  CG   LEU A 160      -3.181 -13.736  -3.894  1.00 56.41      A    C
ATOM    934  CD1  LEU A 160      -2.064 -14.752  -3.955  1.00 56.41      A    C
ATOM    935  CD2  LEU A 160      -3.929 -13.805  -2.560  1.00 56.41      A    C
ATOM    936  C    LEU A 160      -3.197  -9.947  -3.804  1.00 51.24      A    C
ATOM    937  O    LEU A 160      -3.648  -9.487  -2.756  1.00 51.24      A    O
ATOM    938  N    TYR A 161      -2.272  -9.327  -4.534  1.00 38.52      A    N
ATOM    939  CA   TYR A 161      -1.726  -8.046  -4.108  1.00 38.52      A    C
ATOM    940  CB   TYR A 161      -0.538  -7.659  -4.970  1.00 38.67      A    C
ATOM    941  CG   TYR A 161       0.543  -8.707  -4.953  1.00 38.67      A    C
ATOM    942  CD1  TYR A 161       0.586  -9.664  -3.945  1.00 38.67      A    C
ATOM    943  CE1  TYR A 161       1.573 -10.624  -3.911  1.00 38.67      A    C
ATOM    944  CD2  TYR A 161       1.525  -8.742  -5.935  1.00 38.67      A    C
ATOM    945  CE2  TYR A 161       2.521  -9.700  -5.907  1.00 38.67      A    C
ATOM    946  CZ   TYR A 161       2.536 -10.635  -4.890  1.00 38.67      A    C
ATOM    947  OH   TYR A 161       3.533 -11.570  -4.830  1.00 38.67      A    O
ATOM    948  C    TYR A 161      -2.748  -6.946  -4.135  1.00 38.52      A    C
ATOM    949  O    TYR A 161      -2.976  -6.281  -3.120  1.00 38.52      A    O
ATOM    950  N    MET A 162      -3.374  -6.754  -5.292  1.00 48.46      A    N
ATOM    951  CA   MET A 162      -4.378  -5.713  -5.416  1.00 48.46      A    C
ATOM    952  CB   MET A 162      -4.992  -5.734  -6.806  1.00 36.74      A    C
ATOM    953  CG   MET A 162      -4.012  -5.353  -7.887  1.00 36.74      A    C
ATOM    954  SD   MET A 162      -3.125  -3.849  -7.477  1.00 36.74      A    S
ATOM    955  CE   MET A 162      -4.456  -2.702  -7.311  1.00 36.74      A    C
ATOM    956  C    MET A 162      -5.454  -5.860  -4.356  1.00 48.46      A    C
ATOM    957  O    MET A 162      -5.816  -4.883  -3.709  1.00 48.46      A    O
ATOM    958  N    TYR A 163      -5.946  -7.079  -4.158  1.00 29.09      A    N
ATOM    959  CA   TYR A 163      -6.984  -7.315  -3.163  1.00 29.09      A    C
ATOM    960  CB   TYR A 163      -7.328  -8.794  -3.078  1.00 36.43      A    C
ATOM    961  CG   TYR A 163      -8.406  -9.074  -2.060  1.00 36.43      A    C
ATOM    962  CD1  TYR A 163      -9.751  -8.942  -2.386  1.00 36.43      A    C
ATOM    963  CE1  TYR A 163     -10.744  -9.185  -1.448  1.00 36.43      A    C
ATOM    964  CD2  TYR A 163      -8.080  -9.451  -0.765  1.00 36.43      A    C
ATOM    965  CE2  TYR A 163      -9.065  -9.695   0.179  1.00 36.43      A    C
ATOM    966  CZ   TYR A 163     -10.394  -9.563  -0.172  1.00 36.43      A    C
ATOM    967  OH   TYR A 163     -11.370  -9.844   0.755  1.00 36.43      A    O
ATOM    968  C    TYR A 163      -6.570  -6.846  -1.776  1.00 29.09      A    C
ATOM    969  O    TYR A 163      -7.342  -6.205  -1.063  1.00 29.09      A    O
ATOM    970  N    GLN A 164      -5.350  -7.193  -1.388  1.00 56.52      A    N
ATOM    971  CA   GLN A 164      -4.844  -6.804  -0.085  1.00 56.52      A    C
ATOM    972  CB   GLN A 164      -3.560  -7.572   0.227  1.00 41.43      A    C
ATOM    973  CG   GLN A 164      -3.760  -9.086   0.310  1.00 41.43      A    C
ATOM    974  CD   GLN A 164      -2.489  -9.826   0.718  1.00 41.43      A    C
ATOM    975  OE1  GLN A 164      -2.152  -9.912   1.904  1.00 41.43      A    O
ATOM    976  NE2  GLN A 164      -1.769 -10.351  -0.271  1.00 41.43      A    N
ATOM    977  C    GLN A 164      -4.609  -5.295  -0.034  1.00 56.52      A    C
ATOM    978  O    GLN A 164      -4.858  -4.661   0.993  1.00 56.52      A    O
ATOM    979  N    LEU A 165      -4.138  -4.713  -1.135  1.00 37.22      A    N
ATOM    980  CA   LEU A 165      -3.912  -3.280  -1.156  1.00 37.22      A    C
ATOM    981  CB   LEU A 165      -3.276  -2.840  -2.473  1.00 29.40      A    C
ATOM    982  CG   LEU A 165      -3.487  -1.365  -2.847  1.00 29.40      A    C
ATOM    983  CD1  LEU A 165      -2.999  -0.465  -1.749  1.00 29.40      A    C
ATOM    984  CD2  LEU A 165      -2.771  -1.056  -4.132  1.00 29.40      A    C
ATOM    985  C    LEU A 165      -5.253  -2.592  -0.988  1.00 37.22      A    C
ATOM    986  O    LEU A 165      -5.379  -1.624  -0.230  1.00 37.22      A    O
ATOM    987  N    PHE A 166      -6.261  -3.090  -1.697  1.00 35.56      A    N
ATOM    988  CA   PHE A 166      -7.584  -2.499  -1.601  1.00 35.56      A    C
ATOM    989  CB   PHE A 166      -8.543  -3.113  -2.622  1.00 36.93      A    C
ATOM    990  CG   PHE A 166      -8.506  -2.429  -3.961  1.00 36.93      A    C
ATOM    991  CD1  PHE A 166      -8.621  -1.037  -4.049  1.00 36.93      A    C
ATOM    992  CD2  PHE A 166      -8.327  -3.158  -5.128  1.00 36.93      A    C
ATOM    993  CE1  PHE A 166      -8.551  -0.387  -5.278  1.00 36.93      A    C
ATOM    994  CE2  PHE A 166      -8.256  -2.516  -6.353  1.00 36.93      A    C
ATOM    995  CZ   PHE A 166      -8.368  -1.124  -6.429  1.00 36.93      A    C
ATOM    996  C    PHE A 166      -8.152  -2.656  -0.212  1.00 35.56      A    C
ATOM    997  O    PHE A 166      -8.824  -1.767   0.298  1.00 35.56      A    O
ATOM    998  N    ARG A 167      -7.873  -3.781   0.417  1.00 34.84      A    N
```

FIG. 3-16

```
ATOM    999  CA   ARG A 167      -8.401  -3.987   1.743  1.00 34.84      A    C
ATOM   1000  CB   ARG A 167      -8.151  -5.429   2.204  1.00 46.61      A    C
ATOM   1001  CG   ARG A 167      -8.954  -5.769   3.436  1.00 46.61      A    C
ATOM   1002  CD   ARG A 167      -8.740  -7.161   3.939  1.00 46.61      A    C
ATOM   1003  NE   ARG A 167      -9.236  -7.239   5.307  1.00 46.61      A    N
ATOM   1004  CZ   ARG A 167      -9.121  -8.305   6.088  1.00 46.61      A    C
ATOM   1005  NH1  ARG A 167      -8.525  -9.398   5.633  1.00 46.61      A    N
ATOM   1006  NH2  ARG A 167      -9.585  -8.270   7.329  1.00 46.61      A    N
ATOM   1007  C    ARG A 167      -7.787  -2.992   2.724  1.00 34.84      A    C
ATOM   1008  O    ARG A 167      -8.486  -2.447   3.572  1.00 34.84      A    O
ATOM   1009  N    SER A 168      -6.486  -2.743   2.590  1.00 42.21      A    N
ATOM   1010  CA   SER A 168      -5.780  -1.819   3.477  1.00 42.21      A    C
ATOM   1011  CB   SER A 168      -4.273  -1.866   3.217  1.00 36.53      A    C
ATOM   1012  OG   SER A 168      -3.933  -1.125   2.062  1.00 36.53      A    O
ATOM   1013  C    SER A 168      -6.271  -0.385   3.303  1.00 42.21      A    C
ATOM   1014  O    SER A 168      -6.373   0.376   4.265  1.00 42.21      A    O
ATOM   1015  N    LEU A 169      -6.556  -0.016   2.064  1.00 40.57      A    N
ATOM   1016  CA   LEU A 169      -7.049   1.318   1.775  1.00 40.57      A    C
ATOM   1017  CB   LEU A 169      -7.142   1.516   0.262  1.00 32.97      A    C
ATOM   1018  CG   LEU A 169      -6.143   2.495  -0.354  1.00 32.97      A    C
ATOM   1019  CD1  LEU A 169      -4.790   2.397   0.332  1.00 32.97      A    C
ATOM   1020  CD2  LEU A 169      -6.031   2.206  -1.835  1.00 32.97      A    C
ATOM   1021  C    LEU A 169      -8.422   1.468   2.416  1.00 40.57      A    C
ATOM   1022  O    LEU A 169      -8.727   2.480   3.038  1.00 40.57      A    O
ATOM   1023  N    ALA A 170      -9.244   0.442   2.266  1.00 31.29      A    N
ATOM   1024  CA   ALA A 170     -10.568   0.455   2.832  1.00 31.29      A    C
ATOM   1025  CB   ALA A 170     -11.227  -0.878   2.600  1.00 19.73      A    C
ATOM   1026  C    ALA A 170     -10.443   0.727   4.321  1.00 31.29      A    C
ATOM   1027  O    ALA A 170     -11.265   1.424   4.924  1.00 31.29      A    O
ATOM   1028  N    TYR A 171      -9.392   0.179   4.911  1.00 39.04      A    N
ATOM   1029  CA   TYR A 171      -9.157   0.346   6.332  1.00 39.04      A    C
ATOM   1030  CB   TYR A 171      -8.028  -0.569   6.780  1.00 41.33      A    C
ATOM   1031  CG   TYR A 171      -7.711  -0.411   8.240  1.00 41.33      A    C
ATOM   1032  CD1  TYR A 171      -8.648  -0.751   9.211  1.00 41.33      A    C
ATOM   1033  CE1  TYR A 171      -8.376  -0.590  10.554  1.00 41.33      A    C
ATOM   1034  CD2  TYR A 171      -6.484   0.098   8.653  1.00 41.33      A    C
ATOM   1035  CE2  TYR A 171      -6.202   0.266  10.001  1.00 41.33      A    C
ATOM   1036  CZ   TYR A 171      -7.154  -0.082  10.944  1.00 41.33      A    C
ATOM   1037  OH   TYR A 171      -6.884   0.074  12.279  1.00 41.33      A    O
ATOM   1038  C    TYR A 171      -8.827   1.777   6.739  1.00 39.04      A    C
ATOM   1039  O    TYR A 171      -9.589   2.424   7.457  1.00 39.04      A    O
ATOM   1040  N    ILE A 172      -7.681   2.270   6.291  1.00 42.22      A    N
ATOM   1041  CA   ILE A 172      -7.290   3.619   6.649  1.00 42.22      A    C
ATOM   1042  CB   ILE A 172      -5.914   3.994   6.065  1.00 42.03      A    C
ATOM   1043  CG2  ILE A 172      -4.845   3.083   6.640  1.00 42.03      A    C
ATOM   1044  CG1  ILE A 172      -5.953   3.920   4.544  1.00 42.03      A    C
ATOM   1045  CD1  ILE A 172      -4.671   4.377   3.884  1.00 42.03      A    C
ATOM   1046  C    ILE A 172      -8.320   4.639   6.190  1.00 42.22      A    C
ATOM   1047  O    ILE A 172      -8.505   5.682   6.822  1.00 42.22      A    O
ATOM   1048  N    HIS A 173      -9.004   4.345   5.097  1.00 42.90      A    N
ATOM   1049  CA   HIS A 173      -9.995   5.282   4.615  1.00 42.90      A    C
ATOM   1050  CB   HIS A 173     -10.468   4.900   3.219  1.00 36.33      A    C
ATOM   1051  CG   HIS A 173      -9.500   5.275   2.142  1.00 36.33      A    C
ATOM   1052  CD2  HIS A 173      -8.254   5.802   2.213  1.00 36.33      A    C
ATOM   1053  ND1  HIS A 173      -9.782   5.139   0.801  1.00 36.33      A    N
ATOM   1054  CE1  HIS A 173      -8.754   5.570   0.093  1.00 36.33      A    C
ATOM   1055  NE2  HIS A 173      -7.814   5.978   0.925  1.00 36.33      A    N
ATOM   1056  C    HIS A 173     -11.176   5.435   5.546  1.00 42.90      A    C
ATOM   1057  O    HIS A 173     -11.833   6.474   5.522  1.00 42.90      A    O
ATOM   1058  N    SER A 174     -11.442   4.430   6.381  1.00 46.63      A    N
ATOM   1059  CA   SER A 174     -12.573   4.524   7.312  1.00 46.63      A    C
ATOM   1060  CB   SER A 174     -12.979   3.144   7.840  1.00 38.44      A    C
ATOM   1061  OG   SER A 174     -11.960   2.600   8.643  1.00 38.44      A    O
ATOM   1062  C    SER A 174     -12.315   5.476   8.490  1.00 46.63      A    C
ATOM   1063  O    SER A 174     -13.233   5.814   9.231  1.00 46.63      A    O
ATOM   1064  N    PHE A 175     -11.072   5.907   8.667  1.00 39.22      A    N
ATOM   1065  CA   PHE A 175     -10.757   6.852   9.732  1.00 39.22      A    C
```

FIG. 3-17

| | | | | | | | | | | |
|---|---|---|---|---|---|---|---|---|---|---|
| ATOM | 1066 | CB | PHE | A | 175 | -9.480 | 6.463 | 10.471 | 1.00 77.58 | A C |
| ATOM | 1067 | CG | PHE | A | 175 | -9.554 | 5.140 | 11.162 | 1.00 77.58 | A C |
| ATOM | 1068 | CD1 | PHE | A | 175 | -9.267 | 3.960 | 10.475 | 1.00 77.58 | A C |
| ATOM | 1069 | CD2 | PHE | A | 175 | -9.919 | 5.070 | 12.505 | 1.00 77.58 | A C |
| ATOM | 1070 | CE1 | PHE | A | 175 | -9.341 | 2.719 | 11.115 | 1.00 77.58 | A C |
| ATOM | 1071 | CE2 | PHE | A | 175 | -9.997 | 3.837 | 13.161 | 1.00 77.58 | A C |
| ATOM | 1072 | CZ | PHE | A | 175 | -9.706 | 2.653 | 12.462 | 1.00 77.58 | A C |
| ATOM | 1073 | C | PHE | A | 175 | -10.523 | 8.197 | 9.069 | 1.00 39.22 | A C |
| ATOM | 1074 | O | PHE | A | 175 | -10.014 | 9.131 | 9.693 | 1.00 39.22 | A O |
| ATOM | 1075 | N | GLY | A | 176 | -10.872 | 8.283 | 7.790 | 1.00 40.56 | A N |
| ATOM | 1076 | CA | GLY | A | 176 | -10.673 | 9.516 | 7.055 | 1.00 40.56 | A C |
| ATOM | 1077 | C | GLY | A | 176 | -9.203 | 9.785 | 6.771 | 1.00 40.56 | A C |
| ATOM | 1078 | O | GLY | A | 176 | -8.782 | 10.932 | 6.603 | 1.00 40.56 | A O |
| ATOM | 1079 | N | ILE | A | 177 | -8.413 | 8.720 | 6.713 | 1.00 39.95 | A N |
| ATOM | 1080 | CA | ILE | A | 177 | -6.993 | 8.845 | 6.435 | 1.00 39.95 | A C |
| ATOM | 1081 | CB | ILE | A | 177 | -6.193 | 7.970 | 7.382 | 1.00 48.78 | A C |
| ATOM | 1082 | CG2 | ILE | A | 177 | -4.733 | 7.982 | 6.980 | 1.00 48.78 | A C |
| ATOM | 1083 | CG1 | ILE | A | 177 | -6.386 | 8.468 | 8.809 | 1.00 48.78 | A C |
| ATOM | 1084 | CD1 | ILE | A | 177 | -5.941 | 7.477 | 9.878 | 1.00 48.78 | A C |
| ATOM | 1085 | C | ILE | A | 177 | -6.685 | 8.440 | 4.989 | 1.00 39.95 | A C |
| ATOM | 1086 | O | ILE | A | 177 | -7.081 | 7.366 | 4.529 | 1.00 39.95 | A O |
| ATOM | 1087 | N | CYS | A | 178 | -5.976 | 9.311 | 4.281 | 1.00 39.41 | A N |
| ATOM | 1088 | CA | CYS | A | 178 | -5.614 | 9.080 | 2.890 | 1.00 39.41 | A C |
| ATOM | 1089 | CB | CYS | A | 178 | -6.099 | 10.258 | 2.043 | 1.00 45.52 | A C |
| ATOM | 1090 | SG | CYS | A | 178 | -5.709 | 10.168 | 0.284 | 1.00 45.52 | A S |
| ATOM | 1091 | C | CYS | A | 178 | -4.100 | 8.916 | 2.748 | 1.00 39.41 | A C |
| ATOM | 1092 | O | CYS | A | 178 | -3.327 | 9.803 | 3.115 | 1.00 39.41 | A O |
| ATOM | 1093 | N | HIS | A | 179 | -3.679 | 7.784 | 2.200 | 1.00 35.87 | A N |
| ATOM | 1094 | CA | HIS | A | 179 | -2.266 | 7.509 | 2.041 | 1.00 35.87 | A C |
| ATOM | 1095 | CB | HIS | A | 179 | -2.082 | 6.120 | 1.438 | 1.00 33.74 | A C |
| ATOM | 1096 | CG | HIS | A | 179 | -0.671 | 5.637 | 1.483 | 1.00 33.74 | A C |
| ATOM | 1097 | CD2 | HIS | A | 179 | 0.000 | 4.940 | 2.430 | 1.00 33.74 | A C |
| ATOM | 1098 | ND1 | HIS | A | 179 | 0.250 | 5.942 | 0.504 | 1.00 33.74 | A N |
| ATOM | 1099 | CE1 | HIS | A | 179 | 1.429 | 5.455 | 0.848 | 1.00 33.74 | A C |
| ATOM | 1100 | NE2 | HIS | A | 179 | 1.304 | 4.845 | 2.013 | 1.00 33.74 | A N |
| ATOM | 1101 | C | HIS | A | 179 | -1.535 | 8.557 | 1.209 | 1.00 35.87 | A C |
| ATOM | 1102 | O | HIS | A | 179 | -0.441 | 8.977 | 1.558 | 1.00 35.87 | A O |
| ATOM | 1103 | N | ARG | A | 180 | -2.146 | 8.976 | 0.108 | 1.00 39.64 | A N |
| ATOM | 1104 | CA | ARG | A | 180 | -1.568 | 9.984 | -0.782 | 1.00 39.64 | A C |
| ATOM | 1105 | CB | ARG | A | 180 | -1.496 | 11.332 | -0.065 | 1.00 38.63 | A C |
| ATOM | 1106 | CG | ARG | A | 180 | -2.829 | 11.842 | 0.413 | 1.00 38.63 | A C |
| ATOM | 1107 | CD | ARG | A | 180 | -2.622 | 12.840 | 1.529 | 1.00 38.63 | A C |
| ATOM | 1108 | NE | ARG | A | 180 | -2.061 | 14.098 | 1.051 | 1.00 38.63 | A N |
| ATOM | 1109 | CZ | ARG | A | 180 | -1.520 | 15.023 | 1.838 | 1.00 38.63 | A C |
| ATOM | 1110 | NH1 | ARG | A | 180 | -1.453 | 14.837 | 3.145 | 1.00 38.63 | A N |
| ATOM | 1111 | NH2 | ARG | A | 180 | -1.061 | 16.147 | 1.313 | 1.00 38.63 | A N |
| ATOM | 1112 | C | ARG | A | 180 | -0.193 | 9.650 | -1.383 | 1.00 39.64 | A C |
| ATOM | 1113 | O | ARG | A | 180 | 0.480 | 10.522 | -1.939 | 1.00 39.64 | A O |
| ATOM | 1114 | N | ASP | A | 181 | 0.232 | 8.398 | -1.263 | 1.00 37.76 | A N |
| ATOM | 1115 | CA | ASP | A | 181 | 1.498 | 7.988 | -1.853 | 1.00 37.76 | A C |
| ATOM | 1116 | CB | ASP | A | 181 | 2.653 | 8.334 | -0.924 | 1.00 48.71 | A C |
| ATOM | 1117 | CG | ASP | A | 181 | 3.998 | 8.182 | -1.596 | 1.00 48.71 | A C |
| ATOM | 1118 | OD1 | ASP | A | 181 | 4.032 | 8.154 | -2.843 | 1.00 48.71 | A O |
| ATOM | 1119 | OD2 | ASP | A | 181 | 5.024 | 8.101 | -0.887 | 1.00 48.71 | A O |
| ATOM | 1120 | C | ASP | A | 181 | 1.527 | 6.500 | -2.221 | 1.00 37.76 | A C |
| ATOM | 1121 | O | ASP | A | 181 | 2.534 | 5.833 | -2.054 | 1.00 37.76 | A O |
| ATOM | 1122 | N | ILE | A | 182 | 0.411 | 5.990 | -2.735 | 1.00 34.86 | A N |
| ATOM | 1123 | CA | ILE | A | 182 | 0.316 | 4.595 | -3.140 | 1.00 34.86 | A C |
| ATOM | 1124 | CB | ILE | A | 182 | -1.144 | 4.186 | -3.481 | 1.00 31.20 | A C |
| ATOM | 1125 | CG2 | ILE | A | 182 | -1.204 | 2.725 | -3.894 | 1.00 31.20 | A C |
| ATOM | 1126 | CG1 | ILE | A | 182 | -2.052 | 4.427 | -2.276 | 1.00 31.20 | A C |
| ATOM | 1127 | CD1 | ILE | A | 182 | -1.708 | 3.602 | -1.066 | 1.00 31.20 | A C |
| ATOM | 1128 | C | ILE | A | 182 | 1.155 | 4.376 | -4.384 | 1.00 34.86 | A C |
| ATOM | 1129 | O | ILE | A | 182 | 0.944 | 5.038 | -5.403 | 1.00 34.86 | A O |
| ATOM | 1130 | N | LYS | A | 183 | 2.109 | 3.450 | -4.281 | 1.00 32.20 | A N |
| ATOM | 1131 | CA | LYS | A | 183 | 2.993 | 3.086 | -5.390 | 1.00 32.20 | A C |
| ATOM | 1132 | CB | LYS | A | 183 | 4.092 | 4.140 | -5.599 | 1.00 49.53 | A C |

FIG. 3-18

| | | | | | | | | | | | |
|---|---|---|---|---|---|---|---|---|---|---|---|
| ATOM | 1133 | CG | LYS | A | 183 | 5.009 | 4.368 | -4.408 | 1.00 | 49.53 | A C |
| ATOM | 1134 | CD | LYS | A | 183 | 6.027 | 5.435 | -4.741 | 1.00 | 49.53 | A C |
| ATOM | 1135 | CE | LYS | A | 183 | 6.850 | 5.839 | -3.536 | 1.00 | 49.53 | A C |
| ATOM | 1136 | NZ | LYS | A | 183 | 7.683 | 7.040 | -3.835 | 1.00 | 49.53 | A N |
| ATOM | 1137 | C | LYS | A | 183 | 3.616 | 1.729 | -5.095 | 1.00 | 32.20 | A C |
| ATOM | 1138 | O | LYS | A | 183 | 3.693 | 1.316 | -3.943 | 1.00 | 32.20 | A O |
| ATOM | 1139 | N | PRO | A | 184 | 4.056 | 1.013 | -6.139 | 1.00 | 36.52 | A N |
| ATOM | 1140 | CD | PRO | A | 184 | 3.958 | 1.354 | -7.568 | 1.00 | 30.06 | A C |
| ATOM | 1141 | CA | PRO | A | 184 | 4.667 | -0.303 | -5.973 | 1.00 | 36.52 | A C |
| ATOM | 1142 | CB | PRO | A | 184 | 5.179 | -0.617 | -7.374 | 1.00 | 30.06 | A C |
| ATOM | 1143 | CG | PRO | A | 184 | 4.141 | 0.003 | -8.231 | 1.00 | 30.06 | A C |
| ATOM | 1144 | C | PRO | A | 184 | 5.770 | -0.333 | -4.925 | 1.00 | 36.52 | A C |
| ATOM | 1145 | O | PRO | A | 184 | 5.898 | -1.305 | -4.177 | 1.00 | 36.52 | A O |
| ATOM | 1146 | N | GLN | A | 185 | 6.552 | 0.739 | -4.863 | 1.00 | 37.17 | A N |
| ATOM | 1147 | CA | GLN | A | 185 | 7.658 | 0.834 | -3.915 | 1.00 | 37.17 | A C |
| ATOM | 1148 | CB | GLN | A | 185 | 8.503 | 2.078 | -4.208 | 1.00 | 39.30 | A C |
| ATOM | 1149 | CG | GLN | A | 185 | 9.192 | 2.065 | -5.570 | 1.00 | 39.30 | A C |
| ATOM | 1150 | CD | GLN | A | 185 | 8.235 | 2.338 | -6.744 | 1.00 | 39.30 | A C |
| ATOM | 1151 | OE1 | GLN | A | 185 | 7.010 | 2.311 | -6.596 | 1.00 | 39.30 | A O |
| ATOM | 1152 | NE2 | GLN | A | 185 | 8.805 | 2.597 | -7.917 | 1.00 | 39.30 | A N |
| ATOM | 1153 | C | GLN | A | 185 | 7.224 | 0.858 | -2.451 | 1.00 | 37.17 | A C |
| ATOM | 1154 | O | GLN | A | 185 | 8.046 | 0.652 | -1.560 | 1.00 | 37.17 | A O |
| ATOM | 1155 | N | ASN | A | 186 | 5.943 | 1.111 | -2.198 | 1.00 | 34.70 | A N |
| ATOM | 1156 | CA | ASN | A | 186 | 5.440 | 1.167 | -0.835 | 1.00 | 34.70 | A C |
| ATOM | 1157 | CB | ASN | A | 186 | 4.689 | 2.478 | -0.575 | 1.00 | 29.65 | A C |
| ATOM | 1158 | CG | ASN | A | 186 | 5.616 | 3.670 | -0.429 | 1.00 | 29.65 | A C |
| ATOM | 1159 | OD1 | ASN | A | 186 | 6.610 | 3.610 | 0.287 | 1.00 | 29.65 | A O |
| ATOM | 1160 | ND2 | ASN | A | 186 | 5.286 | 4.763 | -1.097 | 1.00 | 29.65 | A N |
| ATOM | 1161 | C | ASN | A | 186 | 4.528 | 0.007 | -0.506 | 1.00 | 34.70 | A C |
| ATOM | 1162 | O | ASN | A | 186 | 3.803 | 0.048 | 0.484 | 1.00 | 34.70 | A O |
| ATOM | 1163 | N | LEU | A | 187 | 4.544 | -1.023 | -1.336 | 1.00 | 28.67 | A N |
| ATOM | 1164 | CA | LEU | A | 187 | 3.717 | -2.185 | -1.066 | 1.00 | 28.67 | A C |
| ATOM | 1165 | CB | LEU | A | 187 | 2.868 | -2.550 | -2.288 | 1.00 | 35.49 | A C |
| ATOM | 1166 | CG | LEU | A | 187 | 1.874 | -1.521 | -2.851 | 1.00 | 35.49 | A C |
| ATOM | 1167 | CD1 | LEU | A | 187 | 1.286 | -2.055 | -4.141 | 1.00 | 35.49 | A C |
| ATOM | 1168 | CD2 | LEU | A | 187 | 0.773 | -1.229 | -1.844 | 1.00 | 35.49 | A C |
| ATOM | 1169 | C | LEU | A | 187 | 4.666 | -3.316 | -0.732 | 1.00 | 28.67 | A C |
| ATOM | 1170 | O | LEU | A | 187 | 5.199 | -3.976 | -1.621 | 1.00 | 28.67 | A O |
| ATOM | 1171 | N | LEU | A | 188 | 4.905 | -3.518 | 0.556 | 1.00 | 50.22 | A N |
| ATOM | 1172 | CA | LEU | A | 188 | 5.802 | -4.577 | 0.994 | 1.00 | 50.22 | A C |
| ATOM | 1173 | CB | LEU | A | 188 | 6.242 | -4.340 | 2.431 | 1.00 | 44.62 | A C |
| ATOM | 1174 | CG | LEU | A | 188 | 6.778 | -2.962 | 2.786 | 1.00 | 44.62 | A C |
| ATOM | 1175 | CD1 | LEU | A | 188 | 7.213 | -3.010 | 4.235 | 1.00 | 44.62 | A C |
| ATOM | 1176 | CD2 | LEU | A | 188 | 7.942 | -2.578 | 1.892 | 1.00 | 44.62 | A C |
| ATOM | 1177 | C | LEU | A | 188 | 5.065 | -5.903 | 0.928 | 1.00 | 50.22 | A C |
| ATOM | 1178 | O | LEU | A | 188 | 3.828 | -5.930 | 0.956 | 1.00 | 50.22 | A O |
| ATOM | 1179 | N | LEU | A | 189 | 5.812 | -7.003 | 0.848 | 1.00 | 39.41 | A N |
| ATOM | 1180 | CA | LEU | A | 189 | 5.183 | -8.314 | 0.796 | 1.00 | 39.41 | A C |
| ATOM | 1181 | CB | LEU | A | 189 | 4.498 | -8.537 | -0.559 | 1.00 | 56.58 | A C |
| ATOM | 1182 | CG | LEU | A | 189 | 5.377 | -8.653 | -1.800 | 1.00 | 56.58 | A C |
| ATOM | 1183 | CD1 | LEU | A | 189 | 4.535 | -8.896 | -3.028 | 1.00 | 56.58 | A C |
| ATOM | 1184 | CD2 | LEU | A | 189 | 6.164 | -7.387 | -1.959 | 1.00 | 56.58 | A C |
| ATOM | 1185 | C | LEU | A | 189 | 6.149 | -9.447 | 1.069 | 1.00 | 39.41 | A C |
| ATOM | 1186 | O | LEU | A | 189 | 7.284 | -9.451 | 0.597 | 1.00 | 39.41 | A O |
| ATOM | 1187 | N | ASP | A | 190 | 5.670 | -10.405 | 1.854 | 1.00 | 53.32 | A N |
| ATOM | 1188 | CA | ASP | A | 190 | 6.419 | -11.595 | 2.228 | 1.00 | 53.32 | A C |
| ATOM | 1189 | CB | ASP | A | 190 | 5.898 | -12.103 | 3.573 | 1.00 | 69.54 | A C |
| ATOM | 1190 | CG | ASP | A | 190 | 6.558 | -13.393 | 4.015 | 1.00 | 69.54 | A C |
| ATOM | 1191 | OD1 | ASP | A | 190 | 6.370 | -14.434 | 3.344 | 1.00 | 69.54 | A O |
| ATOM | 1192 | OD2 | ASP | A | 190 | 7.267 | -13.368 | 5.043 | 1.00 | 69.54 | A O |
| ATOM | 1193 | C | ASP | A | 190 | 6.218 | -12.651 | 1.134 | 1.00 | 53.32 | A C |
| ATOM | 1194 | O | ASP | A | 190 | 5.126 | -13.195 | 0.968 | 1.00 | 53.32 | A O |
| ATOM | 1195 | N | PRO | A | 191 | 7.282 | -12.966 | 0.385 | 1.00 | 61.39 | A N |
| ATOM | 1196 | CD | PRO | A | 191 | 8.686 | -12.602 | 0.659 | 1.00 | 73.41 | A C |
| ATOM | 1197 | CA | PRO | A | 191 | 7.202 | -13.957 | -0.693 | 1.00 | 61.39 | A C |
| ATOM | 1198 | CB | PRO | A | 191 | 8.645 | -14.031 | -1.198 | 1.00 | 73.41 | A C |
| ATOM | 1199 | CG | PRO | A | 191 | 9.448 | -13.773 | 0.066 | 1.00 | 73.41 | A C |

FIG. 3-19

| ATOM | 1200 | C | PRO | A | 191 | 6.627 | -15.338 | -0.325 | 1.00 | 61.39 | A | C |
|---|---|---|---|---|---|---|---|---|---|---|---|---|
| ATOM | 1201 | O | PRO | A | 191 | 5.838 | -15.892 | -1.086 | 1.00 | 61.39 | A | O |
| ATOM | 1202 | N | ASP | A | 192 | 6.995 | -15.893 | 0.827 | 1.00 | 42.47 | A | N |
| ATOM | 1203 | CA | ASP | A | 192 | 6.484 | -17.218 | 1.190 | 1.00 | 42.47 | A | C |
| ATOM | 1204 | CB | ASP | A | 192 | 7.370 | -17.888 | 2.256 | 1.00 | 72.10 | A | C |
| ATOM | 1205 | CG | ASP | A | 192 | 8.847 | -17.942 | 1.868 | 1.00 | 72.10 | A | C |
| ATOM | 1206 | OD1 | ASP | A | 192 | 9.184 | -18.343 | 0.725 | 1.00 | 72.10 | A | O |
| ATOM | 1207 | OD2 | ASP | A | 192 | 9.675 | -17.591 | 2.736 | 1.00 | 72.10 | A | O |
| ATOM | 1208 | C | ASP | A | 192 | 5.044 | -17.240 | 1.701 | 1.00 | 42.47 | A | C |
| ATOM | 1209 | O | ASP | A | 192 | 4.415 | -18.302 | 1.751 | 1.00 | 42.47 | A | O |
| ATOM | 1210 | N | THR | A | 193 | 4.518 | -16.093 | 2.109 | 1.00 | 43.70 | A | N |
| ATOM | 1211 | CA | THR | A | 193 | 3.150 | -16.068 | 2.617 | 1.00 | 43.70 | A | C |
| ATOM | 1212 | CB | THR | A | 193 | 3.072 | -15.470 | 4.040 | 1.00 | 50.47 | A | C |
| ATOM | 1213 | OG1 | THR | A | 193 | 3.762 | -14.215 | 4.084 | 1.00 | 50.47 | A | O |
| ATOM | 1214 | CG2 | THR | A | 193 | 3.692 | -16.413 | 5.035 | 1.00 | 50.47 | A | C |
| ATOM | 1215 | C | THR | A | 193 | 2.233 | -15.295 | 1.700 | 1.00 | 43.70 | A | C |
| ATOM | 1216 | O | THR | A | 193 | 1.014 | -15.464 | 1.742 | 1.00 | 43.70 | A | O |
| ATOM | 1217 | N | ALA | A | 194 | 2.842 | -14.455 | 0.871 | 1.00 | 46.87 | A | N |
| ATOM | 1218 | CA | ALA | A | 194 | 2.123 | -13.634 | -0.097 | 1.00 | 46.87 | A | C |
| ATOM | 1219 | CB | ALA | A | 194 | 1.274 | -14.526 | -1.011 | 1.00 | 39.81 | A | C |
| ATOM | 1220 | C | ALA | A | 194 | 1.251 | -12.544 | 0.528 | 1.00 | 46.87 | A | C |
| ATOM | 1221 | O | ALA | A | 194 | 0.272 | -12.109 | -0.071 | 1.00 | 46.87 | A | O |
| ATOM | 1222 | N | VAL | A | 195 | 1.593 | -12.097 | 1.729 | 1.00 | 32.58 | A | N |
| ATOM | 1223 | CA | VAL | A | 195 | 0.803 | -11.051 | 2.347 | 1.00 | 32.58 | A | C |
| ATOM | 1224 | CB | VAL | A | 195 | 0.713 | -11.249 | 3.880 | 1.00 | 41.42 | A | C |
| ATOM | 1225 | CG1 | VAL | A | 195 | 0.689 | -12.737 | 4.196 | 1.00 | 41.42 | A | C |
| ATOM | 1226 | CG2 | VAL | A | 195 | 1.852 | -10.532 | 4.594 | 1.00 | 41.42 | A | C |
| ATOM | 1227 | C | VAL | A | 195 | 1.425 | -9.695 | 2.005 | 1.00 | 32.58 | A | C |
| ATOM | 1228 | O | VAL | A | 195 | 2.648 | -9.539 | 1.977 | 1.00 | 32.58 | A | O |
| ATOM | 1229 | N | LEU | A | 196 | 0.573 | -8.721 | 1.718 | 1.00 | 47.57 | A | N |
| ATOM | 1230 | CA | LEU | A | 196 | 1.044 | -7.391 | 1.368 | 1.00 | 47.57 | A | C |
| ATOM | 1231 | CB | LEU | A | 196 | 0.324 | -6.910 | 0.101 | 1.00 | 27.30 | A | C |
| ATOM | 1232 | CG | LEU | A | 196 | 0.630 | -5.527 | -0.477 | 1.00 | 27.30 | A | C |
| ATOM | 1233 | CD1 | LEU | A | 196 | 0.367 | -5.541 | -1.945 | 1.00 | 27.30 | A | C |
| ATOM | 1234 | CD2 | LEU | A | 196 | -0.212 | -4.481 | 0.188 | 1.00 | 27.30 | A | C |
| ATOM | 1235 | C | LEU | A | 196 | 0.812 | -6.420 | 2.525 | 1.00 | 47.57 | A | C |
| ATOM | 1236 | O | LEU | A | 196 | -0.126 | -6.584 | 3.317 | 1.00 | 47.57 | A | O |
| ATOM | 1237 | N | LYS | A | 197 | 1.670 | -5.410 | 2.625 | 1.00 | 56.26 | A | N |
| ATOM | 1238 | CA | LYS | A | 197 | 1.554 | -4.426 | 3.690 | 1.00 | 56.26 | A | C |
| ATOM | 1239 | CB | LYS | A | 197 | 2.529 | -4.754 | 4.818 | 1.00 | 43.34 | A | C |
| ATOM | 1240 | CG | LYS | A | 197 | 2.137 | -5.980 | 5.573 | 1.00 | 43.34 | A | C |
| ATOM | 1241 | CD | LYS | A | 197 | 3.228 | -6.470 | 6.466 | 1.00 | 43.34 | A | C |
| ATOM | 1242 | CE | LYS | A | 197 | 2.729 | -7.685 | 7.217 | 1.00 | 43.34 | A | C |
| ATOM | 1243 | NZ | LYS | A | 197 | 1.392 | -7.388 | 7.799 | 1.00 | 43.34 | A | N |
| ATOM | 1244 | C | LYS | A | 197 | 1.820 | -3.018 | 3.214 | 1.00 | 56.26 | A | C |
| ATOM | 1245 | O | LYS | A | 197 | 2.875 | -2.728 | 2.641 | 1.00 | 56.26 | A | O |
| ATOM | 1246 | N | LEU | A | 198 | 0.861 | -2.134 | 3.444 | 1.00 | 37.07 | A | N |
| ATOM | 1247 | CA | LEU | A | 198 | 1.055 | -0.759 | 3.061 | 1.00 | 37.07 | A | C |
| ATOM | 1248 | CB | LEU | A | 198 | -0.255 | 0.017 | 3.190 | 1.00 | 46.50 | A | C |
| ATOM | 1249 | CG | LEU | A | 198 | -0.727 | 0.860 | 1.993 | 1.00 | 46.50 | A | C |
| ATOM | 1250 | CD1 | LEU | A | 198 | -1.917 | 1.695 | 2.420 | 1.00 | 46.50 | A | C |
| ATOM | 1251 | CD2 | LEU | A | 198 | 0.378 | 1.765 | 1.493 | 1.00 | 46.50 | A | C |
| ATOM | 1252 | C | LEU | A | 198 | 2.074 | -0.214 | 4.055 | 1.00 | 37.07 | A | C |
| ATOM | 1253 | O | LEU | A | 198 | 1.999 | -0.505 | 5.254 | 1.00 | 37.07 | A | O |
| ATOM | 1254 | N | CYS | A | 199 | 3.045 | 0.542 | 3.558 | 1.00 | 43.73 | A | N |
| ATOM | 1255 | CA | CYS | A | 199 | 4.034 | 1.157 | 4.431 | 1.00 | 43.73 | A | C |
| ATOM | 1256 | CB | CYS | A | 199 | 5.333 | 0.327 | 4.502 | 1.00 | 58.44 | A | C |
| ATOM | 1257 | SG | CYS | A | 199 | 6.464 | 0.479 | 3.086 | 1.00 | 58.44 | A | S |
| ATOM | 1258 | C | CYS | A | 199 | 4.309 | 2.554 | 3.888 | 1.00 | 43.73 | A | C |
| ATOM | 1259 | O | CYS | A | 199 | 3.873 | 2.890 | 2.799 | 1.00 | 43.73 | A | O |
| ATOM | 1260 | N | ASP | A | 200 | 5.039 | 3.355 | 4.657 | 1.00 | 51.23 | A | N |
| ATOM | 1261 | CA | ASP | A | 200 | 5.383 | 4.736 | 4.312 | 1.00 | 51.23 | A | C |
| ATOM | 1262 | CB | ASP | A | 200 | 5.992 | 4.844 | 2.917 | 1.00 | 60.23 | A | C |
| ATOM | 1263 | CG | ASP | A | 200 | 6.639 | 6.207 | 2.679 | 1.00 | 60.23 | A | C |
| ATOM | 1264 | OD1 | ASP | A | 200 | 6.448 | 7.103 | 3.538 | 1.00 | 60.23 | A | O |
| ATOM | 1265 | OD2 | ASP | A | 200 | 7.335 | 6.394 | 1.644 | 1.00 | 60.23 | A | O |
| ATOM | 1266 | C | ASP | A | 200 | 4.168 | 5.647 | 4.400 | 1.00 | 51.23 | A | C |

FIG. 3-20

```
ATOM   1267  O    ASP A 200       3.537   5.969   3.391  1.00 51.23      A  O
ATOM   1268  N    PHE A 201       3.839   6.048   5.623  1.00 36.54      A  N
ATOM   1269  CA   PHE A 201       2.713   6.932   5.845  1.00 36.54      A  C
ATOM   1270  CB   PHE A 201       1.896   6.460   7.051  1.00 39.75      A  C
ATOM   1271  CG   PHE A 201       1.023   5.258   6.769  1.00 39.75      A  C
ATOM   1272  CD1  PHE A 201       1.578   3.993   6.621  1.00 39.75      A  C
ATOM   1273  CD2  PHE A 201      -0.367   5.394   6.670  1.00 39.75      A  C
ATOM   1274  CE1  PHE A 201       0.760   2.881   6.379  1.00 39.75      A  C
ATOM   1275  CE2  PHE A 201      -1.192   4.292   6.431  1.00 39.75      A  C
ATOM   1276  CZ   PHE A 201      -0.633   3.037   6.286  1.00 39.75      A  C
ATOM   1277  C    PHE A 201       3.222   8.347   6.066  1.00 36.54      A  C
ATOM   1278  O    PHE A 201       2.576   9.145   6.735  1.00 36.54      A  O
ATOM   1279  N    GLY A 202       4.380   8.651   5.484  1.00 40.97      A  N
ATOM   1280  CA   GLY A 202       4.973   9.969   5.636  1.00 40.97      A  C
ATOM   1281  C    GLY A 202       4.275  11.085   4.875  1.00 40.97      A  C
ATOM   1282  O    GLY A 202       4.645  12.245   5.017  1.00 40.97      A  O
ATOM   1283  N    SER A 203       3.276  10.733   4.067  1.00 41.55      A  N
ATOM   1284  CA   SER A 203       2.510  11.691   3.266  1.00 41.55      A  C
ATOM   1285  CB   SER A 203       2.714  11.440   1.770  1.00 37.73      A  C
ATOM   1286  OG   SER A 203       4.084  11.415   1.428  1.00 37.73      A  O
ATOM   1287  C    SER A 203       1.034  11.498   3.569  1.00 41.55      A  C
ATOM   1288  O    SER A 203       0.179  12.202   3.030  1.00 41.55      A  O
ATOM   1289  N    ALA A 204       0.743  10.513   4.414  1.00 49.19      A  N
ATOM   1290  CA   ALA A 204      -0.629  10.206   4.784  1.00 49.19      A  C
ATOM   1291  CB   ALA A 204      -0.675   8.914   5.615  1.00 27.24      A  C
ATOM   1292  C    ALA A 204      -1.205  11.374   5.571  1.00 49.19      A  C
ATOM   1293  O    ALA A 204      -0.479  12.064   6.282  1.00 49.19      A  O
ATOM   1294  N    LYS A 205      -2.508  11.593   5.449  1.00 33.17      A  N
ATOM   1295  CA   LYS A 205      -3.148  12.686   6.155  1.00 33.17      A  C
ATOM   1296  CB   LYS A 205      -2.875  14.001   5.434  1.00 30.26      A  C
ATOM   1297  CG   LYS A 205      -3.725  15.175   5.889  1.00 30.26      A  C
ATOM   1298  CD   LYS A 205      -3.254  16.440   5.189  1.00 30.26      A  C
ATOM   1299  CE   LYS A 205      -4.027  17.671   5.618  1.00 30.26      A  C
ATOM   1300  NZ   LYS A 205      -3.506  18.859   4.891  1.00 30.26      A  N
ATOM   1301  C    LYS A 205      -4.637  12.505   6.280  1.00 33.17      A  C
ATOM   1302  O    LYS A 205      -5.300  12.029   5.360  1.00 33.17      A  O
ATOM   1303  N    GLN A 206      -5.165  12.888   7.432  1.00 61.09      A  N
ATOM   1304  CA   GLN A 206      -6.595  12.804   7.657  1.00 61.09      A  C
ATOM   1305  CB   GLN A 206      -6.897  12.891   9.151  1.00 99.25      A  C
ATOM   1306  CG   GLN A 206      -8.366  12.756   9.475  1.00 99.25      A  C
ATOM   1307  CD   GLN A 206      -8.598  12.072  10.810  1.00 99.25      A  C
ATOM   1308  OE1  GLN A 206      -9.718  12.101  11.350  1.00 99.25      A  O
ATOM   1309  NE2  GLN A 206      -7.540  11.441  11.357  1.00 99.25      A  N
ATOM   1310  C    GLN A 206      -7.185  13.995   6.911  1.00 61.09      A  C
ATOM   1311  O    GLN A 206      -6.825  15.141   7.177  1.00 61.09      A  O
ATOM   1312  N    LEU A 207      -8.067  13.724   5.957  1.00 49.78      A  N
ATOM   1313  CA   LEU A 207      -8.663  14.797   5.166  1.00 49.78      A  C
ATOM   1314  CB   LEU A 207      -8.888  14.356   3.719  1.00 30.14      A  C
ATOM   1315  CG   LEU A 207      -7.656  13.896   2.936  1.00 30.14      A  C
ATOM   1316  CD1  LEU A 207      -8.112  13.300   1.626  1.00 30.14      A  C
ATOM   1317  CD2  LEU A 207      -6.678  15.044   2.722  1.00 30.14      A  C
ATOM   1318  C    LEU A 207      -9.975  15.238   5.760  1.00 49.78      A  C
ATOM   1319  O    LEU A 207     -10.831  14.414   6.102  1.00 49.78      A  O
ATOM   1320  N    VAL A 208     -10.111  16.553   5.887  1.00 43.58      A  N
ATOM   1321  CA   VAL A 208     -11.306  17.166   6.433  1.00 43.58      A  C
ATOM   1322  CB   VAL A 208     -10.966  18.046   7.662  1.00 49.68      A  C
ATOM   1323  CG1  VAL A 208     -11.995  19.145   7.826  1.00 49.68      A  C
ATOM   1324  CG2  VAL A 208     -10.937  17.190   8.918  1.00 49.68      A  C
ATOM   1325  C    VAL A 208     -11.944  18.015   5.348  1.00 43.58      A  C
ATOM   1326  O    VAL A 208     -11.289  18.875   4.737  1.00 43.58      A  O
ATOM   1327  N    ARG A 209     -13.222  17.759   5.102  1.00 43.13      A  N
ATOM   1328  CA   ARG A 209     -13.945  18.511   4.092  1.00 43.13      A  C
ATOM   1329  CB   ARG A 209     -15.400  18.052   4.040  1.00 93.17      A  C
ATOM   1330  CG   ARG A 209     -16.184  18.609   2.846  1.00 93.17      A  C
ATOM   1331  CD   ARG A 209     -17.605  18.061   2.841  1.00 93.17      A  C
ATOM   1332  NE   ARG A 209     -17.597  16.639   3.190  1.00 93.17      A  N
ATOM   1333  CZ   ARG A 209     -18.687  15.908   3.417  1.00 93.17      A  C
```

FIG. 3-21

```
ATOM   1334  NH1 ARG A 209     -19.905  16.461   3.328  1.00 93.17      A  N
ATOM   1335  NH2 ARG A 209     -18.553  14.625   3.760  1.00 93.17      A  N
ATOM   1336  C   ARG A 209     -13.893  19.993   4.443  1.00 43.13      A  C
ATOM   1337  O   ARG A 209     -14.405  20.405   5.488  1.00 43.13      A  O
ATOM   1338  N   GLY A 210     -13.273  20.794   3.583  1.00 50.74      A  N
ATOM   1339  CA  GLY A 210     -13.200  22.219   3.852  1.00 50.74      A  C
ATOM   1340  C   GLY A 210     -11.782  22.736   3.978  1.00 50.74      A  C
ATOM   1341  O   GLY A 210     -11.435  23.790   3.423  1.00 50.74      A  O
ATOM   1342  N   GLU A 211     -10.955  22.000   4.715  1.00 57.36      A  N
ATOM   1343  CA  GLU A 211      -9.565  22.403   4.890  1.00 57.36      A  C
ATOM   1344  CB  GLU A 211      -9.005  21.755   6.158  1.00 66.68      A  C
ATOM   1345  CG  GLU A 211      -9.878  21.991   7.381  1.00 66.68      A  C
ATOM   1346  CD  GLU A 211      -9.536  21.060   8.538  1.00 66.68      A  C
ATOM   1347  OE1 GLU A 211     -10.171  21.184   9.617  1.00 66.68      A  O
ATOM   1348  OE2 GLU A 211      -8.639  20.200   8.365  1.00 66.68      A  O
ATOM   1349  C   GLU A 211      -8.787  21.962   3.645  1.00 57.36      A  C
ATOM   1350  O   GLU A 211      -8.667  20.774   3.362  1.00 57.36      A  O
ATOM   1351  N   PRO A 212      -8.277  22.922   2.865  1.00 49.93      A  N
ATOM   1352  CD  PRO A 212      -8.293  24.377   3.086  1.00 52.84      A  C
ATOM   1353  CA  PRO A 212      -7.522  22.585   1.651  1.00 49.93      A  C
ATOM   1354  CB  PRO A 212      -7.149  23.955   1.079  1.00 52.84      A  C
ATOM   1355  CG  PRO A 212      -7.069  24.825   2.304  1.00 52.84      A  C
ATOM   1356  C   PRO A 212      -6.297  21.722   1.903  1.00 49.93      A  C
ATOM   1357  O   PRO A 212      -5.757  21.708   3.009  1.00 49.93      A  O
ATOM   1358  N   ASN A 213      -5.868  21.010   0.862  1.00 44.51      A  N
ATOM   1359  CA  ASN A 213      -4.703  20.132   0.934  1.00 44.51      A  C
ATOM   1360  CB  ASN A 213      -5.150  18.674   0.920  1.00 37.35      A  C
ATOM   1361  CG  ASN A 213      -6.212  18.389   1.946  1.00 37.35      A  C
ATOM   1362  OD1 ASN A 213      -5.974  18.495   3.142  1.00 37.35      A  O
ATOM   1363  ND2 ASN A 213      -7.403  18.035   1.483  1.00 37.35      A  N
ATOM   1364  C   ASN A 213      -3.795  20.388  -0.261  1.00 44.51      A  C
ATOM   1365  O   ASN A 213      -4.256  20.836  -1.300  1.00 44.51      A  O
ATOM   1366  N   VAL A 214      -2.507  20.105  -0.111  1.00 34.13      A  N
ATOM   1367  CA  VAL A 214      -1.549  20.293  -1.197  1.00 34.13      A  C
ATOM   1368  CB  VAL A 214      -0.109  19.954  -0.726  1.00 35.10      A  C
ATOM   1369  CG1 VAL A 214       0.831  19.824  -1.917  1.00 35.10      A  C
ATOM   1370  CG2 VAL A 214       0.388  21.032   0.207  1.00 35.10      A  C
ATOM   1371  C   VAL A 214      -1.920  19.384  -2.366  1.00 34.13      A  C
ATOM   1372  O   VAL A 214      -2.209  18.202  -2.173  1.00 34.13      A  O
ATOM   1373  N   SER A 215      -1.915  19.928  -3.578  1.00 42.10      A  N
ATOM   1374  CA  SER A 215      -2.270  19.118  -4.734  1.00 42.10      A  C
ATOM   1375  CB  SER A 215      -2.597  20.006  -5.943  1.00 53.16      A  C
ATOM   1376  OG  SER A 215      -1.539  20.897  -6.248  1.00 53.16      A  O
ATOM   1377  C   SER A 215      -1.153  18.125  -5.061  1.00 42.10      A  C
ATOM   1378  O   SER A 215      -0.885  17.800  -6.219  1.00 42.10      A  O
ATOM   1379  N   PTY A 216       0.671  19.561  -5.342  1.00 45.96      A  N
ATOM   1380  CA  PTY A 216       1.727  18.589  -5.592  1.00 45.96      A  C
ATOM   1381  C   PTY A 216       1.903  17.684  -4.381  1.00 45.96      A  C
ATOM   1382  O   PTY A 216       2.851  16.901  -4.309  1.00 45.96      A  O
ATOM   1383  CB  PTY A 216       3.033  19.319  -5.870  1.00 45.96      A  C
ATOM   1384  CG  PTY A 216       3.913  18.570  -6.766  1.00 45.96      A  C
ATOM   1385  CD1 PTY A 216       3.639  18.539  -8.205  1.00 45.96      A  C
ATOM   1386  CD2 PTY A 216       5.184  18.076  -6.235  1.00 45.96      A  C
ATOM   1387  CE1 PTY A 216       4.663  18.012  -9.107  1.00 45.96      A  C
ATOM   1388  CE2 PTY A 216       6.187  17.560  -7.164  1.00 45.96      A  C
ATOM   1389  CZ  PTY A 216       5.944  17.522  -8.604  1.00 45.96      A  C
ATOM   1390  OH  PTY A 216       6.920  17.109  -9.474  1.00 45.96      A  O
ATOM   1391  P   PTY A 216       6.966  15.626  -9.781  1.00 45.96      A  P
ATOM   1392  OP1 PTY A 216       6.050  15.498 -10.957  1.00 45.96      A  O
ATOM   1393  OP2 PTY A 216       6.561  14.822  -8.498  1.00 45.96      A  O
ATOM   1394  OP3 PTY A 216       8.365  15.302 -10.211  1.00 45.96      A  O
ATOM   1395  N   ILE A 217       0.818  15.558  -4.827  1.00 44.35      A  N
ATOM   1396  CA  ILE A 217       1.502  14.532  -4.070  1.00 44.35      A  C
ATOM   1397  CB  ILE A 217       0.869  14.335  -2.658  1.00 56.22      A  C
ATOM   1398  CG2 ILE A 217       1.335  15.430  -1.707  1.00 56.22      A  C
ATOM   1399  CG1 ILE A 217      -0.658  14.302  -2.760  1.00 56.22      A  C
ATOM   1400  CD1 ILE A 217      -1.275  15.611  -3.165  1.00 56.22      A  C
```

FIG. 3-22

| | | | | | | | | | | |
|---|---|---|---|---|---|---|---|---|---|---|
| ATOM | 1401 | C | ILE | A | 217 | 1.419 | 13.232 | -4.854 | 1.00 44.35 | A C |
| ATOM | 1402 | O | ILE | A | 217 | 0.807 | 13.191 | -5.919 | 1.00 44.35 | A O |
| ATOM | 1403 | N | CYS | A | 218 | 2.023 | 12.181 | -4.307 | 1.00 40.34 | A N |
| ATOM | 1404 | CA | CYS | A | 218 | 2.069 | 10.856 | -4.931 | 1.00 40.34 | A C |
| ATOM | 1405 | CB | CYS | A | 218 | 0.762 | 10.486 | -5.646 | 1.00 47.49 | A C |
| ATOM | 1406 | SG | CYS | A | 218 | -0.761 | 10.832 | -4.804 | 1.00 47.49 | A S |
| ATOM | 1407 | C | CYS | A | 218 | 3.153 | 10.885 | -5.984 | 1.00 40.34 | A C |
| ATOM | 1408 | O | CYS | A | 218 | 3.417 | 11.934 | -6.570 | 1.00 40.34 | A O |
| ATOM | 1409 | N | SER | A | 219 | 3.787 | 9.746 | -6.238 | 1.00 33.71 | A N |
| ATOM | 1410 | CA | SER | A | 219 | 4.787 | 9.732 | -7.284 | 1.00 33.71 | A C |
| ATOM | 1411 | CB | SER | A | 219 | 5.409 | 8.350 | -7.435 | 1.00 48.03 | A C |
| ATOM | 1412 | OG | SER | A | 219 | 6.105 | 7.993 | -6.261 | 1.00 48.03 | A O |
| ATOM | 1413 | C | SER | A | 219 | 4.008 | 10.079 | -8.535 | 1.00 33.71 | A C |
| ATOM | 1414 | O | SER | A | 219 | 2.895 | 9.616 | -8.722 | 1.00 33.71 | A O |
| ATOM | 1415 | N | ARG | A | 220 | 4.596 | 10.905 | -9.382 | 1.00 36.99 | A N |
| ATOM | 1416 | CA | ARG | A | 220 | 3.977 | 11.338 | -10.628 | 1.00 36.99 | A C |
| ATOM | 1417 | CB | ARG | A | 220 | 5.051 | 11.889 | -11.549 | 1.00 44.99 | A C |
| ATOM | 1418 | CG | ARG | A | 220 | 4.518 | 12.508 | -12.795 | 1.00 44.99 | A C |
| ATOM | 1419 | CD | ARG | A | 220 | 5.516 | 13.515 | -13.306 | 1.00 44.99 | A C |
| ATOM | 1420 | NE | ARG | A | 220 | 6.722 | 12.887 | -13.831 | 1.00 44.99 | A N |
| ATOM | 1421 | CZ | ARG | A | 220 | 7.928 | 13.434 | -13.761 | 1.00 44.99 | A C |
| ATOM | 1422 | NH1 | ARG | A | 220 | 8.092 | 14.617 | -13.178 | 1.00 44.99 | A N |
| ATOM | 1423 | NH2 | ARG | A | 220 | 8.965 | 12.809 | -14.288 | 1.00 44.99 | A N |
| ATOM | 1424 | C | ARG | A | 220 | 3.179 | 10.288 | -11.383 | 1.00 36.99 | A C |
| ATOM | 1425 | O | ARG | A | 220 | 2.012 | 10.497 | -11.705 | 1.00 36.99 | A O |
| ATOM | 1426 | N | TYR | A | 221 | 3.820 | 9.166 | -11.676 | 1.00 39.79 | A N |
| ATOM | 1427 | CA | TYR | A | 221 | 3.174 | 8.089 | -12.421 | 1.00 39.79 | A C |
| ATOM | 1428 | CB | TYR | A | 221 | 4.087 | 6.867 | -12.498 | 1.00 43.50 | A C |
| ATOM | 1429 | CG | TYR | A | 221 | 5.325 | 7.051 | -13.342 | 1.00 43.50 | A C |
| ATOM | 1430 | CD1 | TYR | A | 221 | 5.687 | 8.309 | -13.824 | 1.00 43.50 | A C |
| ATOM | 1431 | CE1 | TYR | A | 221 | 6.815 | 8.476 | -14.594 | 1.00 43.50 | A C |
| ATOM | 1432 | CD2 | TYR | A | 221 | 6.135 | 5.964 | -13.654 | 1.00 43.50 | A C |
| ATOM | 1433 | CE2 | TYR | A | 221 | 7.269 | 6.124 | -14.422 | 1.00 43.50 | A C |
| ATOM | 1434 | CZ | TYR | A | 221 | 7.602 | 7.382 | -14.891 | 1.00 43.50 | A C |
| ATOM | 1435 | OH | TYR | A | 221 | 8.721 | 7.542 | -15.668 | 1.00 43.50 | A O |
| ATOM | 1436 | C | TYR | A | 221 | 1.866 | 7.651 | -11.812 | 1.00 39.79 | A C |
| ATOM | 1437 | O | TYR | A | 221 | 0.938 | 7.265 | -12.519 | 1.00 39.79 | A O |
| ATOM | 1438 | N | TYR | A | 222 | 1.802 | 7.710 | -10.489 | 1.00 39.86 | A N |
| ATOM | 1439 | CA | TYR | A | 222 | 0.629 | 7.270 | -9.764 | 1.00 39.86 | A C |
| ATOM | 1440 | CB | TYR | A | 222 | 1.087 | 6.372 | -8.620 | 1.00 41.27 | A C |
| ATOM | 1441 | CG | TYR | A | 222 | 2.057 | 5.323 | -9.099 | 1.00 41.27 | A C |
| ATOM | 1442 | CD1 | TYR | A | 222 | 3.423 | 5.592 | -9.174 | 1.00 41.27 | A C |
| ATOM | 1443 | CE1 | TYR | A | 222 | 4.310 | 4.671 | -9.732 | 1.00 41.27 | A C |
| ATOM | 1444 | CD2 | TYR | A | 222 | 1.603 | 4.095 | -9.590 | 1.00 41.27 | A C |
| ATOM | 1445 | CE2 | TYR | A | 222 | 2.487 | 3.171 | -10.151 | 1.00 41.27 | A C |
| ATOM | 1446 | CZ | TYR | A | 222 | 3.834 | 3.473 | -10.217 | 1.00 41.27 | A C |
| ATOM | 1447 | OH | TYR | A | 222 | 4.704 | 2.582 | -10.773 | 1.00 41.27 | A O |
| ATOM | 1448 | C | TYR | A | 222 | -0.257 | 8.386 | -9.249 | 1.00 39.86 | A C |
| ATOM | 1449 | O | TYR | A | 222 | -1.182 | 8.140 | -8.485 | 1.00 39.86 | A O |
| ATOM | 1450 | N | ARG | A | 223 | 0.013 | 9.607 | -9.694 | 1.00 31.66 | A N |
| ATOM | 1451 | CA | ARG | A | 223 | -0.745 | 10.774 | -9.275 | 1.00 31.66 | A C |
| ATOM | 1452 | CB | ARG | A | 223 | 0.111 | 12.027 | -9.486 | 1.00 40.78 | A C |
| ATOM | 1453 | CG | ARG | A | 223 | -0.644 | 13.331 | -9.304 | 1.00 40.78 | A C |
| ATOM | 1454 | CD | ARG | A | 223 | 0.225 | 14.421 | -8.714 | 1.00 40.78 | A C |
| ATOM | 1455 | NE | ARG | A | 223 | 1.327 | 14.800 | -9.589 | 1.00 40.78 | A N |
| ATOM | 1456 | CZ | ARG | A | 223 | 2.618 | 14.612 | -9.308 | 1.00 40.78 | A C |
| ATOM | 1457 | NH1 | ARG | A | 223 | 2.986 | 14.044 | -8.168 | 1.00 40.78 | A N |
| ATOM | 1458 | NH2 | ARG | A | 223 | 3.546 | 15.001 | -10.173 | 1.00 40.78 | A N |
| ATOM | 1459 | C | ARG | A | 223 | -2.102 | 10.927 | -9.976 | 1.00 31.66 | A C |
| ATOM | 1460 | O | ARG | A | 223 | -2.190 | 10.879 | -11.203 | 1.00 31.66 | A O |
| ATOM | 1461 | N | ALA | A | 224 | -3.157 | 11.114 | -9.185 | 1.00 34.54 | A N |
| ATOM | 1462 | CA | ALA | A | 224 | -4.512 | 11.288 | -9.706 | 1.00 34.54 | A C |
| ATOM | 1463 | CB | ALA | A | 224 | -5.506 | 11.385 | -8.561 | 1.00 40.36 | A C |
| ATOM | 1464 | C | ALA | A | 224 | -4.610 | 12.533 | -10.569 | 1.00 34.54 | A C |
| ATOM | 1465 | O | ALA | A | 224 | -3.993 | 13.559 | -10.276 | 1.00 34.54 | A O |
| ATOM | 1466 | N | PRO | A | 225 | -5.420 | 12.475 | -11.633 | 1.00 41.95 | A N |
| ATOM | 1467 | CD | PRO | A | 225 | -6.399 | 11.423 | -11.946 | 1.00 35.18 | A C |

FIG. 3-23

```
ATOM   1468  CA   PRO A 225      -5.583  13.617 -12.535  1.00 41.95      A  C
ATOM   1469  CB   PRO A 225      -6.548  13.076 -13.587  1.00 35.18      A  C
ATOM   1470  CG   PRO A 225      -7.401  12.162 -12.800  1.00 35.18      A  C
ATOM   1471  C    PRO A 225      -6.059  14.909 -11.849  1.00 41.95      A  C
ATOM   1472  O    PRO A 225      -5.661  16.004 -12.247  1.00 41.95      A  O
ATOM   1473  N    GLU A 226      -6.901  14.795 -10.822  1.00 50.90      A  N
ATOM   1474  CA   GLU A 226      -7.353  15.991 -10.117  1.00 50.90      A  C
ATOM   1475  CB   GLU A 226      -8.106  15.654  -8.839  1.00 32.83      A  C
ATOM   1476  CG   GLU A 226      -9.252  14.730  -9.034  1.00 32.83      A  C
ATOM   1477  CD   GLU A 226      -8.921  13.348  -8.590  1.00 32.83      A  C
ATOM   1478  OE1  GLU A 226      -9.006  13.077  -7.376  1.00 32.83      A  O
ATOM   1479  OE2  GLU A 226      -8.561  12.538  -9.459  1.00 32.83      A  O
ATOM   1480  C    GLU A 226      -6.113  16.752  -9.717  1.00 50.90      A  C
ATOM   1481  O    GLU A 226      -5.927  17.897 -10.105  1.00 50.90      A  O
ATOM   1482  N    LEU A 227      -5.260  16.089  -8.942  1.00 38.71      A  N
ATOM   1483  CA   LEU A 227      -4.018  16.670  -8.450  1.00 38.71      A  C
ATOM   1484  CB   LEU A 227      -3.134  15.584  -7.838  1.00 24.50      A  C
ATOM   1485  CG   LEU A 227      -3.754  14.754  -6.722  1.00 24.50      A  C
ATOM   1486  CD1  LEU A 227      -2.812  13.624  -6.373  1.00 24.50      A  C
ATOM   1487  CD2  LEU A 227      -4.054  15.633  -5.519  1.00 24.50      A  C
ATOM   1488  C    LEU A 227      -3.216  17.421  -9.505  1.00 38.71      A  C
ATOM   1489  O    LEU A 227      -2.697  18.495  -9.234  1.00 38.71      A  O
ATOM   1490  N    ILE A 228      -3.100  16.863 -10.703  1.00 34.36      A  N
ATOM   1491  CA   ILE A 228      -2.336  17.536 -11.736  1.00 34.36      A  C
ATOM   1492  CB   ILE A 228      -2.254  16.705 -13.013  1.00 33.07      A  C
ATOM   1493  CG2  ILE A 228      -1.316  17.386 -14.007  1.00 33.07      A  C
ATOM   1494  CG1  ILE A 228      -1.768  15.294 -12.683  1.00 33.07      A  C
ATOM   1495  CD1  ILE A 228      -1.729  14.380 -13.878  1.00 33.07      A  C
ATOM   1496  C    ILE A 228      -3.010  18.852 -12.055  1.00 34.36      A  C
ATOM   1497  O    ILE A 228      -2.335  19.840 -12.348  1.00 34.36      A  O
ATOM   1498  N    PHE A 229      -4.346  18.847 -11.991  1.00 56.03      A  N
ATOM   1499  CA   PHE A 229      -5.181  20.026 -12.247  1.00 56.03      A  C
ATOM   1500  CB   PHE A 229      -6.636  19.604 -12.453  1.00 33.98      A  C
ATOM   1501  CG   PHE A 229      -7.003  19.354 -13.884  1.00 33.98      A  C
ATOM   1502  CD1  PHE A 229      -7.194  20.410 -14.761  1.00 33.98      A  C
ATOM   1503  CD2  PHE A 229      -7.186  18.058 -14.349  1.00 33.98      A  C
ATOM   1504  CE1  PHE A 229      -7.563  20.176 -16.074  1.00 33.98      A  C
ATOM   1505  CE2  PHE A 229      -7.556  17.811 -15.660  1.00 33.98      A  C
ATOM   1506  CZ   PHE A 229      -7.746  18.874 -16.524  1.00 33.98      A  C
ATOM   1507  C    PHE A 229      -5.134  21.062 -11.116  1.00 56.03      A  C
ATOM   1508  O    PHE A 229      -5.856  22.059 -11.156  1.00 56.03      A  O
ATOM   1509  N    GLY A 230      -4.308  20.813 -10.103  1.00 40.53      A  N
ATOM   1510  CA   GLY A 230      -4.180  21.752  -9.001  1.00 40.53      A  C
ATOM   1511  C    GLY A 230      -5.238  21.651  -7.922  1.00 40.53      A  C
ATOM   1512  O    GLY A 230      -5.241  22.439  -6.978  1.00 40.53      A  O
ATOM   1513  N    ALA A 231      -6.134  20.683  -8.055  1.00 36.52      A  N
ATOM   1514  CA   ALA A 231      -7.192  20.495  -7.072  1.00 36.52      A  C
ATOM   1515  CB   ALA A 231      -7.959  19.223  -7.388  1.00 49.82      A  C
ATOM   1516  C    ALA A 231      -6.633  20.432  -5.649  1.00 36.52      A  C
ATOM   1517  O    ALA A 231      -5.671  19.707  -5.379  1.00 36.52      A  O
ATOM   1518  N    THR A 232      -7.230  21.190  -4.736  1.00 32.87      A  N
ATOM   1519  CA   THR A 232      -6.766  21.192  -3.351  1.00 32.87      A  C
ATOM   1520  CB   THR A 232      -6.330  22.586  -2.910  1.00 46.99      A  C
ATOM   1521  OG1  THR A 232      -7.488  23.371  -2.620  1.00 46.99      A  O
ATOM   1522  CG2  THR A 232      -5.538  23.264  -4.015  1.00 46.99      A  C
ATOM   1523  C    THR A 232      -7.851  20.707  -2.399  1.00 32.87      A  C
ATOM   1524  O    THR A 232      -7.628  20.604  -1.191  1.00 32.87      A  O
ATOM   1525  N    ASP A 233      -9.026  20.412  -2.950  1.00 41.01      A  N
ATOM   1526  CA   ASP A 233     -10.138  19.912  -2.153  1.00 41.01      A  C
ATOM   1527  CB   ASP A 233     -11.376  20.767  -2.366  1.00 68.81      A  C
ATOM   1528  CG   ASP A 233     -12.025  20.500  -3.706  1.00 68.81      A  C
ATOM   1529  OD1  ASP A 233     -11.269  20.427  -4.710  1.00 68.81      A  O
ATOM   1530  OD2  ASP A 233     -13.280  20.359  -3.751  1.00 68.81      A  O
ATOM   1531  C    ASP A 233     -10.442  18.497  -2.613  1.00 41.01      A  C
ATOM   1532  O    ASP A 233     -11.607  18.115  -2.756  1.00 41.01      A  O
ATOM   1533  N    TYR A 234      -9.390  17.720  -2.854  1.00 55.35      A  N
ATOM   1534  CA   TYR A 234      -9.560  16.345  -3.304  1.00 55.35      A  C
```

FIG. 3-24

```
ATOM   1535  CB   TYR A 234      -8.277  15.843  -3.969  1.00 44.61      A    C
ATOM   1536  CG   TYR A 234      -7.033  16.004  -3.134  1.00 44.61      A    C
ATOM   1537  CD1  TYR A 234      -6.677  15.043  -2.187  1.00 44.61      A    C
ATOM   1538  CE1  TYR A 234      -5.510  15.163  -1.452  1.00 44.61      A    C
ATOM   1539  CD2  TYR A 234      -6.184  17.102  -3.316  1.00 44.61      A    C
ATOM   1540  CE2  TYR A 234      -5.011  17.231  -2.581  1.00 44.61      A    C
ATOM   1541  CZ   TYR A 234      -4.681  16.258  -1.654  1.00 44.61      A    C
ATOM   1542  OH   TYR A 234      -3.521  16.378  -0.926  1.00 44.61      A    O
ATOM   1543  C    TYR A 234      -9.965  15.444  -2.156  1.00 55.35      A    C
ATOM   1544  O    TYR A 234      -9.923  15.845  -0.994  1.00 55.35      A    O
ATOM   1545  N    THR A 235     -10.380  14.232  -2.488  1.00 40.07      A    N
ATOM   1546  CA   THR A 235     -10.812  13.271  -1.484  1.00 40.07      A    C
ATOM   1547  CB   THR A 235     -12.197  12.736  -1.828  1.00 34.31      A    C
ATOM   1548  OG1  THR A 235     -12.103  11.867  -2.963  1.00 34.31      A    O
ATOM   1549  CG2  THR A 235     -13.117  13.884  -2.185  1.00 34.31      A    C
ATOM   1550  C    THR A 235      -9.829  12.108  -1.453  1.00 40.07      A    C
ATOM   1551  O    THR A 235      -8.788  12.153  -2.108  1.00 40.07      A    O
ATOM   1552  N    SER A 236     -10.155  11.060  -0.703  1.00 34.29      A    N
ATOM   1553  CA   SER A 236      -9.264   9.912  -0.638  1.00 34.29      A    C
ATOM   1554  CB   SER A 236      -9.531   9.086   0.621  1.00 24.86      A    C
ATOM   1555  OG   SER A 236     -10.805   8.494   0.582  1.00 24.86      A    O
ATOM   1556  C    SER A 236      -9.388   9.034  -1.882  1.00 34.29      A    C
ATOM   1557  O    SER A 236      -8.699   8.032  -2.017  1.00 34.29      A    O
ATOM   1558  N    SER A 237     -10.254   9.414  -2.806  1.00 38.67      A    N
ATOM   1559  CA   SER A 237     -10.401   8.627  -4.017  1.00 38.67      A    C
ATOM   1560  CB   SER A 237     -11.604   9.104  -4.838  1.00 38.35      A    C
ATOM   1561  OG   SER A 237     -11.521  10.489  -5.105  1.00 38.35      A    O
ATOM   1562  C    SER A 237      -9.120   8.722  -4.833  1.00 38.67      A    C
ATOM   1563  O    SER A 237      -8.943   7.998  -5.801  1.00 38.67      A    O
ATOM   1564  N    ILE A 238      -8.219   9.614  -4.449  1.00 25.97      A    N
ATOM   1565  CA   ILE A 238      -6.962   9.719  -5.170  1.00 25.97      A    C
ATOM   1566  CB   ILE A 238      -6.126  10.918  -4.685  1.00 39.07      A    C
ATOM   1567  CG2  ILE A 238      -6.819  12.210  -5.051  1.00 39.07      A    C
ATOM   1568  CG1  ILE A 238      -5.901  10.816  -3.171  1.00 39.07      A    C
ATOM   1569  CD1  ILE A 238      -4.869  11.770  -2.640  1.00 39.07      A    C
ATOM   1570  C    ILE A 238      -6.154   8.428  -4.957  1.00 25.97      A    C
ATOM   1571  O    ILE A 238      -5.398   8.004  -5.825  1.00 25.97      A    O
ATOM   1572  N    ASP A 239      -6.307   7.801  -3.795  1.00 38.94      A    N
ATOM   1573  CA   ASP A 239      -5.582   6.569  -3.544  1.00 38.94      A    C
ATOM   1574  CB   ASP A 239      -5.783   6.075  -2.109  1.00 42.83      A    C
ATOM   1575  CG   ASP A 239      -5.004   6.880  -1.094  1.00 42.83      A    C
ATOM   1576  OD1  ASP A 239      -3.902   7.369  -1.420  1.00 42.83      A    O
ATOM   1577  OD2  ASP A 239      -5.484   7.010   0.046  1.00 42.83      A    O
ATOM   1578  C    ASP A 239      -6.079   5.511  -4.504  1.00 38.94      A    C
ATOM   1579  O    ASP A 239      -5.299   4.708  -5.012  1.00 38.94      A    O
ATOM   1580  N    VAL A 240      -7.383   5.510  -4.755  1.00 36.32      A    N
ATOM   1581  CA   VAL A 240      -7.966   4.526  -5.646  1.00 36.32      A    C
ATOM   1582  CB   VAL A 240      -9.485   4.578  -5.597  1.00 24.73      A    C
ATOM   1583  CG1  VAL A 240     -10.069   3.661  -6.661  1.00 24.73      A    C
ATOM   1584  CG2  VAL A 240      -9.954   4.153  -4.221  1.00 24.73      A    C
ATOM   1585  C    VAL A 240      -7.477   4.715  -7.072  1.00 36.32      A    C
ATOM   1586  O    VAL A 240      -7.348   3.745  -7.820  1.00 36.32      A    O
ATOM   1587  N    TRP A 241      -7.205   5.960  -7.459  1.00 47.06      A    N
ATOM   1588  CA   TRP A 241      -6.684   6.201  -8.791  1.00 47.06      A    C
ATOM   1589  CB   TRP A 241      -6.601   7.695  -9.093  1.00 31.46      A    C
ATOM   1590  CG   TRP A 241      -5.765   8.010 -10.318  1.00 31.46      A    C
ATOM   1591  CD2  TRP A 241      -6.234   8.203 -11.664  1.00 31.46      A    C
ATOM   1592  CE2  TRP A 241      -5.094   8.429 -12.472  1.00 31.46      A    C
ATOM   1593  CE3  TRP A 241      -7.503   8.243 -12.261  1.00 31.46      A    C
ATOM   1594  CD1  TRP A 241      -4.404   8.103 -10.375  1.00 31.46      A    C
ATOM   1595  NE1  TRP A 241      -3.997   8.349 -11.663  1.00 31.46      A    N
ATOM   1596  CZ2  TRP A 241      -5.188   8.644 -13.852  1.00 31.46      A    C
ATOM   1597  CZ3  TRP A 241      -7.591   8.461 -13.633  1.00 31.46      A    C
ATOM   1598  CH2  TRP A 241      -6.438   8.673 -14.407  1.00 31.46      A    C
ATOM   1599  C    TRP A 241      -5.294   5.577  -8.785  1.00 47.06      A    C
ATOM   1600  O    TRP A 241      -4.930   4.845  -9.700  1.00 47.06      A    O
ATOM   1601  N    SER A 242      -4.531   5.854  -7.728  1.00 42.65      A    N
```

FIG. 3-25

```
ATOM   1602  CA   SER A 242      -3.174    5.320   -7.569  1.00 42.65      A    C
ATOM   1603  CB   SER A 242      -2.554    5.800   -6.252  1.00 32.57      A    C
ATOM   1604  OG   SER A 242      -2.418    7.200   -6.221  1.00 32.57      A    O
ATOM   1605  C    SER A 242      -3.175    3.798   -7.573  1.00 42.65      A    C
ATOM   1606  O    SER A 242      -2.269    3.177   -8.115  1.00 42.65      A    O
ATOM   1607  N    ALA A 243      -4.189    3.203   -6.954  1.00 27.23      A    N
ATOM   1608  CA   ALA A 243      -4.291    1.756   -6.892  1.00 27.23      A    C
ATOM   1609  CB   ALA A 243      -5.425    1.357   -5.977  1.00 17.91      A    C
ATOM   1610  C    ALA A 243      -4.516    1.198   -8.286  1.00 27.23      A    C
ATOM   1611  O    ALA A 243      -3.958    0.172   -8.654  1.00 27.23      A    O
ATOM   1612  N    GLY A 244      -5.339    1.886   -9.061  1.00 30.07      A    N
ATOM   1613  CA   GLY A 244      -5.612    1.443  -10.409  1.00 30.07      A    C
ATOM   1614  C    GLY A 244      -4.408    1.586  -11.318  1.00 30.07      A    C
ATOM   1615  O    GLY A 244      -4.352    0.961  -12.372  1.00 30.07      A    O
ATOM   1616  N    CYS A 245      -3.450    2.421  -10.925  1.00 35.94      A    N
ATOM   1617  CA   CYS A 245      -2.238    2.613  -11.719  1.00 35.94      A    C
ATOM   1618  CB   CYS A 245      -1.577    3.959  -11.375  1.00 32.20      A    C
ATOM   1619  SG   CYS A 245      -2.342    5.417  -12.174  1.00 32.20      A    S
ATOM   1620  C    CYS A 245      -1.265    1.452  -11.480  1.00 35.94      A    C
ATOM   1621  O    CYS A 245      -0.475    1.092  -12.356  1.00 35.94      A    O
ATOM   1622  N    VAL A 246      -1.342    0.867  -10.287  1.00 43.26      A    N
ATOM   1623  CA   VAL A 246      -0.509   -0.269   -9.920  1.00 43.26      A    C
ATOM   1624  CB   VAL A 246      -0.550   -0.539   -8.394  1.00 42.20      A    C
ATOM   1625  CG1  VAL A 246       0.225   -1.799   -8.070  1.00 42.20      A    C
ATOM   1626  CG2  VAL A 246       0.014    0.639   -7.636  1.00 42.20      A    C
ATOM   1627  C    VAL A 246      -1.051   -1.501  -10.636  1.00 43.26      A    C
ATOM   1628  O    VAL A 246      -0.293   -2.288  -11.189  1.00 43.26      A    O
ATOM   1629  N    LEU A 247      -2.367   -1.669  -10.614  1.00 40.13      A    N
ATOM   1630  CA   LEU A 247      -2.981   -2.800  -11.275  1.00 40.13      A    C
ATOM   1631  CB   LEU A 247      -4.484   -2.787  -11.053  1.00 34.27      A    C
ATOM   1632  CG   LEU A 247      -5.269   -3.769  -11.925  1.00 34.27      A    C
ATOM   1633  CD1  LEU A 247      -4.762   -5.170  -11.672  1.00 34.27      A    C
ATOM   1634  CD2  LEU A 247      -6.754   -3.662  -11.632  1.00 34.27      A    C
ATOM   1635  C    LEU A 247      -2.692   -2.765  -12.772  1.00 40.13      A    C
ATOM   1636  O    LEU A 247      -2.270   -3.754  -13.357  1.00 40.13      A    O
ATOM   1637  N    ALA A 248      -2.924   -1.624  -13.400  1.00 30.55      A    N
ATOM   1638  CA   ALA A 248      -2.667   -1.515  -14.822  1.00 30.55      A    C
ATOM   1639  CB   ALA A 248      -2.931   -0.087  -15.290  1.00 18.90      A    C
ATOM   1640  C    ALA A 248      -1.224   -1.925  -15.128  1.00 30.55      A    C
ATOM   1641  O    ALA A 248      -0.964   -2.655  -16.078  1.00 30.55      A    O
ATOM   1642  N    GLU A 249      -0.295   -1.461  -14.300  1.00 38.22      A    N
ATOM   1643  CA   GLU A 249       1.128   -1.740  -14.470  1.00 38.22      A    C
ATOM   1644  CB   GLU A 249       1.932   -0.954  -13.440  1.00 49.27      A    C
ATOM   1645  CG   GLU A 249       3.409   -0.961  -13.742  1.00 49.27      A    C
ATOM   1646  CD   GLU A 249       4.212   -0.074  -12.812  1.00 49.27      A    C
ATOM   1647  OE1  GLU A 249       3.781    1.081  -12.586  1.00 49.27      A    O
ATOM   1648  OE2  GLU A 249       5.277   -0.535  -12.327  1.00 49.27      A    O
ATOM   1649  C    GLU A 249       1.487   -3.215  -14.350  1.00 38.22      A    C
ATOM   1650  O    GLU A 249       2.396   -3.708  -15.017  1.00 38.22      A    O
ATOM   1651  N    LEU A 250       0.770   -3.918  -13.487  1.00 30.95      A    N
ATOM   1652  CA   LEU A 250       1.029   -5.324  -13.275  1.00 30.95      A    C
ATOM   1653  CB   LEU A 250       0.389   -5.768  -11.971  1.00 23.60      A    C
ATOM   1654  CG   LEU A 250       1.018   -5.049  -10.782  1.00 23.60      A    C
ATOM   1655  CD1  LEU A 250       0.232   -5.374   -9.532  1.00 23.60      A    C
ATOM   1656  CD2  LEU A 250       2.479   -5.453  -10.634  1.00 23.60      A    C
ATOM   1657  C    LEU A 250       0.542   -6.175  -14.422  1.00 30.95      A    C
ATOM   1658  O    LEU A 250       1.096   -7.237  -14.678  1.00 30.95      A    O
ATOM   1659  N    LEU A 251      -0.497   -5.712  -15.107  1.00 30.22      A    N
ATOM   1660  CA   LEU A 251      -1.056   -6.425  -16.251  1.00 30.22      A    C
ATOM   1661  CB   LEU A 251      -2.522   -6.049  -16.463  1.00 25.42      A    C
ATOM   1662  CG   LEU A 251      -3.543   -6.144  -15.338  1.00 25.42      A    C
ATOM   1663  CD1  LEU A 251      -4.875   -5.676  -15.872  1.00 25.42      A    C
ATOM   1664  CD2  LEU A 251      -3.644   -7.560  -14.820  1.00 25.42      A    C
ATOM   1665  C    LEU A 251      -0.282   -6.004  -17.490  1.00 30.22      A    C
ATOM   1666  O    LEU A 251      -0.222   -6.726  -18.482  1.00 30.22      A    O
ATOM   1667  N    LEU A 252       0.302   -4.814  -17.410  1.00 41.77      A    N
ATOM   1668  CA   LEU A 252       1.050   -4.214  -18.499  1.00 41.77      A    C
```

FIG. 3-26

```
ATOM   1669  CB   LEU A 252       0.843  -2.703 -18.479  1.00 49.78      A  C
ATOM   1670  CG   LEU A 252       0.202  -2.040 -19.691  1.00 49.78      A  C
ATOM   1671  CD1  LEU A 252      -1.139  -2.687 -20.006  1.00 49.78      A  C
ATOM   1672  CD2  LEU A 252       0.024  -0.564 -19.398  1.00 49.78      A  C
ATOM   1673  C    LEU A 252       2.538  -4.499 -18.484  1.00 41.77      A  C
ATOM   1674  O    LEU A 252       3.169  -4.534 -19.537  1.00 41.77      A  O
ATOM   1675  N    GLY A 253       3.111  -4.680 -17.303  1.00 36.25      A  N
ATOM   1676  CA   GLY A 253       4.534  -4.942 -17.237  1.00 36.25      A  C
ATOM   1677  C    GLY A 253       5.355  -3.662 -17.242  1.00 36.25      A  C
ATOM   1678  O    GLY A 253       6.585  -3.694 -17.229  1.00 36.25      A  O
ATOM   1679  N    GLN A 254       4.673  -2.525 -17.270  1.00 48.82      A  N
ATOM   1680  CA   GLN A 254       5.333  -1.223 -17.256  1.00 48.82      A  C
ATOM   1681  CB   GLN A 254       5.859  -0.891 -18.647  1.00 52.67      A  C
ATOM   1682  CG   GLN A 254       4.817  -1.056 -19.733  1.00 52.67      A  C
ATOM   1683  CD   GLN A 254       5.193  -0.339 -21.018  1.00 52.67      A  C
ATOM   1684  OE1  GLN A 254       5.131   0.894 -21.105  1.00 52.67      A  O
ATOM   1685  NE2  GLN A 254       5.592  -1.106 -22.024  1.00 52.67      A  N
ATOM   1686  C    GLN A 254       4.316  -0.165 -16.802  1.00 48.82      A  C
ATOM   1687  O    GLN A 254       3.108  -0.362 -16.939  1.00 48.82      A  O
ATOM   1688  N    PRO A 255       4.786   0.958 -16.237  1.00 45.25      A  N
ATOM   1689  CD   PRO A 255       6.166   1.358 -15.916  1.00 51.96      A  C
ATOM   1690  CA   PRO A 255       3.834   1.980 -15.798  1.00 45.25      A  C
ATOM   1691  CB   PRO A 255       4.745   3.134 -15.403  1.00 51.96      A  C
ATOM   1692  CG   PRO A 255       5.950   2.431 -14.874  1.00 51.96      A  C
ATOM   1693  C    PRO A 255       2.866   2.351 -16.920  1.00 45.25      A  C
ATOM   1694  O    PRO A 255       3.275   2.500 -18.068  1.00 45.25      A  O
ATOM   1695  N    ILE A 256       1.588   2.487 -16.594  1.00 29.72      A  N
ATOM   1696  CA   ILE A 256       0.584   2.830 -17.589  1.00 29.72      A  C
ATOM   1697  CB   ILE A 256      -0.844   2.578 -17.028  1.00 40.28      A  C
ATOM   1698  CG2  ILE A 256      -1.035   3.303 -15.711  1.00 40.28      A  C
ATOM   1699  CG1  ILE A 256      -1.903   3.026 -18.030  1.00 40.28      A  C
ATOM   1700  CD1  ILE A 256      -2.098   2.081 -19.154  1.00 40.28      A  C
ATOM   1701  C    ILE A 256       0.718   4.279 -18.073  1.00 29.72      A  C
ATOM   1702  O    ILE A 256       0.599   4.549 -19.263  1.00 29.72      A  O
ATOM   1703  N    PHE A 257       0.969   5.211 -17.160  1.00 35.25      A  N
ATOM   1704  CA   PHE A 257       1.127   6.620 -17.532  1.00 35.25      A  C
ATOM   1705  CB   PHE A 257       0.034   7.493 -16.901  1.00 33.99      A  C
ATOM   1706  CG   PHE A 257      -1.362   6.980 -17.092  1.00 33.99      A  C
ATOM   1707  CD1  PHE A 257      -1.867   6.738 -18.361  1.00 33.99      A  C
ATOM   1708  CD2  PHE A 257      -2.182   6.752 -15.992  1.00 33.99      A  C
ATOM   1709  CE1  PHE A 257      -3.172   6.272 -18.530  1.00 33.99      A  C
ATOM   1710  CE2  PHE A 257      -3.482   6.289 -16.151  1.00 33.99      A  C
ATOM   1711  CZ   PHE A 257      -3.980   6.047 -17.426  1.00 33.99      A  C
ATOM   1712  C    PHE A 257       2.480   7.142 -17.050  1.00 35.25      A  C
ATOM   1713  O    PHE A 257       2.585   7.644 -15.935  1.00 35.25      A  O
ATOM   1714  N    PRO A 258       3.525   7.041 -17.883  1.00 36.00      A  N
ATOM   1715  CD   PRO A 258       3.540   6.230 -19.117  1.00 39.52      A  C
ATOM   1716  CA   PRO A 258       4.883   7.496 -17.554  1.00 36.00      A  C
ATOM   1717  CB   PRO A 258       5.749   6.499 -18.306  1.00 39.52      A  C
ATOM   1718  CG   PRO A 258       4.983   6.367 -19.590  1.00 39.52      A  C
ATOM   1719  C    PRO A 258       5.214   8.937 -17.958  1.00 36.00      A  C
ATOM   1720  O    PRO A 258       6.059   9.161 -18.822  1.00 36.00      A  O
ATOM   1721  N    GLY A 259       4.567   9.909 -17.331  1.00 49.21      A  N
ATOM   1722  CA   GLY A 259       4.833  11.297 -17.678  1.00 49.21      A  C
ATOM   1723  C    GLY A 259       6.267  11.723 -17.406  1.00 49.21      A  C
ATOM   1724  O    GLY A 259       6.852  11.309 -16.397  1.00 49.21      A  O
ATOM   1725  N    ASP A 260       6.851  12.544 -18.282  1.00 50.37      A  N
ATOM   1726  CA   ASP A 260       8.229  12.976 -18.040  1.00 50.37      A  C
ATOM   1727  CB   ASP A 260       8.957  13.314 -19.352  1.00 49.10      A  C
ATOM   1728  CG   ASP A 260       8.456  14.591 -19.993  1.00 49.10      A  C
ATOM   1729  OD1  ASP A 260       8.033  15.498 -19.239  1.00 49.10      A  O
ATOM   1730  OD2  ASP A 260       8.505  14.697 -21.244  1.00 49.10      A  O
ATOM   1731  C    ASP A 260       8.263  14.171 -17.087  1.00 50.37      A  C
ATOM   1732  O    ASP A 260       9.325  14.617 -16.670  1.00 50.37      A  O
ATOM   1733  N    SER A 261       7.088  14.688 -16.751  1.00 42.96      A  N
ATOM   1734  CA   SER A 261       6.987  15.813 -15.835  1.00 42.96      A  C
ATOM   1735  CB   SER A 261       7.336  17.114 -16.545  1.00 45.55      A  C
```

FIG. 3-27

```
ATOM   1736  OG   SER A 261       6.269  17.511 -17.379  1.00 45.55      A   O
ATOM   1737  C    SER A 261       5.566  15.895 -15.284  1.00 42.96      A   C
ATOM   1738  O    SER A 261       4.647  15.281 -15.821  1.00 42.96      A   O
ATOM   1739  N    GLY A 262       5.398  16.650 -14.200  1.00 60.21      A   N
ATOM   1740  CA   GLY A 262       4.092  16.796 -13.583  1.00 60.21      A   C
ATOM   1741  C    GLY A 262       2.970  17.101 -14.562  1.00 60.21      A   C
ATOM   1742  O    GLY A 262       1.832  16.695 -14.339  1.00 60.21      A   O
ATOM   1743  N    VAL A 263       3.282  17.812 -15.644  1.00 49.75      A   N
ATOM   1744  CA   VAL A 263       2.276  18.165 -16.642  1.00 49.75      A   C
ATOM   1745  CB   VAL A 263       2.548  19.585 -17.229  1.00 52.93      A   C
ATOM   1746  CG1  VAL A 263       1.633  19.846 -18.431  1.00 52.93      A   C
ATOM   1747  CG2  VAL A 263       2.316  20.647 -16.150  1.00 52.93      A   C
ATOM   1748  C    VAL A 263       2.196  17.136 -17.775  1.00 49.75      A   C
ATOM   1749  O    VAL A 263       1.109  16.823 -18.250  1.00 49.75      A   O
ATOM   1750  N    ASP A 264       3.341  16.618 -18.211  1.00 56.04      A   N
ATOM   1751  CA   ASP A 264       3.368  15.605 -19.269  1.00 56.04      A   C
ATOM   1752  CB   ASP A 264       4.820  15.137 -19.511  1.00 69.02      A   C
ATOM   1753  CG   ASP A 264       4.947  14.119 -20.659  1.00 69.02      A   C
ATOM   1754  OD1  ASP A 264       5.907  13.315 -20.620  1.00 69.02      A   O
ATOM   1755  OD2  ASP A 264       4.109  14.127 -21.601  1.00 69.02      A   O
ATOM   1756  C    ASP A 264       2.514  14.422 -18.773  1.00 56.04      A   C
ATOM   1757  O    ASP A 264       1.884  13.699 -19.559  1.00 56.04      A   O
ATOM   1758  N    GLN A 265       2.496  14.250 -17.452  1.00 51.13      A   N
ATOM   1759  CA   GLN A 265       1.754  13.177 -16.808  1.00 51.13      A   C
ATOM   1760  CB   GLN A 265       1.807  13.341 -15.286  1.00 33.26      A   C
ATOM   1761  CG   GLN A 265       1.176  12.196 -14.506  1.00 33.26      A   C
ATOM   1762  CD   GLN A 265       1.738  10.860 -14.914  1.00 33.26      A   C
ATOM   1763  OE1  GLN A 265       2.888  10.771 -15.354  1.00 33.26      A   O
ATOM   1764  NE2  GLN A 265       0.942   9.806 -14.762  1.00 33.26      A   N
ATOM   1765  C    GLN A 265       0.312  13.191 -17.270  1.00 51.13      A   C
ATOM   1766  O    GLN A 265      -0.258  12.149 -17.604  1.00 51.13      A   O
ATOM   1767  N    LEU A 266      -0.279  14.379 -17.276  1.00 43.43      A   N
ATOM   1768  CA   LEU A 266      -1.653  14.527 -17.698  1.00 43.43      A   C
ATOM   1769  CB   LEU A 266      -2.078  15.979 -17.516  1.00 40.66      A   C
ATOM   1770  CG   LEU A 266      -3.545  16.365 -17.701  1.00 40.66      A   C
ATOM   1771  CD1  LEU A 266      -4.461  15.407 -16.924  1.00 40.66      A   C
ATOM   1772  CD2  LEU A 266      -3.725  17.801 -17.220  1.00 40.66      A   C
ATOM   1773  C    LEU A 266      -1.768  14.093 -19.159  1.00 43.43      A   C
ATOM   1774  O    LEU A 266      -2.685  13.353 -19.528  1.00 43.43      A   O
ATOM   1775  N    VAL A 267      -0.824  14.535 -19.985  1.00 42.78      A   N
ATOM   1776  CA   VAL A 267      -0.837  14.178 -21.397  1.00 42.78      A   C
ATOM   1777  CB   VAL A 267       0.411  14.718 -22.134  1.00 29.31      A   C
ATOM   1778  CG1  VAL A 267       0.379  14.289 -23.590  1.00 29.31      A   C
ATOM   1779  CG2  VAL A 267       0.458  16.231 -22.030  1.00 29.31      A   C
ATOM   1780  C    VAL A 267      -0.898  12.664 -21.567  1.00 42.78      A   C
ATOM   1781  O    VAL A 267      -1.787  12.147 -22.244  1.00 42.78      A   O
ATOM   1782  N    GLU A 268       0.045  11.958 -20.950  1.00 45.75      A   N
ATOM   1783  CA   GLU A 268       0.082  10.499 -21.035  1.00 45.75      A   C
ATOM   1784  CB   GLU A 268       1.179   9.940 -20.117  1.00 47.62      A   C
ATOM   1785  CG   GLU A 268       2.603  10.221 -20.579  1.00 47.62      A   C
ATOM   1786  CD   GLU A 268       2.938   9.542 -21.895  1.00 47.62      A   C
ATOM   1787  OE1  GLU A 268       2.779   8.307 -21.990  1.00 47.62      A   O
ATOM   1788  OE2  GLU A 268       3.365  10.242 -22.836  1.00 47.62      A   O
ATOM   1789  C    GLU A 268      -1.269   9.884 -20.661  1.00 45.75      A   C
ATOM   1790  O    GLU A 268      -1.734   8.964 -21.322  1.00 45.75      A   O
ATOM   1791  N    ILE A 269      -1.879  10.396 -19.593  1.00 43.94      A   N
ATOM   1792  CA   ILE A 269      -3.181   9.927 -19.114  1.00 43.94      A   C
ATOM   1793  CB   ILE A 269      -3.649  10.728 -17.865  1.00 34.06      A   C
ATOM   1794  CG2  ILE A 269      -5.154  10.566 -17.672  1.00 34.06      A   C
ATOM   1795  CG1  ILE A 269      -2.888  10.269 -16.620  1.00 34.06      A   C
ATOM   1796  CD1  ILE A 269      -3.280  11.012 -15.353  1.00 34.06      A   C
ATOM   1797  C    ILE A 269      -4.218  10.123 -20.203  1.00 43.94      A   C
ATOM   1798  O    ILE A 269      -4.976   9.212 -20.536  1.00 43.94      A   O
ATOM   1799  N    ILE A 270      -4.249  11.337 -20.736  1.00 44.97      A   N
ATOM   1800  CA   ILE A 270      -5.175  11.706 -21.799  1.00 44.97      A   C
ATOM   1801  CB   ILE A 270      -4.986  13.201 -22.188  1.00 35.31      A   C
ATOM   1802  CG2  ILE A 270      -5.629  13.490 -23.537  1.00 35.31      A   C
```

FIG. 3-28

```
ATOM   1803  CG1  ILE A 270      -5.573  14.089 -21.086  1.00 35.31      A    C
ATOM   1804  CD1  ILE A 270      -5.258  15.551 -21.238  1.00 35.31      A    C
ATOM   1805  C    ILE A 270      -4.996  10.830 -23.040  1.00 44.97      A    C
ATOM   1806  O    ILE A 270      -5.941  10.619 -23.794  1.00 44.97      A    O
ATOM   1807  N    LYS A 271      -3.789  10.310 -23.239  1.00 39.25      A    N
ATOM   1808  CA   LYS A 271      -3.515   9.471 -24.396  1.00 39.25      A    C
ATOM   1809  CB   LYS A 271      -2.012   9.211 -24.508  1.00 39.58      A    C
ATOM   1810  CG   LYS A 271      -1.244  10.483 -24.776  1.00 39.58      A    C
ATOM   1811  CD   LYS A 271       0.249  10.301 -24.667  1.00 39.58      A    C
ATOM   1812  CE   LYS A 271       0.783   9.397 -25.754  1.00 39.58      A    C
ATOM   1813  NZ   LYS A 271       2.271   9.258 -25.682  1.00 39.58      A    N
ATOM   1814  C    LYS A 271      -4.296   8.159 -24.405  1.00 39.25      A    C
ATOM   1815  O    LYS A 271      -4.505   7.570 -25.463  1.00 39.25      A    O
ATOM   1816  N    VAL A 272      -4.741   7.698 -23.245  1.00 37.32      A    N
ATOM   1817  CA   VAL A 272      -5.510   6.467 -23.229  1.00 37.32      A    C
ATOM   1818  CB   VAL A 272      -4.910   5.402 -22.244  1.00 35.30      A    C
ATOM   1819  CG1  VAL A 272      -3.400   5.388 -22.330  1.00 35.30      A    C
ATOM   1820  CG2  VAL A 272      -5.353   5.672 -20.844  1.00 35.30      A    C
ATOM   1821  C    VAL A 272      -6.962   6.777 -22.856  1.00 37.32      A    C
ATOM   1822  O    VAL A 272      -7.891   6.286 -23.487  1.00 37.32      A    O
ATOM   1823  N    LEU A 273      -7.162   7.608 -21.842  1.00 49.24      A    N
ATOM   1824  CA   LEU A 273      -8.518   7.943 -21.420  1.00 49.24      A    C
ATOM   1825  CB   LEU A 273      -8.515   8.522 -19.994  1.00 43.30      A    C
ATOM   1826  CG   LEU A 273      -7.910   7.756 -18.804  1.00 43.30      A    C
ATOM   1827  CD1  LEU A 273      -8.360   8.459 -17.525  1.00 43.30      A    C
ATOM   1828  CD2  LEU A 273      -8.352   6.295 -18.779  1.00 43.30      A    C
ATOM   1829  C    LEU A 273      -9.176   8.949 -22.371  1.00 49.24      A    C
ATOM   1830  O    LEU A 273     -10.405   9.064 -22.419  1.00 49.24      A    O
ATOM   1831  N    GLY A 274      -8.355   9.671 -23.126  1.00 45.66      A    N
ATOM   1832  CA   GLY A 274      -8.882  10.670 -24.038  1.00 45.66      A    C
ATOM   1833  C    GLY A 274      -9.126  11.989 -23.326  1.00 45.66      A    C
ATOM   1834  O    GLY A 274      -9.197  12.018 -22.100  1.00 45.66      A    O
ATOM   1835  N    THR A 275      -9.245  13.083 -24.075  1.00 39.05      A    N
ATOM   1836  CA   THR A 275      -9.484  14.396 -23.476  1.00 39.05      A    C
ATOM   1837  CB   THR A 275      -9.758  15.443 -24.551  1.00 28.30      A    C
ATOM   1838  OG1  THR A 275      -8.667  15.475 -25.475  1.00 28.30      A    O
ATOM   1839  CG2  THR A 275      -9.914  16.804 -23.926  1.00 28.30      A    C
ATOM   1840  C    THR A 275     -10.676  14.355 -22.516  1.00 39.05      A    C
ATOM   1841  O    THR A 275     -11.714  13.777 -22.834  1.00 39.05      A    O
ATOM   1842  N    PRO A 276     -10.548  14.976 -21.327  1.00 41.23      A    N
ATOM   1843  CD   PRO A 276      -9.427  15.780 -20.819  1.00 28.41      A    C
ATOM   1844  CA   PRO A 276     -11.652  14.968 -20.360  1.00 41.23      A    C
ATOM   1845  CB   PRO A 276     -10.989  15.441 -19.062  1.00 28.41      A    C
ATOM   1846  CG   PRO A 276      -9.510  15.514 -19.364  1.00 28.41      A    C
ATOM   1847  C    PRO A 276     -12.767  15.910 -20.787  1.00 41.23      A    C
ATOM   1848  O    PRO A 276     -12.496  16.979 -21.331  1.00 41.23      A    O
ATOM   1849  N    THR A 277     -14.017  15.529 -20.546  1.00 38.31      A    N
ATOM   1850  CA   THR A 277     -15.139  16.387 -20.921  1.00 38.31      A    C
ATOM   1851  CB   THR A 277     -16.492  15.677 -20.749  1.00 27.13      A    C
ATOM   1852  OG1  THR A 277     -16.866  15.678 -19.367  1.00 27.13      A    O
ATOM   1853  CG2  THR A 277     -16.401  14.249 -21.233  1.00 27.13      A    C
ATOM   1854  C    THR A 277     -15.127  17.620 -20.030  1.00 38.31      A    C
ATOM   1855  O    THR A 277     -14.623  17.578 -18.914  1.00 38.31      A    O
ATOM   1856  N    ARG A 278     -15.658  18.722 -20.546  1.00 37.70      A    N
ATOM   1857  CA   ARG A 278     -15.720  19.983 -19.808  1.00 37.70      A    C
ATOM   1858  CB   ARG A 278     -16.673  20.957 -20.513  1.00 49.87      A    C
ATOM   1859  CG   ARG A 278     -16.755  22.342 -19.863  1.00 49.87      A    C
ATOM   1860  CD   ARG A 278     -17.913  23.183 -20.415  1.00 49.87      A    C
ATOM   1861  NE   ARG A 278     -17.846  23.348 -21.867  1.00 49.87      A    N
ATOM   1862  CZ   ARG A 278     -18.914  23.415 -22.655  1.00 49.87      A    C
ATOM   1863  NH1  ARG A 278     -20.131  23.335 -22.133  1.00 49.87      A    N
ATOM   1864  NH2  ARG A 278     -18.766  23.533 -23.969  1.00 49.87      A    N
ATOM   1865  C    ARG A 278     -16.215  19.751 -18.389  1.00 37.70      A    C
ATOM   1866  O    ARG A 278     -15.655  20.277 -17.424  1.00 37.70      A    O
ATOM   1867  N    GLU A 279     -17.278  18.960 -18.278  1.00 44.02      A    N
ATOM   1868  CA   GLU A 279     -17.885  18.656 -16.989  1.00 44.02      A    C
ATOM   1869  CB   GLU A 279     -19.174  17.849 -17.178  1.00 44.87      A    C
```

FIG. 3-29

```
ATOM   1870  CG  GLU A 279     -20.358  18.639 -17.730  1.00 44.87      A  C
ATOM   1871  CD  GLU A 279     -20.103  19.240 -19.103  1.00 44.87      A  C
ATOM   1872  OE1 GLU A 279     -20.064  20.493 -19.192  1.00 44.87      A  O
ATOM   1873  OE2 GLU A 279     -19.943  18.464 -20.080  1.00 44.87      A  O
ATOM   1874  C   GLU A 279     -16.924  17.876 -16.111  1.00 44.02      A  C
ATOM   1875  O   GLU A 279     -16.819  18.132 -14.904  1.00 44.02      A  O
ATOM   1876  N   GLN A 280     -16.231  16.918 -16.723  1.00 46.53      A  N
ATOM   1877  CA  GLN A 280     -15.274  16.099 -15.996  1.00 46.53      A  C
ATOM   1878  CB  GLN A 280     -14.599  15.105 -16.943  1.00 27.94      A  C
ATOM   1879  CG  GLN A 280     -15.190  13.704 -16.857  1.00 27.94      A  C
ATOM   1880  CD  GLN A 280     -14.742  12.811 -17.982  1.00 27.94      A  C
ATOM   1881  OE1 GLN A 280     -15.000  11.611 -17.972  1.00 27.94      A  O
ATOM   1882  NE2 GLN A 280     -14.077  13.392 -18.972  1.00 27.94      A  N
ATOM   1883  C   GLN A 280     -14.247  16.990 -15.327  1.00 46.53      A  C
ATOM   1884  O   GLN A 280     -14.029  16.905 -14.113  1.00 46.53      A  O
ATOM   1885  N   ILE A 281     -13.637  17.862 -16.121  1.00 42.30      A  N
ATOM   1886  CA  ILE A 281     -12.643  18.796 -15.615  1.00 42.30      A  C
ATOM   1887  CB  ILE A 281     -12.219  19.770 -16.722  1.00 20.23      A  C
ATOM   1888  CG2 ILE A 281     -11.245  20.785 -16.183  1.00 20.23      A  C
ATOM   1889  CG1 ILE A 281     -11.581  18.980 -17.864  1.00 20.23      A  C
ATOM   1890  CD1 ILE A 281     -11.287  19.787 -19.095  1.00 20.23      A  C
ATOM   1891  C   ILE A 281     -13.171  19.568 -14.399  1.00 42.30      A  C
ATOM   1892  O   ILE A 281     -12.410  19.927 -13.504  1.00 42.30      A  O
ATOM   1893  N   ALA A 282     -14.478  19.806 -14.351  1.00 51.57      A  N
ATOM   1894  CA  ALA A 282     -15.061  20.527 -13.220  1.00 51.57      A  C
ATOM   1895  CB  ALA A 282     -16.474  21.009 -13.576  1.00 29.00      A  C
ATOM   1896  C   ALA A 282     -15.096  19.661 -11.946  1.00 51.57      A  C
ATOM   1897  O   ALA A 282     -14.911  20.163 -10.833  1.00 51.57      A  O
ATOM   1898  N   GLU A 283     -15.316  18.361 -12.116  1.00 53.16      A  N
ATOM   1899  CA  GLU A 283     -15.397  17.445 -10.979  1.00 53.16      A  C
ATOM   1900  CB  GLU A 283     -16.050  16.140 -11.439  1.00 67.12      A  C
ATOM   1901  CG  GLU A 283     -17.351  16.346 -12.198  1.00 67.12      A  C
ATOM   1902  CD  GLU A 283     -17.661  15.179 -13.138  1.00 67.12      A  C
ATOM   1903  OE1 GLU A 283     -16.791  14.858 -13.983  1.00 67.12      A  O
ATOM   1904  OE2 GLU A 283     -18.763  14.580 -13.038  1.00 67.12      A  O
ATOM   1905  C   GLU A 283     -14.038  17.161 -10.290  1.00 53.16      A  C
ATOM   1906  O   GLU A 283     -13.992  16.829  -9.098  1.00 53.16      A  O
ATOM   1907  N   MET A 284     -12.952  17.286 -11.054  1.00 50.66      A  N
ATOM   1908  CA  MET A 284     -11.597  17.087 -10.548  1.00 50.66      A  C
ATOM   1909  CB  MET A 284     -10.617  16.854 -11.713  1.00 46.46      A  C
ATOM   1910  CG  MET A 284     -10.620  15.428 -12.271  1.00 46.46      A  C
ATOM   1911  SD  MET A 284     -10.040  15.239 -13.979  1.00 46.46      A  S
ATOM   1912  CE  MET A 284      -8.440  15.367 -13.763  1.00 46.46      A  C
ATOM   1913  C   MET A 284     -11.216  18.363  -9.806  1.00 50.66      A  C
ATOM   1914  O   MET A 284     -10.715  18.328  -8.683  1.00 50.66      A  O
ATOM   1915  N   ASN A 285     -11.473  19.497 -10.444  1.00 41.14      A  N
ATOM   1916  CA  ASN A 285     -11.166  20.791  -9.860  1.00 41.14      A  C
ATOM   1917  CB  ASN A 285      -9.696  21.150 -10.070  1.00 63.31      A  C
ATOM   1918  CG  ASN A 285      -9.420  22.604  -9.776  1.00 63.31      A  C
ATOM   1919  OD1 ASN A 285      -9.955  23.156  -8.808  1.00 63.31      A  O
ATOM   1920  ND2 ASN A 285      -8.585  23.241 -10.602  1.00 63.31      A  N
ATOM   1921  C   ASN A 285     -12.039  21.864 -10.488  1.00 41.14      A  C
ATOM   1922  O   ASN A 285     -11.855  22.230 -11.656  1.00 41.14      A  O
ATOM   1923  N   PRO A 286     -12.977  22.410  -9.692  1.00 92.65      A  N
ATOM   1924  CD  PRO A 286     -12.916  22.175  -8.231  1.00 84.61      A  C
ATOM   1925  CA  PRO A 286     -13.973  23.454 -10.001  1.00 92.65      A  C
ATOM   1926  CB  PRO A 286     -14.614  23.729  -8.636  1.00 84.61      A  C
ATOM   1927  CG  PRO A 286     -13.463  23.485  -7.673  1.00 84.61      A  C
ATOM   1928  C   PRO A 286     -13.461  24.745 -10.653  1.00 92.65      A  C
ATOM   1929  O   PRO A 286     -13.884  25.121 -11.757  1.00 92.65      A  O
ATOM   1930  N   ASN A 287     -12.549  25.415  -9.957  1.00 95.33      A  N
ATOM   1931  CA  ASN A 287     -11.985  26.681 -10.418  1.00 95.33      A  C
ATOM   1932  CB  ASN A 287     -11.130  27.262  -9.292  1.00 70.89      A  C
ATOM   1933  CG  ASN A 287     -11.868  27.244  -7.951  1.00 70.89      A  C
ATOM   1934  OD1 ASN A 287     -12.711  28.112  -7.683  1.00 70.89      A  O
ATOM   1935  ND2 ASN A 287     -11.577  26.229  -7.116  1.00 70.89      A  N
ATOM   1936  C   ASN A 287     -11.196  26.602 -11.730  1.00 95.33      A  C
```

FIG. 3-30

```
ATOM   1937  O    ASN A 287     -11.179  25.558 -12.401  1.00 95.33      A    O
ATOM   1938  N    ALA A 288     -10.555  27.715 -12.086  1.00 73.11      A    N
ATOM   1939  CA   ALA A 288      -9.785  27.812 -13.326  1.00 73.11      A    C
ATOM   1940  CB   ALA A 288      -9.145  29.207 -13.431  1.00 84.42      A    C
ATOM   1941  C    ALA A 288      -8.715  26.724 -13.460  1.00 73.11      A    C
ATOM   1942  O    ALA A 288      -7.689  26.742 -12.765  1.00 73.11      A    O
ATOM   1943  N    ALA A 294      -6.486  20.477 -26.814  1.00 71.03      A    N
ATOM   1944  CA   ALA A 294      -5.706  19.328 -27.287  1.00 71.03      A    C
ATOM   1945  CB   ALA A 294      -4.479  19.112 -26.372  1.00 41.44      A    C
ATOM   1946  C    ALA A 294      -6.612  18.082 -27.288  1.00 71.03      A    C
ATOM   1947  O    ALA A 294      -6.401  17.139 -26.505  1.00 71.03      A    O
ATOM   1948  N    ALA A 295      -7.607  18.091 -28.184  1.00 62.93      A    N
ATOM   1949  CA   ALA A 295      -8.608  17.019 -28.292  1.00 62.93      A    C
ATOM   1950  CB   ALA A 295      -9.808  17.530 -29.068  1.00 47.90      A    C
ATOM   1951  C    ALA A 295      -8.167  15.681 -28.872  1.00 62.93      A    C
ATOM   1952  O    ALA A 295      -7.975  15.555 -30.078  1.00 62.93      A    O
ATOM   1953  N    ALA A 296      -8.035  14.681 -28.002  1.00 51.79      A    N
ATOM   1954  CA   ALA A 296      -7.640  13.331 -28.408  1.00 51.79      A    C
ATOM   1955  CB   ALA A 296      -6.436  12.855 -27.590  1.00 24.97      A    C
ATOM   1956  C    ALA A 296      -8.831  12.388 -28.203  1.00 51.79      A    C
ATOM   1957  O    ALA A 296      -9.629  12.589 -27.291  1.00 51.79      A    O
ATOM   1958  N    ALA A 297      -8.958  11.380 -29.065  1.00 55.43      A    N
ATOM   1959  CA   ALA A 297     -10.056  10.429 -28.968  1.00 55.43      A    C
ATOM   1960  CB   ALA A 297      -9.959   9.388 -30.074  1.00 32.74      A    C
ATOM   1961  C    ALA A 297     -10.009   9.760 -27.605  1.00 55.43      A    C
ATOM   1962  O    ALA A 297     -10.079  10.434 -26.586  1.00 55.43      A    O
ATOM   1963  N    ALA A 298      -9.889   8.440 -27.580  1.00 47.14      A    N
ATOM   1964  CA   ALA A 298      -9.845   7.707 -26.327  1.00 47.14      A    C
ATOM   1965  CB   ALA A 298     -11.134   7.885 -25.564  1.00 48.38      A    C
ATOM   1966  C    ALA A 298      -9.656   6.254 -26.683  1.00 47.14      A    C
ATOM   1967  O    ALA A 298     -10.565   5.604 -27.180  1.00 47.14      A    O
ATOM   1968  N    HIS A 299      -8.459   5.754 -26.436  1.00 48.29      A    N
ATOM   1969  CA   HIS A 299      -8.123   4.380 -26.740  1.00 48.29      A    C
ATOM   1970  CB   HIS A 299      -6.653   4.141 -26.409  1.00 61.92      A    C
ATOM   1971  CG   HIS A 299      -5.979   3.173 -27.323  1.00 61.92      A    C
ATOM   1972  CD2  HIS A 299      -5.664   3.263 -28.635  1.00 61.92      A    C
ATOM   1973  ND1  HIS A 299      -5.507   1.949 -26.896  1.00 61.92      A    N
ATOM   1974  CE1  HIS A 299      -4.923   1.330 -27.907  1.00 61.92      A    C
ATOM   1975  NE2  HIS A 299      -5.004   2.106 -28.973  1.00 61.92      A    N
ATOM   1976  C    HIS A 299      -8.985   3.395 -25.961  1.00 48.29      A    C
ATOM   1977  O    HIS A 299      -9.155   3.520 -24.746  1.00 48.29      A    O
ATOM   1978  N    PRO A 300      -9.563   2.408 -26.662  1.00 67.72      A    N
ATOM   1979  CD   PRO A 300      -9.463   2.168 -28.114  1.00 46.60      A    C
ATOM   1980  CA   PRO A 300     -10.406   1.396 -26.007  1.00 67.72      A    C
ATOM   1981  CB   PRO A 300     -10.938   0.577 -27.183  1.00 46.60      A    C
ATOM   1982  CG   PRO A 300      -9.827   0.704 -28.211  1.00 46.60      A    C
ATOM   1983  C    PRO A 300      -9.580   0.551 -25.015  1.00 67.72      A    C
ATOM   1984  O    PRO A 300      -8.594  -0.097 -25.395  1.00 67.72      A    O
ATOM   1985  N    TRP A 301      -9.995   0.569 -23.747  1.00 65.47      A    N
ATOM   1986  CA   TRP A 301      -9.313  -0.155 -22.679  1.00 65.47      A    C
ATOM   1987  CB   TRP A 301     -10.250  -0.329 -21.483  1.00 52.29      A    C
ATOM   1988  CG   TRP A 301     -10.172   0.808 -20.508  1.00 52.29      A    C
ATOM   1989  CD2  TRP A 301      -8.994   1.284 -19.833  1.00 52.29      A    C
ATOM   1990  CE2  TRP A 301      -9.376   2.404 -19.058  1.00 52.29      A    C
ATOM   1991  CE3  TRP A 301      -7.660   0.864 -19.799  1.00 52.29      A    C
ATOM   1992  CD1  TRP A 301     -11.193   1.637 -20.124  1.00 52.29      A    C
ATOM   1993  NE1  TRP A 301     -10.719   2.603 -19.253  1.00 52.29      A    N
ATOM   1994  CZ2  TRP A 301      -8.464   3.120 -18.275  1.00 52.29      A    C
ATOM   1995  CZ3  TRP A 301      -6.750   1.576 -19.015  1.00 52.29      A    C
ATOM   1996  CH2  TRP A 301      -7.159   2.687 -18.262  1.00 52.29      A    C
ATOM   1997  C    TRP A 301      -8.746  -1.509 -23.086  1.00 65.47      A    C
ATOM   1998  O    TRP A 301      -7.607  -1.847 -22.748  1.00 65.47      A    O
ATOM   1999  N    THR A 302      -9.537  -2.281 -23.818  1.00 59.65      A    N
ATOM   2000  CA   THR A 302      -9.114  -3.608 -24.253  1.00 59.65      A    C
ATOM   2001  CB   THR A 302     -10.254  -4.333 -24.995  1.00 64.90      A    C
ATOM   2002  OG1  THR A 302     -10.580  -3.601 -26.190  1.00 64.90      A    O
ATOM   2003  CG2  THR A 302     -11.492  -4.443 -24.097  1.00 64.90      A    C
```

FIG. 3-31

```
ATOM   2004  C    THR A 302      -7.878  -3.582 -25.157  1.00 59.65           A  C
ATOM   2005  O    THR A 302      -6.946  -4.360 -24.967  1.00 59.65           A  O
ATOM   2006  N    ALA A 303      -7.864  -2.700 -26.145  1.00 56.57           A  N
ATOM   2007  CA   ALA A 303      -6.711  -2.632 -27.038  1.00 56.57           A  C
ATOM   2008  CB   ALA A 303      -7.071  -1.829 -28.311  1.00 85.17           A  C
ATOM   2009  C    ALA A 303      -5.514  -1.996 -26.318  1.00 56.57           A  C
ATOM   2010  O    ALA A 303      -4.515  -1.632 -26.947  1.00 56.57           A  O
ATOM   2011  N    VAL A 304      -5.630  -1.863 -24.997  1.00 46.02           A  N
ATOM   2012  CA   VAL A 304      -4.578  -1.273 -24.176  1.00 46.02           A  C
ATOM   2013  CB   VAL A 304      -5.175  -0.329 -23.096  1.00 45.10           A  C
ATOM   2014  CG1  VAL A 304      -4.065   0.242 -22.205  1.00 45.10           A  C
ATOM   2015  CG2  VAL A 304      -5.951   0.789 -23.768  1.00 45.10           A  C
ATOM   2016  C    VAL A 304      -3.765  -2.356 -23.481  1.00 46.02           A  C
ATOM   2017  O    VAL A 304      -2.565  -2.195 -23.263  1.00 46.02           A  O
ATOM   2018  N    PHE A 305      -4.420  -3.461 -23.137  1.00 50.92           A  N
ATOM   2019  CA   PHE A 305      -3.741  -4.559 -22.457  1.00 50.92           A  C
ATOM   2020  CB   PHE A 305      -4.620  -5.071 -21.316  1.00 50.44           A  C
ATOM   2021  CG   PHE A 305      -4.796  -4.074 -20.212  1.00 50.44           A  C
ATOM   2022  CD1  PHE A 305      -3.872  -3.996 -19.180  1.00 50.44           A  C
ATOM   2023  CD2  PHE A 305      -5.844  -3.155 -20.249  1.00 50.44           A  C
ATOM   2024  CE1  PHE A 305      -3.982  -3.011 -18.198  1.00 50.44           A  C
ATOM   2025  CE2  PHE A 305      -5.961  -2.166 -19.274  1.00 50.44           A  C
ATOM   2026  CZ   PHE A 305      -5.027  -2.093 -18.246  1.00 50.44           A  C
ATOM   2027  C    PHE A 305      -3.363  -5.701 -23.391  1.00 50.92           A  C
ATOM   2028  O    PHE A 305      -3.917  -5.827 -24.479  1.00 50.92           A  O
ATOM   2029  N    ARG A 306      -2.400  -6.523 -22.986  1.00 53.83           A  N
ATOM   2030  CA   ARG A 306      -2.010  -7.633 -23.840  1.00 53.83           A  C
ATOM   2031  CB   ARG A 306      -0.896  -8.475 -23.192  1.00 79.13           A  C
ATOM   2032  CG   ARG A 306      -1.112  -8.860 -21.721  1.00 79.13           A  C
ATOM   2033  CD   ARG A 306      -0.107  -9.939 -21.275  1.00 79.13           A  C
ATOM   2034  NE   ARG A 306      -0.651 -11.289 -21.426  1.00 79.13           A  N
ATOM   2035  CZ   ARG A 306      -1.489 -11.861 -20.560  1.00 79.13           A  C
ATOM   2036  NH1  ARG A 306      -1.884 -11.202 -19.466  1.00 79.13           A  N
ATOM   2037  NH2  ARG A 306      -1.934 -13.094 -20.782  1.00 79.13           A  N
ATOM   2038  C    ARG A 306      -3.251  -8.486 -24.104  1.00 53.83           A  C
ATOM   2039  O    ARG A 306      -4.195  -8.498 -23.302  1.00 53.83           A  O
ATOM   2040  N    PRO A 307      -3.272  -9.191 -25.244  1.00 56.50           A  N
ATOM   2041  CD   PRO A 307      -2.185  -9.123 -26.239  1.00 62.89           A  C
ATOM   2042  CA   PRO A 307      -4.346 -10.070 -25.719  1.00 56.50           A  C
ATOM   2043  CB   PRO A 307      -3.644 -10.901 -26.786  1.00 62.89           A  C
ATOM   2044  CG   PRO A 307      -2.766  -9.886 -27.426  1.00 62.89           A  C
ATOM   2045  C    PRO A 307      -5.076 -10.937 -24.692  1.00 56.50           A  C
ATOM   2046  O    PRO A 307      -6.296 -10.820 -24.524  1.00 56.50           A  O
ATOM   2047  N    ALA A 308      -4.339 -11.808 -24.010  1.00 65.02           A  N
ATOM   2048  CA   ALA A 308      -4.957 -12.708 -23.035  1.00 65.02           A  C
ATOM   2049  CB   ALA A 308      -4.147 -14.016 -22.949  1.00 90.94           A  C
ATOM   2050  C    ALA A 308      -5.170 -12.118 -21.630  1.00 65.02           A  C
ATOM   2051  O    ALA A 308      -5.159 -12.844 -20.631  1.00 65.02           A  O
ATOM   2052  N    THR A 309      -5.382 -10.806 -21.568  1.00 57.74           A  N
ATOM   2053  CA   THR A 309      -5.627 -10.113 -20.305  1.00 57.74           A  C
ATOM   2054  CB   THR A 309      -5.462  -8.589 -20.471  1.00 32.02           A  C
ATOM   2055  OG1  THR A 309      -4.113  -8.289 -20.859  1.00 32.02           A  O
ATOM   2056  CG2  THR A 309      -5.799  -7.878 -19.168  1.00 32.02           A  C
ATOM   2057  C    THR A 309      -7.047 -10.396 -19.804  1.00 57.74           A  C
ATOM   2058  O    THR A 309      -8.025 -10.095 -20.482  1.00 57.74           A  O
ATOM   2059  N    PRO A 310      -7.174 -10.977 -18.603  1.00 64.90           A  N
ATOM   2060  CD   PRO A 310      -6.102 -11.258 -17.629  1.00 34.19           A  C
ATOM   2061  CA   PRO A 310      -8.495 -11.289 -18.037  1.00 64.90           A  C
ATOM   2062  CB   PRO A 310      -8.176 -11.599 -16.577  1.00 34.19           A  C
ATOM   2063  CG   PRO A 310      -6.793 -12.169 -16.647  1.00 34.19           A  C
ATOM   2064  C    PRO A 310      -9.491 -10.128 -18.168  1.00 64.90           A  C
ATOM   2065  O    PRO A 310      -9.234  -9.013 -17.703  1.00 64.90           A  O
ATOM   2066  N    PRO A 311     -10.641 -10.373 -18.809  1.00 64.09           A  N
ATOM   2067  CD   PRO A 311     -10.984 -11.599 -19.545  1.00 52.92           A  C
ATOM   2068  CA   PRO A 311     -11.676  -9.355 -19.001  1.00 64.09           A  C
ATOM   2069  CB   PRO A 311     -12.844 -10.164 -19.529  1.00 52.92           A  C
ATOM   2070  CG   PRO A 311     -12.149 -11.136 -20.410  1.00 52.92           A  C
```

FIG. 3-32

```
ATOM   2071  C   PRO A 311     -12.034  -8.581 -17.733  1.00 64.09      A  C
ATOM   2072  O   PRO A 311     -12.141  -7.351 -17.771  1.00 64.09      A  O
ATOM   2073  N   GLU A 312     -12.219  -9.288 -16.620  1.00 55.01      A  N
ATOM   2074  CA  GLU A 312     -12.568  -8.628 -15.368  1.00 55.01      A  C
ATOM   2075  CB  GLU A 312     -12.942  -9.639 -14.287  1.00100.00      A  C
ATOM   2076  CG  GLU A 312     -14.076 -10.550 -14.681  1.00100.00      A  C
ATOM   2077  CD  GLU A 312     -13.598 -11.761 -15.476  1.00100.00      A  C
ATOM   2078  OE1 GLU A 312     -12.767 -11.598 -16.419  1.00100.00      A  O
ATOM   2079  OE2 GLU A 312     -14.071 -12.880 -15.150  1.00100.00      A  O
ATOM   2080  C   GLU A 312     -11.429  -7.761 -14.862  1.00 55.01      A  C
ATOM   2081  O   GLU A 312     -11.670  -6.766 -14.189  1.00 55.01      A  O
ATOM   2082  N   ALA A 313     -10.190  -8.133 -15.160  1.00 30.55      A  N
ATOM   2083  CA  ALA A 313      -9.066  -7.317 -14.727  1.00 30.55      A  C
ATOM   2084  CB  ALA A 313      -7.757  -7.932 -15.199  1.00 36.01      A  C
ATOM   2085  C   ALA A 313      -9.278  -5.951 -15.375  1.00 30.55      A  C
ATOM   2086  O   ALA A 313      -9.151  -4.906 -14.738  1.00 30.55      A  O
ATOM   2087  N   ILE A 314      -9.624  -5.979 -16.655  1.00 47.62      A  N
ATOM   2088  CA  ILE A 314      -9.879  -4.766 -17.421  1.00 47.62      A  C
ATOM   2089  CB  ILE A 314     -10.104  -5.113 -18.907  1.00 40.14      A  C
ATOM   2090  CG2 ILE A 314     -10.517  -3.866 -19.685  1.00 40.14      A  C
ATOM   2091  CG1 ILE A 314      -8.823  -5.725 -19.486  1.00 40.14      A  C
ATOM   2092  CD1 ILE A 314      -8.966  -6.262 -20.895  1.00 40.14      A  C
ATOM   2093  C   ILE A 314     -11.098  -4.002 -16.878  1.00 47.62      A  C
ATOM   2094  O   ILE A 314     -11.048  -2.788 -16.671  1.00 47.62      A  O
ATOM   2095  N   ALA A 315     -12.192  -4.714 -16.652  1.00 42.81      A  N
ATOM   2096  CA  ALA A 315     -13.386  -4.083 -16.137  1.00 42.81      A  C
ATOM   2097  CB  ALA A 315     -14.425  -5.139 -15.799  1.00 51.11      A  C
ATOM   2098  C   ALA A 315     -13.030  -3.290 -14.890  1.00 42.81      A  C
ATOM   2099  O   ALA A 315     -13.289  -2.083 -14.806  1.00 42.81      A  O
ATOM   2100  N   LEU A 316     -12.436  -3.986 -13.924  1.00 38.88      A  N
ATOM   2101  CA  LEU A 316     -12.037  -3.395 -12.658  1.00 38.88      A  C
ATOM   2102  CB  LEU A 316     -11.305  -4.429 -11.806  1.00 26.88      A  C
ATOM   2103  CG  LEU A 316     -10.479  -3.879 -10.640  1.00 26.88      A  C
ATOM   2104  CD1 LEU A 316     -11.381  -3.233  -9.603  1.00 26.88      A  C
ATOM   2105  CD2 LEU A 316      -9.670  -4.993 -10.028  1.00 26.88      A  C
ATOM   2106  C   LEU A 316     -11.134  -2.208 -12.879  1.00 38.88      A  C
ATOM   2107  O   LEU A 316     -11.288  -1.174 -12.249  1.00 38.88      A  O
ATOM   2108  N   CYS A 317     -10.187  -2.357 -13.786  1.00 44.68      A  N
ATOM   2109  CA  CYS A 317      -9.254  -1.284 -14.042  1.00 44.68      A  C
ATOM   2110  CB  CYS A 317      -8.233  -1.726 -15.083  1.00 39.70      A  C
ATOM   2111  SG  CYS A 317      -6.836  -0.625 -15.195  1.00 39.70      A  S
ATOM   2112  C   CYS A 317      -9.946  -0.008 -14.495  1.00 44.68      A  C
ATOM   2113  O   CYS A 317      -9.604   1.086 -14.040  1.00 44.68      A  O
ATOM   2114  N   SER A 318     -10.930  -0.146 -15.378  1.00 50.01      A  N
ATOM   2115  CA  SER A 318     -11.654   1.011 -15.909  1.00 50.01      A  C
ATOM   2116  CB  SER A 318     -12.497   0.575 -17.093  1.00 37.17      A  C
ATOM   2117  OG  SER A 318     -13.380  -0.444 -16.672  1.00 37.17      A  O
ATOM   2118  C   SER A 318     -12.544   1.735 -14.890  1.00 50.01      A  C
ATOM   2119  O   SER A 318     -12.875   2.909 -15.060  1.00 50.01      A  O
ATOM   2120  N   ARG A 319     -12.936   1.038 -13.837  1.00 35.75      A  N
ATOM   2121  CA  ARG A 319     -13.772   1.646 -12.812  1.00 35.75      A  C
ATOM   2122  CB  ARG A 319     -14.722   0.594 -12.244  1.00 54.31      A  C
ATOM   2123  CG  ARG A 319     -15.717   0.069 -13.259  1.00 54.31      A  C
ATOM   2124  CD  ARG A 319     -16.815   1.090 -13.563  1.00 54.31      A  C
ATOM   2125  NE  ARG A 319     -17.713   1.260 -12.426  1.00 54.31      A  N
ATOM   2126  CZ  ARG A 319     -17.727   2.333 -11.643  1.00 54.31      A  C
ATOM   2127  NH1 ARG A 319     -16.887   3.335 -11.884  1.00 54.31      A  N
ATOM   2128  NH2 ARG A 319     -18.573   2.398 -10.617  1.00 54.31      A  N
ATOM   2129  C   ARG A 319     -12.920   2.238 -11.690  1.00 35.75      A  C
ATOM   2130  O   ARG A 319     -13.431   2.669 -10.660  1.00 35.75      A  O
ATOM   2131  N   LEU A 320     -11.611   2.232 -11.898  1.00 34.41      A  N
ATOM   2132  CA  LEU A 320     -10.668   2.759 -10.932  1.00 34.41      A  C
ATOM   2133  CB  LEU A 320      -9.573   1.726 -10.654  1.00 28.61      A  C
ATOM   2134  CG  LEU A 320     -10.005   0.436  -9.942  1.00 28.61      A  C
ATOM   2135  CD1 LEU A 320      -8.839  -0.545  -9.884  1.00 28.61      A  C
ATOM   2136  CD2 LEU A 320     -10.495   0.762  -8.536  1.00 28.61      A  C
ATOM   2137  C   LEU A 320     -10.068   3.999 -11.559  1.00 34.41      A  C
```

FIG. 3-33

| ATOM | 2138 | O | LEU | A | 320 | -9.974 | 5.053 | -10.936 | 1.00 | 34.41 | A | O |
|---|---|---|---|---|---|---|---|---|---|---|---|---|
| ATOM | 2139 | N | LEU | A | 321 | -9.687 | 3.861 | -12.822 | 1.00 | 36.39 | A | N |
| ATOM | 2140 | CA | LEU | A | 321 | -9.085 | 4.950 | -13.561 | 1.00 | 36.39 | A | C |
| ATOM | 2141 | CB | LEU | A | 321 | -8.046 | 4.394 | -14.535 | 1.00 | 35.46 | A | C |
| ATOM | 2142 | CG | LEU | A | 321 | -6.886 | 3.658 | -13.857 | 1.00 | 35.46 | A | C |
| ATOM | 2143 | CD1 | LEU | A | 321 | -5.992 | 3.011 | -14.909 | 1.00 | 35.46 | A | C |
| ATOM | 2144 | CD2 | LEU | A | 321 | -6.108 | 4.629 | -12.992 | 1.00 | 35.46 | A | C |
| ATOM | 2145 | C | LEU | A | 321 | -10.116 | 5.782 | -14.298 | 1.00 | 36.39 | A | C |
| ATOM | 2146 | O | LEU | A | 321 | -10.236 | 5.708 | -15.517 | 1.00 | 36.39 | A | O |
| ATOM | 2147 | N | GLU | A | 322 | -10.865 | 6.570 | -13.537 | 1.00 | 40.80 | A | N |
| ATOM | 2148 | CA | GLU | A | 322 | -11.883 | 7.449 | -14.098 | 1.00 | 40.80 | A | C |
| ATOM | 2149 | CB | GLU | A | 322 | -13.256 | 7.146 | -13.483 | 1.00 | 49.19 | A | C |
| ATOM | 2150 | CG | GLU | A | 322 | -13.761 | 5.732 | -13.759 | 1.00 | 49.19 | A | C |
| ATOM | 2151 | CD | GLU | A | 322 | -15.005 | 5.592 | -14.645 | 1.00 | 49.19 | A | C |
| ATOM | 2152 | OE1 | GLU | A | 322 | -15.056 | 6.415 | -15.667 | 1.00 | 49.19 | A | O |
| ATOM | 2153 | OE2 | GLU | A | 322 | -15.928 | 4.911 | -14.317 | 1.00 | 49.19 | A | O |
| ATOM | 2154 | C | GLU | A | 322 | -11.483 | 8.880 | -13.781 | 1.00 | 40.80 | A | C |
| ATOM | 2155 | O | GLU | A | 322 | -10.897 | 9.135 | -12.734 | 1.00 | 40.80 | A | O |
| ATOM | 2156 | N | TYR | A | 323 | -11.772 | 9.811 | -14.683 | 1.00 | 36.98 | A | N |
| ATOM | 2157 | CA | TYR | A | 323 | -11.438 | 11.210 | -14.436 | 1.00 | 36.98 | A | C |
| ATOM | 2158 | CB | TYR | A | 323 | -11.783 | 12.073 | -15.646 | 1.00 | 41.83 | A | C |
| ATOM | 2159 | CG | TYR | A | 323 | -10.776 | 12.038 | -16.766 | 1.00 | 41.83 | A | C |
| ATOM | 2160 | CD1 | TYR | A | 323 | -9.512 | 12.611 | -16.615 | 1.00 | 41.83 | A | C |
| ATOM | 2161 | CE1 | TYR | A | 323 | -8.598 | 12.610 | -17.662 | 1.00 | 41.83 | A | C |
| ATOM | 2162 | CD2 | TYR | A | 323 | -11.095 | 11.460 | -17.993 | 1.00 | 41.83 | A | C |
| ATOM | 2163 | CE2 | TYR | A | 323 | -10.192 | 11.457 | -19.043 | 1.00 | 41.83 | A | C |
| ATOM | 2164 | CZ | TYR | A | 323 | -8.949 | 12.032 | -18.874 | 1.00 | 41.83 | A | C |
| ATOM | 2165 | OH | TYR | A | 323 | -8.072 | 12.031 | -19.931 | 1.00 | 41.83 | A | O |
| ATOM | 2166 | C | TYR | A | 323 | -12.222 | 11.712 | -13.232 | 1.00 | 36.98 | A | C |
| ATOM | 2167 | O | TYR | A | 323 | -11.655 | 12.267 | -12.297 | 1.00 | 36.98 | A | O |
| ATOM | 2168 | N | THR | A | 324 | -13.533 | 11.506 | -13.264 | 1.00 | 36.28 | A | N |
| ATOM | 2169 | CA | THR | A | 324 | -14.409 | 11.942 | -12.183 | 1.00 | 36.28 | A | C |
| ATOM | 2170 | CB | THR | A | 324 | -15.899 | 11.733 | -12.559 | 1.00 | 52.97 | A | C |
| ATOM | 2171 | OG1 | THR | A | 324 | -16.213 | 12.520 | -13.713 | 1.00 | 52.97 | A | O |
| ATOM | 2172 | CG2 | THR | A | 324 | -16.813 | 12.141 | -11.419 | 1.00 | 52.97 | A | C |
| ATOM | 2173 | C | THR | A | 324 | -14.101 | 11.165 | -10.912 | 1.00 | 36.28 | A | C |
| ATOM | 2174 | O | THR | A | 324 | -14.412 | 9.980 | -10.812 | 1.00 | 36.28 | A | O |
| ATOM | 2175 | N | PRO | A | 325 | -13.471 | 11.828 | -9.925 | 1.00 | 39.52 | A | N |
| ATOM | 2176 | CD | PRO | A | 325 | -13.087 | 13.252 | -9.959 | 1.00 | 33.38 | A | C |
| ATOM | 2177 | CA | PRO | A | 325 | -13.104 | 11.227 | -8.639 | 1.00 | 39.52 | A | C |
| ATOM | 2178 | CB | PRO | A | 325 | -12.750 | 12.435 | -7.794 | 1.00 | 33.38 | A | C |
| ATOM | 2179 | CG | PRO | A | 325 | -12.136 | 13.358 | -8.798 | 1.00 | 33.38 | A | C |
| ATOM | 2180 | C | PRO | A | 325 | -14.268 | 10.463 | -8.063 | 1.00 | 39.52 | A | C |
| ATOM | 2181 | O | PRO | A | 325 | -14.141 | 9.324 | -7.638 | 1.00 | 39.52 | A | O |
| ATOM | 2182 | N | THR | A | 326 | -15.416 | 11.115 | -8.078 | 1.00 | 30.83 | A | N |
| ATOM | 2183 | CA | THR | A | 326 | -16.656 | 10.562 | -7.557 | 1.00 | 30.83 | A | C |
| ATOM | 2184 | CB | THR | A | 326 | -17.753 | 11.648 | -7.646 | 1.00 | 38.12 | A | C |
| ATOM | 2185 | OG1 | THR | A | 326 | -18.320 | 11.847 | -6.348 | 1.00 | 38.12 | A | O |
| ATOM | 2186 | CG2 | THR | A | 326 | -18.852 | 11.272 | -8.664 | 1.00 | 38.12 | A | C |
| ATOM | 2187 | C | THR | A | 326 | -17.125 | 9.277 | -8.246 | 1.00 | 30.83 | A | C |
| ATOM | 2188 | O | THR | A | 326 | -17.937 | 8.537 | -7.708 | 1.00 | 30.83 | A | O |
| ATOM | 2189 | N | ALA | A | 327 | -16.600 | 9.013 | -9.432 | 1.00 | 35.79 | A | N |
| ATOM | 2190 | CA | ALA | A | 327 | -16.989 | 7.842 | -10.209 | 1.00 | 35.79 | A | C |
| ATOM | 2191 | CB | ALA | A | 327 | -16.865 | 8.163 | -11.684 | 1.00 | 47.40 | A | C |
| ATOM | 2192 | C | ALA | A | 327 | -16.226 | 6.548 | -9.914 | 1.00 | 35.79 | A | C |
| ATOM | 2193 | O | ALA | A | 327 | -16.699 | 5.457 | -10.233 | 1.00 | 35.79 | A | O |
| ATOM | 2194 | N | ARG | A | 328 | -15.045 | 6.675 | -9.317 | 1.00 | 44.41 | A | N |
| ATOM | 2195 | CA | ARG | A | 328 | -14.207 | 5.526 | -9.008 | 1.00 | 44.41 | A | C |
| ATOM | 2196 | CB | ARG | A | 328 | -12.839 | 6.005 | -8.543 | 1.00 | 37.43 | A | C |
| ATOM | 2197 | CG | ARG | A | 328 | -12.119 | 6.786 | -9.600 | 1.00 | 37.43 | A | C |
| ATOM | 2198 | CD | ARG | A | 328 | -10.983 | 7.593 | -9.039 | 1.00 | 37.43 | A | C |
| ATOM | 2199 | NE | ARG | A | 328 | -10.534 | 8.556 | -10.031 | 1.00 | 37.43 | A | N |
| ATOM | 2200 | CZ | ARG | A | 328 | -9.899 | 9.682 | -9.747 | 1.00 | 37.43 | A | C |
| ATOM | 2201 | NH1 | ARG | A | 328 | -9.627 | 9.997 | -8.490 | 1.00 | 37.43 | A | N |
| ATOM | 2202 | NH2 | ARG | A | 328 | -9.560 | 10.502 | -10.729 | 1.00 | 37.43 | A | N |
| ATOM | 2203 | C | ARG | A | 328 | -14.814 | 4.640 | -7.955 | 1.00 | 44.41 | A | C |
| ATOM | 2204 | O | ARG | A | 328 | -15.559 | 5.113 | -7.106 | 1.00 | 44.41 | A | O |

FIG. 3-34

```
ATOM   2205  N    LEU A 329     -14.501    3.352   -8.012  1.00 31.71      A    N
ATOM   2206  CA   LEU A 329     -15.012    2.417   -7.022  1.00 31.71      A    C
ATOM   2207  CB   LEU A 329     -14.626    0.986   -7.398  1.00 44.09      A    C
ATOM   2208  CG   LEU A 329     -15.485    0.103   -8.308  1.00 44.09      A    C
ATOM   2209  CD1  LEU A 329     -16.026    0.914   -9.439  1.00 44.09      A    C
ATOM   2210  CD2  LEU A 329     -14.646   -1.064   -8.830  1.00 44.09      A    C
ATOM   2211  C    LEU A 329     -14.402    2.751   -5.657  1.00 31.71      A    C
ATOM   2212  O    LEU A 329     -13.382    3.432   -5.566  1.00 31.71      A    O
ATOM   2213  N    THR A 330     -15.036    2.282   -4.593  1.00 35.01      A    N
ATOM   2214  CA   THR A 330     -14.511    2.504   -3.257  1.00 35.01      A    C
ATOM   2215  CB   THR A 330     -15.635    2.559   -2.208  1.00 39.37      A    C
ATOM   2216  OG1  THR A 330     -16.357    1.317   -2.203  1.00 39.37      A    O
ATOM   2217  CG2  THR A 330     -16.575    3.706   -2.506  1.00 39.37      A    C
ATOM   2218  C    THR A 330     -13.629    1.299   -2.960  1.00 35.01      A    C
ATOM   2219  O    THR A 330     -13.822    0.235   -3.531  1.00 35.01      A    O
ATOM   2220  N    PRO A 331     -12.652    1.444   -2.060  1.00 43.16      A    N
ATOM   2221  CD   PRO A 331     -12.221    2.626   -1.294  1.00 39.68      A    C
ATOM   2222  CA   PRO A 331     -11.798    0.296   -1.767  1.00 43.16      A    C
ATOM   2223  CB   PRO A 331     -10.970    0.790   -0.587  1.00 39.68      A    C
ATOM   2224  CG   PRO A 331     -10.818    2.245   -0.882  1.00 39.68      A    C
ATOM   2225  C    PRO A 331     -12.580   -0.987   -1.456  1.00 43.16      A    C
ATOM   2226  O    PRO A 331     -12.283   -2.051   -2.004  1.00 43.16      A    O
ATOM   2227  N    LEU A 332     -13.576   -0.899   -0.583  1.00 38.54      A    N
ATOM   2228  CA   LEU A 332     -14.348   -2.088   -0.252  1.00 38.54      A    C
ATOM   2229  CB   LEU A 332     -15.407   -1.778    0.798  1.00 56.75      A    C
ATOM   2230  CG   LEU A 332     -15.209   -2.451    2.152  1.00 56.75      A    C
ATOM   2231  CD1  LEU A 332     -16.511   -2.395    2.941  1.00 56.75      A    C
ATOM   2232  CD2  LEU A 332     -14.797   -3.894    1.954  1.00 56.75      A    C
ATOM   2233  C    LEU A 332     -15.027   -2.626   -1.495  1.00 38.54      A    C
ATOM   2234  O    LEU A 332     -15.173   -3.833   -1.655  1.00 38.54      A    O
ATOM   2235  N    GLU A 333     -15.448   -1.713   -2.366  1.00 45.56      A    N
ATOM   2236  CA   GLU A 333     -16.112   -2.074   -3.609  1.00 45.56      A    C
ATOM   2237  CB   GLU A 333     -16.568   -0.813   -4.335  1.00 58.40      A    C
ATOM   2238  CG   GLU A 333     -18.067   -0.612   -4.335  1.00 58.40      A    C
ATOM   2239  CD   GLU A 333     -18.457    0.850   -4.361  1.00 58.40      A    C
ATOM   2240  OE1  GLU A 333     -18.002    1.583   -5.277  1.00 58.40      A    O
ATOM   2241  OE2  GLU A 333     -19.225    1.261   -3.456  1.00 58.40      A    O
ATOM   2242  C    GLU A 333     -15.175   -2.874   -4.500  1.00 45.56      A    C
ATOM   2243  O    GLU A 333     -15.569   -3.886   -5.077  1.00 45.56      A    O
ATOM   2244  N    ALA A 334     -13.931   -2.419   -4.603  1.00 40.06      A    N
ATOM   2245  CA   ALA A 334     -12.933   -3.090   -5.419  1.00 40.06      A    C
ATOM   2246  CB   ALA A 334     -11.640   -2.289   -5.413  1.00 17.92      A    C
ATOM   2247  C    ALA A 334     -12.673   -4.528   -4.960  1.00 40.06      A    C
ATOM   2248  O    ALA A 334     -12.500   -5.423   -5.791  1.00 40.06      A    O
ATOM   2249  N    CYS A 335     -12.645   -4.752   -3.647  1.00 38.43      A    N
ATOM   2250  CA   CYS A 335     -12.402   -6.097   -3.116  1.00 38.43      A    C
ATOM   2251  CB   CYS A 335     -12.346   -6.098   -1.584  1.00 44.58      A    C
ATOM   2252  SG   CYS A 335     -10.950   -5.235   -0.871  1.00 44.58      A    S
ATOM   2253  C    CYS A 335     -13.551   -6.967   -3.548  1.00 38.43      A    C
ATOM   2254  O    CYS A 335     -13.389   -8.154   -3.827  1.00 38.43      A    O
ATOM   2255  N    ALA A 336     -14.724   -6.353   -3.597  1.00 43.52      A    N
ATOM   2256  CA   ALA A 336     -15.932   -7.051   -3.979  1.00 43.52      A    C
ATOM   2257  CB   ALA A 336     -17.136   -6.206   -3.622  1.00 51.07      A    C
ATOM   2258  C    ALA A 336     -15.946   -7.388   -5.461  1.00 43.52      A    C
ATOM   2259  O    ALA A 336     -16.671   -8.282   -5.891  1.00 43.52      A    O
ATOM   2260  N    HIS A 337     -15.141   -6.683   -6.243  1.00 45.08      A    N
ATOM   2261  CA   HIS A 337     -15.104   -6.935   -7.674  1.00 45.08      A    C
ATOM   2262  CB   HIS A 337     -14.008   -6.119   -8.335  1.00 41.50      A    C
ATOM   2263  CG   HIS A 337     -14.110   -6.089   -9.826  1.00 41.50      A    C
ATOM   2264  CD2  HIS A 337     -13.737   -6.992  -10.762  1.00 41.50      A    C
ATOM   2265  ND1  HIS A 337     -14.637   -5.017  -10.515  1.00 41.50      A    N
ATOM   2266  CE1  HIS A 337     -14.577   -5.257  -11.812  1.00 41.50      A    C
ATOM   2267  NE2  HIS A 337     -14.034   -6.448  -11.988  1.00 41.50      A    N
ATOM   2268  C    HIS A 337     -14.883   -8.414   -7.982  1.00 45.08      A    C
ATOM   2269  O    HIS A 337     -14.167   -9.110   -7.251  1.00 45.08      A    O
ATOM   2270  N    SER A 338     -15.484   -8.888   -9.073  1.00 58.56      A    N
ATOM   2271  CA   SER A 338     -15.371  -10.295   -9.460  1.00 58.56      A    C
```

FIG. 3-35

```
ATOM   2272  CB   SER A 338     -16.439  -10.647  -10.508  1.00 54.47      A  C
ATOM   2273  OG   SER A 338     -16.452   -9.716  -11.574  1.00 54.47      A  O
ATOM   2274  C    SER A 338     -13.985  -10.710   -9.955  1.00 58.56      A  C
ATOM   2275  O    SER A 338     -13.694  -11.898  -10.061  1.00 58.56      A  O
ATOM   2276  N    PHE A 339     -13.136   -9.737  -10.271  1.00 48.63      A  N
ATOM   2277  CA   PHE A 339     -11.775  -10.030  -10.703  1.00 48.63      A  C
ATOM   2278  CB   PHE A 339     -10.997   -8.716  -10.864  1.00 43.11      A  C
ATOM   2279  CG   PHE A 339      -9.503   -8.886  -11.058  1.00 43.11      A  C
ATOM   2280  CD1  PHE A 339      -8.993   -9.638  -12.111  1.00 43.11      A  C
ATOM   2281  CD2  PHE A 339      -8.607   -8.231  -10.226  1.00 43.11      A  C
ATOM   2282  CE1  PHE A 339      -7.609   -9.726  -12.328  1.00 43.11      A  C
ATOM   2283  CE2  PHE A 339      -7.229   -8.315  -10.438  1.00 43.11      A  C
ATOM   2284  CZ   PHE A 339      -6.733   -9.060  -11.488  1.00 43.11      A  C
ATOM   2285  C    PHE A 339     -11.142  -10.877   -9.596  1.00 48.63      A  C
ATOM   2286  O    PHE A 339     -10.318  -11.761   -9.852  1.00 48.63      A  O
ATOM   2287  N    PHE A 340     -11.566  -10.607   -8.362  1.00 52.47      A  N
ATOM   2288  CA   PHE A 340     -11.040  -11.297   -7.194  1.00 52.47      A  C
ATOM   2289  CB   PHE A 340     -10.966  -10.328   -6.012  1.00 35.35      A  C
ATOM   2290  CG   PHE A 340     -10.144   -9.103   -6.275  1.00 35.35      A  C
ATOM   2291  CD1  PHE A 340      -8.809   -9.204   -6.639  1.00 35.35      A  C
ATOM   2292  CD2  PHE A 340     -10.697   -7.841   -6.127  1.00 35.35      A  C
ATOM   2293  CE1  PHE A 340      -8.034   -8.067   -6.849  1.00 35.35      A  C
ATOM   2294  CE2  PHE A 340      -9.929   -6.699   -6.334  1.00 35.35      A  C
ATOM   2295  CZ   PHE A 340      -8.593   -6.817   -6.696  1.00 35.35      A  C
ATOM   2296  C    PHE A 340     -11.816  -12.537   -6.758  1.00 52.47      A  C
ATOM   2297  O    PHE A 340     -11.427  -13.183   -5.780  1.00 52.47      A  O
ATOM   2298  N    ASP A 341     -12.899  -12.875   -7.459  1.00 44.49      A  N
ATOM   2299  CA   ASP A 341     -13.702  -14.049   -7.088  1.00 44.49      A  C
ATOM   2300  CB   ASP A 341     -14.732  -14.386   -8.175  1.00 40.97      A  C
ATOM   2301  CG   ASP A 341     -15.805  -13.313   -8.327  1.00 40.97      A  C
ATOM   2302  OD1  ASP A 341     -16.010  -12.524   -7.381  1.00 40.97      A  O
ATOM   2303  OD2  ASP A 341     -16.454  -13.268   -9.393  1.00 40.97      A  O
ATOM   2304  C    ASP A 341     -12.856  -15.287   -6.801  1.00 44.49      A  C
ATOM   2305  O    ASP A 341     -13.080  -15.982   -5.816  1.00 44.49      A  O
ATOM   2306  N    GLU A 342     -11.881  -15.565   -7.655  1.00 48.42      A  N
ATOM   2307  CA   GLU A 342     -11.022  -16.721   -7.449  1.00 48.42      A  C
ATOM   2308  CB   GLU A 342      -9.854  -16.699   -8.443  1.00 44.98      A  C
ATOM   2309  CG   GLU A 342      -8.763  -17.710   -8.138  1.00 44.98      A  C
ATOM   2310  CD   GLU A 342      -7.765  -17.861   -9.270  1.00 44.98      A  C
ATOM   2311  OE1  GLU A 342      -7.328  -16.836   -9.839  1.00 44.98      A  O
ATOM   2312  OE2  GLU A 342      -7.405  -19.014   -9.589  1.00 44.98      A  O
ATOM   2313  C    GLU A 342     -10.489  -16.793   -6.011  1.00 48.42      A  C
ATOM   2314  O    GLU A 342     -10.270  -17.878   -5.479  1.00 48.42      A  O
ATOM   2315  N    LEU A 343     -10.286  -15.643   -5.375  1.00 46.83      A  N
ATOM   2316  CA   LEU A 343      -9.777  -15.622   -4.004  1.00 46.83      A  C
ATOM   2317  CB   LEU A 343      -9.328  -14.202   -3.630  1.00 33.87      A  C
ATOM   2318  CG   LEU A 343      -8.248  -13.585   -4.518  1.00 33.87      A  C
ATOM   2319  CD1  LEU A 343      -7.945  -12.193   -4.029  1.00 33.87      A  C
ATOM   2320  CD2  LEU A 343      -6.990  -14.442   -4.507  1.00 33.87      A  C
ATOM   2321  C    LEU A 343     -10.844  -16.097   -3.024  1.00 46.83      A  C
ATOM   2322  O    LEU A 343     -10.544  -16.519   -1.907  1.00 46.83      A  O
ATOM   2323  N    ARG A 344     -12.095  -16.023   -3.459  1.00 56.15      A  N
ATOM   2324  CA   ARG A 344     -13.225  -16.425   -2.628  1.00 56.15      A  C
ATOM   2325  CB   ARG A 344     -14.458  -15.576   -2.985  1.00 57.40      A  C
ATOM   2326  CG   ARG A 344     -14.522  -14.247   -2.227  1.00 57.40      A  C
ATOM   2327  CD   ARG A 344     -15.555  -13.317   -2.829  1.00 57.40      A  C
ATOM   2328  NE   ARG A 344     -15.090  -12.800   -4.114  1.00 57.40      A  N
ATOM   2329  CZ   ARG A 344     -14.531  -11.603   -4.286  1.00 57.40      A  C
ATOM   2330  NH1  ARG A 344     -14.372  -10.783   -3.250  1.00 57.40      A  N
ATOM   2331  NH2  ARG A 344     -14.116  -11.233   -5.493  1.00 57.40      A  N
ATOM   2332  C    ARG A 344     -13.523  -17.920   -2.750  1.00 56.15      A  C
ATOM   2333  O    ARG A 344     -14.295  -18.490   -1.970  1.00 56.15      A  O
ATOM   2334  N    ASP A 345     -12.899  -18.540   -3.743  1.00 68.84      A  N
ATOM   2335  CA   ASP A 345     -13.024  -19.973   -3.976  1.00 68.84      A  C
ATOM   2336  CB   ASP A 345     -12.181  -20.325   -5.204  1.00 65.99      A  C
ATOM   2337  CG   ASP A 345     -12.172  -21.814   -5.528  1.00 65.99      A  C
ATOM   2338  OD1  ASP A 345     -12.232  -22.660   -4.594  1.00 65.99      A  O
```

FIG. 3-36

```
ATOM   2339  OD2 ASP A 345     -12.068 -22.128  -6.744  1.00 65.99      A  O
ATOM   2340  C   ASP A 345     -12.464 -20.666  -2.705  1.00 68.84      A  C
ATOM   2341  O   ASP A 345     -11.407 -20.273  -2.178  1.00 68.84      A  O
ATOM   2342  N   PRO A 346     -13.162 -21.697  -2.191  1.00 61.03      A  N
ATOM   2343  CD  PRO A 346     -14.382 -22.349  -2.697  1.00 39.82      A  C
ATOM   2344  CA  PRO A 346     -12.673 -22.384  -0.989  1.00 61.03      A  C
ATOM   2345  CB  PRO A 346     -13.849 -23.270  -0.611  1.00 39.82      A  C
ATOM   2346  CG  PRO A 346     -14.358 -23.681  -1.959  1.00 39.82      A  C
ATOM   2347  C   PRO A 346     -11.409 -23.197  -1.275  1.00 61.03      A  C
ATOM   2348  O   PRO A 346     -10.673 -23.567  -0.359  1.00 61.03      A  O
ATOM   2349  N   ASN A 347     -11.159 -23.454  -2.554  1.00 48.33      A  N
ATOM   2350  CA  ASN A 347     -10.005 -24.238  -2.985  1.00 48.33      A  C
ATOM   2351  CB  ASN A 347     -10.374 -25.045  -4.229  1.00 80.59      A  C
ATOM   2352  CG  ASN A 347     -11.509 -26.020  -3.977  1.00 80.59      A  C
ATOM   2353  OD1 ASN A 347     -12.282 -26.343  -4.893  1.00 80.59      A  O
ATOM   2354  ND2 ASN A 347     -11.615 -26.505  -2.731  1.00 80.59      A  N
ATOM   2355  C   ASN A 347      -8.757 -23.425  -3.297  1.00 48.33      A  C
ATOM   2356  O   ASN A 347      -7.637 -23.931  -3.193  1.00 48.33      A  O
ATOM   2357  N   VAL A 348      -8.945 -22.170  -3.695  1.00 69.45      A  N
ATOM   2358  CA  VAL A 348      -7.807 -21.324  -4.056  1.00 69.45      A  C
ATOM   2359  CB  VAL A 348      -8.177 -19.820  -4.066  1.00 73.02      A  C
ATOM   2360  CG1 VAL A 348      -8.676 -19.394  -2.697  1.00 73.02      A  C
ATOM   2361  CG2 VAL A 348      -6.960 -18.993  -4.474  1.00 73.02      A  C
ATOM   2362  C   VAL A 348      -6.629 -21.516  -3.124  1.00 69.45      A  C
ATOM   2363  O   VAL A 348      -6.791 -21.521  -1.902  1.00 69.45      A  O
ATOM   2364  N   LYS A 349      -5.450 -21.692  -3.708  1.00 50.24      A  N
ATOM   2365  CA  LYS A 349      -4.237 -21.864  -2.920  1.00 50.24      A  C
ATOM   2366  CB  LYS A 349      -3.887 -23.350  -2.784  1.00 75.12      A  C
ATOM   2367  CG  LYS A 349      -5.094 -24.228  -2.437  1.00 75.12      A  C
ATOM   2368  CD  LYS A 349      -4.685 -25.570  -1.841  1.00 75.12      A  C
ATOM   2369  CE  LYS A 349      -4.213 -25.412  -0.393  1.00 75.12      A  C
ATOM   2370  NZ  LYS A 349      -5.328 -24.960   0.496  1.00 75.12      A  N
ATOM   2371  C   LYS A 349      -3.134 -21.123  -3.640  1.00 50.24      A  C
ATOM   2372  O   LYS A 349      -3.277 -20.791  -4.813  1.00 50.24      A  O
ATOM   2373  N   LEU A 350      -2.043 -20.837  -2.952  1.00 40.61      A  N
ATOM   2374  CA  LEU A 350      -0.968 -20.124  -3.614  1.00 40.61      A  C
ATOM   2375  CB  LEU A 350       0.012 -19.564  -2.585  1.00 47.11      A  C
ATOM   2376  CG  LEU A 350      -0.550 -18.682  -1.469  1.00 47.11      A  C
ATOM   2377  CD1 LEU A 350       0.555 -18.310  -0.498  1.00 47.11      A  C
ATOM   2378  CD2 LEU A 350      -1.158 -17.446  -2.072  1.00 47.11      A  C
ATOM   2379  C   LEU A 350      -0.256 -21.112  -4.519  1.00 40.61      A  C
ATOM   2380  O   LEU A 350      -0.394 -22.325  -4.355  1.00 40.61      A  O
ATOM   2381  N   PRO A 351       0.509 -20.615  -5.498  1.00 56.15      A  N
ATOM   2382  CD  PRO A 351       0.797 -19.213  -5.849  1.00 61.09      A  C
ATOM   2383  CA  PRO A 351       1.219 -21.540  -6.386  1.00 56.15      A  C
ATOM   2384  CB  PRO A 351       1.747 -20.622  -7.488  1.00 61.09      A  C
ATOM   2385  CG  PRO A 351       2.001 -19.345  -6.763  1.00 61.09      A  C
ATOM   2386  C   PRO A 351       2.330 -22.180  -5.558  1.00 56.15      A  C
ATOM   2387  O   PRO A 351       3.202 -22.891  -6.058  1.00 56.15      A  O
ATOM   2388  N   ASN A 352       2.255 -21.906  -4.266  1.00 54.62      A  N
ATOM   2389  CA  ASN A 352       3.194 -22.381  -3.269  1.00 54.62      A  C
ATOM   2390  CB  ASN A 352       3.311 -21.324  -2.180  1.00 69.15      A  C
ATOM   2391  CG  ASN A 352       4.678 -21.262  -1.599  1.00 69.15      A  C
ATOM   2392  OD1 ASN A 352       4.996 -20.356  -0.825  1.00 69.15      A  O
ATOM   2393  ND2 ASN A 352       5.520 -22.231  -1.971  1.00 69.15      A  N
ATOM   2394  C   ASN A 352       2.711 -23.676  -2.631  1.00 54.62      A  C
ATOM   2395  O   ASN A 352       3.450 -24.323  -1.889  1.00 54.62      A  O
ATOM   2396  N   GLY A 353       1.464 -24.040  -2.920  1.00 62.87      A  N
ATOM   2397  CA  GLY A 353       0.875 -25.230  -2.336  1.00 62.87      A  C
ATOM   2398  C   GLY A 353       0.216 -24.806  -1.033  1.00 62.87      A  C
ATOM   2399  O   GLY A 353      -0.768 -25.409  -0.566  1.00 62.87      A  O
ATOM   2400  N   ARG A 354       0.763 -23.732  -0.461  1.00 80.42      A  N
ATOM   2401  CA  ARG A 354       0.289 -23.165   0.806  1.00 80.42      A  C
ATOM   2402  CB  ARG A 354       1.345 -22.224   1.376  1.00 87.86      A  C
ATOM   2403  CG  ARG A 354       2.730 -22.831   1.394  1.00 87.86      A  C
ATOM   2404  CD  ARG A 354       3.787 -21.819   1.809  1.00 87.86      A  C
ATOM   2405  NE  ARG A 354       3.427 -21.151   3.059  1.00 87.86      A  N
```

FIG. 3-37

```
ATOM   2406  CZ   ARG A 354       4.304 -20.573   3.878  1.00 87.86      A  C
ATOM   2407  NH1  ARG A 354       5.606 -20.583   3.579  1.00 87.86      A  N
ATOM   2408  NH2  ARG A 354       3.878 -19.989   4.997  1.00 87.86      A  N
ATOM   2409  C    ARG A 354      -1.002 -22.393   0.604  1.00 80.42      A  C
ATOM   2410  O    ARG A 354      -1.302 -21.938  -0.511  1.00 80.42      A  O
ATOM   2411  N    ASP A 355      -1.765 -22.235   1.677  1.00 63.73      A  N
ATOM   2412  CA   ASP A 355      -3.017 -21.506   1.576  1.00 63.73      A  C
ATOM   2413  CB   ASP A 355      -3.899 -21.794   2.778  1.00 69.07      A  C
ATOM   2414  CG   ASP A 355      -3.886 -23.247   3.155  1.00 69.07      A  C
ATOM   2415  OD1  ASP A 355      -2.823 -23.696   3.652  1.00 69.07      A  O
ATOM   2416  OD2  ASP A 355      -4.919 -23.934   2.945  1.00 69.07      A  O
ATOM   2417  C    ASP A 355      -2.748 -20.016   1.493  1.00 63.73      A  C
ATOM   2418  O    ASP A 355      -1.652 -19.544   1.815  1.00 63.73      A  O
ATOM   2419  N    THR A 356      -3.757 -19.286   1.038  1.00 46.73      A  N
ATOM   2420  CA   THR A 356      -3.661 -17.845   0.912  1.00 46.73      A  C
ATOM   2421  CB   THR A 356      -4.771 -17.303   0.018  1.00 52.88      A  C
ATOM   2422  OG1  THR A 356      -6.028 -17.818   0.473  1.00 52.88      A  O
ATOM   2423  CG2  THR A 356      -4.550 -17.725  -1.423  1.00 52.88      A  C
ATOM   2424  C    THR A 356      -3.842 -17.250   2.293  1.00 46.73      A  C
ATOM   2425  O    THR A 356      -4.486 -17.849   3.154  1.00 46.73      A  O
ATOM   2426  N    PRO A 357      -3.269 -16.062   2.526  1.00 51.89      A  N
ATOM   2427  CD   PRO A 357      -2.511 -15.190   1.612  1.00 50.65      A  C
ATOM   2428  CA   PRO A 357      -3.420 -15.441   3.841  1.00 51.89      A  C
ATOM   2429  CB   PRO A 357      -2.671 -14.114   3.683  1.00 50.65      A  C
ATOM   2430  CG   PRO A 357      -2.755 -13.834   2.200  1.00 50.65      A  C
ATOM   2431  C    PRO A 357      -4.902 -15.253   4.155  1.00 51.89      A  C
ATOM   2432  O    PRO A 357      -5.760 -15.576   3.332  1.00 51.89      A  O
ATOM   2433  N    ALA A 358      -5.201 -14.755   5.350  1.00 59.43      A  N
ATOM   2434  CA   ALA A 358      -6.587 -14.511   5.740  1.00 59.43      A  C
ATOM   2435  CB   ALA A 358      -6.657 -14.204   7.233  1.00 59.13      A  C
ATOM   2436  C    ALA A 358      -7.110 -13.319   4.929  1.00 59.43      A  C
ATOM   2437  O    ALA A 358      -6.674 -12.193   5.136  1.00 59.43      A  O
ATOM   2438  N    LEU A 359      -8.041 -13.555   4.015  1.00 57.16      A  N
ATOM   2439  CA   LEU A 359      -8.552 -12.466   3.191  1.00 57.16      A  C
ATOM   2440  CB   LEU A 359      -8.435 -12.853   1.717  1.00 46.83      A  C
ATOM   2441  CG   LEU A 359      -7.035 -13.351   1.361  1.00 46.83      A  C
ATOM   2442  CD1  LEU A 359      -7.017 -13.954  -0.042  1.00 46.83      A  C
ATOM   2443  CD2  LEU A 359      -6.059 -12.191   1.491  1.00 46.83      A  C
ATOM   2444  C    LEU A 359      -9.992 -12.084   3.498  1.00 57.16      A  C
ATOM   2445  O    LEU A 359     -10.581 -11.264   2.783  1.00 57.16      A  O
ATOM   2446  N    PHE A 360     -10.550 -12.651   4.567  1.00 65.53      A  N
ATOM   2447  CA   PHE A 360     -11.943 -12.388   4.904  1.00 65.53      A  C
ATOM   2448  CB   PHE A 360     -12.786 -13.628   4.603  1.00 62.70      A  C
ATOM   2449  CG   PHE A 360     -12.464 -14.274   3.284  1.00 62.70      A  C
ATOM   2450  CD1  PHE A 360     -12.665 -13.588   2.090  1.00 62.70      A  C
ATOM   2451  CD2  PHE A 360     -11.948 -15.570   3.237  1.00 62.70      A  C
ATOM   2452  CE1  PHE A 360     -12.357 -14.180   0.863  1.00 62.70      A  C
ATOM   2453  CE2  PHE A 360     -11.635 -16.173   2.015  1.00 62.70      A  C
ATOM   2454  CZ   PHE A 360     -11.841 -15.475   0.821  1.00 62.70      A  C
ATOM   2455  C    PHE A 360     -12.220 -11.959   6.336  1.00 65.53      A  C
ATOM   2456  O    PHE A 360     -13.361 -11.611   6.653  1.00 65.53      A  O
ATOM   2457  N    ASN A 361     -11.217 -11.993   7.211  1.00 44.89      A  N
ATOM   2458  CA   ASN A 361     -11.464 -11.597   8.589  1.00 44.89      A  C
ATOM   2459  CB   ASN A 361     -10.337 -12.095   9.517  1.00 67.57      A  C
ATOM   2460  CG   ASN A 361      -8.949 -11.672   9.056  1.00 67.57      A  C
ATOM   2461  OD1  ASN A 361      -8.590 -11.842   7.886  1.00 67.57      A  O
ATOM   2462  ND2  ASN A 361      -8.150 -11.129   9.984  1.00 67.57      A  N
ATOM   2463  C    ASN A 361     -11.641 -10.086   8.652  1.00 44.89      A  C
ATOM   2464  O    ASN A 361     -10.796  -9.353   9.158  1.00 44.89      A  O
ATOM   2465  N    PHE A 362     -12.762  -9.632   8.108  1.00 49.94      A  N
ATOM   2466  CA   PHE A 362     -13.109  -8.219   8.065  1.00 49.94      A  C
ATOM   2467  CB   PHE A 362     -14.157  -7.967   6.983  1.00 51.09      A  C
ATOM   2468  CG   PHE A 362     -13.615  -7.949   5.590  1.00 51.09      A  C
ATOM   2469  CD1  PHE A 362     -13.177  -6.756   5.023  1.00 51.09      A  C
ATOM   2470  CD2  PHE A 362     -13.564  -9.119   4.834  1.00 51.09      A  C
ATOM   2471  CE1  PHE A 362     -12.697  -6.725   3.714  1.00 51.09      A  C
ATOM   2472  CE2  PHE A 362     -13.088  -9.101   3.535  1.00 51.09      A  C
```

FIG. 3-38

```
ATOM   2473  CZ   PHE A 362     -12.653   -7.902    2.971  1.00 51.09      A  C
ATOM   2474  C    PHE A 362     -13.711   -7.779    9.384  1.00 49.94      A  C
ATOM   2475  O    PHE A 362     -14.428   -8.549   10.030  1.00 49.94      A  O
ATOM   2476  N    THR A 363     -13.444   -6.532    9.765  1.00 64.01      A  N
ATOM   2477  CA   THR A 363     -14.000   -5.978   10.995  1.00 64.01      A  C
ATOM   2478  CB   THR A 363     -12.918   -5.308   11.847  1.00 55.01      A  C
ATOM   2479  OG1  THR A 363     -12.420   -4.146   11.162  1.00 55.01      A  O
ATOM   2480  CG2  THR A 363     -11.782   -6.292   12.116  1.00 55.01      A  C
ATOM   2481  C    THR A 363     -15.048   -4.928   10.628  1.00 64.01      A  C
ATOM   2482  O    THR A 363     -14.932   -4.271    9.585  1.00 64.01      A  O
ATOM   2483  N    THR A 364     -16.061   -4.766   11.478  1.00 67.58      A  N
ATOM   2484  CA   THR A 364     -17.127   -3.793   11.225  1.00 67.58      A  C
ATOM   2485  CB   THR A 364     -18.003   -3.570   12.457  1.00 49.68      A  C
ATOM   2486  OG1  THR A 364     -17.342   -2.650   13.336  1.00 49.68      A  O
ATOM   2487  CG2  THR A 364     -18.261   -4.896   13.172  1.00 49.68      A  C
ATOM   2488  C    THR A 364     -16.553   -2.438   10.824  1.00 67.58      A  C
ATOM   2489  O    THR A 364     -17.209   -1.653   10.128  1.00 67.58      A  O
ATOM   2490  N    GLN A 365     -15.337   -2.162   11.283  1.00 41.43      A  N
ATOM   2491  CA   GLN A 365     -14.676   -0.912   10.950  1.00 41.43      A  C
ATOM   2492  CB   GLN A 365     -13.399   -0.749   11.778  1.00 50.15      A  C
ATOM   2493  CG   GLN A 365     -12.534    0.438   11.372  1.00 50.15      A  C
ATOM   2494  CD   GLN A 365     -13.122    1.773   11.780  1.00 50.15      A  C
ATOM   2495  OE1  GLN A 365     -14.251    1.847   12.276  1.00 50.15      A  O
ATOM   2496  NE2  GLN A 365     -12.359    2.843   11.572  1.00 50.15      A  N
ATOM   2497  C    GLN A 365     -14.329   -0.931    9.466  1.00 41.43      A  C
ATOM   2498  O    GLN A 365     -14.517    0.055    8.767  1.00 41.43      A  O
ATOM   2499  N    GLU A 366     -13.822   -2.061    8.987  1.00 41.89      A  N
ATOM   2500  CA   GLU A 366     -13.447   -2.184    7.584  1.00 41.89      A  C
ATOM   2501  CB   GLU A 366     -12.732   -3.523    7.312  1.00 64.07      A  C
ATOM   2502  CG   GLU A 366     -11.487   -3.833    8.150  1.00 64.07      A  C
ATOM   2503  CD   GLU A 366     -10.799   -5.132    7.710  1.00 64.07      A  C
ATOM   2504  OE1  GLU A 366     -10.265   -5.177    6.572  1.00 64.07      A  O
ATOM   2505  OE2  GLU A 366     -10.800   -6.110    8.502  1.00 64.07      A  O
ATOM   2506  C    GLU A 366     -14.706   -2.128    6.724  1.00 41.89      A  C
ATOM   2507  O    GLU A 366     -14.765   -1.411    5.718  1.00 41.89      A  O
ATOM   2508  N    LEU A 367     -15.710   -2.897    7.137  1.00 44.41      A  N
ATOM   2509  CA   LEU A 367     -16.972   -2.992    6.419  1.00 44.41      A  C
ATOM   2510  CB   LEU A 367     -17.699   -4.262    6.846  1.00 52.04      A  C
ATOM   2511  CG   LEU A 367     -16.933   -5.573    6.660  1.00 52.04      A  C
ATOM   2512  CD1  LEU A 367     -17.418   -6.595    7.679  1.00 52.04      A  C
ATOM   2513  CD2  LEU A 367     -17.109   -6.082    5.234  1.00 52.04      A  C
ATOM   2514  C    LEU A 367     -17.891   -1.800    6.650  1.00 44.41      A  C
ATOM   2515  O    LEU A 367     -18.960   -1.707    6.047  1.00 44.41      A  O
ATOM   2516  N    SER A 368     -17.475   -0.877    7.509  1.00 55.71      A  N
ATOM   2517  CA   SER A 368     -18.313    0.273    7.826  1.00 55.71      A  C
ATOM   2518  CB   SER A 368     -17.559    1.237    8.745  1.00 56.33      A  C
ATOM   2519  OG   SER A 368     -16.431    1.788    8.089  1.00 56.33      A  O
ATOM   2520  C    SER A 368     -18.902    1.045    6.638  1.00 55.71      A  C
ATOM   2521  O    SER A 368     -20.117    1.249    6.592  1.00 55.71      A  O
ATOM   2522  N    SER A 369     -18.063    1.455    5.682  1.00 48.39      A  N
ATOM   2523  CA   SER A 369     -18.533    2.233    4.527  1.00 48.39      A  C
ATOM   2524  CB   SER A 369     -17.390    2.505    3.545  1.00 45.64      A  C
ATOM   2525  OG   SER A 369     -17.409    1.583    2.467  1.00 45.64      A  O
ATOM   2526  C    SER A 369     -19.697    1.619    3.753  1.00 48.39      A  C
ATOM   2527  O    SER A 369     -20.434    2.334    3.080  1.00 48.39      A  O
ATOM   2528  N    ASN A 370     -19.865    0.304    3.840  1.00 51.22      A  N
ATOM   2529  CA   ASN A 370     -20.956   -0.349    3.122  1.00 51.22      A  C
ATOM   2530  CB   ASN A 370     -20.655   -0.376    1.630  1.00 61.82      A  C
ATOM   2531  CG   ASN A 370     -21.829   -0.844    0.828  1.00 61.82      A  C
ATOM   2532  OD1  ASN A 370     -22.379   -1.924    1.085  1.00 61.82      A  O
ATOM   2533  ND2  ASN A 370     -22.239   -0.037   -0.148  1.00 61.82      A  N
ATOM   2534  C    ASN A 370     -21.208   -1.776    3.609  1.00 51.22      A  C
ATOM   2535  O    ASN A 370     -20.988   -2.750    2.881  1.00 51.22      A  O
ATOM   2536  N    PRO A 371     -21.701   -1.912    4.845  1.00 57.40      A  N
ATOM   2537  CD   PRO A 371     -22.101   -0.795    5.719  1.00 29.62      A  C
ATOM   2538  CA   PRO A 371     -21.998   -3.193    5.484  1.00 57.40      A  C
ATOM   2539  CB   PRO A 371     -23.016   -2.799    6.542  1.00 29.62      A  C
```

FIG. 3-39

```
ATOM   2540  CG   PRO A 371     -22.450   -1.498    7.012  1.00  29.62      A  C
ATOM   2541  C    PRO A 371     -22.453   -4.376    4.614  1.00  57.40      A  C
ATOM   2542  O    PRO A 371     -21.766   -5.400    4.531  1.00  57.40      A  O
ATOM   2543  N    PRO A 372     -23.600   -4.251    3.938  1.00  72.78      A  N
ATOM   2544  CD   PRO A 372     -24.408   -3.053    3.657  1.00  59.42      A  C
ATOM   2545  CA   PRO A 372     -24.046   -5.379    3.115  1.00  72.78      A  C
ATOM   2546  CB   PRO A 372     -25.294   -4.829    2.424  1.00  59.42      A  C
ATOM   2547  CG   PRO A 372     -24.985   -3.383    2.295  1.00  59.42      A  C
ATOM   2548  C    PRO A 372     -23.047   -5.997    2.128  1.00  72.78      A  C
ATOM   2549  O    PRO A 372     -23.314   -7.076    1.598  1.00  72.78      A  O
ATOM   2550  N    LEU A 373     -21.912   -5.343    1.868  1.00  63.86      A  N
ATOM   2551  CA   LEU A 373     -20.935   -5.920    0.936  1.00  63.86      A  C
ATOM   2552  CB   LEU A 373     -19.814   -4.927    0.648  1.00  45.84      A  C
ATOM   2553  CG   LEU A 373     -20.137   -3.974   -0.509  1.00  45.84      A  C
ATOM   2554  CD1  LEU A 373     -19.069   -2.895   -0.634  1.00  45.84      A  C
ATOM   2555  CD2  LEU A 373     -20.237   -4.789   -1.796  1.00  45.84      A  C
ATOM   2556  C    LEU A 373     -20.366   -7.208    1.518  1.00  63.86      A  C
ATOM   2557  O    LEU A 373     -19.760   -8.029    0.816  1.00  63.86      A  O
ATOM   2558  N    ALA A 374     -20.603   -7.389    2.812  1.00  60.89      A  N
ATOM   2559  CA   ALA A 374     -20.128   -8.557    3.530  1.00  60.89      A  C
ATOM   2560  CB   ALA A 374     -20.497   -8.436    5.004  1.00  39.32      A  C
ATOM   2561  C    ALA A 374     -20.667   -9.863    2.959  1.00  60.89      A  C
ATOM   2562  O    ALA A 374     -20.058  -10.924    3.144  1.00  60.89      A  O
ATOM   2563  N    THR A 375     -21.800   -9.803    2.269  1.00  55.55      A  N
ATOM   2564  CA   THR A 375     -22.370  -11.025    1.709  1.00  55.55      A  C
ATOM   2565  CB   THR A 375     -23.818  -10.832    1.221  1.00  73.65      A  C
ATOM   2566  OG1  THR A 375     -23.888   -9.685    0.362  1.00  73.65      A  O
ATOM   2567  CG2  THR A 375     -24.763  -10.667    2.410  1.00  73.65      A  C
ATOM   2568  C    THR A 375     -21.536  -11.504    0.543  1.00  55.55      A  C
ATOM   2569  O    THR A 375     -21.614  -12.674    0.149  1.00  55.55      A  O
ATOM   2570  N    ILE A 376     -20.735  -10.598   -0.013  1.00  60.14      A  N
ATOM   2571  CA   ILE A 376     -19.876  -10.964   -1.129  1.00  60.14      A  C
ATOM   2572  CB   ILE A 376     -19.880   -9.887   -2.237  1.00  45.17      A  C
ATOM   2573  CG2  ILE A 376     -19.032  -10.354   -3.413  1.00  45.17      A  C
ATOM   2574  CG1  ILE A 376     -21.309   -9.625   -2.719  1.00  45.17      A  C
ATOM   2575  CD1  ILE A 376     -21.389   -8.620   -3.852  1.00  45.17      A  C
ATOM   2576  C    ILE A 376     -18.443  -11.152   -0.640  1.00  60.14      A  C
ATOM   2577  O    ILE A 376     -17.776  -12.136   -0.987  1.00  60.14      A  O
ATOM   2578  N    LEU A 377     -17.977  -10.213    0.179  1.00  63.34      A  N
ATOM   2579  CA   LEU A 377     -16.613  -10.266    0.690  1.00  63.34      A  C
ATOM   2580  CB   LEU A 377     -16.305   -8.985    1.457  1.00  35.39      A  C
ATOM   2581  CG   LEU A 377     -16.416   -7.775    0.529  1.00  35.39      A  C
ATOM   2582  CD1  LEU A 377     -16.396   -6.496    1.340  1.00  35.39      A  C
ATOM   2583  CD2  LEU A 377     -15.292   -7.804   -0.483  1.00  35.39      A  C
ATOM   2584  C    LEU A 377     -16.319  -11.493    1.552  1.00  63.34      A  C
ATOM   2585  O    LEU A 377     -15.225  -12.068    1.463  1.00  63.34      A  O
ATOM   2586  N    ILE A 378     -17.286  -11.902    2.373  1.00  67.00      A  N
ATOM   2587  CA   ILE A 378     -17.096  -13.063    3.235  1.00  67.00      A  C
ATOM   2588  CB   ILE A 378     -17.598  -12.800    4.664  1.00  48.05      A  C
ATOM   2589  CG2  ILE A 378     -17.451  -14.064    5.496  1.00  48.05      A  C
ATOM   2590  CG1  ILE A 378     -16.798  -11.663    5.307  1.00  48.05      A  C
ATOM   2591  CD1  ILE A 378     -17.311  -11.238    6.671  1.00  48.05      A  C
ATOM   2592  C    ILE A 378     -17.860  -14.250    2.669  1.00  67.00      A  C
ATOM   2593  O    ILE A 378     -19.029  -14.469    3.006  1.00  67.00      A  O
ATOM   2594  N    PRO A 379     -17.210  -15.036    1.796  1.00  69.87      A  N
ATOM   2595  CD   PRO A 379     -15.769  -15.039    1.490  1.00  61.17      A  C
ATOM   2596  CA   PRO A 379     -17.870  -16.196    1.199  1.00  69.87      A  C
ATOM   2597  CB   PRO A 379     -16.768  -16.818    0.342  1.00  61.17      A  C
ATOM   2598  CG   PRO A 379     -15.526  -16.487    1.105  1.00  61.17      A  C
ATOM   2599  C    PRO A 379     -18.364  -17.126    2.290  1.00  69.87      A  C
ATOM   2600  O    PRO A 379     -17.868  -17.084    3.424  1.00  69.87      A  O
ATOM   2601  N    PRO A 380     -19.355  -17.977    1.966  1.00  73.20      A  N
ATOM   2602  CD   PRO A 380     -20.011  -18.078    0.650  1.00  70.26      A  C
ATOM   2603  CA   PRO A 380     -19.945  -18.935    2.909  1.00  73.20      A  C
ATOM   2604  CB   PRO A 380     -20.908  -19.721    2.032  1.00  70.26      A  C
ATOM   2605  CG   PRO A 380     -21.334  -18.689    1.018  1.00  70.26      A  C
ATOM   2606  C    PRO A 380     -18.909  -19.833    3.576  1.00  73.20      A  C
```

FIG. 3-40

```
ATOM   2607  O    PRO A 380     -18.876 -19.956   4.810  1.00 73.20      A    O
ATOM   2608  N    HIS A 381     -18.052 -20.437   2.752  1.00 52.54      A    N
ATOM   2609  CA   HIS A 381     -17.029 -21.337   3.257  1.00 52.54      A    C
ATOM   2610  CB   HIS A 381     -16.143 -21.818   2.105  1.00 74.51      A    C
ATOM   2611  CG   HIS A 381     -14.978 -20.924   1.812  1.00 74.51      A    C
ATOM   2612  CD2  HIS A 381     -14.706 -20.131   0.747  1.00 74.51      A    C
ATOM   2613  ND1  HIS A 381     -13.891 -20.817   2.656  1.00 74.51      A    N
ATOM   2614  CE1  HIS A 381     -12.999 -20.001   2.120  1.00 74.51      A    C
ATOM   2615  NE2  HIS A 381     -13.468 -19.571   0.960  1.00 74.51      A    N
ATOM   2616  C    HIS A 381     -16.183 -20.698   4.366  1.00 52.54      A    C
ATOM   2617  O    HIS A 381     -15.547 -21.402   5.151  1.00 52.54      A    O
ATOM   2618  N    ALA A 382     -16.166 -19.367   4.431  1.00 81.03      A    N
ATOM   2619  CA   ALA A 382     -15.404 -18.671   5.468  1.00 81.03      A    C
ATOM   2620  CB   ALA A 382     -15.106 -17.257   5.035  1.00 72.20      A    C
ATOM   2621  C    ALA A 382     -16.207 -18.667   6.771  1.00 81.03      A    C
ATOM   2622  O    ALA A 382     -15.638 -18.783   7.868  1.00 81.03      A    O
ATOM   2623  N    ARG A 383     -17.530 -18.534   6.636  1.00 93.51      A    N
ATOM   2624  CA   ARG A 383     -18.454 -18.535   7.777  1.00 93.51      A    C
ATOM   2625  CB   ARG A 383     -19.905 -18.383   7.285  1.00 78.07      A    C
ATOM   2626  CG   ARG A 383     -20.266 -16.980   6.825  1.00 78.07      A    C
ATOM   2627  CD   ARG A 383     -20.412 -16.847   5.312  1.00 78.07      A    C
ATOM   2628  NE   ARG A 383     -21.809 -16.588   4.931  1.00 78.07      A    N
ATOM   2629  CZ   ARG A 383     -22.225 -16.157   3.730  1.00 78.07      A    C
ATOM   2630  NH1  ARG A 383     -21.360 -15.916   2.739  1.00 78.07      A    N
ATOM   2631  NH2  ARG A 383     -23.527 -15.957   3.520  1.00 78.07      A    N
ATOM   2632  C    ARG A 383     -18.330 -19.813   8.638  1.00 93.51      A    C
ATOM   2633  O    ARG A 383     -18.677 -19.743   9.845  1.00 93.51      A    O
ATOM   2634  OXT  ARG A 383     -17.909 -20.875   8.098  1.00 78.07      A    O
TER    2635       ARG A 383                                              A
ATOM   2636  CB   VAL B  37     -19.635  28.376  41.499  1.00 50.53      B    C
ATOM   2637  CG1  VAL B  37     -18.762  29.367  42.258  1.00 50.53      B    C
ATOM   2638  CG2  VAL B  37     -19.080  28.209  40.079  1.00 50.53      B    C
ATOM   2639  C    VAL B  37     -19.604  27.308  43.741  1.00 61.52      B    C
ATOM   2640  O    VAL B  37     -20.550  27.856  44.296  1.00 61.52      B    O
ATOM   2641  N    VAL B  37     -20.798  26.159  41.802  1.00 61.52      B    N
ATOM   2642  CA   VAL B  37     -19.647  27.015  42.239  1.00 61.52      B    C
ATOM   2643  N    THR B  38     -18.496  26.945  44.388  1.00 54.53      B    N
ATOM   2644  CA   THR B  38     -18.306  27.186  45.824  1.00 54.53      B    C
ATOM   2645  CB   THR B  38     -17.681  25.969  46.531  1.00 49.70      B    C
ATOM   2646  OG1  THR B  38     -18.449  24.793  46.247  1.00 49.70      B    O
ATOM   2647  CG2  THR B  38     -17.643  26.192  48.035  1.00 49.70      B    C
ATOM   2648  C    THR B  38     -17.345  28.364  46.016  1.00 54.53      B    C
ATOM   2649  O    THR B  38     -16.373  28.516  45.265  1.00 54.53      B    O
ATOM   2650  N    THR B  39     -17.625  29.199  47.015  1.00 56.75      B    N
ATOM   2651  CA   THR B  39     -16.783  30.361  47.326  1.00 56.75      B    C
ATOM   2652  CB   THR B  39     -17.495  31.706  46.989  1.00 42.46      B    C
ATOM   2653  OG1  THR B  39     -17.592  31.847  45.566  1.00 42.46      B    O
ATOM   2654  CG2  THR B  39     -16.715  32.897  47.565  1.00 42.46      B    C
ATOM   2655  C    THR B  39     -16.410  30.354  48.808  1.00 56.75      B    C
ATOM   2656  O    THR B  39     -17.269  30.351  49.689  1.00 56.75      B    O
ATOM   2657  N    VAL B  40     -15.117  30.353  49.076  1.00 48.63      B    N
ATOM   2658  CA   VAL B  40     -14.644  30.330  50.445  1.00 48.63      B    C
ATOM   2659  CB   VAL B  40     -14.005  28.964  50.771  1.00 36.13      B    C
ATOM   2660  CG1  VAL B  40     -15.042  27.850  50.622  1.00 36.13      B    C
ATOM   2661  CG2  VAL B  40     -12.807  28.722  49.848  1.00 36.13      B    C
ATOM   2662  C    VAL B  40     -13.598  31.410  50.663  1.00 48.63      B    C
ATOM   2663  O    VAL B  40     -13.001  31.924  49.711  1.00 48.63      B    O
ATOM   2664  N    VAL B  41     -13.384  31.774  51.918  1.00 41.12      B    N
ATOM   2665  CA   VAL B  41     -12.366  32.764  52.213  1.00 41.12      B    C
ATOM   2666  CB   VAL B  41     -12.826  33.772  53.286  1.00 40.90      B    C
ATOM   2667  CG1  VAL B  41     -11.667  34.680  53.675  1.00 40.90      B    C
ATOM   2668  CG2  VAL B  41     -13.971  34.610  52.742  1.00 40.90      B    C
ATOM   2669  C    VAL B  41     -11.196  31.941  52.719  1.00 41.12      B    C
ATOM   2670  O    VAL B  41     -11.227  31.410  53.830  1.00 41.12      B    O
ATOM   2671  N    ALA B  42     -10.174  31.823  51.878  1.00 39.58      B    N
ATOM   2672  CA   ALA B  42      -9.006  31.035  52.216  1.00 39.58      B    C
ATOM   2673  CB   ALA B  42      -8.836  29.925  51.199  1.00 68.93      B    C
```

FIG. 3-41

```
ATOM   2674  C    ALA B  42      -7.707  31.807  52.343  1.00 39.58      B  C
ATOM   2675  O    ALA B  42      -7.366  32.640  51.499  1.00 39.58      B  O
ATOM   2676  N    THR B  43      -6.989  31.505  53.420  1.00 43.86      B  N
ATOM   2677  CA   THR B  43      -5.691  32.097  53.693  1.00 43.86      B  C
ATOM   2678  CB   THR B  43      -5.243  31.808  55.143  1.00 44.15      B  C
ATOM   2679  OG1  THR B  43      -6.363  31.920  56.029  1.00 44.15      B  O
ATOM   2680  CG2  THR B  43      -4.172  32.790  55.569  1.00 44.15      B  C
ATOM   2681  C    THR B  43      -4.746  31.357  52.739  1.00 43.86      B  C
ATOM   2682  O    THR B  43      -4.888  30.153  52.536  1.00 43.86      B  O
ATOM   2683  N    PRO B  44      -3.786  32.066  52.129  1.00 46.61      B  N
ATOM   2684  CD   PRO B  44      -3.617  33.525  52.063  1.00 57.80      B  C
ATOM   2685  CA   PRO B  44      -2.861  31.396  51.210  1.00 46.61      B  C
ATOM   2686  CB   PRO B  44      -2.124  32.563  50.556  1.00 57.80      B  C
ATOM   2687  CG   PRO B  44      -3.116  33.700  50.657  1.00 57.80      B  C
ATOM   2688  C    PRO B  44      -1.923  30.465  51.987  1.00 46.61      B  C
ATOM   2689  O    PRO B  44      -1.640  30.699  53.168  1.00 46.61      B  O
ATOM   2690  N    GLY B  45      -1.450  29.413  51.321  1.00 68.92      B  N
ATOM   2691  CA   GLY B  45      -0.573  28.441  51.959  1.00 68.92      B  C
ATOM   2692  C    GLY B  45       0.688  29.055  52.524  1.00 68.92      B  C
ATOM   2693  O    GLY B  45       0.799  29.293  53.732  1.00 68.92      B  O
ATOM   2694  N    ASP B  46       1.669  29.276  51.661  1.00 76.76      B  N
ATOM   2695  CA   ASP B  46       2.901  29.912  52.103  1.00 76.76      B  C
ATOM   2696  CB   ASP B  46       4.124  29.328  51.364  1.00 99.39      B  C
ATOM   2697  CG   ASP B  46       5.389  30.209  51.509  1.00 99.39      B  C
ATOM   2698  OD1  ASP B  46       6.287  30.137  50.627  1.00 99.39      B  O
ATOM   2699  OD2  ASP B  46       5.492  30.975  52.502  1.00 99.39      B  O
ATOM   2700  C    ASP B  46       2.703  31.379  51.728  1.00 76.76      B  C
ATOM   2701  O    ASP B  46       2.523  31.707  50.549  1.00 76.76      B  O
ATOM   2702  N    GLY B  47       2.702  32.259  52.717  1.00 62.38      B  N
ATOM   2703  CA   GLY B  47       2.546  33.662  52.397  1.00 62.38      B  C
ATOM   2704  C    GLY B  47       2.111  34.499  53.575  1.00 62.38      B  C
ATOM   2705  O    GLY B  47       2.263  34.080  54.722  1.00 62.38      B  O
ATOM   2706  N    PRO B  48       1.545  35.689  53.328  1.00 56.60      B  N
ATOM   2707  CD   PRO B  48       1.010  36.187  52.053  1.00 67.11      B  C
ATOM   2708  CA   PRO B  48       1.105  36.548  54.425  1.00 56.60      B  C
ATOM   2709  CB   PRO B  48       0.966  37.920  53.760  1.00 67.11      B  C
ATOM   2710  CG   PRO B  48       1.180  37.667  52.227  1.00 67.11      B  C
ATOM   2711  C    PRO B  48      -0.230  36.000  54.908  1.00 56.60      B  C
ATOM   2712  O    PRO B  48      -1.159  35.838  54.114  1.00 56.60      B  O
ATOM   2713  N    ASP B  49      -0.309  35.690  56.198  1.00 57.88      B  N
ATOM   2714  CA   ASP B  49      -1.526  35.136  56.794  1.00 57.88      B  C
ATOM   2715  CB   ASP B  49      -1.294  34.850  58.281  1.00 72.56      B  C
ATOM   2716  CG   ASP B  49      -2.425  34.057  58.899  1.00 72.56      B  C
ATOM   2717  OD1  ASP B  49      -3.575  34.275  58.459  1.00 72.56      B  O
ATOM   2718  OD2  ASP B  49      -2.179  33.227  59.819  1.00 72.56      B  O
ATOM   2719  C    ASP B  49      -2.689  36.117  56.640  1.00 57.88      B  C
ATOM   2720  O    ASP B  49      -3.103  36.748  57.611  1.00 57.88      B  O
ATOM   2721  N    ARG B  50      -3.230  36.225  55.429  1.00 53.04      B  N
ATOM   2722  CA   ARG B  50      -4.312  37.169  55.167  1.00 53.04      B  C
ATOM   2723  CB   ARG B  50      -3.694  38.534  54.880  1.00 99.46      B  C
ATOM   2724  CG   ARG B  50      -4.598  39.689  55.244  1.00 99.46      B  C
ATOM   2725  CD   ARG B  50      -3.869  41.023  55.155  1.00 99.46      B  C
ATOM   2726  NE   ARG B  50      -3.122  41.218  53.905  1.00 99.46      B  N
ATOM   2727  CZ   ARG B  50      -3.467  40.775  52.692  1.00 99.46      B  C
ATOM   2728  NH1  ARG B  50      -4.578  40.069  52.515  1.00 99.46      B  N
ATOM   2729  NH2  ARG B  50      -2.702  41.059  51.639  1.00 99.46      B  N
ATOM   2730  C    ARG B  50      -5.211  36.719  54.001  1.00 53.04      B  C
ATOM   2731  O    ARG B  50      -4.913  36.972  52.833  1.00 53.04      B  O
ATOM   2732  N    PRO B  51      -6.348  36.084  54.327  1.00 48.03      B  N
ATOM   2733  CD   PRO B  51      -6.827  36.143  55.718  1.00 54.83      B  C
ATOM   2734  CA   PRO B  51      -7.395  35.519  53.470  1.00 48.03      B  C
ATOM   2735  CB   PRO B  51      -8.420  35.007  54.479  1.00 54.83      B  C
ATOM   2736  CG   PRO B  51      -8.325  35.996  55.553  1.00 54.83      B  C
ATOM   2737  C    PRO B  51      -8.048  36.337  52.369  1.00 48.03      B  C
ATOM   2738  O    PRO B  51      -8.231  37.542  52.493  1.00 48.03      B  O
ATOM   2739  N    GLN B  52      -8.405  35.631  51.294  1.00 50.19      B  N
ATOM   2740  CA   GLN B  52      -9.058  36.203  50.123  1.00 50.19      B  C
```

FIG. 3-42

```
ATOM   2741  CB   GLN B  52      -8.040  36.528  49.040  1.00 71.07      B  C
ATOM   2742  CG   GLN B  52      -6.986  35.472  48.875  1.00 71.07      B  C
ATOM   2743  CD   GLN B  52      -5.824  35.949  48.020  1.00 71.07      B  C
ATOM   2744  OE1  GLN B  52      -5.792  35.721  46.802  1.00 71.07      B  O
ATOM   2745  NE2  GLN B  52      -4.863  36.632  48.653  1.00 71.07      B  N
ATOM   2746  C    GLN B  52     -10.058  35.206  49.592  1.00 50.19      B  C
ATOM   2747  O    GLN B  52     -10.015  34.027  49.931  1.00 50.19      B  O
ATOM   2748  N    GLU B  53     -10.971  35.685  48.760  1.00 51.68      B  N
ATOM   2749  CA   GLU B  53     -11.996  34.814  48.204  1.00 51.68      B  C
ATOM   2750  CB   GLU B  53     -13.148  35.641  47.636  1.00 57.81      B  C
ATOM   2751  CG   GLU B  53     -14.046  36.238  48.704  1.00 57.81      B  C
ATOM   2752  CD   GLU B  53     -15.004  37.260  48.138  1.00 57.81      B  C
ATOM   2753  OE1  GLU B  53     -15.616  36.977  47.096  1.00 57.81      B  O
ATOM   2754  OE2  GLU B  53     -15.152  38.339  48.734  1.00 57.81      B  O
ATOM   2755  C    GLU B  53     -11.454  33.874  47.144  1.00 51.68      B  C
ATOM   2756  O    GLU B  53     -10.623  34.243  46.312  1.00 51.68      B  O
ATOM   2757  N    VAL B  54     -11.939  32.641  47.202  1.00 45.60      B  N
ATOM   2758  CA   VAL B  54     -11.544  31.599  46.273  1.00 45.60      B  C
ATOM   2759  CB   VAL B  54     -10.554  30.623  46.928  1.00 40.95      B  C
ATOM   2760  CG1  VAL B  54     -10.205  29.515  45.949  1.00 40.95      B  C
ATOM   2761  CG2  VAL B  54      -9.310  31.368  47.387  1.00 40.95      B  C
ATOM   2762  C    VAL B  54     -12.777  30.811  45.856  1.00 45.60      B  C
ATOM   2763  O    VAL B  54     -13.553  30.360  46.703  1.00 45.60      B  O
ATOM   2764  N    SER B  55     -12.963  30.662  44.549  1.00 52.05      B  N
ATOM   2765  CA   SER B  55     -14.097  29.898  44.036  1.00 52.05      B  C
ATOM   2766  CB   SER B  55     -14.991  30.780  43.154  1.00 63.44      B  C
ATOM   2767  OG   SER B  55     -15.703  31.726  43.942  1.00 63.44      B  O
ATOM   2768  C    SER B  55     -13.627  28.669  43.255  1.00 52.05      B  C
ATOM   2769  O    SER B  55     -12.667  28.723  42.481  1.00 52.05      B  O
ATOM   2770  N    TYR B  56     -14.299  27.551  43.484  1.00 50.76      B  N
ATOM   2771  CA   TYR B  56     -13.947  26.317  42.809  1.00 50.76      B  C
ATOM   2772  CB   TYR B  56     -13.006  25.465  43.680  1.00 37.39      B  C
ATOM   2773  CG   TYR B  56     -13.557  25.060  45.033  1.00 37.39      B  C
ATOM   2774  CD1  TYR B  56     -14.585  24.124  45.144  1.00 37.39      B  C
ATOM   2775  CE1  TYR B  56     -15.087  23.750  46.390  1.00 37.39      B  C
ATOM   2776  CD2  TYR B  56     -13.045  25.614  46.206  1.00 37.39      B  C
ATOM   2777  CE2  TYR B  56     -13.535  25.251  47.452  1.00 37.39      B  C
ATOM   2778  CZ   TYR B  56     -14.554  24.318  47.538  1.00 37.39      B  C
ATOM   2779  OH   TYR B  56     -15.029  23.940  48.775  1.00 37.39      B  O
ATOM   2780  C    TYR B  56     -15.215  25.553  42.497  1.00 50.76      B  C
ATOM   2781  O    TYR B  56     -16.263  25.788  43.106  1.00 50.76      B  O
ATOM   2782  N    THR B  57     -15.123  24.634  41.545  1.00 59.31      B  N
ATOM   2783  CA   THR B  57     -16.287  23.858  41.176  1.00 59.31      B  C
ATOM   2784  CB   THR B  57     -17.055  24.570  40.055  1.00 51.89      B  C
ATOM   2785  OG1  THR B  57     -18.298  23.890  39.812  1.00 51.89      B  O
ATOM   2786  CG2  THR B  57     -16.204  24.608  38.789  1.00 51.89      B  C
ATOM   2787  C    THR B  57     -15.891  22.457  40.718  1.00 59.31      B  C
ATOM   2788  O    THR B  57     -14.730  22.066  40.827  1.00 59.31      B  O
ATOM   2789  N    ASP B  58     -16.867  21.713  40.205  1.00 57.73      B  N
ATOM   2790  CA   ASP B  58     -16.639  20.358  39.723  1.00 57.73      B  C
ATOM   2791  CB   ASP B  58     -15.660  20.341  38.529  1.00 49.12      B  C
ATOM   2792  CG   ASP B  58     -16.122  21.200  37.363  1.00 49.12      B  C
ATOM   2793  OD1  ASP B  58     -17.310  21.588  37.338  1.00 49.12      B  O
ATOM   2794  OD2  ASP B  58     -15.299  21.480  36.464  1.00 49.12      B  O
ATOM   2795  C    ASP B  58     -16.034  19.548  40.849  1.00 57.73      B  C
ATOM   2796  O    ASP B  58     -15.186  18.690  40.613  1.00 57.73      B  O
ATOM   2797  N    THR B  59     -16.455  19.805  42.079  1.00 58.58      B  N
ATOM   2798  CA   THR B  59     -15.867  19.056  43.188  1.00 58.58      B  C
ATOM   2799  CB   THR B  59     -16.102  19.761  44.535  1.00 55.03      B  C
ATOM   2800  OG1  THR B  59     -17.389  19.407  45.042  1.00 55.03      B  O
ATOM   2801  CG2  THR B  59     -16.037  21.267  44.362  1.00 55.03      B  C
ATOM   2802  C    THR B  59     -16.374  17.614  43.297  1.00 58.58      B  C
ATOM   2803  O    THR B  59     -17.587  17.366  43.286  1.00 58.58      B  O
ATOM   2804  N    LYS B  60     -15.441  16.666  43.391  1.00 58.77      B  N
ATOM   2805  CA   LYS B  60     -15.798  15.252  43.531  1.00 58.77      B  C
ATOM   2806  CB   LYS B  60     -15.793  14.547  42.168  1.00 52.32      B  C
ATOM   2807  CG   LYS B  60     -14.457  14.520  41.471  1.00 52.32      B  C
```

FIG. 3-43

```
ATOM   2808  CD   LYS B  60     -14.498  13.537  40.310  1.00 52.32      B    C
ATOM   2809  CE   LYS B  60     -13.235  13.627  39.457  1.00 52.32      B    C
ATOM   2810  NZ   LYS B  60     -13.286  12.773  38.232  1.00 52.32      B    N
ATOM   2811  C    LYS B  60     -14.852  14.525  44.499  1.00 58.77      B    C
ATOM   2812  O    LYS B  60     -13.653  14.825  44.558  1.00 58.77      B    O
ATOM   2813  N    VAL B  61     -15.403  13.572  45.253  1.00 48.28      B    N
ATOM   2814  CA   VAL B  61     -14.635  12.811  46.230  1.00 48.28      B    C
ATOM   2815  CB   VAL B  61     -15.555  11.952  47.112  1.00 39.27      B    C
ATOM   2816  CG1  VAL B  61     -14.720  11.113  48.072  1.00 39.27      B    C
ATOM   2817  CG2  VAL B  61     -16.512  12.849  47.884  1.00 39.27      B    C
ATOM   2818  C    VAL B  61     -13.606  11.897  45.583  1.00 48.28      B    C
ATOM   2819  O    VAL B  61     -13.910  11.214  44.605  1.00 48.28      B    O
ATOM   2820  N    ILE B  62     -12.391  11.879  46.136  1.00 43.29      B    N
ATOM   2821  CA   ILE B  62     -11.323  11.033  45.602  1.00 43.29      B    C
ATOM   2822  CB   ILE B  62     -10.398  11.840  44.664  1.00 35.10      B    C
ATOM   2823  CG2  ILE B  62     -11.233  12.596  43.648  1.00 35.10      B    C
ATOM   2824  CG1  ILE B  62      -9.549  12.830  45.460  1.00 35.10      B    C
ATOM   2825  CD1  ILE B  62      -8.440  13.453  44.635  1.00 35.10      B    C
ATOM   2826  C    ILE B  62     -10.454  10.337  46.662  1.00 43.29      B    C
ATOM   2827  O    ILE B  62      -9.421   9.742  46.337  1.00 43.29      B    O
ATOM   2828  N    GLY B  63     -10.868  10.400  47.924  1.00 43.15      B    N
ATOM   2829  CA   GLY B  63     -10.079   9.767  48.961  1.00 43.15      B    C
ATOM   2830  C    GLY B  63     -10.671   9.819  50.353  1.00 43.15      B    C
ATOM   2831  O    GLY B  63     -11.252  10.821  50.743  1.00 43.15      B    O
ATOM   2832  N    ASN B  64     -10.519   8.720  51.091  1.00 60.26      B    N
ATOM   2833  CA   ASN B  64     -11.004   8.577  52.470  1.00 60.26      B    C
ATOM   2834  CB   ASN B  64     -11.571   7.171  52.699  1.00 61.40      B    C
ATOM   2835  CG   ASN B  64     -12.943   6.998  52.121  1.00 61.40      B    C
ATOM   2836  OD1  ASN B  64     -13.957   7.315  52.758  1.00 61.40      B    O
ATOM   2837  ND2  ASN B  64     -12.994   6.507  50.891  1.00 61.40      B    N
ATOM   2838  C    ASN B  64      -9.828   8.767  53.414  1.00 60.26      B    C
ATOM   2839  O    ASN B  64      -8.881   9.476  53.103  1.00 60.26      B    O
ATOM   2840  N    GLY B  65      -9.878   8.103  54.560  1.00 39.44      B    N
ATOM   2841  CA   GLY B  65      -8.796   8.209  55.515  1.00 39.44      B    C
ATOM   2842  C    GLY B  65      -9.369   8.472  56.881  1.00 39.44      B    C
ATOM   2843  O    GLY B  65     -10.526   8.878  57.001  1.00 39.44      B    O
ATOM   2844  N    SER B  66      -8.567   8.231  57.912  1.00 50.77      B    N
ATOM   2845  CA   SER B  66      -9.004   8.450  59.294  1.00 50.77      B    C
ATOM   2846  CB   SER B  66      -8.031   7.779  60.269  1.00 60.25      B    C
ATOM   2847  OG   SER B  66      -6.705   8.246  60.055  1.00 60.25      B    O
ATOM   2848  C    SER B  66      -9.067   9.946  59.580  1.00 50.77      B    C
ATOM   2849  O    SER B  66      -9.640  10.374  60.577  1.00 50.77      B    O
ATOM   2850  N    PHE B  67      -8.471  10.725  58.683  1.00 51.21      B    N
ATOM   2851  CA   PHE B  67      -8.431  12.171  58.801  1.00 51.21      B    C
ATOM   2852  CB   PHE B  67      -7.256  12.696  57.998  1.00 59.32      B    C
ATOM   2853  CG   PHE B  67      -7.315  12.341  56.544  1.00 59.32      B    C
ATOM   2854  CD1  PHE B  67      -8.172  13.024  55.677  1.00 59.32      B    C
ATOM   2855  CD2  PHE B  67      -6.493  11.346  56.030  1.00 59.32      B    C
ATOM   2856  CE1  PHE B  67      -8.202  12.726  54.315  1.00 59.32      B    C
ATOM   2857  CE2  PHE B  67      -6.512  11.036  54.667  1.00 59.32      B    C
ATOM   2858  CZ   PHE B  67      -7.367  11.729  53.807  1.00 59.32      B    C
ATOM   2859  C    PHE B  67      -9.714  12.816  58.294  1.00 51.21      B    C
ATOM   2860  O    PHE B  67     -10.141  13.854  58.803  1.00 51.21      B    O
ATOM   2861  N    GLY B  68     -10.313  12.203  57.276  1.00 45.10      B    N
ATOM   2862  CA   GLY B  68     -11.535  12.733  56.714  1.00 45.10      B    C
ATOM   2863  C    GLY B  68     -11.655  12.317  55.269  1.00 45.10      B    C
ATOM   2864  O    GLY B  68     -11.368  11.167  54.930  1.00 45.10      B    O
ATOM   2865  N    VAL B  69     -12.070  13.257  54.420  1.00 52.52      B    N
ATOM   2866  CA   VAL B  69     -12.248  13.019  52.990  1.00 52.52      B    C
ATOM   2867  CB   VAL B  69     -13.701  13.295  52.570  1.00 33.15      B    C
ATOM   2868  CG1  VAL B  69     -13.907  12.929  51.110  1.00 33.15      B    C
ATOM   2869  CG2  VAL B  69     -14.644  12.514  53.452  1.00 33.15      B    C
ATOM   2870  C    VAL B  69     -11.341  13.928  52.165  1.00 52.52      B    C
ATOM   2871  O    VAL B  69     -10.770  14.881  52.681  1.00 52.52      B    O
ATOM   2872  N    VAL B  70     -11.213  13.627  50.881  1.00 34.24      B    N
ATOM   2873  CA   VAL B  70     -10.400  14.426  49.984  1.00 34.24      B    C
ATOM   2874  CB   VAL B  70      -9.069  13.753  49.663  1.00 38.47      B    C
```

FIG. 3-44

| | | | | | | | | | | | |
|---|---|---|---|---|---|---|---|---|---|---|---|
| ATOM | 2875 | CG1 | VAL | B | 70 | -8.160 | 14.732 | 48.961 | 1.00 38.47 | B | C |
| ATOM | 2876 | CG2 | VAL | B | 70 | -8.434 | 13.239 | 50.919 | 1.00 38.47 | B | C |
| ATOM | 2877 | C | VAL | B | 70 | -11.154 | 14.562 | 48.671 | 1.00 34.24 | B | C |
| ATOM | 2878 | O | VAL | B | 70 | -11.398 | 13.571 | 47.979 | 1.00 34.24 | B | O |
| ATOM | 2879 | N | TYR | B | 71 | -11.526 | 15.786 | 48.323 | 1.00 47.78 | B | N |
| ATOM | 2880 | CA | TYR | B | 71 | -12.233 | 16.008 | 47.082 | 1.00 47.78 | B | C |
| ATOM | 2881 | CB | TYR | B | 71 | -13.341 | 17.048 | 47.260 | 1.00 45.77 | B | C |
| ATOM | 2882 | CG | TYR | B | 71 | -14.233 | 16.851 | 48.461 | 1.00 45.77 | B | C |
| ATOM | 2883 | CD1 | TYR | B | 71 | -13.775 | 17.125 | 49.747 | 1.00 45.77 | B | C |
| ATOM | 2884 | CE1 | TYR | B | 71 | -14.614 | 16.983 | 50.854 | 1.00 45.77 | B | C |
| ATOM | 2885 | CD2 | TYR | B | 71 | -15.555 | 16.423 | 48.310 | 1.00 45.77 | B | C |
| ATOM | 2886 | CE2 | TYR | B | 71 | -16.402 | 16.276 | 49.416 | 1.00 45.77 | B | C |
| ATOM | 2887 | CZ | TYR | B | 71 | -15.922 | 16.561 | 50.681 | 1.00 45.77 | B | C |
| ATOM | 2888 | OH | TYR | B | 71 | -16.748 | 16.432 | 51.773 | 1.00 45.77 | B | O |
| ATOM | 2889 | C | TYR | B | 71 | -11.245 | 16.543 | 46.063 | 1.00 47.78 | B | C |
| ATOM | 2890 | O | TYR | B | 71 | -10.089 | 16.848 | 46.392 | 1.00 47.78 | B | O |
| ATOM | 2891 | N | GLN | B | 72 | -11.699 | 16.631 | 44.816 | 1.00 32.24 | B | N |
| ATOM | 2892 | CA | GLN | B | 72 | -10.895 | 17.215 | 43.764 | 1.00 32.24 | B | C |
| ATOM | 2893 | CB | GLN | B | 72 | -10.740 | 16.285 | 42.587 | 1.00 46.73 | B | C |
| ATOM | 2894 | CG | GLN | B | 72 | -9.994 | 16.956 | 41.465 | 1.00 46.73 | B | C |
| ATOM | 2895 | CD | GLN | B | 72 | -10.174 | 16.265 | 40.143 | 1.00 46.73 | B | C |
| ATOM | 2896 | OE1 | GLN | B | 72 | -11.277 | 16.233 | 39.585 | 1.00 46.73 | B | O |
| ATOM | 2897 | NE2 | GLN | B | 72 | -9.090 | 15.702 | 39.626 | 1.00 46.73 | B | N |
| ATOM | 2898 | C | GLN | B | 72 | -11.757 | 18.390 | 43.349 | 1.00 32.24 | B | C |
| ATOM | 2899 | O | GLN | B | 72 | -12.962 | 18.370 | 43.587 | 1.00 32.24 | B | O |
| ATOM | 2900 | N | ALA | B | 73 | -11.163 | 19.408 | 42.739 | 1.00 39.42 | B | N |
| ATOM | 2901 | CA | ALA | B | 73 | -11.938 | 20.569 | 42.326 | 1.00 39.42 | B | C |
| ATOM | 2902 | CB | ALA | B | 73 | -12.330 | 21.404 | 43.543 | 1.00 44.25 | B | C |
| ATOM | 2903 | C | ALA | B | 73 | -11.198 | 21.431 | 41.326 | 1.00 39.42 | B | C |
| ATOM | 2904 | O | ALA | B | 73 | -10.001 | 21.259 | 41.091 | 1.00 39.42 | B | O |
| ATOM | 2905 | N | LYS | B | 74 | -11.926 | 22.378 | 40.753 | 1.00 50.48 | B | N |
| ATOM | 2906 | CA | LYS | B | 74 | -11.370 | 23.257 | 39.747 | 1.00 50.48 | B | C |
| ATOM | 2907 | CB | LYS | B | 74 | -12.060 | 22.970 | 38.417 | 1.00 65.03 | B | C |
| ATOM | 2908 | CG | LYS | B | 74 | -11.551 | 23.748 | 37.230 | 1.00 65.03 | B | C |
| ATOM | 2909 | CD | LYS | B | 74 | -12.427 | 23.421 | 36.026 | 1.00 65.03 | B | C |
| ATOM | 2910 | CE | LYS | B | 74 | -12.215 | 24.370 | 34.861 | 1.00 65.03 | B | C |
| ATOM | 2911 | NZ | LYS | B | 74 | -13.126 | 23.985 | 33.739 | 1.00 65.03 | B | N |
| ATOM | 2912 | C | LYS | B | 74 | -11.545 | 24.716 | 40.149 | 1.00 50.48 | B | C |
| ATOM | 2913 | O | LYS | B | 74 | -12.656 | 25.171 | 40.424 | 1.00 50.48 | B | O |
| ATOM | 2914 | N | LEU | B | 75 | -10.429 | 25.437 | 40.193 | 1.00 55.36 | B | N |
| ATOM | 2915 | CA | LEU | B | 75 | -10.439 | 26.838 | 40.564 | 1.00 55.36 | B | C |
| ATOM | 2916 | CB | LEU | B | 75 | -9.005 | 27.330 | 40.816 | 1.00 30.41 | B | C |
| ATOM | 2917 | CG | LEU | B | 75 | -8.177 | 26.676 | 41.928 | 1.00 30.41 | B | C |
| ATOM | 2918 | CD1 | LEU | B | 75 | -6.946 | 27.525 | 42.202 | 1.00 30.41 | B | C |
| ATOM | 2919 | CD2 | LEU | B | 75 | -8.992 | 26.558 | 43.192 | 1.00 30.41 | B | C |
| ATOM | 2920 | C | LEU | B | 75 | -11.080 | 27.635 | 39.434 | 1.00 55.36 | B | C |
| ATOM | 2921 | O | LEU | B | 75 | -10.703 | 27.493 | 38.270 | 1.00 55.36 | B | O |
| ATOM | 2922 | N | CYS | B | 76 | -12.050 | 28.474 | 39.777 | 1.00 57.25 | B | N |
| ATOM | 2923 | CA | CYS | B | 76 | -12.731 | 29.278 | 38.772 | 1.00 57.25 | B | C |
| ATOM | 2924 | CB | CYS | B | 76 | -14.002 | 29.903 | 39.359 | 1.00 55.73 | B | C |
| ATOM | 2925 | SG | CYS | B | 76 | -15.472 | 28.888 | 39.121 | 1.00 55.73 | B | S |
| ATOM | 2926 | C | CYS | B | 76 | -11.873 | 30.366 | 38.147 | 1.00 57.25 | B | C |
| ATOM | 2927 | O | CYS | B | 76 | -12.349 | 31.103 | 37.294 | 1.00 57.25 | B | O |
| ATOM | 2928 | N | ASP | B | 77 | -10.613 | 30.467 | 38.545 | 1.00 56.58 | B | N |
| ATOM | 2929 | CA | ASP | B | 77 | -9.743 | 31.502 | 37.986 | 1.00 56.58 | B | C |
| ATOM | 2930 | CB | ASP | B | 77 | -8.787 | 32.043 | 39.048 | 1.00100.00 | B | C |
| ATOM | 2931 | CG | ASP | B | 77 | -9.472 | 32.304 | 40.374 | 1.00100.00 | B | C |
| ATOM | 2932 | OD1 | ASP | B | 77 | -9.794 | 31.310 | 41.102 | 1.00100.00 | B | O |
| ATOM | 2933 | OD2 | ASP | B | 77 | -9.686 | 33.513 | 40.673 | 1.00100.00 | B | O |
| ATOM | 2934 | C | ASP | B | 77 | -8.902 | 30.969 | 36.843 | 1.00 56.58 | B | C |
| ATOM | 2935 | O | ASP | B | 77 | -9.018 | 31.407 | 35.698 | 1.00 56.58 | B | O |
| ATOM | 2936 | N | SER | B | 78 | -8.041 | 30.020 | 37.183 | 1.00 55.77 | B | N |
| ATOM | 2937 | CA | SER | B | 78 | -7.144 | 29.404 | 36.219 | 1.00 55.77 | B | C |
| ATOM | 2938 | CB | SER | B | 78 | -5.767 | 29.244 | 36.857 | 1.00 62.64 | B | C |
| ATOM | 2939 | OG | SER | B | 78 | -5.895 | 28.606 | 38.123 | 1.00 62.64 | B | O |
| ATOM | 2940 | C | SER | B | 78 | -7.664 | 28.040 | 35.770 | 1.00 55.77 | B | C |
| ATOM | 2941 | O | SER | B | 78 | -7.052 | 27.374 | 34.934 | 1.00 55.77 | B | O |

FIG. 3-45

```
ATOM   2942  N    GLY B  79      -8.796  27.625  36.321  1.00 62.24      B    N
ATOM   2943  CA   GLY B  79      -9.317  26.329  35.952  1.00 62.24      B    C
ATOM   2944  C    GLY B  79      -8.395  25.278  36.552  1.00 62.24      B    C
ATOM   2945  O    GLY B  79      -8.728  24.084  36.580  1.00 62.24      B    O
ATOM   2946  N    GLU B  80      -7.234  25.725  37.042  1.00 40.03      B    N
ATOM   2947  CA   GLU B  80      -6.256  24.831  37.659  1.00 40.03      B    C
ATOM   2948  CB   GLU B  80      -5.217  25.632  38.437  1.00 58.38      B    C
ATOM   2949  CG   GLU B  80      -4.075  26.170  37.600  1.00 58.38      B    C
ATOM   2950  CD   GLU B  80      -3.101  27.004  38.416  1.00 58.38      B    C
ATOM   2951  OE1  GLU B  80      -3.401  28.196  38.658  1.00 58.38      B    O
ATOM   2952  OE2  GLU B  80      -2.045  26.461  38.829  1.00 58.38      B    O
ATOM   2953  C    GLU B  80      -6.914  23.836  38.598  1.00 40.03      B    C
ATOM   2954  O    GLU B  80      -7.752  24.196  39.423  1.00 40.03      B    O
ATOM   2955  N    LEU B  81      -6.524  22.579  38.466  1.00 43.48      B    N
ATOM   2956  CA   LEU B  81      -7.079  21.537  39.307  1.00 43.48      B    C
ATOM   2957  CB   LEU B  81      -6.921  20.177  38.624  1.00 64.15      B    C
ATOM   2958  CG   LEU B  81      -7.790  19.986  37.382  1.00 64.15      B    C
ATOM   2959  CD1  LEU B  81      -7.586  18.585  36.837  1.00 64.15      B    C
ATOM   2960  CD2  LEU B  81      -9.263  20.202  37.755  1.00 64.15      B    C
ATOM   2961  C    LEU B  81      -6.425  21.514  40.682  1.00 43.48      B    C
ATOM   2962  O    LEU B  81      -5.252  21.870  40.834  1.00 43.48      B    O
ATOM   2963  N    VAL B  82      -7.197  21.093  41.678  1.00 43.88      B    N
ATOM   2964  CA   VAL B  82      -6.711  21.019  43.052  1.00 43.88      B    C
ATOM   2965  CB   VAL B  82      -7.031  22.315  43.843  1.00 52.14      B    C
ATOM   2966  CG1  VAL B  82      -6.366  23.509  43.194  1.00 52.14      B    C
ATOM   2967  CG2  VAL B  82      -8.548  22.523  43.920  1.00 52.14      B    C
ATOM   2968  C    VAL B  82      -7.338  19.861  43.822  1.00 43.88      B    C
ATOM   2969  O    VAL B  82      -8.294  19.226  43.368  1.00 43.88      B    O
ATOM   2970  N    ALA B  83      -6.790  19.598  45.000  1.00 53.39      B    N
ATOM   2971  CA   ALA B  83      -7.298  18.544  45.869  1.00 53.39      B    C
ATOM   2972  CB   ALA B  83      -6.253  17.440  46.039  1.00 33.41      B    C
ATOM   2973  C    ALA B  83      -7.571  19.217  47.203  1.00 53.39      B    C
ATOM   2974  O    ALA B  83      -6.723  19.955  47.707  1.00 53.39      B    O
ATOM   2975  N    ILE B  84      -8.748  18.994  47.770  1.00 36.28      B    N
ATOM   2976  CA   ILE B  84      -9.050  19.614  49.045  1.00 36.28      B    C
ATOM   2977  CB   ILE B  84     -10.358  20.429  48.964  1.00 36.65      B    C
ATOM   2978  CG2  ILE B  84     -10.590  21.188  50.264  1.00 36.65      B    C
ATOM   2979  CG1  ILE B  84     -10.261  21.431  47.806  1.00 36.65      B    C
ATOM   2980  CD1  ILE B  84     -11.494  22.273  47.598  1.00 36.65      B    C
ATOM   2981  C    ILE B  84      -9.137  18.553  50.127  1.00 36.28      B    C
ATOM   2982  O    ILE B  84     -10.041  17.715  50.125  1.00 36.28      B    O
ATOM   2983  N    LYS B  85      -8.174  18.580  51.044  1.00 39.65      B    N
ATOM   2984  CA   LYS B  85      -8.147  17.611  52.128  1.00 39.65      B    C
ATOM   2985  CB   LYS B  85      -6.701  17.341  52.546  1.00 46.41      B    C
ATOM   2986  CG   LYS B  85      -6.518  16.146  53.458  1.00 46.41      B    C
ATOM   2987  CD   LYS B  85      -5.054  15.968  53.854  1.00 46.41      B    C
ATOM   2988  CE   LYS B  85      -4.904  14.972  55.016  1.00 46.41      B    C
ATOM   2989  NZ   LYS B  85      -3.476  14.654  55.342  1.00 46.41      B    N
ATOM   2990  C    LYS B  85      -8.971  18.156  53.291  1.00 39.65      B    C
ATOM   2991  O    LYS B  85      -8.566  19.093  53.969  1.00 39.65      B    O
ATOM   2992  N    LYS B  86     -10.150  17.582  53.497  1.00 40.84      B    N
ATOM   2993  CA   LYS B  86     -11.031  18.027  54.566  1.00 40.84      B    C
ATOM   2994  CB   LYS B  86     -12.509  17.828  54.166  1.00 46.80      B    C
ATOM   2995  CG   LYS B  86     -13.469  18.719  54.941  1.00 46.80      B    C
ATOM   2996  CD   LYS B  86     -14.852  18.101  55.150  1.00 46.80      B    C
ATOM   2997  CE   LYS B  86     -15.756  18.218  53.928  1.00 46.80      B    C
ATOM   2998  NZ   LYS B  86     -16.104  19.638  53.576  1.00 46.80      B    N
ATOM   2999  C    LYS B  86     -10.695  17.218  55.814  1.00 40.84      B    C
ATOM   3000  O    LYS B  86     -10.683  15.994  55.783  1.00 40.84      B    O
ATOM   3001  N    VAL B  87     -10.418  17.905  56.912  1.00 48.08      B    N
ATOM   3002  CA   VAL B  87     -10.060  17.231  58.154  1.00 48.08      B    C
ATOM   3003  CB   VAL B  87      -8.551  17.379  58.464  1.00 35.08      B    C
ATOM   3004  CG1  VAL B  87      -8.262  16.852  59.847  1.00 35.08      B    C
ATOM   3005  CG2  VAL B  87      -7.718  16.641  57.439  1.00 35.08      B    C
ATOM   3006  C    VAL B  87     -10.815  17.786  59.349  1.00 48.08      B    C
ATOM   3007  O    VAL B  87     -10.931  19.003  59.503  1.00 48.08      B    O
ATOM   3008  N    LEU B  88     -11.322  16.895  60.197  1.00 63.03      B    N
```

FIG. 3-46

| ATOM | 3009 | CA | LEU | B | 88 | -12.037 | 17.322 | 61.398 | 1.00 | 63.03 | B | C |
|------|------|------|------|---|----|---------|--------|--------|------|-------|---|---|
| ATOM | 3010 | CB | LEU | B | 88 | -12.735 | 16.125 | 62.065 | 1.00 | 61.29 | B | C |
| ATOM | 3011 | CG | LEU | B | 88 | -13.706 | 16.269 | 63.260 | 1.00 | 61.29 | B | C |
| ATOM | 3012 | CD1 | LEU | B | 88 | -13.045 | 17.023 | 64.411 | 1.00 | 61.29 | B | C |
| ATOM | 3013 | CD2 | LEU | B | 88 | -14.988 | 16.979 | 62.805 | 1.00 | 61.29 | B | C |
| ATOM | 3014 | C | LEU | B | 88 | -10.950 | 17.861 | 62.325 | 1.00 | 63.03 | B | C |
| ATOM | 3015 | O | LEU | B | 88 | -10.150 | 17.084 | 62.842 | 1.00 | 63.03 | B | O |
| ATOM | 3016 | N | GLN | B | 89 | -10.890 | 19.176 | 62.511 | 1.00 | 56.81 | B | N |
| ATOM | 3017 | CA | GLN | B | 89 | -9.876 | 19.738 | 63.391 | 1.00 | 56.81 | B | C |
| ATOM | 3018 | CB | GLN | B | 89 | -9.100 | 20.860 | 62.704 | 1.00 | 70.27 | B | C |
| ATOM | 3019 | CG | GLN | B | 89 | -7.982 | 21.427 | 63.575 | 1.00 | 70.27 | B | C |
| ATOM | 3020 | CD | GLN | B | 89 | -7.035 | 20.346 | 64.109 | 1.00 | 70.27 | B | C |
| ATOM | 3021 | OE1 | GLN | B | 89 | -7.226 | 19.140 | 63.854 | 1.00 | 70.27 | B | O |
| ATOM | 3022 | NE2 | GLN | B | 89 | -6.006 | 20.772 | 64.859 | 1.00 | 70.27 | B | N |
| ATOM | 3023 | C | GLN | B | 89 | -10.482 | 20.259 | 64.680 | 1.00 | 56.81 | B | C |
| ATOM | 3024 | O | GLN | B | 89 | -11.527 | 20.911 | 64.678 | 1.00 | 56.81 | B | O |
| ATOM | 3025 | N | ASP | B | 90 | -9.805 | 19.973 | 65.784 | 1.00 | 85.43 | B | N |
| ATOM | 3026 | CA | ASP | B | 90 | -10.270 | 20.378 | 67.109 | 1.00 | 85.43 | B | C |
| ATOM | 3027 | CB | ASP | B | 90 | -9.806 | 19.325 | 68.115 | 1.00 | 95.80 | B | C |
| ATOM | 3028 | CG | ASP | B | 90 | -10.090 | 19.713 | 69.548 | 1.00 | 95.80 | B | C |
| ATOM | 3029 | OD1 | ASP | B | 90 | -9.953 | 18.814 | 70.422 | 1.00 | 95.80 | B | O |
| ATOM | 3030 | OD2 | ASP | B | 90 | -10.434 | 20.897 | 69.803 | 1.00 | 95.80 | B | O |
| ATOM | 3031 | C | ASP | B | 90 | -9.743 | 21.768 | 67.501 | 1.00 | 85.43 | B | C |
| ATOM | 3032 | O | ASP | B | 90 | -8.724 | 21.864 | 68.178 | 1.00 | 85.43 | B | O |
| ATOM | 3033 | N | LYS | B | 91 | -10.433 | 22.832 | 67.076 | 1.00 | 91.44 | B | N |
| ATOM | 3034 | CA | LYS | B | 91 | -10.030 | 24.232 | 67.326 | 1.00 | 91.44 | B | C |
| ATOM | 3035 | CB | LYS | B | 91 | -11.287 | 25.110 | 67.389 | 1.00 | 90.01 | B | C |
| ATOM | 3036 | CG | LYS | B | 91 | -11.814 | 25.535 | 66.001 | 1.00 | 90.01 | B | C |
| ATOM | 3037 | CD | LYS | B | 91 | -11.086 | 26.779 | 65.416 | 1.00 | 90.01 | B | C |
| ATOM | 3038 | CE | LYS | B | 91 | -9.553 | 26.601 | 65.292 | 1.00 | 90.01 | B | C |
| ATOM | 3039 | NZ | LYS | B | 91 | -8.839 | 27.828 | 64.789 | 1.00 | 90.01 | B | N |
| ATOM | 3040 | C | LYS | B | 91 | -9.064 | 24.625 | 68.484 | 1.00 | 91.44 | B | C |
| ATOM | 3041 | O | LYS | B | 91 | -8.222 | 25.518 | 68.320 | 1.00 | 91.44 | B | O |
| ATOM | 3042 | N | ALA | B | 92 | -9.192 | 23.979 | 69.635 | 1.00 | 79.01 | B | N |
| ATOM | 3043 | CA | ALA | B | 92 | -8.364 | 24.218 | 70.826 | 1.00 | 79.01 | B | C |
| ATOM | 3044 | CB | ALA | B | 92 | -8.852 | 23.291 | 71.949 | 1.00 | 74.41 | B | C |
| ATOM | 3045 | C | ALA | B | 92 | -6.855 | 23.987 | 70.564 | 1.00 | 79.01 | B | C |
| ATOM | 3046 | O | ALA | B | 92 | -5.981 | 24.665 | 71.135 | 1.00 | 79.01 | B | O |
| ATOM | 3047 | N | ALA | B | 93 | -6.568 | 23.016 | 69.700 | 1.00 | 86.92 | B | N |
| ATOM | 3048 | CA | ALA | B | 93 | -5.198 | 22.669 | 69.337 | 1.00 | 86.92 | B | C |
| ATOM | 3049 | CB | ALA | B | 93 | -4.945 | 21.180 | 69.612 | 1.00 | 53.15 | B | C |
| ATOM | 3050 | C | ALA | B | 93 | -4.926 | 22.993 | 67.860 | 1.00 | 86.92 | B | C |
| ATOM | 3051 | O | ALA | B | 93 | -5.809 | 22.839 | 66.995 | 1.00 | 86.92 | B | O |
| ATOM | 3052 | N | ALA | B | 94 | -3.703 | 23.457 | 67.588 | 1.00 | 73.93 | B | N |
| ATOM | 3053 | CA | ALA | B | 94 | -3.289 | 23.790 | 66.228 | 1.00 | 73.93 | B | C |
| ATOM | 3054 | CB | ALA | B | 94 | -2.005 | 24.619 | 66.252 | 1.00 | 49.39 | B | C |
| ATOM | 3055 | C | ALA | B | 94 | -3.057 | 22.478 | 65.487 | 1.00 | 73.93 | B | C |
| ATOM | 3056 | O | ALA | B | 94 | -2.632 | 21.479 | 66.091 | 1.00 | 73.93 | B | O |
| ATOM | 3057 | N | ASN | B | 95 | -3.342 | 22.489 | 64.183 | 1.00 | 40.63 | B | N |
| ATOM | 3058 | CA | ASN | B | 95 | -3.185 | 21.316 | 63.317 | 1.00 | 40.63 | B | C |
| ATOM | 3059 | CB | ASN | B | 95 | -4.062 | 21.506 | 62.076 | 1.00 | 49.60 | B | C |
| ATOM | 3060 | CG | ASN | B | 95 | -4.137 | 20.266 | 61.212 | 1.00 | 49.60 | B | C |
| ATOM | 3061 | OD1 | ASN | B | 95 | -3.259 | 20.019 | 60.381 | 1.00 | 49.60 | B | O |
| ATOM | 3062 | ND2 | ASN | B | 95 | -5.186 | 19.473 | 61.406 | 1.00 | 49.60 | B | N |
| ATOM | 3063 | C | ASN | B | 95 | -1.712 | 21.102 | 62.926 | 1.00 | 40.63 | B | C |
| ATOM | 3064 | O | ASN | B | 95 | -1.081 | 21.975 | 62.328 | 1.00 | 40.63 | B | O |
| ATOM | 3065 | N | ARG | B | 96 | -1.169 | 19.938 | 63.268 | 1.00 | 44.26 | B | N |
| ATOM | 3066 | CA | ARG | B | 96 | 0.229 | 19.640 | 62.973 | 1.00 | 44.26 | B | C |
| ATOM | 3067 | CB | ARG | B | 96 | 0.631 | 18.313 | 63.612 | 1.00 | 55.54 | B | C |
| ATOM | 3068 | CG | ARG | B | 96 | 2.121 | 18.084 | 63.648 | 1.00 | 55.54 | B | C |
| ATOM | 3069 | CD | ARG | B | 96 | 2.476 | 16.687 | 64.176 | 1.00 | 55.54 | B | C |
| ATOM | 3070 | NE | ARG | B | 96 | 2.543 | 16.589 | 65.637 | 1.00 | 55.54 | B | N |
| ATOM | 3071 | CZ | ARG | B | 96 | 2.712 | 15.440 | 66.292 | 1.00 | 55.54 | B | C |
| ATOM | 3072 | NH1 | ARG | B | 96 | 2.826 | 14.303 | 65.611 | 1.00 | 55.54 | B | N |
| ATOM | 3073 | NH2 | ARG | B | 96 | 2.760 | 15.415 | 67.619 | 1.00 | 55.54 | B | N |
| ATOM | 3074 | C | ARG | B | 96 | 0.562 | 19.617 | 61.478 | 1.00 | 44.26 | B | C |
| ATOM | 3075 | O | ARG | B | 96 | 1.586 | 20.158 | 61.060 | 1.00 | 44.26 | B | O |

FIG. 3-47

| | | | | | | | | | | |
|---|---|---|---|---|---|---|---|---|---|---|
| ATOM | 3076 | N | GLU | B | 97 | -0.291 | 19.000 | 60.667 | 1.00 38.77 | B N |
| ATOM | 3077 | CA | GLU | B | 97 | -0.032 | 18.948 | 59.237 | 1.00 38.77 | B C |
| ATOM | 3078 | CB | GLU | B | 97 | -1.116 | 18.137 | 58.527 | 1.00 40.61 | B C |
| ATOM | 3079 | CG | GLU | B | 97 | -0.828 | 17.885 | 57.056 | 1.00 40.61 | B C |
| ATOM | 3080 | CD | GLU | B | 97 | -1.835 | 16.944 | 56.427 | 1.00 40.61 | B C |
| ATOM | 3081 | OE1 | GLU | B | 97 | -2.608 | 16.319 | 57.190 | 1.00 40.61 | B O |
| ATOM | 3082 | OE2 | GLU | B | 97 | -1.847 | 16.813 | 55.181 | 1.00 40.61 | B O |
| ATOM | 3083 | C | GLU | B | 97 | 0.027 | 20.351 | 58.638 | 1.00 38.77 | B C |
| ATOM | 3084 | O | GLU | B | 97 | 0.901 | 20.651 | 57.831 | 1.00 38.77 | B O |
| ATOM | 3085 | N | LEU | B | 98 | -0.910 | 21.209 | 59.030 | 1.00 32.75 | B N |
| ATOM | 3086 | CA | LEU | B | 98 | -0.946 | 22.565 | 58.502 | 1.00 32.75 | B C |
| ATOM | 3087 | CB | LEU | B | 98 | -2.189 | 23.299 | 59.020 | 1.00 30.03 | B C |
| ATOM | 3088 | CG | LEU | B | 98 | -2.302 | 24.779 | 58.640 | 1.00 30.03 | B C |
| ATOM | 3089 | CD1 | LEU | B | 98 | -2.025 | 24.945 | 57.152 | 1.00 30.03 | B C |
| ATOM | 3090 | CD2 | LEU | B | 98 | -3.681 | 25.303 | 59.001 | 1.00 30.03 | B C |
| ATOM | 3091 | C | LEU | B | 98 | 0.317 | 23.363 | 58.839 | 1.00 32.75 | B C |
| ATOM | 3092 | O | LEU | B | 98 | 0.859 | 24.080 | 57.994 | 1.00 32.75 | B O |
| ATOM | 3093 | N | GLN | B | 99 | 0.787 | 23.236 | 60.074 | 1.00 56.98 | B N |
| ATOM | 3094 | CA | GLN | B | 99 | 1.978 | 23.954 | 60.495 | 1.00 56.98 | B C |
| ATOM | 3095 | CB | GLN | B | 99 | 2.225 | 23.748 | 61.994 | 1.00 96.79 | B C |
| ATOM | 3096 | CG | GLN | B | 99 | 1.362 | 24.621 | 62.902 | 1.00 96.79 | B C |
| ATOM | 3097 | CD | GLN | B | 99 | 1.640 | 24.371 | 64.389 | 1.00 96.79 | B C |
| ATOM | 3098 | OE1 | GLN | B | 99 | 1.056 | 25.034 | 65.266 | 1.00 96.79 | B O |
| ATOM | 3099 | NE2 | GLN | B | 99 | 2.530 | 23.404 | 64.682 | 1.00 96.79 | B N |
| ATOM | 3100 | C | GLN | B | 99 | 3.210 | 23.534 | 59.701 | 1.00 56.98 | B C |
| ATOM | 3101 | O | GLN | B | 99 | 4.011 | 24.381 | 59.309 | 1.00 56.98 | B O |
| ATOM | 3102 | N | ILE | B | 100 | 3.368 | 22.236 | 59.468 | 1.00 41.38 | B N |
| ATOM | 3103 | CA | ILE | B | 100 | 4.509 | 21.749 | 58.702 | 1.00 41.38 | B C |
| ATOM | 3104 | CB | ILE | B | 100 | 4.599 | 20.208 | 58.744 | 1.00 32.04 | B C |
| ATOM | 3105 | CG2 | ILE | B | 100 | 5.651 | 19.718 | 57.767 | 1.00 32.04 | B C |
| ATOM | 3106 | CG1 | ILE | B | 100 | 4.931 | 19.751 | 60.169 | 1.00 32.04 | B C |
| ATOM | 3107 | CD1 | ILE | B | 100 | 4.935 | 18.261 | 60.362 | 1.00 32.04 | B C |
| ATOM | 3108 | C | ILE | B | 100 | 4.360 | 22.190 | 57.257 | 1.00 41.38 | B C |
| ATOM | 3109 | O | ILE | B | 100 | 5.219 | 22.871 | 56.704 | 1.00 41.38 | B O |
| ATOM | 3110 | N | MET | B | 101 | 3.242 | 21.798 | 56.662 | 1.00 53.97 | B N |
| ATOM | 3111 | CA | MET | B | 101 | 2.911 | 22.104 | 55.282 | 1.00 53.97 | B C |
| ATOM | 3112 | CB | MET | B | 101 | 1.435 | 21.801 | 55.051 | 1.00 58.31 | B C |
| ATOM | 3113 | CG | MET | B | 101 | 1.078 | 21.624 | 53.610 | 1.00 58.31 | B C |
| ATOM | 3114 | SD | MET | B | 101 | 1.852 | 20.117 | 52.967 | 1.00 58.31 | B S |
| ATOM | 3115 | CE | MET | B | 101 | 0.431 | 18.907 | 53.135 | 1.00 58.31 | B C |
| ATOM | 3116 | C | MET | B | 101 | 3.178 | 23.564 | 54.948 | 1.00 53.97 | B C |
| ATOM | 3117 | O | MET | B | 101 | 3.835 | 23.890 | 53.954 | 1.00 53.97 | B O |
| ATOM | 3118 | N | ARG | B | 102 | 2.661 | 24.436 | 55.803 | 1.00 37.14 | B N |
| ATOM | 3119 | CA | ARG | B | 102 | 2.762 | 25.883 | 55.642 | 1.00 37.14 | B C |
| ATOM | 3120 | CB | ARG | B | 102 | 1.996 | 26.546 | 56.789 | 1.00 62.24 | B C |
| ATOM | 3121 | CG | ARG | B | 102 | 1.642 | 28.006 | 56.591 | 1.00 62.24 | B C |
| ATOM | 3122 | CD | ARG | B | 102 | 0.182 | 28.185 | 56.202 | 1.00 62.24 | B C |
| ATOM | 3123 | NE | ARG | B | 102 | -0.228 | 29.585 | 56.315 | 1.00 62.24 | B N |
| ATOM | 3124 | CZ | ARG | B | 102 | -0.504 | 30.188 | 57.466 | 1.00 62.24 | B C |
| ATOM | 3125 | NH1 | ARG | B | 102 | -0.420 | 29.510 | 58.603 | 1.00 62.24 | B N |
| ATOM | 3126 | NH2 | ARG | B | 102 | -0.857 | 31.467 | 57.479 | 1.00 62.24 | B N |
| ATOM | 3127 | C | ARG | B | 102 | 4.169 | 26.487 | 55.547 | 1.00 37.14 | B C |
| ATOM | 3128 | O | ARG | B | 102 | 4.321 | 27.605 | 55.067 | 1.00 37.14 | B O |
| ATOM | 3129 | N | LYS | B | 103 | 5.194 | 25.767 | 55.997 | 1.00 42.28 | B N |
| ATOM | 3130 | CA | LYS | B | 103 | 6.557 | 26.308 | 55.956 | 1.00 42.28 | B C |
| ATOM | 3131 | CB | LYS | B | 103 | 7.205 | 26.256 | 57.350 | 1.00 60.27 | B C |
| ATOM | 3132 | CG | LYS | B | 103 | 7.750 | 24.899 | 57.749 | 1.00 60.27 | B C |
| ATOM | 3133 | CD | LYS | B | 103 | 8.501 | 24.930 | 59.086 | 1.00 60.27 | B C |
| ATOM | 3134 | CE | LYS | B | 103 | 7.561 | 25.112 | 60.276 | 1.00 60.27 | B C |
| ATOM | 3135 | NZ | LYS | B | 103 | 8.194 | 24.712 | 61.568 | 1.00 60.27 | B N |
| ATOM | 3136 | C | LYS | B | 103 | 7.472 | 25.612 | 54.964 | 1.00 42.28 | B C |
| ATOM | 3137 | O | LYS | B | 103 | 8.690 | 25.761 | 55.025 | 1.00 42.28 | B O |
| ATOM | 3138 | N | LEU | B | 104 | 6.877 | 24.851 | 54.055 | 1.00 50.04 | B N |
| ATOM | 3139 | CA | LEU | B | 104 | 7.630 | 24.127 | 53.041 | 1.00 50.04 | B C |
| ATOM | 3140 | CB | LEU | B | 104 | 7.203 | 22.659 | 53.025 | 1.00 41.16 | B C |
| ATOM | 3141 | CG | LEU | B | 104 | 7.991 | 21.643 | 53.855 | 1.00 41.16 | B C |
| ATOM | 3142 | CD1 | LEU | B | 104 | 8.357 | 22.193 | 55.217 | 1.00 41.16 | B C |

FIG. 3-48

| | | | | | | | | | | | |
|---|---|---|---|---|---|---|---|---|---|---|---|
| ATOM | 3143 | CD2 | LEU | B | 104 | 7.150 | 20.384 | 53.976 | 1.00 | 41.16 | B | C |
| ATOM | 3144 | C | LEU | B | 104 | 7.428 | 24.722 | 51.652 | 1.00 | 50.04 | B | C |
| ATOM | 3145 | O | LEU | B | 104 | 6.324 | 25.115 | 51.283 | 1.00 | 50.04 | B | O |
| ATOM | 3146 | N | ASP | B | 105 | 8.506 | 24.802 | 50.886 | 1.00 | 45.95 | B | N |
| ATOM | 3147 | CA | ASP | B | 105 | 8.429 | 25.308 | 49.522 | 1.00 | 45.95 | B | C |
| ATOM | 3148 | CB | ASP | B | 105 | 8.648 | 26.817 | 49.476 | 1.00 | 60.25 | B | C |
| ATOM | 3149 | CG | ASP | B | 105 | 8.411 | 27.401 | 48.070 | 1.00 | 60.25 | B | C |
| ATOM | 3150 | OD1 | ASP | B | 105 | 8.071 | 26.621 | 47.129 | 1.00 | 60.25 | B | O |
| ATOM | 3151 | OD2 | ASP | B | 105 | 8.568 | 28.642 | 47.932 | 1.00 | 60.25 | B | O |
| ATOM | 3152 | C | ASP | B | 105 | 9.473 | 24.607 | 48.670 | 1.00 | 45.95 | B | C |
| ATOM | 3153 | O | ASP | B | 105 | 10.592 | 25.094 | 48.505 | 1.00 | 45.95 | B | O |
| ATOM | 3154 | N | HIS | B | 106 | 9.092 | 23.457 | 48.129 | 1.00 | 50.78 | B | N |
| ATOM | 3155 | CA | HIS | B | 106 | 10.006 | 22.674 | 47.322 | 1.00 | 50.78 | B | C |
| ATOM | 3156 | CB | HIS | B | 106 | 10.624 | 21.542 | 48.156 | 1.00 | 50.33 | B | C |
| ATOM | 3157 | CG | HIS | B | 106 | 11.915 | 21.026 | 47.621 | 1.00 | 50.33 | B | C |
| ATOM | 3158 | CD2 | HIS | B | 106 | 13.186 | 21.172 | 48.058 | 1.00 | 50.33 | B | C |
| ATOM | 3159 | ND1 | HIS | B | 106 | 11.999 | 20.226 | 46.491 | 1.00 | 50.33 | B | N |
| ATOM | 3160 | CE1 | HIS | B | 106 | 13.259 | 19.909 | 46.275 | 1.00 | 50.33 | B | C |
| ATOM | 3161 | NE2 | HIS | B | 106 | 14.005 | 20.471 | 47.216 | 1.00 | 50.33 | B | N |
| ATOM | 3162 | C | HIS | B | 106 | 9.235 | 22.107 | 46.159 | 1.00 | 50.78 | B | C |
| ATOM | 3163 | O | HIS | B | 106 | 8.111 | 21.562 | 46.312 | 1.00 | 50.78 | B | O |
| ATOM | 3164 | N | CYS | B | 107 | 9.845 | 22.241 | 44.992 | 1.00 | 35.53 | B | N |
| ATOM | 3165 | CA | CYS | B | 107 | 9.175 | 21.757 | 43.846 | 1.00 | 35.53 | B | C |
| ATOM | 3166 | CB | CYS | B | 107 | 9.834 | 22.295 | 42.578 | 1.00 | 66.39 | B | C |
| ATOM | 3167 | SG | CYS | B | 107 | 9.222 | 24.019 | 42.193 | 1.00 | 66.39 | B | S |
| ATOM | 3168 | C | CYS | B | 107 | 9.032 | 20.256 | 43.855 | 1.00 | 35.53 | B | C |
| ATOM | 3169 | O | CYS | B | 107 | 8.482 | 19.681 | 42.916 | 1.00 | 35.53 | B | O |
| ATOM | 3170 | N | ASN | B | 108 | 9.462 | 19.600 | 44.927 | 1.00 | 40.59 | B | N |
| ATOM | 3171 | CA | ASN | B | 108 | 9.272 | 18.172 | 44.926 | 1.00 | 40.59 | B | C |
| ATOM | 3172 | CB | ASN | B | 108 | 10.595 | 17.440 | 45.084 | 1.00 | 31.95 | B | C |
| ATOM | 3173 | CG | ASN | B | 108 | 11.351 | 17.342 | 43.778 | 1.00 | 31.95 | B | C |
| ATOM | 3174 | OD1 | ASN | B | 108 | 12.493 | 17.765 | 43.677 | 1.00 | 31.95 | B | O |
| ATOM | 3175 | ND2 | ASN | B | 108 | 10.704 | 16.774 | 42.761 | 1.00 | 31.95 | B | N |
| ATOM | 3176 | C | ASN | B | 108 | 8.302 | 17.818 | 46.017 | 1.00 | 40.59 | B | C |
| ATOM | 3177 | O | ASN | B | 108 | 8.239 | 16.679 | 46.449 | 1.00 | 40.59 | B | O |
| ATOM | 3178 | N | ILE | B | 109 | 7.523 | 18.811 | 46.443 | 1.00 | 26.36 | B | N |
| ATOM | 3179 | CA | ILE | B | 109 | 6.515 | 18.622 | 47.477 | 1.00 | 26.36 | B | C |
| ATOM | 3180 | CB | ILE | B | 109 | 6.978 | 19.250 | 48.815 | 1.00 | 38.53 | B | C |
| ATOM | 3181 | CG2 | ILE | B | 109 | 5.880 | 19.186 | 49.853 | 1.00 | 38.53 | B | C |
| ATOM | 3182 | CG1 | ILE | B | 109 | 8.200 | 18.496 | 49.318 | 1.00 | 38.53 | B | C |
| ATOM | 3183 | CD1 | ILE | B | 109 | 8.712 | 18.985 | 50.633 | 1.00 | 38.53 | B | C |
| ATOM | 3184 | C | ILE | B | 109 | 5.223 | 19.280 | 47.018 | 1.00 | 26.36 | B | C |
| ATOM | 3185 | O | ILE | B | 109 | 5.273 | 20.368 | 46.456 | 1.00 | 26.36 | B | O |
| ATOM | 3186 | N | VAL | B | 110 | 4.077 | 18.632 | 47.230 | 1.00 | 35.57 | B | N |
| ATOM | 3187 | CA | VAL | B | 110 | 2.817 | 19.251 | 46.819 | 1.00 | 35.57 | B | C |
| ATOM | 3188 | CB | VAL | B | 110 | 1.561 | 18.489 | 47.269 | 1.00 | 46.26 | B | C |
| ATOM | 3189 | CG1 | VAL | B | 110 | 1.503 | 17.143 | 46.608 | 1.00 | 46.26 | B | C |
| ATOM | 3190 | CG2 | VAL | B | 110 | 1.544 | 18.367 | 48.778 | 1.00 | 46.26 | B | C |
| ATOM | 3191 | C | VAL | B | 110 | 2.753 | 20.596 | 47.493 | 1.00 | 35.57 | B | C |
| ATOM | 3192 | O | VAL | B | 110 | 3.096 | 20.726 | 48.661 | 1.00 | 35.57 | B | O |
| ATOM | 3193 | N | ARG | B | 111 | 2.319 | 21.602 | 46.751 | 1.00 | 48.70 | B | N |
| ATOM | 3194 | CA | ARG | B | 111 | 2.207 | 22.939 | 47.292 | 1.00 | 48.70 | B | C |
| ATOM | 3195 | CB | ARG | B | 111 | 2.378 | 23.980 | 46.172 | 1.00 | 76.02 | B | C |
| ATOM | 3196 | CG | ARG | B | 111 | 2.270 | 25.367 | 46.741 | 1.00 | 76.02 | B | C |
| ATOM | 3197 | CD | ARG | B | 111 | 2.605 | 26.467 | 45.925 | 1.00 | 76.02 | B | C |
| ATOM | 3198 | NE | ARG | B | 111 | 2.034 | 26.367 | 44.682 | 1.00 | 76.02 | B | N |
| ATOM | 3199 | CZ | ARG | B | 111 | 1.821 | 27.331 | 43.828 | 1.00 | 76.02 | B | C |
| ATOM | 3200 | NH1 | ARG | B | 111 | 2.079 | 28.641 | 44.060 | 1.00 | 76.02 | B | N |
| ATOM | 3201 | NH2 | ARG | B | 111 | 1.525 | 26.863 | 42.633 | 1.00 | 76.02 | B | N |
| ATOM | 3202 | C | ARG | B | 111 | 0.838 | 23.099 | 47.967 | 1.00 | 48.70 | B | C |
| ATOM | 3203 | O | ARG | B | 111 | -0.164 | 22.524 | 47.523 | 1.00 | 48.70 | B | O |
| ATOM | 3204 | N | LEU | B | 112 | 0.808 | 23.846 | 49.065 | 1.00 | 47.15 | B | N |
| ATOM | 3205 | CA | LEU | B | 112 | -0.436 | 24.109 | 49.762 | 1.00 | 47.15 | B | C |
| ATOM | 3206 | CB | LEU | B | 112 | -0.208 | 24.149 | 51.270 | 1.00 | 31.61 | B | C |
| ATOM | 3207 | CG | LEU | B | 112 | -1.380 | 24.619 | 52.134 | 1.00 | 31.61 | B | C |
| ATOM | 3208 | CD1 | LEU | B | 112 | -2.407 | 23.509 | 52.249 | 1.00 | 31.61 | B | C |
| ATOM | 3209 | CD2 | LEU | B | 112 | -0.885 | 25.002 | 53.509 | 1.00 | 31.61 | B | C |

FIG. 3-49

```
ATOM   3210  C    LEU B 112      -0.822  25.493  49.257  1.00 47.15      B  C
ATOM   3211  O    LEU B 112      -0.280  26.494  49.722  1.00 47.15      B  O
ATOM   3212  N    ARG B 113      -1.735  25.544  48.290  1.00 51.35      B  N
ATOM   3213  CA   ARG B 113      -2.185  26.808  47.712  1.00 51.35      B  C
ATOM   3214  CB   ARG B 113      -3.136  26.546  46.541  1.00 63.30      B  C
ATOM   3215  CG   ARG B 113      -2.575  25.614  45.474  1.00 63.30      B  C
ATOM   3216  CD   ARG B 113      -1.436  26.271  44.704  1.00 63.30      B  C
ATOM   3217  NE   ARG B 113      -1.908  27.068  43.571  1.00 63.30      B  N
ATOM   3218  CZ   ARG B 113      -2.465  26.553  42.474  1.00 63.30      B  C
ATOM   3219  NH1  ARG B 113      -2.623  25.235  42.356  1.00 63.30      B  N
ATOM   3220  NH2  ARG B 113      -2.861  27.355  41.493  1.00 63.30      B  N
ATOM   3221  C    ARG B 113      -2.892  27.679  48.745  1.00 51.35      B  C
ATOM   3222  O    ARG B 113      -2.595  28.869  48.869  1.00 51.35      B  O
ATOM   3223  N    TYR B 114      -3.829  27.083  49.476  1.00 39.49      B  N
ATOM   3224  CA   TYR B 114      -4.595  27.797  50.495  1.00 39.49      B  C
ATOM   3225  CB   TYR B 114      -5.871  28.430  49.910  1.00 48.51      B  C
ATOM   3226  CG   TYR B 114      -5.700  29.192  48.623  1.00 48.51      B  C
ATOM   3227  CD1  TYR B 114      -5.087  30.443  48.603  1.00 48.51      B  C
ATOM   3228  CE1  TYR B 114      -4.888  31.120  47.406  1.00 48.51      B  C
ATOM   3229  CD2  TYR B 114      -6.112  28.640  47.410  1.00 48.51      B  C
ATOM   3230  CE2  TYR B 114      -5.916  29.309  46.213  1.00 48.51      B  C
ATOM   3231  CZ   TYR B 114      -5.302  30.547  46.219  1.00 48.51      B  C
ATOM   3232  OH   TYR B 114      -5.084  31.211  45.037  1.00 48.51      B  O
ATOM   3233  C    TYR B 114      -5.065  26.789  51.519  1.00 39.49      B  C
ATOM   3234  O    TYR B 114      -4.844  25.586  51.386  1.00 39.49      B  O
ATOM   3235  N    PHE B 115      -5.730  27.296  52.543  1.00 41.15      B  N
ATOM   3236  CA   PHE B 115      -6.325  26.449  53.554  1.00 41.15      B  C
ATOM   3237  CB   PHE B 115      -5.305  26.040  54.632  1.00 43.07      B  C
ATOM   3238  CG   PHE B 115      -4.899  27.139  55.564  1.00 43.07      B  C
ATOM   3239  CD1  PHE B 115      -5.600  27.361  56.740  1.00 43.07      B  C
ATOM   3240  CD2  PHE B 115      -3.773  27.907  55.303  1.00 43.07      B  C
ATOM   3241  CE1  PHE B 115      -5.180  28.327  57.645  1.00 43.07      B  C
ATOM   3242  CE2  PHE B 115      -3.347  28.875  56.203  1.00 43.07      B  C
ATOM   3243  CZ   PHE B 115      -4.048  29.082  57.374  1.00 43.07      B  C
ATOM   3244  C    PHE B 115      -7.472  27.286  54.094  1.00 41.15      B  C
ATOM   3245  O    PHE B 115      -7.379  28.516  54.159  1.00 41.15      B  O
ATOM   3246  N    PHE B 116      -8.580  26.632  54.412  1.00 41.56      B  N
ATOM   3247  CA   PHE B 116      -9.725  27.352  54.923  1.00 41.56      B  C
ATOM   3248  CB   PHE B 116     -10.579  27.868  53.750  1.00 48.02      B  C
ATOM   3249  CG   PHE B 116     -11.284  26.789  52.962  1.00 48.02      B  C
ATOM   3250  CD1  PHE B 116     -12.506  26.270  53.395  1.00 48.02      B  C
ATOM   3251  CD2  PHE B 116     -10.755  26.324  51.760  1.00 48.02      B  C
ATOM   3252  CE1  PHE B 116     -13.197  25.308  52.637  1.00 48.02      B  C
ATOM   3253  CE2  PHE B 116     -11.442  25.358  50.994  1.00 48.02      B  C
ATOM   3254  CZ   PHE B 116     -12.664  24.855  51.437  1.00 48.02      B  C
ATOM   3255  C    PHE B 116     -10.528  26.460  55.850  1.00 41.56      B  C
ATOM   3256  O    PHE B 116     -10.311  25.252  55.891  1.00 41.56      B  O
ATOM   3257  N    TYR B 117     -11.440  27.063  56.605  1.00 53.88      B  N
ATOM   3258  CA   TYR B 117     -12.270  26.319  57.541  1.00 53.88      B  C
ATOM   3259  CB   TYR B 117     -12.194  26.973  58.914  1.00 45.96      B  C
ATOM   3260  CG   TYR B 117     -10.787  26.974  59.438  1.00 45.96      B  C
ATOM   3261  CD1  TYR B 117     -10.275  25.870  60.116  1.00 45.96      B  C
ATOM   3262  CE1  TYR B 117      -8.937  25.827  60.514  1.00 45.96      B  C
ATOM   3263  CD2  TYR B 117      -9.931  28.041  59.173  1.00 45.96      B  C
ATOM   3264  CE2  TYR B 117      -8.597  28.006  59.560  1.00 45.96      B  C
ATOM   3265  CZ   TYR B 117      -8.110  26.899  60.228  1.00 45.96      B  C
ATOM   3266  OH   TYR B 117      -6.794  26.866  60.602  1.00 45.96      B  O
ATOM   3267  C    TYR B 117     -13.712  26.232  57.057  1.00 53.88      B  C
ATOM   3268  O    TYR B 117     -14.110  26.944  56.129  1.00 53.88      B  O
ATOM   3269  N    SER B 118     -14.495  25.356  57.681  1.00 53.94      B  N
ATOM   3270  CA   SER B 118     -15.876  25.183  57.277  1.00 53.94      B  C
ATOM   3271  CB   SER B 118     -15.921  24.507  55.908  1.00 45.85      B  C
ATOM   3272  OG   SER B 118     -15.060  23.391  55.879  1.00 45.85      B  O
ATOM   3273  C    SER B 118     -16.711  24.387  58.265  1.00 53.94      B  C
ATOM   3274  O    SER B 118     -16.202  23.870  59.265  1.00 53.94      B  O
ATOM   3275  N    SER B 119     -18.005  24.289  57.973  1.00 57.31      B  N
ATOM   3276  CA   SER B 119     -18.932  23.554  58.831  1.00 57.31      B  C
```

FIG. 3-50

```
ATOM   3277  CB   SER B 119     -20.176  24.411  59.102  1.00 96.33      B  C
ATOM   3278  OG   SER B 119     -19.833  25.595  59.818  1.00 96.33      B  O
ATOM   3279  C    SER B 119     -19.340  22.223  58.200  1.00 57.31      B  C
ATOM   3280  O    SER B 119     -19.233  21.169  58.829  1.00 57.31      B  O
ATOM   3281  N    ALA B 125     -18.780  21.720  65.100  1.00 95.31      B  N
ATOM   3282  CA   ALA B 125     -17.407  21.298  64.818  1.00 95.31      B  C
ATOM   3283  CB   ALA B 125     -17.373  19.799  64.509  1.00 41.56      B  C
ATOM   3284  C    ALA B 125     -16.822  22.099  63.647  1.00 95.31      B  C
ATOM   3285  O    ALA B 125     -17.570  22.602  62.793  1.00 95.31      B  O
ATOM   3286  N    ALA B 126     -15.493  22.221  63.608  1.00 64.13      B  N
ATOM   3287  CA   ALA B 126     -14.828  22.969  62.543  1.00 64.13      B  C
ATOM   3288  CB   ALA B 126     -14.119  24.189  63.133  1.00 29.48      B  C
ATOM   3289  C    ALA B 126     -13.831  22.084  61.786  1.00 64.13      B  C
ATOM   3290  O    ALA B 126     -12.924  21.508  62.389  1.00 64.13      B  O
ATOM   3291  N    TYR B 127     -14.004  21.973  60.467  1.00 48.62      B  N
ATOM   3292  CA   TYR B 127     -13.117  21.156  59.634  1.00 48.62      B  C
ATOM   3293  CB   TYR B 127     -13.888  20.446  58.518  1.00 77.40      B  C
ATOM   3294  CG   TYR B 127     -15.042  19.578  58.960  1.00 77.40      B  C
ATOM   3295  CD1  TYR B 127     -16.156  20.137  59.590  1.00 77.40      B  C
ATOM   3296  CE1  TYR B 127     -17.250  19.353  59.958  1.00 77.40      B  C
ATOM   3297  CD2  TYR B 127     -15.042  18.201  58.707  1.00 77.40      B  C
ATOM   3298  CE2  TYR B 127     -16.130  17.397  59.067  1.00 77.40      B  C
ATOM   3299  CZ   TYR B 127     -17.236  17.980  59.692  1.00 77.40      B  C
ATOM   3300  OH   TYR B 127     -18.333  17.207  60.049  1.00 77.40      B  O
ATOM   3301  C    TYR B 127     -12.071  22.033  58.971  1.00 48.62      B  C
ATOM   3302  O    TYR B 127     -12.370  23.144  58.541  1.00 48.62      B  O
ATOM   3303  N    LEU B 128     -10.847  21.525  58.884  1.00 51.66      B  N
ATOM   3304  CA   LEU B 128      -9.754  22.253  58.246  1.00 51.66      B  C
ATOM   3305  CB   LEU B 128      -8.422  21.924  58.922  1.00 42.01      B  C
ATOM   3306  CG   LEU B 128      -7.170  22.468  58.238  1.00 42.01      B  C
ATOM   3307  CD1  LEU B 128      -7.214  23.989  58.213  1.00 42.01      B  C
ATOM   3308  CD2  LEU B 128      -5.941  21.977  58.976  1.00 42.01      B  C
ATOM   3309  C    LEU B 128      -9.720  21.792  56.799  1.00 51.66      B  C
ATOM   3310  O    LEU B 128      -9.969  20.619  56.517  1.00 51.66      B  O
ATOM   3311  N    ASN B 129      -9.414  22.701  55.879  1.00 46.18      B  N
ATOM   3312  CA   ASN B 129      -9.380  22.341  54.466  1.00 46.18      B  C
ATOM   3313  CB   ASN B 129     -10.525  23.024  53.722  1.00 41.67      B  C
ATOM   3314  CG   ASN B 129     -11.884  22.573  54.212  1.00 41.67      B  C
ATOM   3315  OD1  ASN B 129     -12.487  21.660  53.649  1.00 41.67      B  O
ATOM   3316  ND2  ASN B 129     -12.370  23.201  55.282  1.00 41.67      B  N
ATOM   3317  C    ASN B 129      -8.063  22.725  53.835  1.00 46.18      B  C
ATOM   3318  O    ASN B 129      -7.715  23.902  53.753  1.00 46.18      B  O
ATOM   3319  N    LEU B 130      -7.328  21.771  53.392  1.00 34.33      B  N
ATOM   3320  CA   LEU B 130      -6.046  21.936  52.753  1.00 34.33      B  C
ATOM   3321  CB   LEU B 130      -5.055  20.860  53.204  1.00 40.79      B  C
ATOM   3322  CG   LEU B 130      -4.780  20.852  54.711  1.00 40.79      B  C
ATOM   3323  CD1  LEU B 130      -4.064  19.587  55.128  1.00 40.79      B  C
ATOM   3324  CD2  LEU B 130      -3.954  22.061  55.060  1.00 40.79      B  C
ATOM   3325  C    LEU B 130      -6.257  21.864  51.258  1.00 34.33      B  C
ATOM   3326  O    LEU B 130      -6.691  20.839  50.749  1.00 34.33      B  O
ATOM   3327  N    VAL B 131      -5.976  22.963  50.566  1.00 36.97      B  N
ATOM   3328  CA   VAL B 131      -6.128  23.018  49.114  1.00 36.97      B  C
ATOM   3329  CB   VAL B 131      -6.624  24.382  48.640  1.00 41.64      B  C
ATOM   3330  CG1  VAL B 131      -6.966  24.313  47.157  1.00 41.64      B  C
ATOM   3331  CG2  VAL B 131      -7.812  24.831  49.479  1.00 41.64      B  C
ATOM   3332  C    VAL B 131      -4.755  22.804  48.524  1.00 36.97      B  C
ATOM   3333  O    VAL B 131      -3.908  23.689  48.599  1.00 36.97      B  O
ATOM   3334  N    LEU B 132      -4.548  21.640  47.920  1.00 44.19      B  N
ATOM   3335  CA   LEU B 132      -3.255  21.279  47.354  1.00 44.19      B  C
ATOM   3336  CB   LEU B 132      -2.805  19.968  47.971  1.00 34.00      B  C
ATOM   3337  CG   LEU B 132      -3.000  19.992  49.480  1.00 34.00      B  C
ATOM   3338  CD1  LEU B 132      -3.293  18.606  49.998  1.00 34.00      B  C
ATOM   3339  CD2  LEU B 132      -1.765  20.595  50.123  1.00 34.00      B  C
ATOM   3340  C    LEU B 132      -3.253  21.128  45.847  1.00 44.19      B  C
ATOM   3341  O    LEU B 132      -4.286  20.843  45.241  1.00 44.19      B  O
ATOM   3342  N    ASP B 133      -2.082  21.317  45.246  1.00 41.24      B  N
ATOM   3343  CA   ASP B 133      -1.923  21.164  43.810  1.00 41.24      B  C
```

FIG. 3-51

```
ATOM   3344  CB   ASP B 133      -0.457  21.232  43.428  1.00 73.21      B   C
ATOM   3345  CG   ASP B 133       0.102  22.638  43.489  1.00 73.21      B   C
ATOM   3346  OD1  ASP B 133       1.351  22.773  43.503  1.00 73.21      B   O
ATOM   3347  OD2  ASP B 133      -0.699  23.607  43.504  1.00 73.21      B   O
ATOM   3348  C    ASP B 133      -2.423  19.777  43.488  1.00 41.24      B   C
ATOM   3349  O    ASP B 133      -2.282  18.864  44.296  1.00 41.24      B   O
ATOM   3350  N    TYR B 134      -3.012  19.608  42.313  1.00 48.00      B   N
ATOM   3351  CA   TYR B 134      -3.500  18.299  41.929  1.00 48.00      B   C
ATOM   3352  CB   TYR B 134      -4.805  18.404  41.158  1.00 57.10      B   C
ATOM   3353  CG   TYR B 134      -5.382  17.051  40.852  1.00 57.10      B   C
ATOM   3354  CD1  TYR B 134      -5.912  16.257  41.875  1.00 57.10      B   C
ATOM   3355  CE1  TYR B 134      -6.408  14.989  41.617  1.00 57.10      B   C
ATOM   3356  CD2  TYR B 134      -5.363  16.538  39.554  1.00 57.10      B   C
ATOM   3357  CE2  TYR B 134      -5.857  15.261  39.282  1.00 57.10      B   C
ATOM   3358  CZ   TYR B 134      -6.377  14.495  40.324  1.00 57.10      B   C
ATOM   3359  OH   TYR B 134      -6.849  13.226  40.092  1.00 57.10      B   O
ATOM   3360  C    TYR B 134      -2.473  17.653  41.034  1.00 48.00      B   C
ATOM   3361  O    TYR B 134      -1.890  18.313  40.183  1.00 48.00      B   O
ATOM   3362  N    VAL B 135      -2.231  16.370  41.248  1.00 34.92      B   N
ATOM   3363  CA   VAL B 135      -1.301  15.628  40.417  1.00 34.92      B   C
ATOM   3364  CB   VAL B 135       0.055  15.447  41.093  1.00 40.08      B   C
ATOM   3365  CG1  VAL B 135       1.069  14.994  40.075  1.00 40.08      B   C
ATOM   3366  CG2  VAL B 135       0.504  16.754  41.715  1.00 40.08      B   C
ATOM   3367  C    VAL B 135      -2.023  14.306  40.273  1.00 34.92      B   C
ATOM   3368  O    VAL B 135      -2.368  13.672  41.269  1.00 34.92      B   O
ATOM   3369  N    PRO B 136      -2.289  13.889  39.022  1.00 51.38      B   N
ATOM   3370  CD   PRO B 136      -1.933  14.643  37.804  1.00 40.54      B   C
ATOM   3371  CA   PRO B 136      -2.995  12.650  38.671  1.00 51.38      B   C
ATOM   3372  CB   PRO B 136      -3.364  12.886  37.212  1.00 40.54      B   C
ATOM   3373  CG   PRO B 136      -2.170  13.628  36.708  1.00 40.54      B   C
ATOM   3374  C    PRO B 136      -2.302  11.306  38.889  1.00 51.38      B   C
ATOM   3375  O    PRO B 136      -2.909  10.364  39.399  1.00 51.38      B   O
ATOM   3376  N    GLU B 137      -1.043  11.198  38.504  1.00 37.55      B   N
ATOM   3377  CA   GLU B 137      -0.363   9.932  38.678  1.00 37.55      B   C
ATOM   3378  CB   GLU B 137       0.634   9.705  37.550  1.00 57.24      B   C
ATOM   3379  CG   GLU B 137       0.045   9.081  36.321  1.00 57.24      B   C
ATOM   3380  CD   GLU B 137      -0.597   7.741  36.605  1.00 57.24      B   C
ATOM   3381  OE1  GLU B 137      -1.728   7.724  37.149  1.00 57.24      B   O
ATOM   3382  OE2  GLU B 137       0.032   6.701  36.289  1.00 57.24      B   O
ATOM   3383  C    GLU B 137       0.355   9.778  40.000  1.00 37.55      B   C
ATOM   3384  O    GLU B 137       0.635  10.755  40.694  1.00 37.55      B   O
ATOM   3385  N    THR B 138       0.636   8.529  40.346  1.00 39.79      B   N
ATOM   3386  CA   THR B 138       1.372   8.220  41.555  1.00 39.79      B   C
ATOM   3387  CB   THR B 138       0.469   7.752  42.700  1.00 43.81      B   C
ATOM   3388  OG1  THR B 138      -0.125   6.496  42.357  1.00 43.81      B   O
ATOM   3389  CG2  THR B 138      -0.610   8.784  42.977  1.00 43.81      B   C
ATOM   3390  C    THR B 138       2.280   7.087  41.157  1.00 39.79      B   C
ATOM   3391  O    THR B 138       1.966   6.324  40.240  1.00 39.79      B   O
ATOM   3392  N    VAL B 139       3.418   6.997  41.824  1.00 35.42      B   N
ATOM   3393  CA   VAL B 139       4.350   5.939  41.523  1.00 35.42      B   C
ATOM   3394  CB   VAL B 139       5.582   5.999  42.455  1.00 27.88      B   C
ATOM   3395  CG1  VAL B 139       6.442   4.751  42.275  1.00 27.88      B   C
ATOM   3396  CG2  VAL B 139       6.402   7.244  42.154  1.00 27.88      B   C
ATOM   3397  C    VAL B 139       3.625   4.610  41.701  1.00 35.42      B   C
ATOM   3398  O    VAL B 139       3.881   3.659  40.970  1.00 35.42      B   O
ATOM   3399  N    TYR B 140       2.700   4.553  42.654  1.00 25.47      B   N
ATOM   3400  CA   TYR B 140       1.963   3.317  42.899  1.00 25.47      B   C
ATOM   3401  CB   TYR B 140       0.924   3.485  44.009  1.00 38.11      B   C
ATOM   3402  CG   TYR B 140       0.154   2.211  44.249  1.00 38.11      B   C
ATOM   3403  CD1  TYR B 140       0.791   1.095  44.779  1.00 38.11      B   C
ATOM   3404  CE1  TYR B 140       0.136  -0.118  44.901  1.00 38.11      B   C
ATOM   3405  CD2  TYR B 140      -1.176   2.085  43.853  1.00 38.11      B   C
ATOM   3406  CE2  TYR B 140      -1.845   0.871  43.970  1.00 38.11      B   C
ATOM   3407  CZ   TYR B 140      -1.175  -0.230  44.494  1.00 38.11      B   C
ATOM   3408  OH   TYR B 140      -1.784  -1.457  44.594  1.00 38.11      B   O
ATOM   3409  C    TYR B 140       1.252   2.868  41.651  1.00 25.47      B   C
ATOM   3410  O    TYR B 140       1.380   1.730  41.225  1.00 25.47      B   O
```

FIG. 3-52

| | | | | | | | | | | |
|---|---|---|---|---|---|---|---|---|---|---|
| ATOM | 3411 | N | ARG | B | 141 | 0.483 | 3.780 | 41.081 | 1.00 40.11 | B N |
| ATOM | 3412 | CA | ARG | B | 141 | -0.259 | 3.504 | 39.868 | 1.00 40.11 | B C |
| ATOM | 3413 | CB | ARG | B | 141 | -1.073 | 4.734 | 39.473 | 1.00 66.47 | B C |
| ATOM | 3414 | CG | ARG | B | 141 | -2.390 | 4.850 | 40.222 | 1.00 66.47 | B C |
| ATOM | 3415 | CD | ARG | B | 141 | -2.912 | 6.274 | 40.250 | 1.00 66.47 | B C |
| ATOM | 3416 | NE | ARG | B | 141 | -4.353 | 6.244 | 40.428 | 1.00 66.47 | B N |
| ATOM | 3417 | CZ | ARG | B | 141 | -5.209 | 6.152 | 39.421 | 1.00 66.47 | B C |
| ATOM | 3418 | NH1 | ARG | B | 141 | -4.745 | 6.100 | 38.174 | 1.00 66.47 | B N |
| ATOM | 3419 | NH2 | ARG | B | 141 | -6.516 | 6.076 | 39.662 | 1.00 66.47 | B N |
| ATOM | 3420 | C | ARG | B | 141 | 0.671 | 3.105 | 38.736 | 1.00 40.11 | B C |
| ATOM | 3421 | O | ARG | B | 141 | 0.451 | 2.099 | 38.071 | 1.00 40.11 | B O |
| ATOM | 3422 | N | VAL | B | 142 | 1.710 | 3.897 | 38.516 | 1.00 52.29 | B N |
| ATOM | 3423 | CA | VAL | B | 142 | 2.662 | 3.598 | 37.456 | 1.00 52.29 | B C |
| ATOM | 3424 | CB | VAL | B | 142 | 3.744 | 4.698 | 37.338 | 1.00 40.91 | B C |
| ATOM | 3425 | CG1 | VAL | B | 142 | 4.890 | 4.214 | 36.487 | 1.00 40.91 | B C |
| ATOM | 3426 | CG2 | VAL | B | 142 | 3.148 | 5.948 | 36.728 | 1.00 40.91 | B C |
| ATOM | 3427 | C | VAL | B | 142 | 3.340 | 2.256 | 37.718 | 1.00 52.29 | B C |
| ATOM | 3428 | O | VAL | B | 142 | 3.470 | 1.437 | 36.816 | 1.00 52.29 | B O |
| ATOM | 3429 | N | ALA | B | 143 | 3.766 | 2.027 | 38.954 | 1.00 41.14 | B N |
| ATOM | 3430 | CA | ALA | B | 143 | 4.437 | 0.783 | 39.297 | 1.00 41.14 | B C |
| ATOM | 3431 | CB | ALA | B | 143 | 4.839 | 0.794 | 40.758 | 1.00 37.11 | B C |
| ATOM | 3432 | C | ALA | B | 143 | 3.527 | -0.398 | 39.025 | 1.00 41.14 | B C |
| ATOM | 3433 | O | ALA | B | 143 | 3.947 | -1.396 | 38.444 | 1.00 41.14 | B O |
| ATOM | 3434 | N | ARG | B | 144 | 2.276 | -0.268 | 39.455 | 1.00 54.22 | B N |
| ATOM | 3435 | CA | ARG | B | 144 | 1.273 | -1.315 | 39.291 | 1.00 54.22 | B C |
| ATOM | 3436 | CB | ARG | B | 144 | -0.058 | -0.843 | 39.895 | 1.00 63.44 | B C |
| ATOM | 3437 | CG | ARG | B | 144 | -1.024 | -1.954 | 40.287 | 1.00 63.44 | B C |
| ATOM | 3438 | CD | ARG | B | 144 | -2.383 | -1.808 | 39.601 | 1.00 63.44 | B C |
| ATOM | 3439 | NE | ARG | B | 144 | -3.199 | -0.686 | 40.078 | 1.00 63.44 | B N |
| ATOM | 3440 | CZ | ARG | B | 144 | -3.850 | -0.652 | 41.247 | 1.00 63.44 | B C |
| ATOM | 3441 | NH1 | ARG | B | 144 | -3.791 | -1.684 | 42.090 | 1.00 63.44 | B N |
| ATOM | 3442 | NH2 | ARG | B | 144 | -4.579 | 0.417 | 41.571 | 1.00 63.44 | B N |
| ATOM | 3443 | C | ARG | B | 144 | 1.096 | -1.619 | 37.805 | 1.00 54.22 | B C |
| ATOM | 3444 | O | ARG | B | 144 | 1.088 | -2.776 | 37.386 | 1.00 54.22 | B O |
| ATOM | 3445 | N | HIS | B | 145 | 0.978 | -0.560 | 37.012 | 1.00 54.25 | B N |
| ATOM | 3446 | CA | HIS | B | 145 | 0.774 | -0.675 | 35.574 | 1.00 54.25 | B C |
| ATOM | 3447 | CB | HIS | B | 145 | 0.657 | 0.730 | 34.970 | 1.00 72.56 | B C |
| ATOM | 3448 | CG | HIS | B | 145 | 0.136 | 0.753 | 33.565 | 1.00 72.56 | B C |
| ATOM | 3449 | CD2 | HIS | B | 145 | -0.040 | -0.242 | 32.661 | 1.00 72.56 | B C |
| ATOM | 3450 | ND1 | HIS | B | 145 | -0.183 | 1.927 | 32.911 | 1.00 72.56 | B N |
| ATOM | 3451 | CE1 | HIS | B | 145 | -0.524 | 1.654 | 31.663 | 1.00 72.56 | B C |
| ATOM | 3452 | NE2 | HIS | B | 145 | -0.443 | 0.345 | 31.485 | 1.00 72.56 | B N |
| ATOM | 3453 | C | HIS | B | 145 | 1.843 | -1.513 | 34.856 | 1.00 54.25 | B C |
| ATOM | 3454 | O | HIS | B | 145 | 1.499 | -2.351 | 34.018 | 1.00 54.25 | B O |
| ATOM | 3455 | N | TYR | B | 146 | 3.125 | -1.313 | 35.164 | 1.00 42.49 | B N |
| ATOM | 3456 | CA | TYR | B | 146 | 4.162 | -2.124 | 34.514 | 1.00 42.49 | B C |
| ATOM | 3457 | CB | TYR | B | 146 | 5.573 | -1.560 | 34.728 | 1.00 35.95 | B C |
| ATOM | 3458 | CG | TYR | B | 146 | 5.885 | -0.312 | 33.949 | 1.00 35.95 | B C |
| ATOM | 3459 | CD1 | TYR | B | 146 | 5.325 | 0.904 | 34.309 | 1.00 35.95 | B C |
| ATOM | 3460 | CE1 | TYR | B | 146 | 5.578 | 2.056 | 33.578 | 1.00 35.95 | B C |
| ATOM | 3461 | CD2 | TYR | B | 146 | 6.720 | -0.348 | 32.832 | 1.00 35.95 | B C |
| ATOM | 3462 | CE2 | TYR | B | 146 | 6.983 | 0.805 | 32.092 | 1.00 35.95 | B C |
| ATOM | 3463 | CZ | TYR | B | 146 | 6.402 | 2.002 | 32.473 | 1.00 35.95 | B C |
| ATOM | 3464 | OH | TYR | B | 146 | 6.598 | 3.146 | 31.738 | 1.00 35.95 | B O |
| ATOM | 3465 | C | TYR | B | 146 | 4.114 | -3.507 | 35.122 | 1.00 42.49 | B C |
| ATOM | 3466 | O | TYR | B | 146 | 4.336 | -4.504 | 34.449 | 1.00 42.49 | B O |
| ATOM | 3467 | N | SER | B | 147 | 3.804 | -3.558 | 36.407 | 1.00 61.05 | B N |
| ATOM | 3468 | CA | SER | B | 147 | 3.757 | -4.823 | 37.131 | 1.00 61.05 | B C |
| ATOM | 3469 | CB | SER | B | 147 | 3.610 | -4.554 | 38.629 | 1.00 54.68 | B C |
| ATOM | 3470 | OG | SER | B | 147 | 3.640 | -5.773 | 39.341 | 1.00 54.68 | B O |
| ATOM | 3471 | C | SER | B | 147 | 2.664 | -5.797 | 36.661 | 1.00 61.05 | B C |
| ATOM | 3472 | O | SER | B | 147 | 2.909 | -6.994 | 36.540 | 1.00 61.05 | B O |
| ATOM | 3473 | N | ARG | B | 148 | 1.464 | -5.291 | 36.400 | 1.00 60.49 | B N |
| ATOM | 3474 | CA | ARG | B | 148 | 0.382 | -6.151 | 35.942 | 1.00 60.49 | B C |
| ATOM | 3475 | CB | ARG | B | 148 | -0.941 | -5.395 | 35.914 | 1.00 70.48 | B C |
| ATOM | 3476 | CG | ARG | B | 148 | -1.691 | -5.365 | 37.219 | 1.00 70.48 | B C |
| ATOM | 3477 | CD | ARG | B | 148 | -2.921 | -4.507 | 37.036 | 1.00 70.48 | B C |

FIG. 3-53

```
ATOM   3478  NE   ARG B 148      -3.673   -4.323   38.275  1.00 70.48      B    N
ATOM   3479  CZ   ARG B 148      -4.552   -3.339   38.457  1.00 70.48      B    C
ATOM   3480  NH1  ARG B 148      -4.774   -2.461   37.476  1.00 70.48      B    N
ATOM   3481  NH2  ARG B 148      -5.196   -3.222   39.617  1.00 70.48      B    N
ATOM   3482  C    ARG B 148       0.657   -6.681   34.544  1.00 60.49      B    C
ATOM   3483  O    ARG B 148       0.191   -7.767   34.183  1.00 60.49      B    O
ATOM   3484  N    ALA B 149       1.394   -5.903   33.752  1.00 49.92      B    N
ATOM   3485  CA   ALA B 149       1.721   -6.305   32.385  1.00 49.92      B    C
ATOM   3486  CB   ALA B 149       1.873   -5.078   31.485  1.00 29.98      B    C
ATOM   3487  C    ALA B 149       3.003   -7.114   32.372  1.00 49.92      B    C
ATOM   3488  O    ALA B 149       3.685   -7.179   31.351  1.00 49.92      B    O
ATOM   3489  N    LYS B 150       3.330   -7.718   33.513  1.00 48.86      B    N
ATOM   3490  CA   LYS B 150       4.532   -8.530   33.626  1.00 48.86      B    C
ATOM   3491  CB   LYS B 150       4.281   -9.886   32.956  1.00 63.94      B    C
ATOM   3492  CG   LYS B 150       4.984  -11.069   33.616  1.00 63.94      B    C
ATOM   3493  CD   LYS B 150       4.243  -11.588   34.866  1.00 63.94      B    C
ATOM   3494  CE   LYS B 150       2.955  -12.342   34.494  1.00 63.94      B    C
ATOM   3495  NZ   LYS B 150       2.464  -13.237   35.593  1.00 63.94      B    N
ATOM   3496  C    LYS B 150       5.694   -7.800   32.934  1.00 48.86      B    C
ATOM   3497  O    LYS B 150       6.387   -8.376   32.110  1.00 48.86      B    O
ATOM   3498  N    GLN B 151       5.894   -6.530   33.283  1.00 61.48      B    N
ATOM   3499  CA   GLN B 151       6.937   -5.673   32.691  1.00 61.48      B    C
ATOM   3500  CB   GLN B 151       6.259   -4.702   31.718  1.00 56.71      B    C
ATOM   3501  CG   GLN B 151       7.183   -3.801   30.936  1.00 56.71      B    C
ATOM   3502  CD   GLN B 151       7.385   -4.290   29.520  1.00 56.71      B    C
ATOM   3503  OE1  GLN B 151       6.419   -4.487   28.777  1.00 56.71      B    O
ATOM   3504  NE2  GLN B 151       8.643   -4.487   29.132  1.00 56.71      B    N
ATOM   3505  C    GLN B 151       7.719   -4.877   33.769  1.00 61.48      B    C
ATOM   3506  O    GLN B 151       7.175   -4.543   34.834  1.00 61.48      B    O
ATOM   3507  N    THR B 152       8.982   -4.559   33.503  1.00 41.09      B    N
ATOM   3508  CA   THR B 152       9.770   -3.812   34.486  1.00 41.09      B    C
ATOM   3509  CB   THR B 152      11.203   -4.426.  34.662  1.00 50.96      B    C
ATOM   3510  OG1  THR B 152      12.196   -3.467   34.274  1.00 50.96      B    O
ATOM   3511  CG2  THR B 152      11.364   -5.683   33.809  1.00 50.96      B    C
ATOM   3512  C    THR B 152       9.899   -2.333   34.127  1.00 41.09      B    C
ATOM   3513  O    THR B 152      10.154   -1.988   32.978  1.00 41.09      B    O
ATOM   3514  N    LEU B 153       9.718   -1.457   35.105  1.00 34.47      B    N
ATOM   3515  CA   LEU B 153       9.836   -0.021   34.864  1.00 34.47      B    C
ATOM   3516  CB   LEU B 153       9.490    0.753   36.140  1.00 49.31      B    C
ATOM   3517  CG   LEU B 153       9.632    2.278   36.102  1.00 49.31      B    C
ATOM   3518  CD1  LEU B 153       8.424    2.870   35.405  1.00 49.31      B    C
ATOM   3519  CD2  LEU B 153       9.753    2.837   37.516  1.00 49.31      B    C
ATOM   3520  C    LEU B 153      11.258    0.341   34.430  1.00 34.47      B    C
ATOM   3521  O    LEU B 153      12.225   -0.043   35.072  1.00 34.47      B    O
ATOM   3522  N    PRO B 154      11.407    1.078   33.325  1.00 41.89      B    N
ATOM   3523  CD   PRO B 154      10.379    1.509   32.360  1.00 32.15      B    C
ATOM   3524  CA   PRO B 154      12.753    1.459   32.870  1.00 41.89      B    C
ATOM   3525  CB   PRO B 154      12.455    2.383   31.690  1.00 32.15      B    C
ATOM   3526  CG   PRO B 154      11.198    1.797   31.131  1.00 32.15      B    C
ATOM   3527  C    PRO B 154      13.583    2.156   33.980  1.00 41.89      B    C
ATOM   3528  O    PRO B 154      13.086    3.062   34.657  1.00 41.89      B    O
ATOM   3529  N    VAL B 155      14.841    1.747   34.155  1.00 47.18      B    N
ATOM   3530  CA   VAL B 155      15.690    2.341   35.186  1.00 47.18      B    C
ATOM   3531  CB   VAL B 155      17.062    1.620   35.321  1.00 27.43      B    C
ATOM   3532  CG1  VAL B 155      16.852    0.184   35.723  1.00 27.43      B    C
ATOM   3533  CG2  VAL B 155      17.838    1.706   34.031  1.00 27.43      B    C
ATOM   3534  C    VAL B 155      15.955    3.833   35.021  1.00 47.18      B    C
ATOM   3535  O    VAL B 155      16.602    4.437   35.875  1.00 47.18      B    O
ATOM   3536  N    ILE B 156      15.483    4.446   33.940  1.00 38.15      B    N
ATOM   3537  CA   ILE B 156      15.704    5.883   33.799  1.00 38.15      B    C
ATOM   3538  CB   ILE B 156      15.614    6.381   32.316  1.00 36.35      B    C
ATOM   3539  CG2  ILE B 156      14.254    6.101   31.731  1.00 36.35      B    C
ATOM   3540  CG1  ILE B 156      15.876    7.889   32.255  1.00 36.35      B    C
ATOM   3541  CD1  ILE B 156      17.263    8.282   32.692  1.00 36.35      B    C
ATOM   3542  C    ILE B 156      14.632    6.555   34.637  1.00 38.15      B    C
ATOM   3543  O    ILE B 156      14.842    7.630   35.182  1.00 38.15      B    O
ATOM   3544  N    TYR B 157      13.481    5.907   34.745  1.00 32.23      B    N
```

FIG. 3-54

```
ATOM   3545  CA   TYR B 157    12.402   6.454  35.546  1.00 32.23     B    C
ATOM   3546  CB   TYR B 157    11.072   5.818  35.144  1.00 48.60     B    C
ATOM   3547  CG   TYR B 157    10.528   6.357  33.845  1.00 48.60     B    C
ATOM   3548  CD1  TYR B 157    10.099   5.495  32.833  1.00 48.60     B    C
ATOM   3549  CE1  TYR B 157     9.605   5.991  31.622  1.00 48.60     B    C
ATOM   3550  CD2  TYR B 157    10.451   7.730  33.622  1.00 48.60     B    C
ATOM   3551  CE2  TYR B 157     9.964   8.240  32.424  1.00 48.60     B    C
ATOM   3552  CZ   TYR B 157     9.540   7.368  31.423  1.00 48.60     B    C
ATOM   3553  OH   TYR B 157     9.053   7.876  30.237  1.00 48.60     B    O
ATOM   3554  C    TYR B 157    12.701   6.181  37.009  1.00 32.23     B    C
ATOM   3555  O    TYR B 157    12.361   6.971  37.886  1.00 32.23     B    O
ATOM   3556  N    VAL B 158    13.355   5.053  37.253  1.00 36.65     B    N
ATOM   3557  CA   VAL B 158    13.724   4.656  38.594  1.00 36.65     B    C
ATOM   3558  CB   VAL B 158    14.334   3.237  38.620  1.00 33.40     B    C
ATOM   3559  CG1  VAL B 158    14.697   2.852  40.044  1.00 33.40     B    C
ATOM   3560  CG2  VAL B 158    13.340   2.237  38.065  1.00 33.40     B    C
ATOM   3561  C    VAL B 158    14.734   5.650  39.128  1.00 36.65     B    C
ATOM   3562  O    VAL B 158    14.684   6.019  40.302  1.00 36.65     B    O
ATOM   3563  N    LYS B 159    15.643   6.096  38.274  1.00 26.24     B    N
ATOM   3564  CA   LYS B 159    16.629   7.067  38.712  1.00 26.24     B    C
ATOM   3565  CB   LYS B 159    17.707   7.235  37.656  1.00 35.29     B    C
ATOM   3566  CG   LYS B 159    18.547   6.006  37.432  1.00 35.29     B    C
ATOM   3567  CD   LYS B 159    19.477   6.219  36.262  1.00 35.29     B    C
ATOM   3568  CE   LYS B 159    20.348   5.011  36.006  1.00 35.29     B    C
ATOM   3569  NZ   LYS B 159    21.421   5.364  35.036  1.00 35.29     B    N
ATOM   3570  C    LYS B 159    15.962   8.414  38.984  1.00 26.24     B    C
ATOM   3571  O    LYS B 159    16.194   9.052  40.010  1.00 26.24     B    O
ATOM   3572  N    LEU B 160    15.120   8.837  38.053  1.00 35.96     B    N
ATOM   3573  CA   LEU B 160    14.411  10.099  38.168  1.00 35.96     B    C
ATOM   3574  CB   LEU B 160    13.547  10.328  36.934  1.00 36.98     B    C
ATOM   3575  CG   LEU B 160    14.327  10.878  35.755  1.00 36.98     B    C
ATOM   3576  CD1  LEU B 160    13.487  10.780  34.500  1.00 36.98     B    C
ATOM   3577  CD2  LEU B 160    14.740  12.317  36.062  1.00 36.98     B    C
ATOM   3578  C    LEU B 160    13.538  10.217  39.396  1.00 35.96     B    C
ATOM   3579  O    LEU B 160    13.583  11.221  40.090  1.00 35.96     B    O
ATOM   3580  N    TYR B 161    12.730   9.202  39.659  1.00 33.69     B    N
ATOM   3581  CA   TYR B 161    11.846   9.258  40.805  1.00 33.69     B    C
ATOM   3582  CB   TYR B 161    10.839   8.116  40.756  1.00 54.12     B    C
ATOM   3583  CG   TYR B 161    10.008   8.129  39.500  1.00 54.12     B    C
ATOM   3584  CD1  TYR B 161     9.920   9.279  38.719  1.00 54.12     B    C
ATOM   3585  CE1  TYR B 161     9.168   9.304  37.570  1.00 54.12     B    C
ATOM   3586  CD2  TYR B 161     9.312   6.998  39.090  1.00 54.12     B    C
ATOM   3587  CE2  TYR B 161     8.554   7.012  37.940  1.00 54.12     B    C
ATOM   3588  CZ   TYR B 161     8.485   8.168  37.187  1.00 54.12     B    C
ATOM   3589  OH   TYR B 161     7.703   8.206  36.057  1.00 54.12     B    O
ATOM   3590  C    TYR B 161    12.584   9.230  42.119  1.00 33.69     B    C
ATOM   3591  O    TYR B 161    12.407  10.119  42.957  1.00 33.69     B    O
ATOM   3592  N    MET B 162    13.411   8.208  42.301  1.00 44.12     B    N
ATOM   3593  CA   MET B 162    14.176   8.084  43.530  1.00 44.12     B    C
ATOM   3594  CB   MET B 162    15.092   6.871  43.464  1.00 36.83     B    C
ATOM   3595  CG   MET B 162    14.337   5.557  43.417  1.00 36.83     B    C
ATOM   3596  SD   MET B 162    13.078   5.433  44.697  1.00 36.83     B    S
ATOM   3597  CE   MET B 162    14.046   5.662  46.165  1.00 36.83     B    C
ATOM   3598  C    MET B 162    14.984   9.344  43.795  1.00 44.12     B    C
ATOM   3599  O    MET B 162    14.980   9.851  44.909  1.00 44.12     B    O
ATOM   3600  N    TYR B 163    15.662   9.859  42.773  1.00 31.39     B    N
ATOM   3601  CA   TYR B 163    16.444  11.070  42.941  1.00 31.39     B    C
ATOM   3602  CB   TYR B 163    17.048  11.512  41.625  1.00 40.37     B    C
ATOM   3603  CG   TYR B 163    17.880  12.764  41.776  1.00 40.37     B    C
ATOM   3604  CD1  TYR B 163    19.210  12.696  42.189  1.00 40.37     B    C
ATOM   3605  CE1  TYR B 163    19.978  13.839  42.325  1.00 40.37     B    C
ATOM   3606  CD2  TYR B 163    17.338  14.018  41.512  1.00 40.37     B    C
ATOM   3607  CE2  TYR B 163    18.101  15.175  41.648  1.00 40.37     B    C
ATOM   3608  CZ   TYR B 163    19.417  15.075  42.049  1.00 40.37     B    C
ATOM   3609  OH   TYR B 163    20.180  16.215  42.136  1.00 40.37     B    O
ATOM   3610  C    TYR B 163    15.616  12.224  43.484  1.00 31.39     B    C
ATOM   3611  O    TYR B 163    16.035  12.921  44.405  1.00 31.39     B    O
```

FIG. 3-55

```
ATOM   3612  N    GLN B 164      14.446  12.442  42.896  1.00 38.31      B    N
ATOM   3613  CA   GLN B 164      13.576  13.517  43.342  1.00 38.31      B    C
ATOM   3614  CB   GLN B 164      12.444  13.721  42.343  1.00 42.66      B    C
ATOM   3615  CG   GLN B 164      12.924  14.114  40.959  1.00 42.66      B    C
ATOM   3616  CD   GLN B 164      11.773  14.395  40.007  1.00 42.66      B    C
ATOM   3617  OE1  GLN B 164      11.193  15.490  40.008  1.00 42.66      B    O
ATOM   3618  NE2  GLN B 164      11.423  13.397  39.198  1.00 42.66      B    N
ATOM   3619  C    GLN B 164      13.022  13.228  44.740  1.00 38.31      B    C
ATOM   3620  O    GLN B 164      12.877  14.136  45.554  1.00 38.31      B    O
ATOM   3621  N    LEU B 165      12.713  11.967  45.025  1.00 36.88      B    N
ATOM   3622  CA   LEU B 165      12.206  11.617  46.343  1.00 36.88      B    C
ATOM   3623  CB   LEU B 165      11.825  10.137  46.414  1.00 30.94      B    C
ATOM   3624  CG   LEU B 165      11.815   9.527  47.821  1.00 30.94      B    C
ATOM   3625  CD1  LEU B 165      10.897  10.305  48.731  1.00 30.94      B    C
ATOM   3626  CD2  LEU B 165      11.385   8.087  47.746  1.00 30.94      B    C
ATOM   3627  C    LEU B 165      13.295  11.906  47.353  1.00 36.88      B    C
ATOM   3628  O    LEU B 165      13.034  12.463  48.415  1.00 36.88      B    O
ATOM   3629  N    PHE B 166      14.523  11.517  47.024  1.00 47.92      B    N
ATOM   3630  CA   PHE B 166      15.641  11.750  47.924  1.00 47.92      B    C
ATOM   3631  CB   PHE B 166      16.914  11.079  47.413  1.00 24.84      B    C
ATOM   3632  CG   PHE B 166      17.056   9.654  47.863  1.00 24.84      B    C
ATOM   3633  CD1  PHE B 166      16.909   9.323  49.213  1.00 24.84      B    C
ATOM   3634  CD2  PHE B 166      17.309   8.641  46.951  1.00 24.84      B    C
ATOM   3635  CE1  PHE B 166      17.007   8.002  49.645  1.00 24.84      B    C
ATOM   3636  CE2  PHE B 166      17.409   7.325  47.373  1.00 24.84      B    C
ATOM   3637  CZ   PHE B 166      17.255   7.005  48.727  1.00 24.84      B    C
ATOM   3638  C    PHE B 166      15.880  13.228  48.108  1.00 47.92      B    C
ATOM   3639  O    PHE B 166      16.198  13.681  49.209  1.00 47.92      B    O
ATOM   3640  N    ARG B 167      15.710  13.995  47.040  1.00 39.10      B    N
ATOM   3641  CA   ARG B 167      15.926  15.417  47.166  1.00 39.10      B    C
ATOM   3642  CB   ARG B 167      15.878  16.097  45.794  1.00 31.17      B    C
ATOM   3643  CG   ARG B 167      16.402  17.513  45.863  1.00 31.17      B    C
ATOM   3644  CD   ARG B 167      16.415  18.220  44.554  1.00 31.17      B    C
ATOM   3645  NE   ARG B 167      16.580  19.648  44.782  1.00 31.17      B    N
ATOM   3646  CZ   ARG B 167      16.482  20.575  43.837  1.00 31.17      B    C
ATOM   3647  NH1  ARG B 167      16.219  20.232  42.582  1.00 31.17      B    N
ATOM   3648  NH2  ARG B 167      16.636  21.849  44.151  1.00 31.17      B    N
ATOM   3649  C    ARG B 167      14.901  16.042  48.118  1.00 39.10      B    C
ATOM   3650  O    ARG B 167      15.247  16.885  48.944  1.00 39.10      B    O
ATOM   3651  N    SER B 168      13.649  15.609  48.019  1.00 33.04      B    N
ATOM   3652  CA   SER B 168      12.589  16.146  48.864  1.00 33.04      B    C
ATOM   3653  CB   SER B 168      11.226  15.606  48.421  1.00 36.87      B    C
ATOM   3654  OG   SER B 168      11.014  14.289  48.895  1.00 36.87      B    O
ATOM   3655  C    SER B 168      12.808  15.805  50.333  1.00 33.04      B    C
ATOM   3656  O    SER B 168      12.531  16.612  51.221  1.00 33.04      B    O
ATOM   3657  N    LEU B 169      13.287  14.594  50.584  1.00 44.38      B    N
ATOM   3658  CA   LEU B 169      13.537  14.154  51.945  1.00 44.38      B    C
ATOM   3659  CB   LEU B 169      13.934  12.683  51.950  1.00 29.63      B    C
ATOM   3660  CG   LEU B 169      12.926  11.705  52.548  1.00 29.63      B    C
ATOM   3661  CD1  LEU B 169      11.517  12.107  52.204  1.00 29.63      B    C
ATOM   3662  CD2  LEU B 169      13.228  10.317  52.038  1.00 29.63      B    C
ATOM   3663  C    LEU B 169      14.653  15.017  52.508  1.00 44.38      B    C
ATOM   3664  O    LEU B 169      14.570  15.511  53.638  1.00 44.38      B    O
ATOM   3665  N    ALA B 170      15.689  15.216  51.703  1.00 38.87      B    N
ATOM   3666  CA   ALA B 170      16.814  16.031  52.114  1.00 38.87      B    C
ATOM   3667  CB   ALA B 170      17.771  16.200  50.961  1.00 26.62      B    C
ATOM   3668  C    ALA B 170      16.277  17.382  52.559  1.00 38.87      B    C
ATOM   3669  O    ALA B 170      16.752  17.976  53.522  1.00 38.87      B    O
ATOM   3670  N    TYR B 171      15.264  17.860  51.855  1.00 46.13      B    N
ATOM   3671  CA   TYR B 171      14.665  19.143  52.173  1.00 46.13      B    C
ATOM   3672  CB   TYR B 171      13.667  19.523  51.093  1.00 43.64      B    C
ATOM   3673  CG   TYR B 171      12.989  20.827  51.378  1.00 43.64      B    C
ATOM   3674  CD1  TYR B 171      13.719  22.012  51.415  1.00 43.64      B    C
ATOM   3675  CE1  TYR B 171      13.106  23.219  51.691  1.00 43.64      B    C
ATOM   3676  CD2  TYR B 171      11.622  20.882  51.629  1.00 43.64      B    C
ATOM   3677  CE2  TYR B 171      10.998  22.090  51.910  1.00 43.64      B    C
ATOM   3678  CZ   TYR B 171      11.749  23.253  51.937  1.00 43.64      B    C
```

FIG. 3-56

| | | | | | | | | | | | |
|---|---|---|---|---|---|---|---|---|---|---|---|
| ATOM | 3679 | OH | TYR | B | 171 | 11.151 | 24.455 | 52.207 | 1.00 | 43.64 | B | O |
| ATOM | 3680 | C | TYR | B | 171 | 13.966 | 19.181 | 53.529 | 1.00 | 46.13 | B | C |
| ATOM | 3681 | O | TYR | B | 171 | 14.407 | 19.874 | 54.445 | 1.00 | 46.13 | B | O |
| ATOM | 3682 | N | ILE | B | 172 | 12.867 | 18.445 | 53.654 | 1.00 | 45.00 | B | N |
| ATOM | 3683 | CA | ILE | B | 172 | 12.125 | 18.443 | 54.902 | 1.00 | 45.00 | B | C |
| ATOM | 3684 | CB | ILE | B | 172 | 10.881 | 17.533 | 54.835 | 1.00 | 31.79 | B | C |
| ATOM | 3685 | CG2 | ILE | B | 172 | 9.927 | 18.055 | 53.796 | 1.00 | 31.79 | B | C |
| ATOM | 3686 | CG1 | ILE | B | 172 | 11.295 | 16.092 | 54.545 | 1.00 | 31.79 | B | C |
| ATOM | 3687 | CD1 | ILE | B | 172 | 10.148 | 15.113 | 54.593 | 1.00 | 31.79 | B | C |
| ATOM | 3688 | C | ILE | B | 172 | 12.999 | 18.003 | 56.069 | 1.00 | 45.00 | B | C |
| ATOM | 3689 | O | ILE | B | 172 | 12.797 | 18.437 | 57.208 | 1.00 | 45.00 | B | O |
| ATOM | 3690 | N | HIS | B | 173 | 13.976 | 17.148 | 55.794 | 1.00 | 49.21 | B | N |
| ATOM | 3691 | CA | HIS | B | 173 | 14.837 | 16.694 | 56.868 | 1.00 | 49.21 | B | C |
| ATOM | 3692 | CB | HIS | B | 173 | 15.699 | 15.518 | 56.418 | 1.00 | 29.72 | B | C |
| ATOM | 3693 | CG | HIS | B | 173 | 14.954 | 14.222 | 56.384 | 1.00 | 29.72 | B | C |
| ATOM | 3694 | CD2 | HIS | B | 173 | 13.642 | 13.945 | 56.582 | 1.00 | 29.72 | B | C |
| ATOM | 3695 | ND1 | HIS | B | 173 | 15.568 | 13.014 | 56.145 | 1.00 | 29.72 | B | N |
| ATOM | 3696 | CE1 | HIS | B | 173 | 14.668 | 12.049 | 56.202 | 1.00 | 29.72 | B | C |
| ATOM | 3697 | NE2 | HIS | B | 173 | 13.492 | 12.587 | 56.466 | 1.00 | 29.72 | B | N |
| ATOM | 3698 | C | HIS | B | 173 | 15.705 | 17.794 | 57.445 | 1.00 | 49.21 | B | C |
| ATOM | 3699 | O | HIS | B | 173 | 16.105 | 17.707 | 58.606 | 1.00 | 49.21 | B | O |
| ATOM | 3700 | N | SER | B | 174 | 15.977 | 18.839 | 56.662 | 1.00 | 49.11 | B | N |
| ATOM | 3701 | CA | SER | B | 174 | 16.803 | 19.937 | 57.160 | 1.00 | 49.11 | B | C |
| ATOM | 3702 | CB | SER | B | 174 | 17.337 | 20.791 | 56.006 | 1.00 | 45.05 | B | C |
| ATOM | 3703 | OG | SER | B | 174 | 16.293 | 21.454 | 55.329 | 1.00 | 45.05 | B | O |
| ATOM | 3704 | C | SER | B | 174 | 16.081 | 20.828 | 58.176 | 1.00 | 49.11 | B | C |
| ATOM | 3705 | O | SER | B | 174 | 16.712 | 21.660 | 58.821 | 1.00 | 49.11 | B | O |
| ATOM | 3706 | N | PHE | B | 175 | 14.767 | 20.671 | 58.309 | 1.00 | 39.55 | B | N |
| ATOM | 3707 | CA | PHE | B | 175 | 14.016 | 21.446 | 59.289 | 1.00 | 39.55 | B | C |
| ATOM | 3708 | CB | PHE | B | 175 | 12.714 | 21.987 | 58.712 | 1.00 | 84.91 | B | C |
| ATOM | 3709 | CG | PHE | B | 175 | 12.897 | 22.928 | 57.566 | 1.00 | 84.91 | B | C |
| ATOM | 3710 | CD1 | PHE | B | 175 | 13.028 | 22.442 | 56.264 | 1.00 | 84.91 | B | C |
| ATOM | 3711 | CD2 | PHE | B | 175 | 12.938 | 24.305 | 57.783 | 1.00 | 84.91 | B | C |
| ATOM | 3712 | CE1 | PHE | B | 175 | 13.198 | 23.319 | 55.181 | 1.00 | 84.91 | B | C |
| ATOM | 3713 | CE2 | PHE | B | 175 | 13.107 | 25.194 | 56.713 | 1.00 | 84.91 | B | C |
| ATOM | 3714 | CZ | PHE | B | 175 | 13.237 | 24.700 | 55.404 | 1.00 | 84.91 | B | C |
| ATOM | 3715 | C | PHE | B | 175 | 13.664 | 20.500 | 60.419 | 1.00 | 39.55 | B | C |
| ATOM | 3716 | O | PHE | B | 175 | 12.823 | 20.815 | 61.271 | 1.00 | 39.55 | B | O |
| ATOM | 3717 | N | GLY | B | 176 | 14.298 | 19.328 | 60.409 | 1.00 | 51.81 | B | N |
| ATOM | 3718 | CA | GLY | B | 176 | 14.039 | 18.333 | 61.433 | 1.00 | 51.81 | B | C |
| ATOM | 3719 | C | GLY | B | 176 | 12.661 | 17.720 | 61.292 | 1.00 | 51.81 | B | C |
| ATOM | 3720 | O | GLY | B | 176 | 12.076 | 17.246 | 62.267 | 1.00 | 51.81 | B | O |
| ATOM | 3721 | N | ILE | B | 177 | 12.135 | 17.726 | 60.074 | 1.00 | 47.81 | B | N |
| ATOM | 3722 | CA | ILE | B | 177 | 10.824 | 17.156 | 59.813 | 1.00 | 47.81 | B | C |
| ATOM | 3723 | CB | ILE | B | 177 | 10.017 | 18.076 | 58.910 | 1.00 | 56.88 | B | C |
| ATOM | 3724 | CG2 | ILE | B | 177 | 8.729 | 17.386 | 58.490 | 1.00 | 56.88 | B | C |
| ATOM | 3725 | CG1 | ILE | B | 177 | 9.743 | 19.386 | 59.644 | 1.00 | 56.88 | B | C |
| ATOM | 3726 | CD1 | ILE | B | 177 | 9.290 | 20.516 | 58.727 | 1.00 | 56.88 | B | C |
| ATOM | 3727 | C | ILE | B | 177 | 10.959 | 15.791 | 59.146 | 1.00 | 47.81 | B | C |
| ATOM | 3728 | O | ILE | B | 177 | 11.678 | 15.645 | 58.156 | 1.00 | 47.81 | B | O |
| ATOM | 3729 | N | CYS | B | 178 | 10.259 | 14.802 | 59.695 | 1.00 | 29.70 | B | N |
| ATOM | 3730 | CA | CYS | B | 178 | 10.293 | 13.437 | 59.179 | 1.00 | 29.70 | B | C |
| ATOM | 3731 | CB | CYS | B | 178 | 10.711 | 12.483 | 60.298 | 1.00 | 46.01 | B | C |
| ATOM | 3732 | SG | CYS | B | 178 | 10.808 | 10.740 | 59.852 | 1.00 | 46.01 | B | S |
| ATOM | 3733 | C | CYS | B | 178 | 8.931 | 13.034 | 58.633 | 1.00 | 29.70 | B | C |
| ATOM | 3734 | O | CYS | B | 178 | 7.935 | 13.055 | 59.346 | 1.00 | 29.70 | B | O |
| ATOM | 3735 | N | HIS | B | 179 | 8.893 | 12.654 | 57.364 | 1.00 | 32.68 | B | N |
| ATOM | 3736 | CA | HIS | B | 179 | 7.647 | 12.265 | 56.731 | 1.00 | 32.68 | B | C |
| ATOM | 3737 | CB | HIS | B | 179 | 7.913 | 11.929 | 55.266 | 1.00 | 35.24 | B | C |
| ATOM | 3738 | CG | HIS | B | 179 | 6.668 | 11.781 | 54.455 | 1.00 | 35.24 | B | C |
| ATOM | 3739 | CD2 | HIS | B | 179 | 5.937 | 12.697 | 53.779 | 1.00 | 35.24 | B | C |
| ATOM | 3740 | ND1 | HIS | B | 179 | 5.970 | 10.597 | 54.378 | 1.00 | 35.24 | B | N |
| ATOM | 3741 | CE1 | HIS | B | 179 | 4.856 | 10.794 | 53.696 | 1.00 | 35.24 | B | C |
| ATOM | 3742 | NE2 | HIS | B | 179 | 4.813 | 12.059 | 53.324 | 1.00 | 35.24 | B | N |
| ATOM | 3743 | C | HIS | B | 179 | 6.936 | 11.101 | 57.436 | 1.00 | 32.68 | B | C |
| ATOM | 3744 | O | HIS | B | 179 | 5.723 | 11.131 | 57.622 | 1.00 | 32.68 | B | O |
| ATOM | 3745 | N | ARG | B | 180 | 7.697 | 10.080 | 57.817 | 1.00 | 29.37 | B | N |

FIG. 3-57

| | | | | | | | | | | | |
|---|---|---|---|---|---|---|---|---|---|---|---|
| ATOM | 3746 | CA  | ARG | B | 180 |  7.165 |  8.917 | 58.523 | 1.00 | 29.37 | B | C |
| ATOM | 3747 | CB  | ARG | B | 180 |  6.643 |  9.336 | 59.899 | 1.00 | 35.88 | B | C |
| ATOM | 3748 | CG  | ARG | B | 180 |  7.675 |  9.967 | 60.792 | 1.00 | 35.88 | B | C |
| ATOM | 3749 | CD  | ARG | B | 180 |  6.982 | 10.797 | 61.843 | 1.00 | 35.88 | B | C |
| ATOM | 3750 | NE  | ARG | B | 180 |  6.321 |  9.990 | 62.861 | 1.00 | 35.88 | B | N |
| ATOM | 3751 | CZ  | ARG | B | 180 |  5.417 | 10.461 | 63.715 | 1.00 | 35.88 | B | C |
| ATOM | 3752 | NH1 | ARG | B | 180 |  5.049 | 11.730 | 63.680 | 1.00 | 35.88 | B | N |
| ATOM | 3753 | NH2 | ARG | B | 180 |  4.896 |  9.661 | 64.626 | 1.00 | 35.88 | B | N |
| ATOM | 3754 | C   | ARG | B | 180 |  6.077 |  8.133 | 57.794 | 1.00 | 29.37 | B | C |
| ATOM | 3755 | O   | ARG | B | 180 |  5.392 |  7.310 | 58.400 | 1.00 | 29.37 | B | O |
| ATOM | 3756 | N   | ASP | B | 181 |  5.904 |  8.394 | 56.505 | 1.00 | 35.63 | B | N |
| ATOM | 3757 | CA  | ASP | B | 181 |  4.920 |  7.662 | 55.721 | 1.00 | 35.63 | B | C |
| ATOM | 3758 | CB  | ASP | B | 181 |  3.535 |  8.265 | 55.898 | 1.00 | 42.67 | B | C |
| ATOM | 3759 | CG  | ASP | B | 181 |  2.451 |  7.392 | 55.324 | 1.00 | 42.67 | B | C |
| ATOM | 3760 | OD1 | ASP | B | 181 |  2.717 |  6.191 | 55.116 | 1.00 | 42.67 | B | O |
| ATOM | 3761 | OD2 | ASP | B | 181 |  1.330 |  7.896 | 55.095 | 1.00 | 42.67 | B | O |
| ATOM | 3762 | C   | ASP | B | 181 |  5.281 |  7.598 | 54.240 | 1.00 | 35.63 | B | C |
| ATOM | 3763 | O   | ASP | B | 181 |  4.414 |  7.693 | 53.379 | 1.00 | 35.63 | B | O |
| ATOM | 3764 | N   | ILE | B | 182 |  6.568 |  7.430 | 53.949 | 1.00 | 37.05 | B | N |
| ATOM | 3765 | CA  | ILE | B | 182 |  7.032 |  7.331 | 52.573 | 1.00 | 37.05 | B | C |
| ATOM | 3766 | CB  | ILE | B | 182 |  8.578 |  7.375 | 52.483 | 1.00 | 30.77 | B | C |
| ATOM | 3767 | CG2 | ILE | B | 182 |  9.027 |  7.275 | 51.035 | 1.00 | 30.77 | B | C |
| ATOM | 3768 | CG1 | ILE | B | 182 |  9.102 |  8.664 | 53.110 | 1.00 | 30.77 | B | C |
| ATOM | 3769 | CD1 | ILE | B | 182 |  8.641 |  9.929 | 52.418 | 1.00 | 30.77 | B | C |
| ATOM | 3770 | C   | ILE | B | 182 |  6.566 |  6.012 | 51.978 | 1.00 | 37.05 | B | C |
| ATOM | 3771 | O   | ILE | B | 182 |  6.848 |  4.936 | 52.516 | 1.00 | 37.05 | B | O |
| ATOM | 3772 | N   | LYS | B | 183 |  5.833 |  6.109 | 50.873 | 1.00 | 31.82 | B | N |
| ATOM | 3773 | CA  | LYS | B | 183 |  5.341 |  4.940 | 50.148 | 1.00 | 31.82 | B | C |
| ATOM | 3774 | CB  | LYS | B | 183 |  4.137 |  4.317 | 50.859 | 1.00 | 40.48 | B | C |
| ATOM | 3775 | CG  | LYS | B | 183 |  2.936 |  5.221 | 51.019 | 1.00 | 40.48 | B | C |
| ATOM | 3776 | CD  | LYS | B | 183 |  1.824 |  4.485 | 51.736 | 1.00 | 40.48 | B | C |
| ATOM | 3777 | CE  | LYS | B | 183 |  0.666 |  5.398 | 52.066 | 1.00 | 40.48 | B | C |
| ATOM | 3778 | NZ  | LYS | B | 183 | -0.298 |  4.740 | 52.994 | 1.00 | 40.48 | B | N |
| ATOM | 3779 | C   | LYS | B | 183 |  4.972 |  5.358 | 48.730 | 1.00 | 31.82 | B | C |
| ATOM | 3780 | O   | LYS | B | 183 |  4.723 |  6.526 | 48.467 | 1.00 | 31.82 | B | O |
| ATOM | 3781 | N   | PRO | B | 184 |  4.956 |  4.405 | 47.788 | 1.00 | 43.83 | B | N |
| ATOM | 3782 | CD  | PRO | B | 184 |  5.294 |  2.978 | 47.938 | 1.00 | 42.42 | B | C |
| ATOM | 3783 | CA  | PRO | B | 184 |  4.617 |  4.711 | 46.397 | 1.00 | 43.83 | B | C |
| ATOM | 3784 | CB  | PRO | B | 184 |  4.530 |  3.329 | 45.760 | 1.00 | 42.42 | B | C |
| ATOM | 3785 | CG  | PRO | B | 184 |  5.570 |  2.568 | 46.505 | 1.00 | 42.42 | B | C |
| ATOM | 3786 | C   | PRO | B | 184 |  3.321 |  5.504 | 46.244 | 1.00 | 43.83 | B | C |
| ATOM | 3787 | O   | PRO | B | 184 |  3.226 |  6.374 | 45.384 | 1.00 | 43.83 | B | O |
| ATOM | 3788 | N   | GLN | B | 185 |  2.333 |  5.203 | 47.084 | 1.00 | 35.05 | B | N |
| ATOM | 3789 | CA  | GLN | B | 185 |  1.037 |  5.865 | 47.038 | 1.00 | 35.05 | B | C |
| ATOM | 3790 | CB  | GLN | B | 185 |  0.055 |  5.176 | 47.988 | 1.00 | 50.01 | B | C |
| ATOM | 3791 | CG  | GLN | B | 185 | -0.285 |  3.736 | 47.617 | 1.00 | 50.01 | B | C |
| ATOM | 3792 | CD  | GLN | B | 185 |  0.825 |  2.738 | 47.950 | 1.00 | 50.01 | B | C |
| ATOM | 3793 | OE1 | GLN | B | 185 |  1.966 |  3.113 | 48.240 | 1.00 | 50.01 | B | O |
| ATOM | 3794 | NE2 | GLN | B | 185 |  0.489 |  1.454 | 47.898 | 1.00 | 50.01 | B | N |
| ATOM | 3795 | C   | GLN | B | 185 |  1.093 |  7.348 | 47.370 | 1.00 | 35.05 | B | C |
| ATOM | 3796 | O   | GLN | B | 185 |  0.149 |  8.080 | 47.081 | 1.00 | 35.05 | B | O |
| ATOM | 3797 | N   | ASN | B | 186 |  2.190 |  7.794 | 47.978 | 1.00 | 32.50 | B | N |
| ATOM | 3798 | CA  | ASN | B | 186 |  2.335 |  9.200 | 48.349 | 1.00 | 32.50 | B | C |
| ATOM | 3799 | CB  | ASN | B | 186 |  2.721 |  9.356 | 49.828 | 1.00 | 38.79 | B | C |
| ATOM | 3800 | CG  | ASN | B | 186 |  1.567 |  9.089 | 50.772 | 1.00 | 38.79 | B | C |
| ATOM | 3801 | OD1 | ASN | B | 186 |  0.468 |  9.598 | 50.577 | 1.00 | 38.79 | B | O |
| ATOM | 3802 | ND2 | ASN | B | 186 |  1.816 |  8.301 | 51.810 | 1.00 | 38.79 | B | N |
| ATOM | 3803 | C   | ASN | B | 186 |  3.360 |  9.929 | 47.503 | 1.00 | 32.50 | B | C |
| ATOM | 3804 | O   | ASN | B | 186 |  3.784 | 11.023 | 47.846 | 1.00 | 32.50 | B | O |
| ATOM | 3805 | N   | LEU | B | 187 |  3.770 |  9.327 | 46.401 | 1.00 | 25.65 | B | N |
| ATOM | 3806 | CA  | LEU | B | 187 |  4.726 |  9.972 | 45.524 | 1.00 | 25.65 | B | C |
| ATOM | 3807 | CB  | LEU | B | 187 |  5.890 |  9.031 | 45.210 | 1.00 | 40.50 | B | C |
| ATOM | 3808 | CG  | LEU | B | 187 |  6.756 |  8.477 | 46.356 | 1.00 | 40.50 | B | C |
| ATOM | 3809 | CD1 | LEU | B | 187 |  7.730 |  7.458 | 45.793 | 1.00 | 40.50 | B | C |
| ATOM | 3810 | CD2 | LEU | B | 187 |  7.506 |  9.607 | 47.061 | 1.00 | 40.50 | B | C |
| ATOM | 3811 | C   | LEU | B | 187 |  3.972 | 10.319 | 44.255 | 1.00 | 25.65 | B | C |
| ATOM | 3812 | O   | LEU | B | 187 |  3.811 |  9.491 | 43.373 | 1.00 | 25.65 | B | O |

FIG. 3-58

```
ATOM   3813  N    LEU B 188       3.477  11.544  44.178  1.00 41.74           B  N
ATOM   3814  CA   LEU B 188       2.739  11.988  43.006  1.00 41.74           B  C
ATOM   3815  CB   LEU B 188       1.935  13.239  43.326  1.00 40.28           B  C
ATOM   3816  CG   LEU B 188       1.060  13.214  44.567  1.00 40.28           B  C
ATOM   3817  CD1  LEU B 188       0.305  14.521  44.598  1.00 40.28           B  C
ATOM   3818  CD2  LEU B 188       0.105  12.030  44.550  1.00 40.28           B  C
ATOM   3819  C    LEU B 188       3.733  12.322  41.912  1.00 41.74           B  C
ATOM   3820  O    LEU B 188       4.906  12.569  42.189  1.00 41.74           B  O
ATOM   3821  N    LEU B 189       3.271  12.338  40.667  1.00 46.18           B  N
ATOM   3822  CA   LEU B 189       4.160  12.661  39.560  1.00 46.18           B  C
ATOM   3823  CB   LEU B 189       5.181  11.536  39.321  1.00 43.25           B  C
ATOM   3824  CG   LEU B 189       4.653  10.194  38.811  1.00 43.25           B  C
ATOM   3825  CD1  LEU B 189       5.793   9.222  38.613  1.00 43.25           B  C
ATOM   3826  CD2  LEU B 189       3.679   9.632  39.803  1.00 43.25           B  C
ATOM   3827  C    LEU B 189       3.420  12.947  38.272  1.00 46.18           B  C
ATOM   3828  O    LEU B 189       2.474  12.260  37.921  1.00 46.18           B  O
ATOM   3829  N    ASP B 190       3.882  13.982  37.583  1.00 47.63           B  N
ATOM   3830  CA   ASP B 190       3.330  14.423  36.315  1.00 47.63           B  C
ATOM   3831  CB   ASP B 190       3.602  15.922  36.151  1.00 60.16           B  C
ATOM   3832  CG   ASP B 190       3.142  16.465  34.810  1.00 60.16           B  C
ATOM   3833  OD1  ASP B 190       3.705  16.076  33.763  1.00 60.16           B  O
ATOM   3834  OD2  ASP B 190       2.211  17.291  34.808  1.00 60.16           B  O
ATOM   3835  C    ASP B 190       3.998  13.621  35.190  1.00 47.63           B  C
ATOM   3836  O    ASP B 190       5.187  13.790  34.897  1.00 47.63           B  O
ATOM   3837  N    PRO B 191       3.229  12.747  34.532  1.00 49.91           B  N
ATOM   3838  CD   PRO B 191       1.757  12.661  34.582  1.00 70.68           B  C
ATOM   3839  CA   PRO B 191       3.765  11.923  33.447  1.00 49.91           B  C
ATOM   3840  CB   PRO B 191       2.532  11.165  32.952  1.00 70.68           B  C
ATOM   3841  CG   PRO B 191       1.414  12.164  33.189  1.00 70.68           B  C
ATOM   3842  C    PRO B 191       4.507  12.659  32.326  1.00 49.91           B  C
ATOM   3843  O    PRO B 191       5.559  12.204  31.897  1.00 49.91           B  O
ATOM   3844  N    ASP B 192       3.992  13.790  31.854  1.00 40.47           B  N
ATOM   3845  CA   ASP B 192       4.671  14.511  30.764  1.00 40.47           B  C
ATOM   3846  CB   ASP B 192       3.712  15.489  30.045  1.00 66.72           B  C
ATOM   3847  CG   ASP B 192       2.408  14.833  29.590  1.00 66.72           B  C
ATOM   3848  OD1  ASP B 192       2.428  13.754  28.948  1.00 66.72           B  O
ATOM   3849  OD2  ASP B 192       1.348  15.430  29.874  1.00 66.72           B  O
ATOM   3850  C    ASP B 192       5.923  15.299  31.174  1.00 40.47           B  C
ATOM   3851  O    ASP B 192       6.729  15.676  30.321  1.00 40.47           B  O
ATOM   3852  N    THR B 193       6.081  15.582  32.462  1.00 38.88           B  N
ATOM   3853  CA   THR B 193       7.257  16.329  32.898  1.00 38.88           B  C
ATOM   3854  CB   THR B 193       6.866  17.586  33.687  1.00 41.95           B  C
ATOM   3855  OG1  THR B 193       5.935  17.244  34.714  1.00 41.95           B  O
ATOM   3856  CG2  THR B 193       6.237  18.596  32.770  1.00 41.95           B  C
ATOM   3857  C    THR B 193       8.184  15.469  33.735  1.00 38.88           B  C
ATOM   3858  O    THR B 193       9.366  15.771  33.872  1.00 38.88           B  O
ATOM   3859  N    ALA B 194       7.631  14.388  34.270  1.00 38.95           B  N
ATOM   3860  CA   ALA B 194       8.375  13.443  35.088  1.00 38.95           B  C
ATOM   3861  CB   ALA B 194       9.582  12.918  34.321  1.00 27.25           B  C
ATOM   3862  C    ALA B 194       8.827  14.009  36.427  1.00 38.95           B  C
ATOM   3863  O    ALA B 194       9.818  13.551  36.988  1.00 38.95           B  O
ATOM   3864  N    VAL B 195       8.115  14.999  36.950  1.00 40.82           B  N
ATOM   3865  CA   VAL B 195       8.508  15.550  38.228  1.00 40.82           B  C
ATOM   3866  CB   VAL B 195       8.263  17.081  38.283  1.00 32.75           B  C
ATOM   3867  CG1  VAL B 195       8.522  17.688  36.915  1.00 32.75           B  C
ATOM   3868  CG2  VAL B 195       6.873  17.390  38.790  1.00 32.75           B  C
ATOM   3869  C    VAL B 195       7.729  14.831  39.320  1.00 40.82           B  C
ATOM   3870  O    VAL B 195       6.554  14.510  39.149  1.00 40.82           B  O
ATOM   3871  N    LEU B 196       8.396  14.554  40.434  1.00 42.74           B  N
ATOM   3872  CA   LEU B 196       7.766  13.859  41.546  1.00 42.74           B  C
ATOM   3873  CB   LEU B 196       8.664  12.696  41.998  1.00 33.47           B  C
ATOM   3874  CG   LEU B 196       8.221  11.800  43.159  1.00 33.47           B  C
ATOM   3875  CD1  LEU B 196       8.820  10.436  42.990  1.00 33.47           B  C
ATOM   3876  CD2  LEU B 196       8.641  12.402  44.473  1.00 33.47           B  C
ATOM   3877  C    LEU B 196       7.500  14.820  42.699  1.00 42.74           B  C
ATOM   3878  O    LEU B 196       8.224  15.793  42.888  1.00 42.74           B  O
ATOM   3879  N    LYS B 197       6.462  14.542  43.474  1.00 35.44           B  N
```

FIG. 3-59

| | | | | | | | | | | | |
|---|---|---|---|---|---|---|---|---|---|---|---|
| ATOM | 3880 | CA | LYS | B | 197 | 6.108 | 15.400 | 44.589 | 1.00 | 35.44 | B C |
| ATOM | 3881 | CB | LYS | B | 197 | 4.978 | 16.344 | 44.188 | 1.00 | 38.85 | B C |
| ATOM | 3882 | CG | LYS | B | 197 | 5.424 | 17.393 | 43.231 | 1.00 | 38.85 | B C |
| ATOM | 3883 | CD | LYS | B | 197 | 4.275 | 18.114 | 42.608 | 1.00 | 38.85 | B C |
| ATOM | 3884 | CE | LYS | B | 197 | 4.822 | 19.176 | 41.682 | 1.00 | 38.85 | B C |
| ATOM | 3885 | NZ | LYS | B | 197 | 5.886 | 19.948 | 42.398 | 1.00 | 38.85 | B N |
| ATOM | 3886 | C | LYS | B | 197 | 5.672 | 14.625 | 45.805 | 1.00 | 35.44 | B C |
| ATOM | 3887 | O | LYS | B | 197 | 4.738 | 13.828 | 45.742 | 1.00 | 35.44 | B O |
| ATOM | 3888 | N | LEU | B | 198 | 6.348 | 14.859 | 46.922 | 1.00 | 38.91 | B N |
| ATOM | 3889 | CA | LEU | B | 198 | 5.970 | 14.189 | 48.143 | 1.00 | 38.91 | B C |
| ATOM | 3890 | CB | LEU | B | 198 | 7.025 | 14.417 | 49.222 | 1.00 | 41.34 | B C |
| ATOM | 3891 | CG | LEU | B | 198 | 7.577 | 13.200 | 49.971 | 1.00 | 41.34 | B C |
| ATOM | 3892 | CD1 | LEU | B | 198 | 8.440 | 13.680 | 51.124 | 1.00 | 41.34 | B C |
| ATOM | 3893 | CD2 | LEU | B | 198 | 6.457 | 12.338 | 50.488 | 1.00 | 41.34 | B C |
| ATOM | 3894 | C | LEU | B | 198 | 4.648 | 14.832 | 48.563 | 1.00 | 38.91 | B C |
| ATOM | 3895 | O | LEU | B | 198 | 4.479 | 16.051 | 48.472 | 1.00 | 38.91 | B O |
| ATOM | 3896 | N | CYS | B | 199 | 3.696 | 14.011 | 48.982 | 1.00 | 36.27 | B N |
| ATOM | 3897 | CA | CYS | B | 199 | 2.422 | 14.529 | 49.448 | 1.00 | 36.27 | B C |
| ATOM | 3898 | CB | CYS | B | 199 | 1.359 | 14.498 | 48.333 | 1.00 | 52.34 | B C |
| ATOM | 3899 | SG | CYS | B | 199 | 0.591 | 12.885 | 48.004 | 1.00 | 52.34 | B S |
| ATOM | 3900 | C | CYS | B | 199 | 1.996 | 13.678 | 50.641 | 1.00 | 36.27 | B C |
| ATOM | 3901 | O | CYS | B | 199 | 2.587 | 12.646 | 50.907 | 1.00 | 36.27 | B O |
| ATOM | 3902 | N | ASP | B | 200 | 0.970 | 14.131 | 51.348 | 1.00 | 53.72 | B N |
| ATOM | 3903 | CA | ASP | B | 200 | 0.435 | 13.460 | 52.530 | 1.00 | 53.72 | B C |
| ATOM | 3904 | CB | ASP | B | 200 | 0.157 | 11.974 | 52.272 | 1.00 | 59.46 | B C |
| ATOM | 3905 | CG | ASP | B | 200 | -0.679 | 11.340 | 53.385 | 1.00 | 59.46 | B C |
| ATOM | 3906 | OD1 | ASP | B | 200 | -0.872 | 11.998 | 54.436 | 1.00 | 59.46 | B O |
| ATOM | 3907 | OD2 | ASP | B | 200 | -1.144 | 10.189 | 53.219 | 1.00 | 59.46 | B O |
| ATOM | 3908 | C | ASP | B | 200 | 1.371 | 13.604 | 53.722 | 1.00 | 53.72 | B C |
| ATOM | 3909 | O | ASP | B | 200 | 2.134 | 12.697 | 54.058 | 1.00 | 53.72 | B O |
| ATOM | 3910 | N | PHE | B | 201 | 1.307 | 14.762 | 54.363 | 1.00 | 33.71 | B N |
| ATOM | 3911 | CA | PHE | B | 201 | 2.144 | 15.023 | 55.517 | 1.00 | 33.71 | B C |
| ATOM | 3912 | CB | PHE | B | 201 | 2.745 | 16.438 | 55.437 | 1.00 | 28.12 | B C |
| ATOM | 3913 | CG | PHE | B | 201 | 3.886 | 16.573 | 54.450 | 1.00 | 28.12 | B C |
| ATOM | 3914 | CD1 | PHE | B | 201 | 3.653 | 16.580 | 53.079 | 1.00 | 28.12 | B C |
| ATOM | 3915 | CD2 | PHE | B | 201 | 5.195 | 16.714 | 54.903 | 1.00 | 28.12 | B C |
| ATOM | 3916 | CE1 | PHE | B | 201 | 4.708 | 16.727 | 52.177 | 1.00 | 28.12 | B C |
| ATOM | 3917 | CE2 | PHE | B | 201 | 6.259 | 16.864 | 54.013 | 1.00 | 28.12 | B C |
| ATOM | 3918 | CZ | PHE | B | 201 | 6.015 | 16.870 | 52.651 | 1.00 | 28.12 | B C |
| ATOM | 3919 | C | PHE | B | 201 | 1.308 | 14.864 | 56.781 | 1.00 | 33.71 | B C |
| ATOM | 3920 | O | PHE | B | 201 | 1.585 | 15.481 | 57.800 | 1.00 | 33.71 | B O |
| ATOM | 3921 | N | GLY | B | 202 | 0.292 | 14.013 | 56.707 | 1.00 | 48.40 | B N |
| ATOM | 3922 | CA | GLY | B | 202 | -0.585 | 13.798 | 57.845 | 1.00 | 48.40 | B C |
| ATOM | 3923 | C | GLY | B | 202 | 0.018 | 12.982 | 58.973 | 1.00 | 48.40 | B C |
| ATOM | 3924 | O | GLY | B | 202 | -0.616 | 12.816 | 60.010 | 1.00 | 48.40 | B O |
| ATOM | 3925 | N | SER | B | 203 | 1.235 | 12.474 | 58.767 | 1.00 | 44.27 | B N |
| ATOM | 3926 | CA | SER | B | 203 | 1.957 | 11.671 | 59.755 | 1.00 | 44.27 | B C |
| ATOM | 3927 | CB | SER | B | 203 | 2.155 | 10.239 | 59.252 | 1.00 | 34.43 | B C |
| ATOM | 3928 | OG | SER | B | 203 | 0.934 | 9.649 | 58.868 | 1.00 | 34.43 | B O |
| ATOM | 3929 | C | SER | B | 203 | 3.332 | 12.291 | 59.976 | 1.00 | 44.27 | B C |
| ATOM | 3930 | O | SER | B | 203 | 4.128 | 11.808 | 60.792 | 1.00 | 44.27 | B O |
| ATOM | 3931 | N | ALA | B | 204 | 3.614 | 13.349 | 59.219 | 1.00 | 41.64 | B N |
| ATOM | 3932 | CA | ALA | B | 204 | 4.888 | 14.051 | 59.316 | 1.00 | 41.64 | B C |
| ATOM | 3933 | CB | ALA | B | 204 | 4.997 | 15.111 | 58.208 | 1.00 | 48.14 | B C |
| ATOM | 3934 | C | ALA | B | 204 | 4.997 | 14.703 | 60.685 | 1.00 | 41.64 | B C |
| ATOM | 3935 | O | ALA | B | 204 | 3.998 | 15.125 | 61.259 | 1.00 | 41.64 | B O |
| ATOM | 3936 | N | LYS | B | 205 | 6.215 | 14.789 | 61.204 | 1.00 | 42.49 | B N |
| ATOM | 3937 | CA | LYS | B | 205 | 6.432 | 15.378 | 62.512 | 1.00 | 42.49 | B C |
| ATOM | 3938 | CB | LYS | B | 205 | 6.070 | 14.373 | 63.598 | 1.00 | 32.64 | B C |
| ATOM | 3939 | CG | LYS | B | 205 | 6.518 | 14.754 | 65.002 | 1.00 | 32.64 | B C |
| ATOM | 3940 | CD | LYS | B | 205 | 5.997 | 13.744 | 66.002 | 1.00 | 32.64 | B C |
| ATOM | 3941 | CE | LYS | B | 205 | 6.369 | 14.075 | 67.419 | 1.00 | 32.64 | B C |
| ATOM | 3942 | NZ | LYS | B | 205 | 5.822 | 13.029 | 68.328 | 1.00 | 32.64 | B N |
| ATOM | 3943 | C | LYS | B | 205 | 7.860 | 15.826 | 62.717 | 1.00 | 42.49 | B C |
| ATOM | 3944 | O | LYS | B | 205 | 8.809 | 15.165 | 62.279 | 1.00 | 42.49 | B O |
| ATOM | 3945 | N | GLN | B | 206 | 8.009 | 16.967 | 63.381 | 1.00 | 51.97 | B N |
| ATOM | 3946 | CA | GLN | B | 206 | 9.335 | 17.482 | 63.683 | 1.00 | 51.97 | B C |

FIG. 3-60

```
ATOM   3947  CB  GLN B 206       9.256  18.957  64.055  1.00 73.48      B    C
ATOM   3948  CG  GLN B 206      10.604  19.581  64.320  1.00 73.48      B    C
ATOM   3949  CD  GLN B 206      10.648  21.049  63.922  1.00 73.48      B    C
ATOM   3950  OE1 GLN B 206      11.588  21.774  64.283  1.00 73.48      B    O
ATOM   3951  NE2 GLN B 206       9.632  21.499  63.162  1.00 73.48      B    N
ATOM   3952  C   GLN B 206       9.825  16.648  64.860  1.00 51.97      B    C
ATOM   3953  O   GLN B 206       9.181  16.591  65.898  1.00 51.97      B    O
ATOM   3954  N   LEU B 207      10.946  15.968  64.683  1.00 41.20      B    N
ATOM   3955  CA  LEU B 207      11.471  15.120  65.740  1.00 41.20      B    C
ATOM   3956  CB  LEU B 207      12.116  13.862  65.153  1.00 41.59      B    C
ATOM   3957  CG  LEU B 207      11.223  12.965  64.287  1.00 41.59      B    C
ATOM   3958  CD1 LEU B 207      12.077  11.902  63.626  1.00 41.59      B    C
ATOM   3959  CD2 LEU B 207      10.101  12.339  65.121  1.00 41.59      B    C
ATOM   3960  C   LEU B 207      12.486  15.871  66.575  1.00 41.20      B    C
ATOM   3961  O   LEU B 207      13.382  16.535  66.052  1.00 41.20      B    O
ATOM   3962  N   VAL B 208      12.321  15.761  67.886  1.00 53.81      B    N
ATOM   3963  CA  VAL B 208      13.198  16.404  68.847  1.00 53.81      B    C
ATOM   3964  CB  VAL B 208      12.395  17.332  69.776  1.00 53.29      B    C
ATOM   3965  CG1 VAL B 208      13.093  17.466  71.120  1.00 53.29      B    C
ATOM   3966  CG2 VAL B 208      12.243  18.698  69.122  1.00 53.29      B    C
ATOM   3967  C   VAL B 208      13.881  15.321  69.662  1.00 53.81      B    C
ATOM   3968  O   VAL B 208      13.227  14.438  70.237  1.00 53.81      B    O
ATOM   3969  N   ARG B 209      15.204  15.382  69.702  1.00 66.20      B    N
ATOM   3970  CA  ARG B 209      15.965  14.399  70.451  1.00 66.20      B    C
ATOM   3971  CB  ARG B 209      17.450  14.720  70.367  1.00100.00      B    C
ATOM   3972  CG  ARG B 209      18.362  13.615  70.919  1.00100.00      B    C
ATOM   3973  CD  ARG B 209      19.841  14.007  70.740  1.00100.00      B    C
ATOM   3974  NE  ARG B 209      20.048  14.636  69.430  1.00100.00      B    N
ATOM   3975  CZ  ARG B 209      21.183  15.209  69.034  1.00100.00      B    C
ATOM   3976  NH1 ARG B 209      22.232  15.229  69.854  1.00100.00      B    N
ATOM   3977  NH2 ARG B 209      21.259  15.781  67.825  1.00100.00      B    N
ATOM   3978  C   ARG B 209      15.523  14.437  71.906  1.00 66.20      B    C
ATOM   3979  O   ARG B 209      15.667  15.467  72.572  1.00 66.20      B    O
ATOM   3980  N   GLY B 210      14.977  13.333  72.405  1.00 62.30      B    N
ATOM   3981  CA  GLY B 210      14.549  13.320  73.793  1.00 62.30      B    C
ATOM   3982  C   GLY B 210      13.065  13.064  73.955  1.00 62.30      B    C
ATOM   3983  O   GLY B 210      12.648  12.259  74.796  1.00 62.30      B    O
ATOM   3984  N   GLU B 211      12.254  13.751  73.157  1.00 66.27      B    N
ATOM   3985  CA  GLU B 211      10.811  13.552  73.222  1.00 66.27      B    C
ATOM   3986  CB  GLU B 211      10.105  14.778  72.645  1.00 67.47      B    C
ATOM   3987  CG  GLU B 211      10.582  16.088  73.268  1.00 67.47      B    C
ATOM   3988  CD  GLU B 211      10.193  17.315  72.449  1.00 67.47      B    C
ATOM   3989  OE1 GLU B 211      10.521  18.447  72.877  1.00 67.47      B    O
ATOM   3990  OE2 GLU B 211       9.567  17.153  71.372  1.00 67.47      B    O
ATOM   3991  C   GLU B 211      10.470  12.280  72.423  1.00 66.27      B    C
ATOM   3992  O   GLU B 211      10.679  12.216  71.209  1.00 66.27      B    O
ATOM   3993  N   PRO B 212       9.970  11.237  73.106  1.00 62.80      B    N
ATOM   3994  CD  PRO B 212       9.630  11.161  74.535  1.00 63.66      B    C
ATOM   3995  CA  PRO B 212       9.619   9.984  72.428  1.00 62.80      B    C
ATOM   3996  CB  PRO B 212       9.123   9.094  73.569  1.00 63.66      B    C
ATOM   3997  CG  PRO B 212       8.564  10.076  74.537  1.00 63.66      B    C
ATOM   3998  C   PRO B 212       8.574  10.160  71.341  1.00 62.80      B    C
ATOM   3999  O   PRO B 212       7.808  11.130  71.359  1.00 62.80      B    O
ATOM   4000  N   ASN B 213       8.551   9.211  70.402  1.00 52.52      B    N
ATOM   4001  CA  ASN B 213       7.611   9.222  69.281  1.00 52.52      B    C
ATOM   4002  CB  ASN B 213       8.348   9.570  67.996  1.00 33.17      B    C
ATOM   4003  CG  ASN B 213       9.161  10.832  68.122  1.00 33.17      B    C
ATOM   4004  OD1 ASN B 213       8.616  11.907  68.320  1.00 33.17      B    O
ATOM   4005  ND2 ASN B 213      10.475  10.705  68.018  1.00 33.17      B    N
ATOM   4006  C   ASN B 213       6.983   7.846  69.147  1.00 52.52      B    C
ATOM   4007  O   ASN B 213       7.568   6.856  69.583  1.00 52.52      B    O
ATOM   4008  N   VAL B 214       5.788   7.786  68.560  1.00 35.95      B    N
ATOM   4009  CA  VAL B 214       5.091   6.514  68.355  1.00 35.95      B    C
ATOM   4010  CB  VAL B 214       3.688   6.743  67.740  1.00 42.51      B    C
ATOM   4011  CG1 VAL B 214       3.117   5.434  67.223  1.00 42.51      B    C
ATOM   4012  CG2 VAL B 214       2.758   7.346  68.784  1.00 42.51      B    C
ATOM   4013  C   VAL B 214       5.913   5.640  67.405  1.00 35.95      B    C
```

FIG. 3-61

```
ATOM   4014  O    VAL B 214       6.389   6.111  66.366  1.00 35.95      B  O
ATOM   4015  N    SER B 215       6.089   4.370  67.753  1.00 46.54      B  N
ATOM   4016  CA   SER B 215       6.879   3.495  66.893  1.00 46.54      B  C
ATOM   4017  CB   SER B 215       7.292   2.221  67.652  1.00 32.83      B  C
ATOM   4018  OG   SER B 215       6.178   1.548  68.194  1.00 32.83      B  O
ATOM   4019  C    SER B 215       6.117   3.159  65.604  1.00 46.54      B  C
ATOM   4020  O    SER B 215       6.193   2.051  65.064  1.00 46.54      B  O
ATOM   4021  N    PTY B 216       4.116   2.221  66.523  1.00 45.96      B  N
ATOM   4022  CA   PTY B 216       3.378   1.977  65.292  1.00 45.96      B  C
ATOM   4023  C    PTY B 216       3.121   3.291  64.569  1.00 45.96      B  C
ATOM   4024  O    PTY B 216       2.378   3.337  63.595  1.00 45.96      B  O
ATOM   4025  CB   PTY B 216       2.053   1.311  65.627  1.00 45.96      B  C
ATOM   4026  CG   PTY B 216       1.592   0.415  64.573  1.00 45.96      B  C
ATOM   4027  CD1  PTY B 216       2.197  -0.906  64.410  1.00 45.96      B  C
ATOM   4028  CD2  PTY B 216       0.363   0.772  63.851  1.00 45.96      B  C
ATOM   4029  CE1  PTY B 216       1.551  -1.879  63.519  1.00 45.96      B  C
ATOM   4030  CE2  PTY B 216      -0.261  -0.215  62.968  1.00 45.96      B  C
ATOM   4031  CZ   PTY B 216       0.317  -1.548  62.792  1.00 45.96      B  C
ATOM   4032  OH   PTY B 216      -0.323  -2.503  62.045  1.00 45.96      B  O
ATOM   4033  P    PTY B 216       0.024  -2.514  60.579  1.00 45.96      B  P
ATOM   4034  OP1  PTY B 216       1.215  -3.422  60.488  1.00 45.96      B  O
ATOM   4035  OP2  PTY B 216       0.267  -1.014  60.088  1.00 45.96      B  O
ATOM   4036  OP3  PTY B 216      -1.142  -3.137  59.860  1.00 45.96      B  O
ATOM   4037  N    ILE B 217       4.676   3.481  62.724  1.00 38.77      B  N
ATOM   4038  CA   ILE B 217       4.065   4.272  61.674  1.00 38.77      B  C
ATOM   4039  CB   ILE B 217       4.374   5.794  61.845  1.00 42.71      B  C
ATOM   4040  CG2  ILE B 217       3.479   6.407  62.910  1.00 42.71      B  C
ATOM   4041  CG1  ILE B 217       5.856   5.995  62.166  1.00 42.71      B  C
ATOM   4042  CD1  ILE B 217       6.278   5.436  63.488  1.00 42.71      B  C
ATOM   4043  C    ILE B 217       4.595   3.788  60.334  1.00 38.77      B  C
ATOM   4044  O    ILE B 217       5.426   2.887  60.289  1.00 38.77      B  O
ATOM   4045  N    CYS B 218       4.120   4.403  59.258  1.00 38.72      B  N
ATOM   4046  CA   CYS B 218       4.501   4.046  57.890  1.00 38.72      B  C
ATOM   4047  CB   CYS B 218       5.994   3.692  57.750  1.00 47.58      B  C
ATOM   4048  SG   CYS B 218       7.167   4.736  58.581  1.00 47.58      B  S
ATOM   4049  C    CYS B 218       3.720   2.807  57.511  1.00 38.72      B  C
ATOM   4050  O    CYS B 218       3.400   1.991  58.372  1.00 38.72      B  O
ATOM   4051  N    SER B 219       3.412   2.657  56.229  1.00 36.32      B  N
ATOM   4052  CA   SER B 219       2.715   1.461  55.809  1.00 36.32      B  C
ATOM   4053  CB   SER B 219       2.459   1.473  54.306  1.00 59.07      B  C
ATOM   4054  OG   SER B 219       1.606   2.546  53.955  1.00 59.07      B  O
ATOM   4055  C    SER B 219       3.684   0.351  56.157  1.00 36.32      B  C
ATOM   4056  O    SER B 219       4.884   0.492  55.962  1.00 36.32      B  O
ATOM   4057  N    ARG B 220       3.157  -0.741  56.684  1.00 36.73      B  N
ATOM   4058  CA   ARG B 220       3.953  -1.895  57.077  1.00 36.73      B  C
ATOM   4059  CB   ARG B 220       3.040  -3.101  57.213  1.00 45.16      B  C
ATOM   4060  CG   ARG B 220       3.715  -4.322  57.738  1.00 45.16      B  C
ATOM   4061  CD   ARG B 220       2.686  -5.199  58.386  1.00 45.16      B  C
ATOM   4062  NE   ARG B 220       1.791  -5.812  57.413  1.00 45.16      B  N
ATOM   4063  CZ   ARG B 220       0.515  -6.093  57.651  1.00 45.16      B  C
ATOM   4064  NH1  ARG B 220      -0.024  -5.808  58.826  1.00 45.16      B  N
ATOM   4065  NH2  ARG B 220      -0.218  -6.677  56.720  1.00 45.16      B  N
ATOM   4066  C    ARG B 220       5.110  -2.259  56.151  1.00 36.73      B  C
ATOM   4067  O    ARG B 220       6.258  -2.380  56.589  1.00 36.73      B  O
ATOM   4068  N    TYR B 221       4.800  -2.449  54.874  1.00 45.52      B  N
ATOM   4069  CA   TYR B 221       5.804  -2.827  53.890  1.00 45.52      B  C
ATOM   4070  CB   TYR B 221       5.199  -2.834  52.486  1.00 45.52      B  C
ATOM   4071  CG   TYR B 221       4.196  -3.930  52.236  1.00 45.52      B  C
ATOM   4072  CD1  TYR B 221       3.722  -4.727  53.281  1.00 45.52      B  C
ATOM   4073  CE1  TYR B 221       2.809  -5.737  53.049  1.00 45.52      B  C
ATOM   4074  CD2  TYR B 221       3.722  -4.175  50.954  1.00 45.52      B  C
ATOM   4075  CE2  TYR B 221       2.806  -5.182  50.712  1.00 45.52      B  C
ATOM   4076  CZ   TYR B 221       2.354  -5.959  51.757  1.00 45.52      B  C
ATOM   4077  OH   TYR B 221       1.450  -6.962  51.500  1.00 45.52      B  O
ATOM   4078  C    TYR B 221       6.989  -1.903  53.875  1.00 45.52      B  C
ATOM   4079  O    TYR B 221       8.116  -2.331  53.616  1.00 45.52      B  O
ATOM   4080  N    TYR B 222       6.725  -0.631  54.144  1.00 41.36      B  N
```

FIG. 3-62

```
ATOM   4081  CA   TYR B 222       7.761   0.383  54.103  1.00 41.36      B    C
ATOM   4082  CB   TYR B 222       7.249   1.569  53.294  1.00 50.21      B    C
ATOM   4083  CG   TYR B 222       6.657   1.119  51.984  1.00 50.21      B    C
ATOM   4084  CD1  TYR B 222       5.322   0.728  51.898  1.00 50.21      B    C
ATOM   4085  CE1  TYR B 222       4.799   0.197  50.721  1.00 50.21      B    C
ATOM   4086  CD2  TYR B 222       7.456   0.975  50.854  1.00 50.21      B    C
ATOM   4087  CE2  TYR B 222       6.945   0.445  49.676  1.00 50.21      B    C
ATOM   4088  CZ   TYR B 222       5.616   0.057  49.615  1.00 50.21      B    C
ATOM   4089  OH   TYR B 222       5.118  -0.472  48.444  1.00 50.21      B    O
ATOM   4090  C    TYR B 222       8.245   0.840  55.452  1.00 41.36      B    C
ATOM   4091  O    TYR B 222       8.982   1.813  55.533  1.00 41.36      B    O
ATOM   4092  N    ARG B 223       7.849   0.123  56.501  1.00 43.99      B    N
ATOM   4093  CA   ARG B 223       8.227   0.450  57.876  1.00 43.99      B    C
ATOM   4094  CB   ARG B 223       7.213  -0.174  58.841  1.00 40.59      B    C
ATOM   4095  CG   ARG B 223       7.608  -0.084  60.297  1.00 40.59      B    C
ATOM   4096  CD   ARG B 223       6.407   0.092  61.195  1.00 40.59      B    C
ATOM   4097  NE   ARG B 223       5.509  -1.057  61.162  1.00 40.59      B    N
ATOM   4098  CZ   ARG B 223       4.255  -1.018  60.718  1.00 40.59      B    C
ATOM   4099  NH1  ARG B 223       3.734   0.118  60.260  1.00 40.59      B    N
ATOM   4100  NH2  ARG B 223       3.517  -2.121  60.741  1.00 40.59      B    N
ATOM   4101  C    ARG B 223       9.651   0.015  58.252  1.00 43.99      B    C
ATOM   4102  O    ARG B 223      10.036  -1.137  58.039  1.00 43.99      B    O
ATOM   4103  N    ALA B 224      10.424   0.947  58.809  1.00 32.45      B    N
ATOM   4104  CA   ALA B 224      11.799   0.679  59.231  1.00 32.45      B    C
ATOM   4105  CB   ALA B 224      12.456   1.951  59.721  1.00 47.06      B    C
ATOM   4106  C    ALA B 224      11.840  -0.368  60.328  1.00 32.45      B    C
ATOM   4107  O    ALA B 224      10.981  -0.401  61.206  1.00 32.45      B    O
ATOM   4108  N    PRO B 225      12.870  -1.221  60.311  1.00 42.38      B    N
ATOM   4109  CD   PRO B 225      14.095  -1.123  59.498  1.00 28.16      B    C
ATOM   4110  CA   PRO B 225      13.003  -2.274  61.318  1.00 42.38      B    C
ATOM   4111  CB   PRO B 225      14.292  -2.980  60.899  1.00 28.16      B    C
ATOM   4112  CG   PRO B 225      15.096  -1.877  60.331  1.00 28.16      B    C
ATOM   4113  C    PRO B 225      13.017  -1.770  62.765  1.00 42.38      B    C
ATOM   4114  O    PRO B 225      12.508  -2.448  63.660  1.00 42.38      B    O
ATOM   4115  N    GLU B 226      13.593  -0.592  63.010  1.00 43.73      B    N
ATOM   4116  CA   GLU B 226      13.611  -0.067  64.372  1.00 43.73      B    C
ATOM   4117  CB   GLU B 226      14.104   1.373  64.423  1.00 44.47      B    C
ATOM   4118  CG   GLU B 226      15.430   1.592  63.783  1.00 44.47      B    C
ATOM   4119  CD   GLU B 226      15.290   2.221  62.436  1.00 44.47      B    C
ATOM   4120  OE1  GLU B 226      15.122   3.453  62.362  1.00 44.47      B    O
ATOM   4121  OE2  GLU B 226      15.332   1.474  61.448  1.00 44.47      B    O
ATOM   4122  C    GLU B 226      12.184  -0.073  64.858  1.00 43.73      B    C
ATOM   4123  O    GLU B 226      11.865  -0.699  65.860  1.00 43.73      B    O
ATOM   4124  N    LEU B 227      11.329   0.630  64.122  1.00 39.21      B    N
ATOM   4125  CA   LEU B 227       9.919   0.749  64.455  1.00 39.21      B    C
ATOM   4126  CB   LEU B 227       9.165   1.376  63.290  1.00 45.83      B    C
ATOM   4127  CG   LEU B 227       9.664   2.730  62.805  1.00 45.83      B    C
ATOM   4128  CD1  LEU B 227       8.920   3.121  61.540  1.00 45.83      B    C
ATOM   4129  CD2  LEU B 227       9.472   3.757  63.898  1.00 45.83      B    C
ATOM   4130  C    LEU B 227       9.248  -0.566  64.825  1.00 39.21      B    C
ATOM   4131  O    LEU B 227       8.453  -0.613  65.749  1.00 39.21      B    O
ATOM   4132  N    ILE B 228       9.546  -1.635  64.102  1.00 34.46      B    N
ATOM   4133  CA   ILE B 228       8.924  -2.915  64.412  1.00 34.46      B    C
ATOM   4134  CB   ILE B 228       9.321  -4.010  63.399  1.00 42.47      B    C
ATOM   4135  CG2  ILE B 228       8.527  -5.288  63.677  1.00 42.47      B    C
ATOM   4136  CG1  ILE B 228       9.054  -3.524  61.973  1.00 42.47      B    C
ATOM   4137  CD1  ILE B 228       9.519  -4.494  60.912  1.00 42.47      B    C
ATOM   4138  C    ILE B 228       9.365  -3.353  65.798  1.00 34.46      B    C
ATOM   4139  O    ILE B 228       8.601  -3.987  66.532  1.00 34.46      B    O
ATOM   4140  N    PHE B 229      10.608  -3.000  66.130  1.00 46.34      B    N
ATOM   4141  CA   PHE B 229      11.230  -3.310  67.420  1.00 46.34      B    C
ATOM   4142  CB   PHE B 229      12.746  -3.138  67.334  1.00 41.94      B    C
ATOM   4143  CG   PHE B 229      13.488  -4.392  66.976  1.00 41.94      B    C
ATOM   4144  CD1  PHE B 229      13.663  -5.402  67.914  1.00 41.94      B    C
ATOM   4145  CD2  PHE B 229      14.037  -4.550  65.708  1.00 41.94      B    C
ATOM   4146  CE1  PHE B 229      14.383  -6.556  67.594  1.00 41.94      B    C
ATOM   4147  CE2  PHE B 229      14.758  -5.692  65.373  1.00 41.94      B    C
```

FIG. 3-63

```
ATOM   4148  CZ   PHE B 229      14.932   -6.699   66.320  1.00 41.94      B    C
ATOM   4149  C    PHE B 229      10.705   -2.436   68.559  1.00 46.34      B    C
ATOM   4150  O    PHE B 229      11.196   -2.513   69.674  1.00 46.34      B    O
ATOM   4151  N    GLY B 230       9.718   -1.597   68.267  1.00 49.04      B    N
ATOM   4152  CA   GLY B 230       9.133   -0.748   69.286  1.00 49.04      B    C
ATOM   4153  C    GLY B 230       9.902    0.518   69.598  1.00 49.04      B    C
ATOM   4154  O    GLY B 230       9.517    1.277   70.501  1.00 49.04      B    O
ATOM   4155  N    ALA B 231      10.980    0.758   68.857  1.00 62.29      B    N
ATOM   4156  CA   ALA B 231      11.801    1.947   69.082  1.00 62.29      B    C
ATOM   4157  CB   ALA B 231      12.874    2.042   68.006  1.00 46.15      B    C
ATOM   4158  C    ALA B 231      10.947    3.219   69.093  1.00 62.29      B    C
ATOM   4159  O    ALA B 231      10.116    3.421   68.196  1.00 62.29      B    O
ATOM   4160  N    THR B 232      11.145    4.070   70.100  1.00 46.16      B    N
ATOM   4161  CA   THR B 232      10.379    5.309   70.194  1.00 46.16      B    C
ATOM   4162  CB   THR B 232       9.587    5.376   71.483  1.00 63.65      B    C
ATOM   4163  OG1  THR B 232      10.473    5.742   72.549  1.00 63.65      B    O
ATOM   4164  CG2  THR B 232       8.944    4.017   71.780  1.00 63.65      B    C
ATOM   4165  C    THR B 232      11.285    6.532   70.136  1.00 46.16      B    C
ATOM   4166  O    THR B 232      10.814    7.670   70.162  1.00 46.16      B    O
ATOM   4167  N    ASP B 233      12.587    6.294   70.061  1.00 56.68      B    N
ATOM   4168  CA   ASP B 233      13.548    7.383   69.967  1.00 56.68      B    C
ATOM   4169  CB   ASP B 233      14.600    7.261   71.056  1.00 84.47      B    C
ATOM   4170  CG   ASP B 233      15.601    6.160   70.757  1.00 84.47      B    C
ATOM   4171  OD1  ASP B 233      15.153    5.057   70.345  1.00 84.47      B    O
ATOM   4172  OD2  ASP B 233      16.825    6.401   70.930  1.00 84.47      B    O
ATOM   4173  C    ASP B 233      14.239    7.267   68.616  1.00 56.68      B    C
ATOM   4174  O    ASP B 233      15.465    7.425   68.517  1.00 56.68      B    O
ATOM   4175  N    TYR B 234      13.456    6.982   67.576  1.00 49.14      B    N
ATOM   4176  CA   TYR B 234      14.015    6.849   66.241  1.00 49.14      B    C
ATOM   4177  CB   TYR B 234      13.059    6.053   65.352  1.00 40.85      B    C
ATOM   4178  CG   TYR B 234      11.647    6.580   65.314  1.00 40.85      B    C
ATOM   4179  CD1  TYR B 234      11.282    7.597   64.431  1.00 40.85      B    C
ATOM   4180  CE1  TYR B 234       9.973    8.057   64.365  1.00 40.85      B    C
ATOM   4181  CD2  TYR B 234      10.659    6.040   66.141  1.00 40.85      B    C
ATOM   4182  CE2  TYR B 234       9.341    6.501   66.079  1.00 40.85      B    C
ATOM   4183  CZ   TYR B 234       9.015    7.510   65.184  1.00 40.85      B    C
ATOM   4184  OH   TYR B 234       7.731    7.978   65.101  1.00 40.85      B    O
ATOM   4185  C    TYR B 234      14.319    8.212   65.643  1.00 49.14      B    C
ATOM   4186  O    TYR B 234      13.928    9.240   66.186  1.00 49.14      B    O
ATOM   4187  N    THR B 235      15.041    8.216   64.534  1.00 45.67      B    N
ATOM   4188  CA   THR B 235      15.413    9.452   63.861  1.00 45.67      B    C
ATOM   4189  CB   THR B 235      16.909    9.490   63.636  1.00 32.74      B    C
ATOM   4190  OG1  THR B 235      17.254    8.556   62.608  1.00 32.74      B    O
ATOM   4191  CG2  THR B 235      17.631    9.094   64.896  1.00 32.74      B    C
ATOM   4192  C    THR B 235      14.717    9.506   62.505  1.00 45.67      B    C
ATOM   4193  O    THR B 235      13.889    8.650   62.194  1.00 45.67      B    O
ATOM   4194  N    SER B 236      15.054   10.497   61.689  1.00 37.65      B    N
ATOM   4195  CA   SER B 236      14.430   10.605   60.378  1.00 37.65      B    C
ATOM   4196  CB   SER B 236      14.556   12.038   59.842  1.00 35.25      B    C
ATOM   4197  OG   SER B 236      15.905   12.373   59.579  1.00 35.25      B    O
ATOM   4198  C    SER B 236      15.024    9.602   59.382  1.00 37.65      B    C
ATOM   4199  O    SER B 236      14.610    9.529   58.227  1.00 37.65      B    O
ATOM   4200  N    SER B 237      15.988    8.811   59.827  1.00 31.55      B    N
ATOM   4201  CA   SER B 237      16.581    7.835   58.930  1.00 31.55      B    C
ATOM   4202  CB   SER B 237      17.821    7.193   59.558  1.00 40.16      B    C
ATOM   4203  OG   SER B 237      17.537    6.638   60.831  1.00 40.16      B    O
ATOM   4204  C    SER B 237      15.540    6.778   58.602  1.00 31.55      B    C
ATOM   4205  O    SER B 237      15.759    5.932   57.754  1.00 31.55      B    O
ATOM   4206  N    ILE B 238      14.403    6.816   59.277  1.00 28.39      B    N
ATOM   4207  CA   ILE B 238      13.361    5.850   58.979  1.00 28.39      B    C
ATOM   4208  CB   ILE B 238      12.200    5.915   60.003  1.00 38.42      B    C
ATOM   4209  CG2  ILE B 238      12.677    5.444   61.358  1.00 38.42      B    C
ATOM   4210  CG1  ILE B 238      11.645    7.338   60.071  1.00 38.42      B    C
ATOM   4211  CD1  ILE B 238      10.352    7.447   60.818  1.00 38.42      B    C
ATOM   4212  C    ILE B 238      12.806    6.133   57.580  1.00 28.39      B    C
ATOM   4213  O    ILE B 238      12.379    5.222   56.878  1.00 28.39      B    O
ATOM   4214  N    ASP B 239      12.807    7.398   57.177  1.00 32.83      B    N
```

FIG. 3-64

```
ATOM   4215  CA   ASP B 239      12.316   7.731  55.850  1.00 32.83      B    C
ATOM   4216  CB   ASP B 239      12.253   9.247  55.623  1.00 38.24      B    C
ATOM   4217  CG   ASP B 239      11.101   9.911  56.346  1.00 38.24      B    C
ATOM   4218  OD1  ASP B 239      10.040   9.281  56.516  1.00 38.24      B    O
ATOM   4219  OD2  ASP B 239      11.246  11.087  56.727  1.00 38.24      B    O
ATOM   4220  C    ASP B 239      13.243   7.122  54.807  1.00 32.83      B    C
ATOM   4221  O    ASP B 239      12.792   6.651  53.767  1.00 32.83      B    O
ATOM   4222  N    VAL B 240      14.541   7.143  55.085  1.00 32.85      B    N
ATOM   4223  CA   VAL B 240      15.504   6.590  54.161  1.00 32.85      B    C
ATOM   4224  CB   VAL B 240      16.922   6.930  54.584  1.00 25.84      B    C
ATOM   4225  CG1  VAL B 240      17.922   6.214  53.692  1.00 25.84      B    C
ATOM   4226  CG2  VAL B 240      17.120   8.430  54.497  1.00 25.84      B    C
ATOM   4227  C    VAL B 240      15.334   5.084  54.031  1.00 32.85      B    C
ATOM   4228  O    VAL B 240      15.577   4.526  52.960  1.00 32.85      B    O
ATOM   4229  N    TRP B 241      14.915   4.417  55.105  1.00 37.39      B    N
ATOM   4230  CA   TRP B 241      14.688   2.986  55.015  1.00 37.39      B    C
ATOM   4231  CB   TRP B 241      14.377   2.378  56.379  1.00 28.29      B    C
ATOM   4232  CG   TRP B 241      13.811   0.981  56.296  1.00 28.29      B    C
ATOM   4233  CD2  TRP B 241      14.529  -0.255  56.419  1.00 28.29      B    C
ATOM   4234  CE2  TRP B 241      13.595  -1.299  56.235  1.00 28.29      B    C
ATOM   4235  CE3  TRP B 241      15.870  -0.584  56.632  1.00 28.29      B    C
ATOM   4236  CD1  TRP B 241      12.511   0.641  56.071  1.00 28.29      B    C
ATOM   4237  NE1  TRP B 241      12.372  -0.723  56.038  1.00 28.29      B    N
ATOM   4238  CZ2  TRP B 241      13.956  -2.645  56.300  1.00 28.29      B    C
ATOM   4239  CZ3  TRP B 241      16.225  -1.927  56.695  1.00 28.29      B    C
ATOM   4240  CH2  TRP B 241      15.272  -2.937  56.514  1.00 28.29      B    C
ATOM   4241  C    TRP B 241      13.499   2.831  54.078  1.00 37.39      B    C
ATOM   4242  O    TRP B 241      13.530   2.011  53.152  1.00 37.39      B    O
ATOM   4243  N    SER B 242      12.466   3.645  54.308  1.00 30.46      B    N
ATOM   4244  CA   SER B 242      11.252   3.630  53.484  1.00 30.46      B    C
ATOM   4245  CB   SER B 242      10.253   4.670  53.971  1.00 30.80      B    C
ATOM   4246  OG   SER B 242       9.811   4.377  55.268  1.00 30.80      B    O
ATOM   4247  C    SER B 242      11.561   3.926  52.025  1.00 30.46      B    C
ATOM   4248  O    SER B 242      10.947   3.357  51.137  1.00 30.46      B    O
ATOM   4249  N    ALA B 243      12.502   4.830  51.786  1.00 27.92      B    N
ATOM   4250  CA   ALA B 243      12.880   5.190  50.438  1.00 27.92      B    C
ATOM   4251  CB   ALA B 243      13.828   6.369  50.472  1.00 22.13      B    C
ATOM   4252  C    ALA B 243      13.542   4.001  49.761  1.00 27.92      B    C
ATOM   4253  O    ALA B 243      13.323   3.734  48.583  1.00 27.92      B    O
ATOM   4254  N    GLY B 244      14.360   3.284  50.521  1.00 39.89      B    N
ATOM   4255  CA   GLY B 244      15.044   2.135  49.972  1.00 39.89      B    C
ATOM   4256  C    GLY B 244      14.094   0.998  49.688  1.00 39.89      B    C
ATOM   4257  O    GLY B 244      14.431   0.083  48.951  1.00 39.89      B    O
ATOM   4258  N    CYS B 245      12.911   1.037  50.287  1.00 37.07      B    N
ATOM   4259  CA   CYS B 245      11.915  -0.008  50.060  1.00 37.07      B    C
ATOM   4260  CB   CYS B 245      10.922  -0.073  51.232  1.00 38.87      B    C
ATOM   4261  SG   CYS B 245      11.510  -0.970  52.704  1.00 38.87      B    S
ATOM   4262  C    CYS B 245      11.174   0.257  48.748  1.00 37.07      B    C
ATOM   4263  O    CYS B 245      10.693  -0.663  48.098  1.00 37.07      B    O
ATOM   4264  N    VAL B 246      11.088   1.527  48.368  1.00 41.56      B    N
ATOM   4265  CA   VAL B 246      10.441   1.923  47.128  1.00 41.56      B    C
ATOM   4266  CB   VAL B 246      10.171   3.433  47.090  1.00 35.23      B    C
ATOM   4267  CG1  VAL B 246       9.619   3.826  45.738  1.00 35.23      B    C
ATOM   4268  CG2  VAL B 246       9.212   3.819  48.188  1.00 35.23      B    C
ATOM   4269  C    VAL B 246      11.381   1.582  45.982  1.00 41.56      B    C
ATOM   4270  O    VAL B 246      10.964   1.051  44.959  1.00 41.56      B    O
ATOM   4271  N    LEU B 247      12.657   1.896  46.152  1.00 32.86      B    N
ATOM   4272  CA   LEU B 247      13.638   1.605  45.124  1.00 32.86      B    C
ATOM   4273  CB   LEU B 247      15.011   2.115  45.545  1.00 33.11      B    C
ATOM   4274  CG   LEU B 247      16.158   1.620  44.668  1.00 33.11      B    C
ATOM   4275  CD1  LEU B 247      15.910   2.026  43.238  1.00 33.11      B    C
ATOM   4276  CD2  LEU B 247      17.467   2.186  45.173  1.00 33.11      B    C
ATOM   4277  C    LEU B 247      13.710   0.112  44.868  1.00 32.86      B    C
ATOM   4278  O    LEU B 247      13.666  -0.338  43.737  1.00 32.86      B    O
ATOM   4279  N    ALA B 248      13.826  -0.665  45.930  1.00 36.03      B    N
ATOM   4280  CA   ALA B 248      13.906  -2.104  45.767  1.00 36.03      B    C
ATOM   4281  CB   ALA B 248      13.967  -2.780  47.131  1.00 12.02      B    C
```

FIG. 3-65

```
ATOM   4282  C    ALA B 248      12.699  -2.606  44.977  1.00 36.03      B  C
ATOM   4283  O    ALA B 248      12.835  -3.436  44.086  1.00 36.03      B  O
ATOM   4284  N    GLU B 249      11.525  -2.076  45.306  1.00 35.82      B  N
ATOM   4285  CA   GLU B 249      10.276  -2.474  44.675  1.00 35.82      B  C
ATOM   4286  CB   GLU B 249       9.102  -1.800  45.368  1.00 36.69      B  C
ATOM   4287  CG   GLU B 249       7.783  -2.377  44.948  1.00 36.69      B  C
ATOM   4288  CD   GLU B 249       6.607  -1.837  45.732  1.00 36.69      B  C
ATOM   4289  OE1  GLU B 249       6.694  -1.767  46.981  1.00 36.69      B  O
ATOM   4290  OE2  GLU B 249       5.587  -1.500  45.092  1.00 36.69      B  O
ATOM   4291  C    GLU B 249      10.223  -2.151  43.203  1.00 35.82      B  C
ATOM   4292  O    GLU B 249       9.639  -2.888  42.418  1.00 35.82      B  O
ATOM   4293  N    LEU B 250      10.838  -1.042  42.828  1.00 38.98      B  N
ATOM   4294  CA   LEU B 250      10.834  -0.618  41.446  1.00 38.98      B  C
ATOM   4295  CB   LEU B 250      11.215   0.853  41.373  1.00 29.76      B  C
ATOM   4296  CG   LEU B 250      10.185   1.730  42.078  1.00 29.76      B  C
ATOM   4297  CD1  LEU B 250      10.688   3.149  42.122  1.00 29.76      B  C
ATOM   4298  CD2  LEU B 250       8.848   1.646  41.352  1.00 29.76      B  C
ATOM   4299  C    LEU B 250      11.750  -1.454  40.581  1.00 38.98      B  C
ATOM   4300  O    LEU B 250      11.520  -1.592  39.384  1.00 38.98      B  O
ATOM   4301  N    LEU B 251      12.791  -2.006  41.187  1.00 32.19      B  N
ATOM   4302  CA   LEU B 251      13.734  -2.847  40.471  1.00 32.19      B  C
ATOM   4303  CB   LEU B 251      15.098  -2.829  41.150  1.00 36.22      B  C
ATOM   4304  CG   LEU B 251      15.829  -1.528  41.463  1.00 36.22      B  C
ATOM   4305  CD1  LEU B 251      17.143  -1.878  42.141  1.00 36.22      B  C
ATOM   4306  CD2  LEU B 251      16.081  -0.728  40.210  1.00 36.22      B  C
ATOM   4307  C    LEU B 251      13.209  -4.268  40.515  1.00 32.19      B  C
ATOM   4308  O    LEU B 251      13.536  -5.093  39.674  1.00 32.19      B  O
ATOM   4309  N    LEU B 252      12.385  -4.535  41.516  1.00 41.40      B  N
ATOM   4310  CA   LEU B 252      11.818  -5.852  41.746  1.00 41.40      B  C
ATOM   4311  CB   LEU B 252      11.691  -6.094  43.245  1.00 45.11      B  C
ATOM   4312  CG   LEU B 252      12.455  -7.269  43.849  1.00 45.11      B  C
ATOM   4313  CD1  LEU B 252      13.946  -7.179  43.519  1.00 45.11      B  C
ATOM   4314  CD2  LEU B 252      12.240  -7.257  45.355  1.00 45.11      B  C
ATOM   4315  C    LEU B 252      10.470  -6.088  41.113  1.00 41.40      B  C
ATOM   4316  O    LEU B 252      10.135  -7.223  40.792  1.00 41.40      B  O
ATOM   4317  N    GLY B 253       9.680  -5.034  40.957  1.00 36.56      B  N
ATOM   4318  CA   GLY B 253       8.367  -5.195  40.365  1.00 36.56      B  C
ATOM   4319  C    GLY B 253       7.325  -5.597  41.390  1.00 36.56      B  C
ATOM   4320  O    GLY B 253       6.169  -5.816  41.051  1.00 36.56      B  O
ATOM   4321  N    GLN B 254       7.736  -5.701  42.647  1.00 39.83      B  N
ATOM   4322  CA   GLN B 254       6.836  -6.076  43.734  1.00 39.83      B  C
ATOM   4323  CB   GLN B 254       6.594  -7.589  43.718  1.00 43.57      B  C
ATOM   4324  CG   GLN B 254       7.871  -8.397  43.646  1.00 43.57      B  C
ATOM   4325  CD   GLN B 254       7.682  -9.836  44.054  1.00 43.57      B  C
ATOM   4326  OE1  GLN B 254       7.503 -10.153  45.234  1.00 43.57      B  O
ATOM   4327  NE2  GLN B 254       7.720 -10.722  43.077  1.00 43.57      B  N
ATOM   4328  C    GLN B 254       7.475  -5.668  45.063  1.00 39.83      B  C
ATOM   4329  O    GLN B 254       8.698  -5.560  45.161  1.00 39.83      B  O
ATOM   4330  N    PRO B 255       6.660  -5.430  46.102  1.00 42.09      B  N
ATOM   4331  CD   PRO B 255       5.193  -5.447  46.193  1.00 31.78      B  C
ATOM   4332  CA   PRO B 255       7.245  -5.039  47.385  1.00 42.09      B  C
ATOM   4333  CB   PRO B 255       6.043  -5.062  48.323  1.00 31.78      B  C
ATOM   4334  CG   PRO B 255       4.942  -4.623  47.436  1.00 31.78      B  C
ATOM   4335  C    PRO B 255       8.352  -6.004  47.808  1.00 42.09      B  C
ATOM   4336  O    PRO B 255       8.208  -7.216  47.676  1.00 42.09      B  O
ATOM   4337  N    ILE B 256       9.458  -5.454  48.301  1.00 40.78      B  N
ATOM   4338  CA   ILE B 256      10.587  -6.263  48.736  1.00 40.78      B  C
ATOM   4339  CB   ILE B 256      11.854  -5.380  48.925  1.00 32.43      B  C
ATOM   4340  CG2  ILE B 256      11.553  -4.221  49.850  1.00 32.43      B  C
ATOM   4341  CG1  ILE B 256      13.013  -6.213  49.460  1.00 32.43      B  C
ATOM   4342  CD1  ILE B 256      13.645  -7.083  48.447  1.00 32.43      B  C
ATOM   4343  C    ILE B 256      10.274  -7.039  50.022  1.00 40.78      B  C
ATOM   4344  O    ILE B 256      10.624  -8.218  50.133  1.00 40.78      B  O
ATOM   4345  N    PHE B 257       9.615  -6.392  50.984  1.00 34.25      B  N
ATOM   4346  CA   PHE B 257       9.263  -7.049  52.250  1.00 34.25      B  C
ATOM   4347  CB   PHE B 257       9.976  -6.396  53.446  1.00 36.22      B  C
ATOM   4348  CG   PHE B 257      11.453  -6.200  53.264  1.00 36.22      B  C
```

FIG. 3-66

```
ATOM   4349  CD1  PHE B 257      12.282   -7.267  52.981  1.00 36.22      B  C
ATOM   4350  CD2  PHE B 257      12.016   -4.933  53.403  1.00 36.22      B  C
ATOM   4351  CE1  PHE B 257      13.653   -7.075  52.837  1.00 36.22      B  C
ATOM   4352  CE2  PHE B 257      13.383   -4.731  53.262  1.00 36.22      B  C
ATOM   4353  CZ   PHE B 257      14.205   -5.801  52.978  1.00 36.22      B  C
ATOM   4354  C    PHE B 257       7.754   -6.955  52.491  1.00 34.25      B  C
ATOM   4355  O    PHE B 257       7.280   -6.005  53.104  1.00 34.25      B  O
ATOM   4356  N    PRO B 258       6.982   -7.949  52.020  1.00 42.22      B  N
ATOM   4357  CD   PRO B 258       7.426   -8.975  51.057  1.00 32.14      B  C
ATOM   4358  CA   PRO B 258       5.522   -7.996  52.169  1.00 42.22      B  C
ATOM   4359  CB   PRO B 258       5.090   -8.705  50.897  1.00 32.14      B  C
ATOM   4360  CG   PRO B 258       6.142   -9.749  50.779  1.00 32.14      B  C
ATOM   4361  C    PRO B 258       5.000   -8.721  53.410  1.00 42.22      B  C
ATOM   4362  O    PRO B 258       4.343   -9.755  53.292  1.00 42.22      B  O
ATOM   4363  N    GLY B 259       5.273   -8.180  54.592  1.00 45.98      B  N
ATOM   4364  CA   GLY B 259       4.818   -8.822  55.811  1.00 45.98      B  C
ATOM   4365  C    GLY B 259       3.308   -8.929  55.896  1.00 45.98      B  C
ATOM   4366  O    GLY B 259       2.603   -8.003  55.487  1.00 45.98      B  O
ATOM   4367  N    ASP B 260       2.791  -10.044  56.416  1.00 57.20      B  N
ATOM   4368  CA   ASP B 260       1.340  -10.173  56.526  1.00 57.20      B  C
ATOM   4369  CB   ASP B 260       0.889  -11.647  56.486  1.00 85.73      B  C
ATOM   4370  CG   ASP B 260       1.242  -12.413  57.755  1.00 85.73      B  C
ATOM   4371  OD1  ASP B 260       1.264  -11.785  58.842  1.00 85.73      B  O
ATOM   4372  OD2  ASP B 260       1.473  -13.649  57.661  1.00 85.73      B  O
ATOM   4373  C    ASP B 260       0.844   -9.500  57.804  1.00 57.20      B  C
ATOM   4374  O    ASP B 260      -0.352   -9.396  58.035  1.00 57.20      B  O
ATOM   4375  N    SER B 261       1.770   -9.047  58.638  1.00 49.50      B  N
ATOM   4376  CA   SER B 261       1.403   -8.362  59.872  1.00 49.50      B  C
ATOM   4377  CB   SER B 261       0.969   -9.363  60.938  1.00 56.87      B  C
ATOM   4378  OG   SER B 261       2.090  -10.062  61.451  1.00 56.87      B  O
ATOM   4379  C    SER B 261       2.604   -7.565  60.371  1.00 49.50      B  C
ATOM   4380  O    SER B 261       3.728   -7.775  59.914  1.00 49.50      B  O
ATOM   4381  N    GLY B 262       2.356   -6.647  61.302  1.00 42.57      B  N
ATOM   4382  CA   GLY B 262       3.416   -5.819  61.853  1.00 42.57      B  C
ATOM   4383  C    GLY B 262       4.643   -6.596  62.286  1.00 42.57      B  C
ATOM   4384  O    GLY B 262       5.747   -6.077  62.229  1.00 42.57      B  O
ATOM   4385  N    VAL B 263       4.460   -7.839  62.717  1.00 48.41      B  N
ATOM   4386  CA   VAL B 263       5.580   -8.668  63.163  1.00 48.41      B  C
ATOM   4387  CB   VAL B 263       5.173   -9.556  64.378  1.00 52.14      B  C
ATOM   4388  CG1  VAL B 263       6.263  -10.575  64.681  1.00 52.14      B  C
ATOM   4389  CG2  VAL B 263       4.931   -8.681  65.605  1.00 52.14      B  C
ATOM   4390  C    VAL B 263       6.135   -9.550  62.038  1.00 48.41      B  C
ATOM   4391  O    VAL B 263       7.347   -9.747  61.941  1.00 48.41      B  O
ATOM   4392  N    ASP B 264       5.257  -10.088  61.195  1.00 49.46      B  N
ATOM   4393  CA   ASP B 264       5.698  -10.916  60.065  1.00 49.46      B  C
ATOM   4394  CB   ASP B 264       4.480  -11.358  59.226  1.00 51.07      B  C
ATOM   4395  CG   ASP B 264       4.856  -12.273  58.046  1.00 51.07      B  C
ATOM   4396  OD1  ASP B 264       4.093  -12.285  57.052  1.00 51.07      B  O
ATOM   4397  OD2  ASP B 264       5.894  -12.982  58.107  1.00 51.07      B  O
ATOM   4398  C    ASP B 264       6.631  -10.035  59.216  1.00 49.46      B  C
ATOM   4399  O    ASP B 264       7.560  -10.525  58.572  1.00 49.46      B  O
ATOM   4400  N    GLN B 265       6.367   -8.728  59.236  1.00 32.91      B  N
ATOM   4401  CA   GLN B 265       7.146   -7.751  58.487  1.00 32.91      B  C
ATOM   4402  CB   GLN B 265       6.688   -6.332  58.850  1.00 37.01      B  C
ATOM   4403  CG   GLN B 265       7.316   -5.223  58.014  1.00 37.01      B  C
ATOM   4404  CD   GLN B 265       7.175   -5.485  56.534  1.00 37.01      B  C
ATOM   4405  OE1  GLN B 265       6.232   -6.140  56.108  1.00 37.01      B  O
ATOM   4406  NE2  GLN B 265       8.104   -4.968  55.742  1.00 37.01      B  N
ATOM   4407  C    GLN B 265       8.630   -7.903  58.784  1.00 32.91      B  C
ATOM   4408  O    GLN B 265       9.470   -7.887  57.881  1.00 32.91      B  O
ATOM   4409  N    LEU B 266       8.944   -8.037  60.063  1.00 47.01      B  N
ATOM   4410  CA   LEU B 266      10.321   -8.196  60.486  1.00 47.01      B  C
ATOM   4411  CB   LEU B 266      10.385   -8.221  62.012  1.00 38.05      B  C
ATOM   4412  CG   LEU B 266      11.740   -8.186  62.719  1.00 38.05      B  C
ATOM   4413  CD1  LEU B 266      12.628   -7.087  62.129  1.00 38.05      B  C
ATOM   4414  CD2  LEU B 266      11.500   -7.945  64.197  1.00 38.05      B  C
ATOM   4415  C    LEU B 266      10.872   -9.493  59.891  1.00 47.01      B  C
```

FIG. 3-67

| ATOM | 4416 | O | LEU | B | 266 | 11.987 | -9.520 | 59.350 | 1.00 | 47.01 | B | O |
| --- | --- | --- | --- | --- | --- | --- | --- | --- | --- | --- | --- | --- |
| ATOM | 4417 | N | VAL | B | 267 | 10.084 | -10.562 | 59.972 | 1.00 | 61.36 | B | N |
| ATOM | 4418 | CA | VAL | B | 267 | 10.507 | -11.845 | 59.430 | 1.00 | 61.36 | B | C |
| ATOM | 4419 | CB | VAL | B | 267 | 9.389 | -12.909 | 59.538 | 1.00 | 35.86 | B | C |
| ATOM | 4420 | CG1 | VAL | B | 267 | 9.855 | -14.227 | 58.927 | 1.00 | 35.86 | B | C |
| ATOM | 4421 | CG2 | VAL | B | 267 | 9.001 | -13.104 | 60.988 | 1.00 | 35.86 | B | C |
| ATOM | 4422 | C | VAL | B | 267 | 10.910 | -11.688 | 57.963 | 1.00 | 61.36 | B | C |
| ATOM | 4423 | O | VAL | B | 267 | 12.032 | -12.033 | 57.590 | 1.00 | 61.36 | B | O |
| ATOM | 4424 | N | GLU | B | 268 | 10.008 | -11.162 | 57.137 | 1.00 | 35.56 | B | N |
| ATOM | 4425 | CA | GLU | B | 268 | 10.295 | -10.963 | 55.718 | 1.00 | 35.56 | B | C |
| ATOM | 4426 | CB | GLU | B | 268 | 9.151 | -10.186 | 55.054 | 1.00 | 52.64 | B | C |
| ATOM | 4427 | CG | GLU | B | 268 | 7.842 | -10.968 | 54.895 | 1.00 | 52.64 | B | C |
| ATOM | 4428 | CD | GLU | B | 268 | 7.987 | -12.190 | 53.983 | 1.00 | 52.64 | B | C |
| ATOM | 4429 | OE1 | GLU | B | 268 | 8.418 | -12.031 | 52.816 | 1.00 | 52.64 | B | O |
| ATOM | 4430 | OE2 | GLU | B | 268 | 7.663 | -13.314 | 54.434 | 1.00 | 52.64 | B | O |
| ATOM | 4431 | C | GLU | B | 268 | 11.612 | -10.216 | 55.518 | 1.00 | 35.56 | B | C |
| ATOM | 4432 | O | GLU | B | 268 | 12.412 | -10.581 | 54.660 | 1.00 | 35.56 | B | O |
| ATOM | 4433 | N | ILE | B | 269 | 11.821 | -9.165 | 56.315 | 1.00 | 47.73 | B | N |
| ATOM | 4434 | CA | ILE | B | 269 | 13.042 | -8.356 | 56.262 | 1.00 | 47.73 | B | C |
| ATOM | 4435 | CB | ILE | B | 269 | 13.025 | -7.226 | 57.324 | 1.00 | 32.01 | B | C |
| ATOM | 4436 | CG2 | ILE | B | 269 | 14.432 | -6.711 | 57.560 | 1.00 | 32.01 | B | C |
| ATOM | 4437 | CG1 | ILE | B | 269 | 12.113 | -6.090 | 56.869 | 1.00 | 32.01 | B | C |
| ATOM | 4438 | CD1 | ILE | B | 269 | 12.026 | -4.947 | 57.846 | 1.00 | 32.01 | B | C |
| ATOM | 4439 | C | ILE | B | 269 | 14.246 | -9.242 | 56.543 | 1.00 | 47.73 | B | C |
| ATOM | 4440 | O | ILE | B | 269 | 15.234 | -9.243 | 55.797 | 1.00 | 47.73 | B | O |
| ATOM | 4441 | N | ILE | B | 270 | 14.146 | -9.984 | 57.641 | 1.00 | 45.98 | B | N |
| ATOM | 4442 | CA | ILE | B | 270 | 15.200 | -10.894 | 58.063 | 1.00 | 45.98 | B | C |
| ATOM | 4443 | CB | ILE | B | 270 | 14.802 | -11.591 | 59.392 | 1.00 | 38.43 | B | C |
| ATOM | 4444 | CG2 | ILE | B | 270 | 15.673 | -12.817 | 59.642 | 1.00 | 38.43 | B | C |
| ATOM | 4445 | CG1 | ILE | B | 270 | 14.928 | -10.589 | 60.542 | 1.00 | 38.43 | B | C |
| ATOM | 4446 | CD1 | ILE | B | 270 | 14.376 | -11.081 | 61.857 | 1.00 | 38.43 | B | C |
| ATOM | 4447 | C | ILE | B | 270 | 15.516 | -11.941 | 56.992 | 1.00 | 45.98 | B | C |
| ATOM | 4448 | O | ILE | B | 270 | 16.642 | -12.429 | 56.897 | 1.00 | 45.98 | B | O |
| ATOM | 4449 | N | LYS | B | 271 | 14.526 | -12.268 | 56.170 | 1.00 | 51.03 | B | N |
| ATOM | 4450 | CA | LYS | B | 271 | 14.721 | -13.268 | 55.129 | 1.00 | 51.03 | B | C |
| ATOM | 4451 | CB | LYS | B | 271 | 13.385 | -13.630 | 54.499 | 1.00 | 48.51 | B | C |
| ATOM | 4452 | CG | LYS | B | 271 | 12.458 | -14.291 | 55.497 | 1.00 | 48.51 | B | C |
| ATOM | 4453 | CD | LYS | B | 271 | 11.033 | -14.442 | 54.972 | 1.00 | 48.51 | B | C |
| ATOM | 4454 | CE | LYS | B | 271 | 10.963 | -15.425 | 53.821 | 1.00 | 48.51 | B | C |
| ATOM | 4455 | NZ | LYS | B | 271 | 9.564 | -15.631 | 53.366 | 1.00 | 48.51 | B | N |
| ATOM | 4456 | C | LYS | B | 271 | 15.728 | -12.872 | 54.065 | 1.00 | 51.03 | B | C |
| ATOM | 4457 | O | LYS | B | 271 | 16.295 | -13.733 | 53.409 | 1.00 | 51.03 | B | O |
| ATOM | 4458 | N | VAL | B | 272 | 15.968 | -11.582 | 53.886 | 1.00 | 40.60 | B | N |
| ATOM | 4459 | CA | VAL | B | 272 | 16.956 | -11.176 | 52.897 | 1.00 | 40.60 | B | C |
| ATOM | 4460 | CB | VAL | B | 272 | 16.380 | -10.142 | 51.867 | 1.00 | 38.82 | B | C |
| ATOM | 4461 | CG1 | VAL | B | 272 | 14.970 | -10.513 | 51.484 | 1.00 | 38.82 | B | C |
| ATOM | 4462 | CG2 | VAL | B | 272 | 16.419 | -8.747 | 52.428 | 1.00 | 38.82 | B | C |
| ATOM | 4463 | C | VAL | B | 272 | 18.183 | -10.587 | 53.608 | 1.00 | 40.60 | B | C |
| ATOM | 4464 | O | VAL | B | 272 | 19.321 | -10.917 | 53.273 | 1.00 | 40.60 | B | O |
| ATOM | 4465 | N | LEU | B | 273 | 17.955 | -9.736 | 54.607 | 1.00 | 50.54 | B | N |
| ATOM | 4466 | CA | LEU | B | 273 | 19.066 | -9.127 | 55.326 | 1.00 | 50.54 | B | C |
| ATOM | 4467 | CB | LEU | B | 273 | 18.604 | -7.868 | 56.080 | 1.00 | 41.36 | B | C |
| ATOM | 4468 | CG | LEU | B | 273 | 17.903 | -6.701 | 55.364 | 1.00 | 41.36 | B | C |
| ATOM | 4469 | CD1 | LEU | B | 273 | 17.881 | -5.515 | 56.323 | 1.00 | 41.36 | B | C |
| ATOM | 4470 | CD2 | LEU | B | 273 | 18.617 | -6.308 | 54.086 | 1.00 | 41.36 | B | C |
| ATOM | 4471 | C | LEU | B | 273 | 19.708 | -10.103 | 56.313 | 1.00 | 50.54 | B | C |
| ATOM | 4472 | O | LEU | B | 273 | 20.863 | -9.926 | 56.718 | 1.00 | 50.54 | B | O |
| ATOM | 4473 | N | GLY | B | 274 | 18.962 | -11.135 | 56.695 | 1.00 | 58.41 | B | N |
| ATOM | 4474 | CA | GLY | B | 274 | 19.479 | -12.104 | 57.648 | 1.00 | 58.41 | B | C |
| ATOM | 4475 | C | GLY | B | 274 | 19.266 | -11.619 | 59.074 | 1.00 | 58.41 | B | C |
| ATOM | 4476 | O | GLY | B | 274 | 19.039 | -10.428 | 59.297 | 1.00 | 58.41 | B | O |
| ATOM | 4477 | N | THR | B | 275 | 19.331 | -12.528 | 60.045 | 1.00 | 52.95 | B | N |
| ATOM | 4478 | CA | THR | B | 275 | 19.141 | -12.153 | 61.445 | 1.00 | 52.95 | B | C |
| ATOM | 4479 | CB | THR | B | 275 | 19.414 | -13.344 | 62.365 | 1.00 | 46.17 | B | C |
| ATOM | 4480 | OG1 | THR | B | 275 | 18.563 | -14.439 | 61.992 | 1.00 | 46.17 | B | O |
| ATOM | 4481 | CG2 | THR | B | 275 | 19.139 | -12.966 | 63.807 | 1.00 | 46.17 | B | C |
| ATOM | 4482 | C | THR | B | 275 | 20.059 | -10.987 | 61.842 | 1.00 | 52.95 | B | C |

FIG. 3-68

```
ATOM   4483  O    THR B 275      21.242 -10.972  61.505  1.00 52.95      B  O
ATOM   4484  N    PRO B 276      19.521  -9.991  62.564  1.00 42.77      B  N
ATOM   4485  CD   PRO B 276      18.168  -9.888  63.126  1.00 27.79      B  C
ATOM   4486  CA   PRO B 276      20.342  -8.845  62.970  1.00 42.77      B  C
ATOM   4487  CB   PRO B 276      19.312  -7.825  63.455  1.00 27.79      B  C
ATOM   4488  CG   PRO B 276      17.951  -8.425  63.101  1.00 27.79      B  C
ATOM   4489  C    PRO B 276      21.304  -9.226  64.088  1.00 42.77      B  C
ATOM   4490  O    PRO B 276      20.949 -10.012  64.970  1.00 42.77      B  O
ATOM   4491  N    THR B 277      22.511  -8.667  64.066  1.00 47.00      B  N
ATOM   4492  CA   THR B 277      23.490  -8.962  65.111  1.00 47.00      B  C
ATOM   4493  CB   THR B 277      24.873  -8.402  64.768  1.00 47.52      B  C
ATOM   4494  OG1  THR B 277      24.901  -6.998  65.044  1.00 47.52      B  O
ATOM   4495  CG2  THR B 277      25.182  -8.604  63.313  1.00 47.52      B  C
ATOM   4496  C    THR B 277      23.058  -8.299  66.419  1.00 47.00      B  C
ATOM   4497  O    THR B 277      22.225  -7.388  66.419  1.00 47.00      B  O
ATOM   4498  N    ALA B 278      23.651  -8.733  67.530  1.00 46.03      B  N
ATOM   4499  CA   ALA B 278      23.326  -8.158  68.832  1.00 46.03      B  C
ATOM   4500  CB   ALA B 278      24.235  -8.766  69.912  1.00 48.64      B  C
ATOM   4501  C    ALA B 278      23.518  -6.638  68.765  1.00 46.03      B  C
ATOM   4502  O    ALA B 278      22.646  -5.856  69.173  1.00 46.03      B  O
ATOM   4503  N    GLU B 279      24.672  -6.241  68.237  1.00 56.62      B  N
ATOM   4504  CA   GLU B 279      25.027  -4.837  68.085  1.00 56.62      B  C
ATOM   4505  CB   GLU B 279      26.322  -4.708  67.285  1.00 92.84      B  C
ATOM   4506  CG   GLU B 279      27.533  -5.432  67.893  1.00 92.84      B  C
ATOM   4507  CD   GLU B 279      27.252  -6.898  68.286  1.00 92.84      B  C
ATOM   4508  OE1  GLU B 279      27.115  -7.162  69.515  1.00 92.84      B  O
ATOM   4509  OE2  GLU B 279      27.165  -7.771  67.378  1.00 92.84      B  O
ATOM   4510  C    GLU B 279      23.896  -4.157  67.331  1.00 56.62      B  C
ATOM   4511  O    GLU B 279      23.199  -3.299  67.886  1.00 56.62      B  O
ATOM   4512  N    GLN B 280      23.727  -4.552  66.066  1.00 49.32      B  N
ATOM   4513  CA   GLN B 280      22.671  -4.030  65.198  1.00 49.32      B  C
ATOM   4514  CB   GLN B 280      22.436  -4.992  64.028  1.00 42.19      B  C
ATOM   4515  CG   GLN B 280      23.384  -4.790  62.851  1.00 42.19      B  C
ATOM   4516  CD   GLN B 280      23.237  -5.871  61.799  1.00 42.19      B  C
ATOM   4517  OE1  GLN B 280      23.698  -5.723  60.660  1.00 42.19      B  O
ATOM   4518  NE2  GLN B 280      22.600  -6.980  62.180  1.00 42.19      B  N
ATOM   4519  C    GLN B 280      21.366  -3.826  65.961  1.00 49.32      B  C
ATOM   4520  O    GLN B 280      20.835  -2.717  66.020  1.00 49.32      B  O
ATOM   4521  N    ILE B 281      20.850  -4.900  66.541  1.00 49.78      B  N
ATOM   4522  CA   ILE B 281      19.618  -4.815  67.312  1.00 49.78      B  C
ATOM   4523  CB   ILE B 281      19.206  -6.203  67.882  1.00 45.29      B  C
ATOM   4524  CG2  ILE B 281      18.097  -6.040  68.915  1.00 45.29      B  C
ATOM   4525  CG1  ILE B 281      18.742  -7.117  66.741  1.00 45.29      B  C
ATOM   4526  CD1  ILE B 281      18.181  -8.460  67.186  1.00 45.29      B  C
ATOM   4527  C    ILE B 281      19.748  -3.820  68.473  1.00 49.78      B  C
ATOM   4528  O    ILE B 281      18.743  -3.427  69.061  1.00 49.78      B  O
ATOM   4529  N    ALA B 282      20.978  -3.408  68.793  1.00 53.14      B  N
ATOM   4530  CA   ALA B 282      21.214  -2.461  69.891  1.00 53.14      B  C
ATOM   4531  CB   ALA B 282      22.588  -2.714  70.533  1.00 71.09      B  C
ATOM   4532  C    ALA B 282      21.100  -0.994  69.476  1.00 53.14      B  C
ATOM   4533  O    ALA B 282      20.740  -0.139  70.290  1.00 53.14      B  O
ATOM   4534  N    GLU B 283      21.410  -0.694  68.222  1.00 40.56      B  N
ATOM   4535  CA   GLU B 283      21.322   0.683  67.755  1.00 40.56      B  C
ATOM   4536  CB   GLU B 283      22.331   0.919  66.639  1.00 68.04      B  C
ATOM   4537  CG   GLU B 283      23.723   0.421  66.982  1.00 68.04      B  C
ATOM   4538  CD   GLU B 283      24.822   1.344  66.462  1.00 68.04      B  C
ATOM   4539  OE1  GLU B 283      25.715   0.863  65.708  1.00 68.04      B  O
ATOM   4540  OE2  GLU B 283      24.785   2.554  66.816  1.00 68.04      B  O
ATOM   4541  C    GLU B 283      19.904   1.032  67.282  1.00 40.56      B  C
ATOM   4542  O    GLU B 283      19.633   2.157  66.849  1.00 40.56      B  O
ATOM   4543  N    MET B 284      19.007   0.055  67.384  1.00 49.75      B  N
ATOM   4544  CA   MET B 284      17.617   0.230  67.004  1.00 49.75      B  C
ATOM   4545  CB   MET B 284      17.107  -1.018  66.257  1.00 52.86      B  C
ATOM   4546  CG   MET B 284      17.624  -1.183  64.807  1.00 52.86      B  C
ATOM   4547  SD   MET B 284      17.371  -2.860  64.070  1.00 52.86      B  S
ATOM   4548  CE   MET B 284      15.705  -2.803  63.774  1.00 52.86      B  C
ATOM   4549  C    MET B 284      16.773   0.461  68.260  1.00 49.75      B  C
```

FIG. 3-69

```
ATOM   4550  O    MET B 284      15.562   0.255  68.240  1.00 49.75      B  O
ATOM   4551  N    GLY B 285      17.404   0.883  69.356  1.00 48.80      B  N
ATOM   4552  CA   GLY B 285      16.661   1.111  70.590  1.00 48.80      B  C
ATOM   4553  C    GLY B 285      15.872  -0.116  71.028  1.00 48.80      B  C
ATOM   4554  O    GLY B 285      16.293  -1.260  70.812  1.00 48.80      B  O
ATOM   4555  N    ALA B 296      17.466 -16.972  58.731  1.00 53.57      B  N
ATOM   4556  CA   ALA B 296      18.559 -16.598  59.620  1.00 53.57      B  C
ATOM   4557  CB   ALA B 296      18.891 -17.773  60.570  1.00 21.86      B  C
ATOM   4558  C    ALA B 296      19.817 -16.147  58.855  1.00 53.57      B  C
ATOM   4559  O    ALA B 296      20.500 -15.215  59.284  1.00 53.57      B  O
ATOM   4560  N    ALA B 297      20.125 -16.784  57.725  1.00 66.06      B  N
ATOM   4561  CA   ALA B 297      21.321 -16.405  56.957  1.00 66.06      B  C
ATOM   4562  CB   ALA B 297      21.935 -17.643  56.293  1.00 40.80      B  C
ATOM   4563  C    ALA B 297      21.045 -15.314  55.907  1.00 66.06      B  C
ATOM   4564  O    ALA B 297      20.015 -15.340  55.223  1.00 66.06      B  O
ATOM   4565  N    ALA B 298      21.975 -14.368  55.777  1.00 36.23      B  N
ATOM   4566  CA   ALA B 298      21.827 -13.256  54.843  1.00 36.23      B  C
ATOM   4567  CB   ALA B 298      22.861 -12.190  55.144  1.00 60.82      B  C
ATOM   4568  C    ALA B 298      21.911 -13.652  53.375  1.00 36.23      B  C
ATOM   4569  O    ALA B 298      22.878 -14.274  52.931  1.00 36.23      B  O
ATOM   4570  N    HIS B 299      20.889 -13.261  52.624  1.00 46.16      B  N
ATOM   4571  CA   HIS B 299      20.791 -13.555  51.199  1.00 46.16      B  C
ATOM   4572  CB   HIS B 299      19.316 -13.570  50.799  1.00 56.19      B  C
ATOM   4573  CG   HIS B 299      19.043 -14.297  49.524  1.00 56.19      B  C
ATOM   4574  CD2  HIS B 299      18.844 -15.613  49.275  1.00 56.19      B  C
ATOM   4575  ND1  HIS B 299      18.963 -13.661  48.303  1.00 56.19      B  N
ATOM   4576  CE1  HIS B 299      18.726 -14.552  47.357  1.00 56.19      B  C
ATOM   4577  NE2  HIS B 299      18.649 -15.744  47.920  1.00 56.19      B  N
ATOM   4578  C    HIS B 299      21.558 -12.488  50.421  1.00 46.16      B  C
ATOM   4579  O    HIS B 299      21.272 -11.301  50.523  1.00 46.16      B  O
ATOM   4580  N    PRO B 300      22.525 -12.900  49.599  1.00 56.26      B  N
ATOM   4581  CD   PRO B 300      22.777 -14.265  49.090  1.00 46.90      B  C
ATOM   4582  CA   PRO B 300      23.290 -11.895  48.845  1.00 56.26      B  C
ATOM   4583  CB   PRO B 300      24.251 -12.749  48.012  1.00 46.90      B  C
ATOM   4584  CG   PRO B 300      23.424 -13.998  47.741  1.00 46.90      B  C
ATOM   4585  C    PRO B 300      22.434 -10.941  47.992  1.00 56.26      B  C
ATOM   4586  O    PRO B 300      21.708 -11.376  47.090  1.00 56.26      B  O
ATOM   4587  N    TRP B 301      22.541  -9.642  48.290  1.00 57.52      B  N
ATOM   4588  CA   TRP B 301      21.795  -8.601  47.582  1.00 57.52      B  C
ATOM   4589  CB   TRP B 301      22.438  -7.231  47.812  1.00 49.94      B  C
ATOM   4590  CG   TRP B 301      21.896  -6.515  49.012  1.00 49.94      B  C
ATOM   4591  CD2  TRP B 301      20.523  -6.198  49.276  1.00 49.94      B  C
ATOM   4592  CE2  TRP B 301      20.468  -5.609  50.562  1.00 49.94      B  C
ATOM   4593  CE3  TRP B 301      19.333  -6.375  48.564  1.00 49.94      B  C
ATOM   4594  CD1  TRP B 301      22.602  -6.092  50.107  1.00 49.94      B  C
ATOM   4595  NE1  TRP B 301      21.749  -5.547  51.043  1.00 49.94      B  N
ATOM   4596  CZ2  TRP B 301      19.264  -5.177  51.139  1.00 49.94      B  C
ATOM   4597  CZ3  TRP B 301      18.136  -5.943  49.139  1.00 49.94      B  C
ATOM   4598  CH2  TRP B 301      18.112  -5.362  50.416  1.00 49.94      B  C
ATOM   4599  C    TRP B 301      21.648  -8.834  46.083  1.00 57.52      B  C
ATOM   4600  O    TRP B 301      20.562  -8.645  45.517  1.00 57.52      B  O
ATOM   4601  N    THR B 302      22.736  -9.242  45.440  1.00 55.30      B  N
ATOM   4602  CA   THR B 302      22.709  -9.484  44.001  1.00 55.30      B  C
ATOM   4603  CB   THR B 302      24.120  -9.827  43.477  1.00 68.12      B  C
ATOM   4604  OG1  THR B 302      24.568 -11.052  44.082  1.00 68.12      B  O
ATOM   4605  CG2  THR B 302      25.096  -8.699  43.817  1.00 68.12      B  C
ATOM   4606  C    THR B 302      21.737 -10.599  43.587  1.00 55.30      B  C
ATOM   4607  O    THR B 302      20.953 -10.435  42.653  1.00 55.30      B  O
ATOM   4608  N    ALA B 303      21.781 -11.731  44.277  1.00 44.24      B  N
ATOM   4609  CA   ALA B 303      20.887 -12.833  43.935  1.00 44.24      B  C
ATOM   4610  CB   ALA B 303      21.370 -14.140  44.618  1.00 66.05      B  C
ATOM   4611  C    ALA B 303      19.451 -12.498  44.355  1.00 44.24      B  C
ATOM   4612  O    ALA B 303      18.575 -13.365  44.372  1.00 44.24      B  O
ATOM   4613  N    VAL B 304      19.225 -11.233  44.696  1.00 47.34      B  N
ATOM   4614  CA   VAL B 304      17.906 -10.767  45.120  1.00 47.34      B  C
ATOM   4615  CB   VAL B 304      18.010  -9.799  46.344  1.00 42.73      B  C
ATOM   4616  CG1  VAL B 304      16.626  -9.278  46.737  1.00 42.73      B  C
```

FIG. 3-70

| ATOM | 4617 | CG2 | VAL | B | 304 | 18.664 | -10.514 | 47.508 | 1.00 | 42.73 | B | C |
| --- | --- | --- | --- | --- | --- | --- | --- | --- | --- | --- | --- | --- |
| ATOM | 4618 | C | VAL | B | 304 | 17.196 | -10.043 | 43.979 | 1.00 | 47.34 | B | C |
| ATOM | 4619 | O | VAL | B | 304 | 15.977 | -10.105 | 43.866 | 1.00 | 47.34 | B | O |
| ATOM | 4620 | N | PHE | B | 305 | 17.965 | -9.363 | 43.136 | 1.00 | 35.28 | B | N |
| ATOM | 4621 | CA | PHE | B | 305 | 17.392 | -8.630 | 42.015 | 1.00 | 35.28 | B | C |
| ATOM | 4622 | CB | PHE | B | 305 | 18.068 | -7.263 | 41.905 | 1.00 | 44.78 | B | C |
| ATOM | 4623 | CG | PHE | B | 305 | 17.764 | -6.363 | 43.056 | 1.00 | 44.78 | B | C |
| ATOM | 4624 | CD1 | PHE | B | 305 | 16.614 | -5.580 | 43.057 | 1.00 | 44.78 | B | C |
| ATOM | 4625 | CD2 | PHE | B | 305 | 18.570 | -6.374 | 44.191 | 1.00 | 44.78 | B | C |
| ATOM | 4626 | CE1 | PHE | B | 305 | 16.266 | -4.826 | 44.178 | 1.00 | 44.78 | B | C |
| ATOM | 4627 | CE2 | PHE | B | 305 | 18.230 | -5.622 | 45.318 | 1.00 | 44.78 | B | C |
| ATOM | 4628 | CZ | PHE | B | 305 | 17.076 | -4.850 | 45.312 | 1.00 | 44.78 | B | C |
| ATOM | 4629 | C | PHE | B | 305 | 17.491 | -9.381 | 40.690 | 1.00 | 35.28 | B | C |
| ATOM | 4630 | O | PHE | B | 305 | 18.303 | -10.289 | 40.538 | 1.00 | 35.28 | B | O |
| ATOM | 4631 | N | ARG | B | 306 | 16.650 | -9.019 | 39.730 | 1.00 | 51.62 | B | N |
| ATOM | 4632 | CA | ARG | B | 306 | 16.724 | -9.698 | 38.448 | 1.00 | 51.62 | B | C |
| ATOM | 4633 | CB | ARG | B | 306 | 15.697 | -9.136 | 37.449 | 1.00 | 89.62 | B | C |
| ATOM | 4634 | CG | ARG | B | 306 | 15.625 | -7.604 | 37.346 | 1.00 | 89.62 | B | C |
| ATOM | 4635 | CD | ARG | B | 306 | 14.773 | -7.169 | 36.148 | 1.00 | 89.62 | B | C |
| ATOM | 4636 | NE | ARG | B | 306 | 15.604 | -6.948 | 34.965 | 1.00 | 89.62 | B | N |
| ATOM | 4637 | CZ | ARG | B | 306 | 16.308 | -5.837 | 34.739 | 1.00 | 89.62 | B | C |
| ATOM | 4638 | NH1 | ARG | B | 306 | 16.281 | -4.835 | 35.619 | 1.00 | 89.62 | B | N |
| ATOM | 4639 | NH2 | ARG | B | 306 | 17.034 | -5.721 | 33.630 | 1.00 | 89.62 | B | N |
| ATOM | 4640 | C | ARG | B | 306 | 18.141 | -9.551 | 37.894 | 1.00 | 51.62 | B | C |
| ATOM | 4641 | O | ARG | B | 306 | 18.860 | -8.602 | 38.222 | 1.00 | 51.62 | B | O |
| ATOM | 4642 | N | PRO | B | 307 | 18.563 | -10.507 | 37.057 | 1.00 | 57.13 | B | N |
| ATOM | 4643 | CD | PRO | B | 307 | 17.759 | -11.704 | 36.733 | 1.00 | 81.46 | B | C |
| ATOM | 4644 | CA | PRO | B | 307 | 19.876 | -10.578 | 36.409 | 1.00 | 57.13 | B | C |
| ATOM | 4645 | CB | PRO | B | 307 | 19.636 | -11.580 | 35.288 | 1.00 | 81.46 | B | C |
| ATOM | 4646 | CG | PRO | B | 307 | 18.752 | -12.586 | 35.972 | 1.00 | 81.46 | B | C |
| ATOM | 4647 | C | PRO | B | 307 | 20.499 | -9.281 | 35.906 | 1.00 | 57.13 | B | C |
| ATOM | 4648 | O | PRO | B | 307 | 21.584 | -8.901 | 36.343 | 1.00 | 57.13 | B | O |
| ATOM | 4649 | N | ALA | B | 308 | 19.826 | -8.602 | 34.984 | 1.00 | 66.58 | B | N |
| ATOM | 4650 | CA | ALA | B | 308 | 20.370 | -7.363 | 34.415 | 1.00 | 66.58 | B | C |
| ATOM | 4651 | CB | ALA | B | 308 | 19.839 | -7.176 | 32.984 | 1.00 | 70.42 | B | C |
| ATOM | 4652 | C | ALA | B | 308 | 20.127 | -6.090 | 35.239 | 1.00 | 66.58 | B | C |
| ATOM | 4653 | O | ALA | B | 308 | 20.043 | -4.992 | 34.687 | 1.00 | 66.58 | B | O |
| ATOM | 4654 | N | THR | B | 309 | 20.031 | -6.244 | 36.558 | 1.00 | 57.01 | B | N |
| ATOM | 4655 | CA | THR | B | 309 | 19.812 | -5.115 | 37.461 | 1.00 | 57.01 | B | C |
| ATOM | 4656 | CB | THR | B | 309 | 19.383 | -5.597 | 38.856 | 1.00 | 39.03 | B | C |
| ATOM | 4657 | OG1 | THR | B | 309 | 18.133 | -6.295 | 38.768 | 1.00 | 39.03 | B | O |
| ATOM | 4658 | CG2 | THR | B | 309 | 19.239 | -4.418 | 39.792 | 1.00 | 39.03 | B | C |
| ATOM | 4659 | C | THR | B | 309 | 21.096 | -4.299 | 37.606 | 1.00 | 57.01 | B | C |
| ATOM | 4660 | O | THR | B | 309 | 22.131 | -4.818 | 38.030 | 1.00 | 57.01 | B | O |
| ATOM | 4661 | N | PRO | B | 310 | 21.049 | -3.008 | 37.252 | 1.00 | 62.05 | B | N |
| ATOM | 4662 | CD | PRO | B | 310 | 19.865 | -2.228 | 36.852 | 1.00 | 35.50 | B | C |
| ATOM | 4663 | CA | PRO | B | 310 | 22.236 | -2.146 | 37.358 | 1.00 | 62.05 | B | C |
| ATOM | 4664 | CB | PRO | B | 310 | 21.658 | -0.745 | 37.180 | 1.00 | 35.50 | B | C |
| ATOM | 4665 | CG | PRO | B | 310 | 20.488 | -0.980 | 36.293 | 1.00 | 35.50 | B | C |
| ATOM | 4666 | C | PRO | B | 310 | 22.975 | -2.295 | 38.704 | 1.00 | 62.05 | B | C |
| ATOM | 4667 | O | PRO | B | 310 | 22.393 | -2.115 | 39.785 | 1.00 | 62.05 | B | O |
| ATOM | 4668 | N | PRO | B | 311 | 24.265 | -2.634 | 38.656 | 1.00 | 54.29 | B | N |
| ATOM | 4669 | CD | PRO | B | 311 | 25.011 | -3.040 | 37.456 | 1.00 | 41.27 | B | C |
| ATOM | 4670 | CA | PRO | B | 311 | 25.084 | -2.803 | 39.860 | 1.00 | 54.29 | B | C |
| ATOM | 4671 | CB | PRO | B | 311 | 26.485 | -2.913 | 39.291 | 1.00 | 41.27 | B | C |
| ATOM | 4672 | CG | PRO | B | 311 | 26.235 | -3.713 | 38.053 | 1.00 | 41.27 | B | C |
| ATOM | 4673 | C | PRO | B | 311 | 24.956 | -1.668 | 40.882 | 1.00 | 54.29 | B | C |
| ATOM | 4674 | O | PRO | B | 311 | 24.799 | -1.917 | 42.088 | 1.00 | 54.29 | B | O |
| ATOM | 4675 | N | GLU | B | 312 | 25.017 | -0.428 | 40.407 | 1.00 | 40.55 | B | N |
| ATOM | 4676 | CA | GLU | B | 312 | 24.907 | 0.715 | 41.298 | 1.00 | 40.55 | B | C |
| ATOM | 4677 | CB | GLU | B | 312 | 25.207 | 2.018 | 40.562 | 1.00 | 52.55 | B | C |
| ATOM | 4678 | CG | GLU | B | 312 | 26.558 | 2.044 | 39.904 | 1.00 | 52.55 | B | C |
| ATOM | 4679 | CD | GLU | B | 312 | 26.535 | 1.434 | 38.518 | 1.00 | 52.55 | B | C |
| ATOM | 4680 | OE1 | GLU | B | 312 | 25.914 | 0.361 | 38.328 | 1.00 | 52.55 | B | O |
| ATOM | 4681 | OE2 | GLU | B | 312 | 27.150 | 2.038 | 37.616 | 1.00 | 52.55 | B | O |
| ATOM | 4682 | C | GLU | B | 312 | 23.527 | 0.808 | 41.928 | 1.00 | 40.55 | B | C |
| ATOM | 4683 | O | GLU | B | 312 | 23.382 | 1.322 | 43.029 | 1.00 | 40.55 | B | O |

FIG. 3-71

| ATOM | 4684 | N | ALA | B | 313 | 22.506 | 0.333 | 41.232 | 1.00 | 24.24 | B | N |
|---|---|---|---|---|---|---|---|---|---|---|---|---|
| ATOM | 4685 | CA | ALA | B | 313 | 21.173 | 0.378 | 41.800 | 1.00 | 24.24 | B | C |
| ATOM | 4686 | CB | ALA | B | 313 | 20.162 | -0.206 | 40.815 | 1.00 | 42.45 | B | C |
| ATOM | 4687 | C | ALA | B | 313 | 21.249 | -0.473 | 43.063 | 1.00 | 24.24 | B | C |
| ATOM | 4688 | O | ALA | B | 313 | 20.747 | -0.106 | 44.119 | 1.00 | 24.24 | B | O |
| ATOM | 4689 | N | ILE | B | 314 | 21.915 | -1.613 | 42.937 | 1.00 | 39.01 | B | N |
| ATOM | 4690 | CA | ILE | B | 314 | 22.076 | -2.541 | 44.044 | 1.00 | 39.01 | B | C |
| ATOM | 4691 | CB | ILE | B | 314 | 22.703 | -3.858 | 43.555 | 1.00 | 34.60 | B | C |
| ATOM | 4692 | CG2 | ILE | B | 314 | 23.005 | -4.772 | 44.740 | 1.00 | 34.60 | B | C |
| ATOM | 4693 | CG1 | ILE | B | 314 | 21.745 | -4.542 | 42.570 | 1.00 | 34.60 | B | C |
| ATOM | 4694 | CD1 | ILE | B | 314 | 22.321 | -5.754 | 41.875 | 1.00 | 34.60 | B | C |
| ATOM | 4695 | C | ILE | B | 314 | 22.938 | -1.937 | 45.148 | 1.00 | 39.01 | B | C |
| ATOM | 4696 | O | ILE | B | 314 | 22.586 | -1.985 | 46.333 | 1.00 | 39.01 | B | O |
| ATOM | 4697 | N | ALA | B | 315 | 24.069 | -1.362 | 44.766 | 1.00 | 39.84 | B | N |
| ATOM | 4698 | CA | ALA | B | 315 | 24.948 | -0.744 | 45.752 | 1.00 | 39.84 | B | C |
| ATOM | 4699 | CB | ALA | B | 315 | 26.081 | -0.010 | 45.058 | 1.00 | 32.99 | B | C |
| ATOM | 4700 | C | ALA | B | 315 | 24.154 | 0.231 | 46.604 | 1.00 | 39.84 | B | C |
| ATOM | 4701 | O | ALA | B | 315 | 24.147 | 0.139 | 47.832 | 1.00 | 39.84 | B | O |
| ATOM | 4702 | N | LEU | B | 316 | 23.490 | 1.171 | 45.932 | 1.00 | 49.95 | B | N |
| ATOM | 4703 | CA | LEU | B | 316 | 22.672 | 2.192 | 46.582 | 1.00 | 49.95 | B | C |
| ATOM | 4704 | CB | LEU | B | 316 | 21.991 | 3.069 | 45.531 | 1.00 | 38.96 | B | C |
| ATOM | 4705 | CG | LEU | B | 316 | 20.815 | 3.910 | 46.024 | 1.00 | 38.96 | B | C |
| ATOM | 4706 | CD1 | LEU | B | 316 | 21.292 | 4.966 | 47.008 | 1.00 | 38.96 | B | C |
| ATOM | 4707 | CD2 | LEU | B | 316 | 20.135 | 4.547 | 44.843 | 1.00 | 38.96 | B | C |
| ATOM | 4708 | C | LEU | B | 316 | 21.610 | 1.577 | 47.468 | 1.00 | 49.95 | B | C |
| ATOM | 4709 | O | LEU | B | 316 | 21.379 | 2.025 | 48.585 | 1.00 | 49.95 | B | O |
| ATOM | 4710 | N | CYS | B | 317 | 20.960 | 0.542 | 46.965 | 1.00 | 32.79 | B | N |
| ATOM | 4711 | CA | CYS | B | 317 | 19.916 | -0.096 | 47.728 | 1.00 | 32.79 | B | C |
| ATOM | 4712 | CB | CYS | B | 317 | 19.287 | -1.208 | 46.899 | 1.00 | 47.83 | B | C |
| ATOM | 4713 | SG | CYS | B | 317 | 17.750 | -1.814 | 47.602 | 1.00 | 47.83 | B | S |
| ATOM | 4714 | C | CYS | B | 317 | 20.421 | -0.648 | 49.054 | 1.00 | 32.79 | B | C |
| ATOM | 4715 | O | CYS | B | 317 | 19.772 | -0.498 | 50.090 | 1.00 | 32.79 | B | O |
| ATOM | 4716 | N | SER | B | 318 | 21.587 | -1.278 | 49.027 | 1.00 | 38.18 | B | N |
| ATOM | 4717 | CA | SER | B | 318 | 22.158 | -1.867 | 50.236 | 1.00 | 38.18 | B | C |
| ATOM | 4718 | CB | SER | B | 318 | 23.337 | -2.756 | 49.863 | 1.00 | 51.43 | B | C |
| ATOM | 4719 | OG | SER | B | 318 | 24.295 | -1.998 | 49.151 | 1.00 | 51.43 | B | O |
| ATOM | 4720 | C | SER | B | 318 | 22.601 | -0.857 | 51.294 | 1.00 | 38.18 | B | C |
| ATOM | 4721 | O | SER | B | 318 | 22.694 | -1.194 | 52.472 | 1.00 | 38.18 | B | O |
| ATOM | 4722 | N | ARG | B | 319 | 22.882 | 0.373 | 50.882 | 1.00 | 38.46 | B | N |
| ATOM | 4723 | CA | ARG | B | 319 | 23.308 | 1.407 | 51.818 | 1.00 | 38.46 | B | C |
| ATOM | 4724 | CB | ARG | B | 319 | 24.301 | 2.340 | 51.141 | 1.00 | 51.85 | B | C |
| ATOM | 4725 | CG | ARG | B | 319 | 25.596 | 1.657 | 50.746 | 1.00 | 51.85 | B | C |
| ATOM | 4726 | CD | ARG | B | 319 | 26.496 | 1.387 | 51.945 | 1.00 | 51.85 | B | C |
| ATOM | 4727 | NE | ARG | B | 319 | 27.046 | 2.630 | 52.480 | 1.00 | 51.85 | B | N |
| ATOM | 4728 | CZ | ARG | B | 319 | 26.655 | 3.181 | 53.626 | 1.00 | 51.85 | B | C |
| ATOM | 4729 | NH1 | ARG | B | 319 | 25.713 | 2.588 | 54.354 | 1.00 | 51.85 | B | N |
| ATOM | 4730 | NH2 | ARG | B | 319 | 27.196 | 4.324 | 54.044 | 1.00 | 51.85 | B | N |
| ATOM | 4731 | C | ARG | B | 319 | 22.116 | 2.204 | 52.326 | 1.00 | 38.46 | B | C |
| ATOM | 4732 | O | ARG | B | 319 | 22.265 | 3.214 | 53.019 | 1.00 | 38.46 | B | O |
| ATOM | 4733 | N | LEU | B | 320 | 20.927 | 1.742 | 51.965 | 1.00 | 39.77 | B | N |
| ATOM | 4734 | CA | LEU | B | 320 | 19.696 | 2.383 | 52.381 | 1.00 | 39.77 | B | C |
| ATOM | 4735 | CB | LEU | B | 320 | 18.802 | 2.637 | 51.173 | 1.00 | 47.78 | B | C |
| ATOM | 4736 | CG | LEU | B | 320 | 19.300 | 3.645 | 50.137 | 1.00 | 47.78 | B | C |
| ATOM | 4737 | CD1 | LEU | B | 320 | 18.354 | 3.652 | 48.941 | 1.00 | 47.78 | B | C |
| ATOM | 4738 | CD2 | LEU | B | 320 | 19.376 | 5.030 | 50.761 | 1.00 | 47.78 | B | C |
| ATOM | 4739 | C | LEU | B | 320 | 19.015 | 1.426 | 53.325 | 1.00 | 39.77 | B | C |
| ATOM | 4740 | O | LEU | B | 320 | 18.551 | 1.812 | 54.398 | 1.00 | 39.77 | B | O |
| ATOM | 4741 | N | LEU | B | 321 | 18.984 | 0.160 | 52.920 | 1.00 | 43.04 | B | N |
| ATOM | 4742 | CA | LEU | B | 321 | 18.356 | -0.884 | 53.715 | 1.00 | 43.04 | B | C |
| ATOM | 4743 | CB | LEU | B | 321 | 17.724 | -1.925 | 52.788 | 1.00 | 40.51 | B | C |
| ATOM | 4744 | CG | LEU | B | 321 | 16.614 | -1.360 | 51.896 | 1.00 | 40.51 | B | C |
| ATOM | 4745 | CD1 | LEU | B | 321 | 16.155 | -2.400 | 50.891 | 1.00 | 40.51 | B | C |
| ATOM | 4746 | CD2 | LEU | B | 321 | 15.466 | -0.894 | 52.769 | 1.00 | 40.51 | B | C |
| ATOM | 4747 | C | LEU | B | 321 | 19.342 | -1.544 | 54.674 | 1.00 | 43.04 | B | C |
| ATOM | 4748 | O | LEU | B | 321 | 19.772 | -2.680 | 54.472 | 1.00 | 43.04 | B | O |
| ATOM | 4749 | N | GLU | B | 322 | 19.702 | -0.811 | 55.722 | 1.00 | 42.45 | B | N |
| ATOM | 4750 | CA | GLU | B | 322 | 20.625 | -1.311 | 56.733 | 1.00 | 42.45 | B | C |

FIG. 3-72

```
ATOM   4751  CB   GLU B 322      21.842   -0.378   56.855  1.00 52.98      B  C
ATOM   4752  CG   GLU B 322      22.687   -0.286   55.574  1.00 52.98      B  C
ATOM   4753  CD   GLU B 322      24.095   -0.888   55.713  1.00 52.98      B  C
ATOM   4754  OE1  GLU B 322      24.241   -2.000   56.275  1.00 52.98      B  O
ATOM   4755  OE2  GLU B 322      25.060   -0.248   55.237  1.00 52.98      B  O
ATOM   4756  C    GLU B 322      19.872   -1.367   58.053  1.00 42.45      B  C
ATOM   4757  O    GLU B 322      19.012   -0.530   58.300  1.00 42.45      B  O
ATOM   4758  N    TYR B 323      20.169   -2.362   58.888  1.00 38.29      B  N
ATOM   4759  CA   TYR B 323      19.506   -2.467   60.187  1.00 38.29      B  C
ATOM   4760  CB   TYR B 323      19.950   -3.734   60.920  1.00 50.18      B  C
ATOM   4761  CG   TYR B 323      19.260   -5.003   60.479  1.00 50.18      B  C
ATOM   4762  CD1  TYR B 323      17.908   -5.220   60.745  1.00 50.18      B  C
ATOM   4763  CE1  TYR B 323      17.287   -6.401   60.365  1.00 50.18      B  C
ATOM   4764  CD2  TYR B 323      19.968   -6.002   59.816  1.00 50.18      B  C
ATOM   4765  CE2  TYR B 323      19.352   -7.185   59.430  1.00 50.18      B  C
ATOM   4766  CZ   TYR B 323      18.018   -7.378   59.707  1.00 50.18      B  C
ATOM   4767  OH   TYR B 323      17.422   -8.556   59.329  1.00 50.18      B  O
ATOM   4768  C    TYR B 323      19.857   -1.249   61.041  1.00 38.29      B  C
ATOM   4769  O    TYR B 323      18.991   -0.572   61.574  1.00 38.29      B  O
ATOM   4770  N    THR B 324      21.148   -0.986   61.163  1.00 34.41      B  N
ATOM   4771  CA   THR B 324      21.634    0.140   61.935  1.00 34.41      B  C
ATOM   4772  CB   THR B 324      23.172    0.099   62.040  1.00 32.99      B  C
ATOM   4773  OG1  THR B 324      23.555   -1.107   62.707  1.00 32.99      B  O
ATOM   4774  CG2  THR B 324      23.709    1.300   62.817  1.00 32.99      B  C
ATOM   4775  C    THR B 324      21.198    1.443   61.287  1.00 34.41      B  C
ATOM   4776  O    THR B 324      21.706    1.828   60.236  1.00 34.41      B  O
ATOM   4777  N    PRO B 325      20.238    2.134   61.912  1.00 48.73      B  N
ATOM   4778  CD   PRO B 325      19.590    1.757   63.181  1.00 36.88      B  C
ATOM   4779  CA   PRO B 325      19.709    3.407   61.421  1.00 48.73      B  C
ATOM   4780  CB   PRO B 325      18.906    3.921   62.615  1.00 36.88      B  C
ATOM   4781  CG   PRO B 325      18.386    2.660   63.222  1.00 36.88      B  C
ATOM   4782  C    PRO B 325      20.841    4.347   61.053  1.00 48.73      B  C
ATOM   4783  O    PRO B 325      20.858    4.959   59.982  1.00 48.73      B  O
ATOM   4784  N    THR B 326      21.794    4.435   61.966  1.00 45.81      B  N
ATOM   4785  CA   THR B 326      22.952    5.291   61.822  1.00 45.81      B  C
ATOM   4786  CB   THR B 326      23.799    5.206   63.126  1.00 47.93      B  C
ATOM   4787  OG1  THR B 326      23.984    6.526   63.652  1.00 47.93      B  O
ATOM   4788  CG2  THR B 326      25.174    4.522   62.874  1.00 47.93      B  C
ATOM   4789  C    THR B 326      23.822    4.979   60.599  1.00 45.81      B  C
ATOM   4790  O    THR B 326      24.606    5.813   60.158  1.00 45.81      B  O
ATOM   4791  N    ALA B 327      23.664    3.785   60.047  1.00 42.43      B  N
ATOM   4792  CA   ALA B 327      24.464    3.347   58.909  1.00 42.43      B  C
ATOM   4793  CB   ALA B 327      24.632    1.833   58.974  1.00 43.15      B  C
ATOM   4794  C    ALA B 327      23.944    3.728   57.530  1.00 42.43      B  C
ATOM   4795  O    ALA B 327      24.696    3.703   56.551  1.00 42.43      B  O
ATOM   4796  N    ARG B 328      22.659    4.062   57.452  1.00 46.97      B  N
ATOM   4797  CA   ARG B 328      22.025    4.403   56.190  1.00 46.97      B  C
ATOM   4798  CB   ARG B 328      20.519    4.480   56.385  1.00 34.46      B  C
ATOM   4799  CG   ARG B 328      19.922    3.162   56.796  1.00 34.46      B  C
ATOM   4800  CD   ARG B 328      18.537    3.313   57.364  1.00 34.46      B  C
ATOM   4801  NE   ARG B 328      18.150    2.083   58.036  1.00 34.46      B  N
ATOM   4802  CZ   ARG B 328      17.241    2.005   58.999  1.00 34.46      B  C
ATOM   4803  NH1  ARG B 328      16.608    3.094   59.416  1.00 34.46      B  N
ATOM   4804  NH2  ARG B 328      16.983    0.832   59.558  1.00 34.46      B  N
ATOM   4805  C    ARG B 328      22.528    5.708   55.636  1.00 46.97      B  C
ATOM   4806  O    ARG B 328      22.934    6.591   56.392  1.00 46.97      B  O
ATOM   4807  N    LEU B 329      22.513    5.825   54.314  1.00 41.63      B  N
ATOM   4808  CA   LEU B 329      22.942    7.053   53.663  1.00 41.63      B  C
ATOM   4809  CB   LEU B 329      22.934    6.875   52.141  1.00 35.76      B  C
ATOM   4810  CG   LEU B 329      24.158    6.359   51.385  1.00 35.76      B  C
ATOM   4811  CD1  LEU B 329      24.780    5.221   52.124  1.00 35.76      B  C
ATOM   4812  CD2  LEU B 329      23.750    5.937   49.999  1.00 35.76      B  C
ATOM   4813  C    LEU B 329      21.969    8.176   54.037  1.00 41.63      B  C
ATOM   4814  O    LEU B 329      20.843    7.919   54.463  1.00 41.63      B  O
ATOM   4815  N    THR B 330      22.415    9.418   53.894  1.00 43.37      B  N
ATOM   4816  CA   THR B 330      21.566   10.561   54.182  1.00 43.37      B  C
ATOM   4817  CB   THR B 330      22.389   11.781   54.670  1.00 40.88      B  C
```

FIG. 3-73

| ATOM | 4818 | OG1 | THR | B | 330 | 23.339 | 12.161 | 53.666 | 1.00 | 40.88 | B | O |
|------|------|-----|-----|---|-----|--------|--------|--------|------|-------|---|---|
| ATOM | 4819 | CG2 | THR | B | 330 | 23.117 | 11.448 | 55.936 | 1.00 | 40.88 | B | C |
| ATOM | 4820 | C | THR | B | 330 | 20.908 | 10.899 | 52.850 | 1.00 | 43.37 | B | C |
| ATOM | 4821 | O | THR | B | 330 | 21.437 | 10.568 | 51.793 | 1.00 | 43.37 | B | O |
| ATOM | 4822 | N | PRO | B | 331 | 19.742 | 11.552 | 52.881 | 1.00 | 42.73 | B | N |
| ATOM | 4823 | CD | PRO | B | 331 | 18.902 | 11.957 | 54.021 | 1.00 | 45.76 | B | C |
| ATOM | 4824 | CA | PRO | B | 331 | 19.098 | 11.884 | 51.610 | 1.00 | 42.73 | B | C |
| ATOM | 4825 | CB | PRO | B | 331 | 17.923 | 12.754 | 52.047 | 1.00 | 45.76 | B | C |
| ATOM | 4826 | CG | PRO | B | 331 | -17.550 | 12.149 | 53.371 | 1.00 | 45.76 | B | C |
| ATOM | 4827 | C | PRO | B | 331 | 20.035 | 12.586 | 50.620 | 1.00 | 42.73 | B | C |
| ATOM | 4828 | O | PRO | B | 331 | 20.103 | 12.207 | 49.457 | 1.00 | 42.73 | B | O |
| ATOM | 4829 | N | LEU | B | 332 | 20.764 | 13.597 | 51.074 | 1.00 | 34.87 | B | N |
| ATOM | 4830 | CA | LEU | B | 332 | 21.662 | 14.300 | 50.172 | 1.00 | 34.87 | B | C |
| ATOM | 4831 | CB | LEU | B | 332 | 22.347 | 15.466 | 50.874 | 1.00 | 39.71 | B | C |
| ATOM | 4832 | CG | LEU | B | 332 | 21.966 | 16.856 | 50.373 | 1.00 | 39.71 | B | C |
| ATOM | 4833 | CD1 | LEU | B | 332 | 22.994 | 17.864 | 50.859 | 1.00 | 39.71 | B | C |
| ATOM | 4834 | CD2 | LEU | B | 332 | 21.919 | 16.864 | 48.861 | 1.00 | 39.71 | B | C |
| ATOM | 4835 | C | LEU | B | 332 | 22.713 | 13.344 | 49.652 | 1.00 | 34.87 | B | C |
| ATOM | 4836 | O | LEU | B | 332 | 23.150 | 13.444 | 48.509 | 1.00 | 34.87 | B | O |
| ATOM | 4837 | N | GLU | B | 333 | 23.123 | 12.415 | 50.505 | 1.00 | 39.21 | B | N |
| ATOM | 4838 | CA | GLU | B | 333 | 24.127 | 11.422 | 50.141 | 1.00 | 39.21 | B | C |
| ATOM | 4839 | CB | GLU | B | 333 | 24.475 | 10.572 | 51.360 | 1.00 | 55.63 | B | C |
| ATOM | 4840 | CG | GLU | B | 333 | 25.845 | 10.827 | 51.915 | 1.00 | 55.63 | B | C |
| ATOM | 4841 | CD | GLU | B | 333 | 25.912 | 10.594 | 53.412 | 1.00 | 55.63 | B | C |
| ATOM | 4842 | OE1 | GLU | B | 333 | 25.559 | 9.478 | 53.862 | 1.00 | 55.63 | B | O |
| ATOM | 4843 | OE2 | GLU | B | 333 | 26.324 | 11.536 | 54.135 | 1.00 | 55.63 | B | O |
| ATOM | 4844 | C | GLU | B | 333 | 23.620 | 10.524 | 49.022 | 1.00 | 39.21 | B | C |
| ATOM | 4845 | O | GLU | B | 333 | 24.355 | 10.206 | 48.099 | 1.00 | 39.21 | B | O |
| ATOM | 4846 | N | ALA | B | 334 | 22.360 | 10.114 | 49.125 | 1.00 | 40.85 | B | N |
| ATOM | 4847 | CA | ALA | B | 334 | 21.734 | 9.262 | 48.126 | 1.00 | 40.85 | B | C |
| ATOM | 4848 | CB | ALA | B | 334 | 20.346 | 8.862 | 48.592 | 1.00 | 15.37 | B | C |
| ATOM | 4849 | C | ALA | B | 334 | 21.666 | 9.932 | 46.744 | 1.00 | 40.85 | B | C |
| ATOM | 4850 | O | ALA | B | 334 | 21.889 | 9.278 | 45.720 | 1.00 | 40.85 | B | O |
| ATOM | 4851 | N | CYS | B | 335 | 21.363 | 11.229 | 46.709 | 1.00 | 51.32 | B | N |
| ATOM | 4852 | CA | CYS | B | 335 | 21.299 | 11.958 | 45.435 | 1.00 | 51.32 | B | C |
| ATOM | 4853 | CB | CYS | B | 335 | 20.879 | 13.422 | 45.635 | 1.00 | 36.41 | B | C |
| ATOM | 4854 | SG | CYS | B | 335 | 19.226 | 13.696 | 46.298 | 1.00 | 36.41 | B | S |
| ATOM | 4855 | C | CYS | B | 335 | 22.684 | 11.942 | 44.824 | 1.00 | 51.32 | B | C |
| ATOM | 4856 | O | CYS | B | 335 | 22.845 | 11.855 | 43.607 | 1.00 | 51.32 | B | O |
| ATOM | 4857 | N | ALA | B | 336 | 23.685 | 12.032 | 45.688 | 1.00 | 43.29 | B | N |
| ATOM | 4858 | CA | ALA | B | 336 | 25.069 | 12.029 | 45.258 | 1.00 | 43.29 | B | C |
| ATOM | 4859 | CB | ALA | B | 336 | 25.959 | 12.450 | 46.412 | 1.00 | 61.77 | B | C |
| ATOM | 4860 | C | ALA | B | 336 | 25.504 | 10.667 | 44.734 | 1.00 | 43.29 | B | C |
| ATOM | 4861 | O | ALA | B | 336 | 26.491 | 10.576 | 44.011 | 1.00 | 43.29 | B | O |
| ATOM | 4862 | N | HIS | B | 337 | 24.773 | 9.616 | 45.089 | 1.00 | 28.49 | B | N |
| ATOM | 4863 | CA | HIS | B | 337 | 25.136 | 8.280 | 44.645 | 1.00 | 28.49 | B | C |
| ATOM | 4864 | CB | HIS | B | 337 | 24.081 | 7.270 | 45.069 | 1.00 | 34.57 | B | C |
| ATOM | 4865 | CG | HIS | B | 337 | 24.518 | 5.847 | 44.912 | 1.00 | 34.57 | B | C |
| ATOM | 4866 | CD2 | HIS | B | 337 | 24.581 | 5.050 | 43.820 | 1.00 | 34.57 | B | C |
| ATOM | 4867 | ND1 | HIS | B | 337 | 24.947 | 5.080 | 45.973 | 1.00 | 34.57 | B | N |
| ATOM | 4868 | CE1 | HIS | B | 337 | 25.249 | 3.868 | 45.542 | 1.00 | 34.57 | B | C |
| ATOM | 4869 | NE2 | HIS | B | 337 | 25.034 | 3.824 | 44.239 | 1.00 | 34.57 | B | N |
| ATOM | 4870 | C | HIS | B | 337 | 25.306 | 8.226 | 43.134 | 1.00 | 28.49 | B | C |
| ATOM | 4871 | O | HIS | B | 337 | 24.605 | 8.915 | 42.404 | 1.00 | 28.49 | B | O |
| ATOM | 4872 | N | SER | B | 338 | 26.229 | 7.390 | 42.668 | 1.00 | 49.69 | B | N |
| ATOM | 4873 | CA | SER | B | 338 | 26.506 | 7.269 | 41.238 | 1.00 | 49.69 | B | C |
| ATOM | 4874 | CB | SER | B | 338 | 27.840 | 6.538 | 41.013 | 1.00 | 46.42 | B | C |
| ATOM | 4875 | OG | SER | B | 338 | 27.908 | 5.335 | 41.750 | 1.00 | 46.42 | B | O |
| ATOM | 4876 | C | SER | B | 338 | 25.401 | 6.606 | 40.427 | 1.00 | 49.69 | B | C |
| ATOM | 4877 | O | SER | B | 338 | 25.416 | 6.669 | 39.202 | 1.00 | 49.69 | B | O |
| ATOM | 4878 | N | PHE | B | 339 | 24.455 | 5.964 | 41.105 | 1.00 | 42.45 | B | N |
| ATOM | 4879 | CA | PHE | B | 339 | 23.331 | 5.324 | 40.425 | 1.00 | 42.45 | B | C |
| ATOM | 4880 | CB | PHE | B | 339 | 22.370 | 4.744 | 41.464 | 1.00 | 45.70 | B | C |
| ATOM | 4881 | CG | PHE | B | 339 | 21.042 | 4.293 | 40.912 | 1.00 | 45.70 | B | C |
| ATOM | 4882 | CD1 | PHE | B | 339 | 20.967 | 3.316 | 39.924 | 1.00 | 45.70 | B | C |
| ATOM | 4883 | CD2 | PHE | B | 339 | 19.852 | 4.799 | 41.437 | 1.00 | 45.70 | B | C |
| ATOM | 4884 | CE1 | PHE | B | 339 | 19.721 | 2.844 | 39.472 | 1.00 | 45.70 | B | C |

FIG. 3-74

```
ATOM   4885  CE2 PHE B 339      18.611    4.338   40.995  1.00 45.70           B  C
ATOM   4886  CZ  PHE B 339      18.545    3.358   40.012  1.00 45.70           B  C
ATOM   4887  C   PHE B 339      22.641    6.423   39.623  1.00 42.45           B  C
ATOM   4888  O   PHE B 339      22.111    6.193   38.536  1.00 42.45           B  O
ATOM   4889  N   PHE B 340      22.694    7.633   40.161  1.00 48.61           B  N
ATOM   4890  CA  PHE B 340      22.065    8.781   39.531  1.00 48.61           B  C
ATOM   4891  CB  PHE B 340      21.514    9.717   40.608  1.00 36.00           B  C
ATOM   4892  CG  PHE B 340      20.552    9.059   41.550  1.00 36.00           B  C
ATOM   4893  CD1 PHE B 340      19.404    8.441   41.073  1.00 36.00           B  C
ATOM   4894  CD2 PHE B 340      20.772    9.090   42.922  1.00 36.00           B  C
ATOM   4895  CE1 PHE B 340      18.486    7.870   41.944  1.00 36.00           B  C
ATOM   4896  CE2 PHE B 340      19.856    8.519   43.800  1.00 36.00           B  C
ATOM   4897  CZ  PHE B 340      18.708    7.909   43.304  1.00 36.00           B  C
ATOM   4898  C   PHE B 340      22.964    9.590   38.594  1.00 48.61           B  C
ATOM   4899  O   PHE B 340      22.505   10.576   38.017  1.00 48.61           B  O
ATOM   4900  N   ASP B 341      24.229    9.196   38.436  1.00 67.58           B  N
ATOM   4901  CA  ASP B 341      25.145    9.945   37.560  1.00 67.58           B  C
ATOM   4902  CB  ASP B 341      26.455    9.183   37.323  1.00 49.28           B  C
ATOM   4903  CG  ASP B 341      27.282    9.034   38.586  1.00 49.28           B  C
ATOM   4904  OD1 ASP B 341      27.065    9.816   39.538  1.00 49.28           B  O
ATOM   4905  OD2 ASP B 341      28.158    8.144   38.623  1.00 49.28           B  O
ATOM   4906  C   ASP B 341      24.527   10.290   36.210  1.00 67.58           B  C
ATOM   4907  O   ASP B 341      24.651   11.419   35.735  1.00 67.58           B  O
ATOM   4908  N   GLU B 342      23.855    9.327   35.593  1.00 47.77           B  N
ATOM   4909  CA  GLU B 342      23.237    9.582   34.305  1.00 47.77           B  C
ATOM   4910  CB  GLU B 342      22.356    8.397   33.902  1.00 61.12           B  C
ATOM   4911  CG  GLU B 342      21.474    8.666   32.687  1.00 61.12           B  C
ATOM   4912  CD  GLU B 342      20.818    7.409   32.140  1.00 61.12           B  C
ATOM   4913  OE1 GLU B 342      20.282    6.587   32.926  1.00 61.12           B  O
ATOM   4914  OE2 GLU B 342      20.832    7.255   30.905  1.00 61.12           B  O
ATOM   4915  C   GLU B 342      22.416   10.875   34.301  1.00 47.77           B  C
ATOM   4916  O   GLU B 342      22.329   11.556   33.282  1.00 47.77           B  O
ATOM   4917  N   LEU B 343      21.821   11.220   35.439  1.00 47.54           B  N
ATOM   4918  CA  LEU B 343      21.011   12.433   35.534  1.00 47.54           B  C
ATOM   4919  CB  LEU B 343      20.207   12.426   36.835  1.00 37.91           B  C
ATOM   4920  CG  LEU B 343      19.274   11.233   37.041  1.00 37.91           B  C
ATOM   4921  CD1 LEU B 343      18.581   11.366   38.378  1.00 37.91           B  C
ATOM   4922  CD2 LEU B 343      18.253   11.162   35.912  1.00 37.91           B  C
ATOM   4923  C   LEU B 343      21.891   13.676   35.488  1.00 47.54           B  C
ATOM   4924  O   LEU B 343      21.425   14.778   35.181  1.00 47.54           B  O
ATOM   4925  N   ARG B 344      23.172   13.487   35.790  1.00 46.24           B  N
ATOM   4926  CA  ARG B 344      24.123   14.586   35.809  1.00 46.24           B  C
ATOM   4927  CB  ARG B 344      25.192   14.326   36.874  1.00 51.22           B  C
ATOM   4928  CG  ARG B 344      24.795   14.819   38.275  1.00 51.22           B  C
ATOM   4929  CD  ARG B 344      25.728   14.270   39.331  1.00 51.22           B  C
ATOM   4930  NE  ARG B 344      25.497   12.845   39.535  1.00 51.22           B  N
ATOM   4931  CZ  ARG B 344      24.762   12.337   40.523  1.00 51.22           B  C
ATOM   4932  NH1 ARG B 344      24.183   13.135   41.416  1.00 51.22           B  N
ATOM   4933  NH2 ARG B 344      24.594   11.025   40.612  1.00 51.22           B  N
ATOM   4934  C   ARG B 344      24.741   14.818   34.444  1.00 46.24           B  C
ATOM   4935  O   ARG B 344      25.411   15.826   34.213  1.00 46.24           B  O
ATOM   4936  N   ASP B 345      24.498   13.875   33.541  1.00 49.45           B  N
ATOM   4937  CA  ASP B 345      24.970   13.954   32.156  1.00 49.45           B  C
ATOM   4938  CB  ASP B 345      24.508   12.688   31.425  1.00 50.74           B  C
ATOM   4939  CG  ASP B 345      24.897   12.657   29.959  1.00 50.74           B  C
ATOM   4940  OD1 ASP B 345      24.925   13.723   29.304  1.00 50.74           B  O
ATOM   4941  OD2 ASP B 345      25.149   11.538   29.452  1.00 50.74           B  O
ATOM   4942  C   ASP B 345      24.305   15.198   31.538  1.00 49.45           B  C
ATOM   4943  O   ASP B 345      23.110   15.425   31.730  1.00 49.45           B  O
ATOM   4944  N   PRO B 346      25.063   16.024   30.798  1.00 46.36           B  N
ATOM   4945  CD  PRO B 346      26.477   15.920   30.407  1.00 26.69           B  C
ATOM   4946  CA  PRO B 346      24.458   17.217   30.195  1.00 46.36           B  C
ATOM   4947  CB  PRO B 346      25.671   17.981   29.690  1.00 26.69           B  C
ATOM   4948  CG  PRO B 346      26.553   16.878   29.235  1.00 26.69           B  C
ATOM   4949  C   PRO B 346      23.481   16.860   29.067  1.00 46.36           B  C
ATOM   4950  O   PRO B 346      22.623   17.666   28.685  1.00 46.36           B  O
ATOM   4951  N   ASN B 347      23.609   15.636   28.560  1.00 48.42           B  N
```

FIG. 3-75

| ATOM | 4952 | CA  | ASN | B | 347 | 22.776 | 15.129 | 27.475 | 1.00 | 48.42 | B | C |
|------|------|-----|-----|---|-----|--------|--------|--------|------|-------|---|---|
| ATOM | 4953 | CB  | ASN | B | 347 | 23.595 | 14.169 | 26.628 | 1.00 | 80.67 | B | C |
| ATOM | 4954 | CG  | ASN | B | 347 | 24.823 | 14.824 | 26.044 | 1.00 | 80.67 | B | C |
| ATOM | 4955 | OD1 | ASN | B | 347 | 25.849 | 14.162 | 25.824 | 1.00 | 80.67 | B | O |
| ATOM | 4956 | ND2 | ASN | B | 347 | 24.731 | 16.132 | 25.777 | 1.00 | 80.67 | B | N |
| ATOM | 4957 | C   | ASN | B | 347 | 21.500 | 14.415 | 27.909 | 1.00 | 48.42 | B | C |
| ATOM | 4958 | O   | ASN | B | 347 | 20.527 | 14.383 | 27.166 | 1.00 | 48.42 | B | O |
| ATOM | 4959 | N   | VAL | B | 348 | 21.507 | 13.826 | 29.099 | 1.00 | 59.70 | B | N |
| ATOM | 4960 | CA  | VAL | B | 348 | 20.339 | 13.093 | 29.572 | 1.00 | 59.70 | B | C |
| ATOM | 4961 | CB  | VAL | B | 348 | 20.376 | 12.862 | 31.103 | 1.00 | 47.92 | B | C |
| ATOM | 4962 | CG1 | VAL | B | 348 | 20.423 | 14.188 | 31.844 | 1.00 | 47.92 | B | C |
| ATOM | 4963 | CG2 | VAL | B | 348 | 19.155 | 12.071 | 31.526 | 1.00 | 47.92 | B | C |
| ATOM | 4964 | C   | VAL | B | 348 | 19.037 | 13.796 | 29.226 | 1.00 | 59.70 | B | C |
| ATOM | 4965 | O   | VAL | B | 348 | 18.896 | 15.007 | 29.424 | 1.00 | 59.70 | B | O |
| ATOM | 4966 | N   | LYS | B | 349 | 18.091 | 13.037 | 28.691 | 1.00 | 43.91 | B | N |
| ATOM | 4967 | CA  | LYS | B | 349 | 16.795 | 13.596 | 28.346 | 1.00 | 43.91 | B | C |
| ATOM | 4968 | CB  | LYS | B | 349 | 16.734 | 13.940 | 26.852 | 1.00 | 63.89 | B | C |
| ATOM | 4969 | CG  | LYS | B | 349 | 17.968 | 14.686 | 26.357 | 1.00 | 63.89 | B | C |
| ATOM | 4970 | CD  | LYS | B | 349 | 17.720 | 15.430 | 25.059 | 1.00 | 63.89 | B | C |
| ATOM | 4971 | CE  | LYS | B | 349 | 16.909 | 16.706 | 25.301 | 1.00 | 63.89 | B | C |
| ATOM | 4972 | NZ  | LYS | B | 349 | 17.651 | 17.701 | 26.144 | 1.00 | 63.89 | B | N |
| ATOM | 4973 | C   | LYS | B | 349 | 15.764 | 12.546 | 28.689 | 1.00 | 43.91 | B | C |
| ATOM | 4974 | O   | LYS | B | 349 | 16.111 | 11.382 | 28.879 | 1.00 | 43.91 | B | O |
| ATOM | 4975 | N   | LEU | B | 350 | 14.503 | 12.940 | 28.795 | 1.00 | 44.58 | B | N |
| ATOM | 4976 | CA  | LEU | B | 350 | 13.486 | 11.952 | 29.108 | 1.00 | 44.58 | B | C |
| ATOM | 4977 | CB  | LEU | B | 350 | 12.196 | 12.634 | 29.554 | 1.00 | 52.90 | B | C |
| ATOM | 4978 | CG  | LEU | B | 350 | 12.278 | 13.628 | 30.714 | 1.00 | 52.90 | B | C |
| ATOM | 4979 | CD1 | LEU | B | 350 | 10.914 | 14.260 | 30.933 | 1.00 | 52.90 | B | C |
| ATOM | 4980 | CD2 | LEU | B | 350 | 12.744 | 12.926 | 31.970 | 1.00 | 52.90 | B | C |
| ATOM | 4981 | C   | LEU | B | 350 | 13.227 | 11.131 | 27.850 | 1.00 | 44.58 | B | C |
| ATOM | 4982 | O   | LEU | B | 350 | 13.562 | 11.558 | 26.736 | 1.00 | 44.58 | B | O |
| ATOM | 4983 | N   | PRO | B | 351 | 12.640 | 9.935  | 28.005 | 1.00 | 61.99 | B | N |
| ATOM | 4984 | CD  | PRO | B | 351 | 12.159 | 9.272  | 29.228 | 1.00 | 53.32 | B | C |
| ATOM | 4985 | CA  | PRO | B | 351 | 12.367 | 9.116  | 26.821 | 1.00 | 61.99 | B | C |
| ATOM | 4986 | CB  | PRO | B | 351 | 11.933 | 7.778  | 27.421 | 1.00 | 53.32 | B | C |
| ATOM | 4987 | CG  | PRO | B | 351 | 11.255 | 8.192  | 28.673 | 1.00 | 53.32 | B | C |
| ATOM | 4988 | C   | PRO | B | 351 | 11.251 | 9.812  | 26.054 | 1.00 | 61.99 | B | C |
| ATOM | 4989 | O   | PRO | B | 351 | 10.688 | 9.291  | 25.087 | 1.00 | 61.99 | B | O |
| ATOM | 4990 | N   | ASN | B | 352 | 10.963 | 11.017 | 26.521 | 1.00 | 53.15 | B | N |
| ATOM | 4991 | CA  | ASN | B | 352 | 9.930  | 11.881 | 25.985 | 1.00 | 53.15 | B | C |
| ATOM | 4992 | CB  | ASN | B | 352 | 9.335  | 12.696 | 27.127 | 1.00 | 71.14 | B | C |
| ATOM | 4993 | CG  | ASN | B | 352 | 7.891  | 12.992 | 26.913 | 1.00 | 71.14 | B | C |
| ATOM | 4994 | OD1 | ASN | B | 352 | 7.201  | 13.502 | 27.804 | 1.00 | 71.14 | B | O |
| ATOM | 4995 | ND2 | ASN | B | 352 | 7.404  | 12.667 | 25.715 | 1.00 | 71.14 | B | N |
| ATOM | 4996 | C   | ASN | B | 352 | 10.499 | 12.840 | 24.966 | 1.00 | 53.15 | B | C |
| ATOM | 4997 | O   | ASN | B | 352 | 9.749  | 13.531 | 24.299 | 1.00 | 53.15 | B | O |
| ATOM | 4998 | N   | GLY | B | 353 | 11.826 | 12.888 | 24.871 | 1.00 | 42.84 | B | N |
| ATOM | 4999 | CA  | GLY | B | 353 | 12.490 | 13.802 | 23.956 | 1.00 | 42.84 | B | C |
| ATOM | 5000 | C   | GLY | B | 353 | 12.721 | 15.108 | 24.697 | 1.00 | 42.84 | B | C |
| ATOM | 5001 | O   | GLY | B | 353 | 13.654 | 15.880 | 24.416 | 1.00 | 42.84 | B | O |
| ATOM | 5002 | N   | ARG | B | 354 | 11.851 | 15.331 | 25.681 | 1.00 | 71.99 | B | N |
| ATOM | 5003 | CA  | ARG | B | 354 | 11.879 | 16.519 | 26.527 | 1.00 | 71.99 | B | C |
| ATOM | 5004 | CB  | ARG | B | 354 | 10.543 | 16.654 | 27.254 | 1.00 | 76.87 | B | C |
| ATOM | 5005 | CG  | ARG | B | 354 | 9.351  | 16.550 | 26.334 | 1.00 | 76.87 | B | C |
| ATOM | 5006 | CD  | ARG | B | 354 | 8.045  | 16.534 | 27.104 | 1.00 | 76.87 | B | C |
| ATOM | 5007 | NE  | ARG | B | 354 | 7.952  | 17.668 | 28.015 | 1.00 | 76.87 | B | N |
| ATOM | 5008 | CZ  | ARG | B | 354 | 6.805  | 18.166 | 28.477 | 1.00 | 76.87 | B | C |
| ATOM | 5009 | NH1 | ARG | B | 354 | 5.645  | 17.618 | 28.100 | 1.00 | 76.87 | B | N |
| ATOM | 5010 | NH2 | ARG | B | 354 | 6.819  | 19.216 | 29.305 | 1.00 | 76.87 | B | N |
| ATOM | 5011 | C   | ARG | B | 354 | 13.001 | 16.428 | 27.554 | 1.00 | 71.99 | B | C |
| ATOM | 5012 | O   | ARG | B | 354 | 13.456 | 15.329 | 27.910 | 1.00 | 71.99 | B | O |
| ATOM | 5013 | N   | ASP | B | 355 | 13.443 | 17.581 | 28.040 | 1.00 | 47.06 | B | N |
| ATOM | 5014 | CA  | ASP | B | 355 | 14.495 | 17.595 | 29.036 | 1.00 | 47.06 | B | C |
| ATOM | 5015 | CB  | ASP | B | 355 | 15.095 | 18.987 | 29.156 | 1.00 | 86.90 | B | C |
| ATOM | 5016 | CG  | ASP | B | 355 | 15.287 | 19.640 | 27.806 | 1.00 | 86.90 | B | C |
| ATOM | 5017 | OD1 | ASP | B | 355 | 14.247 | 20.001 | 27.190 | 1.00 | 86.90 | B | O |
| ATOM | 5018 | OD2 | ASP | B | 355 | 16.462 | 19.774 | 27.357 | 1.00 | 86.90 | B | O |

FIG. 3-76

```
ATOM   5019  C    ASP B 355      13.941  17.170  30.382  1.00 47.06      B  C
ATOM   5020  O    ASP B 355      12.730  17.151  30.608  1.00 47.06      B  O
ATOM   5021  N    THR B 356      14.855  16.810  31.269  1.00 51.49      B  N
ATOM   5022  CA   THR B 356      14.497  16.389  32.607  1.00 51.49      B  C
ATOM   5023  CB   THR B 356      15.659  15.640  33.269  1.00 41.96      B  C
ATOM   5024  OG1  THR B 356      16.849  16.428  33.153  1.00 41.96      B  O
ATOM   5025  CG2  THR B 356      15.877  14.288  32.604  1.00 41.96      B  C
ATOM   5026  C    THR B 356      14.214  17.634  33.424  1.00 51.49      B  C
ATOM   5027  O    THR B 356      14.742  18.709  33.135  1.00 51.49      B  O
ATOM   5028  N    PRO B 357      13.371  17.508  34.455  1.00 36.38      B  N
ATOM   5029  CD   PRO B 357      12.692  16.305  34.968  1.00 39.95      B  C
ATOM   5030  CA   PRO B 357      13.073  18.676  35.280  1.00 36.38      B  C
ATOM   5031  CB   PRO B 357      12.118  18.115  36.341  1.00 39.95      B  C
ATOM   5032  CG   PRO B 357      12.481  16.656  36.414  1.00 39.95      B  C
ATOM   5033  C    PRO B 357      14.368  19.230  35.873  1.00 36.38      B  C
ATOM   5034  O    PRO B 357      15.440  18.672  35.657  1.00 36.38      B  O
ATOM   5035  N    ALA B 358      14.270  20.338  36.599  1.00 45.42      B  N
ATOM   5036  CA   ALA B 358      15.444  20.942  37.219  1.00 45.42      B  C
ATOM   5037  CB   ALA B 358      15.101  22.328  37.740  1.00 50.02      B  C
ATOM   5038  C    ALA B 358      15.883  20.047  38.371  1.00 45.42      B  C
ATOM   5039  O    ALA B 358      15.193  19.962  39.380  1.00 45.42      B  O
ATOM   5040  N    LEU B 359      17.031  19.390  38.235  1.00 54.53      B  N
ATOM   5041  CA   LEU B 359      17.493  18.491  39.289  1.00 54.53      B  C
ATOM   5042  CB   LEU B 359      17.814  17.119  38.685  1.00 47.13      B  C
ATOM   5043  CG   LEU B 359      16.666  16.603  37.817  1.00 47.13      B  C
ATOM   5044  CD1  LEU B 359      17.107  15.377  37.024  1.00 47.13      B  C
ATOM   5045  CD2  LEU B 359      15.461  16.315  38.708  1.00 47.13      B  C
ATOM   5046  C    LEU B 359      18.705  19.004  40.059  1.00 54.53      B  C
ATOM   5047  O    LEU B 359      19.245  18.293  40.916  1.00 54.53      B  O
ATOM   5048  N    PHE B 360      19.111  20.242  39.786  1.00 58.89      B  N
ATOM   5049  CA   PHE B 360      20.287  20.798  40.434  1.00 58.89      B  C
ATOM   5050  CB   PHE B 360      21.410  20.912  39.415  1.00 49.50      B  C
ATOM   5051  CG   PHE B 360      21.544  19.711  38.529  1.00 49.50      B  C
ATOM   5052  CD1  PHE B 360      21.860  18.469  39.065  1.00 49.50      B  C
ATOM   5053  CD2  PHE B 360      21.346  19.819  37.155  1.00 49.50      B  C
ATOM   5054  CE1  PHE B 360      21.978  17.341  38.247  1.00 49.50      B  C
ATOM   5055  CE2  PHE B 360      21.461  18.699  36.327  1.00 49.50      B  C
ATOM   5056  CZ   PHE B 360      21.778  17.451  36.878  1.00 49.50      B  C
ATOM   5057  C    PHE B 360      20.121  22.152  41.115  1.00 58.89      B  C
ATOM   5058  O    PHE B 360      21.058  22.629  41.763  1.00 58.89      B  O
ATOM   5059  N    ASN B 361      18.966  22.796  40.969  1.00 64.68      B  N
ATOM   5060  CA   ASN B 361      18.785  24.096  41.617  1.00 64.68      B  C
ATOM   5061  CB   ASN B 361      17.588  24.860  41.014  1.00 60.33      B  C
ATOM   5062  CG   ASN B 361      16.299  24.053  41.009  1.00 60.33      B  C
ATOM   5063  OD1  ASN B 361      16.281  22.893  40.598  1.00 60.33      B  O
ATOM   5064  ND2  ASN B 361      15.208  24.674  41.446  1.00 60.33      B  N
ATOM   5065  C    ASN B 361      18.624  23.897  43.120  1.00 64.68      B  C
ATOM   5066  O    ASN B 361      17.543  24.086  43.681  1.00 64.68      B  O
ATOM   5067  N    PHE B 362      19.725  23.499  43.753  1.00 52.01      B  N
ATOM   5068  CA   PHE B 362      19.782  23.252  45.189  1.00 52.01      B  C
ATOM   5069  CB   PHE B 362      20.986  22.377  45.524  1.00 42.20      B  C
ATOM   5070  CG   PHE B 362      20.792  20.926  45.211  1.00 42.20      B  C
ATOM   5071  CD1  PHE B 362      20.268  20.061  46.172  1.00 42.20      B  C
ATOM   5072  CD2  PHE B 362      21.144  20.420  43.966  1.00 42.20      B  C
ATOM   5073  CE1  PHE B 362      20.103  18.709  45.894  1.00 42.20      B  C
ATOM   5074  CE2  PHE B 362      20.984  19.079  43.676  1.00 42.20      B  C
ATOM   5075  CZ   PHE B 362      20.462  18.216  44.644  1.00 42.20      B  C
ATOM   5076  C    PHE B 362      19.937  24.545  45.951  1.00 52.01      B  C
ATOM   5077  O    PHE B 362      20.603  25.461  45.483  1.00 52.01      B  O
ATOM   5078  N    THR B 363      19.336  24.616  47.131  1.00 48.45      B  N
ATOM   5079  CA   THR B 363      19.458  25.802  47.967  1.00 48.45      B  C
ATOM   5080  CB   THR B 363      18.093  26.278  48.468  1.00 49.95      B  C
ATOM   5081  OG1  THR B 363      17.549  25.305  49.373  1.00 49.95      B  O
ATOM   5082  CG2  THR B 363      17.149  26.498  47.283  1.00 49.95      B  C
ATOM   5083  C    THR B 363      20.327  25.453  49.175  1.00 48.45      B  C
ATOM   5084  O    THR B 363      20.348  24.296  49.619  1.00 48.45      B  O
ATOM   5085  N    THR B 364      21.042  26.446  49.704  1.00 68.37      B  N
```

FIG. 3-77

| ATOM | 5086 | CA | THR | B | 364 | 21.916 | 26.225 | 50.864 | 1.00 | 68.37 | B | C |
|---|---|---|---|---|---|---|---|---|---|---|---|---|
| ATOM | 5087 | CB | THR | B | 364 | 22.425 | 27.541 | 51.477 | 1.00 | 46.75 | B | C |
| ATOM | 5088 | OG1 | THR | B | 364 | 21.414 | 28.076 | 52.341 | 1.00 | 46.75 | B | O |
| ATOM | 5089 | CG2 | THR | B | 364 | 22.771 | 28.539 | 50.384 | 1.00 | 46.75 | B | C |
| ATOM | 5090 | C | THR | B | 364 | 21.182 | 25.475 | 51.970 | 1.00 | 68.37 | B | C |
| ATOM | 5091 | O | THR | B | 364 | 21.811 | 24.803 | 52.794 | 1.00 | 68.37 | B | O |
| ATOM | 5092 | N | GLN | B | 365 | 19.856 | 25.610 | 51.993 | 1.00 | 42.99 | B | N |
| ATOM | 5093 | CA | GLN | B | 365 | 19.046 | 24.922 | 52.981 | 1.00 | 42.99 | B | C |
| ATOM | 5094 | CB | GLN | B | 365 | 17.612 | 25.438 | 52.946 | 1.00 | 52.17 | B | C |
| ATOM | 5095 | CG | GLN | B | 365 | 16.639 | 24.640 | 53.825 | 1.00 | 52.17 | B | C |
| ATOM | 5096 | CD | GLN | B | 365 | 16.827 | 24.891 | 55.311 | 1.00 | 52.17 | B | C |
| ATOM | 5097 | OE1 | GLN | B | 365 | 17.768 | 25.572 | 55.724 | 1.00 | 52.17 | B | O |
| ATOM | 5098 | NE2 | GLN | B | 365 | 15.932 | 24.340 | 56.123 | 1.00 | 52.17 | B | N |
| ATOM | 5099 | C | GLN | B | 365 | 19.064 | 23.428 | 52.668 | 1.00 | 42.99 | B | C |
| ATOM | 5100 | O | GLN | B | 365 | 19.195 | 22.605 | 53.566 | 1.00 | 42.99 | B | O |
| ATOM | 5101 | N | GLU | B | 366 | 18.935 | 23.082 | 51.391 | 1.00 | 45.28 | B | N |
| ATOM | 5102 | CA | GLU | B | 366 | 18.939 | 21.679 | 50.985 | 1.00 | 45.28 | B | C |
| ATOM | 5103 | CB | GLU | B | 366 | 18.597 | 21.524 | 49.495 | 1.00 | 51.55 | B | C |
| ATOM | 5104 | CG | GLU | B | 366 | 17.292 | 22.160 | 49.002 | 1.00 | 51.55 | B | C |
| ATOM | 5105 | CD | GLU | B | 366 | 17.040 | 21.860 | 47.520 | 1.00 | 51.55 | B | C |
| ATOM | 5106 | OE1 | GLU | B | 366 | 16.852 | 20.667 | 47.168 | 1.00 | 51.55 | B | O |
| ATOM | 5107 | OE2 | GLU | B | 366 | 17.038 | 22.813 | 46.710 | 1.00 | 51.55 | B | O |
| ATOM | 5108 | C | GLU | B | 366 | 20.327 | 21.093 | 51.217 | 1.00 | 45.28 | B | C |
| ATOM | 5109 | O | GLU | B | 366 | 20.472 | 19.998 | 51.777 | 1.00 | 45.28 | B | O |
| ATOM | 5110 | N | LEU | B | 367 | 21.342 | 21.834 | 50.778 | 1.00 | 56.74 | B | N |
| ATOM | 5111 | CA | LEU | B | 367 | 22.734 | 21.405 | 50.901 | 1.00 | 56.74 | B | C |
| ATOM | 5112 | CB | LEU | B | 367 | 23.595 | 22.201 | 49.922 | 1.00 | 60.11 | B | C |
| ATOM | 5113 | CG | LEU | B | 367 | 23.193 | 22.132 | 48.446 | 1.00 | 60.11 | B | C |
| ATOM | 5114 | CD1 | LEU | B | 367 | 23.625 | 23.407 | 47.727 | 1.00 | 60.11 | B | C |
| ATOM | 5115 | CD2 | LEU | B | 367 | 23.808 | 20.891 | 47.805 | 1.00 | 60.11 | B | C |
| ATOM | 5116 | C | LEU | B | 367 | 23.303 | 21.577 | 52.310 | 1.00 | 56.74 | B | C |
| ATOM | 5117 | O | LEU | B | 367 | 24.440 | 21.188 | 52.574 | 1.00 | 56.74 | B | O |
| ATOM | 5118 | N | SER | B | 368 | 22.514 | 22.138 | 53.219 | 1.00 | 55.54 | B | N |
| ATOM | 5119 | CA | SER | B | 368 | 23.005 | 22.387 | 54.566 | 1.00 | 55.54 | B | C |
| ATOM | 5120 | CB | SER | B | 368 | 21.879 | 22.943 | 55.446 | 1.00 | 46.32 | B | C |
| ATOM | 5121 | OG | SER | B | 368 | 20.856 | 21.989 | 55.633 | 1.00 | 46.32 | B | O |
| ATOM | 5122 | C | SER | B | 368 | 23.687 | 21.212 | 55.272 | 1.00 | 55.54 | B | C |
| ATOM | 5123 | O | SER | B | 368 | 24.812 | 21.353 | 55.751 | 1.00 | 55.54 | B | O |
| ATOM | 5124 | N | SER | B | 369 | 23.034 | 20.053 | 55.321 | 1.00 | 47.27 | B | N |
| ATOM | 5125 | CA | SER | B | 369 | 23.596 | 18.892 | 56.021 | 1.00 | 47.27 | B | C |
| ATOM | 5126 | CB | SER | B | 369 | 22.680 | 17.673 | 55.867 | 1.00 | 42.97 | B | C |
| ATOM | 5127 | OG | SER | B | 369 | 23.125 | 16.822 | 54.824 | 1.00 | 42.97 | B | O |
| ATOM | 5128 | C | SER | B | 369 | 25.013 | 18.491 | 55.610 | 1.00 | 47.27 | B | C |
| ATOM | 5129 | O | SER | B | 369 | 25.717 | 17.831 | 56.373 | 1.00 | 47.27 | B | O |
| ATOM | 5130 | N | ASN | B | 370 | 25.437 | 18.879 | 54.411 | 1.00 | 49.80 | B | N |
| ATOM | 5131 | CA | ASN | B | 370 | 26.771 | 18.520 | 53.944 | 1.00 | 49.80 | B | C |
| ATOM | 5132 | CB | ASN | B | 370 | 26.823 | 17.035 | 53.627 | 1.00 | 43.79 | B | C |
| ATOM | 5133 | CG | ASN | B | 370 | 28.221 | 16.563 | 53.338 | 1.00 | 43.79 | B | C |
| ATOM | 5134 | OD1 | ASN | B | 370 | 28.905 | 17.115 | 52.481 | 1.00 | 43.79 | B | O |
| ATOM | 5135 | ND2 | ASN | B | 370 | 28.660 | 15.534 | 54.053 | 1.00 | 43.79 | B | N |
| ATOM | 5136 | C | ASN | B | 370 | 27.178 | 19.313 | 52.705 | 1.00 | 49.80 | B | C |
| ATOM | 5137 | O | ASN | B | 370 | 27.340 | 18.754 | 51.612 | 1.00 | 49.80 | B | O |
| ATOM | 5138 | N | PRO | B | 371 | 27.369 | 20.630 | 52.868 | 1.00 | 42.27 | B | N |
| ATOM | 5139 | CD | PRO | B | 371 | 27.296 | 21.334 | 54.162 | 1.00 | 39.04 | B | C |
| ATOM | 5140 | CA | PRO | B | 371 | 27.752 | 21.551 | 51.800 | 1.00 | 42.27 | B | C |
| ATOM | 5141 | CB | PRO | B | 371 | 28.375 | 22.700 | 52.573 | 1.00 | 39.04 | B | C |
| ATOM | 5142 | CG | PRO | B | 371 | 27.456 | 22.782 | 53.757 | 1.00 | 39.04 | B | C |
| ATOM | 5143 | C | PRO | B | 371 | 28.646 | 21.035 | 50.664 | 1.00 | 42.27 | B | C |
| ATOM | 5144 | O | PRO | B | 371 | 28.243 | 21.028 | 49.502 | 1.00 | 42.27 | B | O |
| ATOM | 5145 | N | PRO | B | 372 | 29.862 | 20.576 | 50.977 | 1.00 | 51.61 | B | N |
| ATOM | 5146 | CD | PRO | B | 372 | 30.450 | 20.240 | 52.282 | 1.00 | 27.30 | B | C |
| ATOM | 5147 | CA | PRO | B | 372 | 30.718 | 20.100 | 49.888 | 1.00 | 51.61 | B | C |
| ATOM | 5148 | CB | PRO | B | 372 | 31.958 | 19.593 | 50.625 | 1.00 | 27.30 | B | C |
| ATOM | 5149 | CG | PRO | B | 372 | 31.402 | 19.131 | 51.908 | 1.00 | 27.30 | B | C |
| ATOM | 5150 | C | PRO | B | 372 | 30.137 | 19.070 | 48.903 | 1.00 | 51.61 | B | C |
| ATOM | 5151 | O | PRO | B | 372 | 30.739 | 18.819 | 47.850 | 1.00 | 51.61 | B | O |
| ATOM | 5152 | N | LEU | B | 373 | 28.989 | 18.473 | 49.218 | 1.00 | 40.62 | B | N |

FIG. 3-78

| ATOM | 5153 | CA | LEU | B | 373 | 28.408 | 17.506 | 48.293 | 1.00 | 40.62 | B | C |
|------|------|-----|-----|---|-----|--------|--------|--------|------|-------|---|---|
| ATOM | 5154 | CB | LEU | B | 373 | 27.208 | 16.810 | 48.929 | 1.00 | 51.31 | B | C |
| ATOM | 5155 | CG | LEU | B | 373 | 27.582 | 15.557 | 49.741 | 1.00 | 51.31 | B | C |
| ATOM | 5156 | CD1 | LEU | B | 373 | 26.366 | 15.017 | 50.470 | 1.00 | 51.31 | B | C |
| ATOM | 5157 | CD2 | LEU | B | 373 | 28.150 | 14.493 | 48.808 | 1.00 | 51.31 | B | C |
| ATOM | 5158 | C | LEU | B | 373 | 27.993 | 18.200 | 46.995 | 1.00 | 40.62 | B | C |
| ATOM | 5159 | O | LEU | B | 373 | 27.749 | 17.559 | 45.963 | 1.00 | 40.62 | B | O |
| ATOM | 5160 | N | ALA | B | 374 | 27.950 | 19.525 | 47.061 | 1.00 | 46.33 | B | N |
| ATOM | 5161 | CA | ALA | B | 374 | 27.573 | 20.350 | 45.932 | 1.00 | 46.33 | B | C |
| ATOM | 5162 | CB | ALA | B | 374 | 27.552 | 21.807 | 46.357 | 1.00 | 26.93 | B | C |
| ATOM | 5163 | C | ALA | B | 374 | 28.498 | 20.166 | 44.733 | 1.00 | 46.33 | B | C |
| ATOM | 5164 | O | ALA | B | 374 | 28.106 | 20.434 | 43.592 | 1.00 | 46.33 | B | O |
| ATOM | 5165 | N | THR | B | 375 | 29.725 | 19.719 | 44.973 | 1.00 | 51.49 | B | N |
| ATOM | 5166 | CA | THR | B | 375 | 30.645 | 19.541 | 43.857 | 1.00 | 51.49 | B | C |
| ATOM | 5167 | CB | THR | B | 375 | 32.091 | 19.321 | 44.321 | 1.00 | 52.84 | B | C |
| ATOM | 5168 | OG1 | THR | B | 375 | 32.121 | 18.311 | 45.339 | 1.00 | 52.84 | B | O |
| ATOM | 5169 | CG2 | THR | B | 375 | 32.677 | 20.622 | 44.853 | 1.00 | 52.84 | B | C |
| ATOM | 5170 | C | THR | B | 375 | 30.224 | 18.359 | 43.018 | 1.00 | 51.49 | B | C |
| ATOM | 5171 | O | THR | B | 375 | 30.613 | 18.253 | 41.855 | 1.00 | 51.49 | B | O |
| ATOM | 5172 | N | ILE | B | 376 | 29.427 | 17.472 | 43.611 | 1.00 | 69.10 | B | N |
| ATOM | 5173 | CA | ILE | B | 376 | 28.948 | 16.298 | 42.891 | 1.00 | 69.10 | B | C |
| ATOM | 5174 | CB | ILE | B | 376 | 28.982 | 15.028 | 43.769 | 1.00 | 55.74 | B | C |
| ATOM | 5175 | CG2 | ILE | B | 376 | 28.553 | 13.817 | 42.944 | 1.00 | 55.74 | B | C |
| ATOM | 5176 | CG1 | ILE | B | 376 | 30.391 | 14.797 | 44.310 | 1.00 | 55.74 | B | C |
| ATOM | 5177 | CD1 | ILE | B | 376 | 30.526 | 13.519 | 45.140 | 1.00 | 55.74 | B | C |
| ATOM | 5178 | C | ILE | B | 376 | 27.510 | 16.519 | 42.424 | 1.00 | 69.10 | B | C |
| ATOM | 5179 | O | ILE | B | 376 | 27.174 | 16.256 | 41.265 | 1.00 | 69.10 | B | O |
| ATOM | 5180 | N | LEU | B | 377 | 26.669 | 17.014 | 43.328 | 1.00 | 53.55 | B | N |
| ATOM | 5181 | CA | LEU | B | 377 | 25.262 | 17.259 | 43.018 | 1.00 | 53.55 | B | C |
| ATOM | 5182 | CB | LEU | B | 377 | 24.524 | 17.693 | 44.281 | 1.00 | 53.61 | B | C |
| ATOM | 5183 | CG | LEU | B | 377 | 24.597 | 16.597 | 45.343 | 1.00 | 53.61 | B | C |
| ATOM | 5184 | CD1 | LEU | B | 377 | 24.124 | 17.131 | 46.679 | 1.00 | 53.61 | B | C |
| ATOM | 5185 | CD2 | LEU | B | 377 | 23.781 | 15.395 | 44.884 | 1.00 | 53.61 | B | C |
| ATOM | 5186 | C | LEU | B | 377 | 25.030 | 18.274 | 41.904 | 1.00 | 53.55 | B | C |
| ATOM | 5187 | O | LEU | B | 377 | 24.121 | 18.102 | 41.094 | 1.00 | 53.55 | B | O |
| ATOM | 5188 | N | ILE | B | 378 | 25.841 | 19.326 | 41.858 | 1.00 | 56.70 | B | N |
| ATOM | 5189 | CA | ILE | B | 378 | 25.697 | 20.349 | 40.823 | 1.00 | 56.70 | B | C |
| ATOM | 5190 | CB | ILE | B | 378 | 25.776 | 21.771 | 41.398 | 1.00 | 42.43 | B | C |
| ATOM | 5191 | CG2 | ILE | B | 378 | 25.682 | 22.772 | 40.270 | 1.00 | 42.43 | B | C |
| ATOM | 5192 | CG1 | ILE | B | 378 | 24.638 | 22.005 | 42.390 | 1.00 | 42.43 | B | C |
| ATOM | 5193 | CD1 | ILE | B | 378 | 24.727 | 23.313 | 43.136 | 1.00 | 42.43 | B | C |
| ATOM | 5194 | C | ILE | B | 378 | 26.806 | 20.189 | 39.796 | 1.00 | 56.70 | B | C |
| ATOM | 5195 | O | ILE | B | 378 | 27.880 | 20.783 | 39.924 | 1.00 | 56.70 | B | O |
| ATOM | 5196 | N | PRO | B | 379 | 26.558 | 19.378 | 38.756 | 1.00 | 60.86 | B | N |
| ATOM | 5197 | CD | PRO | B | 379 | 25.268 | 18.792 | 38.357 | 1.00 | 40.56 | B | C |
| ATOM | 5198 | CA | PRO | B | 379 | 27.566 | 19.160 | 37.723 | 1.00 | 60.86 | B | C |
| ATOM | 5199 | CB | PRO | B | 379 | 26.854 | 18.225 | 36.753 | 1.00 | 40.56 | B | C |
| ATOM | 5200 | CG | PRO | B | 379 | 25.430 | 18.660 | 36.871 | 1.00 | 40.56 | B | C |
| ATOM | 5201 | C | PRO | B | 379 | 27.970 | 20.486 | 37.092 | 1.00 | 60.86 | B | C |
| ATOM | 5202 | O | PRO | B | 379 | 27.224 | 21.470 | 37.156 | 1.00 | 60.86 | B | O |
| ATOM | 5203 | N | PRO | B | 380 | 29.162 | 20.531 | 36.479 | 1.00 | 78.88 | B | N |
| ATOM | 5204 | CD | PRO | B | 380 | 30.131 | 19.424 | 36.387 | 1.00 | 81.30 | B | C |
| ATOM | 5205 | CA | PRO | B | 380 | 29.690 | 21.736 | 35.831 | 1.00 | 78.88 | B | C |
| ATOM | 5206 | CB | PRO | B | 380 | 30.980 | 21.238 | 35.187 | 1.00 | 81.30 | B | C |
| ATOM | 5207 | CG | PRO | B | 380 | 31.426 | 20.161 | 36.153 | 1.00 | 81.30 | B | C |
| ATOM | 5208 | C | PRO | B | 380 | 28.743 | 22.393 | 34.821 | 1.00 | 78.88 | B | C |
| ATOM | 5209 | O | PRO | B | 380 | 28.437 | 23.586 | 34.944 | 1.00 | 78.88 | B | O |
| ATOM | 5210 | N | HIS | B | 381 | 28.277 | 21.629 | 33.830 | 1.00 | 61.90 | B | N |
| ATOM | 5211 | CA | HIS | B | 381 | 27.376 | 22.166 | 32.803 | 1.00 | 61.90 | B | C |
| ATOM | 5212 | CB | HIS | B | 381 | 26.906 | 21.038 | 31.879 | 1.00 | 63.66 | B | C |
| ATOM | 5213 | CG | HIS | B | 381 | 25.734 | 20.268 | 32.411 | 1.00 | 63.66 | B | C |
| ATOM | 5214 | CD2 | HIS | B | 381 | 25.666 | 19.076 | 33.052 | 1.00 | 63.66 | B | C |
| ATOM | 5215 | ND1 | HIS | B | 381 | 24.437 | 20.738 | 32.339 | 1.00 | 63.66 | B | N |
| ATOM | 5216 | CE1 | HIS | B | 381 | 23.622 | 19.869 | 32.912 | 1.00 | 63.66 | B | C |
| ATOM | 5217 | NE2 | HIS | B | 381 | 24.343 | 18.852 | 33.353 | 1.00 | 63.66 | B | N |
| ATOM | 5218 | C | HIS | B | 381 | 26.148 | 22.892 | 33.382 | 1.00 | 61.90 | B | C |
| ATOM | 5219 | O | HIS | B | 381 | 25.527 | 23.704 | 32.701 | 1.00 | 61.90 | B | O |

FIG. 3-79

```
ATOM   5220  N   ALA B 382      25.783  22.601  34.627  1.00 75.54      B  N
ATOM   5221  CA  ALA B 382      24.624  23.254  35.229  1.00 75.54      B  C
ATOM   5222  CB  ALA B 382      23.912  22.291  36.163  1.00 65.68      B  C
ATOM   5223  C   ALA B 382      25.023  24.530  35.984  1.00 75.54      B  C
ATOM   5224  O   ALA B 382      24.157  25.305  36.439  1.00 75.54      B  O
ATOM   5225  N   ARG B 383      26.335  24.742  36.123  1.00 79.78      B  N
ATOM   5226  CA  ARG B 383      26.855  25.926  36.801  1.00 79.78      B  C
ATOM   5227  CB  ARG B 383      28.351  25.748  37.102  1.00 75.02      B  C
ATOM   5228  CG  ARG B 383      28.627  25.262  38.518  1.00 75.02      B  C
ATOM   5229  CD  ARG B 383      28.969  23.785  38.604  1.00 75.02      B  C
ATOM   5230  NE  ARG B 383      30.409  23.542  38.470  1.00 75.02      B  N
ATOM   5231  CZ  ARG B 383      31.090  22.614  39.152  1.00 75.02      B  C
ATOM   5232  NH1 ARG B 383      30.476  21.823  40.036  1.00 75.02      B  N
ATOM   5233  NH2 ARG B 383      32.397  22.467  38.948  1.00 75.02      B  N
ATOM   5234  C   ARG B 383      26.616  27.174  35.938  1.00 79.78      B  C
ATOM   5235  O   ARG B 383      27.028  28.286  36.293  1.00 79.78      B  O
ATOM   5236  N   ILE B 384      25.934  26.952  34.809  1.00100.00      B  N
ATOM   5237  CA  ILE B 384      25.561  27.977  33.816  1.00100.00      B  C
ATOM   5238  CB  ILE B 384      24.128  28.555  34.128  1.00 99.74      B  C
ATOM   5239  CG2 ILE B 384      23.581  29.336  32.905  1.00 99.74      B  C
ATOM   5240  CG1 ILE B 384      23.171  27.406  34.489  1.00 99.74      B  C
ATOM   5241  CD1 ILE B 384      21.698  27.831  34.666  1.00 99.74      B  C
ATOM   5242  C   ILE B 384      26.555  29.152  33.649  1.00100.00      B  C
ATOM   5243  O   ILE B 384      27.205  29.217  32.566  1.00100.00      B  O
ATOM   5244  OXT ILE B 384      26.671  29.989  34.591  1.00 99.74      B  O
TER    5245      ILE B 384                                              B
ATOM   5246  C1  4A  I   1      10.253   5.669   5.097  1.00 70.71      I  C
ATOM   5247  C2  4A  I   1      10.050   4.331   5.628  1.00 70.71      I  C
ATOM   5248  C3  4A  I   1       9.835   3.230   4.683  1.00 70.71      I  C
ATOM   5249  C4  4A  I   1       9.812   3.459   3.221  1.00 70.71      I  C
ATOM   5250  C5  4A  I   1      10.017   4.802   2.685  1.00 70.71      I  C
ATOM   5251  C6  4A  I   1      10.241   5.919   3.625  1.00 70.71      I  C
ATOM   5252  C12 4A  I   1       9.669   1.857   5.189  1.00 70.71      I  C
ATOM   5253  N13 4A  I   1       8.568   1.644   6.036  1.00 70.71      I  N
ATOM   5254  N14 4A  I   1       8.268   0.428   6.607  1.00 70.71      I  N
ATOM   5255  C15 4A  I   1       9.024  -0.745   6.430  1.00 70.71      I  C
ATOM   5256  C16 4A  I   1      10.190  -0.720   5.584  1.00 70.71      I  C
ATOM   5257  C17 4A  I   1      10.549   0.584   4.906  1.00 70.71      I  C
ATOM   5258  C18 4A  I   1      11.664   0.642   3.864  1.00 70.71      I  C
ATOM   5259  C19 4A  I   1      12.881   1.458   4.005  1.00 70.71      I  C
ATOM   5260  C20 4A  I   1      13.847   1.510   2.891  1.00 70.71      I  C
ATOM   5261  C21 4A  I   1      13.597   0.739   1.633  1.00 70.71      I  C
ATOM   5262  C22 4A  I   1      12.378  -0.100   1.477  1.00 70.71      I  C
ATOM   5263  C23 4A  I   1      11.427  -0.146   2.581  1.00 70.71      I  C
ATOM   5264  N29 4A  I   1       8.887  -2.028   6.887  1.00 70.71      I  N
ATOM   5265  N1  4A  I   1       9.907  -2.787   6.360  1.00 70.71      I  N
ATOM   5266  C31 4A  I   1      10.738  -2.052   5.564  1.00 70.71      I  C
ATOM   5267  N32 4A  I   1      11.990  -2.299   4.816  1.00 70.71      I  N
TER    5268      4A  I   1                                              I
ATOM   5269  C1  4B  J   1      -4.156  13.281  52.166  1.00 63.32      J  C
ATOM   5270  C2  4B  J   1      -3.989  13.950  50.879  1.00 63.32      J  C
ATOM   5271  C3  4B  J   1      -3.476  13.224  49.702  1.00 63.32      J  C
ATOM   5272  C4  4B  J   1      -3.138  11.794  49.844  1.00 63.32      J  C
ATOM   5273  C5  4B  J   1      -3.314  11.124  51.155  1.00 63.32      J  C
ATOM   5274  C6  4B  J   1      -3.821  11.866  52.320  1.00 63.32      J  C
ATOM   5275  C12 4B  J   1      -3.263  13.932  48.405  1.00 63.32      J  C
ATOM   5276  N13 4B  J   1      -2.461  15.111  48.508  1.00 63.32      J  N
ATOM   5277  N14 4B  J   1      -2.104  15.935  47.447  1.00 63.32      J  N
ATOM   5278  C15 4B  J   1      -2.495  15.715  46.132  1.00 63.32      J  C
ATOM   5279  C16 4B  J   1      -3.308  14.574  45.818  1.00 63.32      J  C
ATOM   5280  C17 4B  J   1      -3.735  13.610  46.936  1.00 63.32      J  C
ATOM   5281  C18 4B  J   1      -4.555  12.369  46.537  1.00 63.32      J  C
ATOM   5282  C19 4B  J   1      -5.940  12.170  46.996  1.00 63.32      J  C
ATOM   5283  C20 4B  J   1      -6.688  10.974  46.565  1.00 63.32      J  C
ATOM   5284  C21 4B  J   1      -6.066   9.967  45.672  1.00 63.32      J  C
ATOM   5285  C22 4B  J   1      -4.680  10.139  45.198  1.00 63.32      J  C
ATOM   5286  C23 4B  J   1      -3.939  11.317  45.626  1.00 63.32      J  C
```

FIG. 3-80

```
ATOM   5287  N29  4B   J   1    -2.278  16.371  44.945  1.00 63.32      J  N
ATOM   5288  N1   4B   J   1    -2.883  15.738  43.909  1.00 63.32      J  N
ATOM   5289  C31  4B   J   1    -3.533  14.629  44.384  1.00 63.32      J  C
ATOM   5290  N32  4B   J   1    -4.412  13.571  43.807  1.00 63.32      J  N
TER    5291       4B   J   1                                             J
ATOM   5292  O    HOH  W   1    -1.499   8.933 -13.094  1.00 26.17      W  O
ATOM   5293  O    HOH  W   2    -3.474  10.448  -6.384  1.00 20.73      W  O
ATOM   5294  O    HOH  W   3    10.121  -2.709  55.746  1.00 23.52      W  O
ATOM   5295  O    HOH  W   4     9.265  10.406  29.771  1.00 32.87      W  O
ATOM   5296  O    HOH  W   5     2.433  -1.556  53.562  1.00 25.79      W  O
ATOM   5297  O    HOH  W   6   -10.271  12.840  -5.136  1.00 28.43      W  O
ATOM   5298  O    HOH  W   7    -9.544  22.066  -6.134  1.00 51.67      W  O
ATOM   5299  O    HOH  W   8     3.275  10.739  67.679  1.00 37.05      W  O
ATOM   5300  O    HOH  W   9     6.641   8.203 -10.828  1.00 34.94      W  O
ATOM   5301  O    HOH  W  10     1.509  17.175 -11.339  1.00 31.08      W  O
ATOM   5302  O    HOH  W  11    -9.030  31.029  55.887  1.00 48.32      W  O
ATOM   5303  O    HOH  W  12     5.198  -3.326  62.884  1.00 39.14      W  O
ATOM   5304  O    HOH  W  13    -3.865  13.932   9.234  1.00 40.44      W  O
ATOM   5305  O    HOH  W  15     2.173   7.983   2.977  1.00 30.25      W  O
ATOM   5306  O    HOH  W  16    -0.614  -9.702 -15.250  1.00 33.85      W  O
ATOM   5307  O    HOH  W  17    22.550  16.289  41.249  1.00 45.82      W  O
ATOM   5308  O    HOH  W  18    14.655  17.087  41.536  1.00 43.86      W  O
ATOM   5309  O    HOH  W  19   -11.850  29.586  56.221  1.00 37.36      W  O
ATOM   5310  O    HOH  W  20    16.052   2.949  31.753  1.00 26.10      W  O
ATOM   5311  O    HOH  W  21    -8.034  18.041   4.405  1.00 43.98      W  O
ATOM   5312  O    HOH  W  22     1.718  -0.681  48.664  1.00 36.25      W  O
ATOM   5313  O    HOH  W  23    -2.152 -16.363 -12.425  1.00 35.35      W  O
ATOM   5314  O    HOH  W  24   -15.048   7.668  -5.828  1.00 36.07      W  O
ATOM   5315  O    HOH  W  25     3.655  11.966  -1.762  1.00 42.93      W  O
ATOM   5316  O    HOH  W  26     8.730   6.832  55.789  1.00 42.73      W  O
ATOM   5317  O    HOH  W  27    -6.767  -9.603   3.297  1.00 62.80      W  O
ATOM   5318  O    HOH  W  28     1.470   5.443 -14.392  1.00 37.15      W  O
ATOM   5319  O    HOH  W  29    20.700  14.552  53.440  1.00 41.48      W  O
ATOM   5320  O    HOH  W  30   -14.476  -3.140  13.989  1.00 42.42      W  O
ATOM   5321  O    HOH  W  31    18.723  28.062  51.847  1.00 40.69      W  O
ATOM   5322  O    HOH  W  32    10.155   3.921  58.239  1.00 32.93      W  O
ATOM   5323  O    HOH  W  33     9.437   7.018  23.941  1.00 46.93      W  O
ATOM   5324  O    HOH  W  34     5.230  -3.459  20.049  1.00 39.47      W  O
ATOM   5325  O    HOH  W  37    11.281  -1.146  -3.827  1.00 58.71      W  O
ATOM   5326  O    HOH  W  38     6.505 -14.066  -6.485  1.00 50.26      W  O
ATOM   5327  O    HOH  W  39     8.895   4.730  -1.163  1.00 71.70      W  O
ATOM   5328  O    HOH  W  40     7.784  12.669   8.842  1.00 52.29      W  O
ATOM   5329  O    HOH  W  41     8.145   8.969   3.989  1.00 36.14      W  O
ATOM   5330  O    HOH  W  42    -1.337  19.127   3.100  1.00 30.02      W  O
ATOM   5331  O    HOH  W  43     6.002  14.573  -4.459  1.00 49.52      W  O
ATOM   5332  O    HOH  W  44     1.275   2.485 -13.625  1.00 39.24      W  O
ATOM   5333  O    HOH  W  45    -2.940  21.659 -16.749  1.00 30.01      W  O
ATOM   5334  O    HOH  W  46   -14.450  18.693  -6.321  1.00 42.63      W  O
ATOM   5335  O    HOH  W  47     7.691  -2.124 -14.096  1.00 51.24      W  O
ATOM   5336  O    HOH  W  48     2.797   3.725 -22.272  1.00 54.13      W  O
ATOM   5337  O    HOH  W  49    12.806  18.864 -20.430  1.00 47.31      W  O
ATOM   5338  O    HOH  W  50     7.761  17.426 -13.700  1.00 47.08      W  O
ATOM   5339  O    HOH  W  51     4.041  17.228 -23.197  1.00 39.31      W  O
ATOM   5340  O    HOH  W  52   -10.596   4.345 -22.103  1.00 44.02      W  O
ATOM   5341  O    HOH  W  53   -12.482   8.523 -20.065  1.00 40.66      W  O
ATOM   5342  O    HOH  W  54   -12.024  19.964 -23.235  1.00 54.21      W  O
ATOM   5343  O    HOH  W  55   -19.664  13.333 -15.537  1.00 22.84      W  O
ATOM   5344  O    HOH  W  56   -18.788   8.054  -5.562  1.00 42.10      W  O
ATOM   5345  O    HOH  W  57   -19.406   4.325  -6.364  1.00 29.43      W  O
ATOM   5346  O    HOH  W  58     3.342 -18.639  -4.174  1.00 40.50      W  O
ATOM   5347  O    HOH  W  59    -1.816  30.431  46.686  1.00 38.80      W  O
ATOM   5348  O    HOH  W  60   -15.890  21.282  50.428  1.00 39.30      W  O
ATOM   5349  O    HOH  W  61   -17.132  24.941  51.488  1.00 51.28      W  O
ATOM   5350  O    HOH  W  62   -15.135  15.048  36.943  1.00 46.52      W  O
ATOM   5351  O    HOH  W  63    -4.489  22.460  36.793  1.00 51.69      W  O
ATOM   5352  O    HOH  W  65     0.311  13.432  37.969  1.00 64.84      W  O
ATOM   5353  O    HOH  W  66    19.128  13.434  56.847  1.00 42.91      W  O
```

FIG. 3-81

| ATOM | 5354 | O | HOH | W | 67 | -1.018 | 16.062 | 53.046 | 1.00 | 52.19 | W | O |
| ATOM | 5355 | O | HOH | W | 68 | 6.056 | 15.597 | 70.872 | 1.00 | 56.66 | W | O |
| ATOM | 5356 | O | HOH | W | 69 | 6.977 | 14.981 | 76.128 | 1.00 | 59.64 | W | O |
| ATOM | 5357 | O | HOH | W | 70 | 0.063 | 5.262 | 69.337 | 1.00 | 45.62 | W | O |
| ATOM | 5358 | O | HOH | W | 71 | 6.082 | 8.758 | 72.399 | 1.00 | 60.12 | W | O |
| ATOM | 5359 | O | HOH | W | 72 | -0.244 | 3.476 | 60.263 | 1.00 | 30.00 | W | O |
| ATOM | 5360 | O | HOH | W | 73 | 15.902 | 5.786 | 62.704 | 1.00 | 52.39 | W | O |
| ATOM | 5361 | O | HOH | W | 74 | 8.904 | -2.399 | 48.896 | 1.00 | 25.48 | W | O |
| ATOM | 5362 | O | HOH | W | 75 | 27.098 | -6.257 | 62.272 | 1.00 | 43.45 | W | O |
| ATOM | 5363 | O | HOH | W | 76 | 26.572 | 7.921 | 56.951 | 1.00 | 25.95 | W | O |
| ATOM | 5364 | O | HOH | W | 77 | 28.602 | 5.817 | 52.562 | 1.00 | 35.56 | W | O |
| ATOM | 5365 | O | HOH | W | 78 | 21.827 | 7.530 | 58.421 | 1.00 | 32.42 | W | O |
| ATOM | 5366 | O | HOH | W | 79 | 21.891 | 17.290 | 33.040 | 1.00 | 59.23 | W | O |
| ATOM | 5367 | O | HOH | W | 80 | -4.881 | 9.861 | 41.937 | 1.00 | 61.23 | W | O |
| ATOM | 5368 | O | HOH | W | 81 | 13.331 | -3.295 | 0.316 | 1.00 | 42.38 | W | O |
| ATOM | 5369 | O | HOH | W | 82 | -5.714 | -8.707 | 7.351 | 1.00 | 32.38 | W | O |
| ATOM | 5370 | O | HOH | W | 83 | 13.104 | 21.394 | 43.241 | 1.00 | 31.90 | W | O |
| TER | 5371 | | HOH | W | 83 | | | | | | W | |
| END | | | | | | | | | | | | |

FIG. 4-1

| | | Atom Type | Resid | # | X | Y | Z | OCC | B | | |
|---|---|---|---|---|---|---|---|---|---|---|---|
| ATOM | 1 | CB | SER A | 25 | 49.677 | 12.283 | 58.759 | 1.00 | 77.22 | A | C |
| ATOM | 2 | OG | SER A | 25 | 50.798 | 12.476 | 59.618 | 1.00 | 77.22 | A | O |
| ATOM | 3 | C | SER A | 25 | 49.980 | 14.594 | 57.816 | 1.00 | 76.64 | A | C |
| ATOM | 4 | O | SER A | 25 | 50.297 | 14.490 | 56.622 | 1.00 | 76.64 | A | O |
| ATOM | 5 | N | SER A | 25 | 47.851 | 13.400 | 57.467 | 1.00 | 76.64 | A | N |
| ATOM | 6 | CA | SER A | 25 | 48.974 | 13.616 | 58.437 | 1.00 | 76.64 | A | C |
| ATOM | 7 | N | MET A | 26 | 50.486 | 15.530 | 58.625 | 1.00 | 62.89 | A | N |
| ATOM | 8 | CA | MET A | 26 | 51.448 | 16.538 | 58.155 | 1.00 | 62.89 | A | C |
| ATOM | 9 | CB | MET A | 26 | 51.284 | 17.826 | 58.955 | 1.00 | 69.43 | A | C |
| ATOM | 10 | CG | MET A | 26 | 50.016 | 18.581 | 58.620 | 1.00 | 69.43 | A | C |
| ATOM | 11 | SD | MET A | 26 | 49.425 | 19.512 | 60.053 | 1.00 | 69.43 | A | S |
| ATOM | 12 | CE | MET A | 26 | 50.822 | 20.744 | 60.221 | 1.00 | 69.43 | A | C |
| ATOM | 13 | C | MET A | 26 | 52.918 | 16.126 | 58.197 | 1.00 | 62.89 | A | C |
| ATOM | 14 | O | MET A | 26 | 53.367 | 15.462 | 59.134 | 1.00 | 62.89 | A | O |
| ATOM | 15 | N | LYS A | 27 | 53.667 | 16.545 | 57.182 | 1.00 | 63.46 | A | N |
| ATOM | 16 | CA | LYS A | 27 | 55.088 | 16.236 | 57.085 | 1.00 | 63.46 | A | C |
| ATOM | 17 | CB | LYS A | 27 | 55.333 | 15.288 | 55.904 | 1.00 | 57.46 | A | C |
| ATOM | 18 | CG | LYS A | 27 | 56.509 | 14.335 | 56.083 | 1.00 | 57.46 | A | C |
| ATOM | 19 | CD | LYS A | 27 | 56.059 | 12.990 | 56.666 | 1.00 | 57.46 | A | C |
| ATOM | 20 | CE | LYS A | 27 | 55.268 | 12.133 | 55.643 | 1.00 | 57.46 | A | C |
| ATOM | 21 | NZ | LYS A | 27 | 56.131 | 11.611 | 54.521 | 1.00 | 57.46 | A | N |
| ATOM | 22 | C | LYS A | 27 | 55.809 | 17.571 | 56.855 | 1.00 | 63.46 | A | C |
| ATOM | 23 | O | LYS A | 27 | 55.912 | 18.053 | 55.714 | 1.00 | 63.46 | A | O |
| ATOM | 24 | N | VAL A | 28 | 56.309 | 18.167 | 57.934 | 1.00 | 59.71 | A | N |
| ATOM | 25 | CA | VAL A | 28 | 56.988 | 19.471 | 57.844 | 1.00 | 59.71 | A | C |
| ATOM | 26 | CB | VAL A | 28 | 56.688 | 20.321 | 59.104 | 1.00 | 58.68 | A | C |
| ATOM | 27 | CG1 | VAL A | 28 | 56.827 | 19.449 | 60.346 | 1.00 | 58.68 | A | C |
| ATOM | 28 | CG2 | VAL A | 28 | 57.659 | 21.515 | 59.189 | 1.00 | 58.68 | A | C |
| ATOM | 29 | C | VAL A | 28 | 58.514 | 19.458 | 57.633 | 1.00 | 59.71 | A | C |
| ATOM | 30 | O | VAL A | 28 | 59.269 | 19.085 | 58.536 | 1.00 | 59.71 | A | O |
| ATOM | 31 | N | GLY A | 29 | 58.954 | 19.902 | 56.453 | 1.00 | 45.44 | A | N |
| ATOM | 32 | CA | GLY A | 29 | 60.372 | 19.948 | 56.124 | 1.00 | 45.44 | A | C |
| ATOM | 33 | C | GLY A | 29 | 60.706 | 21.326 | 55.590 | 1.00 | 45.44 | A | C |
| ATOM | 34 | O | GLY A | 29 | 59.909 | 21.922 | 54.870 | 1.00 | 45.44 | A | O |
| ATOM | 35 | N | ARG A | 30 | 61.879 | 21.844 | 55.939 | 1.00 | 87.33 | A | N |
| ATOM | 36 | CA | ARG A | 30 | 62.293 | 23.179 | 55.490 | 1.00 | 87.33 | A | C |
| ATOM | 37 | CB | ARG A | 30 | 63.008 | 23.915 | 56.637 | 1.00 | 70.93 | A | C |
| ATOM | 38 | CG | ARG A | 30 | 63.531 | 25.306 | 56.281 | 1.00 | 70.93 | A | C |
| ATOM | 39 | CD | ARG A | 30 | 64.167 | 25.982 | 57.480 | 1.00 | 70.93 | A | C |
| ATOM | 40 | NE | ARG A | 30 | 63.179 | 26.355 | 58.504 | 1.00 | 70.93 | A | N |
| ATOM | 41 | CZ | ARG A | 30 | 62.657 | 25.531 | 59.422 | 1.00 | 70.93 | A | C |
| ATOM | 42 | NH1 | ARG A | 30 | 61.760 | 25.983 | 60.304 | 1.00 | 70.93 | A | N |
| ATOM | 43 | NH2 | ARG A | 30 | 63.035 | 24.258 | 59.474 | 1.00 | 70.93 | A | N |
| ATOM | 44 | C | ARG A | 30 | 63.209 | 23.143 | 54.250 | 1.00 | 87.33 | A | C |
| ATOM | 45 | O | ARG A | 30 | 64.440 | 22.992 | 54.370 | 1.00 | 87.33 | A | O |
| ATOM | 46 | N | GLY A | 31 | 62.621 | 23.301 | 53.064 | 1.00 | 66.72 | A | N |
| ATOM | 47 | CA | GLY A | 31 | 63.428 | 23.265 | 51.853 | 1.00 | 66.72 | A | C |
| ATOM | 48 | C | GLY A | 31 | 63.292 | 24.475 | 50.945 | 1.00 | 66.72 | A | C |
| ATOM | 49 | O | GLY A | 31 | 62.246 | 25.145 | 50.941 | 1.00 | 66.72 | A | O |
| ATOM | 50 | N | GLY A | 32 | 64.349 | 24.743 | 50.166 | 1.00 | 100.00 | A | N |
| ATOM | 51 | CA | GLY A | 32 | 64.355 | 25.882 | 49.257 | 1.00 | 100.00 | A | C |
| ATOM | 52 | C | GLY A | 32 | 64.616 | 27.197 | 49.995 | 1.00 | 100.00 | A | C |
| ATOM | 53 | O | GLY A | 32 | 63.920 | 27.531 | 50.992 | 1.00 | 100.00 | A | O |
| ATOM | 54 | N | GLY A | 33 | 65.621 | 27.940 | 49.510 | 1.00 | 74.90 | A | N |
| ATOM | 55 | CA | GLY A | 33 | 66.002 | 29.208 | 50.123 | 1.00 | 74.90 | A | C |
| ATOM | 56 | C | GLY A | 33 | 65.695 | 29.288 | 51.624 | 1.00 | 74.90 | A | C |
| ATOM | 57 | O | GLY A | 33 | 65.168 | 30.296 | 52.116 | 1.00 | 74.90 | A | O |
| ATOM | 58 | N | GLY A | 34 | 65.998 | 28.216 | 52.356 | 1.00 | 74.22 | A | N |
| ATOM | 59 | CA | GLY A | 34 | 65.745 | 28.202 | 53.791 | 1.00 | 74.22 | A | C |
| ATOM | 60 | C | GLY A | 34 | 64.337 | 28.566 | 54.271 | 1.00 | 74.22 | A | C |
| ATOM | 61 | O | GLY A | 34 | 64.146 | 28.959 | 55.433 | 1.00 | 74.22 | A | O |

FIG. 4-2

```
ATOM     62  N   GLY A  35      63.343  28.451  53.393  1.00 88.79           A  N
ATOM     63  CA  GLY A  35      61.979  28.754  53.801  1.00 88.79           A  C
ATOM     64  C   GLY A  35      61.375  27.487  54.392  1.00 88.79           A  C
ATOM     65  O   GLY A  35      61.716  26.385  53.937  1.00 88.79           A  O
ATOM     66  N   LYS A  36      60.515  27.607  55.405  1.00 59.36           A  N
ATOM     67  CA  LYS A  36      59.888  26.415  55.987  1.00 59.36           A  C
ATOM     68  CB  LYS A  36      59.296  26.711  57.359  1.00 44.45           A  C
ATOM     69  CG  LYS A  36      58.399  25.587  57.832  1.00 44.45           A  C
ATOM     70  CD  LYS A  36      57.847  25.826  59.217  1.00 44.45           A  C
ATOM     71  CE  LYS A  36      56.700  24.854  59.475  1.00 44.45           A  C
ATOM     72  NZ  LYS A  36      56.252  24.849  60.899  1.00 44.45           A  N
ATOM     73  C   LYS A  36      58.772  25.864  55.087  1.00 59.36           A  C
ATOM     74  O   LYS A  36      58.139  26.624  54.344  1.00 59.36           A  O
ATOM     75  N   VAL A  37      58.523  24.554  55.168  1.00 48.63           A  N
ATOM     76  CA  VAL A  37      57.492  23.917  54.341  1.00 48.63           A  C
ATOM     77  CB  VAL A  37      58.109  23.287  53.069  1.00 26.72           A  C
ATOM     78  CG1 VAL A  37      57.012  22.685  52.200  1.00 26.72           A  C
ATOM     79  CG2 VAL A  37      58.896  24.334  52.296  1.00 26.72           A  C
ATOM     80  C   VAL A  37      56.646  22.830  55.014  1.00 48.63           A  C
ATOM     81  O   VAL A  37      57.166  21.953  55.715  1.00 48.63           A  O
ATOM     82  N   THR A  38      55.333  22.898  54.792  1.00 43.29           A  N
ATOM     83  CA  THR A  38      54.414  21.900  55.329  1.00 43.29           A  C
ATOM     84  CB  THR A  38      53.210  22.535  56.069  1.00 22.74           A  C
ATOM     85  OG1 THR A  38      53.681  23.437  57.073  1.00 22.74           A  O
ATOM     86  CG2 THR A  38      52.376  21.459  56.755  1.00 22.74           A  C
ATOM     87  C   THR A  38      53.885  21.091  54.145  1.00 43.29           A  C
ATOM     88  O   THR A  38      53.501  21.646  53.108  1.00 43.29           A  O
ATOM     89  N   THR A  39      53.876  19.775  54.291  1.00 27.07           A  N
ATOM     90  CA  THR A  39      53.379  18.927  53.229  1.00 27.07           A  C
ATOM     91  CB  THR A  39      54.531  18.146  52.549  1.00 40.75           A  C
ATOM     92  OG1 THR A  39      55.214  19.012  51.633  1.00 40.75           A  O
ATOM     93  CG2 THR A  39      54.000  16.944  51.784  1.00 40.75           A  C
ATOM     94  C   THR A  39      52.368  17.966  53.804  1.00 27.07           A  C
ATOM     95  O   THR A  39      52.627  17.301  54.802  1.00 27.07           A  O
ATOM     96  N   VAL A  40      51.206  17.891  53.177  1.00 38.31           A  N
ATOM     97  CA  VAL A  40      50.173  17.004  53.671  1.00 38.31           A  C
ATOM     98  CB  VAL A  40      49.196  17.759  54.581  1.00 55.79           A  C
ATOM     99  CG1 VAL A  40      48.321  18.709  53.737  1.00 55.79           A  C
ATOM    100  CG2 VAL A  40      48.355  16.756  55.369  1.00 55.79           A  C
ATOM    101  C   VAL A  40      49.392  16.416  52.503  1.00 38.31           A  C
ATOM    102  O   VAL A  40      49.392  16.972  51.403  1.00 38.31           A  O
ATOM    103  N   VAL A  41      48.737  15.283  52.738  1.00 39.91           A  N
ATOM    104  CA  VAL A  41      47.918  14.681  51.699  1.00 39.91           A  C
ATOM    105  CB  VAL A  41      48.000  13.135  51.703  1.00 39.28           A  C
ATOM    106  CG1 VAL A  41      47.414  12.584  50.400  1.00 39.28           A  C
ATOM    107  CG2 VAL A  41      49.450  12.688  51.838  1.00 39.28           A  C
ATOM    108  C   VAL A  41      46.484  15.125  51.976  1.00 39.91           A  C
ATOM    109  O   VAL A  41      45.936  14.848  53.044  1.00 39.91           A  O
ATOM    110  N   ALA A  42      45.885  15.834  51.022  1.00 43.86           A  N
ATOM    111  CA  ALA A  42      44.521  16.328  51.193  1.00 43.86           A  C
ATOM    112  CB  ALA A  42      44.518  17.856  51.185  1.00 60.53           A  C
ATOM    113  C   ALA A  42      43.526  15.800  50.156  1.00 43.86           A  C
ATOM    114  O   ALA A  42      43.910  15.238  49.129  1.00 43.86           A  O
ATOM    115  N   THR A  43      42.243  15.994  50.438  1.00 39.40           A  N
ATOM    116  CA  THR A  43      41.173  15.559  49.547  1.00 39.40           A  C
ATOM    117  CB  THR A  43      39.955  15.041  50.345  1.00 43.81           A  C
ATOM    118  OG1 THR A  43      40.408  14.168  51.381  1.00 43.81           A  O
ATOM    119  CG2 THR A  43      38.983  14.282  49.444  1.00 43.81           A  C
ATOM    120  C   THR A  43      40.701  16.773  48.758  1.00 39.40           A  C
ATOM    121  O   THR A  43      40.443  17.828  49.335  1.00 39.40           A  O
ATOM    122  N   PRO A  44      40.551  16.630  47.435  1.00 42.91           A  N
ATOM    123  CD  PRO A  44      40.761  15.420  46.632  1.00 32.42           A  C
ATOM    124  CA  PRO A  44      40.101  17.746  46.588  1.00 42.91           A  C
ATOM    125  CB  PRO A  44      40.184  17.172  45.167  1.00 32.42           A  C
ATOM    126  CG  PRO A  44      41.107  16.012  45.288  1.00 32.42           A  C
ATOM    127  C   PRO A  44      38.667  18.162  46.938  1.00 42.91           A  C
ATOM    128  O   PRO A  44      37.771  17.317  47.000  1.00 42.91           A  O
```

FIG. 4-3

```
ATOM    129  N    GLY A  45      38.455  19.458  47.142  1.00 34.24      A     N
ATOM    130  CA   GLY A  45      37.133  19.961  47.495  1.00 34.24      A     C
ATOM    131  C    GLY A  45      35.983  19.419  46.673  1.00 34.24      A     C
ATOM    132  O    GLY A  45      34.961  19.002  47.222  1.00 34.24      A     O
ATOM    133  N    ALA A  46      36.133  19.456  45.355  1.00 56.92      A     N
ATOM    134  CA   ALA A  46      35.114  18.926  44.458  1.00 56.92      A     C
ATOM    135  CB   ALA A  46      34.593  20.034  43.535  1.00 28.93      A     C
ATOM    136  C    ALA A  46      35.801  17.802  43.660  1.00 56.92      A     C
ATOM    137  O    ALA A  46      37.032  17.791  43.535  1.00 56.92      A     O
ATOM    138  N    GLY A  47      35.026  16.858  43.131  1.00 57.70      A     N
ATOM    139  CA   GLY A  47      35.635  15.768  42.389  1.00 57.70      A     C
ATOM    140  C    GLY A  47      35.685  14.558  43.304  1.00 57.70      A     C
ATOM    141  O    GLY A  47      35.382  14.677  44.504  1.00 57.70      A     O
ATOM    142  N    PRO A  48      36.053  13.378  42.770  1.00 55.33      A     N
ATOM    143  CD   PRO A  48      36.218  13.124  41.329  1.00 66.97      A     C
ATOM    144  CA   PRO A  48      36.143  12.118  43.530  1.00 55.33      A     C
ATOM    145  CB   PRO A  48      36.248  11.056  42.435  1.00 66.97      A     C
ATOM    146  CG   PRO A  48      35.661  11.749  41.208  1.00 66.97      A     C
ATOM    147  C    PRO A  48      37.334  12.066  44.493  1.00 55.33      A     C
ATOM    148  O    PRO A  48      38.455  12.476  44.151  1.00 55.33      A     O
ATOM    149  N    ASP A  49      37.072  11.545  45.691  1.00 63.53      A     N
ATOM    150  CA   ASP A  49      38.082  11.450  46.743  1.00 63.53      A     C
ATOM    151  CB   ASP A  49      37.561  10.652  47.948  1.00 58.40      A     C
ATOM    152  CG   ASP A  49      38.534  10.687  49.153  1.00 58.40      A     C
ATOM    153  OD1  ASP A  49      39.761  10.932  48.950  1.00 58.40      A     O
ATOM    154  OD2  ASP A  49      38.054  10.457  50.298  1.00 58.40      A     O
ATOM    155  C    ASP A  49      39.348  10.784  46.225  1.00 63.53      A     C
ATOM    156  O    ASP A  49      39.462   9.555  46.232  1.00 63.53      A     O
ATOM    157  N    ARG A  50      40.295  11.595  45.776  1.00 42.09      A     N
ATOM    158  CA   ARG A  50      41.553  11.085  45.272  1.00 42.09      A     C
ATOM    159  CB   ARG A  50      41.579  11.199  43.761  1.00 56.18      A     C
ATOM    160  CG   ARG A  50      40.560  10.275  43.139  1.00 56.18      A     C
ATOM    161  CD   ARG A  50      40.979   8.823  43.316  1.00 56.18      A     C
ATOM    162  NE   ARG A  50      41.681   8.332  42.132  1.00 56.18      A     N
ATOM    163  CZ   ARG A  50      42.345   7.182  42.061  1.00 56.18      A     C
ATOM    164  NH1  ARG A  50      42.418   6.374  43.124  1.00 56.18      A     N
ATOM    165  NH2  ARG A  50      42.922   6.838  40.911  1.00 56.18      A     N
ATOM    166  C    ARG A  50      42.615  11.930  45.915  1.00 42.09      A     C
ATOM    167  O    ARG A  50      43.021  12.955  45.372  1.00 42.09      A     O
ATOM    168  N    PRO A  51      43.108  11.481  47.078  1.00 27.89      A     N
ATOM    169  CD   PRO A  51      43.255  10.029  47.271  1.00 37.14      A     C
ATOM    170  CA   PRO A  51      44.122  12.179  47.856  1.00 27.89      A     C
ATOM    171  CB   PRO A  51      44.704  11.080  48.748  1.00 37.14      A     C
ATOM    172  CG   PRO A  51      43.760   9.950  48.657  1.00 37.14      A     C
ATOM    173  C    PRO A  51      45.190  12.700  46.920  1.00 27.89      A     C
ATOM    174  O    PRO A  51      45.356  12.201  45.812  1.00 27.89      A     O
ATOM    175  N    GLN A  52      45.922  13.700  47.379  1.00 53.50      A     N
ATOM    176  CA   GLN A  52      47.000  14.260  46.595  1.00 53.50      A     C
ATOM    177  CB   GLN A  52      46.437  15.106  45.456  1.00 61.95      A     C
ATOM    178  CG   GLN A  52      45.042  15.643  45.712  1.00 61.95      A     C
ATOM    179  CD   GLN A  52      44.230  15.796  44.413  1.00 61.95      A     C
ATOM    180  OE1  GLN A  52      44.094  14.835  43.633  1.00 61.95      A     O
ATOM    181  NE2  GLN A  52      43.681  17.003  44.180  1.00 61.95      A     N
ATOM    182  C    GLN A  52      47.864  15.105  47.508  1.00 53.50      A     C
ATOM    183  O    GLN A  52      47.363  15.766  48.426  1.00 53.50      A     O
ATOM    184  N    GLU A  53      49.170  15.063  47.264  1.00 33.58      A     N
ATOM    185  CA   GLU A  53      50.102  15.809  48.086  1.00 33.58      A     C
ATOM    186  CB   GLU A  53      51.539  15.432  47.764  1.00 40.36      A     C
ATOM    187  CG   GLU A  53      52.026  14.202  48.454  1.00 40.36      A     C
ATOM    188  CD   GLU A  53      53.539  14.139  48.480  1.00 40.36      A     C
ATOM    189  OE1  GLU A  53      54.074  13.164  49.056  1.00 40.36      A     O
ATOM    190  OE2  GLU A  53      54.186  15.066  47.928  1.00 40.36      A     O
ATOM    191  C    GLU A  53      49.955  17.297  47.848  1.00 33.58      A     C
ATOM    192  O    GLU A  53      49.840  17.745  46.717  1.00 33.58      A     O
ATOM    193  N    VAL A  54      49.951  18.058  48.933  1.00 44.16      A     N
ATOM    194  CA   VAL A  54      49.872  19.505  48.858  1.00 44.16      A     C
ATOM    195  CB   VAL A  54      48.501  20.070  49.304  1.00 23.21      A     C
```

FIG. 4-4

```
ATOM    196  CG1 VAL A  54      48.601  21.573  49.443  1.00 23.21       A  C
ATOM    197  CG2 VAL A  54      47.426  19.736  48.290  1.00 23.21       A  C
ATOM    198  C   VAL A  54      50.919  20.041  49.818  1.00 44.16       A  C
ATOM    199  O   VAL A  54      51.055  19.546  50.941  1.00 44.16       A  O
ATOM    200  N   SER A  55      51.664  21.045  49.378  1.00 39.07       A  N
ATOM    201  CA  SER A  55      52.692  21.628  50.229  1.00 39.07       A  C
ATOM    202  CB  SER A  55      54.083  21.135  49.818  1.00 33.53       A  C
ATOM    203  OG  SER A  55      54.432  21.631  48.537  1.00 33.53       A  O
ATOM    204  C   SER A  55      52.655  23.152  50.155  1.00 39.07       A  C
ATOM    205  O   SER A  55      52.713  23.746  49.074  1.00 39.07       A  O
ATOM    206  N   TYR A  56      52.566  23.790  51.315  1.00 45.38       A  N
ATOM    207  CA  TYR A  56      52.532  25.243  51.357  1.00 45.38       A  C
ATOM    208  CB  TYR A  56      51.168  25.729  51.808  1.00 33.25       A  C
ATOM    209  CG  TYR A  56      50.730  25.088  53.096  1.00 33.25       A  C
ATOM    210  CD1 TYR A  56      51.309  25.441  54.301  1.00 33.25       A  C
ATOM    211  CE1 TYR A  56      50.900  24.857  55.476  1.00 33.25       A  C
ATOM    212  CD2 TYR A  56      49.730  24.124  53.105  1.00 33.25       A  C
ATOM    213  CE2 TYR A  56      49.317  23.533  54.280  1.00 33.25       A  C
ATOM    214  CZ  TYR A  56      49.903  23.905  55.462  1.00 33.25       A  C
ATOM    215  OH  TYR A  56      49.476  23.332  56.636  1.00 33.25       A  O
ATOM    216  C   TYR A  56      53.591  25.780  52.298  1.00 45.38       A  C
ATOM    217  O   TYR A  56      54.306  25.013  52.948  1.00 45.38       A  O
ATOM    218  N   THR A  57      53.690  27.102  52.368  1.00 37.57       A  N
ATOM    219  CA  THR A  57      54.654  27.748  53.247  1.00 37.57       A  C
ATOM    220  CB  THR A  57      56.006  28.053  52.562  1.00 51.42       A  C
ATOM    221  OG1 THR A  57      55.812  29.052  51.550  1.00 51.42       A  O
ATOM    222  CG2 THR A  57      56.597  26.806  51.938  1.00 51.42       A  C
ATOM    223  C   THR A  57      54.123  29.099  53.656  1.00 37.57       A  C
ATOM    224  O   THR A  57      53.010  29.478  53.299  1.00 37.57       A  O
ATOM    225  N   ASP A  58      54.971  29.838  54.363  1.00 50.96       A  N
ATOM    226  CA  ASP A  58      54.657  31.173  54.850  1.00 50.96       A  C
ATOM    227  CB  ASP A  58      54.569  32.182  53.698  1.00 40.68       A  C
ATOM    228  CG  ASP A  58      55.847  32.265  52.888  1.00 40.68       A  C
ATOM    229  OD1 ASP A  58      56.938  32.193  53.497  1.00 40.68       A  O
ATOM    230  OD2 ASP A  58      55.754  32.418  51.647  1.00 40.68       A  O
ATOM    231  C   ASP A  58      53.354  31.220  55.632  1.00 50.96       A  C
ATOM    232  O   ASP A  58      52.672  32.246  55.628  1.00 50.96       A  O
ATOM    233  N   THR A  59      53.003  30.135  56.311  1.00 35.45       A  N
ATOM    234  CA  THR A  59      51.750  30.145  57.050  1.00 35.45       A  C
ATOM    235  CB  THR A  59      51.463  28.818  57.758  1.00 43.10       A  C
ATOM    236  OG1 THR A  59      52.375  28.654  58.847  1.00 43.10       A  O
ATOM    237  CG2 THR A  59      51.606  27.667  56.808  1.00 43.10       A  C
ATOM    238  C   THR A  59      51.777  31.210  58.123  1.00 35.45       A  C
ATOM    239  O   THR A  59      52.750  31.310  58.865  1.00 35.45       A  O
ATOM    240  N   LYS A  60      50.704  32.000  58.199  1.00 53.69       A  N
ATOM    241  CA  LYS A  60      50.592  33.063  59.191  1.00 53.69       A  C
ATOM    242  CB  LYS A  60      51.114  34.386  58.612  1.00 44.14       A  C
ATOM    243  CG  LYS A  60      50.133  35.127  57.732  1.00 44.14       A  C
ATOM    244  CD  LYS A  60      50.672  36.487  57.248  1.00 44.14       A  C
ATOM    245  CE  LYS A  60      51.625  36.336  56.042  1.00 44.14       A  C
ATOM    246  NZ  LYS A  60      52.860  35.506  56.349  1.00 44.14       A  N
ATOM    247  C   LYS A  60      49.134  33.212  59.622  1.00 53.69       A  C
ATOM    248  O   LYS A  60      48.241  33.278  58.789  1.00 53.69       A  O
ATOM    249  N   VAL A  61      48.902  33.254  60.929  1.00 56.03       A  N
ATOM    250  CA  VAL A  61      47.556  33.381  61.486  1.00 56.03       A  C
ATOM    251  CB  VAL A  61      47.612  33.266  63.022  1.00 44.24       A  C
ATOM    252  CG1 VAL A  61      46.216  33.021  63.578  1.00 44.24       A  C
ATOM    253  CG2 VAL A  61      48.571  32.145  63.432  1.00 44.24       A  C
ATOM    254  C   VAL A  61      46.906  34.711  61.109  1.00 56.03       A  C
ATOM    255  O   VAL A  61      47.431  35.768  61.458  1.00 56.03       A  O
ATOM    256  N   ILE A  62      45.759  34.657  60.425  1.00 43.60       A  N
ATOM    257  CA  ILE A  62      45.070  35.871  59.978  1.00 43.60       A  C
ATOM    258  CB  ILE A  62      44.935  35.895  58.445  1.00 28.57       A  C
ATOM    259  CG2 ILE A  62      46.312  35.967  57.801  1.00 28.57       A  C
ATOM    260  CG1 ILE A  62      44.151  34.673  57.980  1.00 28.57       A  C
ATOM    261  CD1 ILE A  62      43.778  34.728  56.521  1.00 28.57       A  C
ATOM    262  C   ILE A  62      43.683  36.034  60.608  1.00 43.60       A  C
```

FIG. 4-5

| | | | | | | | | | | | |
|---|---|---|---|---|---|---|---|---|---|---|---|
| ATOM | 263 | O | ILE | A | 62 | 42.934 | 36.958 | 60.291 | 1.00 43.60 | A | O |
| ATOM | 264 | N | GLY | A | 63 | 43.355 | 35.128 | 61.512 | 1.00 39.40 | A | N |
| ATOM | 265 | CA | GLY | A | 63 | 42.075 | 35.174 | 62.182 | 1.00 39.40 | A | C |
| ATOM | 266 | C | GLY | A | 63 | 42.101 | 34.047 | 63.204 | 1.00 39.40 | A | C |
| ATOM | 267 | O | GLY | A | 63 | 42.778 | 33.043 | 62.985 | 1.00 39.40 | A | O |
| ATOM | 268 | N | ASN | A | 64 | 41.380 | 34.214 | 64.311 | 1.00 51.69 | A | N |
| ATOM | 269 | CA | ASN | A | 64 | 41.316 | 33.231 | 65.407 | 1.00 51.69 | A | C |
| ATOM | 270 | CB | ASN | A | 64 | 41.884 | 33.765 | 66.712 | 1.00 55.00 | A | C |
| ATOM | 271 | CG | ASN | A | 64 | 43.295 | 34.128 | 66.628 | 1.00 55.00 | A | C |
| ATOM | 272 | OD1 | ASN | A | 64 | 44.160 | 33.352 | 67.039 | 1.00 55.00 | A | O |
| ATOM | 273 | ND2 | ASN | A | 64 | 43.573 | 35.323 | 66.094 | 1.00 55.00 | A | N |
| ATOM | 274 | C | ASN | A | 64 | 39.879 | 32.990 | 65.809 | 1.00 51.69 | A | C |
| ATOM | 275 | O | ASN | A | 64 | 39.615 | 32.437 | 66.886 | 1.00 51.69 | A | O |
| ATOM | 276 | N | GLY | A | 65 | 38.966 | 33.452 | 64.977 | 1.00 52.62 | A | N |
| ATOM | 277 | CA | GLY | A | 65 | 37.561 | 33.391 | 65.305 | 1.00 52.62 | A | C |
| ATOM | 278 | C | GLY | A | 65 | 36.764 | 32.200 | 65.800 | 1.00 52.62 | A | C |
| ATOM | 279 | O | GLY | A | 65 | 36.748 | 31.086 | 65.237 | 1.00 52.62 | A | O |
| ATOM | 280 | N | SER | A | 66 | 36.072 | 32.497 | 66.894 | 1.00 99.97 | A | N |
| ATOM | 281 | CA | SER | A | 66 | 35.159 | 31.581 | 67.540 | 1.00 99.97 | A | C |
| ATOM | 282 | CB | SER | A | 66 | 33.871 | 31.536 | 66.692 | 1.00 88.22 | A | C |
| ATOM | 283 | OG | SER | A | 66 | 33.386 | 32.855 | 66.430 | 1.00 88.22 | A | O |
| ATOM | 284 | C | SER | A | 66 | 35.782 | 30.201 | 67.736 | 1.00 99.97 | A | C |
| ATOM | 285 | O | SER | A | 66 | 36.614 | 29.969 | 68.634 | 1.00 99.97 | A | O |
| ATOM | 286 | N | PHE | A | 67 | 35.360 | 29.313 | 66.863 | 1.00 67.65 | A | N |
| ATOM | 287 | CA | PHE | A | 67 | 35.764 | 27.923 | 66.777 | 1.00 67.65 | A | C |
| ATOM | 288 | CB | PHE | A | 67 | 35.201 | 27.440 | 65.441 | 1.00 100.00 | A | C |
| ATOM | 289 | CG | PHE | A | 67 | 34.046 | 28.313 | 64.944 | 1.00 100.00 | A | C |
| ATOM | 290 | CD1 | PHE | A | 67 | 34.092 | 28.921 | 63.682 | 1.00 100.00 | A | C |
| ATOM | 291 | CD2 | PHE | A | 67 | 32.934 | 28.570 | 65.776 | 1.00 100.00 | A | C |
| ATOM | 292 | CE1 | PHE | A | 67 | 33.057 | 29.772 | 63.251 | 1.00 100.00 | A | C |
| ATOM | 293 | CE2 | PHE | A | 67 | 31.888 | 29.421 | 65.360 | 1.00 100.00 | A | C |
| ATOM | 294 | CZ | PHE | A | 67 | 31.953 | 30.024 | 64.092 | 1.00 100.00 | A | C |
| ATOM | 295 | C | PHE | A | 67 | 37.283 | 27.665 | 66.910 | 1.00 67.65 | A | C |
| ATOM | 296 | O | PHE | A | 67 | 37.748 | 27.165 | 67.943 | 1.00 67.65 | A | O |
| ATOM | 297 | N | GLY | A | 68 | 38.049 | 28.016 | 65.880 | 1.00 52.60 | A | N |
| ATOM | 298 | CA | GLY | A | 68 | 39.489 | 27.797 | 65.922 | 1.00 52.60 | A | C |
| ATOM | 299 | C | GLY | A | 68 | 40.305 | 28.838 | 65.170 | 1.00 52.60 | A | C |
| ATOM | 300 | O | GLY | A | 68 | 40.021 | 30.035 | 65.266 | 1.00 52.60 | A | O |
| ATOM | 301 | N | VAL | A | 69 | 41.295 | 28.392 | 64.397 | 1.00 37.21 | A | N |
| ATOM | 302 | CA | VAL | A | 69 | 42.164 | 29.319 | 63.667 | 1.00 37.21 | A | C |
| ATOM | 303 | CB | VAL | A | 69 | 43.657 | 29.018 | 63.928 | 1.00 46.84 | A | C |
| ATOM | 304 | CG1 | VAL | A | 69 | 44.514 | 30.207 | 63.473 | 1.00 46.84 | A | C |
| ATOM | 305 | CG2 | VAL | A | 69 | 43.885 | 28.707 | 65.405 | 1.00 46.84 | A | C |
| ATOM | 306 | C | VAL | A | 69 | 41.991 | 29.353 | 62.154 | 1.00 37.21 | A | C |
| ATOM | 307 | O | VAL | A | 69 | 41.537 | 28.377 | 61.543 | 1.00 37.21 | A | O |
| ATOM | 308 | N | VAL | A | 70 | 42.381 | 30.484 | 61.564 | 1.00 42.09 | A | N |
| ATOM | 309 | CA | VAL | A | 70 | 42.320 | 30.692 | 60.118 | 1.00 42.09 | A | C |
| ATOM | 310 | CB | VAL | A | 70 | 41.225 | 31.693 | 59.727 | 1.00 31.10 | A | C |
| ATOM | 311 | CG1 | VAL | A | 70 | 41.479 | 32.225 | 58.306 | 1.00 31.10 | A | C |
| ATOM | 312 | CG2 | VAL | A | 70 | 39.870 | 31.013 | 59.815 | 1.00 31.10 | A | C |
| ATOM | 313 | C | VAL | A | 70 | 43.658 | 31.233 | 59.649 | 1.00 42.09 | A | C |
| ATOM | 314 | O | VAL | A | 70 | 44.034 | 32.366 | 59.981 | 1.00 42.09 | A | O |
| ATOM | 315 | N | TYR | A | 71 | 44.374 | 30.427 | 58.870 | 1.00 40.02 | A | N |
| ATOM | 316 | CA | TYR | A | 71 | 45.688 | 30.836 | 58.400 | 1.00 40.02 | A | C |
| ATOM | 317 | CB | TYR | A | 71 | 46.730 | 29.732 | 58.632 | 1.00 52.79 | A | C |
| ATOM | 318 | CG | TYR | A | 71 | 46.656 | 29.032 | 59.967 | 1.00 52.79 | A | C |
| ATOM | 319 | CD1 | TYR | A | 71 | 45.708 | 28.039 | 60.211 | 1.00 52.79 | A | C |
| ATOM | 320 | CE1 | TYR | A | 71 | 45.656 | 27.380 | 61.444 | 1.00 52.79 | A | C |
| ATOM | 321 | CD2 | TYR | A | 71 | 47.546 | 29.351 | 60.986 | 1.00 52.79 | A | C |
| ATOM | 322 | CE2 | TYR | A | 71 | 47.502 | 28.698 | 62.223 | 1.00 52.79 | A | C |
| ATOM | 323 | CZ | TYR | A | 71 | 46.560 | 27.719 | 62.441 | 1.00 52.79 | A | C |
| ATOM | 324 | OH | TYR | A | 71 | 46.533 | 27.085 | 63.660 | 1.00 52.79 | A | O |
| ATOM | 325 | C | TYR | A | 71 | 45.715 | 31.195 | 56.927 | 1.00 40.02 | A | C |
| ATOM | 326 | O | TYR | A | 71 | 44.825 | 30.839 | 56.158 | 1.00 40.02 | A | O |
| ATOM | 327 | N | GLN | A | 72 | 46.767 | 31.900 | 56.549 | 1.00 43.31 | A | N |
| ATOM | 328 | CA | GLN | A | 72 | 46.969 | 32.301 | 55.176 | 1.00 43.31 | A | C |
| ATOM | 329 | CB | GLN | A | 72 | 47.156 | 33.810 | 55.093 | 1.00 52.63 | A | C |

FIG. 4-6

| ATOM | 330 | CG | GLN | A | 72 | 47.084 | 34.319 | 53.683 | 1.00 | 52.63 | A | C |
| --- | --- | --- | --- | --- | --- | --- | --- | --- | --- | --- | --- | --- |
| ATOM | 331 | CD | GLN | A | 72 | 48.371 | 34.943 | 53.228 | 1.00 | 52.63 | A | C |
| ATOM | 332 | OE1 | GLN | A | 72 | 49.447 | 34.402 | 53.488 | 1.00 | 52.63 | A | O |
| ATOM | 333 | NE2 | GLN | A | 72 | 48.280 | 36.083 | 52.528 | 1.00 | 52.63 | A | N |
| ATOM | 334 | C | GLN | A | 72 | 48.252 | 31.584 | 54.788 | 1.00 | 43.31 | A | C |
| ATOM | 335 | O | GLN | A | 72 | 49.195 | 31.523 | 55.587 | 1.00 | 43.31 | A | O |
| ATOM | 336 | N | ALA | A | 73 | 48.291 | 31.032 | 53.580 | 1.00 | 43.37 | A | N |
| ATOM | 337 | CA | ALA | A | 73 | 49.471 | 30.303 | 53.136 | 1.00 | 43.37 | A | C |
| ATOM | 338 | CB | ALA | A | 73 | 49.310 | 28.827 | 53.462 | 1.00 | 18.00 | A | C |
| ATOM | 339 | C | ALA | A | 73 | 49.749 | 30.479 | 51.651 | 1.00 | 43.37 | A | C |
| ATOM | 340 | O | ALA | A | 73 | 48.914 | 30.993 | 50.898 | 1.00 | 43.37 | A | O |
| ATOM | 341 | N | LYS | A | 74 | 50.940 | 30.056 | 51.241 | 1.00 | 46.43 | A | N |
| ATOM | 342 | CA | LYS | A | 74 | 51.344 | 30.152 | 49.852 | 1.00 | 46.43 | A | C |
| ATOM | 343 | CB | LYS | A | 74 | 52.632 | 30.976 | 49.735 | 1.00 | 58.50 | A | C |
| ATOM | 344 | CG | LYS | A | 74 | 53.130 | 31.181 | 48.307 | 1.00 | 58.50 | A | C |
| ATOM | 345 | CD | LYS | A | 74 | 54.170 | 32.306 | 48.247 | 1.00 | 58.50 | A | C |
| ATOM | 346 | CE | LYS | A | 74 | 54.796 | 32.443 | 46.851 | 1.00 | 58.50 | A | C |
| ATOM | 347 | NZ | LYS | A | 74 | 55.734 | 31.281 | 46.489 | 1.00 | 58.50 | A | N |
| ATOM | 348 | C | LYS | A | 74 | 51.567 | 28.742 | 49.323 | 1.00 | 46.43 | A | C |
| ATOM | 349 | O | LYS | A | 74 | 52.326 | 27.964 | 49.909 | 1.00 | 46.43 | A | O |
| ATOM | 350 | N | LEU | A | 75 | 50.872 | 28.395 | 48.244 | 1.00 | 51.71 | A | N |
| ATOM | 351 | CA | LEU | A | 75 | 51.057 | 27.080 | 47.657 | 1.00 | 51.71 | A | C |
| ATOM | 352 | CB | LEU | A | 75 | 49.960 | 26.771 | 46.628 | 1.00 | 27.95 | A | C |
| ATOM | 353 | CG | LEU | A | 75 | 48.566 | 26.409 | 47.169 | 1.00 | 27.95 | A | C |
| ATOM | 354 | CD1 | LEU | A | 75 | 47.851 | 25.504 | 46.186 | 1.00 | 27.95 | A | C |
| ATOM | 355 | CD2 | LEU | A | 75 | 48.689 | 25.703 | 48.488 | 1.00 | 27.95 | A | C |
| ATOM | 356 | C | LEU | A | 75 | 52.448 | 27.066 | 47.011 | 1.00 | 51.71 | A | C |
| ATOM | 357 | O | LEU | A | 75 | 52.795 | 27.932 | 46.183 | 1.00 | 51.71 | A | O |
| ATOM | 358 | N | CYS | A | 76 | 53.239 | 26.070 | 47.410 | 1.00 | 65.32 | A | N |
| ATOM | 359 | CA | CYS | A | 76 | 54.613 | 25.917 | 46.939 | 1.00 | 65.32 | A | C |
| ATOM | 360 | CB | CYS | A | 76 | 55.212 | 24.617 | 47.465 | 1.00 | 35.49 | A | C |
| ATOM | 361 | SG | CYS | A | 76 | 55.669 | 24.745 | 49.166 | 1.00 | 35.49 | A | S |
| ATOM | 362 | C | CYS | A | 76 | 54.883 | 26.002 | 45.454 | 1.00 | 65.32 | A | C |
| ATOM | 363 | O | CYS | A | 76 | 55.771 | 26.747 | 45.027 | 1.00 | 65.32 | A | O |
| ATOM | 364 | N | ASP | A | 77 | 54.138 | 25.258 | 44.651 | 1.00 | 60.93 | A | N |
| ATOM | 365 | CA | ASP | A | 77 | 54.422 | 25.307 | 43.238 | 1.00 | 60.93 | A | C |
| ATOM | 366 | CB | ASP | A | 77 | 54.263 | 23.909 | 42.659 | 1.00 | 74.12 | A | C |
| ATOM | 367 | CG | ASP | A | 77 | 55.148 | 22.881 | 43.383 | 1.00 | 74.12 | A | C |
| ATOM | 368 | OD1 | ASP | A | 77 | 56.353 | 23.188 | 43.624 | 1.00 | 74.12 | A | O |
| ATOM | 369 | OD2 | ASP | A | 77 | 54.629 | 21.777 | 43.700 | 1.00 | 74.12 | A | O |
| ATOM | 370 | C | ASP | A | 77 | 53.639 | 26.343 | 42.452 | 1.00 | 60.93 | A | C |
| ATOM | 371 | O | ASP | A | 77 | 54.177 | 26.959 | 41.521 | 1.00 | 60.93 | A | O |
| ATOM | 372 | N | SER | A | 78 | 52.383 | 26.560 | 42.832 | 1.00 | 48.47 | A | N |
| ATOM | 373 | CA | SER | A | 78 | 51.559 | 27.547 | 42.138 | 1.00 | 48.47 | A | C |
| ATOM | 374 | CB | SER | A | 78 | 50.079 | 27.204 | 42.297 | 1.00 | 58.39 | A | C |
| ATOM | 375 | OG | SER | A | 78 | 49.722 | 27.176 | 43.669 | 1.00 | 58.39 | A | O |
| ATOM | 376 | C | SER | A | 78 | 51.805 | 28.977 | 42.635 | 1.00 | 48.47 | A | C |
| ATOM | 377 | O | SER | A | 78 | 51.609 | 29.936 | 41.887 | 1.00 | 48.47 | A | O |
| ATOM | 378 | N | GLY | A | 79 | 52.241 | 29.111 | 43.891 | 1.00 | 30.20 | A | N |
| ATOM | 379 | CA | GLY | A | 79 | 52.486 | 30.424 | 44.463 | 1.00 | 30.20 | A | C |
| ATOM | 380 | C | GLY | A | 79 | 51.181 | 31.017 | 44.968 | 1.00 | 30.20 | A | C |
| ATOM | 381 | O | GLY | A | 79 | 51.166 | 31.986 | 45.733 | 1.00 | 30.20 | A | O |
| ATOM | 382 | N | GLU | A | 80 | 50.076 | 30.425 | 44.530 | 1.00 | 45.07 | A | N |
| ATOM | 383 | CA | GLU | A | 80 | 48.746 | 30.867 | 44.926 | 1.00 | 45.07 | A | C |
| ATOM | 384 | CB | GLU | A | 80 | 47.708 | 29.912 | 44.340 | 1.00 | 56.84 | A | C |
| ATOM | 385 | CG | GLU | A | 80 | 47.675 | 29.942 | 42.820 | 1.00 | 56.84 | A | C |
| ATOM | 386 | CD | GLU | A | 80 | 46.967 | 28.739 | 42.223 | 1.00 | 56.84 | A | C |
| ATOM | 387 | OE1 | GLU | A | 80 | 45.824 | 28.432 | 42.656 | 1.00 | 56.84 | A | O |
| ATOM | 388 | OE2 | GLU | A | 80 | 47.566 | 28.109 | 41.317 | 1.00 | 56.84 | A | O |
| ATOM | 389 | C | GLU | A | 80 | 48.597 | 30.944 | 46.446 | 1.00 | 45.07 | A | C |
| ATOM | 390 | O | GLU | A | 80 | 49.114 | 30.101 | 47.176 | 1.00 | 45.07 | A | O |
| ATOM | 391 | N | LEU | A | 81 | 47.901 | 31.971 | 46.918 | 1.00 | 43.41 | A | N |
| ATOM | 392 | CA | LEU | A | 81 | 47.684 | 32.165 | 48.346 | 1.00 | 43.41 | A | C |
| ATOM | 393 | CB | LEU | A | 81 | 47.533 | 33.653 | 48.643 | 1.00 | 34.35 | A | C |
| ATOM | 394 | CG | LEU | A | 81 | 48.868 | 34.390 | 48.684 | 1.00 | 34.35 | A | C |
| ATOM | 395 | CD1 | LEU | A | 81 | 48.678 | 35.894 | 48.608 | 1.00 | 34.35 | A | C |
| ATOM | 396 | CD2 | LEU | A | 81 | 49.581 | 33.988 | 49.975 | 1.00 | 34.35 | A | C |

FIG. 4-7

```
ATOM    397  C    LEU A  81      46.425  31.438  48.751  1.00 43.41       A  C
ATOM    398  O    LEU A  81      45.490  31.361  47.966  1.00 43.41       A  O
ATOM    399  N    VAL A  82      46.397  30.901  49.965  1.00 36.49       A  N
ATOM    400  CA   VAL A  82      45.219  30.191  50.446  1.00 36.49       A  C
ATOM    401  CB   VAL A  82      45.376  28.676  50.249  1.00 27.68       A  C
ATOM    402  CG1  VAL A  82      45.705  28.373  48.808  1.00 27.68       A  C
ATOM    403  CG2  VAL A  82      46.472  28.152  51.163  1.00 27.68       A  C
ATOM    404  C    VAL A  82      44.896  30.448  51.924  1.00 36.49       A  C
ATOM    405  O    VAL A  82      45.749  30.853  52.717  1.00 36.49       A  O
ATOM    406  N    ALA A  83      43.650  30.200  52.293  1.00 32.59       A  N
ATOM    407  CA   ALA A  83      43.222  30.380  53.667  1.00 32.59       A  C
ATOM    408  CB   ALA A  83      42.005  31.270  53.712  1.00 35.22       A  C
ATOM    409  C    ALA A  83      42.886  29.006  54.224  1.00 32.59       A  C
ATOM    410  O    ALA A  83      42.195  28.217  53.578  1.00 32.59       A  O
ATOM    411  N    ILE A  84      43.369  28.710  55.420  1.00 27.53       A  N
ATOM    412  CA   ILE A  84      43.080  27.421  56.009  1.00 27.53       A  C
ATOM    413  CB   ILE A  84      44.358  26.603  56.224  1.00 39.25       A  C
ATOM    414  CG2  ILE A  84      43.992  25.198  56.662  1.00 39.25       A  C
ATOM    415  CG1  ILE A  84      45.169  26.548  54.926  1.00 39.25       A  C
ATOM    416  CD1  ILE A  84      46.476  25.780  55.039  1.00 39.25       A  C
ATOM    417  C    ILE A  84      42.350  27.545  57.335  1.00 27.53       A  C
ATOM    418  O    ILE A  84      42.960  27.688  58.400  1.00 27.53       A  O
ATOM    419  N    LYS A  85      41.029  27.505  57.267  1.00 40.37       A  N
ATOM    420  CA   LYS A  85      40.244  27.580  58.477  1.00 40.37       A  C
ATOM    421  CB   LYS A  85      38.773  27.866  58.145  1.00 37.30       A  C
ATOM    422  CG   LYS A  85      37.794  27.528  59.270  1.00 37.30       A  C
ATOM    423  CD   LYS A  85      36.453  28.215  59.094  1.00 37.30       A  C
ATOM    424  CE   LYS A  85      35.546  27.907  60.287  1.00 37.30       A  C
ATOM    425  NZ   LYS A  85      34.155  28.417  60.129  1.00 37.30       A  N
ATOM    426  C    LYS A  85      40.384  26.214  59.132  1.00 40.37       A  C
ATOM    427  O    LYS A  85      39.972  25.203  58.559  1.00 40.37       A  O
ATOM    428  N    LYS A  86      41.002  26.182  60.309  1.00 50.17       A  N
ATOM    429  CA   LYS A  86      41.157  24.934  61.046  1.00 50.17       A  C
ATOM    430  CB   LYS A  86      42.583  24.790  61.612  1.00 53.30       A  C
ATOM    431  CG   LYS A  86      42.688  23.767  62.752  1.00 53.30       A  C
ATOM    432  CD   LYS A  86      43.979  22.901  62.724  1.00 53.30       A  C
ATOM    433  CE   LYS A  86      45.276  23.721  62.826  1.00 53.30       A  C
ATOM    434  NZ   LYS A  86      46.458  22.818  62.951  1.00 53.30       A  N
ATOM    435  C    LYS A  86      40.133  24.946  62.178  1.00 50.17       A  C
ATOM    436  O    LYS A  86      40.207  25.769  63.093  1.00 50.17       A  O
ATOM    437  N    VAL A  87      39.152  24.057  62.094  1.00 62.26       A  N
ATOM    438  CA   VAL A  87      38.144  23.986  63.136  1.00 62.26       A  C
ATOM    439  CB   VAL A  87      36.726  24.057  62.551  1.00 40.17       A  C
ATOM    440  CG1  VAL A  87      35.903  22.833  62.974  1.00 40.17       A  C
ATOM    441  CG2  VAL A  87      36.068  25.339  63.026  1.00 40.17       A  C
ATOM    442  C    VAL A  87      38.337  22.694  63.921  1.00 62.26       A  C
ATOM    443  O    VAL A  87      38.841  21.704  63.380  1.00 62.26       A  O
ATOM    444  N    LEU A  88      37.945  22.714  65.197  1.00 70.44       A  N
ATOM    445  CA   LEU A  88      38.098  21.551  66.070  1.00 70.44       A  C
ATOM    446  CB   LEU A  88      37.788  21.938  67.525  1.00 54.57       A  C
ATOM    447  CG   LEU A  88      38.304  20.988  68.621  1.00 54.57       A  C
ATOM    448  CD1  LEU A  88      37.422  19.718  68.722  1.00 54.57       A  C
ATOM    449  CD2  LEU A  88      39.772  20.628  68.315  1.00 54.57       A  C
ATOM    450  C    LEU A  88      37.191  20.412  65.616  1.00 70.44       A  C
ATOM    451  O    LEU A  88      36.187  20.119  66.261  1.00 70.44       A  O
ATOM    452  N    ALA A  89      37.561  19.777  64.505  1.00 68.97       A  N
ATOM    453  CA   ALA A  89      36.783  18.682  63.927  1.00 68.97       A  C
ATOM    454  CB   ALA A  89      37.603  17.951  62.868  1.00 71.54       A  C
ATOM    455  C    ALA A  89      36.330  17.699  64.984  1.00 68.97       A  C
ATOM    456  O    ALA A  89      37.095  16.819  65.375  1.00 68.97       A  O
ATOM    457  N    ALA A  90      35.088  17.862  65.442  1.00 83.82       A  N
ATOM    458  CA   ALA A  90      34.507  16.981  66.453  1.00 83.82       A  C
ATOM    459  CB   ALA A  90      33.102  17.482  66.847  1.00 23.65       A  C
ATOM    460  C    ALA A  90      34.419  15.548  65.901  1.00 83.82       A  C
ATOM    461  O    ALA A  90      35.216  15.132  65.036  1.00 83.82       A  O
ATOM    462  N    ALA A  91      33.432  14.802  66.392  1.00 62.13       A  N
ATOM    463  CA   ALA A  91      33.233  13.426  65.957  1.00 62.13       A  C
```

FIG. 4-8

```
ATOM    464  CB   ALA A  91      34.138  12.476  66.770  1.00 74.56           A  C
ATOM    465  C    ALA A  91      31.766  13.079  66.160  1.00 62.13           A  C
ATOM    466  O    ALA A  91      31.141  12.401  65.330  1.00 62.13           A  O
ATOM    467  N    ALA A  92      31.216  13.562  67.268  1.00 55.16           A  N
ATOM    468  CA   ALA A  92      29.815  13.316  67.561  1.00 55.16           A  C
ATOM    469  CB   ALA A  92      29.322  14.279  68.657  1.00 43.81           A  C
ATOM    470  C    ALA A  92      28.967  13.478  66.283  1.00 55.16           A  C
ATOM    471  O    ALA A  92      28.010  12.737  66.084  1.00 55.16           A  O
ATOM    472  N    ALA A  93      29.327  14.425  65.414  1.00 71.33           A  N
ATOM    473  CA   ALA A  93      28.576  14.672  64.170  1.00 71.33           A  C
ATOM    474  CB   ALA A  93      27.644  15.903  64.351  1.00 34.18           A  C
ATOM    475  C    ALA A  93      29.453  14.864  62.913  1.00 71.33           A  C
ATOM    476  O    ALA A  93      30.677  14.668  62.936  1.00 71.33           A  O
ATOM    477  N    ALA A  94      28.804  15.243  61.815  1.00 60.71           A  N
ATOM    478  CA   ALA A  94      29.487  15.473  60.540  1.00 60.71           A  C
ATOM    479  CB   ALA A  94      28.632  14.929  59.386  1.00 38.92           A  C
ATOM    480  C    ALA A  94      29.702  16.978  60.370  1.00 60.71           A  C
ATOM    481  O    ALA A  94      28.896  17.773  60.857  1.00 60.71           A  O
ATOM    482  N    ASN A  95      30.767  17.387  59.689  1.00 35.64           A  N
ATOM    483  CA   ASN A  95      30.977  18.822  59.519  1.00 35.64           A  C
ATOM    484  CB   ASN A  95      32.430  19.126  59.201  1.00 36.43           A  C
ATOM    485  CG   ASN A  95      32.803  20.537  59.571  1.00 36.43           A  C
ATOM    486  OD1  ASN A  95      32.619  21.474  58.780  1.00 36.43           A  O
ATOM    487  ND2  ASN A  95      33.314  20.707  60.795  1.00 36.43           A  N
ATOM    488  C    ASN A  95      30.054  19.381  58.437  1.00 35.64           A  C
ATOM    489  O    ASN A  95      30.204  19.092  57.245  1.00 35.64           A  O
ATOM    490  N    ARG A  96      29.093  20.186  58.879  1.00 32.87           A  N
ATOM    491  CA   ARG A  96      28.086  20.779  58.012  1.00 32.87           A  C
ATOM    492  CB   ARG A  96      27.027  21.454  58.886  1.00 48.40           A  C
ATOM    493  CG   ARG A  96      25.963  22.225  58.135  1.00 48.40           A  C
ATOM    494  CD   ARG A  96      24.939  22.841  59.101  1.00 48.40           A  C
ATOM    495  NE   ARG A  96      24.286  21.811  59.911  1.00 48.40           A  N
ATOM    496  CZ   ARG A  96      23.295  22.026  60.774  1.00 48.40           A  C
ATOM    497  NH1  ARG A  96      22.821  23.249  60.962  1.00 48.40           A  N
ATOM    498  NH2  ARG A  96      22.765  21.008  61.441  1.00 48.40           A  N
ATOM    499  C    ARG A  96      28.650  21.767  56.999  1.00 32.87           A  C
ATOM    500  O    ARG A  96      28.202  21.803  55.851  1.00 32.87           A  O
ATOM    501  N    GLU A  97      29.616  22.576  57.420  1.00 29.99           A  N
ATOM    502  CA   GLU A  97      30.228  23.531  56.510  1.00 29.99           A  C
ATOM    503  CB   GLU A  97      31.232  24.426  57.245  1.00 25.35           A  C
ATOM    504  CG   GLU A  97      32.161  25.173  56.318  1.00 25.35           A  C
ATOM    505  CD   GLU A  97      32.845  26.357  56.976  1.00 25.35           A  C
ATOM    506  OE1  GLU A  97      33.221  26.242  58.158  1.00 25.35           A  O
ATOM    507  OE2  GLU A  97      33.025  27.400  56.304  1.00 25.35           A  O
ATOM    508  C    GLU A  97      30.921  22.750  55.407  1.00 29.99           A  C
ATOM    509  O    GLU A  97      30.669  22.979  54.230  1.00 29.99           A  O
ATOM    510  N    LEU A  98      31.779  21.813  55.797  1.00 37.36           A  N
ATOM    511  CA   LEU A  98      32.488  20.978  54.837  1.00 37.36           A  C
ATOM    512  CB   LEU A  98      33.300  19.913  55.555  1.00 28.06           A  C
ATOM    513  CG   LEU A  98      33.986  18.945  54.597  1.00 28.06           A  C
ATOM    514  CD1  LEU A  98      34.775  19.715  53.563  1.00 28.06           A  C
ATOM    515  CD2  LEU A  98      34.893  18.027  55.384  1.00 28.06           A  C
ATOM    516  C    LEU A  98      31.526  20.288  53.889  1.00 37.36           A  C
ATOM    517  O    LEU A  98      31.730  20.284  52.681  1.00 37.36           A  O
ATOM    518  N    GLN A  99      30.478  19.694  54.439  1.00 38.99           A  N
ATOM    519  CA   GLN A  99      29.515  19.006  53.604  1.00 38.99           A  C
ATOM    520  CB   GLN A  99      28.376  18.431  54.455  1.00 92.00           A  C
ATOM    521  CG   GLN A  99      28.832  17.229  55.304  1.00 92.00           A  C
ATOM    522  CD   GLN A  99      29.937  16.386  54.593  1.00 92.00           A  C
ATOM    523  OE1  GLN A  99      29.756  15.911  53.449  1.00 92.00           A  O
ATOM    524  NE2  GLN A  99      31.087  16.216  55.271  1.00 92.00           A  N
ATOM    525  C    GLN A  99      28.978  19.935  52.532  1.00 38.99           A  C
ATOM    526  O    GLN A  99      28.976  19.586  51.352  1.00 38.99           A  O
ATOM    527  N    ILE A 100      28.545  21.121  52.937  1.00 33.64           A  N
ATOM    528  CA   ILE A 100      27.996  22.106  52.007  1.00 33.64           A  C
ATOM    529  CB   ILE A 100      27.445  23.315  52.788  1.00 33.36           A  C
ATOM    530  CG2  ILE A 100      27.114  24.449  51.825  1.00 33.36           A  C
```

FIG. 4-9

```
ATOM    531  CG1 ILE A 100      26.235  22.883  53.621  1.00 33.36      A    C
ATOM    532  CD1 ILE A 100      25.552  24.023  54.339  1.00 33.36      A    C
ATOM    533  C   ILE A 100      29.014  22.624  50.986  1.00 33.64      A    C
ATOM    534  O   ILE A 100      28.720  22.720  49.795  1.00 33.64      A    O
ATOM    535  N   MET A 101      30.205  22.966  51.463  1.00 29.35      A    N
ATOM    536  CA  MET A 101      31.280  23.475  50.604  1.00 29.35      A    C
ATOM    537  CB  MET A 101      32.547  23.711  51.440  1.00 46.68      A    C
ATOM    538  CG  MET A 101      32.467  24.820  52.479  1.00 46.68      A    C
ATOM    539  SD  MET A 101      32.274  26.402  51.682  1.00 46.68      A    S
ATOM    540  CE  MET A 101      33.954  26.658  51.082  1.00 46.68      A    C
ATOM    541  C   MET A 101      31.604  22.479  49.496  1.00 29.35      A    C
ATOM    542  O   MET A 101      31.848  22.830  48.342  1.00 29.35      A    O
ATOM    543  N   ARG A 102      31.622  21.224  49.903  1.00 32.04      A    N
ATOM    544  CA  ARG A 102      31.907  20.087  49.060  1.00 32.04      A    C
ATOM    545  CB  ARG A 102      31.741  18.857  49.949  1.00 56.25      A    C
ATOM    546  CG  ARG A 102      32.589  17.691  49.607  1.00 56.25      A    C
ATOM    547  CD  ARG A 102      33.722  17.550  50.577  1.00 56.25      A    C
ATOM    548  NE  ARG A 102      34.347  16.254  50.367  1.00 56.25      A    N
ATOM    549  CZ  ARG A 102      33.754  15.091  50.627  1.00 56.25      A    C
ATOM    550  NH1 ARG A 102      32.518  15.055  51.119  1.00 56.25      A    N
ATOM    551  NH2 ARG A 102      34.395  13.957  50.380  1.00 56.25      A    N
ATOM    552  C   ARG A 102      30.975  19.986  47.838  1.00 32.04      A    C
ATOM    553  O   ARG A 102      31.359  19.435  46.807  1.00 32.04      A    O
ATOM    554  N   LYS A 103      29.756  20.505  47.960  1.00 25.30      A    N
ATOM    555  CA  LYS A 103      28.798  20.427  46.866  1.00 25.30      A    C
ATOM    556  CB  LYS A 103      27.498  19.745  47.339  1.00 44.25      A    C
ATOM    557  CG  LYS A 103      26.735  20.405  48.500  1.00 44.25      A    C
ATOM    558  CD  LYS A 103      25.356  20.971  48.071  1.00 44.25      A    C
ATOM    559  CE  LYS A 103      24.353  19.913  47.553  1.00 44.25      A    C
ATOM    560  NZ  LYS A 103      23.772  19.026  48.618  1.00 44.25      A    N
ATOM    561  C   LYS A 103      28.467  21.757  46.227  1.00 25.30      A    C
ATOM    562  O   LYS A 103      27.437  21.895  45.576  1.00 25.30      A    O
ATOM    563  N   LEU A 104      29.342  22.735  46.408  1.00 28.40      A    N
ATOM    564  CA  LEU A 104      29.139  24.049  45.822  1.00 28.40      A    C
ATOM    565  CB  LEU A 104      29.066  25.105  46.922  1.00 25.15      A    C
ATOM    566  CG  LEU A 104      27.689  25.624  47.366  1.00 25.15      A    C
ATOM    567  CD1 LEU A 104      26.688  24.493  47.484  1.00 25.15      A    C
ATOM    568  CD2 LEU A 104      27.842  26.349  48.707  1.00 25.15      A    C
ATOM    569  C   LEU A 104      30.260  24.378  44.858  1.00 28.40      A    C
ATOM    570  O   LEU A 104      31.423  24.118  45.135  1.00 28.40      A    O
ATOM    571  N   ASP A 105      29.889  24.926  43.710  1.00 35.77      A    N
ATOM    572  CA  ASP A 105      30.836  25.313  42.675  1.00 35.77      A    C
ATOM    573  CB  ASP A 105      31.203  24.101  41.810  1.00 40.56      A    C
ATOM    574  CG  ASP A 105      32.194  24.441  40.696  1.00 40.56      A    C
ATOM    575  OD1 ASP A 105      33.107  25.270  40.915  1.00 40.56      A    O
ATOM    576  OD2 ASP A 105      32.069  23.864  39.596  1.00 40.56      A    O
ATOM    577  C   ASP A 105      30.142  26.384  41.857  1.00 35.77      A    C
ATOM    578  O   ASP A 105      29.207  26.111  41.084  1.00 35.77      A    O
ATOM    579  N   HIS A 106      30.589  27.617  42.067  1.00 22.21      A    N
ATOM    580  CA  HIS A 106      30.023  28.771  41.387  1.00 22.21      A    C
ATOM    581  CB  HIS A 106      28.769  29.228  42.131  1.00 31.23      A    C
ATOM    582  CG  HIS A 106      28.044  30.343  41.456  1.00 31.23      A    C
ATOM    583  CD2 HIS A 106      26.909  30.353  40.718  1.00 31.23      A    C
ATOM    584  ND1 HIS A 106      28.501  31.643  41.478  1.00 31.23      A    N
ATOM    585  CE1 HIS A 106      27.678  32.407  40.780  1.00 31.23      A    C
ATOM    586  NE2 HIS A 106      26.703  31.649  40.308  1.00 31.23      A    N
ATOM    587  C   HIS A 106      31.087  29.858  41.340  1.00 22.21      A    C
ATOM    588  O   HIS A 106      31.873  29.994  42.265  1.00 22.21      A    O
ATOM    589  N   CYS A 107      31.120  30.611  40.246  1.00 27.47      A    N
ATOM    590  CA  CYS A 107      32.113  31.662  40.061  1.00 27.47      A    C
ATOM    591  CB  CYS A 107      31.947  32.289  38.666  1.00 42.62      A    C
ATOM    592  SG  CYS A 107      30.474  33.363  38.427  1.00 42.62      A    S
ATOM    593  C   CYS A 107      32.057  32.743  41.133  1.00 27.47      A    C
ATOM    594  O   CYS A 107      32.939  33.585  41.210  1.00 27.47      A    O
ATOM    595  N   ASN A 108      31.022  32.719  41.962  1.00 29.12      A    N
ATOM    596  CA  ASN A 108      30.878  33.722  43.011  1.00 29.12      A    C
ATOM    597  CB  ASN A 108      29.609  34.541  42.766  1.00 32.48      A    C
```

FIG. 4-10

| | | | | | | | | | | | |
|---|---|---|---|---|---|---|---|---|---|---|---|
| ATOM | 598 | CG | ASN | A | 108 | 29.683 | 35.356 | 41.487 | 1.00 | 32.48 | A C |
| ATOM | 599 | OD1 | ASN | A | 108 | 28.820 | 35.276 | 40.620 | 1.00 | 32.48 | A O |
| ATOM | 600 | ND2 | ASN | A | 108 | 30.717 | 36.158 | 41.378 | 1.00 | 32.48 | A N |
| ATOM | 601 | C | ASN | A | 108 | 30.871 | 33.130 | 44.429 | 1.00 | 29.12 | A C |
| ATOM | 602 | O | ASN | A | 108 | 30.273 | 33.686 | 45.337 | 1.00 | 29.12 | A O |
| ATOM | 603 | N | ILE | A | 109 | 31.539 | 32.004 | 44.619 | 1.00 | 22.15 | A N |
| ATOM | 604 | CA | ILE | A | 109 | 31.623 | 31.371 | 45.933 | 1.00 | 22.15 | A C |
| ATOM | 605 | CB | ILE | A | 109 | 30.820 | 30.054 | 45.985 | 1.00 | 16.82 | A C |
| ATOM | 606 | CG2 | ILE | A | 109 | 30.812 | 29.508 | 47.391 | 1.00 | 16.82 | A C |
| ATOM | 607 | CG1 | ILE | A | 109 | 29.401 | 30.257 | 45.468 | 1.00 | 16.82 | A C |
| ATOM | 608 | CD1 | ILE | A | 109 | 28.407 | 30.682 | 46.503 | 1.00 | 16.82 | A C |
| ATOM | 609 | C | ILE | A | 109 | 33.095 | 30.973 | 46.144 | 1.00 | 22.15 | A C |
| ATOM | 610 | O | ILE | A | 109 | 33.705 | 30.364 | 45.263 | 1.00 | 22.15 | A O |
| ATOM | 611 | N | VAL | A | 110 | 33.674 | 31.287 | 47.293 | 1.00 | 18.62 | A N |
| ATOM | 612 | CA | VAL | A | 110 | 35.061 | 30.903 | 47.503 | 1.00 | 18.62 | A C |
| ATOM | 613 | CB | VAL | A | 110 | 35.540 | 31.080 | 48.946 | 1.00 | 15.07 | A C |
| ATOM | 614 | CG1 | VAL | A | 110 | 35.828 | 32.525 | 49.222 | 1.00 | 15.07 | A C |
| ATOM | 615 | CG2 | VAL | A | 110 | 34.509 | 30.517 | 49.906 | 1.00 | 15.07 | A C |
| ATOM | 616 | C | VAL | A | 110 | 35.153 | 29.427 | 47.237 | 1.00 | 18.62 | A C |
| ATOM | 617 | O | VAL | A | 110 | 34.273 | 28.676 | 47.624 | 1.00 | 18.62 | A O |
| ATOM | 618 | N | ARG | A | 111 | 36.235 | 29.014 | 46.600 | 1.00 | 33.04 | A N |
| ATOM | 619 | CA | ARG | A | 111 | 36.443 | 27.618 | 46.282 | 1.00 | 33.04 | A C |
| ATOM | 620 | CB | ARG | A | 111 | 37.272 | 27.525 | 44.999 | 1.00 | 59.15 | A C |
| ATOM | 621 | CG | ARG | A | 111 | 37.405 | 26.131 | 44.394 | 1.00 | 59.15 | A C |
| ATOM | 622 | CD | ARG | A | 111 | 38.213 | 26.193 | 43.093 | 1.00 | 59.15 | A C |
| ATOM | 623 | NE | ARG | A | 111 | 39.581 | 26.687 | 43.317 | 1.00 | 59.15 | A N |
| ATOM | 624 | CZ | ARG | A | 111 | 40.197 | 27.616 | 42.575 | 1.00 | 59.15 | A C |
| ATOM | 625 | NH1 | ARG | A | 111 | 39.568 | 28.171 | 41.535 | 1.00 | 59.15 | A N |
| ATOM | 626 | NH2 | ARG | A | 111 | 41.442 | 28.000 | 42.881 | 1.00 | 59.15 | A N |
| ATOM | 627 | C | ARG | A | 111 | 37.146 | 26.866 | 47.411 | 1.00 | 33.04 | A C |
| ATOM | 628 | O | ARG | A | 111 | 38.020 | 27.410 | 48.087 | 1.00 | 33.04 | A O |
| ATOM | 629 | N | LEU | A | 112 | 36.751 | 25.614 | 47.616 | 1.00 | 37.72 | A N |
| ATOM | 630 | CA | LEU | A | 112 | 37.360 | 24.777 | 48.640 | 1.00 | 37.72 | A C |
| ATOM | 631 | CB | LEU | A | 112 | 36.302 | 23.897 | 49.330 | 1.00 | 17.99 | A C |
| ATOM | 632 | CG | LEU | A | 112 | 36.917 | 22.962 | 50.379 | 1.00 | 17.99 | A C |
| ATOM | 633 | CD1 | LEU | A | 112 | 37.560 | 23.800 | 51.476 | 1.00 | 17.99 | A C |
| ATOM | 634 | CD2 | LEU | A | 112 | 35.878 | 22.010 | 50.943 | 1.00 | 17.99 | A C |
| ATOM | 635 | C | LEU | A | 112 | 38.413 | 23.899 | 47.950 | 1.00 | 37.72 | A C |
| ATOM | 636 | O | LEU | A | 112 | 38.165 | 22.740 | 47.655 | 1.00 | 37.72 | A O |
| ATOM | 637 | N | ARG | A | 113 | 39.585 | 24.459 | 47.683 | 1.00 | 29.46 | A N |
| ATOM | 638 | CA | ARG | A | 113 | 40.656 | 23.713 | 47.023 | 1.00 | 29.46 | A C |
| ATOM | 639 | CB | ARG | A | 113 | 41.973 | 24.487 | 47.136 | 1.00 | 48.42 | A C |
| ATOM | 640 | CG | ARG | A | 113 | 41.923 | 25.924 | 46.632 | 1.00 | 48.42 | A C |
| ATOM | 641 | CD | ARG | A | 113 | 41.958 | 25.992 | 45.106 | 1.00 | 48.42 | A C |
| ATOM | 642 | NE | ARG | A | 113 | 43.286 | 25.704 | 44.548 | 1.00 | 48.42 | A N |
| ATOM | 643 | CZ | ARG | A | 113 | 44.312 | 26.556 | 44.551 | 1.00 | 48.42 | A C |
| ATOM | 644 | NH1 | ARG | A | 113 | 44.167 | 27.763 | 45.089 | 1.00 | 48.42 | A N |
| ATOM | 645 | NH2 | ARG | A | 113 | 45.479 | 26.204 | 44.006 | 1.00 | 48.42 | A N |
| ATOM | 646 | C | ARG | A | 113 | 40.872 | 22.295 | 47.569 | 1.00 | 29.46 | A C |
| ATOM | 647 | O | ARG | A | 113 | 40.866 | 21.327 | 46.822 | 1.00 | 29.46 | A O |
| ATOM | 648 | N | TYR | A | 114 | 41.081 | 22.184 | 48.875 | 1.00 | 35.20 | A N |
| ATOM | 649 | CA | TYR | A | 114 | 41.318 | 20.903 | 49.518 | 1.00 | 35.20 | A C |
| ATOM | 650 | CB | TYR | A | 114 | 42.807 | 20.585 | 49.554 | 1.00 | 27.30 | A C |
| ATOM | 651 | CG | TYR | A | 114 | 43.530 | 20.726 | 48.245 | 1.00 | 27.30 | A C |
| ATOM | 652 | CD1 | TYR | A | 114 | 43.481 | 19.723 | 47.285 | 1.00 | 27.30 | A C |
| ATOM | 653 | CE1 | TYR | A | 114 | 44.184 | 19.842 | 46.087 | 1.00 | 27.30 | A C |
| ATOM | 654 | CD2 | TYR | A | 114 | 44.297 | 21.855 | 47.976 | 1.00 | 27.30 | A C |
| ATOM | 655 | CE2 | TYR | A | 114 | 44.998 | 21.982 | 46.787 | 1.00 | 27.30 | A C |
| ATOM | 656 | CZ | TYR | A | 114 | 44.936 | 20.974 | 45.850 | 1.00 | 27.30 | A C |
| ATOM | 657 | OH | TYR | A | 114 | 45.615 | 21.106 | 44.666 | 1.00 | 27.30 | A O |
| ATOM | 658 | C | TYR | A | 114 | 40.856 | 21.024 | 50.956 | 1.00 | 35.20 | A C |
| ATOM | 659 | O | TYR | A | 114 | 40.539 | 22.112 | 51.438 | 1.00 | 35.20 | A O |
| ATOM | 660 | N | PHE | A | 115 | 40.832 | 19.887 | 51.637 | 1.00 | 43.80 | A N |
| ATOM | 661 | CA | PHE | A | 115 | 40.489 | 19.839 | 53.045 | 1.00 | 43.80 | A C |
| ATOM | 662 | CB | PHE | A | 115 | 38.970 | 19.800 | 53.235 | 1.00 | 32.92 | A C |
| ATOM | 663 | CG | PHE | A | 115 | 38.345 | 18.490 | 52.917 | 1.00 | 32.92 | A C |
| ATOM | 664 | CD1 | PHE | A | 115 | 38.305 | 17.480 | 53.861 | 1.00 | 32.92 | A C |

FIG. 4-11

```
ATOM    665  CD2 PHE A 115      37.759  18.269  51.678  1.00 32.92      A    C
ATOM    666  CE1 PHE A 115      37.679  16.264  53.572  1.00 32.92      A    C
ATOM    667  CE2 PHE A 115      37.127  17.047  51.377  1.00 32.92      A    C
ATOM    668  CZ  PHE A 115      37.086  16.051  52.321  1.00 32.92      A    C
ATOM    669  C   PHE A 115      41.184  18.606  53.633  1.00 43.80      A    C
ATOM    670  O   PHE A 115      41.296  17.579  52.968  1.00 43.80      A    O
ATOM    671  N   PHE A 116      41.691  18.725  54.855  1.00 37.21      A    N
ATOM    672  CA  PHE A 116      42.378  17.611  55.486  1.00 37.21      A    C
ATOM    673  CB  PHE A 116      43.821  17.564  55.012  1.00 34.78      A    C
ATOM    674  CG  PHE A 116      44.658  18.724  55.488  1.00 34.78      A    C
ATOM    675  CD1 PHE A 116      45.273  18.688  56.727  1.00 34.78      A    C
ATOM    676  CD2 PHE A 116      44.827  19.857  54.695  1.00 34.78      A    C
ATOM    677  CE1 PHE A 116      46.041  19.753  57.158  1.00 34.78      A    C
ATOM    678  CE2 PHE A 116      45.601  20.931  55.129  1.00 34.78      A    C
ATOM    679  CZ  PHE A 116      46.203  20.878  56.355  1.00 34.78      A    C
ATOM    680  C   PHE A 116      42.346  17.662  57.006  1.00 37.21      A    C
ATOM    681  O   PHE A 116      42.095  18.707  57.607  1.00 37.21      A    O
ATOM    682  N   TYR A 117      42.604  16.516  57.622  1.00 53.98      A    N
ATOM    683  CA  TYR A 117      42.620  16.413  59.076  1.00 53.98      A    C
ATOM    684  CB  TYR A 117      41.848  15.173  59.499  1.00 34.79      A    C
ATOM    685  CG  TYR A 117      40.396  15.194  59.079  1.00 34.79      A    C
ATOM    686  CD1 TYR A 117      39.445  15.899  59.830  1.00 34.79      A    C
ATOM    687  CE1 TYR A 117      38.111  15.954  59.432  1.00 34.79      A    C
ATOM    688  CD2 TYR A 117      39.973  14.536  57.912  1.00 34.79      A    C
ATOM    689  CE2 TYR A 117      38.649  14.584  57.502  1.00 34.79      A    C
ATOM    690  CZ  TYR A 117      37.721  15.299  58.265  1.00 34.79      A    C
ATOM    691  OH  TYR A 117      36.408  15.396  57.850  1.00 34.79      A    O
ATOM    692  C   TYR A 117      44.071  16.319  59.561  1.00 53.98      A    C
ATOM    693  O   TYR A 117      44.890  15.650  58.929  1.00 53.98      A    O
ATOM    694  N   SER A 118      44.399  16.978  60.671  1.00 60.68      A    N
ATOM    695  CA  SER A 118      45.781  16.961  61.170  1.00 60.68      A    C
ATOM    696  CB  SER A 118      46.483  18.259  60.775  1.00 52.20      A    C
ATOM    697  OG  SER A 118      45.914  19.350  61.484  1.00 52.20      A    O
ATOM    698  C   SER A 118      45.853  16.799  62.686  1.00 60.68      A    C
ATOM    699  O   SER A 118      46.895  16.472  63.280  1.00 60.68      A    O
ATOM    700  N   SER A 119      44.707  17.055  63.285  1.00 98.84      A    N
ATOM    701  CA  SER A 119      44.475  17.011  64.721  1.00 98.84      A    C
ATOM    702  CB  SER A 119      45.428  17.985  65.476  1.00 52.54      A    C
ATOM    703  OG  SER A 119      46.788  17.538  65.446  1.00 52.54      A    O
ATOM    704  C   SER A 119      42.966  17.563  64.670  1.00 98.84      A    C
ATOM    705  O   SER A 119      42.115  17.172  65.493  1.00 98.84      A    O
ATOM    706  N   TYR A 127      42.659  18.424  63.664  1.00 82.31      A    N
ATOM    707  CA  TYR A 127      41.310  19.055  63.415  1.00 82.31      A    C
ATOM    708  CB  TYR A 127      41.247  20.529  63.867  1.00 68.57      A    C
ATOM    709  CG  TYR A 127      41.791  20.942  65.213  1.00 68.57      A    C
ATOM    710  CD1 TYR A 127      41.395  22.171  65.780  1.00 68.57      A    C
ATOM    711  CE1 TYR A 127      41.927  22.614  67.001  1.00 68.57      A    C
ATOM    712  CD2 TYR A 127      42.728  20.162  65.896  1.00 68.57      A    C
ATOM    713  CE2 TYR A 127      43.271  20.578  67.107  1.00 68.57      A    C
ATOM    714  CZ  TYR A 127      42.870  21.811  67.661  1.00 68.57      A    C
ATOM    715  OH  TYR A 127      43.407  22.246  68.860  1.00 68.57      A    O
ATOM    716  C   TYR A 127      40.970  19.124  61.898  1.00 82.31      A    C
ATOM    717  O   TYR A 127      41.807  18.794  61.055  1.00 82.31      A    O
ATOM    718  N   LEU A 128      39.764  19.610  61.557  1.00 41.85      A    N
ATOM    719  CA  LEU A 128      39.353  19.772  60.142  1.00 41.85      A    C
ATOM    720  CB  LEU A 128      37.829  19.954  59.992  1.00 37.86      A    C
ATOM    721  CG  LEU A 128      37.370  20.254  58.550  1.00 37.86      A    C
ATOM    722  CD1 LEU A 128      37.836  19.132  57.644  1.00 37.86      A    C
ATOM    723  CD2 LEU A 128      35.866  20.404  58.458  1.00 37.86      A    C
ATOM    724  C   LEU A 128      40.046  21.011  59.568  1.00 41.85      A    C
ATOM    725  O   LEU A 128      39.937  22.113  60.129  1.00 41.85      A    O
ATOM    726  N   ASN A 129      40.748  20.834  58.452  1.00 41.60      A    N
ATOM    727  CA  ASN A 129      41.458  21.939  57.823  1.00 41.60      A    C
ATOM    728  CB  ASN A 129      42.950  21.611  57.670  1.00 28.06      A    C
ATOM    729  CG  ASN A 129      43.649  21.444  59.001  1.00 28.06      A    C
ATOM    730  OD1 ASN A 129      43.262  20.594  59.800  1.00 28.06      A    O
ATOM    731  ND2 ASN A 129      44.680  22.253  59.252  1.00 28.06      A    N
```

FIG. 4-12

```
ATOM    732  C   ASN A 129      40.891  22.246  56.464  1.00 41.60      A  C
ATOM    733  O   ASN A 129      41.142  21.504  55.523  1.00 41.60      A  O
ATOM    734  N   LEU A 130      40.140  23.339  56.355  1.00 41.24      A  N
ATOM    735  CA  LEU A 130      39.557  23.735  55.076  1.00 41.24      A  C
ATOM    736  CB  LEU A 130      38.196  24.387  55.304  1.00 31.07      A  C
ATOM    737  CG  LEU A 130      37.185  23.502  56.033  1.00 31.07      A  C
ATOM    738  CD1 LEU A 130      36.012  24.342  56.498  1.00 31.07      A  C
ATOM    739  CD2 LEU A 130      36.728  22.387  55.124  1.00 31.07      A  C
ATOM    740  C   LEU A 130      40.487  24.701  54.360  1.00 41.24      A  C
ATOM    741  O   LEU A 130      40.770  25.784  54.868  1.00 41.24      A  O
ATOM    742  N   VAL A 131      40.977  24.293  53.190  1.00 35.40      A  N
ATOM    743  CA  VAL A 131      41.876  25.127  52.396  1.00 35.40      A  C
ATOM    744  CB  VAL A 131      42.980  24.297  51.712  1.00 29.92      A  C
ATOM    745  CG1 VAL A 131      44.036  25.225  51.138  1.00 29.92      A  C
ATOM    746  CG2 VAL A 131      43.607  23.352  52.715  1.00 29.92      A  C
ATOM    747  C   VAL A 131      41.057  25.815  51.325  1.00 35.40      A  C
ATOM    748  O   VAL A 131      40.723  25.198  50.312  1.00 35.40      A  O
ATOM    749  N   LEU A 132      40.723  27.084  51.555  1.00 27.18      A  N
ATOM    750  CA  LEU A 132      39.918  27.838  50.592  1.00 27.18      A  C
ATOM    751  CB  LEU A 132      38.779  28.596  51.276  1.00 27.88      A  C
ATOM    752  CG  LEU A 132      37.951  27.859  52.317  1.00 27.88      A  C
ATOM    753  CD1 LEU A 132      38.508  28.155  53.696  1.00 27.88      A  C
ATOM    754  CD2 LEU A 132      36.502  28.301  52.214  1.00 27.88      A  C
ATOM    755  C   LEU A 132      40.728  28.844  49.817  1.00 27.18      A  C
ATOM    756  O   LEU A 132      41.799  29.258  50.255  1.00 27.18      A  O
ATOM    757  N   ASP A 133      40.218  29.244  48.660  1.00 36.71      A  N
ATOM    758  CA  ASP A 133      40.925  30.230  47.866  1.00 36.71      A  C
ATOM    759  CB  ASP A 133      40.101  30.667  46.660  1.00 44.92      A  C
ATOM    760  CG  ASP A 133      40.275  29.759  45.466  1.00 44.92      A  C
ATOM    761  OD1 ASP A 133      41.352  29.114  45.379  1.00 44.92      A  O
ATOM    762  OD2 ASP A 133      39.343  29.723  44.617  1.00 44.92      A  O
ATOM    763  C   ASP A 133      41.115  31.442  48.746  1.00 36.71      A  C
ATOM    764  O   ASP A 133      40.288  31.700  49.610  1.00 36.71      A  O
ATOM    765  N   TYR A 134      42.189  32.190  48.539  1.00 29.35      A  N
ATOM    766  CA  TYR A 134      42.390  33.394  49.328  1.00 29.35      A  C
ATOM    767  CB  TYR A 134      43.769  33.422  49.980  1.00 40.36      A  C
ATOM    768  CG  TYR A 134      44.044  34.742  50.669  1.00 40.36      A  C
ATOM    769  CD1 TYR A 134      43.617  34.969  51.982  1.00 40.36      A  C
ATOM    770  CE1 TYR A 134      43.784  36.215  52.591  1.00 40.36      A  C
ATOM    771  CD2 TYR A 134      44.654  35.794  49.977  1.00 40.36      A  C
ATOM    772  CE2 TYR A 134      44.825  37.040  50.568  1.00 40.36      A  C
ATOM    773  CZ  TYR A 134      44.386  37.248  51.876  1.00 40.36      A  C
ATOM    774  OH  TYR A 134      44.531  38.497  52.446  1.00 40.36      A  O
ATOM    775  C   TYR A 134      42.229  34.642  48.482  1.00 29.35      A  C
ATOM    776  O   TYR A 134      42.987  34.856  47.538  1.00 29.35      A  O
ATOM    777  N   VAL A 135      41.239  35.458  48.829  1.00 24.33      A  N
ATOM    778  CA  VAL A 135      40.970  36.699  48.123  1.00 24.33      A  C
ATOM    779  CB  VAL A 135      39.467  36.887  47.863  1.00 34.47      A  C
ATOM    780  CG1 VAL A 135      39.241  38.128  47.009  1.00 34.47      A  C
ATOM    781  CG2 VAL A 135      38.905  35.642  47.163  1.00 34.47      A  C
ATOM    782  C   VAL A 135      41.503  37.809  49.007  1.00 24.33      A  C
ATOM    783  O   VAL A 135      41.270  37.808  50.204  1.00 24.33      A  O
ATOM    784  N   PRO A 136      42.236  38.768  48.426  1.00 35.10      A  N
ATOM    785  CD  PRO A 136      42.697  38.770  47.029  1.00 21.20      A  C
ATOM    786  CA  PRO A 136      42.822  39.892  49.158  1.00 35.10      A  C
ATOM    787  CB  PRO A 136      43.968  40.301  48.257  1.00 21.20      A  C
ATOM    788  CG  PRO A 136      43.368  40.116  46.919  1.00 21.20      A  C
ATOM    789  C   PRO A 136      41.953  41.089  49.545  1.00 35.10      A  C
ATOM    790  O   PRO A 136      42.422  41.982  50.235  1.00 35.10      A  O
ATOM    791  N   GLU A 137      40.703  41.139  49.117  1.00 29.78      A  N
ATOM    792  CA  GLU A 137      39.882  42.275  49.486  1.00 29.78      A  C
ATOM    793  CB  GLU A 137      39.801  43.224  48.293  1.00 31.81      A  C
ATOM    794  CG  GLU A 137      39.272  44.591  48.620  1.00 31.81      A  C
ATOM    795  CD  GLU A 137      40.145  45.337  49.613  1.00 31.81      A  C
ATOM    796  OE1 GLU A 137      40.990  46.139  49.181  1.00 31.81      A  O
ATOM    797  OE2 GLU A 137      39.994  45.120  50.831  1.00 31.81      A  O
ATOM    798  C   GLU A 137      38.492  41.818  49.900  1.00 29.78      A  C
```

FIG. 4-13

```
ATOM    799  O    GLU A 137      38.088  40.676  49.648  1.00 29.78      A  O
ATOM    800  N    THR A 138      37.761  42.710  50.553  1.00 23.95      A  N
ATOM    801  CA   THR A 138      36.411  42.403  50.994  1.00 23.95      A  C
ATOM    802  CB   THR A 138      36.400  42.044  52.464  1.00 23.03      A  C
ATOM    803  OG1  THR A 138      36.553  43.236  53.243  1.00 23.03      A  O
ATOM    804  CG2  THR A 138      37.537  41.056  52.759  1.00 23.03      A  C
ATOM    805  C    THR A 138      35.575  43.649  50.742  1.00 23.95      A  C
ATOM    806  O    THR A 138      36.072  44.759  50.861  1.00 23.95      A  O
ATOM    807  N    VAL A 139      34.322  43.470  50.345  1.00 17.50      A  N
ATOM    808  CA   VAL A 139      33.452  44.605  50.094  1.00 17.50      A  C
ATOM    809  CB   VAL A 139      32.021  44.117  49.815  1.00 17.20      A  C
ATOM    810  CG1  VAL A 139      31.019  45.205  50.092  1.00 17.20      A  C
ATOM    811  CG2  VAL A 139      31.916  43.685  48.370  1.00 17.20      A  C
ATOM    812  C    VAL A 139      33.493  45.505  51.318  1.00 17.50      A  C
ATOM    813  O    VAL A 139      33.475  46.725  51.213  1.00 17.50      A  O
ATOM    814  N    TYR A 140      33.585  44.883  52.485  1.00 33.12      A  N
ATOM    815  CA   TYR A 140      33.639  45.615  53.737  1.00 33.12      A  C
ATOM    816  CB   TYR A 140      33.755  44.644  54.902  1.00 29.86      A  C
ATOM    817  CG   TYR A 140      33.944  45.348  56.214  1.00 29.86      A  C
ATOM    818  CD1  TYR A 140      32.848  45.807  56.947  1.00 29.86      A  C
ATOM    819  CE1  TYR A 140      33.026  46.507  58.129  1.00 29.86      A  C
ATOM    820  CD2  TYR A 140      35.224  45.607  56.698  1.00 29.86      A  C
ATOM    821  CE2  TYR A 140      35.413  46.303  57.868  1.00 29.86      A  C
ATOM    822  CZ   TYR A 140      34.316  46.751  58.583  1.00 29.86      A  C
ATOM    823  OH   TYR A 140      34.524  47.437  59.754  1.00 29.86      A  O
ATOM    824  C    TYR A 140      34.789  46.619  53.788  1.00 33.12      A  C
ATOM    825  O    TYR A 140      34.561  47.797  54.047  1.00 33.12      A  O
ATOM    826  N    ARG A 141      36.018  46.160  53.552  1.00 29.44      A  N
ATOM    827  CA   ARG A 141      37.175  47.056  53.579  1.00 29.44      A  C
ATOM    828  CB   ARG A 141      38.468  46.281  53.335  1.00 45.77      A  C
ATOM    829  CG   ARG A 141      38.668  45.100  54.259  1.00 45.77      A  C
ATOM    830  CD   ARG A 141      40.149  44.831  54.466  1.00 45.77      A  C
ATOM    831  NE   ARG A 141      40.942  45.326  53.342  1.00 45.77      A  N
ATOM    832  CZ   ARG A 141      42.250  45.131  53.196  1.00 45.77      A  C
ATOM    833  NH1  ARG A 141      42.925  44.444  54.112  1.00 45.77      A  N
ATOM    834  NH2  ARG A 141      42.875  45.617  52.123  1.00 45.77      A  N
ATOM    835  C    ARG A 141      37.044  48.155  52.532  1.00 29.44      A  C
ATOM    836  O    ARG A 141      37.315  49.317  52.807  1.00 29.44      A  O
ATOM    837  N    VAL A 142      36.623  47.790  51.330  1.00 26.03      A  N
ATOM    838  CA   VAL A 142      36.467  48.768  50.271  1.00 26.03      A  C
ATOM    839  CB   VAL A 142      36.127  48.084  48.934  1.00 26.17      A  C
ATOM    840  CG1  VAL A 142      35.595  49.101  47.934  1.00 26.17      A  C
ATOM    841  CG2  VAL A 142      37.387  47.422  48.375  1.00 26.17      A  C
ATOM    842  C    VAL A 142      35.424  49.823  50.597  1.00 26.03      A  C
ATOM    843  O    VAL A 142      35.627  50.988  50.289  1.00 26.03      A  O
ATOM    844  N    ALA A 143      34.316  49.434  51.213  1.00 18.87      A  N
ATOM    845  CA   ALA A 143      33.285  50.408  51.554  1.00 18.87      A  C
ATOM    846  CB   ALA A 143      32.053  49.703  52.060  1.00 22.77      A  C
ATOM    847  C    ALA A 143      33.798  51.373  52.608  1.00 18.87      A  C
ATOM    848  O    ALA A 143      33.561  52.574  52.538  1.00 18.87      A  O
ATOM    849  N    ARG A 144      34.501  50.826  53.586  1.00 28.56      A  N
ATOM    850  CA   ARG A 144      35.061  51.599  54.671  1.00 28.56      A  C
ATOM    851  CB   ARG A 144      35.756  50.648  55.618  1.00 76.36      A  C
ATOM    852  CG   ARG A 144      36.730  51.255  56.567  1.00 76.36      A  C
ATOM    853  CD   ARG A 144      37.143  50.195  57.579  1.00 76.36      A  C
ATOM    854  NE   ARG A 144      38.233  50.643  58.450  1.00 76.36      A  N
ATOM    855  CZ   ARG A 144      38.254  51.797  59.128  1.00 76.36      A  C
ATOM    856  NH1  ARG A 144      37.230  52.653  59.043  1.00 76.36      A  N
ATOM    857  NH2  ARG A 144      39.304  52.087  59.905  1.00 76.36      A  N
ATOM    858  C    ARG A 144      36.012  52.658  54.159  1.00 28.56      A  C
ATOM    859  O    ARG A 144      36.032  53.774  54.673  1.00 28.56      A  O
ATOM    860  N    HIS A 145      36.801  52.302  53.149  1.00 33.41      A  N
ATOM    861  CA   HIS A 145      37.758  53.222  52.538  1.00 33.41      A  C
ATOM    862  CB   HIS A 145      38.504  52.475  51.425  1.00 53.58      A  C
ATOM    863  CG   HIS A 145      39.633  53.237  50.806  1.00 53.58      A  C
ATOM    864  CD2  HIS A 145      40.970  53.015  50.820  1.00 53.58      A  C
ATOM    865  ND1  HIS A 145      39.435  54.305  49.955  1.00 53.58      A  N
```

FIG. 4-14

```
ATOM    866  CE1 HIS A 145      40.598  54.698  49.462  1.00 53.58      A  C
ATOM    867  NE2 HIS A 145      41.545  53.930  49.970  1.00 53.58      A  N
ATOM    868  C   HIS A 145      37.030  54.456  51.985  1.00 33.41      A  C
ATOM    869  O   HIS A 145      37.299  55.591  52.400  1.00 33.41      A  O
ATOM    870  N   TYR A 146      36.094  54.220  51.067  1.00 38.87      A  N
ATOM    871  CA  TYR A 146      35.320  55.301  50.459  1.00 38.87      A  C
ATOM    872  CB  TYR A 146      34.327  54.749  49.434  1.00 24.39      A  C
ATOM    873  CG  TYR A 146      35.001  54.373  48.156  1.00 24.39      A  C
ATOM    874  CD1 TYR A 146      35.957  53.379  48.134  1.00 24.39      A  C
ATOM    875  CE1 TYR A 146      36.679  53.108  46.989  1.00 24.39      A  C
ATOM    876  CD2 TYR A 146      34.768  55.083  46.992  1.00 24.39      A  C
ATOM    877  CE2 TYR A 146      35.483  54.823  45.836  1.00 24.39      A  C
ATOM    878  CZ  TYR A 146      36.450  53.833  45.839  1.00 24.39      A  C
ATOM    879  OH  TYR A 146      37.240  53.587  44.727  1.00 24.39      A  O
ATOM    880  C   TYR A 146      34.570  56.085  51.521  1.00 38.87      A  C
ATOM    881  O   TYR A 146      34.440  57.305  51.439  1.00 38.87      A  O
ATOM    882  N   SER A 147      34.089  55.380  52.531  1.00 41.51      A  N
ATOM    883  CA  SER A 147      33.341  56.030  53.589  1.00 41.51      A  C
ATOM    884  CB  SER A 147      32.704  54.991  54.493  1.00 32.78      A  C
ATOM    885  OG  SER A 147      32.061  55.635  55.569  1.00 32.78      A  O
ATOM    886  C   SER A 147      34.230  56.934  54.417  1.00 41.51      A  C
ATOM    887  O   SER A 147      33.836  58.046  54.771  1.00 41.51      A  O
ATOM    888  N   ARG A 148      35.425  56.440  54.735  1.00 41.62      A  N
ATOM    889  CA  ARG A 148      36.389  57.205  55.509  1.00 41.62      A  C
ATOM    890  CB  ARG A 148      37.688  56.419  55.669  1.00 65.42      A  C
ATOM    891  CG  ARG A 148      37.690  55.402  56.786  1.00 65.42      A  C
ATOM    892  CD  ARG A 148      39.031  54.669  56.814  1.00 65.42      A  C
ATOM    893  NE  ARG A 148      39.549  54.533  58.178  1.00 65.42      A  N
ATOM    894  CZ  ARG A 148      40.061  55.531  58.908  1.00 65.42      A  C
ATOM    895  NH1 ARG A 148      40.135  56.767  58.412  1.00 65.42      A  N
ATOM    896  NH2 ARG A 148      40.507  55.298  60.143  1.00 65.42      A  N
ATOM    897  C   ARG A 148      36.675  58.494  54.760  1.00 41.62      A  C
ATOM    898  O   ARG A 148      36.526  59.582  55.302  1.00 41.62      A  O
ATOM    899  N   ALA A 149      37.082  58.350  53.502  1.00 40.20      A  N
ATOM    900  CA  ALA A 149      37.396  59.479  52.640  1.00 40.20      A  C
ATOM    901  CB  ALA A 149      38.069  58.985  51.356  1.00 27.77      A  C
ATOM    902  C   ALA A 149      36.122  60.254  52.285  1.00 40.20      A  C
ATOM    903  O   ALA A 149      36.115  61.001  51.307  1.00 40.20      A  O
ATOM    904  N   LYS A 150      35.060  60.081  53.075  1.00 41.83      A  N
ATOM    905  CA  LYS A 150      33.774  60.749  52.842  1.00 41.83      A  C
ATOM    906  CB  LYS A 150      33.775  62.180  53.406  1.00 53.62      A  C
ATOM    907  CG  LYS A 150      33.635  62.272  54.923  1.00 53.62      A  C
ATOM    908  CD  LYS A 150      32.651  63.387  55.364  1.00 53.62      A  C
ATOM    909  CE  LYS A 150      33.146  64.812  55.025  1.00 53.62      A  C
ATOM    910  NZ  LYS A 150      32.268  65.890  55.620  1.00 53.62      A  N
ATOM    911  C   LYS A 150      33.392  60.795  51.365  1.00 41.83      A  C
ATOM    912  O   LYS A 150      32.978  61.830  50.851  1.00 41.83      A  O
ATOM    913  N   GLN A 151      33.551  59.671  50.680  1.00 43.44      A  N
ATOM    914  CA  GLN A 151      33.193  59.582  49.274  1.00 43.44      A  C
ATOM    915  CB  GLN A 151      34.415  59.233  48.451  1.00 48.03      A  C
ATOM    916  CG  GLN A 151      35.655  59.971  48.837  1.00 48.03      A  C
ATOM    917  CD  GLN A 151      36.788  59.703  47.854  1.00 48.03      A  C
ATOM    918  OE1 GLN A 151      37.974  59.751  48.223  1.00 48.03      A  O
ATOM    919  NE2 GLN A 151      36.430  59.422  46.582  1.00 48.03      A  N
ATOM    920  C   GLN A 151      32.157  58.470  49.099  1.00 43.44      A  C
ATOM    921  O   GLN A 151      31.711  57.850  50.068  1.00 43.44      A  O
ATOM    922  N   THR A 152      31.769  58.218  47.858  1.00 43.50      A  N
ATOM    923  CA  THR A 152      30.814  57.155  47.606  1.00 43.50      A  C
ATOM    924  CB  THR A 152      29.463  57.699  47.083  1.00 66.50      A  C
ATOM    925  OG1 THR A 152      28.559  57.872  48.184  1.00 66.50      A  O
ATOM    926  CG2 THR A 152      28.848  56.741  46.058  1.00 66.50      A  C
ATOM    927  C   THR A 152      31.404  56.184  46.600  1.00 43.50      A  C
ATOM    928  O   THR A 152      32.116  56.574  45.671  1.00 43.50      A  O
ATOM    929  N   LEU A 153      31.123  54.910  46.797  1.00 33.25      A  N
ATOM    930  CA  LEU A 153      31.626  53.919  45.879  1.00 33.25      A  C
ATOM    931  CB  LEU A 153      31.409  52.509  46.424  1.00 35.15      A  C
ATOM    932  CG  LEU A 153      31.955  51.435  45.489  1.00 35.15      A  C
```

FIG. 4-15

```
ATOM    933  CD1 LEU A 153      33.476  51.558  45.445  1.00 35.15      A    C
ATOM    934  CD2 LEU A 153      31.520  50.063  45.967  1.00 35.15      A    C
ATOM    935  C   LEU A 153      30.869  54.072  44.567  1.00 33.25      A    C
ATOM    936  O   LEU A 153      29.634  54.079  44.547  1.00 33.25      A    O
ATOM    937  N   PRO A 154      31.600  54.222  43.455  1.00 30.73      A    N
ATOM    938  CD  PRO A 154      33.067  54.302  43.355  1.00 33.43      A    C
ATOM    939  CA  PRO A 154      30.968  54.367  42.142  1.00 30.73      A    C
ATOM    940  CB  PRO A 154      32.140  54.207  41.184  1.00 33.43      A    C
ATOM    941  CG  PRO A 154      33.267  54.814  41.940  1.00 33.43      A    C
ATOM    942  C   PRO A 154      29.926  53.265  41.936  1.00 30.73      A    C
ATOM    943  O   PRO A 154      30.246  52.072  41.960  1.00 30.73      A    O
ATOM    944  N   VAL A 155      28.681  53.675  41.724  1.00 36.26      A    N
ATOM    945  CA  VAL A 155      27.573  52.752  41.521  1.00 36.26      A    C
ATOM    946  CB  VAL A 155      26.346  53.504  40.993  1.00 39.09      A    C
ATOM    947  CG1 VAL A 155      26.050  54.709  41.893  1.00 39.09      A    C
ATOM    948  CG2 VAL A 155      26.590  53.932  39.568  1.00 39.09      A    C
ATOM    949  C   VAL A 155      27.905  51.598  40.572  1.00 36.26      A    C
ATOM    950  O   VAL A 155      27.410  50.489  40.739  1.00 36.26      A    O
ATOM    951  N   ILE A 156      28.744  51.848  39.579  1.00 23.38      A    N
ATOM    952  CA  ILE A 156      29.096  50.799  38.638  1.00 23.38      A    C
ATOM    953  CB  ILE A 156      30.180  51.280  37.658  1.00 23.03      A    C
ATOM    954  CG2 ILE A 156      31.352  51.879  38.436  1.00 23.03      A    C
ATOM    955  CG1 ILE A 156      30.633  50.127  36.761  1.00 23.03      A    C
ATOM    956  CD1 ILE A 156      29.556  49.560  35.907  1.00 23.03      A    C
ATOM    957  C   ILE A 156      29.603  49.597  39.411  1.00 23.38      A    C
ATOM    958  O   ILE A 156      29.350  48.460  39.031  1.00 23.38      A    O
ATOM    959  N   TYR A 157      30.326  49.860  40.496  1.00 31.92      A    N
ATOM    960  CA  TYR A 157      30.853  48.799  41.347  1.00 31.92      A    C
ATOM    961  CB  TYR A 157      31.939  49.339  42.273  1.00 37.39      A    C
ATOM    962  CG  TYR A 157      33.249  49.528  41.560  1.00 37.39      A    C
ATOM    963  CD1 TYR A 157      33.854  50.784  41.472  1.00 37.39      A    C
ATOM    964  CE1 TYR A 157      35.043  50.953  40.769  1.00 37.39      A    C
ATOM    965  CD2 TYR A 157      33.869  48.448  40.931  1.00 37.39      A    C
ATOM    966  CE2 TYR A 157      35.046  48.603  40.229  1.00 37.39      A    C
ATOM    967  CZ  TYR A 157      35.632  49.855  40.149  1.00 37.39      A    C
ATOM    968  OH  TYR A 157      36.813  50.003  39.460  1.00 37.39      A    O
ATOM    969  C   TYR A 157      29.728  48.224  42.180  1.00 31.92      A    C
ATOM    970  O   TYR A 157      29.647  47.017  42.389  1.00 31.92      A    O
ATOM    971  N   VAL A 158      28.867  49.107  42.670  1.00 29.52      A    N
ATOM    972  CA  VAL A 158      27.729  48.684  43.463  1.00 29.52      A    C
ATOM    973  CB  VAL A 158      26.807  49.886  43.799  1.00 20.87      A    C
ATOM    974  CG1 VAL A 158      25.562  49.410  44.540  1.00 20.87      A    C
ATOM    975  CG2 VAL A 158      27.564  50.903  44.635  1.00 20.87      A    C
ATOM    976  C   VAL A 158      26.960  47.668  42.626  1.00 29.52      A    C
ATOM    977  O   VAL A 158      26.588  46.598  43.111  1.00 29.52      A    O
ATOM    978  N   LYS A 159      26.729  48.012  41.363  1.00 21.26      A    N
ATOM    979  CA  LYS A 159      26.019  47.131  40.456  1.00 21.26      A    C
ATOM    980  CB  LYS A 159      25.894  47.778  39.077  1.00 23.81      A    C
ATOM    981  CG  LYS A 159      24.843  48.883  39.041  1.00 23.81      A    C
ATOM    982  CD  LYS A 159      24.833  49.665  37.744  1.00 23.81      A    C
ATOM    983  CE  LYS A 159      23.813  50.774  37.816  1.00 23.81      A    C
ATOM    984  NZ  LYS A 159      24.120  51.889  36.896  1.00 23.81      A    N
ATOM    985  C   LYS A 159      26.763  45.817  40.369  1.00 21.26      A    C
ATOM    986  O   LYS A 159      26.236  44.783  40.771  1.00 21.26      A    O
ATOM    987  N   LEU A 160      27.987  45.859  39.851  1.00 19.23      A    N
ATOM    988  CA  LEU A 160      28.815  44.661  39.730  1.00 19.23      A    C
ATOM    989  CB  LEU A 160      30.258  45.048  39.430  1.00 22.21      A    C
ATOM    990  CG  LEU A 160      30.614  45.232  37.963  1.00 22.21      A    C
ATOM    991  CD1 LEU A 160      31.963  45.888  37.854  1.00 22.21      A    C
ATOM    992  CD2 LEU A 160      30.620  43.877  37.278  1.00 22.21      A    C
ATOM    993  C   LEU A 160      28.797  43.774  40.964  1.00 19.23      A    C
ATOM    994  O   LEU A 160      28.488  42.594  40.869  1.00 19.23      A    O
ATOM    995  N   TYR A 161      29.133  44.340  42.120  1.00 36.30      A    N
ATOM    996  CA  TYR A 161      29.167  43.567  43.355  1.00 36.30      A    C
ATOM    997  CB  TYR A 161      29.760  44.416  44.495  1.00 27.20      A    C
ATOM    998  CG  TYR A 161      31.175  44.957  44.253  1.00 27.20      A    C
ATOM    999  CD1 TYR A 161      32.106  44.258  43.485  1.00 27.20      A    C
```

FIG. 4-16

| | | | | | | | | | | | |
|---|---|---|---|---|---|---|---|---|---|---|---|
| ATOM | 1000 | CE1 | TYR | A | 161 | 33.395 | 44.757 | 43.277 | 1.00 27.20 | A | C |
| ATOM | 1001 | CD2 | TYR | A | 161 | 31.578 | 46.167 | 44.805 | 1.00 27.20 | A | C |
| ATOM | 1002 | CE2 | TYR | A | 161 | 32.861 | 46.666 | 44.602 | 1.00 27.20 | A | C |
| ATOM | 1003 | CZ | TYR | A | 161 | 33.763 | 45.958 | 43.840 | 1.00 27.20 | A | C |
| ATOM | 1004 | OH | TYR | A | 161 | 35.040 | 46.445 | 43.655 | 1.00 27.20 | A | O |
| ATOM | 1005 | C | TYR | A | 161 | 27.802 | 42.989 | 43.752 | 1.00 36.30 | A | C |
| ATOM | 1006 | O | TYR | A | 161 | 27.674 | 41.783 | 43.978 | 1.00 36.30 | A | O |
| ATOM | 1007 | N | MET | A | 162 | 26.776 | 43.829 | 43.816 | 1.00 25.99 | A | N |
| ATOM | 1008 | CA | MET | A | 162 | 25.465 | 43.333 | 44.194 | 1.00 25.99 | A | C |
| ATOM | 1009 | CB | MET | A | 162 | 24.468 | 44.485 | 44.293 | 1.00 24.75 | A | C |
| ATOM | 1010 | CG | MET | A | 162 | 24.722 | 45.419 | 45.482 | 1.00 24.75 | A | C |
| ATOM | 1011 | SD | MET | A | 162 | 24.940 | 44.534 | 47.033 | 1.00 24.75 | A | S |
| ATOM | 1012 | CE | MET | A | 162 | 23.360 | 43.816 | 47.220 | 1.00 24.75 | A | C |
| ATOM | 1013 | C | MET | A | 162 | 24.945 | 42.254 | 43.266 | 1.00 25.99 | A | C |
| ATOM | 1014 | O | MET | A | 162 | 24.413 | 41.251 | 43.729 | 1.00 25.99 | A | O |
| ATOM | 1015 | N | TYR | A | 163 | 25.100 | 42.457 | 41.959 | 1.00 19.18 | A | N |
| ATOM | 1016 | CA | TYR | A | 163 | 24.643 | 41.491 | 40.969 | 1.00 19.18 | A | C |
| ATOM | 1017 | CB | TYR | A | 163 | 25.077 | 41.942 | 39.581 | 1.00 22.75 | A | C |
| ATOM | 1018 | CG | TYR | A | 163 | 24.716 | 40.977 | 38.481 | 1.00 22.75 | A | C |
| ATOM | 1019 | CD1 | TYR | A | 163 | 23.412 | 40.868 | 38.027 | 1.00 22.75 | A | C |
| ATOM | 1020 | CE1 | TYR | A | 163 | 23.074 | 39.948 | 37.049 | 1.00 22.75 | A | C |
| ATOM | 1021 | CD2 | TYR | A | 163 | 25.679 | 40.140 | 37.925 | 1.00 22.75 | A | C |
| ATOM | 1022 | CE2 | TYR | A | 163 | 25.353 | 39.211 | 36.941 | 1.00 22.75 | A | C |
| ATOM | 1023 | CZ | TYR | A | 163 | 24.050 | 39.117 | 36.501 | 1.00 22.75 | A | C |
| ATOM | 1024 | OH | TYR | A | 163 | 23.730 | 38.220 | 35.495 | 1.00 22.75 | A | O |
| ATOM | 1025 | C | TYR | A | 163 | 25.263 | 40.146 | 41.277 | 1.00 19.18 | A | C |
| ATOM | 1026 | O | TYR | A | 163 | 24.567 | 39.150 | 41.426 | 1.00 19.18 | A | O |
| ATOM | 1027 | N | GLN | A | 164 | 26.584 | 40.126 | 41.378 | 1.00 27.19 | A | N |
| ATOM | 1028 | CA | GLN | A | 164 | 27.301 | 38.900 | 41.670 | 1.00 27.19 | A | C |
| ATOM | 1029 | CB | GLN | A | 164 | 28.799 | 39.178 | 41.727 | 1.00 12.65 | A | C |
| ATOM | 1030 | CG | GLN | A | 164 | 29.324 | 39.725 | 40.420 | 1.00 12.65 | A | C |
| ATOM | 1031 | CD | GLN | A | 164 | 30.818 | 39.712 | 40.336 | 1.00 12.65 | A | C |
| ATOM | 1032 | OE1 | GLN | A | 164 | 31.429 | 38.667 | 40.454 | 1.00 12.65 | A | O |
| ATOM | 1033 | NE2 | GLN | A | 164 | 31.419 | 40.873 | 40.120 | 1.00 12.65 | A | N |
| ATOM | 1034 | C | GLN | A | 164 | 26.808 | 38.287 | 42.968 | 1.00 27.19 | A | C |
| ATOM | 1035 | O | GLN | A | 164 | 26.597 | 37.078 | 43.036 | 1.00 27.19 | A | O |
| ATOM | 1036 | N | LEU | A | 165 | 26.608 | 39.106 | 43.995 | 1.00 21.52 | A | N |
| ATOM | 1037 | CA | LEU | A | 165 | 26.116 | 38.569 | 45.258 | 1.00 21.52 | A | C |
| ATOM | 1038 | CB | LEU | A | 165 | 25.953 | 39.681 | 46.296 | 1.00 18.83 | A | C |
| ATOM | 1039 | CG | LEU | A | 165 | 25.103 | 39.371 | 47.538 | 1.00 18.83 | A | C |
| ATOM | 1040 | CD1 | LEU | A | 165 | 25.688 | 38.215 | 48.321 | 1.00 18.83 | A | C |
| ATOM | 1041 | CD2 | LEU | A | 165 | 25.025 | 40.594 | 48.406 | 1.00 18.83 | A | C |
| ATOM | 1042 | C | LEU | A | 165 | 24.791 | 37.843 | 45.062 | 1.00 21.52 | A | C |
| ATOM | 1043 | O | LEU | A | 165 | 24.587 | 36.757 | 45.602 | 1.00 21.52 | A | O |
| ATOM | 1044 | N | PHE | A | 166 | 23.891 | 38.437 | 44.285 | 1.00 16.76 | A | N |
| ATOM | 1045 | CA | PHE | A | 166 | 22.599 | 37.823 | 44.047 | 1.00 16.76 | A | C |
| ATOM | 1046 | CB | PHE | A | 166 | 21.701 | 38.813 | 43.307 | 1.00 14.70 | A | C |
| ATOM | 1047 | CG | PHE | A | 166 | 21.039 | 39.820 | 44.219 | 1.00 14.70 | A | C |
| ATOM | 1048 | CD1 | PHE | A | 166 | 20.300 | 39.401 | 45.326 | 1.00 14.70 | A | C |
| ATOM | 1049 | CD2 | PHE | A | 166 | 21.155 | 41.180 | 43.985 | 1.00 14.70 | A | C |
| ATOM | 1050 | CE1 | PHE | A | 166 | 19.698 | 40.324 | 46.181 | 1.00 14.70 | A | C |
| ATOM | 1051 | CE2 | PHE | A | 166 | 20.553 | 42.100 | 44.839 | 1.00 14.70 | A | C |
| ATOM | 1052 | CZ | PHE | A | 166 | 19.827 | 41.668 | 45.933 | 1.00 14.70 | A | C |
| ATOM | 1053 | C | PHE | A | 166 | 22.740 | 36.506 | 43.296 | 1.00 16.76 | A | C |
| ATOM | 1054 | O | PHE | A | 166 | 22.045 | 35.528 | 43.589 | 1.00 16.76 | A | O |
| ATOM | 1055 | N | ARG | A | 167 | 23.671 | 36.470 | 42.347 | 1.00 29.87 | A | N |
| ATOM | 1056 | CA | ARG | A | 167 | 23.892 | 35.259 | 41.579 | 1.00 29.87 | A | C |
| ATOM | 1057 | CB | ARG | A | 167 | 24.850 | 35.533 | 40.419 | 1.00 30.66 | A | C |
| ATOM | 1058 | CG | ARG | A | 167 | 24.719 | 34.523 | 39.273 | 1.00 30.66 | A | C |
| ATOM | 1059 | CD | ARG | A | 167 | 25.749 | 34.763 | 38.194 | 1.00 30.66 | A | C |
| ATOM | 1060 | NE | ARG | A | 167 | 25.993 | 33.551 | 37.424 | 1.00 30.66 | A | N |
| ATOM | 1061 | CZ | ARG | A | 167 | 27.015 | 33.398 | 36.592 | 1.00 30.66 | A | C |
| ATOM | 1062 | NH1 | ARG | A | 167 | 27.887 | 34.386 | 36.430 | 1.00 30.66 | A | N |
| ATOM | 1063 | NH2 | ARG | A | 167 | 27.162 | 32.264 | 35.923 | 1.00 30.66 | A | N |
| ATOM | 1064 | C | ARG | A | 167 | 24.417 | 34.134 | 42.466 | 1.00 29.87 | A | C |
| ATOM | 1065 | O | ARG | A | 167 | 24.118 | 32.966 | 42.224 | 1.00 29.87 | A | O |
| ATOM | 1066 | N | SER | A | 168 | 25.180 | 34.476 | 43.500 | 1.00 22.74 | A | N |

FIG. 4-17

```
ATOM   1067  CA   SER A 168      25.702  33.450  44.387  1.00 22.74      A    C
ATOM   1068  CB   SER A 168      26.860  33.986  45.224  1.00 27.05      A    C
ATOM   1069  OG   SER A 168      26.424  34.955  46.152  1.00 27.05      A    O
ATOM   1070  C    SER A 168      24.570  32.994  45.279  1.00 22.74      A    C
ATOM   1071  O    SER A 168      24.472  31.819  45.607  1.00 22.74      A    O
ATOM   1072  N    LEU A 169      23.697  33.927  45.644  1.00 28.51      A    N
ATOM   1073  CA   LEU A 169      22.563  33.612  46.495  1.00 28.51      A    C
ATOM   1074  CB   LEU A 169      21.855  34.895  46.928  1.00 18.89      A    C
ATOM   1075  CG   LEU A 169      21.823  35.221  48.424  1.00 18.89      A    C
ATOM   1076  CD1  LEU A 169      23.212  35.260  48.981  1.00 18.89      A    C
ATOM   1077  CD2  LEU A 169      21.129  36.547  48.636  1.00 18.89      A    C
ATOM   1078  C    LEU A 169      21.602  32.712  45.745  1.00 28.51      A    C
ATOM   1079  O    LEU A 169      21.136  31.714  46.285  1.00 28.51      A    O
ATOM   1080  N    ALA A 170      21.320  33.060  44.491  1.00 23.92      A    N
ATOM   1081  CA   ALA A 170      20.412  32.273  43.662  1.00 23.92      A    C
ATOM   1082  CB   ALA A 170      20.293  32.899  42.278  1.00 18.89      A    C
ATOM   1083  C    ALA A 170      20.934  30.844  43.550  1.00 23.92      A    C
ATOM   1084  O    ALA A 170      20.167  29.879  43.498  1.00 23.92      A    O
ATOM   1085  N    TYR A 171      22.251  30.713  43.536  1.00 26.18      A    N
ATOM   1086  CA   TYR A 171      22.866  29.406  43.413  1.00 26.18      A    C
ATOM   1087  CB   TYR A 171      24.347  29.560  43.077  1.00 38.36      A    C
ATOM   1088  CG   TYR A 171      25.082  28.246  42.974  1.00 38.36      A    C
ATOM   1089  CD1  TYR A 171      24.788  27.343  41.962  1.00 38.36      A    C
ATOM   1090  CE1  TYR A 171      25.470  26.143  41.853  1.00 38.36      A    C
ATOM   1091  CD2  TYR A 171      26.080  27.912  43.883  1.00 38.36      A    C
ATOM   1092  CE2  TYR A 171      26.772  26.709  43.783  1.00 38.36      A    C
ATOM   1093  CZ   TYR A 171      26.466  25.829  42.764  1.00 38.36      A    C
ATOM   1094  OH   TYR A 171      27.181  24.655  42.647  1.00 38.36      A    O
ATOM   1095  C    TYR A 171      22.723  28.522  44.635  1.00 26.18      A    C
ATOM   1096  O    TYR A 171      22.280  27.380  44.533  1.00 26.18      A    O
ATOM   1097  N    ILE A 172      23.103  29.034  45.795  1.00 14.66      A    N
ATOM   1098  CA   ILE A 172      23.005  28.215  46.977  1.00 14.66      A    C
ATOM   1099  CB   ILE A 172      23.785  28.830  48.163  1.00 21.63      A    C
ATOM   1100  CG2  ILE A 172      25.255  28.963  47.794  1.00 21.63      A    C
ATOM   1101  CG1  ILE A 172      23.199  30.186  48.544  1.00 21.63      A    C
ATOM   1102  CD1  ILE A 172      23.570  30.625  49.929  1.00 21.63      A    C
ATOM   1103  C    ILE A 172      21.549  28.000  47.333  1.00 14.66      A    C
ATOM   1104  O    ILE A 172      21.174  26.920  47.772  1.00 14.66      A    O
ATOM   1105  N    HIS A 173      20.718  29.011  47.122  1.00 21.18      A    N
ATOM   1106  CA   HIS A 173      19.306  28.870  47.447  1.00 21.18      A    C
ATOM   1107  CB   HIS A 173      18.579  30.199  47.228  1.00 24.09      A    C
ATOM   1108  CG   HIS A 173      18.817  31.199  48.318  1.00 24.09      A    C
ATOM   1109  CD2  HIS A 173      19.618  31.152  49.408  1.00 24.09      A    C
ATOM   1110  ND1  HIS A 173      18.197  32.428  48.355  1.00 24.09      A    N
ATOM   1111  CE1  HIS A 173      18.607  33.093  49.421  1.00 24.09      A    C
ATOM   1112  NE2  HIS A 173      19.470  32.341  50.076  1.00 24.09      A    N
ATOM   1113  C    HIS A 173      18.691  27.764  46.600  1.00 21.18      A    C
ATOM   1114  O    HIS A 173      17.722  27.115  46.988  1.00 21.18      A    O
ATOM   1115  N    SER A 174      19.289  27.558  45.436  1.00 36.15      A    N
ATOM   1116  CA   SER A 174      18.851  26.550  44.493  1.00 36.15      A    C
ATOM   1117  CB   SER A 174      19.824  26.546  43.321  1.00 53.54      A    C
ATOM   1118  OG   SER A 174      19.552  25.503  42.413  1.00 53.54      A    O
ATOM   1119  C    SER A 174      18.854  25.198  45.184  1.00 36.15      A    C
ATOM   1120  O    SER A 174      17.920  24.427  45.035  1.00 36.15      A    O
ATOM   1121  N    PHE A 175      19.915  24.912  45.928  1.00 30.64      A    N
ATOM   1122  CA   PHE A 175      20.029  23.653  46.657  1.00 30.64      A    C
ATOM   1123  CB   PHE A 175      21.495  23.366  46.992  1.00 43.25      A    C
ATOM   1124  CG   PHE A 175      22.379  23.086  45.805  1.00 43.25      A    C
ATOM   1125  CD1  PHE A 175      22.607  21.785  45.379  1.00 43.25      A    C
ATOM   1126  CD2  PHE A 175      23.076  24.114  45.182  1.00 43.25      A    C
ATOM   1127  CE1  PHE A 175      23.526  21.512  44.360  1.00 43.25      A    C
ATOM   1128  CE2  PHE A 175      24.001  23.846  44.155  1.00 43.25      A    C
ATOM   1129  CZ   PHE A 175      24.225  22.547  43.750  1.00 43.25      A    C
ATOM   1130  C    PHE A 175      19.267  23.730  47.985  1.00 30.64      A    C
ATOM   1131  O    PHE A 175      19.416  22.856  48.841  1.00 30.64      A    O
ATOM   1132  N    GLY A 176      18.480  24.789  48.166  1.00 38.74      A    N
ATOM   1133  CA   GLY A 176      17.717  24.955  49.395  1.00 38.74      A    C
```

FIG. 4-18

| | | | | | | | | | | | |
|---|---|---|---|---|---|---|---|---|---|---|---|
| ATOM | 1134 | C | GLY | A | 176 | 18.543 | 25.412 | 50.580 | 1.00 | 38.74 | A C |
| ATOM | 1135 | O | GLY | A | 176 | 18.042 | 25.479 | 51.702 | 1.00 | 38.74 | A O |
| ATOM | 1136 | N | ILE | A | 177 | 19.809 | 25.731 | 50.321 | 1.00 | 32.10 | A N |
| ATOM | 1137 | CA | ILE | A | 177 | 20.744 | 26.195 | 51.340 | 1.00 | 32.10 | A C |
| ATOM | 1138 | CB | ILE | A | 177 | 22.180 | 25.839 | 50.921 | 1.00 | 40.60 | A C |
| ATOM | 1139 | CG2 | ILE | A | 177 | 23.184 | 26.352 | 51.953 | 1.00 | 40.60 | A C |
| ATOM | 1140 | CG1 | ILE | A | 177 | 22.292 | 24.325 | 50.743 | 1.00 | 40.60 | A C |
| ATOM | 1141 | CD1 | ILE | A | 177 | 23.698 | 23.847 | 50.351 | 1.00 | 40.60 | A C |
| ATOM | 1142 | C | ILE | A | 177 | 20.656 | 27.706 | 51.564 | 1.00 | 32.10 | A C |
| ATOM | 1143 | O | ILE | A | 177 | 20.510 | 28.479 | 50.611 | 1.00 | 32.10 | A O |
| ATOM | 1144 | N | CYS | A | 178 | 20.762 | 28.108 | 52.833 | 1.00 | 31.99 | A N |
| ATOM | 1145 | CA | CYS | A | 178 | 20.688 | 29.511 | 53.243 | 1.00 | 31.99 | A C |
| ATOM | 1146 | CB | CYS | A | 178 | 19.534 | 29.696 | 54.225 | 1.00 | 35.38 | A C |
| ATOM | 1147 | SG | CYS | A | 178 | 19.131 | 31.389 | 54.607 | 1.00 | 35.38 | A S |
| ATOM | 1148 | C | CYS | A | 178 | 21.997 | 29.877 | 53.909 | 1.00 | 31.99 | A C |
| ATOM | 1149 | O | CYS | A | 178 | 22.462 | 29.163 | 54.788 | 1.00 | 31.99 | A O |
| ATOM | 1150 | N | HIS | A | 179 | 22.606 | 30.975 | 53.484 | 1.00 | 29.87 | A N |
| ATOM | 1151 | CA | HIS | A | 179 | 23.880 | 31.380 | 54.062 | 1.00 | 29.87 | A C |
| ATOM | 1152 | CB | HIS | A | 179 | 24.518 | 32.488 | 53.215 | 1.00 | 20.76 | A C |
| ATOM | 1153 | CG | HIS | A | 179 | 25.925 | 32.822 | 53.613 | 1.00 | 20.76 | A C |
| ATOM | 1154 | CD2 | HIS | A | 179 | 27.110 | 32.525 | 53.030 | 1.00 | 20.76 | A C |
| ATOM | 1155 | ND1 | HIS | A | 179 | 26.230 | 33.511 | 54.766 | 1.00 | 20.76 | A N |
| ATOM | 1156 | CE1 | HIS | A | 179 | 27.541 | 33.622 | 54.878 | 1.00 | 20.76 | A C |
| ATOM | 1157 | NE2 | HIS | A | 179 | 28.098 | 33.030 | 53.838 | 1.00 | 20.76 | A N |
| ATOM | 1158 | C | HIS | A | 179 | 23.710 | 31.835 | 55.504 | 1.00 | 29.87 | A C |
| ATOM | 1159 | O | HIS | A | 179 | 24.555 | 31.569 | 56.349 | 1.00 | 29.87 | A O |
| ATOM | 1160 | N | ARG | A | 180 | 22.612 | 32.524 | 55.773 | 1.00 | 36.47 | A N |
| ATOM | 1161 | CA | ARG | A | 180 | 22.313 | 33.005 | 57.110 | 1.00 | 36.47 | A C |
| ATOM | 1162 | CB | ARG | A | 180 | 22.321 | 31.842 | 58.085 | 1.00 | 20.19 | A C |
| ATOM | 1163 | CG | ARG | A | 180 | 21.094 | 30.980 | 58.119 | 1.00 | 20.19 | A C |
| ATOM | 1164 | CD | ARG | A | 180 | 21.499 | 29.801 | 58.955 | 1.00 | 20.19 | A C |
| ATOM | 1165 | NE | ARG | A | 180 | 20.436 | 29.175 | 59.718 | 1.00 | 20.19 | A N |
| ATOM | 1166 | CZ | ARG | A | 180 | 20.683 | 28.273 | 60.654 | 1.00 | 20.19 | A C |
| ATOM | 1167 | NH1 | ARG | A | 180 | 21.942 | 27.937 | 60.900 | 1.00 | 20.19 | A N |
| ATOM | 1168 | NH2 | ARG | A | 180 | 19.695 | 27.715 | 61.342 | 1.00 | 20.19 | A N |
| ATOM | 1169 | C | ARG | A | 180 | 23.203 | 34.109 | 57.665 | 1.00 | 36.47 | A C |
| ATOM | 1170 | O | ARG | A | 180 | 22.906 | 34.638 | 58.739 | 1.00 | 36.47 | A O |
| ATOM | 1171 | N | ASP | A | 181 | 24.281 | 34.465 | 56.973 | 1.00 | 25.40 | A N |
| ATOM | 1172 | CA | ASP | A | 181 | 25.131 | 35.534 | 57.484 | 1.00 | 25.40 | A C |
| ATOM | 1173 | CB | ASP | A | 181 | 26.238 | 34.961 | 58.354 | 1.00 | 35.53 | A C |
| ATOM | 1174 | CG | ASP | A | 181 | 26.911 | 36.023 | 59.182 | 1.00 | 35.53 | A C |
| ATOM | 1175 | OD1 | ASP | A | 181 | 26.267 | 37.073 | 59.394 | 1.00 | 35.53 | A O |
| ATOM | 1176 | OD2 | ASP | A | 181 | 28.059 | 35.814 | 59.630 | 1.00 | 35.53 | A O |
| ATOM | 1177 | C | ASP | A | 181 | 25.724 | 36.419 | 56.403 | 1.00 | 25.40 | A C |
| ATOM | 1178 | O | ASP | A | 181 | 26.934 | 36.579 | 56.291 | 1.00 | 25.40 | A O |
| ATOM | 1179 | N | ILE | A | 182 | 24.851 | 37.009 | 55.614 | 1.00 | 13.99 | A N |
| ATOM | 1180 | CA | ILE | A | 182 | 25.291 | 37.872 | 54.549 | 1.00 | 13.99 | A C |
| ATOM | 1181 | CB | ILE | A | 182 | 24.181 | 38.005 | 53.465 | 1.00 | 18.72 | A C |
| ATOM | 1182 | CG2 | ILE | A | 182 | 24.629 | 38.890 | 52.328 | 1.00 | 18.72 | A C |
| ATOM | 1183 | CG1 | ILE | A | 182 | 23.796 | 36.625 | 52.937 | 1.00 | 18.72 | A C |
| ATOM | 1184 | CD1 | ILE | A | 182 | 24.882 | 35.915 | 52.248 | 1.00 | 18.72 | A C |
| ATOM | 1185 | C | ILE | A | 182 | 25.612 | 39.240 | 55.127 | 1.00 | 13.99 | A C |
| ATOM | 1186 | O | ILE | A | 182 | 24.750 | 39.926 | 55.662 | 1.00 | 13.99 | A O |
| ATOM | 1187 | N | LYS | A | 183 | 26.872 | 39.619 | 55.027 | 1.00 | 17.89 | A N |
| ATOM | 1188 | CA | LYS | A | 183 | 27.315 | 40.918 | 55.477 | 1.00 | 17.89 | A C |
| ATOM | 1189 | CB | LYS | A | 183 | 27.608 | 40.915 | 56.973 | 1.00 | 21.96 | A C |
| ATOM | 1190 | CG | LYS | A | 183 | 28.818 | 40.107 | 57.402 | 1.00 | 21.96 | A C |
| ATOM | 1191 | CD | LYS | A | 183 | 29.061 | 40.316 | 58.882 | 1.00 | 21.96 | A C |
| ATOM | 1192 | CE | LYS | A | 183 | 30.106 | 39.376 | 59.444 | 1.00 | 21.96 | A C |
| ATOM | 1193 | NZ | LYS | A | 183 | 29.630 | 37.972 | 59.469 | 1.00 | 21.96 | A N |
| ATOM | 1194 | C | LYS | A | 183 | 28.573 | 41.228 | 54.680 | 1.00 | 17.89 | A C |
| ATOM | 1195 | O | LYS | A | 183 | 29.283 | 40.327 | 54.252 | 1.00 | 17.89 | A O |
| ATOM | 1196 | N | PRO | A | 184 | 28.860 | 42.512 | 54.464 | 1.00 | 31.37 | A N |
| ATOM | 1197 | CD | PRO | A | 184 | 28.091 | 43.655 | 54.981 | 1.00 | 32.42 | A C |
| ATOM | 1198 | CA | PRO | A | 184 | 30.032 | 42.965 | 53.716 | 1.00 | 31.37 | A C |
| ATOM | 1199 | CB | PRO | A | 184 | 30.135 | 44.421 | 54.118 | 1.00 | 32.42 | A C |
| ATOM | 1200 | CG | PRO | A | 184 | 28.686 | 44.805 | 54.223 | 1.00 | 32.42 | A C |

FIG. 4-19

```
ATOM   1201  C    PRO A 184      31.316  42.181  53.989  1.00 31.37           A  C
ATOM   1202  O    PRO A 184      32.044  41.841  53.057  1.00 31.37           A  O
ATOM   1203  N    GLN A 185      31.592  41.889  55.256  1.00 19.40           A  N
ATOM   1204  CA   GLN A 185      32.801  41.152  55.604  1.00 19.40           A  C
ATOM   1205  CB   GLN A 185      32.901  40.971  57.127  1.00 41.36           A  C
ATOM   1206  CG   GLN A 185      33.123  42.250  57.949  1.00 41.36           A  C
ATOM   1207  CD   GLN A 185      31.918  42.592  58.859  1.00 41.36           A  C
ATOM   1208  OE1  GLN A 185      30.844  43.025  58.383  1.00 41.36           A  O
ATOM   1209  NE2  GLN A 185      32.094  42.382  60.174  1.00 41.36           A  N
ATOM   1210  C    GLN A 185      32.899  39.782  54.932  1.00 19.40           A  C
ATOM   1211  O    GLN A 185      33.984  39.228  54.819  1.00 19.40           A  O
ATOM   1212  N    ASN A 186      31.770  39.244  54.487  1.00 20.13           A  N
ATOM   1213  CA   ASN A 186      31.750  37.934  53.856  1.00 20.13           A  C
ATOM   1214  CB   ASN A 186      30.545  37.118  54.323  1.00 23.76           A  C
ATOM   1215  CG   ASN A 186      30.649  36.709  55.792  1.00 23.76           A  C
ATOM   1216  OD1  ASN A 186      31.687  36.208  56.227  1.00 23.76           A  O
ATOM   1217  ND2  ASN A 186      29.574  36.918  56.555  1.00 23.76           A  N
ATOM   1218  C    ASN A 186      31.731  38.017  52.369  1.00 20.13           A  C
ATOM   1219  O    ASN A 186      31.571  37.004  51.714  1.00 20.13           A  O
ATOM   1220  N    LEU A 187      31.889  39.222  51.837  1.00 17.81           A  N
ATOM   1221  CA   LEU A 187      31.898  39.431  50.399  1.00 17.81           A  C
ATOM   1222  CB   LEU A 187      30.954  40.570  50.027  1.00 13.56           A  C
ATOM   1223  CG   LEU A 187      29.513  40.311  50.442  1.00 13.56           A  C
ATOM   1224  CD1  LEU A 187      28.644  41.444  49.995  1.00 13.56           A  C
ATOM   1225  CD2  LEU A 187      29.055  39.002  49.864  1.00 13.56           A  C
ATOM   1226  C    LEU A 187      33.313  39.747  49.947  1.00 17.81           A  C
ATOM   1227  O    LEU A 187      33.734  40.900  49.945  1.00 17.81           A  O
ATOM   1228  N    LEU A 188      34.053  38.706  49.588  1.00 27.82           A  N
ATOM   1229  CA   LEU A 188      35.423  38.865  49.123  1.00 27.82           A  C
ATOM   1230  CB   LEU A 188      36.181  37.548  49.202  1.00 26.49           A  C
ATOM   1231  CG   LEU A 188      36.049  36.763  50.505  1.00 26.49           A  C
ATOM   1232  CD1  LEU A 188      36.878  35.511  50.366  1.00 26.49           A  C
ATOM   1233  CD2  LEU A 188      36.505  37.584  51.707  1.00 26.49           A  C
ATOM   1234  C    LEU A 188      35.413  39.302  47.680  1.00 27.82           A  C
ATOM   1235  O    LEU A 188      34.557  38.883  46.891  1.00 27.82           A  O
ATOM   1236  N    LEU A 189      36.378  40.131  47.319  1.00 26.97           A  N
ATOM   1237  CA   LEU A 189      36.438  40.571  45.948  1.00 26.97           A  C
ATOM   1238  CB   LEU A 189      35.502  41.764  45.734  1.00 43.18           A  C
ATOM   1239  CG   LEU A 189      35.867  43.147  46.266  1.00 43.18           A  C
ATOM   1240  CD1  LEU A 189      34.581  43.940  46.408  1.00 43.18           A  C
ATOM   1241  CD2  LEU A 189      36.575  43.052  47.607  1.00 43.18           A  C
ATOM   1242  C    LEU A 189      37.840  40.892  45.498  1.00 26.97           A  C
ATOM   1243  O    LEU A 189      38.639  41.454  46.235  1.00 26.97           A  O
ATOM   1244  N    ASP A 190      38.133  40.470  44.280  1.00 33.93           A  N
ATOM   1245  CA   ASP A 190      39.412  40.699  43.648  1.00 33.93           A  C
ATOM   1246  CB   ASP A 190      39.597  39.647  42.557  1.00 47.01           A  C
ATOM   1247  CG   ASP A 190      40.731  39.970  41.607  1.00 47.01           A  C
ATOM   1248  OD1  ASP A 190      41.170  41.152  41.577  1.00 47.01           A  O
ATOM   1249  OD2  ASP A 190      41.159  39.037  40.880  1.00 47.01           A  O
ATOM   1250  C    ASP A 190      39.315  42.105  43.062  1.00 33.93           A  C
ATOM   1251  O    ASP A 190      38.405  42.417  42.302  1.00 33.93           A  O
ATOM   1252  N    PRO A 191      40.245  42.981  43.428  1.00 47.44           A  N
ATOM   1253  CD   PRO A 191      41.327  42.710  44.391  1.00 42.50           A  C
ATOM   1254  CA   PRO A 191      40.285  44.373  42.953  1.00 47.44           A  C
ATOM   1255  CB   PRO A 191      41.392  44.988  43.806  1.00 42.50           A  C
ATOM   1256  CG   PRO A 191      42.297  43.818  44.082  1.00 42.50           A  C
ATOM   1257  C    PRO A 191      40.519  44.577  41.458  1.00 47.44           A  C
ATOM   1258  O    PRO A 191      39.986  45.524  40.860  1.00 47.44           A  O
ATOM   1259  N    ASP A 192      41.312  43.703  40.849  1.00 55.08           A  N
ATOM   1260  CA   ASP A 192      41.564  43.845  39.429  1.00 55.08           A  C
ATOM   1261  CB   ASP A 192      42.885  43.166  39.066  1.00 72.16           A  C
ATOM   1262  CG   ASP A 192      44.079  43.839  39.742  1.00 72.16           A  C
ATOM   1263  OD1  ASP A 192      44.024  45.090  39.892  1.00 72.16           A  O
ATOM   1264  OD2  ASP A 192      45.055  43.127  40.108  1.00 72.16           A  O
ATOM   1265  C    ASP A 192      40.413  43.336  38.564  1.00 55.08           A  C
ATOM   1266  O    ASP A 192      39.873  44.084  37.748  1.00 55.08           A  O
ATOM   1267  N    THR A 193      40.023  42.081  38.764  1.00 36.37           A  N
```

FIG. 4-20

```
ATOM   1268  CA   THR A 193      38.958  41.474  37.983  1.00 36.37      A    C
ATOM   1269  CB   THR A 193      38.959  39.953  38.165  1.00 33.81      A    C
ATOM   1270  OG1  THR A 193      38.771  39.647  39.549  1.00 33.81      A    O
ATOM   1271  CG2  THR A 193      40.281  39.368  37.724  1.00 33.81      A    C
ATOM   1272  C    THR A 193      37.585  41.999  38.347  1.00 36.37      A    C
ATOM   1273  O    THR A 193      36.695  42.001  37.509  1.00 36.37      A    O
ATOM   1274  N    ALA A 194      37.413  42.437  39.592  1.00 29.10      A    N
ATOM   1275  CA   ALA A 194      36.128  42.955  40.068  1.00 29.10      A    C
ATOM   1276  CB   ALA A 194      35.525  43.917  39.052  1.00 21.98      A    C
ATOM   1277  C    ALA A 194      35.133  41.837  40.364  1.00 29.10      A    C
ATOM   1278  O    ALA A 194      33.940  42.095  40.538  1.00 29.10      A    O
ATOM   1279  N    VAL A 195      35.604  40.594  40.423  1.00 43.02      A    N
ATOM   1280  CA   VAL A 195      34.686  39.494  40.702  1.00 43.02      A    C
ATOM   1281  CB   VAL A 195      35.109  38.136  39.996  1.00 25.11      A    C
ATOM   1282  CG1  VAL A 195      36.335  38.336  39.156  1.00 25.11      A    C
ATOM   1283  CG2  VAL A 195      35.300  37.013  41.019  1.00 25.11      A    C
ATOM   1284  C    VAL A 195      34.498  39.284  42.194  1.00 43.02      A    C
ATOM   1285  O    VAL A 195      35.461  39.185  42.941  1.00 43.02      A    O
ATOM   1286  N    LEU A 196      33.241  39.224  42.618  1.00 30.70      A    N
ATOM   1287  CA   LEU A 196      32.917  39.028  44.018  1.00 30.70      A    C
ATOM   1288  CB   LEU A 196      31.612  39.753  44.358  1.00 13.71      A    C
ATOM   1289  CG   LEU A 196      31.145  39.705  45.816  1.00 13.71      A    C
ATOM   1290  CD1  LEU A 196      30.257  40.875  46.110  1.00 13.71      A    C
ATOM   1291  CD2  LEU A 196      30.429  38.423  46.102  1.00 13.71      A    C
ATOM   1292  C    LEU A 196      32.793  37.541  44.306  1.00 30.70      A    C
ATOM   1293  O    LEU A 196      32.419  36.761  43.432  1.00 30.70      A    O
ATOM   1294  N    LYS A 197      33.110  37.149  45.535  1.00 30.89      A    N
ATOM   1295  CA   LYS A 197      33.024  35.751  45.920  1.00 30.89      A    C
ATOM   1296  CB   LYS A 197      34.387  35.074  45.776  1.00 31.44      A    C
ATOM   1297  CG   LYS A 197      34.771  34.688  44.363  1.00 31.44      A    C
ATOM   1298  CD   LYS A 197      36.117  34.008  44.369  1.00 31.44      A    C
ATOM   1299  CE   LYS A 197      36.499  33.537  42.978  1.00 31.44      A    C
ATOM   1300  NZ   LYS A 197      35.583  32.473  42.464  1.00 31.44      A    N
ATOM   1301  C    LYS A 197      32.544  35.587  47.348  1.00 30.89      A    C
ATOM   1302  O    LYS A 197      33.234  35.978  48.273  1.00 30.89      A    O
ATOM   1303  N    LEU A 198      31.380  34.979  47.525  1.00 23.21      A    N
ATOM   1304  CA   LEU A 198      30.812  34.776  48.851  1.00 23.21      A    C
ATOM   1305  CB   LEU A 198      29.400  34.217  48.736  1.00 24.78      A    C
ATOM   1306  CG   LEU A 198      28.353  34.690  49.745  1.00 24.78      A    C
ATOM   1307  CD1  LEU A 198      27.231  33.663  49.819  1.00 24.78      A    C
ATOM   1308  CD2  LEU A 198      28.974  34.885  51.103  1.00 24.78      A    C
ATOM   1309  C    LEU A 198      31.640  33.796  49.651  1.00 23.21      A    C
ATOM   1310  O    LEU A 198      32.118  32.811  49.111  1.00 23.21      A    O
ATOM   1311  N    CYS A 199      31.803  34.053  50.940  1.00 18.42      A    N
ATOM   1312  CA   CYS A 199      32.569  33.140  51.776  1.00 18.42      A    C
ATOM   1313  CB   CYS A 199      34.018  33.614  51.919  1.00 22.44      A    C
ATOM   1314  SG   CYS A 199      34.285  35.202  52.689  1.00 22.44      A    S
ATOM   1315  C    CYS A 199      31.944  33.018  53.148  1.00 18.42      A    C
ATOM   1316  O    CYS A 199      30.954  33.676  53.433  1.00 18.42      A    O
ATOM   1317  N    ASP A 200      32.519  32.152  53.980  1.00 34.83      A    N
ATOM   1318  CA   ASP A 200      32.057  31.936  55.350  1.00 34.83      A    C
ATOM   1319  CB   ASP A 200      31.980  33.266  56.082  1.00 37.26      A    C
ATOM   1320  CG   ASP A 200      32.197  33.118  57.555  1.00 37.26      A    C
ATOM   1321  OD1  ASP A 200      31.851  32.027  58.069  1.00 37.26      A    O
ATOM   1322  OD2  ASP A 200      32.702  34.088  58.176  1.00 37.26      A    O
ATOM   1323  C    ASP A 200      30.708  31.254  55.465  1.00 34.83      A    C
ATOM   1324  O    ASP A 200      29.732  31.883  55.866  1.00 34.83      A    O
ATOM   1325  N    PHE A 201      30.647  29.972  55.131  1.00 31.27      A    N
ATOM   1326  CA   PHE A 201      29.386  29.251  55.214  1.00 31.27      A    C
ATOM   1327  CB   PHE A 201      29.253  28.277  54.040  1.00 21.48      A    C
ATOM   1328  CG   PHE A 201      29.143  28.960  52.708  1.00 21.48      A    C
ATOM   1329  CD1  PHE A 201      30.245  29.580  52.134  1.00 21.48      A    C
ATOM   1330  CD2  PHE A 201      27.932  29.011  52.037  1.00 21.48      A    C
ATOM   1331  CE1  PHE A 201      30.140  30.246  50.900  1.00 21.48      A    C
ATOM   1332  CE2  PHE A 201      27.819  29.674  50.806  1.00 21.48      A    C
ATOM   1333  CZ   PHE A 201      28.926  30.291  50.240  1.00 21.48      A    C
ATOM   1334  C    PHE A 201      29.292  28.518  56.542  1.00 31.27      A    C
```

FIG. 4-21

```
ATOM   1335  O    PHE A 201      28.580  27.522  56.673  1.00 31.27      A    O
ATOM   1336  N    GLY A 202      30.011  29.047  57.527  1.00 24.98      A    N
ATOM   1337  CA   GLY A 202      30.021  28.470  58.855  1.00 24.98      A    C
ATOM   1338  C    GLY A 202      28.655  28.488  59.502  1.00 24.98      A    C
ATOM   1339  O    GLY A 202      28.422  27.773  60.471  1.00 24.98      A    O
ATOM   1340  N    SER A 203      27.749  29.299  58.969  1.00 25.88      A    N
ATOM   1341  CA   SER A 203      26.398  29.391  59.502  1.00 25.88      A    C
ATOM   1342  CB   SER A 203      26.079  30.842  59.839  1.00 34.02      A    C
ATOM   1343  OG   SER A 203      26.962  31.317  60.839  1.00 34.02      A    O
ATOM   1344  C    SER A 203      25.375  28.842  58.515  1.00 25.88      A    C
ATOM   1345  O    SER A 203      24.217  28.639  58.856  1.00 25.88      A    O
ATOM   1346  N    ALA A 204      25.811  28.594  57.286  1.00 23.03      A    N
ATOM   1347  CA   ALA A 204      24.922  28.077  56.263  1.00 23.03      A    C
ATOM   1348  CB   ALA A 204      25.681  27.861  54.971  1.00  9.35      A    C
ATOM   1349  C    ALA A 204      24.288  26.777  56.701  1.00 23.03      A    C
ATOM   1350  O    ALA A 204      24.912  25.948  57.346  1.00 23.03      A    O
ATOM   1351  N    LYS A 205      23.035  26.611  56.328  1.00 25.13      A    N
ATOM   1352  CA   LYS A 205      22.295  25.421  56.651  1.00 25.13      A    C
ATOM   1353  CB   LYS A 205      21.654  25.568  58.017  1.00 32.01      A    C
ATOM   1354  CG   LYS A 205      20.949  24.311  58.461  1.00 32.01      A    C
ATOM   1355  CD   LYS A 205      20.035  24.539  59.645  1.00 32.01      A    C
ATOM   1356  CE   LYS A 205      19.320  23.258  60.014  1.00 32.01      A    C
ATOM   1357  NZ   LYS A 205      18.427  23.425  61.188  1.00 32.01      A    N
ATOM   1358  C    LYS A 205      21.208  25.235  55.604  1.00 25.13      A    C
ATOM   1359  O    LYS A 205      20.733  26.185  54.989  1.00 25.13      A    O
ATOM   1360  N    GLN A 206      20.823  23.986  55.417  1.00 35.29      A    N
ATOM   1361  CA   GLN A 206      19.786  23.598  54.489  1.00 35.29      A    C
ATOM   1362  CB   GLN A 206      20.024  22.129  54.149  1.00 47.39      A    C
ATOM   1363  CG   GLN A 206      18.804  21.366  53.686  1.00 47.39      A    C
ATOM   1364  CD   GLN A 206      18.940  20.851  52.269  1.00 47.39      A    C
ATOM   1365  OE1  GLN A 206      17.984  20.307  51.702  1.00 47.39      A    O
ATOM   1366  NE2  GLN A 206      20.133  21.014  51.684  1.00 47.39      A    N
ATOM   1367  C    GLN A 206      18.449  23.791  55.209  1.00 35.29      A    C
ATOM   1368  O    GLN A 206      18.184  23.121  56.203  1.00 35.29      A    O
ATOM   1369  N    LEU A 207      17.619  24.714  54.737  1.00 24.64      A    N
ATOM   1370  CA   LEU A 207      16.331  24.935  55.379  1.00 24.64      A    C
ATOM   1371  CB   LEU A 207      15.896  26.383  55.223  1.00 18.39      A    C
ATOM   1372  CG   LEU A 207      16.883  27.445  55.711  1.00 18.39      A    C
ATOM   1373  CD1  LEU A 207      16.117  28.749  55.914  1.00 18.39      A    C
ATOM   1374  CD2  LEU A 207      17.554  27.013  57.017  1.00 18.39      A    C
ATOM   1375  C    LEU A 207      15.288  24.008  54.776  1.00 24.64      A    C
ATOM   1376  O    LEU A 207      15.199  23.863  53.560  1.00 24.64      A    O
ATOM   1377  N    VAL A 208      14.515  23.360  55.633  1.00 40.58      A    N
ATOM   1378  CA   VAL A 208      13.471  22.444  55.186  1.00 40.58      A    C
ATOM   1379  CB   VAL A 208      13.775  21.008  55.627  1.00 25.52      A    C
ATOM   1380  CG1  VAL A 208      12.647  20.088  55.211  1.00 25.52      A    C
ATOM   1381  CG2  VAL A 208      15.089  20.559  55.043  1.00 25.52      A    C
ATOM   1382  C    VAL A 208      12.143  22.846  55.819  1.00 40.58      A    C
ATOM   1383  O    VAL A 208      12.025  22.884  57.045  1.00 40.58      A    O
ATOM   1384  N    ARG A 209      11.142  23.131  54.996  1.00 44.30      A    N
ATOM   1385  CA   ARG A 209       9.852  23.544  55.525  1.00 44.30      A    C
ATOM   1386  CB   ARG A 209       8.789  23.492  54.440  1.00 68.10      A    C
ATOM   1387  CG   ARG A 209       7.703  24.557  54.561  1.00 68.10      A    C
ATOM   1388  CD   ARG A 209       6.814  24.523  53.312  1.00 68.10      A    C
ATOM   1389  NE   ARG A 209       7.591  24.132  52.124  1.00 68.10      A    N
ATOM   1390  CZ   ARG A 209       7.088  23.897  50.907  1.00 68.10      A    C
ATOM   1391  NH1  ARG A 209       5.781  24.015  50.676  1.00 68.10      A    N
ATOM   1392  NH2  ARG A 209       7.898  23.507  49.919  1.00 68.10      A    N
ATOM   1393  C    ARG A 209       9.487  22.598  56.644  1.00 44.30      A    C
ATOM   1394  O    ARG A 209       9.804  21.406  56.581  1.00 44.30      A    O
ATOM   1395  N    GLY A 210       8.848  23.140  57.677  1.00 51.16      A    N
ATOM   1396  CA   GLY A 210       8.452  22.331  58.816  1.00 51.16      A    C
ATOM   1397  C    GLY A 210       9.532  22.180  59.880  1.00 51.16      A    C
ATOM   1398  O    GLY A 210       9.245  21.870  61.049  1.00 51.16      A    O
ATOM   1399  N    GLU A 211      10.785  22.381  59.484  1.00 50.56      A    N
ATOM   1400  CA   GLU A 211      11.889  22.279  60.438  1.00 50.56      A    C
ATOM   1401  CB   GLU A 211      13.151  21.748  59.771  1.00 70.61      A    C
```

FIG. 4-22

```
ATOM   1402  CG   GLU A 211     13.328  20.248  59.918  1.00 70.61      A  C
ATOM   1403  CD   GLU A 211     14.531  19.738  59.130  1.00 70.61      A  C
ATOM   1404  OE1  GLU A 211     14.886  18.531  59.289  1.00 70.61      A  O
ATOM   1405  OE2  GLU A 211     15.097  20.563  58.355  1.00 70.61      A  O
ATOM   1406  C    GLU A 211     12.165  23.644  61.023  1.00 50.56      A  C
ATOM   1407  O    GLU A 211     12.222  24.625  60.315  1.00 50.56      A  O
ATOM   1408  N    PRO A 212     12.328  23.722  62.335  1.00 43.08      A  N
ATOM   1409  CD   PRO A 212     12.145  22.652  63.327  1.00 38.80      A  C
ATOM   1410  CA   PRO A 212     12.591  24.998  62.990  1.00 43.08      A  C
ATOM   1411  CB   PRO A 212     12.034  24.762  64.385  1.00 38.80      A  C
ATOM   1412  CG   PRO A 212     12.456  23.364  64.638  1.00 38.80      A  C
ATOM   1413  C    PRO A 212     14.090  25.243  62.979  1.00 43.08      A  C
ATOM   1414  O    PRO A 212     14.870  24.285  62.940  1.00 43.08      A  O
ATOM   1415  N    ASN A 213     14.490  26.512  62.993  1.00 40.58      A  N
ATOM   1416  CA   ASN A 213     15.908  26.856  63.005  1.00 40.58      A  C
ATOM   1417  CB   ASN A 213     16.359  27.262  61.616  1.00 25.80      A  C
ATOM   1418  CG   ASN A 213     16.174  26.165  60.624  1.00 25.80      A  C
ATOM   1419  OD1  ASN A 213     16.940  25.205  60.597  1.00 25.80      A  O
ATOM   1420  ND2  ASN A 213     15.137  26.281  59.808  1.00 25.80      A  N
ATOM   1421  C    ASN A 213     16.197  27.985  63.980  1.00 40.58      A  C
ATOM   1422  O    ASN A 213     15.360  28.864  64.194  1.00 40.58      A  O
ATOM   1423  N    VAL A 214     17.387  27.956  64.570  1.00 21.29      A  N
ATOM   1424  CA   VAL A 214     17.781  28.972  65.531  1.00 21.29      A  C
ATOM   1425  CB   VAL A 214     19.212  28.741  65.994  1.00 19.26      A  C
ATOM   1426  CG1  VAL A 214     19.324  27.364  66.600  1.00 19.26      A  C
ATOM   1427  CG2  VAL A 214     20.172  28.911  64.814  1.00 19.26      A  C
ATOM   1428  C    VAL A 214     17.664  30.387  64.966  1.00 21.29      A  C
ATOM   1429  O    VAL A 214     18.009  30.645  63.814  1.00 21.29      A  O
ATOM   1430  N    SER A 215     17.195  31.314  65.788  1.00 31.77      A  N
ATOM   1431  CA   SER A 215     17.023  32.677  65.324  1.00 31.77      A  C
ATOM   1432  CB   SER A 215     15.637  33.211  65.737  1.00 43.62      A  C
ATOM   1433  OG   SER A 215     15.265  32.797  67.041  1.00 43.62      A  O
ATOM   1434  C    SER A 215     18.115  33.628  65.778  1.00 31.77      A  C
ATOM   1435  O    SER A 215     17.931  34.839  65.733  1.00 31.77      A  O
ATOM   1436  N    TYR A 216     19.242  33.094  66.231  1.00 28.27      A  N
ATOM   1437  CA   TYR A 216     20.354  33.956  66.638  1.00 28.27      A  C
ATOM   1438  CB   TYR A 216     20.781  33.656  68.073  1.00 26.32      A  C
ATOM   1439  CG   TYR A 216     20.927  32.201  68.375  1.00 26.32      A  C
ATOM   1440  CD1  TYR A 216     21.967  31.460  67.832  1.00 26.32      A  C
ATOM   1441  CE1  TYR A 216     22.095  30.115  68.101  1.00 26.32      A  C
ATOM   1442  CD2  TYR A 216     20.013  31.556  69.200  1.00 26.32      A  C
ATOM   1443  CE2  TYR A 216     20.128  30.205  69.478  1.00 26.32      A  C
ATOM   1444  CZ   TYR A 216     21.171  29.491  68.924  1.00 26.32      A  C
ATOM   1445  OH   TYR A 216     21.277  28.148  69.186  1.00 26.32      A  O
ATOM   1446  C    TYR A 216     21.549  33.802  65.682  1.00 28.27      A  C
ATOM   1447  O    TYR A 216     22.714  33.869  66.090  1.00 28.27      A  O
ATOM   1448  N    ILE A 217     21.246  33.652  64.391  1.00 38.24      A  N
ATOM   1449  CA   ILE A 217     22.282  33.421  63.401  1.00 38.24      A  C
ATOM   1450  CB   ILE A 217     21.890  32.306  62.401  1.00 46.69      A  C
ATOM   1451  CG2  ILE A 217     22.395  30.983  62.889  1.00 46.69      A  C
ATOM   1452  CG1  ILE A 217     20.388  32.344  62.136  1.00 46.69      A  C
ATOM   1453  CD1  ILE A 217     19.893  33.732  61.745  1.00 46.69      A  C
ATOM   1454  C    ILE A 217     22.859  34.536  62.543  1.00 38.24      A  C
ATOM   1455  O    ILE A 217     24.016  34.450  62.120  1.00 38.24      A  O
ATOM   1456  N    CYS A 218     22.099  35.573  62.253  1.00 24.43      A  N
ATOM   1457  CA   CYS A 218     22.663  36.597  61.383  1.00 24.43      A  C
ATOM   1458  CB   CYS A 218     21.532  37.186  60.547  1.00 25.90      A  C
ATOM   1459  SG   CYS A 218     22.011  38.102  59.142  1.00 25.90      A  S
ATOM   1460  C    CYS A 218     23.346  37.690  62.197  1.00 24.43      A  C
ATOM   1461  O    CYS A 218     23.021  37.883  63.362  1.00 24.43      A  O
ATOM   1462  N    SER A 219     24.276  38.413  61.580  1.00 25.88      A  N
ATOM   1463  CA   SER A 219     25.015  39.480  62.258  1.00 25.88      A  C
ATOM   1464  CB   SER A 219     26.317  39.764  61.513  1.00 38.59      A  C
ATOM   1465  OG   SER A 219     27.147  38.613  61.525  1.00 38.59      A  O
ATOM   1466  C    SER A 219     24.227  40.775  62.424  1.00 25.88      A  C
ATOM   1467  O    SER A 219     23.325  41.057  61.660  1.00 25.88      A  O
ATOM   1468  N    ALA A 220     24.583  41.558  63.434  1.00 43.88      A  N
```

FIG. 4-23

| | | | | | | | | | | |
|---|---|---|---|---|---|---|---|---|---|---|
| ATOM | 1469 | CA | ALA | A | 220 | 23.903 | 42.819 | 63.721 | 1.00 43.88 | A C |
| ATOM | 1470 | CB | ALA | A | 220 | 24.509 | 43.469 | 64.973 | 1.00 46.88 | A C |
| ATOM | 1471 | C | ALA | A | 220 | 23.987 | 43.777 | 62.542 | 1.00 43.88 | A C |
| ATOM | 1472 | O | ALA | A | 220 | 25.028 | 43.888 | 61.885 | 1.00 43.88 | A O |
| ATOM | 1473 | N | TYR | A | 221 | 22.887 | 44.480 | 62.295 | 1.00 28.11 | A N |
| ATOM | 1474 | CA | TYR | A | 221 | 22.791 | 45.444 | 61.197 | 1.00 28.11 | A C |
| ATOM | 1475 | CB | TYR | A | 221 | 24.151 | 46.093 | 60.874 | 1.00 42.62 | A C |
| ATOM | 1476 | CG | TYR | A | 221 | 24.748 | 47.007 | 61.942 | 1.00 42.62 | A C |
| ATOM | 1477 | CD1 | TYR | A | 221 | 24.168 | 47.134 | 63.209 | 1.00 42.62 | A C |
| ATOM | 1478 | CE1 | TYR | A | 221 | 24.760 | 47.944 | 64.195 | 1.00 42.62 | A C |
| ATOM | 1479 | CD2 | TYR | A | 221 | 25.932 | 47.717 | 61.689 | 1.00 42.62 | A C |
| ATOM | 1480 | CE2 | TYR | A | 221 | 26.526 | 48.521 | 62.661 | 1.00 42.62 | A C |
| ATOM | 1481 | CZ | TYR | A | 221 | 25.938 | 48.629 | 63.907 | 1.00 42.62 | A C |
| ATOM | 1482 | OH | TYR | A | 221 | 26.532 | 49.413 | 64.868 | 1.00 42.62 | A O |
| ATOM | 1483 | C | TYR | A | 221 | 22.234 | 44.833 | 59.913 | 1.00 28.11 | A C |
| ATOM | 1484 | O | TYR | A | 221 | 21.744 | 45.556 | 59.048 | 1.00 28.11 | A O |
| ATOM | 1485 | N | TYR | A | 222 | 22.290 | 43.511 | 59.797 | 1.00 26.75 | A N |
| ATOM | 1486 | CA | TYR | A | 222 | 21.816 | 42.843 | 58.590 | 1.00 26.75 | A C |
| ATOM | 1487 | CB | TYR | A | 222 | 23.004 | 42.233 | 57.864 | 1.00 17.88 | A C |
| ATOM | 1488 | CG | TYR | A | 222 | 24.135 | 43.207 | 57.694 | 1.00 17.88 | A C |
| ATOM | 1489 | CD1 | TYR | A | 222 | 24.167 | 44.085 | 56.620 | 1.00 17.88 | A C |
| ATOM | 1490 | CE1 | TYR | A | 222 | 25.191 | 45.019 | 56.496 | 1.00 17.88 | A C |
| ATOM | 1491 | CD2 | TYR | A | 222 | 25.152 | 43.286 | 58.640 | 1.00 17.88 | A C |
| ATOM | 1492 | CE2 | TYR | A | 222 | 26.175 | 44.220 | 58.525 | 1.00 17.88 | A C |
| ATOM | 1493 | CZ | TYR | A | 222 | 26.190 | 45.080 | 57.456 | 1.00 17.88 | A C |
| ATOM | 1494 | OH | TYR | A | 222 | 27.198 | 46.005 | 57.368 | 1.00 17.88 | A O |
| ATOM | 1495 | C | TYR | A | 222 | 20.786 | 41.755 | 58.825 | 1.00 26.75 | A C |
| ATOM | 1496 | O | TYR | A | 222 | 20.453 | 41.016 | 57.901 | 1.00 26.75 | A O |
| ATOM | 1497 | N | ARG | A | 223 | 20.279 | 41.660 | 60.049 | 1.00 16.93 | A N |
| ATOM | 1498 | CA | ARG | A | 223 | 19.306 | 40.636 | 60.381 | 1.00 16.93 | A C |
| ATOM | 1499 | CB | ARG | A | 223 | 19.281 | 40.410 | 61.887 | 1.00 37.89 | A C |
| ATOM | 1500 | CG | ARG | A | 223 | 20.648 | 40.515 | 62.523 | 1.00 37.89 | A C |
| ATOM | 1501 | CD | ARG | A | 223 | 20.613 | 40.249 | 64.030 | 1.00 37.89 | A C |
| ATOM | 1502 | NE | ARG | A | 223 | 20.373 | 38.836 | 64.299 | 1.00 37.89 | A N |
| ATOM | 1503 | CZ | ARG | A | 223 | 19.289 | 38.364 | 64.897 | 1.00 37.89 | A C |
| ATOM | 1504 | NH1 | ARG | A | 223 | 18.339 | 39.196 | 65.300 | 1.00 37.89 | A N |
| ATOM | 1505 | NH2 | ARG | A | 223 | 19.156 | 37.057 | 65.079 | 1.00 37.89 | A N |
| ATOM | 1506 | C | ARG | A | 223 | 17.927 | 41.036 | 59.907 | 1.00 16.93 | A C |
| ATOM | 1507 | O | ARG | A | 223 | 17.519 | 42.174 | 60.074 | 1.00 16.93 | A O |
| ATOM | 1508 | N | ALA | A | 224 | 17.221 | 40.092 | 59.298 | 1.00 35.15 | A N |
| ATOM | 1509 | CA | ALA | A | 224 | 15.867 | 40.329 | 58.809 | 1.00 35.15 | A C |
| ATOM | 1510 | CB | ALA | A | 224 | 15.375 | 39.118 | 58.039 | 1.00 39.28 | A C |
| ATOM | 1511 | C | ALA | A | 224 | 14.952 | 40.594 | 60.000 | 1.00 35.15 | A C |
| ATOM | 1512 | O | ALA | A | 224 | 15.215 | 40.123 | 61.099 | 1.00 35.15 | A O |
| ATOM | 1513 | N | PRO | A | 225 | 13.862 | 41.349 | 59.798 | 1.00 29.83 | A N |
| ATOM | 1514 | CD | PRO | A | 225 | 13.372 | 41.930 | 58.540 | 1.00 20.02 | A C |
| ATOM | 1515 | CA | PRO | A | 225 | 12.940 | 41.646 | 60.897 | 1.00 29.83 | A C |
| ATOM | 1516 | CB | PRO | A | 225 | 11.792 | 42.367 | 60.203 | 1.00 20.02 | A C |
| ATOM | 1517 | CG | PRO | A | 225 | 12.445 | 42.997 | 59.039 | 1.00 20.02 | A C |
| ATOM | 1518 | C | PRO | A | 225 | 12.447 | 40.397 | 61.624 | 1.00 29.83 | A C |
| ATOM | 1519 | O | PRO | A | 225 | 12.275 | 40.414 | 62.841 | 1.00 29.83 | A O |
| ATOM | 1520 | N | GLU | A | 226 | 12.213 | 39.391 | 60.876 | 1.00 29.64 | A N |
| ATOM | 1521 | CA | GLU | A | 226 | 11.718 | 38.073 | 61.464 | 1.00 29.64 | A C |
| ATOM | 1522 | CB | GLU | A | 226 | 11.486 | 36.994 | 60.403 | 1.00 40.23 | A C |
| ATOM | 1523 | CG | GLU | A | 226 | 10.982 | 37.480 | 59.077 | 1.00 40.23 | A C |
| ATOM | 1524 | CD | GLU | A | 226 | 12.107 | 37.849 | 58.138 | 1.00 40.23 | A C |
| ATOM | 1525 | OE1 | GLU | A | 226 | 12.788 | 36.930 | 57.617 | 1.00 40.23 | A O |
| ATOM | 1526 | OE2 | GLU | A | 226 | 12.306 | 39.065 | 57.932 | 1.00 40.23 | A O |
| ATOM | 1527 | C | GLU | A | 226 | 12.738 | 37.526 | 62.449 | 1.00 29.64 | A C |
| ATOM | 1528 | O | GLU | A | 226 | 12.408 | 37.133 | 63.576 | 1.00 29.64 | A O |
| ATOM | 1529 | N | LEU | A | 227 | 13.983 | 37.467 | 61.993 | 1.00 35.73 | A N |
| ATOM | 1530 | CA | LEU | A | 227 | 15.055 | 36.985 | 62.838 | 1.00 35.73 | A C |
| ATOM | 1531 | CB | LEU | A | 227 | 16.409 | 37.172 | 62.142 | 1.00 16.70 | A C |
| ATOM | 1532 | CG | LEU | A | 227 | 16.693 | 36.265 | 60.942 | 1.00 16.70 | A C |
| ATOM | 1533 | CD1 | LEU | A | 227 | 18.105 | 36.492 | 60.450 | 1.00 16.70 | A C |
| ATOM | 1534 | CD2 | LEU | A | 227 | 16.508 | 34.807 | 61.345 | 1.00 16.70 | A C |
| ATOM | 1535 | C | LEU | A | 227 | 15.048 | 37.713 | 64.181 | 1.00 35.73 | A C |

FIG. 4-24

```
ATOM   1536  O    LEU A 227      15.283  37.101  65.214  1.00 35.73      A    O
ATOM   1537  N    ILE A 228      14.770  39.015  64.153  1.00 25.39      A    N
ATOM   1538  CA   ILE A 228      14.738  39.854  65.344  1.00 25.39      A    C
ATOM   1539  CB   ILE A 228      14.704  41.342  64.953  1.00 15.89      A    C
ATOM   1540  CG2  ILE A 228      14.482  42.199  66.165  1.00 15.89      A    C
ATOM   1541  CG1  ILE A 228      16.013  41.723  64.264  1.00 15.89      A    C
ATOM   1542  CD1  ILE A 228      16.019  43.124  63.683  1.00 15.89      A    C
ATOM   1543  C    ILE A 228      13.521  39.536  66.184  1.00 25.39      A    C
ATOM   1544  O    ILE A 228      13.539  39.718  67.397  1.00 25.39      A    O
ATOM   1545  N    PHE A 229      12.461  39.063  65.531  1.00 29.84      A    N
ATOM   1546  CA   PHE A 229      11.228  38.705  66.229  1.00 29.84      A    C
ATOM   1547  CB   PHE A 229      10.029  38.842  65.297  1.00 31.67      A    C
ATOM   1548  CG   PHE A 229       9.498  40.228  65.212  1.00 31.67      A    C
ATOM   1549  CD1  PHE A 229       8.940  40.837  66.324  1.00 31.67      A    C
ATOM   1550  CD2  PHE A 229       9.580  40.942  64.033  1.00 31.67      A    C
ATOM   1551  CE1  PHE A 229       8.480  42.133  66.265  1.00 31.67      A    C
ATOM   1552  CE2  PHE A 229       9.118  42.250  63.969  1.00 31.67      A    C
ATOM   1553  CZ   PHE A 229       8.568  42.842  65.090  1.00 31.67      A    C
ATOM   1554  C    PHE A 229      11.295  37.278  66.767  1.00 29.84      A    C
ATOM   1555  O    PHE A 229      10.298  36.730  67.254  1.00 29.84      A    O
ATOM   1556  N    GLY A 230      12.472  36.676  66.659  1.00 36.74      A    N
ATOM   1557  CA   GLY A 230      12.656  35.335  67.174  1.00 36.74      A    C
ATOM   1558  C    GLY A 230      12.022  34.228  66.357  1.00 36.74      A    C
ATOM   1559  O    GLY A 230      11.994  33.081  66.799  1.00 36.74      A    O
ATOM   1560  N    ALA A 231      11.516  34.551  65.169  1.00 22.97      A    N
ATOM   1561  CA   ALA A 231      10.899  33.525  64.331  1.00 22.97      A    C
ATOM   1562  CB   ALA A 231      10.503  34.108  62.985  1.00 11.00      A    C
ATOM   1563  C    ALA A 231      11.878  32.377  64.133  1.00 22.97      A    C
ATOM   1564  O    ALA A 231      13.093  32.578  64.129  1.00 22.97      A    O
ATOM   1565  N    THR A 232      11.352  31.166  63.983  1.00 28.56      A    N
ATOM   1566  CA   THR A 232      12.216  30.011  63.781  1.00 28.56      A    C
ATOM   1567  CB   THR A 232      12.174  29.074  64.979  1.00 29.30      A    C
ATOM   1568  OG1  THR A 232      10.865  28.512  65.094  1.00 29.30      A    O
ATOM   1569  CG2  THR A 232      12.523  29.832  66.250  1.00 29.30      A    C
ATOM   1570  C    THR A 232      11.831  29.233  62.532  1.00 28.56      A    C
ATOM   1571  O    THR A 232      12.387  28.165  62.244  1.00 28.56      A    O
ATOM   1572  N    ASP A 233      10.880  29.789  61.790  1.00 25.06      A    N
ATOM   1573  CA   ASP A 233      10.403  29.185  60.552  1.00 25.06      A    C
ATOM   1574  CB   ASP A 233       8.897  28.980  60.633  1.00 35.46      A    C
ATOM   1575  CG   ASP A 233       8.148  30.290  60.782  1.00 35.46      A    C
ATOM   1576  OD1  ASP A 233       8.807  31.351  60.833  1.00 35.46      A    O
ATOM   1577  OD2  ASP A 233       6.902  30.259  60.854  1.00 35.46      A    O
ATOM   1578  C    ASP A 233      10.721  30.106  59.372  1.00 25.06      A    C
ATOM   1579  O    ASP A 233       9.965  30.177  58.397  1.00 25.06      A    O
ATOM   1580  N    TYR A 234      11.837  30.817  59.473  1.00 23.49      A    N
ATOM   1581  CA   TYR A 234      12.241  31.728  58.421  1.00 23.49      A    C
ATOM   1582  CB   TYR A 234      13.345  32.661  58.933  1.00 19.44      A    C
ATOM   1583  CG   TYR A 234      14.538  31.961  59.532  1.00 19.44      A    C
ATOM   1584  CD1  TYR A 234      15.641  31.634  58.751  1.00 19.44      A    C
ATOM   1585  CE1  TYR A 234      16.755  31.009  59.308  1.00 19.44      A    C
ATOM   1586  CD2  TYR A 234      14.574  31.639  60.887  1.00 19.44      A    C
ATOM   1587  CE2  TYR A 234      15.675  31.017  61.450  1.00 19.44      A    C
ATOM   1588  CZ   TYR A 234      16.762  30.707  60.656  1.00 19.44      A    C
ATOM   1589  OH   TYR A 234      17.866  30.106  61.202  1.00 19.44      A    O
ATOM   1590  C    TYR A 234      12.693  30.958  57.184  1.00 23.49      A    C
ATOM   1591  O    TYR A 234      13.073  29.791  57.263  1.00 23.49      A    O
ATOM   1592  N    THR A 235      12.625  31.621  56.037  1.00 31.88      A    N
ATOM   1593  CA   THR A 235      13.027  31.018  54.777  1.00 31.88      A    C
ATOM   1594  CB   THR A 235      11.939  31.150  53.726  1.00 18.71      A    C
ATOM   1595  OG1  THR A 235      11.818  32.523  53.342  1.00 18.71      A    O
ATOM   1596  CG2  THR A 235      10.629  30.677  54.272  1.00 18.71      A    C
ATOM   1597  C    THR A 235      14.265  31.697  54.223  1.00 31.88      A    C
ATOM   1598  O    THR A 235      14.741  32.681  54.773  1.00 31.88      A    O
ATOM   1599  N    SER A 236      14.788  31.181  53.121  1.00 30.52      A    N
ATOM   1600  CA   SER A 236      15.979  31.780  52.529  1.00 30.52      A    C
ATOM   1601  CB   SER A 236      16.323  31.083  51.220  1.00 26.32      A    C
ATOM   1602  OG   SER A 236      16.803  29.781  51.472  1.00 26.32      A    O
```

FIG. 4-25

```
ATOM   1603  C    SER A 236      15.845  33.277  52.276  1.00 30.52      A  C
ATOM   1604  O    SER A 236      16.827  33.955  52.006  1.00 30.52      A  O
ATOM   1605  N    SER A 237      14.630  33.796  52.358  1.00 26.49      A  N
ATOM   1606  CA   SER A 237      14.422  35.206  52.118  1.00 26.49      A  C
ATOM   1607  CB   SER A 237      12.940  35.541  52.173  1.00 46.05      A  C
ATOM   1608  OG   SER A 237      12.346  35.074  53.370  1.00 46.05      A  O
ATOM   1609  C    SER A 237      15.178  36.048  53.114  1.00 26.49      A  C
ATOM   1610  O    SER A 237      15.258  37.259  52.944  1.00 26.49      A  O
ATOM   1611  N    ILE A 238      15.734  35.421  54.150  1.00 26.16      A  N
ATOM   1612  CA   ILE A 238      16.480  36.198  55.131  1.00 26.16      A  C
ATOM   1613  CB   ILE A 238      16.822  35.419  56.418  1.00 27.50      A  C
ATOM   1614  CG2  ILE A 238      15.574  34.799  56.998  1.00 27.50      A  C
ATOM   1615  CG1  ILE A 238      17.894  34.377  56.138  1.00 27.50      A  C
ATOM   1616  CD1  ILE A 238      18.581  33.887  57.392  1.00 27.50      A  C
ATOM   1617  C    ILE A 238      17.764  36.721  54.498  1.00 26.16      A  C
ATOM   1618  O    ILE A 238      18.208  37.825  54.804  1.00 26.16      A  O
ATOM   1619  N    ASP A 239      18.346  35.932  53.601  1.00 17.20      A  N
ATOM   1620  CA   ASP A 239      19.557  36.334  52.905  1.00 17.20      A  C
ATOM   1621  CB   ASP A 239      20.103  35.197  52.046  1.00 29.89      A  C
ATOM   1622  CG   ASP A 239      20.864  34.170  52.846  1.00 29.89      A  C
ATOM   1623  OD1  ASP A 239      21.323  34.485  53.965  1.00 29.89      A  O
ATOM   1624  OD2  ASP A 239      21.021  33.044  52.340  1.00 29.89      A  O
ATOM   1625  C    ASP A 239      19.254  37.507  52.003  1.00 17.20      A  C
ATOM   1626  O    ASP A 239      20.038  38.436  51.924  1.00 17.20      A  O
ATOM   1627  N    VAL A 240      18.118  37.466  51.319  1.00 21.44      A  N
ATOM   1628  CA   VAL A 240      17.761  38.547  50.415  1.00 21.44      A  C
ATOM   1629  CB   VAL A 240      16.436  38.253  49.693  1.00 11.49      A  C
ATOM   1630  CG1  VAL A 240      16.025  39.442  48.818  1.00 11.49      A  C
ATOM   1631  CG2  VAL A 240      16.606  37.007  48.846  1.00 11.49      A  C
ATOM   1632  C    VAL A 240      17.666  39.862  51.164  1.00 21.44      A  C
ATOM   1633  O    VAL A 240      18.063  40.907  50.649  1.00 21.44      A  O
ATOM   1634  N    TRP A 241      17.163  39.793  52.394  1.00 26.09      A  N
ATOM   1635  CA   TRP A 241      17.010  40.978  53.226  1.00 26.09      A  C
ATOM   1636  CB   TRP A 241      16.330  40.624  54.553  1.00 20.95      A  C
ATOM   1637  CG   TRP A 241      16.293  41.764  55.537  1.00 20.95      A  C
ATOM   1638  CD2  TRP A 241      15.248  42.732  55.700  1.00 20.95      A  C
ATOM   1639  CE2  TRP A 241      15.668  43.636  56.696  1.00 20.95      A  C
ATOM   1640  CE3  TRP A 241      13.992  42.919  55.104  1.00 20.95      A  C
ATOM   1641  CD1  TRP A 241      17.275  42.116  56.412  1.00 20.95      A  C
ATOM   1642  NE1  TRP A 241      16.911  43.238  57.110  1.00 20.95      A  N
ATOM   1643  CZ2  TRP A 241      14.890  44.719  57.103  1.00 20.95      A  C
ATOM   1644  CZ3  TRP A 241      13.213  44.000  55.511  1.00 20.95      A  C
ATOM   1645  CH2  TRP A 241      13.666  44.883  56.505  1.00 20.95      A  C
ATOM   1646  C    TRP A 241      18.379  41.543  53.502  1.00 26.09      A  C
ATOM   1647  O    TRP A 241      18.646  42.720  53.261  1.00 26.09      A  O
ATOM   1648  N    SER A 242      19.240  40.680  54.014  1.00 22.40      A  N
ATOM   1649  CA   SER A 242      20.595  41.060  54.337  1.00 22.40      A  C
ATOM   1650  CB   SER A 242      21.386  39.831  54.781  1.00 36.07      A  C
ATOM   1651  OG   SER A 242      20.709  39.139  55.817  1.00 36.07      A  O
ATOM   1652  C    SER A 242      21.236  41.695  53.112  1.00 22.40      A  C
ATOM   1653  O    SER A 242      21.926  42.712  53.213  1.00 22.40      A  O
ATOM   1654  N    ALA A 243      20.990  41.082  51.957  1.00 30.21      A  N
ATOM   1655  CA   ALA A 243      21.522  41.544  50.682  1.00 30.21      A  C
ATOM   1656  CB   ALA A 243      21.005  40.662  49.576  1.00 31.59      A  C
ATOM   1657  C    ALA A 243      21.101  42.995  50.461  1.00 30.21      A  C
ATOM   1658  O    ALA A 243      21.931  43.857  50.144  1.00 30.21      A  O
ATOM   1659  N    GLY A 244      19.804  43.247  50.629  1.00 29.66      A  N
ATOM   1660  CA   GLY A 244      19.273  44.593  50.502  1.00 29.66      A  C
ATOM   1661  C    GLY A 244      19.980  45.554  51.453  1.00 29.66      A  C
ATOM   1662  O    GLY A 244      20.322  46.678  51.078  1.00 29.66      A  O
ATOM   1663  N    CYS A 245      20.217  45.112  52.686  1.00 39.51      A  N
ATOM   1664  CA   CYS A 245      20.893  45.946  53.674  1.00 39.51      A  C
ATOM   1665  CB   CYS A 245      20.932  45.247  55.029  1.00 24.59      A  C
ATOM   1666  SG   CYS A 245      19.331  44.946  55.720  1.00 24.59      A  S
ATOM   1667  C    CYS A 245      22.313  46.312  53.247  1.00 39.51      A  C
ATOM   1668  O    CYS A 245      22.842  47.355  53.658  1.00 39.51      A  O
ATOM   1669  N    VAL A 246      22.929  45.455  52.435  1.00 16.32      A  N
```

FIG. 4-26

```
ATOM   1670  CA   VAL A 246      24.279  45.712  51.936  1.00 16.32           A  C
ATOM   1671  CB   VAL A 246      24.941  44.426  51.403  1.00 15.28           A  C
ATOM   1672  CG1  VAL A 246      26.151  44.772  50.543  1.00 15.28           A  C
ATOM   1673  CG2  VAL A 246      25.365  43.558  52.576  1.00 15.28           A  C
ATOM   1674  C    VAL A 246      24.240  46.753  50.821  1.00 16.32           A  C
ATOM   1675  O    VAL A 246      25.091  47.647  50.757  1.00 16.32           A  O
ATOM   1676  N    LEU A 247      23.235  46.631  49.956  1.00 18.03           A  N
ATOM   1677  CA   LEU A 247      23.049  47.548  48.844  1.00 18.03           A  C
ATOM   1678  CB   LEU A 247      21.854  47.111  47.999  1.00 28.31           A  C
ATOM   1679  CG   LEU A 247      21.376  48.066  46.898  1.00 28.31           A  C
ATOM   1680  CD1  LEU A 247      22.466  48.328  45.849  1.00 28.31           A  C
ATOM   1681  CD2  LEU A 247      20.147  47.466  46.264  1.00 28.31           A  C
ATOM   1682  C    LEU A 247      22.801  48.937  49.399  1.00 18.03           A  C
ATOM   1683  O    LEU A 247      23.455  49.902  49.019  1.00 18.03           A  O
ATOM   1684  N    ALA A 248      21.838  49.035  50.301  1.00 21.61           A  N
ATOM   1685  CA   ALA A 248      21.525  50.310  50.911  1.00 21.61           A  C
ATOM   1686  CB   ALA A 248      20.347  50.158  51.855  1.00 36.42           A  C
ATOM   1687  C    ALA A 248      22.737  50.853  51.662  1.00 21.61           A  C
ATOM   1688  O    ALA A 248      22.917  52.060  51.782  1.00 21.61           A  O
ATOM   1689  N    GLU A 249      23.573  49.961  52.174  1.00 14.50           A  N
ATOM   1690  CA   GLU A 249      24.748  50.408  52.893  1.00 14.50           A  C
ATOM   1691  CB   GLU A 249      25.335  49.252  53.700  1.00 22.79           A  C
ATOM   1692  CG   GLU A 249      26.394  49.700  54.716  1.00 22.79           A  C
ATOM   1693  CD   GLU A 249      26.916  48.574  55.551  1.00 22.79           A  C
ATOM   1694  OE1  GLU A 249      26.088  47.844  56.104  1.00 22.79           A  O
ATOM   1695  OE2  GLU A 249      28.140  48.417  55.676  1.00 22.79           A  O
ATOM   1696  C    GLU A 249      25.799  50.980  51.943  1.00 14.50           A  C
ATOM   1697  O    GLU A 249      26.478  51.950  52.274  1.00 14.50           A  O
ATOM   1698  N    LEU A 250      25.951  50.374  50.770  1.00 32.33           A  N
ATOM   1699  CA   LEU A 250      26.921  50.870  49.807  1.00 32.33           A  C
ATOM   1700  CB   LEU A 250      27.186  49.830  48.729  1.00 22.86           A  C
ATOM   1701  CG   LEU A 250      27.965  48.601  49.188  1.00 22.86           A  C
ATOM   1702  CD1  LEU A 250      28.239  47.715  47.984  1.00 22.86           A  C
ATOM   1703  CD2  LEU A 250      29.263  49.024  49.850  1.00 22.86           A  C
ATOM   1704  C    LEU A 250      26.453  52.172  49.172  1.00 32.33           A  C
ATOM   1705  O    LEU A 250      27.262  52.972  48.720  1.00 32.33           A  O
ATOM   1706  N    LEU A 251      25.148  52.396  49.152  1.00 27.55           A  N
ATOM   1707  CA   LEU A 251      24.616  53.618  48.578  1.00 27.55           A  C
ATOM   1708  CB   LEU A 251      23.194  53.386  48.082  1.00 17.54           A  C
ATOM   1709  CG   LEU A 251      23.072  52.482  46.858  1.00 17.54           A  C
ATOM   1710  CD1  LEU A 251      21.630  52.098  46.653  1.00 17.54           A  C
ATOM   1711  CD2  LEU A 251      23.619  53.177  45.652  1.00 17.54           A  C
ATOM   1712  C    LEU A 251      24.628  54.760  49.585  1.00 27.55           A  C
ATOM   1713  O    LEU A 251      24.774  55.915  49.205  1.00 27.55           A  O
ATOM   1714  N    LEU A 252      24.469  54.444  50.864  1.00 22.97           A  N
ATOM   1715  CA   LEU A 252      24.463  55.466  51.904  1.00 22.97           A  C
ATOM   1716  CB   LEU A 252      23.631  55.018  53.090  1.00 46.75           A  C
ATOM   1717  CG   LEU A 252      22.116  54.952  52.963  1.00 46.75           A  C
ATOM   1718  CD1  LEU A 252      21.518  54.664  54.363  1.00 46.75           A  C
ATOM   1719  CD2  LEU A 252      21.581  56.270  52.419  1.00 46.75           A  C
ATOM   1720  C    LEU A 252      25.833  55.808  52.443  1.00 22.97           A  C
ATOM   1721  O    LEU A 252      26.072  56.934  52.856  1.00 22.97           A  O
ATOM   1722  N    GLY A 253      26.722  54.823  52.480  1.00 31.05           A  N
ATOM   1723  CA   GLY A 253      28.050  55.065  53.010  1.00 31.05           A  C
ATOM   1724  C    GLY A 253      28.061  54.769  54.502  1.00 31.05           A  C
ATOM   1725  O    GLY A 253      28.958  55.177  55.240  1.00 31.05           A  O
ATOM   1726  N    GLN A 254      27.036  54.054  54.948  1.00 35.51           A  N
ATOM   1727  CA   GLN A 254      26.913  53.659  56.343  1.00 35.51           A  C
ATOM   1728  CB   GLN A 254      26.691  54.884  57.222  1.00 42.91           A  C
ATOM   1729  CG   GLN A 254      25.430  55.640  56.885  1.00 42.91           A  C
ATOM   1730  CD   GLN A 254      25.292  56.945  57.658  1.00 42.91           A  C
ATOM   1731  OE1  GLN A 254      25.267  56.958  58.897  1.00 42.91           A  O
ATOM   1732  NE2  GLN A 254      25.202  58.058  56.921  1.00 42.91           A  N
ATOM   1733  C    GLN A 254      25.717  52.724  56.439  1.00 35.51           A  C
ATOM   1734  O    GLN A 254      24.848  52.740  55.574  1.00 35.51           A  O
ATOM   1735  N    PRO A 255      25.655  51.893  57.488  1.00 21.73           A  N
ATOM   1736  CD   PRO A 255      26.644  51.685  58.555  1.00 22.30           A  C
```

FIG. 4-27

| | | | | | | | | | | | |
|---|---|---|---|---|---|---|---|---|---|---|---|
| ATOM | 1737 | CA | PRO | A | 255 | 24.540 | 50.967 | 57.644 | 1.00 | 21.73 | A C |
| ATOM | 1738 | CB | PRO | A | 255 | 24.845 | 50.292 | 58.976 | 1.00 | 22.30 | A C |
| ATOM | 1739 | CG | PRO | A | 255 | 26.318 | 50.295 | 59.015 | 1.00 | 22.30 | A C |
| ATOM | 1740 | C | PRO | A | 255 | 23.210 | 51.686 | 57.660 | 1.00 | 21.73 | A C |
| ATOM | 1741 | O | PRO | A | 255 | 23.096 | 52.778 | 58.213 | 1.00 | 21.73 | A O |
| ATOM | 1742 | N | ILE | A | 256 | 22.207 | 51.069 | 57.046 | 1.00 | 26.92 | A N |
| ATOM | 1743 | CA | ILE | A | 256 | 20.874 | 51.646 | 57.005 | 1.00 | 26.92 | A C |
| ATOM | 1744 | CB | ILE | A | 256 | 20.133 | 51.232 | 55.692 | 1.00 | 21.17 | A C |
| ATOM | 1745 | CG2 | ILE | A | 256 | 19.915 | 49.719 | 55.649 | 1.00 | 21.17 | A C |
| ATOM | 1746 | CG1 | ILE | A | 256 | 18.811 | 52.001 | 55.578 | 1.00 | 21.17 | A C |
| ATOM | 1747 | CD1 | ILE | A | 256 | 18.171 | 51.956 | 54.216 | 1.00 | 21.17 | A C |
| ATOM | 1748 | C | ILE | A | 256 | 20.022 | 51.308 | 58.243 | 1.00 | 26.92 | A C |
| ATOM | 1749 | O | ILE | A | 256 | 19.204 | 52.121 | 58.660 | 1.00 | 26.92 | A O |
| ATOM | 1750 | N | PHE | A | 257 | 20.218 | 50.135 | 58.846 | 1.00 | 26.77 | A N |
| ATOM | 1751 | CA | PHE | A | 257 | 19.439 | 49.760 | 60.033 | 1.00 | 26.77 | A C |
| ATOM | 1752 | CB | PHE | A | 257 | 18.498 | 48.605 | 59.695 | 1.00 | 27.68 | A C |
| ATOM | 1753 | CG | PHE | A | 257 | 17.563 | 48.902 | 58.575 | 1.00 | 27.68 | A C |
| ATOM | 1754 | CD1 | PHE | A | 257 | 16.850 | 50.097 | 58.541 | 1.00 | 27.68 | A C |
| ATOM | 1755 | CD2 | PHE | A | 257 | 17.398 | 47.997 | 57.541 | 1.00 | 27.68 | A C |
| ATOM | 1756 | CE1 | PHE | A | 257 | 15.985 | 50.390 | 57.482 | 1.00 | 27.68 | A C |
| ATOM | 1757 | CE2 | PHE | A | 257 | 16.533 | 48.279 | 56.475 | 1.00 | 27.68 | A C |
| ATOM | 1758 | CZ | PHE | A | 257 | 15.824 | 49.481 | 56.447 | 1.00 | 27.68 | A C |
| ATOM | 1759 | C | PHE | A | 257 | 20.285 | 49.384 | 61.261 | 1.00 | 26.77 | A C |
| ATOM | 1760 | O | PHE | A | 257 | 20.221 | 48.256 | 61.761 | 1.00 | 26.77 | A O |
| ATOM | 1761 | N | PRO | A | 258 | 21.081 | 50.336 | 61.774 | 1.00 | 31.39 | A N |
| ATOM | 1762 | CD | PRO | A | 258 | 21.240 | 51.711 | 61.268 | 1.00 | 27.63 | A C |
| ATOM | 1763 | CA | PRO | A | 258 | 21.941 | 50.126 | 62.937 | 1.00 | 31.39 | A C |
| ATOM | 1764 | CB | PRO | A | 258 | 22.845 | 51.350 | 62.901 | 1.00 | 27.63 | A C |
| ATOM | 1765 | CG | PRO | A | 258 | 21.933 | 52.396 | 62.422 | 1.00 | 27.63 | A C |
| ATOM | 1766 | C | PRO | A | 258 | 21.154 | 50.014 | 64.238 | 1.00 | 31.39 | A C |
| ATOM | 1767 | O | PRO | A | 258 | 19.919 | 50.046 | 64.235 | 1.00 | 31.39 | A O |
| ATOM | 1768 | N | GLY | A | 259 | 21.887 | 49.876 | 65.342 | 1.00 | 33.64 | A N |
| ATOM | 1769 | CA | GLY | A | 259 | 21.282 | 49.762 | 66.655 | 1.00 | 33.64 | A C |
| ATOM | 1770 | C | GLY | A | 259 | 22.026 | 48.716 | 67.443 | 1.00 | 33.64 | A C |
| ATOM | 1771 | O | GLY | A | 259 | 22.488 | 47.729 | 66.872 | 1.00 | 33.64 | A O |
| ATOM | 1772 | N | ASP | A | 260 | 22.163 | 48.933 | 68.745 | 1.00 | 27.12 | A N |
| ATOM | 1773 | CA | ASP | A | 260 | 22.862 | 47.988 | 69.601 | 1.00 | 27.12 | A C |
| ATOM | 1774 | CB | ASP | A | 260 | 23.556 | 48.721 | 70.753 | 1.00 | 43.49 | A C |
| ATOM | 1775 | CG | ASP | A | 260 | 24.769 | 49.514 | 70.301 | 1.00 | 43.49 | A C |
| ATOM | 1776 | OD1 | ASP | A | 260 | 25.100 | 49.452 | 69.097 | 1.00 | 43.49 | A O |
| ATOM | 1777 | OD2 | ASP | A | 260 | 25.390 | 50.198 | 71.149 | 1.00 | 43.49 | A O |
| ATOM | 1778 | C | ASP | A | 260 | 21.881 | 46.986 | 70.171 | 1.00 | 27.12 | A C |
| ATOM | 1779 | O | ASP | A | 260 | 22.261 | 46.114 | 70.935 | 1.00 | 27.12 | A O |
| ATOM | 1780 | N | SER | A | 261 | 20.615 | 47.109 | 69.800 | 1.00 | 19.99 | A N |
| ATOM | 1781 | CA | SER | A | 261 | 19.600 | 46.201 | 70.315 | 1.00 | 19.99 | A C |
| ATOM | 1782 | CB | SER | A | 261 | 18.931 | 46.794 | 71.548 | 1.00 | 13.89 | A C |
| ATOM | 1783 | OG | SER | A | 261 | 18.027 | 47.820 | 71.174 | 1.00 | 13.89 | A O |
| ATOM | 1784 | C | SER | A | 261 | 18.544 | 46.001 | 69.259 | 1.00 | 19.99 | A C |
| ATOM | 1785 | O | SER | A | 261 | 18.383 | 46.837 | 68.378 | 1.00 | 19.99 | A O |
| ATOM | 1786 | N | GLY | A | 262 | 17.818 | 44.895 | 69.367 | 1.00 | 32.23 | A N |
| ATOM | 1787 | CA | GLY | A | 262 | 16.765 | 44.608 | 68.414 | 1.00 | 32.23 | A C |
| ATOM | 1788 | C | GLY | A | 262 | 15.830 | 45.794 | 68.401 | 1.00 | 32.23 | A C |
| ATOM | 1789 | O | GLY | A | 262 | 15.483 | 46.329 | 67.354 | 1.00 | 32.23 | A O |
| ATOM | 1790 | N | VAL | A | 263 | 15.435 | 46.224 | 69.586 | 1.00 | 26.96 | A N |
| ATOM | 1791 | CA | VAL | A | 263 | 14.545 | 47.361 | 69.716 | 1.00 | 26.96 | A C |
| ATOM | 1792 | CB | VAL | A | 263 | 14.408 | 47.765 | 71.199 | 1.00 | 25.92 | A C |
| ATOM | 1793 | CG1 | VAL | A | 263 | 13.398 | 48.885 | 71.363 | 1.00 | 25.92 | A C |
| ATOM | 1794 | CG2 | VAL | A | 263 | 13.981 | 46.566 | 72.004 | 1.00 | 25.92 | A C |
| ATOM | 1795 | C | VAL | A | 263 | 15.039 | 48.546 | 68.890 | 1.00 | 26.96 | A C |
| ATOM | 1796 | O | VAL | A | 263 | 14.293 | 49.099 | 68.093 | 1.00 | 26.96 | A O |
| ATOM | 1797 | N | ASP | A | 264 | 16.291 | 48.939 | 69.074 | 1.00 | 24.07 | A N |
| ATOM | 1798 | CA | ASP | A | 264 | 16.811 | 50.060 | 68.308 | 1.00 | 24.07 | A C |
| ATOM | 1799 | CB | ASP | A | 264 | 18.259 | 50.341 | 68.693 | 1.00 | 43.34 | A C |
| ATOM | 1800 | CG | ASP | A | 264 | 18.376 | 50.971 | 70.056 | 1.00 | 43.34 | A C |
| ATOM | 1801 | OD1 | ASP | A | 264 | 17.547 | 51.847 | 70.359 | 1.00 | 43.34 | A O |
| ATOM | 1802 | OD2 | ASP | A | 264 | 19.293 | 50.614 | 70.820 | 1.00 | 43.34 | A O |
| ATOM | 1803 | C | ASP | A | 264 | 16.711 | 49.795 | 66.817 | 1.00 | 24.07 | A C |

FIG. 4-28

```
ATOM   1804  O    ASP A 264      16.216  50.628  66.061  1.00 24.07           A    O
ATOM   1805  N    GLN A 265      17.176  48.625  66.396  1.00 28.99           A    N
ATOM   1806  CA   GLN A 265      17.133  48.254  64.992  1.00 28.99           A    C
ATOM   1807  CB   GLN A 265      17.590  46.812  64.835  1.00 25.25           A    C
ATOM   1808  CG   GLN A 265      19.036  46.622  65.224  1.00 25.25           A    C
ATOM   1809  CD   GLN A 265      19.470  45.186  65.155  1.00 25.25           A    C
ATOM   1810  OE1  GLN A 265      19.273  44.531  64.139  1.00 25.25           A    O
ATOM   1811  NE2  GLN A 265      20.076  44.683  66.231  1.00 25.25           A    N
ATOM   1812  C    GLN A 265      15.721  48.422  64.454  1.00 28.99           A    C
ATOM   1813  O    GLN A 265      15.507  49.064  63.428  1.00 28.99           A    O
ATOM   1814  N    LEU A 266      14.747  47.853  65.149  1.00 28.89           A    N
ATOM   1815  CA   LEU A 266      13.371  47.965  64.694  1.00 28.89           A    C
ATOM   1816  CB   LEU A 266      12.426  47.221  65.631  1.00 13.31           A    C
ATOM   1817  CG   LEU A 266      12.087  45.808  65.177  1.00 13.31           A    C
ATOM   1818  CD1  LEU A 266      13.351  45.047  64.912  1.00 13.31           A    C
ATOM   1819  CD2  LEU A 266      11.255  45.128  66.232  1.00 13.31           A    C
ATOM   1820  C    LEU A 266      12.932  49.411  64.551  1.00 28.89           A    C
ATOM   1821  O    LEU A 266      12.168  49.745  63.649  1.00 28.89           A    O
ATOM   1822  N    VAL A 267      13.419  50.271  65.440  1.00 31.51           A    N
ATOM   1823  CA   VAL A 267      13.069  51.688  65.387  1.00 31.51           A    C
ATOM   1824  CB   VAL A 267      13.753  52.489  66.526  1.00 22.59           A    C
ATOM   1825  CG1  VAL A 267      13.833  53.974  66.167  1.00 22.59           A    C
ATOM   1826  CG2  VAL A 267      13.011  52.293  67.815  1.00 22.59           A    C
ATOM   1827  C    VAL A 267      13.599  52.197  64.059  1.00 31.51           A    C
ATOM   1828  O    VAL A 267      12.892  52.858  63.301  1.00 31.51           A    O
ATOM   1829  N    GLU A 268      14.858  51.887  63.781  1.00 36.26           A    N
ATOM   1830  CA   GLU A 268      15.457  52.321  62.534  1.00 36.26           A    C
ATOM   1831  CB   GLU A 268      16.943  51.973  62.501  1.00 38.51           A    C
ATOM   1832  CG   GLU A 268      17.803  52.925  63.291  1.00 38.51           A    C
ATOM   1833  CD   GLU A 268      17.452  54.382  63.005  1.00 38.51           A    C
ATOM   1834  OE1  GLU A 268      17.225  54.740  61.826  1.00 38.51           A    O
ATOM   1835  OE2  GLU A 268      17.405  55.180  63.960  1.00 38.51           A    O
ATOM   1836  C    GLU A 268      14.767  51.759  61.291  1.00 36.26           A    C
ATOM   1837  O    GLU A 268      14.734  52.419  60.260  1.00 36.26           A    O
ATOM   1838  N    ILE A 269      14.225  50.545  61.377  1.00 28.41           A    N
ATOM   1839  CA   ILE A 269      13.534  49.941  60.240  1.00 28.41           A    C
ATOM   1840  CB   ILE A 269      13.335  48.435  60.450  1.00 16.63           A    C
ATOM   1841  CG2  ILE A 269      12.459  47.854  59.362  1.00 16.63           A    C
ATOM   1842  CG1  ILE A 269      14.680  47.729  60.418  1.00 16.63           A    C
ATOM   1843  CD1  ILE A 269      14.547  46.221  60.498  1.00 16.63           A    C
ATOM   1844  C    ILE A 269      12.164  50.585  60.030  1.00 28.41           A    C
ATOM   1845  O    ILE A 269      11.756  50.833  58.898  1.00 28.41           A    O
ATOM   1846  N    ILE A 270      11.452  50.840  61.126  1.00 36.68           A    N
ATOM   1847  CA   ILE A 270      10.138  51.468  61.054  1.00 36.68           A    C
ATOM   1848  CB   ILE A 270       9.433  51.511  62.424  1.00 20.94           A    C
ATOM   1849  CG2  ILE A 270       8.140  52.278  62.309  1.00 20.94           A    C
ATOM   1850  CG1  ILE A 270       9.140  50.089  62.902  1.00 20.94           A    C
ATOM   1851  CD1  ILE A 270       8.451  50.012  64.218  1.00 20.94           A    C
ATOM   1852  C    ILE A 270      10.297  52.899  60.552  1.00 36.68           A    C
ATOM   1853  O    ILE A 270       9.492  53.374  59.749  1.00 36.68           A    O
ATOM   1854  N    LYS A 271      11.339  53.582  61.020  1.00 33.68           A    N
ATOM   1855  CA   LYS A 271      11.580  54.956  60.601  1.00 33.68           A    C
ATOM   1856  CB   LYS A 271      12.961  55.459  61.063  1.00 45.14           A    C
ATOM   1857  CG   LYS A 271      13.039  55.996  62.489  1.00 45.14           A    C
ATOM   1858  CD   LYS A 271      14.379  56.743  62.738  1.00 45.14           A    C
ATOM   1859  CE   LYS A 271      14.508  57.270  64.191  1.00 45.14           A    C
ATOM   1860  NZ   LYS A 271      15.708  58.166  64.393  1.00 45.14           A    N
ATOM   1861  C    LYS A 271      11.494  55.075  59.078  1.00 33.68           A    C
ATOM   1862  O    LYS A 271      11.046  56.098  58.562  1.00 33.68           A    O
ATOM   1863  N    VAL A 272      11.923  54.039  58.358  1.00 44.43           A    N
ATOM   1864  CA   VAL A 272      11.882  54.065  56.892  1.00 44.43           A    C
ATOM   1865  CB   VAL A 272      13.131  53.441  56.274  1.00 50.48           A    C
ATOM   1866  CG1  VAL A 272      14.290  54.402  56.360  1.00 50.48           A    C
ATOM   1867  CG2  VAL A 272      13.461  52.153  57.002  1.00 50.48           A    C
ATOM   1868  C    VAL A 272      10.671  53.325  56.327  1.00 44.43           A    C
ATOM   1869  O    VAL A 272       9.790  53.942  55.721  1.00 44.43           A    O
ATOM   1870  N    LEU A 273      10.632  52.009  56.524  1.00 29.32           A    N
```

FIG. 4-29

```
ATOM   1871  CA   LEU A 273       9.520  51.195  56.039  1.00  29.32      A    C
ATOM   1872  CB   LEU A 273       9.745  49.715  56.360  1.00  22.66      A    C
ATOM   1873  CG   LEU A 273      10.903  49.014  55.673  1.00  22.66      A    C
ATOM   1874  CD1  LEU A 273      10.648  47.523  55.789  1.00  22.66      A    C
ATOM   1875  CD2  LEU A 273      10.992  49.431  54.213  1.00  22.66      A    C
ATOM   1876  C    LEU A 273       8.155  51.600  56.594  1.00  29.32      A    C
ATOM   1877  O    LEU A 273       7.129  51.378  55.953  1.00  29.32      A    O
ATOM   1878  N    GLY A 274       8.149  52.204  57.776  1.00  52.62      A    N
ATOM   1879  CA   GLY A 274       6.898  52.579  58.401  1.00  52.62      A    C
ATOM   1880  C    GLY A 274       6.430  51.450  59.309  1.00  52.62      A    C
ATOM   1881  O    GLY A 274       6.860  50.294  59.194  1.00  52.62      A    O
ATOM   1882  N    THR A 275       5.556  51.788  60.241  1.00  43.83      A    N
ATOM   1883  CA   THR A 275       5.012  50.801  61.161  1.00  43.83      A    C
ATOM   1884  CB   THR A 275       3.924  51.463  62.067  1.00  45.06      A    C
ATOM   1885  OG1  THR A 275       4.505  52.558  62.792  1.00  45.06      A    O
ATOM   1886  CG2  THR A 275       3.343  50.466  63.050  1.00  45.06      A    C
ATOM   1887  C    THR A 275       4.397  49.605  60.407  1.00  43.83      A    C
ATOM   1888  O    THR A 275       3.602  49.752  59.473  1.00  43.83      A    O
ATOM   1889  N    PRO A 276       4.761  48.395  60.820  1.00  45.90      A    N
ATOM   1890  CD   PRO A 276       5.700  48.063  61.902  1.00  40.12      A    C
ATOM   1891  CA   PRO A 276       4.234  47.203  60.170  1.00  45.90      A    C
ATOM   1892  CB   PRO A 276       5.203  46.109  60.599  1.00  40.12      A    C
ATOM   1893  CG   PRO A 276       5.687  46.547  61.925  1.00  40.12      A    C
ATOM   1894  C    PRO A 276       2.800  46.885  60.543  1.00  45.90      A    C
ATOM   1895  O    PRO A 276       2.426  46.822  61.726  1.00  45.90      A    O
ATOM   1896  N    THR A 277       2.004  46.676  59.502  1.00  49.26      A    N
ATOM   1897  CA   THR A 277       0.611  46.343  59.673  1.00  49.26      A    C
ATOM   1898  CB   THR A 277       0.103  46.229  58.321  1.00  42.51      A    C
ATOM   1899  OG1  THR A 277       0.278  45.003  57.678  1.00  42.51      A    O
ATOM   1900  CG2  THR A 277       0.282  47.422  57.430  1.00  42.51      A    C
ATOM   1901  C    THR A 277       0.552  45.012  60.389  1.00  49.26      A    C
ATOM   1902  O    THR A 277       1.421  44.161  60.209  1.00  49.26      A    O
ATOM   1903  N    ALA A 278      -0.461  44.845  61.224  1.00  47.32      A    N
ATOM   1904  CA   ALA A 278      -0.619  43.611  61.984  1.00  47.32      A    C
ATOM   1905  CB   ALA A 278      -1.938  43.632  62.740  0.00  34.21      A    C
ATOM   1906  C    ALA A 278      -0.548  42.388  61.071  1.00  47.32      A    C
ATOM   1907  O    ALA A 278       0.058  41.358  61.416  1.00  47.32      A    O
ATOM   1908  N    GLU A 279      -1.163  42.501  59.896  1.00  66.97      A    N
ATOM   1909  CA   GLU A 279      -1.133  41.381  58.962  1.00  66.97      A    C
ATOM   1910  CB   GLU A 279      -1.981  41.682  57.708  1.00  80.79      A    C
ATOM   1911  CG   GLU A 279      -2.704  40.441  57.168  1.00  80.79      A    C
ATOM   1912  CD   GLU A 279      -1.851  39.169  57.321  1.00  80.79      A    C
ATOM   1913  OE1  GLU A 279      -0.810  39.062  56.608  1.00  80.79      A    O
ATOM   1914  OE2  GLU A 279      -2.227  38.295  58.157  1.00  80.79      A    O
ATOM   1915  C    GLU A 279       0.345  41.130  58.581  1.00  66.97      A    C
ATOM   1916  O    GLU A 279       0.826  39.982  58.536  1.00  66.97      A    O
ATOM   1917  N    GLN A 280       1.067  42.214  58.305  1.00  52.80      A    N
ATOM   1918  CA   GLN A 280       2.483  42.106  57.945  1.00  52.80      A    C
ATOM   1919  CB   GLN A 280       3.084  43.505  57.724  1.00  41.24      A    C
ATOM   1920  CG   GLN A 280       3.085  43.971  56.274  1.00  41.24      A    C
ATOM   1921  CD   GLN A 280       3.436  45.440  56.141  1.00  41.24      A    C
ATOM   1922  OE1  GLN A 280       3.956  45.868  55.107  1.00  41.24      A    O
ATOM   1923  NE2  GLN A 280       3.149  46.228  57.187  1.00  41.24      A    N
ATOM   1924  C    GLN A 280       3.269  41.361  59.031  1.00  52.80      A    C
ATOM   1925  O    GLN A 280       4.145  40.520  58.742  1.00  52.80      A    O
ATOM   1926  N    ILE A 281       2.938  41.652  60.286  1.00  55.19      A    N
ATOM   1927  CA   ILE A 281       3.627  41.010  61.387  1.00  55.19      A    C
ATOM   1928  CB   ILE A 281       3.108  41.511  62.729  1.00  62.37      A    C
ATOM   1929  CG2  ILE A 281       3.932  40.894  63.852  1.00  62.37      A    C
ATOM   1930  CG1  ILE A 281       3.166  43.042  62.752  1.00  62.37      A    C
ATOM   1931  CD1  ILE A 281       3.047  43.656  64.137  1.00  62.37      A    C
ATOM   1932  C    ILE A 281       3.462  39.501  61.333  1.00  55.19      A    C
ATOM   1933  O    ILE A 281       4.336  38.750  61.793  1.00  55.19      A    O
ATOM   1934  N    ALA A 282       2.340  39.061  60.771  1.00  46.44      A    N
ATOM   1935  CA   ALA A 282       2.066  37.637  60.669  1.00  46.44      A    C
ATOM   1936  CB   ALA A 282       0.815  37.396  59.856  1.00  74.25      A    C
ATOM   1937  C    ALA A 282       3.247  36.936  60.025  1.00  46.44      A    C
```

FIG. 4-30

| | | | | | | | | | | |
|---|---|---|---|---|---|---|---|---|---|---|
| ATOM | 1938 | O   | ALA | A | 282 | 3.868  | 36.064 | 60.647 | 1.00 46.44 | A O |
| ATOM | 1939 | N   | GLU | A | 283 | 3.565  | 37.322 | 58.785 | 1.00 68.04 | A N |
| ATOM | 1940 | CA  | GLU | A | 283 | 4.686  | 36.709 | 58.061 | 1.00 68.04 | A C |
| ATOM | 1941 | CB  | GLU | A | 283 | 4.932  | 37.416 | 56.726 | 0.00 68.87 | A C |
| ATOM | 1942 | CG  | GLU | A | 283 | 3.849  | 37.149 | 55.707 | 0.00 68.87 | A C |
| ATOM | 1943 | CD  | GLU | A | 283 | 2.694  | 38.121 | 55.826 | 1.00 68.87 | A C |
| ATOM | 1944 | OE1 | GLU | A | 283 | 2.213  | 38.357 | 56.963 | 1.00 68.87 | A O |
| ATOM | 1945 | OE2 | GLU | A | 283 | 2.254  | 38.636 | 54.772 | 1.00 68.87 | A O |
| ATOM | 1946 | C   | GLU | A | 283 | 5.970  | 36.689 | 58.898 | 1.00 68.04 | A C |
| ATOM | 1947 | O   | GLU | A | 283 | 6.839  | 35.816 | 58.715 | 1.00 68.04 | A O |
| ATOM | 1948 | N   | MET | A | 284 | 6.076  | 37.643 | 59.829 | 1.00 62.97 | A N |
| ATOM | 1949 | CA  | MET | A | 284 | 7.228  | 37.702 | 60.722 | 1.00 62.97 | A C |
| ATOM | 1950 | CB  | MET | A | 284 | 7.294  | 39.043 | 61.460 | 1.00 52.89 | A C |
| ATOM | 1951 | CG  | MET | A | 284 | 8.474  | 39.872 | 61.011 | 1.00 52.89 | A C |
| ATOM | 1952 | SD  | MET | A | 284 | 8.146  | 40.539 | 59.380 | 1.00 52.89 | A S |
| ATOM | 1953 | CE  | MET | A | 284 | 8.041  | 42.227 | 59.852 | 1.00 52.89 | A C |
| ATOM | 1954 | C   | MET | A | 284 | 7.182  | 36.560 | 61.739 | 1.00 62.97 | A C |
| ATOM | 1955 | O   | MET | A | 284 | 8.127  | 35.774 | 61.858 | 1.00 62.97 | A O |
| ATOM | 1956 | N   | ALA | A | 290 | 3.093  | 54.291 | 64.785 | 1.00 46.31 | A N |
| ATOM | 1957 | CA  | ALA | A | 290 | 2.842  | 55.103 | 63.603 | 1.00 46.31 | A C |
| ATOM | 1958 | CB  | ALA | A | 290 | 2.124  | 56.351 | 64.007 | 1.00 24.08 | A C |
| ATOM | 1959 | C   | ALA | A | 290 | 4.141  | 55.463 | 62.861 | 1.00 46.31 | A C |
| ATOM | 1960 | O   | ALA | A | 290 | 5.217  | 55.567 | 63.470 | 1.00 46.31 | A O |
| ATOM | 1961 | N   | ALA | A | 291 | 4.039  | 55.653 | 61.544 | 1.00 76.21 | A N |
| ATOM | 1962 | CA  | ALA | A | 291 | 5.204  | 56.008 | 60.726 | 1.00 76.21 | A C |
| ATOM | 1963 | CB  | ALA | A | 291 | 6.394  | 55.093 | 61.083 | 1.00 64.41 | A C |
| ATOM | 1964 | C   | ALA | A | 291 | 4.929  | 55.978 | 59.200 | 1.00 76.21 | A C |
| ATOM | 1965 | O   | ALA | A | 291 | 3.971  | 56.612 | 58.730 | 1.00 76.21 | A O |
| ATOM | 1966 | N   | ALA | A | 292 | 5.775  | 55.263 | 58.442 | 1.00 98.91 | A N |
| ATOM | 1967 | CA  | ALA | A | 292 | 5.661  | 55.142 | 56.969 | 1.00 98.91 | A C |
| ATOM | 1968 | CB  | ALA | A | 292 | 4.201  | 54.875 | 56.559 | 1.00 44.14 | A C |
| ATOM | 1969 | C   | ALA | A | 292 | 6.190  | 56.405 | 56.261 | 1.00 98.91 | A C |
| ATOM | 1970 | O   | ALA | A | 292 | 5.533  | 57.458 | 56.288 | 1.00 98.91 | A O |
| ATOM | 1971 | N   | ALA | A | 293 | 7.358  | 56.302 | 55.619 | 1.00 79.55 | A N |
| ATOM | 1972 | CA  | ALA | A | 293 | 7.956  | 57.468 | 54.949 | 1.00 79.55 | A C |
| ATOM | 1973 | CB  | ALA | A | 293 | 9.021  | 58.117 | 55.871 | 1.00 86.47 | A C |
| ATOM | 1974 | C   | ALA | A | 293 | 8.580  | 57.130 | 53.593 | 1.00 79.55 | A C |
| ATOM | 1975 | O   | ALA | A | 293 | 8.711  | 55.956 | 53.236 | 1.00 79.55 | A O |
| ATOM | 1976 | N   | PRO | A | 294 | 9.016  | 58.153 | 52.832 | 1.00 69.16 | A N |
| ATOM | 1977 | CD  | PRO | A | 294 | 9.199  | 59.593 | 53.104 | 1.00 76.85 | A C |
| ATOM | 1978 | CA  | PRO | A | 294 | 9.593  | 57.798 | 51.532 | 1.00 69.16 | A C |
| ATOM | 1979 | CB  | PRO | A | 294 | 9.707  | 59.139 | 50.824 | 1.00 76.85 | A C |
| ATOM | 1980 | CG  | PRO | A | 294 | 10.167 | 60.028 | 51.969 | 1.00 76.85 | A C |
| ATOM | 1981 | C   | PRO | A | 294 | 10.933 | 57.110 | 51.638 | 1.00 69.16 | A C |
| ATOM | 1982 | O   | PRO | A | 294 | 11.596 | 57.150 | 52.681 | 1.00 69.16 | A O |
| ATOM | 1983 | N   | TRP | A | 301 | 11.306 | 56.499 | 50.521 | 1.00 52.65 | A N |
| ATOM | 1984 | CA  | TRP | A | 301 | 12.541 | 55.757 | 50.373 | 1.00 52.65 | A C |
| ATOM | 1985 | CB  | TRP | A | 301 | 12.296 | 54.517 | 49.518 | 1.00 34.69 | A C |
| ATOM | 1986 | CG  | TRP | A | 301 | 12.371 | 53.228 | 50.258 | 1.00 34.69 | A C |
| ATOM | 1987 | CD2 | TRP | A | 301 | 13.527 | 52.676 | 50.888 | 1.00 34.69 | A C |
| ATOM | 1988 | CE2 | TRP | A | 301 | 13.169 | 51.393 | 51.366 | 1.00 34.69 | A C |
| ATOM | 1989 | CE3 | TRP | A | 301 | 14.840 | 53.138 | 51.094 | 1.00 34.69 | A C |
| ATOM | 1990 | CD1 | TRP | A | 301 | 11.379 | 52.294 | 50.383 | 1.00 34.69 | A C |
| ATOM | 1991 | NE1 | TRP | A | 301 | 11.853 | 51.187 | 51.045 | 1.00 34.69 | A N |
| ATOM | 1992 | CZ2 | TRP | A | 301 | 14.073 | 50.563 | 52.036 | 1.00 34.69 | A C |
| ATOM | 1993 | CZ3 | TRP | A | 301 | 15.743 | 52.313 | 51.760 | 1.00 34.69 | A C |
| ATOM | 1994 | CH2 | TRP | A | 301 | 15.352 | 51.038 | 52.223 | 1.00 34.69 | A C |
| ATOM | 1995 | C   | TRP | A | 301 | 13.502 | 56.662 | 49.645 | 1.00 52.65 | A C |
| ATOM | 1996 | O   | TRP | A | 301 | 14.719 | 56.477 | 49.703 | 1.00 52.65 | A O |
| ATOM | 1997 | N   | THR | A | 302 | 12.943 | 57.636 | 48.943 | 1.00 40.98 | A N |
| ATOM | 1998 | CA  | THR | A | 302 | 13.758 | 58.566 | 48.178 | 1.00 40.98 | A C |
| ATOM | 1999 | CB  | THR | A | 302 | 12.912 | 59.277 | 47.110 | 1.00 62.98 | A C |
| ATOM | 2000 | OG1 | THR | A | 302 | 11.538 | 59.271 | 47.526 | 1.00 62.98 | A O |
| ATOM | 2001 | CG2 | THR | A | 302 | 13.065 | 58.582 | 45.734 | 1.00 62.98 | A C |
| ATOM | 2002 | C   | THR | A | 302 | 14.408 | 59.578 | 49.112 | 1.00 40.98 | A C |
| ATOM | 2003 | O   | THR | A | 302 | 15.523 | 60.054 | 48.871 | 1.00 40.98 | A O |
| ATOM | 2004 | N   | ALA | A | 303 | 13.713 | 59.900 | 50.192 | 1.00 38.10 | A N |

FIG. 4-31

| ATOM | 2005 | CA | ALA | A | 303 | 14.271 | 60.829 | 51.164 | 1.00 | 38.10 | A | C |
|---|---|---|---|---|---|---|---|---|---|---|---|---|
| ATOM | 2006 | CB | ALA | A | 303 | 13.212 | 61.173 | 52.219 | 1.00 | 49.99 | A | C |
| ATOM | 2007 | C | ALA | A | 303 | 15.486 | 60.166 | 51.831 | 1.00 | 38.10 | A | C |
| ATOM | 2008 | O | ALA | A | 303 | 16.351 | 60.825 | 52.420 | 1.00 | 38.10 | A | O |
| ATOM | 2009 | N | VAL | A | 304 | 15.532 | 58.847 | 51.718 | 1.00 | 36.96 | A | N |
| ATOM | 2010 | CA | VAL | A | 304 | 16.577 | 58.045 | 52.319 | 1.00 | 36.96 | A | C |
| ATOM | 2011 | CB | VAL | A | 304 | 16.205 | 56.562 | 52.283 | 1.00 | 42.39 | A | C |
| ATOM | 2012 | CG1 | VAL | A | 304 | 17.272 | 55.746 | 52.996 | 1.00 | 42.39 | A | C |
| ATOM | 2013 | CG2 | VAL | A | 304 | 14.837 | 56.358 | 52.910 | 1.00 | 42.39 | A | C |
| ATOM | 2014 | C | VAL | A | 304 | 17.981 | 58.166 | 51.751 | 1.00 | 36.96 | A | C |
| ATOM | 2015 | O | VAL | A | 304 | 18.943 | 58.158 | 52.511 | 1.00 | 36.96 | A | O |
| ATOM | 2016 | N | PHE | A | 305 | 18.117 | 58.263 | 50.432 | 1.00 | 28.00 | A | N |
| ATOM | 2017 | CA | PHE | A | 305 | 19.449 | 58.341 | 49.834 | 1.00 | 28.00 | A | C |
| ATOM | 2018 | CB | PHE | A | 305 | 19.537 | 57.383 | 48.662 | 1.00 | 31.80 | A | C |
| ATOM | 2019 | CG | PHE | A | 305 | 19.137 | 55.997 | 49.016 | 1.00 | 31.80 | A | C |
| ATOM | 2020 | CD1 | PHE | A | 305 | 19.986 | 55.193 | 49.775 | 1.00 | 31.80 | A | C |
| ATOM | 2021 | CD2 | PHE | A | 305 | 17.892 | 55.495 | 48.628 | 1.00 | 31.80 | A | C |
| ATOM | 2022 | CE1 | PHE | A | 305 | 19.605 | 53.889 | 50.153 | 1.00 | 31.80 | A | C |
| ATOM | 2023 | CE2 | PHE | A | 305 | 17.490 | 54.192 | 48.993 | 1.00 | 31.80 | A | C |
| ATOM | 2024 | CZ | PHE | A | 305 | 18.354 | 53.384 | 49.762 | 1.00 | 31.80 | A | C |
| ATOM | 2025 | C | PHE | A | 305 | 19.844 | 59.723 | 49.375 | 1.00 | 28.00 | A | C |
| ATOM | 2026 | O | PHE | A | 305 | 19.068 | 60.664 | 49.494 | 1.00 | 28.00 | A | O |
| ATOM | 2027 | N | ARG | A | 306 | 21.072 | 59.835 | 48.871 | 1.00 | 38.93 | A | N |
| ATOM | 2028 | CA | ARG | A | 306 | 21.584 | 61.101 | 48.367 | 1.00 | 38.93 | A | C |
| ATOM | 2029 | CB | ARG | A | 306 | 23.038 | 60.969 | 47.908 | 1.00 | 54.66 | A | C |
| ATOM | 2030 | CG | ARG | A | 306 | 23.948 | 60.159 | 48.801 | 1.00 | 54.66 | A | C |
| ATOM | 2031 | CD | ARG | A | 306 | 25.285 | 59.938 | 48.076 | 1.00 | 54.66 | A | C |
| ATOM | 2032 | NE | ARG | A | 306 | 25.123 | 59.895 | 46.616 | 1.00 | 54.66 | A | N |
| ATOM | 2033 | CZ | ARG | A | 306 | 26.105 | 59.673 | 45.738 | 1.00 | 54.66 | A | C |
| ATOM | 2034 | NH1 | ARG | A | 306 | 27.347 | 59.457 | 46.156 | 1.00 | 54.66 | A | N |
| ATOM | 2035 | NH2 | ARG | A | 306 | 25.849 | 59.699 | 44.433 | 1.00 | 54.66 | A | N |
| ATOM | 2036 | C | ARG | A | 306 | 20.739 | 61.513 | 47.163 | 1.00 | 38.93 | A | C |
| ATOM | 2037 | O | ARG | A | 306 | 20.261 | 60.680 | 46.389 | 1.00 | 38.93 | A | O |
| ATOM | 2038 | N | PRO | A | 307 | 20.558 | 62.817 | 46.982 | 1.00 | 61.10 | A | N |
| ATOM | 2039 | CD | PRO | A | 307 | 21.084 | 63.898 | 47.839 | 1.00 | 69.15 | A | C |
| ATOM | 2040 | CA | PRO | A | 307 | 19.762 | 63.346 | 45.872 | 1.00 | 61.10 | A | C |
| ATOM | 2041 | CB | PRO | A | 307 | 20.006 | 64.851 | 45.968 | 1.00 | 69.15 | A | C |
| ATOM | 2042 | CG | PRO | A | 307 | 20.179 | 65.063 | 47.477 | 1.00 | 69.15 | A | C |
| ATOM | 2043 | C | PRO | A | 307 | 20.080 | 62.784 | 44.479 | 1.00 | 61.10 | A | C |
| ATOM | 2044 | O | PRO | A | 307 | 19.162 | 62.522 | 43.696 | 1.00 | 61.10 | A | O |
| ATOM | 2045 | N | ALA | A | 308 | 21.359 | 62.597 | 44.159 | 1.00 | 31.52 | A | N |
| ATOM | 2046 | CA | ALA | A | 308 | 21.717 | 62.083 | 42.834 | 1.00 | 31.52 | A | C |
| ATOM | 2047 | CB | ALA | A | 308 | 23.144 | 62.515 | 42.480 | 1.00 | 53.50 | A | C |
| ATOM | 2048 | C | ALA | A | 308 | 21.584 | 60.556 | 42.675 | 1.00 | 31.52 | A | C |
| ATOM | 2049 | O | ALA | A | 308 | 21.883 | 60.008 | 41.617 | 1.00 | 31.52 | A | O |
| ATOM | 2050 | N | THR | A | 309 | 21.127 | 59.870 | 43.715 | 1.00 | 23.81 | A | N |
| ATOM | 2051 | CA | THR | A | 309 | 21.004 | 58.417 | 43.661 | 1.00 | 23.81 | A | C |
| ATOM | 2052 | CB | THR | A | 309 | 20.519 | 57.840 | 45.010 | 1.00 | 28.68 | A | C |
| ATOM | 2053 | OG1 | THR | A | 309 | 21.526 | 58.027 | 46.012 | 1.00 | 28.68 | A | O |
| ATOM | 2054 | CG2 | THR | A | 309 | 20.226 | 56.361 | 44.880 | 1.00 | 28.68 | A | C |
| ATOM | 2055 | C | THR | A | 309 | 20.039 | 57.957 | 42.586 | 1.00 | 23.81 | A | C |
| ATOM | 2056 | O | THR | A | 309 | 18.934 | 58.480 | 42.487 | 1.00 | 23.81 | A | O |
| ATOM | 2057 | N | PRO | A | 310 | 20.451 | 56.984 | 41.750 | 1.00 | 33.83 | A | N |
| ATOM | 2058 | CD | PRO | A | 310 | 21.820 | 56.497 | 41.543 | 1.00 | 16.70 | A | C |
| ATOM | 2059 | CA | PRO | A | 310 | 19.570 | 56.481 | 40.692 | 1.00 | 33.83 | A | C |
| ATOM | 2060 | CB | PRO | A | 310 | 20.459 | 55.500 | 39.919 | 1.00 | 16.70 | A | C |
| ATOM | 2061 | CG | PRO | A | 310 | 21.562 | 55.204 | 40.833 | 1.00 | 16.70 | A | C |
| ATOM | 2062 | C | PRO | A | 310 | 18.296 | 55.837 | 41.231 | 1.00 | 33.83 | A | C |
| ATOM | 2063 | O | PRO | A | 310 | 18.330 | 55.043 | 42.168 | 1.00 | 33.83 | A | O |
| ATOM | 2064 | N | PRO | A | 311 | 17.146 | 56.181 | 40.640 | 1.00 | 44.00 | A | N |
| ATOM | 2065 | CD | PRO | A | 311 | 16.978 | 57.145 | 39.540 | 1.00 | 35.22 | A | C |
| ATOM | 2066 | CA | PRO | A | 311 | 15.850 | 55.648 | 41.060 | 1.00 | 44.00 | A | C |
| ATOM | 2067 | CB | PRO | A | 311 | 14.870 | 56.335 | 40.110 | 1.00 | 35.22 | A | C |
| ATOM | 2068 | CG | PRO | A | 311 | 15.569 | 57.602 | 39.752 | 1.00 | 35.22 | A | C |
| ATOM | 2069 | C | PRO | A | 311 | 15.750 | 54.129 | 40.983 | 1.00 | 44.00 | A | C |
| ATOM | 2070 | O | PRO | A | 311 | 14.961 | 53.511 | 41.712 | 1.00 | 44.00 | A | O |
| ATOM | 2071 | N | GLU | A | 312 | 16.550 | 53.538 | 40.103 | 1.00 | 24.22 | A | N |

FIG. 4-32

```
ATOM   2072  CA   GLU A 312      16.560  52.083  39.903  1.00 24.22      A    C
ATOM   2073  CB   GLU A 312      17.367  51.729  38.644  1.00 62.63      A    C
ATOM   2074  CG   GLU A 312      16.879  52.389  37.370  1.00 62.63      A    C
ATOM   2075  CD   GLU A 312      16.758  53.921  37.485  1.00 62.63      A    C
ATOM   2076  OE1  GLU A 312      17.711  54.548  38.037  1.00 62.63      A    O
ATOM   2077  OE2  GLU A 312      15.715  54.475  37.014  1.00 62.63      A    O
ATOM   2078  C    GLU A 312      17.174  51.340  41.093  1.00 24.22      A    C
ATOM   2079  O    GLU A 312      16.722  50.251  41.465  1.00 24.22      A    O
ATOM   2080  N    ALA A 313      18.222  51.928  41.663  1.00 27.51      A    N
ATOM   2081  CA   ALA A 313      18.915  51.346  42.806  1.00 27.51      A    C
ATOM   2082  CB   ALA A 313      20.254  52.055  43.034  1.00 32.80      A    C
ATOM   2083  C    ALA A 313      18.046  51.469  44.040  1.00 27.51      A    C
ATOM   2084  O    ALA A 313      18.024  50.582  44.899  1.00 27.51      A    O
ATOM   2085  N    ILE A 314      17.314  52.570  44.109  1.00 37.36      A    N
ATOM   2086  CA   ILE A 314      16.448  52.808  45.232  1.00 37.36      A    C
ATOM   2087  CB   ILE A 314      16.261  54.327  45.426  1.00 55.52      A    C
ATOM   2088  CG2  ILE A 314      16.039  54.998  44.125  1.00 55.52      A    C
ATOM   2089  CG1  ILE A 314      15.151  54.604  46.416  1.00 55.52      A    C
ATOM   2090  CD1  ILE A 314      14.977  56.090  46.674  1.00 55.52      A    C
ATOM   2091  C    ILE A 314      15.148  52.031  45.045  1.00 37.36      A    C
ATOM   2092  O    ILE A 314      14.444  51.719  46.010  1.00 37.36      A    O
ATOM   2093  N    ALA A 315      14.852  51.670  43.806  1.00 27.66      A    N
ATOM   2094  CA   ALA A 315      13.658  50.881  43.532  1.00 27.66      A    C
ATOM   2095  CB   ALA A 315      13.389  50.836  42.036  1.00  7.33      A    C
ATOM   2096  C    ALA A 315      13.923  49.473  44.064  1.00 27.66      A    C
ATOM   2097  O    ALA A 315      13.132  48.921  44.826  1.00 27.66      A    O
ATOM   2098  N    LEU A 316      15.057  48.909  43.659  1.00 24.56      A    N
ATOM   2099  CA   LEU A 316      15.469  47.574  44.068  1.00 24.56      A    C
ATOM   2100  CB   LEU A 316      16.859  47.276  43.503  1.00 17.80      A    C
ATOM   2101  CG   LEU A 316      17.502  45.933  43.835  1.00 17.80      A    C
ATOM   2102  CD1  LEU A 316      16.627  44.808  43.387  1.00 17.80      A    C
ATOM   2103  CD2  LEU A 316      18.842  45.845  43.170  1.00 17.80      A    C
ATOM   2104  C    LEU A 316      15.472  47.408  45.589  1.00 24.56      A    C
ATOM   2105  O    LEU A 316      15.040  46.377  46.108  1.00 24.56      A    O
ATOM   2106  N    CYS A 317      15.948  48.420  46.307  1.00 25.76      A    N
ATOM   2107  CA   CYS A 317      15.988  48.337  47.762  1.00 25.76      A    C
ATOM   2108  CB   CYS A 317      16.507  49.628  48.377  1.00 30.60      A    C
ATOM   2109  SG   CYS A 317      18.176  50.026  47.998  1.00 30.60      A    S
ATOM   2110  C    CYS A 317      14.614  48.072  48.338  1.00 25.76      A    C
ATOM   2111  O    CYS A 317      14.420  47.131  49.098  1.00 25.76      A    O
ATOM   2112  N    SER A 318      13.661  48.920  47.976  1.00 30.58      A    N
ATOM   2113  CA   SER A 318      12.304  48.796  48.475  1.00 30.58      A    C
ATOM   2114  CB   SER A 318      11.411  49.842  47.820  1.00 41.98      A    C
ATOM   2115  OG   SER A 318      11.197  49.512  46.461  1.00 41.98      A    O
ATOM   2116  C    SER A 318      11.733  47.414  48.211  1.00 30.58      A    C
ATOM   2117  O    SER A 318      10.846  46.956  48.932  1.00 30.58      A    O
ATOM   2118  N    ARG A 319      12.252  46.753  47.180  1.00 29.39      A    N
ATOM   2119  CA   ARG A 319      11.784  45.428  46.807  1.00 29.39      A    C
ATOM   2120  CB   ARG A 319      11.844  45.277  45.289  1.00 37.05      A    C
ATOM   2121  CG   ARG A 319      11.050  46.333  44.545  1.00 37.05      A    C
ATOM   2122  CD   ARG A 319       9.536  46.223  44.775  1.00 37.05      A    C
ATOM   2123  NE   ARG A 319       8.954  44.984  44.254  1.00 37.05      A    N
ATOM   2124  CZ   ARG A 319       8.683  43.901  44.984  1.00 37.05      A    C
ATOM   2125  NH1  ARG A 319       8.927  43.882  46.294  1.00 37.05      A    N
ATOM   2126  NH2  ARG A 319       8.181  42.822  44.395  1.00 37.05      A    N
ATOM   2127  C    ARG A 319      12.568  44.309  47.473  1.00 29.39      A    C
ATOM   2128  O    ARG A 319      12.280  43.132  47.263  1.00 29.39      A    O
ATOM   2129  N    LEU A 320      13.562  44.682  48.272  1.00 33.48      A    N
ATOM   2130  CA   LEU A 320      14.383  43.715  48.982  1.00 33.48      A    C
ATOM   2131  CB   LEU A 320      15.868  43.962  48.713  1.00 24.56      A    C
ATOM   2132  CG   LEU A 320      16.332  43.750  47.271  1.00 24.56      A    C
ATOM   2133  CD1  LEU A 320      17.728  44.252  47.124  1.00 24.56      A    C
ATOM   2134  CD2  LEU A 320      16.260  42.280  46.900  1.00 24.56      A    C
ATOM   2135  C    LEU A 320      14.101  43.835  50.464  1.00 33.48      A    C
ATOM   2136  O    LEU A 320      14.081  42.834  51.175  1.00 33.48      A    O
ATOM   2137  N    LEU A 321      13.867  45.062  50.922  1.00 20.95      A    N
ATOM   2138  CA   LEU A 321      13.591  45.320  52.332  1.00 20.95      A    C
```

FIG. 4-33

| | | | | | | | | | | | |
|---|---|---|---|---|---|---|---|---|---|---|---|
| ATOM | 2139 | CB | LEU | A | 321 | 14.304 | 46.597 | 52.771 | 1.00 | 9.43 | A C |
| ATOM | 2140 | CG | LEU | A | 321 | 15.808 | 46.577 | 52.505 | 1.00 | 9.43 | A C |
| ATOM | 2141 | CD1 | LEU | A | 321 | 16.402 | 47.885 | 52.951 | 1.00 | 9.43 | A C |
| ATOM | 2142 | CD2 | LEU | A | 321 | 16.452 | 45.400 | 53.208 | 1.00 | 9.43 | A C |
| ATOM | 2143 | C | LEU | A | 321 | 12.086 | 45.416 | 52.596 | 1.00 | 20.95 | A C |
| ATOM | 2144 | O | LEU | A | 321 | 11.548 | 46.492 | 52.839 | 1.00 | 20.95 | A O |
| ATOM | 2145 | N | GLU | A | 322 | 11.420 | 44.268 | 52.537 | 1.00 | 25.12 | A N |
| ATOM | 2146 | CA | GLU | A | 322 | 9.976 | 44.179 | 52.744 | 1.00 | 25.12 | A C |
| ATOM | 2147 | CB | GLU | A | 322 | 9.302 | 43.453 | 51.563 | 1.00 | 35.51 | A C |
| ATOM | 2148 | CG | GLU | A | 322 | 9.454 | 44.130 | 50.206 | 1.00 | 35.51 | A C |
| ATOM | 2149 | CD | GLU | A | 322 | 8.220 | 44.898 | 49.778 | 1.00 | 35.51 | A C |
| ATOM | 2150 | OE1 | GLU | A | 322 | 7.531 | 45.455 | 50.665 | 1.00 | 35.51 | A O |
| ATOM | 2151 | OE2 | GLU | A | 322 | 7.961 | 44.949 | 48.550 | 1.00 | 35.51 | A O |
| ATOM | 2152 | C | GLU | A | 322 | 9.679 | 43.395 | 54.010 | 1.00 | 25.12 | A C |
| ATOM | 2153 | O | GLU | A | 322 | 10.239 | 42.327 | 54.199 | 1.00 | 25.12 | A O |
| ATOM | 2154 | N | TYR | A | 323 | 8.796 | 43.898 | 54.871 | 1.00 | 18.04 | A N |
| ATOM | 2155 | CA | TYR | A | 323 | 8.482 | 43.169 | 56.090 | 1.00 | 18.04 | A C |
| ATOM | 2156 | CB | TYR | A | 323 | 7.303 | 43.792 | 56.845 | 1.00 | 29.33 | A C |
| ATOM | 2157 | CG | TYR | A | 323 | 7.599 | 45.059 | 57.622 | 1.00 | 29.33 | A C |
| ATOM | 2158 | CD1 | TYR | A | 323 | 8.669 | 45.124 | 58.530 | 1.00 | 29.33 | A C |
| ATOM | 2159 | CE1 | TYR | A | 323 | 8.949 | 46.297 | 59.240 | 1.00 | 29.33 | A C |
| ATOM | 2160 | CD2 | TYR | A | 323 | 6.807 | 46.197 | 57.444 | 1.00 | 29.33 | A C |
| ATOM | 2161 | CE2 | TYR | A | 323 | 7.069 | 47.383 | 58.143 | 1.00 | 29.33 | A C |
| ATOM | 2162 | CZ | TYR | A | 323 | 8.142 | 47.430 | 59.040 | 1.00 | 29.33 | A C |
| ATOM | 2163 | OH | TYR | A | 323 | 8.397 | 48.606 | 59.724 | 1.00 | 29.33 | A O |
| ATOM | 2164 | C | TYR | A | 323 | 8.105 | 41.756 | 55.697 | 1.00 | 18.04 | A C |
| ATOM | 2165 | O | TYR | A | 323 | 8.743 | 40.798 | 56.095 | 1.00 | 18.04 | A O |
| ATOM | 2166 | N | THR | A | 324 | 7.067 | 41.629 | 54.888 | 1.00 | 20.44 | A N |
| ATOM | 2167 | CA | THR | A | 324 | 6.616 | 40.316 | 54.464 | 1.00 | 20.44 | A C |
| ATOM | 2168 | CB | THR | A | 324 | 5.389 | 40.451 | 53.555 | 1.00 | 43.66 | A C |
| ATOM | 2169 | OG1 | THR | A | 324 | 4.346 | 41.139 | 54.263 | 1.00 | 43.66 | A O |
| ATOM | 2170 | CG2 | THR | A | 324 | 4.897 | 39.079 | 53.109 | 1.00 | 43.66 | A C |
| ATOM | 2171 | C | THR | A | 324 | 7.737 | 39.613 | 53.709 | 1.00 | 20.44 | A C |
| ATOM | 2172 | O | THR | A | 324 | 8.092 | 40.000 | 52.596 | 1.00 | 20.44 | A O |
| ATOM | 2173 | N | PRO | A | 325 | 8.306 | 38.562 | 54.310 | 1.00 | 31.15 | A N |
| ATOM | 2174 | CD | PRO | A | 325 | 7.983 | 38.061 | 55.652 | 1.00 | 28.89 | A C |
| ATOM | 2175 | CA | PRO | A | 325 | 9.398 | 37.785 | 53.714 | 1.00 | 31.15 | A C |
| ATOM | 2176 | CB | PRO | A | 325 | 9.628 | 36.676 | 54.743 | 1.00 | 28.89 | A C |
| ATOM | 2177 | CG | PRO | A | 325 | 9.244 | 37.328 | 56.019 | 1.00 | 28.89 | A C |
| ATOM | 2178 | C | PRO | A | 325 | 9.078 | 37.241 | 52.333 | 1.00 | 31.15 | A C |
| ATOM | 2179 | O | PRO | A | 325 | 9.946 | 37.146 | 51.477 | 1.00 | 31.15 | A O |
| ATOM | 2180 | N | THR | A | 326 | 7.813 | 36.911 | 52.129 | 1.00 | 23.05 | A N |
| ATOM | 2181 | CA | THR | A | 326 | 7.334 | 36.344 | 50.886 | 1.00 | 23.05 | A C |
| ATOM | 2182 | CB | THR | A | 326 | 5.992 | 35.642 | 51.185 | 1.00 | 26.65 | A C |
| ATOM | 2183 | OG1 | THR | A | 326 | 5.785 | 34.605 | 50.237 | 1.00 | 26.65 | A O |
| ATOM | 2184 | CG2 | THR | A | 326 | 4.831 | 36.612 | 51.129 | 1.00 | 26.65 | A C |
| ATOM | 2185 | C | THR | A | 326 | 7.201 | 37.389 | 49.765 | 1.00 | 23.05 | A C |
| ATOM | 2186 | O | THR | A | 326 | 7.131 | 37.040 | 48.591 | 1.00 | 23.05 | A O |
| ATOM | 2187 | N | ALA | A | 327 | 7.193 | 38.670 | 50.130 | 1.00 | 29.64 | A N |
| ATOM | 2188 | CA | ALA | A | 327 | 7.064 | 39.754 | 49.151 | 1.00 | 29.64 | A C |
| ATOM | 2189 | CB | ALA | A | 327 | 6.246 | 40.891 | 49.743 | 1.00 | 1.79 | A C |
| ATOM | 2190 | C | ALA | A | 327 | 8.397 | 40.302 | 48.635 | 1.00 | 29.64 | A C |
| ATOM | 2191 | O | ALA | A | 327 | 8.430 | 41.171 | 47.763 | 1.00 | 29.64 | A O |
| ATOM | 2192 | N | ARG | A | 328 | 9.500 | 39.807 | 49.181 | 1.00 | 36.12 | A N |
| ATOM | 2193 | CA | ARG | A | 328 | 10.803 | 40.266 | 48.750 | 1.00 | 36.12 | A C |
| ATOM | 2194 | CB | ARG | A | 328 | 11.860 | 39.855 | 49.766 | 1.00 | 20.53 | A C |
| ATOM | 2195 | CG | ARG | A | 328 | 11.676 | 40.498 | 51.122 | 1.00 | 20.53 | A C |
| ATOM | 2196 | CD | ARG | A | 328 | 12.482 | 39.792 | 52.183 | 1.00 | 20.53 | A C |
| ATOM | 2197 | NE | ARG | A | 328 | 12.221 | 40.372 | 53.491 | 1.00 | 20.53 | A N |
| ATOM | 2198 | CZ | ARG | A | 328 | 12.294 | 39.709 | 54.640 | 1.00 | 20.53 | A C |
| ATOM | 2199 | NH1 | ARG | A | 328 | 12.615 | 38.427 | 54.665 | 1.00 | 20.53 | A N |
| ATOM | 2200 | NH2 | ARG | A | 328 | 12.054 | 40.333 | 55.775 | 1.00 | 20.53 | A N |
| ATOM | 2201 | C | ARG | A | 328 | 11.090 | 39.619 | 47.412 | 1.00 | 36.12 | A C |
| ATOM | 2202 | O | ARG | A | 328 | 10.416 | 38.667 | 47.024 | 1.00 | 36.12 | A O |
| ATOM | 2203 | N | LEU | A | 329 | 12.081 | 40.147 | 46.701 | 1.00 | 27.39 | A N |
| ATOM | 2204 | CA | LEU | A | 329 | 12.460 | 39.601 | 45.411 | 1.00 | 27.39 | A C |
| ATOM | 2205 | CB | LEU | A | 329 | 13.257 | 40.628 | 44.609 | 1.00 | 27.92 | A C |

FIG. 4-34

```
ATOM   2206  CG   LEU A 329      12.472  41.592  43.726  1.00 27.92      A  C
ATOM   2207  CD1  LEU A 329      11.304  42.173  44.494  1.00 27.92      A  C
ATOM   2208  CD2  LEU A 329      13.407  42.675  43.240  1.00 27.92      A  C
ATOM   2209  C    LEU A 329      13.307  38.367  45.621  1.00 27.39      A  C
ATOM   2210  O    LEU A 329      13.928  38.196  46.669  1.00 27.39      A  O
ATOM   2211  N    THR A 330      13.318  37.487  44.634  1.00 28.11      A  N
ATOM   2212  CA   THR A 330      14.136  36.297  44.752  1.00 28.11      A  C
ATOM   2213  CB   THR A 330      13.544  35.111  43.991  1.00 20.87      A  C
ATOM   2214  OG1  THR A 330      13.693  35.322  42.584  1.00 20.87      A  O
ATOM   2215  CG2  THR A 330      12.078  34.961  44.318  1.00 20.87      A  C
ATOM   2216  C    THR A 330      15.471  36.652  44.136  1.00 28.11      A  C
ATOM   2217  O    THR A 330      15.531  37.434  43.189  1.00 28.11      A  O
ATOM   2218  N    PRO A 331      16.560  36.091  44.676  1.00 28.11      A  N
ATOM   2219  CD   PRO A 331      16.583  35.022  45.689  1.00 13.37      A  C
ATOM   2220  CA   PRO A 331      17.902  36.354  44.167  1.00 28.11      A  C
ATOM   2221  CB   PRO A 331      18.677  35.137  44.648  1.00 13.37      A  C
ATOM   2222  CG   PRO A 331      18.051  34.881  45.992  1.00 13.37      A  C
ATOM   2223  C    PRO A 331      17.910  36.505  42.648  1.00 28.11      A  C
ATOM   2224  O    PRO A 331      18.459  37.480  42.125  1.00 28.11      A  O
ATOM   2225  N    LEU A 332      17.286  35.557  41.939  1.00 27.74      A  N
ATOM   2226  CA   LEU A 332      17.259  35.625  40.481  1.00 27.74      A  C
ATOM   2227  CB   LEU A 332      16.712  34.346  39.856  1.00 27.63      A  C
ATOM   2228  CG   LEU A 332      17.719  33.419  39.163  1.00 27.63      A  C
ATOM   2229  CD1  LEU A 332      16.958  32.375  38.387  1.00 27.63      A  C
ATOM   2230  CD2  LEU A 332      18.622  34.190  38.226  1.00 27.63      A  C
ATOM   2231  C    LEU A 332      16.432  36.802  40.020  1.00 27.74      A  C
ATOM   2232  O    LEU A 332      16.824  37.513  39.104  1.00 27.74      A  O
ATOM   2233  N    GLU A 333      15.286  37.006  40.658  1.00 38.98      A  N
ATOM   2234  CA   GLU A 333      14.427  38.140  40.323  1.00 38.98      A  C
ATOM   2235  CB   GLU A 333      13.174  38.174  41.217  1.00 36.47      A  C
ATOM   2236  CG   GLU A 333      12.123  37.131  40.865  1.00 36.47      A  C
ATOM   2237  CD   GLU A 333      10.937  37.126  41.812  1.00 36.47      A  C
ATOM   2238  OE1  GLU A 333      11.095  37.565  42.979  1.00 36.47      A  O
ATOM   2239  OE2  GLU A 333       9.856  36.661  41.383  1.00 36.47      A  O
ATOM   2240  C    GLU A 333      15.206  39.444  40.507  1.00 38.98      A  C
ATOM   2241  O    GLU A 333      14.977  40.421  39.794  1.00 38.98      A  O
ATOM   2242  N    ALA A 334      16.128  39.449  41.466  1.00 30.87      A  N
ATOM   2243  CA   ALA A 334      16.936  40.621  41.743  1.00 30.87      A  C
ATOM   2244  CB   ALA A 334      17.625  40.461  43.055  1.00 27.95      A  C
ATOM   2245  C    ALA A 334      17.958  40.830  40.641  1.00 30.87      A  C
ATOM   2246  O    ALA A 334      18.193  41.955  40.227  1.00 30.87      A  O
ATOM   2247  N    CYS A 335      18.572  39.748  40.173  1.00 26.93      A  N
ATOM   2248  CA   CYS A 335      19.550  39.849  39.095  1.00 26.93      A  C
ATOM   2249  CB   CYS A 335      20.116  38.476  38.740  1.00 32.61      A  C
ATOM   2250  SG   CYS A 335      21.388  37.885  39.834  1.00 32.61      A  S
ATOM   2251  C    CYS A 335      18.941  40.456  37.836  1.00 26.93      A  C
ATOM   2252  O    CYS A 335      19.618  41.143  37.086  1.00 26.93      A  O
ATOM   2253  N    ALA A 336      17.656  40.200  37.625  1.00 28.02      A  N
ATOM   2254  CA   ALA A 336      16.940  40.667  36.456  1.00 28.02      A  C
ATOM   2255  CB   ALA A 336      15.818  39.716  36.160  1.00 18.31      A  C
ATOM   2256  C    ALA A 336      16.390  42.061  36.638  1.00 28.02      A  C
ATOM   2257  O    ALA A 336      15.688  42.559  35.763  1.00 28.02      A  O
ATOM   2258  N    HIS A 337      16.680  42.685  37.778  1.00 29.34      A  N
ATOM   2259  CA   HIS A 337      16.203  44.045  38.035  1.00 29.34      A  C
ATOM   2260  CB   HIS A 337      16.419  44.436  39.500  1.00 26.90      A  C
ATOM   2261  CG   HIS A 337      15.784  45.741  39.866  1.00 26.90      A  C
ATOM   2262  CD2  HIS A 337      16.212  47.016  39.718  1.00 26.90      A  C
ATOM   2263  ND1  HIS A 337      14.509  45.823  40.383  1.00 26.90      A  N
ATOM   2264  CE1  HIS A 337      14.179  47.093  40.536  1.00 26.90      A  C
ATOM   2265  NE2  HIS A 337      15.195  47.838  40.138  1.00 26.90      A  N
ATOM   2266  C    HIS A 337      16.914  45.064  37.122  1.00 29.34      A  C
ATOM   2267  O    HIS A 337      18.107  44.932  36.807  1.00 29.34      A  O
ATOM   2268  N    SER A 338      16.173  46.088  36.709  1.00 30.66      A  N
ATOM   2269  CA   SER A 338      16.701  47.106  35.813  1.00 30.66      A  C
ATOM   2270  CB   SER A 338      15.581  48.047  35.396  1.00 37.71      A  C
ATOM   2271  OG   SER A 338      14.747  48.335  36.498  1.00 37.71      A  O
ATOM   2272  C    SER A 338      17.878  47.899  36.363  1.00 30.66      A  C
```

FIG. 4-35

```
ATOM   2273  O    SER A 338     18.509  48.661  35.638  1.00 30.66      A  O
ATOM   2274  N    PHE A 339     18.178  47.722  37.641  1.00 28.31      A  N
ATOM   2275  CA   PHE A 339     19.309  48.411  38.245  1.00 28.31      A  C
ATOM   2276  CB   PHE A 339     19.295  48.236  39.769  1.00 25.07      A  C
ATOM   2277  CG   PHE A 339     20.555  48.709  40.461  1.00 25.07      A  C
ATOM   2278  CD1  PHE A 339     21.047  49.995  40.259  1.00 25.07      A  C
ATOM   2279  CD2  PHE A 339     21.243  47.864  41.330  1.00 25.07      A  C
ATOM   2280  CE1  PHE A 339     22.206  50.426  40.916  1.00 25.07      A  C
ATOM   2281  CE2  PHE A 339     22.402  48.288  41.990  1.00 25.07      A  C
ATOM   2282  CZ   PHE A 339     22.882  49.567  41.783  1.00 25.07      A  C
ATOM   2283  C    PHE A 339     20.582  47.802  37.689  1.00 28.31      A  C
ATOM   2284  O    PHE A 339     21.631  48.427  37.697  1.00 28.31      A  O
ATOM   2285  N    PHE A 340     20.478  46.575  37.208  1.00 27.07      A  N
ATOM   2286  CA   PHE A 340     21.624  45.877  36.663  1.00 27.07      A  C
ATOM   2287  CB   PHE A 340     21.646  44.451  37.191  1.00 23.90      A  C
ATOM   2288  CG   PHE A 340     21.651  44.358  38.683  1.00 23.90      A  C
ATOM   2289  CD1  PHE A 340     22.773  44.722  39.415  1.00 23.90      A  C
ATOM   2290  CD2  PHE A 340     20.533  43.887  39.359  1.00 23.90      A  C
ATOM   2291  CE1  PHE A 340     22.771  44.615  40.795  1.00 23.90      A  C
ATOM   2292  CE2  PHE A 340     20.528  43.779  40.729  1.00 23.90      A  C
ATOM   2293  CZ   PHE A 340     21.644  44.140  41.449  1.00 23.90      A  C
ATOM   2294  C    PHE A 340     21.613  45.845  35.145  1.00 27.07      A  C
ATOM   2295  O    PHE A 340     22.329  45.042  34.531  1.00 27.07      A  O
ATOM   2296  N    ASP A 341     20.801  46.696  34.526  1.00 33.66      A  N
ATOM   2297  CA   ASP A 341     20.758  46.703  33.076  1.00 33.66      A  C
ATOM   2298  CB   ASP A 341     19.709  47.708  32.579  1.00 40.09      A  C
ATOM   2299  CG   ASP A 341     18.306  47.100  32.476  1.00 40.09      A  C
ATOM   2300  OD1  ASP A 341     18.187  45.885  32.190  1.00 40.09      A  O
ATOM   2301  OD2  ASP A 341     17.315  47.844  32.657  1.00 40.09      A  O
ATOM   2302  C    ASP A 341     22.136  47.018  32.488  1.00 33.66      A  C
ATOM   2303  O    ASP A 341     22.627  46.309  31.611  1.00 33.66      A  O
ATOM   2304  N    GLU A 342     22.765  48.065  33.009  1.00 35.21      A  N
ATOM   2305  CA   GLU A 342     24.069  48.508  32.543  1.00 35.21      A  C
ATOM   2306  CB   GLU A 342     24.641  49.541  33.520  1.00 45.61      A  C
ATOM   2307  CG   GLU A 342     25.943  50.172  33.056  1.00 45.61      A  C
ATOM   2308  CD   GLU A 342     26.439  51.280  33.986  1.00 45.61      A  C
ATOM   2309  OE1  GLU A 342     25.568  51.980  34.564  1.00 45.61      A  O
ATOM   2310  OE2  GLU A 342     27.684  51.454  34.117  1.00 45.61      A  O
ATOM   2311  C    GLU A 342     25.057  47.370  32.370  1.00 35.21      A  C
ATOM   2312  O    GLU A 342     25.918  47.427  31.498  1.00 35.21      A  O
ATOM   2313  N    LEU A 343     24.925  46.329  33.183  1.00 24.43      A  N
ATOM   2314  CA   LEU A 343     25.848  45.213  33.109  1.00 24.43      A  C
ATOM   2315  CB   LEU A 343     25.730  44.355  34.371  1.00 26.21      A  C
ATOM   2316  CG   LEU A 343     25.870  45.122  35.694  1.00 26.21      A  C
ATOM   2317  CD1  LEU A 343     25.819  44.177  36.882  1.00 26.21      A  C
ATOM   2318  CD2  LEU A 343     27.194  45.885  35.692  1.00 26.21      A  C
ATOM   2319  C    LEU A 343     25.539  44.389  31.877  1.00 24.43      A  C
ATOM   2320  O    LEU A 343     26.402  43.703  31.337  1.00 24.43      A  O
ATOM   2321  N    ARG A 344     24.294  44.467  31.433  1.00 22.77      A  N
ATOM   2322  CA   ARG A 344     23.859  43.720  30.268  1.00 22.77      A  C
ATOM   2323  CB   ARG A 344     22.361  43.437  30.354  1.00 27.26      A  C
ATOM   2324  CG   ARG A 344     22.008  42.171  31.119  1.00 27.26      A  C
ATOM   2325  CD   ARG A 344     20.495  41.962  31.183  1.00 27.26      A  C
ATOM   2326  NE   ARG A 344     19.817  42.953  32.018  1.00 27.26      A  N
ATOM   2327  CZ   ARG A 344     19.732  42.892  33.344  1.00 27.26      A  C
ATOM   2328  NH1  ARG A 344     20.275  41.886  34.015  1.00 27.26      A  N
ATOM   2329  NH2  ARG A 344     19.098  43.844  34.006  1.00 27.26      A  N
ATOM   2330  C    ARG A 344     24.190  44.465  28.983  1.00 22.77      A  C
ATOM   2331  O    ARG A 344     24.061  43.934  27.886  1.00 22.77      A  O
ATOM   2332  N    ASP A 345     24.614  45.709  29.130  1.00 29.72      A  N
ATOM   2333  CA   ASP A 345     25.010  46.525  27.992  1.00 29.72      A  C
ATOM   2334  CB   ASP A 345     25.462  47.906  28.485  1.00 58.81      A  C
ATOM   2335  CG   ASP A 345     25.788  48.875  27.342  1.00 58.81      A  C
ATOM   2336  OD1  ASP A 345     26.575  48.493  26.432  1.00 58.81      A  O
ATOM   2337  OD2  ASP A 345     25.256  50.019  27.367  1.00 58.81      A  O
ATOM   2338  C    ASP A 345     26.195  45.801  27.347  1.00 29.72      A  C
ATOM   2339  O    ASP A 345     27.093  45.310  28.031  1.00 29.72      A  O
```

FIG. 4-36

```
ATOM   2340  N    PRO A 346      26.213  45.726  26.017  1.00 34.64      A  N
ATOM   2341  CD   PRO A 346      25.235  46.245  25.051  1.00 28.88      A  C
ATOM   2342  CA   PRO A 346      27.318  45.046  25.340  1.00 34.64      A  C
ATOM   2343  CB   PRO A 346      26.826  44.972  23.906  1.00 28.88      A  C
ATOM   2344  CG   PRO A 346      26.028  46.240  23.783  1.00 28.88      A  C
ATOM   2345  C    PRO A 346      28.623  45.804  25.474  1.00 34.64      A  C
ATOM   2346  O    PRO A 346      29.700  45.207  25.459  1.00 34.64      A  O
ATOM   2347  N    ASN A 347      28.525  47.120  25.627  1.00 41.18      A  N
ATOM   2348  CA   ASN A 347      29.729  47.931  25.757  1.00 41.18      A  C
ATOM   2349  CB   ASN A 347      29.562  49.259  25.010  1.00 55.72      A  C
ATOM   2350  CG   ASN A 347      29.919  49.138  23.532  1.00 55.72      A  C
ATOM   2351  OD1  ASN A 347      29.126  48.639  22.719  1.00 55.72      A  O
ATOM   2352  ND2  ASN A 347      31.137  49.571  23.183  1.00 55.72      A  N
ATOM   2353  C    ASN A 347      30.263  48.184  27.163  1.00 41.18      A  C
ATOM   2354  O    ASN A 347      31.285  48.859  27.326  1.00 41.18      A  O
ATOM   2355  N    VAL A 348      29.594  47.627  28.172  1.00 40.49      A  N
ATOM   2356  CA   VAL A 348      30.021  47.816  29.556  1.00 40.49      A  C
ATOM   2357  CB   VAL A 348      29.137  47.011  30.542  1.00 35.15      A  C
ATOM   2358  CG1  VAL A 348      29.303  45.522  30.300  1.00 35.15      A  C
ATOM   2359  CG2  VAL A 348      29.497  47.369  31.976  1.00 35.15      A  C
ATOM   2360  C    VAL A 348      31.478  47.395  29.754  1.00 40.49      A  C
ATOM   2361  O    VAL A 348      31.912  46.362  29.240  1.00 40.49      A  O
ATOM   2362  N    LYS A 349      32.229  48.216  30.483  1.00 29.53      A  N
ATOM   2363  CA   LYS A 349      33.621  47.929  30.791  1.00 29.53      A  C
ATOM   2364  CB   LYS A 349      34.562  48.508  29.716  1.00 50.78      A  C
ATOM   2365  CG   LYS A 349      34.343  47.928  28.310  1.00 50.78      A  C
ATOM   2366  CD   LYS A 349      35.654  47.672  27.587  1.00 50.78      A  C
ATOM   2367  CE   LYS A 349      36.374  46.443  28.155  1.00 50.78      A  C
ATOM   2368  NZ   LYS A 349      37.814  46.324  27.691  1.00 50.78      A  N
ATOM   2369  C    LYS A 349      33.976  48.476  32.187  1.00 29.53      A  C
ATOM   2370  O    LYS A 349      33.313  49.367  32.727  1.00 29.53      A  O
ATOM   2371  N    LEU A 350      35.012  47.932  32.797  1.00 41.51      A  N
ATOM   2372  CA   LEU A 350      35.377  48.423  34.111  1.00 41.51      A  C
ATOM   2373  CB   LEU A 350      36.319  47.425  34.794  1.00 53.76      A  C
ATOM   2374  CG   LEU A 350      35.550  46.166  35.131  1.00 53.76      A  C
ATOM   2375  CD1  LEU A 350      36.388  45.075  35.739  1.00 53.76      A  C
ATOM   2376  CD2  LEU A 350      34.365  46.519  35.996  1.00 53.76      A  C
ATOM   2377  C    LEU A 350      36.020  49.796  34.006  1.00 41.51      A  C
ATOM   2378  O    LEU A 350      36.639  50.108  32.982  1.00 41.51      A  O
ATOM   2379  N    PRO A 351      35.891  50.634  35.057  1.00 34.17      A  N
ATOM   2380  CD   PRO A 351      35.450  50.397  36.444  1.00 51.93      A  C
ATOM   2381  CA   PRO A 351      36.527  51.952  34.927  1.00 34.17      A  C
ATOM   2382  CB   PRO A 351      36.229  52.621  36.264  1.00 51.93      A  C
ATOM   2383  CG   PRO A 351      36.216  51.474  37.216  1.00 51.93      A  C
ATOM   2384  C    PRO A 351      38.009  51.671  34.737  1.00 34.17      A  C
ATOM   2385  O    PRO A 351      38.711  52.349  33.987  1.00 34.17      A  O
ATOM   2386  N    ASN A 352      38.422  50.619  35.437  1.00 48.43      A  N
ATOM   2387  CA   ASN A 352      39.748  50.031  35.462  1.00 48.43      A  C
ATOM   2388  CB   ASN A 352      39.570  48.635  36.069  1.00 77.92      A  C
ATOM   2389  CG   ASN A 352      40.722  47.705  35.784  1.00 77.92      A  C
ATOM   2390  OD1  ASN A 352      41.283  47.708  34.680  1.00 77.92      A  O
ATOM   2391  ND2  ASN A 352      41.069  46.868  36.779  1.00 77.92      A  N
ATOM   2392  C    ASN A 352      40.311  49.945  34.048  1.00 48.43      A  C
ATOM   2393  O    ASN A 352      41.503  50.149  33.841  1.00 48.43      A  O
ATOM   2394  N    GLY A 353      39.448  49.640  33.077  1.00 41.47      A  N
ATOM   2395  CA   GLY A 353      39.882  49.523  31.690  1.00 41.47      A  C
ATOM   2396  C    GLY A 353      39.598  48.140  31.103  1.00 41.47      A  C
ATOM   2397  O    GLY A 353      39.253  47.992  29.921  1.00 41.47      A  O
ATOM   2398  N    ARG A 354      39.746  47.115  31.946  1.00 42.07      A  N
ATOM   2399  CA   ARG A 354      39.511  45.723  31.549  1.00 42.07      A  C
ATOM   2400  CB   ARG A 354      39.952  44.767  32.672  1.00 78.17      A  C
ATOM   2401  CG   ARG A 354      41.175  45.245  33.434  1.00 78.17      A  C
ATOM   2402  CD   ARG A 354      41.569  44.345  34.605  1.00 78.17      A  C
ATOM   2403  NE   ARG A 354      42.295  43.147  34.178  1.00 78.17      A  N
ATOM   2404  CZ   ARG A 354      43.127  42.451  34.956  1.00 78.17      A  C
ATOM   2405  NH1  ARG A 354      43.340  42.842  36.213  1.00 78.17      A  N
ATOM   2406  NH2  ARG A 354      43.747  41.368  34.474  1.00 78.17      A  N
```

FIG. 4-37

```
ATOM   2407  C    ARG A 354      38.039  45.430  31.248  1.00 42.07      A    C
ATOM   2408  O    ARG A 354      37.184  46.321  31.238  1.00 42.07      A    O
ATOM   2409  N    ASP A 355      37.759  44.154  31.029  1.00 34.98      A    N
ATOM   2410  CA   ASP A 355      36.414  43.676  30.743  1.00 34.98      A    C
ATOM   2411  CB   ASP A 355      36.495  42.437  29.861  1.00 79.47      A    C
ATOM   2412  CG   ASP A 355      35.897  42.650  28.489  1.00 79.47      A    C
ATOM   2413  OD1  ASP A 355      34.745  43.167  28.418  1.00 79.47      A    O
ATOM   2414  OD2  ASP A 355      36.589  42.277  27.501  1.00 79.47      A    O
ATOM   2415  C    ASP A 355      35.659  43.292  32.017  1.00 34.98      A    C
ATOM   2416  O    ASP A 355      36.260  42.979  33.055  1.00 34.98      A    O
ATOM   2417  N    THR A 356      34.335  43.282  31.930  1.00 37.81      A    N
ATOM   2418  CA   THR A 356      33.558  42.913  33.099  1.00 37.81      A    C
ATOM   2419  CB   THR A 356      32.061  43.251  32.949  1.00 31.34      A    C
ATOM   2420  OG1  THR A 356      31.344  42.080  32.553  1.00 31.34      A    O
ATOM   2421  CG2  THR A 356      31.861  44.322  31.918  1.00 31.34      A    C
ATOM   2422  C    THR A 356      33.729  41.408  33.234  1.00 37.81      A    C
ATOM   2423  O    THR A 356      33.905  40.703  32.234  1.00 37.81      A    O
ATOM   2424  N    PRO A 357      33.693  40.888  34.469  1.00 29.15      A    N
ATOM   2425  CD   PRO A 357      33.378  41.510  35.770  1.00 38.66      A    C
ATOM   2426  CA   PRO A 357      33.861  39.440  34.605  1.00 29.15      A    C
ATOM   2427  CB   PRO A 357      34.003  39.259  36.113  1.00 38.66      A    C
ATOM   2428  CG   PRO A 357      33.049  40.305  36.645  1.00 38.66      A    C
ATOM   2429  C    PRO A 357      32.644  38.714  34.045  1.00 29.15      A    C
ATOM   2430  O    PRO A 357      31.714  39.335  33.518  1.00 29.15      A    O
ATOM   2431  N    ALA A 358      32.661  37.393  34.153  1.00 39.07      A    N
ATOM   2432  CA   ALA A 358      31.549  36.586  33.690  1.00 39.07      A    C
ATOM   2433  CB   ALA A 358      31.825  35.138  33.958  1.00 33.19      A    C
ATOM   2434  C    ALA A 358      30.318  37.015  34.462  1.00 39.07      A    C
ATOM   2435  O    ALA A 358      30.358  37.100  35.686  1.00 39.07      A    O
ATOM   2436  N    LEU A 359      29.222  37.293  33.772  1.00 28.37      A    N
ATOM   2437  CA   LEU A 359      28.014  37.681  34.483  1.00 28.37      A    C
ATOM   2438  CB   LEU A 359      27.738  39.178  34.345  1.00 25.93      A    C
ATOM   2439  CG   LEU A 359      28.764  40.169  34.887  1.00 25.93      A    C
ATOM   2440  CD1  LEU A 359      28.127  41.551  34.902  1.00 25.93      A    C
ATOM   2441  CD2  LEU A 359      29.214  39.781  36.280  1.00 25.93      A    C
ATOM   2442  C    LEU A 359      26.821  36.925  33.944  1.00 28.37      A    C
ATOM   2443  O    LEU A 359      25.760  36.913  34.560  1.00 28.37      A    O
ATOM   2444  N    PHE A 360      27.003  36.283  32.795  1.00 31.80      A    N
ATOM   2445  CA   PHE A 360      25.912  35.560  32.153  1.00 31.80      A    C
ATOM   2446  CB   PHE A 360      25.639  36.194  30.794  1.00 29.36      A    C
ATOM   2447  CG   PHE A 360      25.803  37.681  30.782  1.00 29.36      A    C
ATOM   2448  CD1  PHE A 360      25.089  38.474  31.658  1.00 29.36      A    C
ATOM   2449  CD2  PHE A 360      26.670  38.293  29.890  1.00 29.36      A    C
ATOM   2450  CE1  PHE A 360      25.231  39.864  31.640  1.00 29.36      A    C
ATOM   2451  CE2  PHE A 360      26.816  39.682  29.868  1.00 29.36      A    C
ATOM   2452  CZ   PHE A 360      26.095  40.466  30.745  1.00 29.36      A    C
ATOM   2453  C    PHE A 360      26.044  34.042  31.979  1.00 31.80      A    C
ATOM   2454  O    PHE A 360      25.123  33.405  31.502  1.00 31.80      A    O
ATOM   2455  N    ASN A 361      27.165  33.450  32.361  1.00 34.36      A    N
ATOM   2456  CA   ASN A 361      27.320  32.008  32.215  1.00 34.36      A    C
ATOM   2457  CB   ASN A 361      28.810  31.641  32.317  1.00 41.86      A    C
ATOM   2458  CG   ASN A 361      29.500  32.265  33.537  1.00 41.86      A    C
ATOM   2459  OD1  ASN A 361      29.067  33.309  34.043  1.00 41.86      A    O
ATOM   2460  ND2  ASN A 361      30.597  31.637  33.999  1.00 41.86      A    N
ATOM   2461  C    ASN A 361      26.463  31.161  33.169  1.00 34.36      A    C
ATOM   2462  O    ASN A 361      26.960  30.231  33.828  1.00 34.36      A    O
ATOM   2463  N    PHE A 362      25.167  31.480  33.210  1.00 48.71      A    N
ATOM   2464  CA   PHE A 362      24.210  30.785  34.066  1.00 48.71      A    C
ATOM   2465  CB   PHE A 362      22.805  31.370  33.872  1.00 37.43      A    C
ATOM   2466  CG   PHE A 362      22.604  32.706  34.543  1.00 37.43      A    C
ATOM   2467  CD1  PHE A 362      22.452  32.791  35.923  1.00 37.43      A    C
ATOM   2468  CD2  PHE A 362      22.580  33.883  33.796  1.00 37.43      A    C
ATOM   2469  CE1  PHE A 362      22.279  34.022  36.540  1.00 37.43      A    C
ATOM   2470  CE2  PHE A 362      22.408  35.115  34.414  1.00 37.43      A    C
ATOM   2471  CZ   PHE A 362      22.258  35.182  35.782  1.00 37.43      A    C
ATOM   2472  C    PHE A 362      24.177  29.300  33.776  1.00 48.71      A    C
ATOM   2473  O    PHE A 362      24.822  28.823  32.847  1.00 48.71      A    O
```

FIG. 4-38

| ATOM | 2474 | N   | THR A 363 | 23.430 | 28.570 | 34.590 | 1.00 | 41.24 | A | N |
| ATOM | 2475 | CA  | THR A 363 | 23.272 | 27.136 | 34.411 | 1.00 | 41.24 | A | C |
| ATOM | 2476 | CB  | THR A 363 | 24.049 | 26.365 | 35.474 | 1.00 | 27.92 | A | C |
| ATOM | 2477 | OG1 | THR A 363 | 23.456 | 26.588 | 36.760 | 1.00 | 27.92 | A | O |
| ATOM | 2478 | CG2 | THR A 363 | 25.494 | 26.832 | 35.494 | 1.00 | 27.92 | A | C |
| ATOM | 2479 | C   | THR A 363 | 21.777 | 26.882 | 34.590 | 1.00 | 41.24 | A | C |
| ATOM | 2480 | O   | THR A 363 | 21.014 | 27.802 | 34.902 | 1.00 | 41.24 | A | O |
| ATOM | 2481 | N   | THR A 364 | 21.342 | 25.650 | 34.386 | 1.00 | 50.91 | A | N |
| ATOM | 2482 | CA  | THR A 364 | 19.927 | 25.343 | 34.562 | 1.00 | 50.91 | A | C |
| ATOM | 2483 | CB  | THR A 364 | 19.598 | 24.019 | 33.912 | 1.00 | 49.45 | A | C |
| ATOM | 2484 | OG1 | THR A 364 | 20.333 | 22.982 | 34.570 | 1.00 | 49.45 | A | O |
| ATOM | 2485 | CG2 | THR A 364 | 19.996 | 24.052 | 32.459 | 1.00 | 49.45 | A | C |
| ATOM | 2486 | C   | THR A 364 | 19.663 | 25.257 | 36.067 | 1.00 | 50.91 | A | C |
| ATOM | 2487 | O   | THR A 364 | 18.553 | 25.516 | 36.554 | 1.00 | 50.91 | A | O |
| ATOM | 2488 | N   | GLN A 365 | 20.710 | 24.884 | 36.792 | 1.00 | 38.49 | A | N |
| ATOM | 2489 | CA  | GLN A 365 | 20.657 | 24.789 | 38.242 | 1.00 | 38.49 | A | C |
| ATOM | 2490 | CB  | GLN A 365 | 22.002 | 24.249 | 38.761 | 1.00 | 32.90 | A | C |
| ATOM | 2491 | CG  | GLN A 365 | 22.134 | 24.200 | 40.266 | 1.00 | 32.90 | A | C |
| ATOM | 2492 | CD  | GLN A 365 | 21.119 | 23.280 | 40.916 | 1.00 | 32.90 | A | C |
| ATOM | 2493 | OE1 | GLN A 365 | 20.077 | 22.974 | 40.329 | 1.00 | 32.90 | A | O |
| ATOM | 2494 | NE2 | GLN A 365 | 21.404 | 22.850 | 42.148 | 1.00 | 32.90 | A | N |
| ATOM | 2495 | C   | GLN A 365 | 20.405 | 26.200 | 38.779 | 1.00 | 38.49 | A | C |
| ATOM | 2496 | O   | GLN A 365 | 19.539 | 26.412 | 39.629 | 1.00 | 38.49 | A | O |
| ATOM | 2497 | N   | GLU A 366 | 21.156 | 27.166 | 38.260 | 1.00 | 30.93 | A | N |
| ATOM | 2498 | CA  | GLU A 366 | 21.017 | 28.542 | 38.695 | 1.00 | 30.93 | A | C |
| ATOM | 2499 | CB  | GLU A 366 | 22.087 | 29.430 | 38.048 | 1.00 | 33.59 | A | C |
| ATOM | 2500 | CG  | GLU A 366 | 23.543 | 29.140 | 38.425 | 1.00 | 33.59 | A | C |
| ATOM | 2501 | CD  | GLU A 366 | 24.510 | 30.281 | 38.039 | 1.00 | 33.59 | A | C |
| ATOM | 2502 | OE1 | GLU A 366 | 24.445 | 31.382 | 38.654 | 1.00 | 33.59 | A | O |
| ATOM | 2503 | OE2 | GLU A 366 | 25.334 | 30.058 | 37.119 | 1.00 | 33.59 | A | O |
| ATOM | 2504 | C   | GLU A 366 | 19.662 | 29.123 | 38.336 | 1.00 | 30.93 | A | C |
| ATOM | 2505 | O   | GLU A 366 | 19.069 | 29.832 | 39.132 | 1.00 | 30.93 | A | O |
| ATOM | 2506 | N   | LEU A 367 | 19.177 | 28.829 | 37.136 | 1.00 | 30.01 | A | N |
| ATOM | 2507 | CA  | LEU A 367 | 17.906 | 29.381 | 36.669 | 1.00 | 30.01 | A | C |
| ATOM | 2508 | CB  | LEU A 367 | 17.976 | 29.567 | 35.149 | 1.00 | 30.23 | A | C |
| ATOM | 2509 | CG  | LEU A 367 | 19.210 | 30.344 | 34.667 | 1.00 | 30.23 | A | C |
| ATOM | 2510 | CD1 | LEU A 367 | 19.511 | 30.004 | 33.236 | 1.00 | 30.23 | A | C |
| ATOM | 2511 | CD2 | LEU A 367 | 19.002 | 31.841 | 34.852 | 1.00 | 30.23 | A | C |
| ATOM | 2512 | C   | LEU A 367 | 16.640 | 28.598 | 37.012 | 1.00 | 30.01 | A | C |
| ATOM | 2513 | O   | LEU A 367 | 15.527 | 29.051 | 36.709 | 1.00 | 30.01 | A | O |
| ATOM | 2514 | N   | SER A 368 | 16.809 | 27.435 | 37.642 | 1.00 | 31.94 | A | N |
| ATOM | 2515 | CA  | SER A 368 | 15.684 | 26.569 | 37.987 | 1.00 | 31.94 | A | C |
| ATOM | 2516 | CB  | SER A 368 | 16.182 | 25.351 | 38.758 | 1.00 | 41.43 | A | C |
| ATOM | 2517 | OG  | SER A 368 | 16.778 | 25.746 | 39.977 | 1.00 | 41.43 | A | O |
| ATOM | 2518 | C   | SER A 368 | 14.526 | 27.208 | 38.755 | 1.00 | 31.94 | A | C |
| ATOM | 2519 | O   | SER A 368 | 13.387 | 26.780 | 38.619 | 1.00 | 31.94 | A | O |
| ATOM | 2520 | N   | SER A 369 | 14.807 | 28.225 | 39.558 | 1.00 | 33.00 | A | N |
| ATOM | 2521 | CA  | SER A 369 | 13.762 | 28.887 | 40.330 | 1.00 | 33.00 | A | C |
| ATOM | 2522 | CB  | SER A 369 | 14.387 | 29.916 | 41.271 | 1.00 | 38.11 | A | C |
| ATOM | 2523 | OG  | SER A 369 | 15.415 | 30.661 | 40.631 | 1.00 | 38.11 | A | O |
| ATOM | 2524 | C   | SER A 369 | 12.738 | 29.566 | 39.437 | 1.00 | 33.00 | A | C |
| ATOM | 2525 | O   | SER A 369 | 11.603 | 29.778 | 39.840 | 1.00 | 33.00 | A | O |
| ATOM | 2526 | N   | ASN A 370 | 13.147 | 29.905 | 38.221 | 1.00 | 49.14 | A | N |
| ATOM | 2527 | CA  | ASN A 370 | 12.268 | 30.584 | 37.273 | 1.00 | 49.14 | A | C |
| ATOM | 2528 | CB  | ASN A 370 | 11.925 | 31.978 | 37.810 | 1.00 | 35.52 | A | C |
| ATOM | 2529 | CG  | ASN A 370 | 10.913 | 32.711 | 36.953 | 1.00 | 35.52 | A | C |
| ATOM | 2530 | OD1 | ASN A 370 | 10.817 | 32.487 | 35.749 | 1.00 | 35.52 | A | O |
| ATOM | 2531 | ND2 | ASN A 370 | 10.162 | 33.611 | 37.570 | 1.00 | 35.52 | A | N |
| ATOM | 2532 | C   | ASN A 370 | 13.002 | 30.702 | 35.928 | 1.00 | 49.14 | A | C |
| ATOM | 2533 | O   | ASN A 370 | 13.416 | 31.789 | 35.524 | 1.00 | 49.14 | A | O |
| ATOM | 2534 | N   | PRO A 371 | 13.177 | 29.578 | 35.214 | 1.00 | 34.57 | A | N |
| ATOM | 2535 | CD  | PRO A 371 | 12.817 | 28.200 | 35.566 | 1.00 | 22.28 | A | C |
| ATOM | 2536 | CA  | PRO A 371 | 13.873 | 29.618 | 33.926 | 1.00 | 34.57 | A | C |
| ATOM | 2537 | CB  | PRO A 371 | 13.607 | 28.231 | 33.337 | 1.00 | 22.28 | A | C |
| ATOM | 2538 | CG  | PRO A 371 | 12.586 | 27.618 | 34.239 | 1.00 | 22.28 | A | C |
| ATOM | 2539 | C   | PRO A 371 | 13.542 | 30.762 | 32.970 | 1.00 | 34.57 | A | C |
| ATOM | 2540 | O   | PRO A 371 | 14.439 | 31.383 | 32.413 | 1.00 | 34.57 | A | O |

FIG. 4-39

```
ATOM   2541  N    PRO A 372      12.260  31.063  32.768  1.00 31.58      A  N
ATOM   2542  CD   PRO A 372      11.075  30.346  33.269  1.00 35.74      A  C
ATOM   2543  CA   PRO A 372      11.864  32.149  31.867  1.00 31.58      A  C
ATOM   2544  CB   PRO A 372      10.399  32.336  32.206  1.00 35.74      A  C
ATOM   2545  CG   PRO A 372       9.964  30.910  32.399  1.00 35.74      A  C
ATOM   2546  C    PRO A 372      12.661  33.442  32.010  1.00 31.58      A  C
ATOM   2547  O    PRO A 372      12.675  34.266  31.092  1.00 31.58      A  O
ATOM   2548  N    LEU A 373      13.326  33.623  33.150  1.00 41.80      A  N
ATOM   2549  CA   LEU A 373      14.116  34.834  33.376  1.00 41.80      A  C
ATOM   2550  CB   LEU A 373      14.411  35.020  34.868  1.00 21.32      A  C
ATOM   2551  CG   LEU A 373      13.203  35.357  35.749  1.00 21.32      A  C
ATOM   2552  CD1  LEU A 373      13.623  35.433  37.217  1.00 21.32      A  C
ATOM   2553  CD2  LEU A 373      12.591  36.665  35.282  1.00 21.32      A  C
ATOM   2554  C    LEU A 373      15.413  34.859  32.574  1.00 41.80      A  C
ATOM   2555  O    LEU A 373      16.115  35.867  32.535  1.00 41.80      A  O
ATOM   2556  N    ALA A 374      15.732  33.746  31.931  1.00 40.40      A  N
ATOM   2557  CA   ALA A 374      16.934  33.680  31.105  1.00 40.40      A  C
ATOM   2558  CB   ALA A 374      17.161  32.244  30.630  1.00 34.26      A  C
ATOM   2559  C    ALA A 374      16.778  34.635  29.907  1.00 40.40      A  C
ATOM   2560  O    ALA A 374      17.760  35.073  29.308  1.00 40.40      A  O
ATOM   2561  N    THR A 375      15.528  34.959  29.581  1.00 30.56      A  N
ATOM   2562  CA   THR A 375      15.217  35.841  28.467  1.00 30.56      A  C
ATOM   2563  CB   THR A 375      13.684  35.968  28.256  1.00 30.03      A  C
ATOM   2564  OG1  THR A 375      13.087  36.565  29.415  1.00 30.03      A  O
ATOM   2565  CG2  THR A 375      13.058  34.601  28.030  1.00 30.03      A  C
ATOM   2566  C    THR A 375      15.757  37.217  28.770  1.00 30.56      A  C
ATOM   2567  O    THR A 375      15.964  38.010  27.861  1.00 30.56      A  O
ATOM   2568  N    ILE A 376      15.953  37.507  30.051  1.00 27.03      A  N
ATOM   2569  CA   ILE A 376      16.499  38.791  30.461  1.00 27.03      A  C
ATOM   2570  CB   ILE A 376      15.644  39.420  31.582  1.00 27.95      A  C
ATOM   2571  CG2  ILE A 376      16.303  40.696  32.081  1.00 27.95      A  C
ATOM   2572  CG1  ILE A 376      14.241  39.737  31.059  1.00 27.95      A  C
ATOM   2573  CD1  ILE A 376      13.340  40.443  32.083  1.00 27.95      A  C
ATOM   2574  C    ILE A 376      17.928  38.627  30.972  1.00 27.03      A  C
ATOM   2575  O    ILE A 376      18.847  39.322  30.533  1.00 27.03      A  O
ATOM   2576  N    LEU A 377      18.116  37.691  31.890  1.00 36.65      A  N
ATOM   2577  CA   LEU A 377      19.438  37.456  32.455  1.00 36.65      A  C
ATOM   2578  CB   LEU A 377      19.371  36.249  33.400  1.00 38.07      A  C
ATOM   2579  CG   LEU A 377      18.414  36.578  34.557  1.00 38.07      A  C
ATOM   2580  CD1  LEU A 377      17.786  35.328  35.108  1.00 38.07      A  C
ATOM   2581  CD2  LEU A 377      19.156  37.337  35.631  1.00 38.07      A  C
ATOM   2582  C    LEU A 377      20.554  37.314  31.419  1.00 36.65      A  C
ATOM   2583  O    LEU A 377      21.637  37.875  31.618  1.00 36.65      A  O
ATOM   2584  N    ILE A 378      20.294  36.601  30.319  1.00 36.19      A  N
ATOM   2585  CA   ILE A 378      21.306  36.430  29.270  1.00 36.19      A  C
ATOM   2586  CB   ILE A 378      21.323  35.006  28.683  1.00 22.57      A  C
ATOM   2587  CG2  ILE A 378      22.478  34.890  27.720  1.00 22.57      A  C
ATOM   2588  CG1  ILE A 378      21.456  33.957  29.788  1.00 22.57      A  C
ATOM   2589  CD1  ILE A 378      20.155  33.671  30.512  1.00 22.57      A  C
ATOM   2590  C    ILE A 378      21.021  37.387  28.122  1.00 36.19      A  C
ATOM   2591  O    ILE A 378      20.152  37.140  27.291  1.00 36.19      A  O
ATOM   2592  N    PRO A 379      21.760  38.497  28.063  1.00 35.50      A  N
ATOM   2593  CD   PRO A 379      22.926  38.769  28.920  1.00 35.03      A  C
ATOM   2594  CA   PRO A 379      21.612  39.520  27.024  1.00 35.50      A  C
ATOM   2595  CB   PRO A 379      22.650  40.560  27.438  1.00 35.03      A  C
ATOM   2596  CG   PRO A 379      23.724  39.718  28.079  1.00 35.03      A  C
ATOM   2597  C    PRO A 379      21.837  38.961  25.612  1.00 35.50      A  C
ATOM   2598  O    PRO A 379      22.551  37.984  25.422  1.00 35.50      A  O
ATOM   2599  N    PRO A 380      21.228  39.589  24.605  1.00 32.46      A  N
ATOM   2600  CD   PRO A 380      20.441  40.824  24.738  1.00 17.91      A  C
ATOM   2601  CA   PRO A 380      21.326  39.186  23.202  1.00 32.46      A  C
ATOM   2602  CB   PRO A 380      20.688  40.365  22.476  1.00 17.91      A  C
ATOM   2603  CG   PRO A 380      19.676  40.857  23.454  1.00 17.91      A  C
ATOM   2604  C    PRO A 380      22.727  38.908  22.715  1.00 32.46      A  C
ATOM   2605  O    PRO A 380      22.991  37.845  22.157  1.00 32.46      A  O
ATOM   2606  N    HIS A 381      23.622  39.864  22.945  1.00 32.83      A  N
ATOM   2607  CA   HIS A 381      25.000  39.761  22.488  1.00 32.83      A  C
```

FIG. 4-40

| | | | | | | | | | | | |
|---|---|---|---|---|---|---|---|---|---|---|---|
| ATOM | 2608 | CB | HIS | A | 381 | 25.714 | 41.100 | 22.728 | 1.00 | 42.18 | A C |
| ATOM | 2609 | CG | HIS | A | 381 | 26.027 | 41.373 | 24.172 | 1.00 | 42.18 | A C |
| ATOM | 2610 | CD2 | HIS | A | 381 | 25.412 | 42.187 | 25.073 | 1.00 | 42.18 | A C |
| ATOM | 2611 | ND1 | HIS | A | 381 | 27.062 | 40.767 | 24.824 | 1.00 | 42.18 | A N |
| ATOM | 2612 | CE1 | HIS | A | 381 | 27.092 | 41.193 | 26.093 | 1.00 | 42.18 | A C |
| ATOM | 2613 | NE2 | HIS | A | 381 | 26.107 | 42.046 | 26.253 | 1.00 | 42.18 | A N |
| ATOM | 2614 | C | HIS | A | 381 | 25.749 | 38.626 | 23.126 | 1.00 | 32.83 | A C |
| ATOM | 2615 | O | HIS | A | 381 | 26.854 | 38.291 | 22.703 | 1.00 | 32.83 | A O |
| ATOM | 2616 | N | ALA | A | 382 | 25.149 | 38.045 | 24.160 | 1.00 | 35.94 | A N |
| ATOM | 2617 | CA | ALA | A | 382 | 25.750 | 36.913 | 24.851 | 1.00 | 35.94 | A C |
| ATOM | 2618 | CB | ALA | A | 382 | 25.304 | 36.881 | 26.284 | 1.00 | 48.18 | A C |
| ATOM | 2619 | C | ALA | A | 382 | 25.269 | 35.671 | 24.123 | 1.00 | 35.94 | A C |
| ATOM | 2620 | O | ALA | A | 382 | 25.953 | 34.634 | 24.080 | 1.00 | 35.94 | A O |
| ATOM | 2621 | N | ARG | A | 383 | 24.079 | 35.787 | 23.536 | 1.00 | 61.46 | A N |
| ATOM | 2622 | CA | ARG | A | 383 | 23.539 | 34.673 | 22.783 | 1.00 | 61.46 | A C |
| ATOM | 2623 | CB | ARG | A | 383 | 22.072 | 34.909 | 22.419 | 1.00 | 43.49 | A C |
| ATOM | 2624 | CG | ARG | A | 383 | 21.123 | 34.447 | 23.550 | 1.00 | 43.49 | A C |
| ATOM | 2625 | CD | ARG | A | 383 | 19.975 | 35.367 | 23.576 | 1.00 | 43.49 | A C |
| ATOM | 2626 | NE | ARG | A | 383 | 19.167 | 35.440 | 24.782 | 1.00 | 43.49 | A N |
| ATOM | 2627 | CZ | ARG | A | 383 | 18.108 | 36.242 | 24.808 | 1.00 | 43.49 | A C |
| ATOM | 2628 | NH1 | ARG | A | 383 | 17.842 | 36.930 | 23.703 | 1.00 | 43.49 | A N |
| ATOM | 2629 | NH2 | ARG | A | 383 | 17.339 | 36.393 | 25.880 | 1.00 | 43.49 | A N |
| ATOM | 2630 | C | ARG | A | 383 | 24.449 | 34.489 | 21.584 | 1.00 | 61.46 | A C |
| ATOM | 2631 | O | ARG | A | 383 | 24.693 | 33.338 | 21.196 | 1.00 | 61.46 | A O |
| ATOM | 2632 | N | ILE | A | 384 | 24.959 | 35.628 | 21.064 | 1.00 | 68.42 | A N |
| ATOM | 2633 | CA | ILE | A | 384 | 25.886 | 35.603 | 20.001 | 1.00 | 68.42 | A C |
| ATOM | 2634 | CB | ILE | A | 384 | 26.367 | 36.951 | 19.427 | 1.00 | 49.18 | A C |
| ATOM | 2635 | CG2 | ILE | A | 384 | 27.272 | 36.810 | 18.201 | 1.00 | 49.18 | A C |
| ATOM | 2636 | CG1 | ILE | A | 384 | 25.121 | 37.519 | 18.765 | 1.00 | 49.18 | A C |
| ATOM | 2637 | CD1 | ILE | A | 384 | 24.953 | 38.970 | 19.035 | 1.00 | 49.18 | A C |
| ATOM | 2638 | C | ILE | A | 384 | 26.846 | 34.539 | 20.305 | 1.00 | 68.42 | A C |
| ATOM | 2639 | O | ILE | A | 384 | 27.613 | 34.386 | 21.334 | 1.00 | 68.42 | A O |
| ATOM | 2640 | N | ALA | A | 385 | 26.910 | 34.423 | 19.023 | 1.00 | 58.85 | A N |
| ATOM | 2641 | CA | ALA | A | 385 | 27.193 | 33.362 | 18.203 | 1.00 | 58.85 | A C |
| ATOM | 2642 | CB | ALA | A | 385 | 26.088 | 33.700 | 17.285 | 1.00 | 76.22 | A C |
| ATOM | 2643 | C | ALA | A | 385 | 27.847 | 32.166 | 17.518 | 1.00 | 58.85 | A C |
| ATOM | 2644 | O | ALA | A | 385 | 29.045 | 32.173 | 17.354 | 1.00 | 58.85 | A O |
| ATOM | 2645 | OXT | ALA | A | 385 | 26.936 | 31.309 | 17.041 | 1.00 | 76.22 | A O |
| TER | 2646 | | ALA | A | 385 | | | | | | A |
| ATOM | 2647 | CB | VAL | B | 37 | 14.350 | 82.418 | 78.901 | 1.00 | 42.36 | B C |
| ATOM | 2648 | CG1 | VAL | B | 37 | 13.496 | 82.004 | 80.100 | 1.00 | 42.36 | B C |
| ATOM | 2649 | CG2 | VAL | B | 37 | 15.683 | 83.003 | 79.347 | 1.00 | 42.36 | B C |
| ATOM | 2650 | C | VAL | B | 37 | 13.197 | 80.644 | 77.668 | 1.00 | 47.65 | B C |
| ATOM | 2651 | O | VAL | B | 37 | 12.400 | 81.301 | 77.002 | 1.00 | 47.65 | B O |
| ATOM | 2652 | N | VAL | B | 37 | 15.414 | 81.523 | 76.791 | 1.00 | 47.65 | B N |
| ATOM | 2653 | CA | VAL | B | 37 | 14.582 | 81.195 | 78.003 | 1.00 | 47.65 | B C |
| ATOM | 2654 | N | THR | B | 38 | 12.914 | 79.436 | 78.139 | 1.00 | 44.52 | B N |
| ATOM | 2655 | CA | THR | B | 38 | 11.631 | 78.807 | 77.890 | 1.00 | 44.52 | B C |
| ATOM | 2656 | CB | THR | B | 38 | 11.815 | 77.429 | 77.233 | 1.00 | 31.95 | B C |
| ATOM | 2657 | OG1 | THR | B | 38 | 12.125 | 77.588 | 75.845 | 1.00 | 31.95 | B O |
| ATOM | 2658 | CG2 | THR | B | 38 | 10.563 | 76.608 | 77.376 | 1.00 | 31.95 | B C |
| ATOM | 2659 | C | THR | B | 38 | 10.894 | 78.621 | 79.209 | 1.00 | 44.52 | B C |
| ATOM | 2660 | O | THR | B | 38 | 11.494 | 78.272 | 80.233 | 1.00 | 44.52 | B O |
| ATOM | 2661 | N | THR | B | 39 | 9.592 | 78.873 | 79.185 | 1.00 | 27.14 | B N |
| ATOM | 2662 | CA | THR | B | 39 | 8.777 | 78.721 | 80.377 | 1.00 | 27.14 | B C |
| ATOM | 2663 | CB | THR | B | 39 | 8.166 | 80.054 | 80.834 | 1.00 | 35.52 | B C |
| ATOM | 2664 | OG1 | THR | B | 39 | 9.202 | 81.031 | 80.966 | 1.00 | 35.52 | B O |
| ATOM | 2665 | CG2 | THR | B | 39 | 7.490 | 79.894 | 82.187 | 1.00 | 35.52 | B C |
| ATOM | 2666 | C | THR | B | 39 | 7.662 | 77.772 | 80.021 | 1.00 | 27.14 | B C |
| ATOM | 2667 | O | THR | B | 39 | 7.048 | 77.901 | 78.976 | 1.00 | 27.14 | B O |
| ATOM | 2668 | N | VAL | B | 40 | 7.403 | 76.807 | 80.884 | 1.00 | 26.48 | B N |
| ATOM | 2669 | CA | VAL | B | 40 | 6.349 | 75.851 | 80.619 | 1.00 | 26.48 | B C |
| ATOM | 2670 | CB | VAL | B | 40 | 6.932 | 74.606 | 79.887 | 1.00 | 32.96 | B C |
| ATOM | 2671 | CG1 | VAL | B | 40 | 8.214 | 74.174 | 80.532 | 1.00 | 32.96 | B C |
| ATOM | 2672 | CG2 | VAL | B | 40 | 5.960 | 73.461 | 79.933 | 1.00 | 32.96 | B C |
| ATOM | 2673 | C | VAL | B | 40 | 5.721 | 75.461 | 81.945 | 1.00 | 26.48 | B C |
| ATOM | 2674 | O | VAL | B | 40 | 6.323 | 75.679 | 82.997 | 1.00 | 26.48 | B O |

FIG. 4-41

```
ATOM   2675  N    VAL B  41       4.501  74.930  81.901  1.00 23.20      B    N
ATOM   2676  CA   VAL B  41       3.804  74.502  83.110  1.00 23.20      B    C
ATOM   2677  CB   VAL B  41       2.313  74.848  83.034  1.00 31.21      B    C
ATOM   2678  CG1  VAL B  41       1.785  74.522  81.660  1.00 31.21      B    C
ATOM   2679  CG2  VAL B  41       1.548  74.074  84.074  1.00 31.21      B    C
ATOM   2680  C    VAL B  41       3.980  72.996  83.101  1.00 23.20      B    C
ATOM   2681  O    VAL B  41       3.522  72.327  82.178  1.00 23.20      B    O
ATOM   2682  N    ALA B  42       4.677  72.473  84.110  1.00 31.57      B    N
ATOM   2683  CA   ALA B  42       4.944  71.042  84.194  1.00 31.57      B    C
ATOM   2684  CB   ALA B  42       6.430  70.793  84.064  1.00  8.97      B    C
ATOM   2685  C    ALA B  42       4.431  70.372  85.454  1.00 31.57      B    C
ATOM   2686  O    ALA B  42       4.234  70.995  86.493  1.00 31.57      B    O
ATOM   2687  N    THR B  43       4.221  69.072  85.334  1.00 35.31      B    N
ATOM   2688  CA   THR B  43       3.724  68.266  86.422  1.00 35.31      B    C
ATOM   2689  CB   THR B  43       2.760  67.198  85.885  1.00 41.63      B    C
ATOM   2690  OG1  THR B  43       1.651  67.845  85.246  1.00 41.63      B    O
ATOM   2691  CG2  THR B  43       2.252  66.304  87.015  1.00 41.63      B    C
ATOM   2692  C    THR B  43       4.897  67.596  87.107  1.00 35.31      B    C
ATOM   2693  O    THR B  43       5.739  66.991  86.455  1.00 35.31      B    O
ATOM   2694  N    PRO B  44       4.995  67.740  88.430  1.00 36.80      B    N
ATOM   2695  CD   PRO B  44       4.348  68.814  89.208  1.00 31.41      B    C
ATOM   2696  CA   PRO B  44       6.075  67.130  89.205  1.00 36.80      B    C
ATOM   2697  CB   PRO B  44       5.763  67.587  90.619  1.00 31.41      B    C
ATOM   2698  CG   PRO B  44       5.319  68.999  90.373  1.00 31.41      B    C
ATOM   2699  C    PRO B  44       6.102  65.605  89.057  1.00 36.80      B    C
ATOM   2700  O    PRO B  44       5.056  64.942  89.089  1.00 36.80      B    O
ATOM   2701  N    GLY B  45       7.311  65.067  88.891  1.00 35.89      B    N
ATOM   2702  CA   GLY B  45       7.494  63.637  88.725  1.00 35.89      B    C
ATOM   2703  C    GLY B  45       6.731  62.881  89.791  1.00 35.89      B    C
ATOM   2704  O    GLY B  45       5.745  62.169  89.522  1.00 35.89      B    O
ATOM   2705  N    ALA B  46       7.182  63.041  91.024  1.00 49.05      B    N
ATOM   2706  CA   ALA B  46       6.515  62.375  92.126  1.00 49.05      B    C
ATOM   2707  CB   ALA B  46       7.491  62.175  93.290  1.00 41.31      B    C
ATOM   2708  C    ALA B  46       5.323  63.231  92.569  1.00 49.05      B    C
ATOM   2709  O    ALA B  46       4.769  64.012  91.783  1.00 49.05      B    O
ATOM   2710  N    GLY B  47       4.919  63.064  93.822  1.00 43.71      B    N
ATOM   2711  CA   GLY B  47       3.825  63.854  94.357  1.00 43.71      B    C
ATOM   2712  C    GLY B  47       2.527  63.931  93.566  1.00 43.71      B    C
ATOM   2713  O    GLY B  47       2.409  63.351  92.482  1.00 43.71      B    O
ATOM   2714  N    PRO B  48       1.520  64.648  94.105  1.00 60.64      B    N
ATOM   2715  CD   PRO B  48       1.592  65.364  95.394  1.00 66.43      B    C
ATOM   2716  CA   PRO B  48       0.198  64.826  93.474  1.00 60.64      B    C
ATOM   2717  CB   PRO B  48      -0.664  65.337  94.623  1.00 66.43      B    C
ATOM   2718  CG   PRO B  48       0.322  66.213  95.379  1.00 66.43      B    C
ATOM   2719  C    PRO B  48       0.239  65.815  92.297  1.00 60.64      B    C
ATOM   2720  O    PRO B  48       0.897  66.857  92.377  1.00 60.64      B    O
ATOM   2721  N    ASP B  49      -0.489  65.497  91.230  1.00 43.48      B    N
ATOM   2722  CA   ASP B  49      -0.510  66.325  90.029  1.00 43.48      B    C
ATOM   2723  CB   ASP B  49      -1.445  65.689  88.988  1.00 68.80      B    C
ATOM   2724  CG   ASP B  49      -1.056  64.238  88.660  1.00 68.80      B    C
ATOM   2725  OD1  ASP B  49      -0.765  63.936  87.466  1.00 68.80      B    O
ATOM   2726  OD2  ASP B  49      -1.040  63.410  89.612  1.00 68.80      B    O
ATOM   2727  C    ASP B  49      -0.853  67.795  90.205  1.00 43.48      B    C
ATOM   2728  O    ASP B  49      -1.944  68.226  89.844  1.00 43.48      B    O
ATOM   2729  N    ARG B  50       0.106  68.550  90.741  1.00 46.20      B    N
ATOM   2730  CA   ARG B  50       0.002  69.994  90.988  1.00 46.20      B    C
ATOM   2731  CB   ARG B  50       0.477  70.308  92.404  1.00 57.67      B    C
ATOM   2732  CG   ARG B  50      -0.589  70.399  93.474  1.00 57.67      B    C
ATOM   2733  CD   ARG B  50      -1.591  69.268  93.392  1.00 57.67      B    C
ATOM   2734  NE   ARG B  50      -2.632  69.551  92.402  1.00 57.67      B    N
ATOM   2735  CZ   ARG B  50      -3.940  69.423  92.632  1.00 57.67      B    C
ATOM   2736  NH1  ARG B  50      -4.351  69.020  93.835  1.00 57.67      B    N
ATOM   2737  NH2  ARG B  50      -4.830  69.681  91.663  1.00 57.67      B    N
ATOM   2738  C    ARG B  50       0.936  70.713  90.002  1.00 46.20      B    C
ATOM   2739  O    ARG B  50       2.085  71.007  90.332  1.00 46.20      B    O
ATOM   2740  N    PRO B  51       0.467  70.988  88.781  1.00 44.00      B    N
ATOM   2741  CD   PRO B  51      -0.637  70.290  88.098  1.00 31.45      B    C
```

FIG. 4-42

| | | | | | | | | | | | | |
|---|---|---|---|---|---|---|---|---|---|---|---|---|
| ATOM | 2742 | CA | PRO | B | 51 | 1.321 | 71.674 | 87.804 | 1.00 | 44.00 | B | C |
| ATOM | 2743 | CB | PRO | B | 51 | 0.492 | 71.604 | 86.525 | 1.00 | 31.45 | B | C |
| ATOM | 2744 | CG | PRO | B | 51 | -0.160 | 70.269 | 86.661 | 1.00 | 31.45 | B | C |
| ATOM | 2745 | C | PRO | B | 51 | 1.805 | 73.073 | 88.105 | 1.00 | 44.00 | B | C |
| ATOM | 2746 | O | PRO | B | 51 | 1.000 | 73.972 | 88.290 | 1.00 | 44.00 | B | O |
| ATOM | 2747 | N | GLN | B | 52 | 3.123 | 73.255 | 88.141 | 1.00 | 27.69 | B | N |
| ATOM | 2748 | CA | GLN | B | 52 | 3.698 | 74.569 | 88.399 | 1.00 | 27.69 | B | C |
| ATOM | 2749 | CB | GLN | B | 52 | 4.576 | 74.542 | 89.649 | 1.00 | 42.73 | B | C |
| ATOM | 2750 | CG | GLN | B | 52 | 5.826 | 73.695 | 89.531 | 1.00 | 42.73 | B | C |
| ATOM | 2751 | CD | GLN | B | 52 | 6.203 | 73.035 | 90.859 | 1.00 | 42.73 | B | C |
| ATOM | 2752 | OE1 | GLN | B | 52 | 7.390 | 72.883 | 91.179 | 1.00 | 42.73 | B | O |
| ATOM | 2753 | NE2 | GLN | B | 52 | 5.185 | 72.626 | 91.634 | 1.00 | 42.73 | B | N |
| ATOM | 2754 | C | GLN | B | 52 | 4.484 | 75.084 | 87.199 | 1.00 | 27.69 | B | C |
| ATOM | 2755 | O | GLN | B | 52 | 4.738 | 74.354 | 86.238 | 1.00 | 27.69 | B | O |
| ATOM | 2756 | N | GLU | B | 53 | 4.842 | 76.360 | 87.243 | 1.00 | 38.58 | B | N |
| ATOM | 2757 | CA | GLU | B | 53 | 5.609 | 76.944 | 86.160 | 1.00 | 38.58 | B | C |
| ATOM | 2758 | CB | GLU | B | 53 | 5.288 | 78.446 | 86.055 | 1.00 | 75.47 | B | C |
| ATOM | 2759 | CG | GLU | B | 53 | 3.796 | 78.696 | 85.712 | 1.00 | 75.47 | B | C |
| ATOM | 2760 | CD | GLU | B | 53 | 3.288 | 80.124 | 86.028 | 1.00 | 75.47 | B | C |
| ATOM | 2761 | OE1 | GLU | B | 53 | 3.861 | 80.746 | 86.972 | 1.00 | 75.47 | B | O |
| ATOM | 2762 | OE2 | GLU | B | 53 | 2.311 | 80.588 | 85.347 | 1.00 | 75.47 | B | O |
| ATOM | 2763 | C | GLU | B | 53 | 7.085 | 76.661 | 86.357 | 1.00 | 38.58 | B | C |
| ATOM | 2764 | O | GLU | B | 53 | 7.597 | 76.723 | 87.474 | 1.00 | 38.58 | B | O |
| ATOM | 2765 | N | VAL | B | 54 | 7.741 | 76.296 | 85.260 | 1.00 | 42.21 | B | N |
| ATOM | 2766 | CA | VAL | B | 54 | 9.159 | 75.951 | 85.244 | 1.00 | 42.21 | B | C |
| ATOM | 2767 | CB | VAL | B | 54 | 9.335 | 74.425 | 85.101 | 1.00 | 31.58 | B | C |
| ATOM | 2768 | CG1 | VAL | B | 54 | 10.813 | 74.074 | 85.015 | 1.00 | 31.58 | B | C |
| ATOM | 2769 | CG2 | VAL | B | 54 | 8.671 | 73.716 | 86.286 | 1.00 | 31.58 | B | C |
| ATOM | 2770 | C | VAL | B | 54 | 9.796 | 76.655 | 84.055 | 1.00 | 42.21 | B | C |
| ATOM | 2771 | O | VAL | B | 54 | 9.248 | 76.640 | 82.950 | 1.00 | 42.21 | B | O |
| ATOM | 2772 | N | SER | B | 55 | 10.945 | 77.284 | 84.290 | 1.00 | 52.24 | B | N |
| ATOM | 2773 | CA | SER | B | 55 | 11.653 | 77.990 | 83.232 | 1.00 | 52.24 | B | C |
| ATOM | 2774 | CB | SER | B | 55 | 11.562 | 79.497 | 83.463 | 1.00 | 55.76 | B | C |
| ATOM | 2775 | OG | SER | B | 55 | 10.205 | 79.912 | 83.435 | 1.00 | 55.76 | B | O |
| ATOM | 2776 | C | SER | B | 55 | 13.102 | 77.537 | 83.158 | 1.00 | 52.24 | B | C |
| ATOM | 2777 | O | SER | B | 55 | 13.789 | 77.419 | 84.172 | 1.00 | 52.24 | B | O |
| ATOM | 2778 | N | TYR | B | 56 | 13.551 | 77.268 | 81.942 | 1.00 | 39.27 | B | N |
| ATOM | 2779 | CA | TYR | B | 56 | 14.904 | 76.808 | 81.713 | 1.00 | 39.27 | B | C |
| ATOM | 2780 | CB | TYR | B | 56 | 14.875 | 75.290 | 81.510 | 1.00 | 28.30 | B | C |
| ATOM | 2781 | CG | TYR | B | 56 | 14.041 | 74.820 | 80.318 | 1.00 | 28.30 | B | C |
| ATOM | 2782 | CD1 | TYR | B | 56 | 14.569 | 74.808 | 79.016 | 1.00 | 28.30 | B | C |
| ATOM | 2783 | CE1 | TYR | B | 56 | 13.817 | 74.339 | 77.926 | 1.00 | 28.30 | B | C |
| ATOM | 2784 | CD2 | TYR | B | 56 | 12.737 | 74.355 | 80.496 | 1.00 | 28.30 | B | C |
| ATOM | 2785 | CE2 | TYR | B | 56 | 11.980 | 73.884 | 79.414 | 1.00 | 28.30 | B | C |
| ATOM | 2786 | CZ | TYR | B | 56 | 12.527 | 73.880 | 78.137 | 1.00 | 28.30 | B | C |
| ATOM | 2787 | OH | TYR | B | 56 | 11.777 | 73.419 | 77.081 | 1.00 | 28.30 | B | O |
| ATOM | 2788 | C | TYR | B | 56 | 15.500 | 77.493 | 80.484 | 1.00 | 39.27 | B | C |
| ATOM | 2789 | O | TYR | B | 56 | 14.781 | 77.939 | 79.573 | 1.00 | 39.27 | B | O |
| ATOM | 2790 | N | THR | B | 57 | 16.827 | 77.549 | 80.455 | 1.00 | 57.44 | B | N |
| ATOM | 2791 | CA | THR | B | 57 | 17.522 | 78.187 | 79.353 | 1.00 | 57.44 | B | C |
| ATOM | 2792 | CB | THR | B | 57 | 17.796 | 79.655 | 79.720 | 1.00 | 40.39 | B | C |
| ATOM | 2793 | OG1 | THR | B | 57 | 18.044 | 80.416 | 78.528 | 1.00 | 40.39 | B | O |
| ATOM | 2794 | CG2 | THR | B | 57 | 18.978 | 79.742 | 80.696 | 1.00 | 40.39 | B | C |
| ATOM | 2795 | C | THR | B | 57 | 18.822 | 77.448 | 79.008 | 1.00 | 57.44 | B | C |
| ATOM | 2796 | O | THR | B | 57 | 19.197 | 76.480 | 79.683 | 1.00 | 57.44 | B | O |
| ATOM | 2797 | N | ASP | B | 58 | 19.498 | 77.955 | 77.955 | 1.00 | 37.63 | B | N |
| ATOM | 2798 | CA | ASP | B | 58 | 20.746 | 77.298 | 77.510 | 1.00 | 37.63 | B | C |
| ATOM | 2799 | CB | ASP | B | 58 | 21.804 | 77.253 | 78.626 | 1.00 | 50.66 | B | C |
| ATOM | 2800 | CG | ASP | B | 58 | 21.902 | 78.555 | 79.396 | 1.00 | 50.66 | B | C |
| ATOM | 2801 | OD1 | ASP | B | 58 | 21.812 | 79.627 | 78.757 | 1.00 | 50.66 | B | O |
| ATOM | 2802 | OD2 | ASP | B | 58 | 22.074 | 78.500 | 80.637 | 1.00 | 50.66 | B | O |
| ATOM | 2803 | C | ASP | B | 58 | 20.442 | 75.892 | 77.082 | 1.00 | 37.63 | B | C |
| ATOM | 2804 | O | ASP | B | 58 | 21.172 | 74.958 | 77.408 | 1.00 | 37.63 | B | O |
| ATOM | 2805 | N | THR | B | 59 | 19.336 | 75.739 | 76.372 | 1.00 | 49.68 | B | N |
| ATOM | 2806 | CA | THR | B | 59 | 18.987 | 74.429 | 75.869 | 1.00 | 49.68 | B | C |
| ATOM | 2807 | CB | THR | B | 59 | 17.670 | 74.489 | 75.081 | 1.00 | 44.03 | B | C |
| ATOM | 2808 | OG1 | THR | B | 59 | 16.586 | 74.620 | 76.007 | 1.00 | 44.03 | B | O |

FIG. 4-43

| | | | | | | | | | | |
|---|---|---|---|---|---|---|---|---|---|---|
| ATOM | 2809 | CG2 | THR | B | 59 | 17.467 | 73.233 | 74.244 | 1.00 44.03 | B C |
| ATOM | 2810 | C | THR | B | 59 | 20.154 | 74.078 | 74.948 | 1.00 49.68 | B C |
| ATOM | 2811 | O | THR | B | 59 | 20.974 | 74.942 | 74.624 | 1.00 49.68 | B O |
| ATOM | 2812 | N | LYS | B | 60 | 20.253 | 72.808 | 74.574 | 1.00 61.63 | B N |
| ATOM | 2813 | CA | LYS | B | 60 | 21.292 | 72.334 | 73.669 | 1.00 61.63 | B C |
| ATOM | 2814 | CB | LYS | B | 60 | 22.698 | 72.579 | 74.257 | 1.00 45.29 | B C |
| ATOM | 2815 | CG | LYS | B | 60 | 23.269 | 71.437 | 75.104 | 1.00 45.29 | B C |
| ATOM | 2816 | CD | LYS | B | 60 | 24.762 | 71.647 | 75.449 | 1.00 45.29 | B C |
| ATOM | 2817 | CE | LYS | B | 60 | 24.989 | 72.588 | 76.656 | 1.00 45.29 | B C |
| ATOM | 2818 | NZ | LYS | B | 60 | 24.639 | 74.042 | 76.429 | 1.00 45.29 | B N |
| ATOM | 2819 | C | LYS | B | 60 | 21.023 | 70.839 | 73.480 | 1.00 61.63 | B C |
| ATOM | 2820 | O | LYS | B | 60 | 20.705 | 70.128 | 74.449 | 1.00 61.63 | B O |
| ATOM | 2821 | N | VAL | B | 61 | 21.100 | 70.373 | 72.234 | 1.00 46.94 | B N |
| ATOM | 2822 | CA | VAL | B | 61 | 20.870 | 68.961 | 71.956 | 1.00 46.94 | B C |
| ATOM | 2823 | CB | VAL | B | 61 | 20.832 | 68.680 | 70.457 | 1.00 31.47 | B C |
| ATOM | 2824 | CG1 | VAL | B | 61 | 20.426 | 67.239 | 70.227 | 1.00 31.47 | B C |
| ATOM | 2825 | CG2 | VAL | B | 61 | 19.857 | 69.633 | 69.778 | 1.00 31.47 | B C |
| ATOM | 2826 | C | VAL | B | 61 | 22.050 | 68.200 | 72.565 | 1.00 46.94 | B C |
| ATOM | 2827 | O | VAL | B | 61 | 23.163 | 68.725 | 72.624 | 1.00 46.94 | B O |
| ATOM | 2828 | N | ILE | B | 62 | 21.816 | 66.983 | 73.048 | 1.00 42.00 | B N |
| ATOM | 2829 | CA | ILE | B | 62 | 22.901 | 66.202 | 73.641 | 1.00 42.00 | B C |
| ATOM | 2830 | CB | ILE | B | 62 | 22.853 | 66.204 | 75.179 | 1.00 32.41 | B C |
| ATOM | 2831 | CG2 | ILE | B | 62 | 22.915 | 67.619 | 75.688 | 1.00 32.41 | B C |
| ATOM | 2832 | CG1 | ILE | B | 62 | 21.585 | 65.503 | 75.673 | 1.00 32.41 | B C |
| ATOM | 2833 | CD1 | ILE | B | 62 | 21.556 | 65.289 | 77.175 | 1.00 32.41 | B C |
| ATOM | 2834 | C | ILE | B | 62 | 22.785 | 64.769 | 73.206 | 1.00 42.00 | B C |
| ATOM | 2835 | O | ILE | B | 62 | 23.616 | 63.916 | 73.531 | 1.00 42.00 | B O |
| ATOM | 2836 | N | GLY | B | 63 | 21.705 | 64.520 | 72.494 | 1.00 48.40 | B N |
| ATOM | 2837 | CA | GLY | B | 63 | 21.442 | 63.211 | 71.967 | 1.00 48.40 | B C |
| ATOM | 2838 | C | GLY | B | 63 | 20.320 | 63.443 | 71.002 | 1.00 48.40 | B C |
| ATOM | 2839 | O | GLY | B | 63 | 19.672 | 64.501 | 71.006 | 1.00 48.40 | B O |
| ATOM | 2840 | N | ASN | B | 64 | 20.140 | 62.478 | 70.124 | 1.00 77.09 | B N |
| ATOM | 2841 | CA | ASN | B | 64 | 19.041 | 62.492 | 69.181 | 1.00 77.09 | B C |
| ATOM | 2842 | CB | ASN | B | 64 | 19.605 | 62.422 | 67.771 | 1.00 79.31 | B C |
| ATOM | 2843 | CG | ASN | B | 64 | 19.627 | 63.793 | 67.102 | 1.00 79.31 | B C |
| ATOM | 2844 | OD1 | ASN | B | 64 | 18.564 | 64.360 | 66.772 | 1.00 79.31 | B O |
| ATOM | 2845 | ND2 | ASN | B | 64 | 20.839 | 64.356 | 66.926 | 1.00 79.31 | B N |
| ATOM | 2846 | C | ASN | B | 64 | 18.585 | 61.183 | 69.736 | 1.00 77.09 | B C |
| ATOM | 2847 | O | ASN | B | 64 | 18.095 | 61.121 | 70.882 | 1.00 77.09 | B O |
| ATOM | 2848 | N | GLY | B | 65 | 18.768 | 60.121 | 68.980 | 1.00 99.74 | B N |
| ATOM | 2849 | CA | GLY | B | 65 | 18.415 | 58.861 | 69.572 | 1.00 99.74 | B C |
| ATOM | 2850 | C | GLY | B | 65 | 17.031 | 58.335 | 69.343 | 1.00 99.74 | B C |
| ATOM | 2851 | O | GLY | B | 65 | 15.997 | 58.893 | 69.773 | 1.00 99.74 | B O |
| ATOM | 2852 | N | SER | B | 66 | 17.055 | 57.260 | 68.571 | 1.00 75.59 | B N |
| ATOM | 2853 | CA | SER | B | 66 | 15.891 | 56.457 | 68.315 | 1.00 75.59 | B C |
| ATOM | 2854 | CB | SER | B | 66 | 16.017 | 55.273 | 69.283 | 1.00 95.52 | B C |
| ATOM | 2855 | OG | SER | B | 66 | 16.715 | 55.736 | 70.444 | 1.00 95.52 | B O |
| ATOM | 2856 | C | SER | B | 66 | 14.546 | 57.171 | 68.546 | 1.00 75.59 | B C |
| ATOM | 2857 | O | SER | B | 66 | 13.934 | 57.708 | 67.607 | 1.00 75.59 | B O |
| ATOM | 2858 | N | ALA | B | 67 | 14.113 | 57.158 | 69.812 | 1.00 52.84 | B N |
| ATOM | 2859 | CA | ALA | B | 67 | 12.836 | 57.740 | 70.225 | 1.00 52.84 | B C |
| ATOM | 2860 | CB | ALA | B | 67 | 12.566 | 57.411 | 71.692 | 1.00 51.78 | B C |
| ATOM | 2861 | C | ALA | B | 67 | 12.691 | 59.245 | 69.986 | 1.00 52.84 | B C |
| ATOM | 2862 | O | ALA | B | 67 | 11.665 | 59.709 | 69.470 | 1.00 52.84 | B O |
| ATOM | 2863 | N | GLY | B | 68 | 13.710 | 60.008 | 70.354 | 1.00 75.27 | B N |
| ATOM | 2864 | CA | GLY | B | 68 | 13.632 | 61.441 | 70.144 | 1.00 75.27 | B C |
| ATOM | 2865 | C | GLY | B | 68 | 14.794 | 62.213 | 70.741 | 1.00 75.27 | B C |
| ATOM | 2866 | O | GLY | B | 68 | 15.546 | 61.713 | 71.603 | 1.00 75.27 | B O |
| ATOM | 2867 | N | VAL | B | 69 | 14.938 | 63.452 | 70.285 | 1.00 49.39 | B N |
| ATOM | 2868 | CA | VAL | B | 69 | 16.018 | 64.298 | 70.761 | 1.00 49.39 | B C |
| ATOM | 2869 | CB | VAL | B | 69 | 15.952 | 65.715 | 70.124 | 1.00 53.98 | B C |
| ATOM | 2870 | CG1 | VAL | B | 69 | 16.977 | 66.648 | 70.790 | 1.00 53.98 | B C |
| ATOM | 2871 | CG2 | VAL | B | 69 | 16.235 | 65.617 | 68.631 | 1.00 53.98 | B C |
| ATOM | 2872 | C | VAL | B | 69 | 16.017 | 64.440 | 72.282 | 1.00 49.39 | B C |
| ATOM | 2873 | O | VAL | B | 69 | 14.963 | 64.570 | 72.914 | 1.00 49.39 | B O |
| ATOM | 2874 | N | VAL | B | 70 | 17.210 | 64.386 | 72.863 | 1.00 40.04 | B N |
| ATOM | 2875 | CA | VAL | B | 70 | 17.360 | 64.556 | 74.295 | 1.00 40.04 | B C |

FIG. 4-44

```
ATOM   2876  CB   VAL B  70      18.012  63.313  74.958  1.00 22.25      B  C
ATOM   2877  CG1  VAL B  70      18.282  63.579  76.417  1.00 22.25      B  C
ATOM   2878  CG2  VAL B  70      17.097  62.112  74.819  1.00 22.25      B  C
ATOM   2879  C    VAL B  70      18.267  65.773  74.440  1.00 40.04      B  C
ATOM   2880  O    VAL B  70      19.384  65.789  73.895  1.00 40.04      B  O
ATOM   2881  N    TYR B  71      17.774  66.794  75.150  1.00 35.91      B  N
ATOM   2882  CA   TYR B  71      18.541  68.021  75.353  1.00 35.91      B  C
ATOM   2883  CB   TYR B  71      17.712  69.281  75.108  1.00 53.07      B  C
ATOM   2884  CG   TYR B  71      16.812  69.294  73.903  1.00 53.07      B  C
ATOM   2885  CD1  TYR B  71      15.689  68.471  73.839  1.00 53.07      B  C
ATOM   2886  CE1  TYR B  71      14.796  68.560  72.776  1.00 53.07      B  C
ATOM   2887  CD2  TYR B  71      17.029  70.203  72.866  1.00 53.07      B  C
ATOM   2888  CE2  TYR B  71      16.146  70.304  71.794  1.00 53.07      B  C
ATOM   2889  CZ   TYR B  71      15.028  69.481  71.753  1.00 53.07      B  C
ATOM   2890  OH   TYR B  71      14.145  69.580  70.693  1.00 53.07      B  O
ATOM   2891  C    TYR B  71      19.028  68.136  76.772  1.00 35.91      B  C
ATOM   2892  O    TYR B  71      18.704  67.318  77.616  1.00 35.91      B  O
ATOM   2893  N    GLN B  72      19.807  69.180  77.011  1.00 46.68      B  N
ATOM   2894  CA   GLN B  72      20.334  69.508  78.325  1.00 46.68      B  C
ATOM   2895  CB   GLN B  72      21.859  69.431  78.318  1.00 35.65      B  C
ATOM   2896  CG   GLN B  72      22.550  70.623  78.964  1.00 35.65      B  C
ATOM   2897  CD   GLN B  72      23.500  70.231  80.091  1.00 35.65      B  C
ATOM   2898  OE1  GLN B  72      24.283  71.051  80.554  1.00 35.65      B  O
ATOM   2899  NE2  GLN B  72      23.429  68.982  80.538  1.00 35.65      B  N
ATOM   2900  C    GLN B  72      19.868  70.955  78.525  1.00 46.68      B  C
ATOM   2901  O    GLN B  72      19.673  71.688  77.537  1.00 46.68      B  O
ATOM   2902  N    ALA B  73      19.690  71.377  79.775  1.00 35.65      B  N
ATOM   2903  CA   ALA B  73      19.232  72.738  80.012  1.00 35.65      B  C
ATOM   2904  CB   ALA B  73      17.748  72.846  79.709  1.00 14.29      B  C
ATOM   2905  C    ALA B  73      19.499  73.195  81.421  1.00 35.65      B  C
ATOM   2906  O    ALA B  73      20.031  72.438  82.238  1.00 35.65      B  O
ATOM   2907  N    LYS B  74      19.117  74.439  81.702  1.00 31.17      B  N
ATOM   2908  CA   LYS B  74      19.321  75.015  83.022  1.00 31.17      B  C
ATOM   2909  CB   LYS B  74      20.386  76.119  82.950  1.00 44.34      B  C
ATOM   2910  CG   LYS B  74      20.924  76.609  84.298  1.00 44.34      B  C
ATOM   2911  CD   LYS B  74      22.212  77.428  84.095  1.00 44.34      B  C
ATOM   2912  CE   LYS B  74      22.886  77.816  85.413  1.00 44.34      B  C
ATOM   2913  NZ   LYS B  74      22.134  78.892  86.140  1.00 44.34      B  N
ATOM   2914  C    LYS B  74      18.028  75.577  83.599  1.00 31.17      B  C
ATOM   2915  O    LYS B  74      17.384  76.427  82.988  1.00 31.17      B  O
ATOM   2916  N    LEU B  75      17.634  75.071  84.764  1.00 35.87      B  N
ATOM   2917  CA   LEU B  75      16.434  75.560  85.434  1.00 35.87      B  C
ATOM   2918  CB   LEU B  75      16.103  74.685  86.651  1.00 13.58      B  C
ATOM   2919  CG   LEU B  75      15.780  73.221  86.331  1.00 13.58      B  C
ATOM   2920  CD1  LEU B  75      15.367  72.495  87.585  1.00 13.58      B  C
ATOM   2921  CD2  LEU B  75      14.696  73.149  85.290  1.00 13.58      B  C
ATOM   2922  C    LEU B  75      16.829  76.966  85.862  1.00 35.87      B  C
ATOM   2923  O    LEU B  75      17.901  77.159  86.430  1.00 35.87      B  O
ATOM   2924  N    CYS B  76      15.984  77.949  85.581  1.00 38.44      B  N
ATOM   2925  CA   CYS B  76      16.313  79.326  85.909  1.00 38.44      B  C
ATOM   2926  CB   CYS B  76      15.244  80.252  85.344  1.00 42.35      B  C
ATOM   2927  SG   CYS B  76      15.114  80.062  83.552  1.00 42.35      B  S
ATOM   2928  C    CYS B  76      16.520  79.591  87.388  1.00 38.44      B  C
ATOM   2929  O    CYS B  76      17.660  79.649  87.855  1.00 38.44      B  O
ATOM   2930  N    ASP B  77      15.426  79.757  88.128  1.00 69.63      B  N
ATOM   2931  CA   ASP B  77      15.539  80.036  89.560  1.00 69.63      B  C
ATOM   2932  CB   ASP B  77      14.172  79.896  90.263  1.00 73.68      B  C
ATOM   2933  CG   ASP B  77      13.483  78.560  89.985  1.00 73.68      B  C
ATOM   2934  OD1  ASP B  77      13.510  78.090  88.820  1.00 73.68      B  O
ATOM   2935  OD2  ASP B  77      12.898  77.990  90.938  1.00 73.68      B  O
ATOM   2936  C    ASP B  77      16.574  79.102  90.173  1.00 69.63      B  C
ATOM   2937  O    ASP B  77      17.634  79.544  90.623  1.00 69.63      B  O
ATOM   2938  N    SER B  78      16.288  77.809  90.131  1.00 44.16      B  N
ATOM   2939  CA   SER B  78      17.181  76.786  90.672  1.00 44.16      B  C
ATOM   2940  CB   SER B  78      16.629  75.389  90.336  1.00 61.16      B  C
ATOM   2941  OG   SER B  78      17.465  74.358  90.840  1.00 61.16      B  O
ATOM   2942  C    SER B  78      18.650  76.871  90.218  1.00 44.16      B  C
```

FIG. 4-45

```
ATOM   2943  O    SER B  78      19.560  76.813  91.038  1.00 44.16      B  O
ATOM   2944  N    GLY B  79      18.886  77.006  88.919  1.00 34.90      B  N
ATOM   2945  CA   GLY B  79      20.254  77.044  88.429  1.00 34.90      B  C
ATOM   2946  C    GLY B  79      20.741  75.644  88.053  1.00 34.90      B  C
ATOM   2947  O    GLY B  79      21.646  75.482  87.225  1.00 34.90      B  O
ATOM   2948  N    GLU B  80      20.126  74.634  88.669  1.00 40.40      B  N
ATOM   2949  CA   GLU B  80      20.445  73.221  88.445  1.00 40.40      B  C
ATOM   2950  CB   GLU B  80      19.532  72.338  89.293  1.00 51.75      B  C
ATOM   2951  CG   GLU B  80      19.861  72.313  90.767  1.00 51.75      B  C
ATOM   2952  CD   GLU B  80      18.792  71.596  91.580  1.00 51.75      B  C
ATOM   2953  OE1  GLU B  80      18.290  70.552  91.109  1.00 51.75      B  O
ATOM   2954  OE2  GLU B  80      18.459  72.067  92.691  1.00 51.75      B  O
ATOM   2955  C    GLU B  80      20.305  72.769  86.999  1.00 40.40      B  C
ATOM   2956  O    GLU B  80      19.486  73.300  86.248  1.00 40.40      B  O
ATOM   2957  N    LEU B  81      21.095  71.766  86.623  1.00 34.93      B  N
ATOM   2958  CA   LEU B  81      21.038  71.221  85.270  1.00 34.93      B  C
ATOM   2959  CB   LEU B  81      22.421  70.749  84.810  1.00 47.60      B  C
ATOM   2960  CG   LEU B  81      23.524  71.773  84.542  1.00 47.60      B  C
ATOM   2961  CD1  LEU B  81      24.686  71.067  83.842  1.00 47.60      B  C
ATOM   2962  CD2  LEU B  81      22.991  72.908  83.658  1.00 47.60      B  C
ATOM   2963  C    LEU B  81      20.068  70.045  85.166  1.00 34.93      B  C
ATOM   2964  O    LEU B  81      20.039  69.161  86.026  1.00 34.93      B  O
ATOM   2965  N    VAL B  82      19.282  70.037  84.097  1.00 34.39      B  N
ATOM   2966  CA   VAL B  82      18.333  68.962  83.864  1.00 34.39      B  C
ATOM   2967  CB   VAL B  82      16.886  69.448  83.995  1.00 28.95      B  C
ATOM   2968  CG1  VAL B  82      16.629  69.934  85.410  1.00 28.95      B  C
ATOM   2969  CG2  VAL B  82      16.620  70.553  82.973  1.00 28.95      B  C
ATOM   2970  C    VAL B  82      18.508  68.416  82.457  1.00 34.39      B  C
ATOM   2971  O    VAL B  82      19.176  69.022  81.619  1.00 34.39      B  O
ATOM   2972  N    ALA B  83      17.898  67.269  82.207  1.00 43.56      B  N
ATOM   2973  CA   ALA B  83      17.952  66.633  80.903  1.00 43.56      B  C
ATOM   2974  CB   ALA B  83      18.673  65.331  81.010  1.00 34.36      B  C
ATOM   2975  C    ALA B  83      16.511  66.402  80.455  1.00 43.56      B  C
ATOM   2976  O    ALA B  83      15.695  65.841  81.201  1.00 43.56      B  O
ATOM   2977  N    ILE B  84      16.187  66.833  79.243  1.00 26.32      B  N
ATOM   2978  CA   ILE B  84      14.834  66.659  78.757  1.00 26.32      B  C
ATOM   2979  CB   ILE B  84      14.234  67.989  78.265  1.00 30.96      B  C
ATOM   2980  CG2  ILE B  84      12.720  67.830  78.087  1.00 30.96      B  C
ATOM   2981  CG1  ILE B  84      14.505  69.099  79.286  1.00 30.96      B  C
ATOM   2982  CD1  ILE B  84      14.048  70.465  78.839  1.00 30.96      B  C
ATOM   2983  C    ILE B  84      14.779  65.657  77.620  1.00 26.32      B  C
ATOM   2984  O    ILE B  84      15.302  65.915  76.537  1.00 26.32      B  O
ATOM   2985  N    LYS B  85      14.156  64.510  77.879  1.00 32.13      B  N
ATOM   2986  CA   LYS B  85      14.007  63.476  76.872  1.00 32.13      B  C
ATOM   2987  CB   LYS B  85      13.956  62.098  77.524  1.00 42.19      B  C
ATOM   2988  CG   LYS B  85      14.171  60.979  76.548  1.00 42.19      B  C
ATOM   2989  CD   LYS B  85      13.456  59.700  76.941  1.00 42.19      B  C
ATOM   2990  CE   LYS B  85      13.633  58.617  75.841  1.00 42.19      B  C
ATOM   2991  NZ   LYS B  85      13.072  57.265  76.222  1.00 42.19      B  N
ATOM   2992  C    LYS B  85      12.680  63.754  76.174  1.00 32.13      B  C
ATOM   2993  O    LYS B  85      11.617  63.623  76.778  1.00 32.13      B  O
ATOM   2994  N    LYS B  86      12.739  64.158  74.911  1.00 33.24      B  N
ATOM   2995  CA   LYS B  86      11.533  64.454  74.145  1.00 33.24      B  C
ATOM   2996  CB   LYS B  86      11.759  65.717  73.319  1.00 47.29      B  C
ATOM   2997  CG   LYS B  86      10.523  66.274  72.658  1.00 47.29      B  C
ATOM   2998  CD   LYS B  86      10.848  67.533  71.851  1.00 47.29      B  C
ATOM   2999  CE   LYS B  86       9.566  68.290  71.476  1.00 47.29      B  C
ATOM   3000  NZ   LYS B  86       9.840  69.426  70.542  1.00 47.29      B  N
ATOM   3001  C    LYS B  86      11.206  63.281  73.222  1.00 33.24      B  C
ATOM   3002  O    LYS B  86      11.945  63.007  72.274  1.00 33.24      B  O
ATOM   3003  N    VAL B  87      10.106  62.588  73.503  1.00 32.07      B  N
ATOM   3004  CA   VAL B  87       9.698  61.450  72.689  1.00 32.07      B  C
ATOM   3005  CB   VAL B  87       9.626  60.147  73.508  1.00 23.22      B  C
ATOM   3006  CG1  VAL B  87      10.612  60.198  74.648  1.00 23.22      B  C
ATOM   3007  CG2  VAL B  87       8.207  59.902  73.987  1.00 23.22      B  C
ATOM   3008  C    VAL B  87       8.322  61.680  72.092  1.00 32.07      B  C
ATOM   3009  O    VAL B  87       7.496  62.390  72.668  1.00 32.07      B  O
```

FIG. 4-46

```
ATOM   3010  N    LEU B  88       8.080  61.078  70.931  1.00 59.76       B  N
ATOM   3011  CA   LEU B  88       6.782  61.201  70.281  1.00 59.76       B  C
ATOM   3012  CB   LEU B  88       6.834  60.622  68.867  1.00 58.01       B  C
ATOM   3013  CG   LEU B  88       5.523  60.627  68.078  1.00 58.01       B  C
ATOM   3014  CD1  LEU B  88       5.242  62.037  67.521  1.00 58.01       B  C
ATOM   3015  CD2  LEU B  88       5.638  59.612  66.950  1.00 58.01       B  C
ATOM   3016  C    LEU B  88       5.804  60.387  71.127  1.00 59.76       B  C
ATOM   3017  O    LEU B  88       6.057  59.211  71.424  1.00 59.76       B  O
ATOM   3018  N    GLN B  89       4.686  60.993  71.514  1.00 46.82       B  N
ATOM   3019  CA   GLN B  89       3.734  60.270  72.348  1.00 46.82       B  C
ATOM   3020  CB   GLN B  89       3.766  60.833  73.771  1.00 72.47       B  C
ATOM   3021  CG   GLN B  89       2.821  60.148  74.755  1.00 72.47       B  C
ATOM   3022  CD   GLN B  89       2.874  58.630  74.646  1.00 72.47       B  C
ATOM   3023  OE1  GLN B  89       3.915  58.039  74.289  1.00 72.47       B  O
ATOM   3024  NE2  GLN B  89       1.749  57.986  74.959  1.00 72.47       B  N
ATOM   3025  C    GLN B  89       2.312  60.292  71.829  1.00 46.82       B  C
ATOM   3026  O    GLN B  89       1.649  61.331  71.879  1.00 46.82       B  O
ATOM   3027  N    ASP B  90       1.845  59.140  71.346  1.00 49.25       B  N
ATOM   3028  CA   ASP B  90       0.488  59.045  70.832  1.00 49.25       B  C
ATOM   3029  CB   ASP B  90       0.237  57.705  70.139  1.00 60.57       B  C
ATOM   3030  CG   ASP B  90      -1.153  57.644  69.481  1.00 60.57       B  C
ATOM   3031  OD1  ASP B  90      -1.696  56.526  69.321  1.00 60.57       B  O
ATOM   3032  OD2  ASP B  90      -1.700  58.717  69.117  1.00 60.57       B  O
ATOM   3033  C    ASP B  90      -0.508  59.187  71.977  1.00 49.25       B  C
ATOM   3034  O    ASP B  90      -0.396  58.502  73.008  1.00 49.25       B  O
ATOM   3035  N    ALA B  91      -1.484  60.077  71.791  1.00 69.71       B  N
ATOM   3036  CA   ALA B  91      -2.513  60.314  72.804  1.00 69.71       B  C
ATOM   3037  CB   ALA B  91      -3.477  61.404  72.334  1.00 42.84       B  C
ATOM   3038  C    ALA B  91      -3.289  59.030  73.127  1.00 69.71       B  C
ATOM   3039  O    ALA B  91      -3.808  58.869  74.238  1.00 69.71       B  O
ATOM   3040  N    ALA B  92      -3.372  58.122  72.153  1.00 56.78       B  N
ATOM   3041  CA   ALA B  92      -4.069  56.854  72.353  1.00 56.78       B  C
ATOM   3042  CB   ALA B  92      -3.766  55.903  71.194  1.00 49.36       B  C
ATOM   3043  C    ALA B  92      -3.657  56.204  73.682  1.00 56.78       B  C
ATOM   3044  O    ALA B  92      -4.387  56.272  74.688  1.00 56.78       B  O
ATOM   3045  N    ALA B  93      -2.476  55.582  73.671  1.00 61.34       B  N
ATOM   3046  CA   ALA B  93      -1.933  54.899  74.841  1.00 61.34       B  C
ATOM   3047  CB   ALA B  93      -1.031  53.770  74.388  1.00 44.58       B  C
ATOM   3048  C    ALA B  93      -1.163  55.845  75.772  1.00 61.34       B  C
ATOM   3049  O    ALA B  93      -0.942  57.017  75.440  1.00 61.34       B  O
ATOM   3050  N    LYS B  94      -0.785  55.333  76.944  1.00 54.57       B  N
ATOM   3051  CA   LYS B  94      -0.016  56.100  77.932  1.00 54.57       B  C
ATOM   3052  CB   LYS B  94      -0.368  55.663  79.358  1.00 60.08       B  C
ATOM   3053  CG   LYS B  94      -1.841  55.784  79.699  1.00 60.08       B  C
ATOM   3054  CD   LYS B  94      -2.171  55.081  81.010  1.00 60.08       B  C
ATOM   3055  CE   LYS B  94      -3.646  55.289  81.389  1.00 60.08       B  C
ATOM   3056  NZ   LYS B  94      -4.569  54.953  80.238  1.00 60.08       B  N
ATOM   3057  C    LYS B  94       1.442  55.773  77.649  1.00 54.57       B  C
ATOM   3058  O    LYS B  94       1.731  54.865  76.869  1.00 54.57       B  O
ATOM   3059  N    ASN B  95       2.361  56.495  78.274  1.00 27.23       B  N
ATOM   3060  CA   ASN B  95       3.773  56.244  78.043  1.00 27.23       B  C
ATOM   3061  CB   ASN B  95       4.523  57.571  77.989  1.00 26.90       B  C
ATOM   3062  CG   ASN B  95       5.997  57.392  77.731  1.00 26.90       B  C
ATOM   3063  OD1  ASN B  95       6.739  56.906  78.585  1.00 26.90       B  O
ATOM   3064  ND2  ASN B  95       6.435  57.774  76.540  1.00 26.90       B  N
ATOM   3065  C    ASN B  95       4.305  55.383  79.172  1.00 27.23       B  C
ATOM   3066  O    ASN B  95       4.306  55.806  80.326  1.00 27.23       B  O
ATOM   3067  N    ARG B  96       4.758  54.176  78.838  1.00 22.12       B  N
ATOM   3068  CA   ARG B  96       5.266  53.251  79.849  1.00 22.12       B  C
ATOM   3069  CB   ARG B  96       5.674  51.917  79.228  1.00 51.11       B  C
ATOM   3070  CG   ARG B  96       5.018  50.714  79.892  1.00 51.11       B  C
ATOM   3071  CD   ARG B  96       6.055  49.705  80.364  1.00 51.11       B  C
ATOM   3072  NE   ARG B  96       6.982  49.331  79.291  1.00 51.11       B  N
ATOM   3073  CZ   ARG B  96       6.701  48.509  78.275  1.00 51.11       B  C
ATOM   3074  NH1  ARG B  96       5.495  47.939  78.173  1.00 51.11       B  N
ATOM   3075  NH2  ARG B  96       7.640  48.265  77.352  1.00 51.11       B  N
ATOM   3076  C    ARG B  96       6.425  53.809  80.649  1.00 22.12       B  C
```

FIG. 4-47

| ATOM | 3077 | O   | ARG | B | 96  | 6.435  | 53.705 | 81.867 | 1.00 | 22.12 | B | O |
|------|------|-----|-----|---|-----|--------|--------|--------|------|-------|---|---|
| ATOM | 3078 | N   | GLU | B | 97  | 7.396  | 54.405 | 79.964 | 1.00 | 33.24 | B | N |
| ATOM | 3079 | CA  | GLU | B | 97  | 8.563  | 54.974 | 80.632 | 1.00 | 33.24 | B | C |
| ATOM | 3080 | CB  | GLU | B | 97  | 9.478  | 55.657 | 79.608 | 1.00 | 25.31 | B | C |
| ATOM | 3081 | CG  | GLU | B | 97  | 10.862 | 56.037 | 80.121 | 1.00 | 25.31 | B | C |
| ATOM | 3082 | CD  | GLU | B | 97  | 11.736 | 56.657 | 79.043 | 1.00 | 25.31 | B | C |
| ATOM | 3083 | OE1 | GLU | B | 97  | 12.944 | 56.851 | 79.286 | 1.00 | 25.31 | B | O |
| ATOM | 3084 | OE2 | GLU | B | 97  | 11.217 | 56.955 | 77.950 | 1.00 | 25.31 | B | O |
| ATOM | 3085 | C   | GLU | B | 97  | 8.067  | 55.985 | 81.657 | 1.00 | 33.24 | B | C |
| ATOM | 3086 | O   | GLU | B | 97  | 8.434  | 55.916 | 82.820 | 1.00 | 33.24 | B | O |
| ATOM | 3087 | N   | LEU | B | 98  | 7.218  | 56.912 | 81.231 | 1.00 | 18.12 | B | N |
| ATOM | 3088 | CA  | LEU | B | 98  | 6.692  | 57.912 | 82.147 | 1.00 | 18.12 | B | C |
| ATOM | 3089 | CB  | LEU | B | 98  | 5.648  | 58.789 | 81.456 | 1.00 | 12.96 | B | C |
| ATOM | 3090 | CG  | LEU | B | 98  | 4.906  | 59.779 | 82.373 | 1.00 | 12.96 | B | C |
| ATOM | 3091 | CD1 | LEU | B | 98  | 5.871  | 60.827 | 82.926 | 1.00 | 12.96 | B | C |
| ATOM | 3092 | CD2 | LEU | B | 98  | 3.802  | 60.467 | 81.606 | 1.00 | 12.96 | B | C |
| ATOM | 3093 | C   | LEU | B | 98  | 6.034  | 57.249 | 83.333 | 1.00 | 18.12 | B | C |
| ATOM | 3094 | O   | LEU | B | 98  | 6.332  | 57.556 | 84.473 | 1.00 | 18.12 | B | O |
| ATOM | 3095 | N   | GLN | B | 99  | 5.121  | 56.340 | 83.041 | 1.00 | 36.34 | B | N |
| ATOM | 3096 | CA  | GLN | B | 99  | 4.396  | 55.637 | 84.072 | 1.00 | 36.34 | B | C |
| ATOM | 3097 | CB  | GLN | B | 99  | 3.519  | 54.551 | 83.455 | 1.00 | 99.29 | B | C |
| ATOM | 3098 | CG  | GLN | B | 99  | 2.696  | 53.800 | 84.500 | 1.00 | 99.29 | B | C |
| ATOM | 3099 | CD  | GLN | B | 99  | 2.055  | 52.504 | 83.979 | 1.00 | 99.29 | B | C |
| ATOM | 3100 | OE1 | GLN | B | 99  | 1.514  | 51.714 | 84.776 | 1.00 | 99.29 | B | O |
| ATOM | 3101 | NE2 | GLN | B | 99  | 2.115  | 52.276 | 82.644 | 1.00 | 99.29 | B | N |
| ATOM | 3102 | C   | GLN | B | 99  | 5.279  | 55.012 | 85.132 | 1.00 | 36.34 | B | C |
| ATOM | 3103 | O   | GLN | B | 99  | 4.975  | 55.133 | 86.314 | 1.00 | 36.34 | B | O |
| ATOM | 3104 | N   | ILE | B | 100 | 6.358  | 54.338 | 84.727 | 1.00 | 34.19 | B | N |
| ATOM | 3105 | CA  | ILE | B | 100 | 7.223  | 53.709 | 85.717 | 1.00 | 34.19 | B | C |
| ATOM | 3106 | CB  | ILE | B | 100 | 8.060  | 52.519 | 85.138 | 1.00 | 25.81 | B | C |
| ATOM | 3107 | CG2 | ILE | B | 100 | 7.358  | 51.875 | 83.998 | 1.00 | 25.81 | B | C |
| ATOM | 3108 | CG1 | ILE | B | 100 | 9.437  | 52.987 | 84.722 | 1.00 | 25.81 | B | C |
| ATOM | 3109 | CD1 | ILE | B | 100 | 10.498 | 52.563 | 85.709 | 1.00 | 25.81 | B | C |
| ATOM | 3110 | C   | ILE | B | 100 | 8.130  | 54.735 | 86.418 | 1.00 | 34.19 | B | C |
| ATOM | 3111 | O   | ILE | B | 100 | 8.426  | 54.595 | 87.604 | 1.00 | 34.19 | B | O |
| ATOM | 3112 | N   | MET | B | 101 | 8.540  | 55.777 | 85.699 | 1.00 | 23.14 | B | N |
| ATOM | 3113 | CA  | MET | B | 101 | 9.381  | 56.826 | 86.273 | 1.00 | 23.14 | B | C |
| ATOM | 3114 | CB  | MET | B | 101 | 9.686  | 57.897 | 85.226 | 1.00 | 41.31 | B | C |
| ATOM | 3115 | CG  | MET | B | 101 | 10.809 | 57.546 | 84.279 | 1.00 | 41.31 | B | C |
| ATOM | 3116 | SD  | MET | B | 101 | 12.380 | 57.518 | 85.109 | 1.00 | 41.31 | B | S |
| ATOM | 3117 | CE  | MET | B | 101 | 12.395 | 55.853 | 85.726 | 1.00 | 41.31 | B | C |
| ATOM | 3118 | C   | MET | B | 101 | 8.633  | 57.475 | 87.422 | 1.00 | 23.14 | B | C |
| ATOM | 3119 | O   | MET | B | 101 | 9.155  | 57.653 | 88.508 | 1.00 | 23.14 | B | O |
| ATOM | 3120 | N   | ARG | B | 102 | 7.389  | 57.823 | 87.164 | 1.00 | 28.05 | B | N |
| ATOM | 3121 | CA  | ARG | B | 102 | 6.566  | 58.469 | 88.157 | 1.00 | 28.05 | B | C |
| ATOM | 3122 | CB  | ARG | B | 102 | 5.178  | 58.712 | 87.589 | 1.00 | 37.12 | B | C |
| ATOM | 3123 | CG  | ARG | B | 102 | 5.193  | 59.715 | 86.475 | 1.00 | 37.12 | B | C |
| ATOM | 3124 | CD  | ARG | B | 102 | 4.727  | 61.033 | 86.980 | 1.00 | 37.12 | B | C |
| ATOM | 3125 | NE  | ARG | B | 102 | 3.279  | 61.134 | 86.931 | 1.00 | 37.12 | B | N |
| ATOM | 3126 | CZ  | ARG | B | 102 | 2.551  | 61.791 | 87.820 | 1.00 | 37.12 | B | C |
| ATOM | 3127 | NH1 | ARG | B | 102 | 3.136  | 62.411 | 88.850 | 1.00 | 37.12 | B | N |
| ATOM | 3128 | NH2 | ARG | B | 102 | 1.233  | 61.830 | 87.666 | 1.00 | 37.12 | B | N |
| ATOM | 3129 | C   | ARG | B | 102 | 6.475  | 57.756 | 89.493 | 1.00 | 28.05 | B | C |
| ATOM | 3130 | O   | ARG | B | 102 | 6.288  | 58.411 | 90.514 | 1.00 | 28.05 | B | O |
| ATOM | 3131 | N   | LYS | B | 103 | 6.622  | 56.432 | 89.502 | 1.00 | 24.99 | B | N |
| ATOM | 3132 | CA  | LYS | B | 103 | 6.526  | 55.684 | 90.757 | 1.00 | 24.99 | B | C |
| ATOM | 3133 | CB  | LYS | B | 103 | 5.589  | 54.481 | 90.593 | 1.00 | 42.26 | B | C |
| ATOM | 3134 | CG  | LYS | B | 103 | 6.257  | 53.201 | 90.133 | 1.00 | 42.26 | B | C |
| ATOM | 3135 | CD  | LYS | B | 103 | 5.234  | 52.079 | 89.981 | 1.00 | 42.26 | B | C |
| ATOM | 3136 | CE  | LYS | B | 103 | 4.320  | 52.311 | 88.763 | 1.00 | 42.26 | B | C |
| ATOM | 3137 | NZ  | LYS | B | 103 | 3.169  | 51.357 | 88.679 | 1.00 | 42.26 | B | N |
| ATOM | 3138 | C   | LYS | B | 103 | 7.864  | 55.226 | 91.339 | 1.00 | 24.99 | B | C |
| ATOM | 3139 | O   | LYS | B | 103 | 7.906  | 54.423 | 92.267 | 1.00 | 24.99 | B | O |
| ATOM | 3140 | N   | LEU | B | 104 | 8.958  | 55.756 | 90.809 | 1.00 | 25.17 | B | N |
| ATOM | 3141 | CA  | LEU | B | 104 | 10.286 | 55.378 | 91.274 | 1.00 | 25.17 | B | C |
| ATOM | 3142 | CB  | LEU | B | 104 | 11.166 | 54.990 | 90.093 | 1.00 | 22.33 | B | C |
| ATOM | 3143 | CG  | LEU | B | 104 | 11.354 | 53.506 | 89.806 | 1.00 | 22.33 | B | C |

FIG. 4-48

| | | | | | | | | | | |
|---|---|---|---|---|---|---|---|---|---|---|
| ATOM | 3144 | CD1 | LEU | B | 104 | 10.024 | 52.792 | 89.791 | 1.00 22.33 | B C |
| ATOM | 3145 | CD2 | LEU | B | 104 | 12.061 | 53.363 | 88.472 | 1.00 22.33 | B C |
| ATOM | 3146 | C | LEU | B | 104 | 10.958 | 56.497 | 92.033 | 1.00 25.17 | B C |
| ATOM | 3147 | O | LEU | B | 104 | 10.962 | 57.641 | 91.589 | 1.00 25.17 | B O |
| ATOM | 3148 | N | ASP | B | 105 | 11.528 | 56.161 | 93.181 | 1.00 26.27 | B N |
| ATOM | 3149 | CA | ASP | B | 105 | 12.229 | 57.137 | 94.002 | 1.00 26.27 | B C |
| ATOM | 3150 | CB | ASP | B | 105 | 11.273 | 57.865 | 94.949 | 1.00 30.41 | B C |
| ATOM | 3151 | CG | ASP | B | 105 | 12.004 | 58.788 | 95.902 | 1.00 30.41 | B C |
| ATOM | 3152 | OD1 | ASP | B | 105 | 12.916 | 59.520 | 95.432 | 1.00 30.41 | B O |
| ATOM | 3153 | OD2 | ASP | B | 105 | 11.655 | 58.771 | 97.106 | 1.00 30.41 | B O |
| ATOM | 3154 | C | ASP | B | 105 | 13.298 | 56.419 | 94.814 | 1.00 26.27 | B C |
| ATOM | 3155 | O | ASP | B | 105 | 13.020 | 55.850 | 95.870 | 1.00 26.27 | B O |
| ATOM | 3156 | N | HIS | B | 106 | 14.528 | 56.457 | 94.306 | 1.00 31.74 | B N |
| ATOM | 3157 | CA | HIS | B | 106 | 15.659 | 55.804 | 94.950 | 1.00 31.74 | B C |
| ATOM | 3158 | CB | HIS | B | 106 | 15.801 | 54.381 | 94.395 | 1.00 19.57 | B C |
| ATOM | 3159 | CG | HIS | B | 106 | 16.793 | 53.530 | 95.130 | 1.00 19.57 | B C |
| ATOM | 3160 | CD2 | HIS | B | 106 | 16.615 | 52.524 | 96.017 | 1.00 19.57 | B C |
| ATOM | 3161 | ND1 | HIS | B | 106 | 18.154 | 53.667 | 94.976 | 1.00 19.57 | B N |
| ATOM | 3162 | CE1 | HIS | B | 106 | 18.770 | 52.781 | 95.735 | 1.00 19.57 | B C |
| ATOM | 3163 | NE2 | HIS | B | 106 | 17.860 | 52.076 | 96.376 | 1.00 19.57 | B N |
| ATOM | 3164 | C | HIS | B | 106 | 16.927 | 56.602 | 94.685 | 1.00 31.74 | B C |
| ATOM | 3165 | O | HIS | B | 106 | 17.151 | 57.040 | 93.572 | 1.00 31.74 | B O |
| ATOM | 3166 | N | CYS | B | 107 | 17.747 | 56.791 | 95.708 | 1.00 18.06 | B N |
| ATOM | 3167 | CA | CYS | B | 107 | 18.979 | 57.559 | 95.593 | 1.00 18.06 | B C |
| ATOM | 3168 | CB | CYS | B | 107 | 19.737 | 57.515 | 96.919 | 1.00 25.39 | B C |
| ATOM | 3169 | SG | CYS | B | 107 | 20.626 | 55.995 | 97.224 | 1.00 25.39 | B S |
| ATOM | 3170 | C | CYS | B | 107 | 19.901 | 57.091 | 94.474 | 1.00 18.06 | B C |
| ATOM | 3171 | O | CYS | B | 107 | 20.869 | 57.761 | 94.147 | 1.00 18.06 | B O |
| ATOM | 3172 | N | ASN | B | 108 | 19.604 | 55.939 | 93.887 | 1.00 21.61 | B N |
| ATOM | 3173 | CA | ASN | B | 108 | 20.433 | 55.413 | 92.820 | 1.00 21.61 | B C |
| ATOM | 3174 | CB | ASN | B | 108 | 20.928 | 54.019 | 93.213 | 1.00 28.65 | B C |
| ATOM | 3175 | CG | ASN | B | 108 | 22.054 | 54.066 | 94.241 | 1.00 28.65 | B C |
| ATOM | 3176 | OD1 | ASN | B | 108 | 22.106 | 53.253 | 95.159 | 1.00 28.65 | B O |
| ATOM | 3177 | ND2 | ASN | B | 108 | 22.967 | 55.008 | 94.074 | 1.00 28.65 | B N |
| ATOM | 3178 | C | ASN | B | 108 | 19.764 | 55.374 | 91.458 | 1.00 21.61 | B C |
| ATOM | 3179 | O | ASN | B | 108 | 20.224 | 54.681 | 90.561 | 1.00 21.61 | B O |
| ATOM | 3180 | N | ILE | B | 109 | 18.671 | 56.107 | 91.301 | 1.00 15.37 | B N |
| ATOM | 3181 | CA | ILE | B | 109 | 17.989 | 56.160 | 90.019 | 1.00 15.37 | B C |
| ATOM | 3182 | CB | ILE | B | 109 | 16.642 | 55.410 | 90.054 | 1.00 23.79 | B C |
| ATOM | 3183 | CG2 | ILE | B | 109 | 15.930 | 55.548 | 88.707 | 1.00 23.79 | B C |
| ATOM | 3184 | CG1 | ILE | B | 109 | 16.897 | 53.925 | 90.327 | 1.00 23.79 | B C |
| ATOM | 3185 | CD1 | ILE | B | 109 | 15.664 | 53.130 | 90.565 | 1.00 23.79 | B C |
| ATOM | 3186 | C | ILE | B | 109 | 17.799 | 57.624 | 89.698 | 1.00 15.37 | B C |
| ATOM | 3187 | O | ILE | B | 109 | 17.471 | 58.414 | 90.575 | 1.00 15.37 | B O |
| ATOM | 3188 | N | VAL | B | 110 | 18.054 | 57.993 | 88.448 | 1.00 17.53 | B N |
| ATOM | 3189 | CA | VAL | B | 110 | 17.903 | 59.375 | 88.025 | 1.00 17.53 | B C |
| ATOM | 3190 | CB | VAL | B | 110 | 18.263 | 59.533 | 86.511 | 1.00 13.38 | B C |
| ATOM | 3191 | CG1 | VAL | B | 110 | 17.155 | 59.003 | 85.625 | 1.00 13.38 | B C |
| ATOM | 3192 | CG2 | VAL | B | 110 | 18.567 | 60.970 | 86.200 | 1.00 13.38 | B C |
| ATOM | 3193 | C | VAL | B | 110 | 16.474 | 59.804 | 88.321 | 1.00 17.53 | B C |
| ATOM | 3194 | O | VAL | B | 110 | 15.526 | 59.045 | 88.124 | 1.00 17.53 | B O |
| ATOM | 3195 | N | ARG | B | 111 | 16.337 | 61.021 | 88.824 | 1.00 25.48 | B N |
| ATOM | 3196 | CA | ARG | B | 111 | 15.035 | 61.568 | 89.168 | 1.00 25.48 | B C |
| ATOM | 3197 | CB | ARG | B | 111 | 15.192 | 62.526 | 90.348 | 1.00 64.22 | B C |
| ATOM | 3198 | CG | ARG | B | 111 | 13.948 | 63.320 | 90.673 | 1.00 64.22 | B C |
| ATOM | 3199 | CD | ARG | B | 111 | 13.593 | 63.204 | 92.146 | 1.00 64.22 | B C |
| ATOM | 3200 | NE | ARG | B | 111 | 13.800 | 64.459 | 92.873 | 1.00 64.22 | B N |
| ATOM | 3201 | CZ | ARG | B | 111 | 14.964 | 65.109 | 92.969 | 1.00 64.22 | B C |
| ATOM | 3202 | NH1 | ARG | B | 111 | 16.060 | 64.637 | 92.378 | 1.00 64.22 | B N |
| ATOM | 3203 | NH2 | ARG | B | 111 | 15.036 | 66.233 | 93.678 | 1.00 64.22 | B N |
| ATOM | 3204 | C | ARG | B | 111 | 14.298 | 62.280 | 88.029 | 1.00 25.48 | B C |
| ATOM | 3205 | O | ARG | B | 111 | 14.895 | 62.999 | 87.225 | 1.00 25.48 | B O |
| ATOM | 3206 | N | LEU | B | 112 | 12.989 | 62.061 | 87.972 | 1.00 20.16 | B N |
| ATOM | 3207 | CA | LEU | B | 112 | 12.132 | 62.711 | 86.993 | 1.00 20.16 | B C |
| ATOM | 3208 | CB | LEU | B | 112 | 10.974 | 61.789 | 86.604 | 1.00 19.51 | B C |
| ATOM | 3209 | CG | LEU | B | 112 | 9.895 | 62.393 | 85.706 | 1.00 19.51 | B C |
| ATOM | 3210 | CD1 | LEU | B | 112 | 10.462 | 62.661 | 84.326 | 1.00 19.51 | B C |

FIG. 4-49

```
ATOM   3211  CD2 LEU B 112       8.705  61.449  85.636  1.00 19.51      B  C
ATOM   3212  C   LEU B 112      11.614  63.955  87.718  1.00 20.16      B  C
ATOM   3213  O   LEU B 112      10.667  63.890  88.489  1.00 20.16      B  O
ATOM   3214  N   ARG B 113      12.263  65.084  87.485  1.00 27.13      B  N
ATOM   3215  CA  ARG B 113      11.890  66.329  88.139  1.00 27.13      B  C
ATOM   3216  CB  ARG B 113      12.906  67.410  87.775  1.00 44.98      B  C
ATOM   3217  CG  ARG B 113      14.330  67.037  88.158  1.00 44.98      B  C
ATOM   3218  CD  ARG B 113      14.478  66.967  89.681  1.00 44.98      B  C
ATOM   3219  NE  ARG B 113      14.592  68.301  90.272  1.00 44.98      B  N
ATOM   3220  CZ  ARG B 113      15.606  69.123  90.024  1.00 44.98      B  C
ATOM   3221  NH1 ARG B 113      16.573  68.718  89.207  1.00 44.98      B  N
ATOM   3222  NH2 ARG B 113      15.644  70.342  90.560  1.00 44.98      B  N
ATOM   3223  C   ARG B 113      10.491  66.757  87.736  1.00 27.13      B  C
ATOM   3224  O   ARG B 113       9.639  67.009  88.585  1.00 27.13      B  O
ATOM   3225  N   TYR B 114      10.264  66.849  86.433  1.00 37.03      B  N
ATOM   3226  CA  TYR B 114       8.969  67.242  85.908  1.00 37.03      B  C
ATOM   3227  CB  TYR B 114       8.954  68.743  85.621  1.00 26.59      B  C
ATOM   3228  CG  TYR B 114       9.244  69.593  86.836  1.00 26.59      B  C
ATOM   3229  CD1 TYR B 114       8.293  69.775  87.827  1.00 26.59      B  C
ATOM   3230  CE1 TYR B 114       8.578  70.507  88.965  1.00 26.59      B  C
ATOM   3231  CD2 TYR B 114      10.485  70.173  87.018  1.00 26.59      B  C
ATOM   3232  CE2 TYR B 114      10.772  70.902  88.155  1.00 26.59      B  C
ATOM   3233  CZ  TYR B 114       9.817  71.059  89.124  1.00 26.59      B  C
ATOM   3234  OH  TYR B 114      10.123  71.730  90.279  1.00 26.59      B  O
ATOM   3235  C   TYR B 114       8.745  66.485  84.621  1.00 37.03      B  C
ATOM   3236  O   TYR B 114       9.555  65.651  84.235  1.00 37.03      B  O
ATOM   3237  N   PHE B 115       7.624  66.760  83.974  1.00 26.55      B  N
ATOM   3238  CA  PHE B 115       7.315  66.144  82.700  1.00 26.55      B  C
ATOM   3239  CB  PHE B 115       6.907  64.655  82.860  1.00 24.05      B  C
ATOM   3240  CG  PHE B 115       5.510  64.415  83.383  1.00 24.05      B  C
ATOM   3241  CD1 PHE B 115       4.418  64.488  82.544  1.00 24.05      B  C
ATOM   3242  CD2 PHE B 115       5.301  64.043  84.710  1.00 24.05      B  C
ATOM   3243  CE1 PHE B 115       3.154  64.192  83.023  1.00 24.05      B  C
ATOM   3244  CE2 PHE B 115       4.032  63.749  85.186  1.00 24.05      B  C
ATOM   3245  CZ  PHE B 115       2.968  63.821  84.348  1.00 24.05      B  C
ATOM   3246  C   PHE B 115       6.220  67.012  82.147  1.00 26.55      B  C
ATOM   3247  O   PHE B 115       5.408  67.531  82.912  1.00 26.55      B  O
ATOM   3248  N   PHE B 116       6.230  67.213  80.833  1.00 32.58      B  N
ATOM   3249  CA  PHE B 116       5.236  68.064  80.196  1.00 32.58      B  C
ATOM   3250  CB  PHE B 116       5.601  69.536  80.432  1.00 30.53      B  C
ATOM   3251  CG  PHE B 116       6.910  69.952  79.821  1.00 30.53      B  C
ATOM   3252  CD1 PHE B 116       6.981  70.351  78.489  1.00 30.53      B  C
ATOM   3253  CD2 PHE B 116       8.076  69.947  80.586  1.00 30.53      B  C
ATOM   3254  CE1 PHE B 116       8.204  70.747  77.927  1.00 30.53      B  C
ATOM   3255  CE2 PHE B 116       9.301  70.336  80.043  1.00 30.53      B  C
ATOM   3256  CZ  PHE B 116       9.369  70.738  78.711  1.00 30.53      B  C
ATOM   3257  C   PHE B 116       5.092  67.816  78.710  1.00 32.58      B  C
ATOM   3258  O   PHE B 116       5.992  67.292  78.069  1.00 32.58      B  O
ATOM   3259  N   TYR B 117       3.939  68.191  78.172  1.00 45.46      B  N
ATOM   3260  CA  TYR B 117       3.687  68.037  76.757  1.00 45.46      B  C
ATOM   3261  CB  TYR B 117       2.286  67.504  76.531  1.00 31.09      B  C
ATOM   3262  CG  TYR B 117       2.031  66.260  77.316  1.00 31.09      B  C
ATOM   3263  CD1 TYR B 117       1.808  66.322  78.676  1.00 31.09      B  C
ATOM   3264  CE1 TYR B 117       1.585  65.173  79.411  1.00 31.09      B  C
ATOM   3265  CD2 TYR B 117       2.025  65.013  76.703  1.00 31.09      B  C
ATOM   3266  CE2 TYR B 117       1.803  63.852  77.435  1.00 31.09      B  C
ATOM   3267  CZ  TYR B 117       1.587  63.943  78.786  1.00 31.09      B  C
ATOM   3268  OH  TYR B 117       1.407  62.802  79.523  1.00 31.09      B  O
ATOM   3269  C   TYR B 117       3.855  69.387  76.078  1.00 45.46      B  C
ATOM   3270  O   TYR B 117       3.594  70.438  76.664  1.00 45.46      B  O
ATOM   3271  N   SER B 118       4.332  69.336  74.847  1.00 60.64      B  N
ATOM   3272  CA  SER B 118       4.542  70.515  74.013  1.00 60.64      B  C
ATOM   3273  CB  SER B 118       5.874  71.186  74.336  1.00 49.95      B  C
ATOM   3274  OG  SER B 118       6.954  70.339  73.983  1.00 49.95      B  O
ATOM   3275  C   SER B 118       4.642  69.835  72.657  1.00 60.64      B  C
ATOM   3276  O   SER B 118       5.628  69.140  72.359  1.00 60.64      B  O
ATOM   3277  N   SER B 119       3.618  69.980  71.842  1.00 70.17      B  N
```

FIG. 4-50

| ATOM | 3278 | CA | SER | B | 119 | 3.673 | 69.338 | 70.537 | 1.00 | 70.17 | B | C |
| ATOM | 3279 | CB | SER | B | 119 | 2.334 | 69.560 | 69.791 | 1.00 | 81.49 | B | C |
| ATOM | 3280 | OG | SER | B | 119 | 2.076 | 70.953 | 69.621 | 1.00 | 81.49 | B | O |
| ATOM | 3281 | C | SER | B | 119 | 4.791 | 70.059 | 69.740 | 1.00 | 70.17 | B | C |
| ATOM | 3282 | O | SER | B | 119 | 5.119 | 71.240 | 69.994 | 1.00 | 70.17 | B | O |
| ATOM | 3283 | N | GLY | B | 120 | 5.345 | 69.349 | 68.760 | 1.00 | 99.28 | B | N |
| ATOM | 3284 | CA | GLY | B | 120 | 6.418 | 69.903 | 67.956 | 1.00 | 99.28 | B | C |
| ATOM | 3285 | C | GLY | B | 120 | 6.005 | 70.033 | 66.513 | 1.00 | 99.28 | B | C |
| ATOM | 3286 | O | GLY | B | 120 | 4.884 | 70.496 | 66.229 | 1.00 | 99.28 | B | O |
| ATOM | 3287 | N | ALA | B | 121 | 6.897 | 69.604 | 65.614 | 1.00 | 98.96 | B | N |
| ATOM | 3288 | CA | ALA | B | 121 | 6.673 | 69.685 | 64.169 | 1.00 | 98.96 | B | C |
| ATOM | 3289 | CB | ALA | B | 121 | 7.574 | 68.657 | 63.454 | 1.00 | 18.56 | B | C |
| ATOM | 3290 | C | ALA | B | 121 | 5.188 | 69.533 | 63.715 | 1.00 | 98.96 | B | C |
| ATOM | 3291 | O | ALA | B | 121 | 4.380 | 70.482 | 63.852 | 1.00 | 98.96 | B | O |
| ATOM | 3292 | N | ALA | B | 122 | 4.832 | 68.352 | 63.195 | 1.00 | 100.00 | B | N |
| ATOM | 3293 | CA | ALA | B | 122 | 3.469 | 68.094 | 62.709 | 1.00 | 100.00 | B | C |
| ATOM | 3294 | CB | ALA | B | 122 | 3.314 | 66.620 | 62.318 | 1.00 | 80.62 | B | C |
| ATOM | 3295 | C | ALA | B | 122 | 2.345 | 68.504 | 63.675 | 1.00 | 100.00 | B | C |
| ATOM | 3296 | O | ALA | B | 122 | 2.532 | 68.564 | 64.903 | 1.00 | 100.00 | B | O |
| ATOM | 3297 | N | ALA | B | 123 | 1.178 | 68.780 | 63.085 | 1.00 | 68.46 | B | N |
| ATOM | 3298 | CA | ALA | B | 123 | -0.030 | 69.223 | 63.801 | 1.00 | 68.46 | B | C |
| ATOM | 3299 | CB | ALA | B | 123 | -1.176 | 69.495 | 62.785 | 1.00 | 56.00 | B | C |
| ATOM | 3300 | C | ALA | B | 123 | -0.531 | 68.273 | 64.886 | 1.00 | 68.46 | B | C |
| ATOM | 3301 | O | ALA | B | 123 | -0.417 | 68.554 | 66.088 | 1.00 | 68.46 | B | O |
| ATOM | 3302 | N | ALA | B | 124 | -1.132 | 67.168 | 64.453 | 1.00 | 100.00 | B | N |
| ATOM | 3303 | CA | ALA | B | 124 | -1.650 | 66.169 | 65.389 | 1.00 | 100.00 | B | C |
| ATOM | 3304 | CB | ALA | B | 124 | -2.684 | 65.265 | 64.688 | 1.00 | 71.71 | B | C |
| ATOM | 3305 | C | ALA | B | 124 | -0.459 | 65.337 | 65.875 | 1.00 | 100.00 | B | C |
| ATOM | 3306 | O | ALA | B | 124 | -0.558 | 64.112 | 66.060 | 1.00 | 100.00 | B | O |
| ATOM | 3307 | N | GLU | B | 125 | 0.668 | 66.027 | 66.059 | 1.00 | 78.20 | B | N |
| ATOM | 3308 | CA | GLU | B | 125 | 1.922 | 65.422 | 66.492 | 1.00 | 78.20 | B | C |
| ATOM | 3309 | CB | GLU | B | 125 | 2.981 | 65.694 | 65.408 | 1.00 | 81.30 | B | C |
| ATOM | 3310 | CG | GLU | B | 125 | 4.273 | 64.892 | 65.512 | 1.00 | 81.30 | B | C |
| ATOM | 3311 | CD | GLU | B | 125 | 5.239 | 65.147 | 64.317 | 1.00 | 81.30 | B | C |
| ATOM | 3312 | OE1 | GLU | B | 125 | 5.209 | 64.380 | 63.302 | 1.00 | 81.30 | B | O |
| ATOM | 3313 | OE2 | GLU | B | 125 | 6.018 | 66.135 | 64.405 | 1.00 | 81.30 | B | O |
| ATOM | 3314 | C | GLU | B | 125 | 2.322 | 66.040 | 67.846 | 1.00 | 78.20 | B | C |
| ATOM | 3315 | O | GLU | B | 125 | 2.801 | 67.189 | 67.908 | 1.00 | 78.20 | B | O |
| ATOM | 3316 | N | VAL | B | 126 | 2.100 | 65.294 | 68.930 | 1.00 | 48.91 | B | N |
| ATOM | 3317 | CA | VAL | B | 126 | 2.438 | 65.811 | 70.259 | 1.00 | 48.91 | B | C |
| ATOM | 3318 | CB | VAL | B | 126 | 1.263 | 65.702 | 71.236 | 1.00 | 42.54 | B | C |
| ATOM | 3319 | CG1 | VAL | B | 126 | 0.038 | 66.299 | 70.611 | 1.00 | 42.54 | B | C |
| ATOM | 3320 | CG2 | VAL | B | 126 | 1.046 | 64.255 | 71.638 | 1.00 | 42.54 | B | C |
| ATOM | 3321 | C | VAL | B | 126 | 3.641 | 65.155 | 70.923 | 1.00 | 48.91 | B | C |
| ATOM | 3322 | O | VAL | B | 126 | 4.021 | 64.013 | 70.616 | 1.00 | 48.91 | B | O |
| ATOM | 3323 | N | TYR | B | 127 | 4.237 | 65.887 | 71.854 | 1.00 | 49.97 | B | N |
| ATOM | 3324 | CA | TYR | B | 127 | 5.392 | 65.358 | 72.540 | 1.00 | 49.97 | B | C |
| ATOM | 3325 | CB | TYR | B | 127 | 6.639 | 66.162 | 72.183 | 1.00 | 68.51 | B | C |
| ATOM | 3326 | CG | TYR | B | 127 | 7.024 | 66.011 | 70.744 | 1.00 | 68.51 | B | C |
| ATOM | 3327 | CD1 | TYR | B | 127 | 6.937 | 67.091 | 69.869 | 1.00 | 68.51 | B | C |
| ATOM | 3328 | CE1 | TYR | B | 127 | 7.237 | 66.947 | 68.515 | 1.00 | 68.51 | B | C |
| ATOM | 3329 | CD2 | TYR | B | 127 | 7.425 | 64.769 | 70.238 | 1.00 | 68.51 | B | C |
| ATOM | 3330 | CE2 | TYR | B | 127 | 7.725 | 64.608 | 68.890 | 1.00 | 68.51 | B | C |
| ATOM | 3331 | CZ | TYR | B | 127 | 7.630 | 65.708 | 68.029 | 1.00 | 68.51 | B | C |
| ATOM | 3332 | OH | TYR | B | 127 | 7.924 | 65.596 | 66.682 | 1.00 | 68.51 | B | O |
| ATOM | 3333 | C | TYR | B | 127 | 5.319 | 65.214 | 74.054 | 1.00 | 49.97 | B | C |
| ATOM | 3334 | O | TYR | B | 127 | 4.628 | 65.971 | 74.747 | 1.00 | 49.97 | B | O |
| ATOM | 3335 | N | LEU | B | 128 | 6.042 | 64.218 | 74.557 | 1.00 | 36.31 | B | N |
| ATOM | 3336 | CA | LEU | B | 128 | 6.128 | 63.984 | 75.984 | 1.00 | 36.31 | B | C |
| ATOM | 3337 | CB | LEU | B | 128 | 6.044 | 62.494 | 76.315 | 1.00 | 34.80 | B | C |
| ATOM | 3338 | CG | LEU | B | 128 | 6.162 | 62.161 | 77.804 | 1.00 | 34.80 | B | C |
| ATOM | 3339 | CD1 | LEU | B | 128 | 4.988 | 62.764 | 78.566 | 1.00 | 34.80 | B | C |
| ATOM | 3340 | CD2 | LEU | B | 128 | 6.192 | 60.657 | 77.982 | 1.00 | 34.80 | B | C |
| ATOM | 3341 | C | LEU | B | 128 | 7.513 | 64.484 | 76.305 | 1.00 | 36.31 | B | C |
| ATOM | 3342 | O | LEU | B | 128 | 8.471 | 64.113 | 75.640 | 1.00 | 36.31 | B | O |
| ATOM | 3343 | N | ASN | B | 129 | 7.619 | 65.362 | 77.288 | 1.00 | 27.12 | B | N |
| ATOM | 3344 | CA | ASN | B | 129 | 8.918 | 65.895 | 77.665 | 1.00 | 27.12 | B | C |

FIG. 4-51

```
ATOM   3345  CB   ASN B 129       8.888  67.422  77.655  1.00 27.30           B  C
ATOM   3346  CG   ASN B 129       8.807  67.992  76.258  1.00 27.30           B  C
ATOM   3347  OD1  ASN B 129       9.821  68.160  75.575  1.00 27.30           B  O
ATOM   3348  ND2  ASN B 129       7.592  68.282  75.816  1.00 27.30           B  N
ATOM   3349  C    ASN B 129       9.240  65.379  79.061  1.00 27.12           B  C
ATOM   3350  O    ASN B 129       8.470  65.583  79.998  1.00 27.12           B  O
ATOM   3351  N    LEU B 130      10.366  64.686  79.197  1.00 36.25           B  N
ATOM   3352  CA   LEU B 130      10.755  64.155  80.492  1.00 36.25           B  C
ATOM   3353  CB   LEU B 130      11.065  62.652  80.402  1.00 25.20           B  C
ATOM   3354  CG   LEU B 130       9.817  61.762  80.344  1.00 25.20           B  C
ATOM   3355  CD1  LEU B 130       9.018  62.111  79.126  1.00 25.20           B  C
ATOM   3356  CD2  LEU B 130      10.190  60.304  80.314  1.00 25.20           B  C
ATOM   3357  C    LEU B 130      11.959  64.912  81.014  1.00 36.25           B  C
ATOM   3358  O    LEU B 130      13.067  64.784  80.498  1.00 36.25           B  O
ATOM   3359  N    VAL B 131      11.718  65.739  82.021  1.00 32.29           B  N
ATOM   3360  CA   VAL B 131      12.781  66.512  82.630  1.00 32.29           B  C
ATOM   3361  CB   VAL B 131      12.244  67.819  83.228  1.00 20.44           B  C
ATOM   3362  CG1  VAL B 131      13.356  68.542  83.978  1.00 20.44           B  C
ATOM   3363  CG2  VAL B 131      11.708  68.705  82.126  1.00 20.44           B  C
ATOM   3364  C    VAL B 131      13.400  65.670  83.737  1.00 32.29           B  C
ATOM   3365  O    VAL B 131      12.825  65.509  84.818  1.00 32.29           B  O
ATOM   3366  N    LEU B 132      14.581  65.137  83.453  1.00 25.43           B  N
ATOM   3367  CA   LEU B 132      15.293  64.294  84.395  1.00 25.43           B  C
ATOM   3368  CB   LEU B 132      15.813  63.067  83.667  1.00 13.04           B  C
ATOM   3369  CG   LEU B 132      14.693  62.276  83.012  1.00 13.04           B  C
ATOM   3370  CD1  LEU B 132      15.119  61.805  81.647  1.00 13.04           B  C
ATOM   3371  CD2  LEU B 132      14.316  61.128  83.916  1.00 13.04           B  C
ATOM   3372  C    LEU B 132      16.451  65.059  84.968  1.00 25.43           B  C
ATOM   3373  O    LEU B 132      16.802  66.115  84.463  1.00 25.43           B  O
ATOM   3374  N    ASP B 133      17.030  64.541  86.040  1.00 23.27           B  N
ATOM   3375  CA   ASP B 133      18.189  65.177  86.635  1.00 23.27           B  C
ATOM   3376  CB   ASP B 133      18.625  64.414  87.872  1.00 34.83           B  C
ATOM   3377  CG   ASP B 133      17.980  64.937  89.132  1.00 34.83           B  C
ATOM   3378  OD1  ASP B 133      17.884  64.138  90.098  1.00 34.83           B  O
ATOM   3379  OD2  ASP B 133      17.590  66.137  89.143  1.00 34.83           B  O
ATOM   3380  C    ASP B 133      19.278  65.074  85.597  1.00 23.27           B  C
ATOM   3381  O    ASP B 133      19.195  64.246  84.698  1.00 23.27           B  O
ATOM   3382  N    TYR B 134      20.287  65.926  85.685  1.00 29.56           B  N
ATOM   3383  CA   TYR B 134      21.386  65.811  84.743  1.00 29.56           B  C
ATOM   3384  CB   TYR B 134      21.689  67.137  84.038  1.00 37.41           B  C
ATOM   3385  CG   TYR B 134      22.869  66.994  83.101  1.00 37.41           B  C
ATOM   3386  CD1  TYR B 134      22.747  66.292  81.900  1.00 37.41           B  C
ATOM   3387  CE1  TYR B 134      23.856  65.982  81.133  1.00 37.41           B  C
ATOM   3388  CD2  TYR B 134      24.141  67.400  83.495  1.00 37.41           B  C
ATOM   3389  CE2  TYR B 134      25.253  67.092  82.737  1.00 37.41           B  C
ATOM   3390  CZ   TYR B 134      25.106  66.377  81.563  1.00 37.41           B  C
ATOM   3391  OH   TYR B 134      26.225  66.006  80.857  1.00 37.41           B  O
ATOM   3392  C    TYR B 134      22.633  65.355  85.506  1.00 29.56           B  C
ATOM   3393  O    TYR B 134      23.037  65.973  86.480  1.00 29.56           B  O
ATOM   3394  N    VAL B 135      23.226  64.257  85.064  1.00 23.65           B  N
ATOM   3395  CA   VAL B 135      24.434  63.732  85.675  1.00 23.65           B  C
ATOM   3396  CB   VAL B 135      24.253  62.257  86.005  1.00 12.68           B  C
ATOM   3397  CG1  VAL B 135      25.449  61.747  86.776  1.00 12.68           B  C
ATOM   3398  CG2  VAL B 135      22.966  62.058  86.764  1.00 12.68           B  C
ATOM   3399  C    VAL B 135      25.543  63.885  84.615  1.00 23.65           B  C
ATOM   3400  O    VAL B 135      25.438  63.388  83.493  1.00 23.65           B  O
ATOM   3401  N    PRO B 136      26.631  64.557  84.977  1.00 32.08           B  N
ATOM   3402  CD   PRO B 136      26.897  64.888  86.387  1.00 35.00           B  C
ATOM   3403  CA   PRO B 136      27.803  64.855  84.162  1.00 32.08           B  C
ATOM   3404  CB   PRO B 136      28.592  65.769  85.069  1.00 35.00           B  C
ATOM   3405  CG   PRO B 136      28.376  65.125  86.390  1.00 35.00           B  C
ATOM   3406  C    PRO B 136      28.660  63.709  83.652  1.00 32.08           B  C
ATOM   3407  O    PRO B 136      29.318  63.852  82.631  1.00 32.08           B  O
ATOM   3408  N    GLU B 137      28.679  62.585  84.352  1.00 21.83           B  N
ATOM   3409  CA   GLU B 137      29.514  61.482  83.899  1.00 21.83           B  C
ATOM   3410  CB   GLU B 137      30.710  61.309  84.842  1.00 49.68           B  C
ATOM   3411  CG   GLU B 137      31.888  60.579  84.210  1.00 49.68           B  C
```

FIG. 4-52

```
ATOM   3412  CD   GLU B 137      32.338  61.247  82.921  1.00 49.68           B  C
ATOM   3413  OE1  GLU B 137      32.990  62.321  82.997  1.00 49.68           B  O
ATOM   3414  OE2  GLU B 137      32.020  60.702  81.838  1.00 49.68           B  O
ATOM   3415  C    GLU B 137      28.751  60.162  83.760  1.00 21.83           B  C
ATOM   3416  O    GLU B 137      27.601  60.050  84.166  1.00 21.83           B  O
ATOM   3417  N    THR B 138      29.390  59.167  83.158  1.00 24.10           B  N
ATOM   3418  CA   THR B 138      28.777  57.854  83.006  1.00 24.10           B  C
ATOM   3419  CB   THR B 138      28.101  57.652  81.635  1.00 24.34           B  C
ATOM   3420  OG1  THR B 138      29.099  57.625  80.609  1.00 24.34           B  O
ATOM   3421  CG2  THR B 138      27.121  58.745  81.352  1.00 24.34           B  C
ATOM   3422  C    THR B 138      29.819  56.759  83.090  1.00 24.10           B  C
ATOM   3423  O    THR B 138      30.930  56.917  82.617  1.00 24.10           B  O
ATOM   3424  N    VAL B 139      29.440  55.631  83.666  1.00 29.14           B  N
ATOM   3425  CA   VAL B 139      30.351  54.510  83.780  1.00 29.14           B  C
ATOM   3426  CB   VAL B 139      29.625  53.263  84.322  1.00 26.52           B  C
ATOM   3427  CG1  VAL B 139      30.490  52.023  84.144  1.00 26.52           B  C
ATOM   3428  CG2  VAL B 139      29.314  53.455  85.801  1.00 26.52           B  C
ATOM   3429  C    VAL B 139      30.970  54.180  82.426  1.00 29.14           B  C
ATOM   3430  O    VAL B 139      32.128  53.799  82.358  1.00 29.14           B  O
ATOM   3431  N    TYR B 140      30.202  54.314  81.354  1.00 34.44           B  N
ATOM   3432  CA   TYR B 140      30.724  54.026  80.021  1.00 34.44           B  C
ATOM   3433  CB   TYR B 140      29.654  54.272  78.958  1.00 29.70           B  C
ATOM   3434  CG   TYR B 140      30.192  54.178  77.551  1.00 29.70           B  C
ATOM   3435  CD1  TYR B 140      30.655  52.966  77.044  1.00 29.70           B  C
ATOM   3436  CE1  TYR B 140      31.194  52.872  75.763  1.00 29.70           B  C
ATOM   3437  CD2  TYR B 140      30.280  55.303  76.737  1.00 29.70           B  C
ATOM   3438  CE2  TYR B 140      30.818  55.219  75.457  1.00 29.70           B  C
ATOM   3439  CZ   TYR B 140      31.274  53.995  74.974  1.00 29.70           B  C
ATOM   3440  OH   TYR B 140      31.812  53.878  73.708  1.00 29.70           B  O
ATOM   3441  C    TYR B 140      31.945  54.895  79.691  1.00 34.44           B  C
ATOM   3442  O    TYR B 140      33.038  54.381  79.447  1.00 34.44           B  O
ATOM   3443  N    ARG B 141      31.757  56.213  79.665  1.00 33.60           B  N
ATOM   3444  CA   ARG B 141      32.856  57.124  79.360  1.00 33.60           B  C
ATOM   3445  CB   ARG B 141      32.448  58.584  79.558  1.00 48.27           B  C
ATOM   3446  CG   ARG B 141      31.232  59.046  78.805  1.00 48.27           B  C
ATOM   3447  CD   ARG B 141      30.992  60.529  79.071  1.00 48.27           B  C
ATOM   3448  NE   ARG B 141      31.972  61.383  78.398  1.00 48.27           B  N
ATOM   3449  CZ   ARG B 141      32.585  62.428  78.956  1.00 48.27           B  C
ATOM   3450  NH1  ARG B 141      32.329  62.771  80.220  1.00 48.27           B  N
ATOM   3451  NH2  ARG B 141      33.470  63.129  78.247  1.00 48.27           B  N
ATOM   3452  C    ARG B 141      34.065  56.866  80.251  1.00 33.60           B  C
ATOM   3453  O    ARG B 141      35.192  56.805  79.773  1.00 33.60           B  O
ATOM   3454  N    VAL B 142      33.823  56.737  81.550  1.00 26.50           B  N
ATOM   3455  CA   VAL B 142      34.882  56.509  82.527  1.00 26.50           B  C
ATOM   3456  CB   VAL B 142      34.312  56.423  83.960  1.00 20.22           B  C
ATOM   3457  CG1  VAL B 142      35.252  55.656  84.857  1.00 20.22           B  C
ATOM   3458  CG2  VAL B 142      34.089  57.817  84.509  1.00 20.22           B  C
ATOM   3459  C    VAL B 142      35.677  55.253  82.256  1.00 26.50           B  C
ATOM   3460  O    VAL B 142      36.890  55.256  82.395  1.00 26.50           B  O
ATOM   3461  N    ALA B 143      34.997  54.178  81.890  1.00 28.17           B  N
ATOM   3462  CA   ALA B 143      35.676  52.924  81.602  1.00 28.17           B  C
ATOM   3463  CB   ALA B 143      34.655  51.826  81.355  1.00 20.98           B  C
ATOM   3464  C    ALA B 143      36.538  53.120  80.364  1.00 28.17           B  C
ATOM   3465  O    ALA B 143      37.686  52.679  80.310  1.00 28.17           B  O
ATOM   3466  N    ARG B 144      35.952  53.783  79.371  1.00 29.64           B  N
ATOM   3467  CA   ARG B 144      36.603  54.071  78.098  1.00 29.64           B  C
ATOM   3468  CB   ARG B 144      35.749  55.069  77.311  1.00 66.90           B  C
ATOM   3469  CG   ARG B 144      35.968  55.094  75.810  1.00 66.90           B  C
ATOM   3470  CD   ARG B 144      35.105  54.035  75.155  1.00 66.90           B  C
ATOM   3471  NE   ARG B 144      35.125  52.804  75.951  1.00 66.90           B  N
ATOM   3472  CZ   ARG B 144      35.000  51.567  75.462  1.00 66.90           B  C
ATOM   3473  NH1  ARG B 144      34.842  51.380  74.149  1.00 66.90           B  N
ATOM   3474  NH2  ARG B 144      35.051  50.513  76.289  1.00 66.90           B  N
ATOM   3475  C    ARG B 144      37.950  54.707  78.376  1.00 29.64           B  C
ATOM   3476  O    ARG B 144      38.980  54.247  77.901  1.00 29.64           B  O
ATOM   3477  N    HIS B 145      37.926  55.774  79.165  1.00 32.22           B  N
ATOM   3478  CA   HIS B 145      39.135  56.499  79.502  1.00 32.22           B  C
```

FIG. 4-53

| | | | | | | | | | | |
|---|---|---|---|---|---|---|---|---|---|---|
| ATOM | 3479 | CB | HIS | B | 145 | 38.793 | 57.710 | 80.381 | 1.00 100.00 | B C |
| ATOM | 3480 | CG | HIS | B | 145 | 37.954 | 58.737 | 79.677 | 1.00 100.00 | B C |
| ATOM | 3481 | CD2 | HIS | B | 145 | 37.505 | 58.795 | 78.395 | 1.00 100.00 | B C |
| ATOM | 3482 | ND1 | HIS | B | 145 | 37.463 | 59.870 | 80.304 | 1.00 100.00 | B N |
| ATOM | 3483 | CE1 | HIS | B | 145 | 36.747 | 60.576 | 79.440 | 1.00 100.00 | B C |
| ATOM | 3484 | NE2 | HIS | B | 145 | 36.757 | 59.946 | 78.274 | 1.00 100.00 | B N |
| ATOM | 3485 | C | HIS | B | 145 | 40.223 | 55.643 | 80.142 | 1.00 32.22 | B C |
| ATOM | 3486 | O | HIS | B | 145 | 41.366 | 55.688 | 79.696 | 1.00 32.22 | B O |
| ATOM | 3487 | N | TYR | B | 146 | 39.899 | 54.870 | 81.174 | 1.00 27.23 | B N |
| ATOM | 3488 | CA | TYR | B | 146 | 40.928 | 54.031 | 81.774 | 1.00 27.23 | B C |
| ATOM | 3489 | CB | TYR | B | 146 | 40.416 | 53.293 | 83.021 | 1.00 28.68 | B C |
| ATOM | 3490 | CG | TYR | B | 146 | 40.320 | 54.143 | 84.270 | 1.00 28.68 | B C |
| ATOM | 3491 | CD1 | TYR | B | 146 | 39.265 | 55.042 | 84.458 | 1.00 28.68 | B C |
| ATOM | 3492 | CE1 | TYR | B | 146 | 39.207 | 55.867 | 85.587 | 1.00 28.68 | B C |
| ATOM | 3493 | CD2 | TYR | B | 146 | 41.311 | 54.085 | 85.245 | 1.00 28.68 | B C |
| ATOM | 3494 | CE2 | TYR | B | 146 | 41.262 | 54.906 | 86.376 | 1.00 28.68 | B C |
| ATOM | 3495 | CZ | TYR | B | 146 | 40.211 | 55.793 | 86.535 | 1.00 28.68 | B C |
| ATOM | 3496 | OH | TYR | B | 146 | 40.181 | 56.626 | 87.627 | 1.00 28.68 | B O |
| ATOM | 3497 | C | TYR | B | 146 | 41.416 | 53.014 | 80.760 | 1.00 27.23 | B C |
| ATOM | 3498 | O | TYR | B | 146 | 42.603 | 52.738 | 80.682 | 1.00 27.23 | B O |
| ATOM | 3499 | N | SER | B | 147 | 40.497 | 52.466 | 79.974 | 1.00 36.56 | B N |
| ATOM | 3500 | CA | SER | B | 147 | 40.846 | 51.474 | 78.965 | 1.00 36.56 | B C |
| ATOM | 3501 | CB | SER | B | 147 | 39.587 | 50.910 | 78.325 | 1.00 48.82 | B C |
| ATOM | 3502 | OG | SER | B | 147 | 39.914 | 49.888 | 77.402 | 1.00 48.82 | B O |
| ATOM | 3503 | C | SER | B | 147 | 41.736 | 52.066 | 77.885 | 1.00 36.56 | B C |
| ATOM | 3504 | O | SER | B | 147 | 42.738 | 51.468 | 77.497 | 1.00 36.56 | B O |
| ATOM | 3505 | N | ARG | B | 148 | 41.368 | 53.244 | 77.399 | 1.00 49.04 | B N |
| ATOM | 3506 | CA | ARG | B | 148 | 42.149 | 53.897 | 76.358 | 1.00 49.04 | B C |
| ATOM | 3507 | CB | ARG | B | 148 | 41.529 | 55.250 | 75.998 | 1.00 51.06 | B C |
| ATOM | 3508 | CG | ARG | B | 148 | 41.599 | 55.593 | 74.517 | 1.00 51.06 | B C |
| ATOM | 3509 | CD | ARG | B | 148 | 40.238 | 56.087 | 73.980 | 1.00 51.06 | B C |
| ATOM | 3510 | NE | ARG | B | 148 | 39.735 | 57.247 | 74.722 | 1.00 51.06 | B N |
| ATOM | 3511 | CZ | ARG | B | 148 | 38.559 | 57.832 | 74.503 | 1.00 51.06 | B C |
| ATOM | 3512 | NH1 | ARG | B | 148 | 37.752 | 57.366 | 73.552 | 1.00 51.06 | B N |
| ATOM | 3513 | NH2 | ARG | B | 148 | 38.184 | 58.868 | 75.255 | 1.00 51.06 | B N |
| ATOM | 3514 | C | ARG | B | 148 | 43.578 | 54.084 | 76.858 | 1.00 49.04 | B C |
| ATOM | 3515 | O | ARG | B | 148 | 44.528 | 53.628 | 76.221 | 1.00 49.04 | B O |
| ATOM | 3516 | N | ALA | B | 149 | 43.726 | 54.739 | 78.007 | 1.00 37.90 | B N |
| ATOM | 3517 | CA | ALA | B | 149 | 45.044 | 54.979 | 78.592 | 1.00 37.90 | B C |
| ATOM | 3518 | CB | ALA | B | 149 | 44.947 | 56.053 | 79.677 | 1.00 38.09 | B C |
| ATOM | 3519 | C | ALA | B | 149 | 45.660 | 53.713 | 79.156 | 1.00 37.90 | B C |
| ATOM | 3520 | O | ALA | B | 149 | 46.472 | 53.761 | 80.081 | 1.00 37.90 | B O |
| ATOM | 3521 | N | ALA | B | 150 | 45.267 | 52.579 | 78.585 | 1.00 42.73 | B N |
| ATOM | 3522 | CA | ALA | B | 150 | 45.779 | 51.283 | 79.006 | 1.00 42.73 | B C |
| ATOM | 3523 | CB | ALA | B | 150 | 47.082 | 50.977 | 78.279 | 1.00 41.86 | B C |
| ATOM | 3524 | C | ALA | B | 150 | 45.992 | 51.291 | 80.511 | 1.00 42.73 | B C |
| ATOM | 3525 | O | ALA | B | 150 | 47.110 | 51.378 | 81.006 | 1.00 42.73 | B O |
| ATOM | 3526 | N | GLN | B | 151 | 44.889 | 51.238 | 81.230 | 1.00 50.70 | B N |
| ATOM | 3527 | CA | GLN | B | 151 | 44.914 | 51.231 | 82.676 | 1.00 50.70 | B C |
| ATOM | 3528 | CB | GLN | B | 151 | 44.986 | 52.660 | 83.221 | 1.00 50.24 | B C |
| ATOM | 3529 | CG | GLN | B | 151 | 46.383 | 53.236 | 83.282 | 1.00 50.24 | B C |
| ATOM | 3530 | CD | GLN | B | 151 | 46.385 | 54.736 | 83.556 | 1.00 50.24 | B C |
| ATOM | 3531 | OE1 | GLN | B | 151 | 45.717 | 55.215 | 84.476 | 1.00 50.24 | B O |
| ATOM | 3532 | NE2 | GLN | B | 151 | 47.145 | 55.486 | 82.758 | 1.00 50.24 | B N |
| ATOM | 3533 | C | GLN | B | 151 | 43.639 | 50.558 | 83.152 | 1.00 50.70 | B C |
| ATOM | 3534 | O | GLN | B | 151 | 42.738 | 50.256 | 82.353 | 1.00 50.70 | B O |
| ATOM | 3535 | N | THR | B | 152 | 43.565 | 50.325 | 84.454 | 1.00 57.34 | B N |
| ATOM | 3536 | CA | THR | B | 152 | 42.397 | 49.703 | 85.045 | 1.00 57.34 | B C |
| ATOM | 3537 | CB | THR | B | 152 | 42.776 | 48.476 | 85.841 | 1.00 72.48 | B C |
| ATOM | 3538 | OG1 | THR | B | 152 | 41.689 | 48.152 | 86.722 | 1.00 72.48 | B O |
| ATOM | 3539 | CG2 | THR | B | 152 | 44.063 | 48.753 | 86.665 | 1.00 72.48 | B C |
| ATOM | 3540 | C | THR | B | 152 | 41.724 | 50.651 | 86.020 | 1.00 57.34 | B C |
| ATOM | 3541 | O | THR | B | 152 | 42.394 | 51.427 | 86.713 | 1.00 57.34 | B O |
| ATOM | 3542 | N | LEU | B | 153 | 40.402 | 50.573 | 86.083 | 1.00 40.88 | B N |
| ATOM | 3543 | CA | LEU | B | 153 | 39.639 | 51.405 | 86.998 | 1.00 40.88 | B C |
| ATOM | 3544 | CB | LEU | B | 153 | 38.161 | 51.338 | 86.632 | 1.00 34.78 | B C |
| ATOM | 3545 | CG | LEU | B | 153 | 37.184 | 52.023 | 87.580 | 1.00 34.78 | B C |

FIG. 4-54

| | | | | | | | | | | | |
|---|---|---|---|---|---|---|---|---|---|---|---|
| ATOM | 3546 | CD1 | LEU | B | 153 | 37.290 | 53.531 | 87.436 | 1.00 | 34.78 | B C |
| ATOM | 3547 | CD2 | LEU | B | 153 | 35.774 | 51.554 | 87.255 | 1.00 | 34.78 | B C |
| ATOM | 3548 | C | LEU | B | 153 | 39.864 | 50.813 | 88.387 | 1.00 | 40.88 | B C |
| ATOM | 3549 | O | LEU | B | 153 | 39.607 | 49.630 | 88.600 | 1.00 | 40.88 | B O |
| ATOM | 3550 | N | PRO | B | 154 | 40.380 | 51.614 | 89.336 | 1.00 | 18.95 | B N |
| ATOM | 3551 | CD | PRO | B | 154 | 40.933 | 52.966 | 89.165 | 1.00 | 22.48 | B C |
| ATOM | 3552 | CA | PRO | B | 154 | 40.630 | 51.142 | 90.696 | 1.00 | 18.95 | B C |
| ATOM | 3553 | CB | PRO | B | 154 | 40.963 | 52.425 | 91.438 | 1.00 | 22.48 | B C |
| ATOM | 3554 | CG | PRO | B | 154 | 41.759 | 53.129 | 90.438 | 1.00 | 22.48 | B C |
| ATOM | 3555 | C | PRO | B | 154 | 39.408 | 50.419 | 91.235 | 1.00 | 18.95 | B C |
| ATOM | 3556 | O | PRO | B | 154 | 38.299 | 50.940 | 91.204 | 1.00 | 18.95 | B O |
| ATOM | 3557 | N | VAL | B | 155 | 39.620 | 49.198 | 91.706 | 1.00 | 30.17 | B N |
| ATOM | 3558 | CA | VAL | B | 155 | 38.534 | 48.368 | 92.217 | 1.00 | 30.17 | B C |
| ATOM | 3559 | CB | VAL | B | 155 | 39.082 | 46.994 | 92.757 | 1.00 | 14.30 | B C |
| ATOM | 3560 | CG1 | VAL | B | 155 | 40.517 | 46.796 | 92.307 | 1.00 | 14.30 | B C |
| ATOM | 3561 | CG2 | VAL | B | 155 | 38.975 | 46.915 | 94.281 | 1.00 | 14.30 | B C |
| ATOM | 3562 | C | VAL | B | 155 | 37.683 | 49.037 | 93.302 | 1.00 | 30.17 | B C |
| ATOM | 3563 | O | VAL | B | 155 | 36.575 | 48.591 | 93.602 | 1.00 | 30.17 | B O |
| ATOM | 3564 | N | ILE | B | 156 | 38.196 | 50.089 | 93.918 | 1.00 | 24.99 | B N |
| ATOM | 3565 | CA | ILE | B | 156 | 37.391 | 50.743 | 94.929 | 1.00 | 24.99 | B C |
| ATOM | 3566 | CB | ILE | B | 156 | 38.169 | 51.904 | 95.611 | 1.00 | 22.87 | B C |
| ATOM | 3567 | CG2 | ILE | B | 156 | 38.744 | 52.845 | 94.578 | 1.00 | 22.87 | B C |
| ATOM | 3568 | CG1 | ILE | B | 156 | 37.252 | 52.652 | 96.578 | 1.00 | 22.87 | B C |
| ATOM | 3569 | CD1 | ILE | B | 156 | 36.659 | 51.771 | 97.664 | 1.00 | 22.87 | B C |
| ATOM | 3570 | C | ILE | B | 156 | 36.155 | 51.251 | 94.194 | 1.00 | 24.99 | B C |
| ATOM | 3571 | O | ILE | B | 156 | 35.031 | 50.990 | 94.605 | 1.00 | 24.99 | B O |
| ATOM | 3572 | N | TYR | B | 157 | 36.380 | 51.950 | 93.087 | 1.00 | 28.38 | B N |
| ATOM | 3573 | CA | TYR | B | 157 | 35.306 | 52.498 | 92.267 | 1.00 | 28.38 | B C |
| ATOM | 3574 | CB | TYR | B | 157 | 35.885 | 53.305 | 91.104 | 1.00 | 35.68 | B C |
| ATOM | 3575 | CG | TYR | B | 157 | 36.488 | 54.624 | 91.528 | 1.00 | 35.68 | B C |
| ATOM | 3576 | CD1 | TYR | B | 157 | 35.796 | 55.474 | 92.381 | 1.00 | 35.68 | B C |
| ATOM | 3577 | CE1 | TYR | B | 157 | 36.319 | 56.690 | 92.764 | 1.00 | 35.68 | B C |
| ATOM | 3578 | CD2 | TYR | B | 157 | 37.735 | 55.034 | 91.062 | 1.00 | 35.68 | B C |
| ATOM | 3579 | CE2 | TYR | B | 157 | 38.269 | 56.260 | 91.440 | 1.00 | 35.68 | B C |
| ATOM | 3580 | CZ | TYR | B | 157 | 37.552 | 57.084 | 92.293 | 1.00 | 35.68 | B C |
| ATOM | 3581 | OH | TYR | B | 157 | 38.060 | 58.308 | 92.675 | 1.00 | 35.68 | B O |
| ATOM | 3582 | C | TYR | B | 157 | 34.410 | 51.405 | 91.727 | 1.00 | 28.38 | B C |
| ATOM | 3583 | O | TYR | B | 157 | 33.193 | 51.553 | 91.714 | 1.00 | 28.38 | B O |
| ATOM | 3584 | N | VAL | B | 158 | 35.020 | 50.322 | 91.257 | 1.00 | 26.28 | B N |
| ATOM | 3585 | CA | VAL | B | 158 | 34.273 | 49.181 | 90.734 | 1.00 | 26.28 | B C |
| ATOM | 3586 | CB | VAL | B | 158 | 35.225 | 48.071 | 90.263 | 1.00 | 12.86 | B C |
| ATOM | 3587 | CG1 | VAL | B | 158 | 34.441 | 46.874 | 89.767 | 1.00 | 12.86 | B C |
| ATOM | 3588 | CG2 | VAL | B | 158 | 36.115 | 48.620 | 89.173 | 1.00 | 12.86 | B C |
| ATOM | 3589 | C | VAL | B | 158 | 33.350 | 48.642 | 91.819 | 1.00 | 26.28 | B C |
| ATOM | 3590 | O | VAL | B | 158 | 32.275 | 48.131 | 91.537 | 1.00 | 26.28 | B O |
| ATOM | 3591 | N | LYS | B | 159 | 33.781 | 48.770 | 93.063 | 1.00 | 26.23 | B N |
| ATOM | 3592 | CA | LYS | B | 159 | 32.985 | 48.338 | 94.201 | 1.00 | 26.23 | B C |
| ATOM | 3593 | CB | LYS | B | 159 | 33.847 | 48.340 | 95.474 | 1.00 | 32.64 | B C |
| ATOM | 3594 | CG | LYS | B | 159 | 34.641 | 47.070 | 95.778 | 1.00 | 32.64 | B C |
| ATOM | 3595 | CD | LYS | B | 159 | 35.284 | 47.208 | 97.142 | 1.00 | 32.64 | B C |
| ATOM | 3596 | CE | LYS | B | 159 | 36.028 | 45.964 | 97.590 | 1.00 | 32.64 | B C |
| ATOM | 3597 | NZ | LYS | B | 159 | 37.441 | 45.937 | 97.186 | 1.00 | 32.64 | B N |
| ATOM | 3598 | C | LYS | B | 159 | 31.821 | 49.329 | 94.389 | 1.00 | 26.23 | B C |
| ATOM | 3599 | O | LYS | B | 159 | 30.654 | 48.945 | 94.456 | 1.00 | 26.23 | B O |
| ATOM | 3600 | N | LEU | B | 160 | 32.156 | 50.610 | 94.488 | 1.00 | 26.95 | B N |
| ATOM | 3601 | CA | LEU | B | 160 | 31.153 | 51.641 | 94.692 | 1.00 | 26.95 | B C |
| ATOM | 3602 | CB | LEU | B | 160 | 31.814 | 53.009 | 94.835 | 1.00 | 38.88 | B C |
| ATOM | 3603 | CG | LEU | B | 160 | 32.424 | 53.341 | 96.197 | 1.00 | 38.88 | B C |
| ATOM | 3604 | CD1 | LEU | B | 160 | 33.090 | 54.690 | 96.116 | 1.00 | 38.88 | B C |
| ATOM | 3605 | CD2 | LEU | B | 160 | 31.356 | 53.345 | 97.273 | 1.00 | 38.88 | B C |
| ATOM | 3606 | C | LEU | B | 160 | 30.110 | 51.711 | 93.592 | 1.00 | 26.95 | B C |
| ATOM | 3607 | O | LEU | B | 160 | 28.933 | 51.948 | 93.850 | 1.00 | 26.95 | B O |
| ATOM | 3608 | N | TYR | B | 161 | 30.545 | 51.523 | 92.357 | 1.00 | 22.18 | B N |
| ATOM | 3609 | CA | TYR | B | 161 | 29.637 | 51.577 | 91.230 | 1.00 | 22.18 | B C |
| ATOM | 3610 | CB | TYR | B | 161 | 30.451 | 51.717 | 89.948 | 1.00 | 37.20 | B C |
| ATOM | 3611 | CG | TYR | B | 161 | 31.244 | 52.996 | 89.887 | 1.00 | 37.20 | B C |
| ATOM | 3612 | CD1 | TYR | B | 161 | 30.942 | 54.053 | 90.739 | 1.00 | 37.20 | B C |

FIG. 4-55

```
ATOM   3613  CE1 TYR B 161      31.640  55.249  90.676  1.00 37.20      B    C
ATOM   3614  CD2 TYR B 161      32.278  53.164  88.956  1.00 37.20      B    C
ATOM   3615  CE2 TYR B 161      32.992  54.363  88.876  1.00 37.20      B    C
ATOM   3616  CZ  TYR B 161      32.664  55.405  89.743  1.00 37.20      B    C
ATOM   3617  OH  TYR B 161      33.326  56.616  89.678  1.00 37.20      B    O
ATOM   3618  C   TYR B 161      28.728  50.345  91.142  1.00 22.18      B    C
ATOM   3619  O   TYR B 161      27.517  50.464  90.942  1.00 22.18      B    O
ATOM   3620  N   MET B 162      29.322  49.162  91.290  1.00 22.94      B    N
ATOM   3621  CA  MET B 162      28.573  47.909  91.210  1.00 22.94      B    C
ATOM   3622  CB  MET B 162      29.517  46.706  91.224  1.00 19.71      B    C
ATOM   3623  CG  MET B 162      30.210  46.445  89.914  1.00 19.71      B    C
ATOM   3624  SD  MET B 162      29.114  46.564  88.510  1.00 19.71      B    S
ATOM   3625  CE  MET B 162      28.023  45.193  88.756  1.00 19.71      B    C
ATOM   3626  C   MET B 162      27.559  47.731  92.327  1.00 22.94      B    C
ATOM   3627  O   MET B 162      26.451  47.255  92.095  1.00 22.94      B    O
ATOM   3628  N   TYR B 163      27.942  48.104  93.541  1.00 27.38      B    N
ATOM   3629  CA  TYR B 163      27.040  47.984  94.682  1.00 27.38      B    C
ATOM   3630  CB  TYR B 163      27.756  48.383  95.985  1.00 18.22      B    C
ATOM   3631  CG  TYR B 163      26.890  48.416  97.241  1.00 18.22      B    C
ATOM   3632  CD1 TYR B 163      26.697  47.286  98.011  1.00 18.22      B    C
ATOM   3633  CE1 TYR B 163      25.944  47.345  99.174  1.00 18.22      B    C
ATOM   3634  CD2 TYR B 163      26.296  49.606  97.669  1.00 18.22      B    C
ATOM   3635  CE2 TYR B 163      25.538  49.672  98.826  1.00 18.22      B    C
ATOM   3636  CZ  TYR B 163      25.367  48.546  99.579  1.00 18.22      B    C
ATOM   3637  OH  TYR B 163      24.646  48.633 100.752  1.00 18.22      B    O
ATOM   3638  C   TYR B 163      25.818  48.872  94.458  1.00 27.38      B    C
ATOM   3639  O   TYR B 163      24.684  48.437  94.617  1.00 27.38      B    O
ATOM   3640  N   GLN B 164      26.056  50.123  94.083  1.00 33.04      B    N
ATOM   3641  CA  GLN B 164      24.966  51.048  93.839  1.00 33.04      B    C
ATOM   3642  CB  GLN B 164      25.524  52.435  93.535  1.00 22.81      B    C
ATOM   3643  CG  GLN B 164      26.350  53.016  94.651  1.00 22.81      B    C
ATOM   3644  CD  GLN B 164      26.713  54.468  94.411  1.00 22.81      B    C
ATOM   3645  OE1 GLN B 164      25.867  55.359  94.469  1.00 22.81      B    O
ATOM   3646  NE2 GLN B 164      27.979  54.709  94.136  1.00 22.81      B    N
ATOM   3647  C   GLN B 164      24.082  50.568  92.681  1.00 33.04      B    C
ATOM   3648  O   GLN B 164      22.879  50.846  92.646  1.00 33.04      B    O
ATOM   3649  N   LEU B 165      24.670  49.848  91.731  1.00 33.23      B    N
ATOM   3650  CA  LEU B 165      23.880  49.357  90.614  1.00 33.23      B    C
ATOM   3651  CB  LEU B 165      24.750  48.651  89.570  1.00 11.12      B    C
ATOM   3652  CG  LEU B 165      24.279  48.669  88.106  1.00 11.12      B    C
ATOM   3653  CD1 LEU B 165      24.998  47.571  87.364  1.00 11.12      B    C
ATOM   3654  CD2 LEU B 165      22.776  48.508  87.987  1.00 11.12      B    C
ATOM   3655  C   LEU B 165      22.923  48.344  91.208  1.00 33.23      B    C
ATOM   3656  O   LEU B 165      21.717  48.440  91.031  1.00 33.23      B    O
ATOM   3657  N   PHE B 166      23.464  47.368  91.923  1.00 22.14      B    N
ATOM   3658  CA  PHE B 166      22.628  46.346  92.532  1.00 22.14      B    C
ATOM   3659  CB  PHE B 166      23.484  45.341  93.318  1.00 13.23      B    C
ATOM   3660  CG  PHE B 166      24.256  44.392  92.450  1.00 13.23      B    C
ATOM   3661  CD1 PHE B 166      23.594  43.562  91.539  1.00 13.23      B    C
ATOM   3662  CD2 PHE B 166      25.645  44.360  92.502  1.00 13.23      B    C
ATOM   3663  CE1 PHE B 166      24.307  42.718  90.686  1.00 13.23      B    C
ATOM   3664  CE2 PHE B 166      26.366  43.529  91.664  1.00 13.23      B    C
ATOM   3665  CZ  PHE B 166      25.695  42.703  90.748  1.00 13.23      B    C
ATOM   3666  C   PHE B 166      21.536  46.924  93.446  1.00 22.14      B    C
ATOM   3667  O   PHE B 166      20.453  46.367  93.541  1.00 22.14      B    O
ATOM   3668  N   ARG B 167      21.815  48.027  94.126  1.00 23.66      B    N
ATOM   3669  CA  ARG B 167      20.821  48.628  95.008  1.00 23.66      B    C
ATOM   3670  CB  ARG B 167      21.433  49.757  95.836  1.00 22.23      B    C
ATOM   3671  CG  ARG B 167      22.082  49.315  97.146  1.00 22.23      B    C
ATOM   3672  CD  ARG B 167      21.367  49.935  98.317  1.00 22.23      B    C
ATOM   3673  NE  ARG B 167      21.720  51.334  98.498  1.00 22.23      B    N
ATOM   3674  CZ  ARG B 167      20.918  52.228  99.062  1.00 22.23      B    C
ATOM   3675  NH1 ARG B 167      19.721  51.871  99.493  1.00 22.23      B    N
ATOM   3676  NH2 ARG B 167      21.312  53.480  99.202  1.00 22.23      B    N
ATOM   3677  C   ARG B 167      19.679  49.192  94.189  1.00 23.66      B    C
ATOM   3678  O   ARG B 167      18.537  49.187  94.623  1.00 23.66      B    O
ATOM   3679  N   SER B 168      19.994  49.699  93.006  1.00 28.83      B    N
```

FIG. 4-56

```
ATOM   3680  CA   SER B 168      18.976  50.255  92.129  1.00 28.83       B  C
ATOM   3681  CB   SER B 168      19.636  51.049  91.007  1.00 14.03       B  C
ATOM   3682  OG   SER B 168      20.062  50.187  89.964  1.00 14.03       B  O
ATOM   3683  C    SER B 168      18.174  49.107  91.514  1.00 28.83       B  C
ATOM   3684  O    SER B 168      16.980  49.229  91.228  1.00 28.83       B  O
ATOM   3685  N    LEU B 169      18.854  47.992  91.289  1.00 28.00       B  N
ATOM   3686  CA   LEU B 169      18.219  46.821  90.706  1.00 28.00       B  C
ATOM   3687  CB   LEU B 169      19.283  45.854  90.190  1.00 11.78       B  C
ATOM   3688  CG   LEU B 169      19.467  45.762  88.675  1.00 11.78       B  C
ATOM   3689  CD1  LEU B 169      19.192  47.069  88.016  1.00 11.78       B  C
ATOM   3690  CD2  LEU B 169      20.855  45.300  88.384  1.00 11.78       B  C
ATOM   3691  C    LEU B 169      17.342  46.134  91.740  1.00 28.00       B  C
ATOM   3692  O    LEU B 169      16.272  45.638  91.422  1.00 28.00       B  O
ATOM   3693  N    ALA B 170      17.797  46.106  92.986  1.00 23.73       B  N
ATOM   3694  CA   ALA B 170      17.023  45.493  94.058  1.00 23.73       B  C
ATOM   3695  CB   ALA B 170      17.851  45.471  95.335  1.00 14.07       B  C
ATOM   3696  C    ALA B 170      15.737  46.292  94.275  1.00 23.73       B  C
ATOM   3697  O    ALA B 170      14.701  45.750  94.669  1.00 23.73       B  O
ATOM   3698  N    TYR B 171      15.824  47.591  94.010  1.00 28.49       B  N
ATOM   3699  CA   TYR B 171      14.693  48.489  94.156  1.00 28.49       B  C
ATOM   3700  CB   TYR B 171      15.153  49.943  94.102  1.00 15.64       B  C
ATOM   3701  CG   TYR B 171      14.022  50.913  94.284  1.00 15.64       B  C
ATOM   3702  CD1  TYR B 171      13.410  51.061  95.515  1.00 15.64       B  C
ATOM   3703  CE1  TYR B 171      12.343  51.926  95.690  1.00 15.64       B  C
ATOM   3704  CD2  TYR B 171      13.537  51.659  93.222  1.00 15.64       B  C
ATOM   3705  CE2  TYR B 171      12.464  52.529  93.389  1.00 15.64       B  C
ATOM   3706  CZ   TYR B 171      11.874  52.657  94.628  1.00 15.64       B  C
ATOM   3707  OH   TYR B 171      10.823  53.520  94.808  1.00 15.64       B  O
ATOM   3708  C    TYR B 171      13.646  48.258  93.071  1.00 28.49       B  C
ATOM   3709  O    TYR B 171      12.535  47.853  93.363  1.00 28.49       B  O
ATOM   3710  N    ILE B 172      13.991  48.506  91.816  1.00 24.30       B  N
ATOM   3711  CA   ILE B 172      13.006  48.330  90.759  1.00 24.30       B  C
ATOM   3712  CB   ILE B 172      13.552  48.716  89.356  1.00 18.18       B  C
ATOM   3713  CG2  ILE B 172      13.875  50.207  89.306  1.00 18.18       B  C
ATOM   3714  CG1  ILE B 172      14.763  47.856  89.001  1.00 18.18       B  C
ATOM   3715  CD1  ILE B 172      15.045  47.809  87.510  1.00 18.18       B  C
ATOM   3716  C    ILE B 172      12.485  46.904  90.692  1.00 24.30       B  C
ATOM   3717  O    ILE B 172      11.341  46.677  90.346  1.00 24.30       B  O
ATOM   3718  N    HIS B 173      13.319  45.933  91.010  1.00 32.78       B  N
ATOM   3719  CA   HIS B 173      12.856  44.562  90.977  1.00 32.78       B  C
ATOM   3720  CB   HIS B 173      14.023  43.596  91.184  1.00 11.26       B  C
ATOM   3721  CG   HIS B 173      14.889  43.425  89.977  1.00 11.26       B  C
ATOM   3722  CD2  HIS B 173      14.973  44.143  88.833  1.00 11.26       B  C
ATOM   3723  ND1  HIS B 173      15.848  42.439  89.881  1.00 11.26       B  N
ATOM   3724  CE1  HIS B 173      16.489  42.565  88.732  1.00 11.26       B  C
ATOM   3725  NE2  HIS B 173      15.977  43.590  88.078  1.00 11.26       B  N
ATOM   3726  C    HIS B 173      11.807  44.313  92.055  1.00 32.78       B  C
ATOM   3727  O    HIS B 173      10.956  43.441  91.900  1.00 32.78       B  O
ATOM   3728  N    SER B 174      11.868  45.072  93.146  1.00 25.19       B  N
ATOM   3729  CA   SER B 174      10.936  44.879  94.238  1.00 25.19       B  C
ATOM   3730  CB   SER B 174      11.301  45.759  95.440  1.00 28.98       B  C
ATOM   3731  OG   SER B 174      10.738  47.053  95.349  1.00 28.98       B  O
ATOM   3732  C    SER B 174       9.515  45.141  93.798  1.00 25.19       B  C
ATOM   3733  O    SER B 174       8.586  44.535  94.324  1.00 25.19       B  O
ATOM   3734  N    PHE B 175       9.351  46.033  92.827  1.00 21.85       B  N
ATOM   3735  CA   PHE B 175       8.035  46.364  92.313  1.00 21.85       B  C
ATOM   3736  CB   PHE B 175       7.991  47.780  91.770  1.00 40.28       B  C
ATOM   3737  CG   PHE B 175       8.221  48.820  92.799  1.00 40.28       B  C
ATOM   3738  CD1  PHE B 175       9.508  49.153  93.183  1.00 40.28       B  C
ATOM   3739  CD2  PHE B 175       7.143  49.481  93.383  1.00 40.28       B  C
ATOM   3740  CE1  PHE B 175       9.722  50.131  94.137  1.00 40.28       B  C
ATOM   3741  CE2  PHE B 175       7.337  50.469  94.349  1.00 40.28       B  C
ATOM   3742  CZ   PHE B 175       8.628  50.800  94.727  1.00 40.28       B  C
ATOM   3743  C    PHE B 175       7.735  45.412  91.183  1.00 21.85       B  C
ATOM   3744  O    PHE B 175       6.683  45.504  90.555  1.00 21.85       B  O
ATOM   3745  N    GLY B 176       8.677  44.514  90.910  1.00 25.12       B  N
ATOM   3746  CA   GLY B 176       8.505  43.554  89.834  1.00 25.12       B  C
```

FIG. 4-57

| | | | | | | | | | | |
|---|---|---|---|---|---|---|---|---|---|---|
| ATOM | 3747 | C | GLY | B | 176 | 8.855 | 44.093 | 88.453 | 1.00 25.12 | B C |
| ATOM | 3748 | O | GLY | B | 176 | 8.510 | 43.491 | 87.431 | 1.00 25.12 | B O |
| ATOM | 3749 | N | ILE | B | 177 | 9.544 | 45.231 | 88.421 | 1.00 25.99 | B N |
| ATOM | 3750 | CA | ILE | B | 177 | 9.941 | 45.875 | 87.171 | 1.00 25.99 | B C |
| ATOM | 3751 | CB | ILE | B | 177 | 9.895 | 47.401 | 87.281 | 1.00 13.91 | B C |
| ATOM | 3752 | CG2 | ILE | B | 177 | 10.441 | 48.024 | 86.012 | 1.00 13.91 | B C |
| ATOM | 3753 | CG1 | ILE | B | 177 | 8.464 | 47.850 | 87.552 | 1.00 13.91 | B C |
| ATOM | 3754 | CD1 | ILE | B | 177 | 8.269 | 49.330 | 87.475 | 1.00 13.91 | B C |
| ATOM | 3755 | C | ILE | B | 177 | 11.347 | 45.494 | 86.731 | 1.00 25.99 | B C |
| ATOM | 3756 | O | ILE | B | 177 | 12.261 | 45.442 | 87.539 | 1.00 25.99 | B O |
| ATOM | 3757 | N | CYS | B | 178 | 11.519 | 45.239 | 85.439 | 1.00 26.49 | B N |
| ATOM | 3758 | CA | CYS | B | 178 | 12.827 | 44.877 | 84.913 | 1.00 26.49 | B C |
| ATOM | 3759 | CB | CYS | B | 178 | 12.735 | 43.575 | 84.122 | 1.00 31.42 | B C |
| ATOM | 3760 | SG | CYS | B | 178 | 14.325 | 42.818 | 83.657 | 1.00 31.42 | B S |
| ATOM | 3761 | C | CYS | B | 178 | 13.305 | 45.995 | 84.008 | 1.00 26.49 | B C |
| ATOM | 3762 | O | CYS | B | 178 | 12.540 | 46.516 | 83.205 | 1.00 26.49 | B O |
| ATOM | 3763 | N | HIS | B | 179 | 14.572 | 46.367 | 84.133 | 1.00 31.89 | B N |
| ATOM | 3764 | CA | HIS | B | 179 | 15.108 | 47.454 | 83.322 | 1.00 31.89 | B C |
| ATOM | 3765 | CB | HIS | B | 179 | 16.458 | 47.919 | 83.871 | 1.00 20.47 | B C |
| ATOM | 3766 | CG | HIS | B | 179 | 17.022 | 49.112 | 83.163 | 1.00 20.47 | B C |
| ATOM | 3767 | CD2 | HIS | B | 179 | 17.100 | 50.412 | 83.537 | 1.00 20.47 | B C |
| ATOM | 3768 | ND1 | HIS | B | 179 | 17.558 | 49.047 | 81.893 | 1.00 20.47 | B N |
| ATOM | 3769 | CE1 | HIS | B | 179 | 17.939 | 50.255 | 81.517 | 1.00 20.47 | B C |
| ATOM | 3770 | NE2 | HIS | B | 179 | 17.671 | 51.102 | 82.496 | 1.00 20.47 | B N |
| ATOM | 3771 | C | HIS | B | 179 | 15.266 | 47.011 | 81.881 | 1.00 31.89 | B C |
| ATOM | 3772 | O | HIS | B | 179 | 15.034 | 47.786 | 80.956 | 1.00 31.89 | B O |
| ATOM | 3773 | N | ARG | B | 180 | 15.673 | 45.760 | 81.703 | 1.00 24.43 | B N |
| ATOM | 3774 | CA | ARG | B | 180 | 15.861 | 45.172 | 80.377 | 1.00 24.43 | B C |
| ATOM | 3775 | CB | ARG | B | 180 | 14.553 | 45.205 | 79.608 | 1.00 37.66 | B C |
| ATOM | 3776 | CG | ARG | B | 180 | 13.520 | 44.225 | 80.065 | 1.00 37.66 | B C |
| ATOM | 3777 | CD | ARG | B | 180 | 12.181 | 44.818 | 79.769 | 1.00 37.66 | B C |
| ATOM | 3778 | NE | ARG | B | 180 | 11.291 | 43.892 | 79.092 | 1.00 37.66 | B N |
| ATOM | 3779 | CZ | ARG | B | 180 | 10.172 | 44.275 | 78.500 | 1.00 37.66 | B C |
| ATOM | 3780 | NH1 | ARG | B | 180 | 9.848 | 45.562 | 78.498 | 1.00 37.66 | B N |
| ATOM | 3781 | NH2 | ARG | B | 180 | 9.346 | 43.374 | 77.978 | 1.00 37.66 | B N |
| ATOM | 3782 | C | ARG | B | 180 | 16.962 | 45.775 | 79.481 | 1.00 24.43 | B C |
| ATOM | 3783 | O | ARG | B | 180 | 17.109 | 45.390 | 78.316 | 1.00 24.43 | B O |
| ATOM | 3784 | N | ASP | B | 181 | 17.728 | 46.721 | 80.008 | 1.00 27.62 | B N |
| ATOM | 3785 | CA | ASP | B | 181 | 18.791 | 47.310 | 79.211 | 1.00 27.62 | B C |
| ATOM | 3786 | CB | ASP | B | 181 | 18.199 | 48.356 | 78.261 | 1.00 24.31 | B C |
| ATOM | 3787 | CG | ASP | B | 181 | 19.169 | 48.789 | 77.175 | 1.00 24.31 | B C |
| ATOM | 3788 | OD1 | ASP | B | 181 | 19.871 | 47.919 | 76.615 | 1.00 24.31 | B O |
| ATOM | 3789 | OD2 | ASP | B | 181 | 19.213 | 50.000 | 76.869 | 1.00 24.31 | B O |
| ATOM | 3790 | C | ASP | B | 181 | 19.934 | 47.893 | 80.054 | 1.00 27.62 | B C |
| ATOM | 3791 | O | ASP | B | 181 | 20.351 | 49.037 | 79.893 | 1.00 27.62 | B O |
| ATOM | 3792 | N | ILE | B | 182 | 20.451 | 47.062 | 80.947 | 1.00 29.58 | B N |
| ATOM | 3793 | CA | ILE | B | 182 | 21.541 | 47.459 | 81.812 | 1.00 29.58 | B C |
| ATOM | 3794 | CB | ILE | B | 182 | 21.618 | 46.555 | 83.073 | 1.00 11.86 | B C |
| ATOM | 3795 | CG2 | ILE | B | 182 | 22.680 | 47.073 | 84.010 | 1.00 11.86 | B C |
| ATOM | 3796 | CG1 | ILE | B | 182 | 20.269 | 46.516 | 83.793 | 1.00 11.86 | B C |
| ATOM | 3797 | CD1 | ILE | B | 182 | 19.870 | 47.818 | 84.419 | 1.00 11.86 | B C |
| ATOM | 3798 | C | ILE | B | 182 | 22.876 | 47.374 | 81.085 | 1.00 29.58 | B C |
| ATOM | 3799 | O | ILE | B | 182 | 23.388 | 46.287 | 80.842 | 1.00 29.58 | B O |
| ATOM | 3800 | N | LYS | B | 183 | 23.430 | 48.527 | 80.738 | 1.00 21.55 | B N |
| ATOM | 3801 | CA | LYS | B | 183 | 24.724 | 48.603 | 80.083 | 1.00 21.55 | B C |
| ATOM | 3802 | CB | LYS | B | 183 | 24.543 | 48.691 | 78.566 | 1.00 14.71 | B C |
| ATOM | 3803 | CG | LYS | B | 183 | 23.632 | 49.803 | 78.118 | 1.00 14.71 | B C |
| ATOM | 3804 | CD | LYS | B | 183 | 23.434 | 49.788 | 76.623 | 1.00 14.71 | B C |
| ATOM | 3805 | CE | LYS | B | 183 | 22.499 | 50.901 | 76.212 | 1.00 14.71 | B C |
| ATOM | 3806 | NZ | LYS | B | 183 | 22.366 | 50.998 | 74.751 | 1.00 14.71 | B N |
| ATOM | 3807 | C | LYS | B | 183 | 25.422 | 49.853 | 80.636 | 1.00 21.55 | B C |
| ATOM | 3808 | O | LYS | B | 183 | 24.763 | 50.760 | 81.148 | 1.00 21.55 | B O |
| ATOM | 3809 | N | PRO | B | 184 | 26.764 | 49.922 | 80.539 | 1.00 24.90 | B N |
| ATOM | 3810 | CD | PRO | B | 184 | 27.668 | 48.940 | 79.917 | 1.00 18.30 | B C |
| ATOM | 3811 | CA | PRO | B | 184 | 27.533 | 51.059 | 81.038 | 1.00 24.90 | B C |
| ATOM | 3812 | CB | PRO | B | 184 | 28.921 | 50.779 | 80.502 | 1.00 18.30 | B C |
| ATOM | 3813 | CG | PRO | B | 184 | 28.972 | 49.302 | 80.513 | 1.00 18.30 | B C |

FIG. 4-58

```
ATOM   3814  C   PRO B 184      27.037  52.433  80.633  1.00 24.90       B  C
ATOM   3815  O   PRO B 184      27.242  53.401  81.365  1.00 24.90       B  O
ATOM   3816  N   GLN B 185      26.397  52.523  79.471  1.00 22.32       B  N
ATOM   3817  CA  GLN B 185      25.884  53.802  79.005  1.00 22.32       B  C
ATOM   3818  CB  GLN B 185      25.484  53.725  77.529  1.00 52.56       B  C
ATOM   3819  CG  GLN B 185      26.641  53.413  76.585  1.00 52.56       B  C
ATOM   3820  CD  GLN B 185      26.663  51.955  76.174  1.00 52.56       B  C
ATOM   3821  OE1 GLN B 185      26.075  51.589  75.153  1.00 52.56       B  O
ATOM   3822  NE2 GLN B 185      27.317  51.106  76.976  1.00 52.56       B  N
ATOM   3823  C   GLN B 185      24.698  54.271  79.846  1.00 22.32       B  C
ATOM   3824  O   GLN B 185      24.411  55.463  79.901  1.00 22.32       B  O
ATOM   3825  N   ASN B 186      24.017  53.340  80.509  1.00 26.83       B  N
ATOM   3826  CA  ASN B 186      22.878  53.698  81.345  1.00 26.83       B  C
ATOM   3827  CB  ASN B 186      21.757  52.676  81.221  1.00 25.78       B  C
ATOM   3828  CG  ASN B 186      21.102  52.710  79.876  1.00 25.78       B  C
ATOM   3829  OD1 ASN B 186      21.007  53.763  79.259  1.00 25.78       B  O
ATOM   3830  ND2 ASN B 186      20.629  51.565  79.413  1.00 25.78       B  N
ATOM   3831  C   ASN B 186      23.246  53.831  82.806  1.00 26.83       B  C
ATOM   3832  O   ASN B 186      22.377  53.871  83.662  1.00 26.83       B  O
ATOM   3833  N   LEU B 187      24.533  53.878  83.095  1.00 24.76       B  N
ATOM   3834  CA  LEU B 187      24.991  54.056  84.463  1.00 24.76       B  C
ATOM   3835  CB  LEU B 187      26.031  52.995  84.799  1.00 29.90       B  C
ATOM   3836  CG  LEU B 187      25.613  51.678  85.451  1.00 29.90       B  C
ATOM   3837  CD1 LEU B 187      24.307  51.176  84.908  1.00 29.90       B  C
ATOM   3838  CD2 LEU B 187      26.707  50.680  85.221  1.00 29.90       B  C
ATOM   3839  C   LEU B 187      25.606  55.456  84.615  1.00 24.76       B  C
ATOM   3840  O   LEU B 187      26.808  55.655  84.406  1.00 24.76       B  O
ATOM   3841  N   LEU B 188      24.772  56.431  84.962  1.00 20.74       B  N
ATOM   3842  CA  LEU B 188      25.244  57.794  85.140  1.00 20.74       B  C
ATOM   3843  CB  LEU B 188      24.073  58.767  85.157  1.00 14.15       B  C
ATOM   3844  CG  LEU B 188      23.024  58.635  84.068  1.00 14.15       B  C
ATOM   3845  CD1 LEU B 188      22.085  59.808  84.173  1.00 14.15       B  C
ATOM   3846  CD2 LEU B 188      23.679  58.570  82.718  1.00 14.15       B  C
ATOM   3847  C   LEU B 188      25.944  57.879  86.477  1.00 20.74       B  C
ATOM   3848  O   LEU B 188      25.568  57.187  87.411  1.00 20.74       B  O
ATOM   3849  N   LEU B 189      26.965  58.720  86.574  1.00 21.23       B  N
ATOM   3850  CA  LEU B 189      27.668  58.885  87.839  1.00 21.23       B  C
ATOM   3851  CB  LEU B 189      28.712  57.773  88.045  1.00 29.57       B  C
ATOM   3852  CG  LEU B 189      29.736  57.413  86.971  1.00 29.57       B  C
ATOM   3853  CD1 LEU B 189      30.737  58.529  86.814  1.00 29.57       B  C
ATOM   3854  CD2 LEU B 189      30.430  56.130  87.359  1.00 29.57       B  C
ATOM   3855  C   LEU B 189      28.304  60.258  87.990  1.00 21.23       B  C
ATOM   3856  O   LEU B 189      28.824  60.823  87.038  1.00 21.23       B  O
ATOM   3857  N   ASP B 190      28.226  60.792  89.204  1.00 32.78       B  N
ATOM   3858  CA  ASP B 190      28.763  62.105  89.530  1.00 32.78       B  C
ATOM   3859  CB  ASP B 190      27.921  62.757  90.621  1.00 40.83       B  C
ATOM   3860  CG  ASP B 190      28.500  64.064  91.094  1.00 40.83       B  C
ATOM   3861  OD1 ASP B 190      29.674  64.076  91.532  1.00 40.83       B  O
ATOM   3862  OD2 ASP B 190      27.770  65.076  91.026  1.00 40.83       B  O
ATOM   3863  C   ASP B 190      30.183  61.929  90.035  1.00 32.78       B  C
ATOM   3864  O   ASP B 190      30.389  61.449  91.146  1.00 32.78       B  O
ATOM   3865  N   PRO B 191      31.181  62.342  89.241  1.00 38.95       B  N
ATOM   3866  CD  PRO B 191      31.074  63.316  88.144  1.00 45.26       B  C
ATOM   3867  CA  PRO B 191      32.579  62.200  89.652  1.00 38.95       B  C
ATOM   3868  CB  PRO B 191      33.328  63.107  88.679  1.00 45.26       B  C
ATOM   3869  CG  PRO B 191      32.322  64.158  88.357  1.00 45.26       B  C
ATOM   3870  C   PRO B 191      32.913  62.543  91.109  1.00 38.95       B  C
ATOM   3871  O   PRO B 191      33.519  61.738  91.826  1.00 38.95       B  O
ATOM   3872  N   ASP B 192      32.512  63.731  91.546  1.00 42.34       B  N
ATOM   3873  CA  ASP B 192      32.830  64.194  92.897  1.00 42.34       B  C
ATOM   3874  CB  ASP B 192      32.519  65.696  93.042  1.00 54.89       B  C
ATOM   3875  CG  ASP B 192      33.153  66.549  91.931  1.00 54.89       B  C
ATOM   3876  OD1 ASP B 192      34.377  66.382  91.673  1.00 54.89       B  O
ATOM   3877  OD2 ASP B 192      32.418  67.384  91.328  1.00 54.89       B  O
ATOM   3878  C   ASP B 192      32.210  63.479  94.089  1.00 42.34       B  C
ATOM   3879  O   ASP B 192      32.827  63.399  95.152  1.00 42.34       B  O
ATOM   3880  N   THR B 193      30.988  62.988  93.932  1.00 23.38       B  N
```

FIG. 4-59

```
ATOM   3881  CA   THR B 193      30.311  62.312  95.025  1.00 23.38      B    C
ATOM   3882  CB   THR B 193      28.808  62.659  95.042  1.00 22.93      B    C
ATOM   3883  OG1  THR B 193      28.127  61.945  94.001  1.00 22.93      B    O
ATOM   3884  CG2  THR B 193      28.620  64.142  94.809  1.00 22.93      B    C
ATOM   3885  C    THR B 193      30.476  60.813  94.875  1.00 23.38      B    C
ATOM   3886  O    THR B 193      30.385  60.075  95.842  1.00 23.38      B    O
ATOM   3887  N    ALA B 194      30.728  60.373  93.648  1.00 26.23      B    N
ATOM   3888  CA   ALA B 194      30.898  58.957  93.345  1.00 26.23      B    C
ATOM   3889  CB   ALA B 194      31.947  58.338  94.273  1.00 19.42      B    C
ATOM   3890  C    ALA B 194      29.574  58.204  93.461  1.00 26.23      B    C
ATOM   3891  O    ALA B 194      29.541  57.017  93.747  1.00 26.23      B    O
ATOM   3892  N    VAL B 195      28.481  58.909  93.230  1.00 32.50      B    N
ATOM   3893  CA   VAL B 195      27.156  58.320  93.295  1.00 32.50      B    C
ATOM   3894  CB   VAL B 195      26.117  59.388  93.689  1.00 22.98      B    C
ATOM   3895  CG1  VAL B 195      24.724  58.806  93.666  1.00 22.98      B    C
ATOM   3896  CG2  VAL B 195      26.443  59.945  95.051  1.00 22.98      B    C
ATOM   3897  C    VAL B 195      26.819  57.824  91.902  1.00 32.50      B    C
ATOM   3898  O    VAL B 195      27.130  58.484  90.906  1.00 32.50      B    O
ATOM   3899  N    LEU B 196      26.194  56.658  91.833  1.00 27.60      B    N
ATOM   3900  CA   LEU B 196      25.795  56.097  90.556  1.00 27.60      B    C
ATOM   3901  CB   LEU B 196      26.174  54.616  90.480  1.00 26.68      B    C
ATOM   3902  CG   LEU B 196      25.837  53.861  89.187  1.00 26.68      B    C
ATOM   3903  CD1  LEU B 196      26.826  52.736  89.000  1.00 26.68      B    C
ATOM   3904  CD2  LEU B 196      24.419  53.326  89.216  1.00 26.68      B    C
ATOM   3905  C    LEU B 196      24.293  56.260  90.472  1.00 27.60      B    C
ATOM   3906  O    LEU B 196      23.608  56.237  91.482  1.00 27.60      B    O
ATOM   3907  N    LYS B 197      23.789  56.457  89.264  1.00 28.47      B    N
ATOM   3908  CA   LYS B 197      22.361  56.627  89.045  1.00 28.47      B    C
ATOM   3909  CB   LYS B 197      22.011  58.113  88.960  1.00 21.98      B    C
ATOM   3910  CG   LYS B 197      21.970  58.752  90.310  1.00 21.98      B    C
ATOM   3911  CD   LYS B 197      21.716  60.230  90.235  1.00 21.98      B    C
ATOM   3912  CE   LYS B 197      20.947  60.688  91.463  1.00 21.98      B    C
ATOM   3913  NZ   LYS B 197      21.329  59.903  92.657  1.00 21.98      B    N
ATOM   3914  C    LYS B 197      21.954  55.918  87.767  1.00 28.47      B    C
ATOM   3915  O    LYS B 197      22.519  56.169  86.705  1.00 28.47      B    O
ATOM   3916  N    LEU B 198      20.994  55.009  87.881  1.00 23.96      B    N
ATOM   3917  CA   LEU B 198      20.519  54.276  86.728  1.00 23.96      B    C
ATOM   3918  CB   LEU B 198      19.796  53.010  87.171  1.00 19.80      B    C
ATOM   3919  CG   LEU B 198      19.290  52.129  86.040  1.00 19.80      B    C
ATOM   3920  CD1  LEU B 198      20.454  51.550  85.279  1.00 19.80      B    C
ATOM   3921  CD2  LEU B 198      18.442  51.044  86.620  1.00 19.80      B    C
ATOM   3922  C    LEU B 198      19.569  55.184  85.968  1.00 23.96      B    C
ATOM   3923  O    LEU B 198      18.890  56.024  86.565  1.00 23.96      B    O
ATOM   3924  N    CYS B 199      19.543  55.022  84.651  1.00 31.58      B    N
ATOM   3925  CA   CYS B 199      18.677  55.819  83.799  1.00 31.58      B    C
ATOM   3926  CB   CYS B 199      19.395  57.098  83.352  1.00 33.88      B    C
ATOM   3927  SG   CYS B 199      20.792  56.837  82.269  1.00 33.88      B    S
ATOM   3928  C    CYS B 199      18.213  55.009  82.586  1.00 31.58      B    C
ATOM   3929  O    CYS B 199      18.522  53.828  82.465  1.00 31.58      B    O
ATOM   3930  N    ASP B 200      17.459  55.656  81.708  1.00 29.06      B    N
ATOM   3931  CA   ASP B 200      16.922  55.043  80.498  1.00 29.06      B    C
ATOM   3932  CB   ASP B 200      18.057  54.653  79.558  1.00 26.76      B    C
ATOM   3933  CG   ASP B 200      17.565  54.306  78.162  1.00 26.76      B    C
ATOM   3934  OD1  ASP B 200      16.445  54.734  77.804  1.00 26.76      B    O
ATOM   3935  OD2  ASP B 200      18.304  53.623  77.415  1.00 26.76      B    O
ATOM   3936  C    ASP B 200      15.995  53.846  80.708  1.00 29.06      B    C
ATOM   3937  O    ASP B 200      16.319  52.723  80.353  1.00 29.06      B    O
ATOM   3938  N    PHE B 201      14.817  54.093  81.265  1.00 38.87      B    N
ATOM   3939  CA   PHE B 201      13.873  53.014  81.490  1.00 38.87      B    C
ATOM   3940  CB   PHE B 201      13.046  53.303  82.738  1.00 20.42      B    C
ATOM   3941  CG   PHE B 201      13.850  53.279  83.995  1.00 20.42      B    C
ATOM   3942  CD1  PHE B 201      14.758  54.283  84.266  1.00 20.42      B    C
ATOM   3943  CD2  PHE B 201      13.760  52.214  84.874  1.00 20.42      B    C
ATOM   3944  CE1  PHE B 201      15.570  54.221  85.391  1.00 20.42      B    C
ATOM   3945  CE2  PHE B 201      14.575  52.147  86.005  1.00 20.42      B    C
ATOM   3946  CZ   PHE B 201      15.478  53.151  86.260  1.00 20.42      B    C
ATOM   3947  C    PHE B 201      12.970  52.834  80.287  1.00 38.87      B    C
```

FIG. 4-60

| | | | | | | | | | | | |
|---|---|---|---|---|---|---|---|---|---|---|---|
| ATOM | 3948 | O | PHE | B | 201 | 11.888 | 52.247 | 80.385 | 1.00 | 38.87 | B O |
| ATOM | 3949 | N | GLY | B | 202 | 13.419 | 53.349 | 79.148 | 1.00 | 25.25 | B N |
| ATOM | 3950 | CA | GLY | B | 202 | 12.633 | 53.247 | 77.937 | 1.00 | 25.25 | B C |
| ATOM | 3951 | C | GLY | B | 202 | 12.262 | 51.812 | 77.614 | 1.00 | 25.25 | B C |
| ATOM | 3952 | O | GLY | B | 202 | 11.267 | 51.571 | 76.934 | 1.00 | 25.25 | B O |
| ATOM | 3953 | N | SER | B | 203 | 13.049 | 50.852 | 78.094 | 1.00 | 42.50 | B N |
| ATOM | 3954 | CA | SER | B | 203 | 12.763 | 49.442 | 77.829 | 1.00 | 42.50 | B C |
| ATOM | 3955 | CB | SER | B | 203 | 14.028 | 48.675 | 77.444 | 1.00 | 26.10 | B C |
| ATOM | 3956 | OG | SER | B | 203 | 14.740 | 49.340 | 76.428 | 1.00 | 26.10 | B O |
| ATOM | 3957 | C | SER | B | 203 | 12.166 | 48.745 | 79.029 | 1.00 | 42.50 | B C |
| ATOM | 3958 | O | SER | B | 203 | 11.672 | 47.626 | 78.907 | 1.00 | 42.50 | B O |
| ATOM | 3959 | N | ALA | B | 204 | 12.225 | 49.393 | 80.187 | 1.00 | 21.17 | B N |
| ATOM | 3960 | CA | ALA | B | 204 | 11.691 | 48.798 | 81.396 | 1.00 | 21.17 | B C |
| ATOM | 3961 | CB | ALA | B | 204 | 11.939 | 49.710 | 82.581 | 1.00 | 26.85 | B C |
| ATOM | 3962 | C | ALA | B | 204 | 10.208 | 48.475 | 81.293 | 1.00 | 21.17 | B C |
| ATOM | 3963 | O | ALA | B | 204 | 9.424 | 49.225 | 80.712 | 1.00 | 21.17 | B O |
| ATOM | 3964 | N | LYS | B | 205 | 9.845 | 47.335 | 81.866 | 1.00 | 33.07 | B N |
| ATOM | 3965 | CA | LYS | B | 205 | 8.471 | 46.860 | 81.902 | 1.00 | 33.07 | B C |
| ATOM | 3966 | CB | LYS | B | 205 | 8.164 | 46.055 | 80.648 | 1.00 | 28.74 | B C |
| ATOM | 3967 | CG | LYS | B | 205 | 6.795 | 45.437 | 80.634 | 1.00 | 28.74 | B C |
| ATOM | 3968 | CD | LYS | B | 205 | 6.509 | 44.707 | 79.332 | 1.00 | 28.74 | B C |
| ATOM | 3969 | CE | LYS | B | 205 | 5.077 | 44.204 | 79.332 | 1.00 | 28.74 | B C |
| ATOM | 3970 | NZ | LYS | B | 205 | 4.825 | 43.218 | 78.243 | 1.00 | 28.74 | B N |
| ATOM | 3971 | C | LYS | B | 205 | 8.244 | 45.972 | 83.121 | 1.00 | 33.07 | B C |
| ATOM | 3972 | O | LYS | B | 205 | 9.180 | 45.358 | 83.636 | 1.00 | 33.07 | B O |
| ATOM | 3973 | N | GLN | B | 206 | 7.006 | 45.910 | 83.593 | 1.00 | 33.01 | B N |
| ATOM | 3974 | CA | GLN | B | 206 | 6.714 | 45.035 | 84.713 | 1.00 | 33.01 | B C |
| ATOM | 3975 | CB | GLN | B | 206 | 5.382 | 45.378 | 85.360 | 1.00 | 59.99 | B C |
| ATOM | 3976 | CG | GLN | B | 206 | 5.388 | 46.643 | 86.171 | 1.00 | 59.99 | B C |
| ATOM | 3977 | CD | GLN | B | 206 | 4.321 | 46.610 | 87.270 | 1.00 | 59.99 | B C |
| ATOM | 3978 | OE1 | GLN | B | 206 | 4.029 | 47.638 | 87.926 | 1.00 | 59.99 | B O |
| ATOM | 3979 | NE2 | GLN | B | 206 | 3.735 | 45.417 | 87.483 | 1.00 | 59.99 | B N |
| ATOM | 3980 | C | GLN | B | 206 | 6.632 | 43.621 | 84.155 | 1.00 | 33.01 | B C |
| ATOM | 3981 | O | GLN | B | 206 | 5.941 | 43.385 | 83.159 | 1.00 | 33.01 | B O |
| ATOM | 3982 | N | LEU | B | 207 | 7.340 | 42.682 | 84.772 | 1.00 | 27.17 | B N |
| ATOM | 3983 | CA | LEU | B | 207 | 7.289 | 41.305 | 84.290 | 1.00 | 27.17 | B C |
| ATOM | 3984 | CB | LEU | B | 207 | 8.676 | 40.672 | 84.262 | 1.00 | 29.69 | B C |
| ATOM | 3985 | CG | LEU | B | 207 | 9.827 | 41.256 | 83.442 | 1.00 | 29.69 | B C |
| ATOM | 3986 | CD1 | LEU | B | 207 | 11.043 | 40.305 | 83.591 | 1.00 | 29.69 | B C |
| ATOM | 3987 | CD2 | LEU | B | 207 | 9.442 | 41.416 | 81.979 | 1.00 | 29.69 | B C |
| ATOM | 3988 | C | LEU | B | 207 | 6.410 | 40.445 | 85.176 | 1.00 | 27.17 | B C |
| ATOM | 3989 | O | LEU | B | 207 | 6.750 | 40.193 | 86.328 | 1.00 | 27.17 | B O |
| ATOM | 3990 | N | VAL | B | 208 | 5.294 | 39.977 | 84.628 | 1.00 | 49.37 | B N |
| ATOM | 3991 | CA | VAL | B | 208 | 4.365 | 39.150 | 85.382 | 1.00 | 49.37 | B C |
| ATOM | 3992 | CB | VAL | B | 208 | 2.930 | 39.649 | 85.209 | 1.00 | 34.51 | B C |
| ATOM | 3993 | CG1 | VAL | B | 208 | 2.048 | 39.011 | 86.262 | 1.00 | 34.51 | B C |
| ATOM | 3994 | CG2 | VAL | B | 208 | 2.896 | 41.177 | 85.302 | 1.00 | 34.51 | B C |
| ATOM | 3995 | C | VAL | B | 208 | 4.458 | 37.709 | 84.915 | 1.00 | 49.37 | B C |
| ATOM | 3996 | O | VAL | B | 208 | 4.442 | 37.452 | 83.714 | 1.00 | 49.37 | B O |
| ATOM | 3997 | N | ALA | B | 209 | 4.566 | 36.775 | 85.856 | 1.00 | 39.04 | B N |
| ATOM | 3998 | CA | ALA | B | 209 | 4.671 | 35.359 | 85.509 | 1.00 | 39.04 | B C |
| ATOM | 3999 | CB | ALA | B | 209 | 4.682 | 34.496 | 86.779 | 1.00 | 21.99 | B C |
| ATOM | 4000 | C | ALA | B | 209 | 3.503 | 34.964 | 84.607 | 1.00 | 39.04 | B C |
| ATOM | 4001 | O | ALA | B | 209 | 2.358 | 35.372 | 84.834 | 1.00 | 39.04 | B O |
| ATOM | 4002 | N | GLY | B | 210 | 3.790 | 34.185 | 83.569 | 1.00 | 39.93 | B N |
| ATOM | 4003 | CA | GLY | B | 210 | 2.725 | 33.769 | 82.678 | 1.00 | 39.93 | B C |
| ATOM | 4004 | C | GLY | B | 210 | 2.635 | 34.651 | 81.450 | 1.00 | 39.93 | B C |
| ATOM | 4005 | O | GLY | B | 210 | 2.223 | 34.190 | 80.376 | 1.00 | 39.93 | B O |
| ATOM | 4006 | N | GLU | B | 211 | 3.021 | 35.916 | 81.599 | 1.00 | 44.65 | B N |
| ATOM | 4007 | CA | GLU | B | 211 | 2.977 | 36.859 | 80.484 | 1.00 | 44.65 | B C |
| ATOM | 4008 | CB | GLU | B | 211 | 2.809 | 38.289 | 80.992 | 1.00 | 51.93 | B C |
| ATOM | 4009 | CG | GLU | B | 211 | 1.766 | 38.454 | 82.064 | 1.00 | 51.93 | B C |
| ATOM | 4010 | CD | GLU | B | 211 | 1.451 | 39.924 | 82.326 | 1.00 | 51.93 | B C |
| ATOM | 4011 | OE1 | GLU | B | 211 | 0.609 | 40.210 | 83.219 | 1.00 | 51.93 | B O |
| ATOM | 4012 | OE2 | GLU | B | 211 | 2.051 | 40.784 | 81.625 | 1.00 | 51.93 | B O |
| ATOM | 4013 | C | GLU | B | 211 | 4.246 | 36.784 | 79.638 | 1.00 | 44.65 | B C |
| ATOM | 4014 | O | GLU | B | 211 | 5.357 | 36.850 | 80.157 | 1.00 | 44.65 | B O |

FIG. 4-61

| ATOM | 4015 | N | PRO | B | 212 | 4.099 | 36.622 | 78.320 | 1.00 | 53.54 | B | N |
| ATOM | 4016 | CD | PRO | B | 212 | 2.921 | 36.173 | 77.555 | 1.00 | 30.17 | B | C |
| ATOM | 4017 | CA | PRO | B | 212 | 5.306 | 36.552 | 77.499 | 1.00 | 53.54 | B | C |
| ATOM | 4018 | CB | PRO | B | 212 | 4.830 | 35.792 | 76.260 | 1.00 | 30.17 | B | C |
| ATOM | 4019 | CG | PRO | B | 212 | 3.421 | 36.226 | 76.130 | 1.00 | 30.17 | B | C |
| ATOM | 4020 | C | PRO | B | 212 | 5.809 | 37.954 | 77.184 | 1.00 | 53.54 | B | C |
| ATOM | 4021 | O | PRO | B | 212 | 5.011 | 38.905 | 77.131 | 1.00 | 53.54 | B | O |
| ATOM | 4022 | N | ASN | B | 213 | 7.122 | 38.081 | 76.985 | 1.00 | 22.95 | B | N |
| ATOM | 4023 | CA | ASN | B | 213 | 7.704 | 39.374 | 76.673 | 1.00 | 22.95 | B | C |
| ATOM | 4024 | CB | ASN | B | 213 | 8.344 | 39.959 | 77.914 | 1.00 | 24.31 | B | C |
| ATOM | 4025 | CG | ASN | B | 213 | 7.335 | 40.255 | 78.992 | 1.00 | 24.31 | B | C |
| ATOM | 4026 | OD1 | ASN | B | 213 | 6.470 | 41.117 | 78.831 | 1.00 | 24.31 | B | O |
| ATOM | 4027 | ND2 | ASN | B | 213 | 7.440 | 39.543 | 80.105 | 1.00 | 24.31 | B | N |
| ATOM | 4028 | C | ASN | B | 213 | 8.710 | 39.259 | 75.554 | 1.00 | 22.95 | B | C |
| ATOM | 4029 | O | ASN | B | 213 | 9.355 | 38.225 | 75.404 | 1.00 | 22.95 | B | O |
| ATOM | 4030 | N | VAL | B | 214 | 8.825 | 40.324 | 74.762 | 1.00 | 31.28 | B | N |
| ATOM | 4031 | CA | VAL | B | 214 | 9.727 | 40.353 | 73.619 | 1.00 | 31.28 | B | C |
| ATOM | 4032 | CB | VAL | B | 214 | 9.650 | 41.698 | 72.909 | 1.00 | 17.02 | B | C |
| ATOM | 4033 | CG1 | VAL | B | 214 | 8.268 | 41.894 | 72.345 | 1.00 | 17.02 | B | C |
| ATOM | 4034 | CG2 | VAL | B | 214 | 9.992 | 42.803 | 73.879 | 1.00 | 17.02 | B | C |
| ATOM | 4035 | C | VAL | B | 214 | 11.162 | 40.082 | 74.033 | 1.00 | 31.28 | B | C |
| ATOM | 4036 | O | VAL | B | 214 | 11.629 | 40.576 | 75.057 | 1.00 | 31.28 | B | O |
| ATOM | 4037 | N | SER | B | 215 | 11.857 | 39.292 | 73.226 | 1.00 | 31.30 | B | N |
| ATOM | 4038 | CA | SER | B | 215 | 13.228 | 38.922 | 73.519 | 1.00 | 31.30 | B | C |
| ATOM | 4039 | CB | SER | B | 215 | 13.472 | 37.478 | 73.096 | 1.00 | 43.00 | B | C |
| ATOM | 4040 | OG | SER | B | 215 | 13.157 | 37.298 | 71.726 | 1.00 | 43.00 | B | O |
| ATOM | 4041 | C | SER | B | 215 | 14.261 | 39.798 | 72.854 | 1.00 | 31.30 | B | C |
| ATOM | 4042 | O | SER | B | 215 | 15.448 | 39.602 | 73.075 | 1.00 | 31.30 | B | O |
| ATOM | 4043 | N | TYR | B | 216 | 13.821 | 40.767 | 72.059 | 1.00 | 26.72 | B | N |
| ATOM | 4044 | CA | TYR | B | 216 | 14.750 | 41.637 | 71.344 | 1.00 | 26.72 | B | C |
| ATOM | 4045 | CB | TYR | B | 216 | 14.201 | 41.934 | 69.941 | 1.00 | 26.88 | B | C |
| ATOM | 4046 | CG | TYR | B | 216 | 12.805 | 42.490 | 69.923 | 1.00 | 26.88 | B | C |
| ATOM | 4047 | CD1 | TYR | B | 216 | 12.558 | 43.841 | 70.204 | 1.00 | 26.88 | B | C |
| ATOM | 4048 | CE1 | TYR | B | 216 | 11.261 | 44.363 | 70.185 | 1.00 | 26.88 | B | C |
| ATOM | 4049 | CD2 | TYR | B | 216 | 11.730 | 41.673 | 69.628 | 1.00 | 26.88 | B | C |
| ATOM | 4050 | CE2 | TYR | B | 216 | 10.435 | 42.175 | 69.606 | 1.00 | 26.88 | B | C |
| ATOM | 4051 | CZ | TYR | B | 216 | 10.205 | 43.521 | 69.883 | 1.00 | 26.88 | B | C |
| ATOM | 4052 | OH | TYR | B | 216 | 8.920 | 44.010 | 69.845 | 1.00 | 26.88 | B | O |
| ATOM | 4053 | C | TYR | B | 216 | 15.037 | 42.913 | 72.111 | 1.00 | 26.72 | B | C |
| ATOM | 4054 | O | TYR | B | 216 | 15.371 | 43.960 | 71.555 | 1.00 | 26.72 | B | O |
| ATOM | 4055 | N | ILE | B | 217 | 14.900 | 42.801 | 73.412 | 1.00 | 27.12 | B | N |
| ATOM | 4056 | CA | ILE | B | 217 | 15.173 | 43.893 | 74.316 | 1.00 | 27.12 | B | C |
| ATOM | 4057 | CB | ILE | B | 217 | 14.274 | 43.720 | 75.569 | 1.00 | 17.41 | B | C |
| ATOM | 4058 | CG2 | ILE | B | 217 | 14.902 | 42.762 | 76.549 | 1.00 | 17.41 | B | C |
| ATOM | 4059 | CG1 | ILE | B | 217 | 13.993 | 45.068 | 76.202 | 1.00 | 17.41 | B | C |
| ATOM | 4060 | CD1 | ILE | B | 217 | 13.006 | 45.879 | 75.396 | 1.00 | 17.41 | B | C |
| ATOM | 4061 | C | ILE | B | 217 | 16.651 | 43.628 | 74.650 | 1.00 | 27.12 | B | C |
| ATOM | 4062 | O | ILE | B | 217 | 17.220 | 42.619 | 74.230 | 1.00 | 27.12 | B | O |
| ATOM | 4063 | N | CYS | B | 218 | 17.264 | 44.530 | 75.395 | 1.00 | 26.58 | B | N |
| ATOM | 4064 | CA | CYS | B | 218 | 18.654 | 44.390 | 75.798 | 1.00 | 26.58 | B | C |
| ATOM | 4065 | CB | CYS | B | 218 | 18.862 | 43.082 | 76.537 | 1.00 | 26.71 | B | C |
| ATOM | 4066 | SG | CYS | B | 218 | 20.246 | 43.222 | 77.607 | 1.00 | 26.71 | B | S |
| ATOM | 4067 | C | CYS | B | 218 | 19.700 | 44.556 | 74.707 | 1.00 | 26.58 | B | C |
| ATOM | 4068 | O | CYS | B | 218 | 19.583 | 44.001 | 73.609 | 1.00 | 26.58 | B | O |
| ATOM | 4069 | N | SER | B | 219 | 20.716 | 45.355 | 75.036 | 1.00 | 24.61 | B | N |
| ATOM | 4070 | CA | SER | B | 219 | 21.835 | 45.653 | 74.143 | 1.00 | 24.61 | B | C |
| ATOM | 4071 | CB | SER | B | 219 | 22.611 | 46.873 | 74.648 | 1.00 | 25.72 | B | C |
| ATOM | 4072 | OG | SER | B | 219 | 21.820 | 48.042 | 74.571 | 1.00 | 25.72 | B | O |
| ATOM | 4073 | C | SER | B | 219 | 22.816 | 44.506 | 73.947 | 1.00 | 24.61 | B | C |
| ATOM | 4074 | O | SER | B | 219 | 22.986 | 43.663 | 74.812 | 1.00 | 24.61 | B | O |
| ATOM | 4075 | N | ARG | B | 220 | 23.487 | 44.536 | 72.800 | 1.00 | 49.64 | B | N |
| ATOM | 4076 | CA | ARG | B | 220 | 24.459 | 43.538 | 72.362 | 1.00 | 49.64 | B | C |
| ATOM | 4077 | CB | ARG | B | 220 | 25.450 | 44.205 | 71.384 | 1.00 | 60.86 | B | C |
| ATOM | 4078 | CG | ARG | B | 220 | 26.691 | 44.875 | 72.003 | 1.00 | 60.86 | B | C |
| ATOM | 4079 | CD | ARG | B | 220 | 26.511 | 46.301 | 72.518 | 1.00 | 60.86 | B | C |
| ATOM | 4080 | NE | ARG | B | 220 | 27.313 | 47.244 | 71.725 | 1.00 | 60.86 | B | N |
| ATOM | 4081 | CZ | ARG | B | 220 | 27.580 | 48.512 | 72.062 | 1.00 | 60.86 | B | C |

FIG. 4-62

| | | | | | | | | | | | |
|---|---|---|---|---|---|---|---|---|---|---|---|
| ATOM | 4082 | NH1 | ARG | B | 220 | 27.108 | 49.017 | 73.199 | 1.00 60.86 | B | N |
| ATOM | 4083 | NH2 | ARG | B | 220 | 28.322 | 49.282 | 71.257 | 1.00 60.86 | B | N |
| ATOM | 4084 | C | ARG | B | 220 | 25.210 | 42.720 | 73.426 | 1.00 49.64 | B | C |
| ATOM | 4085 | O | ARG | B | 220 | 24.704 | 41.699 | 73.895 | 1.00 49.64 | B | O |
| ATOM | 4086 | N | TYR | B | 221 | 26.401 | 43.175 | 73.798 | 1.00 22.39 | B | N |
| ATOM | 4087 | CA | TYR | B | 221 | 27.273 | 42.513 | 74.765 | 1.00 22.39 | B | C |
| ATOM | 4088 | CB | TYR | B | 221 | 28.546 | 43.349 | 74.956 | 1.00 40.76 | B | C |
| ATOM | 4089 | CG | TYR | B | 221 | 29.235 | 43.694 | 73.656 | 1.00 40.76 | B | C |
| ATOM | 4090 | CD1 | TYR | B | 221 | 29.217 | 42.799 | 72.584 | 1.00 40.76 | B | C |
| ATOM | 4091 | CE1 | TYR | B | 221 | 29.845 | 43.091 | 71.381 | 1.00 40.76 | B | C |
| ATOM | 4092 | CD2 | TYR | B | 221 | 29.911 | 44.903 | 73.489 | 1.00 40.76 | B | C |
| ATOM | 4093 | CE2 | TYR | B | 221 | 30.549 | 45.201 | 72.283 | 1.00 40.76 | B | C |
| ATOM | 4094 | CZ | TYR | B | 221 | 30.506 | 44.285 | 71.238 | 1.00 40.76 | B | C |
| ATOM | 4095 | OH | TYR | B | 221 | 31.115 | 44.549 | 70.040 | 1.00 40.76 | B | O |
| ATOM | 4096 | C | TYR | B | 221 | 26.732 | 42.167 | 76.144 | 1.00 22.39 | B | C |
| ATOM | 4097 | O | TYR | B | 221 | 27.382 | 41.419 | 76.866 | 1.00 22.39 | B | O |
| ATOM | 4098 | N | TYR | B | 222 | 25.563 | 42.684 | 76.518 | 1.00 20.48 | B | N |
| ATOM | 4099 | CA | TYR | B | 222 | 25.022 | 42.424 | 77.852 | 1.00 20.48 | B | C |
| ATOM | 4100 | CB | TYR | B | 222 | 24.795 | 43.753 | 78.576 | 1.00 26.43 | B | C |
| ATOM | 4101 | CG | TYR | B | 222 | 25.942 | 44.708 | 78.383 | 1.00 26.43 | B | C |
| ATOM | 4102 | CD1 | TYR | B | 222 | 27.044 | 44.684 | 79.216 | 1.00 26.43 | B | C |
| ATOM | 4103 | CE1 | TYR | B | 222 | 28.128 | 45.523 | 78.981 | 1.00 26.43 | B | C |
| ATOM | 4104 | CD2 | TYR | B | 222 | 25.953 | 45.595 | 77.314 | 1.00 26.43 | B | C |
| ATOM | 4105 | CE2 | TYR | B | 222 | 27.028 | 46.429 | 77.076 | 1.00 26.43 | B | C |
| ATOM | 4106 | CZ | TYR | B | 222 | 28.112 | 46.391 | 77.908 | 1.00 26.43 | B | C |
| ATOM | 4107 | OH | TYR | B | 222 | 29.179 | 47.224 | 77.667 | 1.00 26.43 | B | O |
| ATOM | 4108 | C | TYR | B | 222 | 23.759 | 41.592 | 77.952 | 1.00 20.48 | B | C |
| ATOM | 4109 | O | TYR | B | 222 | 23.195 | 41.476 | 79.034 | 1.00 20.48 | B | O |
| ATOM | 4110 | N | ARG | B | 223 | 23.329 | 41.000 | 76.847 | 1.00 16.85 | B | N |
| ATOM | 4111 | CA | ARG | B | 223 | 22.116 | 40.191 | 76.832 | 1.00 16.85 | B | C |
| ATOM | 4112 | CB | ARG | B | 223 | 21.637 | 40.030 | 75.398 | 1.00 21.43 | B | C |
| ATOM | 4113 | CG | ARG | B | 223 | 21.648 | 41.332 | 74.637 | 1.00 21.43 | B | C |
| ATOM | 4114 | CD | ARG | B | 223 | 21.234 | 41.169 | 73.195 | 1.00 21.43 | B | C |
| ATOM | 4115 | NE | ARG | B | 223 | 19.809 | 40.913 | 73.054 | 1.00 21.43 | B | N |
| ATOM | 4116 | CZ | ARG | B | 223 | 19.321 | 39.799 | 72.532 | 1.00 21.43 | B | C |
| ATOM | 4117 | NH1 | ARG | B | 223 | 20.153 | 38.859 | 72.117 | 1.00 21.43 | B | N |
| ATOM | 4118 | NH2 | ARG | B | 223 | 18.014 | 39.635 | 72.414 | 1.00 21.43 | B | N |
| ATOM | 4119 | C | ARG | B | 223 | 22.279 | 38.820 | 77.469 | 1.00 16.85 | B | C |
| ATOM | 4120 | O | ARG | B | 223 | 23.211 | 38.094 | 77.164 | 1.00 16.85 | B | O |
| ATOM | 4121 | N | ALA | B | 224 | 21.363 | 38.466 | 78.359 | 1.00 21.16 | B | N |
| ATOM | 4122 | CA | ALA | B | 224 | 21.429 | 37.170 | 79.025 | 1.00 21.16 | B | C |
| ATOM | 4123 | CB | ALA | B | 224 | 20.317 | 37.049 | 80.051 | 1.00 16.30 | B | C |
| ATOM | 4124 | C | ALA | B | 224 | 21.329 | 36.040 | 78.020 | 1.00 21.16 | B | C |
| ATOM | 4125 | O | ALA | B | 224 | 20.653 | 36.149 | 77.001 | 1.00 21.16 | B | O |
| ATOM | 4126 | N | PRO | B | 225 | 21.999 | 34.924 | 78.296 | 1.00 25.24 | B | N |
| ATOM | 4127 | CD | PRO | B | 225 | 22.876 | 34.615 | 79.430 | 1.00 32.24 | B | C |
| ATOM | 4128 | CA | PRO | B | 225 | 21.923 | 33.817 | 77.350 | 1.00 25.24 | B | C |
| ATOM | 4129 | CB | PRO | B | 225 | 22.695 | 32.713 | 78.054 | 1.00 32.24 | B | C |
| ATOM | 4130 | CG | PRO | B | 225 | 22.720 | 33.162 | 79.514 | 1.00 32.24 | B | C |
| ATOM | 4131 | C | PRO | B | 225 | 20.504 | 33.453 | 76.943 | 1.00 25.24 | B | C |
| ATOM | 4132 | O | PRO | B | 225 | 20.281 | 33.197 | 75.781 | 1.00 25.24 | B | O |
| ATOM | 4133 | N | GLU | B | 226 | 19.542 | 33.470 | 77.860 | 1.00 26.45 | B | N |
| ATOM | 4134 | CA | GLU | B | 226 | 18.160 | 33.145 | 77.494 | 1.00 26.45 | B | C |
| ATOM | 4135 | CB | GLU | B | 226 | 17.256 | 33.074 | 78.735 | 1.00 20.80 | B | C |
| ATOM | 4136 | CG | GLU | B | 226 | 17.195 | 34.344 | 79.569 | 1.00 20.80 | B | C |
| ATOM | 4137 | CD | GLU | B | 226 | 18.166 | 34.332 | 80.727 | 1.00 20.80 | B | C |
| ATOM | 4138 | OE1 | GLU | B | 226 | 19.322 | 33.945 | 80.513 | 1.00 20.80 | B | O |
| ATOM | 4139 | OE2 | GLU | B | 226 | 17.790 | 34.715 | 81.852 | 1.00 20.80 | B | O |
| ATOM | 4140 | C | GLU | B | 226 | 17.574 | 34.138 | 76.497 | 1.00 26.45 | B | C |
| ATOM | 4141 | O | GLU | B | 226 | 16.739 | 33.768 | 75.672 | 1.00 26.45 | B | O |
| ATOM | 4142 | N | LEU | B | 227 | 17.991 | 35.397 | 76.566 | 1.00 24.06 | B | N |
| ATOM | 4143 | CA | LEU | B | 227 | 17.458 | 36.374 | 75.626 | 1.00 24.06 | B | C |
| ATOM | 4144 | CB | LEU | B | 227 | 17.869 | 37.793 | 76.016 | 1.00 19.28 | B | C |
| ATOM | 4145 | CG | LEU | B | 227 | 17.267 | 38.307 | 77.318 | 1.00 19.28 | B | C |
| ATOM | 4146 | CD1 | LEU | B | 227 | 17.775 | 39.708 | 77.542 | 1.00 19.28 | B | C |
| ATOM | 4147 | CD2 | LEU | B | 227 | 15.758 | 38.277 | 77.263 | 1.00 19.28 | B | C |
| ATOM | 4148 | C | LEU | B | 227 | 17.976 | 36.040 | 74.230 | 1.00 24.06 | B | C |

FIG. 4-63

```
ATOM   4149  O    LEU B 227      17.286  36.246  73.232  1.00 24.06      B    O
ATOM   4150  N    ILE B 228      19.194  35.515  74.165  1.00 23.42      B    N
ATOM   4151  CA   ILE B 228      19.769  35.152  72.887  1.00 23.42      B    C
ATOM   4152  CB   ILE B 228      21.269  34.836  73.022  1.00 16.11      B    C
ATOM   4153  CG2  ILE B 228      21.817  34.339  71.694  1.00 16.11      B    C
ATOM   4154  CG1  ILE B 228      22.029  36.102  73.435  1.00 16.11      B    C
ATOM   4155  CD1  ILE B 228      23.483  35.860  73.803  1.00 16.11      B    C
ATOM   4156  C    ILE B 228      19.031  33.944  72.316  1.00 23.42      B    C
ATOM   4157  O    ILE B 228      18.849  33.838  71.104  1.00 23.42      B    O
ATOM   4158  N    PHE B 229      18.590  33.042  73.187  1.00 34.60      B    N
ATOM   4159  CA   PHE B 229      17.862  31.859  72.743  1.00 34.60      B    C
ATOM   4160  CB   PHE B 229      17.938  30.746  73.789  1.00 19.68      B    C
ATOM   4161  CG   PHE B 229      19.298  30.135  73.948  1.00 19.68      B    C
ATOM   4162  CD1  PHE B 229      19.920  29.506  72.879  1.00 19.68      B    C
ATOM   4163  CD2  PHE B 229      19.941  30.148  75.182  1.00 19.68      B    C
ATOM   4164  CE1  PHE B 229      21.158  28.893  73.028  1.00 19.68      B    C
ATOM   4165  CE2  PHE B 229      21.186  29.532  75.340  1.00 19.68      B    C
ATOM   4166  CZ   PHE B 229      21.795  28.904  74.259  1.00 19.68      B    C
ATOM   4167  C    PHE B 229      16.389  32.148  72.428  1.00 34.60      B    C
ATOM   4168  O    PHE B 229      15.592  31.217  72.260  1.00 34.60      B    O
ATOM   4169  N    GLY B 230      16.024  33.426  72.367  1.00 31.91      B    N
ATOM   4170  CA   GLY B 230      14.653  33.798  72.044  1.00 31.91      B    C
ATOM   4171  C    GLY B 230      13.571  33.530  73.079  1.00 31.91      B    C
ATOM   4172  O    GLY B 230      12.380  33.657  72.784  1.00 31.91      B    O
ATOM   4173  N    ALA B 231      13.974  33.148  74.287  1.00 24.97      B    N
ATOM   4174  CA   ALA B 231      13.025  32.891  75.365  1.00 24.97      B    C
ATOM   4175  CB   ALA B 231      13.766  32.594  76.645  1.00 15.84      B    C
ATOM   4176  C    ALA B 231      12.139  34.110  75.561  1.00 24.97      B    C
ATOM   4177  O    ALA B 231      12.584  35.237  75.386  1.00 24.97      B    O
ATOM   4178  N    THR B 232      10.883  33.891  75.918  1.00 39.88      B    N
ATOM   4179  CA   THR B 232       9.973  35.008  76.132  1.00 39.88      B    C
ATOM   4180  CB   THR B 232       8.857  35.024  75.085  1.00 33.65      B    C
ATOM   4181  OG1  THR B 232       8.114  33.801  75.171  1.00 33.65      B    O
ATOM   4182  CG2  THR B 232       9.437  35.185  73.693  1.00 33.65      B    C
ATOM   4183  C    THR B 232       9.328  34.959  77.512  1.00 39.88      B    C
ATOM   4184  O    THR B 232       8.356  35.679  77.777  1.00 39.88      B    O
ATOM   4185  N    ASP B 233       9.870  34.104  78.375  1.00 23.86      B    N
ATOM   4186  CA   ASP B 233       9.379  33.954  79.736  1.00 23.86      B    C
ATOM   4187  CB   ASP B 233       8.882  32.539  79.958  1.00 23.48      B    C
ATOM   4188  CG   ASP B 233       9.952  31.513  79.708  1.00 23.48      B    C
ATOM   4189  OD1  ASP B 233      11.008  31.864  79.137  1.00 23.48      B    O
ATOM   4190  OD2  ASP B 233       9.733  30.347  80.078  1.00 23.48      B    O
ATOM   4191  C    ASP B 233      10.516  34.253  80.700  1.00 23.86      B    C
ATOM   4192  O    ASP B 233      10.584  33.705  81.802  1.00 23.86      B    O
ATOM   4193  N    TYR B 234      11.412  35.137  80.275  1.00 32.46      B    N
ATOM   4194  CA   TYR B 234      12.541  35.518  81.106  1.00 32.46      B    C
ATOM   4195  CB   TYR B 234      13.530  36.354  80.290  1.00 23.59      B    C
ATOM   4196  CG   TYR B 234      12.953  37.588  79.631  1.00 23.59      B    C
ATOM   4197  CD1  TYR B 234      12.158  37.495  78.495  1.00 23.59      B    C
ATOM   4198  CE1  TYR B 234      11.679  38.638  77.850  1.00 23.59      B    C
ATOM   4199  CD2  TYR B 234      13.248  38.855  80.112  1.00 23.59      B    C
ATOM   4200  CE2  TYR B 234      12.770  39.998  79.476  1.00 23.59      B    C
ATOM   4201  CZ   TYR B 234      11.990  39.885  78.348  1.00 23.59      B    C
ATOM   4202  OH   TYR B 234      11.537  41.034  77.737  1.00 23.59      B    O
ATOM   4203  C    TYR B 234      12.096  36.286  82.351  1.00 32.46      B    C
ATOM   4204  O    TYR B 234      11.012  36.871  82.382  1.00 32.46      B    O
ATOM   4205  N    THR B 235      12.943  36.271  83.378  1.00 28.86      B    N
ATOM   4206  CA   THR B 235      12.649  36.950  84.639  1.00 28.86      B    C
ATOM   4207  CB   THR B 235      12.990  36.071  85.835  1.00 26.02      B    C
ATOM   4208  OG1  THR B 235      14.415  35.936  85.935  1.00 26.02      B    O
ATOM   4209  CG2  THR B 235      12.367  34.706  85.674  1.00 26.02      B    C
ATOM   4210  C    THR B 235      13.499  38.194  84.760  1.00 28.86      B    C
ATOM   4211  O    THR B 235      14.212  38.567  83.835  1.00 28.86      B    O
ATOM   4212  N    SER B 236      13.420  38.838  85.913  1.00 29.36      B    N
ATOM   4213  CA   SER B 236      14.213  40.025  86.148  1.00 29.36      B    C
ATOM   4214  CB   SER B 236      13.747  40.719  87.420  1.00 65.06      B    C
ATOM   4215  OG   SER B 236      12.472  41.299  87.192  1.00 65.06      B    O
```

FIG. 4-64

```
ATOM   4216  C    SER B 236     15.673  39.639  86.245  1.00 29.36      B  C
ATOM   4217  O    SER B 236     16.547  40.496  86.208  1.00 29.36      B  O
ATOM   4218  N    SER B 237     15.925  38.338  86.340  1.00 26.30      B  N
ATOM   4219  CA   SER B 237     17.277  37.810  86.429  1.00 26.30      B  C
ATOM   4220  CB   SER B 237     17.220  36.288  86.387  1.00 45.78      B  C
ATOM   4221  OG   SER B 237     18.520  35.744  86.450  1.00 45.78      B  O
ATOM   4222  C    SER B 237     18.095  38.334  85.257  1.00 26.30      B  C
ATOM   4223  O    SER B 237     19.322  38.407  85.304  1.00 26.30      B  O
ATOM   4224  N    ILE B 238     17.381  38.691  84.201  1.00 25.85      B  N
ATOM   4225  CA   ILE B 238     17.958  39.241  82.991  1.00 25.85      B  C
ATOM   4226  CB   ILE B 238     16.794  39.748  82.087  1.00 28.25      B  C
ATOM   4227  CG2  ILE B 238     16.949  41.226  81.753  1.00 28.25      B  C
ATOM   4228  CG1  ILE B 238     16.743  38.944  80.797  1.00 28.25      B  C
ATOM   4229  CD1  ILE B 238     16.549  37.489  81.002  1.00 28.25      B  C
ATOM   4230  C    ILE B 238     18.903  40.393  83.343  1.00 25.85      B  C
ATOM   4231  O    ILE B 238     20.009  40.480  82.828  1.00 25.85      B  O
ATOM   4232  N    ASP B 239     18.452  41.282  84.217  1.00 15.97      B  N
ATOM   4233  CA   ASP B 239     19.260  42.410  84.632  1.00 15.97      B  C
ATOM   4234  CB   ASP B 239     18.431  43.367  85.485  1.00 29.29      B  C
ATOM   4235  CG   ASP B 239     17.408  44.144  84.662  1.00 29.29      B  C
ATOM   4236  OD1  ASP B 239     17.674  44.411  83.461  1.00 29.29      B  O
ATOM   4237  OD2  ASP B 239     16.346  44.501  85.225  1.00 29.29      B  O
ATOM   4238  C    ASP B 239     20.490  41.959  85.402  1.00 15.97      B  C
ATOM   4239  O    ASP B 239     21.586  42.439  85.162  1.00 15.97      B  O
ATOM   4240  N    VAL B 240     20.314  41.023  86.321  1.00 14.56      B  N
ATOM   4241  CA   VAL B 240     21.430  40.552  87.106  1.00 14.56      B  C
ATOM   4242  CB   VAL B 240     20.998  39.391  88.021  1.00 17.75      B  C
ATOM   4243  CG1  VAL B 240     22.198  38.788  88.725  1.00 17.75      B  C
ATOM   4244  CG2  VAL B 240     20.015  39.897  89.062  1.00 17.75      B  C
ATOM   4245  C    VAL B 240     22.558  40.120  86.196  1.00 14.56      B  C
ATOM   4246  O    VAL B 240     23.702  40.467  86.443  1.00 14.56      B  O
ATOM   4247  N    TRP B 241     22.241  39.370  85.142  1.00 17.93      B  N
ATOM   4248  CA   TRP B 241     23.264  38.911  84.207  1.00 17.93      B  C
ATOM   4249  CB   TRP B 241     22.659  38.019  83.121  1.00 27.72      B  C
ATOM   4250  CG   TRP B 241     23.579  37.758  81.936  1.00 27.72      B  C
ATOM   4251  CD2  TRP B 241     24.390  36.597  81.695  1.00 27.72      B  C
ATOM   4252  CE2  TRP B 241     25.103  36.818  80.498  1.00 27.72      B  C
ATOM   4253  CE3  TRP B 241     24.575  35.375  82.373  1.00 27.72      B  C
ATOM   4254  CD1  TRP B 241     23.836  38.613  80.902  1.00 27.72      B  C
ATOM   4255  NE1  TRP B 241     24.749  38.062  80.039  1.00 27.72      B  N
ATOM   4256  CZ2  TRP B 241     26.002  35.890  79.965  1.00 27.72      B  C
ATOM   4257  CZ3  TRP B 241     25.471  34.443  81.840  1.00 27.72      B  C
ATOM   4258  CH2  TRP B 241     26.167  34.706  80.644  1.00 27.72      B  C
ATOM   4259  C    TRP B 241     23.938  40.102  83.580  1.00 17.93      B  C
ATOM   4260  O    TRP B 241     25.158  40.174  83.559  1.00 17.93      B  O
ATOM   4261  N    SER B 242     23.142  41.039  83.077  1.00 11.89      B  N
ATOM   4262  CA   SER B 242     23.682  42.245  82.457  1.00 11.89      B  C
ATOM   4263  CB   SER B 242     22.551  43.208  82.078  1.00 32.88      B  C
ATOM   4264  OG   SER B 242     21.591  42.599  81.233  1.00 32.88      B  O
ATOM   4265  C    SER B 242     24.608  42.938  83.447  1.00 11.89      B  C
ATOM   4266  O    SER B 242     25.646  43.475  83.082  1.00 11.89      B  O
ATOM   4267  N    ALA B 243     24.207  42.925  84.712  1.00 22.79      B  N
ATOM   4268  CA   ALA B 243     24.980  43.537  85.772  1.00 22.79      B  C
ATOM   4269  CB   ALA B 243     24.235  43.409  87.055  1.00 14.79      B  C
ATOM   4270  C    ALA B 243     26.322  42.828  85.861  1.00 22.79      B  C
ATOM   4271  O    ALA B 243     27.364  43.467  85.941  1.00 22.79      B  O
ATOM   4272  N    GLY B 244     26.296  41.502  85.825  1.00 30.07      B  N
ATOM   4273  CA   GLY B 244     27.529  40.743  85.895  1.00 30.07      B  C
ATOM   4274  C    GLY B 244     28.418  40.934  84.677  1.00 30.07      B  C
ATOM   4275  O    GLY B 244     29.607  40.653  84.728  1.00 30.07      B  O
ATOM   4276  N    CYS B 245     27.854  41.403  83.573  1.00 28.83      B  N
ATOM   4277  CA   CYS B 245     28.655  41.637  82.379  1.00 28.83      B  C
ATOM   4278  CB   CYS B 245     27.778  41.642  81.129  1.00 19.60      B  C
ATOM   4279  SG   CYS B 245     27.203  40.034  80.584  1.00 19.60      B  S
ATOM   4280  C    CYS B 245     29.354  42.987  82.517  1.00 28.83      B  C
ATOM   4281  O    CYS B 245     30.401  43.216  81.917  1.00 28.83      B  O
ATOM   4282  N    VAL B 246     28.766  43.892  83.298  1.00 29.43      B  N
```

FIG. 4-65

```
ATOM   4283  CA   VAL B 246      29.362  45.206  83.506  1.00 29.43       B  C
ATOM   4284  CB   VAL B 246      28.340  46.212  84.069  1.00 19.81       B  C
ATOM   4285  CG1  VAL B 246      29.016  47.526  84.399  1.00 19.81       B  C
ATOM   4286  CG2  VAL B 246      27.239  46.433  83.064  1.00 19.81       B  C
ATOM   4287  C    VAL B 246      30.524  45.079  84.478  1.00 29.43       B  C
ATOM   4288  O    VAL B 246      31.569  45.688  84.271  1.00 29.43       B  O
ATOM   4289  N    LEU B 247      30.342  44.281  85.531  1.00 20.35       B  N
ATOM   4290  CA   LEU B 247      31.386  44.073  86.528  1.00 20.35       B  C
ATOM   4291  CB   LEU B 247      30.882  43.167  87.652  1.00 14.58       B  C
ATOM   4292  CG   LEU B 247      31.931  42.538  88.572  1.00 14.58       B  C
ATOM   4293  CD1  LEU B 247      32.561  43.581  89.452  1.00 14.58       B  C
ATOM   4294  CD2  LEU B 247      31.286  41.470  89.394  1.00 14.58       B  C
ATOM   4295  C    LEU B 247      32.576  43.424  85.866  1.00 20.35       B  C
ATOM   4296  O    LEU B 247      33.708  43.833  86.076  1.00 20.35       B  O
ATOM   4297  N    ALA B 248      32.315  42.399  85.068  1.00 26.30       B  N
ATOM   4298  CA   ALA B 248      33.386  41.709  84.380  1.00 26.30       B  C
ATOM   4299  CB   ALA B 248      32.826  40.552  83.596  1.00 26.17       B  C
ATOM   4300  C    ALA B 248      34.096  42.680  83.450  1.00 26.30       B  C
ATOM   4301  O    ALA B 248      35.323  42.686  83.363  1.00 26.30       B  O
ATOM   4302  N    GLU B 249      33.326  43.510  82.759  1.00 21.36       B  N
ATOM   4303  CA   GLU B 249      33.914  44.475  81.845  1.00 21.36       B  C
ATOM   4304  CB   GLU B 249      32.815  45.221  81.080  1.00 22.74       B  C
ATOM   4305  CG   GLU B 249      33.327  46.086  79.935  1.00 22.74       B  C
ATOM   4306  CD   GLU B 249      32.226  46.545  78.999  1.00 22.74       B  C
ATOM   4307  OE1  GLU B 249      31.290  45.763  78.738  1.00 22.74       B  O
ATOM   4308  OE2  GLU B 249      32.307  47.683  78.503  1.00 22.74       B  O
ATOM   4309  C    GLU B 249      34.821  45.476  82.561  1.00 21.36       B  C
ATOM   4310  O    GLU B 249      35.886  45.813  82.061  1.00 21.36       B  O
ATOM   4311  N    LEU B 250      34.403  45.943  83.735  1.00 33.51       B  N
ATOM   4312  CA   LEU B 250      35.189  46.916  84.486  1.00 33.51       B  C
ATOM   4313  CB   LEU B 250      34.363  47.498  85.631  1.00 17.10       B  C
ATOM   4314  CG   LEU B 250      33.203  48.411  85.250  1.00 17.10       B  C
ATOM   4315  CD1  LEU B 250      32.393  48.759  86.486  1.00 17.10       B  C
ATOM   4316  CD2  LEU B 250      33.743  49.657  84.597  1.00 17.10       B  C
ATOM   4317  C    LEU B 250      36.459  46.307  85.046  1.00 33.51       B  C
ATOM   4318  O    LEU B 250      37.419  47.023  85.338  1.00 33.51       B  O
ATOM   4319  N    LEU B 251      36.459  44.988  85.214  1.00 32.68       B  N
ATOM   4320  CA   LEU B 251      37.638  44.311  85.725  1.00 32.68       B  C
ATOM   4321  CB   LEU B 251      37.272  42.959  86.360  1.00 23.35       B  C
ATOM   4322  CG   LEU B 251      36.310  42.957  87.564  1.00 23.35       B  C
ATOM   4323  CD1  LEU B 251      35.941  41.527  87.920  1.00 23.35       B  C
ATOM   4324  CD2  LEU B 251      36.931  43.658  88.767  1.00 23.35       B  C
ATOM   4325  C    LEU B 251      38.609  44.098  84.574  1.00 32.68       B  C
ATOM   4326  O    LEU B 251      39.784  44.416  84.690  1.00 32.68       B  O
ATOM   4327  N    LEU B 252      38.110  43.595  83.452  1.00 23.85       B  N
ATOM   4328  CA   LEU B 252      38.940  43.318  82.284  1.00 23.85       B  C
ATOM   4329  CB   LEU B 252      38.227  42.313  81.382  1.00 36.48       B  C
ATOM   4330  CG   LEU B 252      38.191  40.854  81.839  1.00 36.48       B  C
ATOM   4331  CD1  LEU B 252      37.074  40.111  81.115  1.00 36.48       B  C
ATOM   4332  CD2  LEU B 252      39.535  40.201  81.564  1.00 36.48       B  C
ATOM   4333  C    LEU B 252      39.380  44.515  81.442  1.00 23.85       B  C
ATOM   4334  O    LEU B 252      40.435  44.468  80.810  1.00 23.85       B  O
ATOM   4335  N    GLY B 253      38.583  45.578  81.413  1.00 19.24       B  N
ATOM   4336  CA   GLY B 253      38.939  46.733  80.603  1.00 19.24       B  C
ATOM   4337  C    GLY B 253      38.394  46.622  79.189  1.00 19.24       B  C
ATOM   4338  O    GLY B 253      38.808  47.346  78.284  1.00 19.24       B  O
ATOM   4339  N    GLN B 254      37.465  45.690  79.006  1.00 36.67       B  N
ATOM   4340  CA   GLN B 254      36.821  45.438  77.720  1.00 36.67       B  C
ATOM   4341  CB   GLN B 254      37.826  44.867  76.724  1.00 49.98       B  C
ATOM   4342  CG   GLN B 254      38.331  43.499  77.091  1.00 49.98       B  C
ATOM   4343  CD   GLN B 254      39.117  42.869  75.967  1.00 49.98       B  C
ATOM   4344  OE1  GLN B 254      39.275  41.650  75.908  1.00 49.98       B  O
ATOM   4345  NE2  GLN B 254      39.622  43.699  75.067  1.00 49.98       B  N
ATOM   4346  C    GLN B 254      35.676  44.448  77.952  1.00 36.67       B  C
ATOM   4347  O    GLN B 254      35.648  43.741  78.956  1.00 36.67       B  O
ATOM   4348  N    PRO B 255      34.720  44.378  77.019  1.00 27.71       B  N
ATOM   4349  CD   PRO B 255      34.641  45.102  75.746  1.00 14.96       B  C
```

FIG. 4-66

```
ATOM   4350  CA   PRO B 255      33.584  43.464  77.169  1.00 27.71      B  C
ATOM   4351  CB   PRO B 255      32.782  43.714  75.892  1.00 14.96      B  C
ATOM   4352  CG   PRO B 255      33.171  45.103  75.497  1.00 14.96      B  C
ATOM   4353  C    PRO B 255      33.993  41.999  77.318  1.00 27.71      B  C
ATOM   4354  O    PRO B 255      34.933  41.553  76.673  1.00 27.71      B  O
ATOM   4355  N    ILE B 256      33.287  41.248  78.154  1.00 35.36      B  N
ATOM   4356  CA   ILE B 256      33.615  39.838  78.345  1.00 35.36      B  C
ATOM   4357  CB   ILE B 256      33.237  39.316  79.757  1.00 31.23      B  C
ATOM   4358  CG2  ILE B 256      31.719  39.403  79.984  1.00 31.23      B  C
ATOM   4359  CG1  ILE B 256      33.694  37.858  79.894  1.00 31.23      B  C
ATOM   4360  CD1  ILE B 256      33.231  37.154  81.175  1.00 31.23      B  C
ATOM   4361  C    ILE B 256      32.947  38.908  77.339  1.00 35.36      B  C
ATOM   4362  O    ILE B 256      33.496  37.866  77.030  1.00 35.36      B  O
ATOM   4363  N    PHE B 257      31.757  39.252  76.855  1.00 30.96      B  N
ATOM   4364  CA   PHE B 257      31.056  38.400  75.886  1.00 30.96      B  C
ATOM   4365  CB   PHE B 257      29.784  37.824  76.503  1.00 18.54      B  C
ATOM   4366  CG   PHE B 257      30.029  36.944  77.673  1.00 18.54      B  C
ATOM   4367  CD1  PHE B 257      31.022  35.972  77.636  1.00 18.54      B  C
ATOM   4368  CD2  PHE B 257      29.285  37.098  78.833  1.00 18.54      B  C
ATOM   4369  CE1  PHE B 257      31.272  35.161  78.752  1.00 18.54      B  C
ATOM   4370  CE2  PHE B 257      29.520  36.302  79.943  1.00 18.54      B  C
ATOM   4371  CZ   PHE B 257      30.520  35.331  79.907  1.00 18.54      B  C
ATOM   4372  C    PHE B 257      30.675  39.126  74.581  1.00 30.96      B  C
ATOM   4373  O    PHE B 257      29.482  39.250  74.250  1.00 30.96      B  O
ATOM   4374  N    PRO B 258      31.679  39.606  73.819  1.00 29.82      B  N
ATOM   4375  CD   PRO B 258      33.133  39.501  74.045  1.00 20.52      B  C
ATOM   4376  CA   PRO B 258      31.422  40.314  72.566  1.00 29.82      B  C
ATOM   4377  CB   PRO B 258      32.745  41.001  72.290  1.00 20.52      B  C
ATOM   4378  CG   PRO B 258      33.708  39.964  72.713  1.00 20.52      B  C
ATOM   4379  C    PRO B 258      31.041  39.382  71.427  1.00 29.82      B  C
ATOM   4380  O    PRO B 258      31.069  38.157  71.564  1.00 29.82      B  O
ATOM   4381  N    GLY B 259      30.701  39.980  70.297  1.00 29.48      B  N
ATOM   4382  CA   GLY B 259      30.314  39.206  69.138  1.00 29.48      B  C
ATOM   4383  C    GLY B 259      29.259  39.941  68.336  1.00 29.48      B  C
ATOM   4384  O    GLY B 259      28.322  40.500  68.896  1.00 29.48      B  O
ATOM   4385  N    ASP B 260      29.395  39.956  67.022  1.00 28.45      B  N
ATOM   4386  CA   ASP B 260      28.403  40.642  66.213  1.00 28.45      B  C
ATOM   4387  CB   ASP B 260      28.960  40.947  64.817  1.00 53.75      B  C
ATOM   4388  CG   ASP B 260      30.035  42.037  64.837  1.00 53.75      B  C
ATOM   4389  OD1  ASP B 260      29.983  42.893  65.756  1.00 53.75      B  O
ATOM   4390  OD2  ASP B 260      30.909  42.039  63.926  1.00 53.75      B  O
ATOM   4391  C    ASP B 260      27.095  39.865  66.083  1.00 28.45      B  C
ATOM   4392  O    ASP B 260      26.079  40.424  65.673  1.00 28.45      B  O
ATOM   4393  N    SER B 261      27.117  38.576  66.414  1.00 25.64      B  N
ATOM   4394  CA   SER B 261      25.907  37.767  66.322  1.00 25.64      B  C
ATOM   4395  CB   SER B 261      25.971  36.814  65.128  1.00 18.81      B  C
ATOM   4396  OG   SER B 261      26.696  35.640  65.440  1.00 18.81      B  O
ATOM   4397  C    SER B 261      25.704  36.959  67.580  1.00 25.64      B  C
ATOM   4398  O    SER B 261      26.633  36.779  68.360  1.00 25.64      B  O
ATOM   4399  N    GLY B 262      24.478  36.477  67.773  1.00 27.61      B  N
ATOM   4400  CA   GLY B 262      24.178  35.676  68.941  1.00 27.61      B  C
ATOM   4401  C    GLY B 262      25.154  34.525  68.991  1.00 27.61      B  C
ATOM   4402  O    GLY B 262      25.727  34.217  70.041  1.00 27.61      B  O
ATOM   4403  N    VAL B 263      25.340  33.892  67.838  1.00 21.64      B  N
ATOM   4404  CA   VAL B 263      26.257  32.772  67.706  1.00 21.64      B  C
ATOM   4405  CB   VAL B 263      26.490  32.402  66.231  1.00 35.29      B  C
ATOM   4406  CG1  VAL B 263      27.649  31.418  66.118  1.00 35.29      B  C
ATOM   4407  CG2  VAL B 263      25.234  31.782  65.656  1.00 35.29      B  C
ATOM   4408  C    VAL B 263      27.607  33.114  68.306  1.00 21.64      B  C
ATOM   4409  O    VAL B 263      28.113  32.404  69.166  1.00 21.64      B  O
ATOM   4410  N    ASP B 264      28.194  34.204  67.836  1.00 35.19      B  N
ATOM   4411  CA   ASP B 264      29.497  34.627  68.333  1.00 35.19      B  C
ATOM   4412  CB   ASP B 264      29.948  35.884  67.589  1.00 37.53      B  C
ATOM   4413  CG   ASP B 264      30.257  35.612  66.144  1.00 37.53      B  C
ATOM   4414  OD1  ASP B 264      30.271  34.421  65.777  1.00 37.53      B  O
ATOM   4415  OD2  ASP B 264      30.489  36.578  65.385  1.00 37.53      B  O
ATOM   4416  C    ASP B 264      29.502  34.876  69.846  1.00 35.19      B  C
```

FIG. 4-67

```
ATOM   4417  O    ASP B 264      30.421  34.462  70.551  1.00 35.19           B    O
ATOM   4418  N    GLN B 265      28.477  35.552  70.340  1.00 26.25           B    N
ATOM   4419  CA   GLN B 265      28.384  35.831  71.757  1.00 26.25           B    C
ATOM   4420  CB   GLN B 265      27.134  36.643  72.051  1.00 36.18           B    C
ATOM   4421  CG   GLN B 265      26.959  37.862  71.176  1.00 36.18           B    C
ATOM   4422  CD   GLN B 265      25.700  38.610  71.505  1.00 36.18           B    C
ATOM   4423  OE1  GLN B 265      25.007  39.085  70.613  1.00 36.18           B    O
ATOM   4424  NE2  GLN B 265      25.385  38.716  72.799  1.00 36.18           B    N
ATOM   4425  C    GLN B 265      28.320  34.524  72.505  1.00 26.25           B    C
ATOM   4426  O    GLN B 265      28.939  34.380  73.550  1.00 26.25           B    O
ATOM   4427  N    LEU B 266      27.560  33.576  71.968  1.00 28.90           B    N
ATOM   4428  CA   LEU B 266      27.430  32.265  72.582  1.00 28.90           B    C
ATOM   4429  CB   LEU B 266      26.402  31.449  71.808  1.00 22.14           B    C
ATOM   4430  CG   LEU B 266      24.981  31.434  72.380  1.00 22.14           B    C
ATOM   4431  CD1  LEU B 266      24.590  32.808  72.880  1.00 22.14           B    C
ATOM   4432  CD2  LEU B 266      24.003  30.947  71.318  1.00 22.14           B    C
ATOM   4433  C    LEU B 266      28.770  31.528  72.617  1.00 28.90           B    C
ATOM   4434  O    LEU B 266      29.080  30.839  73.590  1.00 28.90           B    O
ATOM   4435  N    VAL B 267      29.578  31.664  71.571  1.00 36.65           B    N
ATOM   4436  CA   VAL B 267      30.861  30.976  71.583  1.00 36.65           B    C
ATOM   4437  CB   VAL B 267      31.597  30.985  70.178  1.00 33.45           B    C
ATOM   4438  CG1  VAL B 267      30.647  31.414  69.082  1.00 33.45           B    C
ATOM   4439  CG2  VAL B 267      32.845  31.871  70.203  1.00 33.45           B    C
ATOM   4440  C    VAL B 267      31.760  31.607  72.627  1.00 36.65           B    C
ATOM   4441  O    VAL B 267      32.619  30.939  73.190  1.00 36.65           B    O
ATOM   4442  N    GLU B 268      31.555  32.893  72.884  1.00 30.24           B    N
ATOM   4443  CA   GLU B 268      32.357  33.607  73.857  1.00 30.24           B    C
ATOM   4444  CB   GLU B 268      32.252  35.106  73.601  1.00 43.19           B    C
ATOM   4445  CG   GLU B 268      32.986  35.486  72.328  1.00 43.19           B    C
ATOM   4446  CD   GLU B 268      34.418  34.998  72.371  1.00 43.19           B    C
ATOM   4447  OE1  GLU B 268      34.990  34.732  71.285  1.00 43.19           B    O
ATOM   4448  OE2  GLU B 268      34.954  34.885  73.504  1.00 43.19           B    O
ATOM   4449  C    GLU B 268      31.941  33.257  75.265  1.00 30.24           B    C
ATOM   4450  O    GLU B 268      32.783  33.187  76.156  1.00 30.24           B    O
ATOM   4451  N    ILE B 269      30.647  33.021  75.457  1.00 43.79           B    N
ATOM   4452  CA   ILE B 269      30.123  32.651  76.766  1.00 43.79           B    C
ATOM   4453  CB   ILE B 269      28.582  32.701  76.794  1.00 24.38           B    C
ATOM   4454  CG2  ILE B 269      28.059  32.012  78.038  1.00 24.38           B    C
ATOM   4455  CG1  ILE B 269      28.114  34.154  76.725  1.00 24.38           B    C
ATOM   4456  CD1  ILE B 269      26.625  34.309  76.585  1.00 24.38           B    C
ATOM   4457  C    ILE B 269      30.576  31.236  77.094  1.00 43.79           B    C
ATOM   4458  O    ILE B 269      31.082  30.979  78.183  1.00 43.79           B    O
ATOM   4459  N    ILE B 270      30.404  30.326  76.140  1.00 32.45           B    N
ATOM   4460  CA   ILE B 270      30.792  28.936  76.323  1.00 32.45           B    C
ATOM   4461  CB   ILE B 270      30.422  28.098  75.079  1.00 27.53           B    C
ATOM   4462  CG2  ILE B 270      30.912  26.665  75.243  1.00 27.53           B    C
ATOM   4463  CG1  ILE B 270      28.905  28.124  74.878  1.00 27.53           B    C
ATOM   4464  CD1  ILE B 270      28.418  27.343  73.693  1.00 27.53           B    C
ATOM   4465  C    ILE B 270      32.282  28.833  76.575  1.00 32.45           B    C
ATOM   4466  O    ILE B 270      32.726  27.971  77.331  1.00 32.45           B    O
ATOM   4467  N    LYS B 271      33.058  29.711  75.948  1.00 35.52           B    N
ATOM   4468  CA   LYS B 271      34.501  29.677  76.154  1.00 35.52           B    C
ATOM   4469  CB   LYS B 271      35.207  30.772  75.348  1.00 46.41           B    C
ATOM   4470  CG   LYS B 271      35.502  30.399  73.904  1.00 46.41           B    C
ATOM   4471  CD   LYS B 271      36.294  31.492  73.182  1.00 46.41           B    C
ATOM   4472  CE   LYS B 271      36.113  31.386  71.664  1.00 46.41           B    C
ATOM   4473  NZ   LYS B 271      36.641  32.582  70.894  1.00 46.41           B    N
ATOM   4474  C    LYS B 271      34.836  29.826  77.635  1.00 35.52           B    C
ATOM   4475  O    LYS B 271      35.795  29.212  78.122  1.00 35.52           B    O
ATOM   4476  N    VAL B 272      34.045  30.612  78.366  1.00 38.83           B    N
ATOM   4477  CA   VAL B 272      34.333  30.788  79.783  1.00 38.83           B    C
ATOM   4478  CB   VAL B 272      34.400  32.310  80.166  1.00 20.73           B    C
ATOM   4479  CG1  VAL B 272      34.199  33.170  78.938  1.00 20.73           B    C
ATOM   4480  CG2  VAL B 272      33.389  32.643  81.253  1.00 20.73           B    C
ATOM   4481  C    VAL B 272      33.431  30.037  80.757  1.00 38.83           B    C
ATOM   4482  O    VAL B 272      33.908  29.619  81.805  1.00 38.83           B    O
ATOM   4483  N    LEU B 273      32.152  29.853  80.427  1.00 33.81           B    N
```

FIG. 4-68

| | | | | | | | | | | |
|---|---|---|---|---|---|---|---|---|---|---|
| ATOM | 4484 | CA | LEU | B | 273 | 31.221 | 29.135 | 81.312 | 1.00 33.81 | B C |
| ATOM | 4485 | CB | LEU | B | 273 | 29.821 | 29.739 | 81.259 | 1.00 23.99 | B C |
| ATOM | 4486 | CG | LEU | B | 273 | 29.511 | 31.133 | 81.778 | 1.00 23.99 | B C |
| ATOM | 4487 | CD1 | LEU | B | 273 | 28.015 | 31.315 | 81.666 | 1.00 23.99 | B C |
| ATOM | 4488 | CD2 | LEU | B | 273 | 29.959 | 31.301 | 83.225 | 1.00 23.99 | B C |
| ATOM | 4489 | C | LEU | B | 273 | 31.083 | 27.693 | 80.868 | 1.00 33.81 | B C |
| ATOM | 4490 | O | LEU | B | 273 | 30.228 | 26.962 | 81.364 | 1.00 33.81 | B O |
| ATOM | 4491 | N | GLY | B | 274 | 31.900 | 27.278 | 79.916 | 1.00 41.43 | B N |
| ATOM | 4492 | CA | GLY | B | 274 | 31.780 | 25.914 | 79.448 | 1.00 41.43 | B C |
| ATOM | 4493 | C | GLY | B | 274 | 30.527 | 25.713 | 78.611 | 1.00 41.43 | B C |
| ATOM | 4494 | O | GLY | B | 274 | 29.763 | 26.646 | 78.379 | 1.00 41.43 | B O |
| ATOM | 4495 | N | THR | B | 275 | 30.310 | 24.493 | 78.150 | 1.00 32.47 | B N |
| ATOM | 4496 | CA | THR | B | 275 | 29.153 | 24.216 | 77.331 | 1.00 32.47 | B C |
| ATOM | 4497 | CB | THR | B | 275 | 29.485 | 23.128 | 76.314 | 1.00 44.57 | B C |
| ATOM | 4498 | OG1 | THR | B | 275 | 30.903 | 23.117 | 76.108 | 1.00 44.57 | B O |
| ATOM | 4499 | CG2 | THR | B | 275 | 28.789 | 23.403 | 74.986 | 1.00 44.57 | B C |
| ATOM | 4500 | C | THR | B | 275 | 27.959 | 23.826 | 78.203 | 1.00 32.47 | B C |
| ATOM | 4501 | O | THR | B | 275 | 27.990 | 22.857 | 78.957 | 1.00 32.47 | B O |
| ATOM | 4502 | N | PRO | B | 276 | 26.877 | 24.588 | 78.098 | 1.00 66.38 | B N |
| ATOM | 4503 | CD | PRO | B | 276 | 26.539 | 25.537 | 77.022 | 1.00 42.61 | B C |
| ATOM | 4504 | CA | PRO | B | 276 | 25.700 | 24.279 | 78.908 | 1.00 66.38 | B C |
| ATOM | 4505 | CB | PRO | B | 276 | 24.622 | 25.209 | 78.345 | 1.00 42.61 | B C |
| ATOM | 4506 | CG | PRO | B | 276 | 25.017 | 25.363 | 76.918 | 1.00 42.61 | B C |
| ATOM | 4507 | C | PRO | B | 276 | 25.282 | 22.832 | 78.856 | 1.00 66.38 | B C |
| ATOM | 4508 | O | PRO | B | 276 | 25.439 | 22.133 | 77.847 | 1.00 66.38 | B O |
| ATOM | 4509 | N | THR | B | 277 | 24.722 | 22.409 | 79.969 | 1.00 48.21 | B N |
| ATOM | 4510 | CA | THR | B | 277 | 24.238 | 21.070 | 80.113 | 1.00 48.21 | B C |
| ATOM | 4511 | CB | THR | B | 277 | 24.134 | 20.733 | 81.563 | 1.00 43.89 | B C |
| ATOM | 4512 | OG1 | THR | B | 277 | 22.881 | 21.204 | 82.063 | 1.00 43.89 | B O |
| ATOM | 4513 | CG2 | THR | B | 277 | 25.262 | 21.442 | 82.323 | 0.00 43.89 | B C |
| ATOM | 4514 | C | THR | B | 277 | 22.847 | 21.161 | 79.538 | 1.00 48.21 | B C |
| ATOM | 4515 | O | THR | B | 277 | 22.262 | 22.253 | 79.474 | 1.00 48.21 | B O |
| ATOM | 4516 | N | ALA | B | 278 | 22.312 | 20.014 | 79.150 | 1.00 55.97 | B N |
| ATOM | 4517 | CA | ALA | B | 278 | 20.981 | 19.951 | 78.574 | 1.00 55.97 | B C |
| ATOM | 4518 | CB | ALA | B | 278 | 20.574 | 18.504 | 78.384 | 1.00 43.89 | B C |
| ATOM | 4519 | C | ALA | B | 278 | 19.995 | 20.654 | 79.481 | 1.00 55.97 | B C |
| ATOM | 4520 | O | ALA | B | 278 | 19.233 | 21.533 | 79.043 | 1.00 55.97 | B O |
| ATOM | 4521 | N | GLU | B | 279 | 20.026 | 20.293 | 80.753 | 0.00 61.38 | B N |
| ATOM | 4522 | CA | GLU | B | 279 | 19.099 | 20.909 | 81.680 | 1.00 61.38 | B C |
| ATOM | 4523 | CB | GLU | B | 279 | 19.356 | 20.419 | 83.109 | 1.00 77.90 | B C |
| ATOM | 4524 | CG | GLU | B | 279 | 20.294 | 21.303 | 83.906 | 1.00 77.90 | B C |
| ATOM | 4525 | CD | GLU | B | 279 | 21.306 | 20.494 | 84.717 | 1.00 77.90 | B C |
| ATOM | 4526 | OE1 | GLU | B | 279 | 20.901 | 19.845 | 85.726 | 1.00 77.90 | B O |
| ATOM | 4527 | OE2 | GLU | B | 279 | 22.508 | 20.510 | 84.330 | 1.00 77.90 | B O |
| ATOM | 4528 | C | GLU | B | 279 | 19.181 | 22.445 | 81.623 | 1.00 61.38 | B C |
| ATOM | 4529 | O | GLU | B | 279 | 18.151 | 23.133 | 81.487 | 1.00 61.38 | B O |
| ATOM | 4530 | N | GLN | B | 280 | 20.403 | 22.972 | 81.713 | 1.00 47.11 | B N |
| ATOM | 4531 | CA | GLN | B | 280 | 20.618 | 24.409 | 81.707 | 1.00 47.11 | B C |
| ATOM | 4532 | CB | GLN | B | 280 | 22.109 | 24.697 | 81.650 | 1.00 48.45 | B C |
| ATOM | 4533 | CG | GLN | B | 280 | 22.822 | 24.509 | 82.973 | 1.00 48.45 | B C |
| ATOM | 4534 | CD | GLN | B | 280 | 24.331 | 24.554 | 82.796 | 1.00 48.45 | B C |
| ATOM | 4535 | OE1 | GLN | B | 280 | 25.095 | 24.612 | 83.772 | 1.00 48.45 | B O |
| ATOM | 4536 | NE2 | GLN | B | 280 | 24.775 | 24.523 | 81.532 | 1.00 48.45 | B N |
| ATOM | 4537 | C | GLN | B | 280 | 19.905 | 25.094 | 80.558 | 1.00 47.11 | B C |
| ATOM | 4538 | O | GLN | B | 280 | 18.986 | 25.886 | 80.766 | 0.00 47.11 | B O |
| ATOM | 4539 | N | ILE | B | 281 | 20.313 | 24.760 | 79.341 | 1.00 54.00 | B N |
| ATOM | 4540 | CA | ILE | B | 281 | 19.711 | 25.354 | 78.157 | 1.00 54.00 | B C |
| ATOM | 4541 | CB | ILE | B | 281 | 20.303 | 24.747 | 76.871 | 0.00 31.68 | B C |
| ATOM | 4542 | CG2 | ILE | B | 281 | 21.555 | 23.967 | 77.178 | 1.00 31.68 | B C |
| ATOM | 4543 | CG1 | ILE | B | 281 | 19.305 | 23.789 | 76.239 | 1.00 31.68 | B C |
| ATOM | 4544 | CD1 | ILE | B | 281 | 19.760 | 23.279 | 74.883 | 1.00 31.68 | B C |
| ATOM | 4545 | C | ILE | B | 281 | 18.184 | 25.186 | 78.163 | 1.00 54.00 | B C |
| ATOM | 4546 | O | ILE | B | 281 | 17.468 | 25.969 | 77.525 | 1.00 54.00 | B O |
| ATOM | 4547 | N | ALA | B | 282 | 17.687 | 24.172 | 78.876 | 1.00 38.46 | B N |
| ATOM | 4548 | CA | ALA | B | 282 | 16.242 | 23.956 | 78.963 | 1.00 38.46 | B C |
| ATOM | 4549 | CB | ALA | B | 282 | 15.953 | 22.567 | 79.448 | 1.00 58.43 | B C |
| ATOM | 4550 | C | ALA | B | 282 | 15.669 | 24.965 | 79.952 | 1.00 38.46 | B C |

FIG. 4-69

```
ATOM   4551  O    ALA B 282      14.463  25.041  80.177  1.00 38.46       B  O
ATOM   4552  N    GLU B 283      16.560  25.740  80.549  1.00 60.70       B  N
ATOM   4553  CA   GLU B 283      16.168  26.747  81.510  1.00 60.70       B  C
ATOM   4554  CB   GLU B 283      17.058  26.699  82.708  1.00 75.14       B  C
ATOM   4555  CG   GLU B 283      16.489  25.802  83.710  1.00 75.14       B  C
ATOM   4556  CD   GLU B 283      17.512  24.820  84.253  1.00 75.14       B  C
ATOM   4557  OE1  GLU B 283      17.283  24.272  85.366  1.00 75.14       B  O
ATOM   4558  OE2  GLU B 283      18.546  24.586  83.572  1.00 75.14       B  O
ATOM   4559  C    GLU B 283      16.246  28.122  80.953  1.00 60.70       B  C
ATOM   4560  O    GLU B 283      15.736  29.061  81.559  1.00 60.70       B  O
ATOM   4561  N    MET B 284      16.916  28.233  79.812  1.00 46.66       B  N
ATOM   4562  CA   MET B 284      17.080  29.499  79.134  1.00 46.66       B  C
ATOM   4563  CB   MET B 284      18.509  29.581  78.631  0.00 51.84       B  C
ATOM   4564  CG   MET B 284      19.480  29.465  79.775  1.00 51.84       B  C
ATOM   4565  SD   MET B 284      21.001  28.637  79.214  1.00 51.84       B  S
ATOM   4566  CE   MET B 284      21.753  29.973  78.493  1.00 51.84       B  C
ATOM   4567  C    MET B 284      16.076  29.705  77.993  1.00 46.66       B  C
ATOM   4568  O    MET B 284      15.461  28.758  77.483  1.00 46.66       B  O
ATOM   4569  N    ALA B 293      25.450  23.481  69.172  1.00 55.70       B  N
ATOM   4570  CA   ALA B 293      26.651  22.854  68.621  1.00 55.70       B  C
ATOM   4571  CB   ALA B 293      27.248  23.768  67.539  1.00 67.37       B  C
ATOM   4572  C    ALA B 293      27.727  22.504  69.679  1.00 55.70       B  C
ATOM   4573  O    ALA B 293      27.412  21.987  70.756  1.00 55.70       B  O
ATOM   4574  N    ALA B 294      28.984  22.802  69.322  1.00 61.42       B  N
ATOM   4575  CA   ALA B 294      30.218  22.603  70.109  1.00 61.42       B  C
ATOM   4576  CB   ALA B 294      30.927  23.940  70.241  1.00 23.63       B  C
ATOM   4577  C    ALA B 294      30.153  21.923  71.489  1.00 61.42       B  C
ATOM   4578  O    ALA B 294      29.105  21.410  71.900  1.00 61.42       B  O
ATOM   4579  N    ALA B 296      31.288  21.939  72.203  1.00 49.92       B  N
ATOM   4580  CA   ALA B 296      31.384  21.309  73.533  1.00 49.92       B  C
ATOM   4581  CB   ALA B 296      31.238  19.760  73.385  1.00 14.54       B  C
ATOM   4582  C    ALA B 296      32.647  21.629  74.371  1.00 49.92       B  C
ATOM   4583  O    ALA B 296      33.342  20.706  74.798  1.00 49.92       B  O
ATOM   4584  N    ALA B 297      32.915  22.914  74.630  1.00 64.10       B  N
ATOM   4585  CA   ALA B 297      34.096  23.362  75.407  1.00 64.10       B  C
ATOM   4586  CB   ALA B 297      34.338  24.859  75.159  1.00 17.11       B  C
ATOM   4587  C    ALA B 297      34.049  23.087  76.929  1.00 64.10       B  C
ATOM   4588  O    ALA B 297      33.269  22.251  77.370  1.00 64.10       B  O
ATOM   4589  N    ALA B 298      34.901  23.780  77.705  1.00 63.90       B  N
ATOM   4590  CA   ALA B 298      34.997  23.661  79.182  1.00 63.90       B  C
ATOM   4591  CB   ALA B 298      36.024  22.597  79.564  1.00 57.47       B  C
ATOM   4592  C    ALA B 298      35.386  25.046  79.771  1.00 63.90       B  C
ATOM   4593  O    ALA B 298      35.829  25.906  79.008  1.00 63.90       B  O
ATOM   4594  N    ALA B 299      35.273  25.258  81.093  1.00 41.08       B  N
ATOM   4595  CA   ALA B 299      35.492  26.594  81.726  1.00 41.08       B  C
ATOM   4596  CB   ALA B 299      34.662  26.625  82.976  1.00 53.01       B  C
ATOM   4597  C    ALA B 299      36.856  27.314  81.993  1.00 41.08       B  C
ATOM   4598  O    ALA B 299      37.813  27.099  81.258  1.00 41.08       B  O
ATOM   4599  N    ALA B 300      36.911  28.216  83.003  1.00 44.10       B  N
ATOM   4600  CA   ALA B 300      38.147  28.958  83.333  1.00 44.10       B  C
ATOM   4601  CB   ALA B 300      38.749  29.483  82.019  1.00 27.81       B  C
ATOM   4602  C    ALA B 300      38.237  30.098  84.420  1.00 44.10       B  C
ATOM   4603  O    ALA B 300      39.339  30.486  84.812  1.00 44.10       B  O
ATOM   4604  N    TRP B 301      37.107  30.633  84.900  1.00 60.18       B  N
ATOM   4605  CA   TRP B 301      37.072  31.808  85.838  1.00 60.18       B  C
ATOM   4606  CB   TRP B 301      36.069  31.604  86.980  1.00 33.08       B  C
ATOM   4607  CG   TRP B 301      34.627  31.926  86.573  1.00 33.08       B  C
ATOM   4608  CD2  TRP B 301      34.179  33.044  85.788  1.00 33.08       B  C
ATOM   4609  CE2  TRP B 301      32.804  32.846  85.515  1.00 33.08       B  C
ATOM   4610  CE3  TRP B 301      34.810  34.186  85.274  1.00 33.08       B  C
ATOM   4611  CD1  TRP B 301      33.520  31.131  86.763  1.00 33.08       B  C
ATOM   4612  NE1  TRP B 301      32.426  31.676  86.126  1.00 33.08       B  N
ATOM   4613  CZ2  TRP B 301      32.051  33.747  84.755  1.00 33.08       B  C
ATOM   4614  CZ3  TRP B 301      34.062  35.082  84.516  1.00 33.08       B  C
ATOM   4615  CH2  TRP B 301      32.697  34.853  84.261  1.00 33.08       B  C
ATOM   4616  C    TRP B 301      38.353  32.460  86.415  1.00 60.18       B  C
ATOM   4617  O    TRP B 301      38.796  33.503  85.914  1.00 60.18       B  O
```

FIG. 4-70

| ATOM | 4618 | N | THR | B | 302 | 38.928 | 31.906 | 87.473 | 1.00 | 44.13 | B | N |
|------|------|---|-----|---|-----|--------|--------|--------|------|-------|---|---|
| ATOM | 4619 | CA | THR | B | 302 | 40.134 | 32.508 | 88.068 | 1.00 | 44.13 | B | C |
| ATOM | 4620 | CB | THR | B | 302 | 40.924 | 31.497 | 88.900 | 1.00 | 55.62 | B | C |
| ATOM | 4621 | OG1 | THR | B | 302 | 40.028 | 30.696 | 89.679 | 1.00 | 55.62 | B | O |
| ATOM | 4622 | CG2 | THR | B | 302 | 41.892 | 32.233 | 89.823 | 1.00 | 55.62 | B | C |
| ATOM | 4623 | C | THR | B | 302 | 41.135 | 33.089 | 87.043 | 1.00 | 44.13 | B | C |
| ATOM | 4624 | O | THR | B | 302 | 41.738 | 34.163 | 87.255 | 1.00 | 44.13 | B | O |
| ATOM | 4625 | N | LYS | B | 303 | 41.324 | 32.359 | 85.943 | 1.00 | 57.98 | B | N |
| ATOM | 4626 | CA | LYS | B | 303 | 42.254 | 32.783 | 84.906 | 1.00 | 57.98 | B | C |
| ATOM | 4627 | CB | LYS | B | 303 | 43.093 | 31.587 | 84.422 | 1.00 | 68.26 | B | C |
| ATOM | 4628 | CG | LYS | B | 303 | 43.904 | 30.933 | 85.556 | 1.00 | 68.26 | B | C |
| ATOM | 4629 | CD | LYS | B | 303 | 45.020 | 30.044 | 85.017 | 1.00 | 68.26 | B | C |
| ATOM | 4630 | CE | LYS | B | 303 | 46.111 | 30.873 | 84.310 | 1.00 | 68.26 | B | C |
| ATOM | 4631 | NZ | LYS | B | 303 | 47.109 | 30.026 | 83.568 | 1.00 | 68.26 | B | N |
| ATOM | 4632 | C | LYS | B | 303 | 41.615 | 33.508 | 83.723 | 1.00 | 57.98 | B | C |
| ATOM | 4633 | O | LYS | B | 303 | 42.123 | 33.449 | 82.614 | 1.00 | 57.98 | B | O |
| ATOM | 4634 | N | VAL | B | 304 | 40.514 | 34.212 | 83.979 | 1.00 | 41.30 | B | N |
| ATOM | 4635 | CA | VAL | B | 304 | 39.813 | 34.994 | 82.962 | 1.00 | 41.30 | B | C |
| ATOM | 4636 | CB | VAL | B | 304 | 38.281 | 34.932 | 83.172 | 1.00 | 19.93 | B | C |
| ATOM | 4637 | CG1 | VAL | B | 304 | 37.596 | 35.955 | 82.313 | 1.00 | 19.93 | B | C |
| ATOM | 4638 | CG2 | VAL | B | 304 | 37.760 | 33.548 | 82.870 | 1.00 | 19.93 | B | C |
| ATOM | 4639 | C | VAL | B | 304 | 40.258 | 36.447 | 83.131 | 1.00 | 41.30 | B | C |
| ATOM | 4640 | O | VAL | B | 304 | 40.326 | 37.206 | 82.160 | 1.00 | 41.30 | B | O |
| ATOM | 4641 | N | PHE | B | 305 | 40.564 | 36.819 | 84.376 | 1.00 | 38.20 | B | N |
| ATOM | 4642 | CA | PHE | B | 305 | 40.988 | 38.176 | 84.709 | 1.00 | 38.20 | B | C |
| ATOM | 4643 | CB | PHE | B | 305 | 40.227 | 38.642 | 85.944 | 1.00 | 32.76 | B | C |
| ATOM | 4644 | CG | PHE | B | 305 | 38.738 | 38.464 | 85.828 | 1.00 | 32.76 | B | C |
| ATOM | 4645 | CD1 | PHE | B | 305 | 37.954 | 39.415 | 85.186 | 1.00 | 32.76 | B | C |
| ATOM | 4646 | CD2 | PHE | B | 305 | 38.120 | 37.320 | 86.321 | 1.00 | 32.76 | B | C |
| ATOM | 4647 | CE1 | PHE | B | 305 | 36.580 | 39.228 | 85.033 | 1.00 | 32.76 | B | C |
| ATOM | 4648 | CE2 | PHE | B | 305 | 36.741 | 37.131 | 86.170 | 1.00 | 32.76 | B | C |
| ATOM | 4649 | CZ | PHE | B | 305 | 35.977 | 38.090 | 85.524 | 1.00 | 32.76 | B | C |
| ATOM | 4650 | C | PHE | B | 305 | 42.483 | 38.302 | 84.941 | 1.00 | 38.20 | B | C |
| ATOM | 4651 | O | PHE | B | 305 | 43.209 | 37.309 | 84.885 | 1.00 | 38.20 | B | O |
| ATOM | 4652 | N | ARG | B | 306 | 42.942 | 39.531 | 85.178 | 1.00 | 34.34 | B | N |
| ATOM | 4653 | CA | ARG | B | 306 | 44.359 | 39.783 | 85.430 | 1.00 | 34.34 | B | C |
| ATOM | 4654 | CB | ARG | B | 306 | 44.606 | 41.269 | 85.676 | 1.00 | 79.12 | B | C |
| ATOM | 4655 | CG | ARG | B | 306 | 44.206 | 42.139 | 84.510 | 1.00 | 79.12 | B | C |
| ATOM | 4656 | CD | ARG | B | 306 | 43.024 | 43.086 | 84.843 | 1.00 | 79.12 | B | C |
| ATOM | 4657 | NE | ARG | B | 306 | 43.391 | 44.497 | 84.654 | 1.00 | 79.12 | B | N |
| ATOM | 4658 | CZ | ARG | B | 306 | 44.393 | 45.103 | 85.300 | 1.00 | 79.12 | B | C |
| ATOM | 4659 | NH1 | ARG | B | 306 | 45.120 | 44.421 | 86.176 | 1.00 | 79.12 | B | N |
| ATOM | 4660 | NH2 | ARG | B | 306 | 44.682 | 46.387 | 85.070 | 1.00 | 79.12 | B | N |
| ATOM | 4661 | C | ARG | B | 306 | 44.799 | 38.978 | 86.648 | 1.00 | 34.34 | B | C |
| ATOM | 4662 | O | ARG | B | 306 | 43.968 | 38.516 | 87.437 | 1.00 | 34.34 | B | O |
| ATOM | 4663 | N | PRO | B | 307 | 46.114 | 38.793 | 86.820 | 1.00 | 55.56 | B | N |
| ATOM | 4664 | CD | PRO | B | 307 | 47.231 | 39.109 | 85.907 | 1.00 | 80.55 | B | C |
| ATOM | 4665 | CA | PRO | B | 307 | 46.584 | 38.020 | 87.974 | 1.00 | 55.56 | B | C |
| ATOM | 4666 | CB | PRO | B | 307 | 48.094 | 37.947 | 87.758 | 1.00 | 80.55 | B | C |
| ATOM | 4667 | CG | PRO | B | 307 | 48.229 | 38.011 | 86.239 | 1.00 | 80.55 | B | C |
| ATOM | 4668 | C | PRO | B | 307 | 46.229 | 38.661 | 89.310 | 1.00 | 55.56 | B | C |
| ATOM | 4669 | O | PRO | B | 307 | 45.662 | 38.020 | 90.192 | 1.00 | 55.56 | B | O |
| ATOM | 4670 | N | ALA | B | 308 | 46.565 | 39.932 | 89.461 | 1.00 | 43.60 | B | N |
| ATOM | 4671 | CA | ALA | B | 308 | 46.278 | 40.628 | 90.710 | 1.00 | 43.60 | B | C |
| ATOM | 4672 | CB | ALA | B | 308 | 46.705 | 42.093 | 90.587 | 1.00 | 69.61 | B | C |
| ATOM | 4673 | C | ALA | B | 308 | 44.810 | 40.544 | 91.174 | 1.00 | 43.60 | B | C |
| ATOM | 4674 | O | ALA | B | 308 | 44.536 | 40.431 | 92.369 | 1.00 | 43.60 | B | O |
| ATOM | 4675 | N | THR | B | 309 | 43.883 | 40.610 | 90.218 | 1.00 | 38.20 | B | N |
| ATOM | 4676 | CA | THR | B | 309 | 42.439 | 40.583 | 90.472 | 1.00 | 38.20 | B | C |
| ATOM | 4677 | CB | THR | B | 309 | 41.675 | 39.937 | 89.296 | 1.00 | 29.06 | B | C |
| ATOM | 4678 | OG1 | THR | B | 309 | 42.058 | 40.567 | 88.067 | 1.00 | 29.06 | B | O |
| ATOM | 4679 | CG2 | THR | B | 309 | 40.176 | 40.109 | 89.495 | 1.00 | 29.06 | B | C |
| ATOM | 4680 | C | THR | B | 309 | 41.996 | 39.880 | 91.741 | 1.00 | 38.20 | B | C |
| ATOM | 4681 | O | THR | B | 309 | 42.288 | 38.713 | 91.939 | 1.00 | 38.20 | B | O |
| ATOM | 4682 | N | PRO | B | 310 | 41.265 | 40.591 | 92.612 | 1.00 | 45.68 | B | N |
| ATOM | 4683 | CD | PRO | B | 310 | 40.902 | 42.011 | 92.472 | 1.00 | 19.85 | B | C |
| ATOM | 4684 | CA | PRO | B | 310 | 40.760 | 40.058 | 93.880 | 1.00 | 45.68 | B | C |

FIG. 4-71

```
ATOM   4685  CB   PRO B 310      39.951  41.219  94.449  1.00 19.85       B    C
ATOM   4686  CG   PRO B 310      40.630  42.408  93.906  1.00 19.85       B    C
ATOM   4687  C    PRO B 310      39.885  38.843  93.634  1.00 45.68       B    C
ATOM   4688  O    PRO B 310      39.087  38.816  92.693  1.00 45.68       B    O
ATOM   4689  N    PRO B 311      40.022  37.815  94.480  1.00 35.96       B    N
ATOM   4690  CD   PRO B 311      40.887  37.672  95.661  1.00 34.46       B    C
ATOM   4691  CA   PRO B 311      39.200  36.621  94.292  1.00 35.96       B    C
ATOM   4692  CB   PRO B 311      39.761  35.656  95.332  1.00 34.46       B    C
ATOM   4693  CG   PRO B 311      40.196  36.568  96.420  1.00 34.46       B    C
ATOM   4694  C    PRO B 311      37.716  36.933  94.485  1.00 35.96       B    C
ATOM   4695  O    PRO B 311      36.884  36.490  93.694  1.00 35.96       B    O
ATOM   4696  N    GLU B 312      37.379  37.711  95.511  1.00 40.71       B    N
ATOM   4697  CA   GLU B 312      35.973  38.031  95.737  1.00 40.71       B    C
ATOM   4698  CB   GLU B 312      35.766  38.797  97.059  1.00 71.15       B    C
ATOM   4699  CG   GLU B 312      36.748  39.934  97.313  1.00 71.15       B    C
ATOM   4700  CD   GLU B 312      38.112  39.427  97.779  1.00 71.15       B    C
ATOM   4701  OE1  GLU B 312      39.118  40.164  97.603  1.00 71.15       B    O
ATOM   4702  OE2  GLU B 312      38.163  38.293  98.325  1.00 71.15       B    O
ATOM   4703  C    GLU B 312      35.276  38.752  94.561  1.00 40.71       B    C
ATOM   4704  O    GLU B 312      34.060  38.625  94.383  1.00 40.71       B    O
ATOM   4705  N    ALA B 313      36.020  39.497  93.750  1.00 32.75       B    N
ATOM   4706  CA   ALA B 313      35.402  40.158  92.601  1.00 32.75       B    C
ATOM   4707  CB   ALA B 313      36.348  41.162  92.017  1.00 34.59       B    C
ATOM   4708  C    ALA B 313      35.114  39.059  91.578  1.00 32.75       B    C
ATOM   4709  O    ALA B 313      34.068  39.034  90.917  1.00 32.75       B    O
ATOM   4710  N    ILE B 314      36.068  38.148  91.448  1.00 29.23       B    N
ATOM   4711  CA   ILE B 314      35.920  37.028  90.529  1.00 29.23       B    C
ATOM   4712  CB   ILE B 314      37.208  36.166  90.479  1.00 29.78       B    C
ATOM   4713  CG2  ILE B 314      36.928  34.830  89.836  1.00 29.78       B    C
ATOM   4714  CG1  ILE B 314      38.310  36.908  89.727  1.00 29.78       B    C
ATOM   4715  CD1  ILE B 314      39.666  36.224  89.801  1.00 29.78       B    C
ATOM   4716  C    ILE B 314      34.783  36.151  91.036  1.00 29.23       B    C
ATOM   4717  O    ILE B 314      33.917  35.726  90.270  1.00 29.23       B    O
ATOM   4718  N    ALA B 315      34.806  35.869  92.335  1.00 31.73       B    N
ATOM   4719  CA   ALA B 315      33.783  35.044  92.963  1.00 31.73       B    C
ATOM   4720  CB   ALA B 315      34.001  35.021  94.464  1.00 18.45       B    C
ATOM   4721  C    ALA B 315      32.374  35.556  92.639  1.00 31.73       B    C
ATOM   4722  O    ALA B 315      31.501  34.796  92.210  1.00 31.73       B    O
ATOM   4723  N    LEU B 316      32.156  36.851  92.854  1.00 32.87       B    N
ATOM   4724  CA   LEU B 316      30.867  37.465  92.567  1.00 32.87       B    C
ATOM   4725  CB   LEU B 316      30.891  38.927  92.983  1.00 24.09       B    C
ATOM   4726  CG   LEU B 316      29.672  39.721  92.550  1.00 24.09       B    C
ATOM   4727  CD1  LEU B 316      28.427  39.072  93.111  1.00 24.09       B    C
ATOM   4728  CD2  LEU B 316      29.825  41.151  93.016  1.00 24.09       B    C
ATOM   4729  C    LEU B 316      30.471  37.345  91.093  1.00 32.87       B    C
ATOM   4730  O    LEU B 316      29.298  37.209  90.786  1.00 32.87       B    O
ATOM   4731  N    CYS B 317      31.432  37.407  90.178  1.00 45.55       B    N
ATOM   4732  CA   CYS B 317      31.105  37.252  88.766  1.00 45.55       B    C
ATOM   4733  CB   CYS B 317      32.353  37.334  87.897  1.00 56.00       B    C
ATOM   4734  SG   CYS B 317      32.713  38.983  87.292  1.00 56.00       B    S
ATOM   4735  C    CYS B 317      30.461  35.908  88.522  1.00 45.55       B    C
ATOM   4736  O    CYS B 317      29.343  35.832  88.012  1.00 45.55       B    O
ATOM   4737  N    SER B 318      31.178  34.850  88.889  1.00 30.83       B    N
ATOM   4738  CA   SER B 318      30.694  33.495  88.689  1.00 30.83       B    C
ATOM   4739  CB   SER B 318      31.700  32.504  89.262  1.00 42.43       B    C
ATOM   4740  OG   SER B 318      32.078  32.899  90.565  1.00 42.43       B    O
ATOM   4741  C    SER B 318      29.322  33.250  89.306  1.00 30.83       B    C
ATOM   4742  O    SER B 318      28.679  32.246  89.008  1.00 30.83       B    O
ATOM   4743  N    ARG B 319      28.869  34.152  90.169  1.00 34.23       B    N
ATOM   4744  CA   ARG B 319      27.566  33.968  90.787  1.00 34.23       B    C
ATOM   4745  CB   ARG B 319      27.616  34.304  92.272  1.00 34.07       B    C
ATOM   4746  CG   ARG B 319      28.417  33.313  93.107  1.00 34.07       B    C
ATOM   4747  CD   ARG B 319      28.096  31.871  92.760  1.00 34.07       B    C
ATOM   4748  NE   ARG B 319      26.667  31.660  92.536  1.00 34.07       B    N
ATOM   4749  CZ   ARG B 319      25.752  31.567  93.496  1.00 34.07       B    C
ATOM   4750  NH1  ARG B 319      26.107  31.666  94.776  1.00 34.07       B    N
ATOM   4751  NH2  ARG B 319      24.475  31.367  93.174  1.00 34.07       B    N
```

FIG. 4-72

```
ATOM   4752  C    ARG B 319      26.527  34.821  90.095  1.00 34.23           B  C
ATOM   4753  O    ARG B 319      25.328  34.742  90.389  1.00 34.23           B  O
ATOM   4754  N    LEU B 320      27.006  35.639  89.166  1.00 42.79           B  N
ATOM   4755  CA   LEU B 320      26.136  36.504  88.377  1.00 42.79           B  C
ATOM   4756  CB   LEU B 320      26.745  37.908  88.270  1.00 19.31           B  C
ATOM   4757  CG   LEU B 320      26.864  38.624  89.617  1.00 19.31           B  C
ATOM   4758  CD1  LEU B 320      27.617  39.926  89.487  1.00 19.31           B  C
ATOM   4759  CD2  LEU B 320      25.465  38.856  90.153  1.00 19.31           B  C
ATOM   4760  C    LEU B 320      25.957  35.892  86.984  1.00 42.79           B  C
ATOM   4761  O    LEU B 320      24.843  35.760  86.479  1.00 42.79           B  O
ATOM   4762  N    LEU B 321      27.064  35.493  86.375  1.00 26.99           B  N
ATOM   4763  CA   LEU B 321      27.011  34.894  85.055  1.00 26.99           B  C
ATOM   4764  CB   LEU B 321      28.305  35.230  84.301  1.00 26.31           B  C
ATOM   4765  CG   LEU B 321      28.601  36.737  84.204  1.00 26.31           B  C
ATOM   4766  CD1  LEU B 321      29.801  36.992  83.321  1.00 26.31           B  C
ATOM   4767  CD2  LEU B 321      27.401  37.463  83.663  1.00 26.31           B  C
ATOM   4768  C    LEU B 321      26.769  33.378  85.096  1.00 26.99           B  C
ATOM   4769  O    LEU B 321      27.667  32.581  84.835  1.00 26.99           B  O
ATOM   4770  N    GLU B 322      25.532  33.004  85.411  1.00 38.35           B  N
ATOM   4771  CA   GLU B 322      25.116  31.610  85.500  1.00 38.35           B  C
ATOM   4772  CB   GLU B 322      24.459  31.363  86.854  1.00 46.96           B  C
ATOM   4773  CG   GLU B 322      24.840  30.050  87.492  1.00 46.96           B  C
ATOM   4774  CD   GLU B 322      26.074  30.167  88.355  1.00 46.96           B  C
ATOM   4775  OE1  GLU B 322      25.968  30.832  89.407  1.00 46.96           B  O
ATOM   4776  OE2  GLU B 322      27.134  29.609  87.989  1.00 46.96           B  O
ATOM   4777  C    GLU B 322      24.101  31.318  84.403  1.00 38.35           B  C
ATOM   4778  O    GLU B 322      23.195  32.113  84.175  1.00 38.35           B  O
ATOM   4779  N    TYR B 323      24.252  30.188  83.719  1.00 46.83           B  N
ATOM   4780  CA   TYR B 323      23.301  29.803  82.670  1.00 46.83           B  C
ATOM   4781  CB   TYR B 323      23.624  28.403  82.141  1.00 30.11           B  C
ATOM   4782  CG   TYR B 323      24.710  28.379  81.098  1.00 30.11           B  C
ATOM   4783  CD1  TYR B 323      24.591  29.123  79.930  1.00 30.11           B  C
ATOM   4784  CE1  TYR B 323      25.590  29.102  78.961  1.00 30.11           B  C
ATOM   4785  CD2  TYR B 323      25.860  27.610  81.269  1.00 30.11           B  C
ATOM   4786  CE2  TYR B 323      26.866  27.584  80.300  1.00 30.11           B  C
ATOM   4787  CZ   TYR B 323      26.716  28.333  79.155  1.00 30.11           B  C
ATOM   4788  OH   TYR B 323      27.690  28.329  78.198  1.00 30.11           B  O
ATOM   4789  C    TYR B 323      21.875  29.800  83.240  1.00 46.83           B  C
ATOM   4790  O    TYR B 323      20.985  30.511  82.762  1.00 46.83           B  O
ATOM   4791  N    THR B 324      21.670  28.990  84.270  1.00 35.80           B  N
ATOM   4792  CA   THR B 324      20.368  28.892  84.899  1.00 35.80           B  C
ATOM   4793  CB   THR B 324      20.361  27.769  85.964  1.00 31.94           B  C
ATOM   4794  OG1  THR B 324      20.220  26.496  85.316  1.00 31.94           B  O
ATOM   4795  CG2  THR B 324      19.224  27.964  86.948  1.00 31.94           B  C
ATOM   4796  C    THR B 324      19.989  30.233  85.530  1.00 35.80           B  C
ATOM   4797  O    THR B 324      20.622  30.681  86.491  1.00 35.80           B  O
ATOM   4798  N    PRO B 325      18.956  30.902  84.986  1.00 38.24           B  N
ATOM   4799  CD   PRO B 325      18.128  30.560  83.815  1.00 29.83           B  C
ATOM   4800  CA   PRO B 325      18.555  32.194  85.554  1.00 38.24           B  C
ATOM   4801  CB   PRO B 325      17.260  32.517  84.826  1.00 29.83           B  C
ATOM   4802  CG   PRO B 325      17.480  31.891  83.479  1.00 29.83           B  C
ATOM   4803  C    PRO B 325      18.334  32.115  87.052  1.00 38.24           B  C
ATOM   4804  O    PRO B 325      18.868  32.925  87.815  1.00 38.24           B  O
ATOM   4805  N    THR B 326      17.559  31.126  87.480  1.00 17.96           B  N
ATOM   4806  CA   THR B 326      17.271  30.990  88.897  1.00 17.96           B  C
ATOM   4807  CB   THR B 326      16.238  29.876  89.157  1.00 26.51           B  C
ATOM   4808  OG1  THR B 326      16.822  28.597  88.895  1.00 26.51           B  O
ATOM   4809  CG2  THR B 326      15.039  30.059  88.260  1.00 26.51           B  C
ATOM   4810  C    THR B 326      18.486  30.770  89.815  1.00 17.96           B  C
ATOM   4811  O    THR B 326      18.381  30.911  91.023  1.00 17.96           B  O
ATOM   4812  N    ALA B 327      19.643  30.446  89.258  1.00 25.28           B  N
ATOM   4813  CA   ALA B 327      20.826  30.217  90.080  1.00 25.28           B  C
ATOM   4814  CB   ALA B 327      21.666  29.148  89.452  1.00 15.72           B  C
ATOM   4815  C    ALA B 327      21.670  31.465  90.290  1.00 25.28           B  C
ATOM   4816  O    ALA B 327      22.604  31.456  91.083  1.00 25.28           B  O
ATOM   4817  N    ARG B 328      21.349  32.539  89.576  1.00 39.75           B  N
ATOM   4818  CA   ARG B 328      22.114  33.777  89.691  1.00 39.75           B  C
```

FIG. 4-73

```
ATOM   4819  CB   ARG B 328      21.787  34.702  88.524  1.00 21.28      B  C
ATOM   4820  CG   ARG B 328      21.926  34.025  87.167  1.00 21.28      B  C
ATOM   4821  CD   ARG B 328      21.342  34.863  86.041  1.00 21.28      B  C
ATOM   4822  NE   ARG B 328      21.229  34.068  84.833  1.00 21.28      B  N
ATOM   4823  CZ   ARG B 328      20.626  34.473  83.735  1.00 21.28      B  C
ATOM   4824  NH1  ARG B 328      20.077  35.680  83.683  1.00 21.28      B  N
ATOM   4825  NH2  ARG B 328      20.563  33.656  82.702  1.00 21.28      B  N
ATOM   4826  C    ARG B 328      21.743  34.457  90.976  1.00 39.75      B  C
ATOM   4827  O    ARG B 328      20.676  34.209  91.497  1.00 39.75      B  O
ATOM   4828  N    LEU B 329      22.617  35.313  91.488  1.00 35.15      B  N
ATOM   4829  CA   LEU B 329      22.329  36.035  92.719  1.00 35.15      B  C
ATOM   4830  CB   LEU B 329      23.570  36.799  93.190  1.00 20.61      B  C
ATOM   4831  CG   LEU B 329      24.546  36.101  94.135  1.00 20.61      B  C
ATOM   4832  CD1  LEU B 329      24.587  34.628  93.849  1.00 20.61      B  C
ATOM   4833  CD2  LEU B 329      25.913  36.708  93.971  1.00 20.61      B  C
ATOM   4834  C    LEU B 329      21.195  37.022  92.497  1.00 35.15      B  C
ATOM   4835  O    LEU B 329      20.833  37.342  91.366  1.00 35.15      B  O
ATOM   4836  N    THR B 330      20.630  37.479  93.603  1.00 32.26      B  N
ATOM   4837  CA   THR B 330      19.567  38.468  93.606  1.00 32.26      B  C
ATOM   4838  CB   THR B 330      18.620  38.213  94.766  1.00 34.27      B  C
ATOM   4839  OG1  THR B 330      17.655  37.243  94.368  1.00 34.27      B  O
ATOM   4840  CG2  THR B 330      17.923  39.487  95.207  1.00 34.27      B  C
ATOM   4841  C    THR B 330      20.260  39.804  93.833  1.00 32.26      B  C
ATOM   4842  O    THR B 330      21.237  39.883  94.569  1.00 32.26      B  O
ATOM   4843  N    PRO B 331      19.765  40.873  93.211  1.00 26.20      B  N
ATOM   4844  CD   PRO B 331      18.581  40.983  92.348  1.00 31.93      B  C
ATOM   4845  CA   PRO B 331      20.394  42.183  93.398  1.00 26.20      B  C
ATOM   4846  CB   PRO B 331      19.336  43.140  92.855  1.00 31.93      B  C
ATOM   4847  CG   PRO B 331      18.753  42.370  91.749  1.00 31.93      B  C
ATOM   4848  C    PRO B 331      20.763  42.465  94.860  1.00 26.20      B  C
ATOM   4849  O    PRO B 331      21.815  43.036  95.157  1.00 26.20      B  O
ATOM   4850  N    LEU B 332      19.898  42.037  95.770  1.00 22.38      B  N
ATOM   4851  CA   LEU B 332      20.116  42.248  97.189  1.00 22.38      B  C
ATOM   4852  CB   LEU B 332      18.789  42.085  97.913  1.00 12.07      B  C
ATOM   4853  CG   LEU B 332      18.716  42.551  99.356  1.00 12.07      B  C
ATOM   4854  CD1  LEU B 332      18.920  44.030  99.448  1.00 12.07      B  C
ATOM   4855  CD2  LEU B 332      17.371  42.158  99.902  1.00 12.07      B  C
ATOM   4856  C    LEU B 332      21.153  41.264  97.718  1.00 22.38      B  C
ATOM   4857  O    LEU B 332      21.947  41.599  98.596  1.00 22.38      B  O
ATOM   4858  N    GLU B 333      21.144  40.052  97.173  1.00 30.57      B  N
ATOM   4859  CA   GLU B 333      22.098  39.032  97.585  1.00 30.57      B  C
ATOM   4860  CB   GLU B 333      21.769  37.678  96.958  1.00 38.47      B  C
ATOM   4861  CG   GLU B 333      20.461  37.054  97.387  1.00 38.47      B  C
ATOM   4862  CD   GLU B 333      20.234  35.707  96.714  1.00 38.47      B  C
ATOM   4863  OE1  GLU B 333      20.480  35.597  95.482  1.00 38.47      B  O
ATOM   4864  OE2  GLU B 333      19.806  34.768  97.428  1.00 38.47      B  O
ATOM   4865  C    GLU B 333      23.461  39.461  97.106  1.00 30.57      B  C
ATOM   4866  O    GLU B 333      24.469  39.137  97.716  1.00 30.57      B  O
ATOM   4867  N    ALA B 334      23.479  40.202  96.006  1.00 27.39      B  N
ATOM   4868  CA   ALA B 334      24.723  40.661  95.431  1.00 27.39      B  C
ATOM   4869  CB   ALA B 334      24.486  41.146  94.007  1.00 31.78      B  C
ATOM   4870  C    ALA B 334      25.278  41.769  96.299  1.00 27.39      B  C
ATOM   4871  O    ALA B 334      26.483  41.832  96.532  1.00 27.39      B  O
ATOM   4872  N    CYS B 335      24.395  42.625  96.793  1.00 22.12      B  N
ATOM   4873  CA   CYS B 335      24.813  43.733  97.637  1.00 22.12      B  C
ATOM   4874  CB   CYS B 335      23.604  44.573  98.037  1.00 29.50      B  C
ATOM   4875  SG   CYS B 335      23.071  45.758  96.793  1.00 29.50      B  S
ATOM   4876  C    CYS B 335      25.511  43.258  98.892  1.00 22.12      B  C
ATOM   4877  O    CYS B 335      26.407  43.928  99.402  1.00 22.12      B  O
ATOM   4878  N    ALA B 336      25.100  42.095  99.384  1.00 19.83      B  N
ATOM   4879  CA   ALA B 336      25.669  41.540 100.604  1.00 19.83      B  C
ATOM   4880  CB   ALA B 336      24.625  40.724 101.351  1.00 10.05      B  C
ATOM   4881  C    ALA B 336      26.906  40.705 100.380  1.00 19.83      B  C
ATOM   4882  O    ALA B 336      27.506  40.230 101.346  1.00 19.83      B  O
ATOM   4883  N    HIS B 337      27.299  40.550  99.118  1.00 20.93      B  N
ATOM   4884  CA   HIS B 337      28.478  39.771  98.781  1.00 20.93      B  C
ATOM   4885  CB   HIS B 337      28.627  39.676  97.264  1.00 31.62      B  C
```

FIG. 4-74

| | | | | | | | | | | | |
|---|---|---|---|---|---|---|---|---|---|---|---|
| ATOM | 4886 | CG | HIS | B | 337 | 29.469 | 38.523 | 96.815 | 1.00 | 31.62 | B C |
| ATOM | 4887 | CD2 | HIS | B | 337 | 29.129 | 37.262 | 96.455 | 1.00 | 31.62 | B C |
| ATOM | 4888 | ND1 | HIS | B | 337 | 30.840 | 38.597 | 96.707 | 1.00 | 31.62 | B N |
| ATOM | 4889 | CE1 | HIS | B | 337 | 31.309 | 37.432 | 96.297 | 1.00 | 31.62 | B C |
| ATOM | 4890 | NE2 | HIS | B | 337 | 30.292 | 36.606 | 96.135 | 1.00 | 31.62 | B N |
| ATOM | 4891 | C | HIS | B | 337 | 29.740 | 40.359 | 99.423 | 1.00 | 20.93 | B C |
| ATOM | 4892 | O | HIS | B | 337 | 29.847 | 41.563 | 99.646 | 1.00 | 20.93 | B O |
| ATOM | 4893 | N | SER | B | 338 | 30.692 | 39.493 | 99.735 | 1.00 | 35.62 | B N |
| ATOM | 4894 | CA | SER | B | 338 | 31.927 | 39.923 | 100.382 | 1.00 | 35.62 | B C |
| ATOM | 4895 | CB | SER | B | 338 | 32.800 | 38.703 | 100.643 | 1.00 | 34.29 | B C |
| ATOM | 4896 | OG | SER | B | 338 | 32.005 | 37.635 | 101.127 | 1.00 | 34.29 | B O |
| ATOM | 4897 | C | SER | B | 338 | 32.710 | 40.960 | 99.583 | 1.00 | 35.62 | B C |
| ATOM | 4898 | O | SER | B | 338 | 33.414 | 41.808 | 100.140 | 1.00 | 35.62 | B O |
| ATOM | 4899 | N | PHE | B | 339 | 32.605 | 40.883 | 98.265 | 1.00 | 42.35 | B N |
| ATOM | 4900 | CA | PHE | B | 339 | 33.313 | 41.830 | 97.426 | 1.00 | 42.35 | B C |
| ATOM | 4901 | CB | PHE | B | 339 | 33.009 | 41.548 | 95.955 | 1.00 | 27.58 | B C |
| ATOM | 4902 | CG | PHE | B | 339 | 33.615 | 42.541 | 95.033 | 1.00 | 27.58 | B C |
| ATOM | 4903 | CD1 | PHE | B | 339 | 34.979 | 42.786 | 95.068 | 1.00 | 27.58 | B C |
| ATOM | 4904 | CD2 | PHE | B | 339 | 32.827 | 43.283 | 94.172 | 1.00 | 27.58 | B C |
| ATOM | 4905 | CE1 | PHE | B | 339 | 35.550 | 43.763 | 94.261 | 1.00 | 27.58 | B C |
| ATOM | 4906 | CE2 | PHE | B | 339 | 33.396 | 44.265 | 93.358 | 1.00 | 27.58 | B C |
| ATOM | 4907 | CZ | PHE | B | 339 | 34.759 | 44.502 | 93.407 | 1.00 | 27.58 | B C |
| ATOM | 4908 | C | PHE | B | 339 | 32.972 | 43.292 | 97.780 | 1.00 | 42.35 | B C |
| ATOM | 4909 | O | PHE | B | 339 | 33.696 | 44.217 | 97.414 | 1.00 | 42.35 | B O |
| ATOM | 4910 | N | PHE | B | 340 | 31.885 | 43.501 | 98.513 | 1.00 | 31.40 | B N |
| ATOM | 4911 | CA | PHE | B | 340 | 31.475 | 44.851 | 98.879 | 1.00 | 31.40 | B C |
| ATOM | 4912 | CB | PHE | B | 340 | 29.994 | 45.036 | 98.548 | 1.00 | 24.44 | B C |
| ATOM | 4913 | CG | PHE | B | 340 | 29.682 | 44.905 | 97.086 | 1.00 | 24.44 | B C |
| ATOM | 4914 | CD1 | PHE | B | 340 | 30.332 | 45.706 | 96.151 | 1.00 | 24.44 | B C |
| ATOM | 4915 | CD2 | PHE | B | 340 | 28.722 | 44.005 | 96.643 | 1.00 | 24.44 | B C |
| ATOM | 4916 | CE1 | PHE | B | 340 | 30.036 | 45.617 | 94.813 | 1.00 | 24.44 | B C |
| ATOM | 4917 | CE2 | PHE | B | 340 | 28.419 | 43.912 | 95.299 | 1.00 | 24.44 | B C |
| ATOM | 4918 | CZ | PHE | B | 340 | 29.079 | 44.722 | 94.384 | 1.00 | 24.44 | B C |
| ATOM | 4919 | C | PHE | B | 340 | 31.718 | 45.160 | 100.354 | 1.00 | 31.40 | B C |
| ATOM | 4920 | O | PHE | B | 340 | 31.229 | 46.155 | 100.876 | 1.00 | 31.40 | B O |
| ATOM | 4921 | N | ASP | B | 341 | 32.478 | 44.298 | 101.018 | 1.00 | 23.54 | B N |
| ATOM | 4922 | CA | ASP | B | 341 | 32.776 | 44.468 | 102.428 | 1.00 | 23.54 | B C |
| ATOM | 4923 | CB | ASP | B | 341 | 33.531 | 43.258 | 102.945 | 1.00 | 44.69 | B C |
| ATOM | 4924 | CG | ASP | B | 341 | 32.606 | 42.140 | 103.346 | 1.00 | 44.69 | B C |
| ATOM | 4925 | OD1 | ASP | B | 341 | 31.700 | 41.820 | 102.552 | 1.00 | 44.69 | B O |
| ATOM | 4926 | OD2 | ASP | B | 341 | 32.777 | 41.584 | 104.451 | 1.00 | 44.69 | B O |
| ATOM | 4927 | C | ASP | B | 341 | 33.572 | 45.719 | 102.729 | 1.00 | 23.54 | B C |
| ATOM | 4928 | O | ASP | B | 341 | 33.398 | 46.331 | 103.771 | 1.00 | 23.54 | B O |
| ATOM | 4929 | N | GLU | B | 342 | 34.457 | 46.108 | 101.831 | 1.00 | 29.22 | B N |
| ATOM | 4930 | CA | GLU | B | 342 | 35.231 | 47.299 | 102.092 | 1.00 | 29.22 | B C |
| ATOM | 4931 | CB | GLU | B | 342 | 36.255 | 47.538 | 100.994 | 1.00 | 33.81 | B C |
| ATOM | 4932 | CG | GLU | B | 342 | 37.004 | 48.831 | 101.186 | 1.00 | 33.81 | B C |
| ATOM | 4933 | CD | GLU | B | 342 | 38.266 | 48.911 | 100.368 | 1.00 | 33.81 | B C |
| ATOM | 4934 | OE1 | GLU | B | 342 | 38.209 | 48.647 | 99.143 | 1.00 | 33.81 | B O |
| ATOM | 4935 | OE2 | GLU | B | 342 | 39.314 | 49.249 | 100.963 | 1.00 | 33.81 | B O |
| ATOM | 4936 | C | GLU | B | 342 | 34.333 | 48.513 | 102.215 | 1.00 | 29.22 | B C |
| ATOM | 4937 | O | GLU | B | 342 | 34.667 | 49.462 | 102.908 | 1.00 | 29.22 | B O |
| ATOM | 4938 | N | LEU | B | 343 | 33.193 | 48.497 | 101.542 | 1.00 | 26.55 | B N |
| ATOM | 4939 | CA | LEU | B | 343 | 32.295 | 49.635 | 101.619 | 1.00 | 26.55 | B C |
| ATOM | 4940 | CB | LEU | B | 343 | 31.220 | 49.541 | 100.540 | 1.00 | 10.33 | B C |
| ATOM | 4941 | CG | LEU | B | 343 | 31.707 | 49.406 | 99.101 | 1.00 | 10.33 | B C |
| ATOM | 4942 | CD1 | LEU | B | 343 | 30.538 | 49.491 | 98.163 | 1.00 | 10.33 | B C |
| ATOM | 4943 | CD2 | LEU | B | 343 | 32.709 | 50.484 | 98.808 | 1.00 | 10.33 | B C |
| ATOM | 4944 | C | LEU | B | 343 | 31.658 | 49.651 | 102.995 | 1.00 | 26.55 | B C |
| ATOM | 4945 | O | LEU | B | 343 | 31.305 | 50.706 | 103.514 | 1.00 | 26.55 | B O |
| ATOM | 4946 | N | ARG | B | 344 | 31.522 | 48.480 | 103.600 | 1.00 | 38.61 | B N |
| ATOM | 4947 | CA | ARG | B | 344 | 30.921 | 48.412 | 104.924 | 1.00 | 38.61 | B C |
| ATOM | 4948 | CB | ARG | B | 344 | 30.298 | 47.035 | 105.152 | 1.00 | 22.01 | B C |
| ATOM | 4949 | CG | ARG | B | 344 | 29.006 | 46.864 | 104.401 | 1.00 | 22.01 | B C |
| ATOM | 4950 | CD | ARG | B | 344 | 28.327 | 45.582 | 104.741 | 1.00 | 22.01 | B C |
| ATOM | 4951 | NE | ARG | B | 344 | 28.812 | 44.476 | 103.929 | 1.00 | 22.01 | B N |
| ATOM | 4952 | CZ | ARG | B | 344 | 28.584 | 44.357 | 102.629 | 1.00 | 22.01 | B C |

FIG. 4-75

| ATOM | 4953 | NH1 | ARG | B | 344 | 27.883 | 45.286 | 101.995 | 1.00 | 22.01 | B | N |
| --- | --- | --- | --- | --- | --- | --- | --- | --- | --- | --- | --- | --- |
| ATOM | 4954 | NH2 | ARG | B | 344 | 29.038 | 43.299 | 101.971 | 1.00 | 22.01 | B | N |
| ATOM | 4955 | C | ARG | B | 344 | 31.903 | 48.755 | 106.046 | 1.00 | 38.61 | B | C |
| ATOM | 4956 | O | ARG | B | 344 | 31.522 | 48.869 | 107.214 | 1.00 | 38.61 | B | O |
| ATOM | 4957 | N | ASP | B | 345 | 33.173 | 48.917 | 105.691 | 1.00 | 39.92 | B | N |
| ATOM | 4958 | CA | ASP | B | 345 | 34.178 | 49.280 | 106.675 | 1.00 | 39.92 | B | C |
| ATOM | 4959 | CB | ASP | B | 345 | 35.574 | 49.188 | 106.060 | 1.00 | 56.74 | B | C |
| ATOM | 4960 | CG | ASP | B | 345 | 36.676 | 49.571 | 107.037 | 1.00 | 56.74 | B | C |
| ATOM | 4961 | OD1 | ASP | B | 345 | 37.737 | 48.892 | 107.020 | 1.00 | 56.74 | B | O |
| ATOM | 4962 | OD2 | ASP | B | 345 | 36.483 | 50.552 | 107.798 | 1.00 | 56.74 | B | O |
| ATOM | 4963 | C | ASP | B | 345 | 33.879 | 50.712 | 107.099 | 1.00 | 39.92 | B | C |
| ATOM | 4964 | O | ASP | B | 345 | 33.586 | 51.561 | 106.259 | 1.00 | 39.92 | B | O |
| ATOM | 4965 | N | PRO | B | 346 | 33.925 | 50.996 | 108.410 | 1.00 | 38.14 | B | N |
| ATOM | 4966 | CD | PRO | B | 346 | 34.190 | 50.072 | 109.525 | 1.00 | 23.04 | B | C |
| ATOM | 4967 | CA | PRO | B | 346 | 33.650 | 52.346 | 108.916 | 1.00 | 38.14 | B | C |
| ATOM | 4968 | CB | PRO | B | 346 | 33.595 | 52.139 | 110.427 | 1.00 | 23.04 | B | C |
| ATOM | 4969 | CG | PRO | B | 346 | 34.553 | 51.026 | 110.647 | 1.00 | 23.04 | B | C |
| ATOM | 4970 | C | PRO | B | 346 | 34.695 | 53.400 | 108.503 | 1.00 | 38.14 | B | C |
| ATOM | 4971 | O | PRO | B | 346 | 34.445 | 54.612 | 108.555 | 1.00 | 38.14 | B | O |
| ATOM | 4972 | N | ASN | B | 347 | 35.864 | 52.929 | 108.085 | 1.00 | 41.84 | B | N |
| ATOM | 4973 | CA | ASN | B | 347 | 36.945 | 53.816 | 107.669 | 1.00 | 41.84 | B | C |
| ATOM | 4974 | CB | ASN | B | 347 | 38.290 | 53.242 | 108.107 | 1.00 | 43.09 | B | C |
| ATOM | 4975 | CG | ASN | B | 347 | 38.393 | 53.057 | 109.599 | 1.00 | 43.09 | B | C |
| ATOM | 4976 | OD1 | ASN | B | 347 | 39.398 | 52.540 | 110.095 | 1.00 | 43.09 | B | O |
| ATOM | 4977 | ND2 | ASN | B | 347 | 37.360 | 53.481 | 110.335 | 1.00 | 43.09 | B | N |
| ATOM | 4978 | C | ASN | B | 347 | 37.021 | 54.005 | 106.157 | 1.00 | 41.84 | B | C |
| ATOM | 4979 | O | ASN | B | 347 | 37.968 | 54.602 | 105.651 | 1.00 | 41.84 | B | O |
| ATOM | 4980 | N | VAL | B | 348 | 36.048 | 53.488 | 105.425 | 1.00 | 37.40 | B | N |
| ATOM | 4981 | CA | VAL | B | 348 | 36.118 | 53.619 | 103.991 | 1.00 | 37.40 | B | C |
| ATOM | 4982 | CB | VAL | B | 348 | 35.037 | 52.759 | 103.293 | 1.00 | 45.60 | B | C |
| ATOM | 4983 | CG1 | VAL | B | 348 | 33.656 | 53.418 | 103.387 | 1.00 | 45.60 | B | C |
| ATOM | 4984 | CG2 | VAL | B | 348 | 35.438 | 52.519 | 101.868 | 1.00 | 45.60 | B | C |
| ATOM | 4985 | C | VAL | B | 348 | 35.983 | 55.075 | 103.625 | 1.00 | 37.40 | B | C |
| ATOM | 4986 | O | VAL | B | 348 | 35.179 | 55.806 | 104.210 | 1.00 | 37.40 | B | O |
| ATOM | 4987 | N | LYS | B | 349 | 36.795 | 55.487 | 102.660 | 1.00 | 35.45 | B | N |
| ATOM | 4988 | CA | LYS | B | 349 | 36.822 | 56.863 | 102.196 | 1.00 | 35.45 | B | C |
| ATOM | 4989 | CB | LYS | B | 349 | 37.954 | 57.582 | 102.919 | 1.00 | 31.92 | B | C |
| ATOM | 4990 | CG | LYS | B | 349 | 37.606 | 58.901 | 103.563 | 1.00 | 31.92 | B | C |
| ATOM | 4991 | CD | LYS | B | 349 | 36.696 | 58.744 | 104.770 | 1.00 | 31.92 | B | C |
| ATOM | 4992 | CE | LYS | B | 349 | 36.695 | 60.011 | 105.627 | 1.00 | 31.92 | B | C |
| ATOM | 4993 | NZ | LYS | B | 349 | 35.784 | 59.892 | 106.810 | 1.00 | 31.92 | B | N |
| ATOM | 4994 | C | LYS | B | 349 | 37.101 | 56.853 | 100.697 | 1.00 | 35.45 | B | C |
| ATOM | 4995 | O | LYS | B | 349 | 37.668 | 55.886 | 100.165 | 1.00 | 35.45 | B | O |
| ATOM | 4996 | N | LEU | B | 350 | 36.699 | 57.924 | 100.016 | 1.00 | 29.15 | B | N |
| ATOM | 4997 | CA | LEU | B | 350 | 36.935 | 58.040 | 98.580 | 1.00 | 29.15 | B | C |
| ATOM | 4998 | CB | LEU | B | 350 | 36.004 | 59.078 | 97.962 | 1.00 | 18.06 | B | C |
| ATOM | 4999 | CG | LEU | B | 350 | 34.544 | 58.640 | 97.906 | 1.00 | 18.06 | B | C |
| ATOM | 5000 | CD1 | LEU | B | 350 | 33.728 | 59.624 | 97.079 | 1.00 | 18.06 | B | C |
| ATOM | 5001 | CD2 | LEU | B | 350 | 34.456 | 57.267 | 97.292 | 1.00 | 18.06 | B | C |
| ATOM | 5002 | C | LEU | B | 350 | 38.364 | 58.459 | 98.329 | 1.00 | 29.15 | B | C |
| ATOM | 5003 | O | LEU | B | 350 | 38.913 | 59.269 | 99.069 | 1.00 | 29.15 | B | O |
| ATOM | 5004 | N | PRO | B | 351 | 38.991 | 57.907 | 97.284 | 1.00 | 37.43 | B | N |
| ATOM | 5005 | CD | PRO | B | 351 | 38.428 | 57.099 | 96.191 | 1.00 | 26.12 | B | C |
| ATOM | 5006 | CA | PRO | B | 351 | 40.376 | 58.283 | 96.993 | 1.00 | 37.43 | B | C |
| ATOM | 5007 | CB | PRO | B | 351 | 40.666 | 57.516 | 95.704 | 1.00 | 26.12 | B | C |
| ATOM | 5008 | CG | PRO | B | 351 | 39.338 | 57.444 | 95.053 | 1.00 | 26.12 | B | C |
| ATOM | 5009 | C | PRO | B | 351 | 40.402 | 59.800 | 96.811 | 1.00 | 37.43 | B | C |
| ATOM | 5010 | O | PRO | B | 351 | 41.381 | 60.472 | 97.146 | 1.00 | 37.43 | B | O |
| ATOM | 5011 | N | ASN | B | 352 | 39.291 | 60.336 | 96.318 | 1.00 | 37.92 | B | N |
| ATOM | 5012 | CA | ASN | B | 352 | 39.187 | 61.771 | 96.104 | 1.00 | 37.92 | B | C |
| ATOM | 5013 | CB | ASN | B | 352 | 37.900 | 62.107 | 95.337 | 1.00 | 46.28 | B | C |
| ATOM | 5014 | CG | ASN | B | 352 | 36.801 | 62.640 | 96.236 | 1.00 | 46.28 | B | C |
| ATOM | 5015 | OD1 | ASN | B | 352 | 36.457 | 62.024 | 97.249 | 1.00 | 46.28 | B | O |
| ATOM | 5016 | ND2 | ASN | B | 352 | 36.233 | 63.790 | 95.864 | 1.00 | 46.28 | B | N |
| ATOM | 5017 | C | ASN | B | 352 | 39.268 | 62.567 | 97.413 | 1.00 | 37.92 | B | C |
| ATOM | 5018 | O | ASN | B | 352 | 39.404 | 63.783 | 97.403 | 1.00 | 37.92 | B | O |
| ATOM | 5019 | N | GLY | B | 353 | 39.181 | 61.878 | 98.541 | 1.00 | 27.22 | B | N |

FIG. 4-76

| | | | | | | | | | | | |
|---|---|---|---|---|---|---|---|---|---|---|---|
| ATOM | 5020 | CA | GLY | B | 353 | 39.281 | 62.556 | 99.818 | 1.00 | 27.22 | B C |
| ATOM | 5021 | C | GLY | B | 353 | 38.005 | 62.643 | 100.618 | 1.00 | 27.22 | B C |
| ATOM | 5022 | O | GLY | B | 353 | 38.039 | 62.497 | 101.844 | 1.00 | 27.22 | B O |
| ATOM | 5023 | N | ARG | B | 354 | 36.876 | 62.884 | 99.957 | 1.00 | 28.21 | B N |
| ATOM | 5024 | CA | ARG | B | 354 | 35.637 | 62.986 | 100.703 | 1.00 | 28.21 | B C |
| ATOM | 5025 | CB | ARG | B | 354 | 34.632 | 63.866 | 99.958 | 1.00 | 48.05 | B C |
| ATOM | 5026 | CG | ARG | B | 354 | 34.137 | 63.366 | 98.645 | 1.00 | 48.05 | B C |
| ATOM | 5027 | CD | ARG | B | 354 | 33.250 | 64.441 | 98.002 | 1.00 | 48.05 | B C |
| ATOM | 5028 | NE | ARG | B | 354 | 34.030 | 65.601 | 97.554 | 1.00 | 48.05 | B N |
| ATOM | 5029 | CZ | ARG | B | 354 | 33.544 | 66.608 | 96.823 | 1.00 | 48.05 | B C |
| ATOM | 5030 | NH1 | ARG | B | 354 | 32.266 | 66.594 | 96.455 | 1.00 | 48.05 | B N |
| ATOM | 5031 | NH2 | ARG | B | 354 | 34.339 | 67.620 | 96.459 | 1.00 | 48.05 | B N |
| ATOM | 5032 | C | ARG | B | 354 | 35.033 | 61.641 | 101.101 | 1.00 | 28.21 | B C |
| ATOM | 5033 | O | ARG | B | 354 | 35.621 | 60.594 | 100.846 | 1.00 | 28.21 | B O |
| ATOM | 5034 | N | ASP | B | 355 | 33.886 | 61.680 | 101.771 | 1.00 | 53.18 | B N |
| ATOM | 5035 | CA | ASP | B | 355 | 33.198 | 60.474 | 102.220 | 1.00 | 53.18 | B C |
| ATOM | 5036 | CB | ASP | B | 355 | 32.170 | 60.827 | 103.286 | 1.00 | 54.41 | B C |
| ATOM | 5037 | CG | ASP | B | 355 | 32.778 | 60.931 | 104.649 | 1.00 | 54.41 | B C |
| ATOM | 5038 | OD1 | ASP | B | 355 | 32.000 | 61.075 | 105.622 | 1.00 | 54.41 | B O |
| ATOM | 5039 | OD2 | ASP | B | 355 | 34.030 | 60.861 | 104.728 | 1.00 | 54.41 | B O |
| ATOM | 5040 | C | ASP | B | 355 | 32.507 | 59.664 | 101.137 | 1.00 | 53.18 | B C |
| ATOM | 5041 | O | ASP | B | 355 | 32.314 | 60.131 | 100.005 | 1.00 | 53.18 | B O |
| ATOM | 5042 | N | THR | B | 356 | 32.154 | 58.437 | 101.496 | 1.00 | 33.81 | B N |
| ATOM | 5043 | CA | THR | B | 356 | 31.441 | 57.568 | 100.581 | 1.00 | 33.81 | B C |
| ATOM | 5044 | CB | THR | B | 356 | 31.395 | 56.107 | 101.093 | 1.00 | 44.24 | B C |
| ATOM | 5045 | OG1 | THR | B | 356 | 30.871 | 56.078 | 102.427 | 1.00 | 44.24 | B O |
| ATOM | 5046 | CG2 | THR | B | 356 | 32.767 | 55.493 | 101.095 | 1.00 | 44.24 | B C |
| ATOM | 5047 | C | THR | B | 356 | 30.010 | 58.109 | 100.539 | 1.00 | 33.81 | B C |
| ATOM | 5048 | O | THR | B | 356 | 29.555 | 58.770 | 101.479 | 1.00 | 33.81 | B O |
| ATOM | 5049 | N | PRO | B | 357 | 29.286 | 57.872 | 99.439 | 1.00 | 27.32 | B N |
| ATOM | 5050 | CD | PRO | B | 357 | 29.655 | 57.397 | 98.094 | 1.00 | 23.87 | B C |
| ATOM | 5051 | CA | PRO | B | 357 | 27.926 | 58.396 | 99.450 | 1.00 | 27.32 | B C |
| ATOM | 5052 | CB | PRO | B | 357 | 27.563 | 58.431 | 97.971 | 1.00 | 23.87 | B C |
| ATOM | 5053 | CG | PRO | B | 357 | 28.314 | 57.276 | 97.419 | 1.00 | 23.87 | B C |
| ATOM | 5054 | C | PRO | B | 357 | 27.054 | 57.443 | 100.248 | 1.00 | 27.32 | B C |
| ATOM | 5055 | O | PRO | B | 357 | 27.545 | 56.444 | 100.779 | 1.00 | 27.32 | B O |
| ATOM | 5056 | N | ALA | B | 358 | 25.766 | 57.752 | 100.337 | 1.00 | 29.72 | B N |
| ATOM | 5057 | CA | ALA | B | 358 | 24.825 | 56.906 | 101.067 | 1.00 | 29.72 | B C |
| ATOM | 5058 | CB | ALA | B | 358 | 23.414 | 57.492 | 100.988 | 1.00 | 40.70 | B C |
| ATOM | 5059 | C | ALA | B | 358 | 24.829 | 55.511 | 100.467 | 1.00 | 29.72 | B C |
| ATOM | 5060 | O | ALA | B | 358 | 24.567 | 55.339 | 99.277 | 1.00 | 29.72 | B O |
| ATOM | 5061 | N | LEU | B | 359 | 25.104 | 54.521 | 101.301 | 1.00 | 24.10 | B N |
| ATOM | 5062 | CA | LEU | B | 359 | 25.156 | 53.147 | 100.856 | 1.00 | 24.10 | B C |
| ATOM | 5063 | CB | LEU | B | 359 | 26.600 | 52.649 | 100.977 | 1.00 | 21.04 | B C |
| ATOM | 5064 | CG | LEU | B | 359 | 27.603 | 52.739 | 99.814 | 1.00 | 21.04 | B C |
| ATOM | 5065 | CD1 | LEU | B | 359 | 27.244 | 53.817 | 98.824 | 1.00 | 21.04 | B C |
| ATOM | 5066 | CD2 | LEU | B | 359 | 28.989 | 52.968 | 100.397 | 1.00 | 21.04 | B C |
| ATOM | 5067 | C | LEU | B | 359 | 24.232 | 52.264 | 101.670 | 1.00 | 24.10 | B C |
| ATOM | 5068 | O | LEU | B | 359 | 23.811 | 51.199 | 101.212 | 1.00 | 24.10 | B O |
| ATOM | 5069 | N | PHE | B | 360 | 23.883 | 52.730 | 102.865 | 1.00 | 33.64 | B N |
| ATOM | 5070 | CA | PHE | B | 360 | 23.063 | 51.930 | 103.768 | 1.00 | 33.64 | B C |
| ATOM | 5071 | CB | PHE | B | 360 | 23.863 | 51.731 | 105.050 | 1.00 | 22.54 | B C |
| ATOM | 5072 | CG | PHE | B | 360 | 25.326 | 51.577 | 104.810 | 1.00 | 22.54 | B C |
| ATOM | 5073 | CD1 | PHE | B | 360 | 25.820 | 50.456 | 104.158 | 1.00 | 22.54 | B C |
| ATOM | 5074 | CD2 | PHE | B | 360 | 26.212 | 52.579 | 105.198 | 1.00 | 22.54 | B C |
| ATOM | 5075 | CE1 | PHE | B | 360 | 27.184 | 50.335 | 103.890 | 1.00 | 22.54 | B C |
| ATOM | 5076 | CE2 | PHE | B | 360 | 27.575 | 52.479 | 104.941 | 1.00 | 22.54 | B C |
| ATOM | 5077 | CZ | PHE | B | 360 | 28.068 | 51.355 | 104.285 | 1.00 | 22.54 | B C |
| ATOM | 5078 | C | PHE | B | 360 | 21.644 | 52.395 | 104.107 | 1.00 | 33.64 | B C |
| ATOM | 5079 | O | PHE | B | 360 | 20.973 | 51.755 | 104.921 | 1.00 | 33.64 | B O |
| ATOM | 5080 | N | ASN | B | 361 | 21.175 | 53.479 | 103.493 | 1.00 | 25.01 | B N |
| ATOM | 5081 | CA | ASN | B | 361 | 19.833 | 53.979 | 103.793 | 1.00 | 25.01 | B C |
| ATOM | 5082 | CB | ASN | B | 361 | 19.686 | 55.455 | 103.362 | 1.00 | 20.81 | B C |
| ATOM | 5083 | CG | ASN | B | 361 | 20.113 | 55.705 | 101.929 | 1.00 | 20.81 | B C |
| ATOM | 5084 | OD1 | ASN | B | 361 | 20.985 | 55.029 | 101.400 | 1.00 | 20.81 | B O |
| ATOM | 5085 | ND2 | ASN | B | 361 | 19.511 | 56.698 | 101.305 | 1.00 | 20.81 | B N |
| ATOM | 5086 | C | ASN | B | 361 | 18.771 | 53.115 | 103.119 | 1.00 | 25.01 | B C |

FIG. 4-77

```
ATOM   5087  O    ASN B 361     17.941  53.604 102.370  1.00 25.01      B  O
ATOM   5088  N    PHE B 362     18.816  51.817 103.386  1.00 18.99      B  N
ATOM   5089  CA   PHE B 362     17.853  50.877 102.835  1.00 18.99      B  C
ATOM   5090  CB   PHE B 362     18.232  49.460 103.223  1.00 24.18      B  C
ATOM   5091  CG   PHE B 362     19.279  48.854 102.365  1.00 24.18      B  C
ATOM   5092  CD1  PHE B 362     18.930  48.143 101.226  1.00 24.18      B  C
ATOM   5093  CD2  PHE B 362     20.620  48.947 102.713  1.00 24.18      B  C
ATOM   5094  CE1  PHE B 362     19.902  47.517 100.446  1.00 24.18      B  C
ATOM   5095  CE2  PHE B 362     21.610  48.326 101.940  1.00 24.18      B  C
ATOM   5096  CZ   PHE B 362     21.249  47.607 100.804  1.00 24.18      B  C
ATOM   5097  C    PHE B 362     16.479  51.144 103.409  1.00 18.99      B  C
ATOM   5098  O    PHE B 362     16.362  51.782 104.430  1.00 18.99      B  O
ATOM   5099  N    THR B 363     15.448  50.639 102.745  1.00 32.21      B  N
ATOM   5100  CA   THR B 363     14.077  50.772 103.220  1.00 32.21      B  C
ATOM   5101  CB   THR B 363     13.210  51.730 102.358  1.00 12.54      B  C
ATOM   5102  OG1  THR B 363     13.240  51.312 100.991  1.00 12.54      B  O
ATOM   5103  CG2  THR B 363     13.699  53.146 102.467  1.00 12.54      B  C
ATOM   5104  C    THR B 363     13.471  49.382 103.145  1.00 32.21      B  C
ATOM   5105  O    THR B 363     14.001  48.505 102.457  1.00 32.21      B  O
ATOM   5106  N    THR B 364     12.378  49.169 103.869  1.00 39.95      B  N
ATOM   5107  CA   THR B 364     11.736  47.866 103.869  1.00 39.95      B  C
ATOM   5108  CB   THR B 364     10.474  47.855 104.755  1.00 36.28      B  C
ATOM   5109  OG1  THR B 364      9.994  49.193 104.918  1.00 36.28      B  O
ATOM   5110  CG2  THR B 364     10.784  47.281 106.115  1.00 36.28      B  C
ATOM   5111  C    THR B 364     11.392  47.431 102.448  1.00 39.95      B  C
ATOM   5112  O    THR B 364     11.537  46.254 102.112  1.00 39.95      B  O
ATOM   5113  N    GLN B 365     10.965  48.374 101.609  1.00 20.67      B  N
ATOM   5114  CA   GLN B 365     10.623  48.050 100.228  1.00 20.67      B  C
ATOM   5115  CB   GLN B 365     10.228  49.308  99.445  1.00 32.56      B  C
ATOM   5116  CG   GLN B 365      8.875  49.228  98.735  1.00 32.56      B  C
ATOM   5117  CD   GLN B 365      8.821  48.177  97.652  1.00 32.56      B  C
ATOM   5118  OE1  GLN B 365      9.042  46.986  97.896  1.00 32.56      B  O
ATOM   5119  NE2  GLN B 365      8.524  48.611  96.443  1.00 32.56      B  N
ATOM   5120  C    GLN B 365     11.821  47.405  99.551  1.00 20.67      B  C
ATOM   5121  O    GLN B 365     11.704  46.382  98.885  1.00 20.67      B  O
ATOM   5122  N    GLU B 366     12.981  48.014  99.759  1.00 42.00      B  N
ATOM   5123  CA   GLU B 366     14.237  47.586  99.167  1.00 42.00      B  C
ATOM   5124  CB   GLU B 366     15.258  48.705  99.353  1.00 23.99      B  C
ATOM   5125  CG   GLU B 366     16.543  48.522  98.588  1.00 23.99      B  C
ATOM   5126  CD   GLU B 366     17.356  49.794  98.538  1.00 23.99      B  C
ATOM   5127  OE1  GLU B 366     17.114  50.671  99.396  1.00 23.99      B  O
ATOM   5128  OE2  GLU B 366     18.231  49.913  97.654  1.00 23.99      B  O
ATOM   5129  C    GLU B 366     14.774  46.268  99.710  1.00 42.00      B  C
ATOM   5130  O    GLU B 366     15.489  45.539  99.004  1.00 42.00      B  O
ATOM   5131  N    LEU B 367     14.416  45.954 100.954  1.00 28.86      B  N
ATOM   5132  CA   LEU B 367     14.883  44.724 101.587  1.00 28.86      B  C
ATOM   5133  CB   LEU B 367     15.217  44.975 103.057  1.00 33.61      B  C
ATOM   5134  CG   LEU B 367     16.281  46.007 103.398  1.00 33.61      B  C
ATOM   5135  CD1  LEU B 367     16.092  46.427 104.839  1.00 33.61      B  C
ATOM   5136  CD2  LEU B 367     17.667  45.422 103.148  1.00 33.61      B  C
ATOM   5137  C    LEU B 367     13.870  43.590 101.509  1.00 28.86      B  C
ATOM   5138  O    LEU B 367     14.207  42.432 101.747  1.00 28.86      B  O
ATOM   5139  N    SER B 368     12.637  43.937 101.166  1.00 26.89      B  N
ATOM   5140  CA   SER B 368     11.534  42.993 101.088  1.00 26.89      B  C
ATOM   5141  CB   SER B 368     10.387  43.603 100.301  1.00 47.59      B  C
ATOM   5142  OG   SER B 368     10.649  43.538  98.911  1.00 47.59      B  O
ATOM   5143  C    SER B 368     11.846  41.639 100.490  1.00 26.89      B  C
ATOM   5144  O    SER B 368     11.273  40.646 100.905  1.00 26.89      B  O
ATOM   5145  N    SER B 369     12.729  41.580  99.505  1.00 43.58      B  N
ATOM   5146  CA   SER B 369     13.045  40.292  98.894  1.00 43.58      B  C
ATOM   5147  CB   SER B 369     13.963  40.475  97.690  1.00 19.53      B  C
ATOM   5148  OG   SER B 369     15.266  40.838  98.094  1.00 19.53      B  O
ATOM   5149  C    SER B 369     13.699  39.306  99.858  1.00 43.58      B  C
ATOM   5150  O    SER B 369     13.681  38.102  99.622  1.00 43.58      B  O
ATOM   5151  N    ASN B 370     14.287  39.817 100.933  1.00 32.25      B  N
ATOM   5152  CA   ASN B 370     14.943  38.977 101.927  1.00 32.25      B  C
ATOM   5153  CB   ASN B 370     16.120  38.242 101.285  1.00 29.13      B  C
```

FIG. 4-78

```
ATOM   5154  CG   ASN B 370      16.924  37.439 102.274  1.00 29.13           B  C
ATOM   5155  OD1  ASN B 370      17.462  36.398 101.936  1.00 29.13           B  O
ATOM   5156  ND2  ASN B 370      17.027  37.927 103.495  1.00 29.13           B  N
ATOM   5157  C    ASN B 370      15.409  39.898 103.053  1.00 32.25           B  C
ATOM   5158  O    ASN B 370      16.583  40.282 103.129  1.00 32.25           B  O
ATOM   5159  N    PRO B 371      14.475  40.262 103.949  1.00 38.02           B  N
ATOM   5160  CD   PRO B 371      13.060  39.841 103.948  1.00 14.24           B  C
ATOM   5161  CA   PRO B 371      14.749  41.148 105.081  1.00 38.02           B  C
ATOM   5162  CB   PRO B 371      13.438  41.121 105.865  1.00 14.24           B  C
ATOM   5163  CG   PRO B 371      12.409  40.901 104.785  1.00 14.24           B  C
ATOM   5164  C    PRO B 371      15.947  40.761 105.931  1.00 38.02           B  C
ATOM   5165  O    PRO B 371      16.752  41.616 106.284  1.00 38.02           B  O
ATOM   5166  N    PRO B 372      16.093  39.471 106.264  1.00 23.96           B  N
ATOM   5167  CD   PRO B 372      15.271  38.300 105.914  1.00 12.61           B  C
ATOM   5168  CA   PRO B 372      17.235  39.072 107.087  1.00 23.96           B  C
ATOM   5169  CB   PRO B 372      17.268  37.562 106.917  1.00 12.61           B  C
ATOM   5170  CG   PRO B 372      15.829  37.229 106.830  1.00 12.61           B  C
ATOM   5171  C    PRO B 372      18.543  39.733 106.685  1.00 23.96           B  C
ATOM   5172  O    PRO B 372      19.339  40.099 107.537  1.00 23.96           B  O
ATOM   5173  N    LEU B 373      18.744  39.901 105.382  1.00 20.62           B  N
ATOM   5174  CA   LEU B 373      19.953  40.508 104.837  1.00 20.62           B  C
ATOM   5175  CB   LEU B 373      19.738  40.763 103.344  1.00 27.09           B  C
ATOM   5176  CG   LEU B 373      20.377  39.777 102.366  1.00 27.09           B  C
ATOM   5177  CD1  LEU B 373      20.648  38.458 103.076  1.00 27.09           B  C
ATOM   5178  CD2  LEU B 373      19.472  39.603 101.151  1.00 27.09           B  C
ATOM   5179  C    LEU B 373      20.370  41.810 105.528  1.00 20.62           B  C
ATOM   5180  O    LEU B 373      21.545  42.181 105.542  1.00 20.62           B  O
ATOM   5181  N    ALA B 374      19.403  42.502 106.106  1.00 32.24           B  N
ATOM   5182  CA   ALA B 374      19.686  43.762 106.767  1.00 32.24           B  C
ATOM   5183  CB   ALA B 374      18.434  44.289 107.444  1.00 11.12           B  C
ATOM   5184  C    ALA B 374      20.799  43.624 107.784  1.00 32.24           B  C
ATOM   5185  O    ALA B 374      21.491  44.593 108.078  1.00 32.24           B  O
ATOM   5186  N    THR B 375      20.985  42.425 108.320  1.00 23.81           B  N
ATOM   5187  CA   THR B 375      22.031  42.231 109.309  1.00 23.81           B  C
ATOM   5188  CB   THR B 375      22.074  40.813 109.840  1.00 40.95           B  C
ATOM   5189  OG1  THR B 375      20.991  40.629 110.757  1.00 40.95           B  O
ATOM   5190  CG2  THR B 375      23.398  40.550 110.550  1.00 40.95           B  C
ATOM   5191  C    THR B 375      23.370  42.556 108.709  1.00 23.81           B  C
ATOM   5192  O    THR B 375      24.238  43.106 109.376  1.00 23.81           B  O
ATOM   5193  N    ILE B 376      23.535  42.211 107.436  1.00 35.60           B  N
ATOM   5194  CA   ILE B 376      24.786  42.482 106.746  1.00 35.60           B  C
ATOM   5195  CB   ILE B 376      25.087  41.443 105.665  1.00 27.48           B  C
ATOM   5196  CG2  ILE B 376      26.252  41.899 104.839  1.00 27.48           B  C
ATOM   5197  CG1  ILE B 376      25.404  40.097 106.301  1.00 27.48           B  C
ATOM   5198  CD1  ILE B 376      25.493  38.969 105.308  1.00 27.48           B  C
ATOM   5199  C    ILE B 376      24.753  43.850 106.065  1.00 35.60           B  C
ATOM   5200  O    ILE B 376      25.602  44.702 106.310  1.00 35.60           B  O
ATOM   5201  N    LEU B 377      23.757  44.047 105.211  1.00 28.84           B  N
ATOM   5202  CA   LEU B 377      23.628  45.282 104.453  1.00 28.84           B  C
ATOM   5203  CB   LEU B 377      22.255  45.343 103.775  1.00 29.20           B  C
ATOM   5204  CG   LEU B 377      22.116  44.627 102.426  1.00 29.20           B  C
ATOM   5205  CD1  LEU B 377      23.316  43.724 102.169  1.00 29.20           B  C
ATOM   5206  CD2  LEU B 377      20.816  43.851 102.401  1.00 29.20           B  C
ATOM   5207  C    LEU B 377      23.876  46.566 105.233  1.00 28.84           B  C
ATOM   5208  O    LEU B 377      24.468  47.504 104.700  1.00 28.84           B  O
ATOM   5209  N    ILE B 378      23.420  46.608 106.489  1.00 35.49           B  N
ATOM   5210  CA   ILE B 378      23.595  47.785 107.348  1.00 35.49           B  C
ATOM   5211  CB   ILE B 378      22.301  48.166 108.084  1.00 25.32           B  C
ATOM   5212  CG2  ILE B 378      22.554  49.375 108.968  1.00 25.32           B  C
ATOM   5213  CG1  ILE B 378      21.196  48.483 107.080  1.00 25.32           B  C
ATOM   5214  CD1  ILE B 378      19.822  48.668 107.725  1.00 25.32           B  C
ATOM   5215  C    ILE B 378      24.663  47.574 108.419  1.00 35.49           B  C
ATOM   5216  O    ILE B 378      24.357  47.175 109.531  1.00 35.49           B  O
ATOM   5217  N    PRO B 379      25.928  47.879 108.113  1.00 33.91           B  N
ATOM   5218  CD   PRO B 379      26.425  48.704 107.004  1.00 37.92           B  C
ATOM   5219  CA   PRO B 379      26.976  47.679 109.112  1.00 33.91           B  C
ATOM   5220  CB   PRO B 379      28.203  48.294 108.449  1.00 37.92           B  C
```

FIG. 4-79

```
ATOM   5221  CG   PRO B 379      27.619  49.380 107.631  1.00 37.92      B  C
ATOM   5222  C    PRO B 379      26.672  48.290 110.473  1.00 33.91      B  C
ATOM   5223  O    PRO B 379      25.893  49.245 110.582  1.00 33.91      B  O
ATOM   5224  N    PRO B 380      27.294  47.738 111.535  1.00 40.78      B  N
ATOM   5225  CD   PRO B 380      28.319  46.680 111.472  1.00 32.38      B  C
ATOM   5226  CA   PRO B 380      27.125  48.187 112.918  1.00 40.78      B  C
ATOM   5227  CB   PRO B 380      28.292  47.524 113.639  1.00 32.38      B  C
ATOM   5228  CG   PRO B 380      28.436  46.265 112.926  1.00 32.38      B  C
ATOM   5229  C    PRO B 380      27.168  49.715 113.057  1.00 40.78      B  C
ATOM   5230  O    PRO B 380      26.228  50.345 113.549  1.00 40.78      B  O
ATOM   5231  N    HIS B 381      28.263  50.306 112.597  1.00 34.22      B  N
ATOM   5232  CA   HIS B 381      28.455  51.747 112.698  1.00 34.22      B  C
ATOM   5233  CB   HIS B 381      29.843  52.108 112.214  1.00 33.19      B  C
ATOM   5234  CG   HIS B 381      29.983  52.023 110.728  1.00 33.19      B  C
ATOM   5235  CD2  HIS B 381      30.511  51.061 109.936  1.00 33.19      B  C
ATOM   5236  ND1  HIS B 381      29.509  53.000 109.881  1.00 33.19      B  N
ATOM   5237  CE1  HIS B 381      29.744  52.647 108.631  1.00 33.19      B  C
ATOM   5238  NE2  HIS B 381      30.351  51.474 108.637  1.00 33.19      B  N
ATOM   5239  C    HIS B 381      27.452  52.637 111.912  1.00 34.22      B  C
ATOM   5240  O    HIS B 381      27.422  53.851 112.106  1.00 34.22      B  O
ATOM   5241  N    ALA B 382      26.651  52.068 111.016  1.00 58.90      B  N
ATOM   5242  CA   ALA B 382      25.717  52.897 110.239  1.00 58.90      B  C
ATOM   5243  CB   ALA B 382      25.610  52.352 108.810  1.00 24.34      B  C
ATOM   5244  C    ALA B 382      24.316  53.028 110.858  1.00 58.90      B  C
ATOM   5245  O    ALA B 382      23.856  52.055 111.506  1.00 58.90      B  O
ATOM   5246  OXT  ALA B 382      23.675  54.089 110.657  1.00 24.34      B  O
TER    5247       ALA B 382                                              B
ATOM   5248  O    HOH W   3      15.375  58.039  78.308  1.00 28.96      W  O
ATOM   5249  O    HOH W   2      36.184  58.995  88.945  1.00 28.59      W  O
ATOM   5250  O    HOH W   4      16.766  58.125  81.755  1.00 22.88      W  O
ATOM   5251  O    HOH W   5      26.239  46.976 102.908  1.00 41.98      W  O
ATOM   5252  O    HOH W   6      22.272  38.560  70.890  1.00 25.85      W  O
ATOM   5253  O    HOH W   7      19.070  41.701  66.616  1.00 21.64      W  O
TER    5254       HOH W   7                                              W
ATOM   5255  C1   INH I   1      40.782  39.301  55.233  1.00 45.17      I  C
ATOM   5256  N2   INH I   1      40.469  38.584  56.389  1.00 45.17      I  N
ATOM   5257  C3   INH I   1      40.087  37.234  56.333  1.00 45.17      I  C
ATOM   5258  N4   INH I   1      40.040  36.640  55.063  1.00 45.17      I  N
ATOM   5259  C5   INH I   1      40.325  37.279  53.869  1.00 45.17      I  C
ATOM   5260  C6   INH I   1      40.713  38.659  53.868  1.00 45.17      I  C
ATOM   5261  C7   INH I   1      41.036  39.402  52.660  1.00 45.17      I  C
ATOM   5262  C8   INH I   1      41.455  40.820  52.793  1.00 45.17      I  C
ATOM   5263  C9   INH I   1      41.544  41.472  54.114  1.00 45.17      I  C
ATOM   5264  C10  INH I   1      41.203  40.697  55.322  1.00 45.17      I  C
ATOM   5265  C15  INH I   1      39.725  36.472  57.531  1.00 45.17      I  C
ATOM   5266  C16  INH I   1      40.267  36.940  58.795  1.00 45.17      I  C
ATOM   5267  C17  INH I   1      39.896  36.180  59.952  1.00 45.17      I  C
ATOM   5268  N18  INH I   1      39.044  35.040  59.824  1.00 45.17      I  N
ATOM   5269  C19  INH I   1      38.512  34.573  58.603  1.00 45.17      I  C
ATOM   5270  C20  INH I   1      38.846  35.296  57.390  1.00 45.17      I  C
ATOM   5271  N25  INH I   1      40.263  36.633  52.626  1.00 45.17      I  N
ATOM   5272  C26  INH I   1      39.762  35.254  52.406  1.00 45.17      I  C
ATOM   5273  N27  INH I   1      40.098  34.408  51.423  1.00 45.17      I  N
ATOM   5274  N1   INH I   1      39.465  33.241  51.604  1.00 45.17      I  N
ATOM   5275  C29  INH I   1      38.695  33.262  52.689  1.00 45.17      I  C
ATOM   5276  C30  INH I   1      38.848  34.534  53.242  1.00 45.17      I  C
ATOM   5277  C33  INH I   1      37.818  32.194  53.256  1.00 45.17      I  C
TER    5278       INH I   1                                              I
END
```

FIG. 5-1

|  | Atom Type | Resid | # | X | Y | Z | Occ | B |  |  |
|---|---|---|---|---|---|---|---|---|---|---|
| ATOM | 1 | CB | SER A | 25 | 50.525 | 13.786 | 60.068 | 1.00 | 58.97 | A | C |
| ATOM | 2 | OG | SER A | 25 | 51.460 | 14.567 | 60.805 | 1.00 | 59.45 | A | O |
| ATOM | 3 | C | SER A | 25 | 50.204 | 15.506 | 58.258 | 1.00 | 58.77 | A | C |
| ATOM | 4 | O | SER A | 25 | 50.006 | 15.267 | 57.052 | 1.00 | 58.51 | A | O |
| ATOM | 5 | N | SER A | 25 | 48.413 | 13.839 | 58.781 | 1.00 | 58.43 | A | N |
| ATOM | 6 | CA | SER A | 25 | 49.505 | 14.680 | 59.350 | 1.00 | 58.91 | A | C |
| ATOM | 7 | N | MET A | 26 | 51.021 | 16.472 | 58.679 | 1.00 | 58.75 | A | N |
| ATOM | 8 | CA | MET A | 26 | 51.731 | 17.328 | 57.737 | 1.00 | 59.40 | A | C |
| ATOM | 9 | CB | MET A | 26 | 51.255 | 18.777 | 57.876 | 1.00 | 60.00 | A | C |
| ATOM | 10 | CG | MET A | 26 | 51.399 | 19.370 | 59.273 | 1.00 | 60.28 | A | C |
| ATOM | 11 | SD | MET A | 26 | 50.974 | 21.150 | 59.298 | 1.00 | 62.28 | A | S |
| ATOM | 12 | CE | MET A | 26 | 49.132 | 21.083 | 59.155 | 1.00 | 59.79 | A | C |
| ATOM | 13 | C | MET A | 26 | 53.259 | 17.292 | 57.868 | 1.00 | 59.88 | A | C |
| ATOM | 14 | O | MET A | 26 | 53.820 | 17.193 | 58.982 | 1.00 | 60.14 | A | O |
| ATOM | 15 | N | LYS A | 27 | 53.920 | 17.376 | 56.716 | 1.00 | 60.01 | A | N |
| ATOM | 16 | CA | LYS A | 27 | 55.378 | 17.377 | 56.622 | 1.00 | 59.77 | A | C |
| ATOM | 17 | CB | LYS A | 27 | 55.794 | 17.002 | 55.194 | 1.00 | 60.08 | A | C |
| ATOM | 18 | CG | LYS A | 27 | 54.712 | 16.211 | 54.420 | 1.00 | 60.25 | A | C |
| ATOM | 19 | CD | LYS A | 27 | 55.021 | 14.718 | 54.320 | 1.00 | 60.62 | A | C |
| ATOM | 20 | CE | LYS A | 27 | 55.273 | 14.086 | 55.695 | 1.00 | 60.17 | A | C |
| ATOM | 21 | NZ | LYS A | 27 | 55.809 | 12.691 | 55.554 | 1.00 | 59.43 | A | N |
| ATOM | 22 | C | LYS A | 27 | 55.756 | 18.826 | 56.923 | 1.00 | 59.87 | A | C |
| ATOM | 23 | O | LYS A | 27 | 54.878 | 19.651 | 57.085 | 1.00 | 60.55 | A | O |
| ATOM | 24 | N | VAL A | 28 | 57.045 | 19.145 | 56.985 | 1.00 | 59.86 | A | N |
| ATOM | 25 | CA | VAL A | 28 | 57.454 | 20.517 | 57.291 | 1.00 | 59.22 | A | C |
| ATOM | 26 | CB | VAL A | 28 | 56.981 | 20.916 | 58.714 | 1.00 | 59.14 | A | C |
| ATOM | 27 | CG1 | VAL A | 28 | 57.268 | 19.766 | 59.689 | 1.00 | 59.26 | A | C |
| ATOM | 28 | CG2 | VAL A | 28 | 57.686 | 22.193 | 59.178 | 1.00 | 58.44 | A | C |
| ATOM | 29 | C | VAL A | 28 | 58.974 | 20.651 | 57.205 | 1.00 | 59.24 | A | C |
| ATOM | 30 | O | VAL A | 28 | 59.698 | 20.003 | 57.954 | 1.00 | 58.99 | A | O |
| ATOM | 31 | N | GLY A | 29 | 59.442 | 21.500 | 56.290 | 1.00 | 59.43 | A | N |
| ATOM | 32 | CA | GLY A | 29 | 60.869 | 21.698 | 56.105 | 1.00 | 60.14 | A | C |
| ATOM | 33 | C | GLY A | 29 | 61.172 | 23.136 | 55.725 | 1.00 | 61.64 | A | C |
| ATOM | 34 | O | GLY A | 29 | 60.397 | 24.042 | 56.054 | 1.00 | 61.50 | A | O |
| ATOM | 35 | N | ARG A | 30 | 62.289 | 23.360 | 55.030 | 1.00 | 62.90 | A | N |
| ATOM | 36 | CA | ARG A | 30 | 62.672 | 24.714 | 54.625 | 1.00 | 64.10 | A | C |
| ATOM | 37 | CB | ARG A | 30 | 63.600 | 25.345 | 55.682 | 1.00 | 63.51 | A | C |
| ATOM | 38 | CG | ARG A | 30 | 62.947 | 25.534 | 57.051 | 1.00 | 64.09 | A | C |
| ATOM | 39 | CD | ARG A | 30 | 63.822 | 26.343 | 58.021 | 1.00 | 64.87 | A | C |
| ATOM | 40 | NE | ARG A | 30 | 63.126 | 26.652 | 59.277 | 1.00 | 64.27 | A | N |
| ATOM | 41 | CZ | ARG A | 30 | 62.622 | 25.739 | 60.110 | 1.00 | 64.27 | A | C |
| ATOM | 42 | NH1 | ARG A | 30 | 62.008 | 26.122 | 61.228 | 1.00 | 63.19 | A | N |
| ATOM | 43 | NH2 | ARG A | 30 | 62.732 | 24.441 | 59.827 | 1.00 | 63.59 | A | N |
| ATOM | 44 | C | ARG A | 30 | 63.361 | 24.726 | 53.258 | 1.00 | 65.03 | A | C |
| ATOM | 45 | O | ARG A | 30 | 62.693 | 24.682 | 52.194 | 1.00 | 65.27 | A | O |
| ATOM | 46 | N | GLY A | 31 | 64.692 | 24.785 | 53.277 | 1.00 | 66.07 | A | N |
| ATOM | 47 | CA | GLY A | 31 | 65.444 | 24.803 | 52.032 | 1.00 | 66.84 | A | C |
| ATOM | 48 | C | GLY A | 31 | 64.930 | 25.911 | 51.131 | 1.00 | 67.49 | A | C |
| ATOM | 49 | O | GLY A | 31 | 64.182 | 26.803 | 51.591 | 1.00 | 67.60 | A | O |
| ATOM | 50 | N | GLY A | 32 | 65.314 | 25.872 | 49.856 | 1.00 | 67.78 | A | N |
| ATOM | 51 | CA | GLY A | 32 | 64.856 | 26.895 | 48.929 | 1.00 | 67.77 | A | C |
| ATOM | 52 | C | GLY A | 32 | 65.294 | 28.302 | 49.318 | 1.00 | 67.71 | A | C |
| ATOM | 53 | O | GLY A | 32 | 64.955 | 29.288 | 48.626 | 1.00 | 67.42 | A | O |
| ATOM | 54 | N | GLY A | 33 | 66.037 | 28.413 | 50.419 | 1.00 | 67.26 | A | N |
| ATOM | 55 | CA | GLY A | 33 | 66.515 | 29.718 | 50.845 | 1.00 | 66.49 | A | C |
| ATOM | 56 | C | GLY A | 33 | 66.116 | 30.193 | 52.233 | 1.00 | 65.96 | A | C |
| ATOM | 57 | O | GLY A | 33 | 65.822 | 31.381 | 52.413 | 1.00 | 66.43 | A | O |
| ATOM | 58 | N | GLY A | 34 | 66.090 | 29.287 | 53.209 | 1.00 | 64.96 | A | N |

FIG. 5-2

```
ATOM     59  CA   GLY A  34      65.747  29.679  54.570  1.00 63.30      A    C
ATOM     60  C    GLY A  34      64.274  29.681  54.965  1.00 62.62      A    C
ATOM     61  O    GLY A  34      63.935  29.321  56.113  1.00 62.57      A    O
ATOM     62  N    GLY A  35      63.399  30.092  54.044  1.00 61.44      A    N
ATOM     63  CA   GLY A  35      61.968  30.140  54.329  1.00 59.61      A    C
ATOM     64  C    GLY A  35      61.351  28.775  54.616  1.00 58.45      A    C
ATOM     65  O    GLY A  35      61.651  27.764  53.907  1.00 58.70      A    O
ATOM     66  N    LYS A  36      60.485  28.740  55.634  1.00 56.00      A    N
ATOM     67  CA   LYS A  36      59.804  27.523  56.097  1.00 53.37      A    C
ATOM     68  CB   LYS A  36      59.270  27.736  57.513  1.00 52.99      A    C
ATOM     69  CG   LYS A  36      58.499  26.548  58.055  1.00 53.34      A    C
ATOM     70  CD   LYS A  36      57.511  26.978  59.141  1.00 53.43      A    C
ATOM     71  CE   LYS A  36      56.682  25.789  59.617  1.00 53.63      A    C
ATOM     72  NZ   LYS A  36      55.630  26.174  60.608  1.00 53.54      A    N
ATOM     73  C    LYS A  36      58.648  27.050  55.217  1.00 52.22      A    C
ATOM     74  O    LYS A  36      57.699  27.798  54.956  1.00 52.26      A    O
ATOM     75  N    VAL A  37      58.709  25.785  54.809  1.00 49.85      A    N
ATOM     76  CA   VAL A  37      57.687  25.207  53.944  1.00 47.09      A    C
ATOM     77  CB   VAL A  37      58.334  24.565  52.709  1.00 47.71      A    C
ATOM     78  CG1  VAL A  37      57.271  23.916  51.830  1.00 47.93      A    C
ATOM     79  CG2  VAL A  37      59.124  25.607  51.947  1.00 47.47      A    C
ATOM     80  C    VAL A  37      56.821  24.144  54.610  1.00 45.60      A    C
ATOM     81  O    VAL A  37      57.328  23.255  55.305  1.00 44.56      A    O
ATOM     82  N    THR A  38      55.512  24.234  54.386  1.00 43.86      A    N
ATOM     83  CA   THR A  38      54.588  23.255  54.941  1.00 42.42      A    C
ATOM     84  CB   THR A  38      53.471  23.922  55.760  1.00 42.44      A    C
ATOM     85  OG1  THR A  38      54.057  24.774  56.756  1.00 43.50      A    O
ATOM     86  CG2  THR A  38      52.620  22.861  56.449  1.00 39.73      A    C
ATOM     87  C    THR A  38      53.971  22.429  53.816  1.00 41.94      A    C
ATOM     88  O    THR A  38      53.277  22.954  52.933  1.00 41.54      A    O
ATOM     89  N    THR A  39      54.248  21.132  53.849  1.00 41.21      A    N
ATOM     90  CA   THR A  39      53.733  20.199  52.863  1.00 39.88      A    C
ATOM     91  CB   THR A  39      54.879  19.348  52.228  1.00 40.37      A    C
ATOM     92  OG1  THR A  39      55.648  20.172  51.343  1.00 41.50      A    O
ATOM     93  CG2  THR A  39      54.315  18.177  51.435  1.00 40.37      A    C
ATOM     94  C    THR A  39      52.718  19.288  53.533  1.00 38.84      A    C
ATOM     95  O    THR A  39      53.009  18.666  54.556  1.00 38.74      A    O
ATOM     96  N    VAL A  40      51.524  19.223  52.951  1.00 37.06      A    N
ATOM     97  CA   VAL A  40      50.445  18.410  53.497  1.00 36.31      A    C
ATOM     98  CB   VAL A  40      49.414  19.312  54.232  1.00 37.19      A    C
ATOM     99  CG1  VAL A  40      48.700  20.213  53.230  1.00 35.51      A    C
ATOM    100  CG2  VAL A  40      48.413  18.458  54.993  1.00 38.77      A    C
ATOM    101  C    VAL A  40      49.729  17.635  52.378  1.00 35.66      A    C
ATOM    102  O    VAL A  40      49.787  18.021  51.221  1.00 36.32      A    O
ATOM    103  N    VAL A  41      49.080  16.527  52.718  1.00 34.41      A    N
ATOM    104  CA   VAL A  41      48.343  15.772  51.712  1.00 32.76      A    C
ATOM    105  CB   VAL A  41      48.433  14.243  51.921  1.00 31.73      A    C
ATOM    106  CG1  VAL A  41      47.594  13.541  50.865  1.00 31.12      A    C
ATOM    107  CG2  VAL A  41      49.881  13.772  51.836  1.00 30.03      A    C
ATOM    108  C    VAL A  41      46.881  16.185  51.856  1.00 33.34      A    C
ATOM    109  O    VAL A  41      46.244  15.907  52.881  1.00 31.86      A    O
ATOM    110  N    ALA A  42      46.345  16.848  50.835  1.00 32.88      A    N
ATOM    111  CA   ALA A  42      44.966  17.308  50.901  1.00 33.72      A    C
ATOM    112  CB   ALA A  42      44.929  18.823  50.793  1.00 34.11      A    C
ATOM    113  C    ALA A  42      44.009  16.694  49.875  1.00 33.79      A    C
ATOM    114  O    ALA A  42      44.422  16.141  48.871  1.00 34.09      A    O
ATOM    115  N    THR A  43      42.715  16.824  50.155  1.00 33.74      A    N
ATOM    116  CA   THR A  43      41.657  16.326  49.285  1.00 33.43      A    C
ATOM    117  CB   THR A  43      40.462  15.796  50.112  1.00 33.68      A    C
ATOM    118  OG1  THR A  43      40.915  14.820  51.060  1.00 32.70      A    O
```

FIG. 5-3

| ATOM | 119 | CG2 | THR | A | 43 | 39.409 | 15.175 | 49.203 | 1.00 | 32.72 | A | C |
|------|-----|-----|-----|---|----|--------|--------|--------|------|-------|---|---|
| ATOM | 120 | C | THR | A | 43 | 41.140 | 17.490 | 48.445 | 1.00 | 34.82 | A | C |
| ATOM | 121 | O | THR | A | 43 | 40.944 | 18.574 | 48.958 | 1.00 | 35.11 | A | O |
| ATOM | 122 | N | PRO | A | 44 | 40.908 | 17.267 | 47.140 | 1.00 | 36.18 | A | N |
| ATOM | 123 | CD | PRO | A | 44 | 41.172 | 16.020 | 46.398 | 1.00 | 35.95 | A | C |
| ATOM | 124 | CA | PRO | A | 44 | 40.408 | 18.316 | 46.240 | 1.00 | 36.40 | A | C |
| ATOM | 125 | CB | PRO | A | 44 | 40.342 | 17.606 | 44.887 | 1.00 | 35.65 | A | C |
| ATOM | 126 | CG | PRO | A | 44 | 41.390 | 16.530 | 45.001 | 1.00 | 36.92 | A | C |
| ATOM | 127 | C | PRO | A | 44 | 39.019 | 18.779 | 46.689 | 1.00 | 37.09 | A | C |
| ATOM | 128 | O | PRO | A | 44 | 38.226 | 17.977 | 47.151 | 1.00 | 35.98 | A | O |
| ATOM | 129 | N | GLY | A | 45 | 38.732 | 20.071 | 46.547 | 1.00 | 38.88 | A | N |
| ATOM | 130 | CA | GLY | A | 45 | 37.425 | 20.575 | 46.944 | 1.00 | 41.67 | A | C |
| ATOM | 131 | C | GLY | A | 45 | 36.305 | 19.915 | 46.158 | 1.00 | 43.54 | A | C |
| ATOM | 132 | O | GLY | A | 45 | 35.312 | 19.504 | 46.723 | 1.00 | 44.32 | A | O |
| ATOM | 133 | N | ALA | A | 46 | 36.478 | 19.817 | 44.843 | 1.00 | 45.58 | A | N |
| ATOM | 134 | CA | ALA | A | 46 | 35.489 | 19.187 | 43.970 | 1.00 | 48.05 | A | C |
| ATOM | 135 | CB | ALA | A | 46 | 35.068 | 20.166 | 42.873 | 1.00 | 47.77 | A | C |
| ATOM | 136 | C | ALA | A | 46 | 36.103 | 17.924 | 43.343 | 1.00 | 49.63 | A | C |
| ATOM | 137 | O | ALA | A | 46 | 37.323 | 17.736 | 43.358 | 1.00 | 49.44 | A | O |
| ATOM | 138 | N | GLY | A | 47 | 35.262 | 17.067 | 42.778 | 1.00 | 51.39 | A | N |
| ATOM | 139 | CA | GLY | A | 47 | 35.774 | 15.849 | 42.173 | 1.00 | 53.09 | A | C |
| ATOM | 140 | C | GLY | A | 47 | 35.907 | 14.789 | 43.247 | 1.00 | 54.67 | A | C |
| ATOM | 141 | O | GLY | A | 47 | 35.760 | 15.100 | 44.428 | 1.00 | 55.27 | A | O |
| ATOM | 142 | N | PRO | A | 48 | 36.186 | 13.528 | 42.882 | 1.00 | 55.40 | A | N |
| ATOM | 143 | CD | PRO | A | 48 | 36.121 | 12.991 | 41.518 | 1.00 | 55.61 | A | C |
| ATOM | 144 | CA | PRO | A | 48 | 36.324 | 12.438 | 43.862 | 1.00 | 55.23 | A | C |
| ATOM | 145 | CB | PRO | A | 48 | 36.210 | 11.176 | 43.003 | 1.00 | 55.88 | A | C |
| ATOM | 146 | CG | PRO | A | 48 | 35.446 | 11.665 | 41.771 | 1.00 | 56.89 | A | C |
| ATOM | 147 | C | PRO | A | 48 | 37.639 | 12.474 | 44.648 | 1.00 | 54.49 | A | C |
| ATOM | 148 | O | PRO | A | 48 | 38.691 | 12.927 | 44.140 | 1.00 | 53.39 | A | O |
| ATOM | 149 | N | ASP | A | 49 | 37.571 | 11.980 | 45.884 | 1.00 | 53.85 | A | N |
| ATOM | 150 | CA | ASP | A | 49 | 38.724 | 11.956 | 46.766 | 1.00 | 52.11 | A | C |
| ATOM | 151 | CB | ASP | A | 49 | 38.436 | 11.145 | 48.027 | 1.00 | 53.04 | A | C |
| ATOM | 152 | CG | ASP | A | 49 | 39.656 | 11.024 | 48.922 | 1.00 | 54.33 | A | C |
| ATOM | 153 | OD1 | ASP | A | 49 | 40.331 | 12.059 | 49.148 | 1.00 | 53.63 | A | O |
| ATOM | 154 | OD2 | ASP | A | 49 | 39.935 | 9.900 | 49.402 | 1.00 | 55.67 | A | O |
| ATOM | 155 | C | ASP | A | 49 | 39.951 | 11.369 | 46.077 | 1.00 | 50.64 | A | C |
| ATOM | 156 | O | ASP | A | 49 | 40.047 | 10.154 | 45.854 | 1.00 | 51.29 | A | O |
| ATOM | 157 | N | ARG | A | 50 | 40.878 | 12.255 | 45.732 | 1.00 | 48.25 | A | N |
| ATOM | 158 | CA | ARG | A | 50 | 42.145 | 11.899 | 45.105 | 1.00 | 45.92 | A | C |
| ATOM | 159 | CB | ARG | A | 50 | 42.100 | 12.149 | 43.600 | 1.00 | 46.66 | A | C |
| ATOM | 160 | CG | ARG | A | 50 | 43.426 | 11.900 | 42.925 | 1.00 | 47.80 | A | C |
| ATOM | 161 | CD | ARG | A | 50 | 43.235 | 11.618 | 41.444 | 1.00 | 50.23 | A | C |
| ATOM | 162 | NE | ARG | A | 50 | 43.166 | 12.822 | 40.624 | 1.00 | 50.76 | A | N |
| ATOM | 163 | CZ | ARG | A | 50 | 42.453 | 12.908 | 39.502 | 1.00 | 51.67 | A | C |
| ATOM | 164 | NH1 | ARG | A | 50 | 41.749 | 11.854 | 39.087 | 1.00 | 50.57 | A | N |
| ATOM | 165 | NH2 | ARG | A | 50 | 42.456 | 14.032 | 38.793 | 1.00 | 51.40 | A | N |
| ATOM | 166 | C | ARG | A | 50 | 43.201 | 12.807 | 45.743 | 1.00 | 43.59 | A | C |
| ATOM | 167 | O | ARG | A | 50 | 43.532 | 13.867 | 45.214 | 1.00 | 42.53 | A | O |
| ATOM | 168 | N | PRO | A | 51 | 43.772 | 12.371 | 46.872 | 1.00 | 42.25 | A | N |
| ATOM | 169 | CD | PRO | A | 51 | 43.870 | 10.949 | 47.240 | 1.00 | 41.38 | A | C |
| ATOM | 170 | CA | PRO | A | 51 | 44.776 | 13.147 | 47.604 | 1.00 | 40.83 | A | C |
| ATOM | 171 | CB | PRO | A | 51 | 45.353 | 12.136 | 48.595 | 1.00 | 40.67 | A | C |
| ATOM | 172 | CG | PRO | A | 51 | 44.339 | 11.039 | 48.659 | 1.00 | 41.56 | A | C |
| ATOM | 173 | C | PRO | A | 51 | 45.879 | 13.690 | 46.721 | 1.00 | 40.24 | A | C |
| ATOM | 174 | O | PRO | A | 51 | 46.152 | 13.169 | 45.655 | 1.00 | 40.61 | A | O |
| ATOM | 175 | N | GLN | A | 52 | 46.538 | 14.732 | 47.199 | 1.00 | 40.74 | A | N |
| ATOM | 176 | CA | GLN | A | 52 | 47.642 | 15.320 | 46.464 | 1.00 | 41.06 | A | C |
| ATOM | 177 | CB | GLN | A | 52 | 47.116 | 16.117 | 45.277 | 1.00 | 43.82 | A | C |
| ATOM | 178 | CG | GLN | A | 52 | 45.734 | 16.675 | 45.493 | 1.00 | 46.93 | A | C |

FIG. 5-4

| | | | | | | | | | | |
|---|---|---|---|---|---|---|---|---|---|---|
| ATOM | 179 | CD | GLN | A | 52 | 44.914 | 16.654 | 44.212 | 1.00 49.85 | A C |
| ATOM | 180 | OE1 | GLN | A | 52 | 44.915 | 15.648 | 43.472 | 1.00 49.51 | A O |
| ATOM | 181 | NE2 | GLN | A | 52 | 44.196 | 17.752 | 43.941 | 1.00 51.56 | A N |
| ATOM | 182 | C | GLN | A | 52 | 48.441 | 16.227 | 47.366 | 1.00 39.71 | A C |
| ATOM | 183 | O | GLN | A | 52 | 47.884 | 16.988 | 48.129 | 1.00 40.61 | A O |
| ATOM | 184 | N | GLU | A | 53 | 49.759 | 16.127 | 47.267 | 1.00 38.79 | A N |
| ATOM | 185 | CA | GLU | A | 53 | 50.632 | 16.933 | 48.096 | 1.00 38.52 | A C |
| ATOM | 186 | CB | GLU | A | 53 | 52.083 | 16.518 | 47.928 | 1.00 39.77 | A C |
| ATOM | 187 | CG | GLU | A | 53 | 52.396 | 15.193 | 48.540 | 1.00 41.60 | A C |
| ATOM | 188 | CD | GLU | A | 53 | 53.876 | 14.942 | 48.579 | 1.00 41.96 | A C |
| ATOM | 189 | OE1 | GLU | A | 53 | 54.272 | 13.864 | 49.064 | 1.00 43.69 | A O |
| ATOM | 190 | OE2 | GLU | A | 53 | 54.637 | 15.828 | 48.129 | 1.00 41.87 | A O |
| ATOM | 191 | C | GLU | A | 53 | 50.528 | 18.401 | 47.757 | 1.00 37.62 | A C |
| ATOM | 192 | O | GLU | A | 53 | 50.575 | 18.784 | 46.602 | 1.00 37.31 | A O |
| ATOM | 193 | N | VAL | A | 54 | 50.393 | 19.221 | 48.787 | 1.00 36.29 | A N |
| ATOM | 194 | CA | VAL | A | 54 | 50.314 | 20.651 | 48.589 | 1.00 35.98 | A C |
| ATOM | 195 | CB | VAL | A | 54 | 48.902 | 21.201 | 48.952 | 1.00 36.75 | A C |
| ATOM | 196 | CG1 | VAL | A | 54 | 48.832 | 22.694 | 48.672 | 1.00 35.95 | A C |
| ATOM | 197 | CG2 | VAL | A | 54 | 47.836 | 20.478 | 48.149 | 1.00 36.23 | A C |
| ATOM | 198 | C | VAL | A | 54 | 51.355 | 21.285 | 49.503 | 1.00 34.98 | A C |
| ATOM | 199 | O | VAL | A | 54 | 51.435 | 20.950 | 50.680 | 1.00 34.94 | A O |
| ATOM | 200 | N | SER | A | 55 | 52.158 | 22.181 | 48.941 | 1.00 33.94 | A N |
| ATOM | 201 | CA | SER | A | 55 | 53.212 | 22.863 | 49.686 | 1.00 34.42 | A C |
| ATOM | 202 | CB | SER | A | 55 | 54.588 | 22.564 | 49.075 | 1.00 35.24 | A C |
| ATOM | 203 | OG | SER | A | 55 | 54.867 | 21.175 | 49.087 | 1.00 37.72 | A O |
| ATOM | 204 | C | SER | A | 55 | 52.984 | 24.365 | 49.642 | 1.00 33.26 | A C |
| ATOM | 205 | O | SER | A | 55 | 52.781 | 24.937 | 48.575 | 1.00 31.61 | A O |
| ATOM | 206 | N | TYR | A | 56 | 53.023 | 25.000 | 50.806 | 1.00 34.02 | A N |
| ATOM | 207 | CA | TYR | A | 56 | 52.826 | 26.441 | 50.877 | 1.00 35.32 | A C |
| ATOM | 208 | CB | TYR | A | 56 | 51.377 | 26.765 | 51.236 | 1.00 35.51 | A C |
| ATOM | 209 | CG | TYR | A | 56 | 50.881 | 26.140 | 52.525 | 1.00 35.43 | A C |
| ATOM | 210 | CD1 | TYR | A | 56 | 51.184 | 26.699 | 53.762 | 1.00 35.08 | A C |
| ATOM | 211 | CE1 | TYR | A | 56 | 50.687 | 26.144 | 54.946 | 1.00 35.64 | A C |
| ATOM | 212 | CD2 | TYR | A | 56 | 50.075 | 25.002 | 52.495 | 1.00 35.75 | A C |
| ATOM | 213 | CE2 | TYR | A | 56 | 49.575 | 24.438 | 53.665 | 1.00 35.84 | A C |
| ATOM | 214 | CZ | TYR | A | 56 | 49.881 | 25.013 | 54.885 | 1.00 36.18 | A C |
| ATOM | 215 | OH | TYR | A | 56 | 49.366 | 24.459 | 56.031 | 1.00 37.16 | A O |
| ATOM | 216 | C | TYR | A | 56 | 53.770 | 27.081 | 51.885 | 1.00 35.63 | A C |
| ATOM | 217 | O | TYR | A | 56 | 54.270 | 26.422 | 52.773 | 1.00 35.68 | A O |
| ATOM | 218 | N | THR | A | 57 | 54.008 | 28.377 | 51.718 | 1.00 37.70 | A N |
| ATOM | 219 | CA | THR | A | 57 | 54.878 | 29.124 | 52.614 | 1.00 40.01 | A C |
| ATOM | 220 | CB | THR | A | 57 | 56.275 | 29.367 | 52.002 | 1.00 41.03 | A C |
| ATOM | 221 | OG1 | THR | A | 57 | 56.736 | 28.180 | 51.348 | 1.00 45.34 | A O |
| ATOM | 222 | CG2 | THR | A | 57 | 57.267 | 29.737 | 53.093 | 1.00 42.02 | A C |
| ATOM | 223 | C | THR | A | 57 | 54.283 | 30.499 | 52.885 | 1.00 40.37 | A C |
| ATOM | 224 | O | THR | A | 57 | 53.144 | 30.771 | 52.533 | 1.00 40.19 | A O |
| ATOM | 225 | N | ASP | A | 58 | 55.092 | 31.360 | 53.498 | 1.00 41.66 | A N |
| ATOM | 226 | CA | ASP | A | 58 | 54.709 | 32.726 | 53.825 | 1.00 42.65 | A C |
| ATOM | 227 | CB | ASP | A | 58 | 54.832 | 33.619 | 52.588 | 1.00 44.47 | A C |
| ATOM | 228 | CG | ASP | A | 58 | 56.247 | 33.667 | 52.049 | 1.00 47.19 | A C |
| ATOM | 229 | OD1 | ASP | A | 58 | 57.162 | 34.057 | 52.822 | 1.00 48.17 | A O |
| ATOM | 230 | OD2 | ASP | A | 58 | 56.437 | 33.317 | 50.855 | 1.00 46.47 | A O |
| ATOM | 231 | C | ASP | A | 58 | 53.306 | 32.854 | 54.394 | 1.00 42.35 | A C |
| ATOM | 232 | O | ASP | A | 58 | 52.510 | 33.639 | 53.895 | 1.00 42.18 | A O |
| ATOM | 233 | N | THR | A | 59 | 52.998 | 32.093 | 55.437 | 1.00 41.67 | A N |
| ATOM | 234 | CA | THR | A | 59 | 51.669 | 32.195 | 56.010 | 1.00 41.28 | A C |
| ATOM | 235 | CB | THR | A | 59 | 51.234 | 30.901 | 56.732 | 1.00 41.78 | A C |
| ATOM | 236 | OG1 | THR | A | 59 | 52.104 | 30.652 | 57.841 | 1.00 43.07 | A O |
| ATOM | 237 | CG2 | THR | A | 59 | 51.265 | 29.719 | 55.772 | 1.00 39.88 | A C |
| ATOM | 238 | C | THR | A | 59 | 51.580 | 33.348 | 56.992 | 1.00 41.08 | A C |

FIG. 5-5

```
ATOM    239  O    THR A  59      52.515  33.627  57.726  1.00 41.18    A    O
ATOM    240  N    LYS A  60      50.446  34.030  56.979  1.00 40.59    A    N
ATOM    241  CA   LYS A  60      50.220  35.146  57.886  1.00 40.60    A    C
ATOM    242  CB   LYS A  60      50.673  36.464  57.255  1.00 40.46    A    C
ATOM    243  CG   LYS A  60      50.004  36.790  55.937  1.00 42.32    A    C
ATOM    244  CD   LYS A  60      50.484  38.126  55.387  1.00 44.33    A    C
ATOM    245  CE   LYS A  60      52.016  38.167  55.222  1.00 46.73    A    C
ATOM    246  NZ   LYS A  60      52.555  37.173  54.225  1.00 47.60    A    N
ATOM    247  C    LYS A  60      48.728  35.201  58.192  1.00 39.63    A    C
ATOM    248  O    LYS A  60      47.905  34.743  57.390  1.00 39.27    A    O
ATOM    249  N    VAL A  61      48.379  35.749  59.350  1.00 38.44    A    N
ATOM    250  CA   VAL A  61      46.979  35.852  59.722  1.00 37.54    A    C
ATOM    251  CB   VAL A  61      46.806  36.101  61.233  1.00 36.66    A    C
ATOM    252  CG1  VAL A  61      45.331  36.201  61.573  1.00 33.77    A    C
ATOM    253  CG2  VAL A  61      47.463  34.970  62.025  1.00 36.27    A    C
ATOM    254  C    VAL A  61      46.339  37.011  58.968  1.00 37.39    A    C
ATOM    255  O    VAL A  61      46.963  38.050  58.756  1.00 36.45    A    O
ATOM    256  N    ILE A  62      45.091  36.823  58.555  1.00 37.26    A    N
ATOM    257  CA   ILE A  62      44.374  37.864  57.834  1.00 36.99    A    C
ATOM    258  CB   ILE A  62      44.300  37.561  56.306  1.00 35.84    A    C
ATOM    259  CG2  ILE A  62      45.698  37.444  55.736  1.00 35.15    A    C
ATOM    260  CG1  ILE A  62      43.528  36.265  56.043  1.00 35.77    A    C
ATOM    261  CD1  ILE A  62      43.376  35.927  54.553  1.00 32.53    A    C
ATOM    262  C    ILE A  62      42.959  38.014  58.378  1.00 37.86    A    C
ATOM    263  O    ILE A  62      42.255  38.989  58.064  1.00 38.57    A    O
ATOM    264  N    GLY A  63      42.538  37.050  59.191  1.00 37.18    A    N
ATOM    265  CA   GLY A  63      41.205  37.119  59.753  1.00 37.58    A    C
ATOM    266  C    GLY A  63      40.997  36.212  60.949  1.00 37.75    A    C
ATOM    267  O    GLY A  63      41.750  35.281  61.171  1.00 38.45    A    O
ATOM    268  N    ASN A  64      39.950  36.496  61.711  1.00 37.92    A    N
ATOM    269  CA   ASN A  64      39.622  35.715  62.892  1.00 37.46    A    C
ATOM    270  CB   ASN A  64      39.903  36.538  64.146  1.00 41.19    A    C
ATOM    271  CG   ASN A  64      40.295  35.681  65.327  1.00 44.57    A    C
ATOM    272  OD1  ASN A  64      41.502  35.329  65.502  1.00 47.77    A    O
ATOM    273  ND2  ASN A  64      39.304  35.312  66.148  1.00 45.47    A    N
ATOM    274  C    ASN A  64      38.131  35.407  62.833  1.00 35.65    A    C
ATOM    275  O    ASN A  64      37.350  36.157  62.218  1.00 34.96    A    O
ATOM    276  N    GLY A  65      37.733  34.322  63.486  1.00 33.01    A    N
ATOM    277  CA   GLY A  65      36.334  33.940  63.503  1.00 31.40    A    C
ATOM    278  C    GLY A  65      36.053  32.978  64.636  1.00 30.43    A    C
ATOM    279  O    GLY A  65      36.962  32.608  65.356  1.00 29.27    A    O
ATOM    280  N    SER A  66      34.799  32.566  64.785  1.00 29.07    A    N
ATOM    281  CA   SER A  66      34.435  31.660  65.860  1.00 30.76    A    C
ATOM    282  CB   SER A  66      32.911  31.576  65.994  1.00 30.92    A    C
ATOM    283  OG   SER A  66      32.380  32.801  66.480  1.00 32.86    A    O
ATOM    284  C    SER A  66      35.032  30.266  65.741  1.00 30.82    A    C
ATOM    285  O    SER A  66      34.772  29.527  64.775  1.00 29.48    A    O
ATOM    286  N    PHE A  67      35.843  29.923  66.741  1.00 30.86    A    N
ATOM    287  CA   PHE A  67      36.495  28.623  66.813  1.00 31.30    A    C
ATOM    288  CB   PHE A  67      35.453  27.509  66.688  1.00 30.03    A    C
ATOM    289  CG   PHE A  67      34.498  27.424  67.856  1.00 29.46    A    C
ATOM    290  CD1  PHE A  67      33.122  27.370  67.641  1.00 28.80    A    C
ATOM    291  CD2  PHE A  67      34.976  27.347  69.159  1.00 28.83    A    C
ATOM    292  CE1  PHE A  67      32.239  27.234  68.706  1.00 28.73    A    C
ATOM    293  CE2  PHE A  67      34.105  27.211  70.230  1.00 29.22    A    C
ATOM    294  CZ   PHE A  67      32.734  27.154  70.006  1.00 29.15    A    C
ATOM    295  C    PHE A  67      37.572  28.425  65.746  1.00 32.43    A    C
ATOM    296  O    PHE A  67      37.941  27.278  65.447  1.00 32.77    A    O
ATOM    297  N    GLY A  68      38.081  29.519  65.174  1.00 30.86    A    N
ATOM    298  CA   GLY A  68      39.105  29.383  64.147  1.00 30.15    A    C
```

FIG. 5-6

```
ATOM    299  C    GLY A  68      39.805  30.644  63.666  1.00 29.81           A    C
ATOM    300  O    GLY A  68      39.566  31.716  64.175  1.00 28.81           A    O
ATOM    301  N    VAL A  69      40.672  30.487  62.663  1.00 29.23           A    N
ATOM    302  CA   VAL A  69      41.436  31.596  62.089  1.00 28.94           A    C
ATOM    303  CB   VAL A  69      42.844  31.699  62.722  1.00 29.44           A    C
ATOM    304  CG1  VAL A  69      43.446  33.059  62.411  1.00 28.13           A    C
ATOM    305  CG2  VAL A  69      42.775  31.458  64.222  1.00 29.37           A    C
ATOM    306  C    VAL A  69      41.633  31.442  60.571  1.00 29.53           A    C
ATOM    307  O    VAL A  69      41.593  30.346  60.037  1.00 28.84           A    O
ATOM    308  N    VAL A  70      41.868  32.560  59.893  1.00 29.93           A    N
ATOM    309  CA   VAL A  70      42.072  32.555  58.452  1.00 30.32           A    C
ATOM    310  CB   VAL A  70      41.072  33.483  57.743  1.00 30.50           A    C
ATOM    311  CG1  VAL A  70      41.188  33.317  56.238  1.00 28.93           A    C
ATOM    312  CG2  VAL A  70      39.667  33.163  58.202  1.00 31.53           A    C
ATOM    313  C    VAL A  70      43.481  33.010  58.099  1.00 30.93           A    C
ATOM    314  O    VAL A  70      43.916  34.105  58.470  1.00 30.84           A    O
ATOM    315  N    TYR A  71      44.196  32.162  57.376  1.00 30.68           A    N
ATOM    316  CA   TYR A  71      45.550  32.488  56.984  1.00 30.62           A    C
ATOM    317  CB   TYR A  71      46.506  31.338  57.299  1.00 30.44           A    C
ATOM    318  CG   TYR A  71      46.585  30.966  58.756  1.00 32.09           A    C
ATOM    319  CD1  TYR A  71      45.610  30.171  59.344  1.00 31.19           A    C
ATOM    320  CE1  TYR A  71      45.690  29.818  60.685  1.00 34.60           A    C
ATOM    321  CD2  TYR A  71      47.645  31.406  59.546  1.00 32.90           A    C
ATOM    322  CE2  TYR A  71      47.737  31.061  60.885  1.00 33.65           A    C
ATOM    323  CZ   TYR A  71      46.759  30.266  61.452  1.00 35.33           A    C
ATOM    324  OH   TYR A  71      46.854  29.903  62.779  1.00 37.58           A    O
ATOM    325  C    TYR A  71      45.663  32.805  55.513  1.00 31.25           A    C
ATOM    326  O    TYR A  71      44.785  32.501  54.714  1.00 30.16           A    O
ATOM    327  N    GLN A  72      46.776  33.439  55.185  1.00 32.97           A    N
ATOM    328  CA   GLN A  72      47.110  33.803  53.828  1.00 34.46           A    C
ATOM    329  CB   GLN A  72      47.472  35.284  53.763  1.00 36.27           A    C
ATOM    330  CG   GLN A  72      47.314  35.911  52.389  1.00 40.42           A    C
ATOM    331  CD   GLN A  72      48.639  36.172  51.692  1.00 41.41           A    C
ATOM    332  OE1  GLN A  72      49.461  36.988  52.143  1.00 39.69           A    O
ATOM    333  NE2  GLN A  72      48.855  35.479  50.584  1.00 44.38           A    N
ATOM    334  C    GLN A  72      48.348  32.946  53.614  1.00 34.55           A    C
ATOM    335  O    GLN A  72      49.186  32.867  54.492  1.00 34.46           A    O
ATOM    336  N    ALA A  73      48.440  32.272  52.477  1.00 34.63           A    N
ATOM    337  CA   ALA A  73      49.600  31.431  52.200  1.00 34.72           A    C
ATOM    338  CB   ALA A  73      49.318  29.990  52.593  1.00 33.70           A    C
ATOM    339  C    ALA A  73      49.935  31.512  50.721  1.00 35.24           A    C
ATOM    340  O    ALA A  73      49.104  31.916  49.910  1.00 35.30           A    O
ATOM    341  N    LYS A  74      51.162  31.134  50.384  1.00 35.39           A    N
ATOM    342  CA   LYS A  74      51.626  31.158  49.004  1.00 36.39           A    C
ATOM    343  CB   LYS A  74      52.808  32.129  48.881  1.00 36.75           A    C
ATOM    344  CG   LYS A  74      53.562  32.103  47.548  1.00 39.09           A    C
ATOM    345  CD   LYS A  74      54.634  33.195  47.538  1.00 40.79           A    C
ATOM    346  CE   LYS A  74      55.639  33.035  46.399  1.00 44.47           A    C
ATOM    347  NZ   LYS A  74      56.606  31.896  46.584  1.00 46.12           A    N
ATOM    348  C    LYS A  74      52.040  29.746  48.601  1.00 36.44           A    C
ATOM    349  O    LYS A  74      52.890  29.130  49.251  1.00 36.48           A    O
ATOM    350  N    LEU A  75      51.422  29.228  47.543  1.00 36.69           A    N
ATOM    351  CA   LEU A  75      51.751  27.892  47.066  1.00 36.99           A    C
ATOM    352  CB   LEU A  75      50.795  27.466  45.943  1.00 35.64           A    C
ATOM    353  CG   LEU A  75      49.304  27.417  46.298  1.00 36.12           A    C
ATOM    354  CD1  LEU A  75      48.477  27.005  45.082  1.00 35.46           A    C
ATOM    355  CD2  LEU A  75      49.091  26.443  47.445  1.00 35.86           A    C
ATOM    356  C    LEU A  75      53.186  27.948  46.553  1.00 37.23           A    C
ATOM    357  O    LEU A  75      53.530  28.796  45.738  1.00 36.86           A    O
ATOM    358  N    CYS A  76      54.014  27.038  47.051  1.00 38.34           A    N
```

FIG. 5-7

| | | | | | | | | | | | |
|---|---|---|---|---|---|---|---|---|---|---|---|
| ATOM | 359 | CA | CYS | A | 76 | 55.416 | 26.975 | 46.684 | 1.00 | 40.14 | A C |
| ATOM | 360 | CB | CYS | A | 76 | 56.035 | 25.714 | 47.259 | 1.00 | 39.64 | A C |
| ATOM | 361 | SG | CYS | A | 76 | 56.171 | 25.851 | 49.024 | 1.00 | 42.10 | A S |
| ATOM | 362 | C | CYS | A | 76 | 55.762 | 27.063 | 45.216 | 1.00 | 42.19 | A C |
| ATOM | 363 | O | CYS | A | 76 | 56.546 | 27.916 | 44.819 | 1.00 | 43.39 | A O |
| ATOM | 364 | N | ASP | A | 77 | 55.178 | 26.190 | 44.407 | 1.00 | 43.44 | A N |
| ATOM | 365 | CA | ASP | A | 77 | 55.504 | 26.180 | 42.992 | 1.00 | 45.48 | A C |
| ATOM | 366 | CB | ASP | A | 77 | 55.147 | 24.814 | 42.408 | 1.00 | 46.72 | A C |
| ATOM | 367 | CG | ASP | A | 77 | 55.702 | 23.670 | 43.246 | 1.00 | 48.58 | A C |
| ATOM | 368 | OD1 | ASP | A | 77 | 56.919 | 23.703 | 43.569 | 1.00 | 48.52 | A O |
| ATOM | 369 | OD2 | ASP | A | 77 | 54.924 | 22.741 | 43.580 | 1.00 | 49.89 | A O |
| ATOM | 370 | C | ASP | A | 77 | 54.901 | 27.305 | 42.150 | 1.00 | 46.46 | A C |
| ATOM | 371 | O | ASP | A | 77 | 55.639 | 28.062 | 41.536 | 1.00 | 47.55 | A O |
| ATOM | 372 | N | SER | A | 78 | 53.575 | 27.424 | 42.114 | 1.00 | 46.40 | A N |
| ATOM | 373 | CA | SER | A | 78 | 52.955 | 28.475 | 41.309 | 1.00 | 46.21 | A C |
| ATOM | 374 | CB | SER | A | 78 | 51.474 | 28.168 | 41.061 | 1.00 | 47.11 | A C |
| ATOM | 375 | OG | SER | A | 78 | 50.746 | 28.119 | 42.287 | 1.00 | 48.83 | A O |
| ATOM | 376 | C | SER | A | 78 | 53.075 | 29.841 | 41.966 | 1.00 | 45.81 | A C |
| ATOM | 377 | O | SER | A | 78 | 52.998 | 30.869 | 41.296 | 1.00 | 45.84 | A O |
| ATOM | 378 | N | GLY | A | 79 | 53.267 | 29.852 | 43.280 | 1.00 | 45.35 | A N |
| ATOM | 379 | CA | GLY | A | 79 | 53.376 | 31.116 | 43.982 | 1.00 | 44.40 | A C |
| ATOM | 380 | C | GLY | A | 79 | 51.998 | 31.731 | 44.145 | 1.00 | 43.72 | A C |
| ATOM | 381 | O | GLY | A | 79 | 51.862 | 32.854 | 44.621 | 1.00 | 44.83 | A O |
| ATOM | 382 | N | GLU | A | 80 | 50.969 | 30.998 | 43.735 | 1.00 | 42.03 | A N |
| ATOM | 383 | CA | GLU | A | 80 | 49.608 | 31.495 | 43.861 | 1.00 | 40.41 | A C |
| ATOM | 384 | CB | GLU | A | 80 | 48.611 | 30.475 | 43.324 | 1.00 | 41.47 | A C |
| ATOM | 385 | CG | GLU | A | 80 | 47.726 | 31.019 | 42.238 | 1.00 | 43.88 | A C |
| ATOM | 386 | CD | GLU | A | 80 | 46.649 | 30.039 | 41.822 | 1.00 | 46.40 | A C |
| ATOM | 387 | OE1 | GLU | A | 80 | 47.001 | 28.941 | 41.322 | 1.00 | 48.05 | A O |
| ATOM | 388 | OE2 | GLU | A | 80 | 45.451 | 30.372 | 41.995 | 1.00 | 46.84 | A O |
| ATOM | 389 | C | GLU | A | 80 | 49.311 | 31.746 | 45.333 | 1.00 | 38.67 | A C |
| ATOM | 390 | O | GLU | A | 80 | 49.733 | 30.992 | 46.191 | 1.00 | 38.27 | A O |
| ATOM | 391 | N | LEU | A | 81 | 48.587 | 32.818 | 45.613 | 1.00 | 36.24 | A N |
| ATOM | 392 | CA | LEU | A | 81 | 48.231 | 33.133 | 46.980 | 1.00 | 34.61 | A C |
| ATOM | 393 | CB | LEU | A | 81 | 48.089 | 34.646 | 47.147 | 1.00 | 34.92 | A C |
| ATOM | 394 | CG | LEU | A | 81 | 49.382 | 35.434 | 46.925 | 1.00 | 34.71 | A C |
| ATOM | 395 | CD1 | LEU | A | 81 | 49.062 | 36.888 | 46.638 | 1.00 | 35.66 | A C |
| ATOM | 396 | CD2 | LEU | A | 81 | 50.279 | 35.291 | 48.145 | 1.00 | 33.74 | A C |
| ATOM | 397 | C | LEU | A | 81 | 46.914 | 32.444 | 47.299 | 1.00 | 32.70 | A C |
| ATOM | 398 | O | LEU | A | 81 | 45.976 | 32.494 | 46.514 | 1.00 | 33.64 | A O |
| ATOM | 399 | N | VAL | A | 82 | 46.853 | 31.783 | 48.443 | 1.00 | 29.90 | A N |
| ATOM | 400 | CA | VAL | A | 82 | 45.633 | 31.110 | 48.837 | 1.00 | 29.56 | A C |
| ATOM | 401 | CB | VAL | A | 82 | 45.769 | 29.576 | 48.799 | 1.00 | 29.32 | A C |
| ATOM | 402 | CG1 | VAL | A | 82 | 45.990 | 29.104 | 47.376 | 1.00 | 28.13 | A C |
| ATOM | 403 | CG2 | VAL | A | 82 | 46.891 | 29.135 | 49.722 | 1.00 | 27.67 | A C |
| ATOM | 404 | C | VAL | A | 82 | 45.269 | 31.497 | 50.252 | 1.00 | 29.12 | A C |
| ATOM | 405 | O | VAL | A | 82 | 46.074 | 32.054 | 50.983 | 1.00 | 28.81 | A O |
| ATOM | 406 | N | ALA | A | 83 | 44.034 | 31.191 | 50.622 | 1.00 | 29.18 | A N |
| ATOM | 407 | CA | ALA | A | 83 | 43.548 | 31.474 | 51.957 | 1.00 | 29.07 | A C |
| ATOM | 408 | CB | ALA | A | 83 | 42.254 | 32.274 | 51.888 | 1.00 | 28.84 | A C |
| ATOM | 409 | C | ALA | A | 83 | 43.298 | 30.126 | 52.612 | 1.00 | 28.44 | A C |
| ATOM | 410 | O | ALA | A | 83 | 42.836 | 29.195 | 51.959 | 1.00 | 28.54 | A O |
| ATOM | 411 | N | ILE | A | 84 | 43.628 | 30.019 | 53.893 | 1.00 | 26.72 | A N |
| ATOM | 412 | CA | ILE | A | 84 | 43.404 | 28.782 | 54.615 | 1.00 | 26.01 | A C |
| ATOM | 413 | CB | ILE | A | 84 | 44.721 | 28.119 | 55.050 | 1.00 | 26.24 | A C |
| ATOM | 414 | CG2 | ILE | A | 84 | 44.417 | 26.852 | 55.834 | 1.00 | 25.63 | A C |
| ATOM | 415 | CG1 | ILE | A | 84 | 45.577 | 27.786 | 53.824 | 1.00 | 27.98 | A C |
| ATOM | 416 | CD1 | ILE | A | 84 | 46.959 | 27.236 | 54.168 | 1.00 | 27.69 | A C |
| ATOM | 417 | C | ILE | A | 84 | 42.586 | 29.078 | 55.860 | 1.00 | 27.11 | A C |
| ATOM | 418 | O | ILE | A | 84 | 43.044 | 29.775 | 56.767 | 1.00 | 26.79 | A O |

FIG. 5-8

| | | | | | | | | | | | |
|---|---|---|---|---|---|---|---|---|---|---|---|
| ATOM | 419 | N | LYS | A | 85 | 41.366 | 28.552 | 55.891 | 1.00 | 26.91 | A N |
| ATOM | 420 | CA | LYS | A | 85 | 40.481 | 28.741 | 57.027 | 1.00 | 25.96 | A C |
| ATOM | 421 | CB | LYS | A | 85 | 39.032 | 28.911 | 56.560 | 1.00 | 24.28 | A C |
| ATOM | 422 | CG | LYS | A | 85 | 38.041 | 29.138 | 57.691 | 1.00 | 22.07 | A C |
| ATOM | 423 | CD | LYS | A | 85 | 36.641 | 29.434 | 57.166 | 1.00 | 22.14 | A C |
| ATOM | 424 | CE | LYS | A | 85 | 35.680 | 29.713 | 58.303 | 1.00 | 19.26 | A C |
| ATOM | 425 | NZ | LYS | A | 85 | 34.395 | 30.290 | 57.848 | 1.00 | 19.29 | A N |
| ATOM | 426 | C | LYS | A | 85 | 40.613 | 27.509 | 57.911 | 1.00 | 27.57 | A C |
| ATOM | 427 | O | LYS | A | 85 | 40.297 | 26.398 | 57.495 | 1.00 | 28.04 | A O |
| ATOM | 428 | N | LYS | A | 86 | 41.094 | 27.721 | 59.129 | 1.00 | 27.79 | A N |
| ATOM | 429 | CA | LYS | A | 86 | 41.296 | 26.631 | 60.072 | 1.00 | 28.55 | A C |
| ATOM | 430 | CB | LYS | A | 86 | 42.763 | 26.599 | 60.507 | 1.00 | 28.39 | A C |
| ATOM | 431 | CG | LYS | A | 86 | 43.109 | 25.484 | 61.455 | 1.00 | 28.76 | A C |
| ATOM | 432 | CD | LYS | A | 86 | 44.599 | 25.452 | 61.717 | 1.00 | 30.21 | A C |
| ATOM | 433 | CE | LYS | A | 86 | 44.982 | 24.208 | 62.490 | 1.00 | 29.24 | A C |
| ATOM | 434 | NZ | LYS | A | 86 | 46.414 | 24.259 | 62.842 | 1.00 | 31.95 | A N |
| ATOM | 435 | C | LYS | A | 86 | 40.397 | 26.808 | 61.282 | 1.00 | 28.53 | A C |
| ATOM | 436 | O | LYS | A | 86 | 40.567 | 27.739 | 62.060 | 1.00 | 29.97 | A O |
| ATOM | 437 | N | VAL | A | 87 | 39.433 | 25.912 | 61.431 | 1.00 | 28.76 | A N |
| ATOM | 438 | CA | VAL | A | 87 | 38.509 | 25.987 | 62.551 | 1.00 | 31.05 | A C |
| ATOM | 439 | CB | VAL | A | 87 | 37.088 | 26.346 | 62.068 | 1.00 | 31.01 | A C |
| ATOM | 440 | CG1 | VAL | A | 87 | 36.537 | 25.220 | 61.196 | 1.00 | 31.31 | A C |
| ATOM | 441 | CG2 | VAL | A | 87 | 36.178 | 26.608 | 63.269 | 1.00 | 33.83 | A C |
| ATOM | 442 | C | VAL | A | 87 | 38.483 | 24.651 | 63.286 | 1.00 | 32.18 | A C |
| ATOM | 443 | O | VAL | A | 87 | 38.869 | 23.623 | 62.736 | 1.00 | 32.86 | A O |
| ATOM | 444 | N | LEU | A | 88 | 38.021 | 24.681 | 64.530 | 1.00 | 33.24 | A N |
| ATOM | 445 | CA | LEU | A | 88 | 37.954 | 23.494 | 65.362 | 1.00 | 33.98 | A C |
| ATOM | 446 | CB | LEU | A | 88 | 37.599 | 23.910 | 66.793 | 1.00 | 35.07 | A C |
| ATOM | 447 | CG | LEU | A | 88 | 37.942 | 22.986 | 67.966 | 1.00 | 35.34 | A C |
| ATOM | 448 | CD1 | LEU | A | 88 | 37.202 | 21.684 | 67.812 | 1.00 | 35.31 | A C |
| ATOM | 449 | CD2 | LEU | A | 88 | 39.444 | 22.749 | 68.018 | 1.00 | 35.33 | A C |
| ATOM | 450 | C | LEU | A | 88 | 36.941 | 22.484 | 64.816 | 1.00 | 35.06 | A C |
| ATOM | 451 | O | LEU | A | 88 | 35.806 | 22.830 | 64.483 | 1.00 | 35.11 | A O |
| ATOM | 452 | N | GLN | A | 89 | 37.366 | 21.227 | 64.736 | 1.00 | 35.30 | A N |
| ATOM | 453 | CA | GLN | A | 89 | 36.533 | 20.147 | 64.219 | 1.00 | 36.13 | A C |
| ATOM | 454 | CB | GLN | A | 89 | 37.385 | 19.240 | 63.321 | 1.00 | 37.17 | A C |
| ATOM | 455 | CG | GLN | A | 89 | 36.713 | 17.965 | 62.810 | 1.00 | 38.28 | A C |
| ATOM | 456 | CD | GLN | A | 89 | 35.380 | 18.205 | 62.098 | 1.00 | 37.76 | A C |
| ATOM | 457 | OE1 | GLN | A | 89 | 35.283 | 18.989 | 61.188 | 1.00 | 38.70 | A O |
| ATOM | 458 | NE2 | GLN | A | 89 | 34.352 | 17.489 | 62.531 | 1.00 | 38.85 | A N |
| ATOM | 459 | C | GLN | A | 89 | 35.905 | 19.328 | 65.334 | 1.00 | 36.18 | A C |
| ATOM | 460 | O | GLN | A | 89 | 36.606 | 18.841 | 66.229 | 1.00 | 36.57 | A O |
| ATOM | 461 | N | ALA | A | 90 | 34.582 | 19.185 | 65.291 | 1.00 | 36.14 | A N |
| ATOM | 462 | CA | ALA | A | 90 | 33.886 | 18.396 | 66.301 | 1.00 | 37.75 | A C |
| ATOM | 463 | CB | ALA | A | 90 | 32.410 | 18.737 | 66.333 | 1.00 | 36.48 | A C |
| ATOM | 464 | C | ALA | A | 90 | 34.090 | 16.936 | 65.910 | 1.00 | 39.57 | A C |
| ATOM | 465 | O | ALA | A | 90 | 33.777 | 16.521 | 64.788 | 1.00 | 39.68 | A O |
| ATOM | 466 | N | ALA | A | 91 | 34.629 | 16.156 | 66.836 | 1.00 | 41.02 | A N |
| ATOM | 467 | CA | ALA | A | 91 | 34.899 | 14.753 | 66.559 | 1.00 | 41.90 | A C |
| ATOM | 468 | CB | ALA | A | 91 | 35.768 | 14.162 | 67.683 | 1.00 | 40.64 | A C |
| ATOM | 469 | C | ALA | A | 91 | 33.606 | 13.941 | 66.381 | 1.00 | 42.48 | A C |
| ATOM | 470 | O | ALA | A | 91 | 33.638 | 12.810 | 65.894 | 1.00 | 43.38 | A O |
| ATOM | 471 | N | ALA | A | 92 | 32.462 | 14.538 | 66.710 | 1.00 | 42.34 | A N |
| ATOM | 472 | CA | ALA | A | 92 | 31.171 | 13.834 | 66.621 | 1.00 | 42.47 | A C |
| ATOM | 473 | CB | ALA | A | 92 | 30.246 | 14.343 | 67.726 | 1.00 | 41.77 | A C |
| ATOM | 474 | C | ALA | A | 92 | 30.404 | 13.852 | 65.285 | 1.00 | 42.56 | A C |
| ATOM | 475 | O | ALA | A | 92 | 29.665 | 12.914 | 64.989 | 1.00 | 42.97 | A O |
| ATOM | 476 | N | ALA | A | 93 | 30.558 | 14.902 | 64.483 | 1.00 | 42.60 | A N |
| ATOM | 477 | CA | ALA | A | 93 | 29.820 | 14.974 | 63.220 | 1.00 | 42.01 | A C |
| ATOM | 478 | CB | ALA | A | 93 | 28.563 | 15.840 | 63.398 | 1.00 | 42.15 | A C |

FIG. 5-9

```
ATOM    479  C   ALA A  93      30.670  15.538  62.099  1.00 41.23      A    C
ATOM    480  O   ALA A  93      31.761  16.068  62.332  1.00 42.07      A    O
ATOM    481  N   ALA A  94      30.178  15.421  60.872  1.00 39.86      A    N
ATOM    482  CA  ALA A  94      30.918  15.963  59.743  1.00 36.91      A    C
ATOM    483  CB  ALA A  94      30.402  15.365  58.432  1.00 38.31      A    C
ATOM    484  C   ALA A  94      30.701  17.476  59.778  1.00 34.55      A    C
ATOM    485  O   ALA A  94      29.674  17.946  60.241  1.00 32.26      A    O
ATOM    486  N   ASN A  95      31.679  18.233  59.306  1.00 32.53      A    N
ATOM    487  CA  ASN A  95      31.559  19.685  59.324  1.00 31.56      A    C
ATOM    488  CB  ASN A  95      32.958  20.312  59.204  1.00 32.90      A    C
ATOM    489  CG  ASN A  95      32.930  21.834  59.174  1.00 33.64      A    C
ATOM    490  OD1 ASN A  95      32.433  22.424  58.240  1.00 34.01      A    O
ATOM    491  ND2 ASN A  95      33.485  22.464  60.207  1.00 33.58      A    N
ATOM    492  C   ASN A  95      30.621  20.215  58.233  1.00 30.12      A    C
ATOM    493  O   ASN A  95      30.877  20.067  57.051  1.00 28.59      A    O
ATOM    494  N   ARG A  96      29.528  20.836  58.662  1.00 27.88      A    N
ATOM    495  CA  ARG A  96      28.525  21.367  57.745  1.00 26.92      A    C
ATOM    496  CB  ARG A  96      27.372  21.984  58.547  1.00 26.31      A    C
ATOM    497  CG  ARG A  96      26.193  22.442  57.700  1.00 27.72      A    C
ATOM    498  CD  ARG A  96      25.224  23.275  58.522  1.00 28.87      A    C
ATOM    499  NE  ARG A  96      24.429  22.461  59.434  1.00 33.63      A    N
ATOM    500  CZ  ARG A  96      23.686  22.951  60.427  1.00 33.88      A    C
ATOM    501  NH1 ARG A  96      23.639  24.265  60.645  1.00 31.87      A    N
ATOM    502  NH2 ARG A  96      22.982  22.124  61.193  1.00 32.49      A    N
ATOM    503  C   ARG A  96      29.054  22.393  56.737  1.00 25.73      A    C
ATOM    504  O   ARG A  96      28.611  22.424  55.592  1.00 24.03      A    O
ATOM    505  N   GLU A  97      29.990  23.236  57.159  1.00 24.16      A    N
ATOM    506  CA  GLU A  97      30.540  24.231  56.247  1.00 24.06      A    C
ATOM    507  CB  GLU A  97      31.478  25.182  56.999  1.00 24.42      A    C
ATOM    508  CG  GLU A  97      32.031  26.334  56.165  1.00 24.60      A    C
ATOM    509  CD  GLU A  97      32.820  27.323  57.009  1.00 26.85      A    C
ATOM    510  OE1 GLU A  97      33.150  26.992  58.168  1.00 27.55      A    O
ATOM    511  OE2 GLU A  97      33.115  28.428  56.515  1.00 26.78      A    O
ATOM    512  C   GLU A  97      31.279  23.533  55.110  1.00 24.85      A    C
ATOM    513  O   GLU A  97      31.148  23.912  53.950  1.00 24.11      A    O
ATOM    514  N   LEU A  98      32.047  22.503  55.459  1.00 24.42      A    N
ATOM    515  CA  LEU A  98      32.797  21.737  54.475  1.00 26.18      A    C
ATOM    516  CB  LEU A  98      33.611  20.648  55.167  1.00 27.48      A    C
ATOM    517  CG  LEU A  98      34.271  19.632  54.234  1.00 25.78      A    C
ATOM    518  CD1 LEU A  98      35.211  20.329  53.258  1.00 21.87      A    C
ATOM    519  CD2 LEU A  98      35.022  18.624  55.076  1.00 25.82      A    C
ATOM    520  C   LEU A  98      31.841  21.092  53.480  1.00 27.37      A    C
ATOM    521  O   LEU A  98      31.966  21.278  52.285  1.00 26.79      A    O
ATOM    522  N   GLN A  99      30.878  20.340  54.001  1.00 28.29      A    N
ATOM    523  CA  GLN A  99      29.913  19.643  53.162  1.00 29.91      A    C
ATOM    524  CB  GLN A  99      28.855  18.963  54.035  1.00 32.74      A    C
ATOM    525  CG  GLN A  99      29.393  17.813  54.885  1.00 36.96      A    C
ATOM    526  CD  GLN A  99      28.313  17.195  55.760  1.00 40.53      A    C
ATOM    527  OE1 GLN A  99      27.932  17.758  56.810  1.00 42.46      A    O
ATOM    528  NE2 GLN A  99      27.797  16.037  55.335  1.00 41.04      A    N
ATOM    529  C   GLN A  99      29.244  20.566  52.151  1.00 30.10      A    C
ATOM    530  O   GLN A  99      28.978  20.174  51.028  1.00 29.94      A    O
ATOM    531  N   ILE A 100      28.982  21.803  52.549  1.00 29.63      A    N
ATOM    532  CA  ILE A 100      28.352  22.745  51.638  1.00 28.47      A    C
ATOM    533  CB  ILE A 100      27.732  23.914  52.429  1.00 28.03      A    C
ATOM    534  CG2 ILE A 100      27.334  25.041  51.496  1.00 28.21      A    C
ATOM    535  CG1 ILE A 100      26.517  23.403  53.216  1.00 28.42      A    C
ATOM    536  CD1 ILE A 100      25.863  24.440  54.122  1.00 27.04      A    C
ATOM    537  C   ILE A 100      29.332  23.280  50.596  1.00 28.22      A    C
ATOM    538  O   ILE A 100      29.006  23.344  49.438  1.00 29.68      A    O
```

FIG. 5-10

| | | | | | | | | | | | |
|---|---|---|---|---|---|---|---|---|---|---|---|
| ATOM | 539 | N | MET | A | 101 | 30.531 | 23.654 | 51.027 | 1.00 | 28.62 | A N |
| ATOM | 540 | CA | MET | A | 101 | 31.555 | 24.175 | 50.122 | 1.00 | 29.44 | A C |
| ATOM | 541 | CB | MET | A | 101 | 32.839 | 24.473 | 50.899 | 1.00 | 31.00 | A C |
| ATOM | 542 | CG | MET | A | 101 | 32.719 | 25.492 | 52.020 | 1.00 | 33.30 | A C |
| ATOM | 543 | SD | MET | A | 101 | 32.696 | 27.165 | 51.414 | 1.00 | 35.35 | A S |
| ATOM | 544 | CE | MET | A | 101 | 34.314 | 27.301 | 50.773 | 1.00 | 35.15 | A C |
| ATOM | 545 | C | MET | A | 101 | 31.888 | 23.159 | 49.033 | 1.00 | 30.68 | A C |
| ATOM | 546 | O | MET | A | 101 | 32.171 | 23.526 | 47.912 | 1.00 | 31.84 | A O |
| ATOM | 547 | N | ARG | A | 102 | 31.863 | 21.878 | 49.388 | 1.00 | 31.84 | A N |
| ATOM | 548 | CA | ARG | A | 102 | 32.195 | 20.826 | 48.441 | 1.00 | 32.66 | A C |
| ATOM | 549 | CB | ARG | A | 102 | 32.285 | 19.477 | 49.149 | 1.00 | 32.24 | A C |
| ATOM | 550 | CG | ARG | A | 102 | 33.431 | 19.404 | 50.126 | 1.00 | 33.70 | A C |
| ATOM | 551 | CD | ARG | A | 102 | 33.641 | 17.985 | 50.604 | 1.00 | 35.68 | A C |
| ATOM | 552 | NE | ARG | A | 102 | 34.271 | 17.149 | 49.586 | 1.00 | 36.80 | A N |
| ATOM | 553 | CZ | ARG | A | 102 | 34.438 | 15.837 | 49.709 | 1.00 | 37.78 | A C |
| ATOM | 554 | NH1 | ARG | A | 102 | 34.016 | 15.216 | 50.806 | 1.00 | 36.61 | A N |
| ATOM | 555 | NH2 | ARG | A | 102 | 35.035 | 15.149 | 48.741 | 1.00 | 37.58 | A N |
| ATOM | 556 | C | ARG | A | 102 | 31.232 | 20.722 | 47.280 | 1.00 | 32.61 | A C |
| ATOM | 557 | O | ARG | A | 102 | 31.615 | 20.293 | 46.206 | 1.00 | 32.16 | A O |
| ATOM | 558 | N | LYS | A | 103 | 29.985 | 21.125 | 47.479 | 1.00 | 31.91 | A N |
| ATOM | 559 | CA | LYS | A | 103 | 29.050 | 21.023 | 46.377 | 1.00 | 32.56 | A C |
| ATOM | 560 | CB | LYS | A | 103 | 27.745 | 20.372 | 46.864 | 1.00 | 33.92 | A C |
| ATOM | 561 | CG | LYS | A | 103 | 26.925 | 21.183 | 47.827 | 1.00 | 35.89 | A C |
| ATOM | 562 | CD | LYS | A | 103 | 25.693 | 20.403 | 48.303 | 1.00 | 37.48 | A C |
| ATOM | 563 | CE | LYS | A | 103 | 26.084 | 19.200 | 49.167 | 1.00 | 39.44 | A C |
| ATOM | 564 | NZ | LYS | A | 103 | 24.919 | 18.460 | 49.742 | 1.00 | 37.19 | A N |
| ATOM | 565 | C | LYS | A | 103 | 28.779 | 22.347 | 45.674 | 1.00 | 31.37 | A C |
| ATOM | 566 | O | LYS | A | 103 | 27.853 | 22.442 | 44.889 | 1.00 | 31.67 | A O |
| ATOM | 567 | N | LEU | A | 104 | 29.615 | 23.352 | 45.933 | 1.00 | 30.60 | A N |
| ATOM | 568 | CA | LEU | A | 104 | 29.451 | 24.668 | 45.308 | 1.00 | 30.00 | A C |
| ATOM | 569 | CB | LEU | A | 104 | 29.440 | 25.763 | 46.383 | 1.00 | 30.57 | A C |
| ATOM | 570 | CG | LEU | A | 104 | 28.092 | 26.090 | 47.051 | 1.00 | 31.61 | A C |
| ATOM | 571 | CD1 | LEU | A | 104 | 27.359 | 24.824 | 47.406 | 1.00 | 31.55 | A C |
| ATOM | 572 | CD2 | LEU | A | 104 | 28.321 | 26.947 | 48.293 | 1.00 | 30.88 | A C |
| ATOM | 573 | C | LEU | A | 104 | 30.511 | 24.985 | 44.252 | 1.00 | 29.44 | A C |
| ATOM | 574 | O | LEU | A | 104 | 31.692 | 24.761 | 44.454 | 1.00 | 28.95 | A O |
| ATOM | 575 | N | ASP | A | 105 | 30.058 | 25.505 | 43.116 | 1.00 | 29.83 | A N |
| ATOM | 576 | CA | ASP | A | 105 | 30.948 | 25.875 | 42.023 | 1.00 | 30.50 | A C |
| ATOM | 577 | CB | ASP | A | 105 | 31.166 | 24.685 | 41.084 | 1.00 | 32.96 | A C |
| ATOM | 578 | CG | ASP | A | 105 | 32.224 | 24.959 | 40.026 | 1.00 | 35.00 | A C |
| ATOM | 579 | OD1 | ASP | A | 105 | 33.320 | 25.438 | 40.389 | 1.00 | 36.67 | A O |
| ATOM | 580 | OD2 | ASP | A | 105 | 31.963 | 24.682 | 38.837 | 1.00 | 35.50 | A O |
| ATOM | 581 | C | ASP | A | 105 | 30.317 | 27.044 | 41.273 | 1.00 | 29.90 | A C |
| ATOM | 582 | O | ASP | A | 105 | 29.458 | 26.859 | 40.406 | 1.00 | 30.14 | A O |
| ATOM | 583 | N | HIS | A | 106 | 30.754 | 28.247 | 41.625 | 1.00 | 27.86 | A N |
| ATOM | 584 | CA | HIS | A | 106 | 30.225 | 29.464 | 41.033 | 1.00 | 25.21 | A C |
| ATOM | 585 | CB | HIS | A | 106 | 28.992 | 29.918 | 41.813 | 1.00 | 23.32 | A C |
| ATOM | 586 | CG | HIS | A | 106 | 28.200 | 30.985 | 41.123 | 1.00 | 24.32 | A C |
| ATOM | 587 | CD2 | HIS | A | 106 | 27.027 | 30.924 | 40.449 | 1.00 | 22.72 | A C |
| ATOM | 588 | ND1 | HIS | A | 106 | 28.593 | 32.303 | 41.094 | 1.00 | 24.26 | A N |
| ATOM | 589 | CE1 | HIS | A | 106 | 27.691 | 33.013 | 40.434 | 1.00 | 24.81 | A C |
| ATOM | 590 | NE2 | HIS | A | 106 | 26.734 | 32.197 | 40.035 | 1.00 | 23.05 | A N |
| ATOM | 591 | C | HIS | A | 106 | 31.287 | 30.548 | 41.056 | 1.00 | 24.83 | A C |
| ATOM | 592 | O | HIS | A | 106 | 32.050 | 30.659 | 42.007 | 1.00 | 24.42 | A O |
| ATOM | 593 | N | CYS | A | 107 | 31.313 | 31.346 | 39.996 | 1.00 | 26.11 | A N |
| ATOM | 594 | CA | CYS | A | 107 | 32.276 | 32.427 | 39.843 | 1.00 | 26.34 | A C |
| ATOM | 595 | CB | CYS | A | 107 | 32.111 | 33.083 | 38.461 | 1.00 | 26.91 | A C |
| ATOM | 596 | SG | CYS | A | 107 | 30.484 | 33.874 | 38.165 | 1.00 | 33.29 | A S |
| ATOM | 597 | C | CYS | A | 107 | 32.177 | 33.487 | 40.936 | 1.00 | 26.23 | A C |
| ATOM | 598 | O | CYS | A | 107 | 33.121 | 34.243 | 41.146 | 1.00 | 25.83 | A O |

FIG. 5-11

| | | | | | | | | | | | |
|---|---|---|---|---|---|---|---|---|---|---|---|
| ATOM | 599 | N | ASN | A | 108 | 31.039 | 33.546 | 41.629 | 1.00 | 25.73 | A | N |
| ATOM | 600 | CA | ASN | A | 108 | 30.861 | 34.533 | 42.698 | 1.00 | 24.30 | A | C |
| ATOM | 601 | CB | ASN | A | 108 | 29.560 | 35.325 | 42.490 | 1.00 | 24.94 | A | C |
| ATOM | 602 | CG | ASN | A | 108 | 29.589 | 36.209 | 41.248 | 1.00 | 23.76 | A | C |
| ATOM | 603 | OD1 | ASN | A | 108 | 28.644 | 36.256 | 40.519 | 1.00 | 25.46 | A | O |
| ATOM | 604 | ND2 | ASN | A | 108 | 30.682 | 36.916 | 41.036 | 1.00 | 23.07 | A | N |
| ATOM | 605 | C | ASN | A | 108 | 30.887 | 33.931 | 44.114 | 1.00 | 25.00 | A | C |
| ATOM | 606 | O | ASN | A | 108 | 30.325 | 34.500 | 45.048 | 1.00 | 24.27 | A | O |
| ATOM | 607 | N | ILE | A | 109 | 31.544 | 32.782 | 44.264 | 1.00 | 24.92 | A | N |
| ATOM | 608 | CA | ILE | A | 109 | 31.679 | 32.119 | 45.563 | 1.00 | 24.42 | A | C |
| ATOM | 609 | CB | ILE | A | 109 | 30.825 | 30.816 | 45.650 | 1.00 | 26.44 | A | C |
| ATOM | 610 | CG2 | ILE | A | 109 | 30.955 | 30.190 | 47.036 | 1.00 | 23.13 | A | C |
| ATOM | 611 | CG1 | ILE | A | 109 | 29.352 | 31.113 | 45.348 | 1.00 | 26.69 | A | C |
| ATOM | 612 | CD1 | ILE | A | 109 | 28.689 | 32.016 | 46.352 | 1.00 | 32.06 | A | C |
| ATOM | 613 | C | ILE | A | 109 | 33.149 | 31.724 | 45.712 | 1.00 | 25.75 | A | C |
| ATOM | 614 | O | ILE | A | 109 | 33.737 | 31.205 | 44.775 | 1.00 | 26.60 | A | O |
| ATOM | 615 | N | VAL | A | 110 | 33.756 | 31.972 | 46.869 | 1.00 | 24.89 | A | N |
| ATOM | 616 | CA | VAL | A | 110 | 35.154 | 31.584 | 47.027 | 1.00 | 25.43 | A | C |
| ATOM | 617 | CB | VAL | A | 110 | 35.706 | 31.847 | 48.442 | 1.00 | 25.74 | A | C |
| ATOM | 618 | CG1 | VAL | A | 110 | 36.265 | 33.239 | 48.511 | 1.00 | 27.82 | A | C |
| ATOM | 619 | CG2 | VAL | A | 110 | 34.623 | 31.626 | 49.495 | 1.00 | 24.55 | A | C |
| ATOM | 620 | C | VAL | A | 110 | 35.262 | 30.095 | 46.755 | 1.00 | 26.31 | A | C |
| ATOM | 621 | O | VAL | A | 110 | 34.450 | 29.312 | 47.226 | 1.00 | 25.50 | A | O |
| ATOM | 622 | N | ARG | A | 111 | 36.278 | 29.711 | 45.998 | 1.00 | 27.27 | A | N |
| ATOM | 623 | CA | ARG | A | 111 | 36.459 | 28.313 | 45.645 | 1.00 | 28.36 | A | C |
| ATOM | 624 | CB | ARG | A | 111 | 37.207 | 28.219 | 44.310 | 1.00 | 31.91 | A | C |
| ATOM | 625 | CG | ARG | A | 111 | 37.234 | 26.833 | 43.642 | 1.00 | 36.37 | A | C |
| ATOM | 626 | CD | ARG | A | 111 | 38.125 | 26.856 | 42.378 | 1.00 | 38.84 | A | C |
| ATOM | 627 | NE | ARG | A | 111 | 39.296 | 25.989 | 42.537 | 1.00 | 44.01 | A | N |
| ATOM | 628 | CZ | ARG | A | 111 | 40.298 | 25.885 | 41.661 | 1.00 | 45.92 | A | C |
| ATOM | 629 | NH1 | ARG | A | 111 | 40.291 | 26.591 | 40.533 | 1.00 | 46.76 | A | N |
| ATOM | 630 | NH2 | ARG | A | 111 | 41.331 | 25.091 | 41.929 | 1.00 | 47.57 | A | N |
| ATOM | 631 | C | ARG | A | 111 | 37.220 | 27.523 | 46.699 | 1.00 | 27.30 | A | C |
| ATOM | 632 | O | ARG | A | 111 | 38.222 | 27.978 | 47.232 | 1.00 | 26.21 | A | O |
| ATOM | 633 | N | LEU | A | 112 | 36.721 | 26.334 | 47.005 | 1.00 | 27.85 | A | N |
| ATOM | 634 | CA | LEU | A | 112 | 37.404 | 25.458 | 47.948 | 1.00 | 28.30 | A | C |
| ATOM | 635 | CB | LEU | A | 112 | 36.408 | 24.538 | 48.652 | 1.00 | 27.34 | A | C |
| ATOM | 636 | CG | LEU | A | 112 | 37.040 | 23.528 | 49.614 | 1.00 | 28.58 | A | C |
| ATOM | 637 | CD1 | LEU | A | 112 | 37.530 | 24.240 | 50.872 | 1.00 | 27.84 | A | C |
| ATOM | 638 | CD2 | LEU | A | 112 | 36.024 | 22.458 | 49.971 | 1.00 | 26.40 | A | C |
| ATOM | 639 | C | LEU | A | 112 | 38.357 | 24.623 | 47.085 | 1.00 | 28.38 | A | C |
| ATOM | 640 | O | LEU | A | 112 | 37.925 | 23.727 | 46.389 | 1.00 | 27.42 | A | O |
| ATOM | 641 | N | ARG | A | 113 | 39.647 | 24.936 | 47.118 | 1.00 | 29.93 | A | N |
| ATOM | 642 | CA | ARG | A | 113 | 40.609 | 24.192 | 46.311 | 1.00 | 32.07 | A | C |
| ATOM | 643 | CB | ARG | A | 113 | 41.898 | 24.999 | 46.122 | 1.00 | 33.62 | A | C |
| ATOM | 644 | CG | ARG | A | 113 | 41.734 | 26.475 | 46.434 | 1.00 | 38.94 | A | C |
| ATOM | 645 | CD | ARG | A | 113 | 41.973 | 27.377 | 45.233 | 1.00 | 41.20 | A | C |
| ATOM | 646 | NE | ARG | A | 113 | 43.379 | 27.380 | 44.841 | 1.00 | 44.83 | A | N |
| ATOM | 647 | CZ | ARG | A | 113 | 43.921 | 28.270 | 44.013 | 1.00 | 44.75 | A | C |
| ATOM | 648 | NH1 | ARG | A | 113 | 43.169 | 29.240 | 43.489 | 1.00 | 42.53 | A | N |
| ATOM | 649 | NH2 | ARG | A | 113 | 45.212 | 28.179 | 43.709 | 1.00 | 43.78 | A | N |
| ATOM | 650 | C | ARG | A | 113 | 40.923 | 22.857 | 46.979 | 1.00 | 31.18 | A | C |
| ATOM | 651 | O | ARG | A | 113 | 40.882 | 21.822 | 46.355 | 1.00 | 32.30 | A | O |
| ATOM | 652 | N | TYR | A | 114 | 41.221 | 22.903 | 48.266 | 1.00 | 31.26 | A | N |
| ATOM | 653 | CA | TYR | A | 114 | 41.542 | 21.702 | 49.023 | 1.00 | 30.92 | A | C |
| ATOM | 654 | CB | TYR | A | 114 | 43.059 | 21.517 | 49.111 | 1.00 | 31.74 | A | C |
| ATOM | 655 | CG | TYR | A | 114 | 43.781 | 21.408 | 47.790 | 1.00 | 34.41 | A | C |
| ATOM | 656 | CD1 | TYR | A | 114 | 43.638 | 20.276 | 46.980 | 1.00 | 37.17 | A | C |
| ATOM | 657 | CE1 | TYR | A | 114 | 44.320 | 20.170 | 45.758 | 1.00 | 38.28 | A | C |
| ATOM | 658 | CD2 | TYR | A | 114 | 44.623 | 22.433 | 47.354 | 1.00 | 35.77 | A | C |

FIG. 5-12

```
ATOM    659  CE2 TYR A 114      45.305  22.341  46.139  1.00 37.03      A    C
ATOM    660  CZ  TYR A 114      45.152  21.211  45.350  1.00 38.59      A    C
ATOM    661  OH  TYR A 114      45.813  21.125  44.149  1.00 41.48      A    O
ATOM    662  C   TYR A 114      41.009  21.807  50.446  1.00 30.08      A    C
ATOM    663  O   TYR A 114      40.527  22.856  50.874  1.00 29.73      A    O
ATOM    664  N   PHE A 115      41.113  20.698  51.168  1.00 29.55      A    N
ATOM    665  CA  PHE A 115      40.726  20.629  52.563  1.00 29.94      A    C
ATOM    666  CB  PHE A 115      39.194  20.494  52.714  1.00 28.30      A    C
ATOM    667  CG  PHE A 115      38.666  19.090  52.629  1.00 28.34      A    C
ATOM    668  CD1 PHE A 115      38.677  18.257  53.745  1.00 28.64      A    C
ATOM    669  CD2 PHE A 115      38.113  18.611  51.445  1.00 28.79      A    C
ATOM    670  CE1 PHE A 115      38.143  16.968  53.686  1.00 28.04      A    C
ATOM    671  CE2 PHE A 115      37.577  17.324  51.376  1.00 28.27      A    C
ATOM    672  CZ  PHE A 115      37.593  16.502  52.500  1.00 28.65      A    C
ATOM    673  C   PHE A 115      41.488  19.456  53.177  1.00 31.17      A    C
ATOM    674  O   PHE A 115      41.646  18.406  52.561  1.00 31.90      A    O
ATOM    675  N   PHE A 116      42.012  19.668  54.378  1.00 32.24      A    N
ATOM    676  CA  PHE A 116      42.772  18.639  55.062  1.00 32.08      A    C
ATOM    677  CB  PHE A 116      44.234  18.681  54.630  1.00 32.39      A    C
ATOM    678  CG  PHE A 116      44.939  19.957  54.977  1.00 31.34      A    C
ATOM    679  CD1 PHE A 116      45.609  20.092  56.190  1.00 30.55      A    C
ATOM    680  CD2 PHE A 116      44.961  21.017  54.075  1.00 30.13      A    C
ATOM    681  CE1 PHE A 116      46.298  21.265  56.496  1.00 29.65      A    C
ATOM    682  CE2 PHE A 116      45.642  22.188  54.369  1.00 30.18      A    C
ATOM    683  CZ  PHE A 116      46.315  22.314  55.583  1.00 29.75      A    C
ATOM    684  C   PHE A 116      42.656  18.842  56.547  1.00 33.30      A    C
ATOM    685  O   PHE A 116      42.134  19.844  56.990  1.00 33.47      A    O
ATOM    686  N   TYR A 117      43.159  17.880  57.308  1.00 34.48      A    N
ATOM    687  CA  TYR A 117      43.093  17.932  58.759  1.00 35.57      A    C
ATOM    688  CB  TYR A 117      42.394  16.672  59.255  1.00 35.84      A    C
ATOM    689  CG  TYR A 117      40.951  16.593  58.825  1.00 37.03      A    C
ATOM    690  CD1 TYR A 117      39.961  17.270  59.535  1.00 37.57      A    C
ATOM    691  CE1 TYR A 117      38.626  17.225  59.135  1.00 37.56      A    C
ATOM    692  CD2 TYR A 117      40.573  15.864  57.695  1.00 37.79      A    C
ATOM    693  CE2 TYR A 117      39.234  15.810  57.282  1.00 36.71      A    C
ATOM    694  CZ  TYR A 117      38.270  16.496  58.010  1.00 38.06      A    C
ATOM    695  OH  TYR A 117      36.948  16.466  57.624  1.00 38.45      A    O
ATOM    696  C   TYR A 117      44.431  18.085  59.450  1.00 36.75      A    C
ATOM    697  O   TYR A 117      45.432  17.535  59.001  1.00 38.74      A    O
ATOM    698  N   SER A 118      44.429  18.831  60.550  1.00 36.72      A    N
ATOM    699  CA  SER A 118      45.635  19.071  61.334  1.00 37.40      A    C
ATOM    700  CB  SER A 118      45.992  20.558  61.332  1.00 37.93      A    C
ATOM    701  OG  SER A 118      46.248  21.021  60.022  1.00 40.53      A    O
ATOM    702  C   SER A 118      45.419  18.625  62.774  1.00 37.39      A    C
ATOM    703  O   SER A 118      46.218  18.949  63.644  1.00 38.48      A    O
ATOM    704  N   TYR A 127      41.390  19.745  63.848  1.00 37.57      A    N
ATOM    705  CA  TYR A 127      41.199  20.948  63.030  1.00 37.96      A    C
ATOM    706  CB  TYR A 127      42.422  21.860  63.146  1.00 39.52      A    C
ATOM    707  CG  TYR A 127      42.579  22.517  64.493  1.00 42.15      A    C
ATOM    708  CD1 TYR A 127      41.862  23.666  64.815  1.00 42.97      A    C
ATOM    709  CE1 TYR A 127      41.979  24.263  66.069  1.00 44.69      A    C
ATOM    710  CD2 TYR A 127      43.423  21.971  65.460  1.00 43.68      A    C
ATOM    711  CE2 TYR A 127      43.550  22.557  66.726  1.00 45.11      A    C
ATOM    712  CZ  TYR A 127      42.819  23.705  67.024  1.00 45.43      A    C
ATOM    713  OH  TYR A 127      42.916  24.293  68.271  1.00 44.98      A    O
ATOM    714  C   TYR A 127      40.935  20.695  61.542  1.00 36.97      A    C
ATOM    715  O   TYR A 127      41.614  19.887  60.902  1.00 37.79      A    O
ATOM    716  N   LEU A 128      39.943  21.396  60.999  1.00 34.67      A    N
ATOM    717  CA  LEU A 128      39.625  21.295  59.579  1.00 32.45      A    C
ATOM    718  CB  LEU A 128      38.111  21.298  59.344  1.00 32.18      A    C
```

FIG. 5-13

| | | | | | | | | | | |
|---|---|---|---|---|---|---|---|---|---|---|
| ATOM | 719 | CG | LEU | A | 128 | 37.660 | 21.626 | 57.915 | 1.00 30.60 | A C |
| ATOM | 720 | CD1 | LEU | A | 128 | 38.258 | 20.639 | 56.933 | 1.00 30.01 | A C |
| ATOM | 721 | CD2 | LEU | A | 128 | 36.150 | 21.601 | 57.849 | 1.00 31.54 | A C |
| ATOM | 722 | C | LEU | A | 128 | 40.242 | 22.515 | 58.909 | 1.00 31.35 | A C |
| ATOM | 723 | O | LEU | A | 128 | 40.040 | 23.625 | 59.352 | 1.00 30.98 | A O |
| ATOM | 724 | N | ASN | A | 129 | 41.010 | 22.287 | 57.849 | 1.00 30.09 | A N |
| ATOM | 725 | CA | ASN | A | 129 | 41.662 | 23.364 | 57.120 | 1.00 29.08 | A C |
| ATOM | 726 | CB | ASN | A | 129 | 43.162 | 23.080 | 56.980 | 1.00 28.44 | A C |
| ATOM | 727 | CG | ASN | A | 129 | 43.877 | 23.004 | 58.323 | 1.00 28.92 | A C |
| ATOM | 728 | OD1 | ASN | A | 129 | 43.803 | 22.002 | 59.017 | 1.00 30.94 | A O |
| ATOM | 729 | ND2 | ASN | A | 129 | 44.567 | 24.075 | 58.689 | 1.00 28.68 | A N |
| ATOM | 730 | C | ASN | A | 129 | 41.030 | 23.497 | 55.738 | 1.00 29.96 | A C |
| ATOM | 731 | O | ASN | A | 129 | 41.002 | 22.526 | 54.949 | 1.00 29.81 | A O |
| ATOM | 732 | N | LEU | A | 130 | 40.511 | 24.683 | 55.434 | 1.00 28.53 | A N |
| ATOM | 733 | CA | LEU | A | 130 | 39.885 | 24.895 | 54.133 | 1.00 27.02 | A C |
| ATOM | 734 | CB | LEU | A | 130 | 38.513 | 25.564 | 54.301 | 1.00 26.92 | A C |
| ATOM | 735 | CG | LEU | A | 130 | 37.440 | 24.828 | 55.113 | 1.00 25.96 | A C |
| ATOM | 736 | CD1 | LEU | A | 130 | 36.347 | 25.817 | 55.477 | 1.00 25.82 | A C |
| ATOM | 737 | CD2 | LEU | A | 130 | 36.872 | 23.653 | 54.338 | 1.00 24.23 | A C |
| ATOM | 738 | C | LEU | A | 130 | 40.784 | 25.756 | 53.259 | 1.00 26.37 | A C |
| ATOM | 739 | O | LEU | A | 130 | 40.991 | 26.916 | 53.539 | 1.00 25.84 | A O |
| ATOM | 740 | N | VAL | A | 131 | 41.327 | 25.157 | 52.203 | 1.00 26.54 | A N |
| ATOM | 741 | CA | VAL | A | 131 | 42.199 | 25.882 | 51.285 | 1.00 26.12 | A C |
| ATOM | 742 | CB | VAL | A | 131 | 43.176 | 24.926 | 50.545 | 1.00 26.38 | A C |
| ATOM | 743 | CG1 | VAL | A | 131 | 44.251 | 25.734 | 49.839 | 1.00 25.73 | A C |
| ATOM | 744 | CG2 | VAL | A | 131 | 43.809 | 23.953 | 51.529 | 1.00 25.29 | A C |
| ATOM | 745 | C | VAL | A | 131 | 41.291 | 26.581 | 50.276 | 1.00 26.60 | A C |
| ATOM | 746 | O | VAL | A | 131 | 40.776 | 25.963 | 49.355 | 1.00 27.40 | A O |
| ATOM | 747 | N | LEU | A | 132 | 41.092 | 27.878 | 50.478 | 1.00 25.68 | A N |
| ATOM | 748 | CA | LEU | A | 132 | 40.223 | 28.666 | 49.619 | 1.00 24.63 | A C |
| ATOM | 749 | CB | LEU | A | 132 | 39.235 | 29.457 | 50.473 | 1.00 23.45 | A C |
| ATOM | 750 | CG | LEU | A | 132 | 38.509 | 28.714 | 51.588 | 1.00 23.88 | A C |
| ATOM | 751 | CD1 | LEU | A | 132 | 37.869 | 29.709 | 52.526 | 1.00 23.36 | A C |
| ATOM | 752 | CD2 | LEU | A | 132 | 37.475 | 27.789 | 51.003 | 1.00 22.29 | A C |
| ATOM | 753 | C | LEU | A | 132 | 41.015 | 29.651 | 48.781 | 1.00 25.28 | A C |
| ATOM | 754 | O | LEU | A | 132 | 42.193 | 29.904 | 49.046 | 1.00 24.89 | A O |
| ATOM | 755 | N | ASP | A | 133 | 40.356 | 30.200 | 47.764 | 1.00 25.85 | A N |
| ATOM | 756 | CA | ASP | A | 133 | 40.982 | 31.204 | 46.924 | 1.00 27.52 | A C |
| ATOM | 757 | CB | ASP | A | 133 | 40.052 | 31.690 | 45.816 | 1.00 30.24 | A C |
| ATOM | 758 | CG | ASP | A | 133 | 39.870 | 30.688 | 44.714 | 1.00 32.98 | A C |
| ATOM | 759 | OD1 | ASP | A | 133 | 40.842 | 29.966 | 44.389 | 1.00 34.80 | A O |
| ATOM | 760 | OD2 | ASP | A | 133 | 38.750 | 30.648 | 44.155 | 1.00 36.35 | A O |
| ATOM | 761 | C | ASP | A | 133 | 41.226 | 32.391 | 47.826 | 1.00 27.54 | A C |
| ATOM | 762 | O | ASP | A | 133 | 40.477 | 32.629 | 48.757 | 1.00 28.23 | A O |
| ATOM | 763 | N | TYR | A | 134 | 42.276 | 33.139 | 47.548 | 1.00 28.07 | A N |
| ATOM | 764 | CA | TYR | A | 134 | 42.534 | 34.320 | 48.336 | 1.00 28.58 | A C |
| ATOM | 765 | CB | TYR | A | 134 | 44.007 | 34.435 | 48.690 | 1.00 29.78 | A C |
| ATOM | 766 | CG | TYR | A | 134 | 44.360 | 35.824 | 49.144 | 1.00 30.31 | A C |
| ATOM | 767 | CD1 | TYR | A | 134 | 44.011 | 36.275 | 50.417 | 1.00 29.57 | A C |
| ATOM | 768 | CE1 | TYR | A | 134 | 44.268 | 37.581 | 50.805 | 1.00 31.23 | A C |
| ATOM | 769 | CD2 | TYR | A | 134 | 44.982 | 36.715 | 48.272 | 1.00 30.73 | A C |
| ATOM | 770 | CE2 | TYR | A | 134 | 45.240 | 38.019 | 48.646 | 1.00 31.63 | A C |
| ATOM | 771 | CZ | TYR | A | 134 | 44.885 | 38.448 | 49.910 | 1.00 32.23 | A C |
| ATOM | 772 | OH | TYR | A | 134 | 45.151 | 39.748 | 50.272 | 1.00 33.70 | A O |
| ATOM | 773 | C | TYR | A | 134 | 42.119 | 35.515 | 47.491 | 1.00 28.83 | A C |
| ATOM | 774 | O | TYR | A | 134 | 42.466 | 35.602 | 46.307 | 1.00 29.47 | A O |
| ATOM | 775 | N | VAL | A | 135 | 41.362 | 36.422 | 48.091 | 1.00 27.56 | A N |
| ATOM | 776 | CA | VAL | A | 135 | 40.915 | 37.621 | 47.399 | 1.00 26.92 | A C |
| ATOM | 777 | CB | VAL | A | 135 | 39.374 | 37.697 | 47.399 | 1.00 27.43 | A C |
| ATOM | 778 | CG1 | VAL | A | 135 | 38.889 | 38.851 | 46.548 | 1.00 24.42 | A C |

FIG. 5-14

```
ATOM    779  CG2 VAL A 135      38.820  36.391  46.860  1.00 25.36      A    C
ATOM    780  C   VAL A 135      41.573  38.756  48.184  1.00 27.34      A    C
ATOM    781  O   VAL A 135      41.580  38.750  49.389  1.00 26.12      A    O
ATOM    782  N   PRO A 136      42.156  39.733  47.479  1.00 28.37      A    N
ATOM    783  CD  PRO A 136      42.039  39.879  46.015  1.00 27.81      A    C
ATOM    784  CA  PRO A 136      42.854  40.885  48.057  1.00 28.39      A    C
ATOM    785  CB  PRO A 136      43.475  41.544  46.832  1.00 27.05      A    C
ATOM    786  CG  PRO A 136      42.425  41.323  45.797  1.00 29.44      A    C
ATOM    787  C   PRO A 136      42.075  41.887  48.896  1.00 28.18      A    C
ATOM    788  O   PRO A 136      42.636  42.522  49.790  1.00 29.18      A    O
ATOM    789  N   GLU A 137      40.788  42.033  48.626  1.00 27.38      A    N
ATOM    790  CA  GLU A 137      40.013  43.022  49.349  1.00 26.22      A    C
ATOM    791  CB  GLU A 137      39.940  44.286  48.482  1.00 27.87      A    C
ATOM    792  CG  GLU A 137      39.646  45.554  49.239  1.00 30.15      A    C
ATOM    793  CD  GLU A 137      40.706  45.876  50.255  1.00 29.54      A    C
ATOM    794  OE1 GLU A 137      41.845  46.200  49.859  1.00 30.88      A    O
ATOM    795  OE2 GLU A 137      40.397  45.799  51.457  1.00 33.09      A    O
ATOM    796  C   GLU A 137      38.610  42.551  49.720  1.00 25.32      A    C
ATOM    797  O   GLU A 137      38.173  41.507  49.294  1.00 24.97      A    O
ATOM    798  N   THR A 138      37.921  43.349  50.531  1.00 25.37      A    N
ATOM    799  CA  THR A 138      36.554  43.053  50.963  1.00 23.31      A    C
ATOM    800  CB  THR A 138      36.476  42.694  52.467  1.00 22.37      A    C
ATOM    801  OG1 THR A 138      36.848  43.836  53.250  1.00 21.65      A    O
ATOM    802  CG2 THR A 138      37.383  41.521  52.790  1.00 17.71      A    C
ATOM    803  C   THR A 138      35.680  44.283  50.766  1.00 24.19      A    C
ATOM    804  O   THR A 138      36.177  45.380  50.599  1.00 25.72      A    O
ATOM    805  N   VAL A 139      34.368  44.089  50.788  1.00 24.02      A    N
ATOM    806  CA  VAL A 139      33.460  45.212  50.646  1.00 22.25      A    C
ATOM    807  CB  VAL A 139      32.016  44.741  50.425  1.00 21.33      A    C
ATOM    808  CG1 VAL A 139      31.064  45.925  50.509  1.00 20.32      A    C
ATOM    809  CG2 VAL A 139      31.895  44.077  49.062  1.00 22.48      A    C
ATOM    810  C   VAL A 139      33.538  46.043  51.927  1.00 23.06      A    C
ATOM    811  O   VAL A 139      33.522  47.263  51.885  1.00 23.39      A    O
ATOM    812  N   TYR A 140      33.637  45.373  53.067  1.00 22.36      A    N
ATOM    813  CA  TYR A 140      33.727  46.089  54.331  1.00 22.67      A    C
ATOM    814  CB  TYR A 140      33.961  45.118  55.484  1.00 20.99      A    C
ATOM    815  CG  TYR A 140      34.085  45.788  56.838  1.00 21.76      A    C
ATOM    816  CD1 TYR A 140      32.976  46.367  57.465  1.00 20.71      A    C
ATOM    817  CE1 TYR A 140      33.094  46.992  58.711  1.00 22.90      A    C
ATOM    818  CD2 TYR A 140      35.314  45.852  57.485  1.00 21.20      A    C
ATOM    819  CE2 TYR A 140      35.445  46.472  58.721  1.00 23.96      A    C
ATOM    820  CZ  TYR A 140      34.337  47.038  59.329  1.00 24.06      A    C
ATOM    821  OH  TYR A 140      34.491  47.635  60.552  1.00 25.70      A    O
ATOM    822  C   TYR A 140      34.862  47.116  54.291  1.00 24.19      A    C
ATOM    823  O   TYR A 140      34.632  48.285  54.541  1.00 24.36      A    O
ATOM    824  N   ARG A 141      36.076  46.669  53.963  1.00 24.94      A    N
ATOM    825  CA  ARG A 141      37.235  47.567  53.907  1.00 25.11      A    C
ATOM    826  CB  ARG A 141      38.512  46.776  53.613  1.00 25.94      A    C
ATOM    827  CG  ARG A 141      38.915  45.795  54.712  1.00 29.78      A    C
ATOM    828  CD  ARG A 141      40.116  44.954  54.288  1.00 33.41      A    C
ATOM    829  NE  ARG A 141      41.349  45.739  54.224  1.00 37.25      A    N
ATOM    830  CZ  ARG A 141      42.337  45.519  53.364  1.00 39.19      A    C
ATOM    831  NH1 ARG A 141      42.245  44.537  52.481  1.00 41.44      A    N
ATOM    832  NH2 ARG A 141      43.430  46.274  53.387  1.00 42.54      A    N
ATOM    833  C   ARG A 141      37.081  48.680  52.874  1.00 25.17      A    C
ATOM    834  O   ARG A 141      37.326  49.845  53.165  1.00 24.16      A    O
ATOM    835  N   VAL A 142      36.671  48.310  51.666  1.00 24.93      A    N
ATOM    836  CA  VAL A 142      36.486  49.278  50.602  1.00 24.76      A    C
ATOM    837  CB  VAL A 142      36.053  48.585  49.297  1.00 24.91      A    C
ATOM    838  CG1 VAL A 142      35.784  49.618  48.220  1.00 23.97      A    C
```

FIG. 5-15

```
ATOM    839  CG2 VAL A 142      37.140  47.636  48.845  1.00 25.06      A    C
ATOM    840  C   VAL A 142      35.455  50.338  50.976  1.00 25.32      A    C
ATOM    841  O   VAL A 142      35.702  51.521  50.819  1.00 24.96      A    O
ATOM    842  N   ALA A 143      34.305  49.907  51.474  1.00 24.11      A    N
ATOM    843  CA  ALA A 143      33.263  50.849  51.855  1.00 26.44      A    C
ATOM    844  CB  ALA A 143      32.032  50.102  52.360  1.00 24.93      A    C
ATOM    845  C   ALA A 143      33.788  51.783  52.935  1.00 27.62      A    C
ATOM    846  O   ALA A 143      33.561  52.975  52.891  1.00 28.58      A    O
ATOM    847  N   ARG A 144      34.498  51.217  53.903  1.00 29.19      A    N
ATOM    848  CA  ARG A 144      35.048  51.995  54.998  1.00 32.22      A    C
ATOM    849  CB  ARG A 144      35.762  51.072  55.981  1.00 35.02      A    C
ATOM    850  CG  ARG A 144      36.132  51.737  57.280  1.00 38.81      A    C
ATOM    851  CD  ARG A 144      37.215  50.973  58.000  1.00 42.99      A    C
ATOM    852  NE  ARG A 144      37.733  51.743  59.125  1.00 46.72      A    N
ATOM    853  CZ  ARG A 144      37.070  51.956  60.258  1.00 48.00      A    C
ATOM    854  NH1 ARG A 144      35.851  51.445  60.426  1.00 47.43      A    N
ATOM    855  NH2 ARG A 144      37.627  52.694  61.217  1.00 48.61      A    N
ATOM    856  C   ARG A 144      36.018  53.057  54.484  1.00 33.14      A    C
ATOM    857  O   ARG A 144      36.038  54.169  54.992  1.00 32.69      A    O
ATOM    858  N   HIS A 145      36.824  52.699  53.481  1.00 34.01      A    N
ATOM    859  CA  HIS A 145      37.776  53.638  52.896  1.00 35.09      A    C
ATOM    860  CB  HIS A 145      38.562  52.989  51.746  1.00 37.71      A    C
ATOM    861  CG  HIS A 145      39.741  52.179  52.194  1.00 41.33      A    C
ATOM    862  CD2 HIS A 145      40.073  50.887  51.968  1.00 42.76      A    C
ATOM    863  ND1 HIS A 145      40.750  52.705  52.978  1.00 42.84      A    N
ATOM    864  CE1 HIS A 145      41.655  51.758  53.216  1.00 43.34      A    C
ATOM    865  NE2 HIS A 145      41.261  50.650  52.612  1.00 43.14      A    N
ATOM    866  C   HIS A 145      37.032  54.857  52.380  1.00 35.20      A    C
ATOM    867  O   HIS A 145      37.360  55.969  52.718  1.00 35.56      A    O
ATOM    868  N   TYR A 146      36.035  54.623  51.532  1.00 34.54      A    N
ATOM    869  CA  TYR A 146      35.250  55.712  50.963  1.00 33.75      A    C
ATOM    870  CB  TYR A 146      34.256  55.185  49.931  1.00 30.94      A    C
ATOM    871  CG  TYR A 146      34.855  54.880  48.581  1.00 27.60      A    C
ATOM    872  CD1 TYR A 146      35.541  53.692  48.349  1.00 27.50      A    C
ATOM    873  CE1 TYR A 146      36.080  53.405  47.095  1.00 24.98      A    C
ATOM    874  CD2 TYR A 146      34.728  55.780  47.529  1.00 25.97      A    C
ATOM    875  CE2 TYR A 146      35.262  55.507  46.282  1.00 25.54      A    C
ATOM    876  CZ  TYR A 146      35.937  54.321  46.071  1.00 24.36      A    C
ATOM    877  OH  TYR A 146      36.472  54.067  44.837  1.00 23.71      A    O
ATOM    878  C   TYR A 146      34.487  56.485  52.027  1.00 34.86      A    C
ATOM    879  O   TYR A 146      34.317  57.688  51.929  1.00 35.20      A    O
ATOM    880  N   SER A 147      34.035  55.773  53.047  1.00 35.60      A    N
ATOM    881  CA  SER A 147      33.279  56.386  54.130  1.00 37.66      A    C
ATOM    882  CB  SER A 147      32.607  55.301  54.970  1.00 37.50      A    C
ATOM    883  OG  SER A 147      31.762  55.871  55.949  1.00 39.07      A    O
ATOM    884  C   SER A 147      34.189  57.237  55.008  1.00 39.51      A    C
ATOM    885  O   SER A 147      33.781  58.281  55.525  1.00 38.73      A    O
ATOM    886  N   ARG A 148      35.427  56.783  55.170  1.00 41.25      A    N
ATOM    887  CA  ARG A 148      36.405  57.501  55.978  1.00 43.49      A    C
ATOM    888  CB  ARG A 148      37.698  56.690  56.108  1.00 45.44      A    C
ATOM    889  CG  ARG A 148      37.780  55.843  57.371  1.00 49.61      A    C
ATOM    890  CD  ARG A 148      37.615  56.727  58.607  1.00 53.54      A    C
ATOM    891  NE  ARG A 148      37.996  56.056  59.848  1.00 56.00      A    N
ATOM    892  CZ  ARG A 148      39.253  55.800  60.205  1.00 57.33      A    C
ATOM    893  NH1 ARG A 148      40.258  56.161  59.410  1.00 57.00      A    N
ATOM    894  NH2 ARG A 148      39.503  55.194  61.365  1.00 58.07      A    N
ATOM    895  C   ARG A 148      36.726  58.857  55.359  1.00 43.77      A    C
ATOM    896  O   ARG A 148      36.967  59.852  56.080  1.00 43.40      A    O
ATOM    897  N   ALA A 149      36.733  58.902  54.030  1.00 43.17      A    N
ATOM    898  CA  ALA A 149      37.031  60.137  53.319  1.00 43.72      A    C
```

FIG. 5-16

| | | | | | | | | | | | |
|---|---|---|---|---|---|---|---|---|---|---|---|
| ATOM | 899 | CB | ALA | A | 149 | 37.890 | 59.834 | 52.093 | 1.00 | 43.41 | A C |
| ATOM | 900 | C | ALA | A | 149 | 35.765 | 60.890 | 52.906 | 1.00 | 44.08 | A C |
| ATOM | 901 | O | ALA | A | 149 | 35.792 | 61.718 | 51.990 | 1.00 | 44.85 | A O |
| ATOM | 902 | N | LYS | A | 150 | 34.658 | 60.599 | 53.578 | 1.00 | 44.43 | A N |
| ATOM | 903 | CA | LYS | A | 150 | 33.390 | 61.259 | 53.291 | 1.00 | 45.35 | A C |
| ATOM | 904 | CB | LYS | A | 150 | 33.451 | 62.706 | 53.801 | 1.00 | 46.87 | A C |
| ATOM | 905 | CG | LYS | A | 150 | 33.765 | 62.778 | 55.299 | 1.00 | 48.25 | A C |
| ATOM | 906 | CD | LYS | A | 150 | 34.014 | 64.195 | 55.803 | 1.00 | 50.09 | A C |
| ATOM | 907 | CE | LYS | A | 150 | 32.721 | 64.998 | 55.916 | 1.00 | 51.38 | A C |
| ATOM | 908 | NZ | LYS | A | 150 | 32.929 | 66.276 | 56.688 | 1.00 | 51.86 | A N |
| ATOM | 909 | C | LYS | A | 150 | 32.982 | 61.222 | 51.812 | 1.00 | 45.10 | A C |
| ATOM | 910 | O | LYS | A | 150 | 32.211 | 62.057 | 51.349 | 1.00 | 44.58 | A O |
| ATOM | 911 | N | GLN | A | 151 | 33.503 | 60.242 | 51.081 | 1.00 | 44.60 | A N |
| ATOM | 912 | CA | GLN | A | 151 | 33.190 | 60.082 | 49.664 | 1.00 | 44.04 | A C |
| ATOM | 913 | CB | GLN | A | 151 | 34.451 | 59.727 | 48.879 | 1.00 | 45.13 | A C |
| ATOM | 914 | CG | GLN | A | 151 | 35.722 | 60.357 | 49.428 | 1.00 | 46.36 | A C |
| ATOM | 915 | CD | GLN | A | 151 | 36.944 | 59.982 | 48.614 | 1.00 | 47.77 | A C |
| ATOM | 916 | OE1 | GLN | A | 151 | 37.165 | 60.513 | 47.522 | 1.00 | 48.90 | A O |
| ATOM | 917 | NE2 | GLN | A | 151 | 37.740 | 59.047 | 49.136 | 1.00 | 48.82 | A N |
| ATOM | 918 | C | GLN | A | 151 | 32.211 | 58.928 | 49.550 | 1.00 | 43.06 | A C |
| ATOM | 919 | O | GLN | A | 151 | 31.859 | 58.300 | 50.540 | 1.00 | 43.20 | A O |
| ATOM | 920 | N | THR | A | 152 | 31.777 | 58.645 | 48.330 | 1.00 | 41.46 | A N |
| ATOM | 921 | CA | THR | A | 152 | 30.861 | 57.540 | 48.115 | 1.00 | 39.10 | A C |
| ATOM | 922 | CB | THR | A | 152 | 29.423 | 58.034 | 47.877 | 1.00 | 40.15 | A C |
| ATOM | 923 | OG1 | THR | A | 152 | 28.547 | 56.903 | 47.778 | 1.00 | 43.16 | A O |
| ATOM | 924 | CG2 | THR | A | 152 | 29.339 | 58.852 | 46.604 | 1.00 | 41.20 | A C |
| ATOM | 925 | C | THR | A | 152 | 31.348 | 56.706 | 46.940 | 1.00 | 35.67 | A C |
| ATOM | 926 | O | THR | A | 152 | 31.980 | 57.223 | 46.023 | 1.00 | 34.37 | A O |
| ATOM | 927 | N | LEU | A | 153 | 31.070 | 55.410 | 46.984 | 1.00 | 32.31 | A N |
| ATOM | 928 | CA | LEU | A | 153 | 31.494 | 54.509 | 45.919 | 1.00 | 30.47 | A C |
| ATOM | 929 | CB | LEU | A | 153 | 31.265 | 53.058 | 46.356 | 1.00 | 30.09 | A C |
| ATOM | 930 | CG | LEU | A | 153 | 31.768 | 51.892 | 45.497 | 1.00 | 31.25 | A C |
| ATOM | 931 | CD1 | LEU | A | 153 | 33.296 | 51.893 | 45.421 | 1.00 | 29.06 | A C |
| ATOM | 932 | CD2 | LEU | A | 153 | 31.281 | 50.585 | 46.122 | 1.00 | 30.39 | A C |
| ATOM | 933 | C | LEU | A | 153 | 30.714 | 54.804 | 44.634 | 1.00 | 28.28 | A C |
| ATOM | 934 | O | LEU | A | 153 | 29.502 | 54.987 | 44.668 | 1.00 | 27.63 | A O |
| ATOM | 935 | N | PRO | A | 154 | 31.412 | 54.884 | 43.490 | 1.00 | 26.06 | A N |
| ATOM | 936 | CD | PRO | A | 154 | 32.870 | 54.805 | 43.307 | 1.00 | 25.35 | A C |
| ATOM | 937 | CA | PRO | A | 154 | 30.732 | 55.155 | 42.220 | 1.00 | 25.69 | A C |
| ATOM | 938 | CB | PRO | A | 154 | 31.862 | 55.073 | 41.195 | 1.00 | 25.62 | A C |
| ATOM | 939 | CG | PRO | A | 154 | 33.066 | 55.504 | 41.985 | 1.00 | 25.69 | A C |
| ATOM | 940 | C | PRO | A | 154 | 29.675 | 54.078 | 42.004 | 1.00 | 25.53 | A C |
| ATOM | 941 | O | PRO | A | 154 | 29.946 | 52.916 | 42.165 | 1.00 | 24.95 | A O |
| ATOM | 942 | N | VAL | A | 155 | 28.470 | 54.496 | 41.636 | 1.00 | 26.12 | A N |
| ATOM | 943 | CA | VAL | A | 155 | 27.369 | 53.570 | 41.427 | 1.00 | 26.91 | A C |
| ATOM | 944 | CB | VAL | A | 155 | 26.115 | 54.331 | 40.945 | 1.00 | 27.47 | A C |
| ATOM | 945 | CG1 | VAL | A | 155 | 25.776 | 55.424 | 41.955 | 1.00 | 28.32 | A C |
| ATOM | 946 | CG2 | VAL | A | 155 | 26.354 | 54.939 | 39.585 | 1.00 | 29.58 | A C |
| ATOM | 947 | C | VAL | A | 155 | 27.692 | 52.403 | 40.493 | 1.00 | 26.27 | A C |
| ATOM | 948 | O | VAL | A | 155 | 27.206 | 51.294 | 40.703 | 1.00 | 24.85 | A O |
| ATOM | 949 | N | ILE | A | 156 | 28.525 | 52.640 | 39.482 | 1.00 | 25.24 | A N |
| ATOM | 950 | CA | ILE | A | 156 | 28.878 | 51.577 | 38.553 | 1.00 | 24.58 | A C |
| ATOM | 951 | CB | ILE | A | 156 | 29.901 | 52.063 | 37.492 | 1.00 | 24.91 | A C |
| ATOM | 952 | CG2 | ILE | A | 156 | 31.203 | 52.451 | 38.157 | 1.00 | 27.44 | A C |
| ATOM | 953 | CG1 | ILE | A | 156 | 30.143 | 50.965 | 36.456 | 1.00 | 24.90 | A C |
| ATOM | 954 | CD1 | ILE | A | 156 | 28.883 | 50.504 | 35.742 | 1.00 | 23.78 | A C |
| ATOM | 955 | C | ILE | A | 156 | 29.436 | 50.383 | 39.335 | 1.00 | 23.61 | A C |
| ATOM | 956 | O | ILE | A | 156 | 29.171 | 49.228 | 38.996 | 1.00 | 22.96 | A O |
| ATOM | 957 | N | TYR | A | 157 | 30.196 | 50.663 | 40.390 | 1.00 | 23.42 | A N |
| ATOM | 958 | CA | TYR | A | 157 | 30.743 | 49.593 | 41.225 | 1.00 | 23.31 | A C |

FIG. 5-17

```
ATOM    959  CB   TYR A 157      31.901  50.105  42.086  1.00 22.84      A    C
ATOM    960  CG   TYR A 157      33.176  50.278  41.312  1.00 24.56      A    C
ATOM    961  CD1  TYR A 157      33.700  51.544  41.061  1.00 25.30      A    C
ATOM    962  CE1  TYR A 157      34.859  51.700  40.314  1.00 26.14      A    C
ATOM    963  CD2  TYR A 157      33.849  49.169  40.792  1.00 24.58      A    C
ATOM    964  CE2  TYR A 157      35.007  49.317  40.046  1.00 25.15      A    C
ATOM    965  CZ   TYR A 157      35.502  50.586  39.812  1.00 26.28      A    C
ATOM    966  OH   TYR A 157      36.647  50.744  39.081  1.00 30.67      A    O
ATOM    967  C    TYR A 157      29.659  49.022  42.126  1.00 22.86      A    C
ATOM    968  O    TYR A 157      29.646  47.842  42.408  1.00 23.77      A    O
ATOM    969  N    VAL A 158      28.756  49.881  42.579  1.00 21.87      A    N
ATOM    970  CA   VAL A 158      27.659  49.433  43.417  1.00 22.49      A    C
ATOM    971  CB   VAL A 158      26.766  50.619  43.832  1.00 23.37      A    C
ATOM    972  CG1  VAL A 158      25.600  50.127  44.678  1.00 22.21      A    C
ATOM    973  CG2  VAL A 158      27.594  51.650  44.594  1.00 22.17      A    C
ATOM    974  C    VAL A 158      26.840  48.431  42.598  1.00 23.15      A    C
ATOM    975  O    VAL A 158      26.441  47.394  43.100  1.00 24.25      A    O
ATOM    976  N    LYS A 159      26.617  48.761  41.327  1.00 21.71      A    N
ATOM    977  CA   LYS A 159      25.860  47.910  40.416  1.00 21.45      A    C
ATOM    978  CB   LYS A 159      25.703  48.593  39.055  1.00 21.82      A    C
ATOM    979  CG   LYS A 159      24.717  49.740  39.040  1.00 21.87      A    C
ATOM    980  CD   LYS A 159      24.615  50.388  37.671  1.00 21.60      A    C
ATOM    981  CE   LYS A 159      23.659  51.573  37.702  1.00 21.37      A    C
ATOM    982  NZ   LYS A 159      23.579  52.247  36.370  1.00 22.49      A    N
ATOM    983  C    LYS A 159      26.537  46.563  40.229  1.00 21.63      A    C
ATOM    984  O    LYS A 159      25.916  45.536  40.396  1.00 20.39      A    O
ATOM    985  N    LEU A 160      27.820  46.587  39.882  1.00 21.81      A    N
ATOM    986  CA   LEU A 160      28.580  45.359  39.671  1.00 22.68      A    C
ATOM    987  CB   LEU A 160      30.007  45.683  39.239  1.00 20.62      A    C
ATOM    988  CG   LEU A 160      30.235  46.141  37.806  1.00 21.92      A    C
ATOM    989  CD1  LEU A 160      31.664  46.644  37.660  1.00 20.65      A    C
ATOM    990  CD2  LEU A 160      29.967  44.987  36.852  1.00 21.55      A    C
ATOM    991  C    LEU A 160      28.636  44.474  40.912  1.00 23.35      A    C
ATOM    992  O    LEU A 160      28.423  43.273  40.829  1.00 24.77      A    O
ATOM    993  N    TYR A 161      28.933  45.078  42.058  1.00 23.09      A    N
ATOM    994  CA   TYR A 161      29.034  44.325  43.301  1.00 22.97      A    C
ATOM    995  CB   TYR A 161      29.575  45.211  44.441  1.00 23.29      A    C
ATOM    996  CG   TYR A 161      30.975  45.768  44.225  1.00 25.50      A    C
ATOM    997  CD1  TYR A 161      31.814  45.270  43.221  1.00 25.11      A    C
ATOM    998  CE1  TYR A 161      33.097  45.794  43.031  1.00 27.40      A    C
ATOM    999  CD2  TYR A 161      31.462  46.806  45.032  1.00 26.64      A    C
ATOM   1000  CE2  TYR A 161      32.738  47.331  44.852  1.00 24.97      A    C
ATOM   1001  CZ   TYR A 161      33.550  46.827  43.854  1.00 27.66      A    C
ATOM   1002  OH   TYR A 161      34.816  47.351  43.681  1.00 30.52      A    O
ATOM   1003  C    TYR A 161      27.717  43.699  43.721  1.00 21.64      A    C
ATOM   1004  O    TYR A 161      27.676  42.532  44.051  1.00 21.38      A    O
ATOM   1005  N    MET A 162      26.644  44.486  43.703  1.00 22.15      A    N
ATOM   1006  CA   MET A 162      25.339  43.976  44.100  1.00 21.26      A    C
ATOM   1007  CB   MET A 162      24.319  45.111  44.180  1.00 21.81      A    C
ATOM   1008  CG   MET A 162      24.531  46.043  45.373  1.00 22.37      A    C
ATOM   1009  SD   MET A 162      24.870  45.141  46.921  1.00 21.68      A    S
ATOM   1010  CE   MET A 162      23.291  44.377  47.212  1.00 21.67      A    C
ATOM   1011  C    MET A 162      24.850  42.904  43.145  1.00 21.23      A    C
ATOM   1012  O    MET A 162      24.328  41.899  43.570  1.00 22.61      A    O
ATOM   1013  N    TYR A 163      25.032  43.130  41.850  1.00 20.57      A    N
ATOM   1014  CA   TYR A 163      24.602  42.167  40.848  1.00 20.38      A    C
ATOM   1015  CB   TYR A 163      25.025  42.636  39.458  1.00 21.22      A    C
ATOM   1016  CG   TYR A 163      24.622  41.690  38.350  1.00 22.32      A    C
ATOM   1017  CD1  TYR A 163      23.352  41.753  37.780  1.00 22.40      A    C
ATOM   1018  CE1  TYR A 163      22.980  40.877  36.758  1.00 25.27      A    C
```

FIG. 5-18

```
ATOM   1019  CD2  TYR A 163      25.509  40.727  37.878  1.00 20.69           A    C
ATOM   1020  CE2  TYR A 163      25.149  39.850  36.863  1.00 21.54           A    C
ATOM   1021  CZ   TYR A 163      23.883  39.933  36.306  1.00 23.36           A    C
ATOM   1022  OH   TYR A 163      23.531  39.090  35.278  1.00 26.02           A    O
ATOM   1023  C    TYR A 163      25.227  40.798  41.132  1.00 20.74           A    C
ATOM   1024  O    TYR A 163      24.530  39.777  41.198  1.00 18.53           A    O
ATOM   1025  N    GLN A 164      26.547  40.786  41.289  1.00 19.75           A    N
ATOM   1026  CA   GLN A 164      27.260  39.544  41.568  1.00 20.34           A    C
ATOM   1027  CB   GLN A 164      28.775  39.805  41.579  1.00 20.02           A    C
ATOM   1028  CG   GLN A 164      29.320  40.266  40.214  1.00 20.98           A    C
ATOM   1029  CD   GLN A 164      30.809  40.601  40.225  1.00 21.58           A    C
ATOM   1030  OE1  GLN A 164      31.637  39.726  40.243  1.00 21.16           A    O
ATOM   1031  NE2  GLN A 164      31.131  41.887  40.219  1.00 19.60           A    N
ATOM   1032  C    GLN A 164      26.796  38.919  42.893  1.00 20.15           A    C
ATOM   1033  O    GLN A 164      26.704  37.706  43.008  1.00 19.97           A    O
ATOM   1034  N    LEU A 165      26.491  39.749  43.885  1.00 19.17           A    N
ATOM   1035  CA   LEU A 165      26.009  39.225  45.158  1.00 19.84           A    C
ATOM   1036  CB   LEU A 165      25.810  40.365  46.162  1.00 18.00           A    C
ATOM   1037  CG   LEU A 165      25.025  40.047  47.444  1.00 21.59           A    C
ATOM   1038  CD1  LEU A 165      25.689  38.910  48.215  1.00 19.52           A    C
ATOM   1039  CD2  LEU A 165      24.931  41.317  48.304  1.00 21.48           A    C
ATOM   1040  C    LEU A 165      24.692  38.467  44.937  1.00 19.03           A    C
ATOM   1041  O    LEU A 165      24.524  37.373  45.415  1.00 17.83           A    O
ATOM   1042  N    PHE A 166      23.770  39.066  44.193  1.00 18.52           A    N
ATOM   1043  CA   PHE A 166      22.497  38.418  43.926  1.00 19.39           A    C
ATOM   1044  CB   PHE A 166      21.546  39.396  43.242  1.00 17.62           A    C
ATOM   1045  CG   PHE A 166      20.977  40.417  44.185  1.00 19.57           A    C
ATOM   1046  CD1  PHE A 166      20.256  40.008  45.303  1.00 17.71           A    C
ATOM   1047  CD2  PHE A 166      21.183  41.779  43.983  1.00 18.94           A    C
ATOM   1048  CE1  PHE A 166      19.753  40.931  46.199  1.00 17.52           A    C
ATOM   1049  CE2  PHE A 166      20.684  42.709  44.876  1.00 17.07           A    C
ATOM   1050  CZ   PHE A 166      19.965  42.283  45.989  1.00 19.21           A    C
ATOM   1051  C    PHE A 166      22.671  37.137  43.119  1.00 20.05           A    C
ATOM   1052  O    PHE A 166      21.955  36.182  43.341  1.00 19.94           A    O
ATOM   1053  N    ARG A 167      23.636  37.107  42.201  1.00 20.69           A    N
ATOM   1054  CA   ARG A 167      23.865  35.883  41.437  1.00 21.34           A    C
ATOM   1055  CB   ARG A 167      24.940  36.067  40.371  1.00 22.24           A    C
ATOM   1056  CG   ARG A 167      24.388  36.204  38.965  1.00 24.84           A    C
ATOM   1057  CD   ARG A 167      25.492  36.099  37.919  1.00 24.84           A    C
ATOM   1058  NE   ARG A 167      25.798  34.717  37.564  1.00 24.78           A    N
ATOM   1059  CZ   ARG A 167      26.712  34.368  36.666  1.00 27.41           A    C
ATOM   1060  NH1  ARG A 167      27.416  35.296  36.032  1.00 25.13           A    N
ATOM   1061  NH2  ARG A 167      26.911  33.090  36.376  1.00 29.55           A    N
ATOM   1062  C    ARG A 167      24.284  34.732  42.351  1.00 20.49           A    C
ATOM   1063  O    ARG A 167      23.804  33.610  42.200  1.00 20.99           A    O
ATOM   1064  N    SER A 168      25.187  35.016  43.289  1.00 19.40           A    N
ATOM   1065  CA   SER A 168      25.656  33.995  44.214  1.00 20.18           A    C
ATOM   1066  CB   SER A 168      26.764  34.544  45.117  1.00 19.91           A    C
ATOM   1067  OG   SER A 168      26.290  35.574  45.956  1.00 19.31           A    O
ATOM   1068  C    SER A 168      24.502  33.483  45.059  1.00 20.36           A    C
ATOM   1069  O    SER A 168      24.402  32.296  45.316  1.00 21.19           A    O
ATOM   1070  N    LEU A 169      23.631  34.394  45.477  1.00 20.43           A    N
ATOM   1071  CA   LEU A 169      22.474  34.026  46.285  1.00 20.80           A    C
ATOM   1072  CB   LEU A 169      21.767  35.283  46.783  1.00 21.14           A    C
ATOM   1073  CG   LEU A 169      22.111  35.787  48.191  1.00 22.65           A    C
ATOM   1074  CD1  LEU A 169      23.570  35.553  48.531  1.00 21.25           A    C
ATOM   1075  CD2  LEU A 169      21.755  37.256  48.273  1.00 19.59           A    C
ATOM   1076  C    LEU A 169      21.512  33.153  45.481  1.00 20.88           A    C
ATOM   1077  O    LEU A 169      21.018  32.136  45.985  1.00 20.39           A    O
ATOM   1078  N    ALA A 170      21.252  33.550  44.236  1.00 20.69           A    N
```

FIG. 5-19

```
ATOM   1079  CA   ALA A 170      20.364  32.788  43.368  1.00 20.55      A    C
ATOM   1080  CB   ALA A 170      20.237  33.469  42.010  1.00 19.38      A    C
ATOM   1081  C    ALA A 170      20.937  31.385  43.207  1.00 20.45      A    C
ATOM   1082  O    ALA A 170      20.208  30.418  43.165  1.00 21.67      A    O
ATOM   1083  N    TYR A 171      22.259  31.287  43.143  1.00 20.49      A    N
ATOM   1084  CA   TYR A 171      22.896  29.991  42.995  1.00 22.64      A    C
ATOM   1085  CB   TYR A 171      24.386  30.154  42.679  1.00 22.36      A    C
ATOM   1086  CG   TYR A 171      25.127  28.838  42.574  1.00 22.82      A    C
ATOM   1087  CD1  TYR A 171      24.903  27.963  41.507  1.00 22.58      A    C
ATOM   1088  CE1  TYR A 171      25.581  26.740  41.420  1.00 22.06      A    C
ATOM   1089  CD2  TYR A 171      26.045  28.458  43.552  1.00 24.15      A    C
ATOM   1090  CE2  TYR A 171      26.728  27.242  43.475  1.00 24.83      A    C
ATOM   1091  CZ   TYR A 171      26.492  26.390  42.408  1.00 24.45      A    C
ATOM   1092  OH   TYR A 171      27.183  25.202  42.336  1.00 26.64      A    O
ATOM   1093  C    TYR A 171      22.738  29.107  44.231  1.00 22.57      A    C
ATOM   1094  O    TYR A 171      22.331  27.975  44.111  1.00 23.58      A    O
ATOM   1095  N    ILE A 172      23.063  29.629  45.412  1.00 22.43      A    N
ATOM   1096  CA   ILE A 172      22.944  28.825  46.627  1.00 22.47      A    C
ATOM   1097  CB   ILE A 172      23.684  29.473  47.842  1.00 21.02      A    C
ATOM   1098  CG2  ILE A 172      25.162  29.626  47.525  1.00 20.11      A    C
ATOM   1099  CG1  ILE A 172      23.079  30.832  48.193  1.00 21.53      A    C
ATOM   1100  CD1  ILE A 172      23.607  31.399  49.509  1.00 19.74      A    C
ATOM   1101  C    ILE A 172      21.493  28.554  46.996  1.00 22.06      A    C
ATOM   1102  O    ILE A 172      21.186  27.506  47.491  1.00 24.17      A    O
ATOM   1103  N    HIS A 173      20.612  29.514  46.736  1.00 23.39      A    N
ATOM   1104  CA   HIS A 173      19.192  29.353  47.029  1.00 23.80      A    C
ATOM   1105  CB   HIS A 173      18.447  30.680  46.817  1.00 24.00      A    C
ATOM   1106  CG   HIS A 173      18.693  31.704  47.889  1.00 25.06      A    C
ATOM   1107  CD2  HIS A 173      19.483  31.678  48.987  1.00 23.88      A    C
ATOM   1108  ND1  HIS A 173      18.086  32.944  47.881  1.00 24.03      A    N
ATOM   1109  CE1  HIS A 173      18.496  33.635  48.930  1.00 23.46      A    C
ATOM   1110  NE2  HIS A 173      19.343  32.892  49.616  1.00 20.63      A    N
ATOM   1111  C    HIS A 173      18.567  28.269  46.143  1.00 24.69      A    C
ATOM   1112  O    HIS A 173      17.658  27.588  46.563  1.00 24.19      A    O
ATOM   1113  N    SER A 174      19.059  28.121  44.915  1.00 25.26      A    N
ATOM   1114  CA   SER A 174      18.510  27.113  44.005  1.00 26.41      A    C
ATOM   1115  CB   SER A 174      19.149  27.215  42.616  1.00 25.59      A    C
ATOM   1116  OG   SER A 174      20.384  26.523  42.562  1.00 26.10      A    O
ATOM   1117  C    SER A 174      18.759  25.719  44.579  1.00 27.90      A    C
ATOM   1118  O    SER A 174      18.145  24.750  44.149  1.00 28.29      A    O
ATOM   1119  N    PHE A 175      19.675  25.633  45.544  1.00 27.17      A    N
ATOM   1120  CA   PHE A 175      19.987  24.367  46.211  1.00 27.47      A    C
ATOM   1121  CB   PHE A 175      21.489  24.262  46.491  1.00 28.29      A    C
ATOM   1122  CG   PHE A 175      22.322  23.882  45.299  1.00 31.85      A    C
ATOM   1123  CD1  PHE A 175      22.165  22.642  44.690  1.00 32.08      A    C
ATOM   1124  CD2  PHE A 175      23.309  24.744  44.821  1.00 32.21      A    C
ATOM   1125  CE1  PHE A 175      22.980  22.257  43.624  1.00 32.88      A    C
ATOM   1126  CE2  PHE A 175      24.132  24.369  43.753  1.00 34.33      A    C
ATOM   1127  CZ   PHE A 175      23.967  23.121  43.154  1.00 33.80      A    C
ATOM   1128  C    PHE A 175      19.248  24.321  47.553  1.00 26.78      A    C
ATOM   1129  O    PHE A 175      19.392  23.359  48.329  1.00 25.52      A    O
ATOM   1130  N    GLY A 176      18.478  25.370  47.828  1.00 25.08      A    N
ATOM   1131  CA   GLY A 176      17.744  25.463  49.079  1.00 25.69      A    C
ATOM   1132  C    GLY A 176      18.611  26.006  50.208  1.00 25.83      A    C
ATOM   1133  O    GLY A 176      18.138  26.199  51.322  1.00 27.19      A    O
ATOM   1134  N    ILE A 177      19.882  26.266  49.913  1.00 23.32      A    N
ATOM   1135  CA   ILE A 177      20.814  26.770  50.916  1.00 23.33      A    C
ATOM   1136  CB   ILE A 177      22.273  26.450  50.537  1.00 23.29      A    C
ATOM   1137  CG2  ILE A 177      23.210  26.946  51.637  1.00 25.07      A    C
ATOM   1138  CG1  ILE A 177      22.447  24.943  50.338  1.00 22.67      A    C
```

FIG. 5-20

```
ATOM   1139  CD1  ILE A 177      23.726  24.570  49.619  1.00 21.61      A    C
ATOM   1140  C    ILE A 177      20.731  28.281  51.170  1.00 22.53      A    C
ATOM   1141  O    ILE A 177      20.777  29.080  50.248  1.00 21.69      A    O
ATOM   1142  N    CYS A 178      20.615  28.650  52.442  1.00 20.86      A    N
ATOM   1143  CA   CYS A 178      20.554  30.050  52.837  1.00 18.66      A    C
ATOM   1144  CB   CYS A 178      19.393  30.279  53.809  1.00 17.32      A    C
ATOM   1145  SG   CYS A 178      19.100  32.001  54.290  1.00 19.61      A    S
ATOM   1146  C    CYS A 178      21.877  30.365  53.519  1.00 18.25      A    C
ATOM   1147  O    CYS A 178      22.362  29.579  54.315  1.00 19.71      A    O
ATOM   1148  N    HIS A 179      22.463  31.510  53.189  1.00 18.16      A    N
ATOM   1149  CA   HIS A 179      23.739  31.913  53.778  1.00 17.78      A    C
ATOM   1150  CB   HIS A 179      24.333  33.076  52.973  1.00 16.49      A    C
ATOM   1151  CG   HIS A 179      25.766  33.370  53.294  1.00 14.10      A    C
ATOM   1152  CD2  HIS A 179      26.910  32.982  52.681  1.00 13.02      A    C
ATOM   1153  ND1  HIS A 179      26.147  34.138  54.369  1.00 13.56      A    N
ATOM   1154  CE1  HIS A 179      27.464  34.215  54.408  1.00 13.07      A    C
ATOM   1155  NE2  HIS A 179      27.950  33.520  53.393  1.00 13.96      A    N
ATOM   1156  C    HIS A 179      23.539  32.308  55.251  1.00 19.49      A    C
ATOM   1157  O    HIS A 179      24.254  31.834  56.132  1.00 19.19      A    O
ATOM   1158  N    ARG A 180      22.557  33.171  55.495  1.00 18.62      A    N
ATOM   1159  CA   ARG A 180      22.208  33.634  56.837  1.00 21.68      A    C
ATOM   1160  CB   ARG A 180      22.085  32.468  57.807  1.00 21.18      A    C
ATOM   1161  CG   ARG A 180      21.112  31.410  57.442  1.00 21.12      A    C
ATOM   1162  CD   ARG A 180      21.516  30.195  58.228  1.00 22.76      A    C
ATOM   1163  NE   ARG A 180      20.494  29.733  59.144  1.00 21.72      A    N
ATOM   1164  CZ   ARG A 180      20.715  28.843  60.103  1.00 19.88      A    C
ATOM   1165  NH1  ARG A 180      21.929  28.330  60.272  1.00 15.18      A    N
ATOM   1166  NH2  ARG A 180      19.713  28.453  60.874  1.00 19.13      A    N
ATOM   1167  C    ARG A 180      23.133  34.651  57.484  1.00 20.91      A    C
ATOM   1168  O    ARG A 180      22.864  35.087  58.575  1.00 24.57      A    O
ATOM   1169  N    ASP A 181      24.229  35.010  56.834  1.00 20.35      A    N
ATOM   1170  CA   ASP A 181      25.125  35.982  57.438  1.00 19.99      A    C
ATOM   1171  CB   ASP A 181      26.216  35.273  58.252   1.00 19.51      A    C
ATOM   1172  CG   ASP A 181      26.906  36.204  59.240  1.00 20.71      A    C
ATOM   1173  OD1  ASP A 181      26.374  37.295  59.521  1.00 18.47      A    O
ATOM   1174  OD2  ASP A 181      27.978  35.836  59.750  1.00 21.37      A    O
ATOM   1175  C    ASP A 181      25.733  36.905  56.398  1.00 18.59      A    C
ATOM   1176  O    ASP A 181      26.909  37.167  56.407  1.00 19.22      A    O
ATOM   1177  N    ILE A 182      24.884  37.392  55.502  1.00 17.64      A    N
ATOM   1178  CA   ILE A 182      25.301  38.304  54.454  1.00 16.25      A    C
ATOM   1179  CB   ILE A 182      24.186  38.484  53.397  1.00 15.61      A    C
ATOM   1180  CG2  ILE A 182      24.597  39.534  52.369  1.00 14.67      A    C
ATOM   1181  CG1  ILE A 182      23.888  37.139  52.725  1.00 14.46      A    C
ATOM   1182  CD1  ILE A 182      25.063  36.534  51.993  1.00 13.03      A    C
ATOM   1183  C    ILE A 182      25.611  39.652  55.096  1.00 17.44      A    C
ATOM   1184  O    ILE A 182      24.785  40.230  55.779  1.00 17.43      A    O
ATOM   1185  N    LYS A 183      26.829  40.123  54.873  1.00 17.35      A    N
ATOM   1186  CA   LYS A 183      27.284  41.392  55.399  1.00 18.18      A    C
ATOM   1187  CB   LYS A 183      27.552  41.282  56.903  1.00 18.75      A    C
ATOM   1188  CG   LYS A 183      28.676  40.331  57.270  1.00 17.72      A    C
ATOM   1189  CD   LYS A 183      28.802  40.217  58.776  1.00 18.58      A    C
ATOM   1190  CE   LYS A 183      29.845  39.206  59.165  1.00 19.80      A    C
ATOM   1191  NZ   LYS A 183      30.013  39.171  60.631  1.00 22.26      A    N
ATOM   1192  C    LYS A 183      28.573  41.758  54.670  1.00 18.52      A    C
ATOM   1193  O    LYS A 183      29.251  40.902  54.132  1.00 19.57      A    O
ATOM   1194  N    PRO A 184      28.920  43.050  54.658  1.00 18.88      A    N
ATOM   1195  CD   PRO A 184      28.172  44.143  55.308  1.00 16.59      A    C
ATOM   1196  CA   PRO A 184      30.126  43.561  53.998  1.00 19.64      A    C
ATOM   1197  CB   PRO A 184      30.231  44.983  54.537  1.00 19.10      A    C
ATOM   1198  CG   PRO A 184      28.783  45.374  54.677  1.00 19.96      A    C
```

FIG. 5-21

```
ATOM   1199  C    PRO A 184      31.397  42.738  54.254  1.00 18.96      A    C
ATOM   1200  O    PRO A 184      32.149  42.478  53.339  1.00 18.11      A    O
ATOM   1201  N    GLN A 185      31.628  42.323  55.494  1.00 20.04      A    N
ATOM   1202  CA   GLN A 185      32.827  41.540  55.790  1.00 22.09      A    C
ATOM   1203  CB   GLN A 185      33.005  41.329  57.294  1.00 23.09      A    C
ATOM   1204  CG   GLN A 185      33.208  42.586  58.086  1.00 27.04      A    C
ATOM   1205  CD   GLN A 185      32.116  42.757  59.114  1.00 32.28      A    C
ATOM   1206  OE1  GLN A 185      30.953  43.150  58.785  1.00 32.89      A    O
ATOM   1207  NE2  GLN A 185      32.443  42.440  60.363  1.00 31.85      A    N
ATOM   1208  C    GLN A 185      32.864  40.178  55.123  1.00 19.62      A    C
ATOM   1209  O    GLN A 185      33.899  39.602  55.021  1.00 19.09      A    O
ATOM   1210  N    ASN A 186      31.718  39.666  54.690  1.00 18.14      A    N
ATOM   1211  CA   ASN A 186      31.713  38.365  54.041  1.00 19.36      A    C
ATOM   1212  CB   ASN A 186      30.567  37.500  54.575  1.00 19.07      A    C
ATOM   1213  CG   ASN A 186      30.793  37.060  56.011  1.00 21.43      A    C
ATOM   1214  OD1  ASN A 186      31.923  36.925  56.446  1.00 19.90      A    O
ATOM   1215  ND2  ASN A 186      29.708  36.828  56.745  1.00 18.80      A    N
ATOM   1216  C    ASN A 186      31.629  38.468  52.529  1.00 18.17      A    C
ATOM   1217  O    ASN A 186      31.339  37.497  51.870  1.00 18.03      A    O
ATOM   1218  N    LEU A 187      31.892  39.662  52.006  1.00 18.75      A    N
ATOM   1219  CA   LEU A 187      31.851  39.916  50.569  1.00 19.90      A    C
ATOM   1220  CB   LEU A 187      30.846  41.021  50.258  1.00 18.13      A    C
ATOM   1221  CG   LEU A 187      29.421  40.794  50.753  1.00 18.67      A    C
ATOM   1222  CD1  LEU A 187      28.574  42.018  50.420  1.00 16.49      A    C
ATOM   1223  CD2  LEU A 187      28.839  39.532  50.114  1.00 19.21      A    C
ATOM   1224  C    LEU A 187      33.235  40.325  50.077  1.00 22.55      A    C
ATOM   1225  O    LEU A 187      33.655  41.474  50.247  1.00 22.40      A    O
ATOM   1226  N    LEU A 188      33.939  39.374  49.469  1.00 23.91      A    N
ATOM   1227  CA   LEU A 188      35.288  39.611  48.958  1.00 24.48      A    C
ATOM   1228  CB   LEU A 188      36.074  38.295  48.934  1.00 24.77      A    C
ATOM   1229  CG   LEU A 188      36.140  37.455  50.217  1.00 23.60      A    C
ATOM   1230  CD1  LEU A 188      36.712  36.091  49.892  1.00 23.69      A    C
ATOM   1231  CD2  LEU A 188      36.996  38.156  51.267  1.00 25.69      A    C
ATOM   1232  C    LEU A 188      35.244  40.202  47.554  1.00 26.02      A    C
ATOM   1233  O    LEU A 188      34.322  39.934  46.797  1.00 25.57      A    O
ATOM   1234  N    LEU A 189      36.242  41.009  47.208  1.00 27.43      A    N
ATOM   1235  CA   LEU A 189      36.264  41.602  45.880  1.00 30.16      A    C
ATOM   1236  CB   LEU A 189      35.383  42.862  45.847  1.00 32.37      A    C
ATOM   1237  CG   LEU A 189      35.883  44.205  46.392  1.00 33.47      A    C
ATOM   1238  CD1  LEU A 189      34.688  45.104  46.711  1.00 33.49      A    C
ATOM   1239  CD2  LEU A 189      36.694  43.996  47.644  1.00 35.85      A    C
ATOM   1240  C    LEU A 189      37.660  41.924  45.370  1.00 31.24      A    C
ATOM   1241  O    LEU A 189      38.540  42.352  46.118  1.00 29.45      A    O
ATOM   1242  N    ASP A 190      37.856  41.687  44.078  1.00 33.90      A    N
ATOM   1243  CA   ASP A 190      39.129  41.969  43.438  1.00 36.18      A    C
ATOM   1244  CB   ASP A 190      39.398  40.965  42.319  1.00 37.22      A    C
ATOM   1245  CG   ASP A 190      40.747  41.180  41.655  1.00 38.85      A    C
ATOM   1246  OD1  ASP A 190      40.926  42.217  40.974  1.00 39.12      A    O
ATOM   1247  OD2  ASP A 190      41.633  40.314  41.827  1.00 38.62      A    O
ATOM   1248  C    ASP A 190      39.000  43.382  42.878  1.00 37.61      A    C
ATOM   1249  O    ASP A 190      38.185  43.641  42.023  1.00 37.68      A    O
ATOM   1250  N    PRO A 191      39.808  44.315  43.382  1.00 39.88      A    N
ATOM   1251  CD   PRO A 191      40.912  44.094  44.333  1.00 40.38      A    C
ATOM   1252  CA   PRO A 191      39.771  45.711  42.925  1.00 40.90      A    C
ATOM   1253  CB   PRO A 191      40.803  46.391  43.825  1.00 42.25      A    C
ATOM   1254  CG   PRO A 191      41.820  45.284  44.045  1.00 42.29      A    C
ATOM   1255  C    PRO A 191      40.068  45.932  41.444  1.00 41.61      A    C
ATOM   1256  O    PRO A 191      39.553  46.883  40.837  1.00 41.28      A    O
ATOM   1257  N    ASP A 192      40.882  45.059  40.858  1.00 41.57      A    N
ATOM   1258  CA   ASP A 192      41.232  45.202  39.452  1.00 41.17      A    C
```

FIG. 5-22

```
ATOM   1259  CB   ASP A 192      42.606  44.587  39.186  1.00 43.68      A    C
ATOM   1260  CG   ASP A 192      43.722  45.340  39.895  1.00 46.09      A    C
ATOM   1261  OD1  ASP A 192      43.684  46.597  39.895  1.00 46.26      A    O
ATOM   1262  OD2  ASP A 192      44.639  44.680  40.443  1.00 47.63      A    O
ATOM   1263  C    ASP A 192      40.213  44.638  38.471  1.00 40.76      A    C
ATOM   1264  O    ASP A 192      39.939  45.263  37.464  1.00 42.95      A    O
ATOM   1265  N    THR A 193      39.654  43.465  38.762  1.00 37.99      A    N
ATOM   1266  CA   THR A 193      38.682  42.847  37.869  1.00 34.58      A    C
ATOM   1267  CB   THR A 193      38.890  41.320  37.812  1.00 35.35      A    C
ATOM   1268  OG1  THR A 193      38.874  40.774  39.138  1.00 36.63      A    O
ATOM   1269  CG2  THR A 193      40.219  40.999  37.163  1.00 34.98      A    C
ATOM   1270  C    THR A 193      37.232  43.152  38.267  1.00 32.98      A    C
ATOM   1271  O    THR A 193      36.303  42.863  37.533  1.00 32.69      A    O
ATOM   1272  N    ALA A 194      37.053  43.742  39.440  1.00 31.61      A    N
ATOM   1273  CA   ALA A 194      35.724  44.080  39.922  1.00 29.36      A    C
ATOM   1274  CB   ALA A 194      35.035  45.028  38.933  1.00 29.52      A    C
ATOM   1275  C    ALA A 194      34.857  42.850  40.181  1.00 28.98      A    C
ATOM   1276  O    ALA A 194      33.640  42.949  40.199  1.00 29.30      A    O
ATOM   1277  N    VAL A 195      35.483  41.689  40.381  1.00 28.53      A    N
ATOM   1278  CA   VAL A 195      34.716  40.478  40.657  1.00 28.65      A    C
ATOM   1279  CB   VAL A 195      35.410  39.187  40.115  1.00 29.89      A    C
ATOM   1280  CG1  VAL A 195      35.888  39.413  38.685  1.00 30.51      A    C
ATOM   1281  CG2  VAL A 195      36.561  38.769  41.011  1.00 32.97      A    C
ATOM   1282  C    VAL A 195      34.477  40.343  42.162  1.00 28.37      A    C
ATOM   1283  O    VAL A 195      35.361  40.646  42.983  1.00 29.07      A    O
ATOM   1284  N    LEU A 196      33.274  39.912  42.522  1.00 25.60      A    N
ATOM   1285  CA   LEU A 196      32.915  39.744  43.917  1.00 23.53      A    C
ATOM   1286  CB   LEU A 196      31.665  40.570  44.238  1.00 22.71      A    C
ATOM   1287  CG   LEU A 196      31.114  40.550  45.670  1.00 21.35      A    C
ATOM   1288  CD1  LEU A 196      30.375  41.846  45.944  1.00 22.02      A    C
ATOM   1289  CD2  LEU A 196      30.201  39.355  45.867  1.00 19.59      A    C
ATOM   1290  C    LEU A 196      32.686  38.279  44.254  1.00 23.99      A    C
ATOM   1291  O    LEU A 196      32.112  37.553  43.484  1.00 25.08      A    O
ATOM   1292  N    LYS A 197      33.165  37.855  45.416  1.00 22.64      A    N
ATOM   1293  CA   LYS A 197      32.984  36.475  45.838  1.00 23.00      A    C
ATOM   1294  CB   LYS A 197      34.302  35.699  45.746  1.00 23.64      A    C
ATOM   1295  CG   LYS A 197      34.755  35.466  44.313  1.00 26.17      A    C
ATOM   1296  CD   LYS A 197      36.154  34.887  44.242  1.00 28.36      A    C
ATOM   1297  CE   LYS A 197      36.573  34.645  42.802  1.00 28.98      A    C
ATOM   1298  NZ   LYS A 197      37.889  33.947  42.751  1.00 31.14      A    N
ATOM   1299  C    LYS A 197      32.443  36.412  47.253  1.00 22.28      A    C
ATOM   1300  O    LYS A 197      32.912  37.108  48.146  1.00 20.40      A    O
ATOM   1301  N    LEU A 198      31.432  35.570  47.426  1.00 21.91      A    N
ATOM   1302  CA   LEU A 198      30.783  35.365  48.710  1.00 22.46      A    C
ATOM   1303  CB   LEU A 198      29.413  34.724  48.495  1.00 23.95      A    C
ATOM   1304  CG   LEU A 198      28.198  35.273  49.237  1.00 25.55      A    C
ATOM   1305  CD1  LEU A 198      27.048  34.289  49.065  1.00 23.19      A    C
ATOM   1306  CD2  LEU A 198      28.515  35.472  50.716  1.00 25.66      A    C
ATOM   1307  C    LEU A 198      31.664  34.406  49.503  1.00 22.38      A    C
ATOM   1308  O    LEU A 198      32.150  33.447  48.954  1.00 23.29      A    O
ATOM   1309  N    CYS A 199      31.881  34.684  50.785  1.00 21.55      A    N
ATOM   1310  CA   CYS A 199      32.690  33.799  51.617  1.00 20.14      A    C
ATOM   1311  CB   CYS A 199      34.099  34.368  51.843  1.00 19.78      A    C
ATOM   1312  SG   CYS A 199      34.226  35.759  53.015  1.00 19.52      A    S
ATOM   1313  C    CYS A 199      32.003  33.607  52.962  1.00 21.14      A    C
ATOM   1314  O    CYS A 199      30.941  34.164  53.204  1.00 20.27      A    O
ATOM   1315  N    ASP A 200      32.639  32.815  53.821  1.00 20.99      A    N
ATOM   1316  CA   ASP A 200      32.152  32.485  55.161  1.00 21.09      A    C
ATOM   1317  CB   ASP A 200      32.046  33.736  56.050  1.00 21.97      A    C
ATOM   1318  CG   ASP A 200      31.694  33.387  57.497  1.00 24.11      A    C
```

FIG. 5-23

```
ATOM   1319  OD1 ASP A 200      31.638  32.181  57.824  1.00 25.48      A  O
ATOM   1320  OD2 ASP A 200      31.474  34.308  58.309  1.00 23.83      A  O
ATOM   1321  C   ASP A 200      30.810  31.759  55.175  1.00 21.48      A  C
ATOM   1322  O   ASP A 200      29.764  32.370  55.381  1.00 19.01      A  O
ATOM   1323  N   PHE A 201      30.849  30.445  54.979  1.00 21.24      A  N
ATOM   1324  CA  PHE A 201      29.628  29.659  54.984  1.00 20.62      A  C
ATOM   1325  CB  PHE A 201      29.624  28.679  53.812  1.00 18.79      A  C
ATOM   1326  CG  PHE A 201      29.365  29.333  52.493  1.00 17.54      A  C
ATOM   1327  CD1 PHE A 201      30.361  30.055  51.855  1.00 17.19      A  C
ATOM   1328  CD2 PHE A 201      28.107  29.270  51.911  1.00 15.42      A  C
ATOM   1329  CE1 PHE A 201      30.107  30.701  50.650  1.00 17.06      A  C
ATOM   1330  CE2 PHE A 201      27.842  29.912  50.709  1.00 14.34      A  C
ATOM   1331  CZ  PHE A 201      28.838  30.632  50.080  1.00 16.14      A  C
ATOM   1332  C   PHE A 201      29.412  28.924  56.300  1.00 20.18      A  C
ATOM   1333  O   PHE A 201      28.715  27.936  56.345  1.00 21.05      A  O
ATOM   1334  N   GLY A 202      30.009  29.445  57.368  1.00 18.60      A  N
ATOM   1335  CA  GLY A 202      29.867  28.842  58.680  1.00 18.49      A  C
ATOM   1336  C   GLY A 202      28.456  28.903  59.241  1.00 20.11      A  C
ATOM   1337  O   GLY A 202      28.122  28.189  60.171  1.00 19.79      A  O
ATOM   1338  N   SER A 203      27.621  29.762  58.674  1.00 20.69      A  N
ATOM   1339  CA  SER A 203      26.245  29.876  59.137  1.00 21.14      A  C
ATOM   1340  CB  SER A 203      25.901  31.344  59.419  1.00 20.93      A  C
ATOM   1341  OG  SER A 203      26.703  31.858  60.468  1.00 23.49      A  O
ATOM   1342  C   SER A 203      25.287  29.298  58.109  1.00 20.46      A  C
ATOM   1343  O   SER A 203      24.126  29.102  58.394  1.00 20.04      A  O
ATOM   1344  N   ALA A 204      25.802  29.018  56.913  1.00 20.25      A  N
ATOM   1345  CA  ALA A 204      24.998  28.471  55.824  1.00 20.24      A  C
ATOM   1346  CB  ALA A 204      25.879  28.210  54.622  1.00 20.89      A  C
ATOM   1347  C   ALA A 204      24.274  27.193  56.217  1.00 21.13      A  C
ATOM   1348  O   ALA A 204      24.821  26.356  56.901  1.00 20.29      A  O
ATOM   1349  N   LYS A 205      23.038  27.066  55.751  1.00 22.01      A  N
ATOM   1350  CA  LYS A 205      22.215  25.902  56.045  1.00 24.22      A  C
ATOM   1351  CB  LYS A 205      21.651  26.023  57.465  1.00 23.86      A  C
ATOM   1352  CG  LYS A 205      20.914  24.790  57.948  1.00 26.26      A  C
ATOM   1353  CD  LYS A 205      20.464  24.931  59.390  1.00 27.03      A  C
ATOM   1354  CE  LYS A 205      19.882  23.621  59.898  1.00 25.43      A  C
ATOM   1355  NZ  LYS A 205      18.754  23.186  59.041  1.00 28.24      A  N
ATOM   1356  C   LYS A 205      21.065  25.730  55.052  1.00 24.71      A  C
ATOM   1357  O   LYS A 205      20.491  26.705  54.554  1.00 22.45      A  O
ATOM   1358  N   GLN A 206      20.731  24.479  54.759  1.00 26.86      A  N
ATOM   1359  CA  GLN A 206      19.623  24.217  53.860  1.00 28.77      A  C
ATOM   1360  CB  GLN A 206      19.641  22.774  53.366  1.00 31.21      A  C
ATOM   1361  CG  GLN A 206      18.552  22.508  52.336  1.00 33.91      A  C
ATOM   1362  CD  GLN A 206      18.680  21.152  51.683  1.00 36.62      A  C
ATOM   1363  OE1 GLN A 206      17.925  20.820  50.782  1.00 39.64      A  O
ATOM   1364  NE2 GLN A 206      19.644  20.362  52.136  1.00 35.67      A  N
ATOM   1365  C   GLN A 206      18.344  24.478  54.653  1.00 28.44      A  C
ATOM   1366  O   GLN A 206      18.196  23.999  55.757  1.00 29.95      A  O
ATOM   1367  N   LEU A 207      17.436  25.260  54.088  1.00 28.95      A  N
ATOM   1368  CA  LEU A 207      16.183  25.562  54.766  1.00 30.71      A  C
ATOM   1369  CB  LEU A 207      15.844  27.049  54.620  1.00 29.63      A  C
ATOM   1370  CG  LEU A 207      16.796  28.039  55.304  1.00 29.84      A  C
ATOM   1371  CD1 LEU A 207      16.263  29.465  55.162  1.00 29.52      A  C
ATOM   1372  CD2 LEU A 207      16.941  27.673  56.767  1.00 29.53      A  C
ATOM   1373  C   LEU A 207      15.040  24.732  54.204  1.00 32.15      A  C
ATOM   1374  O   LEU A 207      14.568  24.983  53.100  1.00 33.45      A  O
ATOM   1375  N   VAL A 208      14.597  23.743  54.971  1.00 34.40      A  N
ATOM   1376  CA  VAL A 208      13.502  22.881  54.537  1.00 35.77      A  C
ATOM   1377  CB  VAL A 208      13.779  21.419  54.926  1.00 36.08      A  C
ATOM   1378  CG1 VAL A 208      12.613  20.518  54.494  1.00 36.89      A  C
```

FIG. 5-24

```
ATOM   1379  CG2 VAL A 208      15.064  20.964  54.266  1.00 34.48      A  C
ATOM   1380  C   VAL A 208      12.193  23.347  55.166  1.00 37.50      A  C
ATOM   1381  O   VAL A 208      12.136  23.602  56.348  1.00 38.00      A  O
ATOM   1382  N   ARG A 209      11.147  23.467  54.353  1.00 39.83      A  N
ATOM   1383  CA  ARG A 209       9.851  23.920  54.846  1.00 41.02      A  C
ATOM   1384  CB  ARG A 209       8.824  23.958  53.710  1.00 43.38      A  C
ATOM   1385  CG  ARG A 209       9.176  24.916  52.563  1.00 49.07      A  C
ATOM   1386  CD  ARG A 209       8.025  24.990  51.536  1.00 52.84      A  C
ATOM   1387  NE  ARG A 209       7.418  23.670  51.343  1.00 55.76      A  N
ATOM   1388  CZ  ARG A 209       6.268  23.445  50.709  1.00 57.50      A  C
ATOM   1389  NH1 ARG A 209       5.574  24.457  50.184  1.00 57.88      A  N
ATOM   1390  NH2 ARG A 209       5.802  22.200  50.621  1.00 58.01      A  N
ATOM   1391  C   ARG A 209       9.347  23.012  55.960  1.00 40.20      A  C
ATOM   1392  O   ARG A 209       9.457  21.778  55.875  1.00 40.11      A  O
ATOM   1393  N   GLY A 210       8.807  23.631  57.007  1.00 38.40      A  N
ATOM   1394  CA  GLY A 210       8.289  22.871  58.129  1.00 36.84      A  C
ATOM   1395  C   GLY A 210       9.333  22.613  59.190  1.00 36.09      A  C
ATOM   1396  O   GLY A 210       8.985  22.284  60.328  1.00 36.77      A  O
ATOM   1397  N   GLU A 211      10.609  22.741  58.834  1.00 33.96      A  N
ATOM   1398  CA  GLU A 211      11.666  22.528  59.821  1.00 34.17      A  C
ATOM   1399  CB  GLU A 211      12.895  21.883  59.173  1.00 35.98      A  C
ATOM   1400  CG  GLU A 211      12.623  20.531  58.526  1.00 38.93      A  C
ATOM   1401  CD  GLU A 211      13.890  19.869  58.012  1.00 41.19      A  C
ATOM   1402  OE1 GLU A 211      13.816  18.708  57.546  1.00 41.62      A  O
ATOM   1403  OE2 GLU A 211      14.965  20.512  58.078  1.00 42.78      A  O
ATOM   1404  C   GLU A 211      12.051  23.864  60.441  1.00 32.36      A  C
ATOM   1405  O   GLU A 211      12.182  24.875  59.741  1.00 31.51      A  O
ATOM   1406  N   PRO A 212      12.206  23.891  61.771  1.00 31.10      A  N
ATOM   1407  CD  PRO A 212      11.838  22.812  62.709  1.00 31.66      A  C
ATOM   1408  CA  PRO A 212      12.578  25.113  62.491  1.00 28.94      A  C
ATOM   1409  CB  PRO A 212      12.081  24.835  63.906  1.00 30.70      A  C
ATOM   1410  CG  PRO A 212      12.309  23.353  64.043  1.00 31.31      A  C
ATOM   1411  C   PRO A 212      14.084  25.358  62.420  1.00 27.46      A  C
ATOM   1412  O   PRO A 212      14.867  24.428  62.240  1.00 26.20      A  O
ATOM   1413  N   ASN A 213      14.473  26.622  62.542  1.00 26.02      A  N
ATOM   1414  CA  ASN A 213      15.877  27.019  62.511  1.00 24.26      A  C
ATOM   1415  CB  ASN A 213      16.258  27.494  61.108  1.00 23.22      A  C
ATOM   1416  CG  ASN A 213      16.329  26.350  60.110  1.00 22.84      A  C
ATOM   1417  OD1 ASN A 213      17.253  25.553  60.135  1.00 23.26      A  O
ATOM   1418  ND2 ASN A 213      15.338  26.264  59.239  1.00 22.17      A  N
ATOM   1419  C   ASN A 213      16.127  28.114  63.538  1.00 23.35      A  C
ATOM   1420  O   ASN A 213      15.240  28.875  63.845  1.00 22.28      A  O
ATOM   1421  N   VAL A 214      17.345  28.173  64.067  1.00 22.95      A  N
ATOM   1422  CA  VAL A 214      17.698  29.164  65.081  1.00 22.87      A  C
ATOM   1423  CB  VAL A 214      19.135  28.925  65.608  1.00 22.74      A  C
ATOM   1424  CG1 VAL A 214      19.263  27.491  66.120  1.00 19.57      A  C
ATOM   1425  CG2 VAL A 214      20.160  29.204  64.513  1.00 21.74      A  C
ATOM   1426  C   VAL A 214      17.575  30.587  64.544  1.00 23.51      A  C
ATOM   1427  O   VAL A 214      17.961  30.879  63.424  1.00 22.27      A  O
ATOM   1428  N   SER A 215      17.023  31.468  65.366  1.00 24.22      A  N
ATOM   1429  CA  SER A 215      16.829  32.844  64.957  1.00 25.98      A  C
ATOM   1430  CB  SER A 215      15.447  33.318  65.414  1.00 26.10      A  C
ATOM   1431  OG  SER A 215      15.242  33.018  66.783  1.00 28.75      A  O
ATOM   1432  C   SER A 215      17.903  33.814  65.437  1.00 25.74      A  C
ATOM   1433  O   SER A 215      17.702  34.999  65.384  1.00 28.23      A  O
ATOM   1434  N   TYR A 216      19.042  33.308  65.895  1.00 24.31      A  N
ATOM   1435  CA  TYR A 216      20.113  34.193  66.351  1.00 25.04      A  C
ATOM   1436  CB  TYR A 216      20.513  33.847  67.790  1.00 23.93      A  C
ATOM   1437  CG  TYR A 216      20.756  32.381  68.026  1.00 24.84      A  C
ATOM   1438  CD1 TYR A 216      21.882  31.743  67.502  1.00 25.13      A  C
```

FIG. 5-25

```
ATOM   1439  CE1 TYR A 216      22.089  30.381  67.686  1.00 24.27      A    C
ATOM   1440  CD2 TYR A 216      19.841  31.614  68.744  1.00 24.66      A    C
ATOM   1441  CE2 TYR A 216      20.042  30.255  68.932  1.00 23.08      A    C
ATOM   1442  CZ  TYR A 216      21.163  29.647  68.400  1.00 23.40      A    C
ATOM   1443  OH  TYR A 216      21.352  28.302  68.584  1.00 24.02      A    O
ATOM   1444  C   TYR A 216      21.334  34.112  65.435  1.00 25.24      A    C
ATOM   1445  O   TYR A 216      22.449  34.329  65.880  1.00 24.80      A    O
ATOM   1446  N   ILE A 217      21.108  33.831  64.150  1.00 25.83      A    N
ATOM   1447  CA  ILE A 217      22.216  33.700  63.212  1.00 26.17      A    C
ATOM   1448  CB  ILE A 217      21.989  32.546  62.202  1.00 25.14      A    C
ATOM   1449  CG2 ILE A 217      22.581  31.262  62.762  1.00 26.35      A    C
ATOM   1450  CG1 ILE A 217      20.505  32.418  61.847  1.00 23.39      A    C
ATOM   1451  CD1 ILE A 217      19.995  33.470  60.893  1.00 18.62      A    C
ATOM   1452  C   ILE A 217      22.755  34.872  62.389  1.00 27.83      A    C
ATOM   1453  O   ILE A 217      23.927  34.825  61.958  1.00 32.85      A    O
ATOM   1454  N   CYS A 218      21.979  35.918  62.154  1.00 24.22      A    N
ATOM   1455  CA  CYS A 218      22.502  36.990  61.298  1.00 23.07      A    C
ATOM   1456  CB  CYS A 218      21.340  37.602  60.507  1.00 23.52      A    C
ATOM   1457  SG  CYS A 218      21.743  38.309  58.907  1.00 22.42      A    S
ATOM   1458  C   CYS A 218      23.276  38.073  62.068  1.00 22.56      A    C
ATOM   1459  O   CYS A 218      23.199  38.133  63.262  1.00 22.72      A    O
ATOM   1460  N   SER A 219      24.025  38.921  61.371  1.00 21.48      A    N
ATOM   1461  CA  SER A 219      24.795  39.961  62.058  1.00 21.35      A    C
ATOM   1462  CB  SER A 219      26.165  40.116  61.407  1.00 21.34      A    C
ATOM   1463  OG  SER A 219      26.992  39.012  61.728  1.00 20.80      A    O
ATOM   1464  C   SER A 219      24.138  41.335  62.182  1.00 21.75      A    C
ATOM   1465  O   SER A 219      23.396  41.772  61.309  1.00 21.07      A    O
ATOM   1466  N   ARG A 220      24.442  42.007  63.289  1.00 22.38      A    N
ATOM   1467  CA  ARG A 220      23.911  43.335  63.598  1.00 23.74      A    C
ATOM   1468  CB  ARG A 220      24.730  43.949  64.734  1.00 26.59      A    C
ATOM   1469  CG  ARG A 220      24.174  45.242  65.290  1.00 32.85      A    C
ATOM   1470  CD  ARG A 220      24.613  45.477  66.739  1.00 37.44      A    C
ATOM   1471  NE  ARG A 220      25.371  46.715  66.904  1.00 40.19      A    N
ATOM   1472  CZ  ARG A 220      26.507  46.978  66.266  1.00 41.61      A    C
ATOM   1473  NH1 ARG A 220      27.017  46.092  65.416  1.00 42.25      A    N
ATOM   1474  NH2 ARG A 220      27.144  48.120  66.486  1.00 41.57      A    N
ATOM   1475  C   ARG A 220      23.915  44.264  62.385  1.00 22.42      A    C
ATOM   1476  O   ARG A 220      24.913  44.379  61.709  1.00 24.35      A    O
ATOM   1477  N   TYR A 221      22.778  44.909  62.135  1.00 21.09      A    N
ATOM   1478  CA  TYR A 221      22.581  45.838  61.016  1.00 21.32      A    C
ATOM   1479  CB  TYR A 221      23.894  46.497  60.531  1.00 20.88      A    C
ATOM   1480  CG  TYR A 221      24.609  47.397  61.511  1.00 23.30      A    C
ATOM   1481  CD1 TYR A 221      23.982  47.846  62.674  1.00 23.59      A    C
ATOM   1482  CE1 TYR A 221      24.654  48.663  63.579  1.00 26.91      A    C
ATOM   1483  CD2 TYR A 221      25.933  47.796  61.271  1.00 23.68      A    C
ATOM   1484  CE2 TYR A 221      26.617  48.615  62.161  1.00 25.70      A    C
ATOM   1485  CZ  TYR A 221      25.971  49.046  63.322  1.00 29.19      A    C
ATOM   1486  OH  TYR A 221      26.642  49.839  64.233  1.00 31.39      A    O
ATOM   1487  C   TYR A 221      21.964  45.166  59.794  1.00 20.64      A    C
ATOM   1488  O   TYR A 221      21.220  45.790  59.044  1.00 20.14      A    O
ATOM   1489  N   TYR A 222      22.275  43.892  59.593  1.00 21.11      A    N
ATOM   1490  CA  TYR A 222      21.787  43.181  58.416  1.00 21.00      A    C
ATOM   1491  CB  TYR A 222      22.981  42.515  57.721  1.00 18.45      A    C
ATOM   1492  CG  TYR A 222      24.127  43.481  57.566  1.00 18.72      A    C
ATOM   1493  CD1 TYR A 222      24.101  44.460  56.570  1.00 18.10      A    C
ATOM   1494  CE1 TYR A 222      25.086  45.433  56.490  1.00 18.10      A    C
ATOM   1495  CD2 TYR A 222      25.179  43.499  58.478  1.00 18.77      A    C
ATOM   1496  CE2 TYR A 222      26.177  44.474  58.409  1.00 18.84      A    C
ATOM   1497  CZ  TYR A 222      26.119  45.440  57.414  1.00 19.57      A    C
ATOM   1498  OH  TYR A 222      27.078  46.421  57.345  1.00 19.23      A    O
```

FIG. 5-26

```
ATOM   1499  C    TYR A 222      20.699  42.148  58.689  1.00 20.92           A    C
ATOM   1500  O    TYR A 222      20.270  41.465  57.792  1.00 20.65           A    O
ATOM   1501  N    ARG A 223      20.239  42.071  59.929  1.00 20.60           A    N
ATOM   1502  CA   ARG A 223      19.232  41.084  60.287  1.00 20.00           A    C
ATOM   1503  CB   ARG A 223      19.207  40.864  61.805  1.00 19.80           A    C
ATOM   1504  CG   ARG A 223      20.555  40.729  62.509  1.00 21.30           A    C
ATOM   1505  CD   ARG A 223      20.343  40.361  63.994  1.00 21.90           A    C
ATOM   1506  NE   ARG A 223      20.033  38.939  64.132  1.00 23.51           A    N
ATOM   1507  CZ   ARG A 223      19.231  38.411  65.052  1.00 23.80           A    C
ATOM   1508  NH1  ARG A 223      18.622  39.174  65.952  1.00 24.92           A    N
ATOM   1509  NH2  ARG A 223      19.040  37.101  65.069  1.00 22.28           A    N
ATOM   1510  C    ARG A 223      17.820  41.438  59.837  1.00 19.85           A    C
ATOM   1511  O    ARG A 223      17.312  42.527  60.120  1.00 21.01           A    O
ATOM   1512  N    ALA A 224      17.186  40.499  59.147  1.00 20.02           A    N
ATOM   1513  CA   ALA A 224      15.822  40.680  58.681  1.00 19.70           A    C
ATOM   1514  CB   ALA A 224      15.398  39.481  57.830  1.00 18.82           A    C
ATOM   1515  C    ALA A 224      14.916  40.804  59.910  1.00 19.36           A    C
ATOM   1516  O    ALA A 224      15.175  40.204  60.935  1.00 18.68           A    O
ATOM   1517  N    PRO A 225      13.840  41.598  59.801  1.00 20.51           A    N
ATOM   1518  CD   PRO A 225      13.438  42.251  58.541  1.00 20.02           A    C
ATOM   1519  CA   PRO A 225      12.853  41.857  60.856  1.00 22.48           A    C
ATOM   1520  CB   PRO A 225      11.730  42.573  60.104  1.00 24.04           A    C
ATOM   1521  CG   PRO A 225      12.444  43.259  59.000  1.00 20.84           A    C
ATOM   1522  C    PRO A 225      12.348  40.588  61.553  1.00 24.51           A    C
ATOM   1523  O    PRO A 225      12.253  40.545  62.790  1.00 25.75           A    O
ATOM   1524  N    GLU A 226      12.020  39.568  60.761  1.00 24.27           A    N
ATOM   1525  CA   GLU A 226      11.531  38.304  61.312  1.00 24.50           A    C
ATOM   1526  CB   GLU A 226      11.199  37.276  60.217  1.00 26.25           A    C
ATOM   1527  CG   GLU A 226      10.769  37.847  58.885  1.00 30.48           A    C
ATOM   1528  CD   GLU A 226      11.941  38.296  58.036  1.00 28.74           A    C
ATOM   1529  OE1  GLU A 226      12.403  37.519  57.169  1.00 27.92           A    O
ATOM   1530  OE2  GLU A 226      12.398  39.432  58.248  1.00 30.29           A    O
ATOM   1531  C    GLU A 226      12.573  37.680  62.239  1.00 23.33           A    C
ATOM   1532  O    GLU A 226      12.220  37.050  63.228  1.00 24.73           A    O
ATOM   1533  N    LEU A 227      13.853  37.835  61.915  1.00 21.87           A    N
ATOM   1534  CA   LEU A 227      14.887  37.264  62.770  1.00 21.72           A    C
ATOM   1535  CB   LEU A 227      16.267  37.321  62.097  1.00 20.27           A    C
ATOM   1536  CG   LEU A 227      16.529  36.432  60.871  1.00 18.67           A    C
ATOM   1537  CD1  LEU A 227      17.976  36.609  60.414  1.00 19.13           A    C
ATOM   1538  CD2  LEU A 227      16.265  34.969  61.217  1.00 16.28           A    C
ATOM   1539  C    LEU A 227      14.912  38.018  64.093  1.00 21.64           A    C
ATOM   1540  O    LEU A 227      14.965  37.424  65.126  1.00 22.23           A    O
ATOM   1541  N    ILE A 228      14.856  39.342  64.028  1.00 21.73           A    N
ATOM   1542  CA   ILE A 228      14.863  40.156  65.234  1.00 24.05           A    C
ATOM   1543  CB   ILE A 228      14.803  41.664  64.880  1.00 23.39           A    C
ATOM   1544  CG2  ILE A 228      14.806  42.505  66.148  1.00 23.59           A    C
ATOM   1545  CG1  ILE A 228      16.011  42.043  64.016  1.00 23.22           A    C
ATOM   1546  CD1  ILE A 228      16.087  43.512  63.668  1.00 22.01           A    C
ATOM   1547  C    ILE A 228      13.657  39.769  66.097  1.00 24.63           A    C
ATOM   1548  O    ILE A 228      13.763  39.649  67.300  1.00 25.29           A    O
ATOM   1549  N    PHE A 229      12.518  39.559  65.446  1.00 24.98           A    N
ATOM   1550  CA   PHE A 229      11.292  39.168  66.130  1.00 24.17           A    C
ATOM   1551  CB   PHE A 229      10.103  39.321  65.181  1.00 23.57           A    C
ATOM   1552  CG   PHE A 229       9.551  40.712  65.126  1.00 23.62           A    C
ATOM   1553  CD1  PHE A 229       9.024  41.305  66.272  1.00 24.77           A    C
ATOM   1554  CD2  PHE A 229       9.552  41.431  63.938  1.00 22.88           A    C
ATOM   1555  CE1  PHE A 229       8.511  42.592  66.235  1.00 24.08           A    C
ATOM   1556  CE2  PHE A 229       9.040  42.722  63.894  1.00 22.38           A    C
ATOM   1557  CZ   PHE A 229       8.517  43.301  65.042  1.00 21.87           A    C
ATOM   1558  C    PHE A 229      11.339  37.735  66.658  1.00 23.31           A    C
```

FIG. 5-27

```
ATOM   1559  O    PHE A 229     10.394  37.273  67.261  1.00 24.41      A    O
ATOM   1560  N    GLY A 230     12.444  37.039  66.413  1.00 23.43      A    N
ATOM   1561  CA   GLY A 230     12.588  35.678  66.898  1.00 23.01      A    C
ATOM   1562  C    GLY A 230     11.828  34.577  66.179  1.00 25.12      A    C
ATOM   1563  O    GLY A 230     11.425  33.592  66.809  1.00 26.12      A    O
ATOM   1564  N    ALA A 231     11.630  34.724  64.872  1.00 24.41      A    N
ATOM   1565  CA   ALA A 231     10.919  33.711  64.096  1.00 24.32      A    C
ATOM   1566  CB   ALA A 231     10.418  34.301  62.787  1.00 24.71      A    C
ATOM   1567  C    ALA A 231     11.870  32.560  63.814  1.00 25.29      A    C
ATOM   1568  O    ALA A 231     13.074  32.759  63.670  1.00 25.15      A    O
ATOM   1569  N    THR A 232     11.320  31.354  63.748  1.00 25.46      A    N
ATOM   1570  CA   THR A 232     12.121  30.169  63.477  1.00 25.39      A    C
ATOM   1571  CB   THR A 232     12.047  29.182  64.655  1.00 26.47      A    C
ATOM   1572  OG1  THR A 232     10.704  28.708  64.797  1.00 26.48      A    O
ATOM   1573  CG2  THR A 232     12.467  29.874  65.941  1.00 26.00      A    C
ATOM   1574  C    THR A 232     11.626  29.477  62.205  1.00 24.62      A    C
ATOM   1575  O    THR A 232     12.090  28.398  61.857  1.00 23.39      A    O
ATOM   1576  N    ASP A 233     10.685  30.119  61.517  1.00 24.23      A    N
ATOM   1577  CA   ASP A 233     10.127  29.571  60.282  1.00 25.86      A    C
ATOM   1578  CB   ASP A 233      8.597  29.491  60.381  1.00 26.67      A    C
ATOM   1579  CG   ASP A 233      7.944  30.861  60.412  1.00 29.74      A    C
ATOM   1580  OD1  ASP A 233      8.600  31.826  60.856  1.00 29.55      A    O
ATOM   1581  OD2  ASP A 233      6.768  30.977  60.007  1.00 33.46      A    O
ATOM   1582  C    ASP A 233     10.505  30.457  59.096  1.00 24.85      A    C
ATOM   1583  O    ASP A 233      9.806  30.484  58.087  1.00 23.56      A    O
ATOM   1584  N    TYR A 234     11.614  31.179  59.224  1.00 23.87      A    N
ATOM   1585  CA   TYR A 234     12.050  32.070  58.154  1.00 23.85      A    C
ATOM   1586  CB   TYR A 234     13.116  33.040  58.674  1.00 22.65      A    C
ATOM   1587  CG   TYR A 234     14.353  32.369  59.223  1.00 21.36      A    C
ATOM   1588  CD1  TYR A 234     15.379  31.960  58.379  1.00 19.80      A    C
ATOM   1589  CE1  TYR A 234     16.518  31.339  58.888  1.00 20.68      A    C
ATOM   1590  CD2  TYR A 234     14.490  32.134  60.596  1.00 21.47      A    C
ATOM   1591  CE2  TYR A 234     15.620  31.509  61.115  1.00 20.06      A    C
ATOM   1592  CZ   TYR A 234     16.629  31.115  60.256  1.00 20.28      A    C
ATOM   1593  OH   TYR A 234     17.744  30.485  60.757  1.00 21.37      A    O
ATOM   1594  C    TYR A 234     12.569  31.322  56.926  1.00 23.90      A    C
ATOM   1595  O    TYR A 234     12.939  30.151  57.000  1.00 23.42      A    O
ATOM   1596  N    THR A 235     12.576  32.013  55.794  1.00 24.75      A    N
ATOM   1597  CA   THR A 235     13.041  31.431  54.541  1.00 26.17      A    C
ATOM   1598  CB   THR A 235     12.013  31.641  53.424  1.00 27.71      A    C
ATOM   1599  OG1  THR A 235     11.956  33.034  53.092  1.00 30.51      A    O
ATOM   1600  CG2  THR A 235     10.623  31.176  53.879  1.00 23.34      A    C
ATOM   1601  C    THR A 235     14.352  32.070  54.108  1.00 25.82      A    C
ATOM   1602  O    THR A 235     14.886  32.950  54.792  1.00 24.42      A    O
ATOM   1603  N    SER A 236     14.866  31.626  52.967  1.00 24.34      A    N
ATOM   1604  CA   SER A 236     16.118  32.154  52.457  1.00 24.64      A    C
ATOM   1605  CB   SER A 236     16.602  31.333  51.263  1.00 26.12      A    C
ATOM   1606  OG   SER A 236     15.882  31.704  50.098  1.00 31.25      A    O
ATOM   1607  C    SER A 236     15.965  33.619  52.058  1.00 22.56      A    C
ATOM   1608  O    SER A 236     16.925  34.259  51.684  1.00 19.92      A    O
ATOM   1609  N    SER A 237     14.748  34.147  52.150  1.00 21.54      A    N
ATOM   1610  CA   SER A 237     14.548  35.541  51.808  1.00 20.50      A    C
ATOM   1611  CB   SER A 237     13.061  35.893  51.716  1.00 19.95      A    C
ATOM   1612  OG   SER A 237     12.436  35.906  52.981  1.00 23.05      A    O
ATOM   1613  C    SER A 237     15.258  36.449  52.814  1.00 21.13      A    C
ATOM   1614  O    SER A 237     15.360  37.661  52.583  1.00 21.45      A    O
ATOM   1615  N    ILE A 238     15.756  35.879  53.918  1.00 17.74      A    N
ATOM   1616  CA   ILE A 238     16.479  36.701  54.888  1.00 17.12      A    C
ATOM   1617  CB   ILE A 238     16.835  35.968  56.200  1.00 15.45      A    C
ATOM   1618  CG2  ILE A 238     15.574  35.607  56.957  1.00 12.81      A    C
```

FIG. 5-28

```
ATOM   1619  CG1 ILE A 238      17.723  34.770  55.907  1.00 15.25           A    C
ATOM   1620  CD1 ILE A 238      18.328  34.167  57.157  1.00 16.44           A    C
ATOM   1621  C   ILE A 238      17.770  37.219  54.240  1.00 18.31           A    C
ATOM   1622  O   ILE A 238      18.236  38.304  54.559  1.00 17.56           A    O
ATOM   1623  N   ASP A 239      18.325  36.435  53.315  1.00 17.56           A    N
ATOM   1624  CA  ASP A 239      19.530  36.832  52.603  1.00 18.92           A    C
ATOM   1625  CB  ASP A 239      20.022  35.700  51.701  1.00 19.79           A    C
ATOM   1626  CG  ASP A 239      20.623  34.546  52.482  1.00 21.07           A    C
ATOM   1627  OD1 ASP A 239      21.118  34.768  53.606  1.00 21.63           A    O
ATOM   1628  OD2 ASP A 239      20.618  33.413  51.955  1.00 24.63           A    O
ATOM   1629  C   ASP A 239      19.251  38.066  51.745  1.00 19.73           A    C
ATOM   1630  O   ASP A 239      20.083  38.946  51.631  1.00 17.98           A    O
ATOM   1631  N   VAL A 240      18.068  38.109  51.142  1.00 18.89           A    N
ATOM   1632  CA  VAL A 240      17.689  39.239  50.309  1.00 19.59           A    C
ATOM   1633  CB  VAL A 240      16.351  38.986  49.577  1.00 19.71           A    C
ATOM   1634  CG1 VAL A 240      15.913  40.240  48.861  1.00 19.47           A    C
ATOM   1635  CG2 VAL A 240      16.521  37.859  48.567  1.00 20.01           A    C
ATOM   1636  C   VAL A 240      17.598  40.511  51.144  1.00 19.83           A    C
ATOM   1637  O   VAL A 240      18.071  41.560  50.722  1.00 19.90           A    O
ATOM   1638  N   TRP A 241      16.997  40.413  52.329  1.00 19.02           A    N
ATOM   1639  CA  TRP A 241      16.901  41.576  53.209  1.00 18.15           A    C
ATOM   1640  CB  TRP A 241      16.165  41.222  54.505  1.00 16.19           A    C
ATOM   1641  CG  TRP A 241      16.218  42.319  55.528  1.00 16.64           A    C
ATOM   1642  CD2 TRP A 241      15.225  43.325  55.759  1.00 16.90           A    C
ATOM   1643  CE2 TRP A 241      15.732  44.191  56.755  1.00 16.17           A    C
ATOM   1644  CE3 TRP A 241      13.961  43.591  55.209  1.00 15.56           A    C
ATOM   1645  CD1 TRP A 241      17.251  42.600  56.379  1.00 15.77           A    C
ATOM   1646  NE1 TRP A 241      16.967  43.719  57.117  1.00 15.00           A    N
ATOM   1647  CZ2 TRP A 241      15.011  45.297  57.228  1.00 16.60           A    C
ATOM   1648  CZ3 TRP A 241      13.245  44.692  55.678  1.00 16.99           A    C
ATOM   1649  CH2 TRP A 241      13.777  45.534  56.674  1.00 17.83           A    C
ATOM   1650  C   TRP A 241      18.322  42.056  53.516  1.00 16.99           A    C
ATOM   1651  O   TRP A 241      18.614  43.240  53.431  1.00 16.62           A    O
ATOM   1652  N   SER A 242      19.201  41.120  53.857  1.00 16.68           A    N
ATOM   1653  CA  SER A 242      20.588  41.461  54.155  1.00 17.39           A    C
ATOM   1654  CB  SER A 242      21.378  40.207  54.524  1.00 16.23           A    C
ATOM   1655  OG  SER A 242      21.008  39.737  55.799  1.00 16.51           A    O
ATOM   1656  C   SER A 242      21.251  42.146  52.964  1.00 17.70           A    C
ATOM   1657  O   SER A 242      21.971  43.117  53.119  1.00 18.92           A    O
ATOM   1658  N   ALA A 243      21.001  41.617  51.773  1.00 17.09           A    N
ATOM   1659  CA  ALA A 243      21.570  42.188  50.567  1.00 17.85           A    C
ATOM   1660  CB  ALA A 243      21.192  41.342  49.355  1.00 18.13           A    C
ATOM   1661  C   ALA A 243      21.054  43.613  50.421  1.00 18.27           A    C
ATOM   1662  O   ALA A 243      21.805  44.522  50.077  1.00 18.76           A    O
ATOM   1663  N   GLY A 244      19.768  43.794  50.697  1.00 18.87           A    N
ATOM   1664  CA  GLY A 244      19.170  45.115  50.626  1.00 18.26           A    C
ATOM   1665  C   GLY A 244      19.853  46.080  51.582  1.00 19.54           A    C
ATOM   1666  O   GLY A 244      20.009  47.246  51.264  1.00 20.43           A    O
ATOM   1667  N   CYS A 245      20.261  45.595  52.754  1.00 17.58           A    N
ATOM   1668  CA  CYS A 245      20.927  46.459  53.722  1.00 17.48           A    C
ATOM   1669  CB  CYS A 245      21.036  45.758  55.082  1.00 15.82           A    C
ATOM   1670  SG  CYS A 245      19.448  45.528  55.931  1.00 16.96           A    S
ATOM   1671  C   CYS A 245      22.313  46.849  53.202  1.00 17.67           A    C
ATOM   1672  O   CYS A 245      22.741  47.965  53.383  1.00 15.55           A    O
ATOM   1673  N   VAL A 246      22.992  45.907  52.553  1.00 15.07           A    N
ATOM   1674  CA  VAL A 246      24.313  46.166  51.986  1.00 17.46           A    C
ATOM   1675  CB  VAL A 246      24.917  44.874  51.372  1.00 16.46           A    C
ATOM   1676  CG1 VAL A 246      26.199  45.182  50.628  1.00 14.47           A    C
ATOM   1677  CG2 VAL A 246      25.172  43.853  52.472  1.00 16.49           A    C
ATOM   1678  C   VAL A 246      24.229  47.243  50.901  1.00 18.71           A    C
```

FIG. 5-29

```
ATOM   1679  O    VAL A 246      25.061  48.157  50.864  1.00 18.67           A  O
ATOM   1680  N    LEU A 247      23.225  47.118  50.030  1.00 18.44           A  N
ATOM   1681  CA   LEU A 247      23.000  48.078  48.952  1.00 19.22           A  C
ATOM   1682  CB   LEU A 247      21.798  47.654  48.096  1.00 20.02           A  C
ATOM   1683  CG   LEU A 247      21.271  48.706  47.108  1.00 21.95           A  C
ATOM   1684  CD1  LEU A 247      22.363  49.074  46.110  1.00 18.27           A  C
ATOM   1685  CD2  LEU A 247      20.025  48.171  46.378  1.00 24.09           A  C
ATOM   1686  C    LEU A 247      22.754  49.461  49.545  1.00 19.30           A  C
ATOM   1687  O    LEU A 247      23.410  50.416  49.189  1.00 20.80           A  O
ATOM   1688  N    ALA A 248      21.798  49.550  50.458  1.00 18.29           A  N
ATOM   1689  CA   ALA A 248      21.476  50.815  51.093  1.00 18.77           A  C
ATOM   1690  CB   ALA A 248      20.385  50.606  52.132  1.00 17.56           A  C
ATOM   1691  C    ALA A 248      22.719  51.439  51.740  1.00 20.52           A  C
ATOM   1692  O    ALA A 248      22.924  52.640  51.641  1.00 20.16           A  O
ATOM   1693  N    GLU A 249      23.545  50.612  52.385  1.00 20.37           A  N
ATOM   1694  CA   GLU A 249      24.756  51.097  53.047  1.00 20.88           A  C
ATOM   1695  CB   GLU A 249      25.392  49.983  53.894  1.00 21.08           A  C
ATOM   1696  CG   GLU A 249      26.499  50.452  54.847  1.00 18.92           A  C
ATOM   1697  CD   GLU A 249      26.915  49.377  55.840  1.00 21.50           A  C
ATOM   1698  OE1  GLU A 249      26.079  48.518  56.163  1.00 22.72           A  O
ATOM   1699  OE2  GLU A 249      28.065  49.391  56.315  1.00 22.94           A  O
ATOM   1700  C    GLU A 249      25.780  51.636  52.060  1.00 20.58           A  C
ATOM   1701  O    GLU A 249      26.415  52.646  52.322  1.00 21.29           A  O
ATOM   1702  N    LEU A 250      25.946  50.953  50.929  1.00 21.81           A  N
ATOM   1703  CA   LEU A 250      26.886  51.396  49.908  1.00 21.37           A  C
ATOM   1704  CB   LEU A 250      27.023  50.329  48.821  1.00 20.07           A  C
ATOM   1705  CG   LEU A 250      27.759  49.032  49.182  1.00 20.08           A  C
ATOM   1706  CD1  LEU A 250      27.800  48.102  47.974  1.00 18.14           A  C
ATOM   1707  CD2  LEU A 250      29.162  49.352  49.648  1.00 19.26           A  C
ATOM   1708  C    LEU A 250      26.420  52.720  49.298  1.00 23.66           A  C
ATOM   1709  O    LEU A 250      27.218  53.539  48.916  1.00 24.74           A  O
ATOM   1710  N    LEU A 251      25.110  52.919  49.228  1.00 24.13           A  N
ATOM   1711  CA   LEU A 251      24.565  54.146  48.666  1.00 24.98           A  C
ATOM   1712  CB   LEU A 251      23.114  53.918  48.226  1.00 24.19           A  C
ATOM   1713  CG   LEU A 251      22.905  52.964  47.044  1.00 25.74           A  C
ATOM   1714  CD1  LEU A 251      21.428  52.660  46.868  1.00 25.68           A  C
ATOM   1715  CD2  LEU A 251      23.481  53.583  45.774  1.00 25.45           A  C
ATOM   1716  C    LEU A 251      24.622  55.277  49.681  1.00 25.55           A  C
ATOM   1717  O    LEU A 251      25.010  56.379  49.360  1.00 27.04           A  O
ATOM   1718  N    LEU A 252      24.256  54.973  50.916  1.00 26.13           A  N
ATOM   1719  CA   LEU A 252      24.204  55.960  51.989  1.00 26.94           A  C
ATOM   1720  CB   LEU A 252      23.243  55.437  53.058  1.00 28.67           A  C
ATOM   1721  CG   LEU A 252      22.404  56.433  53.854  1.00 32.52           A  C
ATOM   1722  CD1  LEU A 252      21.210  56.911  53.028  1.00 31.94           A  C
ATOM   1723  CD2  LEU A 252      21.916  55.748  55.121  1.00 34.91           A  C
ATOM   1724  C    LEU A 252      25.539  56.345  52.645  1.00 26.15           A  C
ATOM   1725  O    LEU A 252      25.660  57.422  53.170  1.00 28.07           A  O
ATOM   1726  N    GLY A 253      26.523  55.451  52.618  1.00 25.41           A  N
ATOM   1727  CA   GLY A 253      27.807  55.737  53.239  1.00 22.23           A  C
ATOM   1728  C    GLY A 253      27.850  55.297  54.692  1.00 22.93           A  C
ATOM   1729  O    GLY A 253      28.843  55.506  55.371  1.00 21.70           A  O
ATOM   1730  N    GLN A 254      26.760  54.686  55.160  1.00 21.55           A  N
ATOM   1731  CA   GLN A 254      26.652  54.206  56.538  1.00 21.86           A  C
ATOM   1732  CB   GLN A 254      26.348  55.374  57.486  1.00 23.52           A  C
ATOM   1733  CG   GLN A 254      24.982  56.037  57.248  1.00 28.30           A  C
ATOM   1734  CD   GLN A 254      24.698  57.219  58.181  1.00 32.70           A  C
ATOM   1735  OE1  GLN A 254      23.558  57.441  58.587  1.00 33.89           A  O
ATOM   1736  NE2  GLN A 254      25.734  57.989  58.505  1.00 35.14           A  N
ATOM   1737  C    GLN A 254      25.517  53.183  56.609  1.00 20.25           A  C
ATOM   1738  O    GLN A 254      24.703  53.101  55.714  1.00 20.50           A  O
```

FIG. 5-30

```
ATOM   1739  N    PRO A 255      25.468  52.381  57.681  1.00 20.14      A    N
ATOM   1740  CD   PRO A 255      26.483  52.240  58.741  1.00 20.65      A    C
ATOM   1741  CA   PRO A 255      24.410  51.374  57.834  1.00 19.64      A    C
ATOM   1742  CB   PRO A 255      24.758  50.707  59.162  1.00 19.15      A    C
ATOM   1743  CG   PRO A 255      26.244  50.825  59.230  1.00 20.07      A    C
ATOM   1744  C    PRO A 255      23.027  52.020  57.872  1.00 20.02      A    C
ATOM   1745  O    PRO A 255      22.817  52.995  58.575  1.00 21.62      A    O
ATOM   1746  N    ILE A 256      22.083  51.459  57.126  1.00 21.00      A    N
ATOM   1747  CA   ILE A 256      20.735  52.005  57.080  1.00 20.37      A    C
ATOM   1748  CB   ILE A 256      19.967  51.468  55.827  1.00 20.91      A    C
ATOM   1749  CG2  ILE A 256      19.785  49.947  55.909  1.00 18.52      A    C
ATOM   1750  CG1  ILE A 256      18.620  52.181  55.704  1.00 21.76      A    C
ATOM   1751  CD1  ILE A 256      17.883  51.908  54.407  1.00 24.16      A    C
ATOM   1752  C    ILE A 256      19.926  51.745  58.353  1.00 20.18      A    C
ATOM   1753  O    ILE A 256      19.146  52.598  58.768  1.00 19.86      A    O
ATOM   1754  N    PHE A 257      20.120  50.583  58.977  1.00 20.20      A    N
ATOM   1755  CA   PHE A 257      19.378  50.253  60.201  1.00 20.68      A    C
ATOM   1756  CB   PHE A 257      18.462  49.052  59.948  1.00 21.02      A    C
ATOM   1757  CG   PHE A 257      17.507  49.240  58.801  1.00 21.13      A    C
ATOM   1758  CD1  PHE A 257      16.690  50.367  58.732  1.00 22.09      A    C
ATOM   1759  CD2  PHE A 257      17.397  48.275  57.806  1.00 20.75      A    C
ATOM   1760  CE1  PHE A 257      15.774  50.524  57.682  1.00 21.86      A    C
ATOM   1761  CE2  PHE A 257      16.485  48.424  56.756  1.00 20.38      A    C
ATOM   1762  CZ   PHE A 257      15.672  49.549  56.694  1.00 18.09      A    C
ATOM   1763  C    PHE A 257      20.305  49.937  61.376  1.00 20.08      A    C
ATOM   1764  O    PHE A 257      20.440  48.794  61.770  1.00 19.49      A    O
ATOM   1765  N    PRO A 258      20.945  50.961  61.957  1.00 20.17      A    N
ATOM   1766  CD   PRO A 258      20.972  52.377  61.553  1.00 21.81      A    C
ATOM   1767  CA   PRO A 258      21.853  50.724  63.083  1.00 20.77      A    C
ATOM   1768  CB   PRO A 258      22.751  51.952  63.054  1.00 20.65      A    C
ATOM   1769  CG   PRO A 258      21.789  53.031  62.665  1.00 20.13      A    C
ATOM   1770  C    PRO A 258      21.137  50.575  64.412  1.00 21.80      A    C
ATOM   1771  O    PRO A 258      19.948  50.853  64.526  1.00 21.28      A    O
ATOM   1772  N    GLY A 259      21.884  50.137  65.418  1.00 21.76      A    N
ATOM   1773  CA   GLY A 259      21.317  49.961  66.737  1.00 20.69      A    C
ATOM   1774  C    GLY A 259      22.021  48.835  67.454  1.00 21.92      A    C
ATOM   1775  O    GLY A 259      22.371  47.838  66.847  1.00 22.99      A    O
ATOM   1776  N    ASP A 260      22.233  49.008  68.752  1.00 21.55      A    N
ATOM   1777  CA   ASP A 260      22.897  48.008  69.564  1.00 21.79      A    C
ATOM   1778  CB   ASP A 260      23.748  48.669  70.641  1.00 25.26      A    C
ATOM   1779  CG   ASP A 260      24.752  49.638  70.069  1.00 27.14      A    C
ATOM   1780  OD1  ASP A 260      25.076  49.509  68.865  1.00 26.38      A    O
ATOM   1781  OD2  ASP A 260      25.214  50.515  70.833  1.00 27.67      A    O
ATOM   1782  C    ASP A 260      21.910  47.075  70.238  1.00 21.06      A    C
ATOM   1783  O    ASP A 260      22.273  46.345  71.128  1.00 21.95      A    O
ATOM   1784  N    SER A 261      20.652  47.129  69.828  1.00 19.62      A    N
ATOM   1785  CA   SER A 261      19.658  46.240  70.402  1.00 19.11      A    C
ATOM   1786  CB   SER A 261      18.977  46.883  71.616  1.00 18.53      A    C
ATOM   1787  OG   SER A 261      17.987  47.819  71.234  1.00 18.77      A    O
ATOM   1788  C    SER A 261      18.620  45.952  69.331  1.00 19.87      A    C
ATOM   1789  O    SER A 261      18.413  46.755  68.428  1.00 20.16      A    O
ATOM   1790  N    GLY A 262      17.976  44.797  69.436  1.00 20.74      A    N
ATOM   1791  CA   GLY A 262      16.953  44.447  68.477  1.00 20.55      A    C
ATOM   1792  C    GLY A 262      15.890  45.529  68.428  1.00 22.06      A    C
ATOM   1793  O    GLY A 262      15.479  45.946  67.358  1.00 22.17      A    O
ATOM   1794  N    VAL A 263      15.461  45.989  69.599  1.00 22.00      A    N
ATOM   1795  CA   VAL A 263      14.447  47.031  69.695  1.00 23.54      A    C
ATOM   1796  CB   VAL A 263      14.188  47.436  71.173  1.00 24.78      A    C
ATOM   1797  CG1  VAL A 263      12.903  48.228  71.272  1.00 26.49      A    C
ATOM   1798  CG2  VAL A 263      14.122  46.211  72.056  1.00 26.55      A    C
```

FIG. 5-31

```
ATOM   1799  C   VAL A 263      14.868  48.282  68.927  1.00 23.14      A    C
ATOM   1800  O   VAL A 263      14.091  48.827  68.169  1.00 22.95      A    O
ATOM   1801  N   ASP A 264      16.107  48.726  69.144  1.00 22.67      A    N
ATOM   1802  CA  ASP A 264      16.630  49.912  68.473  1.00 22.53      A    C
ATOM   1803  CB  ASP A 264      18.013  50.271  69.032  1.00 21.68      A    C
ATOM   1804  CG  ASP A 264      17.928  50.935  70.403  1.00 22.73      A    C
ATOM   1805  OD1 ASP A 264      16.811  51.347  70.779  1.00 23.53      A    O
ATOM   1806  OD2 ASP A 264      18.958  51.062  71.097  1.00 23.65      A    O
ATOM   1807  C   ASP A 264      16.679  49.717  66.954  1.00 22.23      A    C
ATOM   1808  O   ASP A 264      16.373  50.617  66.203  1.00 22.69      A    O
ATOM   1809  N   GLN A 265      17.055  48.521  66.520  1.00 20.63      A    N
ATOM   1810  CA  GLN A 265      17.111  48.219  65.106  1.00 20.98      A    C
ATOM   1811  CB  GLN A 265      17.674  46.820  64.891  1.00 18.91      A    C
ATOM   1812  CG  GLN A 265      19.168  46.749  65.093  1.00 20.51      A    C
ATOM   1813  CD  GLN A 265      19.629  45.381  65.542  1.00 23.62      A    C
ATOM   1814  OE1 GLN A 265      19.075  44.370  65.143  1.00 20.92      A    O
ATOM   1815  NE2 GLN A 265      20.666  45.352  66.379  1.00 24.53      A    N
ATOM   1816  C   GLN A 265      15.698  48.311  64.544  1.00 20.93      A    C
ATOM   1817  O   GLN A 265      15.477  48.896  63.491  1.00 18.95      A    O
ATOM   1818  N   LEU A 266      14.744  47.737  65.266  1.00 21.03      A    N
ATOM   1819  CA  LEU A 266      13.355  47.770  64.833  1.00 22.88      A    C
ATOM   1820  CB  LEU A 266      12.469  47.007  65.817  1.00 24.42      A    C
ATOM   1821  CG  LEU A 266      11.875  45.725  65.233  1.00 24.76      A    C
ATOM   1822  CD1 LEU A 266      12.934  44.960  64.473  1.00 26.33      A    C
ATOM   1823  CD2 LEU A 266      11.300  44.877  66.350  1.00 26.09      A    C
ATOM   1824  C   LEU A 266      12.839  49.192  64.664  1.00 22.84      A    C
ATOM   1825  O   LEU A 266      12.156  49.491  63.692  1.00 22.54      A    O
ATOM   1826  N   VAL A 267      13.182  50.062  65.609  1.00 21.29      A    N
ATOM   1827  CA  VAL A 267      12.761  51.456  65.541  1.00 22.26      A    C
ATOM   1828  CB  VAL A 267      13.260  52.251  66.758  1.00 21.58      A    C
ATOM   1829  CG1 VAL A 267      13.056  53.732  66.522  1.00 18.41      A    C
ATOM   1830  CG2 VAL A 267      12.534  51.795  68.008  1.00 19.55      A    C
ATOM   1831  C   VAL A 267      13.339  52.111  64.290  1.00 22.84      A    C
ATOM   1832  O   VAL A 267      12.661  52.877  63.604  1.00 23.39      A    O
ATOM   1833  N   GLU A 268      14.603  51.816  64.013  1.00 22.26      A    N
ATOM   1834  CA  GLU A 268      15.258  52.379  62.849  1.00 22.21      A    C
ATOM   1835  CB  GLU A 268      16.730  51.965  62.794  1.00 23.64      A    C
ATOM   1836  CG  GLU A 268      17.614  52.644  63.827  1.00 27.30      A    C
ATOM   1837  CD  GLU A 268      17.555  54.162  63.746  1.00 30.66      A    C
ATOM   1838  OE1 GLU A 268      17.654  54.705  62.621  1.00 31.13      A    O
ATOM   1839  OE2 GLU A 268      17.417  54.807  64.813  1.00 30.86      A    O
ATOM   1840  C   GLU A 268      14.546  51.907  61.586  1.00 22.05      A    C
ATOM   1841  O   GLU A 268      14.365  52.670  60.661  1.00 20.47      A    O
ATOM   1842  N   ILE A 269      14.146  50.640  61.554  1.00 21.96      A    N
ATOM   1843  CA  ILE A 269      13.455  50.118  60.383  1.00 24.17      A    C
ATOM   1844  CB  ILE A 269      13.296  48.585  60.429  1.00 22.70      A    C
ATOM   1845  CG2 ILE A 269      12.398  48.121  59.286  1.00 21.84      A    C
ATOM   1846  CG1 ILE A 269      14.666  47.919  60.323  1.00 21.67      A    C
ATOM   1847  CD1 ILE A 269      14.635  46.438  60.551  1.00 19.34      A    C
ATOM   1848  C   ILE A 269      12.073  50.743  60.272  1.00 26.16      A    C
ATOM   1849  O   ILE A 269      11.599  51.031  59.173  1.00 26.24      A    O
ATOM   1850  N   ILE A 270      11.437  50.951  61.422  1.00 26.94      A    N
ATOM   1851  CA  ILE A 270      10.118  51.553  61.465  1.00 27.39      A    C
ATOM   1852  CB  ILE A 270       9.516  51.485  62.896  1.00 26.42      A    C
ATOM   1853  CG2 ILE A 270       8.259  52.340  62.982  1.00 27.68      A    C
ATOM   1854  CG1 ILE A 270       9.187  50.031  63.243  1.00 24.85      A    C
ATOM   1855  CD1 ILE A 270       8.777  49.795  64.675  1.00 23.03      A    C
ATOM   1856  C   ILE A 270      10.182  53.005  60.980  1.00 27.78      A    C
ATOM   1857  O   ILE A 270       9.306  53.446  60.274  1.00 28.70      A    O
ATOM   1858  N   LYS A 271      11.242  53.727  61.341  1.00 28.60      A    N
```

FIG. 5-32

```
ATOM   1859  CA   LYS A 271      11.380  55.117  60.916  1.00 29.22           A    C
ATOM   1860  CB   LYS A 271      12.647  55.755  61.498  1.00 29.65           A    C
ATOM   1861  CG   LYS A 271      12.633  55.992  62.995  1.00 33.54           A    C
ATOM   1862  CD   LYS A 271      13.797  56.896  63.399  1.00 36.47           A    C
ATOM   1863  CE   LYS A 271      14.407  56.453  64.713  1.00 39.12           A    C
ATOM   1864  NZ   LYS A 271      14.677  57.616  65.627  1.00 43.57           A    N
ATOM   1865  C    LYS A 271      11.415  55.283  59.393  1.00 30.54           A    C
ATOM   1866  O    LYS A 271      11.246  56.384  58.895  1.00 30.70           A    O
ATOM   1867  N    VAL A 272      11.648  54.202  58.652  1.00 30.52           A    N
ATOM   1868  CA   VAL A 272      11.672  54.322  57.201  1.00 30.17           A    C
ATOM   1869  CB   VAL A 272      13.035  53.881  56.580  1.00 30.73           A    C
ATOM   1870  CG1  VAL A 272      14.197  54.546  57.311  1.00 28.40           A    C
ATOM   1871  CG2  VAL A 272      13.158  52.386  56.603  1.00 33.61           A    C
ATOM   1872  C    VAL A 272      10.550  53.560  56.514  1.00 29.95           A    C
ATOM   1873  O    VAL A 272       9.941  54.081  55.592  1.00 31.86           A    O
ATOM   1874  N    LEU A 273      10.261  52.343  56.964  1.00 29.24           A    N
ATOM   1875  CA   LEU A 273       9.196  51.548  56.349  1.00 28.82           A    C
ATOM   1876  CB   LEU A 273       9.465  50.049  56.535  1.00 27.62           A    C
ATOM   1877  CG   LEU A 273      10.633  49.392  55.792  1.00 26.98           A    C
ATOM   1878  CD1  LEU A 273      10.587  47.893  56.003  1.00 23.92           A    C
ATOM   1879  CD2  LEU A 273      10.538  49.711  54.308  1.00 28.04           A    C
ATOM   1880  C    LEU A 273       7.825  51.863  56.916  1.00 29.85           A    C
ATOM   1881  O    LEU A 273       6.817  51.597  56.294  1.00 30.72           A    O
ATOM   1882  N    GLY A 274       7.806  52.432  58.112  1.00 29.58           A    N
ATOM   1883  CA   GLY A 274       6.549  52.730  58.759  1.00 30.38           A    C
ATOM   1884  C    GLY A 274       6.286  51.543  59.656  1.00 31.41           A    C
ATOM   1885  O    GLY A 274       6.904  50.478  59.494  1.00 29.55           A    O
ATOM   1886  N    THR A 275       5.379  51.729  60.604  1.00 32.10           A    N
ATOM   1887  CA   THR A 275       5.025  50.688  61.549  1.00 33.11           A    C
ATOM   1888  CB   THR A 275       4.063  51.247  62.606  1.00 32.43           A    C
ATOM   1889  OG1  THR A 275       4.620  52.452  63.146  1.00 30.38           A    O
ATOM   1890  CG2  THR A 275       3.872  50.251  63.734  1.00 34.23           A    C
ATOM   1891  C    THR A 275       4.388  49.525  60.794  1.00 33.87           A    C
ATOM   1892  O    THR A 275       3.584  49.727  59.885  1.00 34.46           A    O
ATOM   1893  N    PRO A 276       4.776  48.288  61.132  1.00 33.03           A    N
ATOM   1894  CD   PRO A 276       5.884  47.864  62.006  1.00 33.31           A    C
ATOM   1895  CA   PRO A 276       4.186  47.144  60.434  1.00 34.01           A    C
ATOM   1896  CB   PRO A 276       5.123  45.993  60.802  1.00 33.61           A    C
ATOM   1897  CG   PRO A 276       5.618  46.379  62.156  1.00 33.03           A    C
ATOM   1898  C    PRO A 276       2.734  46.867  60.829  1.00 34.65           A    C
ATOM   1899  O    PRO A 276       2.351  46.971  61.993  1.00 35.03           A    O
ATOM   1900  N    THR A 277       1.934  46.507  59.836  1.00 35.12           A    N
ATOM   1901  CA   THR A 277       0.526  46.204  60.044  1.00 34.44           A    C
ATOM   1902  CB   THR A 277      -0.210  46.156  58.692  1.00 33.20           A    C
ATOM   1903  OG1  THR A 277       0.263  45.039  57.927  1.00 32.89           A    O
ATOM   1904  CG2  THR A 277       0.052  47.434  57.904  1.00 31.06           A    C
ATOM   1905  C    THR A 277       0.411  44.849  60.740  1.00 35.39           A    C
ATOM   1906  O    THR A 277       1.392  44.106  60.833  1.00 35.16           A    O
ATOM   1907  N    ALA A 278      -0.782  44.533  61.231  1.00 35.51           A    N
ATOM   1908  CA   ALA A 278      -1.001  43.268  61.919  1.00 35.92           A    C
ATOM   1909  CB   ALA A 278      -2.450  43.166  62.391  1.00 37.57           A    C
ATOM   1910  C    ALA A 278      -0.679  42.109  60.995  1.00 35.25           A    C
ATOM   1911  O    ALA A 278      -0.017  41.149  61.392  1.00 35.23           A    O
ATOM   1912  N    ALA A 279      -1.152  42.212  59.756  1.00 35.14           A    N
ATOM   1913  CA   ALA A 279      -0.937  41.169  58.759  1.00 35.77           A    C
ATOM   1914  CB   ALA A 279      -1.675  41.524  57.456  1.00 33.47           A    C
ATOM   1915  C    ALA A 279       0.556  40.967  58.493  1.00 35.63           A    C
ATOM   1916  O    ALA A 279       1.025  39.829  58.326  1.00 36.30           A    O
ATOM   1917  N    GLN A 280       1.299  42.067  58.461  1.00 35.02           A    N
ATOM   1918  CA   GLN A 280       2.734  41.992  58.223  1.00 34.97           A    C
```

FIG. 5-33

```
ATOM   1919  CB   GLN A 280       3.295  43.396  58.000  1.00 33.88      A    C
ATOM   1920  CG   GLN A 280       2.932  43.969  56.641  1.00 32.79      A    C
ATOM   1921  CD   GLN A 280       3.331  45.420  56.477  1.00 33.33      A    C
ATOM   1922  OE1  GLN A 280       3.716  45.853  55.381  1.00 32.27      A    O
ATOM   1923  NE2  GLN A 280       3.228  46.191  57.560  1.00 31.22      A    N
ATOM   1924  C    GLN A 280       3.444  41.289  59.386  1.00 36.10      A    C
ATOM   1925  O    GLN A 280       4.411  40.523  59.182  1.00 35.36      A    O
ATOM   1926  N    ALA A 281       2.968  41.536  60.602  1.00 36.11      A    N
ATOM   1927  CA   ALA A 281       3.553  40.897  61.769  1.00 36.54      A    C
ATOM   1928  CB   ALA A 281       2.892  41.406  63.044  1.00 37.37      A    C
ATOM   1929  C    ALA A 281       3.334  39.398  61.630  1.00 37.38      A    C
ATOM   1930  O    ALA A 281       4.220  38.595  61.936  1.00 36.62      A    O
ATOM   1931  N    ALA A 282       2.150  39.024  61.148  1.00 38.09      A    N
ATOM   1932  CA   ALA A 282       1.808  37.615  60.977  1.00 38.76      A    C
ATOM   1933  CB   ALA A 282       0.383  37.485  60.446  1.00 39.32      A    C
ATOM   1934  C    ALA A 282       2.774  36.891  60.041  1.00 39.44      A    C
ATOM   1935  O    ALA A 282       3.257  35.801  60.360  1.00 39.40      A    O
ATOM   1936  N    ALA A 283       3.045  37.502  58.889  1.00 39.72      A    N
ATOM   1937  CA   ALA A 283       3.937  36.913  57.897  1.00 39.85      A    C
ATOM   1938  CB   ALA A 283       3.950  37.763  56.633  1.00 39.77      A    C
ATOM   1939  C    ALA A 283       5.353  36.740  58.433  1.00 39.40      A    C
ATOM   1940  O    ALA A 283       5.998  35.711  58.179  1.00 39.41      A    O
ATOM   1941  N    MET A 284       5.840  37.748  59.161  1.00 39.37      A    N
ATOM   1942  CA   MET A 284       7.179  37.678  59.753  1.00 39.28      A    C
ATOM   1943  CB   MET A 284       7.616  39.053  60.269  1.00 37.37      A    C
ATOM   1944  CG   MET A 284       7.738  40.109  59.179  1.00 36.82      A    C
ATOM   1945  SD   MET A 284       8.496  41.668  59.697  1.00 31.23      A    S
ATOM   1946  CE   MET A 284       7.143  42.434  60.635  1.00 32.69      A    C
ATOM   1947  C    MET A 284       7.155  36.639  60.879  1.00 39.40      A    C
ATOM   1948  O    MET A 284       8.181  36.045  61.222  1.00 38.91      A    O
ATOM   1949  N    ASN A 285       5.969  36.442  61.449  1.00 40.86      A    N
ATOM   1950  CA   ASN A 285       5.743  35.429  62.479  1.00 41.64      A    C
ATOM   1951  CB   ASN A 285       5.780  34.058  61.813  1.00 42.06      A    C
ATOM   1952  CG   ASN A 285       4.924  33.036  62.528  1.00 42.83      A    C
ATOM   1953  OD1  ASN A 285       4.831  33.023  63.767  1.00 42.65      A    O
ATOM   1954  ND2  ASN A 285       4.296  32.160  61.754  1.00 42.68      A    N
ATOM   1955  C    ASN A 285       6.727  35.428  63.643  1.00 41.88      A    C
ATOM   1956  O    ASN A 285       7.531  34.508  63.780  1.00 41.13      A    O
ATOM   1957  N    PRO A 286       6.664  36.439  64.512  1.00 43.03      A    N
ATOM   1958  CD   PRO A 286       5.742  37.587  64.499  1.00 43.64      A    C
ATOM   1959  CA   PRO A 286       7.584  36.496  65.658  1.00 43.94      A    C
ATOM   1960  CB   PRO A 286       7.435  37.935  66.142  1.00 45.24      A    C
ATOM   1961  CG   PRO A 286       5.991  38.229  65.862  1.00 45.21      A    C
ATOM   1962  C    PRO A 286       7.255  35.479  66.753  1.00 43.53      A    C
ATOM   1963  O    PRO A 286       6.109  35.028  66.852  1.00 43.19      A    O
ATOM   1964  N    ASN A 287       8.248  35.112  67.568  1.00 43.55      A    N
ATOM   1965  CA   ASN A 287       7.987  34.173  68.655  1.00 43.99      A    C
ATOM   1966  CB   ASN A 287       9.289  33.767  69.392  1.00 42.48      A    C
ATOM   1967  CG   ASN A 287      10.069  34.953  69.978  1.00 42.15      A    C
ATOM   1968  OD1  ASN A 287       9.662  36.119  69.866  1.00 39.50      A    O
ATOM   1969  ND2  ASN A 287      11.212  34.646  70.616  1.00 39.81      A    N
ATOM   1970  C    ASN A 287       6.973  34.827  69.598  1.00 44.16      A    C
ATOM   1971  O    ASN A 287       6.074  34.173  70.103  1.00 44.13      A    O
ATOM   1972  N    TYR A 288       7.124  36.135  69.803  1.00 45.02      A    N
ATOM   1973  CA   TYR A 288       6.206  36.915  70.631  1.00 45.95      A    C
ATOM   1974  CB   TYR A 288       6.414  36.682  72.131  1.00 46.67      A    C
ATOM   1975  CG   TYR A 288       5.538  37.600  72.955  1.00 47.83      A    C
ATOM   1976  CD1  TYR A 288       4.144  37.490  72.911  1.00 49.04      A    C
ATOM   1977  CE1  TYR A 288       3.326  38.370  73.617  1.00 50.03      A    C
ATOM   1978  CD2  TYR A 288       6.094  38.613  73.736  1.00 48.07      A    C
```

FIG. 5-34

```
ATOM   1979  CE2 TYR A 288       5.288  39.500  74.448  1.00 49.43           A    C
ATOM   1980  CZ  TYR A 288       3.902  39.370  74.387  1.00 50.66           A    C
ATOM   1981  OH  TYR A 288       3.090  40.233  75.101  1.00 51.30           A    O
ATOM   1982  C   TYR A 288       6.367  38.404  70.366  1.00 46.28           A    C
ATOM   1983  O   TYR A 288       7.491  38.921  70.248  1.00 46.95           A    O
ATOM   1984  N   GLY A 289       5.240  39.098  70.286  1.00 45.93           A    N
ATOM   1985  CA  GLY A 289       5.276  40.525  70.050  1.00 45.71           A    C
ATOM   1986  C   GLY A 289       4.190  41.178  70.883  1.00 46.08           A    C
ATOM   1987  O   GLY A 289       3.161  40.553  71.174  1.00 45.17           A    O
ATOM   1988  N   ALA A 290       4.417  42.425  71.278  1.00 45.39           A    N
ATOM   1989  CA  ALA A 290       3.440  43.153  72.063  1.00 45.68           A    C
ATOM   1990  CB  ALA A 290       4.067  43.638  73.372  1.00 45.69           A    C
ATOM   1991  C   ALA A 290       2.953  44.336  71.237  1.00 45.63           A    C
ATOM   1992  O   ALA A 290       1.795  44.705  71.307  1.00 45.67           A    O
ATOM   2004  N   TRP A 301      11.214  56.597  50.481  1.00 45.06           A    N
ATOM   2005  CA  TRP A 301      12.541  56.076  50.210  1.00 43.81           A    C
ATOM   2006  CB  TRP A 301      12.441  54.838  49.325  1.00 42.40           A    C
ATOM   2007  CG  TRP A 301      12.170  53.594  50.089  1.00 41.47           A    C
ATOM   2008  CD2 TRP A 301      13.127  52.838  50.832  1.00 40.02           A    C
ATOM   2009  CE2 TRP A 301      12.453  51.724  51.384  1.00 39.64           A    C
ATOM   2010  CE3 TRP A 301      14.498  52.990  51.090  1.00 39.55           A    C
ATOM   2011  CD1 TRP A 301      10.977  52.940  50.212  1.00 41.82           A    C
ATOM   2012  NE1 TRP A 301      11.136  51.808  50.990  1.00 41.59           A    N
ATOM   2013  CZ2 TRP A 301      13.094  50.768  52.170  1.00 39.13           A    C
ATOM   2014  CZ3 TRP A 301      15.141  52.042  51.874  1.00 39.37           A    C
ATOM   2015  CH2 TRP A 301      14.437  50.943  52.405  1.00 38.91           A    C
ATOM   2016  C   TRP A 301      13.403  57.118  49.524  1.00 43.97           A    C
ATOM   2017  O   TRP A 301      14.612  57.133  49.673  1.00 44.02           A    O
ATOM   2018  N   THR A 302      12.763  57.995  48.767  1.00 44.65           A    N
ATOM   2019  CA  THR A 302      13.483  59.027  48.046  1.00 44.70           A    C
ATOM   2020  CB  THR A 302      12.544  59.760  47.079  1.00 45.51           A    C
ATOM   2021  OG1 THR A 302      11.221  59.212  47.199  1.00 47.43           A    O
ATOM   2022  CG2 THR A 302      13.025  59.584  45.643  1.00 44.92           A    C
ATOM   2023  C   THR A 302      14.120  60.011  49.014  1.00 43.43           A    C
ATOM   2024  O   THR A 302      15.179  60.550  48.742  1.00 43.88           A    O
ATOM   2025  N   ALA A 303      13.477  60.217  50.157  1.00 42.24           A    N
ATOM   2026  CA  ALA A 303      13.998  61.127  51.169  1.00 40.88           A    C
ATOM   2027  CB  ALA A 303      12.909  61.412  52.209  1.00 40.11           A    C
ATOM   2028  C   ALA A 303      15.221  60.500  51.847  1.00 39.65           A    C
ATOM   2029  O   ALA A 303      16.103  61.194  52.350  1.00 39.99           A    O
ATOM   2030  N   VAL A 304      15.257  59.173  51.847  1.00 37.86           A    N
ATOM   2031  CA  VAL A 304      16.333  58.429  52.487  1.00 35.43           A    C
ATOM   2032  CB  VAL A 304      16.058  56.903  52.425  1.00 34.87           A    C
ATOM   2033  CG1 VAL A 304      17.274  56.120  52.908  1.00 32.37           A    C
ATOM   2034  CG2 VAL A 304      14.844  56.566  53.276  1.00 32.48           A    C
ATOM   2035  C   VAL A 304      17.731  58.692  51.926  1.00 34.73           A    C
ATOM   2036  O   VAL A 304      18.676  58.874  52.682  1.00 33.78           A    O
ATOM   2037  N   PHE A 305      17.863  58.718  50.603  1.00 33.59           A    N
ATOM   2038  CA  PHE A 305      19.169  58.902  49.994  1.00 32.69           A    C
ATOM   2039  CB  PHE A 305      19.330  57.914  48.847  1.00 30.63           A    C
ATOM   2040  CG  PHE A 305      19.138  56.490  49.258  1.00 28.96           A    C
ATOM   2041  CD1 PHE A 305      20.135  55.812  49.950  1.00 25.66           A    C
ATOM   2042  CD2 PHE A 305      17.942  55.831  48.980  1.00 26.44           A    C
ATOM   2043  CE1 PHE A 305      19.942  54.496  50.361  1.00 25.79           A    C
ATOM   2044  CE2 PHE A 305      17.743  54.520  49.387  1.00 24.79           A    C
ATOM   2045  CZ  PHE A 305      18.742  53.849  50.076  1.00 23.69           A    C
ATOM   2046  C   PHE A 305      19.497  60.297  49.480  1.00 34.95           A    C
ATOM   2047  O   PHE A 305      18.623  61.146  49.314  1.00 34.78           A    O
ATOM   2048  N   ARG A 306      20.777  60.513  49.200  1.00 37.40           A    N
ATOM   2049  CA  ARG A 306      21.229  61.798  48.700  1.00 39.51           A    C
```

FIG. 5-35

```
ATOM   2050  CB   ARG A 306      22.759  61.797  48.525  1.00 40.32           A    C
ATOM   2051  CG   ARG A 306      23.343  60.778  47.533  1.00 43.39           A    C
ATOM   2052  CD   ARG A 306      24.881  60.812  47.560  1.00 46.22           A    C
ATOM   2053  NE   ARG A 306      25.501  60.466  46.275  1.00 49.82           A    N
ATOM   2054  CZ   ARG A 306      25.957  59.258  45.935  1.00 52.51           A    C
ATOM   2055  NH1  ARG A 306      25.881  58.232  46.785  1.00 52.45           A    N
ATOM   2056  NH2  ARG A 306      26.497  59.075  44.730  1.00 52.94           A    N
ATOM   2057  C    ARG A 306      20.524  62.125  47.395  1.00 41.07           A    C
ATOM   2058  O    ARG A 306      20.258  61.248  46.588  1.00 41.37           A    O
ATOM   2059  N    PRO A 307      20.197  63.407  47.188  1.00 41.64           A    N
ATOM   2060  CD   PRO A 307      20.623  64.504  48.078  1.00 42.48           A    C
ATOM   2061  CA   PRO A 307      19.510  63.942  46.009  1.00 43.02           A    C
ATOM   2062  CB   PRO A 307      19.957  65.401  46.004  1.00 42.91           A    C
ATOM   2063  CG   PRO A 307      19.933  65.723  47.463  1.00 43.48           A    C
ATOM   2064  C    PRO A 307      19.758  63.265  44.657  1.00 43.10           A    C
ATOM   2065  O    PRO A 307      18.804  62.788  44.016  1.00 43.71           A    O
ATOM   2066  N    ALA A 308      21.017  63.231  44.221  1.00 41.64           A    N
ATOM   2067  CA   ALA A 308      21.357  62.652  42.919  1.00 40.52           A    C
ATOM   2068  CB   ALA A 308      22.764  63.096  42.504  1.00 41.00           A    C
ATOM   2069  C    ALA A 308      21.239  61.130  42.791  1.00 39.22           A    C
ATOM   2070  O    ALA A 308      21.394  60.583  41.711  1.00 38.32           A    O
ATOM   2071  N    THR A 309      20.951  60.450  43.893  1.00 37.40           A    N
ATOM   2072  CA   THR A 309      20.850  58.999  43.859  1.00 36.03           A    C
ATOM   2073  CB   THR A 309      20.291  58.457  45.171  1.00 35.60           A    C
ATOM   2074  OG1  THR A 309      21.128  58.887  46.250  1.00 34.01           A    O
ATOM   2075  CG2  THR A 309      20.257  56.936  45.138  1.00 34.95           A    C
ATOM   2076  C    THR A 309      19.959  58.525  42.722  1.00 35.20           A    C
ATOM   2077  O    THR A 309      18.897  59.051  42.503  1.00 34.87           A    O
ATOM   2078  N    PRO A 310      20.420  57.526  41.963  1.00 34.41           A    N
ATOM   2079  CD   PRO A 310      21.783  56.980  41.926  1.00 33.93           A    C
ATOM   2080  CA   PRO A 310      19.621  57.006  40.853  1.00 34.35           A    C
ATOM   2081  CB   PRO A 310      20.554  55.984  40.193  1.00 33.67           A    C
ATOM   2082  CG   PRO A 310      21.551  55.661  41.266  1.00 35.69           A    C
ATOM   2083  C    PRO A 310      18.309  56.390  41.330  1.00 33.76           A    C
ATOM   2084  O    PRO A 310      18.292  55.573  42.250  1.00 34.57           A    O
ATOM   2085  N    PRO A 311      17.191  56.794  40.710  1.00 33.11           A    N
ATOM   2086  CD   PRO A 311      17.146  57.764  39.602  1.00 31.68           A    C
ATOM   2087  CA   PRO A 311      15.845  56.309  41.037  1.00 31.82           A    C
ATOM   2088  CB   PRO A 311      14.983  56.906  39.928  1.00 32.46           A    C
ATOM   2089  CG   PRO A 311      15.696  58.170  39.588  1.00 32.92           A    C
ATOM   2090  C    PRO A 311      15.750  54.787  41.050  1.00 31.44           A    C
ATOM   2091  O    PRO A 311      15.095  54.202  41.923  1.00 31.89           A    O
ATOM   2092  N    GLU A 312      16.393  54.144  40.075  1.00 30.47           A    N
ATOM   2093  CA   GLU A 312      16.356  52.686  39.984  1.00 30.21           A    C
ATOM   2094  CB   GLU A 312      17.121  52.185  38.751  1.00 31.71           A    C
ATOM   2095  CG   GLU A 312      16.671  52.726  37.402  1.00 35.62           A    C
ATOM   2096  CD   GLU A 312      17.147  54.155  37.128  1.00 39.45           A    C
ATOM   2097  OE1  GLU A 312      18.120  54.624  37.771  1.00 39.22           A    O
ATOM   2098  OE2  GLU A 312      16.548  54.805  36.244  1.00 41.86           A    O
ATOM   2099  C    GLU A 312      16.965  52.020  41.221  1.00 29.24           A    C
ATOM   2100  O    GLU A 312      16.528  50.952  41.635  1.00 28.83           A    O
ATOM   2101  N    ALA A 313      17.992  52.647  41.787  1.00 27.49           A    N
ATOM   2102  CA   ALA A 313      18.649  52.110  42.973  1.00 26.21           A    C
ATOM   2103  CB   ALA A 313      19.860  52.961  43.336  1.00 24.09           A    C
ATOM   2104  C    ALA A 313      17.657  52.115  44.121  1.00 25.84           A    C
ATOM   2105  O    ALA A 313      17.529  51.145  44.860  1.00 22.94           A    O
ATOM   2106  N    ILE A 314      16.952  53.233  44.254  1.00 27.14           A    N
ATOM   2107  CA   ILE A 314      15.971  53.391  45.315  1.00 28.41           A    C
ATOM   2108  CB   ILE A 314      15.453  54.841  45.353  1.00 29.47           A    C
ATOM   2109  CG2  ILE A 314      14.383  54.995  46.430  1.00 31.27           A    C
```

FIG. 5-36

| ATOM | 2110 | CG1 | ILE A 314 | 16.626 | 55.781 | 45.651 | 1.00 | 30.70 | A | C |
|---|---|---|---|---|---|---|---|---|---|---|
| ATOM | 2111 | CD1 | ILE A 314 | 16.291 | 57.244 | 45.534 | 1.00 | 29.93 | A | C |
| ATOM | 2112 | C | ILE A 314 | 14.811 | 52.417 | 45.158 | 1.00 | 27.99 | A | C |
| ATOM | 2113 | O | ILE A 314 | 14.355 | 51.830 | 46.140 | 1.00 | 27.91 | A | O |
| ATOM | 2114 | N | ALA A 315 | 14.357 | 52.242 | 43.921 | 1.00 | 26.99 | A | N |
| ATOM | 2115 | CA | ALA A 315 | 13.255 | 51.338 | 43.623 | 1.00 | 27.18 | A | C |
| ATOM | 2116 | CB | ALA A 315 | 12.936 | 51.366 | 42.124 | 1.00 | 25.67 | A | C |
| ATOM | 2117 | C | ALA A 315 | 13.638 | 49.934 | 44.055 | 1.00 | 26.46 | A | C |
| ATOM | 2118 | O | ALA A 315 | 12.860 | 49.243 | 44.695 | 1.00 | 26.99 | A | O |
| ATOM | 2119 | N | LEU A 316 | 14.850 | 49.526 | 43.696 | 1.00 | 25.48 | A | N |
| ATOM | 2120 | CA | LEU A 316 | 15.347 | 48.203 | 44.056 | 1.00 | 25.14 | A | C |
| ATOM | 2121 | CB | LEU A 316 | 16.763 | 48.005 | 43.497 | 1.00 | 22.99 | A | C |
| ATOM | 2122 | CG | LEU A 316 | 17.519 | 46.751 | 43.954 | 1.00 | 24.83 | A | C |
| ATOM | 2123 | CD1 | LEU A 316 | 16.679 | 45.511 | 43.679 | 1.00 | 22.07 | A | C |
| ATOM | 2124 | CD2 | LEU A 316 | 18.861 | 46.664 | 43.235 | 1.00 | 23.72 | A | C |
| ATOM | 2125 | C | LEU A 316 | 15.344 | 48.033 | 45.579 | 1.00 | 24.81 | A | C |
| ATOM | 2126 | O | LEU A 316 | 14.879 | 47.021 | 46.082 | 1.00 | 25.21 | A | O |
| ATOM | 2127 | N | CYS A 317 | 15.851 | 49.030 | 46.303 | 1.00 | 24.47 | A | N |
| ATOM | 2128 | CA | CYS A 317 | 15.882 | 48.960 | 47.763 | 1.00 | 26.27 | A | C |
| ATOM | 2129 | CB | CYS A 317 | 16.445 | 50.239 | 48.389 | 1.00 | 26.91 | A | C |
| ATOM | 2130 | SG | CYS A 317 | 18.232 | 50.414 | 48.359 | 1.00 | 31.13 | A | S |
| ATOM | 2131 | C | CYS A 317 | 14.499 | 48.727 | 48.347 | 1.00 | 26.12 | A | C |
| ATOM | 2132 | O | CYS A 317 | 14.330 | 47.920 | 49.251 | 1.00 | 26.44 | A | O |
| ATOM | 2133 | N | SER A 318 | 13.511 | 49.447 | 47.834 | 1.00 | 25.86 | A | N |
| ATOM | 2134 | CA | SER A 318 | 12.159 | 49.293 | 48.349 | 1.00 | 26.58 | A | C |
| ATOM | 2135 | CB | SER A 318 | 11.219 | 50.323 | 47.727 | 1.00 | 27.14 | A | C |
| ATOM | 2136 | OG | SER A 318 | 10.875 | 49.959 | 46.407 | 1.00 | 30.27 | A | O |
| ATOM | 2137 | C | SER A 318 | 11.616 | 47.884 | 48.101 | 1.00 | 26.40 | A | C |
| ATOM | 2138 | O | SER A 318 | 10.777 | 47.405 | 48.854 | 1.00 | 26.62 | A | O |
| ATOM | 2139 | N | ARG A 319 | 12.106 | 47.217 | 47.057 | 1.00 | 25.73 | A | N |
| ATOM | 2140 | CA | ARG A 319 | 11.625 | 45.876 | 46.740 | 1.00 | 25.90 | A | C |
| ATOM | 2141 | CB | ARG A 319 | 11.659 | 45.652 | 45.230 | 1.00 | 26.84 | A | C |
| ATOM | 2142 | CG | ARG A 319 | 10.806 | 46.647 | 44.479 | 1.00 | 29.32 | A | C |
| ATOM | 2143 | CD | ARG A 319 | 9.318 | 46.437 | 44.755 | 1.00 | 31.31 | A | C |
| ATOM | 2144 | NE | ARG A 319 | 8.778 | 45.391 | 43.895 | 1.00 | 33.81 | A | N |
| ATOM | 2145 | CZ | ARG A 319 | 8.721 | 44.099 | 44.208 | 1.00 | 35.41 | A | C |
| ATOM | 2146 | NH1 | ARG A 319 | 9.162 | 43.665 | 45.385 | 1.00 | 36.68 | A | N |
| ATOM | 2147 | NH2 | ARG A 319 | 8.249 | 43.233 | 43.324 | 1.00 | 33.23 | A | N |
| ATOM | 2148 | C | ARG A 319 | 12.408 | 44.774 | 47.440 | 1.00 | 26.29 | A | C |
| ATOM | 2149 | O | ARG A 319 | 12.092 | 43.581 | 47.309 | 1.00 | 25.97 | A | O |
| ATOM | 2150 | N | LEU A 320 | 13.430 | 45.178 | 48.183 | 1.00 | 25.71 | A | N |
| ATOM | 2151 | CA | LEU A 320 | 14.261 | 44.240 | 48.920 | 1.00 | 24.46 | A | C |
| ATOM | 2152 | CB | LEU A 320 | 15.747 | 44.546 | 48.698 | 1.00 | 23.01 | A | C |
| ATOM | 2153 | CG | LEU A 320 | 16.315 | 44.482 | 47.276 | 1.00 | 21.96 | A | C |
| ATOM | 2154 | CD1 | LEU A 320 | 17.795 | 44.819 | 47.313 | 1.00 | 20.47 | A | C |
| ATOM | 2155 | CD2 | LEU A 320 | 16.112 | 43.091 | 46.686 | 1.00 | 21.59 | A | C |
| ATOM | 2156 | C | LEU A 320 | 13.935 | 44.342 | 50.401 | 1.00 | 24.05 | A | C |
| ATOM | 2157 | O | LEU A 320 | 13.678 | 43.352 | 51.057 | 1.00 | 24.07 | A | O |
| ATOM | 2158 | N | LEU A 321 | 13.949 | 45.567 | 50.909 | 1.00 | 24.89 | A | N |
| ATOM | 2159 | CA | LEU A 321 | 13.671 | 45.832 | 52.312 | 1.00 | 24.70 | A | C |
| ATOM | 2160 | CB | LEU A 321 | 14.386 | 47.125 | 52.717 | 1.00 | 23.75 | A | C |
| ATOM | 2161 | CG | LEU A 321 | 15.895 | 47.053 | 52.425 | 1.00 | 22.70 | A | C |
| ATOM | 2162 | CD1 | LEU A 321 | 16.557 | 48.400 | 52.672 | 1.00 | 22.21 | A | C |
| ATOM | 2163 | CD2 | LEU A 321 | 16.535 | 45.970 | 53.295 | 1.00 | 20.58 | A | C |
| ATOM | 2164 | C | LEU A 321 | 12.158 | 45.917 | 52.548 | 1.00 | 25.11 | A | C |
| ATOM | 2165 | O | LEU A 321 | 11.589 | 46.989 | 52.643 | 1.00 | 26.40 | A | O |
| ATOM | 2166 | N | GLU A 322 | 11.518 | 44.758 | 52.626 | 1.00 | 24.72 | A | N |
| ATOM | 2167 | CA | GLU A 322 | 10.080 | 44.699 | 52.842 | 1.00 | 26.51 | A | C |
| ATOM | 2168 | CB | GLU A 322 | 9.372 | 44.148 | 51.603 | 1.00 | 26.96 | A | C |
| ATOM | 2169 | CG | GLU A 322 | 9.688 | 44.889 | 50.325 | 1.00 | 31.52 | A | C |

FIG. 5-37

```
ATOM   2170  CD   GLU A 322       8.440  45.341  49.597  1.00 33.86      A  C
ATOM   2171  OE1  GLU A 322       7.669  46.128  50.191  1.00 36.19      A  O
ATOM   2172  OE2  GLU A 322       8.231  44.912  48.438  1.00 33.19      A  O
ATOM   2173  C    GLU A 322       9.752  43.801  54.031  1.00 26.06      A  C
ATOM   2174  O    GLU A 322      10.362  42.762  54.209  1.00 26.23      A  O
ATOM   2175  N    TYR A 323       8.777  44.215  54.833  1.00 26.28      A  N
ATOM   2176  CA   TYR A 323       8.376  43.433  55.997  1.00 25.93      A  C
ATOM   2177  CB   TYR A 323       7.226  44.122  56.738  1.00 25.73      A  C
ATOM   2178  CG   TYR A 323       7.656  45.267  57.620  1.00 24.57      A  C
ATOM   2179  CD1  TYR A 323       8.569  45.071  58.658  1.00 23.90      A  C
ATOM   2180  CE1  TYR A 323       8.944  46.118  59.492  1.00 24.02      A  C
ATOM   2181  CD2  TYR A 323       7.133  46.543  57.433  1.00 23.87      A  C
ATOM   2182  CE2  TYR A 323       7.500  47.594  58.256  1.00 24.56      A  C
ATOM   2183  CZ   TYR A 323       8.405  47.379  59.284  1.00 25.67      A  C
ATOM   2184  OH   TYR A 323       8.754  48.433  60.096  1.00 25.93      A  O
ATOM   2185  C    TYR A 323       7.948  42.023  55.589  1.00 25.13      A  C
ATOM   2186  O    TYR A 323       8.484  41.021  56.087  1.00 24.40      A  O
ATOM   2187  N    THR A 324       6.984  41.947  54.684  1.00 24.41      A  N
ATOM   2188  CA   THR A 324       6.504  40.657  54.218  1.00 24.91      A  C
ATOM   2189  CB   THR A 324       5.310  40.828  53.251  1.00 25.79      A  C
ATOM   2190  OG1  THR A 324       4.277  41.583  53.899  1.00 25.90      A  O
ATOM   2191  CG2  THR A 324       4.750  39.473  52.849  1.00 25.36      A  C
ATOM   2192  C    THR A 324       7.663  39.973  53.507  1.00 23.59      A  C
ATOM   2193  O    THR A 324       8.095  40.412  52.474  1.00 24.84      A  O
ATOM   2194  N    PRO A 325       8.183  38.886  54.088  1.00 24.10      A  N
ATOM   2195  CD   PRO A 325       7.739  38.253  55.344  1.00 23.78      A  C
ATOM   2196  CA   PRO A 325       9.305  38.147  53.509  1.00 24.48      A  C
ATOM   2197  CB   PRO A 325       9.487  36.982  54.479  1.00 24.85      A  C
ATOM   2198  CG   PRO A 325       8.970  37.532  55.782  1.00 23.36      A  C
ATOM   2199  C    PRO A 325       9.053  37.675  52.088  1.00 25.66      A  C
ATOM   2200  O    PRO A 325       9.934  37.735  51.247  1.00 24.22      A  O
ATOM   2201  N    THR A 326       7.830  37.214  51.844  1.00 27.02      A  N
ATOM   2202  CA   THR A 326       7.419  36.689  50.550  1.00 26.74      A  C
ATOM   2203  CB   THR A 326       6.085  35.927  50.695  1.00 29.59      A  C
ATOM   2204  OG1  THR A 326       5.840  35.157  49.515  1.00 33.02      A  O
ATOM   2205  CG2  THR A 326       4.935  36.902  50.904  1.00 27.84      A  C
ATOM   2206  C    THR A 326       7.271  37.776  49.481  1.00 26.97      A  C
ATOM   2207  O    THR A 326       7.229  37.483  48.284  1.00 25.81      A  O
ATOM   2208  N    ALA A 327       7.189  39.028  49.911  1.00 25.61      A  N
ATOM   2209  CA   ALA A 327       7.038  40.133  48.968  1.00 25.41      A  C
ATOM   2210  CB   ALA A 327       6.340  41.304  49.635  1.00 24.03      A  C
ATOM   2211  C    ALA A 327       8.391  40.580  48.410  1.00 25.75      A  C
ATOM   2212  O    ALA A 327       8.469  41.178  47.340  1.00 25.62      A  O
ATOM   2213  N    ARG A 328       9.452  40.279  49.143  1.00 24.18      A  N
ATOM   2214  CA   ARG A 328      10.785  40.655  48.718  1.00 24.33      A  C
ATOM   2215  CB   ARG A 328      11.796  40.237  49.781  1.00 21.44      A  C
ATOM   2216  CG   ARG A 328      11.505  40.847  51.136  1.00 22.88      A  C
ATOM   2217  CD   ARG A 328      12.340  40.219  52.224  1.00 20.95      A  C
ATOM   2218  NE   ARG A 328      11.873  40.630  53.545  1.00 22.65      A  N
ATOM   2219  CZ   ARG A 328      12.177  40.002  54.674  1.00 20.63      A  C
ATOM   2220  NH1  ARG A 328      12.951  38.925  54.654  1.00 18.03      A  N
ATOM   2221  NH2  ARG A 328      11.706  40.456  55.823  1.00 20.79      A  N
ATOM   2222  C    ARG A 328      11.138  40.009  47.381  1.00 24.96      A  C
ATOM   2223  O    ARG A 328      10.677  38.933  47.061  1.00 26.89      A  O
ATOM   2224  N    LEU A 329      11.957  40.696  46.604  1.00 23.72      A  N
ATOM   2225  CA   LEU A 329      12.387  40.181  45.319  1.00 22.62      A  C
ATOM   2226  CB   LEU A 329      13.236  41.224  44.607  1.00 22.13      A  C
ATOM   2227  CG   LEU A 329      12.734  41.968  43.378  1.00 23.10      A  C
ATOM   2228  CD1  LEU A 329      11.279  42.346  43.497  1.00 24.14      A  C
ATOM   2229  CD2  LEU A 329      13.615  43.197  43.213  1.00 23.03      A  C
```

FIG. 5-38

```
ATOM   2230  C    LEU A 329      13.240  38.953  45.553  1.00 22.27           A  C
ATOM   2231  O    LEU A 329      13.847  38.805  46.616  1.00 19.94           A  O
ATOM   2232  N    THR A 330      13.282  38.072  44.561  1.00 21.28           A  N
ATOM   2233  CA   THR A 330      14.124  36.897  44.667  1.00 22.23           A  C
ATOM   2234  CB   THR A 330      13.608  35.714  43.838  1.00 23.51           A  C
ATOM   2235  OG1  THR A 330      13.637  36.051  42.448  1.00 24.62           A  O
ATOM   2236  CG2  THR A 330      12.181  35.351  44.252  1.00 24.27           A  C
ATOM   2237  C    THR A 330      15.474  37.336  44.114  1.00 22.58           A  C
ATOM   2238  O    THR A 330      15.557  38.316  43.393  1.00 22.85           A  O
ATOM   2239  N    PRO A 331      16.553  36.633  44.476  1.00 23.47           A  N
ATOM   2240  CD   PRO A 331      16.679  35.568  45.484  1.00 21.96           A  C
ATOM   2241  CA   PRO A 331      17.864  37.020  43.959  1.00 23.24           A  C
ATOM   2242  CB   PRO A 331      18.765  35.897  44.454  1.00 23.79           A  C
ATOM   2243  CG   PRO A 331      18.156  35.579  45.783  1.00 22.46           A  C
ATOM   2244  C    PRO A 331      17.852  37.135  42.428  1.00 23.13           A  C
ATOM   2245  O    PRO A 331      18.316  38.123  41.885  1.00 22.39           A  O
ATOM   2246  N    LEU A 332      17.308  36.131  41.738  1.00 24.17           A  N
ATOM   2247  CA   LEU A 332      17.260  36.185  40.275  1.00 23.38           A  C
ATOM   2248  CB   LEU A 332      16.604  34.945  39.677  1.00 24.20           A  C
ATOM   2249  CG   LEU A 332      17.487  33.868  39.040  1.00 24.72           A  C
ATOM   2250  CD1  LEU A 332      16.587  32.990  38.178  1.00 24.97           A  C
ATOM   2251  CD2  LEU A 332      18.590  34.472  38.184  1.00 23.04           A  C
ATOM   2252  C    LEU A 332      16.486  37.401  39.800  1.00 24.53           A  C
ATOM   2253  O    LEU A 332      16.924  38.107  38.898  1.00 24.59           A  O
ATOM   2254  N    GLU A 333      15.320  37.630  40.399  1.00 25.02           A  N
ATOM   2255  CA   GLU A 333      14.499  38.782  40.035  1.00 24.40           A  C
ATOM   2256  CB   GLU A 333      13.221  38.823  40.880  1.00 24.55           A  C
ATOM   2257  CG   GLU A 333      12.193  37.765  40.491  1.00 24.74           A  C
ATOM   2258  CD   GLU A 333      11.093  37.596  41.530  1.00 27.07           A  C
ATOM   2259  OE1  GLU A 333      11.114  38.318  42.547  1.00 25.88           A  O
ATOM   2260  OE2  GLU A 333      10.208  36.733  41.335  1.00 29.21           A  O
ATOM   2261  C    GLU A 333      15.304  40.068  40.223  1.00 23.78           A  C
ATOM   2262  O    GLU A 333      15.290  40.944  39.360  1.00 22.76           A  O
ATOM   2263  N    ALA A 334      16.009  40.161  41.348  1.00 22.05           A  N
ATOM   2264  CA   ALA A 334      16.836  41.329  41.636  1.00 21.29           A  C
ATOM   2265  CB   ALA A 334      17.581  41.151  42.970  1.00 18.46           A  C
ATOM   2266  C    ALA A 334      17.831  41.512  40.492  1.00 20.08           A  C
ATOM   2267  O    ALA A 334      18.002  42.600  40.001  1.00 21.09           A  O
ATOM   2268  N    CYS A 335      18.474  40.423  40.082  1.00 19.66           A  N
ATOM   2269  CA   CYS A 335      19.433  40.465  38.992  1.00 21.00           A  C
ATOM   2270  CB   CYS A 335      19.952  39.063  38.677  1.00 21.69           A  C
ATOM   2271  SG   CYS A 335      21.350  38.518  39.685  1.00 21.88           A  S
ATOM   2272  C    CYS A 335      18.828  41.063  37.726  1.00 22.43           A  C
ATOM   2273  O    CYS A 335      19.531  41.686  36.952  1.00 22.19           A  O
ATOM   2274  N    ALA A 336      17.524  40.865  37.540  1.00 23.65           A  N
ATOM   2275  CA   ALA A 336      16.815  41.361  36.366  1.00 24.08           A  C
ATOM   2276  CB   ALA A 336      15.651  40.441  36.050  1.00 22.39           A  C
ATOM   2277  C    ALA A 336      16.304  42.790  36.526  1.00 24.92           A  C
ATOM   2278  O    ALA A 336      15.799  43.355  35.591  1.00 24.50           A  O
ATOM   2279  N    HIS A 337      16.443  43.363  37.719  1.00 25.99           A  N
ATOM   2280  CA   HIS A 337      15.967  44.723  37.972  1.00 25.61           A  C
ATOM   2281  CB   HIS A 337      16.251  45.132  39.424  1.00 25.29           A  C
ATOM   2282  CG   HIS A 337      15.482  46.336  39.875  1.00 25.53           A  C
ATOM   2283  CD2  HIS A 337      15.797  47.653  39.866  1.00 24.56           A  C
ATOM   2284  ND1  HIS A 337      14.210  46.254  40.401  1.00 26.12           A  N
ATOM   2285  CE1  HIS A 337      13.777  47.468  40.698  1.00 23.20           A  C
ATOM   2286  NE2  HIS A 337      14.721  48.334  40.383  1.00 23.05           A  N
ATOM   2287  C    HIS A 337      16.604  45.739  37.030  1.00 26.29           A  C
ATOM   2288  O    HIS A 337      17.750  45.596  36.644  1.00 26.04           A  O
ATOM   2289  N    SER A 338      15.849  46.775  36.680  1.00 27.22           A  N
```

FIG. 5-39

```
ATOM   2290  CA   SER A 338      16.345  47.794  35.762  1.00 28.25      A    C
ATOM   2291  CB   SER A 338      15.250  48.832  35.477  1.00 29.56      A    C
ATOM   2292  OG   SER A 338      15.004  49.634  36.618  1.00 34.72      A    O
ATOM   2293  C    SER A 338      17.604  48.491  36.272  1.00 27.07      A    C
ATOM   2294  O    SER A 338      18.355  49.042  35.484  1.00 27.12      A    O
ATOM   2295  N    PHE A 339      17.834  48.454  37.584  1.00 25.78      A    N
ATOM   2296  CA   PHE A 339      19.020  49.083  38.166  1.00 24.26      A    C
ATOM   2297  CB   PHE A 339      19.034  48.894  39.691  1.00 25.56      A    C
ATOM   2298  CG   PHE A 339      20.268  49.449  40.368  1.00 24.73      A    C
ATOM   2299  CD1  PHE A 339      20.611  50.790  40.229  1.00 24.19      A    C
ATOM   2300  CD2  PHE A 339      21.087  48.628  41.140  1.00 25.29      A    C
ATOM   2301  CE1  PHE A 339      21.751  51.306  40.847  1.00 23.85      A    C
ATOM   2302  CE2  PHE A 339      22.236  49.140  41.764  1.00 22.59      A    C
ATOM   2303  CZ   PHE A 339      22.563  50.477  41.615  1.00 22.17      A    C
ATOM   2304  C    PHE A 339      20.297  48.493  37.577  1.00 23.16      A    C
ATOM   2305  O    PHE A 339      21.330  49.144  37.554  1.00 22.05      A    O
ATOM   2306  N    PHE A 340      20.212  47.256  37.098  1.00 23.05      A    N
ATOM   2307  CA   PHE A 340      21.369  46.584  36.516  1.00 24.33      A    C
ATOM   2308  CB   PHE A 340      21.423  45.124  36.984  1.00 21.25      A    C
ATOM   2309  CG   PHE A 340      21.501  44.964  38.476  1.00 20.77      A    C
ATOM   2310  CD1  PHE A 340      22.608  45.428  39.185  1.00 20.07      A    C
ATOM   2311  CD2  PHE A 340      20.472  44.347  39.175  1.00 18.91      A    C
ATOM   2312  CE1  PHE A 340      22.688  45.278  40.567  1.00 19.80      A    C
ATOM   2313  CE2  PHE A 340      20.541  44.191  40.553  1.00 21.51      A    C
ATOM   2314  CZ   PHE A 340      21.659  44.662  41.253  1.00 21.21      A    C
ATOM   2315  C    PHE A 340      21.380  46.637  34.989  1.00 24.66      A    C
ATOM   2316  O    PHE A 340      22.153  45.894  34.361  1.00 26.20      A    O
ATOM   2317  N    ASP A 341      20.535  47.441  34.379  1.00 24.72      A    N
ATOM   2318  CA   ASP A 341      20.512  47.499  32.912  1.00 26.03      A    C
ATOM   2319  CB   ASP A 341      19.410  48.438  32.415  1.00 25.59      A    C
ATOM   2320  CG   ASP A 341      18.022  47.882  32.655  1.00 27.02      A    C
ATOM   2321  OD1  ASP A 341      17.887  46.664  32.901  1.00 27.88      A    O
ATOM   2322  OD2  ASP A 341      17.057  48.660  32.589  1.00 29.89      A    O
ATOM   2323  C    ASP A 341      21.854  47.916  32.312  1.00 25.52      A    C
ATOM   2324  O    ASP A 341      22.270  47.381  31.285  1.00 25.27      A    O
ATOM   2325  N    GLU A 342      22.531  48.856  32.966  1.00 24.57      A    N
ATOM   2326  CA   GLU A 342      23.820  49.332  32.487  1.00 26.48      A    C
ATOM   2327  CB   GLU A 342      24.394  50.358  33.456  1.00 27.29      A    C
ATOM   2328  CG   GLU A 342      25.388  51.307  32.811  1.00 31.64      A    C
ATOM   2329  CD   GLU A 342      26.154  52.139  33.824  1.00 32.83      A    C
ATOM   2330  OE1  GLU A 342      25.526  52.696  34.752  1.00 34.69      A    O
ATOM   2331  OE2  GLU A 342      27.390  52.241  33.682  1.00 34.17      A    O
ATOM   2332  C    GLU A 342      24.822  48.183  32.319  1.00 26.14      A    C
ATOM   2333  O    GLU A 342      25.624  48.182  31.397  1.00 25.00      A    O
ATOM   2334  N    LEU A 343      24.763  47.207  33.219  1.00 25.71      A    N
ATOM   2335  CA   LEU A 343      25.673  46.077  33.157  1.00 25.67      A    C
ATOM   2336  CB   LEU A 343      25.533  45.205  34.411  1.00 24.21      A    C
ATOM   2337  CG   LEU A 343      25.755  45.878  35.765  1.00 25.39      A    C
ATOM   2338  CD1  LEU A 343      25.643  44.884  36.873  1.00 21.34      A    C
ATOM   2339  CD2  LEU A 343      27.130  46.554  35.786  1.00 23.56      A    C
ATOM   2340  C    LEU A 343      25.389  45.229  31.931  1.00 24.73      A    C
ATOM   2341  O    LEU A 343      26.234  44.511  31.489  1.00 25.16      A    O
ATOM   2342  N    ARG A 344      24.176  45.320  31.399  1.00 26.15      A    N
ATOM   2343  CA   ARG A 344      23.806  44.538  30.223  1.00 28.53      A    C
ATOM   2344  CB   ARG A 344      22.325  44.149  30.297  1.00 27.72      A    C
ATOM   2345  CG   ARG A 344      22.046  43.012  31.281  1.00 26.01      A    C
ATOM   2346  CD   ARG A 344      20.563  42.668  31.344  1.00 25.58      A    C
ATOM   2347  NE   ARG A 344      19.802  43.619  32.149  1.00 26.26      A    N
ATOM   2348  CZ   ARG A 344      19.619  43.524  33.463  1.00 26.67      A    C
ATOM   2349  NH1  ARG A 344      20.143  42.509  34.138  1.00 24.77      A    N
```

FIG. 5-40

```
ATOM   2350  NH2 ARG A 344      18.911  44.451  34.104  1.00 26.42      A    N
ATOM   2351  C   ARG A 344      24.104  45.260  28.912  1.00 29.77      A    C
ATOM   2352  O   ARG A 344      24.013  44.682  27.848  1.00 29.60      A    O
ATOM   2353  N   ASP A 345      24.460  46.535  29.012  1.00 31.85      A    N
ATOM   2354  CA  ASP A 345      24.803  47.333  27.846  1.00 32.99      A    C
ATOM   2355  CB  ASP A 345      25.095  48.772  28.271  1.00 35.59      A    C
ATOM   2356  CG  ASP A 345      25.313  49.698  27.093  1.00 37.69      A    C
ATOM   2357  OD1 ASP A 345      26.188  49.397  26.245  1.00 37.99      A    O
ATOM   2358  OD2 ASP A 345      24.610  50.730  27.022  1.00 37.09      A    O
ATOM   2359  C   ASP A 345      26.058  46.700  27.256  1.00 33.00      A    C
ATOM   2360  O   ASP A 345      26.990  46.403  27.974  1.00 32.36      A    O
ATOM   2361  N   PRO A 346      26.082  46.479  25.933  1.00 33.50      A    N
ATOM   2362  CD  PRO A 346      25.039  46.802  24.945  1.00 33.43      A    C
ATOM   2363  CA  PRO A 346      27.249  45.874  25.283  1.00 33.90      A    C
ATOM   2364  CB  PRO A 346      26.762  45.653  23.854  1.00 34.78      A    C
ATOM   2365  CG  PRO A 346      25.825  46.812  23.649  1.00 34.54      A    C
ATOM   2366  C   PRO A 346      28.514  46.730  25.346  1.00 34.67      A    C
ATOM   2367  O   PRO A 346      29.612  46.201  25.305  1.00 34.73      A    O
ATOM   2368  N   ASN A 347      28.353  48.044  25.465  1.00 34.66      A    N
ATOM   2369  CA  ASN A 347      29.508  48.938  25.520  1.00 37.48      A    C
ATOM   2370  CB  ASN A 347      29.134  50.276  24.875  1.00 38.16      A    C
ATOM   2371  CG  ASN A 347      28.557  50.094  23.485  1.00 40.41      A    C
ATOM   2372  OD1 ASN A 347      27.454  50.604  23.170  1.00 39.94      A    O
ATOM   2373  ND2 ASN A 347      29.278  49.348  22.642  1.00 39.73      A    N
ATOM   2374  C   ASN A 347      30.089  49.173  26.911  1.00 37.25      A    C
ATOM   2375  O   ASN A 347      31.199  49.695  27.043  1.00 37.97      A    O
ATOM   2376  N   VAL A 348      29.357  48.768  27.944  1.00 37.04      A    N
ATOM   2377  CA  VAL A 348      29.818  48.981  29.309  1.00 36.37      A    C
ATOM   2378  CB  VAL A 348      28.824  48.397  30.344  1.00 34.79      A    C
ATOM   2379  CG1 VAL A 348      28.889  46.869  30.357  1.00 31.47      A    C
ATOM   2380  CG2 VAL A 348      29.126  48.974  31.721  1.00 33.15      A    C
ATOM   2381  C   VAL A 348      31.206  48.427  29.599  1.00 37.06      A    C
ATOM   2382  O   VAL A 348      31.543  47.316  29.225  1.00 37.25      A    O
ATOM   2383  N   LYS A 349      32.005  49.248  30.270  1.00 39.24      A    N
ATOM   2384  CA  LYS A 349      33.353  48.886  30.663  1.00 40.12      A    C
ATOM   2385  CB  LYS A 349      34.366  49.411  29.642  1.00 43.03      A    C
ATOM   2386  CG  LYS A 349      34.313  48.660  28.302  1.00 45.52      A    C
ATOM   2387  CD  LYS A 349      35.354  49.179  27.310  1.00 47.88      A    C
ATOM   2388  CE  LYS A 349      36.781  48.819  27.739  1.00 47.89      A    C
ATOM   2389  NZ  LYS A 349      37.807  49.359  26.774  1.00 47.26      A    N
ATOM   2390  C   LYS A 349      33.610  49.450  32.049  1.00 40.40      A    C
ATOM   2391  O   LYS A 349      32.809  50.206  32.560  1.00 39.36      A    O
ATOM   2392  N   LEU A 350      34.717  49.048  32.665  1.00 41.08      A    N
ATOM   2393  CA  LEU A 350      35.062  49.548  33.985  1.00 41.94      A    C
ATOM   2394  CB  LEU A 350      35.971  48.559  34.714  1.00 41.32      A    C
ATOM   2395  CG  LEU A 350      35.421  47.143  34.889  1.00 40.27      A    C
ATOM   2396  CD1 LEU A 350      36.355  46.348  35.757  1.00 40.05      A    C
ATOM   2397  CD2 LEU A 350      34.050  47.198  35.512  1.00 39.52      A    C
ATOM   2398  C   LEU A 350      35.790  50.871  33.802  1.00 43.68      A    C
ATOM   2399  O   LEU A 350      36.382  51.112  32.758  1.00 43.58      A    O
ATOM   2400  N   PRO A 351      35.719  51.763  34.804  1.00 45.55      A    N
ATOM   2401  CD  PRO A 351      35.186  51.594  36.165  1.00 45.78      A    C
ATOM   2402  CA  PRO A 351      36.423  53.043  34.664  1.00 46.61      A    C
ATOM   2403  CB  PRO A 351      36.233  53.697  36.035  1.00 46.23      A    C
ATOM   2404  CG  PRO A 351      36.082  52.516  36.960  1.00 46.86      A    C
ATOM   2405  C   PRO A 351      37.861  52.624  34.379  1.00 47.59      A    C
ATOM   2406  O   PRO A 351      38.558  53.212  33.576  1.00 47.54      A    O
ATOM   2407  N   ASN A 352      38.234  51.534  35.042  1.00 49.21      A    N
ATOM   2408  CA  ASN A 352      39.534  50.881  34.952  1.00 49.72      A    C
ATOM   2409  CB  ASN A 352      39.385  49.481  35.533  1.00 51.32      A    C
```

FIG. 5-41

```
ATOM   2410  CG   ASN A 352      40.692  48.769  35.675  1.00 53.22      A    C
ATOM   2411  OD1  ASN A 352      41.591  48.906  34.824  1.00 54.71      A    O
ATOM   2412  ND2  ASN A 352      40.819  47.979  36.743  1.00 53.01      A    N
ATOM   2413  C    ASN A 352      40.000  50.779  33.498  1.00 50.01      A    C
ATOM   2414  O    ASN A 352      41.204  50.717  33.217  1.00 50.18      A    O
ATOM   2415  N    GLY A 353      39.037  50.757  32.579  1.00 49.52      A    N
ATOM   2416  CA   GLY A 353      39.352  50.634  31.170  1.00 47.60      A    C
ATOM   2417  C    GLY A 353      39.147  49.194  30.712  1.00 47.40      A    C
ATOM   2418  O    GLY A 353      38.792  48.927  29.541  1.00 46.87      A    O
ATOM   2419  N    ARG A 354      39.362  48.260  31.635  1.00 45.39      A    N
ATOM   2420  CA   ARG A 354      39.229  46.834  31.350  1.00 44.99      A    C
ATOM   2421  CB   ARG A 354      39.793  46.004  32.527  1.00 46.73      A    C
ATOM   2422  CG   ARG A 354      41.145  46.495  33.084  1.00 48.43      A    C
ATOM   2423  CD   ARG A 354      41.635  45.679  34.302  1.00 50.79      A    C
ATOM   2424  NE   ARG A 354      41.984  44.295  33.960  1.00 53.35      A    N
ATOM   2425  CZ   ARG A 354      42.438  43.387  34.830  1.00 54.46      A    C
ATOM   2426  NH1  ARG A 354      42.605  43.708  36.109  1.00 54.97      A    N
ATOM   2427  NH2  ARG A 354      42.718  42.148  34.423  1.00 53.27      A    N
ATOM   2428  C    ARG A 354      37.760  46.458  31.140  1.00 43.54      A    C
ATOM   2429  O    ARG A 354      36.842  47.265  31.394  1.00 42.89      A    O
ATOM   2430  N    ASP A 355      37.537  45.232  30.679  1.00 42.30      A    N
ATOM   2431  CA   ASP A 355      36.187  44.733  30.457  1.00 41.67      A    C
ATOM   2432  CB   ASP A 355      36.202  43.540  29.491  1.00 42.68      A    C
ATOM   2433  CG   ASP A 355      35.802  43.931  28.072  1.00 44.56      A    C
ATOM   2434  OD1  ASP A 355      34.811  43.365  27.555  1.00 44.63      A    O
ATOM   2435  OD2  ASP A 355      36.470  44.806  27.472  1.00 45.58      A    O
ATOM   2436  C    ASP A 355      35.557  44.309  31.784  1.00 40.59      A    C
ATOM   2437  O    ASP A 355      36.250  44.087  32.762  1.00 40.84      A    O
ATOM   2438  N    THR A 356      34.232  44.224  31.815  1.00 38.63      A    N
ATOM   2439  CA   THR A 356      33.545  43.796  33.021  1.00 36.65      A    C
ATOM   2440  CB   THR A 356      32.033  44.093  32.982  1.00 35.85      A    C
ATOM   2441  OG1  THR A 356      31.502  43.689  31.717  1.00 36.83      A    O
ATOM   2442  CG2  THR A 356      31.769  45.556  33.213  1.00 35.16      A    C
ATOM   2443  C    THR A 356      33.705  42.290  33.107  1.00 35.54      A    C
ATOM   2444  O    THR A 356      33.920  41.631  32.100  1.00 35.71      A    O
ATOM   2445  N    PRO A 357      33.612  41.729  34.319  1.00 34.54      A    N
ATOM   2446  CD   PRO A 357      33.466  42.346  35.649  1.00 32.89      A    C
ATOM   2447  CA   PRO A 357      33.755  40.279  34.427  1.00 33.29      A    C
ATOM   2448  CB   PRO A 357      33.832  40.048  35.931  1.00 33.35      A    C
ATOM   2449  CG   PRO A 357      33.015  41.173  36.486  1.00 32.84      A    C
ATOM   2450  C    PRO A 357      32.545  39.585  33.812  1.00 33.03      A    C
ATOM   2451  O    PRO A 357      31.642  40.231  33.278  1.00 31.81      A    O
ATOM   2452  N    ALA A 358      32.538  38.262  33.902  1.00 33.91      A    N
ATOM   2453  CA   ALA A 358      31.447  37.469  33.365  1.00 34.14      A    C
ATOM   2454  CB   ALA A 358      31.798  35.982  33.439  1.00 36.10      A    C
ATOM   2455  C    ALA A 358      30.195  37.769  34.190  1.00 32.98      A    C
ATOM   2456  O    ALA A 358      30.218  37.685  35.415  1.00 35.01      A    O
ATOM   2457  N    LEU A 359      29.107  38.120  33.517  1.00 31.67      A    N
ATOM   2458  CA   LEU A 359      27.874  38.458  34.209  1.00 29.19      A    C
ATOM   2459  CB   LEU A 359      27.596  39.958  34.069  1.00 28.75      A    C
ATOM   2460  CG   LEU A 359      28.626  40.946  34.616  1.00 29.69      A    C
ATOM   2461  CD1  LEU A 359      28.122  42.368  34.391  1.00 29.71      A    C
ATOM   2462  CD2  LEU A 359      28.855  40.697  36.104  1.00 27.24      A    C
ATOM   2463  C    LEU A 359      26.667  37.698  33.674  1.00 28.40      A    C
ATOM   2464  O    LEU A 359      25.607  37.662  34.312  1.00 25.60      A    O
ATOM   2465  N    PHE A 360      26.839  37.084  32.507  1.00 28.29      A    N
ATOM   2466  CA   PHE A 360      25.748  36.379  31.854  1.00 28.55      A    C
ATOM   2467  CB   PHE A 360      25.464  37.072  30.520  1.00 29.41      A    C
ATOM   2468  CG   PHE A 360      25.595  38.576  30.581  1.00 28.68      A    C
ATOM   2469  CD1  PHE A 360      24.714  39.334  31.342  1.00 26.61      A    C
```

FIG. 5-42

```
ATOM   2470  CD2 PHE A 360      26.624  39.229  29.906  1.00 28.94      A    C
ATOM   2471  CE1 PHE A 360      24.855  40.718  31.428  1.00 26.66      A    C
ATOM   2472  CE2 PHE A 360      26.770  40.616  29.989  1.00 26.78      A    C
ATOM   2473  CZ  PHE A 360      25.885  41.357  30.753  1.00 25.41      A    C
ATOM   2474  C   PHE A 360      25.896  34.873  31.631  1.00 28.98      A    C
ATOM   2475  O   PHE A 360      25.055  34.275  31.008  1.00 29.89      A    O
ATOM   2476  N   ASN A 361      26.955  34.269  32.156  1.00 29.63      A    N
ATOM   2477  CA  ASN A 361      27.177  32.833  31.987  1.00 30.30      A    C
ATOM   2478  CB  ASN A 361      28.656  32.510  32.227  1.00 31.70      A    C
ATOM   2479  CG  ASN A 361      29.218  33.235  33.437  1.00 35.98      A    C
ATOM   2480  OD1 ASN A 361      28.937  34.437  33.649  1.00 38.15      A    O
ATOM   2481  ND2 ASN A 361      30.023  32.528  34.240  1.00 37.88      A    N
ATOM   2482  C   ASN A 361      26.278  31.990  32.892  1.00 30.10      A    C
ATOM   2483  O   ASN A 361      26.738  31.078  33.567  1.00 29.39      A    O
ATOM   2484  N   PHE A 362      24.987  32.307  32.876  1.00 28.93      A    N
ATOM   2485  CA  PHE A 362      23.987  31.616  33.683  1.00 29.14      A    C
ATOM   2486  CB  PHE A 362      22.638  32.337  33.555  1.00 29.19      A    C
ATOM   2487  CG  PHE A 362      22.545  33.615  34.342  1.00 27.33      A    C
ATOM   2488  CD1 PHE A 362      22.416  33.584  35.726  1.00 27.59      A    C
ATOM   2489  CD2 PHE A 362      22.578  34.850  33.699  1.00 27.96      A    C
ATOM   2490  CE1 PHE A 362      22.321  34.765  36.459  1.00 26.49      A    C
ATOM   2491  CE2 PHE A 362      22.484  36.038  34.422  1.00 27.95      A    C
ATOM   2492  CZ  PHE A 362      22.354  35.996  35.806  1.00 26.91      A    C
ATOM   2493  C   PHE A 362      23.785  30.145  33.301  1.00 30.86      A    C
ATOM   2494  O   PHE A 362      23.663  29.810  32.118  1.00 31.63      A    O
ATOM   2495  N   THR A 363      23.746  29.274  34.303  1.00 30.86      A    N
ATOM   2496  CA  THR A 363      23.512  27.848  34.079  1.00 31.77      A    C
ATOM   2497  CB  THR A 363      24.246  26.989  35.106  1.00 30.63      A    C
ATOM   2498  OG1 THR A 363      23.716  27.262  36.408  1.00 31.03      A    O
ATOM   2499  CG2 THR A 363      25.737  27.283  35.084  1.00 27.78      A    C
ATOM   2500  C   THR A 363      22.015  27.634  34.286  1.00 32.75      A    C
ATOM   2501  O   THR A 363      21.330  28.518  34.807  1.00 34.68      A    O
ATOM   2502  N   THR A 364      21.510  26.466  33.896  1.00 33.39      A    N
ATOM   2503  CA  THR A 364      20.083  26.173  34.038  1.00 33.20      A    C
ATOM   2504  CB  THR A 364      19.691  24.892  33.217  1.00 34.61      A    C
ATOM   2505  OG1 THR A 364      19.450  23.788  34.096  1.00 36.53      A    O
ATOM   2506  CG2 THR A 364      20.810  24.518  32.264  1.00 32.07      A    C
ATOM   2507  C   THR A 364      19.776  26.010  35.530  1.00 33.05      A    C
ATOM   2508  O   THR A 364      18.692  26.330  35.990  1.00 33.48      A    O
ATOM   2509  N   GLN A 365      20.769  25.533  36.272  1.00 32.28      A    N
ATOM   2510  CA  GLN A 365      20.655  25.361  37.718  1.00 32.81      A    C
ATOM   2511  CB  GLN A 365      21.958  24.776  38.270  1.00 35.24      A    C
ATOM   2512  CG  GLN A 365      22.082  24.818  39.788  1.00 37.35      A    C
ATOM   2513  CD  GLN A 365      21.272  23.730  40.470  1.00 38.62      A    C
ATOM   2514  OE1 GLN A 365      20.876  23.874  41.607  1.00 38.48      A    O
ATOM   2515  NE2 GLN A 365      21.040  22.627  39.764  1.00 38.95      A    N
ATOM   2516  C   GLN A 365      20.420  26.740  38.342  1.00 32.91      A    C
ATOM   2517  O   GLN A 365      19.573  26.899  39.224  1.00 32.67      A    O
ATOM   2518  N   GLU A 366      21.179  27.730  37.869  1.00 31.69      A    N
ATOM   2519  CA  GLU A 366      21.071  29.105  38.358  1.00 30.32      A    C
ATOM   2520  CB  GLU A 366      22.167  29.990  37.750  1.00 30.88      A    C
ATOM   2521  CG  GLU A 366      23.515  29.889  38.417  1.00 32.22      A    C
ATOM   2522  CD  GLU A 366      24.489  30.955  37.931  1.00 32.66      A    C
ATOM   2523  OE1 GLU A 366      24.253  32.152  38.202  1.00 30.99      A    O
ATOM   2524  OE2 GLU A 366      25.489  30.588  37.277  1.00 34.81      A    O
ATOM   2525  C   GLU A 366      19.724  29.764  38.059  1.00 29.25      A    C
ATOM   2526  O   GLU A 366      19.225  30.558  38.853  1.00 27.47      A    O
ATOM   2527  N   LEU A 367      19.152  29.435  36.903  1.00 29.63      A    N
ATOM   2528  CA  LEU A 367      17.877  30.007  36.481  1.00 28.50      A    C
ATOM   2529  CB  LEU A 367      17.878  30.196  34.962  1.00 28.97      A    C
```

FIG. 5-43

```
ATOM   2530  CG   LEU A 367      18.997  31.076  34.404  1.00 29.75      A    C
ATOM   2531  CD1  LEU A 367      19.244  30.745  32.938  1.00 28.31      A    C
ATOM   2532  CD2  LEU A 367      18.625  32.540  34.599  1.00 25.35      A    C
ATOM   2533  C    LEU A 367      16.661  29.162  36.861  1.00 28.17      A    C
ATOM   2534  O    LEU A 367      15.536  29.584  36.660  1.00 28.25      A    O
ATOM   2535  N    SER A 368      16.891  27.979  37.421  1.00 28.97      A    N
ATOM   2536  CA   SER A 368      15.784  27.095  37.763  1.00 29.89      A    C
ATOM   2537  CB   SER A 368      16.297  25.866  38.528  1.00 30.01      A    C
ATOM   2538  OG   SER A 368      16.938  26.205  39.743  1.00 32.56      A    O
ATOM   2539  C    SER A 368      14.602  27.728  38.501  1.00 30.57      A    C
ATOM   2540  O    SER A 368      13.482  27.306  38.317  1.00 31.09      A    O
ATOM   2541  N    SER A 369      14.845  28.758  39.303  1.00 30.70      A    N
ATOM   2542  CA   SER A 369      13.756  29.398  40.046  1.00 31.32      A    C
ATOM   2543  CB   SER A 369      14.324  30.382  41.082  1.00 29.95      A    C
ATOM   2544  OG   SER A 369      14.841  31.558  40.469  1.00 30.40      A    O
ATOM   2545  C    SER A 369      12.775  30.135  39.144  1.00 31.09      A    C
ATOM   2546  O    SER A 369      11.638  30.353  39.525  1.00 29.92      A    O
ATOM   2547  N    ASN A 370      13.225  30.512  37.950  1.00 31.56      A    N
ATOM   2548  CA   ASN A 370      12.374  31.248  37.013  1.00 31.80      A    C
ATOM   2549  CB   ASN A 370      12.136  32.653  37.563  1.00 31.57      A    C
ATOM   2550  CG   ASN A 370      10.889  33.296  37.009  1.00 32.92      A    C
ATOM   2551  OD1  ASN A 370      10.449  32.977  35.900  1.00 35.29      A    O
ATOM   2552  ND2  ASN A 370      10.313  34.221  37.774  1.00 32.07      A    N
ATOM   2553  C    ASN A 370      13.072  31.324  35.642  1.00 33.49      A    C
ATOM   2554  O    ASN A 370      13.471  32.391  35.207  1.00 34.24      A    O
ATOM   2555  N    PRO A 371      13.237  30.173  34.955  1.00 34.76      A    N
ATOM   2556  CD   PRO A 371      12.907  28.806  35.389  1.00 34.81      A    C
ATOM   2557  CA   PRO A 371      13.896  30.151  33.643  1.00 34.26      A    C
ATOM   2558  CB   PRO A 371      13.538  28.765  33.071  1.00 34.24      A    C
ATOM   2559  CG   PRO A 371      12.597  28.141  34.083  1.00 35.26      A    C
ATOM   2560  C    PRO A 371      13.598  31.301  32.682  1.00 34.41      A    C
ATOM   2561  O    PRO A 371      14.505  31.900  32.155  1.00 36.21      A    O
ATOM   2562  N    PRO A 372      12.316  31.623  32.459  1.00 33.69      A    N
ATOM   2563  CD   PRO A 372      11.135  30.956  33.033  1.00 33.28      A    C
ATOM   2564  CA   PRO A 372      11.918  32.711  31.554  1.00 32.81      A    C
ATOM   2565  CB   PRO A 372      10.420  32.827  31.809  1.00 33.43      A    C
ATOM   2566  CG   PRO A 372      10.032  31.404  32.111  1.00 33.66      A    C
ATOM   2567  C    PRO A 372      12.653  34.035  31.801  1.00 32.53      A    C
ATOM   2568  O    PRO A 372      12.723  34.876  30.912  1.00 32.11      A    O
ATOM   2569  N    LEU A 373      13.193  34.224  33.004  1.00 31.52      A    N
ATOM   2570  CA   LEU A 373      13.915  35.459  33.300  1.00 31.96      A    C
ATOM   2571  CB   LEU A 373      14.300  35.532  34.784  1.00 31.89      A    C
ATOM   2572  CG   LEU A 373      13.206  35.955  35.770  1.00 32.00      A    C
ATOM   2573  CD1  LEU A 373      13.776  35.943  37.190  1.00 31.19      A    C
ATOM   2574  CD2  LEU A 373      12.688  37.350  35.407  1.00 28.40      A    C
ATOM   2575  C    LEU A 373      15.155  35.591  32.433  1.00 32.08      A    C
ATOM   2576  O    LEU A 373      15.651  36.694  32.223  1.00 32.06      A    O
ATOM   2577  N    ALA A 374      15.639  34.460  31.924  1.00 33.21      A    N
ATOM   2578  CA   ALA A 374      16.816  34.434  31.056  1.00 34.19      A    C
ATOM   2579  CB   ALA A 374      17.031  33.032  30.504  1.00 33.39      A    C
ATOM   2580  C    ALA A 374      16.676  35.422  29.907  1.00 34.29      A    C
ATOM   2581  O    ALA A 374      17.668  35.891  29.373  1.00 34.36      A    O
ATOM   2582  N    THR A 375      15.435  35.739  29.543  1.00 35.43      A    N
ATOM   2583  CA   THR A 375      15.172  36.656  28.432  1.00 36.83      A    C
ATOM   2584  CB   THR A 375      13.683  36.587  27.986  1.00 38.00      A    C
ATOM   2585  OG1  THR A 375      12.848  37.204  28.980  1.00 38.00      A    O
ATOM   2586  CG2  THR A 375      13.247  35.122  27.798  1.00 37.91      A    C
ATOM   2587  C    THR A 375      15.491  38.090  28.814  1.00 36.46      A    C
ATOM   2588  O    THR A 375      15.233  38.998  28.061  1.00 36.82      A    O
ATOM   2589  N    ILE A 376      16.039  38.284  30.006  1.00 35.99      A    N
```

FIG. 5-44

```
ATOM   2590  CA   ILE A 376      16.406  39.621  30.457  1.00 34.98      A    C
ATOM   2591  CB   ILE A 376      15.506  40.089  31.622  1.00 35.89      A    C
ATOM   2592  CG2  ILE A 376      16.077  41.344  32.263  1.00 35.50      A    C
ATOM   2593  CG1  ILE A 376      14.089  40.352  31.118  1.00 36.27      A    C
ATOM   2594  CD1  ILE A 376      13.100  40.612  32.230  1.00 35.44      A    C
ATOM   2595  C    ILE A 376      17.837  39.560  30.944  1.00 34.64      A    C
ATOM   2596  O    ILE A 376      18.618  40.460  30.693  1.00 34.50      A    O
ATOM   2597  N    LEU A 377      18.154  38.467  31.633  1.00 33.68      A    N
ATOM   2598  CA   LEU A 377      19.475  38.228  32.187  1.00 32.69      A    C
ATOM   2599  CB   LEU A 377      19.425  36.990  33.074  1.00 32.34      A    C
ATOM   2600  CG   LEU A 377      18.455  37.147  34.250  1.00 32.26      A    C
ATOM   2601  CD1  LEU A 377      18.375  35.835  34.997  1.00 32.36      A    C
ATOM   2602  CD2  LEU A 377      18.922  38.275  35.181  1.00 31.05      A    C
ATOM   2603  C    LEU A 377      20.537  38.070  31.113  1.00 33.40      A    C
ATOM   2604  O    LEU A 377      21.646  38.558  31.264  1.00 34.81      A    O
ATOM   2605  N    ILE A 378      20.207  37.367  30.034  1.00 32.83      A    N
ATOM   2606  CA   ILE A 378      21.174  37.186  28.958  1.00 32.78      A    C
ATOM   2607  CB   ILE A 378      21.139  35.757  28.385  1.00 31.82      A    C
ATOM   2608  CG2  ILE A 378      22.228  35.591  27.364  1.00 32.60      A    C
ATOM   2609  CG1  ILE A 378      21.379  34.735  29.490  1.00 33.59      A    C
ATOM   2610  CD1  ILE A 378      20.187  34.489  30.363  1.00 36.15      A    C
ATOM   2611  C    ILE A 378      20.814  38.182  27.851  1.00 32.56      A    C
ATOM   2612  O    ILE A 378      19.839  38.011  27.146  1.00 32.66      A    O
ATOM   2613  N    PRO A 379      21.593  39.260  27.718  1.00 31.91      A    N
ATOM   2614  CD   PRO A 379      22.712  39.727  28.560  1.00 31.90      A    C
ATOM   2615  CA   PRO A 379      21.280  40.232  26.671  1.00 32.11      A    C
ATOM   2616  CB   PRO A 379      22.090  41.459  27.082  1.00 30.20      A    C
ATOM   2617  CG   PRO A 379      23.306  40.847  27.722  1.00 30.36      A    C
ATOM   2618  C    PRO A 379      21.620  39.730  25.267  1.00 32.65      A    C
ATOM   2619  O    PRO A 379      22.444  38.824  25.096  1.00 33.21      A    O
ATOM   2620  N    PRO A 380      20.976  40.308  24.244  1.00 32.59      A    N
ATOM   2621  CD   PRO A 380      19.941  41.357  24.311  1.00 32.34      A    C
ATOM   2622  CA   PRO A 380      21.220  39.908  22.858  1.00 32.94      A    C
ATOM   2623  CB   PRO A 380      20.637  41.074  22.069  1.00 32.83      A    C
ATOM   2624  CG   PRO A 380      19.414  41.400  22.866  1.00 34.46      A    C
ATOM   2625  C    PRO A 380      22.668  39.626  22.508  1.00 33.50      A    C
ATOM   2626  O    PRO A 380      22.966  38.553  22.006  1.00 34.93      A    O
ATOM   2627  N    HIS A 381      23.568  40.570  22.781  1.00 33.97      A    N
ATOM   2628  CA   HIS A 381      24.978  40.369  22.442  1.00 35.02      A    C
ATOM   2629  CB   HIS A 381      25.774  41.659  22.698  1.00 34.66      A    C
ATOM   2630  CG   HIS A 381      26.073  41.923  24.144  1.00 35.87      A    C
ATOM   2631  CD2  HIS A 381      25.494  42.756  25.039  1.00 35.39      A    C
ATOM   2632  ND1  HIS A 381      27.083  41.272  24.821  1.00 35.59      A    N
ATOM   2633  CE1  HIS A 381      27.114  41.697  26.073  1.00 35.58      A    C
ATOM   2634  NE2  HIS A 381      26.160  42.597  26.233  1.00 35.01      A    N
ATOM   2635  C    HIS A 381      25.589  39.191  23.188  1.00 36.21      A    C
ATOM   2636  O    HIS A 381      25.056  38.824  24.262  1.00 37.56      A    O
ATOM   2637  OXT  HIS A 381      26.598  38.652  22.683  1.00 37.26      A    O
TER    2638       HIS A 381                                              A
ATOM   2639  CB   VAL B  37      14.181  81.964  79.298  1.00 45.87      B    C
ATOM   2640  CG1  VAL B  37      13.322  81.636  80.518  1.00 46.03      B    C
ATOM   2641  CG2  VAL B  37      15.571  82.399  79.726  1.00 47.05      B    C
ATOM   2642  C    VAL B  37      12.914  80.144  78.170  1.00 43.89      B    C
ATOM   2643  O    VAL B  37      12.062  80.753  77.527  1.00 43.66      B    O
ATOM   2644  N    VAL B  37      14.982  81.089  77.109  1.00 45.22      B    N
ATOM   2645  CA   VAL B  37      14.303  80.737  78.393  1.00 45.09      B    C
ATOM   2646  N    THR B  38      12.693  78.955  78.725  1.00 42.23      B    N
ATOM   2647  CA   THR B  38      11.421  78.264  78.553  1.00 40.10      B    C
ATOM   2648  CB   THR B  38      11.644  76.858  77.958  1.00 40.16      B    C
ATOM   2649  OG1  THR B  38      12.425  76.963  76.762  1.00 39.95      B    O
```

FIG. 5-45

| | | | | | | | | | | | |
|---|---|---|---|---|---|---|---|---|---|---|---|
| ATOM | 2650 | CG2 | THR | B | 38 | 10.312 | 76.194 | 77.629 | 1.00 | 39.73 | B C |
| ATOM | 2651 | C | THR | B | 38 | 10.653 | 78.102 | 79.855 | 1.00 | 38.49 | B C |
| ATOM | 2652 | O | THR | B | 38 | 11.202 | 77.670 | 80.866 | 1.00 | 38.24 | B O |
| ATOM | 2653 | N | THR | B | 39 | 9.373 | 78.449 | 79.814 | 1.00 | 36.91 | B N |
| ATOM | 2654 | CA | THR | B | 39 | 8.520 | 78.324 | 80.985 | 1.00 | 36.56 | B C |
| ATOM | 2655 | CB | THR | B | 39 | 7.912 | 79.682 | 81.388 | 1.00 | 37.22 | B C |
| ATOM | 2656 | OG1 | THR | B | 39 | 8.969 | 80.595 | 81.718 | 1.00 | 37.58 | B O |
| ATOM | 2657 | CG2 | THR | B | 39 | 7.011 | 79.521 | 82.599 | 1.00 | 36.13 | B C |
| ATOM | 2658 | C | THR | B | 39 | 7.419 | 77.345 | 80.607 | 1.00 | 35.14 | B C |
| ATOM | 2659 | O | THR | B | 39 | 6.752 | 77.499 | 79.587 | 1.00 | 34.79 | B O |
| ATOM | 2660 | N | VAL | B | 40 | 7.252 | 76.323 | 81.432 | 1.00 | 33.44 | B N |
| ATOM | 2661 | CA | VAL | B | 40 | 6.253 | 75.306 | 81.176 | 1.00 | 32.53 | B C |
| ATOM | 2662 | CB | VAL | B | 40 | 6.939 | 74.009 | 80.642 | 1.00 | 32.52 | B C |
| ATOM | 2663 | CG1 | VAL | B | 40 | 7.724 | 73.320 | 81.758 | 1.00 | 29.12 | B C |
| ATOM | 2664 | CG2 | VAL | B | 40 | 5.910 | 73.078 | 80.050 | 1.00 | 33.55 | B C |
| ATOM | 2665 | C | VAL | B | 40 | 5.533 | 75.000 | 82.479 | 1.00 | 32.46 | B C |
| ATOM | 2666 | O | VAL | B | 40 | 6.010 | 75.362 | 83.537 | 1.00 | 32.96 | B O |
| ATOM | 2667 | N | VAL | B | 41 | 4.367 | 74.368 | 82.395 | 1.00 | 31.78 | B N |
| ATOM | 2668 | CA | VAL | B | 41 | 3.648 | 73.983 | 83.603 | 1.00 | 32.95 | B C |
| ATOM | 2669 | CB | VAL | B | 41 | 2.165 | 74.467 | 83.582 | 1.00 | 32.38 | B C |
| ATOM | 2670 | CG1 | VAL | B | 41 | 1.586 | 74.333 | 82.196 | 1.00 | 35.48 | B C |
| ATOM | 2671 | CG2 | VAL | B | 41 | 1.349 | 73.692 | 84.591 | 1.00 | 30.37 | B C |
| ATOM | 2672 | C | VAL | B | 41 | 3.771 | 72.464 | 83.656 | 1.00 | 33.05 | B C |
| ATOM | 2673 | O | VAL | B | 41 | 3.191 | 71.763 | 82.859 | 1.00 | 33.78 | B O |
| ATOM | 2674 | N | ALA | B | 42 | 4.567 | 71.981 | 84.604 | 1.00 | 33.16 | B N |
| ATOM | 2675 | CA | ALA | B | 42 | 4.841 | 70.554 | 84.739 | 1.00 | 33.30 | B C |
| ATOM | 2676 | CB | ALA | B | 42 | 6.352 | 70.336 | 84.688 | 1.00 | 31.60 | B C |
| ATOM | 2677 | C | ALA | B | 42 | 4.273 | 69.882 | 85.981 | 1.00 | 33.33 | B C |
| ATOM | 2678 | O | ALA | B | 42 | 3.987 | 70.528 | 86.979 | 1.00 | 33.60 | B O |
| ATOM | 2679 | N | THR | B | 43 | 4.145 | 68.560 | 85.898 | 1.00 | 33.17 | B N |
| ATOM | 2680 | CA | THR | B | 43 | 3.604 | 67.756 | 86.983 | 1.00 | 33.71 | B C |
| ATOM | 2681 | CB | THR | B | 43 | 2.650 | 66.680 | 86.442 | 1.00 | 32.89 | B C |
| ATOM | 2682 | OG1 | THR | B | 43 | 1.761 | 67.273 | 85.489 | 1.00 | 33.03 | B O |
| ATOM | 2683 | CG2 | THR | B | 43 | 1.842 | 66.076 | 87.570 | 1.00 | 32.03 | B C |
| ATOM | 2684 | C | THR | B | 43 | 4.745 | 67.071 | 87.727 | 1.00 | 34.19 | B C |
| ATOM | 2685 | O | THR | B | 43 | 5.598 | 66.428 | 87.115 | 1.00 | 33.92 | B O |
| ATOM | 2686 | N | PRO | B | 44 | 4.777 | 67.206 | 89.064 | 1.00 | 35.11 | B N |
| ATOM | 2687 | CD | PRO | B | 44 | 3.908 | 68.054 | 89.901 | 1.00 | 34.33 | B C |
| ATOM | 2688 | CA | PRO | B | 44 | 5.830 | 66.582 | 89.869 | 1.00 | 35.02 | B C |
| ATOM | 2689 | CB | PRO | B | 44 | 5.440 | 66.951 | 91.299 | 1.00 | 34.20 | B C |
| ATOM | 2690 | CG | PRO | B | 44 | 4.773 | 68.290 | 91.114 | 1.00 | 34.80 | B C |
| ATOM | 2691 | C | PRO | B | 44 | 5.904 | 65.076 | 89.652 | 1.00 | 35.32 | B C |
| ATOM | 2692 | O | PRO | B | 44 | 4.880 | 64.411 | 89.532 | 1.00 | 34.69 | B O |
| ATOM | 2693 | N | GLY | B | 45 | 7.131 | 64.559 | 89.598 | 1.00 | 37.74 | B N |
| ATOM | 2694 | CA | GLY | B | 45 | 7.356 | 63.138 | 89.397 | 1.00 | 40.39 | B C |
| ATOM | 2695 | C | GLY | B | 45 | 6.619 | 62.286 | 90.417 | 1.00 | 42.87 | B C |
| ATOM | 2696 | O | GLY | B | 45 | 5.884 | 61.358 | 90.051 | 1.00 | 42.92 | B O |
| ATOM | 2697 | N | ALA | B | 46 | 6.815 | 62.597 | 91.698 | 1.00 | 45.11 | B N |
| ATOM | 2698 | CA | ALA | B | 46 | 6.153 | 61.869 | 92.778 | 1.00 | 47.84 | B C |
| ATOM | 2699 | CB | ALA | B | 46 | 7.107 | 61.685 | 93.957 | 1.00 | 47.70 | B C |
| ATOM | 2700 | C | ALA | B | 46 | 4.908 | 62.636 | 93.226 | 1.00 | 49.45 | B C |
| ATOM | 2701 | O | ALA | B | 46 | 4.438 | 63.538 | 92.518 | 1.00 | 49.67 | B O |
| ATOM | 2702 | N | GLY | B | 47 | 4.377 | 62.270 | 94.394 | 1.00 | 50.91 | B N |
| ATOM | 2703 | CA | GLY | B | 47 | 3.193 | 62.937 | 94.926 | 1.00 | 51.56 | B C |
| ATOM | 2704 | C | GLY | B | 47 | 1.997 | 62.954 | 93.983 | 1.00 | 51.63 | B C |
| ATOM | 2705 | O | GLY | B | 47 | 2.040 | 62.347 | 92.899 | 1.00 | 51.16 | B O |
| ATOM | 2706 | N | PRO | B | 48 | 0.911 | 63.651 | 94.366 | 1.00 | 52.03 | B N |
| ATOM | 2707 | CD | PRO | B | 48 | 0.780 | 64.440 | 95.609 | 1.00 | 52.32 | B C |
| ATOM | 2708 | CA | PRO | B | 48 | -0.308 | 63.756 | 93.557 | 1.00 | 51.83 | B C |
| ATOM | 2709 | CB | PRO | B | 48 | -1.361 | 64.109 | 94.593 | 1.00 | 52.98 | B C |

FIG. 5-46

```
ATOM   2710  CG  PRO B  48      -0.600  65.098  95.455  1.00 52.84        B  C
ATOM   2711  C   PRO B  48      -0.135  64.860  92.514  1.00 50.88        B  C
ATOM   2712  O   PRO B  48       0.640  65.809  92.735  1.00 51.04        B  O
ATOM   2713  N   ASP B  49      -0.861  64.757  91.401  1.00 49.65        B  N
ATOM   2714  CA  ASP B  49      -0.765  65.744  90.323  1.00 49.14        B  C
ATOM   2715  CB  ASP B  49      -1.626  65.300  89.124  1.00 50.19        B  C
ATOM   2716  CG  ASP B  49      -1.165  63.958  88.518  1.00 52.24        B  C
ATOM   2717  OD1 ASP B  49      -1.738  63.537  87.480  1.00 52.15        B  O
ATOM   2718  OD2 ASP B  49      -0.234  63.320  89.069  1.00 52.77        B  O
ATOM   2719  C   ASP B  49      -1.098  67.183  90.706  1.00 47.67        B  C
ATOM   2720  O   ASP B  49      -2.241  67.605  90.633  1.00 47.17        B  O
ATOM   2721  N   ARG B  50      -0.058  67.922  91.084  1.00 46.45        B  N
ATOM   2722  CA  ARG B  50      -0.155  69.327  91.493  1.00 45.36        B  C
ATOM   2723  CB  ARG B  50       0.271  69.435  92.961  1.00 47.64        B  C
ATOM   2724  CG  ARG B  50      -0.550  70.387  93.819  1.00 52.01        B  C
ATOM   2725  CD  ARG B  50      -1.006  69.689  95.106  1.00 56.22        B  C
ATOM   2726  NE  ARG B  50      -1.931  68.591  94.808  1.00 58.58        B  N
ATOM   2727  CZ  ARG B  50      -3.220  68.756  94.500  1.00 60.24        B  C
ATOM   2728  NH1 ARG B  50      -3.743  69.982  94.459  1.00 59.12        B  N
ATOM   2729  NH2 ARG B  50      -3.979  67.695  94.208  1.00 60.37        B  N
ATOM   2730  C   ARG B  50       0.802  70.130  90.598  1.00 42.46        B  C
ATOM   2731  O   ARG B  50       1.892  70.478  91.011  1.00 41.22        B  O
ATOM   2732  N   PRO B  51       0.398  70.418  89.352  1.00 40.85        B  N
ATOM   2733  CD  PRO B  51      -0.714  69.803  88.604  1.00 40.77        B  C
ATOM   2734  CA  PRO B  51       1.263  71.180  88.446  1.00 40.21        B  C
ATOM   2735  CB  PRO B  51       0.447  71.237  87.156  1.00 40.07        B  C
ATOM   2736  CG  PRO B  51      -0.225  69.902  87.148  1.00 40.01        B  C
ATOM   2737  C   PRO B  51       1.752  72.538  88.896  1.00 39.51        B  C
ATOM   2738  O   PRO B  51       1.049  73.261  89.568  1.00 39.62        B  O
ATOM   2739  N   GLN B  52       2.989  72.851  88.523  1.00 38.55        B  N
ATOM   2740  CA  GLN B  52       3.594  74.134  88.844  1.00 39.09        B  C
ATOM   2741  CB  GLN B  52       4.478  74.050  90.090  1.00 38.77        B  C
ATOM   2742  CG  GLN B  52       5.359  72.826  90.164  1.00 40.53        B  C
ATOM   2743  CD  GLN B  52       6.040  72.697  91.514  1.00 40.09        B  C
ATOM   2744  OE1 GLN B  52       7.125  73.232  91.730  1.00 38.90        B  O
ATOM   2745  NE2 GLN B  52       5.388  71.994  92.438  1.00 39.28        B  N
ATOM   2746  C   GLN B  52       4.387  74.631  87.665  1.00 39.06        B  C
ATOM   2747  O   GLN B  52       4.726  73.874  86.754  1.00 40.34        B  O
ATOM   2748  N   GLU B  53       4.657  75.924  87.674  1.00 38.55        B  N
ATOM   2749  CA  GLU B  53       5.430  76.543  86.615  1.00 38.19        B  C
ATOM   2750  CB  GLU B  53       5.204  78.049  86.658  1.00 40.23        B  C
ATOM   2751  CG  GLU B  53       5.458  78.791  85.378  1.00 44.18        B  C
ATOM   2752  CD  GLU B  53       5.342  80.294  85.553  1.00 46.76        B  C
ATOM   2753  OE1 GLU B  53       6.137  80.842  86.348  1.00 46.88        B  O
ATOM   2754  OE2 GLU B  53       4.471  80.924  84.893  1.00 48.45        B  O
ATOM   2755  C   GLU B  53       6.892  76.226  86.847  1.00 37.85        B  C
ATOM   2756  O   GLU B  53       7.363  76.197  88.001  1.00 37.70        B  O
ATOM   2757  N   VAL B  54       7.604  75.957  85.757  1.00 36.95        B  N
ATOM   2758  CA  VAL B  54       9.022  75.641  85.831  1.00 35.93        B  C
ATOM   2759  CB  VAL B  54       9.266  74.125  85.793  1.00 36.09        B  C
ATOM   2760  CG1 VAL B  54      10.762  73.837  85.830  1.00 35.17        B  C
ATOM   2761  CG2 VAL B  54       8.575  73.473  86.988  1.00 33.64        B  C
ATOM   2762  C   VAL B  54       9.699  76.318  84.662  1.00 35.70        B  C
ATOM   2763  O   VAL B  54       9.257  76.190  83.525  1.00 35.35        B  O
ATOM   2764  N   SER B  55      10.748  77.079  84.964  1.00 35.94        B  N
ATOM   2765  CA  SER B  55      11.512  77.797  83.953  1.00 36.22        B  C
ATOM   2766  CB  SER B  55      11.528  79.295  84.263  1.00 37.61        B  C
ATOM   2767  OG  SER B  55      10.227  79.854  84.138  1.00 41.50        B  O
ATOM   2768  C   SER B  55      12.942  77.283  83.897  1.00 35.47        B  C
ATOM   2769  O   SER B  55      13.593  77.113  84.931  1.00 34.02        B  O
```

FIG. 5-47

```
ATOM   2770  N    TYR B  56      13.423  77.049  82.680  1.00 34.65           B  N
ATOM   2771  CA   TYR B  56      14.774  76.558  82.459  1.00 34.64           B  C
ATOM   2772  CB   TYR B  56      14.752  75.032  82.315  1.00 31.97           B  C
ATOM   2773  CG   TYR B  56      13.931  74.503  81.150  1.00 30.99           B  C
ATOM   2774  CD1  TYR B  56      14.435  74.516  79.850  1.00 30.26           B  C
ATOM   2775  CE1  TYR B  56      13.695  73.995  78.781  1.00 29.41           B  C
ATOM   2776  CD2  TYR B  56      12.659  73.962  81.353  1.00 29.02           B  C
ATOM   2777  CE2  TYR B  56      11.918  73.442  80.293  1.00 28.75           B  C
ATOM   2778  CZ   TYR B  56      12.442  73.463  79.016  1.00 28.31           B  C
ATOM   2779  OH   TYR B  56      11.715  72.944  77.977  1.00 28.95           B  O
ATOM   2780  C    TYR B  56      15.394  77.210  81.233  1.00 36.33           B  C
ATOM   2781  O    TYR B  56      14.689  77.652  80.329  1.00 36.12           B  O
ATOM   2782  N    THR B  57      16.722  77.265  81.212  1.00 38.39           B  N
ATOM   2783  CA   THR B  57      17.442  77.898  80.115  1.00 40.35           B  C
ATOM   2784  CB   THR B  57      17.645  79.387  80.455  1.00 40.96           B  C
ATOM   2785  OG1  THR B  57      18.300  80.057  79.371  1.00 42.01           B  O
ATOM   2786  CG2  THR B  57      18.449  79.522  81.740  1.00 39.97           B  C
ATOM   2787  C    THR B  57      18.785  77.191  79.891  1.00 40.83           B  C
ATOM   2788  O    THR B  57      19.117  76.248  80.606  1.00 42.14           B  O
ATOM   2789  N    ASP B  58      19.546  77.644  78.897  1.00 41.24           B  N
ATOM   2790  CA   ASP B  58      20.846  77.047  78.573  1.00 41.80           B  C
ATOM   2791  CB   ASP B  58      21.832  77.160  79.750  1.00 43.00           B  C
ATOM   2792  CG   ASP B  58      21.991  78.579  80.262  1.00 45.46           B  C
ATOM   2793  OD1  ASP B  58      21.918  79.534  79.450  1.00 46.44           B  O
ATOM   2794  OD2  ASP B  58      22.215  78.730  81.489  1.00 46.33           B  O
ATOM   2795  C    ASP B  58      20.657  75.572  78.253  1.00 41.14           B  C
ATOM   2796  O    ASP B  58      21.258  74.708  78.887  1.00 40.66           B  O
ATOM   2797  N    THR B  59      19.819  75.292  77.266  1.00 40.96           B  N
ATOM   2798  CA   THR B  59      19.539  73.921  76.875  1.00 41.42           B  C
ATOM   2799  CB   THR B  59      18.086  73.805  76.387  1.00 41.68           B  C
ATOM   2800  OG1  THR B  59      17.933  74.533  75.162  1.00 42.59           B  O
ATOM   2801  CG2  THR B  59      17.135  74.403  77.421  1.00 41.42           B  C
ATOM   2802  C    THR B  59      20.483  73.457  75.772  1.00 41.72           B  C
ATOM   2803  O    THR B  59      20.711  74.162  74.798  1.00 42.32           B  O
ATOM   2804  N    LYS B  60      21.040  72.266  75.939  1.00 41.97           B  N
ATOM   2805  CA   LYS B  60      21.945  71.713  74.942  1.00 42.41           B  C
ATOM   2806  CB   LYS B  60      23.399  72.022  75.319  1.00 43.13           B  C
ATOM   2807  CG   LYS B  60      23.771  71.600  76.735  1.00 44.49           B  C
ATOM   2808  CD   LYS B  60      25.227  71.927  77.058  1.00 45.77           B  C
ATOM   2809  CE   LYS B  60      25.538  73.416  76.849  1.00 46.79           B  C
ATOM   2810  NZ   LYS B  60      24.883  74.323  77.843  1.00 47.25           B  N
ATOM   2811  C    LYS B  60      21.730  70.211  74.881  1.00 41.48           B  C
ATOM   2812  O    LYS B  60      21.292  69.604  75.852  1.00 41.14           B  O
ATOM   2813  N    VAL B  61      22.020  69.622  73.729  1.00 40.90           B  N
ATOM   2814  CA   VAL B  61      21.866  68.183  73.557  1.00 40.39           B  C
ATOM   2815  CB   VAL B  61      21.902  67.789  72.078  1.00 39.66           B  C
ATOM   2816  CG1  VAL B  61      21.748  66.283  71.946  1.00 40.11           B  C
ATOM   2817  CG2  VAL B  61      20.804  68.514  71.326  1.00 39.16           B  C
ATOM   2818  C    VAL B  61      23.012  67.469  74.247  1.00 40.21           B  C
ATOM   2819  O    VAL B  61      24.129  67.948  74.222  1.00 39.99           B  O
ATOM   2820  N    ILE B  62      22.724  66.329  74.872  1.00 40.28           B  N
ATOM   2821  CA   ILE B  62      23.773  65.559  75.530  1.00 39.95           B  C
ATOM   2822  CB   ILE B  62      23.764  65.741  77.072  1.00 39.71           B  C
ATOM   2823  CG2  ILE B  62      24.058  67.196  77.418  1.00 39.47           B  C
ATOM   2824  CG1  ILE B  62      22.417  65.342  77.666  1.00 39.02           B  C
ATOM   2825  CD1  ILE B  62      22.411  65.421  79.181  1.00 37.18           B  C
ATOM   2826  C    ILE B  62      23.661  64.083  75.196  1.00 40.63           B  C
ATOM   2827  O    ILE B  62      24.600  63.295  75.448  1.00 41.36           B  O
ATOM   2828  N    GLY B  63      22.525  63.709  74.611  1.00 40.07           B  N
ATOM   2829  CA   GLY B  63      22.306  62.323  74.254  1.00 38.83           B  C
```

FIG. 5-48

| | | | | | | | | | | | |
|---|---|---|---|---|---|---|---|---|---|---|---|
| ATOM | 2830 | C | GLY | B | 63 | 21.210 | 62.119 | 73.225 | 1.00 | 39.22 | B C |
| ATOM | 2831 | O | GLY | B | 63 | 20.388 | 62.995 | 72.981 | 1.00 | 38.22 | B O |
| ATOM | 2832 | N | ASN | B | 64 | 21.207 | 60.935 | 72.625 | 1.00 | 40.15 | B N |
| ATOM | 2833 | CA | ASN | B | 64 | 20.215 | 60.585 | 71.622 | 1.00 | 40.36 | B C |
| ATOM | 2834 | CB | ASN | B | 64 | 20.879 | 60.498 | 70.249 | 1.00 | 42.53 | B C |
| ATOM | 2835 | CG | ASN | B | 64 | 19.954 | 60.933 | 69.150 | 1.00 | 46.72 | B C |
| ATOM | 2836 | OD1 | ASN | B | 64 | 18.820 | 60.456 | 69.063 | 1.00 | 50.94 | B O |
| ATOM | 2837 | ND2 | ASN | B | 64 | 20.417 | 61.851 | 68.303 | 1.00 | 48.26 | B N |
| ATOM | 2838 | C | ASN | B | 64 | 19.606 | 59.237 | 72.011 | 1.00 | 38.17 | B C |
| ATOM | 2839 | O | ASN | B | 64 | 20.119 | 58.574 | 72.875 | 1.00 | 37.75 | B O |
| ATOM | 2840 | N | GLY | B | 65 | 18.509 | 58.848 | 71.369 | 1.00 | 36.95 | B N |
| ATOM | 2841 | CA | GLY | B | 65 | 17.885 | 57.579 | 71.696 | 1.00 | 35.86 | B C |
| ATOM | 2842 | C | GLY | B | 65 | 16.640 | 57.348 | 70.858 | 1.00 | 36.18 | B C |
| ATOM | 2843 | O | GLY | B | 65 | 16.101 | 58.268 | 70.247 | 1.00 | 37.93 | B O |
| ATOM | 2844 | N | SER | B | 66 | 16.178 | 56.108 | 70.829 | 1.00 | 35.10 | B N |
| ATOM | 2845 | CA | SER | B | 66 | 14.988 | 55.749 | 70.069 | 1.00 | 34.94 | B C |
| ATOM | 2846 | CB | SER | B | 66 | 14.499 | 54.353 | 70.484 | 1.00 | 35.95 | B C |
| ATOM | 2847 | OG | SER | B | 66 | 15.055 | 53.333 | 69.679 | 1.00 | 35.94 | B O |
| ATOM | 2848 | C | SER | B | 66 | 13.820 | 56.721 | 70.263 | 1.00 | 34.71 | B C |
| ATOM | 2849 | O | SER | B | 66 | 13.272 | 56.839 | 71.368 | 1.00 | 34.39 | B O |
| ATOM | 2850 | N | PHE | B | 67 | 13.436 | 57.401 | 69.190 | 1.00 | 33.84 | B N |
| ATOM | 2851 | CA | PHE | B | 67 | 12.308 | 58.320 | 69.231 | 1.00 | 32.96 | B C |
| ATOM | 2852 | CB | PHE | B | 67 | 11.048 | 57.553 | 69.629 | 1.00 | 33.92 | B C |
| ATOM | 2853 | CG | PHE | B | 67 | 10.594 | 56.574 | 68.594 | 1.00 | 34.01 | B C |
| ATOM | 2854 | CD1 | PHE | B | 67 | 10.151 | 55.306 | 68.957 | 1.00 | 33.42 | B C |
| ATOM | 2855 | CD2 | PHE | B | 67 | 10.590 | 56.935 | 67.248 | 1.00 | 34.03 | B C |
| ATOM | 2856 | CE1 | PHE | B | 67 | 9.708 | 54.409 | 67.989 | 1.00 | 34.42 | B C |
| ATOM | 2857 | CE2 | PHE | B | 67 | 10.154 | 56.057 | 66.273 | 1.00 | 32.30 | B C |
| ATOM | 2858 | CZ | PHE | B | 67 | 9.709 | 54.790 | 66.639 | 1.00 | 33.72 | B C |
| ATOM | 2859 | C | PHE | B | 67 | 12.462 | 59.513 | 70.149 | 1.00 | 32.00 | B C |
| ATOM | 2860 | O | PHE | B | 67 | 11.473 | 60.083 | 70.572 | 1.00 | 31.80 | B O |
| ATOM | 2861 | N | GLY | B | 68 | 13.690 | 59.894 | 70.462 | 1.00 | 30.68 | B N |
| ATOM | 2862 | CA | GLY | B | 68 | 13.842 | 61.037 | 71.339 | 1.00 | 31.23 | B C |
| ATOM | 2863 | C | GLY | B | 68 | 15.241 | 61.572 | 71.516 | 1.00 | 30.46 | B C |
| ATOM | 2864 | O | GLY | B | 68 | 16.189 | 61.050 | 70.978 | 1.00 | 31.01 | B O |
| ATOM | 2865 | N | VAL | B | 69 | 15.341 | 62.629 | 72.312 | 1.00 | 29.66 | B N |
| ATOM | 2866 | CA | VAL | B | 69 | 16.606 | 63.277 | 72.579 | 1.00 | 27.83 | B C |
| ATOM | 2867 | CB | VAL | B | 69 | 16.748 | 64.554 | 71.717 | 1.00 | 28.08 | B C |
| ATOM | 2868 | CG1 | VAL | B | 69 | 18.135 | 65.154 | 71.887 | 1.00 | 25.91 | B C |
| ATOM | 2869 | CG2 | VAL | B | 69 | 16.467 | 64.228 | 70.259 | 1.00 | 26.53 | B C |
| ATOM | 2870 | C | VAL | B | 69 | 16.663 | 63.661 | 74.054 | 1.00 | 28.85 | B C |
| ATOM | 2871 | O | VAL | B | 69 | 15.633 | 63.803 | 74.716 | 1.00 | 26.81 | B O |
| ATOM | 2872 | N | VAL | B | 70 | 17.878 | 63.829 | 74.560 | 1.00 | 28.60 | B N |
| ATOM | 2873 | CA | VAL | B | 70 | 18.073 | 64.210 | 75.946 | 1.00 | 28.61 | B C |
| ATOM | 2874 | CB | VAL | B | 70 | 18.832 | 63.129 | 76.724 | 1.00 | 28.25 | B C |
| ATOM | 2875 | CG1 | VAL | B | 70 | 18.542 | 63.262 | 78.205 | 1.00 | 27.74 | B C |
| ATOM | 2876 | CG2 | VAL | B | 70 | 18.445 | 61.760 | 76.222 | 1.00 | 29.37 | B C |
| ATOM | 2877 | C | VAL | B | 70 | 18.893 | 65.490 | 75.963 | 1.00 | 29.77 | B C |
| ATOM | 2878 | O | VAL | B | 70 | 20.013 | 65.534 | 75.431 | 1.00 | 28.78 | B O |
| ATOM | 2879 | N | TYR | B | 71 | 18.326 | 66.535 | 76.558 | 1.00 | 30.50 | B N |
| ATOM | 2880 | CA | TYR | B | 71 | 19.006 | 67.819 | 76.648 | 1.00 | 31.25 | B C |
| ATOM | 2881 | CB | TYR | B | 71 | 18.087 | 68.968 | 76.220 | 1.00 | 31.70 | B C |
| ATOM | 2882 | CG | TYR | B | 71 | 17.411 | 68.801 | 74.879 | 1.00 | 33.21 | B C |
| ATOM | 2883 | CD1 | TYR | B | 71 | 16.358 | 67.905 | 74.715 | 1.00 | 32.74 | B C |
| ATOM | 2884 | CE1 | TYR | B | 71 | 15.722 | 67.761 | 73.491 | 1.00 | 33.81 | B C |
| ATOM | 2885 | CD2 | TYR | B | 71 | 17.811 | 69.554 | 73.780 | 1.00 | 33.50 | B C |
| ATOM | 2886 | CE2 | TYR | B | 71 | 17.182 | 69.418 | 72.549 | 1.00 | 33.71 | B C |
| ATOM | 2887 | CZ | TYR | B | 71 | 16.134 | 68.520 | 72.412 | 1.00 | 34.48 | B C |
| ATOM | 2888 | OH | TYR | B | 71 | 15.493 | 68.370 | 71.201 | 1.00 | 36.82 | B O |
| ATOM | 2889 | C | TYR | B | 71 | 19.400 | 68.060 | 78.089 | 1.00 | 31.39 | B C |

FIG. 5-49

```
ATOM   2890  O    TYR B  71      18.910  67.395  78.992  1.00 32.09      B  O
ATOM   2891  N    GLN B  72      20.309  69.003  78.297  1.00 30.90      B  N
ATOM   2892  CA   GLN B  72      20.699  69.371  79.647  1.00 30.66      B  C
ATOM   2893  CB   GLN B  72      22.209  69.461  79.800  1.00 30.09      B  C
ATOM   2894  CG   GLN B  72      22.616  69.902  81.191  1.00 30.34      B  C
ATOM   2895  CD   GLN B  72      24.071  70.306  81.278  1.00 31.51      B  C
ATOM   2896  OE1  GLN B  72      24.491  71.254  80.643  1.00 31.18      B  O
ATOM   2897  NE2  GLN B  72      24.843  69.579  82.077  1.00 32.22      B  N
ATOM   2898  C    GLN B  72      20.117  70.763  79.773  1.00 31.30      B  C
ATOM   2899  O    GLN B  72      20.010  71.468  78.773  1.00 30.92      B  O
ATOM   2900  N    ALA B  73      19.741  71.161  80.981  1.00 31.44      B  N
ATOM   2901  CA   ALA B  73      19.171  72.489  81.177  1.00 32.11      B  C
ATOM   2902  CB   ALA B  73      17.676  72.474  80.852  1.00 31.04      B  C
ATOM   2903  C    ALA B  73      19.391  72.952  82.605  1.00 33.46      B  C
ATOM   2904  O    ALA B  73      19.699  72.150  83.478  1.00 32.81      B  O
ATOM   2905  N    LYS B  74      19.228  74.256  82.828  1.00 35.22      B  N
ATOM   2906  CA   LYS B  74      19.407  74.847  84.150  1.00 35.87      B  C
ATOM   2907  CB   LYS B  74      20.454  75.976  84.098  1.00 37.42      B  C
ATOM   2908  CG   LYS B  74      21.090  76.331  85.455  1.00 38.63      B  C
ATOM   2909  CD   LYS B  74      21.909  77.628  85.403  1.00 40.43      B  C
ATOM   2910  CE   LYS B  74      20.992  78.874  85.369  1.00 43.61      B  C
ATOM   2911  NZ   LYS B  74      21.709  80.194  85.264  1.00 43.36      B  N
ATOM   2912  C    LYS B  74      18.070  75.416  84.623  1.00 36.31      B  C
ATOM   2913  O    LYS B  74      17.430  76.210  83.916  1.00 36.29      B  O
ATOM   2914  N    LEU B  75      17.638  74.993  85.806  1.00 36.45      B  N
ATOM   2915  CA   LEU B  75      16.392  75.485  86.370  1.00 37.19      B  C
ATOM   2916  CB   LEU B  75      16.022  74.665  87.604  1.00 35.56      B  C
ATOM   2917  CG   LEU B  75      15.801  73.173  87.337  1.00 34.79      B  C
ATOM   2918  CD1  LEU B  75      15.468  72.455  88.639  1.00 33.11      B  C
ATOM   2919  CD2  LEU B  75      14.679  72.997  86.316  1.00 32.99      B  C
ATOM   2920  C    LEU B  75      16.646  76.941  86.752  1.00 38.58      B  C
ATOM   2921  O    LEU B  75      17.580  77.236  87.505  1.00 39.12      B  O
ATOM   2922  N    CYS B  76      15.823  77.846  86.233  1.00 39.46      B  N
ATOM   2923  CA   CYS B  76      15.985  79.275  86.500  1.00 40.69      B  C
ATOM   2924  CB   CYS B  76      14.875  80.060  85.808  1.00 38.41      B  C
ATOM   2925  SG   CYS B  76      15.046  80.024  84.032  1.00 39.56      B  S
ATOM   2926  C    CYS B  76      16.071  79.710  87.962  1.00 42.06      B  C
ATOM   2927  O    CYS B  76      16.948  80.505  88.323  1.00 42.20      B  O
ATOM   2928  N    ASP B  77      15.183  79.202  88.808  1.00 43.56      B  N
ATOM   2929  CA   ASP B  77      15.207  79.607  90.209  1.00 45.52      B  C
ATOM   2930  CB   ASP B  77      13.868  79.273  90.897  1.00 47.95      B  C
ATOM   2931  CG   ASP B  77      13.495  77.797  90.794  1.00 49.88      B  C
ATOM   2932  OD1  ASP B  77      13.813  77.177  89.751  1.00 51.56      B  O
ATOM   2933  OD2  ASP B  77      12.866  77.260  91.744  1.00 50.61      B  O
ATOM   2934  C    ASP B  77      16.366  79.035  91.011  1.00 45.85      B  C
ATOM   2935  O    ASP B  77      17.146  79.793  91.598  1.00 47.71      B  O
ATOM   2936  N    SER B  78      16.492  77.710  91.040  1.00 44.95      B  N
ATOM   2937  CA   SER B  78      17.561  77.069  91.808  1.00 43.46      B  C
ATOM   2938  CB   SER B  78      17.155  75.644  92.192  1.00 43.80      B  C
ATOM   2939  OG   SER B  78      17.043  74.813  91.046  1.00 42.95      B  O
ATOM   2940  C    SER B  78      18.903  77.020  91.078  1.00 43.16      B  C
ATOM   2941  O    SER B  78      19.928  76.723  91.684  1.00 44.41      B  O
ATOM   2942  N    GLY B  79      18.900  77.308  89.782  1.00 41.71      B  N
ATOM   2943  CA   GLY B  79      20.142  77.260  89.032  1.00 41.11      B  C
ATOM   2944  C    GLY B  79      20.673  75.840  88.883  1.00 40.59      B  C
ATOM   2945  O    GLY B  79      21.739  75.631  88.335  1.00 40.52      B  O
ATOM   2946  N    GLU B  80      19.920  74.865  89.379  1.00 39.43      B  N
ATOM   2947  CA   GLU B  80      20.313  73.462  89.289  1.00 39.79      B  C
ATOM   2948  CB   GLU B  80      19.420  72.605  90.181  1.00 40.68      B  C
ATOM   2949  CG   GLU B  80      19.741  72.683  91.650  1.00 44.91      B  C
```

FIG. 5-50

```
ATOM   2950  CD   GLU B  80      18.612  72.142  92.503  1.00 46.94      B  C
ATOM   2951  OE1  GLU B  80      18.094  71.045  92.171  1.00 46.01      B  O
ATOM   2952  OE2  GLU B  80      18.255  72.816  93.505  1.00 48.33      B  O
ATOM   2953  C    GLU B  80      20.234  72.906  87.872  1.00 37.73      B  C
ATOM   2954  O    GLU B  80      19.337  73.270  87.093  1.00 37.55      B  O
ATOM   2955  N    LEU B  81      21.165  72.010  87.552  1.00 34.45      B  N
ATOM   2956  CA   LEU B  81      21.195  71.375  86.243  1.00 32.16      B  C
ATOM   2957  CB   LEU B  81      22.629  70.994  85.872  1.00 32.40      B  C
ATOM   2958  CG   LEU B  81      23.622  72.154  85.748  1.00 33.28      B  C
ATOM   2959  CD1  LEU B  81      25.048  71.618  85.757  1.00 32.03      B  C
ATOM   2960  CD2  LEU B  81      23.342  72.937  84.471  1.00 32.23      B  C
ATOM   2961  C    LEU B  81      20.314  70.123  86.249  1.00 30.49      B  C
ATOM   2962  O    LEU B  81      20.349  69.331  87.182  1.00 29.49      B  O
ATOM   2963  N    VAL B  82      19.519  69.970  85.194  1.00 28.84      B  N
ATOM   2964  CA   VAL B  82      18.624  68.833  85.038  1.00 26.86      B  C
ATOM   2965  CB   VAL B  82      17.144  69.219  85.249  1.00 27.13      B  C
ATOM   2966  CG1  VAL B  82      16.892  69.637  86.692  1.00 27.54      B  C
ATOM   2967  CG2  VAL B  82      16.773  70.338  84.287  1.00 27.24      B  C
ATOM   2968  C    VAL B  82      18.734  68.328  83.609  1.00 26.54      B  C
ATOM   2969  O    VAL B  82      19.213  69.030  82.724  1.00 26.19      B  O
ATOM   2970  N    ALA B  83      18.274  67.103  83.396  1.00 24.80      B  N
ATOM   2971  CA   ALA B  83      18.283  66.499  82.079  1.00 24.83      B  C
ATOM   2972  CB   ALA B  83      18.895  65.108  82.144  1.00 22.79      B  C
ATOM   2973  C    ALA B  83      16.829  66.410  81.650  1.00 25.03      B  C
ATOM   2974  O    ALA B  83      15.958  66.160  82.470  1.00 26.82      B  O
ATOM   2975  N    ILE B  84      16.569  66.633  80.369  1.00 24.30      B  N
ATOM   2976  CA   ILE B  84      15.207  66.551  79.866  1.00 24.79      B  C
ATOM   2977  CB   ILE B  84      14.705  67.921  79.332  1.00 24.79      B  C
ATOM   2978  CG2  ILE B  84      13.295  67.782  78.766  1.00 23.59      B  C
ATOM   2979  CG1  ILE B  84      14.724  68.954  80.460  1.00 23.42      B  C
ATOM   2980  CD1  ILE B  84      14.215  70.312  80.053  1.00 24.56      B  C
ATOM   2981  C    ILE B  84      15.151  65.528  78.746  1.00 24.67      B  C
ATOM   2982  O    ILE B  84      15.795  65.685  77.729  1.00 25.63      B  O
ATOM   2983  N    LYS B  85      14.377  64.471  78.959  1.00 24.66      B  N
ATOM   2984  CA   LYS B  85      14.237  63.423  77.962  1.00 24.96      B  C
ATOM   2985  CB   LYS B  85      14.244  62.053  78.638  1.00 23.28      B  C
ATOM   2986  CG   LYS B  85      14.175  60.884  77.675  1.00 21.99      B  C
ATOM   2987  CD   LYS B  85      14.436  59.565  78.391  1.00 20.16      B  C
ATOM   2988  CE   LYS B  85      14.304  58.402  77.447  1.00 19.31      B  C
ATOM   2989  NZ   LYS B  85      14.751  57.127  78.039  1.00 20.35      B  N
ATOM   2990  C    LYS B  85      12.933  63.654  77.209  1.00 26.55      B  C
ATOM   2991  O    LYS B  85      11.837  63.563  77.775  1.00 25.23      B  O
ATOM   2992  N    LYS B  86      13.075  63.955  75.923  1.00 27.62      B  N
ATOM   2993  CA   LYS B  86      11.948  64.244  75.051  1.00 28.89      B  C
ATOM   2994  CB   LYS B  86      12.239  65.534  74.284  1.00 28.86      B  C
ATOM   2995  CG   LYS B  86      11.039  66.192  73.631  1.00 31.54      B  C
ATOM   2996  CD   LYS B  86      11.464  67.509  73.009  1.00 31.29      B  C
ATOM   2997  CE   LYS B  86      10.275  68.319  72.534  1.00 33.43      B  C
ATOM   2998  NZ   LYS B  86      10.699  69.670  72.045  1.00 35.19      B  N
ATOM   2999  C    LYS B  86      11.695  63.108  74.066  1.00 29.90      B  C
ATOM   3000  O    LYS B  86      12.466  62.911  73.140  1.00 31.52      B  O
ATOM   3001  N    VAL B  87      10.619  62.355  74.281  1.00 30.70      B  N
ATOM   3002  CA   VAL B  87      10.275  61.266  73.380  1.00 31.49      B  C
ATOM   3003  CB   VAL B  87      10.234  59.887  74.094  1.00 31.38      B  C
ATOM   3004  CG1  VAL B  87      11.566  59.609  74.772  1.00 31.79      B  C
ATOM   3005  CG2  VAL B  87       9.091  59.839  75.095  1.00 30.40      B  C
ATOM   3006  C    VAL B  87       8.912  61.504  72.746  1.00 33.21      B  C
ATOM   3007  O    VAL B  87       8.030  62.136  73.325  1.00 32.82      B  O
ATOM   3008  N    LEU B  88       8.762  60.998  71.532  1.00 34.72      B  N
ATOM   3009  CA   LEU B  88       7.516  61.106  70.804  1.00 37.39      B  C
```

FIG. 5-51

```
ATOM   3010  CB   LEU B  88       7.678  60.463  69.434  1.00 37.72      B  C
ATOM   3011  CG   LEU B  88       6.399  60.346  68.617  1.00 37.64      B  C
ATOM   3012  CD1  LEU B  88       6.031  61.723  68.064  1.00 37.34      B  C
ATOM   3013  CD2  LEU B  88       6.618  59.331  67.495  1.00 39.26      B  C
ATOM   3014  C    LEU B  88       6.458  60.344  71.600  1.00 38.79      B  C
ATOM   3015  O    LEU B  88       6.735  59.261  72.117  1.00 38.51      B  O
ATOM   3016  N    GLN B  89       5.250  60.898  71.691  1.00 40.50      B  N
ATOM   3017  CA   GLN B  89       4.177  60.243  72.438  1.00 44.17      B  C
ATOM   3018  CB   GLN B  89       3.959  60.963  73.771  1.00 44.86      B  C
ATOM   3019  CG   GLN B  89       2.828  60.402  74.633  1.00 46.81      B  C
ATOM   3020  CD   GLN B  89       3.037  58.938  75.001  1.00 48.36      B  C
ATOM   3021  OE1  GLN B  89       4.168  58.423  74.964  1.00 48.42      B  O
ATOM   3022  NE2  GLN B  89       1.950  58.260  75.377  1.00 49.10      B  N
ATOM   3023  C    GLN B  89       2.861  60.227  71.672  1.00 46.16      B  C
ATOM   3024  O    GLN B  89       2.511  61.201  71.008  1.00 47.77      B  O
ATOM   3025  N    ASP B  90       2.133  59.121  71.758  1.00 47.82      B  N
ATOM   3026  CA   ASP B  90       0.836  59.048  71.096  1.00 50.10      B  C
ATOM   3027  CB   ASP B  90       0.833  57.991  69.991  1.00 52.08      B  C
ATOM   3028  CG   ASP B  90      -0.449  58.018  69.170  1.00 54.43      B  C
ATOM   3029  OD1  ASP B  90      -1.529  57.763  69.762  1.00 54.41      B  O
ATOM   3030  OD2  ASP B  90      -0.374  58.303  67.943  1.00 54.89      B  O
ATOM   3031  C    ASP B  90      -0.229  58.719  72.147  1.00 50.67      B  C
ATOM   3032  O    ASP B  90      -0.012  57.854  73.033  1.00 48.83      B  O
ATOM   3033  N    ALA B  91      -1.371  59.410  72.045  1.00 51.54      B  N
ATOM   3034  CA   ALA B  91      -2.492  59.245  72.979  1.00 51.47      B  C
ATOM   3035  CB   ALA B  91      -3.516  60.360  72.759  1.00 51.46      B  C
ATOM   3036  C    ALA B  91      -3.191  57.881  72.929  1.00 51.09      B  C
ATOM   3037  O    ALA B  91      -4.097  57.610  73.729  1.00 50.84      B  O
ATOM   3038  N    ALA B  92      -2.772  57.023  72.003  1.00 50.96      B  N
ATOM   3039  CA   ALA B  92      -3.366  55.695  71.887  1.00 50.64      B  C
ATOM   3040  CB   ALA B  92      -2.821  54.967  70.661  1.00 50.30      B  C
ATOM   3041  C    ALA B  92      -3.106  54.871  73.148  1.00 50.22      B  C
ATOM   3042  O    ALA B  92      -3.922  54.054  73.532  1.00 50.82      B  O
ATOM   3043  N    ALA B  93      -1.969  55.095  73.799  1.00 49.50      B  N
ATOM   3044  CA   ALA B  93      -1.665  54.340  75.010  1.00 48.41      B  C
ATOM   3045  CB   ALA B  93      -0.810  53.110  74.664  1.00 49.00      B  C
ATOM   3046  C    ALA B  93      -0.969  55.191  76.072  1.00 47.28      B  C
ATOM   3047  O    ALA B  93      -0.657  56.364  75.849  1.00 46.84      B  O
ATOM   3048  N    LYS B  94      -0.733  54.586  77.231  1.00 45.33      B  N
ATOM   3049  CA   LYS B  94      -0.084  55.265  78.349  1.00 43.20      B  C
ATOM   3050  CB   LYS B  94      -0.685  54.752  79.659  1.00 45.03      B  C
ATOM   3051  CG   LYS B  94      -0.206  55.481  80.896  1.00 48.73      B  C
ATOM   3052  CD   LYS B  94      -0.813  54.888  82.171  1.00 50.90      B  C
ATOM   3053  CE   LYS B  94      -2.270  55.344  82.373  1.00 52.71      B  C
ATOM   3054  NZ   LYS B  94      -2.781  54.980  83.737  1.00 53.37      B  N
ATOM   3055  C    LYS B  94       1.415  54.970  78.289  1.00 40.73      B  C
ATOM   3056  O    LYS B  94       1.804  53.832  78.099  1.00 40.73      B  O
ATOM   3057  N    ASN B  95       2.251  55.998  78.440  1.00 37.76      B  N
ATOM   3058  CA   ASN B  95       3.705  55.814  78.373  1.00 34.01      B  C
ATOM   3059  CB   ASN B  95       4.419  57.157  78.361  1.00 31.80      B  C
ATOM   3060  CG   ASN B  95       5.904  57.002  78.168  1.00 31.14      B  C
ATOM   3061  OD1  ASN B  95       6.606  56.530  79.060  1.00 29.75      B  O
ATOM   3062  ND2  ASN B  95       6.391  57.373  76.986  1.00 27.24      B  N
ATOM   3063  C    ASN B  95       4.214  54.973  79.530  1.00 31.59      B  C
ATOM   3064  O    ASN B  95       4.159  55.384  80.689  1.00 32.00      B  O
ATOM   3065  N    ARG B  96       4.721  53.793  79.204  1.00 29.01      B  N
ATOM   3066  CA   ARG B  96       5.221  52.885  80.219  1.00 27.71      B  C
ATOM   3067  CB   ARG B  96       5.584  51.540  79.602  1.00 28.48      B  C
ATOM   3068  CG   ARG B  96       5.576  50.417  80.619  1.00 32.19      B  C
ATOM   3069  CD   ARG B  96       6.533  49.309  80.248  1.00 34.58      B  C
```

FIG. 5-52

| | | | | | | | | | | | |
|---|---|---|---|---|---|---|---|---|---|---|---|
| ATOM | 3070 | NE | ARG | B | 96 | 6.256 | 48.687 | 78.957 | 1.00 | 39.97 | B | N |
| ATOM | 3071 | CZ | ARG | B | 96 | 5.214 | 47.895 | 78.697 | 1.00 | 42.25 | B | C |
| ATOM | 3072 | NH1 | ARG | B | 96 | 4.319 | 47.615 | 79.642 | 1.00 | 45.03 | B | N |
| ATOM | 3073 | NH2 | ARG | B | 96 | 5.079 | 47.355 | 77.493 | 1.00 | 41.46 | B | N |
| ATOM | 3074 | C | ARG | B | 96 | 6.417 | 53.443 | 80.998 | 1.00 | 27.16 | B | C |
| ATOM | 3075 | O | ARG | B | 96 | 6.463 | 53.341 | 82.217 | 1.00 | 26.17 | B | O |
| ATOM | 3076 | N | GLU | B | 97 | 7.375 | 54.041 | 80.295 | 1.00 | 24.68 | B | N |
| ATOM | 3077 | CA | GLU | B | 97 | 8.550 | 54.598 | 80.953 | 1.00 | 23.54 | B | C |
| ATOM | 3078 | CB | GLU | B | 97 | 9.456 | 55.287 | 79.927 | 1.00 | 21.38 | B | C |
| ATOM | 3079 | CG | GLU | B | 97 | 10.776 | 55.778 | 80.509 | 1.00 | 20.14 | B | C |
| ATOM | 3080 | CD | GLU | B | 97 | 11.763 | 56.260 | 79.454 | 1.00 | 17.80 | B | C |
| ATOM | 3081 | OE1 | GLU | B | 97 | 12.932 | 56.502 | 79.811 | 1.00 | 18.16 | B | O |
| ATOM | 3082 | OE2 | GLU | B | 97 | 11.379 | 56.402 | 78.277 | 1.00 | 19.14 | B | O |
| ATOM | 3083 | C | GLU | B | 97 | 8.125 | 55.599 | 82.031 | 1.00 | 22.96 | B | C |
| ATOM | 3084 | O | GLU | B | 97 | 8.625 | 55.568 | 83.140 | 1.00 | 22.16 | B | O |
| ATOM | 3085 | N | LEU | B | 98 | 7.198 | 56.487 | 81.690 | 1.00 | 23.57 | B | N |
| ATOM | 3086 | CA | LEU | B | 98 | 6.724 | 57.483 | 82.639 | 1.00 | 23.39 | B | C |
| ATOM | 3087 | CB | LEU | B | 98 | 5.718 | 58.431 | 81.973 | 1.00 | 24.66 | B | C |
| ATOM | 3088 | CG | LEU | B | 98 | 4.917 | 59.349 | 82.913 | 1.00 | 23.96 | B | C |
| ATOM | 3089 | CD1 | LEU | B | 98 | 5.857 | 60.302 | 83.634 | 1.00 | 23.87 | B | C |
| ATOM | 3090 | CD2 | LEU | B | 98 | 3.889 | 60.140 | 82.119 | 1.00 | 25.69 | B | C |
| ATOM | 3091 | C | LEU | B | 98 | 6.064 | 56.827 | 83.842 | 1.00 | 24.79 | B | C |
| ATOM | 3092 | O | LEU | B | 98 | 6.366 | 57.160 | 84.986 | 1.00 | 22.59 | B | O |
| ATOM | 3093 | N | GLN | B | 99 | 5.161 | 55.891 | 83.561 | 1.00 | 26.62 | B | N |
| ATOM | 3094 | CA | GLN | B | 99 | 4.443 | 55.177 | 84.604 | 1.00 | 28.24 | B | C |
| ATOM | 3095 | CB | GLN | B | 99 | 3.548 | 54.088 | 84.001 | 1.00 | 31.93 | B | C |
| ATOM | 3096 | CG | GLN | B | 99 | 2.838 | 53.246 | 85.050 | 1.00 | 38.20 | B | C |
| ATOM | 3097 | CD | GLN | B | 99 | 1.990 | 52.113 | 84.464 | 1.00 | 43.07 | B | C |
| ATOM | 3098 | OE1 | GLN | B | 99 | 1.349 | 51.333 | 85.220 | 1.00 | 43.76 | B | O |
| ATOM | 3099 | NE2 | GLN | B | 99 | 1.975 | 52.002 | 83.125 | 1.00 | 44.63 | B | N |
| ATOM | 3100 | C | GLN | B | 99 | 5.380 | 54.557 | 85.624 | 1.00 | 28.23 | B | C |
| ATOM | 3101 | O | GLN | B | 99 | 5.124 | 54.651 | 86.820 | 1.00 | 26.96 | B | O |
| ATOM | 3102 | N | ILE | B | 100 | 6.471 | 53.940 | 85.166 | 1.00 | 26.64 | B | N |
| ATOM | 3103 | CA | ILE | B | 100 | 7.375 | 53.313 | 86.117 | 1.00 | 26.42 | B | C |
| ATOM | 3104 | CB | ILE | B | 100 | 8.202 | 52.151 | 85.480 | 1.00 | 26.54 | B | C |
| ATOM | 3105 | CG2 | ILE | B | 100 | 7.632 | 51.759 | 84.141 | 1.00 | 26.76 | B | C |
| ATOM | 3106 | CG1 | ILE | B | 100 | 9.674 | 52.515 | 85.412 | 1.00 | 25.09 | B | C |
| ATOM | 3107 | CD1 | ILE | B | 100 | 10.502 | 51.618 | 86.280 | 1.00 | 26.99 | B | C |
| ATOM | 3108 | C | ILE | B | 100 | 8.281 | 54.299 | 86.859 | 1.00 | 25.59 | B | C |
| ATOM | 3109 | O | ILE | B | 100 | 8.558 | 54.100 | 88.017 | 1.00 | 25.70 | B | O |
| ATOM | 3110 | N | MET | B | 101 | 8.716 | 55.364 | 86.190 | 1.00 | 25.68 | B | N |
| ATOM | 3111 | CA | MET | B | 101 | 9.570 | 56.363 | 86.828 | 1.00 | 27.09 | B | C |
| ATOM | 3112 | CB | MET | B | 101 | 9.999 | 57.429 | 85.818 | 1.00 | 27.05 | B | C |
| ATOM | 3113 | CG | MET | B | 101 | 10.909 | 56.916 | 84.709 | 1.00 | 28.17 | B | C |
| ATOM | 3114 | SD | MET | B | 101 | 12.574 | 57.556 | 84.861 | 1.00 | 29.73 | B | S |
| ATOM | 3115 | CE | MET | B | 101 | 13.220 | 56.459 | 86.109 | 1.00 | 30.12 | B | C |
| ATOM | 3116 | C | MET | B | 101 | 8.802 | 57.031 | 87.971 | 1.00 | 27.58 | B | C |
| ATOM | 3117 | O | MET | B | 101 | 9.368 | 57.392 | 88.970 | 1.00 | 27.76 | B | O |
| ATOM | 3118 | N | ARG | B | 102 | 7.496 | 57.174 | 87.788 | 1.00 | 28.46 | B | N |
| ATOM | 3119 | CA | ARG | B | 102 | 6.632 | 57.793 | 88.779 | 1.00 | 30.62 | B | C |
| ATOM | 3120 | CB | ARG | B | 102 | 5.204 | 57.873 | 88.245 | 1.00 | 32.28 | B | C |
| ATOM | 3121 | CG | ARG | B | 102 | 5.026 | 58.886 | 87.125 | 1.00 | 35.24 | B | C |
| ATOM | 3122 | CD | ARG | B | 102 | 4.457 | 60.175 | 87.670 | 1.00 | 37.73 | B | C |
| ATOM | 3123 | NE | ARG | B | 102 | 3.054 | 60.331 | 87.311 | 1.00 | 39.04 | B | N |
| ATOM | 3124 | CZ | ARG | B | 102 | 2.212 | 61.155 | 87.924 | 1.00 | 39.47 | B | C |
| ATOM | 3125 | NH1 | ARG | B | 102 | 2.623 | 61.899 | 88.947 | 1.00 | 39.46 | B | N |
| ATOM | 3126 | NH2 | ARG | B | 102 | 0.962 | 61.253 | 87.493 | 1.00 | 40.13 | B | N |
| ATOM | 3127 | C | ARG | B | 102 | 6.635 | 57.059 | 90.113 | 1.00 | 30.20 | B | C |
| ATOM | 3128 | O | ARG | B | 102 | 6.551 | 57.686 | 91.144 | 1.00 | 29.54 | B | O |
| ATOM | 3129 | N | LYS | B | 103 | 6.734 | 55.735 | 90.095 | 1.00 | 29.63 | B | N |

FIG. 5-53

| | | | | | | | | | | | |
|---|---|---|---|---|---|---|---|---|---|---|---|
| ATOM | 3130 | CA | LYS | B | 103 | 6.730 | 55.004 | 91.353 | 1.00 | 32.48 | B C |
| ATOM | 3131 | CB | LYS | B | 103 | 5.818 | 53.774 | 91.271 | 1.00 | 34.00 | B C |
| ATOM | 3132 | CG | LYS | B | 103 | 6.233 | 52.732 | 90.272 | 1.00 | 38.09 | B C |
| ATOM | 3133 | CD | LYS | B | 103 | 5.146 | 51.667 | 90.099 | 1.00 | 40.56 | B C |
| ATOM | 3134 | CE | LYS | B | 103 | 3.822 | 52.272 | 89.621 | 1.00 | 42.60 | B C |
| ATOM | 3135 | NZ | LYS | B | 103 | 2.843 | 51.198 | 89.276 | 1.00 | 43.62 | B N |
| ATOM | 3136 | C | LYS | B | 103 | 8.115 | 54.601 | 91.859 | 1.00 | 31.82 | B C |
| ATOM | 3137 | O | LYS | B | 103 | 8.240 | 53.767 | 92.742 | 1.00 | 33.01 | B O |
| ATOM | 3138 | N | LEU | B | 104 | 9.156 | 55.214 | 91.308 | 1.00 | 30.75 | B N |
| ATOM | 3139 | CA | LEU | B | 104 | 10.514 | 54.898 | 91.734 | 1.00 | 28.25 | B C |
| ATOM | 3140 | CB | LEU | B | 104 | 11.412 | 54.665 | 90.511 | 1.00 | 27.60 | B C |
| ATOM | 3141 | CG | LEU | B | 104 | 11.609 | 53.237 | 89.993 | 1.00 | 30.03 | B C |
| ATOM | 3142 | CD1 | LEU | B | 104 | 10.285 | 52.504 | 89.910 | 1.00 | 27.85 | B C |
| ATOM | 3143 | CD2 | LEU | B | 104 | 12.292 | 53.293 | 88.620 | 1.00 | 30.19 | B C |
| ATOM | 3144 | C | LEU | B | 104 | 11.116 | 55.997 | 92.598 | 1.00 | 26.48 | B C |
| ATOM | 3145 | O | LEU | B | 104 | 11.058 | 57.142 | 92.259 | 1.00 | 24.83 | B O |
| ATOM | 3146 | N | ASP | B | 105 | 11.688 | 55.608 | 93.731 | 1.00 | 26.35 | B N |
| ATOM | 3147 | CA | ASP | B | 105 | 12.319 | 56.553 | 94.637 | 1.00 | 26.73 | B C |
| ATOM | 3148 | CB | ASP | B | 105 | 11.321 | 57.051 | 95.679 | 1.00 | 29.61 | B C |
| ATOM | 3149 | CG | ASP | B | 105 | 11.933 | 58.061 | 96.635 | 1.00 | 31.21 | B C |
| ATOM | 3150 | OD1 | ASP | B | 105 | 12.654 | 58.962 | 96.160 | 1.00 | 33.72 | B O |
| ATOM | 3151 | OD2 | ASP | B | 105 | 11.686 | 57.965 | 97.856 | 1.00 | 34.06 | B O |
| ATOM | 3152 | C | ASP | B | 105 | 13.474 | 55.844 | 95.327 | 1.00 | 25.93 | B C |
| ATOM | 3153 | O | ASP | B | 105 | 13.289 | 55.158 | 96.351 | 1.00 | 24.30 | B O |
| ATOM | 3154 | N | HIS | B | 106 | 14.664 | 56.008 | 94.753 | 1.00 | 25.02 | B N |
| ATOM | 3155 | CA | HIS | B | 106 | 15.871 | 55.382 | 95.277 | 1.00 | 23.21 | B C |
| ATOM | 3156 | CB | HIS | B | 106 | 16.022 | 53.977 | 94.678 | 1.00 | 21.26 | B C |
| ATOM | 3157 | CG | HIS | B | 106 | 17.083 | 53.150 | 95.328 | 1.00 | 21.90 | B C |
| ATOM | 3158 | CD2 | HIS | B | 106 | 17.005 | 52.198 | 96.291 | 1.00 | 21.79 | B C |
| ATOM | 3159 | ND1 | HIS | B | 106 | 18.418 | 53.263 | 95.012 | 1.00 | 21.85 | B N |
| ATOM | 3160 | CE1 | HIS | B | 106 | 19.118 | 52.419 | 95.752 | 1.00 | 22.43 | B C |
| ATOM | 3161 | NE2 | HIS | B | 106 | 18.281 | 51.764 | 96.535 | 1.00 | 23.54 | B N |
| ATOM | 3162 | C | HIS | B | 106 | 17.099 | 56.226 | 94.961 | 1.00 | 21.84 | B C |
| ATOM | 3163 | O | HIS | B | 106 | 17.198 | 56.788 | 93.903 | 1.00 | 19.76 | B O |
| ATOM | 3164 | N | CYS | B | 107 | 18.027 | 56.290 | 95.912 | 1.00 | 22.14 | B N |
| ATOM | 3165 | CA | CYS | B | 107 | 19.250 | 57.072 | 95.773 | 1.00 | 22.96 | B C |
| ATOM | 3166 | CB | CYS | B | 107 | 20.068 | 56.988 | 97.065 | 1.00 | 22.25 | B C |
| ATOM | 3167 | SG | CYS | B | 107 | 20.662 | 55.327 | 97.485 | 1.00 | 26.72 | B S |
| ATOM | 3168 | C | CYS | B | 107 | 20.126 | 56.646 | 94.596 | 1.00 | 22.77 | B C |
| ATOM | 3169 | O | CYS | B | 107 | 20.988 | 57.394 | 94.173 | 1.00 | 22.42 | B O |
| ATOM | 3170 | N | ASN | B | 108 | 19.888 | 55.447 | 94.072 | 1.00 | 21.75 | B N |
| ATOM | 3171 | CA | ASN | B | 108 | 20.669 | 54.935 | 92.957 | 1.00 | 20.80 | B C |
| ATOM | 3172 | CB | ASN | B | 108 | 21.220 | 53.546 | 93.317 | 1.00 | 20.59 | B C |
| ATOM | 3173 | CG | ASN | B | 108 | 22.385 | 53.613 | 94.304 | 1.00 | 21.06 | B C |
| ATOM | 3174 | OD1 | ASN | B | 108 | 22.389 | 52.943 | 95.314 | 1.00 | 21.00 | B O |
| ATOM | 3175 | ND2 | ASN | B | 108 | 23.380 | 54.427 | 93.988 | 1.00 | 20.95 | B N |
| ATOM | 3176 | C | ASN | B | 108 | 19.893 | 54.884 | 91.631 | 1.00 | 20.93 | B C |
| ATOM | 3177 | O | ASN | B | 108 | 20.231 | 54.120 | 90.732 | 1.00 | 20.68 | B O |
| ATOM | 3178 | N | ILE | B | 109 | 18.857 | 55.710 | 91.522 | 1.00 | 19.80 | B N |
| ATOM | 3179 | CA | ILE | B | 109 | 18.044 | 55.793 | 90.314 | 1.00 | 19.37 | B C |
| ATOM | 3180 | CB | ILE | B | 109 | 16.696 | 55.048 | 90.487 | 1.00 | 19.98 | B C |
| ATOM | 3181 | CG2 | ILE | B | 109 | 15.735 | 55.417 | 89.355 | 1.00 | 19.11 | B C |
| ATOM | 3182 | CG1 | ILE | B | 109 | 16.945 | 53.538 | 90.507 | 1.00 | 20.54 | B C |
| ATOM | 3183 | CD1 | ILE | B | 109 | 15.730 | 52.701 | 90.855 | 1.00 | 20.51 | B C |
| ATOM | 3184 | C | ILE | B | 109 | 17.781 | 57.266 | 89.997 | 1.00 | 20.47 | B C |
| ATOM | 3185 | O | ILE | B | 109 | 17.333 | 58.032 | 90.857 | 1.00 | 19.75 | B O |
| ATOM | 3186 | N | VAL | B | 110 | 18.076 | 57.668 | 88.767 | 1.00 | 19.92 | B N |
| ATOM | 3187 | CA | VAL | B | 110 | 17.866 | 59.050 | 88.377 | 1.00 | 21.91 | B C |
| ATOM | 3188 | CB | VAL | B | 110 | 18.193 | 59.264 | 86.874 | 1.00 | 21.51 | B C |
| ATOM | 3189 | CG1 | VAL | B | 110 | 17.296 | 58.415 | 86.004 | 1.00 | 19.89 | B C |

FIG. 5-54

```
ATOM   3190  CG2  VAL B 110      18.051  60.729  86.527  1.00 25.44      B    C
ATOM   3191  C    VAL B 110      16.431  59.470  88.701  1.00 21.92      B    C
ATOM   3192  O    VAL B 110      15.481  58.840  88.278  1.00 19.95      B    O
ATOM   3193  N    ARG B 111      16.307  60.541  89.481  1.00 23.46      B    N
ATOM   3194  CA   ARG B 111      15.006  61.042  89.913  1.00 25.61      B    C
ATOM   3195  CB   ARG B 111      15.159  61.924  91.164  1.00 26.91      B    C
ATOM   3196  CG   ARG B 111      13.854  62.627  91.579  1.00 33.08      B    C
ATOM   3197  CD   ARG B 111      13.879  63.229  93.002  1.00 36.93      B    C
ATOM   3198  NE   ARG B 111      14.380  64.606  93.052  1.00 42.45      B    N
ATOM   3199  CZ   ARG B 111      15.657  64.949  93.248  1.00 45.10      B    C
ATOM   3200  NH1  ARG B 111      16.589  64.011  93.413  1.00 44.65      B    N
ATOM   3201  NH2  ARG B 111      16.004  66.234  93.290  1.00 44.22      B    N
ATOM   3202  C    ARG B 111      14.196  61.803  88.875  1.00 25.18      B    C
ATOM   3203  O    ARG B 111      14.705  62.655  88.180  1.00 23.87      B    O
ATOM   3204  N    LEU B 112      12.915  61.466  88.790  1.00 25.93      B    N
ATOM   3205  CA   LEU B 112      12.005  62.144  87.879  1.00 26.23      B    C
ATOM   3206  CB   LEU B 112      10.857  61.212  87.473  1.00 24.02      B    C
ATOM   3207  CG   LEU B 112       9.840  61.848  86.512  1.00 23.47      B    C
ATOM   3208  CD1  LEU B 112      10.529  62.173  85.195  1.00 21.60      B    C
ATOM   3209  CD2  LEU B 112       8.655  60.924  86.293  1.00 20.41      B    C
ATOM   3210  C    LEU B 112      11.449  63.356  88.637  1.00 27.06      B    C
ATOM   3211  O    LEU B 112      10.547  63.222  89.440  1.00 27.48      B    O
ATOM   3212  N    ARG B 113      12.013  64.530  88.385  1.00 28.15      B    N
ATOM   3213  CA   ARG B 113      11.563  65.754  89.048  1.00 31.19      B    C
ATOM   3214  CB   ARG B 113      12.549  66.899  88.773  1.00 32.97      B    C
ATOM   3215  CG   ARG B 113      14.024  66.652  89.130  1.00 36.86      B    C
ATOM   3216  CD   ARG B 113      14.333  66.856  90.617  1.00 42.50      B    C
ATOM   3217  NE   ARG B 113      15.664  67.450  90.814  1.00 47.31      B    N
ATOM   3218  CZ   ARG B 113      15.970  68.713  90.507  1.00 48.14      B    C
ATOM   3219  NH1  ARG B 113      15.039  69.515  90.005  1.00 48.91      B    N
ATOM   3220  NH2  ARG B 113      17.208  69.171  90.668  1.00 48.41      B    N
ATOM   3221  C    ARG B 113      10.184  66.162  88.522  1.00 30.94      B    C
ATOM   3222  O    ARG B 113       9.255  66.355  89.277  1.00 30.37      B    O
ATOM   3223  N    TYR B 114      10.078  66.298  87.207  1.00 31.12      B    N
ATOM   3224  CA   TYR B 114       8.827  66.691  86.583  1.00 32.52      B    C
ATOM   3225  CB   TYR B 114       8.806  68.204  86.332  1.00 33.71      B    C
ATOM   3226  CG   TYR B 114       9.053  69.069  87.544  1.00 35.20      B    C
ATOM   3227  CD1  TYR B 114       8.098  69.188  88.553  1.00 35.80      B    C
ATOM   3228  CE1  TYR B 114       8.337  69.990  89.680  1.00 37.72      B    C
ATOM   3229  CD2  TYR B 114      10.251  69.766  87.683  1.00 35.01      B    C
ATOM   3230  CE2  TYR B 114      10.497  70.562  88.795  1.00 37.04      B    C
ATOM   3231  CZ   TYR B 114       9.543  70.670  89.789  1.00 36.93      B    C
ATOM   3232  OH   TYR B 114       9.813  71.457  90.886  1.00 39.07      B    O
ATOM   3233  C    TYR B 114       8.679  66.008  85.233  1.00 32.54      B    C
ATOM   3234  O    TYR B 114       9.616  65.390  84.715  1.00 33.29      B    O
ATOM   3235  N    PHE B 115       7.480  66.135  84.676  1.00 31.18      B    N
ATOM   3236  CA   PHE B 115       7.171  65.629  83.352  1.00 30.16      B    C
ATOM   3237  CB   PHE B 115       6.712  64.159  83.394  1.00 28.72      B    C
ATOM   3238  CG   PHE B 115       5.325  63.951  83.922  1.00 26.93      B    C
ATOM   3239  CD1  PHE B 115       4.224  64.013  83.073  1.00 27.95      B    C
ATOM   3240  CD2  PHE B 115       5.119  63.660  85.267  1.00 27.34      B    C
ATOM   3241  CE1  PHE B 115       2.938  63.787  83.555  1.00 26.30      B    C
ATOM   3242  CE2  PHE B 115       3.841  63.432  85.762  1.00 26.35      B    C
ATOM   3243  CZ   PHE B 115       2.747  63.493  84.905  1.00 26.95      B    C
ATOM   3244  C    PHE B 115       6.102  66.572  82.794  1.00 30.54      B    C
ATOM   3245  O    PHE B 115       5.292  67.133  83.551  1.00 30.66      B    O
ATOM   3246  N    PHE B 116       6.132  66.783  81.483  1.00 29.85      B    N
ATOM   3247  CA   PHE B 116       5.180  67.663  80.823  1.00 29.99      B    C
ATOM   3248  CB   PHE B 116       5.548  69.131  81.093  1.00 28.10      B    C
ATOM   3249  CG   PHE B 116       6.870  69.570  80.485  1.00 27.56      B    C
```

FIG. 5-55

```
ATOM   3250  CD1  PHE B 116      6.948  69.976  79.150  1.00 27.34      B  C
ATOM   3251  CD2  PHE B 116      8.035  69.584  81.254  1.00 26.63      B  C
ATOM   3252  CE1  PHE B 116      8.168  70.391  78.593  1.00 27.15      B  C
ATOM   3253  CE2  PHE B 116      9.258  69.995  80.709  1.00 25.61      B  C
ATOM   3254  CZ   PHE B 116      9.326  70.399  79.379  1.00 25.95      B  C
ATOM   3255  C    PHE B 116      5.172  67.395  79.321  1.00 31.02      B  C
ATOM   3256  O    PHE B 116      6.101  66.814  78.791  1.00 29.79      B  O
ATOM   3257  N    TYR B 117      4.115  67.833  78.647  1.00 31.65      B  N
ATOM   3258  CA   TYR B 117      3.997  67.629  77.213  1.00 32.90      B  C
ATOM   3259  CB   TYR B 117      2.601  67.121  76.881  1.00 32.86      B  C
ATOM   3260  CG   TYR B 117      2.269  65.859  77.638  1.00 33.06      B  C
ATOM   3261  CD1  TYR B 117      1.663  65.911  78.895  1.00 32.13      B  C
ATOM   3262  CE1  TYR B 117      1.408  64.742  79.621  1.00 33.48      B  C
ATOM   3263  CD2  TYR B 117      2.611  64.616  77.123  1.00 32.71      B  C
ATOM   3264  CE2  TYR B 117      2.361  63.448  77.833  1.00 33.12      B  C
ATOM   3265  CZ   TYR B 117      1.762  63.515  79.076  1.00 33.64      B  C
ATOM   3266  OH   TYR B 117      1.521  62.344  79.754  1.00 35.67      B  O
ATOM   3267  C    TYR B 117      4.287  68.915  76.446  1.00 33.98      B  C
ATOM   3268  O    TYR B 117      4.112  70.006  76.973  1.00 35.53      B  O
ATOM   3269  N    SER B 118      4.734  68.776  75.200  1.00 34.62      B  N
ATOM   3270  CA   SER B 118      5.047  69.927  74.355  1.00 35.91      B  C
ATOM   3271  CB   SER B 118      6.382  70.541  74.763  1.00 36.30      B  C
ATOM   3272  OG   SER B 118      7.445  69.644  74.482  1.00 36.08      B  O
ATOM   3273  C    SER B 118      5.146  69.529  72.891  1.00 37.26      B  C
ATOM   3274  O    SER B 118      5.026  68.360  72.545  1.00 36.84      B  O
ATOM   3275  N    SER B 119      5.375  70.517  72.034  1.00 39.40      B  N
ATOM   3276  CA   SER B 119      5.516  70.258  70.610  1.00 41.76      B  C
ATOM   3277  CB   SER B 119      5.294  71.539  69.808  1.00 43.05      B  C
ATOM   3278  OG   SER B 119      3.911  71.797  69.646  1.00 46.48      B  O
ATOM   3279  C    SER B 119      6.909  69.705  70.314  1.00 42.34      B  C
ATOM   3280  O    SER B 119      7.806  69.777  71.155  1.00 42.61      B  O
ATOM   3281  N    VAL B 126      2.685  65.135  69.551  1.00 35.13      B  N
ATOM   3282  CA   VAL B 126      2.963  65.550  70.922  1.00 35.05      B  C
ATOM   3283  CB   VAL B 126      1.722  65.367  71.846  1.00 35.66      B  C
ATOM   3284  CG1  VAL B 126      0.512  66.066  71.241  1.00 36.14      B  C
ATOM   3285  CG2  VAL B 126      1.441  63.891  72.071  1.00 36.17      B  C
ATOM   3286  C    VAL B 126      4.137  64.781  71.527  1.00 34.04      B  C
ATOM   3287  O    VAL B 126      4.367  63.600  71.214  1.00 34.58      B  O
ATOM   3288  N    TYR B 127      4.874  65.458  72.399  1.00 32.21      B  N
ATOM   3289  CA   TYR B 127      6.023  64.857  73.051  1.00 30.32      B  C
ATOM   3290  CB   TYR B 127      7.304  65.606  72.688  1.00 32.58      B  C
ATOM   3291  CG   TYR B 127      7.670  65.563  71.229  1.00 35.04      B  C
ATOM   3292  CD1  TYR B 127      7.235  66.554  70.351  1.00 36.90      B  C
ATOM   3293  CE1  TYR B 127      7.572  66.517  68.997  1.00 39.03      B  C
ATOM   3294  CD2  TYR B 127      8.450  64.528  70.723  1.00 36.75      B  C
ATOM   3295  CE2  TYR B 127      8.794  64.479  69.370  1.00 39.00      B  C
ATOM   3296  CZ   TYR B 127      8.355  65.477  68.517  1.00 39.19      B  C
ATOM   3297  OH   TYR B 127      8.719  65.443  67.192  1.00 38.94      B  O
ATOM   3298  C    TYR B 127      5.910  64.837  74.563  1.00 28.75      B  C
ATOM   3299  O    TYR B 127      5.327  65.723  75.172  1.00 27.27      B  O
ATOM   3300  N    LEU B 128      6.492  63.802  75.150  1.00 26.92      B  N
ATOM   3301  CA   LEU B 128      6.529  63.639  76.584  1.00 25.28      B  C
ATOM   3302  CB   LEU B 128      6.360  62.170  76.950  1.00 25.56      B  C
ATOM   3303  CG   LEU B 128      6.621  61.824  78.414  1.00 24.73      B  C
ATOM   3304  CD1  LEU B 128      5.696  62.630  79.319  1.00 22.95      B  C
ATOM   3305  CD2  LEU B 128      6.433  60.328  78.611  1.00 23.83      B  C
ATOM   3306  C    LEU B 128      7.910  64.120  76.998  1.00 25.48      B  C
ATOM   3307  O    LEU B 128      8.909  63.716  76.416  1.00 24.97      B  O
ATOM   3308  N    ASN B 129      7.949  64.996  77.992  1.00 24.91      B  N
ATOM   3309  CA   ASN B 129      9.193  65.557  78.495  1.00 24.80      B  C
```

FIG. 5-56

```
ATOM   3310  CB  ASN B 129       9.138  67.087  78.458  1.00 25.13      B   C
ATOM   3311  CG  ASN B 129       9.192  67.641  77.053  1.00 25.63      B   C
ATOM   3312  OD1 ASN B 129      10.237  68.081  76.596  1.00 27.02      B   O
ATOM   3313  ND2 ASN B 129       8.060  67.614  76.357  1.00 25.06      B   N
ATOM   3314  C   ASN B 129       9.460  65.119  79.926  1.00 24.76      B   C
ATOM   3315  O   ASN B 129       8.735  65.478  80.821  1.00 25.89      B   O
ATOM   3316  N   LEU B 130      10.517  64.341  80.127  1.00 24.71      B   N
ATOM   3317  CA  LEU B 130      10.866  63.895  81.467  1.00 24.32      B   C
ATOM   3318  CB  LEU B 130      11.267  62.411  81.453  1.00 25.00      B   C
ATOM   3319  CG  LEU B 130      10.165  61.372  81.209  1.00 25.81      B   C
ATOM   3320  CD1 LEU B 130       9.715  61.428  79.777  1.00 29.93      B   C
ATOM   3321  CD2 LEU B 130      10.681  59.981  81.512  1.00 27.10      B   C
ATOM   3322  C   LEU B 130      12.014  64.750  82.011  1.00 23.56      B   C
ATOM   3323  O   LEU B 130      13.090  64.793  81.419  1.00 23.85      B   O
ATOM   3324  N   VAL B 131      11.771  65.452  83.116  1.00 23.09      B   N
ATOM   3325  CA  VAL B 131      12.816  66.279  83.722  1.00 23.23      B   C
ATOM   3326  CB  VAL B 131      12.268  67.580  84.345  1.00 23.20      B   C
ATOM   3327  CG1 VAL B 131      13.420  68.397  84.909  1.00 21.29      B   C
ATOM   3328  CG2 VAL B 131      11.528  68.394  83.295  1.00 21.92      B   C
ATOM   3329  C   VAL B 131      13.470  65.453  84.813  1.00 23.26      B   C
ATOM   3330  O   VAL B 131      12.906  65.239  85.880  1.00 24.05      B   O
ATOM   3331  N   LEU B 132      14.675  64.993  84.526  1.00 23.07      B   N
ATOM   3332  CA  LEU B 132      15.410  64.146  85.444  1.00 21.73      B   C
ATOM   3333  CB  LEU B 132      15.844  62.889  84.697  1.00 21.89      B   C
ATOM   3334  CG  LEU B 132      14.723  62.227  83.888  1.00 20.35      B   C
ATOM   3335  CD1 LEU B 132      15.295  61.473  82.704  1.00 21.52      B   C
ATOM   3336  CD2 LEU B 132      13.924  61.314  84.801  1.00 19.23      B   C
ATOM   3337  C   LEU B 132      16.635  64.840  85.996  1.00 22.45      B   C
ATOM   3338  O   LEU B 132      17.071  65.868  85.483  1.00 21.95      B   O
ATOM   3339  N   ASP B 133      17.190  64.260  87.051  1.00 22.31      B   N
ATOM   3340  CA  ASP B 133      18.400  64.801  87.636  1.00 24.14      B   C
ATOM   3341  CB  ASP B 133      18.805  64.000  88.871  1.00 25.74      B   C
ATOM   3342  CG  ASP B 133      18.061  64.426  90.120  1.00 28.64      B   C
ATOM   3343  OD1 ASP B 133      18.139  63.674  91.119  1.00 30.83      B   O
ATOM   3344  OD2 ASP B 133      17.416  65.507  90.115  1.00 28.19      B   O
ATOM   3345  C   ASP B 133      19.486  64.663  86.578  1.00 24.57      B   C
ATOM   3346  O   ASP B 133      19.467  63.724  85.781  1.00 24.25      B   O
ATOM   3347  N   TYR B 134      20.414  65.611  86.558  1.00 25.18      B   N
ATOM   3348  CA  TYR B 134      21.516  65.558  85.617  1.00 25.17      B   C
ATOM   3349  CB  TYR B 134      21.910  66.954  85.133  1.00 25.49      B   C
ATOM   3350  CG  TYR B 134      23.196  66.940  84.329  1.00 26.49      B   C
ATOM   3351  CD1 TYR B 134      23.212  66.453  83.023  1.00 27.70      B   C
ATOM   3352  CE1 TYR B 134      24.395  66.358  82.297  1.00 27.11      B   C
ATOM   3353  CD2 TYR B 134      24.407  67.337  84.898  1.00 25.93      B   C
ATOM   3354  CE2 TYR B 134      25.601  67.245  84.178  1.00 27.67      B   C
ATOM   3355  CZ  TYR B 134      25.583  66.752  82.881  1.00 27.14      B   C
ATOM   3356  OH  TYR B 134      26.745  66.646  82.161  1.00 28.84      B   O
ATOM   3357  C   TYR B 134      22.703  64.940  86.337  1.00 25.04      B   C
ATOM   3358  O   TYR B 134      22.980  65.270  87.479  1.00 24.34      B   O
ATOM   3359  N   VAL B 135      23.387  64.029  85.663  1.00 24.40      B   N
ATOM   3360  CA  VAL B 135      24.559  63.390  86.234  1.00 24.60      B   C
ATOM   3361  CB  VAL B 135      24.339  61.871  86.375  1.00 24.14      B   C
ATOM   3362  CG1 VAL B 135      25.470  61.241  87.175  1.00 22.36      B   C
ATOM   3363  CG2 VAL B 135      23.011  61.623  87.069  1.00 22.74      B   C
ATOM   3364  C   VAL B 135      25.689  63.719  85.254  1.00 25.16      B   C
ATOM   3365  O   VAL B 135      25.536  63.573  84.048  1.00 25.65      B   O
ATOM   3366  N   PRO B 136      26.831  64.188  85.769  1.00 25.69      B   N
ATOM   3367  CD  PRO B 136      27.146  64.266  87.208  1.00 26.83      B   C
ATOM   3368  CA  PRO B 136      27.990  64.563  84.952  1.00 26.29      B   C
ATOM   3369  CB  PRO B 136      28.961  65.136  85.980  1.00 26.41      B   C
```

FIG. 5-57

| ATOM | 3370 | CG | PRO | B | 136 | 28.660 | 64.319 | 87.209 | 1.00 | 28.38 | B | C |
|---|---|---|---|---|---|---|---|---|---|---|---|---|
| ATOM | 3371 | C | PRO | B | 136 | 28.650 | 63.515 | 84.058 | 1.00 | 27.47 | B | C |
| ATOM | 3372 | O | PRO | B | 136 | 29.102 | 63.833 | 82.973 | 1.00 | 27.21 | B | O |
| ATOM | 3373 | N | GLU | B | 137 | 28.710 | 62.264 | 84.502 | 1.00 | 28.50 | B | N |
| ATOM | 3374 | CA | GLU | B | 137 | 29.365 | 61.255 | 83.691 | 1.00 | 28.59 | B | C |
| ATOM | 3375 | CB | GLU | B | 137 | 30.797 | 61.048 | 84.200 | 1.00 | 30.35 | B | C |
| ATOM | 3376 | CG | GLU | B | 137 | 31.829 | 60.724 | 83.118 | 1.00 | 34.51 | B | C |
| ATOM | 3377 | CD | GLU | B | 137 | 32.493 | 61.955 | 82.525 | 1.00 | 36.01 | B | C |
| ATOM | 3378 | OE1 | GLU | B | 137 | 32.559 | 63.005 | 83.202 | 1.00 | 38.26 | B | O |
| ATOM | 3379 | OE2 | GLU | B | 137 | 32.978 | 61.865 | 81.383 | 1.00 | 39.63 | B | O |
| ATOM | 3380 | C | GLU | B | 137 | 28.613 | 59.927 | 83.684 | 1.00 | 28.74 | B | C |
| ATOM | 3381 | O | GLU | B | 137 | 27.544 | 59.804 | 84.263 | 1.00 | 29.50 | B | O |
| ATOM | 3382 | N | THR | B | 138 | 29.184 | 58.940 | 83.004 | 1.00 | 26.67 | B | N |
| ATOM | 3383 | CA | THR | B | 138 | 28.589 | 57.615 | 82.911 | 1.00 | 26.13 | B | C |
| ATOM | 3384 | CB | THR | B | 138 | 27.842 | 57.426 | 81.580 | 1.00 | 25.95 | B | C |
| ATOM | 3385 | OG1 | THR | B | 138 | 28.781 | 57.434 | 80.501 | 1.00 | 27.78 | B | O |
| ATOM | 3386 | CG2 | THR | B | 138 | 26.838 | 58.538 | 81.362 | 1.00 | 26.46 | B | C |
| ATOM | 3387 | C | THR | B | 138 | 29.697 | 56.570 | 82.977 | 1.00 | 25.87 | B | C |
| ATOM | 3388 | O | THR | B | 138 | 30.855 | 56.884 | 82.749 | 1.00 | 25.23 | B | O |
| ATOM | 3389 | N | VAL | B | 139 | 29.343 | 55.326 | 83.275 | 1.00 | 25.65 | B | N |
| ATOM | 3390 | CA | VAL | B | 139 | 30.350 | 54.274 | 83.350 | 1.00 | 25.96 | B | C |
| ATOM | 3391 | CB | VAL | B | 139 | 29.756 | 52.958 | 83.911 | 1.00 | 27.02 | B | C |
| ATOM | 3392 | CG1 | VAL | B | 139 | 30.753 | 51.819 | 83.759 | 1.00 | 22.51 | B | C |
| ATOM | 3393 | CG2 | VAL | B | 139 | 29.414 | 53.136 | 85.379 | 1.00 | 24.86 | B | C |
| ATOM | 3394 | C | VAL | B | 139 | 30.954 | 54.030 | 81.971 | 1.00 | 26.04 | B | C |
| ATOM | 3395 | O | VAL | B | 139 | 32.128 | 53.740 | 81.854 | 1.00 | 24.86 | B | O |
| ATOM | 3396 | N | TYR | B | 140 | 30.138 | 54.159 | 80.930 | 1.00 | 26.51 | B | N |
| ATOM | 3397 | CA | TYR | B | 140 | 30.633 | 53.981 | 79.572 | 1.00 | 27.78 | B | C |
| ATOM | 3398 | CB | TYR | B | 140 | 29.547 | 54.290 | 78.543 | 1.00 | 27.01 | B | C |
| ATOM | 3399 | CG | TYR | B | 140 | 30.040 | 54.125 | 77.125 | 1.00 | 26.24 | B | C |
| ATOM | 3400 | CD1 | TYR | B | 140 | 30.312 | 52.862 | 76.611 | 1.00 | 26.21 | B | C |
| ATOM | 3401 | CE1 | TYR | B | 140 | 30.816 | 52.701 | 75.329 | 1.00 | 26.92 | B | C |
| ATOM | 3402 | CD2 | TYR | B | 140 | 30.282 | 55.237 | 76.311 | 1.00 | 26.89 | B | C |
| ATOM | 3403 | CE2 | TYR | B | 140 | 30.787 | 55.091 | 75.022 | 1.00 | 26.37 | B | C |
| ATOM | 3404 | CZ | TYR | B | 140 | 31.052 | 53.817 | 74.538 | 1.00 | 28.74 | B | C |
| ATOM | 3405 | OH | TYR | B | 140 | 31.564 | 53.649 | 73.271 | 1.00 | 30.22 | B | O |
| ATOM | 3406 | C | TYR | B | 140 | 31.838 | 54.894 | 79.291 | 1.00 | 28.60 | B | C |
| ATOM | 3407 | O | TYR | B | 140 | 32.877 | 54.422 | 78.847 | 1.00 | 28.78 | B | O |
| ATOM | 3408 | N | ARG | B | 141 | 31.688 | 56.194 | 79.545 | 1.00 | 27.50 | B | N |
| ATOM | 3409 | CA | ARG | B | 141 | 32.776 | 57.147 | 79.299 | 1.00 | 27.92 | B | C |
| ATOM | 3410 | CB | ARG | B | 141 | 32.294 | 58.584 | 79.472 | 1.00 | 27.57 | B | C |
| ATOM | 3411 | CG | ARG | B | 141 | 31.100 | 58.954 | 78.638 | 1.00 | 30.10 | B | C |
| ATOM | 3412 | CD | ARG | B | 141 | 30.641 | 60.338 | 79.022 | 1.00 | 32.27 | B | C |
| ATOM | 3413 | NE | ARG | B | 141 | 31.049 | 61.316 | 78.025 | 1.00 | 37.27 | B | N |
| ATOM | 3414 | CZ | ARG | B | 141 | 31.449 | 62.548 | 78.306 | 1.00 | 38.16 | B | C |
| ATOM | 3415 | NH1 | ARG | B | 141 | 31.509 | 62.959 | 79.567 | 1.00 | 38.91 | B | N |
| ATOM | 3416 | NH2 | ARG | B | 141 | 31.767 | 63.373 | 77.318 | 1.00 | 41.92 | B | N |
| ATOM | 3417 | C | ARG | B | 141 | 33.962 | 56.928 | 80.221 | 1.00 | 27.02 | B | C |
| ATOM | 3418 | O | ARG | B | 141 | 35.094 | 56.961 | 79.788 | 1.00 | 28.42 | B | O |
| ATOM | 3419 | N | VAL | B | 142 | 33.690 | 56.735 | 81.502 | 1.00 | 27.37 | B | N |
| ATOM | 3420 | CA | VAL | B | 142 | 34.743 | 56.501 | 82.475 | 1.00 | 28.11 | B | C |
| ATOM | 3421 | CB | VAL | B | 142 | 34.149 | 56.278 | 83.864 | 1.00 | 28.21 | B | C |
| ATOM | 3422 | CG1 | VAL | B | 142 | 35.212 | 55.760 | 84.815 | 1.00 | 26.55 | B | C |
| ATOM | 3423 | CG2 | VAL | B | 142 | 33.561 | 57.595 | 84.377 | 1.00 | 28.68 | B | C |
| ATOM | 3424 | C | VAL | B | 142 | 35.574 | 55.285 | 82.074 | 1.00 | 30.53 | B | C |
| ATOM | 3425 | O | VAL | B | 142 | 36.806 | 55.358 | 82.017 | 1.00 | 29.04 | B | O |
| ATOM | 3426 | N | ALA | B | 143 | 34.895 | 54.176 | 81.785 | 1.00 | 30.77 | B | N |
| ATOM | 3427 | CA | ALA | B | 143 | 35.577 | 52.957 | 81.375 | 1.00 | 31.81 | B | C |
| ATOM | 3428 | CB | ALA | B | 143 | 34.562 | 51.861 | 81.046 | 1.00 | 31.46 | B | C |
| ATOM | 3429 | C | ALA | B | 143 | 36.448 | 53.238 | 80.155 | 1.00 | 33.02 | B | C |

FIG. 5-58

| | | | | | | | | | | | |
|---|---|---|---|---|---|---|---|---|---|---|---|
| ATOM | 3430 | O   | ALA | B | 143 | 37.569 | 52.763 | 80.076 | 1.00 | 33.27 | B | O |
| ATOM | 3431 | N   | ARG | B | 144 | 35.922 | 54.019 | 79.214 | 1.00 | 33.55 | B | N |
| ATOM | 3432 | CA  | ARG | B | 144 | 36.654 | 54.346 | 77.993 | 1.00 | 35.56 | B | C |
| ATOM | 3433 | CB  | ARG | B | 144 | 35.789 | 55.197 | 77.063 | 1.00 | 37.03 | B | C |
| ATOM | 3434 | CG  | ARG | B | 144 | 35.795 | 54.724 | 75.620 | 1.00 | 40.50 | B | C |
| ATOM | 3435 | CD  | ARG | B | 144 | 35.120 | 55.723 | 74.672 | 1.00 | 44.64 | B | C |
| ATOM | 3436 | NE  | ARG | B | 144 | 34.691 | 55.054 | 73.447 | 1.00 | 49.27 | B | N |
| ATOM | 3437 | CZ  | ARG | B | 144 | 34.302 | 55.671 | 72.334 | 1.00 | 51.57 | B | C |
| ATOM | 3438 | NH1 | ARG | B | 144 | 34.285 | 57.002 | 72.268 | 1.00 | 52.08 | B | N |
| ATOM | 3439 | NH2 | ARG | B | 144 | 33.924 | 54.949 | 71.282 | 1.00 | 52.28 | B | N |
| ATOM | 3440 | C   | ARG | B | 144 | 37.953 | 55.084 | 78.290 | 1.00 | 35.40 | B | C |
| ATOM | 3441 | O   | ARG | B | 144 | 39.000 | 54.685 | 77.844 | 1.00 | 35.35 | B | O |
| ATOM | 3442 | N   | HIS | B | 145 | 37.854 | 56.174 | 79.042 | 1.00 | 36.15 | B | N |
| ATOM | 3443 | CA  | HIS | B | 145 | 39.015 | 56.974 | 79.426 | 1.00 | 36.67 | B | C |
| ATOM | 3444 | CB  | HIS | B | 145 | 38.600 | 58.017 | 80.469 | 1.00 | 39.26 | B | C |
| ATOM | 3445 | CG  | HIS | B | 145 | 37.609 | 59.023 | 79.965 | 1.00 | 44.12 | B | C |
| ATOM | 3446 | CD2 | HIS | B | 145 | 37.316 | 59.436 | 78.704 | 1.00 | 45.34 | B | C |
| ATOM | 3447 | ND1 | HIS | B | 145 | 36.804 | 59.765 | 80.807 | 1.00 | 46.26 | B | N |
| ATOM | 3448 | CE1 | HIS | B | 145 | 36.058 | 60.589 | 80.089 | 1.00 | 47.02 | B | C |
| ATOM | 3449 | NE2 | HIS | B | 145 | 36.349 | 60.412 | 78.813 | 1.00 | 46.44 | B | N |
| ATOM | 3450 | C   | HIS | B | 145 | 40.127 | 56.091 | 79.999 | 1.00 | 35.59 | B | C |
| ATOM | 3451 | O   | HIS | B | 145 | 41.298 | 56.300 | 79.715 | 1.00 | 35.93 | B | O |
| ATOM | 3452 | N   | TYR | B | 146 | 39.760 | 55.107 | 80.812 | 1.00 | 34.78 | B | N |
| ATOM | 3453 | CA  | TYR | B | 146 | 40.762 | 54.229 | 81.395 | 1.00 | 34.96 | B | C |
| ATOM | 3454 | CB  | TYR | B | 146 | 40.177 | 53.423 | 82.554 | 1.00 | 33.21 | B | C |
| ATOM | 3455 | CG  | TYR | B | 146 | 40.140 | 54.168 | 83.865 | 1.00 | 32.58 | B | C |
| ATOM | 3456 | CD1 | TYR | B | 146 | 39.123 | 55.086 | 84.146 | 1.00 | 32.15 | B | C |
| ATOM | 3457 | CE1 | TYR | B | 146 | 39.100 | 55.794 | 85.351 | 1.00 | 31.29 | B | C |
| ATOM | 3458 | CD2 | TYR | B | 146 | 41.139 | 53.969 | 84.825 | 1.00 | 32.81 | B | C |
| ATOM | 3459 | CE2 | TYR | B | 146 | 41.128 | 54.670 | 86.033 | 1.00 | 32.39 | B | C |
| ATOM | 3460 | CZ  | TYR | B | 146 | 40.105 | 55.578 | 86.291 | 1.00 | 32.02 | B | C |
| ATOM | 3461 | OH  | TYR | B | 146 | 40.091 | 56.258 | 87.491 | 1.00 | 32.34 | B | O |
| ATOM | 3462 | C   | TYR | B | 146 | 41.313 | 53.280 | 80.343 | 1.00 | 36.61 | B | C |
| ATOM | 3463 | O   | TYR | B | 146 | 42.516 | 53.056 | 80.268 | 1.00 | 36.46 | B | O |
| ATOM | 3464 | N   | SER | B | 147 | 40.419 | 52.732 | 79.528 | 1.00 | 37.20 | B | N |
| ATOM | 3465 | CA  | SER | B | 147 | 40.808 | 51.803 | 78.481 | 1.00 | 38.55 | B | C |
| ATOM | 3466 | CB  | SER | B | 147 | 39.566 | 51.332 | 77.729 | 1.00 | 37.57 | B | C |
| ATOM | 3467 | OG  | SER | B | 147 | 39.830 | 50.129 | 77.038 | 1.00 | 40.67 | B | O |
| ATOM | 3468 | C   | SER | B | 147 | 41.781 | 52.494 | 77.529 | 1.00 | 40.32 | B | C |
| ATOM | 3469 | O   | SER | B | 147 | 42.874 | 52.000 | 77.292 | 1.00 | 39.67 | B | O |
| ATOM | 3470 | N   | ARG | B | 148 | 41.373 | 53.643 | 76.992 | 1.00 | 42.12 | B | N |
| ATOM | 3471 | CA  | ARG | B | 148 | 42.218 | 54.426 | 76.085 | 1.00 | 44.20 | B | C |
| ATOM | 3472 | CB  | ARG | B | 148 | 41.579 | 55.800 | 75.801 | 1.00 | 46.25 | B | C |
| ATOM | 3473 | CG  | ARG | B | 148 | 40.730 | 55.905 | 74.530 | 1.00 | 49.56 | B | C |
| ATOM | 3474 | CD  | ARG | B | 148 | 41.568 | 55.598 | 73.294 | 1.00 | 53.58 | B | C |
| ATOM | 3475 | NE  | ARG | B | 148 | 40.930 | 55.970 | 72.027 | 1.00 | 56.02 | B | N |
| ATOM | 3476 | CZ  | ARG | B | 148 | 40.941 | 57.197 | 71.504 | 1.00 | 57.54 | B | C |
| ATOM | 3477 | NH1 | ARG | B | 148 | 41.556 | 58.196 | 72.137 | 1.00 | 57.74 | B | N |
| ATOM | 3478 | NH2 | ARG | B | 148 | 40.363 | 57.422 | 70.328 | 1.00 | 58.16 | B | N |
| ATOM | 3479 | C   | ARG | B | 148 | 43.601 | 54.651 | 76.711 | 1.00 | 44.29 | B | C |
| ATOM | 3480 | O   | ARG | B | 148 | 44.626 | 54.427 | 76.072 | 1.00 | 44.48 | B | O |
| ATOM | 3481 | N   | ALA | B | 149 | 43.611 | 55.095 | 77.966 | 1.00 | 44.16 | B | N |
| ATOM | 3482 | CA  | ALA | B | 149 | 44.850 | 55.375 | 78.689 | 1.00 | 44.28 | B | C |
| ATOM | 3483 | CB  | ALA | B | 149 | 44.551 | 56.186 | 79.943 | 1.00 | 43.04 | B | C |
| ATOM | 3484 | C   | ALA | B | 149 | 45.610 | 54.109 | 79.067 | 1.00 | 45.22 | B | C |
| ATOM | 3485 | O   | ALA | B | 149 | 46.476 | 54.125 | 79.967 | 1.00 | 45.19 | B | O |
| ATOM | 3486 | N   | ALA | B | 150 | 45.290 | 53.008 | 78.397 | 1.00 | 45.12 | B | N |
| ATOM | 3487 | CA  | ALA | B | 150 | 45.966 | 51.750 | 78.670 | 1.00 | 45.16 | B | C |
| ATOM | 3488 | CB  | ALA | B | 150 | 47.389 | 51.799 | 78.120 | 1.00 | 44.88 | B | C |
| ATOM | 3489 | C   | ALA | B | 150 | 45.990 | 51.461 | 80.165 | 1.00 | 45.56 | B | C |

FIG. 5-59

```
ATOM   3490  O    ALA B 150      46.973  50.931  80.692  1.00 46.93       B  O
ATOM   3491  N    GLN B 151      44.908  51.810  80.853  1.00 45.39       B  N
ATOM   3492  CA   GLN B 151      44.827  51.560  82.283  1.00 44.36       B  C
ATOM   3493  CB   GLN B 151      45.089  52.837  83.062  1.00 46.16       B  C
ATOM   3494  CG   GLN B 151      46.468  53.388  82.864  1.00 48.61       B  C
ATOM   3495  CD   GLN B 151      46.894  54.163  84.065  1.00 49.02       B  C
ATOM   3496  OE1  GLN B 151      46.108  54.884  84.637  1.00 50.40       B  O
ATOM   3497  NE2  GLN B 151      48.149  54.011  84.458  1.00 50.14       B  N
ATOM   3498  C    GLN B 151      43.504  50.976  82.762  1.00 43.12       B  C
ATOM   3499  O    GLN B 151      42.510  50.949  82.034  1.00 42.20       B  O
ATOM   3500  N    THR B 152      43.500  50.539  84.016  1.00 40.80       B  N
ATOM   3501  CA   THR B 152      42.314  49.942  84.610  1.00 40.17       B  C
ATOM   3502  CB   THR B 152      42.629  48.540  85.168  1.00 40.98       B  C
ATOM   3503  OG1  THR B 152      41.732  48.252  86.251  1.00 43.52       B  O
ATOM   3504  CG2  THR B 152      44.064  48.477  85.676  1.00 41.18       B  C
ATOM   3505  C    THR B 152      41.736  50.769  85.759  1.00 37.44       B  C
ATOM   3506  O    THR B 152      42.471  51.417  86.524  1.00 36.99       B  O
ATOM   3507  N    LEU B 153      40.414  50.725  85.880  1.00 33.99       B  N
ATOM   3508  CA   LEU B 153      39.716  51.457  86.919  1.00 31.50       B  C
ATOM   3509  CB   LEU B 153      38.208  51.406  86.665  1.00 30.57       B  C
ATOM   3510  CG   LEU B 153      37.289  52.046  87.705  1.00 31.09       B  C
ATOM   3511  CD1  LEU B 153      37.528  53.557  87.759  1.00 29.89       B  C
ATOM   3512  CD2  LEU B 153      35.839  51.753  87.333  1.00 31.46       B  C
ATOM   3513  C    LEU B 153      40.036  50.843  88.284  1.00 30.81       B  C
ATOM   3514  O    LEU B 153      39.875  49.644  88.481  1.00 30.56       B  O
ATOM   3515  N    PRO B 154      40.521  51.658  89.236  1.00 28.71       B  N
ATOM   3516  CD   PRO B 154      40.896  53.079  89.145  1.00 28.24       B  C
ATOM   3517  CA   PRO B 154      40.834  51.111  90.564  1.00 28.81       B  C
ATOM   3518  CB   PRO B 154      41.116  52.366  91.390  1.00 28.88       B  C
ATOM   3519  CG   PRO B 154      41.777  53.267  90.367  1.00 29.18       B  C
ATOM   3520  C    PRO B 154      39.655  50.286  91.101  1.00 28.18       B  C
ATOM   3521  O    PRO B 154      38.518  50.689  90.999  1.00 27.62       B  O
ATOM   3522  N    VAL B 155      39.950  49.120  91.658  1.00 28.64       B  N
ATOM   3523  CA   VAL B 155      38.908  48.236  92.166  1.00 29.32       B  C
ATOM   3524  CB   VAL B 155      39.519  46.941  92.753  1.00 30.82       B  C
ATOM   3525  CG1  VAL B 155      40.441  46.292  91.727  1.00 33.38       B  C
ATOM   3526  CG2  VAL B 155      40.273  47.246  94.029  1.00 30.45       B  C
ATOM   3527  C    VAL B 155      37.993  48.857  93.223  1.00 28.81       B  C
ATOM   3528  O    VAL B 155      36.892  48.395  93.423  1.00 28.57       B  O
ATOM   3529  N    ILE B 156      38.457  49.896  93.909  1.00 28.44       B  N
ATOM   3530  CA   ILE B 156      37.617  50.504  94.921  1.00 26.70       B  C
ATOM   3531  CB   ILE B 156      38.391  51.582  95.729  1.00 27.48       B  C
ATOM   3532  CG2  ILE B 156      39.022  52.599  94.794  1.00 27.95       B  C
ATOM   3533  CG1  ILE B 156      37.447  52.272  96.718  1.00 27.56       B  C
ATOM   3534  CD1  ILE B 156      36.828  51.324  97.719  1.00 27.27       B  C
ATOM   3535  C    ILE B 156      36.390  51.096  94.235  1.00 25.15       B  C
ATOM   3536  O    ILE B 156      35.297  51.000  94.738  1.00 23.86       B  O
ATOM   3537  N    TYR B 157      36.596  51.683  93.060  1.00 25.03       B  N
ATOM   3538  CA   TYR B 157      35.501  52.273  92.294  1.00 24.90       B  C
ATOM   3539  CB   TYR B 157      36.043  53.176  91.183  1.00 27.49       B  C
ATOM   3540  CG   TYR B 157      36.581  54.491  91.692  1.00 30.64       B  C
ATOM   3541  CD1  TYR B 157      35.742  55.409  92.327  1.00 31.25       B  C
ATOM   3542  CE1  TYR B 157      36.228  56.635  92.772  1.00 33.95       B  C
ATOM   3543  CD2  TYR B 157      37.922  54.830  91.517  1.00 32.08       B  C
ATOM   3544  CE2  TYR B 157      38.420  56.052  91.958  1.00 33.66       B  C
ATOM   3545  CZ   TYR B 157      37.572  56.950  92.575  1.00 35.06       B  C
ATOM   3546  OH   TYR B 157      38.064  58.172  92.967  1.00 37.01       B  O
ATOM   3547  C    TYR B 157      34.635  51.179  91.693  1.00 24.46       B  C
ATOM   3548  O    TYR B 157      33.415  51.305  91.632  1.00 23.17       B  O
ATOM   3549  N    VAL B 158      35.277  50.106  91.245  1.00 22.43       B  N
```

FIG. 5-60

```
ATOM   3550  CA   VAL B 158      34.545  48.990  90.671  1.00 21.94      B  C
ATOM   3551  CB   VAL B 158      35.492  47.869  90.189  1.00 22.46      B  C
ATOM   3552  CG1  VAL B 158      34.678  46.681  89.702  1.00 20.20      B  C
ATOM   3553  CG2  VAL B 158      36.386  48.391  89.061  1.00 20.75      B  C
ATOM   3554  C    VAL B 158      33.608  48.433  91.742  1.00 21.97      B  C
ATOM   3555  O    VAL B 158      32.504  47.992  91.438  1.00 21.12      B  O
ATOM   3556  N    LYS B 159      34.062  48.463  92.995  1.00 21.21      B  N
ATOM   3557  CA   LYS B 159      33.254  47.983  94.107  1.00 21.53      B  C
ATOM   3558  CB   LYS B 159      34.091  47.880  95.385  1.00 22.50      B  C
ATOM   3559  CG   LYS B 159      34.997  46.666  95.458  1.00 21.22      B  C
ATOM   3560  CD   LYS B 159      35.815  46.694  96.722  1.00 19.70      B  C
ATOM   3561  CE   LYS B 159      36.753  45.499  96.805  1.00 20.38      B  C
ATOM   3562  NZ   LYS B 159      37.641  45.611  97.999  1.00 22.34      B  N
ATOM   3563  C    LYS B 159      32.080  48.931  94.350  1.00 21.81      B  C
ATOM   3564  O    LYS B 159      30.929  48.506  94.434  1.00 20.81      B  O
ATOM   3565  N    LEU B 160      32.384  50.219  94.460  1.00 21.78      B  N
ATOM   3566  CA   LEU B 160      31.357  51.223  94.690  1.00 22.22      B  C
ATOM   3567  CB   LEU B 160      31.999  52.610  94.797  1.00 22.88      B  C
ATOM   3568  CG   LEU B 160      32.756  52.951  96.089  1.00 24.90      B  C
ATOM   3569  CD1  LEU B 160      33.691  54.120  95.831  1.00 21.47      B  C
ATOM   3570  CD2  LEU B 160      31.764  53.272  97.216  1.00 23.45      B  C
ATOM   3571  C    LEU B 160      30.293  51.240  93.596  1.00 22.54      B  C
ATOM   3572  O    LEU B 160      29.118  51.250  93.881  1.00 21.35      B  O
ATOM   3573  N    TYR B 161      30.726  51.239  92.339  1.00 22.98      B  N
ATOM   3574  CA   TYR B 161      29.794  51.287  91.220  1.00 23.30      B  C
ATOM   3575  CB   TYR B 161      30.559  51.511  89.914  1.00 24.73      B  C
ATOM   3576  CG   TYR B 161      31.315  52.827  89.869  1.00 26.16      B  C
ATOM   3577  CD1  TYR B 161      30.983  53.875  90.728  1.00 25.50      B  C
ATOM   3578  CE1  TYR B 161      31.638  55.108  90.649  1.00 28.02      B  C
ATOM   3579  CD2  TYR B 161      32.329  53.040  88.929  1.00 26.06      B  C
ATOM   3580  CE2  TYR B 161      32.991  54.268  88.838  1.00 27.43      B  C
ATOM   3581  CZ   TYR B 161      32.638  55.299  89.702  1.00 28.35      B  C
ATOM   3582  OH   TYR B 161      33.259  56.525  89.606  1.00 30.25      B  O
ATOM   3583  C    TYR B 161      28.898  50.051  91.102  1.00 21.99      B  C
ATOM   3584  O    TYR B 161      27.695  50.176  90.944  1.00 19.35      B  O
ATOM   3585  N    MET B 162      29.497  48.867  91.190  1.00 20.57      B  N
ATOM   3586  CA   MET B 162      28.742  47.627  91.086  1.00 19.93      B  C
ATOM   3587  CB   MET B 162      29.686  46.422  91.013  1.00 20.07      B  C
ATOM   3588  CG   MET B 162      30.505  46.315  89.725  1.00 22.07      B  C
ATOM   3589  SD   MET B 162      29.528  46.389  88.196  1.00 23.25      B  S
ATOM   3590  CE   MET B 162      28.440  44.964  88.404  1.00 19.06      B  C
ATOM   3591  C    MET B 162      27.780  47.444  92.252  1.00 19.82      B  C
ATOM   3592  O    MET B 162      26.672  46.971  92.074  1.00 17.95      B  O
ATOM   3593  N    TYR B 163      28.221  47.814  93.449  1.00 19.40      B  N
ATOM   3594  CA   TYR B 163      27.377  47.692  94.628  1.00 19.22      B  C
ATOM   3595  CB   TYR B 163      28.117  48.154  95.881  1.00 19.98      B  C
ATOM   3596  CG   TYR B 163      27.269  48.138  97.138  1.00 20.59      B  C
ATOM   3597  CD1  TYR B 163      27.129  46.978  97.898  1.00 19.76      B  C
ATOM   3598  CE1  TYR B 163      26.361  46.966  99.066  1.00 19.05      B  C
ATOM   3599  CD2  TYR B 163      26.616  49.291  97.574  1.00 21.01      B  C
ATOM   3600  CE2  TYR B 163      25.848  49.292  98.735  1.00 19.15      B  C
ATOM   3601  CZ   TYR B 163      25.727  48.130  99.476  1.00 19.28      B  C
ATOM   3602  OH   TYR B 163      24.976  48.136 100.624  1.00 18.32      B  O
ATOM   3603  C    TYR B 163      26.112  48.521  94.471  1.00 18.27      B  C
ATOM   3604  O    TYR B 163      25.030  48.044  94.750  1.00 19.93      B  O
ATOM   3605  N    GLN B 164      26.267  49.763  94.023  1.00 16.69      B  N
ATOM   3606  CA   GLN B 164      25.129  50.648  93.845  1.00 16.70      B  C
ATOM   3607  CB   GLN B 164      25.615  52.077  93.593  1.00 17.20      B  C
ATOM   3608  CG   GLN B 164      26.448  52.638  94.749  1.00 19.19      B  C
ATOM   3609  CD   GLN B 164      27.077  53.983  94.433  1.00 21.90      B  C
```

FIG. 5-61

```
ATOM   3610  OE1 GLN B 164      26.422  55.014  94.495  1.00 20.75      B  O
ATOM   3611  NE2 GLN B 164      28.359  53.967  94.074  1.00 21.44      B  N
ATOM   3612  C   GLN B 164      24.223  50.161  92.721  1.00 17.39      B  C
ATOM   3613  O   GLN B 164      23.036  50.350  92.774  1.00 16.87      B  O
ATOM   3614  N   LEU B 165      24.809  49.517  91.715  1.00 17.33      B  N
ATOM   3615  CA  LEU B 165      24.050  48.992  90.586  1.00 17.65      B  C
ATOM   3616  CB  LEU B 165      24.989  48.365  89.547  1.00 16.79      B  C
ATOM   3617  CG  LEU B 165      24.553  48.286  88.073  1.00 19.32      B  C
ATOM   3618  CD1 LEU B 165      25.367  47.205  87.376  1.00 14.83      B  C
ATOM   3619  CD2 LEU B 165      23.063  48.012  87.942  1.00 15.93      B  C
ATOM   3620  C   LEU B 165      23.125  47.899  91.123  1.00 17.98      B  C
ATOM   3621  O   LEU B 165      21.957  47.877  90.835  1.00 17.86      B  O
ATOM   3622  N   PHE B 166      23.692  46.986  91.905  1.00 18.65      B  N
ATOM   3623  CA  PHE B 166      22.913  45.896  92.467  1.00 18.86      B  C
ATOM   3624  CB  PHE B 166      23.832  44.893  93.176  1.00 17.46      B  C
ATOM   3625  CG  PHE B 166      24.585  43.983  92.231  1.00 17.81      B  C
ATOM   3626  CD1 PHE B 166      23.897  43.170  91.329  1.00 18.30      B  C
ATOM   3627  CD2 PHE B 166      25.978  43.933  92.243  1.00 17.89      B  C
ATOM   3628  CE1 PHE B 166      24.583  42.324  90.455  1.00 15.97      B  C
ATOM   3629  CE2 PHE B 166      26.672  43.089  91.371  1.00 17.33      B  C
ATOM   3630  CZ  PHE B 166      25.971  42.284  90.476  1.00 16.86      B  C
ATOM   3631  C   PHE B 166      21.824  46.423  93.401  1.00 20.31      B  C
ATOM   3632  O   PHE B 166      20.751  45.863  93.468  1.00 20.76      B  O
ATOM   3633  N   ARG B 167      22.113  47.513  94.106  1.00 20.34      B  N
ATOM   3634  CA  ARG B 167      21.128  48.127  94.989  1.00 19.69      B  C
ATOM   3635  CB  ARG B 167      21.743  49.331  95.705  1.00 20.99      B  C
ATOM   3636  CG  ARG B 167      22.235  49.036  97.107  1.00 23.78      B  C
ATOM   3637  CD  ARG B 167      21.324  49.690  98.130  1.00 25.21      B  C
ATOM   3638  NE  ARG B 167      21.905  50.918  98.646  1.00 26.75      B  N
ATOM   3639  CZ  ARG B 167      21.279  51.782  99.436  1.00 27.08      B  C
ATOM   3640  NH1 ARG B 167      20.024  51.564  99.808  1.00 25.34      B  N
ATOM   3641  NH2 ARG B 167      21.925  52.857  99.871  1.00 27.28      B  N
ATOM   3642  C   ARG B 167      19.920  48.588  94.172  1.00 19.18      B  C
ATOM   3643  O   ARG B 167      18.792  48.312  94.538  1.00 18.10      B  O
ATOM   3644  N   SER B 168      20.167  49.290  93.066  1.00 18.41      B  N
ATOM   3645  CA  SER B 168      19.066  49.771  92.235  1.00 19.60      B  C
ATOM   3646  CB  SER B 168      19.583  50.657  91.087  1.00 19.13      B  C
ATOM   3647  OG  SER B 168      20.296  49.921  90.112  1.00 15.20      B  O
ATOM   3648  C   SER B 168      18.264  48.586  91.680  1.00 20.66      B  C
ATOM   3649  O   SER B 168      17.055  48.624  91.649  1.00 22.59      B  O
ATOM   3650  N   LEU B 169      18.956  47.534  91.256  1.00 19.58      B  N
ATOM   3651  CA  LEU B 169      18.287  46.355  90.732  1.00 19.52      B  C
ATOM   3652  CB  LEU B 169      19.321  45.360  90.206  1.00 19.00      B  C
ATOM   3653  CG  LEU B 169      19.616  45.276  88.699  1.00 20.42      B  C
ATOM   3654  CD1 LEU B 169      19.438  46.611  88.000  1.00 19.90      B  C
ATOM   3655  CD2 LEU B 169      21.023  44.753  88.517  1.00 18.86      B  C
ATOM   3656  C   LEU B 169      17.412  45.697  91.803  1.00 20.38      B  C
ATOM   3657  O   LEU B 169      16.293  45.304  91.526  1.00 19.37      B  O
ATOM   3658  N   ALA B 170      17.932  45.576  93.022  1.00 20.42      B  N
ATOM   3659  CA  ALA B 170      17.162  44.989  94.117  1.00 21.59      B  C
ATOM   3660  CB  ALA B 170      17.997  44.950  95.404  1.00 21.41      B  C
ATOM   3661  C   ALA B 170      15.897  45.819  94.332  1.00 20.96      B  C
ATOM   3662  O   ALA B 170      14.830  45.278  94.549  1.00 21.26      B  O
ATOM   3663  N   TYR B 171      16.029  47.140  94.256  1.00 21.12      B  N
ATOM   3664  CA  TYR B 171      14.882  48.020  94.433  1.00 21.70      B  C
ATOM   3665  CB  TYR B 171      15.313  49.490  94.384  1.00 23.35      B  C
ATOM   3666  CG  TYR B 171      14.166  50.475  94.521  1.00 23.33      B  C
ATOM   3667  CD1 TYR B 171      13.476  50.613  95.725  1.00 24.00      B  C
ATOM   3668  CE1 TYR B 171      12.399  51.498  95.846  1.00 23.82      B  C
ATOM   3669  CD2 TYR B 171      13.748  51.245  93.434  1.00 25.41      B  C
```

FIG. 5-62

```
ATOM   3670  CE2  TYR B 171      12.669  52.131  93.542  1.00 24.08      B    C
ATOM   3671  CZ   TYR B 171      12.000  52.247  94.751  1.00 23.87      B    C
ATOM   3672  OH   TYR B 171      10.926  53.095  94.863  1.00 25.05      B    O
ATOM   3673  C    TYR B 171      13.818  47.756  93.360  1.00 22.68      B    C
ATOM   3674  O    TYR B 171      12.710  47.357  93.680  1.00 22.57      B    O
ATOM   3675  N    ILE B 172      14.155  47.973  92.089  1.00 20.43      B    N
ATOM   3676  CA   ILE B 172      13.173  47.751  91.032  1.00 20.83      B    C
ATOM   3677  CB   ILE B 172      13.720  48.115  89.618  1.00 21.45      B    C
ATOM   3678  CG2  ILE B 172      13.962  49.622  89.531  1.00 18.27      B    C
ATOM   3679  CG1  ILE B 172      14.988  47.321  89.294  1.00 20.89      B    C
ATOM   3680  CD1  ILE B 172      15.377  47.391  87.819  1.00 20.73      B    C
ATOM   3681  C    ILE B 172      12.620  46.323  91.012  1.00 20.40      B    C
ATOM   3682  O    ILE B 172      11.427  46.137  90.849  1.00 20.85      B    O
ATOM   3683  N    HIS B 173      13.482  45.324  91.204  1.00 20.17      B    N
ATOM   3684  CA   HIS B 173      13.039  43.929  91.208  1.00 21.35      B    C
ATOM   3685  CB   HIS B 173      14.235  42.961  91.349  1.00 21.95      B    C
ATOM   3686  CG   HIS B 173      15.100  42.874  90.124  1.00 24.88      B    C
ATOM   3687  CD2  HIS B 173      15.101  43.600  88.978  1.00 23.62      B    C
ATOM   3688  ND1  HIS B 173      16.128  41.964  89.999  1.00 25.44      B    N
ATOM   3689  CE1  HIS B 173      16.726  42.132  88.830  1.00 24.51      B    C
ATOM   3690  NE2  HIS B 173      16.119  43.120  88.194  1.00 23.62      B    N
ATOM   3691  C    HIS B 173      12.017  43.647  92.317  1.00 21.56      B    C
ATOM   3692  O    HIS B 173      11.117  42.851  92.129  1.00 20.59      B    O
ATOM   3693  N    SER B 174      12.157  44.307  93.463  1.00 20.64      B    N
ATOM   3694  CA   SER B 174      11.218  44.100  94.557  1.00 22.46      B    C
ATOM   3695  CB   SER B 174      11.594  44.938  95.780  1.00 20.63      B    C
ATOM   3696  OG   SER B 174      11.159  46.273  95.625  1.00 20.84      B    O
ATOM   3697  C    SER B 174       9.809  44.475  94.092  1.00 24.09      B    C
ATOM   3698  O    SER B 174       8.842  44.021  94.651  1.00 25.84      B    O
ATOM   3699  N    PHE B 175       9.714  45.313  93.064  1.00 24.80      B    N
ATOM   3700  CA   PHE B 175       8.418  45.709  92.527  1.00 25.57      B    C
ATOM   3701  CB   PHE B 175       8.419  47.172  92.087  1.00 26.92      B    C
ATOM   3702  CG   PHE B 175       8.446  48.143  93.222  1.00 30.64      B    C
ATOM   3703  CD1  PHE B 175       9.625  48.786  93.574  1.00 30.26      B    C
ATOM   3704  CD2  PHE B 175       7.285  48.412  93.945  1.00 32.51      B    C
ATOM   3705  CE1  PHE B 175       9.656  49.689  94.630  1.00 32.46      B    C
ATOM   3706  CE2  PHE B 175       7.301  49.316  95.009  1.00 36.01      B    C
ATOM   3707  CZ   PHE B 175       8.495  49.958  95.352  1.00 34.69      B    C
ATOM   3708  C    PHE B 175       8.080  44.844  91.323  1.00 25.57      B    C
ATOM   3709  O    PHE B 175       7.104  45.090  90.644  1.00 25.44      B    O
ATOM   3710  N    GLY B 176       8.909  43.835  91.073  1.00 24.32      B    N
ATOM   3711  CA   GLY B 176       8.696  42.958  89.935  1.00 24.39      B    C
ATOM   3712  C    GLY B 176       9.144  43.561  88.609  1.00 24.36      B    C
ATOM   3713  O    GLY B 176       9.004  42.939  87.552  1.00 24.07      B    O
ATOM   3714  N    ILE B 177       9.698  44.770  88.669  1.00 23.66      B    N
ATOM   3715  CA   ILE B 177      10.151  45.478  87.476  1.00 22.96      B    C
ATOM   3716  CB   ILE B 177      10.048  47.010  87.698  1.00 23.38      B    C
ATOM   3717  CG2  ILE B 177      10.585  47.766  86.487  1.00 23.52      B    C
ATOM   3718  CG1  ILE B 177       8.584  47.380  87.972  1.00 22.36      B    C
ATOM   3719  CD1  ILE B 177       8.333  48.855  88.182  1.00 20.71      B    C
ATOM   3720  C    ILE B 177      11.566  45.106  87.040  1.00 22.24      B    C
ATOM   3721  O    ILE B 177      12.491  45.130  87.830  1.00 20.00      B    O
ATOM   3722  N    CYS B 178      11.703  44.739  85.770  1.00 21.94      B    N
ATOM   3723  CA   CYS B 178      12.997  44.371  85.197  1.00 20.74      B    C
ATOM   3724  CB   CYS B 178      12.902  43.044  84.445  1.00 22.76      B    C
ATOM   3725  SG   CYS B 178      14.485  42.451  83.803  1.00 23.40      B    S
ATOM   3726  C    CYS B 178      13.407  45.469  84.228  1.00 20.07      B    C
ATOM   3727  O    CYS B 178      12.616  45.896  83.374  1.00 18.12      B    O
ATOM   3728  N    HIS B 179      14.648  45.919  84.367  1.00 19.45      B    N
ATOM   3729  CA   HIS B 179      15.179  46.981  83.528  1.00 18.29      B    C
```

FIG. 5-63

```
ATOM   3730  CB   HIS B 179      16.532  47.424  84.075  1.00 17.40       B  C
ATOM   3731  CG   HIS B 179      17.073  48.648  83.411  1.00 14.71       B  C
ATOM   3732  CD2  HIS B 179      17.115  49.935  83.822  1.00 14.81       B  C
ATOM   3733  ND1  HIS B 179      17.622  48.624  82.149  1.00 13.45       B  N
ATOM   3734  CE1  HIS B 179      17.981  49.849  81.808  1.00 15.68       B  C
ATOM   3735  NE2  HIS B 179      17.683  50.663  82.806  1.00 15.19       B  N
ATOM   3736  C    HIS B 179      15.285  46.537  82.071  1.00 19.97       B  C
ATOM   3737  O    HIS B 179      14.804  47.224  81.180  1.00 19.85       B  O
ATOM   3738  N    ARG B 180      15.928  45.389  81.858  1.00 19.86       B  N
ATOM   3739  CA   ARG B 180      16.093  44.781  80.537  1.00 21.26       B  C
ATOM   3740  CB   ARG B 180      14.742  44.707  79.826  1.00 20.78       B  C
ATOM   3741  CG   ARG B 180      13.683  43.959  80.595  1.00 21.99       B  C
ATOM   3742  CD   ARG B 180      12.329  44.378  80.080  1.00 23.94       B  C
ATOM   3743  NE   ARG B 180      11.764  43.429  79.135  1.00 24.23       B  N
ATOM   3744  CZ   ARG B 180      10.877  43.746  78.199  1.00 23.78       B  C
ATOM   3745  NH1  ARG B 180      10.457  45.001  78.066  1.00 22.69       B  N
ATOM   3746  NH2  ARG B 180      10.383  42.797  77.421  1.00 21.12       B  N
ATOM   3747  C    ARG B 180      17.111  45.405  79.594  1.00 20.45       B  C
ATOM   3748  O    ARG B 180      17.281  44.923  78.488  1.00 22.35       B  O
ATOM   3749  N    ASP B 181      17.772  46.477  80.017  1.00 20.41       B  N
ATOM   3750  CA   ASP B 181      18.792  47.099  79.174  1.00 20.56       B  C
ATOM   3751  CB   ASP B 181      18.173  48.204  78.307  1.00 19.42       B  C
ATOM   3752  CG   ASP B 181      19.020  48.526  77.083  1.00 20.25       B  C
ATOM   3753  OD1  ASP B 181      19.867  47.691  76.701  1.00 19.97       B  O
ATOM   3754  OD2  ASP B 181      18.834  49.607  76.496  1.00 21.94       B  O
ATOM   3755  C    ASP B 181      19.957  47.656  80.003  1.00 19.76       B  C
ATOM   3756  O    ASP B 181      20.375  48.782  79.823  1.00 19.12       B  O
ATOM   3757  N    ILE B 182      20.459  46.836  80.925  1.00 19.93       B  N
ATOM   3758  CA   ILE B 182      21.582  47.211  81.770  1.00 18.29       B  C
ATOM   3759  CB   ILE B 182      21.753  46.239  82.968  1.00 18.18       B  C
ATOM   3760  CG2  ILE B 182      23.058  46.531  83.692  1.00 18.34       B  C
ATOM   3761  CG1  ILE B 182      20.548  46.332  83.913  1.00 19.15       B  C
ATOM   3762  CD1  ILE B 182      20.366  47.670  84.600  1.00 19.51       B  C
ATOM   3763  C    ILE B 182      22.843  47.147  80.915  1.00 18.91       B  C
ATOM   3764  O    ILE B 182      23.162  46.099  80.335  1.00 18.27       B  O
ATOM   3765  N    LYS B 183      23.536  48.278  80.841  1.00 18.82       B  N
ATOM   3766  CA   LYS B 183      24.770  48.422  80.078  1.00 19.33       B  C
ATOM   3767  CB   LYS B 183      24.470  48.489  78.575  1.00 18.66       B  C
ATOM   3768  CG   LYS B 183      23.419  49.509  78.171  1.00 19.97       B  C
ATOM   3769  CD   LYS B 183      23.393  49.694  76.660  1.00 19.81       B  C
ATOM   3770  CE   LYS B 183      22.228  50.562  76.210  1.00 21.53       B  C
ATOM   3771  NZ   LYS B 183      22.305  50.883  74.755  1.00 21.65       B  N
ATOM   3772  C    LYS B 183      25.483  49.701  80.533  1.00 20.15       B  C
ATOM   3773  O    LYS B 183      24.866  50.588  81.072  1.00 19.09       B  O
ATOM   3774  N    PRO B 184      26.807  49.790  80.317  1.00 21.23       B  N
ATOM   3775  CD   PRO B 184      27.663  48.797  79.641  1.00 18.82       B  C
ATOM   3776  CA   PRO B 184      27.586  50.971  80.718  1.00 21.66       B  C
ATOM   3777  CB   PRO B 184      28.915  50.769  79.990  1.00 20.95       B  C
ATOM   3778  CG   PRO B 184      29.058  49.267  79.986  1.00 20.35       B  C
ATOM   3779  C    PRO B 184      26.942  52.327  80.414  1.00 21.24       B  C
ATOM   3780  O    PRO B 184      26.950  53.207  81.260  1.00 20.40       B  O
ATOM   3781  N    GLN B 185      26.385  52.475  79.209  1.00 22.24       B  N
ATOM   3782  CA   GLN B 185      25.729  53.716  78.777  1.00 22.91       B  C
ATOM   3783  CB   GLN B 185      25.269  53.608  77.327  1.00 24.70       B  C
ATOM   3784  CG   GLN B 185      26.389  53.429  76.325  1.00 31.01       B  C
ATOM   3785  CD   GLN B 185      25.982  53.839  74.927  1.00 35.53       B  C
ATOM   3786  OE1  GLN B 185      26.778  53.759  73.996  1.00 37.89       B  O
ATOM   3787  NE2  GLN B 185      24.724  54.273  74.767  1.00 37.49       B  N
ATOM   3788  C    GLN B 185      24.525  54.136  79.615  1.00 22.24       B  C
ATOM   3789  O    GLN B 185      24.163  55.298  79.634  1.00 21.83       B  O
```

FIG. 5-64

```
ATOM   3790  N    ASN B 186      23.902  53.185  80.296  1.00 21.04      B    N
ATOM   3791  CA   ASN B 186      22.739  53.502  81.109  1.00 20.91      B    C
ATOM   3792  CB   ASN B 186      21.643  52.464  80.872  1.00 21.11      B    C
ATOM   3793  CG   ASN B 186      21.041  52.574  79.487  1.00 22.98      B    C
ATOM   3794  OD1  ASN B 186      21.047  53.641  78.893  1.00 21.56      B    O
ATOM   3795  ND2  ASN B 186      20.501  51.470  78.977  1.00 24.20      B    N
ATOM   3796  C    ASN B 186      23.078  53.586  82.590  1.00 20.70      B    C
ATOM   3797  O    ASN B 186      22.204  53.526  83.444  1.00 20.56      B    O
ATOM   3798  N    LEU B 187      24.367  53.718  82.874  1.00 20.37      B    N
ATOM   3799  CA   LEU B 187      24.862  53.822  84.235  1.00 21.68      B    C
ATOM   3800  CB   LEU B 187      25.857  52.686  84.507  1.00 21.08      B    C
ATOM   3801  CG   LEU B 187      25.345  51.384  85.147  1.00 23.12      B    C
ATOM   3802  CD1  LEU B 187      23.953  51.053  84.676  1.00 23.01      B    C
ATOM   3803  CD2  LEU B 187      26.311  50.254  84.837  1.00 21.69      B    C
ATOM   3804  C    LEU B 187      25.531  55.184  84.428  1.00 22.94      B    C
ATOM   3805  O    LEU B 187      26.654  55.400  83.998  1.00 23.78      B    O
ATOM   3806  N    LEU B 188      24.815  56.100  85.070  1.00 22.73      B    N
ATOM   3807  CA   LEU B 188      25.317  57.451  85.313  1.00 21.92      B    C
ATOM   3808  CB   LEU B 188      24.144  58.422  85.478  1.00 21.07      B    C
ATOM   3809  CG   LEU B 188      23.019  58.386  84.436  1.00 22.25      B    C
ATOM   3810  CD1  LEU B 188      21.832  59.189  84.940  1.00 22.66      B    C
ATOM   3811  CD2  LEU B 188      23.499  58.921  83.113  1.00 23.75      B    C
ATOM   3812  C    LEU B 188      26.157  57.470  86.587  1.00 22.02      B    C
ATOM   3813  O    LEU B 188      25.943  56.667  87.498  1.00 17.40      B    O
ATOM   3814  N    LEU B 189      27.119  58.384  86.650  1.00 23.47      B    N
ATOM   3815  CA   LEU B 189      27.944  58.486  87.841  1.00 28.29      B    C
ATOM   3816  CB   LEU B 189      29.070  57.441  87.822  1.00 30.86      B    C
ATOM   3817  CG   LEU B 189      30.085  57.420  86.680  1.00 34.10      B    C
ATOM   3818  CD1  LEU B 189      31.060  58.594  86.841  1.00 35.95      B    C
ATOM   3819  CD2  LEU B 189      30.845  56.096  86.690  1.00 34.00      B    C
ATOM   3820  C    LEU B 189      28.518  59.864  88.061  1.00 29.27      B    C
ATOM   3821  O    LEU B 189      28.860  60.566  87.128  1.00 30.36      B    O
ATOM   3822  N    ASP B 190      28.583  60.252  89.324  1.00 31.26      B    N
ATOM   3823  CA   ASP B 190      29.127  61.543  89.691  1.00 33.94      B    C
ATOM   3824  CB   ASP B 190      28.314  62.152  90.828  1.00 35.10      B    C
ATOM   3825  CG   ASP B 190      28.759  63.552  91.160  1.00 36.45      B    C
ATOM   3826  OD1  ASP B 190      29.942  63.723  91.529  1.00 38.19      B    O
ATOM   3827  OD2  ASP B 190      27.933  64.483  91.043  1.00 38.48      B    O
ATOM   3828  C    ASP B 190      30.560  61.279  90.146  1.00 34.46      B    C
ATOM   3829  O    ASP B 190      30.780  60.700  91.183  1.00 34.62      B    O
ATOM   3830  N    PRO B 191      31.546  61.711  89.353  1.00 36.30      B    N
ATOM   3831  CD   PRO B 191      31.395  62.662  88.239  1.00 36.97      B    C
ATOM   3832  CA   PRO B 191      32.963  61.511  89.671  1.00 37.27      B    C
ATOM   3833  CB   PRO B 191      33.678  62.316  88.585  1.00 37.64      B    C
ATOM   3834  CG   PRO B 191      32.714  63.424  88.295  1.00 37.84      B    C
ATOM   3835  C    PRO B 191      33.371  61.938  91.080  1.00 37.42      B    C
ATOM   3836  O    PRO B 191      34.105  61.228  91.768  1.00 38.47      B    O
ATOM   3837  N    ASP B 192      32.874  63.085  91.516  1.00 36.60      B    N
ATOM   3838  CA   ASP B 192      33.235  63.602  92.824  1.00 37.14      B    C
ATOM   3839  CB   ASP B 192      32.936  65.102  92.885  1.00 38.13      B    C
ATOM   3840  CG   ASP B 192      33.708  65.881  91.837  1.00 40.13      B    C
ATOM   3841  OD1  ASP B 192      34.910  65.581  91.657  1.00 41.22      B    O
ATOM   3842  OD2  ASP B 192      33.129  66.790  91.199  1.00 41.40      B    O
ATOM   3843  C    ASP B 192      32.632  62.906  94.039  1.00 36.28      B    C
ATOM   3844  O    ASP B 192      33.296  62.791  95.063  1.00 37.01      B    O
ATOM   3845  N    THR B 193      31.389  62.447  93.937  1.00 33.67      B    N
ATOM   3846  CA   THR B 193      30.744  61.774  95.067  1.00 30.70      B    C
ATOM   3847  CB   THR B 193      29.284  62.232  95.223  1.00 31.07      B    C
ATOM   3848  OG1  THR B 193      28.571  61.964  94.010  1.00 30.40      B    O
ATOM   3849  CG2  THR B 193      29.218  63.730  95.529  1.00 28.84      B    C
```

FIG. 5-65

```
ATOM   3850  C    THR B 193      30.744  60.256  94.946  1.00 28.29      B  C
ATOM   3851  O    THR B 193      30.404  59.570  95.885  1.00 27.69      B  O
ATOM   3852  N    ALA B 194      31.124  59.753  93.774  1.00 26.20      B  N
ATOM   3853  CA   ALA B 194      31.167  58.315  93.512  1.00 25.82      B  C
ATOM   3854  CB   ALA B 194      32.104  57.620  94.519  1.00 23.20      B  C
ATOM   3855  C    ALA B 194      29.771  57.678  93.559  1.00 24.35      B  C
ATOM   3856  O    ALA B 194      29.630  56.501  93.793  1.00 22.79      B  O
ATOM   3857  N    VAL B 195      28.748  58.487  93.317  1.00 24.20      B  N
ATOM   3858  CA   VAL B 195      27.373  58.008  93.316  1.00 24.68      B  C
ATOM   3859  CB   VAL B 195      26.401  59.135  93.752  1.00 26.38      B  C
ATOM   3860  CG1  VAL B 195      24.946  58.711  93.501  1.00 26.09      B  C
ATOM   3861  CG2  VAL B 195      26.609  59.456  95.240  1.00 23.95      B  C
ATOM   3862  C    VAL B 195      26.977  57.522  91.918  1.00 24.97      B  C
ATOM   3863  O    VAL B 195      27.272  58.170  90.919  1.00 24.97      B  O
ATOM   3864  N    LEU B 196      26.312  56.372  91.860  1.00 23.36      B  N
ATOM   3865  CA   LEU B 196      25.880  55.814  90.588  1.00 22.63      B  C
ATOM   3866  CB   LEU B 196      26.439  54.389  90.413  1.00 23.07      B  C
ATOM   3867  CG   LEU B 196      25.995  53.568  89.188  1.00 22.32      B  C
ATOM   3868  CD1  LEU B 196      27.031  52.513  88.835  1.00 20.89      B  C
ATOM   3869  CD2  LEU B 196      24.658  52.922  89.471  1.00 20.34      B  C
ATOM   3870  C    LEU B 196      24.366  55.799  90.506  1.00 22.12      B  C
ATOM   3871  O    LEU B 196      23.692  55.444  91.455  1.00 22.46      B  O
ATOM   3872  N    LYS B 197      23.840  56.205  89.359  1.00 21.40      B  N
ATOM   3873  CA   LYS B 197      22.401  56.230  89.155  1.00 20.52      B  C
ATOM   3874  CB   LYS B 197      21.884  57.672  89.111  1.00 21.80      B  C
ATOM   3875  CG   LYS B 197      22.102  58.463  90.397  1.00 23.52      B  C
ATOM   3876  CD   LYS B 197      21.410  59.820  90.329  1.00 27.44      B  C
ATOM   3877  CE   LYS B 197      21.757  60.694  91.530  1.00 26.35      B  C
ATOM   3878  NZ   LYS B 197      21.603  59.944  92.793  1.00 29.52      B  N
ATOM   3879  C    LYS B 197      22.008  55.517  87.873  1.00 20.15      B  C
ATOM   3880  O    LYS B 197      22.571  55.761  86.821  1.00 16.06      B  O
ATOM   3881  N    LEU B 198      21.035  54.622  87.990  1.00 18.98      B  N
ATOM   3882  CA   LEU B 198      20.527  53.881  86.852  1.00 18.22      B  C
ATOM   3883  CB   LEU B 198      19.777  52.640  87.349  1.00 17.57      B  C
ATOM   3884  CG   LEU B 198      19.200  51.671  86.318  1.00 16.99      B  C
ATOM   3885  CD1  LEU B 198      20.318  51.095  85.468  1.00 17.46      B  C
ATOM   3886  CD2  LEU B 198      18.451  50.565  87.035  1.00 15.22      B  C
ATOM   3887  C    LEU B 198      19.581  54.815  86.097  1.00 18.35      B  C
ATOM   3888  O    LEU B 198      18.847  55.573  86.716  1.00 18.41      B  O
ATOM   3889  N    CYS B 199      19.624  54.765  84.766  1.00 18.99      B  N
ATOM   3890  CA   CYS B 199      18.776  55.606  83.914  1.00 18.78      B  C
ATOM   3891  CB   CYS B 199      19.554  56.832  83.414  1.00 18.96      B  C
ATOM   3892  SG   CYS B 199      20.731  56.503  82.075  1.00 19.73      B  S
ATOM   3893  C    CYS B 199      18.257  54.815  82.714  1.00 19.20      B  C
ATOM   3894  O    CYS B 199      18.576  53.648  82.552  1.00 18.40      B  O
ATOM   3895  N    ASP B 200      17.469  55.480  81.875  1.00 19.26      B  N
ATOM   3896  CA   ASP B 200      16.887  54.882  80.675  1.00 21.20      B  C
ATOM   3897  CB   ASP B 200      17.986  54.494  79.679  1.00 21.39      B  C
ATOM   3898  CG   ASP B 200      17.426  53.973  78.368  1.00 22.10      B  C
ATOM   3899  OD1  ASP B 200      16.210  54.111  78.135  1.00 23.97      B  O
ATOM   3900  OD2  ASP B 200      18.198  53.427  77.564  1.00 24.08      B  O
ATOM   3901  C    ASP B 200      15.982  53.679  80.956  1.00 21.59      B  C
ATOM   3902  O    ASP B 200      16.381  52.513  80.808  1.00 22.15      B  O
ATOM   3903  N    PHE B 201      14.752  53.976  81.351  1.00 20.94      B  N
ATOM   3904  CA   PHE B 201      13.782  52.940  81.647  1.00 20.87      B  C
ATOM   3905  CB   PHE B 201      13.009  53.305  82.917  1.00 20.01      B  C
ATOM   3906  CG   PHE B 201      13.818  53.152  84.164  1.00 20.27      B  C
ATOM   3907  CD1  PHE B 201      14.845  54.047  84.460  1.00 19.83      B  C
ATOM   3908  CD2  PHE B 201      13.613  52.065  85.005  1.00 18.14      B  C
ATOM   3909  CE1  PHE B 201      15.659  53.858  85.573  1.00 16.64      B  C
```

FIG. 5-66

```
ATOM   3910  CE2 PHE B 201      14.419  51.864  86.117  1.00 20.03      B  C
ATOM   3911  CZ  PHE B 201      15.448  52.763  86.403  1.00 17.76      B  C
ATOM   3912  C   PHE B 201      12.833  52.676  80.488  1.00 19.77      B  C
ATOM   3913  O   PHE B 201      11.745  52.186  80.685  1.00 21.01      B  O
ATOM   3914  N   GLY B 202      13.283  52.995  79.276  1.00 20.60      B  N
ATOM   3915  CA  GLY B 202      12.471  52.780  78.089  1.00 19.16      B  C
ATOM   3916  C   GLY B 202      12.211  51.315  77.768  1.00 19.09      B  C
ATOM   3917  O   GLY B 202      11.342  51.011  76.981  1.00 19.34      B  O
ATOM   3918  N   SER B 203      12.969  50.410  78.374  1.00 18.23      B  N
ATOM   3919  CA  SER B 203      12.772  48.981  78.143  1.00 21.08      B  C
ATOM   3920  CB  SER B 203      14.097  48.303  77.769  1.00 20.35      B  C
ATOM   3921  OG  SER B 203      14.625  48.819  76.565  1.00 22.39      B  O
ATOM   3922  C   SER B 203      12.218  48.303  79.402  1.00 21.25      B  C
ATOM   3923  O   SER B 203      11.814  47.151  79.366  1.00 21.87      B  O
ATOM   3924  N   ALA B 204      12.210  49.029  80.514  1.00 21.58      B  N
ATOM   3925  CA  ALA B 204      11.737  48.466  81.770  1.00 21.26      B  C
ATOM   3926  CB  ALA B 204      11.852  49.485  82.879  1.00 21.06      B  C
ATOM   3927  C   ALA B 204      10.310  47.945  81.694  1.00 22.75      B  C
ATOM   3928  O   ALA B 204       9.465  48.533  81.055  1.00 19.66      B  O
ATOM   3929  N   LYS B 205      10.064  46.820  82.357  1.00 24.34      B  N
ATOM   3930  CA  LYS B 205       8.733  46.232  82.369  1.00 25.50      B  C
ATOM   3931  CB  LYS B 205       8.456  45.506  81.049  1.00 26.87      B  C
ATOM   3932  CG  LYS B 205       7.063  44.887  80.975  1.00 29.53      B  C
ATOM   3933  CD  LYS B 205       6.785  44.232  79.628  1.00 32.14      B  C
ATOM   3934  CE  LYS B 205       5.423  43.533  79.624  1.00 32.08      B  C
ATOM   3935  NZ  LYS B 205       5.199  42.772  78.353  1.00 38.10      B  N
ATOM   3936  C   LYS B 205       8.507  45.262  83.529  1.00 25.37      B  C
ATOM   3937  O   LYS B 205       9.393  44.501  83.914  1.00 24.30      B  O
ATOM   3938  N   GLN B 206       7.307  45.295  84.090  1.00 26.61      B  N
ATOM   3939  CA  GLN B 206       6.995  44.385  85.176  1.00 28.25      B  C
ATOM   3940  CB  GLN B 206       5.665  44.762  85.839  1.00 31.79      B  C
ATOM   3941  CG  GLN B 206       5.370  43.975  87.119  1.00 36.57      B  C
ATOM   3942  CD  GLN B 206       4.183  44.532  87.912  1.00 40.82      B  C
ATOM   3943  OE1 GLN B 206       3.916  44.098  89.062  1.00 42.49      B  O
ATOM   3944  NE2 GLN B 206       3.461  45.488  87.316  1.00 41.19      B  N
ATOM   3945  C   GLN B 206       6.894  43.008  84.545  1.00 28.60      B  C
ATOM   3946  O   GLN B 206       6.188  42.828  83.548  1.00 28.36      B  O
ATOM   3947  N   LEU B 207       7.626  42.048  85.099  1.00 28.92      B  N
ATOM   3948  CA  LEU B 207       7.606  40.689  84.579  1.00 29.53      B  C
ATOM   3949  CB  LEU B 207       9.025  40.118  84.498  1.00 28.73      B  C
ATOM   3950  CG  LEU B 207      10.064  40.834  83.620  1.00 28.73      B  C
ATOM   3951  CD1 LEU B 207      11.356  40.027  83.602  1.00 27.04      B  C
ATOM   3952  CD2 LEU B 207       9.535  41.001  82.214  1.00 26.77      B  C
ATOM   3953  C   LEU B 207       6.733  39.805  85.465  1.00 31.83      B  C
ATOM   3954  O   LEU B 207       7.081  39.525  86.605  1.00 32.51      B  O
ATOM   3955  N   VAL B 208       5.593  39.382  84.925  1.00 32.85      B  N
ATOM   3956  CA  VAL B 208       4.651  38.526  85.639  1.00 32.67      B  C
ATOM   3957  CB  VAL B 208       3.190  38.969  85.372  1.00 33.21      B  C
ATOM   3958  CG1 VAL B 208       2.219  38.066  86.137  1.00 33.10      B  C
ATOM   3959  CG2 VAL B 208       3.005  40.430  85.788  1.00 30.55      B  C
ATOM   3960  C   VAL B 208       4.828  37.081  85.166  1.00 33.20      B  C
ATOM   3961  O   VAL B 208       4.955  36.827  83.959  1.00 32.70      B  O
ATOM   3962  N   ALA B 209       4.837  36.139  86.109  1.00 33.05      B  N
ATOM   3963  CA  ALA B 209       5.007  34.724  85.775  1.00 33.77      B  C
ATOM   3964  CB  ALA B 209       5.096  33.889  87.047  1.00 33.63      B  C
ATOM   3965  C   ALA B 209       3.873  34.215  84.890  1.00 33.72      B  C
ATOM   3966  O   ALA B 209       2.703  34.491  85.139  1.00 34.36      B  O
ATOM   3967  N   GLY B 210       4.232  33.477  83.846  1.00 34.07      B  N
ATOM   3968  CA  GLY B 210       3.223  32.964  82.940  1.00 33.96      B  C
ATOM   3969  C   GLY B 210       2.947  33.903  81.772  1.00 34.33      B  C
```

FIG. 5-67

```
ATOM   3970  O    GLY B 210       2.317  33.517  80.797  1.00 34.80           B  O
ATOM   3971  N    GLU B 211       3.395  35.149  81.869  1.00 33.95           B  N
ATOM   3972  CA   GLU B 211       3.181  36.093  80.773  1.00 34.51           B  C
ATOM   3973  CB   GLU B 211       2.901  37.506  81.302  1.00 35.74           B  C
ATOM   3974  CG   GLU B 211       1.576  37.660  82.039  1.00 37.35           B  C
ATOM   3975  CD   GLU B 211       1.319  39.090  82.488  1.00 39.05           B  C
ATOM   3976  OE1  GLU B 211       0.232  39.350  83.051  1.00 41.80           B  O
ATOM   3977  OE2  GLU B 211       2.199  39.959  82.281  1.00 38.46           B  O
ATOM   3978  C    GLU B 211       4.425  36.127  79.876  1.00 33.84           B  C
ATOM   3979  O    GLU B 211       5.547  36.158  80.361  1.00 33.91           B  O
ATOM   3980  N    PRO B 212       4.236  36.099  78.551  1.00 32.61           B  N
ATOM   3981  CD   PRO B 212       3.029  35.721  77.793  1.00 32.06           B  C
ATOM   3982  CA   PRO B 212       5.418  36.130  77.686  1.00 31.05           B  C
ATOM   3983  CB   PRO B 212       4.944  35.406  76.432  1.00 31.34           B  C
ATOM   3984  CG   PRO B 212       3.500  35.819  76.349  1.00 33.13           B  C
ATOM   3985  C    PRO B 212       5.919  37.544  77.392  1.00 29.70           B  C
ATOM   3986  O    PRO B 212       5.146  38.499  77.355  1.00 28.93           B  O
ATOM   3987  N    ASN B 213       7.224  37.660  77.176  1.00 26.44           B  N
ATOM   3988  CA   ASN B 213       7.829  38.946  76.893  1.00 24.71           B  C
ATOM   3989  CB   ASN B 213       8.512  39.465  78.154  1.00 24.12           B  C
ATOM   3990  CG   ASN B 213       7.508  39.813  79.238  1.00 24.81           B  C
ATOM   3991  OD1  ASN B 213       6.789  40.807  79.130  1.00 25.19           B  O
ATOM   3992  ND2  ASN B 213       7.431  38.979  80.273  1.00 20.74           B  N
ATOM   3993  C    ASN B 213       8.810  38.842  75.732  1.00 24.37           B  C
ATOM   3994  O    ASN B 213       9.464  37.813  75.551  1.00 23.57           B  O
ATOM   3995  N    VAL B 214       8.891  39.915  74.945  1.00 23.72           B  N
ATOM   3996  CA   VAL B 214       9.771  39.953  73.784  1.00 22.40           B  C
ATOM   3997  CB   VAL B 214       9.721  41.335  73.089  1.00 23.09           B  C
ATOM   3998  CG1  VAL B 214       8.279  41.659  72.711  1.00 23.23           B  C
ATOM   3999  CG2  VAL B 214      10.295  42.423  74.002  1.00 23.43           B  C
ATOM   4000  C    VAL B 214      11.204  39.616  74.158  1.00 22.65           B  C
ATOM   4001  O    VAL B 214      11.686  39.996  75.222  1.00 20.95           B  O
ATOM   4002  N    SER B 215      11.891  38.894  73.283  1.00 23.20           B  N
ATOM   4003  CA   SER B 215      13.260  38.515  73.594  1.00 24.77           B  C
ATOM   4004  CB   SER B 215      13.478  37.018  73.312  1.00 26.83           B  C
ATOM   4005  OG   SER B 215      13.280  36.689  71.945  1.00 26.38           B  O
ATOM   4006  C    SER B 215      14.321  39.343  72.871  1.00 24.55           B  C
ATOM   4007  O    SER B 215      15.485  39.021  72.933  1.00 26.32           B  O
ATOM   4008  N    TYR B 216      13.916  40.420  72.210  1.00 22.14           B  N
ATOM   4009  CA   TYR B 216      14.870  41.255  71.477  1.00 23.30           B  C
ATOM   4010  CB   TYR B 216      14.315  41.550  70.080  1.00 22.47           B  C
ATOM   4011  CG   TYR B 216      12.900  42.096  70.084  1.00 24.45           B  C
ATOM   4012  CD1  TYR B 216      12.637  43.429  70.412  1.00 26.49           B  C
ATOM   4013  CE1  TYR B 216      11.324  43.924  70.417  1.00 26.61           B  C
ATOM   4014  CD2  TYR B 216      11.820  41.273  69.773  1.00 23.82           B  C
ATOM   4015  CE2  TYR B 216      10.515  41.750  69.779  1.00 22.15           B  C
ATOM   4016  CZ   TYR B 216      10.269  43.069  70.099  1.00 26.83           B  C
ATOM   4017  OH   TYR B 216       8.969  43.531  70.090  1.00 27.14           B  O
ATOM   4018  C    TYR B 216      15.160  42.569  72.192  1.00 22.00           B  C
ATOM   4019  O    TYR B 216      15.546  43.547  71.572  1.00 20.70           B  O
ATOM   4020  N    ILE B 217      15.020  42.541  73.513  1.00 23.21           B  N
ATOM   4021  CA   ILE B 217      15.154  43.711  74.365  1.00 24.46           B  C
ATOM   4022  CB   ILE B 217      14.186  43.536  75.572  1.00 24.58           B  C
ATOM   4023  CG2  ILE B 217      14.795  42.621  76.650  1.00 21.47           B  C
ATOM   4024  CG1  ILE B 217      13.826  44.897  76.137  1.00 26.80           B  C
ATOM   4025  CD1  ILE B 217      12.891  45.650  75.237  1.00 27.53           B  C
ATOM   4026  C    ILE B 217      16.498  44.204  74.918  1.00 25.63           B  C
ATOM   4027  O    ILE B 217      16.637  45.412  75.225  1.00 31.55           B  O
ATOM   4028  N    CYS B 218      17.487  43.333  75.059  1.00 23.77           B  N
ATOM   4029  CA   CYS B 218      18.752  43.778  75.659  1.00 21.88           B  C
```

FIG. 5-68

```
ATOM   4030  CB   CYS B 218      19.252  42.671  76.597  1.00 20.93      B  C
ATOM   4031  SG   CYS B 218      20.451  43.132  77.853  1.00 18.00      B  S
ATOM   4032  C    CYS B 218      19.820  44.171  74.619  1.00 20.36      B  C
ATOM   4033  O    CYS B 218      19.697  43.855  73.454  1.00 19.25      B  O
ATOM   4034  N    SER B 219      20.861  44.872  75.054  1.00 20.20      B  N
ATOM   4035  CA   SER B 219      21.910  45.324  74.142  1.00 20.24      B  C
ATOM   4036  CB   SER B 219      22.427  46.692  74.593  1.00 21.62      B  C
ATOM   4037  OG   SER B 219      21.467  47.703  74.344  1.00 22.61      B  O
ATOM   4038  C    SER B 219      23.090  44.380  73.927  1.00 20.73      B  C
ATOM   4039  O    SER B 219      23.507  43.699  74.837  1.00 20.26      B  O
ATOM   4040  N    ALA B 220      23.614  44.365  72.701  1.00 21.57      B  N
ATOM   4041  CA   ALA B 220      24.755  43.524  72.320  1.00 22.45      B  C
ATOM   4042  CB   ALA B 220      25.296  43.971  70.962  1.00 23.18      B  C
ATOM   4043  C    ALA B 220      25.873  43.577  73.346  1.00 20.42      B  C
ATOM   4044  O    ALA B 220      26.277  44.630  73.724  1.00 19.81      B  O
ATOM   4045  N    TYR B 221      26.365  42.399  73.728  1.00 20.58      B  N
ATOM   4046  CA   TYR B 221      27.435  42.216  74.717  1.00 20.23      B  C
ATOM   4047  CB   TYR B 221      28.346  43.450  74.867  1.00 21.68      B  C
ATOM   4048  CG   TYR B 221      29.188  43.883  73.675  1.00 24.04      B  C
ATOM   4049  CD1  TYR B 221      29.327  43.080  72.536  1.00 25.90      B  C
ATOM   4050  CE1  TYR B 221      30.098  43.502  71.445  1.00 26.31      B  C
ATOM   4051  CD2  TYR B 221      29.843  45.115  73.693  1.00 23.88      B  C
ATOM   4052  CE2  TYR B 221      30.612  45.540  72.621  1.00 27.25      B  C
ATOM   4053  CZ   TYR B 221      30.738  44.734  71.500  1.00 26.91      B  C
ATOM   4054  OH   TYR B 221      31.512  45.165  70.446  1.00 28.71      B  O
ATOM   4055  C    TYR B 221      26.881  41.914  76.102  1.00 19.77      B  C
ATOM   4056  O    TYR B 221      27.462  41.140  76.822  1.00 20.31      B  O
ATOM   4057  N    TYR B 222      25.759  42.533  76.465  1.00 19.15      B  N
ATOM   4058  CA   TYR B 222      25.178  42.360  77.802  1.00 20.26      B  C
ATOM   4059  CB   TYR B 222      24.870  43.745  78.383  1.00 18.46      B  C
ATOM   4060  CG   TYR B 222      26.021  44.706  78.194  1.00 19.13      B  C
ATOM   4061  CD1  TYR B 222      27.136  44.669  79.039  1.00 19.51      B  C
ATOM   4062  CE1  TYR B 222      28.256  45.467  78.791  1.00 19.49      B  C
ATOM   4063  CD2  TYR B 222      26.055  45.566  77.099  1.00 18.02      B  C
ATOM   4064  CE2  TYR B 222      27.167  46.366  76.843  1.00 18.28      B  C
ATOM   4065  CZ   TYR B 222      28.263  46.307  77.684  1.00 19.86      B  C
ATOM   4066  OH   TYR B 222      29.362  47.083  77.411  1.00 19.68      B  O
ATOM   4067  C    TYR B 222      23.938  41.480  77.899  1.00 19.48      B  C
ATOM   4068  O    TYR B 222      23.352  41.376  78.949  1.00 19.34      B  O
ATOM   4069  N    ARG B 223      23.569  40.837  76.798  1.00 18.11      B  N
ATOM   4070  CA   ARG B 223      22.381  39.994  76.761  1.00 18.48      B  C
ATOM   4071  CB   ARG B 223      21.912  39.843  75.321  1.00 17.53      B  C
ATOM   4072  CG   ARG B 223      21.889  41.142  74.556  1.00 19.07      B  C
ATOM   4073  CD   ARG B 223      21.320  40.928  73.177  1.00 19.87      B  C
ATOM   4074  NE   ARG B 223      19.865  40.942  73.200  1.00 20.11      B  N
ATOM   4075  CZ   ARG B 223      19.097  40.053  72.584  1.00 20.06      B  C
ATOM   4076  NH1  ARG B 223      19.638  39.057  71.895  1.00 19.59      B  N
ATOM   4077  NH2  ARG B 223      17.781  40.180  72.638  1.00 20.18      B  N
ATOM   4078  C    ARG B 223      22.580  38.612  77.379  1.00 19.44      B  C
ATOM   4079  O    ARG B 223      23.547  37.914  77.082  1.00 19.76      B  O
ATOM   4080  N    ALA B 224      21.653  38.223  78.243  1.00 19.05      B  N
ATOM   4081  CA   ALA B 224      21.722  36.920  78.880  1.00 19.06      B  C
ATOM   4082  CB   ALA B 224      20.647  36.792  79.951  1.00 16.11      B  C
ATOM   4083  C    ALA B 224      21.521  35.858  77.802  1.00 20.32      B  C
ATOM   4084  O    ALA B 224      20.811  36.082  76.821  1.00 20.41      B  O
ATOM   4085  N    PRO B 225      22.165  34.694  77.969  1.00 20.46      B  N
ATOM   4086  CD   PRO B 225      23.060  34.345  79.084  1.00 20.79      B  C
ATOM   4087  CA   PRO B 225      22.057  33.589  77.017  1.00 18.96      B  C
ATOM   4088  CB   PRO B 225      22.851  32.466  77.688  1.00 19.69      B  C
ATOM   4089  CG   PRO B 225      22.873  32.867  79.159  1.00 20.59      B  C
```

FIG. 5-69

| ATOM | 4090 | C | PRO | B | 225 | 20.615 | 33.207 | 76.669 | 1.00 | 18.78 | B | C |
|------|------|------|-----|---|-----|--------|--------|--------|------|-------|---|---|
| ATOM | 4091 | O | PRO | B | 225 | 20.327 | 32.945 | 75.530 | 1.00 | 18.47 | B | O |
| ATOM | 4092 | N | GLU | B | 226 | 19.712 | 33.205 | 77.646 | 1.00 | 19.13 | B | N |
| ATOM | 4093 | CA | GLU | B | 226 | 18.323 | 32.855 | 77.355 | 1.00 | 20.23 | B | C |
| ATOM | 4094 | CB | GLU | B | 226 | 17.484 | 32.816 | 78.638 | 1.00 | 21.15 | B | C |
| ATOM | 4095 | CG | GLU | B | 226 | 17.497 | 34.097 | 79.450 | 1.00 | 20.87 | B | C |
| ATOM | 4096 | CD | GLU | B | 226 | 18.509 | 34.053 | 80.581 | 1.00 | 21.43 | B | C |
| ATOM | 4097 | OE1 | GLU | B | 226 | 19.614 | 33.511 | 80.377 | 1.00 | 21.23 | B | O |
| ATOM | 4098 | OE2 | GLU | B | 226 | 18.199 | 34.569 | 81.672 | 1.00 | 20.39 | B | O |
| ATOM | 4099 | C | GLU | B | 226 | 17.695 | 33.824 | 76.354 | 1.00 | 20.03 | B | C |
| ATOM | 4100 | O | GLU | B | 226 | 16.861 | 33.433 | 75.565 | 1.00 | 19.93 | B | O |
| ATOM | 4101 | N | LEU | B | 227 | 18.103 | 35.090 | 76.404 | 1.00 | 20.03 | B | N |
| ATOM | 4102 | CA | LEU | B | 227 | 17.580 | 36.093 | 75.479 | 1.00 | 19.66 | B | C |
| ATOM | 4103 | CB | LEU | B | 227 | 18.003 | 37.503 | 75.900 | 1.00 | 18.23 | B | C |
| ATOM | 4104 | CG | LEU | B | 227 | 17.467 | 38.115 | 77.197 | 1.00 | 18.85 | B | C |
| ATOM | 4105 | CD1 | LEU | B | 227 | 18.034 | 39.510 | 77.335 | 1.00 | 16.46 | B | C |
| ATOM | 4106 | CD2 | LEU | B | 227 | 15.942 | 38.160 | 77.195 | 1.00 | 14.82 | B | C |
| ATOM | 4107 | C | LEU | B | 227 | 18.103 | 35.822 | 74.069 | 1.00 | 20.56 | B | C |
| ATOM | 4108 | O | LEU | B | 227 | 17.376 | 35.926 | 73.102 | 1.00 | 20.42 | B | O |
| ATOM | 4109 | N | ILE | B | 228 | 19.382 | 35.482 | 73.966 | 1.00 | 20.20 | B | N |
| ATOM | 4110 | CA | ILE | B | 228 | 19.967 | 35.193 | 72.669 | 1.00 | 21.28 | B | C |
| ATOM | 4111 | CB | ILE | B | 228 | 21.477 | 34.917 | 72.782 | 1.00 | 22.09 | B | C |
| ATOM | 4112 | CG2 | ILE | B | 228 | 22.047 | 34.650 | 71.395 | 1.00 | 21.31 | B | C |
| ATOM | 4113 | CG1 | ILE | B | 228 | 22.179 | 36.111 | 73.449 | 1.00 | 22.87 | B | C |
| ATOM | 4114 | CD1 | ILE | B | 228 | 23.675 | 35.945 | 73.620 | 1.00 | 19.17 | B | C |
| ATOM | 4115 | C | ILE | B | 228 | 19.264 | 33.967 | 72.073 | 1.00 | 21.15 | B | C |
| ATOM | 4116 | O | ILE | B | 228 | 18.960 | 33.930 | 70.889 | 1.00 | 19.46 | B | O |
| ATOM | 4117 | N | PHE | B | 229 | 19.007 | 32.978 | 72.924 | 1.00 | 21.12 | B | N |
| ATOM | 4118 | CA | PHE | B | 229 | 18.333 | 31.761 | 72.507 | 1.00 | 22.54 | B | C |
| ATOM | 4119 | CB | PHE | B | 229 | 18.441 | 30.691 | 73.597 | 1.00 | 21.61 | B | C |
| ATOM | 4120 | CG | PHE | B | 229 | 19.747 | 29.935 | 73.595 | 1.00 | 22.04 | B | C |
| ATOM | 4121 | CD1 | PHE | B | 229 | 20.147 | 29.205 | 72.479 | 1.00 | 22.75 | B | C |
| ATOM | 4122 | CD2 | PHE | B | 229 | 20.554 | 29.913 | 74.729 | 1.00 | 22.62 | B | C |
| ATOM | 4123 | CE1 | PHE | B | 229 | 21.334 | 28.458 | 72.499 | 1.00 | 24.68 | B | C |
| ATOM | 4124 | CE2 | PHE | B | 229 | 21.740 | 29.171 | 74.757 | 1.00 | 21.88 | B | C |
| ATOM | 4125 | CZ | PHE | B | 229 | 22.129 | 28.441 | 73.641 | 1.00 | 21.95 | B | C |
| ATOM | 4126 | C | PHE | B | 229 | 16.867 | 32.011 | 72.149 | 1.00 | 23.69 | B | C |
| ATOM | 4127 | O | PHE | B | 229 | 16.210 | 31.136 | 71.636 | 1.00 | 25.36 | B | O |
| ATOM | 4128 | N | GLY | B | 230 | 16.365 | 33.212 | 72.437 | 1.00 | 23.28 | B | N |
| ATOM | 4129 | CA | GLY | B | 230 | 14.991 | 33.546 | 72.092 | 1.00 | 22.60 | B | C |
| ATOM | 4130 | C | GLY | B | 230 | 13.886 | 33.186 | 73.073 | 1.00 | 22.98 | B | C |
| ATOM | 4131 | O | GLY | B | 230 | 12.729 | 33.081 | 72.687 | 1.00 | 23.31 | B | O |
| ATOM | 4132 | N | ALA | B | 231 | 14.233 | 32.993 | 74.341 | 1.00 | 22.37 | B | N |
| ATOM | 4133 | CA | ALA | B | 231 | 13.231 | 32.658 | 75.344 | 1.00 | 21.04 | B | C |
| ATOM | 4134 | CB | ALA | B | 231 | 13.906 | 32.227 | 76.644 | 1.00 | 21.67 | B | C |
| ATOM | 4135 | C | ALA | B | 231 | 12.345 | 33.864 | 75.594 | 1.00 | 20.81 | B | C |
| ATOM | 4136 | O | ALA | B | 231 | 12.793 | 34.987 | 75.497 | 1.00 | 20.98 | B | O |
| ATOM | 4137 | N | THR | B | 232 | 11.079 | 33.608 | 75.901 | 1.00 | 21.63 | B | N |
| ATOM | 4138 | CA | THR | B | 232 | 10.122 | 34.667 | 76.185 | 1.00 | 21.91 | B | C |
| ATOM | 4139 | CB | THR | B | 232 | 8.954 | 34.659 | 75.181 | 1.00 | 22.66 | B | C |
| ATOM | 4140 | OG1 | THR | B | 232 | 8.249 | 33.418 | 75.284 | 1.00 | 22.84 | B | O |
| ATOM | 4141 | CG2 | THR | B | 232 | 9.472 | 34.839 | 73.751 | 1.00 | 22.60 | B | C |
| ATOM | 4142 | C | THR | B | 232 | 9.559 | 34.500 | 77.592 | 1.00 | 22.71 | B | C |
| ATOM | 4143 | O | THR | B | 232 | 8.645 | 35.212 | 77.990 | 1.00 | 22.59 | B | O |
| ATOM | 4144 | N | ASP | B | 233 | 10.119 | 33.550 | 78.338 | 1.00 | 22.46 | B | N |
| ATOM | 4145 | CA | ASP | B | 233 | 9.682 | 33.280 | 79.706 | 1.00 | 24.98 | B | C |
| ATOM | 4146 | CB | ASP | B | 233 | 9.273 | 31.810 | 79.846 | 1.00 | 25.12 | B | C |
| ATOM | 4147 | CG | ASP | B | 233 | 10.450 | 30.869 | 79.711 | 1.00 | 28.36 | B | C |
| ATOM | 4148 | OD1 | ASP | B | 233 | 11.380 | 31.181 | 78.932 | 1.00 | 29.73 | B | O |
| ATOM | 4149 | OD2 | ASP | B | 233 | 10.444 | 29.806 | 80.367 | 1.00 | 30.28 | B | O |

FIG. 5-70

```
ATOM   4150  C    ASP B 233      10.822  33.593  80.671  1.00 24.58      B    C
ATOM   4151  O    ASP B 233      10.952  32.967  81.723  1.00 23.76      B    O
ATOM   4152  N    TYR B 234      11.651  34.567  80.301  1.00 23.58      B    N
ATOM   4153  CA   TYR B 234      12.786  34.943  81.137  1.00 21.60      B    C
ATOM   4154  CB   TYR B 234      13.809  35.730  80.325  1.00 19.91      B    C
ATOM   4155  CG   TYR B 234      13.254  36.975  79.659  1.00 19.23      B    C
ATOM   4156  CD1  TYR B 234      12.743  36.927  78.361  1.00 18.95      B    C
ATOM   4157  CE1  TYR B 234      12.253  38.074  77.734  1.00 19.39      B    C
ATOM   4158  CD2  TYR B 234      13.253  38.202  80.319  1.00 17.93      B    C
ATOM   4159  CE2  TYR B 234      12.766  39.356  79.700  1.00 17.98      B    C
ATOM   4160  CZ   TYR B 234      12.269  39.284  78.413  1.00 18.72      B    C
ATOM   4161  OH   TYR B 234      11.785  40.409  77.796  1.00 17.19      B    O
ATOM   4162  C    TYR B 234      12.354  35.763  82.343  1.00 21.61      B    C
ATOM   4163  O    TYR B 234      11.302  36.350  82.339  1.00 23.80      B    O
ATOM   4164  N    THR B 235      13.194  35.789  83.374  1.00 22.93      B    N
ATOM   4165  CA   THR B 235      12.906  36.544  84.591  1.00 23.36      B    C
ATOM   4166  CB   THR B 235      13.169  35.686  85.833  1.00 25.09      B    C
ATOM   4167  OG1  THR B 235      14.540  35.272  85.836  1.00 23.05      B    O
ATOM   4168  CG2  THR B 235      12.267  34.454  85.834  1.00 25.19      B    C
ATOM   4169  C    THR B 235      13.768  37.801  84.694  1.00 23.20      B    C
ATOM   4170  O    THR B 235      14.510  38.132  83.778  1.00 22.48      B    O
ATOM   4171  N    SER B 236      13.663  38.484  85.829  1.00 21.85      B    N
ATOM   4172  CA   SER B 236      14.429  39.696  86.095  1.00 22.91      B    C
ATOM   4173  CB   SER B 236      13.972  40.328  87.416  1.00 23.54      B    C
ATOM   4174  OG   SER B 236      12.651  40.841  87.310  1.00 29.80      B    O
ATOM   4175  C    SER B 236      15.919  39.364  86.184  1.00 21.39      B    C
ATOM   4176  O    SER B 236      16.776  40.242  86.136  1.00 18.93      B    O
ATOM   4177  N    SER B 237      16.197  38.076  86.318  1.00 19.44      B    N
ATOM   4178  CA   SER B 237      17.547  37.544  86.411  1.00 20.67      B    C
ATOM   4179  CB   SER B 237      17.442  36.021  86.426  1.00 21.10      B    C
ATOM   4180  OG   SER B 237      18.612  35.427  86.912  1.00 29.43      B    O
ATOM   4181  C    SER B 237      18.398  38.008  85.211  1.00 20.00      B    C
ATOM   4182  O    SER B 237      19.619  37.935  85.223  1.00 18.04      B    O
ATOM   4183  N    ILE B 238      17.709  38.452  84.170  1.00 18.38      B    N
ATOM   4184  CA   ILE B 238      18.332  38.964  82.958  1.00 20.29      B    C
ATOM   4185  CB   ILE B 238      17.194  39.436  81.983  1.00 20.99      B    C
ATOM   4186  CG2  ILE B 238      17.359  40.878  81.577  1.00 24.39      B    C
ATOM   4187  CG1  ILE B 238      17.117  38.502  80.796  1.00 21.26      B    C
ATOM   4188  CD1  ILE B 238      16.662  37.140  81.174  1.00 25.68      B    C
ATOM   4189  C    ILE B 238      19.254  40.133  83.324  1.00 18.33      B    C
ATOM   4190  O    ILE B 238      20.346  40.247  82.799  1.00 18.89      B    O
ATOM   4191  N    ASP B 239      18.791  40.988  84.236  1.00 17.71      B    N
ATOM   4192  CA   ASP B 239      19.570  42.142  84.679  1.00 16.54      B    C
ATOM   4193  CB   ASP B 239      18.745  43.039  85.611  1.00 16.46      B    C
ATOM   4194  CG   ASP B 239      17.584  43.722  84.903  1.00 17.67      B    C
ATOM   4195  OD1  ASP B 239      17.640  43.885  83.668  1.00 19.90      B    O
ATOM   4196  OD2  ASP B 239      16.617  44.111  85.590  1.00 17.84      B    O
ATOM   4197  C    ASP B 239      20.851  41.721  85.403  1.00 16.47      B    C
ATOM   4198  O    ASP B 239      21.892  42.354  85.264  1.00 14.36      B    O
ATOM   4199  N    VAL B 240      20.762  40.650  86.179  1.00 15.84      B    N
ATOM   4200  CA   VAL B 240      21.916  40.164  86.914  1.00 16.97      B    C
ATOM   4201  CB   VAL B 240      21.533  39.000  87.844  1.00 15.91      B    C
ATOM   4202  CG1  VAL B 240      22.777  38.392  88.463  1.00 18.68      B    C
ATOM   4203  CG2  VAL B 240      20.607  39.507  88.937  1.00 18.95      B    C
ATOM   4204  C    VAL B 240      23.014  39.715  85.950  1.00 17.33      B    C
ATOM   4205  O    VAL B 240      24.199  39.968  86.193  1.00 17.59      B    O
ATOM   4206  N    TRP B 241      22.630  39.047  84.865  1.00 16.11      B    N
ATOM   4207  CA   TRP B 241      23.623  38.609  83.893  1.00 16.45      B    C
ATOM   4208  CB   TRP B 241      22.988  37.716  82.813  1.00 15.82      B    C
ATOM   4209  CG   TRP B 241      23.918  37.419  81.659  1.00 16.49      B    C
```

FIG. 5-71

```
ATOM   4210  CD2  TRP B 241      24.718  36.244  81.466  1.00 17.69      B    C
ATOM   4211  CE2  TRP B 241      25.469  36.433  80.288  1.00 17.18      B    C
ATOM   4212  CE3  TRP B 241      24.876  35.041  82.177  1.00 16.22      B    C
ATOM   4213  CD1  TRP B 241      24.209  38.248  80.611  1.00 14.97      B    C
ATOM   4214  NE1  TRP B 241      25.134  37.669  79.788  1.00 16.23      B    N
ATOM   4215  CZ2  TRP B 241      26.363  35.480  79.800  1.00 17.92      B    C
ATOM   4216  CZ3  TRP B 241      25.765  34.091  81.693  1.00 16.87      B    C
ATOM   4217  CH2  TRP B 241      26.497  34.315  80.516  1.00 17.97      B    C
ATOM   4218  C    TRP B 241      24.261  39.853  83.267  1.00 16.07      B    C
ATOM   4219  O    TRP B 241      25.470  39.910  83.093  1.00 14.40      B    O
ATOM   4220  N    SER B 242      23.434  40.846  82.941  1.00 15.43      B    N
ATOM   4221  CA   SER B 242      23.940  42.088  82.366  1.00 15.51      B    C
ATOM   4222  CB   SER B 242      22.799  43.060  82.059  1.00 15.11      B    C
ATOM   4223  OG   SER B 242      22.076  42.659  80.914  1.00 14.78      B    O
ATOM   4224  C    SER B 242      24.913  42.741  83.339  1.00 17.40      B    C
ATOM   4225  O    SER B 242      25.980  43.188  82.939  1.00 18.71      B    O
ATOM   4226  N    ALA B 243      24.539  42.787  84.616  1.00 16.36      B    N
ATOM   4227  CA   ALA B 243      25.404  43.381  85.628  1.00 17.00      B    C
ATOM   4228  CB   ALA B 243      24.740  43.319  86.993  1.00 15.86      B    C
ATOM   4229  C    ALA B 243      26.740  42.636  85.655  1.00 17.11      B    C
ATOM   4230  O    ALA B 243      27.799  43.245  85.740  1.00 17.20      B    O
ATOM   4231  N    GLY B 244      26.673  41.315  85.578  1.00 17.37      B    N
ATOM   4232  CA   GLY B 244      27.882  40.514  85.586  1.00 15.78      B    C
ATOM   4233  C    GLY B 244      28.792  40.865  84.424  1.00 18.09      B    C
ATOM   4234  O    GLY B 244      30.007  40.862  84.570  1.00 17.96      B    O
ATOM   4235  N    CYS B 245      28.199  41.164  83.265  1.00 16.86      B    N
ATOM   4236  CA   CYS B 245      28.978  41.534  82.091  1.00 17.34      B    C
ATOM   4237  CB   CYS B 245      28.099  41.569  80.835  1.00 16.67      B    C
ATOM   4238  SG   CYS B 245      27.486  39.962  80.295  1.00 19.19      B    S
ATOM   4239  C    CYS B 245      29.649  42.894  82.289  1.00 15.76      B    C
ATOM   4240  O    CYS B 245      30.722  43.128  81.779  1.00 14.91      B    O
ATOM   4241  N    VAL B 246      28.999  43.784  83.032  1.00 14.70      B    N
ATOM   4242  CA   VAL B 246      29.565  45.099  83.297  1.00 15.45      B    C
ATOM   4243  CB   VAL B 246      28.539  46.037  83.957  1.00 15.75      B    C
ATOM   4244  CG1  VAL B 246      29.224  47.314  84.439  1.00 13.36      B    C
ATOM   4245  CG2  VAL B 246      27.437  46.364  82.960  1.00 15.46      B    C
ATOM   4246  C    VAL B 246      30.758  44.919  84.235  1.00 17.58      B    C
ATOM   4247  O    VAL B 246      31.832  45.479  84.001  1.00 18.48      B    O
ATOM   4248  N    LEU B 247      30.562  44.128  85.290  1.00 17.17      B    N
ATOM   4249  CA   LEU B 247      31.625  43.863  86.256  1.00 19.91      B    C
ATOM   4250  CB   LEU B 247      31.167  42.839  87.314  1.00 19.07      B    C
ATOM   4251  CG   LEU B 247      32.246  42.212  88.222  1.00 21.55      B    C
ATOM   4252  CD1  LEU B 247      32.969  43.307  89.000  1.00 19.84      B    C
ATOM   4253  CD2  LEU B 247      31.613  41.199  89.194  1.00 19.90      B    C
ATOM   4254  C    LEU B 247      32.853  43.314  85.547  1.00 20.90      B    C
ATOM   4255  O    LEU B 247      33.949  43.812  85.720  1.00 20.69      B    O
ATOM   4256  N    ALA B 248      32.641  42.272  84.753  1.00 20.76      B    N
ATOM   4257  CA   ALA B 248      33.726  41.647  84.018  1.00 21.55      B    C
ATOM   4258  CB   ALA B 248      33.189  40.502  83.157  1.00 19.96      B    C
ATOM   4259  C    ALA B 248      34.447  42.666  83.144  1.00 21.66      B    C
ATOM   4260  O    ALA B 248      35.671  42.704  83.122  1.00 22.29      B    O
ATOM   4261  N    GLU B 249      33.678  43.493  82.437  1.00 21.26      B    N
ATOM   4262  CA   GLU B 249      34.245  44.503  81.545  1.00 20.43      B    C
ATOM   4263  CB   GLU B 249      33.135  45.249  80.796  1.00 20.55      B    C
ATOM   4264  CG   GLU B 249      33.630  45.995  79.564  1.00 19.07      B    C
ATOM   4265  CD   GLU B 249      32.510  46.508  78.670  1.00 19.83      B    C
ATOM   4266  OE1  GLU B 249      31.433  45.880  78.629  1.00 18.24      B    O
ATOM   4267  OE2  GLU B 249      32.720  47.530  77.987  1.00 20.19      B    O
ATOM   4268  C    GLU B 249      35.120  45.497  82.312  1.00 20.65      B    C
ATOM   4269  O    GLU B 249      36.236  45.787  81.908  1.00 21.15      B    O
```

FIG. 5-72

| ATOM | 4270 | N | LEU | B | 250 | 34.607 | 46.009 | 83.423 | 1.00 | 20.69 | B | N |
|------|------|------|-----|---|-----|--------|--------|--------|------|-------|---|---|
| ATOM | 4271 | CA | LEU | B | 250 | 35.358 | 46.964 | 84.226 | 1.00 | 22.44 | B | C |
| ATOM | 4272 | CB | LEU | B | 250 | 34.510 | 47.464 | 85.400 | 1.00 | 22.33 | B | C |
| ATOM | 4273 | CG | LEU | B | 250 | 33.242 | 48.268 | 85.087 | 1.00 | 22.02 | B | C |
| ATOM | 4274 | CD1 | LEU | B | 250 | 32.577 | 48.684 | 86.392 | 1.00 | 20.39 | B | C |
| ATOM | 4275 | CD2 | LEU | B | 250 | 33.587 | 49.490 | 84.258 | 1.00 | 20.81 | B | C |
| ATOM | 4276 | C | LEU | B | 250 | 36.663 | 46.347 | 84.753 | 1.00 | 23.96 | B | C |
| ATOM | 4277 | O | LEU | B | 250 | 37.628 | 47.052 | 84.976 | 1.00 | 24.30 | B | O |
| ATOM | 4278 | N | LEU | B | 251 | 36.680 | 45.030 | 84.945 | 1.00 | 23.91 | B | N |
| ATOM | 4279 | CA | LEU | B | 251 | 37.878 | 44.356 | 85.430 | 1.00 | 25.82 | B | C |
| ATOM | 4280 | CB | LEU | B | 251 | 37.528 | 43.032 | 86.116 | 1.00 | 25.27 | B | C |
| ATOM | 4281 | CG | LEU | B | 251 | 36.711 | 43.098 | 87.402 | 1.00 | 24.96 | B | C |
| ATOM | 4282 | CD1 | LEU | B | 251 | 36.294 | 41.699 | 87.815 | 1.00 | 24.06 | B | C |
| ATOM | 4283 | CD2 | LEU | B | 251 | 37.531 | 43.769 | 88.491 | 1.00 | 23.69 | B | C |
| ATOM | 4284 | C | LEU | B | 251 | 38.838 | 44.064 | 84.281 | 1.00 | 27.08 | B | C |
| ATOM | 4285 | O | LEU | B | 251 | 40.021 | 44.251 | 84.415 | 1.00 | 28.30 | B | O |
| ATOM | 4286 | N | LEU | B | 252 | 38.299 | 43.611 | 83.151 | 1.00 | 27.15 | B | N |
| ATOM | 4287 | CA | LEU | B | 252 | 39.112 | 43.274 | 81.988 | 1.00 | 26.81 | B | C |
| ATOM | 4288 | CB | LEU | B | 252 | 38.382 | 42.245 | 81.116 | 1.00 | 27.29 | B | C |
| ATOM | 4289 | CG | LEU | B | 252 | 38.452 | 40.770 | 81.543 | 1.00 | 28.26 | B | C |
| ATOM | 4290 | CD1 | LEU | B | 252 | 37.345 | 39.981 | 80.862 | 1.00 | 28.49 | B | C |
| ATOM | 4291 | CD2 | LEU | B | 252 | 39.812 | 40.191 | 81.202 | 1.00 | 26.61 | B | C |
| ATOM | 4292 | C | LEU | B | 252 | 39.570 | 44.441 | 81.106 | 1.00 | 26.86 | B | C |
| ATOM | 4293 | O | LEU | B | 252 | 40.627 | 44.376 | 80.510 | 1.00 | 25.89 | B | O |
| ATOM | 4294 | N | GLY | B | 253 | 38.774 | 45.505 | 81.024 | 1.00 | 25.72 | B | N |
| ATOM | 4295 | CA | GLY | B | 253 | 39.148 | 46.626 | 80.180 | 1.00 | 23.26 | B | C |
| ATOM | 4296 | C | GLY | B | 253 | 38.495 | 46.539 | 78.809 | 1.00 | 23.33 | B | C |
| ATOM | 4297 | O | GLY | B | 253 | 38.740 | 47.373 | 77.943 | 1.00 | 23.03 | B | O |
| ATOM | 4298 | N | GLN | B | 254 | 37.671 | 45.513 | 78.614 | 1.00 | 22.16 | B | N |
| ATOM | 4299 | CA | GLN | B | 254 | 36.949 | 45.305 | 77.355 | 1.00 | 23.80 | B | C |
| ATOM | 4300 | CB | GLN | B | 254 | 37.870 | 44.698 | 76.289 | 1.00 | 25.24 | B | C |
| ATOM | 4301 | CG | GLN | B | 254 | 38.667 | 43.489 | 76.744 | 1.00 | 29.25 | B | C |
| ATOM | 4302 | CD | GLN | B | 254 | 39.550 | 42.924 | 75.641 | 1.00 | 32.94 | B | C |
| ATOM | 4303 | OE1 | GLN | B | 254 | 39.073 | 42.224 | 74.740 | 1.00 | 34.35 | B | O |
| ATOM | 4304 | NE2 | GLN | B | 254 | 40.845 | 43.230 | 75.703 | 1.00 | 33.94 | B | N |
| ATOM | 4305 | C | GLN | B | 254 | 35.766 | 44.376 | 77.606 | 1.00 | 22.34 | B | C |
| ATOM | 4306 | O | GLN | B | 254 | 35.707 | 43.727 | 78.623 | 1.00 | 23.11 | B | O |
| ATOM | 4307 | N | PRO | B | 255 | 34.807 | 44.312 | 76.673 | 1.00 | 20.37 | B | N |
| ATOM | 4308 | CD | PRO | B | 255 | 34.689 | 45.040 | 75.402 | 1.00 | 19.12 | B | C |
| ATOM | 4309 | CA | PRO | B | 255 | 33.653 | 43.427 | 76.882 | 1.00 | 19.33 | B | C |
| ATOM | 4310 | CB | PRO | B | 255 | 32.814 | 43.649 | 75.623 | 1.00 | 19.07 | B | C |
| ATOM | 4311 | CG | PRO | B | 255 | 33.201 | 45.029 | 75.185 | 1.00 | 20.39 | B | C |
| ATOM | 4312 | C | PRO | B | 255 | 34.116 | 41.970 | 77.020 | 1.00 | 19.64 | B | C |
| ATOM | 4313 | O | PRO | B | 255 | 35.065 | 41.553 | 76.362 | 1.00 | 18.39 | B | O |
| ATOM | 4314 | N | ILE | B | 256 | 33.444 | 41.204 | 77.876 | 1.00 | 19.48 | B | N |
| ATOM | 4315 | CA | ILE | B | 256 | 33.804 | 39.814 | 78.087 | 1.00 | 19.22 | B | C |
| ATOM | 4316 | CB | ILE | B | 256 | 33.383 | 39.317 | 79.491 | 1.00 | 21.34 | B | C |
| ATOM | 4317 | CG2 | ILE | B | 256 | 31.858 | 39.376 | 79.639 | 1.00 | 19.53 | B | C |
| ATOM | 4318 | CG1 | ILE | B | 256 | 33.911 | 37.890 | 79.710 | 1.00 | 20.79 | B | C |
| ATOM | 4319 | CD1 | ILE | B | 256 | 33.831 | 37.401 | 81.148 | 1.00 | 18.89 | B | C |
| ATOM | 4320 | C | ILE | B | 256 | 33.195 | 38.888 | 77.033 | 1.00 | 20.64 | B | C |
| ATOM | 4321 | O | ILE | B | 256 | 33.785 | 37.885 | 76.680 | 1.00 | 19.92 | B | O |
| ATOM | 4322 | N | PHE | B | 257 | 32.016 | 39.238 | 76.528 | 1.00 | 20.72 | B | N |
| ATOM | 4323 | CA | PHE | B | 257 | 31.355 | 38.418 | 75.515 | 1.00 | 19.92 | B | C |
| ATOM | 4324 | CB | PHE | B | 257 | 30.100 | 37.756 | 76.096 | 1.00 | 18.00 | B | C |
| ATOM | 4325 | CG | PHE | B | 257 | 30.368 | 36.885 | 77.291 | 1.00 | 19.45 | B | C |
| ATOM | 4326 | CD1 | PHE | B | 257 | 31.380 | 35.926 | 77.262 | 1.00 | 20.42 | B | C |
| ATOM | 4327 | CD2 | PHE | B | 257 | 29.602 | 37.012 | 78.446 | 1.00 | 19.96 | B | C |
| ATOM | 4328 | CE1 | PHE | B | 257 | 31.625 | 35.111 | 78.365 | 1.00 | 20.59 | B | C |
| ATOM | 4329 | CE2 | PHE | B | 257 | 29.839 | 36.201 | 79.551 | 1.00 | 20.07 | B | C |

FIG. 5-73

```
ATOM   4330  CZ   PHE B 257    30.855  35.247  79.513  1.00 19.52      B    C
ATOM   4331  C    PHE B 257    30.977  39.228  74.276  1.00 20.28      B    C
ATOM   4332  O    PHE B 257    29.822  39.516  74.053  1.00 20.93      B    O
ATOM   4333  N    PRO B 258    31.970  39.610  73.462  1.00 20.75      B    N
ATOM   4334  CD   PRO B 258    33.417  39.468  73.710  1.00 19.68      B    C
ATOM   4335  CA   PRO B 258    31.728  40.388  72.244  1.00 19.66      B    C
ATOM   4336  CB   PRO B 258    33.101  40.978  71.936  1.00 19.46      B    C
ATOM   4337  CG   PRO B 258    34.023  39.888  72.376  1.00 18.19      B    C
ATOM   4338  C    PRO B 258    31.215  39.519  71.112  1.00 20.92      B    C
ATOM   4339  O    PRO B 258    31.140  38.316  71.245  1.00 23.05      B    O
ATOM   4340  N    GLY B 259    30.876  40.149  69.994  1.00 21.99      B    N
ATOM   4341  CA   GLY B 259    30.372  39.415  68.851  1.00 22.30      B    C
ATOM   4342  C    GLY B 259    29.268  40.201  68.180  1.00 24.26      B    C
ATOM   4343  O    GLY B 259    28.428  40.783  68.850  1.00 24.30      B    O
ATOM   4344  N    ASP B 260    29.267  40.213  66.854  1.00 23.77      B    N
ATOM   4345  CA   ASP B 260    28.261  40.957  66.114  1.00 26.22      B    C
ATOM   4346  CB   ASP B 260    28.875  41.513  64.829  1.00 30.10      B    C
ATOM   4347  CG   ASP B 260    30.100  42.380  65.100  1.00 33.70      B    C
ATOM   4348  OD1  ASP B 260    30.284  42.811  66.267  1.00 33.87      B    O
ATOM   4349  OD2  ASP B 260    30.869  42.637  64.146  1.00 36.21      B    O
ATOM   4350  C    ASP B 260    27.008  40.149  65.796  1.00 24.83      B    C
ATOM   4351  O    ASP B 260    26.092  40.645  65.162  1.00 26.33      B    O
ATOM   4352  N    SER B 261    26.980  38.904  66.250  1.00 24.08      B    N
ATOM   4353  CA   SER B 261    25.834  38.038  66.027  1.00 21.60      B    C
ATOM   4354  CB   SER B 261    26.116  37.050  64.894  1.00 21.44      B    C
ATOM   4355  OG   SER B 261    27.163  36.165  65.241  1.00 22.83      B    O
ATOM   4356  C    SER B 261    25.566  37.274  67.312  1.00 21.91      B    C
ATOM   4357  O    SER B 261    26.447  37.174  68.184  1.00 19.20      B    O
ATOM   4358  N    GLY B 262    24.351  36.746  67.425  1.00 20.02      B    N
ATOM   4359  CA   GLY B 262    23.991  35.970  68.593  1.00 21.70      B    C
ATOM   4360  C    GLY B 262    24.868  34.734  68.685  1.00 21.26      B    C
ATOM   4361  O    GLY B 262    25.333  34.382  69.754  1.00 20.17      B    O
ATOM   4362  N    VAL B 263    25.096  34.083  67.548  1.00 21.98      B    N
ATOM   4363  CA   VAL B 263    25.938  32.890  67.523  1.00 23.15      B    C
ATOM   4364  CB   VAL B 263    26.001  32.246  66.101  1.00 22.75      B    C
ATOM   4365  CG1  VAL B 263    24.630  31.795  65.686  1.00 24.44      B    C
ATOM   4366  CG2  VAL B 263    26.553  33.234  65.090  1.00 22.70      B    C
ATOM   4367  C    VAL B 263    27.358  33.215  67.988  1.00 22.06      B    C
ATOM   4368  O    VAL B 263    27.918  32.491  68.771  1.00 21.55      B    O
ATOM   4369  N    ASP B 264    27.920  34.317  67.502  1.00 22.01      B    N
ATOM   4370  CA   ASP B 264    29.272  34.705  67.893  1.00 23.09      B    C
ATOM   4371  CB   ASP B 264    29.745  35.914  67.058  1.00 22.78      B    C
ATOM   4372  CG   ASP B 264    30.148  35.534  65.630  1.00 24.32      B    C
ATOM   4373  OD1  ASP B 264    30.265  34.327  65.334  1.00 25.53      B    O
ATOM   4374  OD2  ASP B 264    30.370  36.444  64.803  1.00 24.79      B    O
ATOM   4375  C    ASP B 264    29.347  35.030  69.386  1.00 22.89      B    C
ATOM   4376  O    ASP B 264    30.338  34.756  70.032  1.00 24.33      B    O
ATOM   4377  N    GLN B 265    28.283  35.619  69.921  1.00 23.27      B    N
ATOM   4378  CA   GLN B 265    28.219  35.954  71.338  1.00 23.07      B    C
ATOM   4379  CB   GLN B 265    26.981  36.814  71.609  1.00 22.60      B    C
ATOM   4380  CG   GLN B 265    27.035  38.159  70.916  1.00 24.03      B    C
ATOM   4381  CD   GLN B 265    25.687  38.855  70.841  1.00 25.26      B    C
ATOM   4382  OE1  GLN B 265    25.521  39.792  70.090  1.00 26.91      B    O
ATOM   4383  NE2  GLN B 265    24.726  38.392  71.626  1.00 25.36      B    N
ATOM   4384  C    GLN B 265    28.161  34.665  72.152  1.00 21.83      B    C
ATOM   4385  O    GLN B 265    28.792  34.555  73.180  1.00 20.92      B    O
ATOM   4386  N    LEU B 266    27.393  33.699  71.656  1.00 21.65      B    N
ATOM   4387  CA   LEU B 266    27.252  32.408  72.311  1.00 23.72      B    C
ATOM   4388  CB   LEU B 266    26.204  31.561  71.589  1.00 24.37      B    C
ATOM   4389  CG   LEU B 266    24.827  31.443  72.251  1.00 28.13      B    C
```

FIG. 5-74

| ATOM | 4390 | CD1 | LEU | B | 266 | 24.346 | 32.801 | 72.661 | 1.00 | 29.34 | B | C |
|---|---|---|---|---|---|---|---|---|---|---|---|---|
| ATOM | 4391 | CD2 | LEU | B | 266 | 23.832 | 30.780 | 71.294 | 1.00 | 26.64 | B | C |
| ATOM | 4392 | C | LEU | B | 266 | 28.577 | 31.658 | 72.357 | 1.00 | 24.07 | B | C |
| ATOM | 4393 | O | LEU | B | 266 | 28.915 | 31.086 | 73.371 | 1.00 | 24.14 | B | O |
| ATOM | 4394 | N | VAL | B | 267 | 29.331 | 31.658 | 71.262 | 1.00 | 24.46 | B | N |
| ATOM | 4395 | CA | VAL | B | 267 | 30.596 | 30.943 | 71.298 | 1.00 | 25.76 | B | C |
| ATOM | 4396 | CB | VAL | B | 267 | 31.272 | 30.855 | 69.898 | 1.00 | 25.92 | B | C |
| ATOM | 4397 | CG1 | VAL | B | 267 | 30.346 | 30.138 | 68.923 | 1.00 | 23.57 | B | C |
| ATOM | 4398 | CG2 | VAL | B | 267 | 31.633 | 32.232 | 69.391 | 1.00 | 29.47 | B | C |
| ATOM | 4399 | C | VAL | B | 267 | 31.526 | 31.610 | 72.300 | 1.00 | 26.25 | B | C |
| ATOM | 4400 | O | VAL | B | 267 | 32.235 | 30.942 | 73.041 | 1.00 | 26.95 | B | O |
| ATOM | 4401 | N | GLU | B | 268 | 31.496 | 32.935 | 72.336 | 1.00 | 26.39 | B | N |
| ATOM | 4402 | CA | GLU | B | 268 | 32.335 | 33.678 | 73.262 | 1.00 | 26.36 | B | C |
| ATOM | 4403 | CB | GLU | B | 268 | 32.116 | 35.176 | 73.036 | 1.00 | 28.65 | B | C |
| ATOM | 4404 | CG | GLU | B | 268 | 33.324 | 36.024 | 73.339 | 1.00 | 32.25 | B | C |
| ATOM | 4405 | CD | GLU | B | 268 | 34.589 | 35.505 | 72.666 | 1.00 | 32.96 | B | C |
| ATOM | 4406 | OE1 | GLU | B | 268 | 34.691 | 35.570 | 71.422 | 1.00 | 31.50 | B | O |
| ATOM | 4407 | OE2 | GLU | B | 268 | 35.478 | 35.024 | 73.397 | 1.00 | 34.30 | B | O |
| ATOM | 4408 | C | GLU | B | 268 | 31.997 | 33.274 | 74.699 | 1.00 | 25.39 | B | C |
| ATOM | 4409 | O | GLU | B | 268 | 32.885 | 33.097 | 75.520 | 1.00 | 24.97 | B | O |
| ATOM | 4410 | N | ILE | B | 269 | 30.705 | 33.115 | 74.977 | 1.00 | 24.06 | B | N |
| ATOM | 4411 | CA | ILE | B | 269 | 30.227 | 32.715 | 76.296 | 1.00 | 24.37 | B | C |
| ATOM | 4412 | CB | ILE | B | 269 | 28.688 | 32.838 | 76.377 | 1.00 | 22.90 | B | C |
| ATOM | 4413 | CG2 | ILE | B | 269 | 28.168 | 32.176 | 77.637 | 1.00 | 21.09 | B | C |
| ATOM | 4414 | CG1 | ILE | B | 269 | 28.283 | 34.313 | 76.320 | 1.00 | 24.81 | B | C |
| ATOM | 4415 | CD1 | ILE | B | 269 | 26.802 | 34.535 | 76.088 | 1.00 | 22.49 | B | C |
| ATOM | 4416 | C | ILE | B | 269 | 30.632 | 31.267 | 76.551 | 1.00 | 25.86 | B | C |
| ATOM | 4417 | O | ILE | B | 269 | 31.028 | 30.920 | 77.648 | 1.00 | 27.37 | B | O |
| ATOM | 4418 | N | ILE | B | 270 | 30.528 | 30.432 | 75.520 | 1.00 | 25.52 | B | N |
| ATOM | 4419 | CA | ILE | B | 270 | 30.894 | 29.029 | 75.639 | 1.00 | 25.98 | B | C |
| ATOM | 4420 | CB | ILE | B | 270 | 30.465 | 28.245 | 74.368 | 1.00 | 25.08 | B | C |
| ATOM | 4421 | CG2 | ILE | B | 270 | 31.104 | 26.873 | 74.344 | 1.00 | 25.73 | B | C |
| ATOM | 4422 | CG1 | ILE | B | 270 | 28.943 | 28.110 | 74.340 | 1.00 | 25.31 | B | C |
| ATOM | 4423 | CD1 | ILE | B | 270 | 28.395 | 27.549 | 73.043 | 1.00 | 26.10 | B | C |
| ATOM | 4424 | C | ILE | B | 270 | 32.395 | 28.857 | 75.891 | 1.00 | 26.52 | B | C |
| ATOM | 4425 | O | ILE | B | 270 | 32.790 | 27.954 | 76.610 | 1.00 | 26.79 | B | O |
| ATOM | 4426 | N | LYS | B | 271 | 33.222 | 29.726 | 75.310 | 1.00 | 26.31 | B | N |
| ATOM | 4427 | CA | LYS | B | 271 | 34.665 | 29.621 | 75.518 | 1.00 | 28.20 | B | C |
| ATOM | 4428 | CB | LYS | B | 271 | 35.436 | 30.544 | 74.566 | 1.00 | 27.64 | B | C |
| ATOM | 4429 | CG | LYS | B | 271 | 35.196 | 30.233 | 73.090 | 1.00 | 30.55 | B | C |
| ATOM | 4430 | CD | LYS | B | 271 | 36.406 | 30.548 | 72.218 | 1.00 | 31.64 | B | C |
| ATOM | 4431 | CE | LYS | B | 271 | 36.830 | 31.987 | 72.313 | 1.00 | 34.01 | B | C |
| ATOM | 4432 | NZ | LYS | B | 271 | 37.948 | 32.242 | 71.381 | 1.00 | 36.53 | B | N |
| ATOM | 4433 | C | LYS | B | 271 | 35.071 | 29.898 | 76.973 | 1.00 | 30.02 | B | C |
| ATOM | 4434 | O | LYS | B | 271 | 36.229 | 29.680 | 77.354 | 1.00 | 30.55 | B | O |
| ATOM | 4435 | N | VAL | B | 272 | 34.142 | 30.375 | 77.797 | 1.00 | 29.13 | B | N |
| ATOM | 4436 | CA | VAL | B | 272 | 34.502 | 30.598 | 79.191 | 1.00 | 29.42 | B | C |
| ATOM | 4437 | CB | VAL | B | 272 | 34.355 | 32.083 | 79.614 | 1.00 | 29.11 | B | C |
| ATOM | 4438 | CG1 | VAL | B | 272 | 35.152 | 32.975 | 78.674 | 1.00 | 26.93 | B | C |
| ATOM | 4439 | CG2 | VAL | B | 272 | 32.905 | 32.476 | 79.645 | 1.00 | 32.30 | B | C |
| ATOM | 4440 | C | VAL | B | 272 | 33.697 | 29.712 | 80.142 | 1.00 | 28.77 | B | C |
| ATOM | 4441 | O | VAL | B | 272 | 34.260 | 29.139 | 81.053 | 1.00 | 28.18 | B | O |
| ATOM | 4442 | N | LEU | B | 273 | 32.390 | 29.582 | 79.913 | 1.00 | 28.62 | B | N |
| ATOM | 4443 | CA | LEU | B | 273 | 31.546 | 28.763 | 80.789 | 1.00 | 28.69 | B | C |
| ATOM | 4444 | CB | LEU | B | 273 | 30.111 | 29.280 | 80.805 | 1.00 | 28.90 | B | C |
| ATOM | 4445 | CG | LEU | B | 273 | 29.833 | 30.615 | 81.488 | 1.00 | 30.45 | B | C |
| ATOM | 4446 | CD1 | LEU | B | 273 | 28.330 | 30.886 | 81.471 | 1.00 | 28.67 | B | C |
| ATOM | 4447 | CD2 | LEU | B | 273 | 30.350 | 30.569 | 82.913 | 1.00 | 30.96 | B | C |
| ATOM | 4448 | C | LEU | B | 273 | 31.492 | 27.305 | 80.374 | 1.00 | 29.35 | B | C |
| ATOM | 4449 | O | LEU | B | 273 | 31.008 | 26.454 | 81.119 | 1.00 | 29.33 | B | O |

FIG. 5-75

```
ATOM   4450  N    GLY B 274      31.984  27.019  79.177  1.00 29.45      B  N
ATOM   4451  CA   GLY B 274      31.936  25.659  78.689  1.00 29.13      B  C
ATOM   4452  C    GLY B 274      30.610  25.476  77.978  1.00 30.27      B  C
ATOM   4453  O    GLY B 274      29.718  26.307  78.121  1.00 29.19      B  O
ATOM   4454  N    THR B 275      30.477  24.404  77.203  1.00 30.51      B  N
ATOM   4455  CA   THR B 275      29.232  24.147  76.490  1.00 30.90      B  C
ATOM   4456  CB   THR B 275      29.342  22.890  75.556  1.00 31.79      B  C
ATOM   4457  OG1  THR B 275      30.536  22.964  74.765  1.00 31.66      B  O
ATOM   4458  CG2  THR B 275      28.141  22.808  74.617  1.00 30.52      B  C
ATOM   4459  C    THR B 275      28.142  23.872  77.523  1.00 32.08      B  C
ATOM   4460  O    THR B 275      28.368  23.151  78.493  1.00 32.20      B  O
ATOM   4461  N    PRO B 276      26.943  24.438  77.327  1.00 32.69      B  N
ATOM   4462  CD   PRO B 276      26.514  25.351  76.252  1.00 32.13      B  C
ATOM   4463  CA   PRO B 276      25.855  24.215  78.279  1.00 33.62      B  C
ATOM   4464  CB   PRO B 276      24.860  25.306  77.908  1.00 32.88      B  C
ATOM   4465  CG   PRO B 276      25.007  25.369  76.429  1.00 32.61      B  C
ATOM   4466  C    PRO B 276      25.248  22.816  78.163  1.00 34.94      B  C
ATOM   4467  O    PRO B 276      25.032  22.325  77.068  1.00 36.62      B  O
ATOM   4468  N    THR B 277      24.967  22.192  79.304  1.00 35.21      B  N
ATOM   4469  CA   THR B 277      24.381  20.857  79.329  1.00 35.04      B  C
ATOM   4470  CB   THR B 277      24.405  20.261  80.741  1.00 33.91      B  C
ATOM   4471  OG1  THR B 277      23.457  20.948  81.568  1.00 33.49      B  O
ATOM   4472  CG2  THR B 277      25.789  20.401  81.346  1.00 33.85      B  C
ATOM   4473  C    THR B 277      22.928  20.920  78.866  1.00 36.68      B  C
ATOM   4474  O    THR B 277      22.288  21.972  78.929  1.00 36.55      B  O
ATOM   4475  N    ALA B 278      22.399  19.789  78.409  1.00 37.71      B  N
ATOM   4476  CA   ALA B 278      21.020  19.762  77.941  1.00 38.44      B  C
ATOM   4477  CB   ALA B 278      20.625  18.341  77.529  1.00 38.44      B  C
ATOM   4478  C    ALA B 278      20.062  20.301  79.005  1.00 38.62      B  C
ATOM   4479  O    ALA B 278      19.017  20.871  78.678  1.00 39.10      B  O
ATOM   4480  N    ALA B 279      20.410  20.132  80.278  1.00 39.05      B  N
ATOM   4481  CA   ALA B 279      19.551  20.632  81.352  1.00 39.31      B  C
ATOM   4482  CB   ALA B 279      20.028  20.103  82.719  1.00 38.66      B  C
ATOM   4483  C    ALA B 279      19.565  22.164  81.345  1.00 38.98      B  C
ATOM   4484  O    ALA B 279      18.535  22.803  81.468  1.00 39.28      B  O
ATOM   4485  N    GLN B 280      20.756  22.733  81.192  1.00 38.64      B  N
ATOM   4486  CA   GLN B 280      20.915  24.177  81.175  1.00 37.09      B  C
ATOM   4487  CB   GLN B 280      22.397  24.513  81.171  1.00 35.48      B  C
ATOM   4488  CG   GLN B 280      23.036  24.280  82.526  1.00 33.98      B  C
ATOM   4489  CD   GLN B 280      24.546  24.303  82.473  1.00 32.84      B  C
ATOM   4490  OE1  GLN B 280      25.200  24.617  83.462  1.00 33.03      B  O
ATOM   4491  NE2  GLN B 280      25.110  23.952  81.319  1.00 28.32      B  N
ATOM   4492  C    GLN B 280      20.202  24.863  80.016  1.00 37.75      B  C
ATOM   4493  O    GLN B 280      19.532  25.866  80.213  1.00 37.93      B  O
ATOM   4494  N    ILE B 281      20.344  24.329  78.808  1.00 38.44      B  N
ATOM   4495  CA   ILE B 281      19.668  24.926  77.661  1.00 39.91      B  C
ATOM   4496  CB   ILE B 281      19.962  24.133  76.383  1.00 41.83      B  C
ATOM   4497  CG2  ILE B 281      19.641  22.682  76.616  1.00 43.81      B  C
ATOM   4498  CG1  ILE B 281      19.129  24.659  75.207  1.00 44.43      B  C
ATOM   4499  CD1  ILE B 281      19.639  25.976  74.594  1.00 46.50      B  C
ATOM   4500  C    ILE B 281      18.172  24.867  77.961  1.00 39.77      B  C
ATOM   4501  O    ILE B 281      17.397  25.741  77.555  1.00 39.64      B  O
ATOM   4502  N    ALA B 282      17.782  23.835  78.703  1.00 39.75      B  N
ATOM   4503  CA   ALA B 282      16.389  23.625  79.073  1.00 39.37      B  C
ATOM   4504  CB   ALA B 282      16.211  22.215  79.653  1.00 40.34      B  C
ATOM   4505  C    ALA B 282      15.892  24.670  80.074  1.00 39.67      B  C
ATOM   4506  O    ALA B 282      14.799  25.219  79.922  1.00 37.97      B  O
ATOM   4507  N    GLU B 283      16.683  24.931  81.107  1.00 39.94      B  N
ATOM   4508  CA   GLU B 283      16.287  25.924  82.099  1.00 40.48      B  C
ATOM   4509  CB   GLU B 283      17.316  25.968  83.236  1.00 42.08      B  C
```

FIG. 5-76

```
ATOM   4510  CG   GLU B 283      17.727  24.565  83.724  1.00 45.84      B   C
ATOM   4511  CD   GLU B 283      18.029  24.505  85.208  1.00 48.33      B   C
ATOM   4512  OE1  GLU B 283      17.108  24.816  86.008  1.00 49.27      B   O
ATOM   4513  OE2  GLU B 283      19.180  24.141  85.575  1.00 49.66      B   O
ATOM   4514  C    GLU B 283      16.160  27.285  81.399  1.00 39.29      B   C
ATOM   4515  O    GLU B 283      15.337  28.117  81.780  1.00 39.33      B   O
ATOM   4516  N    MET B 284      16.961  27.485  80.355  1.00 37.42      B   N
ATOM   4517  CA   MET B 284      16.932  28.724  79.586  1.00 37.52      B   C
ATOM   4518  CB   MET B 284      18.265  28.953  78.866  1.00 36.91      B   C
ATOM   4519  CG   MET B 284      19.546  28.822  79.673  1.00 37.86      B   C
ATOM   4520  SD   MET B 284      21.027  29.115  78.617  1.00 37.58      B   S
ATOM   4521  CE   MET B 284      22.023  29.988  79.695  1.00 40.12      B   C
ATOM   4522  C    MET B 284      15.866  28.643  78.497  1.00 37.61      B   C
ATOM   4523  O    MET B 284      15.405  29.680  77.978  1.00 36.17      B   O
ATOM   4524  N    ASN B 285      15.484  27.408  78.171  1.00 38.35      B   N
ATOM   4525  CA   ASN B 285      14.560  27.080  77.078  1.00 40.83      B   C
ATOM   4526  CB   ASN B 285      13.185  26.586  77.586  1.00 42.17      B   C
ATOM   4527  CG   ASN B 285      12.283  27.694  78.012  1.00 43.04      B   C
ATOM   4528  OD1  ASN B 285      12.727  28.657  78.632  1.00 48.16      B   O
ATOM   4529  ND2  ASN B 285      10.994  27.569  77.695  1.00 40.21      B   N
ATOM   4530  C    ASN B 285      14.381  28.131  75.988  1.00 40.48      B   C
ATOM   4531  O    ASN B 285      13.656  29.093  76.146  1.00 40.15      B   O
ATOM   4532  N    PRO B 286      15.069  27.939  74.850  1.00 41.48      B   N
ATOM   4533  CD   PRO B 286      16.051  26.862  74.605  1.00 42.10      B   C
ATOM   4534  CA   PRO B 286      15.007  28.849  73.702  1.00 42.55      B   C
ATOM   4535  CB   PRO B 286      16.277  28.507  72.929  1.00 42.83      B   C
ATOM   4536  CG   PRO B 286      16.372  27.033  73.117  1.00 42.44      B   C
ATOM   4537  C    PRO B 286      13.775  28.571  72.862  1.00 42.88      B   C
ATOM   4538  O    PRO B 286      13.035  27.635  73.136  1.00 43.24      B   O
ATOM   4539  N    ASN B 287      13.566  29.384  71.827  1.00 43.95      B   N
ATOM   4540  CA   ASN B 287      12.443  29.124  70.940  1.00 44.04      B   C
ATOM   4541  CB   ASN B 287      12.256  30.236  69.900  1.00 43.89      B   C
ATOM   4542  CG   ASN B 287      13.570  30.837  69.418  1.00 44.76      B   C
ATOM   4543  OD1  ASN B 287      14.619  30.170  69.382  1.00 44.79      B   O
ATOM   4544  ND2  ASN B 287      13.511  32.105  69.004  1.00 43.67      B   N
ATOM   4545  C    ASN B 287      12.872  27.832  70.259  1.00 44.63      B   C
ATOM   4546  O    ASN B 287      12.085  26.891  70.117  1.00 45.43      B   O
ATOM   4547  N    TYR B 288      14.152  27.774  69.897  1.00 44.76      B   N
ATOM   4548  CA   TYR B 288      14.710  26.604  69.241  1.00 45.03      B   C
ATOM   4549  CB   TYR B 288      14.115  26.463  67.841  1.00 44.88      B   C
ATOM   4550  CG   TYR B 288      14.765  25.383  67.004  1.00 46.28      B   C
ATOM   4551  CD1  TYR B 288      15.492  25.706  65.860  1.00 45.84      B   C
ATOM   4552  CE1  TYR B 288      16.109  24.720  65.103  1.00 48.08      B   C
ATOM   4553  CD2  TYR B 288      14.668  24.038  67.374  1.00 46.98      B   C
ATOM   4554  CE2  TYR B 288      15.279  23.035  66.628  1.00 47.94      B   C
ATOM   4555  CZ   TYR B 288      15.998  23.383  65.491  1.00 49.21      B   C
ATOM   4556  OH   TYR B 288      16.606  22.402  64.741  1.00 49.87      B   O
ATOM   4557  C    TYR B 288      16.221  26.705  69.135  1.00 45.52      B   C
ATOM   4558  O    TYR B 288      16.785  27.793  69.013  1.00 46.00      B   O
ATOM   4559  N    ALA B 289      16.876  25.557  69.190  1.00 46.29      B   N
ATOM   4560  CA   ALA B 289      18.326  25.508  69.069  1.00 47.83      B   C
ATOM   4561  CB   ALA B 289      19.000  25.805  70.413  1.00 47.95      B   C
ATOM   4562  C    ALA B 289      18.717  24.121  68.605  1.00 47.44      B   C
ATOM   4563  O    ALA B 289      18.054  23.147  68.928  1.00 47.57      B   O
ATOM   4564  N    GLU B 290      19.774  24.045  67.809  1.00 47.36      B   N
ATOM   4565  CA   GLU B 290      20.271  22.752  67.368  1.00 48.25      B   C
ATOM   4566  CB   GLU B 290      20.885  22.839  65.974  1.00 47.83      B   C
ATOM   4567  CG   GLU B 290      20.018  23.485  64.927  1.00 46.60      B   C
ATOM   4568  CD   GLU B 290      20.775  23.663  63.619  1.00 46.76      B   C
ATOM   4569  OE1  GLU B 290      21.161  24.817  63.297  1.00 46.43      B   O
```

FIG. 5-77

| ATOM | 4570 | OE2 | GLU | B | 290 | 21.003 | 22.642 | 62.924 | 1.00 | 45.01 | B | O |
|------|------|-----|-----|---|-----|--------|--------|--------|------|-------|---|---|
| ATOM | 4571 | C | GLU | B | 290 | 21.388 | 22.514 | 68.379 | 1.00 | 48.76 | B | C |
| ATOM | 4572 | O | GLU | B | 290 | 22.108 | 23.453 | 68.754 | 1.00 | 50.08 | B | O |
| ATOM | 4573 | N | PHE | B | 291 | 21.554 | 21.280 | 68.819 | 1.00 | 48.54 | B | N |
| ATOM | 4574 | CA | PHE | B | 291 | 22.593 | 20.994 | 69.790 | 1.00 | 48.27 | B | C |
| ATOM | 4575 | CB | PHE | B | 291 | 22.150 | 19.805 | 70.647 | 1.00 | 46.73 | B | C |
| ATOM | 4576 | CG | PHE | B | 291 | 20.920 | 20.104 | 71.451 | 1.00 | 45.58 | B | C |
| ATOM | 4577 | CD1 | PHE | B | 291 | 19.668 | 20.101 | 70.835 | 1.00 | 44.62 | B | C |
| ATOM | 4578 | CD2 | PHE | B | 291 | 21.016 | 20.513 | 72.778 | 1.00 | 44.68 | B | C |
| ATOM | 4579 | CE1 | PHE | B | 291 | 18.530 | 20.509 | 71.520 | 1.00 | 44.48 | B | C |
| ATOM | 4580 | CE2 | PHE | B | 291 | 19.881 | 20.923 | 73.478 | 1.00 | 44.64 | B | C |
| ATOM | 4581 | CZ | PHE | B | 291 | 18.633 | 20.924 | 72.846 | 1.00 | 44.65 | B | C |
| ATOM | 4582 | C | PHE | B | 291 | 23.929 | 20.764 | 69.087 | 1.00 | 48.41 | B | C |
| ATOM | 4583 | O | PHE | B | 291 | 24.512 | 19.686 | 69.150 | 1.00 | 48.19 | B | O |
| ATOM | 4584 | N | LYS | B | 292 | 24.393 | 21.827 | 68.429 | 1.00 | 48.84 | B | N |
| ATOM | 4585 | CA | LYS | B | 292 | 25.645 | 21.844 | 67.676 | 1.00 | 49.03 | B | C |
| ATOM | 4586 | CB | LYS | B | 292 | 25.357 | 22.087 | 66.189 | 1.00 | 49.54 | B | C |
| ATOM | 4587 | CG | LYS | B | 292 | 24.377 | 21.100 | 65.550 | 1.00 | 50.85 | B | C |
| ATOM | 4588 | CD | LYS | B | 292 | 25.089 | 19.853 | 65.054 | 1.00 | 52.56 | B | C |
| ATOM | 4589 | CE | LYS | B | 292 | 24.223 | 19.065 | 64.082 | 1.00 | 54.48 | B | C |
| ATOM | 4590 | NZ | LYS | B | 292 | 22.934 | 18.661 | 64.725 | 1.00 | 54.20 | B | N |
| ATOM | 4591 | C | LYS | B | 292 | 26.504 | 23.000 | 68.185 | 1.00 | 48.82 | B | C |
| ATOM | 4592 | O | LYS | B | 292 | 26.169 | 24.155 | 67.955 | 1.00 | 50.24 | B | O |
| ATOM | 4593 | N | PHE | B | 293 | 27.597 | 22.704 | 68.881 | 1.00 | 47.42 | B | N |
| ATOM | 4594 | CA | PHE | B | 293 | 28.466 | 23.773 | 69.357 | 1.00 | 46.47 | B | C |
| ATOM | 4595 | CB | PHE | B | 293 | 27.830 | 24.477 | 70.564 | 1.00 | 44.76 | B | C |
| ATOM | 4596 | CG | PHE | B | 293 | 27.144 | 25.775 | 70.222 | 1.00 | 42.93 | B | C |
| ATOM | 4597 | CD1 | PHE | B | 293 | 25.793 | 25.967 | 70.518 | 1.00 | 42.19 | B | C |
| ATOM | 4598 | CD2 | PHE | B | 293 | 27.854 | 26.812 | 69.615 | 1.00 | 41.65 | B | C |
| ATOM | 4599 | CE1 | PHE | B | 293 | 25.156 | 27.179 | 70.214 | 1.00 | 41.40 | B | C |
| ATOM | 4600 | CE2 | PHE | B | 293 | 27.235 | 28.024 | 69.307 | 1.00 | 41.12 | B | C |
| ATOM | 4601 | CZ | PHE | B | 293 | 25.882 | 28.213 | 69.606 | 1.00 | 41.96 | B | C |
| ATOM | 4602 | C | PHE | B | 293 | 29.861 | 23.263 | 69.714 | 1.00 | 46.24 | B | C |
| ATOM | 4603 | O | PHE | B | 293 | 30.098 | 22.057 | 69.740 | 1.00 | 45.25 | B | O |
| ATOM | 4608 | N | TRP | B | 301 | 37.768 | 30.531 | 85.621 | 1.00 | 33.70 | B | N |
| ATOM | 4609 | CA | TRP | B | 301 | 37.545 | 31.952 | 85.847 | 1.00 | 33.06 | B | C |
| ATOM | 4610 | CB | TRP | B | 301 | 36.453 | 32.158 | 86.894 | 1.00 | 31.08 | B | C |
| ATOM | 4611 | CG | TRP | B | 301 | 35.096 | 32.090 | 86.297 | 1.00 | 29.17 | B | C |
| ATOM | 4612 | CD2 | TRP | B | 301 | 34.485 | 33.074 | 85.456 | 1.00 | 27.03 | B | C |
| ATOM | 4613 | CE2 | TRP | B | 301 | 33.212 | 32.588 | 85.098 | 1.00 | 27.60 | B | C |
| ATOM | 4614 | CE3 | TRP | B | 301 | 34.889 | 34.327 | 84.970 | 1.00 | 26.66 | B | C |
| ATOM | 4615 | CD1 | TRP | B | 301 | 34.198 | 31.070 | 86.411 | 1.00 | 28.84 | B | C |
| ATOM | 4616 | NE1 | TRP | B | 301 | 33.062 | 31.359 | 85.695 | 1.00 | 28.04 | B | N |
| ATOM | 4617 | CZ2 | TRP | B | 301 | 32.336 | 33.304 | 84.273 | 1.00 | 28.28 | B | C |
| ATOM | 4618 | CZ3 | TRP | B | 301 | 34.022 | 35.041 | 84.151 | 1.00 | 25.91 | B | C |
| ATOM | 4619 | CH2 | TRP | B | 301 | 32.759 | 34.530 | 83.813 | 1.00 | 26.22 | B | C |
| ATOM | 4620 | C | TRP | B | 301 | 38.778 | 32.760 | 86.222 | 1.00 | 33.58 | B | C |
| ATOM | 4621 | O | TRP | B | 301 | 38.967 | 33.877 | 85.725 | 1.00 | 33.77 | B | O |
| ATOM | 4622 | N | THR | B | 302 | 39.622 | 32.201 | 87.084 | 1.00 | 34.88 | B | N |
| ATOM | 4623 | CA | THR | B | 302 | 40.825 | 32.903 | 87.515 | 1.00 | 36.12 | B | C |
| ATOM | 4624 | CB | THR | B | 302 | 41.577 | 32.110 | 88.584 | 1.00 | 36.50 | B | C |
| ATOM | 4625 | OG1 | THR | B | 302 | 40.649 | 31.654 | 89.574 | 1.00 | 35.65 | B | O |
| ATOM | 4626 | CG2 | THR | B | 302 | 42.634 | 32.998 | 89.257 | 1.00 | 36.54 | B | C |
| ATOM | 4627 | C | THR | B | 302 | 41.794 | 33.211 | 86.370 | 1.00 | 36.96 | B | C |
| ATOM | 4628 | O | THR | B | 302 | 42.619 | 34.124 | 86.477 | 1.00 | 37.46 | B | O |
| ATOM | 4629 | N | LYS | B | 303 | 41.703 | 32.460 | 85.278 | 1.00 | 36.83 | B | N |
| ATOM | 4630 | CA | LYS | B | 303 | 42.589 | 32.717 | 84.151 | 1.00 | 37.34 | B | C |
| ATOM | 4631 | CB | LYS | B | 303 | 43.017 | 31.393 | 83.516 | 1.00 | 40.09 | B | C |
| ATOM | 4632 | CG | LYS | B | 303 | 43.868 | 30.544 | 84.475 | 1.00 | 42.92 | B | C |
| ATOM | 4633 | CD | LYS | B | 303 | 44.770 | 29.590 | 83.720 | 1.00 | 45.66 | B | C |

FIG. 5-78

```
ATOM   4634  CE   LYS B 303      45.746  28.864  84.644  1.00 47.53      B   C
ATOM   4635  NZ   LYS B 303      46.734  28.062  83.844  1.00 46.97      B   N
ATOM   4636  C    LYS B 303      41.970  33.666  83.119  1.00 36.24      B   C
ATOM   4637  O    LYS B 303      42.608  34.042  82.147  1.00 35.66      B   O
ATOM   4638  N    VAL B 304      40.728  34.061  83.364  1.00 34.79      B   N
ATOM   4639  CA   VAL B 304      40.007  34.990  82.498  1.00 34.93      B   C
ATOM   4640  CB   VAL B 304      38.484  34.972  82.819  1.00 34.91      B   C
ATOM   4641  CG1  VAL B 304      37.769  36.111  82.087  1.00 32.44      B   C
ATOM   4642  CG2  VAL B 304      37.886  33.619  82.446  1.00 33.32      B   C
ATOM   4643  C    VAL B 304      40.510  36.414  82.709  1.00 34.84      B   C
ATOM   4644  O    VAL B 304      40.617  37.183  81.766  1.00 34.93      B   O
ATOM   4645  N    PHE B 305      40.819  36.740  83.962  1.00 33.78      B   N
ATOM   4646  CA   PHE B 305      41.271  38.076  84.344  1.00 34.67      B   C
ATOM   4647  CB   PHE B 305      40.516  38.505  85.611  1.00 31.76      B   C
ATOM   4648  CG   PHE B 305      39.020  38.368  85.501  1.00 28.26      B   C
ATOM   4649  CD1  PHE B 305      38.248  39.395  84.968  1.00 27.03      B   C
ATOM   4650  CD2  PHE B 305      38.384  37.196  85.901  1.00 27.85      B   C
ATOM   4651  CE1  PHE B 305      36.864  39.264  84.838  1.00 24.27      B   C
ATOM   4652  CE2  PHE B 305      36.997  37.051  85.776  1.00 27.29      B   C
ATOM   4653  CZ   PHE B 305      36.237  38.091  85.239  1.00 25.87      B   C
ATOM   4654  C    PHE B 305      42.779  38.172  84.571  1.00 36.62      B   C
ATOM   4655  O    PHE B 305      43.481  37.160  84.564  1.00 37.06      B   O
ATOM   4656  N    ARG B 306      43.266  39.399  84.764  1.00 38.68      B   N
ATOM   4657  CA   ARG B 306      44.691  39.639  85.001  1.00 41.34      B   C
ATOM   4658  CB   ARG B 306      44.954  41.124  85.208  1.00 43.31      B   C
ATOM   4659  CG   ARG B 306      44.554  41.993  84.035  1.00 48.75      B   C
ATOM   4660  CD   ARG B 306      44.365  43.427  84.505  1.00 51.25      B   C
ATOM   4661  NE   ARG B 306      43.776  43.433  85.841  1.00 53.87      B   N
ATOM   4662  CZ   ARG B 306      43.216  44.491  86.415  1.00 55.76      B   C
ATOM   4663  NH1  ARG B 306      43.163  45.648  85.762  1.00 56.29      B   N
ATOM   4664  NH2  ARG B 306      42.717  44.387  87.648  1.00 56.11      B   N
ATOM   4665  C    ARG B 306      45.088  38.875  86.264  1.00 42.00      B   C
ATOM   4666  O    ARG B 306      44.235  38.479  87.052  1.00 41.36      B   O
ATOM   4667  N    PRO B 307      46.394  38.652  86.459  1.00 42.77      B   N
ATOM   4668  CD   PRO B 307      47.450  38.784  85.439  1.00 43.61      B   C
ATOM   4669  CA   PRO B 307      46.895  37.931  87.631  1.00 43.22      B   C
ATOM   4670  CB   PRO B 307      48.393  37.818  87.353  1.00 43.40      B   C
ATOM   4671  CG   PRO B 307      48.427  37.694  85.846  1.00 43.30      B   C
ATOM   4672  C    PRO B 307      46.591  38.566  88.989  1.00 43.52      B   C
ATOM   4673  O    PRO B 307      46.231  37.868  89.936  1.00 44.25      B   O
ATOM   4674  N    ALA B 308      46.725  39.883  89.082  1.00 43.22      B   N
ATOM   4675  CA   ALA B 308      46.480  40.591  90.342  1.00 43.23      B   C
ATOM   4676  CB   ALA B 308      46.952  42.047  90.205  1.00 44.62      B   C
ATOM   4677  C    ALA B 308      45.009  40.559  90.782  1.00 42.25      B   C
ATOM   4678  O    ALA B 308      44.720  40.485  91.965  1.00 43.89      B   O
ATOM   4679  N    THR B 309      44.097  40.617  89.817  1.00 39.85      B   N
ATOM   4680  CA   THR B 309      42.656  40.612  90.074  1.00 36.44      B   C
ATOM   4681  CB   THR B 309      41.877  39.942  88.904  1.00 36.02      B   C
ATOM   4682  OG1  THR B 309      42.229  40.570  87.664  1.00 34.20      B   O
ATOM   4683  CG2  THR B 309      40.375  40.079  89.116  1.00 33.39      B   C
ATOM   4684  C    THR B 309      42.225  39.937  91.375  1.00 34.50      B   C
ATOM   4685  O    THR B 309      42.495  38.774  91.596  1.00 33.92      B   O
ATOM   4686  N    PRO B 310      41.524  40.681  92.242  1.00 34.02      B   N
ATOM   4687  CD   PRO B 310      41.097  42.075  92.033  1.00 33.66      B   C
ATOM   4688  CA   PRO B 310      41.037  40.181  93.531  1.00 33.91      B   C
ATOM   4689  CB   PRO B 310      40.236  41.359  94.080  1.00 33.33      B   C
ATOM   4690  CG   PRO B 310      40.880  42.547  93.439  1.00 34.03      B   C
ATOM   4691  C    PRO B 310      40.174  38.929  93.375  1.00 33.50      B   C
ATOM   4692  O    PRO B 310      39.200  38.925  92.631  1.00 33.08      B   O
ATOM   4693  N    PRO B 311      40.520  37.856  94.098  1.00 33.46      B   N
```

FIG. 5-79

| ATOM | 4694 | CD | PRO | B | 311 | 41.602 | 37.750 | 95.094 | 1.00 | 33.78 | B | C |
|------|------|------|-----|---|-----|--------|--------|--------|------|-------|---|---|
| ATOM | 4695 | CA | PRO | B | 311 | 39.758 | 36.609 | 94.015 | 1.00 | 32.88 | B | C |
| ATOM | 4696 | CB | PRO | B | 311 | 40.479 | 35.686 | 95.002 | 1.00 | 32.47 | B | C |
| ATOM | 4697 | CG | PRO | B | 311 | 41.104 | 36.630 | 95.979 | 1.00 | 34.03 | B | C |
| ATOM | 4698 | C | PRO | B | 311 | 38.263 | 36.747 | 94.288 | 1.00 | 32.52 | B | C |
| ATOM | 4699 | O | PRO | B | 311 | 37.467 | 36.026 | 93.692 | 1.00 | 32.74 | B | O |
| ATOM | 4700 | N | GLU | B | 312 | 37.870 | 37.665 | 95.169 | 1.00 | 32.49 | B | N |
| ATOM | 4701 | CA | GLU | B | 312 | 36.439 | 37.826 | 95.431 | 1.00 | 32.71 | B | C |
| ATOM | 4702 | CB | GLU | B | 312 | 36.175 | 38.669 | 96.687 | 1.00 | 35.32 | B | C |
| ATOM | 4703 | CG | GLU | B | 312 | 37.250 | 39.668 | 97.039 | 1.00 | 41.49 | B | C |
| ATOM | 4704 | CD | GLU | B | 312 | 38.433 | 39.015 | 97.737 | 1.00 | 43.16 | B | C |
| ATOM | 4705 | OE1 | GLU | B | 312 | 39.538 | 39.004 | 97.150 | 1.00 | 42.47 | B | O |
| ATOM | 4706 | OE2 | GLU | B | 312 | 38.249 | 38.518 | 98.877 | 1.00 | 44.10 | B | O |
| ATOM | 4707 | C | GLU | B | 312 | 35.692 | 38.410 | 94.224 | 1.00 | 30.99 | B | C |
| ATOM | 4708 | O | GLU | B | 312 | 34.534 | 38.086 | 94.002 | 1.00 | 29.65 | B | O |
| ATOM | 4709 | N | ALA | B | 313 | 36.364 | 39.250 | 93.439 | 1.00 | 28.61 | B | N |
| ATOM | 4710 | CA | ALA | B | 313 | 35.736 | 39.832 | 92.257 | 1.00 | 28.28 | B | C |
| ATOM | 4711 | CB | ALA | B | 313 | 36.680 | 40.847 | 91.587 | 1.00 | 27.99 | B | C |
| ATOM | 4712 | C | ALA | B | 313 | 35.408 | 38.685 | 91.294 | 1.00 | 27.74 | B | C |
| ATOM | 4713 | O | ALA | B | 313 | 34.305 | 38.600 | 90.755 | 1.00 | 25.60 | B | O |
| ATOM | 4714 | N | ILE | B | 314 | 36.386 | 37.805 | 91.101 | 1.00 | 26.81 | B | N |
| ATOM | 4715 | CA | ILE | B | 314 | 36.234 | 36.650 | 90.229 | 1.00 | 27.52 | B | C |
| ATOM | 4716 | CB | ILE | B | 314 | 37.553 | 35.839 | 90.161 | 1.00 | 27.83 | B | C |
| ATOM | 4717 | CG2 | ILE | B | 314 | 37.328 | 34.510 | 89.448 | 1.00 | 27.37 | B | C |
| ATOM | 4718 | CG1 | ILE | B | 314 | 38.614 | 36.658 | 89.425 | 1.00 | 26.77 | B | C |
| ATOM | 4719 | CD1 | ILE | B | 314 | 39.988 | 36.037 | 89.426 | 1.00 | 26.43 | B | C |
| ATOM | 4720 | C | ILE | B | 314 | 35.106 | 35.750 | 90.729 | 1.00 | 28.18 | B | C |
| ATOM | 4721 | O | ILE | B | 314 | 34.268 | 35.309 | 89.948 | 1.00 | 28.99 | B | O |
| ATOM | 4722 | N | ALA | B | 315 | 35.089 | 35.484 | 92.034 | 1.00 | 27.61 | B | N |
| ATOM | 4723 | CA | ALA | B | 315 | 34.051 | 34.644 | 92.624 | 1.00 | 26.83 | B | C |
| ATOM | 4724 | CB | ALA | B | 315 | 34.229 | 34.579 | 94.136 | 1.00 | 27.84 | B | C |
| ATOM | 4725 | C | ALA | B | 315 | 32.674 | 35.212 | 92.278 | 1.00 | 26.06 | B | C |
| ATOM | 4726 | O | ALA | B | 315 | 31.811 | 34.500 | 91.766 | 1.00 | 26.97 | B | O |
| ATOM | 4727 | N | LEU | B | 316 | 32.486 | 36.501 | 92.555 | 1.00 | 24.90 | B | N |
| ATOM | 4728 | CA | LEU | B | 316 | 31.222 | 37.174 | 92.269 | 1.00 | 23.50 | B | C |
| ATOM | 4729 | CB | LEU | B | 316 | 31.310 | 38.670 | 92.613 | 1.00 | 20.43 | B | C |
| ATOM | 4730 | CG | LEU | B | 316 | 30.056 | 39.531 | 92.383 | 1.00 | 18.30 | B | C |
| ATOM | 4731 | CD1 | LEU | B | 316 | 28.856 | 38.863 | 93.025 | 1.00 | 17.27 | B | C |
| ATOM | 4732 | CD2 | LEU | B | 316 | 30.262 | 40.932 | 92.956 | 1.00 | 14.27 | B | C |
| ATOM | 4733 | C | LEU | B | 316 | 30.832 | 36.992 | 90.802 | 1.00 | 23.09 | B | C |
| ATOM | 4734 | O | LEU | B | 316 | 29.697 | 36.667 | 90.500 | 1.00 | 21.07 | B | O |
| ATOM | 4735 | N | CYS | B | 317 | 31.788 | 37.203 | 89.900 | 1.00 | 23.42 | B | N |
| ATOM | 4736 | CA | CYS | B | 317 | 31.527 | 37.032 | 88.478 | 1.00 | 25.74 | B | C |
| ATOM | 4737 | CB | CYS | B | 317 | 32.804 | 37.231 | 87.664 | 1.00 | 27.81 | B | C |
| ATOM | 4738 | SG | CYS | B | 317 | 33.142 | 38.925 | 87.210 | 1.00 | 34.98 | B | S |
| ATOM | 4739 | C | CYS | B | 317 | 30.994 | 35.643 | 88.184 | 1.00 | 26.22 | B | C |
| ATOM | 4740 | O | CYS | B | 317 | 30.033 | 35.488 | 87.438 | 1.00 | 28.08 | B | O |
| ATOM | 4741 | N | SER | B | 318 | 31.625 | 34.630 | 88.769 | 1.00 | 25.35 | B | N |
| ATOM | 4742 | CA | SER | B | 318 | 31.217 | 33.258 | 88.523 | 1.00 | 25.44 | B | C |
| ATOM | 4743 | CB | SER | B | 318 | 32.234 | 32.276 | 89.127 | 1.00 | 27.76 | B | C |
| ATOM | 4744 | OG | SER | B | 318 | 32.200 | 32.278 | 90.551 | 1.00 | 31.85 | B | O |
| ATOM | 4745 | C | SER | B | 318 | 29.835 | 32.963 | 89.059 | 1.00 | 24.60 | B | C |
| ATOM | 4746 | O | SER | B | 318 | 29.226 | 32.011 | 88.643 | 1.00 | 24.43 | B | O |
| ATOM | 4747 | N | ARG | B | 319 | 29.353 | 33.788 | 89.986 | 1.00 | 24.03 | B | N |
| ATOM | 4748 | CA | ARG | B | 319 | 28.023 | 33.583 | 90.548 | 1.00 | 24.21 | B | C |
| ATOM | 4749 | CB | ARG | B | 319 | 28.023 | 33.838 | 92.062 | 1.00 | 25.91 | B | C |
| ATOM | 4750 | CG | ARG | B | 319 | 28.788 | 32.787 | 92.886 | 1.00 | 29.97 | B | C |
| ATOM | 4751 | CD | ARG | B | 319 | 28.390 | 31.347 | 92.535 | 1.00 | 34.05 | B | C |
| ATOM | 4752 | NE | ARG | B | 319 | 26.938 | 31.190 | 92.399 | 1.00 | 39.33 | B | N |
| ATOM | 4753 | CZ | ARG | B | 319 | 26.064 | 31.365 | 93.387 | 1.00 | 39.40 | B | C |

FIG. 5-80

| ATOM | 4754 | NH1 | ARG | B | 319 | 26.487 | 31.698 | 94.601 | 1.00 | 39.76 | B | N |
|---|---|---|---|---|---|---|---|---|---|---|---|---|
| ATOM | 4755 | NH2 | ARG | B | 319 | 24.760 | 31.235 | 93.155 | 1.00 | 38.52 | B | N |
| ATOM | 4756 | C | ARG | B | 319 | 26.988 | 34.463 | 89.853 | 1.00 | 23.04 | B | C |
| ATOM | 4757 | O | ARG | B | 319 | 25.815 | 34.390 | 90.148 | 1.00 | 22.96 | B | O |
| ATOM | 4758 | N | LEU | B | 320 | 27.440 | 35.287 | 88.918 | 1.00 | 21.83 | B | N |
| ATOM | 4759 | CA | LEU | B | 320 | 26.533 | 36.154 | 88.172 | 1.00 | 22.05 | B | C |
| ATOM | 4760 | CB | LEU | B | 320 | 27.128 | 37.563 | 88.055 | 1.00 | 19.96 | B | C |
| ATOM | 4761 | CG | LEU | B | 320 | 27.288 | 38.273 | 89.401 | 1.00 | 19.20 | B | C |
| ATOM | 4762 | CD1 | LEU | B | 320 | 28.111 | 39.533 | 89.267 | 1.00 | 19.11 | B | C |
| ATOM | 4763 | CD2 | LEU | B | 320 | 25.914 | 38.575 | 89.942 | 1.00 | 17.65 | B | C |
| ATOM | 4764 | C | LEU | B | 320 | 26.326 | 35.551 | 86.784 | 1.00 | 22.71 | B | C |
| ATOM | 4765 | O | LEU | B | 320 | 25.210 | 35.217 | 86.397 | 1.00 | 22.55 | B | O |
| ATOM | 4766 | N | LEU | B | 321 | 27.432 | 35.396 | 86.063 | 1.00 | 22.24 | B | N |
| ATOM | 4767 | CA | LEU | B | 321 | 27.434 | 34.851 | 84.711 | 1.00 | 22.52 | B | C |
| ATOM | 4768 | CB | LEU | B | 321 | 28.742 | 35.244 | 84.027 | 1.00 | 20.62 | B | C |
| ATOM | 4769 | CG | LEU | B | 321 | 28.944 | 36.755 | 84.143 | 1.00 | 19.98 | B | C |
| ATOM | 4770 | CD1 | LEU | B | 321 | 30.353 | 37.140 | 83.776 | 1.00 | 18.38 | B | C |
| ATOM | 4771 | CD2 | LEU | B | 321 | 27.917 | 37.452 | 83.252 | 1.00 | 19.80 | B | C |
| ATOM | 4772 | C | LEU | B | 321 | 27.267 | 33.338 | 84.734 | 1.00 | 21.42 | B | C |
| ATOM | 4773 | O | LEU | B | 321 | 28.208 | 32.595 | 84.576 | 1.00 | 19.75 | B | O |
| ATOM | 4774 | N | GLU | B | 322 | 26.024 | 32.920 | 84.910 | 1.00 | 22.64 | B | N |
| ATOM | 4775 | CA | GLU | B | 322 | 25.666 | 31.517 | 85.019 | 1.00 | 24.14 | B | C |
| ATOM | 4776 | CB | GLU | B | 322 | 25.175 | 31.284 | 86.446 | 1.00 | 26.90 | B | C |
| ATOM | 4777 | CG | GLU | B | 322 | 25.420 | 29.916 | 87.001 | 1.00 | 34.64 | B | C |
| ATOM | 4778 | CD | GLU | B | 322 | 26.104 | 29.958 | 88.357 | 1.00 | 37.65 | B | C |
| ATOM | 4779 | OE1 | GLU | B | 322 | 25.728 | 30.803 | 89.194 | 1.00 | 39.58 | B | O |
| ATOM | 4780 | OE2 | GLU | B | 322 | 27.013 | 29.138 | 88.594 | 1.00 | 40.88 | B | O |
| ATOM | 4781 | C | GLU | B | 322 | 24.564 | 31.187 | 84.010 | 1.00 | 23.52 | B | C |
| ATOM | 4782 | O | GLU | B | 322 | 23.633 | 31.970 | 83.823 | 1.00 | 23.28 | B | O |
| ATOM | 4783 | N | TYR | B | 323 | 24.681 | 30.032 | 83.362 | 1.00 | 22.96 | B | N |
| ATOM | 4784 | CA | TYR | B | 323 | 23.682 | 29.602 | 82.386 | 1.00 | 22.52 | B | C |
| ATOM | 4785 | CB | TYR | B | 323 | 24.063 | 28.243 | 81.800 | 1.00 | 21.41 | B | C |
| ATOM | 4786 | CG | TYR | B | 323 | 25.135 | 28.293 | 80.731 | 1.00 | 20.64 | B | C |
| ATOM | 4787 | CD1 | TYR | B | 323 | 24.927 | 28.982 | 79.542 | 1.00 | 19.55 | B | C |
| ATOM | 4788 | CE1 | TYR | B | 323 | 25.871 | 28.983 | 78.530 | 1.00 | 20.78 | B | C |
| ATOM | 4789 | CD2 | TYR | B | 323 | 26.335 | 27.598 | 80.884 | 1.00 | 21.41 | B | C |
| ATOM | 4790 | CE2 | TYR | B | 323 | 27.293 | 27.589 | 79.873 | 1.00 | 22.23 | B | C |
| ATOM | 4791 | CZ | TYR | B | 323 | 27.050 | 28.283 | 78.696 | 1.00 | 22.70 | B | C |
| ATOM | 4792 | OH | TYR | B | 323 | 27.979 | 28.271 | 77.683 | 1.00 | 23.44 | B | O |
| ATOM | 4793 | C | TYR | B | 323 | 22.291 | 29.506 | 83.006 | 1.00 | 22.56 | B | C |
| ATOM | 4794 | O | TYR | B | 323 | 21.343 | 30.100 | 82.510 | 1.00 | 21.17 | B | O |
| ATOM | 4795 | N | THR | B | 324 | 22.178 | 28.742 | 84.088 | 1.00 | 21.98 | B | N |
| ATOM | 4796 | CA | THR | B | 324 | 20.893 | 28.580 | 84.747 | 1.00 | 23.78 | B | C |
| ATOM | 4797 | CB | THR | B | 324 | 20.949 | 27.483 | 85.827 | 1.00 | 24.69 | B | C |
| ATOM | 4798 | OG1 | THR | B | 324 | 21.456 | 26.275 | 85.247 | 1.00 | 23.78 | B | O |
| ATOM | 4799 | CG2 | THR | B | 324 | 19.554 | 27.215 | 86.386 | 1.00 | 24.73 | B | C |
| ATOM | 4800 | C | THR | B | 324 | 20.504 | 29.915 | 85.366 | 1.00 | 23.12 | B | C |
| ATOM | 4801 | O | THR | B | 324 | 21.143 | 30.395 | 86.279 | 1.00 | 25.20 | B | O |
| ATOM | 4802 | N | PRO | B | 325 | 19.449 | 30.539 | 84.840 | 1.00 | 23.45 | B | N |
| ATOM | 4803 | CD | PRO | B | 325 | 18.630 | 30.094 | 83.697 | 1.00 | 23.72 | B | C |
| ATOM | 4804 | CA | PRO | B | 325 | 18.988 | 31.832 | 85.355 | 1.00 | 22.55 | B | C |
| ATOM | 4805 | CB | PRO | B | 325 | 17.719 | 32.103 | 84.544 | 1.00 | 22.16 | B | C |
| ATOM | 4806 | CG | PRO | B | 325 | 17.981 | 31.396 | 83.241 | 1.00 | 24.49 | B | C |
| ATOM | 4807 | C | PRO | B | 325 | 18.719 | 31.816 | 86.857 | 1.00 | 23.11 | B | C |
| ATOM | 4808 | O | PRO | B | 325 | 19.126 | 32.725 | 87.564 | 1.00 | 22.38 | B | O |
| ATOM | 4809 | N | THR | B | 326 | 18.035 | 30.776 | 87.334 | 1.00 | 23.85 | B | N |
| ATOM | 4810 | CA | THR | B | 326 | 17.704 | 30.657 | 88.758 | 1.00 | 23.82 | B | C |
| ATOM | 4811 | CB | THR | B | 326 | 16.707 | 29.495 | 89.022 | 1.00 | 24.98 | B | C |
| ATOM | 4812 | OG1 | THR | B | 326 | 17.267 | 28.262 | 88.553 | 1.00 | 26.02 | B | O |
| ATOM | 4813 | CG2 | THR | B | 326 | 15.384 | 29.748 | 88.321 | 1.00 | 25.23 | B | C |

FIG. 5-81

| ATOM | 4814 | C | THR | B | 326 | 18.911 | 30.448 | 89.664 | 1.00 | 23.37 | B | C |
| --- | --- | --- | --- | --- | --- | --- | --- | --- | --- | --- | --- | --- |
| ATOM | 4815 | O | THR | B | 326 | 18.808 | 30.601 | 90.875 | 1.00 | 23.10 | B | O |
| ATOM | 4816 | N | ALA | B | 327 | 20.050 | 30.098 | 89.077 | 1.00 | 22.41 | B | N |
| ATOM | 4817 | CA | ALA | B | 327 | 21.270 | 29.871 | 89.855 | 1.00 | 23.11 | B | C |
| ATOM | 4818 | CB | ALA | B | 327 | 22.178 | 28.916 | 89.118 | 1.00 | 22.34 | B | C |
| ATOM | 4819 | C | ALA | B | 327 | 22.019 | 31.170 | 90.136 | 1.00 | 23.55 | B | C |
| ATOM | 4820 | O | ALA | B | 327 | 22.772 | 31.258 | 91.086 | 1.00 | 23.42 | B | O |
| ATOM | 4821 | N | ARG | B | 328 | 21.802 | 32.172 | 89.294 | 1.00 | 23.04 | B | N |
| ATOM | 4822 | CA | ARG | B | 328 | 22.479 | 33.452 | 89.456 | 1.00 | 22.84 | B | C |
| ATOM | 4823 | CB | ARG | B | 328 | 22.128 | 34.396 | 88.302 | 1.00 | 20.05 | B | C |
| ATOM | 4824 | CG | ARG | B | 328 | 22.458 | 33.845 | 86.918 | 1.00 | 20.00 | B | C |
| ATOM | 4825 | CD | ARG | B | 328 | 21.780 | 34.648 | 85.819 | 1.00 | 18.05 | B | C |
| ATOM | 4826 | NE | ARG | B | 328 | 21.954 | 34.021 | 84.516 | 1.00 | 18.51 | B | N |
| ATOM | 4827 | CZ | ARG | B | 328 | 21.201 | 34.272 | 83.453 | 1.00 | 17.85 | B | C |
| ATOM | 4828 | NH1 | ARG | B | 328 | 20.204 | 35.145 | 83.523 | 1.00 | 17.01 | B | N |
| ATOM | 4829 | NH2 | ARG | B | 328 | 21.447 | 33.640 | 82.317 | 1.00 | 19.64 | B | N |
| ATOM | 4830 | C | ARG | B | 328 | 22.102 | 34.111 | 90.770 | 1.00 | 23.25 | B | C |
| ATOM | 4831 | O | ARG | B | 328 | 21.027 | 33.894 | 91.289 | 1.00 | 22.12 | B | O |
| ATOM | 4832 | N | LEU | B | 329 | 23.019 | 34.907 | 91.300 | 1.00 | 23.71 | B | N |
| ATOM | 4833 | CA | LEU | B | 329 | 22.763 | 35.625 | 92.535 | 1.00 | 23.63 | B | C |
| ATOM | 4834 | CB | LEU | B | 329 | 24.003 | 36.391 | 92.979 | 1.00 | 22.01 | B | C |
| ATOM | 4835 | CG | LEU | B | 329 | 24.911 | 35.722 | 94.002 | 1.00 | 24.74 | B | C |
| ATOM | 4836 | CD1 | LEU | B | 329 | 25.052 | 34.252 | 93.689 | 1.00 | 25.55 | B | C |
| ATOM | 4837 | CD2 | LEU | B | 329 | 26.262 | 36.423 | 94.001 | 1.00 | 21.98 | B | C |
| ATOM | 4838 | C | LEU | B | 329 | 21.641 | 36.624 | 92.329 | 1.00 | 23.40 | B | C |
| ATOM | 4839 | O | LEU | B | 329 | 21.347 | 37.049 | 91.205 | 1.00 | 22.56 | B | O |
| ATOM | 4840 | N | THR | B | 330 | 21.024 | 36.981 | 93.443 | 1.00 | 23.07 | B | N |
| ATOM | 4841 | CA | THR | B | 330 | 19.957 | 37.967 | 93.496 | 1.00 | 22.79 | B | C |
| ATOM | 4842 | CB | THR | B | 330 | 19.136 | 37.812 | 94.808 | 1.00 | 23.51 | B | C |
| ATOM | 4843 | OG1 | THR | B | 330 | 18.344 | 36.621 | 94.758 | 1.00 | 29.16 | B | O |
| ATOM | 4844 | CG2 | THR | B | 330 | 18.244 | 39.013 | 95.033 | 1.00 | 26.07 | B | C |
| ATOM | 4845 | C | THR | B | 330 | 20.711 | 39.276 | 93.636 | 1.00 | 20.93 | B | C |
| ATOM | 4846 | O | THR | B | 330 | 21.829 | 39.284 | 94.119 | 1.00 | 19.09 | B | O |
| ATOM | 4847 | N | PRO | B | 331 | 20.115 | 40.394 | 93.207 | 1.00 | 19.73 | B | N |
| ATOM | 4848 | CD | PRO | B | 331 | 18.955 | 40.550 | 92.313 | 1.00 | 20.77 | B | C |
| ATOM | 4849 | CA | PRO | B | 331 | 20.831 | 41.657 | 93.359 | 1.00 | 20.17 | B | C |
| ATOM | 4850 | CB | PRO | B | 331 | 19.841 | 42.671 | 92.806 | 1.00 | 20.27 | B | C |
| ATOM | 4851 | CG | PRO | B | 331 | 19.203 | 41.907 | 91.688 | 1.00 | 18.56 | B | C |
| ATOM | 4852 | C | PRO | B | 331 | 21.165 | 41.884 | 94.839 | 1.00 | 21.15 | B | C |
| ATOM | 4853 | O | PRO | B | 331 | 22.273 | 42.275 | 95.170 | 1.00 | 22.52 | B | O |
| ATOM | 4854 | N | LEU | B | 332 | 20.211 | 41.599 | 95.725 | 1.00 | 20.27 | B | N |
| ATOM | 4855 | CA | LEU | B | 332 | 20.440 | 41.798 | 97.153 | 1.00 | 22.53 | B | C |
| ATOM | 4856 | CB | LEU | B | 332 | 19.149 | 41.555 | 97.946 | 1.00 | 22.63 | B | C |
| ATOM | 4857 | CG | LEU | B | 332 | 19.165 | 42.101 | 99.380 | 1.00 | 24.61 | B | C |
| ATOM | 4858 | CD1 | LEU | B | 332 | 19.293 | 43.630 | 99.360 | 1.00 | 24.26 | B | C |
| ATOM | 4859 | CD2 | LEU | B | 332 | 17.890 | 41.683 | 100.095 | 1.00 | 24.48 | B | C |
| ATOM | 4860 | C | LEU | B | 332 | 21.560 | 40.881 | 97.641 | 1.00 | 22.91 | B | C |
| ATOM | 4861 | O | LEU | B | 332 | 22.420 | 41.307 | 98.406 | 1.00 | 21.91 | B | O |
| ATOM | 4862 | N | GLU | B | 333 | 21.549 | 39.629 | 97.185 | 1.00 | 22.31 | B | N |
| ATOM | 4863 | CA | GLU | B | 333 | 22.589 | 38.676 | 97.553 | 1.00 | 23.59 | B | C |
| ATOM | 4864 | CB | GLU | B | 333 | 22.326 | 37.297 | 96.925 | 1.00 | 24.78 | B | C |
| ATOM | 4865 | CG | GLU | B | 333 | 21.099 | 36.564 | 97.488 | 1.00 | 29.10 | B | C |
| ATOM | 4866 | CD | GLU | B | 333 | 20.734 | 35.298 | 96.712 | 1.00 | 29.76 | B | C |
| ATOM | 4867 | OE1 | GLU | B | 333 | 21.366 | 35.020 | 95.672 | 1.00 | 31.60 | B | O |
| ATOM | 4868 | OE2 | GLU | B | 333 | 19.802 | 34.585 | 97.142 | 1.00 | 31.48 | B | O |
| ATOM | 4869 | C | GLU | B | 333 | 23.922 | 39.216 | 97.056 | 1.00 | 23.81 | B | C |
| ATOM | 4870 | O | GLU | B | 333 | 24.897 | 39.183 | 97.766 | 1.00 | 24.22 | B | O |
| ATOM | 4871 | N | ALA | B | 334 | 23.949 | 39.720 | 95.822 | 1.00 | 23.95 | B | N |
| ATOM | 4872 | CA | ALA | B | 334 | 25.187 | 40.256 | 95.267 | 1.00 | 23.82 | B | C |
| ATOM | 4873 | CB | ALA | B | 334 | 24.947 | 40.784 | 93.850 | 1.00 | 22.52 | B | C |

FIG. 5-82

```
ATOM   4874  C    ALA B 334      25.708  41.369  96.185  1.00 23.52      B  C
ATOM   4875  O    ALA B 334      26.880  41.430  96.468  1.00 22.39      B  O
ATOM   4876  N    CYS B 335      24.805  42.230  96.645  1.00 23.22      B  N
ATOM   4877  CA   CYS B 335      25.174  43.317  97.543  1.00 22.90      B  C
ATOM   4878  CB   CYS B 335      23.925  44.108  97.960  1.00 23.13      B  C
ATOM   4879  SG   CYS B 335      23.216  45.222  96.696  1.00 22.65      B  S
ATOM   4880  C    CYS B 335      25.883  42.781  98.793  1.00 24.18      B  C
ATOM   4881  O    CYS B 335      26.797  43.407  99.304  1.00 23.61      B  O
ATOM   4882  N    ALA B 336      25.461  41.611  99.265  1.00 23.53      B  N
ATOM   4883  CA   ALA B 336      26.041  41.007 100.460  1.00 24.28      B  C
ATOM   4884  CB   ALA B 336      25.031  40.065 101.105  1.00 22.83      B  C
ATOM   4885  C    ALA B 336      27.351  40.264 100.230  1.00 24.78      B  C
ATOM   4886  O    ALA B 336      28.030  39.878 101.194  1.00 24.50      B  O
ATOM   4887  N    HIS B 337      27.709  40.071  98.967  1.00 23.22      B  N
ATOM   4888  CA   HIS B 337      28.930  39.347  98.624  1.00 24.07      B  C
ATOM   4889  CB   HIS B 337      29.100  39.338  97.107  1.00 24.21      B  C
ATOM   4890  CG   HIS B 337      30.001  38.255  96.611  1.00 23.83      B  C
ATOM   4891  CD2  HIS B 337      29.736  36.987  96.209  1.00 21.55      B  C
ATOM   4892  ND1  HIS B 337      31.366  38.406  96.519  1.00 24.34      B  N
ATOM   4893  CE1  HIS B 337      31.904  37.282  96.082  1.00 23.68      B  C
ATOM   4894  NE2  HIS B 337      30.932  36.404  95.888  1.00 22.14      B  N
ATOM   4895  C    HIS B 337      30.183  39.925  99.304  1.00 23.67      B  C
ATOM   4896  O    HIS B 337      30.281  41.120  99.539  1.00 21.21      B  O
ATOM   4897  N    SER B 338      31.135  39.050  99.611  1.00 24.00      B  N
ATOM   4898  CA   SER B 338      32.373  39.459 100.263  1.00 26.48      B  C
ATOM   4899  CB   SER B 338      33.272  38.248 100.518  1.00 27.52      B  C
ATOM   4900  OG   SER B 338      32.655  37.372 101.441  1.00 31.32      B  O
ATOM   4901  C    SER B 338      33.145  40.504  99.474  1.00 25.88      B  C
ATOM   4902  O    SER B 338      33.866  41.315 100.055  1.00 26.28      B  O
ATOM   4903  N    PHE B 339      32.993  40.487  98.153  1.00 24.47      B  N
ATOM   4904  CA   PHE B 339      33.689  41.450  97.309  1.00 23.54      B  C
ATOM   4905  CB   PHE B 339      33.307  41.264  95.840  1.00 21.99      B  C
ATOM   4906  CG   PHE B 339      33.969  42.247  94.919  1.00 20.69      B  C
ATOM   4907  CD1  PHE B 339      35.354  42.298  94.817  1.00 21.07      B  C
ATOM   4908  CD2  PHE B 339      33.211  43.125  94.158  1.00 21.99      B  C
ATOM   4909  CE1  PHE B 339      35.977  43.214  93.966  1.00 22.10      B  C
ATOM   4910  CE2  PHE B 339      33.825  44.045  93.303  1.00 24.62      B  C
ATOM   4911  CZ   PHE B 339      35.211  44.091  93.206  1.00 22.56      B  C
ATOM   4912  C    PHE B 339      33.390  42.883  97.728  1.00 23.82      B  C
ATOM   4913  O    PHE B 339      34.167  43.775  97.471  1.00 25.31      B  O
ATOM   4914  N    PHE B 340      32.257  43.096  98.383  1.00 23.73      B  N
ATOM   4915  CA   PHE B 340      31.886  44.440  98.809  1.00 23.92      B  C
ATOM   4916  CB   PHE B 340      30.401  44.679  98.515  1.00 22.64      B  C
ATOM   4917  CG   PHE B 340      30.053  44.594  97.041  1.00 23.75      B  C
ATOM   4918  CD1  PHE B 340      30.632  45.473  96.122  1.00 21.37      B  C
ATOM   4919  CD2  PHE B 340      29.155  43.631  96.573  1.00 20.44      B  C
ATOM   4920  CE1  PHE B 340      30.325  45.397  94.767  1.00 18.92      B  C
ATOM   4921  CE2  PHE B 340      28.844  43.551  95.219  1.00 21.42      B  C
ATOM   4922  CZ   PHE B 340      29.432  44.438  94.313  1.00 20.94      B  C
ATOM   4923  C    PHE B 340      32.189  44.706 100.286  1.00 24.19      B  C
ATOM   4924  O    PHE B 340      31.794  45.732 100.827  1.00 24.46      B  O
ATOM   4925  N    ASP B 341      32.903  43.787 100.928  1.00 23.88      B  N
ATOM   4926  CA   ASP B 341      33.236  43.939 102.344  1.00 25.42      B  C
ATOM   4927  CB   ASP B 341      34.087  42.767 102.830  1.00 23.55      B  C
ATOM   4928  CG   ASP B 341      33.289  41.503 102.983  1.00 25.11      B  C
ATOM   4929  OD1  ASP B 341      32.044  41.583 102.942  1.00 23.29      B  O
ATOM   4930  OD2  ASP B 341      33.903  40.430 103.154  1.00 27.05      B  O
ATOM   4931  C    ASP B 341      33.970  45.234 102.659  1.00 25.43      B  C
ATOM   4932  O    ASP B 341      33.739  45.823 103.683  1.00 27.00      B  O
ATOM   4933  N    GLU B 342      34.860  45.660 101.770  1.00 25.32      B  N
```

FIG. 5-83

```
ATOM   4934  CA  GLU B 342      35.604  46.883 102.005  1.00 27.03       B  C
ATOM   4935  CB  GLU B 342      36.598  47.141 100.861  1.00 28.22       B  C
ATOM   4936  CG  GLU B 342      37.309  48.502 100.934  1.00 31.21       B  C
ATOM   4937  CD  GLU B 342      38.533  48.616 100.013  1.00 32.07       B  C
ATOM   4938  OE1 GLU B 342      38.489  48.117  98.863  1.00 29.84       B  O
ATOM   4939  OE2 GLU B 342      39.538  49.227 100.445  1.00 35.15       B  O
ATOM   4940  C   GLU B 342      34.661  48.066 102.183  1.00 27.02       B  C
ATOM   4941  O   GLU B 342      34.876  48.894 103.047  1.00 25.83       B  O
ATOM   4942  N   LEU B 343      33.605  48.130 101.374  1.00 26.44       B  N
ATOM   4943  CA  LEU B 343      32.661  49.237 101.474  1.00 26.04       B  C
ATOM   4944  CB  LEU B 343      31.581  49.144 100.389  1.00 24.65       B  C
ATOM   4945  CG  LEU B 343      32.059  49.135  98.929  1.00 25.00       B  C
ATOM   4946  CD1 LEU B 343      30.855  49.095  97.983  1.00 21.25       B  C
ATOM   4947  CD2 LEU B 343      32.914  50.356  98.657  1.00 23.12       B  C
ATOM   4948  C   LEU B 343      32.009  49.284 102.852  1.00 26.52       B  C
ATOM   4949  O   LEU B 343      31.597  50.333 103.303  1.00 27.13       B  O
ATOM   4950  N   ARG B 344      31.946  48.139 103.524  1.00 26.89       B  N
ATOM   4951  CA  ARG B 344      31.328  48.074 104.841  1.00 27.93       B  C
ATOM   4952  CB  ARG B 344      30.664  46.711 105.036  1.00 26.31       B  C
ATOM   4953  CG  ARG B 344      29.413  46.527 104.186  1.00 23.72       B  C
ATOM   4954  CD  ARG B 344      28.770  45.199 104.470  1.00 23.25       B  C
ATOM   4955  NE  ARG B 344      29.419  44.113 103.745  1.00 22.03       B  N
ATOM   4956  CZ  ARG B 344      29.141  43.787 102.488  1.00 21.32       B  C
ATOM   4957  NH1 ARG B 344      28.221  44.465 101.816  1.00 19.06       B  N
ATOM   4958  NH2 ARG B 344      29.780  42.780 101.905  1.00 19.94       B  N
ATOM   4959  C   ARG B 344      32.308  48.359 105.977  1.00 29.92       B  C
ATOM   4960  O   ARG B 344      31.938  48.359 107.145  1.00 31.20       B  O
ATOM   4961  N   ASP B 345      33.561  48.608 105.621  1.00 32.06       B  N
ATOM   4962  CA  ASP B 345      34.590  48.913 106.602  1.00 33.37       B  C
ATOM   4963  CB  ASP B 345      35.970  48.721 105.967  1.00 34.50       B  C
ATOM   4964  CG  ASP B 345      37.110  48.948 106.945  1.00 37.00       B  C
ATOM   4965  OD1 ASP B 345      37.911  48.011 107.147  1.00 39.20       B  O
ATOM   4966  OD2 ASP B 345      37.213  50.060 107.506  1.00 37.35       B  O
ATOM   4967  C   ASP B 345      34.401  50.376 107.030  1.00 34.23       B  C
ATOM   4968  O   ASP B 345      34.492  51.283 106.211  1.00 35.01       B  O
ATOM   4969  N   PRO B 346      34.135  50.616 108.328  1.00 35.02       B  N
ATOM   4970  CD  PRO B 346      34.152  49.641 109.431  1.00 34.65       B  C
ATOM   4971  CA  PRO B 346      33.934  51.973 108.845  1.00 35.03       B  C
ATOM   4972  CB  PRO B 346      33.859  51.767 110.357  1.00 34.47       B  C
ATOM   4973  CG  PRO B 346      34.633  50.502 110.579  1.00 36.17       B  C
ATOM   4974  C   PRO B 346      34.990  53.016 108.460  1.00 36.38       B  C
ATOM   4975  O   PRO B 346      34.700  54.207 108.428  1.00 37.71       B  O
ATOM   4976  N   ASN B 347      36.206  52.574 108.164  1.00 37.49       B  N
ATOM   4977  CA  ASN B 347      37.289  53.491 107.810  1.00 37.99       B  C
ATOM   4978  CB  ASN B 347      38.628  52.950 108.292  1.00 40.84       B  C
ATOM   4979  CG  ASN B 347      38.721  52.868 109.786  1.00 42.67       B  C
ATOM   4980  OD1 ASN B 347      39.550  52.130 110.312  1.00 45.31       B  O
ATOM   4981  ND2 ASN B 347      37.881  53.633 110.489  1.00 43.33       B  N
ATOM   4982  C   ASN B 347      37.438  53.731 106.317  1.00 38.00       B  C
ATOM   4983  O   ASN B 347      38.305  54.489 105.898  1.00 38.30       B  O
ATOM   4984  N   VAL B 348      36.613  53.076 105.511  1.00 36.49       B  N
ATOM   4985  CA  VAL B 348      36.729  53.247 104.077  1.00 35.65       B  C
ATOM   4986  CB  VAL B 348      35.689  52.400 103.312  1.00 35.36       B  C
ATOM   4987  CG1 VAL B 348      34.289  52.982 103.483  1.00 35.20       B  C
ATOM   4988  CG2 VAL B 348      36.074  52.331 101.853  1.00 34.49       B  C
ATOM   4989  C   VAL B 348      36.559  54.714 103.718  1.00 35.01       B  C
ATOM   4990  O   VAL B 348      35.840  55.429 104.371  1.00 34.42       B  O
ATOM   4991  N   LYS B 349      37.230  55.138 102.653  1.00 35.22       B  N
ATOM   4992  CA  LYS B 349      37.184  56.522 102.213  1.00 35.87       B  C
ATOM   4993  CB  LYS B 349      38.271  57.321 102.958  1.00 36.43       B  C
```

FIG. 5-84

```
ATOM   4994  CG  LYS B 349      37.848  58.637 103.631  1.00 38.79      B  C
ATOM   4995  CD  LYS B 349      37.141  58.421 104.972  1.00 37.91      B  C
ATOM   4996  CE  LYS B 349      36.972  59.741 105.735  1.00 39.57      B  C
ATOM   4997  NZ  LYS B 349      36.133  59.596 106.970  1.00 38.40      B  N
ATOM   4998  C   LYS B 349      37.512  56.523 100.714  1.00 36.55      B  C
ATOM   4999  O   LYS B 349      38.168  55.617 100.213  1.00 36.18      B  O
ATOM   5000  N   LEU B 350      37.063  57.547 100.002  1.00 37.03      B  N
ATOM   5001  CA  LEU B 350      37.335  57.642  98.575  1.00 37.44      B  C
ATOM   5002  CB  LEU B 350      36.346  58.614  97.929  1.00 34.68      B  C
ATOM   5003  CG  LEU B 350      34.869  58.357  98.236  1.00 34.46      B  C
ATOM   5004  CD1 LEU B 350      34.047  59.542  97.794  1.00 33.31      B  C
ATOM   5005  CD2 LEU B 350      34.394  57.084  97.532  1.00 33.14      B  C
ATOM   5006  C   LEU B 350      38.764  58.163  98.388  1.00 38.26      B  C
ATOM   5007  O   LEU B 350      39.238  58.934  99.183  1.00 37.25      B  O
ATOM   5008  N   PRO B 351      39.460  57.733  97.322  1.00 40.73      B  N
ATOM   5009  CD  PRO B 351      38.953  57.021  96.136  1.00 41.70      B  C
ATOM   5010  CA  PRO B 351      40.839  58.207  97.099  1.00 41.65      B  C
ATOM   5011  CB  PRO B 351      41.206  57.590  95.751  1.00 42.14      B  C
ATOM   5012  CG  PRO B 351      39.883  57.539  95.034  1.00 42.52      B  C
ATOM   5013  C   PRO B 351      40.764  59.720  97.008  1.00 41.47      B  C
ATOM   5014  O   PRO B 351      41.752  60.434  97.091  1.00 41.77      B  O
ATOM   5015  N   ASN B 352      39.531  60.160  96.827  1.00 41.76      B  N
ATOM   5016  CA  ASN B 352      39.124  61.548  96.722  1.00 42.17      B  C
ATOM   5017  CB  ASN B 352      37.621  61.552  96.450  1.00 43.59      B  C
ATOM   5018  CG  ASN B 352      37.140  62.825  95.814  1.00 43.75      B  C
ATOM   5019  OD1 ASN B 352      35.949  62.959  95.492  1.00 42.35      B  O
ATOM   5020  ND2 ASN B 352      38.055  63.771  95.612  1.00 44.16      B  N
ATOM   5021  C   ASN B 352      39.376  62.245  98.052  1.00 41.52      B  C
ATOM   5022  O   ASN B 352      39.534  63.459  98.117  1.00 40.01      B  O
ATOM   5023  N   GLY B 353      39.366  61.446  99.114  1.00 41.86      B  N
ATOM   5024  CA  GLY B 353      39.559  61.969 100.449  1.00 42.93      B  C
ATOM   5025  C   GLY B 353      38.215  62.110 101.137  1.00 42.86      B  C
ATOM   5026  O   GLY B 353      38.120  61.935 102.334  1.00 42.99      B  O
ATOM   5027  N   ARG B 354      37.168  62.415 100.376  1.00 42.97      B  N
ATOM   5028  CA  ARG B 354      35.856  62.565 100.984  1.00 43.17      B  C
ATOM   5029  CB  ARG B 354      34.953  63.449 100.114  1.00 44.06      B  C
ATOM   5030  CG  ARG B 354      34.672  62.961  98.717  1.00 45.60      B  C
ATOM   5031  CD  ARG B 354      33.619  63.866  98.058  1.00 46.42      B  C
ATOM   5032  NE  ARG B 354      34.141  65.173  97.653  1.00 47.22      B  N
ATOM   5033  CZ  ARG B 354      33.388  66.143  97.136  1.00 48.28      B  C
ATOM   5034  NH1 ARG B 354      32.081  65.951  96.975  1.00 47.90      B  N
ATOM   5035  NH2 ARG B 354      33.937  67.293  96.753  1.00 47.14      B  N
ATOM   5036  C   ARG B 354      35.190  61.230 101.325  1.00 42.28      B  C
ATOM   5037  O   ARG B 354      35.658  60.174 100.916  1.00 43.09      B  O
ATOM   5038  N   ASP B 355      34.118  61.283 102.108  1.00 41.26      B  N
ATOM   5039  CA  ASP B 355      33.404  60.075 102.528  1.00 41.03      B  C
ATOM   5040  CB  ASP B 355      32.408  60.410 103.640  1.00 43.37      B  C
ATOM   5041  CG  ASP B 355      33.065  60.517 104.991  1.00 46.36      B  C
ATOM   5042  OD1 ASP B 355      32.442  61.101 105.914  1.00 48.01      B  O
ATOM   5043  OD2 ASP B 355      34.202  60.005 105.130  1.00 47.07      B  O
ATOM   5044  C   ASP B 355      32.644  59.367 101.420  1.00 38.45      B  C
ATOM   5045  O   ASP B 355      32.237  59.979 100.439  1.00 37.11      B  O
ATOM   5046  N   THR B 356      32.446  58.066 101.605  1.00 35.96      B  N
ATOM   5047  CA  THR B 356      31.696  57.280 100.639  1.00 34.21      B  C
ATOM   5048  CB  THR B 356      31.758  55.766 100.979  1.00 34.60      B  C
ATOM   5049  OG1 THR B 356      31.431  55.565 102.362  1.00 35.17      B  O
ATOM   5050  CG2 THR B 356      33.147  55.217 100.706  1.00 34.18      B  C
ATOM   5051  C   THR B 356      30.248  57.754 100.713  1.00 32.15      B  C
ATOM   5052  O   THR B 356      29.806  58.293 101.734  1.00 29.87      B  O
ATOM   5053  N   PRO B 357      29.496  57.590  99.616  1.00 31.03      B  N
```

FIG. 5-85

```
ATOM   5054  CD   PRO B 357      29.884  57.011  98.316  1.00 30.30      B  C
ATOM   5055  CA   PRO B 357      28.094  58.010  99.610  1.00 29.67      B  C
ATOM   5056  CB   PRO B 357      27.729  57.945  98.134  1.00 29.34      B  C
ATOM   5057  CG   PRO B 357      28.541  56.776  97.655  1.00 30.39      B  C
ATOM   5058  C    PRO B 357      27.293  57.040 100.458  1.00 29.08      B  C
ATOM   5059  O    PRO B 357      27.848  56.079 100.991  1.00 27.86      B  O
ATOM   5060  N    ALA B 358      25.996  57.296 100.584  1.00 30.37      B  N
ATOM   5061  CA   ALA B 358      25.110  56.429 101.362  1.00 31.52      B  C
ATOM   5062  CB   ALA B 358      23.707  57.034 101.403  1.00 32.97      B  C
ATOM   5063  C    ALA B 358      25.076  55.049 100.705  1.00 29.74      B  C
ATOM   5064  O    ALA B 358      24.822  54.928  99.511  1.00 31.37      B  O
ATOM   5065  N    LEU B 359      25.337  54.021 101.503  1.00 26.93      B  N
ATOM   5066  CA   LEU B 359      25.370  52.655 101.023  1.00 25.83      B  C
ATOM   5067  CB   LEU B 359      26.815  52.147 101.066  1.00 24.76      B  C
ATOM   5068  CG   LEU B 359      27.762  52.315  99.868  1.00 26.91      B  C
ATOM   5069  CD1  LEU B 359      27.324  53.444  98.954  1.00 24.36      B  C
ATOM   5070  CD2  LEU B 359      29.178  52.537 100.400  1.00 23.98      B  C
ATOM   5071  C    LEU B 359      24.484  51.732 101.845  1.00 24.60      B  C
ATOM   5072  O    LEU B 359      24.112  50.693 101.385  1.00 23.07      B  O
ATOM   5073  N    PHE B 360      24.134  52.149 103.058  1.00 24.60      B  N
ATOM   5074  CA   PHE B 360      23.349  51.291 103.945  1.00 25.30      B  C
ATOM   5075  CB   PHE B 360      24.167  51.046 105.204  1.00 25.56      B  C
ATOM   5076  CG   PHE B 360      25.644  51.017 104.946  1.00 26.58      B  C
ATOM   5077  CD1  PHE B 360      26.204  50.028 104.143  1.00 27.01      B  C
ATOM   5078  CD2  PHE B 360      26.467  52.013 105.456  1.00 26.20      B  C
ATOM   5079  CE1  PHE B 360      27.562  50.036 103.848  1.00 27.42      B  C
ATOM   5080  CE2  PHE B 360      27.824  52.032 105.168  1.00 26.38      B  C
ATOM   5081  CZ   PHE B 360      28.372  51.042 104.363  1.00 28.10      B  C
ATOM   5082  C    PHE B 360      21.943  51.750 104.318  1.00 24.82      B  C
ATOM   5083  O    PHE B 360      21.321  51.149 105.181  1.00 26.12      B  O
ATOM   5084  N    ASN B 361      21.435  52.794 103.670  1.00 24.33      B  N
ATOM   5085  CA   ASN B 361      20.089  53.273 103.978  1.00 24.98      B  C
ATOM   5086  CB   ASN B 361      19.893  54.716 103.474  1.00 26.58      B  C
ATOM   5087  CG   ASN B 361      20.321  54.901 102.024  1.00 29.42      B  C
ATOM   5088  OD1  ASN B 361      20.132  54.039 101.196  1.00 32.21      B  O
ATOM   5089  ND2  ASN B 361      20.889  56.055 101.724  1.00 33.29      B  N
ATOM   5090  C    ASN B 361      19.029  52.364 103.344  1.00 24.38      B  C
ATOM   5091  O    ASN B 361      18.175  52.813 102.599  1.00 23.67      B  O
ATOM   5092  N    PHE B 362      19.098  51.077 103.645  1.00 24.57      B  N
ATOM   5093  CA   PHE B 362      18.140  50.129 103.093  1.00 24.89      B  C
ATOM   5094  CB   PHE B 362      18.609  48.700 103.375  1.00 23.91      B  C
ATOM   5095  CG   PHE B 362      19.772  48.253 102.528  1.00 25.46      B  C
ATOM   5096  CD1  PHE B 362      19.565  47.762 101.236  1.00 26.59      B  C
ATOM   5097  CD2  PHE B 362      21.072  48.295 103.025  1.00 24.87      B  C
ATOM   5098  CE1  PHE B 362      20.635  47.314 100.451  1.00 23.17      B  C
ATOM   5099  CE2  PHE B 362      22.150  47.852 102.249  1.00 25.96      B  C
ATOM   5100  CZ   PHE B 362      21.927  47.357 100.957  1.00 23.58      B  C
ATOM   5101  C    PHE B 362      16.740  50.325 103.689  1.00 24.67      B  C
ATOM   5102  O    PHE B 362      16.610  50.616 104.871  1.00 22.10      B  O
ATOM   5103  N    THR B 363      15.704  50.190 102.860  1.00 24.90      B  N
ATOM   5104  CA   THR B 363      14.323  50.283 103.352  1.00 26.09      B  C
ATOM   5105  CB   THR B 363      13.389  51.066 102.402  1.00 24.99      B  C
ATOM   5106  OG1  THR B 363      13.351  50.416 101.128  1.00 25.92      B  O
ATOM   5107  CG2  THR B 363      13.856  52.499 102.241  1.00 22.62      B  C
ATOM   5108  C    THR B 363      13.823  48.839 103.413  1.00 27.30      B  C
ATOM   5109  O    THR B 363      14.477  47.933 102.875  1.00 25.90      B  O
ATOM   5110  N    THR B 364      12.678  48.608 104.052  1.00 28.13      B  N
ATOM   5111  CA   THR B 364      12.165  47.244 104.138  1.00 29.66      B  C
ATOM   5112  CB   THR B 364      11.015  47.095 105.181  1.00 30.27      B  C
ATOM   5113  OG1  THR B 364       9.826  47.707 104.679  1.00 33.06      B  O
```

FIG. 5-86

```
ATOM   5114  CG2 THR B 364      11.392  47.751 106.512  1.00 31.83      B  C
ATOM   5115  C   THR B 364      11.657  46.779 102.769  1.00 29.64      B  C
ATOM   5116  O   THR B 364      11.570  45.588 102.499  1.00 31.36      B  O
ATOM   5117  N   GLN B 365      11.332  47.725 101.901  1.00 28.47      B  N
ATOM   5118  CA  GLN B 365      10.855  47.369 100.580  1.00 27.36      B  C
ATOM   5119  CB  GLN B 365      10.264  48.606  99.902  1.00 27.42      B  C
ATOM   5120  CG  GLN B 365       8.982  48.316  99.143  1.00 32.91      B  C
ATOM   5121  CD  GLN B 365       9.268  47.680  97.819  1.00 31.95      B  C
ATOM   5122  OE1 GLN B 365       8.544  46.825  97.353  1.00 30.31      B  O
ATOM   5123  NE2 GLN B 365      10.348  48.121  97.197  1.00 35.72      B  N
ATOM   5124  C   GLN B 365      12.049  46.802  99.805  1.00 26.95      B  C
ATOM   5125  O   GLN B 365      11.947  45.781  99.112  1.00 23.62      B  O
ATOM   5126  N   GLU B 366      13.193  47.458  99.987  1.00 26.52      B  N
ATOM   5127  CA  GLU B 366      14.450  47.098  99.348  1.00 25.70      B  C
ATOM   5128  CB  GLU B 366      15.466  48.223  99.586  1.00 27.11      B  C
ATOM   5129  CG  GLU B 366      16.788  48.058  98.872  1.00 28.21      B  C
ATOM   5130  CD  GLU B 366      17.615  49.340  98.857  1.00 29.14      B  C
ATOM   5131  OE1 GLU B 366      17.233  50.317  99.535  1.00 27.79      B  O
ATOM   5132  OE2 GLU B 366      18.653  49.367  98.162  1.00 29.80      B  O
ATOM   5133  C   GLU B 366      15.009  45.768  99.836  1.00 24.99      B  C
ATOM   5134  O   GLU B 366      15.732  45.112  99.122  1.00 24.61      B  O
ATOM   5135  N   LEU B 367      14.649  45.364 101.050  1.00 25.72      B  N
ATOM   5136  CA  LEU B 367      15.152  44.111 101.606  1.00 25.96      B  C
ATOM   5137  CB  LEU B 367      15.595  44.340 103.058  1.00 26.67      B  C
ATOM   5138  CG  LEU B 367      16.763  45.311 103.276  1.00 26.61      B  C
ATOM   5139  CD1 LEU B 367      16.788  45.775 104.726  1.00 26.07      B  C
ATOM   5140  CD2 LEU B 367      18.070  44.630 102.903  1.00 26.33      B  C
ATOM   5141  C   LEU B 367      14.120  42.995 101.553  1.00 26.19      B  C
ATOM   5142  O   LEU B 367      14.427  41.856 101.882  1.00 27.97      B  O
ATOM   5143  N   SER B 368      12.912  43.328 101.110  1.00 25.96      B  N
ATOM   5144  CA  SER B 368      11.806  42.371 101.055  1.00 27.28      B  C
ATOM   5145  CB  SER B 368      10.609  42.982 100.300  1.00 28.01      B  C
ATOM   5146  OG  SER B 368      10.872  43.170  98.914  1.00 28.25      B  O
ATOM   5147  C   SER B 368      12.098  40.979 100.489  1.00 27.62      B  C
ATOM   5148  O   SER B 368      11.494  39.996 100.920  1.00 27.98      B  O
ATOM   5149  N   SER B 369      13.020  40.874  99.542  1.00 27.00      B  N
ATOM   5150  CA  SER B 369      13.302  39.568  98.966  1.00 27.25      B  C
ATOM   5151  CB  SER B 369      14.050  39.694  97.643  1.00 25.41      B  C
ATOM   5152  OG  SER B 369      15.442  39.664  97.860  1.00 25.22      B  O
ATOM   5153  C   SER B 369      14.099  38.647  99.893  1.00 28.69      B  C
ATOM   5154  O   SER B 369      14.191  37.442  99.643  1.00 29.05      B  O
ATOM   5155  N   ASN B 370      14.680  39.202 100.955  1.00 28.49      B  N
ATOM   5156  CA  ASN B 370      15.463  38.391 101.890  1.00 27.75      B  C
ATOM   5157  CB  ASN B 370      16.702  37.837 101.174  1.00 27.25      B  C
ATOM   5158  CG  ASN B 370      17.373  36.695 101.936  1.00 27.50      B  C
ATOM   5159  OD1 ASN B 370      18.102  35.887 101.348  1.00 24.58      B  O
ATOM   5160  ND2 ASN B 370      17.139  36.630 103.240  1.00 27.81      B  N
ATOM   5161  C   ASN B 370      15.876  39.250 103.091  1.00 28.17      B  C
ATOM   5162  O   ASN B 370      17.046  39.565 103.268  1.00 27.11      B  O
ATOM   5163  N   PRO B 371      14.898  39.622 103.936  1.00 28.17      B  N
ATOM   5164  CD  PRO B 371      13.508  39.133 103.858  1.00 27.14      B  C
ATOM   5165  CA  PRO B 371      15.088  40.449 105.135  1.00 28.11      B  C
ATOM   5166  CB  PRO B 371      13.794  40.231 105.914  1.00 27.45      B  C
ATOM   5167  CG  PRO B 371      12.785  40.048 104.819  1.00 28.42      B  C
ATOM   5168  C   PRO B 371      16.320  40.125 105.980  1.00 27.42      B  C
ATOM   5169  O   PRO B 371      17.088  41.018 106.313  1.00 26.80      B  O
ATOM   5170  N   PRO B 372      16.519  38.844 106.345  1.00 27.69      B  N
ATOM   5171  CD  PRO B 372      15.664  37.656 106.189  1.00 28.66      B  C
ATOM   5172  CA  PRO B 372      17.696  38.530 107.156  1.00 28.34      B  C
ATOM   5173  CB  PRO B 372      17.653  37.000 107.284  1.00 28.21      B  C
```

FIG. 5-87

| ATOM | 5174 | CG | PRO | B | 372 | 16.666 | 36.555 | 106.233 | 1.00 | 29.29 | B | C |
| --- | --- | --- | --- | --- | --- | --- | --- | --- | --- | --- | --- | --- |
| ATOM | 5175 | C | PRO | B | 372 | 19.033 | 39.050 | 106.625 | 1.00 | 28.31 | B | C |
| ATOM | 5176 | O | PRO | B | 372 | 19.964 | 39.261 | 107.389 | 1.00 | 28.76 | B | O |
| ATOM | 5177 | N | LEU | B | 373 | 19.117 | 39.270 | 105.316 | 1.00 | 27.97 | B | N |
| ATOM | 5178 | CA | LEU | B | 373 | 20.347 | 39.768 | 104.710 | 1.00 | 27.53 | B | C |
| ATOM | 5179 | CB | LEU | B | 373 | 20.142 | 39.967 | 103.202 | 1.00 | 26.84 | B | C |
| ATOM | 5180 | CG | LEU | B | 373 | 21.005 | 39.192 | 102.188 | 1.00 | 28.15 | B | C |
| ATOM | 5181 | CD1 | LEU | B | 373 | 21.285 | 37.768 | 102.665 | 1.00 | 27.32 | B | C |
| ATOM | 5182 | CD2 | LEU | B | 373 | 20.286 | 39.180 | 100.841 | 1.00 | 26.41 | B | C |
| ATOM | 5183 | C | LEU | B | 373 | 20.759 | 41.097 | 105.372 | 1.00 | 27.64 | B | C |
| ATOM | 5184 | O | LEU | B | 373 | 21.931 | 41.484 | 105.351 | 1.00 | 26.89 | B | O |
| ATOM | 5185 | N | ALA | B | 374 | 19.798 | 41.798 | 105.964 | 1.00 | 26.31 | B | N |
| ATOM | 5186 | CA | ALA | B | 374 | 20.121 | 43.056 | 106.619 | 1.00 | 28.47 | B | C |
| ATOM | 5187 | CB | ALA | B | 374 | 18.905 | 43.588 | 107.365 | 1.00 | 26.79 | B | C |
| ATOM | 5188 | C | ALA | B | 374 | 21.300 | 42.911 | 107.592 | 1.00 | 28.95 | B | C |
| ATOM | 5189 | O | ALA | B | 374 | 22.063 | 43.845 | 107.786 | 1.00 | 27.39 | B | O |
| ATOM | 5190 | N | THR | B | 375 | 21.441 | 41.730 | 108.192 | 1.00 | 29.88 | B | N |
| ATOM | 5191 | CA | THR | B | 375 | 22.528 | 41.479 | 109.132 | 1.00 | 32.45 | B | C |
| ATOM | 5192 | CB | THR | B | 375 | 22.586 | 40.014 | 109.590 | 1.00 | 33.38 | B | C |
| ATOM | 5193 | OG1 | THR | B | 375 | 21.345 | 39.652 | 110.200 | 1.00 | 37.85 | B | O |
| ATOM | 5194 | CG2 | THR | B | 375 | 23.698 | 39.830 | 110.603 | 1.00 | 36.44 | B | C |
| ATOM | 5195 | C | THR | B | 375 | 23.889 | 41.814 | 108.533 | 1.00 | 32.33 | B | C |
| ATOM | 5196 | O | THR | B | 375 | 24.785 | 42.239 | 109.234 | 1.00 | 32.47 | B | O |
| ATOM | 5197 | N | ILE | B | 376 | 24.033 | 41.598 | 107.231 | 1.00 | 33.08 | B | N |
| ATOM | 5198 | CA | ILE | B | 376 | 25.286 | 41.880 | 106.548 | 1.00 | 32.97 | B | C |
| ATOM | 5199 | CB | ILE | B | 376 | 25.568 | 40.859 | 105.446 | 1.00 | 33.68 | B | C |
| ATOM | 5200 | CG2 | ILE | B | 376 | 26.826 | 41.270 | 104.674 | 1.00 | 33.49 | B | C |
| ATOM | 5201 | CG1 | ILE | B | 376 | 25.716 | 39.468 | 106.064 | 1.00 | 34.23 | B | C |
| ATOM | 5202 | CD1 | ILE | B | 376 | 25.820 | 38.355 | 105.040 | 1.00 | 34.11 | B | C |
| ATOM | 5203 | C | ILE | B | 376 | 25.260 | 43.266 | 105.913 | 1.00 | 32.85 | B | C |
| ATOM | 5204 | O | ILE | B | 376 | 26.180 | 44.074 | 106.102 | 1.00 | 34.10 | B | O |
| ATOM | 5205 | N | LEU | B | 377 | 24.201 | 43.535 | 105.161 | 1.00 | 31.94 | B | N |
| ATOM | 5206 | CA | LEU | B | 377 | 24.046 | 44.809 | 104.470 | 1.00 | 30.79 | B | C |
| ATOM | 5207 | CB | LEU | B | 377 | 22.672 | 44.891 | 103.795 | 1.00 | 28.09 | B | C |
| ATOM | 5208 | CG | LEU | B | 377 | 22.523 | 44.098 | 102.494 | 1.00 | 27.11 | B | C |
| ATOM | 5209 | CD1 | LEU | B | 377 | 23.825 | 44.177 | 101.695 | 1.00 | 24.92 | B | C |
| ATOM | 5210 | CD2 | LEU | B | 377 | 22.207 | 42.677 | 102.796 | 1.00 | 27.01 | B | C |
| ATOM | 5211 | C | LEU | B | 377 | 24.235 | 46.043 | 105.333 | 1.00 | 30.37 | B | C |
| ATOM | 5212 | O | LEU | B | 377 | 24.834 | 47.019 | 104.900 | 1.00 | 28.54 | B | O |
| ATOM | 5213 | N | ILE | B | 378 | 23.691 | 46.005 | 106.545 | 1.00 | 31.01 | B | N |
| ATOM | 5214 | CA | ILE | B | 378 | 23.820 | 47.129 | 107.458 | 1.00 | 30.89 | B | C |
| ATOM | 5215 | CB | ILE | B | 378 | 22.479 | 47.463 | 108.123 | 1.00 | 29.77 | B | C |
| ATOM | 5216 | CG2 | ILE | B | 378 | 22.636 | 48.671 | 109.028 | 1.00 | 30.86 | B | C |
| ATOM | 5217 | CG1 | ILE | B | 378 | 21.444 | 47.795 | 107.048 | 1.00 | 30.55 | B | C |
| ATOM | 5218 | CD1 | ILE | B | 378 | 20.063 | 48.086 | 107.589 | 1.00 | 30.68 | B | C |
| ATOM | 5219 | C | ILE | B | 378 | 24.851 | 46.779 | 108.512 | 1.00 | 31.39 | B | C |
| ATOM | 5220 | O | ILE | B | 378 | 24.567 | 46.078 | 109.450 | 1.00 | 31.67 | B | O |
| ATOM | 5221 | N | PRO | B | 379 | 26.082 | 47.274 | 108.341 | 1.00 | 32.55 | B | N |
| ATOM | 5222 | CD | PRO | B | 379 | 26.499 | 48.217 | 107.288 | 1.00 | 32.85 | B | C |
| ATOM | 5223 | CA | PRO | B | 379 | 27.182 | 47.007 | 109.275 | 1.00 | 33.33 | B | C |
| ATOM | 5224 | CB | PRO | B | 379 | 28.396 | 47.530 | 108.521 | 1.00 | 32.72 | B | C |
| ATOM | 5225 | CG | PRO | B | 379 | 27.836 | 48.719 | 107.808 | 1.00 | 33.74 | B | C |
| ATOM | 5226 | C | PRO | B | 379 | 26.994 | 47.673 | 110.637 | 1.00 | 34.29 | B | C |
| ATOM | 5227 | O | PRO | B | 379 | 26.373 | 48.741 | 110.751 | 1.00 | 33.62 | B | O |
| ATOM | 5228 | N | PRO | B | 380 | 27.552 | 47.055 | 111.689 | 1.00 | 35.13 | B | N |
| ATOM | 5229 | CD | PRO | B | 380 | 28.513 | 45.938 | 111.615 | 1.00 | 35.49 | B | C |
| ATOM | 5230 | CA | PRO | B | 380 | 27.459 | 47.558 | 113.058 | 1.00 | 35.71 | B | C |
| ATOM | 5231 | CB | PRO | B | 380 | 28.649 | 46.897 | 113.741 | 1.00 | 36.44 | B | C |
| ATOM | 5232 | CG | PRO | B | 380 | 28.686 | 45.556 | 113.072 | 1.00 | 35.68 | B | C |
| ATOM | 5233 | C | PRO | B | 380 | 27.478 | 49.089 | 113.194 | 1.00 | 36.41 | B | C |

FIG. 5-88

| | | | | | | | | | | |
|---|---|---|---|---|---|---|---|---|---|---|
| ATOM | 5234 | O | PRO | B | 380 | 26.595 | 49.674 | 113.831 | 1.00 35.02 | B O |
| ATOM | 5235 | N | HIS | B | 381 | 28.458 | 49.732 | 112.565 | 1.00 36.09 | B N |
| ATOM | 5236 | CA | HIS | B | 381 | 28.629 | 51.183 | 112.681 | 1.00 37.29 | B C |
| ATOM | 5237 | CB | HIS | B | 381 | 30.038 | 51.556 | 112.213 | 1.00 37.38 | B C |
| ATOM | 5238 | CG | HIS | B | 381 | 30.283 | 51.284 | 110.759 | 1.00 38.62 | B C |
| ATOM | 5239 | CD2 | HIS | B | 381 | 30.608 | 50.140 | 110.109 | 1.00 38.36 | B C |
| ATOM | 5240 | ND1 | HIS | B | 381 | 30.183 | 52.260 | 109.790 | 1.00 37.99 | B N |
| ATOM | 5241 | CE1 | HIS | B | 381 | 30.438 | 51.731 | 108.605 | 1.00 36.87 | B C |
| ATOM | 5242 | NE2 | HIS | B | 381 | 30.699 | 50.447 | 108.772 | 1.00 37.78 | B N |
| ATOM | 5243 | C | HIS | B | 381 | 27.640 | 52.190 | 112.062 | 1.00 38.44 | B C |
| ATOM | 5244 | O | HIS | B | 381 | 27.429 | 53.256 | 112.627 | 1.00 38.56 | B O |
| ATOM | 5245 | N | ALA | B | 382 | 27.025 | 51.881 | 110.926 | 1.00 40.21 | B N |
| ATOM | 5246 | CA | ALA | B | 382 | 26.119 | 52.857 | 110.309 | 1.00 42.27 | B C |
| ATOM | 5247 | CB | ALA | B | 382 | 25.947 | 52.537 | 108.818 | 1.00 43.33 | B C |
| ATOM | 5248 | C | ALA | B | 382 | 24.748 | 52.998 | 110.972 | 1.00 42.94 | B C |
| ATOM | 5249 | O | ALA | B | 382 | 23.915 | 53.783 | 110.455 | 1.00 43.42 | B O |
| ATOM | 5250 | OXT | ALA | B | 382 | 24.526 | 52.334 | 112.008 | 1.00 45.84 | B O |
| TER | 5251 | | ALA | B | 382 | | | | | B |
| ATOM | 5252 | O | HOH | W | 1 | 20.170 | 40.353 | 79.716 | 1.00 16.22 | W O |
| ATOM | 5253 | O | HOH | W | 2 | 21.694 | 40.432 | 33.508 | 1.00 18.07 | W O |
| ATOM | 5254 | O | HOH | W | 3 | 18.991 | 26.492 | 62.341 | 1.00 16.94 | W O |
| ATOM | 5255 | O | HOH | W | 4 | 16.128 | 39.802 | 91.548 | 1.00 23.87 | W O |
| ATOM | 5256 | O | HOH | W | 5 | 19.619 | 43.910 | 81.460 | 1.00 18.68 | W O |
| ATOM | 5257 | O | HOH | W | 6 | 26.256 | 38.744 | 77.201 | 1.00 19.01 | W O |
| ATOM | 5258 | O | HOH | W | 7 | 22.022 | 36.866 | 55.577 | 1.00 17.22 | W O |
| ATOM | 5259 | O | HOH | W | 8 | 20.330 | 43.777 | 62.453 | 1.00 19.57 | W O |
| ATOM | 5260 | O | HOH | W | 9 | 7.721 | 42.017 | 76.700 | 1.00 21.49 | W O |
| ATOM | 5261 | O | HOH | W | 10 | 22.350 | 37.509 | 65.625 | 1.00 15.73 | W O |
| ATOM | 5262 | O | HOH | W | 11 | 5.141 | 47.547 | 83.429 | 1.00 22.45 | W O |
| ATOM | 5263 | O | HOH | W | 12 | 23.883 | 52.889 | 97.574 | 1.00 18.56 | W O |
| ATOM | 5264 | O | HOH | W | 13 | 38.167 | 50.269 | 81.471 | 1.00 20.23 | W O |
| ATOM | 5265 | O | HOH | W | 14 | 18.785 | 38.566 | 57.421 | 1.00 18.92 | W O |
| ATOM | 5266 | O | HOH | W | 15 | 18.628 | 34.067 | 89.684 | 1.00 18.94 | W O |
| ATOM | 5267 | O | HOH | W | 16 | 27.656 | 35.217 | 62.487 | 1.00 20.76 | W O |
| ATOM | 5268 | O | HOH | W | 17 | 14.756 | 50.177 | 80.590 | 1.00 16.02 | W O |
| ATOM | 5269 | O | HOH | W | 18 | 14.319 | 56.748 | 82.076 | 1.00 18.50 | W O |
| ATOM | 5270 | O | HOH | W | 19 | 31.278 | 38.735 | 65.562 | 1.00 23.82 | W O |
| ATOM | 5271 | O | HOH | W | 20 | 30.303 | 41.113 | 77.352 | 1.00 20.28 | W O |
| ATOM | 5272 | O | HOH | W | 21 | 37.674 | 36.510 | 59.142 | 1.00 15.70 | W O |
| ATOM | 5273 | O | HOH | W | 22 | 36.720 | 42.940 | 55.960 | 1.00 22.03 | W O |
| ATOM | 5274 | O | HOH | W | 23 | 19.248 | 42.101 | 66.364 | 1.00 23.60 | W O |
| ATOM | 5275 | O | HOH | W | 24 | 25.184 | 57.421 | 78.018 | 1.00 20.72 | W O |
| ATOM | 5276 | O | HOH | W | 25 | 26.186 | 46.519 | 102.789 | 1.00 19.56 | W O |
| ATOM | 5277 | O | HOH | W | 26 | 13.488 | 57.294 | 90.029 | 1.00 22.16 | W O |
| ATOM | 5278 | O | HOH | W | 27 | 23.467 | 20.728 | 51.526 | 1.00 29.77 | W O |
| ATOM | 5279 | O | HOH | W | 28 | 12.329 | 34.775 | 55.691 | 1.00 23.91 | W O |
| ATOM | 5280 | O | HOH | W | 29 | 34.706 | 37.587 | 57.062 | 1.00 14.54 | W O |
| ATOM | 5281 | O | HOH | W | 30 | 48.261 | 26.008 | 58.716 | 1.00 34.91 | W O |
| ATOM | 5282 | O | HOH | W | 32 | 21.261 | 51.525 | 69.728 | 1.00 24.43 | W O |
| ATOM | 5283 | O | HOH | W | 33 | 22.268 | 38.919 | 70.367 | 1.00 26.10 | W O |
| ATOM | 5284 | O | HOH | W | 34 | 32.508 | 25.192 | 60.102 | 1.00 26.27 | W O |
| ATOM | 5285 | O | HOH | W | 35 | 35.879 | 44.067 | 99.705 | 1.00 25.28 | W O |
| ATOM | 5286 | O | HOH | W | 36 | 17.788 | 41.357 | 68.938 | 1.00 17.26 | W O |
| ATOM | 5287 | O | HOH | W | 37 | 12.366 | 70.858 | 75.814 | 1.00 42.21 | W O |
| ATOM | 5288 | O | HOH | W | 38 | 12.992 | 55.584 | 76.464 | 1.00 27.43 | W O |
| ATOM | 5289 | O | HOH | W | 39 | 28.573 | 37.205 | 38.001 | 1.00 19.37 | W O |
| ATOM | 5290 | O | HOH | W | 40 | 15.855 | 34.842 | 82.986 | 1.00 22.08 | W O |
| ATOM | 5291 | O | HOH | W | 41 | 3.098 | 77.686 | 89.384 | 1.00 34.74 | W O |
| ATOM | 5292 | O | HOH | W | 42 | 9.951 | 48.891 | 50.913 | 1.00 28.22 | W O |
| ATOM | 5293 | O | HOH | W | 43 | 3.758 | 49.864 | 86.297 | 1.00 48.04 | W O |

FIG. 5-89

```
ATOM   5294  O    HOH W   44      24.704  25.652  87.767  1.00 39.40      W    O
ATOM   5295  O    HOH W   45      18.394  45.159  59.331  1.00 23.94      W    O
ATOM   5296  O    HOH W   46      12.921  42.159  38.628  1.00 23.08      W    O
ATOM   5297  O    HOH W   47      22.591  22.024  55.775  1.00 21.24      W    O
ATOM   5298  O    HOH W   48      36.386  40.253  56.603  1.00 23.35      W    O
ATOM   5299  O    HOH W   49      24.318  54.904 104.654  1.00 22.79      W    O
ATOM   5300  O    HOH W   50      27.230  38.495  74.285  1.00 23.18      W    O
ATOM   5301  O    HOH W   51      30.150  47.609  56.541  1.00 33.23      W    O
ATOM   5302  O    HOH W   52      31.107  43.072  79.230  1.00 20.70      W    O
ATOM   5303  O    HOH W   53      18.270  59.794  92.761  1.00 25.35      W    O
ATOM   5304  O    HOH W   54      17.789  48.989  73.761  1.00 17.16      W    O
ATOM   5305  O    HOH W   55      22.809  42.920  23.972  1.00 38.67      W    O
ATOM   5306  O    HOH W   56      28.490  33.149  59.393  1.00 23.17      W    O
ATOM   5307  O    HOH W   57      29.607  51.883  55.707  1.00 31.48      W    O
ATOM   5308  O    HOH W   58      33.481  52.076  77.290  1.00 32.53      W    O
ATOM   5309  O    HOH W   59      13.117  40.892  94.180  1.00 23.53      W    O
ATOM   5310  O    HOH W   60      33.783  56.942 104.073  1.00 33.16      W    O
ATOM   5311  O    HOH W   61      14.023  29.012  51.865  1.00 25.40      W    O
ATOM   5312  O    HOH W   62       8.827  36.806  80.408  1.00 23.35      W    O
ATOM   5313  O    HOH W   63      33.570  20.752  62.952  1.00 33.83      W    O
ATOM   5314  O    HOH W   64      11.221  37.791  87.180  1.00 23.44      W    O
ATOM   5315  O    HOH W   65      13.376  37.065  48.517  1.00 20.68      W    O
ATOM   5316  O    HOH W   66      33.551  29.277  54.124  1.00 23.71      W    O
ATOM   5317  O    HOH W   67      27.813  57.206  77.637  1.00 21.24      W    O
ATOM   5318  O    HOH W   68      16.797  58.134  81.617  1.00 23.90      W    O
ATOM   5319  O    HOH W   69      27.438  31.317  56.455  1.00 22.34      W    O
ATOM   5320  O    HOH W   70       7.638  36.875  83.067  1.00 28.72      W    O
ATOM   5321  O    HOH W   71      10.825  36.839  48.773  1.00 20.05      W    O
ATOM   5322  O    HOH W   72      15.124  42.298  98.046  1.00 27.21      W    O
ATOM   5323  O    HOH W   73      22.074  46.280  77.847  1.00 24.95      W    O
ATOM   5324  O    HOH W   74      12.802  28.789  81.633  1.00 30.80      W    O
ATOM   5325  O    HOH W   75      11.457  27.773  55.431  1.00 30.03      W    O
ATOM   5326  O    HOH W   76      16.195  33.533  42.818  1.00 33.19      W    O
ATOM   5327  O    HOH W   77       7.093  31.328  56.591  1.00 35.40      W    O
ATOM   5328  O    HOH W   78      16.886  37.254  66.838  1.00 34.93      W    O
ATOM   5329  O    HOH W   79       2.322  39.540  55.049  1.00 33.60      W    O
ATOM   5330  O    HOH W   80      10.595  41.337  97.163  1.00 37.30      W    O
ATOM   5331  O    HOH W   81      30.347  60.873  98.638  1.00 25.44      W    O
ATOM   5332  O    HOH W   82      24.621  50.354  73.304  1.00 35.73      W    O
ATOM   5333  O    HOH W   83      53.422  19.857  46.543  1.00 34.90      W    O
ATOM   5334  O    HOH W   84      30.161  36.044  99.404  1.00 32.32      W    O
ATOM   5335  O    HOH W   85      23.154  41.314  66.764  1.00 42.51      W    O
ATOM   5336  O    HOH W   86       2.720  55.131  87.673  1.00 30.01      W    O
ATOM   5337  O    HOH W   87      16.181  28.960  49.005  1.00 25.06      W    O
ATOM   5338  O    HOH W   88      29.221  33.001  62.883  1.00 31.57      W    O
ATOM   5339  O    HOH W   89      32.302  16.244  52.693  1.00 44.89      W    O
ATOM   5340  O    HOH W   90       7.361  46.542  54.030  1.00 32.56      W    O
ATOM   5341  O    HOH W   91      23.464  48.554  55.840  1.00 22.07      W    O
ATOM   5342  O    HOH W   92      33.062  28.605  44.044  1.00 30.51      W    O
ATOM   5343  O    HOH W   93      16.534  50.785  77.003  1.00 20.12      W    O
ATOM   5344  O    HOH W   94       9.702  33.771  56.558  1.00 30.62      W    O
ATOM   5345  O    HOH W   95      18.790  46.428  61.982  1.00 31.65      W    O
ATOM   5346  O    HOH W   96      36.726  59.543  90.341  1.00 40.54      W    O
ATOM   5347  O    HOH W   97      26.064  36.652  98.818  1.00 26.06      W    O
ATOM   5348  O    HOH W   98      25.101  39.398  58.631  1.00 23.14      W    O
ATOM   5349  O    HOH W   99      11.532  40.940  89.802  1.00 29.66      W    O
ATOM   5350  O    HOH W  100      14.955  57.618  92.205  1.00 17.12      W    O
ATOM   5351  O    HOH W  101      18.430  42.132  28.131  1.00 42.95      W    O
ATOM   5352  O    HOH W  102      21.607  58.760  75.590  1.00 21.99      W    O
ATOM   5353  O    HOH W  103      22.044  56.244  77.461  1.00 28.13      W    O
```

FIG. 5-90

```
ATOM   5354  O    HOH W 104      23.638  56.292  75.230  1.00 32.64           W  O
ATOM   5355  O    HOH W 105      23.772  59.281  76.631  1.00 28.52           W  O
ATOM   5356  O    HOH W 106      27.895  56.780  72.597  1.00 36.26           W  O
ATOM   5357  O    HOH W 107      26.759  50.633  76.922  1.00 24.71           W  O
ATOM   5358  O    HOH W 108      15.784  23.473  57.448  1.00 25.74           W  O
ATOM   5359  O    HOH W 109      33.054  38.529  60.395  1.00 35.76           W  O
ATOM   5360  O    HOH W 110      35.210  31.735  53.876  1.00 21.45           W  O
TER    5361       HOH W 110                                                    W
ATOM   5362  C1   448 I   1      41.090  41.549  53.570  1.00 28.57           I  C
ATOM   5363  C2   448 I   1      41.082  40.476  52.485  1.00 29.88           I  C
ATOM   5364  C3   448 I   1      40.874  39.064  52.906  1.00 28.88           I  C
ATOM   5365  C4   448 I   1      40.739  38.760  54.371  1.00 30.14           I  C
ATOM   5366  C5   448 I   1      40.583  39.736  55.423  1.00 30.77           I  C
ATOM   5367  C6   448 I   1      40.818  41.121  55.007  1.00 29.89           I  C
ATOM   5368  N12  448 I   1      40.827  38.109  51.899  1.00 29.03           I  N
ATOM   5369  C13  448 I   1      40.184  36.879  51.933  1.00 28.36           I  C
ATOM   5370  N14  448 I   1      40.417  35.960  50.947  1.00 28.06           I  N
ATOM   5371  C15  448 I   1      39.747  34.717  51.134  1.00 27.41           I  C
ATOM   5372  C16  448 I   1      38.871  34.333  52.234  1.00 27.22           I  C
ATOM   5373  C17  448 I   1      38.646  35.329  53.272  1.00 26.03           I  C
ATOM   5374  N18  448 I   1      39.340  36.526  53.024  1.00 28.32           I  N
ATOM   5375  C20  448 I   1      37.738  35.331  54.509  1.00 25.51           I  C
ATOM   5376  C21  448 I   1      37.559  34.125  55.010  1.00 25.54           I  C
ATOM   5377  C22  448 I   1      36.602  34.628  56.043  1.00 25.44           I  C
ATOM   5378  N23  448 I   1      36.475  36.147  56.002  1.00 24.44           I  N
ATOM   5379  C24  448 I   1      37.314  36.564  54.816  1.00 26.32           I  C
ATOM   5380  C25  448 I   1      38.258  33.003  52.196  1.00 27.01           I  C
ATOM   5381  C30  448 I   1      35.845  33.802  57.034  1.00 24.78           I  C
ATOM   5382  O31  448 I   1      35.608  32.678  56.669  1.00 23.74           I  O
ATOM   5383  N32  448 I   1      35.490  34.356  58.181  1.00 23.50           I  N
ATOM   5384  C33  448 I   1      34.606  33.769  59.087  1.00 22.50           I  C
ATOM   5385  C34  448 I   1      33.941  34.868  59.938  1.00 21.89           I  C
ATOM   5386  O35  448 I   1      33.229  35.720  59.134  1.00 21.64           I  O
ATOM   5387  C38  448 I   1      35.329  32.832  60.026  1.00 21.55           I  C
ATOM   5388  C40  448 I   1      36.827  32.800  60.086  1.00 19.97           I  C
ATOM   5389  C41  448 I   1      37.498  31.807  61.016  1.00 21.08           I  C
ATOM   5390  C42  448 I   1      36.660  30.923  61.911  1.00 21.00           I  C
ATOM   5391  C43  448 I   1      35.157  30.985  61.840  1.00 19.39           I  C
ATOM   5392  C44  448 I   1      34.502  31.903  60.877  1.00 19.71           I  C
TER    5393       448 I   1                                                    I
ATOM   5394  C1   449 J   1      27.316  62.175  79.708  1.00 30.96           J  C
ATOM   5395  C2   449 J   1      26.414  62.601  80.882  1.00 30.39           J  C
ATOM   5396  C3   449 J   1      24.947  62.479  80.667  1.00 28.87           J  C
ATOM   5397  C4   449 J   1      24.455  61.952  79.333  1.00 30.33           J  C
ATOM   5398  C5   449 J   1      25.286  61.413  78.285  1.00 31.43           J  C
ATOM   5399  C6   449 J   1      26.707  61.599  78.440  1.00 29.55           J  C
ATOM   5400  N12  449 J   1      24.126  62.897  81.728  1.00 28.10           J  N
ATOM   5401  C13  449 J   1      22.861  62.380  82.015  1.00 25.83           J  C
ATOM   5402  N14  449 J   1      22.168  62.861  83.108  1.00 25.15           J  N
ATOM   5403  C15  449 J   1      20.869  62.338  83.264  1.00 24.03           J  C
ATOM   5404  C16  449 J   1      20.203  61.368  82.387  1.00 24.98           J  C
ATOM   5405  C17  449 J   1      20.959  60.880  81.234  1.00 25.32           J  C
ATOM   5406  N18  449 J   1      22.246  61.430  81.143  1.00 23.60           J  N
ATOM   5407  C20  449 J   1      20.621  59.824  80.143  1.00 25.68           J  C
ATOM   5408  C21  449 J   1      19.325  59.771  79.864  1.00 25.60           J  C
ATOM   5409  C22  449 J   1      19.572  58.681  78.850  1.00 25.43           J  C
ATOM   5410  N23  449 J   1      21.062  58.372  78.684  1.00 24.96           J  N
ATOM   5411  C24  449 J   1      21.728  59.195  79.718  1.00 26.88           J  C
ATOM   5412  C25  449 J   1      18.884  60.854  82.765  1.00 26.81           J  C
ATOM   5413  C30  449 J   1      18.531  57.921  78.082  1.00 24.42           J  C
```

FIG. 5-91

```
ATOM   5414  O31  449 J   1      17.447  57.814  78.618  1.00 22.75      J    O
ATOM   5415  N32  449 J   1      18.897  57.417  76.910  1.00 23.50      J    N
ATOM   5416  C33  449 J   1      18.031  56.509  76.218  1.00 21.55      J    C
ATOM   5417  C34  449 J   1      18.862  55.602  75.337  1.00 20.27      J    C
ATOM   5418  O35  449 J   1      19.574  54.753  76.137  1.00 21.10      J    O
ATOM   5419  C38  449 J   1      17.033  57.274  75.362  1.00 21.26      J    C
ATOM   5420  C40  449 J   1      17.208  58.747  75.084  1.00 21.26      J    C
ATOM   5421  C41  449 J   1      16.185  59.467  74.225  1.00 22.35      J    C
ATOM   5422  C42  449 J   1      15.020  58.689  73.651  1.00 21.25      J    C
ATOM   5423  C43  449 J   1      14.867  57.229  73.931  1.00 21.27      J    C
ATOM   5424  C44  449 J   1      15.853  56.541  74.796  1.00 21.84      J    C
TER    5425       449 J   1                                              J
END
```

FIG. 6-1

| | Atom Type | Resid | | # | X | Y | Z | Occ | B | | |
|---|---|---|---|---|---|---|---|---|---|---|---|
| ATOM | 1 | CB | LYS | A | 36 | 59.641 | 27.464 | 57.131 | 1.00 | 51.95 | A | C |
| ATOM | 2 | CG | LYS | A | 36 | 58.660 | 26.332 | 57.498 | 1.00 | 51.95 | A | C |
| ATOM | 3 | CD | LYS | A | 36 | 57.961 | 26.551 | 58.834 | 1.00 | 51.95 | A | C |
| ATOM | 4 | CE | LYS | A | 36 | 56.777 | 25.596 | 58.967 | 1.00 | 51.95 | A | C |
| ATOM | 5 | NZ | LYS | A | 36 | 55.963 | 25.820 | 60.203 | 1.00 | 51.95 | A | N |
| ATOM | 6 | C | LYS | A | 36 | 59.062 | 26.875 | 54.830 | 1.00 | 56.75 | A | C |
| ATOM | 7 | O | LYS | A | 36 | 58.240 | 27.702 | 54.419 | 1.00 | 56.75 | A | O |
| ATOM | 8 | N | LYS | A | 36 | 60.903 | 28.540 | 55.247 | 1.00 | 56.75 | A | N |
| ATOM | 9 | CA | LYS | A | 36 | 60.212 | 27.296 | 55.721 | 1.00 | 56.75 | A | C |
| ATOM | 10 | N | VAL | A | 37 | 58.976 | 25.574 | 54.577 | 1.00 | 43.54 | A | N |
| ATOM | 11 | CA | VAL | A | 37 | 57.917 | 25.054 | 53.734 | 1.00 | 43.54 | A | C |
| ATOM | 12 | CB | VAL | A | 37 | 58.495 | 24.409 | 52.496 | 1.00 | 35.30 | A | C |
| ATOM | 13 | CG1 | VAL | A | 37 | 57.375 | 24.070 | 51.526 | 1.00 | 35.30 | A | C |
| ATOM | 14 | CG2 | VAL | A | 37 | 59.517 | 25.339 | 51.875 | 1.00 | 35.30 | A | C |
| ATOM | 15 | C | VAL | A | 37 | 57.048 | 24.029 | 54.442 | 1.00 | 43.54 | A | C |
| ATOM | 16 | O | VAL | A | 37 | 57.513 | 23.309 | 55.332 | 1.00 | 43.54 | A | O |
| ATOM | 17 | N | THR | A | 38 | 55.780 | 23.973 | 54.047 | 1.00 | 38.06 | A | N |
| ATOM | 18 | CA | THR | A | 38 | 54.856 | 23.021 | 54.635 | 1.00 | 38.06 | A | C |
| ATOM | 19 | CB | THR | A | 38 | 53.695 | 23.705 | 55.372 | 1.00 | 30.23 | A | C |
| ATOM | 20 | OG1 | THR | A | 38 | 54.215 | 24.625 | 56.333 | 1.00 | 30.23 | A | O |
| ATOM | 21 | CG2 | THR | A | 38 | 52.848 | 22.676 | 56.089 | 1.00 | 30.23 | A | C |
| ATOM | 22 | C | THR | A | 38 | 54.259 | 22.178 | 53.522 | 1.00 | 38.06 | A | C |
| ATOM | 23 | O | THR | A | 38 | 53.657 | 22.712 | 52.584 | 1.00 | 38.06 | A | O |
| ATOM | 24 | N | THR | A | 39 | 54.438 | 20.862 | 53.624 | 1.00 | 34.77 | A | N |
| ATOM | 25 | CA | THR | A | 39 | 53.901 | 19.948 | 52.630 | 1.00 | 34.77 | A | C |
| ATOM | 26 | CB | THR | A | 39 | 55.015 | 19.178 | 51.897 | 1.00 | 28.29 | A | C |
| ATOM | 27 | OG1 | THR | A | 39 | 55.692 | 20.069 | 51.009 | 1.00 | 28.29 | A | O |
| ATOM | 28 | CG2 | THR | A | 39 | 54.429 | 18.046 | 51.067 | 1.00 | 28.29 | A | C |
| ATOM | 29 | C | THR | A | 39 | 52.962 | 18.970 | 53.299 | 1.00 | 34.77 | A | C |
| ATOM | 30 | O | THR | A | 39 | 53.329 | 18.325 | 54.272 | 1.00 | 34.77 | A | O |
| ATOM | 31 | N | VAL | A | 40 | 51.746 | 18.872 | 52.773 | 1.00 | 45.36 | A | N |
| ATOM | 32 | CA | VAL | A | 40 | 50.741 | 17.984 | 53.341 | 1.00 | 45.36 | A | C |
| ATOM | 33 | CB | VAL | A | 40 | 49.682 | 18.801 | 54.156 | 1.00 | 77.60 | A | C |
| ATOM | 34 | CG1 | VAL | A | 40 | 49.062 | 19.894 | 53.285 | 1.00 | 77.60 | A | C |
| ATOM | 35 | CG2 | VAL | A | 40 | 48.589 | 17.859 | 54.691 | 1.00 | 77.60 | A | C |
| ATOM | 36 | C | VAL | A | 40 | 50.042 | 17.162 | 52.260 | 1.00 | 45.36 | A | C |
| ATOM | 37 | O | VAL | A | 40 | 50.332 | 17.318 | 51.078 | 1.00 | 45.36 | A | O |
| ATOM | 38 | N | VAL | A | 41 | 49.153 | 16.260 | 52.652 | 1.00 | 38.14 | A | N |
| ATOM | 39 | CA | VAL | A | 41 | 48.421 | 15.493 | 51.652 | 1.00 | 38.14 | A | C |
| ATOM | 40 | CB | VAL | A | 41 | 48.532 | 13.962 | 51.873 | 1.00 | 21.48 | A | C |
| ATOM | 41 | CG1 | VAL | A | 41 | 47.745 | 13.225 | 50.793 | 1.00 | 21.48 | A | C |
| ATOM | 42 | CG2 | VAL | A | 41 | 49.994 | 13.537 | 51.833 | 1.00 | 21.48 | A | C |
| ATOM | 43 | C | VAL | A | 41 | 46.961 | 15.917 | 51.768 | 1.00 | 38.14 | A | C |
| ATOM | 44 | O | VAL | A | 41 | 46.319 | 15.669 | 52.791 | 1.00 | 38.14 | A | O |
| ATOM | 45 | N | ALA | A | 42 | 46.438 | 16.557 | 50.724 | 1.00 | 42.43 | A | N |
| ATOM | 46 | CA | ALA | A | 42 | 45.061 | 17.036 | 50.765 | 1.00 | 42.43 | A | C |
| ATOM | 47 | CB | ALA | A | 42 | 45.039 | 18.546 | 50.581 | 1.00 | 38.94 | A | C |
| ATOM | 48 | C | ALA | A | 42 | 44.088 | 16.392 | 49.781 | 1.00 | 42.43 | A | C |
| ATOM | 49 | O | ALA | A | 42 | 44.484 | 15.745 | 48.805 | 1.00 | 42.43 | A | O |
| ATOM | 50 | N | THR | A | 43 | 42.804 | 16.602 | 50.056 | 1.00 | 46.78 | A | N |
| ATOM | 51 | CA | THR | A | 43 | 41.720 | 16.088 | 49.235 | 1.00 | 46.78 | A | C |
| ATOM | 52 | CB | THR | A | 43 | 40.578 | 15.571 | 50.117 | 1.00 | 35.10 | A | C |
| ATOM | 53 | OG1 | THR | A | 43 | 41.104 | 14.668 | 51.095 | 1.00 | 35.10 | A | O |
| ATOM | 54 | CG2 | THR | A | 43 | 39.526 | 14.863 | 49.284 | 1.00 | 35.10 | A | C |
| ATOM | 55 | C | THR | A | 43 | 41.160 | 17.231 | 48.394 | 1.00 | 46.78 | A | C |
| ATOM | 56 | O | THR | A | 43 | 40.965 | 18.340 | 48.895 | 1.00 | 46.78 | A | O |
| ATOM | 57 | N | PRO | A | 44 | 40.895 | 16.979 | 47.106 | 1.00 | 38.20 | A | N |

FIG. 6-2

| ATOM | 58 | CD | PRO A | 44 | 41.291 | 15.786 | 46.345 | 1.00 | 43.73 | A | C |
|------|-----|-----|-------|----|--------|--------|--------|------|-------|---|---|
| ATOM | 59 | CA | PRO A | 44 | 40.350 | 18.000 | 46.209 | 1.00 | 38.20 | A | C |
| ATOM | 60 | CB | PRO A | 44 | 40.281 | 17.271 | 44.871 | 1.00 | 43.73 | A | C |
| ATOM | 61 | CG | PRO A | 44 | 41.430 | 16.346 | 44.946 | 1.00 | 43.73 | A | C |
| ATOM | 62 | C | PRO A | 44 | 38.959 | 18.439 | 46.686 | 1.00 | 38.20 | A | C |
| ATOM | 63 | O | PRO A | 44 | 38.205 | 17.629 | 47.238 | 1.00 | 38.20 | A | O |
| ATOM | 64 | N | GLY A | 45 | 38.628 | 19.714 | 46.476 | 1.00 | 41.76 | A | N |
| ATOM | 65 | CA | GLY A | 45 | 37.327 | 20.216 | 46.878 | 1.00 | 41.76 | A | C |
| ATOM | 66 | C | GLY A | 45 | 36.231 | 19.497 | 46.118 | 1.00 | 41.76 | A | C |
| ATOM | 67 | O | GLY A | 45 | 35.233 | 19.061 | 46.705 | 1.00 | 41.76 | A | O |
| ATOM | 68 | N | ALA A | 46 | 36.431 | 19.366 | 44.803 | 1.00 | 75.71 | A | N |
| ATOM | 69 | CA | ALA A | 46 | 35.487 | 18.684 | 43.918 | 1.00 | 75.71 | A | C |
| ATOM | 70 | CB | ALA A | 46 | 34.960 | 19.667 | 42.876 | 1.00 | 42.88 | A | C |
| ATOM | 71 | C | ALA A | 46 | 36.170 | 17.479 | 43.239 | 1.00 | 75.71 | A | C |
| ATOM | 72 | O | ALA A | 46 | 37.402 | 17.441 | 43.100 | 1.00 | 75.71 | A | O |
| ATOM | 73 | N | GLY A | 47 | 35.366 | 16.504 | 42.812 | 1.00 | 65.07 | A | N |
| ATOM | 74 | CA | GLY A | 47 | 35.911 | 15.307 | 42.190 | 1.00 | 65.07 | A | C |
| ATOM | 75 | C | GLY A | 47 | 36.134 | 14.269 | 43.283 | 1.00 | 65.07 | A | C |
| ATOM | 76 | O | GLY A | 47 | 36.183 | 14.637 | 44.466 | 1.00 | 65.07 | A | O |
| ATOM | 77 | N | PRO A | 48 | 36.256 | 12.968 | 42.941 | 1.00 | 71.08 | A | N |
| ATOM | 78 | CD | PRO A | 48 | 35.816 | 12.375 | 41.666 | 1.00 | 86.91 | A | C |
| ATOM | 79 | CA | PRO A | 48 | 36.469 | 11.912 | 43.944 | 1.00 | 71.08 | A | C |
| ATOM | 80 | CB | PRO A | 48 | 36.357 | 10.630 | 43.120 | 1.00 | 86.91 | A | C |
| ATOM | 81 | CG | PRO A | 48 | 35.314 | 11.000 | 42.117 | 1.00 | 86.91 | A | C |
| ATOM | 82 | C | PRO A | 48 | 37.788 | 11.992 | 44.721 | 1.00 | 71.08 | A | C |
| ATOM | 83 | O | PRO A | 48 | 38.839 | 12.350 | 44.165 | 1.00 | 71.08 | A | O |
| ATOM | 84 | N | ASP A | 49 | 37.727 | 11.637 | 46.006 | 1.00 | 50.89 | A | N |
| ATOM | 85 | CA | ASP A | 49 | 38.910 | 11.689 | 46.849 | 1.00 | 50.89 | A | C |
| ATOM | 86 | CB | ASP A | 49 | 38.683 | 11.060 | 48.234 | 1.00 | 46.24 | A | C |
| ATOM | 87 | CG | ASP A | 49 | 39.978 | 11.005 | 49.065 | 1.00 | 46.24 | A | C |
| ATOM | 88 | OD1 | ASP A | 49 | 40.831 | 11.905 | 48.888 | 1.00 | 46.24 | A | O |
| ATOM | 89 | OD2 | ASP A | 49 | 40.154 | 10.082 | 49.900 | 1.00 | 46.24 | A | O |
| ATOM | 90 | C | ASP A | 49 | 40.103 | 11.016 | 46.197 | 1.00 | 50.89 | A | C |
| ATOM | 91 | O | ASP A | 49 | 40.167 | 9.796 | 46.103 | 1.00 | 50.89 | A | O |
| ATOM | 92 | N | ARG A | 50 | 41.032 | 11.838 | 45.731 | 1.00 | 42.12 | A | N |
| ATOM | 93 | CA | ARG A | 50 | 42.270 | 11.368 | 45.128 | 1.00 | 42.12 | A | C |
| ATOM | 94 | CB | ARG A | 50 | 42.189 | 11.435 | 43.601 | 1.00 | 90.07 | A | C |
| ATOM | 95 | CG | ARG A | 50 | 42.446 | 10.085 | 42.972 | 1.00 | 90.07 | A | C |
| ATOM | 96 | CD | ARG A | 50 | 42.105 | 9.997 | 41.480 | 1.00 | 90.07 | A | C |
| ATOM | 97 | NE | ARG A | 50 | 42.309 | 8.617 | 41.054 | 1.00 | 90.07 | A | N |
| ATOM | 98 | CZ | ARG A | 50 | 41.618 | 7.595 | 41.560 | 1.00 | 90.07 | A | C |
| ATOM | 99 | NH1 | ARG A | 50 | 40.674 | 7.826 | 42.483 | 1.00 | 90.07 | A | N |
| ATOM | 100 | NH2 | ARG A | 50 | 41.911 | 6.341 | 41.204 | 1.00 | 90.07 | A | N |
| ATOM | 101 | C | ARG A | 50 | 43.333 | 12.328 | 45.650 | 1.00 | 42.12 | A | C |
| ATOM | 102 | O | ARG A | 50 | 43.835 | 13.179 | 44.926 | 1.00 | 42.12 | A | O |
| ATOM | 103 | N | PRO A | 51 | 43.718 | 12.154 | 46.917 | 1.00 | 24.73 | A | N |
| ATOM | 104 | CD | PRO A | 51 | 43.793 | 10.758 | 47.391 | 1.00 | 35.32 | A | C |
| ATOM | 105 | CA | PRO A | 51 | 44.697 | 12.968 | 47.637 | 1.00 | 24.73 | A | C |
| ATOM | 106 | CB | PRO A | 51 | 45.123 | 12.054 | 48.785 | 1.00 | 35.32 | A | C |
| ATOM | 107 | CG | PRO A | 51 | 45.103 | 10.737 | 48.149 | 1.00 | 35.32 | A | C |
| ATOM | 108 | C | PRO A | 51 | 45.852 | 13.345 | 46.772 | 1.00 | 24.73 | A | C |
| ATOM | 109 | O | PRO A | 51 | 46.109 | 12.713 | 45.768 | 1.00 | 24.73 | A | O |
| ATOM | 110 | N | GLN A | 52 | 46.552 | 14.389 | 47.178 | 1.00 | 40.86 | A | N |
| ATOM | 111 | CA | GLN A | 52 | 47.716 | 14.853 | 46.449 | 1.00 | 40.86 | A | C |
| ATOM | 112 | CB | GLN A | 52 | 47.275 | 15.608 | 45.206 | 1.00 | 68.82 | A | C |
| ATOM | 113 | CG | GLN A | 52 | 45.882 | 16.189 | 45.328 | 1.00 | 68.82 | A | C |
| ATOM | 114 | CD | GLN A | 52 | 45.117 | 16.119 | 44.013 | 1.00 | 68.82 | A | C |
| ATOM | 115 | OE1 | GLN A | 52 | 44.710 | 17.148 | 43.462 | 1.00 | 68.82 | A | O |
| ATOM | 116 | NE2 | GLN A | 52 | 44.932 | 14.906 | 43.493 | 1.00 | 68.82 | A | N |
| ATOM | 117 | C | GLN A | 52 | 48.533 | 15.769 | 47.353 | 1.00 | 40.86 | A | C |

FIG. 6-3

```
ATOM    118  O    GLN A  52      48.006  16.450  48.240  1.00 40.86      A    O
ATOM    119  N    GLU A  53      49.839  15.739  47.127  1.00 43.20      A    N
ATOM    120  CA   GLU A  53      50.780  16.530  47.888  1.00 43.20      A    C
ATOM    121  CB   GLU A  53      52.202  16.154  47.521  1.00 43.19      A    C
ATOM    122  CG   GLU A  53      52.736  14.966  48.248  1.00 43.19      A    C
ATOM    123  CD   GLU A  53      54.232  14.999  48.278  1.00 43.19      A    C
ATOM    124  OE1  GLU A  53      54.828  14.143  48.956  1.00 43.19      A    O
ATOM    125  OE2  GLU A  53      54.809  15.895  47.625  1.00 43.19      A    O
ATOM    126  C    GLU A  53      50.591  17.992  47.533  1.00 43.20      A    C
ATOM    127  O    GLU A  53      50.448  18.359  46.366  1.00 43.20      A    O
ATOM    128  N    VAL A  54      50.599  18.829  48.552  1.00 28.32      A    N
ATOM    129  CA   VAL A  54      50.458  20.248  48.337  1.00 28.32      A    C
ATOM    130  CB   VAL A  54      49.082  20.792  48.793  1.00 38.47      A    C
ATOM    131  CG1  VAL A  54      49.046  22.298  48.581  1.00 38.47      A    C
ATOM    132  CG2  VAL A  54      47.953  20.121  48.023  1.00 38.47      A    C
ATOM    133  C    VAL A  54      51.516  20.908  49.197  1.00 28.32      A    C
ATOM    134  O    VAL A  54      51.676  20.575  50.381  1.00 28.32      A    O
ATOM    135  N    SER A  55      52.237  21.841  48.593  1.00 49.20      A    N
ATOM    136  CA   SER A  55      53.292  22.562  49.292  1.00 49.20      A    C
ATOM    137  CB   SER A  55      54.644  22.318  48.616  1.00 39.01      A    C
ATOM    138  OG   SER A  55      54.994  20.952  48.700  1.00 39.01      A    O
ATOM    139  C    SER A  55      53.003  24.055  49.285  1.00 49.20      A    C
ATOM    140  O    SER A  55      52.630  24.631  48.258  1.00 49.20      A    O
ATOM    141  N    TYR A  56      53.192  24.691  50.427  1.00 44.73      A    N
ATOM    142  CA   TYR A  56      52.924  26.109  50.500  1.00 44.73      A    C
ATOM    143  CB   TYR A  56      51.451  26.339  50.781  1.00 34.73      A    C
ATOM    144  CG   TYR A  56      51.009  25.826  52.116  1.00 34.73      A    C
ATOM    145  CD1  TYR A  56      51.235  26.566  53.265  1.00 34.73      A    C
ATOM    146  CE1  TYR A  56      50.803  26.120  54.505  1.00 34.73      A    C
ATOM    147  CD2  TYR A  56      50.343  24.608  52.228  1.00 34.73      A    C
ATOM    148  CE2  TYR A  56      49.899  24.145  53.467  1.00 34.73      A    C
ATOM    149  CZ   TYR A  56      50.136  24.910  54.601  1.00 34.73      A    C
ATOM    150  OH   TYR A  56      49.705  24.477  55.828  1.00 34.73      A    O
ATOM    151  C    TYR A  56      53.769  26.758  51.569  1.00 44.73      A    C
ATOM    152  O    TYR A  56      54.033  26.169  52.615  1.00 44.73      A    O
ATOM    153  N    THR A  57      54.169  27.989  51.300  1.00 51.41      A    N
ATOM    154  CA   THR A  57      55.024  28.731  52.203  1.00 51.41      A    C
ATOM    155  CB   THR A  57      56.432  28.862  51.593  1.00 58.53      A    C
ATOM    156  OG1  THR A  57      57.249  29.690  52.431  1.00 58.53      A    O
ATOM    157  CG2  THR A  57      56.344  29.485  50.189  1.00 58.53      A    C
ATOM    158  C    THR A  57      54.476  30.128  52.470  1.00 51.41      A    C
ATOM    159  O    THR A  57      53.324  30.415  52.163  1.00 51.41      A    O
ATOM    160  N    ASP A  58      55.323  30.994  53.024  1.00 45.63      A    N
ATOM    161  CA   ASP A  58      54.956  32.369  53.341  1.00 45.63      A    C
ATOM    162  CB   ASP A  58      54.889  33.229  52.071  1.00 63.56      A    C
ATOM    163  CG   ASP A  58      56.253  33.457  51.440  1.00 63.56      A    C
ATOM    164  OD1  ASP A  58      57.226  33.707  52.190  1.00 63.56      A    O
ATOM    165  OD2  ASP A  58      56.349  33.402  50.188  1.00 63.56      A    O
ATOM    166  C    ASP A  58      53.634  32.477  54.085  1.00 45.63      A    C
ATOM    167  O    ASP A  58      52.881  33.431  53.885  1.00 45.63      A    O
ATOM    168  N    THR A  59      53.348  31.504  54.940  1.00 31.47      A    N
ATOM    169  CA   THR A  59      52.105  31.527  55.695  1.00 31.47      A    C
ATOM    170  CB   THR A  59      51.941  30.230  56.544  1.00 38.11      A    C
ATOM    171  OG1  THR A  59      50.708  30.279  57.273  1.00 38.11      A    O
ATOM    172  CG2  THR A  59      53.100  30.078  57.531  1.00 38.11      A    C
ATOM    173  C    THR A  59      52.063  32.739  56.619  1.00 31.47      A    C
ATOM    174  O    THR A  59      53.097  33.196  57.085  1.00 31.47      A    O
ATOM    175  N    LYS A  60      50.862  33.260  56.857  1.00 56.55      A    N
ATOM    176  CA   LYS A  60      50.651  34.404  57.747  1.00 56.55      A    C
ATOM    177  CB   LYS A  60      51.121  35.712  57.094  1.00 30.87      A    C
```

FIG. 6-4

```
ATOM    178  CG   LYS A  60      50.182  36.278  56.050  1.00 30.87           A    C
ATOM    179  CD   LYS A  60      50.717  37.564  55.444  1.00 30.87           A    C
ATOM    180  CE   LYS A  60      51.802  37.309  54.384  1.00 30.87           A    C
ATOM    181  NZ   LYS A  60      53.075  36.786  54.941  1.00 30.87           A    N
ATOM    182  C    LYS A  60      49.163  34.500  58.100  1.00 56.55           A    C
ATOM    183  O    LYS A  60      48.298  34.048  57.335  1.00 56.55           A    O
ATOM    184  N    VAL A  61      48.855  35.083  59.252  1.00 43.34           A    N
ATOM    185  CA   VAL A  61      47.465  35.206  59.651  1.00 43.34           A    C
ATOM    186  CB   VAL A  61      47.302  35.189  61.154  1.00 31.64           A    C
ATOM    187  CG1  VAL A  61      45.815  35.114  61.491  1.00 31.64           A    C
ATOM    188  CG2  VAL A  61      48.071  34.026  61.745  1.00 31.64           A    C
ATOM    189  C    VAL A  61      46.846  36.500  59.164  1.00 43.34           A    C
ATOM    190  O    VAL A  61      47.433  37.564  59.330  1.00 43.34           A    O
ATOM    191  N    ILE A  62      45.660  36.418  58.566  1.00 47.96           A    N
ATOM    192  CA   ILE A  62      44.991  37.627  58.096  1.00 47.96           A    C
ATOM    193  CB   ILE A  62      44.593  37.559  56.587  1.00 53.40           A    C
ATOM    194  CG2  ILE A  62      45.839  37.583  55.706  1.00 53.40           A    C
ATOM    195  CG1  ILE A  62      43.774  36.304  56.303  1.00 53.40           A    C
ATOM    196  CD1  ILE A  62      43.540  36.053  54.812  1.00 53.40           A    C
ATOM    197  C    ILE A  62      43.738  37.899  58.902  1.00 47.96           A    C
ATOM    198  O    ILE A  62      43.253  39.028  58.933  1.00 47.96           A    O
ATOM    199  N    GLY A  63      43.218  36.865  59.558  1.00 36.83           A    N
ATOM    200  CA   GLY A  63      42.019  37.042  60.352  1.00 36.83           A    C
ATOM    201  C    GLY A  63      41.806  35.945  61.366  1.00 36.83           A    C
ATOM    202  O    GLY A  63      41.755  34.762  61.011  1.00 36.83           A    O
ATOM    203  N    ASN A  64      41.678  36.330  62.635  1.00 87.22           A    N
ATOM    204  CA   ASN A  64      41.460  35.359  63.716  1.00 87.22           A    C
ATOM    205  CB   ASN A  64      42.582  35.463  64.762  1.00 69.96           A    C
ATOM    206  CG   ASN A  64      42.319  34.604  65.980  1.00 69.96           A    C
ATOM    207  OD1  ASN A  64      41.679  35.043  66.940  1.00 69.96           A    O
ATOM    208  ND2  ASN A  64      42.800  33.360  65.944  1.00 69.96           A    N
ATOM    209  C    ASN A  64      40.101  35.559  64.383  1.00 87.22           A    C
ATOM    210  O    ASN A  64      39.992  36.205  65.420  1.00 87.22           A    O
ATOM    211  N    GLY A  65      39.059  35.008  63.776  1.00 61.88           A    N
ATOM    212  CA   GLY A  65      37.741  35.174  64.356  1.00 61.88           A    C
ATOM    213  C    GLY A  65      37.099  33.915  64.933  1.00 61.88           A    C
ATOM    214  O    GLY A  65      37.481  32.768  64.636  1.00 61.88           A    O
ATOM    215  N    SER A  66      36.078  34.167  65.749  1.00 90.58           A    N
ATOM    216  CA   SER A  66      35.299  33.133  66.430  1.00 90.58           A    C
ATOM    217  CB   SER A  66      33.828  33.595  66.552  1.00 43.35           A    C
ATOM    218  OG   SER A  66      33.241  33.838  65.280  1.00 43.35           A    O
ATOM    219  C    SER A  66      35.351  31.689  65.871  1.00 90.58           A    C
ATOM    220  O    SER A  66      35.642  30.736  66.627  1.00 90.58           A    O
ATOM    221  N    PHE A  67      35.061  31.523  64.576  1.00 88.57           A    N
ATOM    222  CA   PHE A  67      35.082  30.188  63.957  1.00 88.57           A    C
ATOM    223  CB   PHE A  67      34.557  30.266  62.526  1.00 73.56           A    C
ATOM    224  CG   PHE A  67      34.967  31.522  61.807  1.00 73.56           A    C
ATOM    225  CD1  PHE A  67      36.290  31.974  61.850  1.00 73.56           A    C
ATOM    226  CD2  PHE A  67      34.034  32.259  61.085  1.00 73.56           A    C
ATOM    227  CE1  PHE A  67      36.687  33.139  61.182  1.00 73.56           A    C
ATOM    228  CE2  PHE A  67      34.420  33.430  60.408  1.00 73.56           A    C
ATOM    229  CZ   PHE A  67      35.754  33.867  60.462  1.00 73.56           A    C
ATOM    230  C    PHE A  67      36.493  29.574  63.950  1.00 88.57           A    C
ATOM    231  O    PHE A  67      36.686  28.435  64.394  1.00 88.57           A    O
ATOM    232  N    GLY A  68      37.464  30.333  63.444  1.00 53.41           A    N
ATOM    233  CA   GLY A  68      38.827  29.854  63.392  1.00 53.41           A    C
ATOM    234  C    GLY A  68      39.815  30.869  62.846  1.00 53.41           A    C
ATOM    235  O    GLY A  68      39.470  32.027  62.554  1.00 53.41           A    O
ATOM    236  N    VAL A  69      41.063  30.436  62.715  1.00 53.52           A    N
ATOM    237  CA   VAL A  69      42.080  31.320  62.191  1.00 53.52           A    C
```

FIG. 6-5

| ATOM | 238 | CB | VAL | A | 69 | 43.487 | 30.957 | 62.705 | 1.00 | 61.53 | A | C |
| --- | --- | --- | --- | --- | --- | --- | --- | --- | --- | --- | --- | --- |
| ATOM | 239 | CG1 | VAL | A | 69 | 44.410 | 32.151 | 62.494 | 1.00 | 61.53 | A | C |
| ATOM | 240 | CG2 | VAL | A | 69 | 43.435 | 30.539 | 64.180 | 1.00 | 61.53 | A | C |
| ATOM | 241 | C | VAL | A | 69 | 42.084 | 31.174 | 60.683 | 1.00 | 53.52 | A | C |
| ATOM | 242 | O | VAL | A | 69 | 42.137 | 30.063 | 60.164 | 1.00 | 53.52 | A | O |
| ATOM | 243 | N | VAL | A | 70 | 42.007 | 32.296 | 59.983 | 1.00 | 35.19 | A | N |
| ATOM | 244 | CA | VAL | A | 70 | 42.045 | 32.285 | 58.530 | 1.00 | 35.19 | A | C |
| ATOM | 245 | CB | VAL | A | 70 | 40.999 | 33.209 | 57.947 | 1.00 | 35.93 | A | C |
| ATOM | 246 | CG1 | VAL | A | 70 | 41.201 | 33.323 | 56.445 | 1.00 | 35.93 | A | C |
| ATOM | 247 | CG2 | VAL | A | 70 | 39.604 | 32.699 | 58.292 | 1.00 | 35.93 | A | C |
| ATOM | 248 | C | VAL | A | 70 | 43.409 | 32.782 | 58.069 | 1.00 | 35.19 | A | C |
| ATOM | 249 | O | VAL | A | 70 | 43.689 | 33.990 | 58.102 | 1.00 | 35.19 | A | O |
| ATOM | 250 | N | TYR | A | 71 | 44.267 | 31.860 | 57.651 | 1.00 | 36.17 | A | N |
| ATOM | 251 | CA | TYR | A | 71 | 45.592 | 32.257 | 57.197 | 1.00 | 36.17 | A | C |
| ATOM | 252 | CB | TYR | A | 71 | 46.628 | 31.164 | 57.449 | 1.00 | 40.57 | A | C |
| ATOM | 253 | CG | TYR | A | 71 | 46.667 | 30.589 | 58.838 | 1.00 | 40.57 | A | C |
| ATOM | 254 | CD1 | TYR | A | 71 | 45.791 | 29.576 | 59.212 | 1.00 | 40.57 | A | C |
| ATOM | 255 | CE1 | TYR | A | 71 | 45.879 | 28.964 | 60.474 | 1.00 | 40.57 | A | C |
| ATOM | 256 | CD2 | TYR | A | 71 | 47.633 | 31.002 | 59.759 | 1.00 | 40.57 | A | C |
| ATOM | 257 | CE2 | TYR | A | 71 | 47.734 | 30.405 | 61.025 | 1.00 | 40.57 | A | C |
| ATOM | 258 | CZ | TYR | A | 71 | 46.851 | 29.380 | 61.380 | 1.00 | 40.57 | A | C |
| ATOM | 259 | OH | TYR | A | 71 | 46.932 | 28.757 | 62.620 | 1.00 | 40.57 | A | O |
| ATOM | 260 | C | TYR | A | 71 | 45.632 | 32.560 | 55.711 | 1.00 | 36.17 | A | C |
| ATOM | 261 | O | TYR | A | 71 | 44.642 | 32.442 | 54.988 | 1.00 | 36.17 | A | O |
| ATOM | 262 | N | GLN | A | 72 | 46.810 | 32.968 | 55.276 | 1.00 | 38.22 | A | N |
| ATOM | 263 | CA | GLN | A | 72 | 47.067 | 33.231 | 53.880 | 1.00 | 38.22 | A | C |
| ATOM | 264 | CB | GLN | A | 72 | 47.265 | 34.717 | 53.600 | 1.00 | 45.37 | A | C |
| ATOM | 265 | CG | GLN | A | 72 | 47.407 | 34.988 | 52.116 | 1.00 | 45.37 | A | C |
| ATOM | 266 | CD | GLN | A | 72 | 48.446 | 36.039 | 51.806 | 1.00 | 45.37 | A | C |
| ATOM | 267 | OE1 | GLN | A | 72 | 49.588 | 35.946 | 52.260 | 1.00 | 45.37 | A | O |
| ATOM | 268 | NE2 | GLN | A | 72 | 48.063 | 37.043 | 51.015 | 1.00 | 45.37 | A | N |
| ATOM | 269 | C | GLN | A | 72 | 48.382 | 32.499 | 53.701 | 1.00 | 38.22 | A | C |
| ATOM | 270 | O | GLN | A | 72 | 49.159 | 32.381 | 54.658 | 1.00 | 38.22 | A | O |
| ATOM | 271 | N | ALA | A | 73 | 48.636 | 32.010 | 52.495 | 1.00 | 32.49 | A | N |
| ATOM | 272 | CA | ALA | A | 73 | 49.855 | 31.269 | 52.231 | 1.00 | 32.49 | A | C |
| ATOM | 273 | CB | ALA | A | 73 | 49.705 | 29.834 | 52.715 | 1.00 | 13.62 | A | C |
| ATOM | 274 | C | ALA | A | 73 | 50.137 | 31.292 | 50.743 | 1.00 | 32.49 | A | C |
| ATOM | 275 | O | ALA | A | 73 | 49.280 | 31.691 | 49.940 | 1.00 | 32.49 | A | O |
| ATOM | 276 | N | LYS | A | 74 | 51.341 | 30.859 | 50.380 | 1.00 | 50.07 | A | N |
| ATOM | 277 | CA | LYS | A | 74 | 51.745 | 30.842 | 48.987 | 1.00 | 50.07 | A | C |
| ATOM | 278 | CB | LYS | A | 74 | 52.955 | 31.764 | 48.770 | 1.00 | 50.67 | A | C |
| ATOM | 279 | CG | LYS | A | 74 | 53.221 | 32.110 | 47.298 | 1.00 | 50.67 | A | C |
| ATOM | 280 | CD | LYS | A | 74 | 54.715 | 32.335 | 47.011 | 1.00 | 50.67 | A | C |
| ATOM | 281 | CE | LYS | A | 74 | 55.482 | 30.996 | 46.923 | 1.00 | 50.67 | A | C |
| ATOM | 282 | NZ | LYS | A | 74 | 56.934 | 31.099 | 46.527 | 1.00 | 50.67 | A | N |
| ATOM | 283 | C | LYS | A | 74 | 52.100 | 29.432 | 48.523 | 1.00 | 50.07 | A | C |
| ATOM | 284 | O | LYS | A | 74 | 52.969 | 28.766 | 49.101 | 1.00 | 50.07 | A | O |
| ATOM | 285 | N | LEU | A | 75 | 51.423 | 28.980 | 47.474 | 1.00 | 36.01 | A | N |
| ATOM | 286 | CA | LEU | A | 75 | 51.707 | 27.670 | 46.931 | 1.00 | 36.01 | A | C |
| ATOM | 287 | CB | LEU | A | 75 | 50.638 | 27.271 | 45.913 | 1.00 | 30.23 | A | C |
| ATOM | 288 | CG | LEU | A | 75 | 49.300 | 26.971 | 46.600 | 1.00 | 30.23 | A | C |
| ATOM | 289 | CD1 | LEU | A | 75 | 48.312 | 26.437 | 45.586 | 1.00 | 30.23 | A | C |
| ATOM | 290 | CD2 | LEU | A | 75 | 49.500 | 25.953 | 47.713 | 1.00 | 30.23 | A | C |
| ATOM | 291 | C | LEU | A | 75 | 53.087 | 27.736 | 46.295 | 1.00 | 36.01 | A | C |
| ATOM | 292 | O | LEU | A | 75 | 53.361 | 28.597 | 45.461 | 1.00 | 36.01 | A | O |
| ATOM | 293 | N | CYS | A | 76 | 53.954 | 26.826 | 46.724 | 1.00 | 56.58 | A | N |
| ATOM | 294 | CA | CYS | A | 76 | 55.327 | 26.748 | 46.246 | 1.00 | 56.58 | A | C |
| ATOM | 295 | CB | CYS | A | 76 | 55.975 | 25.488 | 46.791 | 1.00 | 46.89 | A | C |
| ATOM | 296 | SG | CYS | A | 76 | 56.289 | 25.583 | 48.533 | 1.00 | 46.89 | A | S |
| ATOM | 297 | C | CYS | A | 76 | 55.558 | 26.789 | 44.735 | 1.00 | 56.58 | A | C |

FIG. 6-6

```
ATOM    298  O    CYS A  76      56.180  27.725  44.205  1.00 56.58          A    O
ATOM    299  N    ASP A  77      55.064  25.774  44.040  1.00 58.16          A    N
ATOM    300  CA   ASP A  77      55.283  25.691  42.610  1.00 58.16          A    C
ATOM    301  CB   ASP A  77      54.991  24.261  42.142  1.00 63.21          A    C
ATOM    302  CG   ASP A  77      55.718  23.205  43.001  1.00 63.21          A    C
ATOM    303  OD1  ASP A  77      56.968  23.318  43.164  1.00 63.21          A    O
ATOM    304  OD2  ASP A  77      55.032  22.273  43.508  1.00 63.21          A    O
ATOM    305  C    ASP A  77      54.522  26.719  41.774  1.00 58.16          A    C
ATOM    306  O    ASP A  77      55.149  27.519  41.066  1.00 58.16          A    O
ATOM    307  N    SER A  78      53.190  26.719  41.851  1.00 49.21          A    N
ATOM    308  CA   SER A  78      52.396  27.666  41.065  1.00 49.21          A    C
ATOM    309  CB   SER A  78      50.902  27.375  41.219  1.00 73.03          A    C
ATOM    310  OG   SER A  78      50.484  27.594  42.553  1.00 73.03          A    O
ATOM    311  C    SER A  78      52.671  29.108  41.465  1.00 49.21          A    C
ATOM    312  O    SER A  78      52.558  30.019  40.645  1.00 49.21          A    O
ATOM    313  N    GLY A  79      53.048  29.309  42.723  1.00 51.16          A    N
ATOM    314  CA   GLY A  79      53.316  30.655  43.196  1.00 51.16          A    C
ATOM    315  C    GLY A  79      52.031  31.349  43.611  1.00 51.16          A    C
ATOM    316  O    GLY A  79      52.060  32.429  44.201  1.00 51.16          A    O
ATOM    317  N    GLU A  80      50.902  30.718  43.314  1.00 34.82          A    N
ATOM    318  CA   GLU A  80      49.606  31.276  43.659  1.00 34.82          A    C
ATOM    319  CB   GLU A  80      48.495  30.330  43.237  1.00 49.18          A    C
ATOM    320  CG   GLU A  80      48.469  30.041  41.770  1.00 49.18          A    C
ATOM    321  CD   GLU A  80      47.217  29.317  41.378  1.00 49.18          A    C
ATOM    322  OE1  GLU A  80      47.062  29.020  40.178  1.00 49.18          A    O
ATOM    323  OE2  GLU A  80      46.391  29.050  42.278  1.00 49.18          A    O
ATOM    324  C    GLU A  80      49.442  31.561  45.146  1.00 34.82          A    C
ATOM    325  O    GLU A  80      50.253  31.148  45.975  1.00 34.82          A    O
ATOM    326  N    LEU A  81      48.365  32.264  45.473  1.00 33.23          A    N
ATOM    327  CA   LEU A  81      48.065  32.617  46.854  1.00 33.23          A    C
ATOM    328  CB   LEU A  81      47.820  34.123  46.949  1.00 39.17          A    C
ATOM    329  CG   LEU A  81      49.104  34.925  46.718  1.00 39.17          A    C
ATOM    330  CD1  LEU A  81      48.769  36.365  46.396  1.00 39.17          A    C
ATOM    331  CD2  LEU A  81      49.986  34.832  47.957  1.00 39.17          A    C
ATOM    332  C    LEU A  81      46.845  31.841  47.323  1.00 33.23          A    C
ATOM    333  O    LEU A  81      45.968  31.528  46.528  1.00 33.23          A    O
ATOM    334  N    VAL A  82      46.786  31.520  48.607  1.00 25.10          A    N
ATOM    335  CA   VAL A  82      45.649  30.767  49.108  1.00 25.10          A    C
ATOM    336  CB   VAL A  82      45.935  29.241  49.129  1.00 28.41          A    C
ATOM    337  CG1  VAL A  82      46.039  28.708  47.708  1.00 28.41          A    C
ATOM    338  CG2  VAL A  82      47.219  28.955  49.898  1.00 28.41          A    C
ATOM    339  C    VAL A  82      45.218  31.186  50.497  1.00 25.10          A    C
ATOM    340  O    VAL A  82      45.964  31.831  51.229  1.00 25.10          A    O
ATOM    341  N    ALA A  83      43.998  30.811  50.849  1.00 24.18          A    N
ATOM    342  CA   ALA A  83      43.453  31.122  52.153  1.00 24.18          A    C
ATOM    343  CB   ALA A  83      42.165  31.897  51.999  1.00  9.22          A    C
ATOM    344  C    ALA A  83      43.205  29.806  52.883  1.00 24.18          A    C
ATOM    345  O    ALA A  83      42.644  28.860  52.319  1.00 24.18          A    O
ATOM    346  N    ILE A  84      43.636  29.737  54.135  1.00 25.59          A    N
ATOM    347  CA   ILE A  84      43.444  28.521  54.891  1.00 25.59          A    C
ATOM    348  CB   ILE A  84      44.797  27.880  55.298  1.00 38.74          A    C
ATOM    349  CG2  ILE A  84      44.543  26.545  56.002  1.00 38.74          A    C
ATOM    350  CG1  ILE A  84      45.663  27.629  54.057  1.00 38.74          A    C
ATOM    351  CD1  ILE A  84      47.060  27.081  54.367  1.00 38.74          A    C
ATOM    352  C    ILE A  84      42.612  28.741  56.137  1.00 25.59          A    C
ATOM    353  O    ILE A  84      43.087  29.300  57.130  1.00 25.59          A    O
ATOM    354  N    LYS A  85      41.360  28.300  56.078  1.00 43.26          A    N
ATOM    355  CA   LYS A  85      40.464  28.420  57.220  1.00 43.26          A    C
ATOM    356  CB   LYS A  85      39.004  28.389  56.762  1.00 41.66          A    C
ATOM    357  CG   LYS A  85      38.024  28.917  57.801  1.00 41.66          A    C
```

FIG. 6-7

| ATOM | 358 | CD | LYS A | 85 | 36.711 | 29.375 | 57.167 | 1.00 | 41.66 | A | C |
| ATOM | 359 | CE | LYS A | 85 | 35.686 | 29.736 | 58.239 | 1.00 | 41.66 | A | C |
| ATOM | 360 | NZ | LYS A | 85 | 34.414 | 30.256 | 57.658 | 1.00 | 41.66 | A | N |
| ATOM | 361 | C | LYS A | 85 | 40.802 | 27.215 | 58.085 | 1.00 | 43.26 | A | C |
| ATOM | 362 | O | LYS A | 85 | 41.007 | 26.115 | 57.571 | 1.00 | 43.26 | A | O |
| ATOM | 363 | N | LYS A | 86 | 40.879 | 27.413 | 59.392 | 1.00 | 38.38 | A | N |
| ATOM | 364 | CA | LYS A | 86 | 41.252 | 26.319 | 60.270 | 1.00 | 38.38 | A | C |
| ATOM | 365 | CB | LYS A | 86 | 42.726 | 26.477 | 60.644 | 1.00 | 38.54 | A | C |
| ATOM | 366 | CG | LYS A | 86 | 43.332 | 25.333 | 61.395 | 1.00 | 38.54 | A | C |
| ATOM | 367 | CD | LYS A | 86 | 44.805 | 25.600 | 61.632 | 1.00 | 38.54 | A | C |
| ATOM | 368 | CE | LYS A | 86 | 45.406 | 24.523 | 62.519 | 1.00 | 38.54 | A | C |
| ATOM | 369 | NZ | LYS A | 86 | 46.854 | 24.746 | 62.778 | 1.00 | 38.54 | A | N |
| ATOM | 370 | C | LYS A | 86 | 40.380 | 26.332 | 61.503 | 1.00 | 38.38 | A | C |
| ATOM | 371 | O | LYS A | 86 | 40.452 | 27.263 | 62.298 | 1.00 | 38.38 | A | O |
| ATOM | 372 | N | VAL A | 87 | 39.556 | 25.301 | 61.660 | 1.00 | 39.10 | A | N |
| ATOM | 373 | CA | VAL A | 87 | 38.656 | 25.215 | 62.802 | 1.00 | 39.10 | A | C |
| ATOM | 374 | CB | VAL A | 87 | 37.219 | 25.578 | 62.386 | 1.00 | 48.18 | A | C |
| ATOM | 375 | CG1 | VAL A | 87 | 36.748 | 24.613 | 61.291 | 1.00 | 48.18 | A | C |
| ATOM | 376 | CG2 | VAL A | 87 | 36.281 | 25.537 | 63.617 | 1.00 | 48.18 | A | C |
| ATOM | 377 | C | VAL A | 87 | 38.646 | 23.820 | 63.421 | 1.00 | 39.10 | A | C |
| ATOM | 378 | O | VAL A | 87 | 38.805 | 22.820 | 62.715 | 1.00 | 39.10 | A | O |
| ATOM | 379 | N | LEU A | 88 | 38.447 | 23.774 | 64.740 | 1.00 | 45.79 | A | N |
| ATOM | 380 | CA | LEU A | 88 | 38.409 | 22.520 | 65.489 | 1.00 | 45.79 | A | C |
| ATOM | 381 | CB | LEU A | 88 | 38.125 | 22.778 | 66.968 | 1.00 | 36.83 | A | C |
| ATOM | 382 | CG | LEU A | 88 | 39.212 | 22.350 | 67.951 | 1.00 | 36.83 | A | C |
| ATOM | 383 | CD1 | LEU A | 88 | 40.143 | 23.522 | 68.191 | 1.00 | 36.83 | A | C |
| ATOM | 384 | CD2 | LEU A | 88 | 38.587 | 21.905 | 69.265 | 1.00 | 36.83 | A | C |
| ATOM | 385 | C | LEU A | 88 | 37.313 | 21.625 | 64.951 | 1.00 | 45.79 | A | C |
| ATOM | 386 | O | LEU A | 88 | 36.195 | 22.090 | 64.708 | 1.00 | 45.79 | A | O |
| ATOM | 387 | N | GLN A | 89 | 37.633 | 20.343 | 64.762 | 1.00 | 80.36 | A | N |
| ATOM | 388 | CA | GLN A | 89 | 36.647 | 19.391 | 64.258 | 1.00 | 80.36 | A | C |
| ATOM | 389 | CB | GLN A | 89 | 37.075 | 18.811 | 62.903 | 1.00 | 60.59 | A | C |
| ATOM | 390 | CG | GLN A | 89 | 35.880 | 18.374 | 62.051 | 1.00 | 60.59 | A | C |
| ATOM | 391 | CD | GLN A | 89 | 34.667 | 19.295 | 62.243 | 1.00 | 60.59 | A | C |
| ATOM | 392 | OE1 | GLN A | 89 | 34.803 | 20.530 | 62.313 | 1.00 | 60.59 | A | O |
| ATOM | 393 | NE2 | GLN A | 89 | 33.476 | 18.697 | 62.332 | 1.00 | 60.59 | A | N |
| ATOM | 394 | C | GLN A | 89 | 36.421 | 18.272 | 65.269 | 1.00 | 80.36 | A | C |
| ATOM | 395 | O | GLN A | 89 | 37.356 | 17.534 | 65.636 | 1.00 | 80.36 | A | O |
| ATOM | 396 | N | ALA A | 90 | 35.171 | 18.164 | 65.719 | 1.00 | 100.00 | A | N |
| ATOM | 397 | CA | ALA A | 90 | 34.792 | 17.161 | 66.713 | 1.00 | 100.00 | A | C |
| ATOM | 398 | CB | ALA A | 90 | 33.628 | 17.688 | 67.589 | 1.00 | 70.85 | A | C |
| ATOM | 399 | C | ALA A | 90 | 34.413 | 15.816 | 66.103 | 1.00 | 100.00 | A | C |
| ATOM | 400 | O | ALA A | 90 | 33.277 | 15.640 | 65.637 | 1.00 | 100.00 | A | O |
| ATOM | 401 | N | ALA A | 91 | 35.372 | 14.884 | 66.133 | 1.00 | 72.86 | A | N |
| ATOM | 402 | CA | ALA A | 91 | 35.225 | 13.520 | 65.612 | 1.00 | 72.86 | A | C |
| ATOM | 403 | CB | ALA A | 91 | 36.088 | 12.569 | 66.447 | 1.00 | 55.19 | A | C |
| ATOM | 404 | C | ALA A | 91 | 33.788 | 12.966 | 65.500 | 1.00 | 72.86 | A | C |
| ATOM | 405 | O | ALA A | 91 | 33.540 | 12.075 | 64.678 | 1.00 | 72.86 | A | O |
| ATOM | 406 | N | ALA A | 92 | 32.854 | 13.478 | 66.313 | 1.00 | 100.00 | A | N |
| ATOM | 407 | CA | ALA A | 92 | 31.444 | 13.036 | 66.275 | 1.00 | 100.00 | A | C |
| ATOM | 408 | CB | ALA A | 92 | 30.581 | 13.900 | 67.224 | 1.00 | 35.15 | A | C |
| ATOM | 409 | C | ALA A | 92 | 30.853 | 13.069 | 64.855 | 1.00 | 100.00 | A | C |
| ATOM | 410 | O | ALA A | 92 | 30.889 | 12.064 | 64.131 | 1.00 | 100.00 | A | O |
| ATOM | 411 | N | ALA A | 93 | 30.311 | 14.217 | 64.449 | 1.00 | 98.66 | A | N |
| ATOM | 412 | CA | ALA A | 93 | 29.712 | 14.331 | 63.105 | 1.00 | 98.66 | A | C |
| ATOM | 413 | CB | ALA A | 93 | 28.389 | 15.125 | 63.172 | 1.00 | 47.13 | A | C |
| ATOM | 414 | C | ALA A | 93 | 30.632 | 14.968 | 62.061 | 1.00 | 98.66 | A | C |
| ATOM | 415 | O | ALA A | 93 | 31.743 | 15.431 | 62.369 | 1.00 | 98.66 | A | O |
| ATOM | 416 | N | ALA A | 94 | 30.150 | 14.990 | 60.821 | 1.00 | 55.10 | A | N |
| ATOM | 417 | CA | ALA A | 94 | 30.902 | 15.587 | 59.723 | 1.00 | 55.10 | A | C |

FIG. 6-8

```
ATOM   418  CB   ALA A  94      30.293  15.149  58.375  1.00 28.93      A    C
ATOM   419  C    ALA A  94      30.843  17.116  59.879  1.00 55.10      A    C
ATOM   420  O    ALA A  94      29.994  17.644  60.605  1.00 55.10      A    O
ATOM   421  N    ASN A  95      31.756  17.821  59.215  1.00 42.24      A    N
ATOM   422  CA   ASN A  95      31.772  19.278  59.287  1.00 42.24      A    C
ATOM   423  CB   ASN A  95      33.180  19.803  59.020  1.00 43.95      A    C
ATOM   424  CG   ASN A  95      33.269  21.310  59.144  1.00 43.95      A    C
ATOM   425  OD1  ASN A  95      33.161  22.041  58.152  1.00 43.95      A    O
ATOM   426  ND2  ASN A  95      33.456  21.786  60.368  1.00 43.95      A    N
ATOM   427  C    ASN A  95      30.779  19.823  58.257  1.00 42.24      A    C
ATOM   428  O    ASN A  95      30.989  19.730  57.040  1.00 42.24      A    O
ATOM   429  N    ARG A  96      29.685  20.385  58.757  1.00 40.20      A    N
ATOM   430  CA   ARG A  96      28.633  20.903  57.893  1.00 40.20      A    C
ATOM   431  CB   ARG A  96      27.528  21.533  58.744  1.00 34.03      A    C
ATOM   432  CG   ARG A  96      26.338  21.994  57.934  1.00 34.03      A    C
ATOM   433  CD   ARG A  96      25.357  22.797  58.777  1.00 34.03      A    C
ATOM   434  NE   ARG A  96      24.495  21.979  59.628  1.00 34.03      A    N
ATOM   435  CZ   ARG A  96      23.716  22.472  60.589  1.00 34.03      A    C
ATOM   436  NH1  ARG A  96      23.702  23.782  60.817  1.00 34.03      A    N
ATOM   437  NH2  ARG A  96      22.943  21.663  61.309  1.00 34.03      A    N
ATOM   438  C    ARG A  96      29.123  21.916  56.845  1.00 40.20      A    C
ATOM   439  O    ARG A  96      28.633  21.939  55.711  1.00 40.20      A    O
ATOM   440  N    GLU A  97      30.083  22.759  57.204  1.00 32.44      A    N
ATOM   441  CA   GLU A  97      30.559  23.725  56.231  1.00 32.44      A    C
ATOM   442  CB   GLU A  97      31.494  24.746  56.894  1.00 25.68      A    C
ATOM   443  CG   GLU A  97      32.125  25.729  55.912  1.00 25.68      A    C
ATOM   444  CD   GLU A  97      32.970  26.808  56.583  1.00 25.68      A    C
ATOM   445  OE1  GLU A  97      33.521  26.545  57.670  1.00 25.68      A    O
ATOM   446  OE2  GLU A  97      33.104  27.915  56.012  1.00 25.68      A    O
ATOM   447  C    GLU A  97      31.274  23.027  55.085  1.00 32.44      A    C
ATOM   448  O    GLU A  97      31.055  23.334  53.920  1.00 32.44      A    O
ATOM   449  N    LEU A  98      32.132  22.080  55.432  1.00 33.81      A    N
ATOM   450  CA   LEU A  98      32.893  21.325  54.449  1.00 33.81      A    C
ATOM   451  CB   LEU A  98      33.734  20.257  55.153  1.00 21.52      A    C
ATOM   452  CG   LEU A  98      34.579  19.367  54.246  1.00 21.52      A    C
ATOM   453  CD1  LEU A  98      35.460  20.225  53.359  1.00 21.52      A    C
ATOM   454  CD2  LEU A  98      35.414  18.444  55.103  1.00 21.52      A    C
ATOM   455  C    LEU A  98      31.961  20.654  53.463  1.00 33.81      A    C
ATOM   456  O    LEU A  98      32.127  20.781  52.250  1.00 33.81      A    O
ATOM   457  N    GLN A  99      30.975  19.939  53.995  1.00 43.72      A    N
ATOM   458  CA   GLN A  99      30.032  19.229  53.149  1.00 43.72      A    C
ATOM   459  CB   GLN A  99      29.110  18.347  54.000  1.00 63.84      A    C
ATOM   460  CG   GLN A  99      29.860  17.148  54.642  1.00 63.84      A    C
ATOM   461  CD   GLN A  99      30.944  16.519  53.712  1.00 63.84      A    C
ATOM   462  OE1  GLN A  99      30.659  16.109  52.574  1.00 63.84      A    O
ATOM   463  NE2  GLN A  99      32.186  16.447  54.211  1.00 63.84      A    N
ATOM   464  C    GLN A  99      29.248  20.127  52.197  1.00 43.72      A    C
ATOM   465  O    GLN A  99      28.800  19.665  51.150  1.00 43.72      A    O
ATOM   466  N    ILE A 100      29.094  21.407  52.537  1.00 26.77      A    N
ATOM   467  CA   ILE A 100      28.402  22.335  51.647  1.00 26.77      A    C
ATOM   468  CB   ILE A 100      27.806  23.528  52.415  1.00 17.29      A    C
ATOM   469  CG2  ILE A 100      27.498  24.666  51.454  1.00 17.29      A    C
ATOM   470  CG1  ILE A 100      26.541  23.073  53.152  1.00 17.29      A    C
ATOM   471  CD1  ILE A 100      25.813  24.154  53.909  1.00 17.29      A    C
ATOM   472  C    ILE A 100      29.392  22.834  50.597  1.00 26.77      A    C
ATOM   473  O    ILE A 100      29.118  22.755  49.396  1.00 26.77      A    O
ATOM   474  N    MET A 101      30.544  23.329  51.052  1.00 25.73      A    N
ATOM   475  CA   MET A 101      31.596  23.804  50.151  1.00 25.73      A    C
ATOM   476  CB   MET A 101      32.885  24.062  50.941  1.00 42.87      A    C
ATOM   477  CG   MET A 101      32.812  25.234  51.924  1.00 42.87      A    C
```

FIG. 6-9

| ATOM | 478 | SD | MET | A | 101 | 32.199 | 26.731 | 51.113 | 1.00 | 42.87 | A | S |
| --- | --- | --- | --- | --- | --- | --- | --- | --- | --- | --- | --- | --- |
| ATOM | 479 | CE | MET | A | 101 | 33.605 | 27.161 | 50.113 | 1.00 | 42.87 | A | C |
| ATOM | 480 | C | MET | A | 101 | 31.858 | 22.762 | 49.051 | 1.00 | 25.73 | A | C |
| ATOM | 481 | O | MET | A | 101 | 31.852 | 23.063 | 47.854 | 1.00 | 25.73 | A | O |
| ATOM | 482 | N | ARG | A | 102 | 32.079 | 21.526 | 49.488 | 1.00 | 39.47 | A | N |
| ATOM | 483 | CA | ARG | A | 102 | 32.334 | 20.386 | 48.613 | 1.00 | 39.47 | A | C |
| ATOM | 484 | CB | ARG | A | 102 | 32.312 | 19.107 | 49.465 | 1.00 | 46.50 | A | C |
| ATOM | 485 | CG | ARG | A | 102 | 33.668 | 18.567 | 49.903 | 1.00 | 46.50 | A | C |
| ATOM | 486 | CD | ARG | A | 102 | 34.159 | 17.565 | 48.859 | 1.00 | 46.50 | A | C |
| ATOM | 487 | NE | ARG | A | 102 | 34.683 | 16.322 | 49.426 | 1.00 | 46.50 | A | N |
| ATOM | 488 | CZ | ARG | A | 102 | 34.103 | 15.632 | 50.408 | 1.00 | 46.50 | A | C |
| ATOM | 489 | NH1 | ARG | A | 102 | 32.969 | 16.060 | 50.955 | 1.00 | 46.50 | A | N |
| ATOM | 490 | NH2 | ARG | A | 102 | 34.652 | 14.500 | 50.840 | 1.00 | 46.50 | A | N |
| ATOM | 491 | C | ARG | A | 102 | 31.338 | 20.254 | 47.451 | 1.00 | 39.47 | A | C |
| ATOM | 492 | O | ARG | A | 102 | 31.656 | 19.646 | 46.435 | 1.00 | 39.47 | A | O |
| ATOM | 493 | N | LYS | A | 103 | 30.143 | 20.813 | 47.576 | 1.00 | 23.86 | A | N |
| ATOM | 494 | CA | LYS | A | 103 | 29.200 | 20.676 | 46.481 | 1.00 | 23.86 | A | C |
| ATOM | 495 | CB | LYS | A | 103 | 27.917 | 19.997 | 46.965 | 1.00 | 68.26 | A | C |
| ATOM | 496 | CG | LYS | A | 103 | 27.098 | 20.791 | 47.962 | 1.00 | 68.26 | A | C |
| ATOM | 497 | CD | LYS | A | 103 | 25.982 | 19.924 | 48.567 | 1.00 | 68.26 | A | C |
| ATOM | 498 | CE | LYS | A | 103 | 25.188 | 20.694 | 49.632 | 1.00 | 68.26 | A | C |
| ATOM | 499 | NZ | LYS | A | 103 | 24.281 | 19.856 | 50.495 | 1.00 | 68.26 | A | N |
| ATOM | 500 | C | LYS | A | 103 | 28.853 | 21.953 | 45.750 | 1.00 | 23.86 | A | C |
| ATOM | 501 | O | LYS | A | 103 | 27.944 | 21.957 | 44.933 | 1.00 | 23.86 | A | O |
| ATOM | 502 | N | LEU | A | 104 | 29.580 | 23.030 | 46.027 | 1.00 | 25.37 | A | N |
| ATOM | 503 | CA | LEU | A | 104 | 29.317 | 24.312 | 45.378 | 1.00 | 25.37 | A | C |
| ATOM | 504 | CB | LEU | A | 104 | 29.259 | 25.433 | 46.419 | 1.00 | 33.38 | A | C |
| ATOM | 505 | CG | LEU | A | 104 | 27.917 | 25.775 | 47.082 | 1.00 | 33.38 | A | C |
| ATOM | 506 | CD1 | LEU | A | 104 | 27.308 | 24.557 | 47.747 | 1.00 | 33.38 | A | C |
| ATOM | 507 | CD2 | LEU | A | 104 | 28.133 | 26.871 | 48.093 | 1.00 | 33.38 | A | C |
| ATOM | 508 | C | LEU | A | 104 | 30.367 | 24.650 | 44.343 | 1.00 | 25.37 | A | C |
| ATOM | 509 | O | LEU | A | 104 | 31.553 | 24.437 | 44.569 | 1.00 | 25.37 | A | O |
| ATOM | 510 | N | ASP | A | 105 | 29.921 | 25.167 | 43.204 | 1.00 | 39.46 | A | N |
| ATOM | 511 | CA | ASP | A | 105 | 30.826 | 25.574 | 42.139 | 1.00 | 39.46 | A | C |
| ATOM | 512 | CB | ASP | A | 105 | 31.168 | 24.383 | 41.242 | 1.00 | 40.28 | A | C |
| ATOM | 513 | CG | ASP | A | 105 | 32.215 | 24.725 | 40.193 | 1.00 | 40.28 | A | C |
| ATOM | 514 | OD1 | ASP | A | 105 | 33.221 | 25.378 | 40.549 | 1.00 | 40.28 | A | O |
| ATOM | 515 | OD2 | ASP | A | 105 | 32.035 | 24.329 | 39.020 | 1.00 | 40.28 | A | O |
| ATOM | 516 | C | ASP | A | 105 | 30.154 | 26.676 | 41.324 | 1.00 | 39.46 | A | C |
| ATOM | 517 | O | ASP | A | 105 | 29.374 | 26.400 | 40.404 | 1.00 | 39.46 | A | O |
| ATOM | 518 | N | HIS | A | 106 | 30.455 | 27.924 | 41.687 | 1.00 | 26.69 | A | N |
| ATOM | 519 | CA | HIS | A | 106 | 29.908 | 29.100 | 41.018 | 1.00 | 26.69 | A | C |
| ATOM | 520 | CB | HIS | A | 106 | 28.713 | 29.624 | 41.809 | 1.00 | 20.40 | A | C |
| ATOM | 521 | CG | HIS | A | 106 | 27.887 | 30.632 | 41.078 | 1.00 | 20.40 | A | C |
| ATOM | 522 | CD2 | HIS | A | 106 | 26.642 | 30.548 | 40.549 | 1.00 | 20.40 | A | C |
| ATOM | 523 | ND1 | HIS | A | 106 | 28.308 | 31.924 | 40.860 | 1.00 | 20.40 | A | N |
| ATOM | 524 | CE1 | HIS | A | 106 | 27.357 | 32.593 | 40.234 | 1.00 | 20.40 | A | C |
| ATOM | 525 | NE2 | HIS | A | 106 | 26.333 | 31.781 | 40.035 | 1.00 | 20.40 | A | N |
| ATOM | 526 | C | HIS | A | 106 | 31.020 | 30.150 | 40.944 | 1.00 | 26.69 | A | C |
| ATOM | 527 | O | HIS | A | 106 | 31.847 | 30.258 | 41.846 | 1.00 | 26.69 | A | O |
| ATOM | 528 | N | CYS | A | 107 | 31.048 | 30.913 | 39.860 | 1.00 | 30.52 | A | N |
| ATOM | 529 | CA | CYS | A | 107 | 32.075 | 31.922 | 39.678 | 1.00 | 30.52 | A | C |
| ATOM | 530 | CB | CYS | A | 107 | 31.957 | 32.542 | 38.287 | 1.00 | 46.42 | A | C |
| ATOM | 531 | SG | CYS | A | 107 | 30.360 | 33.343 | 37.933 | 1.00 | 46.42 | A | S |
| ATOM | 532 | C | CYS | A | 107 | 32.001 | 33.001 | 40.736 | 1.00 | 30.52 | A | C |
| ATOM | 533 | O | CYS | A | 107 | 32.953 | 33.762 | 40.917 | 1.00 | 30.52 | A | O |
| ATOM | 534 | N | ASN | A | 108 | 30.876 | 33.052 | 41.446 | 1.00 | 31.80 | A | N |
| ATOM | 535 | CA | ASN | A | 108 | 30.663 | 34.055 | 42.483 | 1.00 | 31.80 | A | C |
| ATOM | 536 | CB | ASN | A | 108 | 29.335 | 34.771 | 42.226 | 1.00 | 33.24 | A | C |
| ATOM | 537 | CG | ASN | A | 108 | 29.405 | 35.715 | 41.041 | 1.00 | 33.24 | A | C |

FIG. 6-10

```
ATOM    538  OD1 ASN A 108      28.483  35.778  40.229  1.00 33.24      A    O
ATOM    539  ND2 ASN A 108      30.499  36.464  40.943  1.00 33.24      A    N
ATOM    540  C   ASN A 108      30.721  33.525  43.914  1.00 31.80      A    C
ATOM    541  O   ASN A 108      30.172  34.126  44.828  1.00 31.80      A    O
ATOM    542  N   ILE A 109      31.388  32.399  44.103  1.00 16.97      A    N
ATOM    543  CA  ILE A 109      31.545  31.805  45.422  1.00 16.97      A    C
ATOM    544  CB  ILE A 109      30.613  30.570  45.587  1.00 38.56      A    C
ATOM    545  CG2 ILE A 109      30.801  29.928  46.963  1.00 38.56      A    C
ATOM    546  CG1 ILE A 109      29.155  31.006  45.405  1.00 38.56      A    C
ATOM    547  CD1 ILE A 109      28.117  29.936  45.719  1.00 38.56      A    C
ATOM    548  C   ILE A 109      33.018  31.387  45.431  1.00 16.97      A    C
ATOM    549  O   ILE A 109      33.549  30.961  44.395  1.00 16.97      A    O
ATOM    550  N   VAL A 110      33.691  31.527  46.572  1.00 21.69      A    N
ATOM    551  CA  VAL A 110      35.102  31.160  46.633  1.00 21.69      A    C
ATOM    552  CB  VAL A 110      35.777  31.522  47.982  1.00 27.20      A    C
ATOM    553  CG1 VAL A 110      37.199  32.013  47.727  1.00 27.20      A    C
ATOM    554  CG2 VAL A 110      34.969  32.534  48.725  1.00 27.20      A    C
ATOM    555  C   VAL A 110      35.242  29.661  46.455  1.00 21.69      A    C
ATOM    556  O   VAL A 110      34.499  28.889  47.054  1.00 21.69      A    O
ATOM    557  N   ARG A 111      36.206  29.252  45.644  1.00 21.09      A    N
ATOM    558  CA  ARG A 111      36.412  27.839  45.407  1.00 21.09      A    C
ATOM    559  CB  ARG A 111      37.060  27.592  44.039  1.00 52.23      A    C
ATOM    560  CG  ARG A 111      37.444  26.125  43.817  1.00 52.23      A    C
ATOM    561  CD  ARG A 111      37.957  25.834  42.403  1.00 52.23      A    C
ATOM    562  NE  ARG A 111      39.020  26.756  41.989  1.00 52.23      A    N
ATOM    563  CZ  ARG A 111      40.227  26.383  41.555  1.00 52.23      A    C
ATOM    564  NH1 ARG A 111      40.544  25.088  41.473  1.00 52.23      A    N
ATOM    565  NH2 ARG A 111     -41.119  27.311  41.202  1.00 52.23      A    N
ATOM    566  C   ARG A 111      37.269  27.191  46.467  1.00 21.09      A    C
ATOM    567  O   ARG A 111      38.293  27.728  46.892  1.00 21.09      A    O
ATOM    568  N   LEU A 112      36.831  26.014  46.880  1.00 29.79      A    N
ATOM    569  CA  LEU A 112      37.547  25.223  47.864  1.00 29.79      A    C
ATOM    570  CB  LEU A 112      36.555  24.348  48.641  1.00 21.10      A    C
ATOM    571  CG  LEU A 112      37.162  23.388  49.656  1.00 21.10      A    C
ATOM    572  CD1 LEU A 112      37.859  24.193  50.747  1.00 21.10      A    C
ATOM    573  CD2 LEU A 112      36.079  22.494  50.233  1.00 21.10      A    C
ATOM    574  C   LEU A 112      38.520  24.359  47.059  1.00 29.79      A    C
ATOM    575  O   LEU A 112      38.096  23.475  46.336  1.00 29.79      A    O
ATOM    576  N   ARG A 113      39.816  24.612  47.159  1.00 21.31      A    N
ATOM    577  CA  ARG A 113      40.747  23.816  46.380  1.00 21.31      A    C
ATOM    578  CB  ARG A 113      42.104  24.509  46.261  1.00 42.03      A    C
ATOM    579  CG  ARG A 113      42.106  26.005  46.555  1.00 42.03      A    C
ATOM    580  CD  ARG A 113      42.669  26.861  45.411  1.00 42.03      A    C
ATOM    581  NE  ARG A 113      43.873  26.293  44.811  1.00 42.03      A    N
ATOM    582  CZ  ARG A 113      44.660  26.940  43.958  1.00 42.03      A    C
ATOM    583  NH1 ARG A 113      44.368  28.192  43.619  1.00 42.03      A    N
ATOM    584  NH2 ARG A 113      45.709  26.319  43.419  1.00 42.03      A    N
ATOM    585  C   ARG A 113      40.936  22.454  47.032  1.00 21.31      A    C
ATOM    586  O   ARG A 113      40.527  21.423  46.508  1.00 21.31      A    O
ATOM    587  N   TYR A 114      41.564  22.468  48.197  1.00 36.43      A    N
ATOM    588  CA  TYR A 114      41.824  21.258  48.942  1.00 36.43      A    C
ATOM    589  CB  TYR A 114      43.329  20.974  48.972  1.00 43.26      A    C
ATOM    590  CG  TYR A 114      44.118  21.443  47.757  1.00 43.26      A    C
ATOM    591  CD1 TYR A 114      44.086  20.743  46.544  1.00 43.26      A    C
ATOM    592  CE1 TYR A 114      44.856  21.157  45.442  1.00 43.26      A    C
ATOM    593  CD2 TYR A 114      44.933  22.571  47.836  1.00 43.26      A    C
ATOM    594  CE2 TYR A 114      45.704  22.997  46.745  1.00 43.26      A    C
ATOM    595  CZ  TYR A 114      45.662  22.289  45.553  1.00 43.26      A    C
ATOM    596  OH  TYR A 114      46.409  22.740  44.479  1.00 43.26      A    O
ATOM    597  C   TYR A 114      41.345  21.424  50.370  1.00 36.43      A    C
```

FIG. 6-11

| ATOM | 598 | O   | TYR | A | 114 | 40.906 | 22.494 | 50.766 | 1.00 | 36.43 | A | O |
|------|-----|-----|-----|---|-----|--------|--------|--------|------|-------|---|---|
| ATOM | 599 | N   | PHE | A | 115 | 41.436 | 20.346 | 51.135 | 1.00 | 37.36 | A | N |
| ATOM | 600 | CA  | PHE | A | 115 | 41.071 | 20.360 | 52.546 | 1.00 | 37.36 | A | C |
| ATOM | 601 | CB  | PHE | A | 115 | 39.547 | 20.330 | 52.727 | 1.00 | 31.41 | A | C |
| ATOM | 602 | CG  | PHE | A | 115 | 38.928 | 18.984 | 52.537 | 1.00 | 31.41 | A | C |
| ATOM | 603 | CD1 | PHE | A | 115 | 38.855 | 18.086 | 53.589 | 1.00 | 31.41 | A | C |
| ATOM | 604 | CD2 | PHE | A | 115 | 38.420 | 18.614 | 51.304 | 1.00 | 31.41 | A | C |
| ATOM | 605 | CE1 | PHE | A | 115 | 38.272 | 16.838 | 53.418 | 1.00 | 31.41 | A | C |
| ATOM | 606 | CE2 | PHE | A | 115 | 37.834 | 17.370 | 51.117 | 1.00 | 31.41 | A | C |
| ATOM | 607 | CZ  | PHE | A | 115 | 37.763 | 16.479 | 52.175 | 1.00 | 31.41 | A | C |
| ATOM | 608 | C   | PHE | A | 115 | 41.731 | 19.130 | 53.161 | 1.00 | 37.36 | A | C |
| ATOM | 609 | O   | PHE | A | 115 | 41.610 | 18.021 | 52.640 | 1.00 | 37.36 | A | O |
| ATOM | 610 | N   | PHE | A | 116 | 42.458 | 19.345 | 54.252 | 1.00 | 34.91 | A | N |
| ATOM | 611 | CA  | PHE | A | 116 | 43.171 | 18.272 | 54.925 | 1.00 | 34.91 | A | C |
| ATOM | 612 | CB  | PHE | A | 116 | 44.667 | 18.386 | 54.615 | 1.00 | 35.65 | A | C |
| ATOM | 613 | CG  | PHE | A | 116 | 45.257 | 19.708 | 54.983 | 1.00 | 35.65 | A | C |
| ATOM | 614 | CD1 | PHE | A | 116 | 45.927 | 19.871 | 56.189 | 1.00 | 35.65 | A | C |
| ATOM | 615 | CD2 | PHE | A | 116 | 45.115 | 20.802 | 54.143 | 1.00 | 35.65 | A | C |
| ATOM | 616 | CE1 | PHE | A | 116 | 46.445 | 21.108 | 56.559 | 1.00 | 35.65 | A | C |
| ATOM | 617 | CE2 | PHE | A | 116 | 45.630 | 22.052 | 54.504 | 1.00 | 35.65 | A | C |
| ATOM | 618 | CZ  | PHE | A | 116 | 46.298 | 22.203 | 55.715 | 1.00 | 35.65 | A | C |
| ATOM | 619 | C   | PHE | A | 116 | 42.912 | 18.295 | 56.428 | 1.00 | 34.91 | A | C |
| ATOM | 620 | O   | PHE | A | 116 | 42.072 | 19.059 | 56.901 | 1.00 | 34.91 | A | O |
| ATOM | 621 | N   | TYR | A | 117 | 43.644 | 17.484 | 57.186 | 1.00 | 53.15 | A | N |
| ATOM | 622 | CA  | TYR | A | 117 | 43.399 | 17.431 | 58.624 | 1.00 | 53.15 | A | C |
| ATOM | 623 | CB  | TYR | A | 117 | 42.578 | 16.176 | 58.938 | 1.00 | 28.74 | A | C |
| ATOM | 624 | CG  | TYR | A | 117 | 41.117 | 16.232 | 58.572 | 1.00 | 28.74 | A | C |
| ATOM | 625 | CD1 | TYR | A | 117 | 40.200 | 16.914 | 59.378 | 1.00 | 28.74 | A | C |
| ATOM | 626 | CE1 | TYR | A | 117 | 38.818 | 16.894 | 59.096 | 1.00 | 28.74 | A | C |
| ATOM | 627 | CD2 | TYR | A | 117 | 40.631 | 15.536 | 57.462 | 1.00 | 28.74 | A | C |
| ATOM | 628 | CE2 | TYR | A | 117 | 39.252 | 15.507 | 57.165 | 1.00 | 28.74 | A | C |
| ATOM | 629 | CZ  | TYR | A | 117 | 38.351 | 16.184 | 57.991 | 1.00 | 28.74 | A | C |
| ATOM | 630 | OH  | TYR | A | 117 | 36.993 | 16.112 | 57.735 | 1.00 | 28.74 | A | O |
| ATOM | 631 | C   | TYR | A | 117 | 44.506 | 17.521 | 59.688 | 1.00 | 53.15 | A | C |
| ATOM | 632 | O   | TYR | A | 117 | 44.991 | 16.494 | 60.165 | 1.00 | 53.15 | A | O |
| ATOM | 633 | N   | SER | A | 118 | 44.911 | 18.734 | 60.057 | 1.00 | 41.96 | A | N |
| ATOM | 634 | CA  | SER | A | 118 | 45.858 | 18.902 | 61.164 | 1.00 | 41.96 | A | C |
| ATOM | 635 | CB  | SER | A | 118 | 46.606 | 20.245 | 61.054 | 1.00 | 60.34 | A | C |
| ATOM | 636 | OG  | SER | A | 118 | 46.934 | 20.788 | 62.339 | 1.00 | 60.34 | A | O |
| ATOM | 637 | C   | SER | A | 118 | 44.736 | 19.007 | 62.243 | 1.00 | 41.96 | A | C |
| ATOM | 638 | O   | SER | A | 118 | 44.798 | 18.354 | 63.295 | 1.00 | 41.96 | A | O |
| ATOM | 639 | N   | TYR | A | 127 | 43.730 | 19.853 | 61.897 | 1.00 | 90.04 | A | N |
| ATOM | 640 | CA  | TYR | A | 127 | 42.417 | 20.205 | 62.567 | 1.00 | 90.04 | A | C |
| ATOM | 641 | CB  | TYR | A | 127 | 42.329 | 21.690 | 62.942 | 1.00 | 72.26 | A | C |
| ATOM | 642 | CG  | TYR | A | 127 | 42.884 | 22.103 | 64.288 | 1.00 | 72.26 | A | C |
| ATOM | 643 | CD1 | TYR | A | 127 | 42.025 | 22.436 | 65.337 | 1.00 | 72.26 | A | C |
| ATOM | 644 | CE1 | TYR | A | 127 | 42.521 | 22.889 | 66.558 | 1.00 | 72.26 | A | C |
| ATOM | 645 | CD2 | TYR | A | 127 | 44.266 | 22.228 | 64.499 | 1.00 | 72.26 | A | C |
| ATOM | 646 | CE2 | TYR | A | 127 | 44.774 | 22.684 | 65.729 | 1.00 | 72.26 | A | C |
| ATOM | 647 | CZ  | TYR | A | 127 | 43.887 | 23.011 | 66.750 | 1.00 | 72.26 | A | C |
| ATOM | 648 | OH  | TYR | A | 127 | 44.348 | 23.467 | 67.969 | 1.00 | 72.26 | A | O |
| ATOM | 649 | C   | TYR | A | 127 | 41.712 | 20.069 | 61.211 | 1.00 | 90.04 | A | C |
| ATOM | 650 | O   | TYR | A | 127 | 42.157 | 19.274 | 60.381 | 1.00 | 90.04 | A | O |
| ATOM | 651 | N   | LEU | A | 128 | 40.660 | 20.835 | 60.941 | 1.00 | 31.65 | A | N |
| ATOM | 652 | CA  | LEU | A | 128 | 40.057 | 20.769 | 59.604 | 1.00 | 31.65 | A | C |
| ATOM | 653 | CB  | LEU | A | 128 | 38.530 | 20.804 | 59.660 | 1.00 | 33.85 | A | C |
| ATOM | 654 | CG  | LEU | A | 128 | 37.915 | 21.066 | 58.272 | 1.00 | 33.85 | A | C |
| ATOM | 655 | CD1 | LEU | A | 128 | 38.331 | 19.977 | 57.291 | 1.00 | 33.85 | A | C |
| ATOM | 656 | CD2 | LEU | A | 128 | 36.418 | 21.122 | 58.371 | 1.00 | 33.85 | A | C |
| ATOM | 657 | C   | LEU | A | 128 | 40.542 | 22.011 | 58.863 | 1.00 | 31.65 | A | C |

FIG. 6-12

| ATOM | 658 | O   | LEU | A | 128 | 40.159 | 23.123 | 59.202 | 1.00 | 31.65 | A | O |
|------|-----|-----|-----|---|-----|--------|--------|--------|------|-------|---|---|
| ATOM | 659 | N   | ASN | A | 129 | 41.380 | 21.841 | 57.850 | 1.00 | 44.05 | A | N |
| ATOM | 660 | CA  | ASN | A | 129 | 41.901 | 23.004 | 57.124 | 1.00 | 44.05 | A | C |
| ATOM | 661 | CB  | ASN | A | 129 | 43.416 | 22.882 | 56.989 | 1.00 | 34.27 | A | C |
| ATOM | 662 | CG  | ASN | A | 129 | 44.098 | 22.637 | 58.329 | 1.00 | 34.27 | A | C |
| ATOM | 663 | OD1 | ASN | A | 129 | 43.718 | 21.735 | 59.080 | 1.00 | 34.27 | A | O |
| ATOM | 664 | ND2 | ASN | A | 129 | 45.112 | 23.435 | 58.631 | 1.00 | 34.27 | A | N |
| ATOM | 665 | C   | ASN | A | 129 | 41.268 | 23.164 | 55.749 | 1.00 | 44.05 | A | C |
| ATOM | 666 | O   | ASN | A | 129 | 41.319 | 22.252 | 54.931 | 1.00 | 44.05 | A | O |
| ATOM | 667 | N   | LEU | A | 130 | 40.664 | 24.317 | 55.490 | 1.00 | 31.79 | A | N |
| ATOM | 668 | CA  | LEU | A | 130 | 40.034 | 24.551 | 54.198 | 1.00 | 31.79 | A | C |
| ATOM | 669 | CB  | LEU | A | 130 | 38.636 | 25.152 | 54.376 | 1.00 | 30.77 | A | C |
| ATOM | 670 | CG  | LEU | A | 130 | 37.513 | 24.314 | 55.000 | 1.00 | 30.77 | A | C |
| ATOM | 671 | CD1 | LEU | A | 130 | 36.439 | 24.075 | 53.966 | 1.00 | 30.77 | A | C |
| ATOM | 672 | CD2 | LEU | A | 130 | 38.042 | 22.986 | 55.512 | 1.00 | 30.77 | A | C |
| ATOM | 673 | C   | LEU | A | 130 | 40.873 | 25.485 | 53.339 | 1.00 | 31.79 | A | C |
| ATOM | 674 | O   | LEU | A | 130 | 40.950 | 26.681 | 53.609 | 1.00 | 31.79 | A | O |
| ATOM | 675 | N   | VAL | A | 131 | 41.500 | 24.937 | 52.302 | 1.00 | 34.74 | A | N |
| ATOM | 676 | CA  | VAL | A | 131 | 42.322 | 25.732 | 51.392 | 1.00 | 34.74 | A | C |
| ATOM | 677 | CB  | VAL | A | 131 | 43.483 | 24.894 | 50.776 | 1.00 | 25.96 | A | C |
| ATOM | 678 | CG1 | VAL | A | 131 | 44.545 | 25.816 | 50.192 | 1.00 | 25.96 | A | C |
| ATOM | 679 | CG2 | VAL | A | 131 | 44.097 | 23.984 | 51.827 | 1.00 | 25.96 | A | C |
| ATOM | 680 | C   | VAL | A | 131 | 41.424 | 26.226 | 50.258 | 1.00 | 34.74 | A | C |
| ATOM | 681 | O   | VAL | A | 131 | 40.990 | 25.434 | 49.421 | 1.00 | 34.74 | A | O |
| ATOM | 682 | N   | LEU | A | 132 | 41.134 | 27.529 | 50.246 | 1.00 | 30.04 | A | N |
| ATOM | 683 | CA  | LEU | A | 132 | 40.282 | 28.123 | 49.212 | 1.00 | 30.04 | A | C |
| ATOM | 684 | CB  | LEU | A | 132 | 39.040 | 28.764 | 49.838 | 1.00 | 13.89 | A | C |
| ATOM | 685 | CG  | LEU | A | 132 | 38.323 | 28.015 | 50.967 | 1.00 | 13.89 | A | C |
| ATOM | 686 | CD1 | LEU | A | 132 | 38.956 | 28.385 | 52.306 | 1.00 | 13.89 | A | C |
| ATOM | 687 | CD2 | LEU | A | 132 | 36.847 | 28.373 | 50.980 | 1.00 | 13.89 | A | C |
| ATOM | 688 | C   | LEU | A | 132 | 41.070 | 29.194 | 48.476 | 1.00 | 30.04 | A | C |
| ATOM | 689 | O   | LEU | A | 132 | 42.142 | 29.595 | 48.932 | 1.00 | 30.04 | A | O |
| ATOM | 690 | N   | ASP | A | 133 | 40.556 | 29.654 | 47.338 | 1.00 | 29.79 | A | N |
| ATOM | 691 | CA  | ASP | A | 133 | 41.253 | 30.704 | 46.602 | 1.00 | 29.79 | A | C |
| ATOM | 692 | CB  | ASP | A | 133 | 40.480 | 31.144 | 45.362 | 1.00 | 40.28 | A | C |
| ATOM | 693 | CG  | ASP | A | 133 | 40.365 | 30.059 | 44.325 | 1.00 | 40.28 | A | C |
| ATOM | 694 | OD1 | ASP | A | 133 | 41.320 | 29.258 | 44.180 | 1.00 | 40.28 | A | O |
| ATOM | 695 | OD2 | ASP | A | 133 | 39.320 | 30.026 | 43.640 | 1.00 | 40.28 | A | O |
| ATOM | 696 | C   | ASP | A | 133 | 41.383 | 31.912 | 47.508 | 1.00 | 29.79 | A | C |
| ATOM | 697 | O   | ASP | A | 133 | 40.493 | 32.191 | 48.304 | 1.00 | 29.79 | A | O |
| ATOM | 698 | N   | TYR | A | 134 | 42.489 | 32.630 | 47.397 | 1.00 | 31.83 | A | N |
| ATOM | 699 | CA  | TYR | A | 134 | 42.655 | 33.816 | 48.214 | 1.00 | 31.83 | A | C |
| ATOM | 700 | CB  | TYR | A | 134 | 44.103 | 33.964 | 48.670 | 1.00 | 33.17 | A | C |
| ATOM | 701 | CG  | TYR | A | 134 | 44.403 | 35.350 | 49.185 | 1.00 | 33.17 | A | C |
| ATOM | 702 | CD1 | TYR | A | 134 | 43.999 | 35.750 | 50.460 | 1.00 | 33.17 | A | C |
| ATOM | 703 | CE1 | TYR | A | 134 | 44.175 | 37.066 | 50.888 | 1.00 | 33.17 | A | C |
| ATOM | 704 | CD2 | TYR | A | 134 | 45.001 | 36.299 | 48.356 | 1.00 | 33.17 | A | C |
| ATOM | 705 | CE2 | TYR | A | 134 | 45.178 | 37.613 | 48.773 | 1.00 | 33.17 | A | C |
| ATOM | 706 | CZ  | TYR | A | 134 | 44.759 | 37.989 | 50.034 | 1.00 | 33.17 | A | C |
| ATOM | 707 | OH  | TYR | A | 134 | 44.881 | 39.294 | 50.426 | 1.00 | 33.17 | A | O |
| ATOM | 708 | C   | TYR | A | 134 | 42.237 | 35.068 | 47.431 | 1.00 | 31.83 | A | C |
| ATOM | 709 | O   | TYR | A | 134 | 42.701 | 35.310 | 46.317 | 1.00 | 31.83 | A | O |
| ATOM | 710 | N   | VAL | A | 135 | 41.337 | 35.848 | 48.013 | 1.00 | 29.74 | A | N |
| ATOM | 711 | CA  | VAL | A | 135 | 40.890 | 37.076 | 47.390 | 1.00 | 29.74 | A | C |
| ATOM | 712 | CB  | VAL | A | 135 | 39.369 | 37.127 | 47.259 | 1.00 | 19.46 | A | C |
| ATOM | 713 | CG1 | VAL | A | 135 | 38.963 | 38.374 | 46.500 | 1.00 | 19.46 | A | C |
| ATOM | 714 | CG2 | VAL | A | 135 | 38.875 | 35.889 | 46.539 | 1.00 | 19.46 | A | C |
| ATOM | 715 | C   | VAL | A | 135 | 41.395 | 38.163 | 48.331 | 1.00 | 29.74 | A | C |
| ATOM | 716 | O   | VAL | A | 135 | 41.230 | 38.075 | 49.545 | 1.00 | 29.74 | A | O |
| ATOM | 717 | N   | PRO | A | 136 | 42.021 | 39.204 | 47.769 | 1.00 | 32.72 | A | N |

FIG. 6-13

| ATOM | 718 | CD | PRO A 136 | 42.131 | 39.376 | 46.306 | 1.00 | 13.44 | A | C |
|---|---|---|---|---|---|---|---|---|---|---|
| ATOM | 719 | CA | PRO A 136 | 42.609 | 40.353 | 48.454 | 1.00 | 32.72 | A | C |
| ATOM | 720 | CB | PRO A 136 | 43.503 | 40.935 | 47.372 | 1.00 | 13.44 | A | C |
| ATOM | 721 | CG | PRO A 136 | 42.625 | 40.790 | 46.171 | 1.00 | 13.44 | A | C |
| ATOM | 722 | C | PRO A 136 | 41.726 | 41.434 | 49.079 | 1.00 | 32.72 | A | C |
| ATOM | 723 | O | PRO A 136 | 42.236 | 42.294 | 49.791 | 1.00 | 32.72 | A | O |
| ATOM | 724 | N | GLU A 137 | 40.426 | 41.424 | 48.844 | 1.00 | 18.95 | A | N |
| ATOM | 725 | CA | GLU A 137 | 39.648 | 42.507 | 49.404 | 1.00 | 18.95 | A | C |
| ATOM | 726 | CB | GLU A 137 | 39.672 | 43.671 | 48.406 | 1.00 | 34.97 | A | C |
| ATOM | 727 | CG | GLU A 137 | 39.314 | 45.020 | 48.986 | 1.00 | 34.97 | A | C |
| ATOM | 728 | CD | GLU A 137 | 40.360 | 45.528 | 49.949 | 1.00 | 34.97 | A | C |
| ATOM | 729 | OE1 | GLU A 137 | 41.460 | 45.916 | 49.504 | 1.00 | 34.97 | A | O |
| ATOM | 730 | OE2 | GLU A 137 | 40.077 | 45.527 | 51.163 | 1.00 | 34.97 | A | O |
| ATOM | 731 | C | GLU A 137 | 38.221 | 42.136 | 49.755 | 1.00 | 18.95 | A | C |
| ATOM | 732 | O | GLU A 137 | 37.668 | 41.187 | 49.225 | 1.00 | 18.95 | A | O |
| ATOM | 733 | N | THR A 138 | 37.626 | 42.896 | 50.680 | 1.00 | 16.14 | A | N |
| ATOM | 734 | CA | THR A 138 | 36.257 | 42.644 | 51.119 | 1.00 | 16.14 | A | C |
| ATOM | 735 | CB | THR A 138 | 36.224 | 42.199 | 52.586 | 1.00 | 2.67 | A | C |
| ATOM | 736 | OG1 | THR A 138 | 36.412 | 43.340 | 53.423 | 1.00 | 2.67 | A | O |
| ATOM | 737 | CG2 | THR A 138 | 37.309 | 41.176 | 52.866 | 1.00 | 2.67 | A | C |
| ATOM | 738 | C | THR A 138 | 35.377 | 43.891 | 50.988 | 1.00 | 16.14 | A | C |
| ATOM | 739 | O | THR A 138 | 35.837 | 45.003 | 51.199 | 1.00 | 16.14 | A | O |
| ATOM | 740 | N | VAL A 139 | 34.107 | 43.710 | 50.650 | 1.00 | 16.21 | A | N |
| ATOM | 741 | CA | VAL A 139 | 33.220 | 44.854 | 50.523 | 1.00 | 16.21 | A | C |
| ATOM | 742 | CB | VAL A 139 | 31.747 | 44.419 | 50.316 | 1.00 | 12.77 | A | C |
| ATOM | 743 | CG1 | VAL A 139 | 30.812 | 45.598 | 50.555 | 1.00 | 12.77 | A | C |
| ATOM | 744 | CG2 | VAL A 139 | 31.552 | 43.905 | 48.897 | 1.00 | 12.77 | A | C |
| ATOM | 745 | C | VAL A 139 | 33.312 | 45.744 | 51.757 | 1.00 | 16.21 | A | C |
| ATOM | 746 | O | VAL A 139 | 33.259 | 46.962 | 51.647 | 1.00 | 16.21 | A | O |
| ATOM | 747 | N | TYR A 140 | 33.444 | 45.130 | 52.928 | 1.00 | 25.49 | A | N |
| ATOM | 748 | CA | TYR A 140 | 33.549 | 45.865 | 54.179 | 1.00 | 25.49 | A | C |
| ATOM | 749 | CB | TYR A 140 | 33.780 | 44.891 | 55.330 | 1.00 | 32.02 | A | C |
| ATOM | 750 | CG | TYR A 140 | 33.996 | 45.568 | 56.663 | 1.00 | 32.02 | A | C |
| ATOM | 751 | CD1 | TYR A 140 | 32.935 | 45.800 | 57.534 | 1.00 | 32.02 | A | C |
| ATOM | 752 | CE1 | TYR A 140 | 33.125 | 46.488 | 58.737 | 1.00 | 32.02 | A | C |
| ATOM | 753 | CD2 | TYR A 140 | 35.250 | 46.032 | 57.025 | 1.00 | 32.02 | A | C |
| ATOM | 754 | CE2 | TYR A 140 | 35.451 | 46.715 | 58.212 | 1.00 | 32.02 | A | C |
| ATOM | 755 | CZ | TYR A 140 | 34.390 | 46.944 | 59.060 | 1.00 | 32.02 | A | C |
| ATOM | 756 | OH | TYR A 140 | 34.612 | 47.658 | 60.211 | 1.00 | 32.02 | A | O |
| ATOM | 757 | C | TYR A 140 | 34.713 | 46.857 | 54.122 | 1.00 | 25.49 | A | C |
| ATOM | 758 | O | TYR A 140 | 34.533 | 48.070 | 54.336 | 1.00 | 25.49 | A | O |
| ATOM | 759 | N | ARG A 141 | 35.908 | 46.326 | 53.849 | 1.00 | 29.45 | A | N |
| ATOM | 760 | CA | ARG A 141 | 37.126 | 47.127 | 53.754 | 1.00 | 29.45 | A | C |
| ATOM | 761 | CB | ARG A 141 | 38.307 | 46.265 | 53.337 | 1.00 | 38.14 | A | C |
| ATOM | 762 | CG | ARG A 141 | 38.820 | 45.305 | 54.362 | 1.00 | 38.14 | A | C |
| ATOM | 763 | CD | ARG A 141 | 40.033 | 44.516 | 53.779 | 1.00 | 38.14 | A | C |
| ATOM | 764 | NE | ARG A 141 | 41.291 | 45.142 | 54.304 | 1.00 | 38.14 | A | N |
| ATOM | 765 | CZ | ARG A 141 | 42.396 | 45.326 | 53.580 | 1.00 | 38.14 | A | C |
| ATOM | 766 | NH1 | ARG A 141 | 42.415 | 45.042 | 52.276 | 1.00 | 38.14 | A | N |
| ATOM | 767 | NH2 | ARG A 141 | 43.502 | 45.772 | 54.169 | 1.00 | 38.14 | A | N |
| ATOM | 768 | C | ARG A 141 | 36.994 | 48.244 | 52.729 | 1.00 | 29.45 | A | C |
| ATOM | 769 | O | ARG A 141 | 37.533 | 49.331 | 52.903 | 1.00 | 29.45 | A | O |
| ATOM | 770 | N | VAL A 142 | 36.289 | 47.954 | 51.647 | 1.00 | 23.63 | A | N |
| ATOM | 771 | CA | VAL A 142 | 36.106 | 48.922 | 50.586 | 1.00 | 23.63 | A | C |
| ATOM | 772 | CB | VAL A 142 | 35.598 | 48.234 | 49.305 | 1.00 | 19.03 | A | C |
| ATOM | 773 | CG1 | VAL A 142 | 35.551 | 49.223 | 48.168 | 1.00 | 19.03 | A | C |
| ATOM | 774 | CG2 | VAL A 142 | 36.496 | 47.063 | 48.959 | 1.00 | 19.03 | A | C |
| ATOM | 775 | C | VAL A 142 | 35.137 | 50.006 | 51.006 | 1.00 | 23.63 | A | C |
| ATOM | 776 | O | VAL A 142 | 35.475 | 51.183 | 50.999 | 1.00 | 23.63 | A | O |
| ATOM | 777 | N | ALA A 143 | 33.931 | 49.605 | 51.377 | 1.00 | 30.71 | A | N |

FIG. 6-14

```
ATOM    778  CA   ALA A 143      32.912  50.550  51.796  1.00 30.71       A    C
ATOM    779  CB   ALA A 143      31.719  49.803  52.355  1.00  6.50       A    C
ATOM    780  C    ALA A 143      33.462  51.503  52.851  1.00 30.71       A    C
ATOM    781  O    ALA A 143      33.176  52.701  52.843  1.00 30.71       A    O
ATOM    782  N    ARG A 144      34.267  50.964  53.753  1.00 33.48       A    N
ATOM    783  CA   ARG A 144      34.824  51.753  54.840  1.00 33.48       A    C
ATOM    784  CB   ARG A 144      35.444  50.801  55.862  1.00 65.81       A    C
ATOM    785  CG   ARG A 144      35.918  51.452  57.130  1.00 65.81       A    C
ATOM    786  CD   ARG A 144      36.438  50.383  58.072  1.00 65.81       A    C
ATOM    787  NE   ARG A 144      37.265  50.920  59.155  1.00 65.81       A    N
ATOM    788  CZ   ARG A 144      36.793  51.607  60.193  1.00 65.81       A    C
ATOM    789  NH1  ARG A 144      35.487  51.845  60.291  1.00 65.81       A    N
ATOM    790  NH2  ARG A 144      37.624  52.054  61.135  1.00 65.81       A    N
ATOM    791  C    ARG A 144      35.840  52.810  54.402  1.00 33.48       A    C
ATOM    792  O    ARG A 144      35.918  53.891  54.990  1.00 33.48       A    O
ATOM    793  N    HIS A 145      36.620  52.490  53.376  1.00 40.62       A    N
ATOM    794  CA   HIS A 145      37.630  53.402  52.856  1.00 40.62       A    C
ATOM    795  CB   HIS A 145      38.503  52.675  51.825  1.00 68.45       A    C
ATOM    796  CG   HIS A 145      39.277  53.590  50.918  1.00 68.45       A    C
ATOM    797  CD2  HIS A 145      38.881  54.346  49.862  1.00 68.45       A    C
ATOM    798  ND1  HIS A 145      40.638  53.805  51.045  1.00 68.45       A    N
ATOM    799  CE1  HIS A 145      41.042  54.648  50.112  1.00 68.45       A    C
ATOM    800  NE2  HIS A 145      39.994  54.993  49.379  1.00 68.45       A    N
ATOM    801  C    HIS A 145      36.950  54.606  52.220  1.00 40.62       A    C
ATOM    802  O    HIS A 145      37.448  55.731  52.306  1.00 40.62       A    O
ATOM    803  N    TYR A 146      35.814  54.357  51.572  1.00 34.93       A    N
ATOM    804  CA   TYR A 146      35.056  55.415  50.923  1.00 34.93       A    C
ATOM    805  CB   TYR A 146      34.095  54.835  49.889  1.00 27.21       A    C
ATOM    806  CG   TYR A 146      34.703  54.588  48.526  1.00 27.21       A    C
ATOM    807  CD1  TYR A 146      35.127  53.317  48.147  1.00 27.21       A    C
ATOM    808  CE1  TYR A 146      35.657  53.080  46.893  1.00 27.21       A    C
ATOM    809  CD2  TYR A 146      34.835  55.622  47.606  1.00 27.21       A    C
ATOM    810  CE2  TYR A 146      35.371  55.389  46.339  1.00 27.21       A    C
ATOM    811  CZ   TYR A 146      35.780  54.110  46.001  1.00 27.21       A    C
ATOM    812  OH   TYR A 146      36.353  53.845  44.788  1.00 27.21       A    O
ATOM    813  C    TYR A 146      34.256  56.203  51.944  1.00 34.93       A    C
ATOM    814  O    TYR A 146      33.966  57.380  51.748  1.00 34.93       A    O
ATOM    815  N    SER A 147      33.903  55.555  53.045  1.00 36.80       A    N
ATOM    816  CA   SER A 147      33.106  56.201  54.073  1.00 36.80       A    C
ATOM    817  CB   SER A 147      32.450  55.145  54.955  1.00 36.25       A    C
ATOM    818  OG   SER A 147      31.575  55.743  55.895  1.00 36.25       A    O
ATOM    819  C    SER A 147      33.899  57.164  54.939  1.00 36.80       A    C
ATOM    820  O    SER A 147      33.361  58.163  55.423  1.00 36.80       A    O
ATOM    821  N    ARG A 148      35.175  56.862  55.149  1.00 47.53       A    N
ATOM    822  CA   ARG A 148      36.006  57.724  55.969  1.00 47.53       A    C
ATOM    823  CB   ARG A 148      37.235  56.967  56.490  1.00 71.97       A    C
ATOM    824  CG   ARG A 148      36.913  55.768  57.363  1.00 71.97       A    C
ATOM    825  CD   ARG A 148      36.722  56.126  58.835  1.00 71.97       A    C
ATOM    826  NE   ARG A 148      37.523  55.225  59.677  1.00 71.97       A    N
ATOM    827  CZ   ARG A 148      38.807  55.428  59.999  1.00 71.97       A    C
ATOM    828  NH1  ARG A 148      39.458  56.518  59.568  1.00 71.97       A    N
ATOM    829  NH2  ARG A 148      39.455  54.522  60.730  1.00 71.97       A    N
ATOM    830  C    ARG A 148      36.443  58.904  55.125  1.00 47.53       A    C
ATOM    831  O    ARG A 148      36.850  59.929  55.664  1.00 47.53       A    O
ATOM    832  N    ALA A 149      36.361  58.762  53.807  1.00 45.63       A    N
ATOM    833  CA   ALA A 149      36.756  59.851  52.920  1.00 45.63       A    C
ATOM    834  CB   ALA A 149      37.397  59.302  51.652  1.00 43.12       A    C
ATOM    835  C    ALA A 149      35.545  60.701  52.561  1.00 45.63       A    C
ATOM    836  O    ALA A 149      35.607  61.539  51.652  1.00 45.63       A    O
ATOM    837  N    LYS A 150      34.446  60.482  53.277  1.00 57.23       A    N
```

FIG. 6-15

```
ATOM    838  CA   LYS A 150      33.218  61.230  53.040  1.00 57.23      A  C
ATOM    839  CB   LYS A 150      33.427  62.725  53.350  1.00 79.42      A  C
ATOM    840  CG   LYS A 150      33.362  63.076  54.846  1.00 79.42      A  C
ATOM    841  CD   LYS A 150      33.392  64.594  55.114  1.00 79.42      A  C
ATOM    842  CE   LYS A 150      32.160  65.347  54.556  1.00 79.42      A  C
ATOM    843  NZ   LYS A 150      32.105  65.438  53.056  1.00 79.42      A  N
ATOM    844  C    LYS A 150      32.676  61.066  51.620  1.00 57.23      A  C
ATOM    845  O    LYS A 150      31.889  61.901  51.150  1.00 57.23      A  O
ATOM    846  N    GLN A 151      33.098  60.004  50.933  1.00 44.00      A  N
ATOM    847  CA   GLN A 151      32.610  59.747  49.577  1.00 44.00      A  C
ATOM    848  CB   GLN A 151      33.754  59.508  48.604  1.00 59.06      A  C
ATOM    849  CG   GLN A 151      35.106  60.059  48.983  1.00 59.06      A  C
ATOM    850  CD   GLN A 151      36.136  59.694  47.909  1.00 59.06      A  C
ATOM    851  OE1  GLN A 151      35.828  59.741  46.704  1.00 59.06      A  O
ATOM    852  NE2  GLN A 151      37.349  59.328  48.330  1.00 59.06      A  N
ATOM    853  C    GLN A 151      31.746  58.490  49.598  1.00 44.00      A  C
ATOM    854  O    GLN A 151      31.551  57.871  50.649  1.00 44.00      A  O
ATOM    855  N    THR A 152      31.234  58.127  48.425  1.00 35.42      A  N
ATOM    856  CA   THR A 152      30.413  56.938  48.267  1.00 35.42      A  C
ATOM    857  CB   THR A 152      28.915  57.322  48.067  1.00 45.83      A  C
ATOM    858  OG1  THR A 152      28.158  56.860  49.198  1.00 45.83      A  O
ATOM    859  CG2  THR A 152      28.338  56.718  46.775  1.00 45.83      A  C
ATOM    860  C    THR A 152      30.957  56.175  47.065  1.00 35.42      A  C
ATOM    861  O    THR A 152      31.432  56.770  46.099  1.00 35.42      A  O
ATOM    862  N    LEU A 153      30.919  54.856  47.149  1.00 23.86      A  N
ATOM    863  CA   LEU A 153      31.380  54.003  46.067  1.00 23.86      A  C
ATOM    864  CB   LEU A 153      31.215  52.545  46.498  1.00 41.54      A  C
ATOM    865  CG   LEU A 153      31.488  51.457  45.460  1.00 41.54      A  C
ATOM    866  CD1  LEU A 153      32.988  51.344  45.214  1.00 41.54      A  C
ATOM    867  CD2  LEU A 153      30.925  50.139  45.962  1.00 41.54      A  C
ATOM    868  C    LEU A 153      30.559  54.277  44.793  1.00 23.86      A  C
ATOM    869  O    LEU A 153      29.333  54.356  44.853  1.00 23.86      A  O
ATOM    870  N    PRO A 154      31.223  54.448  43.633  1.00 23.34      A  N
ATOM    871  CD   PRO A 154      32.682  54.476  43.446  1.00 17.97      A  C
ATOM    872  CA   PRO A 154      30.522  54.705  42.366  1.00 23.34      A  C
ATOM    873  CB   PRO A 154      31.629  54.600  41.328  1.00 17.97      A  C
ATOM    874  CG   PRO A 154      32.822  55.039  42.056  1.00 17.97      A  C
ATOM    875  C    PRO A 154      29.461  53.631  42.137  1.00 23.34      A  C
ATOM    876  O    PRO A 154      29.712  52.445  42.361  1.00 23.34      A  O
ATOM    877  N    VAL A 155      28.287  54.032  41.664  1.00 33.96      A  N
ATOM    878  CA   VAL A 155      27.212  53.072  41.458  1.00 33.96      A  C
ATOM    879  CB   VAL A 155      25.917  53.791  41.063  1.00 27.12      A  C
ATOM    880  CG1  VAL A 155      25.611  54.854  42.097  1.00 27.12      A  C
ATOM    881  CG2  VAL A 155      26.041  54.395  39.675  1.00 27.12      A  C
ATOM    882  C    VAL A 155      27.525  51.947  40.467  1.00 33.96      A  C
ATOM    883  O    VAL A 155      26.992  50.841  40.596  1.00 33.96      A  O
ATOM    884  N    ILE A 156      28.380  52.209  39.486  1.00 23.34      A  N
ATOM    885  CA   ILE A 156      28.701  51.165  38.535  1.00 23.34      A  C
ATOM    886  CB   ILE A 156      29.771  51.634  37.527  1.00 16.35      A  C
ATOM    887  CG2  ILE A 156      30.983  52.163  38.266  1.00 16.35      A  C
ATOM    888  CG1  ILE A 156      30.166  50.479  36.603  1.00 16.35      A  C
ATOM    889  CD1  ILE A 156      29.030  49.947  35.760  1.00 16.35      A  C
ATOM    890  C    ILE A 156      29.206  49.963  39.328  1.00 23.34      A  C
ATOM    891  O    ILE A 156      28.882  48.820  39.010  1.00 23.34      A  O
ATOM    892  N    TYR A 157      29.983  50.236  40.373  1.00 21.81      A  N
ATOM    893  CA   TYR A 157      30.528  49.192  41.246  1.00 21.81      A  C
ATOM    894  CB   TYR A 157      31.638  49.766  42.140  1.00 43.54      A  C
ATOM    895  CG   TYR A 157      32.934  49.949  41.406  1.00 43.54      A  C
ATOM    896  CD1  TYR A 157      33.640  51.148  41.471  1.00 43.54      A  C
ATOM    897  CE1  TYR A 157      34.805  51.328  40.732  1.00 43.54      A  C
```

FIG. 6-16

| ATOM | 898 | CD2 | TYR A 157 | 33.427 | 48.931 | 40.591 | 1.00 | 43.54 | A | C |
|---|---|---|---|---|---|---|---|---|---|---|
| ATOM | 899 | CE2 | TYR A 157 | 34.585 | 49.098 | 39.852 | 1.00 | 43.54 | A | C |
| ATOM | 900 | CZ | TYR A 157 | 35.265 | 50.297 | 39.923 | 1.00 | 43.54 | A | C |
| ATOM | 901 | OH | TYR A 157 | 36.393 | 50.467 | 39.163 | 1.00 | 43.54 | A | O |
| ATOM | 902 | C | TYR A 157 | 29.449 | 48.585 | 42.131 | 1.00 | 21.81 | A | C |
| ATOM | 903 | O | TYR A 157 | 29.436 | 47.384 | 42.374 | 1.00 | 21.81 | A | O |
| ATOM | 904 | N | VAL A 158 | 28.555 | 49.434 | 42.626 | 1.00 | 24.10 | A | N |
| ATOM | 905 | CA | VAL A 158 | 27.464 | 48.989 | 43.479 | 1.00 | 24.10 | A | C |
| ATOM | 906 | CB | VAL A 158 | 26.672 | 50.209 | 44.034 | 1.00 | 17.15 | A | C |
| ATOM | 907 | CG1 | VAL A 158 | 25.524 | 49.742 | 44.902 | 1.00 | 17.15 | A | C |
| ATOM | 908 | CG2 | VAL A 158 | 27.593 | 51.100 | 44.839 | 1.00 | 17.15 | A | C |
| ATOM | 909 | C | VAL A 158 | 26.543 | 48.067 | 42.678 | 1.00 | 24.10 | A | C |
| ATOM | 910 | O | VAL A 158 | 25.893 | 47.185 | 43.236 | 1.00 | 24.10 | A | O |
| ATOM | 911 | N | LYS A 159 | 26.500 | 48.279 | 41.368 | 1.00 | 20.02 | A | N |
| ATOM | 912 | CA | LYS A 159 | 25.692 | 47.464 | 40.485 | 1.00 | 20.02 | A | C |
| ATOM | 913 | CB | LYS A 159 | 25.603 | 48.128 | 39.111 | 1.00 | 28.50 | A | C |
| ATOM | 914 | CG | LYS A 159 | 24.290 | 48.852 | 38.871 | 1.00 | 28.50 | A | C |
| ATOM | 915 | CD | LYS A 159 | 24.323 | 49.734 | 37.630 | 1.00 | 28.50 | A | C |
| ATOM | 916 | CE | LYS A 159 | 23.817 | 51.133 | 37.965 | 1.00 | 28.50 | A | C |
| ATOM | 917 | NZ | LYS A 159 | 23.130 | 51.843 | 36.836 | 1.00 | 28.50 | A | N |
| ATOM | 918 | C | LYS A 159 | 26.362 | 46.106 | 40.364 | 1.00 | 20.02 | A | C |
| ATOM | 919 | O | LYS A 159 | 25.771 | 45.076 | 40.694 | 1.00 | 20.02 | A | O |
| ATOM | 920 | N | LEU A 160 | 27.608 | 46.126 | 39.897 | 1.00 | 17.34 | A | N |
| ATOM | 921 | CA | LEU A 160 | 28.405 | 44.924 | 39.705 | 1.00 | 17.34 | A | C |
| ATOM | 922 | CB | LEU A 160 | 29.820 | 45.305 | 39.298 | 1.00 | 29.38 | A | C |
| ATOM | 923 | CG | LEU A 160 | 29.995 | 45.598 | 37.811 | 1.00 | 29.38 | A | C |
| ATOM | 924 | CD1 | LEU A 160 | 31.334 | 46.265 | 37.570 | 1.00 | 29.38 | A | C |
| ATOM | 925 | CD2 | LEU A 160 | 29.879 | 44.292 | 37.032 | 1.00 | 29.38 | A | C |
| ATOM | 926 | C | LEU A 160 | 28.469 | 43.998 | 40.901 | 1.00 | 17.34 | A | C |
| ATOM | 927 | O | LEU A 160 | 28.170 | 42.814 | 40.793 | 1.00 | 17.34 | A | O |
| ATOM | 928 | N | TYR A 161 | 28.875 | 44.542 | 42.041 | 1.00 | 23.02 | A | N |
| ATOM | 929 | CA | TYR A 161 | 28.985 | 43.755 | 43.251 | 1.00 | 23.02 | A | C |
| ATOM | 930 | CB | TYR A 161 | 29.591 | 44.595 | 44.387 | 1.00 | 20.95 | A | C |
| ATOM | 931 | CG | TYR A 161 | 30.978 | 45.164 | 44.108 | 1.00 | 20.95 | A | C |
| ATOM | 932 | CD1 | TYR A 161 | 31.877 | 44.500 | 43.268 | 1.00 | 20.95 | A | C |
| ATOM | 933 | CE1 | TYR A 161 | 33.158 | 45.004 | 43.047 | 1.00 | 20.95 | A | C |
| ATOM | 934 | CD2 | TYR A 161 | 31.404 | 46.352 | 44.719 | 1.00 | 20.95 | A | C |
| ATOM | 935 | CE2 | TYR A 161 | 32.678 | 46.860 | 44.500 | 1.00 | 20.95 | A | C |
| ATOM | 936 | CZ | TYR A 161 | 33.551 | 46.186 | 43.669 | 1.00 | 20.95 | A | C |
| ATOM | 937 | OH | TYR A 161 | 34.813 | 46.704 | 43.467 | 1.00 | 20.95 | A | O |
| ATOM | 938 | C | TYR A 161 | 27.630 | 43.195 | 43.672 | 1.00 | 23.02 | A | C |
| ATOM | 939 | O | TYR A 161 | 27.478 | 41.984 | 43.855 | 1.00 | 23.02 | A | O |
| ATOM | 940 | N | MET A 162 | 26.639 | 44.069 | 43.800 | 1.00 | 28.41 | A | N |
| ATOM | 941 | CA | MET A 162 | 25.324 | 43.628 | 44.220 | 1.00 | 28.41 | A | C |
| ATOM | 942 | CB | MET A 162 | 24.419 | 44.839 | 44.479 | 1.00 | 26.10 | A | C |
| ATOM | 943 | CG | MET A 162 | 24.757 | 45.581 | 45.782 | 1.00 | 26.10 | A | C |
| ATOM | 944 | SD | MET A 162 | 25.020 | 44.426 | 47.159 | 1.00 | 26.10 | A | S |
| ATOM | 945 | CE | MET A 162 | 23.384 | 43.953 | 47.447 | 1.00 | 26.10 | A | C |
| ATOM | 946 | C | MET A 162 | 24.657 | 42.641 | 43.286 | 1.00 | 28.41 | A | C |
| ATOM | 947 | O | MET A 162 | 23.814 | 41.861 | 43.720 | 1.00 | 28.41 | A | O |
| ATOM | 948 | N | TYR A 163 | 25.034 | 42.662 | 42.011 | 1.00 | 21.23 | A | N |
| ATOM | 949 | CA | TYR A 163 | 24.460 | 41.748 | 41.027 | 1.00 | 21.23 | A | C |
| ATOM | 950 | CB | TYR A 163 | 24.752 | 42.260 | 39.619 | 1.00 | 27.81 | A | C |
| ATOM | 951 | CG | TYR A 163 | 24.279 | 41.346 | 38.505 | 1.00 | 27.81 | A | C |
| ATOM | 952 | CD1 | TYR A 163 | 22.979 | 41.429 | 38.010 | 1.00 | 27.81 | A | C |
| ATOM | 953 | CE1 | TYR A 163 | 22.545 | 40.591 | 36.997 | 1.00 | 27.81 | A | C |
| ATOM | 954 | CD2 | TYR A 163 | 25.136 | 40.395 | 37.955 | 1.00 | 27.81 | A | C |
| ATOM | 955 | CE2 | TYR A 163 | 24.714 | 39.551 | 36.946 | 1.00 | 27.81 | A | C |
| ATOM | 956 | CZ | TYR A 163 | 23.417 | 39.651 | 36.460 | 1.00 | 27.81 | A | C |
| ATOM | 957 | OH | TYR A 163 | 23.004 | 38.837 | 35.411 | 1.00 | 27.81 | A | O |

FIG. 6-17

| | | | | | | | | | | |
|---|---|---|---|---|---|---|---|---|---|---|
| ATOM | 958 | C | TYR | A | 163 | 25.104 | 40.393 | 41.231 | 1.00 21.23 | A C |
| ATOM | 959 | O | TYR | A | 163 | 24.426 | 39.379 | 41.329 | 1.00 21.23 | A O |
| ATOM | 960 | N | GLN | A | 164 | 26.428 | 40.385 | 41.299 | 1.00 20.80 | A N |
| ATOM | 961 | CA | GLN | A | 164 | 27.169 | 39.155 | 41.510 | 1.00 20.80 | A C |
| ATOM | 962 | CB | GLN | A | 164 | 28.665 | 39.441 | 41.482 | 1.00 16.33 | A C |
| ATOM | 963 | CG | GLN | A | 164 | 29.158 | 40.082 | 40.210 | 1.00 16.33 | A C |
| ATOM | 964 | CD | GLN | A | 164 | 30.667 | 40.176 | 40.175 | 1.00 16.33 | A C |
| ATOM | 965 | OE1 | GLN | A | 164 | 31.353 | 39.163 | 40.123 | 1.00 16.33 | A O |
| ATOM | 966 | NE2 | GLN | A | 164 | 31.193 | 41.395 | 40.217 | 1.00 16.33 | A N |
| ATOM | 967 | C | GLN | A | 164 | 26.807 | 38.487 | 42.830 | 1.00 20.80 | A C |
| ATOM | 968 | O | GLN | A | 164 | 26.989 | 37.287 | 42.981 | 1.00 20.80 | A O |
| ATOM | 969 | N | LEU | A | 165 | 26.313 | 39.260 | 43.791 | 1.00 22.27 | A N |
| ATOM | 970 | CA | LEU | A | 165 | 25.929 | 38.695 | 45.082 | 1.00 22.27 | A C |
| ATOM | 971 | CB | LEU | A | 165 | 25.776 | 39.796 | 46.137 | 1.00 17.10 | A C |
| ATOM | 972 | CG | LEU | A | 165 | 25.078 | 39.400 | 47.442 | 1.00 17.10 | A C |
| ATOM | 973 | CD1 | LEU | A | 165 | 25.988 | 38.593 | 48.334 | 1.00 17.10 | A C |
| ATOM | 974 | CD2 | LEU | A | 165 | 24.654 | 40.643 | 48.158 | 1.00 17.10 | A C |
| ATOM | 975 | C | LEU | A | 165 | 24.615 | 37.951 | 44.940 | 1.00 22.27 | A C |
| ATOM | 976 | O | LEU | A | 165 | 24.399 | 36.923 | 45.585 | 1.00 22.27 | A O |
| ATOM | 977 | N | PHE | A | 166 | 23.733 | 38.472 | 44.095 | 1.00 19.30 | A N |
| ATOM | 978 | CA | PHE | A | 166 | 22.461 | 37.817 | 43.909 | 1.00 19.30 | A C |
| ATOM | 979 | CB | PHE | A | 166 | 21.448 | 38.787 | 43.298 | 1.00 15.89 | A C |
| ATOM | 980 | CG | PHE | A | 166 | 20.812 | 39.694 | 44.319 | 1.00 15.89 | A C |
| ATOM | 981 | CD1 | PHE | A | 166 | 20.210 | 39.159 | 45.457 | 1.00 15.89 | A C |
| ATOM | 982 | CD2 | PHE | A | 166 | 20.815 | 41.071 | 44.159 | 1.00 15.89 | A C |
| ATOM | 983 | CE1 | PHE | A | 166 | 19.626 | 39.985 | 46.421 | 1.00 15.89 | A C |
| ATOM | 984 | CE2 | PHE | A | 166 | 20.235 | 41.903 | 45.119 | 1.00 15.89 | A C |
| ATOM | 985 | CZ | PHE | A | 166 | 19.637 | 41.357 | 46.248 | 1.00 15.89 | A C |
| ATOM | 986 | C | PHE | A | 166 | 22.623 | 36.538 | 43.105 | 1.00 19.30 | A C |
| ATOM | 987 | O | PHE | A | 166 | 21.931 | 35.559 | 43.356 | 1.00 19.30 | A O |
| ATOM | 988 | N | ARG | A | 167 | 23.564 | 36.522 | 42.172 | 1.00 23.59 | A N |
| ATOM | 989 | CA | ARG | A | 167 | 23.796 | 35.320 | 41.393 | 1.00 23.59 | A C |
| ATOM | 990 | CB | ARG | A | 167 | 24.835 | 35.558 | 40.308 | 1.00 25.39 | A C |
| ATOM | 991 | CG | ARG | A | 167 | 24.246 | 35.956 | 38.969 | 1.00 25.39 | A C |
| ATOM | 992 | CD | ARG | A | 167 | 25.275 | 35.828 | 37.849 | 1.00 25.39 | A C |
| ATOM | 993 | NE | ARG | A | 167 | 25.537 | 34.438 | 37.475 | 1.00 25.39 | A N |
| ATOM | 994 | CZ | ARG | A | 167 | 26.552 | 34.053 | 36.712 | 1.00 25.39 | A C |
| ATOM | 995 | NH1 | ARG | A | 167 | 27.411 | 34.933 | 36.246 | 1.00 25.39 | A N |
| ATOM | 996 | NH2 | ARG | A | 167 | 26.691 | 32.789 | 36.385 | 1.00 25.39 | A N |
| ATOM | 997 | C | ARG | A | 167 | 24.272 | 34.186 | 42.279 | 1.00 23.59 | A C |
| ATOM | 998 | O | ARG | A | 167 | 23.942 | 33.027 | 42.031 | 1.00 23.59 | A O |
| ATOM | 999 | N | SER | A | 168 | 25.058 | 34.515 | 43.303 | 1.00 20.74 | A N |
| ATOM | 1000 | CA | SER | A | 168 | 25.558 | 33.496 | 44.220 | 1.00 20.74 | A C |
| ATOM | 1001 | CB | SER | A | 168 | 26.718 | 34.038 | 45.069 | 1.00 19.61 | A C |
| ATOM | 1002 | OG | SER | A | 168 | 26.284 | 35.023 | 45.985 | 1.00 19.61 | A O |
| ATOM | 1003 | C | SER | A | 168 | 24.415 | 33.038 | 45.110 | 1.00 20.74 | A C |
| ATOM | 1004 | O | SER | A | 168 | 24.326 | 31.874 | 45.470 | 1.00 20.74 | A O |
| ATOM | 1005 | N | LEU | A | 169 | 23.532 | 33.967 | 45.436 | 1.00 18.88 | A N |
| ATOM | 1006 | CA | LEU | A | 169 | 22.381 | 33.680 | 46.266 | 1.00 18.88 | A C |
| ATOM | 1007 | CB | LEU | A | 169 | 21.723 | 34.992 | 46.677 | 1.00 22.01 | A C |
| ATOM | 1008 | CG | LEU | A | 169 | 21.769 | 35.369 | 48.155 | 1.00 22.01 | A C |
| ATOM | 1009 | CD1 | LEU | A | 169 | 23.097 | 35.013 | 48.780 | 1.00 22.01 | A C |
| ATOM | 1010 | CD2 | LEU | A | 169 | 21.501 | 36.840 | 48.273 | 1.00 22.01 | A C |
| ATOM | 1011 | C | LEU | A | 169 | 21.388 | 32.813 | 45.502 | 1.00 18.88 | A C |
| ATOM | 1012 | O | LEU | A | 169 | 20.853 | 31.846 | 46.042 | 1.00 18.88 | A O |
| ATOM | 1013 | N | ALA | A | 170 | 21.150 | 33.156 | 44.242 | 1.00 16.34 | A N |
| ATOM | 1014 | CA | ALA | A | 170 | 20.218 | 32.394 | 43.428 | 1.00 16.34 | A C |
| ATOM | 1015 | CB | ALA | A | 170 | 20.000 | 33.077 | 42.092 | 1.00 10.39 | A C |
| ATOM | 1016 | C | ALA | A | 170 | 20.770 | 31.001 | 43.217 | 1.00 16.34 | A C |
| ATOM | 1017 | O | ALA | A | 170 | 20.022 | 30.045 | 43.020 | 1.00 16.34 | A O |

FIG. 6-18

```
ATOM   1018  N    TYR A 171      22.092  30.888  43.271  1.00 32.57      A  N
ATOM   1019  CA   TYR A 171      22.745  29.602  43.074  1.00 32.57      A  C
ATOM   1020  CB   TYR A 171      24.242  29.777  42.829  1.00 25.76      A  C
ATOM   1021  CG   TYR A 171      24.996  28.462  42.692  1.00 25.76      A  C
ATOM   1022  CD1  TYR A 171      24.742  27.592  41.631  1.00 25.76      A  C
ATOM   1023  CE1  TYR A 171      25.446  26.380  41.498  1.00 25.76      A  C
ATOM   1024  CD2  TYR A 171      25.973  28.092  43.619  1.00 25.76      A  C
ATOM   1025  CE2  TYR A 171      26.677  26.891  43.493  1.00 25.76      A  C
ATOM   1026  CZ   TYR A 171      26.413  26.039  42.431  1.00 25.76      A  C
ATOM   1027  OH   TYR A 171      27.130  24.864  42.307  1.00 25.76      A  O
ATOM   1028  C    TYR A 171      22.554  28.688  44.259  1.00 32.57      A  C
ATOM   1029  O    TYR A 171      21.932  27.637  44.138  1.00 32.57      A  O
ATOM   1030  N    ILE A 172      23.093  29.078  45.407  1.00 26.47      A  N
ATOM   1031  CA   ILE A 172      22.970  28.243  46.588  1.00 26.47      A  C
ATOM   1032  CB   ILE A 172      23.764  28.819  47.775  1.00 20.39      A  C
ATOM   1033  CG2  ILE A 172      25.241  28.816  47.450  1.00 20.39      A  C
ATOM   1034  CG1  ILE A 172      23.270  30.225  48.110  1.00 20.39      A  C
ATOM   1035  CD1  ILE A 172      23.849  30.784  49.393  1.00 20.39      A  C
ATOM   1036  C    ILE A 172      21.521  28.010  47.010  1.00 26.47      A  C
ATOM   1037  O    ILE A 172      21.194  26.965  47.556  1.00 26.47      A  O
ATOM   1038  N    HIS A 173      20.645  28.972  46.757  1.00 20.06      A  N
ATOM   1039  CA   HIS A 173      19.261  28.773  47.137  1.00 20.06      A  C
ATOM   1040  CB   HIS A 173      18.459  30.074  47.005  1.00 19.53      A  C
ATOM   1041  CG   HIS A 173      18.766  31.081  48.075  1.00 19.53      A  C
ATOM   1042  CD2  HIS A 173      19.557  31.003  49.174  1.00 19.53      A  C
ATOM   1043  ND1  HIS A 173      18.254  32.361  48.066  1.00 19.53      A  N
ATOM   1044  CE1  HIS A 173      18.720  33.026  49.107  1.00 19.53      A  C
ATOM   1045  NE2  HIS A 173      19.513  32.226  49.794  1.00 19.53      A  N
ATOM   1046  C    HIS A 173      18.656  27.666  46.294  1.00 20.06      A  C
ATOM   1047  O    HIS A 173      17.895  26.862  46.808  1.00 20.06      A  O
ATOM   1048  N    SER A 174      19.004  27.596  45.012  1.00 29.63      A  N
ATOM   1049  CA   SER A 174      18.450  26.548  44.151  1.00 29.63      A  C
ATOM   1050  CB   SER A 174      19.023  26.639  42.727  1.00 28.82      A  C
ATOM   1051  OG   SER A 174      20.343  26.131 -42.654  1.00 28.82      A  O
ATOM   1052  C    SER A 174      18.743  25.164  44.741  1.00 29.63      A  C
ATOM   1053  O    SER A 174      18.114  24.178  44.380  1.00 29.63      A  O
ATOM   1054  N    PHE A 175      19.700  25.101  45.652  1.00 23.50      A  N
ATOM   1055  CA   PHE A 175      20.042  23.850  46.302  1.00 23.50      A  C
ATOM   1056  CB   PHE A 175      21.554  23.781  46.534  1.00 45.44      A  C
ATOM   1057  CG   PHE A 175      22.338  23.338  45.338  1.00 45.44      A  C
ATOM   1058  CD1  PHE A 175      22.577  21.986  45.111  1.00 45.44      A  C
ATOM   1059  CD2  PHE A 175      22.843  24.269  44.441  1.00 45.44      A  C
ATOM   1060  CE1  PHE A 175      23.307  21.566  44.009  1.00 45.44      A  C
ATOM   1061  CE2  PHE A 175      23.580  23.863  43.326  1.00 45.44      A  C
ATOM   1062  CZ   PHE A 175      23.813  22.508  43.111  1.00 45.44      A  C
ATOM   1063  C    PHE A 175      19.348  23.780  47.653  1.00 23.50      A  C
ATOM   1064  O    PHE A 175      19.482  22.790  48.363  1.00 23.50      A  O
ATOM   1065  N    GLY A 176      18.624  24.836  48.011  1.00 24.00      A  N
ATOM   1066  CA   GLY A 176      17.949  24.874  49.297  1.00 24.00      A  C
ATOM   1067  C    GLY A 176      18.932  25.133  50.424  1.00 24.00      A  C
ATOM   1068  O    GLY A 176      18.737  24.665  51.538  1.00 24.00      A  O
ATOM   1069  N    ILE A 177      19.996  25.870  50.125  1.00 27.54      A  N
ATOM   1070  CA   ILE A 177      21.023  26.209  51.102  1.00 27.54      A  C
ATOM   1071  CB   ILE A 177      22.427  25.917  50.561  1.00 38.36      A  C
ATOM   1072  CG2  ILE A 177      23.464  26.225  51.620  1.00 38.36      A  C
ATOM   1073  CG1  ILE A 177      22.524  24.461  50.117  1.00 38.36      A  C
ATOM   1074  CD1  ILE A 177      23.858  24.118  49.444  1.00 38.36      A  C
ATOM   1075  C    ILE A 177      20.942  27.701  51.391  1.00 27.54      A  C
ATOM   1076  O    ILE A 177      20.911  28.518  50.471  1.00 27.54      A  O
ATOM   1077  N    CYS A 178      20.919  28.041  52.674  1.00 24.00      A  N
```

FIG. 6-19

```
ATOM   1078  CA   CYS A 178      20.819  29.419  53.114  1.00 24.00      A    C
ATOM   1079  CB   CYS A 178      19.703  29.536  54.140  1.00 21.11      A    C
ATOM   1080  SG   CYS A 178      19.050  31.174  54.358  1.00 21.11      A    S
ATOM   1081  C    CYS A 178      22.137  29.798  53.747  1.00 24.00      A    C
ATOM   1082  O    CYS A 178      22.710  29.011  54.492  1.00 24.00      A    O
ATOM   1083  N    HIS A 179      22.624  30.999  53.450  1.00 20.94      A    N
ATOM   1084  CA   HIS A 179      23.885  31.462  54.014  1.00 20.94      A    C
ATOM   1085  CB   HIS A 179      24.395  32.667  53.235  1.00 15.09      A    C
ATOM   1086  CG   HIS A 179      25.828  32.989  53.505  1.00 15.09      A    C
ATOM   1087  CD2  HIS A 179      26.948  32.701  52.805  1.00 15.09      A    C
ATOM   1088  ND1  HIS A 179      26.244  33.660  54.636  1.00 15.09      A    N
ATOM   1089  CE1  HIS A 179      27.558  33.770  54.621  1.00 15.09      A    C
ATOM   1090  NE2  HIS A 179      28.011  33.195  53.522  1.00 15.09      A    N
ATOM   1091  C    HIS A 179      23.701  31.824  55.487  1.00 20.94      A    C
ATOM   1092  O    HIS A 179      24.487  31.408  56.334  1.00 20.94      A    O
ATOM   1093  N    ARG A 180      22.653  32.596  55.771  1.00 32.96      A    N
ATOM   1094  CA   ARG A 180      22.314  33.019  57.126  1.00 32.96      A    C
ATOM   1095  CB   ARG A 180      22.311  31.822  58.058  1.00 22.71      A    C
ATOM   1096  CG   ARG A 180      21.227  30.816  57.779  1.00 22.71      A    C
ATOM   1097  CD   ARG A 180      21.630  29.546  58.434  1.00 22.71      A    C
ATOM   1098  NE   ARG A 180      20.586  28.978  59.253  1.00 22.71      A    N
ATOM   1099  CZ   ARG A 180      20.816  28.059  60.176  1.00 22.71      A    C
ATOM   1100  NH1  ARG A 180      22.053  27.628  60.383  1.00 22.71      A    N
ATOM   1101  NH2  ARG A 180      19.813  27.565  60.884  1.00 22.71      A    N
ATOM   1102  C    ARG A 180      23.222  34.095  57.722  1.00 32.96      A    C
ATOM   1103  O    ARG A 180      22.979  34.585  58.830  1.00 32.96      A    O
ATOM   1104  N    ASP A 181      24.266  34.471  56.992  1.00 20.89      A    N
ATOM   1105  CA   ASP A 181      25.176  35.476  57.502  1.00 20.89      A    C
ATOM   1106  CB   ASP A 181      26.249  34.796  58.358  1.00 33.02      A    C
ATOM   1107  CG   ASP A 181      27.059  35.780  59.181  1.00 33.02      A    C
ATOM   1108  OD1  ASP A 181      26.455  36.709  59.768  1.00 33.02      A    O
ATOM   1109  OD2  ASP A 181      28.299  35.615  59.250  1.00 33.02      A    O
ATOM   1110  C    ASP A 181      25.805  36.344  56.416  1.00 20.89      A    C
ATOM   1111  O    ASP A 181      27.025  36.537  56.362  1.00 20.89      A    O
ATOM   1112  N    ILE A 182      24.951  36.866  55.549  1.00 13.90      A    N
ATOM   1113  CA   ILE A 182      25.400  37.744  54.494  1.00 13.90      A    C
ATOM   1114  CB   ILE A 182      24.316  37.916  53.408  1.00  7.58      A    C
ATOM   1115  CG2  ILE A 182      24.764  38.929  52.380  1.00  7.58      A    C
ATOM   1116  CG1  ILE A 182      23.976  36.563  52.777  1.00  7.58      A    C
ATOM   1117  CD1  ILE A 182      25.068  35.971  51.953  1.00  7.58      A    C
ATOM   1118  C    ILE A 182      25.676  39.098  55.148  1.00 13.90      A    C
ATOM   1119  O    ILE A 182      24.805  39.702  55.777  1.00 13.90      A    O
ATOM   1120  N    LYS A 183      26.914  39.550  55.022  1.00 21.14      A    N
ATOM   1121  CA   LYS A 183      27.339  40.840  55.559  1.00 21.14      A    C
ATOM   1122  CB   LYS A 183      27.748  40.744  57.019  1.00 14.96      A    C
ATOM   1123  CG   LYS A 183      28.857  39.744  57.323  1.00 14.96      A    C
ATOM   1124  CD   LYS A 183      28.950  39.510  58.818  1.00 14.96      A    C
ATOM   1125  CE   LYS A 183      29.991  38.469  59.154  1.00 14.96      A    C
ATOM   1126  NZ   LYS A 183      30.032  38.184  60.605  1.00 14.96      A    N
ATOM   1127  C    LYS A 183      28.523  41.253  54.711  1.00 21.14      A    C
ATOM   1128  O    LYS A 183      29.214  40.402  54.153  1.00 21.14      A    O
ATOM   1129  N    PRO A 184      28.758  42.569  54.565  1.00 23.23      A    N
ATOM   1130  CD   PRO A 184      27.869  43.679  54.932  1.00 14.33      A    C
ATOM   1131  CA   PRO A 184      29.891  43.059  53.780  1.00 23.23      A    C
ATOM   1132  CB   PRO A 184      29.954  44.505  54.191  1.00 14.33      A    C
ATOM   1133  CG   PRO A 184      28.522  44.841  54.267  1.00 14.33      A    C
ATOM   1134  C    PRO A 184      31.227  42.349  54.020  1.00 23.23      A    C
ATOM   1135  O    PRO A 184      32.044  42.204  53.109  1.00 23.23      A    O
ATOM   1136  N    GLN A 185      31.475  41.922  55.245  1.00 23.24      A    N
ATOM   1137  CA   GLN A 185      32.728  41.250  55.570  1.00 23.24      A    C
```

FIG. 6-20

```
ATOM   1138  CB   GLN A 185      32.844  41.133  57.080  1.00 56.98       A    C
ATOM   1139  CG   GLN A 185      34.263  41.061  57.554  1.00 56.98       A    C
ATOM   1140  CD   GLN A 185      34.430  40.091  58.713  1.00 56.98       A    C
ATOM   1141  OE1  GLN A 185      35.486  39.472  58.862  1.00 56.98       A    O
ATOM   1142  NE2  GLN A 185      33.392  39.972  59.563  1.00 56.98       A    N
ATOM   1143  C    GLN A 185      32.829  39.867  54.927  1.00 23.24       A    C
ATOM   1144  O    GLN A 185      33.923  39.340  54.764  1.00 23.24       A    O
ATOM   1145  N    ASN A 186      31.690  39.290  54.570  1.00 23.76       A    N
ATOM   1146  CA   ASN A 186      31.648  37.976  53.939  1.00 23.76       A    C
ATOM   1147  CB   ASN A 186      30.401  37.215  54.354  1.00 27.48       A    C
ATOM   1148  CG   ASN A 186      30.589  36.452  55.625  1.00 27.48       A    C
ATOM   1149  OD1  ASN A 186      31.710  36.348  56.130  1.00 27.48       A    O
ATOM   1150  ND2  ASN A 186      29.508  35.915  56.166  1.00 27.48       A    N
ATOM   1151  C    ASN A 186      31.674  38.089  52.441  1.00 23.76       A    C
ATOM   1152  O    ASN A 186      31.599  37.080  51.755  1.00 23.76       A    O
ATOM   1153  N    LEU A 187      31.755  39.317  51.938  1.00 17.74       A    N
ATOM   1154  CA   LEU A 187      31.781  39.557  50.503  1.00 17.74       A    C
ATOM   1155  CB   LEU A 187      30.792  40.652  50.144  1.00 18.83       A    C
ATOM   1156  CG   LEU A 187      29.359  40.389  50.586  1.00 18.83       A    C
ATOM   1157  CD1  LEU A 187      28.471  41.526  50.111  1.00 18.83       A    C
ATOM   1158  CD2  LEU A 187      28.869  39.070  50.023  1.00 18.83       A    C
ATOM   1159  C    LEU A 187      33.180  39.942  50.028  1.00 17.74       A    C
ATOM   1160  O    LEU A 187      33.594  41.088  50.145  1.00 17.74       A    O
ATOM   1161  N    LEU A 188      33.900  38.959  49.496  1.00 27.59       A    N
ATOM   1162  CA   LEU A 188      35.253  39.150  48.973  1.00 27.59       A    C
ATOM   1163  CB   LEU A 188      35.998  37.813  48.906  1.00 36.69       A    C
ATOM   1164  CG   LEU A 188      36.072  36.885  50.115  1.00 36.69       A    C
ATOM   1165  CD1  LEU A 188      36.622  35.549  49.681  1.00 36.69       A    C
ATOM   1166  CD2  LEU A 188      36.943  37.502  51.189  1.00 36.69       A    C
ATOM   1167  C    LEU A 188      35.159  39.697  47.557  1.00 27.59       A    C
ATOM   1168  O    LEU A 188      34.180  39.442  46.852  1.00 27.59       A    O
ATOM   1169  N    LEU A 189      36.169  40.444  47.131  1.00 24.81       A    N
ATOM   1170  CA   LEU A 189      36.161  40.972  45.776  1.00 24.81       A    C
ATOM   1171  CB   LEU A 189      35.237  42.204  45.673  1.00 41.46       A    C
ATOM   1172  CG   LEU A 189      35.596  43.572  46.264  1.00 41.46       A    C
ATOM   1173  CD1  LEU A 189      34.317  44.330  46.594  1.00 41.46       A    C
ATOM   1174  CD2  LEU A 189      36.401  43.406  47.516  1.00 41.46       A    C
ATOM   1175  C    LEU A 189      37.566  41.291  45.294  1.00 24.81       A    C
ATOM   1176  O    LEU A 189      38.493  41.437  46.089  1.00 24.81       A    O
ATOM   1177  N    ASP A 190      37.724  41.339  43.977  1.00 36.67       A    N
ATOM   1178  CA   ASP A 190      39.004  41.658  43.370  1.00 36.67       A    C
ATOM   1179  CB   ASP A 190      39.333  40.670  42.252  1.00 40.59       A    C
ATOM   1180  CG   ASP A 190      40.750  40.831  41.737  1.00 40.59       A    C
ATOM   1181  OD1  ASP A 190      41.678  40.682  42.553  1.00 40.59       A    O
ATOM   1182  OD2  ASP A 190      40.944  41.107  40.530  1.00 40.59       A    O
ATOM   1183  C    ASP A 190      38.814  43.060  42.806  1.00 36.67       A    C
ATOM   1184  O    ASP A 190      37.932  43.293  41.975  1.00 36.67       A    O
ATOM   1185  N    PRO A 191      39.635  44.015  43.253  1.00 42.36       A    N
ATOM   1186  CD   PRO A 191      40.759  43.837  44.182  1.00 47.79       A    C
ATOM   1187  CA   PRO A 191      39.551  45.409  42.797  1.00 42.36       A    C
ATOM   1188  CB   PRO A 191      40.668  46.098  43.574  1.00 47.79       A    C
ATOM   1189  CG   PRO A 191      40.858  45.204  44.785  1.00 47.79       A    C
ATOM   1190  C    PRO A 191      39.732  45.588  41.291  1.00 42.36       A    C
ATOM   1191  O    PRO A 191      39.049  46.396  40.659  1.00 42.36       A    O
ATOM   1192  N    ASP A 192      40.653  44.835  40.711  1.00 49.12       A    N
ATOM   1193  CA   ASP A 192      40.881  44.984  39.293  1.00 49.12       A    C
ATOM   1194  CB   ASP A 192      42.246  44.425  38.916  1.00 49.22       A    C
ATOM   1195  CG   ASP A 192      43.359  45.087  39.693  1.00 49.22       A    C
ATOM   1196  OD1  ASP A 192      43.228  46.307  39.986  1.00 49.22       A    O
ATOM   1197  OD2  ASP A 192      44.352  44.389  40.006  1.00 49.22       A    O
```

FIG. 6-21

```
ATOM   1198  C    ASP A 192      39.788  44.360  38.435  1.00 49.12      A   C
ATOM   1199  O    ASP A 192      39.170  45.051  37.610  1.00 49.12      A   O
ATOM   1200  N    THR A 193      39.530  43.068  38.619  1.00 29.20      A   N
ATOM   1201  CA   THR A 193      38.503  42.430  37.814  1.00 29.20      A   C
ATOM   1202  CB   THR A 193      38.691  40.895  37.752  1.00 26.36      A   C
ATOM   1203  OG1  THR A 193      38.782  40.354  39.071  1.00 26.36      A   O
ATOM   1204  CG2  THR A 193      39.950  40.557  36.996  1.00 26.36      A   C
ATOM   1205  C    THR A 193      37.074  42.751  38.249  1.00 29.20      A   C
ATOM   1206  O    THR A 193      36.133  42.476  37.513  1.00 29.20      A   O
ATOM   1207  N    ALA A 194      36.918  43.347  39.430  1.00 22.39      A   N
ATOM   1208  CA   ALA A 194      35.605  43.705  39.965  1.00 22.39      A   C
ATOM   1209  CB   ALA A 194      34.881  44.641  39.010  1.00  8.33      A   C
ATOM   1210  C    ALA A 194      34.741  42.487  40.249  1.00 22.39      A   C
ATOM   1211  O    ALA A 194      33.524  42.601  40.382  1.00 22.39      A   O
ATOM   1212  N    VAL A 195      35.370  41.318  40.341  1.00 30.34      A   N
ATOM   1213  CA   VAL A 195      34.638  40.085  40.613  1.00 30.34      A   C
ATOM   1214  CB   VAL A 195      35.361  38.864  39.995  1.00 40.89      A   C
ATOM   1215  CG1  VAL A 195      36.832  38.976  40.229  1.00 40.89      A   C
ATOM   1216  CG2  VAL A 195      34.829  37.569  40.602  1.00 40.89      A   C
ATOM   1217  C    VAL A 195      34.397  39.859  42.111  1.00 30.34      A   C
ATOM   1218  O    VAL A 195      35.323  39.910  42.930  1.00 30.34      A   O
ATOM   1219  N    LEU A 196      33.133  39.633  42.458  1.00 34.55      A   N
ATOM   1220  CA   LEU A 196      32.742  39.406  43.838  1.00 34.55      A   C
ATOM   1221  CB   LEU A 196      31.475  40.200  44.162  1.00 15.74      A   C
ATOM   1222  CG   LEU A 196      31.062  40.239  45.635  1.00 15.74      A   C
ATOM   1223  CD1  LEU A 196      30.369  41.552  45.917  1.00 15.74      A   C
ATOM   1224  CD2  LEU A 196      30.166  39.080  45.971  1.00 15.74      A   C
ATOM   1225  C    LEU A 196      32.526  37.924  44.107  1.00 34.55      A   C
ATOM   1226  O    LEU A 196      31.972  37.203  43.280  1.00 34.55      A   O
ATOM   1227  N    LYS A 197      32.979  37.474  45.271  1.00 22.73      A   N
ATOM   1228  CA   LYS A 197      32.852  36.079  45.652  1.00 22.73      A   C
ATOM   1229  CB   LYS A 197      34.203  35.377  45.506  1.00 26.65      A   C
ATOM   1230  CG   LYS A 197      34.627  35.271  44.054  1.00 26.65      A   C
ATOM   1231  CD   LYS A 197      35.867  34.442  43.823  1.00 26.65      A   C
ATOM   1232  CE   LYS A 197      36.092  34.336  42.322  1.00 26.65      A   C
ATOM   1233  NZ   LYS A 197      37.036  33.258  41.912  1.00 26.65      A   N
ATOM   1234  C    LYS A 197      32.354  35.992  47.078  1.00 22.73      A   C
ATOM   1235  O    LYS A 197      32.863  36.674  47.962  1.00 22.73      A   O
ATOM   1236  N    LEU A 198      31.342  35.161  47.290  1.00 27.40      A   N
ATOM   1237  CA   LEU A 198      30.756  34.967  48.611  1.00 27.40      A   C
ATOM   1238  CB   LEU A 198      29.355  34.375  48.481  1.00 24.98      A   C
ATOM   1239  CG   LEU A 198      28.303  34.786  49.503  1.00 24.98      A   C
ATOM   1240  CD1  LEU A 198      27.194  33.749  49.531  1.00 24.98      A   C
ATOM   1241  CD2  LEU A 198      28.931  34.908  50.855  1.00 24.98      A   C
ATOM   1242  C    LEU A 198      31.639  33.969  49.353  1.00 27.40      A   C
ATOM   1243  O    LEU A 198      32.227  33.092  48.731  1.00 27.40      A   O
ATOM   1244  N    CYS A 199      31.740  34.095  50.673  1.00 15.48      A   N
ATOM   1245  CA   CYS A 199      32.548  33.164  51.435  1.00 15.48      A   C
ATOM   1246  CB   CYS A 199      34.001  33.648  51.526  1.00 17.26      A   C
ATOM   1247  SG   CYS A 199      34.334  35.049  52.579  1.00 17.26      A   S
ATOM   1248  C    CYS A 199      31.978  32.965  52.821  1.00 15.48      A   C
ATOM   1249  O    CYS A 199      30.895  33.456  53.123  1.00 15.48      A   O
ATOM   1250  N    ASP A 200      32.704  32.211  53.646  1.00 24.37      A   N
ATOM   1251  CA   ASP A 200      32.325  31.936  55.032  1.00 24.37      A   C
ATOM   1252  CB   ASP A 200      32.358  33.244  55.829  1.00 47.06      A   C
ATOM   1253  CG   ASP A 200      32.402  33.030  57.342  1.00 47.06      A   C
ATOM   1254  OD1  ASP A 200      32.343  31.857  57.808  1.00 47.06      A   O
ATOM   1255  OD2  ASP A 200      32.499  34.061  58.064  1.00 47.06      A   O
ATOM   1256  C    ASP A 200      30.953  31.283  55.168  1.00 24.37      A   C
ATOM   1257  O    ASP A 200      29.989  31.927  55.567  1.00 24.37      A   O
```

FIG. 6-22

```
ATOM   1258  N    PHE A 201      30.871  29.999  54.843  1.00 30.20      A  N
ATOM   1259  CA   PHE A 201      29.610  29.278  54.947  1.00 30.20      A  C
ATOM   1260  CB   PHE A 201      29.460  28.296  53.788  1.00 25.93      A  C
ATOM   1261  CG   PHE A 201      29.331  28.961  52.458  1.00 25.93      A  C
ATOM   1262  CD1  PHE A 201      30.401  29.659  51.915  1.00 25.93      A  C
ATOM   1263  CD2  PHE A 201      28.127  28.933  51.764  1.00 25.93      A  C
ATOM   1264  CE1  PHE A 201      30.279  30.322  50.697  1.00 25.93      A  C
ATOM   1265  CE2  PHE A 201      27.991  29.591  50.550  1.00 25.93      A  C
ATOM   1266  CZ   PHE A 201      29.073  30.291  50.017  1.00 25.93      A  C
ATOM   1267  C    PHE A 201      29.533  28.541  56.272  1.00 30.20      A  C
ATOM   1268  O    PHE A 201      28.889  27.496  56.383  1.00 30.20      A  O
ATOM   1269  N    GLY A 202      30.200  29.100  57.274  1.00 23.48      A  N
ATOM   1270  CA   GLY A 202      30.191  28.501  58.593  1.00 23.48      A  C
ATOM   1271  C    GLY A 202      28.851  28.628  59.295  1.00 23.48      A  C
ATOM   1272  O    GLY A 202      28.700  28.158  60.405  1.00 23.48      A  O
ATOM   1273  N    SER A 203      27.875  29.264  58.666  1.00 24.05      A  N
ATOM   1274  CA   SER A 203      26.564  29.400  59.283  1.00 24.05      A  C
ATOM   1275  CB   SER A 203      26.270  30.860  59.634  1.00 26.29      A  C
ATOM   1276  OG   SER A 203      27.124  31.317  60.662  1.00 26.29      A  O
ATOM   1277  C    SER A 203      25.495  28.884  58.336  1.00 24.05      A  C
ATOM   1278  O    SER A 203      24.313  28.867  58.666  1.00 24.05      A  O
ATOM   1279  N    ALA A 204      25.916  28.453  57.156  1.00 25.04      A  N
ATOM   1280  CA   ALA A 204      24.982  27.948  56.172  1.00 25.04      A  C
ATOM   1281  CB   ALA A 204      25.671  27.819  54.831  1.00 29.87      A  C
ATOM   1282  C    ALA A 204      24.378  26.614  56.563  1.00 25.04      A  C
ATOM   1283  O    ALA A 204      25.001  25.799  57.236  1.00 25.04      A  O
ATOM   1284  N    LYS A 205      23.151  26.400  56.114  1.00 29.49      A  N
ATOM   1285  CA   LYS A 205      22.431  25.168  56.376  1.00 29.49      A  C
ATOM   1286  CB   LYS A 205      21.632  25.272  57.674  1.00 46.29      A  C
ATOM   1287  CG   LYS A 205      20.968  23.954  58.047  1.00 46.29      A  C
ATOM   1288  CD   LYS A 205      19.819  24.087  59.031  1.00 46.29      A  C
ATOM   1289  CE   LYS A 205      19.373  22.698  59.463  1.00 46.29      A  C
ATOM   1290  NZ   LYS A 205      18.148  22.694  60.317  1.00 46.29      A  N
ATOM   1291  C    LYS A 205      21.457  24.886  55.224  1.00 29.49      A  C
ATOM   1292  O    LYS A 205      20.948  25.808  54.575  1.00 29.49      A  O
ATOM   1293  N    GLN A 206      21.199  23.604  54.989  1.00 41.39      A  N
ATOM   1294  CA   GLN A 206      20.278  23.162  53.952  1.00 41.39      A  C
ATOM   1295  CB   GLN A 206      20.605  21.708  53.602  1.00 38.22      A  C
ATOM   1296  CG   GLN A 206      20.617  21.356  52.112  1.00 38.22      A  C
ATOM   1297  CD   GLN A 206      19.249  20.939  51.608  1.00 38.22      A  C
ATOM   1298  OE1  GLN A 206      18.524  20.212  52.285  1.00 38.22      A  O
ATOM   1299  NE2  GLN A 206      18.893  21.385  50.414  1.00 38.22      A  N
ATOM   1300  C    GLN A 206      18.874  23.273  54.548  1.00 41.39      A  C
ATOM   1301  O    GLN A 206      18.418  22.351  55.201  1.00 41.39      A  O
ATOM   1302  N    LEU A 207      18.187  24.389  54.332  1.00 33.88      A  N
ATOM   1303  CA   LEU A 207      16.857  24.585  54.907  1.00 33.88      A  C
ATOM   1304  CB   LEU A 207      16.427  26.042  54.772  1.00 20.86      A  C
ATOM   1305  CG   LEU A 207      17.289  27.097  55.467  1.00 20.86      A  C
ATOM   1306  CD1  LEU A 207      16.509  28.407  55.451  1.00 20.86      A  C
ATOM   1307  CD2  LEU A 207      17.637  26.692  56.907  1.00 20.86      A  C
ATOM   1308  C    LEU A 207      15.721  23.711  54.396  1.00 33.88      A  C
ATOM   1309  O    LEU A 207      15.133  23.982  53.357  1.00 33.88      A  O
ATOM   1310  N    VAL A 208      15.389  22.676  55.150  1.00 36.07      A  N
ATOM   1311  CA   VAL A 208      14.303  21.788  54.780  1.00 36.07      A  C
ATOM   1312  CB   VAL A 208      14.454  20.412  55.429  1.00 30.05      A  C
ATOM   1313  CG1  VAL A 208      13.247  19.563  55.102  1.00 30.05      A  C
ATOM   1314  CG2  VAL A 208      15.750  19.755  54.969  1.00 30.05      A  C
ATOM   1315  C    VAL A 208      13.004  22.382  55.288  1.00 36.07      A  C
ATOM   1316  O    VAL A 208      12.967  22.955  56.371  1.00 36.07      A  O
ATOM   1317  N    ARG A 209      11.937  22.233  54.514  1.00 48.38      A  N
```

FIG. 6-23

```
ATOM   1318  CA   ARG A 209      10.627  22.751  54.900  1.00 48.38      A    C
ATOM   1319  CB   ARG A 209       9.655  22.709  53.717  1.00 87.17      A    C
ATOM   1320  CG   ARG A 209       8.221  23.002  54.102  1.00 87.17      A    C
ATOM   1321  CD   ARG A 209       7.720  24.281  53.449  1.00 87.17      A    C
ATOM   1322  NE   ARG A 209       6.878  24.020  52.276  1.00 87.17      A    N
ATOM   1323  CZ   ARG A 209       7.288  23.426  51.151  1.00 87.17      A    C
ATOM   1324  NH1  ARG A 209       8.552  23.013  51.021  1.00 87.17      A    N
ATOM   1325  NH2  ARG A 209       6.428  23.251  50.147  1.00 87.17      A    N
ATOM   1326  C    ARG A 209      10.056  21.920  56.033  1.00 48.38      A    C
ATOM   1327  O    ARG A 209      10.146  20.687  56.020  1.00 48.38      A    O
ATOM   1328  N    GLY A 210       9.460  22.608  57.004  1.00 42.37      A    N
ATOM   1329  CA   GLY A 210       8.869  21.937  58.146  1.00 42.37      A    C
ATOM   1330  C    GLY A 210       9.875  21.787  59.260  1.00 42.37      A    C
ATOM   1331  O    GLY A 210       9.513  21.738  60.431  1.00 42.37      A    O
ATOM   1332  N    GLU A 211      11.149  21.716  58.902  1.00 51.86      A    N
ATOM   1333  CA   GLU A 211      12.191  21.575  59.912  1.00 51.86      A    C
ATOM   1334  CB   GLU A 211      13.426  20.930  59.295  1.00 63.27      A    C
ATOM   1335  CG   GLU A 211      13.274  19.428  59.160  1.00 63.27      A    C
ATOM   1336  CD   GLU A 211      14.371  18.799  58.338  1.00 63.27      A    C
ATOM   1337  OE1  GLU A 211      15.557  19.142  58.551  1.00 63.27      A    O
ATOM   1338  OE2  GLU A 211      14.037  17.953  57.482  1.00 63.27      A    O
ATOM   1339  C    GLU A 211      12.543  22.925  60.524  1.00 51.86      A    C
ATOM   1340  O    GLU A 211      12.675  23.925  59.812  1.00 51.86      A    O
ATOM   1341  N    PRO A 212      12.675  22.977  61.860  1.00 41.65      A    N
ATOM   1342  CD   PRO A 212      12.238  21.968  62.842  1.00 22.84      A    C
ATOM   1343  CA   PRO A 212      13.012  24.236  62.528  1.00 41.65      A    C
ATOM   1344  CB   PRO A 212      12.444  24.036  63.931  1.00 22.84      A    C
ATOM   1345  CG   PRO A 212      12.660  22.585  64.160  1.00 22.84      A    C
ATOM   1346  C    PRO A 212      14.496  24.543  62.523  1.00 41.65      A    C
ATOM   1347  O    PRO A 212      15.326  23.641  62.565  1.00 41.65      A    O
ATOM   1348  N    ASN A 213      14.818  25.830  62.464  1.00 28.49      A    N
ATOM   1349  CA   ASN A 213      16.204  26.285  62.452  1.00 28.49      A    C
ATOM   1350  CB   ASN A 213      16.550  26.787  61.068  1.00 27.65      A    C
ATOM   1351  CG   ASN A 213      16.254  25.766  60.030  1.00 27.65      A    C
ATOM   1352  OD1  ASN A 213      16.914  24.737  59.964  1.00 27.65      A    O
ATOM   1353  ND2  ASN A 213      15.236  26.020  59.225  1.00 27.65      A    N
ATOM   1354  C    ASN A 213      16.378  27.379  63.490  1.00 28.49      A    C
ATOM   1355  O    ASN A 213      15.443  28.119  63.790  1.00 28.49      A    O
ATOM   1356  N    VAL A 214      17.581  27.471  64.044  1.00 24.30      A    N
ATOM   1357  CA   VAL A 214      17.862  28.460  65.073  1.00 24.30      A    C
ATOM   1358  CB   VAL A 214      19.288  28.268  65.629  1.00 19.14      A    C
ATOM   1359  CG1  VAL A 214      19.382  26.930  66.325  1.00 19.14      A    C
ATOM   1360  CG2  VAL A 214      20.307  28.339  64.501  1.00 19.14      A    C
ATOM   1361  C    VAL A 214      17.682  29.886  64.564  1.00 24.30      A    C
ATOM   1362  O    VAL A 214      17.854  30.155  63.385  1.00 24.30      A    O
ATOM   1363  N    SER A 215      17.337  30.802  65.460  1.00 19.39      A    N
ATOM   1364  CA   SER A 215      17.121  32.185  65.057  1.00 19.39      A    C
ATOM   1365  CB   SER A 215      15.758  32.677  65.557  1.00 32.97      A    C
ATOM   1366  OG   SER A 215      15.610  32.445  66.944  1.00 32.97      A    O
ATOM   1367  C    SER A 215      18.204  33.143  65.511  1.00 19.39      A    C
ATOM   1368  O    SER A 215      18.102  34.334  65.298  1.00 19.39      A    O
ATOM   1369  N    TYR A 216      19.245  32.627  66.136  1.00 30.90      A    N
ATOM   1370  CA   TYR A 216      20.333  33.486  66.584  1.00 30.90      A    C
ATOM   1371  CB   TYR A 216      20.761  33.077  67.995  1.00 36.20      A    C
ATOM   1372  CG   TYR A 216      21.058  31.607  68.130  1.00 36.20      A    C
ATOM   1373  CD1  TYR A 216      22.220  31.056  67.594  1.00 36.20      A    C
ATOM   1374  CE1  TYR A 216      22.510  29.712  67.742  1.00 36.20      A    C
ATOM   1375  CD2  TYR A 216      20.191  30.769  68.812  1.00 36.20      A    C
ATOM   1376  CE2  TYR A 216      20.471  29.423  68.967  1.00 36.20      A    C
ATOM   1377  CZ   TYR A 216      21.632  28.901  68.435  1.00 36.20      A    C
```

FIG. 6-24

```
ATOM   1378  OH   TYR A 216      21.930  27.571  68.628  1.00 36.20      A    O
ATOM   1379  C    TYR A 216      21.510  33.387  65.610  1.00 30.90      A    C
ATOM   1380  O    TYR A 216      22.675  33.480  66.007  1.00 30.90      A    O
ATOM   1381  N    ILE A 217      21.184  33.242  64.328  1.00 33.95      A    N
ATOM   1382  CA   ILE A 217      22.180  33.074  63.286  1.00 33.95      A    C
ATOM   1383  CB   ILE A 217      21.665  32.147  62.172  1.00 23.35      A    C
ATOM   1384  CG2  ILE A 217      22.060  30.711  62.471  1.00 23.35      A    C
ATOM   1385  CG1  ILE A 217      20.171  32.388  61.965  1.00 23.35      A    C
ATOM   1386  CD1  ILE A 217      19.745  32.263  60.548  1.00 23.35      A    C
ATOM   1387  C    ILE A 217      22.779  34.271  62.564  1.00 33.95      A    C
ATOM   1388  O    ILE A 217      23.972  34.250  62.222  1.00 33.95      A    O
ATOM   1389  N    CYS A 218      21.986  35.301  62.307  1.00 27.47      A    N
ATOM   1390  CA   CYS A 218      22.515  36.417  61.537  1.00 27.47      A    C
ATOM   1391  CB   CYS A 218      21.365  37.062  60.766  1.00 21.91      A    C
ATOM   1392  SG   CYS A 218      21.878  38.063  59.388  1.00 21.91      A    S
ATOM   1393  C    CYS A 218      23.279  37.463  62.334  1.00 27.47      A    C
ATOM   1394  O    CYS A 218      23.194  37.497  63.552  1.00 27.47      A    O
ATOM   1395  N    SER A 219      24.029  38.311  61.643  1.00 17.71      A    N
ATOM   1396  CA   SER A 219      24.804  39.358  62.296  1.00 17.71      A    C
ATOM   1397  CB   SER A 219      26.111  39.599  61.537  1.00 37.76      A    C
ATOM   1398  OG   SER A 219      26.946  38.451  61.592  1.00 37.76      A    O
ATOM   1399  C    SER A 219      24.031  40.664  62.422  1.00 17.71      A    C
ATOM   1400  O    SER A 219      23.157  40.962  61.619  1.00 17.71      A    O
ATOM   1401  N    ARG A 220      24.367  41.436  63.446  1.00 26.36      A    N
ATOM   1402  CA   ARG A 220      23.735  42.724  63.721  1.00 26.36      A    C
ATOM   1403  CB   ARG A 220      24.453  43.358  64.918  1.00 47.85      A    C
ATOM   1404  CG   ARG A 220      24.362  44.868  65.075  1.00 47.85      A    C
ATOM   1405  CD   ARG A 220      24.662  45.241  66.532  1.00 47.85      A    C
ATOM   1406  NE   ARG A 220      25.169  46.600  66.722  1.00 47.85      A    N
ATOM   1407  CZ   ARG A 220      26.401  47.002  66.408  1.00 47.85      A    C
ATOM   1408  NH1  ARG A 220      27.284  46.157  65.869  1.00 47.85      A    N
ATOM   1409  NH2  ARG A 220      26.764  48.253  66.664  1.00 47.85      A    N
ATOM   1410  C    ARG A 220      23.756  43.644  62.502  1.00 26.36      A    C
ATOM   1411  O    ARG A 220      24.728  43.672  61.763  1.00 26.36      A    O
ATOM   1412  N    TYR A 221      22.677  44.393  62.303  1.00 19.12      A    N
ATOM   1413  CA   TYR A 221      22.532  45.310  61.172  1.00 19.12      A    C
ATOM   1414  CB   TYR A 221      23.859  45.936  60.746  1.00 43.64      A    C
ATOM   1415  CG   TYR A 221      24.521  46.861  61.737  1.00 43.64      A    C
ATOM   1416  CD1  TYR A 221      23.907  47.208  62.943  1.00 43.64      A    C
ATOM   1417  CE1  TYR A 221      24.560  48.038  63.867  1.00 43.64      A    C
ATOM   1418  CD2  TYR A 221      25.796  47.372  61.471  1.00 43.64      A    C
ATOM   1419  CE2  TYR A 221      26.453  48.197  62.371  1.00 43.64      A    C
ATOM   1420  CZ   TYR A 221      25.838  48.529  63.567  1.00 43.64      A    C
ATOM   1421  OH   TYR A 221      26.515  49.357  64.444  1.00 43.64      A    O
ATOM   1422  C    TYR A 221      21.947  44.633  59.938  1.00 19.12      A    C
ATOM   1423  O    TYR A 221      21.317  45.286  59.111  1.00 19.12      A    O
ATOM   1424  N    TYR A 222      22.137  43.325  59.814  1.00 21.81      A    N
ATOM   1425  CA   TYR A 222      21.668  42.622  58.624  1.00 21.81      A    C
ATOM   1426  CB   TYR A 222      22.873  41.976  57.945  1.00 22.08      A    C
ATOM   1427  CG   TYR A 222      24.000  42.953  57.800  1.00 22.08      A    C
ATOM   1428  CD1  TYR A 222      23.941  43.973  56.852  1.00 22.08      A    C
ATOM   1429  CE1  TYR A 222      24.938  44.930  56.763  1.00 22.08      A    C
ATOM   1430  CD2  TYR A 222      25.090  42.911  58.658  1.00 22.08      A    C
ATOM   1431  CE2  TYR A 222      26.101  43.870  58.577  1.00 22.08      A    C
ATOM   1432  CZ   TYR A 222      26.017  44.878  57.627  1.00 22.08      A    C
ATOM   1433  OH   TYR A 222      27.003  45.832  57.559  1.00 22.08      A    O
ATOM   1434  C    TYR A 222      20.573  41.591  58.808  1.00 21.81      A    C
ATOM   1435  O    TYR A 222      20.057  41.048  57.832  1.00 21.81      A    O
ATOM   1436  N    ARG A 223      20.215  41.336  60.056  1.00 20.07      A    N
ATOM   1437  CA   ARG A 223      19.198  40.353  60.379  1.00 20.07      A    C
```

FIG. 6-25

| | | | | | | | | | | | |
|---|---|---|---|---|---|---|---|---|---|---|---|
| ATOM | 1438 | CB | ARG | A | 223 | 19.194 | 40.081 | 61.875 | 1.00 | 32.25 | A C |
| ATOM | 1439 | CG | ARG | A | 223 | 20.575 | 39.876 | 62.450 | 1.00 | 32.25 | A C |
| ATOM | 1440 | CD | ARG | A | 223 | 20.486 | 39.687 | 63.927 | 1.00 | 32.25 | A C |
| ATOM | 1441 | NE | ARG | A | 223 | 19.861 | 38.412 | 64.231 | 1.00 | 32.25 | A N |
| ATOM | 1442 | CZ | ARG | A | 223 | 19.151 | 38.187 | 65.323 | 1.00 | 32.25 | A C |
| ATOM | 1443 | NH1 | ARG | A | 223 | 18.982 | 39.163 | 66.208 | 1.00 | 32.25 | A N |
| ATOM | 1444 | NH2 | ARG | A | 223 | 18.613 | 36.998 | 65.524 | 1.00 | 32.25 | A N |
| ATOM | 1445 | C | ARG | A | 223 | 17.815 | 40.774 | 59.935 | 1.00 | 20.07 | A C |
| ATOM | 1446 | O | ARG | A | 223 | 17.406 | 41.922 | 60.116 | 1.00 | 20.07 | A O |
| ATOM | 1447 | N | ALA | A | 224 | 17.099 | 39.822 | 59.349 | 1.00 | 39.74 | A N |
| ATOM | 1448 | CA | ALA | A | 224 | 15.748 | 40.055 | 58.859 | 1.00 | 39.74 | A C |
| ATOM | 1449 | CB | ALA | A | 224 | 15.332 | 38.935 | 57.930 | 1.00 | 38.16 | A C |
| ATOM | 1450 | C | ALA | A | 224 | 14.789 | 40.158 | 60.030 | 1.00 | 39.74 | A C |
| ATOM | 1451 | O | ALA | A | 224 | 14.984 | 39.519 | 61.054 | 1.00 | 39.74 | A O |
| ATOM | 1452 | N | PRO | A | 225 | 13.727 | 40.953 | 59.882 | 1.00 | 29.06 | A N |
| ATOM | 1453 | CD | PRO | A | 225 | 13.321 | 41.572 | 58.610 | 1.00 | 31.89 | A C |
| ATOM | 1454 | CA | PRO | A | 225 | 12.709 | 41.174 | 60.918 | 1.00 | 29.06 | A C |
| ATOM | 1455 | CB | PRO | A | 225 | 11.588 | 41.872 | 60.152 | 1.00 | 31.89 | A C |
| ATOM | 1456 | CG | PRO | A | 225 | 12.321 | 42.588 | 59.061 | 1.00 | 31.89 | A C |
| ATOM | 1457 | C | PRO | A | 225 | 12.216 | 39.919 | 61.626 | 1.00 | 29.06 | A C |
| ATOM | 1458 | O | PRO | A | 225 | 11.963 | 39.937 | 62.826 | 1.00 | 29.06 | A O |
| ATOM | 1459 | N | GLU | A | 226 | 12.074 | 38.834 | 60.875 | 1.00 | 29.04 | A N |
| ATOM | 1460 | CA | GLU | A | 226 | 11.601 | 37.581 | 61.436 | 1.00 | 29.04 | A C |
| ATOM | 1461 | CB | GLU | A | 226 | 11.171 | 36.643 | 60.313 | 1.00 | 30.42 | A C |
| ATOM | 1462 | CG | GLU | A | 226 | 10.811 | 37.354 | 59.003 | 1.00 | 30.42 | A C |
| ATOM | 1463 | CD | GLU | A | 226 | 11.991 | 37.475 | 58.042 | 1.00 | 30.42 | A C |
| ATOM | 1464 | OE1 | GLU | A | 226 | 12.562 | 36.435 | 57.649 | 1.00 | 30.42 | A O |
| ATOM | 1465 | OE2 | GLU | A | 226 | 12.344 | 38.609 | 57.674 | 1.00 | 30.42 | A O |
| ATOM | 1466 | C | GLU | A | 226 | 12.675 | 36.911 | 62.287 | 1.00 | 29.04 | A C |
| ATOM | 1467 | O | GLU | A | 226 | 12.380 | 36.061 | 63.123 | 1.00 | 29.04 | A O |
| ATOM | 1468 | N | LEU | A | 227 | 13.929 | 37.270 | 62.071 | 1.00 | 30.09 | A N |
| ATOM | 1469 | CA | LEU | A | 227 | 14.984 | 36.676 | 62.873 | 1.00 | 30.09 | A C |
| ATOM | 1470 | CB | LEU | A | 227 | 16.335 | 36.770 | 62.152 | 1.00 | 14.48 | A C |
| ATOM | 1471 | CG | LEU | A | 227 | 16.511 | 35.843 | 60.939 | 1.00 | 14.48 | A C |
| ATOM | 1472 | CD1 | LEU | A | 227 | 17.902 | 36.054 | 60.366 | 1.00 | 14.48 | A C |
| ATOM | 1473 | CD2 | LEU | A | 227 | 16.317 | 34.379 | 61.320 | 1.00 | 14.48 | A C |
| ATOM | 1474 | C | LEU | A | 227 | 15.028 | 37.414 | 64.202 | 1.00 | 30.09 | A C |
| ATOM | 1475 | O | LEU | A | 227 | 15.310 | 36.829 | 65.244 | 1.00 | 30.09 | A O |
| ATOM | 1476 | N | ILE | A | 228 | 14.722 | 38.702 | 64.158 | 1.00 | 22.58 | A N |
| ATOM | 1477 | CA | ILE | A | 228 | 14.727 | 39.523 | 65.352 | 1.00 | 22.58 | A C |
| ATOM | 1478 | CB | ILE | A | 228 | 14.562 | 41.019 | 64.990 | 1.00 | 17.70 | A C |
| ATOM | 1479 | CG2 | ILE | A | 228 | 14.296 | 41.837 | 66.238 | 1.00 | 17.70 | A C |
| ATOM | 1480 | CG1 | ILE | A | 228 | 15.811 | 41.519 | 64.255 | 1.00 | 17.70 | A C |
| ATOM | 1481 | CD1 | ILE | A | 228 | 15.633 | 42.891 | 63.602 | 1.00 | 17.70 | A C |
| ATOM | 1482 | C | ILE | A | 228 | 13.569 | 39.073 | 66.220 | 1.00 | 22.58 | A C |
| ATOM | 1483 | O | ILE | A | 228 | 13.646 | 39.102 | 67.442 | 1.00 | 22.58 | A O |
| ATOM | 1484 | N | PHE | A | 229 | 12.497 | 38.641 | 65.571 | 1.00 | 34.78 | A N |
| ATOM | 1485 | CA | PHE | A | 229 | 11.308 | 38.179 | 66.271 | 1.00 | 34.78 | A C |
| ATOM | 1486 | CB | PHE | A | 229 | 10.072 | 38.324 | 65.382 | 1.00 | 23.42 | A C |
| ATOM | 1487 | CG | PHE | A | 229 | 9.541 | 39.723 | 65.298 | 1.00 | 23.42 | A C |
| ATOM | 1488 | CD1 | PHE | A | 229 | 9.099 | 40.385 | 66.441 | 1.00 | 23.42 | A C |
| ATOM | 1489 | CD2 | PHE | A | 229 | 9.464 | 40.376 | 64.075 | 1.00 | 23.42 | A C |
| ATOM | 1490 | CE1 | PHE | A | 229 | 8.589 | 41.680 | 66.365 | 1.00 | 23.42 | A C |
| ATOM | 1491 | CE2 | PHE | A | 229 | 8.959 | 41.670 | 63.989 | 1.00 | 23.42 | A C |
| ATOM | 1492 | CZ | PHE | A | 229 | 8.519 | 42.323 | 65.133 | 1.00 | 23.42 | A C |
| ATOM | 1493 | C | PHE | A | 229 | 11.425 | 36.729 | 66.706 | 1.00 | 34.78 | A C |
| ATOM | 1494 | O | PHE | A | 229 | 10.438 | 36.138 | 67.113 | 1.00 | 34.78 | A O |
| ATOM | 1495 | N | GLY | A | 230 | 12.620 | 36.157 | 66.596 | 1.00 | 32.23 | A N |
| ATOM | 1496 | CA | GLY | A | 230 | 12.843 | 34.783 | 67.016 | 1.00 | 32.23 | A C |
| ATOM | 1497 | C | GLY | A | 230 | 12.188 | 33.680 | 66.205 | 1.00 | 32.23 | A C |

FIG. 6-26

```
ATOM   1498  O    GLY A 230      12.112  32.540  66.660  1.00 32.23      A  O
ATOM   1499  N    ALA A 231      11.714  34.004  65.006  1.00 28.55      A  N
ATOM   1500  CA   ALA A 231      11.083  32.997  64.154  1.00 28.55      A  C
ATOM   1501  CB   ALA A 231      10.648  33.619  62.834  1.00  8.54      A  C
ATOM   1502  C    ALA A 231      12.071  31.870  63.892  1.00 28.55      A  C
ATOM   1503  O    ALA A 231      13.265  32.108  63.750  1.00 28.55      A  O
ATOM   1504  N    THR A 232      11.584  30.637  63.842  1.00 39.05      A  N
ATOM   1505  CA   THR A 232      12.469  29.509  63.565  1.00 39.05      A  C
ATOM   1506  CB   THR A 232      12.511  28.526  64.733  1.00 32.41      A  C
ATOM   1507  OG1  THR A 232      11.176  28.198  65.112  1.00 32.41      A  O
ATOM   1508  CG2  THR A 232      13.240  29.127  65.914  1.00 32.41      A  C
ATOM   1509  C    THR A 232      12.012  28.761  62.309  1.00 39.05      A  C
ATOM   1510  O    THR A 232      12.594  27.735  61.926  1.00 39.05      A  O
ATOM   1511  N    ASP A 233      10.974  29.291  61.667  1.00 29.68      A  N
ATOM   1512  CA   ASP A 233      10.446  28.699  60.444  1.00 29.68      A  C
ATOM   1513  CB   ASP A 233       8.940  28.463  60.587  1.00 30.27      A  C
ATOM   1514  CG   ASP A 233       8.145  29.752  60.554  1.00 30.27      A  C
ATOM   1515  OD1  ASP A 233       8.537  30.711  61.247  1.00 30.27      A  O
ATOM   1516  OD2  ASP A 233       7.126  29.812  59.839  1.00 30.27      A  O
ATOM   1517  C    ASP A 233      10.733  29.624  59.256  1.00 29.68      A  C
ATOM   1518  O    ASP A 233       9.914  29.778  58.344  1.00 29.68      A  O
ATOM   1519  N    TYR A 234      11.910  30.237  59.276  1.00 31.59      A  N
ATOM   1520  CA   TYR A 234      12.310  31.155  58.216  1.00 31.59      A  C
ATOM   1521  CB   TYR A 234      13.355  32.153  58.740  1.00 11.36      A  C
ATOM   1522  CG   TYR A 234      14.615  31.511  59.295  1.00 11.36      A  C
ATOM   1523  CD1  TYR A 234      15.626  31.059  58.449  1.00 11.36      A  C
ATOM   1524  CE1  TYR A 234      16.785  30.477  58.963  1.00 11.36      A  C
ATOM   1525  CD2  TYR A 234      14.796  31.360  60.673  1.00 11.36      A  C
ATOM   1526  CE2  TYR A 234      15.950  30.777  61.190  1.00 11.36      A  C
ATOM   1527  CZ   TYR A 234      16.937  30.339  60.329  1.00 11.36      A  C
ATOM   1528  OH   TYR A 234      18.076  29.757  60.817  1.00 11.36      A  O
ATOM   1529  C    TYR A 234      12.849  30.438  56.986  1.00 31.59      A  C
ATOM   1530  O    TYR A 234      13.284  29.290  57.048  1.00 31.59      A  O
ATOM   1531  N    THR A 235      12.821  31.145  55.866  1.00 32.65      A  N
ATOM   1532  CA   THR A 235      13.295  30.609  54.605  1.00 32.65      A  C
ATOM   1533  CB   THR A 235      12.183  30.633  53.565  1.00 33.38      A  C
ATOM   1534  OG1  THR A 235      11.831  31.990  53.287  1.00 33.38      A  O
ATOM   1535  CG2  THR A 235      10.960  29.912  54.089  1.00 33.38      A  C
ATOM   1536  C    THR A 235      14.466  31.444  54.101  1.00 32.65      A  C
ATOM   1537  O    THR A 235      14.894  32.385  54.757  1.00 32.65      A  O
ATOM   1538  N    SER A 236      14.971  31.095  52.928  1.00 23.70      A  N
ATOM   1539  CA   SER A 236      16.098  31.788  52.333  1.00 23.70      A  C
ATOM   1540  CB   SER A 236      16.423  31.149  50.987  1.00 20.73      A  C
ATOM   1541  OG   SER A 236      16.789  29.793  51.138  1.00 20.73      A  O
ATOM   1542  C    SER A 236      15.880  33.283  52.148  1.00 23.70      A  C
ATOM   1543  O    SER A 236      16.815  34.019  51.834  1.00 23.70      A  O
ATOM   1544  N    SER A 237      14.647  33.734  52.331  1.00 21.91      A  N
ATOM   1545  CA   SER A 237      14.347  35.141  52.169  1.00 21.91      A  C
ATOM   1546  CB   SER A 237      12.890  35.416  52.500  1.00 44.41      A  C
ATOM   1547  OG   SER A 237      12.144  34.212  52.532  1.00 44.41      A  O
ATOM   1548  C    SER A 237      15.232  35.973  53.073  1.00 21.91      A  C
ATOM   1549  O    SER A 237      15.502  37.132  52.761  1.00 21.91      A  O
ATOM   1550  N    ILE A 238      15.688  35.392  54.186  1.00 15.47      A  N
ATOM   1551  CA   ILE A 238      16.536  36.129  55.115  1.00 15.47      A  C
ATOM   1552  CB   ILE A 238      16.938  35.289  56.353  1.00 19.37      A  C
ATOM   1553  CG2  ILE A 238      15.702  34.868  57.119  1.00 19.37      A  C
ATOM   1554  CG1  ILE A 238      17.783  34.091  55.936  1.00 19.37      A  C
ATOM   1555  CD1  ILE A 238      18.383  33.352  57.111  1.00 19.37      A  C
ATOM   1556  C    ILE A 238      17.792  36.636  54.434  1.00 15.47      A  C
ATOM   1557  O    ILE A 238      18.266  37.726  54.732  1.00 15.47      A  O
```

FIG. 6-27

```
ATOM   1558  N    ASP A 239      18.313  35.842  53.507  1.00 27.65      A  N
ATOM   1559  CA   ASP A 239      19.503  36.208  52.756  1.00 27.65      A  C
ATOM   1560  CB   ASP A 239      19.974  35.035  51.902  1.00 25.40      A  C
ATOM   1561  CG   ASP A 239      20.830  34.060  52.669  1.00 25.40      A  C
ATOM   1562  OD1  ASP A 239      21.003  34.235  53.889  1.00 25.40      A  O
ATOM   1563  OD2  ASP A 239      21.339  33.110  52.052  1.00 25.40      A  O
ATOM   1564  C    ASP A 239      19.185  37.382  51.854  1.00 27.65      A  C
ATOM   1565  O    ASP A 239      20.022  38.253  51.655  1.00 27.65      A  O
ATOM   1566  N    VAL A 240      17.975  37.405  51.306  1.00 27.60      A  N
ATOM   1567  CA   VAL A 240      17.582  38.486  50.413  1.00 27.60      A  C
ATOM   1568  CB   VAL A 240      16.252  38.162  49.675  1.00 24.32      A  C
ATOM   1569  CG1  VAL A 240      15.867  39.315  48.736  1.00 24.32      A  C
ATOM   1570  CG2  VAL A 240      16.413  36.860  48.876  1.00 24.32      A  C
ATOM   1571  C    VAL A 240      17.445  39.803  51.149  1.00 27.60      A  C
ATOM   1572  O    VAL A 240      17.668  40.867  50.572  1.00 27.60      A  O
ATOM   1573  N    TRP A 241      17.083  39.722  52.426  1.00 20.61      A  N
ATOM   1574  CA   TRP A 241      16.924  40.903  53.262  1.00 20.61      A  C
ATOM   1575  CB   TRP A 241      16.156  40.540  54.533  1.00 22.37      A  C
ATOM   1576  CG   TRP A 241      16.088  41.646  55.553  1.00 22.37      A  C
ATOM   1577  CD2  TRP A 241      15.029  42.599  55.702  1.00 22.37      A  C
ATOM   1578  CE2  TRP A 241      15.419  43.463  56.757  1.00 22.37      A  C
ATOM   1579  CE3  TRP A 241      13.773  42.740  55.123  1.00 22.37      A  C
ATOM   1580  CD1  TRP A 241      17.054  42.000  56.445  1.00 22.37      A  C
ATOM   1581  NE1  TRP A 241      16.659  43.101  57.158  1.00 22.37      A  N
ATOM   1582  CZ2  TRP A 241      14.612  44.545  57.149  1.00 22.37      A  C
ATOM   1583  CZ3  TRP A 241      12.978  43.808  55.522  1.00 22.37      A  C
ATOM   1584  CH2  TRP A 241      13.387  44.671  56.560  1.00 22.37      A  C
ATOM   1585  C    TRP A 241      18.297  41.447  53.606  1.00 20.61      A  C
ATOM   1586  O    TRP A 241      18.552  42.641  53.486  1.00 20.61      A  O
ATOM   1587  N    SER A 242      19.181  40.555  54.024  1.00 24.28      A  N
ATOM   1588  CA   SER A 242      20.528  40.942  54.385  1.00 24.28      A  C
ATOM   1589  CB   SER A 242      21.281  39.750  54.968  1.00 51.96      A  C
ATOM   1590  OG   SER A 242      21.367  38.719  54.010  1.00 51.96      A  O
ATOM   1591  C    SER A 242      21.258  41.500  53.177  1.00 24.28      A  C
ATOM   1592  O    SER A 242      22.085  42.395  53.307  1.00 24.28      A  O
ATOM   1593  N    ALA A 243      20.935  40.979  52.000  1.00 27.27      A  N
ATOM   1594  CA   ALA A 243      21.569  41.436  50.773  1.00 27.27      A  C
ATOM   1595  CB   ALA A 243      21.195  40.537  49.615  1.00 19.62      A  C
ATOM   1596  C    ALA A 243      21.098  42.853  50.528  1.00 27.27      A  C
ATOM   1597  O    ALA A 243      21.883  43.725  50.144  1.00 27.27      A  O
ATOM   1598  N    GLY A 244      19.813  43.080  50.779  1.00 23.34      A  N
ATOM   1599  CA   GLY A 244      19.237  44.397  50.589  1.00 23.34      A  C
ATOM   1600  C    GLY A 244      19.853  45.415  51.523  1.00 23.34      A  C
ATOM   1601  O    GLY A 244      19.968  46.587  51.182  1.00 23.34      A  O
ATOM   1602  N    CYS A 245      20.237  44.970  52.713  1.00 28.06      A  N
ATOM   1603  CA   CYS A 245      20.859  45.851  53.692  1.00 28.06      A  C
ATOM   1604  CB   CYS A 245      20.998  45.139  55.030  1.00 18.34      A  C
ATOM   1605  SG   CYS A 245      19.452  44.946  55.870  1.00 18.34      A  S
ATOM   1606  C    CYS A 245      22.230  46.276  53.188  1.00 28.06      A  C
ATOM   1607  O    CYS A 245      22.715  47.354  53.511  1.00 28.06      A  O
ATOM   1608  N    VAL A 246      22.860  45.420  52.399  1.00 18.53      A  N
ATOM   1609  CA   VAL A 246      24.156  45.756  51.844  1.00 18.53      A  C
ATOM   1610  CB   VAL A 246      24.866  44.517  51.315  1.00 28.80      A  C
ATOM   1611  CG1  VAL A 246      26.152  44.929  50.565  1.00 28.80      A  C
ATOM   1612  CG2  VAL A 246      25.178  43.583  52.489  1.00 28.80      A  C
ATOM   1613  C    VAL A 246      23.993  46.766  50.709  1.00 18.53      A  C
ATOM   1614  O    VAL A 246      24.771  47.707  50.586  1.00 18.53      A  O
ATOM   1615  N    LEU A 247      22.980  46.574  49.883  1.00 15.05      A  N
ATOM   1616  CA   LEU A 247      22.738  47.501  48.799  1.00 15.05      A  C
ATOM   1617  CB   LEU A 247      21.523  47.059  47.991  1.00 23.78      A  C
```

FIG. 6-28

| ATOM | 1618 | CG | LEU | A | 247 | 21.196 | 47.935 | 46.787 | 1.00 | 23.78 | A | C |
|---|---|---|---|---|---|---|---|---|---|---|---|---|
| ATOM | 1619 | CD1 | LEU | A | 247 | 22.345 | 47.897 | 45.797 | 1.00 | 23.78 | A | C |
| ATOM | 1620 | CD2 | LEU | A | 247 | 19.907 | 47.457 | 46.148 | 1.00 | 23.78 | A | C |
| ATOM | 1621 | C | LEU | A | 247 | 22.484 | 48.883 | 49.389 | 1.00 | 15.05 | A | C |
| ATOM | 1622 | O | LEU | A | 247 | 23.106 | 49.876 | 49.005 | 1.00 | 15.05 | A | O |
| ATOM | 1623 | N | ALA | A | 248 | 21.560 | 48.938 | 50.338 | 1.00 | 29.33 | A | N |
| ATOM | 1624 | CA | ALA | A | 248 | 21.208 | 50.189 | 50.976 | 1.00 | 29.33 | A | C |
| ATOM | 1625 | CB | ALA | A | 248 | 20.056 | 49.977 | 51.934 | 1.00 | 29.28 | A | C |
| ATOM | 1626 | C | ALA | A | 248 | 22.394 | 50.798 | 51.701 | 1.00 | 29.33 | A | C |
| ATOM | 1627 | O | ALA | A | 248 | 22.507 | 52.018 | 51.763 | 1.00 | 29.33 | A | O |
| ATOM | 1628 | N | GLU | A | 249 | 23.280 | 49.966 | 52.243 | 1.00 | 23.27 | A | N |
| ATOM | 1629 | CA | GLU | A | 249 | 24.454 | 50.477 | 52.949 | 1.00 | 23.27 | A | C |
| ATOM | 1630 | CB | GLU | A | 249 | 25.086 | 49.392 | 53.836 | 1.00 | 21.28 | A | C |
| ATOM | 1631 | CG | GLU | A | 249 | 26.201 | 49.917 | 54.763 | 1.00 | 21.28 | A | C |
| ATOM | 1632 | CD | GLU | A | 249 | 26.807 | 48.848 | 55.661 | 1.00 | 21.28 | A | C |
| ATOM | 1633 | OE1 | GLU | A | 249 | 26.043 | 48.082 | 56.274 | 1.00 | 21.28 | A | O |
| ATOM | 1634 | OE2 | GLU | A | 249 | 28.046 | 48.783 | 55.770 | 1.00 | 21.28 | A | O |
| ATOM | 1635 | C | GLU | A | 249 | 25.515 | 51.011 | 52.009 | 1.00 | 23.27 | A | C |
| ATOM | 1636 | O | GLU | A | 249 | 26.317 | 51.855 | 52.395 | 1.00 | 23.27 | A | O |
| ATOM | 1637 | N | LEU | A | 250 | 25.545 | 50.518 | 50.779 | 1.00 | 29.28 | A | N |
| ATOM | 1638 | CA | LEU | A | 250 | 26.543 | 51.005 | 49.838 | 1.00 | 29.28 | A | C |
| ATOM | 1639 | CB | LEU | A | 250 | 26.853 | 49.941 | 48.786 | 1.00 | 17.65 | A | C |
| ATOM | 1640 | CG | LEU | A | 250 | 27.688 | 48.781 | 49.346 | 1.00 | 17.65 | A | C |
| ATOM | 1641 | CD1 | LEU | A | 250 | 27.984 | 47.744 | 48.268 | 1.00 | 17.65 | A | C |
| ATOM | 1642 | CD2 | LEU | A | 250 | 28.976 | 49.325 | 49.916 | 1.00 | 17.65 | A | C |
| ATOM | 1643 | C | LEU | A | 250 | 26.084 | 52.308 | 49.208 | 1.00 | 29.28 | A | C |
| ATOM | 1644 | O | LEU | A | 250 | 26.899 | 53.161 | 48.878 | 1.00 | 29.28 | A | O |
| ATOM | 1645 | N | LEU | A | 251 | 24.777 | 52.475 | 49.064 | 1.00 | 33.91 | A | N |
| ATOM | 1646 | CA | LEU | A | 251 | 24.250 | 53.706 | 48.503 | 1.00 | 33.91 | A | C |
| ATOM | 1647 | CB | LEU | A | 251 | 22.810 | 53.518 | 48.040 | 1.00 | 17.87 | A | C |
| ATOM | 1648 | CG | LEU | A | 251 | 22.586 | 52.544 | 46.893 | 1.00 | 17.87 | A | C |
| ATOM | 1649 | CD1 | LEU | A | 251 | 21.106 | 52.441 | 46.626 | 1.00 | 17.87 | A | C |
| ATOM | 1650 | CD2 | LEU | A | 251 | 23.334 | 53.003 | 45.649 | 1.00 | 17.87 | A | C |
| ATOM | 1651 | C | LEU | A | 251 | 24.291 | 54.805 | 49.556 | 1.00 | 33.91 | A | C |
| ATOM | 1652 | O | LEU | A | 251 | 24.632 | 55.948 | 49.259 | 1.00 | 33.91 | A | O |
| ATOM | 1653 | N | LEU | A | 252 | 23.960 | 54.454 | 50.791 | 1.00 | 24.63 | A | N |
| ATOM | 1654 | CA | LEU | A | 252 | 23.918 | 55.420 | 51.874 | 1.00 | 24.63 | A | C |
| ATOM | 1655 | CB | LEU | A | 252 | 23.040 | 54.877 | 53.006 | 1.00 | 51.78 | A | C |
| ATOM | 1656 | CG | LEU | A | 252 | 22.366 | 55.940 | 53.898 | 1.00 | 51.78 | A | C |
| ATOM | 1657 | CD1 | LEU | A | 252 | 21.095 | 56.435 | 53.197 | 1.00 | 51.78 | A | C |
| ATOM | 1658 | CD2 | LEU | A | 252 | 22.010 | 55.368 | 55.281 | 1.00 | 51.78 | A | C |
| ATOM | 1659 | C | LEU | A | 252 | 25.268 | 55.822 | 52.448 | 1.00 | 24.63 | A | C |
| ATOM | 1660 | O | LEU | A | 252 | 25.445 | 56.966 | 52.845 | 1.00 | 24.63 | A | O |
| ATOM | 1661 | N | GLY | A | 253 | 26.211 | 54.889 | 52.509 | 1.00 | 22.47 | A | N |
| ATOM | 1662 | CA | GLY | A | 253 | 27.516 | 55.196 | 53.065 | 1.00 | 22.47 | A | C |
| ATOM | 1663 | C | GLY | A | 253 | 27.625 | 54.797 | 54.525 | 1.00 | 22.47 | A | C |
| ATOM | 1664 | O | GLY | A | 253 | 28.633 | 55.040 | 55.187 | 1.00 | 22.47 | A | O |
| ATOM | 1665 | N | GLN | A | 254 | 26.572 | 54.173 | 55.031 | 1.00 | 20.71 | A | N |
| ATOM | 1666 | CA | GLN | A | 254 | 26.532 | 53.711 | 56.407 | 1.00 | 20.71 | A | C |
| ATOM | 1667 | CB | GLN | A | 254 | 26.332 | 54.891 | 57.350 | 1.00 | 46.21 | A | C |
| ATOM | 1668 | CG | GLN | A | 254 | 25.211 | 55.825 | 56.932 | 1.00 | 46.21 | A | C |
| ATOM | 1669 | CD | GLN | A | 254 | 24.534 | 56.458 | 58.130 | 1.00 | 46.21 | A | C |
| ATOM | 1670 | OE1 | GLN | A | 254 | 24.059 | 55.749 | 59.022 | 1.00 | 46.21 | A | O |
| ATOM | 1671 | NE2 | GLN | A | 254 | 24.480 | 57.789 | 58.163 | 1.00 | 46.21 | A | N |
| ATOM | 1672 | C | GLN | A | 254 | 25.366 | 52.738 | 56.525 | 1.00 | 20.71 | A | C |
| ATOM | 1673 | O | GLN | A | 254 | 24.488 | 52.717 | 55.676 | 1.00 | 20.71 | A | O |
| ATOM | 1674 | N | PRO | A | 255 | 25.348 | 51.915 | 57.580 | 1.00 | 15.57 | A | N |
| ATOM | 1675 | CD | PRO | A | 255 | 26.420 | 51.769 | 58.573 | 1.00 | 27.15 | A | C |
| ATOM | 1676 | CA | PRO | A | 255 | 24.295 | 50.928 | 57.828 | 1.00 | 15.57 | A | C |
| ATOM | 1677 | CB | PRO | A | 255 | 24.743 | 50.279 | 59.129 | 1.00 | 27.15 | A | C |

FIG. 6-29

```
ATOM   1678  CG   PRO A 255      26.214  50.358  59.034  1.00 27.15      A    C
ATOM   1679  C    PRO A 255      22.876  51.499  57.926  1.00 15.57      A    C
ATOM   1680  O    PRO A 255      22.600  52.391  58.721  1.00 15.57      A    O
ATOM   1681  N    ILE A 256      21.971  50.945  57.130  1.00 22.32      A    N
ATOM   1682  CA   ILE A 256      20.598  51.417  57.109  1.00 22.32      A    C
ATOM   1683  CB   ILE A 256      19.851  50.947  55.813  1.00 25.12      A    C
ATOM   1684  CG2  ILE A 256      19.696  49.436  55.777  1.00 25.12      A    C
ATOM   1685  CG1  ILE A 256      18.493  51.639  55.731  1.00 25.12      A    C
ATOM   1686  CD1  ILE A 256      17.842  51.523  54.382  1.00 25.12      A    C
ATOM   1687  C    ILE A 256      19.773  51.092  58.352  1.00 22.32      A    C
ATOM   1688  O    ILE A 256      19.025  51.949  58.815  1.00 22.32      A    O
ATOM   1689  N    PHE A 257      19.898  49.884  58.902  1.00 24.26      A    N
ATOM   1690  CA   PHE A 257      19.135  49.534  60.116  1.00 24.26      A    C
ATOM   1691  CB   PHE A 257      18.205  48.344  59.851  1.00 15.35      A    C
ATOM   1692  CG   PHE A 257      17.269  48.543  58.704  1.00 15.35      A    C
ATOM   1693  CD1  PHE A 257      16.415  49.635  58.665  1.00 15.35      A    C
ATOM   1694  CD2  PHE A 257      17.217  47.617  57.672  1.00 15.35      A    C
ATOM   1695  CE1  PHE A 257      15.522  49.807  57.616  1.00 15.35      A    C
ATOM   1696  CE2  PHE A 257      16.328  47.780  56.620  1.00 15.35      A    C
ATOM   1697  CZ   PHE A 257      15.477  48.878  56.595  1.00 15.35      A    C
ATOM   1698  C    PHE A 257      20.047  49.186  61.306  1.00 24.26      A    C
ATOM   1699  O    PHE A 257      20.075  48.052  61.774  1.00 24.26      A    O
ATOM   1700  N    PRO A 258      20.789  50.170  61.822  1.00 21.64      A    N
ATOM   1701  CD   PRO A 258      20.787  51.588  61.414  1.00 26.29      A    C
ATOM   1702  CA   PRO A 258      21.701  49.947  62.948  1.00 21.64      A    C
ATOM   1703  CB   PRO A 258      22.595  51.174  62.897  1.00 26.29      A    C
ATOM   1704  CG   PRO A 258      21.622  52.250  62.500  1.00 26.29      A    C
ATOM   1705  C    PRO A 258      21.015  49.766  64.302  1.00 21.64      A    C
ATOM   1706  O    PRO A 258      19.801  49.888  64.417  1.00 21.64      A    O
ATOM   1707  N    GLY A 259      21.807  49.474  65.322  1.00 17.78      A    N
ATOM   1708  CA   GLY A 259      21.254  49.273  66.648  1.00 17.78      A    C
ATOM   1709  C    GLY A 259      21.923  48.118  67.366  1.00 17.78      A    C
ATOM   1710  O    GLY A 259      22.204  47.080  66.759  1.00 17.78      A    O
ATOM   1711  N    ASP A 260      22.197  48.282  68.655  1.00 29.38      A    N
ATOM   1712  CA   ASP A 260      22.835  47.201  69.392  1.00 29.38      A    C
ATOM   1713  CB   ASP A 260      23.787  47.759  70.460  1.00 60.06      A    C
ATOM   1714  CG   ASP A 260      25.049  48.368  69.851  1.00 60.06      A    C
ATOM   1715  OD1  ASP A 260      25.214  48.271  68.613  1.00 60.06      A    O
ATOM   1716  OD2  ASP A 260      25.879  48.939  70.604  1.00 60.06      A    O
ATOM   1717  C    ASP A 260      21.818  46.268  70.026  1.00 29.38      A    C
ATOM   1718  O    ASP A 260      22.173  45.316  70.707  1.00 29.38      A    O
ATOM   1719  N    SER A 261      20.545  46.538  69.792  1.00 25.76      A    N
ATOM   1720  CA   SER A 261      19.504  45.696  70.342  1.00 25.76      A    C
ATOM   1721  CB   SER A 261      18.829  46.375  71.533  1.00 22.94      A    C
ATOM   1722  OG   SER A 261      17.897  47.344  71.092  1.00 22.94      A    O
ATOM   1723  C    SER A 261      18.477  45.462  69.252  1.00 25.76      A    C
ATOM   1724  O    SER A 261      18.369  46.244  68.315  1.00 25.76      A    O
ATOM   1725  N    GLY A 262      17.731  44.374  69.378  1.00 27.23      A    N
ATOM   1726  CA   GLY A 262      16.702  44.086  68.405  1.00 27.23      A    C
ATOM   1727  C    GLY A 262      15.694  45.210  68.464  1.00 27.23      A    C
ATOM   1728  O    GLY A 262      15.196  45.664  67.447  1.00 27.23      A    O
ATOM   1729  N    VAL A 263      15.390  45.670  69.665  1.00 26.78      A    N
ATOM   1730  CA   VAL A 263      14.452  46.759  69.799  1.00 26.78      A    C
ATOM   1731  CB   VAL A 263      14.223  47.119  71.290  1.00 33.29      A    C
ATOM   1732  CG1  VAL A 263      13.568  48.480  71.416  1.00 33.29      A    C
ATOM   1733  CG2  VAL A 263      13.330  46.082  71.925  1.00 33.29      A    C
ATOM   1734  C    VAL A 263      14.956  47.982  69.040  1.00 26.78      A    C
ATOM   1735  O    VAL A 263      14.209  48.620  68.304  1.00 26.78      A    O
ATOM   1736  N    ASP A 264      16.225  48.320  69.209  1.00 27.87      A    N
ATOM   1737  CA   ASP A 264      16.726  49.474  68.496  1.00 27.87      A    C
```

FIG. 6-30

```
ATOM   1738  CB   ASP A 264      18.124  49.850  68.999  1.00 26.70      A    C
ATOM   1739  CG   ASP A 264      18.066  50.551  70.347  1.00 26.70      A    C
ATOM   1740  OD1  ASP A 264      19.041  51.227  70.751  1.00 26.70      A    O
ATOM   1741  OD2  ASP A 264      17.012  50.410  71.002  1.00 26.70      A    O
ATOM   1742  C    ASP A 264      16.688  49.245  66.988  1.00 27.87      A    C
ATOM   1743  O    ASP A 264      16.309  50.141  66.231  1.00 27.87      A    O
ATOM   1744  N    GLN A 265      17.045  48.037  66.564  1.00 27.08      A    N
ATOM   1745  CA   GLN A 265      17.046  47.692  65.145  1.00 27.08      A    C
ATOM   1746  CB   GLN A 265      17.551  46.262  64.946  1.00 30.70      A    C
ATOM   1747  CG   GLN A 265      19.038  46.132  64.815  1.00 30.70      A    C
ATOM   1748  CD   GLN A 265      19.547  44.806  65.349  1.00 30.70      A    C
ATOM   1749  OE1  GLN A 265      18.908  43.764  65.182  1.00 30.70      A    O
ATOM   1750  NE2  GLN A 265      20.710  44.836  65.987  1.00 30.70      A    N
ATOM   1751  C    GLN A 265      15.632  47.812  64.588  1.00 27.08      A    C
ATOM   1752  O    GLN A 265      15.414  48.373  63.517  1.00 27.08      A    O
ATOM   1753  N    LEU A 266      14.671  47.279  65.325  1.00 20.92      A    N
ATOM   1754  CA   LEU A 266      13.285  47.337  64.906  1.00 20.92      A    C
ATOM   1755  CB   LEU A 266      12.412  46.584  65.898  1.00 21.87      A    C
ATOM   1756  CG   LEU A 266      11.795  45.304  65.368  1.00 21.87      A    C
ATOM   1757  CD1  LEU A 266      12.796  44.547  64.541  1.00 21.87      A    C
ATOM   1758  CD2  LEU A 266      11.329  44.486  66.537  1.00 21.87      A    C
ATOM   1759  C    LEU A 266      12.745  48.762  64.739  1.00 20.92      A    C
ATOM   1760  O    LEU A 266      11.898  49.010  63.893  1.00 20.92      A    O
ATOM   1761  N    VAL A 267      13.216  49.696  65.554  1.00 23.75      A    N
ATOM   1762  CA   VAL A 267      12.757  51.072  65.439  1.00 23.75      A    C
ATOM   1763  CB   VAL A 267      13.313  51.950  66.575  1.00 33.02      A    C
ATOM   1764  CG1  VAL A 267      13.234  53.417  66.184  1.00 33.02      A    C
ATOM   1765  CG2  VAL A 267      12.534  51.703  67.855  1.00 33.02      A    C
ATOM   1766  C    VAL A 267      13.257  51.642  64.116  1.00 23.75      A    C
ATOM   1767  O    VAL A 267      12.508  52.258  63.360  1.00 23.75      A    O
ATOM   1768  N    GLU A 268      14.543  51.436  63.860  1.00 27.05      A    N
ATOM   1769  CA   GLU A 268      15.182  51.899  62.645  1.00 27.05      A    C
ATOM   1770  CB   GLU A 268      16.640  51.447  62.639  1.00 50.90      A    C
ATOM   1771  CG   GLU A 268      17.680  52.550  62.811  1.00 50.90      A    C
ATOM   1772  CD   GLU A 268      17.217  53.675  63.725  1.00 50.90      A    C
ATOM   1773  OE1  GLU A 268      16.391  54.494  63.256  1.00 50.90      A    O
ATOM   1774  OE2  GLU A 268      17.672  53.739  64.901  1.00 50.90      A    O
ATOM   1775  C    GLU A 268      14.468  51.352  61.405  1.00 27.05      A    C
ATOM   1776  O    GLU A 268      14.274  52.072  60.427  1.00 27.05      A    O
ATOM   1777  N    ILE A 269      14.077  50.078  61.441  1.00 28.63      A    N
ATOM   1778  CA   ILE A 269      13.393  49.466  60.303  1.00 28.63      A    C
ATOM   1779  CB   ILE A 269      13.173  47.939  60.491  1.00 19.00      A    C
ATOM   1780  CG2  ILE A 269      12.276  47.395  59.375  1.00 19.00      A    C
ATOM   1781  CG1  ILE A 269      14.513  47.208  60.507  1.00 19.00      A    C
ATOM   1782  CD1  ILE A 269      14.386  45.763  60.852  1.00 19.00      A    C
ATOM   1783  C    ILE A 269      12.033  50.096  60.104  1.00 28.63      A    C
ATOM   1784  O    ILE A 269      11.671  50.445  58.987  1.00 28.63      A    O
ATOM   1785  N    ILE A 270      11.277  50.219  61.195  1.00 40.36      A    N
ATOM   1786  CA   ILE A 270       9.945  50.816  61.154  1.00 40.36      A    C
ATOM   1787  CB   ILE A 270       9.277  50.791  62.527  1.00 25.65      A    C
ATOM   1788  CG2  ILE A 270       8.029  51.638  62.507  1.00 25.65      A    C
ATOM   1789  CG1  ILE A 270       8.917  49.356  62.898  1.00 25.65      A    C
ATOM   1790  CD1  ILE A 270       8.307  49.222  64.280  1.00 25.65      A    C
ATOM   1791  C    ILE A 270      10.009  52.261  60.660  1.00 40.36      A    C
ATOM   1792  O    ILE A 270       9.115  52.716  59.940  1.00 40.36      A    O
ATOM   1793  N    LYS A 271      11.066  52.977  61.050  1.00 33.44      A    N
ATOM   1794  CA   LYS A 271      11.250  54.355  60.618  1.00 33.44      A    C
ATOM   1795  CB   LYS A 271      12.659  54.869  60.951  1.00 43.40      A    C
ATOM   1796  CG   LYS A 271      12.817  55.531  62.297  1.00 43.40      A    C
ATOM   1797  CD   LYS A 271      14.157  56.269  62.394  1.00 43.40      A    C
```

FIG. 6-31

| ATOM | 1798 | CE  | LYS | A | 271 | 14.348 | 56.917 | 63.771 | 1.00 | 43.40 | A  | C |
|------|------|-----|-----|---|-----|--------|--------|--------|------|-------|----|---|
| ATOM | 1799 | NZ  | LYS | A | 271 | 15.555 | 57.810 | 63.828 | 1.00 | 43.40 | A  | N |
| ATOM | 1800 | C   | LYS | A | 271 | 11.086 | 54.432 | 59.106 | 1.00 | 33.44 | A  | C |
| ATOM | 1801 | O   | LYS | A | 271 | 10.432 | 55.329 | 58.582 | 1.00 | 33.44 | A  | O |
| ATOM | 1802 | N   | VAL | A | 272 | 11.675 | 53.479 | 58.400 | 1.00 | 28.34 | A  | N |
| ATOM | 1803 | CA  | VAL | A | 272 | 11.607 | 53.533 | 56.958 | 1.00 | 28.34 | A  | C |
| ATOM | 1804 | CB  | VAL | A | 272 | 13.018 | 53.392 | 56.335 | 1.00 | 33.65 | A  | C |
| ATOM | 1805 | CG1 | VAL | A | 272 | 14.074 | 53.908 | 57.299 | 1.00 | 33.65 | A  | C |
| ATOM | 1806 | CG2 | VAL | A | 272 | 13.276 | 51.957 | 55.958 | 1.00 | 33.65 | A  | C |
| ATOM | 1807 | C   | VAL | A | 272 | 10.678 | 52.574 | 56.230 | 1.00 | 28.34 | A  | C |
| ATOM | 1808 | O   | VAL | A | 272 | 10.624 | 52.616 | 55.016 | 1.00 | 28.34 | A  | O |
| ATOM | 1809 | N   | LEU | A | 273 | 9.969  | 51.702 | 56.932 | 1.00 | 29.75 | A  | N |
| ATOM | 1810 | CA  | LEU | A | 273 | 9.053  | 50.783 | 56.255 | 1.00 | 29.75 | A  | C |
| ATOM | 1811 | CB  | LEU | A | 273 | 9.384  | 49.307 | 56.525 | 1.00 | 12.18 | A  | C |
| ATOM | 1812 | CG  | LEU | A | 273 | 10.705 | 48.622 | 56.196 | 1.00 | 12.18 | A  | C |
| ATOM | 1813 | CD1 | LEU | A | 273 | 10.419 | 47.149 | 55.973 | 1.00 | 12.18 | A  | C |
| ATOM | 1814 | CD2 | LEU | A | 273 | 11.342 | 49.219 | 54.975 | 1.00 | 12.18 | A  | C |
| ATOM | 1815 | C   | LEU | A | 273 | 7.656  | 51.024 | 56.770 | 1.00 | 29.75 | A  | C |
| ATOM | 1816 | O   | LEU | A | 273 | 6.708  | 50.383 | 56.330 | 1.00 | 29.75 | A  | O |
| ATOM | 1817 | N   | GLY | A | 274 | 7.532  | 51.937 | 57.725 | 1.00 | 42.91 | A  | N |
| ATOM | 1818 | CA  | GLY | A | 274 | 6.235  | 52.207 | 58.311 | 1.00 | 42.91 | A  | C |
| ATOM | 1819 | C   | GLY | A | 274 | 5.897  | 51.109 | 59.307 | 1.00 | 42.91 | A  | C |
| ATOM | 1820 | O   | GLY | A | 274 | 6.561  | 50.066 | 59.361 | 1.00 | 42.91 | A  | O |
| ATOM | 1821 | N   | THR | A | 275 | 4.870  | 51.349 | 60.111 | 1.00 | 42.54 | A  | N |
| ATOM | 1822 | CA  | THR | A | 275 | 4.429  | 50.376 | 61.102 | 1.00 | 42.54 | A  | C |
| ATOM | 1823 | CB  | THR | A | 275 | 3.333  | 50.980 | 62.030 | 1.00 | 43.47 | A  | C |
| ATOM | 1824 | OG1 | THR | A | 275 | 3.913  | 51.981 | 62.878 | 1.00 | 43.47 | A  | O |
| ATOM | 1825 | CG2 | THR | A | 275 | 2.684  | 49.896 | 62.882 | 1.00 | 43.47 | A· | C |
| ATOM | 1826 | C   | THR | A | 275 | 3.835  | 49.168 | 60.370 | 1.00 | 42.54 | A  | C |
| ATOM | 1827 | O   | THR | A | 275 | 2.917  | 49.314 | 59.551 | 1.00 | 42.54 | A  | O |
| ATOM | 1828 | N   | PRO | A | 276 | 4.356  | 47.959 | 60.652 | 1.00 | 47.64 | A  | N |
| ATOM | 1829 | CD  | PRO | A | 276 | 5.425  | 47.590 | 61.595 | 1.00 | 34.03 | A  | C |
| ATOM | 1830 | CA  | PRO | A | 276 | 3.830  | 46.764 | 59.992 | 1.00 | 47.64 | A  | C |
| ATOM | 1831 | CB  | PRO | A | 276 | 4.701  | 45.639 | 60.548 | 1.00 | 34.03 | A  | C |
| ATOM | 1832 | CG  | PRO | A | 276 | 5.091  | 46.140 | 61.888 | 1.00 | 34.03 | A  | C |
| ATOM | 1833 | C   | PRO | A | 276 | 2.369  | 46.544 | 60.287 | 1.00 | 47.64 | A  | C |
| ATOM | 1834 | O   | PRO | A | 276 | 1.923  | 46.724 | 61.422 | 1.00 | 47.64 | A  | O |
| ATOM | 1835 | N   | THR | A | 277 | 1.629  | 46.157 | 59.254 | 1.00 | 64.64 | A  | N |
| ATOM | 1836 | CA  | THR | A | 277 | 0.210  | 45.889 | 59.392 | 1.00 | 64.64 | A  | C |
| ATOM | 1837 | CB  | THR | A | 277 | -0.426 | 45.645 | 58.027 | 1.00 | 35.35 | A  | C |
| ATOM | 1838 | OG1 | THR | A | 277 | 0.065  | 44.410 | 57.490 | 1.00 | 35.35 | A  | O |
| ATOM | 1839 | CG2 | THR | A | 277 | -0.076 | 46.781 | 57.081 | 1.00 | 35.35 | A  | C |
| ATOM | 1840 | C   | THR | A | 277 | 0.115  | 44.628 | 60.236 | 1.00 | 64.64 | A  | C |
| ATOM | 1841 | O   | THR | A | 277 | 1.125  | 44.178 | 60.815 | 1.00 | 64.64 | A  | O |
| ATOM | 1842 | N   | ARG | A | 278 | -1.084 | 44.055 | 60.329 | 1.00 | 63.77 | A  | N |
| ATOM | 1843 | CA  | ARG | A | 278 | -1.233 | 42.829 | 61.101 | 1.00 | 63.77 | A  | C |
| ATOM | 1844 | CB  | ARG | A | 278 | -2.649 | 42.297 | 60.968 | 1.00 | 95.57 | A  | C |
| ATOM | 1845 | CG  | ARG | A | 278 | -2.943 | 41.189 | 61.944 | 1.00 | 95.57 | A  | C |
| ATOM | 1846 | CD  | ARG | A | 278 | -2.724 | 41.636 | 63.386 | 1.00 | 95.57 | A  | C |
| ATOM | 1847 | NE  | ARG | A | 278 | -3.959 | 41.491 | 64.156 | 1.00 | 95.57 | A  | N |
| ATOM | 1848 | CZ  | ARG | A | 278 | -5.069 | 42.203 | 63.936 | 1.00 | 95.57 | A  | C |
| ATOM | 1849 | NH1 | ARG | A | 278 | -5.097 | 43.125 | 62.968 | 1.00 | 95.57 | A  | N |
| ATOM | 1850 | NH2 | ARG | A | 278 | -6.161 | 41.981 | 64.671 | 1.00 | 95.57 | A  | N |
| ATOM | 1851 | C   | ARG | A | 278 | -0.222 | 41.811 | 60.546 | 1.00 | 63.77 | A  | C |
| ATOM | 1852 | O   | ARG | A | 278 | 0.081  | 40.802 | 61.203 | 1.00 | 63.77 | A  | O |
| ATOM | 1853 | N   | GLU | A | 279 | 0.287  | 42.122 | 59.340 | 1.00 | 54.18 | A  | N |
| ATOM | 1854 | CA  | GLU | A | 279 | 1.292  | 41.346 | 58.601 | 1.00 | 54.18 | A  | C |
| ATOM | 1855 | CB  | GLU | A | 279 | 1.870  | 42.202 | 57.464 | 1.00 | 37.58 | A  | C |
| ATOM | 1856 | CG  | GLU | A | 279 | 2.654  | 43.466 | 57.903 | 1.00 | 37.58 | A  | C |
| ATOM | 1857 | CD  | GLU | A | 279 | 3.002  | 44.404 | 56.720 | 1.00 | 37.58 | A  | C |

FIG. 6-32

| | | | | | | | | | | |
|---|---|---|---|---|---|---|---|---|---|---|
| ATOM | 1858 | OE1 | GLU | A | 279 | 3.446 | 43.910 | 55.656 | 1.00 37.58 | A | O |
| ATOM | 1859 | OE2 | GLU | A | 279 | 2.844 | 45.638 | 56.855 | 1.00 37.58 | A | O |
| ATOM | 1860 | C | GLU | A | 279 | 2.441 | 40.822 | 59.478 | 1.00 54.18 | A | C |
| ATOM | 1861 | O | GLU | A | 279 | 3.256 | 40.005 | 59.034 | 1.00 54.18 | A | O |
| ATOM | 1862 | N | ALA | A | 280 | 2.518 | 41.311 | 60.713 | 1.00 49.67 | A | N |
| ATOM | 1863 | CA | ALA | A | 280 | 3.532 | 40.840 | 61.640 | 1.00 49.67 | A | C |
| ATOM | 1864 | CB | ALA | A | 280 | 3.312 | 41.470 | 63.022 | 1.00 25.58 | A | C |
| ATOM | 1865 | C | ALA | A | 280 | 3.364 | 39.315 | 61.719 | 1.00 49.67 | A | C |
| ATOM | 1866 | O | ALA | A | 280 | 4.326 | 38.571 | 61.937 | 1.00 49.67 | A | O |
| ATOM | 1867 | N | ALA | A | 281 | 2.129 | 38.856 | 61.528 | 1.00 45.53 | A | N |
| ATOM | 1868 | CA | ALA | A | 281 | 1.816 | 37.430 | 61.582 | 1.00 45.53 | A | C |
| ATOM | 1869 | CB | ALA | A | 281 | 0.350 | 37.206 | 61.223 | 1.00 26.83 | A | C |
| ATOM | 1870 | C | ALA | A | 281 | 2.716 | 36.578 | 60.679 | 1.00 45.53 | A | C |
| ATOM | 1871 | O | ALA | A | 281 | 3.119 | 35.470 | 61.048 | 1.00 45.53 | A | O |
| ATOM | 1872 | N | ARG | A | 282 | 3.034 | 37.088 | 59.496 | 1.00 64.41 | A | N |
| ATOM | 1873 | CA | ARG | A | 282 | 3.884 | 36.334 | 58.584 | 1.00 64.41 | A | C |
| ATOM | 1874 | CB | ARG | A | 282 | 3.721 | 36.851 | 57.151 | 1.00 67.90 | A | C |
| ATOM | 1875 | CG | ARG | A | 282 | 2.366 | 36.476 | 56.555 | 1.00 67.90 | A | C |
| ATOM | 1876 | CD | ARG | A | 282 | 2.089 | 37.151 | 55.224 | 1.00 67.90 | A | C |
| ATOM | 1877 | NE | ARG | A | 282 | 2.112 | 38.620 | 55.294 | 1.00 67.90 | A | N |
| ATOM | 1878 | CZ | ARG | A | 282 | 1.264 | 39.418 | 54.631 | 1.00 67.90 | A | C |
| ATOM | 1879 | NH1 | ARG | A | 282 | 0.312 | 38.882 | 53.860 | 1.00 67.90 | A | N |
| ATOM | 1880 | NH2 | ARG | A | 282 | 1.389 | 40.748 | 54.698 | 1.00 67.90 | A | N |
| ATOM | 1881 | C | ARG | A | 282 | 5.355 | 36.339 | 58.985 | 1.00 64.41 | A | C |
| ATOM | 1882 | O | ARG | A | 282 | 6.207 | 35.919 | 58.204 | 1.00 64.41 | A | O |
| ATOM | 1883 | N | GLU | A | 283 | 5.652 | 36.792 | 60.206 | 1.00 66.41 | A | N |
| ATOM | 1884 | CA | GLU | A | 283 | 7.031 | 36.821 | 60.685 | 1.00 66.41 | A | C |
| ATOM | 1885 | CB | GLU | A | 283 | 7.559 | 38.259 | 60.784 | 1.00 37.54 | A | C |
| ATOM | 1886 | CG | GLU | A | 283 | 7.072 | 39.256 | 59.741 | 1.00 37.54 | A | C |
| ATOM | 1887 | CD | GLU | A | 283 | 7.776 | 40.612 | 59.882 | 1.00 37.54 | A | C |
| ATOM | 1888 | OE1 | GLU | A | 283 | 8.936 | 40.710 | 59.450 | 1.00 37.54 | A | O |
| ATOM | 1889 | OE2 | GLU | A | 283 | 7.189 | 41.572 | 60.436 | 1.00 37.54 | A | O |
| ATOM | 1890 | C | GLU | A | 283 | 7.163 | 36.193 | 62.074 | 1.00 66.41 | A | C |
| ATOM | 1891 | O | GLU | A | 283 | 7.676 | 35.074 | 62.231 | 1.00 66.41 | A | O |
| ATOM | 1892 | N | ALA | A | 284 | 6.678 | 36.938 | 63.069 | 1.00 56.51 | A | N |
| ATOM | 1893 | CA | ALA | A | 284 | 6.740 | 36.601 | 64.503 | 1.00 56.51 | A | C |
| ATOM | 1894 | CB | ALA | A | 284 | 5.764 | 37.507 | 65.270 | 1.00 25.98 | A | C |
| ATOM | 1895 | C | ALA | A | 284 | 6.596 | 35.173 | 65.037 | 1.00 56.51 | A | C |
| ATOM | 1896 | O | ALA | A | 284 | 7.582 | 34.517 | 65.398 | 1.00 56.51 | A | O |
| ATOM | 1897 | N | GLY | A | 285 | 5.355 | 34.719 | 65.122 | 1.00 66.12 | A | N |
| ATOM | 1898 | CA | GLY | A | 285 | 5.076 | 33.410 | 65.687 | 1.00 66.12 | A | C |
| ATOM | 1899 | C | GLY | A | 285 | 4.065 | 33.722 | 66.780 | 1.00 66.12 | A | C |
| ATOM | 1900 | O | GLY | A | 285 | 3.053 | 33.041 | 66.929 | 1.00 66.12 | A | O |
| ATOM | 1901 | N | GLY | A | 286 | 4.348 | 34.782 | 67.533 | 1.00 48.45 | A | N |
| ATOM | 1902 | CA | GLY | A | 286 | 3.459 | 35.246 | 68.583 | 1.00 48.45 | A | C |
| ATOM | 1903 | C | GLY | A | 286 | 3.235 | 36.719 | 68.261 | 1.00 48.45 | A | C |
| ATOM | 1904 | O | GLY | A | 286 | 4.211 | 37.412 | 67.958 | 1.00 48.45 | A | O |
| ATOM | 1905 | N | GLY | A | 287 | 1.985 | 37.199 | 68.307 | 1.00 84.78 | A | N |
| ATOM | 1906 | CA | GLY | A | 287 | 1.684 | 38.593 | 67.981 | 1.00 84.78 | A | C |
| ATOM | 1907 | C | GLY | A | 287 | 1.533 | 39.533 | 69.173 | 1.00 84.78 | A | C |
| ATOM | 1908 | O | GLY | A | 287 | 0.485 | 39.590 | 69.837 | 1.00 84.78 | A | O |
| ATOM | 1909 | N | TRP | A | 301 | 11.237 | 56.187 | 52.176 | 1.00 41.92 | A | N |
| ATOM | 1910 | CA | TRP | A | 301 | 12.210 | 55.612 | 51.243 | 1.00 41.92 | A | C |
| ATOM | 1911 | CB | TRP | A | 301 | 11.539 | 54.561 | 50.337 | 1.00 39.24 | A | C |
| ATOM | 1912 | CG | TRP | A | 301 | 11.679 | 53.121 | 50.831 | 1.00 39.24 | A | C |
| ATOM | 1913 | CD2 | TRP | A | 301 | 12.903 | 52.443 | 51.200 | 1.00 39.24 | A | C |
| ATOM | 1914 | CE2 | TRP | A | 301 | 12.543 | 51.130 | 51.607 | 1.00 39.24 | A | C |
| ATOM | 1915 | CE3 | TRP | A | 301 | 14.244 | 52.840 | 51.284 | 1.00 39.24 | A | C |
| ATOM | 1916 | CD1 | TRP | A | 301 | 10.673 | 52.198 | 50.985 | 1.00 39.24 | A | C |
| ATOM | 1917 | NE1 | TRP | A | 301 | 11.197 | 50.996 | 51.444 | 1.00 39.24 | A | N |

FIG. 6-33

```
ATOM   1918  CZ2  TRP A 301      13.505  50.193  52.017  1.00 39.24      A    C
ATOM   1919  CZ3  TRP A 301      15.194  51.899  51.702  1.00 39.24      A    C
ATOM   1920  CH2  TRP A 301      14.813  50.605  52.089  1.00 39.24      A    C
ATOM   1921  C    TRP A 301      12.869  56.684  50.384  1.00 41.92      A    C
ATOM   1922  O    TRP A 301      14.058  56.620  50.079  1.00 41.92      A    O
ATOM   1923  N    THR A 302      12.092  57.683  50.004  1.00 59.13      A    N
ATOM   1924  CA   THR A 302      12.613  58.755  49.174  1.00 59.13      A    C
ATOM   1925  CB   THR A 302      11.487  59.407  48.416  1.00 65.93      A    C
ATOM   1926  OG1  THR A 302      10.559  59.936  49.367  1.00 65.93      A    O
ATOM   1927  CG2  THR A 302      10.758  58.374  47.536  1.00 65.93      A    C
ATOM   1928  C    THR A 302      13.332  59.828  49.984  1.00 59.13      A    C
ATOM   1929  O    THR A 302      13.959  60.715  49.418  1.00 59.13      A    O
ATOM   1930  N    ALA A 303      13.223  59.768  51.304  1.00 43.27      A    N
ATOM   1931  CA   ALA A 303      13.909  60.742  52.149  1.00 43.27      A    C
ATOM   1932  CB   ALA A 303      13.030  61.114  53.353  1.00 30.80      A    C
ATOM   1933  C    ALA A 303      15.212  60.094  52.625  1.00 43.27      A    C
ATOM   1934  O    ALA A 303      16.125  60.772  53.112  1.00 43.27      A    O
ATOM   1935  N    VAL A 304      15.293  58.775  52.455  1.00 23.52      A    N
ATOM   1936  CA   VAL A 304      16.448  58.013  52.900  1.00 23.52      A    C
ATOM   1937  CB   VAL A 304      16.178  56.487  52.826  1.00 33.44      A    C
ATOM   1938  CG1  VAL A 304      17.446  55.709  53.194  1.00 33.44      A    C
ATOM   1939  CG2  VAL A 304      15.036  56.115  53.763  1.00 33.44      A    C
ATOM   1940  C    VAL A 304      17.768  58.274  52.186  1.00 23.52      A    C
ATOM   1941  O    VAL A 304      18.774  58.571  52.825  1.00 23.52      A    O
ATOM   1942  N    PHE A 305      17.768  58.166  50.861  1.00 28.00      A    N
ATOM   1943  CA   PHE A 305      18.997  58.335  50.093  1.00 28.00      A    C
ATOM   1944  CB   PHE A 305      18.967  57.393  48.900  1.00 29.64      A    C
ATOM   1945  CG   PHE A 305      18.858  55.952  49.287  1.00 29.64      A    C
ATOM   1946  CD1  PHE A 305      19.938  55.295  49.877  1.00 29.64      A    C
ATOM   1947  CD2  PHE A 305      17.664  55.255  49.101  1.00 29.64      A    C
ATOM   1948  CE1  PHE A 305      19.832  53.961  50.267  1.00 29.64      A    C
ATOM   1949  CE2  PHE A 305      17.549  53.925  49.486  1.00 29.64      A    C
ATOM   1950  CZ   PHE A 305      18.632  53.274  50.075  1.00 29.64      A    C
ATOM   1951  C    PHE A 305      19.376  59.719  49.625  1.00 28.00      A    C
ATOM   1952  O    PHE A 305      18.518  60.559  49.372  1.00 28.00      A    O
ATOM   1953  N    ARG A 306      20.687  59.929  49.496  1.00 52.15      A    N
ATOM   1954  CA   ARG A 306      21.255  61.209  49.070  1.00 52.15      A    C
ATOM   1955  CB   ARG A 306      22.792  61.129  49.094  1.00 70.11      A    C
ATOM   1956  CG   ARG A 306      23.453  60.474  47.873  1.00 70.11      A    C
ATOM   1957  CD   ARG A 306      24.971  60.320  48.086  1.00 70.11      A    C
ATOM   1958  NE   ARG A 306      25.726  60.114  46.845  1.00 70.11      A    N
ATOM   1959  CZ   ARG A 306      25.646  59.033  46.064  1.00 70.11      A    C
ATOM   1960  NH1  ARG A 306      24.829  58.024  46.386  1.00 70.11      A    N
ATOM   1961  NH2  ARG A 306      26.389  58.957  44.958  1.00 70.11      A    N
ATOM   1962  C    ARG A 306      20.756  61.628  47.687  1.00 52.15      A    C
ATOM   1963  O    ARG A 306      20.417  60.787  46.855  1.00 52.15      A    O
ATOM   1964  N    PRO A 307      20.719  62.944  47.423  1.00 67.61      A    N
ATOM   1965  CD   PRO A 307      21.489  63.941  48.200  1.00 39.85      A    C
ATOM   1966  CA   PRO A 307      20.262  63.528  46.157  1.00 67.61      A    C
ATOM   1967  CB   PRO A 307      21.209  64.709  45.983  1.00 39.85      A    C
ATOM   1968  CG   PRO A 307      21.325  65.215  47.389  1.00 39.85      A    C
ATOM   1969  C    PRO A 307      20.204  62.653  44.898  1.00 67.61      A    C
ATOM   1970  O    PRO A 307      19.227  61.925  44.684  1.00 67.61      A    O
ATOM   1971  N    ALA A 308      21.239  62.730  44.065  1.00 35.09      A    N
ATOM   1972  CA   ALA A 308      21.246  61.988  42.804  1.00 35.09      A    C
ATOM   1973  CB   ALA A 308      22.414  62.481  41.934  1.00 58.83      A    C
ATOM   1974  C    ALA A 308      21.236  60.449  42.865  1.00 35.09      A    C
ATOM   1975  O    ALA A 308      21.704  59.783  41.932  1.00 35.09      A    O
ATOM   1976  N    THR A 309      20.699  59.885  43.945  1.00 29.58      A    N
ATOM   1977  CA   THR A 309      20.631  58.435  44.075  1.00 29.58      A    C
```

FIG. 6-34

```
ATOM   1978  CB   THR A 309      20.065  57.997  45.438  1.00 34.47           A C
ATOM   1979  OG1  THR A 309      20.915  58.476  46.485  1.00 34.47           A O
ATOM   1980  CG2  THR A 309      19.994  56.467  45.517  1.00 34.47           A C
ATOM   1981  C    THR A 309      19.702  57.928  42.990  1.00 29.58           A C
ATOM   1982  O    THR A 309      18.563  58.371  42.904  1.00 29.58           A O
ATOM   1983  N    PRO A 310      20.177  57.011  42.129  1.00 40.87           A N
ATOM   1984  CD   PRO A 310      21.566  56.637  41.825  1.00 21.05           A C
ATOM   1985  CA   PRO A 310      19.270  56.525  41.081  1.00 40.87           A C
ATOM   1986  CB   PRO A 310      20.147  55.577  40.238  1.00 21.05           A C
ATOM   1987  CG   PRO A 310      21.377  55.349  41.057  1.00 21.05           A C
ATOM   1988  C    PRO A 310      18.003  55.859  41.579  1.00 40.87           A C
ATOM   1989  O    PRO A 310      18.045  54.999  42.450  1.00 40.87           A O
ATOM   1990  N    PRO A 311      16.853  56.272  41.035  1.00 30.99           A N
ATOM   1991  CD   PRO A 311      16.730  57.382  40.075  1.00 28.33           A C
ATOM   1992  CA   PRO A 311      15.533  55.744  41.388  1.00 30.99           A C
ATOM   1993  CB   PRO A 311      14.613  56.432  40.388  1.00 28.33           A C
ATOM   1994  CG   PRO A 311      15.268  57.761  40.219  1.00 28.33           A C
ATOM   1995  C    PRO A 311      15.443  54.221  41.289  1.00 30.99           A C
ATOM   1996  O    PRO A 311      14.808  53.588  42.123  1.00 30.99           A O
ATOM   1997  N    GLU A 312      16.059  53.627  40.272  1.00 27.46           A N
ATOM   1998  CA   GLU A 312      16.009  52.173  40.133  1.00 27.46           A C
ATOM   1999  CB   GLU A 312      16.861  51.687  38.951  1.00 55.32           A C
ATOM   2000  CG   GLU A 312      16.373  52.102  37.587  1.00 55.32           A C
ATOM   2001  CD   GLU A 312      16.159  53.596  37.496  1.00 55.32           A C
ATOM   2002  OE1  GLU A 312      17.036  54.359  37.982  1.00 55.32           A O
ATOM   2003  OE2  GLU A 312      15.114  54.005  36.936  1.00 55.32           A O
ATOM   2004  C    GLU A 312      16.551  51.526  41.403  1.00 27.46           A C
ATOM   2005  O    GLU A 312      15.955  50.591  41.948  1.00 27.46           A O
ATOM   2006  N    ALA A 313      17.700  52.028  41.852  1.00 23.66           A N
ATOM   2007  CA   ALA A 313      18.371  51.534  43.048  1.00 23.66           A C
ATOM   2008  CB   ALA A 313      19.632  52.340  43.304  1.00 27.46           A C
ATOM   2009  C    ALA A 313      17.473  51.590  44.270  1.00 23.66           A C
ATOM   2010  O    ALA A 313      17.398  50.638  45.049  1.00 23.66           A O
ATOM   2011  N    ILE A 314      16.791  52.713  44.437  1.00 27.49           A N
ATOM   2012  CA   ILE A 314      15.912  52.878  45.574  1.00 27.49           A C
ATOM   2013  CB   ILE A 314      15.557  54.379  45.755  1.00 65.11           A C
ATOM   2014  CG2  ILE A 314      15.163  54.981  44.442  1.00 65.11           A C
ATOM   2015  CG1  ILE A 314      14.456  54.549  46.801  1.00 65.11           A C
ATOM   2016  CD1  ILE A 314      14.128  55.996  47.079  1.00 65.11           A C
ATOM   2017  C    ILE A 314      14.676  51.996  45.468  1.00 27.49           A C
ATOM   2018  O    ILE A 314      14.094  51.609  46.478  1.00 27.49           A O
ATOM   2019  N    ALA A 315      14.307  51.652  44.241  1.00 25.32           A N
ATOM   2020  CA   ALA A 315      13.153  50.792  43.990  1.00 25.32           A C
ATOM   2021  CB   ALA A 315      12.776  50.837  42.499  1.00 20.65           A C
ATOM   2022  C    ALA A 315      13.490  49.356  44.413  1.00 25.32           A C
ATOM   2023  O    ALA A 315      12.695  48.687  45.076  1.00 25.32           A O
ATOM   2024  N    LEU A 316      14.680  48.896  44.033  1.00 29.86           A N
ATOM   2025  CA   LEU A 316      15.121  47.542  44.353  1.00 29.86           A C
ATOM   2026  CB   LEU A 316      16.434  47.231  43.625  1.00 16.30           A C
ATOM   2027  CG   LEU A 316      17.021  45.844  43.892  1.00 16.30           A C
ATOM   2028  CD1  LEU A 316      16.059  44.780  43.396  1.00 16.30           A C
ATOM   2029  CD2  LEU A 316      18.372  45.707  43.213  1.00 16.30           A C
ATOM   2030  C    LEU A 316      15.281  47.333  45.864  1.00 29.86           A C
ATOM   2031  O    LEU A 316      15.140  46.225  46.364  1.00 29.86           A O
ATOM   2032  N    CYS A 317      15.573  48.402  46.591  1.00 32.62           A N
ATOM   2033  CA   CYS A 317      15.723  48.303  48.035  1.00 32.62           A C
ATOM   2034  CB   CYS A 317      16.294  49.593  48.636  1.00 28.06           A C
ATOM   2035  SG   CYS A 317      18.048  49.858  48.418  1.00 28.06           A S
ATOM   2036  C    CYS A 317      14.399  48.045  48.709  1.00 32.62           A C
ATOM   2037  O    CYS A 317      14.336  47.317  49.698  1.00 32.62           A O
```

FIG. 6-35

```
ATOM   2038  N    SER A 318      13.348  48.668  48.181  1.00 25.43       A    N
ATOM   2039  CA   SER A 318      11.999  48.539  48.738  1.00 25.43       A    C
ATOM   2040  CB   SER A 318      11.091  49.617  48.159  1.00 32.84       A    C
ATOM   2041  OG   SER A 318      11.035  49.480  46.750  1.00 32.84       A    O
ATOM   2042  C    SER A 318      11.384  47.170  48.468  1.00 25.43       A    C
ATOM   2043  O    SER A 318      10.539  46.690  49.230  1.00 25.43       A    O
ATOM   2044  N    ARG A 319      11.808  46.558  47.369  1.00 29.94       A    N
ATOM   2045  CA   ARG A 319      11.317  45.250  46.980  1.00 29.94       A    C
ATOM   2046  CB   ARG A 319      11.343  45.111  45.465  1.00 43.35       A    C
ATOM   2047  CG   ARG A 319      10.577  46.203  44.747  1.00 43.35       A    C
ATOM   2048  CD   ARG A 319       9.076  46.107  44.951  1.00 43.35       A    C
ATOM   2049  NE   ARG A 319       8.507  44.916  44.325  1.00 43.35       A    N
ATOM   2050  CZ   ARG A 319       8.392  43.734  44.931  1.00 43.35       A    C
ATOM   2051  NH1  ARG A 319       8.808  43.586  46.185  1.00 43.35       A    N
ATOM   2052  NH2  ARG A 319       7.853  42.695  44.294  1.00 43.35       A    N
ATOM   2053  C    ARG A 319      12.162  44.160  47.619  1.00 29.94       A    C
ATOM   2054  O    ARG A 319      11.827  42.977  47.543  1.00 29.94       A    O
ATOM   2055  N    LEU A 320      13.258  44.558  48.255  1.00 15.48       A    N
ATOM   2056  CA   LEU A 320      14.130  43.600  48.905  1.00 15.48       A    C
ATOM   2057  CB   LEU A 320      15.595  43.969  48.651  1.00 12.94       A    C
ATOM   2058  CG   LEU A 320      16.104  43.671  47.232  1.00 12.94       A    C
ATOM   2059  CD1  LEU A 320      17.545  44.111  47.074  1.00 12.94       A    C
ATOM   2060  CD2  LEU A 320      15.977  42.182  46.957  1.00 12.94       A    C
ATOM   2061  C    LEU A 320      13.829  43.586  50.385  1.00 15.48       A    C
ATOM   2062  O    LEU A 320      13.659  42.533  50.990  1.00 15.48       A    O
ATOM   2063  N    LEU A 321      13.739  44.780  50.950  1.00 22.14       A    N
ATOM   2064  CA   LEU A 321      13.470  44.956  52.363  1.00 22.14       A    C
ATOM   2065  CB   LEU A 321      14.210  46.196  52.860  1.00 13.09       A    C
ATOM   2066  CG   LEU A 321      15.722  46.126  52.633  1.00 13.09       A    C
ATOM   2067  CD1  LEU A 321      16.354  47.470  52.936  1.00 13.09       A    C
ATOM   2068  CD2  LEU A 321      16.323  45.029  53.494  1.00 13.09       A    C
ATOM   2069  C    LEU A 321      11.972  45.085  52.600  1.00 22.14       A    C
ATOM   2070  O    LEU A 321      11.455  46.179  52.794  1.00 22.14       A    O
ATOM   2071  N    GLU A 322      11.283  43.950  52.576  1.00 39.55       A    N
ATOM   2072  CA   GLU A 322       9.837  43.906  52.778  1.00 39.55       A    C
ATOM   2073  CB   GLU A 322       9.154  43.265  51.563  1.00 39.14       A    C
ATOM   2074  CG   GLU A 322       9.408  44.001  50.266  1.00 39.14       A    C
ATOM   2075  CD   GLU A 322       8.129  44.516  49.616  1.00 39.14       A    C
ATOM   2076  OE1  GLU A 322       7.164  44.838  50.350  1.00 39.14       A    O
ATOM   2077  OE2  GLU A 322       8.098  44.614  48.365  1.00 39.14       A    O
ATOM   2078  C    GLU A 322       9.514  43.083  54.022  1.00 39.55       A    C
ATOM   2079  O    GLU A 322      10.126  42.039  54.241  1.00 39.55       A    O
ATOM   2080  N    TYR A 323       8.556  43.534  54.831  1.00 18.00       A    N
ATOM   2081  CA   TYR A 323       8.202  42.797  56.038  1.00 18.00       A    C
ATOM   2082  CB   TYR A 323       7.027  43.460  56.757  1.00 27.51       A    C
ATOM   2083  CG   TYR A 323       7.414  44.653  57.598  1.00 27.51       A    C
ATOM   2084  CD1  TYR A 323       8.369  44.538  58.614  1.00 27.51       A    C
ATOM   2085  CE1  TYR A 323       8.731  45.633  59.396  1.00 27.51       A    C
ATOM   2086  CD2  TYR A 323       6.825  45.894  57.386  1.00 27.51       A    C
ATOM   2087  CE2  TYR A 323       7.174  47.001  58.165  1.00 27.51       A    C
ATOM   2088  CZ   TYR A 323       8.130  46.867  59.168  1.00 27.51       A    C
ATOM   2089  OH   TYR A 323       8.480  47.972  59.919  1.00 27.51       A    O
ATOM   2090  C    TYR A 323       7.864  41.344  55.759  1.00 18.00       A    C
ATOM   2091  O    TYR A 323       8.456  40.441  56.338  1.00 18.00       A    O
ATOM   2092  N    THR A 324       6.906  41.114  54.874  1.00 31.56       A    N
ATOM   2093  CA   THR A 324       6.525  39.750  54.538  1.00 31.56       A    C
ATOM   2094  CB   THR A 324       5.279  39.710  53.650  1.00 37.28       A    C
ATOM   2095  OG1  THR A 324       4.172  40.305  54.344  1.00 37.28       A    O
ATOM   2096  CG2  THR A 324       4.950  38.268  53.288  1.00 37.28       A    C
ATOM   2097  C    THR A 324       7.661  39.078  53.782  1.00 31.56       A    C
```

FIG. 6-36

```
ATOM   2098  O    THR A 324       7.983  39.441  52.649  1.00 31.56      A    O
ATOM   2099  N    PRO A 325       8.280  38.073  54.400  1.00 22.39      A    N
ATOM   2100  CD   PRO A 325       8.071  37.549  55.754  1.00 18.66      A    C
ATOM   2101  CA   PRO A 325       9.380  37.396  53.721  1.00 22.39      A    C
ATOM   2102  CB   PRO A 325       9.783  36.300  54.713  1.00 18.66      A    C
ATOM   2103  CG   PRO A 325       8.614  36.179  55.632  1.00 18.66      A    C
ATOM   2104  C    PRO A 325       9.013  36.874  52.349  1.00 22.39      A    C
ATOM   2105  O    PRO A 325       9.818  36.885  51.436  1.00 22.39      A    O
ATOM   2106  N    THR A 326       7.770  36.463  52.201  1.00 23.30      A    N
ATOM   2107  CA   THR A 326       7.279  35.892  50.955  1.00 23.30      A    C
ATOM   2108  CB   THR A 326       5.948  35.174  51.240  1.00 25.06      A    C
ATOM   2109  OG1  THR A 326       5.851  34.007  50.425  1.00 25.06      A    O
ATOM   2110  CG2  THR A 326       4.772  36.099  50.979  1.00 25.06      A    C
ATOM   2111  C    THR A 326       7.104  36.926  49.845  1.00 23.30      A    C
ATOM   2112  O    THR A 326       7.032  36.578  48.666  1.00 23.30      A    O
ATOM   2113  N    ALA A 327       7.050  38.196  50.239  1.00 44.50      A    N
ATOM   2114  CA   ALA A 327       6.872  39.304  49.299  1.00 44.50      A    C
ATOM   2115  CB   ALA A 327       6.063  40.414  49.961  1.00 16.21      A    C
ATOM   2116  C    ALA A 327       8.185  39.872  48.748  1.00 44.50      A    C
ATOM   2117  O    ALA A 327       8.182  40.640  47.783  1.00 44.50      A    O
ATOM   2118  N    ARG A 328       9.312  39.508  49.348  1.00 30.85      A    N
ATOM   2119  CA   ARG A 328      10.583  40.018  48.860  1.00 30.85      A    C
ATOM   2120  CB   ARG A 328      11.700  39.682  49.841  1.00 16.09      A    C
ATOM   2121  CG   ARG A 328      11.524  40.354  51.170  1.00 16.09      A    C
ATOM   2122  CD   ARG A 328      12.386  39.735  52.242  1.00 16.09      A    C
ATOM   2123  NE   ARG A 328      11.793  39.984  53.546  1.00 16.09      A    N
ATOM   2124  CZ   ARG A 328      12.142  39.366  54.662  1.00 16.09      A    C
ATOM   2125  NH1  ARG A 328      13.098  38.451  54.658  1.00 16.09      A    N
ATOM   2126  NH2  ARG A 328      11.508  39.652  55.780  1.00 16.09      A    N
ATOM   2127  C    ARG A 328      10.873  39.413  47.504  1.00 30.85      A    C
ATOM   2128  O    ARG A 328      10.252  38.433  47.126  1.00 30.85      A    O
ATOM   2129  N    LEU A 329      11.804  40.006  46.766  1.00 25.19      A    N
ATOM   2130  CA   LEU A 329      12.169  39.483  45.455  1.00 25.19      A    C
ATOM   2131  CB   LEU A 329      12.904  40.543  44.637  1.00 20.15      A    C
ATOM   2132  CG   LEU A 329      12.113  41.532  43.791  1.00 20.15      A    C
ATOM   2133  CD1  LEU A 329      10.782  41.843  44.417  1.00 20.15      A    C
ATOM   2134  CD2  LEU A 329      12.941  42.787  43.640  1.00 20.15      A    C
ATOM   2135  C    LEU A 329      13.079  38.285  45.627  1.00 25.19      A    C
ATOM   2136  O    LEU A 329      13.736  38.137  46.656  1.00 25.19      A    O
ATOM   2137  N    THR A 330      13.114  37.421  44.628  1.00 24.41      A    N
ATOM   2138  CA   THR A 330      13.989  36.273  44.703  1.00 24.41      A    C
ATOM   2139  CB   THR A 330      13.474  35.104  43.856  1.00 21.52      A    C
ATOM   2140  OG1  THR A 330      13.442  35.492  42.479  1.00 21.52      A    O
ATOM   2141  CG2  THR A 330      12.086  34.693  44.296  1.00 21.52      A    C
ATOM   2142  C    THR A 330      15.323  36.722  44.149  1.00 24.41      A    C
ATOM   2143  O    THR A 330      15.385  37.691  43.400  1.00 24.41      A    O
ATOM   2144  N    PRO A 331      16.414  36.037  44.521  1.00 29.54      A    N
ATOM   2145  CD   PRO A 331      16.502  34.899  45.454  1.00 13.64      A    C
ATOM   2146  CA   PRO A 331      17.741  36.408  44.023  1.00 29.54      A    C
ATOM   2147  CB   PRO A 331      18.599  35.217  44.430  1.00 13.64      A    C
ATOM   2148  CG   PRO A 331      17.986  34.802  45.721  1.00 13.64      A    C
ATOM   2149  C    PRO A 331      17.740  36.628  42.506  1.00 29.54      A    C
ATOM   2150  O    PRO A 331      18.295  37.608  42.019  1.00 29.54      A    O
ATOM   2151  N    LEU A 332      17.106  35.724  41.762  1.00 31.33      A    N
ATOM   2152  CA   LEU A 332      17.066  35.853  40.313  1.00 31.33      A    C
ATOM   2153  CB   LEU A 332      16.515  34.596  39.651  1.00 33.42      A    C
ATOM   2154  CG   LEU A 332      17.535  33.667  38.999  1.00 33.42      A    C
ATOM   2155  CD1  LEU A 332      16.797  32.577  38.239  1.00 33.42      A    C
ATOM   2156  CD2  LEU A 332      18.423  34.452  38.067  1.00 33.42      A    C
ATOM   2157  C    LEU A 332      16.241  37.030  39.854  1.00 31.33      A    C
```

FIG. 6-37

```
ATOM   2158  O    LEU A 332      16.604  37.702  38.892  1.00 31.33      A   O
ATOM   2159  N    GLU A 333      15.120  37.278  40.523  1.00 27.63      A   N
ATOM   2160  CA   GLU A 333      14.264  38.400  40.143  1.00 27.63      A   C
ATOM   2161  CB   GLU A 333      12.952  38.383  40.923  1.00 30.53      A   C
ATOM   2162  CG   GLU A 333      12.091  37.177  40.668  1.00 30.53      A   C
ATOM   2163  CD   GLU A 333      10.945  37.100  41.639  1.00 30.53      A   C
ATOM   2164  OE1  GLU A 333      11.113  37.557  42.792  1.00 30.53      A   O
ATOM   2165  OE2  GLU A 333       9.878  36.575  41.272  1.00 30.53      A   O
ATOM   2166  C    GLU A 333      14.992  39.699  40.430  1.00 27.63      A   C
ATOM   2167  O    GLU A 333      14.690  40.741  39.846  1.00 27.63      A   O
ATOM   2168  N    ALA A 334      15.947  39.628  41.348  1.00 21.92      A   N
ATOM   2169  CA   ALA A 334      16.727  40.797  41.701  1.00 21.92      A   C
ATOM   2170  CB   ALA A 334      17.431  40.586  43.039  1.00 38.95      A   C
ATOM   2171  C    ALA A 334      17.737  41.008  40.587  1.00 21.92      A   C
ATOM   2172  O    ALA A 334      17.878  42.109  40.068  1.00 21.92      A   O
ATOM   2173  N    CYS A 335      18.431  39.944  40.211  1.00 28.10      A   N
ATOM   2174  CA   CYS A 335      19.415  40.039  39.139  1.00 28.10      A   C
ATOM   2175  CB   CYS A 335      19.932  38.655  38.747  1.00 26.43      A   C
ATOM   2176  SG   CYS A 335      21.134  37.920  39.855  1.00 26.43      A   S
ATOM   2177  C    CYS A 335      18.816  40.683  37.901  1.00 28.10      A   C
ATOM   2178  O    CYS A 335      19.481  41.445  37.198  1.00 28.10      A   O
ATOM   2179  N    ALA A 336      17.550  40.361  37.648  1.00 19.08      A   N
ATOM   2180  CA   ALA A 336      16.819  40.851  36.490  1.00 19.08      A   C
ATOM   2181  CB   ALA A 336      15.774  39.835  36.101  1.00 20.87      A   C
ATOM   2182  C    ALA A 336      16.170  42.204  36.696  1.00 19.08      A   C
ATOM   2183  O    ALA A 336      15.474  42.688  35.816  1.00 19.08      A   O
ATOM   2184  N    HIS A 337      16.399  42.815  37.854  1.00 31.75      A   N
ATOM   2185  CA   HIS A 337      15.806  44.116  38.158  1.00 31.75      A   C
ATOM   2186  CB   HIS A 337      16.097  44.541  39.593  1.00 27.83      A   C
ATOM   2187  CG   HIS A 337      15.377  45.786  40.003  1.00 27.83      A   C
ATOM   2188  CD2  HIS A 337      15.786  47.073  40.070  1.00 27.83      A   C
ATOM   2189  ND1  HIS A 337      14.057  45.786  40.396  1.00 27.83      A   N
ATOM   2190  CE1  HIS A 337      13.685  47.018  40.691  1.00 27.83      A   C
ATOM   2191  NE2  HIS A 337      14.718  47.820  40.502  1.00 27.83      A   N
ATOM   2192  C    HIS A 337      16.338  45.176  37.222  1.00 31.75      A   C
ATOM   2193  O    HIS A 337      17.455  45.063  36.720  1.00 31.75      A   O
ATOM   2194  N    SER A 338      15.539  46.216  37.005  1.00 34.32      A   N
ATOM   2195  CA   SER A 338      15.922  47.279  36.095  1.00 34.32      A   C
ATOM   2196  CB   SER A 338      14.782  48.290  35.957  1.00 33.71      A   C
ATOM   2197  OG   SER A 338      14.909  49.341  36.892  1.00 33.71      A   O
ATOM   2198  C    SER A 338      17.208  47.977  36.521  1.00 34.32      A   C
ATOM   2199  O    SER A 338      17.978  48.424  35.670  1.00 34.32      A   O
ATOM   2200  N    PHE A 339      17.446  48.052  37.829  1.00 19.65      A   N
ATOM   2201  CA   PHE A 339      18.642  48.702  38.367  1.00 19.65      A   C
ATOM   2202  CB   PHE A 339      18.693  48.515  39.891  1.00 24.09      A   C
ATOM   2203  CG   PHE A 339      19.953  49.033  40.538  1.00 24.09      A   C
ATOM   2204  CD1  PHE A 339      20.366  50.350  40.352  1.00 24.09      A   C
ATOM   2205  CD2  PHE A 339      20.720  48.205  41.345  1.00 24.09      A   C
ATOM   2206  CE1  PHE A 339      21.527  50.829  40.962  1.00 24.09      A   C
ATOM   2207  CE2  PHE A 339      21.881  48.674  41.956  1.00 24.09      A   C
ATOM   2208  CZ   PHE A 339      22.284  49.987  41.766  1.00 24.09      A   C
ATOM   2209  C    PHE A 339      19.926  48.182  37.738  1.00 19.65      A   C
ATOM   2210  O    PHE A 339      20.904  48.915  37.631  1.00 19.65      A   O
ATOM   2211  N    PHE A 340      19.901  46.922  37.306  1.00 17.89      A   N
ATOM   2212  CA   PHE A 340      21.055  46.255  36.695  1.00 17.89      A   C
ATOM   2213  CB   PHE A 340      21.087  44.800  37.142  1.00 22.64      A   C
ATOM   2214  CG   PHE A 340      21.231  44.641  38.614  1.00 22.64      A   C
ATOM   2215  CD1  PHE A 340      22.400  45.021  39.249  1.00 22.64      A   C
ATOM   2216  CD2  PHE A 340      20.197  44.118  39.374  1.00 22.64      A   C
ATOM   2217  CE1  PHE A 340      22.527  44.910  40.624  1.00 22.64      A   C
```

FIG. 6-38

| ATOM | 2218 | CE2 | PHE | A | 340 | 20.315 | 44.005 | 40.748 | 1.00 | 22.64 | A | C |
| --- | --- | --- | --- | --- | --- | --- | --- | --- | --- | --- | --- | --- |
| ATOM | 2219 | CZ  | PHE | A | 340 | 21.483 | 44.389 | 41.373 | 1.00 | 22.64 | A | C |
| ATOM | 2220 | C   | PHE | A | 340 | 21.142 | 46.307 | 35.168 | 1.00 | 17.89 | A | C |
| ATOM | 2221 | O   | PHE | A | 340 | 22.050 | 45.738 | 34.573 | 1.00 | 17.89 | A | O |
| ATOM | 2222 | N   | ASP | A | 341 | 20.208 | 46.989 | 34.530 | 1.00 | 36.31 | A | N |
| ATOM | 2223 | CA  | ASP | A | 341 | 20.238 | 47.092 | 33.082 | 1.00 | 36.31 | A | C |
| ATOM | 2224 | CB  | ASP | A | 341 | 19.159 | 48.072 | 32.604 | 1.00 | 45.23 | A | C |
| ATOM | 2225 | CG  | ASP | A | 341 | 17.752 | 47.452 | 32.602 | 1.00 | 45.23 | A | C |
| ATOM | 2226 | OD1 | ASP | A | 341 | 17.626 | 46.234 | 32.897 | 1.00 | 45.23 | A | O |
| ATOM | 2227 | OD2 | ASP | A | 341 | 16.767 | 48.175 | 32.297 | 1.00 | 45.23 | A | O |
| ATOM | 2228 | C   | ASP | A | 341 | 21.602 | 47.496 | 32.510 | 1.00 | 36.31 | A | C |
| ATOM | 2229 | O   | ASP | A | 341 | 22.053 | 46.900 | 31.533 | 1.00 | 36.31 | A | O |
| ATOM | 2230 | N   | GLU | A | 342 | 22.261 | 48.487 | 33.114 | 1.00 | 23.08 | A | N |
| ATOM | 2231 | CA  | GLU | A | 342 | 23.562 | 48.949 | 32.626 | 1.00 | 23.08 | A | C |
| ATOM | 2232 | CB  | GLU | A | 342 | 24.176 | 49.956 | 33.591 | 1.00 | 35.33 | A | C |
| ATOM | 2233 | CG  | GLU | A | 342 | 25.407 | 50.676 | 33.033 | 1.00 | 35.33 | A | C |
| ATOM | 2234 | CD  | GLU | A | 342 | 25.912 | 51.798 | 33.952 | 1.00 | 35.33 | A | C |
| ATOM | 2235 | OE1 | GLU | A | 342 | 25.068 | 52.552 | 34.490 | 1.00 | 35.33 | A | O |
| ATOM | 2236 | OE2 | GLU | A | 342 | 27.144 | 51.941 | 34.131 | 1.00 | 35.33 | A | O |
| ATOM | 2237 | C   | GLU | A | 342 | 24.563 | 47.818 | 32.410 | 1.00 | 23.08 | A | C |
| ATOM | 2238 | O   | GLU | A | 342 | 25.389 | 47.875 | 31.501 | 1.00 | 23.08 | A | O |
| ATOM | 2239 | N   | LEU | A | 343 | 24.490 | 46.790 | 33.247 | 1.00 | 15.62 | A | N |
| ATOM | 2240 | CA  | LEU | A | 343 | 25.405 | 45.663 | 33.140 | 1.00 | 15.62 | A | C |
| ATOM | 2241 | CB  | LEU | A | 343 | 25.303 | 44.790 | 34.389 | 1.00 | 34.06 | A | C |
| ATOM | 2242 | CG  | LEU | A | 343 | 25.480 | 45.518 | 35.726 | 1.00 | 34.06 | A | C |
| ATOM | 2243 | CD1 | LEU | A | 343 | 25.331 | 44.530 | 36.896 | 1.00 | 34.06 | A | C |
| ATOM | 2244 | CD2 | LEU | A | 343 | 26.855 | 46.208 | 35.742 | 1.00 | 34.06 | A | C |
| ATOM | 2245 | C   | LEU | A | 343 | 25.087 | 44.833 | 31.920 | 1.00 | 15.62 | A | C |
| ATOM | 2246 | O   | LEU | A | 343 | 25.935 | 44.127 | 31.395 | 1.00 | 15.62 | A | O |
| ATOM | 2247 | N   | ARG | A | 344 | 23.842 | 44.915 | 31.477 | 1.00 | 39.47 | A | N |
| ATOM | 2248 | CA  | ARG | A | 344 | 23.402 | 44.167 | 30.310 | 1.00 | 39.47 | A | C |
| ATOM | 2249 | CB  | ARG | A | 344 | 21.918 | 43.832 | 30.434 | 1.00 | 24.87 | A | C |
| ATOM | 2250 | CG  | ARG | A | 344 | 21.666 | 42.611 | 31.298 | 1.00 | 24.87 | A | C |
| ATOM | 2251 | CD  | ARG | A | 344 | 20.194 | 42.309 | 31.412 | 1.00 | 24.87 | A | C |
| ATOM | 2252 | NE  | ARG | A | 344 | 19.499 | 43.210 | 32.331 | 1.00 | 24.87 | A | N |
| ATOM | 2253 | CZ  | ARG | A | 344 | 19.408 | 43.029 | 33.647 | 1.00 | 24.87 | A | C |
| ATOM | 2254 | NH1 | ARG | A | 344 | 19.970 | 41.972 | 34.226 | 1.00 | 24.87 | A | N |
| ATOM | 2255 | NH2 | ARG | A | 344 | 18.741 | 43.907 | 34.385 | 1.00 | 24.87 | A | N |
| ATOM | 2256 | C   | ARG | A | 344 | 23.687 | 44.913 | 29.010 | 1.00 | 39.47 | A | C |
| ATOM | 2257 | O   | ARG | A | 344 | 23.548 | 44.355 | 27.927 | 1.00 | 39.47 | A | O |
| ATOM | 2258 | N   | ASP | A | 345 | 24.087 | 46.176 | 29.121 | 1.00 | 39.02 | A | N |
| ATOM | 2259 | CA  | ASP | A | 345 | 24.441 | 46.960 | 27.948 | 1.00 | 39.02 | A | C |
| ATOM | 2260 | CB  | ASP | A | 345 | 24.695 | 48.418 | 28.357 | 1.00 | 33.23 | A | C |
| ATOM | 2261 | CG  | ASP | A | 345 | 25.125 | 49.306 | 27.189 | 1.00 | 33.23 | A | C |
| ATOM | 2262 | OD1 | ASP | A | 345 | 25.985 | 48.893 | 26.384 | 1.00 | 33.23 | A | O |
| ATOM | 2263 | OD2 | ASP | A | 345 | 24.615 | 50.437 | 27.099 | 1.00 | 33.23 | A | O |
| ATOM | 2264 | C   | ASP | A | 345 | 25.721 | 46.320 | 27.395 | 1.00 | 39.02 | A | C |
| ATOM | 2265 | O   | ASP | A | 345 | 26.615 | 45.950 | 28.160 | 1.00 | 39.02 | A | O |
| ATOM | 2266 | N   | PRO | A | 346 | 25.811 | 46.154 | 26.065 | 1.00 | 29.11 | A | N |
| ATOM | 2267 | CD  | PRO | A | 346 | 24.746 | 46.385 | 25.074 | 1.00 | 15.50 | A | C |
| ATOM | 2268 | CA  | PRO | A | 346 | 26.993 | 45.554 | 25.431 | 1.00 | 29.11 | A | C |
| ATOM | 2269 | CB  | PRO | A | 346 | 26.522 | 45.302 | 24.003 | 1.00 | 15.50 | A | C |
| ATOM | 2270 | CG  | PRO | A | 346 | 25.515 | 46.395 | 23.788 | 1.00 | 15.50 | A | C |
| ATOM | 2271 | C   | PRO | A | 346 | 28.248 | 46.431 | 25.488 | 1.00 | 29.11 | A | C |
| ATOM | 2272 | O   | PRO | A | 346 | 29.370 | 45.931 | 25.431 | 1.00 | 29.11 | A | O |
| ATOM | 2273 | N   | ASN | A | 347 | 28.051 | 47.734 | 25.628 | 1.00 | 43.93 | A | N |
| ATOM | 2274 | CA  | ASN | A | 347 | 29.163 | 48.676 | 25.675 | 1.00 | 43.93 | A | C |
| ATOM | 2275 | CB  | ASN | A | 347 | 28.730 | 49.987 | 25.038 | 1.00 | 45.58 | A | C |
| ATOM | 2276 | CG  | ASN | A | 347 | 28.522 | 49.850 | 23.553 | 1.00 | 45.58 | A | C |
| ATOM | 2277 | OD1 | ASN | A | 347 | 27.705 | 50.566 | 22.962 | 1.00 | 45.58 | A | O |

FIG. 6-39

| ATOM | 2278 | ND2 | ASN | A | 347 | 29.265 | 48.924 | 22.931 | 1.00 | 45.58 | A | N |
| ATOM | 2279 | C | ASN | A | 347 | 29.744 | 48.949 | 27.058 | 1.00 | 43.93 | A | C |
| ATOM | 2280 | O | ASN | A | 347 | 30.772 | 49.624 | 27.194 | 1.00 | 43.93 | A | O |
| ATOM | 2281 | N | VAL | A | 348 | 29.095 | 48.415 | 28.082 | 1.00 | 34.26 | A | N |
| ATOM | 2282 | CA | VAL | A | 348 | 29.556 | 48.627 | 29.432 | 1.00 | 34.26 | A | C |
| ATOM | 2283 | CB | VAL | A | 348 | 28.593 | 47.988 | 30.446 | 1.00 | 26.97 | A | C |
| ATOM | 2284 | CG1 | VAL | A | 348 | 28.742 | 46.482 | 30.445 | 1.00 | 26.97 | A | C |
| ATOM | 2285 | CG2 | VAL | A | 348 | 28.842 | 48.577 | 31.820 | 1.00 | 26.97 | A | C |
| ATOM | 2286 | C | VAL | A | 348 | 30.962 | 48.099 | 29.653 | 1.00 | 34.26 | A | C |
| ATOM | 2287 | O | VAL | A | 348 | 31.288 | 46.963 | 29.298 | 1.00 | 34.26 | A | O |
| ATOM | 2288 | N | LYS | A | 349 | 31.790 | 48.967 | 30.225 | 1.00 | 38.62 | A | N |
| ATOM | 2289 | CA | LYS | A | 349 | 33.179 | 48.671 | 30.558 | 1.00 | 38.62 | A | C |
| ATOM | 2290 | CB | LYS | A | 349 | 34.134 | 49.366 | 29.574 | 1.00 | 44.36 | A | C |
| ATOM | 2291 | CG | LYS | A | 349 | 34.190 | 48.725 | 28.183 | 1.00 | 44.36 | A | C |
| ATOM | 2292 | CD | LYS | A | 349 | 34.312 | 47.188 | 28.282 | 1.00 | 44.36 | A | C |
| ATOM | 2293 | CE | LYS | A | 349 | 35.064 | 46.547 | 27.106 | 1.00 | 44.36 | A | C |
| ATOM | 2294 | NZ | LYS | A | 349 | 36.549 | 46.520 | 27.324 | 1.00 | 44.36 | A | N |
| ATOM | 2295 | C | LYS | A | 349 | 33.420 | 49.171 | 31.989 | 1.00 | 38.62 | A | C |
| ATOM | 2296 | O | LYS | A | 349 | 32.594 | 49.909 | 32.540 | 1.00 | 38.62 | A | O |
| ATOM | 2297 | N | LEU | A | 350 | 34.532 | 48.763 | 32.594 | 1.00 | 42.94 | A | N |
| ATOM | 2298 | CA | LEU | A | 350 | 34.845 | 49.197 | 33.949 | 1.00 | 42.94 | A | C |
| ATOM | 2299 | CB | LEU | A | 350 | 35.752 | 48.183 | 34.639 | 1.00 | 53.75 | A | C |
| ATOM | 2300 | CG | LEU | A | 350 | 35.084 | 46.845 | 34.957 | 1.00 | 53.75 | A | C |
| ATOM | 2301 | CD1 | LEU | A | 350 | 36.142 | 45.837 | 35.380 | 1.00 | 53.75 | A | C |
| ATOM | 2302 | CD2 | LEU | A | 350 | 34.055 | 47.028 | 36.043 | 1.00 | 53.75 | A | C |
| ATOM | 2303 | C | LEU | A | 350 | 35.534 | 50.551 | 33.919 | 1.00 | 42.94 | A | C |
| ATOM | 2304 | O | LEU | A | 350 | 36.042 | 50.978 | 32.878 | 1.00 | 42.94 | A | O |
| ATOM | 2305 | N | PRO | A | 351 | 35.562 | 51.250 | 35.063 | 1.00 | 41.49 | A | N |
| ATOM | 2306 | CD | PRO | A | 351 | 35.067 | 50.922 | 36.407 | 1.00 | 51.76 | A | C |
| ATOM | 2307 | CA | PRO | A | 351 | 36.222 | 52.553 | 35.063 | 1.00 | 41.49 | A | C |
| ATOM | 2308 | CB | PRO | A | 351 | 36.046 | 53.034 | 36.503 | 1.00 | 51.76 | A | C |
| ATOM | 2309 | CG | PRO | A | 351 | 34.854 | 52.284 | 36.974 | 1.00 | 51.76 | A | C |
| ATOM | 2310 | C | PRO | A | 351 | 37.690 | 52.357 | 34.693 | 1.00 | 41.49 | A | C |
| ATOM | 2311 | O | PRO | A | 351 | 38.307 | 53.187 | 34.025 | 1.00 | 41.49 | A | O |
| ATOM | 2312 | N | ASN | A | 352 | 38.226 | 51.220 | 35.114 | 1.00 | 49.39 | A | N |
| ATOM | 2313 | CA | ASN | A | 352 | 39.623 | 50.901 | 34.880 | 1.00 | 49.39 | A | C |
| ATOM | 2314 | CB | ASN | A | 352 | 40.030 | 49.751 | 35.821 | 1.00 | 64.51 | A | C |
| ATOM | 2315 | CG | ASN | A | 352 | 39.875 | 48.373 | 35.187 | 1.00 | 64.51 | A | C |
| ATOM | 2316 | OD1 | ASN | A | 352 | 39.148 | 48.192 | 34.196 | 1.00 | 64.51 | A | O |
| ATOM | 2317 | ND2 | ASN | A | 352 | 40.556 | 47.380 | 35.773 | 1.00 | 64.51 | A | N |
| ATOM | 2318 | C | ASN | A | 352 | 39.933 | 50.571 | 33.427 | 1.00 | 49.39 | A | C |
| ATOM | 2319 | O | ASN | A | 352 | 41.078 | 50.291 | 33.087 | 1.00 | 49.39 | A | O |
| ATOM | 2320 | N | GLY | A | 353 | 38.916 | 50.614 | 32.572 | 1.00 | 56.36 | A | N |
| ATOM | 2321 | CA | GLY | A | 353 | 39.130 | 50.307 | 31.170 | 1.00 | 56.36 | A | C |
| ATOM | 2322 | C | GLY | A | 353 | 38.632 | 48.924 | 30.761 | 1.00 | 56.36 | A | C |
| ATOM | 2323 | O | GLY | A | 353 | 37.757 | 48.812 | 29.890 | 1.00 | 56.36 | A | O |
| ATOM | 2324 | N | ARG | A | 354 | 39.201 | 47.880 | 31.371 | 1.00 | 54.38 | A | N |
| ATOM | 2325 | CA | ARG | A | 354 | 38.849 | 46.479 | 31.102 | 1.00 | 54.38 | A | C |
| ATOM | 2326 | CB | ARG | A | 354 | 39.243 | 45.600 | 32.277 | 1.00 | 64.32 | A | C |
| ATOM | 2327 | CG | ARG | A | 354 | 40.705 | 45.465 | 32.560 | 1.00 | 64.32 | A | C |
| ATOM | 2328 | CD | ARG | A | 354 | 40.858 | 45.002 | 33.989 | 1.00 | 64.32 | A | C |
| ATOM | 2329 | NE | ARG | A | 354 | 41.811 | 43.907 | 34.149 | 1.00 | 64.32 | A | N |
| ATOM | 2330 | CZ | ARG | A | 354 | 42.752 | 43.880 | 35.095 | 1.00 | 64.32 | A | C |
| ATOM | 2331 | NH1 | ARG | A | 354 | 42.862 | 44.894 | 35.954 | 1.00 | 64.32 | A | N |
| ATOM | 2332 | NH2 | ARG | A | 354 | 43.575 | 42.842 | 35.193 | 1.00 | 64.32 | A | N |
| ATOM | 2333 | C | ARG | A | 354 | 37.377 | 46.163 | 30.854 | 1.00 | 54.38 | A | C |
| ATOM | 2334 | O | ARG | A | 354 | 36.497 | 47.027 | 30.897 | 1.00 | 54.38 | A | O |
| ATOM | 2335 | N | ASP | A | 355 | 37.118 | 44.875 | 30.664 | 1.00 | 54.92 | A | N |
| ATOM | 2336 | CA | ASP | A | 355 | 35.769 | 44.401 | 30.431 | 1.00 | 54.92 | A | C |
| ATOM | 2337 | CB | ASP | A | 355 | 35.790 | 43.168 | 29.547 | 1.00 | 61.21 | A | C |

FIG. 6-40

```
ATOM   2338  CG   ASP A 355      34.822  43.274  28.401  1.00 61.21           A    C
ATOM   2339  OD1  ASP A 355      33.617  43.557  28.629  1.00 61.21           A    O
ATOM   2340  OD2  ASP A 355      35.279  43.078  27.262  1.00 61.21           A    O
ATOM   2341  C    ASP A 355      35.182  44.027  31.769  1.00 54.92           A    C
ATOM   2342  O    ASP A 355      35.917  43.926  32.753  1.00 54.92           A    O
ATOM   2343  N    THR A 356      33.868  43.821  31.826  1.00 33.41           A    N
ATOM   2344  CA   THR A 356      33.280  43.424  33.095  1.00 33.41           A    C
ATOM   2345  CB   THR A 356      31.766  43.744  33.214  1.00 32.80           A    C
ATOM   2346  OG1  THR A 356      31.027  42.914  32.319  1.00 32.80           A    O
ATOM   2347  CG2  THR A 356      31.492  45.208  32.908  1.00 32.80           A    C
ATOM   2348  C    THR A 356      33.457  41.918  33.211  1.00 33.41           A    C
ATOM   2349  O    THR A 356      33.768  41.240  32.240  1.00 33.41           A    O
ATOM   2350  N    PRO A 357      33.278  41.375  34.413  1.00 22.19           A    N
ATOM   2351  CD   PRO A 357      32.895  42.021  35.682  1.00 42.65           A    C
ATOM   2352  CA   PRO A 357      33.437  39.926  34.569  1.00 22.19           A    C
ATOM   2353  CB   PRO A 357      33.323  39.711  36.081  1.00 42.65           A    C
ATOM   2354  CG   PRO A 357      33.508  41.111  36.682  1.00 42.65           A    C
ATOM   2355  C    PRO A 357      32.297  39.224  33.848  1.00 22.19           A    C
ATOM   2356  O    PRO A 357      31.454  39.864  33.222  1.00 22.19           A    O
ATOM   2357  N    ALA A 358      32.275  37.901  33.974  1.00 48.19           A    N
ATOM   2358  CA   ALA A 358      31.256  37.061  33.358  1.00 48.19           A    C
ATOM   2359  CB   ALA A 358      31.718  35.625  33.359  1.00 55.58           A    C
ATOM   2360  C    ALA A 358      29.942  37.193  34.122  1.00 48.19           A    C
ATOM   2361  O    ALA A 358      29.816  36.654  35.217  1.00 48.19           A    O
ATOM   2362  N    LEU A 359      28.965  37.891  33.545  1.00 28.69           A    N
ATOM   2363  CA   LEU A 359      27.691  38.097  34.224  1.00 28.69           A    C
ATOM   2364  CB   LEU A 359      27.344  39.581  34.227  1.00 19.29           A    C
ATOM   2365  CG   LEU A 359      28.413  40.546  34.715  1.00 19.29           A    C
ATOM   2366  CD1  LEU A 359      28.027  41.942  34.279  1.00 19.29           A    C
ATOM   2367  CD2  LEU A 359      28.557  40.459  36.225  1.00 19.29           A    C
ATOM   2368  C    LEU A 359      26.496  37.344  33.655  1.00 28.69           A    C
ATOM   2369  O    LEU A 359      25.415  37.361  34.250  1.00 28.69           A    O
ATOM   2370  N    PHE A 360      26.667  36.686  32.513  1.00 16.37           A    N
ATOM   2371  CA   PHE A 360      25.538  35.988  31.912  1.00 16.37           A    C
ATOM   2372  CB   PHE A 360      25.179  36.690  30.610  1.00 21.72           A    C
ATOM   2373  CG   PHE A 360      25.151  38.182  30.737  1.00 21.72           A    C
ATOM   2374  CD1  PHE A 360      24.217  38.801  31.554  1.00 21.72           A    C
ATOM   2375  CD2  PHE A 360      26.090  38.973  30.078  1.00 21.72           A    C
ATOM   2376  CE1  PHE A 360      24.220  40.193  31.715  1.00 21.72           A    C
ATOM   2377  CE2  PHE A 360      26.100  40.353  30.235  1.00 21.72           A    C
ATOM   2378  CZ   PHE A 360      25.166  40.965  31.053  1.00 21.72           A    C
ATOM   2379  C    PHE A 360      25.669  34.478  31.694  1.00 16.37           A    C
ATOM   2380  O    PHE A 360      24.750  33.839  31.197  1.00 16.37           A    O
ATOM   2381  N    ASN A 361      26.798  33.908  32.090  1.00 19.29           A    N
ATOM   2382  CA   ASN A 361      27.026  32.481  31.932  1.00 19.29           A    C
ATOM   2383  CB   ASN A 361      28.519  32.185  32.128  1.00 26.28           A    C
ATOM   2384  CG   ASN A 361      29.066  32.741  33.436  1.00 26.28           A    C
ATOM   2385  OD1  ASN A 361      28.379  33.480  34.155  1.00 26.28           A    O
ATOM   2386  ND2  ASN A 361      30.315  32.393  33.750  1.00 26.28           A    N
ATOM   2387  C    ASN A 361      26.150  31.603  32.851  1.00 19.29           A    C
ATOM   2388  O    ASN A 361      26.614  30.619  33.441  1.00 19.29           A    O
ATOM   2389  N    PHE A 362      24.870  31.958  32.946  1.00 33.58           A    N
ATOM   2390  CA   PHE A 362      23.910  31.240  33.787  1.00 33.58           A    C
ATOM   2391  CB   PHE A 362      22.523  31.886  33.677  1.00 29.79           A    C
ATOM   2392  CG   PHE A 362      22.409  33.227  34.349  1.00 29.79           A    C
ATOM   2393  CD1  PHE A 362      22.484  33.338  35.728  1.00 29.79           A    C
ATOM   2394  CD2  PHE A 362      22.166  34.375  33.599  1.00 29.79           A    C
ATOM   2395  CE1  PHE A 362      22.323  34.573  36.347  1.00 29.79           A    C
ATOM   2396  CE2  PHE A 362      22.005  35.609  34.206  1.00 29.79           A    C
ATOM   2397  CZ   PHE A 362      22.077  35.710  35.582  1.00 29.79           A    C
```

FIG. 6-41

```
ATOM   2398  C    PHE A 362      23.773  29.768  33.421  1.00 33.58      A  C
ATOM   2399  O    PHE A 362      23.881  29.408  32.253  1.00 33.58      A  O
ATOM   2400  N    THR A 363      23.530  28.921  34.416  1.00 30.86      A  N
ATOM   2401  CA   THR A 363      23.329  27.491  34.173  1.00 30.86      A  C
ATOM   2402  CB   THR A 363      24.059  26.606  35.204  1.00 16.07      A  C
ATOM   2403  OG1  THR A 363      23.635  26.968  36.525  1.00 16.07      A  O
ATOM   2404  CG2  THR A 363      25.578  26.742  35.066  1.00 16.07      A  C
ATOM   2405  C    THR A 363      21.839  27.225  34.337  1.00 30.86      A  C
ATOM   2406  O    THR A 363      21.091  28.116  34.768  1.00 30.86      A  O
ATOM   2407  N    THR A 364      21.398  26.015  33.999  1.00 39.51      A  N
ATOM   2408  CA   THR A 364      19.979  25.695  34.138  1.00 39.51      A  C
ATOM   2409  CB   THR A 364      19.614  24.406  33.382  1.00 39.12      A  C
ATOM   2410  OG1  THR A 364      20.506  23.360  33.777  1.00 39.12      A  O
ATOM   2411  CG2  THR A 364      19.715  24.629  31.864  1.00 39.12      A  C
ATOM   2412  C    THR A 364      19.659  25.551  35.613  1.00 39.51      A  C
ATOM   2413  O    THR A 364      18.537  25.821  36.039  1.00 39.51      A  O
ATOM   2414  N    GLN A 365      20.666  25.132  36.379  1.00 36.75      A  N
ATOM   2415  CA   GLN A 365      20.573  24.962  37.833  1.00 36.75      A  C
ATOM   2416  CB   GLN A 365      21.894  24.367  38.346  1.00 47.16      A  C
ATOM   2417  CG   GLN A 365      22.070  24.335  39.862  1.00 47.16      A  C
ATOM   2418  CD   GLN A 365      21.009  23.497  40.549  1.00 47.16      A  C
ATOM   2419  OE1  GLN A 365      20.071  23.019  39.897  1.00 47.16      A  O
ATOM   2420  NE2  GLN A 365      21.138  23.319  41.872  1.00 47.16      A  N
ATOM   2421  C    GLN A 365      20.365  26.339  38.450  1.00 36.75      A  C
ATOM   2422  O    GLN A 365      19.545  26.530  39.339  1.00 36.75      A  O
ATOM   2423  N    GLU A 366      21.133  27.292  37.946  1.00 37.67      A  N
ATOM   2424  CA   GLU A 366      21.102  28.665  38.403  1.00 37.67      A  C
ATOM   2425  CB   GLU A 366      22.240  29.422  37.694  1.00 37.36      A  C
ATOM   2426  CG   GLU A 366      22.602  30.784  38.261  1.00 37.36      A  C
ATOM   2427  CD   GLU A 366      24.055  31.181  37.966  1.00 37.36      A  C
ATOM   2428  OE1  GLU A 366      24.463  32.297  38.366  1.00 37.36      A  O
ATOM   2429  OE2  GLU A 366      24.791  30.374  37.346  1.00 37.36      A  O
ATOM   2430  C    GLU A 366      19.752  29.304  38.108  1.00 37.67      A  C
ATOM   2431  O    GLU A 366      19.254  30.105  38.904  1.00 37.67      A  O
ATOM   2432  N    LEU A 367      19.152  28.927  36.981  1.00 25.31      A  N
ATOM   2433  CA   LEU A 367      17.872  29.496  36.550  1.00 25.31      A  C
ATOM   2434  CB   LEU A 367      17.909  29.693  35.029  1.00 31.66      A  C
ATOM   2435  CG   LEU A 367      18.921  30.735  34.509  1.00 31.66      A  C
ATOM   2436  CD1  LEU A 367      19.415  30.364  33.113  1.00 31.66      A  C
ATOM   2437  CD2  LEU A 367      18.272  32.117  34.512  1.00 31.66      A  C
ATOM   2438  C    LEU A 367      16.617  28.704  36.947  1.00 25.31      A  C
ATOM   2439  O    LEU A 367      15.485  29.176  36.778  1.00 25.31      A  O
ATOM   2440  N    SER A 368      16.825  27.513  37.496  1.00 20.65      A  N
ATOM   2441  CA   SER A 368      15.730  26.652  37.890  1.00 20.65      A  C
ATOM   2442  CB   SER A 368      16.280  25.457  38.653  1.00 28.35      A  C
ATOM   2443  OG   SER A 368      17.176  25.873  39.652  1.00 28.35      A  O
ATOM   2444  C    SER A 368      14.605  27.318  38.669  1.00 20.65      A  C
ATOM   2445  O    SER A 368      13.446  26.962  38.501  1.00 20.65      A  O
ATOM   2446  N    SER A 369      14.931  28.284  39.516  1.00 34.66      A  N
ATOM   2447  CA   SER A 369      13.905  28.979  40.295  1.00 34.66      A  C
ATOM   2448  CB   SER A 369      14.541  30.112  41.106  1.00 33.79      A  C
ATOM   2449  OG   SER A 369      15.471  30.836  40.320  1.00 33.79      A  O
ATOM   2450  C    SER A 369      12.808  29.548  39.400  1.00 34.66      A  C
ATOM   2451  O    SER A 369      11.645  29.612  39.789  1.00 34.66      A  O
ATOM   2452  N    ASN A 370      13.191  29.951  38.194  1.00 35.26      A  N
ATOM   2453  CA   ASN A 370      12.256  30.550  37.247  1.00 35.26      A  C
ATOM   2454  CB   ASN A 370      11.783  31.898  37.776  1.00 37.19      A  C
ATOM   2455  CG   ASN A 370      10.816  32.572  36.848  1.00 37.19      A  C
ATOM   2456  OD1  ASN A 370      10.690  33.790  36.866  1.00 37.19      A  O
ATOM   2457  ND2  ASN A 370      10.111  31.787  36.033  1.00 37.19      A  N
```

FIG. 6-42

```
ATOM   2458  C   ASN A 370      12.961  30.739  35.900  1.00 35.26      A    C
ATOM   2459  O   ASN A 370      13.481  31.814  35.599  1.00 35.26      A    O
ATOM   2460  N   PRO A 371      12.970  29.686  35.066  1.00 34.97      A    N
ATOM   2461  CD  PRO A 371      12.208  28.449  35.327  1.00 15.23      A    C
ATOM   2462  CA  PRO A 371      13.594  29.639  33.736  1.00 34.97      A    C
ATOM   2463  CB  PRO A 371      13.082  28.315  33.169  1.00 15.23      A    C
ATOM   2464  CG  PRO A 371      12.865  27.482  34.402  1.00 15.23      A    C
ATOM   2465  C   PRO A 371      13.303  30.814  32.799  1.00 34.97      A    C
ATOM   2466  O   PRO A 371      14.218  31.420  32.255  1.00 34.97      A    O
ATOM   2467  N   PRO A 372      12.021  31.149  32.593  1.00 27.53      A    N
ATOM   2468  CD  PRO A 372      10.793  30.557  33.143  1.00 21.88      A    C
ATOM   2469  CA  PRO A 372      11.686  32.259  31.702  1.00 27.53      A    C
ATOM   2470  CB  PRO A 372      10.156  32.294  31.749  1.00 21.88      A    C
ATOM   2471  CG  PRO A 372       9.834  31.717  33.051  1.00 21.88      A    C
ATOM   2472  C   PRO A 372      12.321  33.612  31.991  1.00 27.53      A    C
ATOM   2473  O   PRO A 372      11.998  34.598  31.336  1.00 27.53      A    O
ATOM   2474  N   LEU A 373      13.216  33.673  32.968  1.00 34.78      A    N
ATOM   2475  CA  LEU A 373      13.877  34.938  33.266  1.00 34.78      A    C
ATOM   2476  CB  LEU A 373      14.281  35.036  34.738  1.00 28.61      A    C
ATOM   2477  CG  LEU A 373      13.158  35.385  35.718  1.00 28.61      A    C
ATOM   2478  CD1 LEU A 373      13.753  35.690  37.099  1.00 28.61      A    C
ATOM   2479  CD2 LEU A 373      12.377  36.588  35.190  1.00 28.61      A    C
ATOM   2480  C   LEU A 373      15.104  35.062  32.391  1.00 34.78      A    C
ATOM   2481  O   LEU A 373      15.615  36.159  32.178  1.00 34.78      A    O
ATOM   2482  N   ALA A 374      15.573  33.923  31.890  1.00 50.14      A    N
ATOM   2483  CA  ALA A 374      16.729  33.901  31.005  1.00 50.14      A    C
ATOM   2484  CB  ALA A 374      16.844  32.545  30.330  1.00 36.86      A    C
ATOM   2485  C   ALA A 374      16.555  34.994  29.956  1.00 50.14      A    C
ATOM   2486  O   ALA A 374      17.509  35.695  29.605  1.00 50.14      A    O
ATOM   2487  N   THR A 375      15.317  35.142  29.486  1.00 34.91      A    N
ATOM   2488  CA  THR A 375      14.955  36.130  28.466  1.00 34.91      A    C
ATOM   2489  CB  THR A 375      13.418  36.058  28.161  1.00 33.40      A    C
ATOM   2490  OG1 THR A 375      12.669  36.663  29.229  1.00 33.40      A    O
ATOM   2491  CG2 THR A 375      12.976  34.605  28.018  1.00 33.40      A    C
ATOM   2492  C   THR A 375      15.314  37.561  28.864  1.00 34.91      A    C
ATOM   2493  O   THR A 375      15.206  38.485  28.067  1.00 34.91      A    O
ATOM   2494  N   ILE A 376      15.705  37.756  30.112  1.00 31.61      A    N
ATOM   2495  CA  ILE A 376      16.104  39.079  30.548  1.00 31.61      A    C
ATOM   2496  CB  ILE A 376      15.224  39.602  31.676  1.00 22.89      A    C
ATOM   2497  CG2 ILE A 376      15.783  40.916  32.179  1.00 22.89      A    C
ATOM   2498  CG1 ILE A 376      13.790  39.783  31.186  1.00 22.89      A    C
ATOM   2499  CD1 ILE A 376      12.895  40.491  32.183  1.00 22.89      A    C
ATOM   2500  C   ILE A 376      17.521  38.954  31.061  1.00 31.61      A    C
ATOM   2501  O   ILE A 376      18.372  39.787  30.776  1.00 31.61      A    O
ATOM   2502  N   LEU A 377      17.772  37.885  31.799  1.00 36.14      A    N
ATOM   2503  CA  LEU A 377      19.085  37.654  32.357  1.00 36.14      A    C
ATOM   2504  CB  LEU A 377      19.031  36.417  33.255  1.00 28.44      A    C
ATOM   2505  CG  LEU A 377      18.157  36.724  34.477  1.00 28.44      A    C
ATOM   2506  CD1 LEU A 377      17.746  35.452  35.170  1.00 28.44      A    C
ATOM   2507  CD2 LEU A 377      18.917  37.656  35.419  1.00 28.44      A    C
ATOM   2508  C   LEU A 377      20.185  37.557  31.306  1.00 36.14      A    C
ATOM   2509  O   LEU A 377      21.228  38.177  31.467  1.00 36.14      A    O
ATOM   2510  N   ILE A 378      19.963  36.803  30.231  1.00 32.93      A    N
ATOM   2511  CA  ILE A 378      20.973  36.685  29.166  1.00 32.93      A    C
ATOM   2512  CB  ILE A 378      20.952  35.299  28.491  1.00 11.15      A    C
ATOM   2513  CG2 ILE A 378      22.005  35.254  27.423  1.00 11.15      A    C
ATOM   2514  CG1 ILE A 378      21.196  34.188  29.504  1.00 11.15      A    C
ATOM   2515  CD1 ILE A 378      20.004  33.880  30.348  1.00 11.15      A    C
ATOM   2516  C   ILE A 378      20.674  37.707  28.063  1.00 32.93      A    C
ATOM   2517  O   ILE A 378      19.805  37.473  27.228  1.00 32.93      A    O
```

FIG. 6-43

```
ATOM   2518  N    PRO A 379      21.385  38.853  28.043  1.00 50.49      A  N
ATOM   2519  CD   PRO A 379      22.459  39.315  28.942  1.00 26.95      A  C
ATOM   2520  CA   PRO A 379      21.113  39.846  26.995  1.00 50.49      A  C
ATOM   2521  CB   PRO A 379      21.962  41.043  27.422  1.00 26.95      A  C
ATOM   2522  CG   PRO A 379      23.112  40.418  28.135  1.00 26.95      A  C
ATOM   2523  C    PRO A 379      21.408  39.339  25.576  1.00 50.49      A  C
ATOM   2524  O    PRO A 379      22.232  38.434  25.379  1.00 50.49      A  O
ATOM   2525  N    PRO A 380      20.722  39.909  24.573  1.00 30.62      A  N
ATOM   2526  CD   PRO A 380      19.705  40.970  24.684  1.00 29.17      A  C
ATOM   2527  CA   PRO A 380      20.906  39.509  23.179  1.00 30.62      A  C
ATOM   2528  CB   PRO A 380      20.255  40.649  22.418  1.00 29.17      A  C
ATOM   2529  CG   PRO A 380      19.075  40.966  23.304  1.00 29.17      A  C
ATOM   2530  C    PRO A 380      22.344  39.248  22.780  1.00 30.62      A  C
ATOM   2531  O    PRO A 380      22.654  38.170  22.276  1.00 30.62      A  O
ATOM   2532  N    HIS A 381      23.234  40.203  23.023  1.00 21.55      A  N
ATOM   2533  CA   HIS A 381      24.620  39.995  22.646  1.00 21.55      A  C
ATOM   2534  CB   HIS A 381      25.397  41.309  22.790  1.00 30.89      A  C
ATOM   2535  CG   HIS A 381      25.501  41.809  24.197  1.00 30.89      A  C
ATOM   2536  CD2  HIS A 381      24.703  42.640  24.910  1.00 30.89      A  C
ATOM   2537  ND1  HIS A 381      26.507  41.416  25.054  1.00 30.89      A  N
ATOM   2538  CE1  HIS A 381      26.324  41.982  26.234  1.00 30.89      A  C
ATOM   2539  NE2  HIS A 381      25.237  42.728  26.174  1.00 30.89      A  N
ATOM   2540  C    HIS A 381      25.284  38.855  23.428  1.00 21.55      A  C
ATOM   2541  O    HIS A 381      24.680  38.332  24.406  1.00 21.55      A  O
ATOM   2542  OXT  HIS A 381      26.416  38.490  23.029  1.00 30.89      A  O
TER    2543       HIS A 381                                              A
ATOM   2544  CB   VAL B  37      15.131  80.790  77.616  1.00 47.59      B  C
ATOM   2545  CG1  VAL B  37      14.611  81.253  76.246  1.00 47.59      B  C
ATOM   2546  CG2  VAL B  37      16.523  81.372  77.882  1.00 47.59      B  C
ATOM   2547  C    VAL B  37      12.855  80.373  78.592  1.00 57.05      B  C
ATOM   2548  O    VAL B  37      11.750  80.925  78.640  1.00 57.05      B  O
ATOM   2549  N    VAL B  37      14.721  81.136  80.095  1.00 57.05      B  N
ATOM   2550  CA   VAL B  37      14.127  81.225  78.722  1.00 57.05      B  C
ATOM   2551  N    THR B  38      12.982  79.048  78.440  1.00 36.93      B  N
ATOM   2552  CA   THR B  38      11.781  78.207  78.316  1.00 36.93      B  C
ATOM   2553  CB   THR B  38      12.105  76.829  77.671  1.00 52.44      B  C
ATOM   2554  OG1  THR B  38      12.653  77.028  76.359  1.00 52.44      B  O
ATOM   2555  CG2  THR B  38      10.833  75.989  77.534  1.00 52.44      B  C
ATOM   2556  C    THR B  38      11.032  77.986  79.637  1.00 36.93      B  C
ATOM   2557  O    THR B  38      11.623  77.626  80.659  1.00 36.93      B  O
ATOM   2558  N    THR B  39       9.723  78.235  79.600  1.00 28.99      B  N
ATOM   2559  CA   THR B  39       8.850  78.072  80.765  1.00 28.99      B  C
ATOM   2560  CB   THR B  39       8.189  79.390  81.191  1.00 45.61      B  C
ATOM   2561  OG1  THR B  39       9.196  80.374  81.464  1.00 45.61      B  O
ATOM   2562  CG2  THR B  39       7.352  79.165  82.434  1.00 45.61      B  C
ATOM   2563  C    THR B  39       7.739  77.121  80.370  1.00 28.99      B  C
ATOM   2564  O    THR B  39       7.103  77.288  79.327  1.00 28.99      B  O
ATOM   2565  N    VAL B  40       7.482  76.140  81.223  1.00 28.06      B  N
ATOM   2566  CA   VAL B  40       6.473  75.142  80.917  1.00 28.06      B  C
ATOM   2567  CB   VAL B  40       7.170  73.902  80.269  1.00 22.26      B  C
ATOM   2568  CG1  VAL B  40       7.757  72.993  81.341  1.00 22.26      B  C
ATOM   2569  CG2  VAL B  40       6.203  73.165  79.373  1.00 22.26      B  C
ATOM   2570  C    VAL B  40       5.747  74.755  82.200  1.00 28.06      B  C
ATOM   2571  O    VAL B  40       6.197  75.090  83.293  1.00 28.06      B  O
ATOM   2572  N    VAL B  41       4.617  74.069  82.062  1.00 15.23      B  N
ATOM   2573  CA   VAL B  41       3.838  73.643  83.214  1.00 15.23      B  C
ATOM   2574  CB   VAL B  41       2.356  74.057  83.055  1.00 16.51      B  C
ATOM   2575  CG1  VAL B  41       1.541  73.576  84.245  1.00 16.51      B  C
ATOM   2576  CG2  VAL B  41       2.256  75.580  82.938  1.00 16.51      B  C
ATOM   2577  C    VAL B  41       3.981  72.134  83.305  1.00 15.23      B  C
```

FIG. 6-44

| ATOM | 2578 | O | VAL | B | 41 | 3.457 | 71.408 | 82.481 | 1.00 | 15.23 | B | O |
| ATOM | 2579 | N | ALA | B | 42 | 4.702 | 71.669 | 84.318 | 1.00 | 29.57 | B | N |
| ATOM | 2580 | CA | ALA | B | 42 | 4.972 | 70.248 | 84.480 | 1.00 | 29.57 | B | C |
| ATOM | 2581 | CB | ALA | B | 42 | 6.484 | 70.009 | 84.456 | 1.00 | 17.99 | B | C |
| ATOM | 2582 | C | ALA | B | 42 | 4.384 | 69.597 | 85.709 | 1.00 | 29.57 | B | C |
| ATOM | 2583 | O | ALA | B | 42 | 4.047 | 70.263 | 86.687 | 1.00 | 29.57 | B | O |
| ATOM | 2584 | N | THR | B | 43 | 4.303 | 68.270 | 85.641 | 1.00 | 30.78 | B | N |
| ATOM | 2585 | CA | THR | B | 43 | 3.759 | 67.442 | 86.702 | 1.00 | 30.78 | B | C |
| ATOM | 2586 | CB | THR | B | 43 | 2.829 | 66.375 | 86.118 | 1.00 | 32.42 | B | C |
| ATOM | 2587 | OG1 | THR | B | 43 | 1.763 | 67.019 | 85.416 | 1.00 | 32.42 | B | O |
| ATOM | 2588 | CG2 | THR | B | 43 | 2.265 | 65.476 | 87.214 | 1.00 | 32.42 | B | C |
| ATOM | 2589 | C | THR | B | 43 | 4.884 | 66.742 | 87.454 | 1.00 | 30.78 | B | C |
| ATOM | 2590 | O | THR | B | 43 | 5.773 | 66.130 | 86.844 | 1.00 | 30.78 | B | O |
| ATOM | 2591 | N | PRO | B | 44 | 4.880 | 66.846 | 88.789 | 1.00 | 26.31 | B | N |
| ATOM | 2592 | CD | PRO | B | 44 | 4.140 | 67.872 | 89.543 | 1.00 | 30.53 | B | C |
| ATOM | 2593 | CA | PRO | B | 44 | 5.889 | 66.218 | 89.644 | 1.00 | 26.31 | B | C |
| ATOM | 2594 | CB | PRO | B | 44 | 5.461 | 66.650 | 91.037 | 1.00 | 30.53 | B | C |
| ATOM | 2595 | CG | PRO | B | 44 | 5.000 | 68.040 | 90.786 | 1.00 | 30.53 | B | C |
| ATOM | 2596 | C | PRO | B | 44 | 5.948 | 64.704 | 89.496 | 1.00 | 26.31 | B | C |
| ATOM | 2597 | O | PRO | B | 44 | 4.915 | 64.033 | 89.432 | 1.00 | 26.31 | B | O |
| ATOM | 2598 | N | GLY | B | 45 | 7.174 | 64.184 | 89.443 | 1.00 | 30.08 | B | N |
| ATOM | 2599 | CA | GLY | B | 45 | 7.392 | 62.757 | 89.287 | 1.00 | 30.08 | B | C |
| ATOM | 2600 | C | GLY | B | 45 | 6.617 | 61.959 | 90.306 | 1.00 | 30.08 | B | C |
| ATOM | 2601 | O | GLY | B | 45 | 5.934 | 60.988 | 89.971 | 1.00 | 30.08 | B | O |
| ATOM | 2602 | N | ALA | B | 46 | 6.717 | 62.377 | 91.560 | 1.00 | 42.85 | B | N |
| ATOM | 2603 | CA | ALA | B | 46 | 6.022 | 61.686 | 92.631 | 1.00 | 42.85 | B | C |
| ATOM | 2604 | CB | ALA | B | 46 | 6.904 | 61.634 | 93.877 | 1.00 | 55.45 | B | C |
| ATOM | 2605 | C | ALA | B | 46 | 4.703 | 62.387 | 92.947 | 1.00 | 42.85 | B | C |
| ATOM | 2606 | O | ALA | B | 46 | 4.094 | 63.028 | 92.083 | 1.00 | 42.85 | B | O |
| ATOM | 2607 | N | GLY | B | 47 | 4.269 | 62.243 | 94.194 | 1.00 | 62.50 | B | N |
| ATOM | 2608 | CA | GLY | B | 47 | 3.036 | 62.858 | 94.655 | 1.00 | 62.50 | B | C |
| ATOM | 2609 | C | GLY | B | 47 | 1.830 | 62.804 | 93.730 | 1.00 | 62.50 | B | C |
| ATOM | 2610 | O | GLY | B | 47 | 1.783 | 62.030 | 92.772 | 1.00 | 62.50 | B | O |
| ATOM | 2611 | N | PRO | B | 48 | 0.814 | 63.631 | 94.013 | 1.00 | 87.34 | B | N |
| ATOM | 2612 | CD | PRO | B | 48 | 0.832 | 64.632 | 95.104 | 1.00 | 67.66 | B | C |
| ATOM | 2613 | CA | PRO | B | 48 | -0.423 | 63.715 | 93.218 | 1.00 | 87.34 | B | C |
| ATOM | 2614 | CB | PRO | B | 48 | -1.364 | 64.446 | 94.158 | 1.00 | 67.66 | B | C |
| ATOM | 2615 | CG | PRO | B | 48 | -0.397 | 65.461 | 94.819 | 1.00 | 67.66 | B | C |
| ATOM | 2616 | C | PRO | B | 48 | -0.083 | 64.559 | 91.987 | 1.00 | 87.34 | B | C |
| ATOM | 2617 | O | PRO | B | 48 | 1.054 | 65.009 | 91.861 | 1.00 | 87.34 | B | O |
| ATOM | 2618 | N | ASP | B | 49 | -1.033 | 64.803 | 91.092 | 1.00 | 46.29 | B | N |
| ATOM | 2619 | CA | ASP | B | 49 | -0.702 | 65.619 | 89.922 | 1.00 | 46.29 | B | C |
| ATOM | 2620 | CB | ASP | B | 49 | -1.410 | 65.089 | 88.669 | 1.00 | 50.78 | B | C |
| ATOM | 2621 | CG | ASP | B | 49 | -1.230 | 63.583 | 88.493 | 1.00 | 50.78 | B | C |
| ATOM | 2622 | OD1 | ASP | B | 49 | -1.193 | 63.105 | 87.327 | 1.00 | 50.78 | B | O |
| ATOM | 2623 | OD2 | ASP | B | 49 | -1.142 | 62.874 | 89.530 | 1.00 | 50.78 | B | O |
| ATOM | 2624 | C | ASP | B | 49 | -1.048 | 67.076 | 90.137 | 1.00 | 46.29 | B | C |
| ATOM | 2625 | O | ASP | B | 49 | -2.139 | 67.520 | 89.786 | 1.00 | 46.29 | B | O |
| ATOM | 2626 | N | ARG | B | 50 | -0.105 | 67.810 | 90.717 | 1.00 | 37.61 | B | N |
| ATOM | 2627 | CA | ARG | B | 50 | -0.282 | 69.230 | 90.984 | 1.00 | 37.61 | B | C |
| ATOM | 2628 | CB | ARG | B | 50 | -0.245 | 69.444 | 92.491 | 1.00 | 67.01 | B | C |
| ATOM | 2629 | CG | ARG | B | 50 | -1.177 | 68.404 | 93.041 | 1.00 | 67.01 | B | C |
| ATOM | 2630 | CD | ARG | B | 50 | -2.322 | 68.790 | 93.978 | 1.00 | 67.01 | B | C |
| ATOM | 2631 | NE | ARG | B | 50 | -1.789 | 68.453 | 95.324 | 1.00 | 67.01 | B | N |
| ATOM | 2632 | CZ | ARG | B | 50 | -2.140 | 67.402 | 96.184 | 1.00 | 67.01 | B | C |
| ATOM | 2633 | NH1 | ARG | B | 50 | -3.049 | 66.496 | 95.937 | 1.00 | 67.01 | B | N |
| ATOM | 2634 | NH2 | ARG | B | 50 | -1.535 | 67.272 | 97.349 | 1.00 | 67.01 | B | N |
| ATOM | 2635 | C | ARG | B | 50 | 0.792 | 70.001 | 90.236 | 1.00 | 37.61 | B | C |
| ATOM | 2636 | O | ARG | B | 50 | 1.805 | 70.417 | 90.808 | 1.00 | 37.61 | B | O |
| ATOM | 2637 | N | PRO | B | 51 | 0.590 | 70.172 | 88.916 | 1.00 | 33.49 | B | N |

FIG. 6-45

| ATOM | 2638 | CD | PRO | B | 51 | -0.438 | 69.496 | 88.113 | 1.00 | 30.36 | B | C |
|------|------|----|----|---|----|--------|--------|--------|------|-------|---|---|
| ATOM | 2639 | CA | PRO | B | 51 | 1.519 | 70.888 | 88.041 | 1.00 | 33.49 | B | C |
| ATOM | 2640 | CB | PRO | B | 51 | 0.909 | 70.715 | 86.643 | 1.00 | 30.36 | B | C |
| ATOM | 2641 | CG | PRO | B | 51 | -0.493 | 70.368 | 86.894 | 1.00 | 30.36 | B | C |
| ATOM | 2642 | C | PRO | B | 51 | 1.851 | 72.325 | 88.366 | 1.00 | 33.49 | B | C |
| ATOM | 2643 | O | PRO | B | 51 | 0.983 | 73.120 | 88.708 | 1.00 | 33.49 | B | O |
| ATOM | 2644 | N | GLN | B | 52 | 3.133 | 72.648 | 88.260 | 1.00 | 31.33 | B | N |
| ATOM | 2645 | CA | GLN | B | 52 | 3.578 | 73.993 | 88.526 | 1.00 | 31.33 | B | C |
| ATOM | 2646 | CB | GLN | B | 52 | 4.326 | 74.062 | 89.858 | 1.00 | 58.78 | B | C |
| ATOM | 2647 | CG | GLN | B | 52 | 4.630 | 75.501 | 90.351 | 1.00 | 58.78 | B | C |
| ATOM | 2648 | CD | GLN | B | 52 | 3.527 | 76.529 | 90.026 | 1.00 | 58.78 | B | C |
| ATOM | 2649 | OE1 | GLN | B | 52 | 2.326 | 76.214 | 90.087 | 1.00 | 58.78 | B | O |
| ATOM | 2650 | NE2 | GLN | B | 52 | 3.936 | 77.768 | 89.693 | 1.00 | 58.78 | B | N |
| ATOM | 2651 | C | GLN | B | 52 | 4.438 | 74.471 | 87.386 | 1.00 | 31.33 | B | C |
| ATOM | 2652 | O | GLN | B | 52 | 4.856 | 73.666 | 86.568 | 1.00 | 31.33 | B | O |
| ATOM | 2653 | N | GLU | B | 53 | 4.670 | 75.781 | 87.304 | 1.00 | 40.33 | B | N |
| ATOM | 2654 | CA | GLU | B | 53 | 5.511 | 76.324 | 86.249 | 1.00 | 40.33 | B | C |
| ATOM | 2655 | CB | GLU | B | 53 | 5.248 | 77.836 | 86.073 | 1.00 | 63.35 | B | C |
| ATOM | 2656 | CG | GLU | B | 53 | 3.899 | 78.137 | 85.354 | 1.00 | 63.35 | B | C |
| ATOM | 2657 | CD | GLU | B | 53 | 3.180 | 79.441 | 85.806 | 1.00 | 63.35 | B | C |
| ATOM | 2658 | OE1 | GLU | B | 53 | 3.442 | 79.916 | 86.937 | 1.00 | 63.35 | B | O |
| ATOM | 2659 | OE2 | GLU | B | 53 | 2.329 | 79.974 | 85.036 | 1.00 | 63.35 | B | O |
| ATOM | 2660 | C | GLU | B | 53 | 6.960 | 76.019 | 86.586 | 1.00 | 40.33 | B | C |
| ATOM | 2661 | O | GLU | B | 53 | 7.353 | 76.033 | 87.755 | 1.00 | 40.33 | B | O |
| ATOM | 2662 | N | VAL | B | 54 | 7.722 | 75.661 | 85.559 | 1.00 | 27.34 | B | N |
| ATOM | 2663 | CA | VAL | B | 54 | 9.132 | 75.357 | 85.699 | 1.00 | 27.34 | B | C |
| ATOM | 2664 | CB | VAL | B | 54 | 9.388 | 73.854 | 85.595 | 1.00 | 15.49 | B | C |
| ATOM | 2665 | CG1 | VAL | B | 54 | 10.873 | 73.565 | 85.722 | 1.00 | 15.49 | B | C |
| ATOM | 2666 | CG2 | VAL | B | 54 | 8.619 | 73.141 | 86.685 | 1.00 | 15.49 | B | C |
| ATOM | 2667 | C | VAL | B | 54 | 9.801 | 76.087 | 84.565 | 1.00 | 27.34 | B | C |
| ATOM | 2668 | O | VAL | B | 54 | 9.280 | 76.097 | 83.442 | 1.00 | 27.34 | B | O |
| ATOM | 2669 | N | SER | B | 55 | 10.925 | 76.735 | 84.866 | 1.00 | 51.28 | B | N |
| ATOM | 2670 | CA | SER | B | 55 | 11.678 | 77.468 | 83.847 | 1.00 | 51.28 | B | C |
| ATOM | 2671 | CB | SER | B | 55 | 11.601 | 78.976 | 84.108 | 1.00 | 57.71 | B | C |
| ATOM | 2672 | OG | SER | B | 55 | 10.302 | 79.477 | 83.805 | 1.00 | 57.71 | B | O |
| ATOM | 2673 | C | SER | B | 55 | 13.122 | 77.013 | 83.778 | 1.00 | 51.28 | B | C |
| ATOM | 2674 | O | SER | B | 55 | 13.793 | 76.876 | 84.802 | 1.00 | 51.28 | B | O |
| ATOM | 2675 | N | TYR | B | 56 | 13.592 | 76.759 | 82.565 | 1.00 | 40.91 | B | N |
| ATOM | 2676 | CA | TYR | B | 56 | 14.968 | 76.321 | 82.369 | 1.00 | 40.91 | B | C |
| ATOM | 2677 | CB | TYR | B | 56 | 15.025 | 74.801 | 82.227 | 1.00 | 18.59 | B | C |
| ATOM | 2678 | CG | TYR | B | 56 | 14.267 | 74.252 | 81.043 | 1.00 | 18.59 | B | C |
| ATOM | 2679 | CD1 | TYR | B | 56 | 14.812 | 74.289 | 79.761 | 1.00 | 18.59 | B | C |
| ATOM | 2680 | CE1 | TYR | B | 56 | 14.127 | 73.764 | 78.682 | 1.00 | 18.59 | B | C |
| ATOM | 2681 | CD2 | TYR | B | 56 | 13.005 | 73.674 | 81.207 | 1.00 | 18.59 | B | C |
| ATOM | 2682 | CE2 | TYR | B | 56 | 12.312 | 73.143 | 80.126 | 1.00 | 18.59 | B | C |
| ATOM | 2683 | CZ | TYR | B | 56 | 12.882 | 73.190 | 78.873 | 1.00 | 18.59 | B | C |
| ATOM | 2684 | OH | TYR | B | 56 | 12.217 | 72.631 | 77.815 | 1.00 | 18.59 | B | O |
| ATOM | 2685 | C | TYR | B | 56 | 15.584 | 76.985 | 81.154 | 1.00 | 40.91 | B | C |
| ATOM | 2686 | O | TYR | B | 56 | 14.890 | 77.363 | 80.193 | 1.00 | 40.91 | B | O |
| ATOM | 2687 | N | THR | B | 57 | 16.903 | 77.107 | 81.203 | 1.00 | 45.57 | B | N |
| ATOM | 2688 | CA | THR | B | 57 | 17.654 | 77.753 | 80.143 | 1.00 | 45.57 | B | C |
| ATOM | 2689 | CB | THR | B | 57 | 18.056 | 79.151 | 80.624 | 1.00 | 48.29 | B | C |
| ATOM | 2690 | OG1 | THR | B | 57 | 18.588 | 79.907 | 79.534 | 1.00 | 48.29 | B | O |
| ATOM | 2691 | CG2 | THR | B | 57 | 19.096 | 79.036 | 81.727 | 1.00 | 48.29 | B | C |
| ATOM | 2692 | C | THR | B | 57 | 18.905 | 76.925 | 79.845 | 1.00 | 45.57 | B | C |
| ATOM | 2693 | O | THR | B | 57 | 19.072 | 75.838 | 80.396 | 1.00 | 45.57 | B | O |
| ATOM | 2694 | N | ASP | B | 58 | 19.773 | 77.452 | 78.982 | 1.00 | 34.14 | B | N |
| ATOM | 2695 | CA | ASP | B | 58 | 21.022 | 76.791 | 78.607 | 1.00 | 34.14 | B | C |
| ATOM | 2696 | CB | ASP | B | 58 | 22.002 | 76.775 | 79.785 | 1.00 | 54.91 | B | C |
| ATOM | 2697 | CG | ASP | B | 58 | 22.321 | 78.162 | 80.302 | 1.00 | 54.91 | B | C |

FIG. 6-46

| ATOM | 2698 | OD1 | ASP | B | 58 | 22.388 | 79.118 | 79.485 | 1.00 | 54.91 | B | O |
|------|------|-----|-----|---|----|--------|--------|--------|------|-------|---|---|
| ATOM | 2699 | OD2 | ASP | B | 58 | 22.523 | 78.287 | 81.530 | 1.00 | 54.91 | B | O |
| ATOM | 2700 | C   | ASP | B | 58 | 20.778 | 75.356 | 78.156 | 1.00 | 34.14 | B | C |
| ATOM | 2701 | O   | ASP | B | 58 | 21.453 | 74.411 | 78.590 | 1.00 | 34.14 | B | O |
| ATOM | 2702 | N   | THR | B | 59 | 19.809 | 75.189 | 77.280 | 1.00 | 40.00 | B | N |
| ATOM | 2703 | CA  | THR | B | 59 | 19.512 | 73.864 | 76.807 | 1.00 | 40.00 | B | C |
| ATOM | 2704 | CB  | THR | B | 59 | 18.140 | 73.828 | 76.170 | 1.00 | 40.48 | B | C |
| ATOM | 2705 | OG1 | THR | B | 59 | 17.204 | 74.458 | 77.055 | 1.00 | 40.48 | B | O |
| ATOM | 2706 | CG2 | THR | B | 59 | 17.718 | 72.377 | 75.912 | 1.00 | 40.48 | B | C |
| ATOM | 2707 | C   | THR | B | 59 | 20.550 | 73.434 | 75.783 | 1.00 | 40.00 | B | C |
| ATOM | 2708 | O   | THR | B | 59 | 21.054 | 74.251 | 75.016 | 1.00 | 40.00 | B | O |
| ATOM | 2709 | N   | LYS | B | 60 | 20.880 | 72.150 | 75.781 | 1.00 | 52.57 | B | N |
| ATOM | 2710 | CA  | LYS | B | 60 | 21.843 | 71.630 | 74.824 | 1.00 | 52.57 | B | C |
| ATOM | 2711 | CB  | LYS | B | 60 | 23.269 | 72.002 | 75.238 | 1.00 | 75.41 | B | C |
| ATOM | 2712 | CG  | LYS | B | 60 | 23.659 | 71.539 | 76.626 | 1.00 | 75.41 | B | C |
| ATOM | 2713 | CD  | LYS | B | 60 | 25.128 | 71.849 | 76.916 | 1.00 | 75.41 | B | C |
| ATOM | 2714 | CE  | LYS | B | 60 | 25.433 | 73.360 | 76.862 | 1.00 | 75.41 | B | C |
| ATOM | 2715 | NZ  | LYS | B | 60 | 25.021 | 74.125 | 78.094 | 1.00 | 75.41 | B | N |
| ATOM | 2716 | C   | LYS | B | 60 | 21.705 | 70.118 | 74.738 | 1.00 | 52.57 | B | C |
| ATOM | 2717 | O   | LYS | B | 60 | 21.409 | 69.445 | 75.726 | 1.00 | 52.57 | B | O |
| ATOM | 2718 | N   | VAL | B | 61 | 21.913 | 69.597 | 73.540 | 1.00 | 37.90 | B | N |
| ATOM | 2719 | CA  | VAL | B | 61 | 21.811 | 68.173 | 73.293 | 1.00 | 37.90 | B | C |
| ATOM | 2720 | CB  | VAL | B | 61 | 21.588 | 67.919 | 71.811 | 1.00 | 36.26 | B | C |
| ATOM | 2721 | CG1 | VAL | B | 61 | 21.392 | 66.436 | 71.563 | 1.00 | 36.26 | B | C |
| ATOM | 2722 | CG2 | VAL | B | 61 | 20.390 | 68.738 | 71.339 | 1.00 | 36.26 | B | C |
| ATOM | 2723 | C   | VAL | B | 61 | 23.062 | 67.435 | 73.728 | 1.00 | 37.90 | B | C |
| ATOM | 2724 | O   | VAL | B | 61 | 24.170 | 67.842 | 73.397 | 1.00 | 37.90 | B | O |
| ATOM | 2725 | N   | ILE | B | 62 | 22.882 | 66.340 | 74.461 | 1.00 | 40.49 | B | N |
| ATOM | 2726 | CA  | ILE | B | 62 | 24.023 | 65.564 | 74.929 | 1.00 | 40.49 | B | C |
| ATOM | 2727 | CB  | ILE | B | 62 | 24.086 | 65.536 | 76.474 | 1.00 | 52.01 | B | C |
| ATOM | 2728 | CG2 | ILE | B | 62 | 23.919 | 66.952 | 77.025 | 1.00 | 52.01 | B | C |
| ATOM | 2729 | CG1 | ILE | B | 62 | 22.966 | 64.689 | 77.056 | 1.00 | 52.01 | B | C |
| ATOM | 2730 | CD1 | ILE | B | 62 | 22.882 | 64.840 | 78.567 | 1.00 | 52.01 | B | C |
| ATOM | 2731 | C   | ILE | B | 62 | 23.977 | 64.145 | 74.402 | 1.00 | 40.49 | B | C |
| ATOM | 2732 | O   | ILE | B | 62 | 24.964 | 63.418 | 74.453 | 1.00 | 40.49 | B | O |
| ATOM | 2733 | N   | GLY | B | 63 | 22.824 | 63.754 | 73.886 | 1.00 | 23.11 | B | N |
| ATOM | 2734 | CA  | GLY | B | 63 | 22.674 | 62.412 | 73.363 | 1.00 | 23.11 | B | C |
| ATOM | 2735 | C   | GLY | B | 63 | 21.504 | 62.414 | 72.416 | 1.00 | 23.11 | B | C |
| ATOM | 2736 | O   | GLY | B | 63 | 20.506 | 63.081 | 72.657 | 1.00 | 23.11 | B | O |
| ATOM | 2737 | N   | ASN | B | 64 | 21.614 | 61.663 | 71.333 | 1.00 | 52.26 | B | N |
| ATOM | 2738 | CA  | ASN | B | 64 | 20.549 | 61.635 | 70.342 | 1.00 | 52.26 | B | C |
| ATOM | 2739 | CB  | ASN | B | 64 | 20.910 | 62.566 | 69.182 | 1.00 | 99.59 | B | C |
| ATOM | 2740 | CG  | ASN | B | 64 | 19.730 | 62.842 | 68.264 | 1.00 | 99.59 | B | C |
| ATOM | 2741 | OD1 | ASN | B | 64 | 19.314 | 61.986 | 67.451 | 1.00 | 99.59 | B | O |
| ATOM | 2742 | ND2 | ASN | B | 64 | 19.172 | 64.053 | 68.389 | 1.00 | 99.59 | B | N |
| ATOM | 2743 | C   | ASN | B | 64 | 20.441 | 60.221 | 69.850 | 1.00 | 52.26 | B | C |
| ATOM | 2744 | O   | ASN | B | 64 | 20.800 | 59.949 | 68.704 | 1.00 | 52.26 | B | O |
| ATOM | 2745 | N   | GLY | B | 65 | 19.992 | 59.329 | 70.734 | 1.00 | 68.33 | B | N |
| ATOM | 2746 | CA  | GLY | B | 65 | 19.840 | 57.931 | 70.390 | 1.00 | 68.33 | B | C |
| ATOM | 2747 | C   | GLY | B | 65 | 18.635 | 57.558 | 69.534 | 1.00 | 68.33 | B | C |
| ATOM | 2748 | O   | GLY | B | 65 | 18.123 | 58.349 | 68.713 | 1.00 | 68.33 | B | O |
| ATOM | 2749 | N   | SER | B | 66 | 18.225 | 56.312 | 69.714 | 1.00 | 79.80 | B | N |
| ATOM | 2750 | CA  | SER | B | 66 | 17.093 | 55.721 | 69.021 | 1.00 | 79.80 | B | C |
| ATOM | 2751 | CB  | SER | B | 66 | 17.309 | 54.201 | 68.946 | 1.00 | 52.53 | B | C |
| ATOM | 2752 | OG  | SER | B | 66 | 16.238 | 53.467 | 69.525 | 1.00 | 52.53 | B | O |
| ATOM | 2753 | C   | SER | B | 66 | 15.817 | 56.084 | 69.811 | 1.00 | 79.80 | B | C |
| ATOM | 2754 | O   | SER | B | 66 | 14.800 | 56.492 | 69.208 | 1.00 | 79.80 | B | O |
| ATOM | 2755 | N   | PHE | B | 67 | 15.885 | 55.938 | 71.137 | 1.00 | 62.02 | B | N |
| ATOM | 2756 | CA  | PHE | B | 67 | 14.768 | 56.237 | 72.043 | 1.00 | 62.02 | B | C |
| ATOM | 2757 | CB  | PHE | B | 67 | 15.234 | 56.042 | 73.491 | 1.00 | 79.95 | B | C |

FIG. 6-47

| ATOM | 2758 | CG | PHE | B | 67 | 16.474 | 56.832 | 73.853 | 1.00 | 79.95 | B | C |
| ATOM | 2759 | CD1 | PHE | B | 67 | 16.371 | 58.091 | 74.458 | 1.00 | 79.95 | B | C |
| ATOM | 2760 | CD2 | PHE | B | 67 | 17.744 | 56.336 | 73.538 | 1.00 | 79.95 | B | C |
| ATOM | 2761 | CE1 | PHE | B | 67 | 17.525 | 58.840 | 74.758 | 1.00 | 79.95 | B | C |
| ATOM | 2762 | CE2 | PHE | B | 67 | 18.910 | 57.068 | 73.827 | 1.00 | 79.95 | B | C |
| ATOM | 2763 | CZ | PHE | B | 67 | 18.805 | 58.324 | 74.434 | 1.00 | 79.95 | B | C |
| ATOM | 2764 | C | PHE | B | 67 | 14.223 | 57.670 | 71.858 | 1.00 | 62.02 | B | C |
| ATOM | 2765 | O | PHE | B | 67 | 13.015 | 57.864 | 71.686 | 1.00 | 62.02 | B | O |
| ATOM | 2766 | N | GLY | B | 68 | 15.138 | 58.637 | 71.845 | 1.00 | 61.32 | B | N |
| ATOM | 2767 | CA | GLY | B | 68 | 14.786 | 60.045 | 71.727 | 1.00 | 61.32 | B | C |
| ATOM | 2768 | C | GLY | B | 68 | 16.027 | 60.922 | 71.870 | 1.00 | 61.32 | B | C |
| ATOM | 2769 | O | GLY | B | 68 | 17.132 | 60.470 | 71.542 | 1.00 | 61.32 | B | O |
| ATOM | 2770 | N | VAL | B | 69 | 15.855 | 62.148 | 72.375 | 1.00 | 50.35 | B | N |
| ATOM | 2771 | CA | VAL | B | 69 | 16.968 | 63.097 | 72.547 | 1.00 | 50.35 | B | C |
| ATOM | 2772 | CB | VAL | B | 69 | 16.823 | 64.410 | 71.766 | 1.00 | 31.36 | B | C |
| ATOM | 2773 | CG1 | VAL | B | 69 | 18.092 | 65.238 | 72.062 | 1.00 | 31.36 | B | C |
| ATOM | 2774 | CG2 | VAL | B | 69 | 16.651 | 64.167 | 70.295 | 1.00 | 31.36 | B | C |
| ATOM | 2775 | C | VAL | B | 69 | 17.054 | 63.490 | 73.990 | 1.00 | 50.35 | B | C |
| ATOM | 2776 | O | VAL | B | 69 | 16.030 | 63.635 | 74.647 | 1.00 | 50.35 | B | O |
| ATOM | 2777 | N | VAL | B | 70 | 18.286 | 63.601 | 74.468 | 1.00 | 40.09 | B | N |
| ATOM | 2778 | CA | VAL | B | 70 | 18.519 | 63.980 | 75.848 | 1.00 | 40.09 | B | C |
| ATOM | 2779 | CB | VAL | B | 70 | 19.277 | 62.888 | 76.591 | 1.00 | 21.98 | B | C |
| ATOM | 2780 | CG1 | VAL | B | 70 | 19.480 | 63.289 | 78.035 | 1.00 | 21.98 | B | C |
| ATOM | 2781 | CG2 | VAL | B | 70 | 18.509 | 61.589 | 76.488 | 1.00 | 21.98 | B | C |
| ATOM | 2782 | C | VAL | B | 70 | 19.289 | 65.289 | 75.927 | 1.00 | 40.09 | B | C |
| ATOM | 2783 | O | VAL | B | 70 | 20.460 | 65.369 | 75.543 | 1.00 | 40.09 | B | O |
| ATOM | 2784 | N | TYR | B | 71 | 18.610 | 66.317 | 76.419 | 1.00 | 30.48 | B | N |
| ATOM | 2785 | CA | TYR | B | 71 | 19.215 | 67.625 | 76.554 | 1.00 | 30.48 | B | C |
| ATOM | 2786 | CB | TYR | B | 71 | 18.210 | 68.737 | 76.239 | 1.00 | 38.18 | B | C |
| ATOM | 2787 | CG | TYR | B | 71 | 17.473 | 68.539 | 74.940 | 1.00 | 38.18 | B | C |
| ATOM | 2788 | CD1 | TYR | B | 71 | 16.534 | 67.526 | 74.810 | 1.00 | 38.18 | B | C |
| ATOM | 2789 | CE1 | TYR | B | 71 | 15.884 | 67.301 | 73.608 | 1.00 | 38.18 | B | C |
| ATOM | 2790 | CD2 | TYR | B | 71 | 17.745 | 69.338 | 73.828 | 1.00 | 38.18 | B | C |
| ATOM | 2791 | CE2 | TYR | B | 71 | 17.103 | 69.122 | 72.619 | 1.00 | 38.18 | B | C |
| ATOM | 2792 | CZ | TYR | B | 71 | 16.171 | 68.097 | 72.513 | 1.00 | 38.18 | B | C |
| ATOM | 2793 | OH | TYR | B | 71 | 15.536 | 67.839 | 71.319 | 1.00 | 38.18 | B | O |
| ATOM | 2794 | C | TYR | B | 71 | 19.644 | 67.764 | 77.983 | 1.00 | 30.48 | B | C |
| ATOM | 2795 | O | TYR | B | 71 | 19.272 | 66.955 | 78.831 | 1.00 | 30.48 | B | O |
| ATOM | 2796 | N | GLN | B | 72 | 20.452 | 68.788 | 78.232 | 1.00 | 39.61 | B | N |
| ATOM | 2797 | CA | GLN | B | 72 | 20.907 | 69.109 | 79.569 | 1.00 | 39.61 | B | C |
| ATOM | 2798 | CB | GLN | B | 72 | 22.422 | 69.123 | 79.665 | 1.00 | 38.68 | B | C |
| ATOM | 2799 | CG | GLN | B | 72 | 22.894 | 69.567 | 81.035 | 1.00 | 38.68 | B | C |
| ATOM | 2800 | CD | GLN | B | 72 | 24.395 | 69.671 | 81.130 | 1.00 | 38.68 | B | C |
| ATOM | 2801 | OE1 | GLN | B | 72 | 24.955 | 69.755 | 82.230 | 1.00 | 38.68 | B | O |
| ATOM | 2802 | NE2 | GLN | B | 72 | 25.065 | 69.669 | 79.979 | 1.00 | 38.68 | B | N |
| ATOM | 2803 | C | GLN | B | 72 | 20.397 | 70.515 | 79.697 | 1.00 | 39.61 | B | C |
| ATOM | 2804 | O | GLN | B | 72 | 20.300 | 71.216 | 78.692 | 1.00 | 39.61 | B | O |
| ATOM | 2805 | N | ALA | B | 73 | 20.065 | 70.935 | 80.906 | 1.00 | 27.59 | B | N |
| ATOM | 2806 | CA | ALA | B | 73 | 19.552 | 72.281 | 81.089 | 1.00 | 27.59 | B | C |
| ATOM | 2807 | CB | ALA | B | 73 | 18.097 | 72.361 | 80.627 | 1.00 | 20.91 | B | C |
| ATOM | 2808 | C | ALA | B | 73 | 19.658 | 72.698 | 82.538 | 1.00 | 27.59 | B | C |
| ATOM | 2809 | O | ALA | B | 73 | 19.923 | 71.872 | 83.423 | 1.00 | 27.59 | B | O |
| ATOM | 2810 | N | LYS | B | 74 | 19.434 | 73.987 | 82.772 | 1.00 | 31.83 | B | N |
| ATOM | 2811 | CA | LYS | B | 74 | 19.518 | 74.540 | 84.112 | 1.00 | 31.83 | B | C |
| ATOM | 2812 | CB | LYS | B | 74 | 20.559 | 75.658 | 84.136 | 1.00 | 49.94 | B | C |
| ATOM | 2813 | CG | LYS | B | 74 | 21.087 | 75.996 | 85.515 | 1.00 | 49.94 | B | C |
| ATOM | 2814 | CD | LYS | B | 74 | 21.617 | 77.433 | 85.552 | 1.00 | 49.94 | B | C |
| ATOM | 2815 | CE | LYS | B | 74 | 22.637 | 77.622 | 86.658 | 1.00 | 49.94 | B | C |
| ATOM | 2816 | NZ | LYS | B | 74 | 23.852 | 76.796 | 86.397 | 1.00 | 49.94 | B | N |
| ATOM | 2817 | C | LYS | B | 74 | 18.165 | 75.072 | 84.579 | 1.00 | 31.83 | B | C |

FIG. 6-48

| | | | | | | | | | | | |
|---|---|---|---|---|---|---|---|---|---|---|---|
| ATOM | 2818 | O | LYS | B | 74 | 17.529 | 75.901 | 83.918 | 1.00 | 31.83 | B O |
| ATOM | 2819 | N | LEU | B | 75 | 17.716 | 74.569 | 85.717 | 1.00 | 35.44 | B N |
| ATOM | 2820 | CA | LEU | B | 75 | 16.463 | 75.021 | 86.269 | 1.00 | 35.44 | B C |
| ATOM | 2821 | CB | LEU | B | 75 | 16.075 | 74.151 | 87.465 | 1.00 | 25.11 | B C |
| ATOM | 2822 | CG | LEU | B | 75 | 15.820 | 72.674 | 87.157 | 1.00 | 25.11 | B C |
| ATOM | 2823 | CD1 | LEU | B | 75 | 15.409 | 71.948 | 88.421 | 1.00 | 25.11 | B C |
| ATOM | 2824 | CD2 | LEU | B | 75 | 14.724 | 72.554 | 86.111 | 1.00 | 25.11 | B C |
| ATOM | 2825 | C | LEU | B | 75 | 16.754 | 76.439 | 86.720 | 1.00 | 35.44 | B C |
| ATOM | 2826 | O | LEU | B | 75 | 17.640 | 76.652 | 87.546 | 1.00 | 35.44 | B O |
| ATOM | 2827 | N | CYS | B | 76 | 16.026 | 77.410 | 86.175 | 1.00 | 39.86 | B N |
| ATOM | 2828 | CA | CYS | B | 76 | 16.242 | 78.807 | 86.535 | 1.00 | 39.86 | B C |
| ATOM | 2829 | CB | CYS | B | 76 | 15.208 | 79.700 | 85.860 | 1.00 | 48.80 | B C |
| ATOM | 2830 | SG | CYS | B | 76 | 15.353 | 79.704 | 84.061 | 1.00 | 48.80 | B S |
| ATOM | 2831 | C | CYS | B | 76 | 16.219 | 79.056 | 88.031 | 1.00 | 39.86 | B C |
| ATOM | 2832 | O | CYS | B | 76 | 17.191 | 79.566 | 88.587 | 1.00 | 39.86 | B O |
| ATOM | 2833 | N | ASP | B | 77 | 15.129 | 78.687 | 88.696 | 1.00 | 49.76 | B N |
| ATOM | 2834 | CA | ASP | B | 77 | 15.033 | 78.934 | 90.134 | 1.00 | 49.76 | B C |
| ATOM | 2835 | CB | ASP | B | 77 | 13.661 | 78.472 | 90.671 | 1.00 | 80.19 | B C |
| ATOM | 2836 | CG | ASP | B | 77 | 13.436 | 76.954 | 90.539 | 1.00 | 80.19 | B C |
| ATOM | 2837 | OD1 | ASP | B | 77 | 13.650 | 76.381 | 89.429 | 1.00 | 80.19 | B O |
| ATOM | 2838 | OD2 | ASP | B | 77 | 13.027 | 76.336 | 91.559 | 1.00 | 80.19 | B O |
| ATOM | 2839 | C | ASP | B | 77 | 16.190 | 78.320 | 90.931 | 1.00 | 49.76 | B C |
| ATOM | 2840 | O | ASP | B | 77 | 17.083 | 79.043 | 91.375 | 1.00 | 49.76 | B O |
| ATOM | 2841 | N | SER | B | 78 | 16.202 | 77.001 | 91.092 | 1.00 | 46.34 | B N |
| ATOM | 2842 | CA | SER | B | 78 | 17.267 | 76.325 | 91.845 | 1.00 | 46.34 | B C |
| ATOM | 2843 | CB | SER | B | 78 | 16.919 | 74.846 | 92.046 | 1.00 | 34.05 | B C |
| ATOM | 2844 | OG | SER | B | 78 | 16.676 | 74.210 | 90.798 | 1.00 | 34.05 | B O |
| ATOM | 2845 | C | SER | B | 78 | 18.642 | 76.411 | 91.191 | 1.00 | 46.34 | B C |
| ATOM | 2846 | O | SER | B | 78 | 19.653 | 76.276 | 91.864 | 1.00 | 46.34 | B O |
| ATOM | 2847 | N | GLY | B | 79 | 18.677 | 76.614 | 89.882 | 1.00 | 31.69 | B N |
| ATOM | 2848 | CA | GLY | B | 79 | 19.952 | 76.687 | 89.191 | 1.00 | 31.69 | B C |
| ATOM | 2849 | C | GLY | B | 79 | 20.607 | 75.323 | 89.020 | 1.00 | 31.69 | B C |
| ATOM | 2850 | O | GLY | B | 79 | 21.757 | 75.234 | 88.595 | 1.00 | 31.69 | B O |
| ATOM | 2851 | N | GLU | B | 80 | 19.872 | 74.261 | 89.338 | 1.00 | 39.92 | B N |
| ATOM | 2852 | CA | GLU | B | 80 | 20.386 | 72.903 | 89.229 | 1.00 | 39.92 | B C |
| ATOM | 2853 | CB | GLU | B | 80 | 19.605 | 71.991 | 90.157 | 1.00 | 51.32 | B C |
| ATOM | 2854 | CG | GLU | B | 80 | 19.441 | 72.543 | 91.561 | 1.00 | 51.32 | B C |
| ATOM | 2855 | CD | GLU | B | 80 | 18.611 | 71.620 | 92.435 | 1.00 | 51.32 | B C |
| ATOM | 2856 | OE1 | GLU | B | 80 | 19.114 | 70.526 | 92.791 | 1.00 | 51.32 | B O |
| ATOM | 2857 | OE2 | GLU | B | 80 | 17.450 | 71.981 | 92.750 | 1.00 | 51.32 | B O |
| ATOM | 2858 | C | GLU | B | 80 | 20.285 | 72.369 | 87.803 | 1.00 | 39.92 | B C |
| ATOM | 2859 | O | GLU | B | 80 | 19.388 | 72.759 | 87.046 | 1.00 | 39.92 | B O |
| ATOM | 2860 | N | LEU | B | 81 | 21.207 | 71.473 | 87.449 | 1.00 | 22.46 | B N |
| ATOM | 2861 | CA | LEU | B | 81 | 21.233 | 70.871 | 86.123 | 1.00 | 22.46 | B C |
| ATOM | 2862 | CB | LEU | B | 81 | 22.652 | 70.413 | 85.779 | 1.00 | 20.85 | B C |
| ATOM | 2863 | CG | LEU | B | 81 | 23.772 | 71.455 | 85.642 | 1.00 | 20.85 | B C |
| ATOM | 2864 | CD1 | LEU | B | 81 | 25.102 | 70.737 | 85.513 | 1.00 | 20.85 | B C |
| ATOM | 2865 | CD2 | LEU | B | 81 | 23.539 | 72.352 | 84.428 | 1.00 | 20.85 | B C |
| ATOM | 2866 | C | LEU | B | 81 | 20.277 | 69.681 | 86.057 | 1.00 | 22.46 | B C |
| ATOM | 2867 | O | LEU | B | 81 | 20.123 | 68.937 | 87.024 | 1.00 | 22.46 | B O |
| ATOM | 2868 | N | VAL | B | 82 | 19.642 | 69.511 | 84.902 | 1.00 | 30.78 | B N |
| ATOM | 2869 | CA | VAL | B | 82 | 18.694 | 68.428 | 84.696 | 1.00 | 30.78 | B C |
| ATOM | 2870 | CB | VAL | B | 82 | 17.242 | 68.898 | 84.884 | 1.00 | 31.08 | B C |
| ATOM | 2871 | CG1 | VAL | B | 82 | 16.991 | 69.253 | 86.329 | 1.00 | 31.08 | B C |
| ATOM | 2872 | CG2 | VAL | B | 82 | 16.965 | 70.084 | 83.970 | 1.00 | 31.08 | B C |
| ATOM | 2873 | C | VAL | B | 82 | 18.779 | 67.839 | 83.306 | 1.00 | 30.78 | B C |
| ATOM | 2874 | O | VAL | B | 82 | 19.204 | 68.495 | 82.358 | 1.00 | 30.78 | B O |
| ATOM | 2875 | N | ALA | B | 83 | 18.342 | 66.592 | 83.199 | 1.00 | 24.30 | B N |
| ATOM | 2876 | CA | ALA | B | 83 | 18.332 | 65.881 | 81.938 | 1.00 | 24.30 | B C |
| ATOM | 2877 | CB | ALA | B | 83 | 18.868 | 64.464 | 82.141 | 1.00 | 22.71 | B C |

FIG. 6-49

| ATOM | 2878 | C | ALA | B | 83 | 16.883 | 65.841 | 81.464 | 1.00 | 24.30 | B | C |
| ATOM | 2879 | O | ALA | B | 83 | 15.964 | 65.725 | 82.273 | 1.00 | 24.30 | B | O |
| ATOM | 2880 | N | ILE | B | 84 | 16.674 | 65.954 | 80.157 | 1.00 | 18.14 | B | N |
| ATOM | 2881 | CA | ILE | B | 84 | 15.323 | 65.918 | 79.629 | 1.00 | 18.14 | B | C |
| ATOM | 2882 | CB | ILE | B | 84 | 14.831 | 67.312 | 79.133 | 1.00 | 21.12 | B | C |
| ATOM | 2883 | CG2 | ILE | B | 84 | 13.371 | 67.216 | 78.684 | 1.00 | 21.12 | B | C |
| ATOM | 2884 | CG1 | ILE | B | 84 | 14.931 | 68.351 | 80.255 | 1.00 | 21.12 | B | C |
| ATOM | 2885 | CD1 | ILE | B | 84 | 14.388 | 69.721 | 79.882 | 1.00 | 21.12 | B | C |
| ATOM | 2886 | C | ILE | B | 84 | 15.232 | 64.951 | 78.475 | 1.00 | 18.14 | B | C |
| ATOM | 2887 | O | ILE | B | 84 | 15.663 | 65.255 | 77.368 | 1.00 | 18.14 | B | O |
| ATOM | 2888 | N | LYS | B | 85 | 14.674 | 63.773 | 78.737 | 1.00 | 28.86 | B | N |
| ATOM | 2889 | CA | LYS | B | 85 | 14.526 | 62.787 | 77.686 | 1.00 | 28.86 | B | C |
| ATOM | 2890 | CB | LYS | B | 85 | 14.564 | 61.369 | 78.244 | 1.00 | 34.67 | B | C |
| ATOM | 2891 | CG | LYS | B | 85 | 14.557 | 60.336 | 77.135 | 1.00 | 34.67 | B | C |
| ATOM | 2892 | CD | LYS | B | 85 | 13.899 | 59.027 | 77.549 | 1.00 | 34.67 | B | C |
| ATOM | 2893 | CE | LYS | B | 85 | 14.853 | 58.118 | 78.298 | 1.00 | 34.67 | B | C |
| ATOM | 2894 | NZ | LYS | B | 85 | 14.233 | 56.781 | 78.443 | 1.00 | 34.67 | B | N |
| ATOM | 2895 | C | LYS | B | 85 | 13.189 | 63.045 | 77.016 | 1.00 | 28.86 | B | C |
| ATOM | 2896 | O | LYS | B | 85 | 12.131 | 62.776 | 77.583 | 1.00 | 28.86 | B | O |
| ATOM | 2897 | N | LYS | B | 86 | 13.254 | 63.594 | 75.809 | 1.00 | 38.23 | B | N |
| ATOM | 2898 | CA | LYS | B | 86 | 12.068 | 63.912 | 75.026 | 1.00 | 38.23 | B | C |
| ATOM | 2899 | CB | LYS | B | 86 | 12.292 | 65.217 | 74.261 | 1.00 | 36.16 | B | C |
| ATOM | 2900 | CG | LYS | B | 86 | 11.086 | 65.659 | 73.467 | 1.00 | 36.16 | B | C |
| ATOM | 2901 | CD | LYS | B | 86 | 11.475 | 66.550 | 72.296 | 1.00 | 36.16 | B | C |
| ATOM | 2902 | CE | LYS | B | 86 | 11.420 | 68.028 | 72.623 | 1.00 | 36.16 | B | C |
| ATOM | 2903 | NZ | LYS | B | 86 | 11.754 | 68.811 | 71.391 | 1.00 | 36.16 | B | N |
| ATOM | 2904 | C | LYS | B | 86 | 11.807 | 62.784 | 74.036 | 1.00 | 38.23 | B | C |
| ATOM | 2905 | O | LYS | B | 86 | 12.725 | 62.376 | 73.325 | 1.00 | 38.23 | B | O |
| ATOM | 2906 | N | VAL | B | 87 | 10.577 | 62.271 | 74.004 | 1.00 | 33.31 | B | N |
| ATOM | 2907 | CA | VAL | B | 87 | 10.222 | 61.195 | 73.075 | 1.00 | 33.31 | B | C |
| ATOM | 2908 | CB | VAL | B | 87 | 10.315 | 59.802 | 73.724 | 1.00 | 19.45 | B | C |
| ATOM | 2909 | CG1 | VAL | B | 87 | 11.573 | 59.696 | 74.551 | 1.00 | 19.45 | B | C |
| ATOM | 2910 | CG2 | VAL | B | 87 | 9.083 | 59.526 | 74.551 | 1.00 | 19.45 | B | C |
| ATOM | 2911 | C | VAL | B | 87 | 8.804 | 61.356 | 72.535 | 1.00 | 33.31 | B | C |
| ATOM | 2912 | O | VAL | B | 87 | 7.900 | 61.818 | 73.233 | 1.00 | 33.31 | B | O |
| ATOM | 2913 | N | LEU | B | 88 | 8.609 | 60.970 | 71.285 | 1.00 | 45.95 | B | N |
| ATOM | 2914 | CA | LEU | B | 88 | 7.299 | 61.076 | 70.677 | 1.00 | 45.95 | B | C |
| ATOM | 2915 | CB | LEU | B | 88 | 7.390 | 60.644 | 69.219 | 1.00 | 48.13 | B | C |
| ATOM | 2916 | CG | LEU | B | 88 | 6.190 | 60.972 | 68.344 | 1.00 | 48.13 | B | C |
| ATOM | 2917 | CD1 | LEU | B | 88 | 6.151 | 62.473 | 68.080 | 1.00 | 48.13 | B | C |
| ATOM | 2918 | CD2 | LEU | B | 88 | 6.300 | 60.190 | 67.051 | 1.00 | 48.13 | B | C |
| ATOM | 2919 | C | LEU | B | 88 | 6.326 | 60.166 | 71.439 | 1.00 | 45.95 | B | C |
| ATOM | 2920 | O | LEU | B | 88 | 6.661 | 59.029 | 71.757 | 1.00 | 45.95 | B | O |
| ATOM | 2921 | N | GLN | B | 89 | 5.135 | 60.666 | 71.750 | 1.00 | 43.61 | B | N |
| ATOM | 2922 | CA | GLN | B | 89 | 4.151 | 59.865 | 72.468 | 1.00 | 43.61 | B | C |
| ATOM | 2923 | CB | GLN | B | 89 | 3.633 | 60.612 | 73.710 | 1.00 | 50.98 | B | C |
| ATOM | 2924 | CG | GLN | B | 89 | 3.560 | 59.816 | 75.042 | 1.00 | 50.98 | B | C |
| ATOM | 2925 | CD | GLN | B | 89 | 3.732 | 58.309 | 74.884 | 1.00 | 50.98 | B | C |
| ATOM | 2926 | OE1 | GLN | B | 89 | 4.763 | 57.839 | 74.391 | 1.00 | 50.98 | B | O |
| ATOM | 2927 | NE2 | GLN | B | 89 | 2.727 | 57.544 | 75.310 | 1.00 | 50.98 | B | N |
| ATOM | 2928 | C | GLN | B | 89 | 3.014 | 59.677 | 71.487 | 1.00 | 43.61 | B | C |
| ATOM | 2929 | O | GLN | B | 89 | 2.940 | 60.387 | 70.483 | 1.00 | 43.61 | B | O |
| ATOM | 2930 | N | ASP | B | 90 | 2.132 | 58.728 | 71.766 | 1.00 | 70.28 | B | N |
| ATOM | 2931 | CA | ASP | B | 90 | 1.000 | 58.476 | 70.888 | 1.00 | 70.28 | B | C |
| ATOM | 2932 | CB | ASP | B | 90 | 1.017 | 57.033 | 70.389 | 1.00 | 81.91 | B | C |
| ATOM | 2933 | CG | ASP | B | 90 | -0.365 | 56.566 | 69.916 | 1.00 | 81.91 | B | C |
| ATOM | 2934 | OD1 | ASP | B | 90 | -0.771 | 55.424 | 70.275 | 1.00 | 81.91 | B | O |
| ATOM | 2935 | OD2 | ASP | B | 90 | -1.048 | 57.342 | 69.198 | 1.00 | 81.91 | B | O |
| ATOM | 2936 | C | ASP | B | 90 | -0.284 | 58.721 | 71.674 | 1.00 | 70.28 | B | C |
| ATOM | 2937 | O | ASP | B | 90 | -0.820 | 57.794 | 72.304 | 1.00 | 70.28 | B | O |

FIG. 6-50

```
ATOM   2938  N    ALA B  91      -0.754  59.973  71.640  1.00 87.37      B    N
ATOM   2939  CA   ALA B  91      -1.974  60.417  72.345  1.00 87.37      B    C
ATOM   2940  CB   ALA B  91      -2.872  61.221  71.383  1.00 51.16      B    C
ATOM   2941  C    ALA B  91      -2.784  59.295  73.002  1.00 87.37      B    C
ATOM   2942  O    ALA B  91      -3.047  59.335  74.204  1.00 87.37      B    O
ATOM   2943  N    ALA B  92      -3.174  58.300  72.207  1.00 59.11      B    N
ATOM   2944  CA   ALA B  92      -3.949  57.163  72.711  1.00 59.11      B    C
ATOM   2945  CB   ALA B  92      -4.128  56.123  71.599  1.00 59.63      B    C
ATOM   2946  C    ALA B  92      -3.305  56.499  73.929  1.00 59.11      B    C
ATOM   2947  O    ALA B  92      -3.694  56.761  75.075  1.00 59.11      B    O
ATOM   2948  N    ALA B  93      -2.318  55.642  73.653  1.00 88.18      B    N
ATOM   2949  CA   ALA B  93      -1.582  54.871  74.668  1.00 88.18      B    C
ATOM   2950  CB   ALA B  93      -0.562  53.930  73.963  1.00 62.13      B    C
ATOM   2951  C    ALA B  93      -0.877  55.675  75.781  1.00 88.18      B    C
ATOM   2952  O    ALA B  93      -0.690  56.894  75.673  1.00 88.18      B    O
ATOM   2953  N    LYS B  94      -0.512  54.963  76.850  1.00 49.48      B    N
ATOM   2954  CA   LYS B  94       0.164  55.533  78.013  1.00 49.48      B    C
ATOM   2955  CB   LYS B  94      -0.497  55.055  79.307  1.00 78.96      B    C
ATOM   2956  CG   LYS B  94      -1.983  55.417  79.413  1.00 78.96      B    C
ATOM   2957  CD   LYS B  94      -2.568  55.121  80.810  1.00 78.96      B    C
ATOM   2958  CE   LYS B  94      -2.915  53.630  81.019  1.00 78.96      B    C
ATOM   2959  NZ   LYS B  94      -1.749  52.696  80.875  1.00 78.96      B    N
ATOM   2960  C    LYS B  94       1.597  55.052  77.994  1.00 49.48      B    C
ATOM   2961  O    LYS B  94       1.852  53.850  77.866  1.00 49.48      B    O
ATOM   2962  N    ASN B  95       2.532  55.984  78.137  1.00 20.37      B    N
ATOM   2963  CA   ASN B  95       3.950  55.652  78.115  1.00 20.37      B    C
ATOM   2964  CB   ASN B  95       4.779  56.927  78.163  1.00 24.54      B    C
ATOM   2965  CG   ASN B  95       6.228  56.667  77.895  1.00 24.54      B    C
ATOM   2966  OD1  ASN B  95       6.890  55.952  78.651  1.00 24.54      B    O
ATOM   2967  ND2  ASN B  95       6.737  57.232  76.803  1.00 24.54      B    N
ATOM   2968  C    ASN B  95       4.364  54.734  79.248  1.00 20.37      B    C
ATOM   2969  O    ASN B  95       4.338  55.128  80.410  1.00 20.37      B    O
ATOM   2970  N    ARG B  96       4.764  53.512  78.904  1.00 33.02      B    N
ATOM   2971  CA   ARG B  96       5.168  52.534  79.915  1.00 33.02      B    C
ATOM   2972  CB   ARG B  96       5.504  51.194  79.259  1.00 40.46      B    C
ATOM   2973  CG   ARG B  96       5.720  50.087  80.264  1.00 40.46      B    C
ATOM   2974  CD   ARG B  96       6.343  48.868  79.627  1.00 40.46      B    C
ATOM   2975  NE   ARG B  96       5.396  48.052  78.876  1.00 40.46      B    N
ATOM   2976  CZ   ARG B  96       5.767  47.121  78.001  1.00 40.46      B    C
ATOM   2977  NH1  ARG B  96       7.067  46.913  77.777  1.00 40.46      B    N
ATOM   2978  NH2  ARG B  96       4.857  46.386  77.365  1.00 40.46      B    N
ATOM   2979  C    ARG B  96       6.346  52.998  80.782  1.00 33.02      B    C
ATOM   2980  O    ARG B  96       6.391  52.753  81.995  1.00 33.02      B    O
ATOM   2981  N    GLU B  97       7.291  53.686  80.158  1.00 31.93      B    N
ATOM   2982  CA   GLU B  97       8.463  54.155  80.868  1.00 31.93      B    C
ATOM   2983  CB   GLU B  97       9.470  54.734  79.892  1.00 29.96      B    C
ATOM   2984  CG   GLU B  97      10.807  55.027  80.523  1.00 29.96      B    C
ATOM   2985  CD   GLU B  97      11.705  55.840  79.618  1.00 29.96      B    C
ATOM   2986  OE1  GLU B  97      11.442  55.878  78.400  1.00 29.96      B    O
ATOM   2987  OE2  GLU B  97      12.681  56.429  80.125  1.00 29.96      B    O
ATOM   2988  C    GLU B  97       8.095  55.203  81.900  1.00 31.93      B    C
ATOM   2989  O    GLU B  97       8.613  55.178  83.005  1.00 31.93      B    O
ATOM   2990  N    LEU B  98       7.210  56.129  81.549  1.00 13.88      B    N
ATOM   2991  CA   LEU B  98       6.820  57.158  82.498  1.00 13.88      B    C
ATOM   2992  CB   LEU B  98       5.868  58.166  81.855  1.00 21.78      B    C
ATOM   2993  CG   LEU B  98       5.112  59.138  82.789  1.00 21.78      B    C
ATOM   2994  CD1  LEU B  98       6.012  60.247  83.332  1.00 21.78      B    C
ATOM   2995  CD2  LEU B  98       3.976  59.758  82.009  1.00 21.78      B    C
ATOM   2996  C    LEU B  98       6.133  56.532  83.692  1.00 13.88      B    C
ATOM   2997  O    LEU B  98       6.336  56.941  84.829  1.00 13.88      B    O
```

FIG. 6-51

| | | | | | | | | | | | |
|---|---|---|---|---|---|---|---|---|---|---|---|
| ATOM | 2998 | N | GLN | B | 99 | 5.304 | 55.538 | 83.397 | 1.00 | 35.56 | B N |
| ATOM | 2999 | CA | GLN | B | 99 | 4.522 | 54.799 | 84.385 | 1.00 | 35.56 | B C |
| ATOM | 3000 | CB | GLN | B | 99 | 3.747 | 53.672 | 83.680 | 1.00 | 75.29 | B C |
| ATOM | 3001 | CG | GLN | B | 99 | 2.942 | 52.763 | 84.617 | 1.00 | 75.29 | B C |
| ATOM | 3002 | CD | GLN | B | 99 | 3.023 | 51.262 | 84.254 | 1.00 | 75.29 | B C |
| ATOM | 3003 | OE1 | GLN | B | 99 | 2.634 | 50.839 | 83.143 | 1.00 | 75.29 | B O |
| ATOM | 3004 | NE2 | GLN | B | 99 | 3.524 | 50.448 | 85.203 | 1.00 | 75.29 | B N |
| ATOM | 3005 | C | GLN | B | 99 | 5.422 | 54.198 | 85.446 | 1.00 | 35.56 | B C |
| ATOM | 3006 | O | GLN | B | 99 | 5.101 | 54.213 | 86.633 | 1.00 | 35.56 | B O |
| ATOM | 3007 | N | ILE | B | 100 | 6.546 | 53.657 | 84.991 | 1.00 | 25.44 | B N |
| ATOM | 3008 | CA | ILE | B | 100 | 7.511 | 53.019 | 85.862 | 1.00 | 25.44 | B C |
| ATOM | 3009 | CB | ILE | B | 100 | 8.390 | 52.062 | 85.031 | 1.00 | 24.37 | B C |
| ATOM | 3010 | CG2 | ILE | B | 100 | 9.561 | 51.536 | 85.846 | 1.00 | 24.37 | B C |
| ATOM | 3011 | CG1 | ILE | B | 100 | 7.501 | 50.928 | 84.517 | 1.00 | 24.37 | B C |
| ATOM | 3012 | CD1 | ILE | B | 100 | 8.245 | 49.745 | 83.962 | 1.00 | 24.37 | B C |
| ATOM | 3013 | C | ILE | B | 100 | 8.335 | 54.065 | 86.618 | 1.00 | 25.44 | B C |
| ATOM | 3014 | O | ILE | B | 100 | 8.480 | 53.969 | 87.834 | 1.00 | 25.44 | B O |
| ATOM | 3015 | N | MET | B | 101 | 8.851 | 55.073 | 85.920 | 1.00 | 17.69 | B N |
| ATOM | 3016 | CA | MET | B | 101 | 9.624 | 56.129 | 86.579 | 1.00 | 17.69 | B C |
| ATOM | 3017 | CB | MET | B | 101 | 9.932 | 57.257 | 85.597 | 1.00 | 43.54 | B C |
| ATOM | 3018 | CG | MET | B | 101 | 10.836 | 56.883 | 84.445 | 1.00 | 43.54 | B C |
| ATOM | 3019 | SD | MET | B | 101 | 12.554 | 56.904 | 84.902 | 1.00 | 43.54 | B S |
| ATOM | 3020 | CE | MET | B | 101 | 12.660 | 55.381 | 85.849 | 1.00 | 43.54 | B C |
| ATOM | 3021 | C | MET | B | 101 | 8.854 | 56.743 | 87.751 | 1.00 | 17.69 | B C |
| ATOM | 3022 | O | MET | B | 101 | 9.411 | 56.971 | 88.819 | 1.00 | 17.69 | B O |
| ATOM | 3023 | N | ARG | B | 102 | 7.576 | 57.027 | 87.508 | 1.00 | 22.85 | B N |
| ATOM | 3024 | CA | ARG | B | 102 | 6.664 | 57.624 | 88.475 | 1.00 | 22.85 | B C |
| ATOM | 3025 | CB | ARG | B | 102 | 5.232 | 57.654 | 87.917 | 1.00 | 40.41 | B C |
| ATOM | 3026 | CG | ARG | B | 102 | 4.893 | 58.798 | 86.959 | 1.00 | 40.41 | B C |
| ATOM | 3027 | CD | ARG | B | 102 | 4.491 | 60.053 | 87.709 | 1.00 | 40.41 | B C |
| ATOM | 3028 | NE | ARG | B | 102 | 3.102 | 60.442 | 87.464 | 1.00 | 40.41 | B N |
| ATOM | 3029 | CZ | ARG | B | 102 | 2.422 | 61.301 | 88.227 | 1.00 | 40.41 | B C |
| ATOM | 3030 | NH1 | ARG | B | 102 | 3.000 | 61.863 | 89.290 | 1.00 | 40.41 | B N |
| ATOM | 3031 | NH2 | ARG | B | 102 | 1.161 | 61.601 | 87.933 | 1.00 | 40.41 | B N |
| ATOM | 3032 | C | ARG | B | 102 | 6.639 | 56.884 | 89.798 | 1.00 | 22.85 | B C |
| ATOM | 3033 | O | ARG | B | 102 | 6.440 | 57.491 | 90.846 | 1.00 | 22.85 | B O |
| ATOM | 3034 | N | LYS | B | 103 | 6.840 | 55.574 | 89.752 | 1.00 | 16.67 | B N |
| ATOM | 3035 | CA | LYS | B | 103 | 6.785 | 54.763 | 90.960 | 1.00 | 16.67 | B C |
| ATOM | 3036 | CB | LYS | B | 103 | 6.128 | 53.425 | 90.632 | 1.00 | 44.32 | B C |
| ATOM | 3037 | CG | LYS | B | 103 | 5.713 | 52.644 | 91.853 | 1.00 | 44.32 | B C |
| ATOM | 3038 | CD | LYS | B | 103 | 5.973 | 51.152 | 91.691 | 1.00 | 44.32 | B C |
| ATOM | 3039 | CE | LYS | B | 103 | 7.475 | 50.839 | 91.613 | 1.00 | 44.32 | B C |
| ATOM | 3040 | NZ | LYS | B | 103 | 8.253 | 51.249 | 92.833 | 1.00 | 44.32 | B N |
| ATOM | 3041 | C | LYS | B | 103 | 8.126 | 54.496 | 91.670 | 1.00 | 16.67 | B C |
| ATOM | 3042 | O | LYS | B | 103 | 8.158 | 54.066 | 92.817 | 1.00 | 16.67 | B O |
| ATOM | 3043 | N | LEU | B | 104 | 9.236 | 54.755 | 91.000 | 1.00 | 28.51 | B N |
| ATOM | 3044 | CA | LEU | B | 104 | 10.536 | 54.488 | 91.595 | 1.00 | 28.51 | B C |
| ATOM | 3045 | CB | LEU | B | 104 | 11.524 | 54.073 | 90.495 | 1.00 | 26.45 | B C |
| ATOM | 3046 | CG | LEU | B | 104 | 11.519 | 52.628 | 89.982 | 1.00 | 26.45 | B C |
| ATOM | 3047 | CD1 | LEU | B | 104 | 10.107 | 52.103 | 89.875 | 1.00 | 26.45 | B C |
| ATOM | 3048 | CD2 | LEU | B | 104 | 12.208 | 52.571 | 88.630 | 1.00 | 26.45 | B C |
| ATOM | 3049 | C | LEU | B | 104 | 11.136 | 55.635 | 92.410 | 1.00 | 28.51 | B C |
| ATOM | 3050 | O | LEU | B | 104 | 11.040 | 56.799 | 92.037 | 1.00 | 28.51 | B O |
| ATOM | 3051 | N | ASP | B | 105 | 11.749 | 55.285 | 93.535 | 1.00 | 26.35 | B N |
| ATOM | 3052 | CA | ASP | B | 105 | 12.403 | 56.251 | 94.409 | 1.00 | 26.35 | B C |
| ATOM | 3053 | CB | ASP | B | 105 | 11.419 | 56.867 | 95.410 | 1.00 | 33.95 | B C |
| ATOM | 3054 | CG | ASP | B | 105 | 12.118 | 57.754 | 96.460 | 1.00 | 33.95 | B C |
| ATOM | 3055 | OD1 | ASP | B | 105 | 12.903 | 58.653 | 96.076 | 1.00 | 33.95 | B O |
| ATOM | 3056 | OD2 | ASP | B | 105 | 11.881 | 57.556 | 97.670 | 1.00 | 33.95 | B O |
| ATOM | 3057 | C | ASP | B | 105 | 13.514 | 55.532 | 95.169 | 1.00 | 26.35 | B C |

FIG. 6-52

```
ATOM   3058  O    ASP B 105      13.279  54.957  96.228  1.00 26.35      B  O
ATOM   3059  N    HIS B 106      14.724  55.564  94.624  1.00 16.48      B  N
ATOM   3060  CA   HIS B 106      15.852  54.892  95.248  1.00 16.48      B  C
ATOM   3061  CB   HIS B 106      15.956  53.466  94.705  1.00 19.33      B  C
ATOM   3062  CG   HIS B 106      17.070  52.670  95.299  1.00 19.33      B  C
ATOM   3063  CD2  HIS B 106      17.057  51.627  96.160  1.00 19.33      B  C
ATOM   3064  ND1  HIS B 106      18.393  52.905  95.002  1.00 19.33      B  N
ATOM   3065  CE1  HIS B 106      19.149  52.039  95.653  1.00 19.33      B  C
ATOM   3066  NE2  HIS B 106      18.363  51.252  96.363  1.00 19.33      B  N
ATOM   3067  C    HIS B 106      17.119  55.685  94.967  1.00 16.48      B  C
ATOM   3068  O    HIS B 106      17.346  56.120  93.852  1.00 16.48      B  O
ATOM   3069  N    CYS B 107      17.936  55.883  95.991  1.00 15.60      B  N
ATOM   3070  CA   CYS B 107      19.158  56.658  95.846  1.00 15.60      B  C
ATOM   3071  CB   CYS B 107      19.976  56.605  97.140  1.00 20.85      B  C
ATOM   3072  SG   CYS B 107      20.729  54.999  97.506  1.00 20.85      B  S
ATOM   3073  C    CYS B 107      20.038  56.202  94.679  1.00 15.60      B  C
ATOM   3074  O    CYS B 107      20.937  56.928  94.254  1.00 15.60      B  O
ATOM   3075  N    ASN B 108      19.791  55.004  94.159  1.00 16.03      B  N
ATOM   3076  CA   ASN B 108      20.595  54.509  93.052  1.00 16.03      B  C
ATOM   3077  CB   ASN B 108      21.253  53.187  93.431  1.00 25.05      B  C
ATOM   3078  CG   ASN B 108      22.450  53.381  94.322  1.00 25.05      B  C
ATOM   3079  OD1  ASN B 108      23.352  54.128  93.983  1.00 25.05      B  O
ATOM   3080  ND2  ASN B 108      22.471  52.710  95.461  1.00 25.05      B  N
ATOM   3081  C    ASN B 108      19.860  54.359  91.717  1.00 16.03      B  C
ATOM   3082  O    ASN B 108      20.140  53.460  90.933  1.00 16.03      B  O
ATOM   3083  N    ILE B 109      18.917  55.260  91.479  1.00 14.89      B  N
ATOM   3084  CA   ILE B 109      18.140  55.304  90.254  1.00 14.89      B  C
ATOM   3085  CB   ILE B 109      16.823  54.526  90.400  1.00 12.94      B  C
ATOM   3086  CG2  ILE B 109      15.971  54.688  89.151  1.00 12.94      B  C
ATOM   3087  CG1  ILE B 109      17.128  53.051  90.641  1.00 12.94      B  C
ATOM   3088  CD1  ILE B 109      15.906  52.167  90.712  1.00 12.94      B  C
ATOM   3089  C    ILE B 109      17.869  56.784  90.043  1.00 14.89      B  C
ATOM   3090  O    ILE B 109      17.498  57.473  90.985  1.00 14.89      B  O
ATOM   3091  N    VAL B 110      18.073  57.296  88.834  1.00  9.20      B  N
ATOM   3092  CA   VAL B 110      17.843  58.722  88.624  1.00  9.20      B  C
ATOM   3093  CB   VAL B 110      18.210  59.198  87.193  1.00 13.61      B  C
ATOM   3094  CG1  VAL B 110      19.689  59.085  86.989  1.00 13.61      B  C
ATOM   3095  CG2  VAL B 110      17.459  58.407  86.146  1.00 13.61      B  C
ATOM   3096  C    VAL B 110      16.413  59.110  88.911  1.00  9.20      B  C
ATOM   3097  O    VAL B 110      15.481  58.435  88.497  1.00  9.20      B  O
ATOM   3098  N    ARG B 111      16.255  60.217  89.619  1.00 27.63      B  N
ATOM   3099  CA   ARG B 111      14.947  60.719  89.994  1.00 27.63      B  C
ATOM   3100  CB   ARG B 111      15.085  61.601  91.241  1.00 47.05      B  C
ATOM   3101  CG   ARG B 111      13.787  62.116  91.831  1.00 47.05      B  C
ATOM   3102  CD   ARG B 111      14.088  63.222  92.817  1.00 47.05      B  C
ATOM   3103  NE   ARG B 111      14.855  64.288  92.169  1.00 47.05      B  N
ATOM   3104  CZ   ARG B 111      15.511  65.253  92.815  1.00 47.05      B  C
ATOM   3105  NH1  ARG B 111      15.491  65.290  94.144  1.00 47.05      B  N
ATOM   3106  NH2  ARG B 111      16.197  66.170  92.132  1.00 47.05      B  N
ATOM   3107  C    ARG B 111      14.272  61.495  88.874  1.00 27.63      B  C
ATOM   3108  O    ARG B 111      14.902  62.291  88.186  1.00 27.63      B  O
ATOM   3109  N    LEU B 112      12.986  61.227  88.676  1.00 22.82      B  N
ATOM   3110  CA   LEU B 112      12.201  61.929  87.674  1.00 22.82      B  C
ATOM   3111  CB   LEU B 112      11.062  61.037  87.163  1.00 21.64      B  C
ATOM   3112  CG   LEU B 112      10.025  61.737  86.278  1.00 21.64      B  C
ATOM   3113  CD1  LEU B 112      10.652  62.115  84.946  1.00 21.64      B  C
ATOM   3114  CD2  LEU B 112       8.823  60.829  86.087  1.00 21.64      B  C
ATOM   3115  C    LEU B 112      11.634  63.130  88.431  1.00 22.82      B  C
ATOM   3116  O    LEU B 112      10.841  62.974  89.353  1.00 22.82      B  O
ATOM   3117  N    ARG B 113      12.055  64.330  88.056  1.00 27.81      B  N
```

FIG. 6-53

| ATOM | 3118 | CA | ARG | B | 113 | 11.596 | 65.529 | 88.743 | 1.00 | 27.81 | B | C |
| --- | --- | --- | --- | --- | --- | --- | --- | --- | --- | --- | --- | --- |
| ATOM | 3119 | CB | ARG | B | 113 | 12.650 | 66.619 | 88.612 | 1.00 | 43.06 | B | C |
| ATOM | 3120 | CG | ARG | B | 113 | 13.927 | 66.392 | 89.397 | 1.00 | 43.06 | B | C |
| ATOM | 3121 | CD | ARG | B | 113 | 14.995 | 67.304 | 88.830 | 1.00 | 43.06 | B | C |
| ATOM | 3122 | NE | ARG | B | 113 | 15.917 | 67.832 | 89.830 | 1.00 | 43.06 | B | N |
| ATOM | 3123 | CZ | ARG | B | 113 | 15.584 | 68.726 | 90.758 | 1.00 | 43.06 | B | C |
| ATOM | 3124 | NH1 | ARG | B | 113 | 14.337 | 69.196 | 90.822 | 1.00 | 43.06 | B | N |
| ATOM | 3125 | NH2 | ARG | B | 113 | 16.504 | 69.166 | 91.611 | 1.00 | 43.06 | B | N |
| ATOM | 3126 | C | ARG | B | 113 | 10.266 | 66.044 | 88.229 | 1.00 | 27.81 | B | C |
| ATOM | 3127 | O | ARG | B | 113 | 9.384 | 66.415 | 88.998 | 1.00 | 27.81 | B | O |
| ATOM | 3128 | N | TYR | B | 114 | 10.133 | 66.070 | 86.915 | 1.00 | 25.55 | B | N |
| ATOM | 3129 | CA | TYR | B | 114 | 8.922 | 66.531 | 86.279 | 1.00 | 25.55 | B | C |
| ATOM | 3130 | CB | TYR | B | 114 | 9.042 | 68.006 | 85.947 | 1.00 | 36.59 | B | C |
| ATOM | 3131 | CG | TYR | B | 114 | 9.207 | 68.885 | 87.152 | 1.00 | 36.59 | B | C |
| ATOM | 3132 | CD1 | TYR | B | 114 | 8.181 | 69.010 | 88.082 | 1.00 | 36.59 | B | C |
| ATOM | 3133 | CE1 | TYR | B | 114 | 8.320 | 69.818 | 89.193 | 1.00 | 36.59 | B | C |
| ATOM | 3134 | CD2 | TYR | B | 114 | 10.389 | 69.595 | 87.367 | 1.00 | 36.59 | B | C |
| ATOM | 3135 | CE2 | TYR | B | 114 | 10.541 | 70.405 | 88.479 | 1.00 | 36.59 | B | C |
| ATOM | 3136 | CZ | TYR | B | 114 | 9.499 | 70.515 | 89.393 | 1.00 | 36.59 | B | C |
| ATOM | 3137 | OH | TYR | B | 114 | 9.620 | 71.310 | 90.517 | 1.00 | 36.59 | B | O |
| ATOM | 3138 | C | TYR | B | 114 | 8.779 | 65.763 | 84.981 | 1.00 | 25.55 | B | C |
| ATOM | 3139 | O | TYR | B | 114 | 9.599 | 64.904 | 84.635 | 1.00 | 25.55 | B | O |
| ATOM | 3140 | N | PHE | B | 115 | 7.703 | 66.084 | 84.281 | 1.00 | 29.31 | B | N |
| ATOM | 3141 | CA | PHE | B | 115 | 7.410 | 65.539 | 82.979 | 1.00 | 29.31 | B | C |
| ATOM | 3142 | CB | PHE | B | 115 | 6.990 | 64.059 | 83.041 | 1.00 | 22.81 | B | C |
| ATOM | 3143 | CG | PHE | B | 115 | 5.648 | 63.804 | 83.666 | 1.00 | 22.81 | B | C |
| ATOM | 3144 | CD1 | PHE | B | 115 | 4.516 | 63.631 | 82.873 | 1.00 | 22.81 | B | C |
| ATOM | 3145 | CD2 | PHE | B | 115 | 5.526 | 63.655 | 85.041 | 1.00 | 22.81 | B | C |
| ATOM | 3146 | CE1 | PHE | B | 115 | 3.284 | 63.312 | 83.440 | 1.00 | 22.81 | B | C |
| ATOM | 3147 | CE2 | PHE | B | 115 | 4.287 | 63.333 | 85.620 | 1.00 | 22.81 | B | C |
| ATOM | 3148 | CZ | PHE | B | 115 | 3.169 | 63.159 | 84.813 | 1.00 | 22.81 | B | C |
| ATOM | 3149 | C | PHE | B | 115 | 6.319 | 66.460 | 82.482 | 1.00 | 29.31 | B | C |
| ATOM | 3150 | O | PHE | B | 115 | 5.529 | 66.974 | 83.273 | 1.00 | 29.31 | B | O |
| ATOM | 3151 | N | PHE | B | 116 | 6.325 | 66.719 | 81.182 | 1.00 | 28.12 | B | N |
| ATOM | 3152 | CA | PHE | B | 116 | 5.353 | 67.601 | 80.566 | 1.00 | 28.12 | B | C |
| ATOM | 3153 | CB | PHE | B | 116 | 5.793 | 69.060 | 80.765 | 1.00 | 25.10 | B | C |
| ATOM | 3154 | CG | PHE | B | 116 | 7.147 | 69.392 | 80.170 | 1.00 | 25.10 | B | C |
| ATOM | 3155 | CD1 | PHE | B | 116 | 7.268 | 69.803 | 78.844 | 1.00 | 25.10 | B | C |
| ATOM | 3156 | CD2 | PHE | B | 116 | 8.299 | 69.318 | 80.942 | 1.00 | 25.10 | B | C |
| ATOM | 3157 | CE1 | PHE | B | 116 | 8.522 | 70.144 | 78.305 | 1.00 | 25.10 | B | C |
| ATOM | 3158 | CE2 | PHE | B | 116 | 9.550 | 69.654 | 80.410 | 1.00 | 25.10 | B | C |
| ATOM | 3159 | CZ | PHE | B | 116 | 9.660 | 70.066 | 79.092 | 1.00 | 25.10 | B | C |
| ATOM | 3160 | C | PHE | B | 116 | 5.262 | 67.272 | 79.084 | 1.00 | 28.12 | B | C |
| ATOM | 3161 | O | PHE | B | 116 | 6.153 | 66.630 | 78.534 | 1.00 | 28.12 | B | O |
| ATOM | 3162 | N | TYR | B | 117 | 4.188 | 67.703 | 78.433 | 1.00 | 23.48 | B | N |
| ATOM | 3163 | CA | TYR | B | 117 | 4.052 | 67.426 | 77.019 | 1.00 | 23.48 | B | C |
| ATOM | 3164 | CB | TYR | B | 117 | 2.682 | 66.862 | 76.717 | 1.00 | 19.00 | B | C |
| ATOM | 3165 | CG | TYR | B | 117 | 2.443 | 65.586 | 77.448 | 1.00 | 19.00 | B | C |
| ATOM | 3166 | CD1 | TYR | B | 117 | 1.994 | 65.597 | 78.767 | 1.00 | 19.00 | B | C |
| ATOM | 3167 | CE1 | TYR | B | 117 | 1.790 | 64.415 | 79.462 | 1.00 | 19.00 | B | C |
| ATOM | 3168 | CD2 | TYR | B | 117 | 2.690 | 64.360 | 76.842 | 1.00 | 19.00 | B | C |
| ATOM | 3169 | CE2 | TYR | B | 117 | 2.489 | 63.171 | 77.535 | 1.00 | 19.00 | B | C |
| ATOM | 3170 | CZ | TYR | B | 117 | 2.035 | 63.214 | 78.841 | 1.00 | 19.00 | B | C |
| ATOM | 3171 | OH | TYR | B | 117 | 1.795 | 62.055 | 79.523 | 1.00 | 19.00 | B | O |
| ATOM | 3172 | C | TYR | B | 117 | 4.309 | 68.638 | 76.153 | 1.00 | 23.48 | B | C |
| ATOM | 3173 | O | TYR | B | 117 | 3.933 | 69.754 | 76.502 | 1.00 | 23.48 | B | O |
| ATOM | 3174 | N | SER | B | 118 | 4.988 | 68.395 | 75.032 | 1.00 | 36.96 | B | N |
| ATOM | 3175 | CA | SER | B | 118 | 5.306 | 69.421 | 74.056 | 1.00 | 36.96 | B | C |
| ATOM | 3176 | CB | SER | B | 118 | 6.768 | 69.877 | 74.154 | 1.00 | 30.83 | B | C |
| ATOM | 3177 | OG | SER | B | 118 | 7.674 | 68.814 | 73.940 | 1.00 | 30.83 | B | O |

FIG. 6-54

| ATOM | 3178 | C | SER | B | 118 | 5.008 | 68.890 | 72.681 | 1.00 | 36.96 | B | C |
| --- | --- | --- | --- | --- | --- | --- | --- | --- | --- | --- | --- | --- |
| ATOM | 3179 | O | SER | B | 118 | 5.008 | 67.685 | 72.463 | 1.00 | 36.96 | B | O |
| ATOM | 3180 | N | SER | B | 119 | 4.708 | 69.779 | 71.751 | 1.00 | 77.94 | B | N |
| ATOM | 3181 | CA | SER | B | 119 | 4.423 | 69.320 | 70.410 | 1.00 | 77.94 | B | C |
| ATOM | 3182 | CB | SER | B | 119 | 3.365 | 70.200 | 69.759 | 1.00 | 91.50 | B | C |
| ATOM | 3183 | OG | SER | B | 119 | 3.921 | 71.480 | 69.509 | 1.00 | 91.50 | B | O |
| ATOM | 3184 | C | SER | B | 119 | 5.721 | 69.405 | 69.605 | 1.00 | 77.94 | B | C |
| ATOM | 3185 | O | SER | B | 119 | 6.828 | 69.497 | 70.179 | 1.00 | 77.94 | B | O |
| ATOM | 3186 | N | GLY | B | 120 | 5.572 | 69.379 | 68.281 | 1.00 | 100.00 | B | N |
| ATOM | 3187 | CA | GLY | B | 120 | 6.718 | 69.460 | 67.400 | 1.00 | 100.00 | B | C |
| ATOM | 3188 | C | GLY | B | 120 | 6.239 | 69.569 | 65.967 | 1.00 | 100.00 | B | C |
| ATOM | 3189 | O | GLY | B | 120 | 5.079 | 69.931 | 65.723 | 1.00 | 100.00 | B | O |
| ATOM | 3190 | N | ALA | B | 121 | 7.138 | 69.251 | 65.034 | 1.00 | 100.00 | B | N |
| ATOM | 3191 | CA | ALA | B | 121 | 6.876 | 69.279 | 63.594 | 1.00 | 100.00 | B | C |
| ATOM | 3192 | CB | ALA | B | 121 | 7.581 | 68.085 | 62.930 | 1.00 | 45.94 | B | C |
| ATOM | 3193 | C | ALA | B | 121 | 5.383 | 69.284 | 63.213 | 1.00 | 100.00 | B | C |
| ATOM | 3194 | O | ALA | B | 121 | 4.753 | 70.355 | 63.094 | 1.00 | 100.00 | B | O |
| ATOM | 3195 | N | ALA | B | 122 | 4.827 | 68.085 | 63.029 | 1.00 | 100.00 | B | N |
| ATOM | 3196 | CA | ALA | B | 122 | 3.422 | 67.932 | 62.647 | 1.00 | 100.00 | B | C |
| ATOM | 3197 | CB | ALA | B | 122 | 3.099 | 66.444 | 62.447 | 1.00 | 67.88 | B | C |
| ATOM | 3198 | C | ALA | B | 122 | 2.440 | 68.538 | 63.659 | 1.00 | 100.00 | B | C |
| ATOM | 3199 | O | ALA | B | 122 | 2.838 | 69.101 | 64.693 | 1.00 | 100.00 | B | O |
| ATOM | 3200 | N | ALA | B | 123 | 1.150 | 68.417 | 63.352 | 1.00 | 100.00 | B | N |
| ATOM | 3201 | CA | ALA | B | 123 | 0.109 | 68.928 | 64.240 | 1.00 | 100.00 | B | C |
| ATOM | 3202 | CB | ALA | B | 123 | -1.236 | 69.028 | 63.487 | 1.00 | 77.16 | B | C |
| ATOM | 3203 | C | ALA | B | 123 | -0.007 | 67.959 | 65.420 | 1.00 | 100.00 | B | C |
| ATOM | 3204 | O | ALA | B | 123 | 0.183 | 68.358 | 66.583 | 1.00 | 100.00 | B | O |
| ATOM | 3205 | N | ALA | B | 124 | -0.295 | 66.688 | 65.108 | 1.00 | 89.24 | B | N |
| ATOM | 3206 | CA | ALA | B | 124 | -0.438 | 65.637 | 66.125 | 1.00 | 89.24 | B | C |
| ATOM | 3207 | CB | ALA | B | 124 | -0.941 | 64.344 | 65.471 | 1.00 | 57.79 | B | C |
| ATOM | 3208 | C | ALA | B | 124 | 0.894 | 65.372 | 66.845 | 1.00 | 89.24 | B | C |
| ATOM | 3209 | O | ALA | B | 124 | 0.922 | 64.768 | 67.925 | 1.00 | 89.24 | B | O |
| ATOM | 3210 | N | ALA | B | 125 | 1.988 | 65.831 | 66.230 | 1.00 | 67.84 | B | N |
| ATOM | 3211 | CA | ALA | B | 125 | 3.346 | 65.657 | 66.764 | 1.00 | 67.84 | B | C |
| ATOM | 3212 | CB | ALA | B | 125 | 4.353 | 66.481 | 65.913 | 1.00 | 67.70 | B | C |
| ATOM | 3213 | C | ALA | B | 125 | 3.491 | 66.031 | 68.244 | 1.00 | 67.84 | B | C |
| ATOM | 3214 | O | ALA | B | 125 | 4.064 | 67.079 | 68.562 | 1.00 | 67.84 | B | O |
| ATOM | 3215 | N | VAL | B | 126 | 2.994 | 65.173 | 69.141 | 1.00 | 47.71 | B | N |
| ATOM | 3216 | CA | VAL | B | 126 | 3.089 | 65.451 | 70.579 | 1.00 | 47.71 | B | C |
| ATOM | 3217 | CB | VAL | B | 126 | 1.764 | 65.122 | 71.324 | 1.00 | 45.00 | B | C |
| ATOM | 3218 | CG1 | VAL | B | 126 | 0.629 | 65.950 | 70.729 | 1.00 | 45.00 | B | C |
| ATOM | 3219 | CG2 | VAL | B | 126 | 1.458 | 63.627 | 71.241 | 1.00 | 45.00 | B | C |
| ATOM | 3220 | C | VAL | B | 126 | 4.251 | 64.737 | 71.288 | 1.00 | 47.71 | B | C |
| ATOM | 3221 | O | VAL | B | 126 | 4.495 | 63.527 | 71.105 | 1.00 | 47.71 | B | O |
| ATOM | 3222 | N | TYR | B | 127 | 4.944 | 65.511 | 72.122 | 1.00 | 44.73 | B | N |
| ATOM | 3223 | CA | TYR | B | 127 | 6.103 | 65.034 | 72.855 | 1.00 | 44.73 | B | C |
| ATOM | 3224 | CB | TYR | B | 127 | 7.328 | 65.842 | 72.434 | 1.00 | 53.40 | B | C |
| ATOM | 3225 | CG | TYR | B | 127 | 7.758 | 65.570 | 71.023 | 1.00 | 53.40 | B | C |
| ATOM | 3226 | CD1 | TYR | B | 127 | 8.239 | 64.314 | 70.652 | 1.00 | 53.40 | B | C |
| ATOM | 3227 | CE1 | TYR | B | 127 | 8.623 | 64.044 | 69.334 | 1.00 | 53.40 | B | C |
| ATOM | 3228 | CD2 | TYR | B | 127 | 7.667 | 66.554 | 70.050 | 1.00 | 53.40 | B | C |
| ATOM | 3229 | CE2 | TYR | B | 127 | 8.047 | 66.299 | 68.724 | 1.00 | 53.40 | B | C |
| ATOM | 3230 | CZ | TYR | B | 127 | 8.522 | 65.043 | 68.377 | 1.00 | 53.40 | B | C |
| ATOM | 3231 | OH | TYR | B | 127 | 8.877 | 64.789 | 67.073 | 1.00 | 53.40 | B | O |
| ATOM | 3232 | C | TYR | B | 127 | 6.090 | 64.925 | 74.368 | 1.00 | 44.73 | B | C |
| ATOM | 3233 | O | TYR | B | 127 | 5.765 | 65.881 | 75.070 | 1.00 | 44.73 | B | O |
| ATOM | 3234 | N | LEU | B | 128 | 6.465 | 63.741 | 74.855 | 1.00 | 40.10 | B | N |
| ATOM | 3235 | CA | LEU | B | 128 | 6.568 | 63.475 | 76.287 | 1.00 | 40.10 | B | C |
| ATOM | 3236 | CB | LEU | B | 128 | 6.346 | 62.002 | 76.594 | 1.00 | 21.48 | B | C |
| ATOM | 3237 | CG | LEU | B | 128 | 6.848 | 61.582 | 77.974 | 1.00 | 21.48 | B | C |

FIG. 6-55

```
ATOM   3238  CD1 LEU B 128       6.107  62.352  79.045  1.00 21.48      B  C
ATOM   3239  CD2 LEU B 128       6.664  60.085  78.153  1.00 21.48      B  C
ATOM   3240  C   LEU B 128       7.978  63.848  76.698  1.00 40.10      B  C
ATOM   3241  O   LEU B 128       8.941  63.320  76.146  1.00 40.10      B  O
ATOM   3242  N   ASN B 129       8.100  64.763  77.656  1.00 29.10      B  N
ATOM   3243  CA  ASN B 129       9.401  65.213  78.140  1.00 29.10      B  C
ATOM   3244  CB  ASN B 129       9.465  66.736  78.125  1.00 25.06      B  C
ATOM   3245  CG  ASN B 129       9.279  67.309  76.742  1.00 25.06      B  C
ATOM   3246  OD1 ASN B 129      10.244  67.565  76.033  1.00 25.06      B  O
ATOM   3247  ND2 ASN B 129       8.031  67.505  76.343  1.00 25.06      B  N
ATOM   3248  C   ASN B 129       9.624  64.724  79.562  1.00 29.10      B  C
ATOM   3249  O   ASN B 129       8.817  64.993  80.444  1.00 29.10      B  O
ATOM   3250  N   LEU B 130      10.721  64.003  79.778  1.00 30.84      B  N
ATOM   3251  CA  LEU B 130      11.065  63.485  81.098  1.00 30.84      B  C
ATOM   3252  CB  LEU B 130      11.469  62.012  80.993  1.00 16.04      B  C
ATOM   3253  CG  LEU B 130      10.420  60.903  80.959  1.00 16.04      B  C
ATOM   3254  CD1 LEU B 130       9.127  61.396  80.363  1.00 16.04      B  C
ATOM   3255  CD2 LEU B 130      10.974  59.746  80.157  1.00 16.04      B  C
ATOM   3256  C   LEU B 130      12.211  64.286  81.703  1.00 30.84      B  C
ATOM   3257  O   LEU B 130      13.365  64.133  81.311  1.00 30.84      B  O
ATOM   3258  N   VAL B 131      11.889  65.139  82.666  1.00 20.22      B  N
ATOM   3259  CA  VAL B 131      12.892  65.960  83.320  1.00 20.22      B  C
ATOM   3260  CB  VAL B 131      12.295  67.309  83.747  1.00 18.78      B  C
ATOM   3261  CG1 VAL B 131      13.370  68.189  84.365  1.00 18.78      B  C
ATOM   3262  CG2 VAL B 131      11.677  67.991  82.537  1.00 18.78      B  C
ATOM   3263  C   VAL B 131      13.477  65.232  84.525  1.00 20.22      B  C
ATOM   3264  O   VAL B 131      12.930  65.249  85.626  1.00 20.22      B  O
ATOM   3265  N   LEU B 132      14.614  64.590  84.285  1.00 28.82      B  N
ATOM   3266  CA  LEU B 132      15.315  63.820  85.305  1.00 28.82      B  C
ATOM   3267  CB  LEU B 132      15.754  62.489  84.703  1.00  8.95      B  C
ATOM   3268  CG  LEU B 132      14.658  61.829  83.873  1.00  8.95      B  C
ATOM   3269  CD1 LEU B 132      14.971  61.954  82.415  1.00  8.95      B  C
ATOM   3270  CD2 LEU B 132      14.546  60.390  84.266  1.00  8.95      B  C
ATOM   3271  C   LEU B 132      16.532  64.571  85.815  1.00 28.82      B  C
ATOM   3272  O   LEU B 132      16.911  65.591  85.252  1.00 28.82      B  O
ATOM   3273  N   ASP B 133      17.132  64.064  86.886  1.00 33.82      B  N
ATOM   3274  CA  ASP B 133      18.337  64.662  87.467  1.00 33.82      B  C
ATOM   3275  CB  ASP B 133      18.765  63.885  88.705  1.00 30.44      B  C
ATOM   3276  CG  ASP B 133      18.147  64.419  89.962  1.00 30.44      B  C
ATOM   3277  OD1 ASP B 133      18.012  63.630  90.925  1.00 30.44      B  O
ATOM   3278  OD2 ASP B 133      17.814  65.629  89.990  1.00 30.44      B  O
ATOM   3279  C   ASP B 133      19.461  64.594  86.452  1.00 33.82      B  C
ATOM   3280  O   ASP B 133      19.354  63.897  85.459  1.00 33.82      B  O
ATOM   3281  N   TYR B 134      20.544  65.311  86.688  1.00 20.94      B  N
ATOM   3282  CA  TYR B 134      21.658  65.244  85.754  1.00 20.94      B  C
ATOM   3283  CB  TYR B 134      22.052  66.639  85.256  1.00 28.15      B  C
ATOM   3284  CG  TYR B 134      23.213  66.602  84.290  1.00 28.15      B  C
ATOM   3285  CD1 TYR B 134      23.013  66.291  82.944  1.00 28.15      B  C
ATOM   3286  CE1 TYR B 134      24.077  66.146  82.080  1.00 28.15      B  C
ATOM   3287  CD2 TYR B 134      24.521  66.777  84.739  1.00 28.15      B  C
ATOM   3288  CE2 TYR B 134      25.594  66.633  83.879  1.00 28.15      B  C
ATOM   3289  CZ  TYR B 134      25.364  66.312  82.555  1.00 28.15      B  C
ATOM   3290  OH  TYR B 134      26.427  66.116  81.714  1.00 28.15      B  O
ATOM   3291  C   TYR B 134      22.864  64.589  86.416  1.00 20.94      B  C
ATOM   3292  O   TYR B 134      23.187  64.901  87.554  1.00 20.94      B  O
ATOM   3293  N   VAL B 135      23.499  63.660  85.711  1.00 32.22      B  N
ATOM   3294  CA  VAL B 135      24.694  62.998  86.222  1.00 32.22      B  C
ATOM   3295  CB  VAL B 135      24.467  61.486  86.466  1.00 23.09      B  C
ATOM   3296  CG1 VAL B 135      25.578  60.929  87.359  1.00 23.09      B  C
ATOM   3297  CG2 VAL B 135      23.115  61.265  87.105  1.00 23.09      B  C
```

FIG. 6-56

| ATOM | 3298 | C | VAL | B | 135 | 25.761 | 63.214 | 85.136 | 1.00 | 32.22 | B | C |
|------|------|---|-----|---|-----|--------|--------|--------|------|-------|---|---|
| ATOM | 3299 | O | VAL | B | 135 | 25.524 | 62.920 | 83.963 | 1.00 | 32.22 | B | O |
| ATOM | 3300 | N | PRO | B | 136 | 26.944 | 63.734 | 85.523 | 1.00 | 21.91 | B | N |
| ATOM | 3301 | CD | PRO | B | 136 | 27.321 | 63.835 | 86.941 | 1.00 | 27.54 | B | C |
| ATOM | 3302 | CA | PRO | B | 136 | 28.099 | 64.043 | 84.669 | 1.00 | 21.91 | B | C |
| ATOM | 3303 | CB | PRO | B | 136 | 29.124 | 64.619 | 85.644 | 1.00 | 27.54 | B | C |
| ATOM | 3304 | CG | PRO | B | 136 | 28.380 | 64.868 | 86.898 | 1.00 | 27.54 | B | C |
| ATOM | 3305 | C | PRO | B | 136 | 28.740 | 62.934 | 83.842 | 1.00 | 21.91 | B | C |
| ATOM | 3306 | O | PRO | B | 136 | 29.275 | 63.204 | 82.780 | 1.00 | 21.91 | B | O |
| ATOM | 3307 | N | GLU | B | 137 | 28.733 | 61.698 | 84.321 | 1.00 | 23.98 | B | N |
| ATOM | 3308 | CA | GLU | B | 137 | 29.379 | 60.650 | 83.547 | 1.00 | 23.98 | B | C |
| ATOM | 3309 | CB | GLU | B | 137 | 30.815 | 60.442 | 84.058 | 1.00 | 38.31 | B | C |
| ATOM | 3310 | CG | GLU | B | 137 | 31.842 | 60.146 | 82.962 | 1.00 | 38.31 | B | C |
| ATOM | 3311 | CD | GLU | B | 137 | 32.361 | 61.399 | 82.297 | 1.00 | 38.31 | B | C |
| ATOM | 3312 | OE1 | GLU | B | 137 | 32.824 | 61.308 | 81.147 | 1.00 | 38.31 | B | O |
| ATOM | 3313 | OE2 | GLU | B | 137 | 32.323 | 62.476 | 82.930 | 1.00 | 38.31 | B | O |
| ATOM | 3314 | C | GLU | B | 137 | 28.633 | 59.321 | 83.540 | 1.00 | 23.98 | B | C |
| ATOM | 3315 | O | GLU | B | 137 | 27.537 | 59.196 | 84.090 | 1.00 | 23.98 | B | O |
| ATOM | 3316 | N | THR | B | 138 | 29.239 | 58.329 | 82.902 | 1.00 | 24.20 | B | N |
| ATOM | 3317 | CA | THR | B | 138 | 28.640 | 57.009 | 82.806 | 1.00 | 24.20 | B | C |
| ATOM | 3318 | CB | THR | B | 138 | 27.845 | 56.855 | 81.509 | 1.00 | 29.04 | B | C |
| ATOM | 3319 | OG1 | THR | B | 138 | 28.753 | 56.753 | 80.409 | 1.00 | 29.04 | B | O |
| ATOM | 3320 | CG2 | THR | B | 138 | 26.940 | 58.054 | 81.296 | 1.00 | 29.04 | B | C |
| ATOM | 3321 | C | THR | B | 138 | 29.721 | 55.950 | 82.809 | 1.00 | 24.20 | B | C |
| ATOM | 3322 | O | THR | B | 138 | 30.820 | 56.190 | 82.346 | 1.00 | 24.20 | B | O |
| ATOM | 3323 | N | VAL | B | 139 | 29.398 | 54.770 | 83.322 | 1.00 | 29.48 | B | N |
| ATOM | 3324 | CA | VAL | B | 139 | 30.357 | 53.677 | 83.364 | 1.00 | 29.48 | B | C |
| ATOM | 3325 | CB | VAL | B | 139 | 29.674 | 52.377 | 83.859 | 1.00 | 23.63 | B | C |
| ATOM | 3326 | CG1 | VAL | B | 139 | 30.486 | 51.151 | 83.443 | 1.00 | 23.63 | B | C |
| ATOM | 3327 | CG2 | VAL | B | 139 | 29.544 | 52.416 | 85.383 | 1.00 | 23.63 | B | C |
| ATOM | 3328 | C | VAL | B | 139 | 31.010 | 53.439 | 81.999 | 1.00 | 29.48 | B | C |
| ATOM | 3329 | O | VAL | B | 139 | 32.197 | 53.161 | 81.912 | 1.00 | 29.48 | B | O |
| ATOM | 3330 | N | TYR | B | 140 | 30.231 | 53.553 | 80.935 | 1.00 | 30.63 | B | N |
| ATOM | 3331 | CA | TYR | B | 140 | 30.739 | 53.351 | 79.584 | 1.00 | 30.63 | B | C |
| ATOM | 3332 | CB | TYR | B | 140 | 29.648 | 53.685 | 78.560 | 1.00 | 34.08 | B | C |
| ATOM | 3333 | CG | TYR | B | 140 | 30.130 | 53.605 | 77.138 | 1.00 | 34.08 | B | C |
| ATOM | 3334 | CD1 | TYR | B | 140 | 30.244 | 52.383 | 76.482 | 1.00 | 34.08 | B | C |
| ATOM | 3335 | CE1 | TYR | B | 140 | 30.785 | 52.306 | 75.188 | 1.00 | 34.08 | B | C |
| ATOM | 3336 | CD2 | TYR | B | 140 | 30.557 | 54.756 | 76.470 | 1.00 | 34.08 | B | C |
| ATOM | 3337 | CE2 | TYR | B | 140 | 31.093 | 54.698 | 75.188 | 1.00 | 34.08 | B | C |
| ATOM | 3338 | CZ | TYR | B | 140 | 31.213 | 53.474 | 74.548 | 1.00 | 34.08 | B | C |
| ATOM | 3339 | OH | TYR | B | 140 | 31.795 | 53.434 | 73.291 | 1.00 | 34.08 | B | O |
| ATOM | 3340 | C | TYR | B | 140 | 31.976 | 54.224 | 79.340 | 1.00 | 30.63 | B | C |
| ATOM | 3341 | O | TYR | B | 140 | 33.049 | 53.717 | 78.999 | 1.00 | 30.63 | B | O |
| ATOM | 3342 | N | ARG | B | 141 | 31.813 | 55.536 | 79.517 | 1.00 | 24.15 | B | N |
| ATOM | 3343 | CA | ARG | B | 141 | 32.897 | 56.500 | 79.332 | 1.00 | 24.15 | B | C |
| ATOM | 3344 | CB | ARG | B | 141 | 32.367 | 57.928 | 79.501 | 1.00 | 27.54 | B | C |
| ATOM | 3345 | CG | ARG | B | 141 | 31.493 | 58.421 | 78.370 | 1.00 | 27.54 | B | C |
| ATOM | 3346 | CD | ARG | B | 141 | 30.514 | 59.450 | 78.896 | 1.00 | 27.54 | B | C |
| ATOM | 3347 | NE | ARG | B | 141 | 31.167 | 60.669 | 79.362 | 1.00 | 27.54 | B | N |
| ATOM | 3348 | CZ | ARG | B | 141 | 31.475 | 61.701 | 78.576 | 1.00 | 27.54 | B | C |
| ATOM | 3349 | NH1 | ARG | B | 141 | 31.185 | 61.668 | 77.282 | 1.00 | 27.54 | B | N |
| ATOM | 3350 | NH2 | ARG | B | 141 | 32.077 | 62.768 | 79.086 | 1.00 | 27.54 | B | N |
| ATOM | 3351 | C | ARG | B | 141 | 34.065 | 56.281 | 80.287 | 1.00 | 24.15 | B | C |
| ATOM | 3352 | O | ARG | B | 141 | 35.207 | 56.247 | 79.869 | 1.00 | 24.15 | B | O |
| ATOM | 3353 | N | VAL | B | 142 | 33.783 | 56.131 | 81.579 | 1.00 | 27.57 | B | N |
| ATOM | 3354 | CA | VAL | B | 142 | 34.830 | 55.939 | 82.588 | 1.00 | 27.57 | B | C |
| ATOM | 3355 | CB | VAL | B | 142 | 34.216 | 55.826 | 84.005 | 1.00 | 9.19 | B | C |
| ATOM | 3356 | CG1 | VAL | B | 142 | 35.271 | 55.447 | 85.013 | 1.00 | 9.19 | B | C |
| ATOM | 3357 | CG2 | VAL | B | 142 | 33.582 | 57.138 | 84.401 | 1.00 | 9.19 | B | C |

FIG. 6-57

```
ATOM   3358  C    VAL B 142      35.717  54.720  82.353  1.00 27.57      B  C
ATOM   3359  O    VAL B 142      36.851  54.694  82.814  1.00 27.57      B  O
ATOM   3360  N    ALA B 143      35.203  53.724  81.651  1.00 43.49      B  N
ATOM   3361  CA   ALA B 143      35.939  52.487  81.396  1.00 43.49      B  C
ATOM   3362  CB   ALA B 143      35.005  51.318  81.572  1.00  2.21      B  C
ATOM   3363  C    ALA B 143      36.600  52.427  80.012  1.00 43.49      B  C
ATOM   3364  O    ALA B 143      37.169  51.384  79.632  1.00 43.49      B  O
ATOM   3365  N    ARG B 144      36.519  53.528  79.274  1.00 30.01      B  N
ATOM   3366  CA   ARG B 144      37.098  53.639  77.941  1.00 30.01      B  C
ATOM   3367  CB   ARG B 144      36.089  54.267  76.948  1.00 99.82      B  C
ATOM   3368  CG   ARG B 144      35.421  55.584  77.375  1.00 99.82      B  C
ATOM   3369  CD   ARG B 144      36.373  56.741  77.125  1.00 99.82      B  C
ATOM   3370  NE   ARG B 144      35.873  58.054  77.540  1.00 99.82      B  N
ATOM   3371  CZ   ARG B 144      36.583  59.166  77.376  1.00 99.82      B  C
ATOM   3372  NH1  ARG B 144      36.124  60.371  77.757  1.00 99.82      B  N
ATOM   3373  NH2  ARG B 144      37.801  59.067  76.812  1.00 99.82      B  N
ATOM   3374  C    ARG B 144      38.281  54.527  78.178  1.00 30.01      B  C
ATOM   3375  O    ARG B 144      39.344  54.341  77.594  1.00 30.01      B  O
ATOM   3376  N    HIS B 145      38.098  55.447  79.099  1.00 38.20      B  N
ATOM   3377  CA   HIS B 145      39.182  56.313  79.433  1.00 38.20      B  C
ATOM   3378  CB   HIS B 145      38.895  57.142  80.574  1.00 85.90      B  C
ATOM   3379  CG   HIS B 145      40.106  57.832  81.051  1.00 85.90      B  C
ATOM   3380  CD2  HIS B 145      40.504  59.097  80.795  1.00 85.90      B  C
ATOM   3381  ND1  HIS B 145      40.945  57.278  81.951  1.00 85.90      B  N
ATOM   3382  CE1  HIS B 145      41.821  58.239  82.325  1.00 85.90      B  C
ATOM   3383  NE2  HIS B 145      41.551  59.332  81.651  1.00 85.90      B  N
ATOM   3384  C    HIS B 145      40.261  55.432  79.976  1.00 38.20      B  C
ATOM   3385  O    HIS B 145      41.450  55.693  79.762  1.00 38.20      B  O
ATOM   3386  N    TYR B 146      39.806  54.490  80.795  1.00 39.49      B  N
ATOM   3387  CA   TYR B 146      40.629  53.496  81.403  1.00 39.49      B  C
ATOM   3388  CB   TYR B 146      40.003  52.864  82.674  1.00 59.95      B  C
ATOM   3389  CG   TYR B 146      40.530  53.483  83.907  1.00 59.95      B  C
ATOM   3390  CD1  TYR B 146      39.725  54.322  84.660  1.00 59.95      B  C
ATOM   3391  CE1  TYR B 146      40.208  55.005  85.730  1.00 59.95      B  C
ATOM   3392  CD2  TYR B 146      41.864  53.316  84.276  1.00 59.95      B  C
ATOM   3393  CE2  TYR B 146      42.373  53.995  85.346  1.00 59.95      B  C
ATOM   3394  CZ   TYR B 146      41.536  54.849  86.068  1.00 59.95      B  C
ATOM   3395  OH   TYR B 146      42.064  55.636  87.055  1.00 59.95      B  O
ATOM   3396  C    TYR B 146      40.924  52.307  80.558  1.00 39.49      B  C
ATOM   3397  O    TYR B 146      41.779  51.492  80.928  1.00 39.49      B  O
ATOM   3398  N    SER B 147      40.427  52.382  79.249  1.00 39.48      B  N
ATOM   3399  CA   SER B 147      40.808  51.272  78.568  1.00 39.48      B  C
ATOM   3400  CB   SER B 147      39.628  50.518  77.909  1.00 47.43      B  C
ATOM   3401  OG   SER B 147      40.221  49.329  77.325  1.00 47.43      B  O
ATOM   3402  C    SER B 147      41.825  51.809  77.692  1.00 39.48      B  C
ATOM   3403  O    SER B 147      42.937  51.250  77.607  1.00 39.48      B  O
ATOM   3404  N    ARG B 148      41.467  52.944  77.124  1.00 46.72      B  N
ATOM   3405  CA   ARG B 148      42.278  53.645  76.189  1.00 46.72      B  C
ATOM   3406  CB   ARG B 148      41.457  54.819  75.661  1.00 74.20      B  C
ATOM   3407  CG   ARG B 148      41.155  54.719  74.166  1.00 74.20      B  C
ATOM   3408  CD   ARG B 148      39.750  55.195  73.805  1.00 74.20      B  C
ATOM   3409  NE   ARG B 148      39.434  56.464  74.451  1.00 74.20      B  N
ATOM   3410  CZ   ARG B 148      38.491  57.301  74.021  1.00 74.20      B  C
ATOM   3411  NH1  ARG B 148      37.773  56.999  72.937  1.00 74.20      B  N
ATOM   3412  NH2  ARG B 148      38.260  58.439  74.669  1.00 74.20      B  N
ATOM   3413  C    ARG B 148      43.617  54.115  76.742  1.00 46.72      B  C
ATOM   3414  O    ARG B 148      44.469  54.546  75.978  1.00 46.72      B  O
ATOM   3415  N    ALA B 149      43.811  54.052  78.053  1.00 48.34      B  N
ATOM   3416  CA   ALA B 149      45.081  54.482  78.636  1.00 48.34      B  C
ATOM   3417  CB   ALA B 149      44.824  55.460  79.772  1.00 23.93      B  C
```

FIG. 6-58

```
ATOM   3418  C    ALA B 149      45.865  53.261  79.143  1.00 48.34      B  C
ATOM   3419  O    ALA B 149      46.673  53.356  80.077  1.00 48.34      B  O
ATOM   3420  N    ALA B 150      45.603  52.112  78.528  1.00 44.48      B  N
ATOM   3421  CA   ALA B 150      46.268  50.872  78.893  1.00 44.48      B  C
ATOM   3422  CB   ALA B 150      47.758  51.012  78.690  1.00 58.73      B  C
ATOM   3423  C    ALA B 150      45.989  50.397  80.319  1.00 44.48      B  C
ATOM   3424  O    ALA B 150      46.576  49.414  80.764  1.00 44.48      B  O
ATOM   3425  N    GLN B 151      45.098  51.057  81.047  1.00 50.44      B  N
ATOM   3426  CA   GLN B 151      44.848  50.588  82.406  1.00 50.44      B  C
ATOM   3427  CB   GLN B 151      45.099  51.687  83.418  1.00 55.44      B  C
ATOM   3428  CG   GLN B 151      45.882  52.833  82.882  1.00 55.44      B  C
ATOM   3429  CD   GLN B 151      46.335  53.722  83.992  1.00 55.44      B  C
ATOM   3430  OE1  GLN B 151      47.060  53.279  84.896  1.00 55.44      B  O
ATOM   3431  NE2  GLN B 151      45.906  54.982  83.955  1.00 55.44      B  N
ATOM   3432  C    GLN B 151      43.468  50.043  82.694  1.00 50.44      B  C
ATOM   3433  O    GLN B 151      42.620  49.978  81.832  1.00 50.44      B  O
ATOM   3434  N    THR B 152      43.260  49.618  83.931  1.00 41.74      B  N
ATOM   3435  CA   THR B 152      41.961  49.107  84.350  1.00 41.74      B  C
ATOM   3436  CB   THR B 152      42.047  47.634  84.832  1.00 41.58      B  C
ATOM   3437  OG1  THR B 152      42.931  47.539  85.957  1.00 41.58      B  O
ATOM   3438  CG2  THR B 152      42.559  46.738  83.705  1.00 41.58      B  C
ATOM   3439  C    THR B 152      41.477  49.977  85.503  1.00 41.74      B  C
ATOM   3440  O    THR B 152      42.288  50.556  86.228  1.00 41.74      B  O
ATOM   3441  N    LEU B 153      40.163  50.095  85.657  1.00 25.89      B  N
ATOM   3442  CA   LEU B 153      39.603  50.892  86.740  1.00 25.89      B  C
ATOM   3443  CB   LEU B 153      38.081  50.952  86.594  1.00 30.62      B  C
ATOM   3444  CG   LEU B 153      37.250  51.421  87.798  1.00 30.62      B  C
ATOM   3445  CD1  LEU B 153      37.463  52.910  88.068  1.00 30.62      B  C
ATOM   3446  CD2  LEU B 153      35.774  51.139  87.515  1.00 30.62      B  C
ATOM   3447  C    LEU B 153      39.970  50.221  88.072  1.00 25.89      B  C
ATOM   3448  O    LEU B 153      39.873  49.000  88.202  1.00 25.89      B  O
ATOM   3449  N    PRO B 154      40.431  51.004  89.065  1.00 23.15      B  N
ATOM   3450  CD   PRO B 154      40.746  52.440  89.009  1.00 20.18      B  C
ATOM   3451  CA   PRO B 154      40.795  50.442  90.372  1.00 23.15      B  C
ATOM   3452  CB   PRO B 154      41.007  51.680  91.229  1.00 20.18      B  C
ATOM   3453  CG   PRO B 154      41.571  52.634  90.265  1.00 20.18      B  C
ATOM   3454  C    PRO B 154      39.645  49.570  90.891  1.00 23.15      B  C
ATOM   3455  O    PRO B 154      38.487  49.854  90.619  1.00 23.15      B  O
ATOM   3456  N    VAL B 155      39.941  48.513  91.636  1.00 28.64      B  N
ATOM   3457  CA   VAL B 155      38.849  47.670  92.127  1.00 28.64      B  C
ATOM   3458  CB   VAL B 155      39.345  46.320  92.713  1.00 29.01      B  C
ATOM   3459  CG1  VAL B 155      40.078  45.529  91.668  1.00 29.01      B  C
ATOM   3460  CG2  VAL B 155      40.219  46.569  93.916  1.00 29.01      B  C
ATOM   3461  C    VAL B 155      37.977  48.296  93.204  1.00 28.64      B  C
ATOM   3462  O    VAL B 155      36.905  47.786  93.494  1.00 28.64      B  O
ATOM   3463  N    ILE B 156      38.435  49.375  93.824  1.00 27.92      B  N
ATOM   3464  CA   ILE B 156      37.632  49.986  94.861  1.00 27.92      B  C
ATOM   3465  CB   ILE B 156      38.421  51.082  95.646  1.00 16.09      B  C
ATOM   3466  CG2  ILE B 156      38.942  52.160  94.718  1.00 16.09      B  C
ATOM   3467  CG1  ILE B 156      37.524  51.701  96.714  1.00 16.09      B  C
ATOM   3468  CD1  ILE B 156      37.046  50.725  97.764  1.00 16.09      B  C
ATOM   3469  C    ILE B 156      36.420  50.555  94.142  1.00 27.92      B  C
ATOM   3470  O    ILE B 156      35.290  50.386  94.588  1.00 27.92      B  O
ATOM   3471  N    TYR B 157      36.659  51.193  93.002  1.00 22.61      B  N
ATOM   3472  CA   TYR B 157      35.582  51.775  92.207  1.00 22.61      B  C
ATOM   3473  CB   TYR B 157      36.153  52.656  91.086  1.00 38.18      B  C
ATOM   3474  CG   TYR B 157      36.678  53.996  91.555  1.00 38.18      B  C
ATOM   3475  CD1  TYR B 157      35.815  54.950  92.094  1.00 38.18      B  C
ATOM   3476  CE1  TYR B 157      36.287  56.191  92.517  1.00 38.18      B  C
ATOM   3477  CD2  TYR B 157      38.038  54.314  91.449  1.00 38.18      B  C
```

FIG. 6-59

```
ATOM   3478  CE2 TYR B 157      38.528  55.560  91.868  1.00 38.18      B    C
ATOM   3479  CZ  TYR B 157      37.648  56.492  92.399  1.00 38.18      B    C
ATOM   3480  OH  TYR B 157      38.120  57.723  92.798  1.00 38.18      B    O
ATOM   3481  C   TYR B 157      34.681  50.699  91.608  1.00 22.61      B    C
ATOM   3482  O   TYR B 157      33.480  50.885  91.516  1.00 22.61      B    O
ATOM   3483  N   VAL B 158      35.270  49.579  91.197  1.00 27.37      B    N
ATOM   3484  CA  VAL B 158      34.513  48.462  90.637  1.00 27.37      B    C
ATOM   3485  CB  VAL B 158      35.450  47.319  90.172  1.00 24.60      B    C
ATOM   3486  CG1 VAL B 158      34.650  46.040  89.930  1.00 24.60      B    C
ATOM   3487  CG2 VAL B 158      36.164  47.737  88.896  1.00 24.60      B    C
ATOM   3488  C   VAL B 158      33.560  47.930  91.706  1.00 27.37      B    C
ATOM   3489  O   VAL B 158      32.432  47.562  91.414  1.00 27.37      B    O
ATOM   3490  N   LYS B 159      34.028  47.896  92.944  1.00 12.85      B    N
ATOM   3491  CA  LYS B 159      33.225  47.439  94.065  1.00 12.85      B    C
ATOM   3492  CB  LYS B 159      34.086  47.331  95.340  1.00 23.85      B    C
ATOM   3493  CG  LYS B 159      34.988  46.116  95.386  1.00 23.85      B    C
ATOM   3494  CD  LYS B 159      35.804  46.037  96.660  1.00 23.85      B    C
ATOM   3495  CE  LYS B 159      36.770  44.862  96.579  1.00 23.85      B    C
ATOM   3496  NZ  LYS B 159      37.625  44.703  97.775  1.00 23.85      B    N
ATOM   3497  C   LYS B 159      32.063  48.396  94.324  1.00 12.85      B    C
ATOM   3498  O   LYS B 159      30.921  47.966  94.463  1.00 12.85      B    O
ATOM   3499  N   LEU B 160      32.378  49.691  94.394  1.00 18.84      B    N
ATOM   3500  CA  LEU B 160      31.398  50.745  94.636  1.00 18.84      B    C
ATOM   3501  CB  LEU B 160      32.092  52.107  94.708  1.00 23.07      B    C
ATOM   3502  CG  LEU B 160      32.874  52.445  95.970  1.00 23.07      B    C
ATOM   3503  CD1 LEU B 160      33.617  53.720  95.731  1.00 23.07      B    C
ATOM   3504  CD2 LEU B 160      31.945  52.576  97.172  1.00 23.07      B    C
ATOM   3505  C   LEU B 160      30.306  50.830  93.587  1.00 18.84      B    C
ATOM   3506  O   LEU B 160      29.124  50.945  93.921  1.00 18.84      B    O
ATOM   3507  N   TYR B 161      30.705  50.798  92.318  1.00 12.79      B    N
ATOM   3508  CA  TYR B 161      29.751  50.874  91.231  1.00 12.79      B    C
ATOM   3509  CB  TYR B 161      30.469  51.097  89.904  1.00 29.69      B    C
ATOM   3510  CG  TYR B 161      31.226  52.404  89.831  1.00 29.69      B    C
ATOM   3511  CD1 TYR B 161      30.986  53.421  90.757  1.00 29.69      B    C
ATOM   3512  CE1 TYR B 161      31.717  54.602  90.733  1.00 29.69      B    C
ATOM   3513  CD2 TYR B 161      32.217  52.611  88.859  1.00 29.69      B    C
ATOM   3514  CE2 TYR B 161      32.955  53.796  88.823  1.00 29.69      B    C
ATOM   3515  CZ  TYR B 161      32.702  54.786  89.767  1.00 29.69      B    C
ATOM   3516  OH  TYR B 161      33.440  55.952  89.762  1.00 29.69      B    O
ATOM   3517  C   TYR B 161      28.918  49.608  91.155  1.00 12.79      B    C
ATOM   3518  O   TYR B 161      27.699  49.676  91.114  1.00 12.79      B    O
ATOM   3519  N   MET B 162      29.571  48.454  91.142  1.00 15.76      B    N
ATOM   3520  CA  MET B 162      28.856  47.183  91.064  1.00 15.76      B    C
ATOM   3521  CB  MET B 162      29.836  46.014  91.086  1.00 27.25      B    C
ATOM   3522  CG  MET B 162      30.608  45.840  89.808  1.00 27.25      B    C
ATOM   3523  SD  MET B 162      29.544  45.941  88.342  1.00 27.25      B    S
ATOM   3524  CE  MET B 162      28.555  44.453  88.512  1.00 27.25      B    C
ATOM   3525  C   MET B 162      27.839  46.981  92.186  1.00 15.76      B    C
ATOM   3526  O   MET B 162      26.740  46.479  91.965  1.00 15.76      B    O
ATOM   3527  N   TYR B 163      28.223  47.357  93.399  1.00 30.15      B    N
ATOM   3528  CA  TYR B 163      27.347  47.231  94.556  1.00 30.15      B    C
ATOM   3529  CB  TYR B 163      28.100  47.621  95.833  1.00 21.46      B    C
ATOM   3530  CG  TYR B 163      27.283  47.587  97.110  1.00 21.46      B    C
ATOM   3531  CD1 TYR B 163      27.000  46.387  97.744  1.00 21.46      B    C
ATOM   3532  CE1 TYR B 163      26.263  46.358  98.917  1.00 21.46      B    C
ATOM   3533  CD2 TYR B 163      26.801  48.768  97.686  1.00 21.46      B    C
ATOM   3534  CE2 TYR B 163      26.061  48.750  98.854  1.00 21.46      B    C
ATOM   3535  CZ  TYR B 163      25.794  47.542  99.468  1.00 21.46      B    C
ATOM   3536  OH  TYR B 163      25.066  47.517 100.638  1.00 21.46      B    O
ATOM   3537  C   TYR B 163      26.103  48.110  94.411  1.00 30.15      B    C
```

FIG. 6-60

```
ATOM   3538  O    TYR B 163      24.987  47.666  94.655  1.00 30.15      B  O
ATOM   3539  N    GLN B 164      26.302  49.363  94.021  1.00 18.17      B  N
ATOM   3540  CA   GLN B 164      25.192  50.277  93.848  1.00 18.17      B  C
ATOM   3541  CB   GLN B 164      25.713  51.684  93.577  1.00 15.62      B  C
ATOM   3542  CG   GLN B 164      26.524  52.219  94.722  1.00 15.62      B  C
ATOM   3543  CD   GLN B 164      27.064  53.603  94.471  1.00 15.62      B  C
ATOM   3544  OE1  GLN B 164      26.311  54.568  94.354  1.00 15.62      B  O
ATOM   3545  NE2  GLN B 164      28.387  53.710  94.381  1.00 15.62      B  N
ATOM   3546  C    GLN B 164      24.263  49.815  92.723  1.00 18.17      B  C
ATOM   3547  O    GLN B 164      23.068  50.105  92.732  1.00 18.17      B  O
ATOM   3548  N    LEU B 165      24.803  49.085  91.759  1.00 17.96      B  N
ATOM   3549  CA   LEU B 165      23.982  48.604  90.663  1.00 17.96      B  C
ATOM   3550  CB   LEU B 165      24.844  47.991  89.560  1.00 12.94      B  C
ATOM   3551  CG   LEU B 165      24.338  47.962  88.114  1.00 12.94      B  C
ATOM   3552  CD1  LEU B 165      25.057  46.843  87.413  1.00 12.94      B  C
ATOM   3553  CD2  LEU B 165      22.837  47.763  88.025  1.00 12.94      B  C
ATOM   3554  C    LEU B 165      23.057  47.521  91.198  1.00 17.96      B  C
ATOM   3555  O    LEU B 165      21.877  47.455  90.856  1.00 17.96      B  O
ATOM   3556  N    PHE B 166      23.608  46.653  92.035  1.00 28.01      B  N
ATOM   3557  CA   PHE B 166      22.823  45.572  92.574  1.00 28.01      B  C
ATOM   3558  CB   PHE B 166      23.719  44.580  93.316  1.00 16.06      B  C
ATOM   3559  CG   PHE B 166      24.535  43.705  92.404  1.00 16.06      B  C
ATOM   3560  CD1  PHE B 166      23.912  42.885  91.463  1.00 16.06      B  C
ATOM   3561  CD2  PHE B 166      25.925  43.715  92.462  1.00 16.06      B  C
ATOM   3562  CE1  PHE B 166      24.666  42.086  90.593  1.00 16.06      B  C
ATOM   3563  CE2  PHE B 166      26.683  42.921  91.599  1.00 16.06      B  C
ATOM   3564  CZ   PHE B 166      26.049  42.110  90.662  1.00 16.06      B  C
ATOM   3565  C    PHE B 166      21.722  46.098  93.466  1.00 28.01      B  C
ATOM   3566  O    PHE B 166      20.619  45.569  93.457  1.00 28.01      B  O
ATOM   3567  N    ARG B 167      21.997  47.147  94.226  1.00 31.87      B  N
ATOM   3568  CA   ARG B 167      20.964  47.689  95.079  1.00 31.87      B  C
ATOM   3569  CB   ARG B 167      21.485  48.848  95.921  1.00 16.29      B  C
ATOM   3570  CG   ARG B 167      22.302  48.435  97.121  1.00 16.29      B  C
ATOM   3571  CD   ARG B 167      22.464  49.601  98.055  1.00 16.29      B  C
ATOM   3572  NE   ARG B 167      21.210  49.956  98.706  1.00 16.29      B  N
ATOM   3573  CZ   ARG B 167      21.011  51.085  99.375  1.00 16.29      B  C
ATOM   3574  NH1  ARG B 167      21.982  51.983  99.478  1.00 16.29      B  N
ATOM   3575  NH2  ARG B 167      19.847  51.307  99.958  1.00 16.29      B  N
ATOM   3576  C    ARG B 167      19.801  48.165  94.229  1.00 31.87      B  C
ATOM   3577  O    ARG B 167      18.645  47.934  94.568  1.00 31.87      B  O
ATOM   3578  N    SER B 168      20.098  48.816  93.114  1.00 18.22      B  N
ATOM   3579  CA   SER B 168      19.030  49.329  92.265  1.00 18.22      B  C
ATOM   3580  CB   SER B 168      19.589  50.285  91.200  1.00 12.02      B  C
ATOM   3581  OG   SER B 168      20.308  49.601  90.201  1.00 12.02      B  O
ATOM   3582  C    SER B 168      18.258  48.190  91.616  1.00 18.22      B  C
ATOM   3583  O    SER B 168      17.059  48.301  91.352  1.00 18.22      B  O
ATOM   3584  N    LEU B 169      18.954  47.087  91.373  1.00 18.80      B  N
ATOM   3585  CA   LEU B 169      18.338  45.916  90.770  1.00 18.80      B  C
ATOM   3586  CB   LEU B 169      19.427  44.982  90.234  1.00 10.10      B  C
ATOM   3587  CG   LEU B 169      19.668  44.920  88.720  1.00 10.10      B  C
ATOM   3588  CD1  LEU B 169      19.329  46.222  88.037  1.00 10.10      B  C
ATOM   3589  CD2  LEU B 169      21.108  44.541  88.479  1.00 10.10      B  C
ATOM   3590  C    LEU B 169      17.470  45.215  91.819  1.00 18.80      B  C
ATOM   3591  O    LEU B 169      16.352  44.792  91.535  1.00 18.80      B  O
ATOM   3592  N    ALA B 170      17.994  45.114  93.039  1.00 25.18      B  N
ATOM   3593  CA   ALA B 170      17.272  44.504  94.155  1.00 25.18      B  C
ATOM   3594  CB   ALA B 170      18.128  44.531  95.414  1.00  6.97      B  C
ATOM   3595  C    ALA B 170      15.991  45.294  94.391  1.00 25.18      B  C
ATOM   3596  O    ALA B 170      14.939  44.727  94.682  1.00 25.18      B  O
ATOM   3597  N    TYR B 171      16.096  46.611  94.263  1.00 23.91      B  N
```

FIG. 6-61

```
ATOM   3598  CA   TYR B 171      14.955  47.482  94.442  1.00 23.91      B    C
ATOM   3599  CB   TYR B 171      15.372  48.945  94.328  1.00 18.06      B    C
ATOM   3600  CG   TYR B 171      14.227  49.930  94.506  1.00 18.06      B    C
ATOM   3601  CD1  TYR B 171      13.676  50.180  95.763  1.00 18.06      B    C
ATOM   3602  CE1  TYR B 171      12.644  51.112  95.932  1.00 18.06      B    C
ATOM   3603  CD2  TYR B 171      13.714  50.632  93.420  1.00 18.06      B    C
ATOM   3604  CE2  TYR B 171      12.689  51.561  93.576  1.00 18.06      B    C
ATOM   3605  CZ   TYR B 171      12.157  51.798  94.833  1.00 18.06      B    C
ATOM   3606  OH   TYR B 171      11.136  52.711  94.989  1.00 18.06      B    O
ATOM   3607  C    TYR B 171      13.892  47.173  93.399  1.00 23.91      B    C
ATOM   3608  O    TYR B 171      12.902  46.513  93.693  1.00 23.91      B    O
ATOM   3609  N    ILE B 172      14.105  47.637  92.173  1.00 17.03      B    N
ATOM   3610  CA   ILE B 172      13.133  47.425  91.109  1.00 17.03      B    C
ATOM   3611  CB   ILE B 172      13.704  47.823  89.731  1.00 21.31      B    C
ATOM   3612  CG2  ILE B 172      14.249  49.247  89.795  1.00 21.31      B    C
ATOM   3613  CG1  ILE B 172      14.773  46.819  89.295  1.00 21.31      B    C
ATOM   3614  CD1  ILE B 172      15.140  46.906  87.830  1.00 21.31      B    C
ATOM   3615  C    ILE B 172      12.606  45.992  91.024  1.00 17.03      B    C
ATOM   3616  O    ILE B 172      11.427  45.770  90.770  1.00 17.03      B    O
ATOM   3617  N    HIS B 173      13.464  45.009  91.240  1.00 24.56      B    N
ATOM   3618  CA   HIS B 173      12.996  43.637  91.155  1.00 24.56      B    C
ATOM   3619  CB   HIS B 173      14.174  42.662  91.221  1.00 17.06      B    C
ATOM   3620  CG   HIS B 173      15.029  42.674  89.989  1.00 17.06      B    C
ATOM   3621  CD2  HIS B 173      14.911  43.364  88.829  1.00 17.06      B    C
ATOM   3622  ND1  HIS B 173      16.177  41.919  89.864  1.00 17.06      B    N
ATOM   3623  CE1  HIS B 173      16.728  42.146  88.684  1.00 17.06      B    C
ATOM   3624  NE2  HIS B 173      15.979  43.019  88.038  1.00 17.06      B    N
ATOM   3625  C    HIS B 173      11.958  43.323  92.225  1.00 24.56      B    C
ATOM   3626  O    HIS B 173      11.023  42.560  91.978  1.00 24.56      B    O
ATOM   3627  N    SER B 174      12.101  43.925  93.402  1.00 27.79      B    N
ATOM   3628  CA   SER B 174      11.146  43.691  94.478  1.00 27.79      B    C
ATOM   3629  CB   SER B 174      11.487  44.525  95.713  1.00 25.93      B    C
ATOM   3630  OG   SER B 174      11.286  45.904  95.474  1.00 25.93      B    O
ATOM   3631  C    SER B 174       9.738  44.029  94.009  1.00 27.79      B    C
ATOM   3632  O    SER B 174       8.769  43.462  94.512  1.00 27.79      B    O
ATOM   3633  N    PHE B 175       9.634  44.953  93.050  1.00 17.77      B    N
ATOM   3634  CA   PHE B 175       8.348  45.365  92.501  1.00 17.77      B    C
ATOM   3635  CB   PHE B 175       8.355  46.826  92.065  1.00 36.06      B    C
ATOM   3636  CG   PHE B 175       8.514  47.792  93.185  1.00 36.06      B    C
ATOM   3637  CD1  PHE B 175       9.778  48.215  93.579  1.00 36.06      B    C
ATOM   3638  CD2  PHE B 175       7.395  48.285  93.855  1.00 36.06      B    C
ATOM   3639  CE1  PHE B 175       9.929  49.115  94.624  1.00 36.06      B    C
ATOM   3640  CE2  PHE B 175       7.537  49.190  94.911  1.00 36.06      B    C
ATOM   3641  CZ   PHE B 175       8.809  49.606  95.295  1.00 36.06      B    C
ATOM   3642  C    PHE B 175       7.987  44.532  91.286  1.00 17.77      B    C
ATOM   3643  O    PHE B 175       6.938  44.747  90.677  1.00 17.77      B    O
ATOM   3644  N    GLY B 176       8.861  43.595  90.924  1.00 26.80      B    N
ATOM   3645  CA   GLY B 176       8.611  42.757  89.762  1.00 26.80      B    C
ATOM   3646  C    GLY B 176       8.851  43.476  88.442  1.00 26.80      B    C
ATOM   3647  O    GLY B 176       8.218  43.191  87.428  1.00 26.80      B    O
ATOM   3648  N    ILE B 177       9.774  44.425  88.464  1.00 23.69      B    N
ATOM   3649  CA   ILE B 177      10.113  45.199  87.283  1.00 23.69      B    C
ATOM   3650  CB   ILE B 177      10.126  46.716  87.602  1.00 18.65      B    C
ATOM   3651  CG2  ILE B 177      10.671  47.508  86.426  1.00 18.65      B    C
ATOM   3652  CG1  ILE B 177       8.710  47.167  87.962  1.00 18.65      B    C
ATOM   3653  CD1  ILE B 177       8.597  48.630  88.309  1.00 18.65      B    C
ATOM   3654  C    ILE B 177      11.488  44.768  86.799  1.00 23.69      B    C
ATOM   3655  O    ILE B 177      12.412  44.629  87.592  1.00 23.69      B    O
ATOM   3656  N    CYS B 178      11.613  44.533  85.498  1.00 20.94      B    N
ATOM   3657  CA   CYS B 178      12.889  44.138  84.925  1.00 20.94      B    C
```

FIG. 6-62

| ATOM | 3658 | CB | CYS | B | 178 | 12.740 | 42.870 | 84.088 | 1.00 | 36.73 | B | C |
|---|---|---|---|---|---|---|---|---|---|---|---|---|
| ATOM | 3659 | SG | CYS | B | 178 | 14.291 | 42.010 | 83.753 | 1.00 | 36.73 | B | S |
| ATOM | 3660 | C | CYS | B | 178 | 13.350 | 45.274 | 84.039 | 1.00 | 20.94 | B | C |
| ATOM | 3661 | O | CYS | B | 178 | 12.545 | 45.875 | 83.325 | 1.00 | 20.94 | B | O |
| ATOM | 3662 | N | HIS | B | 179 | 14.643 | 45.571 | 84.098 | 1.00 | 12.33 | B | N |
| ATOM | 3663 | CA | HIS | B | 179 | 15.214 | 46.640 | 83.301 | 1.00 | 12.33 | B | C |
| ATOM | 3664 | CB | HIS | B | 179 | 16.579 | 47.031 | 83.865 | 1.00 | 14.66 | B | C |
| ATOM | 3665 | CG | HIS | B | 179 | 17.133 | 48.282 | 83.273 | 1.00 | 14.66 | B | C |
| ATOM | 3666 | CD2 | HIS | B | 179 | 17.130 | 49.556 | 83.727 | 1.00 | 14.66 | B | C |
| ATOM | 3667 | ND1 | HIS | B | 179 | 17.720 | 48.320 | 82.025 | 1.00 | 14.66 | B | N |
| ATOM | 3668 | CE1 | HIS | B | 179 | 18.050 | 49.564 | 81.738 | 1.00 | 14.66 | B | C |
| ATOM | 3669 | NE2 | HIS | B | 179 | 17.702 | 50.335 | 82.753 | 1.00 | 14.66 | B | N |
| ATOM | 3670 | C | HIS | B | 179 | 15.338 | 46.193 | 81.851 | 1.00 | 12.33 | B | C |
| ATOM | 3671 | O | HIS | B | 179 | 15.035 | 46.954 | 80.935 | 1.00 | 12.33 | B | O |
| ATOM | 3672 | N | ARG | B | 180 | 15.774 | 44.949 | 81.663 | 1.00 | 24.62 | B | N |
| ATOM | 3673 | CA | ARG | B | 180 | 15.951 | 44.342 | 80.343 | 1.00 | 24.62 | B | C |
| ATOM | 3674 | CB | ARG | B | 180 | 14.602 | 44.280 | 79.623 | 1.00 | 20.65 | B | C |
| ATOM | 3675 | CG | ARG | B | 180 | 13.566 | 43.407 | 80.299 | 1.00 | 20.65 | B | C |
| ATOM | 3676 | CD | ARG | B | 180 | 12.200 | 43.989 | 80.011 | 1.00 | 20.65 | B | C |
| ATOM | 3677 | NE | ARG | B | 180 | 11.507 | 43.338 | 78.909 | 1.00 | 20.65 | B | N |
| ATOM | 3678 | CZ | ARG | B | 180 | 10.694 | 43.964 | 78.066 | 1.00 | 20.65 | B | C |
| ATOM | 3679 | NH1 | ARG | B | 180 | 10.471 | 45.269 | 78.172 | 1.00 | 20.65 | B | N |
| ATOM | 3680 | NH2 | ARG | B | 180 | 10.071 | 43.268 | 77.133 | 1.00 | 20.65 | B | N |
| ATOM | 3681 | C | ARG | B | 180 | 17.002 | 45.001 | 79.430 | 1.00 | 24.62 | B | C |
| ATOM | 3682 | O | ARG | B | 180 | 17.163 | 44.602 | 78.272 | 1.00 | 24.62 | B | O |
| ATOM | 3683 | N | ASP | B | 181 | 17.715 | 46.003 | 79.944 | 1.00 | 28.53 | B | N |
| ATOM | 3684 | CA | ASP | B | 181 | 18.746 | 46.667 | 79.154 | 1.00 | 28.53 | B | C |
| ATOM | 3685 | CB | ASP | B | 181 | 18.140 | 47.782 | 78.308 | 1.00 | 34.26 | B | C |
| ATOM | 3686 | CG | ASP | B | 181 | 19.115 | 48.308 | 77.272 | 1.00 | 34.26 | B | C |
| ATOM | 3687 | OD1 | ASP | B | 181 | 19.750 | 47.465 | 76.600 | 1.00 | 34.26 | B | O |
| ATOM | 3688 | OD2 | ASP | B | 181 | 19.240 | 49.550 | 77.127 | 1.00 | 34.26 | B | O |
| ATOM | 3689 | C | ASP | B | 181 | 19.915 | 47.234 | 79.965 | 1.00 | 28.53 | B | C |
| ATOM | 3690 | O | ASP | B | 181 | 20.376 | 48.355 | 79.720 | 1.00 | 28.53 | B | O |
| ATOM | 3691 | N | ILE | B | 182 | 20.402 | 46.449 | 80.919 | 1.00 | 18.84 | B | N |
| ATOM | 3692 | CA | ILE | B | 182 | 21.524 | 46.877 | 81.728 | 1.00 | 18.84 | B | C |
| ATOM | 3693 | CB | ILE | B | 182 | 21.731 | 45.974 | 82.962 | 1.00 | 17.27 | B | C |
| ATOM | 3694 | CG2 | ILE | B | 182 | 22.978 | 46.403 | 83.723 | 1.00 | 17.27 | B | C |
| ATOM | 3695 | CG1 | ILE | B | 182 | 20.517 | 46.048 | 83.881 | 1.00 | 17.27 | B | C |
| ATOM | 3696 | CD1 | ILE | B | 182 | 20.401 | 47.326 | 84.611 | 1.00 | 17.27 | B | C |
| ATOM | 3697 | C | ILE | B | 182 | 22.771 | 46.794 | 80.877 | 1.00 | 18.84 | B | C |
| ATOM | 3698 | O | ILE | B | 182 | 23.123 | 45.726 | 80.380 | 1.00 | 18.84 | B | O |
| ATOM | 3699 | N | LYS | B | 183 | 23.415 | 47.940 | 80.694 | 1.00 | 16.86 | B | N |
| ATOM | 3700 | CA | LYS | B | 183 | 24.654 | 48.041 | 79.944 | 1.00 | 16.86 | B | C |
| ATOM | 3701 | CB | LYS | B | 183 | 24.379 | 48.179 | 78.450 | 1.00 | 19.22 | B | C |
| ATOM | 3702 | CG | LYS | B | 183 | 23.410 | 49.283 | 78.039 | 1.00 | 19.22 | B | C |
| ATOM | 3703 | CD | LYS | B | 183 | 23.061 | 49.138 | 76.568 | 1.00 | 19.22 | B | C |
| ATOM | 3704 | CE | LYS | B | 183 | 22.250 | 50.302 | 76.058 | 1.00 | 19.22 | B | C |
| ATOM | 3705 | NZ | LYS | B | 183 | 21.948 | 50.146 | 74.616 | 1.00 | 19.22 | B | N |
| ATOM | 3706 | C | LYS | B | 183 | 25.375 | 49.266 | 80.488 | 1.00 | 16.86 | B | C |
| ATOM | 3707 | O | LYS | B | 183 | 24.740 | 50.187 | 81.004 | 1.00 | 16.86 | B | O |
| ATOM | 3708 | N | PRO | B | 184 | 26.714 | 49.288 | 80.387 | 1.00 | 19.99 | B | N |
| ATOM | 3709 | CD | PRO | B | 184 | 27.543 | 48.288 | 79.692 | 1.00 | 9.83 | B | C |
| ATOM | 3710 | CA | PRO | B | 184 | 27.548 | 50.387 | 80.870 | 1.00 | 19.99 | B | C |
| ATOM | 3711 | CB | PRO | B | 184 | 28.911 | 50.068 | 80.265 | 1.00 | 9.83 | B | C |
| ATOM | 3712 | CG | PRO | B | 184 | 28.913 | 48.595 | 80.221 | 1.00 | 9.83 | B | C |
| ATOM | 3713 | C | PRO | B | 184 | 27.071 | 51.784 | 80.505 | 1.00 | 19.99 | B | C |
| ATOM | 3714 | O | PRO | B | 184 | 27.314 | 52.726 | 81.252 | 1.00 | 19.99 | B | O |
| ATOM | 3715 | N | GLN | B | 185 | 26.406 | 51.920 | 79.363 | 1.00 | 17.94 | B | N |
| ATOM | 3716 | CA | GLN | B | 185 | 25.922 | 53.225 | 78.930 | 1.00 | 17.94 | B | C |
| ATOM | 3717 | CB | GLN | B | 185 | 25.508 | 53.204 | 77.460 | 1.00 | 42.77 | B | C |

FIG. 6-63

```
ATOM   3718  CG   GLN B 185      25.088  54.590  76.993  1.00 42.77      B    C
ATOM   3719  CD   GLN B 185      24.522  54.647  75.580  1.00 42.77      B    C
ATOM   3720  OE1  GLN B 185      24.092  55.713  75.132  1.00 42.77      B    O
ATOM   3721  NE2  GLN B 185      24.518  53.514  74.874  1.00 42.77      B    N
ATOM   3722  C    GLN B 185      24.749  53.726  79.766  1.00 17.94      B    C
ATOM   3723  O    GLN B 185      24.543  54.935  79.897  1.00 17.94      B    O
ATOM   3724  N    ASN B 186      23.994  52.778  80.324  1.00 23.18      B    N
ATOM   3725  CA   ASN B 186      22.827  53.068  81.151  1.00 23.18      B    C
ATOM   3726  CB   ASN B 186      21.759  51.993  80.988  1.00 29.63      B    C
ATOM   3727  CG   ASN B 186      20.994  52.136  79.703  1.00 29.63      B    C
ATOM   3728  OD1  ASN B 186      20.861  53.242  79.170  1.00 29.63      B    O
ATOM   3729  ND2  ASN B 186      20.466  51.022  79.198  1.00 29.63      B    N
ATOM   3730  C    ASN B 186      23.173  53.197  82.618  1.00 23.18      B    C
ATOM   3731  O    ASN B 186      22.295  53.300  83.461  1.00 23.18      B    O
ATOM   3732  N    LEU B 187      24.461  53.178  82.920  1.00 21.52      B    N
ATOM   3733  CA   LEU B 187      24.930  53.320  84.289  1.00 21.52      B    C
ATOM   3734  CB   LEU B 187      25.945  52.227  84.610  1.00 19.24      B    C
ATOM   3735  CG   LEU B 187      25.484  50.897  85.200  1.00 19.24      B    C
ATOM   3736  CD1  LEU B 187      24.157  50.468  84.645  1.00 19.24      B    C
ATOM   3737  CD2  LEU B 187      26.554  49.862  84.921  1.00 19.24      B    C
ATOM   3738  C    LEU B 187      25.574  54.687  84.483  1.00 21.52      B    C
ATOM   3739  O    LEU B 187      26.745  54.876  84.170  1.00 21.52      B    O
ATOM   3740  N    LEU B 188      24.804  55.640  84.991  1.00 21.48      B    N
ATOM   3741  CA   LEU B 188      25.309  56.993  85.225  1.00 21.48      B    C
ATOM   3742  CB   LEU B 188      24.140  57.980  85.330  1.00 20.19      B    C
ATOM   3743  CG   LEU B 188      23.072  57.975  84.233  1.00 20.19      B    C
ATOM   3744  CD1  LEU B 188      21.926  58.840  84.683  1.00 20.19      B    C
ATOM   3745  CD2  LEU B 188      23.639  58.478  82.916  1.00 20.19      B    C
ATOM   3746  C    LEU B 188      26.101  57.033  86.533  1.00 21.48      B    C
ATOM   3747  O    LEU B 188      25.846  56.254  87.440  1.00 21.48      B    O
ATOM   3748  N    LEU B 189      27.070  57.932  86.633  1.00 27.21      B    N
ATOM   3749  CA   LEU B 189      27.833  58.045  87.871  1.00 27.21      B    C
ATOM   3750  CB   LEU B 189      28.882  56.936  87.954  1.00 36.98      B    C
ATOM   3751  CG   LEU B 189      29.939  56.891  86.854  1.00 36.98      B    C
ATOM   3752  CD1  LEU B 189      30.944  58.018  87.056  1.00 36.98      B    C
ATOM   3753  CD2  LEU B 189      30.641  55.546  86.893  1.00 36.98      B    C
ATOM   3754  C    LEU B 189      28.503  59.399  88.051  1.00 27.21      B    C
ATOM   3755  O    LEU B 189      28.881  60.053  87.082  1.00 27.21      B    O
ATOM   3756  N    ASP B 190      28.633  59.809  89.308  1.00 29.66      B    N
ATOM   3757  CA   ASP B 190      29.272  61.071  89.651  1.00 29.66      B    C
ATOM   3758  CB   ASP B 190      28.535  61.736  90.810  1.00 32.26      B    C
ATOM   3759  CG   ASP B 190      28.901  63.197  90.972  1.00 32.26      B    C
ATOM   3760  OD1  ASP B 190      30.045  63.492  91.381  1.00 32.26      B    O
ATOM   3761  OD2  ASP B 190      28.046  64.056  90.683  1.00 32.26      B    O
ATOM   3762  C    ASP B 190      30.699  60.731  90.062  1.00 29.66      B    C
ATOM   3763  O    ASP B 190      30.917  60.042  91.051  1.00 29.66      B    O
ATOM   3764  N    PRO B 191      31.690  61.214  89.307  1.00 44.08      B    N
ATOM   3765  CD   PRO B 191      31.572  62.198  88.218  1.00 90.75      B    C
ATOM   3766  CA   PRO B 191      33.098  60.935  89.607  1.00 44.08      B    C
ATOM   3767  CB   PRO B 191      33.853  61.774  88.572  1.00 90.75      B    C
ATOM   3768  CG   PRO B 191      32.854  61.970  87.459  1.00 90.75      B    C
ATOM   3769  C    PRO B 191      33.505  61.295  91.031  1.00 44.08      B    C
ATOM   3770  O    PRO B 191      34.142  60.505  91.739  1.00 44.08      B    O
ATOM   3771  N    ASP B 192      33.116  62.487  91.455  1.00 33.29      B    N
ATOM   3772  CA   ASP B 192      33.483  62.948  92.777  1.00 33.29      B    C
ATOM   3773  CB   ASP B 192      33.296  64.468  92.846  1.00 43.52      B    C
ATOM   3774  CG   ASP B 192      34.058  65.205  91.723  1.00 43.52      B    C
ATOM   3775  OD1  ASP B 192      34.935  64.583  91.066  1.00 43.52      B    O
ATOM   3776  OD2  ASP B 192      33.790  66.409  91.500  1.00 43.52      B    O
ATOM   3777  C    ASP B 192      32.808  62.248  93.950  1.00 33.29      B    C
```

FIG. 6-64

```
ATOM   3778  O    ASP B 192      33.475  61.946  94.927  1.00 33.29           B  O
ATOM   3779  N    THR B 193      31.508  61.971  93.868  1.00 19.77           B  N
ATOM   3780  CA   THR B 193      30.834  61.298  94.973  1.00 19.77           B  C
ATOM   3781  CB   THR B 193      29.395  61.747  95.097  1.00 25.39           B  C
ATOM   3782  OG1  THR B 193      28.690  61.442  93.895  1.00 25.39           B  O
ATOM   3783  CG2  THR B 193      29.344  63.223  95.331  1.00 25.39           B  C
ATOM   3784  C    THR B 193      30.853  59.794  94.828  1.00 19.77           B  C
ATOM   3785  O    THR B 193      30.587  59.080  95.785  1.00 19.77           B  O
ATOM   3786  N    ALA B 194      31.177  59.316  93.631  1.00 26.84           B  N
ATOM   3787  CA   ALA B 194      31.245  57.878  93.345  1.00 26.84           B  C
ATOM   3788  CB   ALA B 194      32.244  57.200  94.304  1.00  7.07           B  C
ATOM   3789  C    ALA B 194      29.854  57.227  93.451  1.00 26.84           B  C
ATOM   3790  O    ALA B 194      29.701  56.038  93.722  1.00 26.84           B  O
ATOM   3791  N    VAL B 195      28.837  58.035  93.226  1.00 31.47           B  N
ATOM   3792  CA   VAL B 195      27.476  57.567  93.279  1.00 31.47           B  C
ATOM   3793  CB   VAL B 195      26.548  58.728  93.659  1.00 19.14           B  C
ATOM   3794  CG1  VAL B 195      25.088  58.316  93.502  1.00 19.14           B  C
ATOM   3795  CG2  VAL B 195      26.852  59.170  95.083  1.00 19.14           B  C
ATOM   3796  C    VAL B 195      27.096  57.033  91.900  1.00 31.47           B  C
ATOM   3797  O    VAL B 195      27.450  57.630  90.881  1.00 31.47           B  O
ATOM   3798  N    LEU B 196      26.393  55.903  91.869  1.00 24.14           B  N
ATOM   3799  CA   LEU B 196      25.961  55.301  90.612  1.00 24.14           B  C
ATOM   3800  CB   LEU B 196      26.452  53.851  90.506  1.00 15.62           B  C
ATOM   3801  CG   LEU B 196      26.087  53.044  89.251  1.00 15.62           B  C
ATOM   3802  CD1  LEU B 196      26.986  51.838  89.161  1.00 15.62           B  C
ATOM   3803  CD2  LEU B 196      24.636  52.606  89.285  1.00 15.62           B  C
ATOM   3804  C    LEU B 196      24.447  55.317  90.576  1.00 24.14           B  C
ATOM   3805  O    LEU B 196      23.794  54.945  91.542  1.00 24.14           B  O
ATOM   3806  N    LYS B 197      23.889  55.732  89.453  1.00 20.25           B  N
ATOM   3807  CA   LYS B 197      22.448  55.791  89.293  1.00 20.25           B  C
ATOM   3808  CB   LYS B 197      21.981  57.245  89.331  1.00 18.19           B  C
ATOM   3809  CG   LYS B 197      22.201  57.942  90.646  1.00 18.19           B  C
ATOM   3810  CD   LYS B 197      21.754  59.386  90.552  1.00 18.19           B  C
ATOM   3811  CE   LYS B 197      21.899  60.097  91.880  1.00 18.19           B  C
ATOM   3812  NZ   LYS B 197      21.040  59.490  92.929  1.00 18.19           B  N
ATOM   3813  C    LYS B 197      21.991  55.163  87.984  1.00 20.25           B  C
ATOM   3814  O    LYS B 197      22.381  55.621  86.911  1.00 20.25           B  O
ATOM   3815  N    LEU B 198      21.163  54.125  88.072  1.00 13.46           B  N
ATOM   3816  CA   LEU B 198      20.641  53.460  86.880  1.00 13.46           B  C
ATOM   3817  CB   LEU B 198      19.903  52.177  87.267  1.00 13.67           B  C
ATOM   3818  CG   LEU B 198      19.224  51.359  86.171  1.00 13.67           B  C
ATOM   3819  CD1  LEU B 198      20.234  50.645  85.315  1.00 13.67           B  C
ATOM   3820  CD2  LEU B 198      18.321  50.350  86.831  1.00 13.67           B  C
ATOM   3821  C    LEU B 198      19.684  54.409  86.174  1.00 13.46           B  C
ATOM   3822  O    LEU B 198      19.079  55.263  86.819  1.00 13.46           B  O
ATOM   3823  N    CYS B 199      19.546  54.252  84.859  1.00 13.25           B  N
ATOM   3824  CA   CYS B 199      18.671  55.106  84.054  1.00 13.25           B  C
ATOM   3825  CB   CYS B 199      19.383  56.413  83.702  1.00 25.34           B  C
ATOM   3826  SG   CYS B 199      20.574  56.287  82.349  1.00 25.34           B  S
ATOM   3827  C    CYS B 199      18.217  54.433  82.763  1.00 13.25           B  C
ATOM   3828  O    CYS B 199      18.645  53.330  82.440  1.00 13.25           B  O
ATOM   3829  N    ASP B 200      17.355  55.122  82.022  1.00 33.37           B  N
ATOM   3830  CA   ASP B 200      16.811  54.614  80.759  1.00 33.37           B  C
ATOM   3831  CB   ASP B 200      17.934  54.286  79.773  1.00 47.67           B  C
ATOM   3832  CG   ASP B 200      17.426  54.077  78.349  1.00 47.67           B  C
ATOM   3833  OD1  ASP B 200      16.224  53.748  78.172  1.00 47.67           B  O
ATOM   3834  OD2  ASP B 200      18.239  54.231  77.403  1.00 47.67           B  O
ATOM   3835  C    ASP B 200      15.938  53.368  80.974  1.00 33.37           B  C
ATOM   3836  O    ASP B 200      16.360  52.231  80.728  1.00 33.37           B  O
ATOM   3837  N    PHE B 201      14.714  53.579  81.438  1.00 27.42           B  N
```

FIG. 6-65

```
ATOM   3838  CA   PHE B 201      13.826  52.452  81.655  1.00 27.42      B   C
ATOM   3839  CB   PHE B 201      13.029  52.643  82.942  1.00 22.69      B   C
ATOM   3840  CG   PHE B 201      13.831  52.392  84.187  1.00 22.69      B   C
ATOM   3841  CD1  PHE B 201      14.849  53.261  84.560  1.00 22.69      B   C
ATOM   3842  CD2  PHE B 201      13.581  51.278  84.980  1.00 22.69      B   C
ATOM   3843  CE1  PHE B 201      15.609  53.026  85.710  1.00 22.69      B   C
ATOM   3844  CE2  PHE B 201      14.334  51.035  86.130  1.00 22.69      B   C
ATOM   3845  CZ   PHE B 201      15.348  51.910  86.494  1.00 22.69      B   C
ATOM   3846  C    PHE B 201      12.895  52.266  80.468  1.00 27.42      B   C
ATOM   3847  O    PHE B 201      11.802  51.716  80.596  1.00 27.42      B   O
ATOM   3848  N    GLY B 202      13.356  52.724  79.308  1.00 20.61      B   N
ATOM   3849  CA   GLY B 202      12.575  52.614  78.093  1.00 20.61      B   C
ATOM   3850  C    GLY B 202      12.374  51.188  77.612  1.00 20.61      B   C
ATOM   3851  O    GLY B 202      11.692  50.959  76.625  1.00 20.61      B   O
ATOM   3852  N    SER B 203      12.968  50.224  78.300  1.00 30.31      B   N
ATOM   3853  CA   SER B 203      12.819  48.827  77.914  1.00 30.31      B   C
ATOM   3854  CB   SER B 203      14.159  48.224  77.477  1.00 35.22      B   C
ATOM   3855  OG   SER B 203      14.666  48.841  76.307  1.00 35.22      B   O
ATOM   3856  C    SER B 203      12.295  48.015  79.076  1.00 30.31      B   C
ATOM   3857  O    SER B 203      12.082  46.814  78.941  1.00 30.31      B   O
ATOM   3858  N    ALA B 204      12.096  48.671  80.218  1.00 29.27      B   N
ATOM   3859  CA   ALA B 204      11.617  47.998  81.414  1.00 29.27      B   C
ATOM   3860  CB   ALA B 204      11.801  48.887  82.626  1.00 17.60      B   C
ATOM   3861  C    ALA B 204      10.167  47.603  81.286  1.00 29.27      B   C
ATOM   3862  O    ALA B 204       9.405  48.220  80.545  1.00 29.27      B   O
ATOM   3863  N    LYS B 205       9.798  46.570  82.034  1.00 27.63      B   N
ATOM   3864  CA   LYS B 205       8.441  46.038  82.053  1.00 27.63      B   C
ATOM   3865  CB   LYS B 205       8.241  45.099  80.856  1.00 29.45      B   C
ATOM   3866  CG   LYS B 205       6.899  44.397  80.784  1.00 29.45      B   C
ATOM   3867  CD   LYS B 205       6.807  43.549  79.518  1.00 29.45      B   C
ATOM   3868  CE   LYS B 205       5.459  42.841  79.364  1.00 29.45      B   C
ATOM   3869  NZ   LYS B 205       5.366  42.159  78.031  1.00 29.45      B   N
ATOM   3870  C    LYS B 205       8.181  45.274  83.356  1.00 27.63      B   C
ATOM   3871  O    LYS B 205       9.075  44.628  83.921  1.00 27.63      B   O
ATOM   3872  N    GLN B 206       6.950  45.373  83.839  1.00 28.11      B   N
ATOM   3873  CA   GLN B 206       6.535  44.660  85.041  1.00 28.11      B   C
ATOM   3874  CB   GLN B 206       5.174  45.188  85.467  1.00 46.32      B   C
ATOM   3875  CG   GLN B 206       5.189  46.150  86.624  1.00 46.32      B   C
ATOM   3876  CD   GLN B 206       4.891  45.444  87.929  1.00 46.32      B   C
ATOM   3877  OE1  GLN B 206       4.926  46.058  89.003  1.00 46.32      B   O
ATOM   3878  NE2  GLN B 206       4.595  44.138  87.846  1.00 46.32      B   N
ATOM   3879  C    GLN B 206       6.409  43.188  84.628  1.00 28.11      B   C
ATOM   3880  O    GLN B 206       5.451  42.831  83.962  1.00 28.11      B   O
ATOM   3881  N    LEU B 207       7.369  42.341  84.989  1.00 34.86      B   N
ATOM   3882  CA   LEU B 207       7.287  40.931  84.596  1.00 34.86      B   C
ATOM   3883  CB   LEU B 207       8.646  40.226  84.677  1.00 17.27      B   C
ATOM   3884  CG   LEU B 207       9.785  40.598  83.725  1.00 17.27      B   C
ATOM   3885  CD1  LEU B 207      10.791  39.462  83.689  1.00 17.27      B   C
ATOM   3886  CD2  LEU B 207       9.250  40.861  82.329  1.00 17.27      B   C
ATOM   3887  C    LEU B 207       6.294  40.147  85.439  1.00 34.86      B   C
ATOM   3888  O    LEU B 207       6.524  39.885  86.623  1.00 34.86      B   O
ATOM   3889  N    VAL B 208       5.194  39.756  84.807  1.00 40.24      B   N
ATOM   3890  CA   VAL B 208       4.140  39.009  85.466  1.00 40.24      B   C
ATOM   3891  CB   VAL B 208       2.768  39.586  85.072  1.00 23.70      B   C
ATOM   3892  CG1  VAL B 208       1.663  38.864  85.795  1.00 23.70      B   C
ATOM   3893  CG2  VAL B 208       2.731  41.061  85.388  1.00 23.70      B   C
ATOM   3894  C    VAL B 208       4.221  37.537  85.062  1.00 40.24      B   C
ATOM   3895  O    VAL B 208       4.140  37.210  83.873  1.00 40.24      B   O
ATOM   3896  N    ALA B 209       4.385  36.665  86.061  1.00 38.06      B   N
ATOM   3897  CA   ALA B 209       4.481  35.217  85.864  1.00 38.06      B   C
```

FIG. 6-66

```
ATOM   3898  CB   ALA B 209       4.315  34.490  87.200  1.00 20.16      B    C
ATOM   3899  C    ALA B 209       3.439  34.713  84.872  1.00 38.06      B    C
ATOM   3900  O    ALA B 209       2.307  35.220  84.815  1.00 38.06      B    O
ATOM   3901  N    GLY B 210       3.832  33.715  84.086  1.00 32.96      B    N
ATOM   3902  CA   GLY B 210       2.925  33.159  83.102  1.00 32.96      B    C
ATOM   3903  C    GLY B 210       2.738  34.028  81.875  1.00 32.96      B    C
ATOM   3904  O    GLY B 210       2.419  33.521  80.805  1.00 32.96      B    O
ATOM   3905  N    GLU B 211       2.910  35.338  82.025  1.00 45.91      B    N
ATOM   3906  CA   GLU B 211       2.756  36.249  80.895  1.00 45.91      B    C
ATOM   3907  CB   GLU B 211       2.490  37.678  81.378  1.00 56.63      B    C
ATOM   3908  CG   GLU B 211       1.156  37.875  82.088  1.00 56.63      B    C
ATOM   3909  CD   GLU B 211       0.802  39.355  82.320  1.00 56.63      B    C
ATOM   3910  OE1  GLU B 211      -0.317  39.620  82.810  1.00 56.63      B    O
ATOM   3911  OE2  GLU B 211       1.629  40.254  82.019  1.00 56.63      B    O
ATOM   3912  C    GLU B 211       4.024  36.218  80.043  1.00 45.91      B    C
ATOM   3913  O    GLU B 211       5.141  36.160  80.563  1.00 45.91      B    O
ATOM   3914  N    PRO B 212       3.872  36.243  78.717  1.00 48.50      B    N
ATOM   3915  CD   PRO B 212       2.626  36.080  77.956  1.00 35.05      B    C
ATOM   3916  CA   PRO B 212       5.037  36.212  77.822  1.00 48.50      B    C
ATOM   3917  CB   PRO B 212       4.437  35.782  76.480  1.00 35.05      B    C
ATOM   3918  CG   PRO B 212       3.085  35.191  76.848  1.00 35.05      B    C
ATOM   3919  C    PRO B 212       5.677  37.593  77.710  1.00 48.50      B    C
ATOM   3920  O    PRO B 212       5.024  38.611  77.952  1.00 48.50      B    O
ATOM   3921  N    ASN B 213       6.952  37.626  77.346  1.00 22.62      B    N
ATOM   3922  CA   ASN B 213       7.641  38.891  77.162  1.00 22.62      B    C
ATOM   3923  CB   ASN B 213       8.515  39.208  78.364  1.00 26.17      B    C
ATOM   3924  CG   ASN B 213       7.747  39.185  79.667  1.00 26.17      B    C
ATOM   3925  OD1  ASN B 213       6.856  40.013  79.901  1.00 26.17      B    O
ATOM   3926  ND2  ASN B 213       8.088  38.229  80.528  1.00 26.17      B    N
ATOM   3927  C    ASN B 213       8.508  38.697  75.945  1.00 22.62      B    C
ATOM   3928  O    ASN B 213       8.979  37.583  75.701  1.00 22.62      B    O
ATOM   3929  N    VAL B 214       8.710  39.767  75.176  1.00 27.02      B    N
ATOM   3930  CA   VAL B 214       9.525  39.677  73.966  1.00 27.02      B    C
ATOM   3931  CB   VAL B 214       9.416  40.961  73.126  1.00 27.52      B    C
ATOM   3932  CG1  VAL B 214       7.977  41.137  72.658  1.00 27.52      B    C
ATOM   3933  CG2  VAL B 214       9.884  42.162  73.927  1.00 27.52      B    C
ATOM   3934  C    VAL B 214      10.987  39.385  74.274  1.00 27.02      B    C
ATOM   3935  O    VAL B 214      11.517  39.822  75.296  1.00 27.02      B    O
ATOM   3936  N    SER B 215      11.637  38.640  73.391  1.00 26.29      B    N
ATOM   3937  CA   SER B 215      13.028  38.275  73.603  1.00 26.29      B    C
ATOM   3938  CB   SER B 215      13.218  36.785  73.301  1.00 37.52      B    C
ATOM   3939  OG   SER B 215      12.713  36.440  72.018  1.00 37.52      B    O
ATOM   3940  C    SER B 215      14.067  39.095  72.842  1.00 26.29      B    C
ATOM   3941  O    SER B 215      15.252  38.800  72.912  1.00 26.29      B    O
ATOM   3942  N    TYR B 216      13.638  40.120  72.121  1.00 34.00      B    N
ATOM   3943  CA   TYR B 216      14.584  40.951  71.382  1.00 34.00      B    C
ATOM   3944  CB   TYR B 216      14.002  41.308  70.008  1.00 25.15      B    C
ATOM   3945  CG   TYR B 216      12.631  41.953  70.040  1.00 25.15      B    C
ATOM   3946  CD1  TYR B 216      12.475  43.319  70.291  1.00 25.15      B    C
ATOM   3947  CE1  TYR B 216      11.210  43.915  70.295  1.00 25.15      B    C
ATOM   3948  CD2  TYR B 216      11.488  41.199  69.800  1.00 25.15      B    C
ATOM   3949  CE2  TYR B 216      10.219  41.783  69.801  1.00 25.15      B    C
ATOM   3950  CZ   TYR B 216      10.088  43.137  70.044  1.00 25.15      B    C
ATOM   3951  OH   TYR B 216       8.839  43.709  69.999  1.00 25.15      B    O
ATOM   3952  C    TYR B 216      14.859  42.223  72.184  1.00 34.00      B    C
ATOM   3953  O    TYR B 216      15.147  43.285  71.623  1.00 34.00      B    O
ATOM   3954  N    ILE B 217      14.827  42.088  73.502  1.00 30.37      B    N
ATOM   3955  CA   ILE B 217      14.968  43.225  74.386  1.00 30.37      B    C
ATOM   3956  CB   ILE B 217      14.033  42.987  75.611  1.00 14.70      B    C
ATOM   3957  CG2  ILE B 217      14.725  42.154  76.681  1.00 14.70      B    C
```

FIG. 6-67

```
ATOM   3958  CG1 ILE B 217      13.569  44.324  76.147  1.00 14.70      B    C
ATOM   3959  CD1 ILE B 217      12.900  45.173  75.071  1.00 14.70      B    C
ATOM   3960  C   ILE B 217      16.334  43.738  74.884  1.00 30.37      B    C
ATOM   3961  O   ILE B 217      16.483  44.932  75.179  1.00 30.37      B    O
ATOM   3962  N   CYS B 218      17.334  42.877  74.968  1.00 25.01      B    N
ATOM   3963  CA  CYS B 218      18.616  43.328  75.499  1.00 25.01      B    C
ATOM   3964  CB  CYS B 218      19.151  42.244  76.433  1.00 26.63      B    C
ATOM   3965  SG  CYS B 218      20.338  42.777  77.643  1.00 26.63      B    S
ATOM   3966  C   CYS B 218      19.677  43.728  74.450  1.00 25.01      B    C
ATOM   3967  O   CYS B 218      19.548  43.415  73.259  1.00 25.01      B    O
ATOM   3968  N   SER B 219      20.718  44.428  74.899  1.00 22.97      B    N
ATOM   3969  CA  SER B 219      21.798  44.869  74.016  1.00 22.97      B    C
ATOM   3970  CB  SER B 219      22.398  46.184  74.510  1.00 35.90      B    C
ATOM   3971  OG  SER B 219      21.494  47.258  74.359  1.00 35.90      B    O
ATOM   3972  C   SER B 219      22.936  43.869  73.860  1.00 22.97      B    C
ATOM   3973  O   SER B 219      23.244  43.112  74.770  1.00 22.97      B    O
ATOM   3974  N   ARG B 220      23.568  43.932  72.692  1.00 41.43      B    N
ATOM   3975  CA  ARG B 220      24.689  43.096  72.237  1.00 41.43      B    C
ATOM   3976  CB  ARG B 220      25.661  43.983  71.457  1.00 71.33      B    C
ATOM   3977  CG  ARG B 220      26.316  43.328  70.229  1.00 71.33      B    C
ATOM   3978  CD  ARG B 220      27.156  44.361  69.465  1.00 71.33      B    C
ATOM   3979  NE  ARG B 220      27.374  45.558  70.284  1.00 71.33      B    N
ATOM   3980  CZ  ARG B 220      28.277  46.506  70.034  1.00 71.33      B    C
ATOM   3981  NH1 ARG B 220      29.079  46.413  68.965  1.00 71.33      B    N
ATOM   3982  NH2 ARG B 220      28.374  47.552  70.862  1.00 71.33      B    N
ATOM   3983  C   ARG B 220      25.498  42.180  73.172  1.00 41.43      B    C
ATOM   3984  O   ARG B 220      25.189  40.985  73.285  1.00 41.43      B    O
ATOM   3985  N   TYR B 221      26.544  42.698  73.812  1.00 20.42      B    N
ATOM   3986  CA  TYR B 221      27.371  41.850  74.683  1.00 20.42      B    C
ATOM   3987  CB  TYR B 221      28.684  42.552  74.996  1.00 38.33      B    C
ATOM   3988  CG  TYR B 221      29.359  43.176  73.809  1.00 38.33      B    C
ATOM   3989  CD1 TYR B 221      29.551  42.454  72.631  1.00 38.33      B    C
ATOM   3990  CE1 TYR B 221      30.218  43.003  71.552  1.00 38.33      B    C
ATOM   3991  CD2 TYR B 221      29.848  44.478  73.872  1.00 38.33      B    C
ATOM   3992  CE2 TYR B 221      30.520  45.040  72.792  1.00 38.33      B    C
ATOM   3993  CZ  TYR B 221      30.699  44.292  71.638  1.00 38.33      B    C
ATOM   3994  OH  TYR B 221      31.378  44.827  70.568  1.00 38.33      B    O
ATOM   3995  C   TYR B 221      26.767  41.444  76.026  1.00 20.42      B    C
ATOM   3996  O   TYR B 221      27.333  40.605  76.720  1.00 20.42      B    O
ATOM   3997  N   TYR B 222      25.618  42.018  76.376  1.00 31.39      B    N
ATOM   3998  CA  TYR B 222      25.005  41.766  77.672  1.00 31.39      B    C
ATOM   3999  CB  TYR B 222      24.718  43.120  78.316  1.00 27.59      B    C
ATOM   4000  CG  TYR B 222      25.860  44.084  78.101  1.00 27.59      B    C
ATOM   4001  CD1 TYR B 222      26.993  44.056  78.920  1.00 27.59      B    C
ATOM   4002  CE1 TYR B 222      28.078  44.896  78.677  1.00 27.59      B    C
ATOM   4003  CD2 TYR B 222      25.840  44.975  77.038  1.00 27.59      B    C
ATOM   4004  CE2 TYR B 222      26.911  45.814  76.788  1.00 27.59      B    C
ATOM   4005  CZ  TYR B 222      28.033  45.778  77.607  1.00 27.59      B    C
ATOM   4006  OH  TYR B 222      29.089  46.634  77.356  1.00 27.59      B    O
ATOM   4007  C   TYR B 222      23.770  40.892  77.774  1.00 31.39      B    C
ATOM   4008  O   TYR B 222      23.235  40.720  78.868  1.00 31.39      B    O
ATOM   4009  N   ARG B 223      23.323  40.329  76.659  1.00 24.07      B    N
ATOM   4010  CA  ARG B 223      22.123  39.497  76.655  1.00 24.07      B    C
ATOM   4011  CB  ARG B 223      21.664  39.239  75.226  1.00 22.52      B    C
ATOM   4012  CG  ARG B 223      21.995  40.349  74.263  1.00 22.52      B    C
ATOM   4013  CD  ARG B 223      21.227  40.170  72.992  1.00 22.52      B    C
ATOM   4014  NE  ARG B 223      19.807  40.372  73.240  1.00 22.52      B    N
ATOM   4015  CZ  ARG B 223      18.845  39.565  72.813  1.00 22.52      B    C
ATOM   4016  NH1 ARG B 223      19.137  38.484  72.105  1.00 22.52      B    N
ATOM   4017  NH2 ARG B 223      17.589  39.839  73.115  1.00 22.52      B    N
```

FIG. 6-68

```
ATOM   4018  C    ARG B 223      22.356  38.168  77.336  1.00 24.07      B  C
ATOM   4019  O    ARG B 223      23.406  37.555  77.167  1.00 24.07      B  O
ATOM   4020  N    ALA B 224      21.372  37.721  78.108  1.00 23.11      B  N
ATOM   4021  CA   ALA B 224      21.479  36.452  78.803  1.00 23.11      B  C
ATOM   4022  CB   ALA B 224      20.420  36.361  79.876  1.00 39.52      B  C
ATOM   4023  C    ALA B 224      21.282  35.349  77.777  1.00 23.11      B  C
ATOM   4024  O    ALA B 224      20.626  35.555  76.751  1.00 23.11      B  O
ATOM   4025  N    PRO B 225      21.848  34.157  78.044  1.00 25.35      B  N
ATOM   4026  CD   PRO B 225      22.498  33.815  79.322  1.00 29.95      B  C
ATOM   4027  CA   PRO B 225      21.763  32.977  77.170  1.00 25.35      B  C
ATOM   4028  CB   PRO B 225      22.314  31.856  78.039  1.00 29.95      B  C
ATOM   4029  CG   PRO B 225      23.236  32.552  78.966  1.00 29.95      B  C
ATOM   4030  C    PRO B 225      20.319  32.705  76.748  1.00 25.35      B  C
ATOM   4031  O    PRO B 225      20.038  32.510  75.575  1.00 25.35      B  O
ATOM   4032  N    GLU B 226      19.401  32.698  77.707  1.00 21.36      B  N
ATOM   4033  CA   GLU B 226      18.005  32.453  77.386  1.00 21.36      B  C
ATOM   4034  CB   GLU B 226      17.133  32.477  78.648  1.00 25.12      B  C
ATOM   4035  CG   GLU B 226      17.170  33.785  79.432  1.00 25.12      B  C
ATOM   4036  CD   GLU B 226      18.056  33.711  80.661  1.00 25.12      B  C
ATOM   4037  OE1  GLU B 226      19.202  33.247  80.534  1.00 25.12      B  O
ATOM   4038  OE2  GLU B 226      17.606  34.119  81.751  1.00 25.12      B  O
ATOM   4039  C    GLU B 226      17.453  33.460  76.383  1.00 21.36      B  C
ATOM   4040  O    GLU B 226      16.589  33.123  75.581  1.00 21.36      B  O
ATOM   4041  N    LEU B 227      17.937  34.697  76.432  1.00 27.19      B  N
ATOM   4042  CA   LEU B 227      17.462  35.715  75.503  1.00 27.19      B  C
ATOM   4043  CB   LEU B 227      17.924  37.109  75.933  1.00 19.10      B  C
ATOM   4044  CG   LEU B 227      17.323  37.750  77.186  1.00 19.10      B  C
ATOM   4045  CD1  LEU B 227      17.618  39.235  77.125  1.00 19.10      B  C
ATOM   4046  CD2  LEU B 227      15.822  37.532  77.253  1.00 19.10      B  C
ATOM   4047  C    LEU B 227      17.962  35.421  74.091  1.00 27.19      B  C
ATOM   4048  O    LEU B 227      17.252  35.634  73.112  1.00 27.19      B  O
ATOM   4049  N    ILE B 228      19.195  34.935  73.997  1.00 22.44      B  N
ATOM   4050  CA   ILE B 228      19.783  34.589  72.722  1.00 22.44      B  C
ATOM   4051  CB   ILE B 228      21.255  34.196  72.908  1.00 11.12      B  C
ATOM   4052  CG2  ILE B 228      21.851  33.741  71.602  1.00 11.12      B  C
ATOM   4053  CG1  ILE B 228      22.037  35.396  73.440  1.00 11.12      B  C
ATOM   4054  CD1  ILE B 228      23.515  35.121  73.695  1.00 11.12      B  C
ATOM   4055  C    ILE B 228      18.999  33.421  72.125  1.00 22.44      B  C
ATOM   4056  O    ILE B 228      18.772  33.349  70.911  1.00 22.44      B  O
ATOM   4057  N    PHE B 229      18.588  32.499  72.988  1.00 26.42      B  N
ATOM   4058  CA   PHE B 229      17.816  31.340  72.549  1.00 26.42      B  C
ATOM   4059  CB   PHE B 229      17.855  30.213  73.588  1.00 16.73      B  C
ATOM   4060  CG   PHE B 229      19.179  29.519  73.693  1.00 16.73      B  C
ATOM   4061  CD1  PHE B 229      19.804  29.009  72.574  1.00 16.73      B  C
ATOM   4062  CD2  PHE B 229      19.786  29.344  74.927  1.00 16.73      B  C
ATOM   4063  CE1  PHE B 229      21.015  28.329  72.681  1.00 16.73      B  C
ATOM   4064  CE2  PHE B 229      20.996  28.664  75.037  1.00 16.73      B  C
ATOM   4065  CZ   PHE B 229      21.606  28.158  73.907  1.00 16.73      B  C
ATOM   4066  C    PHE B 229      16.359  31.686  72.246  1.00 26.42      B  C
ATOM   4067  O    PHE B 229      15.592  30.810  71.861  1.00 26.42      B  O
ATOM   4068  N    GLY B 230      15.979  32.949  72.429  1.00 22.42      B  N
ATOM   4069  CA   GLY B 230      14.616  33.365  72.138  1.00 22.42      B  C
ATOM   4070  C    GLY B 230      13.569  33.072  73.200  1.00 22.42      B  C
ATOM   4071  O    GLY B 230      12.379  33.234  72.955  1.00 22.42      B  O
ATOM   4072  N    ALA B 231      13.992  32.639  74.378  1.00 17.62      B  N
ATOM   4073  CA   ALA B 231      13.041  32.358  75.434  1.00 17.62      B  C
ATOM   4074  CB   ALA B 231      13.770  32.005  76.705  1.00  7.73      B  C
ATOM   4075  C    ALA B 231      12.186  33.588  75.650  1.00 17.62      B  C
ATOM   4076  O    ALA B 231      12.667  34.704  75.501  1.00 17.62      B  O
ATOM   4077  N    THR B 232      10.916  33.390  75.990  1.00 34.74      B  N
```

FIG. 6-69

```
ATOM   4078  CA   THR B 232      10.019  34.513  76.234  1.00 34.74      B    C
ATOM   4079  CB   THR B 232       8.834  34.495  75.276  1.00 53.64      B    C
ATOM   4080  OG1  THR B 232       8.118  33.263  75.448  1.00 53.64      B    O
ATOM   4081  CG2  THR B 232       9.313  34.649  73.825  1.00 53.64      B    C
ATOM   4082  C    THR B 232       9.478  34.448  77.649  1.00 34.74      B    C
ATOM   4083  O    THR B 232       8.756  35.342  78.101  1.00 34.74      B    O
ATOM   4084  N    ASP B 233       9.840  33.378  78.340  1.00 23.31      B    N
ATOM   4085  CA   ASP B 233       9.403  33.133  79.708  1.00 23.31      B    C
ATOM   4086  CB   ASP B 233       8.988  31.679  79.830  1.00 35.56      B    C
ATOM   4087  CG   ASP B 233      10.123  30.752  79.497  1.00 35.56      B    C
ATOM   4088  OD1  ASP B 233      11.016  31.187  78.733  1.00 35.56      B    O
ATOM   4089  OD2  ASP B 233      10.136  29.600  79.980  1.00 35.56      B    O
ATOM   4090  C    ASP B 233      10.562  33.413  80.663  1.00 23.31      B    C
ATOM   4091  O    ASP B 233      10.790  32.665  81.613  1.00 23.31      B    O
ATOM   4092  N    TYR B 234      11.290  34.495  80.409  1.00 32.53      B    N
ATOM   4093  CA   TYR B 234      12.423  34.859  81.254  1.00 32.53      B    C
ATOM   4094  CB   TYR B 234      13.470  35.653  80.452  1.00 18.24      B    C
ATOM   4095  CG   TYR B 234      12.966  36.903  79.746  1.00 18.24      B    C
ATOM   4096  CD1  TYR B 234      12.317  36.822  78.520  1.00 18.24      B    C
ATOM   4097  CE1  TYR B 234      11.878  37.973  77.852  1.00 18.24      B    C
ATOM   4098  CD2  TYR B 234      13.166  38.172  80.295  1.00 18.24      B    C
ATOM   4099  CE2  TYR B 234      12.727  39.330  79.635  1.00 18.24      B    C
ATOM   4100  CZ   TYR B 234      12.080  39.219  78.414  1.00 18.24      B    C
ATOM   4101  OH   TYR B 234      11.599  40.339  77.772  1.00 18.24      B    O
ATOM   4102  C    TYR B 234      12.020  35.671  82.474  1.00 32.53      B    C
ATOM   4103  O    TYR B 234      10.966  36.304  82.488  1.00 32.53      B    O
ATOM   4104  N    THR B 235      12.866  35.647  83.496  1.00 20.87      B    N
ATOM   4105  CA   THR B 235      12.617  36.417  84.707  1.00 20.87      B    C
ATOM   4106  CB   THR B 235      12.776  35.572  85.983  1.00 27.25      B    C
ATOM   4107  OG1  THR B 235      13.736  34.537  85.756  1.00 27.25      B    O
ATOM   4108  CG2  THR B 235      11.444  34.972  86.396  1.00 27.25      B    C
ATOM   4109  C    THR B 235      13.568  37.590  84.815  1.00 20.87      B    C
ATOM   4110  O    THR B 235      14.148  38.034  83.831  1.00 20.87      B    O
ATOM   4111  N    SER B 236      13.719  38.101  86.025  1.00 27.16      B    N
ATOM   4112  CA   SER B 236      14.614  39.221  86.249  1.00 27.16      B    C
ATOM   4113  CB   SER B 236      14.307  39.880  87.581  1.00 24.74      B    C
ATOM   4114  OG   SER B 236      12.990  40.358  87.560  1.00 24.74      B    O
ATOM   4115  C    SER B 236      16.056  38.749  86.257  1.00 27.16      B    C
ATOM   4116  O    SER B 236      16.970  39.561  86.330  1.00 27.16      B    O
ATOM   4117  N    SER B 237      16.259  37.438  86.195  1.00 25.87      B    N
ATOM   4118  CA   SER B 237      17.613  36.911  86.215  1.00 25.87      B    C
ATOM   4119  CB   SER B 237      17.636  35.378  86.076  1.00 31.90      B    C
ATOM   4120  OG   SER B 237      16.361  34.791  86.244  1.00 31.90      B    O
ATOM   4121  C    SER B 237      18.418  37.506  85.068  1.00 25.87      B    C
ATOM   4122  O    SER B 237      19.652  37.557  85.126  1.00 25.87      B    O
ATOM   4123  N    ILE B 238      17.718  37.964  84.033  1.00 17.87      B    N
ATOM   4124  CA   ILE B 238      18.388  38.530  82.877  1.00 17.87      B    C
ATOM   4125  CB   ILE B 238      17.394  38.833  81.729  1.00 19.74      B    C
ATOM   4126  CG2  ILE B 238      16.351  37.757  81.661  1.00 19.74      B    C
ATOM   4127  CG1  ILE B 238      16.688  40.160  81.944  1.00 19.74      B    C
ATOM   4128  CD1  ILE B 238      15.960  40.607  80.717  1.00 19.74      B    C
ATOM   4129  C    ILE B 238      19.172  39.793  83.222  1.00 17.87      B    C
ATOM   4130  O    ILE B 238      20.202  40.080  82.602  1.00 17.87      B    O
ATOM   4131  N    ASP B 239      18.688  40.545  84.206  1.00 17.36      B    N
ATOM   4132  CA   ASP B 239      19.382  41.754  84.628  1.00 17.36      B    C
ATOM   4133  CB   ASP B 239      18.484  42.654  85.479  1.00 17.79      B    C
ATOM   4134  CG   ASP B 239      17.501  43.456  84.644  1.00 17.79      B    C
ATOM   4135  OD1  ASP B 239      17.770  43.686  83.446  1.00 17.79      B    O
ATOM   4136  OD2  ASP B 239      16.465  43.873  85.197  1.00 17.79      B    O
ATOM   4137  C    ASP B 239      20.621  41.386  85.418  1.00 17.36      B    C
```

FIG. 6-70

```
ATOM   4138  O    ASP B 239      21.615  42.097  85.380  1.00 17.36      B  O
ATOM   4139  N    VAL B 240      20.553  40.263  86.121  1.00 23.77      B  N
ATOM   4140  CA   VAL B 240      21.667  39.772  86.922  1.00 23.77      B  C
ATOM   4141  CB   VAL B 240      21.225  38.584  87.803  1.00 20.93      B  C
ATOM   4142  CG1  VAL B 240      22.434  37.909  88.424  1.00 20.93      B  C
ATOM   4143  CG2  VAL B 240      20.286  39.078  88.896  1.00 20.93      B  C
ATOM   4144  C    VAL B 240      22.813  39.329  86.012  1.00 23.77      B  C
ATOM   4145  O    VAL B 240      23.985  39.523  86.331  1.00 23.77      B  O
ATOM   4146  N    TRP B 241      22.465  38.722  84.882  1.00 18.13      B  N
ATOM   4147  CA   TRP B 241      23.463  38.268  83.929  1.00 18.13      B  C
ATOM   4148  CB   TRP B 241      22.810  37.384  82.846  1.00 23.70      B  C
ATOM   4149  CG   TRP B 241      23.736  37.018  81.672  1.00 23.70      B  C
ATOM   4150  CD2  TRP B 241      24.463  35.790  81.499  1.00 23.70      B  C
ATOM   4151  CE2  TRP B 241      25.223  35.920  80.311  1.00 23.70      B  C
ATOM   4152  CE3  TRP B 241      24.555  34.601  82.236  1.00 23.70      B  C
ATOM   4153  CD1  TRP B 241      24.073  37.808  80.601  1.00 23.70      B  C
ATOM   4154  NE1  TRP B 241      24.962  37.154  79.787  1.00 23.70      B  N
ATOM   4155  CZ2  TRP B 241      26.053  34.897  79.842  1.00 23.70      B  C
ATOM   4156  CZ3  TRP B 241      25.382  33.587  81.766  1.00 23.70      B  C
ATOM   4157  CH2  TRP B 241      26.124  33.745  80.582  1.00 23.70      B  C
ATOM   4158  C    TRP B 241      24.104  39.513  83.312  1.00 18.13      B  C
ATOM   4159  O    TRP B 241      25.328  39.625  83.224  1.00 18.13      B  O
ATOM   4160  N    SER B 242      23.267  40.454  82.894  1.00 14.88      B  N
ATOM   4161  CA   SER B 242      23.767  41.687  82.299  1.00 14.88      B  C
ATOM   4162  CB   SER B 242      22.609  42.630  81.952  1.00 25.53      B  C
ATOM   4163  OG   SER B 242      21.744  42.045  80.996  1.00 25.53      B  O
ATOM   4164  C    SER B 242      24.681  42.366  83.303  1.00 14.88      B  C
ATOM   4165  O    SER B 242      25.759  42.836  82.966  1.00 14.88      B  O
ATOM   4166  N    ALA B 243      24.235  42.419  84.548  1.00 26.41      B  N
ATOM   4167  CA   ALA B 243      25.040  43.015  85.601  1.00 26.41      B  C
ATOM   4168  CB   ALA B 243      24.352  42.837  86.932  1.00  7.85      B  C
ATOM   4169  C    ALA B 243      26.407  42.337  85.628  1.00 26.41      B  C
ATOM   4170  O    ALA B 243      27.442  43.002  85.598  1.00 26.41      B  O
ATOM   4171  N    GLY B 244      26.399  41.010  85.676  1.00 21.74      B  N
ATOM   4172  CA   GLY B 244      27.633  40.251  85.703  1.00 21.74      B  C
ATOM   4173  C    GLY B 244      28.551  40.524  84.531  1.00 21.74      B  C
ATOM   4174  O    GLY B 244      29.771  40.489  84.691  1.00 21.74      B  O
ATOM   4175  N    CYS B 245      27.988  40.779  83.351  1.00 29.73      B  N
ATOM   4176  CA   CYS B 245      28.822  41.077  82.191  1.00 29.73      B  C
ATOM   4177  CB   CYS B 245      28.006  41.096  80.893  1.00 22.96      B  C
ATOM   4178  SG   CYS B 245      27.324  39.543  80.330  1.00 22.96      B  S
ATOM   4179  C    CYS B 245      29.495  42.443  82.356  1.00 29.73      B  C
ATOM   4180  O    CYS B 245      30.484  42.740  81.690  1.00 29.73      B  O
ATOM   4181  N    VAL B 246      28.946  43.289  83.218  1.00 24.92      B  N
ATOM   4182  CA   VAL B 246      29.547  44.591  83.441  1.00 24.92      B  C
ATOM   4183  CB   VAL B 246      28.527  45.585  84.025  1.00 14.74      B  C
ATOM   4184  CG1  VAL B 246      29.191  46.932  84.299  1.00 14.74      B  C
ATOM   4185  CG2  VAL B 246      27.384  45.761  83.042  1.00 14.74      B  C
ATOM   4186  C    VAL B 246      30.698  44.373  84.410  1.00 24.92      B  C
ATOM   4187  O    VAL B 246      31.794  44.872  84.203  1.00 24.92      B  O
ATOM   4188  N    LEU B 247      30.448  43.598  85.457  1.00 22.14      B  N
ATOM   4189  CA   LEU B 247      31.473  43.313  86.454  1.00 22.14      B  C
ATOM   4190  CB   LEU B 247      30.940  42.308  87.493  1.00 15.79      B  C
ATOM   4191  CG   LEU B 247      31.610  42.098  88.857  1.00 15.79      B  C
ATOM   4192  CD1  LEU B 247      31.498  40.633  89.208  1.00 15.79      B  C
ATOM   4193  CD2  LEU B 247      33.064  42.497  88.841  1.00 15.79      B  C
ATOM   4194  C    LEU B 247      32.686  42.722  85.748  1.00 22.14      B  C
ATOM   4195  O    LEU B 247      33.806  43.184  85.923  1.00 22.14      B  O
ATOM   4196  N    ALA B 248      32.451  41.693  84.944  1.00 32.65      B  N
ATOM   4197  CA   ALA B 248      33.531  41.047  84.223  1.00 32.65      B  C
```

FIG. 6-71

| ATOM | 4198 | CB | ALA | B | 248 | 32.992 | 39.905 | 83.378 | 1.00 | 7.67 | B | C |
| ATOM | 4199 | C | ALA | B | 248 | 34.265 | 42.044 | 83.347 | 1.00 | 32.65 | B | C |
| ATOM | 4200 | O | ALA | B | 248 | 35.492 | 42.075 | 83.340 | 1.00 | 32.65 | B | O |
| ATOM | 4201 | N | GLU | B | 249 | 33.508 | 42.865 | 82.620 | 1.00 | 20.30 | B | N |
| ATOM | 4202 | CA | GLU | B | 249 | 34.078 | 43.863 | 81.717 | 1.00 | 20.30 | B | C |
| ATOM | 4203 | CB | GLU | B | 249 | 32.966 | 44.612 | 81.001 | 1.00 | 23.58 | B | C |
| ATOM | 4204 | CG | GLU | B | 249 | 33.426 | 45.429 | 79.815 | 1.00 | 23.58 | B | C |
| ATOM | 4205 | CD | GLU | B | 249 | 32.276 | 45.756 | 78.894 | 1.00 | 23.58 | B | C |
| ATOM | 4206 | OE1 | GLU | B | 249 | 31.467 | 44.843 | 78.638 | 1.00 | 23.58 | B | O |
| ATOM | 4207 | OE2 | GLU | B | 249 | 32.180 | 46.905 | 78.420 | 1.00 | 23.58 | B | O |
| ATOM | 4208 | C | GLU | B | 249 | 34.984 | 44.870 | 82.415 | 1.00 | 20.30 | B | C |
| ATOM | 4209 | O | GLU | B | 249 | 36.016 | 45.251 | 81.890 | 1.00 | 20.30 | B | O |
| ATOM | 4210 | N | LEU | B | 250 | 34.590 | 45.305 | 83.600 | 1.00 | 27.64 | B | N |
| ATOM | 4211 | CA | LEU | B | 250 | 35.375 | 46.263 | 84.347 | 1.00 | 27.64 | B | C |
| ATOM | 4212 | CB | LEU | B | 250 | 34.519 | 46.870 | 85.448 | 1.00 | 24.89 | B | C |
| ATOM | 4213 | CG | LEU | B | 250 | 33.524 | 47.884 | 84.899 | 1.00 | 24.89 | B | C |
| ATOM | 4214 | CD1 | LEU | B | 250 | 32.614 | 48.350 | 86.008 | 1.00 | 24.89 | B | C |
| ATOM | 4215 | CD2 | LEU | B | 250 | 34.280 | 49.058 | 84.294 | 1.00 | 24.89 | B | C |
| ATOM | 4216 | C | LEU | B | 250 | 36.648 | 45.667 | 84.943 | 1.00 | 27.64 | B | C |
| ATOM | 4217 | O | LEU | B | 250 | 37.592 | 46.394 | 85.248 | 1.00 | 27.64 | B | O |
| ATOM | 4218 | N | LEU | B | 251 | 36.671 | 44.349 | 85.123 | 1.00 | 21.76 | B | N |
| ATOM | 4219 | CA | LEU | B | 251 | 37.845 | 43.683 | 85.658 | 1.00 | 21.76 | B | C |
| ATOM | 4220 | CB | LEU | B | 251 | 37.460 | 42.380 | 86.344 | 1.00 | 14.59 | B | C |
| ATOM | 4221 | CG | LEU | B | 251 | 36.527 | 42.478 | 87.541 | 1.00 | 14.59 | B | C |
| ATOM | 4222 | CD1 | LEU | B | 251 | 36.110 | 41.087 | 87.954 | 1.00 | 14.59 | B | C |
| ATOM | 4223 | CD2 | LEU | B | 251 | 37.214 | 43.203 | 88.670 | 1.00 | 14.59 | B | C |
| ATOM | 4224 | C | LEU | B | 251 | 38.780 | 43.374 | 84.501 | 1.00 | 21.76 | B | C |
| ATOM | 4225 | O | LEU | B | 251 | 39.995 | 43.532 | 84.615 | 1.00 | 21.76 | B | O |
| ATOM | 4226 | N | LEU | B | 252 | 38.209 | 42.939 | 83.381 | 1.00 | 22.32 | B | N |
| ATOM | 4227 | CA | LEU | B | 252 | 39.001 | 42.607 | 82.205 | 1.00 | 22.32 | B | C |
| ATOM | 4228 | CB | LEU | B | 252 | 38.225 | 41.674 | 81.283 | 1.00 | 27.03 | B | C |
| ATOM | 4229 | CG | LEU | B | 252 | 38.371 | 40.212 | 81.710 | 1.00 | 27.03 | B | C |
| ATOM | 4230 | CD1 | LEU | B | 252 | 37.295 | 39.380 | 81.023 | 1.00 | 27.03 | B | C |
| ATOM | 4231 | CD2 | LEU | B | 252 | 39.782 | 39.704 | 81.377 | 1.00 | 27.03 | B | C |
| ATOM | 4232 | C | LEU | B | 252 | 39.504 | 43.815 | 81.431 | 1.00 | 22.32 | B | C |
| ATOM | 4233 | O | LEU | B | 252 | 40.687 | 43.883 | 81.096 | 1.00 | 22.32 | B | O |
| ATOM | 4234 | N | GLY | B | 253 | 38.619 | 44.769 | 81.160 | 1.00 | 20.41 | B | N |
| ATOM | 4235 | CA | GLY | B | 253 | 39.017 | 45.960 | 80.428 | 1.00 | 20.41 | B | C |
| ATOM | 4236 | C | GLY | B | 253 | 38.460 | 45.938 | 79.028 | 1.00 | 20.41 | B | C |
| ATOM | 4237 | O | GLY | B | 253 | 38.801 | 46.775 | 78.196 | 1.00 | 20.41 | B | O |
| ATOM | 4238 | N | GLN | B | 254 | 37.608 | 44.949 | 78.776 | 1.00 | 45.04 | B | N |
| ATOM | 4239 | CA | GLN | B | 254 | 36.952 | 44.767 | 77.485 | 1.00 | 45.04 | B | C |
| ATOM | 4240 | CB | GLN | B | 254 | 37.926 | 44.165 | 76.462 | 1.00 | 38.17 | B | C |
| ATOM | 4241 | CG | GLN | B | 254 | 38.728 | 42.997 | 76.971 | 1.00 | 38.17 | B | C |
| ATOM | 4242 | CD | GLN | B | 254 | 39.516 | 42.321 | 75.864 | 1.00 | 38.17 | B | C |
| ATOM | 4243 | OE1 | GLN | B | 254 | 40.482 | 42.872 | 75.346 | 1.00 | 38.17 | B | O |
| ATOM | 4244 | NE2 | GLN | B | 254 | 39.097 | 41.120 | 75.491 | 1.00 | 38.17 | B | N |
| ATOM | 4245 | C | GLN | B | 254 | 35.755 | 43.849 | 77.683 | 1.00 | 45.04 | B | C |
| ATOM | 4246 | O | GLN | B | 254 | 35.643 | 43.193 | 78.708 | 1.00 | 45.04 | B | O |
| ATOM | 4247 | N | PRO | B | 255 | 34.841 | 43.790 | 76.709 | 1.00 | 27.88 | B | N |
| ATOM | 4248 | CD | PRO | B | 255 | 34.728 | 44.590 | 75.479 | 1.00 | 17.14 | B | C |
| ATOM | 4249 | CA | PRO | B | 255 | 33.674 | 42.916 | 76.877 | 1.00 | 27.88 | B | C |
| ATOM | 4250 | CB | PRO | B | 255 | 32.891 | 43.151 | 75.584 | 1.00 | 17.14 | B | C |
| ATOM | 4251 | CG | PRO | B | 255 | 33.234 | 44.586 | 75.243 | 1.00 | 17.14 | B | C |
| ATOM | 4252 | C | PRO | B | 255 | 34.057 | 41.450 | 77.076 | 1.00 | 27.88 | B | C |
| ATOM | 4253 | O | PRO | B | 255 | 34.969 | 40.960 | 76.432 | 1.00 | 27.88 | B | O |
| ATOM | 4254 | N | ILE | B | 256 | 33.352 | 40.755 | 77.962 | 1.00 | 19.18 | B | N |
| ATOM | 4255 | CA | ILE | B | 256 | 33.630 | 39.351 | 78.231 | 1.00 | 19.18 | B | C |
| ATOM | 4256 | CB | ILE | B | 256 | 33.141 | 38.954 | 79.644 | 1.00 | 28.68 | B | C |
| ATOM | 4257 | CG2 | ILE | B | 256 | 31.705 | 39.361 | 79.832 | 1.00 | 28.68 | B | C |

FIG. 6-72

```
ATOM   4258  CG1 ILE B 256      33.282  37.448  79.855  1.00 28.68           B  C
ATOM   4259  CD1 ILE B 256      34.689  36.971  79.856  1.00 28.68           B  C
ATOM   4260  C   ILE B 256      33.033  38.394  77.208  1.00 19.18           B  C
ATOM   4261  O   ILE B 256      33.678  37.411  76.848  1.00 19.18           B  O
ATOM   4262  N   PHE B 257      31.812  38.672  76.746  1.00 23.68           B  N
ATOM   4263  CA  PHE B 257      31.137  37.821  75.753  1.00 23.68           B  C
ATOM   4264  CB  PHE B 257      29.858  37.233  76.344  1.00 33.17           B  C
ATOM   4265  CG  PHE B 257      30.073  36.445  77.596  1.00 33.17           B  C
ATOM   4266  CD1 PHE B 257      31.064  35.468  77.661  1.00 33.17           B  C
ATOM   4267  CD2 PHE B 257      29.279  36.669  78.709  1.00 33.17           B  C
ATOM   4268  CE1 PHE B 257      31.255  34.722  78.818  1.00 33.17           B  C
ATOM   4269  CE2 PHE B 257      29.456  35.935  79.867  1.00 33.17           B  C
ATOM   4270  CZ  PHE B 257      30.450  34.957  79.924  1.00 33.17           B  C
ATOM   4271  C   PHE B 257      30.778  38.584  74.470  1.00 23.68           B  C
ATOM   4272  O   PHE B 257      29.601  38.737  74.145  1.00 23.68           B  O
ATOM   4273  N   PRO B 258      31.785  39.040  73.706  1.00 33.74           B  N
ATOM   4274  CD  PRO B 258      33.241  38.858  73.876  1.00 18.69           B  C
ATOM   4275  CA  PRO B 258      31.500  39.784  72.473  1.00 33.74           B  C
ATOM   4276  CB  PRO B 258      32.831  40.455  72.176  1.00 18.69           B  C
ATOM   4277  CG  PRO B 258      33.798  39.366  72.545  1.00 18.69           B  C
ATOM   4278  C   PRO B 258      31.038  38.919  71.314  1.00 33.74           B  C
ATOM   4279  O   PRO B 258      31.107  37.684  71.375  1.00 33.74           B  O
ATOM   4280  N   GLY B 259      30.588  39.587  70.255  1.00 29.83           B  N
ATOM   4281  CA  GLY B 259      30.108  38.893  69.068  1.00 29.83           B  C
ATOM   4282  C   GLY B 259      28.936  39.617  68.438  1.00 29.83           B  C
ATOM   4283  O   GLY B 259      28.042  40.081  69.147  1.00 29.83           B  O
ATOM   4284  N   ASP B 260      28.934  39.721  67.113  1.00 21.48           B  N
ATOM   4285  CA  ASP B 260      27.854  40.410  66.418  1.00 21.48           B  C
ATOM   4286  CB  ASP B 260      28.354  41.000  65.103  1.00 53.56           B  C
ATOM   4287  CG  ASP B 260      29.434  42.035  65.316  1.00 53.56           B  C
ATOM   4288  OD1 ASP B 260      29.199  42.972  66.121  1.00 53.56           B  O
ATOM   4289  OD2 ASP B 260      30.519  41.914  64.683  1.00 53.56           B  O
ATOM   4290  C   ASP B 260      26.670  39.506  66.153  1.00 21.48           B  C
ATOM   4291  O   ASP B 260      25.625  39.955  65.701  1.00 21.48           B  O
ATOM   4292  N   SER B 261      26.831  38.224  66.427  1.00 22.48           B  N
ATOM   4293  CA  SER B 261      25.742  37.304  66.206  1.00 22.48           B  C
ATOM   4294  CB  SER B 261      26.055  36.372  65.047  1.00 16.57           B  C
ATOM   4295  OG  SER B 261      26.806  35.269  65.499  1.00 16.57           B  O
ATOM   4296  C   SER B 261      25.545  36.494  67.469  1.00 22.48           B  C
ATOM   4297  O   SER B 261      26.478  36.325  68.248  1.00 22.48           B  O
ATOM   4298  N   GLY B 262      24.323  36.008  67.669  1.00 32.89           B  N
ATOM   4299  CA  GLY B 262      24.035  35.205  68.840  1.00 32.89           B  C
ATOM   4300  C   GLY B 262      24.973  34.023  68.852  1.00 32.89           B  C
ATOM   4301  O   GLY B 262      25.506  33.642  69.898  1.00 32.89           B  O
ATOM   4302  N   VAL B 263      25.169  33.439  67.677  1.00 30.51           B  N
ATOM   4303  CA  VAL B 263      26.064  32.310  67.548  1.00 30.51           B  C
ATOM   4304  CB  VAL B 263      26.204  31.867  66.076  1.00 37.28           B  C
ATOM   4305  CG1 VAL B 263      27.000  30.583  65.993  1.00 37.28           B  C
ATOM   4306  CG2 VAL B 263      24.840  31.666  65.471  1.00 37.28           B  C
ATOM   4307  C   VAL B 263      27.426  32.738  68.095  1.00 30.51           B  C
ATOM   4308  O   VAL B 263      27.922  32.144  69.042  1.00 30.51           B  O
ATOM   4309  N   ASP B 264      28.027  33.774  67.519  1.00 28.22           B  N
ATOM   4310  CA  ASP B 264      29.328  34.228  68.006  1.00 28.22           B  C
ATOM   4311  CB  ASP B 264      29.744  35.537  67.327  1.00 35.54           B  C
ATOM   4312  CG  ASP B 264      30.209  35.342  65.901  1.00 35.54           B  C
ATOM   4313  OD1 ASP B 264      30.443  34.183  65.513  1.00 35.54           B  O
ATOM   4314  OD2 ASP B 264      30.353  36.349  65.177  1.00 35.54           B  O
ATOM   4315  C   ASP B 264      29.334  34.444  69.520  1.00 28.22           B  C
ATOM   4316  O   ASP B 264      30.258  34.025  70.208  1.00 28.22           B  O
ATOM   4317  N   GLN B 265      28.305  35.116  70.025  1.00 25.46           B  N
```

FIG. 6-73

```
ATOM   4318  CA   GLN B 265      28.176  35.393  71.452  1.00 25.46      B   C
ATOM   4319  CB   GLN B 265      26.900  36.197  71.732  1.00 20.33      B   C
ATOM   4320  CG   GLN B 265      26.926  37.607  71.184  1.00 20.33      B   C
ATOM   4321  CD   GLN B 265      25.556  38.233  71.141  1.00 20.33      B   C
ATOM   4322  OE1  GLN B 265      25.389  39.335  70.625  1.00 20.33      B   O
ATOM   4323  NE2  GLN B 265      24.562  37.535  71.678  1.00 20.33      B   N
ATOM   4324  C    GLN B 265      28.128  34.108  72.236  1.00 25.46      B   C
ATOM   4325  O    GLN B 265      28.774  33.978  73.276  1.00 25.46      B   O
ATOM   4326  N    LEU B 266      27.348  33.164  71.725  1.00 19.47      B   N
ATOM   4327  CA   LEU B 266      27.183  31.877  72.364  1.00 19.47      B   C
ATOM   4328  CB   LEU B 266      26.117  31.080  71.622  1.00 18.40      B   C
ATOM   4329  CG   LEU B 266      24.928  30.552  72.421  1.00 18.40      B   C
ATOM   4330  CD1  LEU B 266      24.223  31.678  73.124  1.00 18.40      B   C
ATOM   4331  CD2  LEU B 266      23.965  29.854  71.484  1.00 18.40      B   C
ATOM   4332  C    LEU B 266      28.486  31.101  72.440  1.00 19.47      B   C
ATOM   4333  O    LEU B 266      28.720  30.408  73.414  1.00 19.47      B   O
ATOM   4334  N    VAL B 267      29.351  31.224  71.439  1.00 20.40      B   N
ATOM   4335  CA   VAL B 267      30.617  30.486  71.478  1.00 20.40      B   C
ATOM   4336  CB   VAL B 267      31.295  30.383  70.043  1.00 35.08      B   C
ATOM   4337  CG1  VAL B 267      30.465  31.122  69.008  1.00 35.08      B   C
ATOM   4338  CG2  VAL B 267      32.745  30.909  70.072  1.00 35.08      B   C
ATOM   4339  C    VAL B 267      31.576  31.078  72.511  1.00 20.40      B   C
ATOM   4340  O    VAL B 267      32.318  30.355  73.176  1.00 20.40      B   O
ATOM   4341  N    GLU B 268      31.535  32.396  72.655  1.00 30.36      B   N
ATOM   4342  CA   GLU B 268      32.377  33.084  73.616  1.00 30.36      B   C
ATOM   4343  CB   GLU B 268      32.236  34.585  73.408  1.00 47.21      B   C
ATOM   4344  CG   GLU B 268      33.559  35.324  73.456  1.00 47.21      B   C
ATOM   4345  CD   GLU B 268      34.483  34.965  72.311  1.00 47.21      B   C
ATOM   4346  OE1  GLU B 268      34.094  35.173  71.142  1.00 47.21      B   O
ATOM   4347  OE2  GLU B 268      35.601  34.481  72.578  1.00 47.21      B   O
ATOM   4348  C    GLU B 268      31.957  32.680  75.036  1.00 30.36      B   C
ATOM   4349  O    GLU B 268      32.802  32.449  75.907  1.00 30.36      B   O
ATOM   4350  N    ILE B 269      30.645  32.583  75.252  1.00 33.57      B   N
ATOM   4351  CA   ILE B 269      30.102  32.191  76.548  1.00 33.57      B   C
ATOM   4352  CB   ILE B 269      28.562  32.271  76.559  1.00 22.05      B   C
ATOM   4353  CG2  ILE B 269      27.996  31.555  77.780  1.00 22.05      B   C
ATOM   4354  CG1  ILE B 269      28.117  33.723  76.565  1.00 22.05      B   C
ATOM   4355  CD1  ILE B 269      26.626  33.864  76.359  1.00 22.05      B   C
ATOM   4356  C    ILE B 269      30.513  30.758  76.864  1.00 33.57      B   C
ATOM   4357  O    ILE B 269      30.995  30.465  77.955  1.00 33.57      B   O
ATOM   4358  N    ILE B 270      30.313  29.863  75.907  1.00 35.14      B   N
ATOM   4359  CA   ILE B 270      30.667  28.467  76.108  1.00 35.14      B   C
ATOM   4360  CB   ILE B 270      30.283  27.635  74.869  1.00 22.39      B   C
ATOM   4361  CG2  ILE B 270      30.874  26.240  74.962  1.00 22.39      B   C
ATOM   4362  CG1  ILE B 270      28.756  27.563  74.772  1.00 22.39      B   C
ATOM   4363  CD1  ILE B 270      28.241  27.009  73.479  1.00 22.39      B   C
ATOM   4364  C    ILE B 270      32.154  28.333  76.414  1.00 35.14      B   C
ATOM   4365  O    ILE B 270      32.548  27.545  77.274  1.00 35.14      B   O
ATOM   4366  N    LYS B 271      32.974  29.117  75.724  1.00 33.16      B   N
ATOM   4367  CA   LYS B 271      34.409  29.092  75.961  1.00 33.16      B   C
ATOM   4368  CB   LYS B 271      35.115  30.224  75.207  1.00 54.07      B   C
ATOM   4369  CG   LYS B 271      35.361  29.985  73.730  1.00 54.07      B   C
ATOM   4370  CD   LYS B 271      36.140  31.155  73.131  1.00 54.07      B   C
ATOM   4371  CE   LYS B 271      36.232  31.054  71.607  1.00 54.07      B   C
ATOM   4372  NZ   LYS B 271      37.012  32.181  70.988  1.00 54.07      B   N
ATOM   4373  C    LYS B 271      34.739  29.231  77.439  1.00 33.16      B   C
ATOM   4374  O    LYS B 271      35.710  28.638  77.905  1.00 33.16      B   O
ATOM   4375  N    VAL B 272      33.947  30.005  78.181  1.00 32.89      B   N
ATOM   4376  CA   VAL B 272      34.255  30.204  79.590  1.00 32.89      B   C
ATOM   4377  CB   VAL B 272      34.339  31.720  79.955  1.00 34.59      B   C
```

FIG. 6-74

| ATOM | 4378 | CG1 | VAL | B | 272 | 34.648 | 32.541 | 78.719 | 1.00 | 34.59 | B | C |
|---|---|---|---|---|---|---|---|---|---|---|---|---|
| ATOM | 4379 | CG2 | VAL | B | 272 | 33.061 | 32.183 | 80.624 | 1.00 | 34.59 | B | C |
| ATOM | 4380 | C | VAL | B | 272 | 33.342 | 29.518 | 80.590 | 1.00 | 32.89 | B | C |
| ATOM | 4381 | O | VAL | B | 272 | 33.689 | 29.427 | 81.758 | 1.00 | 32.89 | B | O |
| ATOM | 4382 | N | LEU | B | 273 | 32.176 | 29.046 | 80.169 | 1.00 | 43.03 | B | N |
| ATOM | 4383 | CA | LEU | B | 273 | 31.286 | 28.365 | 81.115 | 1.00 | 43.03 | B | C |
| ATOM | 4384 | CB | LEU | B | 273 | 29.848 | 28.893 | 81.010 | 1.00 | 41.26 | B | C |
| ATOM | 4385 | CG | LEU | B | 273 | 29.487 | 30.334 | 81.379 | 1.00 | 41.26 | B | C |
| ATOM | 4386 | CD1 | LEU | B | 273 | 27.967 | 30.488 | 81.336 | 1.00 | 41.26 | B | C |
| ATOM | 4387 | CD2 | LEU | B | 273 | 30.001 | 30.675 | 82.761 | 1.00 | 41.26 | B | C |
| ATOM | 4388 | C | LEU | B | 273 | 31.269 | 26.865 | 80.835 | 1.00 | 43.03 | B | C |
| ATOM | 4389 | O | LEU | B | 273 | 30.674 | 26.082 | 81.572 | 1.00 | 43.03 | B | O |
| ATOM | 4390 | N | GLY | B | 274 | 31.929 | 26.463 | 79.759 | 1.00 | 45.55 | B | N |
| ATOM | 4391 | CA | GLY | B | 274 | 31.925 | 25.061 | 79.402 | 1.00 | 45.55 | B | C |
| ATOM | 4392 | C | GLY | B | 274 | 30.690 | 24.810 | 78.559 | 1.00 | 45.55 | B | C |
| ATOM | 4393 | O | GLY | B | 274 | 29.863 | 25.705 | 78.360 | 1.00 | 45.55 | B | O |
| ATOM | 4394 | N | THR | B | 275 | 30.560 | 23.598 | 78.039 | 1.00 | 53.69 | B | N |
| ATOM | 4395 | CA | THR | B | 275 | 29.394 | 23.273 | 77.231 | 1.00 | 53.69 | B | C |
| ATOM | 4396 | CB | THR | B | 275 | 29.691 | 22.059 | 76.291 | 1.00 | 69.03 | B | C |
| ATOM | 4397 | OG1 | THR | B | 275 | 30.631 | 22.461 | 75.278 | 1.00 | 69.03 | B | O |
| ATOM | 4398 | CG2 | THR | B | 275 | 28.392 | 21.529 | 75.631 | 1.00 | 69.03 | B | C |
| ATOM | 4399 | C | THR | B | 275 | 28.234 | 22.972 | 78.180 | 1.00 | 53.69 | B | C |
| ATOM | 4400 | O | THR | B | 275 | 28.357 | 22.152 | 79.082 | 1.00 | 53.69 | B | O |
| ATOM | 4401 | N | PRO | B | 276 | 27.093 | 23.639 | 77.987 | 1.00 | 48.85 | B | N |
| ATOM | 4402 | CD | PRO | B | 276 | 26.727 | 24.420 | 76.797 | 1.00 | 25.57 | B | C |
| ATOM | 4403 | CA | PRO | B | 276 | 25.928 | 23.419 | 78.854 | 1.00 | 48.85 | B | C |
| ATOM | 4404 | CB | PRO | B | 276 | 24.809 | 24.203 | 78.158 | 1.00 | 25.57 | B | C |
| ATOM | 4405 | CG | PRO | B | 276 | 25.528 | 25.179 | 77.280 | 1.00 | 25.57 | B | C |
| ATOM | 4406 | C | PRO | B | 276 | 25.559 | 21.937 | 78.956 | 1.00 | 48.85 | B | C |
| ATOM | 4407 | O | PRO | B | 276 | 25.763 | 21.173 | 78.008 | 1.00 | 48.85 | B | O |
| ATOM | 4408 | N | THR | B | 277 | 25.020 | 21.538 | 80.108 | 1.00 | 39.27 | B | N |
| ATOM | 4409 | CA | THR | B | 277 | 24.572 | 20.167 | 80.315 | 1.00 | 39.27 | B | C |
| ATOM | 4410 | CB | THR | B | 277 | 24.227 | 19.908 | 81.775 | 1.00 | 37.39 | B | C |
| ATOM | 4411 | OG1 | THR | B | 277 | 22.994 | 20.574 | 82.090 | 1.00 | 37.39 | B | O |
| ATOM | 4412 | CG2 | THR | B | 277 | 25.343 | 20.424 | 82.682 | 1.00 | 37.39 | B | C |
| ATOM | 4413 | C | THR | B | 277 | 23.264 | 20.150 | 79.544 | 1.00 | 39.27 | B | C |
| ATOM | 4414 | O | THR | B | 277 | 23.153 | 20.808 | 78.522 | 1.00 | 39.27 | B | O |
| ATOM | 4415 | N | ALA | B | 278 | 22.265 | 19.422 | 80.034 | 1.00 | 60.15 | B | N |
| ATOM | 4416 | CA | ALA | B | 278 | 20.965 | 19.409 | 79.354 | 1.00 | 60.15 | B | C |
| ATOM | 4417 | CB | ALA | B | 278 | 20.088 | 18.276 | 79.891 | 1.00 | 54.16 | B | C |
| ATOM | 4418 | C | ALA | B | 278 | 20.311 | 20.772 | 79.632 | 1.00 | 60.15 | B | C |
| ATOM | 4419 | O | ALA | B | 278 | 19.197 | 21.048 | 79.163 | 1.00 | 60.15 | B | O |
| ATOM | 4420 | N | GLU | B | 279 | 21.037 | 21.595 | 80.410 | 1.00 | 72.61 | B | N |
| ATOM | 4421 | CA | GLU | B | 279 | 20.648 | 22.959 | 80.810 | 1.00 | 72.61 | B | C |
| ATOM | 4422 | CB | GLU | B | 279 | 21.893 | 23.785 | 81.181 | 1.00 | 28.73 | B | C |
| ATOM | 4423 | CG | GLU | B | 279 | 22.461 | 23.548 | 82.586 | 1.00 | 28.73 | B | C |
| ATOM | 4424 | CD | GLU | B | 279 | 23.966 | 23.844 | 82.686 | 1.00 | 28.73 | B | C |
| ATOM | 4425 | OE1 | GLU | B | 279 | 24.489 | 23.961 | 83.820 | 1.00 | 28.73 | B | O |
| ATOM | 4426 | OE2 | GLU | B | 279 | 24.634 | 23.944 | 81.628 | 1.00 | 28.73 | B | O |
| ATOM | 4427 | C | GLU | B | 279 | 19.884 | 23.692 | 79.710 | 1.00 | 72.61 | B | C |
| ATOM | 4428 | O | GLU | B | 279 | 19.042 | 24.538 | 80.002 | 1.00 | 72.61 | B | O |
| ATOM | 4429 | N | GLN | B | 280 | 20.195 | 23.393 | 78.451 | 1.00 | 48.17 | B | N |
| ATOM | 4430 | CA | GLN | B | 280 | 19.479 | 24.013 | 77.344 | 1.00 | 48.17 | B | C |
| ATOM | 4431 | CB | GLN | B | 280 | 19.603 | 23.149 | 76.084 | 1.00 | 75.64 | B | C |
| ATOM | 4432 | CG | GLN | B | 280 | 20.910 | 23.340 | 75.332 | 1.00 | 75.64 | B | C |
| ATOM | 4433 | CD | GLN | B | 280 | 22.109 | 23.381 | 76.258 | 1.00 | 75.64 | B | C |
| ATOM | 4434 | OE1 | GLN | B | 280 | 22.536 | 22.352 | 76.790 | 1.00 | 75.64 | B | O |
| ATOM | 4435 | NE2 | GLN | B | 280 | 22.654 | 24.586 | 76.472 | 1.00 | 75.64 | B | N |
| ATOM | 4436 | C | GLN | B | 280 | 18.023 | 24.076 | 77.776 | 1.00 | 48.17 | B | C |
| ATOM | 4437 | O | GLN | B | 280 | 17.331 | 25.074 | 77.575 | 1.00 | 48.17 | B | O |

FIG. 6-75

```
ATOM   4438  N    ALA B 281      17.576  22.987  78.388  1.00 43.37      B  N
ATOM   4439  CA   ALA B 281      16.219  22.886  78.883  1.00 43.37      B  C
ATOM   4440  CB   ALA B 281      16.084  21.633  79.783  1.00 69.66      B  C
ATOM   4441  C    ALA B 281      15.914  24.152  79.676  1.00 43.37      B  C
ATOM   4442  O    ALA B 281      15.025  24.931  79.317  1.00 43.37      B  O
ATOM   4443  N    ALA B 282      16.677  24.343  80.750  1.00 69.80      B  N
ATOM   4444  CA   ALA B 282      16.536  25.500  81.634  1.00 69.80      B  C
ATOM   4445  CB   ALA B 282      17.637  25.466  82.711  1.00 54.43      B  C
ATOM   4446  C    ALA B 282      16.580  26.833  80.864  1.00 69.80      B  C
ATOM   4447  O    ALA B 282      15.812  27.758  81.173  1.00 69.80      B  O
ATOM   4448  N    GLU B 283      17.470  26.924  79.870  1.00 48.81      B  N
ATOM   4449  CA   GLU B 283      17.605  28.133  79.049  1.00 48.81      B  C
ATOM   4450  CB   GLU B 283      19.018  28.242  78.475  1.00 39.92      B  C
ATOM   4451  CG   GLU B 283      20.105  28.298  79.528  1.00 39.92      B  C
ATOM   4452  CD   GLU B 283      21.486  28.297  78.921  1.00 39.92      B  C
ATOM   4453  OE1  GLU B 283      21.854  27.294  78.268  1.00 39.92      B  O
ATOM   4454  OE2  GLU B 283      22.203  29.304  79.090  1.00 39.92      B  O
ATOM   4455  C    GLU B 283      16.604  28.106  77.899  1.00 48.81      B  C
ATOM   4456  O    GLU B 283      15.683  28.922  77.851  1.00 48.81      B  O
ATOM   4457  N    TRP B 301      36.661  29.269  84.514  1.00 62.04      B  N
ATOM   4458  CA   TRP B 301      37.086  30.614  84.905  1.00 62.04      B  C
ATOM   4459  CB   TRP B 301      36.259  31.102  86.099  1.00 30.73      B  C
ATOM   4460  CG   TRP B 301      34.827  31.431  85.753  1.00 30.73      B  C
ATOM   4461  CD2  TRP B 301      34.360  32.655  85.183  1.00 30.73      B  C
ATOM   4462  CE2  TRP B 301      32.967  32.523  84.990  1.00 30.73      B  C
ATOM   4463  CE3  TRP B 301      34.988  33.849  84.809  1.00 30.73      B  C
ATOM   4464  CD1  TRP B 301      33.727  30.623  85.887  1.00 30.73      B  C
ATOM   4465  NE1  TRP B 301      32.606  31.277  85.430  1.00 30.73      B  N
ATOM   4466  CZ2  TRP B 301      32.189  33.549  84.440  1.00 30.73      B  C
ATOM   4467  CZ3  TRP B 301      34.214  34.869  84.261  1.00 30.73      B  C
ATOM   4468  CH2  TRP B 301      32.830  34.710  84.080  1.00 30.73      B  C
ATOM   4469  C    TRP B 301      38.580  30.673  85.245  1.00 62.04      B  C
ATOM   4470  O    TRP B 301      39.397  30.033  84.565  1.00 62.04      B  O
ATOM   4471  N    THR B 302      38.919  31.452  86.279  1.00 60.34      B  N
ATOM   4472  CA   THR B 302      40.294  31.645  86.783  1.00 60.34      B  C
ATOM   4473  CB   THR B 302      40.616  30.681  87.972  1.00 58.11      B  C
ATOM   4474  OG1  THR B 302      39.410  30.087  88.462  1.00 58.11      B  O
ATOM   4475  CG2  THR B 302      41.257  31.455  89.125  1.00 58.11      B  C
ATOM   4476  C    THR B 302      41.450  31.538  85.777  1.00 60.34      B  C
ATOM   4477  O    THR B 302      42.592  31.255  86.151  1.00 60.34      B  O
ATOM   4478  N    LYS B 303      41.160  31.767  84.504  1.00 56.89      B  N
ATOM   4479  CA   LYS B 303      42.186  31.724  83.466  1.00 56.89      B  C
ATOM   4480  CB   LYS B 303      42.223  30.346  82.781  1.00 71.54      B  C
ATOM   4481  CG   LYS B 303      43.188  29.315  83.413  1.00 71.54      B  C
ATOM   4482  CD   LYS B 303      44.396  29.014  82.488  1.00 71.54      B  C
ATOM   4483  CE   LYS B 303      45.526  30.030  82.644  1.00 71.54      B  C
ATOM   4484  NZ   LYS B 303      46.118  29.939  84.019  1.00 71.54      B  N
ATOM   4485  C    LYS B 303      41.738  32.796  82.489  1.00 56.89      B  C
ATOM   4486  O    LYS B 303      42.308  32.977  81.411  1.00 56.89      B  O
ATOM   4487  N    VAL B 304      40.704  33.512  82.917  1.00 42.84      B  N
ATOM   4488  CA   VAL B 304      40.085  34.581  82.157  1.00 42.84      B  C
ATOM   4489  CB   VAL B 304      38.568  34.549  82.393  1.00 37.64      B  C
ATOM   4490  CG1  VAL B 304      37.909  35.731  81.717  1.00 37.64      B  C
ATOM   4491  CG2  VAL B 304      37.999  33.227  81.907  1.00 37.64      B  C
ATOM   4492  C    VAL B 304      40.591  35.963  82.530  1.00 42.84      B  C
ATOM   4493  O    VAL B 304      40.737  36.820  81.657  1.00 42.84      B  O
ATOM   4494  N    PHE B 305      40.854  36.175  83.821  1.00 41.53      B  N
ATOM   4495  CA   PHE B 305      41.294  37.486  84.317  1.00 41.53      B  C
ATOM   4496  CB   PHE B 305      40.599  37.763  85.655  1.00 28.42      B  C
ATOM   4497  CG   PHE B 305      39.109  37.862  85.529  1.00 28.42      B  C
```

FIG. 6-76

```
ATOM   4498  CD1  PHE B 305      38.511  39.056  85.116  1.00 28.42       B    C
ATOM   4499  CD2  PHE B 305      38.305  36.742  85.732  1.00 28.42       B    C
ATOM   4500  CE1  PHE B 305      37.139  39.132  84.910  1.00 28.42       B    C
ATOM   4501  CE2  PHE B 305      36.928  36.808  85.526  1.00 28.42       B    C
ATOM   4502  CZ   PHE B 305      36.346  38.002  85.112  1.00 28.42       B    C
ATOM   4503  C    PHE B 305      42.807  37.705  84.427  1.00 41.53       B    C
ATOM   4504  O    PHE B 305      43.590  36.751  84.399  1.00 41.53       B    O
ATOM   4505  N    ARG B 306      43.208  38.972  84.534  1.00 34.43       B    N
ATOM   4506  CA   ARG B 306      44.624  39.306  84.648  1.00 34.43       B    C
ATOM   4507  CB   ARG B 306      44.831  40.823  84.701  1.00 92.00       B    C
ATOM   4508  CG   ARG B 306      44.210  41.493  85.912  1.00 92.00       B    C
ATOM   4509  CD   ARG B 306      45.278  42.174  86.767  1.00 92.00       B    C
ATOM   4510  NE   ARG B 306      45.756  43.425  86.168  1.00 92.00       B    N
ATOM   4511  CZ   ARG B 306      45.055  44.561  86.136  1.00 92.00       B    C
ATOM   4512  NH1  ARG B 306      43.836  44.611  86.678  1.00 92.00       B    N
ATOM   4513  NH2  ARG B 306      45.564  45.647  85.550  1.00 92.00       B    N
ATOM   4514  C    ARG B 306      45.164  38.654  85.921  1.00 34.43       B    C
ATOM   4515  O    ARG B 306      44.430  37.985  86.653  1.00 34.43       B    O
ATOM   4516  N    PRO B 307      46.461  38.845  86.207  1.00 53.97       B    N
ATOM   4517  CD   PRO B 307      47.513  39.427  85.348  1.00 90.25       B    C
ATOM   4518  CA   PRO B 307      47.057  38.245  87.406  1.00 53.97       B    C
ATOM   4519  CB   PRO B 307      48.528  38.655  87.301  1.00 90.25       B    C
ATOM   4520  CG   PRO B 307      48.757  38.682  85.813  1.00 90.25       B    C
ATOM   4521  C    PRO B 307      46.449  38.582  88.777  1.00 53.97       B    C
ATOM   4522  O    PRO B 307      45.706  37.785  89.368  1.00 53.97       B    O
ATOM   4523  N    ALA B 308      46.781  39.762  89.285  1.00 59.73       B    N
ATOM   4524  CA   ALA B 308      46.308  40.194  90.598  1.00 59.73       B    C
ATOM   4525  CB   ALA B 308      46.748  41.633  90.852  1.00 67.44       B    C
ATOM   4526  C    ALA B 308      44.800  40.074  90.831  1.00 59.73       B    C
ATOM   4527  O    ALA B 308      44.362  40.005  91.982  1.00 59.73       B    O
ATOM   4528  N    THR B 309      44.011  40.066  89.757  1.00 42.81       B    N
ATOM   4529  CA   THR B 309      42.556  39.965  89.879  1.00 42.81       B    C
ATOM   4530  CB   THR B 309      41.939  39.197  88.687  1.00 51.20       B    C
ATOM   4531  OG1  THR B 309      41.981  40.011  87.507  1.00 51.20       B    O
ATOM   4532  CG2  THR B 309      40.484  38.833  88.992  1.00 51.20       B    C
ATOM   4533  C    THR B 309      42.087  39.274  91.155  1.00 42.81       B    C
ATOM   4534  O    THR B 309      42.283  38.073  91.328  1.00 42.81       B    O
ATOM   4535  N    PRO B 310      41.441  40.026  92.058  1.00 50.22       B    N
ATOM   4536  CD   PRO B 310      41.084  41.451  91.952  1.00 21.85       B    C
ATOM   4537  CA   PRO B 310      40.951  39.460  93.321  1.00 50.22       B    C
ATOM   4538  CB   PRO B 310      40.113  40.592  93.912  1.00 21.85       B    C
ATOM   4539  CG   PRO B 310      40.794  41.803  93.403  1.00 21.85       B    C
ATOM   4540  C    PRO B 310      40.117  38.199  93.106  1.00 50.22       B    C
ATOM   4541  O    PRO B 310      39.261  38.149  92.219  1.00 50.22       B    O
ATOM   4542  N    PRO B 311      40.362  37.158  93.914  1.00 39.44       B    N
ATOM   4543  CD   PRO B 311      41.310  37.040  95.034  1.00 29.28       B    C
ATOM   4544  CA   PRO B 311      39.591  35.930  93.761  1.00 39.44       B    C
ATOM   4545  CB   PRO B 311      40.234  34.990  94.779  1.00 29.28       B    C
ATOM   4546  CG   PRO B 311      40.695  35.921  95.847  1.00 29.28       B    C
ATOM   4547  C    PRO B 311      38.118  36.180  94.033  1.00 39.44       B    C
ATOM   4548  O    PRO B 311      37.271  35.718  93.284  1.00 39.44       B    O
ATOM   4549  N    GLU B 312      37.815  36.917  95.098  1.00 30.58       B    N
ATOM   4550  CA   GLU B 312      36.426  37.220  95.447  1.00 30.58       B    C
ATOM   4551  CB   GLU B 312      36.365  38.189  96.639  1.00 67.01       B    C
ATOM   4552  CG   GLU B 312      37.636  38.994  96.851  1.00 67.01       B    C
ATOM   4553  CD   GLU B 312      38.731  38.170  97.518  1.00 67.01       B    C
ATOM   4554  OE1  GLU B 312      39.938  38.506  97.350  1.00 67.01       B    O
ATOM   4555  OE2  GLU B 312      38.372  37.194  98.223  1.00 67.01       B    O
ATOM   4556  C    GLU B 312      35.659  37.793  94.252  1.00 30.58       B    C
ATOM   4557  O    GLU B 312      34.485  37.464  94.042  1.00 30.58       B    O
```

FIG. 6-77

| ATOM | 4558 | N | ALA | B | 313 | 36.326 | 38.635 | 93.467 | 1.00 | 24.22 | B | N |
|------|------|------|-----|---|-----|--------|--------|--------|------|-------|---|---|
| ATOM | 4559 | CA | ALA | B | 313 | 35.698 | 39.232 | 92.300 | 1.00 | 24.22 | B | C |
| ATOM | 4560 | CB | ALA | B | 313 | 36.638 | 40.251 | 91.679 | 1.00 | 19.24 | B | C |
| ATOM | 4561 | C | ALA | B | 313 | 35.345 | 38.133 | 91.289 | 1.00 | 24.22 | B | C |
| ATOM | 4562 | O | ALA | B | 313 | 34.225 | 38.090 | 90.761 | 1.00 | 24.22 | B | O |
| ATOM | 4563 | N | ILE | B | 314 | 36.303 | 37.246 | 91.036 | 1.00 | 18.97 | B | N |
| ATOM | 4564 | CA | ILE | B | 314 | 36.115 | 36.139 | 90.105 | 1.00 | 18.97 | B | C |
| ATOM | 4565 | CB | ILE | B | 314 | 37.393 | 35.272 | 90.003 | 1.00 | 19.96 | B | C |
| ATOM | 4566 | CG2 | ILE | B | 314 | 37.164 | 34.096 | 89.080 | 1.00 | 19.96 | B | C |
| ATOM | 4567 | CG1 | ILE | B | 314 | 38.547 | 36.110 | 89.468 | 1.00 | 19.96 | B | C |
| ATOM | 4568 | CD1 | ILE | B | 314 | 39.811 | 35.334 | 89.299 | 1.00 | 19.96 | B | C |
| ATOM | 4569 | C | ILE | B | 314 | 34.964 | 35.256 | 90.600 | 1.00 | 18.97 | B | C |
| ATOM | 4570 | O | ILE | B | 314 | 34.082 | 34.850 | 89.842 | 1.00 | 18.97 | B | O |
| ATOM | 4571 | N | ALA | B | 315 | 34.983 | 34.965 | 91.890 | 1.00 | 40.39 | B | N |
| ATOM | 4572 | CA | ALA | B | 315 | 33.948 | 34.146 | 92.498 | 1.00 | 40.39 | B | C |
| ATOM | 4573 | CB | ALA | B | 315 | 34.157 | 34.113 | 93.993 | 1.00 | 27.17 | B | C |
| ATOM | 4574 | C | ALA | B | 315 | 32.540 | 34.668 | 92.184 | 1.00 | 40.39 | B | C |
| ATOM | 4575 | O | ALA | B | 315 | 31.658 | 33.909 | 91.764 | 1.00 | 40.39 | B | O |
| ATOM | 4576 | N | LEU | B | 316 | 32.344 | 35.970 | 92.404 | 1.00 | 34.20 | B | N |
| ATOM | 4577 | CA | LEU | B | 316 | 31.073 | 36.635 | 92.152 | 1.00 | 34.20 | B | C |
| ATOM | 4578 | CB | LEU | B | 316 | 31.130 | 38.080 | 92.652 | 1.00 | 21.83 | B | C |
| ATOM | 4579 | CG | LEU | B | 316 | 29.907 | 38.952 | 92.372 | 1.00 | 21.83 | B | C |
| ATOM | 4580 | CD1 | LEU | B | 316 | 28.678 | 38.333 | 92.984 | 1.00 | 21.83 | B | C |
| ATOM | 4581 | CD2 | LEU | B | 316 | 30.128 | 40.335 | 92.920 | 1.00 | 21.83 | B | C |
| ATOM | 4582 | C | LEU | B | 316 | 30.692 | 36.607 | 90.679 | 1.00 | 34.20 | B | C |
| ATOM | 4583 | O | LEU | B | 316 | 29.510 | 36.657 | 90.351 | 1.00 | 34.20 | B | O |
| ATOM | 4584 | N | CYS | B | 317 | 31.663 | 36.532 | 89.782 | 1.00 | 23.37 | B | N |
| ATOM | 4585 | CA | CYS | B | 317 | 31.285 | 36.479 | 88.376 | 1.00 | 23.37 | B | C |
| ATOM | 4586 | CB | CYS | B | 317 | 32.500 | 36.604 | 87.465 | 1.00 | 39.29 | B | C |
| ATOM | 4587 | SG | CYS | B | 317 | 32.958 | 38.291 | 87.128 | 1.00 | 39.29 | B | S |
| ATOM | 4588 | C | CYS | B | 317 | 30.608 | 35.147 | 88.104 | 1.00 | 23.37 | B | C |
| ATOM | 4589 | O | CYS | B | 317 | 29.492 | 35.078 | 87.578 | 1.00 | 23.37 | B | O |
| ATOM | 4590 | N | SER | B | 318 | 31.309 | 34.086 | 88.469 | 1.00 | 30.53 | B | N |
| ATOM | 4591 | CA | SER | B | 318 | 30.832 | 32.733 | 88.270 | 1.00 | 30.53 | B | C |
| ATOM | 4592 | CB | SER | B | 318 | 31.791 | 31.772 | 88.947 | 1.00 | 64.27 | B | C |
| ATOM | 4593 | OG | SER | B | 318 | 32.324 | 32.371 | 90.120 | 1.00 | 64.27 | B | O |
| ATOM | 4594 | C | SER | B | 318 | 29.438 | 32.514 | 88.808 | 1.00 | 30.53 | B | C |
| ATOM | 4595 | O | SER | B | 318 | 28.650 | 31.780 | 88.207 | 1.00 | 30.53 | B | O |
| ATOM | 4596 | N | ARG | B | 319 | 29.137 | 33.144 | 89.942 | 1.00 | 30.82 | B | N |
| ATOM | 4597 | CA | ARG | B | 319 | 27.826 | 33.008 | 90.572 | 1.00 | 30.82 | B | C |
| ATOM | 4598 | CB | ARG | B | 319 | 27.928 | 33.291 | 92.080 | 1.00 | 34.18 | B | C |
| ATOM | 4599 | CG | ARG | B | 319 | 28.700 | 32.253 | 92.882 | 1.00 | 34.18 | B | C |
| ATOM | 4600 | CD | ARG | B | 319 | 28.306 | 30.834 | 92.492 | 1.00 | 34.18 | B | C |
| ATOM | 4601 | NE | ARG | B | 319 | 26.868 | 30.687 | 92.272 | 1.00 | 34.18 | B | N |
| ATOM | 4602 | CZ | ARG | B | 319 | 25.952 | 30.653 | 93.237 | 1.00 | 34.18 | B | C |
| ATOM | 4603 | NH1 | ARG | B | 319 | 26.314 | 30.754 | 94.511 | 1.00 | 34.18 | B | N |
| ATOM | 4604 | NH2 | ARG | B | 319 | 24.665 | 30.517 | 92.926 | 1.00 | 34.18 | B | N |
| ATOM | 4605 | C | ARG | B | 319 | 26.779 | 33.929 | 89.952 | 1.00 | 30.82 | B | C |
| ATOM | 4606 | O | ARG | B | 319 | 25.600 | 33.877 | 90.317 | 1.00 | 30.82 | B | O |
| ATOM | 4607 | N | LEU | B | 320 | 27.217 | 34.780 | 89.030 | 1.00 | 26.79 | B | N |
| ATOM | 4608 | CA | LEU | B | 320 | 26.314 | 35.697 | 88.346 | 1.00 | 26.79 | B | C |
| ATOM | 4609 | CB | LEU | B | 320 | 26.924 | 37.099 | 88.258 | 1.00 | 10.35 | B | C |
| ATOM | 4610 | CG | LEU | B | 320 | 26.935 | 37.904 | 89.549 | 1.00 | 10.35 | B | C |
| ATOM | 4611 | CD1 | LEU | B | 320 | 27.723 | 39.181 | 89.386 | 1.00 | 10.35 | B | C |
| ATOM | 4612 | CD2 | LEU | B | 320 | 25.503 | 38.192 | 89.939 | 1.00 | 10.35 | B | C |
| ATOM | 4613 | C | LEU | B | 320 | 26.053 | 35.172 | 86.944 | 1.00 | 26.79 | B | C |
| ATOM | 4614 | O | LEU | B | 320 | 24.908 | 35.075 | 86.503 | 1.00 | 26.79 | B | O |
| ATOM | 4615 | N | LEU | B | 321 | 27.130 | 34.818 | 86.252 | 1.00 | 21.49 | B | N |
| ATOM | 4616 | CA | LEU | B | 321 | 27.021 | 34.320 | 84.897 | 1.00 | 21.49 | B | C |
| ATOM | 4617 | CB | LEU | B | 321 | 28.253 | 34.745 | 84.104 | 1.00 | 15.20 | B | C |

FIG. 6-78

```
ATOM   4618  CG   LEU B 321      28.459  36.260  84.125  1.00 15.20      B  C
ATOM   4619  CD1  LEU B 321      29.767  36.615  83.472  1.00 15.20      B  C
ATOM   4620  CD2  LEU B 321      27.299  36.938  83.437  1.00 15.20      B  C
ATOM   4621  C    LEU B 321      26.854  32.818  84.852  1.00 21.49      B  C
ATOM   4622  O    LEU B 321      27.758  32.105  84.437  1.00 21.49      B  O
ATOM   4623  N    GLU B 322      25.680  32.354  85.277  1.00 35.41      B  N
ATOM   4624  CA   GLU B 322      25.341  30.925  85.309  1.00 35.41      B  C
ATOM   4625  CB   GLU B 322      24.807  30.544  86.701  1.00 55.23      B  C
ATOM   4626  CG   GLU B 322      25.412  29.258  87.294  1.00 55.23      B  C
ATOM   4627  CD   GLU B 322      26.294  29.513  88.531  1.00 55.23      B  C
ATOM   4628  OE1  GLU B 322      25.809  30.132  89.517  1.00 55.23      B  O
ATOM   4629  OE2  GLU B 322      27.473  29.083  88.526  1.00 55.23      B  O
ATOM   4630  C    GLU B 322      24.282  30.622  84.255  1.00 35.41      B  C
ATOM   4631  O    GLU B 322      23.384  31.432  84.043  1.00 35.41      B  O
ATOM   4632  N    TYR B 323      24.390  29.464  83.597  1.00 25.83      B  N
ATOM   4633  CA   TYR B 323      23.424  29.064  82.565  1.00 25.83      B  C
ATOM   4634  CB   TYR B 323      23.804  27.702  81.973  1.00 22.98      B  C
ATOM   4635  CG   TYR B 323      24.925  27.730  80.953  1.00 22.98      B  C
ATOM   4636  CD1  TYR B 323      24.768  28.368  79.722  1.00 22.98      B  C
ATOM   4637  CE1  TYR B 323      25.774  28.341  78.761  1.00 22.98      B  C
ATOM   4638  CD2  TYR B 323      26.129  27.071  81.198  1.00 22.98      B  C
ATOM   4639  CE2  TYR B 323      27.146  27.041  80.239  1.00 22.98      B  C
ATOM   4640  CZ   TYR B 323      26.958  27.673  79.027  1.00 22.98      B  C
ATOM   4641  OH   TYR B 323      27.946  27.608  78.078  1.00 22.98      B  O
ATOM   4642  C    TYR B 323      21.986  29.012  83.106  1.00 25.83      B  C
ATOM   4643  O    TYR B 323      21.095  29.676  82.583  1.00 25.83      B  O
ATOM   4644  N    THR B 324      21.745  28.227  84.147  1.00 29.80      B  N
ATOM   4645  CA   THR B 324      20.399  28.174  84.692  1.00 29.80      B  C
ATOM   4646  CB   THR B 324      20.240  27.084  85.757  1.00 44.00      B  C
ATOM   4647  OG1  THR B 324      20.390  25.796  85.150  1.00 44.00      B  O
ATOM   4648  CG2  THR B 324      18.861  27.183  86.409  1.00 44.00      B  C
ATOM   4649  C    THR B 324      20.057  29.512  85.331  1.00 29.80      B  C
ATOM   4650  O    THR B 324      20.684  29.936  86.300  1.00 29.80      B  O
ATOM   4651  N    PRO B 325      19.043  30.195  84.795  1.00 40.32      B  N
ATOM   4652  CD   PRO B 325      18.201  29.794  83.653  1.00 43.14      B  C
ATOM   4653  CA   PRO B 325      18.635  31.493  85.329  1.00 40.32      B  C
ATOM   4654  CB   PRO B 325      17.387  31.827  84.512  1.00 43.14      B  C
ATOM   4655  CG   PRO B 325      17.615  31.122  83.210  1.00 43.14      B  C
ATOM   4656  C    PRO B 325      18.338  31.423  86.819  1.00 40.32      B  C
ATOM   4657  O    PRO B 325      18.670  32.344  87.567  1.00 40.32      B  O
ATOM   4658  N    THR B 326      17.727  30.327  87.262  1.00 30.35      B  N
ATOM   4659  CA   THR B 326      17.391  30.191  88.678  1.00 30.35      B  C
ATOM   4660  CB   THR B 326      16.453  29.010  88.959  1.00 21.05      B  C
ATOM   4661  OG1  THR B 326      17.209  27.790  88.973  1.00 21.05      B  O
ATOM   4662  CG2  THR B 326      15.378  28.918  87.906  1.00 21.05      B  C
ATOM   4663  C    THR B 326      18.591  29.971  89.582  1.00 30.35      B  C
ATOM   4664  O    THR B 326      18.465  30.047  90.797  1.00 30.35      B  O
ATOM   4665  N    ALA B 327      19.751  29.684  89.010  1.00 18.44      B  N
ATOM   4666  CA   ALA B 327      20.924  29.416  89.824  1.00 18.44      B  C
ATOM   4667  CB   ALA B 327      21.729  28.306  89.212  1.00 15.66      B  C
ATOM   4668  C    ALA B 327      21.799  30.627  90.004  1.00 18.44      B  C
ATOM   4669  O    ALA B 327      22.827  30.559  90.672  1.00 18.44      B  O
ATOM   4670  N    ARG B 328      21.397  31.737  89.405  1.00 27.31      B  N
ATOM   4671  CA   ARG B 328      22.186  32.957  89.505  1.00 27.31      B  C
ATOM   4672  CB   ARG B 328      21.853  33.907  88.353  1.00 11.21      B  C
ATOM   4673  CG   ARG B 328      22.018  33.282  86.991  1.00 11.21      B  C
ATOM   4674  CD   ARG B 328      21.396  34.102  85.886  1.00 11.21      B  C
ATOM   4675  NE   ARG B 328      21.451  33.344  84.646  1.00 11.21      B  N
ATOM   4676  CZ   ARG B 328      20.734  33.604  83.565  1.00 11.21      B  C
ATOM   4677  NH1  ARG B 328      19.890  34.620  83.543  1.00 11.21      B  N
```

FIG. 6-79

```
ATOM   4678  NH2 ARG B 328      20.849  32.821  82.513  1.00 11.21      B    N
ATOM   4679  C   ARG B 328      21.854  33.641  90.806  1.00 27.31      B    C
ATOM   4680  O   ARG B 328      20.741  33.514  91.310  1.00 27.31      B    O
ATOM   4681  N   LEU B 329      22.821  34.363  91.350  1.00 21.75      B    N
ATOM   4682  CA  LEU B 329      22.599  35.088  92.585  1.00 21.75      B    C
ATOM   4683  CB  LEU B 329      23.847  35.866  92.966  1.00 25.64      B    C
ATOM   4684  CG  LEU B 329      24.865  35.236  93.913  1.00 25.64      B    C
ATOM   4685  CD1 LEU B 329      24.984  33.743  93.692  1.00 25.64      B    C
ATOM   4686  CD2 LEU B 329      26.197  35.941  93.686  1.00 25.64      B    C
ATOM   4687  C   LEU B 329      21.460  36.064  92.384  1.00 21.75      B    C
ATOM   4688  O   LEU B 329      21.024  36.322  91.259  1.00 21.75      B    O
ATOM   4689  N   THR B 330      20.983  36.596  93.496  1.00 25.41      B    N
ATOM   4690  CA  THR B 330      19.904  37.570  93.511  1.00 25.41      B    C
ATOM   4691  CB  THR B 330      19.010  37.358  94.751  1.00 50.79      B    C
ATOM   4692  OG1 THR B 330      18.289  36.130  94.604  1.00 50.79      B    O
ATOM   4693  CG2 THR B 330      18.031  38.521  94.946  1.00 50.79      B    C
ATOM   4694  C   THR B 330      20.636  38.881  93.678  1.00 25.41      B    C
ATOM   4695  O   THR B 330      21.762  38.897  94.175  1.00 25.41      B    O
ATOM   4696  N   PRO B 331      20.035  39.992  93.244  1.00 20.00      B    N
ATOM   4697  CD  PRO B 331      18.905  40.127  92.314  1.00 30.41      B    C
ATOM   4698  CA  PRO B 331      20.723  41.272  93.412  1.00 20.00      B    C
ATOM   4699  CB  PRO B 331      19.695  42.268  92.917  1.00 30.41      B    C
ATOM   4700  CG  PRO B 331      19.106  41.524  91.767  1.00 30.41      B    C
ATOM   4701  C   PRO B 331      21.120  41.508  94.871  1.00 20.00      B    C
ATOM   4702  O   PRO B 331      22.179  42.055  95.169  1.00 20.00      B    O
ATOM   4703  N   LEU B 332      20.269  41.071  95.784  1.00 28.39      B    N
ATOM   4704  CA  LEU B 332      20.550  41.249  97.197  1.00 28.39      B    C
ATOM   4705  CB  LEU B 332      19.273  40.980  97.990  1.00 22.19      B    C
ATOM   4706  CG  LEU B 332      19.186  41.701  99.326  1.00 22.19      B    C
ATOM   4707  CD1 LEU B 332      19.571  43.164  99.168  1.00 22.19      B    C
ATOM   4708  CD2 LEU B 332      17.777  41.566  99.850  1.00 22.19      B    C
ATOM   4709  C   LEU B 332      21.689  40.336  97.643  1.00 28.39      B    C
ATOM   4710  O   LEU B 332      22.614  40.783  98.324  1.00 28.39      B    O
ATOM   4711  N   GLU B 333      21.631  39.064  97.243  1.00 28.81      B    N
ATOM   4712  CA  GLU B 333      22.674  38.112  97.620  1.00 28.81      B    C
ATOM   4713  CB  GLU B 333      22.339  36.703  97.147  1.00 27.28      B    C
ATOM   4714  CG  GLU B 333      21.037  36.176  97.688  1.00 27.28      B    C
ATOM   4715  CD  GLU B 333      20.663  34.829  97.096  1.00 27.28      B    C
ATOM   4716  OE1 GLU B 333      20.991  34.596  95.913  1.00 27.28      B    O
ATOM   4717  OE2 GLU B 333      20.028  34.022  97.806  1.00 27.28      B    O
ATOM   4718  C   GLU B 333      23.990  38.538  97.026  1.00 28.81      B    C
ATOM   4719  O   GLU B 333      25.043  38.177  97.538  1.00 28.81      B    O
ATOM   4720  N   ALA B 334      23.922  39.302  95.939  1.00 31.79      B    N
ATOM   4721  CA  ALA B 334      25.123  39.795  95.279  1.00 31.79      B    C
ATOM   4722  CB  ALA B 334      24.797  40.267  93.850  1.00 37.89      B    C
ATOM   4723  C   ALA B 334      25.699  40.936  96.108  1.00 31.79      B    C
ATOM   4724  O   ALA B 334      26.912  41.032  96.275  1.00 31.79      B    O
ATOM   4725  N   CYS B 335      24.817  41.783  96.635  1.00 24.00      B    N
ATOM   4726  CA  CYS B 335      25.233  42.907  97.468  1.00 24.00      B    C
ATOM   4727  CB  CYS B 335      24.019  43.689  97.966  1.00 23.27      B    C
ATOM   4728  SG  CYS B 335      23.279  44.785  96.758  1.00 23.27      B    S
ATOM   4729  C   CYS B 335      25.981  42.377  98.675  1.00 24.00      B    C
ATOM   4730  O   CYS B 335      26.978  42.950  99.111  1.00 24.00      B    O
ATOM   4731  N   ALA B 336      25.482  41.265  99.202  1.00 29.00      B    N
ATOM   4732  CA  ALA B 336      26.050  40.641 100.384  1.00 29.00      B    C
ATOM   4733  CB  ALA B 336      24.976  39.857 101.111  1.00 15.99      B    C
ATOM   4734  C   ALA B 336      27.228  39.739 100.109  1.00 29.00      B    C
ATOM   4735  O   ALA B 336      27.724  39.098 101.019  1.00 29.00      B    O
ATOM   4736  N   HIS B 337      27.682  39.687  98.864  1.00 19.93      B    N
ATOM   4737  CA  HIS B 337      28.807  38.837  98.512  1.00 19.93      B    C
```

FIG. 6-80

| | | | | | | | | | | | |
|---|---|---|---|---|---|---|---|---|---|---|---|
| ATOM | 4738 | CB | HIS | B | 337 | 28.972 | 38.795 | 96.989 | 1.00 | 32.75 | B C |
| ATOM | 4739 | CG | HIS | B | 337 | 29.886 | 37.708 | 96.511 | 1.00 | 32.75 | B C |
| ATOM | 4740 | CD2 | HIS | B | 337 | 29.623 | 36.452 | 96.077 | 1.00 | 32.75 | B C |
| ATOM | 4741 | ND1 | HIS | B | 337 | 31.262 | 37.829 | 96.522 | 1.00 | 32.75 | B N |
| ATOM | 4742 | CE1 | HIS | B | 337 | 31.803 | 36.694 | 96.121 | 1.00 | 32.75 | B C |
| ATOM | 4743 | NE2 | HIS | B | 337 | 30.830 | 35.842 | 95.846 | 1.00 | 32.75 | B N |
| ATOM | 4744 | C | HIS | B | 337 | 30.094 | 39.310 | 99.178 | 1.00 | 19.93 | B C |
| ATOM | 4745 | O | HIS | B | 337 | 30.265 | 40.486 | 99.475 | 1.00 | 19.93 | B O |
| ATOM | 4746 | N | SER | B | 338 | 31.005 | 38.379 | 99.411 | 1.00 | 28.34 | B N |
| ATOM | 4747 | CA | SER | B | 338 | 32.271 | 38.697 | 100.052 | 1.00 | 28.34 | B C |
| ATOM | 4748 | CB | SER | B | 338 | 33.108 | 37.424 | 100.178 | 1.00 | 51.45 | B C |
| ATOM | 4749 | OG | SER | B | 338 | 34.043 | 37.539 | 101.236 | 1.00 | 51.45 | B O |
| ATOM | 4750 | C | SER | B | 338 | 33.069 | 39.781 | 99.306 | 1.00 | 28.34 | B C |
| ATOM | 4751 | O | SER | B | 338 | 33.743 | 40.614 | 99.918 | 1.00 | 28.34 | B O |
| ATOM | 4752 | N | PHE | B | 339 | 32.996 | 39.764 | 97.981 | 1.00 | 30.23 | B N |
| ATOM | 4753 | CA | PHE | B | 339 | 33.697 | 40.752 | 97.173 | 1.00 | 30.23 | B C |
| ATOM | 4754 | CB | PHE | B | 339 | 33.278 | 40.604 | 95.712 | 1.00 | 19.76 | B C |
| ATOM | 4755 | CG | PHE | B | 339 | 33.845 | 41.653 | 94.814 | 1.00 | 19.76 | B C |
| ATOM | 4756 | CD1 | PHE | B | 339 | 35.209 | 41.725 | 94.590 | 1.00 | 19.76 | B C |
| ATOM | 4757 | CD2 | PHE | B | 339 | 33.017 | 42.587 | 94.214 | 1.00 | 19.76 | B C |
| ATOM | 4758 | CE1 | PHE | B | 339 | 35.749 | 42.719 | 93.783 | 1.00 | 19.76 | B C |
| ATOM | 4759 | CE2 | PHE | B | 339 | 33.540 | 43.585 | 93.407 | 1.00 | 19.76 | B C |
| ATOM | 4760 | CZ | PHE | B | 339 | 34.914 | 43.653 | 93.187 | 1.00 | 19.76 | B C |
| ATOM | 4761 | C | PHE | B | 339 | 33.444 | 42.200 | 97.631 | 1.00 | 30.23 | B C |
| ATOM | 4762 | O | PHE | B | 339 | 34.286 | 43.067 | 97.425 | 1.00 | 30.23 | B O |
| ATOM | 4763 | N | PHE | B | 340 | 32.300 | 42.462 | 98.260 | 1.00 | 23.95 | B N |
| ATOM | 4764 | CA | PHE | B | 340 | 31.976 | 43.823 | 98.692 | 1.00 | 23.95 | B C |
| ATOM | 4765 | CB | PHE | B | 340 | 30.503 | 44.127 | 98.396 | 1.00 | 41.57 | B C |
| ATOM | 4766 | CG | PHE | B | 340 | 30.168 | 44.117 | 96.928 | 1.00 | 41.57 | B C |
| ATOM | 4767 | CD1 | PHE | B | 340 | 30.671 | 45.102 | 96.078 | 1.00 | 41.57 | B C |
| ATOM | 4768 | CD2 | PHE | B | 340 | 29.368 | 43.114 | 96.386 | 1.00 | 41.57 | B C |
| ATOM | 4769 | CE1 | PHE | B | 340 | 30.373 | 45.084 | 94.717 | 1.00 | 41.57 | B C |
| ATOM | 4770 | CE2 | PHE | B | 340 | 29.070 | 43.094 | 95.029 | 1.00 | 41.57 | B C |
| ATOM | 4771 | CZ | PHE | B | 340 | 29.571 | 44.076 | 94.196 | 1.00 | 41.57 | B C |
| ATOM | 4772 | C | PHE | B | 340 | 32.271 | 44.168 | 100.147 | 1.00 | 23.95 | B C |
| ATOM | 4773 | O | PHE | B | 340 | 31.939 | 45.259 | 100.617 | 1.00 | 23.95 | B O |
| ATOM | 4774 | N | ASP | B | 341 | 32.900 | 43.242 | 100.855 | 1.00 | 19.60 | B N |
| ATOM | 4775 | CA | ASP | B | 341 | 33.227 | 43.460 | 102.247 | 1.00 | 19.60 | B C |
| ATOM | 4776 | CB | ASP | B | 341 | 34.096 | 42.326 | 102.749 | 1.00 | 28.00 | B C |
| ATOM | 4777 | CG | ASP | B | 341 | 33.363 | 41.026 | 102.787 | 1.00 | 28.00 | B C |
| ATOM | 4778 | OD1 | ASP | B | 341 | 32.118 | 41.063 | 102.824 | 1.00 | 28.00 | B O |
| ATOM | 4779 | OD2 | ASP | B | 341 | 34.029 | 39.973 | 102.794 | 1.00 | 28.00 | B O |
| ATOM | 4780 | C | ASP | B | 341 | 33.930 | 44.785 | 102.505 | 1.00 | 19.60 | B C |
| ATOM | 4781 | O | ASP | B | 341 | 33.575 | 45.517 | 103.416 | 1.00 | 19.60 | B O |
| ATOM | 4782 | N | GLU | B | 342 | 34.940 | 45.080 | 101.706 | 1.00 | 21.23 | B N |
| ATOM | 4783 | CA | GLU | B | 342 | 35.700 | 46.309 | 101.858 | 1.00 | 21.23 | B C |
| ATOM | 4784 | CB | GLU | B | 342 | 36.689 | 46.444 | 100.696 | 1.00 | 38.47 | B C |
| ATOM | 4785 | CG | GLU | B | 342 | 37.574 | 47.678 | 100.757 | 1.00 | 38.47 | B C |
| ATOM | 4786 | CD | GLU | B | 342 | 38.522 | 47.807 | 99.559 | 1.00 | 38.47 | B C |
| ATOM | 4787 | OE1 | GLU | B | 342 | 39.238 | 48.826 | 99.504 | 1.00 | 38.47 | B O |
| ATOM | 4788 | OE2 | GLU | B | 342 | 38.561 | 46.908 | 98.676 | 1.00 | 38.47 | B O |
| ATOM | 4789 | C | GLU | B | 342 | 34.836 | 47.563 | 101.945 | 1.00 | 21.23 | B C |
| ATOM | 4790 | O | GLU | B | 342 | 35.297 | 48.602 | 102.412 | 1.00 | 21.23 | B O |
| ATOM | 4791 | N | LEU | B | 343 | 33.592 | 47.476 | 101.488 | 1.00 | 16.96 | B N |
| ATOM | 4792 | CA | LEU | B | 343 | 32.701 | 48.631 | 101.520 | 1.00 | 16.96 | B C |
| ATOM | 4793 | CB | LEU | B | 343 | 31.649 | 48.522 | 100.415 | 1.00 | 16.76 | B C |
| ATOM | 4794 | CG | LEU | B | 343 | 32.164 | 48.517 | 98.977 | 1.00 | 16.76 | B C |
| ATOM | 4795 | CD1 | LEU | B | 343 | 31.001 | 48.457 | 98.019 | 1.00 | 16.76 | B C |
| ATOM | 4796 | CD2 | LEU | B | 343 | 32.987 | 49.760 | 98.725 | 1.00 | 16.76 | B C |
| ATOM | 4797 | C | LEU | B | 343 | 32.030 | 48.692 | 102.882 | 1.00 | 16.96 | B C |

FIG. 6-81

```
ATOM   4798  O    LEU B 343      31.615  49.753 103.352  1.00 16.96      B    O
ATOM   4799  N    ARG B 344      31.935  47.535 103.517  1.00 37.49      B    N
ATOM   4800  CA   ARG B 344      31.324  47.446 104.823  1.00 37.49      B    C
ATOM   4801  CB   ARG B 344      30.694  46.076 105.024  1.00 29.30      B    C
ATOM   4802  CG   ARG B 344      29.335  45.942 104.383  1.00 29.30      B    C
ATOM   4803  CD   ARG B 344      28.867  44.516 104.479  1.00 29.30      B    C
ATOM   4804  NE   ARG B 344      29.666  43.647 103.625  1.00 29.30      B    N
ATOM   4805  CZ   ARG B 344      29.360  43.361 102.367  1.00 29.30      B    C
ATOM   4806  NH1  ARG B 344      28.269  43.874 101.811  1.00 29.30      B    N
ATOM   4807  NH2  ARG B 344      30.143  42.553 101.668  1.00 29.30      B    N
ATOM   4808  C    ARG B 344      32.339  47.716 105.916  1.00 37.49      B    C
ATOM   4809  O    ARG B 344      32.019  47.642 107.108  1.00 37.49      B    O
ATOM   4810  N    ASP B 345      33.569  48.019 105.517  1.00 32.41      B    N
ATOM   4811  CA   ASP B 345      34.595  48.321 106.493  1.00 32.41      B    C
ATOM   4812  CB   ASP B 345      35.982  48.167 105.889  1.00 43.73      B    C
ATOM   4813  CG   ASP B 345      37.079  48.197 106.944  1.00 43.73      B    C
ATOM   4814  OD1  ASP B 345      37.609  47.100 107.248  1.00 43.73      B    O
ATOM   4815  OD2  ASP B 345      37.399  49.296 107.476  1.00 43.73      B    O
ATOM   4816  C    ASP B 345      34.394  49.777 106.903  1.00 32.41      B    C
ATOM   4817  O    ASP B 345      34.366  50.675 106.055  1.00 32.41      B    O
ATOM   4818  N    PRO B 346      34.261  50.031 108.211  1.00 32.35      B    N
ATOM   4819  CD   PRO B 346      34.511  49.069 109.296  1.00 35.21      B    C
ATOM   4820  CA   PRO B 346      34.062  51.374 108.761  1.00 32.35      B    C
ATOM   4821  CB   PRO B 346      34.112  51.133 110.264  1.00 35.21      B    C
ATOM   4822  CG   PRO B 346      35.045  49.971 110.377  1.00 35.21      B    C
ATOM   4823  C    PRO B 346      35.094  52.407 108.333  1.00 32.35      B    C
ATOM   4824  O    PRO B 346      34.783  53.587 108.212  1.00 32.35      B    O
ATOM   4825  N    ASN B 347      36.327  51.965 108.112  1.00 36.58      B    N
ATOM   4826  CA   ASN B 347      37.407  52.872 107.730  1.00 36.58      B    C
ATOM   4827  CB   ASN B 347      38.734  52.352 108.284  1.00 55.21      B    C
ATOM   4828  CG   ASN B 347      38.849  52.526 109.791  1.00 55.21      B    C
ATOM   4829  OD1  ASN B 347      39.798  52.030 110.417  1.00 55.21      B    O
ATOM   4830  ND2  ASN B 347      37.886  53.240 110.385  1.00 55.21      B    N
ATOM   4831  C    ASN B 347      37.565  53.125 106.240  1.00 36.58      B    C
ATOM   4832  O    ASN B 347      38.482  53.834 105.832  1.00 36.58      B    O
ATOM   4833  N    VAL B 348      36.684  52.559 105.421  1.00 39.90      B    N
ATOM   4834  CA   VAL B 348      36.812  52.752 103.984  1.00 39.90      B    C
ATOM   4835  CB   VAL B 348      35.848  51.851 103.170  1.00 31.32      B    C
ATOM   4836  CG1  VAL B 348      34.420  52.351 103.272  1.00 31.32      B    C
ATOM   4837  CG2  VAL B 348      36.300  51.823 101.725  1.00 31.32      B    C
ATOM   4838  C    VAL B 348      36.578  54.202 103.590  1.00 39.90      B    C
ATOM   4839  O    VAL B 348      35.653  54.864 104.079  1.00 39.90      B    O
ATOM   4840  N    LYS B 349      37.437  54.692 102.707  1.00 25.40      B    N
ATOM   4841  CA   LYS B 349      37.349  56.059 102.220  1.00 25.40      B    C
ATOM   4842  CB   LYS B 349      38.466  56.904 102.836  1.00 35.84      B    C
ATOM   4843  CG   LYS B 349      38.026  58.264 103.361  1.00 35.84      B    C
ATOM   4844  CD   LYS B 349      37.371  58.166 104.741  1.00 35.84      B    C
ATOM   4845  CE   LYS B 349      36.968  59.552 105.258  1.00 35.84      B    C
ATOM   4846  NZ   LYS B 349      36.585  59.524 106.699  1.00 35.84      B    N
ATOM   4847  C    LYS B 349      37.530  55.981 100.709  1.00 25.40      B    C
ATOM   4848  O    LYS B 349      37.854  54.924 100.174  1.00 25.40      B    O
ATOM   4849  N    LEU B 350      37.322  57.088 100.012  1.00 37.15      B    N
ATOM   4850  CA   LEU B 350      37.478  57.078  98.563  1.00 37.15      B    C
ATOM   4851  CB   LEU B 350      36.508  58.062  97.914  1.00 13.22      B    C
ATOM   4852  CG   LEU B 350      35.022  57.804  98.154  1.00 13.22      B    C
ATOM   4853  CD1  LEU B 350      34.234  58.923  97.521  1.00 13.22      B    C
ATOM   4854  CD2  LEU B 350      34.605  56.456  97.586  1.00 13.22      B    C
ATOM   4855  C    LEU B 350      38.905  57.460  98.215  1.00 37.15      B    C
ATOM   4856  O    LEU B 350      39.649  57.946  99.060  1.00 37.15      B    O
ATOM   4857  N    PRO B 351      39.311  57.254  96.958  1.00 39.18      B    N
```

FIG. 6-82

| | | | | | | | | | | | |
|---|---|---|---|---|---|---|---|---|---|---|---|
| ATOM | 4858 | CD | PRO | B | 351 | 38.598 | 56.761 | 95.772 | 1.00 36.83 | B | C |
| ATOM | 4859 | CA | PRO | B | 351 | 40.687 | 57.619 | 96.622 | 1.00 39.18 | B | C |
| ATOM | 4860 | CB | PRO | B | 351 | 40.864 | 57.048 | 95.212 | 1.00 36.83 | B | C |
| ATOM | 4861 | CG | PRO | B | 351 | 39.700 | 56.094 | 95.035 | 1.00 36.83 | B | C |
| ATOM | 4862 | C | PRO | B | 351 | 40.837 | 59.138 | 96.626 | 1.00 39.18 | B | C |
| ATOM | 4863 | O | PRO | B | 351 | 41.946 | 59.660 | 96.629 | 1.00 39.18 | B | O |
| ATOM | 4864 | N | ASN | B | 352 | 39.718 | 59.852 | 96.616 | 1.00 25.97 | B | N |
| ATOM | 4865 | CA | ASN | B | 352 | 39.780 | 61.306 | 96.615 | 1.00 25.97 | B | C |
| ATOM | 4866 | CB | ASN | B | 352 | 38.695 | 61.884 | 95.700 | 1.00 37.02 | B | C |
| ATOM | 4867 | CG | ASN | B | 352 | 37.337 | 62.005 | 96.376 | 1.00 37.02 | B | C |
| ATOM | 4868 | OD1 | ASN | B | 352 | 36.352 | 62.359 | 95.733 | 1.00 37.02 | B | O |
| ATOM | 4869 | ND2 | ASN | B | 352 | 37.281 | 61.728 | 97.671 | 1.00 37.02 | B | N |
| ATOM | 4870 | C | ASN | B | 352 | 39.672 | 61.893 | 98.023 | 1.00 25.97 | B | C |
| ATOM | 4871 | O | ASN | B | 352 | 39.508 | 63.095 | 98.206 | 1.00 25.97 | B | O |
| ATOM | 4872 | N | GLY | B | 353 | 39.725 | 61.021 | 99.018 | 1.00 35.80 | B | N |
| ATOM | 4873 | CA | GLY | B | 353 | 39.675 | 61.474 | 100.387 | 1.00 35.80 | B | C |
| ATOM | 4874 | C | GLY | B | 353 | 38.327 | 61.569 | 101.067 | 1.00 35.80 | B | C |
| ATOM | 4875 | O | GLY | B | 353 | 38.269 | 61.454 | 102.295 | 1.00 35.80 | B | O |
| ATOM | 4876 | N | ARG | B | 354 | 37.246 | 61.789 | 100.324 | 1.00 36.30 | B | N |
| ATOM | 4877 | CA | ARG | B | 354 | 35.947 | 61.893 | 100.982 | 1.00 36.30 | B | C |
| ATOM | 4878 | CB | ARG | B | 354 | 34.974 | 62.725 | 100.143 | 1.00 45.23 | B | C |
| ATOM | 4879 | CG | ARG | B | 354 | 34.924 | 62.417 | 98.674 | 1.00 45.23 | B | C |
| ATOM | 4880 | CD | ARG | B | 354 | 34.017 | 63.418 | 97.940 | 1.00 45.23 | B | C |
| ATOM | 4881 | NE | ARG | B | 354 | 34.722 | 64.622 | 97.483 | 1.00 45.23 | B | N |
| ATOM | 4882 | CZ | ARG | B | 354 | 34.125 | 65.661 | 96.890 | 1.00 45.23 | B | C |
| ATOM | 4883 | NH1 | ARG | B | 354 | 32.807 | 65.649 | 96.686 | 1.00 45.23 | B | N |
| ATOM | 4884 | NH2 | ARG | B | 354 | 34.840 | 66.706 | 96.482 | 1.00 45.23 | B | N |
| ATOM | 4885 | C | ARG | B | 354 | 35.335 | 60.549 | 101.363 | 1.00 36.30 | B | C |
| ATOM | 4886 | O | ARG | B | 354 | 35.903 | 59.498 | 101.073 | 1.00 36.30 | B | O |
| ATOM | 4887 | N | ASP | B | 355 | 34.198 | 60.581 | 102.051 | 1.00 38.82 | B | N |
| ATOM | 4888 | CA | ASP | B | 355 | 33.547 | 59.346 | 102.474 | 1.00 38.82 | B | C |
| ATOM | 4889 | CB | ASP | B | 355 | 32.612 | 59.598 | 103.653 | 1.00 60.40 | B | C |
| ATOM | 4890 | CG | ASP | B | 355 | 33.334 | 60.188 | 104.834 | 1.00 60.40 | B | C |
| ATOM | 4891 | OD1 | ASP | B | 355 | 33.771 | 61.363 | 104.724 | 1.00 60.40 | B | O |
| ATOM | 4892 | OD2 | ASP | B | 355 | 33.484 | 59.480 | 105.863 | 1.00 60.40 | B | O |
| ATOM | 4893 | C | ASP | B | 355 | 32.769 | 58.717 | 101.348 | 1.00 38.82 | B | C |
| ATOM | 4894 | O | ASP | B | 355 | 32.411 | 59.377 | 100.373 | 1.00 38.82 | B | O |
| ATOM | 4895 | N | THR | B | 356 | 32.518 | 57.427 | 101.489 | 1.00 34.74 | B | N |
| ATOM | 4896 | CA | THR | B | 356 | 31.769 | 56.698 | 100.491 | 1.00 34.74 | B | C |
| ATOM | 4897 | CB | THR | B | 356 | 31.916 | 55.186 | 100.734 | 1.00 34.59 | B | C |
| ATOM | 4898 | OG1 | THR | B | 356 | 31.670 | 54.899 | 102.116 | 1.00 34.59 | B | O |
| ATOM | 4899 | CG2 | THR | B | 356 | 33.321 | 54.735 | 100.395 | 1.00 34.59 | B | C |
| ATOM | 4900 | C | THR | B | 356 | 30.304 | 57.124 | 100.594 | 1.00 34.74 | B | C |
| ATOM | 4901 | O | THR | B | 356 | 29.847 | 57.570 | 101.653 | 1.00 34.74 | B | O |
| ATOM | 4902 | N | PRO | B | 357 | 29.556 | 57.021 | 99.486 | 1.00 16.76 | B | N |
| ATOM | 4903 | CD | PRO | B | 357 | 29.983 | 56.591 | 98.145 | 1.00 21.95 | B | C |
| ATOM | 4904 | CA | PRO | B | 357 | 28.146 | 57.400 | 99.486 | 1.00 16.76 | B | C |
| ATOM | 4905 | CB | PRO | B | 357 | 27.794 | 57.392 | 98.006 | 1.00 21.95 | B | C |
| ATOM | 4906 | CG | PRO | B | 357 | 28.670 | 56.336 | 97.468 | 1.00 21.95 | B | C |
| ATOM | 4907 | C | PRO | B | 357 | 27.307 | 56.442 | 100.313 | 1.00 16.76 | B | C |
| ATOM | 4908 | O | PRO | B | 357 | 27.813 | 55.445 | 100.808 | 1.00 16.76 | B | O |
| ATOM | 4909 | N | ALA | B | 358 | 26.033 | 56.766 | 100.484 | 1.00 26.37 | B | N |
| ATOM | 4910 | CA | ALA | B | 358 | 25.109 | 55.926 | 101.247 | 1.00 26.37 | B | C |
| ATOM | 4911 | CB | ALA | B | 358 | 23.696 | 56.501 | 101.146 | 1.00 23.45 | B | C |
| ATOM | 4912 | C | ALA | B | 358 | 25.132 | 54.520 | 100.666 | 1.00 26.37 | B | C |
| ATOM | 4913 | O | ALA | B | 358 | 24.879 | 54.337 | 99.475 | 1.00 26.37 | B | O |
| ATOM | 4914 | N | LEU | B | 359 | 25.414 | 53.527 | 101.499 | 1.00 23.95 | B | N |
| ATOM | 4915 | CA | LEU | B | 359 | 25.492 | 52.151 | 101.023 | 1.00 23.95 | B | C |
| ATOM | 4916 | CB | LEU | B | 359 | 26.948 | 51.690 | 101.096 | 1.00 21.92 | B | C |
| ATOM | 4917 | CG | LEU | B | 359 | 27.868 | 51.807 | 99.872 | 1.00 21.92 | B | C |

FIG. 6-83

| | | | | | | | | | | |
|---|---|---|---|---|---|---|---|---|---|---|
| ATOM | 4918 | CD1 | LEU | B | 359 | 27.549 | 53.015 | 99.032 | 1.00 21.92 | B C |
| ATOM | 4919 | CD2 | LEU | B | 359 | 29.302 | 51.866 | 100.352 | 1.00 21.92 | B C |
| ATOM | 4920 | C | LEU | B | 359 | 24.617 | 51.193 | 101.810 | 1.00 23.95 | B C |
| ATOM | 4921 | O | LEU | B | 359 | 24.251 | 50.122 | 101.320 | 1.00 23.95 | B O |
| ATOM | 4922 | N | PHE | B | 360 | 24.260 | 51.609 | 103.021 | 1.00 29.67 | B N |
| ATOM | 4923 | CA | PHE | B | 360 | 23.491 | 50.774 | 103.927 | 1.00 29.67 | B C |
| ATOM | 4924 | CB | PHE | B | 360 | 24.319 | 50.573 | 105.187 | 1.00 23.59 | B C |
| ATOM | 4925 | CG | PHE | B | 360 | 25.777 | 50.487 | 104.916 | 1.00 23.59 | B C |
| ATOM | 4926 | CD1 | PHE | B | 360 | 26.298 | 49.419 | 104.196 | 1.00 23.59 | B C |
| ATOM | 4927 | CD2 | PHE | B | 360 | 26.626 | 51.492 | 105.329 | 1.00 23.59 | B C |
| ATOM | 4928 | CE1 | PHE | B | 360 | 27.649 | 49.363 | 103.881 | 1.00 23.59 | B C |
| ATOM | 4929 | CE2 | PHE | B | 360 | 27.972 | 51.451 | 105.023 | 1.00 23.59 | B C |
| ATOM | 4930 | CZ | PHE | B | 360 | 28.489 | 50.383 | 104.298 | 1.00 23.59 | B C |
| ATOM | 4931 | C | PHE | B | 360 | 22.109 | 51.264 | 104.313 | 1.00 29.67 | B C |
| ATOM | 4932 | O | PHE | B | 360 | 21.492 | 50.692 | 105.203 | 1.00 29.67 | B O |
| ATOM | 4933 | N | ASN | B | 361 | 21.619 | 52.313 | 103.665 | 1.00 27.09 | B N |
| ATOM | 4934 | CA | ASN | B | 361 | 20.298 | 52.841 | 103.992 | 1.00 27.09 | B C |
| ATOM | 4935 | CB | ASN | B | 361 | 20.185 | 54.287 | 103.512 | 1.00 19.24 | B C |
| ATOM | 4936 | CG | ASN | B | 361 | 20.409 | 54.426 | 102.021 | 1.00 19.24 | B C |
| ATOM | 4937 | OD1 | ASN | B | 361 | 21.218 | 53.711 | 101.431 | 1.00 19.24 | B O |
| ATOM | 4938 | ND2 | ASN | B | 361 | 19.706 | 55.361 | 101.406 | 1.00 19.24 | B N |
| ATOM | 4939 | C | ASN | B | 361 | 19.203 | 51.993 | 103.353 | 1.00 27.09 | B C |
| ATOM | 4940 | O | ASN | B | 361 | 18.332 | 52.507 | 102.663 | 1.00 27.09 | B O |
| ATOM | 4941 | N | PHE | B | 362 | 19.261 | 50.689 | 103.583 | 1.00 14.79 | B N |
| ATOM | 4942 | CA | PHE | B | 362 | 18.274 | 49.767 | 103.046 | 1.00 14.79 | B C |
| ATOM | 4943 | CB | PHE | B | 362 | 18.673 | 48.332 | 103.379 | 1.00 29.26 | B C |
| ATOM | 4944 | CG | PHE | B | 362 | 19.821 | 47.821 | 102.576 | 1.00 29.26 | B C |
| ATOM | 4945 | CD1 | PHE | B | 362 | 19.638 | 47.429 | 101.254 | 1.00 29.26 | B C |
| ATOM | 4946 | CD2 | PHE | B | 362 | 21.093 | 47.746 | 103.126 | 1.00 29.26 | B C |
| ATOM | 4947 | CE1 | PHE | B | 362 | 20.707 | 46.971 | 100.494 | 1.00 29.26 | B C |
| ATOM | 4948 | CE2 | PHE | B | 362 | 22.163 | 47.289 | 102.368 | 1.00 29.26 | B C |
| ATOM | 4949 | CZ | PHE | B | 362 | 21.967 | 46.902 | 101.053 | 1.00 29.26 | B C |
| ATOM | 4950 | C | PHE | B | 362 | 16.903 | 50.030 | 103.649 | 1.00 14.79 | B C |
| ATOM | 4951 | O | PHE | B | 362 | 16.794 | 50.551 | 104.756 | 1.00 14.79 | B O |
| ATOM | 4952 | N | THR | B | 363 | 15.861 | 49.665 | 102.905 | 1.00 23.27 | B N |
| ATOM | 4953 | CA | THR | B | 363 | 14.484 | 49.788 | 103.368 | 1.00 23.27 | B C |
| ATOM | 4954 | CB | THR | B | 363 | 13.630 | 50.640 | 102.446 | 1.00 14.99 | B C |
| ATOM | 4955 | OG1 | THR | B | 363 | 13.622 | 50.056 | 101.140 | 1.00 14.99 | B O |
| ATOM | 4956 | CG2 | THR | B | 363 | 14.156 | 52.041 | 102.393 | 1.00 14.99 | B C |
| ATOM | 4957 | C | THR | B | 363 | 13.903 | 48.377 | 103.379 | 1.00 23.27 | B C |
| ATOM | 4958 | O | THR | B | 363 | 14.467 | 47.470 | 102.766 | 1.00 23.27 | B O |
| ATOM | 4959 | N | THR | B | 364 | 12.780 | 48.187 | 104.067 | 1.00 29.59 | B N |
| ATOM | 4960 | CA | THR | B | 364 | 12.159 | 46.866 | 104.114 | 1.00 29.59 | B C |
| ATOM | 4961 | CB | THR | B | 364 | 10.932 | 46.835 | 105.068 | 1.00 29.47 | B C |
| ATOM | 4962 | OG1 | THR | B | 364 | 9.964 | 47.794 | 104.643 | 1.00 29.47 | B O |
| ATOM | 4963 | CG2 | THR | B | 364 | 11.348 | 47.178 | 106.495 | 1.00 29.47 | B C |
| ATOM | 4964 | C | THR | B | 364 | 11.740 | 46.387 | 102.714 | 1.00 29.59 | B C |
| ATOM | 4965 | O | THR | B | 364 | 11.779 | 45.197 | 102.438 | 1.00 29.59 | B O |
| ATOM | 4966 | N | GLN | B | 365 | 11.349 | 47.305 | 101.830 | 1.00 30.05 | B N |
| ATOM | 4967 | CA | GLN | B | 365 | 10.965 | 46.922 | 100.473 | 1.00 30.05 | B C |
| ATOM | 4968 | CB | GLN | B | 365 | 10.452 | 48.119 | 99.668 | 1.00 27.65 | B C |
| ATOM | 4969 | CG | GLN | B | 365 | 8.988 | 48.028 | 99.226 | 1.00 27.65 | B C |
| ATOM | 4970 | CD | GLN | B | 365 | 8.716 | 46.925 | 98.217 | 1.00 27.65 | B C |
| ATOM | 4971 | OE1 | GLN | B | 365 | 9.164 | 46.990 | 97.082 | 1.00 27.65 | B O |
| ATOM | 4972 | NE2 | GLN | B | 365 | 7.975 | 45.907 | 98.634 | 1.00 27.65 | B N |
| ATOM | 4973 | C | GLN | B | 365 | 12.191 | 46.374 | 99.762 | 1.00 30.05 | B C |
| ATOM | 4974 | O | GLN | B | 365 | 12.140 | 45.360 | 99.062 | 1.00 30.05 | B O |
| ATOM | 4975 | N | GLU | B | 366 | 13.303 | 47.072 | 99.954 | 1.00 38.74 | B N |
| ATOM | 4976 | CA | GLU | B | 366 | 14.556 | 46.718 | 99.322 | 1.00 38.74 | B C |
| ATOM | 4977 | CB | GLU | B | 366 | 15.535 | 47.888 | 99.490 | 1.00 27.83 | B C |

FIG. 6-84

```
ATOM   4978  CG   GLU B 366      16.957  47.601  99.061  1.00 27.83      B  C
ATOM   4979  CD   GLU B 366      17.761  48.858  98.828  1.00 27.83      B  C
ATOM   4980  OE1  GLU B 366      17.549  49.854  99.543  1.00 27.83      B  O
ATOM   4981  OE2  GLU B 366      18.617  48.846  97.931  1.00 27.83      B  O
ATOM   4982  C    GLU B 366      15.123  45.403  99.862  1.00 38.74      B  C
ATOM   4983  O    GLU B 366      15.932  44.745  99.202  1.00 38.74      B  O
ATOM   4984  N    LEU B 367      14.683  45.003 101.049  1.00 32.77      B  N
ATOM   4985  CA   LEU B 367      15.174  43.758 101.637  1.00 32.77      B  C
ATOM   4986  CB   LEU B 367      15.571  43.964 103.101  1.00 26.49      B  C
ATOM   4987  CG   LEU B 367      16.766  44.883 103.388  1.00 26.49      B  C
ATOM   4988  CD1  LEU B 367      16.802  45.194 104.865  1.00 26.49      B  C
ATOM   4989  CD2  LEU B 367      18.069  44.241 102.932  1.00 26.49      B  C
ATOM   4990  C    LEU B 367      14.141  42.647 101.558  1.00 32.77      B  C
ATOM   4991  O    LEU B 367      14.427  41.506 101.913  1.00 32.77      B  O
ATOM   4992  N    SER B 368      12.949  42.984 101.079  1.00 17.32      B  N
ATOM   4993  CA   SER B 368      11.860  42.025 100.968  1.00 17.32      B  C
ATOM   4994  CB   SER B 368      10.768  42.585 100.059  1.00 28.23      B  C
ATOM   4995  OG   SER B 368      11.104  42.412  98.694  1.00 28.23      B  O
ATOM   4996  C    SER B 368      12.297  40.658 100.424  1.00 17.32      B  C
ATOM   4997  O    SER B 368      11.965  39.613 100.982  1.00 17.32      B  O
ATOM   4998  N    SER B 369      13.041  40.664  99.332  1.00 37.96      B  N
ATOM   4999  CA   SER B 369      13.479  39.417  98.723  1.00 37.96      B  C
ATOM   5000  CB   SER B 369      14.503  39.702  97.627  1.00 39.95      B  C
ATOM   5001  OG   SER B 369      15.730  39.048  97.914  1.00 39.95      B  O
ATOM   5002  C    SER B 369      14.085  38.425  99.716  1.00 37.96      B  C
ATOM   5003  O    SER B 369      14.061  37.212  99.492  1.00 37.96      B  O
ATOM   5004  N    ASN B 370      14.629  38.933 100.814  1.00 24.96      B  N
ATOM   5005  CA   ASN B 370      15.255  38.062 101.797  1.00 24.96      B  C
ATOM   5006  CB   ASN B 370      16.397  37.300 101.117  1.00 22.74      B  C
ATOM   5007  CG   ASN B 370      17.270  36.529 102.090  1.00 22.74      B  C
ATOM   5008  OD1  ASN B 370      18.201  35.840 101.675  1.00 22.74      B  O
ATOM   5009  ND2  ASN B 370      16.983  36.638 103.380  1.00 22.74      B  N
ATOM   5010  C    ASN B 370      15.781  38.881 102.977  1.00 24.96      B  C
ATOM   5011  O    ASN B 370      16.978  39.141 103.083  1.00 24.96      B  O
ATOM   5012  N    PRO B 371      14.875  39.287 103.885  1.00 21.40      B  N
ATOM   5013  CD   PRO B 371      13.428  39.025 103.749  1.00 15.76      B  C
ATOM   5014  CA   PRO B 371      15.139  40.082 105.093  1.00 21.40      B  C
ATOM   5015  CB   PRO B 371      13.834  39.964 105.868  1.00 15.76      B  C
ATOM   5016  CG   PRO B 371      12.825  39.982 104.768  1.00 15.76      B  C
ATOM   5017  C    PRO B 371      16.350  39.695 105.935  1.00 21.40      B  C
ATOM   5018  O    PRO B 371      17.136  40.545 106.327  1.00 21.40      B  O
ATOM   5019  N    PRO B 372      16.511  38.407 106.233  1.00 29.97      B  N
ATOM   5020  CD   PRO B 372      15.629  37.282 105.877  1.00 15.38      B  C
ATOM   5021  CA   PRO B 372      17.641  37.941 107.036  1.00 29.97      B  C
ATOM   5022  CB   PRO B 372      17.576  36.435 106.861  1.00 15.38      B  C
ATOM   5023  CG   PRO B 372      16.117  36.187 106.788  1.00 15.38      B  C
ATOM   5024  C    PRO B 372      18.989  38.493 106.607  1.00 29.97      B  C
ATOM   5025  O    PRO B 372      19.922  38.557 107.403  1.00 29.97      B  O
ATOM   5026  N    LEU B 373      19.101  38.878 105.344  1.00 34.38      B  N
ATOM   5027  CA   LEU B 373      20.357  39.405 104.838  1.00 34.38      B  C
ATOM   5028  CB   LEU B 373      20.293  39.522 103.315  1.00 52.52      B  C
ATOM   5029  CG   LEU B 373      21.137  38.498 102.542  1.00 52.52      B  C
ATOM   5030  CD1  LEU B 373      20.564  37.111 102.717  1.00 52.52      B  C
ATOM   5031  CD2  LEU B 373      21.162  38.877 101.072  1.00 52.52      B  C
ATOM   5032  C    LEU B 373      20.758  40.748 105.455  1.00 34.38      B  C
ATOM   5033  O    LEU B 373      21.912  41.171 105.340  1.00 34.38      B  O
ATOM   5034  N    ALA B 374      19.821  41.419 106.114  1.00 27.92      B  N
ATOM   5035  CA   ALA B 374      20.144  42.703 106.726  1.00 27.92      B  C
ATOM   5036  CB   ALA B 374      18.923  43.266 107.443  1.00 14.14      B  C
ATOM   5037  C    ALA B 374      21.300  42.564 107.716  1.00 27.92      B  C
```

FIG. 6-85

| ATOM | 5038 | O | ALA | B | 374 | 22.007 | 43.530 | 107.995 | 1.00 | 27.92 | B | O |
|---|---|---|---|---|---|---|---|---|---|---|---|---|
| ATOM | 5039 | N | THR | B | 375 | 21.492 | 41.357 | 108.242 | 1.00 | 30.95 | B | N |
| ATOM | 5040 | CA | THR | B | 375 | 22.555 | 41.136 | 109.214 | 1.00 | 30.95 | B | C |
| ATOM | 5041 | CB | THR | B | 375 | 22.539 | 39.719 | 109.794 | 1.00 | 35.18 | B | C |
| ATOM | 5042 | OG1 | THR | B | 375 | 21.202 | 39.374 | 110.154 | 1.00 | 35.18 | B | O |
| ATOM | 5043 | CG2 | THR | B | 375 | 23.388 | 39.654 | 111.057 | 1.00 | 35.18 | B | C |
| ATOM | 5044 | C | THR | B | 375 | 23.901 | 41.396 | 108.564 | 1.00 | 30.95 | B | C |
| ATOM | 5045 | O | THR | B | 375 | 24.826 | 41.894 | 109.207 | 1.00 | 30.95 | B | O |
| ATOM | 5046 | N | ILE | B | 376 | 24.005 | 41.062 | 107.283 | 1.00 | 37.43 | B | N |
| ATOM | 5047 | CA | ILE | B | 376 | 25.237 | 41.269 | 106.540 | 1.00 | 37.43 | B | C |
| ATOM | 5048 | CB | ILE | B | 376 | 25.453 | 40.209 | 105.481 | 1.00 | 29.24 | B | C |
| ATOM | 5049 | CG2 | ILE | B | 376 | 26.764 | 40.473 | 104.774 | 1.00 | 29.24 | B | C |
| ATOM | 5050 | CG1 | ILE | B | 376 | 25.446 | 38.823 | 106.114 | 1.00 | 29.24 | B | C |
| ATOM | 5051 | CD1 | ILE | B | 376 | 25.556 | 37.706 | 105.095 | 1.00 | 29.24 | B | C |
| ATOM | 5052 | C | ILE | B | 376 | 25.221 | 42.608 | 105.819 | 1.00 | 37.43 | B | C |
| ATOM | 5053 | O | ILE | B | 376 | 26.196 | 43.356 | 105.867 | 1.00 | 37.43 | B | O |
| ATOM | 5054 | N | LEU | B | 377 | 24.111 | 42.914 | 105.153 | 1.00 | 17.91 | B | N |
| ATOM | 5055 | CA | LEU | B | 377 | 24.013 | 44.162 | 104.419 | 1.00 | 17.91 | B | C |
| ATOM | 5056 | CB | LEU | B | 377 | 22.671 | 44.244 | 103.684 | 1.00 | 18.81 | B | C |
| ATOM | 5057 | CG | LEU | B | 377 | 22.554 | 43.487 | 102.350 | 1.00 | 18.81 | B | C |
| ATOM | 5058 | CD1 | LEU | B | 377 | 23.899 | 43.475 | 101.634 | 1.00 | 18.81 | B | C |
| ATOM | 5059 | CD2 | LEU | B | 377 | 22.097 | 42.079 | 102.593 | 1.00 | 18.81 | B | C |
| ATOM | 5060 | C | LEU | B | 377 | 24.253 | 45.440 | 105.233 | 1.00 | 17.91 | B | C |
| ATOM | 5061 | O | LEU | B | 377 | 24.903 | 46.371 | 104.755 | 1.00 | 17.91 | B | O |
| ATOM | 5062 | N | ILE | B | 378 | 23.732 | 45.496 | 106.457 | 1.00 | 26.15 | B | N |
| ATOM | 5063 | CA | ILE | B | 378 | 23.919 | 46.679 | 107.302 | 1.00 | 26.15 | B | C |
| ATOM | 5064 | CB | ILE | B | 378 | 22.626 | 47.112 | 108.016 | 1.00 | 17.20 | B | C |
| ATOM | 5065 | CG2 | ILE | B | 378 | 22.877 | 48.400 | 108.792 | 1.00 | 17.20 | B | C |
| ATOM | 5066 | CG1 | ILE | B | 378 | 21.522 | 47.386 | 107.002 | 1.00 | 17.20 | B | C |
| ATOM | 5067 | CD1 | ILE | B | 378 | 20.200 | 47.649 | 107.636 | 1.00 | 17.20 | B | C |
| ATOM | 5068 | C | ILE | B | 378 | 24.978 | 46.389 | 108.348 | 1.00 | 26.15 | B | C |
| ATOM | 5069 | O | ILE | B | 378 | 24.701 | 45.763 | 109.364 | 1.00 | 26.15 | B | O |
| ATOM | 5070 | N | PRO | B | 379 | 26.215 | 46.857 | 108.111 | 1.00 | 33.94 | B | N |
| ATOM | 5071 | CD | PRO | B | 379 | 26.638 | 47.720 | 106.997 | 1.00 | 27.24 | B | C |
| ATOM | 5072 | CA | PRO | B | 379 | 27.337 | 46.643 | 109.023 | 1.00 | 33.94 | B | C |
| ATOM | 5073 | CB | PRO | B | 379 | 28.503 | 47.287 | 108.276 | 1.00 | 27.24 | B | C |
| ATOM | 5074 | CG | PRO | B | 379 | 27.853 | 48.403 | 107.575 | 1.00 | 27.24 | B | C |
| ATOM | 5075 | C | PRO | B | 379 | 27.142 | 47.228 | 110.419 | 1.00 | 33.94 | B | C |
| ATOM | 5076 | O | PRO | B | 379 | 26.520 | 48.275 | 110.594 | 1.00 | 33.94 | B | O |
| ATOM | 5077 | N | PRO | B | 380 | 27.709 | 46.560 | 111.430 | 1.00 | 33.97 | B | N |
| ATOM | 5078 | CD | PRO | B | 380 | 28.618 | 45.414 | 111.243 | 1.00 | 32.45 | B | C |
| ATOM | 5079 | CA | PRO | B | 380 | 27.641 | 46.935 | 112.841 | 1.00 | 33.97 | B | C |
| ATOM | 5080 | CB | PRO | B | 380 | 28.766 | 46.120 | 113.471 | 1.00 | 32.45 | B | C |
| ATOM | 5081 | CG | PRO | B | 380 | 28.781 | 44.888 | 112.657 | 1.00 | 32.45 | B | C |
| ATOM | 5082 | C | PRO | B | 380 | 27.796 | 48.415 | 113.152 | 1.00 | 33.97 | B | C |
| ATOM | 5083 | O | PRO | B | 380 | 27.334 | 48.876 | 114.189 | 1.00 | 33.97 | B | O |
| ATOM | 5084 | N | HIS | B | 381 | 28.444 | 49.157 | 112.267 | 1.00 | 33.16 | B | N |
| ATOM | 5085 | CA | HIS | B | 381 | 28.676 | 50.571 | 112.519 | 1.00 | 33.16 | B | C |
| ATOM | 5086 | CB | HIS | B | 381 | 30.126 | 50.917 | 112.172 | 1.00 | 25.36 | B | C |
| ATOM | 5087 | CG | HIS | B | 381 | 30.453 | 50.774 | 110.718 | 1.00 | 25.36 | B | C |
| ATOM | 5088 | CD2 | HIS | B | 381 | 30.827 | 49.697 | 109.990 | 1.00 | 25.36 | B | C |
| ATOM | 5089 | ND1 | HIS | B | 381 | 30.376 | 51.826 | 109.830 | 1.00 | 25.36 | B | N |
| ATOM | 5090 | CE1 | HIS | B | 381 | 30.689 | 51.404 | 108.620 | 1.00 | 25.36 | B | C |
| ATOM | 5091 | NE2 | HIS | B | 381 | 30.967 | 50.114 | 108.689 | 1.00 | 25.36 | B | N |
| ATOM | 5092 | C | HIS | B | 381 | 27.751 | 51.543 | 111.793 | 1.00 | 33.16 | B | C |
| ATOM | 5093 | O | HIS | B | 381 | 27.703 | 52.716 | 112.138 | 1.00 | 33.16 | B | O |
| ATOM | 5094 | N | ALA | B | 382 | 27.002 | 51.077 | 110.804 | 1.00 | 34.55 | B | N |
| ATOM | 5095 | CA | ALA | B | 382 | 26.137 | 51.982 | 110.047 | 1.00 | 34.55 | B | C |
| ATOM | 5096 | CB | ALA | B | 382 | 25.826 | 51.367 | 108.699 | 1.00 | 51.30 | B | C |
| ATOM | 5097 | C | ALA | B | 382 | 24.837 | 52.404 | 110.742 | 1.00 | 34.55 | B | C |

FIG. 6-86

```
ATOM   5098  O    ALA B 382      24.687  53.616 110.995  1.00 34.55           B    O
ATOM   5099  OXT  ALA B 382      23.975  51.543 111.022  1.00 51.30           B    O
TER    5100       ALA B 382                                                   B
ATOM   5101  O    HOH W   1       6.884  43.261  76.228  1.00  4.71           W    O
ATOM   5102  O    HOH W   2      13.671  71.230  75.371  1.00 26.58           W    O
ATOM   5103  O    HOH W   3      24.031  52.355  97.568  1.00 18.47           W    O
ATOM   5104  O    HOH W   4      21.920  45.607  77.747  1.00 21.56           W    O
ATOM   5105  O    HOH W   5      14.844  49.877  80.739  1.00 27.44           W    O
ATOM   5106  O    HOH W   6      12.108  34.233  55.498  1.00 10.13           W    O
ATOM   5107  O    HOH W   7      30.003  40.262  77.662  1.00 35.85           W    O
ATOM   5108  O    HOH W   8      19.970  39.689  79.413  1.00 17.86           W    O
ATOM   5109  O    HOH W   9      18.645  38.017  57.432  1.00 20.91           W    O
ATOM   5110  O    HOH W  10       9.591  53.585  97.286  1.00  6.30           W    O
ATOM   5111  O    HOH W  11      13.130  31.272  80.326  1.00 25.36           W    O
ATOM   5112  O    HOH W  12      26.690  45.855 102.976  1.00 30.90           W    O
ATOM   5113  O    HOH W  13       4.791  33.157  61.302  1.00 40.39           W    O
ATOM   5114  O    HOH W  14      39.534  46.733  87.188  1.00 25.98           W    O
ATOM   5115  O    HOH W  15      14.615  57.255  92.346  1.00 22.22           W    O
ATOM   5116  O    HOH W  16      31.695  51.737 105.400  1.00 25.68           W    O
ATOM   5117  O    HOH W  17      26.193  37.668  77.252  1.00 18.51           W    O
ATOM   5118  O    HOH W  18      20.267  43.312  62.793  1.00 33.57           W    O
ATOM   5119  O    HOH W  19      18.709  60.142  91.276  1.00 28.86           W    O
ATOM   5120  O    HOH W  20      25.039  55.741  96.972  1.00 19.09           W    O
ATOM   5121  O    HOH W  21      12.205  58.941  89.719  1.00 20.06           W    O
ATOM   5122  O    HOH W  22      19.044  43.587  81.053  1.00 30.63           W    O
ATOM   5123  O    HOH W  23      23.292  26.709  85.852  1.00 37.91           W    O
ATOM   5124  O    HOH W  24      24.830  49.824  73.410  1.00 35.22           W    O
ATOM   5125  O    HOH W  25      22.858  22.020  56.688  1.00 23.79           W    O
ATOM   5126  O    HOH W  26       9.077  54.896  76.657  1.00 23.67           W    O
ATOM   5127  O    HOH W  27       2.986  60.035  77.857  1.00 36.42           W    O
ATOM   5128  O    HOH W  28      10.147  36.275  69.986  1.00 31.72           W    O
ATOM   5129  O    HOH W  29       3.329  71.512  92.548  1.00 22.56           W    O
ATOM   5130  O    HOH W  30      22.205  36.195  55.588  1.00 29.04           W    O
ATOM   5131  O    HOH W  31      36.733  59.106  90.404  1.00 29.08           W    O
ATOM   5132  O    HOH W  32      30.254  65.353  78.598  1.00 32.14           W    O
ATOM   5133  O    HOH W  33      10.344  49.830 102.685  1.00 24.89           W    O
ATOM   5134  O    HOH W  34      30.323  22.013  38.917  1.00 38.50           W    O
ATOM   5135  O    HOH W  35      55.593  18.422  47.168  1.00 22.50           W    O
ATOM   5136  O    HOH W  36      16.081  33.453  43.021  1.00 21.23           W    O
ATOM   5137  O    HOH W  37      39.507  29.603  40.903  1.00 26.28           W    O
ATOM   5138  O    HOH W  38      27.976  43.384 108.440  1.00 26.60           W    O
ATOM   5139  O    HOH W  39      15.808  27.157  34.475  1.00 43.88           W    O
ATOM   5140  O    HOH W  40      12.584  42.992 104.279  1.00 46.10           W    O
ATOM   5141  O    HOH W  41      34.804  47.633  78.254  1.00 32.79           W    O
ATOM   5142  O    HOH W  42      27.642  34.834  62.584  1.00 24.77           W    O
ATOM   5143  O    HOH W  43      36.584  62.345  45.774  1.00 24.67           W    O
ATOM   5144  O    HOH W  44      41.906   7.567  49.764  1.00 40.25           W    O
ATOM   5145  O    HOH W  45      26.998  50.322  77.314  1.00 38.44           W    O
ATOM   5146  O    HOH W  46      26.508  66.828  79.027  1.00 24.04           W    O
ATOM   5147  O    HOH W  47      27.119  22.719  81.301  1.00 43.04           W    O
ATOM   5148  O    HOH W  48      18.611  44.709  59.301  1.00 24.30           W    O
ATOM   5149  O    HOH W  49      36.817  31.604  44.199  1.00 45.47           W    O
ATOM   5150  O    HOH W  50      42.993  58.011  98.756  1.00 39.71           W    O
ATOM   5151  O    HOH W  51      23.099  40.340  70.072  1.00 32.55           W    O
ATOM   5152  O    HOH W  52      28.783  51.727  53.480  1.00 23.57           W    O
ATOM   5153  O    HOH W  53      36.426  48.130  81.024  1.00 27.94           W    O
ATOM   5154  O    HOH W  54      27.319  23.187  40.149  1.00 46.42           W    O
ATOM   5155  O    HOH W  55      16.054  39.188  91.189  1.00 27.75           W    O
ATOM   5156  O    HOH W  56      16.909  41.384  68.972  1.00 37.02           W    O
ATOM   5157  O    HOH W  57      27.355  43.934  62.307  1.00 30.09           W    O
```

FIG. 6-87

```
ATOM   5158  O    HOH W  58      21.903  53.438  73.576  1.00 46.74           W    O
ATOM   5159  O    HOH W  59      26.606  51.934  75.017  1.00 32.05           W    O
ATOM   5160  O    HOH W  60      27.600  31.159  56.303  1.00 34.50           W    O
ATOM   5161  O    HOH W  61      23.136  48.022  56.078  1.00 18.85           W    O
ATOM   5162  O    HOH W  62      29.544  45.688  57.642  1.00 44.18           W    O
ATOM   5163  O    HOH W  63      29.332  61.464  75.261  1.00 37.80           W    O
ATOM   5164  O    HOH W  64      30.900  49.454  77.309  1.00 57.04           W    O
ATOM   5165  O    HOH W  65       6.078  33.390  80.922  1.00 38.03           W    O
ATOM   5166  O    HOH W  66      40.212  20.720  43.696  1.00 27.79           W    O
ATOM   5167  O    HOH W  67      21.894  51.741  69.426  1.00 32.99           W    O
ATOM   5168  O    HOH W  68      21.749  42.402  69.793  1.00 17.20           W    O
ATOM   5169  O    HOH W  69       6.889  34.009  54.593  1.00 26.05           W    O
ATOM   5170  O    HOH W  70      20.193  47.911  29.110  1.00 18.73           W    O
ATOM   5171  O    HOH W  71       9.706  30.727  41.672  1.00 38.56           W    O
ATOM   5172  O    HOH W  72      35.643  43.555  99.767  1.00 56.19           W    O
ATOM   5173  O    HOH W  73      11.363  59.321  69.910  1.00 23.40           W    O
ATOM   5174  O    HOH W  74      36.659  36.969  76.675  1.00 37.35           W    O
ATOM   5175  O    HOH W  75      11.880  43.841  38.931  1.00 24.39           W    O
ATOM   5176  O    HOH W  76      42.132  52.296 112.553  1.00 36.58           W    O
ATOM   5177  O    HOH W  77      28.105  67.017  88.993  1.00 66.30           W    O
ATOM   5178  O    HOH W  78       8.451  37.166  44.627  1.00 47.12           W    O
ATOM   5179  O    HOH W  79       5.468  42.975  53.416  1.00 29.78           W    O
ATOM   5180  O    HOH W  80      16.235  28.112  48.850  1.00 27.07           W    O
ATOM   5181  O    HOH W  81      10.940  34.131  40.697  1.00 29.39           W    O
ATOM   5182  O    HOH W  82      28.730  48.582  73.292  1.00 49.76           W    O
ATOM   5183  O    HOH W  83      16.724  50.571  77.535  1.00 24.75           W    O
ATOM   5184  O    HOH W  84      32.742  37.557  68.570  1.00 29.09           W    O
ATOM   5185  O    HOH W  85      17.738  63.594  93.861  1.00 36.19           W    O
ATOM   5186  O    HOH W  86      28.035  37.039  37.905  1.00 36.51           W    O
ATOM   5187  O    HOH W  87      26.123  57.217  77.087  1.00 47.19           W    O
ATOM   5188  O    HOH W  88      44.377  59.550  94.892  1.00 27.17           W    O
ATOM   5189  O    HOH W  89      19.999  53.082  75.659  1.00 61.91           W    O
ATOM   5190  O    HOH W  90      49.638  29.061  39.391  1.00 32.08           W    O
ATOM   5191  O    HOH W  91       5.802  44.337  97.832  1.00 46.90           W    O
ATOM   5192  O    HOH W  92       6.229  48.186  98.929  1.00 35.44           W    O
ATOM   5193  O    HOH W  93      25.587  59.175  99.589  1.00 34.16           W    O
ATOM   5194  O    HOH W  94      41.158  56.390  71.372  1.00 29.53           W    O
ATOM   5195  O    HOH W  95      21.618  38.349  70.855  1.00 39.71           W    O
ATOM   5196  O    HOH W  96       2.765  40.979  79.475  1.00 21.32           W    O
ATOM   5197  O    HOH W  97      12.805  57.569  66.310  1.00 37.38           W    O
ATOM   5198  O    HOH W  98      17.056  57.174  66.071  1.00 42.50           W    O
ATOM   5199  O    HOH W  99      36.884  43.052  55.832  1.00 16.23           W    O
TER    5200       HOH W  99                                                   W
ATOM   5201  C1   12A I   1      41.595  41.642  53.375  1.00 38.54           I    C
ATOM   5202  C2   12A I   1      40.567  41.087  54.312  1.00 38.54           I    C
ATOM   5203  C3   12A I   1      40.191  39.658  54.166  1.00 38.54           I    C
ATOM   5204  C4   12A I   1      40.858  38.816  53.052  1.00 38.54           I    C
ATOM   5205  C5   12A I   1      41.871  39.344  52.194  1.00 38.54           I    C
ATOM   5206  C6   12A I   1      42.246  40.759  52.344  1.00 38.54           I    C
ATOM   5207  N11  12A I   1      39.180  39.128  55.015  1.00 38.54           I    N
ATOM   5208  C12  12A I   1      38.740  37.849  54.862  1.00 38.54           I    C
ATOM   5209  N13  12A I   1      39.484  37.165  53.967  1.00 38.54           I    N
ATOM   5210  C14  12A I   1      40.403  37.531  52.9    1.00 38.54           I    C
ATOM   5211  N15  12A I   1      40.873  36.636  52.051  1.00 38.54           I    N
ATOM   5212  C16  12A I   1      40.172  35.463  51.474  1.00 38.54           I    C
ATOM   5213  C17  12A I   1      39.277  34.574  52.246  1.00 38.54           I    C
ATOM   5214  C18  12A I   1      38.794  33.517  51.324  1.00 38.54           I    C
ATOM   5215  N19  12A I   1      39.448  33.831  50.182  1.00 38.54           I    N
ATOM   5216  N20  12A I   1      40.229  34.904  50.284  1.00 38.54           I    N
ATOM   5217  C21  12A I   1      38.831  34.481  53.660  1.00 38.54           I    C
```

FIG. 6-88

| | | | | | | | | | | | |
|---|---|---|---|---|---|---|---|---|---|---|---|
| ATOM | 5218 | C22 | 12A | I | 1 | 37.788 | 33.621 | 54.155 | 1.00 | 38.54 | I C |
| ATOM | 5219 | C23 | 12A | I | 1 | 37.324 | 32.564 | 53.200 | 1.00 | 38.54 | I C |
| ATOM | 5220 | C24 | 12A | I | 1 | 37.839 | 32.487 | 51.796 | 1.00 | 38.54 | I C |
| ATOM | 5221 | C29 | 12A | I | 1 | 37.817 | 37.229 | 55.744 | 1.00 | 38.54 | I C |
| ATOM | 5222 | C30 | 12A | I | 1 | 38.134 | 36.851 | 57.114 | 1.00 | 38.54 | I C |
| ATOM | 5223 | C31 | 12A | I | 1 | 37.009 | 36.379 | 57.992 | 1.00 | 38.54 | I C |
| ATOM | 5224 | C32 | 12A | I | 1 | 35.643 | 36.244 | 57.450 | 1.00 | 38.54 | I C |
| ATOM | 5225 | C33 | 12A | I | 1 | 35.372 | 36.591 | 56.012 | 1.00 | 38.54 | I C |
| ATOM | 5226 | C34 | 12A | I | 1 | 36.501 | 37.087 | 55.181 | 1.00 | 38.54 | I C |
| ATOM | 5227 | C39 | 12A | I | 1 | 39.518 | 36.900 | 57.738 | 1.00 | 38.54 | I C |
| ATOM | 5228 | F40 | 12A | I | 1 | 39.832 | 35.670 | 58.027 | 1.00 | 38.54 | I F |
| ATOM | 5229 | F41 | 12A | I | 1 | 39.470 | 37.659 | 58.853 | 1.00 | 38.54 | I F |
| ATOM | 5230 | F42 | 12A | I | 1 | 40.508 | 37.437 | 56.949 | 1.00 | 38.54 | I F |
| TER | 5231 | | 12A | I | 1 | | | | | | I |
| ATOM | 5232 | C1 | 12B | J | 1 | 28.164 | 61.927 | 79.557 | 1.00 | 38.48 | J C |
| ATOM | 5233 | C2 | 12B | J | 1 | 27.275 | 60.912 | 78.898 | 1.00 | 38.48 | J C |
| ATOM | 5234 | C3 | 12B | J | 1 | 25.827 | 60.876 | 79.289 | 1.00 | 38.48 | J C |
| ATOM | 5235 | C4 | 12B | J | 1 | 25.300 | 61.898 | 80.352 | 1.00 | 38.48 | J C |
| ATOM | 5236 | C5 | 12B | J | 1 | 26.153 | 62.897 | 80.970 | 1.00 | 38.48 | J C |
| ATOM | 5237 | C6 | 12B | J | 1 | 27.583 | 62.920 | 80.543 | 1.00 | 38.48 | J C |
| ATOM | 5238 | N11 | 12B | J | 1 | 24.996 | 59.871 | 78.752 | 1.00 | 38.48 | J N |
| ATOM | 5239 | C12 | 12B | J | 1 | 23.721 | 59.743 | 79.164 | 1.00 | 38.48 | J C |
| ATOM | 5240 | N13 | 12B | J | 1 | 23.313 | 60.777 | 79.957 | 1.00 | 38.48 | J N |
| ATOM | 5241 | C14 | 12B | J | 1 | 23.972 | 61.744 | 80.661 | 1.00 | 38.48 | J C |
| ATOM | 5242 | N15 | 12B | J | 1 | 23.333 | 62.535 | 81.572 | 1.00 | 38.48 | J N |
| ATOM | 5243 | C16 | 12B | J | 1 | 22.227 | 62.185 | 82.473 | 1.00 | 38.48 | J C |
| ATOM | 5244 | C17 | 12B | J | 1 | 21.052 | 61.421 | 82.024 | 1.00 | 38.48 | J C |
| ATOM | 5245 | C18 | 12B | J | 1 | 20.124 | 61.295 | 83.172 | 1.00 | 38.48 | J C |
| ATOM | 5246 | N19 | 12B | J | 1 | 20.804 | 61.972 | 84.134 | 1.00 | 38.48 | J N |
| ATOM | 5247 | N20 | 12B | J | 1 | 21.979 | 62.488 | 83.726 | 1.00 | 38.48 | J N |
| ATOM | 5248 | C21 | 12B | J | 1 | 20.592 | 60.821 | 80.721 | 1.00 | 38.48 | J C |
| ATOM | 5249 | C22 | 12B | J | 1 | 19.403 | 60.017 | 80.537 | 1.00 | 38.48 | J C |
| ATOM | 5250 | C23 | 12B | J | 1 | 18.503 | 59.923 | 81.721 | 1.00 | 38.48 | J C |
| ATOM | 5251 | C24 | 12B | J | 1 | 18.840 | 60.558 | 83.033 | 1.00 | 38.48 | J C |
| ATOM | 5252 | C29 | 12B | J | 1 | 22.808 | 58.858 | 78.496 | 1.00 | 38.48 | J C |
| ATOM | 5253 | C30 | 12B | J | 1 | 22.261 | 59.070 | 77.113 | 1.00 | 38.48 | J C |
| ATOM | 5254 | C31 | 12B | J | 1 | 21.446 | 57.955 | 76.507 | 1.00 | 38.48 | J C |
| ATOM | 5255 | C32 | 12B | J | 1 | 21.117 | 56.757 | 77.302 | 1.00 | 38.48 | J C |
| ATOM | 5256 | C33 | 12B | J | 1 | 21.638 | 56.637 | 78.706 | 1.00 | 38.48 | J C |
| ATOM | 5257 | C34 | 12B | J | 1 | 22.496 | 57.711 | 79.287 | 1.00 | 38.48 | J C |
| ATOM | 5258 | C39 | 12B | J | 1 | 22.493 | 60.360 | 76.292 | 1.00 | 38.48 | J C |
| ATOM | 5259 | F40 | 12B | J | 1 | 23.050 | 61.351 | 76.922 | 1.00 | 38.48 | J F |
| ATOM | 5260 | F41 | 12B | J | 1 | 21.334 | 60.883 | 75.995 | 1.00 | 38.48 | J F |
| ATOM | 5261 | F42 | 12B | J | 1 | 23.275 | 60.056 | 75.224 | 1.00 | 38.48 | J F |
| TER | 5262 | | 12B | J | 1 | | | | | | J |
| END | | | | | | | | | | | |

FIG. 7-1

|  | Atom Type | Resid |  | # | X | Y | Z | OCC | B |  |
|---|---|---|---|---|---|---|---|---|---|---|
| ATOM | 1 | CB | VAL A | 37 | 1.918 | 33.912 | 12.559 | 1.00 | 42.12 | C |
| ATOM | 2 | CG1 | VAL A | 37 | 2.177 | 34.532 | 13.927 | 1.00 | 42.12 | C |
| ATOM | 3 | CG2 | VAL A | 37 | 2.837 | 34.529 | 11.500 | 1.00 | 42.12 | C |
| ATOM | 4 | C | VAL A | 37 | 1.443 | 31.855 | 13.860 | 1.00 | 53.45 | C |
| ATOM | 5 | O | VAL A | 37 | 0.232 | 31.634 | 13.845 | 1.00 | 53.45 | O |
| ATOM | 6 | N | VAL A | 37 | 1.733 | 31.713 | 11.355 | 1.00 | 53.45 | N |
| ATOM | 7 | CA | VAL A | 37 | 2.155 | 32.392 | 12.623 | 1.00 | 53.45 | C |
| ATOM | 8 | N | THR A | 38 | 2.202 | 31.664 | 14.936 | 1.00 | 52.22 | N |
| ATOM | 9 | CA | THR A | 38 | 1.640 | 31.130 | 16.171 | 1.00 | 52.22 | C |
| ATOM | 10 | CB | THR A | 38 | 2.243 | 29.757 | 16.518 | 1.00 | 59.61 | C |
| ATOM | 11 | OG1 | THR A | 38 | 2.046 | 28.857 | 15.422 | 1.00 | 59.61 | O |
| ATOM | 12 | CG2 | THR A | 38 | 1.573 | 29.175 | 17.756 | 1.00 | 59.61 | C |
| ATOM | 13 | C | THR A | 38 | 1.858 | 32.047 | 17.352 | 1.00 | 52.22 | C |
| ATOM | 14 | O | THR A | 38 | 2.901 | 32.693 | 17.464 | 1.00 | 52.22 | O |
| ATOM | 15 | N | THR A | 39 | 0.862 | 32.090 | 18.233 | 1.00 | 39.26 | N |
| ATOM | 16 | CA | THR A | 39 | 0.929 | 32.929 | 19.427 | 1.00 | 39.26 | C |
| ATOM | 17 | CB | THR A | 39 | 0.003 | 34.152 | 19.303 | 1.00 | 43.32 | C |
| ATOM | 18 | OG1 | THR A | 39 | 0.351 | 34.890 | 18.127 | 1.00 | 43.32 | O |
| ATOM | 19 | CG2 | THR A | 39 | 0.153 | 35.062 | 20.510 | 1.00 | 43.32 | C |
| ATOM | 20 | C | THR A | 39 | 0.550 | 32.143 | 20.678 | 1.00 | 39.26 | C |
| ATOM | 21 | O | THR A | 39 | 0.407 | 31.381 | 20.671 | 1.00 | 39.26 | O |
| ATOM | 22 | N | VAL A | 40 | 1.318 | 32.323 | 21.747 | 1.00 | 35.33 | N |
| ATOM | 23 | CA | VAL A | 40 | 1.054 | 31.623 | 22.994 | 1.00 | 35.33 | C |
| ATOM | 24 | CB | VAL A | 40 | 1.896 | 30.317 | 23.113 | 1.00 | 33.55 | C |
| ATOM | 25 | CG1 | VAL A | 40 | 1.580 | 29.381 | 21.969 | 1.00 | 33.55 | C |
| ATOM | 26 | CG2 | VAL A | 40 | 3.376 | 30.647 | 23.126 | 1.00 | 33.55 | C |
| ATOM | 27 | C | VAL A | 40 | 1.377 | 32.500 | 24.193 | 1.00 | 35.33 | C |
| ATOM | 28 | O | VAL A | 40 | 1.861 | 33.624 | 24.057 | 1.00 | 35.33 | O |
| ATOM | 29 | N | VAL A | 41 | 1.084 | 31.980 | 25.373 | 1.00 | 39.77 | N |
| ATOM | 30 | CA | VAL A | 41 | 1.381 | 32.697 | 26.593 | 1.00 | 39.77 | C |
| ATOM | 31 | CB | VAL A | 41 | 0.147 | 32.807 | 27.510 | 1.00 | 31.47 | C |
| ATOM | 32 | CG1 | VAL A | 41 | 0.518 | 33.580 | 28.763 | 1.00 | 31.47 | C |
| ATOM | 33 | CG2 | VAL A | 41 | -1.010 | 33.453 | 26.756 | 1.00 | 31.47 | C |
| ATOM | 34 | C | VAL A | 41 | 2.435 | 31.827 | 27.252 | 1.00 | 39.77 | C |
| ATOM | 35 | O | VAL A | 41 | 2.147 | 30.718 | 27.723 | 1.00 | 39.77 | O |
| ATOM | 36 | N | ALA A | 42 | 3.664 | 32.324 | 27.260 | 1.00 | 37.34 | N |
| ATOM | 37 | CA | ALA A | 42 | 4.767 | 31.568 | 27.830 | 1.00 | 37.34 | C |
| ATOM | 38 | CB | ALA A | 42 | 5.815 | 31.290 | 26.734 | 1.00 | 21.39 | C |
| ATOM | 39 | C | ALA A | 42 | 5.392 | 32.308 | 29.008 | 1.00 | 37.34 | C |
| ATOM | 40 | O | ALA A | 42 | 5.167 | 33.503 | 29.185 | 1.00 | 37.34 | O |
| ATOM | 41 | N | THR A | 43 | 6.172 | 31.589 | 29.807 | 1.00 | 44.44 | N |
| ATOM | 42 | CA | THR A | 43 | 6.839 | 32.160 | 30.973 | 1.00 | 44.44 | C |
| ATOM | 43 | CB | THR A | 43 | 6.501 | 31.338 | 32.227 | 1.00 | 33.32 | C |
| ATOM | 44 | OG1 | THR A | 43 | 5.088 | 31.369 | 32.455 | 1.00 | 33.32 | O |
| ATOM | 45 | CG2 | THR A | 43 | 7.238 | 31.871 | 33.434 | 1.00 | 33.32 | C |
| ATOM | 46 | C | THR A | 43 | 8.354 | 32.117 | 30.756 | 1.00 | 44.44 | C |
| ATOM | 47 | O | THR A | 43 | 8.890 | 31.111 | 30.328 | 1.00 | 44.44 | O |
| ATOM | 48 | N | PRO A | 44 | 9.078 | 33.201 | 31.062 | 1.00 | 38.15 | N |
| ATOM | 49 | CD | PRO A | 44 | 8.753 | 34.418 | 31.812 | 1.00 | 42.08 | C |
| ATOM | 50 | CA | PRO A | 44 | 10.523 | 33.074 | 30.829 | 1.00 | 38.15 | C |
| ATOM | 51 | CB | PRO A | 44 | 11.067 | 34.480 | 31.048 | 1.00 | 42.08 | C |
| ATOM | 52 | CG | PRO A | 44 | 9.896 | 35.289 | 31.518 | 1.00 | 42.08 | C |
| ATOM | 53 | C | PRO A | 44 | 11.156 | 32.091 | 31.795 | 1.00 | 38.15 | C |
| ATOM | 54 | O | PRO A | 44 | 10.600 | 31.813 | 32.853 | 1.00 | 38.15 | O |
| ATOM | 55 | N | GLY A | 45 | 12.309 | 31.551 | 31.418 | 1.00 | 36.57 | N |
| ATOM | 56 | CA | GLY A | 45 | 12.982 | 30.573 | 32.249 | 1.00 | 36.57 | C |
| ATOM | 57 | C | GLY A | 45 | 13.647 | 31.080 | 33.508 | 1.00 | 36.57 | C |

FIG. 7-2

```
ATOM     58  O   GLY A  45      13.574  30.406  34.542  1.00 36.57           O
ATOM     59  N   ALA A  46      14.280  32.251  33.436  1.00 62.30           N
ATOM     60  CA  ALA A  46      15.035  32.785  34.568  1.00 62.30           C
ATOM     61  CB  ALA A  46      16.488  32.991  34.145  1.00 63.64           C
ATOM     62  C   ALA A  46      14.492  34.062  35.201  1.00 62.30           C
ATOM     63  O   ALA A  46      14.530  34.197  36.428  1.00 62.30           O
ATOM     64  N   GLY A  47      13.974  34.984  34.388  1.00 90.60           N
ATOM     65  CA  GLY A  47      13.463  36.240  34.918  1.00 90.60           C
ATOM     66  C   GLY A  47      12.381  35.986  35.938  1.00 90.60           C
ATOM     67  O   GLY A  47      12.415  34.998  36.661  1.00 90.60           O
ATOM     68  N   PRO A  48      11.379  36.851  36.015  1.00 87.43           N
ATOM     69  CD  PRO A  48      11.181  38.126  35.308  1.00 75.51           C
ATOM     70  CA  PRO A  48      10.329  36.607  37.007  1.00 87.43           C
ATOM     71  CB  PRO A  48       9.708  37.971  37.167  1.00 75.51           C
ATOM     72  CG  PRO A  48       9.822  38.503  35.746  1.00 75.51           C
ATOM     73  C   PRO A  48       9.325  35.595  36.525  1.00 87.43           C
ATOM     74  O   PRO A  48       9.304  35.259  35.350  1.00 87.43           O
ATOM     75  N   ASP A  49       8.506  35.067  37.417  1.00 61.52           N
ATOM     76  CA  ASP A  49       7.541  34.116  36.913  1.00 61.52           C
ATOM     77  CB  ASP A  49       7.181  33.047  37.953  1.00 58.30           C
ATOM     78  CG  ASP A  49       6.498  31.838  37.320  1.00 58.30           C
ATOM     79  OD1 ASP A  49       6.743  30.691  37.782  1.00 58.30           O
ATOM     80  OD2 ASP A  49       5.718  32.069  36.358  1.00 58.30           O
ATOM     81  C   ASP A  49       6.360  34.966  36.550  1.00 61.52           C
ATOM     82  O   ASP A  49       5.492  35.196  37.383  1.00 61.52           O
ATOM     83  N   ARG A  50       6.389  35.500  35.328  1.00 65.48           N
ATOM     84  CA  ARG A  50       5.316  36.356  34.833  1.00 65.48           C
ATOM     85  CB  ARG A  50       5.703  37.824  34.944  1.00 92.34           C
ATOM     86  CG  ARG A  50       4.572  38.688  35.482  1.00 92.34           C
ATOM     87  CD  ARG A  50       4.777  40.130  35.077  1.00 92.34           C
ATOM     88  NE  ARG A  50       4.258  41.091  36.055  1.00 92.34           N
ATOM     89  CZ  ARG A  50       3.053  41.677  36.021  1.00 92.34           C
ATOM     90  NH1 ARG A  50       2.168  41.427  35.044  1.00 92.34           N
ATOM     91  NH2 ARG A  50       2.726  42.542  36.978  1.00 92.34           N
ATOM     92  C   ARG A  50       5.024  36.027  33.374  1.00 65.48           C
ATOM     93  O   ARG A  50       5.807  36.337  32.487  1.00 65.48           O
ATOM     94  N   PRO A  51       3.871  35.413  33.100  1.00 33.34           N
ATOM     95  CD  PRO A  51       2.758  35.214  34.034  1.00 36.17           C
ATOM     96  CA  PRO A  51       3.485  35.040  31.732  1.00 33.34           C
ATOM     97  CB  PRO A  51       2.078  34.479  31.894  1.00 36.17           C
ATOM     98  CG  PRO A  51       1.958  34.200  33.326  1.00 36.17           C
ATOM     99  C   PRO A  51       3.487  36.206  30.755  1.00 33.34           C
ATOM    100  O   PRO A  51       3.142  37.341  31.102  1.00 33.34           O
ATOM    101  N   GLN A  52       3.876  35.932  29.523  1.00 55.88           N
ATOM    102  CA  GLN A  52       3.889  36.974  28.507  1.00 55.88           C
ATOM    103  CB  GLN A  52       5.256  37.630  28.385  1.00 32.84           C
ATOM    104  CG  GLN A  52       6.321  36.806  27.693  1.00 32.84           C
ATOM    105  CD  GLN A  52       7.660  37.534  27.685  1.00 32.84           C
ATOM    106  OE1 GLN A  52       8.092  38.059  26.653  1.00 32.84           O
ATOM    107  NE2 GLN A  52       8.326  37.566  28.838  1.00 32.84           N
ATOM    108  C   GLN A  52       3.573  36.280  27.221  1.00 55.88           C
ATOM    109  O   GLN A  52       3.757  35.058  27.101  1.00 55.88           O
ATOM    110  N   GLU A  53       3.048  37.030  26.264  1.00 57.27           N
ATOM    111  CA  GLU A  53       2.767  36.379  25.002  1.00 57.27           C
ATOM    112  CB  GLU A  53       1.492  36.914  24.357  1.00 68.20           C
ATOM    113  CG  GLU A  53       1.706  37.689  23.118  1.00 68.20           C
ATOM    114  CD  GLU A  53       0.448  38.317  22.668  1.00 68.20           C
ATOM    115  OE1 GLU A  53      -0.525  38.355  23.471  1.00 68.20           O
ATOM    116  OE2 GLU A  53       0.466  38.767  21.512  1.00 68.20           O
ATOM    117  C   GLU A  53       3.964  36.469  24.057  1.00 57.27           C
```

FIG. 7-3

```
ATOM    118  O    GLU A  53       4.618   37.509   23.890  1.00 57.27           O
ATOM    119  N    VAL A  54       4.247   35.325   23.460  1.00 47.62           N
ATOM    120  CA   VAL A  54       5.350   35.169   22.542  1.00 47.62           C
ATOM    121  CB   VAL A  54       6.369   34.171   23.126  1.00 67.98           C
ATOM    122  CG1  VAL A  54       7.589   34.078   22.247  1.00 67.98           C
ATOM    123  CG2  VAL A  54       6.740   34.589   24.537  1.00 67.98           C
ATOM    124  C    VAL A  54       4.805   34.621   21.223  1.00 47.62           C
ATOM    125  O    VAL A  54       4.025   33.661   21.204  1.00 47.62           O
ATOM    126  N    SER A  55       5.197   35.242   20.118  1.00 38.73           N
ATOM    127  CA   SER A  55       4.747   34.788   18.813  1.00 38.73           C
ATOM    128  CB   SER A  55       3.940   35.870   18.119  1.00 74.91           C
ATOM    129  OG   SER A  55       2.651   35.957   18.688  1.00 74.91           O
ATOM    130  C    SER A  55       5.918   34.410   17.942  1.00 38.73           C
ATOM    131  O    SER A  55       6.924   35.121   17.879  1.00 38.73           O
ATOM    132  N    TYR A  56       5.784   33.289   17.258  1.00 48.72           N
ATOM    133  CA   TYR A  56       6.856   32.837   16.407  1.00 48.72           C
ATOM    134  CB   TYR A  56       7.643   31.725   17.094  1.00 43.32           C
ATOM    135  CG   TYR A  56       6.822   30.515   17.438  1.00 43.32           C
ATOM    136  CD1  TYR A  56       6.523   29.570   16.465  1.00 43.32           C
ATOM    137  CE1  TYR A  56       5.780   28.450   16.763  1.00 43.32           C
ATOM    138  CD2  TYR A  56       6.344   30.311   18.736  1.00 43.32           C
ATOM    139  CE2  TYR A  56       5.594   29.190   19.051  1.00 43.32           C
ATOM    140  CZ   TYR A  56       5.317   28.258   18.057  1.00 43.32           C
ATOM    141  OH   TYR A  56       4.601   27.117   18.355  1.00 43.32           O
ATOM    142  C    TYR A  56       6.252   32.349   15.121  1.00 48.72           C
ATOM    143  O    TYR A  56       5.048   32.462   14.913  1.00 48.72           O
ATOM    144  N    THR A  57       7.088   31.790   14.260  1.00 96.81           N
ATOM    145  CA   THR A  57       6.608   31.330   12.977  1.00 96.81           C
ATOM    146  CB   THR A  57       6.274   32.555   12.116  1.00 76.27           C
ATOM    147  OG1  THR A  57       5.608   32.141   10.919  1.00 76.27           O
ATOM    148  CG2  THR A  57       7.552   33.327   11.790  1.00 76.27           C
ATOM    149  C    THR A  57       7.669   30.469   12.294  1.00 96.81           C
ATOM    150  O    THR A  57       8.776   30.312   12.817  1.00 96.81           O
ATOM    151  N    ASP A  58       7.332   29.913   11.132  1.00 56.40           N
ATOM    152  CA   ASP A  58       8.269   29.066   10.401  1.00 56.40           C
ATOM    153  CB   ASP A  58       9.508   29.865    9.998  1.00 93.62           C
ATOM    154  CG   ASP A  58       9.244   30.808    8.846  1.00 93.62           C
ATOM    155  OD1  ASP A  58       8.976   30.320    7.727  1.00 93.62           O
ATOM    156  OD2  ASP A  58       9.300   32.039    9.055  1.00 93.62           O
ATOM    157  C    ASP A  58       8.692   27.880   11.262  1.00 56.40           C
ATOM    158  O    ASP A  58       9.885   27.604   11.409  1.00 56.40           O
ATOM    159  N    THR A  59       7.709   27.188   11.832  1.00 71.62           N
ATOM    160  CA   THR A  59       7.972   26.028   12.681  1.00 71.62           C
ATOM    161  CB   THR A  59       6.778   25.758   13.614  1.00 73.90           C
ATOM    162  OG1  THR A  59       6.460   26.962   14.324  1.00 73.90           O
ATOM    163  CG2  THR A  59       7.118   24.671   14.619  1.00 73.90           C
ATOM    164  C    THR A  59       8.236   24.799   11.813  1.00 71.62           C
ATOM    165  O    THR A  59       7.418   24.446   10.970  1.00 71.62           O
ATOM    166  N    LYS A  60       9.370   24.142   12.028  1.00 49.31           N
ATOM    167  CA   LYS A  60       9.738   22.982   11.221  1.00 49.31           C
ATOM    168  CB   LYS A  60      10.773   23.389   10.175  1.00 73.59           C
ATOM    169  CG   LYS A  60      10.884   24.903    9.980  1.00 73.59           C
ATOM    170  CD   LYS A  60      12.291   25.346    9.624  1.00 73.59           C
ATOM    171  CE   LYS A  60      12.678   24.889    8.244  1.00 73.59           C
ATOM    172  NZ   LYS A  60      13.424   25.970    7.537  1.00 73.59           N
ATOM    173  C    LYS A  60      10.348   21.949   12.139  1.00 49.31           C
ATOM    174  O    LYS A  60      11.047   22.309   13.076  1.00 49.31           O
ATOM    175  N    VAL A  61      10.114   20.672   11.884  1.00 43.56           N
ATOM    176  CA   VAL A  61      10.674   19.672   12.782  1.00 43.56           C
ATOM    177  CB   VAL A  61       9.949   18.325   12.659  1.00 33.04           C
```

FIG. 7-4

```
ATOM    178  CG1 VAL A  61      10.198  17.504  13.917  1.00 33.04           C
ATOM    179  CG2 VAL A  61       8.450  18.560  12.420  1.00 33.04           C
ATOM    180  C   VAL A  61      12.157  19.461  12.522  1.00 43.56           C
ATOM    181  O   VAL A  61      12.604  19.533  11.376  1.00 43.56           O
ATOM    182  N   ILE A  62      12.914  19.222  13.590  1.00 45.16           N
ATOM    183  CA  ILE A  62      14.336  18.992  13.489  1.00 45.16           C
ATOM    184  CB  ILE A  62      15.167  20.315  13.777  1.00 36.34           C
ATOM    185  CG2 ILE A  62      14.891  21.367  12.719  1.00 36.34           C
ATOM    186  CG1 ILE A  62      14.768  20.920  15.110  1.00 36.34           C
ATOM    187  CD1 ILE A  62      15.423  22.307  15.347  1.00 36.34           C
ATOM    188  C   ILE A  62      14.826  17.833  14.379  1.00 45.16           C
ATOM    189  O   ILE A  62      15.547  17.018  13.866  1.00 45.16           O
ATOM    190  N   GLY A  63      14.416  17.678  15.638  1.00 39.89           N
ATOM    191  CA  GLY A  63      15.002  16.592  16.417  1.00 39.89           C
ATOM    192  C   GLY A  63      14.038  15.510  16.891  1.00 39.89           C
ATOM    193  O   GLY A  63      12.895  15.775  17.217  1.00 39.89           O
ATOM    194  N   ASN A  64      14.603  14.321  17.140  1.00 43.43           N
ATOM    195  CA  ASN A  64      13.774  13.276  17.691  1.00 43.43           C
ATOM    196  CB  ASN A  64      13.378  12.229  16.672  1.00 74.61           C
ATOM    197  CG  ASN A  64      12.242  12.746  15.736  1.00 74.61           C
ATOM    198  OD1 ASN A  64      11.397  11.970  15.281  1.00 74.61           O
ATOM    199  ND2 ASN A  64      12.256  14.059  15.424  1.00 74.61           N
ATOM    200  C   ASN A  64      14.154  12.638  18.983  1.00 43.43           C
ATOM    201  O   ASN A  64      13.548  12.987  19.961  1.00 43.43           O
ATOM    202  N   GLY A  65      15.022  11.642  18.992  1.00 30.93           N
ATOM    203  CA  GLY A  65      15.356  11.005  20.244  1.00 30.93           C
ATOM    204  C   GLY A  65      14.172  10.448  21.023  1.00 30.93           C
ATOM    205  O   GLY A  65      13.021  10.568  20.610  1.00 30.93           O
ATOM    206  N   SER A  66      14.495   9.771  22.122  1.00 80.13           N
ATOM    207  CA  SER A  66      13.514   9.137  22.994  1.00 80.13           C
ATOM    208  CB  SER A  66      14.069   8.969  24.400  1.00 68.64           C
ATOM    209  OG  SER A  66      15.063   7.973  24.408  1.00 68.64           O
ATOM    210  C   SER A  66      12.156   9.819  23.127  1.00 80.13           C
ATOM    211  O   SER A  66      11.242   9.537  22.350  1.00 80.13           O
ATOM    212  N   ALA A  67      12.001  10.661  24.152  1.00 76.33           N
ATOM    213  CA  ALA A  67      10.719  11.299  24.418  1.00 76.33           C
ATOM    214  CB  ALA A  67      10.342  11.064  25.863  1.00 58.91           C
ATOM    215  C   ALA A  67      10.763  12.780  24.122  1.00 76.33           C
ATOM    216  O   ALA A  67      11.407  13.545  24.833  1.00 76.33           O
ATOM    217  N   GLY A  68      10.087  13.180  23.058  1.00 66.99           N
ATOM    218  CA  GLY A  68      10.051  14.585  22.728  1.00 66.99           C
ATOM    219  C   GLY A  68      10.647  15.038  21.418  1.00 66.99           C
ATOM    220  O   GLY A  68      11.859  14.933  21.159  1.00 66.99           O
ATOM    221  N   VAL A  69       9.799  15.586  20.569  1.00 47.39           N
ATOM    222  CA  VAL A  69      10.331  16.072  19.315  1.00 47.39           C
ATOM    223  CB  VAL A  69       9.363  15.755  18.129  1.00 51.90           C
ATOM    224  CG1 VAL A  69       9.372  16.869  17.066  1.00 51.90           C
ATOM    225  CG2 VAL A  69       9.821  14.444  17.428  1.00 51.90           C
ATOM    226  C   VAL A  69      10.624  17.555  19.444  1.00 47.39           C
ATOM    227  O   VAL A  69       9.935  18.274  20.161  1.00 47.39           O
ATOM    228  N   VAL A  70      11.640  17.991  18.714  1.00 39.11           N
ATOM    229  CA  VAL A  70      12.103  19.364  18.762  1.00 39.11           C
ATOM    230  CB  VAL A  70      13.628  19.390  19.068  1.00 46.74           C
ATOM    231  CG1 VAL A  70      14.167  20.798  19.020  1.00 46.74           C
ATOM    232  CG2 VAL A  70      13.890  18.763  20.431  1.00 46.74           C
ATOM    233  C   VAL A  70      11.832  20.025  17.419  1.00 39.11           C
ATOM    234  O   VAL A  70      12.084  19.446  16.354  1.00 39.11           O
ATOM    235  N   TYR A  71      11.294  21.237  17.485  1.00 46.83           N
ATOM    236  CA  TYR A  71      10.977  22.007  16.299  1.00 46.83           C
ATOM    237  CB  TYR A  71       9.528  22.501  16.359  1.00 53.95           C
```

FIG. 7-5

```
ATOM    238  CG   TYR A  71       8.458  21.427  16.400  1.00 53.95           C
ATOM    239  CD1  TYR A  71       8.419  20.479  17.425  1.00 53.95           C
ATOM    240  CE1  TYR A  71       7.399  19.520  17.482  1.00 53.95           C
ATOM    241  CD2  TYR A  71       7.450  21.392  15.430  1.00 53.95           C
ATOM    242  CE2  TYR A  71       6.426  20.447  15.478  1.00 53.95           C
ATOM    243  CZ   TYR A  71       6.405  19.513  16.505  1.00 53.95           C
ATOM    244  OH   TYR A  71       5.387  18.583  16.548  1.00 53.95           O
ATOM    245  C    TYR A  71      11.907  23.211  16.259  1.00 46.83           C
ATOM    246  O    TYR A  71      12.634  23.479  17.210  1.00 46.83           O
ATOM    247  N    GLN A  72      11.861  23.941  15.156  1.00 51.45           N
ATOM    248  CA   GLN A  72      12.676  25.136  14.971  1.00 51.45           C
ATOM    249  CB   GLN A  72      13.730  24.884  13.892  1.00 78.04           C
ATOM    250  CG   GLN A  72      14.722  26.021  13.671  1.00 78.04           C
ATOM    251  CD   GLN A  72      14.392  26.865  12.458  1.00 78.04           C
ATOM    252  OE1  GLN A  72      13.460  27.669  12.478  1.00 78.04           O
ATOM    253  NE2  GLN A  72      15.155  26.679  11.385  1.00 78.04           N
ATOM    254  C    GLN A  72      11.717  26.239  14.534  1.00 51.45           C
ATOM    255  O    GLN A  72      10.863  26.013  13.678  1.00 51.45           O
ATOM    256  N    ALA A  73      11.847  27.426  15.121  1.00 39.89           N
ATOM    257  CA   ALA A  73      10.953  28.531  14.791  1.00 39.89           C
ATOM    258  CB   ALA A  73       9.811  28.588  15.788  1.00 60.92           C
ATOM    259  C    ALA A  73      11.659  29.867  14.760  1.00 39.89           C
ATOM    260  O    ALA A  73      12.873  29.945  14.949  1.00 39.89           O
ATOM    261  N    LYS A  74      10.883  30.923  14.533  1.00 46.58           N
ATOM    262  CA   LYS A  74      11.435  32.266  14.469  1.00 46.58           C
ATOM    263  CB   LYS A  74      11.625  32.675  13.006  1.00 90.82           C
ATOM    264  CG   LYS A  74      12.349  34.004  12.807  1.00 90.82           C
ATOM    265  CD   LYS A  74      11.381  35.145  12.546  1.00 90.82           C
ATOM    266  CE   LYS A  74      11.662  35.819  11.213  1.00 90.82           C
ATOM    267  NZ   LYS A  74      11.393  34.932  10.047  1.00 90.82           N
ATOM    268  C    LYS A  74      10.577  33.303  15.189  1.00 46.58           C
ATOM    269  O    LYS A  74       9.490  33.667  14.729  1.00 46.58           O
ATOM    270  N    LEU A  75      11.070  33.770  16.329  1.00 70.67           N
ATOM    271  CA   LEU A  75      10.367  34.781  17.101  1.00 70.67           C
ATOM    272  CB   LEU A  75      11.245  35.258  18.259  1.00 47.72           C
ATOM    273  CG   LEU A  75      11.844  34.145  19.114  1.00 47.72           C
ATOM    274  CD1  LEU A  75      12.721  34.743  20.205  1.00 47.72           C
ATOM    275  CD2  LEU A  75      10.724  33.312  19.704  1.00 47.72           C
ATOM    276  C    LEU A  75      10.109  35.931  16.143  1.00 70.67           C
ATOM    277  O    LEU A  75      10.929  36.205  15.268  1.00 70.67           O
ATOM    278  N    CYS A  76       8.979  36.608  16.311  1.00 63.01           N
ATOM    279  CA   CYS A  76       8.628  37.715  15.433  1.00 63.01           C
ATOM    280  CB   CYS A  76       7.115  37.822  15.341  1.00 56.47           C
ATOM    281  SG   CYS A  76       6.376  36.251  14.858  1.00 56.47           S
ATOM    282  C    CYS A  76       9.227  39.042  15.868  1.00 63.01           C
ATOM    283  O    CYS A  76       9.762  39.778  15.048  1.00 63.01           O
ATOM    284  N    ASP A  77       9.159  39.331  17.161  1.00 82.56           N
ATOM    285  CA   ASP A  77       9.684  40.577  17.717  1.00 82.56           C
ATOM    286  CB   ASP A  77       9.403  40.619  19.218  1.00 98.35           C
ATOM    287  CG   ASP A  77      10.123  39.519  19.965  1.00 98.35           C
ATOM    288  OD1  ASP A  77      10.839  38.730  19.315  1.00 98.35           O
ATOM    289  OD2  ASP A  77       9.978  39.435  21.201  1.00 98.35           O
ATOM    290  C    ASP A  77      11.186  40.826  17.494  1.00 82.56           C
ATOM    291  O    ASP A  77      11.669  41.942  17.705  1.00 82.56           O
ATOM    292  N    SER A  78      11.928  39.802  17.081  1.00 56.03           N
ATOM    293  CA   SER A  78      13.366  39.963  16.870  1.00 56.03           C
ATOM    294  CB   SER A  78      14.131  39.469  18.099  1.00 73.70           C
ATOM    295  OG   SER A  78      13.805  38.119  18.377  1.00 73.70           O
ATOM    296  C    SER A  78      13.854  39.218  15.639  1.00 56.03           C
ATOM    297  O    SER A  78      14.887  39.553  15.066  1.00 56.03           O
```

FIG. 7-6

```
ATOM    298  N    GLY A  79      13.101  38.207  15.235  1.00 44.63           N
ATOM    299  CA   GLY A  79      13.488  37.440  14.074  1.00 44.63           C
ATOM    300  C    GLY A  79      14.506  36.393  14.463  1.00 44.63           C
ATOM    301  O    GLY A  79      15.034  35.704  13.598  1.00 44.63           O
ATOM    302  N    GLU A  80      14.775  36.266  15.762  1.00 40.60           N
ATOM    303  CA   GLU A  80      15.742  35.292  16.253  1.00 40.60           C
ATOM    304  CB   GLU A  80      16.004  35.484  17.751  1.00 68.27           C
ATOM    305  CG   GLU A  80      16.276  36.909  18.174  1.00 68.27           C
ATOM    306  CD   GLU A  80      16.439  37.033  19.672  1.00 68.27           C
ATOM    307  OE1  GLU A  80      15.914  38.012  20.252  1.00 68.27           O
ATOM    308  OE2  GLU A  80      17.099  36.152  20.266  1.00 68.27           O
ATOM    309  C    GLU A  80      15.258  33.865  16.020  1.00 40.60           C
ATOM    310  O    GLU A  80      14.056  33.579  16.072  1.00 40.60           O
ATOM    311  N    LEU A  81      16.212  32.979  15.749  1.00 62.69           N
ATOM    312  CA   LEU A  81      15.932  31.569  15.532  1.00 62.69           C
ATOM    313  CB   LEU A  81      17.016  30.937  14.665  1.00 53.78           C
ATOM    314  CG   LEU A  81      16.710  30.915  13.174  1.00 53.78           C
ATOM    315  CD1  LEU A  81      17.932  30.456  12.423  1.00 53.78           C
ATOM    316  CD2  LEU A  81      15.537  29.987  12.911  1.00 53.78           C
ATOM    317  C    LEU A  81      15.915  30.893  16.889  1.00 62.69           C
ATOM    318  O    LEU A  81      16.831  31.071  17.699  1.00 62.69           O
ATOM    319  N    VAL A  82      14.867  30.127  17.150  1.00 33.64           N
ATOM    320  CA   VAL A  82      14.777  29.440  18.420  1.00 33.64           C
ATOM    321  CB   VAL A  82      13.688  30.061  19.340  1.00 30.34           C
ATOM    322  CG1  VAL A  82      14.026  31.499  19.635  1.00 30.34           C
ATOM    323  CG2  VAL A  82      12.321  29.981  18.684  1.00 30.34           C
ATOM    324  C    VAL A  82      14.433  28.005  18.158  1.00 33.64           C
ATOM    325  O    VAL A  82      14.114  27.626  17.035  1.00 33.64           O
ATOM    326  N    ALA A  83      14.529  27.207  19.207  1.00 40.13           N
ATOM    327  CA   ALA A  83      14.181  25.800  19.149  1.00 40.13           C
ATOM    328  CB   ALA A  83      15.361  24.944  19.575  1.00 12.91           C
ATOM    329  C    ALA A  83      13.010  25.615  20.117  1.00 40.13           C
ATOM    330  O    ALA A  83      12.853  26.368  21.087  1.00 40.13           O
ATOM    331  N    ILE A  84      12.171  24.627  19.846  1.00 35.00           N
ATOM    332  CA   ILE A  84      11.035  24.379  20.715  1.00 35.00           C
ATOM    333  CB   ILE A  84       9.711  24.907  20.104  1.00 35.93           C
ATOM    334  CG2  ILE A  84       8.569  24.675  21.075  1.00 35.93          .C
ATOM    335  CG1  ILE A  84       9.813  26.407  19.818  1.00 35.93           C
ATOM    336  CD1  ILE A  84       8.526  26.997  19.267  1.00 35.93           C
ATOM    337  C    ILE A  84      10.905  22.895  20.962  1.00 35.00           C
ATOM    338  O    ILE A  84      10.612  22.120  20.054  1.00 35.00           O
ATOM    339  N    LYS A  85      11.128  22.497  22.199  1.00 26.59           N
ATOM    340  CA   LYS A  85      11.030  21.091  22.520  1.00 26.59           C
ATOM    341  CB   LYS A  85      12.114  20.695  23.518  1.00 20.88           C
ATOM    342  CG   LYS A  85      12.160  19.201  23.798  1.00 20.88           C
ATOM    343  CD   LYS A  85      13.235  18.902  24.826  1.00 20.88           C
ATOM    344  CE   LYS A  85      13.357  17.426  25.086  1.00 20.88           C
ATOM    345  NZ   LYS A  85      14.423  17.170  26.087  1.00 20.88           N
ATOM    346  C    LYS A  85       9.656  20.774  23.097  1.00 26.59           C
ATOM    347  O    LYS A  85       9.323  21.207  24.211  1.00 26.59           O
ATOM    348  N    LYS A  86       8.861  20.024  22.334  1.00 42.98           N
ATOM    349  CA   LYS A  86       7.523  19.635  22.776  1.00 42.98           C
ATOM    350  CB   LYS A  86       6.537  19.649  21.609  1.00 66.38           C
ATOM    351  CG   LYS A  86       5.141  20.127  21.989  1.00 66.38           C
ATOM    352  CD   LYS A  86       4.314  20.434  20.762  1.00 66.38           C
ATOM    353  CE   LYS A  86       3.798  19.172  20.112  1.00 66.38           C
ATOM    354  NZ   LYS A  86       3.465  19.426  18.680  1.00 66.38           N
ATOM    355  C    LYS A  86       7.655  18.234  23.338  1.00 42.98           C
ATOM    356  O    LYS A  86       8.040  17.311  22.618  1.00 42.98           O
ATOM    357  N    VAL A  87       7.356  18.087  24.628  1.00 50.70           N
```

FIG. 7-7

```
ATOM    358  CA   VAL A  87       7.473  16.799  25.312  1.00 50.70           C
ATOM    359  CB   VAL A  87       8.657  16.787  26.285  1.00 48.68           C
ATOM    360  CG1  VAL A  87       8.736  15.441  26.979  1.00 48.68           C
ATOM    361  CG2  VAL A  87       9.943  17.083  25.537  1.00 48.68           C
ATOM    362  C    VAL A  87       6.243  16.424  26.112  1.00 50.70           C
ATOM    363  O    VAL A  87       5.759  17.207  26.925  1.00 50.70           O
ATOM    364  N    LEU A  88       5.758  15.208  25.899  1.00 41.76           N
ATOM    365  CA   LEU A  88       4.579  14.741  26.598  1.00 41.76           C
ATOM    366  CB   LEU A  88       4.033  13.478  25.934  1.00 44.55           C
ATOM    367  CG   LEU A  88       2.595  13.116  26.320  1.00 44.55           C
ATOM    368  CD1  LEU A  88       1.865  12.644  25.093  1.00 44.55           C
ATOM    369  CD2  LEU A  88       2.577  12.045  27.397  1.00 44.55           C
ATOM    370  C    LEU A  88       4.848  14.465  28.065  1.00 41.76           C
ATOM    371  O    LEU A  88       5.869  13.872  28.422  1.00 41.76           O
ATOM    372  N    GLN A  89       3.903  14.897  28.897  1.00 54.87           N
ATOM    373  CA   GLN A  89       3.959  14.744  30.348  1.00 54.87           C
ATOM    374  CB   GLN A  89       3.275  15.930  31.017  1.00 42.26           C
ATOM    375  CG   GLN A  89       3.965  17.272  30.765  1.00 23.68           C
ATOM    376  CD   GLN A  89       5.423  17.274  31.261  1.00 23.68           C
ATOM    377  OE1  GLN A  89       5.696  16.929  32.433  1.00 23.68           O
ATOM    378  NE2  GLN A  89       6.364  17.659  30.380  1.00 23.68           N
ATOM    379  C    GLN A  89       3.216  13.505  30.679  1.00 54.87           C
ATOM    380  O    GLN A  89       2.051  13.374  30.300  1.00 54.87           O
ATOM    381  N    ASP A  90       3.830  12.588  31.395  1.00 57.98           N
ATOM    382  CA   ASP A  90       3.078  11.391  31.633  1.00 57.98           C
ATOM    383  CB   ASP A  90       3.319  10.425  30.457  1.00 78.54           C
ATOM    384  CG   ASP A  90       4.029   9.167  30.837  1.00 78.54           C
ATOM    385  OD1  ASP A  90       3.447   8.324  31.565  1.00 78.54           O
ATOM    386  OD2  ASP A  90       5.157   9.017  30.332  1.00 78.54           O
ATOM    387  C    ASP A  90       3.433  10.863  33.036  1.00 57.98           C
ATOM    388  O    ASP A  90       4.608  10.795  33.449  1.00 57.98           O
ATOM    389  N    ALA A  91       2.391  10.612  33.823  1.00 56.75           N
ATOM    390  CA   ALA A  91       2.563  10.151  35.201  1.00 56.75           C
ATOM    391  CB   ALA A  91       1.266  10.270  35.945  1.00 36.46           C
ATOM    392  C    ALA A  91       3.161   8.759  35.451  1.00 56.75           C
ATOM    393  O    ALA A  91       3.261   8.364  36.616  1.00 56.75           O
ATOM    394  N    GLY A  92       3.585   8.024  34.421  1.00 76.24           N
ATOM    395  CA   GLY A  92       4.179   6.724  34.687  1.00 76.24           C
ATOM    396  C    GLY A  92       5.458   7.007  35.436  1.00 76.24           C
ATOM    397  O    GLY A  92       5.996   6.121  36.091  1.00 76.24           O
ATOM    398  N    PHE A  93       5.922   8.259  35.381  1.00 84.86           N
ATOM    399  CA   PHE A  93       7.197   8.635  36.022  1.00 84.86           C
ATOM    400  CB   PHE A  93       8.417   8.260  35.144  1.00 23.68           C
ATOM    401  CG   PHE A  93       8.133   7.161  34.141  1.00 23.68           C
ATOM    402  CD1  PHE A  93       7.255   7.436  33.072  1.00 23.68           C
ATOM    403  CD2  PHE A  93       8.576   5.819  34.350  1.00 23.68           C
ATOM    404  CE1  PHE A  93       6.785   6.423  32.230  1.00 23.68           C
ATOM    405  CE2  PHE A  93       8.111   4.759  33.508  1.00 23.68           C
ATOM    406  CZ   PHE A  93       7.203   5.072  32.441  1.00 23.68           C
ATOM    407  C    PHE A  93       7.336  10.100  36.349  1.00 84.86           C
ATOM    408  O    PHE A  93       6.511  10.935  35.978  1.00 84.86           O
ATOM    409  N    LYS A  94       8.454  10.403  36.989  1.00 48.04           N
ATOM    410  CA   LYS A  94       8.742  11.748  37.427  1.00 48.04           C
ATOM    411  CB   LYS A  94       9.648  11.686  38.657  1.00 56.53           C
ATOM    412  CG   LYS A  94       9.547  10.377  39.466  1.00 56.53           C
ATOM    413  CD   LYS A  94       9.029  10.598  40.883  1.00 56.53           C
ATOM    414  CE   LYS A  94       9.667   9.593  41.831  1.00 56.53           C
ATOM    415  NZ   LYS A  94       8.683   8.993  42.773  1.00 56.53           N
ATOM    416  C    LYS A  94       9.359  12.634  36.347  1.00 48.04           C
ATOM    417  O    LYS A  94      10.184  12.185  35.538  1.00 48.04           O
```

FIG. 7-8

| | | | | | | | | | | |
|---|---|---|---|---|---|---|---|---|---|---|
| ATOM | 418 | N | ASN | A | 95 | 8.956 | 13.903 | 36.362 | 1.00 67.64 | N |
| ATOM | 419 | CA | ASN | A | 95 | 9.402 | 14.903 | 35.395 | 1.00 67.64 | C |
| ATOM | 420 | CB | ASN | A | 95 | 8.176 | 15.478 | 34.679 | 1.00 93.97 | C |
| ATOM | 421 | CG | ASN | A | 95 | 7.158 | 14.393 | 34.294 | 1.00 93.97 | C |
| ATOM | 422 | OD1 | ASN | A | 95 | 6.551 | 13.762 | 35.164 | 1.00 93.97 | O |
| ATOM | 423 | ND2 | ASN | A | 95 | 6.968 | 14.180 | 32.993 | 1.00 93.97 | N |
| ATOM | 424 | C | ASN | A | 95 | 10.158 | 16.014 | 36.092 | 1.00 67.64 | C |
| ATOM | 425 | O | ASN | A | 95 | 9.581 | 16.724 | 36.907 | 1.00 67.64 | O |
| ATOM | 426 | N | ARG | A | 96 | 11.436 | 16.181 | 35.784 | 1.00 37.22 | N |
| ATOM | 427 | CA | ARG | A | 96 | 12.198 | 17.242 | 36.442 | 1.00 37.22 | C |
| ATOM | 428 | CB | ARG | A | 96 | 13.188 | 16.626 | 37.382 | 1.00 37.63 | C |
| ATOM | 429 | CG | ARG | A | 96 | 12.671 | 15.325 | 37.929 | 1.00 37.63 | C |
| ATOM | 430 | CD | ARG | A | 96 | 13.631 | 14.744 | 38.910 | 1.00 37.63 | C |
| ATOM | 431 | NE | ARG | A | 96 | 13.040 | 13.622 | 39.635 | 1.00 37.63 | N |
| ATOM | 432 | CZ | ARG | A | 96 | 13.128 | 12.330 | 39.296 | 1.00 37.63 | C |
| ATOM | 433 | NH1 | ARG | A | 96 | 13.801 | 11.922 | 38.211 | 1.00 37.63 | N |
| ATOM | 434 | NH2 | ARG | A | 96 | 12.528 | 11.424 | 40.064 | 1.00 37.63 | N |
| ATOM | 435 | C | ARG | A | 96 | 12.941 | 18.130 | 35.452 | 1.00 37.22 | C |
| ATOM | 436 | O | ARG | A | 96 | 13.621 | 19.089 | 35.828 | 1.00 37.22 | O |
| ATOM | 437 | N | GLU | A | 97 | 12.762 | 17.820 | 34.177 | 1.00 42.30 | N |
| ATOM | 438 | CA | GLU | A | 97 | 13.417 | 18.553 | 33.133 | 1.00 42.30 | C |
| ATOM | 439 | CB | GLU | A | 97 | 12.981 | 18.005 | 31.774 | 1.00 47.72 | C |
| ATOM | 440 | CG | GLU | A | 97 | 12.913 | 19.020 | 30.681 | 1.00 47.72 | C |
| ATOM | 441 | CD | GLU | A | 97 | 13.215 | 18.422 | 29.319 | 1.00 47.72 | C |
| ATOM | 442 | OE1 | GLU | A | 97 | 12.349 | 17.699 | 28.774 | 1.00 47.72 | O |
| ATOM | 443 | OE2 | GLU | A | 97 | 14.334 | 18.672 | 28.815 | 1.00 47.72 | O |
| ATOM | 444 | C | GLU | A | 97 | 13.111 | 20.024 | 33.311 | 1.00 42.30 | C |
| ATOM | 445 | O | GLU | A | 97 | 14.035 | 20.813 | 33.434 | 1.00 42.30 | O |
| ATOM | 446 | N | LEU | A | 98 | 11.833 | 20.401 | 33.359 | 1.00 30.62 | N |
| ATOM | 447 | CA | LEU | A | 98 | 11.506 | 21.821 | 33.571 | 1.00 30.62 | C |
| ATOM | 448 | CB | LEU | A | 98 | 9.986 | 22.085 | 33.691 | 1.00 15.17 | C |
| ATOM | 449 | CG | LEU | A | 98 | 9.594 | 23.589 | 33.876 | 1.00 15.17 | C |
| ATOM | 450 | CD1 | LEU | A | 98 | 10.041 | 24.474 | 32.695 | 1.00 15.17 | C |
| ATOM | 451 | CD2 | LEU | A | 98 | 8.067 | 23.693 | 34.020 | 1.00 15.17 | C |
| ATOM | 452 | C | LEU | A | 98 | 12.195 | 22.375 | 34.825 | 1.00 30.62 | C |
| ATOM | 453 | O | LEU | A | 98 | 12.848 | 23.406 | 34.742 | 1.00 30.62 | O |
| ATOM | 454 | N | GLN | A | 99 | 12.043 | 21.698 | 35.968 | 1.00 41.17 | N |
| ATOM | 455 | CA | GLN | A | 99 | 12.648 | 22.108 | 37.248 | 1.00 41.17 | C |
| ATOM | 456 | CB | GLN | A | 99 | 12.549 | 20.981 | 38.276 | 1.00 61.47 | C |
| ATOM | 457 | CG | GLN | A | 99 | 11.157 | 20.495 | 38.602 | 1.00 61.47 | C |
| ATOM | 458 | CD | GLN | A | 99 | 11.182 | 19.155 | 39.331 | 1.00 61.47 | C |
| ATOM | 459 | OE1 | GLN | A | 99 | 10.332 | 18.298 | 39.089 | 1.00 61.47 | O |
| ATOM | 460 | NE2 | GLN | A | 99 | 12.154 | 18.972 | 40.227 | 1.00 61.47 | N |
| ATOM | 461 | C | GLN | A | 99 | 14.121 | 22.465 | 37.128 | 1.00 41.17 | C |
| ATOM | 462 | O | GLN | A | 99 | 14.514 | 23.605 | 37.375 | 1.00 41.17 | O |
| ATOM | 463 | N | ILE | A | 100 | 14.934 | 21.465 | 36.787 | 1.00 32.75 | N |
| ATOM | 464 | CA | ILE | A | 100 | 16.371 | 21.655 | 36.649 | 1.00 32.75 | C |
| ATOM | 465 | CB | ILE | A | 100 | 17.059 | 20.375 | 36.119 | 1.00 26.40 | C |
| ATOM | 466 | CG2 | ILE | A | 100 | 18.432 | 20.699 | 35.546 | 1.00 26.40 | C |
| ATOM | 467 | CG1 | ILE | A | 100 | 17.219 | 19.367 | 37.257 | 1.00 26.40 | C |
| ATOM | 468 | CD1 | ILE | A | 100 | 16.038 | 18.466 | 37.451 | 1.00 26.40 | C |
| ATOM | 469 | C | ILE | A | 100 | 16.634 | 22.789 | 35.688 | 1.00 32.75 | C |
| ATOM | 470 | O | ILE | A | 100 | 17.222 | 23.803 | 36.049 | 1.00 32.75 | O |
| ATOM | 471 | N | MET | A | 101 | 16.186 | 22.584 | 34.459 | 1.00 33.05 | N |
| ATOM | 472 | CA | MET | A | 101 | 16.320 | 23.539 | 33.371 | 1.00 33.05 | C |
| ATOM | 473 | CB | MET | A | 101 | 15.258 | 23.218 | 32.318 | 1.00 49.78 | C |
| ATOM | 474 | CG | MET | A | 101 | 15.417 | 23.952 | 31.019 | 1.00 49.78 | C |
| ATOM | 475 | SD | MET | A | 101 | 16.628 | 23.137 | 29.988 | 1.00 49.78 | S |
| ATOM | 476 | CE | MET | A | 101 | 15.678 | 21.737 | 29.462 | 1.00 49.78 | C |
| ATOM | 477 | C | MET | A | 101 | 16.155 | 24.990 | 33.846 | 1.00 33.05 | C |

FIG. 7-9

| ATOM | 478 | O | MET | A | 101 | 17.034 | 25.836 | 33.652 | 1.00 | 33.05 | O |
| ATOM | 479 | N | ARG | A | 102 | 15.024 | 25.270 | 34.478 | 1.00 | 42.97 | N |
| ATOM | 480 | CA | ARG | A | 102 | 14.728 | 26.611 | 34.961 | 1.00 | 42.97 | C |
| ATOM | 481 | CB | ARG | A | 102 | 13.380 | 26.616 | 35.658 | 1.00 | 35.14 | C |
| ATOM | 482 | CG | ARG | A | 102 | 12.268 | 26.172 | 34.777 | 1.00 | 35.14 | C |
| ATOM | 483 | CD | ARG | A | 102 | 10.987 | 26.416 | 35.473 | 1.00 | 35.14 | C |
| ATOM | 484 | NE | ARG | A | 102 | 10.913 | 27.816 | 35.866 | 1.00 | 35.14 | N |
| ATOM | 485 | CZ | ARG | A | 102 | 9.893 | 28.361 | 36.526 | 1.00 | 35.14 | C |
| ATOM | 486 | NH1 | ARG | A | 102 | 8.841 | 27.623 | 36.881 | 1.00 | 35.14 | N |
| ATOM | 487 | NH2 | ARG | A | 102 | 9.922 | 29.656 | 36.821 | 1.00 | 35.14 | N |
| ATOM | 488 | C | ARG | A | 102 | 15.757 | 27.264 | 35.882 | 1.00 | 42.97 | C |
| ATOM | 489 | O | ARG | A | 102 | 15.767 | 28.483 | 36.025 | 1.00 | 42.97 | O |
| ATOM | 490 | N | LYS | A | 103 | 16.624 | 26.480 | 36.508 | 1.00 | 42.60 | N |
| ATOM | 491 | CA | LYS | A | 103 | 17.605 | 27.066 | 37.405 | 1.00 | 42.60 | C |
| ATOM | 492 | CB | LYS | A | 103 | 17.454 | 26.465 | 38.800 | 1.00 | 41.71 | C |
| ATOM | 493 | CG | LYS | A | 103 | 17.505 | 24.957 | 38.839 | 1.00 | 41.71 | C |
| ATOM | 494 | CD | LYS | A | 103 | 17.237 | 24.459 | 40.260 | 1.00 | 41.71 | C |
| ATOM | 495 | CE | LYS | A | 103 | 16.878 | 22.970 | 40.294 | 1.00 | 41.71 | C |
| ATOM | 496 | NZ | LYS | A | 103 | 16.500 | 22.530 | 41.657 | 1.00 | 41.71 | N |
| ATOM | 497 | C | LYS | A | 103 | 19.046 | 26.922 | 36.937 | 1.00 | 42.60 | C |
| ATOM | 498 | O | LYS | A | 103 | 19.975 | 27.044 | 37.733 | 1.00 | 42.60 | O |
| ATOM | 499 | N | LEU | A | 104 | 19.239 | 26.664 | 35.650 | 1.00 | 32.41 | N |
| ATOM | 500 | CA | LEU | A | 104 | 20.587 | 26.516 | 35.112 | 1.00 | 32.41 | C |
| ATOM | 501 | CB | LEU | A | 104 | 20.657 | 25.293 | 34.190 | 1.00 | 33.79 | C |
| ATOM | 502 | CG | LEU | A | 104 | 20.922 | 23.927 | 34.832 | 1.00 | 33.79 | C |
| ATOM | 503 | CD1 | LEU | A | 104 | 20.276 | 23.834 | 36.192 | 1.00 | 33.79 | C |
| ATOM | 504 | CD2 | LEU | A | 104 | 20.397 | 22.849 | 33.928 | 1.00 | 33.79 | C |
| ATOM | 505 | C | LEU | A | 104 | 20.981 | 27.763 | 34.341 | 1.00 | 32.41 | C |
| ATOM | 506 | O | LEU | A | 104 | 20.145 | 28.398 | 33.710 | 1.00 | 32.41 | O |
| ATOM | 507 | N | ASP | A | 105 | 22.255 | 28.123 | 34.403 | 1.00 | 36.32 | N |
| ATOM | 508 | CA | ASP | A | 105 | 22.731 | 29.299 | 33.691 | 1.00 | 36.32 | C |
| ATOM | 509 | CB | ASP | A | 105 | 22.407 | 30.586 | 34.448 | 1.00 | 33.72 | C |
| ATOM | 510 | CG | ASP | A | 105 | 22.860 | 31.824 | 33.698 | 1.00 | 33.72 | C |
| ATOM | 511 | OD1 | ASP | A | 105 | 22.981 | 32.886 | 34.334 | 1.00 | 33.72 | O |
| ATOM | 512 | OD2 | ASP | A | 105 | 23.077 | 31.730 | 32.466 | 1.00 | 33.72 | O |
| ATOM | 513 | C | ASP | A | 105 | 24.223 | 29.198 | 33.526 | 1.00 | 36.32 | C |
| ATOM | 514 | O | ASP | A | 105 | 24.994 | 29.720 | 34.346 | 1.00 | 36.32 | O |
| ATOM | 515 | N | HIS | A | 106 | 24.622 | 28.514 | 32.463 | 1.00 | 64.52 | N |
| ATOM | 516 | CA | HIS | A | 106 | 26.027 | 28.303 | 32.160 | 1.00 | 64.52 | C |
| ATOM | 517 | CB | HIS | A | 106 | 26.426 | 26.881 | 32.575 | 1.00 | 45.87 | C |
| ATOM | 518 | CG | HIS | A | 106 | 27.899 | 26.622 | 32.538 | 1.00 | 45.87 | C |
| ATOM | 519 | CD2 | HIS | A | 106 | 28.885 | 26.957 | 33.391 | 1.00 | 45.87 | C |
| ATOM | 520 | ND1 | HIS | A | 106 | 28.498 | 25.915 | 31.515 | 1.00 | 45.87 | N |
| ATOM | 521 | CE1 | HIS | A | 106 | 29.795 | 25.825 | 31.749 | 1.00 | 45.87 | C |
| ATOM | 522 | NE2 | HIS | A | 106 | 30.060 | 26.449 | 32.876 | 1.00 | 45.87 | N |
| ATOM | 523 | C | HIS | A | 106 | 26.258 | 28.519 | 30.663 | 1.00 | 64.52 | C |
| ATOM | 524 | O | HIS | A | 106 | 25.331 | 28.369 | 29.857 | 1.00 | 64.52 | O |
| ATOM | 525 | N | CYS | A | 107 | 27.495 | 28.861 | 30.305 | 1.00 | 38.72 | N |
| ATOM | 526 | CA | CYS | A | 107 | 27.901 | 29.124 | 28.920 | 1.00 | 38.72 | C |
| ATOM | 527 | CB | CYS | A | 107 | 29.303 | 29.716 | 28.890 | 1.00 | 49.67 | C |
| ATOM | 528 | SG | CYS | A | 107 | 30.473 | 28.762 | 29.771 | 1.00 | 49.67 | S |
| ATOM | 529 | C | CYS | A | 107 | 27.883 | 27.912 | 28.018 | 1.00 | 38.72 | C |
| ATOM | 530 | O | CYS | A | 107 | 27.878 | 28.040 | 26.797 | 1.00 | 38.72 | O |
| ATOM | 531 | N | ASN | A | 108 | 27.874 | 26.734 | 28.615 | 1.00 | 26.21 | N |
| ATOM | 532 | CA | ASN | A | 108 | 27.881 | 25.513 | 27.833 | 1.00 | 26.21 | C |
| ATOM | 533 | CB | ASN | A | 108 | 29.206 | 24.810 | 28.043 | 1.00 | 39.72 | C |
| ATOM | 534 | CG | ASN | A | 108 | 30.338 | 25.528 | 27.357 | 1.00 | 39.72 | C |
| ATOM | 535 | OD1 | ASN | A | 108 | 31.384 | 25.743 | 27.943 | 1.00 | 39.72 | O |
| ATOM | 536 | ND2 | ASN | A | 108 | 30.127 | 25.913 | 26.101 | 1.00 | 39.72 | N |
| ATOM | 537 | C | ASN | A | 108 | 26.691 | 24.594 | 28.125 | 1.00 | 26.21 | C |

FIG. 7-10

```
ATOM    538  O    ASN A 108      26.769  23.361  28.098  1.00 26.21           O
ATOM    539  N    ILE A 109      25.577  25.255  28.386  1.00 27.27           N
ATOM    540  CA   ILE A 109      24.305  24.624  28.625  1.00 27.27           C
ATOM    541  CB   ILE A 109      23.998  24.596  30.101  1.00 16.97           C
ATOM    542  CG2  ILE A 109      22.574  24.094  30.329  1.00 16.97           C
ATOM    543  CG1  ILE A 109      25.035  23.702  30.796  1.00 16.97           C
ATOM    544  CD1  ILE A 109      24.817  23.540  32.313  1.00 16.97           C
ATOM    545  C    ILE A 109      23.311  25.492  27.863  1.00 27.27           C
ATOM    546  O    ILE A 109      23.413  26.721  27.880  1.00 27.27           O
ATOM    547  N    VAL A 110      22.380  24.850  27.166  1.00 26.69           N
ATOM    548  CA   VAL A 110      21.401  25.584  26.390  1.00 26.69           C
ATOM    549  CB   VAL A 110      20.447  24.680  25.655  1.00 17.52           C
ATOM    550  CG1  VAL A 110      19.954  25.387  24.402  1.00 17.52           C
ATOM    551  CG2  VAL A 110      21.117  23.380  25.339  1.00 17.52           C
ATOM    552  C    VAL A 110      20.558  26.453  27.278  1.00 26.69           C
ATOM    553  O    VAL A 110      20.073  26.018  28.324  1.00 26.69           O
ATOM    554  N    ARG A 111      20.373  27.689  26.850  1.00 23.32           N
ATOM    555  CA   ARG A 111      19.570  28.614  27.609  1.00 23.32           C
ATOM    556  CB   ARG A 111      19.996  30.029  27.254  1.00 47.27           C
ATOM    557  CG   ARG A 111      18.939  31.101  27.396  1.00 47.27           C
ATOM    558  CD   ARG A 111      19.656  32.430  27.444  1.00 47.27           C
ATOM    559  NE   ARG A 111      18.834  33.595  27.134  1.00 47.27           N
ATOM    560  CZ   ARG A 111      18.918  34.292  26.003  1.00 47.27           C
ATOM    561  NH1  ARG A 111      19.783  33.940  25.058  1.00 47.27           N
ATOM    562  NH2  ARG A 111      18.159  35.366  25.835  1.00 47.27           N
ATOM    563  C    ARG A 111      18.078  28.417  27.358  1.00 23.32           C
ATOM    564  O    ARG A 111      17.626  28.420  26.208  1.00 23.32           O
ATOM    565  N    LEU A 112      17.325  28.209  28.437  1.00 27.65           N
ATOM    566  CA   LEU A 112      15.873  28.056  28.344  1.00 27.65           C
ATOM    567  CB   LEU A 112      15.318  27.284  29.543  1.00 33.64           C
ATOM    568  CG   LEU A 112      13.790  27.280  29.620  1.00 33.64           C
ATOM    569  CD1  LEU A 112      13.194  26.362  28.540  1.00 33.64           C
ATOM    570  CD2  LEU A 112      13.365  26.828  31.013  1.00 33.64           C
ATOM    571  C    LEU A 112      15.303  29.473  28.337  1.00 27.65           C
ATOM    572  O    LEU A 112      15.488  30.236  29.278  1.00 27.65           O
ATOM    573  N    ARG A 113      14.608  29.822  27.268  1.00 32.67           N
ATOM    574  CA   ARG A 113      14.060  31.162  27.140  1.00 32.67           C
ATOM    575  CB   ARG A 113      13.993  31.538  25.661  1.00 52.67           C
ATOM    576  CG   ARG A 113      15.343  31.495  24.963  1.00 52.67           C
ATOM    577  CD   ARG A 113      15.729  32.863  24.477  1.00 52.67           C
ATOM    578  NE   ARG A 113      16.140  32.835  23.078  1.00 52.67           N
ATOM    579  CZ   ARG A 113      16.036  33.875  22.255  1.00 52.67           C
ATOM    580  NH1  ARG A 113      15.531  35.030  22.690  1.00 52.67           N
ATOM    581  NH2  ARG A 113      16.431  33.763  20.995  1.00 52.67           N
ATOM    582  C    ARG A 113      12.696  31.307  27.771  1.00 32.67           C
ATOM    583  O    ARG A 113      12.530  32.015  28.762  1.00 32.67           O
ATOM    584  N    TYR A 114      11.723  30.637  27.168  1.00 39.41           N
ATOM    585  CA   TYR A 114      10.354  30.664  27.644  1.00 39.41           C
ATOM    586  CB   TYR A 114       9.440  31.357  26.631  1.00 38.00           C
ATOM    587  CG   TYR A 114       9.888  32.739  26.225  1.00 38.00           C
ATOM    588  CD1  TYR A 114       9.689  33.832  27.071  1.00 38.00           C
ATOM    589  CE1  TYR A 114      10.130  35.097  26.719  1.00 38.00           C
ATOM    590  CD2  TYR A 114      10.541  32.952  25.008  1.00 38.00           C
ATOM    591  CE2  TYR A 114      10.993  34.216  24.646  1.00 38.00           C
ATOM    592  CZ   TYR A 114      10.784  35.287  25.508  1.00 38.00           C
ATOM    593  OH   TYR A 114      11.250  36.545  25.175  1.00 38.00           O
ATOM    594  C    TYR A 114       9.940  29.220  27.731  1.00 39.41           C
ATOM    595  O    TYR A 114      10.720  28.317  27.431  1.00 39.41           O
ATOM    596  N    PHE A 115       8.702  29.010  28.144  1.00 42.29           N
ATOM    597  CA   PHE A 115       8.138  27.676  28.224  1.00 42.29           C
```

FIG. 7-11

| | | | | | | | | | |
|---|---|---|---|---|---|---|---|---|---|
| ATOM | 598 | CB | PHE | A | 115 | 8.713 | 26.868 | 29.395 | 1.00 29.66 | C |
| ATOM | 599 | CG | PHE | A | 115 | 8.308 | 27.376 | 30.743 | 1.00 29.66 | C |
| ATOM | 600 | CD1 | PHE | A | 115 | 7.195 | 26.850 | 31.400 | 1.00 29.66 | C |
| ATOM | 601 | CD2 | PHE | A | 115 | 9.046 | 28.382 | 31.365 | 1.00 29.66 | C |
| ATOM | 602 | CE1 | PHE | A | 115 | 6.832 | 27.308 | 32.642 | 1.00 29.66 | C |
| ATOM | 603 | CE2 | PHE | A | 115 | 8.695 | 28.850 | 32.608 | 1.00 29.66 | C |
| ATOM | 604 | CZ | PHE | A | 115 | 7.584 | 28.314 | 33.256 | 1.00 29.66 | C |
| ATOM | 605 | C | PHE | A | 115 | 6.649 | 27.891 | 28.378 | 1.00 42.29 | C |
| ATOM | 606 | O | PHE | A | 115 | 6.186 | 28.977 | 28.753 | 1.00 42.29 | O |
| ATOM | 607 | N | PHE | A | 116 | 5.902 | 26.853 | 28.046 | 1.00 38.49 | N |
| ATOM | 608 | CA | PHE | A | 116 | 4.465 | 26.913 | 28.126 | 1.00 38.49 | C |
| ATOM | 609 | CB | PHE | A | 116 | 3.941 | 27.879 | 27.062 | 1.00 47.12 | C |
| ATOM | 610 | CG | PHE | A | 116 | 4.256 | 27.466 | 25.653 | 1.00 47.12 | C |
| ATOM | 611 | CD1 | PHE | A | 116 | 3.363 | 26.677 | 24.938 | 1.00 47.12 | C |
| ATOM | 612 | CD2 | PHE | A | 116 | 5.426 | 27.886 | 25.026 | 1.00 47.12 | C |
| ATOM | 613 | CE1 | PHE | A | 116 | 3.619 | 26.313 | 23.616 | 1.00 47.12 | C |
| ATOM | 614 | CE2 | PHE | A | 116 | 5.693 | 27.523 | 23.691 | 1.00 47.12 | C |
| ATOM | 615 | CZ | PHE | A | 116 | 4.785 | 26.738 | 22.990 | 1.00 47.12 | C |
| ATOM | 616 | C | PHE | A | 116 | 3.916 | 25.520 | 27.917 | 1.00 38.49 | C |
| ATOM | 617 | O | PHE | A | 116 | 4.579 | 24.658 | 27.332 | 1.00 38.49 | O |
| ATOM | 618 | N | TYR | A | 117 | 2.713 | 25.295 | 28.426 | 1.00 36.04 | N |
| ATOM | 619 | CA | TYR | A | 117 | 2.065 | 23.995 | 28.296 | 1.00 36.04 | C |
| ATOM | 620 | CB | TYR | A | 117 | 1.393 | 23.604 | 29.609 | 1.00 41.26 | C |
| ATOM | 621 | CG | TYR | A | 117 | 2.374 | 23.114 | 30.634 | 1.00 41.26 | C |
| ATOM | 622 | CD1 | TYR | A | 117 | 2.787 | 21.794 | 30.636 | 1.00 41.26 | C |
| ATOM | 623 | CE1 | TYR | A | 117 | 3.727 | 21.340 | 31.542 | 1.00 41.26 | C |
| ATOM | 624 | CD2 | TYR | A | 117 | 2.923 | 23.980 | 31.570 | 1.00 41.26 | C |
| ATOM | 625 | CE2 | TYR | A | 117 | 3.867 | 23.543 | 32.484 | 1.00 41.26 | C |
| ATOM | 626 | CZ | TYR | A | 117 | 4.269 | 22.217 | 32.469 | 1.00 41.26 | C |
| ATOM | 627 | OH | TYR | A | 117 | 5.209 | 21.758 | 33.379 | 1.00 41.26 | O |
| ATOM | 628 | C | TYR | A | 117 | 1.048 | 24.056 | 27.179 | 1.00 36.04 | C |
| ATOM | 629 | O | TYR | A | 117 | 0.569 | 25.138 | 26.837 | 1.00 36.04 | O |
| ATOM | 630 | N | SER | A | 118 | 0.724 | 22.893 | 26.616 | 1.00 28.41 | N |
| ATOM | 631 | CA | SER | A | 118 | -0.216 | 22.817 | 25.500 | 1.00 28.41 | C |
| ATOM | 632 | CB | SER | A | 118 | 0.520 | 23.061 | 24.181 | 1.00 53.28 | C |
| ATOM | 633 | OG | SER | A | 118 | 0.413 | 21.936 | 23.323 | 1.00 53.28 | O |
| ATOM | 634 | C | SER | A | 118 | -0.897 | 21.475 | 25.438 | 1.00 28.41 | C |
| ATOM | 635 | O | SER | A | 118 | -0.470 | 20.514 | 26.099 | 1.00 28.41 | O |
| ATOM | 636 | N | SER | A | 119 | -1.948 | 21.380 | 24.637 | 1.00 67.47 | N |
| ATOM | 637 | CA | SER | A | 119 | -2.622 | 20.096 | 24.548 | 1.00 67.47 | C |
| ATOM | 638 | CB | SER | A | 119 | -4.115 | 20.205 | 24.863 | 1.00 58.15 | C |
| ATOM | 639 | OG | SER | A | 119 | -4.565 | 21.552 | 25.033 | 1.00 58.15 | O |
| ATOM | 640 | C | SER | A | 119 | -2.424 | 19.474 | 23.168 | 1.00 67.47 | C |
| ATOM | 641 | O | SER | A | 119 | -2.324 | 20.124 | 22.143 | 1.00 67.47 | O |
| ATOM | 642 | N | GLY | A | 120 | -2.341 | 18.163 | 23.180 | 1.00 79.78 | N |
| ATOM | 643 | CA | GLY | A | 120 | -2.139 | 17.413 | 21.958 | 1.00 79.78 | C |
| ATOM | 644 | C | GLY | A | 120 | -3.323 | 16.570 | 21.472 | 1.00 79.78 | C |
| ATOM | 645 | O | GLY | A | 120 | -3.155 | 15.430 | 20.977 | 1.00 79.78 | O |
| ATOM | 646 | N | ALA | A | 121 | -4.534 | 17.093 | 21.661 | 1.00103.54 | N |
| ATOM | 647 | CA | ALA | A | 121 | -5.739 | 16.425 | 21.195 | 1.00103.54 | C |
| ATOM | 648 | CB | ALA | A | 121 | -5.803 | 16.537 | 19.683 | 1.00 48.24 | C |
| ATOM | 649 | C | ALA | A | 121 | -5.826 | 14.970 | 21.621 | 1.00103.54 | C |
| ATOM | 650 | O | ALA | A | 121 | -5.925 | 14.088 | 20.780 | 1.00103.54 | O |
| ATOM | 651 | N | GLY | A | 122 | -5.799 | 14.725 | 22.926 | 1.00 72.86 | N |
| ATOM | 652 | CA | GLY | A | 122 | -5.888 | 13.363 | 23.414 | 1.00 72.86 | C |
| ATOM | 653 | C | GLY | A | 122 | -6.871 | 13.218 | 24.554 | 1.00 72.86 | C |
| ATOM | 654 | O | GLY | A | 122 | -7.764 | 14.052 | 24.728 | 1.00 72.86 | O |
| ATOM | 655 | N | GLY | A | 123 | -6.708 | 12.156 | 25.334 | 1.00 80.74 | N |
| ATOM | 656 | CA | GLY | A | 123 | -7.599 | 11.925 | 26.460 | 1.00 80.74 | C |
| ATOM | 657 | C | GLY | A | 123 | -6.945 | 12.401 | 27.732 | 1.00 80.74 | C |

FIG. 7-12

```
ATOM    658  O    GLY A 123      -6.390   11.612   28.502  1.00 80.74           O
ATOM    659  N    ALA A 124      -7.005   13.706   27.944  1.00 74.32           N
ATOM    660  CA   ALA A 124      -6.387   14.309   29.110  1.00 74.32           C
ATOM    661  CB   ALA A 124      -6.918   13.675   30.437  1.00 89.05           C
ATOM    662  C    ALA A 124      -4.898   14.152   28.974  1.00 74.32           C
ATOM    663  O    ALA A 124      -4.296   13.357   29.682  1.00 74.32           O
ATOM    664  N    GLU A 125      -4.319   14.891   28.030  1.00 72.44           N
ATOM    665  CA   GLU A 125      -2.883   14.826   27.807  1.00 72.44           C
ATOM    666  CB   GLU A 125      -2.572   13.809   26.699  1.00 85.94           C
ATOM    667  CG   GLU A 125      -2.424   14.342   25.276  1.00 85.94           C
ATOM    668  CD   GLU A 125      -2.266   13.192   24.281  1.00 85.94           C
ATOM    669  OE1  GLU A 125      -2.385   13.430   23.058  1.00 85.94           O
ATOM    670  OE2  GLU A 125      -2.025   12.047   24.740  1.00 85.94           O
ATOM    671  C    GLU A 125      -2.252   16.205   27.534  1.00 72.44           C
ATOM    672  O    GLU A 125      -2.574   16.878   26.574  1.00 72.44           O
ATOM    673  N    VAL A 126      -1.342   16.585   28.422  1.00 44.28           N
ATOM    674  CA   VAL A 126      -0.614   17.858   28.482  1.00 44.28           C
ATOM    675  CB   VAL A 126      -0.552   18.180   29.961  1.00 65.54           C
ATOM    676  CG1  VAL A 126       0.171   19.442   30.244  1.00 65.54           C
ATOM    677  CG2  VAL A 126      -2.001   18.182   30.510  1.00 65.54           C
ATOM    678  C    VAL A 126       0.833   17.743   27.869  1.00 44.28           C
ATOM    679  O    VAL A 126       1.531   16.721   27.975  1.00 44.28           O
ATOM    680  N    TYR A 127       1.270   18.778   27.162  1.00 41.43           N
ATOM    681  CA   TYR A 127       2.659   18.774   26.629  1.00 41.43           C
ATOM    682  CB   TYR A 127       2.723   18.869   25.084  1.00 75.34           C
ATOM    683  CG   TYR A 127       2.353   17.591   24.347  1.00 75.34           C
ATOM    684  CD1  TYR A 127       1.031   17.336   24.015  1.00 75.34           C
ATOM    685  CE1  TYR A 127       0.656   16.161   23.401  1.00 75.34           C
ATOM    686  CD2  TYR A 127       3.312   16.618   24.024  1.00 75.34           C
ATOM    687  CE2  TYR A 127       2.942   15.430   23.402  1.00 75.34           C
ATOM    688  CZ   TYR A 127       1.612   15.210   23.096  1.00 75.34           C
ATOM    689  OH   TYR A 127       1.234   14.017   22.520  1.00 75.34           O
ATOM    690  C    TYR A 127       3.458   19.945   27.194  1.00 41.43           C
ATOM    691  O    TYR A 127       2.903   21.002   27.495  1.00 41.43           O
ATOM    692  N    LEU A 128       4.757   19.755   27.385  1.00 34.78           N
ATOM    693  CA   LEU A 128       5.567   20.876   27.848  1.00 34.78           C
ATOM    694  CB   LEU A 128       6.526   20.493   28.990  1.00 51.00           C
ATOM    695  CG   LEU A 128       7.729   21.455   28.976  1.00 51.00           C
ATOM    696  CD1  LEU A 128       7.313   22.821   29.502  1.00 51.00           C
ATOM    697  CD2  LEU A 128       8.870   20.886   29.776  1.00 51.00           C
ATOM    698  C    LEU A 128       6.394   21.428   26.689  1.00 34.78           C
ATOM    699  O    LEU A 128       7.169   20.711   26.076  1.00 34.78           O
ATOM    700  N    ASN A 129       6.259   22.710   26.401  1.00 36.64           N
ATOM    701  CA   ASN A 129       7.042   23.289   25.315  1.00 36.64           C
ATOM    702  CB   ASN A 129       6.145   24.104   24.390  1.00 48.50           C
ATOM    703  CG   ASN A 129       4.900   23.351   23.985  1.00 48.50           C
ATOM    704  OD1  ASN A 129       4.708   23.037   22.815  1.00 48.50           O
ATOM    705  ND2  ASN A 129       4.043   23.052   24.959  1.00 48.50           N
ATOM    706  C    ASN A 129       8.162   24.170   25.860  1.00 36.64           C
ATOM    707  O    ASN A 129       7.922   25.139   26.573  1.00 36.64           O
ATOM    708  N    LEU A 130       9.392   23.823   25.513  1.00 39.80           N
ATOM    709  CA   LEU A 130      10.542   24.571   25.971  1.00 39.80           C
ATOM    710  CB   LEU A 130      11.577   23.604   26.536  1.00 23.13           C
ATOM    711  CG   LEU A 130      11.104   22.763   27.721  1.00 23.13           C
ATOM    712  CD1  LEU A 130      12.071   21.621   27.975  1.00 23.13           C
ATOM    713  CD2  LEU A 130      10.988   23.652   28.937  1.00 23.13           C
ATOM    714  C    LEU A 130      11.152   25.352   24.825  1.00 39.80           C
ATOM    715  O    LEU A 130      11.647   24.770   23.873  1.00 39.80           O
ATOM    716  N    VAL A 131      11.103   26.672   24.907  1.00 29.49           N
ATOM    717  CA   VAL A 131      11.690   27.506   23.872  1.00 29.49           C
```

FIG. 7-13

```
ATOM    718  CB   VAL A 131      10.959  28.864  23.756  1.00 35.65           C
ATOM    719  CG1  VAL A 131      11.474  29.634  22.528  1.00 35.65           C
ATOM    720  CG2  VAL A 131       9.453  28.633  23.672  1.00 35.65           C
ATOM    721  C    VAL A 131      13.140  27.738  24.298  1.00 29.49           C
ATOM    722  O    VAL A 131      13.413  28.353  25.337  1.00 29.49           O
ATOM    723  N    LEU A 132      14.068  27.240  23.494  1.00 34.39           N
ATOM    724  CA   LEU A 132      15.480  27.360  23.811  1.00 34.39           C
ATOM    725  CB   LEU A 132      16.075  25.956  23.921  1.00 23.32           C
ATOM    726  CG   LEU A 132      15.185  24.921  24.636  1.00 23.32           C
ATOM    727  CD1  LEU A 132      15.772  23.544  24.465  1.00 23.32           C
ATOM    728  CD2  LEU A 132      15.044  25.261  26.122  1.00 23.32           C
ATOM    729  C    LEU A 132      16.213  28.148  22.736  1.00 34.39           C
ATOM    730  O    LEU A 132      15.598  28.631  21.784  1.00 34.39           O
ATOM    731  N    ASP A 133      17.522  28.315  22.909  1.00 31.22           N
ATOM    732  CA   ASP A 133      18.315  28.992  21.898  1.00 31.22           C
ATOM    733  CB   ASP A 133      19.705  29.326  22.418  1.00 32.83           C
ATOM    734  CG   ASP A 133      19.734  30.593  23.205  1.00 32.83           C
ATOM    735  OD1  ASP A 133      20.748  30.845  23.882  1.00 32.83           O
ATOM    736  OD2  ASP A 133      18.745  31.347  23.145  1.00 32.83           O
ATOM    737  C    ASP A 133      18.456  27.954  20.804  1.00 31.22           C
ATOM    738  O    ASP A 133      18.453  26.749  21.085  1.00 31.22           O
ATOM    739  N    TYR A 134      18.573  28.390  19.561  1.00 25.59           N
ATOM    740  CA   TYR A 134      18.736  27.419  18.494  1.00 25.59           C
ATOM    741  CB   TYR A 134      18.066  27.906  17.210  1.00 55.10           C
ATOM    742  CG   TYR A 134      18.352  26.993  16.051  1.00 55.10           C
ATOM    743  CD1  TYR A 134      17.736  25.746  15.951  1.00 55.10           C
ATOM    744  CE1  TYR A 134      18.069  24.862  14.932  1.00 55.10           C
ATOM    745  CD2  TYR A 134      19.304  27.334  15.097  1.00 55.10           C
ATOM    746  CE2  TYR A 134      19.642  26.457  14.081  1.00 55.10           C
ATOM    747  CZ   TYR A 134      19.025  25.226  14.003  1.00 55.10           C
ATOM    748  OH   TYR A 134      19.368  24.357  12.992  1.00 55.10           O
ATOM    749  C    TYR A 134      20.228  27.151  18.226  1.00 25.59           C
ATOM    750  O    TYR A 134      20.997  28.087  17.999  1.00 25.59           O
ATOM    751  N    VAL A 135      20.632  25.880  18.270  1.00 32.70           N
ATOM    752  CA   VAL A 135      22.020  25.495  18.005  1.00 32.70           C
ATOM    753  CB   VAL A 135      22.619  24.710  19.182  1.00 41.13           C
ATOM    754  CG1  VAL A 135      24.117  24.526  18.984  1.00 41.13           C
ATOM    755  CG2  VAL A 135      22.353  25.457  20.461  1.00 41.13           C
ATOM    756  C    VAL A 135      22.003  24.636  16.738  1.00 32.70           C
ATOM    757  O    VAL A 135      21.388  23.564  16.713  1.00 32.70           O
ATOM    758  N    PRO A 136      22.709  25.088  15.679  1.00 28.31           N
ATOM    759  CD   PRO A 136      23.751  26.123  15.783  1.00 33.29           C
ATOM    760  CA   PRO A 136      22.800  24.431  14.371  1.00 28.31           C
ATOM    761  CB   PRO A 136      23.847  25.269  13.632  1.00 33.29           C
ATOM    762  CG   PRO A 136      23.866  26.564  14.364  1.00 33.29           C
ATOM    763  C    PRO A 136      23.131  22.940  14.289  1.00 28.31           C
ATOM    764  O    PRO A 136      22.544  22.222  13.479  1.00 28.31           O
ATOM    765  N    GLU A 137      24.067  22.470  15.106  1.00 23.09           N
ATOM    766  CA   GLU A 137      24.449  21.074  15.009  1.00 23.09           C
ATOM    767  CB   GLU A 137      25.725  20.972  14.148  1.00 74.63           C
ATOM    768  CG   GLU A 137      25.668  19.979  12.975  1.00 74.63           C
ATOM    769  CD   GLU A 137      25.599  20.661  11.618  1.00 74.63           C
ATOM    770  OE1  GLU A 137      25.635  19.957  10.583  1.00 74.63           O
ATOM    771  OE2  GLU A 137      25.509  21.905  11.590  1.00 74.63           O
ATOM    772  C    GLU A 137      24.666  20.375  16.358  1.00 23.09           C
ATOM    773  O    GLU A 137      24.410  20.952  17.417  1.00 23.09           O
ATOM    774  N    THR A 138      25.108  19.117  16.300  1.00 18.36           N
ATOM    775  CA   THR A 138      25.413  18.336  17.501  1.00 18.36           C
ATOM    776  CB   THR A 138      24.401  17.229  17.793  1.00 23.68           C
ATOM    777  OG1  THR A 138      24.423  16.285  16.719  1.00 23.68           O
```

FIG. 7-14

```
ATOM    778  CG2 THR A 138      23.020  17.794  17.981  1.00 23.68           C
ATOM    779  C   THR A 138      26.744  17.617  17.326  1.00 18.36           C
ATOM    780  O   THR A 138      27.265  17.492  16.215  1.00 18.36           O
ATOM    781  N   VAL A 139      27.276  17.113  18.429  1.00 37.43           N
ATOM    782  CA  VAL A 139      28.541  16.415  18.374  1.00 37.43           C
ATOM    783  CB  VAL A 139      29.048  16.070  19.782  1.00 27.08           C
ATOM    784  CG1 VAL A 139      30.329  15.262  19.689  1.00 27.08           C
ATOM    785  CG2 VAL A 139      29.308  17.345  20.557  1.00 27.08           C
ATOM    786  C   VAL A 139      28.426  15.143  17.545  1.00 37.43           C
ATOM    787  O   VAL A 139      29.390  14.734  16.902  1.00 37.43           O
ATOM    788  N   TYR A 140      27.247  14.528  17.542  1.00 37.38           N
ATOM    789  CA  TYR A 140      27.036  13.303  16.777  1.00 37.38           C
ATOM    790  CB  TYR A 140      25.664  12.700  17.082  1.00 39.64           C
ATOM    791  CG  TYR A 140      25.457  11.349  16.446  1.00 39.64           C
ATOM    792  CD1 TYR A 140      26.203  10.246  16.862  1.00 39.64           C
ATOM    793  CE1 TYR A 140      26.016   8.986  16.291  1.00 39.64           C
ATOM    794  CD2 TYR A 140      24.521  11.167  15.434  1.00 39.64           C
ATOM    795  CE2 TYR A 140      24.328   9.912  14.852  1.00 39.64           C
ATOM    796  CZ  TYR A 140      25.079   8.823  15.292  1.00 39.64           C
ATOM    797  OH  TYR A 140      24.880   7.566  14.767  1.00 39.64           O
ATOM    798  C   TYR A 140      27.106  13.596  15.290  1.00 37.38           C
ATOM    799  O   TYR A 140      27.935  13.031  14.567  1.00 37.38           O
ATOM    800  N   ARG A 141      26.212  14.479  14.848  1.00 30.09           N
ATOM    801  CA  ARG A 141      26.130  14.871  13.453  1.00 30.09           C
ATOM    802  CB  ARG A 141      25.273  16.134  13.321  1.00 74.54           C
ATOM    803  CG  ARG A 141      24.297  16.078  12.168  1.00 74.54           C
ATOM    804  CD  ARG A 141      24.343  17.335  11.309  1.00 74.54           C
ATOM    805  NE  ARG A 141      23.206  18.226  11.535  1.00 74.54           N
ATOM    806  CZ  ARG A 141      22.573  18.869  10.556  1.00 74.54           C
ATOM    807  NH1 ARG A 141      22.962  18.713   9.292  1.00 74.54           N
ATOM    808  NH2 ARG A 141      21.561  19.678  10.834  1.00 74.54           N
ATOM    809  C   ARG A 141      27.540  15.117  12.898  1.00 30.09           C
ATOM    810  O   ARG A 141      27.893  14.641  11.822  1.00 30.09           O
ATOM    811  N   VAL A 142      28.348  15.850  13.654  1.00 34.17           N
ATOM    812  CA  VAL A 142      29.712  16.153  13.245  1.00 34.17           C
ATOM    813  CB  VAL A 142      30.348  17.200  14.198  1.00 20.19           C
ATOM    814  CG1 VAL A 142      31.843  17.351  13.917  1.00 20.19           C
ATOM    815  CG2 VAL A 142      29.641  18.542  14.019  1.00 20.19           C
ATOM    816  C   VAL A 142      30.570  14.891  13.222  1.00 34.17           C
ATOM    817  O   VAL A 142      31.281  14.621  12.253  1.00 34.17           O
ATOM    818  N   ALA A 143      30.513  14.121  14.301  1.00 35.19           N
ATOM    819  CA  ALA A 143      31.287  12.882  14.393  1.00 35.19           C
ATOM    820  CB  ALA A 143      30.922  12.117  15.650  1.00  7.68           C
ATOM    821  C   ALA A 143      30.965  12.039  13.193  1.00 35.19           C
ATOM    822  O   ALA A 143      31.858  11.574  12.494  1.00 35.19           O
ATOM    823  N   ARG A 144      29.666  11.845  12.991  1.00 36.20           N
ATOM    824  CA  ARG A 144      29.115  11.074  11.887  1.00 36.20           C
ATOM    825  CB  ARG A 144      27.586  11.279  11.872  1.00 51.75           C
ATOM    826  CG  ARG A 144      26.744  10.180  11.209  1.00 51.75           C
ATOM    827  CD  ARG A 144      26.563   8.919  12.072  1.00 51.75           C
ATOM    828  NE  ARG A 144      27.708   8.006  12.016  1.00 51.75           N
ATOM    829  CZ  ARG A 144      28.066   7.301  10.942  1.00 51.75           C
ATOM    830  NH1 ARG A 144      27.373   7.389   9.814  1.00 51.75           N
ATOM    831  NH2 ARG A 144      29.131   6.510  10.987  1.00 51.75           N
ATOM    832  C   ARG A 144      29.767  11.551  10.562  1.00 36.20           C
ATOM    833  O   ARG A 144      30.278  10.746   9.776  1.00 36.20           O
ATOM    834  N   HIS A 145      29.783  12.866  10.348  1.00 41.63           N
ATOM    835  CA  HIS A 145      30.353  13.482   9.142  1.00 41.63           C
ATOM    836  CB  HIS A 145      30.287  15.006   9.275  1.00 48.91           C
ATOM    837  CG  HIS A 145      30.570  15.749   8.004  1.00 48.91           C
```

FIG. 7-15

```
ATOM    838  CD2 HIS A 145      29.735  16.334   7.112  1.00 48.91           C
ATOM    839  ND1 HIS A 145      31.848  15.985   7.545  1.00 48.91           N
ATOM    840  CE1 HIS A 145      31.788  16.687   6.428  1.00 48.91           C
ATOM    841  NE2 HIS A 145      30.519  16.912   6.143  1.00 48.91           N
ATOM    842  C   HIS A 145      31.791  13.059   8.837  1.00 41.63           C
ATOM    843  O   HIS A 145      32.171  12.898   7.675  1.00 41.63           O
ATOM    844  N   TYR A 146      32.594  12.899   9.879  1.00 37.91           N
ATOM    845  CA  TYR A 146      33.969  12.493   9.683  1.00 37.91           C
ATOM    846  CB  TYR A 146      34.813  12.774  10.922  1.00 36.82           C
ATOM    847  CG  TYR A 146      35.365  14.169  10.913  1.00 36.82           C
ATOM    848  CD1 TYR A 146      34.541  15.278  11.156  1.00 36.82           C
ATOM    849  CE1 TYR A 146      35.028  16.578  11.017  1.00 36.82           C
ATOM    850  CD2 TYR A 146      36.681  14.398  10.543  1.00 36.82           C
ATOM    851  CE2 TYR A 146      37.166  15.676  10.404  1.00 36.82           C
ATOM    852  CZ  TYR A 146      36.342  16.759  10.637  1.00 36.82           C
ATOM    853  OH  TYR A 146      36.842  18.022  10.466  1.00 36.82           O
ATOM    854  C   TYR A 146      33.989  11.031   9.375  1.00 37.91           C
ATOM    855  O   TYR A 146      34.442  10.640   8.317  1.00 37.91           O
ATOM    856  N   SER A 147      33.511  10.223  10.312  1.00 36.88           N
ATOM    857  CA  SER A 147      33.439   8.785  10.125  1.00 36.88           C
ATOM    858  CB  SER A 147      32.520   8.192  11.199  1.00 63.45           C
ATOM    859  OG  SER A 147      31.923   6.983  10.765  1.00 63.45           O
ATOM    860  C   SER A 147      32.900   8.465   8.718  1.00 36.88           C
ATOM    861  O   SER A 147      33.445   7.625   8.003  1.00 36.88           O
ATOM    862  N   ARG A 148      31.839   9.157   8.317  1.00 47.80           N
ATOM    863  CA  ARG A 148      31.235   8.929   7.012  1.00 47.80           C
ATOM    864  CB  ARG A 148      29.949   9.740   6.890  1.00 48.33           C
ATOM    865  CG  ARG A 148      28.990   9.196   5.867  1.00 48.33           C
ATOM    866  CD  ARG A 148      27.853  10.153   5.561  1.00 48.33           C
ATOM    867  NE  ARG A 148      26.884  10.280   6.646  1.00 48.33           N
ATOM    868  CZ  ARG A 148      26.960  11.177   7.624  1.00 48.33           C
ATOM    869  NH1 ARG A 148      27.970  12.036   7.661  1.00 48.33           N
ATOM    870  NH2 ARG A 148      26.011  11.232   8.552  1.00 48.33           N
ATOM    871  C   ARG A 148      32.192   9.290   5.874  1.00 47.80           C
ATOM    872  O   ARG A 148      32.072   8.776   4.761  1.00 47.80           O
ATOM    873  N   ALA A 149      33.137  10.181   6.149  1.00 37.14           N
ATOM    874  CA  ALA A 149      34.118  10.595   5.150  1.00 37.14           C
ATOM    875  CB  ALA A 149      34.372  12.098   5.228  1.00 33.18           C
ATOM    876  C   ALA A 149      35.405   9.846   5.426  1.00 37.14           C
ATOM    877  O   ALA A 149      36.483  10.248   4.984  1.00 37.14           O
ATOM    878  N   LYS A 150      35.288   8.762   6.182  1.00 46.06           N
ATOM    879  CA  LYS A 150      36.440   7.936   6.528  1.00 46.06           C
ATOM    880  CB  LYS A 150      36.909   7.136   5.303  1.00 73.01           C
ATOM    881  CG  LYS A 150      35.907   6.101   4.739  1.00 73.01           C
ATOM    882  CD  LYS A 150      34.832   6.715   3.831  1.00 73.01           C
ATOM    883  CE  LYS A 150      34.239   5.680   2.865  1.00 73.01           C
ATOM    884  NZ  LYS A 150      33.843   4.407   3.525  1.00 73.01           N
ATOM    885  C   LYS A 150      37.618   8.728   7.113  1.00 46.06           C
ATOM    886  O   LYS A 150      38.755   8.270   7.077  1.00 46.06           O
ATOM    887  N   GLN A 151      37.349   9.916   7.646  1.00 62.86           N
ATOM    888  CA  GLN A 151      38.397  10.728   8.262  1.00 62.86           C
ATOM    889  CB  GLN A 151      38.332  12.184   7.812  1.00 54.44           C
ATOM    890  CG  GLN A 151      38.408  12.416   6.336  1.00 54.44           C
ATOM    891  CD  GLN A 151      38.744  13.859   6.012  1.00 54.44           C
ATOM    892  OE1 GLN A 151      38.200  14.794   6.611  1.00 54.44           O
ATOM    893  NE2 GLN A 151      39.647  14.049   5.056  1.00 54.44           N
ATOM    894  C   GLN A 151      38.187  10.700   9.766  1.00 62.86           C
ATOM    895  O   GLN A 151      37.162  10.214  10.254  1.00 62.86           O
ATOM    896  N   THR A 152      39.149  11.246  10.499  1.00 62.58           N
ATOM    897  CA  THR A 152      39.061  11.286  11.952  1.00 62.58           C
```

FIG. 7-16

```
ATOM    898  CB   THR A 152      40.220  10.477  12.590  1.00 43.99           C
ATOM    899  OG1  THR A 152      40.086  10.480  14.018  1.00 43.99           O
ATOM    900  CG2  THR A 152      41.567  11.064  12.181  1.00 43.99           C
ATOM    901  C    THR A 152      39.088  12.731  12.454  1.00 62.58           C
ATOM    902  O    THR A 152      39.941  13.525  12.051  1.00 62.58           O
ATOM    903  N    LEU A 153      38.137  13.054  13.328  1.00 31.93           N
ATOM    904  CA   LEU A 153      37.990  14.389  13.917  1.00 31.93           C
ATOM    905  CB   LEU A 153      36.906  14.367  14.995  1.00 42.36           C
ATOM    906  CG   LEU A 153      36.645  15.697  15.695  1.00 42.36           C
ATOM    907  CD1  LEU A 153      35.838  16.584  14.774  1.00 42.36           C
ATOM    908  CD2  LEU A 153      35.908  15.463  17.000  1.00 42.36           C
ATOM    909  C    LEU A 153      39.282  14.917  14.530  1.00 31.93           C
ATOM    910  O    LEU A 153      39.908  14.254  15.360  1.00 31.93           O
ATOM    911  N    PRO A 154      39.689  16.131  14.132  1.00 56.82           N
ATOM    912  CD   PRO A 154      38.986  16.929  13.112  1.00 35.32           C
ATOM    913  CA   PRO A 154      40.901  16.825  14.593  1.00 56.82           C
ATOM    914  CB   PRO A 154      40.836  18.155  13.847  1.00 35.32           C
ATOM    915  CG   PRO A 154      40.077  17.815  12.596  1.00 35.32           C
ATOM    916  C    PRO A 154      40.957  17.033  16.111  1.00 56.82           C
ATOM    917  O    PRO A 154      40.098  17.711  16.671  1.00 56.82           O
ATOM    918  N    VAL A 155      41.977  16.469  16.760  1.00 40.65           N
ATOM    919  CA   VAL A 155      42.149  16.575  18.212  1.00 40.65           C
ATOM    920  CB   VAL A 155      43.603  16.268  18.638  1.00 36.21           C
ATOM    921  CG1  VAL A 155      43.912  14.806  18.394  1.00 36.21           C
ATOM    922  CG2  VAL A 155      44.575  17.160  17.868  1.00 36.21           C
ATOM    923  C    VAL A 155      41.765  17.928  18.803  1.00 40.65           C
ATOM    924  O    VAL A 155      41.214  17.996  19.899  1.00 40.65           O
ATOM    925  N    ILE A 156      42.069  19.006  18.092  1.00 36.26           N
ATOM    926  CA   ILE A 156      41.701  20.322  18.582  1.00 36.26           C
ATOM    927  CB   ILE A 156      41.969  21.406  17.522  1.00 41.68           C
ATOM    928  CG2  ILE A 156      41.117  21.159  16.276  1.00 41.68           C
ATOM    929  CG1  ILE A 156      41.633  22.781  18.099  1.00 41.68           C
ATOM    930  CD1  ILE A 156      42.420  23.146  19.344  1.00 41.68           C
ATOM    931  C    ILE A 156      40.209  20.336  18.958  1.00 36.26           C
ATOM    932  O    ILE A 156      39.828  20.864  19.997  1.00 36.26           O
ATOM    933  N    TYR A 157      39.379  19.739  18.111  1.00 21.98           N
ATOM    934  CA   TYR A 157      37.944  19.666  18.341  1.00 21.98           C
ATOM    935  CB   TYR A 157      37.236  19.249  17.053  1.00 31.03           C
ATOM    936  CG   TYR A 157      37.359  20.300  15.979  1.00 31.03           C
ATOM    937  CD1  TYR A 157      37.931  20.003  14.740  1.00 31.03           C
ATOM    938  CE1  TYR A 157      38.108  20.997  13.773  1.00 31.03           C
ATOM    939  CD2  TYR A 157      36.957  21.618  16.226  1.00 31.03           C
ATOM    940  CE2  TYR A 157      37.125  22.615  15.274  1.00 31.03           C
ATOM    941  CZ   TYR A 157      37.701  22.307  14.048  1.00 31.03           C
ATOM    942  OH   TYR A 157      37.863  23.315  13.106  1.00 31.03           O
ATOM    943  C    TYR A 157      37.610  18.695  19.459  1.00 21.98           C
ATOM    944  O    TYR A 157      36.703  18.943  20.259  1.00 21.98           O
ATOM    945  N    VAL A 158      38.329  17.580  19.512  1.00 23.88           N
ATOM    946  CA   VAL A 158      38.103  16.611  20.568  1.00 23.88           C
ATOM    947  CB   VAL A 158      39.054  15.417  20.431  1.00 29.93           C
ATOM    948  CG1  VAL A 158      38.782  14.392  21.527  1.00 29.93           C
ATOM    949  CG2  VAL A 158      38.871  14.791  19.053  1.00 29.93           C
ATOM    950  C    VAL A 158      38.362  17.347  21.876  1.00 23.88           C
ATOM    951  O    VAL A 158      37.589  17.229  22.832  1.00 23.88           O
ATOM    952  N    LYS A 159      39.435  18.137  21.900  1.00 43.02           N
ATOM    953  CA   LYS A 159      39.795  18.912  23.088  1.00 43.02           C
ATOM    954  CB   LYS A 159      41.134  19.633  22.889  1.00 28.29           C
ATOM    955  CG   LYS A 159      42.346  18.705  22.801  1.00 28.29           C
ATOM    956  CD   LYS A 159      43.646  19.465  22.457  1.00 28.29           C
ATOM    957  CE   LYS A 159      44.846  18.519  22.292  1.00 28.29           C
```

FIG. 7-17

| | | | | | | | | | |
|---|---|---|---|---|---|---|---|---|---|
| ATOM | 958 | NZ | LYS A 159 | 46.098 | 19.248 | 21.968 | 1.00 | 28.29 | N |
| ATOM | 959 | C | LYS A 159 | 38.715 | 19.939 | 23.388 | 1.00 | 43.02 | C |
| ATOM | 960 | O | LYS A 159 | 38.151 | 19.954 | 24.485 | 1.00 | 43.02 | O |
| ATOM | 961 | N | LEU A 160 | 38.429 | 20.787 | 22.402 | 1.00 | 31.72 | N |
| ATOM | 962 | CA | LEU A 160 | 37.419 | 21.831 | 22.549 | 1.00 | 31.72 | C |
| ATOM | 963 | CB | LEU A 160 | 37.255 | 22.616 | 21.252 | 1.00 | 16.45 | C |
| ATOM | 964 | CG | LEU A 160 | 38.320 | 23.672 | 20.934 | 1.00 | 16.45 | C |
| ATOM | 965 | CD1 | LEU A 160 | 38.127 | 24.214 | 19.522 | 1.00 | 16.45 | C |
| ATOM | 966 | CD2 | LEU A 160 | 38.212 | 24.807 | 21.947 | 1.00 | 16.45 | C |
| ATOM | 967 | C | LEU A 160 | 36.059 | 21.313 | 22.984 | 1.00 | 31.72 | C |
| ATOM | 968 | O | LEU A 160 | 35.418 | 21.921 | 23.840 | 1.00 | 31.72 | O |
| ATOM | 969 | N | TYR A 161 | 35.595 | 20.206 | 22.410 | 1.00 | 35.85 | N |
| ATOM | 970 | CA | TYR A 161 | 34.293 | 19.689 | 22.814 | 1.00 | 35.85 | C |
| ATOM | 971 | CB | TYR A 161 | 33.749 | 18.706 | 21.775 | 1.00 | 32.78 | C |
| ATOM | 972 | CG | TYR A 161 | 33.616 | 19.298 | 20.388 | 1.00 | 32.78 | C |
| ATOM | 973 | CD1 | TYR A 161 | 33.349 | 20.659 | 20.218 | 1.00 | 32.78 | C |
| ATOM | 974 | CE1 | TYR A 161 | 33.275 | 21.227 | 18.942 | 1.00 | 32.78 | C |
| ATOM | 975 | CD2 | TYR A 161 | 33.798 | 18.505 | 19.240 | 1.00 | 32.78 | C |
| ATOM | 976 | CE2 | TYR A 161 | 33.724 | 19.059 | 17.955 | 1.00 | 32.78 | C |
| ATOM | 977 | CZ | TYR A 161 | 33.470 | 20.418 | 17.811 | 1.00 | 32.78 | C |
| ATOM | 978 | OH | TYR A 161 | 33.455 | 20.960 | 16.540 | 1.00 | 32.78 | O |
| ATOM | 979 | C | TYR A 161 | 34.328 | 19.026 | 24.189 | 1.00 | 35.85 | C |
| ATOM | 980 | O | TYR A 161 | 33.496 | 19.316 | 25.045 | 1.00 | 35.85 | O |
| ATOM | 981 | N | MET A 162 | 35.299 | 18.153 | 24.418 | 1.00 | 38.07 | N |
| ATOM | 982 | CA | MET A 162 | 35.371 | 17.464 | 25.696 | 1.00 | 38.07 | C |
| ATOM | 983 | CB | MET A 162 | 36.516 | 16.458 | 25.676 | 1.00 | 28.87 | C |
| ATOM | 984 | CG | MET A 162 | 36.236 | 15.309 | 24.736 | 1.00 | 28.87 | C |
| ATOM | 985 | SD | MET A 162 | 34.586 | 14.591 | 25.047 | 1.00 | 28.87 | S |
| ATOM | 986 | CE | MET A 162 | 34.879 | 13.932 | 26.695 | 1.00 | 28.87 | C |
| ATOM | 987 | C | MET A 162 | 35.521 | 18.438 | 26.848 | 1.00 | 38.07 | C |
| ATOM | 988 | O | MET A 162 | 34.883 | 18.307 | 27.901 | 1.00 | 38.07 | O |
| ATOM | 989 | N | TYR A 163 | 36.355 | 19.441 | 26.638 | 1.00 | 37.79 | N |
| ATOM | 990 | CA | TYR A 163 | 36.569 | 20.425 | 27.671 | 1.00 | 37.79 | C |
| ATOM | 991 | CB | TYR A 163 | 37.580 | 21.458 | 27.203 | 1.00 | 36.19 | C |
| ATOM | 992 | CG | TYR A 163 | 37.820 | 22.549 | 28.211 | 1.00 | 36.19 | C |
| ATOM | 993 | CD1 | TYR A 163 | 37.055 | 23.729 | 28.206 | 1.00 | 36.19 | C |
| ATOM | 994 | CE1 | TYR A 163 | 37.266 | 24.718 | 29.155 | 1.00 | 36.19 | C |
| ATOM | 995 | CD2 | TYR A 163 | 38.792 | 22.393 | 29.191 | 1.00 | 36.19 | C |
| ATOM | 996 | CE2 | TYR A 163 | 39.005 | 23.364 | 30.131 | 1.00 | 36.19 | C |
| ATOM | 997 | CZ | TYR A 163 | 38.244 | 24.516 | 30.108 | 1.00 | 36.19 | C |
| ATOM | 998 | OH | TYR A 163 | 38.484 | 25.477 | 31.038 | 1.00 | 36.19 | O |
| ATOM | 999 | C | TYR A 163 | 35.275 | 21.120 | 28.084 | 1.00 | 37.79 | C |
| ATOM | 1000 | O | TYR A 163 | 35.008 | 21.266 | 29.274 | 1.00 | 37.79 | O |
| ATOM | 1001 | N | GLN A 164 | 34.485 | 21.558 | 27.104 | 1.00 | 26.79 | N |
| ATOM | 1002 | CA | GLN A 164 | 33.237 | 22.256 | 27.397 | 1.00 | 26.79 | C |
| ATOM | 1003 | CB | GLN A 164 | 32.677 | 22.919 | 26.130 | 1.00 | 29.86 | C |
| ATOM | 1004 | CG | GLN A 164 | 33.611 | 23.990 | 25.561 | 1.00 | 29.86 | C |
| ATOM | 1005 | CD | GLN A 164 | 33.099 | 24.601 | 24.270 | 1.00 | 29.86 | C |
| ATOM | 1006 | OE1 | GLN A 164 | 32.298 | 25.529 | 24.285 | 1.00 | 29.86 | O |
| ATOM | 1007 | NE2 | GLN A 164 | 33.556 | 24.072 | 23.142 | 1.00 | 29.86 | N |
| ATOM | 1008 | C | GLN A 164 | 32.239 | 21.287 | 28.015 | 1.00 | 26.79 | C |
| ATOM | 1009 | O | GLN A 164 | 31.435 | 21.675 | 28.867 | 1.00 | 26.79 | O |
| ATOM | 1010 | N | LEU A 165 | 32.320 | 20.020 | 27.607 | 1.00 | 24.79 | N |
| ATOM | 1011 | CA | LEU A 165 | 31.446 | 18.982 | 28.147 | 1.00 | 24.79 | C |
| ATOM | 1012 | CB | LEU A 165 | 31.806 | 17.617 | 27.563 | 1.00 | 34.42 | C |
| ATOM | 1013 | CG | LEU A 165 | 30.708 | 16.548 | 27.528 | 1.00 | 34.42 | C |
| ATOM | 1014 | CD1 | LEU A 165 | 31.378 | 15.182 | 27.372 | 1.00 | 34.42 | C |
| ATOM | 1015 | CD2 | LEU A 165 | 29.836 | 16.604 | 28.783 | 1.00 | 34.42 | C |
| ATOM | 1016 | C | LEU A 165 | 31.676 | 18.932 | 29.654 | 1.00 | 24.79 | C |
| ATOM | 1017 | O | LEU A 165 | 30.745 | 19.072 | 30.450 | 1.00 | 24.79 | O |

FIG. 7-18

```
ATOM   1018  N    PHE A 166      32.935  18.733  30.033  1.00 24.41           N
ATOM   1019  CA   PHE A 166      33.312  18.653  31.436  1.00 24.41           C
ATOM   1020  CB   PHE A 166      34.806  18.358  31.563  1.00 31.21           C
ATOM   1021  CG   PHE A 166      35.184  16.971  31.131  1.00 31.21           C
ATOM   1022  CD1  PHE A 166      34.536  15.853  31.678  1.00 31.21           C
ATOM   1023  CD2  PHE A 166      36.163  16.773  30.156  1.00 31.21           C
ATOM   1024  CE1  PHE A 166      34.852  14.559  31.260  1.00 31.21           C
ATOM   1025  CE2  PHE A 166      36.487  15.482  29.731  1.00 31.21           C
ATOM   1026  CZ   PHE A 166      35.824  14.375  30.289  1.00 31.21           C
ATOM   1027  C    PHE A 166      32.963  19.879  32.264  1.00 24.41           C
ATOM   1028  O    PHE A 166      32.680  19.761  33.458  1.00 24.41           O
ATOM   1029  N    ARG A 167      32.982  21.056  31.649  1.00 33.03           N
ATOM   1030  CA   ARG A 167      32.649  22.279  32.382  1.00 33.03           C
ATOM   1031  CB   ARG A 167      32.938  23.531  31.558  1.00 30.50           C
ATOM   1032  CG   ARG A 167      34.335  24.072  31.720  1.00 30.50           C
ATOM   1033  CD   ARG A 167      34.417  25.477  31.183  1.00 30.50           C
ATOM   1034  NE   ARG A 167      33.792  26.463  32.066  1.00 30.50           N
ATOM   1035  CZ   ARG A 167      33.663  27.754  31.759  1.00 30.50           C
ATOM   1036  NH1  ARG A 167      34.108  28.214  30.596  1.00 30.50           N
ATOM   1037  NH2  ARG A 167      33.098  28.591  32.616  1.00 30.50           N
ATOM   1038  C    ARG A 167      31.189  22.287  32.766  1.00 33.03           C
ATOM   1039  O    ARG A 167      30.841  22.600  33.902  1.00 33.03           O
ATOM   1040  N    SER A 168      30.337  21.959  31.804  1.00 25.48           N
ATOM   1041  CA   SER A 168      28.898  21.899  32.044  1.00 25.48           C
ATOM   1042  CB   SER A 168      28.150  21.555  30.739  1.00 19.51           C
ATOM   1043  OG   SER A 168      28.451  20.248  30.263  1.00 19.51           O
ATOM   1044  C    SER A 168      28.612  20.829  33.110  1.00 25.48           C
ATOM   1045  O    SER A 168      27.726  20.989  33.952  1.00 25.48           O
ATOM   1046  N    LEU A 169      29.374  19.738  33.065  1.00 16.31           N
ATOM   1047  CA   LEU A 169      29.195  18.651  34.021  1.00 16.31           C
ATOM   1048  CB   LEU A 169      29.981  17.411  33.584  1.00 30.58           C
ATOM   1049  CG   LEU A 169      29.442  16.753  32.309  1.00 30.58           C
ATOM   1050  CD1  LEU A 169      30.323  15.592  31.892  1.00 30.58           C
ATOM   1051  CD2  LEU A 169      28.013  16.277  32.559  1.00 30.58           C
ATOM   1052  C    LEU A 169      29.629  19.090  35.402  1.00 16.31           C
ATOM   1053  O    LEU A 169      29.017  18.721  36.392  1.00 16.31           O
ATOM   1054  N    ALA A 170      30.682  19.899  35.473  1.00 22.58           N
ATOM   1055  CA   ALA A 170      31.153  20.379  36.771  1.00 22.58           C
ATOM   1056  CB   ALA A 170      32.494  21.095  36.625  1.00 27.67           C
ATOM   1057  C    ALA A 170      30.126  21.315  37.378  1.00 22.58           C
ATOM   1058  O    ALA A 170      29.887  21.292  38.581  1.00 22.58           O
ATOM   1059  N    TYR A 171      29.520  22.131  36.525  1.00 22.18           N
ATOM   1060  CA   TYR A 171      28.501  23.083  36.951  1.00 22.18           C
ATOM   1061  CB   TYR A 171      27.981  23.894  35.759  1.00 28.29           C
ATOM   1062  CG   TYR A 171      26.894  24.892  36.110  1.00 28.29           C
ATOM   1063  CD1  TYR A 171      27.203  26.112  36.711  1.00 28.29           C
ATOM   1064  CE1  TYR A 171      26.205  27.057  36.992  1.00 28.29           C
ATOM   1065  CD2  TYR A 171      25.557  24.630  35.807  1.00 28.29           C
ATOM   1066  CE2  TYR A 171      24.547  25.565  36.082  1.00 28.29           C
ATOM   1067  CZ   TYR A 171      24.874  26.775  36.673  1.00 28.29           C
ATOM   1068  OH   TYR A 171      23.863  27.682  36.935  1.00 28.29           O
ATOM   1069  C    TYR A 171      27.329  22.363  37.603  1.00 22.18           C
ATOM   1070  O    TYR A 171      27.127  22.441  38.813  1.00 22.18           O
ATOM   1071  N    ILE A 172      26.563  21.646  36.796  1.00 24.16           N
ATOM   1072  CA   ILE A 172      25.407  20.959  37.317  1.00 24.16           C
ATOM   1073  CB   ILE A 172      24.723  20.108  36.241  1.00 20.28           C
ATOM   1074  CG2  ILE A 172      24.261  20.985  35.104  1.00 20.28           C
ATOM   1075  CG1  ILE A 172      25.689  19.035  35.741  1.00 20.28           C
ATOM   1076  CD1  ILE A 172      25.053  17.994  34.801  1.00 20.28           C
ATOM   1077  C    ILE A 172      25.751  20.067  38.504  1.00 24.16           C
```

FIG. 7-19

```
ATOM   1078  O    ILE A 172      24.966  19.965  39.449  1.00 24.16           O
ATOM   1079  N    HIS A 173      26.916  19.425  38.476  1.00 26.38           N
ATOM   1080  CA   HIS A 173      27.291  18.536  39.576  1.00 26.38           C
ATOM   1081  CB   HIS A 173      28.595  17.797  39.266  1.00 19.20           C
ATOM   1082  CG   HIS A 173      28.428  16.625  38.342  1.00 19.20           C
ATOM   1083  CD2  HIS A 173      27.363  16.204  37.613  1.00 19.20           C
ATOM   1084  ND1  HIS A 173      29.462  15.761  38.040  1.00 19.20           N
ATOM   1085  CE1  HIS A 173      29.044  14.866  37.164  1.00 19.20           C
ATOM   1086  NE2  HIS A 173      27.776  15.113  36.887  1.00 19.20           N
ATOM   1087  C    HIS A 173      27.428  19.267  40.904  1.00 26.38           C
ATOM   1088  O    HIS A 173      27.203  18.691  41.975  1.00 26.38           O
ATOM   1089  N    SER A 174      27.787  20.541  40.833  1.00 24.68           N
ATOM   1090  CA   SER A 174      27.962  21.345  42.033  1.00 24.68           C
ATOM   1091  CB   SER A 174      28.691  22.650  41.700  1.00 23.96           C
ATOM   1092  OG   SER A 174      27.892  23.471  40.878  1.00 23.96           O
ATOM   1093  C    SER A 174      26.616  21.655  42.663  1.00 24.68           C
ATOM   1094  O    SER A 174      26.546  22.216  43.755  1.00 24.68           O
ATOM   1095  N    PHE A 175      25.552  21.302  41.951  1.00 20.70           N
ATOM   1096  CA   PHE A 175      24.189  21.499  42.425  1.00 20.70           C
ATOM   1097  CB   PHE A 175      23.342  22.209  41.372  1.00 23.38           C
ATOM   1098  CG   PHE A 175      23.661  23.662  41.217  1.00 23.38           C
ATOM   1099  CD1  PHE A 175      24.101  24.173  39.996  1.00 23.38           C
ATOM   1100  CD2  PHE A 175      23.526  24.527  42.298  1.00 23.38           C
ATOM   1101  CE1  PHE A 175      24.400  25.528  39.865  1.00 23.38           C
ATOM   1102  CE2  PHE A 175      23.822  25.879  42.187  1.00 23.38           C
ATOM   1103  CZ   PHE A 175      24.259  26.385  40.972  1.00 23.38           C
ATOM   1104  C    PHE A 175      23.582  20.134  42.700  1.00 20.70           C
ATOM   1105  O    PHE A 175      22.384  20.015  42.942  1.00 20.70           O
ATOM   1106  N    GLY A 176      24.415  19.099  42.635  1.00 34.72           N
ATOM   1107  CA   GLY A 176      23.942  17.752  42.877  1.00 34.72           C
ATOM   1108  C    GLY A 176      23.068  17.198  41.763  1.00 34.72           C
ATOM   1109  O    GLY A 176      22.448  16.134  41.922  1.00 34.72           O
ATOM   1110  N    ILE A 177      23.009  17.915  40.640  1.00 28.18           N
ATOM   1111  CA   ILE A 177      22.211  17.472  39.497  1.00 28.18           C
ATOM   1112  CB   ILE A 177      21.720  18.643  38.637  1.00 32.28           C
ATOM   1113  CG2  ILE A 177      20.910  18.105  37.471  1.00 32.28           C
ATOM   1114  CG1  ILE A 177      20.863  19.591  39.475  1.00 32.28           C
ATOM   1115  CD1  ILE A 177      20.427  20.857  38.702  1.00 32.28           C
ATOM   1116  C    ILE A 177      23.025  16.542  38.596  1.00 28.18           C
ATOM   1117  O    ILE A 177      24.140  16.862  38.192  1.00 28.18           O
ATOM   1118  N    CYS A 178      22.457  15.383  38.293  1.00 25.93           N
ATOM   1119  CA   CYS A 178      23.113  14.398  37.444  1.00 25.93           C
ATOM   1120  CB   CYS A 178      23.148  13.026  38.135  1.00 27.96           C
ATOM   1121  SG   CYS A 178      23.916  11.754  37.085  1.00 27.96           S
ATOM   1122  C    CYS A 178      22.339  14.319  36.143  1.00 25.93           C
ATOM   1123  O    CYS A 178      21.134  14.107  36.144  1.00 25.93           O
ATOM   1124  N    HIS A 179      23.045  14.494  35.035  1.00 39.21           N
ATOM   1125  CA   HIS A 179      22.416  14.492  33.724  1.00 39.21           C
ATOM   1126  CB   HIS A 179      23.439  14.832  32.638  1.00 32.96           C
ATOM   1127  CG   HIS A 179      22.822  15.179  31.317  1.00 32.96           C
ATOM   1128  CD2  HIS A 179      22.462  16.364  30.785  1.00 32.96           C
ATOM   1129  ND1  HIS A 179      22.449  14.215  30.399  1.00 32.96           N
ATOM   1130  CE1  HIS A 179      21.885  14.804  29.360  1.00 32.96           C
ATOM   1131  NE2  HIS A 179      21.875  16.102  29.564  1.00 32.96           N
ATOM   1132  C    HIS A 179      21.780  13.157  33.448  1.00 39.21           C
ATOM   1133  O    HIS A 179      20.638  13.091  33.009  1.00 39.21           O
ATOM   1134  N    ARG A 180      22.530  12.098  33.719  1.00 34.87           N
ATOM   1135  CA   ARG A 180      22.051  10.736  33.517  1.00 34.87           C
ATOM   1136  CB   ARG A 180      20.721  10.567  34.247  1.00 36.57           C
ATOM   1137  CG   ARG A 180      20.918  10.107  35.665  1.00 36.57           C
```

FIG. 7-20

| | | | | | | | | | |
|---|---|---|---|---|---|---|---|---|---|
| ATOM | 1138 | CD | ARG | A | 180 | 19.651 | 10.251 | 36.490 | 1.00 36.57 | C |
| ATOM | 1139 | NE | ARG | A | 180 | 19.354 | 8.975 | 37.129 | 1.00 36.57 | N |
| ATOM | 1140 | CZ | ARG | A | 180 | 18.134 | 8.470 | 37.249 | 1.00 36.57 | C |
| ATOM | 1141 | NH1 | ARG | A | 180 | 17.106 | 9.160 | 36.766 | 1.00 36.57 | N |
| ATOM | 1142 | NH2 | ARG | A | 180 | 17.939 | 7.288 | 37.845 | 1.00 36.57 | N |
| ATOM | 1143 | C | ARG | A | 180 | 21.895 | 10.237 | 32.062 | 1.00 34.87 | C |
| ATOM | 1144 | O | ARG | A | 180 | 21.421 | 9.112 | 31.842 | 1.00 34.87 | O |
| ATOM | 1145 | N | ASP | A | 181 | 22.286 | 11.044 | 31.076 | 1.00 28.81 | N |
| ATOM | 1146 | CA | ASP | A | 181 | 22.164 | 10.648 | 29.685 | 1.00 28.81 | C |
| ATOM | 1147 | CB | ASP | A | 181 | 20.741 | 10.889 | 29.177 | 1.00 34.86 | C |
| ATOM | 1148 | CG | ASP | A | 181 | 20.464 | 10.144 | 27.892 | 1.00 34.86 | C |
| ATOM | 1149 | OD1 | ASP | A | 181 | 21.216 | 9.164 | 27.631 | 1.00 34.86 | O |
| ATOM | 1150 | OD2 | ASP | A | 181 | 19.499 | 10.501 | 27.178 | 1.00 34.86 | O |
| ATOM | 1151 | C | ASP | A | 181 | 23.148 | 11.394 | 28.803 | 1.00 28.81 | C |
| ATOM | 1152 | O | ASP | A | 181 | 22.775 | 11.931 | 27.757 | 1.00 28.81 | O |
| ATOM | 1153 | N | ILE | A | 182 | 24.408 | 11.412 | 29.212 | 1.00 29.00 | N |
| ATOM | 1154 | CA | ILE | A | 182 | 25.429 | 12.095 | 28.438 | 1.00 29.00 | C |
| ATOM | 1155 | CB | ILE | A | 182 | 26.663 | 12.431 | 29.309 | 1.00 12.99 | C |
| ATOM | 1156 | CG2 | ILE | A | 182 | 27.734 | 13.107 | 28.466 | 1.00 12.99 | C |
| ATOM | 1157 | CG1 | ILE | A | 182 | 26.256 | 13.394 | 30.436 | 1.00 12.99 | C |
| ATOM | 1158 | CD1 | ILE | A | 182 | 25.823 | 14.755 | 29.960 | 1.00 12.99 | C |
| ATOM | 1159 | C | ILE | A | 182 | 25.846 | 11.242 | 27.254 | 1.00 29.00 | C |
| ATOM | 1160 | O | ILE | A | 182 | 26.456 | 10.196 | 27.426 | 1.00 29.00 | O |
| ATOM | 1161 | N | LYS | A | 183 | 25.481 | 11.691 | 26.058 | 1.00 28.26 | N |
| ATOM | 1162 | CA | LYS | A | 183 | 25.800 | 11.003 | 24.820 | 1.00 28.26 | C |
| ATOM | 1163 | CB | LYS | A | 183 | 24.670 | 10.048 | 24.439 | 1.00 27.22 | C |
| ATOM | 1164 | CG | LYS | A | 183 | 23.353 | 10.745 | 24.225 | 1.00 27.22 | C |
| ATOM | 1165 | CD | LYS | A | 183 | 22.271 | 9.769 | 23.845 | 1.00 27.22 | C |
| ATOM | 1166 | CE | LYS | A | 183 | 20.892 | 10.437 | 23.847 | 1.00 27.22 | C |
| ATOM | 1167 | NZ | LYS | A | 183 | 19.753 | 9.504 | 23.533 | 1.00 27.22 | N |
| ATOM | 1168 | C | LYS | A | 183 | 25.930 | 12.098 | 23.759 | 1.00 28.26 | C |
| ATOM | 1169 | O | LYS | A | 183 | 25.362 | 13.181 | 23.910 | 1.00 28.26 | O |
| ATOM | 1170 | N | PRO | A | 184 | 26.657 | 11.819 | 22.660 | 1.00 38.15 | N |
| ATOM | 1171 | CD | PRO | A | 184 | 27.084 | 10.454 | 22.313 | 1.00 14.24 | C |
| ATOM | 1172 | CA | PRO | A | 184 | 26.911 | 12.723 | 21.528 | 1.00 38.15 | C |
| ATOM | 1173 | CB | PRO | A | 184 | 27.347 | 11.764 | 20.434 | 1.00 14.24 | C |
| ATOM | 1174 | CG | PRO | A | 184 | 28.031 | 10.702 | 21.183 | 1.00 14.24 | C |
| ATOM | 1175 | C | PRO | A | 184 | 25.706 | 13.548 | 21.074 | 1.00 38.15 | C |
| ATOM | 1176 | O | PRO | A | 184 | 25.816 | 14.743 | 20.782 | 1.00 38.15 | O |
| ATOM | 1177 | N | GLN | A | 185 | 24.566 | 12.865 | 21.000 | 1.00 32.77 | N |
| ATOM | 1178 | CA | GLN | A | 185 | 23.291 | 13.424 | 20.563 | 1.00 32.77 | C |
| ATOM | 1179 | CB | GLN | A | 185 | 22.241 | 12.310 | 20.478 | 1.00 41.74 | C |
| ATOM | 1180 | CG | GLN | A | 185 | 22.586 | 11.195 | 19.499 | 1.00 41.74 | C |
| ATOM | 1181 | CD | GLN | A | 185 | 23.507 | 10.142 | 20.081 | 1.00 41.74 | C |
| ATOM | 1182 | OE1 | GLN | A | 185 | 24.278 | 10.406 | 21.010 | 1.00 41.74 | O |
| ATOM | 1183 | NE2 | GLN | A | 185 | 23.444 | 8.938 | 19.525 | 1.00 41.74 | N |
| ATOM | 1184 | C | GLN | A | 185 | 22.732 | 14.573 | 21.399 | 1.00 32.77 | C |
| ATOM | 1185 | O | GLN | A | 185 | 21.997 | 15.406 | 20.867 | 1.00 32.77 | O |
| ATOM | 1186 | N | ASN | A | 186 | 23.061 | 14.613 | 22.695 | 1.00 29.39 | N |
| ATOM | 1187 | CA | ASN | A | 186 | 22.575 | 15.678 | 23.590 | 1.00 29.39 | C |
| ATOM | 1188 | CB | ASN | A | 186 | 22.210 | 15.132 | 24.983 | 1.00 32.60 | C |
| ATOM | 1189 | CG | ASN | A | 186 | 21.181 | 14.047 | 24.934 | 1.00 32.60 | C |
| ATOM | 1190 | OD1 | ASN | A | 186 | 20.300 | 14.081 | 24.104 | 1.00 32.60 | O |
| ATOM | 1191 | ND2 | ASN | A | 186 | 21.278 | 13.080 | 25.839 | 1.00 32.60 | N |
| ATOM | 1192 | C | ASN | A | 186 | 23.605 | 16.794 | 23.784 | 1.00 29.39 | C |
| ATOM | 1193 | O | ASN | A | 186 | 23.511 | 17.585 | 24.732 | 1.00 29.39 | O |
| ATOM | 1194 | N | LEU | A | 187 | 24.594 | 16.842 | 22.896 | 1.00 36.77 | N |
| ATOM | 1195 | CA | LEU | A | 187 | 25.634 | 17.859 | 22.956 | 1.00 36.77 | C |
| ATOM | 1196 | CB | LEU | A | 187 | 27.010 | 17.201 | 23.044 | 1.00 19.99 | C |
| ATOM | 1197 | CG | LEU | A | 187 | 27.275 | 16.151 | 24.137 | 1.00 19.99 | C |

FIG. 7-21

```
ATOM   1198  CD1 LEU A 187      28.680  15.581  23.931  1.00 19.99           C
ATOM   1199  CD2 LEU A 187      27.129  16.753  25.545  1.00 19.99           C
ATOM   1200  C   LEU A 187      25.560  18.717  21.696  1.00 36.77           C
ATOM   1201  O   LEU A 187      26.114  18.347  20.665  1.00 36.77           O
ATOM   1202  N   LEU A 188      24.866  19.853  21.788  1.00 29.86           N
ATOM   1203  CA  LEU A 188      24.702  20.785  20.665  1.00 29.86           C
ATOM   1204  CB  LEU A 188      23.544  21.754  20.926  1.00 16.82           C
ATOM   1205  CG  LEU A 188      22.291  21.128  21.558  1.00 16.82           C
ATOM   1206  CD1 LEU A 188      21.252  22.199  21.758  1.00 16.82           C
ATOM   1207  CD2 LEU A 188      21.743  19.974  20.682  1.00 16.82           C
ATOM   1208  C   LEU A 188      25.951  21.613  20.475  1.00 29.86           C
ATOM   1209  O   LEU A 188      26.729  21.806  21.408  1.00 29.86           O
ATOM   1210  N   LEU A 189      26.154  22.115  19.271  1.00 26.56           N
ATOM   1211  CA  LEU A 189      27.322  22.941  19.061  1.00 26.56           C
ATOM   1212  CB  LEU A 189      28.592  22.084  19.137  1.00 41.86           C
ATOM   1213  CG  LEU A 189      28.842  21.051  18.046  1.00 41.86           C
ATOM   1214  CD1 LEU A 189      29.301  21.762  16.791  1.00 41.86           C
ATOM   1215  CD2 LEU A 189      29.916  20.071  18.485  1.00 41.86           C
ATOM   1216  C   LEU A 189      27.292  23.749  17.769  1.00 26.56           C
ATOM   1217  O   LEU A 189      26.711  23.324  16.763  1.00 26.56           O
ATOM   1218  N   ASP A 190      27.896  24.936  17.827  1.00 40.08           N
ATOM   1219  CA  ASP A 190      27.996  25.814  16.672  1.00 40.08           C
ATOM   1220  CB  ASP A 190      27.942  27.278  17.094  1.00 55.08           C
ATOM   1221  CG  ASP A 190      27.546  28.190  15.954  1.00 55.08           C
ATOM   1222  OD1 ASP A 190      28.416  28.500  15.101  1.00 55.08           O
ATOM   1223  OD2 ASP A 190      26.352  28.576  15.908  1.00 55.08           O
ATOM   1224  C   ASP A 190      29.356  25.484  16.083  1.00 40.08           C
ATOM   1225  O   ASP A 190      30.395  25.821  16.661  1.00 40.08           O
ATOM   1226  N   PRO A 191      29.367  24.823  14.915  1.00 44.37           N
ATOM   1227  CD  PRO A 191      28.226  24.766  13.988  1.00 60.41           C
ATOM   1228  CA  PRO A 191      30.613  24.429  14.247  1.00 44.37           C
ATOM   1229  CB  PRO A 191      30.142  23.601  13.041  1.00 60.41           C
ATOM   1230  CG  PRO A 191      28.630  23.683  13.033  1.00 60.41           C
ATOM   1231  C   PRO A 191      31.532  25.568  13.832  1.00 44.37           C
ATOM   1232  O   PRO A 191      32.698  25.337  13.529  1.00 44.37           O
ATOM   1233  N   ASP A 192      31.014  26.791  13.810  1.00 43.59           N
ATOM   1234  CA  ASP A 192      31.839  27.930  13.434  1.00 43.59           C
ATOM   1235  CB  ASP A 192      31.005  29.010  12.758  1.00 71.88           C
ATOM   1236  CG  ASP A 192      30.633  28.641  11.343  1.00 71.88           C
ATOM   1237  OD1 ASP A 192      31.474  28.037  10.644  1.00 71.88           O
ATOM   1238  OD2 ASP A 192      29.506  28.964  10.923  1.00 71.88           O
ATOM   1239  C   ASP A 192      32.555  28.513  14.631  1.00 43.59           C
ATOM   1240  O   ASP A 192      33.748  28.800  14.573  1.00 43.59           O
ATOM   1241  N   THR A 193      31.824  28.685  15.722  1.00 30.17           N
ATOM   1242  CA  THR A 193      32.417  29.227  16.937  1.00 30.17           C
ATOM   1243  CB  THR A 193      31.385  30.007  17.739  1.00 29.26           C
ATOM   1244  OG1 THR A 193      30.313  29.128  18.090  1.00 29.26           O
ATOM   1245  CG2 THR A 193      30.844  31.166  16.910  1.00 29.26           C
ATOM   1246  C   THR A 193      32.977  28.100  17.804  1.00 30.17           C
ATOM   1247  O   THR A 193      33.744  28.343  18.743  1.00 30.17           O
ATOM   1248  N   ALA A 194      32.573  26.872  17.485  1.00 26.36           N
ATOM   1249  CA  ALA A 194      33.031  25.684  18.199  1.00 26.36           C
ATOM   1250  CB  ALA A 194      34.555  25.670  18.234  1.00 11.10           C
ATOM   1251  C   ALA A 194      32.488  25.552  19.624  1.00 26.36           C
ATOM   1252  O   ALA A 194      33.017  24.762  20.420  1.00 26.36           O
ATOM   1253  N   VAL A 195      31.437  26.307  19.940  1.00 23.80           N
ATOM   1254  CA  VAL A 195      30.871  26.279  21.282  1.00 23.80           C
ATOM   1255  CB  VAL A 195      30.160  27.632  21.628  1.00 37.97           C
ATOM   1256  CG1 VAL A 195      30.990  28.806  21.094  1.00 37.97           C
ATOM   1257  CG2 VAL A 195      28.754  27.667  21.064  1.00 37.97           C
```

FIG. 7-22

```
ATOM   1258  C   VAL A 195      29.919  25.103  21.483  1.00 23.80           C
ATOM   1259  O   VAL A 195      29.095  24.781  20.626  1.00 23.80           O
ATOM   1260  N   LEU A 196      30.048  24.462  22.636  1.00 35.42           N
ATOM   1261  CA  LEU A 196      29.245  23.301  22.953  1.00 35.42           C
ATOM   1262  CB  LEU A 196      30.179  22.182  23.392  1.00 24.79           C
ATOM   1263  CG  LEU A 196      29.538  20.848  23.743  1.00 24.79           C
ATOM   1264  CD1 LEU A 196      30.491  19.729  23.367  1.00 24.79           C
ATOM   1265  CD2 LEU A 196      29.180  20.810  25.228  1.00 24.79           C
ATOM   1266  C   LEU A 196      28.205  23.590  24.030  1.00 35.42           C
ATOM   1267  O   LEU A 196      28.505  24.228  25.030  1.00 35.42           O
ATOM   1268  N   LYS A 197      26.982  23.108  23.819  1.00 34.18           N
ATOM   1269  CA  LYS A 197      25.887  23.319  24.759  1.00 34.18           C
ATOM   1270  CB  LYS A 197      24.839  24.235  24.130  1.00 24.21           C
ATOM   1271  CG  LYS A 197      25.363  25.549  23.594  1.00 24.21           C
ATOM   1272  CD  LYS A 197      25.357  26.662  24.641  1.00 24.21           C
ATOM   1273  CE  LYS A 197      25.711  28.022  24.011  1.00 24.21           C
ATOM   1274  NZ  LYS A 197      25.568  29.177  24.948  1.00 24.21           N
ATOM   1275  C   LYS A 197      25.197  22.012  25.161  1.00 34.18           C
ATOM   1276  O   LYS A 197      24.617  21.323  24.315  1.00 34.18           O
ATOM   1277  N   LEU A 198      25.244  21.690  26.453  1.00 23.66           N
ATOM   1278  CA  LEU A 198      24.604  20.495  26.990  1.00 23.66           C
ATOM   1279  CB  LEU A 198      25.010  20.308  28.442  1.00 19.87           C
ATOM   1280  CG  LEU A 198      24.470  19.067  29.139  1.00 19.87           C
ATOM   1281  CD1 LEU A 198      25.010  17.822  28.463  1.00 19.87           C
ATOM   1282  CD2 LEU A 198      24.871  19.120  30.606  1.00 19.87           C
ATOM   1283  C   LEU A 198      23.101  20.709  26.932  1.00 23.66           C
ATOM   1284  O   LEU A 198      22.626  21.754  27.367  1.00 23.66           O
ATOM   1285  N   CYS A 199      22.354  19.739  26.400  1.00 20.98           N
ATOM   1286  CA  CYS A 199      20.891  19.864  26.315  1.00 20.98           C
ATOM   1287  CB  CYS A 199      20.469  20.154  24.880  1.00 29.42           C
ATOM   1288  SG  CYS A 199      20.630  18.692  23.817  1.00 29.42           S
ATOM   1289  C   CYS A 199      20.169  18.596  26.781  1.00 20.98           C
ATOM   1290  O   CYS A 199      20.797  17.595  27.106  1.00 20.98           O
ATOM   1291  N   ASP A 200      18.842  18.657  26.812  1.00 34.06           N
ATOM   1292  CA  ASP A 200      18.026  17.513  27.200  1.00 34.06           C
ATOM   1293  CB  ASP A 200      18.319  16.345  26.250  1.00 48.97           C
ATOM   1294  CG  ASP A 200      17.372  15.174  26.431  1.00 48.97           C
ATOM   1295  OD1 ASP A 200      16.369  15.307  27.156  1.00 48.97           O
ATOM   1296  OD2 ASP A 200      17.625  14.113  25.827  1.00 48.97           O
ATOM   1297  C   ASP A 200      18.213  17.052  28.645  1.00 34.06           C
ATOM   1298  O   ASP A 200      19.108  16.260  28.940  1.00 34.06           O
ATOM   1299  N   PHE A 201      17.363  17.527  29.545  1.00 45.49           N
ATOM   1300  CA  PHE A 201      17.458  17.102  30.936  1.00 45.49           C
ATOM   1301  CB  PHE A 201      17.649  18.307  31.861  1.00 30.56           C
ATOM   1302  CG  PHE A 201      18.934  19.039  31.632  1.00 30.56           C
ATOM   1303  CD1 PHE A 201      19.007  20.064  30.682  1.00 30.56           C
ATOM   1304  CD2 PHE A 201      20.091  18.666  32.328  1.00 30.56           C
ATOM   1305  CE1 PHE A 201      20.219  20.710  30.422  1.00 30.56           C
ATOM   1306  CE2 PHE A 201      21.309  19.298  32.083  1.00 30.56           C
ATOM   1307  CZ  PHE A 201      21.377  20.327  31.122  1.00 30.56           C
ATOM   1308  C   PHE A 201      16.225  16.306  31.357  1.00 45.49           C
ATOM   1309  O   PHE A 201      15.696  16.485  32.461  1.00 45.49           O
ATOM   1310  N   GLY A 202      15.781  15.423  30.467  1.00 44.79           N
ATOM   1311  CA  GLY A 202      14.618  14.600  30.738  1.00 44.79           C
ATOM   1312  C   GLY A 202      15.006  13.524  31.721  1.00 44.79           C
ATOM   1313  O   GLY A 202      14.253  13.206  32.637  1.00 44.79           O
ATOM   1314  N   SER A 203      16.200  12.972  31.543  1.00 24.03           N
ATOM   1315  CA  SER A 203      16.697  11.924  32.438  1.00 24.03           C
ATOM   1316  CB  SER A 203      17.698  11.041  31.699  1.00 34.17           C
ATOM   1317  OG  SER A 203      17.126  10.584  30.495  1.00 34.17           O
```

FIG. 7-23

```
ATOM   1318  C    SER A 203      17.367  12.475  33.705  1.00 24.03           C
ATOM   1319  O    SER A 203      17.644  11.711  34.643  1.00 24.03           O
ATOM   1320  N    ALA A 204      17.630  13.788  33.717  1.00 31.63           N
ATOM   1321  CA   ALA A 204      18.289  14.468  34.844  1.00 31.63           C
ATOM   1322  CB   ALA A 204      18.519  15.990  34.541  1.00  8.87           C
ATOM   1323  C    ALA A 204      17.533  14.326  36.146  1.00 31.63           C
ATOM   1324  O    ALA A 204      16.318  14.101  36.176  1.00 31.63           O
ATOM   1325  N    LYS A 205      18.270  14.509  37.232  1.00 47.66           N
ATOM   1326  CA   LYS A 205      17.716  14.379  38.570  1.00 47.66           C
ATOM   1327  CB   LYS A 205      17.251  12.939  38.780  1.00 37.58           C
ATOM   1328  CG   LYS A 205      16.704  12.640  40.161  1.00 37.58           C
ATOM   1329  CD   LYS A 205      16.547  11.140  40.353  1.00 37.58           C
ATOM   1330  CE   LYS A 205      15.866  10.802  41.661  1.00 37.58           C
ATOM   1331  NZ   LYS A 205      15.729   9.338  41.873  1.00 37.58           N
ATOM   1332  C    LYS A 205      18.797  14.713  39.589  1.00 47.66           C
ATOM   1333  O    LYS A 205      19.987  14.487  39.344  1.00 47.66           O
ATOM   1334  N    GLN A 206      18.392  15.255  40.732  1.00 42.57           N
ATOM   1335  CA   GLN A 206      19.368  15.580  41.762  1.00 42.57           C
ATOM   1336  CB   GLN A 206      18.963  16.826  42.534  1.00 45.57           C
ATOM   1337  CG   GLN A 206      17.829  17.575  41.909  1.00 45.57           C
ATOM   1338  CD   GLN A 206      17.781  19.000  42.372  1.00 45.57           C
ATOM   1339  OE1  GLN A 206      16.793  19.696  42.144  1.00 45.57           O
ATOM   1340  NE2  GLN A 206      18.853  19.456  43.020  1.00 45.57           N
ATOM   1341  C    GLN A 206      19.410  14.377  42.674  1.00 42.57           C
ATOM   1342  O    GLN A 206      18.449  14.077  43.384  1.00 42.57           O
ATOM   1343  N    LEU A 207      20.528  13.675  42.631  1.00 34.88           N
ATOM   1344  CA   LEU A 207      20.690  12.482  43.418  1.00 34.88           C
ATOM   1345  CB   LEU A 207      21.732  11.582  42.763  1.00 34.24           C
ATOM   1346  CG   LEU A 207      21.746  11.423  41.245  1.00 34.24           C
ATOM   1347  CD1  LEU A 207      22.939  10.549  40.898  1.00 34.24           C
ATOM   1348  CD2  LEU A 207      20.433  10.813  40.718  1.00 34.24           C
ATOM   1349  C    LEU A 207      21.094  12.743  44.864  1.00 34.88           C
ATOM   1350  O    LEU A 207      22.103  13.410  45.149  1.00 34.88           O
ATOM   1351  N    VAL A 208      20.296  12.194  45.773  1.00 39.95           N
ATOM   1352  CA   VAL A 208      20.553  12.298  47.200  1.00 39.95           C
ATOM   1353  CB   VAL A 208      19.404  12.981  47.930  1.00 54.85           C
ATOM   1354  CG1  VAL A 208      19.293  14.383  47.460  1.00 54.85           C
ATOM   1355  CG2  VAL A 208      18.107  12.250  47.672  1.00 54.85           C
ATOM   1356  C    VAL A 208      20.670  10.870  47.702  1.00 39.95           C
ATOM   1357  O    VAL A 208      19.805  10.033  47.416  1.00 39.95           O
ATOM   1358  N    ARG A 209      21.743  10.585  48.431  1.00 35.64           N
ATOM   1359  CA   ARG A 209      21.962   9.240  48.947  1.00 35.64           C
ATOM   1360  CB   ARG A 209      23.307   9.176  49.663  1.00 34.73           C
ATOM   1361  CG   ARG A 209      24.224   8.122  49.120  1.00 34.73           C
ATOM   1362  CD   ARG A 209      23.912   6.828  49.780  1.00 34.73           C
ATOM   1363  NE   ARG A 209      24.418   6.807  51.152  1.00 34.73           N
ATOM   1364  CZ   ARG A 209      25.546   6.209  51.548  1.00 34.73           C
ATOM   1365  NH1  ARG A 209      26.330   5.560  50.677  1.00 34.73           N
ATOM   1366  NH2  ARG A 209      25.881   6.226  52.837  1.00 34.73           N
ATOM   1367  C    ARG A 209      20.832   8.803  49.881  1.00 35.64           C
ATOM   1368  O    ARG A 209      20.302   9.596  50.670  1.00 35.64           O
ATOM   1369  N    GLY A 210      20.462   7.531  49.775  1.00 44.07           N
ATOM   1370  CA   GLY A 210      19.396   6.998  50.600  1.00 44.07           C
ATOM   1371  C    GLY A 210      18.103   6.940  49.813  1.00 44.07           C
ATOM   1372  O    GLY A 210      17.270   6.045  49.991  1.00 44.07           O
ATOM   1373  N    GLU A 211      17.933   7.914  48.929  1.00 45.77           N
ATOM   1374  CA   GLU A 211      16.744   7.983  48.082  1.00 45.77           C
ATOM   1375  CB   GLU A 211      16.358   9.438  47.834  1.00 67.80           C
ATOM   1376  CG   GLU A 211      14.873   9.639  47.681  1.00 67.80           C
ATOM   1377  CD   GLU A 211      14.149   9.565  49.008  1.00 67.80           C
```

FIG. 7-24

```
ATOM   1378  OE1 GLU A 211     14.351  10.468  49.848  1.00 67.80           O
ATOM   1379  OE2 GLU A 211     13.382   8.604  49.215  1.00 67.80           O
ATOM   1380  C   GLU A 211     17.092   7.304  46.754  1.00 45.77           C
ATOM   1381  O   GLU A 211     17.648   7.931  45.855  1.00 45.77           O
ATOM   1382  N   PRO A 212     16.726   6.019  46.610  1.00 40.11           N
ATOM   1383  CD  PRO A 212     15.668   5.419  47.440  1.00 14.05           C
ATOM   1384  CA  PRO A 212     16.969   5.172  45.443  1.00 40.11           C
ATOM   1385  CB  PRO A 212     16.186   3.913  45.758  1.00 14.05           C
ATOM   1386  CG  PRO A 212     15.021   4.448  46.466  1.00 14.05           C
ATOM   1387  C   PRO A 212     16.622   5.728  44.088  1.00 40.11           C
ATOM   1388  O   PRO A 212     15.564   6.309  43.855  1.00 40.11           O
ATOM   1389  N   ASN A 213     17.550   5.486  43.183  1.00 39.80           N
ATOM   1390  CA  ASN A 213     17.444   5.961  41.826  1.00 39.80           C
ATOM   1391  CB  ASN A 213     18.635   6.846  41.534  1.00 39.29           C
ATOM   1392  CG  ASN A 213     18.900   7.831  42.646  1.00 39.29           C
ATOM   1393  OD1 ASN A 213     18.261   8.884  42.719  1.00 39.29           O
ATOM   1394  ND2 ASN A 213     19.834   7.485  43.542  1.00 39.29           N
ATOM   1395  C   ASN A 213     17.433   4.752  40.947  1.00 39.80           C
ATOM   1396  O   ASN A 213     18.113   3.777  41.264  1.00 39.80           O
ATOM   1397  N   VAL A 214     16.678   4.821  39.853  1.00 34.97           N
ATOM   1398  CA  VAL A 214     16.512   3.686  38.950  1.00 34.97           C
ATOM   1399  CB  VAL A 214     15.534   4.016  37.812  1.00 30.29           C
ATOM   1400  CG1 VAL A 214     16.153   4.989  36.836  1.00 30.29           C
ATOM   1401  CG2 VAL A 214     15.139   2.732  37.112  1.00 30.29           C
ATOM   1402  C   VAL A 214     17.810   3.159  38.338  1.00 34.97           C
ATOM   1403  O   VAL A 214     18.659   3.929  37.941  1.00 34.97           O
ATOM   1404  N   SER A 215     17.990   1.854  38.205  1.00 58.90           N
ATOM   1405  CA  SER A 215     19.253   1.398  37.612  1.00 58.90           C
ATOM   1406  CB  SER A 215     19.560  -0.076  37.920  1.00 57.81           C
ATOM   1407  OG  SER A 215     18.639  -0.723  38.816  1.00 57.81           O
ATOM   1408  C   SER A 215     18.696   1.483  36.213  1.00 58.90           C
ATOM   1409  O   SER A 215     17.720   2.161  36.040  1.00 58.90           O
ATOM   1410  N   PTY A 216     19.225   0.724  35.245  1.00 36.49           N
ATOM   1411  CA  PTY A 216     18.739   0.735  33.841  1.00 36.49           C
ATOM   1412  C   PTY A 216     18.523   2.186  33.405  1.00 36.49           C
ATOM   1413  O   PTY A 216     17.390   2.725  33.625  1.00 36.49           O
ATOM   1414  CB  PTY A 216     17.451  -0.144  33.686  1.00 80.44           C
ATOM   1415  CG  PTY A 216     17.498  -0.412  32.177  1.00 80.44           C
ATOM   1416  CD1 PTY A 216     16.360   0.085  31.436  1.00 80.44           C
ATOM   1417  CD2 PTY A 216     18.565  -1.108  31.406  1.00 80.44           C
ATOM   1418  CE1 PTY A 216     16.237  -0.086  29.981  1.00 80.44           C
ATOM   1419  CE2 PTY A 216     18.454  -1.290  29.947  1.00 80.44           C
ATOM   1420  CZ  PTY A 216     17.286  -0.785  29.194  1.00 80.44           C
ATOM   1421  OH  PTY A 216     17.134  -0.909  27.784  1.00 80.44           O
ATOM   1422  P   PTY A 216     18.246  -0.970  26.713  1.00 80.44           P
ATOM   1423  OP1 PTY A 216     18.909   0.292  26.591  1.00 80.44           O
ATOM   1424  OP2 PTY A 216     17.419  -1.327  25.461  1.00 80.44           O
ATOM   1425  OP3 PTY A 216     19.179  -2.008  27.015  1.00 80.44           O
ATOM   1426  N   ILE A 217     19.571   2.846  32.911  1.00 42.50           N
ATOM   1427  CA  ILE A 217     19.383   4.228  32.533  1.00 42.50           C
ATOM   1428  CB  ILE A 217.    19.183   5.109  33.740  1.00 28.87           C
ATOM   1429  CG2 ILE A 217     20.527   5.592  34.308  1.00 28.87           C
ATOM   1430  CG1 ILE A 217     18.287   6.225  33.299  1.00 28.87           C
ATOM   1431  CD1 ILE A 217     18.178   7.266  34.252  1.00 28.87           C
ATOM   1432  C   ILE A 217     20.594   4.731  31.803  1.00 42.50           C
ATOM   1433  O   ILE A 217     21.724   4.279  32.058  1.00 42.50           O
ATOM   1434  N   CYS A 218     20.355   5.660  30.887  1.00 45.77           N
ATOM   1435  CA  CYS A 218     21.416   6.230  30.093  1.00 45.77           C
ATOM   1436  CB  CYS A 218     22.678   6.400  30.949  1.00 59.57           C
ATOM   1437  SG  CYS A 218     24.130   7.076  30.122  1.00 59.57           S
```

FIG. 7-25

```
ATOM   1438  C    CYS A 218      21.704   5.368  28.875  1.00 45.77           C
ATOM   1439  O    CYS A 218      21.898   4.151  28.986  1.00 45.77           O
ATOM   1440  N    SER A 219      21.726   6.007  27.711  1.00 47.72           N
ATOM   1441  CA   SER A 219      22.019   5.304  26.466  1.00 47.72           C
ATOM   1442  CB   SER A 219      22.644   6.276  25.451  1.00 44.18           C
ATOM   1443  OG   SER A 219      21.694   6.604  24.448  1.00 44.18           O
ATOM   1444  C    SER A 219      22.938   4.083  26.683  1.00 47.72           C
ATOM   1445  O    SER A 219      24.066   4.236  27.167  1.00 47.72           O
ATOM   1446  N    ARG A 220      22.446   2.884  26.349  1.00 26.24           N
ATOM   1447  CA   ARG A 220      23.206   1.649  26.528  1.00 26.24           C
ATOM   1448  CB   ARG A 220      22.721   0.547  25.581  1.00 68.23           C
ATOM   1449  CG   ARG A 220      23.815  -0.580  25.407  1.00 68.23           C
ATOM   1450  CD   ARG A 220      23.266  -1.951  25.057  1.00 68.23           C
ATOM   1451  NE   ARG A 220      22.090  -1.703  24.253  1.00 68.23           N
ATOM   1452  CZ   ARG A 220      20.971  -1.240  24.791  1.00 68.23           C
ATOM   1453  NH1  ARG A 220      20.953  -1.018  26.111  1.00 68.23           N
ATOM   1454  NH2  ARG A 220      19.913  -0.972  24.028  1.00 68.23           N
ATOM   1455  C    ARG A 220      24.704   1.774  26.304  1.00 26.24           C
ATOM   1456  O    ARG A 220      25.500   1.226  27.062  1.00 26.24           O
ATOM   1457  N    TYR A 221      25.047   2.506  25.246  1.00 41.63           N
ATOM   1458  CA   TYR A 221      26.418   2.666  24.810  1.00 41.63           C
ATOM   1459  CB   TYR A 221      26.437   3.301  23.426  1.00 68.07           C
ATOM   1460  CG   TYR A 221      26.013   2.409  22.305  1.00 68.07           C
ATOM   1461  CD1  TYR A 221      25.327   1.201  22.510  1.00 68.07           C
ATOM   1462  CE1  TYR A 221      24.973   0.398  21.417  1.00 68.07           C
ATOM   1463  CD2  TYR A 221      26.322   2.778  21.013  1.00 68.07           C
ATOM   1464  CE2  TYR A 221      25.987   1.984  19.923  1.00 68.07           C
ATOM   1465  CZ   TYR A 221      25.309   0.796  20.126  1.00 68.07           C
ATOM   1466  OH   TYR A 221      24.959   0.011  19.047  1.00 68.07           O
ATOM   1467  C    TYR A 221      27.289   3.465  25.730  1.00 41.63           C
ATOM   1468  O    TYR A 221      28.496   3.223  25.825  1.00 41.63           O
ATOM   1469  N    TYR A 222      26.649   4.417  26.397  1.00 37.92           N
ATOM   1470  CA   TYR A 222      27.310   5.338  27.305  1.00 37.92           C
ATOM   1471  CB   TYR A 222      26.861   6.743  26.942  1.00 39.51           C
ATOM   1472  CG   TYR A 222      27.229   7.091  25.529  1.00 39.51           C
ATOM   1473  CD1  TYR A 222      26.341   6.881  24.456  1.00 39.51           C
ATOM   1474  CE1  TYR A 222      26.737   7.188  23.148  1.00 39.51           C
ATOM   1475  CD2  TYR A 222      28.500   7.602  25.257  1.00 39.51           C
ATOM   1476  CE2  TYR A 222      28.890   7.901  23.982  1.00 39.51           C
ATOM   1477  CZ   TYR A 222      28.011   7.694  22.936  1.00 39.51           C
ATOM   1478  OH   TYR A 222      28.380   8.005  21.662  1.00 39.51           O
ATOM   1479  C    TYR A 222      27.033   5.066  28.773  1.00 37.92           C
ATOM   1480  O    TYR A 222      27.455   5.815  29.656  1.00 37.92           O
ATOM   1481  N    ARG A 223      26.334   3.976  29.026  1.00 42.25           N
ATOM   1482  CA   ARG A 223      25.976   3.616  30.366  1.00 42.25           C
ATOM   1483  CB   ARG A 223      24.838   2.629  30.299  1.00 51.01           C
ATOM   1484  CG   ARG A 223      23.906   2.793  31.419  1.00 51.01           C
ATOM   1485  CD   ARG A 223      22.530   2.353  31.008  1.00 51.01           C
ATOM   1486  NE   ARG A 223      22.412   0.944  30.704  1.00 51.01           N
ATOM   1487  CZ   ARG A 223      21.585   0.476  29.773  1.00 51.01           C
ATOM   1488  NH1  ARG A 223      20.807   1.311  29.058  1.00 51.01           N
ATOM   1489  NH2  ARG A 223      21.543  -0.830  29.540  1.00 51.01           N
ATOM   1490  C    ARG A 223      27.154   3.069  31.179  1.00 42.25           C
ATOM   1491  O    ARG A 223      27.888   2.168  30.755  1.00 42.25           O
ATOM   1492  N    ALA A 224      27.342   3.677  32.342  1.00 38.57           N
ATOM   1493  CA   ALA A 224      28.397   3.310  33.295  1.00 38.57           C
ATOM   1494  CB   ALA A 224      28.377   4.251  34.470  1.00 62.40           C
ATOM   1495  C    ALA A 224      28.207   1.868  33.777  1.00 38.57           C
ATOM   1496  O    ALA A 224      27.100   1.446  34.039  1.00 38.57           O
ATOM   1497  N    PRO A 225      29.297   1.148  34.023  1.00 42.00           N
```

FIG. 7-26

```
ATOM   1498  CD   PRO A 225      30.639   1.696  34.266  1.00 47.49           C
ATOM   1499  CA   PRO A 225      29.201  -0.259  34.483  1.00 42.00           C
ATOM   1500  CB   PRO A 225      30.669  -0.597  34.796  1.00 47.49           C
ATOM   1501  CG   PRO A 225      31.197   0.703  35.242  1.00 47.49           C
ATOM   1502  C    PRO A 225      28.214  -0.646  35.621  1.00 42.00           C
ATOM   1503  O    PRO A 225      27.394  -1.568  35.477  1.00 42.00           O
ATOM   1504  N    GLU A 226      28.285   0.082  36.736  1.00 51.36           N
ATOM   1505  CA   GLU A 226      27.485  -0.162  37.935  1.00 51.36           C
ATOM   1506  CB   GLU A 226      27.946   0.814  39.010  1.00 45.00           C
ATOM   1507  CG   GLU A 226      29.229   1.592  38.594  1.00 45.00           C
ATOM   1508  CD   GLU A 226      28.952   3.030  38.154  1.00 45.00           C
ATOM   1509  OE1  GLU A 226      28.318   3.775  38.923  1.00 45.00           O
ATOM   1510  OE2  GLU A 226      29.374   3.421  37.055  1.00 45.00           O
ATOM   1511  C    GLU A 226      25.995  -0.036  37.687  1.00 51.36           C
ATOM   1512  O    GLU A 226      25.201  -0.529  38.470  1.00 51.36           O
ATOM   1513  N    LEU A 227      25.615   0.611  36.592  1.00 44.44           N
ATOM   1514  CA   LEU A 227      24.204   0.753  36.271  1.00 44.44           C
ATOM   1515  CB   LEU A 227      24.004   1.893  35.282  1.00 59.63           C
ATOM   1516  CG   LEU A 227      23.493   3.128  36.011  1.00 59.63           C
ATOM   1517  CD1  LEU A 227      23.997   4.382  35.341  1.00 59.63           C
ATOM   1518  CD2  LEU A 227      21.980   3.072  36.043  1.00 59.63           C
ATOM   1519  C    LEU A 227      23.684  -0.552  35.697  1.00 44.44           C
ATOM   1520  O    LEU A 227      22.522  -0.910  35.903  1.00 44.44           O
ATOM   1521  N    ALA A 228      24.553  -1.263  34.980  1.00 63.12           N
ATOM   1522  CA   ALA A 228      24.188  -2.549  34.393  1.00 63.12           C
ATOM   1523  CB   ALA A 228      25.182  -2.941  33.287  1.00 32.33           C
ATOM   1524  C    ALA A 228      24.227  -3.568  35.526  1.00 63.12           C
ATOM   1525  O    ALA A 228      23.649  -4.653  35.438  1.00 63.12           O
ATOM   1526  N    PHE A 229      24.922  -3.197  36.595  1.00 41.64           N
ATOM   1527  CA   PHE A 229      25.044  -4.046  37.765  1.00 41.64           C
ATOM   1528  CB   PHE A 229      26.388  -3.816  38.451  1.00 53.25           C
ATOM   1529  CG   PHE A 229      27.513  -4.629  37.874  1.00 53.25           C
ATOM   1530  CD1  PHE A 229      27.396  -6.006  37.747  1.00 53.25           C
ATOM   1531  CD2  PHE A 229      28.706  -4.025  37.494  1.00 53.25           C
ATOM   1532  CE1  PHE A 229      28.450  -6.767  37.260  1.00 53.25           C
ATOM   1533  CE2  PHE A 229      29.765  -4.783  37.007  1.00 53.25           C
ATOM   1534  CZ   PHE A 229      29.634  -6.156  36.890  1.00 53.25           C
ATOM   1535  C    PHE A 229      23.913  -3.781  38.745  1.00 41.64           C
ATOM   1536  O    PHE A 229      23.998  -4.159  39.909  1.00 41.64           O
ATOM   1537  N    GLY A 230      22.870  -3.108  38.265  1.00 50.34           N
ATOM   1538  CA   GLY A 230      21.701  -2.824  39.081  1.00 50.34           C
ATOM   1539  C    GLY A 230      21.842  -1.924  40.294  1.00 50.34           C
ATOM   1540  O    GLY A 230      20.929  -1.884  41.116  1.00 50.34           O
ATOM   1541  N    ALA A 231      22.965  -1.218  40.425  1.00 34.19           N
ATOM   1542  CA   ALA A 231      23.157  -0.306  41.559  1.00 34.19           C
ATOM   1543  CB   ALA A 231      24.559   0.310  41.527  1.00 22.48           C
ATOM   1544  C    ALA A 231      22.102   0.803  41.501  1.00 34.19           C
ATOM   1545  O    ALA A 231      21.911   1.431  40.459  1.00 34.19           O
ATOM   1546  N    THR A 232      21.412   1.037  42.614  1.00 44.97           N
ATOM   1547  CA   THR A 232      20.388   2.078  42.646  1.00 44.97           C
ATOM   1548  CB   THR A 232      19.042   1.545  43.163  1.00 52.29           C
ATOM   1549  OG1  THR A 232      19.224   0.972  44.465  1.00 52.29           O
ATOM   1550  CG2  THR A 232      18.479   0.510  42.199  1.00 52.29           C
ATOM   1551  C    THR A 232      20.828   3.230  43.533  1.00 44.97           C
ATOM   1552  O    THR A 232      20.124   4.229  43.673  1.00 44.97           O
ATOM   1553  N    ASP A 233      22.010   3.085  44.117  1.00 35.44           N
ATOM   1554  CA   ASP A 233      22.548   4.109  44.986  1.00 35.44           C
ATOM   1555  CB   ASP A 233      22.815   3.524  46.371  1.00 47.23           C
ATOM   1556  CG   ASP A 233      22.460   4.479  47.488  1.00 47.23           C
ATOM   1557  OD1  ASP A 233      22.777   4.153  48.654  1.00 47.23           O
```

FIG. 7-27

```
ATOM   1558  OD2 ASP A 233      21.857    5.540   47.206  1.00 47.23           O
ATOM   1559  C   ASP A 233      23.846    4.628   44.390  1.00 35.44           C
ATOM   1560  O   ASP A 233      24.865    4.683   45.084  1.00 35.44           O
ATOM   1561  N   TYR A 234      23.811    5.002   43.109  1.00 33.77           N
ATOM   1562  CA  TYR A 234      24.999    5.525   42.417  1.00 33.77           C
ATOM   1563  CB  TYR A 234      24.968    5.122   40.939  1.00 21.49           C
ATOM   1564  CG  TYR A 234      23.659    5.426   40.240  1.00 21.49           C
ATOM   1565  CD1 TYR A 234      23.412    6.680   39.680  1.00 21.49           C
ATOM   1566  CE1 TYR A 234      22.172    6.965   39.071  1.00 21.49           C
ATOM   1567  CD2 TYR A 234      22.645    4.469   40.176  1.00 21.49           C
ATOM   1568  CE2 TYR A 234      21.417    4.748   39.572  1.00 21.49           C
ATOM   1569  CZ  TYR A 234      21.194    5.982   39.028  1.00 21.49           C
ATOM   1570  OH  TYR A 234      20.005    6.209   38.418  1.00 21.49           O
ATOM   1571  C   TYR A 234      25.137    7.045   42.540  1.00 33.77           C
ATOM   1572  O   TYR A 234      24.223    7.723   42.990  1.00 33.77           O
ATOM   1573  N   THR A 235      26.286    7.573   42.136  1.00 31.78           N
ATOM   1574  CA  THR A 235      26.552    9.008   42.218  1.00 31.78           C
ATOM   1575  CB  THR A 235      27.905    9.279   42.876  1.00 44.33           C
ATOM   1576  OG1 THR A 235      28.953    8.893   41.981  1.00 44.33           O
ATOM   1577  CG2 THR A 235      28.042    8.479   44.156  1.00 44.33           C
ATOM   1578  C   THR A 235      26.569    9.662   40.844  1.00 31.78           C
ATOM   1579  O   THR A 235      26.435    8.989   39.819  1.00 31.78           O
ATOM   1580  N   SER A 236      26.741   10.977   40.820  1.00 38.26           N
ATOM   1581  CA  SER A 236      26.759   11.700   39.552  1.00 38.26           C
ATOM   1582  CB  SER A 236      26.764   13.205   39.794  1.00 41.33           C
ATOM   1583  OG  SER A 236      27.940   13.576   40.475  1.00 41.33           O
ATOM   1584  C   SER A 236      27.976   11.320   38.718  1.00 38.26           C
ATOM   1585  O   SER A 236      28.081   11.682   37.537  1.00 38.26           O
ATOM   1586  N   SER A 237      28.896   10.587   39.336  1.00 49.94           N
ATOM   1587  CA  SER A 237      30.108   10.157   38.653  1.00 49.94           C
ATOM   1588  CB  SER A 237      31.006    9.351   39.606  1.00 47.98           C
ATOM   1589  OG  SER A 237      30.382    8.159   40.056  1.00 47.98           O
ATOM   1590  C   SER A 237      29.780    9.325   37.416  1.00 49.94           C
ATOM   1591  O   SER A 237      30.622    9.148   36.536  1.00 49.94           O
ATOM   1592  N   ILE A 238      28.553    8.825   37.338  1.00 34.32           N
ATOM   1593  CA  ILE A 238      28.161    8.015   36.195  1.00 34.32           C
ATOM   1594  CB  ILE A 238      26.755    7.386   36.391  1.00 19.16           C
ATOM   1595  CG2 ILE A 238      26.717    6.605   37.702  1.00 19.16           C
ATOM   1596  CG1 ILE A 238      25.679    8.470   36.373  1.00 19.16           C
ATOM   1597  CD1 ILE A 238      24.269    7.916   36.462  1.00 19.16           C
ATOM   1598  C   ILE A 238      28.192    8.829   34.905  1.00 34.32           C
ATOM   1599  O   ILE A 238      28.286    8.268   33.813  1.00 34.32           O
ATOM   1600  N   ASP A 239      28.105   10.151   35.035  1.00 26.01           N
ATOM   1601  CA  ASP A 239      28.158   11.046   33.879  1.00 26.01           C
ATOM   1602  CB  ASP A 239      27.679   12.465   34.274  1.00 32.48           C
ATOM   1603  CG  ASP A 239      26.166   12.549   34.483  1.00 32.48           C
ATOM   1604  OD1 ASP A 239      25.456   11.613   34.076  1.00 32.48           O
ATOM   1605  OD2 ASP A 239      25.674   13.552   35.036  1.00 32.48           O
ATOM   1606  C   ASP A 239      29.603   11.111   33.333  1.00 26.01           C
ATOM   1607  O   ASP A 239      29.826   11.327   32.138  1.00 26.01           O
ATOM   1608  N   VAL A 240      30.570   10.903   34.224  1.00 20.88           N
ATOM   1609  CA  VAL A 240      31.973   10.960   33.865  1.00 20.88           C
ATOM   1610  CB  VAL A 240      32.881   10.895   35.098  1.00 18.97           C
ATOM   1611  CG1 VAL A 240      34.332   11.204   34.699  1.00 18.97           C
ATOM   1612  CG2 VAL A 240      32.392   11.880   36.143  1.00 18.97           C
ATOM   1613  C   VAL A 240      32.321    9.810   32.963  1.00 20.88           C
ATOM   1614  O   VAL A 240      33.127    9.966   32.034  1.00 20.88           O
ATOM   1615  N   TRP A 241      31.715    8.655   33.239  1.00 32.86           N
ATOM   1616  CA  TRP A 241      31.940    7.453   32.438  1.00 32.86           C
ATOM   1617  CB  TRP A 241      31.270    6.239   33.095  1.00 34.44           C
```

FIG. 7-28

```
ATOM   1618  CG   TRP A 241      31.285   4.985  32.248  1.00 34.44           C
ATOM   1619  CD2  TRP A 241      32.271   3.938  32.279  1.00 34.44           C
ATOM   1620  CE2  TRP A 241      31.880   2.973  31.308  1.00 34.44           C
ATOM   1621  CE3  TRP A 241      33.425   3.709  33.046  1.00 34.44           C
ATOM   1622  CD1  TRP A 241      30.382   4.633  31.277  1.00 34.44           C
ATOM   1623  NE1  TRP A 241      30.737   3.425  30.711  1.00 34.44           N
ATOM   1624  CZ2  TRP A 241      32.633   1.813  31.068  1.00 34.44           C
ATOM   1625  CZ3  TRP A 241      34.166   2.557  32.805  1.00 34.44           C
ATOM   1626  CH2  TRP A 241      33.757   1.615  31.831  1.00 34.44           C
ATOM   1627  C    TRP A 241      31.397   7.649  31.022  1.00 32.86           C
ATOM   1628  O    TRP A 241      32.036   7.278  30.032  1.00 32.86           O
ATOM   1629  N    SER A 242      30.214   8.239  30.926  1.00 40.81           N
ATOM   1630  CA   SER A 242      29.618   8.489  29.626  1.00 40.81           C
ATOM   1631  CB   SER A 242      28.212   9.055  29.793  1.00 35.24           C
ATOM   1632  OG   SER A 242      27.443   8.218  30.629  1.00 35.24           O
ATOM   1633  C    SER A 242      30.486   9.490  28.876  1.00 40.81           C
ATOM   1634  O    SER A 242      30.619   9.409  27.649  1.00 40.81           O
ATOM   1635  N    ALA A 243      31.063  10.438  29.620  1.00 25.31           N
ATOM   1636  CA   ALA A 243      31.927  11.455  29.034  1.00 25.31           C
ATOM   1637  CB   ALA A 243      32.391  12.432  30.107  1.00 49.37           C
ATOM   1638  C    ALA A 243      33.112  10.717  28.436  1.00 25.31           C
ATOM   1639  O    ALA A 243      33.537  10.991  27.312  1.00 25.31           O
ATOM   1640  N    GLY A 244      33.620   9.753  29.197  1.00 28.18           N
ATOM   1641  CA   GLY A 244      34.750   8.963  28.748  1.00 28.18           C
ATOM   1642  C    GLY A 244      34.395   8.194  27.500  1.00 28.18           C
ATOM   1643  O    GLY A 244      35.214   8.033  26.582  1.00 28.18           O
ATOM   1644  N    CYS A 245      33.157   7.720  27.465  1.00 38.39           N
ATOM   1645  CA   CYS A 245      32.680   6.967  26.321  1.00 38.39           C
ATOM   1646  CB   CYS A 245      31.280   6.427  26.573  1.00 29.10           C
ATOM   1647  SG   CYS A 245      31.200   5.180  27.838  1.00 29.10           S
ATOM   1648  C    CYS A 245      32.658   7.863  25.108  1.00 38.39           C
ATOM   1649  O    CYS A 245      32.999   7.427  24.020  1.00 38.39           O
ATOM   1650  N    VAL A 246      32.254   9.115  25.297  1.00 42.15           N
ATOM   1651  CA   VAL A 246      32.197  10.064  24.195  1.00 42.15           C
ATOM   1652  CB   VAL A 246      31.480  11.384  24.620  1.00 22.39           C
ATOM   1653  CG1  VAL A 246      31.423  12.360  23.441  1.00 22.39           C
ATOM   1654  CG2  VAL A 246      30.063  11.072  25.115  1.00 22.39           C
ATOM   1655  C    VAL A 246      33.613  10.371  23.707  1.00 42.15           C
ATOM   1656  O    VAL A 246      33.883  10.332  22.504  1.00 42.15           O
ATOM   1657  N    LEU A 247      34.516  10.670  24.640  1.00 38.53           N
ATOM   1658  CA   LEU A 247      35.898  10.970  24.276  1.00 38.53           C
ATOM   1659  CB   LEU A 247      36.771  11.180  25.516  1.00 30.05           C
ATOM   1660  CG   LEU A 247      38.271  11.205  25.181  1.00 30.05           C
ATOM   1661  CD1  LEU A 247      38.582  12.449  24.346  1.00 30.05           C
ATOM   1662  CD2  LEU A 247      39.096  11.187  26.444  1.00 30.05           C
ATOM   1663  C    LEU A 247      36.467   9.806  23.485  1.00 38.53           C
ATOM   1664  O    LEU A 247      37.105   9.993  22.446  1.00 38.53           O
ATOM   1665  N    ALA A 248      36.250   8.598  23.999  1.00 32.57           N
ATOM   1666  CA   ALA A 248      36.738   7.403  23.330  1.00 32.57           C
ATOM   1667  CB   ALA A 248      36.273   6.173  24.081  1.00 27.10           C
ATOM   1668  C    ALA A 248      36.202   7.380  21.900  1.00 32.57           C
ATOM   1669  O    ALA A 248      36.956   7.261  20.931  1.00 32.57           O
ATOM   1670  N    GLU A 249      34.886   7.509  21.793  1.00 45.84           N
ATOM   1671  CA   GLU A 249      34.168   7.513  20.526  1.00 45.84           C
ATOM   1672  CB   GLU A 249      32.676   7.687  20.813  1.00 35.09           C
ATOM   1673  CG   GLU A 249      31.804   7.735  19.592  1.00 35.09           C
ATOM   1674  CD   GLU A 249      30.376   7.417  19.919  1.00 35.09           C
ATOM   1675  OE1  GLU A 249      30.155   6.787  20.988  1.00 35.09           O
ATOM   1676  OE2  GLU A 249      29.494   7.778  19.099  1.00 35.09           O
ATOM   1677  C    GLU A 249      34.647   8.588  19.543  1.00 45.84           C
```

FIG. 7-29

```
ATOM   1678  O    GLU A 249      34.514    8.430   18.331  1.00 45.84           O
ATOM   1679  N    LEU A 250      35.186    9.690   20.055  1.00 34.77           N
ATOM   1680  CA   LEU A 250      35.683   10.743   19.180  1.00 34.77           C
ATOM   1681  CB   LEU A 250      35.823   12.050   19.943  1.00 36.13           C
ATOM   1682  CG   LEU A 250      34.502   12.772   20.158  1.00 36.13           C
ATOM   1683  CD1  LEU A 250      34.725   13.951   21.087  1.00 36.13           C
ATOM   1684  CD2  LEU A 250      33.949   13.219   18.817  1.00 36.13           C
ATOM   1685  C    LEU A 250      37.032   10.347   18.619  1.00 34.77           C
ATOM   1686  O    LEU A 250      37.362   10.654   17.472  1.00 34.77           O
ATOM   1687  N    LEU A 251      37.814    9.668   19.446  1.00 47.64           N
ATOM   1688  CA   LEU A 251      39.133    9.209   19.052  1.00 47.64           C
ATOM   1689  CB   LEU A 251      39.948    8.857   20.296  1.00 23.98           C
ATOM   1690  CG   LEU A 251      40.337   10.062   21.135  1.00 23.98           C
ATOM   1691  CD1  LEU A 251      41.142    9.605   22.347  1.00 23.98           C
ATOM   1692  CD2  LEU A 251      41.134   11.026   20.255  1.00 23.98           C
ATOM   1693  C    LEU A 251      39.027    7.985   18.155  1.00 47.64           C
ATOM   1694  O    LEU A 251      39.900    7.739   17.314  1.00 47.64           O
ATOM   1695  N    LEU A 252      37.948    7.230   18.338  1.00 46.58           N
ATOM   1696  CA   LEU A 252      37.740    6.007   17.583  1.00 46.58           C
ATOM   1697  CB   LEU A 252      37.070    4.942   18.452  1.00 46.31           C
ATOM   1698  CG   LEU A 252      37.820    3.648   18.707  1.00 46.31           C
ATOM   1699  CD1  LEU A 252      38.946    3.923   19.622  1.00 46.31           C
ATOM   1700  CD2  LEU A 252      36.893    2.640   19.336  1.00 46.31           C
ATOM   1701  C    LEU A 252      36.911    6.191   16.340  1.00 46.58           C
ATOM   1702  O    LEU A 252      36.934    5.338   15.468  1.00 46.58           O
ATOM   1703  N    GLY A 253      36.186    7.297   16.241  1.00 28.57           N
ATOM   1704  CA   GLY A 253      35.361    7.499   15.065  1.00 28.57           C
ATOM   1705  C    GLY A 253      34.173    6.562   15.122  1.00 28.57           C
ATOM   1706  O    GLY A 253      33.582    6.232   14.098  1.00 28.57           O
ATOM   1707  N    GLN A 254      33.838    6.125   16.335  1.00 27.85           N
ATOM   1708  CA   GLN A 254      32.704    5.238   16.579  1.00 27.85           C
ATOM   1709  CB   GLN A 254      32.716    4.087   15.596  1.00 49.54           C
ATOM   1710  CG   GLN A 254      33.990    3.316   15.651  1.00 49.54           C
ATOM   1711  CD   GLN A 254      33.788    1.888   15.237  1.00 49.54           C
ATOM   1712  OE1  GLN A 254      33.707    0.988   16.080  1.00 49.54           O
ATOM   1713  NE2  GLN A 254      33.684    1.664   13.929  1.00 49.54           N
ATOM   1714  C    GLN A 254      32.683    4.674   18.005  1.00 27.85           C
ATOM   1715  O    GLN A 254      33.724    4.504   18.649  1.00 27.85           O
ATOM   1716  N    PRO A 255      31.481    4.362   18.503  1.00 29.97           N
ATOM   1717  CD   PRO A 255      30.246    4.399   17.700  1.00 18.84           C
ATOM   1718  CA   PRO A 255      31.224    3.812   19.839  1.00 29.97           C
ATOM   1719  CB   PRO A 255      29.819    3.245   19.707  1.00 18.84           C
ATOM   1720  CG   PRO A 255      29.176    4.193   18.732  1.00 18.84           C
ATOM   1721  C    PRO A 255      32.222    2.739   20.242  1.00 29.97           C
ATOM   1722  O    PRO A 255      32.461    1.798   19.490  1.00 29.97           O
ATOM   1723  N    ILE A 256      32.782    2.877   21.440  1.00 42.67           N
ATOM   1724  CA   ILE A 256      33.759    1.925   21.971  1.00 42.67           C
ATOM   1725  CB   ILE A 256      34.675    2.622   22.983  1.00 27.42           C
ATOM   1726  CG2  ILE A 256      33.850    3.159   24.121  1.00 27.42           C
ATOM   1727  CG1  ILE A 256      35.713    1.652   23.522  1.00 27.42           C
ATOM   1728  CD1  ILE A 256      36.742    2.318   24.398  1.00 27.42           C
ATOM   1729  C    ILE A 256      33.101    0.721   22.649  1.00 42.67           C
ATOM   1730  O    ILE A 256      33.695   -0.348   22.741  1.00 42.67           O
ATOM   1731  N    PHE A 257      31.879    0.905   23.134  1.00 49.60           N
ATOM   1732  CA   PHE A 257      31.145   -0.171   23.792  1.00 49.60           C
ATOM   1733  CB   PHE A 257      30.934    0.136   25.281  1.00 31.85           C
ATOM   1734  CG   PHE A 257      32.221    0.304   26.062  1.00 31.85           C
ATOM   1735  CD1  PHE A 257      33.280   -0.592   25.895  1.00 31.85           C
ATOM   1736  CD2  PHE A 257      32.376    1.364   26.961  1.00 31.85           C
ATOM   1737  CE1  PHE A 257      34.473   -0.435   26.605  1.00 31.85           C
```

FIG. 7-30

| ATOM | 1738 | CE2 | PHE | A | 257 | 33.565 | 1.526 | 27.676 | 1.00 | 31.85 | C |
|---|---|---|---|---|---|---|---|---|---|---|---|
| ATOM | 1739 | CZ | PHE | A | 257 | 34.618 | 0.621 | 27.494 | 1.00 | 31.85 | C |
| ATOM | 1740 | C | PHE | A | 257 | 29.807 | -0.295 | 23.090 | 1.00 | 49.60 | C |
| ATOM | 1741 | O | PHE | A | 257 | 28.760 | 0.047 | 23.639 | 1.00 | 49.60 | O |
| ATOM | 1742 | N | PRO | A | 258 | 29.833 | -0.785 | 21.850 | 1.00 | 74.41 | N |
| ATOM | 1743 | CD | PRO | A | 258 | 31.056 | -1.288 | 21.203 | 1.00 | 59.92 | C |
| ATOM | 1744 | CA | PRO | A | 258 | 28.664 | -0.984 | 20.993 | 1.00 | 74.41 | C |
| ATOM | 1745 | CB | PRO | A | 258 | 29.287 | -1.196 | 19.626 | 1.00 | 59.92 | C |
| ATOM | 1746 | CG | PRO | A | 258 | 30.517 | -1.961 | 19.963 | 1.00 | 59.92 | C |
| ATOM | 1747 | C | PRO | A | 258 | 27.841 | -2.174 | 21.460 | 1.00 | 74.41 | C |
| ATOM | 1748 | O | PRO | A | 258 | 27.191 | -2.854 | 20.659 | 1.00 | 74.41 | O |
| ATOM | 1749 | N | GLY | A | 259 | 27.884 | -2.403 | 22.773 | 1.00 | 41.04 | N |
| ATOM | 1750 | CA | GLY | A | 259 | 27.152 | -3.496 | 23.388 | 1.00 | 41.04 | C |
| ATOM | 1751 | C | GLY | A | 259 | 25.715 | -3.584 | 22.913 | 1.00 | 41.04 | C |
| ATOM | 1752 | O | GLY | A | 259 | 25.065 | -2.559 | 22.699 | 1.00 | 41.04 | O |
| ATOM | 1753 | N | ASP | A | 260 | 25.213 | -4.810 | 22.765 | 1.00 | 78.48 | N |
| ATOM | 1754 | CA | ASP | A | 260 | 23.853 | -5.011 | 22.283 | 1.00 | 78.48 | C |
| ATOM | 1755 | CB | ASP | A | 260 | 23.795 | -6.235 | 21.338 | 1.00 | 81.48 | C |
| ATOM | 1756 | CG | ASP | A | 260 | 23.597 | -7.569 | 22.068 | 1.00 | 81.48 | C |
| ATOM | 1757 | OD1 | ASP | A | 260 | 23.030 | -8.497 | 21.449 | 1.00 | 81.48 | O |
| ATOM | 1758 | OD2 | ASP | A | 260 | 24.008 | -7.711 | 23.239 | 1.00 | 81.48 | O |
| ATOM | 1759 | C | ASP | A | 260 | 22.734 | -5.101 | 23.328 | 1.00 | 78.48 | C |
| ATOM | 1760 | O | ASP | A | 260 | 21.597 | -4.709 | 23.046 | 1.00 | 78.48 | O |
| ATOM | 1761 | N | SER | A | 261 | 23.048 | -5.588 | 24.527 | 1.00 | 63.04 | N |
| ATOM | 1762 | CA | SER | A | 261 | 22.040 | -5.732 | 25.572 | 1.00 | 63.04 | C |
| ATOM | 1763 | CB | SER | A | 261 | 21.181 | -6.971 | 25.285 | 1.00 | 76.61 | C |
| ATOM | 1764 | OG | SER | A | 261 | 20.145 | -7.131 | 26.237 | 1.00 | 76.61 | O |
| ATOM | 1765 | C | SER | A | 261 | 22.777 | -5.902 | 26.881 | 1.00 | 63.04 | C |
| ATOM | 1766 | O | SER | A | 261 | 23.735 | -6.664 | 26.936 | 1.00 | 63.04 | O |
| ATOM | 1767 | N | GLY | A | 262 | 22.337 | -5.188 | 27.917 | 1.00 | 55.63 | N |
| ATOM | 1768 | CA | GLY | A | 262 | 22.973 | -5.274 | 29.225 | 1.00 | 55.63 | C |
| ATOM | 1769 | C | GLY | A | 262 | 23.988 | -6.394 | 29.366 | 1.00 | 55.63 | C |
| ATOM | 1770 | O | GLY | A | 262 | 25.101 | -6.170 | 29.860 | 1.00 | 55.63 | O |
| ATOM | 1771 | N | GLY | A | 263 | 23.593 | -7.599 | 28.946 | 1.00 | 46.75 | N |
| ATOM | 1772 | CA | GLY | A | 263 | 24.486 | -8.742 | 29.001 | 1.00 | 46.75 | C |
| ATOM | 1773 | C | GLY | A | 263 | 25.741 | -8.500 | 28.178 | 1.00 | 46.75 | C |
| ATOM | 1774 | O | GLY | A | 263 | 26.845 | -8.737 | 28.653 | 1.00 | 46.75 | O |
| ATOM | 1775 | N | ASP | A | 264 | 25.597 | -8.011 | 26.951 | 1.00 | 72.15 | N |
| ATOM | 1776 | CA | ASP | A | 264 | 26.776 | -7.779 | 26.131 | 1.00 | 72.15 | C |
| ATOM | 1777 | CB | ASP | A | 264 | 26.423 | -7.812 | 24.638 | 1.00 | 79.37 | C |
| ATOM | 1778 | CG | ASP | A | 264 | 27.617 | -8.174 | 23.766 | 1.00 | 79.37 | C |
| ATOM | 1779 | OD1 | ASP | A | 264 | 27.640 | -7.776 | 22.583 | 1.00 | 79.37 | O |
| ATOM | 1780 | OD2 | ASP | A | 264 | 28.531 | -8.865 | 24.263 | 1.00 | 79.37 | O |
| ATOM | 1781 | C | ASP | A | 264 | 27.462 | -6.459 | 26.464 | 1.00 | 72.15 | C |
| ATOM | 1782 | O | ASP | A | 264 | 28.677 | -6.328 | 26.280 | 1.00 | 72.15 | O |
| ATOM | 1783 | N | GLN | A | 265 | 26.702 | -5.481 | 26.952 | 1.00 | 44.20 | N |
| ATOM | 1784 | CA | GLN | A | 265 | 27.304 | -4.199 | 27.283 | 1.00 | 44.20 | C |
| ATOM | 1785 | CB | GLN | A | 265 | 26.255 | -3.253 | 27.884 | 1.00 | 38.28 | C |
| ATOM | 1786 | CG | GLN | A | 265 | 26.694 | -1.779 | 28.080 | 1.00 | 38.28 | C |
| ATOM | 1787 | CD | GLN | A | 265 | 27.405 | -1.182 | 26.871 | 1.00 | 38.28 | C |
| ATOM | 1788 | OE1 | GLN | A | 265 | 26.959 | -1.330 | 25.733 | 1.00 | 38.28 | O |
| ATOM | 1789 | NE2 | GLN | A | 265 | 28.510 | -0.491 | 27.121 | 1.00 | 38.28 | N |
| ATOM | 1790 | C | GLN | A | 265 | 28.476 | -4.419 | 28.246 | 1.00 | 44.20 | C |
| ATOM | 1791 | O | GLN | A | 265 | 29.580 | -3.912 | 28.014 | 1.00 | 44.20 | O |
| ATOM | 1792 | N | LEU | A | 266 | 28.260 | -5.196 | 29.306 | 1.00 | 39.57 | N |
| ATOM | 1793 | CA | LEU | A | 266 | 29.342 | -5.450 | 30.255 | 1.00 | 39.57 | C |
| ATOM | 1794 | CB | LEU | A | 266 | 28.827 | -6.131 | 31.528 | 1.00 | 46.71 | C |
| ATOM | 1795 | CG | LEU | A | 266 | 29.945 | -6.504 | 32.519 | 1.00 | 46.71 | C |
| ATOM | 1796 | CD1 | LEU | A | 266 | 30.777 | -5.269 | 32.872 | 1.00 | 46.71 | C |
| ATOM | 1797 | CD2 | LEU | A | 266 | 29.340 | -7.106 | 33.769 | 1.00 | 46.71 | C |

FIG. 7-31

```
ATOM   1798  C    LEU A 266      30.477  -6.286  29.666  1.00 39.57           C
ATOM   1799  O    LEU A 266      31.613  -6.224  30.146  1.00 39.57           O
ATOM   1800  N    VAL A 267      30.188  -7.087  28.649  1.00 46.20           N
ATOM   1801  CA   VAL A 267      31.257  -7.872  28.054  1.00 46.20           C
ATOM   1802  CB   VAL A 267      30.710  -8.857  27.013  1.00 60.14           C
ATOM   1803  CG1  VAL A 267      31.579  -8.859  25.770  1.00 60.14           C
ATOM   1804  CG2  VAL A 267      30.687 -10.245  27.611  1.00 60.14           C
ATOM   1805  C    VAL A 267      32.242  -6.910  27.409  1.00 46.20           C
ATOM   1806  O    VAL A 267      33.432  -6.871  27.756  1.00 46.20           O
ATOM   1807  N    GLU A 268      31.714  -6.115  26.486  1.00 41.45           N
ATOM   1808  CA   GLU A 268      32.493  -5.111  25.787  1.00 41.45           C
ATOM   1809  CB   GLU A 268      31.547  -4.099  25.132  1.00 51.39           C
ATOM   1810  CG   GLU A 268      31.051  -4.526  23.770  1.00 51.39           C
ATOM   1811  CD   GLU A 268      32.135  -4.413  22.732  1.00 51.39           C
ATOM   1812  OE1  GLU A 268      33.292  -4.133  23.105  1.00 51.39           O
ATOM   1813  OE2  GLU A 268      31.836  -4.604  21.542  1.00 51.39           O
ATOM   1814  C    GLU A 268      33.444  -4.389  26.737  1.00 41.45           C
ATOM   1815  O    GLU A 268      34.624  -4.220  26.444  1.00 41.45           O
ATOM   1816  N    ILE A 269      32.927  -3.985  27.887  1.00 40.82           N
ATOM   1817  CA   ILE A 269      33.727  -3.261  28.858  1.00 40.82           C
ATOM   1818  CB   ILE A 269      32.820  -2.724  29.979  1.00 42.65           C
ATOM   1819  CG2  ILE A 269      33.537  -1.631  30.783  1.00 42.65           C
ATOM   1820  CG1  ILE A 269      31.544  -2.175  29.333  1.00 42.65           C
ATOM   1821  CD1  ILE A 269      30.835  -1.137  30.126  1.00 42.65           C
ATOM   1822  C    ILE A 269      34.843  -4.126  29.429  1.00 40.82           C
ATOM   1823  O    ILE A 269      36.006  -3.690  29.544  1.00 40.82           O
ATOM   1824  N    ILE A 270      34.496  -5.363  29.766  1.00 57.32           N
ATOM   1825  CA   ILE A 270      35.473  -6.279  30.321  1.00 57.32           C
ATOM   1826  CB   ILE A 270      34.760  -7.489  30.997  1.00 69.21           C
ATOM   1827  CG2  ILE A 270      35.767  -8.565  31.346  1.00 69.21           C
ATOM   1828  CG1  ILE A 270      34.041  -7.017  32.272  1.00 69.21           C
ATOM   1829  CD1  ILE A 270      33.293  -8.078  33.001  1.00 69.21           C
ATOM   1830  C    ILE A 270      36.439  -6.738  29.225  1.00 57.32           C
ATOM   1831  O    ILE A 270      37.522  -7.237  29.518  1.00 57.32           O
ATOM   1832  N    LYS A 271      36.064  -6.521  27.968  1.00 59.60           N
ATOM   1833  CA   LYS A 271      36.884  -6.935  26.834  1.00 59.60           C
ATOM   1834  CB   LYS A 271      36.007  -7.041  25.578  1.00 76.71           C
ATOM   1835  CG   LYS A 271      36.417  -8.148  24.616  1.00 76.71           C
ATOM   1836  CD   LYS A 271      35.718  -9.449  24.966  1.00 76.71           C
ATOM   1837  CE   LYS A 271      34.528  -9.693  24.058  1.00 76.71           C
ATOM   1838  NZ   LYS A 271      33.685 -10.823  24.536  1.00 76.71           N
ATOM   1839  C    LYS A 271      38.011  -5.943  26.574  1.00 59.60           C
ATOM   1840  O    LYS A 271      38.890  -6.183  25.742  1.00 59.60           O
ATOM   1841  N    VAL A 272      37.997  -4.851  27.321  1.00 51.34           N
ATOM   1842  CA   VAL A 272      38.953  -3.772  27.135  1.00 51.34           C
ATOM   1843  CB   VAL A 272      38.211  -2.561  26.563  1.00 63.55           C
ATOM   1844  CG1  VAL A 272      36.795  -2.562  27.102  1.00 63.55           C
ATOM   1845  CG2  VAL A 272      38.898  -1.264  26.961  1.00 63.55           C
ATOM   1846  C    VAL A 272      39.571  -3.383  28.450  1.00 51.34           C
ATOM   1847  O    VAL A 272      40.739  -2.997  28.514  1.00 51.34           O
ATOM   1848  N    LEU A 273      38.762  -3.479  29.495  1.00 49.43           N
ATOM   1849  CA   LEU A 273      39.191  -3.121  30.833  1.00 49.43           C
ATOM   1850  CB   LEU A 273      38.077  -2.325  31.507  1.00 45.16           C
ATOM   1851  CG   LEU A 273      38.078  -0.877  31.107  1.00 45.16           C
ATOM   1852  CD1  LEU A 273      37.008  -0.097  31.838  1.00 45.16           C
ATOM   1853  CD2  LEU A 273      39.440  -0.399  31.472  1.00 45.16           C
ATOM   1854  C    LEU A 273      39.616  -4.287  31.726  1.00 49.43           C
ATOM   1855  O    LEU A 273      40.184  -4.083  32.803  1.00 49.43           O
ATOM   1856  N    GLY A 274      39.375  -5.506  31.265  1.00 48.33           N
ATOM   1857  CA   GLY A 274      39.736  -6.659  32.058  1.00 48.33           C
```

FIG. 7-32

```
ATOM   1858  C    GLY A 274      38.612  -6.963  33.013  1.00 48.33           C
ATOM   1859  O    GLY A 274      37.648  -6.200  33.130  1.00 48.33           O
ATOM   1860  N    THR A 275      38.725  -8.096  33.686  1.00 53.25           N
ATOM   1861  CA   THR A 275      37.708  -8.482  34.630  1.00 53.25           C
ATOM   1862  CB   THR A 275      37.869  -9.970  35.006  1.00 42.47           C
ATOM   1863  OG1  THR A 275      37.149 -10.763  34.060  1.00 42.47           O
ATOM   1864  CG2  THR A 275      37.343 -10.260  36.392  1.00 42.47           C
ATOM   1865  C    THR A 275      37.806  -7.585  35.854  1.00 53.25           C
ATOM   1866  O    THR A 275      38.905  -7.173  36.255  1.00 53.25           O
ATOM   1867  N    PRO A 276      36.648  -7.223  36.427  1.00 51.75           N
ATOM   1868  CD   PRO A 276      35.297  -7.572  35.951  1.00 37.19           C
ATOM   1869  CA   PRO A 276      36.617  -6.370  37.615  1.00 51.75           C
ATOM   1870  CB   PRO A 276      35.267  -5.671  37.514  1.00 37.19           C
ATOM   1871  CG   PRO A 276      34.395  -6.669  36.783  1.00 37.19           C
ATOM   1872  C    PRO A 276      36.758  -7.208  38.878  1.00 51.75           C
ATOM   1873  O    PRO A 276      36.031  -8.189  39.060  1.00 51.75           O
ATOM   1874  N    THR A 277      37.676  -6.792  39.750  1.00 57.70           N
ATOM   1875  CA   THR A 277      37.973  -7.473  41.013  1.00 57.70           C
ATOM   1876  CB   THR A 277      39.083  -6.725  41.783  1.00 52.56           C
ATOM   1877  OG1  THR A 277      38.582  -5.462  42.260  1.00 52.56           O
ATOM   1878  CG2  THR A 277      40.284  -6.477  40.861  1.00 52.56           C
ATOM   1879  C    THR A 277      36.741  -7.587  41.915  1.00 57.70           C
ATOM   1880  O    THR A 277      35.818  -6.782  41.807  1.00 57.70           O
ATOM   1881  N    ARG A 278      36.722  -8.582  42.800  1.00 67.76           N
ATOM   1882  CA   ARG A 278      35.577  -8.756  43.687  1.00 67.76           C
ATOM   1883  CB   ARG A 278      35.801  -9.926  44.658  1.00 82.36           C
ATOM   1884  CG   ARG A 278      35.966 -11.298  43.986  1.00 82.36           C
ATOM   1885  CD   ARG A 278      35.526 -12.440  44.911  1.00 82.36           C
ATOM   1886  NE   ARG A 278      35.855 -12.174  46.312  1.00 82.36           N
ATOM   1887  CZ   ARG A 278      35.606 -13.006  47.322  1.00 82.36           C
ATOM   1888  NH1  ARG A 278      35.020 -14.181  47.105  1.00 82.36           N
ATOM   1889  NH2  ARG A 278      35.936 -12.653  48.558  1.00 82.36           N
ATOM   1890  C    ARG A 278      35.312  -7.465  44.456  1.00 67.76           C
ATOM   1891  O    ARG A 278      34.171  -7.146  44.773  1.00 67.76           O
ATOM   1892  N    GLU A 279      36.368  -6.713  44.744  1.00 52.27           N
ATOM   1893  CA   GLU A 279      36.210  -5.454  45.453  1.00 52.27           C
ATOM   1894  CB   GLU A 279      37.574  -4.914  45.884  1.00103.68           C
ATOM   1895  CG   GLU A 279      38.020  -5.406  47.257  1.00103.68           C
ATOM   1896  CD   GLU A 279      38.191  -6.913  47.331  1.00103.68           C
ATOM   1897  OE1  GLU A 279      38.209  -7.441  48.464  1.00103.68           O
ATOM   1898  OE2  GLU A 279      38.318  -7.566  46.268  1.00103.68           O
ATOM   1899  C    GLU A 279      35.488  -4.447  44.559  1.00 52.27           C
ATOM   1900  O    GLU A 279      34.472  -3.873  44.970  1.00 52.27           O
ATOM   1901  N    GLN A 280      36.004  -4.249  43.340  1.00 47.01           N
ATOM   1902  CA   GLN A 280      35.395  -3.329  42.369  1.00 47.01           C
ATOM   1903  CB   GLN A 280      36.078  -3.430  41.001  1.00 53.57           C
ATOM   1904  CG   GLN A 280      37.430  -2.728  40.934  1.00 53.57           C
ATOM   1905  CD   GLN A 280      38.229  -3.082  39.687  1.00 53.57           C
ATOM   1906  OE1  GLN A 280      38.046  -4.145  39.098  1.00 53.57           O
ATOM   1907  NE2  GLN A 280      39.136  -2.200  39.296  1.00 53.57           N
ATOM   1908  C    GLN A 280      33.923  -3.642  42.208  1.00 47.01           C
ATOM   1909  O    GLN A 280      33.134  -2.785  41.843  1.00 47.01           O
ATOM   1910  N    ILE A 281      33.551  -4.878  42.481  1.00 36.21           N
ATOM   1911  CA   ILE A 281      32.159  -5.259  42.372  1.00 36.21           C
ATOM   1912  CB   ILE A 281      31.996  -6.785  42.514  1.00 53.52           C
ATOM   1913  CG2  ILE A 281      30.588  -7.189  42.105  1.00 53.52           C
ATOM   1914  CG1  ILE A 281      33.028  -7.515  41.645  1.00 53.52           C
ATOM   1915  CD1  ILE A 281      32.831  -7.358  40.163  1.00 53.52           C
ATOM   1916  C    ILE A 281      31.360  -4.552  43.481  1.00 36.21           C
ATOM   1917  O    ILE A 281      30.324  -3.926  43.218  1.00 36.21           O
```

FIG. 7-33

```
ATOM   1918  N    ALA A 282      31.849  -4.655  44.716  1.00 67.82           N
ATOM   1919  CA   ALA A 282      31.194  -4.021  45.855  1.00 67.82           C
ATOM   1920  CB   ALA A 282      31.993  -4.280  47.138  1.00 36.59           C
ATOM   1921  C    ALA A 282      31.121  -2.526  45.580  1.00 67.82           C
ATOM   1922  O    ALA A 282      30.048  -1.921  45.633  1.00 67.82           O
ATOM   1923  N    GLU A 283      32.279  -1.945  45.281  1.00 65.09           N
ATOM   1924  CA   GLU A 283      32.383  -0.527  44.989  1.00 65.09           C
ATOM   1925  CB   GLU A 283      33.790  -0.231  44.457  1.00 47.29           C
ATOM   1926  CG   GLU A 283      34.894  -0.583  45.484  1.00 47.29           C
ATOM   1927  CD   GLU A 283      36.344  -0.525  44.944  1.00 47.29           C
ATOM   1928  OE1  GLU A 283      36.736  -1.424  44.159  1.00 47.29           O
ATOM   1929  OE2  GLU A 283      37.097   0.412  45.320  1.00 47.29           O
ATOM   1930  C    GLU A 283      31.303  -0.080  43.997  1.00 65.09           C
ATOM   1931  O    GLU A 283      30.701   0.980  44.160  1.00 65.09           O
ATOM   1932  N    MET A 284      31.036  -0.895  42.984  1.00 40.50           N
ATOM   1933  CA   MET A 284      30.019  -0.536  42.001  1.00 40.50           C
ATOM   1934  CB   MET A 284      30.162  -1.394  40.743  1.00 61.67           C
ATOM   1935  CG   MET A 284      31.518  -1.262  40.059  1.00 61.67           C
ATOM   1936  SD   MET A 284      31.628  -2.303  38.597  1.00 61.67           S
ATOM   1937  CE   MET A 284      30.620  -1.428  37.655  1.00 61.67           C
ATOM   1938  C    MET A 284      28.625  -0.699  42.589  1.00 40.50           C
ATOM   1939  O    MET A 284      27.847   0.255  42.640  1.00 40.50           O
ATOM   1940  N    ASN A 285      28.308  -1.916  43.021  1.00 45.74           N
ATOM   1941  CA   ASN A 285      27.016  -2.216  43.632  1.00 45.74           C
ATOM   1942  CB   ASN A 285      25.963  -2.611  42.594  1.00 33.96           C
ATOM   1943  CG   ASN A 285      24.713  -3.208  43.238  1.00 33.96           C
ATOM   1944  OD1  ASN A 285      24.555  -3.155  44.455  1.00 33.96           O
ATOM   1945  ND2  ASN A 285      23.821  -3.769  42.426  1.00 33.96           N
ATOM   1946  C    ASN A 285      27.205  -3.374  44.573  1.00 45.74           C
ATOM   1947  O    ASN A 285      27.436  -4.490  44.142  1.00 45.74           O
ATOM   1948  N    PRO A 286      27.119  -3.128  45.878  1.00 72.20           N
ATOM   1949  CD   PRO A 286      27.071  -1.854  46.607  1.00 29.05           C
ATOM   1950  CA   PRO A 286      27.300  -4.254  46.792  1.00 72.20           C
ATOM   1951  CB   PRO A 286      27.330  -3.583  48.169  1.00 29.05           C
ATOM   1952  CG   PRO A 286      26.582  -2.295  47.951  1.00 29.05           C
ATOM   1953  C    PRO A 286      26.232  -5.350  46.654  1.00 72.20           C
ATOM   1954  O    PRO A 286      26.554  -6.533  46.727  1.00 72.20           O
ATOM   1955  N    ASN A 287      24.978  -4.968  46.424  1.00 55.18           N
ATOM   1956  CA   ASN A 287      23.904  -5.953  46.277  1.00 55.18           C
ATOM   1957  CB   ASN A 287      22.548  -5.257  46.141  1.00 76.93           C
ATOM   1958  CG   ASN A 287      22.288  -4.261  47.256  1.00 76.93           C
ATOM   1959  OD1  ASN A 287      21.140  -4.049  47.660  1.00 76.93           O
ATOM   1960  ND2  ASN A 287      23.351  -3.633  47.751  1.00 76.93           N
ATOM   1961  C    ASN A 287      24.126  -6.861  45.068  1.00 55.18           C
ATOM   1962  O    ASN A 287      23.477  -7.902  44.929  1.00 55.18           O
ATOM   1963  N    ALA A 294      35.182 -14.914  34.965  1.00 46.50           N
ATOM   1964  CA   ALA A 294      36.394 -15.530  34.431  1.00 46.50           C
ATOM   1965  CB   ALA A 294      36.106 -16.163  33.081  1.00 34.59           C
ATOM   1966  C    ALA A 294      37.493 -14.486  34.290  1.00 46.50           C
ATOM   1967  O    ALA A 294      37.532 -13.755  33.300  1.00 46.50           O
ATOM   1968  N    ALA A 295      38.383 -14.414  35.274  1.00 65.10           N
ATOM   1969  CA   ALA A 295      39.468 -13.436  35.245  1.00 65.10           C
ATOM   1970  CB   ALA A 295      40.586 -13.868  36.177  1.00 28.74           C
ATOM   1971  C    ALA A 295      40.037 -13.247  33.844  1.00 65.10           C
ATOM   1972  O    ALA A 295      40.432 -14.214  33.209  1.00 65.10           O
ATOM   1973  N    ALA A 296      40.086 -12.013  33.354  1.00 55.28           N
ATOM   1974  CA   ALA A 296      40.647 -11.755  32.031  1.00 55.28           C
ATOM   1975  CB   ALA A 296      39.512 -11.617  30.954  1.00 27.51           C
ATOM   1976  C    ALA A 296      41.480 -10.486  32.115  1.00 55.28           C
ATOM   1977  O    ALA A 296      41.059  -9.488  32.732  1.00 55.28           O
```

FIG. 7-34

```
ATOM   1978  N    ALA A 297      42.674  -10.551   31.529  1.00 78.25           N
ATOM   1979  CA   ALA A 297      43.594   -9.419   31.487  1.00 78.25           C
ATOM   1980  CB   ALA A 297      44.828   -9.793   30.698  1.00 53.02           C
ATOM   1981  C    ALA A 297      42.883   -8.250   30.813  1.00 78.25           C
ATOM   1982  O    ALA A 297      41.667   -8.297   30.572  1.00 78.25           O
ATOM   1983  N    ALA A 298      43.603   -7.191   30.496  1.00 80.48           N
ATOM   1984  CA   ALA A 298      42.912   -6.107   29.842  1.00 80.48           C
ATOM   1985  CB   ALA A 298      42.554   -5.005   30.829  1.00 61.69           C
ATOM   1986  C    ALA A 298      43.797   -5.589   28.774  1.00 80.48           C
ATOM   1987  O    ALA A 298      45.009   -5.459   28.956  1.00 80.48           O
ATOM   1988  N    HIS A 299      43.176   -5.291   27.650  1.00 76.13           N
ATOM   1989  CA   HIS A 299      43.933   -4.801   26.551  1.00 76.13           C
ATOM   1990  CB   HIS A 299      42.995   -4.512   25.365  1.00 32.75           C
ATOM   1991  CG   HIS A 299      43.645   -4.684   24.032  1.00 23.68           C
ATOM   1992  CD2  HIS A 299      43.900   -3.800   23.042  1.00 23.68           C
ATOM   1993  ND1  HIS A 299      44.108   -5.916   23.591  1.00 23.68           N
ATOM   1994  CE1  HIS A 299      44.623   -5.770   22.376  1.00 23.68           C
ATOM   1995  NE2  HIS A 299      44.515   -4.502   22.021  1.00 23.68           N
ATOM   1996  C    HIS A 299      44.475   -3.508   27.086  1.00 76.13           C
ATOM   1997  O    HIS A 299      43.942   -2.976   27.995  1.00 76.13           O
ATOM   1998  N    PRO A 300      45.585   -3.021   26.563  1.00 51.41           N
ATOM   1999  CD   PRO A 300      46.601   -3.841   25.915  1.00 68.30           C
ATOM   2000  CA   PRO A 300      46.157   -1.746   27.025  1.00 51.41           C
ATOM   2001  CB   PRO A 300      47.398   -1.595   26.171  1.00 68.30           C
ATOM   2002  CG   PRO A 300      47.788   -2.953   25.952  1.00 68.30           C
ATOM   2003  C    PRO A 300      45.142   -0.744   26.584  1.00 51.41           C
ATOM   2004  O    PRO A 300      44.110   -1.136   26.049  1.00 51.41           O
ATOM   2005  N    TRP A 301      45.439    0.531   26.785  1.00 53.94           N
ATOM   2006  CA   TRP A 301      44.519    1.577   26.396  1.00 53.94           C
ATOM   2007  CB   TRP A 301      44.606    2.735   27.374  1.00 51.46           C
ATOM   2008  CG   TRP A 301      43.759    2.431   28.485  1.00 51.46           C
ATOM   2009  CD2  TRP A 301      42.336    2.388   28.462  1.00 51.46           C
ATOM   2010  CE2  TRP A 301      41.945    1.923   29.737  1.00 51.46           C
ATOM   2011  CE3  TRP A 301      41.375    2.682   27.491  1.00 51.46           C
ATOM   2012  CD1  TRP A 301      44.145    2.010   29.714  1.00 51.46           C
ATOM   2013  NE1  TRP A 301      43.049    1.696   30.468  1.00 51.46           N
ATOM   2014  CZ2  TRP A 301      40.594    1.769   30.051  1.00 51.46           C
ATOM   2015  CZ3  TRP A 301      40.053    2.512   27.811  1.00 51.46           C
ATOM   2016  CH2  TRP A 301      39.668    2.062   29.081  1.00 51.46           C
ATOM   2017  C    TRP A 301      44.933    1.991   25.024  1.00 53.94           C
ATOM   2018  O    TRP A 301      44.121    2.299   24.144  1.00 53.94           O
ATOM   2019  N    THR A 302      46.240    1.897   24.864  1.00 51.94           N
ATOM   2020  CA   THR A 302      46.975    2.237   23.666  1.00 51.94           C
ATOM   2021  CB   THR A 302      48.443    2.356   24.035  1.00 54.81           C
ATOM   2022  OG1  THR A 302      49.161    2.871   22.918  1.00 54.81           O
ATOM   2023  CG2  THR A 302      48.989    1.009   24.488  1.00 54.81           C
ATOM   2024  C    THR A 302      46.804    1.246   22.508  1.00 51.94           C
ATOM   2025  O    THR A 302      47.024    1.594   21.338  1.00 51.94           O
ATOM   2026  N    ALA A 303      46.393    0.030   22.844  1.00 55.43           N
ATOM   2027  CA   ALA A 303      46.211   -1.003   21.861  1.00 55.43           C
ATOM   2028  CB   ALA A 303      46.418   -2.368   22.517  1.00 65.28           C
ATOM   2029  C    ALA A 303      44.827   -0.849   21.331  1.00 55.43           C
ATOM   2030  O    ALA A 303      44.378   -1.641   20.518  1.00 55.43           O
ATOM   2031  N    VAL A 304      44.188    0.219   21.784  1.00 60.12           N
ATOM   2032  CA   VAL A 304      42.815    0.529   21.428  1.00 60.12           C
ATOM   2033  CB   VAL A 304      42.050    0.732   22.733  1.00 65.14           C
ATOM   2034  CG1  VAL A 304      40.613    1.144   22.502  1.00 65.14           C
ATOM   2035  CG2  VAL A 304      42.137   -0.561   23.531  1.00 65.14           C
ATOM   2036  C    VAL A 304      42.564    1.706   20.479  1.00 60.12           C
ATOM   2037  O    VAL A 304      41.623    1.694   19.679  1.00 60.12           O
```

FIG. 7-35

```
ATOM   2038  N    PHE A 305      43.407   2.721  20.535  1.00 63.30           N
ATOM   2039  CA   PHE A 305      43.178   3.864  19.686  1.00 63.30           C
ATOM   2040  CB   PHE A 305      43.303   5.145  20.506  1.00 50.37           C
ATOM   2041  CG   PHE A 305      42.202   5.309  21.516  1.00 50.37           C
ATOM   2042  CD1  PHE A 305      40.904   5.638  21.118  1.00 50.37           C
ATOM   2043  CD2  PHE A 305      42.433   5.007  22.844  1.00 50.37           C
ATOM   2044  CE1  PHE A 305      39.858   5.650  22.039  1.00 50.37           C
ATOM   2045  CE2  PHE A 305      41.410   5.016  23.756  1.00 50.37           C
ATOM   2046  CZ   PHE A 305      40.115   5.332  23.362  1.00 50.37           C
ATOM   2047  C    PHE A 305      44.218   3.731  18.631  1.00 63.30           C
ATOM   2048  O    PHE A 305      45.084   2.855  18.713  1.00 63.30           O
ATOM   2049  N    ARG A 306      44.116   4.567  17.619  1.00 78.76           N
ATOM   2050  CA   ARG A 306      45.044   4.492  16.528  1.00 78.76           C
ATOM   2051  CB   ARG A 306      44.789   5.628  15.538  1.00103.68           C
ATOM   2052  CG   ARG A 306      43.547   5.394  14.716  1.00103.68           C
ATOM   2053  CD   ARG A 306      42.306   5.411  15.606  1.00103.68           C
ATOM   2054  NE   ARG A 306      41.152   4.710  15.034  1.00103.68           N
ATOM   2055  CZ   ARG A 306      40.951   3.387  15.084  1.00103.68           C
ATOM   2056  NH1  ARG A 306      41.823   2.571  15.690  1.00103.68           N
ATOM   2057  NH2  ARG A 306      39.859   2.866  14.529  1.00103.68           N
ATOM   2058  C    ARG A 306      46.467   4.574  16.984  1.00 78.76           C
ATOM   2059  O    ARG A 306      46.767   4.995  18.104  1.00 78.76           O
ATOM   2060  N    PRO A 307      47.382   4.131  16.130  1.00 60.85           N
ATOM   2061  CD   PRO A 307      47.239   3.396  14.864  1.00 52.78           C
ATOM   2062  CA   PRO A 307      48.779   4.224  16.547  1.00 60.85           C
ATOM   2063  CB   PRO A 307      49.527   3.818  15.295  1.00 52.78           C
ATOM   2064  CG   PRO A 307      48.603   2.831  14.678  1.00 52.78           C
ATOM   2065  C    PRO A 307      49.012   5.694  16.874  1.00 60.85           C
ATOM   2066  O    PRO A 307      49.388   6.052  17.990  1.00 60.85           O
ATOM   2067  N    ALA A 308      48.705   6.535  15.892  1.00 59.09           N
ATOM   2068  CA   ALA A 308      48.847   7.994  16.002  1.00 59.09           C
ATOM   2069  CB   ALA A 308      48.416   8.641  14.698  1.00 33.38           C
ATOM   2070  C    ALA A 308      48.181   8.765  17.170  1.00 59.09           C
ATOM   2071  O    ALA A 308      48.650   9.854  17.513  1.00 59.09           O
ATOM   2072  N    THR A 309      47.110   8.240  17.765  1.00 53.54           N
ATOM   2073  CA   THR A 309      46.429   8.916  18.873  1.00 53.54           C
ATOM   2074  CB   THR A 309      45.460   7.948  19.564  1.00 60.52           C
ATOM   2075  OG1  THR A 309      44.826   7.127  18.575  1.00 60.52           O
ATOM   2076  CG2  THR A 309      44.393   8.716  20.309  1.00 60.52           C
ATOM   2077  C    THR A 309      47.406   9.490  19.916  1.00 53.54           C
ATOM   2078  O    THR A 309      48.381   8.847  20.306  1.00 53.54           O
ATOM   2079  N    PRO A 310      47.148  10.724  20.375  1.00 46.26           N
ATOM   2080  CD   PRO A 310      46.108  11.633  19.870  1.00 37.32           C
ATOM   2081  CA   PRO A 310      47.977  11.411  21.365  1.00 46.26           C
ATOM   2082  CB   PRO A 310      47.329  12.782  21.467  1.00 37.32           C
ATOM   2083  CG   PRO A 310      46.731  12.969  20.132  1.00 37.32           C
ATOM   2084  C    PRO A 310      47.979  10.694  22.704  1.00 46.26           C
ATOM   2085  O    PRO A 310      46.931  10.356  23.255  1.00 46.26           O
ATOM   2086  N    PRO A 311      49.167  10.481  23.260  1.00 42.77           N
ATOM   2087  CD   PRO A 311      50.461  10.996  22.787  1.00 28.90           C
ATOM   2088  CA   PRO A 311      49.308   9.797  24.545  1.00 42.77           C
ATOM   2089  CB   PRO A 311      50.793   9.970  24.864  1.00 28.90           C
ATOM   2090  CG   PRO A 311      51.429  10.116  23.527  1.00 28.90           C
ATOM   2091  C    PRO A 311      48.419  10.392  25.634  1.00 42.77           C
ATOM   2092  O    PRO A 311      47.808   9.669  26.431  1.00 42.77           O
ATOM   2093  N    GLU A 312      48.349  11.718  25.652  1.00 54.66           N
ATOM   2094  CA   GLU A 312      47.572  12.421  26.658  1.00 54.66           C
ATOM   2095  CB   GLU A 312      47.926  13.903  26.636  1.00 69.68           C
ATOM   2096  CG   GLU A 312      47.966  14.501  28.020  1.00 69.68           C
ATOM   2097  CD   GLU A 312      48.933  13.770  28.938  1.00 69.68           C
```

FIG. 7-36

```
ATOM   2098  OE1 GLU A 312      50.159  13.964  28.791  1.00 69.68           O
ATOM   2099  OE2 GLU A 312      48.468  12.991  29.800  1.00 69.68           O
ATOM   2100  C   GLU A 312      46.068  12.238  26.515  1.00 54.66           C
ATOM   2101  O   GLU A 312      45.318  12.467  27.460  1.00 54.66           O
ATOM   2102  N   ALA A 313      45.625  11.826  25.335  1.00 40.49           N
ATOM   2103  CA  ALA A 313      44.207  11.603  25.120  1.00 40.49           C
ATOM   2104  CB  ALA A 313      43.886  11.640  23.629  1.00 29.07           C
ATOM   2105  C   ALA A 313      43.881  10.236  25.702  1.00 40.49           C
ATOM   2106  O   ALA A 313      42.816  10.028  26.291  1.00 40.49           O
ATOM   2107  N   ILE A 314      44.820   9.310  25.538  1.00 46.94           N
ATOM   2108  CA  ILE A 314      44.649   7.958  26.041  1.00 46.94           C
ATOM   2109  CB  ILE A 314      45.668   6.995  25.404  1.00 40.68           C
ATOM   2110  CG2 ILE A 314      45.335   5.549  25.795  1.00 40.68           C
ATOM   2111  CG1 ILE A 314      45.638   7.167  23.879  1.00 40.68           C
ATOM   2112  CD1 ILE A 314      46.664   6.366  23.123  1.00 40.68           C
ATOM   2113  C   ILE A 314      44.813   7.953  27.553  1.00 46.94           C
ATOM   2114  O   ILE A 314      44.257   7.099  28.236  1.00 46.94           O
ATOM   2115  N   ALA A 315      45.570   8.911  28.076  1.00 48.22           N
ATOM   2116  CA  ALA A 315      45.771   9.006  29.519  1.00 48.22           C
ATOM   2117  CB  ALA A 315      46.874  10.012  29.821  1.00 30.87           C
ATOM   2118  C   ALA A 315      44.451   9.448  30.166  1.00 48.22           C
ATOM   2119  O   ALA A 315      43.917   8.781  31.057  1.00 48.22           O
ATOM   2120  N   LEU A 316      43.931  10.579  29.697  1.00 48.77           N
ATOM   2121  CA  LEU A 316      42.677  11.131  30.197  1.00 48.77           C
ATOM   2122  CB  LEU A 316      42.261  12.328  29.342  1.00 55.08           C
ATOM   2123  CG  LEU A 316      40.914  12.985  29.643  1.00 55.08           C
ATOM   2124  CD1 LEU A 316      40.956  13.640  31.009  1.00 55.08           C
ATOM   2125  CD2 LEU A 316      40.609  14.015  28.576  1.00 55.08           C
ATOM   2126  C   LEU A 316      41.579  10.083  30.141  1.00 48.77           C
ATOM   2127  O   LEU A 316      40.779   9.952  31.059  1.00 48.77           O
ATOM   2128  N   CYS A 317      41.556   9.335  29.048  1.00 47.14           N
ATOM   2129  CA  CYS A 317      40.548   8.315  28.844  1.00 47.14           C
ATOM   2130  CB  CYS A 317      40.643   7.778  27.403  1.00 38.56           C
ATOM   2131  SG  CYS A 317      39.252   6.729  26.866  1.00 38.56           S
ATOM   2132  C   CYS A 317      40.687   7.186  29.859  1.00 47.14           C
ATOM   2133  O   CYS A 317      39.694   6.597  30.279  1.00 47.14           O
ATOM   2134  N   SER A 318      41.914   6.891  30.269  1.00 43.48           N
ATOM   2135  CA  SER A 318      42.123   5.813  31.230  1.00 43.48           C
ATOM   2136  CB  SER A 318      43.591   5.380  31.252  1.00 48.56           C
ATOM   2137  OG  SER A 318      44.435   6.438  31.667  1.00 48.56           O
ATOM   2138  C   SER A 318      41.684   6.200  32.639  1.00 43.48           C
ATOM   2139  O   SER A 318      41.477   5.326  33.480  1.00 43.48           O
ATOM   2140  N   ARG A 319      41.545   7.505  32.891  1.00 45.47           N
ATOM   2141  CA  ARG A 319      41.115   8.005  34.199  1.00 45.47           C
ATOM   2142  CB  ARG A 319      41.907   9.259  34.583  1.00 82.71           C
ATOM   2143  CG  ARG A 319      43.344   8.982  35.002  1.00 82.71           C
ATOM   2144  CD  ARG A 319      43.424   8.130  36.276  1.00 82.71           C
ATOM   2145  NE  ARG A 319      42.892   8.814  37.458  1.00 82.71           N
ATOM   2146  CZ  ARG A 319      42.881   8.294  38.686  1.00 82.71           C
ATOM   2147  NH1 ARG A 319      43.372   7.077  38.906  1.00 82.71           N
ATOM   2148  NH2 ARG A 319      42.384   8.990  39.701  1.00 82.71           N
ATOM   2149  C   ARG A 319      39.616   8.311  34.231  1.00 45.47           C
ATOM   2150  O   ARG A 319      39.093   8.800  35.235  1.00 45.47           O
ATOM   2151  N   LEU A 320      38.935   8.019  33.126  1.00 36.24           N
ATOM   2152  CA  LEU A 320      37.499   8.244  33.021  1.00 36.24           C
ATOM   2153  CB  LEU A 320      37.171   9.047  31.760  1.00 26.54           C
ATOM   2154  CG  LEU A 320      37.836  10.416  31.558  1.00 26.54           C
ATOM   2155  CD1 LEU A 320      37.400  10.983  30.217  1.00 26.54           C
ATOM   2156  CD2 LEU A 320      37.470  11.370  32.680  1.00 26.54           C
ATOM   2157  C   LEU A 320      36.737   6.917  32.968  1.00 36.24           C
```

FIG. 7-37

```
ATOM   2158  O    LEU A 320      35.667   6.776  33.570  1.00 36.24           O
ATOM   2159  N    LEU A 321      37.290   5.946  32.243  1.00 46.23           N
ATOM   2160  CA   LEU A 321      36.647   4.648  32.099  1.00 46.23           C
ATOM   2161  CB   LEU A 321      36.805   4.164  30.658  1.00 37.73           C
ATOM   2162  CG   LEU A 321      36.182   5.127  29.634  1.00 37.73           C
ATOM   2163  CD1  LEU A 321      36.420   4.619  28.216  1.00 37.73           C
ATOM   2164  CD2  LEU A 321      34.689   5.269  29.905  1.00 37.73           C
ATOM   2165  C    LEU A 321      37.171   3.604  33.080  1.00 46.23           C
ATOM   2166  O    LEU A 321      37.873   2.664  32.699  1.00 46.23           O
ATOM   2167  N    GLU A 322      36.799   3.776  34.347  1.00 49.21           N
ATOM   2168  CA   GLU A 322      37.215   2.876  35.421  1.00 49.21           C
ATOM   2169  CB   GLU A 322      38.115   3.620  36.401  1.00 58.28           C
ATOM   2170  CG   GLU A 322      39.120   4.523  35.739  1.00 58.28           C
ATOM   2171  CD   GLU A 322      40.370   4.682  36.574  1.00 58.28           C
ATOM   2172  OE1  GLU A 322      40.991   3.654  36.919  1.00 58.28           O
ATOM   2173  OE2  GLU A 322      40.746   5.828  36.887  1.00 58.28           O
ATOM   2174  C    GLU A 322      36.018   2.314  36.185  1.00 49.21           C
ATOM   2175  O    GLU A 322      35.027   3.010  36.392  1.00 49.21           O
ATOM   2176  N    TYR A 323      36.127   1.061  36.619  1.00 58.48           N
ATOM   2177  CA   TYR A 323      35.050   0.413  37.357  1.00 58.48           C
ATOM   2178  CB   TYR A 323      35.417  -1.039  37.680  1.00 58.49           C
ATOM   2179  CG   TYR A 323      35.323  -1.969  36.495  1.00 58.49           C
ATOM   2180  CD1  TYR A 323      34.110  -2.161  35.831  1.00 58.49           C
ATOM   2181  CE1  TYR A 323      34.026  -2.983  34.709  1.00 58.49           C
ATOM   2182  CD2  TYR A 323      36.450  -2.630  36.012  1.00 58.49           C
ATOM   2183  CE2  TYR A 323      36.373  -3.452  34.894  1.00 58.49           C
ATOM   2184  CZ   TYR A 323      35.164  -3.620  34.247  1.00 58.49           C
ATOM   2185  OH   TYR A 323      35.111  -4.405  33.124  1.00 58.49           O
ATOM   2186  C    TYR A 323      34.688   1.140  38.649  1.00 58.48           C
ATOM   2187  O    TYR A 323      33.507   1.395  38.908  1.00 58.48           O
ATOM   2188  N    THR A 324      35.695   1.458  39.463  1.00 39.53           N
ATOM   2189  CA   THR A 324      35.458   2.151  40.725  1.00 39.53           C
ATOM   2190  CB   THR A 324      36.758   2.271  41.533  1.00 64.34           C
ATOM   2191  OG1  THR A 324      37.193   0.968  41.929  1.00 64.34           O
ATOM   2192  CG2  THR A 324      36.542   3.112  42.763  1.00 64.34           C
ATOM   2193  C    THR A 324      34.903   3.546  40.429  1.00 39.53           C
ATOM   2194  O    THR A 324      35.638   4.456  40.044  1.00 39.53           O
ATOM   2195  N    PRO A 325      33.591   3.732  40.615  1.00 50.25           N
ATOM   2196  CD   PRO A 325      32.652   2.776  41.220  1.00 40.06           C
ATOM   2197  CA   PRO A 325      32.937   5.022  40.357  1.00 50.25           C
ATOM   2198  CB   PRO A 325      31.520   4.805  40.883  1.00 40.06           C
ATOM   2199  CG   PRO A 325      31.329   3.323  40.772  1.00 40.06           C
ATOM   2200  C    PRO A 325      33.603   6.216  41.036  1.00 50.25           C
ATOM   2201  O    PRO A 325      33.439   7.363  40.616  1.00 50.25           O
ATOM   2202  N    THR A 326      34.361   5.941  42.085  1.00 35.83           N
ATOM   2203  CA   THR A 326      35.010   6.992  42.844  1.00 35.83           C
ATOM   2204  CB   THR A 326      34.942   6.670  44.316  1.00 32.41           C
ATOM   2205  OG1  THR A 326      35.662   5.452  44.555  1.00 32.41           O
ATOM   2206  CG2  THR A 326      33.484   6.482  44.741  1.00 32.41           C
ATOM   2207  C    THR A 326      36.454   7.157  42.444  1.00 35.83           C
ATOM   2208  O    THR A 326      37.144   8.044  42.939  1.00 35.83           O
ATOM   2209  N    ALA A 327      36.910   6.288  41.551  1.00 33.10           N
ATOM   2210  CA   ALA A 327      38.283   6.336  41.053  1.00 33.10           C
ATOM   2211  CB   ALA A 327      38.727   4.939  40.621  1.00 24.97           C
ATOM   2212  C    ALA A 327      38.370   7.306  39.869  1.00 33.10           C
ATOM   2213  O    ALA A 327      39.437   7.863  39.573  1.00 33.10           O
ATOM   2214  N    ARG A 328      37.228   7.497  39.208  1.00 33.80           N
ATOM   2215  CA   ARG A 328      37.111   8.371  38.054  1.00 33.80           C
ATOM   2216  CB   ARG A 328      35.703   8.299  37.494  1.00 38.44           C
ATOM   2217  CG   ARG A 328      35.360   6.939  37.012  1.00 38.44           C
```

FIG. 7-38

| | | | | | | | | | |
|---|---|---|---|---|---|---|---|---|---|
| ATOM | 2218 | CD | ARG | A | 328 | 33.890 | 6.800 | 36.792 | 1.00 38.44 | C |
| ATOM | 2219 | NE | ARG | A | 328 | 33.550 | 5.389 | 36.741 | 1.00 38.44 | N |
| ATOM | 2220 | CZ | ARG | A | 328 | 32.311 | 4.923 | 36.756 | 1.00 38.44 | C |
| ATOM | 2221 | NH1 | ARG | A | 328 | 31.287 | 5.770 | 36.812 | 1.00 38.44 | N |
| ATOM | 2222 | NH2 | ARG | A | 328 | 32.101 | 3.610 | 36.754 | 1.00 38.44 | N |
| ATOM | 2223 | C | ARG | A | 328 | 37.421 | 9.808 | 38.381 | 1.00 33.80 | C |
| ATOM | 2224 | O | ARG | A | 328 | 37.336 | 10.233 | 39.528 | 1.00 33.80 | O |
| ATOM | 2225 | N | LEU | A | 329 | 37.788 | 10.556 | 37.353 | 1.00 32.96 | N |
| ATOM | 2226 | CA | LEU | A | 329 | 38.075 | 11.961 | 37.523 | 1.00 32.96 | C |
| ATOM | 2227 | CB | LEU | A | 329 | 38.799 | 12.504 | 36.296 | 1.00 42.22 | C |
| ATOM | 2228 | CG | LEU | A | 329 | 40.316 | 12.656 | 36.400 | 1.00 42.22 | C |
| ATOM | 2229 | CD1 | LEU | A | 329 | 40.929 | 11.372 | 36.939 | 1.00 42.22 | C |
| ATOM | 2230 | CD2 | LEU | A | 329 | 40.884 | 13.011 | 35.034 | 1.00 42.22 | C |
| ATOM | 2231 | C | LEU | A | 329 | 36.759 | 12.701 | 37.715 | 1.00 32.96 | C |
| ATOM | 2232 | O | LEU | A | 329 | 35.681 | 12.187 | 37.416 | 1.00 32.96 | O |
| ATOM | 2233 | N | THR | A | 330 | 36.860 | 13.913 | 38.225 | 1.00 30.95 | N |
| ATOM | 2234 | CA | THR | A | 330 | 35.696 | 14.731 | 38.453 | 1.00 30.95 | C |
| ATOM | 2235 | CB | THR | A | 330 | 35.808 | 15.465 | 39.782 | 1.00 17.99 | C |
| ATOM | 2236 | OG1 | THR | A | 330 | 36.861 | 16.431 | 39.693 | 1.00 17.99 | O |
| ATOM | 2237 | CG2 | THR | A | 330 | 36.140 | 14.506 | 40.900 | 1.00 17.99 | C |
| ATOM | 2238 | C | THR | A | 330 | 35.745 | 15.757 | 37.346 | 1.00 30.95 | C |
| ATOM | 2239 | O | THR | A | 330 | 36.830 | 16.116 | 36.879 | 1.00 30.95 | O |
| ATOM | 2240 | N | PRO | A | 331 | 34.579 | 16.232 | 36.890 | 1.00 23.95 | N |
| ATOM | 2241 | CD | PRO | A | 331 | 33.221 | 15.818 | 37.290 | 1.00 22.40 | C |
| ATOM | 2242 | CA | PRO | A | 331 | 34.527 | 17.238 | 35.822 | 1.00 23.95 | C |
| ATOM | 2243 | CB | PRO | A | 331 | 33.145 | 17.843 | 36.014 | 1.00 22.40 | C |
| ATOM | 2244 | CG | PRO | A | 331 | 32.334 | 16.610 | 36.322 | 1.00 22.40 | C |
| ATOM | 2245 | C | PRO | A | 331 | 35.654 | 18.278 | 35.901 | 1.00 23.95 | C |
| ATOM | 2246 | O | PRO | A | 331 | 36.348 | 18.515 | 34.910 | 1.00 23.95 | O |
| ATOM | 2247 | N | LEU | A | 332 | 35.851 | 18.883 | 37.075 | 1.00 25.00 | N |
| ATOM | 2248 | CA | LEU | A | 332 | 36.914 | 19.886 | 37.224 | 1.00 25.00 | C |
| ATOM | 2249 | CB | LEU | A | 332 | 36.912 | 20.500 | 38.625 | 1.00 26.96 | C |
| ATOM | 2250 | CG | LEU | A | 332 | 36.204 | 21.840 | 38.801 | 1.00 26.96 | C |
| ATOM | 2251 | CD1 | LEU | A | 332 | 36.522 | 22.383 | 40.179 | 1.00 26.96 | C |
| ATOM | 2252 | CD2 | LEU | A | 332 | 36.659 | 22.817 | 37.740 | 1.00 26.96 | C |
| ATOM | 2253 | C | LEU | A | 332 | 38.306 | 19.323 | 36.949 | 1.00 25.00 | C |
| ATOM | 2254 | O | LEU | A | 332 | 39.108 | 19.902 | 36.206 | 1.00 25.00 | O |
| ATOM | 2255 | N | GLU | A | 333 | 38.602 | 18.192 | 37.569 | 1.00 39.30 | N |
| ATOM | 2256 | CA | GLU | A | 333 | 39.896 | 17.578 | 37.370 | 1.00 39.30 | C |
| ATOM | 2257 | CB | GLU | A | 333 | 39.975 | 16.265 | 38.151 | 1.00 35.74 | C |
| ATOM | 2258 | CG | GLU | A | 333 | 39.834 | 16.496 | 39.647 | 1.00 35.74 | C |
| ATOM | 2259 | CD | GLU | A | 333 | 39.749 | 15.223 | 40.448 | 1.00 35.74 | C |
| ATOM | 2260 | OE1 | GLU | A | 333 | 39.193 | 14.245 | 39.916 | 1.00 35.74 | O |
| ATOM | 2261 | OE2 | GLU | A | 333 | 40.213 | 15.203 | 41.616 | 1.00 35.74 | O |
| ATOM | 2262 | C | GLU | A | 333 | 40.098 | 17.358 | 35.882 | 1.00 39.30 | C |
| ATOM | 2263 | O | GLU | A | 333 | 41.071 | 17.844 | 35.305 | 1.00 39.30 | O |
| ATOM | 2264 | N | ALA | A | 334 | 39.159 | 16.662 | 35.253 | 1.00 33.96 | N |
| ATOM | 2265 | CA | ALA | A | 334 | 39.270 | 16.399 | 33.832 | 1.00 33.96 | C |
| ATOM | 2266 | CB | ALA | A | 334 | 37.994 | 15.766 | 33.318 | 1.00 13.33 | C |
| ATOM | 2267 | C | ALA | A | 334 | 39.591 | 17.666 | 33.033 | 1.00 33.96 | C |
| ATOM | 2268 | O | ALA | A | 334 | 40.367 | 17.608 | 32.085 | 1.00 33.96 | O |
| ATOM | 2269 | N | CYS | A | 335 | 39.007 | 18.805 | 33.407 | 1.00 23.90 | N |
| ATOM | 2270 | CA | CYS | A | 335 | 39.261 | 20.062 | 32.680 | 1.00 23.90 | C |
| ATOM | 2271 | CB | CYS | A | 335 | 38.398 | 21.207 | 33.211 | 1.00 32.10 | C |
| ATOM | 2272 | SG | CYS | A | 335 | 36.677 | 21.134 | 32.784 | 1.00 32.10 | S |
| ATOM | 2273 | C | CYS | A | 335 | 40.703 | 20.492 | 32.806 | 1.00 23.90 | C |
| ATOM | 2274 | O | CYS | A | 335 | 41.279 | 21.054 | 31.872 | 1.00 23.90 | O |
| ATOM | 2275 | N | ALA | A | 336 | 41.268 | 20.231 | 33.981 | 1.00 33.55 | N |
| ATOM | 2276 | CA | ALA | A | 336 | 42.643 | 20.602 | 34.285 | 1.00 33.55 | C |
| ATOM | 2277 | CB | ALA | A | 336 | 42.834 | 20.714 | 35.824 | 1.00 9.24 | C |

FIG. 7-39

```
ATOM   2278  C    ALA A 336      43.657  19.633  33.695  1.00 33.55           C
ATOM   2279  O    ALA A 336      44.851  19.912  33.701  1.00 33.55           O
ATOM   2280  N    HIS A 337      43.181  18.500  33.185  1.00 26.51           N
ATOM   2281  CA   HIS A 337      44.061  17.493  32.593  1.00 26.51           C
ATOM   2282  CB   HIS A 337      43.239  16.336  32.038  1.00 39.46           C
ATOM   2283  CG   HIS A 337      44.044  15.108  31.760  1.00 39.46           C
ATOM   2284  CD2  HIS A 337      44.621  14.657  30.621  1.00 39.46           C
ATOM   2285  ND1  HIS A 337      44.336  14.179  32.733  1.00 39.46           N
ATOM   2286  CE1  HIS A 337      45.054  13.205  32.205  1.00 39.46           C
ATOM   2287  NE2  HIS A 337      45.241  13.471  30.924  1.00 39.46           N
ATOM   2288  C    HIS A 337      44.967  18.064  31.482  1.00 26.51           C
ATOM   2289  O    HIS A 337      44.624  19.045  30.801  1.00 26.51           O
ATOM   2290  N    SER A 338      46.126  17.433  31.309  1.00 42.41           N
ATOM   2291  CA   SER A 338      47.110  17.854  30.321  1.00 42.41           C
ATOM   2292  CB   SER A 338      48.344  16.966  30.415  1.00 57.76           C
ATOM   2293  OG   SER A 338      48.958  17.075  31.684  1.00 57.76           O
ATOM   2294  C    SER A 338      46.584  17.816  28.895  1.00 42.41           C
ATOM   2295  O    SER A 338      47.007  18.595  28.043  1.00 42.41           O
ATOM   2296  N    PHE A 339      45.677  16.890  28.624  1.00 23.73           N
ATOM   2297  CA   PHE A 339      45.112  16.771  27.288  1.00 23.73           C
ATOM   2298  CB   PHE A 339      44.037  15.686  27.265  1.00 38.37           C
ATOM   2299  CG   PHE A 339      43.402  15.500  25.927  1.00 38.37           C
ATOM   2300  CD1  PHE A 339      44.154  15.077  24.837  1.00 38.37           C
ATOM   2301  CD2  PHE A 339      42.056  15.775  25.742  1.00 38.37           C
ATOM   2302  CE1  PHE A 339      43.573  14.933  23.575  1.00 38.37           C
ATOM   2303  CE2  PHE A 339      41.465  15.634  24.483  1.00 38.37           C
ATOM   2304  CZ   PHE A 339      42.228  15.212  23.398  1.00 38.37           C
ATOM   2305  C    PHE A 339      44.526  18.093  26.802  1.00 23.73           C
ATOM   2306  O    PHE A 339      44.490  18.370  25.603  1.00 23.73           O
ATOM   2307  N    PHE A 340      44.078  18.920  27.734  1.00 31.39           N
ATOM   2308  CA   PHE A 340      43.497  20.202  27.361  1.00 31.39           C
ATOM   2309  CB   PHE A 340      42.298  20.504  28.246  1.00 38.70           C
ATOM   2310  CG   PHE A 340      41.253  19.462  28.187  1.00 38.70           C
ATOM   2311  CD1  PHE A 340      40.501  19.296  27.038  1.00 38.70           C
ATOM   2312  CD2  PHE A 340      41.041  18.613  29.267  1.00 38.70           C
ATOM   2313  CE1  PHE A 340      39.547  18.297  26.963  1.00 38.70           C
ATOM   2314  CE2  PHE A 340      40.087  17.606  29.205  1.00 38.70           C
ATOM   2315  CZ   PHE A 340      39.338  17.444  28.056  1.00 38.70           C
ATOM   2316  C    PHE A 340      44.481  21.347  27.456  1.00 31.39           C
ATOM   2317  O    PHE A 340      44.091  22.513  27.342  1.00 31.39           O
ATOM   2318  N    ASP A 341      45.755  21.022  27.655  1.00 34.82           N
ATOM   2319  CA   ASP A 341      46.772  22.059  27.773  1.00 34.82           C
ATOM   2320  CB   ASP A 341      48.153  21.452  28.040  1.00 48.46           C
ATOM   2321  CG   ASP A 341      48.291  20.927  29.459  1.00 48.46           C
ATOM   2322  OD1  ASP A 341      47.364  21.160  30.272  1.00 48.46           O
ATOM   2323  OD2  ASP A 341      49.326  20.289  29.762  1.00 48.46           O
ATOM   2324  C    ASP A 341      46.829  22.976  26.560  1.00 34.82           C
ATOM   2325  O    ASP A 341      47.020  24.189  26.712  1.00 34.82           O
ATOM   2326  N    GLU A 342      46.643  22.419  25.363  1.00 31.21           N
ATOM   2327  CA   GLU A 342      46.692  23.257  24.174  1.00 31.21           C
ATOM   2328  CB   GLU A 342      46.430  22.458  22.896  1.00 31.06           C
ATOM   2329  CG   GLU A 342      46.732  23.280  21.643  1.00 31.06           C
ATOM   2330  CD   GLU A 342      46.383  22.578  20.345  1.00 31.06           C
ATOM   2331  OE1  GLU A 342      46.188  21.344  20.340  1.00 31.06           O
ATOM   2332  OE2  GLU A 342      46.317  23.268  19.313  1.00 31.06           O
ATOM   2333  C    GLU A 342      45.674  24.374  24.280  1.00 31.21           C
ATOM   2334  O    GLU A 342      45.945  25.508  23.875  1.00 31.21           O
ATOM   2335  N    LEU A 343      44.507  24.057  24.835  1.00 29.10           N
ATOM   2336  CA   LEU A 343      43.441  25.043  24.975  1.00 29.10           C
ATOM   2337  CB   LEU A 343      42.182  24.395  25.553  1.00 26.20           C
```

FIG. 7-40

```
ATOM   2338  CG   LEU A 343      41.504  23.359  24.658  1.00 26.20           C
ATOM   2339  CD1  LEU A 343      40.258  22.861  25.323  1.00 26.20           C
ATOM   2340  CD2  LEU A 343      41.167  23.980  23.322  1.00 26.20           C
ATOM   2341  C    LEU A 343      43.839  26.204  25.859  1.00 29.10           C
ATOM   2342  O    LEU A 343      43.379  27.332  25.660  1.00 29.10           O
ATOM   2343  N    ARG A 344      44.684  25.915  26.844  1.00 30.56           N
ATOM   2344  CA   ARG A 344      45.154  26.927  27.784  1.00 30.56           C
ATOM   2345  CB   ARG A 344      45.715  26.247  29.030  1.00 34.12           C
ATOM   2346  CG   ARG A 344      44.712  26.160  30.171  1.00 34.12           C
ATOM   2347  CD   ARG A 344      45.278  25.366  31.330  1.00 34.12           C
ATOM   2348  NE   ARG A 344      45.164  23.931  31.106  1.00 34.12           N
ATOM   2349  CZ   ARG A 344      44.029  23.253  31.210  1.00 34.12           C
ATOM   2350  NH1  ARG A 344      42.893  23.874  31.533  1.00 34.12           N
ATOM   2351  NH2  ARG A 344      44.040  21.944  31.019  1.00 34.12           N
ATOM   2352  C    ARG A 344      46.203  27.861  27.190  1.00 30.56           C
ATOM   2353  O    ARG A 344      46.569  28.879  27.793  1.00 30.56           O
ATOM   2354  N    ASP A 345      46.672  27.501  26.000  1.00 29.41           N
ATOM   2355  CA   ASP A 345      47.675  28.271  25.294  1.00 29.41           C
ATOM   2356  CB   ASP A 345      48.088  27.532  24.031  1.00 42.08           C
ATOM   2357  CG   ASP A 345      49.229  28.212  23.304  1.00 42.08           C
ATOM   2358  OD1  ASP A 345      50.268  27.547  23.118  1.00 42.08           O
ATOM   2359  OD2  ASP A 345      49.096  29.398  22.917  1.00 42.08           O
ATOM   2360  C    ASP A 345      47.088  29.623  24.932  1.00 29.41           C
ATOM   2361  O    ASP A 345      45.916  29.722  24.564  1.00 29.41           O
ATOM   2362  N    PRO A 346      47.893  30.687  25.035  1.00 50.05           N
ATOM   2363  CD   PRO A 346      49.242  30.727  25.630  1.00 36.94           C
ATOM   2364  CA   PRO A 346      47.417  32.033  24.710  1.00 50.05           C
ATOM   2365  CB   PRO A 346      48.453  32.926  25.379  1.00 36.94           C
ATOM   2366  CG   PRO A 346      49.714  32.107  25.266  1.00 36.94           C
ATOM   2367  C    PRO A 346      47.256  32.335  23.212  1.00 50.05           C
ATOM   2368  O    PRO A 346      46.734  33.384  22.855  1.00 50.05           O
ATOM   2369  N    ASN A 347      47.687  31.426  22.339  1.00 44.11           N
ATOM   2370  CA   ASN A 347      47.576  31.651  20.894  1.00 44.11           C
ATOM   2371  CB   ASN A 347      48.950  31.582  20.251  1.00 39.11           C
ATOM   2372  CG   ASN A 347      49.889  32.624  20.792  1.00 39.11           C
ATOM   2373  OD1  ASN A 347      49.626  33.827  20.705  1.00 39.11           O
ATOM   2374  ND2  ASN A 347      50.998  32.174  21.358  1.00 39.11           N
ATOM   2375  C    ASN A 347      46.646  30.694  20.148  1.00 44.11           C
ATOM   2376  O    ASN A 347      46.223  30.974  19.026  1.00 44.11           O
ATOM   2377  N    VAL A 348      46.351  29.558  20.764  1.00 49.39           N
ATOM   2378  CA   VAL A 348      45.470  28.582  20.157  1.00 49.39           C
ATOM   2379  CB   VAL A 348      44.987  27.552  21.188  1.00 33.81           C
ATOM   2380  CG1  VAL A 348      44.343  28.266  22.372  1.00 33.81           C
ATOM   2381  CG2  VAL A 348      43.999  26.595  20.534  1.00 33.81           C
ATOM   2382  C    VAL A 348      44.246  29.249  19.548  1.00 49.39           C
ATOM   2383  O    VAL A 348      43.542  30.022  20.194  1.00 49.39           O
ATOM   2384  N    LYS A 349      44.000  28.943  18.286  1.00 35.34           N
ATOM   2385  CA   LYS A 349      42.852  29.490  17.594  1.00 35.34           C
ATOM   2386  CB   LYS A 349      43.280  30.640  16.684  1.00 73.38           C
ATOM   2387  CG   LYS A 349      43.704  31.905  17.410  1.00 73.38           C
ATOM   2388  CD   LYS A 349      44.378  32.880  16.450  1.00 73.38           C
ATOM   2389  CE   LYS A 349      45.645  32.265  15.856  1.00 73.38           C
ATOM   2390  NZ   LYS A 349      46.361  33.176  14.924  1.00 73.38           N
ATOM   2391  C    LYS A 349      42.278  28.355  16.763  1.00 35.34           C
ATOM   2392  O    LYS A 349      42.966  27.364  16.519  1.00 35.34           O
ATOM   2393  N    LEU A 350      41.024  28.506  16.336  1.00 40.56           N
ATOM   2394  CA   LEU A 350      40.339  27.508  15.528  1.00 40.56           C
ATOM   2395  CB   LEU A 350      38.868  27.917  15.349  1.00 42.75           C
ATOM   2396  CG   LEU A 350      38.000  28.154  16.589  1.00 42.75           C
ATOM   2397  CD1  LEU A 350      36.673  28.767  16.157  1.00 42.75           C
```

FIG. 7-41

```
ATOM   2398  CD2 LEU A 350      37.766  26.847  17.306  1.00 42.75           C
ATOM   2399  C   LEU A 350      40.997  27.425  14.150  1.00 40.56           C
ATOM   2400  O   LEU A 350      41.420  28.433  13.593  1.00 40.56           O
ATOM   2401  N   PRO A 351      41.077  26.223  13.571  1.00 40.85           N
ATOM   2402  CD  PRO A 351      40.421  24.965  13.921  1.00 56.73           C
ATOM   2403  CA  PRO A 351      41.709  26.162  12.256  1.00 40.85           C
ATOM   2404  CB  PRO A 351      41.816  24.671  11.967  1.00 56.73           C
ATOM   2405  CG  PRO A 351      41.070  24.000  13.040  1.00 56.73           C
ATOM   2406  C   PRO A 351      40.830  26.862  11.280  1.00 40.85           C
ATOM   2407  O   PRO A 351      41.162  26.975  10.113  1.00 40.85           O
ATOM   2408  N   ASN A 352      39.722  27.366  11.790  1.00 42.11           N
ATOM   2409  CA  ASN A 352      38.772  28.085  10.973  1.00 42.11           C
ATOM   2410  CB  ASN A 352      37.360  27.880  11.524  1.00 45.39           C
ATOM   2411  CG  ASN A 352      36.630  29.179  11.756  1.00 45.39           C
ATOM   2412  OD1 ASN A 352      37.039  29.983  12.588  1.00 45.39           O
ATOM   2413  ND2 ASN A 352      35.547  29.399  11.017  1.00 45.39           N
ATOM   2414  C   ASN A 352      39.114  29.569  10.910  1.00 42.11           C
ATOM   2415  O   ASN A 352      38.403  30.361  10.283  1.00 42.11           O
ATOM   2416  N   GLY A 353      40.212  29.943  11.549  1.00 41.59           N
ATOM   2417  CA  GLY A 353      40.602  31.336  11.552  1.00 41.59           C
ATOM   2418  C   GLY A 353      40.403  32.020  12.900  1.00 41.59           C
ATOM   2419  O   GLY A 353      41.377  32.381  13.554  1.00 41.59           O
ATOM   2420  N   ARG A 354      39.152  32.204  13.319  1.00 43.09           N
ATOM   2421  CA  ARG A 354      38.848  32.893  14.579  1.00 43.09           C
ATOM   2422  CB  ARG A 354      37.334  33.097  14.712  1.00 55.05           C
ATOM   2423  CG  ARG A 354      36.531  31.826  14.785  1.00 55.05           C
ATOM   2424  CD  ARG A 354      35.056  32.129  14.970  1.00 55.05           C
ATOM   2425  NE  ARG A 354      34.507  32.872  13.840  1.00 55.05           N
ATOM   2426  CZ  ARG A 354      33.235  33.252  13.742  1.00 55.05           C
ATOM   2427  NH1 ARG A 354      32.371  32.955  14.706  1.00 55.05           N
ATOM   2428  NH2 ARG A 354      32.824  33.946  12.690  1.00 55.05           N
ATOM   2429  C   ARG A 354      39.385  32.269  15.872  1.00 43.09           C
ATOM   2430  O   ARG A 354      39.877  31.134  15.895  1.00 43.09           O
ATOM   2431  N   ASP A 355      39.299  33.043  16.951  1.00 68.70           N
ATOM   2432  CA  ASP A 355      39.752  32.575  18.248  1.00 68.70           C
ATOM   2433  CB  ASP A 355      40.025  33.749  19.218  1.00 86.20           C
ATOM   2434  CG  ASP A 355      39.164  34.984  18.943  1.00 86.20           C
ATOM   2435  OD1 ASP A 355      38.085  34.870  18.330  1.00 86.20           O
ATOM   2436  OD2 ASP A 355      39.570  36.088  19.368  1.00 86.20           O
ATOM   2437  C   ASP A 355      38.732  31.618  18.853  1.00 68.70           C
ATOM   2438  O   ASP A 355      37.584  31.545  18.405  1.00 68.70           O
ATOM   2439  N   THR A 356      39.165  30.869  19.861  1.00 39.43           N
ATOM   2440  CA  THR A 356      38.293  29.911  20.529  1.00 39.43           C
ATOM   2441  CB  THR A 356      39.087  28.946  21.425  1.00 61.06           C
ATOM   2442  OG1 THR A 356      39.497  29.629  22.618  1.00 61.06           O
ATOM   2443  CG2 THR A 356      40.308  28.428  20.694  1.00 61.06           C
ATOM   2444  C   THR A 356      37.286  30.638  21.420  1.00 39.43           C
ATOM   2445  O   THR A 356      37.413  31.837  21.684  1.00 39.43           O
ATOM   2446  N   PRO A 357      36.259  29.915  21.885  1.00 44.47           N
ATOM   2447  CD  PRO A 357      35.902  28.546  21.457  1.00 30.18           C
ATOM   2448  CA  PRO A 357      35.225  30.490  22.753  1.00 44.47           C
ATOM   2449  CB  PRO A 357      34.094  29.474  22.659  1.00 30.18           C
ATOM   2450  CG  PRO A 357      34.827  28.161  22.447  1.00 30.18           C
ATOM   2451  C   PRO A 357      35.704  30.682  24.185  1.00 44.47           C
ATOM   2452  O   PRO A 357      36.864  30.401  24.504  1.00 44.47           O
ATOM   2453  N   ALA A 358      34.808  31.160  25.044  1.00 46.92           N
ATOM   2454  CA  ALA A 358      35.145  31.382  26.447  1.00 46.92           C
ATOM   2455  CB  ALA A 358      34.014  32.094  27.150  1.00 46.66           C
ATOM   2456  C   ALA A 358      35.415  30.050  27.122  1.00 46.92           C
ATOM   2457  O   ALA A 358      34.570  29.159  27.097  1.00 46.92           O
```

FIG. 7-42

```
ATOM   2458  N    LEU A 359      36.586  29.911  27.736  1.00 25.84           N
ATOM   2459  CA   LEU A 359      36.929  28.654  28.384  1.00 25.84           C
ATOM   2460  CB   LEU A 359      37.962  27.911  27.535  1.00 16.03           C
ATOM   2461  CG   LEU A 359      37.651  27.849  26.036  1.00 16.03           C
ATOM   2462  CD1  LEU A 359      38.846  27.325  25.291  1.00 16.03           C
ATOM   2463  CD2  LEU A 359      36.431  26.997  25.796  1.00 16.03           C
ATOM   2464  C    LEU A 359      37.476  28.821  29.796  1.00 25.84           C
ATOM   2465  O    LEU A 359      37.634  27.837  30.528  1.00 25.84           O
ATOM   2466  N    PHE A 360      37.743  30.062  30.195  1.00 37.29           N
ATOM   2467  CA   PHE A 360      38.325  30.297  31.514  1.00 37.29           C
ATOM   2468  CB   PHE A 360      39.739  30.852  31.344  1.00 32.66           C
ATOM   2469  CG   PHE A 360      40.553  30.089  30.366  1.00 32.66           C
ATOM   2470  CD1  PHE A 360      40.880  28.759  30.616  1.00 32.66           C
ATOM   2471  CD2  PHE A 360      40.930  30.670  29.160  1.00 32.66           C
ATOM   2472  CE1  PHE A 360      41.571  28.011  29.669  1.00 32.66           C
ATOM   2473  CE2  PHE A 360      41.616  29.941  28.207  1.00 32.66           C
ATOM   2474  CZ   PHE A 360      41.941  28.605  28.454  1.00 32.66           C
ATOM   2475  C    PHE A 360      37.551  31.197  32.462  1.00 37.29           C
ATOM   2476  O    PHE A 360      38.084  31.619  33.494  1.00 37.29           O
ATOM   2477  N    ASN A 361      36.305  31.495  32.117  1.00 34.80           N
ATOM   2478  CA   ASN A 361      35.480  32.339  32.967  1.00 34.80           C
ATOM   2479  CB   ASN A 361      34.514  33.165  32.107  1.00 39.17           C
ATOM   2480  CG   ASN A 361      33.619  32.308  31.228  1.00 39.17           C
ATOM   2481  OD1  ASN A 361      33.991  31.208  30.822  1.00 39.17           O
ATOM   2482  ND2  ASN A 361      32.437  32.823  30.912  1.00 39.17           N
ATOM   2483  C    ASN A 361      34.726  31.499  34.006  1.00 34.80           C
ATOM   2484  O    ASN A 361      33.499  31.539  34.107  1.00 34.80           O
ATOM   2485  N    PHE A 362      35.491  30.737  34.778  1.00 33.97           N
ATOM   2486  CA   PHE A 362      34.958  29.879  35.823  1.00 33.97           C
ATOM   2487  CB   PHE A 362      36.045  28.959  36.357  1.00 34.37           C
ATOM   2488  CG   PHE A 362      36.377  27.837  35.463  1.00 34.37           C
ATOM   2489  CD1  PHE A 362      35.676  26.642  35.554  1.00 34.37           C
ATOM   2490  CD2  PHE A 362      37.393  27.967  34.525  1.00 34.37           C
ATOM   2491  CE1  PHE A 362      35.980  25.579  34.721  1.00 34.37           C
ATOM   2492  CE2  PHE A 362      37.710  26.924  33.688  1.00 34.37           C
ATOM   2493  CZ   PHE A 362      36.999  25.715  33.785  1.00 34.37           C
ATOM   2494  C    PHE A 362      34.476  30.705  36.988  1.00 33.97           C
ATOM   2495  O    PHE A 362      35.220  31.532  37.500  1.00 33.97           O
ATOM   2496  N    THR A 363      33.250  30.458  37.425  1.00 32.52           N
ATOM   2497  CA   THR A 363      32.694  31.176  38.553  1.00 32.52           C
ATOM   2498  CB   THR A 363      31.176  31.276  38.471  1.00 21.33           C
ATOM   2499  OG1  THR A 363      30.598  29.962  38.485  1.00 21.33           O
ATOM   2500  CG2  THR A 363      30.781  32.042  37.218  1.00 21.33           C
ATOM   2501  C    THR A 363      33.048  30.440  39.821  1.00 32.52           C
ATOM   2502  O    THR A 363      33.293  29.237  39.798  1.00 32.52           O
ATOM   2503  N    THR A 364      33.067  31.163  40.933  1.00 30.27           N
ATOM   2504  CA   THR A 364      33.400  30.566  42.217  1.00 30.27           C
ATOM   2505  CB   THR A 364      33.125  31.621  43.328  1.00 27.41           C
ATOM   2506  OG1  THR A 364      33.012  30.985  44.604  1.00 27.41           O
ATOM   2507  CG2  THR A 364      31.872  32.417  42.995  1.00 27.41           C
ATOM   2508  C    THR A 364      32.656  29.211  42.440  1.00 30.27           C
ATOM   2509  O    THR A 364      33.262  28.194  42.825  1.00 30.27           O
ATOM   2510  N    GLN A 365      31.356  29.196  42.154  1.00 29.93           N
ATOM   2511  CA   GLN A 365      30.514  27.996  42.288  1.00 29.93           C
ATOM   2512  CB   GLN A 365      29.099  28.332  41.817  1.00 35.17           C
ATOM   2513  CG   GLN A 365      28.207  27.145  41.516  1.00 35.17           C
ATOM   2514  CD   GLN A 365      27.319  26.783  42.687  1.00 35.17           C
ATOM   2515  OE1  GLN A 365      26.772  27.667  43.350  1.00 35.17           O
ATOM   2516  NE2  GLN A 365      27.153  25.483  42.940  1.00 35.17           N
ATOM   2517  C    GLN A 365      31.049  26.832  41.454  1.00 29.93           C
```

FIG. 7-43

```
ATOM   2518  O    GLN A 365      31.197  25.705  41.924  1.00 29.93           O
ATOM   2519  N    GLU A 366      31.313  27.140  40.195  1.00 29.68           N
ATOM   2520  CA   GLU A 366      31.826  26.189  39.222  1.00 29.68           C
ATOM   2521  CB   GLU A 366      32.073  26.938  37.908  1.00 41.27           C
ATOM   2522  CG   GLU A 366      31.795  26.150  36.657  1.00 41.27           C
ATOM   2523  CD   GLU A 366      32.017  26.973  35.418  1.00 41.27           C
ATOM   2524  OE1  GLU A 366      32.391  26.375  34.389  1.00 41.27           O
ATOM   2525  OE2  GLU A 366      31.810  28.211  35.468  1.00 41.27           O
ATOM   2526  C    GLU A 366      33.127  25.520  39.698  1.00 29.68           C
ATOM   2527  O    GLU A 366      33.487  24.420  39.260  1.00 29.68           O
ATOM   2528  N    LEU A 367      33.834  26.203  40.588  1.00 30.00           N
ATOM   2529  CA   LEU A 367      35.085  25.690  41.112  1.00 30.00           C
ATOM   2530  CB   LEU A 367      36.096  26.834  41.232  1.00 31.99           C
ATOM   2531  CG   LEU A 367      36.624  27.216  39.849  1.00 31.99           C
ATOM   2532  CD1  LEU A 367      37.348  28.533  39.879  1.00 31.99           C
ATOM   2533  CD2  LEU A 367      37.546  26.111  39.372  1.00 31.99           C
ATOM   2534  C    LEU A 367      34.873  25.011  42.455  1.00 30.00           C
ATOM   2535  O    LEU A 367      35.670  24.171  42.865  1.00 30.00           O
ATOM   2536  N    SER A 368      33.779  25.373  43.117  1.00 29.55           N
ATOM   2537  CA   SER A 368      33.414  24.832  44.423  1.00 29.55           C
ATOM   2538  CB   SER A 368      31.889  24.788  44.546  1.00 33.45           C
ATOM   2539  OG   SER A 368      31.356  23.791  43.696  1.00 33.45           O
ATOM   2540  C    SER A 368      33.991  23.460  44.858  1.00 29.55           C
ATOM   2541  O    SER A 368      34.470  23.337  45.988  1.00 29.55           O
ATOM   2542  N    SER A 369      33.953  22.438  43.997  1.00 29.73           N
ATOM   2543  CA   SER A 369      34.449  21.104  44.384  1.00 29.73           C
ATOM   2544  CB   SER A 369      34.083  20.052  43.332  1.00 41.05           C
ATOM   2545  OG   SER A 369      34.814  20.233  42.131  1.00 41.05           O
ATOM   2546  C    SER A 369      35.949  21.016  44.654  1.00 29.73           C
ATOM   2547  O    SER A 369      36.415  20.084  45.306  1.00 29.73           O
ATOM   2548  N    ASN A 370      36.711  21.974  44.147  1.00 28.55           N
ATOM   2549  CA   ASN A 370      38.143  21.976  44.359  1.00 28.55           C
ATOM   2550  CB   ASN A 370      38.768  20.814  43.592  1.00 33.26           C
ATOM   2551  CG   ASN A 370      40.166  20.494  44.065  1.00 33.26           C
ATOM   2552  OD1  ASN A 370      40.999  21.383  44.206  1.00 33.26           O
ATOM   2553  ND2  ASN A 370      40.433  19.218  44.306  1.00 33.26           N
ATOM   2554  C    ASN A 370      38.689  23.321  43.865  1.00 28.55           C
ATOM   2555  O    ASN A 370      39.221  23.432  42.762  1.00 28.55           O
ATOM   2556  N    PRO A 371      38.535  24.374  44.686  1.00 42.14           N
ATOM   2557  CD   PRO A 371      37.771  24.358  45.945  1.00 29.58           C
ATOM   2558  CA   PRO A 371      38.984  25.734  44.388  1.00 42.14           C
ATOM   2559  CB   PRO A 371      38.679  26.476  45.673  1.00 29.58           C
ATOM   2560  CG   PRO A 371      37.424  25.816  46.111  1.00 29.58           C
ATOM   2561  C    PRO A 371      40.433  25.877  43.976  1.00 42.14           C
ATOM   2562  O    PRO A 371      40.737  26.670  43.099  1.00 42.14           O
ATOM   2563  N    PRO A 372      41.350  25.118  44.601  1.00 45.38           N
ATOM   2564  CD   PRO A 372      41.194  24.202  45.744  1.00 44.11           C
ATOM   2565  CA   PRO A 372      42.761  25.226  44.233  1.00 45.38           C
ATOM   2566  CB   PRO A 372      43.466  24.489  45.370  1.00 44.11           C
ATOM   2567  CG   PRO A 372      42.508  23.449  45.732  1.00 44.11           C
ATOM   2568  C    PRO A 372      43.142  24.693  42.846  1.00 45.38           C
ATOM   2569  O    PRO A 372      44.305  24.785  42.449  1.00 45.38           O
ATOM   2570  N    LEU A 373      42.184  24.129  42.114  1.00 30.67           N
ATOM   2571  CA   LEU A 373      42.469  23.645  40.761  1.00 30.67           C
ATOM   2572  CB   LEU A 373      41.425  22.639  40.291  1.00 32.38           C
ATOM   2573  CG   LEU A 373      41.415  21.257  40.928  1.00 32.38           C
ATOM   2574  CD1  LEU A 373      40.256  20.468  40.373  1.00 32.38           C
ATOM   2575  CD2  LEU A 373      42.708  20.539  40.635  1.00 32.38           C
ATOM   2576  C    LEU A 373      42.440  24.822  39.800  1.00 30.67           C
ATOM   2577  O    LEU A 373      42.810  24.680  38.638  1.00 30.67           O
```

FIG. 7-44

```
ATOM   2578  N   ALA A 374      41.988  25.975  40.292  1.00 40.84           N
ATOM   2579  CA  ALA A 374      41.878  27.188  39.483  1.00 40.84           C
ATOM   2580  CB  ALA A 374      41.044  28.251  40.223  1.00 19.66           C
ATOM   2581  C   ALA A 374      43.226  27.769  39.087  1.00 40.84           C
ATOM   2582  O   ALA A 374      43.328  28.489  38.090  1.00 40.84           O
ATOM   2583  N   THR A 375      44.263  27.464  39.858  1.00 43.92           N
ATOM   2584  CA  THR A 375      45.590  27.977  39.535  1.00 43.92           C
ATOM   2585  CB  THR A 375      46.575  27.779  40.724  1.00 44.87           C
ATOM   2586  OG1 THR A 375      46.694  26.390  41.037  1.00 44.87           O
ATOM   2587  CG2 THR A 375      46.049  28.473  41.960  1.00 44.87           C
ATOM   2588  C   THR A 375      46.105  27.280  38.274  1.00 43.92           C
ATOM   2589  O   THR A 375      47.161  27.631  37.756  1.00 43.92           O
ATOM   2590  N   ILE A 376      45.340  26.296  37.791  1.00 50.95           N
ATOM   2591  CA  ILE A 376      45.665  25.542  36.572  1.00 50.95           C
ATOM   2592  CB  ILE A 376      45.656  24.009  36.798  1.00 15.54           C
ATOM   2593  CG2 ILE A 376      45.845  23.274  35.462  1.00 15.54           C
ATOM   2594  CG1 ILE A 376      46.756  23.609  37.769  1.00 15.54           C
ATOM   2595  CD1 ILE A 376      46.914  22.096  37.873  1.00 15.54           C
ATOM   2596  C   ILE A 376      44.634  25.820  35.480  1.00 50.95           C
ATOM   2597  O   ILE A 376      44.975  25.998  34.310  1.00 50.95           O
ATOM   2598  N   LEU A 377      43.368  25.826  35.873  1.00 41.31           N
ATOM   2599  CA  LEU A 377      42.274  26.069  34.950  1.00 41.31           C
ATOM   2600  CB  LEU A 377      40.948  25.810  35.661  1.00 21.36           C
ATOM   2601  CG  LEU A 377      40.707  24.344  36.042  1.00 21.36           C
ATOM   2602  CD1 LEU A 377      39.605  24.236  37.070  1.00 21.36           C
ATOM   2603  CD2 LEU A 377      40.357  23.553  34.800  1.00 21.36           C
ATOM   2604  C   LEU A 377      42.304  27.488  34.390  1.00 41.31           C
ATOM   2605  O   LEU A 377      41.889  27.719  33.251  1.00 41.31           O
ATOM   2606  N   ILE A 378      42.785  28.438  35.187  1.00 47.30           N
ATOM   2607  CA  ILE A 378      42.860  29.818  34.728  1.00 47.30           C
ATOM   2608  CB  ILE A 378      42.256  30.796  35.761  1.00 45.25           C
ATOM   2609  CG2 ILE A 378      42.033  32.163  35.123  1.00 45.25           C
ATOM   2610  CG1 ILE A 378      40.911  30.260  36.243  1.00 45.25           C
ATOM   2611  CD1 ILE A 378      40.244  31.127  37.283  1.00 45.25           C
ATOM   2612  C   ILE A 378      44.308  30.215  34.459  1.00 47.30           C
ATOM   2613  O   ILE A 378      45.052  30.549  35.380  1.00 47.30           O
ATOM   2614  N   PRO A 379      44.727  30.174  33.185  1.00 29.86           N
ATOM   2615  CD  PRO A 379      43.930  29.853  31.990  1.00 35.20           C
ATOM   2616  CA  PRO A 379      46.094  30.535  32.809  1.00 29.86           C
ATOM   2617  CB  PRO A 379      46.143  30.174  31.328  1.00 35.20           C
ATOM   2618  CG  PRO A 379      44.758  30.467  30.880  1.00 35.20           C
ATOM   2619  C   PRO A 379      46.361  32.021  33.069  1.00 29.86           C
ATOM   2620  O   PRO A 379      45.446  32.841  33.056  1.00 29.86           O
ATOM   2621  N   PRO A 380      47.630  32.382  33.294  1.00 45.90           N
ATOM   2622  CD  PRO A 380      48.823  31.548  33.047  1.00 35.29           C
ATOM   2623  CA  PRO A 380      48.011  33.772  33.564  1.00 45.90           C
ATOM   2624  CB  PRO A 380      49.497  33.786  33.225  1.00 35.29           C
ATOM   2625  CG  PRO A 380      49.933  32.395  33.626  1.00 35.29           C
ATOM   2626  C   PRO A 380      47.223  34.805  32.763  1.00 45.90           C
ATOM   2627  O   PRO A 380      46.529  35.650  33.335  1.00 45.90           O
ATOM   2628  N   HIS A 381      47.333  34.732  31.440  1.00 38.40           N
ATOM   2629  CA  HIS A 381      46.641  35.673  30.561  1.00 38.40           C
ATOM   2630  CB  HIS A 381      46.903  35.309  29.087  1.00 61.92           C
ATOM   2631  CG  HIS A 381      46.246  34.037  28.640  1.00 61.92           C
ATOM   2632  CD2 HIS A 381      46.654  32.748  28.714  1.00 61.92           C
ATOM   2633  ND1 HIS A 381      45.001  34.011  28.046  1.00 61.92           N
ATOM   2634  CE1 HIS A 381      44.670  32.761  27.776  1.00 61.92           C
ATOM   2635  NE2 HIS A 381      45.655  31.974  28.171  1.00 61.92           N
ATOM   2636  C   HIS A 381      45.139  35.733  30.844  1.00 38.40           C
ATOM   2637  O   HIS A 381      44.540  36.804  30.793  1.00 38.40           O
```

FIG. 7-45

```
ATOM   2638  N   ALA A 382      44.538  34.588  31.156  1.00 35.85           N
ATOM   2639  CA  ALA A 382      43.102  34.529  31.445  1.00 35.85           C
ATOM   2640  CB  ALA A 382      42.675  33.071  31.740  1.00 32.13           C
ATOM   2641  C   ALA A 382      42.711  35.449  32.614  1.00 35.85           C
ATOM   2642  O   ALA A 382      41.657  36.085  32.592  1.00 35.85           O
ATOM   2643  N   ARG A 383      43.562  35.511  33.632  1.00 55.72           N
ATOM   2644  CA  ARG A 383      43.307  36.362  34.783  1.00 55.72           C
ATOM   2645  CB  ARG A 383      44.431  36.187  35.818  1.00 55.55           C
ATOM   2646  CG  ARG A 383      44.879  34.726  36.035  1.00 55.55           C
ATOM   2647  CD  ARG A 383      45.854  34.587  37.213  1.00 55.55           C
ATOM   2648  NE  ARG A 383      45.203  34.108  38.433  1.00 55.55           N
ATOM   2649  CZ  ARG A 383      45.128  32.827  38.800  1.00 55.55           C
ATOM   2650  NH1 ARG A 383      45.673  31.873  38.053  1.00 55.55           N
ATOM   2651  NH2 ARG A 383      44.488  32.486  39.911  1.00 55.55           N
ATOM   2652  C   ARG A 383      43.233  37.822  34.286  1.00 55.72           C
ATOM   2653  O   ARG A 383      44.286  38.493  34.244  1.00 55.72           O
ATOM   2654  OXT ARG A 383      42.127  38.281  33.901  1.00 55.55           O
TER    2655      ARG A 383
ATOM   2656  CB  VAL B  37      21.755  33.564  97.403  1.00 27.95           C
ATOM   2657  CG1 VAL B  37      22.602  34.021  96.220  1.00 27.95           C
ATOM   2658  CG2 VAL B  37      20.383  34.212  97.411  1.00 27.95           C
ATOM   2659  C   VAL B  37      22.981  31.442  97.304  1.00 45.39           C
ATOM   2660  O   VAL B  37      23.858  31.784  98.086  1.00 45.39           O
ATOM   2661  N   VAL B  37      20.805  31.581  98.557  1.00 45.39           N
ATOM   2662  CA  VAL B  37      21.591  32.056  97.377  1.00 45.39           C
ATOM   2663  N   THR B  38      23.181  30.552  96.340  1.00 46.04           N
ATOM   2664  CA  THR B  38      24.454  29.867  96.159  1.00 46.04           C
ATOM   2665  CB  THR B  38      24.231  28.512  95.452  1.00 37.12           C
ATOM   2666  OG1 THR B  38      23.308  27.718  96.212  1.00 37.12           O
ATOM   2667  CG2 THR B  38      25.547  27.766  95.289  1.00 37.12           C
ATOM   2668  C   THR B  38      25.428  30.685  95.320  1.00 46.04           C
ATOM   2669  O   THR B  38      25.056  31.213  94.271  1.00 46.04           O
ATOM   2670  N   THR B  39      26.671  30.801  95.777  1.00 42.59           N
ATOM   2671  CA  THR B  39      27.659  31.530  94.989  1.00 42.59           C
ATOM   2672  CB  THR B  39      27.994  32.902  95.596  1.00 52.78           C
ATOM   2673  OG1 THR B  39      26.800  33.692  95.691  1.00 52.78           O
ATOM   2674  CG2 THR B  39      28.984  33.632  94.703  1.00 52.78           C
ATOM   2675  C   THR B  39      28.957  30.746  94.767  1.00 42.59           C
ATOM   2676  O   THR B  39      29.570  30.223  95.712  1.00 42.59           O
ATOM   2677  N   VAL B  40      29.354  30.678  93.495  1.00 30.11           N
ATOM   2678  CA  VAL B  40      30.557  29.968  93.073  1.00 30.11           C
ATOM   2679  CB  VAL B  40      30.206  28.609  92.421  1.00 27.23           C
ATOM   2680  CG1 VAL B  40      29.379  27.773  93.378  1.00 27.23           C
ATOM   2681  CG2 VAL B  40      29.443  28.831  91.116  1.00 27.23           C
ATOM   2682  C   VAL B  40      31.354  30.754  92.046  1.00 30.11           C
ATOM   2683  O   VAL B  40      30.924  31.799  91.547  1.00 30.11           O
ATOM   2684  N   VAL B  41      32.529  30.232  91.733  1.00 30.49           N
ATOM   2685  CA  VAL B  41      33.385  30.833  90.724  1.00 30.49           C
ATOM   2686  CB  VAL B  41      34.837  31.008  91.231  1.00 13.85           C
ATOM   2687  CG1 VAL B  41      35.675  31.759  90.184  1.00 13.85           C
ATOM   2688  CG2 VAL B  41      34.828  31.743  92.565  1.00 13.85           C
ATOM   2689  C   VAL B  41      33.359  29.814  89.594  1.00 30.49           C
ATOM   2690  O   VAL B  41      33.866  28.709  89.747  1.00 30.49           O
ATOM   2691  N   ALA B  42      32.735  30.168  88.478  1.00 41.92           N
ATOM   2692  CA  ALA B  42      32.656  29.251  87.346  1.00 41.92           C
ATOM   2693  CB  ALA B  42      31.188  28.954  87.004  1.00 23.84           C
ATOM   2694  C   ALA B  42      33.375  29.849  86.142  1.00 41.92           C
ATOM   2695  O   ALA B  42      33.742  31.021  86.152  1.00 41.92           O
ATOM   2696  N   THR B  43      33.591  29.041  85.112  1.00 34.45           N
ATOM   2697  CA  THR B  43      34.261  29.527  83.919  1.00 34.45           C
```

FIG. 7-46

```
ATOM   2698  CB   THR B  43      35.514  28.693  83.585  1.00 32.66           C
ATOM   2699  OG1  THR B  43      36.333  28.539  84.747  1.00 32.66           O
ATOM   2700  CG2  THR B  43      36.312  29.395  82.513  1.00 32.66           C
ATOM   2701  C    THR B  43      33.293  29.408  82.747  1.00 34.45           C
ATOM   2702  O    THR B  43      32.580  28.417  82.623  1.00 34.45           O
ATOM   2703  N    PRO B  44      33.225  30.429  81.881  1.00 54.52           N
ATOM   2704  CD   PRO B  44      33.607  31.835  82.033  1.00 52.03           C
ATOM   2705  CA   PRO B  44      32.279  30.252  80.773  1.00 54.52           C
ATOM   2706  CB   PRO B  44      32.291  31.600  80.064  1.00 52.03           C
ATOM   2707  CG   PRO B  44      33.414  32.336  80.685  1.00 52.03           C
ATOM   2708  C    PRO B  44      32.693  29.122  79.867  1.00 54.52           C
ATOM   2709  O    PRO B  44      33.869  28.780  79.814  1.00 54.52           O
ATOM   2710  N    GLY B  45      31.729  28.527  79.174  1.00 41.04           N
ATOM   2711  CA   GLY B  45      32.040  27.402  78.314  1.00 41.04           C
ATOM   2712  C    GLY B  45      32.842  27.880  77.143  1.00 41.04           C
ATOM   2713  O    GLY B  45      33.883  27.307  76.804  1.00 41.04           O
ATOM   2714  N    GLN B  46      32.367  28.959  76.539  1.00 74.52           N
ATOM   2715  CA   GLN B  46      33.037  29.506  75.376  1.00 74.52           C
ATOM   2716  CB   GLN B  46      32.018  29.917  74.335  1.00 62.23           C
ATOM   2717  CG   GLN B  46      30.887  28.918  74.256  1.00 23.68           C
ATOM   2718  CD   GLN B  46      30.824  28.228  72.887  1.00 23.68           C
ATOM   2719  OE1  GLN B  46      31.816  27.592  72.440  1.00 23.68           O
ATOM   2720  NE2  GLN B  46      29.654  28.325  72.218  1.00 23.68           N
ATOM   2721  C    GLN B  46      33.932  30.677  75.671  1.00 74.52           C
ATOM   2722  O    GLN B  46      35.117  30.594  75.375  1.00 74.52           O
ATOM   2723  N    GLY B  47      33.366  31.757  76.218  1.00 83.59           N
ATOM   2724  CA   GLY B  47      34.126  32.953  76.546  1.00 83.59           C
ATOM   2725  C    GLY B  47      35.603  32.726  76.818  1.00 83.59           C
ATOM   2726  O    GLY B  47      36.080  31.605  76.856  1.00 83.59           O
ATOM   2727  N    PRO B  48      36.377  33.783  77.029  1.00 60.48           N
ATOM   2728  CD   PRO B  48      36.140  35.231  76.957  1.00 65.93           C
ATOM   2729  CA   PRO B  48      37.794  33.481  77.283  1.00 60.48           C
ATOM   2730  CB   PRO B  48      38.414  34.847  77.417  1.00 65.93           C
ATOM   2731  CG   PRO B  48      37.470  35.721  76.608  1.00 65.93           C
ATOM   2732  C    PRO B  48      37.900  32.727  78.594  1.00 60.48           C
ATOM   2733  O    PRO B  48      37.142  33.007  79.505  1.00 60.48           O
ATOM   2734  N    ASP B  49      38.818  31.768  78.681  1.00 52.11           N
ATOM   2735  CA   ASP B  49      38.981  30.956  79.886  1.00 52.11           C
ATOM   2736  CB   ASP B  49      40.070  29.895  79.666  1.00 46.62           C
ATOM   2737  CG   ASP B  49      40.092  28.848  80.765  1.00 46.62           C
ATOM   2738  OD1  ASP B  49      40.166  29.240  81.947  1.00 46.62           O
ATOM   2739  OD2  ASP B  49      40.040  27.635  80.462  1.00 46.62           O
ATOM   2740  C    ASP B  49      39.344  31.887  81.035  1.00 52.11           C
ATOM   2741  O    ASP B  49      40.519  32.105  81.322  1.00 52.11           O
ATOM   2742  N    ARG B  50      38.320  32.447  81.675  1.00 42.35           N
ATOM   2743  CA   ARG B  50      38.510  33.385  82.771  1.00 42.35           C
ATOM   2744  CB   ARG B  50      38.454  34.830  82.255  1.00 96.20           C
ATOM   2745  CG   ARG B  50      39.371  35.088  81.065  1.00 96.20           C
ATOM   2746  CD   ARG B  50      40.264  36.306  81.265  1.00 96.20           C
ATOM   2747  NE   ARG B  50      39.750  37.504  80.605  1.00 96.20           N
ATOM   2748  CZ   ARG B  50      40.478  38.598  80.399  1.00 96.20           C
ATOM   2749  NH1  ARG B  50      41.745  38.637  80.803  1.00 96.20           N
ATOM   2750  NH2  ARG B  50      39.947  39.651  79.790  1.00 96.20           N
ATOM   2751  C    ARG B  50      37.425  33.178  83.807  1.00 42.35           C
ATOM   2752  O    ARG B  50      36.268  33.538  83.593  1.00 42.35           O
ATOM   2753  N    PRO B  51      37.785  32.604  84.956  1.00 37.14           N
ATOM   2754  CD   PRO B  51      39.141  32.314  85.447  1.00 29.69           C
ATOM   2755  CA   PRO B  51      36.790  32.368  86.003  1.00 37.14           C
ATOM   2756  CB   PRO B  51      37.619  31.766  87.135  1.00 29.69           C
ATOM   2757  CG   PRO B  51      38.963  32.409  86.948  1.00 29.69           C
```

FIG. 7-47

```
ATOM   2758  C    PRO B  51      36.060  33.629  86.431  1.00 37.14           C
ATOM   2759  O    PRO B  51      36.568  34.733  86.272  1.00 37.14           O
ATOM   2760  N    GLN B  52      34.860  33.447  86.966  1.00 39.00           N
ATOM   2761  CA   GLN B  52      34.044  34.557  87.438  1.00 39.00           C
ATOM   2762  CB   GLN B  52      33.367  35.276  86.264  1.00 31.91           C
ATOM   2763  CG   GLN B  52      32.525  34.400  85.347  1.00 31.91           C
ATOM   2764  CD   GLN B  52      31.620  35.233  84.448  1.00 31.91           C
ATOM   2765  OE1  GLN B  52      30.713  35.907  84.928  1.00 31.91           O
ATOM   2766  NE2  GLN B  52      31.872  35.197  83.140  1.00 31.91           N
ATOM   2767  C    GLN B  52      32.988  34.097  88.436  1.00 39.00           C
ATOM   2768  O    GLN B  52      32.675  32.910  88.532  1.00 39.00           O
ATOM   2769  N    GLU B  53      32.443  35.048  89.181  1.00 51.90           N
ATOM   2770  CA   GLU B  53      31.431  34.729  90.173  1.00 51.90           C
ATOM   2771  CB   GLU B  53      31.240  35.905  91.132  1.00 68.62           C
ATOM   2772  CG   GLU B  53      30.450  35.533  92.385  1.00 68.62           C
ATOM   2773  CD   GLU B  53      30.255  36.716  93.295  1.00 68.62           C
ATOM   2774  OE1  GLU B  53      29.727  36.599  94.413  1.00 68.62           O
ATOM   2775  OE2  GLU B  53      30.633  37.795  92.880  1.00 68.62           O
ATOM   2776  C    GLU B  53      30.109  34.397  89.496  1.00 51.90           C
ATOM   2777  O    GLU B  53      29.715  35.047  88.530  1.00 51.90           O
ATOM   2778  N    VAL B  54      29.425  33.380  89.997  1.00 38.89           N
ATOM   2779  CA   VAL B  54      28.153  32.999  89.415  1.00 38.89           C
ATOM   2780  CB   VAL B  54      28.312  31.754  88.482  1.00 16.21           C
ATOM   2781  CG1  VAL B  54      26.945  31.355  87.924  1.00 16.21           C
ATOM   2782  CG2  VAL B  54      29.264  32.073  87.309  1.00 16.21           C
ATOM   2783  C    VAL B  54      27.144  32.697  90.523  1.00 38.89           C
ATOM   2784  O    VAL B  54      27.266  31.697  91.234  1.00 38.89           O
ATOM   2785  N    SER B  55      26.149  33.566  90.681  1.00 46.06           N
ATOM   2786  CA   SER B  55      25.151  33.354  91.724  1.00 46.06           C
ATOM   2787  CB   SER B  55      24.930  34.635  92.526  1.00 61.81           C
ATOM   2788  OG   SER B  55      26.001  34.846  93.431  1.00 61.81           O
ATOM   2789  C    SER B  55      23.826  32.849  91.193  1.00 46.06           C
ATOM   2790  O    SER B  55      23.357  33.272  90.137  1.00 46.06           O
ATOM   2791  N    TYR B  56      23.225  31.934  91.940  1.00 36.50           N
ATOM   2792  CA   TYR B  56      21.957  31.357  91.546  1.00 36.50           C
ATOM   2793  CB   TYR B  56      22.182  30.181  90.583  1.00 26.32           C
ATOM   2794  CG   TYR B  56      23.110  29.098  91.091  1.00 26.32           C
ATOM   2795  CD1  TYR B  56      22.635  28.057  91.885  1.00 26.32           C
ATOM   2796  CE1  TYR B  56      23.491  27.037  92.323  1.00 26.32           C
ATOM   2797  CD2  TYR B  56      24.470  29.102  90.745  1.00 26.32           C
ATOM   2798  CE2  TYR B  56      25.336  28.095  91.172  1.00 26.32           C
ATOM   2799  CZ   TYR B  56      24.841  27.064  91.958  1.00 26.32           C
ATOM   2800  OH   TYR B  56      25.681  26.056  92.362  1.00 26.32           O
ATOM   2801  C    TYR B  56      21.163  30.902  92.753  1.00 36.50           C
ATOM   2802  O    TYR B  56      21.721  30.644  93.822  1.00 36.50           O
ATOM   2803  N    THR B  57      19.856  30.787  92.563  1.00 51.95           N
ATOM   2804  CA   THR B  57      18.966  30.380  93.635  1.00 51.95           C
ATOM   2805  CB   THR B  57      18.242  31.592  94.212  1.00 37.29           C
ATOM   2806  OG1  THR B  57      17.880  32.478  93.142  1.00 37.29           O
ATOM   2807  CG2  THR B  57      19.122  32.300  95.215  1.00 37.29           C
ATOM   2808  C    THR B  57      17.906  29.402  93.169  1.00 51.95           C
ATOM   2809  O    THR B  57      17.864  29.026  91.996  1.00 51.95           O
ATOM   2810  N    ASP B  58      17.058  28.996  94.111  1.00 65.44           N
ATOM   2811  CA   ASP B  58      15.953  28.100  93.824  1.00 65.44           C
ATOM   2812  CB   ASP B  58      14.920  28.845  92.964  1.00 51.07           C
ATOM   2813  CG   ASP B  58      14.763  30.329  93.361  1.00 51.07           C
ATOM   2814  OD1  ASP B  58      14.055  30.622  94.341  1.00 51.07           O
ATOM   2815  OD2  ASP B  58      15.350  31.212  92.696  1.00 51.07           O
ATOM   2816  C    ASP B  58      16.468  26.863  93.091  1.00 65.44           C
ATOM   2817  O    ASP B  58      16.049  26.561  91.973  1.00 65.44           O
```

FIG. 7-48

```
ATOM   2818  N    THR B  59      17.389  26.159  93.732  1.00 33.46           N
ATOM   2819  CA   THR B  59      17.984  24.961  93.165  1.00 33.46           C
ATOM   2820  CB   THR B  59      19.433  24.831  93.643  1.00 29.94           C
ATOM   2821  OG1  THR B  59      19.471  24.689  95.068  1.00 29.94           O
ATOM   2822  CG2  THR B  59      20.190  26.077  93.289  1.00 29.94           C
ATOM   2823  C    THR B  59      17.186  23.711  93.540  1.00 33.46           C
ATOM   2824  O    THR B  59      17.123  23.335  94.708  1.00 33.46           O
ATOM   2825  N    LYS B  60      16.592  23.066  92.542  1.00 45.53           N
ATOM   2826  CA   LYS B  60      15.768  21.888  92.771  1.00 45.53           C
ATOM   2827  CB   LYS B  60      14.309  22.256  92.517  1.00 34.55           C
ATOM   2828  CG   LYS B  60      14.134  23.286  91.390  1.00 34.55           C
ATOM   2829  CD   LYS B  60      12.757  23.947  91.399  1.00 34.55           C
ATOM   2830  CE   LYS B  60      12.570  24.783  92.644  1.00 34.55           C
ATOM   2831  NZ   LYS B  60      11.340  25.606  92.589  1.00 34.55           N
ATOM   2832  C    LYS B  60      16.194  20.723  91.896  1.00 45.53           C
ATOM   2833  O    LYS B  60      16.719  20.924  90.798  1.00 45.53           O
ATOM   2834  N    VAL B  61      15.972  19.509  92.387  1.00 46.69           N
ATOM   2835  CA   VAL B  61      16.362  18.314  91.663  1.00 46.69           C
ATOM   2836  CB   VAL B  61      16.448  17.101  92.611  1.00 37.01           C
ATOM   2837  CG1  VAL B  61      17.234  15.987  91.961  1.00 37.01           C
ATOM   2838  CG2  VAL B  61      17.102  17.508  93.931  1.00 37.01           C
ATOM   2839  C    VAL B  61      15.373  18.036  90.553  1.00 46.69           C
ATOM   2840  O    VAL B  61      14.168  18.277  90.705  1.00 46.69           O
ATOM   2841  N    ILE B  62      15.893  17.552  89.432  1.00 39.48           N
ATOM   2842  CA   ILE B  62      15.067  17.269  88.274  1.00 39.48           C
ATOM   2843  CB   ILE B  62      15.648  17.941  87.023  1.00 28.45           C
ATOM   2844  CG2  ILE B  62      14.757  17.688  85.795  1.00 28.45           C
ATOM   2845  CG1  ILE B  62      15.789  19.430  87.284  1.00 28.45           C
ATOM   2846  CD1  ILE B  62      15.807  20.264  86.044  1.00 28.45           C
ATOM   2847  C    ILE B  62      15.036  15.789  88.020  1.00 39.48           C
ATOM   2848  O    ILE B  62      14.016  15.116  88.177  1.00 39.48           O
ATOM   2849  N    GLY B  63      16.189  15.296  87.610  1.00 70.45           N
ATOM   2850  CA   GLY B  63      16.325  13.893  87.328  1.00 70.45           C
ATOM   2851  C    GLY B  63      17.771  13.511  87.442  1.00 70.45           C
ATOM   2852  O    GLY B  63      18.565  14.191  88.106  1.00 70.45           O
ATOM   2853  N    ASN B  64      18.118  12.439  86.745  1.00 65.27           N
ATOM   2854  CA   ASN B  64      19.469  11.890  86.747  1.00 65.27           C
ATOM   2855  CB   ASN B  64      19.895  11.452  88.166  1.00 49.33           C
ATOM   2856  CG   ASN B  64      18.769  10.806  88.950  1.00 49.33           C
ATOM   2857  OD1  ASN B  64      17.998  10.008  88.416  1.00 49.33           O
ATOM   2858  ND2  ASN B  64      18.685  11.132  90.230  1.00 49.33           N
ATOM   2859  C    ASN B  64      19.418  10.677  85.832  1.00 65.27           C
ATOM   2860  O    ASN B  64      18.379  10.016  85.731  1.00 65.27           O
ATOM   2861  N    GLY B  65      20.545  10.400  85.181  1.00 54.13           N
ATOM   2862  CA   GLY B  65      20.651   9.280  84.275  1.00 54.13           C
ATOM   2863  C    GLY B  65      21.523   8.237  84.912  1.00 54.13           C
ATOM   2864  O    GLY B  65      21.487   8.060  86.131  1.00 54.13           O
ATOM   2865  N    SER B  66      22.295   7.548  84.086  1.00 99.97           N
ATOM   2866  CA   SER B  66      23.194   6.524  84.573  1.00 99.97           C
ATOM   2867  CB   SER B  66      23.988   5.934  83.403  1.00 23.68           C
ATOM   2868  OG   SER B  66      23.295   4.838  82.795  1.00 23.68           O
ATOM   2869  C    SER B  66      24.146   7.158  85.587  1.00 99.97           C
ATOM   2870  O    SER B  66      24.265   6.692  86.720  1.00 99.97           O
ATOM   2871  N    PHE B  67      24.796   8.243  85.183  1.00 93.06           N
ATOM   2872  CA   PHE B  67      25.766   8.931  86.037  1.00 93.06           C
ATOM   2873  CB   PHE B  67      27.214   8.845  85.475  1.00 59.78           C
ATOM   2874  CG   PHE B  67      27.557   7.516  84.880  1.00 59.78           C
ATOM   2875  CD1  PHE B  67      27.498   7.325  83.495  1.00 59.78           C
ATOM   2876  CD2  PHE B  67      27.832   6.427  85.711  1.00 59.78           C
ATOM   2877  CE1  PHE B  67      27.698   6.079  82.946  1.00 59.78           C
```

FIG. 7-49

```
ATOM   2878  CE2  PHE B  67      28.031   5.182  85.185  1.00 59.78           C
ATOM   2879  CZ   PHE B  67      27.963   4.997  83.793  1.00 59.78           C
ATOM   2880  C    PHE B  67      25.341  10.352  85.970  1.00 93.06           C
ATOM   2881  O    PHE B  67      24.910  10.792  84.918  1.00 93.06           O
ATOM   2882  N    GLY B  68      25.525  11.089  87.056  1.00 49.67           N
ATOM   2883  CA   GLY B  68      25.133  12.489  87.061  1.00 49.67           C
ATOM   2884  C    GLY B  68      23.678  12.850  87.395  1.00 49.67           C
ATOM   2885  O    GLY B  68      22.711  12.391  86.760  1.00 49.67           O
ATOM   2886  N    VAL B  69      23.547  13.743  88.373  1.00 42.78           N
ATOM   2887  CA   VAL B  69      22.279  14.232  88.858  1.00 42.78           C
ATOM   2888  CB   VAL B  69      22.240  14.123  90.376  1.00 42.42           C
ATOM   2889  CG1  VAL B  69      23.635  14.300  90.928  1.00 42.42           C
ATOM   2890  CG2  VAL B  69      21.279  15.145  90.955  1.00 42.42           C
ATOM   2891  C    VAL B  69      22.092  15.679  88.423  1.00 42.78           C
ATOM   2892  O    VAL B  69      22.923  16.547  88.692  1.00 42.78           O
ATOM   2893  N    VAL B  70      20.978  15.920  87.745  1.00 47.47           N
ATOM   2894  CA   VAL B  70      20.659  17.252  87.255  1.00 47.47           C
ATOM   2895  CB   VAL B  70      20.104  17.169  85.834  1.00 27.15           C
ATOM   2896  CG1  VAL B  70      20.086  18.578  85.207  1.00 27.15           C
ATOM   2897  CG2  VAL B  70      20.988  16.228  85.023  1.00 27.15           C
ATOM   2898  C    VAL B  70      19.731  18.131  88.117  1.00 47.47           C
ATOM   2899  O    VAL B  70      18.672  17.706  88.582  1.00 47.47           O
ATOM   2900  N    TYR B  71      20.152  19.380  88.317  1.00 32.02           N
ATOM   2901  CA   TYR B  71      19.402  20.363  89.106  1.00 32.02           C
ATOM   2902  CB   TYR B  71      20.244  20.888  90.266  1.00 46.76           C
ATOM   2903  CG   TYR B  71      20.637  19.863  91.299  1.00 46.76           C
ATOM   2904  CD1  TYR B  71      21.762  19.060  91.127  1.00 46.76           C
ATOM   2905  CE1  TYR B  71      22.137  18.132  92.098  1.00 46.76           C
ATOM   2906  CD2  TYR B  71      19.896  19.711  92.468  1.00 46.76           C
ATOM   2907  CE2  TYR B  71      20.263  18.789  93.435  1.00 46.76           C
ATOM   2908  CZ   TYR B  71      21.383  18.004  93.241  1.00 46.76           C
ATOM   2909  OH   TYR B  71      21.737  17.071  94.181  1.00 46.76           O
ATOM   2910  C    TYR B  71      18.973  21.578  88.282  1.00 32.02           C
ATOM   2911  O    TYR B  71      19.579  21.899  87.256  1.00 32.02           O
ATOM   2912  N    GLN B  72      17.921  22.251  88.737  1.00 36.33           N
ATOM   2913  CA   GLN B  72      17.466  23.453  88.060  1.00 36.33           C
ATOM   2914  CB   GLN B  72      15.948  23.476  87.847  1.00 32.86           C
ATOM   2915  CG   GLN B  72      15.505  24.775  87.157  1.00 32.86           C
ATOM   2916  CD   GLN B  72      14.020  25.020  87.225  1.00 32.86           C
ATOM   2917  OE1  GLN B  72      13.359  25.164  86.201  1.00 32.86           O
ATOM   2918  NE2  GLN B  72      13.484  25.078  88.434  1.00 32.86           N
ATOM   2919  C    GLN B  72      17.828  24.586  88.992  1.00 36.33           C
ATOM   2920  O    GLN B  72      17.905  24.392  90.198  1.00 36.33           O
ATOM   2921  N    ALA B  73      18.063  25.768  88.445  1.00 31.94           N
ATOM   2922  CA   ALA B  73      18.391  26.900  89.289  1.00 31.94           C
ATOM   2923  CB   ALA B  73      19.825  26.824  89.718  1.00  7.09           C
ATOM   2924  C    ALA B  73      18.136  28.184  88.537  1.00 31.94           C
ATOM   2925  O    ALA B  73      17.946  28.165  87.317  1.00 31.94           O
ATOM   2926  N    LYS B  74      18.131  29.298  89.265  1.00 37.21           N
ATOM   2927  CA   LYS B  74      17.884  30.594  88.652  1.00 37.21           C
ATOM   2928  CB   LYS B  74      16.598  31.206  89.224  1.00 39.75           C
ATOM   2929  CG   LYS B  74      16.014  32.389  88.448  1.00 39.75           C
ATOM   2930  CD   LYS B  74      14.780  32.917  89.177  1.00 39.75           C
ATOM   2931  CE   LYS B  74      14.094  34.023  88.411  1.00 39.75           C
ATOM   2932  NZ   LYS B  74      12.978  34.613  89.195  1.00 39.75           N
ATOM   2933  C    LYS B  74      19.062  31.521  88.893  1.00 37.21           C
ATOM   2934  O    LYS B  74      19.469  31.744  90.033  1.00 37.21           O
ATOM   2935  N    LEU B  75      19.613  32.041  87.801  1.00 31.31           N
ATOM   2936  CA   LEU B  75      20.739  32.963  87.859  1.00 31.31           C
ATOM   2937  CB   LEU B  75      21.384  33.113  86.476  1.00 25.85           C
```

FIG. 7-50

| | | | | | | | | | | |
|---|---|---|---|---|---|---|---|---|---|---|
| ATOM | 2938 | CG | LEU | B | 75 | 21.781 | 31.758 | 85.878 | 1.00 25.85 | C |
| ATOM | 2939 | CD1 | LEU | B | 75 | 22.488 | 31.953 | 84.553 | 1.00 25.85 | C |
| ATOM | 2940 | CD2 | LEU | B | 75 | 22.677 | 30.983 | 86.875 | 1.00 25.85 | C |
| ATOM | 2941 | C | LEU | B | 75 | 20.199 | 34.296 | 88.322 | 1.00 31.31 | C |
| ATOM | 2942 | O | LEU | B | 75 | 19.233 | 34.801 | 87.756 | 1.00 31.31 | O |
| ATOM | 2943 | N | CYS | B | 76 | 20.823 | 34.855 | 89.357 | 1.00 40.78 | N |
| ATOM | 2944 | CA | CYS | B | 76 | 20.409 | 36.135 | 89.931 | 1.00 40.78 | C |
| ATOM | 2945 | CB | CYS | B | 76 | 21.187 | 36.402 | 91.219 | 1.00 35.55 | C |
| ATOM | 2946 | SG | CYS | B | 76 | 21.279 | 35.009 | 92.333 | 1.00 35.55 | S |
| ATOM | 2947 | C | CYS | B | 76 | 20.705 | 37.245 | 88.942 | 1.00 40.78 | C |
| ATOM | 2948 | O | CYS | B | 76 | 20.009 | 38.263 | 88.873 | 1.00 40.78 | O |
| ATOM | 2949 | N | ASP | B | 77 | 21.761 | 37.015 | 88.176 | 1.00 60.55 | N |
| ATOM | 2950 | CA | ASP | B | 77 | 22.246 | 37.955 | 87.188 | 1.00 60.55 | C |
| ATOM | 2951 | CB | ASP | B | 77 | 23.452 | 37.338 | 86.460 | 1.00 84.67 | C |
| ATOM | 2952 | CG | ASP | B | 77 | 24.505 | 36.778 | 87.428 | 1.00 84.67 | C |
| ATOM | 2953 | OD1 | ASP | B | 77 | 24.439 | 35.574 | 87.765 | 1.00 84.67 | O |
| ATOM | 2954 | OD2 | ASP | B | 77 | 25.393 | 37.546 | 87.867 | 1.00 84.67 | O |
| ATOM | 2955 | C | ASP | B | 77 | 21.173 | 38.376 | 86.191 | 1.00 60.55 | C |
| ATOM | 2956 | O | ASP | B | 77 | 21.184 | 39.502 | 85.697 | 1.00 60.55 | O |
| ATOM | 2957 | N | SER | B | 78 | 20.228 | 37.486 | 85.912 | 1.00 67.21 | N |
| ATOM | 2958 | CA | SER | B | 78 | 19.186 | 37.798 | 84.942 | 1.00 67.21 | C |
| ATOM | 2959 | CB | SER | B | 78 | 19.666 | 37.418 | 83.550 | 1.00 51.67 | C |
| ATOM | 2960 | OG | SER | B | 78 | 19.956 | 36.030 | 83.504 | 1.00 51.67 | O |
| ATOM | 2961 | C | SER | B | 78 | 17.871 | 37.082 | 85.207 | 1.00 67.21 | C |
| ATOM | 2962 | O | SER | B | 78 | 16.928 | 37.208 | 84.424 | 1.00 67.21 | O |
| ATOM | 2963 | N | GLY | B | 79 | 17.812 | 36.321 | 86.295 | 1.00 48.03 | N |
| ATOM | 2964 | CA | GLY | B | 79 | 16.594 | 35.608 | 86.624 | 1.00 48.03 | C |
| ATOM | 2965 | C | GLY | B | 79 | 16.286 | 34.517 | 85.619 | 1.00 48.03 | C |
| ATOM | 2966 | O | GLY | B | 79 | 15.161 | 34.012 | 85.559 | 1.00 48.03 | O |
| ATOM | 2967 | N | GLU | B | 80 | 17.285 | 34.153 | 84.820 | 1.00 42.19 | N |
| ATOM | 2968 | CA | GLU | B | 80 | 17.107 | 33.103 | 83.825 | 1.00 42.19 | C |
| ATOM | 2969 | CB | GLU | B | 80 | 18.226 | 33.137 | 82.795 | 1.00 63.41 | C |
| ATOM | 2970 | CG | GLU | B | 80 | 18.342 | 34.413 | 82.014 | 1.00 63.41 | C |
| ATOM | 2971 | CD | GLU | B | 80 | 18.926 | 34.170 | 80.645 | 1.00 63.41 | C |
| ATOM | 2972 | OE1 | GLU | B | 80 | 18.189 | 33.640 | 79.794 | 1.00 63.41 | O |
| ATOM | 2973 | OE2 | GLU | B | 80 | 20.113 | 34.489 | 80.420 | 1.00 63.41 | O |
| ATOM | 2974 | C | GLU | B | 80 | 17.124 | 31.738 | 84.493 | 1.00 42.19 | C |
| ATOM | 2975 | O | GLU | B | 80 | 17.700 | 31.571 | 85.574 | 1.00 42.19 | O |
| ATOM | 2976 | N | LEU | B | 81 | 16.499 | 30.761 | 83.841 | 1.00 33.86 | N |
| ATOM | 2977 | CA | LEU | B | 81 | 16.465 | 29.391 | 84.361 | 1.00 33.86 | C |
| ATOM | 2978 | CB | LEU | B | 81 | 15.123 | 28.722 | 84.059 | 1.00 30.28 | C |
| ATOM | 2979 | CG | LEU | B | 81 | 14.138 | 28.724 | 85.233 | 1.00 30.28 | C |
| ATOM | 2980 | CD1 | LEU | B | 81 | 13.854 | 30.153 | 85.673 | 1.00 30.28 | C |
| ATOM | 2981 | CD2 | LEU | B | 81 | 12.844 | 28.029 | 84.816 | 1.00 30.28 | C |
| ATOM | 2982 | C | LEU | B | 81 | 17.585 | 28.567 | 83.754 | 1.00 33.86 | C |
| ATOM | 2983 | O | LEU | B | 81 | 17.845 | 28.656 | 82.556 | 1.00 33.86 | O |
| ATOM | 2984 | N | VAL | B | 82 | 18.260 | 27.773 | 84.574 | 1.00 40.41 | N |
| ATOM | 2985 | CA | VAL | B | 82 | 19.353 | 26.954 | 84.065 | 1.00 40.41 | C |
| ATOM | 2986 | CB | VAL | B | 82 | 20.750 | 27.617 | 84.269 | 1.00 25.85 | C |
| ATOM | 2987 | CG1 | VAL | B | 82 | 20.863 | 28.893 | 83.428 | 1.00 25.85 | C |
| ATOM | 2988 | CG2 | VAL | B | 82 | 20.975 | 27.918 | 85.750 | 1.00 25.85 | C |
| ATOM | 2989 | C | VAL | B | 82 | 19.394 | 25.601 | 84.724 | 1.00 40.41 | C |
| ATOM | 2990 | O | VAL | B | 82 | 18.787 | 25.370 | 85.774 | 1.00 40.41 | O |
| ATOM | 2991 | N | ALA | B | 83 | 20.135 | 24.708 | 84.089 | 1.00 26.94 | N |
| ATOM | 2992 | CA | ALA | B | 83 | 20.284 | 23.362 | 84.584 | 1.00 26.94 | C |
| ATOM | 2993 | CB | ALA | B | 83 | 19.811 | 22.385 | 83.536 | 1.00 21.59 | C |
| ATOM | 2994 | C | ALA | B | 83 | 21.741 | 23.097 | 84.940 | 1.00 26.94 | C |
| ATOM | 2995 | O | ALA | B | 83 | 22.650 | 23.451 | 84.188 | 1.00 26.94 | O |
| ATOM | 2996 | N | ILE | B | 84 | 21.953 | 22.468 | 86.091 | 1.00 26.70 | N |
| ATOM | 2997 | CA | ILE | B | 84 | 23.295 | 22.147 | 86.550 | 1.00 26.70 | C |

FIG. 7-51

| ATOM | 2998 | CB | ILE | B | 84 | 23.552 | 22.727 | 87.964 | 1.00 | 23.72 | C |
|---|---|---|---|---|---|---|---|---|---|---|---|
| ATOM | 2999 | CG2 | ILE | B | 84 | 24.979 | 22.456 | 88.393 | 1.00 | 23.72 | C |
| ATOM | 3000 | CG1 | ILE | B | 84 | 23.301 | 24.230 | 87.971 | 1.00 | 23.72 | C |
| ATOM | 3001 | CD1 | ILE | B | 84 | 23.318 | 24.826 | 89.360 | 1.00 | 23.72 | C |
| ATOM | 3002 | C | ILE | B | 84 | 23.483 | 20.636 | 86.617 | 1.00 | 26.70 | C |
| ATOM | 3003 | O | ILE | B | 84 | 22.969 | 19.982 | 87.533 | 1.00 | 26.70 | O |
| ATOM | 3004 | N | LYS | B | 85 | 24.200 | 20.071 | 85.650 | 1.00 | 14.28 | N |
| ATOM | 3005 | CA | LYS | B | 85 | 24.448 | 18.634 | 85.681 | 1.00 | 14.28 | C |
| ATOM | 3006 | CB | LYS | B | 85 | 24.781 | 18.103 | 84.287 | 1.00 | 12.82 | C |
| ATOM | 3007 | CG | LYS | B | 85 | 25.163 | 16.611 | 84.269 | 1.00 | 12.82 | C |
| ATOM | 3008 | CD | LYS | B | 85 | 25.308 | 16.118 | 82.836 | 1.00 | 12.82 | C |
| ATOM | 3009 | CE | LYS | B | 85 | 25.941 | 14.747 | 82.756 | 1.00 | 12.82 | C |
| ATOM | 3010 | NZ | LYS | B | 85 | 26.016 | 14.221 | 81.350 | 1.00 | 12.82 | N |
| ATOM | 3011 | C | LYS | B | 85 | 25.633 | 18.414 | 86.629 | 1.00 | 14.28 | C |
| ATOM | 3012 | O | LYS | B | 85 | 26.714 | 18.972 | 86.425 | 1.00 | 14.28 | O |
| ATOM | 3013 | N | LYS | B | 86 | 25.429 | 17.623 | 87.679 | 1.00 | 22.41 | N |
| ATOM | 3014 | CA | LYS | B | 86 | 26.498 | 17.369 | 88.645 | 1.00 | 22.41 | C |
| ATOM | 3015 | CB | LYS | B | 86 | 25.974 | 17.602 | 90.068 | 1.00 | 44.09 | C |
| ATOM | 3016 | CG | LYS | B | 86 | 27.003 | 18.103 | 91.078 | 1.00 | 44.09 | C |
| ATOM | 3017 | CD | LYS | B | 86 | 26.444 | 18.014 | 92.501 | 1.00 | 44.09 | C |
| ATOM | 3018 | CE | LYS | B | 86 | 27.107 | 18.998 | 93.486 | 1.00 | 44.09 | C |
| ATOM | 3019 | NZ | LYS | B | 86 | 26.692 | 20.454 | 93.346 | 1.00 | 44.09 | N |
| ATOM | 3020 | C | LYS | B | 86 | 26.983 | 15.924 | 88.499 | 1.00 | 22.41 | C |
| ATOM | 3021 | O | LYS | B | 86 | 26.411 | 15.013 | 89.093 | 1.00 | 22.41 | O |
| ATOM | 3022 | N | VAL | B | 87 | 28.021 | 15.708 | 87.697 | 1.00 | 31.96 | N |
| ATOM | 3023 | CA | VAL | B | 87 | 28.540 | 14.350 | 87.518 | 1.00 | 31.96 | C |
| ATOM | 3024 | CB | VAL | B | 87 | 28.771 | 13.968 | 86.035 | 1.00 | 47.85 | C |
| ATOM | 3025 | CG1 | VAL | B | 87 | 27.458 | 13.865 | 85.313 | 1.00 | 47.85 | C |
| ATOM | 3026 | CG2 | VAL | B | 87 | 29.668 | 14.978 | 85.369 | 1.00 | 47.85 | C |
| ATOM | 3027 | C | VAL | B | 87 | 29.858 | 14.126 | 88.231 | 1.00 | 31.96 | C |
| ATOM | 3028 | O | VAL | B | 87 | 30.772 | 14.961 | 88.160 | 1.00 | 31.96 | O |
| ATOM | 3029 | N | LEU | B | 88 | 29.955 | 12.987 | 88.908 | 1.00 | 46.44 | N |
| ATOM | 3030 | CA | LEU | B | 88 | 31.160 | 12.631 | 89.642 | 1.00 | 46.44 | C |
| ATOM | 3031 | CB | LEU | B | 88 | 30.924 | 11.375 | 90.448 | 1.00 | 36.52 | C |
| ATOM | 3032 | CG | LEU | B | 88 | 32.145 | 10.785 | 91.120 | 1.00 | 36.52 | C |
| ATOM | 3033 | CD1 | LEU | B | 88 | 32.243 | 11.384 | 92.486 | 1.00 | 36.52 | C |
| ATOM | 3034 | CD2 | LEU | B | 88 | 32.009 | 9.292 | 91.205 | 1.00 | 36.52 | C |
| ATOM | 3035 | C | LEU | B | 88 | 32.302 | 12.365 | 88.693 | 1.00 | 46.44 | C |
| ATOM | 3036 | O | LEU | B | 88 | 32.077 | 11.987 | 87.545 | 1.00 | 46.44 | O |
| ATOM | 3037 | N | GLN | B | 89 | 33.525 | 12.554 | 89.174 | 1.00 | 54.38 | N |
| ATOM | 3038 | CA | GLN | B | 89 | 34.704 | 12.307 | 88.352 | 1.00 | 54.38 | C |
| ATOM | 3039 | CB | GLN | B | 89 | 35.708 | 13.430 | 88.515 | 1.00 | 54.83 | C |
| ATOM | 3040 | CG | GLN | B | 89 | 35.960 | 14.146 | 87.200 | 1.00 | 54.83 | C |
| ATOM | 3041 | CD | GLN | B | 89 | 34.696 | 14.769 | 86.609 | 1.00 | 54.83 | C |
| ATOM | 3042 | OE1 | GLN | B | 89 | 34.517 | 15.977 | 86.678 | 1.00 | 54.83 | O |
| ATOM | 3043 | NE2 | GLN | B | 89 | 33.828 | 13.952 | 86.018 | 1.00 | 54.83 | N |
| ATOM | 3044 | C | GLN | B | 89 | 35.357 | 10.992 | 88.728 | 1.00 | 54.38 | C |
| ATOM | 3045 | O | GLN | B | 89 | 35.556 | 10.726 | 89.909 | 1.00 | 54.38 | O |
| ATOM | 3046 | N | ASP | B | 90 | 35.706 | 10.171 | 87.746 | 1.00 | 32.91 | N |
| ATOM | 3047 | CA | ASP | B | 90 | 36.310 | 8.889 | 88.055 | 1.00 | 32.91 | C |
| ATOM | 3048 | CB | ASP | B | 90 | 35.359 | 7.760 | 87.664 | 1.00 | 43.97 | C |
| ATOM | 3049 | CG | ASP | B | 90 | 35.735 | 6.435 | 88.292 | 1.00 | 43.97 | C |
| ATOM | 3050 | OD1 | ASP | B | 90 | 34.871 | 5.535 | 88.314 | 1.00 | 43.97 | O |
| ATOM | 3051 | OD2 | ASP | B | 90 | 36.888 | 6.296 | 88.757 | 1.00 | 43.97 | O |
| ATOM | 3052 | C | ASP | B | 90 | 37.634 | 8.710 | 87.333 | 1.00 | 32.91 | C |
| ATOM | 3053 | O | ASP | B | 90 | 37.663 | 8.509 | 86.122 | 1.00 | 32.91 | O |
| ATOM | 3054 | N | GLY | B | 91 | 38.728 | 8.768 | 88.086 | 1.00 | 35.99 | N |
| ATOM | 3055 | CA | GLY | B | 91 | 40.045 | 8.599 | 87.501 | 1.00 | 35.99 | C |
| ATOM | 3056 | C | GLY | B | 91 | 40.157 | 7.275 | 86.775 | 1.00 | 35.99 | C |
| ATOM | 3057 | O | GLY | B | 91 | 41.046 | 7.101 | 85.938 | 1.00 | 35.99 | O |

FIG. 7-52

```
ATOM   3058  N    ALA B  92      39.301   6.317  87.110  1.00 53.18           N
ATOM   3059  CA   ALA B  92      39.384   5.035  86.429  1.00 53.18           C
ATOM   3060  CB   ALA B  92      38.983   3.905  87.366  1.00  7.11           C
ATOM   3061  C    ALA B  92      38.561   4.955  85.150  1.00 53.18           C
ATOM   3062  O    ALA B  92      38.445   3.877  84.552  1.00 53.18           O
ATOM   3063  N    PHE B  93      38.017   6.078  84.700  1.00 60.78           N
ATOM   3064  CA   PHE B  93      37.207   6.028  83.500  1.00 60.78           C
ATOM   3065  CB   PHE B  93      35.729   6.025  83.880  1.00 66.95           C
ATOM   3066  CG   PHE B  93      35.181   4.628  84.079  1.00 66.95           C
ATOM   3067  CD1  PHE B  93      35.196   3.735  83.003  1.00 66.95           C
ATOM   3068  CD2  PHE B  93      34.717   4.165  85.323  1.00 66.95           C
ATOM   3069  CE1  PHE B  93      34.767   2.400  83.132  1.00 66.95           C
ATOM   3070  CE2  PHE B  93      34.280   2.815  85.465  1.00 66.95           C
ATOM   3071  CZ   PHE B  93      34.309   1.937  84.363  1.00 66.95           C
ATOM   3072  C    PHE B  93      37.523   7.018  82.389  1.00 60.78           C
ATOM   3073  O    PHE B  93      37.186   6.756  81.245  1.00 60.78           O
ATOM   3074  N    LYS B  94      38.207   8.120  82.696  1.00 50.24           N
ATOM   3075  CA   LYS B  94      38.605   9.088  81.658  1.00 50.24           C
ATOM   3076  CB   LYS B  94      39.615   8.378  80.760  1.00 23.68           C
ATOM   3077  CG   LYS B  94      39.579   8.815  79.303  1.00 23.68           C
ATOM   3078  CD   LYS B  94      40.047   7.735  78.353  1.00 23.68           C
ATOM   3079  CE   LYS B  94      41.355   8.205  77.772  1.00 23.68           C
ATOM   3080  NZ   LYS B  94      42.134   7.017  77.310  1.00 23.68           N
ATOM   3081  C    LYS B  94      37.547   9.807  80.777  1.00 50.24           C
ATOM   3082  O    LYS B  94      37.468   9.607  79.568  1.00 50.24           O
ATOM   3083  N    ASN B  95      36.775  10.704  81.354  1.00 44.11           N
ATOM   3084  CA   ASN B  95      35.752  11.384  80.573  1.00 44.11           C
ATOM   3085  CB   ASN B  95      34.560  11.529  81.516  1.00 78.25           C
ATOM   3086  CG   ASN B  95      33.546  12.539  81.079  1.00 78.25           C
ATOM   3087  OD1  ASN B  95      33.769  13.326  80.178  1.00 78.25           O
ATOM   3088  ND2  ASN B  95      32.411  12.546  81.769  1.00 78.25           N
ATOM   3089  C    ASN B  95      36.203  12.728  79.946  1.00 44.11           C
ATOM   3090  O    ASN B  95      37.100  13.424  80.449  1.00 44.11           O
ATOM   3091  N    ARG B  96      35.564  13.060  78.825  1.00 26.55           N
ATOM   3092  CA   ARG B  96      35.813  14.298  78.078  1.00 26.55           C
ATOM   3093  CB   ARG B  96      36.466  13.945  76.761  1.00 33.08           C
ATOM   3094  CG   ARG B  96      37.100  12.620  76.832  1.00 33.08           C
ATOM   3095  CD   ARG B  96      36.967  11.918  75.533  1.00 33.08           C
ATOM   3096  NE   ARG B  96      37.892  10.785  75.467  1.00 33.08           N
ATOM   3097  CZ   ARG B  96      37.566   9.488  75.571  1.00 33.08           C
ATOM   3098  NH1  ARG B  96      36.302   9.097  75.755  1.00 33.08           N
ATOM   3099  NH2  ARG B  96      38.513   8.554  75.458  1.00 33.08           N
ATOM   3100  C    ARG B  96      34.525  15.074  77.814  1.00 26.55           C
ATOM   3101  O    ARG B  96      34.411  15.803  76.839  1.00 26.55           O
ATOM   3102  N    GLU B  97      33.575  14.921  78.719  1.00 32.59           N
ATOM   3103  CA   GLU B  97      32.283  15.545  78.591  1.00 32.59           C
ATOM   3104  CB   GLU B  97      31.373  15.095  79.736  1.00 28.80           C
ATOM   3105  CG   GLU B  97      30.284  16.055  80.070  1.00 28.80           C
ATOM   3106  CD   GLU B  97      29.060  15.362  80.588  1.00 28.80           C
ATOM   3107  OE1  GLU B  97      29.182  14.587  81.569  1.00 28.80           O
ATOM   3108  OE2  GLU B  97      27.980  15.608  80.001  1.00 28.80           O
ATOM   3109  C    GLU B  97      32.472  17.032  78.598  1.00 32.59           C
ATOM   3110  O    GLU B  97      31.763  17.760  77.915  1.00 32.59           O
ATOM   3111  N    LEU B  98      33.459  17.483  79.361  1.00 38.44           N
ATOM   3112  CA   LEU B  98      33.723  18.906  79.450  1.00 38.44           C
ATOM   3113  CB   LEU B  98      34.512  19.228  80.717  1.00 17.39           C
ATOM   3114  CG   LEU B  98      35.068  20.657  80.823  1.00 17.39           C
ATOM   3115  CD1  LEU B  98      33.998  21.713  80.602  1.00 17.39           C
ATOM   3116  CD2  LEU B  98      35.684  20.821  82.201  1.00 17.39           C
ATOM   3117  C    LEU B  98      34.457  19.406  78.218  1.00 38.44           C
```

FIG. 7-53

| | | | | | | | | | | |
|---|---|---|---|---|---|---|---|---|---|---|
| ATOM | 3118 | O | LEU | B | 98 | 34.146 | 20.478 | 77.714 | 1.00 38.44 | O |
| ATOM | 3119 | N | GLN | B | 99 | 35.420 | 18.631 | 77.726 | 1.00 30.31 | N |
| ATOM | 3120 | CA | GLN | B | 99 | 36.166 | 19.022 | 76.540 | 1.00 30.31 | C |
| ATOM | 3121 | CB | GLN | B | 99 | 37.125 | 17.924 | 76.079 | 1.00 95.46 | C |
| ATOM | 3122 | CG | GLN | B | 99 | 38.147 | 17.428 | 77.070 | 1.00 95.46 | C |
| ATOM | 3123 | CD | GLN | B | 99 | 38.976 | 16.297 | 76.486 | 1.00 95.46 | C |
| ATOM | 3124 | OE1 | GLN | B | 99 | 39.723 | 15.622 | 77.195 | 1.00 95.46 | O |
| ATOM | 3125 | NE2 | GLN | B | 99 | 38.844 | 16.086 | 75.178 | 1.00 95.46 | N |
| ATOM | 3126 | C | GLN | B | 99 | 35.185 | 19.240 | 75.407 | 1.00 30.31 | C |
| ATOM | 3127 | O | GLN | B | 99 | 34.969 | 20.366 | 74.970 | 1.00 30.31 | O |
| ATOM | 3128 | N | ILE | B | 100 | 34.606 | 18.137 | 74.928 | 1.00 26.38 | N |
| ATOM | 3129 | CA | ILE | B | 100 | 33.667 | 18.168 | 73.808 | 1.00 26.38 | C |
| ATOM | 3130 | CB | ILE | B | 100 | 32.885 | 16.833 | 73.675 | 1.00 55.67 | C |
| ATOM | 3131 | CG2 | ILE | B | 100 | 31.710 | 17.007 | 72.713 | 1.00 55.67 | C |
| ATOM | 3132 | CG1 | ILE | B | 100 | 33.805 | 15.727 | 73.154 | 1.00 55.67 | C |
| ATOM | 3133 | CD1 | ILE | B | 100 | 34.936 | 15.388 | 74.067 | 1.00 55.67 | C |
| ATOM | 3134 | C | ILE | B | 100 | 32.666 | 19.293 | 73.963 | 1.00 26.38 | C |
| ATOM | 3135 | O | ILE | B | 100 | 32.635 | 20.235 | 73.169 | 1.00 26.38 | O |
| ATOM | 3136 | N | MET | B | 101 | 31.856 | 19.168 | 75.005 | 1.00 31.19 | N |
| ATOM | 3137 | CA | MET | B | 101 | 30.824 | 20.129 | 75.332 | 1.00 31.19 | C |
| ATOM | 3138 | CB | MET | B | 101 | 30.387 | 19.897 | 76.775 | 1.00 36.33 | C |
| ATOM | 3139 | CG | MET | B | 101 | 29.223 | 20.731 | 77.234 | 1.00 36.33 | C |
| ATOM | 3140 | SD | MET | B | 101 | 27.649 | 19.924 | 76.910 | 1.00 36.33 | S |
| ATOM | 3141 | CE | MET | B | 101 | 27.572 | 18.699 | 78.247 | 1.00 36.33 | C |
| ATOM | 3142 | C | MET | B | 101 | 31.343 | 21.562 | 75.165 | 1.00 31.19 | C |
| ATOM | 3143 | O | MET | B | 101 | 30.717 | 22.411 | 74.523 | 1.00 31.19 | O |
| ATOM | 3144 | N | ARG | B | 102 | 32.522 | 21.806 | 75.714 | 1.00 51.94 | N |
| ATOM | 3145 | CA | ARG | B | 102 | 33.113 | 23.128 | 75.696 | 1.00 51.94 | C |
| ATOM | 3146 | CB | ARG | B | 102 | 34.308 | 23.137 | 76.638 | 1.00 41.63 | C |
| ATOM | 3147 | CG | ARG | B | 102 | 34.577 | 24.479 | 77.221 | 1.00 41.63 | C |
| ATOM | 3148 | CD | ARG | B | 102 | 35.794 | 24.453 | 78.085 | 1.00 41.63 | C |
| ATOM | 3149 | NE | ARG | B | 102 | 36.151 | 25.812 | 78.447 | 1.00 41.63 | N |
| ATOM | 3150 | CZ | ARG | B | 102 | 37.225 | 26.141 | 79.152 | 1.00 41.63 | C |
| ATOM | 3151 | NH1 | ARG | B | 102 | 38.060 | 25.204 | 79.577 | 1.00 41.63 | N |
| ATOM | 3152 | NH2 | ARG | B | 102 | 37.461 | 27.416 | 79.437 | 1.00 41.63 | N |
| ATOM | 3153 | C | ARG | B | 102 | 33.507 | 23.733 | 74.346 | 1.00 51.94 | C |
| ATOM | 3154 | O | ARG | B | 102 | 34.016 | 24.851 | 74.304 | 1.00 51.94 | O |
| ATOM | 3155 | N | LYS | B | 103 | 33.281 | 23.027 | 73.245 | 1.00 26.57 | N |
| ATOM | 3156 | CA | LYS | B | 103 | 33.630 | 23.591 | 71.936 | 1.00 26.57 | C |
| ATOM | 3157 | CB | LYS | B | 103 | 34.864 | 22.878 | 71.344 | 1.00 56.85 | C |
| ATOM | 3158 | CG | LYS | B | 103 | 34.652 | 21.432 | 70.916 | 1.00 56.85 | C |
| ATOM | 3159 | CD | LYS | B | 103 | 35.806 | 20.876 | 70.028 | 1.00 56.85 | C |
| ATOM | 3160 | CE | LYS | B | 103 | 37.091 | 20.549 | 70.806 | 1.00 56.85 | C |
| ATOM | 3161 | NZ | LYS | B | 103 | 37.883 | 19.445 | 70.175 | 1.00 56.85 | N |
| ATOM | 3162 | C | LYS | B | 103 | 32.437 | 23.518 | 70.965 | 1.00 26.57 | C |
| ATOM | 3163 | O | LYS | B | 103 | 32.508 | 23.953 | 69.815 | 1.00 26.57 | O |
| ATOM | 3164 | N | LEU | B | 104 | 31.325 | 22.987 | 71.457 | 1.00 31.99 | N |
| ATOM | 3165 | CA | LEU | B | 104 | 30.123 | 22.834 | 70.654 | 1.00 31.99 | C |
| ATOM | 3166 | CB | LEU | B | 104 | 29.308 | 21.656 | 71.197 | 1.00 29.97 | C |
| ATOM | 3167 | CG | LEU | B | 104 | 29.487 | 20.266 | 70.573 | 1.00 29.97 | C |
| ATOM | 3168 | CD1 | LEU | B | 104 | 30.932 | 19.993 | 70.247 | 1.00 29.97 | C |
| ATOM | 3169 | CD2 | LEU | B | 104 | 28.944 | 19.230 | 71.529 | 1.00 29.97 | C |
| ATOM | 3170 | C | LEU | B | 104 | 29.260 | 24.089 | 70.617 | 1.00 31.99 | C |
| ATOM | 3171 | O | LEU | B | 104 | 29.121 | 24.795 | 71.608 | 1.00 31.99 | O |
| ATOM | 3172 | N | ASP | B | 105 | 28.684 | 24.369 | 69.459 | 1.00 41.97 | N |
| ATOM | 3173 | CA | ASP | B | 105 | 27.821 | 25.529 | 69.321 | 1.00 41.97 | C |
| ATOM | 3174 | CB | ASP | B | 105 | 28.638 | 26.777 | 69.021 | 1.00 60.41 | C |
| ATOM | 3175 | CG | ASP | B | 105 | 27.794 | 28.042 | 69.057 | 1.00 60.41 | C |
| ATOM | 3176 | OD1 | ASP | B | 105 | 26.645 | 28.018 | 68.566 | 1.00 60.41 | O |
| ATOM | 3177 | OD2 | ASP | B | 105 | 28.278 | 29.071 | 69.571 | 1.00 60.41 | O |

FIG. 7-54

```
ATOM   3178  C   ASP B 105      26.834  25.300  68.188  1.00 41.97           C
ATOM   3179  O   ASP B 105      27.127  25.621  67.033  1.00 41.97           O
ATOM   3180  N   HIS B 106      25.668  24.743  68.515  1.00 28.68           N
ATOM   3181  CA  HIS B 106      24.645  24.470  67.511  1.00 28.68           C
ATOM   3182  CB  HIS B 106      24.797  23.041  66.974  1.00 26.89           C
ATOM   3183  CG  HIS B 106      24.005  22.777  65.733  1.00 26.89           C
ATOM   3184  CD2 HIS B 106      24.383  22.696  64.434  1.00 26.89           C
ATOM   3185  ND1 HIS B 106      22.641  22.590  65.747  1.00 26.89           N
ATOM   3186  CE1 HIS B 106      22.214  22.406  64.509  1.00 26.89           C
ATOM   3187  NE2 HIS B 106      23.251  22.467  63.694  1.00 26.89           N
ATOM   3188  C   HIS B 106      23.266  24.676  68.128  1.00 28.68           C
ATOM   3189  O   HIS B 106      23.070  24.455  69.328  1.00 28.68           O
ATOM   3190  N   CYS B 107      22.317  25.116  67.307  1.00 37.82           N
ATOM   3191  CA  CYS B 107      20.963  25.380  67.779  1.00 37.82           C
ATOM   3192  CB  CYS B 107      20.161  26.072  66.690  1.00 38.39           C
ATOM   3193  SG  CYS B 107      20.322  25.302  65.093  1.00 38.39           S
ATOM   3194  C   CYS B 107      20.248  24.121  68.219  1.00 37.82           C
ATOM   3195  O   CYS B 107      19.193  24.171  68.858  1.00 37.82           O
ATOM   3196  N   ASN B 108      20.828  22.981  67.884  1.00 45.79           N
ATOM   3197  CA  ASN B 108      20.227  21.723  68.262  1.00 45.79           C
ATOM   3198  CB  ASN B 108      19.880  20.938  67.003  1.00 30.50           C
ATOM   3199  CG  ASN B 108      18.728  21.567  66.240  1.00 30.50           C
ATOM   3200  OD1 ASN B 108      18.808  21.772  65.032  1.00 30.50           O
ATOM   3201  ND2 ASN B 108      17.641  21.873  66.952  1.00 30.50           N
ATOM   3202  C   ASN B 108      21.149  20.950  69.188  1.00 45.79           C
ATOM   3203  O   ASN B 108      21.339  19.738  69.061  1.00 45.79           O
ATOM   3204  N   ILE B 109      21.718  21.689  70.130  1.00 27.52           N
ATOM   3205  CA  ILE B 109      22.617  21.135  71.128  1.00 27.52           C
ATOM   3206  CB  ILE B 109      24.080  21.016  70.565  1.00 27.17           C
ATOM   3207  CG2 ILE B 109      25.051  20.528  71.666  1.00 27.17           C
ATOM   3208  CG1 ILE B 109      24.097  20.041  69.382  1.00 27.17           C
ATOM   3209  CD1 ILE B 109      25.460  19.812  68.791  1.00 27.17           C
ATOM   3210  C   ILE B 109      22.578  22.073  72.330  1.00 27.52           C
ATOM   3211  O   ILE B 109      22.895  23.251  72.203  1.00 27.52           O
ATOM   3212  N   VAL B 110      22.171  21.568  73.489  1.00 27.96           N
ATOM   3213  CA  VAL B 110      22.118  22.417  74.674  1.00 27.96           C
ATOM   3214  CB  VAL B 110      21.880  21.608  75.969  1.00 27.90           C
ATOM   3215  CG1 VAL B 110      20.396  21.328  76.133  1.00 27.90           C
ATOM   3216  CG2 VAL B 110      22.668  20.307  75.936  1.00 27.90           C
ATOM   3217  C   VAL B 110      23.409  23.198  74.823  1.00 27.96           C
ATOM   3218  O   VAL B 110      24.483  22.697  74.535  1.00 27.96           O
ATOM   3219  N   ARG B 111      23.297  24.440  75.263  1.00 31.01           N
ATOM   3220  CA  ARG B 111      24.470  25.269  75.426  1.00 31.01           C
ATOM   3221  CB  ARG B 111      24.131  26.710  75.095  1.00 52.45           C
ATOM   3222  CG  ARG B 111      25.329  27.616  75.005  1.00 52.45           C
ATOM   3223  CD  ARG B 111      24.842  29.021  74.885  1.00 52.45           C
ATOM   3224  NE  ARG B 111      23.787  29.247  75.862  1.00 52.45           N
ATOM   3225  CZ  ARG B 111      23.136  30.395  75.998  1.00 52.45           C
ATOM   3226  NH1 ARG B 111      23.436  31.423  75.216  1.00 52.45           N
ATOM   3227  NH2 ARG B 111      22.182  30.517  76.910  1.00 52.45           N
ATOM   3228  C   ARG B 111      25.034  25.201  76.833  1.00 31.01           C
ATOM   3229  O   ARG B 111      24.289  25.116  77.812  1.00 31.01           O
ATOM   3230  N   LEU B 112      26.362  25.232  76.911  1.00 34.91           N
ATOM   3231  CA  LEU B 112      27.082  25.202  78.179  1.00 34.91           C
ATOM   3232  CB  LEU B 112      28.418  24.457  78.027  1.00 33.62           C
ATOM   3233  CG  LEU B 112      29.458  24.514  79.151  1.00 33.62           C
ATOM   3234  CD1 LEU B 112      28.892  23.921  80.439  1.00 33.62           C
ATOM   3235  CD2 LEU B 112      30.701  23.762  78.702  1.00 33.62           C
ATOM   3236  C   LEU B 112      27.343  26.652  78.530  1.00 34.91           C
ATOM   3237  O   LEU B 112      28.089  27.350  77.838  1.00 34.91           O
```

FIG. 7-55

```
ATOM   3238  N    ARG B 113      26.707  27.109  79.598  1.00 32.97           N
ATOM   3239  CA   ARG B 113      26.870  28.478  80.036  1.00 32.97           C
ATOM   3240  CB   ARG B 113      25.708  28.871  80.932  1.00 38.81           C
ATOM   3241  CG   ARG B 113      24.378  28.840  80.238  1.00 38.81           C
ATOM   3242  CD   ARG B 113      23.735  30.205  80.321  1.00 38.81           C
ATOM   3243  NE   ARG B 113      22.294  30.162  80.099  1.00 38.81           N
ATOM   3244  CZ   ARG B 113      21.518  31.242  80.078  1.00 38.81           C
ATOM   3245  NH1  ARG B 113      22.046  32.448  80.266  1.00 38.81           N
ATOM   3246  NH2  ARG B 113      20.215  31.115  79.866  1.00 38.81           N
ATOM   3247  C    ARG B 113      28.179  28.591  80.795  1.00 32.97           C
ATOM   3248  O    ARG B 113      29.114  29.259  80.351  1.00 32.97           O
ATOM   3249  N    TYR B 114      28.235  27.914  81.935  1.00 35.36           N
ATOM   3250  CA   TYR B 114      29.411  27.912  82.793  1.00 35.36           C
ATOM   3251  CB   TYR B 114      29.144  28.762  84.036  1.00 46.62           C
ATOM   3252  CG   TYR B 114      28.731  30.187  83.734  1.00 46.62           C
ATOM   3253  CD1  TYR B 114      29.671  31.137  83.296  1.00 46.62           C
ATOM   3254  CE1  TYR B 114      29.298  32.459  83.036  1.00 46.62           C
ATOM   3255  CD2  TYR B 114      27.402  30.596  83.899  1.00 46.62           C
ATOM   3256  CE2  TYR B 114      27.014  31.918  83.640  1.00 46.62           C
ATOM   3257  CZ   TYR B 114      27.968  32.845  83.211  1.00 46.62           C
ATOM   3258  OH   TYR B 114      27.593  34.156  82.973  1.00 46.62           O
ATOM   3259  C    TYR B 114      29.723  26.483  83.222  1.00 35.36           C
ATOM   3260  O    TYR B 114      29.025  25.541  82.852  1.00 35.36           O
ATOM   3261  N    PHE B 115      30.784  26.329  83.998  1.00 31.05           N
ATOM   3262  CA   PHE B 115      31.169  25.028  84.514  1.00 31.05           C
ATOM   3263  CB   PHE B 115      31.819  24.187  83.419  1.00 39.53           C
ATOM   3264  CG   PHE B 115      33.229  24.589  83.103  1.00 39.53           C
ATOM   3265  CD1  PHE B 115      34.288  24.111  83.865  1.00 39.53           C
ATOM   3266  CD2  PHE B 115      33.501  25.451  82.039  1.00 39.53           C
ATOM   3267  CE1  PHE B 115      35.596  24.481  83.570  1.00 39.53           C
ATOM   3268  CE2  PHE B 115      34.812  25.831  81.734  1.00 39.53           C
ATOM   3269  CZ   PHE B 115      35.860  25.346  82.497  1.00 39.53           C
ATOM   3270  C    PHE B 115      32.140  25.256  85.667  1.00 31.05           C
ATOM   3271  O    PHE B 115      32.957  26.177  85.646  1.00 31.05           O
ATOM   3272  N    PHE B 116      32.031  24.425  86.690  1.00 20.29           N
ATOM   3273  CA   PHE B 116      32.902  24.555  87.843  1.00 20.29           C
ATOM   3274  CB   PHE B 116      32.341  25.596  88.826  1.00 35.64           C
ATOM   3275  CG   PHE B 116      31.017  25.218  89.432  1.00 35.64           C
ATOM   3276  CD1  PHE B 116      30.955  24.467  90.601  1.00 35.64           C
ATOM   3277  CD2  PHE B 116      29.828  25.621  88.832  1.00 35.64           C
ATOM   3278  CE1  PHE B 116      29.730  24.128  91.164  1.00 35.64           C
ATOM   3279  CE2  PHE B 116      28.593  25.282  89.390  1.00 35.64           C
ATOM   3280  CZ   PHE B 116      28.545  24.534  90.560  1.00 35.64           C
ATOM   3281  C    PHE B 116      33.044  23.210  88.518  1.00 20.29           C
ATOM   3282  O    PHE B 116      32.332  22.252  88.182  1.00 20.29           O
ATOM   3283  N    TYR B 117      33.985  23.123  89.450  1.00 34.16           N
ATOM   3284  CA   TYR B 117      34.185  21.867  90.159  1.00 34.16           C
ATOM   3285  CB   TYR B 117      35.629  21.381  90.020  1.00 36.67           C
ATOM   3286  CG   TYR B 117      35.959  20.855  88.645  1.00 36.67           C
ATOM   3287  CD1  TYR B 117      35.809  19.509  88.336  1.00 36.67           C
ATOM   3288  CE1  TYR B 117      36.084  19.035  87.052  1.00 36.67           C
ATOM   3289  CD2  TYR B 117      36.390  21.716  87.641  1.00 36.67           C
ATOM   3290  CE2  TYR B 117      36.661  21.254  86.359  1.00 36.67           C
ATOM   3291  CZ   TYR B 117      36.507  19.923  86.069  1.00 36.67           C
ATOM   3292  OH   TYR B 117      36.769  19.514  84.784  1.00 36.67           O
ATOM   3293  C    TYR B 117      33.829  22.070  91.614  1.00 34.16           C
ATOM   3294  O    TYR B 117      33.924  23.183  92.140  1.00 34.16           O
ATOM   3295  N    SER B 118      33.400  20.991  92.255  1.00 27.15           N
ATOM   3296  CA   SER B 118      33.005  21.062  93.654  1.00 27.15           C
ATOM   3297  CB   SER B 118      31.557  21.555  93.799  1.00 33.36           C
```

FIG. 7-56

| ATOM | 3298 | OG | SER | B | 118 | 30.617 | 20.594 | 93.371 | 1.00 | 33.36 | O |
|---|---|---|---|---|---|---|---|---|---|---|---|
| ATOM | 3299 | C | SER | B | 118 | 33.138 | 19.723 | 94.321 | 1.00 | 27.15 | C |
| ATOM | 3300 | O | SER | B | 118 | 33.285 | 18.698 | 93.652 | 1.00 | 27.15 | O |
| ATOM | 3301 | N | SER | B | 119 | 33.043 | 19.751 | 95.646 | 1.00 | 54.51 | N |
| ATOM | 3302 | CA | SER | B | 119 | 33.184 | 18.554 | 96.451 | 1.00 | 54.51 | C |
| ATOM | 3303 | CB | SER | B | 119 | 33.882 | 18.870 | 97.780 | 1.00 | 50.46 | C |
| ATOM | 3304 | OG | SER | B | 119 | 34.772 | 19.981 | 97.663 | 1.00 | 50.46 | O |
| ATOM | 3305 | C | SER | B | 119 | 31.783 | 18.085 | 96.699 | 1.00 | 54.51 | C |
| ATOM | 3306 | O | SER | B | 119 | 30.906 | 18.888 | 96.922 | 1.00 | 54.51 | O |
| ATOM | 3307 | N | GLY | B | 120 | 31.570 | 16.785 | 96.610 | 1.00 | 75.25 | N |
| ATOM | 3308 | CA | GLY | B | 120 | 30.240 | 16.240 | 96.828 | 1.00 | 75.25 | C |
| ATOM | 3309 | C | GLY | B | 120 | 30.412 | 14.987 | 97.657 | 1.00 | 75.25 | C |
| ATOM | 3310 | O | GLY | B | 120 | 31.389 | 14.950 | 98.395 | 1.00 | 75.25 | O |
| ATOM | 3311 | N | GLY | B | 121 | 29.530 | 13.981 | 97.527 | 1.00 | 82.88 | N |
| ATOM | 3312 | CA | GLY | B | 121 | 29.627 | 12.734 | 98.305 | 1.00 | 82.88 | C |
| ATOM | 3313 | C | GLY | B | 121 | 30.891 | 12.680 | 99.150 | 1.00 | 82.88 | C |
| ATOM | 3314 | O | GLY | B | 121 | 31.811 | 11.914 | 98.827 | 1.00 | 82.88 | O |
| ATOM | 3315 | N | ALA | B | 122 | 30.913 | 13.477 | 100.232 | 1.00 | 92.89 | N |
| ATOM | 3316 | CA | ALA | B | 122 | 32.080 | 13.624 | 101.098 | 1.00 | 92.89 | C |
| ATOM | 3317 | CB | ALA | B | 122 | 31.672 | 13.916 | 102.511 | 1.00 | 83.51 | C |
| ATOM | 3318 | C | ALA | B | 122 | 33.002 | 12.398 | 101.033 | 1.00 | 92.89 | C |
| ATOM | 3319 | O | ALA | B | 122 | 32.644 | 11.253 | 101.243 | 1.00 | 92.89 | O |
| ATOM | 3320 | N | GLY | B | 123 | 34.220 | 12.711 | 100.660 | 1.00 | 88.35 | N |
| ATOM | 3321 | CA | GLY | B | 123 | 35.271 | 11.741 | 100.494 | 1.00 | 88.35 | C |
| ATOM | 3322 | C | GLY | B | 123 | 36.279 | 12.431 | 99.606 | 1.00 | 88.35 | C |
| ATOM | 3323 | O | GLY | B | 123 | 36.562 | 13.589 | 99.879 | 1.00 | 88.35 | O |
| ATOM | 3324 | N | ASP | B | 124 | 36.832 | 11.758 | 98.593 | 1.00 | 73.41 | N |
| ATOM | 3325 | CA | ASP | B | 124 | 37.838 | 12.363 | 97.700 | 1.00 | 73.41 | C |
| ATOM | 3326 | CB | ASP | B | 124 | 38.848 | 11.318 | 97.224 | 1.00 | 26.37 | C |
| ATOM | 3327 | CG | ASP | B | 124 | 40.163 | 11.425 | 97.943 | 1.00 | 23.68 | C |
| ATOM | 3328 | OD1 | ASP | B | 124 | 40.460 | 12.567 | 98.409 | 1.00 | 23.68 | O |
| ATOM | 3329 | OD2 | ASP | B | 124 | 40.889 | 10.394 | 98.036 | 1.00 | 23.68 | O |
| ATOM | 3330 | C | ASP | B | 124 | 37.226 | 12.963 | 96.439 | 1.00 | 73.41 | C |
| ATOM | 3331 | O | ASP | B | 124 | 37.670 | 14.002 | 95.918 | 1.00 | 73.41 | O |
| ATOM | 3332 | N | ALA | B | 125 | 36.218 | 12.277 | 95.926 | 1.00 | 58.67 | N |
| ATOM | 3333 | CA | ALA | B | 125 | 35.577 | 12.661 | 94.683 | 1.00 | 58.67 | C |
| ATOM | 3334 | CB | ALA | B | 125 | 34.427 | 11.807 | 94.481 | 1.00 | 58.02 | C |
| ATOM | 3335 | C | ALA | B | 125 | 35.200 | 14.119 | 94.473 | 1.00 | 58.67 | C |
| ATOM | 3336 | O | ALA | B | 125 | 34.553 | 14.782 | 95.309 | 1.00 | 58.67 | O |
| ATOM | 3337 | N | VAL | B | 126 | 35.664 | 14.581 | 93.324 | 1.00 | 42.31 | N |
| ATOM | 3338 | CA | VAL | B | 126 | 35.474 | 15.912 | 92.837 | 1.00 | 42.31 | C |
| ATOM | 3339 | CB | VAL | B | 126 | 36.717 | 16.361 | 92.032 | 1.00 | 48.86 | C |
| ATOM | 3340 | CG1 | VAL | B | 126 | 37.054 | 17.737 | 92.369 | 1.00 | 48.86 | C |
| ATOM | 3341 | CG2 | VAL | B | 126 | 37.900 | 15.438 | 92.299 | 1.00 | 48.86 | C |
| ATOM | 3342 | C | VAL | B | 126 | 34.294 | 15.783 | 91.910 | 1.00 | 42.31 | C |
| ATOM | 3343 | O | VAL | B | 126 | 34.088 | 14.715 | 91.341 | 1.00 | 42.31 | O |
| ATOM | 3344 | N | TYR | B | 127 | 33.523 | 16.855 | 91.772 | 1.00 | 42.86 | N |
| ATOM | 3345 | CA | TYR | B | 127 | 32.378 | 16.821 | 90.890 | 1.00 | 42.86 | C |
| ATOM | 3346 | CB | TYR | B | 127 | 31.075 | 17.032 | 91.658 | 1.00 | 54.30 | C |
| ATOM | 3347 | CG | TYR | B | 127 | 30.576 | 15.820 | 92.412 | 1.00 | 54.30 | C |
| ATOM | 3348 | CD1 | TYR | B | 127 | 31.054 | 15.519 | 93.685 | 1.00 | 54.30 | C |
| ATOM | 3349 | CE1 | TYR | B | 127 | 30.570 | 14.424 | 94.395 | 1.00 | 54.30 | C |
| ATOM | 3350 | CD2 | TYR | B | 127 | 29.604 | 14.987 | 91.863 | 1.00 | 54.30 | C |
| ATOM | 3351 | CE2 | TYR | B | 127 | 29.117 | 13.889 | 92.564 | 1.00 | 54.30 | C |
| ATOM | 3352 | CZ | TYR | B | 127 | 29.598 | 13.615 | 93.830 | 1.00 | 54.30 | C |
| ATOM | 3353 | OH | TYR | B | 127 | 29.082 | 12.552 | 94.539 | 1.00 | 54.30 | O |
| ATOM | 3354 | C | TYR | B | 127 | 32.491 | 17.894 | 89.837 | 1.00 | 42.86 | C |
| ATOM | 3355 | O | TYR | B | 127 | 33.006 | 18.985 | 90.107 | 1.00 | 42.86 | O |
| ATOM | 3356 | N | LEU | B | 128 | 32.025 | 17.573 | 88.633 | 1.00 | 28.51 | N |
| ATOM | 3357 | CA | LEU | B | 128 | 32.027 | 18.537 | 87.545 | 1.00 | 28.51 | C |

FIG. 7-57

```
ATOM   3358  CB   LEU B 128      32.364  17.884  86.205  1.00 22.80           C
ATOM   3359  CG   LEU B 128      32.181  18.793  84.982  1.00 22.80           C
ATOM   3360  CD1  LEU B 128      33.110  20.001  85.078  1.00 22.80           C
ATOM   3361  CD2  LEU B 128      32.447  17.996  83.711  1.00 22.80           C
ATOM   3362  C    LEU B 128      30.609  19.061  87.516  1.00 28.51           C
ATOM   3363  O    LEU B 128      29.665  18.282  87.637  1.00 28.51           O
ATOM   3364  N    ASN B 129      30.466  20.377  87.389  1.00 35.31           N
ATOM   3365  CA   ASN B 129      29.157  21.017  87.357  1.00 35.31           C
ATOM   3366  CB   ASN B 129      29.030  22.019  88.496  1.00 33.40           C
ATOM   3367  CG   ASN B 129      29.017  21.364  89.851  1.00 33.40           C
ATOM   3368  OD1  ASN B 129      27.995  20.845  90.289  1.00 33.40           O
ATOM   3369  ND2  ASN B 129      30.158  21.382  90.526  1.00 33.40           N
ATOM   3370  C    ASN B 129      28.962  21.748  86.051  1.00 35.31           C
ATOM   3371  O    ASN B 129      29.594  22.771  85.802  1.00 35.31           O
ATOM   3372  N    LEU B 130      28.088  21.221  85.214  1.00 34.22           N
ATOM   3373  CA   LEU B 130      27.806  21.857  83.942  1.00 34.22           C
ATOM   3374  CB   LEU B 130      27.634  20.801  82.853  1.00 14.79           C
ATOM   3375  CG   LEU B 130      28.854  19.896  82.725  1.00 14.79           C
ATOM   3376  CD1  LEU B 130      28.535  18.727  81.790  1.00 14.79           C
ATOM   3377  CD2  LEU B 130      30.055  20.722  82.238  1.00 14.79           C
ATOM   3378  C    LEU B 130      26.541  22.705  84.055  1.00 34.22           C
ATOM   3379  O    LEU B 130      25.448  22.193  84.329  1.00 34.22           O
ATOM   3380  N    VAL B 131      26.705  24.010  83.869  1.00 35.73           N
ATOM   3381  CA   VAL B 131      25.583  24.929  83.918  1.00 35.73           C
ATOM   3382  CB   VAL B 131      26.006  26.275  84.483  1.00 31.72           C
ATOM   3383  CG1  VAL B 131      24.790  27.132  84.710  1.00 31.72           C
ATOM   3384  CG2  VAL B 131      26.772  26.066  85.768  1.00 31.72           C
ATOM   3385  C    VAL B 131      25.136  25.088  82.472  1.00 35.73           C
ATOM   3386  O    VAL B 131      25.834  25.696  81.652  1.00 35.73           O
ATOM   3387  N    LEU B 132      23.979  24.513  82.165  1.00 38.34           N
ATOM   3388  CA   LEU B 132      23.436  24.538  80.811  1.00 38.34           C
ATOM   3389  CB   LEU B 132      23.156  23.105  80.329  1.00 19.98           C
ATOM   3390  CG   LEU B 132      24.010  21.954  80.862  1.00 19.98           C
ATOM   3391  CD1  LEU B 132      23.292  20.658  80.574  1.00 19.98           C
ATOM   3392  CD2  LEU B 132      25.400  21.971  80.244  1.00 19.98           C
ATOM   3393  C    LEU B 132      22.131  25.295  80.775  1.00 38.34           C
ATOM   3394  O    LEU B 132      21.614  25.705  81.807  1.00 38.34           O
ATOM   3395  N    ASP B 133      21.598  25.471  79.571  1.00 41.35           N
ATOM   3396  CA   ASP B 133      20.309  26.125  79.413  1.00 41.35           C
ATOM   3397  CB   ASP B 133      19.992  26.351  77.929  1.00 42.55           C
ATOM   3398  CG   ASP B 133      20.573  27.655  77.393  1.00 42.55           C
ATOM   3399  OD1  ASP B 133      20.630  27.806  76.155  1.00 42.55           O
ATOM   3400  OD2  ASP B 133      20.959  28.533  78.199  1.00 42.55           O
ATOM   3401  C    ASP B 133      19.293  25.162  80.016  1.00 41.35           C
ATOM   3402  O    ASP B 133      19.589  23.982  80.241  1.00 41.35           O
ATOM   3403  N    TYR B 134      18.101  25.658  80.305  1.00 29.27           N
ATOM   3404  CA   TYR B 134      17.087  24.781  80.860  1.00 29.27           C
ATOM   3405  CB   TYR B 134      16.374  25.463  82.019  1.00 28.48           C
ATOM   3406  CG   TYR B 134      15.280  24.619  82.581  1.00 28.48           C
ATOM   3407  CD1  TYR B 134      15.570  23.419  83.224  1.00 28.48           C
ATOM   3408  CE1  TYR B 134      14.553  22.585  83.669  1.00 28.48           C
ATOM   3409  CD2  TYR B 134      13.942  24.970  82.402  1.00 28.48           C
ATOM   3410  CE2  TYR B 134      12.924  24.145  82.844  1.00 28.48           C
ATOM   3411  CZ   TYR B 134      13.231  22.956  83.473  1.00 28.48           C
ATOM   3412  OH   TYR B 134      12.220  22.129  83.905  1.00 28.48           O
ATOM   3413  C    TYR B 134      16.082  24.376  79.776  1.00 29.27           C
ATOM   3414  O    TYR B 134      15.660  25.198  78.968  1.00 29.27           O
ATOM   3415  N    VAL B 135      15.721  23.099  79.752  1.00 34.03           N
ATOM   3416  CA   VAL B 135      14.774  22.597  78.767  1.00 34.03           C
ATOM   3417  CB   VAL B 135      15.502  21.836  77.631  1.00 31.23           C
```

FIG. 7-58

| ATOM | 3418 | CG1 | VAL | B | 135 | 14.545 | 21.597 | 76.472 | 1.00 | 31.23 | C |
| ATOM | 3419 | CG2 | VAL | B | 135 | 16.707 | 22.631 | 77.152 | 1.00 | 31.23 | C |
| ATOM | 3420 | C | VAL | B | 135 | 13.771 | 21.675 | 79.466 | 1.00 | 34.03 | C |
| ATOM | 3421 | O | VAL | B | 135 | 14.117 | 20.586 | 79.916 | 1.00 | 34.03 | O |
| ATOM | 3422 | N | PRO | B | 136 | 12.497 | 22.102 | 79.531 | 1.00 | 35.64 | N |
| ATOM | 3423 | CD | PRO | B | 136 | 12.032 | 23.176 | 78.638 | 1.00 | 54.78 | C |
| ATOM | 3424 | CA | PRO | B | 136 | 11.342 | 21.438 | 80.152 | 1.00 | 35.64 | C |
| ATOM | 3425 | CB | PRO | B | 136 | 10.154 | 22.218 | 79.586 | 1.00 | 54.78 | C |
| ATOM | 3426 | CG | PRO | B | 136 | 10.727 | 23.532 | 79.257 | 1.00 | 54.78 | C |
| ATOM | 3427 | C | PRO | B | 136 | 11.182 | 19.929 | 79.940 | 1.00 | 35.64 | C |
| ATOM | 3428 | O | PRO | B | 136 | 11.312 | 19.139 | 80.883 | 1.00 | 35.64 | O |
| ATOM | 3429 | N | GLU | B | 137 | 10.899 | 19.532 | 78.701 | 1.00 | 30.25 | N |
| ATOM | 3430 | CA | GLU | B | 137 | 10.679 | 18.126 | 78.402 | 1.00 | 30.25 | C |
| ATOM | 3431 | CB | GLU | B | 137 | 9.303 | 17.953 | 77.738 | 1.00 | 48.55 | C |
| ATOM | 3432 | CG | GLU | B | 137 | 8.123 | 18.447 | 78.582 | 1.00 | 48.55 | C |
| ATOM | 3433 | CD | GLU | B | 137 | 7.879 | 17.610 | 79.824 | 1.00 | 48.55 | C |
| ATOM | 3434 | OE1 | GLU | B | 137 | 6.923 | 17.919 | 80.557 | 1.00 | 48.55 | O |
| ATOM | 3435 | OE2 | GLU | B | 137 | 8.636 | 16.646 | 80.074 | 1.00 | 48.55 | O |
| ATOM | 3436 | C | GLU | B | 137 | 11.756 | 17.437 | 77.567 | 1.00 | 30.25 | C |
| ATOM | 3437 | O | GLU | B | 137 | 12.781 | 18.026 | 77.206 | 1.00 | 30.25 | O |
| ATOM | 3438 | N | THR | B | 138 | 11.524 | 16.156 | 77.307 | 1.00 | 26.46 | N |
| ATOM | 3439 | CA | THR | B | 138 | 12.436 | 15.353 | 76.503 | 1.00 | 26.46 | C |
| ATOM | 3440 | CB | THR | B | 138 | 13.272 | 14.362 | 77.350 | 1.00 | 49.15 | C |
| ATOM | 3441 | OG1 | THR | B | 138 | 12.419 | 13.356 | 77.910 | 1.00 | 49.15 | O |
| ATOM | 3442 | CG2 | THR | B | 138 | 13.981 | 15.079 | 78.456 | 1.00 | 49.15 | C |
| ATOM | 3443 | C | THR | B | 138 | 11.626 | 14.521 | 75.525 | 1.00 | 26.46 | C |
| ATOM | 3444 | O | THR | B | 138 | 10.451 | 14.254 | 75.742 | 1.00 | 26.46 | O |
| ATOM | 3445 | N | VAL | B | 139 | 12.258 | 14.109 | 74.441 | 1.00 | 35.89 | N |
| ATOM | 3446 | CA | VAL | B | 139 | 11.581 | 13.283 | 73.462 | 1.00 | 35.89 | C |
| ATOM | 3447 | CB | VAL | B | 139 | 12.571 | 12.749 | 72.424 | 1.00 | 28.93 | C |
| ATOM | 3448 | CG1 | VAL | B | 139 | 11.918 | 11.657 | 71.595 | 1.00 | 28.93 | C |
| ATOM | 3449 | CG2 | VAL | B | 139 | 13.055 | 13.907 | 71.545 | 1.00 | 28.93 | C |
| ATOM | 3450 | C | VAL | B | 139 | 10.953 | 12.104 | 74.185 | 1.00 | 35.89 | C |
| ATOM | 3451 | O | VAL | B | 139 | 9.770 | 11.799 | 74.009 | 1.00 | 35.89 | O |
| ATOM | 3452 | N | TYR | B | 140 | 11.756 | 11.451 | 75.013 | 1.00 | 35.57 | N |
| ATOM | 3453 | CA | TYR | B | 140 | 11.289 | 10.298 | 75.759 | 1.00 | 35.57 | C |
| ATOM | 3454 | CB | TYR | B | 140 | 12.404 | 9.779 | 76.654 | 1.00 | 39.41 | C |
| ATOM | 3455 | CG | TYR | B | 140 | 11.935 | 8.723 | 77.602 | 1.00 | 39.41 | C |
| ATOM | 3456 | CD1 | TYR | B | 140 | 11.721 | 7.399 | 77.179 | 1.00 | 39.41 | C |
| ATOM | 3457 | CE1 | TYR | B | 140 | 11.172 | 6.449 | 78.047 | 1.00 | 39.41 | C |
| ATOM | 3458 | CD2 | TYR | B | 140 | 11.598 | 9.063 | 78.907 | 1.00 | 39.41 | C |
| ATOM | 3459 | CE2 | TYR | B | 140 | 11.055 | 8.136 | 79.768 | 1.00 | 39.41 | C |
| ATOM | 3460 | CZ | TYR | B | 140 | 10.843 | 6.836 | 79.340 | 1.00 | 39.41 | C |
| ATOM | 3461 | OH | TYR | B | 140 | 10.320 | 5.934 | 80.235 | 1.00 | 39.41 | O |
| ATOM | 3462 | C | TYR | B | 140 | 10.044 | 10.569 | 76.609 | 1.00 | 35.57 | C |
| ATOM | 3463 | O | TYR | B | 140 | 9.077 | 9.817 | 76.541 | 1.00 | 35.57 | O |
| ATOM | 3464 | N | ARG | B | 141 | 10.074 | 11.635 | 77.410 | 1.00 | 38.35 | N |
| ATOM | 3465 | CA | ARG | B | 141 | 8.952 | 11.974 | 78.279 | 1.00 | 38.35 | C |
| ATOM | 3466 | CB | ARG | B | 141 | 9.285 | 13.228 | 79.107 | 1.00 | 81.94 | C |
| ATOM | 3467 | CG | ARG | B | 141 | 8.522 | 13.334 | 80.428 | 1.00 | 81.94 | C |
| ATOM | 3468 | CD | ARG | B | 141 | 9.369 | 14.061 | 81.464 | 1.00 | 81.94 | C |
| ATOM | 3469 | NE | ARG | B | 141 | 10.718 | 13.491 | 81.540 | 1.00 | 81.94 | N |
| ATOM | 3470 | CZ | ARG | B | 141 | 11.032 | 12.347 | 82.151 | 1.00 | 81.94 | C |
| ATOM | 3471 | NH1 | ARG | B | 141 | 10.098 | 11.627 | 82.764 | 1.00 | 81.94 | N |
| ATOM | 3472 | NH2 | ARG | B | 141 | 12.285 | 11.908 | 82.132 | 1.00 | 81.94 | N |
| ATOM | 3473 | C | ARG | B | 141 | 7.685 | 12.182 | 77.447 | 1.00 | 38.35 | C |
| ATOM | 3474 | O | ARG | B | 141 | 6.599 | 11.747 | 77.829 | 1.00 | 38.35 | O |
| ATOM | 3475 | N | VAL | B | 142 | 7.834 | 12.827 | 76.298 | 1.00 | 31.20 | N |
| ATOM | 3476 | CA | VAL | B | 142 | 6.713 | 13.088 | 75.400 | 1.00 | 31.20 | C |
| ATOM | 3477 | CB | VAL | B | 142 | 7.111 | 14.098 | 74.300 | 1.00 | 36.06 | C |

FIG. 7-59

| ATOM | 3478 | CG1 | VAL | B | 142 | 6.010 | 14.199 | 73.260 | 1.00 | 36.06 | C |
|------|------|-----|-----|---|-----|-------|--------|--------|------|-------|---|
| ATOM | 3479 | CG2 | VAL | B | 142 | 7.384 | 15.468 | 74.923 | 1.00 | 36.06 | C |
| ATOM | 3480 | C | VAL | B | 142 | 6.236 | 11.814 | 74.716 | 1.00 | 31.20 | C |
| ATOM | 3481 | O | VAL | B | 142 | 5.044 | 11.608 | 74.526 | 1.00 | 31.20 | O |
| ATOM | 3482 | N | ALA | B | 143 | 7.180 | 10.964 | 74.338 | 1.00 | 43.38 | N |
| ATOM | 3483 | CA | ALA | B | 143 | 6.837 | 9.729 | 73.671 | 1.00 | 43.38 | C |
| ATOM | 3484 | CB | ALA | B | 143 | 8.089 | 9.050 | 73.159 | 1.00 | 18.36 | C |
| ATOM | 3485 | C | ALA | B | 143 | 6.088 | 8.824 | 74.641 | 1.00 | 43.38 | C |
| ATOM | 3486 | O | ALA | B | 143 | 5.077 | 8.223 | 74.272 | 1.00 | 43.38 | O |
| ATOM | 3487 | N | ARG | B | 144 | 6.567 | 8.728 | 75.881 | 1.00 | 36.24 | N |
| ATOM | 3488 | CA | ARG | B | 144 | 5.895 | 7.878 | 76.866 | 1.00 | 36.24 | C |
| ATOM | 3489 | CB | ARG | B | 144 | 6.693 | 7.774 | 78.159 | 1.00 | 77.18 | C |
| ATOM | 3490 | CG | ARG | B | 144 | 7.286 | 6.397 | 78.412 | 1.00 | 77.18 | C |
| ATOM | 3491 | CD | ARG | B | 144 | 6.776 | 5.851 | 79.727 | 1.00 | 77.18 | C |
| ATOM | 3492 | NE | ARG | B | 144 | 5.463 | 5.219 | 79.596 | 1.00 | 77.18 | N |
| ATOM | 3493 | CZ | ARG | B | 144 | 5.237 | 4.146 | 78.841 | 1.00 | 77.18 | C |
| ATOM | 3494 | NH1 | ARG | B | 144 | 6.244 | 3.591 | 78.156 | 1.00 | 77.18 | N |
| ATOM | 3495 | NH2 | ARG | B | 144 | 4.011 | 3.639 | 78.742 | 1.00 | 77.18 | N |
| ATOM | 3496 | C | ARG | B | 144 | 4.516 | 8.439 | 77.158 | 1.00 | 36.24 | C |
| ATOM | 3497 | O | ARG | B | 144 | 3.605 | 7.705 | 77.547 | 1.00 | 36.24 | O |
| ATOM | 3498 | N | HIS | B | 145 | 4.356 | 9.742 | 76.963 | 1.00 | 43.14 | N |
| ATOM | 3499 | CA | HIS | B | 145 | 3.062 | 10.339 | 77.193 | 1.00 | 43.14 | C |
| ATOM | 3500 | CB | HIS | B | 145 | 3.084 | 11.829 | 76.891 | 1.00 | 57.22 | C |
| ATOM | 3501 | CG | HIS | B | 145 | 1.731 | 12.450 | 76.953 | 1.00 | 57.22 | C |
| ATOM | 3502 | CD2 | HIS | B | 145 | 1.111 | 13.140 | 77.938 | 1.00 | 57.22 | C |
| ATOM | 3503 | ND1 | HIS | B | 145 | 0.797 | 12.285 | 75.954 | 1.00 | 57.22 | N |
| ATOM | 3504 | CE1 | HIS | B | 145 | -0.342 | 12.843 | 76.322 | 1.00 | 57.22 | C |
| ATOM | 3505 | NE2 | HIS | B | 145 | -0.177 | 13.369 | 77.523 | 1.00 | 57.22 | N |
| ATOM | 3506 | C | HIS | B | 145 | 2.047 | 9.638 | 76.290 | 1.00 | 43.14 | C |
| ATOM | 3507 | O | HIS | B | 145 | 1.079 | 9.052 | 76.768 | 1.00 | 43.14 | O |
| ATOM | 3508 | N | TYR | B | 146 | 2.282 | 9.693 | 74.984 | 1.00 | 44.84 | N |
| ATOM | 3509 | CA | TYR | B | 146 | 1.399 | 9.054 | 74.012 | 1.00 | 44.84 | C |
| ATOM | 3510 | CB | TYR | B | 146 | 1.893 | 9.328 | 72.588 | 1.00 | 40.49 | C |
| ATOM | 3511 | CG | TYR | B | 146 | 1.634 | 10.740 | 72.117 | 1.00 | 40.49 | C |
| ATOM | 3512 | CD1 | TYR | B | 146 | 2.305 | 11.819 | 72.679 | 1.00 | 40.49 | C |
| ATOM | 3513 | CE1 | TYR | B | 146 | 2.023 | 13.119 | 72.280 | 1.00 | 40.49 | C |
| ATOM | 3514 | CD2 | TYR | B | 146 | 0.674 | 11.001 | 71.137 | 1.00 | 40.49 | C |
| ATOM | 3515 | CE2 | TYR | B | 146 | 0.384 | 12.295 | 70.738 | 1.00 | 40.49 | C |
| ATOM | 3516 | CZ | TYR | B | 146 | 1.058 | 13.342 | 71.311 | 1.00 | 40.49 | C |
| ATOM | 3517 | OH | TYR | B | 146 | 0.740 | 14.615 | 70.922 | 1.00 | 40.49 | O |
| ATOM | 3518 | C | TYR | B | 146 | 1.206 | 7.545 | 74.202 | 1.00 | 44.84 | C |
| ATOM | 3519 | O | TYR | B | 146 | 0.081 | 7.082 | 74.320 | 1.00 | 44.84 | O |
| ATOM | 3520 | N | SER | B | 147 | 2.279 | 6.767 | 74.221 | 1.00 | 47.13 | N |
| ATOM | 3521 | CA | SER | B | 147 | 2.122 | 5.325 | 74.395 | 1.00 | 47.13 | C |
| ATOM | 3522 | CB | SER | B | 147 | 3.496 | 4.655 | 74.464 | 1.00 | 88.12 | C |
| ATOM | 3523 | OG | SER | B | 147 | 3.369 | 3.245 | 74.561 | 1.00 | 88.12 | O |
| ATOM | 3524 | C | SER | B | 147 | 1.309 | 4.967 | 75.653 | 1.00 | 47.13 | C |
| ATOM | 3525 | O | SER | B | 147 | 0.631 | 3.936 | 75.699 | 1.00 | 47.13 | O |
| ATOM | 3526 | N | ARG | B | 148 | 1.391 | 5.825 | 76.668 | 1.00 | 62.04 | N |
| ATOM | 3527 | CA | ARG | B | 148 | 0.681 | 5.618 | 77.934 | 1.00 | 62.04 | C |
| ATOM | 3528 | CB | ARG | B | 148 | 1.170 | 6.633 | 78.959 | 1.00 | 54.51 | C |
| ATOM | 3529 | CG | ARG | B | 148 | 1.290 | 6.057 | 80.357 | 1.00 | 54.51 | C |
| ATOM | 3530 | CD | ARG | B | 148 | 1.881 | 7.050 | 81.351 | 1.00 | 54.51 | C |
| ATOM | 3531 | NE | ARG | B | 148 | 3.345 | 7.071 | 81.339 | 1.00 | 54.51 | N |
| ATOM | 3532 | CZ | ARG | B | 148 | 4.075 | 8.187 | 81.353 | 1.00 | 54.51 | C |
| ATOM | 3533 | NH1 | ARG | B | 148 | 3.483 | 9.389 | 81.362 | 1.00 | 54.51 | N |
| ATOM | 3534 | NH2 | ARG | B | 148 | 5.402 | 8.111 | 81.403 | 1.00 | 54.51 | N |
| ATOM | 3535 | C | ARG | B | 148 | -0.775 | 5.886 | 77.586 | 1.00 | 62.04 | C |
| ATOM | 3536 | O | ARG | B | 148 | -1.721 | 5.230 | 78.044 | 1.00 | 62.04 | O |
| ATOM | 3537 | N | ALA | B | 149 | -0.891 | 6.858 | 76.695 | 1.00 | 61.50 | N |

FIG. 7-60

```
ATOM   3538  CA   ALA B 149      -2.147    7.362   76.161  1.00 61.50           C
ATOM   3539  CB   ALA B 149      -1.927    8.744   75.504  1.00 42.34           C
ATOM   3540  C    ALA B 149      -2.704    6.426   75.144  1.00 61.50           C
ATOM   3541  O    ALA B 149      -3.685    6.746   74.478  1.00 61.50           O
ATOM   3542  N    LYS B 150      -2.061    5.274   75.023  1.00 43.70           N
ATOM   3543  CA   LYS B 150      -2.481    4.261   74.073  1.00 43.70           C
ATOM   3544  CB   LYS B 150      -3.828    3.677   74.523  1.00 58.15           C
ATOM   3545  CG   LYS B 150      -3.730    2.400   75.351  1.00 58.15           C
ATOM   3546  CD   LYS B 150      -2.328    2.156   75.876  1.00 58.15           C
ATOM   3547  CE   LYS B 150      -2.382    1.331   77.157  1.00 58.15           C
ATOM   3548  NZ   LYS B 150      -3.609    0.457   77.209  1.00 58.15           N
ATOM   3549  C    LYS B 150      -2.580    4.794   72.634  1.00 43.70           C
ATOM   3550  O    LYS B 150      -3.221    4.178   71.781  1.00 43.70           O
ATOM   3551  N    GLN B 151      -1.923    5.913   72.357  1.00 77.00           N
ATOM   3552  CA   GLN B 151      -1.980    6.522   71.038  1.00 77.00           C
ATOM   3553  CB   GLN B 151      -2.780    7.816   71.110  1.00 91.71           C
ATOM   3554  CG   GLN B 151      -2.175    8.820   72.049  1.00 91.71           C
ATOM   3555  CD   GLN B 151      -2.850   10.165   71.934  1.00 91.71           C
ATOM   3556  OE1  GLN B 151      -2.671   11.043   72.781  1.00 91.71           O
ATOM   3557  NE2  GLN B 151      -3.623   10.344   70.870  1.00 91.71           N
ATOM   3558  C    GLN B 151      -0.579    6.807   70.536  1.00 77.00           C
ATOM   3559  O    GLN B 151       0.383    6.704   71.297  1.00 77.00           O
ATOM   3560  N    THR B 152      -0.465    7.191   69.268  1.00 46.21           N
ATOM   3561  CA   THR B 152       0.856    7.445   68.706  1.00 46.21           C
ATOM   3562  CB   THR B 152       1.114    6.596   67.430  1.00 59.19           C
ATOM   3563  OG1  THR B 152       2.525    6.539   67.171  1.00 59.19           O
ATOM   3564  CG2  THR B 152       0.403    7.201   66.227  1.00 59.19           C
ATOM   3565  C    THR B 152       1.135    8.897   68.378  1.00 46.21           C
ATOM   3566  O    THR B 152       0.226    9.642   68.005  1.00 46.21           O
ATOM   3567  N    LEU B 153       2.403    9.287   68.510  1.00 58.02           N
ATOM   3568  CA   LEU B 153       2.825   10.664   68.222  1.00 58.02           C
ATOM   3569  CB   LEU B 153       4.285   10.880   68.614  1.00 26.27           C
ATOM   3570  CG   LEU B 153       4.883   12.198   68.137  1.00 26.27           C
ATOM   3571  CD1  LEU B 153       4.617   13.281   69.169  1.00 26.27           C
ATOM   3572  CD2  LEU B 153       6.367   12.008   67.895  1.00 26.27           C
ATOM   3573  C    LEU B 153       2.671   11.031   66.748  1.00 58.02           C
ATOM   3574  O    LEU B 153       3.067   10.271   65.873  1.00 58.02           O
ATOM   3575  N    PRO B 154       2.097   12.205   66.458  1.00 58.93           N
ATOM   3576  CD   PRO B 154       1.518   13.121   67.455  1.00 39.19           C
ATOM   3577  CA   PRO B 154       1.882   12.704   65.094  1.00 58.93           C
ATOM   3578  CB   PRO B 154       1.347   14.109   65.314  1.00 39.19           C
ATOM   3579  CG   PRO B 154       0.640   14.000   66.608  1.00 39.19           C
ATOM   3580  C    PRO B 154       3.190   12.755   64.314  1.00 58.93           C
ATOM   3581  O    PRO B 154       4.206   13.256   64.808  1.00 58.93           O
ATOM   3582  N    VAL B 155       3.151   12.268   63.084  1.00 38.38           N
ATOM   3583  CA   VAL B 155       4.321   12.266   62.221  1.00 38.38           C
ATOM   3584  CB   VAL B 155       3.948   11.762   60.811  1.00 30.29           C
ATOM   3585  CG1  VAL B 155       3.291   10.394   60.916  1.00 30.29           C
ATOM   3586  CG2  VAL B 155       3.003   12.764   60.124  1.00 30.29           C
ATOM   3587  C    VAL B 155       4.987   13.638   62.075  1.00 38.38           C
ATOM   3588  O    VAL B 155       6.187   13.714   61.815  1.00 38.38           O
ATOM   3589  N    ILE B 156       4.217   14.714   62.229  1.00 27.91           N
ATOM   3590  CA   ILE B 156       4.780   16.055   62.085  1.00 27.91           C
ATOM   3591  CB   ILE B 156       3.704   17.146   62.318  1.00 36.60           C
ATOM   3592  CG2  ILE B 156       3.196   17.086   63.736  1.00 36.60           C
ATOM   3593  CG1  ILE B 156       4.288   18.528   62.035  1.00 36.60           C
ATOM   3594  CD1  ILE B 156       4.758   18.698   60.606  1.00 36.60           C
ATOM   3595  C    ILE B 156       5.902   16.204   63.109  1.00 27.91           C
ATOM   3596  O    ILE B 156       6.959   16.771   62.824  1.00 27.91           O
ATOM   3597  N    TYR B 157       5.662   15.667   64.300  1.00 33.67           N
```

FIG. 7-61

```
ATOM   3598  CA   TYR B 157       6.636  15.714  65.382  1.00 33.67           C
ATOM   3599  CB   TYR B 157       5.942  15.400  66.703  1.00 36.45           C
ATOM   3600  CG   TYR B 157       4.958  16.466  67.108  1.00 36.45           C
ATOM   3601  CD1  TYR B 157       3.626  16.146  67.397  1.00 36.45           C
ATOM   3602  CE1  TYR B 157       2.720  17.136  67.774  1.00 36.45           C
ATOM   3603  CD2  TYR B 157       5.355  17.798  67.204  1.00 36.45           C
ATOM   3604  CE2  TYR B 157       4.463  18.788  67.579  1.00 36.45           C
ATOM   3605  CZ   TYR B 157       3.148  18.458  67.862  1.00 36.45           C
ATOM   3606  OH   TYR B 157       2.271  19.446  68.244  1.00 36.45           O
ATOM   3607  C    TYR B 157       7.765  14.713  65.135  1.00 33.67           C
ATOM   3608  O    TYR B 157       8.944  14.996  65.382  1.00 33.67           O
ATOM   3609  N    VAL B 158       7.394  13.533  64.653  1.00 28.34           N
ATOM   3610  CA   VAL B 158       8.388  12.524  64.364  1.00 28.34           C
ATOM   3611  CB   VAL B 158       7.749  11.248  63.783  1.00 25.63           C
ATOM   3612  CG1  VAL B 158       8.785  10.141  63.706  1.00 25.63           C
ATOM   3613  CG2  VAL B 158       6.586  10.809  64.653  1.00 25.63           C
ATOM   3614  C    VAL B 158       9.364  13.112  63.355  1.00 28.34           C
ATOM   3615  O    VAL B 158      10.561  12.873  63.446  1.00 28.34           O
ATOM   3616  N    LYS B 159       8.848  13.884  62.399  1.00 42.04           N
ATOM   3617  CA   LYS B 159       9.693  14.518  61.384  1.00 42.04           C
ATOM   3618  CB   LYS B 159       8.843  15.100  60.243  1.00 49.36           C
ATOM   3619  CG   LYS B 159       8.055  14.076  59.431  1.00 49.36           C
ATOM   3620  CD   LYS B 159       7.154  14.748  58.391  1.00 49.36           C
ATOM   3621  CE   LYS B 159       6.336  13.736  57.591  1.00 49.36           C
ATOM   3622  NZ   LYS B 159       5.598  14.397  56.480  1.00 49.36           N
ATOM   3623  C    LYS B 159      10.508  15.636  62.045  1.00 42.04           C
ATOM   3624  O    LYS B 159      11.729  15.660  61.949  1.00 42.04           O
ATOM   3625  N    LEU B 160       9.833  16.557  62.723  1.00 25.63           N
ATOM   3626  CA   LEU B 160      10.520  17.658  63.402  1.00 25.63           C
ATOM   3627  CB   LEU B 160       9.515  18.502  64.205  1.00 31.02           C
ATOM   3628  CG   LEU B 160       8.700  19.556  63.456  1.00 31.02           C
ATOM   3629  CD1  LEU B 160       7.647  20.157  64.388  1.00 31.02           C
ATOM   3630  CD2  LEU B 160       9.636  20.626  62.916  1.00 31.02           C
ATOM   3631  C    LEU B 160      11.639  17.202  64.347  1.00 25.63           C
ATOM   3632  O    LEU B 160      12.725  17.791  64.366  1.00 25.63           O
ATOM   3633  N    TYR B 161      11.372  16.159  65.135  1.00 19.56           N
ATOM   3634  CA   TYR B 161      12.361  15.678  66.093  1.00 19.56           C
ATOM   3635  CB   TYR B 161      11.725  14.768  67.141  1.00 28.88           C
ATOM   3636  CG   TYR B 161      10.604  15.395  67.936  1.00 28.88           C
ATOM   3637  CD1  TYR B 161      10.533  16.778  68.130  1.00 28.88           C
ATOM   3638  CE1  TYR B 161       9.478  17.348  68.864  1.00 28.88           C
ATOM   3639  CD2  TYR B 161       9.605  14.596  68.499  1.00 28.88           C
ATOM   3640  CE2  TYR B 161       8.552  15.148  69.239  1.00 28.88           C
ATOM   3641  CZ   TYR B 161       8.485  16.517  69.417  1.00 28.88           C
ATOM   3642  OH   TYR B 161       7.412  17.037  70.119  1.00 28.88           O
ATOM   3643  C    TYR B 161      13.508  14.945  65.437  1.00 19.56           C
ATOM   3644  O    TYR B 161      14.677  15.141  65.792  1.00 19.56           O
ATOM   3645  N    MET B 162      13.178  14.101  64.470  1.00 30.21           N
ATOM   3646  CA   MET B 162      14.212  13.350  63.796  1.00 30.21           C
ATOM   3647  CB   MET B 162      13.607  12.227  62.955  1.00 29.18           C
ATOM   3648  CG   MET B 162      13.087  11.048  63.794  1.00 29.18           C
ATOM   3649  SD   MET B 162      14.303  10.412  64.990  1.00 29.18           S
ATOM   3650  CE   MET B 162      15.625  10.012  63.910  1.00 29.18           C
ATOM   3651  C    MET B 162      15.078  14.246  62.947  1.00 30.21           C
ATOM   3652  O    MET B 162      16.287  14.026  62.879  1.00 30.21           O
ATOM   3653  N    TYR B 163      14.468  15.264  62.330  1.00 26.87           N
ATOM   3654  CA   TYR B 163      15.192  16.213  61.474  1.00 26.87           C
ATOM   3655  CB   TYR B 163      14.240  17.237  60.848  1.00 28.70           C
ATOM   3656  CG   TYR B 163      14.932  18.200  59.909  1.00 28.70           C
ATOM   3657  CD1  TYR B 163      15.417  17.769  58.666  1.00 28.70           C
```

FIG. 7-62

```
ATOM   3658  CE1 TYR B 163      16.063  18.646  57.792  1.00 28.70           C
ATOM   3659  CD2 TYR B 163      15.115  19.537  60.258  1.00 28.70           C
ATOM   3660  CE2 TYR B 163      15.758  20.428  59.394  1.00 28.70           C
ATOM   3661  CZ  TYR B 163      16.229  19.982  58.162  1.00 28.70           C
ATOM   3662  OH  TYR B 163      16.836  20.875  57.296  1.00 28.70           O
ATOM   3663  C   TYR B 163      16.243  16.953  62.277  1.00 26.87           C
ATOM   3664  O   TYR B 163      17.400  17.038  61.869  1.00 26.87           O
ATOM   3665  N   GLN B 164      15.834  17.477  63.427  1.00 24.33           N
ATOM   3666  CA  GLN B 164      16.743  18.219  64.293  1.00 24.33           C
ATOM   3667  CB  GLN B 164      15.944  18.927  65.386  1.00 22.96           C
ATOM   3668  CG  GLN B 164      14.852  19.802  64.829  1.00 22.96           C
ATOM   3669  CD  GLN B 164      14.111  20.558  65.897  1.00 22.96           C
ATOM   3670  OE1 GLN B 164      14.617  21.533  66.450  1.00 22.96           O
ATOM   3671  NE2 GLN B 164      12.905  20.108  66.206  1.00 22.96           N
ATOM   3672  C   GLN B 164      17.831  17.323  64.897  1.00 24.33           C
ATOM   3673  O   GLN B 164      18.977  17.740  65.080  1.00 24.33           O
ATOM   3674  N   LEU B 165      17.478  16.084  65.199  1.00 28.76           N
ATOM   3675  CA  LEU B 165      18.451  15.157  65.736  1.00 28.76           C
ATOM   3676  CB  LEU B 165      17.791  13.813  66.040  1.00 16.84           C
ATOM   3677  CG  LEU B 165      18.736  12.627  66.293  1.00 16.84           C
ATOM   3678  CD1 LEU B 165      19.578  12.901  67.518  1.00 16.84           C
ATOM   3679  CD2 LEU B 165      17.941  11.322  66.466  1.00 16.84           C
ATOM   3680  C   LEU B 165      19.556  14.952  64.708  1.00 28.76           C
ATOM   3681  O   LEU B 165      20.736  15.013  65.043  1.00 28.76           O
ATOM   3682  N   PHE B 166      19.170  14.707  63.455  1.00 17.54           N
ATOM   3683  CA  PHE B 166      20.146  14.471  62.394  1.00 17.54           C
ATOM   3684  CB  PHE B 166      19.452  14.052  61.095  1.00 25.20           C
ATOM   3685  CG  PHE B 166      19.103  12.591  61.048  1.00 25.20           C
ATOM   3686  CD1 PHE B 166      20.087  11.628  61.245  1.00 25.20           C
ATOM   3687  CD2 PHE B 166      17.782  12.179  60.865  1.00 25.20           C
ATOM   3688  CE1 PHE B 166      19.769  10.276  61.270  1.00 25.20           C
ATOM   3689  CE2 PHE B 166      17.447  10.818  60.890  1.00 25.20           C
ATOM   3690  CZ  PHE B 166      18.452   9.863  61.096  1.00 25.20           C
ATOM   3691  C   PHE B 166      21.041  15.665  62.130  1.00 17.54           C
ATOM   3692  O   PHE B 166      22.212  15.527  61.729  1.00 17.54           O
ATOM   3693  N   ARG B 167      20.498  16.844  62.375  1.00 22.45           N
ATOM   3694  CA  ARG B 167      21.273  18.035  62.143  1.00 22.45           C
ATOM   3695  CB  ARG B 167      20.363  19.254  62.123  1.00 35.91           C
ATOM   3696  CG  ARG B 167      21.053  20.446  61.520  1.00 35.91           C
ATOM   3697  CD  ARG B 167      20.132  21.619  61.437  1.00 35.91           C
ATOM   3698  NE  ARG B 167      20.882  22.846  61.239  1.00 35.91           N
ATOM   3699  CZ  ARG B 167      20.351  24.051  61.360  1.00 35.91           C
ATOM   3700  NH1 ARG B 167      19.069  24.172  61.682  1.00 35.91           N
ATOM   3701  NH2 ARG B 167      21.096  25.126  61.157  1.00 35.91           N
ATOM   3702  C   ARG B 167      22.371  18.181  63.196  1.00 22.45           C
ATOM   3703  O   ARG B 167      23.529  18.483  62.876  1.00 22.45           O
ATOM   3704  N   SER B 168      22.023  17.953  64.456  1.00 23.29           N
ATOM   3705  CA  SER B 168      23.022  18.068  65.507  1.00 23.29           C
ATOM   3706  CB  SER B 168      22.358  17.908  66.876  1.00 24.10           C
ATOM   3707  OG  SER B 168      21.923  16.577  67.089  1.00 24.10           O
ATOM   3708  C   SER B 168      24.084  16.983  65.299  1.00 23.29           C
ATOM   3709  O   SER B 168      25.266  17.152  65.638  1.00 23.29           O
ATOM   3710  N   LEU B 169      23.645  15.865  64.730  1.00 21.95           N
ATOM   3711  CA  LEU B 169      24.527  14.740  64.466  1.00 21.95           C
ATOM   3712  CB  LEU B 169      23.691  13.519  64.083  1.00 22.38           C
ATOM   3713  CG  LEU B 169      23.839  12.290  64.969  1.00 22.38           C
ATOM   3714  CD1 LEU B 169      23.999  12.727  66.394  1.00 22.38           C
ATOM   3715  CD2 LEU B 169      22.636  11.398  64.789  1.00 22.38           C
ATOM   3716  C   LEU B 169      25.510  15.114  63.357  1.00 21.95           C
ATOM   3717  O   LEU B 169      26.701  14.853  63.451  1.00 21.95           O
```

FIG. 7-63

| | | | | | | | | | |
|---|---|---|---|---|---|---|---|---|---|
| ATOM | 3718 | N | ALA | B 170 | 25.011 | 15.768 | 62.320 | 1.00 36.28 | N |
| ATOM | 3719 | CA | ALA | B 170 | 25.867 | 16.196 | 61.221 | 1.00 36.28 | C |
| ATOM | 3720 | CB | ALA | B 170 | 25.009 | 16.791 | 60.119 | 1.00 30.60 | C |
| ATOM | 3721 | C | ALA | B 170 | 26.902 | 17.225 | 61.693 | 1.00 36.28 | C |
| ATOM | 3722 | O | ALA | B 170 | 28.028 | 17.260 | 61.198 | 1.00 36.28 | O |
| ATOM | 3723 | N | TYR | B 171 | 26.503 | 18.066 | 62.645 | 1.00 28.14 | N |
| ATOM | 3724 | CA | TYR | B 171 | 27.372 | 19.098 | 63.198 | 1.00 28.14 | C |
| ATOM | 3725 | CB | TYR | B 171 | 26.595 | 19.981 | 64.172 | 1.00 31.16 | C |
| ATOM | 3726 | CG | TYR | B 171 | 27.452 | 21.014 | 64.884 | 1.00 31.16 | C |
| ATOM | 3727 | CD1 | TYR | B 171 | 27.808 | 22.209 | 64.263 | 1.00 31.16 | C |
| ATOM | 3728 | CE1 | TYR | B 171 | 28.584 | 23.164 | 64.925 | 1.00 31.16 | C |
| ATOM | 3729 | CD2 | TYR | B 171 | 27.901 | 20.800 | 66.188 | 1.00 31.16 | C |
| ATOM | 3730 | CE2 | TYR | B 171 | 28.679 | 21.753 | 66.854 | 1.00 31.16 | C |
| ATOM | 3731 | CZ | TYR | B 171 | 29.013 | 22.925 | 66.216 | 1.00 31.16 | C |
| ATOM | 3732 | OH | TYR | B 171 | 29.790 | 23.847 | 66.867 | 1.00 31.16 | O |
| ATOM | 3733 | C | TYR | B 171 | 28.565 | 18.493 | 63.919 | 1.00 28.14 | C |
| ATOM | 3734 | O | TYR | B 171 | 29.708 | 18.699 | 63.510 | 1.00 28.14 | O |
| ATOM | 3735 | N | ILE | B 172 | 28.305 | 17.740 | 64.987 | 1.00 28.53 | N |
| ATOM | 3736 | CA | ILE | B 172 | 29.392 | 17.138 | 65.752 | 1.00 28.53 | C |
| ATOM | 3737 | CB | ILE | B 172 | 28.887 | 16.364 | 66.994 | 1.00 21.79 | C |
| ATOM | 3738 | CG2 | ILE | B 172 | 28.107 | 17.300 | 67.915 | 1.00 21.79 | C |
| ATOM | 3739 | CG1 | ILE | B 172 | 28.023 | 15.181 | 66.565 | 1.00 21.79 | C |
| ATOM | 3740 | CD1 | ILE | B 172 | 27.491 | 14.352 | 67.740 | 1.00 21.79 | C |
| ATOM | 3741 | C | ILE | B 172 | 30.204 | 16.185 | 64.907 | 1.00 28.53 | C |
| ATOM | 3742 | O | ILE | B 172 | 31.418 | 16.055 | 65.092 | 1.00 28.53 | O |
| ATOM | 3743 | N | HIS | B 173 | 29.540 | 15.522 | 63.968 | 1.00 27.16 | N |
| ATOM | 3744 | CA | HIS | B 173 | 30.251 | 14.578 | 63.138 | 1.00 27.16 | C |
| ATOM | 3745 | CB | HIS | B 173 | 29.280 | 13.742 | 62.301 | 1.00 23.08 | C |
| ATOM | 3746 | CG | HIS | B 173 | 28.602 | 12.657 | 63.079 | 1.00 23.08 | C |
| ATOM | 3747 | CD2 | HIS | B 173 | 28.577 | 12.401 | 64.409 | 1.00 23.08 | C |
| ATOM | 3748 | ND1 | HIS | B 173 | 27.787 | 11.713 | 62.490 | 1.00 23.08 | N |
| ATOM | 3749 | CE1 | HIS | B 173 | 27.284 | 10.926 | 63.424 | 1.00 23.08 | C |
| ATOM | 3750 | NE2 | HIS | B 173 | 27.746 | 11.320 | 64.597 | 1.00 23.08 | N |
| ATOM | 3751 | C | HIS | B 173 | 31.275 | 15.265 | 62.258 | 1.00 27.16 | C |
| ATOM | 3752 | O | HIS | B 173 | 32.321 | 14.689 | 61.951 | 1.00 27.16 | O |
| ATOM | 3753 | N | SER | B 174 | 30.992 | 16.499 | 61.863 | 1.00 31.32 | N |
| ATOM | 3754 | CA | SER | B 174 | 31.929 | 17.241 | 61.024 | 1.00 31.32 | C |
| ATOM | 3755 | CB | SER | B 174 | 31.275 | 18.527 | 60.533 | 1.00 26.18 | C |
| ATOM | 3756 | OG | SER | B 174 | 31.066 | 19.429 | 61.611 | 1.00 26.18 | O |
| ATOM | 3757 | C | SER | B 174 | 33.206 | 17.568 | 61.822 | 1.00 31.32 | C |
| ATOM | 3758 | O | SER | B 174 | 34.176 | 18.094 | 61.280 | 1.00 31.32 | O |
| ATOM | 3759 | N | PHE | B 175 | 33.182 | 17.245 | 63.113 | 1.00 38.44 | N |
| ATOM | 3760 | CA | PHE | B 175 | 34.308 | 17.479 | 64.008 | 1.00 38.44 | C |
| ATOM | 3761 | CB | PHE | B 175 | 33.860 | 18.229 | 65.249 | 1.00 46.02 | C |
| ATOM | 3762 | CG | PHE | B 175 | 33.414 | 19.616 | 64.977 | 1.00 46.02 | C |
| ATOM | 3763 | CD1 | PHE | B 175 | 32.077 | 19.967 | 65.092 | 1.00 46.02 | C |
| ATOM | 3764 | CD2 | PHE | B 175 | 34.336 | 20.585 | 64.610 | 1.00 46.02 | C |
| ATOM | 3765 | CE1 | PHE | B 175 | 31.667 | 21.273 | 64.846 | 1.00 46.02 | C |
| ATOM | 3766 | CE2 | PHE | B 175 | 33.938 | 21.887 | 64.364 | 1.00 46.02 | C |
| ATOM | 3767 | CZ | PHE | B 175 | 32.604 | 22.236 | 64.481 | 1.00 46.02 | C |
| ATOM | 3768 | C | PHE | B 175 | 34.908 | 16.166 | 64.450 | 1.00 38.44 | C |
| ATOM | 3769 | O | PHE | B 175 | 35.843 | 16.149 | 65.251 | 1.00 38.44 | O |
| ATOM | 3770 | N | GLY | B 176 | 34.351 | 15.072 | 63.932 | 1.00 23.23 | N |
| ATOM | 3771 | CA | GLY | B 176 | 34.823 | 13.744 | 64.283 | 1.00 23.23 | C |
| ATOM | 3772 | C | GLY | B 176 | 34.345 | 13.334 | 65.660 | 1.00 23.23 | C |
| ATOM | 3773 | O | GLY | B 176 | 34.782 | 12.328 | 66.211 | 1.00 23.23 | O |
| ATOM | 3774 | N | ILE | B 177 | 33.441 | 14.115 | 66.231 | 1.00 27.95 | N |
| ATOM | 3775 | CA | ILE | B 177 | 32.941 | 13.790 | 67.553 | 1.00 27.95 | C |
| ATOM | 3776 | CB | ILE | B 177 | 32.600 | 15.068 | 68.344 | 1.00 22.65 | C |
| ATOM | 3777 | CG2 | ILE | B 177 | 32.023 | 14.692 | 69.715 | 1.00 22.65 | C |

FIG. 7-64

```
ATOM   3778  CG1 ILE B 177      33.864  15.924  68.510  1.00 22.65           C
ATOM   3779  CD1 ILE B 177      33.610  17.305  69.150  1.00 22.65           C
ATOM   3780  C   ILE B 177      31.710  12.884  67.454  1.00 27.95           C
ATOM   3781  O   ILE B 177      30.700  13.244  66.845  1.00 27.95           O
ATOM   3782  N   CYS B 178      31.810  11.698  68.049  1.00 21.35           N
ATOM   3783  CA  CYS B 178      30.732  10.725  68.025  1.00 21.35           C
ATOM   3784  CB  CYS B 178      31.290   9.330  67.738  1.00 32.94           C
ATOM   3785  SG  CYS B 178      30.028   8.025  67.672  1.00 32.94           S
ATOM   3786  C   CYS B 178      30.067  10.745  69.382  1.00 21.35           C
ATOM   3787  O   CYS B 178      30.749  10.762  70.404  1.00 21.35           O
ATOM   3788  N   HIS B 179      28.733  10.728  69.386  1.00 18.04           N
ATOM   3789  CA  HIS B 179      27.954  10.765  70.621  1.00 18.04           C
ATOM   3790  CB  HIS B 179      26.497  11.123  70.313  1.00 29.44           C
ATOM   3791  CG  HIS B 179      25.696  11.488  71.528  1.00 29.44           C
ATOM   3792  CD2 HIS B 179      25.431  12.695  72.088  1.00 29.44           C
ATOM   3793  ND1 HIS B 179      25.092  10.549  72.338  1.00 29.44           N
ATOM   3794  CE1 HIS B 179      24.491  11.159  73.344  1.00 29.44           C
ATOM   3795  NE2 HIS B 179      24.683  12.461  73.215  1.00 29.44           N
ATOM   3796  C   HIS B 179      28.003   9.480  71.429  1.00 18.04           C
ATOM   3797  O   HIS B 179      28.121   9.526  72.641  1.00 18.04           O
ATOM   3798  N   ARG B 180      27.887   8.339  70.757  1.00 40.69           N
ATOM   3799  CA  ARG B 180      27.929   7.026  71.407  1.00 40.69           C
ATOM   3800  CB  ARG B 180      29.291   6.816  72.073  1.00 26.75           C
ATOM   3801  CG  ARG B 180      30.439   6.894  71.092  1.00 26.75           C
ATOM   3802  CD  ARG B 180      31.716   7.278  71.783  1.00 26.75           C
ATOM   3803  NE  ARG B 180      32.427   6.151  72.364  1.00 26.75           N
ATOM   3804  CZ  ARG B 180      33.193   6.232  73.444  1.00 26.75           C
ATOM   3805  NH1 ARG B 180      33.341   7.386  74.074  1.00 26.75           N
ATOM   3806  NH2 ARG B 180      33.828   5.159  73.885  1.00 26.75           N
ATOM   3807  C   ARG B 180      26.819   6.733  72.415  1.00 40.69           C
ATOM   3808  O   ARG B 180      26.889   5.752  73.140  1.00 40.69           O
ATOM   3809  N   ASP B 181      25.794   7.571  72.471  1.00 34.91           N
ATOM   3810  CA  ASP B 181      24.703   7.310  73.389  1.00 34.91           C
ATOM   3811  CB  ASP B 181      25.118   7.661  74.816  1.00 31.20           C
ATOM   3812  CG  ASP B 181      24.181   7.058  75.865  1.00 31.20           C
ATOM   3813  OD1 ASP B 181      23.894   5.839  75.829  1.00 31.20           O
ATOM   3814  OD2 ASP B 181      23.735   7.812  76.747  1.00 31.20           O
ATOM   3815  C   ASP B 181      23.418   8.039  72.997  1.00 34.91           C
ATOM   3816  O   ASP B 181      22.739   8.638  73.832  1.00 34.91           O
ATOM   3817  N   ILE B 182      23.088   7.971  71.712  1.00 24.87           N
ATOM   3818  CA  ILE B 182      21.883   8.594  71.198  1.00 24.87           C
ATOM   3819  CB  ILE B 182      21.944   8.741  69.645  1.00 25.01           C
ATOM   3820  CG2 ILE B 182      20.601   9.201  69.117  1.00 25.01           C
ATOM   3821  CG1 ILE B 182      23.029   9.752  69.240  1.00 25.01           C
ATOM   3822  CD1 ILE B 182      22.804  11.188  69.764  1.00 25.01           C
ATOM   3823  C   ILE B 182      20.672   7.744  71.598  1.00 24.87           C
ATOM   3824  O   ILE B 182      20.566   6.562  71.249  1.00 24.87           O
ATOM   3825  N   LYS B 183      19.765   8.363  72.345  1.00 33.76           N
ATOM   3826  CA  LYS B 183      18.560   7.704  72.829  1.00 33.76           C
ATOM   3827  CB  LYS B 183      18.868   6.903  74.102  1.00 37.09           C
ATOM   3828  CG  LYS B 183      19.187   7.797  75.308  1.00 37.09           C
ATOM   3829  CD  LYS B 183      20.190   7.189  76.300  1.00 37.09           C
ATOM   3830  CE  LYS B 183      19.590   6.077  77.127  1.00 37.09           C
ATOM   3831  NZ  LYS B 183      20.551   5.621  78.170  1.00 37.09           N
ATOM   3832  C   LYS B 183      17.600   8.835  73.162  1.00 33.76           C
ATOM   3833  O   LYS B 183      18.021   9.977  73.358  1.00 33.76           O
ATOM   3834  N   PRO B 184      16.299   8.526  73.259  1.00 36.14           N
ATOM   3835  CD  PRO B 184      15.746   7.165  73.140  1.00 18.13           C
ATOM   3836  CA  PRO B 184      15.235   9.491  73.570  1.00 36.14           C
ATOM   3837  CB  PRO B 184      14.035   8.593  73.808  1.00 18.13           C
```

FIG. 7-65

```
ATOM   3838  CG   PRO B 184      14.299   7.445  72.905  1.00 18.13           C
ATOM   3839  C    PRO B 184      15.508  10.392  74.777  1.00 36.14           C
ATOM   3840  O    PRO B 184      15.295  11.604  74.735  1.00 36.14           O
ATOM   3841  N    GLN B 185      15.964   9.775  75.857  1.00 32.24           N
ATOM   3842  CA   GLN B 185      16.248  10.480  77.092  1.00 32.24           C
ATOM   3843  CB   GLN B 185      16.658   9.487  78.181  1.00 31.31           C
ATOM   3844  CG   GLN B 185      15.570   8.509  78.566  1.00 31.31           C
ATOM   3845  CD   GLN B 185      15.448   7.316  77.605  1.00 31.31           C
ATOM   3846  OE1  GLN B 185      15.791   7.412  76.417  1.00 31.31           O
ATOM   3847  NE2  GLN B 185      14.939   6.186  78.120  1.00 31.31           N
ATOM   3848  C    GLN B 185      17.305  11.571  76.984  1.00 32.24           C
ATOM   3849  O    GLN B 185      17.364  12.436  77.866  1.00 32.24           O
ATOM   3850  N    ASN B 186      18.138  11.531  75.932  1.00 31.92           N
ATOM   3851  CA   ASN B 186      19.202  12.542  75.731  1.00 31.92           C
ATOM   3852  CB   ASN B 186      20.527  11.882  75.358  1.00 32.49           C
ATOM   3853  CG   ASN B 186      21.083  11.066  76.479  1.00 32.49           C
ATOM   3854  OD1  ASN B 186      20.946  11.449  77.626  1.00 32.49           O
ATOM   3855  ND2  ASN B 186      21.717   9.944  76.163  1.00 32.49           N
ATOM   3856  C    ASN B 186      18.866  13.596  74.683  1.00 31.92           C
ATOM   3857  O    ASN B 186      19.731  14.344  74.215  1.00 31.92           O
ATOM   3858  N    LEU B 187      17.591  13.640  74.332  1.00 32.37           N
ATOM   3859  CA   LEU B 187      17.082  14.578  73.357  1.00 32.37           C
ATOM   3860  CB   LEU B 187      16.390  13.820  72.227  1.00 17.23           C
ATOM   3861  CG   LEU B 187      17.233  12.763  71.486  1.00 17.23           C
ATOM   3862  CD1  LEU B 187      16.389  12.125  70.386  1.00 17.23           C
ATOM   3863  CD2  LEU B 187      18.481  13.395  70.886  1.00 17.23           C
ATOM   3864  C    LEU B 187      16.091  15.457  74.091  1.00 32.37           C
ATOM   3865  O    LEU B 187      14.967  15.046  74.366  1.00 32.37           O
ATOM   3866  N    LEU B 188      16.528  16.663  74.425  1.00 30.81           N
ATOM   3867  CA   LEU B 188      15.688  17.606  75.141  1.00 30.81           C
ATOM   3868  CB   LEU B 188      16.546  18.583  75.942  1.00 28.21           C
ATOM   3869  CG   LEU B 188      17.683  18.015  76.794  1.00 28.21           C
ATOM   3870  CD1  LEU B 188      18.389  19.157  77.470  1.00 28.21           C
ATOM   3871  CD2  LEU B 188      17.162  17.041  77.833  1.00 28.21           C
ATOM   3872  C    LEU B 188      14.885  18.385  74.137  1.00 30.81           C
ATOM   3873  O    LEU B 188      15.319  18.558  73.000  1.00 30.81           O
ATOM   3874  N    LEU B 189      13.711  18.852  74.551  1.00 34.53           N
ATOM   3875  CA   LEU B 189      12.886  19.652  73.658  1.00 34.53           C
ATOM   3876  CB   LEU B 189      12.145  18.752  72.668  1.00 40.73           C
ATOM   3877  CG   LEU B 189      10.878  18.052  73.128  1.00 40.73           C
ATOM   3878  CD1  LEU B 189       9.675  18.668  72.417  1.00 40.73           C
ATOM   3879  CD2  LEU B 189      10.982  16.573  72.808  1.00 40.73           C
ATOM   3880  C    LEU B 189      11.899  20.595  74.343  1.00 34.53           C
ATOM   3881  O    LEU B 189      11.466  20.371  75.477  1.00 34.53           O
ATOM   3882  N    ASP B 190      11.588  21.676  73.636  1.00 37.98           N
ATOM   3883  CA   ASP B 190      10.640  22.675  74.092  1.00 37.98           C
ATOM   3884  CB   ASP B 190      11.060  24.057  73.599  1.00 52.35           C
ATOM   3885  CG   ASP B 190      10.221  25.155  74.185  1.00 52.35           C
ATOM   3886  OD1  ASP B 190       8.992  25.153  73.957  1.00 52.35           O
ATOM   3887  OD2  ASP B 190      10.791  26.020  74.880  1.00 52.35           O
ATOM   3888  C    ASP B 190       9.310  22.252  73.454  1.00 37.98           C
ATOM   3889  O    ASP B 190       9.146  22.281  72.223  1.00 37.98           O
ATOM   3890  N    PRO B 191       8.342  21.853  74.289  1.00 58.59           N
ATOM   3891  CD   PRO B 191       8.339  22.047  75.750  1.00 53.31           C
ATOM   3892  CA   PRO B 191       7.025  21.406  73.832  1.00 58.59           C
ATOM   3893  CB   PRO B 191       6.336  21.018  75.129  1.00 53.31           C
ATOM   3894  CG   PRO B 191       6.861  22.055  76.068  1.00 53.31           C
ATOM   3895  C    PRO B 191       6.208  22.411  73.035  1.00 58.59           C
ATOM   3896  O    PRO B 191       5.291  22.017  72.322  1.00 58.59           O
ATOM   3897  N    ASP B 192       6.536  23.696  73.148  1.00 31.52           N
```

FIG. 7-66

| ATOM | 3898 | CA | ASP | B | 192 | 5.786 | 24.730 | 72.433 | 1.00 | 31.52 | C |
|---|---|---|---|---|---|---|---|---|---|---|---|
| ATOM | 3899 | CB | ASP | B | 192 | 5.608 | 25.962 | 73.306 | 1.00 | 52.70 | C |
| ATOM | 3900 | CG | ASP | B | 192 | 4.877 | 25.658 | 74.580 | 1.00 | 52.70 | C |
| ATOM | 3901 | OD1 | ASP | B | 192 | 3.756 | 25.104 | 74.511 | 1.00 | 52.70 | O |
| ATOM | 3902 | OD2 | ASP | B | 192 | 5.428 | 25.973 | 75.651 | 1.00 | 52.70 | O |
| ATOM | 3903 | C | ASP | B | 192 | 6.401 | 25.159 | 71.122 | 1.00 | 31.52 | C |
| ATOM | 3904 | O | ASP | B | 192 | 5.682 | 25.419 | 70.157 | 1.00 | 31.52 | O |
| ATOM | 3905 | N | THR | B | 193 | 7.728 | 25.258 | 71.090 | 1.00 | 32.76 | N |
| ATOM | 3906 | CA | THR | B | 193 | 8.420 | 25.657 | 69.870 | 1.00 | 32.76 | C |
| ATOM | 3907 | CB | THR | B | 193 | 9.691 | 26.463 | 70.187 | 1.00 | 42.96 | C |
| ATOM | 3908 | OG1 | THR | B | 193 | 10.507 | 25.751 | 71.127 | 1.00 | 42.96 | O |
| ATOM | 3909 | CG2 | THR | B | 193 | 9.316 | 27.796 | 70.773 | 1.00 | 42.96 | C |
| ATOM | 3910 | C | THR | B | 193 | 8.792 | 24.443 | 69.039 | 1.00 | 32.76 | C |
| ATOM | 3911 | O | THR | B | 193 | 9.079 | 24.555 | 67.846 | 1.00 | 32.76 | O |
| ATOM | 3912 | N | ALA | B | 194 | 8.758 | 23.282 | 69.688 | 1.00 | 32.55 | N |
| ATOM | 3913 | CA | ALA | B | 194 | 9.087 | 22.011 | 69.058 | 1.00 | 32.55 | C |
| ATOM | 3914 | CB | ALA | B | 194 | 8.245 | 21.794 | 67.803 | 1.00 | 24.57 | C |
| ATOM | 3915 | C | ALA | B | 194 | 10.559 | 21.962 | 68.706 | 1.00 | 32.55 | C |
| ATOM | 3916 | O | ALA | B | 194 | 10.960 | 21.252 | 67.793 | 1.00 | 32.55 | O |
| ATOM | 3917 | N | VAL | B | 195 | 11.363 | 22.721 | 69.441 | 1.00 | 37.11 | N |
| ATOM | 3918 | CA | VAL | B | 195 | 12.803 | 22.762 | 69.213 | 1.00 | 37.11 | C |
| ATOM | 3919 | CB | VAL | B | 195 | 13.384 | 24.147 | 69.602 | 1.00 | 17.51 | C |
| ATOM | 3920 | CG1 | VAL | B | 195 | 14.891 | 24.182 | 69.388 | 1.00 | 17.51 | C |
| ATOM | 3921 | CG2 | VAL | B | 195 | 12.715 | 25.223 | 68.771 | 1.00 | 17.51 | C |
| ATOM | 3922 | C | VAL | B | 195 | 13.499 | 21.671 | 70.019 | 1.00 | 37.11 | C |
| ATOM | 3923 | O | VAL | B | 195 | 13.238 | 21.497 | 71.212 | 1.00 | 37.11 | O |
| ATOM | 3924 | N | LEU | B | 196 | 14.385 | 20.939 | 69.354 | 1.00 | 30.07 | N |
| ATOM | 3925 | CA | LEU | B | 196 | 15.115 | 19.856 | 69.995 | 1.00 | 30.07 | C |
| ATOM | 3926 | CB | LEU | B | 196 | 15.055 | 18.599 | 69.116 | 1.00 | 24.26 | C |
| ATOM | 3927 | CG | LEU | B | 196 | 15.759 | 17.351 | 69.652 | 1.00 | 24.26 | C |
| ATOM | 3928 | CD1 | LEU | B | 196 | 15.056 | 16.104 | 69.116 | 1.00 | 24.26 | C |
| ATOM | 3929 | CD2 | LEU | B | 196 | 17.248 | 17.384 | 69.282 | 1.00 | 24.26 | C |
| ATOM | 3930 | C | LEU | B | 196 | 16.563 | 20.246 | 70.276 | 1.00 | 30.07 | C |
| ATOM | 3931 | O | LEU | B | 196 | 17.159 | 21.036 | 69.536 | 1.00 | 30.07 | O |
| ATOM | 3932 | N | LYS | B | 197 | 17.108 | 19.692 | 71.359 | 1.00 | 26.26 | N |
| ATOM | 3933 | CA | LYS | B | 197 | 18.478 | 19.961 | 71.767 | 1.00 | 26.26 | C |
| ATOM | 3934 | CB | LYS | B | 197 | 18.499 | 21.106 | 72.778 | 1.00 | 45.24 | C |
| ATOM | 3935 | CG | LYS | B | 197 | 18.366 | 22.468 | 72.127 | 1.00 | 45.24 | C |
| ATOM | 3936 | CD | LYS | B | 197 | 18.368 | 23.573 | 73.150 | 1.00 | 45.24 | C |
| ATOM | 3937 | CE | LYS | B | 197 | 18.598 | 24.921 | 72.489 | 1.00 | 45.24 | C |
| ATOM | 3938 | NZ | LYS | B | 197 | 20.023 | 25.059 | 72.052 | 1.00 | 45.24 | N |
| ATOM | 3939 | C | LYS | B | 197 | 19.210 | 18.749 | 72.338 | 1.00 | 26.26 | C |
| ATOM | 3940 | O | LYS | B | 197 | 18.839 | 18.226 | 73.397 | 1.00 | 26.26 | O |
| ATOM | 3941 | N | LEU | B | 198 | 20.261 | 18.323 | 71.638 | 1.00 | 29.86 | N |
| ATOM | 3942 | CA | LEU | B | 198 | 21.056 | 17.174 | 72.056 | 1.00 | 29.86 | C |
| ATOM | 3943 | CB | LEU | B | 198 | 22.107 | 16.840 | 71.008 | 1.00 | 18.44 | C |
| ATOM | 3944 | CG | LEU | B | 198 | 22.337 | 15.374 | 70.707 | 1.00 | 18.44 | C |
| ATOM | 3945 | CD1 | LEU | B | 198 | 23.693 | 15.195 | 70.064 | 1.00 | 18.44 | C |
| ATOM | 3946 | CD2 | LEU | B | 198 | 22.246 | 14.628 | 71.976 | 1.00 | 18.44 | C |
| ATOM | 3947 | C | LEU | B | 198 | 21.776 | 17.509 | 73.345 | 1.00 | 29.86 | C |
| ATOM | 3948 | O | LEU | B | 198 | 22.267 | 18.622 | 73.506 | 1.00 | 29.86 | O |
| ATOM | 3949 | N | CYS | B | 199 | 21.853 | 16.548 | 74.259 | 1.00 | 32.10 | N |
| ATOM | 3950 | CA | CYS | B | 199 | 22.534 | 16.791 | 75.520 | 1.00 | 32.10 | C |
| ATOM | 3951 | CB | CYS | B | 199 | 21.543 | 17.229 | 76.601 | 1.00 | 32.64 | C |
| ATOM | 3952 | SG | CYS | B | 199 | 20.582 | 15.881 | 77.312 | 1.00 | 32.64 | S |
| ATOM | 3953 | C | CYS | B | 199 | 23.280 | 15.556 | 75.990 | 1.00 | 32.10 | C |
| ATOM | 3954 | O | CYS | B | 199 | 23.239 | 14.508 | 75.343 | 1.00 | 32.10 | O |
| ATOM | 3955 | N | ASP | B | 200 | 23.979 | 15.699 | 77.111 | 1.00 | 29.54 | N |
| ATOM | 3956 | CA | ASP | B | 200 | 24.730 | 14.596 | 77.665 | 1.00 | 29.54 | C |
| ATOM | 3957 | CB | ASP | B | 200 | 23.795 | 13.440 | 77.942 | 1.00 | 50.97 | C |

FIG. 7-67

```
ATOM   3958  CG   ASP B 200      24.502  12.233  78.544  1.00 50.97           C
ATOM   3959  OD1  ASP B 200      25.354  12.394  79.447  1.00 50.97           O
ATOM   3960  OD2  ASP B 200      24.173  11.109  78.123  1.00 50.97           O
ATOM   3961  C    ASP B 200      25.817  14.103  76.744  1.00 29.54           C
ATOM   3962  O    ASP B 200      25.536  13.319  75.852  1.00 29.54           O
ATOM   3963  N    PHE B 201      27.054  14.530  76.970  1.00 33.51           N
ATOM   3964  CA   PHE B 201      28.151  14.087  76.130  1.00 33.51           C
ATOM   3965  CB   PHE B 201      28.768  15.275  75.377  1.00 19.60           C
ATOM   3966  CG   PHE B 201      27.810  15.923  74.403  1.00 19.60           C
ATOM   3967  CD1  PHE B 201      26.670  16.594  74.871  1.00 19.60           C
ATOM   3968  CD2  PHE B 201      27.972  15.747  73.022  1.00 19.60           C
ATOM   3969  CE1  PHE B 201      25.714  17.062  73.979  1.00 19.60           C
ATOM   3970  CE2  PHE B 201      27.031  16.207  72.129  1.00 19.60           C
ATOM   3971  CZ   PHE B 201      25.897  16.863  72.595  1.00 19.60           C
ATOM   3972  C    PHE B 201      29.165  13.382  76.977  1.00 33.51           C
ATOM   3973  O    PHE B 201      30.368  13.399  76.671  1.00 33.51           O
ATOM   3974  N    GLY B 202      28.650  12.771  78.049  1.00 26.43           N
ATOM   3975  CA   GLY B 202      29.458  12.010  78.996  1.00 26.43           C
ATOM   3976  C    GLY B 202      30.028  10.738  78.363  1.00 26.43           C
ATOM   3977  O    GLY B 202      30.961  10.131  78.874  1.00 26.43           O
ATOM   3978  N    SER B 203      29.501  10.352  77.210  1.00 49.15           N
ATOM   3979  CA   SER B 203      29.981   9.174  76.489  1.00 49.15           C
ATOM   3980  CB   SER B 203      28.967   8.006  76.460  1.00 34.69           C
ATOM   3981  OG   SER B 203      27.875   8.104  77.391  1.00 34.69           O
ATOM   3982  C    SER B 203      30.018   9.810  75.164  1.00 49.15           C
ATOM   3983  O    SER B 203      28.979  10.023  74.566  1.00 49.15           O
ATOM   3984  N    ALA B 204      31.208  10.205  74.763  1.00 22.47           N
ATOM   3985  CA   ALA B 204      31.389  10.858  73.491  1.00 22.47           C
ATOM   3986  CB   ALA B 204      30.698  12.211  73.461  1.00 30.84           C
ATOM   3987  C    ALA B 204      32.871  11.031  73.306  1.00 22.47           C
ATOM   3988  O    ALA B 204      33.576  11.516  74.195  1.00 22.47           O
ATOM   3989  N    LYS B 205      33.337  10.629  72.136  1.00 34.03           N
ATOM   3990  CA   LYS B 205      34.739  10.692  71.812  1.00 34.03           C
ATOM   3991  CB   LYS B 205      35.389   9.323  72.083  1.00 39.35           C
ATOM   3992  CG   LYS B 205      36.906   9.379  72.139  1.00 39.35           C
ATOM   3993  CD   LYS B 205      37.428   8.030  71.742  1.00 39.35           C
ATOM   3994  CE   LYS B 205      38.696   7.690  72.484  1.00 39.35           C
ATOM   3995  NZ   LYS B 205      39.319   6.455  71.913  1.00 39.35           N
ATOM   3996  C    LYS B 205      34.925  11.097  70.378  1.00 34.03           C
ATOM   3997  O    LYS B 205      34.090  10.835  69.522  1.00 34.03           O
ATOM   3998  N    GLN B 206      36.023  11.788  70.146  1.00 41.77           N
ATOM   3999  CA   GLN B 206      36.343  12.194  68.817  1.00 41.77           C
ATOM   4000  CB   GLN B 206      37.257  13.388  68.865  1.00 59.16           C
ATOM   4001  CG   GLN B 206      37.466  14.020  67.542  1.00 59.16           C
ATOM   4002  CD   GLN B 206      38.357  15.212  67.640  1.00 59.16           C
ATOM   4003  OE1  GLN B 206      38.102  16.136  68.423  1.00 59.16           O
ATOM   4004  NE2  GLN B 206      39.419  15.213  66.842  1.00 59.16           N
ATOM   4005  C    GLN B 206      37.068  10.997  68.283  1.00 41.77           C
ATOM   4006  O    GLN B 206      38.240  10.806  68.582  1.00 41.77           O
ATOM   4007  N    LEU B 207      36.357  10.177  67.520  1.00 34.07           N
ATOM   4008  CA   LEU B 207      36.934   8.960  66.985  1.00 34.07           C
ATOM   4009  CB   LEU B 207      35.848   8.122  66.324  1.00 31.55           C
ATOM   4010  CG   LEU B 207      34.497   8.065  67.048  1.00 31.55           C
ATOM   4011  CD1  LEU B 207      33.499   7.278  66.226  1.00 31.55           C
ATOM   4012  CD2  LEU B 207      34.677   7.447  68.405  1.00 31.55           C
ATOM   4013  C    LEU B 207      38.042   9.213  65.988  1.00 34.07           C
ATOM   4014  O    LEU B 207      37.907  10.054  65.102  1.00 34.07           O
ATOM   4015  N    VAL B 208      39.137   8.474  66.165  1.00 50.99           N
ATOM   4016  CA   VAL B 208      40.306   8.516  65.293  1.00 50.99           C
ATOM   4017  CB   VAL B 208      41.564   8.994  66.042  1.00 38.31           C
```

FIG. 7-68

```
ATOM   4018  CG1 VAL B 208      42.782   8.897  65.126  1.00 38.31           C
ATOM   4019  CG2 VAL B 208      41.361  10.427  66.547  1.00 38.31           C
ATOM   4020  C   VAL B 208      40.498   7.061  64.884  1.00 50.99           C
ATOM   4021  O   VAL B 208      40.202   6.148  65.666  1.00 50.99           O
ATOM   4022  N   ARG B 209      40.968   6.837  63.663  1.00 50.78           N
ATOM   4023  CA  ARG B 209      41.166   5.475  63.189  1.00 50.78           C
ATOM   4024  CB  ARG B 209      40.874   5.391  61.700  1.00 99.98           C
ATOM   4025  CG  ARG B 209      41.186   6.664  60.974  1.00 99.98           C
ATOM   4026  CD  ARG B 209      41.109   6.465  59.489  1.00 99.98           C
ATOM   4027  NE  ARG B 209      41.160   7.744  58.796  1.00 99.98           N
ATOM   4028  CZ  ARG B 209      41.478   7.879  57.514  1.00 99.98           C
ATOM   4029  NH1 ARG B 209      41.779   6.808  56.789  1.00 99.98           N
ATOM   4030  NH2 ARG B 209      41.488   9.080  56.955  1.00 99.98           N
ATOM   4031  C   ARG B 209      42.574   4.993  63.473  1.00 50.78           C
ATOM   4032  O   ARG B 209      43.554   5.651  63.112  1.00 50.78           O
ATOM   4033  N   GLY B 210      42.654   3.827  64.109  1.00 70.49           N
ATOM   4034  CA  GLY B 210      43.929   3.248  64.486  1.00 70.49           C
ATOM   4035  C   GLY B 210      43.919   3.246  65.999  1.00 70.49           C
ATOM   4036  O   GLY B 210      44.499   2.382  66.661  1.00 70.49           O
ATOM   4037  N   GLU B 211      43.244   4.249  66.544  1.00 57.60           N
ATOM   4038  CA  GLU B 211      43.097   4.380  67.975  1.00 57.60           C
ATOM   4039  CB  GLU B 211      43.053   5.858  68.338  1.00 61.71           C
ATOM   4040  CG  GLU B 211      44.114   6.667  67.594  1.00 61.71           C
ATOM   4041  CD  GLU B 211      44.370   8.034  68.209  1.00 61.71           C
ATOM   4042  OE1 GLU B 211      45.228   8.776  67.676  1.00 61.71           O
ATOM   4043  OE2 GLU B 211      43.716   8.363  69.226  1.00 61.71           O
ATOM   4044  C   GLU B 211      41.769   3.681  68.264  1.00 57.60           C
ATOM   4045  O   GLU B 211      40.716   4.095  67.767  1.00 57.60           O
ATOM   4046  N   PRO B 212      41.811   2.591  69.048  1.00 34.38           N
ATOM   4047  CD  PRO B 212      43.047   2.027  69.611  1.00 43.35           C
ATOM   4048  CA  PRO B 212      40.657   1.772  69.438  1.00 34.38           C
ATOM   4049  CB  PRO B 212      41.299   0.533  70.070  1.00 43.35           C
ATOM   4050  CG  PRO B 212      42.737   0.569  69.609  1.00 43.35           C
ATOM   4051  C   PRO B 212      39.727   2.462  70.418  1.00 34.38           C
ATOM   4052  O   PRO B 212      40.154   3.300  71.210  1.00 34.38           O
ATOM   4053  N   ASN B 213      38.452   2.094  70.360  1.00 37.24           N
ATOM   4054  CA  ASN B 213      37.449   2.650  71.258  1.00 37.24           C
ATOM   4055  CB  ASN B 213      36.440   3.495  70.487  1.00 34.37           C
ATOM   4056  CG  ASN B 213      37.074   4.251  69.356  1.00 34.37           C
ATOM   4057  OD1 ASN B 213      37.798   5.225  69.563  1.00 34.37           O
ATOM   4058  ND2 ASN B 213      36.825   3.792  68.141  1.00 34.37           N
ATOM   4059  C   ASN B 213      36.744   1.462  71.883  1.00 37.24           C
ATOM   4060  O   ASN B 213      36.724   0.376  71.300  1.00 37.24           O
ATOM   4061  N   VAL B 214      36.178   1.673  73.067  1.00 22.64           N
ATOM   4062  CA  VAL B 214      35.468   0.627  73.793  1.00 22.64           C
ATOM   4063  CB  VAL B 214      34.936   1.155  75.125  1.00 28.92           C
ATOM   4064  CG1 VAL B 214      33.924   2.266  74.862  1.00 28.92           C
ATOM   4065  CG2 VAL B 214      34.312   0.017  75.934  1.00 28.92           C
ATOM   4066  C   VAL B 214      34.295   0.064  72.985  1.00 22.64           C
ATOM   4067  O   VAL B 214      33.646   0.785  72.221  1.00 22.64           O
ATOM   4068  N   SER B 215      34.022  -1.223  73.165  1.00 38.91           N
ATOM   4069  CA  SER B 215      32.955  -1.864  72.422  1.00 38.91           C
ATOM   4070  CB  SER B 215      33.348  -3.301  72.080  1.00 43.77           C
ATOM   4071  OG  SER B 215      34.570  -3.324  71.354  1.00 43.77           O
ATOM   4072  C   SER B 215      31.644  -1.837  73.182  1.00 38.91           C
ATOM   4073  O   SER B 215      30.600  -1.573  72.599  1.00 38.91           O
ATOM   4074  N   PTY B 216      31.686  -2.107  74.481  1.00 37.64           N
ATOM   4075  CA  PTY B 216      30.460  -2.077  75.260  1.00 37.64           C
ATOM   4076  C   PTY B 216      30.177  -0.597  75.496  1.00 37.64           C
ATOM   4077  O   PTY B 216      30.525  -0.015  76.518  1.00 37.64           O
```

FIG. 7-69

```
ATOM   4078  CB   PTY B 216      30.625  -2.844  76.580  1.00 49.59           C
ATOM   4079  CG   PTY B 216      29.332  -3.212  77.227  1.00 49.59           C
ATOM   4080  CD1  PTY B 216      28.337  -4.210  76.759  1.00 49.59           C
ATOM   4081  CD2  PTY B 216      29.073  -2.450  78.434  1.00 49.59           C
ATOM   4082  CE1  PTY B 216      27.097  -4.414  77.531  1.00 49.59           C
ATOM   4083  CE2  PTY B 216      27.840  -2.651  79.191  1.00 49.59           C
ATOM   4084  CZ   PTY B 216      26.858  -3.623  78.751  1.00 49.59           C
ATOM   4085  OH   PTY B 216      25.853  -3.750  79.600  1.00 49.59           O
ATOM   4086  P    PTY B 216      24.445  -4.080  79.047  1.00 49.59           P
ATOM   4087  OP1  PTY B 216      24.013  -3.215  78.007  1.00 49.59           O
ATOM   4088  OP2  PTY B 216      24.335  -5.510  78.412  1.00 49.59           O
ATOM   4089  OP3  PTY B 216      23.631  -3.871  80.199  1.00 49.59           O
ATOM   4090  N    ILE B 217      29.541   0.004  74.502  1.00 35.27           N
ATOM   4091  CA   ILE B 217      29.199   1.410  74.542  1.00 35.27           C
ATOM   4092  CB   ILE B 217      30.201   2.214  73.686  1.00 15.85           C
ATOM   4093  CG2  ILE B 217      29.913   1.998  72.190  1.00 15.85           C
ATOM   4094  CG1  ILE B 217      30.144   3.698  74.061  1.00 15.85           C
ATOM   4095  CD1  ILE B 217      30.579   3.961  75.454  1.00 15.85           C
ATOM   4096  C    ILE B 217      27.793   1.611  73.991  1.00 35.27           C
ATOM   4097  O    ILE B 217      27.382   0.881  73.103  1.00 35.27           O
ATOM   4098  N    CYS B 218      27.072   2.600  74.516  1.00 29.69           N
ATOM   4099  CA   CYS B 218      25.713   2.913  74.068  1.00 29.69           C
ATOM   4100  CB   CYS B 218      25.609   2.724  72.553  1.00 43.14           C
ATOM   4101  SG   CYS B 218      24.235   3.538  71.749  1.00 43.14           S
ATOM   4102  C    CYS B 218      24.724   2.005  74.779  1.00 29.69           C
ATOM   4103  O    CYS B 218      25.003   0.817  74.967  1.00 29.69           O
ATOM   4104  N    SER B 219      23.578   2.566  75.173  1.00 28.41           N
ATOM   4105  CA   SER B 219      22.553   1.799  75.886  1.00 28.41           C
ATOM   4106  CB   SER B 219      21.399   2.700  76.331  1.00 35.10           C
ATOM   4107  OG   SER B 219      21.815   4.051  76.325  1.00 35.10           O
ATOM   4108  C    SER B 219      22.024   0.659  75.033  1.00 28.41           C
ATOM   4109  O    SER B 219      21.578   0.870  73.901  1.00 28.41           O
ATOM   4110  N    ARG B 220      22.118  -0.543  75.594  1.00 30.04           N
ATOM   4111  CA   ARG B 220      21.697  -1.797  74.978  1.00 30.04           C
ATOM   4112  CB   ARG B 220      21.011  -2.625  76.069  1.00 50.55           C
ATOM   4113  CG   ARG B 220      21.225  -4.122  76.017  1.00 50.55           C
ATOM   4114  CD   ARG B 220      21.095  -4.643  77.436  1.00 50.55           C
ATOM   4115  NE   ARG B 220      19.913  -4.091  78.093  1.00 50.55           N
ATOM   4116  CZ   ARG B 220      19.669  -4.256  79.386  1.00 50.55           C
ATOM   4117  NH1  ARG B 220      20.530  -4.968  80.112  1.00 50.55           N
ATOM   4118  NH2  ARG B 220      18.623  -3.676  79.975  1.00 50.55           N
ATOM   4119  C    ARG B 220      20.755  -1.619  73.764  1.00 30.04           C
ATOM   4120  O    ARG B 220      21.087  -1.971  72.620  1.00 30.04           O
ATOM   4121  N    TYR B 221      19.582  -1.067  74.056  1.00 18.10           N
ATOM   4122  CA   TYR B 221      18.512  -0.835  73.111  1.00 18.10           C
ATOM   4123  CB   TYR B 221      17.440  -0.019  73.801  1.00 35.14           C
ATOM   4124  CG   TYR B 221      16.538  -0.856  74.662  1.00 35.14           C
ATOM   4125  CD1  TYR B 221      17.039  -1.908  75.450  1.00 35.14           C
ATOM   4126  CE1  TYR B 221      16.192  -2.672  76.255  1.00 35.14           C
ATOM   4127  CD2  TYR B 221      15.175  -0.598  74.709  1.00 35.14           C
ATOM   4128  CE2  TYR B 221      14.328  -1.356  75.512  1.00 35.14           C
ATOM   4129  CZ   TYR B 221      14.839  -2.384  76.275  1.00 35.14           C
ATOM   4130  OH   TYR B 221      13.970  -3.137  77.024  1.00 35.14           O
ATOM   4131  C    TYR B 221      18.898  -0.144  71.825  1.00 18.10           C
ATOM   4132  O    TYR B 221      18.393  -0.496  70.751  1.00 18.10           O
ATOM   4133  N    TYR B 222      19.766   0.857  71.921  1.00 22.19           N
ATOM   4134  CA   TYR B 222      20.145   1.603  70.737  1.00 22.19           C
ATOM   4135  CB   TYR B 222      19.882   3.085  70.980  1.00 27.11           C
ATOM   4136  CG   TYR B 222      18.570   3.341  71.703  1.00 27.11           C
ATOM   4137  CD1  TYR B 222      18.466   3.136  73.086  1.00 27.11           C
```

FIG. 7-70

| ATOM | 4138 | CE1 | TYR B 222 | 17.274 | 3.329 | 73.746 | 1.00 | 27.11 | C |
|------|------|-----|-----------|--------|-------|--------|------|-------|---|
| ATOM | 4139 | CD2 | TYR B 222 | 17.421 | 3.748 | 71.001 | 1.00 | 27.11 | C |
| ATOM | 4140 | CE2 | TYR B 222 | 16.219 | 3.940 | 71.664 | 1.00 | 27.11 | C |
| ATOM | 4141 | CZ  | TYR B 222 | 16.161 | 3.729 | 73.035 | 1.00 | 27.11 | C |
| ATOM | 4142 | OH  | TYR B 222 | 14.990 | 3.943 | 73.706 | 1.00 | 27.11 | O |
| ATOM | 4143 | C   | TYR B 222 | 21.592 | 1.369 | 70.363 | 1.00 | 22.19 | C |
| ATOM | 4144 | O   | TYR B 222 | 22.187 | 2.157 | 69.630 | 1.00 | 22.19 | O |
| ATOM | 4145 | N   | ARG B 223 | 22.148 | 0.280 | 70.879 | 1.00 | 26.61 | N |
| ATOM | 4146 | CA  | ARG B 223 | 23.522 | -0.081 | 70.592 | 1.00 | 26.61 | C |
| ATOM | 4147 | CB  | ARG B 223 | 24.056 | -1.052 | 71.661 | 1.00 | 42.92 | C |
| ATOM | 4148 | CG  | ARG B 223 | 25.440 | -1.659 | 71.371 | 1.00 | 42.92 | C |
| ATOM | 4149 | CD  | ARG B 223 | 26.250 | -1.783 | 72.660 | 1.00 | 42.92 | C |
| ATOM | 4150 | NE  | ARG B 223 | 25.431 | -2.282 | 73.762 | 1.00 | 42.92 | N |
| ATOM | 4151 | CZ  | ARG B 223 | 25.616 | -1.982 | 75.045 | 1.00 | 42.92 | C |
| ATOM | 4152 | NH1 | ARG B 223 | 26.606 | -1.175 | 75.416 | 1.00 | 42.92 | N |
| ATOM | 4153 | NH2 | ARG B 223 | 24.790 | -2.468 | 75.958 | 1.00 | 42.92 | N |
| ATOM | 4154 | C   | ARG B 223 | 23.566 | -0.714 | 69.206 | 1.00 | 26.61 | C |
| ATOM | 4155 | O   | ARG B 223 | 22.857 | -1.684 | 68.918 | 1.00 | 26.61 | O |
| ATOM | 4156 | N   | ALA B 224 | 24.391 | -0.134 | 68.340 | 1.00 | 28.20 | N |
| ATOM | 4157 | CA  | ALA B 224 | 24.554 | -0.633 | 66.975 | 1.00 | 28.20 | C |
| ATOM | 4158 | CB  | ALA B 224 | 25.569 | 0.222 | 66.215 | 1.00 | 13.65 | C |
| ATOM | 4159 | C   | ALA B 224 | 25.017 | -2.088 | 67.019 | 1.00 | 28.20 | C |
| ATOM | 4160 | O   | ALA B 224 | 25.612 | -2.530 | 68.002 | 1.00 | 28.20 | O |
| ATOM | 4161 | N   | PRO B 225 | 24.759 | -2.852 | 65.949 | 1.00 | 42.94 | N |
| ATOM | 4162 | CD  | PRO B 225 | 24.164 | -2.444 | 64.662 | 1.00 | 40.19 | C |
| ATOM | 4163 | CA  | PRO B 225 | 25.169 | -4.260 | 65.920 | 1.00 | 42.94 | C |
| ATOM | 4164 | CB  | PRO B 225 | 24.631 | -4.742 | 64.574 | 1.00 | 40.19 | C |
| ATOM | 4165 | CG  | PRO B 225 | 24.674 | -3.498 | 63.723 | 1.00 | 40.19 | C |
| ATOM | 4166 | C   | PRO B 225 | 26.678 | -4.493 | 66.086 | 1.00 | 42.94 | C |
| ATOM | 4167 | O   | PRO B 225 | 27.090 | -5.323 | 66.901 | 1.00 | 42.94 | O |
| ATOM | 4168 | N   | GLU B 226 | 27.490 | -3.755 | 65.327 | 1.00 | 47.96 | N |
| ATOM | 4169 | CA  | GLU B 226 | 28.948 | -3.881 | 65.384 | 1.00 | 47.96 | C |
| ATOM | 4170 | CB  | GLU B 226 | 29.624 | -2.733 | 64.638 | 1.00 | 31.25 | C |
| ATOM | 4171 | CG  | GLU B 226 | 28.873 | -2.259 | 63.429 | 1.00 | 31.25 | C |
| ATOM | 4172 | CD  | GLU B 226 | 28.116 | -0.972 | 63.696 | 1.00 | 31.25 | C |
| ATOM | 4173 | OE1 | GLU B 226 | 28.765 | 0.078 | 63.888 | 1.00 | 31.25 | O |
| ATOM | 4174 | OE2 | GLU B 226 | 26.871 | -1.010 | 63.722 | 1.00 | 31.25 | O |
| ATOM | 4175 | C   | GLU B 226 | 29.471 | -3.883 | 66.812 | 1.00 | 47.96 | C |
| ATOM | 4176 | O   | GLU B 226 | 30.311 | -4.704 | 67.172 | 1.00 | 47.96 | O |
| ATOM | 4177 | N   | LEU B 227 | 28.990 | -2.947 | 67.620 | 1.00 | 43.36 | N |
| ATOM | 4178 | CA  | LEU B 227 | 29.428 | -2.871 | 69.000 | 1.00 | 43.36 | C |
| ATOM | 4179 | CB  | LEU B 227 | 28.677 | -1.740 | 69.718 | 1.00 | 26.27 | C |
| ATOM | 4180 | CG  | LEU B 227 | 28.762 | -0.352 | 69.048 | 1.00 | 26.27 | C |
| ATOM | 4181 | CD1 | LEU B 227 | 27.926 | 0.633 | 69.835 | 1.00 | 26.27 | C |
| ATOM | 4182 | CD2 | LEU B 227 | 30.214 | 0.140 | 68.951 | 1.00 | 26.27 | C |
| ATOM | 4183 | C   | LEU B 227 | 29.200 | -4.220 | 69.694 | 1.00 | 43.36 | C |
| ATOM | 4184 | O   | LEU B 227 | 30.099 | -4.748 | 70.348 | 1.00 | 43.36 | O |
| ATOM | 4185 | N   | ILE B 228 | 28.003 | -4.778 | 69.541 | 1.00 | 54.79 | N |
| ATOM | 4186 | CA  | ILE B 228 | 27.667 | -6.071 | 70.136 | 1.00 | 54.79 | C |
| ATOM | 4187 | CB  | ILE B 228 | 26.220 | -6.461 | 69.760 | 1.00 | 48.10 | C |
| ATOM | 4188 | CG2 | ILE B 228 | 25.846 | -7.802 | 70.392 | 1.00 | 48.10 | C |
| ATOM | 4189 | CG1 | ILE B 228 | 25.271 | -5.338 | 70.201 | 1.00 | 48.10 | C |
| ATOM | 4190 | CD1 | ILE B 228 | 23.840 | -5.526 | 69.793 | 1.00 | 48.10 | C |
| ATOM | 4191 | C   | ILE B 228 | 28.647 | -7.149 | 69.635 | 1.00 | 54.79 | C |
| ATOM | 4192 | O   | ILE B 228 | 28.967 | -8.106 | 70.346 | 1.00 | 54.79 | O |
| ATOM | 4193 | N   | PHE B 229 | 29.116 | -6.973 | 68.402 | 1.00 | 32.87 | N |
| ATOM | 4194 | CA  | PHE B 229 | 30.067 | -7.886 | 67.781 | 1.00 | 32.87 | C |
| ATOM | 4195 | CB  | PHE B 229 | 29.907 | -7.846 | 66.263 | 1.00 | 66.75 | C |
| ATOM | 4196 | CG  | PHE B 229 | 28.689 | -8.561 | 65.774 | 1.00 | 66.75 | C |
| ATOM | 4197 | CD1 | PHE B 229 | 28.799 | -9.566 | 64.824 | 1.00 | 66.75 | C |

FIG. 7-71

```
ATOM   4198  CD2 PHE B 229      27.436  -8.260  66.290  1.00 66.75           C
ATOM   4199  CE1 PHE B 229      27.678 -10.266  64.399  1.00 66.75           C
ATOM   4200  CE2 PHE B 229      26.309  -8.955  65.869  1.00 66.75           C
ATOM   4201  CZ  PHE B 229      26.431  -9.958  64.925  1.00 66.75           C
ATOM   4202  C   PHE B 229      31.511  -7.562  68.167  1.00 32.87           C
ATOM   4203  O   PHE B 229      32.455  -8.021  67.528  1.00 32.87           O
ATOM   4204  N   GLY B 230      31.672  -6.747  69.203  1.00 46.55           N
ATOM   4205  CA  GLY B 230      33.000  -6.409  69.680  1.00 46.55           C
ATOM   4206  C   GLY B 230      33.875  -5.487  68.852  1.00 46.55           C
ATOM   4207  O   GLY B 230      35.070  -5.356  69.126  1.00 46.55           O
ATOM   4208  N   ALA B 231      33.308  -4.851  67.838  1.00 48.81           N
ATOM   4209  CA  ALA B 231      34.097  -3.935  67.029  1.00 48.81           C
ATOM   4210  CB  ALA B 231      33.205  -3.266  65.990  1.00 20.78           C
ATOM   4211  C   ALA B 231      34.708  -2.883  67.958  1.00 48.81           C
ATOM   4212  O   ALA B 231      34.078  -2.455  68.923  1.00 48.81           O
ATOM   4213  N   THR B 232      35.935  -2.472  67.684  1.00 46.21           N
ATOM   4214  CA  THR B 232      36.575  -1.466  68.520  1.00 46.21           C
ATOM   4215  CB  THR B 232      37.795  -2.061  69.294  1.00 29.55           C
ATOM   4216  OG1 THR B 232      38.786  -2.516  68.358  1.00 29.55           O
ATOM   4217  CG2 THR B 232      37.359  -3.230  70.178  1.00 29.55           C
ATOM   4218  C   THR B 232      37.049  -0.367  67.579  1.00 46.21           C
ATOM   4219  O   THR B 232      37.444   0.729  67.998  1.00 46.21           O
ATOM   4220  N   ASP B 233      36.981  -0.691  66.293  1.00 41.91           N
ATOM   4221  CA  ASP B 233      37.414   0.192  65.223  1.00 41.91           C
ATOM   4222  CB  ASP B 233      38.358  -0.580  64.294  1.00 94.75           C
ATOM   4223  CG  ASP B 233      37.842  -1.975  63.955  1.00 94.75           C
ATOM   4224  OD1 ASP B 233      37.465  -2.739  64.875  1.00 94.75           O
ATOM   4225  OD2 ASP B 233      37.824  -2.319  62.756  1.00 94.75           O
ATOM   4226  C   ASP B 233      36.243   0.786  64.436  1.00 41.91           C
ATOM   4227  O   ASP B 233      36.374   1.097  63.249  1.00 41.91           O
ATOM   4228  N   TYR B 234      35.109   0.967  65.116  1.00 27.87           N
ATOM   4229  CA  TYR B 234      33.901   1.521  64.508  1.00 27.87           C
ATOM   4230  CB  TYR B 234      32.702   1.262  65.420  1.00 29.14           C
ATOM   4231  CG  TYR B 234      32.902   1.733  66.845  1.00 29.14           C
ATOM   4232  CD1 TYR B 234      32.712   3.074  67.203  1.00 29.14           C
ATOM   4233  CE1 TYR B 234      32.892   3.490  68.524  1.00 29.14           C
ATOM   4234  CD2 TYR B 234      33.278   0.831  67.840  1.00 29.14           C
ATOM   4235  CE2 TYR B 234      33.457   1.233  69.147  1.00 29.14           C
ATOM   4236  CZ  TYR B 234      33.262   2.553  69.487  1.00 29.14           C
ATOM   4237  OH  TYR B 234      33.419   2.926  70.800  1.00 29.14           O
ATOM   4238  C   TYR B 234      33.995   3.012  64.236  1.00 27.87           C
ATOM   4239  O   TYR B 234      34.943   3.680  64.657  1.00 27.87           O
ATOM   4240  N   THR B 235      32.996   3.540  63.539  1.00 37.97           N
ATOM   4241  CA  THR B 235      32.984   4.967  63.233  1.00 37.97           C
ATOM   4242  CB  THR B 235      32.951   5.226  61.719  1.00 36.63           C
ATOM   4243  OG1 THR B 235      31.641   4.930  61.212  1.00 36.63           O
ATOM   4244  CG2 THR B 235      33.988   4.359  61.014  1.00 36.63           C
ATOM   4245  C   THR B 235      31.793   5.692  63.845  1.00 37.97           C
ATOM   4246  O   THR B 235      30.957   5.105  64.541  1.00 37.97           O
ATOM   4247  N   SER B 236      31.725   6.986  63.575  1.00 34.82           N
ATOM   4248  CA  SER B 236      30.636   7.785  64.093  1.00 34.82           C
ATOM   4249  CB  SER B 236      30.962   9.287  64.023  1.00 41.56           C
ATOM   4250  OG  SER B 236      31.075   9.745  62.686  1.00 41.56           O
ATOM   4251  C   SER B 236      29.380   7.477  63.300  1.00 34.82           C
ATOM   4252  O   SER B 236      28.451   8.273  63.268  1.00 34.82           O
ATOM   4253  N   SER B 237      29.359   6.317  62.651  1.00 39.31           N
ATOM   4254  CA  SER B 237      28.180   5.904  61.893  1.00 39.31           C
ATOM   4255  CB  SER B 237      28.558   5.056  60.669  1.00 55.67           C
ATOM   4256  OG  SER B 237      29.110   3.805  61.041  1.00 55.67           O
ATOM   4257  C   SER B 237      27.298   5.087  62.822  1.00 39.31           C
```

FIG. 7-72

```
ATOM   4258  O    SER B 237      26.237   4.620  62.433  1.00 39.31           O
ATOM   4259  N    ILE B 238      27.744   4.921  64.061  1.00 29.82           N
ATOM   4260  CA   ILE B 238      26.977   4.162  65.039  1.00 29.82           C
ATOM   4261  CB   ILE B 238      27.889   3.605  66.148  1.00 25.88           C
ATOM   4262  CG2  ILE B 238      28.997   2.801  65.532  1.00 25.88           C
ATOM   4263  CG1  ILE B 238      28.501   4.749  66.946  1.00 25.88           C
ATOM   4264  CD1  ILE B 238      29.011   4.338  68.317  1.00 25.88           C
ATOM   4265  C    ILE B 238      25.859   5.010  65.665  1.00 29.82           C
ATOM   4266  O    ILE B 238      24.930   4.474  66.271  1.00 29.82           O
ATOM   4267  N    ASP B 239      25.967   6.333  65.524  1.00 20.72           N
ATOM   4268  CA   ASP B 239      24.956   7.255  66.030  1.00 20.72           C
ATOM   4269  CB   ASP B 239      25.481   8.702  66.072  1.00 20.04           C
ATOM   4270  CG   ASP B 239      26.350   8.997  67.303  1.00 20.04           C
ATOM   4271  OD1  ASP B 239      26.064   8.445  68.386  1.00 20.04           O
ATOM   4272  OD2  ASP B 239      27.304   9.801  67.205  1.00 20.04           O
ATOM   4273  C    ASP B 239      23.752   7.197  65.092  1.00 20.72           C
ATOM   4274  O    ASP B 239      22.608   7.393  65.513  1.00 20.72           O
ATOM   4275  N    VAL B 240      24.019   6.934  63.817  1.00 23.28           N
ATOM   4276  CA   VAL B 240      22.962   6.855  62.826  1.00 23.28           C
ATOM   4277  CB   VAL B 240      23.549   6.719  61.421  1.00 24.25           C
ATOM   4278  CG1  VAL B 240      22.430   6.606  60.411  1.00 24.25           C
ATOM   4279  CG2  VAL B 240      24.434   7.916  61.113  1.00 24.25           C
ATOM   4280  C    VAL B 240      22.056   5.661  63.120  1.00 23.28           C
ATOM   4281  O    VAL B 240      20.839   5.721  62.915  1.00 23.28           O
ATOM   4282  N    TRP B 241      22.657   4.573  63.595  1.00 24.82           N
ATOM   4283  CA   TRP B 241      21.898   3.379  63.948  1.00 24.82           C
ATOM   4284  CB   TRP B 241      22.841   2.295  64.467  1.00 25.44           C
ATOM   4285  CG   TRP B 241      22.132   1.088  64.981  1.00 25.44           C
ATOM   4286  CD2  TRP B 241      21.711  -0.033  64.210  1.00 25.44           C
ATOM   4287  CE2  TRP B 241      21.032  -0.915  65.087  1.00 25.44           C
ATOM   4288  CE3  TRP B 241      21.870  -0.401  62.867  1.00 25.44           C
ATOM   4289  CD1  TRP B 241      21.688   0.869  66.256  1.00 25.44           C
ATOM   4290  NE1  TRP B 241      21.021  -0.330  66.325  1.00 25.44           N
ATOM   4291  CZ2  TRP B 241      20.467  -2.126  64.651  1.00 25.44           C
ATOM   4292  CZ3  TRP B 241      21.307  -1.615  62.430  1.00 25.44           C
ATOM   4293  CH2  TRP B 241      20.630  -2.466  63.329  1.00 25.44           C
ATOM   4294  C    TRP B 241      20.914   3.767  65.042  1.00 24.82           C
ATOM   4295  O    TRP B 241      19.710   3.553  64.919  1.00 24.82           O
ATOM   4296  N    SER B 242      21.459   4.330  66.116  1.00 24.85           N
ATOM   4297  CA   SER B 242      20.678   4.793  67.249  1.00 24.85           C
ATOM   4298  CB   SER B 242      21.590   5.534  68.240  1.00 26.97           C
ATOM   4299  OG   SER B 242      22.735   4.767  68.584  1.00 26.97           O
ATOM   4300  C    SER B 242      19.598   5.745  66.721  1.00 24.85           C
ATOM   4301  O    SER B 242      18.446   5.715  67.159  1.00 24.85           O
ATOM   4302  N    ALA B 243      19.976   6.598  65.774  1.00 25.24           N
ATOM   4303  CA   ALA B 243      19.023   7.535  65.189  1.00 25.24           C
ATOM   4304  CB   ALA B 243      19.702   8.348  64.101  1.00 27.33           C
ATOM   4305  C    ALA B 243      17.841   6.735  64.618  1.00 25.24           C
ATOM   4306  O    ALA B 243      16.677   7.052  64.874  1.00 25.24           O
ATOM   4307  N    GLY B 244      18.152   5.694  63.852  1.00 26.88           N
ATOM   4308  CA   GLY B 244      17.114   4.846  63.298  1.00 26.88           C
ATOM   4309  C    GLY B 244      16.310   4.152  64.396  1.00 26.88           C
ATOM   4310  O    GLY B 244      15.100   3.949  64.251  1.00 26.88           O
ATOM   4311  N    CYS B 245      16.969   3.800  65.502  1.00 36.99           N
ATOM   4312  CA   CYS B 245      16.294   3.125  66.612  1.00 36.99           C
ATOM   4313  CB   CYS B 245      17.301   2.610  67.650  1.00 29.55           C
ATOM   4314  SG   CYS B 245      18.170   1.086  67.175  1.00 29.55           S
ATOM   4315  C    CYS B 245      15.310   4.045  67.293  1.00 36.99           C
ATOM   4316  O    CYS B 245      14.285   3.601  67.815  1.00 36.99           O
ATOM   4317  N    VAL B 246      15.618   5.334  67.294  1.00 19.27           N
```

FIG. 7-73

| | | | | | | | | | | |
|---|---|---|---|---|---|---|---|---|---|---|
| ATOM | 4318 | CA | VAL | B | 246 | 14.730 | 6.288 | 67.933 | 1.00 19.27 | C |
| ATOM | 4319 | CB | VAL | B | 246 | 15.467 | 7.632 | 68.237 | 1.00 11.03 | C |
| ATOM | 4320 | CG1 | VAL | B | 246 | 14.482 | 8.687 | 68.766 | 1.00 11.03 | C |
| ATOM | 4321 | CG2 | VAL | B | 246 | 16.560 | 7.392 | 69.261 | 1.00 11.03 | C |
| ATOM | 4322 | C | VAL | B | 246 | 13.536 | 6.523 | 67.016 | 1.00 19.27 | C |
| ATOM | 4323 | O | VAL | B | 246 | 12.390 | 6.562 | 67.471 | 1.00 19.27 | O |
| ATOM | 4324 | N | LEU | B | 247 | 13.821 | 6.656 | 65.722 | 1.00 27.56 | N |
| ATOM | 4325 | CA | LEU | B | 247 | 12.794 | 6.885 | 64.720 | 1.00 27.56 | C |
| ATOM | 4326 | CB | LEU | B | 247 | 13.420 | 6.983 | 63.331 | 1.00 23.05 | C |
| ATOM | 4327 | CG | LEU | B | 247 | 12.453 | 7.041 | 62.144 | 1.00 23.05 | C |
| ATOM | 4328 | CD1 | LEU | B | 247 | 11.548 | 8.273 | 62.237 | 1.00 23.05 | C |
| ATOM | 4329 | CD2 | LEU | B | 247 | 13.264 | 7.050 | 60.858 | 1.00 23.05 | C |
| ATOM | 4330 | C | LEU | B | 247 | 11.810 | 5.735 | 64.742 | 1.00 27.56 | C |
| ATOM | 4331 | O | LEU | B | 247 | 10.590 | 5.934 | 64.845 | 1.00 27.56 | O |
| ATOM | 4332 | N | ALA | B | 248 | 12.350 | 4.526 | 64.644 | 1.00 30.09 | N |
| ATOM | 4333 | CA | ALA | B | 248 | 11.515 | 3.339 | 64.640 | 1.00 30.09 | C |
| ATOM | 4334 | CB | ALA | B | 248 | 12.367 | 2.114 | 64.629 | 1.00 4.68 | C |
| ATOM | 4335 | C | ALA | B | 248 | 10.634 | 3.338 | 65.867 | 1.00 30.09 | C |
| ATOM | 4336 | O | ALA | B | 248 | 9.434 | 3.051 | 65.795 | 1.00 30.09 | O |
| ATOM | 4337 | N | GLU | B | 249 | 11.245 | 3.680 | 66.994 | 1.00 31.18 | N |
| ATOM | 4338 | CA | GLU | B | 249 | 10.547 | 3.723 | 68.265 | 1.00 31.18 | C |
| ATOM | 4339 | CB | GLU | B | 249 | 11.538 | 4.039 | 69.376 | 1.00 22.39 | C |
| ATOM | 4340 | CG | GLU | B | 249 | 10.980 | 3.869 | 70.782 | 1.00 22.39 | C |
| ATOM | 4341 | CD | GLU | B | 249 | 12.048 | 4.034 | 71.837 | 1.00 22.39 | C |
| ATOM | 4342 | OE1 | GLU | B | 249 | 13.173 | 3.564 | 71.603 | 1.00 22.39 | O |
| ATOM | 4343 | OE2 | GLU | B | 249 | 11.774 | 4.616 | 72.899 | 1.00 22.39 | O |
| ATOM | 4344 | C | GLU | B | 249 | 9.415 | 4.736 | 68.296 | 1.00 31.18 | C |
| ATOM | 4345 | O | GLU | B | 249 | 8.385 | 4.503 | 68.931 | 1.00 31.18 | O |
| ATOM | 4346 | N | LEU | B | 250 | 9.617 | 5.869 | 67.627 | 1.00 29.29 | N |
| ATOM | 4347 | CA | LEU | B | 250 | 8.602 | 6.909 | 67.585 | 1.00 29.29 | C |
| ATOM | 4348 | CB | LEU | B | 250 | 9.205 | 8.206 | 67.050 | 1.00 14.11 | C |
| ATOM | 4349 | CG | LEU | B | 250 | 10.156 | 8.927 | 68.018 | 1.00 14.11 | C |
| ATOM | 4350 | CD1 | LEU | B | 250 | 10.557 | 10.286 | 67.409 | 1.00 14.11 | C |
| ATOM | 4351 | CD2 | LEU | B | 250 | 9.493 | 9.132 | 69.392 | 1.00 14.11 | C |
| ATOM | 4352 | C | LEU | B | 250 | 7.447 | 6.450 | 66.712 | 1.00 29.29 | C |
| ATOM | 4353 | O | LEU | B | 250 | 6.292 | 6.760 | 66.968 | 1.00 29.29 | O |
| ATOM | 4354 | N | LEU | B | 251 | 7.768 | 5.682 | 65.684 | 1.00 35.46 | N |
| ATOM | 4355 | CA | LEU | B | 251 | 6.745 | 5.193 | 64.795 | 1.00 35.46 | C |
| ATOM | 4356 | CB | LEU | B | 251 | 7.375 | 4.710 | 63.488 | 1.00 20.66 | C |
| ATOM | 4357 | CG | LEU | B | 251 | 7.983 | 5.807 | 62.621 | 1.00 20.66 | C |
| ATOM | 4358 | CD1 | LEU | B | 251 | 8.573 | 5.157 | 61.361 | 1.00 20.66 | C |
| ATOM | 4359 | CD2 | LEU | B | 251 | 6.910 | 6.850 | 62.295 | 1.00 20.66 | C |
| ATOM | 4360 | C | LEU | B | 251 | 5.994 | 4.064 | 65.475 | 1.00 35.46 | C |
| ATOM | 4361 | O | LEU | B | 251 | 4.767 | 3.989 | 65.377 | 1.00 35.46 | O |
| ATOM | 4362 | N | LEU | B | 252 | 6.729 | 3.218 | 66.202 | 1.00 37.91 | N |
| ATOM | 4363 | CA | LEU | B | 252 | 6.131 | 2.070 | 66.869 | 1.00 37.91 | C |
| ATOM | 4364 | CB | LEU | B | 252 | 7.195 | 1.020 | 67.189 | 1.00 41.94 | C |
| ATOM | 4365 | CG | LEU | B | 252 | 6.899 | -0.394 | 66.711 | 1.00 41.94 | C |
| ATOM | 4366 | CD1 | LEU | B | 252 | 6.724 | -0.361 | 65.211 | 1.00 41.94 | C |
| ATOM | 4367 | CD2 | LEU | B | 252 | 8.034 | -1.344 | 67.129 | 1.00 41.94 | C |
| ATOM | 4368 | C | LEU | B | 252 | 5.378 | 2.473 | 68.130 | 1.00 37.91 | C |
| ATOM | 4369 | O | LEU | B | 252 | 4.210 | 2.185 | 68.243 | 1.00 37.91 | O |
| ATOM | 4370 | N | GLY | B | 253 | 6.010 | 3.169 | 69.063 | 1.00 40.49 | N |
| ATOM | 4371 | CA | GLY | B | 253 | 5.314 | 3.544 | 70.279 | 1.00 40.49 | C |
| ATOM | 4372 | C | GLY | B | 253 | 5.983 | 2.771 | 71.403 | 1.00 40.49 | C |
| ATOM | 4373 | O | GLY | B | 253 | 5.494 | 2.792 | 72.523 | 1.00 40.49 | O |
| ATOM | 4374 | N | GLN | B | 254 | 7.091 | 2.078 | 71.098 | 1.00 32.48 | N |
| ATOM | 4375 | CA | GLN | B | 254 | 7.858 | 1.286 | 72.064 | 1.00 32.48 | C |
| ATOM | 4376 | CB | GLN | B | 254 | 7.127 | -0.046 | 72.370 | 1.00 40.68 | C |
| ATOM | 4377 | CG | GLN | B | 254 | 7.155 | -1.136 | 71.293 | 1.00 40.68 | C |

FIG. 7-74

```
ATOM   4378  CD   GLN B 254       6.170  -2.249  71.593  1.00 40.68           C
ATOM   4379  OE1  GLN B 254       6.408  -3.104  72.458  1.00 40.68           O
ATOM   4380  NE2  GLN B 254       5.042  -2.235  70.889  1.00 40.68           N
ATOM   4381  C    GLN B 254       9.196   1.025  71.400  1.00 32.48           C
ATOM   4382  O    GLN B 254       9.337   1.086  70.197  1.00 32.48           O
ATOM   4383  N    PRO B 255      10.199   0.751  72.181  1.00 83.88           N
ATOM   4384  CD   PRO B 255      10.084   0.679  73.632  1.00 28.67           C
ATOM   4385  CA   PRO B 255      11.551   0.467  71.719  1.00 83.88           C
ATOM   4386  CB   PRO B 255      12.264   0.113  72.988  1.00 28.67           C
ATOM   4387  CG   PRO B 255      11.452   0.816  74.011  1.00 28.67           C
ATOM   4388  C    PRO B 255      11.534  -0.699  70.786  1.00 83.88           C
ATOM   4389  O    PRO B 255      11.146  -1.785  71.177  1.00 83.88           O
ATOM   4390  N    ILE B 256      11.935  -0.464  69.550  1.00 29.28           N
ATOM   4391  CA   ILE B 256      11.968  -1.504  68.517  1.00 29.28           C
ATOM   4392  CB   ILE B 256      12.508  -0.894  67.200  1.00 16.86           C
ATOM   4393  CG2  ILE B 256      13.916  -0.344  67.400  1.00 16.86           C
ATOM   4394  CG1  ILE B 256      12.388  -1.903  66.073  1.00 16.86           C
ATOM   4395  CD1  ILE B 256      13.393  -1.715  65.044  1.00 16.86           C
ATOM   4396  C    ILE B 256      12.777  -2.770  68.877  1.00 29.28           C
ATOM   4397  O    ILE B 256      12.357  -3.904  68.587  1.00 29.28           O
ATOM   4398  N    PHE B 257      13.935  -2.568  69.500  1.00 50.32           N
ATOM   4399  CA   PHE B 257      14.819  -3.673  69.905  1.00 50.32           C
ATOM   4400  CB   PHE B 257      16.123  -3.597  69.132  1.00 32.91           C
ATOM   4401  CG   PHE B 257      15.935  -3.668  67.652  1.00 32.91           C
ATOM   4402  CD1  PHE B 257      15.204  -4.714  67.115  1.00 32.91           C
ATOM   4403  CD2  PHE B 257      16.480  -2.705  66.784  1.00 32.91           C
ATOM   4404  CE1  PHE B 257      15.013  -4.822  65.759  1.00 32.91           C
ATOM   4405  CE2  PHE B 257      16.289  -2.814  65.398  1.00 32.91           C
ATOM   4406  CZ   PHE B 257      15.549  -3.885  64.892  1.00 32.91           C
ATOM   4407  C    PHE B 257      15.092  -3.616  71.399  1.00 50.32           C
ATOM   4408  O    PHE B 257      16.113  -3.080  71.851  1.00 50.32           O
ATOM   4409  N    PRO B 258      14.173  -4.199  72.180  1.00 44.88           N
ATOM   4410  CD   PRO B 258      12.969  -4.889  71.673  1.00 30.26           C
ATOM   4411  CA   PRO B 258      14.231  -4.251  73.640  1.00 44.88           C
ATOM   4412  CB   PRO B 258      12.760  -4.294  74.027  1.00 30.26           C
ATOM   4413  CG   PRO B 258      12.140  -5.147  72.940  1.00 30.26           C
ATOM   4414  C    PRO B 258      15.032  -5.359  74.289  1.00 44.88           C
ATOM   4415  O    PRO B 258      14.605  -5.939  75.282  1.00 44.88           O
ATOM   4416  N    GLY B 259      16.205  -5.643  73.739  1.00 61.44           N
ATOM   4417  CA   GLY B 259      17.036  -6.688  74.305  1.00 61.44           C
ATOM   4418  C    GLY B 259      17.416  -6.403  75.754  1.00 61.44           C
ATOM   4419  O    GLY B 259      17.471  -5.248  76.178  1.00 61.44           O
ATOM   4420  N    ASP B 260      17.684  -7.459  76.516  1.00 42.39           N
ATOM   4421  CA   ASP B 260      18.060  -7.333  77.919  1.00 42.39           C
ATOM   4422  CB   ASP B 260      17.234  -8.296  78.769  1.00 29.22           C
ATOM   4423  CG   ASP B 260      17.324  -8.006  80.265  1.00 29.22           C
ATOM   4424  OD1  ASP B 260      17.640  -8.940  81.038  1.00 29.22           O
ATOM   4425  OD2  ASP B 260      17.053  -6.857  80.668  1.00 29.22           O
ATOM   4426  C    ASP B 260      19.538  -7.658  78.082  1.00 42.39           C
ATOM   4427  O    ASP B 260      20.090  -7.586  79.185  1.00 42.39           O
ATOM   4428  N    SER B 261      20.183  -8.044  76.992  1.00 33.88           N
ATOM   4429  CA   SER B 261      21.593  -8.355  77.075  1.00 33.88           C
ATOM   4430  CB   SER B 261      21.782  -9.691  77.799  1.00 32.74           C
ATOM   4431  OG   SER B 261      22.226 -10.698  76.896  1.00 32.74           O
ATOM   4432  C    SER B 261      22.199  -8.426  75.671  1.00 33.88           C
ATOM   4433  O    SER B 261      21.471  -8.520  74.695  1.00 33.88           O
ATOM   4434  N    GLY B 262      23.526  -8.378  75.577  1.00 43.12           N
ATOM   4435  CA   GLY B 262      24.184  -8.459  74.288  1.00 43.12           C
ATOM   4436  C    GLY B 262      23.527  -9.518  73.422  1.00 43.12           C
ATOM   4437  O    GLY B 262      23.551  -9.440  72.198  1.00 43.12           O
```

FIG. 7-75

```
ATOM   4438  N    VAL B 263      22.966 -10.541  74.057  1.00 37.23           N
ATOM   4439  CA   VAL B 263      22.309 -11.651  73.351  1.00 37.23           C
ATOM   4440  CB   VAL B 263      22.074 -12.797  74.292  1.00 39.36           C
ATOM   4441  CG1  VAL B 263      21.391 -13.975  73.680  1.00 39.36           C
ATOM   4442  CG2  VAL B 263      23.311 -13.310  74.560  1.00 39.36           C
ATOM   4443  C    VAL B 263      20.987 -11.327  72.700  1.00 37.23           C
ATOM   4444  O    VAL B 263      20.883 -11.333  71.477  1.00 37.23           O
ATOM   4445  N    ASP B 264      19.972 -11.063  73.510  1.00 65.81           N
ATOM   4446  CA   ASP B 264      18.639 -10.779  73.012  1.00 65.81           C
ATOM   4447  CB   ASP B 264      17.706 -10.576  74.192  1.00 50.02           C
ATOM   4448  CG   ASP B 264      18.163 -11.340  75.419  1.00 50.02           C
ATOM   4449  OD1  ASP B 264      19.129 -12.138  75.320  1.00 50.02           O
ATOM   4450  OD2  ASP B 264      17.540 -11.133  76.476  1.00 50.02           O
ATOM   4451  C    ASP B 264      18.722  -9.543  72.170  1.00 65.81           C
ATOM   4452  O    ASP B 264      18.026  -9.423  71.169  1.00 65.81           O
ATOM   4453  N    GLN B 265      19.591  -8.626  72.579  1.00 43.16           N
ATOM   4454  CA   GLN B 265      19.780  -7.382  71.850  1.00 43.16           C
ATOM   4455  CB   GLN B 265      20.905  -6.558  72.478  1.00 31.93           C
ATOM   4456  CG   GLN B 265      20.895  -5.113  72.050  1.00 31.93           C
ATOM   4457  CD   GLN B 265      19.476  -4.587  71.867  1.00 31.93           C
ATOM   4458  OE1  GLN B 265      18.630  -4.688  72.772  1.00 31.93           O
ATOM   4459  NE2  GLN B 265      19.205  -4.025  70.697  1.00 31.93           N
ATOM   4460  C    GLN B 265      20.121  -7.716  70.412  1.00 43.16           C
ATOM   4461  O    GLN B 265      19.821  -6.969  69.491  1.00 43.16           O
ATOM   4462  N    LEU B 266      20.745  -8.864  70.222  1.00 36.95           N
ATOM   4463  CA   LEU B 266      21.116  -9.288  68.894  1.00 36.95           C
ATOM   4464  CB   LEU B 266      22.410 -10.091  68.960  1.00 43.56           C
ATOM   4465  CG   LEU B 266      22.900 -10.720  67.656  1.00 43.56           C
ATOM   4466  CD1  LEU B 266      22.578  -9.828  66.452  1.00 43.56           C
ATOM   4467  CD2  LEU B 266      24.387 -10.966  67.775  1.00 43.56           C
ATOM   4468  C    LEU B 266      19.995 -10.095  68.231  1.00 36.95           C
ATOM   4469  O    LEU B 266      19.872 -10.087  67.001  1.00 36.95           O
ATOM   4470  N    ALA B 267      19.169 -10.778  69.024  1.00 52.70           N
ATOM   4471  CA   ALA B 267      18.067 -11.550  68.460  1.00 52.70           C
ATOM   4472  CB   ALA B 267      17.459 -12.499  69.520  1.00 47.57           C
ATOM   4473  C    ALA B 267      17.053 -10.529  67.999  1.00 52.70           C
ATOM   4474  O    ALA B 267      16.617 -10.554  66.852  1.00 52.70           O
ATOM   4475  N    GLU B 268      16.740  -9.599  68.894  1.00 39.75           N
ATOM   4476  CA   GLU B 268      15.793  -8.543  68.626  1.00 39.75           C
ATOM   4477  CB   GLU B 268      15.969  -7.421  69.639  1.00 43.11           C
ATOM   4478  CG   GLU B 268      14.637  -6.967  70.183  1.00 43.11           C
ATOM   4479  CD   GLU B 268      13.760  -8.125  70.591  1.00 43.11           C
ATOM   4480  OE1  GLU B 268      14.160  -8.828  71.544  1.00 43.11           O
ATOM   4481  OE2  GLU B 268      12.693  -8.310  69.957  1.00 43.11           O
ATOM   4482  C    GLU B 268      16.004  -8.022  67.222  1.00 39.75           C
ATOM   4483  O    GLU B 268      15.053  -7.949  66.437  1.00 39.75           O
ATOM   4484  N    ILE B 269      17.265  -7.739  66.899  1.00 34.19           N
ATOM   4485  CA   ILE B 269      17.633  -7.199  65.598  1.00 34.19           C
ATOM   4486  CB   ILE B 269      19.080  -6.639  65.606  1.00 25.87           C
ATOM   4487  CG2  ILE B 269      19.428  -6.054  64.251  1.00 25.87           C
ATOM   4488  CG1  ILE B 269      19.191  -5.535  66.664  1.00 25.87           C
ATOM   4489  CD1  ILE B 269      20.529  -4.834  66.703  1.00 25.87           C
ATOM   4490  C    ILE B 269      17.491  -8.253  64.513  1.00 34.19           C
ATOM   4491  O    ILE B 269      16.948  -7.980  63.440  1.00 34.19           O
ATOM   4492  N    ILE B 270      17.977  -9.455  64.801  1.00 48.74           N
ATOM   4493  CA   ILE B 270      17.902 -10.576  63.866  1.00 48.74           C
ATOM   4494  CB   ILE B 270      18.480 -11.844  64.502  1.00 40.74           C
ATOM   4495  CG2  ILE B 270      17.622 -13.030  64.140  1.00 40.74           C
ATOM   4496  CG1  ILE B 270      19.934 -12.029  64.069  1.00 40.74           C
ATOM   4497  CD1  ILE B 270      20.761 -12.736  65.115  1.00 40.74           C
```

FIG. 7-76

```
ATOM   4498  C    ILE B 270      16.462 -10.884  63.433  1.00 48.74           C
ATOM   4499  O    ILE B 270      16.170 -11.014  62.242  1.00 48.74           O
ATOM   4500  N    LYS B 271      15.572 -11.009  64.413  1.00 47.88           N
ATOM   4501  CA   LYS B 271      14.178 -11.346  64.161  1.00 47.88           C
ATOM   4502  CB   LYS B 271      13.450 -11.469  65.490  1.00 53.58           C
ATOM   4503  CG   LYS B 271      13.782 -12.792  66.187  1.00 53.58           C
ATOM   4504  CD   LYS B 271      12.592 -13.333  66.966  1.00 53.58           C
ATOM   4505  CE   LYS B 271      11.784 -14.381  66.184  1.00 53.58           C
ATOM   4506  NZ   LYS B 271      10.379 -14.541  66.716  1.00 53.58           N
ATOM   4507  C    LYS B 271      13.415 -10.418  63.215  1.00 47.88           C
ATOM   4508  O    LYS B 271      12.280 -10.724  62.803  1.00 47.88           O
ATOM   4509  N    VAL B 272      14.062  -9.318  62.843  1.00 51.66           N
ATOM   4510  CA   VAL B 272      13.485  -8.309  61.964  1.00 51.66           C
ATOM   4511  CB   VAL B 272      13.346  -6.942  62.663  1.00 56.86           C
ATOM   4512  CG1  VAL B 272      14.462  -6.760  63.653  1.00 56.86           C
ATOM   4513  CG2  VAL B 272      13.397  -5.812  61.613  1.00 56.86           C
ATOM   4514  C    VAL B 272      14.414  -8.124  60.806  1.00 51.66           C
ATOM   4515  O    VAL B 272      14.030  -8.344  59.671  1.00 51.66           O
ATOM   4516  N    LEU B 273      15.637  -7.703  61.108  1.00 38.93           N
ATOM   4517  CA   LEU B 273      16.629  -7.480  60.076  1.00 38.93           C
ATOM   4518  CB   LEU B 273      17.814  -6.666  60.610  1.00 37.69           C
ATOM   4519  CG   LEU B 273      17.609  -5.169  60.484  1.00 37.69           C
ATOM   4520  CD1  LEU B 273      18.897  -4.457  60.768  1.00 37.69           C
ATOM   4521  CD2  LEU B 273      17.140  -4.880  59.063  1.00 37.69           C
ATOM   4522  C    LEU B 273      17.129  -8.754  59.423  1.00 38.93           C
ATOM   4523  O    LEU B 273      17.693  -8.691  58.332  1.00 38.93           O
ATOM   4524  N    GLY B 274      16.890  -9.904  60.056  1.00 49.33           N
ATOM   4525  CA   GLY B 274      17.325 -11.168  59.494  1.00 49.33           C
ATOM   4526  C    GLY B 274      18.703 -11.525  59.992  1.00 49.33           C
ATOM   4527  O    GLY B 274      19.216 -10.926  60.933  1.00 49.33           O
ATOM   4528  N    THR B 275      19.306 -12.503  59.338  1.00 45.74           N
ATOM   4529  CA   THR B 275      20.630 -12.979  59.694  1.00 45.74           C
ATOM   4530  CB   THR B 275      20.693 -14.500  59.526  1.00 55.99           C
ATOM   4531  OG1  THR B 275      20.102 -15.102  60.681  1.00 55.99           O
ATOM   4532  CG2  THR B 275      22.131 -14.990  59.346  1.00 55.99           C
ATOM   4533  C    THR B 275      21.813 -12.336  58.961  1.00 45.74           C
ATOM   4534  O    THR B 275      21.940 -12.416  57.732  1.00 45.74           O
ATOM   4535  N    PRO B 276      22.712 -11.708  59.733  1.00 49.46           N
ATOM   4536  CD   PRO B 276      22.662 -11.710  61.208  1.00 49.54           C
ATOM   4537  CA   PRO B 276      23.917 -11.031  59.249  1.00 49.46           C
ATOM   4538  CB   PRO B 276      24.696 -10.761  60.534  1.00 49.54           C
ATOM   4539  CG   PRO B 276      23.621 -10.614  61.566  1.00 49.54           C
ATOM   4540  C    PRO B 276      24.693 -11.945  58.305  1.00 49.46           C
ATOM   4541  O    PRO B 276      24.932 -13.105  58.625  1.00 49.46           O
ATOM   4542  N    THR B 277      25.089 -11.432  57.148  1.00 54.80           N
ATOM   4543  CA   THR B 277      25.840 -12.246  56.198  1.00 54.80           C
ATOM   4544  CB   THR B 277      25.739 -11.692  54.781  1.00 47.56           C
ATOM   4545  OG1  THR B 277      26.717 -10.658  54.613  1.00 47.56           O
ATOM   4546  CG2  THR B 277      24.343 -11.124  54.524  1.00 47.56           C
ATOM   4547  C    THR B 277      27.317 -12.243  56.582  1.00 54.80           C
ATOM   4548  O    THR B 277      27.747 -11.418  57.396  1.00 54.80           O
ATOM   4549  N    ARG B 278      28.092 -13.156  55.997  1.00 75.77           N
ATOM   4550  CA   ARG B 278      29.522 -13.231  56.290  1.00 75.77           C
ATOM   4551  CB   ARG B 278      30.231 -14.235  55.366  1.00 92.31           C
ATOM   4552  CG   ARG B 278      31.579 -14.724  55.921  1.00 92.31           C
ATOM   4553  CD   ARG B 278      32.709 -14.846  54.887  1.00 92.31           C
ATOM   4554  NE   ARG B 278      32.523 -15.929  53.922  1.00 92.31           N
ATOM   4555  CZ   ARG B 278      33.523 -16.639  53.396  1.00 92.31           C
ATOM   4556  NH1  ARG B 278      34.783 -16.389  53.747  1.00 92.31           N
ATOM   4557  NH2  ARG B 278      33.269 -17.590  52.505  1.00 92.31           N
```

FIG. 7-77

```
ATOM   4558  C    ARG B 278      30.113 -11.841  56.066  1.00 75.77           C
ATOM   4559  O    ARG B 278      30.599 -11.200  57.002  1.00 75.77           O
ATOM   4560  N    GLU B 279      30.054 -11.387  54.816  1.00 73.27           N
ATOM   4561  CA   GLU B 279      30.560 -10.077  54.434  1.00 73.27           C
ATOM   4562  CB   GLU B 279      30.123  -9.750  53.000  1.00101.71           C
ATOM   4563  CG   GLU B 279      30.504  -8.354  52.508  1.00101.71           C
ATOM   4564  CD   GLU B 279      30.276  -8.170  51.011  1.00101.71           C
ATOM   4565  OE1  GLU B 279      30.193  -7.006  50.555  1.00101.71           O
ATOM   4566  OE2  GLU B 279      30.192  -9.187  50.287  1.00101.71           O
ATOM   4567  C    GLU B 279      30.050  -9.013  55.403  1.00 73.27           C
ATOM   4568  O    GLU B 279      30.816  -8.159  55.857  1.00 73.27           O
ATOM   4569  N    GLN B 280      28.762  -9.065  55.730  1.00 71.30           N
ATOM   4570  CA   GLN B 280      28.201  -8.090  56.649  1.00 71.30           C
ATOM   4571  CB   GLN B 280      26.717  -8.350  56.883  1.00 41.61           C
ATOM   4572  CG   GLN B 280      25.858  -7.930  55.699  1.00 41.61           C
ATOM   4573  CD   GLN B 280      24.360  -7.982  55.977  1.00 41.61           C
ATOM   4574  OE1  GLN B 280      23.896  -8.762  56.815  1.00 41.61           O
ATOM   4575  NE2  GLN B 280      23.592  -7.160  55.254  1.00 41.61           N
ATOM   4576  C    GLN B 280      28.961  -8.153  57.950  1.00 71.30           C
ATOM   4577  O    GLN B 280      29.280  -7.122  58.528  1.00 71.30           O
ATOM   4578  N    ILE B 281      29.261  -9.359  58.412  1.00 51.52           N
ATOM   4579  CA   ILE B 281      30.019  -9.489  59.643  1.00 51.52           C
ATOM   4580  CB   ILE B 281      29.964 -10.937  60.171  1.00 47.30           C
ATOM   4581  CG2  ILE B 281      30.971 -11.134  61.317  1.00 47.30           C
ATOM   4582  CG1  ILE B 281      28.533 -11.236  60.626  1.00 47.30           C
ATOM   4583  CD1  ILE B 281      28.380 -12.510  61.426  1.00 47.30           C
ATOM   4584  C    ILE B 281      31.477  -9.040  59.437  1.00 51.52           C
ATOM   4585  O    ILE B 281      32.139  -8.597  60.374  1.00 51.52           O
ATOM   4586  N    ALA B 282      31.974  -9.139  58.211  1.00 56.64           N
ATOM   4587  CA   ALA B 282      33.339  -8.711  57.941  1.00 56.64           C
ATOM   4588  CB   ALA B 282      33.793  -9.216  56.569  1.00 49.86           C
ATOM   4589  C    ALA B 282      33.416  -7.180  57.994  1.00 56.64           C
ATOM   4590  O    ALA B 282      34.488  -6.606  58.228  1.00 56.64           O
ATOM   4591  N    GLU B 283      32.280  -6.518  57.788  1.00 48.02           N
ATOM   4592  CA   GLU B 283      32.254  -5.059  57.801  1.00 48.02           C
ATOM   4593  CB   GLU B 283      31.364  -4.549  56.674  1.00 63.40           C
ATOM   4594  CG   GLU B 283      31.933  -4.870  55.310  1.00 63.40           C
ATOM   4595  CD   GLU B 283      31.112  -4.301  54.176  1.00 63.40           C
ATOM   4596  OE1  GLU B 283      29.914  -4.649  54.081  1.00 63.40           O
ATOM   4597  OE2  GLU B 283      31.670  -3.510  53.380  1.00 63.40           O
ATOM   4598  C    GLU B 283      31.838  -4.426  59.125  1.00 48.02           C
ATOM   4599  O    GLU B 283      32.027  -3.226  59.326  1.00 48.02           O
ATOM   4600  N    MET B 284      31.257  -5.222  60.016  1.00 52.12           N
ATOM   4601  CA   MET B 284      30.863  -4.732  61.333  1.00 52.12           C
ATOM   4602  CB   MET B 284      29.731  -5.592  61.905  1.00 50.31           C
ATOM   4603  CG   MET B 284      28.364  -5.318  61.314  1.00 50.31           C
ATOM   4604  SD   MET B 284      27.179  -6.584  61.740  1.00 50.31           S
ATOM   4605  CE   MET B 284      27.188  -6.471  63.513  1.00 50.31           C
ATOM   4606  C    MET B 284      32.118  -4.875  62.202  1.00 52.12           C
ATOM   4607  O    MET B 284      32.552  -3.929  62.867  1.00 52.12           O
ATOM   4608  N    ASN B 285      32.685  -6.079  62.179  1.00 67.72           N
ATOM   4609  CA   ASN B 285      33.902  -6.413  62.909  1.00 67.72           C
ATOM   4610  CB   ASN B 285      33.566  -7.021  64.272  1.00 50.00           C
ATOM   4611  CG   ASN B 285      34.804  -7.419  65.043  1.00 50.00           C
ATOM   4612  OD1  ASN B 285      35.909  -7.023  64.689  1.00 50.00           O
ATOM   4613  ND2  ASN B 285      34.629  -8.195  66.104  1.00 50.00           N
ATOM   4614  C    ASN B 285      34.676  -7.420  62.054  1.00 67.72           C
ATOM   4615  O    ASN B 285      34.346  -8.605  62.022  1.00 67.72           O
ATOM   4616  N    PRO B 286      35.718  -6.953  61.345  1.00 87.67           N
ATOM   4617  CD   PRO B 286      36.261  -5.583  61.399  1.00 57.11           C
```

FIG. 7-78

```
ATOM   4618  CA   PRO B 286      36.542  -7.805  60.479  1.00 87.67           C
ATOM   4619  CB   PRO B 286      37.607  -6.836  59.959  1.00 57.11           C
ATOM   4620  CG   PRO B 286      37.703  -5.806  61.052  1.00 57.11           C
ATOM   4621  C    PRO B 286      37.147  -9.042  61.140  1.00 87.67           C
ATOM   4622  O    PRO B 286      37.824  -9.832  60.476  1.00 87.67           O
ATOM   4623  N    ASN B 287      36.872  -9.221  62.432  1.00 63.45           N
ATOM   4624  CA   ASN B 287      37.414 -10.341  63.201  1.00 63.45           C
ATOM   4625  CB   ASN B 287      38.603  -9.851  64.030  1.00 65.66           C
ATOM   4626  CG   ASN B 287      38.604  -8.335  64.212  1.00 65.66           C
ATOM   4627  OD1  ASN B 287      38.698  -7.582  63.241  1.00 65.66           O
ATOM   4628  ND2  ASN B 287      38.500  -7.885  65.454  1.00 65.66           N
ATOM   4629  C    ASN B 287      36.377 -10.972  64.114  1.00 63.45           C
ATOM   4630  O    ASN B 287      35.430 -11.591  63.648  1.00 63.45           O
ATOM   4631  N    ALA B 294      20.909 -19.334  63.293  1.00 71.46           N
ATOM   4632  CA   ALA B 294      21.429 -19.855  62.029  1.00 71.46           C
ATOM   4633  CB   ALA B 294      21.115 -21.350  61.898  1.00 40.27           C
ATOM   4634  C    ALA B 294      20.871 -19.108  60.824  1.00 71.46           C
ATOM   4635  O    ALA B 294      21.330 -18.020  60.511  1.00 71.46           O
ATOM   4636  N    ALA B 295      19.894 -19.697  60.141  1.00 74.97           N
ATOM   4637  CA   ALA B 295      19.302 -19.064  58.966  1.00 74.97           C
ATOM   4638  CB   ALA B 295      19.022 -20.103  57.893  1.00 56.78           C
ATOM   4639  C    ALA B 295      18.019 -18.346  59.343  1.00 74.97           C
ATOM   4640  O    ALA B 295      17.062 -18.967  59.805  1.00 74.97           O
ATOM   4641  N    ALA B 296      17.995 -17.037  59.137  1.00 58.20           N
ATOM   4642  CA   ALA B 296      16.818 -16.236  59.475  1.00 58.20           C
ATOM   4643  CB   ALA B 296      17.071 -15.434  60.726  1.00 29.15           C
ATOM   4644  C    ALA B 296      16.505 -15.282  58.334  1.00 58.20           C
ATOM   4645  O    ALA B 296      17.365 -14.458  57.987  1.00 58.20           O
ATOM   4646  N    ALA B 297      15.302 -15.370  57.756  1.00 55.77           N
ATOM   4647  CA   ALA B 297      14.970 -14.474  56.654  1.00 55.77           C
ATOM   4648  CB   ALA B 297      13.815 -15.033  55.813  1.00 47.98           C
ATOM   4649  C    ALA B 297      14.620 -13.155  57.297  1.00 55.77           C
ATOM   4650  O    ALA B 297      14.169 -13.127  58.435  1.00 55.77           O
ATOM   4651  N    ALA B 298      14.934 -12.069  56.598  1.00 59.68           N
ATOM   4652  CA   ALA B 298      14.670 -10.731  57.110  1.00 59.68           C
ATOM   4653  CB   ALA B 298      15.223  -9.692  56.154  1.00 30.06           C
ATOM   4654  C    ALA B 298      13.164 -10.575  57.235  1.00 59.68           C
ATOM   4655  O    ALA B 298      12.413 -11.341  56.650  1.00 59.68           O
ATOM   4656  N    HIS B 299      12.712  -9.613  58.020  1.00 60.83           N
ATOM   4657  CA   HIS B 299      11.283  -9.395  58.155  1.00 60.83           C
ATOM   4658  CB   HIS B 299      10.868  -9.371  59.620  1.00 44.31           C
ATOM   4659  CG   HIS B 299       9.392  -9.482  59.825  1.00 44.31           C
ATOM   4660  CD2  HIS B 299       8.436  -8.532  59.964  1.00 44.31           C
ATOM   4661  ND1  HIS B 299       8.741 -10.696  59.901  1.00 44.31           N
ATOM   4662  CE1  HIS B 299       7.450 -10.489  60.084  1.00 44.31           C
ATOM   4663  NE2  HIS B 299       7.238  -9.184  60.126  1.00 44.31           N
ATOM   4664  C    HIS B 299      10.962  -8.049  57.515  1.00 60.83           C
ATOM   4665  O    HIS B 299      11.469  -7.013  57.940  1.00 60.83           O
ATOM   4666  N    PRO B 300      10.108  -8.049  56.484  1.00 59.29           N
ATOM   4667  CD   PRO B 300       9.324  -9.214  56.042  1.00 65.44           C
ATOM   4668  CA   PRO B 300       9.700  -6.839  55.759  1.00 59.29           C
ATOM   4669  CB   PRO B 300       8.463  -7.299  54.997  1.00 65.44           C
ATOM   4670  CG   PRO B 300       8.772  -8.739  54.726  1.00 65.44           C
ATOM   4671  C    PRO B 300       9.419  -5.640  56.667  1.00 59.29           C
ATOM   4672  O    PRO B 300       8.617  -5.716  57.598  1.00 59.29           O
ATOM   4673  N    TRP B 301      10.085  -4.530  56.377  1.00 41.97           N
ATOM   4674  CA   TRP B 301       9.929  -3.318  57.163  1.00 41.97           C
ATOM   4675  CB   TRP B 301      10.804  -2.200  56.568  1.00 30.44           C
ATOM   4676  CG   TRP B 301      12.245  -2.274  57.022  1.00 30.44           C
ATOM   4677  CD2  TRP B 301      12.713  -2.200  58.379  1.00 30.44           C
```

FIG. 7-79

```
ATOM   4678  CE2 TRP B 301      14.131  -2.309  58.330  1.00 30.44           C
ATOM   4679  CE3 TRP B 301      12.086  -1.962  59.610  1.00 30.44           C
ATOM   4680  CD1 TRP B 301      13.352  -2.482  56.243  1.00 30.44           C
ATOM   4681  NE1 TRP B 301      14.487  -2.517  57.031  1.00 30.44           N
ATOM   4682  CZ2 TRP B 301      14.914  -2.303  59.494  1.00 30.44           C
ATOM   4683  CZ3 TRP B 301      12.874  -1.947  60.770  1.00 30.44           C
ATOM   4684  CH2 TRP B 301      14.278  -2.074  60.694  1.00 30.44           C
ATOM   4685  C   TRP B 301       8.484  -2.859  57.278  1.00 41.97           C
ATOM   4686  O   TRP B 301       8.061  -2.341  58.321  1.00 41.97           O
ATOM   4687  N   THR B 302       7.728  -3.058  56.209  1.00 39.00           N
ATOM   4688  CA  THR B 302       6.340  -2.638  56.185  1.00 39.00           C
ATOM   4689  CB  THR B 302       5.739  -2.826  54.796  1.00 43.08           C
ATOM   4690  OG1 THR B 302       6.788  -2.847  53.818  1.00 43.08           O
ATOM   4691  CG2 THR B 302       4.822  -1.675  54.482  1.00 43.08           C
ATOM   4692  C   THR B 302       5.495  -3.396  57.200  1.00 39.00           C
ATOM   4693  O   THR B 302       4.589  -2.823  57.815  1.00 39.00           O
ATOM   4694  N   ALA B 303       5.812  -4.674  57.386  1.00 39.92           N
ATOM   4695  CA  ALA B 303       5.083  -5.524  58.318  1.00 39.92           C
ATOM   4696  CB  ALA B 303       5.305  -6.993  57.973  1.00 61.07           C
ATOM   4697  C   ALA B 303       5.518  -5.254  59.749  1.00 39.92           C
ATOM   4698  O   ALA B 303       4.850  -5.666  60.702  1.00 39.92           O
ATOM   4699  N   VAL B 304       6.639  -4.556  59.898  1.00 37.90           N
ATOM   4700  CA  VAL B 304       7.157  -4.228  61.221  1.00 37.90           C
ATOM   4701  CB  VAL B 304       8.624  -3.793  61.157  1.00 43.52           C
ATOM   4702  CG1 VAL B 304       9.154  -3.573  62.562  1.00 43.52           C
ATOM   4703  CG2 VAL B 304       9.447  -4.837  60.422  1.00 43.52           C
ATOM   4704  C   VAL B 304       6.367  -3.103  61.861  1.00 37.90           C
ATOM   4705  O   VAL B 304       6.155  -3.101  63.068  1.00 37.90           O
ATOM   4706  N   PHE B 305       5.921  -2.151  61.048  1.00 39.18           N
ATOM   4707  CA  PHE B 305       5.171  -1.009  61.567  1.00 39.18           C
ATOM   4708  CB  PHE B 305       5.679   0.284  60.932  1.00 28.88           C
ATOM   4709  CG  PHE B 305       7.115   0.565  61.223  1.00 28.88           C
ATOM   4710  CD1 PHE B 305       7.492   1.110  62.436  1.00 28.88           C
ATOM   4711  CD2 PHE B 305       8.099   0.264  60.287  1.00 28.88           C
ATOM   4712  CE1 PHE B 305       8.833   1.354  62.720  1.00 28.88           C
ATOM   4713  CE2 PHE B 305       9.450   0.504  60.565  1.00 28.88           C
ATOM   4714  CZ  PHE B 305       9.814   1.047  61.778  1.00 28.88           C
ATOM   4715  C   PHE B 305       3.680  -1.118  61.347  1.00 39.18           C
ATOM   4716  O   PHE B 305       3.213  -1.982  60.613  1.00 39.18           O
ATOM   4717  N   ARG B 306       2.939  -0.218  61.980  1.00 58.92           N
ATOM   4718  CA  ARG B 306       1.494  -0.228  61.866  1.00 58.92           C
ATOM   4719  CB  ARG B 306       0.898   0.738  62.893  1.00 95.92           C
ATOM   4720  CG  ARG B 306       1.400   0.406  64.308  1.00 95.92           C
ATOM   4721  CD  ARG B 306       0.650   1.099  65.439  1.00 95.92           C
ATOM   4722  NE  ARG B 306       0.912   2.532  65.519  1.00 95.92           N
ATOM   4723  CZ  ARG B 306       0.410   3.436  64.681  1.00 95.92           C
ATOM   4724  NH1 ARG B 306      -0.390   3.068  63.685  1.00 95.92           N
ATOM   4725  NH2 ARG B 306       0.703   4.717  64.845  1.00 95.92           N
ATOM   4726  C   ARG B 306       1.088   0.100  60.432  1.00 58.92           C
ATOM   4727  O   ARG B 306       1.700   0.946  59.784  1.00 58.92           O
ATOM   4728  N   PRO B 307       0.054  -0.591  59.920  1.00 61.29           N
ATOM   4729  CD  PRO B 307      -0.888  -1.272  60.821  1.00 63.64           C
ATOM   4730  CA  PRO B 307      -0.529  -0.489  58.575  1.00 61.29           C
ATOM   4731  CB  PRO B 307      -1.871  -1.203  58.729  1.00 63.64           C
ATOM   4732  CG  PRO B 307      -2.203  -0.974  60.160  1.00 63.64           C
ATOM   4733  C   PRO B 307      -0.675   0.910  57.981  1.00 61.29           C
ATOM   4734  O   PRO B 307      -0.634   1.080  56.756  1.00 61.29           O
ATOM   4735  N   ALA B 308      -0.840   1.911  58.838  1.00 54.69           N
ATOM   4736  CA  ALA B 308      -0.999   3.277  58.360  1.00 54.69           C
ATOM   4737  CB  ALA B 308      -1.804   4.082  59.369  1.00 42.92           C
```

FIG. 7-80

| | | | | | | | | | |
|---|---|---|---|---|---|---|---|---|---|
| ATOM | 4738 | C | ALA | B | 308 | 0.347 | 3.960 | 58.085 | 1.00 54.69 | C |
| ATOM | 4739 | O | ALA | B | 308 | 0.450 | 4.782 | 57.174 | 1.00 54.69 | O |
| ATOM | 4740 | N | THR | B | 309 | 1.364 | 3.612 | 58.877 | 1.00 50.38 | N |
| ATOM | 4741 | CA | THR | B | 309 | 2.721 | 4.168 | 58.775 | 1.00 50.38 | C |
| ATOM | 4742 | CB | THR | B | 309 | 3.768 | 3.134 | 59.245 | 1.00 62.72 | C |
| ATOM | 4743 | OG1 | THR | B | 309 | 3.401 | 2.640 | 60.540 | 1.00 62.72 | O |
| ATOM | 4744 | CG2 | THR | B | 309 | 5.149 | 3.766 | 59.330 | 1.00 62.72 | C |
| ATOM | 4745 | C | THR | B | 309 | 3.128 | 4.662 | 57.381 | 1.00 50.38 | C |
| ATOM | 4746 | O | THR | B | 309 | 3.129 | 3.897 | 56.407 | 1.00 50.38 | O |
| ATOM | 4747 | N | PRO | B | 310 | 3.505 | 5.951 | 57.281 | 1.00 27.06 | N |
| ATOM | 4748 | CD | PRO | B | 310 | 3.597 | 6.926 | 58.380 | 1.00 25.15 | C |
| ATOM | 4749 | CA | PRO | B | 310 | 3.915 | 6.570 | 56.020 | 1.00 27.06 | C |
| ATOM | 4750 | CB | PRO | B | 310 | 4.264 | 8.007 | 56.426 | 1.00 25.15 | C |
| ATOM | 4751 | CG | PRO | B | 310 | 3.435 | 8.245 | 57.641 | 1.00 25.15 | C |
| ATOM | 4752 | C | PRO | B | 310 | 5.092 | 5.850 | 55.376 | 1.00 27.06 | C |
| ATOM | 4753 | O | PRO | B | 310 | 6.120 | 5.598 | 56.012 | 1.00 27.06 | O |
| ATOM | 4754 | N | PRO | B | 311 | 4.947 | 5.499 | 54.098 | 1.00 32.68 | N |
| ATOM | 4755 | CD | PRO | B | 311 | 3.720 | 5.653 | 53.300 | 1.00 20.54 | C |
| ATOM | 4756 | CA | PRO | B | 311 | 5.977 | 4.805 | 53.329 | 1.00 32.68 | C |
| ATOM | 4757 | CB | PRO | B | 311 | 5.418 | 4.856 | 51.916 | 1.00 20.54 | C |
| ATOM | 4758 | CG | PRO | B | 311 | 3.962 | 4.690 | 52.170 | 1.00 20.54 | C |
| ATOM | 4759 | C | PRO | B | 311 | 7.363 | 5.445 | 53.434 | 1.00 32.68 | C |
| ATOM | 4760 | O | PRO | B | 311 | 8.367 | 4.747 | 53.595 | 1.00 32.68 | O |
| ATOM | 4761 | N | GLU | B | 312 | 7.413 | 6.771 | 53.347 | 1.00 32.51 | N |
| ATOM | 4762 | CA | GLU | B | 312 | 8.686 | 7.490 | 53.426 | 1.00 32.51 | C |
| ATOM | 4763 | CB | GLU | B | 312 | 8.472 | 8.993 | 53.192 | 1.00 61.45 | C |
| ATOM | 4764 | CG | GLU | B | 312 | 7.635 | 9.354 | 51.968 | 1.00 61.45 | C |
| ATOM | 4765 | CD | GLU | B | 312 | 6.148 | 9.322 | 52.253 | 1.00 61.45 | C |
| ATOM | 4766 | OE1 | GLU | B | 312 | 5.380 | 9.817 | 51.400 | 1.00 61.45 | O |
| ATOM | 4767 | OE2 | GLU | B | 312 | 5.748 | 8.807 | 53.322 | 1.00 61.45 | O |
| ATOM | 4768 | C | GLU | B | 312 | 9.385 | 7.273 | 54.777 | 1.00 32.51 | C |
| ATOM | 4769 | O | GLU | B | 312 | 10.615 | 7.203 | 54.863 | 1.00 32.51 | O |
| ATOM | 4770 | N | ALA | B | 313 | 8.588 | 7.169 | 55.833 | 1.00 40.51 | N |
| ATOM | 4771 | CA | ALA | B | 313 | 9.119 | 6.944 | 57.168 | 1.00 40.51 | C |
| ATOM | 4772 | CB | ALA | B | 313 | 7.995 | 6.962 | 58.159 | 1.00 19.43 | C |
| ATOM | 4773 | C | ALA | B | 313 | 9.818 | 5.591 | 57.182 | 1.00 40.51 | C |
| ATOM | 4774 | O | ALA | B | 313 | 10.972 | 5.474 | 57.587 | 1.00 40.51 | O |
| ATOM | 4775 | N | ILE | B | 314 | 9.102 | 4.571 | 56.729 | 1.00 38.19 | N |
| ATOM | 4776 | CA | ILE | B | 314 | 9.638 | 3.219 | 56.652 | 1.00 38.19 | C |
| ATOM | 4777 | CB | ILE | B | 314 | 8.606 | 2.281 | 56.024 | 1.00 39.09 | C |
| ATOM | 4778 | CG2 | ILE | B | 314 | 9.062 | 0.845 | 56.154 | 1.00 39.09 | C |
| ATOM | 4779 | CG1 | ILE | B | 314 | 7.264 | 2.463 | 56.734 | 1.00 39.09 | C |
| ATOM | 4780 | CD1 | ILE | B | 314 | 6.112 | 1.785 | 56.049 | 1.00 39.09 | C |
| ATOM | 4781 | C | ILE | B | 314 | 10.909 | 3.205 | 55.801 | 1.00 38.19 | C |
| ATOM | 4782 | O | ILE | B | 314 | 11.924 | 2.626 | 56.178 | 1.00 38.19 | O |
| ATOM | 4783 | N | ALA | B | 315 | 10.845 | 3.864 | 54.650 | 1.00 27.52 | N |
| ATOM | 4784 | CA | ALA | B | 315 | 11.983 | 3.931 | 53.747 | 1.00 27.52 | C |
| ATOM | 4785 | CB | ALA | B | 315 | 11.623 | 4.758 | 52.535 | 1.00 39.25 | C |
| ATOM | 4786 | C | ALA | B | 315 | 13.228 | 4.503 | 54.418 | 1.00 27.52 | C |
| ATOM | 4787 | O | ALA | B | 315 | 14.290 | 3.893 | 54.363 | 1.00 27.52 | O |
| ATOM | 4788 | N | LEU | B | 316 | 13.100 | 5.670 | 55.049 | 1.00 26.07 | N |
| ATOM | 4789 | CA | LEU | B | 316 | 14.243 | 6.299 | 55.702 | 1.00 26.07 | C |
| ATOM | 4790 | CB | LEU | B | 316 | 13.820 | 7.562 | 56.453 | 1.00 23.58 | C |
| ATOM | 4791 | CG | LEU | B | 316 | 14.885 | 8.157 | 57.377 | 1.00 23.58 | C |
| ATOM | 4792 | CD1 | LEU | B | 316 | 16.100 | 8.596 | 56.586 | 1.00 23.58 | C |
| ATOM | 4793 | CD2 | LEU | B | 316 | 14.281 | 9.325 | 58.143 | 1.00 23.58 | C |
| ATOM | 4794 | C | LEU | B | 316 | 14.822 | 5.310 | 56.672 | 1.00 26.07 | C |
| ATOM | 4795 | O | LEU | B | 316 | 16.008 | 5.001 | 56.642 | 1.00 26.07 | O |
| ATOM | 4796 | N | CYS | B | 317 | 13.952 | 4.800 | 57.527 | 1.00 34.50 | N |
| ATOM | 4797 | CA | CYS | B | 317 | 14.334 | 3.827 | 58.531 | 1.00 34.50 | C |

FIG. 7-81

| ATOM | 4798 | CB  | CYS B 317 | 13.067 |  3.270 | 59.161 | 1.00 | 45.62 | C |
|------|------|-----|-----------|--------|--------|--------|------|-------|---|
| ATOM | 4799 | SG  | CYS B 317 | 13.346 |  2.371 | 60.641 | 1.00 | 45.62 | S |
| ATOM | 4800 | C   | CYS B 317 | 15.189 |  2.690 | 57.949 | 1.00 | 34.50 | C |
| ATOM | 4801 | O   | CYS B 317 | 16.157 |  2.255 | 58.565 | 1.00 | 34.50 | O |
| ATOM | 4802 | N   | SER B 318 | 14.825 |  2.222 | 56.758 | 1.00 | 28.95 | N |
| ATOM | 4803 | CA  | SER B 318 | 15.540 |  1.144 | 56.099 | 1.00 | 28.95 | C |
| ATOM | 4804 | CB  | SER B 318 | 14.854 |  0.801 | 54.782 | 1.00 | 29.18 | C |
| ATOM | 4805 | OG  | SER B 318 | 15.387 |  1.588 | 53.733 | 1.00 | 29.18 | O |
| ATOM | 4806 | C   | SER B 318 | 17.001 |  1.531 | 55.819 | 1.00 | 28.95 | C |
| ATOM | 4807 | O   | SER B 318 | 17.900 |  0.681 | 55.850 | 1.00 | 28.95 | O |
| ATOM | 4808 | N   | ARG B 319 | 17.238 |  2.814 | 55.549 | 1.00 | 32.46 | N |
| ATOM | 4809 | CA  | ARG B 319 | 18.588 |  3.297 | 55.239 | 1.00 | 32.46 | C |
| ATOM | 4810 | CB  | ARG B 319 | 18.522 |  4.529 | 54.341 | 1.00 | 47.50 | C |
| ATOM | 4811 | CG  | ARG B 319 | 17.559 |  4.421 | 53.162 | 1.00 | 47.50 | C |
| ATOM | 4812 | CD  | ARG B 319 | 17.981 |  3.389 | 52.114 | 1.00 | 47.50 | C |
| ATOM | 4813 | NE  | ARG B 319 | 19.270 |  3.673 | 51.478 | 1.00 | 47.50 | N |
| ATOM | 4814 | CZ  | ARG B 319 | 20.427 |  3.186 | 51.911 | 1.00 | 47.50 | C |
| ATOM | 4815 | NH1 | ARG B 319 | 20.446 |  2.397 | 52.974 | 1.00 | 47.50 | N |
| ATOM | 4816 | NH2 | ARG B 319 | 21.561 |  3.473 | 51.281 | 1.00 | 47.50 | N |
| ATOM | 4817 | C   | ARG B 319 | 19.396 |  3.646 | 56.487 | 1.00 | 32.46 | C |
| ATOM | 4818 | O   | ARG B 319 | 20.549 |  4.081 | 56.392 | 1.00 | 32.46 | O |
| ATOM | 4819 | N   | LEU B 320 | 18.782 |  3.457 | 57.653 | 1.00 | 30.92 | N |
| ATOM | 4820 | CA  | LEU B 320 | 19.429 |  3.740 | 58.930 | 1.00 | 30.92 | C |
| ATOM | 4821 | CB  | LEU B 320 | 18.514 |  4.630 | 59.772 | 1.00 | 25.28 | C |
| ATOM | 4822 | CG  | LEU B 320 | 18.288 |  6.016 | 59.165 | 1.00 | 25.28 | C |
| ATOM | 4823 | CD1 | LEU B 320 | 17.181 |  6.719 | 59.901 | 1.00 | 25.28 | C |
| ATOM | 4824 | CD2 | LEU B 320 | 19.554 |  6.838 | 59.247 | 1.00 | 25.28 | C |
| ATOM | 4825 | C   | LEU B 320 | 19.765 |  2.448 | 59.689 | 1.00 | 30.92 | C |
| ATOM | 4826 | O   | LEU B 320 | 20.856 |  2.280 | 60.233 | 1.00 | 30.92 | O |
| ATOM | 4827 | N   | LEU B 321 | 18.818 |  1.528 | 59.718 | 1.00 | 39.82 | N |
| ATOM | 4828 | CA  | LEU B 321 | 19.046 |  0.283 | 60.412 | 1.00 | 39.82 | C |
| ATOM | 4829 | CB  | LEU B 321 | 17.742 | -0.207 | 61.027 | 1.00 | 29.49 | C |
| ATOM | 4830 | CG  | LEU B 321 | 17.120 |  0.772 | 62.022 | 1.00 | 29.49 | C |
| ATOM | 4831 | CD1 | LEU B 321 | 15.921 |  0.112 | 62.673 | 1.00 | 29.49 | C |
| ATOM | 4832 | CD2 | LEU B 321 | 18.150 |  1.193 | 63.075 | 1.00 | 29.49 | C |
| ATOM | 4833 | C   | LEU B 321 | 19.612 | -0.751 | 59.454 | 1.00 | 39.82 | C |
| ATOM | 4834 | O   | LEU B 321 | 18.872 | -1.493 | 58.808 | 1.00 | 39.82 | O |
| ATOM | 4835 | N   | GLU B 322 | 20.935 | -0.786 | 59.360 | 1.00 | 34.98 | N |
| ATOM | 4836 | CA  | GLU B 322 | 21.607 | -1.723 | 58.481 | 1.00 | 34.98 | C |
| ATOM | 4837 | CB  | GLU B 322 | 22.047 | -1.020 | 57.202 | 1.00 | 42.89 | C |
| ATOM | 4838 | CG  | GLU B 322 | 20.965 | -0.222 | 56.529 | 1.00 | 42.89 | C |
| ATOM | 4839 | CD  | GLU B 322 | 21.267 |  0.003 | 55.065 | 1.00 | 42.89 | C |
| ATOM | 4840 | OE1 | GLU B 322 | 21.043 | -0.920 | 54.261 | 1.00 | 42.89 | O |
| ATOM | 4841 | OE2 | GLU B 322 | 21.749 |  1.093 | 54.709 | 1.00 | 42.89 | O |
| ATOM | 4842 | C   | GLU B 322 | 22.824 | -2.303 | 59.180 | 1.00 | 34.98 | C |
| ATOM | 4843 | O   | GLU B 322 | 23.411 | -1.659 | 60.049 | 1.00 | 34.98 | O |
| ATOM | 4844 | N   | TYR B 323 | 23.199 | -3.518 | 58.793 | 1.00 | 23.84 | N |
| ATOM | 4845 | CA  | TYR B 323 | 24.358 | -4.166 | 59.385 | 1.00 | 23.84 | C |
| ATOM | 4846 | CB  | TYR B 323 | 24.390 | -5.655 | 59.040 | 1.00 | 52.21 | C |
| ATOM | 4847 | CG  | TYR B 323 | 23.405 | -6.473 | 59.830 | 1.00 | 52.21 | C |
| ATOM | 4848 | CD1 | TYR B 323 | 23.432 | -6.465 | 61.215 | 1.00 | 52.21 | C |
| ATOM | 4849 | CE1 | TYR B 323 | 22.524 | -7.193 | 61.944 | 1.00 | 52.21 | C |
| ATOM | 4850 | CD2 | TYR B 323 | 22.432 | -7.241 | 59.190 | 1.00 | 52.21 | C |
| ATOM | 4851 | CE2 | TYR B 323 | 21.517 | -7.974 | 59.910 | 1.00 | 52.21 | C |
| ATOM | 4852 | CZ  | TYR B 323 | 21.567 | -7.946 | 61.286 | 1.00 | 52.21 | C |
| ATOM | 4853 | OH  | TYR B 323 | 20.657 | -8.683 | 61.999 | 1.00 | 52.21 | O |
| ATOM | 4854 | C   | TYR B 323 | 25.641 | -3.501 | 58.925 | 1.00 | 23.84 | C |
| ATOM | 4855 | O   | TYR B 323 | 26.473 | -3.143 | 59.749 | 1.00 | 23.84 | O |
| ATOM | 4856 | N   | THR B 324 | 25.820 | -3.339 | 57.619 | 1.00 | 43.22 | N |
| ATOM | 4857 | CA  | THR B 324 | 27.028 | -2.679 | 57.130 | 1.00 | 43.22 | C |

FIG. 7-82

| ATOM | 4858 | CB  | THR B 324 | 27.122 | -2.724 | 55.578 | 1.00 | 41.65 | C |
| --- | --- | --- | --- | --- | --- | --- | --- | --- | --- |
| ATOM | 4859 | OG1 | THR B 324 | 27.051 | -4.089 | 55.136 | 1.00 | 41.65 | O |
| ATOM | 4860 | CG2 | THR B 324 | 28.443 | -2.113 | 55.103 | 1.00 | 41.65 | C |
| ATOM | 4861 | C   | THR B 324 | 26.935 | -1.228 | 57.620 | 1.00 | 43.22 | C |
| ATOM | 4862 | O   | THR B 324 | 26.017 | -0.486 | 57.258 | 1.00 | 43.22 | O |
| ATOM | 4863 | N   | PRO B 325 | 27.884 | -0.806 | 58.464 | 1.00 | 39.69 | N |
| ATOM | 4864 | CD  | PRO B 325 | 29.012 | -1.548 | 59.045 | 1.00 | 19.04 | C |
| ATOM | 4865 | CA  | PRO B 325 | 27.840 | 0.565  | 58.977 | 1.00 | 39.69 | C |
| ATOM | 4866 | CB  | PRO B 325 | 29.048 | 0.623  | 59.904 | 1.00 | 19.04 | C |
| ATOM | 4867 | CG  | PRO B 325 | 29.201 | -0.805 | 60.345 | 1.00 | 19.04 | C |
| ATOM | 4868 | C   | PRO B 325 | 27.890 | 1.633  | 57.896 | 1.00 | 39.69 | C |
| ATOM | 4869 | O   | PRO B 325 | 27.153 | 2.622  | 57.951 | 1.00 | 39.69 | O |
| ATOM | 4870 | N   | THR B 326 | 28.762 | 1.424  | 56.913 | 1.00 | 32.90 | N |
| ATOM | 4871 | CA  | THR B 326 | 28.943 | 2.364  | 55.809 | 1.00 | 32.90 | C |
| ATOM | 4872 | CB  | THR B 326 | 30.147 | 1.951  | 54.967 | 1.00 | 35.11 | C |
| ATOM | 4873 | OG1 | THR B 326 | 29.886 | 0.677  | 54.357 | 1.00 | 35.11 | O |
| ATOM | 4874 | CG2 | THR B 326 | 31.386 | 1.849  | 55.853 | 1.00 | 35.11 | C |
| ATOM | 4875 | C   | THR B 326 | 27.724 | 2.484  | 54.889 | 1.00 | 32.90 | C |
| ATOM | 4876 | O   | THR B 326 | 27.561 | 3.466  | 54.163 | 1.00 | 32.90 | O |
| ATOM | 4877 | N   | ALA B 327 | 26.869 | 1.472  | 54.924 | 1.00 | 31.75 | N |
| ATOM | 4878 | CA  | ALA B 327 | 25.670 | 1.451  | 54.093 | 1.00 | 31.75 | C |
| ATOM | 4879 | CB  | ALA B 327 | 25.066 | 0.051  | 54.103 | 1.00 | 22.22 | C |
| ATOM | 4880 | C   | ALA B 327 | 24.640 | 2.474  | 54.559 | 1.00 | 31.75 | C |
| ATOM | 4881 | O   | ALA B 327 | 23.814 | 2.940  | 53.775 | 1.00 | 31.75 | O |
| ATOM | 4882 | N   | ARG B 328 | 24.713 | 2.815  | 55.841 | 1.00 | 18.46 | N |
| ATOM | 4883 | CA  | ARG B 328 | 23.825 | 3.779  | 56.473 | 1.00 | 18.46 | C |
| ATOM | 4884 | CB  | ARG B 328 | 24.119 | 3.868  | 57.968 | 1.00 | 38.50 | C |
| ATOM | 4885 | CG  | ARG B 328 | 23.739 | 2.645  | 58.740 | 1.00 | 38.50 | C |
| ATOM | 4886 | CD  | ARG B 328 | 24.496 | 2.547  | 60.052 | 1.00 | 38.50 | C |
| ATOM | 4887 | NE  | ARG B 328 | 24.409 | 1.189  | 60.583 | 1.00 | 38.50 | N |
| ATOM | 4888 | CZ  | ARG B 328 | 25.180 | 0.693  | 61.540 | 1.00 | 38.50 | C |
| ATOM | 4889 | NH1 | ARG B 328 | 26.126 | 1.420  | 62.115 | 1.00 | 38.50 | N |
| ATOM | 4890 | NH2 | ARG B 328 | 25.004 | -0.555 | 61.910 | 1.00 | 38.50 | N |
| ATOM | 4891 | C   | ARG B 328 | 23.955 | 5.171  | 55.892 | 1.00 | 18.46 | C |
| ATOM | 4892 | O   | ARG B 328 | 24.978 | 5.554  | 55.324 | 1.00 | 18.46 | O |
| ATOM | 4893 | N   | LEU B 329 | 22.901 | 5.947  | 56.050 | 1.00 | 28.73 | N |
| ATOM | 4894 | CA  | LEU B 329 | 22.936 | 7.297  | 55.556 | 1.00 | 28.73 | C |
| ATOM | 4895 | CB  | LEU B 329 | 21.532 | 7.901  | 55.566 | 1.00 | 28.39 | C |
| ATOM | 4896 | CG  | LEU B 329 | 20.542 | 7.178  | 54.656 | 1.00 | 28.39 | C |
| ATOM | 4897 | CD1 | LEU B 329 | 19.164 | 7.845  | 54.731 | 1.00 | 28.39 | C |
| ATOM | 4898 | CD2 | LEU B 329 | 21.083 | 7.194  | 53.242 | 1.00 | 28.39 | C |
| ATOM | 4899 | C   | LEU B 329 | 23.844 | 8.088  | 56.480 | 1.00 | 28.73 | C |
| ATOM | 4900 | O   | LEU B 329 | 24.314 | 7.580  | 57.505 | 1.00 | 28.73 | O |
| ATOM | 4901 | N   | THR B 330 | 24.109 | 9.327  | 56.086 | 1.00 | 27.92 | N |
| ATOM | 4902 | CA  | THR B 330 | 24.910 | 10.233 | 56.887 | 1.00 | 27.92 | C |
| ATOM | 4903 | CB  | THR B 330 | 25.967 | 10.985 | 56.048 | 1.00 | 35.01 | C |
| ATOM | 4904 | OG1 | THR B 330 | 25.320 | 11.961 | 55.213 | 1.00 | 35.01 | O |
| ATOM | 4905 | CG2 | THR B 330 | 26.745 | 10.020 | 55.192 | 1.00 | 35.01 | C |
| ATOM | 4906 | C   | THR B 330 | 23.902 | 11.252 | 57.413 | 1.00 | 27.92 | C |
| ATOM | 4907 | O   | THR B 330 | 22.889 | 11.537 | 56.759 | 1.00 | 27.92 | O |
| ATOM | 4908 | N   | PRO B 331 | 24.161 | 11.808 | 58.603 | 1.00 | 32.26 | N |
| ATOM | 4909 | CD  | PRO B 331 | 25.326 | 11.606 | 59.488 | 1.00 | 48.20 | C |
| ATOM | 4910 | CA  | PRO B 331 | 23.240 | 12.795 | 59.168 | 1.00 | 32.26 | C |
| ATOM | 4911 | CB  | PRO B 331 | 24.102 | 13.492 | 60.219 | 1.00 | 48.20 | C |
| ATOM | 4912 | CG  | PRO B 331 | 24.913 | 12.350 | 60.760 | 1.00 | 48.20 | C |
| ATOM | 4913 | C   | PRO B 331 | 22.680 | 13.764 | 58.122 | 1.00 | 32.26 | C |
| ATOM | 4914 | O   | PRO B 331 | 21.467 | 13.989 | 58.063 | 1.00 | 32.26 | O |
| ATOM | 4915 | N   | LEU B 332 | 23.566 | 14.332 | 57.299 | 1.00 | 31.38 | N |
| ATOM | 4916 | CA  | LEU B 332 | 23.152 | 15.281 | 56.264 | 1.00 | 31.38 | C |
| ATOM | 4917 | CB  | LEU B 332 | 24.372 | 15.849 | 55.534 | 1.00 | 44.06 | C |

FIG. 7-83

| | | | | | | | | | |
|---|---|---|---|---|---|---|---|---|---|
| ATOM | 4918 | CG | LEU | B | 332 | 24.845 | 17.232 | 56.003 | 1.00 44.06 | C |
| ATOM | 4919 | CD1 | LEU | B | 332 | 26.107 | 17.621 | 55.240 | 1.00 44.06 | C |
| ATOM | 4920 | CD2 | LEU | B | 332 | 23.741 | 18.273 | 55.797 | 1.00 44.06 | C |
| ATOM | 4921 | C | LEU | B | 332 | 22.195 | 14.669 | 55.253 | 1.00 31.38 | C |
| ATOM | 4922 | O | LEU | B | 332 | 21.186 | 15.284 | 54.900 | 1.00 31.38 | O |
| ATOM | 4923 | N | GLU | B | 333 | 22.522 | 13.461 | 54.792 | 1.00 22.08 | N |
| ATOM | 4924 | CA | GLU | B | 333 | 21.701 | 12.746 | 53.821 | 1.00 22.08 | C |
| ATOM | 4925 | CB | GLU | B | 333 | 22.407 | 11.449 | 53.432 | 1.00 42.09 | C |
| ATOM | 4926 | CG | GLU | B | 333 | 23.713 | 11.673 | 52.686 | 1.00 42.09 | C |
| ATOM | 4927 | CD | GLU | B | 333 | 24.553 | 10.402 | 52.568 | 1.00 42.09 | C |
| ATOM | 4928 | OE1 | GLU | B | 333 | 23.984 | 9.302 | 52.723 | 1.00 42.09 | O |
| ATOM | 4929 | OE2 | GLU | B | 333 | 25.779 | 10.495 | 52.313 | 1.00 42.09 | O |
| ATOM | 4930 | C | GLU | B | 333 | 20.303 | 12.458 | 54.388 | 1.00 22.08 | C |
| ATOM | 4931 | O | GLU | B | 333 | 19.282 | 12.599 | 53.697 | 1.00 22.08 | O |
| ATOM | 4932 | N | ALA | B | 334 | 20.271 | 12.065 | 55.657 | 1.00 27.55 | N |
| ATOM | 4933 | CA | ALA | B | 334 | 19.024 | 11.775 | 56.339 | 1.00 27.55 | C |
| ATOM | 4934 | CB | ALA | B | 334 | 19.304 | 11.333 | 57.758 | 1.00 33.37 | C |
| ATOM | 4935 | C | ALA | B | 334 | 18.178 | 13.036 | 56.345 | 1.00 27.55 | C |
| ATOM | 4936 | O | ALA | B | 334 | 16.965 | 12.990 | 56.162 | 1.00 27.55 | O |
| ATOM | 4937 | N | CYS | B | 335 | 18.824 | 14.172 | 56.553 | 1.00 35.72 | N |
| ATOM | 4938 | CA | CYS | B | 335 | 18.113 | 15.442 | 56.576 | 1.00 35.72 | C |
| ATOM | 4939 | CB | CYS | B | 335 | 19.058 | 16.569 | 56.992 | 1.00 27.72 | C |
| ATOM | 4940 | SG | CYS | B | 335 | 19.451 | 16.624 | 58.730 | 1.00 27.72 | S |
| ATOM | 4941 | C | CYS | B | 335 | 17.495 | 15.802 | 55.229 | 1.00 35.72 | C |
| ATOM | 4942 | O | CYS | B | 335 | 16.531 | 16.556 | 55.164 | 1.00 35.72 | O |
| ATOM | 4943 | N | ALA | B | 336 | 18.062 | 15.280 | 54.153 | 1.00 43.40 | N |
| ATOM | 4944 | CA | ALA | B | 336 | 17.552 | 15.586 | 52.827 | 1.00 43.40 | C |
| ATOM | 4945 | CB | ALA | B | 336 | 18.718 | 15.734 | 51.848 | 1.00 17.69 | C |
| ATOM | 4946 | C | ALA | B | 336 | 16.575 | 14.519 | 52.332 | 1.00 43.40 | C |
| ATOM | 4947 | O | ALA | B | 336 | 16.103 | 14.577 | 51.194 | 1.00 43.40 | O |
| ATOM | 4948 | N | HIS | B | 337 | 16.266 | 13.552 | 53.190 | 1.00 32.55 | N |
| ATOM | 4949 | CA | HIS | B | 337 | 15.360 | 12.479 | 52.815 | 1.00 32.55 | C |
| ATOM | 4950 | CB | HIS | B | 337 | 15.342 | 11.395 | 53.887 | 1.00 33.66 | C |
| ATOM | 4951 | CG | HIS | B | 337 | 14.514 | 10.204 | 53.516 | 1.00 33.66 | C |
| ATOM | 4952 | CD2 | HIS | B | 337 | 13.179 | 9.991 | 53.592 | 1.00 33.66 | C |
| ATOM | 4953 | ND1 | HIS | B | 337 | 15.051 | 9.077 | 52.932 | 1.00 33.66 | N |
| ATOM | 4954 | CE1 | HIS | B | 337 | 14.081 | 8.223 | 52.663 | 1.00 33.66 | C |
| ATOM | 4955 | NE2 | HIS | B | 337 | 12.934 | 8.753 | 53.051 | 1.00 33.66 | N |
| ATOM | 4956 | C | HIS | B | 337 | 13.951 | 12.993 | 52.608 | 1.00 32.55 | C |
| ATOM | 4957 | O | HIS | B | 337 | 13.513 | 13.926 | 53.281 | 1.00 32.55 | O |
| ATOM | 4958 | N | SER | B | 338 | 13.234 | 12.362 | 51.688 | 1.00 31.72 | N |
| ATOM | 4959 | CA | SER | B | 338 | 11.863 | 12.755 | 51.390 | 1.00 31.72 | C |
| ATOM | 4960 | CB | SER | B | 338 | 11.346 | 11.948 | 50.216 | 1.00 31.21 | C |
| ATOM | 4961 | OG | SER | B | 338 | 11.343 | 10.574 | 50.557 | 1.00 31.21 | O |
| ATOM | 4962 | C | SER | B | 338 | 10.879 | 12.616 | 52.556 | 1.00 31.72 | C |
| ATOM | 4963 | O | SER | B | 338 | 9.699 | 12.915 | 52.397 | 1.00 31.72 | O |
| ATOM | 4964 | N | PHE | B | 339 | 11.333 | 12.150 | 53.717 | 1.00 27.70 | N |
| ATOM | 4965 | CA | PHE | B | 339 | 10.420 | 12.032 | 54.858 | 1.00 27.70 | C |
| ATOM | 4966 | CB | PHE | B | 339 | 10.962 | 11.062 | 55.910 | 1.00 25.70 | C |
| ATOM | 4967 | CG | PHE | B | 339 | 10.144 | 11.023 | 57.178 | 1.00 25.70 | C |
| ATOM | 4968 | CD1 | PHE | B | 339 | 8.783 | 10.742 | 57.137 | 1.00 25.70 | C |
| ATOM | 4969 | CD2 | PHE | B | 339 | 10.746 | 11.241 | 58.419 | 1.00 25.70 | C |
| ATOM | 4970 | CE1 | PHE | B | 339 | 8.034 | 10.673 | 58.316 | 1.00 25.70 | C |
| ATOM | 4971 | CE2 | PHE | B | 339 | 10.007 | 11.175 | 59.604 | 1.00 25.70 | C |
| ATOM | 4972 | CZ | PHE | B | 339 | 8.650 | 10.889 | 59.552 | 1.00 25.70 | C |
| ATOM | 4973 | C | PHE | B | 339 | 10.277 | 13.410 | 55.473 | 1.00 27.70 | C |
| ATOM | 4974 | O | PHE | B | 339 | 9.272 | 13.742 | 56.106 | 1.00 27.70 | O |
| ATOM | 4975 | N | PHE | B | 340 | 11.311 | 14.211 | 55.261 | 1.00 52.41 | N |
| ATOM | 4976 | CA | PHE | B | 340 | 11.346 | 15.562 | 55.770 | 1.00 52.41 | C |
| ATOM | 4977 | CB | PHE | B | 340 | 12.727 | 15.851 | 56.353 | 1.00 37.23 | C |

FIG. 7-84

```
ATOM   4978  CG   PHE B 340      13.122  14.918  57.466  1.00 37.23           C
ATOM   4979  CD1  PHE B 340      12.358  14.825  58.627  1.00 37.23           C
ATOM   4980  CD2  PHE B 340      14.252  14.117  57.343  1.00 37.23           C
ATOM   4981  CE1  PHE B 340      12.719  13.947  59.641  1.00 37.23           C
ATOM   4982  CE2  PHE B 340      14.619  13.237  58.351  1.00 37.23           C
ATOM   4983  CZ   PHE B 340      13.853  13.151  59.499  1.00 37.23           C
ATOM   4984  C    PHE B 340      11.011  16.582  54.684  1.00 52.41           C
ATOM   4985  O    PHE B 340      11.458  17.721  54.741  1.00 52.41           O
ATOM   4986  N    ASP B 341      10.236  16.178  53.686  1.00 52.29           N
ATOM   4987  CA   ASP B 341       9.863  17.112  52.637  1.00 52.29           C
ATOM   4988  CB   ASP B 341       9.333  16.356  51.409  1.00 37.13           C
ATOM   4989  CG   ASP B 341      10.451  15.730  50.569  1.00 37.13           C
ATOM   4990  OD1  ASP B 341      11.645  15.953  50.880  1.00 37.13           O
ATOM   4991  OD2  ASP B 341      10.133  15.018  49.587  1.00 37.13           O
ATOM   4992  C    ASP B 341       8.794  18.067  53.190  1.00 52.29           C
ATOM   4993  O    ASP B 341       8.778  19.258  52.857  1.00 52.29           O
ATOM   4994  N    GLU B 342       7.915  17.544  54.046  1.00 34.93           N
ATOM   4995  CA   GLU B 342       6.859  18.357  54.630  1.00 34.93           C
ATOM   4996  CB   GLU B 342       5.962  17.535  55.555  1.00 34.72           C
ATOM   4997  CG   GLU B 342       4.874  18.372  56.188  1.00 34.72           C
ATOM   4998  CD   GLU B 342       4.087  17.649  57.262  1.00 34.72           C
ATOM   4999  OE1  GLU B 342       4.667  16.832  58.013  1.00 34.72           O
ATOM   5000  OE2  GLU B 342       2.877  17.920  57.378  1.00 34.72           O
ATOM   5001  C    GLU B 342       7.448  19.515  55.413  1.00 34.93           C
ATOM   5002  O    GLU B 342       6.789  20.533  55.584  1.00 34.93           O
ATOM   5003  N    LEU B 343       8.677  19.369  55.903  1.00 29.89           N
ATOM   5004  CA   LEU B 343       9.297  20.458  56.648  1.00 29.89           C
ATOM   5005  CB   LEU B 343      10.491  19.962  57.462  1.00 22.88           C
ATOM   5006  CG   LEU B 343      10.252  18.948  58.580  1.00 22.88           C
ATOM   5007  CD1  LEU B 343      11.553  18.733  59.359  1.00 22.88           C
ATOM   5008  CD2  LEU B 343       9.141  19.452  59.484  1.00 22.88           C
ATOM   5009  C    LEU B 343       9.769  21.529  55.676  1.00 29.89           C
ATOM   5010  O    LEU B 343       9.658  22.724  55.947  1.00 29.89           O
ATOM   5011  N    ARG B 344      10.302  21.096  54.541  1.00 41.81           N
ATOM   5012  CA   ARG B 344      10.801  22.031  53.528  1.00 41.81           C
ATOM   5013  CB   ARG B 344      11.663  21.293  52.492  1.00 26.01           C
ATOM   5014  CG   ARG B 344      13.135  21.155  52.863  1.00 26.01           C
ATOM   5015  CD   ARG B 344      13.861  20.289  51.837  1.00 26.01           C
ATOM   5016  NE   ARG B 344      13.392  18.908  51.881  1.00 26.01           N
ATOM   5017  CZ   ARG B 344      13.844  17.992  52.727  1.00 26.01           C
ATOM   5018  NH1  ARG B 344      14.789  18.308  53.588  1.00 26.01           N
ATOM   5019  NH2  ARG B 344      13.318  16.775  52.736  1.00 26.01           N
ATOM   5020  C    ARG B 344       9.699  22.826  52.811  1.00 41.81           C
ATOM   5021  O    ARG B 344       9.967  23.570  51.855  1.00 41.81           O
ATOM   5022  N    ASP B 345       8.468  22.675  53.288  1.00 47.48           N
ATOM   5023  CA   ASP B 345       7.306  23.370  52.728  1.00 47.48           C
ATOM   5024  CB   ASP B 345       6.054  22.587  53.117  1.00 54.74           C
ATOM   5025  CG   ASP B 345       4.810  23.072  52.407  1.00 54.74           C
ATOM   5026  OD1  ASP B 345       4.137  22.243  51.752  1.00 54.74           O
ATOM   5027  OD2  ASP B 345       4.496  24.275  52.515  1.00 54.74           O
ATOM   5028  C    ASP B 345       7.256  24.818  53.283  1.00 47.48           C
ATOM   5029  O    ASP B 345       7.425  25.035  54.470  1.00 47.48           O
ATOM   5030  N    PRO B 346       7.038  25.827  52.422  1.00 53.82           N
ATOM   5031  CD   PRO B 346       7.127  25.608  50.975  1.00 40.08           C
ATOM   5032  CA   PRO B 346       6.959  27.265  52.765  1.00 53.82           C
ATOM   5033  CB   PRO B 346       6.625  27.932  51.446  1.00 40.08           C
ATOM   5034  CG   PRO B 346       6.965  26.953  50.426  1.00 40.08           C
ATOM   5035  C    PRO B 346       5.900  27.650  53.786  1.00 53.82           C
ATOM   5036  O    PRO B 346       5.973  28.707  54.433  1.00 53.82           O
ATOM   5037  N    ASN B 347       4.893  26.798  53.906  1.00 63.12           N
```

FIG. 7-85

| ATOM | 5038 | CA | ASN | B | 347 | 3.780 | 27.060 | 54.803 | 1.00 | 63.12 | C |
| ATOM | 5039 | CB | ASN | B | 347 | 2.630 | 27.518 | 53.933 | 1.00 | 77.79 | C |
| ATOM | 5040 | CG | ASN | B | 347 | 2.625 | 26.805 | 52.598 | 1.00 | 77.79 | C |
| ATOM | 5041 | OD1 | ASN | B | 347 | 1.734 | 26.011 | 52.329 | 1.00 | 77.79 | O |
| ATOM | 5042 | ND2 | ASN | B | 347 | 3.630 | 27.076 | 51.757 | 1.00 | 77.79 | N |
| ATOM | 5043 | C | ASN | B | 347 | 3.405 | 25.824 | 55.627 | 1.00 | 63.12 | C |
| ATOM | 5044 | O | ASN | B | 347 | 2.301 | 25.285 | 55.516 | 1.00 | 63.12 | O |
| ATOM | 5045 | N | VAL | B | 348 | 4.339 | 25.413 | 56.469 | 1.00 | 74.40 | N |
| ATOM | 5046 | CA | VAL | B | 348 | 4.190 | 24.255 | 57.329 | 1.00 | 74.40 | C |
| ATOM | 5047 | CB | VAL | B | 348 | 5.352 | 23.253 | 57.166 | 1.00 | 67.21 | C |
| ATOM | 5048 | CG1 | VAL | B | 348 | 4.915 | 22.055 | 56.390 | 1.00 | 67.21 | C |
| ATOM | 5049 | CG2 | VAL | B | 348 | 6.521 | 23.912 | 56.496 | 1.00 | 67.21 | C |
| ATOM | 5050 | C | VAL | B | 348 | 4.259 | 24.760 | 58.735 | 1.00 | 74.40 | C |
| ATOM | 5051 | O | VAL | B | 348 | 5.309 | 25.181 | 59.191 | 1.00 | 74.40 | O |
| ATOM | 5052 | N | LYS | B | 349 | 3.145 | 24.727 | 59.433 | 1.00 | 70.15 | N |
| ATOM | 5053 | CA | LYS | B | 349 | 3.151 | 25.213 | 60.793 | 1.00 | 70.15 | C |
| ATOM | 5054 | CB | LYS | B | 349 | 2.140 | 26.335 | 60.889 | 1.00 | 62.03 | C |
| ATOM | 5055 | CG | LYS | B | 349 | 2.627 | 27.552 | 60.150 | 1.00 | 62.03 | C |
| ATOM | 5056 | CD | LYS | B | 349 | 1.523 | 28.436 | 59.655 | 1.00 | 62.03 | C |
| ATOM | 5057 | CE | LYS | B | 349 | 2.103 | 29.817 | 59.404 | 1.00 | 62.03 | C |
| ATOM | 5058 | NZ | LYS | B | 349 | 3.601 | 29.774 | 59.237 | 1.00 | 62.03 | N |
| ATOM | 5059 | C | LYS | B | 349 | 2.853 | 24.060 | 61.710 | 1.00 | 70.15 | C |
| ATOM | 5060 | O | LYS | B | 349 | 2.433 | 23.002 | 61.213 | 1.00 | 70.15 | O |
| ATOM | 5061 | N | LEU | B | 350 | 3.071 | 24.219 | 63.015 | 1.00 | 48.99 | N |
| ATOM | 5062 | CA | LEU | B | 350 | 2.827 | 23.110 | 63.913 | 1.00 | 48.99 | C |
| ATOM | 5063 | CB | LEU | B | 350 | 3.493 | 23.389 | 65.266 | 1.00 | 33.83 | C |
| ATOM | 5064 | CG | LEU | B | 350 | 4.854 | 24.067 | 65.247 | 1.00 | 33.83 | C |
| ATOM | 5065 | CD1 | LEU | B | 350 | 5.215 | 24.406 | 66.660 | 1.00 | 33.83 | C |
| ATOM | 5066 | CD2 | LEU | B | 350 | 5.855 | 23.149 | 64.647 | 1.00 | 33.83 | C |
| ATOM | 5067 | C | LEU | B | 350 | 1.317 | 22.971 | 64.085 | 1.00 | 48.99 | C |
| ATOM | 5068 | O | LEU | B | 350 | 0.556 | 23.760 | 63.579 | 1.00 | 48.99 | O |
| ATOM | 5069 | N | PRO | B | 351 | 0.872 | 21.953 | 64.802 | 1.00 | 42.22 | N |
| ATOM | 5070 | CD | PRO | B | 351 | 1.524 | 20.660 | 64.938 | 1.00 | 27.80 | C |
| ATOM | 5071 | CA | PRO | B | 351 | -0.586 | 21.820 | 64.952 | 1.00 | 42.22 | C |
| ATOM | 5072 | CB | PRO | B | 351 | -0.732 | 20.651 | 65.950 | 1.00 | 27.80 | C |
| ATOM | 5073 | CG | PRO | B | 351 | 0.719 | 20.050 | 66.019 | 1.00 | 27.80 | C |
| ATOM | 5074 | C | PRO | B | 351 | -1.199 | 23.069 | 65.405 | 1.00 | 42.22 | C |
| ATOM | 5075 | O | PRO | B | 351 | -2.324 | 23.382 | 65.024 | 1.00 | 42.22 | O |
| ATOM | 5076 | N | ASN | B | 352 | -0.407 | 23.807 | 66.153 | 1.00 | 56.68 | N |
| ATOM | 5077 | CA | ASN | B | 352 | -0.862 | 25.073 | 66.671 | 1.00 | 56.68 | C |
| ATOM | 5078 | CB | ASN | B | 352 | -0.187 | 25.339 | 68.001 | 1.00 | 64.57 | C |
| ATOM | 5079 | CG | ASN | B | 352 | 1.281 | 25.752 | 67.854 | 1.00 | 64.57 | C |
| ATOM | 5080 | OD1 | ASN | B | 352 | 2.024 | 25.723 | 68.827 | 1.00 | 64.57 | O |
| ATOM | 5081 | ND2 | ASN | B | 352 | 1.691 | 26.162 | 66.653 | 1.00 | 64.57 | N |
| ATOM | 5082 | C | ASN | B | 352 | -0.754 | 26.358 | 65.835 | 1.00 | 56.68 | C |
| ATOM | 5083 | O | ASN | B | 352 | -0.731 | 27.446 | 66.411 | 1.00 | 56.68 | O |
| ATOM | 5084 | N | GLY | B | 353 | -0.731 | 26.260 | 64.510 | 1.00 | 46.93 | N |
| ATOM | 5085 | CA | GLY | B | 353 | -0.615 | 27.459 | 63.690 | 1.00 | 46.93 | C |
| ATOM | 5086 | C | GLY | B | 353 | 0.645 | 28.294 | 63.856 | 1.00 | 46.93 | C |
| ATOM | 5087 | O | GLY | B | 353 | 0.973 | 29.044 | 62.933 | 1.00 | 46.93 | O |
| ATOM | 5088 | N | ARG | B | 354 | 1.403 | 28.091 | 64.938 | 1.00 | 54.48 | N |
| ATOM | 5089 | CA | ARG | B | 354 | 2.606 | 28.865 | 65.131 | 1.00 | 54.48 | C |
| ATOM | 5090 | CB | ARG | B | 354 | 3.106 | 28.779 | 66.591 | 1.00 | 99.39 | C |
| ATOM | 5091 | CG | ARG | B | 354 | 2.400 | 29.706 | 67.609 | 1.00 | 99.39 | C |
| ATOM | 5092 | CD | ARG | B | 354 | 3.011 | 29.547 | 69.025 | 1.00 | 99.39 | C |
| ATOM | 5093 | NE | ARG | B | 354 | 2.262 | 30.313 | 70.025 | 1.00 | 99.39 | N |
| ATOM | 5094 | CZ | ARG | B | 354 | 2.598 | 30.391 | 71.314 | 1.00 | 99.39 | C |
| ATOM | 5095 | NH1 | ARG | B | 354 | 1.863 | 31.107 | 72.166 | 1.00 | 99.39 | N |
| ATOM | 5096 | NH2 | ARG | B | 354 | 3.661 | 29.721 | 71.768 | 1.00 | 99.39 | N |
| ATOM | 5097 | C | ARG | B | 354 | 3.602 | 28.325 | 64.166 | 1.00 | 54.48 | C |

FIG. 7-86

| ATOM | 5098 | O | ARG | B | 354 | 3.437 | 27.204 | 63.699 | 1.00 | 54.48 | O |
|---|---|---|---|---|---|---|---|---|---|---|---|
| ATOM | 5099 | N | ASP | B | 355 | 4.605 | 29.138 | 63.853 | 1.00 | 38.07 | N |
| ATOM | 5100 | CA | ASP | B | 355 | 5.652 | 28.745 | 62.911 | 1.00 | 38.07 | C |
| ATOM | 5101 | CB | ASP | B | 355 | 6.574 | 29.936 | 62.616 | 1.00 | 57.46 | C |
| ATOM | 5102 | CG | ASP | B | 355 | 6.308 | 30.576 | 61.266 | 1.00 | 57.46 | C |
| ATOM | 5103 | OD1 | ASP | B | 355 | 6.109 | 29.840 | 60.257 | 1.00 | 57.46 | O |
| ATOM | 5104 | OD2 | ASP | B | 355 | 6.350 | 31.824 | 61.226 | 1.00 | 57.46 | O |
| ATOM | 5105 | C | ASP | B | 355 | 6.523 | 27.581 | 63.393 | 1.00 | 38.07 | C |
| ATOM | 5106 | O | ASP | B | 355 | 6.606 | 27.326 | 64.584 | 1.00 | 38.07 | O |
| ATOM | 5107 | N | THR | B | 356 | 7.207 | 26.905 | 62.479 | 1.00 | 43.54 | N |
| ATOM | 5108 | CA | THR | B | 356 | 8.086 | 25.819 | 62.871 | 1.00 | 43.54 | C |
| ATOM | 5109 | CB | THR | B | 356 | 8.305 | 24.852 | 61.688 | 1.00 | 38.93 | C |
| ATOM | 5110 | OG1 | THR | B | 356 | 8.678 | 25.590 | 60.506 | 1.00 | 38.93 | O |
| ATOM | 5111 | CG2 | THR | B | 356 | 7.011 | 24.081 | 61.409 | 1.00 | 38.93 | C |
| ATOM | 5112 | C | THR | B | 356 | 9.407 | 26.481 | 63.265 | 1.00 | 43.54 | C |
| ATOM | 5113 | O | THR | B | 356 | 9.613 | 27.655 | 62.972 | 1.00 | 43.54 | O |
| ATOM | 5114 | N | PRO | B | 357 | 10.290 | 25.750 | 63.971 | 1.00 | 33.58 | N |
| ATOM | 5115 | CD | PRO | B | 357 | 10.008 | 24.510 | 64.717 | 1.00 | 42.70 | C |
| ATOM | 5116 | CA | PRO | B | 357 | 11.580 | 26.311 | 64.389 | 1.00 | 33.58 | C |
| ATOM | 5117 | CB | PRO | B | 357 | 12.038 | 25.338 | 65.474 | 1.00 | 42.70 | C |
| ATOM | 5118 | CG | PRO | B | 357 | 11.375 | 24.038 | 65.101 | 1.00 | 42.70 | C |
| ATOM | 5119 | C | PRO | B | 357 | 12.576 | 26.448 | 63.270 | 1.00 | 33.58 | C |
| ATOM | 5120 | O | PRO | B | 357 | 12.281 | 26.079 | 62.144 | 1.00 | 33.58 | O |
| ATOM | 5121 | N | ALA | B | 358 | 13.740 | 27.010 | 63.569 | 1.00 | 40.19 | N |
| ATOM | 5122 | CA | ALA | B | 358 | 14.763 | 27.168 | 62.545 | 1.00 | 40.19 | C |
| ATOM | 5123 | CB | ALA | B | 358 | 15.989 | 27.863 | 63.118 | 1.00 | 29.36 | C |
| ATOM | 5124 | C | ALA | B | 358 | 15.155 | 25.793 | 62.016 | 1.00 | 40.19 | C |
| ATOM | 5125 | O | ALA | B | 358 | 15.444 | 24.881 | 62.797 | 1.00 | 40.19 | O |
| ATOM | 5126 | N | LEU | B | 359 | 15.180 | 25.632 | 60.697 | 1.00 | 31.70 | N |
| ATOM | 5127 | CA | LEU | B | 359 | 15.555 | 24.338 | 60.143 | 1.00 | 31.70 | C |
| ATOM | 5128 | CB | LEU | B | 359 | 14.303 | 23.568 | 59.710 | 1.00 | 28.28 | C |
| ATOM | 5129 | CG | LEU | B | 359 | 13.255 | 23.276 | 60.790 | 1.00 | 28.28 | C |
| ATOM | 5130 | CD1 | LEU | B | 359 | 12.022 | 22.650 | 60.142 | 1.00 | 28.28 | C |
| ATOM | 5131 | CD2 | LEU | B | 359 | 13.826 | 22.356 | 61.849 | 1.00 | 28.28 | C |
| ATOM | 5132 | C | LEU | B | 359 | 16.505 | 24.431 | 58.965 | 1.00 | 31.70 | C |
| ATOM | 5133 | O | LEU | B | 359 | 17.156 | 23.446 | 58.609 | 1.00 | 31.70 | O |
| ATOM | 5134 | N | PHE | B | 360 | 16.616 | 25.617 | 58.380 | 1.00 | 48.61 | N |
| ATOM | 5135 | CA | PHE | B | 360 | 17.442 | 25.762 | 57.192 | 1.00 | 48.61 | C |
| ATOM | 5136 | CB | PHE | B | 360 | 16.560 | 26.245 | 56.035 | 1.00 | 44.87 | C |
| ATOM | 5137 | CG | PHE | B | 360 | 15.230 | 25.553 | 55.964 | 1.00 | 44.87 | C |
| ATOM | 5138 | CD1 | PHE | B | 360 | 15.143 | 24.218 | 55.587 | 1.00 | 44.87 | C |
| ATOM | 5139 | CD2 | PHE | B | 360 | 14.073 | 26.220 | 56.330 | 1.00 | 44.87 | C |
| ATOM | 5140 | CE1 | PHE | B | 360 | 13.919 | 23.558 | 55.581 | 1.00 | 44.87 | C |
| ATOM | 5141 | CE2 | PHE | B | 360 | 12.849 | 25.571 | 56.327 | 1.00 | 44.87 | C |
| ATOM | 5142 | CZ | PHE | B | 360 | 12.770 | 24.236 | 55.953 | 1.00 | 44.87 | C |
| ATOM | 5143 | C | PHE | B | 360 | 18.657 | 26.658 | 57.294 | 1.00 | 48.61 | C |
| ATOM | 5144 | O | PHE | B | 360 | 19.332 | 26.893 | 56.294 | 1.00 | 48.61 | O |
| ATOM | 5145 | N | ASN | B | 361 | 18.955 | 27.152 | 58.486 | 1.00 | 32.42 | N |
| ATOM | 5146 | CA | ASN | B | 361 | 20.102 | 28.034 | 58.632 | 1.00 | 32.42 | C |
| ATOM | 5147 | CB | ASN | B | 361 | 19.927 | 28.911 | 59.866 | 1.00 | 38.75 | C |
| ATOM | 5148 | CG | ASN | B | 361 | 19.831 | 28.105 | 61.141 | 1.00 | 38.75 | C |
| ATOM | 5149 | OD1 | ASN | B | 361 | 19.077 | 27.143 | 61.226 | 1.00 | 38.75 | O |
| ATOM | 5150 | ND2 | ASN | B | 361 | 20.595 | 28.501 | 62.147 | 1.00 | 38.75 | N |
| ATOM | 5151 | C | ASN | B | 361 | 21.419 | 27.276 | 58.707 | 1.00 | 32.42 | C |
| ATOM | 5152 | O | ASN | B | 361 | 22.247 | 27.537 | 59.578 | 1.00 | 32.42 | O |
| ATOM | 5153 | N | PHE | B | 362 | 21.619 | 26.333 | 57.796 | 1.00 | 34.23 | N |
| ATOM | 5154 | CA | PHE | B | 362 | 22.859 | 25.568 | 57.797 | 1.00 | 34.23 | C |
| ATOM | 5155 | CB | PHE | B | 362 | 22.852 | 24.551 | 56.659 | 1.00 | 40.30 | C |
| ATOM | 5156 | CG | PHE | B | 362 | 21.829 | 23.489 | 56.832 | 1.00 | 40.30 | C |
| ATOM | 5157 | CD1 | PHE | B | 362 | 22.001 | 22.502 | 57.790 | 1.00 | 40.30 | C |

FIG. 7-87

```
ATOM   5158  CD2 PHE B 362      20.668  23.499  56.078  1.00 40.30           C
ATOM   5159  CE1 PHE B 362      21.032  21.537  58.004  1.00 40.30           C
ATOM   5160  CE2 PHE B 362      19.684  22.535  56.282  1.00 40.30           C
ATOM   5161  CZ  PHE B 362      19.868  21.548  57.253  1.00 40.30           C
ATOM   5162  C   PHE B 362      24.078  26.475  57.665  1.00 34.23           C
ATOM   5163  O   PHE B 362      23.972  27.628  57.236  1.00 34.23           O
ATOM   5164  N   THR B 363      25.237  25.955  58.044  1.00 48.58           N
ATOM   5165  CA  THR B 363      26.468  26.722  57.943  1.00 48.58           C
ATOM   5166  CB  THR B 363      27.166  26.926  59.321  1.00 49.03           C
ATOM   5167  OG1 THR B 363      27.619  25.667  59.843  1.00 49.03           O
ATOM   5168  CG2 THR B 363      26.208  27.562  60.302  1.00 49.03           C
ATOM   5169  C   THR B 363      27.389  25.923  57.059  1.00 48.58           C
ATOM   5170  O   THR B 363      27.289  24.702  56.996  1.00 48.58           O
ATOM   5171  N   THR B 364      28.286  26.612  56.374  1.00 66.27           N
ATOM   5172  CA  THR B 364      29.234  25.949  55.494  1.00 66.27           C
ATOM   5173  CB  THR B 364      30.287  26.961  55.019  1.00 43.80           C
ATOM   5174  OG1 THR B 364      30.983  27.489  56.153  1.00 43.80           O
ATOM   5175  CG2 THR B 364      29.611  28.115  54.287  1.00 43.80           C
ATOM   5176  C   THR B 364      29.920  24.753  56.182  1.00 66.27           C
ATOM   5177  O   THR B 364      30.371  23.811  55.520  1.00 66.27           O
ATOM   5178  N   GLN B 365      29.993  24.804  57.510  1.00 46.92           N
ATOM   5179  CA  GLN B 365      30.600  23.747  58.317  1.00 46.92           C
ATOM   5180  CB  GLN B 365      30.816  24.256  59.752  1.00 60.59           C
ATOM   5181  CG  GLN B 365      31.018  23.180  60.812  1.00 60.59           C
ATOM   5182  CD  GLN B 365      32.451  22.705  60.918  1.00 60.59           C
ATOM   5183  OE1 GLN B 365      32.735  21.709  61.583  1.00 60.59           O
ATOM   5184  NE2 GLN B 365      33.365  23.419  60.273  1.00 60.59           N
ATOM   5185  C   GLN B 365      29.656  22.547  58.327  1.00 46.92           C
ATOM   5186  O   GLN B 365      30.075  21.405  58.098  1.00 46.92           O
ATOM   5187  N   GLU B 366      28.379  22.818  58.597  1.00 44.48           N
ATOM   5188  CA  GLU B 366      27.369  21.766  58.637  1.00 44.48           C
ATOM   5189  CB  GLU B 366      25.974  22.354  58.876  1.00 50.96           C
ATOM   5190  CG  GLU B 366      25.822  23.136  60.163  1.00 50.96           C
ATOM   5191  CD  GLU B 366      24.370  23.381  60.508  1.00 50.96           C
ATOM   5192  OE1 GLU B 366      23.644  22.379  60.701  1.00 50.96           O
ATOM   5193  OE2 GLU B 366      23.955  24.564  60.583  1.00 50.96           O
ATOM   5194  C   GLU B 366      27.358  20.989  57.329  1.00 44.48           C
ATOM   5195  O   GLU B 366      27.330  19.760  57.335  1.00 44.48           O
ATOM   5196  N   LEU B 367      27.397  21.713  56.212  1.00 46.28           N
ATOM   5197  CA  LEU B 367      27.368  21.113  54.879  1.00 46.28           C
ATOM   5198  CB  LEU B 367      26.834  22.140  53.887  1.00 29.99           C
ATOM   5199  CG  LEU B 367      25.538  22.835  54.315  1.00 29.99           C
ATOM   5200  CD1 LEU B 367      25.195  23.957  53.333  1.00 29.99           C
ATOM   5201  CD2 LEU B 367      24.398  21.817  54.374  1.00 29.99           C
ATOM   5202  C   LEU B 367      28.717  20.578  54.377  1.00 46.28           C
ATOM   5203  O   LEU B 367      28.823  20.107  53.242  1.00 46.28           O
ATOM   5204  N   SER B 368      29.739  20.644  55.226  1.00 42.12           N
ATOM   5205  CA  SER B 368      31.076  20.188  54.862  1.00 42.12           C
ATOM   5206  CB  SER B 368      32.006  20.191  56.085  1.00 41.88           C
ATOM   5207  OG  SER B 368      31.713  19.138  56.991  1.00 41.88           O
ATOM   5208  C   SER B 368      31.126  18.812  54.220  1.00 42.12           C
ATOM   5209  O   SER B 368      31.753  18.647  53.177  1.00 42.12           O
ATOM   5210  N   SER B 369      30.474  17.827  54.837  1.00 75.62           N
ATOM   5211  CA  SER B 369      30.499  16.453  54.328  1.00 75.62           C
ATOM   5212  CB  SER B 369      29.748  15.518  55.276  1.00 30.91           C
ATOM   5213  OG  SER B 369      28.350  15.656  55.121  1.00 30.91           O
ATOM   5214  C   SER B 369      29.939  16.290  52.920  1.00 75.62           C
ATOM   5215  O   SER B 369      30.273  15.328  52.224  1.00 75.62           O
ATOM   5216  N   ASN B 370      29.076  17.217  52.511  1.00 44.71           N
ATOM   5217  CA  ASN B 370      28.487  17.181  51.175  1.00 44.71           C
```

FIG. 7-88

```
ATOM   5218  CB   ASN B 370      27.547  15.988  51.015  1.00 46.21           C
ATOM   5219  CG   ASN B 370      26.973  15.894  49.622  1.00 46.21           C
ATOM   5220  OD1  ASN B 370      25.945  16.497  49.330  1.00 46.21           O
ATOM   5221  ND2  ASN B 370      27.646  15.154  48.744  1.00 46.21           N
ATOM   5222  C    ASN B 370      27.743  18.463  50.841  1.00 44.71           C
ATOM   5223  O    ASN B 370      26.520  18.532  50.944  1.00 44.71           O
ATOM   5224  N    PRO B 371      28.488  19.497  50.417  1.00 44.39           N
ATOM   5225  CD   PRO B 371      29.954  19.445  50.247  1.00 14.29           C
ATOM   5226  CA   PRO B 371      27.977  20.818  50.045  1.00 44.39           C
ATOM   5227  CB   PRO B 371      29.200  21.491  49.446  1.00 14.29           C
ATOM   5228  CG   PRO B 371      30.321  20.901  50.237  1.00 14.29           C
ATOM   5229  C    PRO B 371      26.787  20.811  49.077  1.00 44.39           C
ATOM   5230  O    PRO B 371      25.773  21.461  49.331  1.00 44.39           O
ATOM   5231  N    PRO B 372      26.896  20.084  47.948  1.00 50.52           N
ATOM   5232  CD   PRO B 372      28.013  19.248  47.477  1.00 51.18           C
ATOM   5233  CA   PRO B 372      25.788  20.043  46.987  1.00 50.52           C
ATOM   5234  CB   PRO B 372      26.281  19.052  45.933  1.00 51.18           C
ATOM   5235  CG   PRO B 372      27.290  18.220  46.664  1.00 51.18           C
ATOM   5236  C    PRO B 372      24.411  19.679  47.538  1.00 50.52           C
ATOM   5237  O    PRO B 372      23.400  19.947  46.892  1.00 50.52           O
ATOM   5238  N    LEU B 373      24.362  19.067  48.720  1.00 33.41           N
ATOM   5239  CA   LEU B 373      23.077  18.704  49.319  1.00 33.41           C
ATOM   5240  CB   LEU B 373      23.280  17.817  50.548  1.00 27.82           C
ATOM   5241  CG   LEU B 373      23.145  16.312  50.317  1.00 27.82           C
ATOM   5242  CD1  LEU B 373      23.175  15.608  51.659  1.00 27.82           C
ATOM   5243  CD2  LEU B 373      21.847  16.012  49.578  1.00 27.82           C
ATOM   5244  C    LEU B 373      22.293  19.934  49.733  1.00 33.41           C
ATOM   5245  O    LEU B 373      21.097  19.857  50.019  1.00 33.41           O
ATOM   5246  N    ALA B 374      22.988  21.065  49.766  1.00 33.79           N
ATOM   5247  CA   ALA B 374      22.401  22.341  50.163  1.00 33.79           C
ATOM   5248  CB   ALA B 374      23.480  23.447  50.131  1.00 16.28           C
ATOM   5249  C    ALA B 374      21.221  22.728  49.282  1.00 33.79           C
ATOM   5250  O    ALA B 374      20.243  23.313  49.756  1.00 33.79           O
ATOM   5251  N    THR B 375      21.325  22.386  48.001  1.00 49.11           N
ATOM   5252  CA   THR B 375      20.293  22.686  47.015  1.00 49.11           C
ATOM   5253  CB   THR B 375      20.658  22.088  45.638  1.00 41.67           C
ATOM   5254  OG1  THR B 375      21.788  22.790  45.100  1.00 41.67           O
ATOM   5255  CG2  THR B 375      19.478  22.190  44.669  1.00 41.67           C
ATOM   5256  C    THR B 375      18.942  22.146  47.439  1.00 49.11           C
ATOM   5257  O    THR B 375      17.902  22.715  47.102  1.00 49.11           O
ATOM   5258  N    ILE B 376      18.971  21.047  48.182  1.00 45.63           N
ATOM   5259  CA   ILE B 376      17.759  20.416  48.667  1.00 45.63           C
ATOM   5260  CB   ILE B 376      17.883  18.908  48.589  1.00 37.88           C
ATOM   5261  CG2  ILE B 376      16.627  18.243  49.151  1.00 37.88           C
ATOM   5262  CG1  ILE B 376      18.118  18.522  47.133  1.00 37.88           C
ATOM   5263  CD1  ILE B 376      18.544  17.121  46.950  1.00 37.88           C
ATOM   5264  C    ILE B 376      17.451  20.807  50.101  1.00 45.63           C
ATOM   5265  O    ILE B 376      16.297  21.064  50.445  1.00 45.63           O
ATOM   5266  N    LEU B 377      18.484  20.847  50.936  1.00 42.98           N
ATOM   5267  CA   LEU B 377      18.311  21.208  52.337  1.00 42.98           C
ATOM   5268  CB   LEU B 377      19.656  21.116  53.064  1.00 27.06           C
ATOM   5269  CG   LEU B 377      20.041  19.674  53.380  1.00 27.06           C
ATOM   5270  CD1  LEU B 377      21.505  19.588  53.802  1.00 27.06           C
ATOM   5271  CD2  LEU B 377      19.115  19.157  54.470  1.00 27.06           C
ATOM   5272  C    LEU B 377      17.729  22.610  52.496  1.00 42.98           C
ATOM   5273  O    LEU B 377      16.833  22.845  53.320  1.00 42.98           O
ATOM   5274  N    ILE B 378      18.239  23.532  51.688  1.00 50.15           N
ATOM   5275  CA   ILE B 378      17.802  24.919  51.738  1.00 50.15           C
ATOM   5276  CB   ILE B 378      19.009  25.842  51.599  1.00 49.14           C
ATOM   5277  CG2  ILE B 378      18.576  27.281  51.778  1.00 49.14           C
```

FIG. 7-89

```
ATOM   5278  CG1 ILE B 378      20.060  25.461  52.650  1.00 49.14           C
ATOM   5279  CD1 ILE B 378      21.418  26.082  52.433  1.00 49.14           C
ATOM   5280  C   ILE B 378      16.793  25.213  50.628  1.00 50.15           C
ATOM   5281  O   ILE B 378      17.175  25.413  49.475  1.00 50.15           O
ATOM   5282  N   PRO B 379      15.487  25.256  50.976  1.00 39.64           N
ATOM   5283  CD  PRO B 379      14.928  25.198  52.334  1.00 33.73           C
ATOM   5284  CA  PRO B 379      14.414  25.517  50.019  1.00 39.64           C
ATOM   5285  CB  PRO B 379      13.140  25.287  50.844  1.00 33.73           C
ATOM   5286  CG  PRO B 379      13.596  24.581  52.062  1.00 33.73           C
ATOM   5287  C   PRO B 379      14.524  26.949  49.546  1.00 39.64           C
ATOM   5288  O   PRO B 379      15.001  27.804  50.280  1.00 39.64           O
ATOM   5289  N   PRO B 380      14.082  27.230  48.314  1.00 67.03           N
ATOM   5290  CD  PRO B 380      13.597  26.271  47.305  1.00 77.46           C
ATOM   5291  CA  PRO B 380      14.139  28.582  47.757  1.00 67.03           C
ATOM   5292  CB  PRO B 380      13.356  28.441  46.461  1.00 77.46           C
ATOM   5293  CG  PRO B 380      13.729  27.057  46.026  1.00 77.46           C
ATOM   5294  C   PRO B 380      13.583  29.685  48.662  1.00 67.03           C
ATOM   5295  O   PRO B 380      14.223  30.725  48.820  1.00 67.03           O
ATOM   5296  N   HIS B 381      12.415  29.459  49.265  1.00 39.48           N
ATOM   5297  CA  HIS B 381      11.794  30.476  50.123  1.00 39.48           C
ATOM   5298  CB  HIS B 381      10.388  30.043  50.546  1.00 66.37           C
ATOM   5299  CG  HIS B 381      10.367  28.962  51.579  1.00 66.37           C
ATOM   5300  CD2 HIS B 381      10.142  27.633  51.470  1.00 66.37           C
ATOM   5301  ND1 HIS B 381      10.602  29.202  52.915  1.00 66.37           N
ATOM   5302  CE1 HIS B 381      10.520  28.066  53.585  1.00 66.37           C
ATOM   5303  NE2 HIS B 381      10.243  27.098  52.731  1.00 66.37           N
ATOM   5304  C   HIS B 381      12.595  30.841  51.362  1.00 39.48           C
ATOM   5305  O   HIS B 381      12.614  31.997  51.770  1.00 39.48           O
ATOM   5306  N   ALA B 382      13.257  29.859  51.959  1.00 68.78           N
ATOM   5307  CA  ALA B 382      14.057  30.113  53.149  1.00 68.78           C
ATOM   5308  CB  ALA B 382      14.384  28.800  53.843  1.00 53.94           C
ATOM   5309  C   ALA B 382      15.343  30.851  52.785  1.00 68.78           C
ATOM   5310  O   ALA B 382      16.155  31.170  53.656  1.00 68.78           O
ATOM   5311  N   ARG B 383      15.519  31.128  51.496  1.00 62.64           N
ATOM   5312  CA  ARG B 383      16.712  31.816  51.028  1.00 62.64           C
ATOM   5313  CB  ARG B 383      16.851  31.623  49.520  1.00 61.02           C
ATOM   5314  CG  ARG B 383      18.264  31.315  49.067  1.00 61.02           C
ATOM   5315  CD  ARG B 383      18.539  29.825  49.040  1.00 61.02           C
ATOM   5316  NE  ARG B 383      17.722  29.164  48.028  1.00 61.02           N
ATOM   5317  CZ  ARG B 383      17.908  27.913  47.615  1.00 61.02           C
ATOM   5318  NH1 ARG B 383      18.892  27.180  48.132  1.00 61.02           N
ATOM   5319  NH2 ARG B 383      17.112  27.397  46.684  1.00 61.02           N
ATOM   5320  C   ARG B 383      16.676  33.315  51.362  1.00 62.64           C
ATOM   5321  O   ARG B 383      17.233  34.110  50.576  1.00 62.64           O
ATOM   5322  OXT ARG B 383      16.114  33.683  52.419  1.00 61.02           O
TER    5323      ARG B 383
ATOM   5324  CB  SER C   3      24.199   4.995  78.942  1.00 61.09           C
ATOM   5325  OG  SER C   3      24.607   5.817  80.023  1.00 61.09           O
ATOM   5326  C   SER C   3      25.505   3.073  79.952  1.00 34.71           C
ATOM   5327  O   SER C   3      25.741   3.303  81.140  1.00 34.71           O
ATOM   5328  N   SER C   3      23.017   3.199  80.239  1.00 34.71           N
ATOM   5329  CA  SER C   3      24.166   3.493  79.318  1.00 34.71           C
ATOM   5330  N   PRO C   4      26.400   2.460  79.151  1.00 35.32           N
ATOM   5331  CD  PRO C   4      26.178   2.096  77.740  1.00 65.93           C
ATOM   5332  CA  PRO C   4      27.710   1.988  79.587  1.00 35.32           C
ATOM   5333  CB  PRO C   4      28.130   1.058  78.458  1.00 65.93           C
ATOM   5334  CG  PRO C   4      27.573   1.714  77.284  1.00 65.93           C
ATOM   5335  C   PRO C   4      28.788   2.999  79.904  1.00 35.32           C
ATOM   5336  O   PRO C   4      28.616   4.213  79.787  1.00 35.32           O
ATOM   5337  N   HIS C   5      29.928   2.454  80.294  1.00 45.56           N
```

FIG. 7-90

| | | | | | | | | | | |
|---|---|---|---|---|---|---|---|---|---|---|
| ATOM | 5338 | CA | HIS | C | 5 | 31.064 | 3.250 | 80.664 | 1.00 45.56 | C |
| ATOM | 5339 | CB | HIS | C | 5 | 31.763 | 2.620 | 81.840 | 1.00 69.60 | C |
| ATOM | 5340 | CG | HIS | C | 5 | 31.283 | 3.138 | 83.151 | 1.00 69.60 | C |
| ATOM | 5341 | CD2 | HIS | C | 5 | 31.152 | 4.407 | 83.604 | 1.00 69.60 | C |
| ATOM | 5342 | ND1 | HIS | C | 5 | 30.866 | 2.317 | 84.176 | 1.00 69.60 | N |
| ATOM | 5343 | CE1 | HIS | C | 5 | 30.498 | 3.057 | 85.206 | 1.00 69.60 | C |
| ATOM | 5344 | NE2 | HIS | C | 5 | 30.662 | 4.328 | 84.887 | 1.00 69.60 | N |
| ATOM | 5345 | C | HIS | C | 5 | 32.074 | 3.497 | 79.601 | 1.00 45.56 | C |
| ATOM | 5346 | O | HIS | C | 5 | 32.213 | 2.742 | 78.639 | 1.00 45.56 | O |
| ATOM | 5347 | N | GLN | C | 6 | 32.789 | 4.585 | 79.817 | 1.00 37.64 | N |
| ATOM | 5348 | CA | GLN | C | 6 | 33.855 | 5.012 | 78.949 | 1.00 37.64 | C |
| ATOM | 5349 | CB | GLN | C | 6 | 34.413 | 6.305 | 79.473 | 1.00 78.39 | C |
| ATOM | 5350 | CG | GLN | C | 6 | 33.530 | 6.908 | 80.496 | 1.00 78.39 | C |
| ATOM | 5351 | CD | GLN | C | 6 | 33.570 | 8.374 | 80.383 | 1.00 78.39 | C |
| ATOM | 5352 | OE1 | GLN | C | 6 | 33.864 | 9.067 | 81.342 | 1.00 78.39 | O |
| ATOM | 5353 | NE2 | GLN | C | 6 | 33.288 | 8.875 | 79.187 | 1.00 78.39 | N |
| ATOM | 5354 | C | GLN | C | 6 | 34.971 | 3.987 | 78.994 | 1.00 37.64 | C |
| ATOM | 5355 | O | GLN | C | 6 | 34.877 | 2.935 | 79.651 | 1.00 37.64 | O |
| ATOM | 5356 | N | PSE | C | 7 | 36.044 | 4.337 | 78.304 | 1.00 49.29 | N |
| ATOM | 5357 | CA | PSE | C | 7 | 37.235 | 3.525 | 78.245 | 1.00 49.29 | C |
| ATOM | 5358 | C | PSE | C | 7 | 38.138 | 4.075 | 79.328 | 1.00 49.29 | C |
| ATOM | 5359 | O | PSE | C | 7 | 38.642 | 5.191 | 79.213 | 1.00 49.29 | O |
| ATOM | 5360 | CB | PSE | C | 7 | 37.926 | 3.784 | 76.961 | 1.00 49.58 | C |
| ATOM | 5361 | OG | PSE | C | 7 | 37.318 | 4.887 | 76.430 | 1.00 49.58 | O |
| ATOM | 5362 | P | PSE | C | 7 | 37.305 | 4.980 | 74.959 | 1.00 49.58 | P |
| ATOM | 5363 | OP1 | PSE | C | 7 | 38.669 | 5.108 | 74.578 | 1.00 49.58 | O |
| ATOM | 5364 | OP2 | PSE | C | 7 | 36.541 | 6.280 | 74.575 | 1.00 49.58 | O |
| ATOM | 5365 | OP3 | PSE | C | 7 | 36.666 | 3.833 | 74.421 | 1.00 49.58 | O |
| ATOM | 5366 | N | GLU | C | 8 | 38.303 | 3.303 | 80.393 | 1.00 65.98 | N |
| ATOM | 5367 | CA | GLU | C | 8 | 39.148 | 3.698 | 81.510 | 1.00 65.98 | C |
| ATOM | 5368 | CB | GLU | C | 8 | 39.369 | 2.518 | 82.439 | 1.00 71.72 | C |
| ATOM | 5369 | CG | GLU | C | 8 | 38.530 | 1.321 | 82.109 | 1.00 71.72 | C |
| ATOM | 5370 | CD | GLU | C | 8 | 38.811 | 0.185 | 83.056 | 1.00 71.72 | C |
| ATOM | 5371 | OE1 | GLU | C | 8 | 39.102 | 0.458 | 84.241 | 1.00 71.72 | O |
| ATOM | 5372 | OE2 | GLU | C | 8 | 38.736 | -0.984 | 82.633 | 1.00 71.72 | O |
| ATOM | 5373 | C | GLU | C | 8 | 40.498 | 4.143 | 80.996 | 1.00 65.98 | C |
| ATOM | 5374 | O | GLU | C | 8 | 41.032 | 3.565 | 80.050 | 1.00 65.98 | O |
| ATOM | 5375 | N | ASP | C | 9 | 41.059 | 5.164 | 81.620 | 1.00 60.49 | N |
| ATOM | 5376 | CA | ASP | C | 9 | 42.355 | 5.618 | 81.190 | 1.00 60.49 | C |
| ATOM | 5377 | CB | ASP | C | 9 | 42.432 | 7.144 | 81.327 | 1.00 71.12 | C |
| ATOM | 5378 | CG | ASP | C | 9 | 43.300 | 7.596 | 82.463 | 1.00 71.12 | C |
| ATOM | 5379 | OD1 | ASP | C | 9 | 44.534 | 7.511 | 82.314 | 1.00 71.12 | O |
| ATOM | 5380 | OD2 | ASP | C | 9 | 42.755 | 8.040 | 83.498 | 1.00 71.12 | O |
| ATOM | 5381 | C | ASP | C | 9 | 43.340 | 4.885 | 82.084 | 1.00 60.49 | C |
| ATOM | 5382 | O | ASP | C | 9 | 43.012 | 4.534 | 83.217 | 1.00 60.49 | O |
| ATOM | 5383 | N | GLU | C | 10 | 44.516 | 4.583 | 81.554 | 1.00 98.32 | N |
| ATOM | 5384 | CA | GLU | C | 10 | 45.541 | 3.900 | 82.334 | 1.00 98.32 | C |
| ATOM | 5385 | CB | GLU | C | 10 | 45.231 | 2.393 | 82.485 | 1.00 89.01 | C |
| ATOM | 5386 | CG | GLU | C | 10 | 44.029 | 1.891 | 81.695 | 1.00 89.01 | C |
| ATOM | 5387 | CD | GLU | C | 10 | 44.419 | 1.155 | 80.433 | 1.00 89.01 | C |
| ATOM | 5388 | OE1 | GLU | C | 10 | 44.536 | -0.088 | 80.477 | 1.00 89.01 | O |
| ATOM | 5389 | OE2 | GLU | C | 10 | 44.617 | 1.819 | 79.397 | 1.00 89.01 | O |
| ATOM | 5390 | C | GLU | C | 10 | 46.877 | 4.093 | 81.639 | 1.00 98.32 | C |
| ATOM | 5391 | O | GLU | C | 10 | 46.877 | 4.216 | 80.397 | 1.00 98.32 | O |
| ATOM | 5392 | OXT | GLU | C | 10 | 47.907 | 4.116 | 82.342 | 1.00 89.01 | O |
| TER | 5393 | | GLU | C | 10 | | | | | |
| ATOM | 5394 | CB | HIS | D | 1 | 12.411 | 6.182 | 23.767 | 1.00 81.17 | C |
| ATOM | 5395 | CG | HIS | D | 1 | 11.804 | 5.342 | 24.857 | 1.00 81.17 | C |
| ATOM | 5396 | CD2 | HIS | D | 1 | 10.558 | 4.855 | 25.011 | 1.00 81.17 | C |
| ATOM | 5397 | ND1 | HIS | D | 1 | 12.550 | 4.815 | 25.897 | 1.00 81.17 | N |

FIG. 7-91

```
ATOM   5398  CE1  HIS  D  1    11.783   4.030  26.633  1.00  81.17           C
ATOM   5399  NE2  HIS  D  1    10.572   4.032  26.120  1.00  81.17           N
ATOM   5400  C    HIS  D  1    14.322   4.890  22.695  1.00  72.25           C
ATOM   5401  O    HIS  D  1    14.566   3.714  22.994  1.00  72.25           O
ATOM   5402  N    HIS  D  1    11.969   4.220  22.307  1.00  72.25           N
ATOM   5403  CA   HIS  D  1    12.880   5.376  22.534  1.00  72.25           C
ATOM   5404  N    SER  D  2    15.274   5.796  22.477  1.00  66.23           N
ATOM   5405  CA   SER  D  2    16.700   5.465  22.584  1.00  66.23           C
ATOM   5406  CB   SER  D  2    17.535   6.446  21.781  1.00  41.95           C
ATOM   5407  OG   SER  D  2    18.915   6.098  21.894  1.00  41.95           O
ATOM   5408  C    SER  D  2    17.297   5.381  24.001  1.00  66.23           C
ATOM   5409  O    SER  D  2    18.155   4.548  24.259  1.00  66.23           O
ATOM   5410  N    SER  D  3    16.887   6.252  24.907  1.00  45.54           N
ATOM   5411  CA   SER  D  3    17.396   6.171  26.256  1.00  45.54           C
ATOM   5412  CB   SER  D  3    17.983   7.514  26.665  1.00  91.16           C
ATOM   5413  OG   SER  D  3    19.302   7.651  26.131  1.00  91.16           O
ATOM   5414  C    SER  D  3    16.209   5.719  27.093  1.00  45.54           C
ATOM   5415  O    SER  D  3    15.067   6.034  26.793  1.00  45.54           O
ATOM   5416  N    PRO  D  4    16.473   4.961  28.153  1.00  38.13           N
ATOM   5417  CD   PRO  D  4    17.825   4.789  28.695  1.00  63.08           C
ATOM   5418  CA   PRO  D  4    15.463   4.423  29.069  1.00  38.13           C
ATOM   5419  CB   PRO  D  4    16.280   3.566  30.020  1.00  63.08           C
ATOM   5420  CG   PRO  D  4    17.675   3.564  29.433  1.00  63.08           C
ATOM   5421  C    PRO  D  4    14.669   5.443  29.848  1.00  38.13           C
ATOM   5422  O    PRO  D  4    15.120   6.564  30.081  1.00  38.13           O
ATOM   5423  N    HIS  D  5    13.494   5.031  30.303  1.00  76.32           N
ATOM   5424  CA   HIS  D  5    12.645   5.904  31.083  1.00  76.32           C
ATOM   5425  CB   HIS  D  5    11.357   5.179  31.464  1.00  83.02           C
ATOM   5426  CG   HIS  D  5    10.219   5.510  30.561  1.00  83.02           C
ATOM   5427  CD2  HIS  D  5     9.628   6.687  30.278  1.00  83.02           C
ATOM   5428  ND1  HIS  D  5     9.598   4.565  29.769  1.00  83.02           N
ATOM   5429  CE1  HIS  D  5     8.672   5.153  29.036  1.00  83.02           C
ATOM   5430  NE2  HIS  D  5     8.668   6.438  29.321  1.00  83.02           N
ATOM   5431  C    HIS  D  5    13.353   6.371  32.310  1.00  76.32           C
ATOM   5432  O    HIS  D  5    14.538   6.074  32.558  1.00  76.32           O
ATOM   5433  N    GLN  D  6    12.620   7.161  33.066  1.00  69.29           N
ATOM   5434  CA   GLN  D  6    13.162   7.659  34.313  1.00  69.29           C
ATOM   5435  CB   GLN  D  6    12.814   9.108  34.522  1.00  73.76           C
ATOM   5436  CG   GLN  D  6    11.517   9.429  33.954  1.00  73.76           C
ATOM   5437  CD   GLN  D  6    11.712   9.889  32.567  1.00  73.76           C
ATOM   5438  OE1  GLN  D  6    12.578   9.382  31.856  1.00  73.76           O
ATOM   5439  NE2  GLN  D  6    10.932  10.863  32.157  1.00  73.76           N
ATOM   5440  C    GLN  D  6    12.461   6.844  35.348  1.00  69.29           C
ATOM   5441  O    GLN  D  6    11.784   5.790  34.919  1.00  69.29           O
ATOM   5442  N    PSE  D  7    12.609   7.261  36.621  1.00  46.32           N
ATOM   5443  CA   PSE  D  7    11.899   6.601  37.713  1.00  46.32           C
ATOM   5444  C    PSE  D  7    10.385   6.773  37.534  1.00  46.32           C
ATOM   5445  O    PSE  D  7     9.901   7.751  36.949  1.00  46.32           O
ATOM   5446  CB   PSE  D  7    12.013   7.328  38.898  1.00  43.95           C
ATOM   5447  OG   PSE  D  7    13.381   7.076  39.045  1.00  43.95           O
ATOM   5448  P    PSE  D  7    14.269   8.284  39.193  1.00  43.95           P
ATOM   5449  OP1  PSE  D  7    13.744   9.078  40.261  1.00  43.95           O
ATOM   5450  OP2  PSE  D  7    15.649   7.569  39.563  1.00  43.95           O
ATOM   5451  OP3  PSE  D  7    14.245   9.057  37.980  1.00  43.95           O
ATOM   5452  N    GLU  D  8     9.654   5.739  37.944  1.00  59.99           N
ATOM   5453  CA   GLU  D  8     8.192   5.706  37.799  1.00  59.99           C
ATOM   5454  CB   GLU  D  8     7.655   4.274  37.982  1.00  84.97           C
ATOM   5455  CG   GLU  D  8     7.950   3.315  36.869  1.00  84.97           C
ATOM   5456  CD   GLU  D  8     7.395   1.936  37.120  1.00  84.97           C
ATOM   5457  OE1  GLU  D  8     6.997   1.653  38.270  1.00  84.97           O
```

FIG. 7-92

| | | | | | | | | | |
|---|---|---|---|---|---|---|---|---|---|
| ATOM | 5458 | OE2 | GLU | D | 8 | 7.368 | 1.132 | 36.162 | 1.00 84.97 | O |
| ATOM | 5459 | C | GLU | D | 8 | 7.460 | 6.627 | 38.784 | 1.00 59.99 | C |
| ATOM | 5460 | O | GLU | D | 8 | 8.057 | 7.063 | 39.767 | 1.00 59.99 | O |
| ATOM | 5461 | N | ASP | D | 9 | 6.172 | 6.894 | 38.576 | 1.00 98.45 | N |
| ATOM | 5462 | CA | ASP | D | 9 | 5.428 | 7.783 | 39.478 | 1.00 98.45 | C |
| ATOM | 5463 | CB | ASP | D | 9 | 4.670 | 8.821 | 38.657 | 1.00103.61 | C |
| ATOM | 5464 | CG | ASP | D | 9 | 3.978 | 9.863 | 39.512 | 1.00103.61 | C |
| ATOM | 5465 | OD1 | ASP | D | 9 | 4.208 | 9.846 | 40.730 | 1.00103.61 | O |
| ATOM | 5466 | OD2 | ASP | D | 9 | 3.215 | 10.712 | 38.984 | 1.00103.61 | O |
| ATOM | 5467 | C | ASP | D | 9 | 4.439 | 7.016 | 40.348 | 1.00 98.45 | C |
| ATOM | 5468 | O | ASP | D | 9 | 4.031 | 7.587 | 41.372 | 1.00 98.45 | O |
| ATOM | 5469 | OXT | ASP | D | 9 | 4.039 | 5.885 | 39.990 | 1.00103.61 | O |
| TER | 5470 | | ASP | D | 9 | | | | | |
| ATOM | 5471 | C1 | AD2 | J | 1 | 18.557 | 22.858 | 17.579 | 1.00 38.95 | C |
| ATOM | 5472 | N2 | AD2 | J | 1 | 18.364 | 21.507 | 17.761 | 1.00 45.03 | N |
| ATOM | 5473 | C3 | AD2 | J | 1 | 18.181 | 21.023 | 19.059 | 1.00 38.95 | C |
| ATOM | 5474 | C4 | AD2 | J | 1 | 18.182 | 21.918 | 20.283 | 1.00 38.95 | C |
| ATOM | 5475 | C5 | AD2 | J | 1 | 18.405 | 23.300 | 19.974 | 1.00 38.95 | C |
| ATOM | 5476 | N6 | AD2 | J | 1 | 18.583 | 23.742 | 18.661 | 1.00 45.03 | N |
| ATOM | 5477 | N8 | AD2 | J | 1 | 17.981 | 19.766 | 19.512 | 1.00 45.03 | N |
| ATOM | 5478 | C9 | AD2 | J | 1 | 17.849 | 19.863 | 20.864 | 1.00 45.03 | C |
| ATOM | 5479 | N10 | AD2 | J | 1 | 17.961 | 21.106 | 21.361 | 1.00 45.03 | N |
| ATOM | 5480 | N12 | AD2 | J | 1 | 18.528 | 24.266 | 20.955 | 1.00 45.03 | N |
| ATOM | 5481 | C13 | AD2 | J | 1 | 18.253 | 18.582 | 18.644 | 1.00 38.95 | C |
| ATOM | 5482 | O14 | AD2 | J | 1 | 17.133 | 17.729 | 18.587 | 1.00 45.03 | O |
| ATOM | 5483 | C15 | AD2 | J | 1 | 17.295 | 16.527 | 19.301 | 1.00 38.95 | C |
| ATOM | 5484 | C16 | AD2 | J | 1 | 18.733 | 16.547 | 19.788 | 1.00 38.95 | C |
| ATOM | 5485 | C17 | AD2 | J | 1 | 19.404 | 17.645 | 19.018 | 1.00 38.95 | C |
| ATOM | 5486 | O21 | AD2 | J | 1 | 19.360 | 15.299 | 19.766 | 1.00 38.95 | O |
| ATOM | 5487 | C22 | AD2 | J | 1 | 16.217 | 16.464 | 20.361 | 1.00 38.95 | C |
| ATOM | 5488 | O1 | AD2 | J | 1 | 19.880 | 17.128 | 17.815 | 1.00 45.03 | O |
| ATOM | 5489 | O29 | AD2 | J | 1 | 16.886 | 16.429 | 21.598 | 1.00 38.95 | O |
| ATOM | 5490 | P1 | AD2 | J | 1 | 16.190 | 16.367 | 22.988 | 1.00 45.03 | P |
| ATOM | 5491 | O33 | AD2 | J | 1 | 14.896 | 15.376 | 22.967 | 1.00 38.95 | O |
| ATOM | 5492 | O34 | AD2 | J | 1 | 15.858 | 17.715 | 23.376 | 1.00 38.95 | O |
| ATOM | 5493 | O35 | AD2 | J | 1 | 17.399 | 15.765 | 23.760 | 1.00 38.95 | O |
| ATOM | 5494 | P2 | AD2 | J | 1 | 14.975 | 13.936 | 23.586 | 1.00 45.03 | P |
| ATOM | 5495 | O38 | AD2 | J | 1 | 14.187 | 12.974 | 22.932 | 1.00 38.95 | O |
| ATOM | 5496 | O39 | AD2 | J | 1 | 14.804 | 13.710 | 25.130 | 1.00 38.95 | O |
| ATOM | 5497 | O40 | AD2 | J | 1 | 16.378 | 13.611 | 23.198 | 1.00 38.95 | O |
| TER | 5498 | | AD2 | J | 1 | | | | | |
| ATOM | 5499 | C1 | AD1 | I | 1 | 16.122 | 19.968 | 81.651 | 1.00 60.87 | C |
| ATOM | 5500 | N2 | AD1 | I | 1 | 16.505 | 18.693 | 81.948 | 1.00 63.71 | N |
| ATOM | 5501 | C3 | AD1 | I | 1 | 17.842 | 18.304 | 81.666 | 1.00 60.87 | C |
| ATOM | 5502 | C4 | AD1 | I | 1 | 18.895 | 19.233 | 81.083 | 1.00 60.87 | C |
| ATOM | 5503 | C5 | AD1 | I | 1 | 18.370 | 20.518 | 80.806 | 1.00 60.87 | C |
| ATOM | 5504 | N6 | AD1 | I | 1 | 17.039 | 20.874 | 81.097 | 1.00 63.71 | N |
| ATOM | 5505 | N8 | AD1 | I | 1 | 18.509 | 17.143 | 81.857 | 1.00 63.71 | N |
| ATOM | 5506 | C9 | AD1 | I | 1 | 19.800 | 17.322 | 81.438 | 1.00 63.71 | C |
| ATOM | 5507 | N10 | AD1 | I | 1 | 20.072 | 18.540 | 80.964 | 1.00 63.71 | N |
| ATOM | 5508 | N12 | AD1 | I | 1 | 19.191 | 21.487 | 80.237 | 1.00 63.71 | N |
| ATOM | 5509 | C13 | AD1 | I | 1 | 17.749 | 15.952 | 82.304 | 1.00 60.87 | C |
| ATOM | 5510 | O14 | AD1 | I | 1 | 18.415 | 15.153 | 83.257 | 1.00 63.71 | O |
| ATOM | 5511 | C15 | AD1 | I | 1 | 18.804 | 13.900 | 82.697 | 1.00 60.87 | C |
| ATOM | 5512 | C16 | AD1 | I | 1 | 18.077 | 13.729 | 81.344 | 1.00 60.87 | C |
| ATOM | 5513 | C17 | AD1 | I | 1 | 17.272 | 15.027 | 81.184 | 1.00 60.87 | C |
| ATOM | 5514 | O21 | AD1 | I | 1 | 17.276 | 12.578 | 81.446 | 1.00 60.87 | O |
| ATOM | 5515 | C22 | AD1 | I | 1 | 20.340 | 13.759 | 82.719 | 1.00 60.87 | C |
| ATOM | 5516 | O1 | AD1 | I | 1 | 15.881 | 14.855 | 81.395 | 1.00 63.71 | O |
| ATOM | 5517 | O29 | AD1 | I | 1 | 20.953 | 14.416 | 81.621 | 1.00 60.87 | O |

FIG. 7-93

```
ATOM   5518  P1   AD1 I   1    22.462  14.183  81.300  1.00 63.71    P
ATOM   5519  O33  AD1 I   1    23.225  13.164  82.317  1.00 60.87    O
ATOM   5520  O34  AD1 I   1    23.134  15.451  81.034  1.00 60.87    O
ATOM   5521  O35  AD1 I   1    22.272  13.380  80.016  1.00 60.87    O
ATOM   5522  P2   AD1 I   1    23.018  11.592  82.047  1.00 63.71    P
ATOM   5523  O38  AD1 I   1    21.605  11.562  81.833  1.00 60.87    O
ATOM   5524  O39  AD1 I   1    23.271  10.718  83.281  1.00 60.87    O
ATOM   5525  O40  AD1 I   1    23.914  10.791  80.900  1.00 60.87    O
TER    5526       AD1 I   1
ATOM   5527  MG   MG  E   2    18.398  13.452  23.509  1.00 28.08
MG
TER    5528       MG  E   2
ATOM   5529  MG   MG  F   3    21.459  11.040  79.674  1.00 46.01
MG
TER    5530       MG  F   3
ATOM   5531  O    HOH W   1    19.003  14.328  31.052  1.00 20.17    O
ATOM   5532  O    HOH W   2    33.835   9.074  76.724  1.00 19.08    O
ATOM   5533  O    HOH W   3    29.271  31.315  41.929  1.00 23.44    O
ATOM   5534  O    HOH W   4    11.735  28.180  93.014  1.00 35.46    O
ATOM   5535  O    HOH W   5    15.794  -9.663  76.193  1.00 29.59    O
ATOM   5536  O    HOH W   7    15.029 -10.473  73.182  1.00 22.74    O
ATOM   5537  O    HOH W   8    37.399  17.234  79.714  1.00 37.43    O
ATOM   5538  O    HOH W   9    16.652  20.334  27.140  1.00 28.12    O
ATOM   5539  O    HOH W  10    36.304  11.294  84.101  1.00 48.22    O
ATOM   5540  O    HOH W  11    27.123   4.860  56.771  1.00 13.91    O
ATOM   5541  O    HOH W  12    15.199   0.336  70.441  1.00 29.67    O
ATOM   5542  O    HOH W  13    28.430   6.028  40.727  1.00 39.66    O
ATOM   5543  O    HOH W  14     4.947  23.786  18.050  1.00 26.26    O
ATOM   5544  O    HOH W  15    32.647  27.989  25.689  1.00 18.11    O
ATOM   5545  O    HOH W  16    33.710  26.403  28.185  1.00 41.53    O
ATOM   5546  O    HOH W  17    36.872  18.366  41.289  1.00 39.01    O
ATOM   5547  O    HOH W  18    13.886  13.318  35.235  1.00 48.82    O
ATOM   5548  O    HOH W  19    30.998  15.417  40.405  1.00 28.44    O
ATOM   5549  O    HOH W  20    23.541  -3.518  55.672  1.00 34.51    O
ATOM   5550  O    HOH W  21    36.719  35.310  16.361  1.00 33.78    O
ATOM   5551  O    HOH W  22    16.917  12.168  28.199  1.00 31.20    O
ATOM   5552  O    HOH W  23    19.678  -1.951  69.208  1.00 30.61    O
ATOM   5553  O    HOH W  24    27.122   5.213  76.529  1.00 52.25    O
ATOM   5554  O    HOH W  25    26.095  12.525  43.440  1.00 22.76    O
ATOM   5555  O    HOH W  26    24.594  15.119  45.793  1.00 29.48    O
ATOM   5556  O    HOH W  27    24.331  22.522  93.476  1.00 22.70    O
ATOM   5557  O    HOH W  28    29.790  30.372  32.816  1.00 36.83    O
ATOM   5558  O    HOH W  29     9.880 -12.937  58.476  1.00 32.42    O
ATOM   5559  O    HOH W  30    30.701   0.664  17.143  1.00 46.78    O
ATOM   5560  O    HOH W  31    24.073  29.316  17.706  1.00 40.34    O
ATOM   5561  O    HOH W  32     9.814  18.393  33.742  1.00 35.42    O
ATOM   5562  O    HOH W  33    37.162  19.106  67.629  1.00 30.46    O
ATOM   5563  O    HOH W  34    14.054  33.888  93.035  1.00 28.61    O
ATOM   5564  O    HOH W  35    25.683  24.262  71.753  1.00 40.38    O
ATOM   5565  O    HOH W  36    16.414  19.968  54.544  1.00 57.48    O
ATOM   5566  O    HOH W  37    11.487  14.595  32.470  1.00 42.52    O
ATOM   5567  O    HOH W  38    33.214  11.246  38.966  1.00 46.27    O
ATOM   5568  O    HOH W  39    25.358  10.138  31.388  1.00 24.33    O
ATOM   5569  O    HOH W  40    26.113  33.092  30.825  1.00 42.45    O
ATOM   5570  O    HOH W  41    14.596  27.086  89.788  1.00 36.96    O
ATOM   5571  O    HOH W  42    14.892  19.885  95.551  1.00 37.47    O
ATOM   5572  O    HOH W  43    31.900   6.761  84.936  1.00 35.38    O
ATOM   5573  O    HOH W  44    18.771  27.551  30.942  1.00 22.54    O
ATOM   5574  O    HOH W  45    11.917  18.894  84.248  1.00 40.30    O
ATOM   5575  O    HOH W  46     6.986  20.428  70.209  1.00 57.28    O
```

FIG. 7-94

```
ATOM   5576  O    HOH W  47      24.987   2.314  68.413  1.00 28.36           O
ATOM   5577  O    HOH W  48      32.977  18.855  39.603  1.00 63.81           O
ATOM   5578  O    HOH W  49      27.160  11.510  82.090  1.00 56.37           O
ATOM   5579  O    HOH W  50      28.650   5.338   7.158  1.00 43.22           O
ATOM   5580  O    HOH W  51      27.767   3.212  46.392  1.00 13.38           O
TER    5581       HOH W  51
E
N
D
```

INHIBITORS OF GSK-3 AND CRYSTAL STRUCTURES OF GSK-3β PROTEIN AND PROTEIN COMPLEXES

This application is a divisional of U.S. application Ser. No. 10/135,255, filed Apr. 29, 2002, now U.S. Pat. No. 7,390,808, which claims the benefit of U.S. Provisional Application No. 60/361,899, filed Feb. 27, 2002, U.S. Provisional Application No. 60/297,094, filed Jun. 8, 2001, and U.S. Provisional Application No. 60/287,366, filed Apr. 30, 2001. Each of these prior applications is hereby incorporated by reference in its entirety.

TECHNICAL FIELD OF INVENTION

The present invention relates to inhibitors of glycogen synthase kinase-3 (GSK-3), a serine/threonine protein kinase, and to methods for producing them. The invention also provides pharmaceutical compositions comprising the inhibitors of the invention and methods of utilizing those compositions in the treatment and prevention of various disease states, such as diabetes and Alzheimer's disease. The present invention also relates to molecules or molecular complexes which comprise binding pockets of GSK-3β, or its homologues. The present invention provides a computer comprising a data storage medium encoded with the structure coordinates of such binding pockets. This invention also relates to methods of using the structure coordinates to solve the structure of homologous proteins or protein complexes. In addition, this invention relates to methods of using the structure coordinates to screen for and design compounds, including inhibitory compounds, that bind to GSK-3β protein or homologues thereof. The invention also relates to crystallizable compositions and crystals comprising GSK-3β protein or GSK-3β protein complexes.

BACKGROUND OF THE INVENTION

Protein kinases mediate intracellular signal transduction by affecting a phosphoryl transfer from a nucleoside triphosphate to a protein acceptor involved in a signaling pathway. There are a number of kinases and pathways through which extracellular and other stimuli cause a variety of cellular responses to occur inside the cell. Examples of such stimuli include environmental and chemical stress signals (e.g., osmotic shock, heat shock, ultraviolet radiation, bacterial endotoxin, $H_2O_2$), cytokines (e.g., interleukin-1 (IL-1) and tumor necrosis factor α (TNF-α)), growth factors (e.g., granulocyte macrophage-colony-stimulating factor (GM-CSF), and fibroblast growth factor (FGF). An extracellular stimulus may affect one or more cellular responses related to cell growth, migration, differentiation, secretion of hormones, activation of transcription factors, muscle contraction, glucose metabolism, control of protein synthesis and regulation of cell cycle. Many disease states are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease and hormone-related diseases.

GSK-3 is a serine/threonine protein kinase and belongs to the superfamily of mitogen-activated protein kinases. MAP kinases are activated by phosphorylation of threonine and/or tyrosine residues in a loop adjacent to the active site. Phosphorylation of MAP kinases is carried out by specific kinases upstream. Activated MAP kinase then phosphorylates the various substrates.

Mammalian cells have α and β isoforms of GSK-3 that are each encoded by distinct genes (Coghlan et al., *Chemistry & Biology*, 7, pp. 793-803 (2000); Kim and Kimmel, *Curr. Opinion Genetics Dev.*, 10, pp. 508-514 (2000)). The core kinase sequences have 97% similarity, but the protein sequences deviate substantially outside the kinase core (Woodgett, J. R., *EMBO J.*, 9, pp. 2431-8 (1990)). GSK-3α is 63 residues longer at the N-terminal end than GSK-3β, however the N-terminal phosphorylation site in both isoforms (S21 for GSK-3α and S9 for GSK-3β) is embedded in a conserved 7 residue motif. The two isoforms are not redundant as GSK-3β deficiency is lethal in embryogenesis due to severe liver degeneration (Hoeflich, K. P., et al., *Nature*, 406, pp. 86-90 (2000)).

GSK-3β has multiple phosphorylation sites. The Serine 9 and Tyrosine 216 phosphorylation sites are well described in the literature. Phosphorylation of Tyrosine 216 activates GSK-3β but phosphorylation of Serine 9 inactivates it. GSK-3β is unique among kinases in that it requires prior phosphorylation of its substrates. GSK-3β does not phosphorylate its multiple substrates in the same manner and with the same efficiency but has different modes of phosphorylation. The canonical phosphorylation sequence recognized by GSK-3β, SXXXS, contains two serines separated by three amino acid residues. Multiple copies of this motif can be present in the substrate. Several protein substrates such as glycogen synthase, eIF2b and APC, are first phosphorylated by a different kinase at the P+4 serine in the $_{p+4}SXXXS_p$ motif before GSK-3β phosphorylates the serine in the P position. This is called primed phosphorylation, and is approximately 100 to 1000 times faster than the phosphorylation without priming (Thomas, G. M., et al., *FEBS Lett.*, 458, pp. 247-51 (1999)). Glycogen synthase has multiple serines separated by four residues (residue 640, 644, 648, and 652) and those serines are phosphorylated sequentially by GSK-3β from the C-terminal end, after S656 has been phosphorylated by Casein Kinase II (Woodgett, J. R. and P. Cohen, *Biochim. Biophys. Acta*, 788, pp. 339-47 (1984); Kuret, J. et al, *Eur. J. Biochem.*, 151, pp. 39-48 (1985)).

Glycogen synthase kinase-3 has been implicated in various diseases including diabetes, Alzheimer's disease, CNS disorders such as manic depressive disorder and neurodegenerative diseases, and cardiomyocete hypertrophy (WO 99/65897; WO 00/38675; and Haq et al., *J. Cell Biol.*, 151, pp. 117 (2000)). These diseases may be caused by, or result in, the abnormal operation of certain cell signaling pathways in which GSK-3 plays a role. GSK-3 phosphorylates and modulates the activity of a number of regulatory proteins. These include glycogen synthase which is the rate limiting enzyme necessary for glycogen synthesis, the microtubule associated protein Tau, the gene transcription factor beta-catenin, the translation initiation factor e1F2B, as well as ATP citrate lyase, axin, heat shock factor-1, c-Jun, c-Myc, c-Myb, CREB and CEPBa. These diverse targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Insulin inactivates GSK-3β via the PKB/Akt pathway, which results in activation of glycogen synthase. (Summers, S. A., et al., *J. Biol. Chem.*, 274, pp. 17934-40 (1999); Ross, S. E., et al., *Mol. Cell. Biol.*, 19, pp. 8433-41 (1999)). The inhibition of GSK-3 leads to increased glycogen synthesis and glucose uptake (Klein et al., *PNAS*, 93, pp. 8455-9 (1996); Cross et al., *Biochem. J.*, 303, pp. 21-26 (1994);

Cohen, *Biochem. Soc. Trans.*, 21, pp. 555-567 (1993); Massillon et al., *Biochem. J.* 299, pp. 123-128 (1994)). However, in a diabetic patient where the insulin response is impaired, glycogen synthesis and glucose uptake fail to increase despite the presence of relatively high blood levels of insulin. This leads to abnormally high blood levels of glucose with acute and long term effects that may ultimately result in cardiovascular diseases, renal failure and blindness. In such patients, the normal insulin-induced inhibition of GSK-3 fails to occur. It has also been reported that in patients with type II diabetes, GSK-3 is overexpressed (WO 00/38675). Therapeutic inhibitors of GSK-3 are therefore potentially useful for treating diabetic patients suffering from an impaired response to insulin.

GSK-3 activity has also been associated with Alzheimer's disease. This disease is characterized by the well-known β-amyloid peptide and the formation of intracellular neurofibrillary tangles. The neurofibrillary tangles contain hyperphosphorylated Tau protein where Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells (Lovestone et al., *Current Biology*, 4, pp. 1077-86 (1994); Brownlees et al., *Neuroreport*, 8, pp. 3251-55 (1997)). Therefore, it is believed that GSK-3 activity may promote generation of the neurofibrillary tangles and the progression of Alzheimer's disease.

Another substrate of GSK-3 is beta-catenin which is degraded after phosphorylation by GSK-3. Reduced levels of beta-catenin have been reported in schizophrenic patients and have also been associated with other diseases related to increase in neuronal cell death (Zhong et al., *Nature*, 395, 698-702 (1998); Takashima et al., *PNAS*, 90, 7789-93 (1993); Pei et al., *J. Neuropathol. Exp.*, 56, 70-78 (1997)).

GSK-3β is also a component of the Wnt signalling pathway. Activation of the Wnt pathway inhibits GSK-3β, which results in accumulation of cytosolic β-catenin (Yost, C., et al., *Cell*, 93, pp. 1031-41 (1998)). The cytosolic β-catenin translocates to the cell nucleus, where it associates with LEF/tcf and stimulates the expression of Wnt target genes resulting in cell proliferation (Ding, V. W., et al., *J. Biol. Chem.*, 275, pp. 32475-81 (2000); Waltzer, L. and M. Bienz, *Cancer Metastasis Rev.* 18, pp. 231-46 (1999); Ikeda, S., et al., *EMBO J.*, 17, pp. 1371-84 (1998); Thomas, G. M., et al., *FEBS Lett*, 458, pp. 247-51 (1999); Salic, A., et al., *Mol. Cell.*, 5, pp. 523-32 (2000)). The activity of GSK-3β is also down regulated by 7-TM receptors that regulate cAMP levels. cAMP-dependent protein kinase A, binds, phosphorylates and inhibits GSK-3β in response to the adenyl cyclase activator forskolin, or the p-adrenergic receptor activator isoproterenol (Fang, X., et al., *Proc. Natl. Acad. Sci. USA*, 97, pp. 11960-5 (2000)).

Small molecule inhibitors of GSK-3 have recently been reported (WO 99/65897 and WO 00/38675). For many of the aforementioned diseases associated with abnormal GSK-3 activity, other protein kinases have also been targeted for treating the same diseases. However, the various protein kinases often act through different biological pathways. Quinazoline derivatives have been reported recently as inhibitors of p38 kinase (WO 00/12497). The compounds are reported to be useful for treating conditions characterized by enhanced p38-α activity and/or enhanced TGF-β activity. While p38 activity has been implicated in a wide variety of diseases, including diabetes, p38 kinase is not reported to be a constituent of an insulin signaling pathway that regulates glycogen synthesis or glucose uptake. Therefore, unlike GSK-3, p38 inhibition would not be expected to enhance glycogen synthesis and/or glucose uptake.

Accordingly, there has been an interest in finding GSK-3 inhibitors that are effective as therapeutic agents due to its important role in diabetes, Alzheimer's disease and other diseases. A challenge has been to find protein kinase inhibitors that act in a selective manner. Since there are numerous protein kinases that are involved in a variety of cellular responses, non-selective inhibitors may lead to unwanted side effects.

In this regard, the three-dimensional structure of the kinase would assist in the rational design of inhibitors. Further, information provided by the X-ray crystal structure of GSK-3β-inhibitor complexes would be extremely useful in iterative drug design of various GSK-3 proteins. The determination of the amino acid residues in GSK-3β binding pockets and the determination of the shape of those binding pockets would allow one to design inhibitors that bind more favorably to this class of enzymes.

SUMMARY OF THE INVENTION

The present invention addresses this need by providing compounds and pharmaceutical compositions thereof that are effective as protein kinase inhibitors, particularly as inhibitors of GSK-3. Applicants have also addressed this need by providing the crystal structures of a unphosphorylated GSK-3β, a phosphorylated GSK-3β, unphosphorylated GSK-3β-inhibitor complexes, a phosphorylated GSK-3β-inhibitor complex and a phosphorylated GSK-3β-ADP-peptide complex. Solving these crystal structures has allowed the determination of the key structural features of GSK-3β, particularly the shape of its substrate and ATP-binding pockets.

The compounds of the present invention have the general formula I:

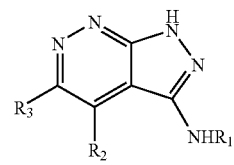

or a pharmaceutically acceptable derivative thereof, wherein:
$R_1$ is selected from H, aliphatic, RC(O)—, RS(O)$_n$—, ROC(O)—, carbocyclyl, heterocyclyl, aryl, aralkyl, heteroaryl, or heteroaralkyl; wherein said aliphatic, carbocyclyl, heterocyclyl, aryl, aralkyl, heteroaryl, or heteroaralkyl is optionally substituted;

$R_2$ and $R_3$ are each independently selected from H, aliphatic, carbocyclyl, heterocyclyl, aryl, aralkyl, heteroaryl, heteroaralkyl, —N(R)$_2$, —NRCOR, —NRCO$_2$R, —NRCO$_2$R, —S(O)$_n$R, —SO$_2$N(R)$_2$, —SR, —OR, —CF$_3$, halo, —NO$_2$, —CN, —C(O)R, —CO$_2$R, —OC(O)R, —CON(R)$_2$, or —OC(O)N(R)$_2$, wherein said aliphatic, carbocyclyl, heterocyclyl, aryl, aralkyl, heteroaryl, or heteroaralkyl is optionally substituted; or $R_2$ and $R_3$ taken together with the intervening atoms optionally form a five- to nine-membered ring that is fused to the pyridazinyl ring of formula I, said fused ring having 0-2 heteroatoms;

each R is independently selected from H, aliphatic, carbocyclyl, heterocyclyl, aryl, aralkyl, heteroaryl, or heteroaralkyl, wherein each member of R except H is optionally substituted; and n is 1 or 2;

provided that when $R_1$ is H, $R_2$ and $R_3$ are not both unsubstituted phenyl; and when $R_1$ is H, $R_2$ and $R_3$ are other than H, halogen, or an unsubstituted alkyl.

In another embodiment, the invention provides pharmaceutical compositions comprising a GSK-3 inhibitor of this invention. These compositions may be utilized in methods for treating or preventing a variety of GSK-3 mediated disorders, such as autoimmune diseases, inflammatory diseases, metabolic, neurological and neurodegenerative diseases, cardiovascular diseases, allergy, asthma, diabetes, Alzheimer's disease, Huntington's Disease, Parkinson's Disease, AIDS-associated dementia, amyotrophic lateral sclerosis (AML, Lou Gehrig's Disease), multiple sclerosis (MS), schizophrenia, cardiomyocyte hypertrophy, reperfusion/ischemia, and baldness.

The compositions of this invention are also useful in methods for enhancing glycogen synthesis and/or lowering blood levels of glucose and therefore are especially useful for diabetic patients. These compositions are also useful in methods for inhibiting the production of hyperphosphorylated Tau protein, which is useful in halting or slowing the progression of Alzheimer's disease. Another embodiment of this invention relates to a method for inhibiting the phosphorylation of β-catenin, which is useful for treating schizophrenia.

In another embodiment, the invention provides methods of synthesizing compounds of formula I and preparing pharmaceutical compositions comprising these compounds.

The present invention also provides molecules or molecular complexes comprising GSK-3β binding pockets, or GSK-3β-like binding pockets that have similar three-dimensional shapes. In one embodiment, the molecules or molecular complexes are GSK-3β proteins, protein complexes or homologues thereof. In another embodiment, the molecules or molecular complexes are in crystalline form.

The invention provides crystallizable compositions and crystal compositions comprising unphosphorylated GSK-3β, phosphorylated GSK-3β or their homologues with or without a chemical entity. The invention also provides a method for crystallizing a GSK-3β protein, protein complex, or homologues thereof.

The invention provides a data storage medium which comprises the structure coordinates of molecules or molecular complexes of the GSK-3β binding pockets or GSK-3β-like binding pockets. In one embodiment, the data storage medium comprises the structure coordinates of the binding pocket. The invention also provides a computer comprising the data storage medium. Such storage medium when read and utilized by a computer programmed with appropriate software can display, on a computer screen or similar viewing device, a three-dimensional graphical representation of such binding pockets.

The invention also provides methods for designing, evaluating and identifying compounds which bind to the molecules or molecular complexes or their binding pockets. Such compounds are potential inhibitors of GSK-3β or its homologues.

The invention also provides a method for determining at least a portion of the three-dimensional structure of molecules or molecular complexes which contain at least some structurally similar features to GSK-3β, particularly GSK-3β homologues. This is achieved by using at least some of the structure coordinates obtained from the unphosphorylated or phosphorylated GSK-3β protein or protein complexes.

BRIEF DESCRIPTION OF THE FIGURES

FIG. 1 lists the atomic structure coordinates for unphosphorylated GSK-3β as derived by X-ray diffraction from the crystal. FIG. 1 depicts residues 25-119, 127-285, 301-384, 37-285 and 291-382 of SEQ ID NO:1, respectively, in order of appearance.

FIG. 2 lists the atomic structure coordinates for phosphorylated GSK-3β. FIG. 2 depicts SEQ ID NOS: 22-27, respectively, in order of appearance.

FIG. 3 lists the atomic structure coordinates for phosphorylated GSK-3β-inhibitor1 complex (inhibitor 1 is 4,5-Diphenyl-1H-pyrazolo[3,4-c]pyridazin-3-ylamine). FIG. 3 depicts SEQ ID NOS: 28-33, respectively, in order of appearance.

FIG. 4 lists the atomic structure coordinates for unphosphorylated GSK-3β-inhibitor 2 complex (inhibitor2 is (5-Methyl-2H-pyrazol-3-yl)-(2-pyridin-4-yl-quinazolin-4-yl)-amine)). FIG. 4 depicts SEQ ID NOS: 34-38, respectively, in order of appearance.

FIG. 5 lists the atomic structure coordinates for unphosphorylated GSK-3β-inhibitor3 complex (inhibitor 3 is 4-(5-Methyl-2-phenylamino-pyrimidin-4-yl)-1H-pyrrole-2-carboxylic acid (2-hydroxy-1-phenyl-ethyl)-amide). FIG. 5 depicts SEQ ID NOS: 39-44, respectively, in order of appearance.

FIG. 6 lists the atomic structure coordinates for unphosphorylated GSK-3β-inhibitor4 complex (inhibitor 4 is (1H-Indazo-1-3-yl)-[2-(2-trifluoromethyl-phenyl)-quinazolin-4-yl]-amine). FIG. 6 depicts SEQ ID NOS:45-49, respectively, in order of appearance.

FIG. 7 lists the atomic structure coordinates for phosphorylated GSK-3β in complex with ADP and glycogen synthase peptide. FIG. 7 depicts SEQ ID NOS: 50 -55, respectively, in order of appearance.

Figure 8:
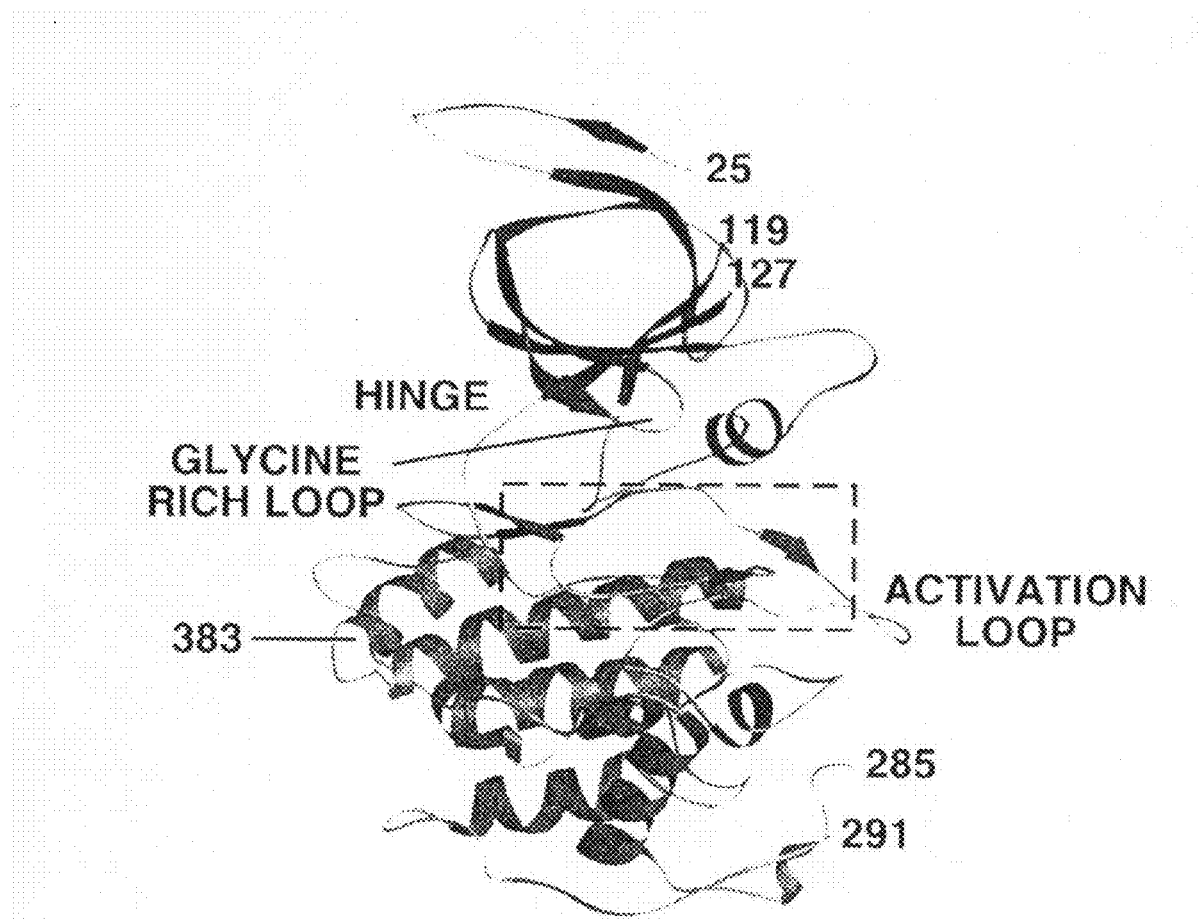
FIG. 8 depicts a ribbon diagram of the overall fold of unphosphorylated GSK-3β. The N-terminal domain corresponds to the β-strand domain and encompasses residues 25 to 138. β-strand 1 was only visible in one of the two molecules in the asymmetric unit and makes hydrogen bonds with β-strand 2 although it is not part of the β-barrel. The α-helical domain corresponds to residues 139 to 349. Key features of the kinase-fold such as the hinge, glycine rich loop and activation-loop are indicated.

The following abbreviations are used in FIGS. 1-5:

"Atom type" refers to the element whose coordinates are measured. The first letter in the column defines the element.

"Res" refers to the amino acid residue in the molecular model.

"X, Y, Z" crystallographically define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in all molecules of the crystal.

DETAILED DESCRIPTION OF THE INVENTION

In order that the invention described herein may be more fully understood, the following detailed description is set forth.

Throughout the specification, the word "comprise" or variations such as "comprises" or "comprising" will be understood to imply the inclusion of a stated integer or groups of integers but not the exclusion of any other integer or groups of integers.

The following abbreviations are used throughout the application:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |
| pS = Phosphorylated Serine | pTy = Phosphorylated Tyrosine |

As used herein, the following definitions shall apply unless otherwise indicated. Also, combinations of substituents or variables are permissible only if such combinations result in stable compounds.

The term "about" when used in the context of RMSD values takes into consideration the standard error of the RMSD value, which is ±0.1 Å.

The term "active site" refers to the area in the protein kinase where the nucleotide binds. This site is located at the interface of the C-terminal α-helical and N-terminal β-strand domain, and is bordered by the glycine rich loop and the hinge (See, Xie et al., *Structure*, 6, pp. 983-991 (1998), incorporated herein by reference).

The term "aliphatic" refers to straight chain or branched hydrocarbons that are completely saturated or that contain one or more units of unsaturation. For example, aliphatic groups include substituted or unsubstituted linear or branched alkyl, alkenyl and alkynyl groups. Unless indicated otherwise, the term "aliphatic" encompasses both substituted and unsubstituted hydrocarbons. The term "alkyl", used alone or as part of a larger moiety, refers to both straight and branched saturated chains containing one to twelve carbon atoms. The terms "alkenyl" and "alkynyl", used alone or as part of a larger moiety, encompass both straight and branched chains containing two to twelve carbon atoms and at least one unit of unsaturation. An alkenyl group contains at least one carbon-carbon double bond and an alkynyl group contains at least one carbon-carbon triple bond.

The term "correspond to" or "corresponding amino acids" when used in the context of amino acid residues that correspond to GSK-3β amino acids refers to particular amino acids or analogues thereof in a protein that correspond to amino acids in the GSK-3β protein. The corresponding amino acid may be an identical, mutated, chemically modified, conserved, conservatively substituted, functionally equivalent or homologous amino acid when compared to the GSK-3β amino acid to which it corresponds.

Methods for identifying a corresponding amino acid are known in the art and are based upon sequence, structural alignment, its functional position or a combination thereof as compared to the GSK-3β protein. For example, corresponding amino acids may be identified by superimposing the backbone atoms of the amino acids in GSK-3β and the protein using well known software applications, such as QUANTA (Molecular Simulations, Inc., San Diego, Calif. ©2000). The corresponding amino acids may also be identified using sequence alignment programs such as the "bestfit" program available from the Genetics Computer Group which uses the local homology algorithm described by Smith and Waterman in *Advances in Applied Mathematics* 2, 482 (1981), which is incorporated herein by reference.

The term "aryl", alone or in combination with other terms, refers to monocyclic or polycyclic aromatic carbon ring systems having five to fourteen members. Examples of aryl groups include, but are not limited to, phenyl (Ph), 1-naphthyl, 2-naphthyl, 1-anthracyl and 2-anthracyl. The term "aralkyl" refers to an alkyl group substituted by an aryl. Also explicitly included within the scope of the term "aralkyl" are alkenyl or alkynyl groups substituted by an aryl. Examples of aralkyl groups include benzyl and phenethyl. The term "aryl", "aryl group" or "aryl ring" also refers to rings that are optionally substituted, unless otherwise indicated.

The term "associating with" refers to a condition of proximity between a chemical entity or compound, or portions thereof, and a binding pocket or binding site on a protein. The association may be non-covalent—wherein the juxtaposition is energetically favored by hydrogen bonding or van der Waals or electrostatic interactions—or it may be covalent.

The term "ATP analogue" refers to a compound derived from Adenosine-5'-triphosphate(ATP). The analogue can be ADP, or non-hydralysable, for example, Adenylyl Imidodiphosphate (AMPPNP). AMPPNP can be in complex with Magnesium or Manganese ions.

The term "binding pocket" refers to a region of a molecule or molecular complex, that, as a result of its shape, favorably associates with another chemical entity or compound.

The term "biological sample" includes, without limitation, cell cultures or extracts thereof; biopsied material obtained from a mammal or extracts thereof; and blood, saliva, urine, feces, semen, tears, or other body fluids or extracts thereof.

The term "carbocylyl" or "carbocyclic", alone or in combination with any other term, refers to monocyclic or polycyclic non-aromatic carbon ring systems, which may contain a specified number of carbon atoms, preferably from 3 to 12 carbon atoms, which are completely saturated or which contain one or more units of unsaturation. A carbocyclic ring system may be monocyclic, bicyclic or tricyclic. A carbocylyl ring may be fused to another ring, such as an aryl ring or another carbocyclic ring. Examples of carbocyclic rings could include cyclohexyl, cyclopentyl, cyclobutyl, cyclopropyl, cyclohexenyl, cyclopentenyl, indanyl, tetrahydronaphthyl and the like. The term "carbocyclic" or "carbocylyl", whether saturated or unsaturated, also refers to rings that are optionally substituted unless indicated. The term "carbocyclic" or "carbocylyl" also encompasses hybrids of aliphatic and carbocyclic groups, such as (cycloalkyl)alkyl, (cycloalkenyl)alkyl and (cycloalkyl)alkenyl.

The term "chemically feasible or stable" refers to a compound structure that is sufficiently stable to allow manufacture and administration to a patient by methods known in the art. Typically, such compounds are stable at a temperature of 40° C. or less, in the absence of moisture or other chemically reactive conditions, for at least one week.

The term "chemical entity" refers to chemical compounds, complexes of at least two chemical compounds, and fragments of such compounds or complexes. The chemical entity can be, for example, a ligand, a substrate, nucleotide triphosphate, a nucleotide, an agonist, antagonist, inhibitor, antibody, peptide, protein or drug. In one embodiment, the chemical entity is selected from the group consisting of an ATP and an inhibitor for the active site. In one embodiment, the inhibitor is 4,5-Diphenyl-1H-pyrazolo[3,4-c]pyridazin-3-ylamine, (5-Methyl-2H-pyrazol-3-yl)-(2-pyridin-4-yl-quinazolin-4-yl)-amine, 4-(5-Methyl-2-phenylamino-pyrimidin-4-yl)-1H-pyrrole-2-carboxylic acid (2-hydroxy-1-phenyl-ethyl)-amide, (1H-Indazol-3-yl)-[2-(2-trifluoromethyl-phenyl)-quinazolin-4-yl]-amine and an ATP analogue such as MgAMP-PNP (adenylyl imidodiphosphate) or ADP. In one embodiment, the chemical entity is selected from the group consisting of a peptide substrate or inhibitor for the substrate binding groove.

The term "crystallization solution" refers to a solution that promotes crystallization of macromolecules. The crystallization solution may contain a precipitant, a buffer, salt, stabilizer, a polyionic agent, a detergent, a lanthanide ion or reducing agent. One of ordinary skilled in the art may adjust the components of the crystallization solution to find a condition suitable for the macromolecule of interest.

The term "conservative substitutions" refers to residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., *Atlas of Protein Sequence and Structure*, 5, pp. 345-352 (1978 & Supp.), which is incorporated herein by reference. Examples of conservative substitutions are substitutions including but not limited to the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

The term "complex" refers to a protein associated with a chemical entity.

The term "domain" refers to a structural unit of the GSK-3β protein or homologue. The domain can comprise a binding pocket, or a sequence or structural motif. In GSK-3β, the protein is separated into two domains, the N-terminal domain which is predominantly β strands and the C-terminal domain which is predominantly α helical.

The term "generating a three-dimensional structure" refers to plotting the structure coordinates in three-dimensional space. This can be achieved through commercially available software. The three-dimensional structure may be used to perform computer modeling, fitting operations, or displayed as a three-dimensional graphical representation.

The term "GSK-3β inhibitor-binding pocket" or "GSK-3β ATP-binding pocket" refers to a binding pocket of a molecule or molecular complex defined by the structure coordinates of a certain set of amino acid residues present in the GSK-3β structure, as described below. This binding pocket is in an area in the GSK-3β protein where the ATP or inhibitor for the active site binds.

The term "GSK-3β-like" refers to all or a portion of a molecule or molecular complex that has a commonality of shape to all or a portion of the GSK-3β protein. For example, in the GSK-3β-like inhibitor binding pocket, the commonality of shape is defined by a root mean square deviation of the structure coordinates of the backbone atoms between the amino acids in the GSK-3β-like inhibitor-binding pocket and the GSK-3β amino acids in the GSK-3β inhibitor-binding pocket (as set forth in any one of FIG. 1-7). Depending on the set of GSK-3β amino acids that define the GSK-3β inhibitor-binding pocket, one skilled in the art would be able to locate the corresponding amino acids that define a GSK-3β-like inhibitor-binding pocket in a protein based on sequence or structural homology.

The term "GSK-3-mediated condition" or "state" refers to any disease or other deleterious condition or state in which GSK-3, in particular GSK-3, is known to play a role. Such diseases or conditions include, without limitation, diabetes, Alzheimer's disease, Huntington's Disease, Parkinson's Disease, AIDS-associated dementia, amyotrophic lateral sclerosis (AML), multiple sclerosis (MS), schizophrenia, cardiomycete hypertrophy, reperfusion/ischemia, and baldness.

The term "halogen" or "halo" means F, Cl, Br, or I.

The term "heteroatom" means N, O, or S and shall include any oxidized form of nitrogen and sulfur, such as N(O), S(O), $S(O)_2$ and the quaternized form of any basic nitrogen.

The term "heterocyclic" or "heterocyclyl" refers to non-aromatic saturated or unsaturated monocyclic or polycyclic ring systems containing one or more heteroatoms and with a ring size of three to fourteen. One having ordinary skill in the art will recognize that the maximum number of heteroatoms in a stable, chemically feasible heterocyclic ring is determined by the size of the ring, degree of unsaturation, and valence. In general, a heterocyclic ring may have one to four heteroatoms so long as the heterocyclic ring is chemically feasible and stable and may be fused to another ring, such as a carbocyclic, aryl or heteroaryl ring, or to another heterocyclic ring. A heterocyclic ring system may be monocyclic, bicyclic or tricyclic. Also included within the scope of within the scope of the term "heterocyclic" or "heterocyclyl", as used herein, is a group in which one or more carbocyclic rings are fused to a heteroaryl.

Examples of heterocyclic rings include, but are not limited to, 3-1H-benzimidazol-2-one, 3-1H-alkyl-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxane, benzotriazol-1-yl, benzopyrrolidine, benzopiperidine, benzoxolane, benzothiolane, benzothiane, aziranyl, oxiranyl, azetidinyl, pyrrolinyl, dioxolanyl, imidazolinyl, imidazolidinyl, pyrazolinyl, pyrazolidinyl, pyranyl, dioxanyl, dithianyl, trithianyl, quinuclidinyl, oxepanyl, and thiepanyl. The term "heterocyclic" ring, whether saturated or unsaturated, also refers to rings that are optionally substituted, unless otherwise indicated.

The term "heteroaryl", alone or in combination with any other term, refers to monocyclic or polycyclic aromatic ring systems having five to fourteen members and one or more heteroatoms. One having ordinary skill in the art will recognize that the maximum number of heteroatoms in a stable, chemically feasible heteroaryl ring is determined by the size of the ring and valence.

The term "heteroaralkyl" refers to an alkyl group substituted by a heteroaryl. Also explicitly included within the scope of the term "heteroaralkyl", are alkenyl or alkynyl groups substituted by a heteroaryl. In general, a heteroaryl ring may have one to four heteroatoms. Heteroaryl groups include, without limitation, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, and 3-thienyl. The term "heteroaryl ring", "heteroaryl group", or "heteroaralkyl" also refers to rings that are optionally substituted.

Examples of fused polycyclic heteroaryl and aryl ring systems in which a carbocyclic aromatic ring or heteroaryl ring is fused to one or more other rings include, tetrahydronaphthyl, benzimidazolyl, benzothienyl, benzofuranyl, indolyl, quinolinyl, benzothiazolyl, benzoxazolyl, benzimidazolyl, isoquinolinyl, isoindolyl, acridinyl, benzoisoxazolyl, and the like.

An aryl, aralkyl, heteroaryl, or heteroaralkyl group may contain one or more independently selected substituents. Examples of suitable substituents on the unsaturated carbon atom of an aryl or heteroaryl group include halogen, $CF_3$, —R', —OR', —OH, —SH, —SR', protected OH (such as acyloxy), —$NO_2$, —CN, —$NH_2$, —NHR', —N(R')$_2$, —NHCOR', —NHCONH$_2$, —NHCONHR', —NHCON(R')$_2$, —NRCOR', —NHCO$_2$H, —NHCO$_2$R', —CO$_2$R', —CO$_2$H, —COR', —CONH$_2$, —CONHR', —CON(R')$_2$, —S(O)$_2$H, —S(O)$_2$R', —SO$_2$NH$_2$, —S(O)H, —S(O)R', —SO$_2$NHR', —SO$_2$N(R')$_2$, —NHS(O)$_2$H, or —NHS(O)$_2$R', where R' is selected from H, aliphatic, carbocyclyl, heterocyclyl, aryl, aralkyl, heteroaryl, or heteroaralkyl and each R' is optionally substituted with halogen, nitro, cyano, amino, —NH— (unsubstituted aliphatic), —N-(unsubstituted aliphatic)$_2$, carboxy, carbamoyl, hydroxy, —O— (unsubstituted aliphatic), —SH, —S— (unsubstituted aliphatic), $CF_3$, —SO$_2$NH$_2$, unsubstituted aliphatic, unsubstituted carbocyclyl, unsubstituted heterocyclyl, unsubstituted aryl, unsubstituted aralkyl, unsubstituted heteroaryl, or unsubstituted heteroaralkyl.

An aliphatic group or a non-aromatic heterocyclic ring may contain one or more substituents. Examples of suitable substituents on the saturated carbon of an aliphatic group or of a non-aromatic heterocyclic ring include those listed above for the unsaturated carbon as well as the following: =O, =S; =NNHR', =NN(R')$_2$, =N—OR', =NNHCOR', =NNHCO$_2$R', =NNHSO$_2$R', =N—CN, or =NR', wherein R' is as defined above. Guided by this specification, the selection of suitable substituents is within the knowledge of one skilled in the art.

A substitutable nitrogen on a heteroaryl or a non-aromatic heterocyclic ring is optionally substituted. Suitable substituents on the nitrogen include R", COR", S(O)$_2$R", and CO$_2$R", where R" is H, an aliphatic group or a substituted aliphatic group.

The term "motif" refers to a group of amino acids in the protein that defines a structural compartment or carries out a function in the protein, for example, catalysis, structural stabilization or phosphorylation. The motif may be conserved in sequence, structure and function when. The motif can be contiguous in primary sequence or three-dimensional space. Examples of a motif include but are not limited to SXXXS motif, phosphorylation lip or activation loop, the glycine-rich phosphate anchor loop, the catalytic loop, the DFG loop and the APE motif (See, Xie et al., *Structure*, 6, pp. 983-991 (1998)).

The term "homologue of GSK-3β" or "GSK-3β homologue" refers to a molecule that is homologous to GSK-3β by structure or sequence, but retains the kinase activity of GSK-3. In one embodiment, the homologue has at least 80%, 90% or 95% sequence homology to GSK-3β. The homologue can be GSK-3α, GSK-3β from another species, with conservative substitutions, conservative additions or deletions thereof; human GSK-3β with conservative substitutions, conservative additions or deletions. For example, the GSK-3β can be full length protein (amino acids 1-420 of SEQ ID NO: 1); a truncated protein with amino acids 7-420, 25-381, 37-381 of SEQ ID NO: 1; the full length protein with conservative substitutions; the truncated protein with conservative mutations.

The term "part of a binding pocket" refers to less than all of the amino acid residues that define the binding pocket. The structure coordinates of residues that constitute part of a binding pocket may be specific for defining the chemical environment of the binding pocket, or useful in designing fragments of an inhibitor that may interact with those residues. For example, the portion of residues may be key residues that play a role in ligand binding, or may be residues that are spatially related and define a three-dimensional compartment of the binding pocket. The residues may be contiguous or non-contiguous in primary sequence.

In one embodiment, part of the binding pocket is at least two amino acid residues. In one embodiment, part of the inhibitor-binding pocket is GSK-3β amino acids D133 and V135. In another embodiment, part of the inhibitor-binding pocket is GSK-3β amino acids K85, L132, D133 and V135. In another embodiment, part of the inhibitor-binding pocket is GSK-3β amino acids K85, M101, V110, L130 and L132. In another embodiment, part of the inhibitor-binding pocket is GSK-3β amino acids I62, V135, P136, T138 and L188. In another embodiment, part of the inhibitor-binding pocket is GSK-3β amino acids V70, V110, L188 and C199. In another embodiment, part of the inhibitor-binding pocket is GSK-3β amino acids F67, V70, Q185 and C199. In one embodiment, part of a substrate binding pocket is GSK-3β amino acids D90, K91, R92, F93, K94. In another embodiment, part of the substrate binding pocket is GSK-3β amino acids R96, R180, K205, N213 and Y234. In another embodiment, part of the substrate binding pocket is GSK-3β amino acids R96, R180 and K205. In another embodiment, part of the substrate binding pocket is GSK-3β amino acids S66, F67 and F93. In another embodiment, part of the substrate binding pocket is GSK-3β amino acids Y216, 1217, C218, S219, R220 and R223.

The term "part of a GSK-3β protein" refers to less than all of the amino acid residues of a GSK-3β protein. In one embodiment, part of a GSK-3β protein defines the binding pockets, domains or motifs of the protein. The structure coordinates of residues that constitute part of a GSK-3β protein may be specific for defining the chemical environment of the protein, or useful in designing fragments of an inhibitor that may interact with those residues. The portion of residues may also be residues that are spatially related and define a three-dimensional compartment of a binding pocket, motif or domain. The residues maybe contiguous or non-contiguous in primary sequence. For example, the portion of residues may be key residues that play a role in ligand or substrate binding, catalysis or structural stabilization.

The term "pharmaceutically acceptable carrier, adjuvant, or vehicle" refers to a non-toxic carrier, adjuvant, or vehicle that may be administered to a patient, together with a compound of this invention, and which does not destroy the pharmacological activity thereof.

The term "patient" includes human and veterinary subjects.

The term "peptide comprising a phosphorylation sequence" refers to a peptide comprising the ZXXXY motif Z can be serine or threonine. Y can be serine, threonine or valine. X can be any amino acid residue. Z or Y can be phosphorylated or unphosphorylated. The phosphorylation of Y facilitates the phosphorylation of X by GSK-3β. Examples of peptide substrates comprising a phosphorylation sequence include but are not limited to, ASVPPS (SEQ ID NO: 2), PSPSLS (SEQ ID NO: 3), LSRHSS (SEQ ID NO: 4), SSPHQS (SEQ ID NO: 5), DSRAGS (SEQ ID NO: 6), LSRRPS (SEQ ID NO: 7), PTPPPT (SEQ ID NO: 8), PTPVPS (SEQ ID NO: 9), KSPVVS (SEQ ID NO: 10), VSGDTS (SEQ ID NO: 11), QSYLDS (SEQ ID NO: 12), DSGIHS (SEQ ID NO: 13), HSGATT (SEQ ID NO: 14), TTTAPS (SEQ ID NO: 15), TSANDS (SEQ ID NO: 16), DSEQQS (SEQ ID NO: 17), SSPLPS (SEQ ID NO: 18), PSSPLS ((SEQ ID NO: 19), and CTPTDV (SEQ ID NO: 20).

The term "pharmaceutically acceptable derivative" or "prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\,alkyl)_4$ salts. This invention also envisions the quaternization of any basic nitrogen-containing groups of the compounds disclosed herein. Water or oil-soluble or dispersible products may be obtained by such quaternization.

The term "protein kinase-mediated condition" or "state" refers to any disease or other deleterious condition or state in which a protein kinase is known to play a role. Such conditions include, without limitation, autoimmune diseases, inflammatory diseases, metabolic, neurological and neurodegenerative diseases, cardiovasclular diseases, allergy and asthma.

The term "root mean square deviation" or "RMSD" refers to the square root of the arithmetic mean of the squares of the deviations from the mean. It is a way to express the deviation or variation from a trend or object. For purposes of this invention, the "root mean square deviation" defines the variation in the backbone of a protein from the backbone of GSK-3β or a binding pocket portion thereof, as defined by the structure coordinates of GSK-3β described herein. It would be readily apparent to those skilled in the art that the calculation of RMSD involves standard error.

The term "soaked" refers to a process in which the crystal is transferred to a solution containing the compound of interest.

The term "structure coordinates" refers to Cartesian coordinates derived from mathematical equations related to the patterns obtained on diffraction of a monochromatic beam of X-rays by the atoms (scattering centers) of a protein or protein complex in crystal form. The diffraction data are used to calculate an electron density map of the repeating unit of the crystal. The electron density maps are then used to establish the positions of the individual atoms of the enzyme or enzyme complex.

The term "substantially all of a GSK-3β binding pocket" or "substantially all of a GSK-3β protein" refers to all or almost all of the amino acids in the GSK-3β binding pocket or protein. For example, substantially all of a GSK-3β binding pocket can be 100%, 95%, 90%, 80%, 70% of the residues defining the GSK-3β binding pocket or protein.

The term "substrate binding groove" refers to an area in a protein kinase where the substrate binds. The substrate binding groove is located at the interface of the β-strand and α-helical domain, and positioned between the activation loop and β-strand domain. Examples of substrates include but are not limited to glycogen synthase, β-catenin, elongation initiation factor 2B ε subunit, cAMP-responsive element binding protein, CCAAT/enhancer binding protein α, microtuble associated protein Tau, axin, Dd-STATa and Cyclin D1.

The term "substrate binding pocket" refers to a binding pocket of a molecule or molecular complex defined by the structure coordinates of a certain set of amino acid residues present in the GSK-3β structure, as described below. This binding pocket is in an area in the GSK-3β protein where the substrate binding groove is located.

The term "sufficiently homologous to GSK-3β" refers to a protein that has a sequence homology of at least 20% compared to GSK-3β protein. In one embodiment, the sequence homology is at least 40%.

Inhibitors of GSK-3

One object of the instant invention is to provide compounds having formula (I):

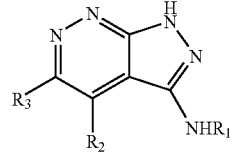

or a pharmaceutically acceptable derivative thereof, wherein:
$R_1$ is selected from H, aliphatic, RC(O)—, $RS(O)_n$—, ROC(O)—, carbocyclyl, heterocyclyl, aryl, aralkyl, heteroaryl, or heteroaralkyl; wherein said aliphatic, carbocyclyl, heterocyclyl, aryl, aralkyl, heteroaryl, or heteroaralkyl is optionally substituted;

$R_2$ and $R_3$ are each independently selected from H, aliphatic, carbocyclyl, heterocyclyl, aryl, aralkyl, heteroaryl, heteroaralkyl, —N(R)$_2$, —NRCOR, —NRCO$_2$R, —NRSO$_2$R, —S(O)$_n$R, —SO$_2$N(R)$_2$, —SR, —OR, —CF$_3$, halo, —NO$_2$, —CN, —C(O)R, —CO$_2$R, —OC(O)R, —CON(R)$_2$, or —OC(O)N(R)$_2$, wherein said aliphatic, carbocyclyl, heterocyclyl, aryl, aralkyl, heteroaryl, or heteroaralkyl is optionally substituted; or $R_2$ and $R_3$ taken together with the intervening atoms optionally form a five- to nine-membered ring that is fused to the pyridazinyl ring of formula I, said fused ring having 0-2 heteroatoms;

each R is independently selected from H, aliphatic, carbocyclyl, heterocyclyl, aryl, aralkyl, heteroaryl, or heteroaralkyl, wherein each member of R except H is optionally substituted; and n is 1 or 2;

provided that when $R_1$ is H, $R_2$ and $R_3$ are not both unsubstituted phenyl; and when $R_1$ is H, $R_2$ and $R_3$ are other than H, halogen, or an unsubstituted alkyl.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C— or $^{14}$C-enriched carbon are within the scope of this invention.

In a preferred embodiment of the invention, $R_1$ is H, RC(O)—, or aralkyl, wherein R is as defined above. In a more preferred embodiment, $R_1$ is H, aliphatic-C(O)—, aryl-C(O)—, or aralkyl. In an even more preferred embodiment, $R_1$ is H, CH$_3$C(O)—, PhC(O)—, or PhCH$_2$—.

In another preferred embodiment, $R_2$ and $R_3$ are independently H, aryl or heteroaryl. In another preferred embodiment, $R_2$ and $R_3$ are independently H, aryl, carbocyclyl, heterocyclyl, or heteroaryl. In another embodiment, $R_2$ and $R_3$ are independently aryl, carbocyclyl, heterocyclyl, or heteroaryl. Preferably, $R_2$ and $R_3$ are independently H, phenyl, naphthyl, pyridyl, thienyl, furanyl, pyrimidinyl, benzodioxolyl, or cyclohexyl, any of which except H is optionally substituted. More preferably, $R_2$ and $R_3$ are independently phenyl, naphthyl, pyridyl, thienyl, furanyl, pyrimidinyl, benzodioxolyl, or cyclohexyl, any of which is optionally substituted. Even more preferably, the substituents on phenyl, naphthyl, pyridyl, thienyl, furanyl, pyrimidinyl, benzodioxolyl, or cyclohexyl are selected from halo, alkyl, —CN, —NO$_2$, —SO$_2$NH$_2$, —SO$_2$NH-(alkyl), —SO$_2$N(alkyl)$_2$, —O-alkyl, —NH$_2$, —N-alkyl, —N-(alkyl)$_2$, —CONH$_2$, —CONH(alkyl), —CONH(alkyl)$_2$, —O-phenyl, or —S-alkyl.

In another preferred embodiment, when $R_1$ is a large group, $R_2$ is a small group. A small group refers to hydrogen or a moiety that contains 3 carbons or less, such as methyl, ethyl, or propyl. A large group refers to a moiety that contains 4 or more carbons.

In another preferred embodiment, $R_1$ is H, and $R_2$ and $R_3$ are independently H or an optionally substituted phenyl.

A more preferred embodiment of the invention is shown in formula Ia:

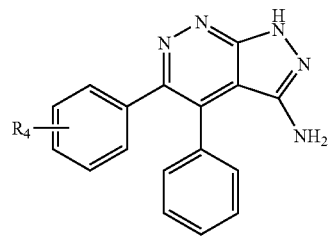

(Ia), wherein $R_4$ is halo. In an even more preferred embodiment, $R_4$ is F.

Representative examples of compounds of the present invention are shown below in Table 1.

TABLE 1

| Compound No. | $R_1$ | $R_2$ | $R_3$ |
|---|---|---|---|
| 1 | H | phenyl | phenyl |
| 2 | H | 4-Cl-phenyl | phenyl |
| 3 | H | 4-F-phenyl | 4-F-phenyl |
| 4 | H | phenyl | 4-F-phenyl |
| 5 | H | 4-F-phenyl | phenyl |
| 6 | H | 3-F-phenyl | phenyl |
| 7 | H | phenyl | 4-pyridyl |

TABLE 1-continued
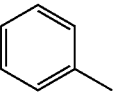
| Compound No. | R₁ | R₂ | R₃ |
|---|---|---|---|
| 8 | H | 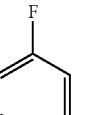 | 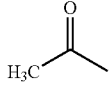 |
| 9 | 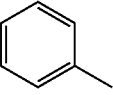 | 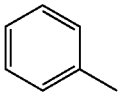 | 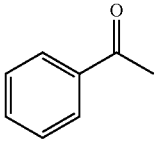 |
| 10 | 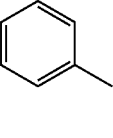 | 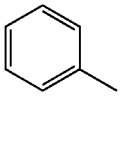 | 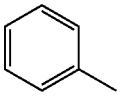 |
| 11 | H | 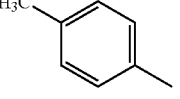 | 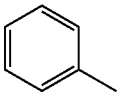 |
| 12 | H | 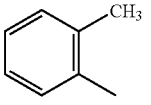 | 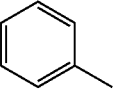 |
| 13 | H | 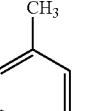 | 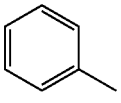 |
| 14 | H | 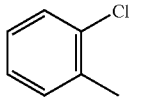 | 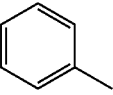 |
| 15 | H | 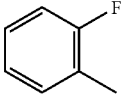 | 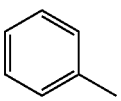 |
| 16 | H | 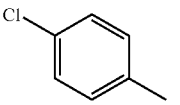 | 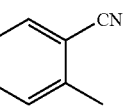 |
| 17 | H | 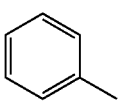 |  |

TABLE 1-continued
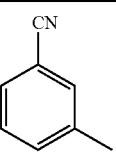
| Compound No. | R₁ | R₂ | R₃ |
|---|---|---|---|
| 18 | H | 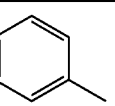 3-CN-phenyl |  phenyl |
| 19 | H |  4-CN-phenyl | 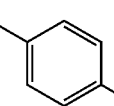 phenyl |
| 20 | H | 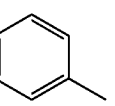 phenyl | 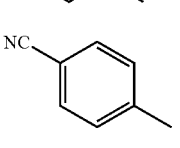 2-CN-phenyl |
| 21 | H | 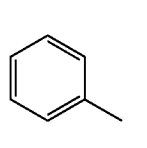 phenyl | 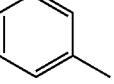 3-CN-phenyl |
| 22 | H | 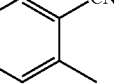 phenyl | 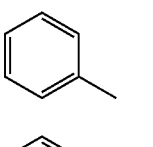 4-CN-phenyl |
| 23 | H | 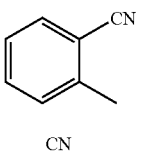 phenyl | 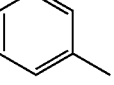 2-pyridyl |
| 24 | H | 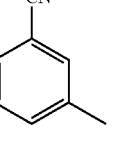 phenyl | 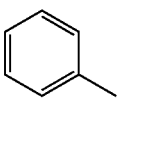 3-pyridyl |
| 25 | 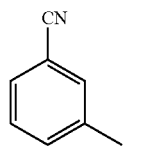 benzyl | 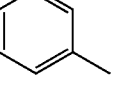 phenyl | 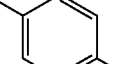 phenyl |
| 26 | H | 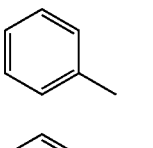 2-pyridyl | 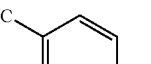 phenyl |
| 27 | H | 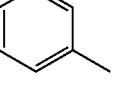 3-pyridyl | 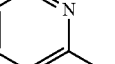 phenyl |
| 28 | H | 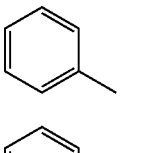 4-pyridyl | 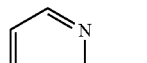 phenyl |

TABLE 1-continued

| Compound No. | R₁ | R₂ | R₃ |
|---|---|---|---|
| 29 | H | phenyl | 2-thienyl |
| 30 | H | 2-furyl | phenyl |
| 31 | H | phenyl | 1-naphthyl |
| 32 | H | phenyl | H |
| 33 | H | H | phenyl |
| 35 | H | 2-methylphenyl | phenyl |
| 36 | H | 3-methylphenyl | phenyl |
| 37 | H | 4-methylphenyl | phenyl |
| 38 | H | 4-nitrophenyl | phenyl |
| 39 | H | 4-sulfamoylphenyl | phenyl |

TABLE 1-continued
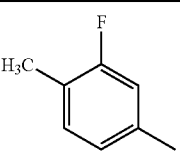
| Compound No. | R₁ | R₂ | R₃ |
|---|---|---|---|
| 40 | H | 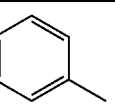 | 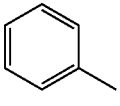 |
| 41 | H | 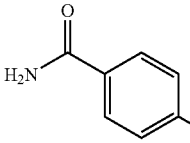 | 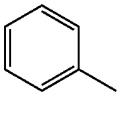 |
| 42 | H | 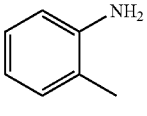 | 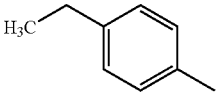 |
| 43 | H |  | 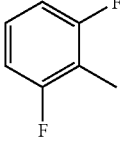 |
| 44 | H | 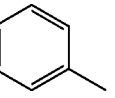 | 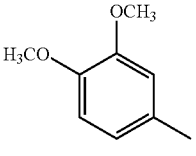 |
| 45 | H | 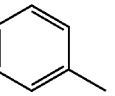 | 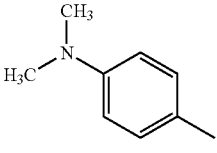 |
| 46 | H | 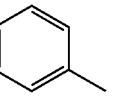 | 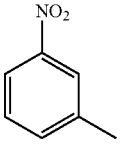 |
| 47 | H | 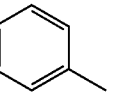 | 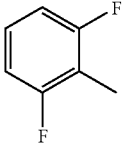 |
| 48 | H | 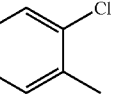 | |

TABLE 1-continued
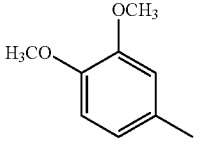
| Compound No. | R₁ | R₂ | R₃ |
|---|---|---|---|
| 49 | H | 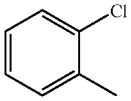 | 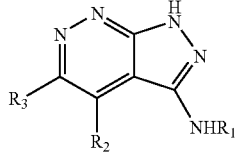 |
| 50 | H | 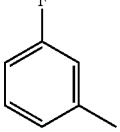 | 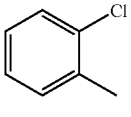 |
| 51 | H | 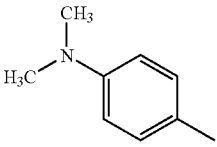 | 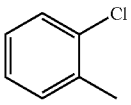 |
| 52 | H | 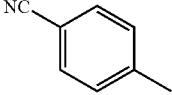 | 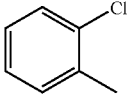 |
| 53 | H | 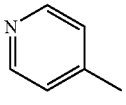 | 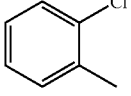 |
| 54 | H | 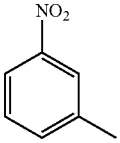 | 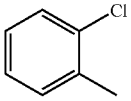 |
| 55 | H | 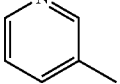 | 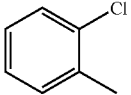 |
| 56 | H | 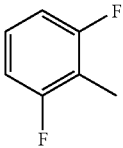 | 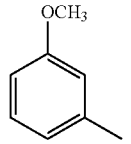 |
| 57 | H | 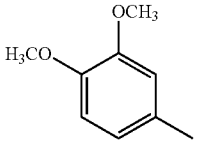 | 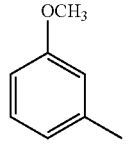 |

TABLE 1-continued
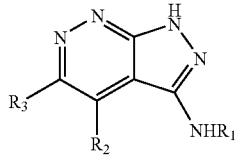
| Compound No. | R₁ | R₂ | R₃ |
|---|---|---|---|
| 58 | H | 3-fluorophenyl | 3-methoxyphenyl |
| 59 | H | 4-(dimethylamino)phenyl | 3-methoxyphenyl |
| 60 | H | 4-cyanophenyl | 3-methoxyphenyl |
| 61 | H | pyridin-4-yl | 3-methoxyphenyl |
| 62 | H | 3-nitrophenyl | 3-methoxyphenyl |
| 63 | H | pyridazin-3-yl | 3-methoxyphenyl |
| 64 | H | 2,6-difluorophenyl | 4-methylphenyl |
| 65 | H | 3,4-dimethoxyphenyl | 4-methylphenyl |

TABLE 1-continued
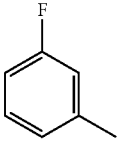
| Compound No. | R₁ | R₂ | R₃ |
|---|---|---|---|
| 66 | H | 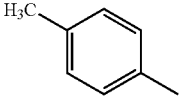 | 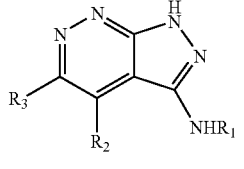 |
| 67 | H | 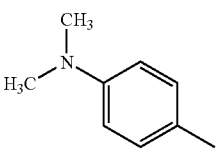 | 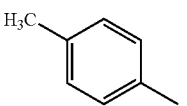 |
| 68 | H | 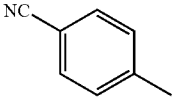 | 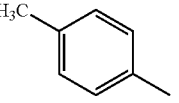 |
| 69 | H | 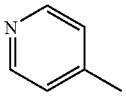 | 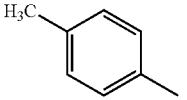 |
| 70 | H | 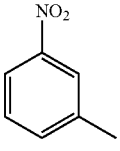 | 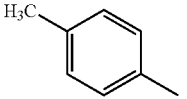 |
| 71 | H | 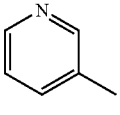 | 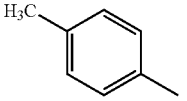 |
| 72 | H | 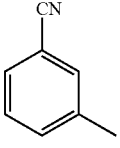 | 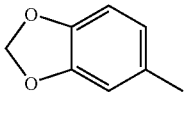 |
| 73 | H | 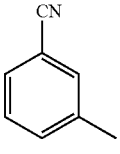 | 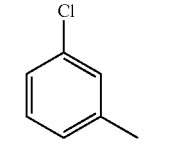 |
| 74 | H | 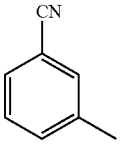 | 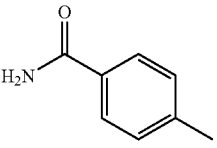 |

TABLE 1-continued
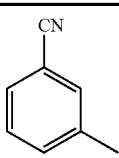
| Compound No. | R₁ | R₂ | R₃ |
|---|---|---|---|
| 75 | H | 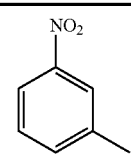 | 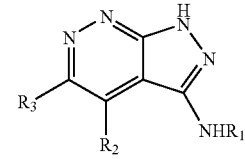 |
| 76 | H |  | 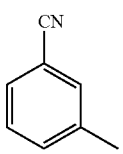 |
| 77 | H | 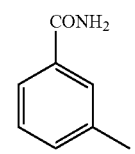 | 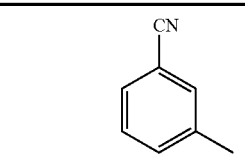 |
| 78 | H | 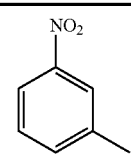 | 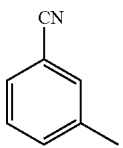 |
| 79 | H | 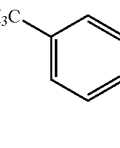 | 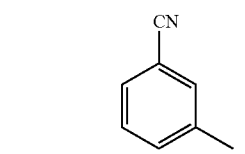 |
| 80 | H | 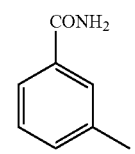 | 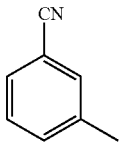 |
| 81 | H | 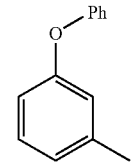 | 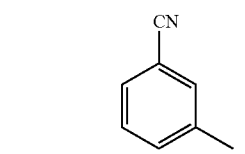 |
| 82 | H | 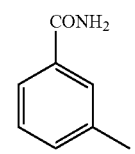 | 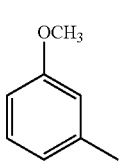 |
| 83 | H | 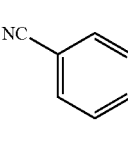 | 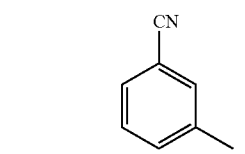 |

TABLE 1-continued
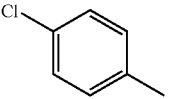
| Compound No. | R₁ | R₂ | R₃ |
|---|---|---|---|
| 84 | H | 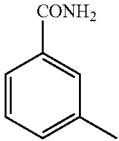 | 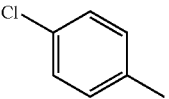 |
| 85 | H | 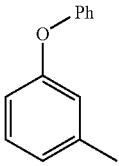 | 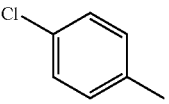 |
| 86 | H | 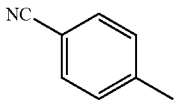 | 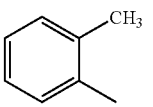 |
| 87 | H | 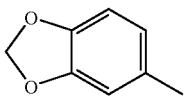 | 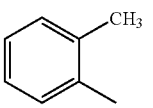 |
| 88 | H | 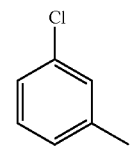 | 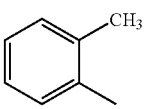 |
| 89 | H | 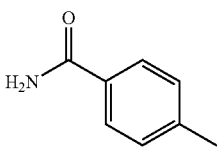 | 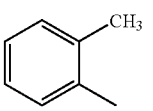 |
| 90 | H | 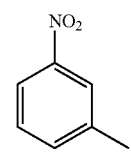 | 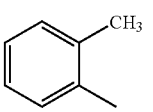 |
| 91 | H | 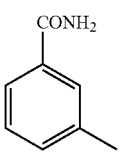 | 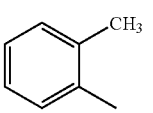 |
| 92 | H | 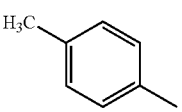 | |

TABLE 1-continued
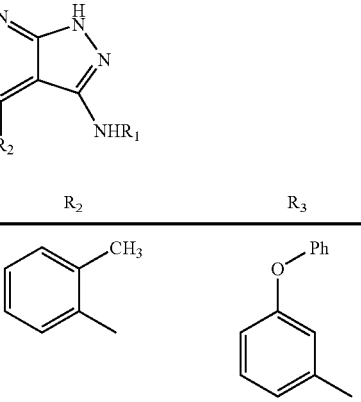
| Compound No. | R₁ | R₂ | R₃ |
|---|---|---|---|
| 93 | H | 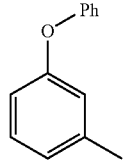 | 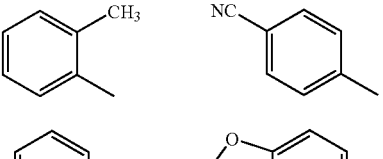 |
| 94 | H | 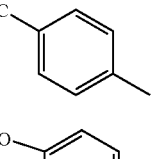 | 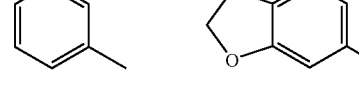 |
| 95 | H | 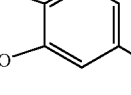 | 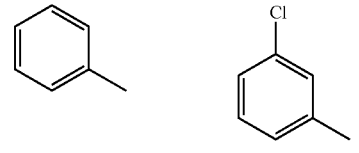 |
| 96 | H | 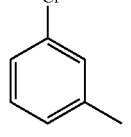 | 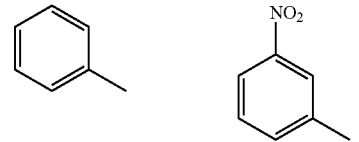 |
| 97 | H | 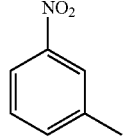 | 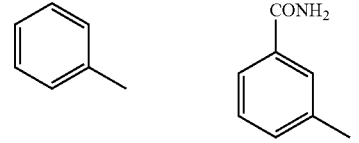 |
| 98 | H | 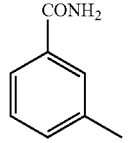 | 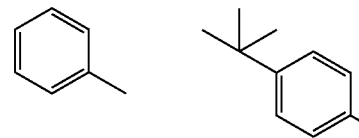 |
| 99 | H | 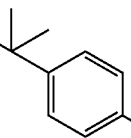 | 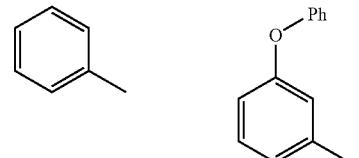 |
| 100 | H | 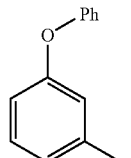 | 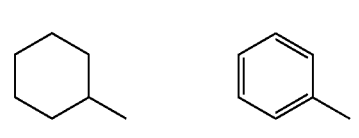 |
| 101 | H | 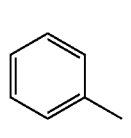 | |

TABLE 1-continued

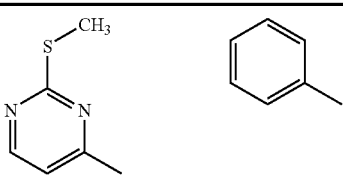

| Compound No. | $R_1$ | $R_2$ | $R_3$ |
|---|---|---|---|
| 102 | H | 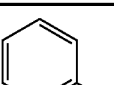 | 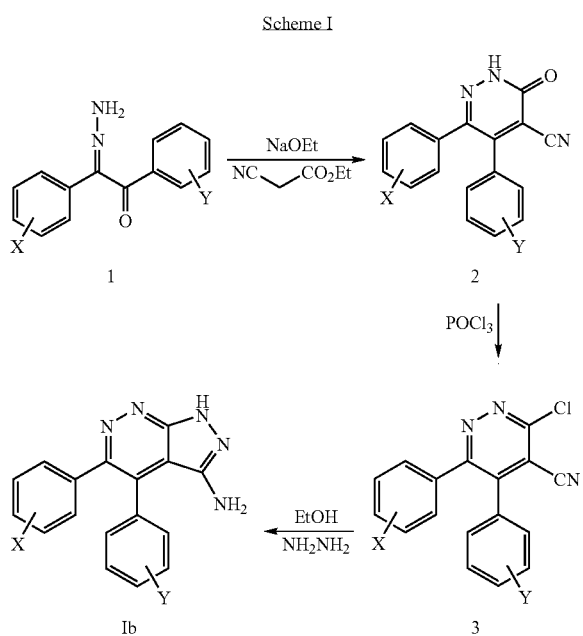 |

In a more preferred embodiment, the compound of the present invention is 3-amino-4-phenyl-5-(3-fluorophenyl)-1H-pyrazolo[3,4-c]pyridazine (Compound 8).

Methods for Producing GSK-3 Inhibitors

The compounds of this invention generally may be prepared from known starting materials, following methods known to those skilled in the art for analogous compounds, as illustrated by general Scheme I and the synthetic examples described below. References that may be useful in making the present compounds include El-Gendy, A. M. et al., *Asian J. Chem.*, 1, 376 (1989); Deeb, A. and Said, S. A., *Collect. Czech. Chem. Comm.*, 50, 2795 (1990); and Shalaby, A. A. *J. Prakt. Chemie*, 332, 104 (1990).

Scheme I

Scheme I shows a general approach for making the present compounds. The unsymmetrical diaryl keto hydrazones (1) were prepared from the corresponding substituted deoxybenzoins as described in U.S. Pat. No. 4,009,022, incorporated herein by reference. The substituted deoxybenzoins were readily synthesized following methods known in the art, for instance, those described in Hill, D. T. et al, *J. Het. Chem.*, 28, 1181 (1991); Rieke, R. D. et al, *J. Org. Chem.*, 56, 1445 (1991); Fujisowa, T. et al, *Chem. Lett.*, 1135 (1981); and Iyoda, M. et al, *Tet. Lett.*, 26, 4777 (1985). To an ethanol solution of diaryl keto hydrazone (1), ethyl cyanoacetate (excess) and sodium ethoxide in tetrahydrofuran (THF) were added. The mixture was refluxed for 6 hours. After cooling, the solvent was removed under vacuum and the residue was taken up in dichloromethane ($CH_2Cl_2$), washed with 0.1 M HCl and water and dried with sodium sulfate. After filtering, the solvent was removed under vacuum and the product, 4-cyano-5,6-diaryl 2(1H) pyridazinone (2) was purified by chromatography on silica gel (5:95 methanol/dichloro-methane).

Purified 4-cyano-5,6-diaryl 2(1H) pyridazinone (2) was added to $POCl_3$ and heated to 100° C. for 5-6 hours. After cooling, the reaction mixture was poured onto ice and stirred for one hour. The resultant 3-chloro-4-cyano-5,6-diaryl pyridazine (3) was filtered off, washed with water, air dried and used in the next step without further purification. Purified 3-chloro-4-cyano-5,6-diaryl pyridazine (3) was further refluxed with 2 equivalents of anhydrous hydrazine in ethanol for several hours. Upon cooling, the product Ib would sometimes precipitate out, in which case compound Ib was purified by recrystallizing from ethanol. Otherwise purification of Ib was achieved by chromatography on silica gel (5:95 methanol/dichloromethane).

One having ordinary skill in that art may synthesize other compounds of this invention following the teachings of the specification using reagents that are readily synthesized or commercially available.

The present invention provides detailed methods of producing representative compounds of the present invention as described in Examples 1-17 below.

The activity of the compounds as protein kinase inhibitors, for example, as GSK-3 inhibitors, may be assayed in vitro, in vivo or in a cell line. In vitro assays include assays that determine inhibition of either the phosphorylation activity or ATPase activity of activated GSK-3. Alternate in vitro assays quantitate the ability of the inhibitor to bind to GSK-3. Inhibitor binding may be measured by radiolabelling the inhibitor prior to binding, isolating the inhibitor/GSK-3 complex and determining the amount of radiolabel bound. Alternatively, inhibitor binding may be determined by running a competition experiment where new inhibitors are incubated with GSK-3 bound to known radioligands.

Pharmaceutical Compositions

According to another embodiment of the invention, the protein kinase inhibitors, particularly GSK-3 inhibitors, or derivatives/salts thereof may be formulated into compositions. In a preferred embodiment, the composition is a pharmaceutical composition. In one embodiment, the composition comprises an amount of the protein kinase inhibitor effective to inhibit GSK-3 in a biological sample or in a patient. In another embodiement, the pharmaceutical compositions, which comprise an amount of the protein kinase inhibitor effective to treat or prevent a GSK-3-mediated condition and a pharmaceutically acceptable carrier, adjuvant, or vehicle, may be formulated for administration to a patient.

The amount effective to inhibit GSK-3 is one that inhibits the kinase activity of GSK-3 at least 50%, more preferably at least 60% or 70%, even more preferably at least 80% or 90%, and most preferably at least 95%, where compared to the GSK-3 activity of the enzyme in the absence of an inhibitor. Any method may be used to determine inhibition. See, e.g., Example 18.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, favoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In addition to the compounds of this invention, pharmaceutically acceptable derivatives or prodrugs of the compounds of this invention may also be employed in compositions to treat or prevent the above-identified diseases or disorders.

The amount of the protein kinase inhibitor that may be combined with the carrier materials to produce a single dosage form will vary depending upon the patient treated and the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Method of Treatment and Prevention of Disease

One aspect of this invention relates to a method for treating a disease state in patients that is alleviated by treatment with a GSK-3 inhibitor, which method comprises administering to a patient in need of such a treatment a therapeutically effective amount of a compound of formula I or a pharmaceutically acceptable derivative thereof.

Another aspect of this invention relates to a method of inhibiting GSK-3 activity in a patient, comprising administering to the patient a composition comprising a compound of formula I or a pharmaceutically acceptable derivative thereof. Another method relates to enhancing glycogen synthesis and/or lowering blood levels of glucose in a patient in need thereof, which method comprises administering to the patient a therapeutically effective amount of a compound of formula I or a pharmaceutically acceptable derivative thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Depending upon the particular protein kinase-mediated condition to be treated or prevented, additional drugs, which are normally administered to treat or prevent that condition, may be administered together with the inhibitors of this invention. For example, in the treatment of diabetes, other anti-diabetic agents may be combined with the GSK-3 inhibitors of this invention to treat diabetes. These agents include, without limitation, insulin, in injectable or inhalation form, glitazones, and sulfonyl ureas.

Those additional agents may be administered separately from the protein kinase inhibitor-containing composition, as part of a multiple dosage regimen. Alternatively, those agents may be part of a single dosage form, mixed together with the protein kinase inhibitor of this invention in a single composition.

Another method of this invention relates to inhibiting GSK-3 activity in a biological sample, which method comprises contacting the biological sample with the GSK-3 inhibitor of formula I or a pharmaceutically acceptable derivative or prodrug thereof, or a pharmaceutical composition thereof, in an amount effective to inhibit GSK-3.

Crystallizable Compositions and Crystals of GSK-3β Protein and Protein Complexes According to one embodiment, the invention provides a crystallizable composition comprising unphosphorylated GSK-3β protein or its homologue and phosphate ions. In one embodiment, the crystallizable composition further comprises between about 5 to 25% v/v of precipitant polyethylene glycol, a buffer that maintains pH between about 4.0 and 8.0; and optionally, a reducing agent of 1-20 mM. In one embodiment, the crystallizable composition comprises unphosphorylated GSK-3β protein, 15% PEG 3350, 50 mM Na/KPO$_4$ at pH 4.1 and 10 mM DTT.

In another embodiment, the invention provides a crystallizable composition comprising phosphorylated GSK-3β protein or its homologue. In one embodiment, the crystallizable composition further comprises between about 5-25% v/v polyethylene glycol, a buffer that maintains pH between about 6.0 and 8.5, and 1-10% dimethyl sulfoxide(DMSO). In one embodiment, the crystallizable composition comprises phosphorylated GSK-3β protein, between about 7-10% PEG 3350, 100 mM Tris HCl and 5% DMSO.

In another embodiment, the invention provides a crystallizable composition comprising GSK-3β protein or its homologue and a chemical entity. The GSK-3β protein may be phosphorylated or unphosphorylated. In one embodiment, the chemical entity is selected from the group consisting of an inhibitor for the active site, a nucleotide triphosphate, an ATP, a substrate or inhibitor for the substrate binding groove, or a peptide comprising a phosphorylation sequence. In one embodiment, the inhibitor for the active site is selected from the group consisting of 4,5-Diphenyl-1H-pyrazolo [3,4-c] pyridazin-3 -ylamine; (5-Methyl-2H-pyrazo 1-3 -yl)-(2-pyridin-4-yl-quinazolin-4-yl)-amine; 4-(5-Methyl-2-phenylamino-pyrimidin-4-yl)- 1H-pyrrole-2-carboxylic acid (2-hydroxy-1 -phenyl-ethyl)-amide; (1H-Indazol-3 -yl)-[2-(2-trifluoromethyl-phenyl)-quinazolin-4-yl]-amine and an ATP analogue. In one embodiment, the crystallizable composition further comprises between about 5-25% v/v polyethylene glycol, and between about 0.1-1 M ammonium fluoride, ammonium formate, potassium formate or potassium fluoride. In one embodiment, the peptide comprising a phosphorylation sequence is HSSPHQpSEDEEE (SEQ ID NO: 21). In one embodiment, the crystallizable composition comprises phosphorylated GSK-3βprotein, HSSPHQpSEDEEE (SEQ ID NO: 21),between about 10-15% v/v polyethylene glycol, and 50 mM ammonium fluoride.

In one embodiment, the GSK-3β protein or its homologue is preferably 85-100% pure prior to forming the crystallizable composition.

According to another embodiment, the invention provides a crystal composition comprising unphosphorylated GSK-3β protein or its homologue and phosphate ions. In another embodiment, the invention provides a crystal composition comprising unphosphorylated GSK-3β protein or its homologue and a chemical entity. Preferably, the chemical entity is an inhibitor for the active site, an ATP analogue or nucleotide triphosphate. Preferably, the crystal has a unit cell dimension of a=83 Å b=86 Å c=178 Å, α=β=γ=90° and belongs to space group P2$_1$2$_1$2$_1$. It will be readily apparent to those skilled in the art that the unit cells of the crystal compositions may deviate ±1-2 Å from the above cell dimensions depending on the deviation in the unit cell calculations.

The invention also provides a crystal composition comprising phosphorylated GSK-3βprotein or its homologue with or without a chemical entity. Preferably, the chemical entity is an inhibitor for the active site, an ATP analogue or nucleotide triphosphate. Preferably, the unit cell dimensions of the crystal is a=64 Å b=67 Å c=67 Å α=100 ° β=103° γ=89.8° or a=64 Å b=67 Å c=67 Å α=80° β=77° γ=89.8° and belongs to the space group P1. In another embodiment, the chemical entity is a substrate or inhibitor to the substrate binding groove, or a peptide comprising a phosphorylation sequence. Preferably, the chemical entity is HSSPHQpSEDEEE (SEQ ID NO: 21) and the unit cell dimensions of the crystal is a=75 Åb=108 Å c=121 Å α=β=γ90° and belongs to the space group $P2_12_12_1$. It will be readily apparent to those skilled in the art that the unit cells of the crystal compositions may deviate ±1-2 Å or ±1-2° from the above cell dimensions depending on the deviation in the unit cell calculations.

As used herein, the GSK-3β protein in the crystallizable or crystal compositions can be the full length GSK-3β protein (amino acids 1-420 of SEQ ID NO: 1); a truncated GSK-3β protein with amino acids 7-420, 25-381, 37-381 of SEQ ID NO: 1; the full length protein with conservative substitutions; said truncated protein with conservative mutations. In one embodiment, the GSK-3β protein is produced from the baculovirus system. The unphosphorylated GSK-3β protein is not phosphorylated at any of the phosphorylation sites. The phosphorylated GSK-3β protein is phosphorylated at any of the phosphorylation sites, for example, at Serine 9 or Tyrosine 216. Preferably, the protein is phosphorylated at Tyrosine 216.

The GSK-3β protein or its homologue may be produced by any well-known method, including synthetic methods, such as solid phase, liquid phase and combination solid phase/liquid phase syntheses; recombinant DNA methods, including cDNA cloning, optionally combined with site directed mutagenesis; and/or purification of the natural products. In one embodiment, the protein is overexpressed from a baculovirus system or *E. Coli* system.

The invention also relates to a method of obtaining a crystal of a GSK-30 protein complex or GSK-3β homologue protein complex comprising a chemical entity that binds to the substrate-binding groove, comprising the steps of:

a) producing and purifying a GSK-3β protein;

b) mixing a crystallization solution with the protein complex to produce a crystallizable composition; and c) subjecting the composition to conditions which promote crystallization.

Conditions for promoting crystallization include, for example, apparatuses and devices for forming crystals, for example, a hanging drop, sitting drop, dialysis or microtube batch device, will promote crystallization. (U.S. Pat. Nos. 4,886,646, 5,096,676, 5,130,105, 5,221,410 and 5,400,741; Pav et al., *Proteins: Structure, Function, and Genetics*, 20, pp. 98-102 (1994), incorporated herein by reference). The hanging drop or sitting drop methods produce crystals by vapor diffusion. The hanging drop or sitting drop which contains the crystallizable composition is equilibrated against a reservoir containing a higher concentration of precipitant. As the drop approaches equilibrium with the reservoir, the protein becomes saturated in solution and crystals form. One of ordinary skilled in the art would be able to vary the crystallization conditions disclosed above and identify other crystallization conditions that would produce crystals for GSK-3 protein or its homologues with or without a chemical entity. Such variations may include adjusting the pH, salt type or concentration, precipitant type or concentration, crystallization temperature, protein concentration. One may also use high throughput crystallization assays to assist in finding or optimizing the crystallization condition.

Binding Pockets of GSK-3β Protein, Protein Complexes or Homologues Thereof

As disclosed above, applicants have provided the three-dimensional X-ray crystal structures of unphosphorylated GSK-3β, phosphorylated GSK-3β, unphosphorylated GSK-3β-inhibitor complexes, phosphorylated GSK-3β-inhibitor complex and phosphorylated GSK-3β-ADP-peptide complex. The crystal structure of GSK-3β presented here is within the GSK-3 subfamily. The invention will be useful for inhibitor design. The atomic coordinate data is presented in FIGS. 1-7.

In order to use the structure coordinates generated for the unphosphorylated and phosphorylated GSK-3β, their complexes or one of its binding pockets or GSK-3β-like binding pocket thereof, it is often times necessary to convert them into a three-dimensional shape. This is achieved through the use of commercially available software that is capable of generating three-dimensional structures of molecules or portions thereof from a set of structure coordinates.

Binding pockets, also referred to as binding sites in the present invention, are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or part of the binding pocket. An understanding of such associations will help lead to the design of drugs having more favorable associations with their target receptor or enzyme, and thus, improved biological effects. Therefore, this information is valuable in designing potential inhibitors of the binding pockets of biologically important targets. The binding pockets of this invention will be important for drug design.

The structure coordinates described above may be used to derive the torsion angles of the side chains (S. C. Lovell et al, *Proteins: Structure, Function, and Genetics*, 40, 389-408, (2000)). For example, in Glutamine, $\chi 1$ defines the torsion angle between N, Cα, Cβ, Cγ; $\chi 2$ defines the torsion angle between Cα, cβ, Cγ, Cδ; and $\chi 3$ defines the torsion angle between Cβ, Cγ, Cδ, Oε.

Surprisingly, it has now been found that for GSK-3β-inhibitor4 complex (FIG. 6), the conformation of Gln185 is very different from the conformations reported for glutamines at this position in unphosphorylated, phosphorylated GSK-3β, GSK-3β-ADP-peptide complex and other protein kinases. A glutamine side chain is able to adopt different conformations, depending on its chemical environment. In the case of Gln185, the molecule that occupies the active site influences the conformation of the side chain of glutamine. When the molecule that occupies the GSK-3β active site contains an ortho-substituted phenyl ring and that ring is within 3.9 Å of Ile 62, Phe 67, Val 70, Asn 186 and Asp 200, the glutamine side chain adopts a conformation with a $\chi 1$ angle of −176.4° and a $\chi 2$ angle of 174°. Taking into consideration the steric hindrance of nearby residues, $\chi 1$ of Gln185 can range from 123° to 180°, $\chi 2$ can range from −174° to −180° and 106° to 180°. The $\chi 1$ can also range from −100° to −180°, and $\chi 2$ can range from −151° to −180° and 126° to 180°.

In order to compare the conformations of GSK-3β and other protein kinases at a particular amino acid site, such as Gln185, along the polypeptide backbone, well-known procedures may be used for doing sequence alignments of the amino acids. Such sequence alignments allow for the equivalent sites to be compared. One such method for doing a sequence alignment is the "bestfit" program available from Genetics Computer Group which uses the local homology algorithm described by Smith and Waterman in *Advances in Applied Mathematics* 2; 482 (1981).

Equivalents of the Gln185 residue of GSK-3β may also be identified by its functional position. Gln185 is located on the α-helical domain of the GSK-3β kinase domain in front of the active site. It is positioned five residues after the conserved RD motif (Arg 180, Asp 181) and just before the beginning of beta-strand β7 (Bax, B. et al. *Structure*, 9, pp 1143-1152, (2001)).

A comparison of the torsion angles between Gln185 in the GSK-3β or GSK-3β complexes and those of corresponding glutamines in other kinases are illustrated in Table 2. The torsion angles were determined by the program QUANTA.

TABLE 2

| Protein | χ1 (°) | χ2 (°) | χ3 (°) |
|---|---|---|---|
| GSK-3β-peptide-ADP | −60.0 | 83.3 | −25.7 |
| Phosphorylated GSK-3β | −59.9 | 83.2 | −22.5 |
| Unphosphorylated GSK-3β | −60.9 | 63.0 | 88.7 |
| GSK-3β-inhibitor1 | −67.1 | 113.9 | −72.2 |
| GSK-3β-inhibitor2 | −60.7 | 90.1 | 98 |
| GSK-3β-inhibitor3 | −63.3 | −158.5 | 179.8 |
| GSK-3β-inhibitor4 | −176.4 | −174.0 | −3.3 |
| CDK2_inhibitor[1] | 87.4 | −172.5 | 73.4 |
| CDK2_cyclin A[2] | −98.1 | −59.2 | 71.2 |

[1] Cyclin-Dependant Kinase 2 in complex with oxindole inhibitor. Davis et al., Science, 291, 134 (2001); Protein Data Bank Accession number 1FVV.
[2] Phosphorylated Cyclin-Dependent Kinase-2 bound to Cyclin A. Russo et al., Nat. Struct. Biol., 3, 696 (1996); Protein Data Bank Accession number 1JST.

In the crystal structure of the phosphorylated GSK-3β-inhibitor1 complex, amino acid residues I62, G63, F67, V70, A83, K85, V110, L132, D133, Y134, V135, T138, N186, L188, C199, and D200 according to FIG. 3 were within 5 Å of the inhibitor bound in the active site. These amino acids residues were identified using the program QUANTA (Molecular Simulations, Inc., San Diego, Calif. ©1998), O (Jones et al., *Acta Crystallogr.* A47, pp. 110-119 (1991)) and RIBBONS (Carson, *J. Appl. Crystallogr.*, 24, pp. 9589-961 (1991)). The programs allow the display and output of all residues within 5 Å from the inhibitor. In addition, amino acid residues V61, I62, G63, N64, G65, F67, V69, V70, A83, K85, K86, V87, E97, M101, V110, R111, L130, V131, L132, D133, Y134, V135, P136, E137, T138, R141, D181, K183, Q185, N186, L187, L188, L189, K197, L198, C199, D200, F201 and G202 according to FIG. 3 were within 8 Å of the inhibitor bound in the active site. These amino acid residues were identified using the programs QUANTA, O and RIBBONS, supra.

In the crystal structure of the unphosphorylated GSK-3β-inhibitor2 complex, amino acid residues I62, G63, V70, A83, V110, L132, D133, Y134, V135, P136, E137, T138, R141, L188 and C199 according to FIG. 4 were within 5 Å of the inhibitor bound in the active site. These amino acid residues were identified using the programs QUANTA, O and RIBBONS. In addition, amino acid residues V61, I62, G63, N64, G65, G68, V69, V70, Y71, Q72, L81, V82, A83, I84, K85, E97, M101, V110, R111, L130, V131, L132, D133, Y134, V135, P136, E137, T138, V139, Y140, R141, Q185, N186, L187, L188, L189, K197, L198, C199, D200 and F201 according to FIG. 4 were within 8 Å of the inhibitor bound in the active site. These amino acids were identified using the programs QUANTA, O and RIBBONS.

In the crystal structure of the unphosphorylated GSK-3β-inhibitor3 complex, amino acid residues I62, N64, G65, S66, F67, G68, V69, V70, A83, K85, K86, V87, E97, V110, L132, D133, Y134, V135, P136, E137, T138, R141, K183, Q185, N186, L188, C199 and D200 according to FIG. 5 were within 5 Å of the inhibitor bound in the active site. These amino acid residues were identified using the programs QUANTA, O and RIBBONS. In addition, amino acid residues V61, I62, G63, N64, G65, S66, F67, G68, V69, V70, Y71, Q72, L81, V82, A83, I84, K85, K86, L88, E97, M101, V110, R111, L130, V131, L132, D133, Y134, V135, P136, E137, T138, V139, Y140, R141, H179, D181, K183, Q185, N186, L187, L188, L189, K197, L198, C199, D200, F201, G202, S203 and S219 according to FIG. 5 were within 8 Å of the inhibitor bound in the active site. These amino acid residues were identified using the programs QUANTA, O and RIBBON.

In the crystal structure of the unphosphorylated GSK-3β-inhibitor4 complex, amino acid residues I62, G63, N64, F67, V70, A83, V110, L132, D133, Y134, V135, P136, E137, T138, R141, Q185, N186, L188, C199 and D200 according to FIG. 6 were within 5 Å of the inhibitor bound in the active site. These amino acid residues were identified using the programs QUANTA, O and RIBBONS. In addition, applicants have determined that amino acid residues V61, I62, G63, N64, G65, S66, F67, G68, V69, V70, Y71, Q72, L81, V82, A83, I84, K85, E97, M101, V110, R111, L130, V131, L132, D133, Y134, V135, P136, E137, T138, V139, Y140, R141, D181, K183, P184, Q185, N186, L187, L188, L189, K197, L198, C199, D200 and F201 according to FIG. 6 were within 8 Å of the inhibitor bound in the active site. These amino acid residues were identified using the programs QUANTA, O and RIBBONS.

Using a multiple alignment program to compare the unphosphorylated GSK-3β structure and structures of other members of the protein kinase family, amino acid residues Y56, T59, K60, V61, V69, V70, Y71, Q72, A73, K74, L75, L81, V82, A83, I84, K85, K86, L98, M101, R102, L104, H106, C107, N108, I109, V110, R111, L112, R113, Y114, F115, F116, L128, N129, L130, V131, L132, D133, Y134, V135, P136, E137, T138, V139, Y140, R141, V142, P154, V155, I156, Y157, V158, K159, L160, Y161, M162, Y163, Q164, L165, F166, R167, S168, L169, A170, Y171, I172, H173, S174, F175, G176, I177, C178, H179, R180, D181, I182, K183, P184, Q185, N186, L187, L188, L189, D190, P191, A194, V195, L196, K197, L198, C199 and D200 according to FIG. 1 were identified as the ATP-binding pocket (Gerstein et al., *J. Mol. Biol.*, 251, pp. 161-175 (1995), incorporated herein by reference). To perform this comparison, first, a sequence alignment between members of the protein kinase family was performed. Second, a putative core was constructed by superimposing a series of corresponding structures in the protein kinase family. Third, residues of high spatial variation were discarded, and the core alignment was iteratively refined. The amino acids that make up the final core structure have low structural variance and have similar local and global conformation relative to the corresponding residues in the protein family.

In the crystal structure of the phosphorylated GSK-3β-ADP-peptide complex, amino acids residues G65, S66, F67, D90, K91, R92, F93, K94, R96, R180, D181, K183, G202, S203, K205, P212, N213, V214, Y216, I217, C218, S219, R223, Y234 according to FIG. 7 were within 5 Å of the peptide bound in the substrate binding groove. These amino acid residues were identified using the programs QUANTA, O and RIBBONS, supra. Amino acid residues D90, K91, R92, F93, K94 made backbone interactions with the peptide substrate. Amino acid residues R96, R180, K205, N213, Y234 bound to pS656 of the peptide substrate. Amino acid residues R96, R180 and K205 formed a positively charged binding pocket surrounding the pS656. Amino acid residue S66 bound to the backbone of amino acid residue S652 from the peptide substrate. Amino acid residues F67, F93 form an aromatic binding pocket surrounding the peptide substrate amino acid residue H650.

In the crystal structure of the phosphorylated GSK-3β-ADP-peptide complex, amino acid residues N64, G65, S66, F67, G68, V87, L88, D90, K91, R92, F93, K94, N95, R96, E97, R180, D181, I182, K183 Q185, N186, D200, F201, G202, S203, A204, K205, Q206, L207, E211, P212, N213, V214, S215, Y216, I217, C218, S219, R220, Y221, Y222, R223, L227, T232 and Y234 according to FIG. 5 were within 8 Å of the peptide bound in the substrate binding groove. These amino acid residues were identified using the programs QUANTA, O and RIBBONS, supra. Amino acid residues Y216, I217, C218, S219, R220 and R223 form a binding pocket that accommodates the proline side chain of the peptide substrate.

In the GSK-3β-ADP-peptide electron density map, the side chains of residues F67, K91, and R92 in the substrate binding pocket could not be located. Alanine and glycine residues were used to build the structure model at these positions. For the purpose of this invention, the structure coordinates of amino acid residues F67, K91 and R92 refer to the structure coordinates of amino acid residues A67, A91 and G92 in FIG. 7, respectively. In FIGS. 1-7, where alanine or glycine residues were built in the model as a result of missing side chains in the electron density map, the same applies to those residues.

In one embodiment, the inhibitor-binding pocket comprises GSK-3β amino acid residues K85, M101, V110, L130 and L132 according to any one of FIGS. 1-7. In another embodiment, the inhibitor-binding pocket comprises GSK-3β amino acid residues I62, V135, P136, T138 and L188 according to any one of FIGS. 1-7. In another embodiment, the inhibitor-binding pocket comprises GSK-3β amino acid residues V70, V110, L188 and C199 according to any one of FIGS. 1-7. In another embodiment, the inhibitor-binding pocket comprises GSK-3β amino acids F67, V70, Q185 and C199 according to any one of FIGS. 1-7.

In one embodiment the inhibitor-binding pocket comprises amino acid residues V61, I62, G63, N64, G65, S66, F67, G68, V69, V70, Y71, Q72, L81, V82, A83, I84, K85, K86, V87, L88, E97, M101, V110, R111, L112, L130, V131, L132, D133, Y134, V135, P136, E137, T138, V139, Y140, R141, H179, D181, K183, P184, Q185, N186, L187, L188, L189, K197, L198, C199, D200, F201, G202, S203 and S219 according to any one of FIGS. 1-7.

In another embodiment, the ATP-binding pocket comprises amino acid residues Y56, T59, K60, V61, V69, V70, Y71, Q72, A73, K74, L75, L81, V82, A83, I84, K85, K86, L98, M101, R102, L104, H106, C107, N108, I109, V110, R111, L112, R113, Y114, F115, F116, L128, N129, L130, V131, L132, D133, Y134, V135, P136, E137, T138, V139, Y140, R141, V142, P154, V155, I156, Y157, V158, K159, L160, Y161, M162, Y163, Q164, L165, F166, R167, S168, L169, A170, Y171, I172, H173, S174, F175, G176, I177, C178, H179, R180, D181, I182, K183, P184, Q185, N186, L187, L188, L189, D190, P191, A194, V195, L196, K197, L198, C199 and D200 according to any one of FIGS. 1-7.

In another embodiment, the substrate binding pocket comprises amino acid residues S66, F67 and F93 according to any one of FIGS. 1-7. In another embodiment, the substrate binding pocket comprises amino acid residues G65, S66, F67 and F93 according to any one of FIGS. 1-7.

In another embodiment, the substrate binding pocket comprises amino acid residues D90, K91, R92, F93, K94 according to any one of FIGS. 1-7.

In another embodiment, the substrate binding pocket comprises amino acid residues R96, R180, K205, N213 and Y234 according to any one of FIGS. 1-7. In another embodiment, the substrate binding pocket comprises amino acid residues R96, R180 and K205 according to any one of FIGS. 1-7.

In another embodiment, the substrate binding pocket comprises amino acid residues Y216, I217, C218, S219, R220 and R223 according to any one of FIGS. 1-7.

In another embodiment, the substrate binding pocket comprises amino acid residues G65, S66, F67, D90, K91, R92, F93, K94, R96, R180, D181, K183, G202, S203, K205, P212, N213, V214, Y216, I217, C218, S219, R223 and Y234 according to any one of FIGS. 1-7.

In yet another embodiment, the substrate binding pocket comprises amino acid residues N64, G65, S66, F67, G68, V87, L88, D90, K91, R92, F93, K94, N95, R96, E97, R180, D181, I182, K183 Q185, N186, D200, F201, G202, S203, A204, K205, Q206, L207, E211, P212, N213, V214, S215, Y216, I217, C218, S219, R220, Y221, Y222, R223, L227, T232 and Y234 according to any one of FIGS. 1-7.

Thus, the binding pockets of this invention are defined by the structure coordinates of the above amino acids, as set forth in FIGS. 1-7.

It will be readily apparent to those of skill in the art that the numbering of amino acid residues in other homologues of GSK-3β may be different than that set forth for GSK-3β. Corresponding amino acid residues in homologues of GSK-3β are easily identified by visual inspection of the amino acid sequences or by using commercially available homology software programs.

Those of skill in the art understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

The variations in coordinates discussed above may be generated because of mathematical manipulations of the GSK-3β structure coordinates. For example, the structure coordinates set forth in any one of FIGS. 1-7 could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within a certain root mean square deviation as compared to the original coordinates, the resulting three-dimensional shape is considered encompassed by this invention. Thus, for example, a ligand that bound to the binding pocket of GSK-3β would also be expected to bind to another binding pocket whose structure coordinates defined a shape that fell within the acceptable root mean square deviation.

Various computational analyses may be necessary to determine whether a molecule or the binding pocket or portion thereof is sufficiently similar to the GSK-3β binding pockets described above. Such analyses may be carried out using well known software applications, such as the Molecular Similarity application of QUANTA (Molecular Simulations Inc., San Diego, Calif. © 1998), CCP4 (*Acta Crystallogr., D*50, 760-763 (1994)) or ProFit (A. C. R. Martin, ProFit version 1.8).

The Molecular Similarity software application permits comparisons between different structures, different conformations of the same structure, and different parts of the same structure. The procedure used in Molecular Similarity to compare structures is divided into four steps: 1) load the structures to be compared; 2) define the atom equivalences in these structures; 3) perform a fitting operation; and 4) analyze the results.

Each structure in the comparison is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms N, C, O and Cα for all corresponding amino acids between the two structures being compared.

The corresponding amino acids may be identified by sequence alignment programs such as the "bestfit" program available from the Genetics Computer Group which uses the local homology algorithm described by Smith and Waterman in *Advances in Applied Mathematics* 2, 482 (1981), which is incorporated herein by reference. The identification of equivalent residues can also be assisted by secondary structure alignment, for example, aligning the α-helices, β-sheets or hinge region (residues 126-135 in GSK-3β) in the structure. For programs that calculate RMSD values of the backbone atoms, an RMSD cutoff value can be used to exclude pairs of equivalent atoms with extreme individual RMSD values, or in situations where the equivalent atom can not be found in the corresponding structure.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

The RMSD values of the inhibitor and substrate-binding pockets between the GSK-3β-ADP-peptide structure (FIG. 7) and other GSK-3β structures (FIGS. 1-6) are illustrated in Tables 3-9. The RMSD values were calculated by the program LSQKAB in CCP4, supra. Backbone atoms (C, O, N and Cα) of all residues in the binding pocket were used in the calculation of the RMSD.

TABLE 3

Inhibitor-binding pocket (K85, M101, V110, L130 and L132)

| GSK-3β structures | RMSD between inhibitor binding pockets (Å) |
| --- | --- |
| unphosphorylated GSK-3β | 0.32 |
| phosphorylated GSK-3β | 0.34 |
| GSK-3β inhibitor1 complex | 0.32 |
| GSK-3β inhibitor2 complex | 0.39 |
| GSK-3β inhibitor3 complex | 0.27 |
| GSK-3β inhibitor4 complex | 0.27 |

TABLE 4

Inhibitor-binding pocket (I62, V135, P136, T138 and L188)

| GSK-3β structures | RMSD between inhibitor binding pockets (Å) |
| --- | --- |
| unphosphorylated GSK-3β | 1.16 |
| phosphorylated GSK-3β | 1.02 |
| GSK-3β inhibitor1 complex | 0.77 |
| GSK-3β inhibitor2 complex | 0.95 |
| GSK-3β inhibitor3 complex | 0.23 |
| GSK-3β inhibitor4 complex | 0.31 |

TABLE 5

Inhibitor-binding pocket (F67, V70, Q185, C199)

| GSK-3β structures | RMSD between inhibitor binding pockets (Å) |
| --- | --- |
| unphosphorylated GSK-3β | 1.83 |
| phosphorylated GSK-3β | 1.89 |
| GSK-3β inhibitor1 complex | 1.67 |
| GSK-3β inhibitor2 complex | 2.23 |
| GSK-3β inhibitor3 complex | 1.71 |
| GSK-3β inhibitor4 complex | 0.80 |

TABLE 6

Inhibitor-binding pocket (V70, V110, L188 and C199)

| GSK-3β structures | RMSD between inhibitor binding pockets (Å) |
| --- | --- |
| unphosphorylated GSK-3β | 0.80 |
| phosphorylated GSK-3β | 0.88 |
| GSK-3β inhibitor1 complex | 0.81 |
| GSK-3β inhibitor2 complex | 0.92 |
| GSK-3β inhibitor3 complex | 0.38 |
| GSK-3β inhibitor4 complex | 0.30 |

TABLE 7

Substrate-binding pocket (G65, S66, F67 and F93)

| GSK-3β structures | RMSD between inhibitor binding pockets (Å) |
| --- | --- |
| unphosphorylated GSK-3β | 1.93 |
| phosphorylated GSK-3β | 1.32 |
| GSK-3β inhibitor1 complex | 1.32 |
| GSK-3β inhibitor2 complex | 1.74 |
| GSK-3β inhibitor3 complex | 1.43 |
| GSK-3β inhibitor4 complex | 2.09 |

TABLE 8

Substrate-binding pocket (R96, R180, K205, N213 and Y234)

| GSK-3β structures | RMSD between inhibitor binding pockets (Å) |
| --- | --- |
| unphosphorylated GSK-3β | 0.67 |
| phosphorylated GSK-3β | 0.59 |
| GSK-3β inhibitor1 complex | 0.64 |
| GSK-3β inhibitor2 complex | 0.71 |
| GSK-3β inhibitor3 complex | 0.71 |
| GSK-3β inhibitor4 complex | 0.65 |

TABLE 9

Substrate-binding pocket (Y216, I217, C218, S219, R220 and R223)

| GSK-3β structures | RMSD between inhibitor binding pockets (Å) |
| --- | --- |
| unphosphorylated GSK-3β | 1.07 |
| phosphorylated GSK-3β | 0.36 |
| GSK-3β inhibitor1 complex | 0.46 |
| GSK-3β inhibitor2 complex | 1.35 |
| GSK-3β inhibitor3 complex | 1.39 |
| GSK-3β inhibitor4 complex | 1.21 |

The RMSD values of the overall structure between the GSK-3β-inhibitor2 structure (FIG. 4) and other GSK-3β structures (FIGS. 1-3, and 5-7) are illustrated in Table 10. The RMSD values were calculated by the program LSQKAB in CCP4, supra. Backbone atoms (C, O, N and Cα) of all residues in the overall structure according to FIGS. 1-7 were used in the calculation of the RMSD.

TABLE 10

| GSK-3β structures | RMSD of overall structure(Å) |
| --- | --- |
| unphosphorylated GSK-3β | 0.52 |
| phosphorylated GSK-3β | 1.27 |
| GSK-3β-ADP-peptide complex | 1.94 |
| GSK-3β inhibitor1 complex | 0.79 |
| GSK-3β inhibitor3 complex | 1.77 |
| GSK-3β inhibitor4 complex | 0.90 |

For the purpose of this invention, any molecule or molecular complex or binding pocket thereof that is within a root mean square deviation for backbone atoms (C, O, N and Cα) when superimposed on the relevant backbone atoms described by structure coordinates listed in any one of FIGS. 1-7 are encompassed by this invention.

In one embodiment, the present invention provides a molecule or molecular complex comprising a binding pocket defined by structure coordinates of amino acid residues which are identical to GSK-3β amino acid residues K85, M101, V110, L130 and L132 according to any one of FIGS. 1-7, wherein the root mean square deviation of the backbone atoms between said amino acid residues and said GSK-3β amino acid residues is not greater than about 3.0 Å. In one embodiment, the RMSD is not greater than about 1.0 Å. In a preferred embodiment, the RMSD is not greater than about 0.5 Å.

In a more preferred embodiment, the root mean square deviation of the backbone atoms between said amino acid residues and said GSK-3β amino acid residues according to FIG. 7 is not greater than about 0.5 Å. In one embodiment, the RMSD is not greater than about 0.2 Å.

In another embodiment, the root mean square deviation of the backbone atoms between said amino acid residues and said GSK-3β amino acid residues according to any one of FIGS. 1-7 is not greater than about 0.3 Å, and wherein at least one of said amino acid residues is not identical to the GSK-3β amino acid residue to which it corresponds. In one embodiment, the RMSD is not greater than about 0.2 Å.

In another embodiment, the present invention provides a molecule or molecular complex comprising a binding pocket defined by structure coordinates of amino acid residues which are identical to GSK-3β amino acid residues I62, V135, P136, T138 and L188 according to any one of FIGS. 1-7, wherein the root mean square deviation of the backbone atoms between said amino acid residues and said GSK-3β amino acid residues is not greater than about 3.0 Å. In one embodiment, the RMSD is not greater than about 1.5 Å. In a preferred embodiment the RMSD is not greater than about 1.0 Å.

In a more preferred embodiment, the root mean square deviation of the backbone atoms between said amino acid residues and said GSK-3β amino acid residues according to FIG. 7 is not greater than about 0.8 Å. In one embodiment, the RMSD is not greater than about 0.5 Å. In one embodiment the RMSD is not greater than about 0.3 Å.

In another embodiment, the root mean square deviation of the backbone atoms between said amino acid residues and said GSK-3β amino acid residues according to any one of FIGS. 1-7 is not greater than about 0.2 Å, and wherein at least one of said amino acid residues is not identical to the GSK-3β amino acid residue to which it corresponds.

In another embodiment, the present invention provides a molecule or molecular complex comprising a binding pocket defined by structure coordinates of amino acid residues which are identical to GSK-3β amino acid residues V70, V110, L188 and C199 according to any one of FIGS. 1-7, wherein the root mean square deviation of the backbone atoms between said amino acid residues and said GSK-3β amino acid residues is not greater than about 3.0 Å. In one embodiment the RMSD is not greater than about 1.5 Å. In a preferred embodiment the RMSD is not greater than about 1.0 Å.

In a more preferred embodiment, the root mean square deviation of the backbone atoms between said amino acid residues and said GSK-3β amino acid residues according to FIG. 7 is not greater than about 0.6 Å. In one embodiment, the RMSD is not greater than about 0.4 Å. In one embodiment, the RMSD is not greater than about 0.2 Å.

In another embodiment, the root mean square deviation of the backbone atoms between said amino acid residues and said GSK-3β amino acid residues according to any one of FIGS. 1-7 is not greater than about 0.2 Å, and wherein at least one of said amino acids is not identical to the GSK-3β amino acid to which it corresponds.

In another embodiment, the present invention provides a molecule or molecular complex comprising a binding pocket defined by structure coordinates of amino acid residues which are identical to GSK-3β amino acid residues V70, F67, Q185 and C199 according to any one of FIGS. 1-7, wherein the root mean square deviation of the backbone atoms between said amino acid residues and said GSK-3β amino acid residues is not greater than about 3.0 Å. In a preferred embodiment, the RMSD is not greater than about 2.5 Å.

In a more preferred embodiment, the root mean square deviation of the backbone atoms between said amino acid residues and said GSK-3β amino acid residues according to FIG. 7 is not greater than about 1.6 Å. In one embodiment, the RMSD is not greater than about 1.1 Å. In one embodiment, the RMSD is not greater than about 0.6 Å. In one embodiment, the RMSD is not greater than about 0.2 Å.

In another embodiment, the root mean square deviation of the backbone atoms between said amino acid residues and said GSK-3β amino acid residue according to any one of FIGS. 1-7 is not greater than about 0.3 Å, and wherein at least one of said amino acid residues is not identical to the GSK-3β amino acid residues to which it corresponds. In one embodiment, the RMSD is not greater than about 0.2 Å.

In another embodiment, the present invention provides a molecule or molecular complex comprising part of a binding pocket, said binding pocket defined by structure coordinates of amino acid residues which correspond to GSK-3β amino acid residues Y56, T59, K60, V61, I62, G63, N64, G65, S66, F67, G68, V69, V70, Y71, Q72, A73, K74, L75, L81, V82, A83, I84, K85, K86, V87, L88, E97, L98, M101, R102, L104, H106, C107, N108, I109, V110, R111, L112, R113, Y114, F115, F116, L128, N129, L130, V131, L132, D133, Y134, V135, P136, E137, T138, V139, Y140, R141, V142, R144, P154, V155, I156, Y157, V158, K159, L160, Y161, M162, Y163, Q164, L165, F166, R167, S168, L169, A170, Y171, I172, H173, S174, F175, G176, I177, C178, H179, R180, D181, I182, K183, P184, Q185, N186, L187, L188, L189, D190, P191, A194, V195, L196, K197, L198, C199, D200, F201, G202, S203 and S219 according to any one of FIGS. 1-7, wherein the root mean square deviation of the backbone atoms between said amino acid residues and said GSK-3β amino acid residues is not greater than about 0.2 Å. In a preferred embodiment, said amino acid residues are identical to said GSK-3β amino acid residues.

In yet another embodiment, the present invention provides a molecule or molecular complex comprising a binding pocket defined by structure coordinates of amino acid residues which are identical to GSK-3β amino acid residues G65, S66, F67 and F93 according to any one of FIGS. 1-7, wherein the root mean square deviation of the backbone atoms between said amino acid residues and said GSK-3β amino acid residues is not greater than about 3.0 Å. In one embodiment, the RMSD is not greater than about 2.5 Å. In a preferred embodiment, the RMSD is not greater than about 2.0 Å.

In a more preferred embodiment, the root mean square deviation of the backbone atoms between said amino acid residues and said GSK-3β amino acid residues according to FIG. 7 is not greater than about 1.5 Å. In one embodiment, the RMSD is not greater than about 1.1 Å. In one embodiment, the RMSD is not greater than about 0.7 Å. In one embodiment, the RMSD is not greater than about 0.5 Å.

In another embodiment, the root mean square deviation of the backbone atoms between said amino acid residues and said GSK-3β amino acid residues according to any one of FIGS. 1-7 is not greater than about 1.1 Å, and wherein at least one of said amino acid residues is not identical to the GSK-3β amino acid residues to which it corresponds. In one embodiment, the RMSD is not greater than about 0.8 Å. In one embodiment, the RMSD is not greater than about 0.4 Å. In one embodiment, the RMSD is not greater than about 0.2 Å.

In another embodiment, the present invention provides a molecule or molecular complex comprising a binding pocket defined by structure coordinates of amino acid residues which correspond to GSK-3β amino acids R96, R180, K205, N213 and Y234 according to any one of FIGS. 1-7, wherein the root mean square deviation of the backbone atoms between said amino acid residues and said GSK-3β amino acid residues is not greater than about 3.0 Å, wherein said binding pocket comprises an amino acid residue asparagine corresponding to said GSK-3β amino acid residue N213. In another embodiment, said amino acid residues are identical to said GSK-3β amino acids. In one embodiment, the RMSD is not greater than about 1.5 Å. In a preferred embodiment, the RMSD is not greater than about 1.0 Å.

In a more preferred embodiment, the root mean square deviation of backbone atoms between said amino acid residues and said GSK-3β amino acid residues according to FIG. 7 is not greater than about 0.4 Å. In one embodiment, the RMSD is not greater than about 0.2 Å.

In another embodiment, the root mean square deviation of the backbone atoms between said amino acid residues and said GSK-3β amino acid residues according to any one of FIGS. 1-7 is not greater than about 3.0 Å, and wherein at least one of said amino acid residues is not identical to the GSK-3β amino acid residues to which it corresponds. In one embodiment, the RMSD is not greater than about 1.2 Å. In one embodiment, the RMSD is not greater than about 0.7 Å. In one embodiment, the RMSD is not greater than about 0.3 Å.

In another embodiment, the present invention provides a molecule or molecular complex comprising a binding pocket defined by structure coordinates of amino acid residues which correspond to GSK-3β amino acid residues Y216, I217, C218, S219, R220 and R223 according to any one of FIGS. 1-7, wherein the root mean square deviation of the backbone atoms between said amino acid residues and said GSK-3β amino acid residues is not greater than about 3.0 Å, wherein said binding pocket comprises a cysteine amino acid residue corresponding to said GSK-3β amino acid residue C218. In another embodiment, said amino acid residues are identical to said GSK-3β amino acids. In one embodiment, the RMSD is not greater than about 2.0 Å. In a preferred embodiment, the RMSD is not greater than about 1.5 Å.

In a more preferred embodiment, the root mean square deviation of backbone atoms between said amino acid residues and said GSK-3β amino acid residues according to FIG. 5 is not greater than about 1.1 Å. In one embodiment, the RMSD is not greater than about 0.5 Å. In one embodiment, the RMSD is not greater than about 0.2 Å.

In another embodiment, the root mean square deviation of the backbone atoms between said amino acid residues and said GSK-3β amino acid residues according to any one of FIGS. 1-7 is not greater than about 1.1 Å, and wherein at least one of said amino acid residues is not identical to the GSK-3β amino acid to which it corresponds. In one embodiment, the RMSD is not greater than about 0.8 Å. In one embodiment, the RMSD is not greater than about 0.5 Å. In one embodiment, the RMSD is not greater than about 0.2 Å.

In another embodiment, the present invention provides a molecule or molecular complex comprising part of a binding pocket, said binding pocket defined by structure coordinates of amino acid residues which correspond to GSK-3β amino acid residues N64, G65, S66, F67, G68, V87, L88, D90, K91, R92, F93, K94, N95, R96, E97, R180, D181, I182, K183 Q185, N186, D200, F201, G202, S203, A204, K205, Q206, L207, E211, P212, N213, V214, S215, Y216, I217, C218, S219, R220, Y221, Y222, R223, L227, T232 and Y234 according to any one of FIGS. 1-7, wherein the root mean square deviation of the backbone atoms between said amino acid residues and said GSK-3β amino acid residues is not greater than about 1.0 Å. In one embodiment, the RMSD is not greater than about 0.7 Å. In one embodiment, the RMSD is not greater than about 0.5 Å. In one embodiment, the RMSD is not greater than about 0.2 Å. In one embodiment, said amino acid residues are identical to said GSK-3β amino acid residues.

In one embodiment, the present invention provides a molecule or molecular complex comprising a GSK-3β protein defined by structure coordinates of the amino acid residues which correspond to GSK-3β amino acid residues according to any one of FIGS. 1-7, wherein the root mean square deviation of the backbone atoms between said amino acid residues and said GSK-3β amino acid residues is not greater than about 2.0 Å. In one embodiment, the RMSD is not greater than about 1.7 Å. In one embodiment, the RMSD is not greater than about 1.1 Å. In one embodiment, the RMSD is not greater than about 0.7 Å. In one embodiment, said amino acid residues are identical to said GSK-3β amino acid residues.

In one embodiment, the present invention provides a molecule or molecular complex comprising a protein kinase comprising a glutamine or glutamic acid residue that corresponds to Gln185 of GSK-3β protein, wherein the χ1 angle is in the range of 123° to 180°, and the χ2 angle is in the range of −174° to −180° and 106° to 180°. In another embodiment, the χ1 angle is in the range of −100° to −180° and the χ2 angle is in the range of −151° to −180° and 126° to 180°.

In one embodiment, the above molecules or molecular complexes are GSK-3β proteins or a GSK-3β homologues. In another embodiment, the above molecules or molecular complexes are in crystalline form.

Computer Systems

According to another embodiment, this invention provides a machine-readable data storage medium, comprising a data storage material encoded with machine-readable data, wherein said data defines the above mentioned molecules or molecular complexes. In one embodiment, the data defines the above mentioned binding pockets by comprising the structure coordinates of said amino acid residues according to any one of FIGS. 1-7.

To use the structure coordinates generated for the GSK-3β, homologues thereof, or one of its binding pockets, it is sometimes necessary to convert them into a three-dimensional shape. This is achieved through the use of commercially available software that is capable of generating a three-dimensional structure of molecules or portions thereof from a set of structure coordinates. The three-dimensional structure may be displayed as a graphical representation.

Therefore, according to another embodiment, this invention provides a machine-readable data storage medium comprising a data storage material encoded with machine readable data. In one embodiment, a machine programmed with instructions for using said data, is capable of generating a three-dimensional structure of any of the molecule or molecular complexes, or binding pockets thereof, that are described herein.

This invention also provides a computer comprising:
a) a machine-readable data storage medium comprising a data storage material encoded with machine-readable data, wherein said data defines any one of the above binding pockets of the molecule or molecular complex;
b) a working memory for storing instructions for processing said machine-readable data;
c) a central processing unit coupled to said working memory and to said machine-readable data storage medium for processing said machine readable data; and
d) output hardware coupled to said central processing unit for outputting information of said binding pocket or information produced by using said binding pocket.

Information of said binding pocket or information produced by using said binding pocket can be outputted through a display terminal, printer or disk drive. The information can be in graphical or alphanumeric form. In another embodiment, the computer further comprises a commercially available software program to display the information as a graphical representation. Examples of software programs include but are not limited to QUANTA (Molecular Simulations, Inc., San Diego, Calif. ©2001), O (Jones et al., Acta Crystallogr. A47, pp. 110-119 (1991)) and RIBBONS (Carson, J. Appl. Crystallogr., 24, pp. 9589-961 (1991)), which are incorporated herein by reference.

Figure 22:
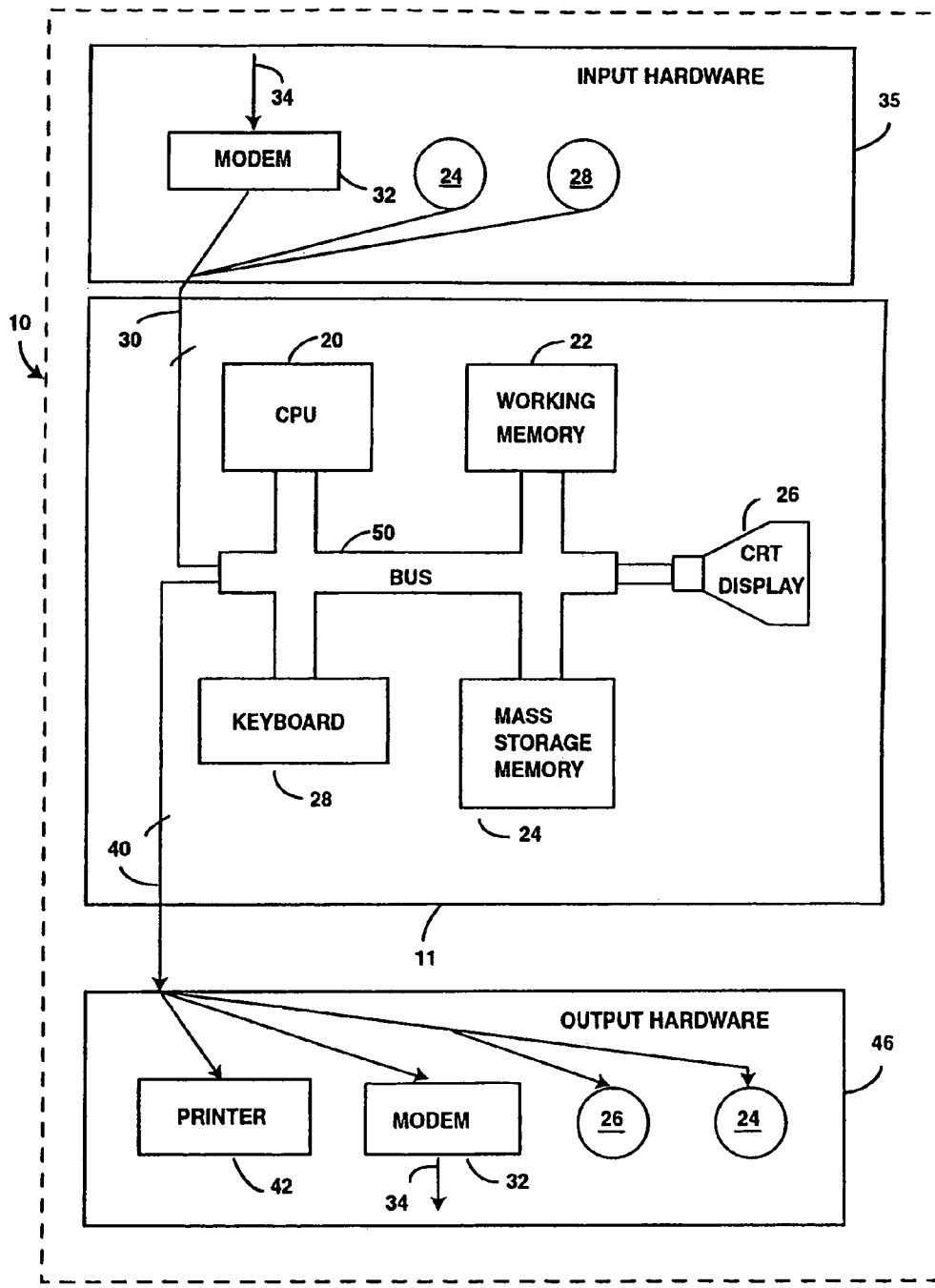
FIG. 22 shows a diagram of a system used to carry out the instructions encoded by the storage medium of FIGS. 23 and 24.

FIG. 22 demonstrates one version of these embodiments. System (10) includes a computer (11) comprising a central processing unit ("CPU") (20), a working memory (22) which may be, e.g., RAM (random-access memory) or "core" memory, mass storage memory (24) (such as one or more disk drives or CD-ROM drives), one or more cathode-ray tube ("CRT") display terminals (26), one or more keyboards (28), one or more input lines (30), and one or more output lines (40), all of which are, interconnected by a conventional bi-directional system bus (50).

Input hardware (35), coupled to computer (11) by input lines (30), may be implemented in a variety of ways. Machine-readable data of this invention may be inputted via the use of a modem or modems (32) connected by a telephone line or dedicated data line (34). Alternatively or additionally, the input hardware (35) may comprise CD-ROM drives or disk drives (24). In conjunction with display terminal (26), keyboard (28) may also be used as an input device.

Output hardware (46), coupled to computer (11) by output lines (40), may similarly be implemented by conventional devices. By way of example, output hardware (46) may include CRT display terminal (26) for displaying a graphical representation of a binding pocket of this invention using a program such as QUANTA as described herein. Output hardware might also include a printer (42), so that hard copy output may be produced, or a disk drive (24), to store system output for later use.

In operation, CPU (20) coordinates the use of the various input and output devices (35), (46), coordinates data accesses from mass storage (24) and accesses to and from working memory (22), and determines the sequence of data processing steps. A number of programs may be used to process the machine-readable data of this invention. Such programs are discussed in reference to the computational methods of drug discovery as described herein. Specific references to components of the hardware system (10) are included as appropriate throughout the following description of the data storage medium.

Figure 23:
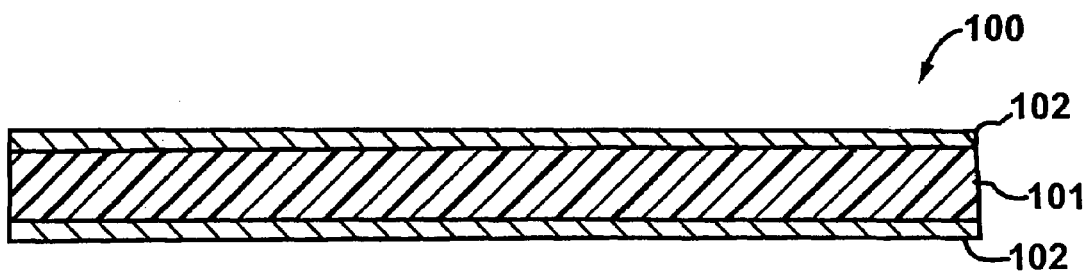
FIG. 23 shows a cross section of a magnetic storage medium.

FIG. 23 shows a cross section of a magnetic data storage medium (100) which can be encoded with a machine-readable data that can be carried out by a system such as system (10) of FIG. 22. Medium (100) can be a conventional floppy diskette or hard disk, having a suitable substrate (101), which may be conventional, and a suitable coating (102), which may be conventional, on one or both sides, containing magnetic domains (not visible) whose polarity or orientation can be altered magnetically. Medium (100) may also have an opening (not shown) for receiving the spindle of a disk drive or other data storage device (24).

The magnetic domains of coating (102) of medium (100) are polarized or oriented so as to encode in manner which may be conventional, machine readable data such as that described herein, for execution by a system such as system (10) of FIG. 22.

Figure 24:
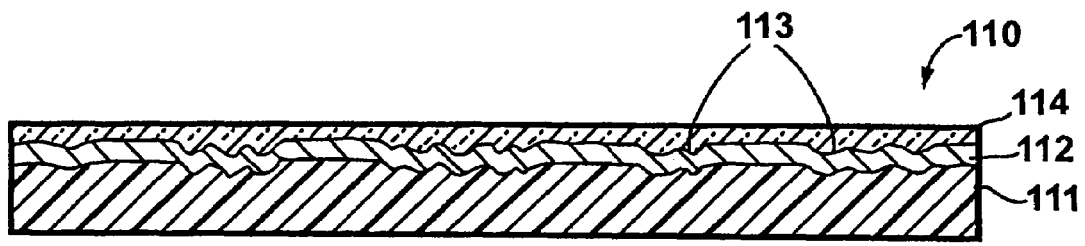
FIG. 24 shows a cross section of a optically-readable data storage medium.

FIG. 24 shows a cross section of an optically-readable data storage medium (110) which also can be encoded with such a machine-readable data, or set of instructions, which can be carried out by a system such as system (10) of FIG. 22. Medium (110) can be a conventional compact disk read only memory (CD-ROM) or a rewritable medium such as a magneto-optical disk which is optically readable and magneto-optically writable. Medium (100) preferably has a suitable substrate (111), which may be conventional, and a suitable coating (112), which may be conventional, usually of one side of substrate (111).

In the case of CD-ROM, as is well known, coating (112) is reflective and is impressed with a plurality of pits (113) to encode the machine-readable data. The arrangement of pits is read by reflecting laser light off the surface of coating (112). A protective coating (114), which preferably is substantially transparent, is provided on top of coating (112).

In the case of a magneto-optical disk, as is well known, coating (112) has no pits (113), but has a plurality of magnetic domains whose polarity or orientation can be changed magnetically when heated above a certain temperature, as by a laser (not shown). The orientation of the domains can be read by measuring the polarization of laser light reflected from coating (112). The arrangement of the domains encodes the data as described above.

Thus, in accordance with the present invention, data capable of generating the three dimensional structure of the above molecules or molecular complexes, or binding pockets thereof, can be stored in a machine-readable storage medium, which is capable of displaying a graphical three-dimensional representation of the structure.

Rational Drug Design

The GSK-3β X-ray coordinate data, when used in conjunction with a computer programmed with software to generate those coordinates into the three-dimensional structure of GSK-3β may be used for a variety of purposes, such as drug discovery. The coordinate data themselves may also be used directly to perform computer modelling and fitting operations.

For example, the structure encoded by the data may be computationally evaluated for its ability to associate with chemical entities. Chemical entities that associate with GSK-3β may inhibit GSK-3β and its homologues, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with a molecule or molecular complex as described previously in the different embodiments.

This method comprises the steps of: a) employing computational means to perform a fitting operation between the chemical entity and a binding pocket of the molecule or molecular complex; b) analyzing the results of said fitting operation to quantify the association between the chemical entity and the binding pocket; and optionally c) outputting said quantified association to a suitable output hardware, such as a CRT display terminal, a printer or a disk drive, as described previously. The method may further comprise the step of generating a three-dimensional graphical representation of the molecule or molecular complex or binding pocket thereof prior to step a).

Alternatively, the structure coordinates of the above binding pockets can be utilized in a method for identifying an agonist or antagonist of a molecule comprising any of the above binding pockets. This method comprises the steps of:
 a) using the three-dimensional structure of said molecule or molecular complex to design or select a chemical entity;
 b) contacting said chemical entity with the molecule or molecular complex and monitoring the activity of the molecule or molecular complex; and
 c) classifying said chemical entity as an agonist or antagonist based on the effect of said chemical entity on the activity of the molecule or molecular complex.

In one embodiment, step a) is using the three-dimensional structure of the binding pocket of the molecule or molecular complex. In another embodiment, the three-dimensional structure is displayed as a graphical representation.

The present invention permits the use of molecular design techniques to identify, select and design chemical entities, including inhibitory compounds, capable of binding to the above binding pockets.

The elucidation of binding pockets on GSK-3β provides the necessary information for designing new chemical entities and compounds that may interact with GSK-3β substrate or ATP-binding pockets, in whole or in part. Due to the homology in the kinase core of GSK-3β and GSK-3α, compounds that inhibit GSK-3β are also expected to inhibit GSK-3α, especially those compounds that bind the ATP-binding pocket.

Throughout this section, discussions about the ability of an entity to bind to, associate with or inhibit the above binding pockets refers to features of the entity alone. Assays to determine if a compound binds to GSK-3β are well known in the art and are exemplified below.

The design of compounds that bind to or inhibit the above binding pockets according to this invention generally involves consideration of two factors. First, the entity must be capable of physically and structurally associating with parts or all of the above binding pockets. Non-covalent molecular interactions important in this association include hydrogen bonding, van der Waals interactions, hydrophobic interactions and electrostatic interactions.

Second, the entity must be able to assume a conformation that allows it to associate with the above binding pockets directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the above binding pockets.

The potential inhibitory or binding effect of a chemical entity on the above binding pockets may be analyzed prior to its actual synthesis and testing by the use of computer modeling techniques. If the theoretical structure of the given entity suggests insufficient interaction and association between it and the above binding pockets, testing of the entity is obviated. However, if computer modeling indicates a strong interaction, the molecule may then be synthesized and tested for its ability to bind to the above binding pocket. This may be achieved by testing the ability of the molecule to inhibit GSK-3β using the assays described in Example 18. In this manner, synthesis of inoperative compounds may be avoided.

A potential inhibitor of the above binding pockets may be computationally evaluated by means of a series of steps in which chemical entities or fragments are screened and selected for their ability to associate with the above binding pockets.

One skilled in the art may use one of several methods to screen chemical entities or fragments for their ability to associate with the above binding pockets. This process may begin by visual inspection of, for example, any of the above binding pockets on the computer screen based on the GSK-3β structure coordinates in any one of FIGS. 1-7 or other coordinates which define a similar shape generated from the machine-readable storage medium. Selected fragments or chemical entities may then be positioned in a variety of orientations, or docked, within that binding pocket as defined supra. Docking may be accomplished using software such as QUANTA and Sybyl, followed by energy minimization and molecular dynamics with standard molecular mechanics force fields, such as CHARMM and AMBER.

Specialized computer programs may also assist in the process of selecting fragments or chemical entities. These include:
 1. GRID (P. J. Goodford, "A Computational Procedure for Determining Energetically Favorable Binding Sites on Biologically Important Macromolecules", *J. Med. Chem.*, 28, pp. 849-857 (1985)). GRID is available from Oxford University, Oxford, UK.
 2. MCSS (A. Miranker et al., "Functionality Maps of Binding Sites: A Multiple Copy Simultaneous Search Method." *Proteins: Structure, Function and Genetics,* 11, pp. 29-34 (1991)). MCSS is available from Molecular Simulations, San Diego, Calif.
 3. AUTODOCK (D. S. Goodsell et al., "Automated Docking of Substrates to Proteins by Simulated Annealing", *Proteins: Structure, Function, and Genetics,* 8, pp. 195-202 (1990)). AUTODOCK is available from Scripps Research Institute, La Jolla, Calif.

4. DOCK (I. D. Kuntz et al., "A Geometric Approach to Macromolecule-Ligand Interactions", *J. Mol. Biol.*, 161, pp. 269-288 (1982)). DOCK is available from University of California, San Francisco, Calif.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of GSK-3β. This would be followed by manual model building using software such as QUANTA or Sybyl (Tripos Associates, St. Louis, Mo.).

Useful programs to aid one of skill in the art in connecting the individual chemical entities or fragments include:

1. CAVEAT (P. A. Bartlett et al., "CAVEAT: A Program to Facilitate the Structure-Derived Design of Biologically Active Molecules", in "*Molecular Recognition in Chemical and Biological Problems*", Special Pub., *Royal Chem. Soc.*, 78, pp. 182-196 (1989); G. Lauri and P. A. Bartlett, "CAVEAT: a Program to Facilitate the Design of Organic Molecules", *J. Comput. Aided Mol. Des.*, 8, pp. 51-66 (1994)). CAVEAT is available from the University of California, Berkeley, Calif.
2. 3D Database systems such as ISIS (MDL Information Systems, San Leandro, Calif.). This area is reviewed in Y. C. Martin, "3D Database Searching in Drug Design", *J. Med. Chem.*, 35, pp. 2145-2154 (1992).
3. HOOK (M. B. Eisen et al., "HOOK: A Program for Finding Novel Molecular Architectures that Satisfy the Chemical and Steric Requirements of a Macromolecule Binding Site", *Proteins: Struct., Funct., Genet.*, 19, pp. 199-221 (1994). HOOK is available from Molecular Simulations, San Diego, Calif.

Instead of proceeding to build an inhibitor of any of the above binding pockets in a step-wise fashion, one fragment or chemical entity at a time as described above, inhibitory or other GSK-3β binding compounds may be designed as a whole or "de novo" using either an empty binding pocket or optionally including some portion(s) of a known inhibitor(s). There are many de novo ligand design methods including:

1. LUDI (H.-J. Bohm, "The Computer Program LUDI: A New Method for the De Novo Design of Enzyme Inhibitors", *J. Comp. Aid. Molec. Design*, 6, pp. 61-78 (1992)). LUDI is available from Molecular Simulations Incorporated, San Diego, Calif.
2. LEGEND (Y. Nishibata et al., *Tetrahedron*, 47, p. 8985 (1991)). LEGEND is available from Molecular Simulations Incorporated, San Diego, Calif.
3. LeapFrog (available from Tripos Associates, St. Louis, Mo.).
4. SPROUT (V. Gillet et al., "SPROUT: A Program for Structure Generation)", *J. Comput. Aided Mol. Design*, 7, pp. 127-153 (1993)). SPROUT is available from the University of Leeds, UK.

Other molecular modeling techniques may also be employed in accordance with this invention (see, e.g., N. C. Cohen et al., "Molecular Modeling Software and Methods for Medicinal Chemistry, *J. Med. Chem.*, 33, pp. 883-894 (1990); see also, M. A. Navia and M. A. Murcko, "The Use of Structural Information in Drug Design", *Current Opinions in Structural Biology*, 2, pp. 202-210 (1992); L. M. Balbes et al., "A Perspective of Modern Methods in Computer-Aided Drug Design", in *Reviews in Computational Chemistry*, Vol. 5, K. B. Lipkowitz and D. B. Boyd, Eds., VCH, New York, pp. 337-380 (1994); see also, W. C. Guida, "Software For Structure-Based Drug Design", *Curr. Opin. Struct. Biology*, 4, pp. 777-781 (1994)).

Once a compound has been designed or selected by the above methods, the efficiency with which that entity may bind to any of the above binding pockets may be tested and optimized by computational evaluation. For example, an effective binding pocket inhibitor must preferably demonstrate a relatively small difference in energy between its bound and free states (i.e., a small deformation energy of binding). Thus, the most efficient binding pocket inhibitors should preferably be designed with a deformation energy of binding of not greater than about 10 kcal/mole, more preferably, not greater than 7 kcal/mole. Binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

An entity designed or selected as binding to any one of the above binding pockets may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. ©1995); AMBER, version 4.1 (P. A. Kollman, University of California at San Francisco, ©1995); QUANTA/CHARMM (Molecular Simulations, Inc., San Diego, Calif. ©1998); Insight II/Discover (Molecular Simulations, Inc., San Diego, Calif. ©1998); DelPhi (Molecular Simulations, Inc., San Diego, Calif. ©1998); and AMSOL (Quantum Chemistry Program Exchange, Indiana University). These programs may be implemented, for instance, using a Silicon Graphics workstation such as an Indigo2 with "IMPACT" graphics. Other hardware systems and software packages will be known to those skilled in the art.

Another approach enabled by this invention, is the computational screening of small molecule databases for chemical entities or compounds that can bind in whole, or in part, to any of the above binding pockets. In this screening, the quality of fit of such entities to the binding pocket may be judged either by shape complementarity or by estimated interaction energy (E. C. Meng et al., *J. Comp. Chem.*, 13, pp. 505-524 (1992)).

Although the phosphorylated and unphosphorylated forms of GSK-3β have similar binding pockets, the subtle differences in water molecules, ions, position of the Y216 residue near the binding pockets as well as deviations in the overall structure may render slightly different results in the calculation of binding energies for inhibitors. By comparing the binding energies of inhibitors to the phosphorylated and unphosphorylated form, one may select inhibitors that are more suitable for one form than the other. Furthermore, the identification of inhibitors for both forms would allow the options of inhibiting GSK-3β prior to or after phosphorylation by upstream kinases in vivo.

Another particularly useful drug design technique enabled by this invention is iterative drug design. Iterative drug design is a method for optimizing associations between a protein and a compound by determining and evaluating the three-dimensional structures of successive sets of protein/compound complexes.

In iterative drug design, crystals of a series of protein or protein complexes are obtained and then the three-dimensional structures of each crystal is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affect the protein/compound associations, these associations may be optimized.

In some cases, iterative drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex. The phosphorylated crystals provided by this invention may be soaked in the presence of a compound or compounds, to provide other crystal complexes.

Structure Determination of Other Molecules

The structure coordinates set forth in any one of FIGS. 1-7 can also be used to aid in obtaining structural information about another crystallized molecule or molecular complex. This may be achieved by any of a number of well-known techniques, including molecular replacement.

According to an alternate embodiment, the machine-readable data storage medium comprises a data storage material encoded with a first set of machine readable data which comprises the Fourier transform of at least a portion of the structure coordinates set forth in any one of FIGS. 1-7, and which, when using a machine programmed with instructions for using said data, can be combined with a second set of machine readable data comprising the X-ray diffraction pattern of a molecule or molecular complex to determine at least a portion of the structure coordinates corresponding to the second set of machine readable data.

In another embodiment, the invention provides a computer for determining at least a portion of the structure coordinates corresponding to X-ray diffraction data obtained from a molecule or molecular complex, wherein said computer comprises:

a) a machine-readable data storage medium comprising a data storage material encoded with machine-readable data, wherein said data comprises at least a portion of the structure coordinates of GSK-3β according to any one of FIGS. 1-7;

b) a machine-readable data storage medium comprising a data storage material encoded with machine-readable data, wherein said data comprises X-ray diffraction data obtained from said molecule or molecular complex; and c) instructions for performing a Fourier transform of the machine readable data of (a) and for processing said machine readable data of (b) into structure coordinates.

For example, the Fourier transform of at least a portion of the structure coordinates set forth in any one of FIGS. 1-7 may be used to determine at least a portion of the structure coordinates of GSK-3β homologues, and other sufficiently homologous kinases such as CDK2. In one embodiment, the molecule is a GSK-3β homologue. In another embodiment, the molecular complex is selected from the group consisting of a GSK-3β protein complex and a GSK-3β homologue complex.

Therefore, in another embodiment this invention provides a method of utilizing molecular replacement to obtain structural information about a molecule or molecular complex whose structure is unknown comprising the steps of:

a) crystallizing said molecule or molecular complex of unknown structure;

b) generating an X-ray diffraction pattern from said crystallized molecule or molecular complex; and c) applying at least a portion of the GSK-3β structure coordinates set forth in any one of FIGS. 1-7 to the X-ray diffraction pattern to generate a three-dimensional electron density map of the molecule or molecular complex whose structure is unknown.

By using molecular replacement, all or part of the structure coordinates of the GSK-3β as provided by this invention (and set forth in any one of FIGS. 1-7) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of the GSK-3β according to any one of FIGS. 1-7 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions", in *Meth. Enzymol.*, 115, pp. 55-77 (1985); M. G. Rossmann, ed., "The Molecular Replacement Method", *Int. Sci. Rev. Ser.*, No. 13, Gordon & Breach, New York (1972)).

The structure of any portion of any crystallized molecule or molecular complex that is sufficiently homologous to any portion of the GSK-3β can be resolved by this method.

In a preferred embodiment, the method of molecular replacement is utilized to obtain structural information about a GSK-3 homologue. The structure coordinates of GSK-3β as provided by this invention are particularly useful in solving the structure of GSK-3β complexes that are bound by ligands, substrates and inhibitors.

Furthermore, the structure coordinates of GSK-3β as provided by this invention are useful in solving the structure of GSK-3β proteins that have amino acid substitutions, additions and/or deletions (referred to collectively as "GSK-3β mutants", as compared to naturally occurring GSK-3β. These GSK-3β mutants may optionally be crystallized in co-complex with a chemical entity, such as a non-hydrolyzable ATP analogue, a suicide substrate or a inhibitor. The crystal structures of a series of such complexes may then be solved by molecular replacement and compared with that of wild-type GSK-3β. Potential sites for modification within the various binding pockets of the enzyme may thus be identified. This information provides an additional tool for determining the most efficient binding interactions, for example, increased hydrophobic interactions, between GSK-3β and a chemical entity or compound.

The structure coordinates are also particularly useful to solving the structure of crystals of GSK-3β or GSK-3β homologues co-complexed with a variety of chemical entities. This approach enables the determination of the optimal sites for interaction between chemical entities, including candidate GSK-3β inhibitors and GSK-3β. For example, high resolution X-ray diffraction data collected from crystals exposed to different types of solvent allows the determination of where each type of solvent molecule resides. Small molecules that bind tightly to those sites can then be designed and synthesized and tested for their GSK-3β inhibition activity.

All of the complexes referred to above may be studied using well-known X-ray diffraction techniques and may be refined versus 1.5-3.4 Å resolution X-ray data to an R value of about 0.30 or less using computer software, such as X-PLOR (Yale University, ©1992, distributed by Molecular Simulations, Inc.; see, e.g., Blundell & Johnson, supra; *Meth. Enzymol.*, vol. 114 & 115, H. W. Wyckoff et al., eds., Academic Press (1985)). This information may thus be used to optimize known GSK-3β inhibitors, and more importantly, to design new GSK-3β inhibitors.

In order that this invention be more fully understood, the following examples are set forth. These examples are for the purpose of illustration only and are not to be construed as limiting the scope of the invention in any way.

EXAMPLE 1

3-Amino-4,5-diphenyl-1H-pyrazolo[3,4-c]pyridazine (Compound 1)

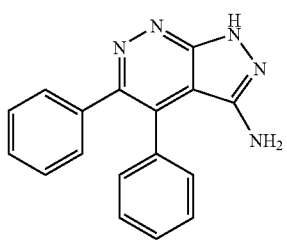

The appropriate diaryl keto hydrazone (see Scheme I, formula 1, wherein X is H and Y is H; 0.85 mmol) and ethyl cyanoacetate (0.9 mmol) were added to 3 mL ethanol. Sodium ethoxide (0.9 mmol) in THF was subsequently added and the mixture refluxed for 6 hours. After cooling, the solvent was removed under vacuum and the residue taken up in 10 mL dichloromethane. It was then washed with 0.1 M HCl, water and dried with sodium sulfate. After filtering, the solvent was removed under vacuum and the product, 4-cyano-5,6-diaryl 2(1H) pyridazinone (Scheme I, formula 2, wherein X is H and Y is H) was purified by chromatography on silica gel (5:95 methanol/dichloromethane).

Purified 4-cyano-5,6-diaryl 2(1H) pyridazinone (100 mg) was added to 2 mL POCl$_3$ and heated to 100° C. for 5-6 hours. After cooling, the reaction mixture was poured onto 10 mL ice and stirred for one hour. The resulting 3-chloro-4-cyano-5,6-diaryl pyridazine (Scheme I, formula 3, wherein X is H and Y is H) was filtered off, washed with water, air dried and used in the next step without further purification.

Crude 3-chloro-4-cyano-5,6-diaryl pyridazine was refluxed with 2 equivalents of anhydrous hydrazine in ethanol for several hours. Upon cooling, the product would sometimes precipitate out, in which case the pure title compound was obtained by recrystallizing from ethanol. Otherwise the title compound was purified by chromatography on silica gel (5:95 methanol-dichloromethane): MS (ES+) m/e: 288.01 (M+H); analytical HPLC(C$_{18}$ column) 2.96 minutes.

EXAMPLE 2

3-Amino-4(4-chlorophenyl)-5-phenyl-1H-pyrazolo [3,4-c]pyridazine (Compound 2)

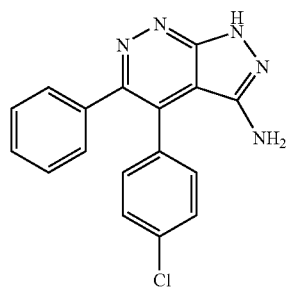

The title compound was obtained according to synthetic procedures described in EXAMPLE 1 using the appropriate diaryl keto hydrazone (X is H and Y is p-Cl): MS (ES+) m/e: 321.89 (M+H); analytical HPLC(C$_{18}$ column) 3.33 minutes.

EXAMPLE 3

3-Amino-4,5-bis(4-fluorophenyl)-1H-pyrazolo[3,4-c]pyridazine (Compound 3)

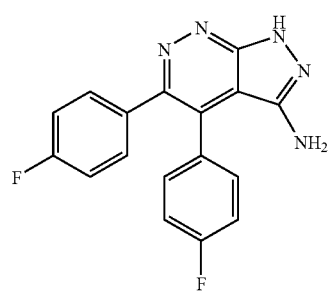

The title compound was obtained according to synthetic procedures described in EXAMPLE 1 using the appropriate diaryl keto hydrazone (X is p-F and Y is p-F): MS (138+) m/e: 324.1 (M+H); analytical HPLC (C$_{18}$ column) 3.26 minutes.

EXAMPLE 4

3-Amino-4-phenyl-5-(4-fluorophenyl)-1H-pyrazolo [3,4-c]pyridazine (Compound 4)

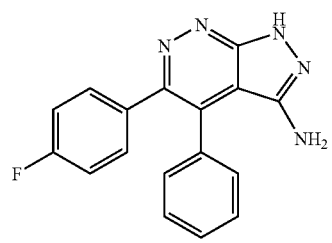

The title compound was obtained according to synthetic procedures described in EXAMPLE 1 using the appropriate diaryl keto hydrazone (X is p-F and Y is H): MS (ES+) m/e: 306.1 (M+H); analytical HPLC ($C_{18}$ column) 3.08 minutes.

EXAMPLE 5

3-Amino-4-(4-fluorophenyl)-5-phenyl-1H-pyrazolo [3,4-c]pyridazine (Compound 5)

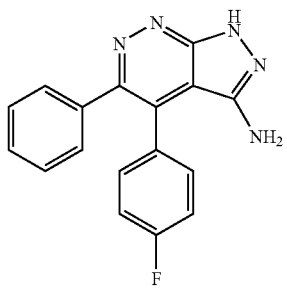

The title compound was obtained according to synthetic procedures described in EXAMPLE 1 using the appropriate diaryl keto hydrazone (X is H and Y is p-F): MS (ES+) m/e: 306.1 (M+H); analytical HPLC ($C_{18}$ column) 3.02 minutes.

EXAMPLE 6

3-Amino-4-(3-fluorophenyl)-5-phenyl-1H-pyrazolo [3,4-c]pyridazine (Compound 6)

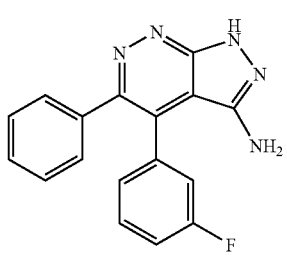

The title compound was obtained according to synthetic procedures described in EXAMPLE 1 using the appropriate diaryl keto hydrazone (X is H and Y is m-F): MS (ES+) m/e: 306.1 (M+H); analytical HPLC($C_{18}$ column) 2.94 minutes.

EXAMPLE 7

3-Amino-4-phenyl-5-(4-pyridyl)-1H-pyrazolo[3,4-c] pyridazine (Compound 7)

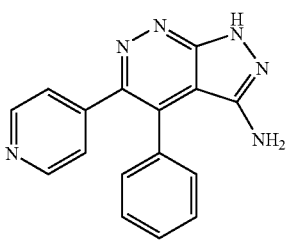

The title compound was obtained according to synthetic procedures described in EXAMPLE 1 using the appropriate heteroaryl aryl keto hydrazone: MS (ES+) m/e: 289.1 (M+H); analytical HPLC ($C_{18}$ column) 1.77 minutes.

EXAMPLE 8

3-Amino-4-phenyl-5-(3-fluorophenyl)-1H-pyrazolo [3,4-c]pyridazine (Compound 8)

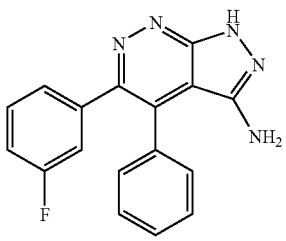

The title compound was obtained according to synthetic procedures described in EXAMPLE 1 using the appropriate diaryl keto hydrazone (X is m-F and Y is H): MS (ES+) m/e: 306.1 (M+H); analytical HPLC ($C_{18}$ column) 3.12 minutes.

EXAMPLE 9

N-(4,5-Diphenyl-1H-pyrazolo[3,4-c]pyridazin-3-yl)-acetamide (Compound 9)

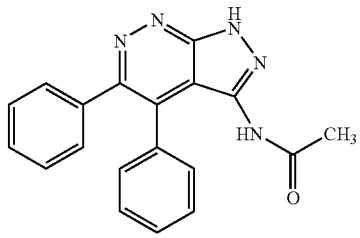

The title compound was obtained according to synthetic procedures described in EXAMPLE 1 using the appropriate diaryl keto hydrazone (X is H and Y is H), followed by amidation with $CH_3CO_2H$: MS (ES+) m/e: 330.1 (M+H); analytical HPLC ($C_{18}$ column) 2.65 minutes.

EXAMPLE 10

N-(4,5-Diphenyl-1H-pyrazolo[3,4-c]pyridazin-3-yl)-benzamide (Compound 10)

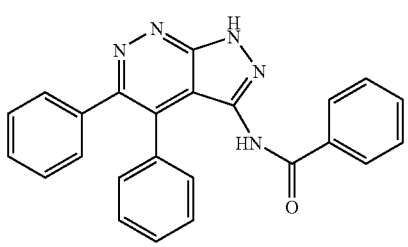

The title compound was obtained according to synthetic procedures described in EXAMPLE 1 using the appropriate diaryl keto hydrazone (X is H and Y is H), followed by amidation with benzoic acid: MS (ES+) m/e: 414.2 (M+Na+); analytical HPLC (C₁₈ column) 2.90 minutes.

EXAMPLE 11

3-Amino-4-phenyl-5-(4-methyl-phenyl)-1H-pyrazolo[3,4-c]pyridazine (Compound 11)

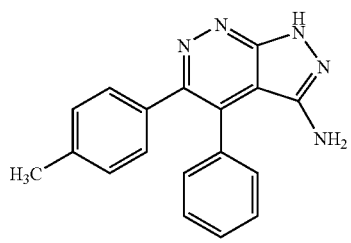

The title compound was obtained according to synthetic procedures described in EXAMPLE 1 using the appropriate diaryl keto hydrazone (X is p-CH₃ and Y is H): MS (ES+) m/e: 302.1 (M+H); analytical HPLC (C₁₈ column) 3.07 minutes.

EXAMPLE 12

3-Amino-4-phenyl-5-(2-methyl-phenyl)-1H-pyrazolo[3,4-c]pyridazine (Compound 12)

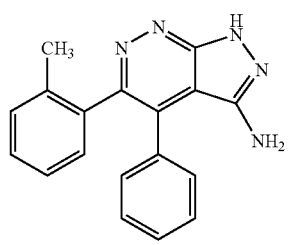

The title compound was obtained according to synthetic procedures described in EXAMPLE 1 using the appropriate diaryl keto hydrazone (X is o-CH₃ and Y is H): MS (ES+) m/e: 302.1 (M+H); analytical HPLC (C₁₈ column) 2.94 minutes.

EXAMPLE 13

3-Amino-4-phenyl-5-(3-methyl-phenyl)-1H-pyrazolo[3,4-c]pyridazine (Compound 13)

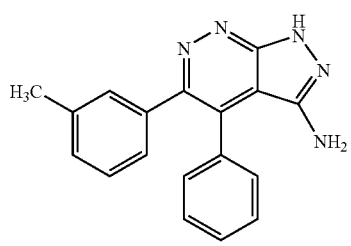

The title compound was obtained according to synthetic procedures described in EXAMPLE 1 using the appropriate diaryl keto hydrazone (X is m-CH₃ and Y is H): MS (ES+) m/e: 302.1 (M+H); analytical HPLC (C₁₈ column) 3.09 minutes.

EXAMPLE 14

3-Amino-4-phenyl-5-(2-chloro-phenyl)-1H-pyrazolo[3,4-c]pyridazine (Compound 14)

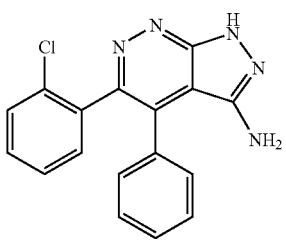

The title compound was obtained according to synthetic procedures described in EXAMPLE 1 using the appropriate diaryl keto hydrazone (X is o-Cl and Y is H): MS (ES+) m/e: 322.1 (M+H); analytical HPLC (C₁₈ column) 3.48 minutes.

EXAMPLE 15

3-Amino-4-phenyl-5-(2-fluorophenyl)-1H-pyrazolo[3,4-c]pyridazine (Compound 15)

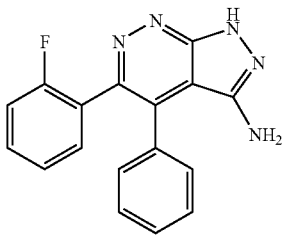

The title compound was obtained according to synthetic procedures described in EXAMPLE 1 using the appropriate diaryl keto hydrazone (X is O—F and Y is H): MS (ES+) m/e: 306.1 (M+H); analytical HPLC (C₁₈ column) 2.97 minutes.

EXAMPLE 16

3-Amino-4-phenyl-5-(4-chloro-phenyl)-1H-pyrazolo[3,4-c]pyridazine (Compound 16)

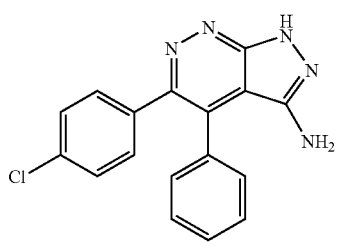

The title compound was obtained according to synthetic procedures described in EXAMPLE 1 using the appropriate diaryl keto hydrazone (X is p-Cl and Y is H): MS (ES+) m/e: 322 (M+H); analytical HPLC ($C_{18}$ column) 4.06 minutes.

EXAMPLE 17

4-Phenyl-1H-pyrazolo[3,4-c]pyridazin-3-ylamine (Compound 32)

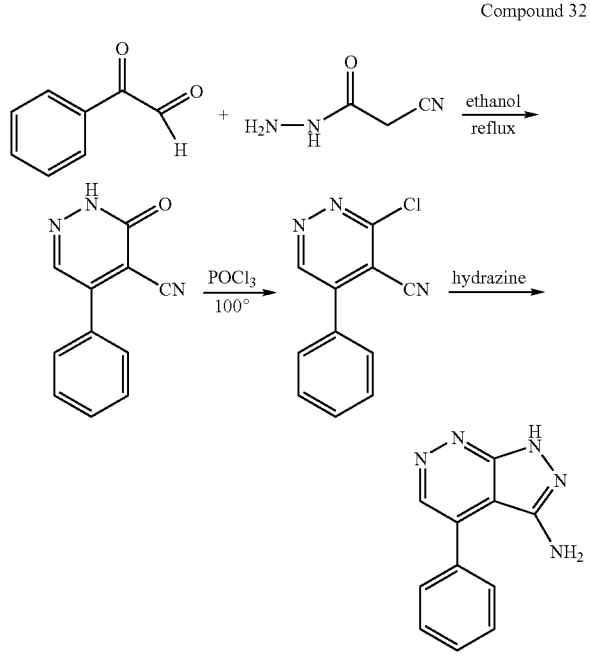

Compound 32

Step A: 3-Oxo-5-phenyl-2,3-dihydro-pyridazine-4-carbonitrile

Phenyl glyoxal (1.0 g, 7.46 mmol) and cyanoacetohydrazide (740 mg, 7.46 mmol) were heated to reflux in 10 mL ethanol for 16 hours. After cooling, the solvent was evaporated and the crude brown mixture was purified by silica chromatography (1:9 methanol/dichloromethane). The still impure product was further recrystallized from methanol affording 70 mg pure product.

Step B: 3-Chloro-5-phenyl-pyridazine-4-carbonitrile

3-Oxo-5-phenyl-2,3-dihydro-pyridazine-4-carbonitrile (70 mg) was suspended in 1 mL phosphorous oxychloride and heated to 100° C. for 6 hours. The mixture was then cooled and poured onto ice. The resulting brown solid product was filtered and air dried and used in the next step without further purification.

Step C: 4-Phenyl-1H-pyrazolo[3,4-c]pyridazin-3-ylamine

3-Chloro-5-phenyl-pyridazine-4-carbonitrile obtained from Step B was suspended in 1 mL ethanol with 23 μL hydrazine and the mixture was refluxed for several hours. The solvent was then evaporated and the title product was purified by silica gel chromatography (1:9 methanol/dichloromethane): MS (ES+) 212 (M+H); HPLC 1.121 minutes.

EXAMPLE 18

$K_i$ Determination for the Inhibition of GSK-3

Compounds were screened for their ability to inhibit GSK-3β (amino acids 1-420) activity using a standard coupled enzyme system (Fox et al. (1998) Protein Sci. 7, 2249). Reactions were carried out in a solution containing 100 mM HEPES (pH 7.5), 10 mM $MgCl_2$, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (HSSPHQS($PO_3H_2$) EDEEE (SEQ ID NO: 21), American Peptide, Sunnyvale, Calif.). Reactions were carried out at 30° C. and 20 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of interest. The assay stock buffer solution (175 μl) was incubated in a 96 well plate with 5 μl of the test compound of interest at final concentrations spanning 0.002 μM to 30 μM at 30° C. for 10 min. Typically, a 12 point titration was conducted by preparing serial dilutions (from 10 mM compound stocks) with DMSO of the test compounds in daughter plates. The reaction was initiated by the addition of 20 μl of ATP (final concentration 20 μM). Reaction rates were obtained using a Molecular Devices Spectramax plate reader (Sunnyvale, Calif.) over 10 min at 30° C. The $K_i$ values were determined from the rate data as a function of inhibitor concentration.

The GSK-3 inhibitory activity of certain compounds of this invention are shown in Table 11. For GSK-3 $K_i$ values, "+++" represents ≦0.1 μM, "++" represents between 0.1 and 10 μM, and "+" represents ≧10 μM.

TABLE 11

| Inhibitory Activity | |
|---|---|
| Compound No. | $K_i$ |
| 1 | +++ |
| 2 | + |
| 3 | ++ |
| 4 | + |
| 5 | +++ |
| 6 | +++ |
| 7 | + |
| 8 | +++ |
| 9 | ++ |
| 10 | ++ |
| 11 | +++ |
| 12 | ++ |
| 13 | ++ |
| 14 | +++ |
| 15 | +++ |
| 16 | ++ |
| 32 | ++ |

EXAMPLE 19

Expression and Purification of GSK-3β

Full length human GSK-3β (1-420) (SEQ ID NO: 1) with an N-terminal hexa-histidine tag (SEQ ID NO: 56) and a thrombin cleavage site was overexpressed in a baculo virus expression system. GSK-3β was purified using Talon metal affinity chromatography (Clontech, Palo Alto, Calif.) followed by size-exclusion on a Superdex 200 column (Pharmacia, Uppsala, Sweden). The hexa-histidine tag (SEQ ID NO: 56) was then removed by incubation with thrombin (Calbiochem, La Jolla, Calif.). In addition to the authentic thrombin site, a second cleavage product was identified 10 amino acids downstream at Threonine 7. Incubation overnight at 4° C. with 12 U mg$^{-1}$ thrombin produced more than 90% GSK-3β (7-420), which was used for crystallographic studies. The reaction was quenched with PMSF and thrombin was removed with benzamidine sepharose (Pharmacia, Uppsala, Sweden). To separate unphosphorylated GSK-3β (7-420) from the phosphorylated species and GSK-3β cleaved at the authentic thrombin cleavage site, the protein was applied to a MonoS 10/10 column (Pharmacia, Uppsala, Sweden) equilibrated in 25 mM HEPES, pH 7.2, 10% Glycerol (v/v), 2 mM DTT. The protein was eluted with a linear gradient from 0 to 300 mM NaCl in 30 column volumes. Unphosphorylated GSK-3β (7-420) eluted at 150 mM NaCl. Phosphorylated GSK-3β (7-420) eluted at around 200 mM NaCl The protein was dialyzed against 25 mM Tris pH 8.0 containing 200 mM NaCl and 2 mM DTT at 4° C., concentrated to 15 mg ml$^{-1}$, and centrifuged at 100,000×g prior to crystallization. All protein molecular weights were confirmed by electrospray mass spectrometry. Phosphorylation on Tyr 216 was confirmed by tryptic digest and MALDI-TOF spectrometry.

EXAMPLE 20

Crystallization of GSK-3β

Crystallization of GSK-3β was carried out using the hanging drop vapor diffusion technique. The unphosphorylated GSK-3β formed diamond shape crystals over a reservoir containing 15% PEG 3350, 50 mM Na/KP04 pH 4.1, 10 mM DTT. The crystallization droplet contained 1 µl of 15 mg ml$^{-1}$ protein solution and 1 µl of reservoir solution. Crystals formed in less than 1 hour and were harvested in a reservoir solution after 12 hrs.

The phosphorylated form (Tyrosine 216) of GSK-3β formed plate-like crystals over a reservoir containing Solution A (7-10% PEG 3350, I00 mM Tris HCl pH 7.5, 5% Dimethylsulphoxide(DMSO)). The component DMSO was important for the crystallaization of phosphorylated GSK-3β. The crystallization droplet contained 1 µl of protein (16 mg/mL) and 1 µl of reservoir solution. The crystals formed overnight and were harvested in Solution A after a few days.

In order to obtain crystals of the ADP-peptide-GSK-3β complex, 0.3 mM protein was mixed with 1.4 mM glycogen synthase peptide (residues 650 to 661), 2 mM ADP and 2 mM MgCl. The mixture was incubated on ice for two hours. Small rod shaped crystals of the complex formed over a reservoir containing 10-15% PEG 3350 and 50 mM ammonium fluoride. Crystals large enough for data collection were obtained after repeated cycles of micro seeding.

Once the above crystals were harvested in reservoir solution, they were transferred to reservoir solutions containing increasing concentrations of glycerol, starting with 2% and increasing to 5, 10, 15, 20, 25 and 30%. After soaking the crystals in 30% glycerol for less than 5 minutes, the crystals were scooped up with a cryo-loop, frozen in liquid nitrogen and stored for data collection.

EXAMPLE 21

Formation of GSK-3β-Inhibitor Complex Crystals

Phosphorylated GSK-3β-inhibitor1 complex crystals were formed by soaking phosphorylated GSK-3β crystals in Solution A that also contained 500 µM of inhibitor 4,5-Diphenyl-1H-pyrazolo[3,4-c]pyridazin-3-ylamine.

Crystals of unphosphorylated GSK-3β-inhibitor2-4 complexes were formed by co-crystallizing the protein with the inhibitors. The inhibitor was added to the concentrated GSK-3β protein solution right before setting up the crystallization drop. Alternatively, inhibitor could be added to a diluted protein solution, and the mixture concentrated to the required concentration. The unphosphorylated GSK-3β protein co-crystallized with inhibitors(5-Methyl-2H-pyrazol-3-yl)-(2-pyridin-4-yl-quinazolin-4-yl)-amine, 4-(5-Methyl-2-phenylamino-pyrimidin-4-yl)-1H-pyrrole-2-carboxylic acid (2-hydroxy-1-phenyl-ethyl)-amide), and (1H-Indazol-3-yl)-[2-(2-trifluoromethyl-phenyl)-quinazolin-4-yl]-amine) over a reservoir solution containing 15-20% PEG 3350, 0.1-1 M of KF, potassium formate or ammonium formate. The crystallization droplet contained 1 µl of 10-20 mg/ml protein solution containing the inhibitor and 1 µl of reservoir solution.

Once the crystals of both forms were harvested, they were transferred to reservoir solutions containing increasing concentrations of glycerol, starting with 5% and increasing to 10, 15, 20, 25 and 30%. After soaking the crystals in 30% glycerol for less than 5 minutes, the crystals were scooped up with a cryo-loop, frozen in liquid nitrogen and stored for data collection.

EXAMPLE 22

X-Ray Data Collection and Structure Determination

X-ray diffraction data for the unphosphorylated GSK-3β, phosphorylated GSK-3β, phosphorylated GSK-3β-inhibitor complex, unphosphorylated GSK-3β-inhibitor complexes, phosphorylated GSK-3β-ADP-peptide complex structures were collected on a Raxis 4 image plate, with mirror-focused CuKa X-rays generated by a rotating-anode source. X-ray data used to refine the unphosphorylated GSK-3β structure was collected at beam line 5.0.2 of the Advanced Light Source Lawrence Berkeley Laboratory, Berkeley, Calif. Data collected on the Raxis 4 image plate was processed with DENZO and SCALEPACK (Otwinowski et al., *Methods Enzymol.*, 180, 51-62 (1989)) Data collected at ALS were processed with the program MOSFLM and the data was scaled using SCALA (Collaborative Computational Project, N., *Acta Cryst., D*50, pp. 760-763 (1994)).

The data statistics of the unphosphorylated form are summarized in Table 12. The spacegroup of the unphosphorylated crystals was P2$_1$2$_1$2$_1$, with unit cell dimensions a=83 b=86 c=178 Å, α=β=γ=90°. The starting phases for unphosphorylated GSK-3β were obtained by molecular replacement using coordinates of CDK2 (Protein Data Bank Accession number 1AQ1) (Lawrie, A. M., et al., *Nat. Struct. Biol.*, 4, pp. 796-801 (1997)) as a search model in the program AMORE (Navaza, *J. Acta. Cryst.*, 50, pp. 157-163 (1994)). The asymmetric unit contained two molecules. Multiple rounds of rebuilding with QUANTA and refinement with CNX resulted in a final model that included amino acid residues 25 to 384 for molecule A and residues 37 to 382 for molecule B, 4 phosphate ions and 46 water molecules. The a carbons in A and B chains have a root-mean-squared deviation after superposition of 0.48 Å. The refined model has a crystallographic R-factor of 23.7% and R-free of 27.4%. The coordinates of the structure have been deposited with the Protein Databank (accession code I109).

The data statistics of the phosphorylated form are summarized in Table 13. The spacegroup of the crystals was P1, with unit cell dimensions a=64 Å b=67.2 Å c=67.4 Å α=100.1°

β=103.5° γ=90° or a=64 Å b=67 Å c=67 Å α=80° β=77° γ=89.8°. The dimensions of the unit cell varied 1-2% from crystal to crystal. The starting phases for phosphorylated GSK-3β were obtained by molecular replacement using coordinates of the unphosphorylated form as a search model in the program AMORE ENRfu, supra. The asymmetric unit contained two molecules. Multiple rounds of rebuilding with QUANTA and refinement with CNX resulted in a final model that included residues 37 to 383 for molecule A and residues 37 to 383 for molecule B and 83 water molecules. All data was included and NCS restraint was applied through out the refinement. The final step of refinement was an individual B-factor refinement. The refined model has a crystallographic R-factor of 23.8% and R-free of 27.6%.

The spacegroup of the unphosphorylated GSK-3β-inhibitor2-4 complex crystals was $P2_12_12_1$, with unit cell dimensions a=83 b=86 c=178 Å, α=β=γ=90°. The starting phases for unphosphorylated GSK-3β-inhibitor complexes were obtained by molecular replacement using coordinates of the unphosphorylated form as a search model in the program AMORE ENRfu, supra. The asymmetric unit contained two molecules. Multiple rounds of rebuilding with QUANTA and refinement with CNX were performed.

The data statistics of the unphosphorylated GSK-3β-inhibitor2 complex are summarized in Table 14. The structure was refined to 2.9 Å, and the R-factor was 24.1% and R-free was 28%. The final model included amino acid residues 25 to 385 for molecule A, residues 37 to 382 for molecule B, inhibitor2 and 6 water molecules.

For the unphosphorylated GSK-3β-inhibitor3 complex, the structure was refined to 2.3 Å, and the R-factor was 25.3% and R-free was 28.6%. For molecule A, residues 25 to 381 were included in the final model. For molecule B, amino acid residues 37 to 382 were included in the final model.

For the unphosphorylated GSK-3β-inhibitor4 complex, the structure was refined to 2.8 Å, and the R-factor was 24.1% and R-free was 28.3%. For molecule A, residues 36 to 381 were included in the final model. For molecule B, amino acid residues 37 to 382 were included in the final model.

The data statistics of the phosphorylated GSK-3β-inhibitor1 complex are summarized in Table 15. The spacegroup of the crystals was P1, with unit cell dimensions a=64 Å b=67 Å c=67 Å α=100° β=103° γ=89.8° or a=64 Å b=67 Å c=67 Å α=80° β=77° γ=89.8°. The starting phases for phosphorylated GSK-3β-inhibitor complex were obtained by molecular replacement using coordinates of the phosphorylated form as a search model in the program AMORE ENRfu, supra. The asymmetric unit contained two molecules. Multiple rounds of rebuilding with QUANTA and refinement with CNX resulted in a final model that included residues 37 to 383 for molecule A and residues 37 to 384 for molecule B, the inihibitors bound to molecule A and B, and 83 water molecules. The structure was refined to 2.8 Å, and had an R-factor of 22.6% and R-free of 26.9%.

The data statistics of the phosphorylated GSK-3β-ADP-peptide complex are summarized in Table 16. The spacegroup of the crystals was $P2_12_12_1$, with unit cell dimensions a=75.16 Å b=107.93 Å c=121.2 Å α=90° β90° γ=90°. The starting phases for phosphorylated GSK-3β were obtained by molecular replacement using coordinates of the unphosphorylated form as a search model in the program AMORE ENRfu, supra. The asymmetric unit contained two molecules. The glycine rich loop was well ordered and could be built in the model. Multiple rounds of rebuilding with QUANTA and refinement with CNX was performed. All data was included and NCS restraint was applied through out the refinement. The final step of refinement was a grouped B-factor refinement. The refined model has a crystallographic R-factor of 23.5% and R-free of 27.2%.

The Ramachandran plot of phosphorylated GSK-3β in complex with ADP and glycogen synthase peptide showed that 80.1% of the residues were in most favored regions and 19.6% in additionally allowed regions. The Ramachandran plot of apo-phosphorylated GSK-3β showed that 85.3% of the amino acid residues were in most favored regions and 14.3% in additionally allowed regions. Two amino acid residues (Cys 218 in molecule A and B) in both crystal structures were in disallowed regions.

In the above models, disordered residues were not included in the model. Alanine or glycine residues were used in the model if the side chains of certain residues could not be located in the electron density.

EXAMPLE 23

Overall Structure of Unphosphorylated GSK-3β

GSK-3β has the typical 2 domain kinase fold (Hanks, S. K., et al., *Science,* 241, pp. 42-52 (1988); Hanks, S. K. and A. M. Quinn, *Methods Enzymol.,* 200, pp. 38-62 (1991)) with a β-strand domain (amino acid residues 25-138) at the N-terminal end and an α-helical domain at the C-terminal end (amino acid residues 139-343) (FIG. 8). The active site is at the interface of the α-helical and β-strand domain, and is bordered by the glycine rich loop and the hinge. The activation loop runs along the surface of the substrate-binding groove. The C-terminal 39 amino acid residues (amino acid residues 344-382) are outside the core kinase fold and form a small domain that packs against the α-helical domain. The β-strand domain consists of seven anti-parallel β-strands. Strands 2 to 6 form a β-barrel that is interrupted between strand 4 and 5 by a short helix (amino acid residues 96-102) which packs against the β-barrel. This helix is conserved in all kinases, and two of its residues play key roles in the catalytic activity of the enzyme. Arginine 96 is involved in the alignment of the two domains. Glutamate 97 is positioned in the active site and forms a salt bridge with lysine 85, a key residue in catalysis.

Phosphorylation of Peptides by GSK-3β

Before a serine/threonine kinase can phosphorylate a substrate, its β-strand and α-helical domains must be aligned into a catalytically active conformation. Most kinases use one or two phosphorylated amino acid residues on the activation loop for this purpose. Polar amino acid residues, typically arginines and lysines, from the β-strand and α-helical domains, bind the phosphate group of the phosphorylated amino acid residue on the activation loop, which leads to proper alignment of the two domains. The second phosphorylated amino acid residue (if present, for example Tyr216 in GSK-3β) opens the substrate-binding groove and allows the substrate to bind.

Figure 10A:
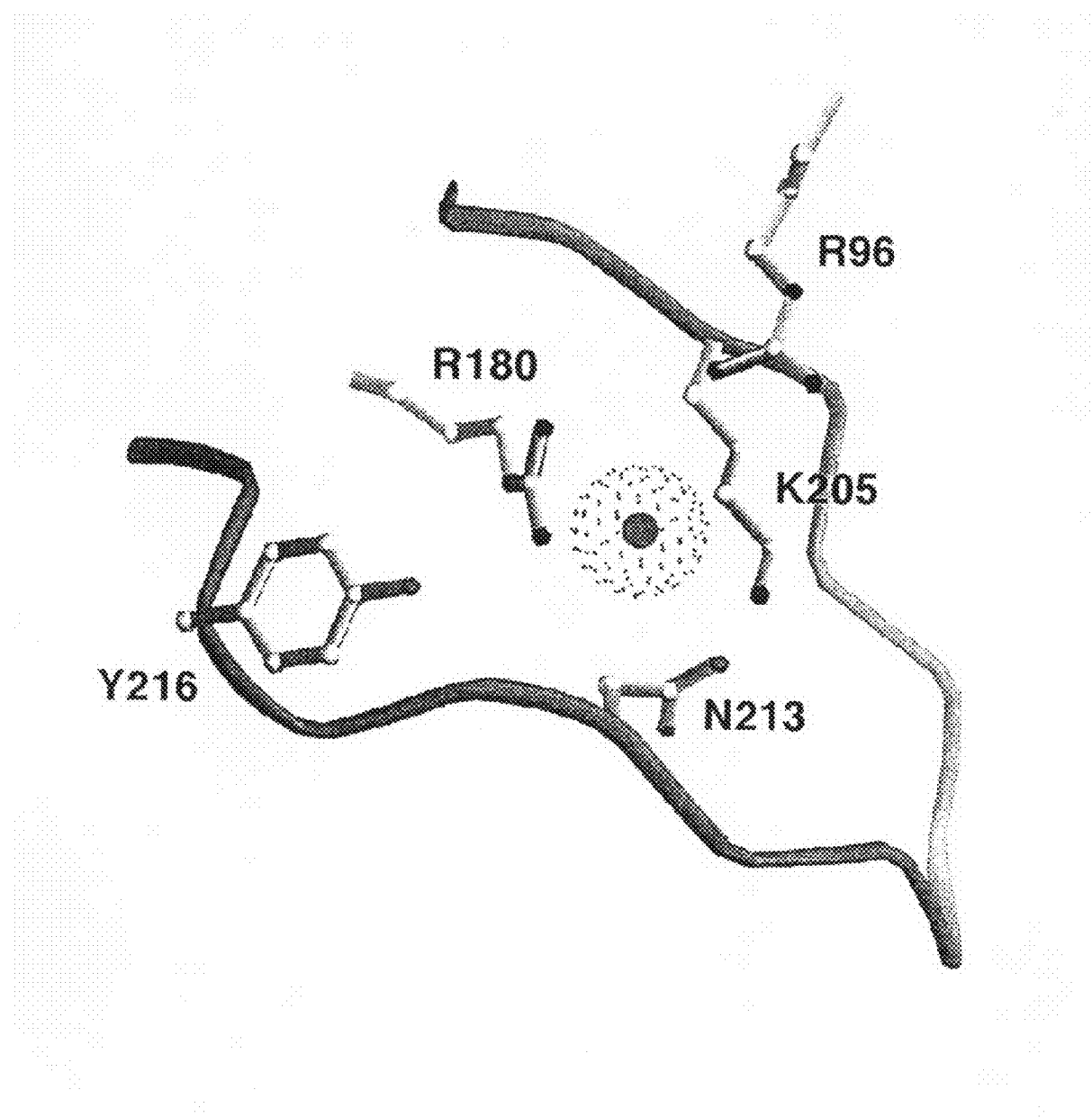
In FIG. 10A, the side chains of residues R96, R180 and K205 are pointing to a phosphate ion that occupies the same position as the phosphate group of the phospho-threonine in activated p38γ (FIG. 10C), activated CDK2 and activated ERK2.
Figure 10B:
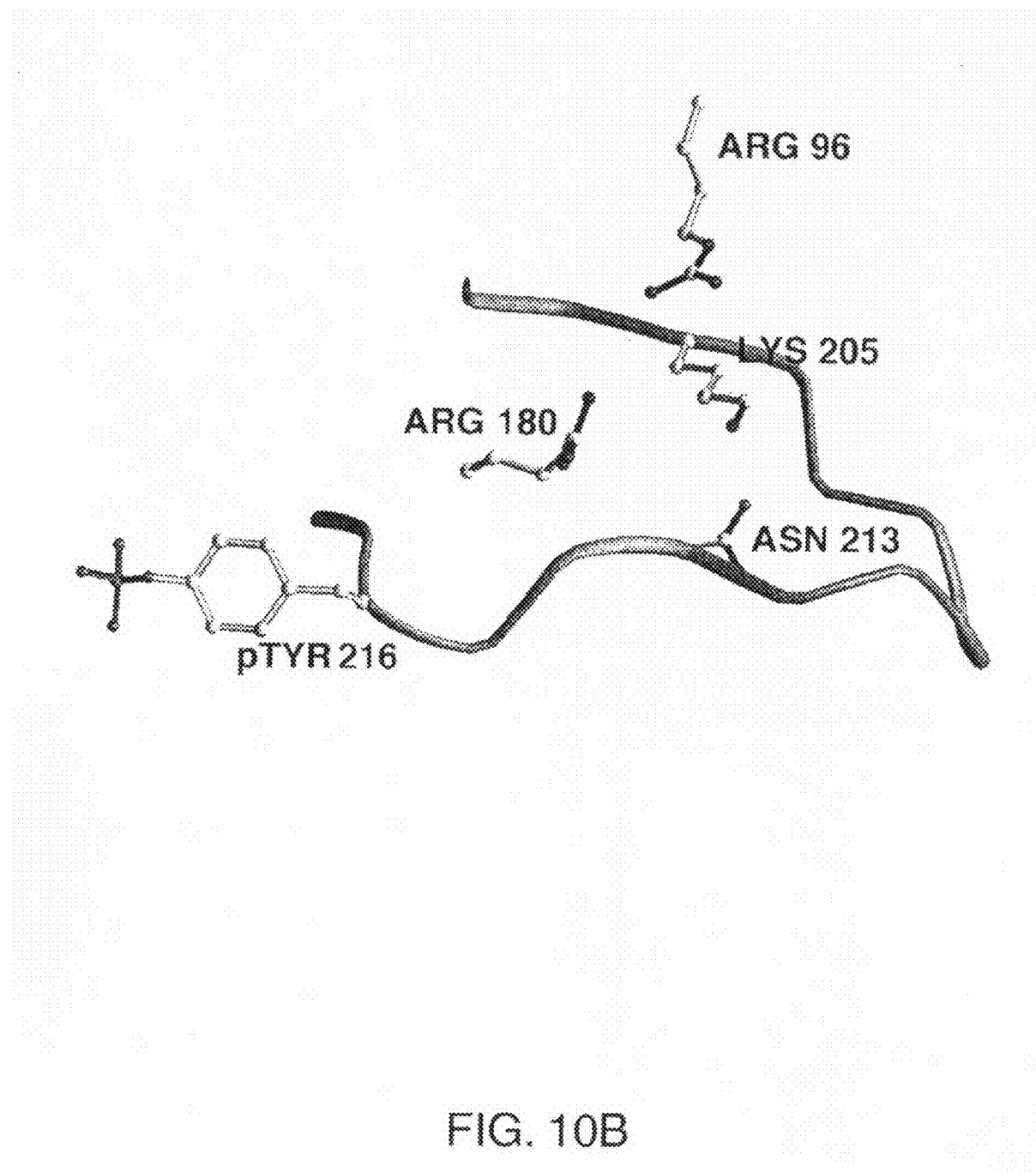
FIG. 10 shows a comparison between the activation loops of unphosphorylated GSK-3β (FIG. 10A), phosphorylated GSK-3β (FIG. 10B), and phosphorylated p38γ (Protein Data Bank accession number 1CM8)(FIG. 7C).
In FIG. 10C, the phosphorylated Y216 is flipped out of the substrate binding groove, which is similar to the position of the phosphorylated Y185 of p38γ.
Figure 10C:
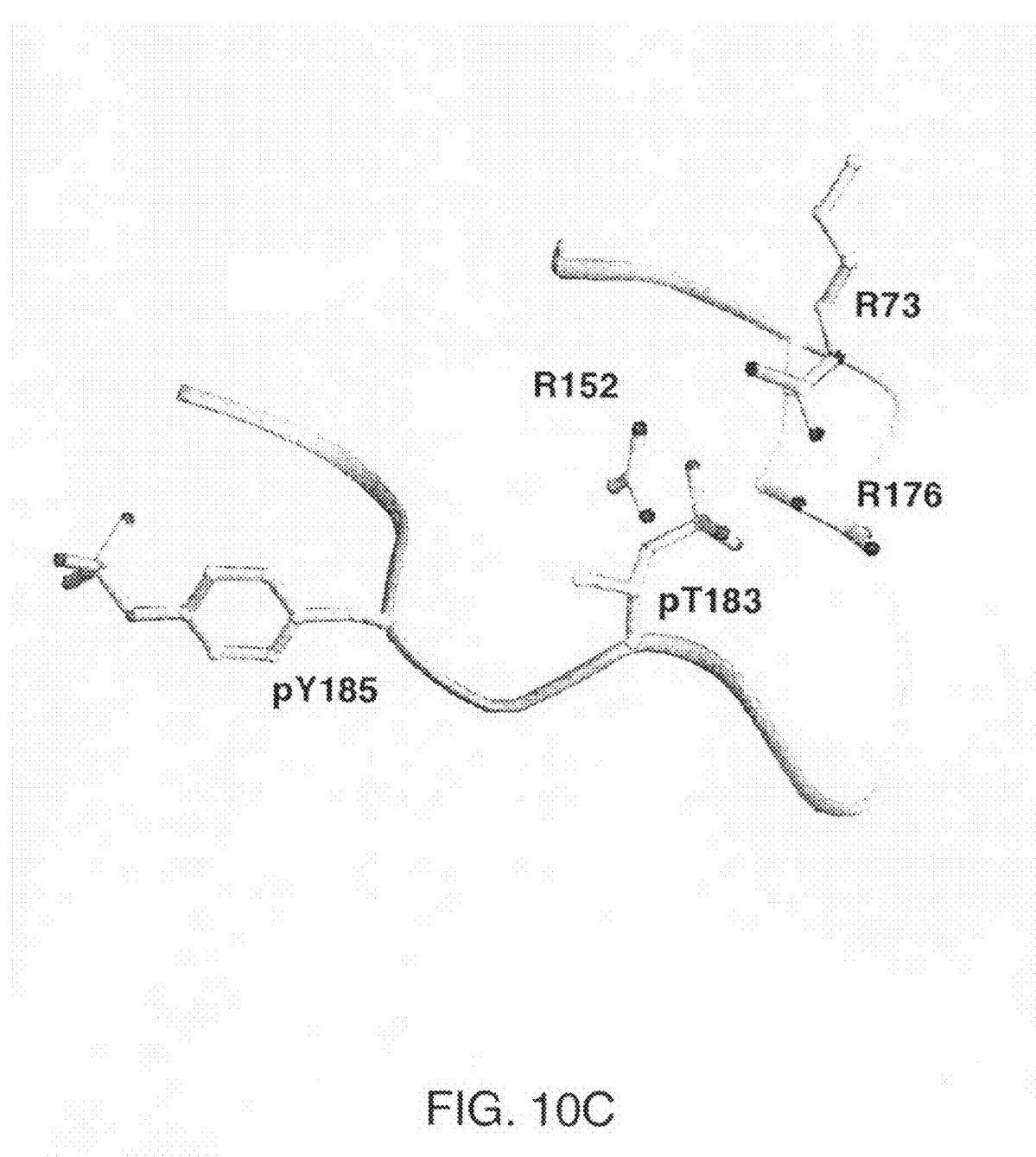

Comparison of the GSK-3β with other kinases such as CDK2, p38γ and ERK2 revealed that the structure of apo-GSK-3β resembles closely the substrate-bound, activated form of a kinase. The activation loop (amino acid residues 200 to 226) in the GSK-3β structure is well ordered, and is positioned against the α-helical domain. This orientation opens the peptide substrate binding groove (FIG. 11), and mimics the position of the activation loop of the activated substrate bound CDK2 (FIG. 10) but not apo-CDK2 (Protein Data Bank Accession number 1HCL) (Schulze-Gahmen, U., et al., *Proteins,* 22, pp. 378-91 (1995)). Comparison of the activation loops of GSK-3β, P38γ (Protein Data Bank Accession number 1CM8) (Bellon, S., et al., *Structure Fold Des*, 7, pp. 1057-65 (1999)), substrate-bound activated CDK2 (Protein Data Bank Acession number 1QMZ) (Brown, N. R., et al., *Nat. Cell. Biol.*, 1, pp. 438-443 (1999)), and ERK2 (Protein Data Bank Accession number 2ERK) (Canagarajah, B. J., et al., *Cell*, 90, pp. 859-69 (1997)) shows that the backbone and side chain atoms of important residues align (FIG. 10). R96, R180 and K205 of GSK-3β (FIG. 10A) superimpose well with R73, R152 and R176 of phosphorylated P38γ, respectively (FIG. 10C). These amino acid residues also superimpose well with the corresponding residues in phosphorylated ERK2 and substrate bound activated CDK2. In p38γ, CDK2 and ERK2, these residues point to the phosphate group from the phosphorylated threonine on the activation loop, the residue that is important for aligning the N-terminal and C-terminal domains. In the GSK-3β structure, R96, R180 and K205 point to a $PO_4^-$ ion that is located in the same position as the phosphate group of the phosphorylated threonine in CDK2, ERK2 and p38γ.

The superposition of the GSK-3β and p38γ activation loops shows that the GSK-3β phosphorylation site, Y216, is located in a similar position as the phospho-tyrosine (amino acid residue 185) of p38γ. The phospho-tyrosine of p38γ acts as a gatekeeper for the substrate-binding groove. When it is phosphorylated, its side chain moves out of the groove allowing substrate peptides to bind. The side chain of Y216 of GSK-3β is also positioned to block access to the substrate-binding groove.

Figure 9:
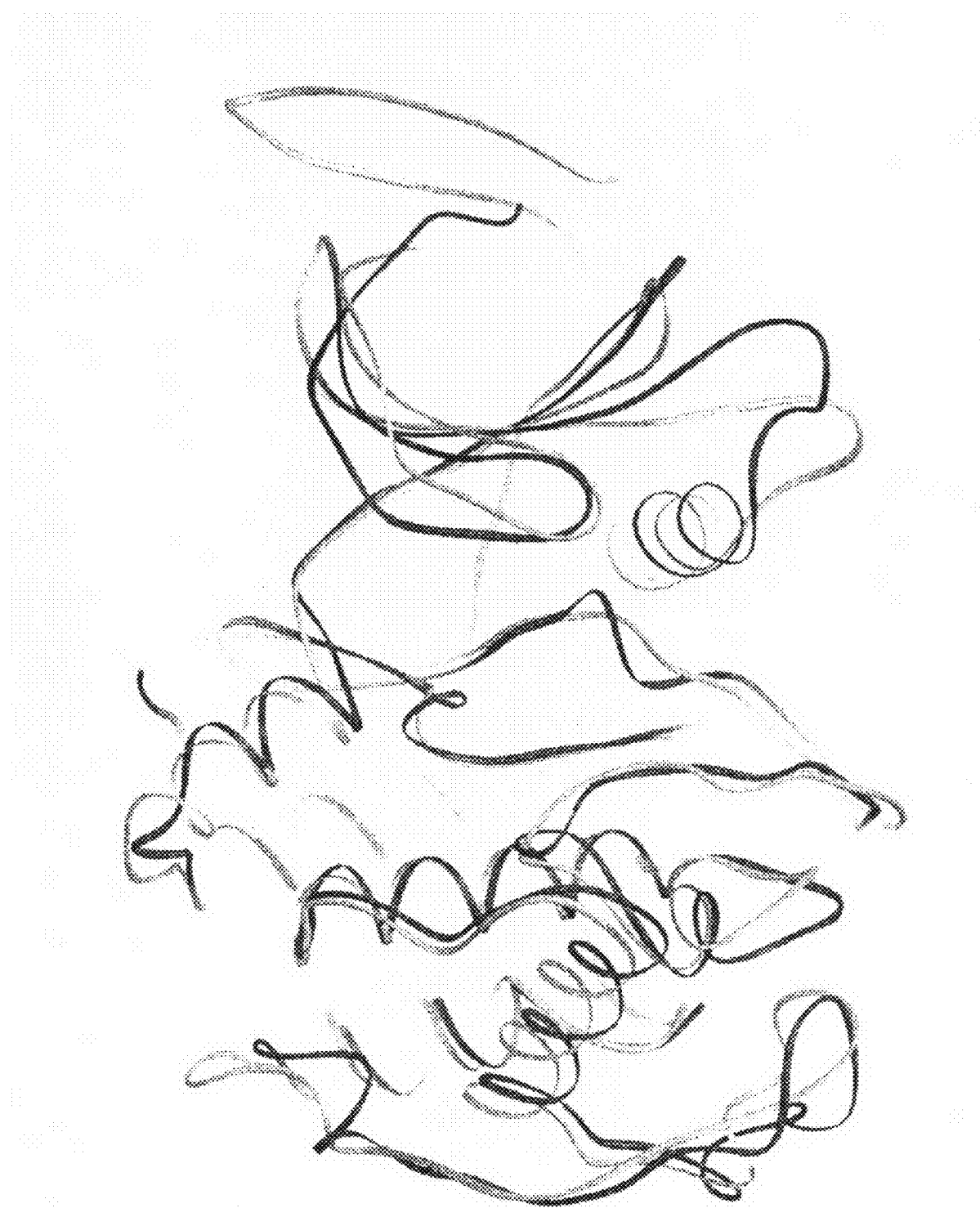
FIG. 9 depicts a superposition of unphosphorylated GSK-3β (light shade) and activated substrate-bound CDK2 (Protein Data Bank accession number 1QMZ) (dark shade). The α-helical domains of GSK-3β and CDK2 were superimposed in QUANTA by aligning matching residues.

The sequence of GSK-3β is 25% identical and 41% similar to the sequence of CDK2. The structure of GSK-3β presented here superimposes well with the structure of activated, substrate-bound CDK2 (FIG. 9). Because of the similarity in sequence and fold, we can use the structure of activated, substrate-bound CDK2 as a model for the substrate binding of GSK-3β.

Primed Phosphorylation

Figure 11A:
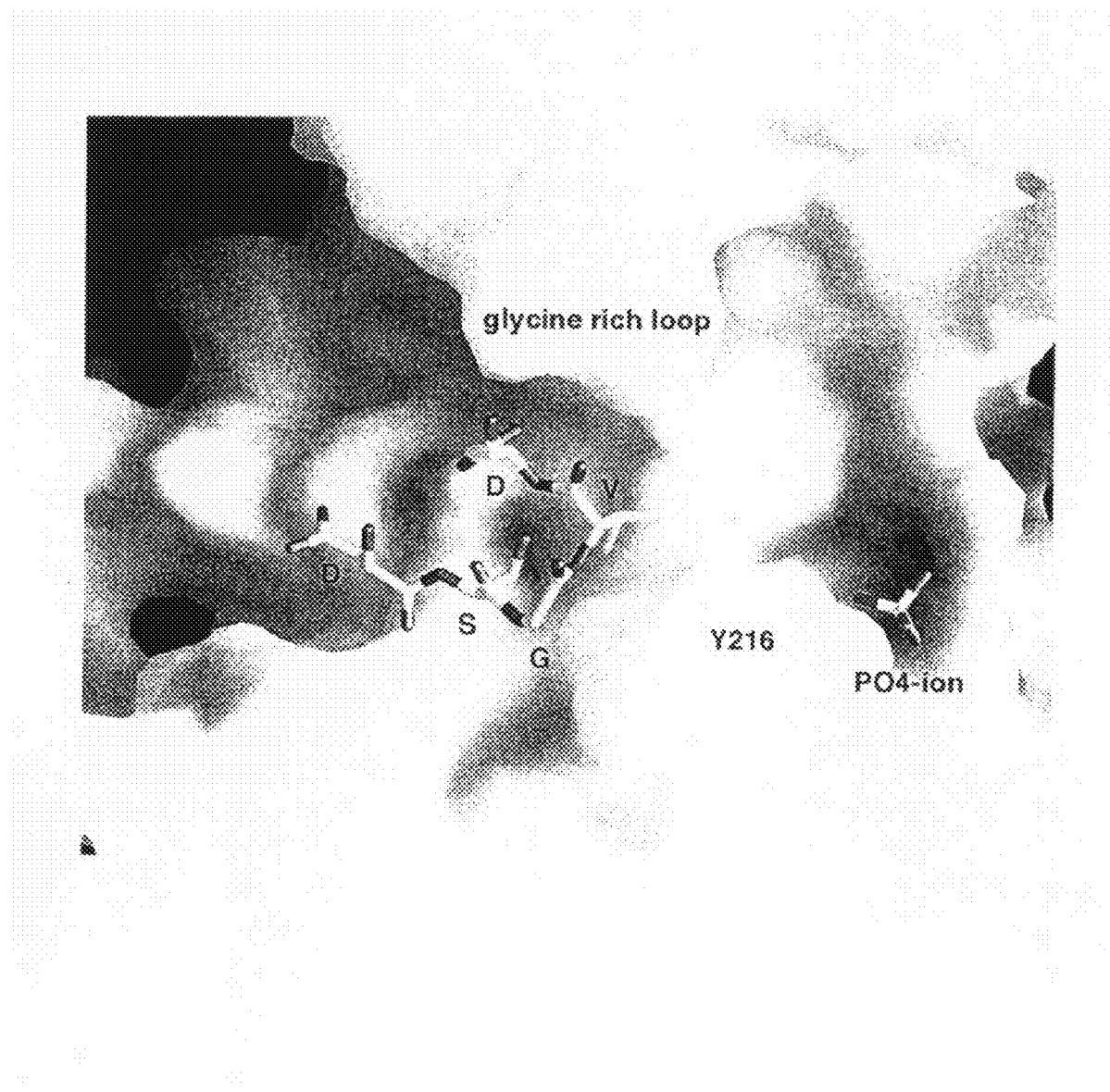
FIG. 11A shows that in the unphosphorylated GSK-3β structure, the GSK-3β substrate-binding groove is occupied by a phosphate ion and residues 260 to 264 of a neighboring GSK-3β molecule.
Figure 11B:
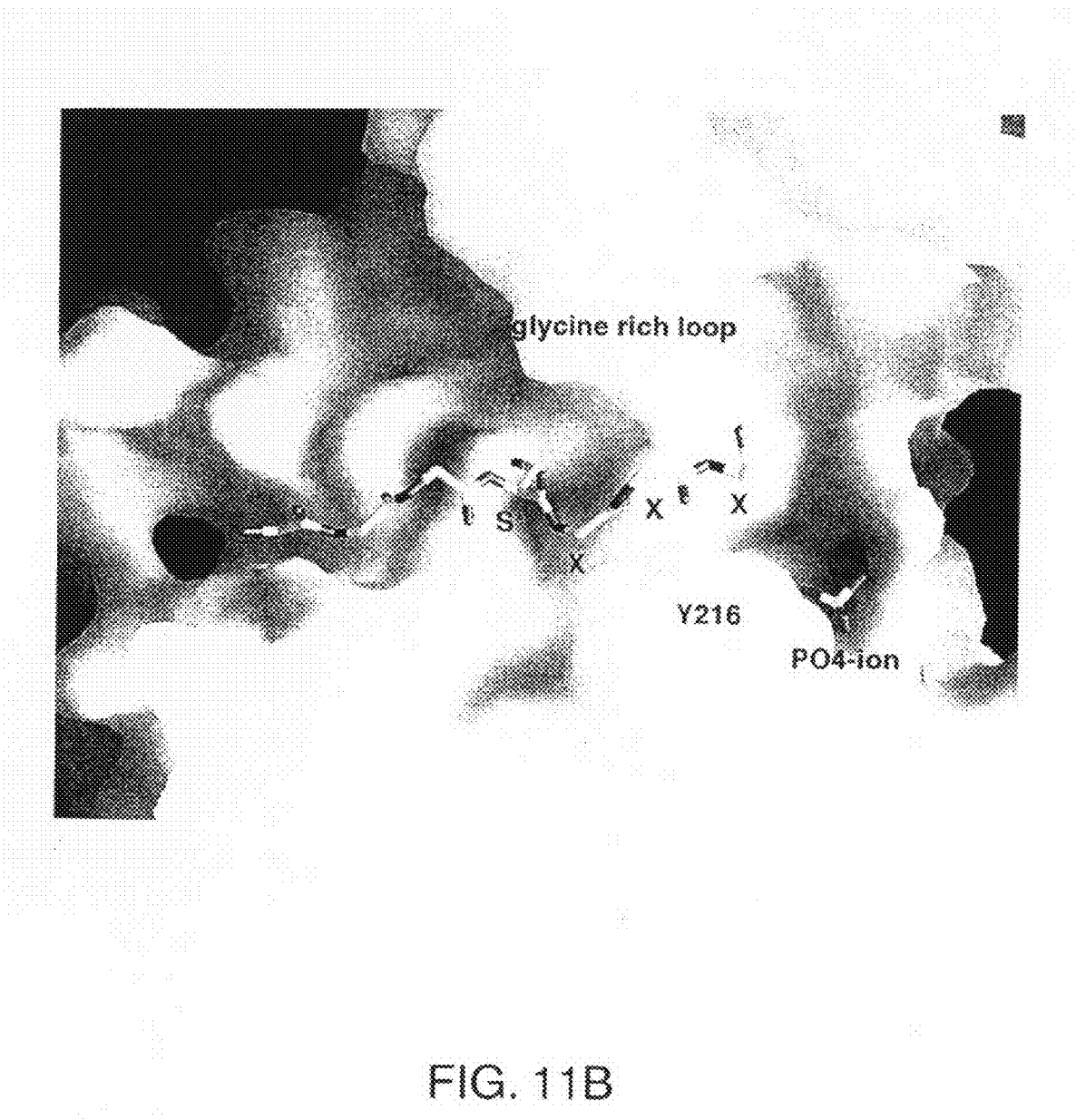
FIG. 11B shows a model for the binding of the SXXXpS motif in the GSK-3β substrate-binding groove. The α-helical domains of GSK-3β and activated substrate bound CDK2 (Protein Data Bank accession number 1QMZ) were superimposed to model the positioning of a primed peptide in the GSK-3β substrate-binding groove. The side chains of the peptide residues except for the target serine S* have been removed for clarity. The phosphorylation site S* is positioned in front of the active site. The model estimates how the SXXXpS motif fits in the substrate-binding groove with the three residues bridging the gap between the P and P+4 serines. The phosphate group of the P+4 serine will occupy the same position as the phosphate ion found in the crystal structure.
Figure 12:
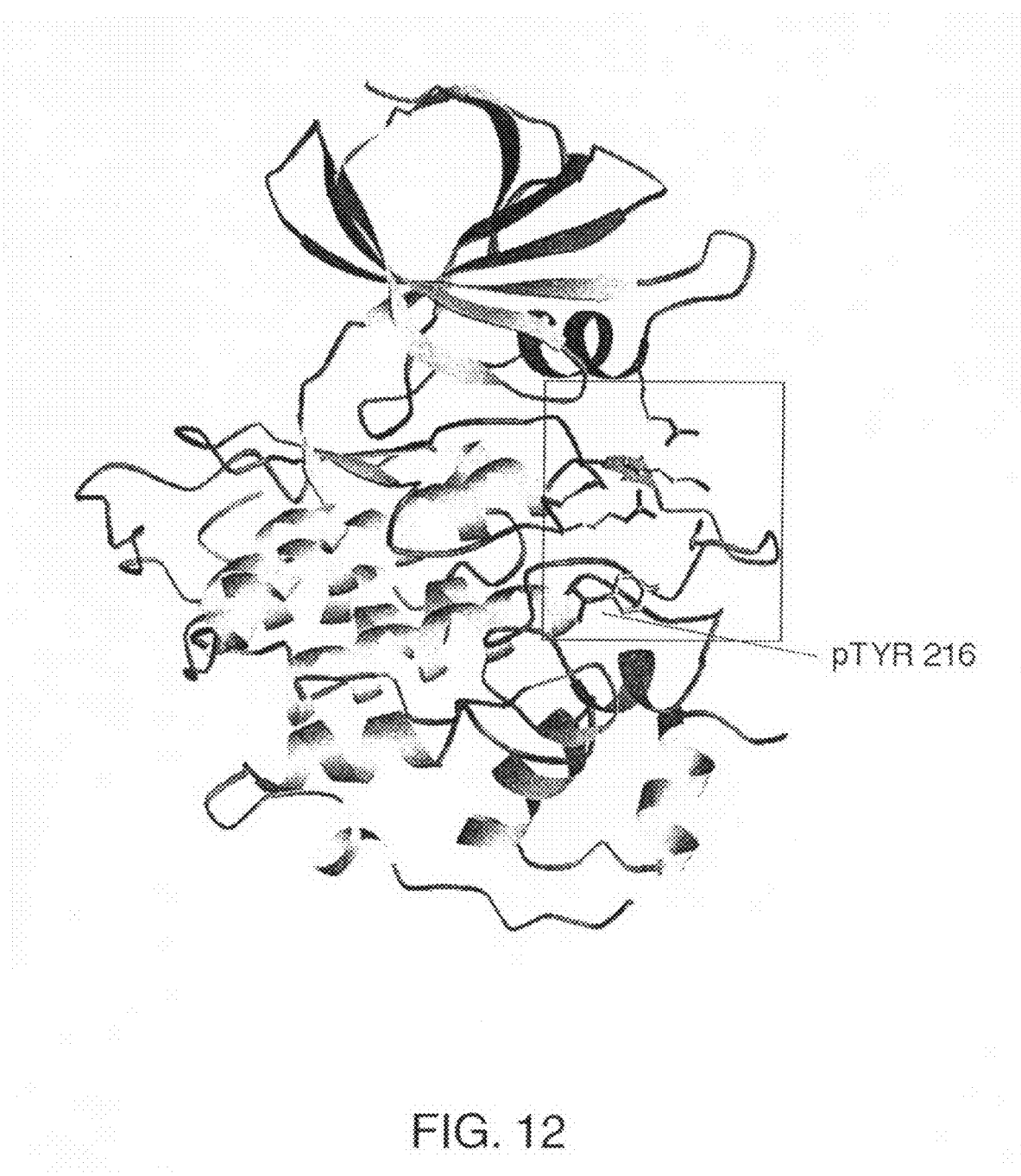
FIG. 12 depicts a ribbon diagram of phosphorylated GSK-3β. The activation loop and the phosphorylated Y216 are indicated.

The GSK-3β substrate-binding groove is partially occupied by a loop from a neighboring GSK-3β molecule in the crystal (FIG. 11A). The loop is positioned in front of the active site. Superposition of the α-helical domains of activated substrate-bound CDK2 and GSK-3β shows that four residues in the loop, DSGV (amino acid residues 260 to 263), are in a very similar position as the peptide in activated substrate-bound CDK2. S261 of the loop in GSK-3β occupies the same position as the target serine in peptide-bound CDK2 (compare position S261 in FIG. 11A with S* in FIG. 11B). The CDK2-bound peptide has an extended conformation, while loop 260-264 in the GSK-3β adopts a turn and occupies a small portion of the substrate-binding groove. It is likely that the natural substrate for GSK-3β also has an extended conformation, similar to the peptide bound to CDK2. If we use the CDK2-bound peptide as a model for a GSK-3β substrate, it becomes clear why GSK-3β prefers a phosphorylated serine or threonine at the P+4 position. The phosphate group at the P+4 position will occupy the same position as the phosphate ion near the activation loop of our structure, contacting R96, R180 and K205 (FIG. 11). This means that while CDK2, p38γ and ERK2 use a phospho-threonine on the activation loop to align the β-strand and α-helical domains, GSK-3β uses the phosphorylated serine at the P+4 position of the substrate to align the two domains for optimal catalytic activity.

EXAMPLE 24

Active Site of GSK-3β-Inhibitor Complexes

Figure 14:
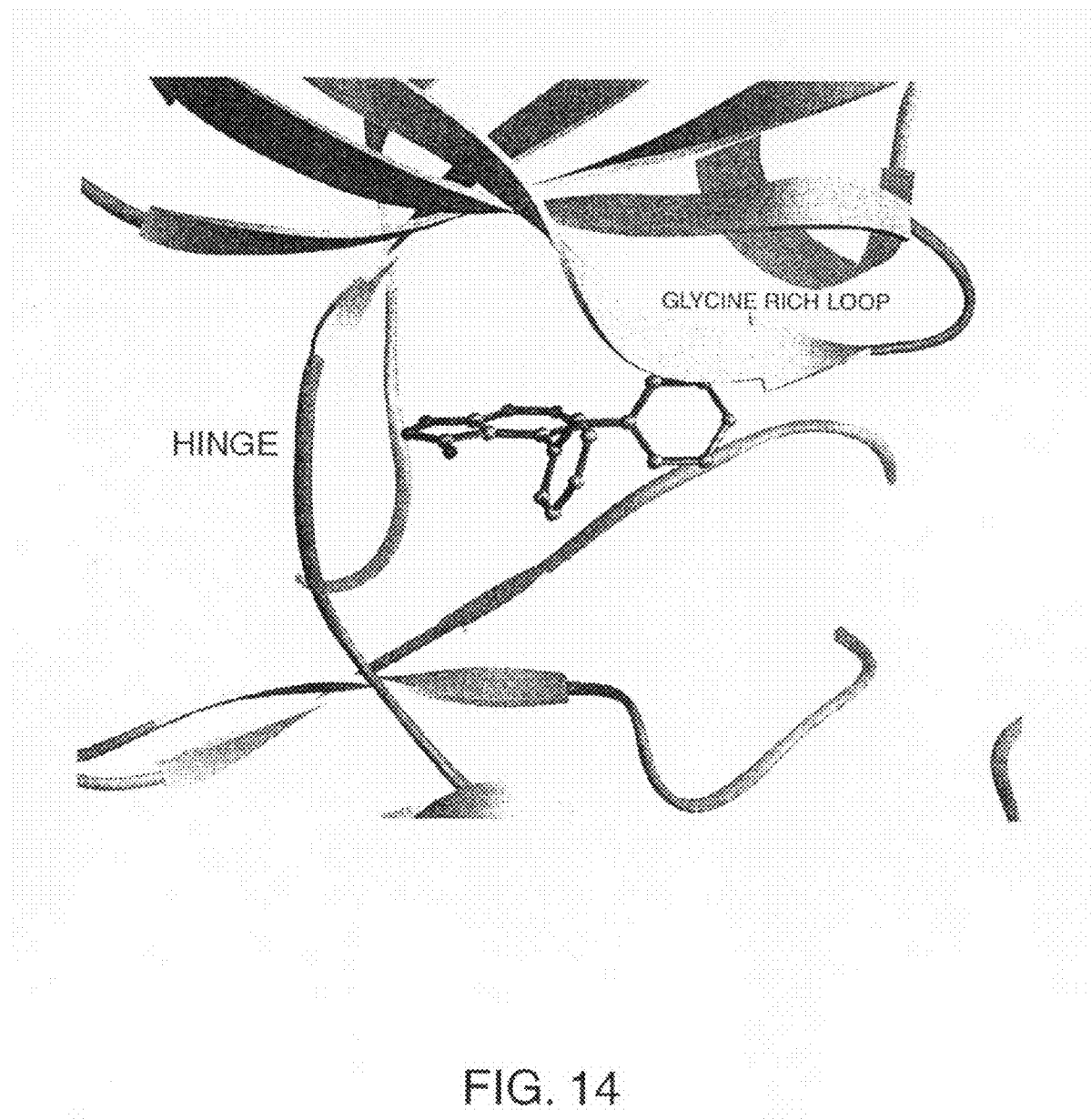
FIG. 14 presents the view of inhibitor1 bound in the active site of phosphorylated GSK-3β.

Inhibitor1 4,5-Diphenyl-1H-pyrazolo[3,4-c]pyridazin-3-ylamine is bound in the deep cleft of the active site in the phosphorylated GSK-3β structure (FIG. 14). Inhibitor1 forms two hydrogen bonds with the hinge portion of the active site. The 1H pyrazole nitrogen shares a proton with the D133 backbone carbonyl. The other pyrazole nitrogen (position 2) accepts a proton from the V135 backbone nitrogen. The side chains of L132 and K85 are positioned inside the active site. K85 is a catalytically important residue and forms a salt bridge with E97 (not shown).

Figure 13:
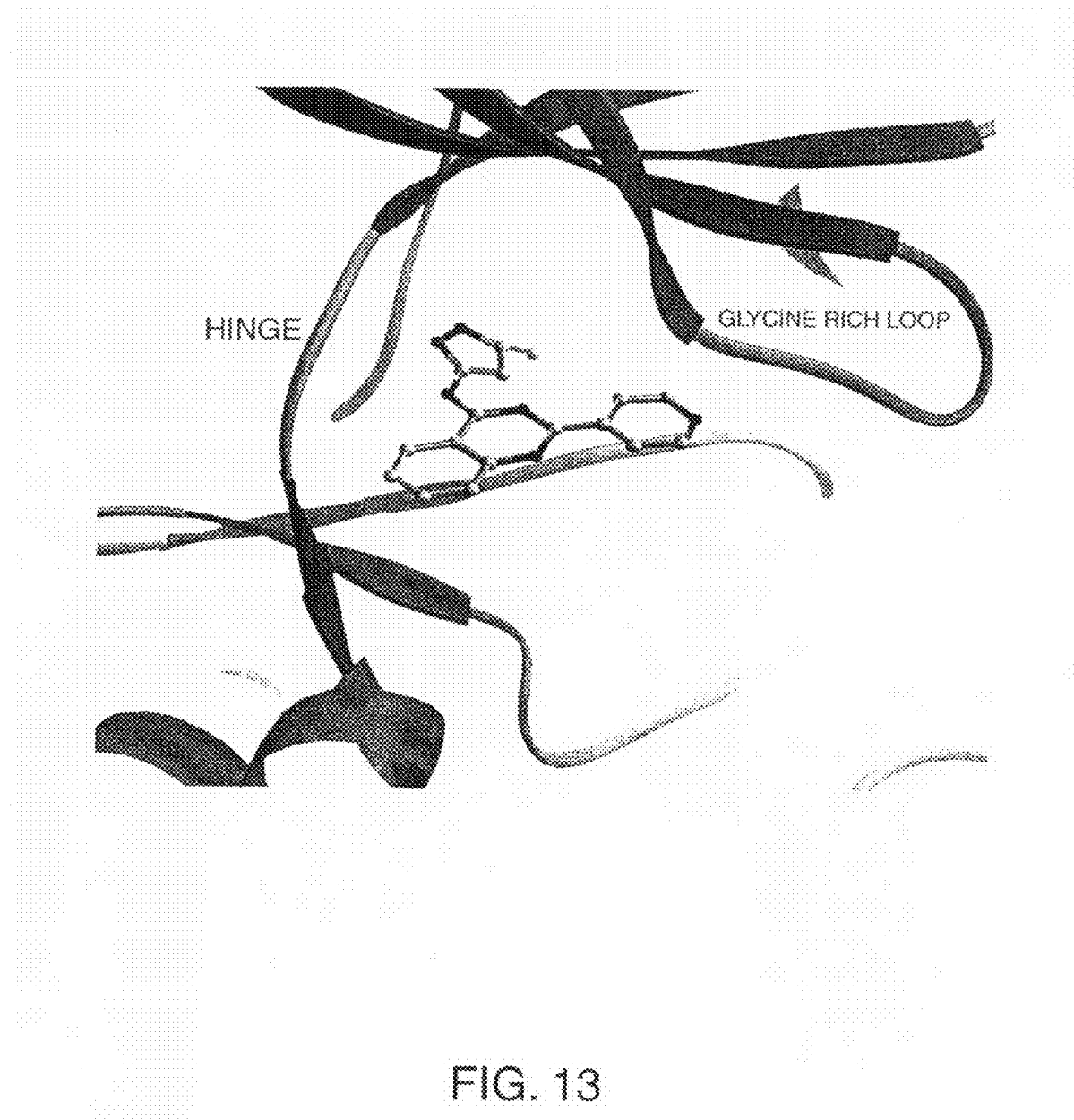
FIG. 13 presents the inhibitor2 bound in the active site of unphosphorylated GSK-3β. The hinge and glycine rich loop are indicated.

Inhibitor2 (5-Methyl-2H-pyrazol-3-yl)-(2-pyridin-4-yl-quinazolin-4-yl)-amine is bound in the active site in the unphosphorylated GSK-3β structure (FIG. 13). The inhibitor2 forms four H-bonds with the hinge backbone. Two hydrogen bonds come from the pyrazole ring. The nitrogen in position one donates a hydrogen to the backbone carbonyl of Asp 133. The nitrogen in position 2 accepts a hydrogen from the Val 135 amide nitrogen. The backbone carbonyl of Val 135 is within hydrogen bonding range of hydrogen donating groups on the inhibitor2. It contacts the linker nitrogen and the quinazoline carbon at position 8.

Figure 15:
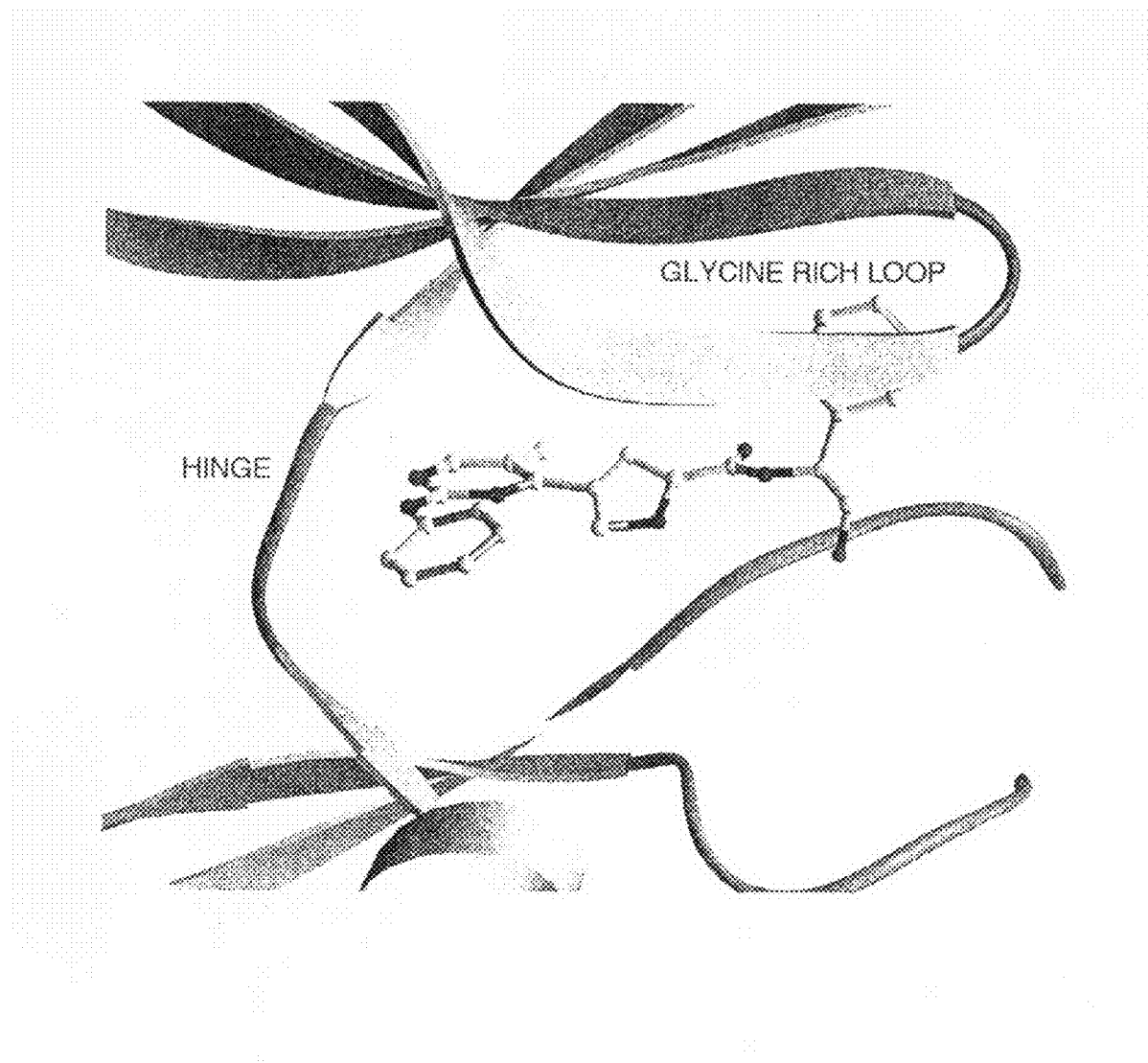
FIG. 15 presents the view of inhibitor3 bound in the active site of unphosphorylated GSK-3β.

Inhibitor3 4-(5-Methyl-2-phenylamino-pyrimidin-4-yl)-1H-pyrrole-2-carboxylic acid (2-hydroxy-1-phenyl-ethyl)-amide) is bound in the active site in the unphosphorylated GSK-3β structure (FIG. 15). Inhibitor3 is a potent inhibitor of GSK-3β with a Ki of 4 nM. Inhibitor3 forms 5 hydrogen bonds with the GSK-3β protein. The three amino-pyrimidine hydrogen bonds contact the hinge backbone. The carbonyl forms a hydrogen bond with the side chain of the catalytic lysine (K85) and the hydroxyl forms a hydrogen bond with the side chain of asparagine 186. Asn186 is a conserved residue in GSK-3β and ERK2. The 5-methyl group of the amino-pyrimidine ring points toward L132 and V110 in GSK-3β. There is limited space between these two residues suggesting that a small substituent is allowed in this position.

Figure 16:
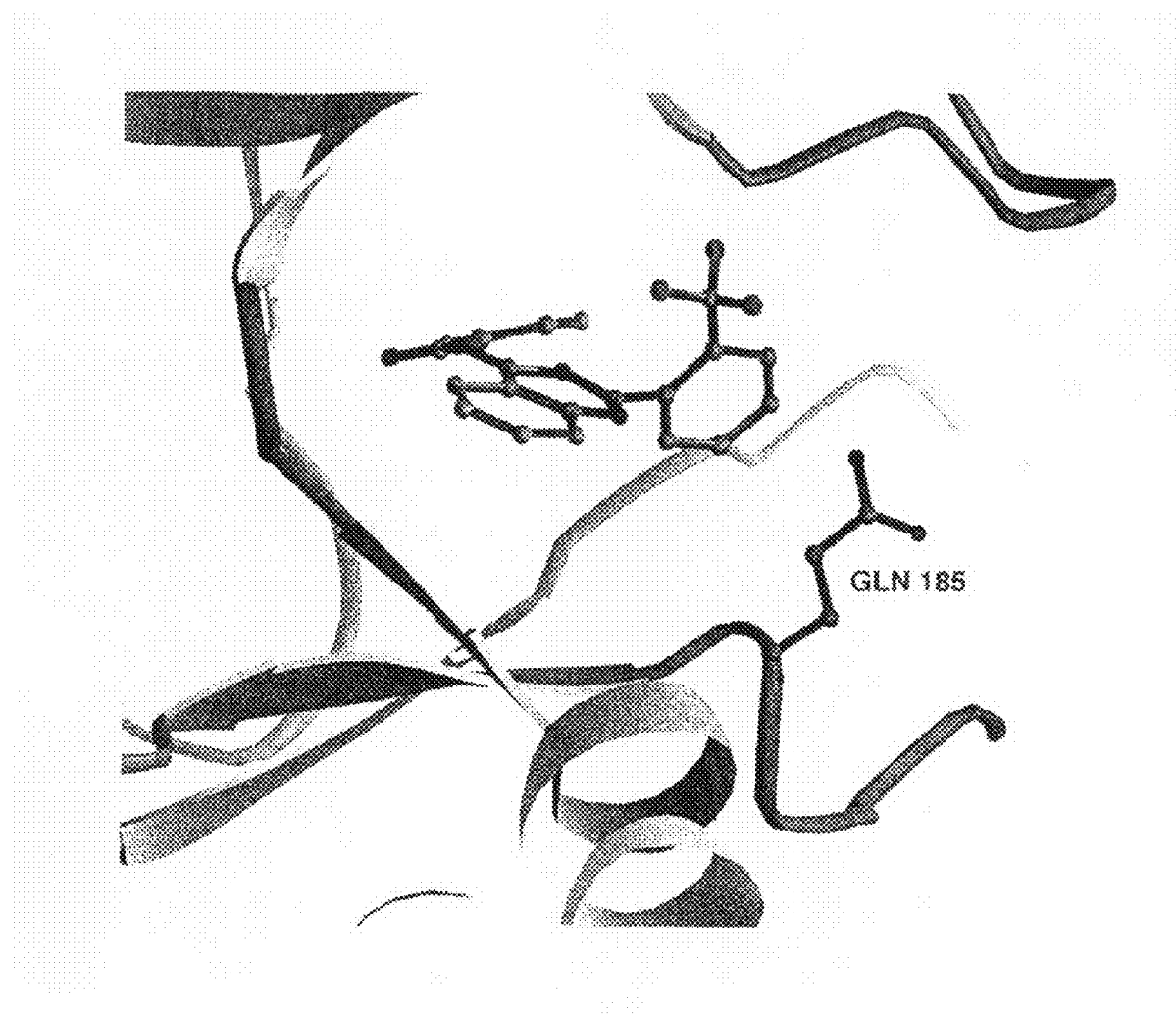
FIG. 16 presents the conformation of Gln185 in the active site when bound to inhibitor4.

Inhibitor4 (1H-Indazol-3-yl)-[2-(2-trifluoromethyl-phenyl)-quinazolin-4-yl]-amine) is bound in the active site in the unphosphorylated GSK-3β structure (FIG. 16). The indazole ring of inhibitor4 forms two hydrogen bonds with the hinge backbone. The nitrogen in position one donates a hydrogen to the backbone carbonyl of Asp 133. The nitrogen in position 2 accepts a hydrogen from the Val 135 amide nitrogen. The backbone carbonyl of Val 135 is within hydrogen bonding range of hydrogen donating groups from inhibitor4. It contacts the linker nitrogen and the quinazoline carbon at position 8. The trifluoromethyl phenyl ring is almost perpendicular to the quinazoline ring with the ortho trifluoromethyl substituent pointing to the glycine rich loop. The side chain of glutamine 185 packs against the trifluoromethyl phenyl ring and points to the glycine rich loop.

EXAMPLE 25

Overall Structure of apo-Phosphorylated GSK-3β and Substrate-bound Phosphorylated GSK-3β

Figure 17:
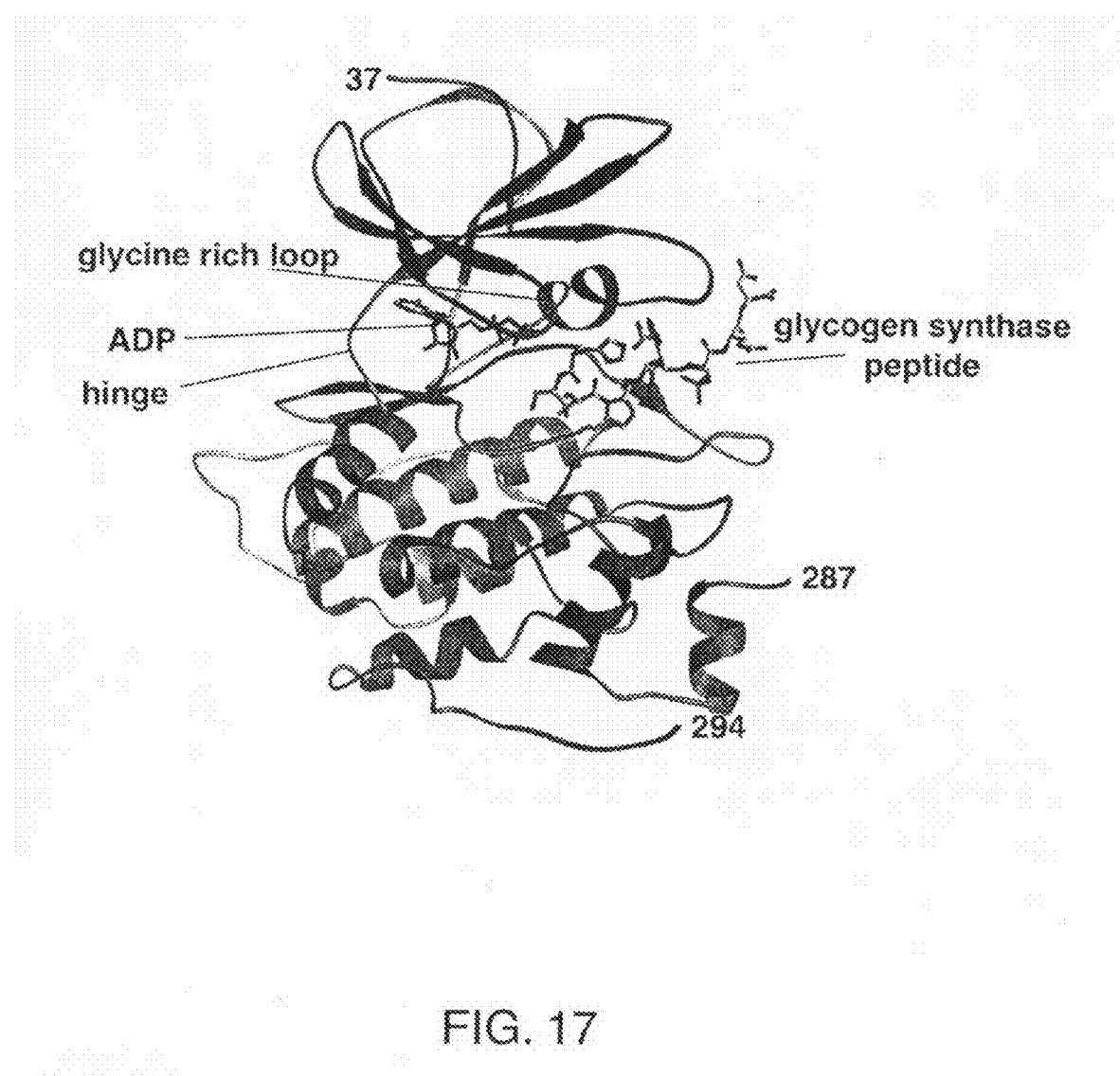
FIG. 17 depicts the overall structure of phosphorylated GSK-3β in complex with ADP and glycogen synthase peptide. The N-terminal domain corresponds to the β-strand domain and includes residues 37 to 138. The α-helical domain of the GSK-3β kinase core corresponds to residues 139 to 343. The C-terminal 34 residues are not part of the kinase core but pack against the α-helical domain. Key features of the kinase fold, such as the glycine rich loop, the hinge and the activation loop are indicated. The ADP-Mg complex occupying the active site is shown. The glycogen synthase peptide (residues 650 to 658) bound in the substrate binding groove is also shown here.

The apo-phosphorylated GSK-3β and substrate-bound phosphorylated GSK-3β structures have the typical two-domain kinase fold (residues 37 to 343) (Hanks, S. K. and Quinn, A. M., *Methods Enzymol.,* 200, pp. 38-62 (1991); Hanks, S. K. and Hunter, T., FASEB J., 9, pp. 576-96 (1995)). The N-terminal β-strand domain (amino acid residues 37 to 138) forms a P-barrel consisting of seven β-strands (FIG. 17). The C-terminal α-helical domain contains amino acid residues 139 to 343. The C-terminal 40 amino acid residues (residues 344 to 383) are not part of the kinase fold, but pack against the α-helical domain.

The active site and the substrate-binding groove are located at the interface of the β-strand and α-helical domain. The active site is bordered by the hinge and the glycine-rich loop and contains an ADP-molecule. The substrate-binding groove contains a 12 amino acid residue phosphorylated peptide derived from the sequence in glycogen synthase recognized by GSK-3β (650 HSSPHQpSEDEEE 661 (SEQ ID NO: 21)). The peptide is positioned between the activation loop (amino acid residues 200 to 226) and the β-strand domain (FIG. 17).

Figure 18:
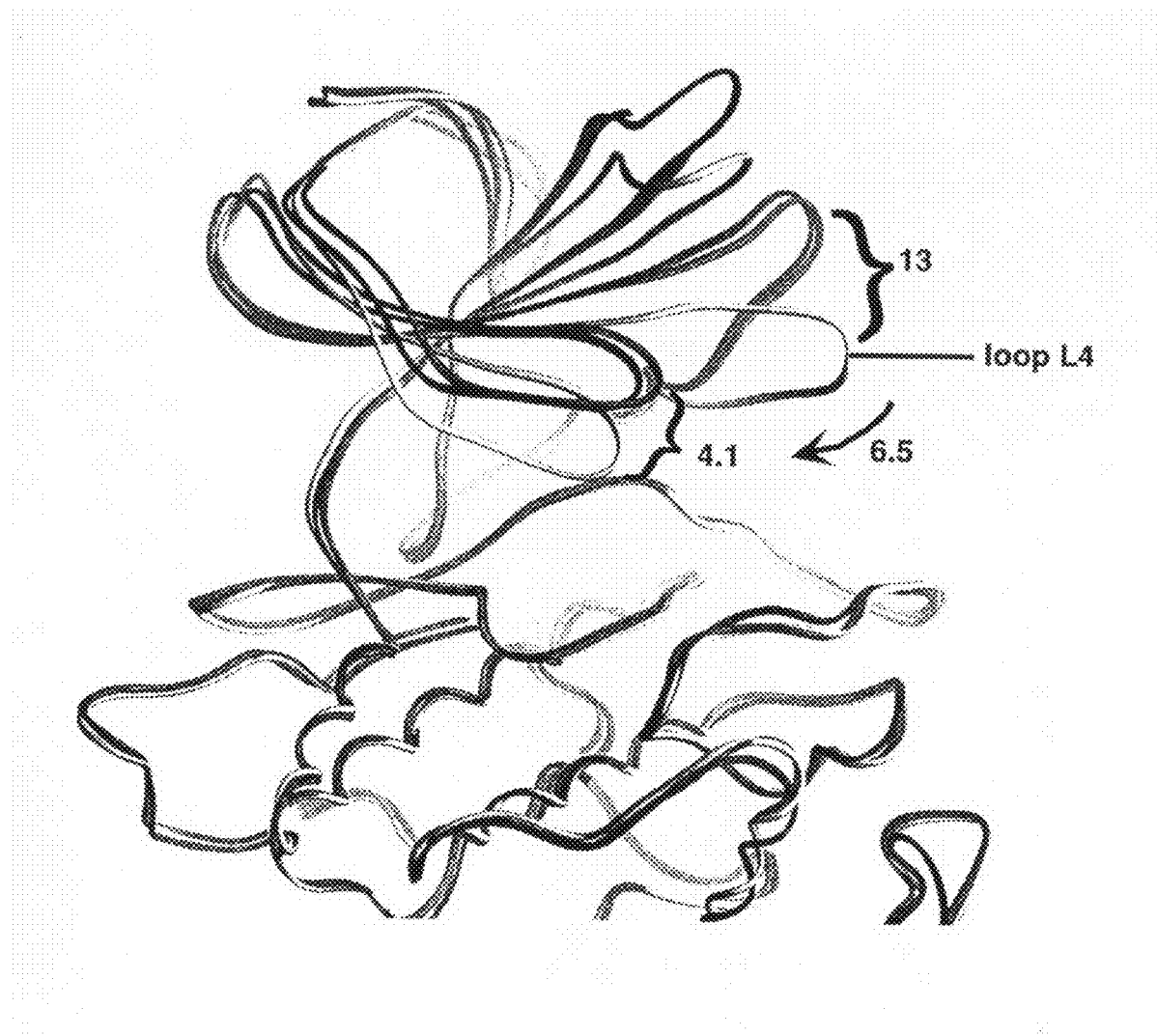
FIG. 18 depicts the β-strand domain rotation induced by ADP and glycogen synthase peptide. Superposition of the α-helical domains of unphosphorylated (dark shade), phosphorylated apo-GSK3 (gray shade) and phosphorylated ADP peptide bound GSK-3β (light shade). The β-strand domain of the phosphorylated GSK-3β-ADP-peptide complex, rotated 6.5 Å in comparison to unphosphorylated and phosphorylated apo-GSK-3. The loop between β-3 and α-C (residues 87 to 95) moved 13 Å to contact the glycogen synthase peptide (not shown).

Comparison between the structures of unphosphorylated, phosphorylated apo-GSK-3β and phosphorylated peptide-bound GSK-3β reveal local differences induced by the presence of the substrates (FIG. 18). Superposition of the protein backbone of unphosphorylated and phosphorylated apo-GSK-3β resulted in a mean displacement of 0.7 Å and a maximum displacement of 3.7 Å of the Ile 217 backbone carbonyl. In the phosphorylated peptide-bound GSK-3β structure, the phosphorylated side chain of Tyr 216 rotated out of the substrate-binding groove and induced a 180° flip of the Ile 217 backbone carbonyl. As a consequence of this adjustment, the torsion angles of Cys 218 appeared in disallowed regions of the Ramachandran plot. In the phosphorylated apo-GSK-3β structure, the side chain of Y216 also flips out of the substrate binding groove (FIG. 10). The N-terminal domain of the phosphorylated peptide-bound GSK-3β rotated by 6.5°, with the glycine rich loop covering the ADP molecule. The reorganization of the glycine rich loop resulted in 4.1 Å translation of the Ser 66 α-carbon. The loop connecting β-3 to α-C (L4, amino acid residues 87 to 95) migrated 13 Å (amino acid residue 92) towards the substrate-binding groove, and form contacts with the backbone atoms of the glycogen synthase peptide. The αG helix (amino acid residues 262 to 273) rotated towards phosphorylated Tyr 216. The rotation of the β-strand domain and the adjustments of the glycine rich loop and L4 were induced by the presence of ADP and the substrate peptide since the β-strand domain of apo-phosphorylated GSK-3β were not rotated in comparison to unphosphorylated GSK-3β.

The loop connecting α1L14 with Trp 301 (amino acid residues 284 to 300) was poorly ordered in the apo- and ADP, peptide-bound structures. This loop is part of the Frat1 binding site (Bax, B. et al., Structure(Camb), 9, pp. 1143-52 (2001)) and covers a hydrophobic groove between αG and amino acid residues 288-294. The loop is separate from the substrate-binding groove and does not seem to influence peptide phosphorylation even when Frat1 is bound to GSK-3β (Thomas, G. M. et al., *FEBS Lett.,* 458, pp. 247-51 (1999)).

EXAMPLE 26

The Active site of the GSK-30-ADP-peptide Complex

The active site is located at the interface of the β-strand and α-helical domain and is enclosed by the glycine rich loop and the hinge. The glycine rich loop is formed by two anti-parallel β-strands. The conformation of the glycine rich loop adjusts to the ligand that occupies the active site. The absence of the γ-phosphate in the ADP molecule allows the glycine rich loop to descend closer to the α-helical domain. A similar adjustment of the glycine rich loop was observed in the PKA-ADP complex (Protein Data Bank Accession number 1JBP) (Madhusudan, Trafny, E. A. et al., *Protein Sci,* 3, pp. 176-87 (1994)).

Figure 19A:
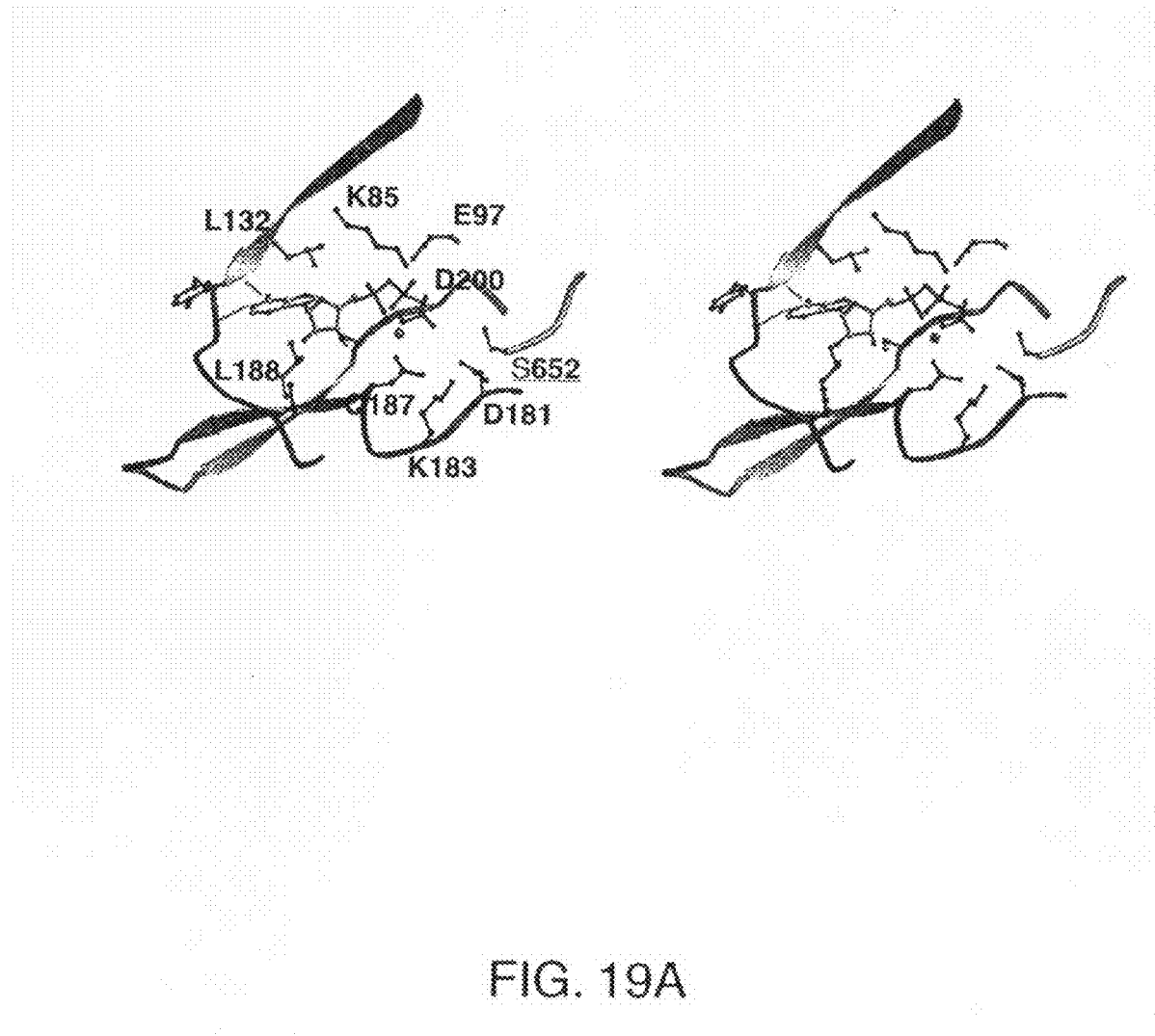
FIG. 19A depicts a stereo view of the active site occupied by the ADP-Mg complex. The adenine base is surrounded by hydrophobic residues and makes two hydrogen bonds with the backbone of the hinge region. The catalytic residues involved in the phosphate transfer to the P-site serine surround the two non-transferable ADP phosphates.
Figure 19B:
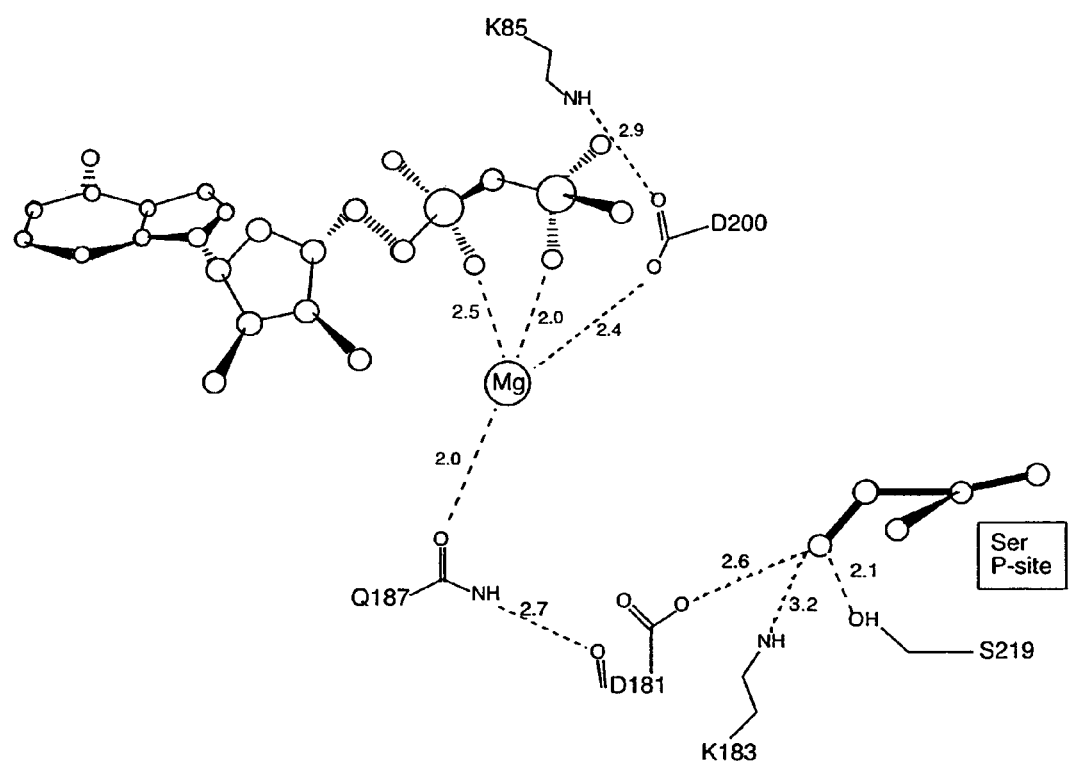
FIG. 19B is a schematic drawing of the hydrogen bond network that connects the ADP-Mg complex to the P-site serine via the catalytic residues.
Figure 20:
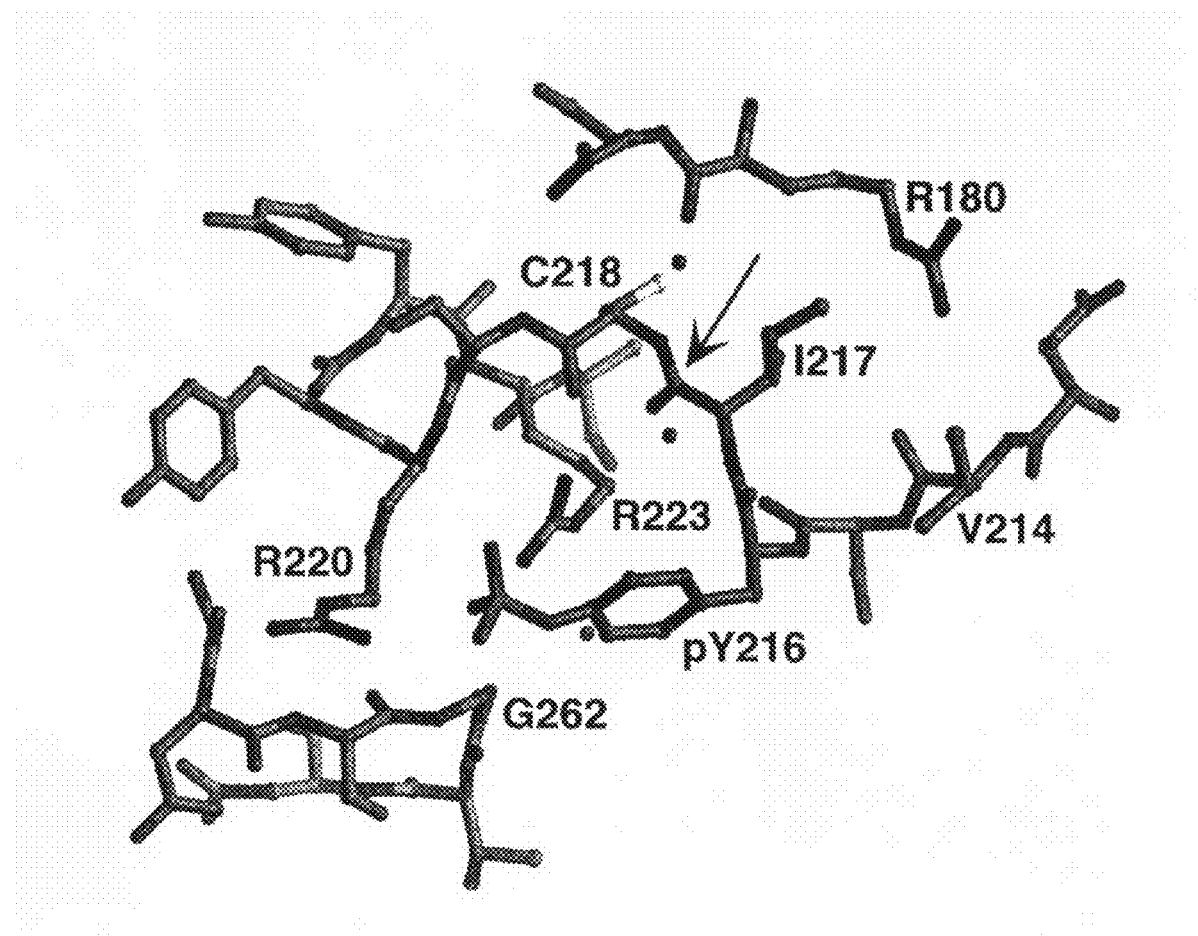
FIG. 20 depicts the environment of phosphotyrosine 216 in the structure of phosphorylated GSK-3β in complex with ADP and glycogen synthase peptide. The phosphate moiety binds two arginine side chains (Arg 220 and Arg 223) resulting in charge neutralization. The arrow indicated the 180 degree flip of I217 backbone carbonyl.

The entire β-strand domain rotated 6.5° as a result of the ADP molecule being bound in the active site. The adenine moiety of ADP is surrounded by hydrophobic amino acid residues from the glycine rich loop (Ile 62, Val 70), from the hinge (Tyr 134) and from the bottom of the active site (Leu 188, Cys 199) (FIG. 19A). Two hydrogen bonds between the base and the hinge backbone were observed. The amino group on position 6 forms a hydrogen bond with the backbone carbonyl of Asp 133, and the N1 nitrogen accepts a hydrogen from Val135 amide nitrogen. The 3' hydroxyl from the ADP ribose donates a hydrogen to the backbone carbonyl of Gln 185. The active site residues that play a role in the serine phosphorylation reaction form a web of hydrogen bonds around the ADP phosphates and the glycogen synthase target serine (FIG. 19B). The two ADP phosphates form a complex with one Mg ion, which in turn contacts the side chains of Asp 200 and Gln 185. Asp 200 is part of the Asp Phe Gly motif and is the first amino acid residue of the activation loop. The Asp 200 homologue in other kinase-AMPPNP complexes binds a second Mg ion (or Mn ion) that is positioned between the β- and γ-phosphate (Bellon, S. et al., *Structure Fold Des.,* 7, pp. 1057-65 (1999); Xie, X. et al., *Structure,* 6, pp. 983-91 (1998); Bossemeyer, D. et al., *EMBO J,* 12, pp. 849-59 (1993)). However, a second Mg ion could not be located in our electron density maps. On the other hand, the structure of the PKA-ADP complex (Protein Data Bank Accession number 1JBP) (Madhusudan, Trafny, E. A. et al., *Protein Sci,* 3, pp. 176-87 (1994)) does not have any Mg ion associated with the phosphate groups.

Lys 85 is positioned between Glu97 and the α- and β-phosphates and likely facilitates the transfer of the γ-phosphate from ATP to the substrate serine. Asp 181 is also a conserved residue in kinases and its side chain is within hydrogen bonding range of the peptide target serine (Ser 652). The backbone carbonyl of Asp 181 forms a hydrogen bond with the Gln 185 side chain. Asp 181 prepares the serine hydroxyl for the nucleophilic attack on the γ-phosphate (Adams, J. A., *Chem. Rev.,* 101, pp. 2271-2290 (2001)). Lys 183 makes a hydrogen bond with the peptide target serine. Lys 183 is positioned between the phosphate groups and the target serine and is involved in the phosphate transfer. When the γ-phosphate is present in the kinase active site, the Lys 183 is likely to contact the terminal phosphate group.

EXAMPLE 27

The Substrate-Binding Groove of the GSK-3β-ADP-Peptide Complex

GSK-3β has one phosphorylation site in the activation loop, Y216, which acts as a gate for the substrate-binding groove. In the crystal structure of unphosphorylated GSK-3β, the unphosphorylated tyrosyl side chain occupied the substrate-binding groove. A comparison between the unphosphorylated and phosphorylated peptide-bound GSK-3β structures showed that there would be space to accommodate the glycogen synthase peptide even if the unphosphorylated tyrosine remains in the substrate-binding groove. The P+2 residue of the peptide (H is 654) is the closest amino acid residue to Tyr 216. Its imidazole ring is part of a cluster of aromatic residues formed by GSK-3β residues Phe 67, Phe 93 and the peptide substrate amino acid residue H is 650.

Figure 21:
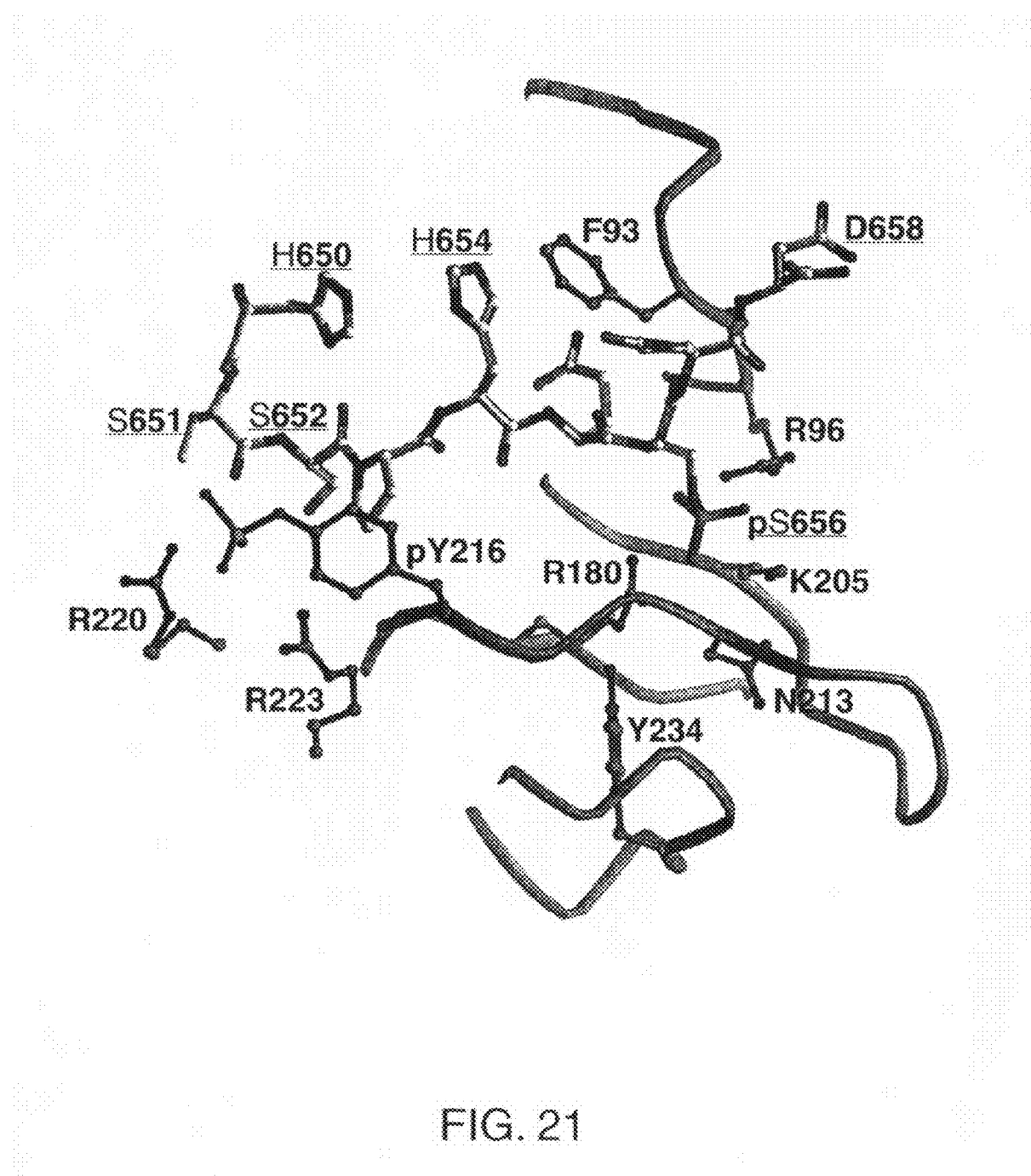
FIG. 21 depicts the glycogen synthase peptide in the substrate binding groove. The phosphoserine (pser 656) binds Arg 96, Arg 180 and Lys 205, which results in the proper alignment of the α-helical and β-strand domains. pTyr 216 moves its side chain out of the substrate binding groove to make contact with the side chains of Arg 220 and Arg 223.

The phosphorylated Tyr216 side chain has moved out of the substrate-binding groove in the GSK-3β-ADP-peptide complex structure (FIG. 21). The phospho-phenol group of Tyr 216 is bound to the side chains of Arg 220 and Arg 223, which results in neutralization of the negative charge of the phosphate group and a 180° flip of the Ile 217 backbone carbonyl. The phospho-phenol group also caused a slight adjustment of the αG helix (residues 262-272), which results in the distance between the phosphate oxygen atoms and amide nitrogen of G262 (which is the closest H-bond donor) outside the H-bonding range (4.4 Å).

Glycogen synthase is a major substrate of GSK-3β with multiple phosphorylation sites. The canonical phosphorylation site for GSK-3β is SXXXpS. The P+4 serine (or threonine) is first phosphorylated by a different kinase, which is called primed phosphorylation. In the case of glycogen synthase, GSK-3β phosphorylates four sites sequentially after it is phosphorylated by casein kinase-II. The co-crystallized peptide present in the substrate-binding groove is derived from glycogen synthase. The sequence (650-HSSPHQ(pS)EDEEE-661 (SEQ ID NO: 21)) contains the canonical GSK-3β phosphorylation motif and GSK-3βcan phosphorylate Ser 652 under the appropriate conditions. Ten of the twelve residues (residues 650 to 659) had visible electron density and were built in the substrate-binding groove (FIG. 21). The peptide has the shape of a large loop with residues 651 to 656 fitting in the substrate binding groove and residues 650, 657 to 659 exposed to solvent. The structure reveals why GSK-3 β prefers a phosphorylated serine or threonine at the P+4 position of the glycogen synthase phosphorylation site. The phosphate group of Ser 656 occupies a positively surface charged pocket formed by residues Arg 96, Arg 180 and Lys 205. These amino acid residues are conserved in serine/threonine kinases and are responsible for the proper alignment of the β-strand and α-helical domains, the latter of which is required for optimal catalytic activity. Other serine/threonine kinases such as CDK2 (Schulze-Gahmen, U. et al., Proteins, 22, pp. 378-91 (1995)), ERK2 (Zhang, F. et al., Nature, 367, pp. 704-11 (1994); Canagarajah, B. J. et al., Cell, 90, pp. 859-69 (1997)) and p38γ (Bellon, S. et al., Structure Fold Des., 7, pp. 1057-65 (1999)) have a phosphorylated threonine in the activation loop for this purpose, but GSK-3 uses a phosphorylated residue from the substrate. The target serine (Ser 652) is positioned in front of the active site, 6.0 Å from the β-phosphate of the ADP molecule. The loop between residues Lys 85 and Arg 96 migrates more than 10 Å to facilitate the glycogen synthase peptide binding. Phe 93 forms a pi-stack with the peptide His 654. Ser 66, which is at the tip of the glycine rich loop, makes a hydrogen bond with the target serine backbone-nitrogen (Ser 652). The backbone carbonyl of pSer 656 forms a hydrogen bond with Lys 94.

The canonical phosphorylation motif for GSK-3β is SXXXpS. There is no sequence requirement for the three residues between the target serine and the phosphoserine. The P+1 residue in the glycogen synthase peptide used here is a proline. Although prolines are not uncommon as the P+1 residue in phosphorylation motifs, the GSK-3β phosphorylation does not require a proline. A sequence analysis of the phosphorylation motifs of the proteins that undergo primed phosphorylation shows that residues such as A, G, Q, E, S, T, R and V can replace the proline at the P+1 position. In the GSK-3β-ADP-peptide structure, the proline side chain fits in a pocket formed by the side chains of pY216, R220, R223 and the backbones of residues 217 to 219. The pocket is shallow, and the distance between the Cγ of Pro 654 and Arg 223 is 3.8 Å. This pocket can only accommodate small residues such as Ala, Ser or Val. Larger residues, such as Arg and Gln will have to point their side chains into the solvent. This might explain the absence of bulky hydrophobic residues at the P+1 position. This fact is reflected in the interactions between the glycogen synthase peptide and GSK-3β. Except for the phosphoserine side chain interactions with the basic residues, the other interactions are with the peptide backbone. The pi-stack interaction between His 654 and Phe 93 is probably specific for the phosphorylation of Ser 652, because there is no aromatic residue at the P+2 position in other motifs of glycogen synthase or eIF2b.

The crystal structure of the GSK-3β-ADP-peptide complex provides a detailed picture of the phosphorylation of the glycogen synthase peptide. Although the ADP molecule does not contain the γ-phosphate, the catalytic residues are located around the ADP molecule similar to the positions in other kinase nucleotide complexes. The phosphoserine of the peptide serves as an anchor for the peptide and is required for the proper alignment of the β-strand and α-helical domains of GSK-3β.

Biological Implications

Activation of the insulin-signaling pathway induces increased glucose uptake and conversion to glycogen. Patients with type II diabetes have decreased sensitivity towards insulin, which reduces glycogen synthesis and increased blood glucose levels. The conversion of glucose into glycogen by glycogen synthase is the rate limiting step in glycogen synthesis and the phosphorylation status of glycogen synthase determines the catalytic rate. Glycogen synthase has at least nine phosphorylation sites and the more it is phosphorylated the lower its catalytic activity. GSK-3β is one of the kinases that phosphorylates and inhibits glycogen synthase. It phosphorylates sequentially multiple sites at the C-terminal end of glycogen synthase after Casein Kinase II phosphorylates glycogen synthase. The canonical sequence recognized by GSK-3β is SXXXpS, which is four times present in glycogen synthase. GSK-3β is a potential therapeutic target for type 2 diabetes because its inhibition leads to increased glycogen synthesis and decreased blood glucose levels.

The crystal structures of apo-phosphorylated GSK-3β and GSK-3β in complex with ADP and glycogen synthase peptide provide insight on how GSK-3β phosphorylates its substrates. The ADP molecule occupies the active site and the glycogen synthase peptide occupies the substrate-binding groove. The phosphorylated serine at the P+4 position of the glycogen synthase peptide binds three well-conserved basic residues, which results in optimal alignment of the β-strand and α-helical domains of the GSK-3β kinase core. Other interactions between GSK-3β and the glycogen synthase peptide involve mostly backbone atoms of the peptide, which might explain the tolerance for different residues at position P+1, P+2 and P+3. The present invention will be helpful in understanding the role of GSK-3β in the insulin-signaling pathway and development of potential new anti-diabetic therapies.

EXAMPLE 28

The Use of GSK-3β Coordinates for Inhibitor Design

The coordinates of any one of FIGS. 1-7 are used to design compounds, including inhibitory compounds, that associate with GSK-3β or GSK-3β homologues. This process may be aided by using a computer comprising a machine-readable data storage medium encoded with a set of machine-executable instructions, wherein the recorded instructions are capable of displaying a three-dimensional representation of the GSK-3β, the GSK-3β homologues or portions thereof. The graphical representation is used according to the methods described herein to design compounds. Such compounds associate with the GSK-3β or GSK-3β homologue at the active site or substrate binding pocket.

While we have described a number of embodiments of this invention, it is apparent that our basic constructions may be altered to provide other embodiments which utilize the products, processes and methods of this invention. Therefore, it will be appreciated that the scope of this invention is to be defined by the appended claims, rather than by the specific embodiments which have been presented by way of example.

U.S. provisional applications 60/287,366, 60/361,899, 60/297,094 are incorporated herein by reference in their entirety.

TABLE 12

Summary of data collection

| Source | R-Axis IV | ALS 5.0.2 |
|---|---|---|
| Wavelength (Å) | 1.54 | 1.1 |
| Resolution (Å) | 3.0 | 2.7 |
| No. of Reflections (measured/unique) | 303687/26039 | 251279/34993 |
| Completeness (%) (overall/outer shell) | 96.7/89.3 | 98.9/99.8 |
| $R_{merge}$ (%)[1] (overall/outer shell) | 0.064/0.30 | 0.070/0.32 |

Structure refinement

| Resolution (Å) | 48.3-2.7 |
|---|---|
| No. of reflections | 34747 |
| R factor | 23.7 |
| Free R factor† | 27.4 |
| Rms deviations | |
| Bond lengths | 0.01 |
| Bond angles | 1.5° |

[1]$R_{merge} = 100 \times \Sigma_h \Sigma_i |I_{hi} - <I_h>|/\Sigma_h \Sigma_i I_{hi}$.
†The Free R factor was calculated with 9.1% of the data.

TABLE 13

Summary of data collection

| Source | R-Axis IV |
|---|---|
| Wavelength (Å) | 1.54 |
| Resolution (Å) | 2.5 |
| No. of Reflections (measured/unique) | 32357/3447 |
| Completeness (%) (overall/outer shell) | 87.0/61.8 |
| I/δ (I) (overall/outer shell) | 10.4/2.3 |
| $R_{merge}$ (%) (overall/outer shell) | 0.064/0.30 |

Structure refinement

| Resolution (Å) | 42.8-2.5 |
|---|---|
| No. of reflections | 32357 |
| R factor | 23.8 |
| Free R factor[1] | 27.6 |
| Rms deviations | |
| Bond lengths | 0.008 |
| Bond angles | 1.5° |
| Bfactor (average)[2] | 45 Å |

[1]The Free R factor was calculated with 10% of the data.
[2]The B-factor of the data (Wilson plot) was 26.4 Å².

TABLE 14

Summary of data collection

| Source | R-Axis IV |
|---|---|
| Wavelength (Å) | 1.54 |
| Resolution (Å) | 2.9 |
| No. of Reflections (measured/unique) | 338559/26836 |
| Completeness (%) (overall/outer shell) | 93.1/85.1 |

TABLE 14-continued

| I/δ (I) (overall/outer shell) | 10.2/2.7 |
|---|---|
| $R_{merge}$ (%) (overall/outer shell) | 0.072/0.29 |

Structure refinement

| Resolution (Å) | 25.7-2.9 |
|---|---|
| No. of reflections | 26796 |
| R factor | 24.0 |
| Free R factor[1] | 27.9 |
| Rms deviations | |
| Bond lengths | 0.011 |
| Bond angles | 1.8° |
| Bfactor (average)[2] | 39.3 Å |

[1]The Free R factor was calculated with 9.4% of the data.
[2]The B-factor of the data (Wilson plot) was 33 Å².

TABLE 15

Summary of data collection

| Source | R-Axis IV |
|---|---|
| Wavelength (Å) | 1.54 |
| Resolution (Å) | 2.8 |
| No. of Reflections (measured/unique) | 71493/23161 |
| Completeness (%) (overall/outer shell) | 88.3/90.3 |
| I/δ (I) (overall/outer shell) | 14.7/2.2 |
| $R_{merge}$ (%) (overall/outer shell) | 0.046/0.33 |

Structure refinement

| Resolution (Å) | 32.2-2.8 |
|---|---|
| No. of reflections | 23148 |
| R factor | 22.5 |
| Free R factor[1] | 26.8 |
| Rms deviations | |
| Bond lengths | 0.013 |
| Bond angles | 1.6° |
| Bfactor (average)[2] | 51.1 Å |

[1]The Free R factor was calculated with 9.4% of the data.
[2]The B-factor of the data (Wilson plot) was 91.3 Å².

TABLE 16

Summary of data collection

| Source | R-Axis IV |
|---|---|
| Wavelength (Å) | 1.54 |
| Resolution (Å) | 2.8 |
| No. of Reflections (measured/unique) | 311458/24709 |
| Completeness (%) (overall/outer shell) | 99.4/99.8 |
| I/δ (I) (overall/outer shell) | 18.4/3.6 |
| $R_{merge}$ (%) (overall/outer shell) | 0.075/0.33 |

Structure refinement

| Resolution (Å) | 49.3-2.8 |
|---|---|
| No. of reflections | 24288 |
| R factor | 23.5 |
| Free R factor[1] | 27.2 |
| Rms deviations | |
| Bond lengths | 0.013 |
| Bond angles | 1.7° |

[1]The Free R factor was calculated with 9.4% of the data.

We claim:

1. A crystal comprising an unphosphorylated Glycogen Synthase Kinase-3β (GSK-3β) protein complexed to a chemical entity, wherein said GSK-3β protein consists of amino acids 7-420 of SEQ ID NO:1;

wherein said crystal is in space group $P2_1 2_1 2_1$, and has unit cell dimensions of a=83±2 Å, b=86±2 Å, c=178±2 Å, $\alpha=\beta=\gamma=90°$; and wherein said chemical entity is selected from the group consisting of: (5-Methyl-2H-pyrazol-3-yl)-(2-pyridin-4-yl-quinazolin-4-yl)-amine; 4-(5-Methyl-2-phenylamino-pyrimidin-4-yl)-1H-pyrrole-2-carboxylic acid (2-hydroxy-1-phenyl-ethyl)-amide; and (1H-Indazol-3-yl)-[2-(2-trifluoromethyl-phenyl)-quinazolin-4-yl]-amine).

2. A method of obtaining a crystal comprising an unphosphorylated Glycogen Synthase Kinase-3β (GSK-3β) protein complexed to a chemical entity, wherein said GSK-3β protein consists of amino acids 7-420 of SEQ ID NO:1, and wherein said crystal is in space group $P2_1 2_1 2_1$, and has unit cell dimensions of a=83±2 Å, b=86±2 Å, c=178±2 Å, $\alpha=\gamma=90°$;

comprising the steps of:

a) producing and purifying said GSK-3β protein;

b) forming a protein complex by contacting the purified GSK-3β protein of step a) with a chemical entity is selected from the group consisting of: (5-ethyl-2H-pyrazol-3-yl)-(2-pyridin-4-yl-quinazolin-4-yl)-amine; 4-(5-Methyl-2-phenylamino-pyrimidin-4-yl)-1H-pyrrole-2-carboxylic acid (2-hydroxy-1-phenyl-ethyl)-amide; and (1H-Indazol-3-yl)-[2-(2-trifluoromethyl-phenyl)-quinazolin-4-yl]-amine);

c) mixing a crystallization solution with the protein complex of step b) to produce a crystallizable composition; and d) subjecting the crystallizable composition of step c) to conditions which promote crystallization, thereby obtaining said crystal.

3. The method of claim 1, wherein the GSK-3β protein is produced from a baculovirus overexpression system.

* * * * *

SEQUENCE LISTING

<160> NUMBER OF SEQ ID NOS: 56

<210> SEQ ID NO 1
<211> LENGTH: 420
<212> TYPE: PRT
<213> ORGANISM: Homo sapiens

<400> SEQUENCE: 1

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Val
    290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys Leu Pro Asn
            340                 345                 350

Gly Arg Asp Thr Pro Ala Leu Phe Asn Phe Thr Thr Gln Glu Leu Ser

-continued

```
                355                 360                 365

Ser Asn Pro Pro Leu Ala Thr Ile Leu Ile Pro Pro His Ala Arg Ile
    370                 375                 380

Gln Ala Ala Ala Ser Thr Pro Thr Asn Ala Thr Ala Ala Ser Asp Ala
385                 390                 395                 400

Asn Thr Gly Asp Arg Gly Gln Thr Asn Asn Ala Ala Ser Ala Ser Ala
                405                 410                 415

Ser Asn Ser Thr
            420

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ser Val Pro Pro Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Ser Pro Ser Leu Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Ser Arg His Ser Ser
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ser Pro His Gln Ser
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 6

Asp Ser Arg Ala Gly Ser
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Ser Arg Arg Pro Ser
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Thr Pro Pro Pro Thr
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Thr Pro Val Pro Ser
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Ser Pro Val Val Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Ser Gly Asp Thr Ser
1               5

<210> SEQ ID NO 12
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 12

Gln Ser Tyr Leu Asp Ser
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Ser Gly Ile His Ser
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Ser Gly Ala Thr Thr
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Thr Thr Ala Pro Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Ser Ala Asn Asp Ser
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Ser Glu Gln Gln Ser
1               5
```

```
<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Ser Pro Leu Pro Ser
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Ser Ser Pro Leu Ser
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Thr Pro Thr Asp Val
1               5

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phosphoylated-Ser

<400> SEQUENCE: 21

His Ser Ser Pro His Gln Ser Asp Glu Glu Glu
1               5                   10

<210> SEQ ID NO 22
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Val Thr Thr Val Val Ala Thr Pro Gly Ala Gly Pro Asp Arg Pro Gln
1               5                   10                  15

Glu Val Ser Tyr Thr Asp Thr Lys Val Ile Gly Asn Gly Ser Phe Gly
            20                  25                  30

Val Val Tyr Gln Ala Lys Leu Cys Asp Ser Gly Glu Leu Val Ala Ile
```

-continued

```
                35                  40                  45
Lys Lys Val Leu Gln Asp Ala Ala Ala Asn Arg Glu Leu Gln Ile
 50                  55                  60

Met Arg Lys Leu Asp His Cys Asn Ile Val Arg Leu Arg Tyr Phe Phe
 65                  70                  75                  80

Tyr Ser Ser

<210> SEQ ID NO 23
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (92)..(92)
<223> OTHER INFORMATION: Phosphoylated-Tyr

<400> SEQUENCE: 23

Ala Ala Tyr Leu Asn Leu Val Leu Asp Tyr Val Pro Glu Thr Val Tyr
 1               5                  10                  15

Arg Val Ala Arg His Tyr Ser Arg Ala Lys Gln Thr Leu Pro Val Ile
                20                  25                  30

Tyr Val Lys Leu Tyr Met Tyr Gln Leu Phe Arg Ser Leu Ala Tyr Ile
             35                  40                  45

His Ser Phe Gly Ile Cys His Arg Asp Ile Lys Pro Gln Asn Leu Leu
 50                  55                  60

Leu Asp Pro Asp Thr Ala Val Leu Lys Leu Cys Asp Phe Gly Ser Ala
 65                  70                  75                  80

Lys Gln Leu Val Arg Gly Glu Pro Asn Val Ser Tyr Ile Cys Ser Arg
                85                  90                  95

Tyr Tyr Arg Ala Pro Glu Leu Ile Phe Gly Ala Thr Asp Tyr Thr Ser
                100                 105                 110

Ser Ile Asp Val Trp Ser Ala Gly Cys Val Leu Ala Glu Leu Leu Leu
            115                 120                 125

Gly Gln Pro Ile Phe Pro Gly Asp Ser Gly Val Asp Gln Leu Val Glu
        130                 135                 140

Ile Ile Lys Val Leu Gly Thr Pro Thr Arg Glu Gln Ile Ala Glu Met
145                 150                 155                 160

Asn Pro Asn

<210> SEQ ID NO 24
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Ala Ala Ala Ala His Pro Trp Thr Ala Val Phe Arg Pro Ala Thr
 1               5                  10                  15

Pro Pro Glu Ala Ile Ala Leu Cys Ser Arg Leu Leu Glu Tyr Thr Pro
                20                  25                  30

Thr Ala Arg Leu Thr Pro Leu Glu Ala Cys Ala His Ser Phe Phe Asp
         35                  40                  45

Glu Leu Arg Asp Pro Asn Val Lys Leu Pro Asn Gly Arg Asp Thr Pro
 50                  55                  60
```

```
Ala Leu Phe Asn Phe Thr Thr Gln Glu Leu Ser Ser Asn Pro Pro Leu
 65                  70                  75                  80

Ala Thr Ile Leu Ile Pro Pro His Ala Arg
                85                  90

<210> SEQ ID NO 25
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Val Thr Thr Val Val Ala Thr Pro Gly Asp Gly Pro Asp Arg Pro Gln
  1               5                  10                  15

Glu Val Ser Tyr Thr Asp Thr Lys Val Ile Gly Asn Gly Ser Phe Gly
                 20                  25                  30

Val Val Tyr Gln Ala Lys Leu Cys Asp Ser Gly Glu Leu Val Ala Ile
             35                  40                  45

Lys Lys Val Leu Gln Asp Lys Ala Ala Asn Arg Glu Leu Gln Ile
 50                  55                  60

Met Arg Lys Leu Asp His Cys Asn Ile Val Arg Leu Arg Tyr Phe Phe
 65                  70                  75                  80

Tyr Ser Ser

<210> SEQ ID NO 26
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (92)..(92)
<223> OTHER INFORMATION: Phosphoylated-Tyr

<400> SEQUENCE: 26

Ala Ala Tyr Leu Asn Leu Val Leu Asp Tyr Val Pro Glu Thr Val Tyr
  1               5                  10                  15

Arg Val Ala Arg His Tyr Ser Arg Ala Lys Gln Thr Leu Pro Val Ile
                 20                  25                  30

Tyr Val Lys Leu Tyr Met Tyr Gln Leu Phe Arg Ser Leu Ala Tyr Ile
             35                  40                  45

His Ser Phe Gly Ile Cys His Arg Asp Ile Lys Pro Gln Asn Leu Leu
 50                  55                  60

Leu Asp Pro Asp Thr Ala Val Leu Lys Leu Cys Asp Phe Gly Ser Ala
 65                  70                  75                  80

Lys Gln Leu Val Arg Gly Glu Pro Asn Val Ser Tyr Ile Cys Ser Arg
                 85                  90                  95

Tyr Tyr Arg Ala Pro Glu Leu Ile Phe Gly Ala Thr Asp Tyr Thr Ser
                100                 105                 110

Ser Ile Asp Val Trp Ser Ala Gly Cys Val Leu Ala Glu Leu Leu Leu
            115                 120                 125

Gly Gln Pro Ile Phe Pro Gly Asp Ser Gly Val Asp Gln Leu Val Glu
130                 135                 140

Ile Ile Lys Val Leu Gly Thr Pro Thr Ala Glu Gln Ile Ala Glu Met
145                 150                 155                 160
```

```
Gly

<210> SEQ ID NO 27
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Ala Ala His Pro Trp Thr Ala Val Phe Arg Pro Ala Thr Pro Pro
1               5                   10                  15

Glu Ala Ile Ala Leu Cys Ser Arg Leu Leu Glu Tyr Thr Pro Thr Ala
            20                  25                  30

Arg Leu Thr Pro Leu Glu Ala Cys Ala His Ser Phe Phe Asp Glu Leu
        35                  40                  45

Arg Asp Pro Asn Val Lys Leu Pro Asn Gly Arg Asp Thr Pro Ala Leu
    50                  55                  60

Phe Asn Phe Thr Thr Gln Glu Leu Ser Ser Asn Pro Pro Leu Ala Thr
65                  70                  75                  80

Ile Leu Ile Pro Pro His Ala Arg
                85

<210> SEQ ID NO 28
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Val Thr Thr Val Val Ala Thr Pro Gly Ala Gly Pro Asp Arg Pro Gln
1               5                   10                  15

Glu Val Ser Tyr Thr Asp Thr Lys Val Ile Gly Asn Gly Ser Phe Gly
            20                  25                  30

Val Val Tyr Gln Ala Lys Leu Cys Asp Ser Gly Glu Leu Val Ala Ile
        35                  40                  45

Lys Lys Val Leu Gln Asp Ala Ala Ala Asn Arg Glu Leu Gln Ile
    50                  55                  60

Met Arg Lys Leu Asp His Cys Asn Ile Val Arg Leu Arg Tyr Phe Phe
65                  70                  75                  80

Tyr Ser Ser

<210> SEQ ID NO 29
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (92)..(92)
<223> OTHER INFORMATION: Phosphoylated-Tyr

<400> SEQUENCE: 29

Ala Ala Tyr Leu Asn Leu Val Leu Asp Tyr Val Pro Glu Thr Val Tyr
1               5                   10                  15

Arg Val Ala Arg His Tyr Ser Arg Ala Lys Gln Thr Leu Pro Val Ile
```

```
                20                  25                  30
Tyr Val Lys Leu Tyr Met Tyr Gln Leu Phe Arg Ser Leu Ala Tyr Ile
            35                  40                  45

His Ser Phe Gly Ile Cys His Arg Asp Ile Lys Pro Gln Asn Leu Leu
 50                  55                  60

Leu Asp Pro Asp Thr Ala Val Leu Lys Leu Cys Asp Phe Gly Ser Ala
 65                  70                  75                  80

Lys Gln Leu Val Arg Gly Glu Pro Asn Val Ser Tyr Ile Cys Ser Arg
                85                  90                  95

Tyr Tyr Arg Ala Pro Glu Leu Ile Phe Gly Ala Thr Asp Tyr Thr Ser
            100                 105                 110

Ser Ile Asp Val Trp Ser Ala Gly Cys Val Leu Ala Glu Leu Leu Leu
            115                 120                 125

Gly Gln Pro Ile Phe Pro Gly Asp Ser Gly Val Asp Gln Leu Val Glu
            130                 135                 140

Ile Ile Lys Val Leu Gly Thr Pro Thr Arg Glu Gln Ile Ala Glu Met
145                 150                 155                 160

Asn Pro Asn Ala

<210> SEQ ID NO 30
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Ala Ala Ala Ala His Pro Trp Thr Ala Val Phe Arg Pro Ala Thr
 1               5                  10                  15

Pro Pro Glu Ala Ile Ala Leu Cys Ser Arg Leu Leu Glu Tyr Thr Pro
                20                  25                  30

Thr Ala Arg Leu Thr Pro Leu Glu Ala Cys Ala His Ser Phe Phe Asp
            35                  40                  45

Glu Leu Arg Asp Pro Asn Val Lys Leu Pro Asn Gly Arg Asp Thr Pro
 50                  55                  60

Ala Leu Phe Asn Phe Thr Thr Gln Glu Leu Ser Ser Asn Pro Pro Leu
 65                  70                  75                  80

Ala Thr Ile Leu Ile Pro Pro His Ala Arg
                85                  90

<210> SEQ ID NO 31
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Val Thr Thr Val Val Ala Thr Pro Gly Asp Gly Pro Asp Arg Pro Gln
 1               5                  10                  15

Glu Val Ser Tyr Thr Asp Thr Lys Val Ile Gly Asn Gly Ser Phe Gly
                20                  25                  30

Val Val Tyr Gln Ala Lys Leu Cys Asp Ser Gly Glu Leu Val Ala Ile
            35                  40                  45

Lys Lys Val Leu Gln Asp Lys Ala Ala Ala Asn Arg Glu Leu Gln Ile
 50                  55                  60
```

```
Met Arg Lys Leu Asp His Cys Asn Ile Val Arg Leu Arg Tyr Phe Phe
 65                  70                  75                  80

Tyr Ser Ser

<210> SEQ ID NO 32
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (92)..(92)
<223> OTHER INFORMATION: Phosphoylated-Tyr

<400> SEQUENCE: 32

Ala Ala Tyr Leu Asn Leu Val Leu Asp Tyr Val Pro Glu Thr Val Tyr
  1               5                  10                  15

Arg Val Ala Arg His Tyr Ser Arg Ala Lys Gln Thr Leu Pro Val Ile
                 20                  25                  30

Tyr Val Lys Leu Tyr Met Tyr Gln Leu Phe Arg Ser Leu Ala Tyr Ile
             35                  40                  45

His Ser Phe Gly Ile Cys His Arg Asp Ile Lys Pro Gln Asn Leu Leu
         50                  55                  60

Leu Asp Pro Asp Thr Ala Val Leu Lys Leu Cys Asp Phe Gly Ser Ala
 65                  70                  75                  80

Lys Gln Leu Val Arg Gly Glu Pro Asn Val Ser Tyr Ile Cys Ser Arg
                 85                  90                  95

Tyr Tyr Arg Ala Pro Glu Leu Ile Phe Gly Ala Thr Asp Tyr Thr Ser
            100                 105                 110

Ser Ile Asp Val Trp Ser Ala Gly Cys Val Leu Ala Glu Leu Leu Leu
        115                 120                 125

Gly Gln Pro Ile Phe Pro Gly Asp Ser Gly Val Asp Gln Leu Val Glu
    130                 135                 140

Ile Ile Lys Val Leu Gly Thr Pro Thr Ala Glu Gln Ile Ala Glu Met
145                 150                 155                 160

Gly

<210> SEQ ID NO 33
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Ala Ala His Pro Trp Thr Ala Val Phe Arg Pro Thr Pro Thr Pro
  1               5                  10                  15

Glu Ala Ile Ala Leu Cys Ser Arg Leu Leu Glu Tyr Thr Pro Thr Ala
                 20                  25                  30

Arg Leu Thr Pro Leu Glu Ala Cys Ala His Ser Phe Phe Asp Glu Leu
             35                  40                  45

Arg Asp Pro Asn Val Lys Leu Pro Asn Gly Arg Asp Thr Pro Ala Leu
         50                  55                  60

Phe Asn Phe Thr Thr Gln Glu Leu Ser Ser Asn Pro Pro Leu Ala Thr
 65                  70                  75                  80
```

Ile Leu Ile Pro Pro His Ala Arg Ile
            85

<210> SEQ ID NO 34
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ser Met Lys Val Gly Arg Gly Gly Gly Lys Val Thr Thr Val
1               5                   10                  15

Val Ala Thr Pro Gly Ala Gly Pro Asp Arg Pro Gln Glu Val Ser Tyr
            20                  25                  30

Thr Asp Thr Lys Val Ile Gly Asn Gly Ser Phe Gly Val Val Tyr Gln
        35                  40                  45

Ala Lys Leu Cys Asp Ser Gly Glu Leu Val Ala Ile Lys Lys Val Leu
    50                  55                  60

Ala Ala Ala Ala Ala Asn Arg Glu Leu Gln Ile Met Arg Lys Leu
65                  70                  75                  80

Asp His Cys Asn Ile Val Arg Leu Arg Tyr Phe Phe Tyr Ser Ser
                85                  90                  95

<210> SEQ ID NO 35
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Tyr Leu Asn Leu Val Leu Asp Tyr Val Pro Glu Thr Val Tyr Arg Val
1               5                   10                  15

Ala Arg His Tyr Ser Arg Ala Lys Gln Thr Leu Pro Val Ile Tyr Val
            20                  25                  30

Lys Leu Tyr Met Tyr Gln Leu Phe Arg Ser Leu Ala Tyr Ile His Ser
        35                  40                  45

Phe Gly Ile Cys His Arg Asp Ile Lys Pro Gln Asn Leu Leu Leu Asp
    50                  55                  60

Pro Asp Thr Ala Val Leu Lys Leu Cys Asp Phe Gly Ser Ala Lys Gln
65                  70                  75                  80

Leu Val Arg Gly Glu Pro Asn Val Ser Tyr Ile Cys Ser Ala Tyr Tyr
                85                  90                  95

Arg Ala Pro Glu Leu Ile Phe Gly Ala Thr Asp Tyr Thr Ser Ser Ile
                100                 105                 110

Asp Val Trp Ser Ala Gly Cys Val Leu Ala Glu Leu Leu Leu Gly Gln
            115                 120                 125

Pro Ile Phe Pro Gly Asp Ser Gly Val Asp Gln Leu Val Glu Ile Ile
        130                 135                 140

Lys Val Leu Gly Thr Pro Thr Ala Glu Gln Ile Ala Glu Met Ala Ala
145                 150                 155                 160

Ala Ala Pro

<210> SEQ ID NO 36
<211> LENGTH: 85
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 36

```
Trp Thr Ala Val Phe Arg Pro Ala Thr Pro Glu Ala Ile Ala Leu
1               5                   10                  15

Cys Ser Arg Leu Leu Glu Tyr Thr Pro Thr Ala Arg Leu Thr Pro Leu
                20                  25                  30

Glu Ala Cys Ala His Ser Phe Phe Asp Glu Leu Arg Asp Pro Asn Val
                35                  40                  45

Lys Leu Pro Asn Gly Arg Asp Thr Pro Ala Leu Phe Asn Phe Thr Thr
    50                  55                  60

Gln Glu Leu Ser Ser Asn Pro Pro Leu Ala Thr Ile Leu Ile Pro Pro
65                  70                  75                  80

His Ala Arg Ile Ala
                85
```

<210> SEQ ID NO 37
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Val Thr Thr Val Val Ala Thr Pro Gly Ala Gly Pro Asp Arg Pro Gln
1               5                   10                  15

Glu Val Ser Tyr Thr Asp Thr Lys Val Ile Gly Asn Gly Ser Ala Gly
                20                  25                  30

Val Val Tyr Gln Ala Lys Leu Cys Asp Ser Gly Glu Leu Val Ala Ile
                35                  40                  45

Lys Lys Val Leu Gln Asp Ala Ala Lys Asn Arg Glu Leu Gln Ile
    50                  55                  60

Met Arg Lys Leu Asp His Cys Asn Ile Val Arg Leu Arg Tyr Phe Phe
65                  70                  75                  80

Tyr Ser Ser Gly Ala Ala Ala Glu Val Tyr Leu Asn Leu Val Leu
                85                  90                  95

Asp Tyr Val Pro Glu Thr Val Tyr Arg Val Ala Arg His Tyr Ser Arg
                100                 105                 110

Ala Ala Gln Thr Leu Pro Val Ile Tyr Val Lys Leu Tyr Met Tyr Gln
            115                 120                 125

Leu Phe Arg Ser Leu Ala Tyr Ile His Ser Phe Gly Ile Cys His Arg
        130                 135                 140

Asp Ile Lys Pro Gln Asn Leu Leu Leu Asp Pro Asp Thr Ala Val Leu
145                 150                 155                 160

Lys Leu Cys Asp Phe Gly Ser Ala Lys Gln Leu Val Ala Gly Glu Pro
                165                 170                 175

Asn Val Ser Tyr Ile Cys Ser Arg Tyr Tyr Arg Ala Pro Glu Leu Ile
                180                 185                 190

Phe Gly Ala Thr Asp Tyr Thr Ser Ser Ile Asp Val Trp Ser Ala Gly
            195                 200                 205

Cys Val Leu Ala Glu Leu Leu Leu Gly Gln Pro Ile Phe Pro Gly Asp
        210                 215                 220

Ser Gly Val Asp Gln Leu Val Glu Ile Ile Lys Val Leu Gly Thr Pro
```

```
225                 230                 235                 240
Thr Ala Glu Gln Ile Ala Glu Met
                245

<210> SEQ ID NO 38
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Ala Ala Ala Ala Trp Thr Lys Val Phe Arg Pro Ala Thr Pro Pro
1               5                   10                  15

Glu Ala Ile Ala Leu Cys Ser Arg Leu Leu Glu Tyr Thr Pro Thr Ala
            20                  25                  30

Arg Leu Thr Pro Leu Glu Ala Cys Ala His Ser Phe Phe Asp Glu Leu
        35                  40                  45

Arg Asp Pro Asn Val Lys Leu Pro Asn Gly Arg Asp Thr Pro Ala Leu
    50                  55                  60

Phe Asn Phe Thr Thr Gln Glu Leu Ser Ser Asn Pro Pro Leu Ala Thr
65                  70                  75                  80

Ile Leu Ile Pro Pro His Ala
                85

<210> SEQ ID NO 39
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser Met Lys Val Gly Arg Gly Gly Gly Gly Lys Val Thr Thr Val
1               5                   10                  15

Val Ala Thr Pro Gly Ala Gly Pro Asp Arg Pro Gln Glu Val Ser Tyr
            20                  25                  30

Thr Asp Thr Lys Val Ile Gly Asn Gly Ser Phe Gly Val Val Tyr Gln
        35                  40                  45

Ala Lys Leu Cys Asp Ser Gly Glu Leu Val Ala Ile Lys Lys Val Leu
    50                  55                  60

Gln Ala Ala Ala Ala Asn Arg Glu Leu Gln Ile Met Arg Lys Leu
65                  70                  75                  80

Asp His Cys Asn Ile Val Arg Leu Arg Tyr Phe Phe Tyr Ser
                85                  90

<210> SEQ ID NO 40
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Tyr Leu Asn Leu Val Leu Asp Tyr Val Pro Glu Thr Val Tyr Arg Val
1               5                   10                  15

Ala Arg His Tyr Ser Arg Ala Lys Gln Thr Leu Pro Val Ile Tyr Val
            20                  25                  30
```

```
Lys Leu Tyr Met Tyr Gln Leu Phe Arg Ser Leu Ala Tyr Ile His Ser
            35                  40                  45

Phe Gly Ile Cys His Arg Asp Ile Lys Pro Gln Asn Leu Leu Leu Asp
    50                  55                  60

Pro Asp Thr Ala Val Leu Lys Leu Cys Asp Phe Gly Ser Ala Lys Gln
65                  70                  75                  80

Leu Val Arg Gly Glu Pro Asn Val Ser Tyr Ile Cys Ser Arg Tyr Tyr
                85                  90                  95

Arg Ala Pro Glu Leu Ile Phe Gly Ala Thr Asp Tyr Thr Ser Ser Ile
            100                 105                 110

Asp Val Trp Ser Ala Gly Cys Val Leu Ala Glu Leu Leu Leu Gly Gln
            115                 120                 125

Pro Ile Phe Pro Gly Asp Ser Gly Val Asp Gln Leu Val Glu Ile Ile
            130                 135                 140

Lys Val Leu Gly Thr Pro Thr Ala Ala Gln Ala Ala Met Asn Pro
145                 150                 155                 160

Asn Tyr Gly Ala

<210> SEQ ID NO 41
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Trp Thr Ala Val Phe Arg Pro Ala Thr Pro Pro Glu Ala Ile Ala Leu
1               5                   10                  15

Cys Ser Arg Leu Leu Glu Tyr Thr Pro Thr Ala Arg Leu Thr Pro Leu
                20                  25                  30

Glu Ala Cys Ala His Ser Phe Phe Asp Glu Leu Arg Asp Pro Asn Val
            35                  40                  45

Lys Leu Pro Asn Gly Arg Asp Thr Pro Ala Leu Phe Asn Phe Thr Thr
    50                  55                  60

Gln Glu Leu Ser Ser Asn Pro Pro Leu Ala Thr Ile Leu Ile Pro Pro
65                  70                  75                  80

His

<210> SEQ ID NO 42
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Val Thr Thr Val Val Ala Thr Pro Gly Ala Gly Pro Asp Arg Pro Gln
1               5                   10                  15

Glu Val Ser Tyr Thr Asp Thr Lys Val Ile Gly Asn Gly Ser Phe Gly
                20                  25                  30

Val Val Tyr Gln Ala Lys Leu Cys Asp Ser Gly Glu Leu Val Ala Ile
            35                  40                  45

Lys Lys Val Leu Gln Asp Ala Ala Ala Lys Asn Arg Glu Leu Gln Ile
    50                  55                  60

Met Arg Lys Leu Asp His Cys Asn Ile Val Arg Leu Arg Tyr Phe Phe
```

```
                65                  70                  75                  80

Tyr Ser Ser

<210> SEQ ID NO 43
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Val Tyr Leu Asn Leu Val Leu Asp Tyr Val Pro Glu Thr Val Tyr Arg
1               5                   10                  15

Val Ala Arg His Tyr Ser Arg Ala Ala Gln Thr Leu Pro Val Ile Tyr
            20                  25                  30

Val Lys Leu Tyr Met Tyr Gln Leu Phe Arg Ser Leu Ala Tyr Ile His
        35                  40                  45

Ser Phe Gly Ile Cys His Arg Asp Ile Lys Pro Gln Asn Leu Leu Leu
    50                  55                  60

Asp Pro Asp Thr Ala Val Leu Lys Leu Cys Asp Phe Gly Ser Ala Lys
65                  70                  75                  80

Gln Leu Val Ala Gly Glu Pro Asn Val Ser Tyr Ile Cys Ser Ala Tyr
                85                  90                  95

Tyr Arg Ala Pro Glu Leu Ile Phe Gly Ala Thr Asp Tyr Thr Ser Ser
            100                 105                 110

Ile Asp Val Trp Ser Ala Gly Cys Val Leu Ala Glu Leu Leu Leu Gly
        115                 120                 125

Gln Pro Ile Phe Pro Gly Asp Ser Gly Val Asp Gln Leu Val Glu Ile
    130                 135                 140

Ile Lys Val Leu Gly Thr Pro Thr Ala Ala Gln Ile Ala Glu Met Asn
145                 150                 155                 160

Pro Asn Tyr Ala Glu Phe Lys Phe
                165

<210> SEQ ID NO 44
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Trp Thr Lys Val Phe Arg Pro Ala Thr Pro Glu Ala Ile Ala Leu
1               5                   10                  15

Cys Ser Arg Leu Leu Glu Tyr Thr Pro Thr Ala Arg Leu Thr Pro Leu
            20                  25                  30

Glu Ala Cys Ala His Ser Phe Phe Asp Glu Leu Arg Asp Pro Asn Val
        35                  40                  45

Lys Leu Pro Asn Gly Arg Asp Thr Pro Ala Leu Phe Asn Phe Thr Thr
    50                  55                  60

Gln Glu Leu Ser Ser Asn Pro Pro Leu Ala Thr Ile Leu Ile Pro Pro
65                  70                  75                  80

His Ala

<210> SEQ ID NO 45
<211> LENGTH: 83
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Lys Val Thr Thr Val Ala Thr Pro Gly Ala Gly Pro Asp Arg Pro
1               5                   10                  15

Gln Glu Val Ser Tyr Thr Asp Thr Lys Val Ile Gly Asn Gly Ser Phe
            20                  25                  30

Gly Val Val Tyr Gln Ala Lys Leu Cys Asp Ser Gly Glu Leu Val Ala
        35                  40                  45

Ile Lys Lys Val Leu Gln Ala Ala Ala Ala Asn Arg Glu Leu Gln
    50                  55                  60

Ile Met Arg Lys Leu Asp His Cys Asn Ile Val Arg Leu Arg Tyr Phe
65                  70                  75                  80

Phe Tyr Ser

<210> SEQ ID NO 46
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Tyr Leu Asn Leu Val Leu Asp Tyr Val Pro Glu Thr Val Tyr Arg Val
1               5                   10                  15

Ala Arg His Tyr Ser Arg Ala Lys Gln Thr Leu Pro Val Ile Tyr Val
            20                  25                  30

Lys Leu Tyr Met Tyr Gln Leu Phe Arg Ser Leu Ala Tyr Ile His Ser
        35                  40                  45

Phe Gly Ile Cys His Arg Asp Ile Lys Pro Gln Asn Leu Leu Leu Asp
    50                  55                  60

Pro Asp Thr Ala Val Leu Lys Leu Cys Asp Phe Gly Ser Ala Lys Gln
65                  70                  75                  80

Leu Val Arg Gly Glu Pro Asn Val Ser Tyr Ile Cys Ser Arg Tyr Tyr
                85                  90                  95

Arg Ala Pro Glu Leu Ile Phe Gly Ala Thr Asp Tyr Thr Ser Ser Ile
            100                 105                 110

Asp Val Trp Ser Ala Gly Cys Val Leu Ala Glu Leu Leu Leu Gly Gln
        115                 120                 125

Pro Ile Phe Pro Gly Asp Ser Gly Val Asp Gln Leu Val Glu Ile Ile
    130                 135                 140

Lys Val Leu Gly Thr Pro Thr Arg Glu Ala Ala Arg Glu Ala Gly Gly
145                 150                 155                 160

Gly

<210> SEQ ID NO 47
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47
```

```
Trp Thr Ala Val Phe Arg Pro Ala Thr Pro Glu Ala Ile Ala Leu
1               5                   10                  15

Cys Ser Arg Leu Leu Glu Tyr Thr Pro Thr Ala Arg Leu Thr Pro Leu
                20                  25                  30

Glu Ala Cys Ala His Ser Phe Phe Asp Glu Leu Arg Asp Pro Asn Val
            35                  40                  45

Lys Leu Pro Asn Gly Arg Asp Thr Pro Ala Leu Phe Asn Phe Thr Thr
50                      55                  60

Gln Glu Leu Ser Ser Asn Pro Pro Leu Ala Thr Ile Leu Ile Pro Pro
65                  70                  75                  80

His
```

<210> SEQ ID NO 48
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Val Thr Thr Val Val Ala Thr Pro Gly Ala Gly Pro Asp Arg Pro Gln
1               5                   10                  15

Glu Val Ser Tyr Thr Asp Thr Lys Val Ile Gly Asn Gly Ser Phe Gly
                20                  25                  30

Val Val Tyr Gln Ala Lys Leu Cys Asp Ser Gly Glu Leu Val Ala Ile
            35                  40                  45

Lys Lys Val Leu Gln Asp Ala Ala Lys Asn Arg Glu Leu Gln Ile
50                  55                  60

Met Arg Lys Leu Asp His Cys Asn Ile Val Arg Leu Arg Tyr Phe Phe
65                  70                  75                  80

Tyr Ser Ser Gly Ala Ala Ala Ala Val Tyr Leu Asn Leu Val Leu
                85                  90                  95

Asp Tyr Val Pro Glu Thr Val Tyr Arg Val Ala Arg His Tyr Ser Arg
            100                 105                 110

Ala Ala Gln Thr Leu Pro Val Ile Tyr Val Lys Leu Tyr Met Tyr Gln
        115                 120                 125

Leu Phe Arg Ser Leu Ala Tyr Ile His Ser Phe Gly Ile Cys His Arg
130                 135                 140

Asp Ile Lys Pro Gln Asn Leu Leu Leu Asp Pro Asp Thr Ala Val Leu
145                 150                 155                 160

Lys Leu Cys Asp Phe Gly Ser Ala Lys Gln Leu Val Ala Gly Glu Pro
                165                 170                 175

Asn Val Ser Tyr Ile Cys Ser Arg Tyr Tyr Arg Ala Pro Glu Leu Ile
            180                 185                 190

Phe Gly Ala Thr Asp Tyr Thr Ser Ser Ile Asp Val Trp Ser Ala Gly
        195                 200                 205

Cys Val Leu Ala Glu Leu Leu Leu Gly Gln Pro Ile Phe Pro Gly Asp
210                 215                 220

Ser Gly Val Asp Gln Leu Val Glu Ile Ile Lys Val Leu Gly Thr Pro
225                 230                 235                 240

Thr Ala Glu Gln Ala Ala Glu
                245
```

<210> SEQ ID NO 49
<211> LENGTH: 82

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Trp Thr Lys Val Phe Arg Pro Ala Thr Pro Glu Ala Ile Ala Leu
1               5                   10                  15

Cys Ser Arg Leu Leu Glu Tyr Thr Pro Thr Ala Arg Leu Thr Pro Leu
            20                  25                  30

Glu Ala Cys Ala His Ser Phe Phe Asp Glu Leu Arg Asp Pro Asn Val
        35                  40                  45

Lys Leu Pro Asn Gly Arg Asp Thr Pro Ala Leu Phe Asn Phe Thr Thr
    50                  55                  60

Gln Glu Leu Ser Ser Asn Pro Pro Leu Ala Thr Ile Leu Ile Pro Pro
65                  70                  75                  80

His Ala

<210> SEQ ID NO 50
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Val Thr Thr Val Val Ala Thr Pro Gly Ala Gly Pro Asp Arg Pro Gln
1               5                   10                  15

Glu Val Ser Tyr Thr Asp Thr Lys Val Ile Gly Asn Gly Ser Ala Gly
            20                  25                  30

Val Val Tyr Gln Ala Lys Leu Cys Asp Ser Gly Glu Leu Val Ala Ile
        35                  40                  45

Lys Lys Val Leu Gln Asp Ala Gly Phe Lys Asn Arg Glu Leu Gln Ile
    50                  55                  60

Met Arg Lys Leu Asp His Cys Asn Ile Val Arg Leu Arg Tyr Phe Phe
65                  70                  75                  80

Tyr Ser Ser Gly Ala Gly Gly Ala Glu Val Tyr Leu Asn Leu Val Leu
                85                  90                  95

Asp Tyr Val Pro Glu Thr Val Tyr Arg Val Ala Arg His Tyr Ser Arg
            100                 105                 110

Ala Lys Gln Thr Leu Pro Val Ile Tyr Val Lys Leu Tyr Met Tyr Gln
        115                 120                 125

Leu Phe Arg Ser Leu Ala Tyr Ile His Ser Phe Gly Ile Cys His Arg
    130                 135                 140

Asp Ile Lys Pro Gln Asn Leu Leu Leu Asp Pro Asp Thr Ala Val Leu
145                 150                 155                 160

Lys Leu Cys Asp Phe Gly Ser Ala Lys Gln Leu Val Arg Gly Glu Pro
                165                 170                 175

Asn Val Ser Tyr Ile Cys Ser Arg Tyr Tyr Arg Ala Pro Glu Leu Ala
            180                 185                 190

Phe Gly Ala Thr Asp Tyr Thr Ser Ser Ile Asp Val Trp Ser Ala Gly
        195                 200                 205

Cys Val Leu Ala Glu Leu Leu Leu Gly Gln Pro Ile Phe Pro Gly Asp
    210                 215                 220

Ser Gly Gly Asp Gln Leu Val Glu Ile Ile Lys Val Leu Gly Thr Pro
```

```
                225                 230                 235                 240

Thr Arg Glu Gln Ile Ala Glu Met Asn Pro Asn
                245                 250

<210> SEQ ID NO 51
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ala Ala Ala Ala His Pro Trp Thr Ala Val Phe Arg Pro Ala Thr
1               5                   10                  15

Pro Pro Glu Ala Ile Ala Leu Cys Ser Arg Leu Leu Glu Tyr Thr Pro
                20                  25                  30

Thr Ala Arg Leu Thr Pro Leu Glu Ala Cys Ala His Ser Phe Phe Asp
            35                  40                  45

Glu Leu Arg Asp Pro Asn Val Lys Leu Pro Asn Gly Arg Asp Thr Pro
    50                  55                  60

Ala Leu Phe Asn Phe Thr Thr Gln Glu Leu Ser Ser Asn Pro Pro Leu
65                  70                  75                  80

Ala Thr Ile Leu Ile Pro Pro His Ala Arg
                85                  90

<210> SEQ ID NO 52
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Val Thr Thr Val Val Ala Thr Pro Gly Gln Gly Pro Asp Arg Pro Gln
1               5                   10                  15

Glu Val Ser Tyr Thr Asp Thr Lys Val Ile Gly Asn Gly Ser Phe Gly
                20                  25                  30

Val Val Tyr Gln Ala Lys Leu Cys Asp Ser Gly Glu Leu Val Ala Ile
            35                  40                  45

Lys Lys Val Leu Gln Asp Gly Ala Phe Lys Asn Arg Glu Leu Gln Ile
    50                  55                  60

Met Arg Lys Leu Asp His Cys Asn Ile Val Arg Leu Arg Tyr Phe Phe
65                  70                  75                  80

Tyr Ser Ser Gly Gly Ala Gly Asp Ala Val Tyr Leu Asn Leu Val Leu
                85                  90                  95

Asp Tyr Val Pro Glu Thr Val Tyr Arg Val Ala Arg His Tyr Ser Arg
                100                 105                 110

Ala Lys Gln Thr Leu Pro Val Ile Tyr Val Lys Leu Tyr Met Tyr Gln
            115                 120                 125

Leu Phe Arg Ser Leu Ala Tyr Ile His Ser Phe Gly Ile Cys His Arg
    130                 135                 140

Asp Ile Lys Pro Gln Asn Leu Leu Leu Asp Pro Asp Thr Ala Val Leu
145                 150                 155                 160

Lys Leu Cys Asp Phe Gly Ser Ala Lys Gln Leu Val Arg Gly Glu Pro
                165                 170                 175

Asn Val Ser Tyr Ile Cys Ser Arg Tyr Tyr Arg Ala Pro Glu Leu Ile
```

```
                        180                 185                 190
Phe Gly Ala Thr Asp Tyr Thr Ser Ser Ile Asp Val Trp Ser Ala Gly
        195                 200                 205
Cys Val Leu Ala Glu Leu Leu Leu Gly Gln Pro Ile Phe Pro Gly Asp
    210                 215                 220
Ser Gly Val Asp Gln Leu Ala Glu Ile Ile Lys Val Leu Gly Thr Pro
225                 230                 235                 240
Thr Arg Glu Gln Ile Ala Glu Met Asn Pro Asn
                245                 250

<210> SEQ ID NO 53
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Ala Ala Ala Ala His Pro Trp Thr Ala Val Phe Arg Pro Ala Thr
1               5                   10                  15
Pro Pro Glu Ala Ile Ala Leu Cys Ser Arg Leu Leu Glu Tyr Thr Pro
            20                  25                  30
Thr Ala Arg Leu Thr Pro Leu Glu Ala Cys Ala His Ser Phe Phe Asp
        35                  40                  45
Glu Leu Arg Asp Pro Asn Val Lys Leu Pro Asn Gly Arg Asp Thr Pro
    50                  55                  60
Ala Leu Phe Asn Phe Thr Thr Gln Glu Leu Ser Ser Asn Pro Pro Leu
65                  70                  75                  80
Ala Thr Ile Leu Ile Pro Pro His Ala Arg
                85                  90

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphoylated-Ser

<400> SEQUENCE: 54

Ser Pro His Gln Ser Glu Asp Glu
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phosphoylated-Ser

<400> SEQUENCE: 55

His Ser Ser Pro His Gln Ser Glu Asp
1               5
```

```
<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 56

His His His His His His
1               5
```